US007452901B2

(12) United States Patent
Boojamra et al.

(10) Patent No.: US 7,452,901 B2
(45) Date of Patent: Nov. 18, 2008

(54) ANTI-CANCER PHOSPHONATE ANALOGS

(75) Inventors: Constantine G. Boojamra, San Francisco, CA (US); Carina Cannizzaro, San Mateo, CA (US); James M. Chen, San Ramon, CA (US); Xiaowu Chen, San Mateo, CA (US); Aesop Cho, Mountain View, CA (US); Lee S. Chong, Newark, CA (US); Maria Fardis, San Carlos, CA (US); Alan X. Huang, San Mateo, CA (US); Choung U. Kim, San Carlos, CA (US); Thorsten Kirschberg, Belmont, CA (US); Steven Krawczyk, San Carlos, CA (US); Christopher P. Lee, San Francisco, CA (US); Kuei-Ying Lin, Fremont, CA (US); Richard L. Mackman, Millbrae, CA (US); David Y. Markevitch, Los Angeles, CA (US); Peter H. Nelson, Los Altos, CA (US); David A. Oare, Belmont, CA (US); Vidya K. Prasad, Burlingame, CA (US); Hyung-Jung Pyun, Freemont, CA (US); Adrian S. Ray, San Mateo, CA (US); Sundaramoorthi Swaminathan, Burlingame, CA (US); William J. Watkins, Sunnyvale, CA (US); Jennifer R. Zhang, Foster City, CA (US); Lijun Zhang, Palo Alto, CA (US)

(73) Assignee: Gilead Sciences, Inc., Foster City, CA (US)

(*) Notice: Subject to any disclaimer, the term of this patent is extended or adjusted under 35 U.S.C. 154(b) by 103 days.

(21) Appl. No.: 10/833,293

(22) Filed: Apr. 26, 2004

(65) Prior Publication Data
US 2006/0079478 A1    Apr. 13, 2006

Related U.S. Application Data

(60) Provisional application No. 60/465,588, filed on Apr. 25, 2003, provisional application No. 60/465,594, filed on Apr. 25, 2003, provisional application No. 60/465,465, filed on Apr. 25, 2003, provisional application No. 60/465,569, filed on Apr. 25, 2003, provisional application No. 60/465,467, filed on Apr. 25, 2003, provisional application No. 60/465,631, filed on Apr. 25, 2003, provisional application No. 60/465,714, filed on Apr. 25, 2003, provisional application No. 60/465,589, filed on Apr. 25, 2003, provisional application No. 60/465,586, filed on Apr. 25, 2003, provisional application No. 60/465,607, filed on Apr. 25, 2003, provisional application No. 60/465,668, filed on Apr. 25, 2003, provisional application No. 60/465,287, filed on Apr. 25, 2003, provisional application No. 60/465,343, filed on Apr. 25, 2003, provisional application No. 60/465,471, filed on Apr. 25, 2003, provisional application No. 60/465,567, filed on Apr. 25, 2003, provisional application No. 60/465,545, filed on Apr. 25, 2003, provisional application No. 60/465,394, filed on Apr. 25, 2003, provisional application No. 60/465,603, filed on Apr. 25, 2003, provisional application No. 60/465,614, filed on Apr. 25, 2003, provisional application No. 60/465,339, filed on Apr. 25, 2003, provisional application No. 60/465,325, filed on Apr. 25, 2003, provisional application No. 60/465,377, filed on Apr. 25, 2003, provisional application No. 60/465,415, filed on Apr. 25, 2003, provisional application No. 60/465,575, filed on Apr. 25, 2003, provisional application No. 60/465,844, filed on Apr. 25, 2003, provisional application No. 60/465,559, filed on Apr. 25, 2003, provisional application No. 60/465,531, filed on Apr. 25, 2003, provisional application No. 60/493,303, filed on Aug. 7, 2003, provisional application No. 60/493,310, filed on Aug. 7, 2003, provisional application No. 60/495,382, filed on Aug. 15, 2003, provisional application No. 60/495,685, filed on Aug. 15, 2003, provisional application No. 60/495,527, filed on Aug. 15, 2003, provisional application No. 60/495,686, filed on Aug. 15, 2003, provisional application No. 60/495,525, filed on Aug. 15, 2003, (Continued)

(51) Int. Cl.
*A61K 31/44* (2006.01)
*C07D 239/00* (2006.01)
(52) U.S. Cl. .................................. 514/300; 544/300
(58) Field of Classification Search ................ 544/254; 514/300
See application file for complete search history.

(56) References Cited

U.S. PATENT DOCUMENTS 5,413,996 A    5/1995    Bodor
5,493,030 A    2/1996    Morgans et al.

(Continued)

FOREIGN PATENT DOCUMENTS

EP    0 267 050    5/1988
EP    0 441 192    1/1991

(Continued)

OTHER PUBLICATIONS

Hostetler's, 1997, CAS:127:185859.*
Allen, Lee F. et al., CI-1040 (PD184352), a Targeted Signal Transduction Inhibitor of MEK (MAPKK), *Seminars in Oncology*, Oct. 2003, pp. 105-116, vol. 30, No. 5, Elsevier Inc.

(Continued)

*Primary Examiner*—Rei-tsang Shiao
(74) *Attorney, Agent, or Firm*—Viksnins, Harris & Padys PLLP

(57) ABSTRACT

The invention is related to phosphorus substituted anti-cancer compounds, compositions containing such compounds, and therapeutic methods that include the administration of such compounds, as well as to processes and intermediates useful for preparing such compounds.

13 Claims, No Drawings

Related U.S. Application Data provisional application No. 60/495,629, filed on Aug. 15, 2003, provisional application No. 60/495,484, filed on Aug. 15, 2003, provisional application No. 60/495,644, filed on Aug. 15, 2003, provisional application No. 60/495,297, filed on Aug. 15, 2003, provisional application No. 60/495,682, filed on Aug. 15, 2003, provisional application No. 60/495,784, filed on Aug. 15, 2003, provisional application No. 60/495,751, filed on Aug. 15, 2003, provisional application No. 60/495,565, filed on Aug. 15, 2003, provisional application No. 60/495,789, filed on Aug. 15, 2003, provisional application No. 60/495,736, filed on Aug. 15, 2003, provisional application No. 60/495,769, filed on Aug. 15, 2003, provisional application No. 60/495,647, filed on Aug. 15, 2003, provisional application No. 60/495,645, filed on Aug. 15, 2003, provisional application No. 60/495,362, filed on Aug. 15, 2003, provisional application No. 60/495,339, filed on Aug. 15, 2003, provisional application No. 60/495,534, filed on Aug. 15, 2003, provisional application No. 60/495,669, filed on Aug. 15, 2003, provisional application No. 60/495,425, filed on Aug. 15, 2003, provisional application No. 60/495,524, filed on Aug. 15, 2003, provisional application No. 60/495,426, filed on Aug. 15, 2003, provisional application No. 60/495,393, filed on Aug. 15, 2003, provisional application No. 60/495,387, filed on Aug. 15, 2003, provisional application No. 60/495,416, filed on Aug. 15, 2003, provisional application No. 60/514,462, filed on Oct. 24, 2003, provisional application No. 60/513,971, filed on Oct. 24, 2003, provisional application No. 60/513,969, filed on Oct. 24, 2003, provisional application No. 60/514,394, filed on Oct. 24, 2003, provisional application No. 60/514,393, filed on Oct. 24, 2003, provisional application No. 60/513,944, filed on Oct. 24, 2003, provisional application No. 60/513,956, filed on Oct. 24, 2003, provisional application No. 60/513,923, filed on Oct. 24, 2003, provisional application No. 60/514,202, filed on Oct. 24, 2003, provisional application No. 60/514,247, filed on Oct. 24, 2003, provisional application No. 60/514,461, filed on Oct. 24, 2003, provisional application No. 60/514,369, filed on Oct. 24, 2003, provisional application No. 60/514,452, filed on Oct. 24, 2003, provisional application No. 60/514,439, filed on Oct. 24, 2003, provisional application No. 60/513,948, filed on Oct. 24, 2003, provisional application No. 60/514,424, filed on Oct. 24, 2003, provisional application No. 60/513,972, filed on Oct. 24, 2003, provisional application No. 60/513,925, filed on Oct. 24, 2003, provisional application No. 60/513,926, filed on Oct. 24, 2003, provisional application No. 60/513,927, filed on Oct. 24, 2003, provisional application No. 60/514,368, filed on Oct. 24, 2003, provisional application No. 60/514,207, filed on Oct. 24, 2003, provisional application No. 60/514,115, filed on Oct. 24, 2003, provisional application No. 60/513,980, filed on Oct. 24, 2003, provisional application No. 60/514,131, filed on Oct. 24, 2003, provisional application No. 60/514,105, filed on Oct. 24, 2003, provisional application No. 60/514,280, filed on Oct. 24, 2003, provisional application No. 60/513,963, filed on Oct. 24, 2003, provisional application No. 60/514,145, filed on Oct. 24, 2003, provisional application No. 60/514,159, filed on Oct. 24, 2003, provisional application No. 60/514,083, filed on Oct. 24, 2003, provisional application No. 60/513,949, filed on Oct. 24, 2003, provisional application No. 60/514,144, filed on Oct. 24, 2003, provisional application No. 60/514,481, filed on Oct. 24, 2003, provisional application No. 60/513,974, filed on Oct. 24, 2003, provisional application No. 60/514,108, filed on Oct. 24, 2003, provisional application No. 60/513,979, filed on Oct. 24, 2003, provisional application No. 60/514,084, filed on Oct. 24, 2003, provisional application No. 60/514,161, filed on Oct. 24, 2003, provisional application No. 60/514,304, filed on Oct. 24, 2003, provisional application No. 60/514,235, filed on Oct. 24, 2003, provisional application No. 60/514,325, filed on Oct. 24, 2003, provisional application No. 60/514,359, filed on Oct. 24, 2003, provisional application No. 60/514,113, filed on Oct. 24, 2003, provisional application No. 60/514,114, filed on Oct. 24, 2003, provisional application No. 60/514,112, filed on Oct. 24, 2003, provisional application No. 60/513,968, filed on Oct. 24, 2003, provisional application No. 60/514,345, filed on Oct. 24, 2003, provisional application No. 60/514,346, filed on Oct. 24, 2003, provisional application No. 60/513,564, filed on Oct. 24, 2003, provisional application No. 60/513,588, filed on Oct. 24, 2003, provisional application No. 60/514,298, filed on Oct. 24, 2003, provisional application No. 60/514,330, filed on Oct. 24, 2003, provisional application No. 60/513,932, filed on Oct. 24, 2003, provisional application No. 60/513,976, filed on Oct. 24, 2003, provisional application No. 60/513,562, filed on Oct. 24, 2003, provisional application No. 60/514,258, filed on Oct. 24, 2003, provisional application No. 60/519,476, filed on Nov. 12, 2003, provisional application No. 60/524,340, filed on Nov. 20, 2003, provisional application No. 60/532,230, filed on Dec. 22, 2003, provisional application No. 60/531,960, filed on Dec. 22, 2003, provisional application No. 60/532,160, filed on Dec. 22, 2003, provisional application No. 60/531,940, filed on Dec. 22, 2003, provisional application No. 60/532,591, filed on Dec. 23, 2003, provisional application No. 60/536,007, filed on Jan. 12, 2004, provisional application No. 60/536,006, filed on Jan. 12, 2004, provisional application No. 60/536,005, filed on Jan. 12, 2004, provisional application No. 60/536,054, filed on Jan. 12, 2004, provisional application No. 60/465,641, filed on Apr. 25, 2003.

(56) References Cited

U.S. PATENT DOCUMENTS

| | | | |
|---|---|---|---|
| 5,585,397 | A | 12/1996 | Tung et al. |
| 5,633,279 | A | 5/1997 | Morgans et al. |
| 5,654,286 | A * | 8/1997 | Hostetler ............... 514/47 |
| 5,670,497 | A | 9/1997 | Bold et al. |
| 5,747,498 | A | 5/1998 | Schnur et al. |
| 5,750,343 | A | 5/1998 | Maag et al. |
| 5,750,493 | A | 5/1998 | Sommadossi et al. |
| 5,811,422 | A | 9/1998 | Lam et al. |
| 5,874,577 | A | 2/1999 | Chen et al. |
| 5,914,332 | A | 6/1999 | Sham et al. |
| 6,072,053 | A | 6/2000 | Vince et al. |
| 6,174,888 | B1 | 1/2001 | McQuire et al. |
| 6,312,662 | B1 | 11/2001 | Erion et al. |
| 6,319,946 | B1 | 11/2001 | Hale et al. |
| 6,395,763 | B1 | 5/2002 | Stamos et al. |

| | | | |
|---|---|---|---|
| 6,608,027 | B1 | 8/2003 | Tsantrizos et al. |
| 6,767,900 | B2 | 7/2004 | Ubasawa et al. |
| 2001/0031773 | A1 | 10/2001 | Camden |
| 2002/0119443 | A1 | 8/2002 | Becker et al. |
| 2003/0109498 | A1 | 6/2003 | Yuasa et al. |
| 2004/0121316 | A1 | 6/2004 | Birkus et al. |
| 2004/0167096 | A1 | 8/2004 | Cheng et al. |

FOREIGN PATENT DOCUMENTS

| | | |
|---|---|---|
| EP | 0 465 297 | 1/1992 |
| EP | 0 531 597 | 3/1993 |
| EP | 0 632 048 | 1/1995 |
| EP | 0 786 455 | 7/1997 |
| EP | 0 852 233 | 7/1998 |
| EP | 0 919 562 | 6/1999 |
| EP | 1 295 879 | 3/2003 |
| WO | WO 88/06158 | 8/1988 |
| WO | WO91/19721 | 12/1991 |
| WO | WO 92/00988 | 1/1992 |
| WO | WO 92/18520 | 10/1992 |
| WO | WO 93/12123 | 6/1993 |
| WO | WO 93/24510 | 12/1993 |
| WO | WO 96/14314 | 5/1996 |
| WO | WO 96/40156 | 12/1996 |
| WO | WO 97/01558 | 1/1997 |
| WO | WO 98/04569 | 2/1998 |
| WO | WO 98/11906 | 3/1998 |
| WO | WO 98/15563 | 4/1998 |
| WO | WO 99/33815 | 7/1999 |
| WO | WO 99/62921 | 12/1999 |
| WO | WO 00/04033 | 1/2000 |
| WO | WO 00/52015 A2 | 9/2000 |
| WO | WO 00/52015 A3 | 2/2001 |
| WO | WO 01/13957 | 3/2001 |
| WO | WO 01/17982 | 3/2001 |
| WO | WO 01/19320 | 3/2001 |
| WO | WO 01/39724 A2 | 6/2001 |
| WO | WO 01/46204 | 6/2001 |
| WO | WO 01/64693 | 9/2001 |
| WO | WO 01/39724 A3 | 10/2001 |
| WO | WO 01/96329 | 12/2001 |
| WO | WO 01/96354 | 12/2001 |
| WO | WO 02/03997 | 1/2002 |
| WO | WO 02/06292 | 1/2002 |
| WO | WO 02/08241 | 1/2002 |
| WO | WO 02/14344 | 2/2002 |
| WO | WO 02/48165 A2 | 6/2002 |
| WO | WO 02/057425 | 7/2002 |
| WO | WO 02/100415 | 12/2002 |
| WO | WO 02/103008 A2 | 12/2002 |
| WO | WO 03/028737 | 4/2003 |
| WO | WO 02/048165 A3 | 5/2003 |
| WO | WO 03/050129 | 6/2003 |
| WO | WO 03/059255 | 7/2003 |
| WO | WO 03/064383 | 8/2003 |
| WO | WO 03/066005 | 8/2003 |
| WO | WO 03/080078 | 10/2003 |
| WO | WO 02/103008 A3 | 11/2003 |
| WO | WO 03/090690 | 11/2003 |
| WO | WO 2004/096234 | 11/2004 |
| WO | WO 2004/096818 A2 | 11/2004 |
| WO | WO 2005/011709 | 2/2005 |
| WO | WO 2005/011709 A1 | 2/2005 |
| WO | WO 2004/096818 A3 | 4/2005 |

OTHER PUBLICATIONS

Bantia, Shanta et al., Purine nucleoside phosphorylase inhibitor BCX-1777 (Immucillin-H)—a novel potent and orally active immunosuppressive agent, *International Immunopharmacology*, 2001, pp. 1199-1210, Elsevier Science B.V.

Beauchamp, Lilia M., et al., Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase, *Journal of Medicinal Chemistry*, 1996, pp. 949-956, American Chemical Society.

Bohani D. W. et al., A-420983: a potent, orally active inhibitor of Ick with efficacy in a model of transplant rejection, *Bioorganic & Medicinal Chemistry Letters*, 2004, vol. 14.

Bzowska, Agnieszka et al., Purine nucleoside phosphorylases: properties, functions, and clinical aspects, *Pharmacology & Therapeutics*, 2000, pp. 349-425, vol. 88, Elsevier Science Inc.

Chapman, H. et al., Practical Synthesis, Separation, and Stereochemical Assignment of the PMPA Pro-Drug GS-7340, Nucleosides, Nucleotides & Nucleic Acids, 2001, pp. 621-628, vol. 20, Nos. 4-7, Marcel Dekker, Inc.

Clark, Jeremy L. et al., Mycophenolic Acid Analogues as Potential Agents Against West Nile Virus Infection.

Conklyn, Maryrose et al., The JAK3 inhibitor CP-690550 selectively reduces NK and CD8+ cell numbers in cynomolgus monkey blood following chronic oral dosing, *Journal of Leukocyte Biology*, Dec. 2004, pp. 1-8, vol. 76, The Society for Leukocyte Biology.

De Clereq, E., Highlights in the Development of New Antiviral Agents, *Mini Reviews in Medicinal Chemistry*, 2002, 163-175, vol. 2, No. 2, Bentham Science Publishers, Ltd.

Evans, Gary B., Exploring Structure—Activity Relationships of Transition State Analogues of Human Purine Nucleoside Phosphorylase, *J. Med. Chem.*, 2003, 3412-3423, vol. 46, No. 15, American Chemical Society.

Gumina, Giuseppe et al., Advances in antiviral agents for hepatitis B virus, *Antiviral Chemistry & Chemotherapy*, 2001, 93-112, vol. 12, Suppl. 1, International Medical Press.

Gobec, S. et al., Phosphonate inhibitors of antiget 85C, a crucial enzyme involved in the biosynthesis of the mycobacterium tuberculosis cell wall, *Bioorganic and Medicinal Chemistry Letters*, 2004, vol. 14.

Hegedus, Louis S. et al., Synthesis of 4'-Methyl and 4'-cyano Carbocyclic 2',3'-Didehydro Nucleoside Analogues via 1,4-Addition to Substituted Cyclopentenones, *J. Org. Chem.*, 2004, 8492-8495, vol. 69, No. 24, American Chemical Society.

Herczegh P., et al., Osteoadsorptive bisphosphonate derivatives of fluoroquinolone antibacterials, *J. Med. Chem.*, 2002, vol. 45.

Hirabayashi, Hideki et al., Bone-Specific Drug Delivery Systems, *Clinical Pharacokinetics*, 2003, 1319-1330, vol. 42, No. 15.

Holy A. et al., Synthesis, *Cllect. Czech. Chem. Commun.*, 1989, vol. 54, pp. 2190-2210.

Jain, Jugnu et al., Characterization of Pharmacological Efficacy of VX-148, a New, Potent Immunosuppressive Inosine 5'-Monophosphate Dehydrogenase Inhibitor, *Journal of Pharmacology and Experimental Therapeutics*, 2002, 1272-1277, vol. 302, No. 3, The American Society for Pharmacology and Experimental Therapeutics.

Karpenko, Inna L. et al., Synthesis and Antiherpetic Activity of Acyclovir Phosphonates, *Nucleosides, Nucleotides & Nucleic Acids*, 2003, 319-328, vol. 22, No. 3, Marcel Dekker, Inc.

Kato, Keisuke et al., Stereoselective synthesis of 4'-.alpha.-alkyclcarbovir derivatives based on an asymmetric synthesis or chemo-enzymatic procedure, *Chemical & Pharmaceutical Bulletin*, 1999, 1256-1264, vol. 49, No. 9, Pharmaceutical Society of Japan.

Kato, Keisuke et al., Enantio- and diastereoselective syntheis of 4'-α-substituted carbocyclic nucleosides, *Tetrahedron: Asymmetry*, 1998, 911-914, vol. 9, Elsevier Science Ltd.

Kilpatrick, J. Michael, Intravenous and oral pharmacokinetic study of BCX-1777, a novel purine nucleoside phosphorylase transition-state inhibitor, In vivo effects on blood 2'-deoxyguanosine in primates, *International Immunopharmacology*, 2003, 541-548, vol. 3, Elsevier Science B.V.

Kim, Choung Un et al., Regiospecific and Highly Stereoselective Electrophilic Addition to Furanoid Glycals: Synthesis of Phosphonate Nucleotide Analogues with Potent Activity against HIV, J. Org. Chem., 1991, 2642-2647, vol. 56, No. 8, American Chemical Society.

Kinsky, Stephen C. et al., Inhibition of cell proliferation by putative metabolites and non-degradable analogs of methotrexate-.gama.-dimyristoylphosphatidylethanolamine, *Biochimica et Biphysica Acta*, 19878, 211-218, vol. 917, No. 2, Elsevier Science Publishers B. V.

Kinsky, Stephen C. et al., Effect of liposomes sentitized with methotrexate-γ-dimyristoylphosphatidylethanolamine on cells that are resistant to methotrexate, *Biochimica et Biophysica Acta*, 1986, 129-135, vol. 885, Elsevier Science Publishers B.V.

Kinsky, Stephen C. et al., Circumvention of the methotrexate transport system by methotrexate-phosphatidylethanolamine derivatives effect of fatty acid chain length, *Biochimica et Biophysica Acta*, 1987, 96-103, vol. 921, Elsevier Science Publishers B.V.

Ko, Ok Hyun et al., Efficient synthesis of novel carbocyclic nucleosides via sequential Claisen rearrangement and ring-closing metathesis, *Tetrahedron Letters*, 2002, 6399-6402, vol. 43, Elsevier Science Ltd.

Reed, Leff et al., Antidiabetic PPARγ Ligands: An update on Compounds in development, *Curr. Med. Chem.—Imun., Endoc. & Metab. Agents*, 2002, 33-47, vol. 2, No. 1, Bentham Science Publishers Ltd.

Lewandowicz, Andrzej et al., Achieving the Ultimate Physiological Goal in Transition State Analogue Inhibitors for Purine Nucleoside Phosphorylase, *The Journal of Biological Chemistry*, 2003, 31465-31468, vol. 278, No. 34, The American Society for Biochemistry and Molecular Biology, Inc.

Pankiewicz, Krzysztof W., Novel Mycophenolic Adenine Bis(phosphonate) Analogues As Potential Differentiation Agents against Human Leukemia, *J. Med. Chem.*, 2002 703-712, vol. 45, No. 3, American Chemical Society.

Ono-Nita, Suzane Kioko et al., Novel Nucleoside Analogue MCC-478 (LY582563) is Effective against Wild-Type or Lamivudine-Resistant Hepatitis B Virus, *Antimicrobial Agents and Chemothrapy*, 2002, 2602-2605, vol. 46, No. 8, American Society for Microbiology.

Parang, Keykavous et al., Novel Approaches for Designing 5'-O-Ester Prodrugs of 3'-Azido-2', 3'-dideoxythymidine (AZT), *Current Medicinal Chemistry*, 2000, 995-1039, vol. 7, No. 10, Bentham Science Publishers Ltd.

Prashad, Mahavir et al., An Efficient and Large-Scale Enantioselective Synthesis of PNP405: A Purine Nucleoside Phosphorylase Inhibitor, *J. Org. Chem.*, 2002, 6612-6617, vol. 67, No. 19, American Chemical Society.

Ray, Adrian S. et al., Role of Purine Nucleoside Phosphorylase in Interactions between 2', 3'-Dideoxyinosine and Allopurinal, Ganciclovir, or Tenofovir, Antimicrobial Agents and Chemotherapy, 2004, 1089-1095, vol. 48, No. 4, American Society for Microbiology.

Roberts, Stanley M., Development of the route to the new anti-AIDS drug abacavir: A highlight of academic/industry laison, *IDrugs*, 1998, 896-899, vol. 1, No. 8, Current Drugs Ltd.

Rosowsky, Andre et al., Methotrexate Analogues—27, *Biochemical Pharmacology*, 1986, 3327-3333, vol. 35, No. 19, Pergamon Journals Ltd.

Rosowsky, Andre et al., Methotrexate Analogues, 32, Chain Extension, α-Carboxyl Replacement by Sulfonate and Phosphonate: Effect on Enzyme Binding and Cell-Growth Inhibition, *J. Med. Chem.*, 1988, 1326-1331, vol. 31, No. 7, American Chemical Society.

Schultz, C., Prodrugs of biologically active phosphate esters, *Bioorganic & Medicinal Chemistry*, 2003, 885-898, vol. 11, Elsevier Science Ltd., GB.

Sekiya, Kouichi et al., 2-Amino-6-arylthio-9-[2-(phosphonomethoxy) ethyl] purine Bis(2,2,2-trifluoroethyl) Esters as Novel HBV-Specific Antiviral Reagents, Journal of Medicinal Chemistry, 2002, 3138-3142, vol. 45, No. 14, American Chemical Society.

Shi, Wuxian et al., *Plasmodium falciparum* Purine Nucleoside Phosphorylase, The Journal of Biological Chemistry, 2004, 18103-18106, vol. 279, No. 18, The American Society of Biochemistry and Molecular Biology, Inc.

Sintchak, Michael D. et al., The structure of inosine 5'-monophosphate dehydrogenase and the design of novel inhibitors, Immunopharmachology, 2000, 163-184, vol. 47, Elsevier.

Srinivas, Ranga V. et al., Metabolism and In Vitro Antiretroviral Activities of Bis(Pivaloyloxymethyl) Prodrugs of Acyclic Nucleoside Phosphonates, Antimicrobial Agents and Chemotherapy, 1993, 2247-2250, vol. 37, No. 10, American Society for Microbiology.

Sturtz, Georges et al., Su rune nouvelle approche de pharmacomodulation du methotrexate: synthese d'analogues gem-diphosphoniques d'amethopterine et de la N-10 deaza amethopterine, Medicinal Chemistry, C. R. Acad. Sci. Paris, 1990, vol. 10, No. 2, 739-742, Academie des Sciences.

Sturtz, Georges et al., Analogues phosphonoglutamiques d'amethopterine (methotrexate), Eur. J. Med. Chem—Chim. Ther., 1984, 267-273, vol. 19, No. 3.

Sturtz, G. et al., Synthesis of gem-bisphosphonic methotrexate conjugates and their biological response towards Walker's osteosarcoma, *Eur. J. Med. Chem.*, 1993, 899-903, vol. 28, Elsevier.

Sturtz, G. et al., A study of the delivery-targeting concept applied to antineoplasic drugs active on human osteosarcoma, I. Synthesis and biological activity in nude mice carrying human osteosarcoma xenografts of gem-bisphosphonic methotrexate analogues, Eur J. Med. Chem., 1992, 825-833, vol. 27, No. 8, Elsevier.

Waegell W. et al. A420983, a novel, small molecule inhibitor of LCK prevents allograft rejection, Transplantation Proceedings, 2002, 1411-1417, vol. 34.

Wroblewski, Andrzej et al., Synthesis of (1R,2S)- and (1S,2S)-3-(4-carbamoyl-1,2,3-triazol-1-yl)-1,2-dihydroxypropylphosphonates, Tetrahedron: Asymmetry, 2004, 1457-1464, vol. 15, Elsevier.

Abdel-Meguid, Sherin S. et al., Inhibition of Human Immunodeficiency Virus-1 Protease by a $C_2$-Symmetric Phosphinate. Synthesis and Crystallographic Analysis, *Biochemistry*, 1993, 1543-1572, vol. 32, No. 31.

De Clercq, Erik, New Developments in Anti-HIV Chemotherapy, *Current Medicinal Chemistry*, 2001, 1543-1572, vol. 8, No. 13, Bentham Science Publishers Ltd.

Dvorakova, Hana et al., Synthesis of 2'-Aminomethyl Derivatives of N-(2-(Phosphonomethoxy)ethyl) Nucleotide Analogues as Potential Antiviral Agents, *J. Med. Chem.*, 1996, 3263-3268. vol. 38, No. 17.

Menendez-Arias, Luis et al. Targeting HIV: antiretroviral therapy and the development of drug resistance, *Trends in Pharmacological Sciences*, 2002, 381-388, vol. 23, No. 8, Elsevier Science Ltd.

Vielhaber, Bernd, Bericht vom 3rd International Workshop on Salvage Therapy for HIV-Infection, *Deutsche Aids-Hilfe e.V. FaxReport zu HIV und AIDS*, 2000, 12-14.

Morgans et al., CAS:124:86709 (1995).

Sturtz et al, CAS:101:143560 (1984).

* cited by examiner

ANTI-CANCER PHOSPHONATE ANALOGS

This non-provisional application claims the benefit of priority under 35 U.S.C. § 119(e) to U.S. Provisional Patent Application Ser. Nos. 60/465,588; 60/465,594; 60/465,465; 60/465,569; 60/465,467; 60/465,631; 60/465,714; 60/465,589; 60/465,586; 60/465,607; 60/465,668; 60/465,287; 60/465,343; 60/465,471; 60/465,567; 60/465,545; 60/465,394; 60/465,603; 60/465,614; 60/465,339; 60/465,325; 60/465,377; 60/465,415; 60/465,575; 60/465,844; 60/465,559; and 60/465,531; all filed Apr. 25, 2003; and to U.S. Provisional Patent Application Ser. Nos. 60/493,303 and 60/493,310; both filed Aug. 7, 2003; and to U.S. Provisional Patent Application Ser. Nos. 60/495,382; 60/495,685; 60/495,527; 60/495,686; 60/495,525; 60/495,629; 60/495,484; 60/495,644; 60/495,297; 60/495,682; 60/495,784; 60/495,751; 60/495,565; 60/495,789; 60/495,736; 60/495,769; 60/495,647; 60/495,645; 60/495,362; 60/495,339; 60/495,534; 60/495,669; 60/495,425; 60/495,524; 60/495,426; 60/495,393; 60/495,387; and 60/495,416; all filed Aug. 15, 2003; and to U.S. Provisional Patent Application Ser. Nos. 60/514,462; 60/513,971; 60/513,969; 60/514,394; 60/514,393; 60/513,944; 60/513,956; 60/513,923; 60/514,202; 60/514,247; 60/514,461; 60/514,369; 60/514,452; 60/514,439; 60/513,948; 60/514,424; 60/513,972; 60/513,925; 60/513,926; 60/513,927; 60/514,368; 60/514,207; 60/514,115; 60/513,980; 60/514,131; 60/514,105; 60/514,280; 60/513,963; 60/514,145; 60/514,159; 60/514,083; 60/513,949; 60/514,144; 60/51,4481; 60/513,974; 60/514,108; 60/513,979; 60/514,084; 60/514,161; 60/514,304; 60/514,235; 60/514,325; 60/514,359; 60/514,113; 60/514,114; 60/514,112; 60/513,968; 60/514,345; 60/514,346; 60/513,564; 60/513,588; 60/514,298; 60/514,330; 60/513,932; 60/513,976; 60/513,562; and 60/514,258; all filed Oct. 24, 2003; and to U.S. Provisional Patent Application Ser. No. 60/519,476 filed Nov. 12, 2003; and to U.S. Provisional Patent Application Ser. No. 60/524,340; filed Nov. 20, 2003; and to U.S. Provisional Patent Application Ser. Nos. 60/532,230; 60/531,960; 60/532,160; and 60/531,940; all filed Dec. 22, 2003; and to U.S. Provisional Patent Application Ser. No. 60/532,591; filed Dec. 23; 2003; and to U.S. Provisional Patent Application Ser. Nos. 60/536,007; 60/536,006; 60/536,005; and 60/536,054; all filed Jan. 12; 2004. The entirety of all Provisional Applications listed above are incorporated herein by reference. This application also claims priority to U.S. Provisional Patent Application Ser. No. 60/465,641; filed Apr. 25, 2003.

FIELD OF THE INVENTION

The invention relates generally to compounds with anti-cancer activity.

BACKGROUND OF THE INVENTION

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the drug with its intracellular target, while minimizing intercellular redistribution of the drug, e.g., to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., glucocorticoids and other anti-inflammatory drugs) that can be administered. By comparison, although oral administration of drugs is generally recognized as a convenient and economical method of administration, oral administration can result in either (a) uptake of the drug through the cellular and tissue barriers, e.g., blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells.

Intracellular targeting may be achieved by methods and compositions which allow accumulation or retention of biologically active agents inside cells.

Many of the current treatment regimes for cell proliferation diseases such as psoriasis and cancer utilize compounds which inhibit DNA synthesis. Such compounds are toxic to cells generally but their toxic effect on rapidly dividing cells such as tumor cells can be beneficial. Alternative approaches to anti-proliferative agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumor cells (Bradshaw, Mutagenesis 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., Ann. Rev. Biochem., 1988, 57, 443; Larsen et al. Ann. Reports in Med. Chem. 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, Advances in Cancer Research, 1993, 60, 43-73) based on families of growth factors which bind to different receptor tyrosine kinases. The classification includes Class I receptor tyrosine kinases comprising the EGF family of receptor tyrosine kinases such as the EGF, TGF.alpha., NEU, erbB, Xmrk, HER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGF.alpha., PDGF.beta. and colony-stimulating factor 1 (CSF1) receptors. It is known that Class I kinases such as the EGF family of receptor tyrosine kinases are frequently present in common human cancers such as breast cancer (Sainsbury et. al., Brit. J. Cancer, 1988, 58, 458; Guerin et al., Oncogene Res., 1988, 3, 21 and Klijn et al., Breast Cancer Res. Treat., 1994, 29, 73), non-small cell lung cancers (NSCLCs) including adenocarcinomas (Cerny et al., Brit. J. Cancer, 1986, 54, 265; Reubi et al., Int. J. Cancer, 1990, 45, 269; and Rusch et al., Cancer Research, 1993, 53, 2379) and squamous cell cancer of the lung (Hendler et al., Cancer Cells, 1989, 7, 347), bladder cancer (Neal et. al., Lancet, 1985, 366), oesophageal cancer (Mukaida et al., Cancer, 1991, 68, 142), gastrointestinal cancer such as colon, rectal or stomach cancer (Bolen et al., Oncogene Res., 1987, 1, 149), cancer of the prostate (Visakorpi et al., Histochem. J., 1992, 24, 481), leukaemia (Konaka et al., Cell, 1984, 37, 1035) and ovarian, bronchial or pancreatic cancer (European Patent Specification No. 0400586). As further human tumor tissues are tested for the EGF family of receptor tyrosine kinases it is expected that their widespread prevalence will be established in further cancers such as thyroid and uterine cancer. It is also known that EGF type tyrosine kinase activity is rarely detected in normal cells whereas it is more frequently detectable in malignant cells (Hunter, Cell, 1987, 50, 823). It has been shown more recently (W. J. Gullick, Brit. Med. Bull., 1991, 47, 87) that EGF receptors which possess tyrosine kinase activity are overexpressed in many human cancers such as brain, lung squamous cell, bladder, gastric, breast, head and neck, oesophageal, gynaecological and thyroid tumors.

Accordingly it has been recognized that an inhibitor of receptor tyrosine kinases should be of value as a selective inhibitor of the growth of mammalian cancer cells (Yaish et al. Science, 1988, 242, 933). Support for this view is provided by the demonstration that erbstatin, an EGF receptor tyrosine kinase inhibitor, specifically attenuates the growth in athymic nude mice of a transplanted human mammary carcinoma which expresses EGF receptor tyrosine kinase but is without effect on the growth of another carcinoma which does not express EGF receptor tyrosine kinase (Toi et al., Eur. J. Cancer Clin. Oncol., 1990, 26, 722.). Various derivatives of styrene are also stated to possess tyrosine kinase inhibitory properties (European Patent Application Nos. 0211363, 0304493 and 0322738) and to be of use as anti-tumor agents. The in vivo inhibitory effect of two such styrene derivatives which are EGF receptor tyrosine kinase inhibitors has been demonstrated against the growth of human squamous cell carcinoma inoculated into nude mice (Yoneda et al., Cancer Research, 1991, 51, 4430). Various known tyrosine kinase inhibitors are disclosed in a more recent review by T. R. Burke Jr. (Drugs of the Future, 1992, 17, 119).

Cancer is a major health problem worldwide. Although drugs targeting tumors and cancerous cells are in wide use and have shown effectiveness, toxicity and side-effects have limited their usefullness.

Assay methods capable of determining the presence, absence or amounts of cancer are of practical utility in the search for anti-cancer compounds as well as for diagnosing the presence of cancer.

Inhibitors of tumor growth are useful to limit the establishment and progression of cancer, as well as in diagnostic assays for cancer.

There is a need for anti-cancer therapeutic agents, i.e. drugs, having improved anti-cancer, as well as pharmacokinetic properties, including enhanced activity against development of cancer, improved oral bioavailability, greater potency and extended effective half-life in vivo. Such anti-cancer compounds should be active against various cancers, have distinct resistance profiles, fewer side effects, less complicated dosing schedules, and orally active. In particular, there is a need for a less onerous dosage regimen, such as one pill, once per day.

SUMMARY OF THE INVENTION

Intracellular targeting may be achieved by methods and compositions that allow accumulation or retention of biologically active agents inside cells. The present invention provides novel analogs of anti-cancer compounds. Such novel anti-cancer compound analogs possess all the utilities of anti-cancer compounds and optionally provide cellular accumulation as set forth below. In addition, the present invention provides compositions and methods for treating cancer or therapeutic activity against cancer.

The present invention relates generally to the accumulation or retention of therapeutic compounds inside cells. The invention is more particularly related to attaining high concentrations of phosphonate-containing molecules in cancer cells. Such effective targeting may be applicable to a variety of therapeutic formulations and procedures.

Accordingly, in one embodiment the invention provides a compound of the invention which is a conjugate comprising a chemotherapeutic agent linked to one or more phosphonate groups.

In another embodiment, the invention provides a compound of any one of formulae 500-601:

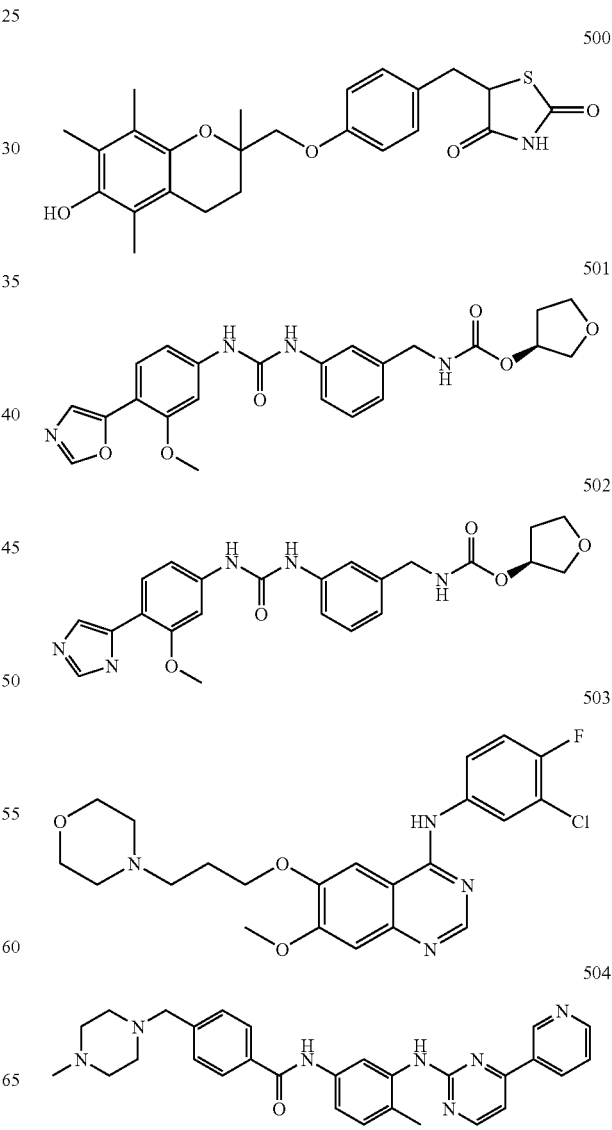

505
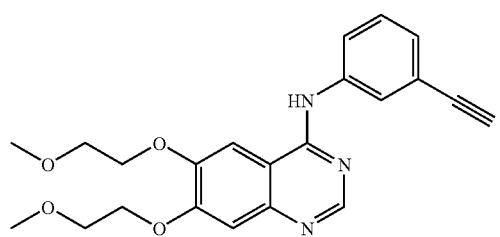
506
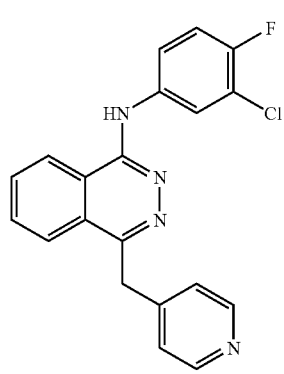
507
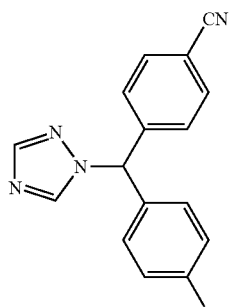
508
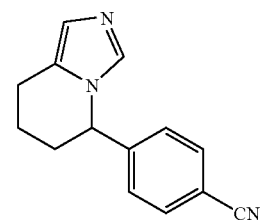
509
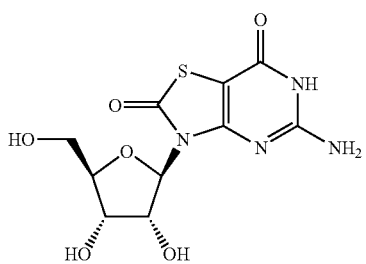
510
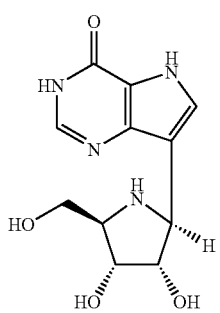
511
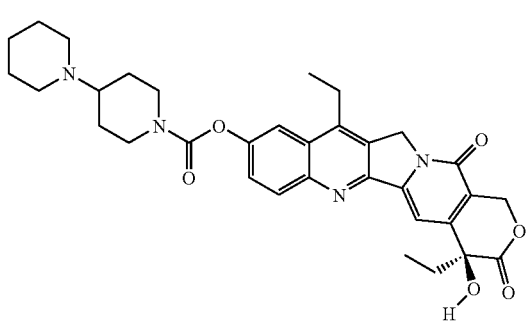
512
513
514

515
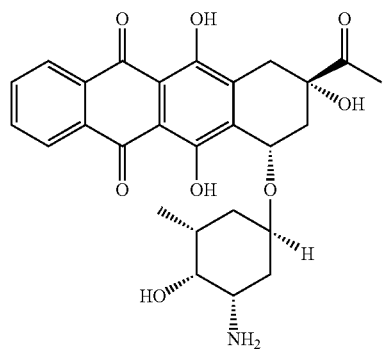
516
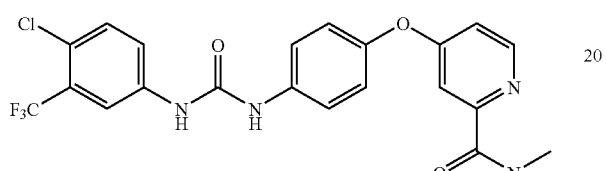
517
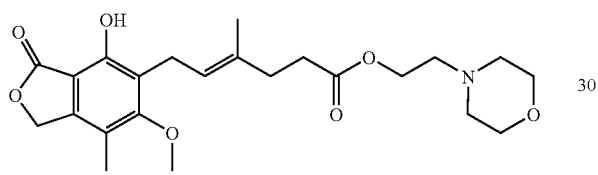
518
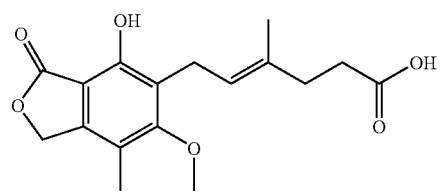
519
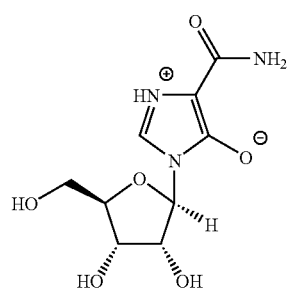
520
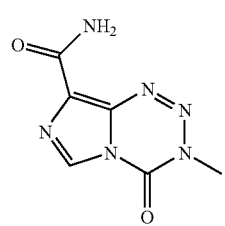
521
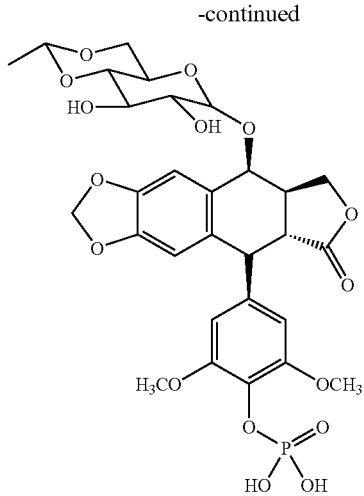
522
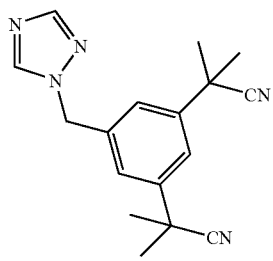
523
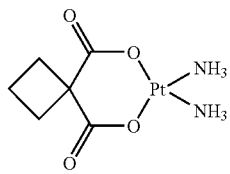
524
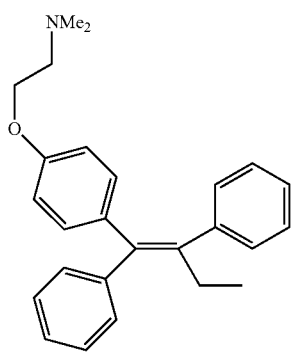

-continued
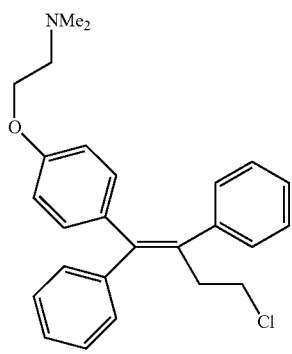
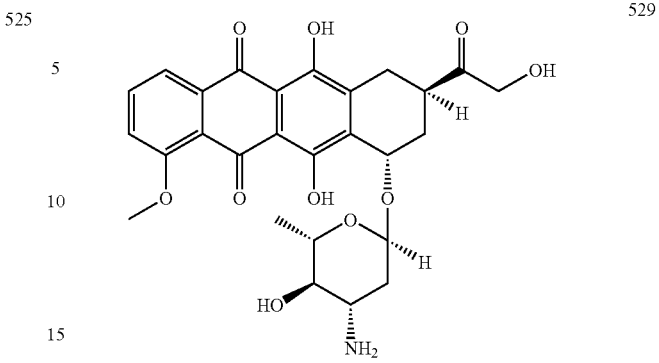
525
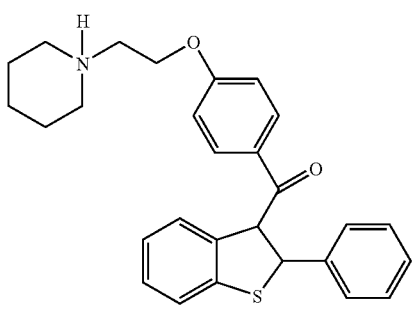
526
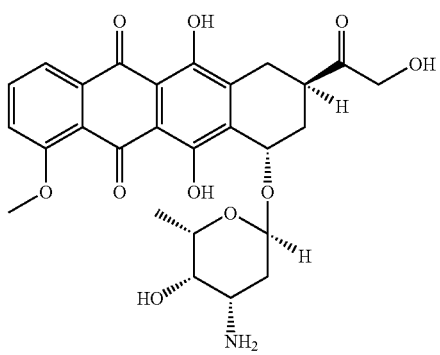
529
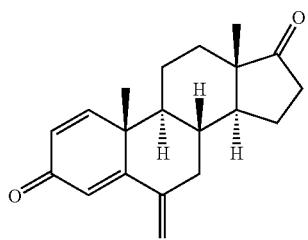
527
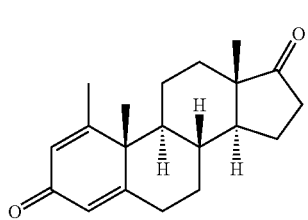
528
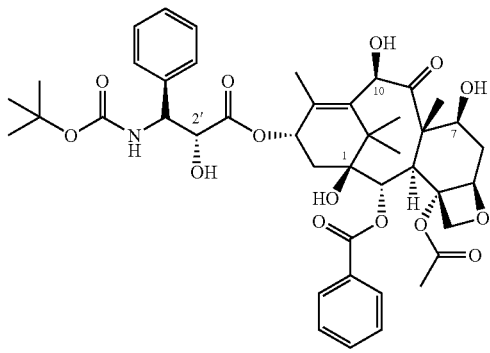
530
531

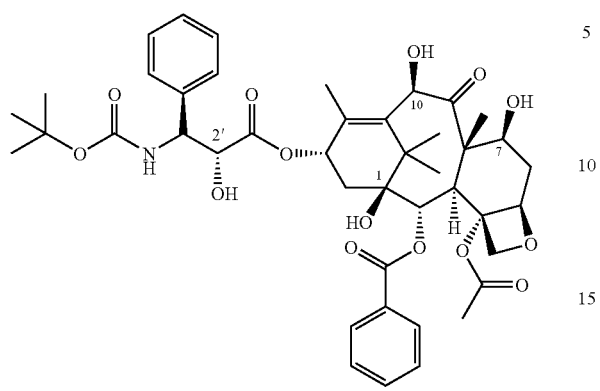
532
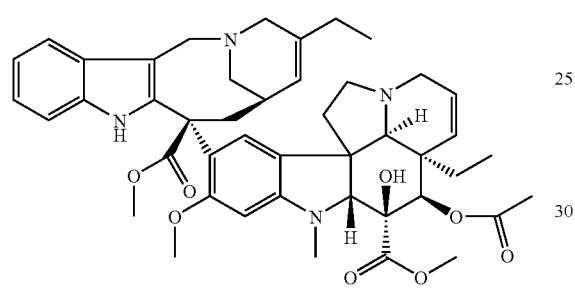
533
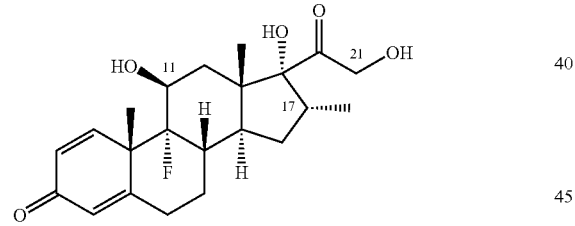
534
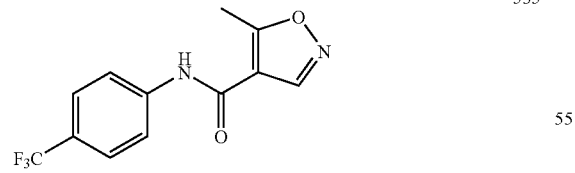
535
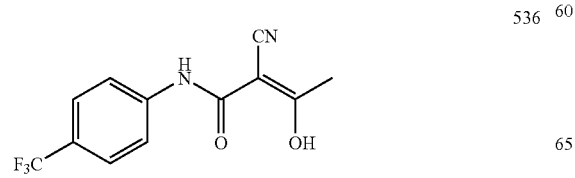
536
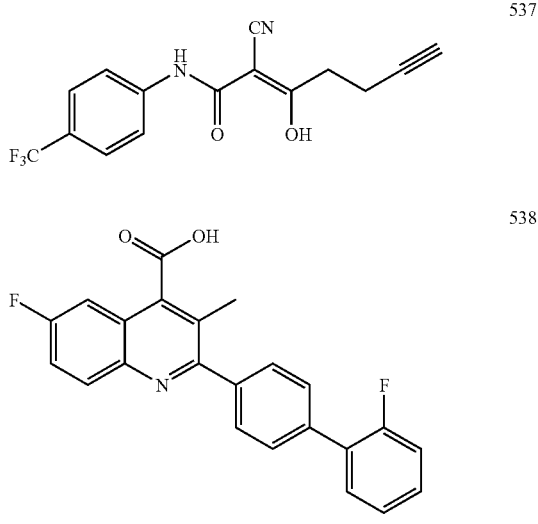
537
538
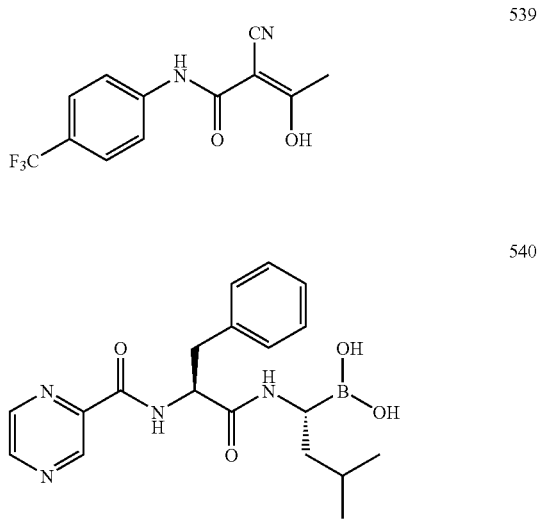
539
540
541
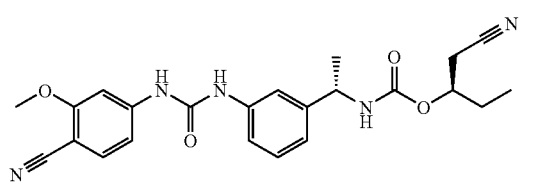
542

-continued
543
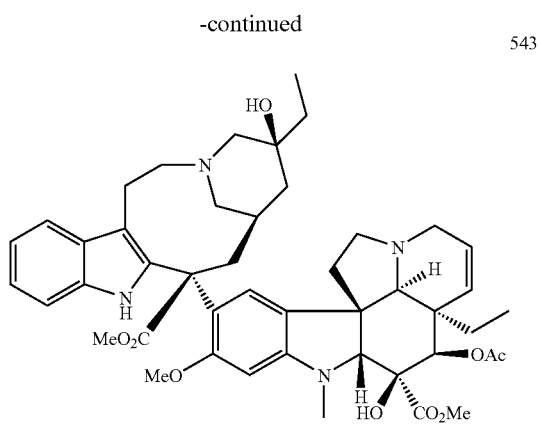
544
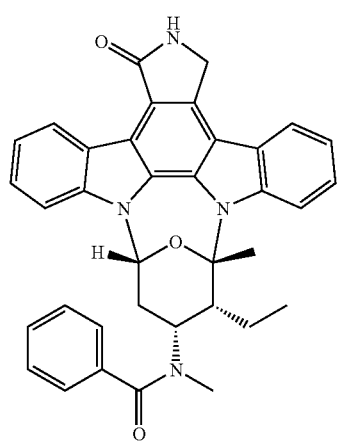
545
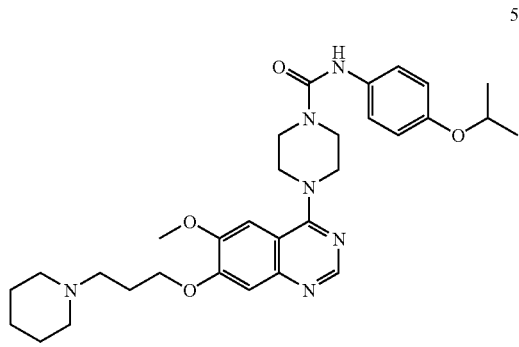
546
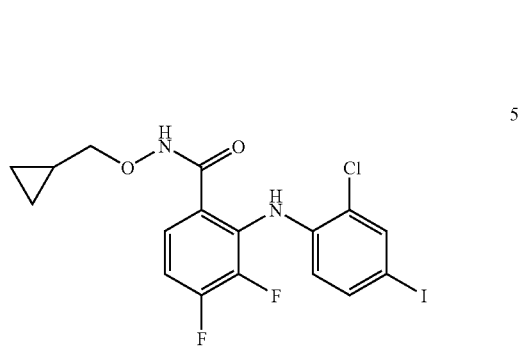
-continued
547
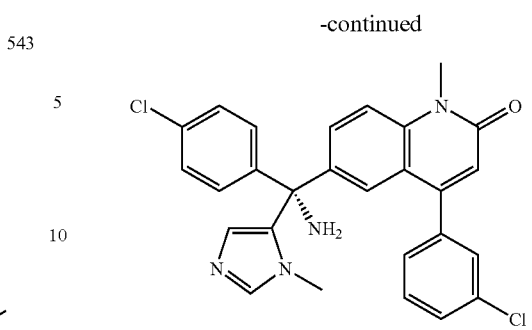
548
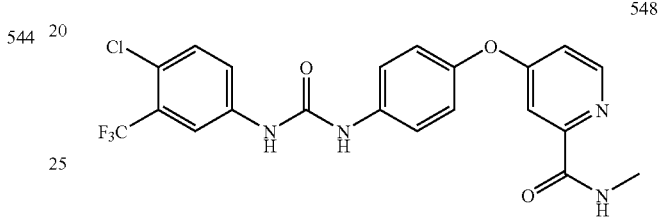
549
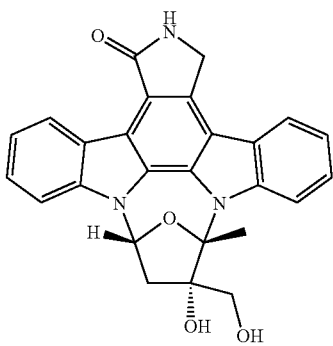
550
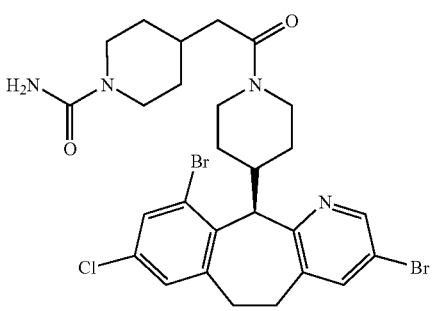

-continued
551 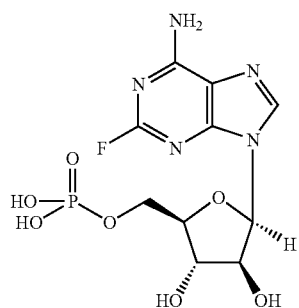
552 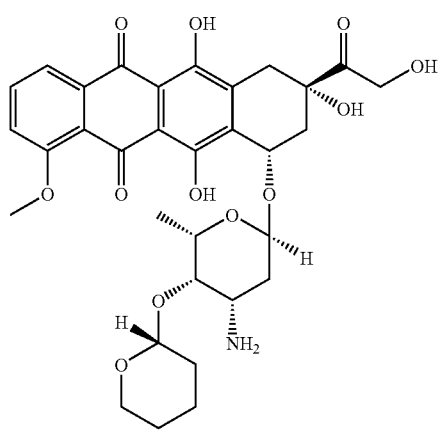
553 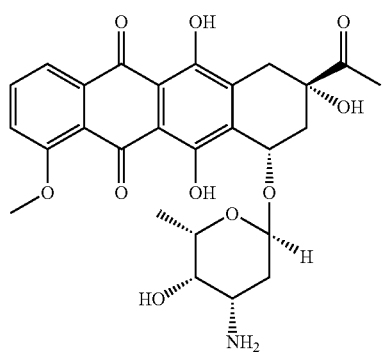
554 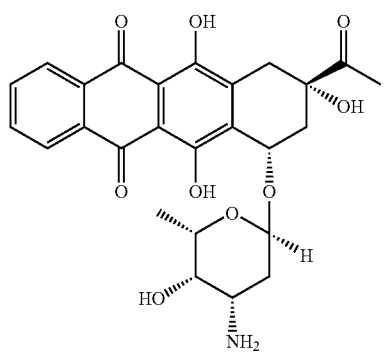
-continued
555 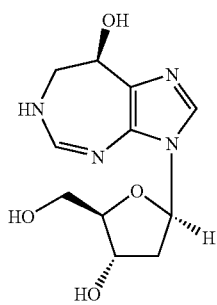
556 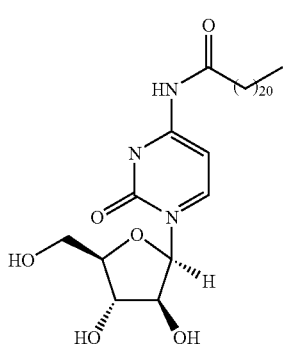
557 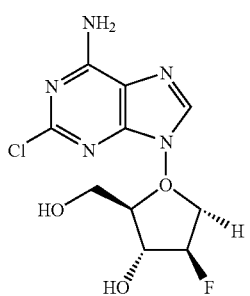
558 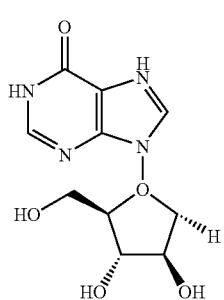

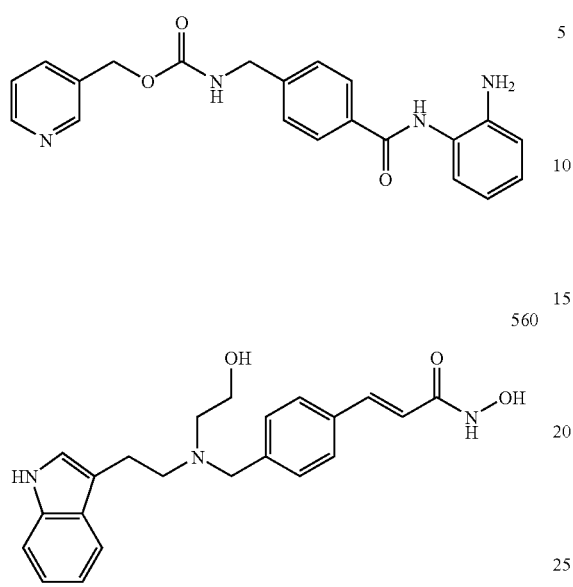
559
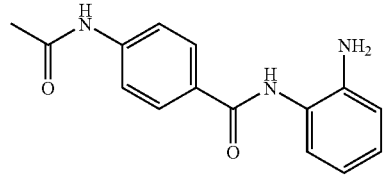
560
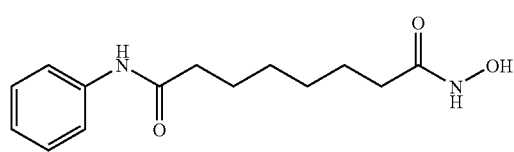
561
562
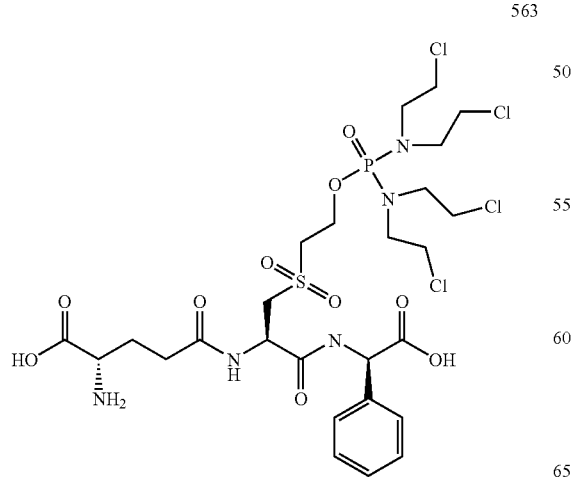
563
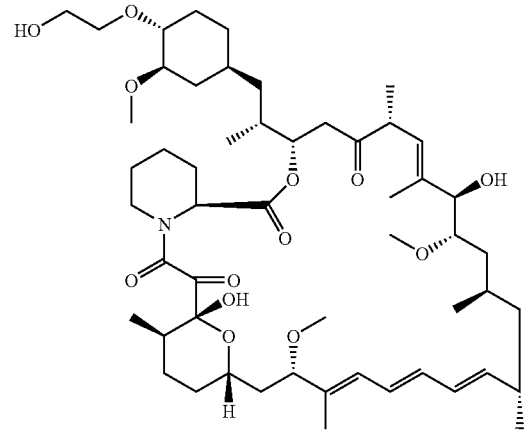
564
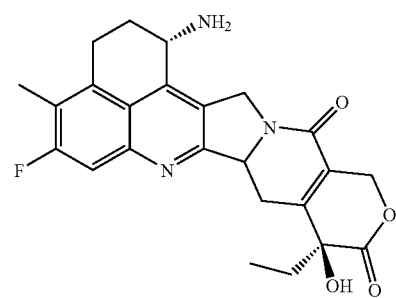
565
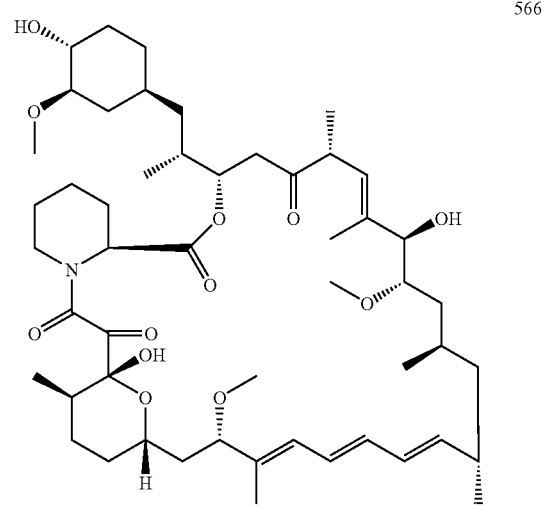
566

567
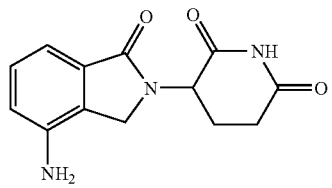
568
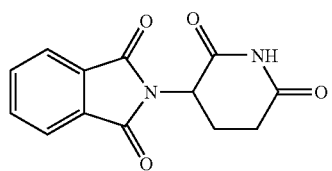
569
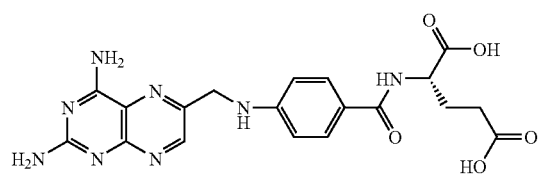
570
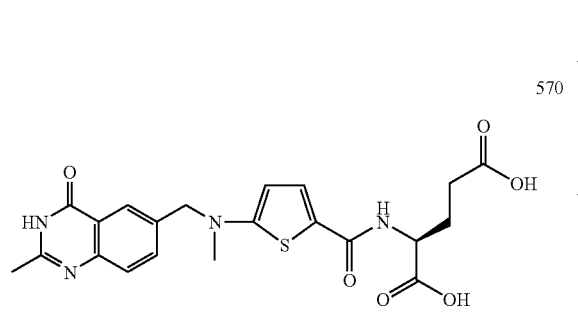
571
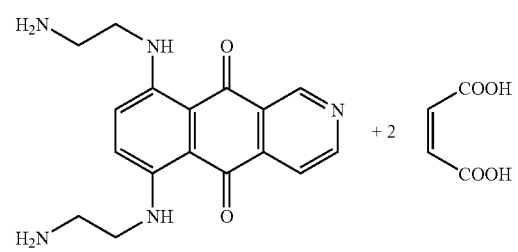
572
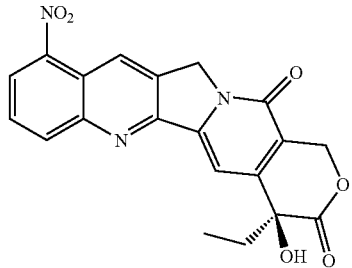
573
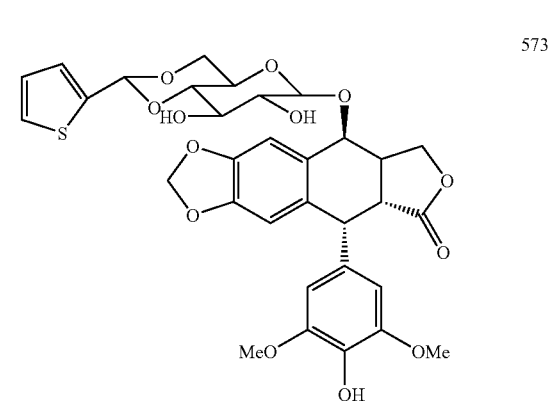
574
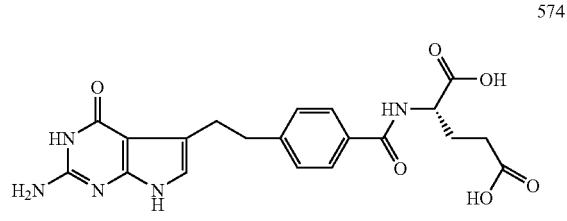
575
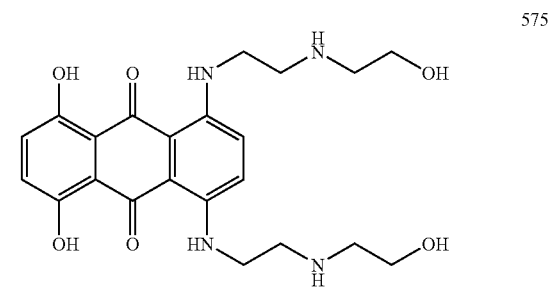
576
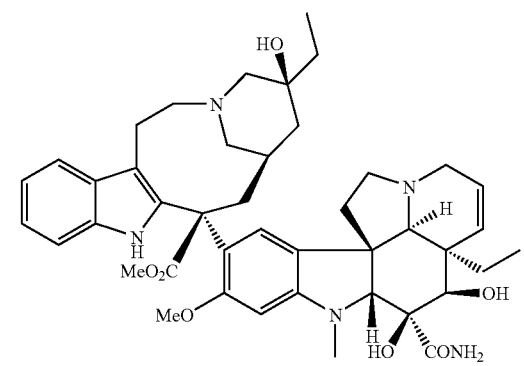

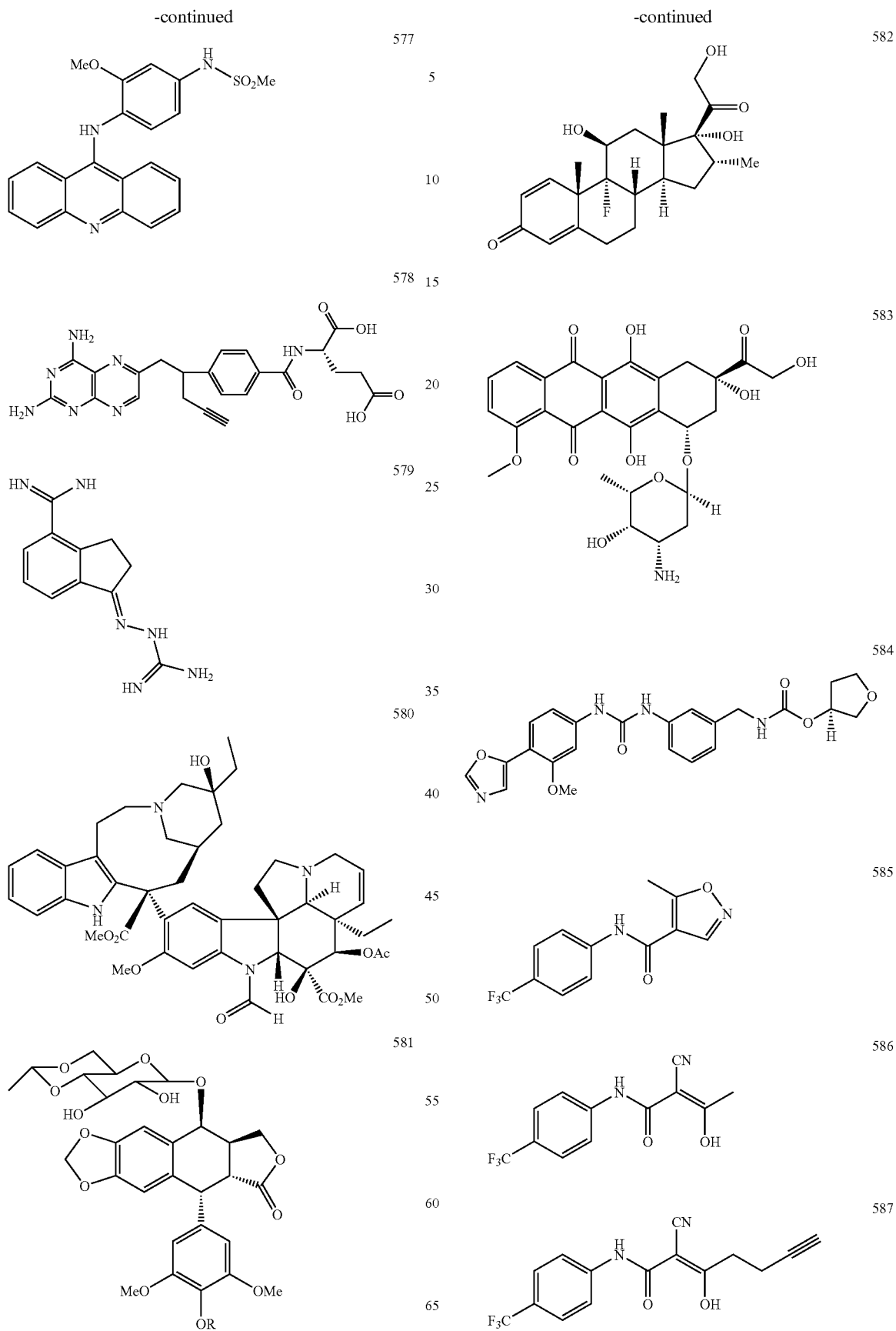

588
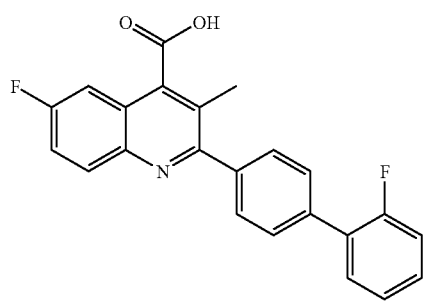
589
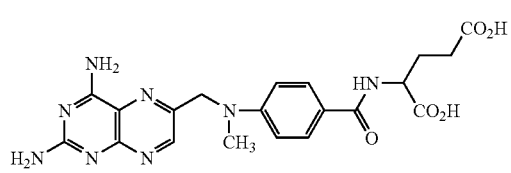
590
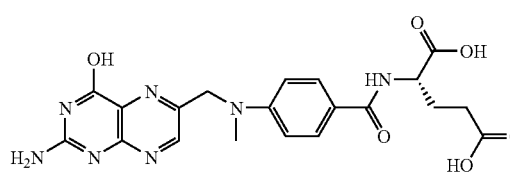
591
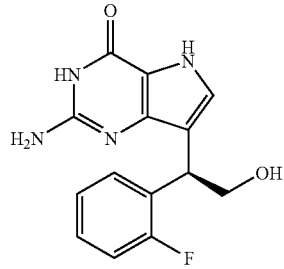
592
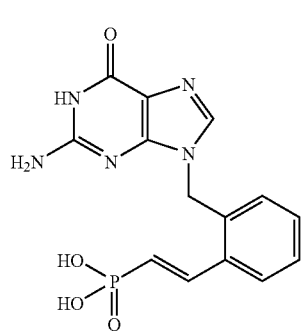
593
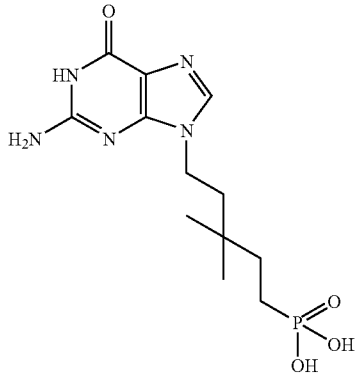
594
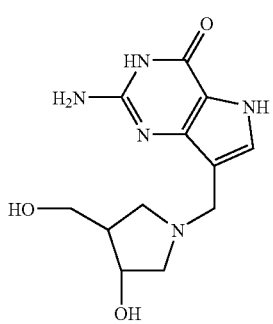
595
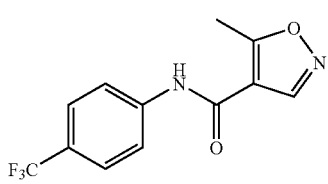
596
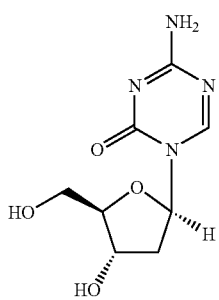

-continued

597
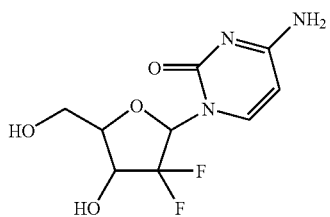

598
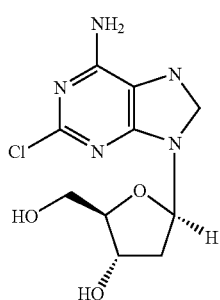

599
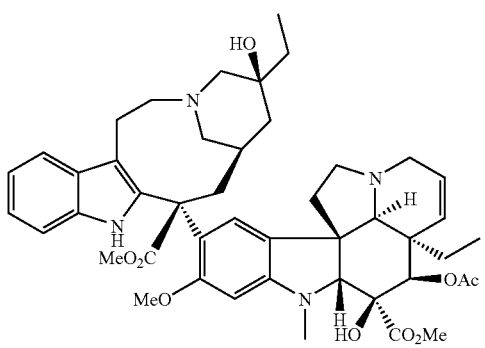

600
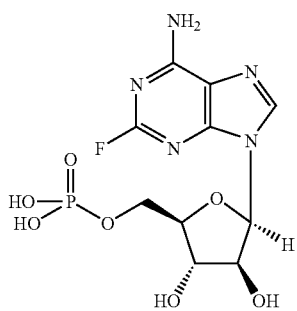

601
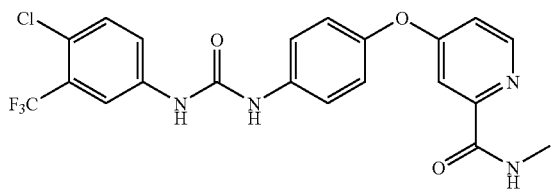

that is substituted with one or more groups $A^o$, wherein:
$A^o$ is $A^1$, $A^2$ or $W^3$ with the proviso that the conjugate includes at least one $A^1$;

$A^1$ is:

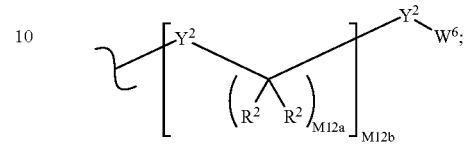

$A^2$ is:


$A^3$ is:

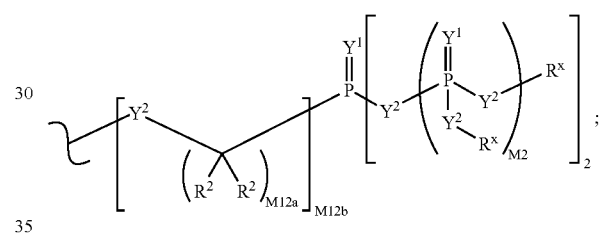

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$; and when $Y^2$ joins two phosphorous atoms $Y^2$ can also be $C(R^2)(R^2)$;

$R^x$ is independently H, $R^1$, $R^2$, $W^3$, a protecting group, or the formula:

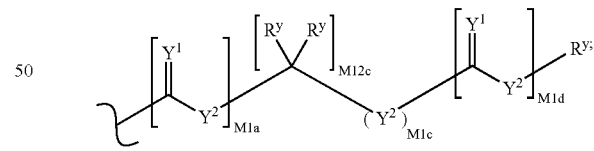

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, $-CN$, $N_3$ or $-NO_2$;
$R^{3b}$ is $Y^1$;
$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, —OC(Y$^1$)(N(R$^x$)(R$^x$)), —SC(Y$^1$)R$^x$, —SC(Y$^1$)OR$^x$, —SC(Y$^1$)(N(R$^x$)(R$^x$)), —N(R$^x$)C(Y$^1$)R$^x$, —N(R$^x$)C(Y$^1$)OR$^x$, or —N(R$^x$)C(Y$^1$)(N(R$^x$)(R$^x$));

R$^{3d}$ is —C(Y$^1$)R$^x$, —C(Y$^1$)OR$^x$ or —C(Y$^1$)(N(R$^x$)(R$^x$));

R$^4$ is an alkyl of 1 to 18 carbon atoms, alkenyl of 2 to 18 carbon atoms, or alkynyl of 2 to 18 carbon atoms;

R$^5$ is R$^4$ wherein each R$^4$ is substituted with 0 to 3 R$^3$ groups;

W$^3$ is W$^4$ or W$^5$;

W$^4$ is R$^5$, —C(Y$^1$)R$^5$, —C(Y$^1$)W$^5$, —SO$_{M2}$R$^5$, or —SO$_{M2}$W$^5$;

W$^5$ is carbocycle or heterocycle wherein W$^5$ is independently substituted with 0 to 3 R$^2$ groups;

W$^6$ is W$^3$ independently substituted with 1, 2, or 3 A$^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12

In another embodiment, the invention provides a compound of the formula:

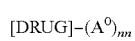

or a pharmaceutically acceptable salt or solvate thereof wherein,

DRUG is a compound of any one of formulae 500-601;

nn is 1, 2, or 3;

A$^0$ is A$^1$, A$^2$ or W$^3$ with the proviso that the conjugate includes at least one A$^1$;

A$^1$ is:

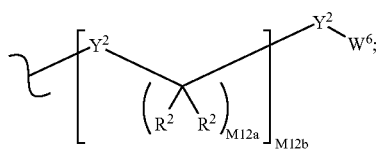

A$^2$ is:

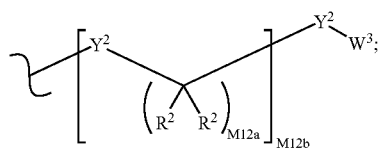

A$^3$ is:

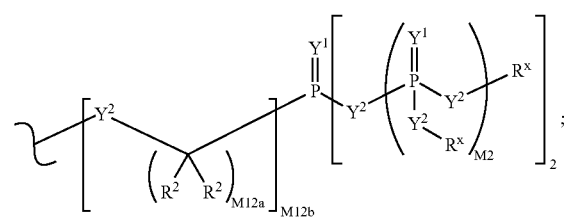

Y$^1$ is independently O, S, N(R$^x$), N(O)(R$^x$), N(OR$^x$), N(O)(OR$^x$), or N(N(R$^x$)(R$^x$));

Y$^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—; and when Y$^2$ joins two phosphorous atoms Y$^2$ can also be C(R$^2$)(R$^2$);

R$^x$ is independently H, R$^1$, R$^2$, W$^3$, a protecting group, or the formula:

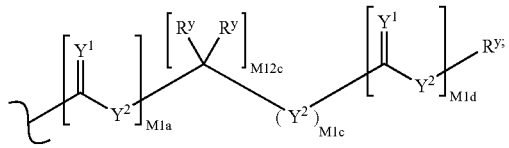

wherein:

R$^y$ is independently H, W$^3$, R$^2$ or a protecting group;

R$^1$ is independently H or alkyl of 1 to 18 carbon atoms;

R$^2$ is independently H, R$^1$, R$^3$ or R$^4$ wherein each R$^4$ is independently substituted with 0 to 3 R$^3$ groups or taken together at a carbon atom, two R$^2$ groups form a ring of 3 to 8 carbons and the ring may be substituted with 0 to 3 R$^3$ groups;

R$^3$ is R$^{3a}$, R$^{3b}$, R$^{3c}$ or R$^{3d}$, provided that when R$^3$ is bound to a heteroatom, then R$^3$ is R$^{3c}$ or R$^{3d}$;

R$^{3a}$ is F, Cl, Br, I, —CN, N$_3$ or —NO$_2$;

R$^{3b}$ is Y$^1$;

R$^{3c}$ is —R$^x$, —N(R$^x$)(R$^x$), —SR$^x$, —S(O)R$^x$, —S(O)$_2$R$^x$, —S(O)(OR$^x$), —S(O)$_2$(OR$^x$), —OC(Y$^1$)R$^x$, —OC(Y$^1$)OR$^x$, —OC(Y$^1$)(N(R$^x$)(R$^x$)), —SC(Y$^1$)R$^x$, —SC(Y$^1$)OR$^x$, —SC(Y$^1$)(N(R$^x$)(R$^x$)), —N(R$^x$)C(Y$^1$)R$^x$, —N(R$^x$)C(Y$^1$)OR$^x$, or —N(R$^x$)C(Y$^1$)(N(R$^x$)(R$^x$));

R$^{3d}$ is —C(Y$^1$)R$^x$, —C(Y$^1$)OR$^x$ or —C(Y$^1$)(N(R$^x$)(R$^x$));

R$^4$ is an alkyl of 1 to 18 carbon atoms, alkenyl of 2 to 18 carbon atoms, or alkynyl of 2 to 18 carbon atoms;

R$^5$ is R$^4$ wherein each R$^4$ is substituted with 0 to 3 R$^3$ groups;

W$^3$ is W$^4$ or W$^5$;

W$^4$ is R$^5$, —C(Y$^1$)R$^5$, —C(Y$^1$)W$^5$, —SO$_{M2}$R$^5$, or —SO$_{M2}$W$^5$;

W$^5$ is carbocycle or heterocycle wherein W$^5$ is independently substituted with 0 to 3 R$^2$ groups;

W$^6$ is W$^3$ independently substituted with 1, 2, or 3 A$^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another embodiment, the invention provides a compound of any one of formulae 1-336:

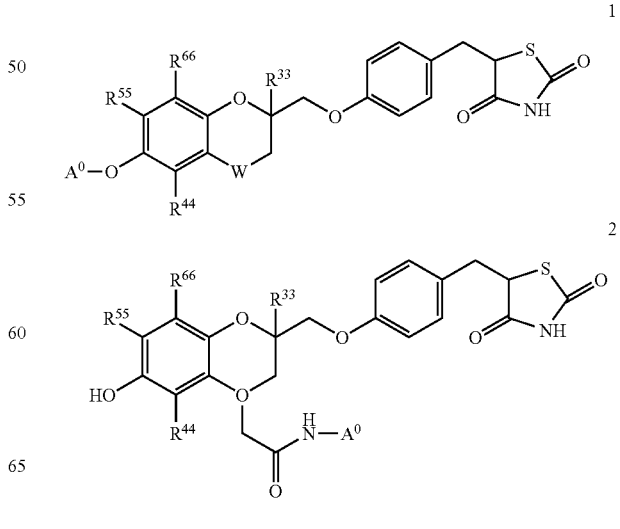

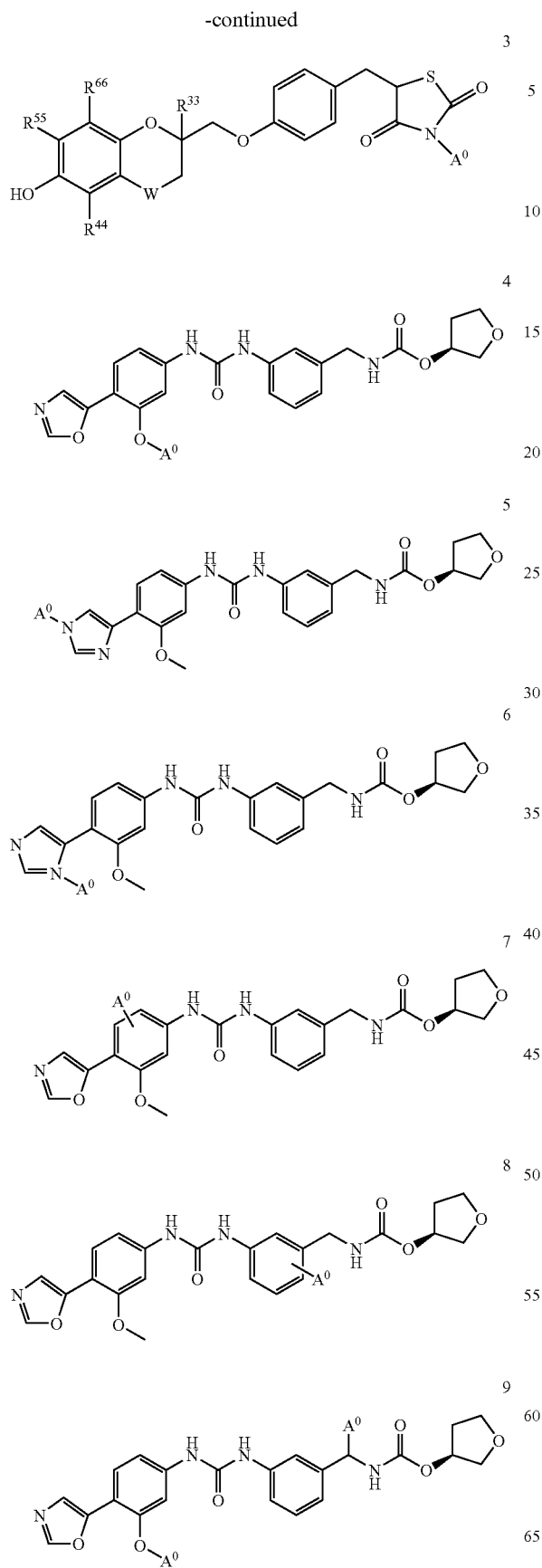

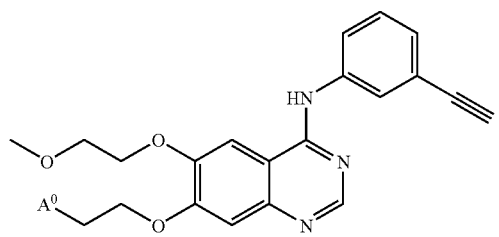
16
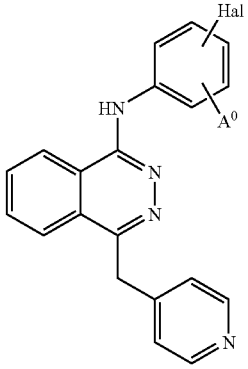
21
17
18
19
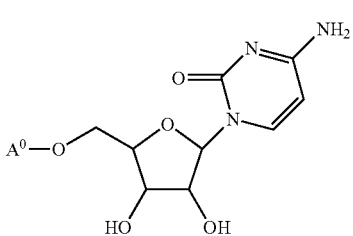
22
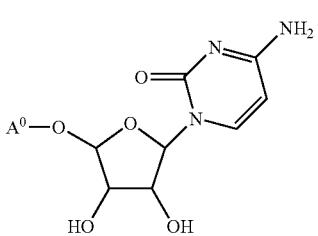
23
20
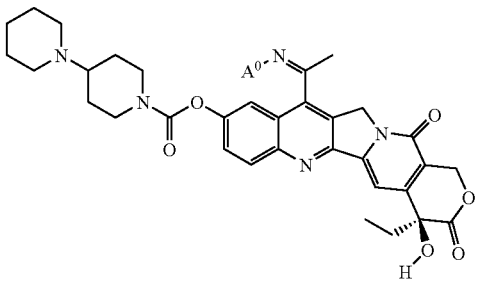
24

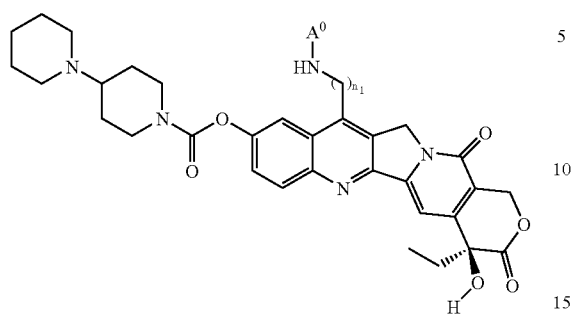
25
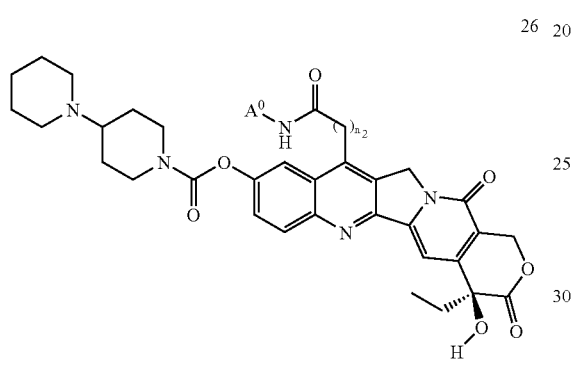
26
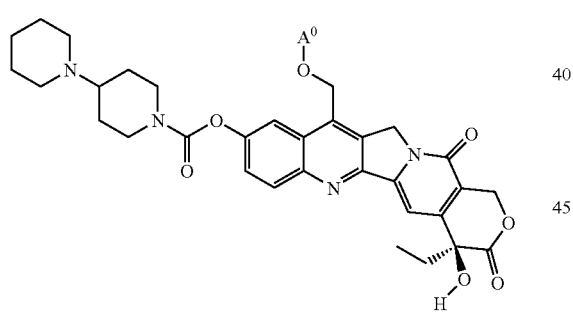
27
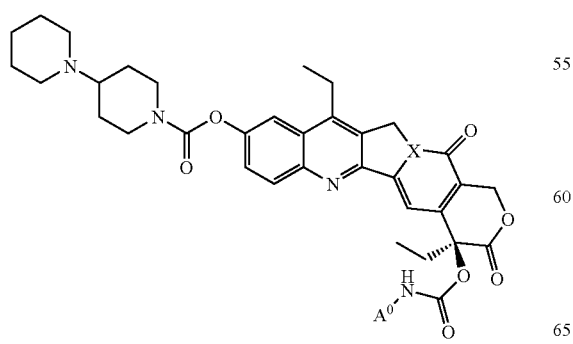
28
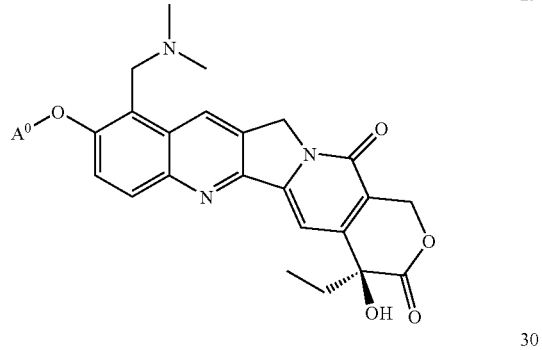
29
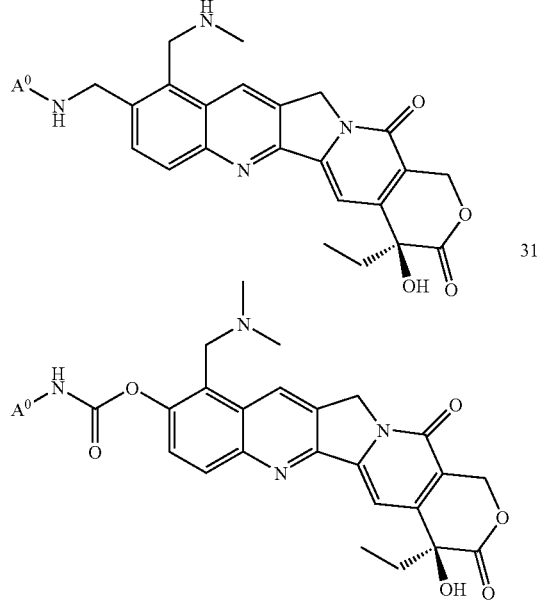
30
31
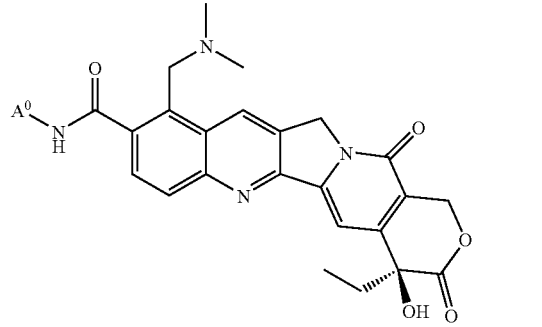
32
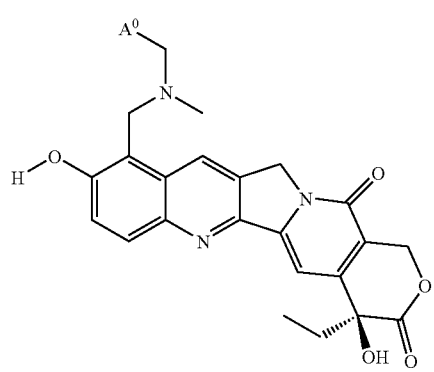
33

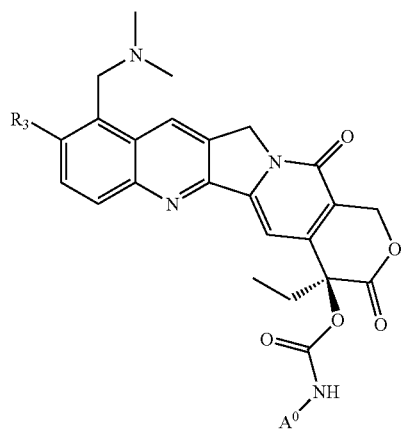
34
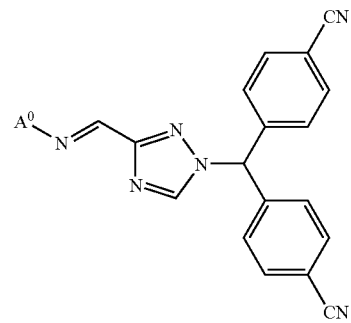
38
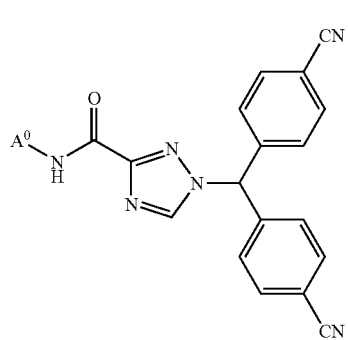
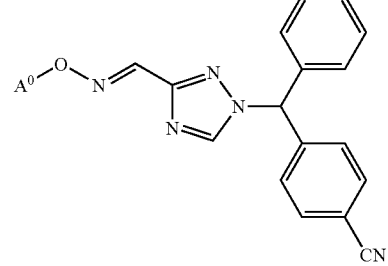
39
35
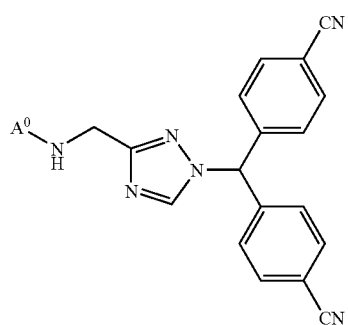
36
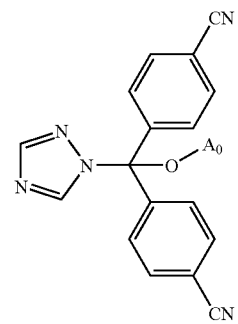
40
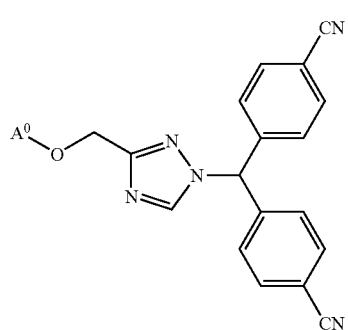
37
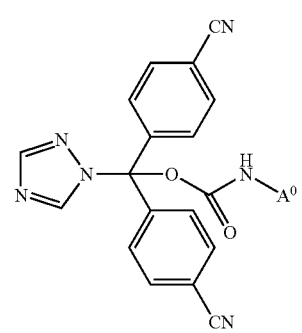
41

42
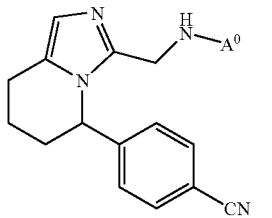
43
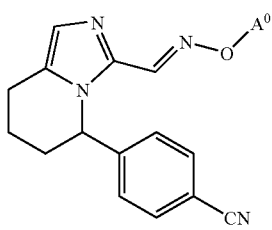
44
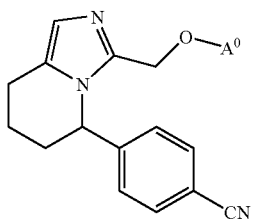
45
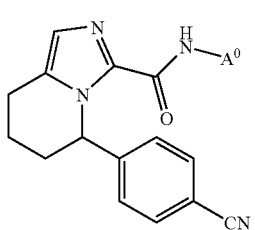
46
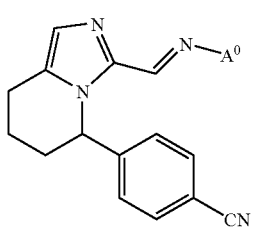
47
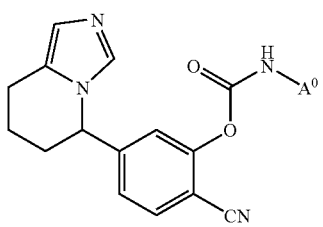
48
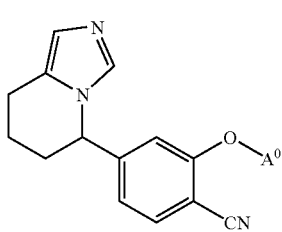
49
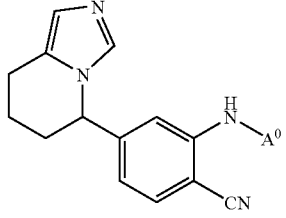
50
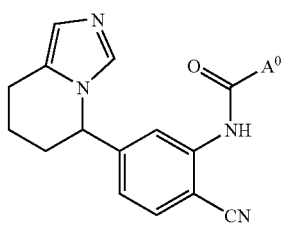
51
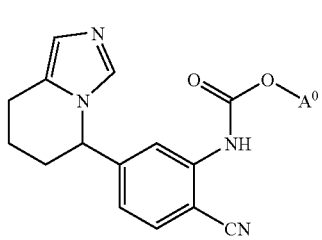
52
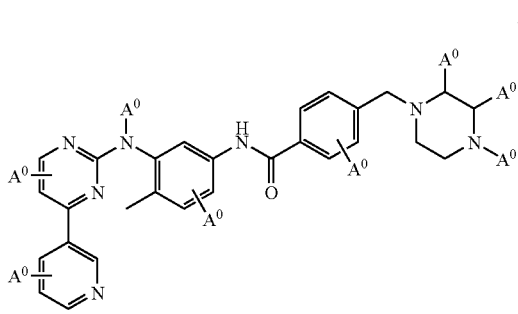
53
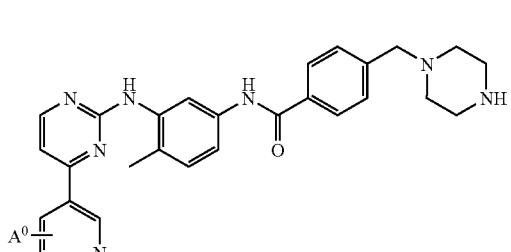
54
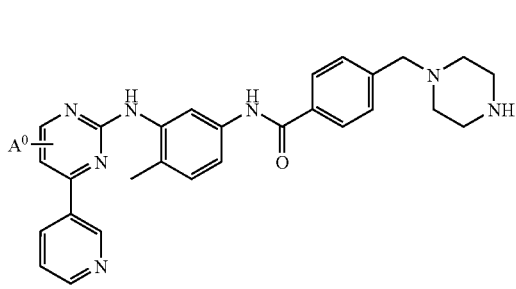

55
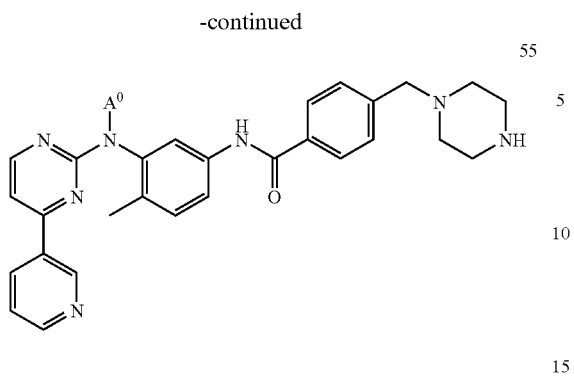
56
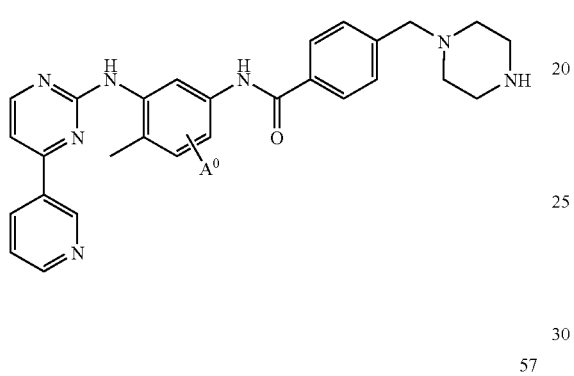
57
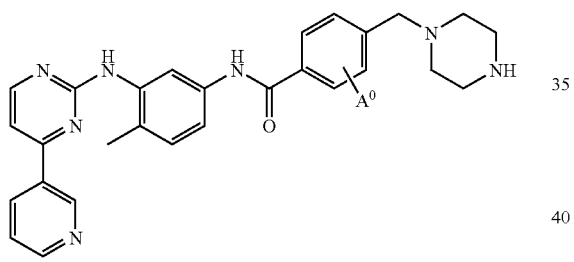
58
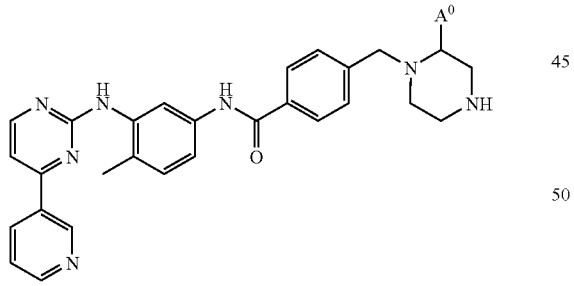
59
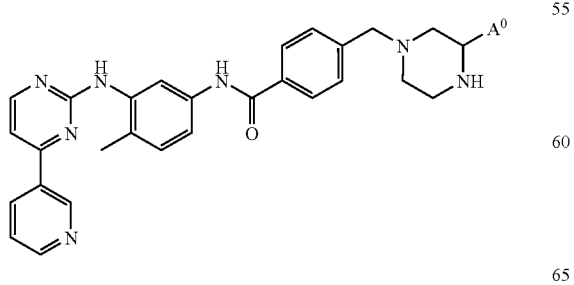
60
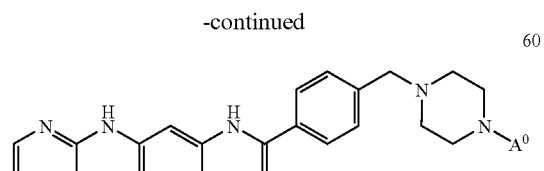
61
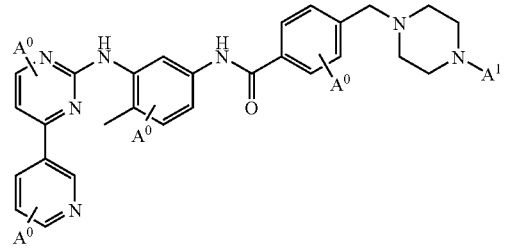
62
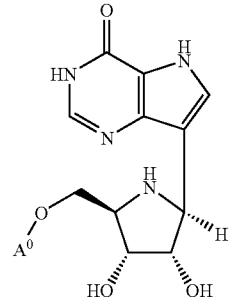
63
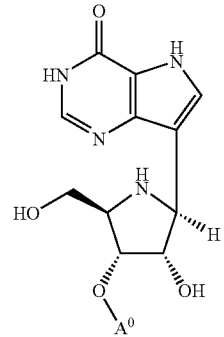

64
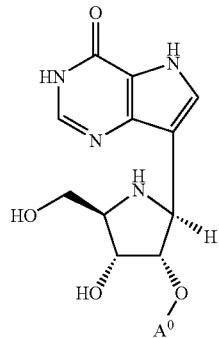
65
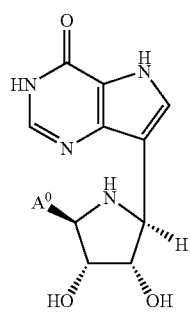
66
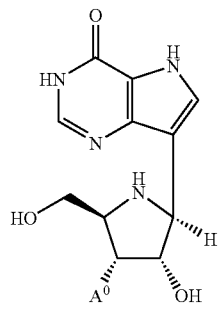
67
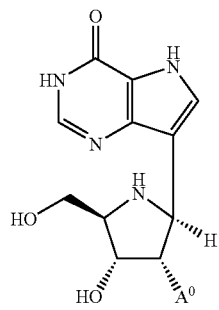
68
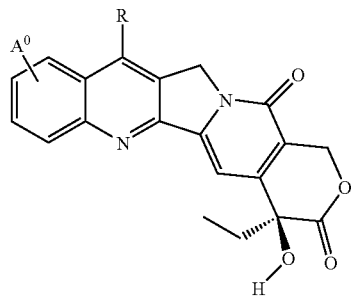
69
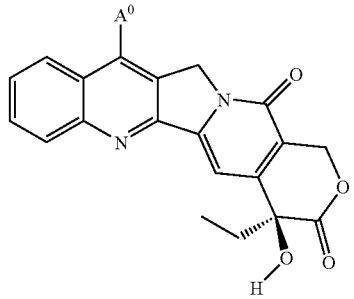
70
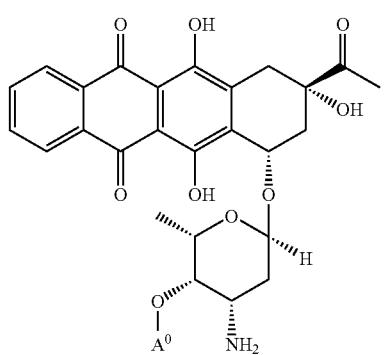
71
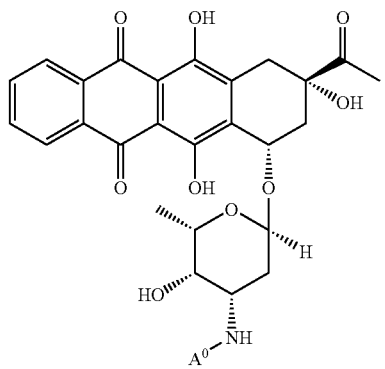
72
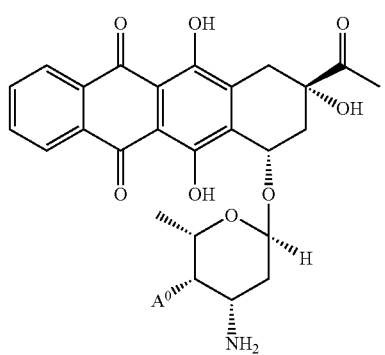

-continued
73
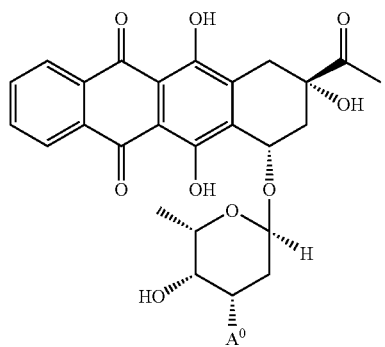
74
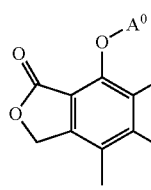
75
76
77
78
79
-continued
80
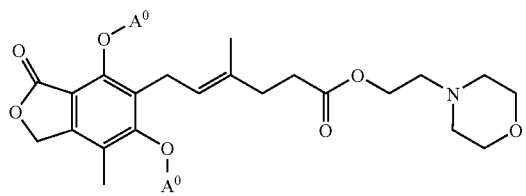
81
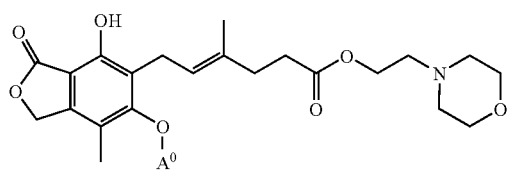
82
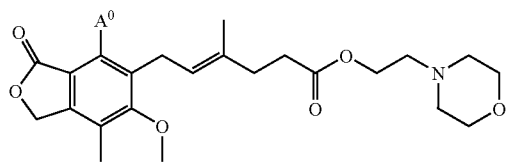
83
84
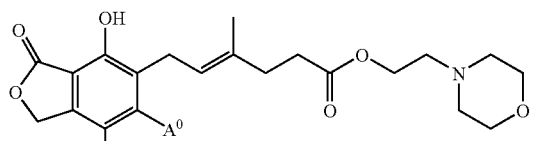
85
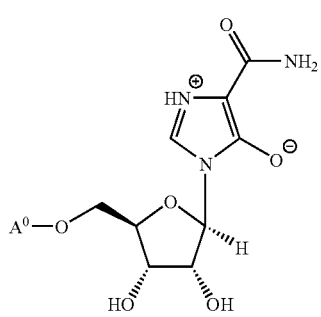

-continued
86 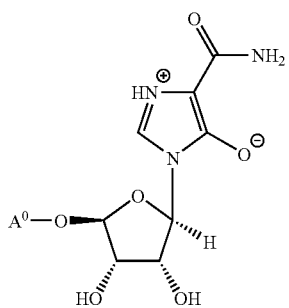
87 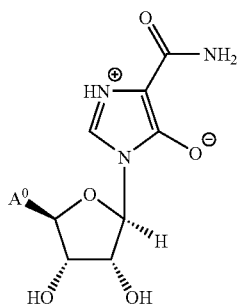
88 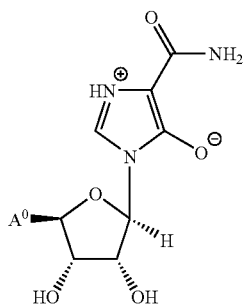
89 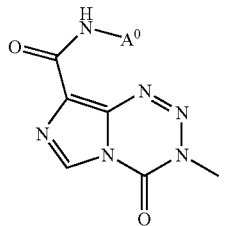
90 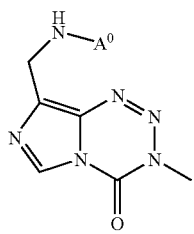
91 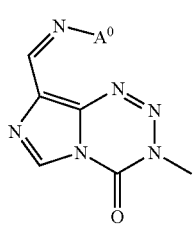
-continued
92 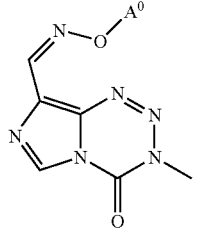
93 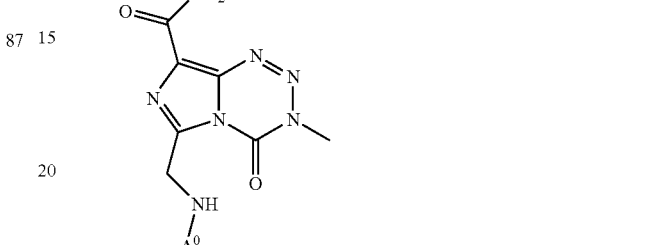
94 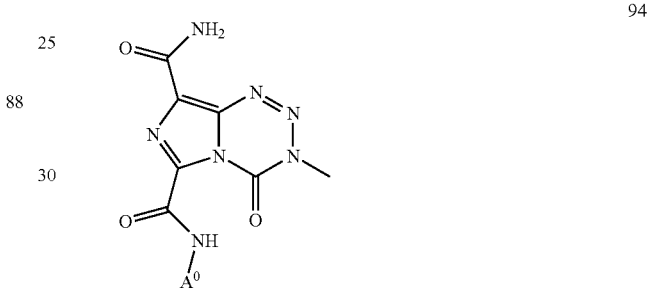
95 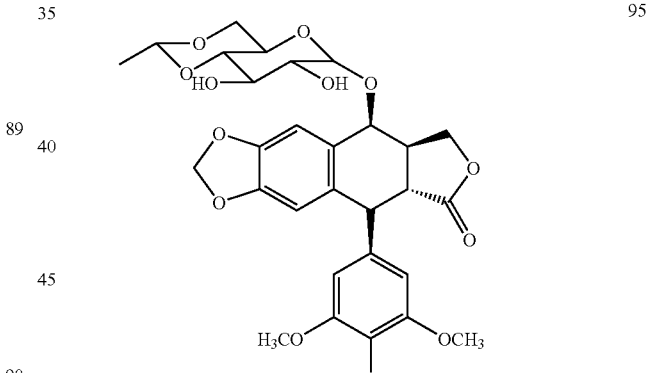
96 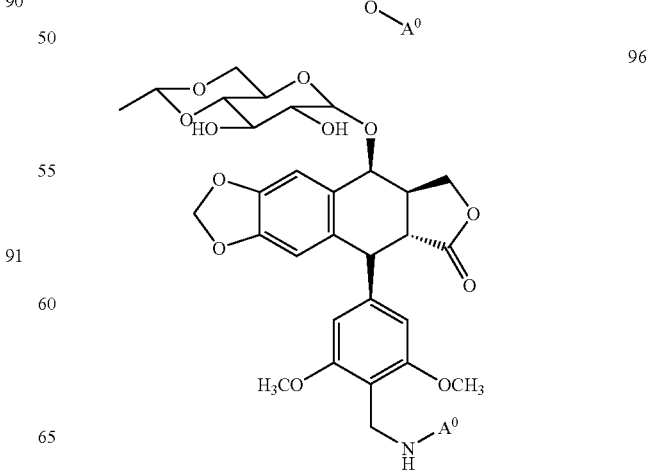

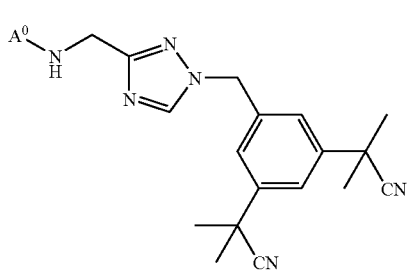
103
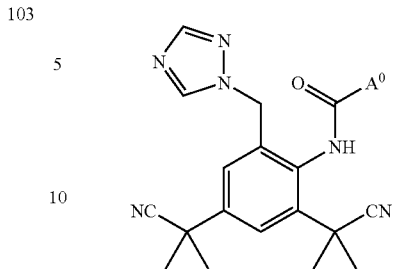
108
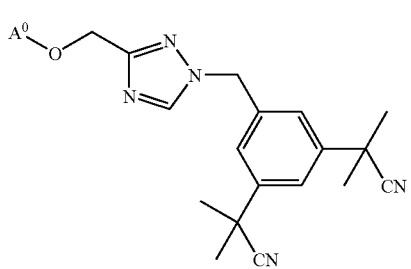
104
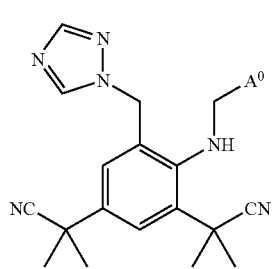
109
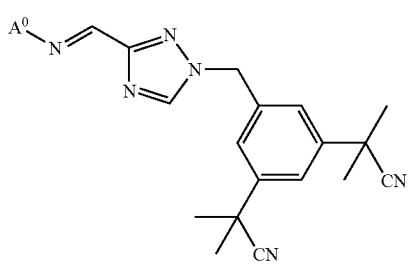
105
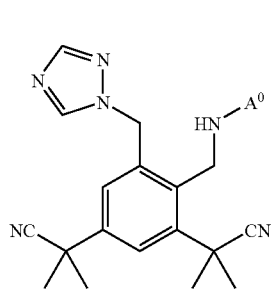
110
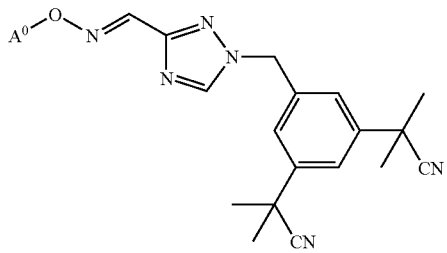
106
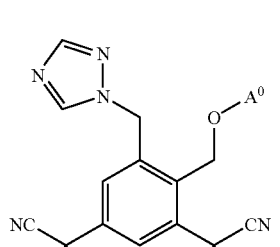
111
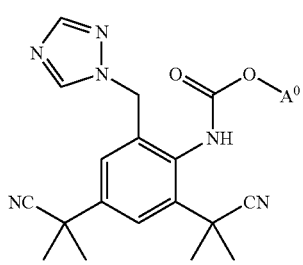
107
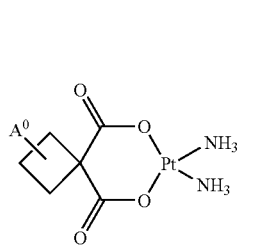
112

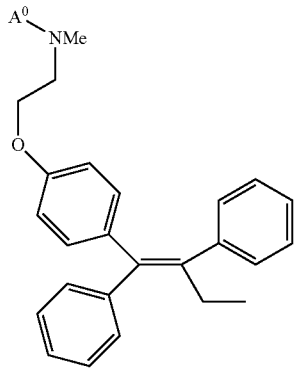
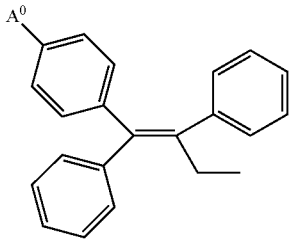
113
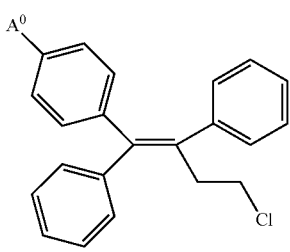
114

115
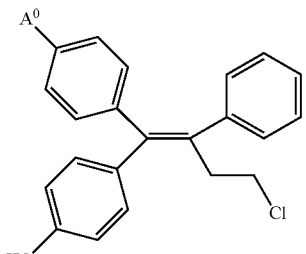
116
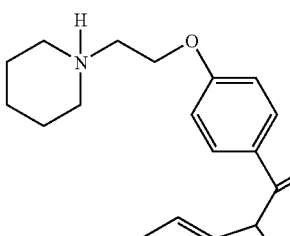
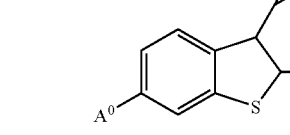
121

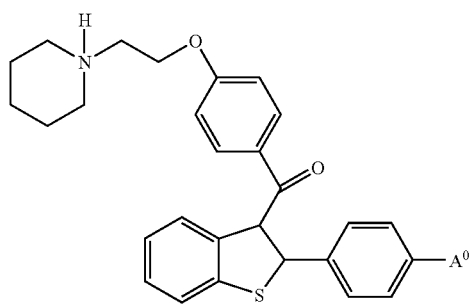
122
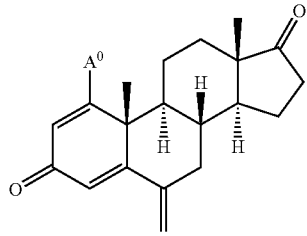
126
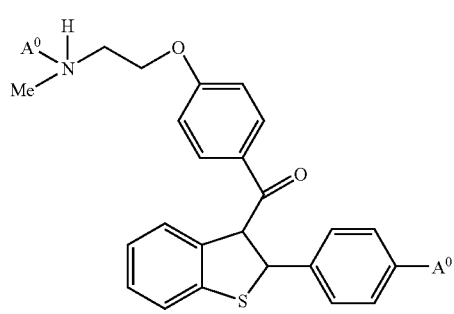
123
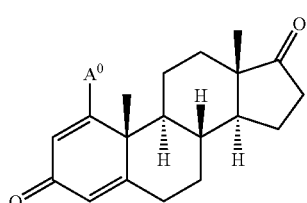
127
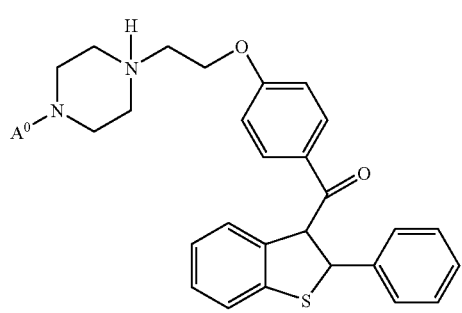
124
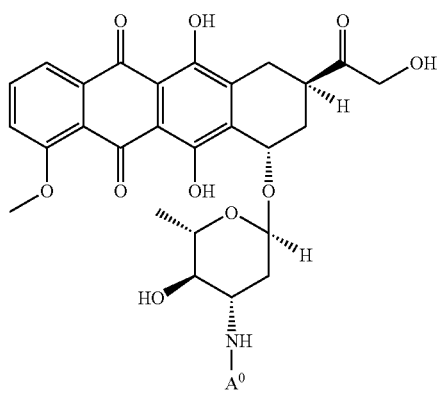
128
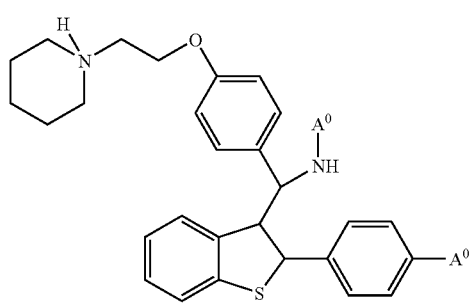
125
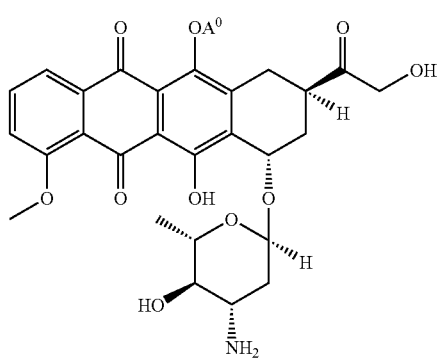
129

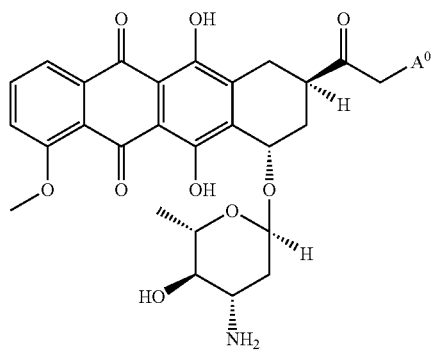
130
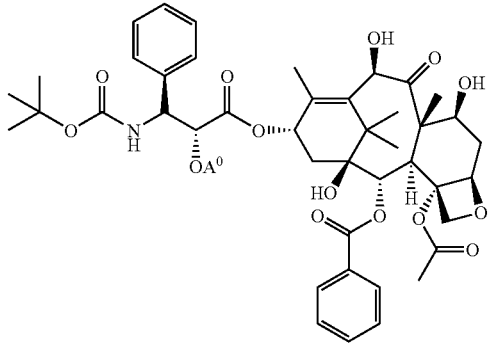
134
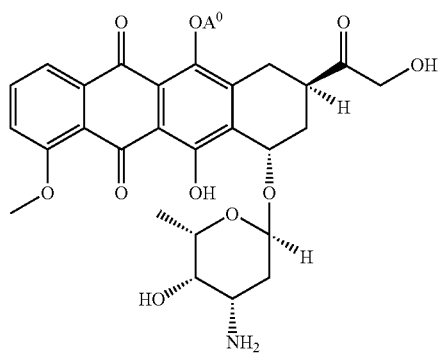
131
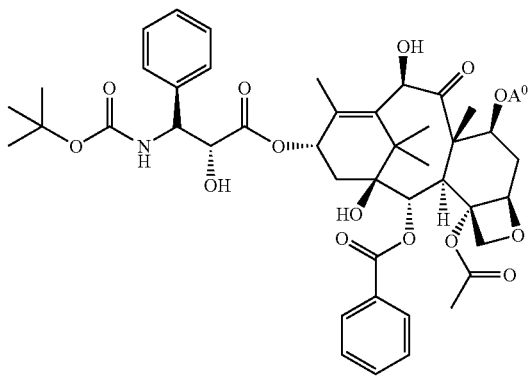
135
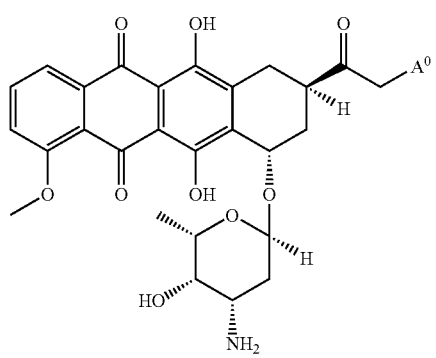
132
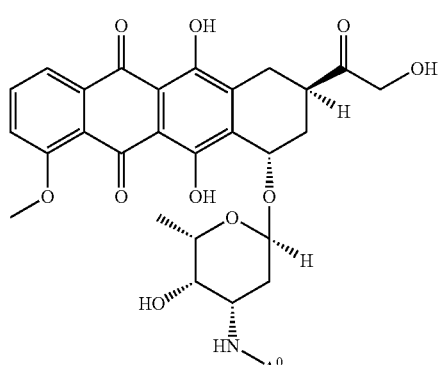
133
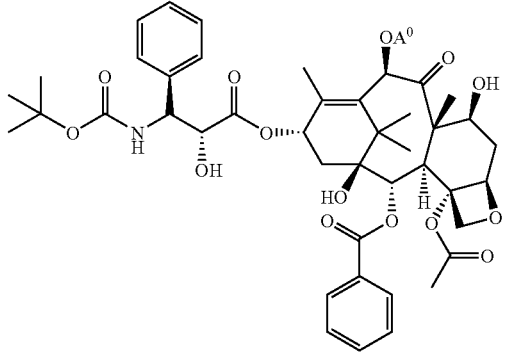
136

-continued
137
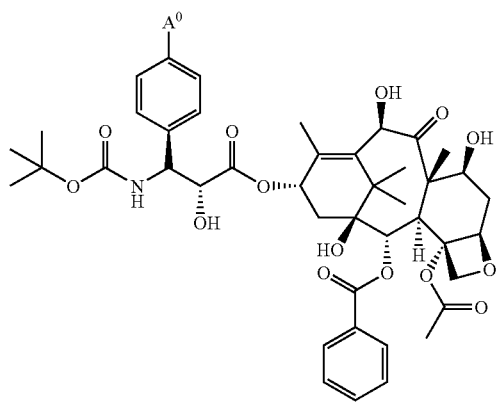
138
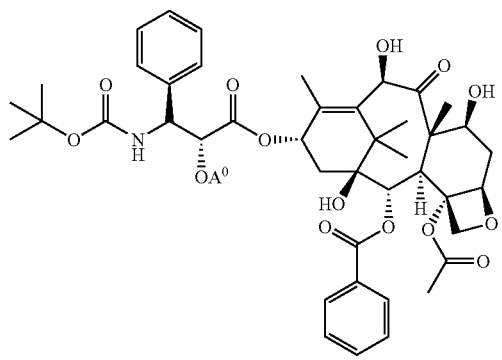
139
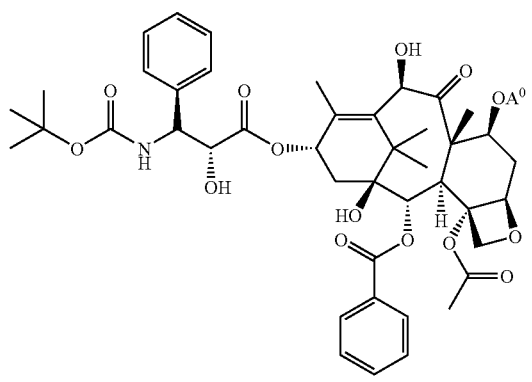
140
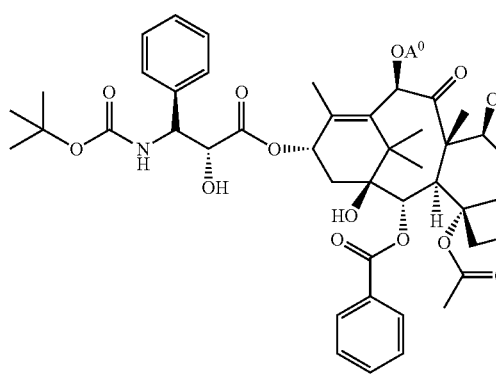
-continued
141
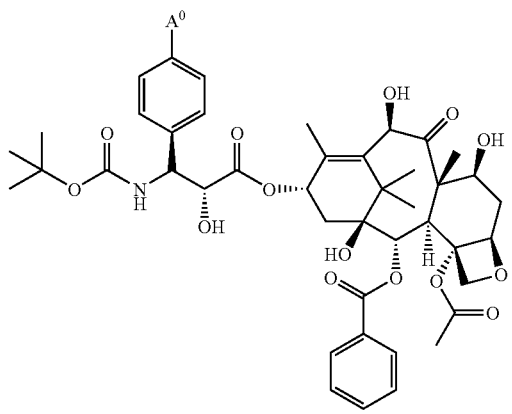
142
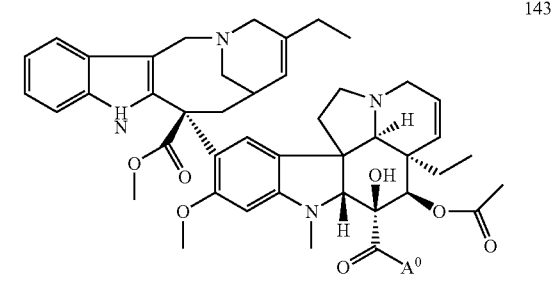
143
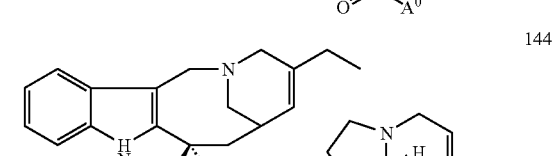
144
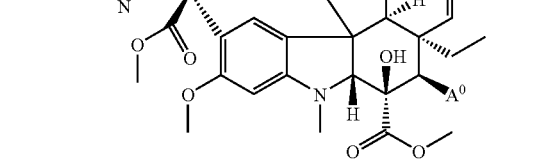
145
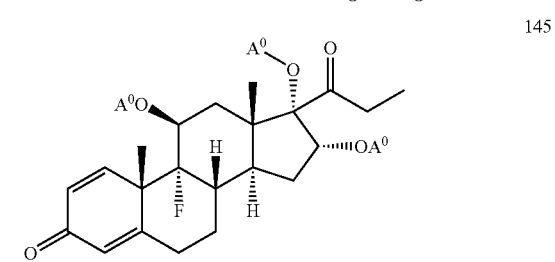

| | |
|---|---|
| 146 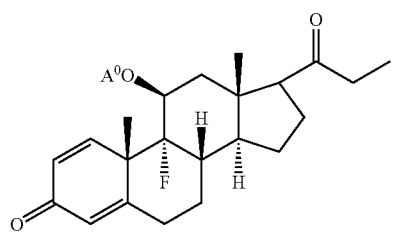 | 153 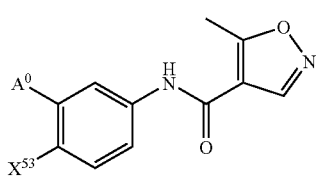 |
| 147 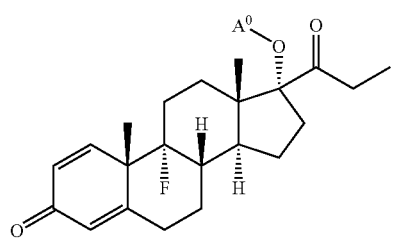 | 154 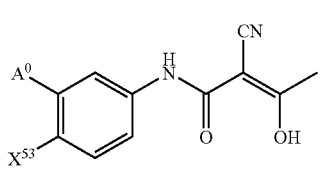 |
| 148 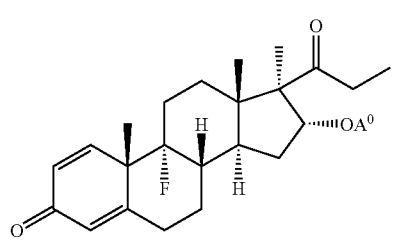 | 155 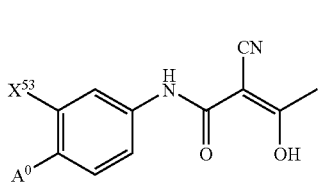 |
| 149 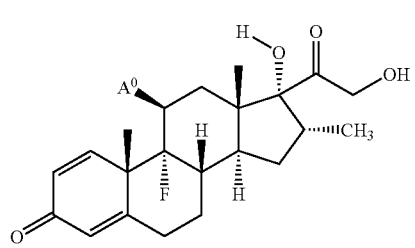 | 156 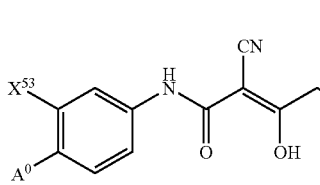 |
| 150 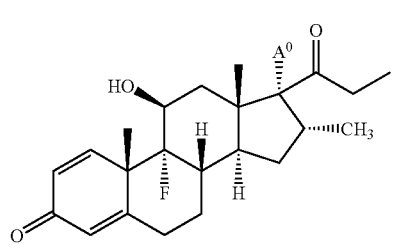 | 157 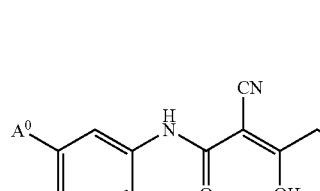 |
| 151 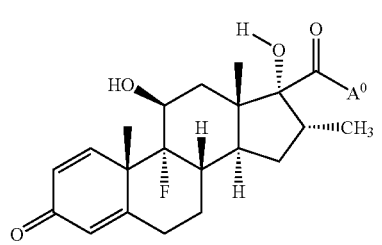 | 158 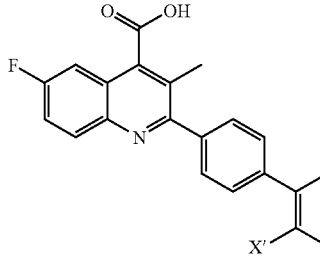 |
| 152 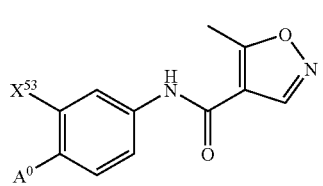 | |

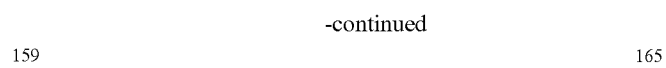
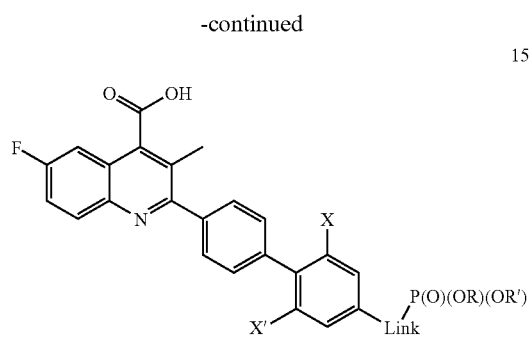
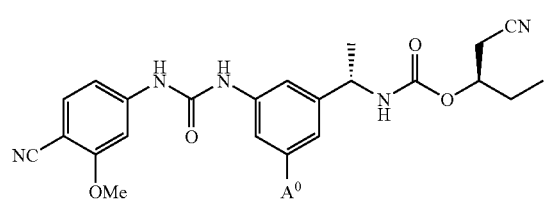
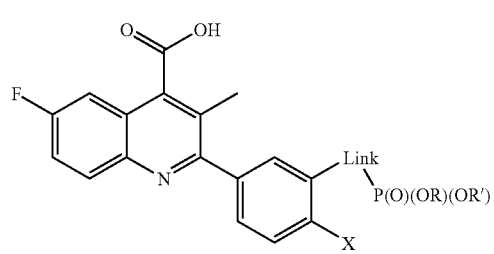
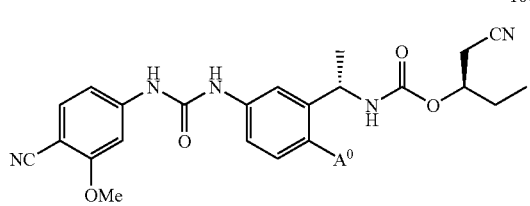
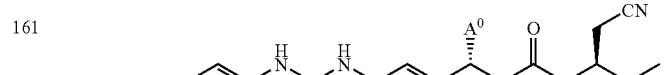
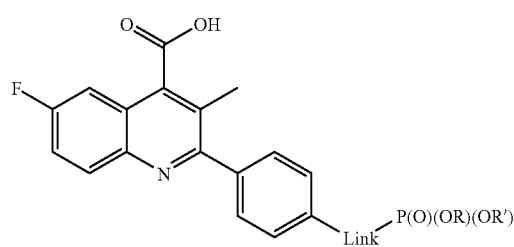
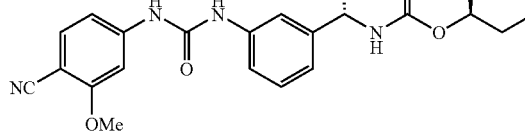
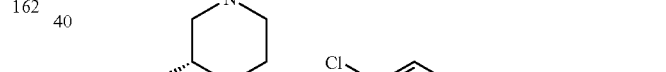
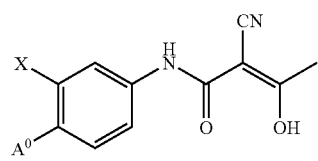
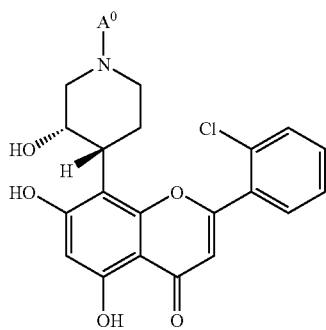
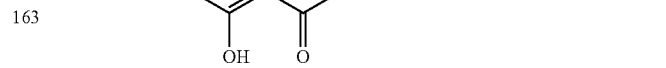
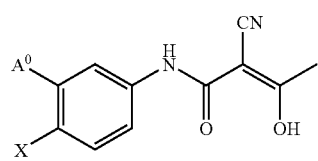
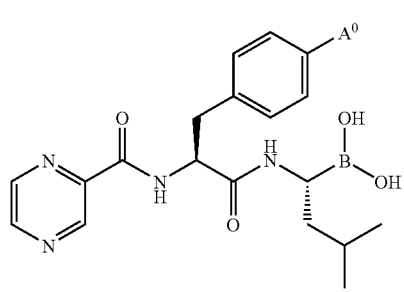
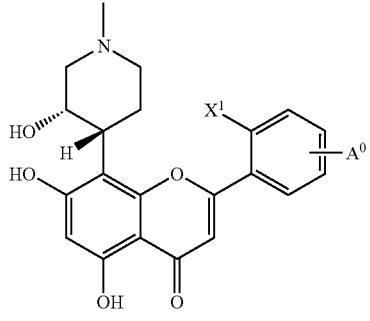

170
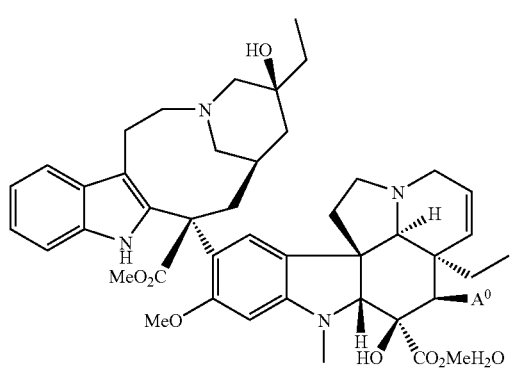
171
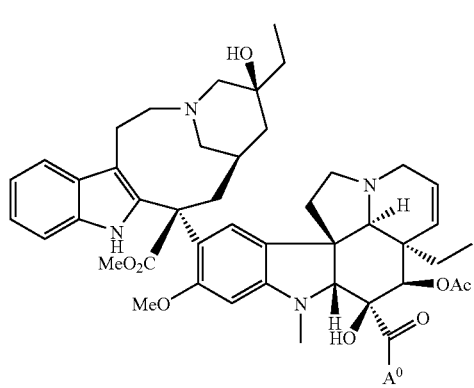
172
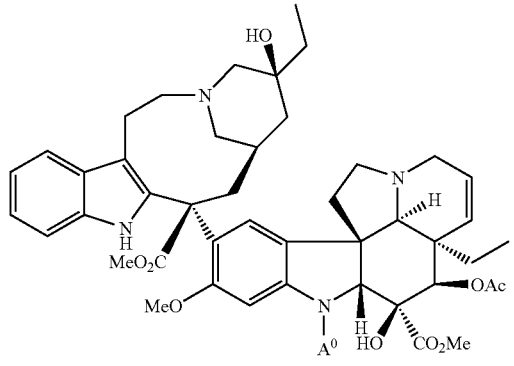
173
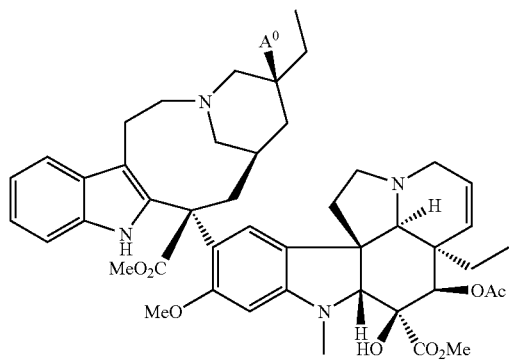
174
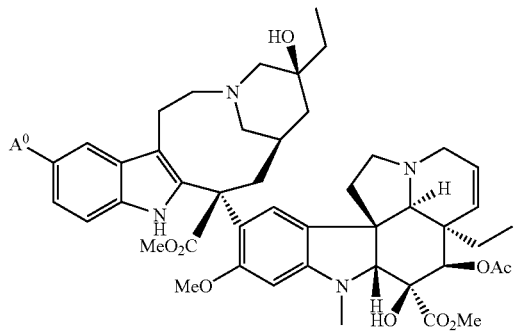
175
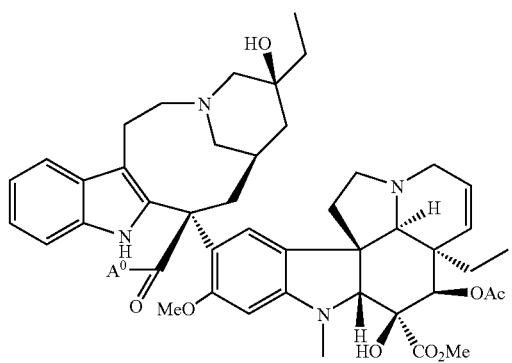
176
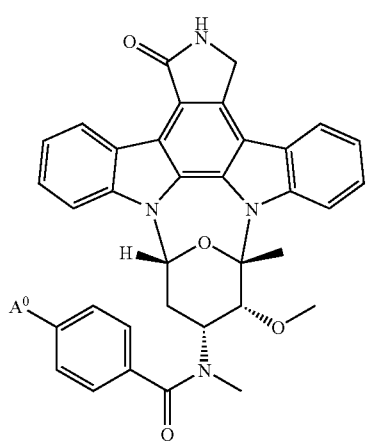

177 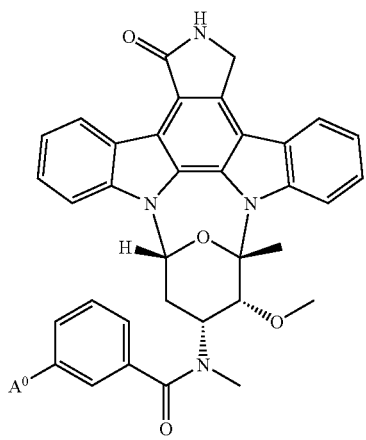
178 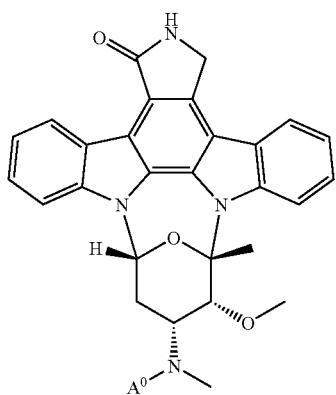
179 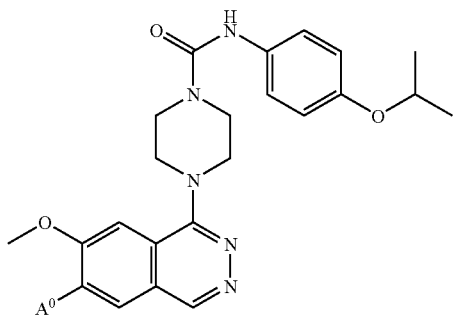
180 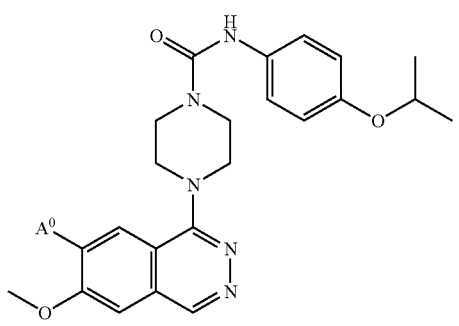
181 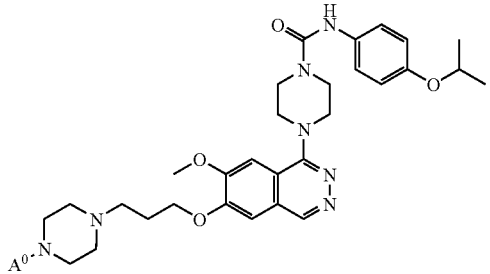
182 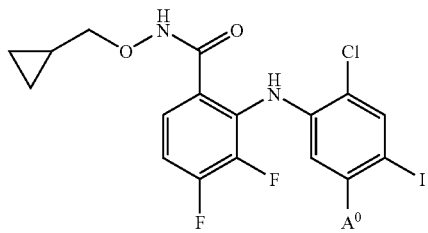
183 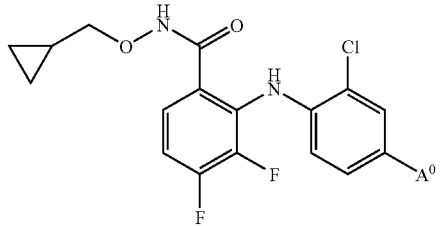
184 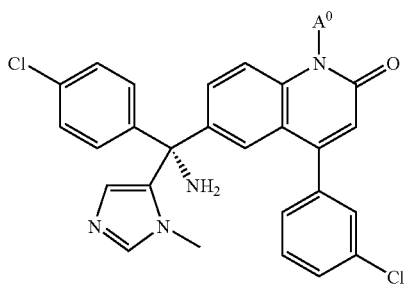
185 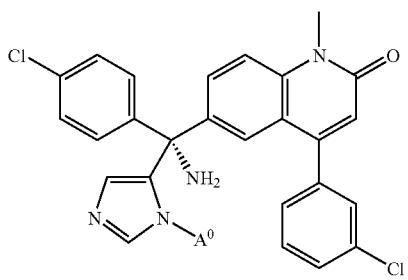

186 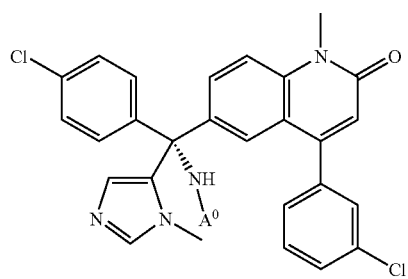
187
188
189
190
191 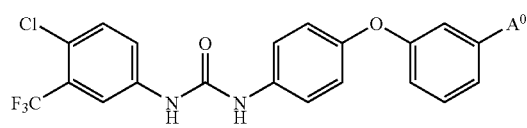
192 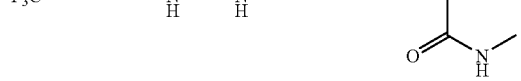
193 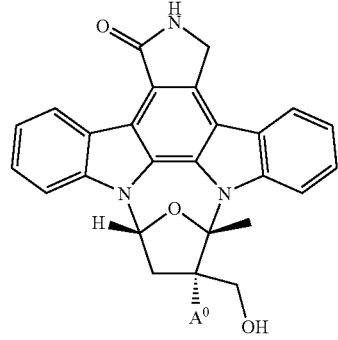
194 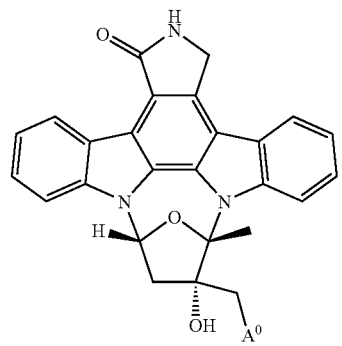

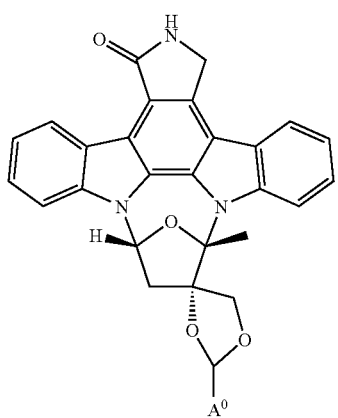
195
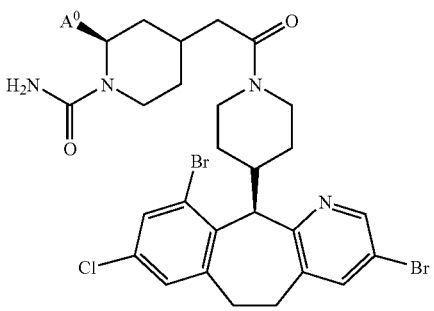
199
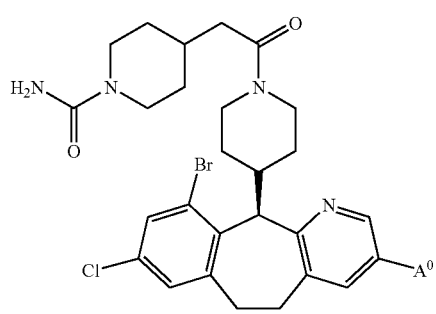
196
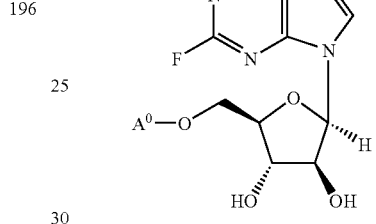
200
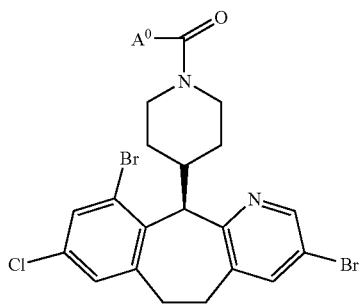
197
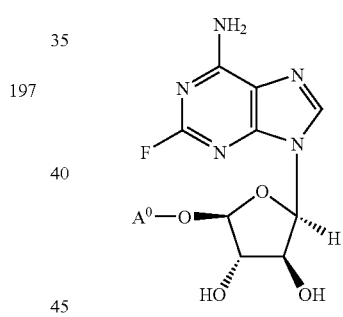
201
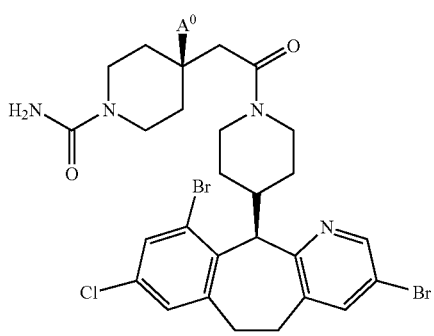
198
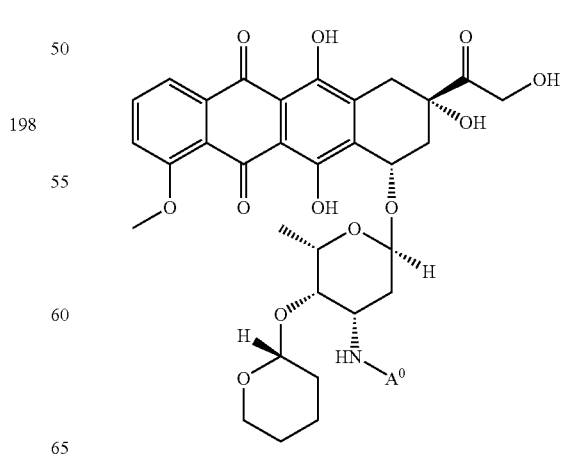
202

-continued
203
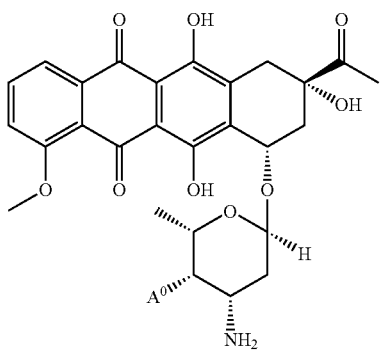
204
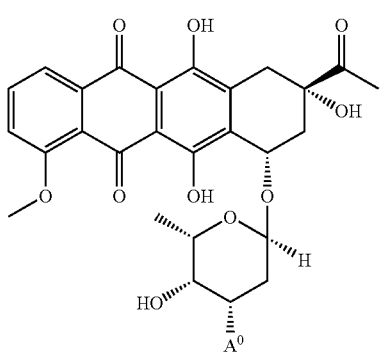
205
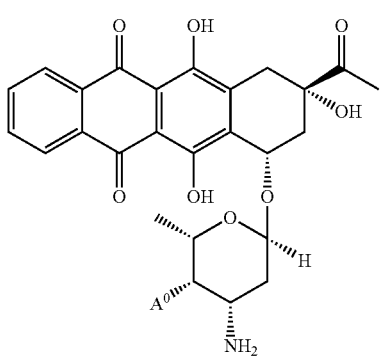
206
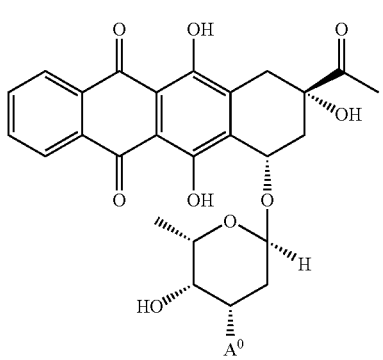
-continued
207
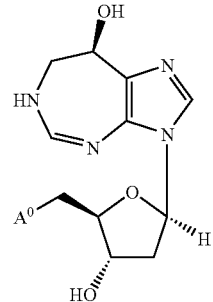
208
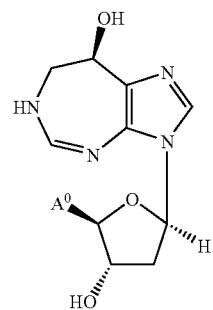
209
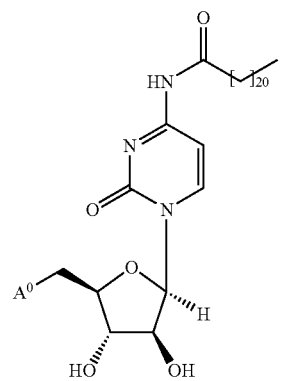
210
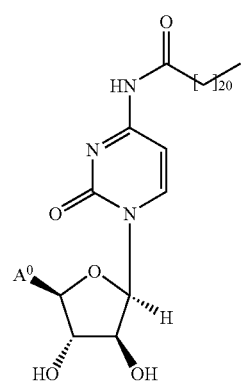

211 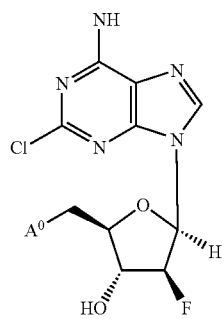
212 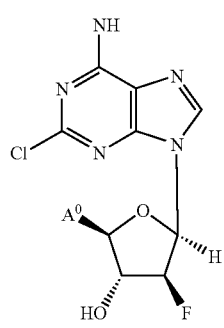
213 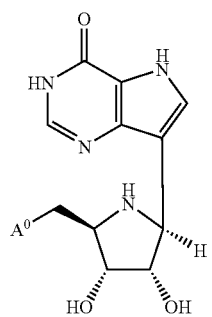
214 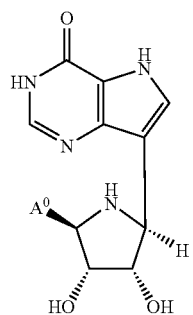
215 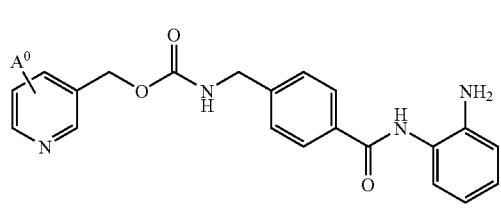
216 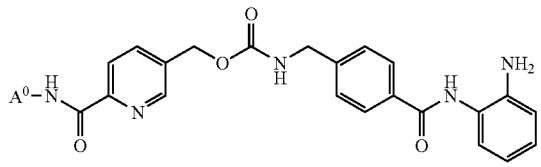
217 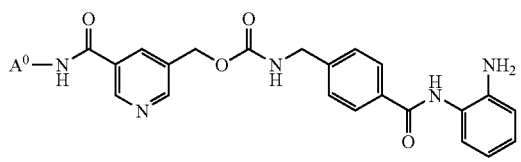
218 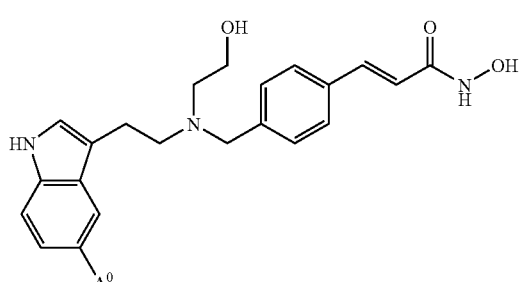
219 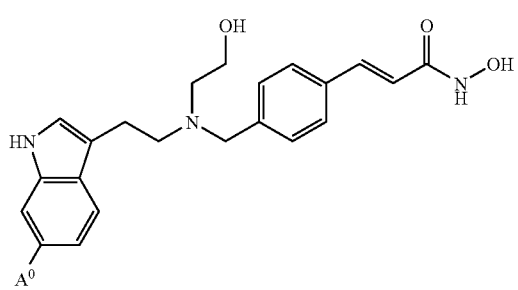
220 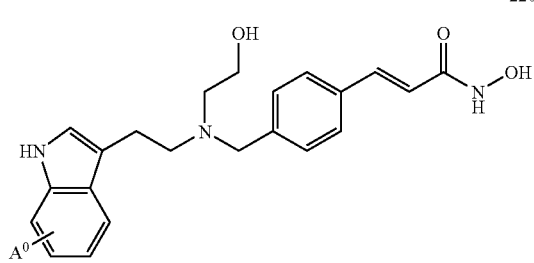
221 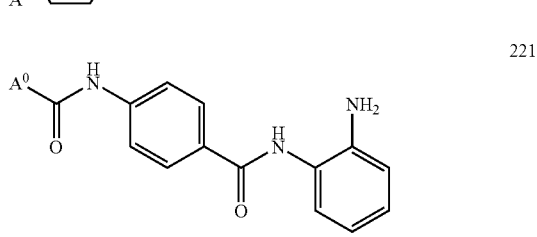

222
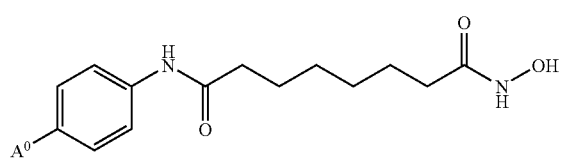
223
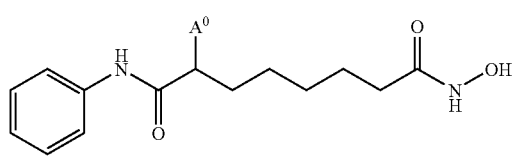
224
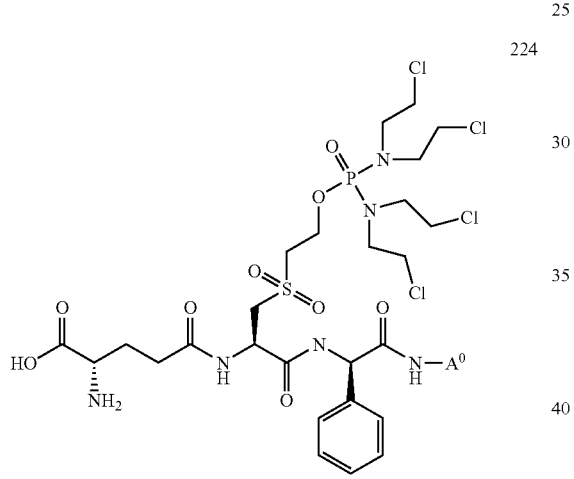
225
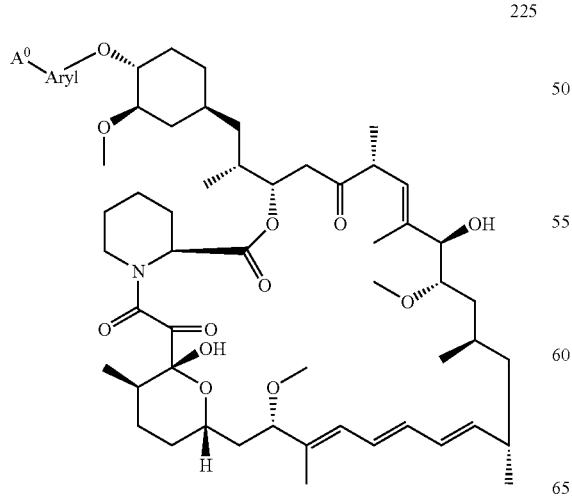
226
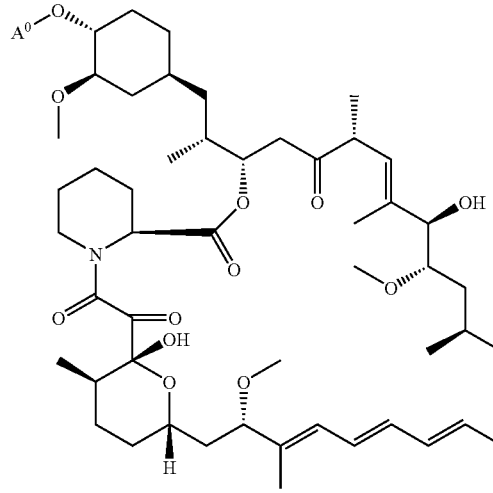
227
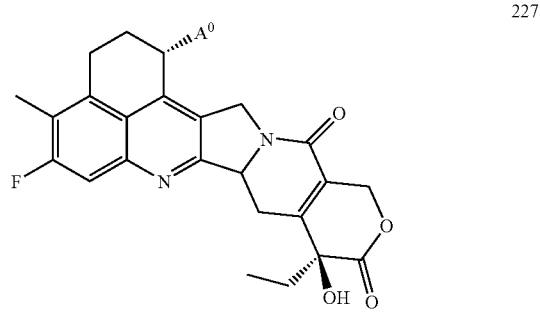
228
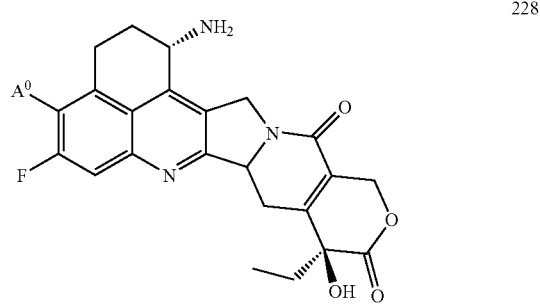

229
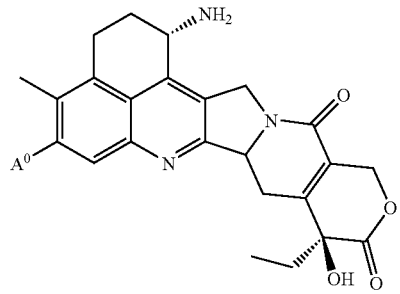
230
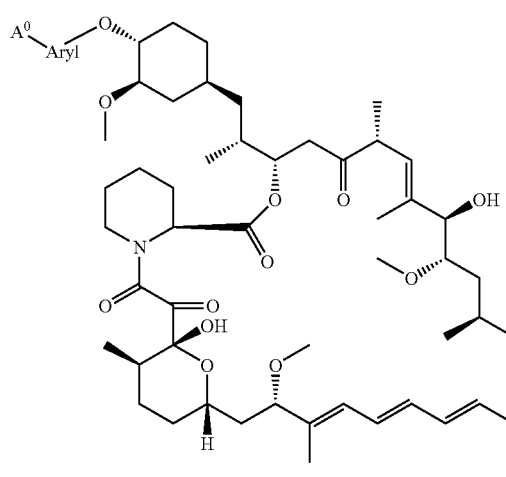
231
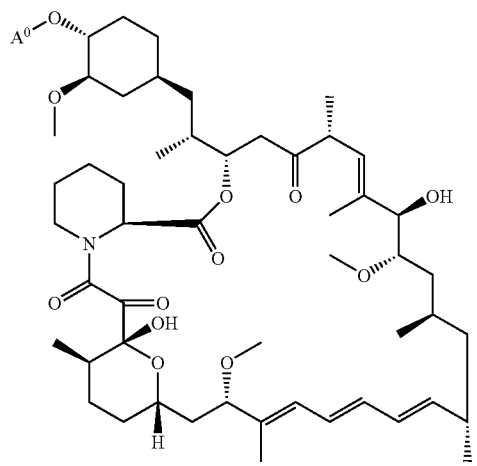
232
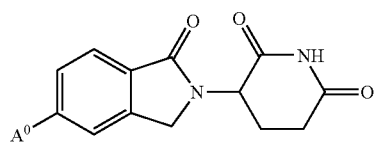
233
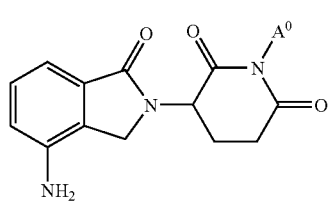
234
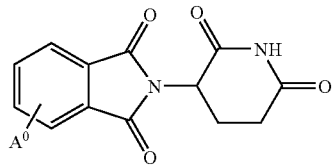
235
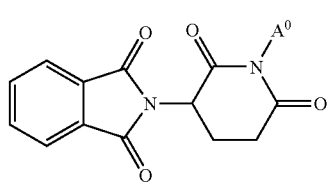
236
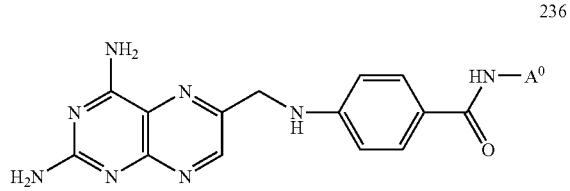
237
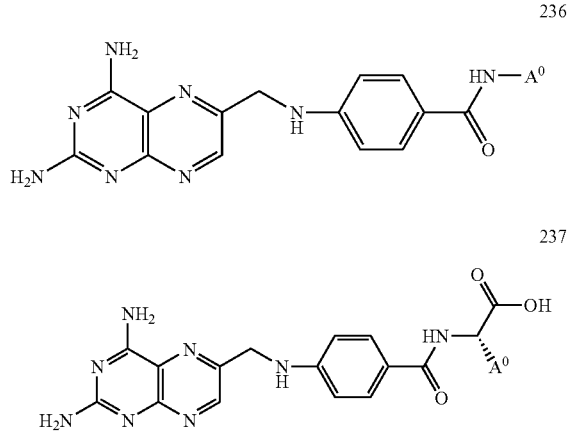
238
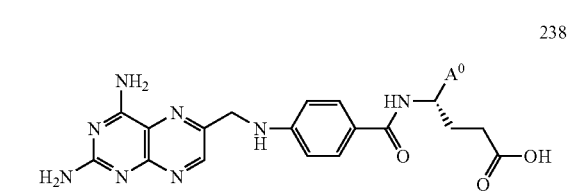
239
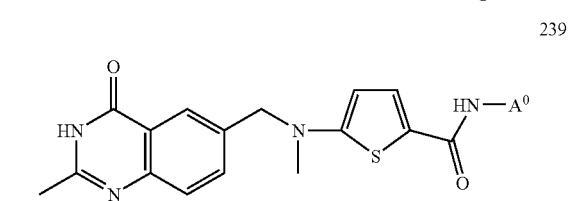
240
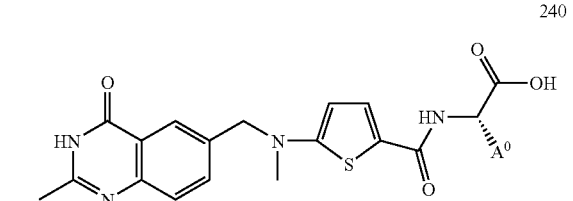
241
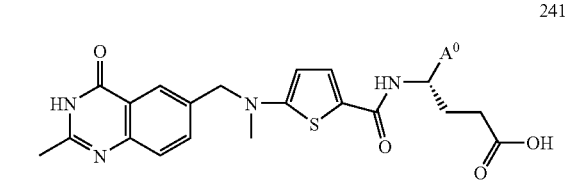

-continued
242
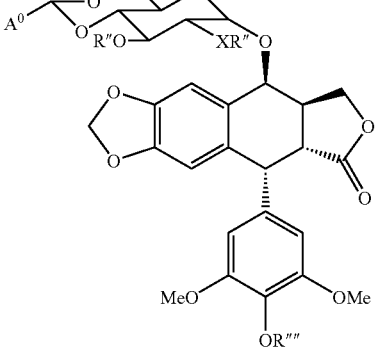
243
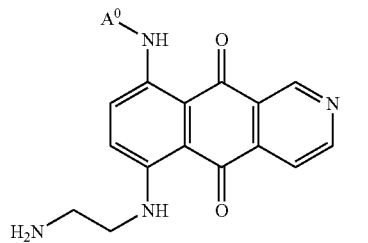
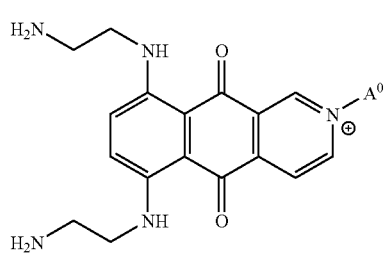
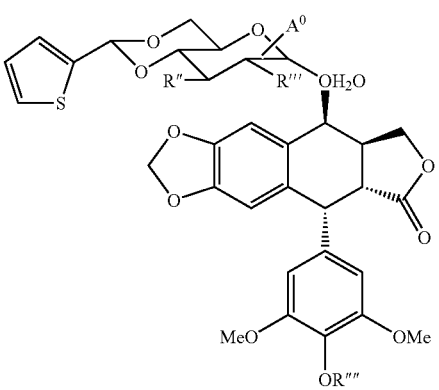
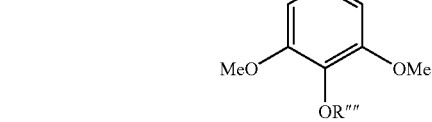
244
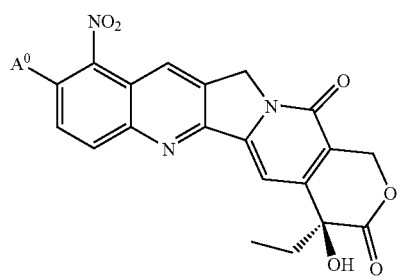
245
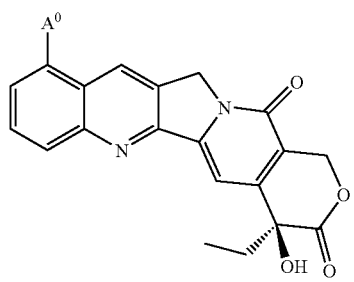
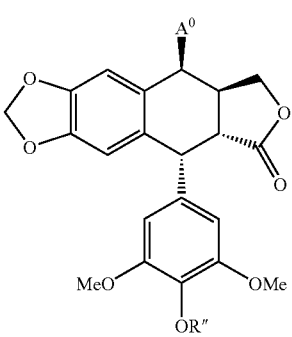
246
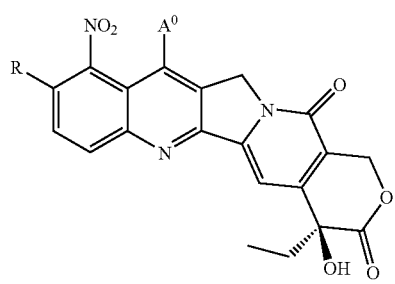
250
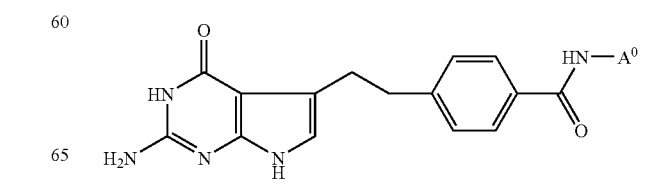

-continued
251
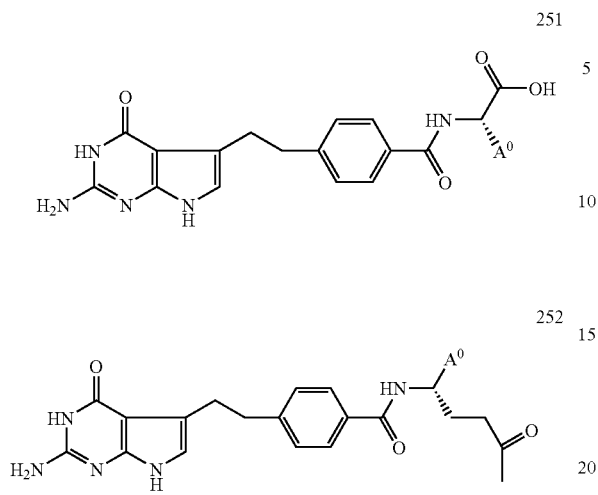
252
253
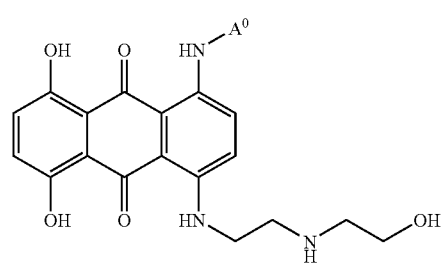
254
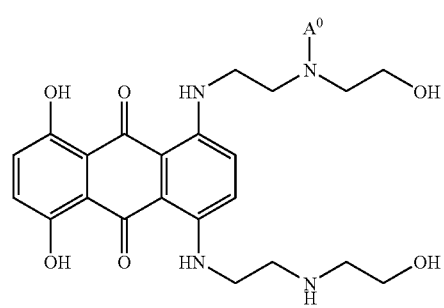
255
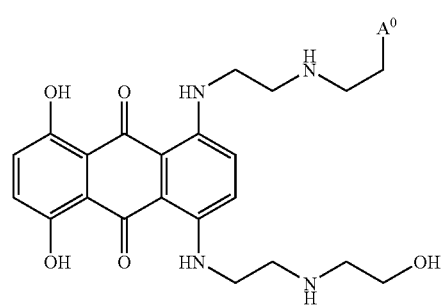
-continued
256
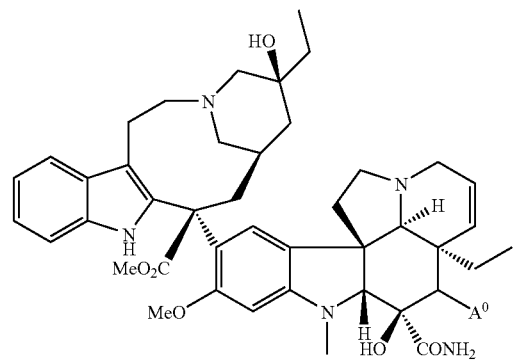
257
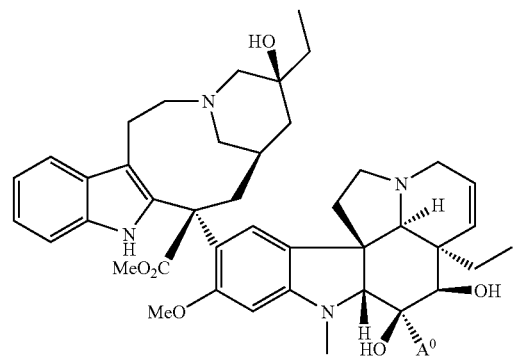
258
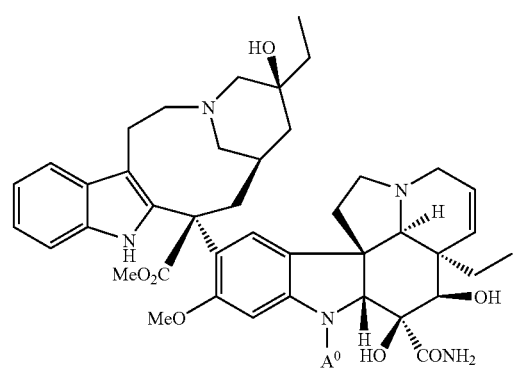

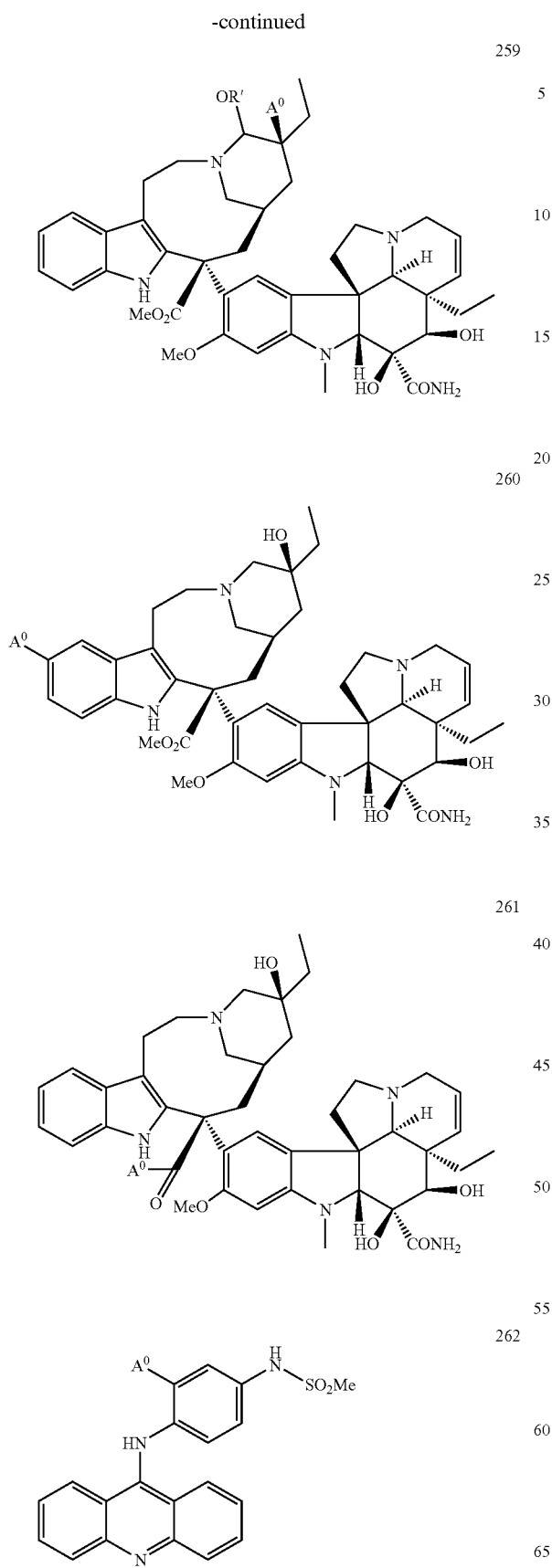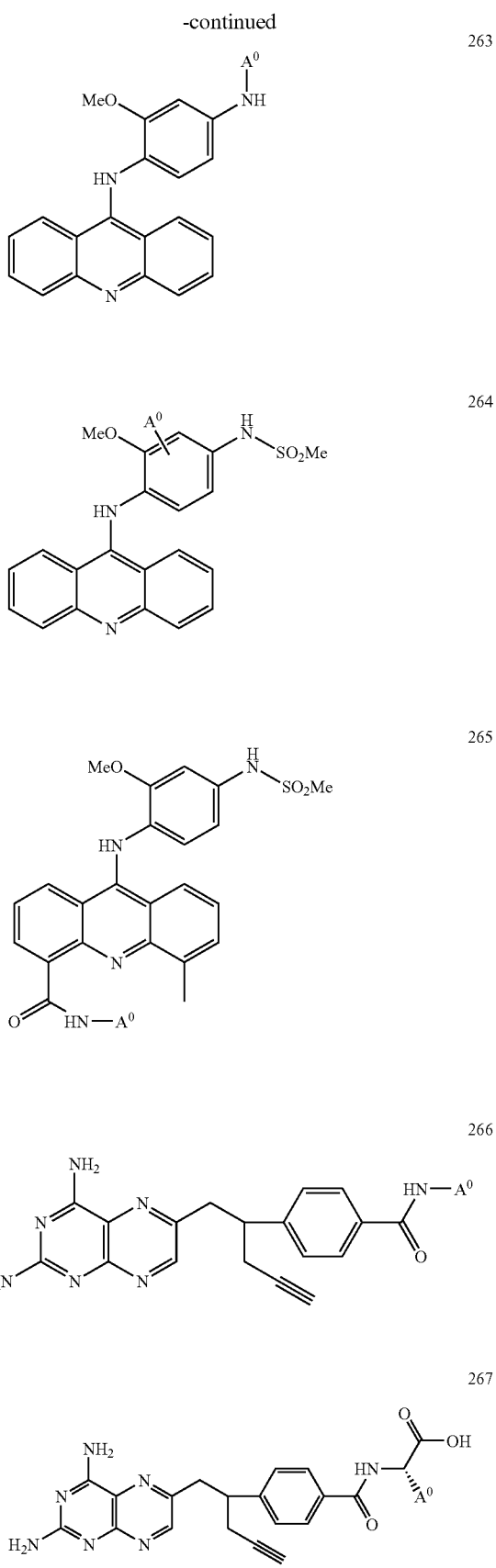

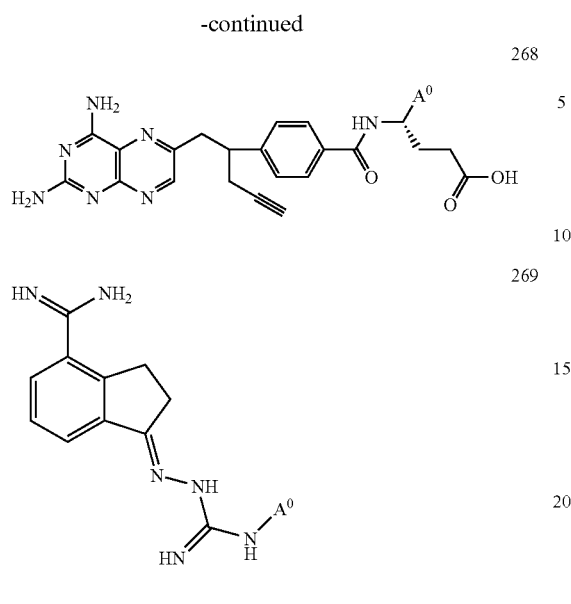
268
269
270
271
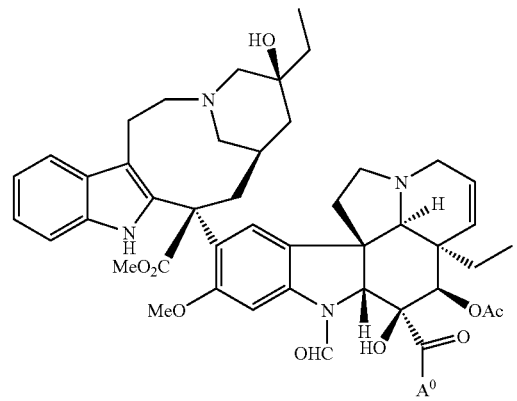
273
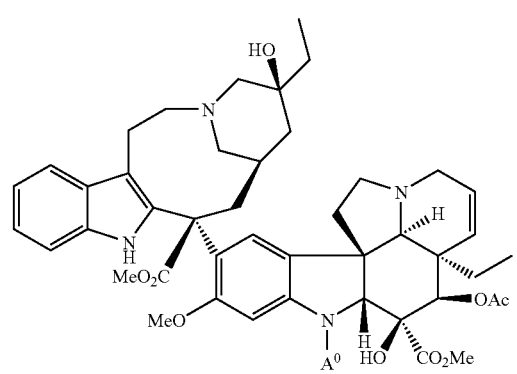
274
272
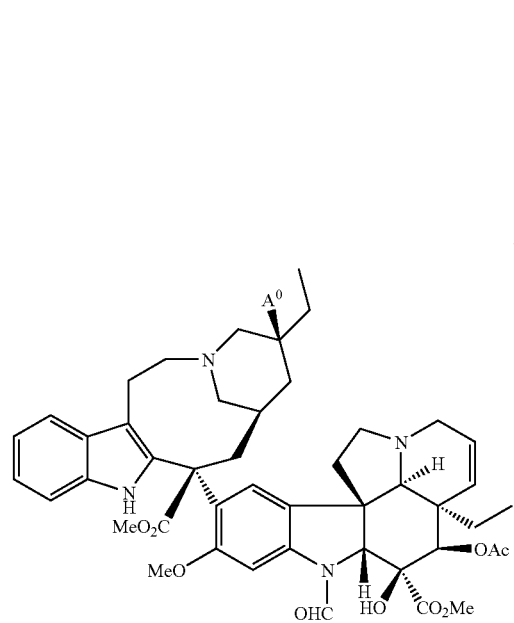
275

-continued
276
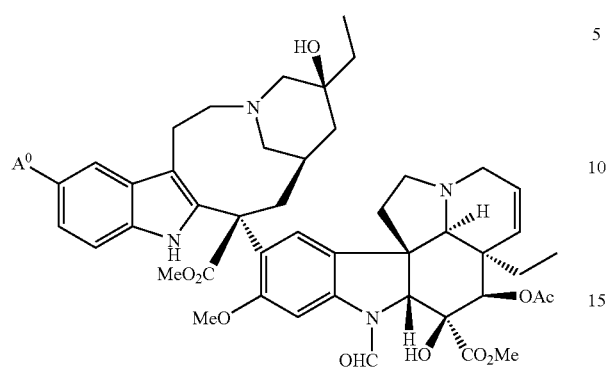
277
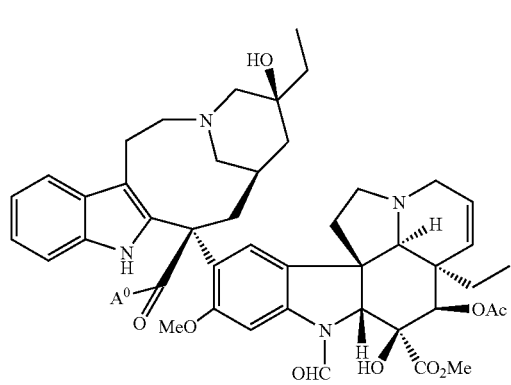
278
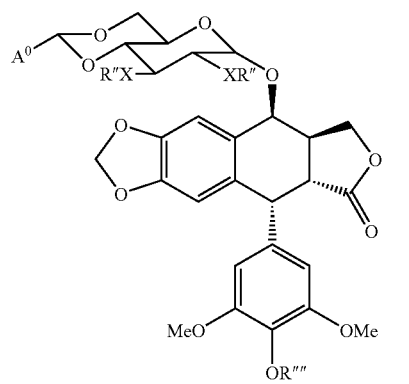
279
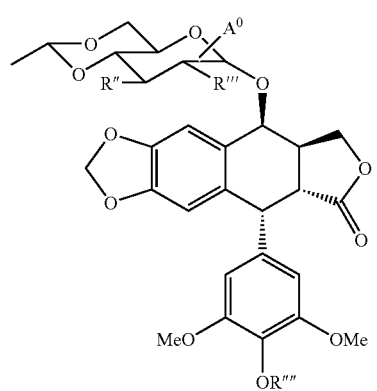
-continued
280
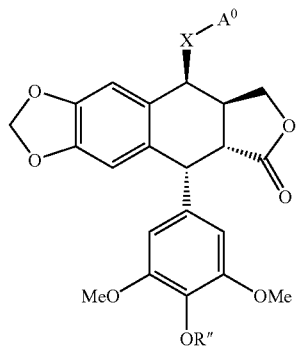
281
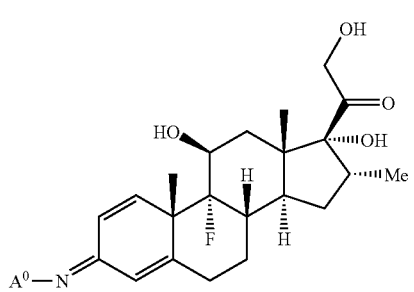
282
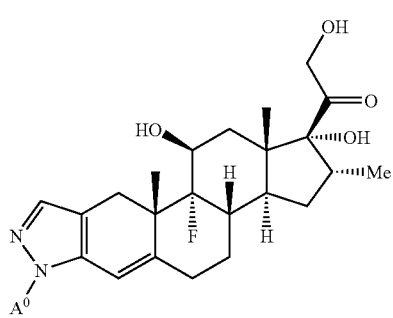
283
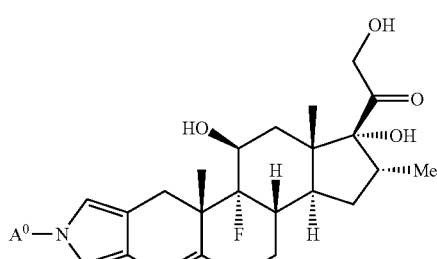

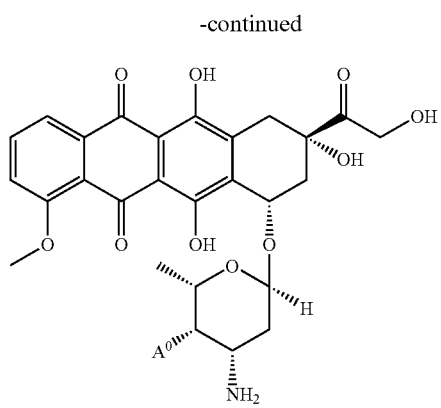
284
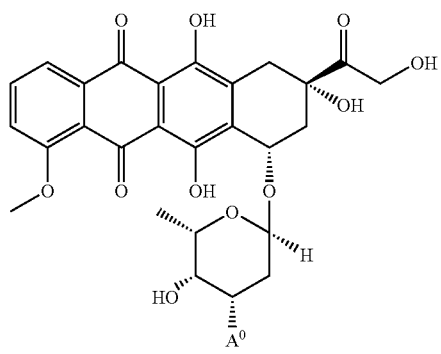
285
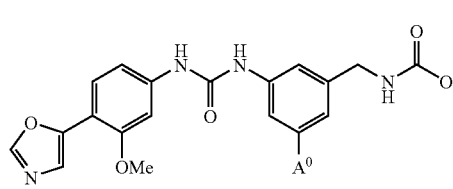
286
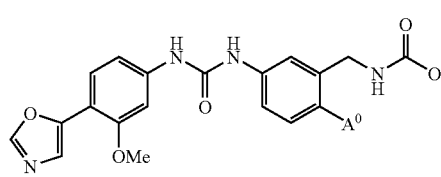
287
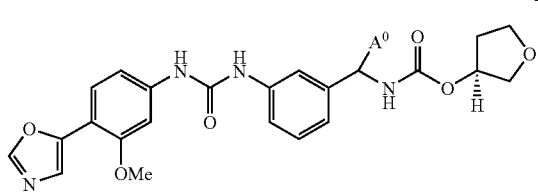
288
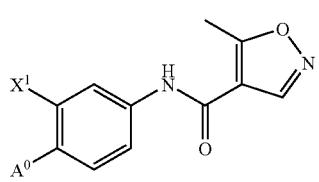
289
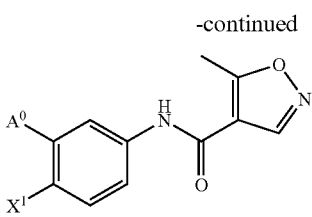
290
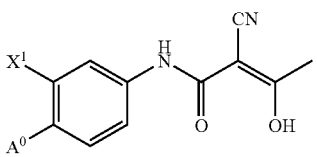
291
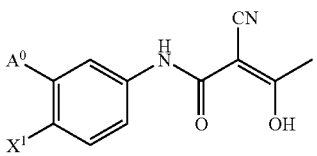
292
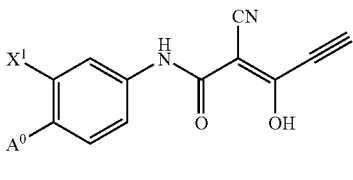
293
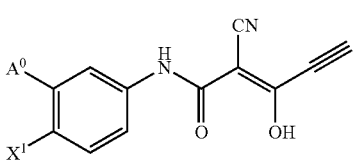
294
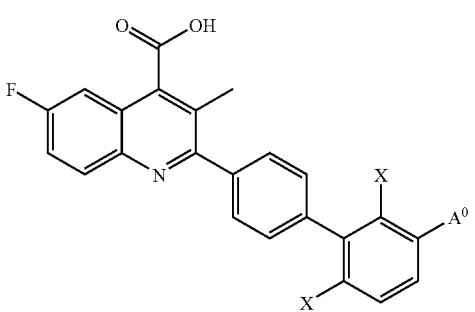
295

-continued
296
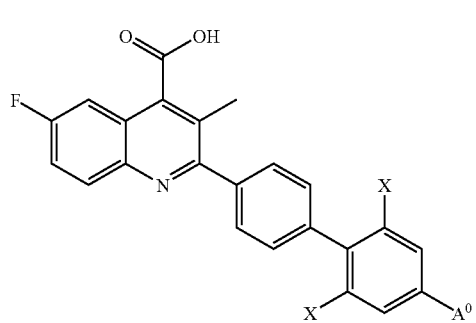
297
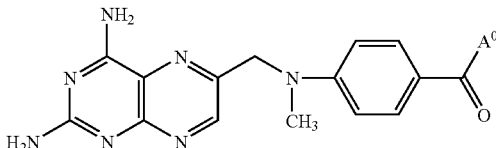
298
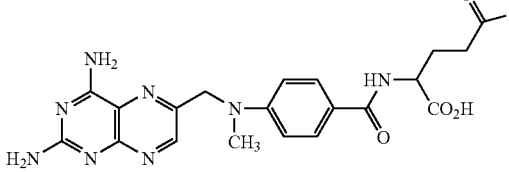
299
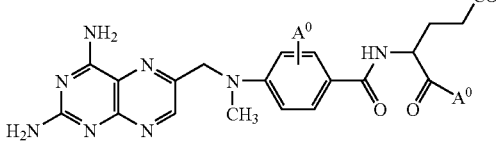
300
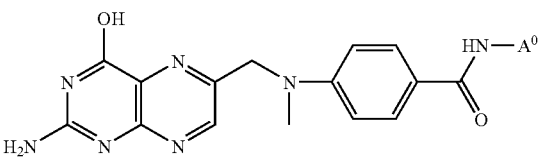
301
302
-continued
303
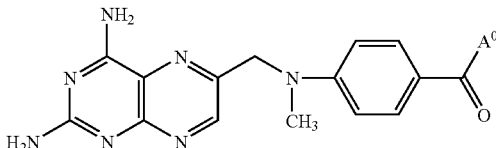
304
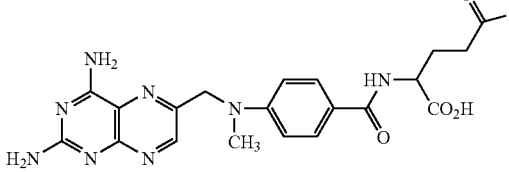
305
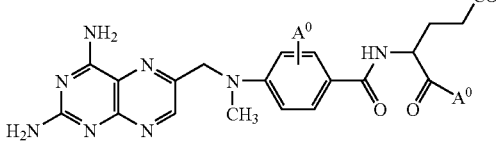
306
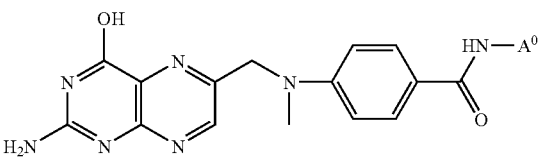
307
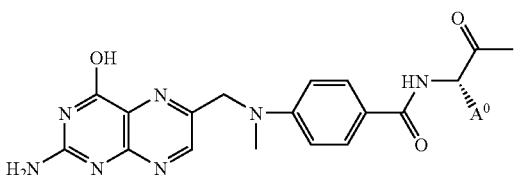
308
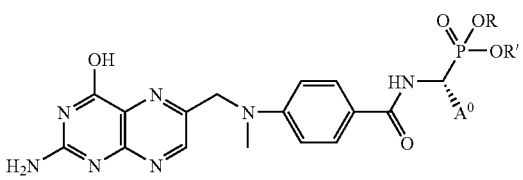

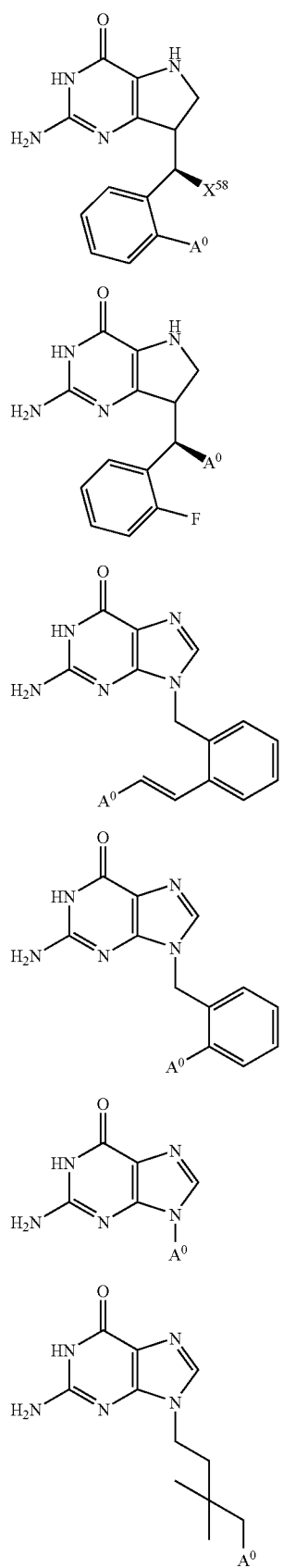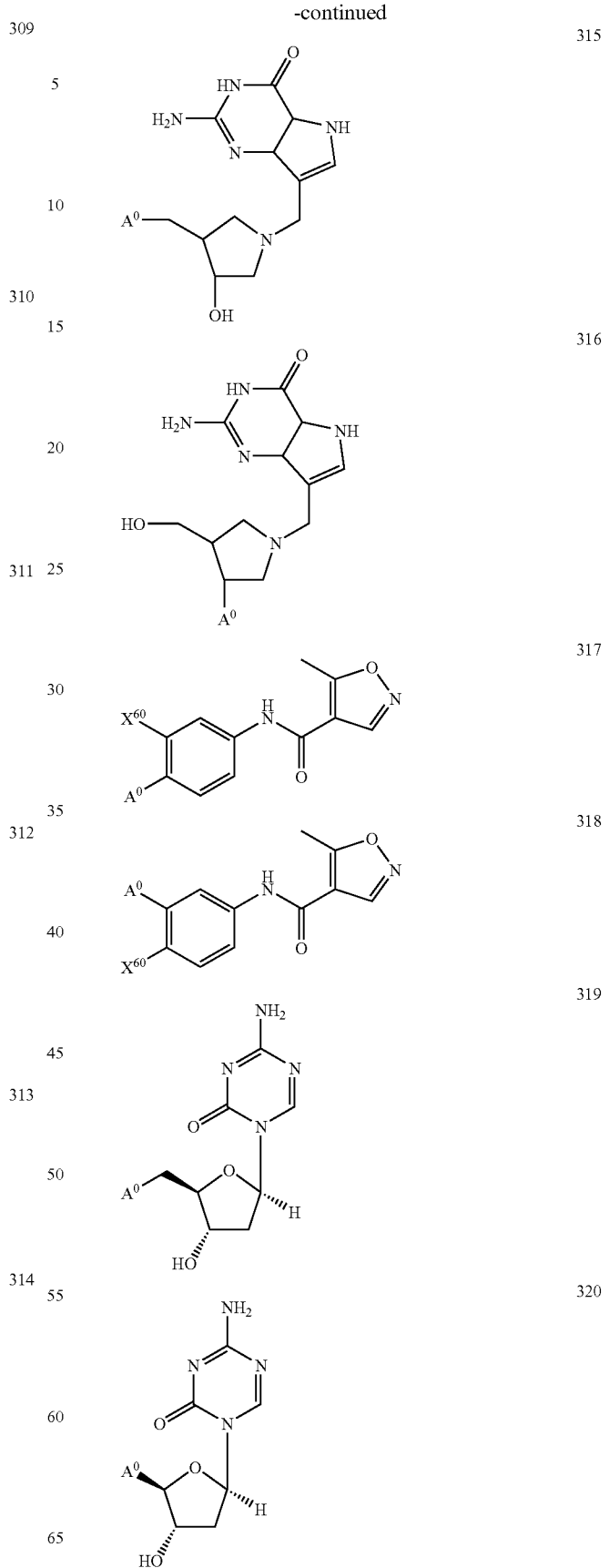

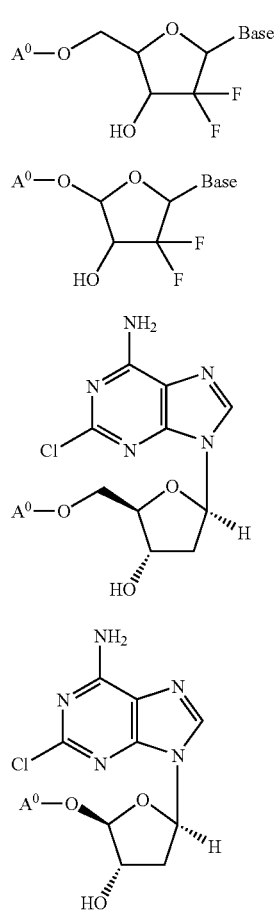
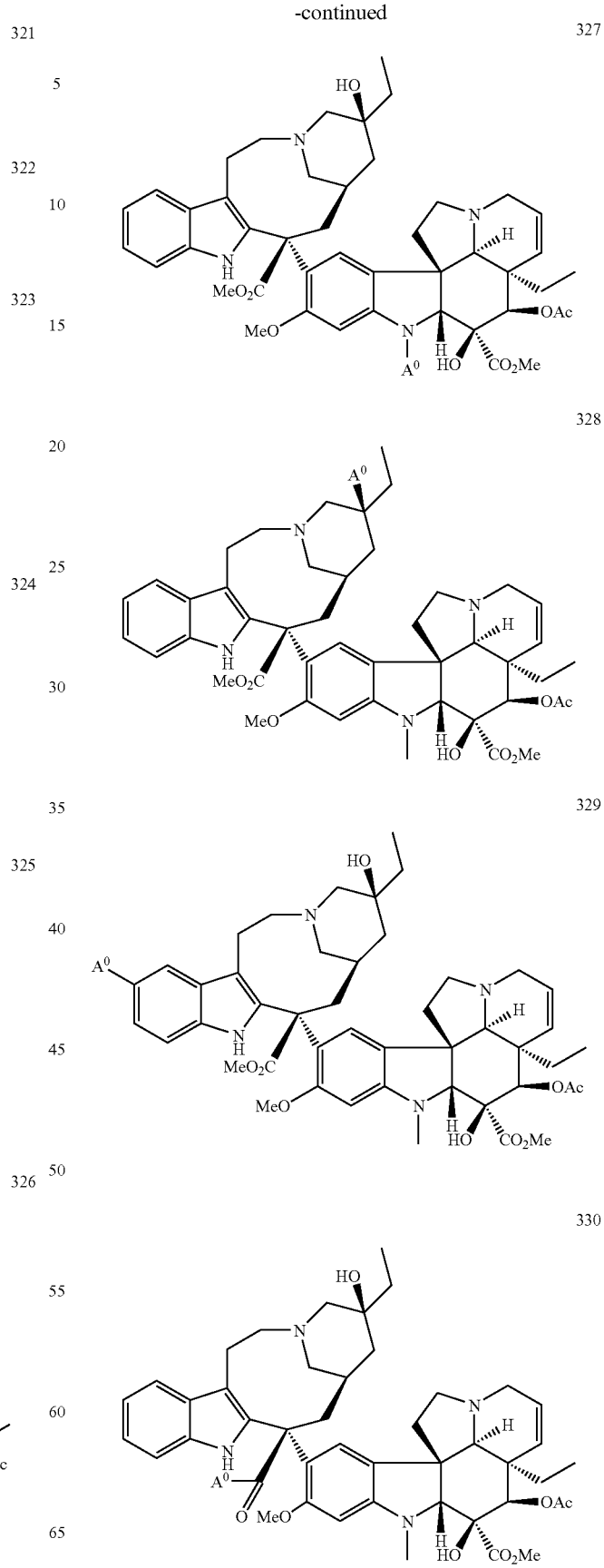

-continued

331

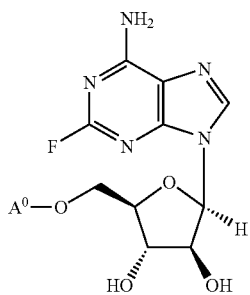

332

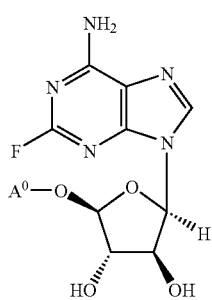

333

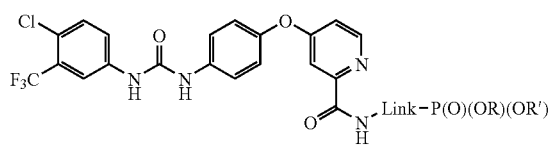

334

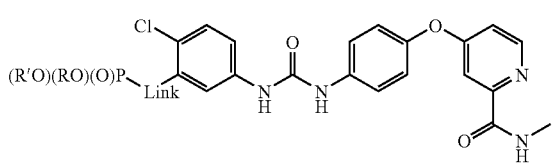

335

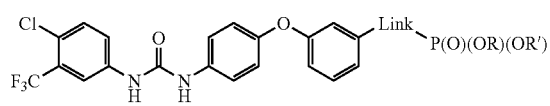

336

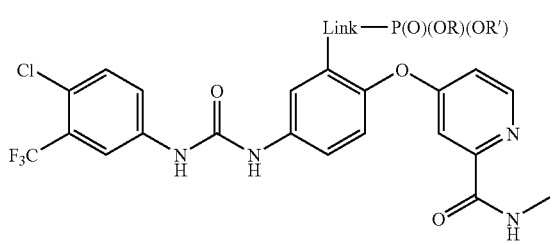

wherein:
$A^0$ is $A^1$;

$A^1$ is:

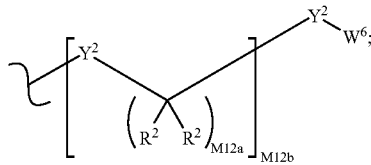

$A^3$ is:

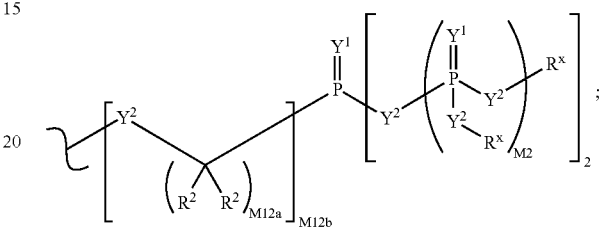

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$; and when $Y^2$ joins two phosphorous atoms Y can also be $C(R^2)(R^2)$;

$R^x$ is independently H, $R^2$, $W^3$, a protecting group, or the formula:

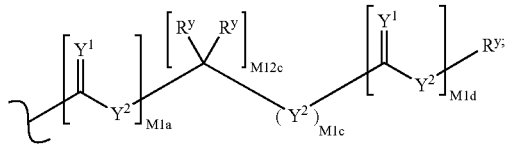

$R^y$ is independently H, $W^3$, $R^2$ or a protecting group;
$R^1$ is independently H or alkyl of 1 to 18 carbon atoms;
$R^2$ is independently H, $R^3$ or $R^4$ wherein each $R^4$ is independently substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, $-CN$, $N_3$ or $-NO_2$;
$R^{3b}$ is $Y^1$;
$R^{3c}$ is $R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;
$R^{3d}$ is $-C(Y^1)R^x$, $-C(Y^1)OR^x$ or $-C(Y^1)(N(R^x)(R^x))$;
$R^4$ is an alkyl of 1 to 18 carbon atoms, alkenyl of 2 to 18 carbon atoms, or alkynyl of 2 to 18 carbon atoms;
$R^5$ is $R^4$ wherein each $R^4$ is substituted with 0 to 3 $R^3$ groups;
$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —$C(Y^1)R^5$, —$C(Y^1)W^5$, —$SO_2R^5$, or —$SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{50}$ is H F, or Cl; and $X^{51}$ is H or Cl.

The invention provides a pharmaceutical composition comprising an effective amount of a compound of the invention, or a pharmaceutically acceptable salt thereof, in combination with a pharmaceutically acceptable diluent or carrier.

This invention provides a method of increasing cellular accumulation and retention of drug compounds, thus improving their therapeutic and diagnostic value, comprising linking the compound to one or more (e.g., 1, 2, 3, or 4) phosphonate groups.

This invention also pertains to a method of increasing cellular accumulation and retention of a chemotherapeutic agent comprising linking the compound to one or more phosphonate groups.

The invention also provides a method of treating cancer in a mammal, comprising administering a compound of the invention to the mammal.

The invention also provides a compound of the invention for use in medical therapy preferably for use in treating cancer, as well as the use of a compound of the invention for the manufacture of a medicament useful for the treatment of cancer.

In another aspect the invention also provides a method for inhibiting cancer activity comprising contacting a sample in need of such treatment with a compound or composition of the invention.

The invention also provides processes and novel intermediates disclosed herein which are useful for preparing compounds of the invention. Some of the compounds of the invention are useful to prepare other compounds of the invention. The invention also provides novel methods for syntheses of the compounds of the invention.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

When tradenames are used herein, applicants intend to independently include the tradename product and the active pharmaceutical ingredient(s) of the tradename product.

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

The terms "phosphonate" and "phosphonate group" include functional groups or moieties within a molecule that comprises a phosphorous that is 1) single-bonded to a carbon, 2) double-bonded to a heteroatom, 3) single-bonded to a heteroatom, and 4) single-bonded to another heteroatom, wherein each heteroatom can be the same or different. The terms "phosphonate" and "phosphonate group" also include functional groups or moieties that comprise a phosphorous in the same oxidation state as the phosphorous described above, as well as functional groups or moieties that comprise a prodrug moiety that can separate from a compound so that the compound retains a phosphorous having the characteriatics described above. For example, the terms "phosphonate" and "phosphonate group" include phosphonic acid, phosphonic monoester, phosphonic diester, phosphonamidate, and phosphonthioate functional groups. In one specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen, and 4) single-bonded to another oxygen, as well as functional groups or moieties that comprise a prodrug moiety that can separate from a compound so that the compound retains a phosphorous having such characteriatics. In another specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen or nitrogen, and 4) single-bonded to another oxygen or nitrogen, as well as functional groups or moieties that comprise a prodrug moiety that can separate from a compound so that the compound retains a phosphorous having such characteristics.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active anti-cancer compound compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2C(=O)R^9$ and acyloxymethyl carbonates —$CH_2C(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC)—$CH_2C(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate the phosphoric acid and the quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.,* 22: 155-174; Benzaria et al. (1996) *J. Med. Chem.* 39: 4958). Cyclic phosphonate esters have also been described as prodrugs of phosphorus-containing compounds (Erion et al., U.S. Pat. No. 6,312,662).

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to, ethylene or vinyl (—CH═CH₂), allyl (—CH₂CH═CH₂), cyclopentenyl (—C₅H₇), and 5-hexenyl (—CH₂ CH₂CH₂CH₂CH═CH₂).

"Alkynyl" is C₂-C₁₈ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH₂C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH₂—) 1,2-ethyl (—CH₂CH₂—), 1,3-propyl (—CH₂CH₂CH₂—), 1,4-butyl (—CH₂CH₂CH₂CH₂—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH₂C≡C—), and 4-pentynyl (—CH₂CH₂CH₂C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp³ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, —O⁻, —OR, —SR, —S⁻, —NR₂, —NR₃, ═NR, —CX₃, —CN, —OCN, —SCN, —N═C═O, —NCS, —NO, —NO₂, ═N₂, —N₃, NC(═O)R, —C(═O)R, —C(═O)NRR— S(═O)₂O⁻, —S(═O)₂OH, —S(═O)₂R, —OS(═O)₂OR, —S(═O)₂ NR, —S(═O)R, —OP(═O)O₂RR, —P(═O)O₂RR— P(═O)(O⁻)₂, —P(═O)(OH)₂, —C(═O)R, —C(═O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds A Series of Monographs*" (John Wiley & Sons, New York, 1950 to present), in particular Volumes 13, 14, 16, 19, and 28; and *J. Am. Chem. Soc*. (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

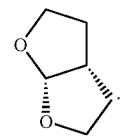

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

"Linker" or "link" refers to a chemical moiety comprising a covalent bond or a chain or group of atoms that covalently attaches a phosphonate group to a drug. Linkers include portions of substituents $A^1$ and $A^3$, which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protection. For example, protecting groups for —OH groups (whether hydroxyl, carboxylic acid, phosphonic acid, or other functions) are claims of "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34: 112-147 (1997) and are included within the scope of the present invention. An exemplary phosphonate ester-forming group is the phenyl carbocycle in substructure $A_3$ having the formula:

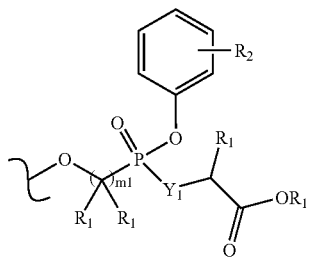

wherein $R_1$ may be H or $C_1$-$C_{12}$ alkyl; m1 is 1, 2, 3, 4, 5, 6, 7 or 8, and the phenyl carbocycle is substituted with 0 to 3 $R_2$ groups. Where $Y_1$ is O, a lactate ester is formed, and where $Y_1$ is $N(R_2)$, $N(OR_2)$ or $N(N(R_2)_2)$, a phosphonamidate ester results.

In its ester-forming role, a protecting group typically is bound to any acidic group such as, by way of example and not limitation, a —$CO_2$H or —C(S)OH group, thereby resulting in —$CO_2R^x$ where $R^x$ is defined herein. Also, $R^x$ for example includes the enumerated ester groups of WO 95/07920.

Examples of protecting groups include:

$C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$-$C_{12}$ heterocycle or aryl substituted with halo, $R^1$, $R_1$—O—$C_1$-$C_{12}$ alkylene, $C_1$-$C_{12}$ alkoxy, CN, $NO_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-, 3- and 4-acetylphenyl, 1,8-dihydroxynaphthyl (—$C_{10}H_6$—OH) and aryloxy ethyl [$C_6$-$C_9$ aryl (including phenoxy ethyl)], 2,2'-dihydroxybiphenyl, 2-, 3- and 4-N,N-dialkylaminophenol, —$C_6H_4CH_2$—$N(CH_3)_2$, trimethoxybenzyl, triethoxybenzyl, 2-alkyl pyridinyl ($C_{1-4}$ alkyl);

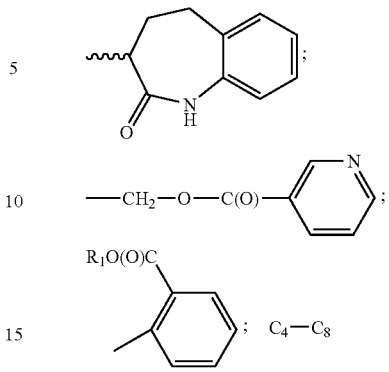

esters of 2-carboxyphenyl; and $C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2CCl_3$), $C_1$-$C_{12}$ alkyl (including methyl and ethyl), $C_2$-$C_{12}$ alkenyl or $C_2$-$C_{12}$ alkynyl; alkoxy ethyl [$C_1$-$C_6$ alkyl including —$CH_2$—$CH_2$—O—$CH_3$ (methoxy ethyl)]; alkyl substituted by any of the groups set forth above for aryl, in particular OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4CH_3$, —$(CH_2)_5CH_3$, —$CH_2CH_2F$, —$CH_2CH_2Cl$, —$CH_2CF_3$, and —$CH_2CCl_3$);

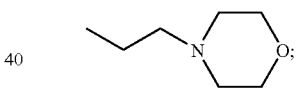

—N-2-propylmorpholino, 2,3-dihydro-6-hydroxyindene, sesamol, catechol monoester, —$CH_2$—C(O)—$N(R^1)_2$, —$CH_2$—S(O)($R^1$), —$CH_2$—$S(O)_2(R^1)$, —$CH_2$—CH(OC(O)$CH_2R^1$)—$CH_2(OC(O)CH_2R^1)$, cholesteryl, enolpyruvate (HOOC—C(=$CH_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* (1974) 5(6):670-671;

cyclic carbonates such as (5-$R_d$-2-oxo-1,3-dioxolen-4-yl) methyl esters (Sakamoto et al., *Chem. Pharm. Bull.* (1984) 32(6)2241-2248) where $R_d$ is $R^1$, $R^4$ or aryl; and

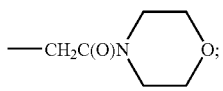

The hydroxyl groups of the compounds of this invention optionally are substituted with one of groups III, IV or V disclosed in WO 94/21604, or with isopropyl.

Table A lists examples of protecting group ester moieties that for example can be bonded via oxygen to —C(O)O— and —P(O)(O—)$_2$ groups. Several amidates also are shown, which are bound directly to —C(O)— or —P(O)$_2$. Esters of structures 1-5, 8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, CsCO$_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

1. —CH$_2$—C(O)—N(R$_1$)$_2$*
2. —CH$_2$—S(O)(R$_1$)
3. —CH$_2$—S(O)$_2$(R$_1$)
4. —CH$_2$—O—C(O)—CH$_2$—C$_6$H$_5$
5. 3-cholesteryl
6. 3-pyridyl
7. N-ethylmorpholino
8. —CH$_2$—O—C(O)—C$_6$H$_5$
9. —CH$_2$—O—C(O)—CH$_2$CH$_3$
10. —CH$_2$—O—C(O)—C(CH$_3$)$_3$
11. —CH$_2$—CCl$_3$
12. —C$_6$H$_5$
13. —NH—CH$_2$—C(O)O—CH$_2$CH$_3$
14. —N(CH$_3$)—CH$_2$—C(O)O—CH$_2$CH$_3$
15. —NHR$_1$
16. —CH$_2$—O—C(O)—C$_{10}$H$_{15}$
17. —CH$_2$—O—C(O)—CH(CH$_3$)$_2$
18. —CH$_2$—C#H(OC(O)CH$_2$R$_1$)—CH$_2$—(OC(O)CH$_2$R$_1$)*

19. 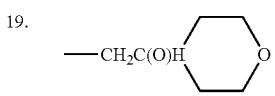

20. 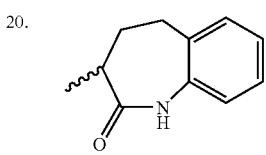

21. 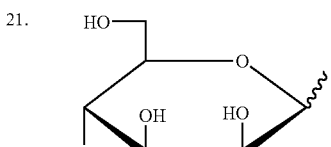

22. 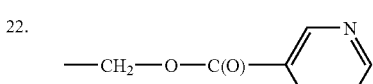

TABLE A-continued

23. 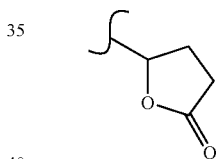

24. CH$_3$O(O)C—

25. CH$_3$CH$_2$O(O)C—

26.

-chiral is (R), (S) or racemate.

Other esters that are suitable for use herein are described in EP 632048.

Protecting groups also includes "double ester" forming profunctionalities such as —CH$_2$OC(O)OCH$_3$, —CH$_2$SCOCH$_3$, —CH$_2$OCON(CH$_3$)$_2$, or alkyl- or aryl-acyloxyalkyl groups of the structure —CH(R$^1$ or W$^5$)O((CO)R$^{37}$) or —CH(R$^1$ or W$^5$)((CO)OR$^{38}$) (linked to oxygen of the acidic group) wherein R$^{37}$ and R$^{38}$ are alkyl, aryl, or alkylaryl groups (see U.S. Pat. No. 4,968,788). Frequently R$^{37}$ and R$^{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including —CH(CH$_2$CH$_2$OCH$_3$)OC(O)C(CH$_3$)$_3$,

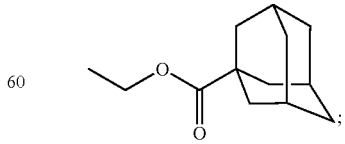

—CH$_2$OC(O)C$_{10}$H$_{15}$, —CH$_2$OC(O)C(CH$_3$)$_3$, —CH(CH$_2$OCH$_3$)OC(O)C(CH$_3$)$_3$, —CH(CH(CH$_3$)$_2$)OC(O)C(CH$_3$)$_3$, —CH$_2$OC(O)CH$_2$CH(CH$_3$)$_2$, —CH$_2$OC(O)C$_6$H$_{11}$,

—CH$_2$OC(O)C$_6$H$_5$, —CH$_2$OC(O)C$_{10}$H$_{15}$, —CH$_2$OC(O)CH$_2$CH$_3$, —CH$_2$OC(O)CH(CH$_3$)$_2$, —CH$_2$OC(O)C(CH$_3$)$_3$ and —CH$_2$OC(O)CH$_2$C$_6$H$_5$.

In some claims the protected acidic group is an ester of the acidic group and is the residue of a hydroxyl-containing functionality. In other claims, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under R$^{31}$ or R$^{35}$), the table on page 105, and pages 21-23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or C$_1$-C$_4$ alkylestercarboxyphenyl (salicylate C$_1$-C$_{12}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);

Substituted Methyl Ethers (Methoxymethyl, Methylthiomethyl, t-Butylthiomethyl, (Phenyldimethylsilyl) methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydrothiopyranyl, 1-Methoxycyclohexyl, 4-Methoxytetrahydropyranyl, 4-Methoxytetrahydrothiopyranyl, 4-Methoxytetrahydrothiopyranyl S,S-Dioxido, 1-[(2-Chloro-4-methyl) phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl));

Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, p-Chlorophenyl, p-Methoxyphenyl, 2,4-Dinitrophenyl, Benzyl);

Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl) bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);

Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl);

Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethyl idine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-, Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

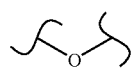

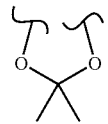

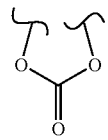

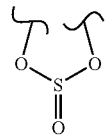

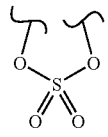

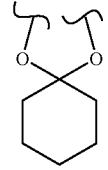

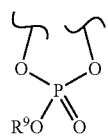

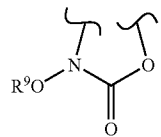

TABLE B-continued

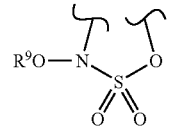

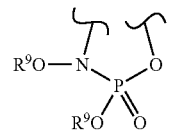

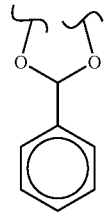

wherein $R^9$ is $C_1$–$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl);

Substituted Ethyl: (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl) propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide);

Imine Derivatives: (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N-isopropylidene, N-p-nitrobenzylidene, N-salicylidene, N-5-chlorosalicylidene, N-(5-chloro-2-hydroxyphenyl) phenylmethylene, N-cyclohexylidene);

Enamine Derivatives: (N-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenyl, N-copper or N-zinc chelate);

N—N Derivatives: (N-nitro, N-nitroso, N-oxide);

N—P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —NHC(O)R$^1$ or —N=CR$^1$N(R$^1$)$_2$. Another protecting group, also useful as a prodrug for amino or —NH(R$^5$), is:

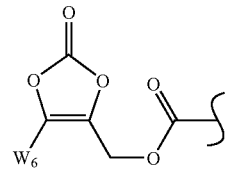

See for example Alexander, J. et al. (1996) *J. Med. Chem.* 39:480-486.

Amino Acid and Polypeptide Protecting Group and Conjugates

An amino acid or polypeptide protecting group of a compound of the invention has the structure R$^{15}$NHCH(R$^{16}$)C(O)—, where R$^{15}$ is H, an amino acid or polypeptide residue, or R$^5$, and R$^{16}$ is defined below.

R$^{16}$ is lower alkyl or lower alkyl (C$_1$-C$_6$) substituted with amino, carboxyl, amide, carboxyl ester, hydroxyl, C$_6$-C$_7$ aryl, guanidinyl, imidazolyl, indolyl, sulfhydryl, sulfoxide, and/or alkylphosphate. R$^{10}$ also is taken together with the amino acid a N to form a proline residue (R$^{10}$=—CH$_2$)$_3$—). However, R$^{10}$ is generally the side group of a naturally-occurring amino acid such as H, —CH$_3$, —CH(CH$_3$)$_2$, —CH$_2$—CH(CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. R$^{10}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, —NHSO$_2$R, NHC(O)R, —N(R)$_2$, NH$_2$ or —NH(R)(H), whereby for example a carboxylic acid is reacted, i.e. coupled, with the amine to form an amide, as in C(O)NR$_2$. A phosphonic acid may be reacted with the amine to form a phosphonamidate, as in —P(O)(OR)(NR$_2$).

In general, amino acids have the structure R$^{17}$C(O)CH(R$^{16}$)NH—, where R$^{17}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono- or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted at $R^3$ of substituents $A^1$, $A^2$ or $A^3$ in Formula I. These conjugates are produced by forming an amide bond between a carboxyl group of the amino acid (or C-terminal amino acid of a polypeptide for example). Similarly, conjugates are formed between $R^3$ (Formula I) and an amino group of an amino acid or polypeptide. Generally, only one of any site in the parental molecule is amidated with an amino acid as described herein, although it is within the scope of this invention to introduce amino acids at more than one permitted site. Usually, a carboxyl group of $R^3$ is amidated with an amino acid. In general, the α-amino or α-carboxyl group of the amino acid or the terminal amino or carboxyl group of a polypeptide are bonded to the parental functionalities, i.e., carboxyl or amino groups in the amino acid side chains generally are not used to form the amide bonds with the parental compound (although these groups may need to be protected during synthesis of the conjugates as described further below).

With respect to the carboxyl-containing side chains of amino acids or polypeptides it will be understood that the carboxyl group optionally will be blocked, e.g., by $R^1$, esterified with $R^5$ or amidated. Similarly, the amino side chains $R^{16}$ optionally will be blocked with $R^1$ or substituted with $R^5$.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, δ-hydroxynorvaline, γ-hydroxynorvaline and ε-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may not need to be immunogenic in an animal typically used to raise antibodies, e.g., rabbit, mouse, horse, or rat, but the final product conjugate should be immunogenic in at least one of such animals. The polypeptide optionally contains a peptidolytic enzyme cleavage site at the peptide bond between the first and second residues adjacent to the acidic heteroatom. Such cleavage sites are flanked by enzymatic recognition structures, e.g., a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In claims where $W_1$ is phosphonate it is expected that this peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence —$X^4$-pro-$X^5$-(where $X^4$ is any amino acid residue and $X^5$ is an amino acid residue, a carboxyl ester of proline, or hydrogen) will be cleaved by luminal carboxypeptidase to yield $X^4$ with a free carboxyl, which in turn is expected to autocatalytically cleave the phosphonoamidate bond. The carboxy group of $X^5$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) *Pharm Res.* 9:969-978). Transport competent peptides can thus be used to enhance bioavailability of the amidate compounds. Di- or tripeptides having one or more amino acids in the D configuration are also compatible with peptide transport and can be utilized in the amidate compounds of this invention. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

SPECIFIC EMBODIMENTS OF THE INVENTION

Specific values described for radicals, substituents, and ranges, as well as specific embodiments of the invention described herein, are for illustration only; they do not exclude other defined values or other values within defined ranges.

In one specific embodiment of the invention, the conjugate is a compound that is substituted with one or more phosphonate groups either directly or indirectly through a linker; and that is optionally substituted with one or more groups $A^0$; or a pharmaceutically acceptable salt thereof, wherein:

$A^0$ is $A^1$, $A^2$ or $W^3$;

$A^1$ is:

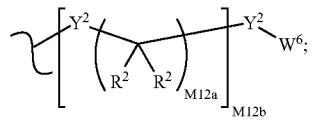

$A^2$ is:

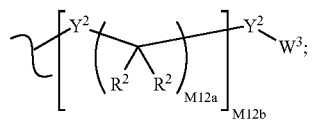

$A^3$ is:

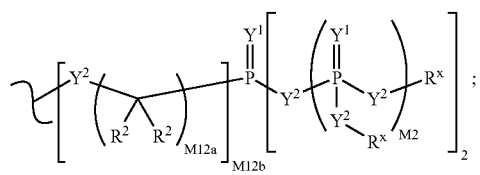

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $R^1$, $W^3$, a protecting group, or the formula:

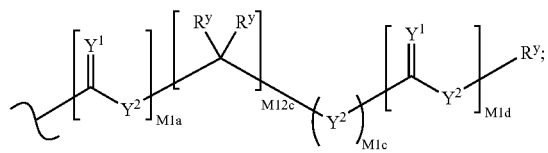

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{1b}$ is $Y^1$;

$R^{3c}$ is $-R^x$, $N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $-C(Y^1)R^5$, $-C(Y^1)W^5$, $-SO_2R^5$, or $-SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another specific embodiment of the invention $A^1$ is of the formula:

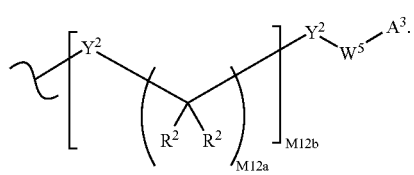

In another specific embodiment of the invention $A^1$ is of the formula:

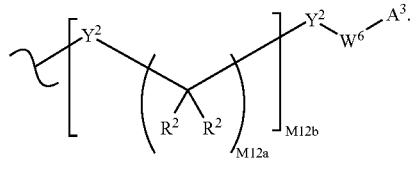

In another specific embodiment of the invention $A^1$ is of the formula:

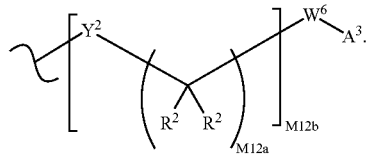

In another specific embodiment of the invention $A^1$ is of the formula:

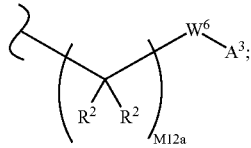

In another specific embodiment of the invention $A^1$ is of the formula:

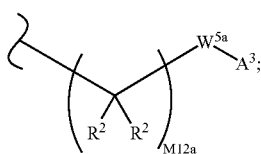

and $W^{5a}$ is a carbocycle or a heterocycle where $W^{5a}$ is independently substituted with 0 or 1 $R^2$ groups. A specific velue for M12a is 1.

In another specific embodiment of the invention $A^1$ is of the formula:

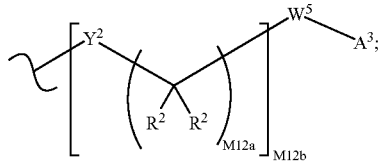

In another specific embodiment of the invention $A^1$ is of the formula:

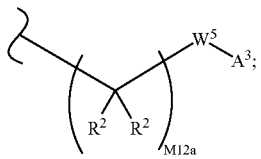

In another specific embodiment of the invention $A^1$ is of the formula:

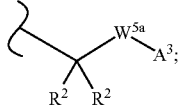

wherein $W^{5a}$ is a carbocycle independently substituted with 0 or 1 $R^2$ groups;

In another specific embodiment of the invention $A^1$ is of the formula:

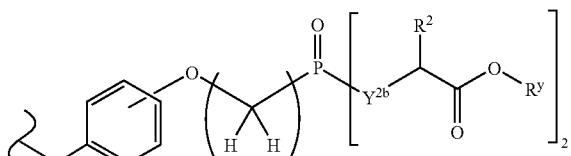

wherein $Y^{2b}$ is O or $N(R^2)$; and M12d is 1, 2, 3, 4, 5, 6, 7 or 8.

In another specific embodiment of the invention $A^1$ is of the formula:

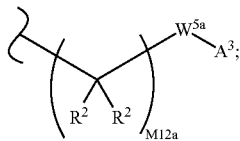

wherein $W^{5a}$ is a carbocycle independently substituted with 0 or 1 $R^2$ groups;

In another specific embodiment of the invention $A^1$ is of the formula:

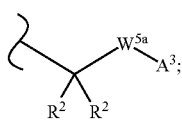

wherein $W^{5a}$ is a carbocycle or heterocycle where $W^{5a}$ is independently substituted with 0 or 1 $R^2$ groups.

In another specific embodiment of the invention $A^1$ is of the formula:

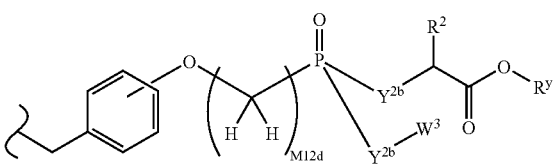

wherein $Y^{2b}$ is O or $N(R^2)$; and M12d is 1, 2, 3, 4, 5, 6, 7 or 8.

In a specific embodiment of the invention $A^2$ is of the formula:

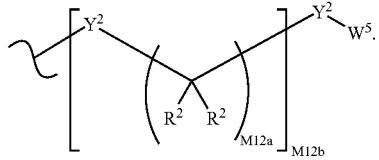

In another specific embodiment of the invention $A^2$ is of the formula:

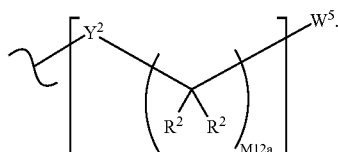

In another specific embodiment of the invention M12b is 1.

In another specific embodiment of the invention e M12b is 0, $Y^2$ is a bond and $W^5$ is a carbocycle or heterocycle where $W^5$ is optionally and independently substituted with 1, 2, or 3 $R^2$ groups.

In another specific embodiment of the invention $A^2$ is of the formula:

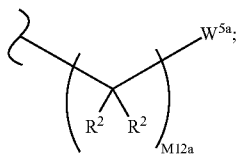

wherein $W^{5a}$ is a carbocycle or heterocycle where $W^{5a}$ is optionally and independently substituted with 1, 2, or 3 $R^2$ groups.

In another specific embodiment of the invention M12a is 1.

In another specific embodiment of the invention $A^2$ is selected from phenyl, substituted phenyl, benzyl, substituted benzyl, pyridyl and substituted pyridyl.

In another specific embodiment of the invention $A^2$ is of the formula:

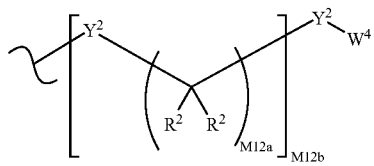

In another specific embodiment of the invention $A^2$ is of the formula:

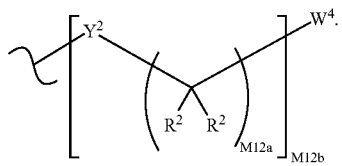

In another specific embodiment of the invention M12b is 1.

In a specific embodiment of the invention $A^3$ is of the formula:

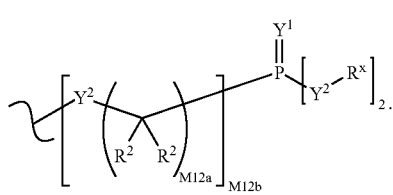

In another specific embodiment of the invention $A^3$ is of the formula:

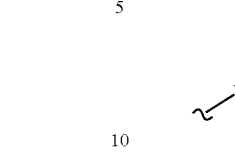

In another specific embodiment of the invention $A^3$ is of the formula:

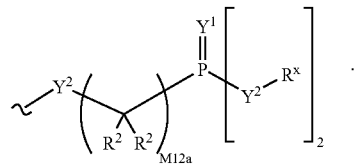

wherein $Y^{1a}$ is O or S; and $Y^{2a}$ is O, $N(R^x)$ or S.

In another specific embodiment of the invention $A^3$ is of the formula:

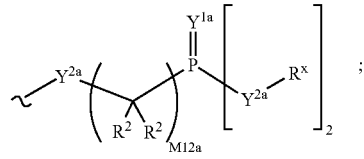

wherein $Y^{2b}$ is O or $N(R^x)$.

In another specific embodiment of the invention $A^3$ is of the formula:

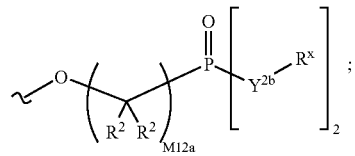

wherein $Y^{2b}$ is O or $N(R^x)$; and M12d is 1, 2, 3, 4, 5, 6, 7 or 8.

In another specific embodiment of the invention $A^3$ is of the formula:

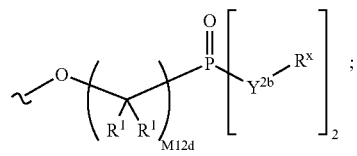

wherein $Y^{2b}$ is O or $N(R^x)$; and M12d is 1, 2, 3, 4, 5, 6, 7 or 8.

In another specific embodiment of the invention M12d is 1.

In another specific embodiment of the invention $A^3$ is of the formula:

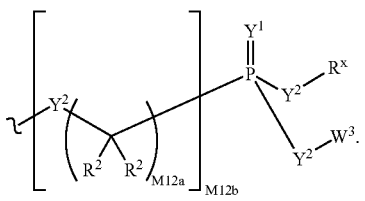

In another specific embodiment of the invention $A^3$ is of the formula:

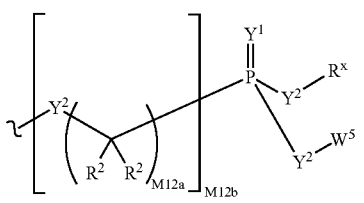

In another specific embodiment of the invention $W^5$ is a carbocycle.

In another specific embodiment of the invention $A^3$ is of the formula:

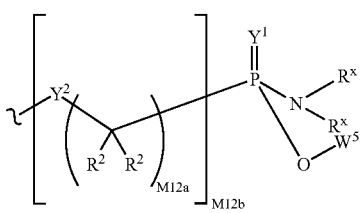

In another specific embodiment of the invention $W^5$ is phenyl.

In another specific embodiment of the invention $A^3$ is of the formula:

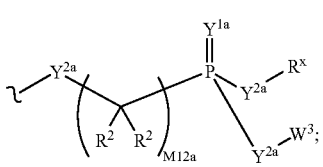

wherein $Y^{1a}$ is O or S; and $Y^{2a}$ is O, $N(R^x)$ or S.

In another specific embodiment of the invention $A^3$ is of the formula:

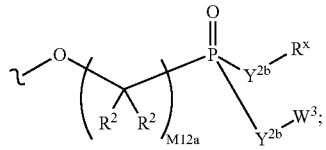

wherein $Y^{2b}$ is O or $N(R^x)$.

In another specific embodiment of the invention $A^3$ is of the formula:

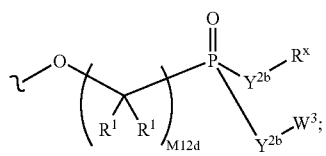

wherein $Y^{2b}$ is O or $N(R^x)$; and M12d is 1, 2, 3, 4, 5, 6, 7 or 8.

In another specific embodiment of the invention $R^1$ is H.

In another specific embodiment of the invention $A^3$ is of the formula:

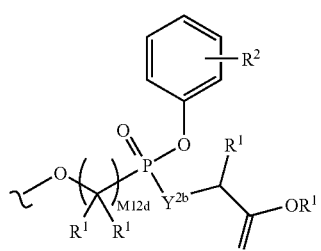

wherein the phenyl carbocycle is substituted with 0, 1, 2, or 3 $R^2$ groups.

In another specific embodiment of the invention A³ is of the formula:

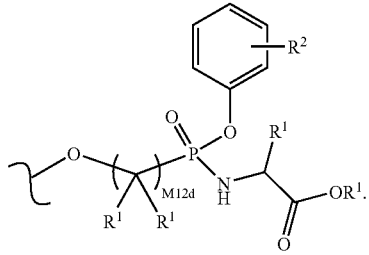

In another specific embodiment of the invention A³ is of the formula:

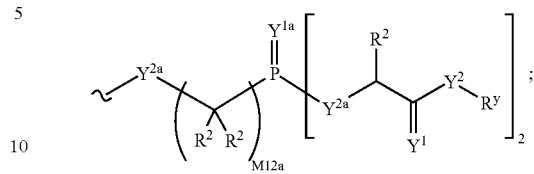

wherein Y$^{1a}$ is O or S; and Y$^{2a}$ is O, N(R²) or S.

In another specific embodiment of the invention A³ is of the formula:

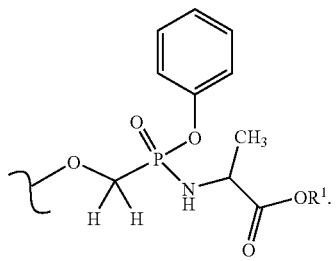

In another specific embodiment of the invention A³ is of the formula:

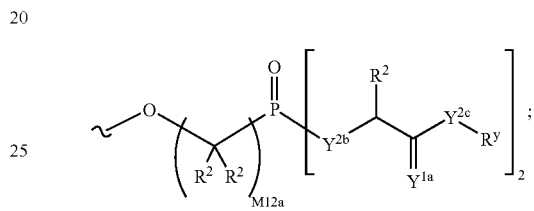

wherein Y$^{1a}$ is O or S; Y$^{2b}$ is O, or N(R²); and Y$^{2c}$ is O, N(R$^y$) or S.

In another specific embodiment of the invention A³ is of the formula:

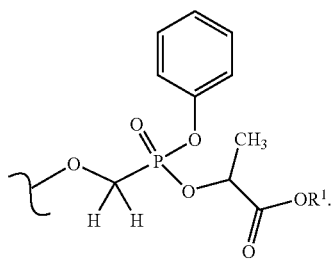

In another specific embodiment of the invention A³ is of the formula:

wheren Y$^{1a}$ is O or S; Y$^{2b}$ is O or N(R²); Y$^{2d}$ is O or N(R$^y$); and M12d is 1, 2, 3, 4, 5, 6, 7 or 8.

In another specific embodiment of the invention A³ is of the formula:

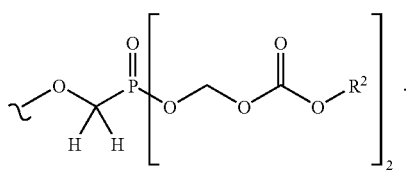

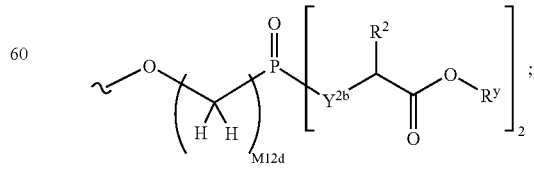

wherein Y$^{2b}$ is O or N(R²); and M12d is 1, 2, 3, 4, 5, 6, 7 or 8.

In another specific embodiment of the invention $A^3$ is of the formula:

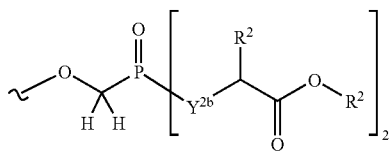

wherein $Y^{2b}$ is O or $N(R^2)$.

In another specific embodiment of the invention $A^3$ is of the formula:

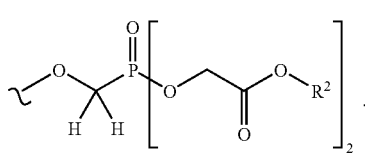

In another specific embodiment of the invention $A^3$ is of the formula:

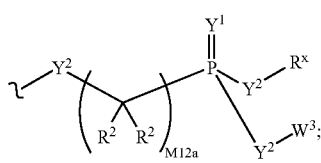

In another specific embodiment of the invention $A^3$ is of the formula:

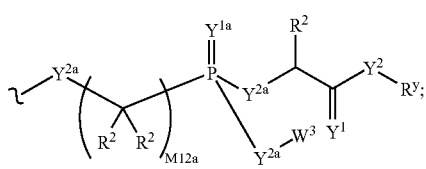

wherein $Y^{1a}$ is O or S; and $Y^{2a}$ is O, $N(R^2)$ or S.

In another specific embodiment of the invention $A^3$ is of the formula:

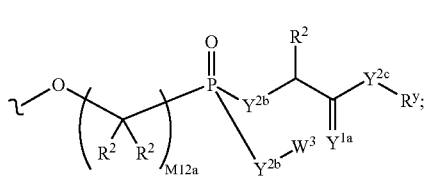

wherein $Y^{1a}$ is O or S; $Y^{2b}$ is O or $N(R^2)$; and $Y^{2c}$ is O, $N(R^y)$ or S.

In another specific embodiment of the invention $A^3$ is of the formula:

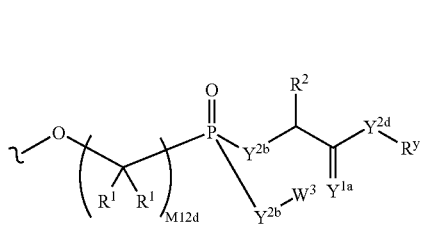

wherein $Y^{1a}$ is O or S; $Y^{2b}$ is O or $N(R^2)$; $Y^{2d}$ is O or $N(R^y)$; and M12d is 1, 2, 3, 4, 5, 6, 7 or 8.

In another specific embodiment of the invention $A^3$ is of the formula:

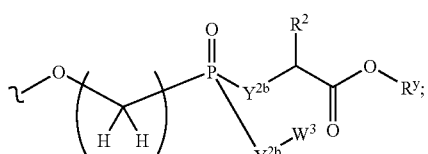

wherein $Y^{2b}$ is O or $N(R^2)$; and M12d is 1, 2, 3, 4, 5, 6, 7 or 8.

In another specific embodiment of the invention $A^3$ is of the formula:

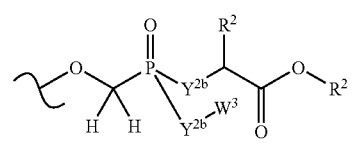

wherein $Y^{2b}$ is O or $N(R^2)$.

In another specific embodiment of the invention $A^3$ is of the formula:

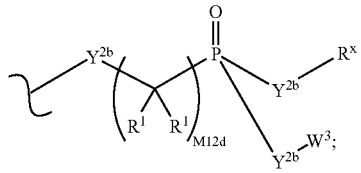

wherein:
$Y^{2b}$ is O or $N(R^x)$; and M12d is 1, 2, 3, 4, 5, 6, 7 or 8.

In another specific embodiment of the invention $A^3$ is of the formula:

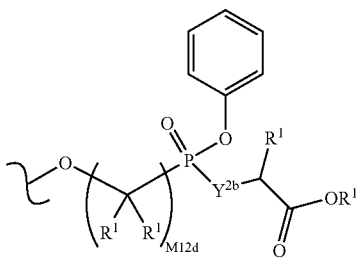

wherein the phenyl carbocycle is substituted with 0, 1, 2, or 3 $R^2$ groups.

In another specific embodiment of the invention $A^3$ is of the formula:

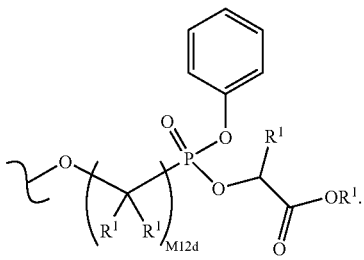

wherein the phenyl carbocycle is substituted with 0, 1, 2, or 3 $R^2$ groups.

In another specific embodiment of the invention $A^3$ is of the formula:

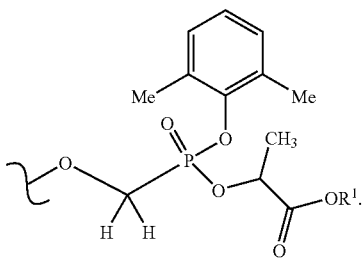

In a specific embodiment of the invention $A^0$ is of the formula:

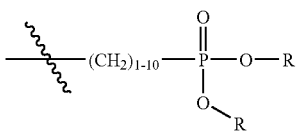

wherein each R is independently $(C_1$-$C_6)$alkyl.

In a specific embodiment of the invention $R^x$ is independently H, $R^1$, $W^3$, a protecting group, or the formula:

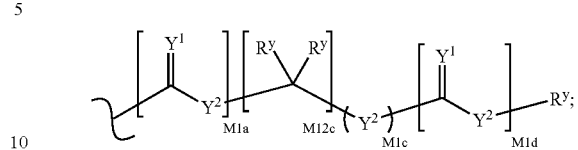

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

In a specific embodiment of the invention $R^x$ is of the formula:

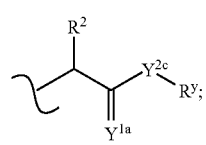

wherein $Y^{1a}$ is O or S; and $Y^{2c}$ is O, $N(R^y)$ or S.

In a specific embodiment of the invention $R^x$ is of the formula:

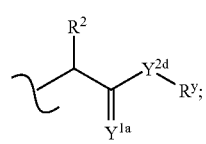

wherein $Y^{1a}$ is O or S; and $Y^{2d}$ is O or $N(R^y)$.

In a specific embodiment of the invention $R^x$ is of the formula:

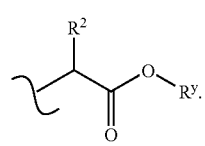

In a specific embodiment of the invention $R^y$ is hydrogen or alkyl of 1 to 10 carbons.

In a specific embodiment of the invention $R^x$ is of the formula:

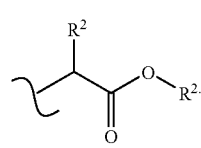

In a specific embodiment of the invention $R^x$ is of the formula:

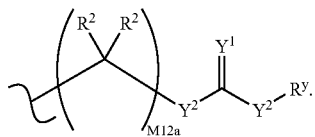

In a specific embodiment of the invention $R^x$ is of the formula:

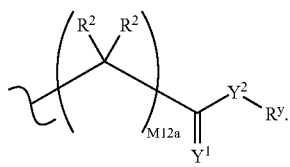

In a specific embodiment of the invention $Y^1$ is O or S.

In a specific embodiment of the invention $Y^2$ is O, $N(R^y)$ or S.

In one specific embodiment of the invention $R^x$ is a group of the formula:

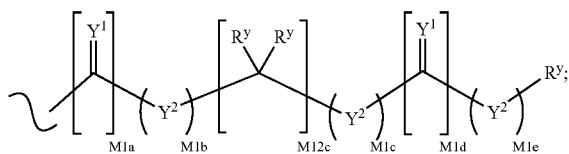

wherein:
m1a, m1b, m1c, m1d and m1e are independently 0 or 1;
m12c is 0, 1, 2, 3, 4, 5, 6, 7, 8, 9, 10, 11 or 12;
$R^y$ is H, $W^3$, $R^2$ or a protecting group; provided that:
if m1a, m12c, and m1d are 0, then m1b, m1c and m1e are 0;
if m1a and m12c are 0 and m1d is not 0, then m1b and m1c are 0;
if m1a and m1d are 0 and m12c is not 0, then m1b and at least one of m1c and m1e are 0;
if m1a is 0 and m12c and m1d are not 0, then m1b is 0;
if m12c and m1d are 0 and m1a is not 0, then at least two of m1b, m1c and m1e are 0;
if m12c is 0 and m1a and m1d are not 0, then at least one of m1b and m1c are 0; and
if m1d is 0 and m1a and m12c are not 0, then at least one of m1c and m1e are 0.

In another specific embodiment, the invention provides a compound of the formula:

[DRUG]–(A⁰)$_{nn}$ or a pharmaceutically acceptable salt thereof wherein,
DRUG is a compound of any one of formulae 500-601:
nn is 1, 2, or 3;
$A^0$ is $A^1$, $A^2$ or $W^3$ with the proviso that the compound includes at least one $A^1$;

$A^1$ is:

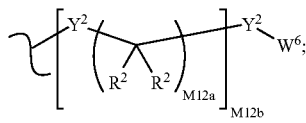

$A^2$ is:

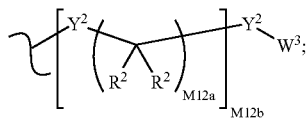

$A^3$ is:

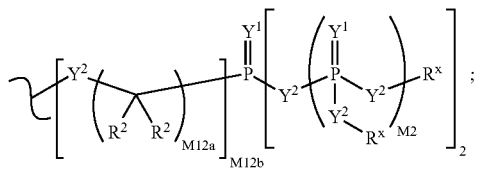

$Y^1$ is independently O, S, $N(R^x)$, $N(O)(R^x)$, $N(OR^x)$, $N(O)(OR^x)$, or $N(N(R^x)(R^x))$;
$Y^2$ is independently a bond, O, $N(R^x)$, $N(O)(R^x)$, $N(OR^x)$, $N(O)(OR^x)$, $N(N(R^x)(R^x))$, —$S(O)_{M2}$—, or —$S(O)_{M2}$—S(O)$_{M2}$—;
$R^x$ is independently H, $R^1$, $W^3$, a protecting group, or the formula:

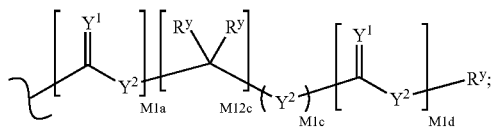

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, —CN, $N_3$ or —$NO_2$;
$R^{3b}$ is $Y^1$;
$R^{3c}$ is $R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;
$R^{3d}$ is —$C(Y^1)R^x$, —$C(Y^1)OR^x$ or —$C(Y^1)(N(R^x)(R^x))$;
$R^4$ is an alkyl of 1 to 18 carbon atoms, alkenyl of 2 to 18 carbon atoms, or alkynyl of 2 to 18 carbon atoms;
$R^5$ is $R^4$ wherein each $R^4$ is substituted with 0 to 3 $R^3$ groups;
$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;
$W^3$ is $W^4$ or $W^5$;

W⁴ is R⁵, —C(Y¹)R⁵, —C(Y¹)W⁵, —SO₂R⁵, or —SO₂W⁵;
W⁵ is carbocycle or heterocycle wherein W⁵ is independently substituted with 0 to 3 R² groups;
W⁶ is W³ independently substituted with 1, 2, or 3 A³ groups;
M2 is 0, 1 or 2;
M2a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1; and
M12c is 0, 1, 2, 3, 4, 5, 6, 7, 8, 9, 10, 11 or 12.
In another specific embodiment, the invention provides a compound of the formula 1-336:
1
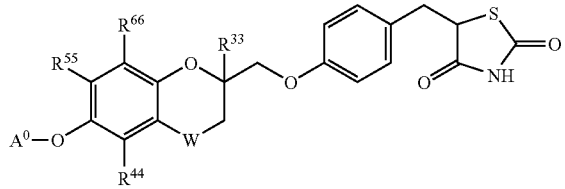
2
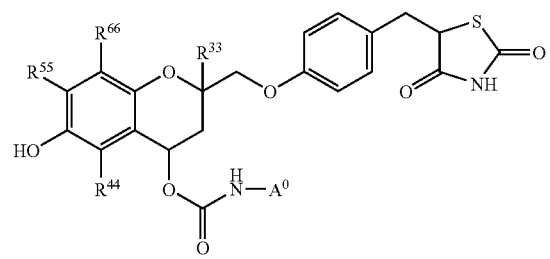
3
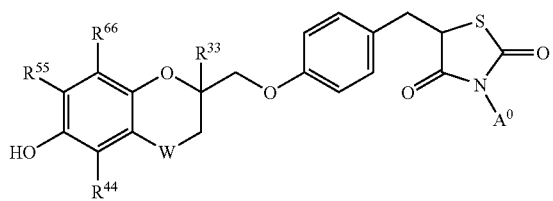
4
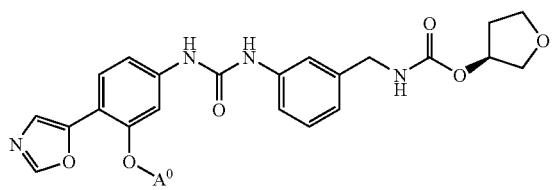
5
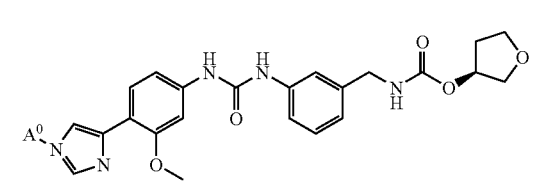
-continued
6
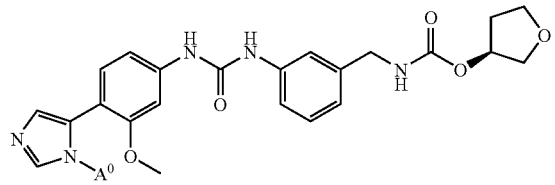
7
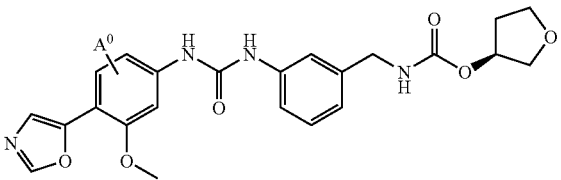
8
9
10
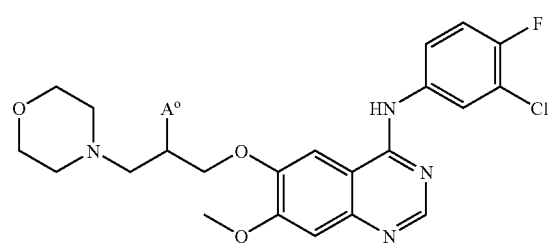

-continued
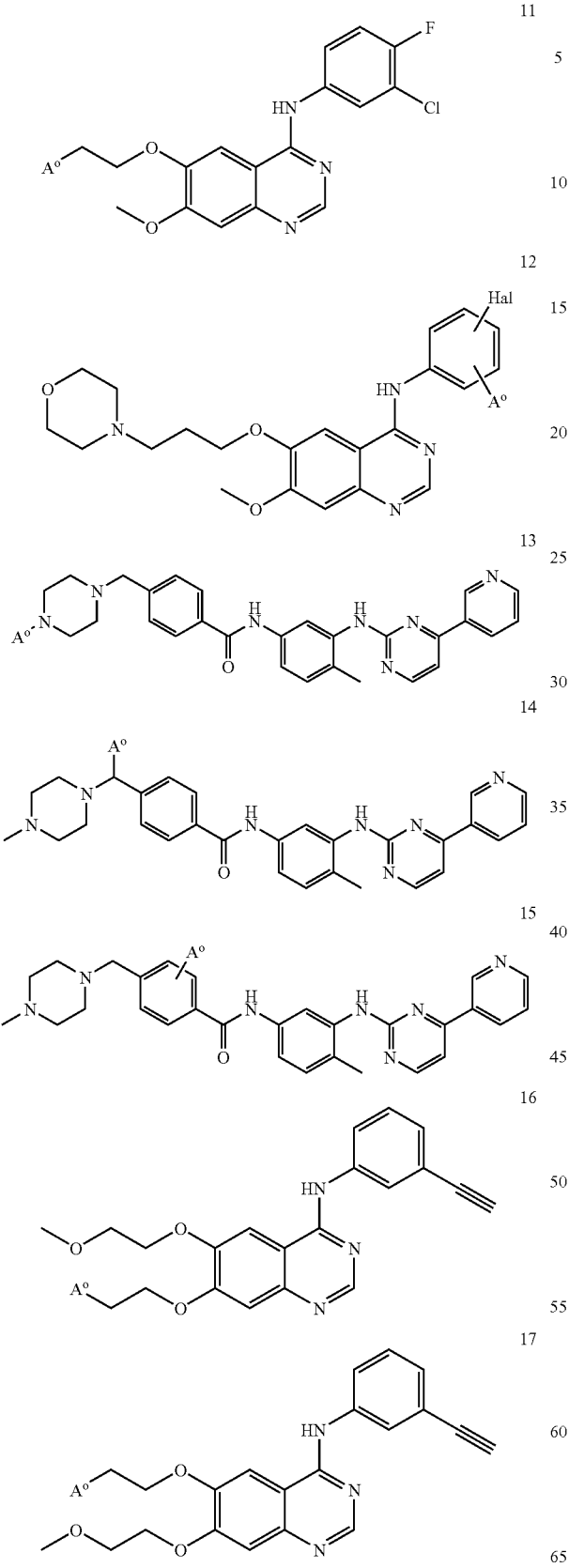
-continued
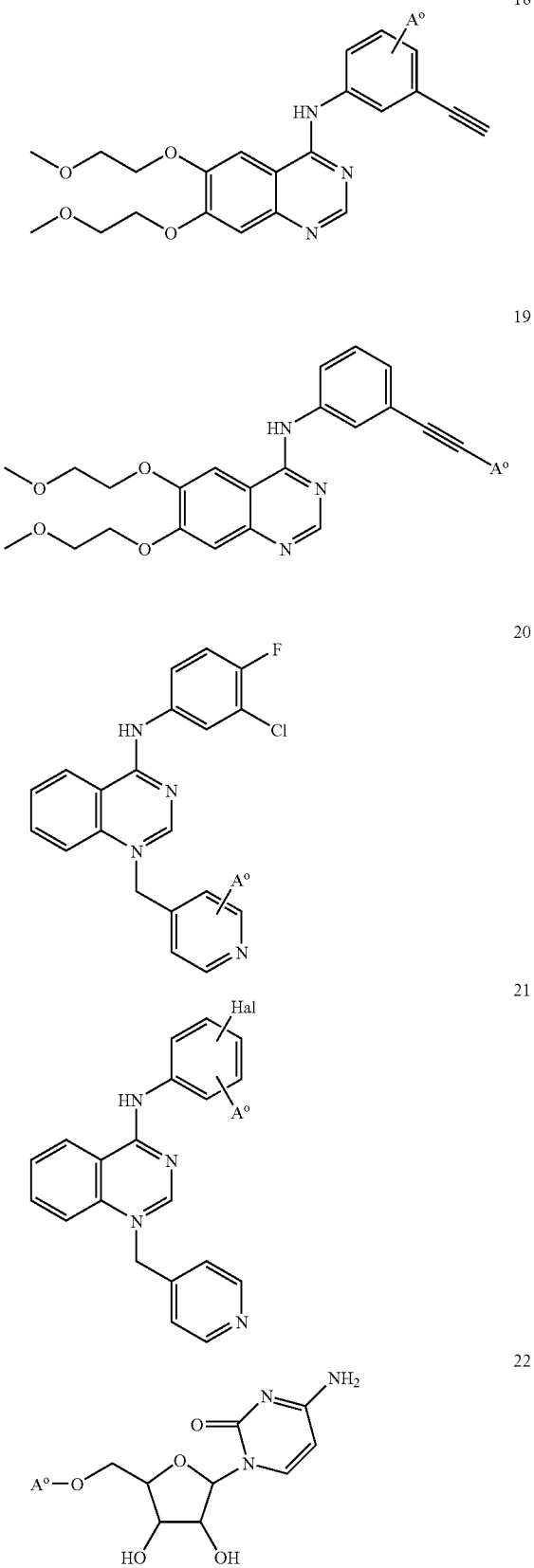

23
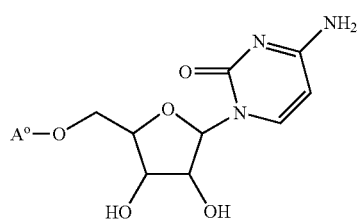
24
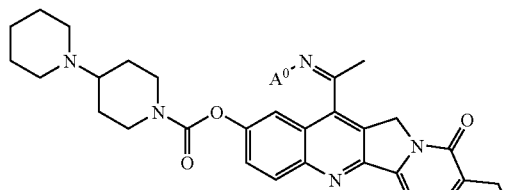
25
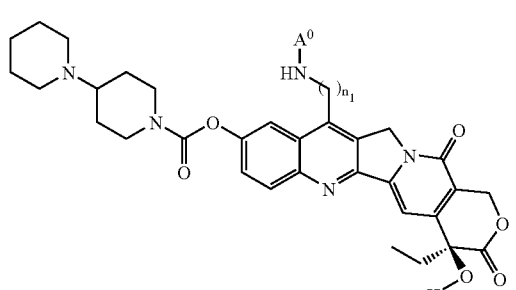
26
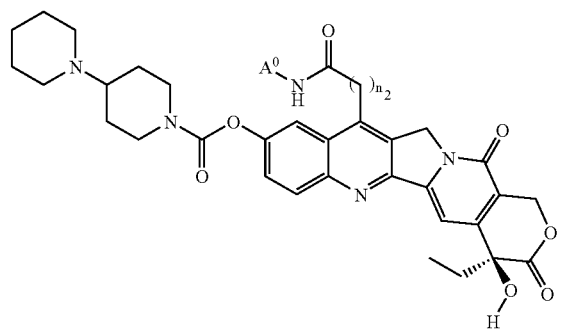
27
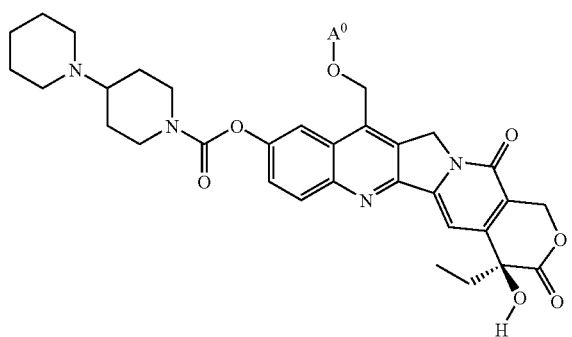
28
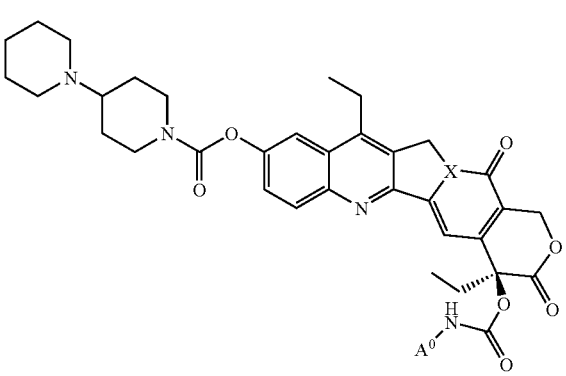
29
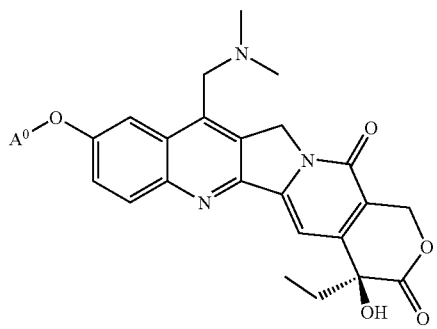
30
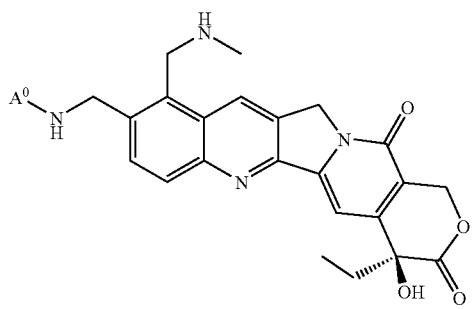
31
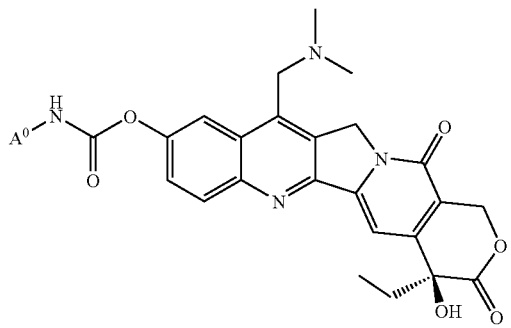

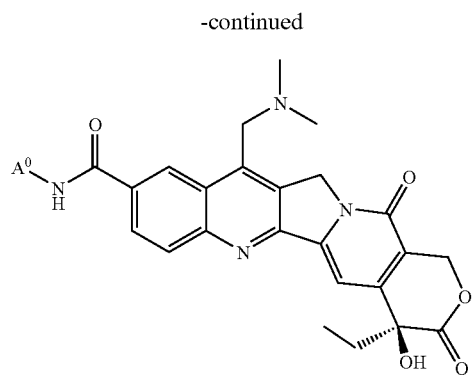
32
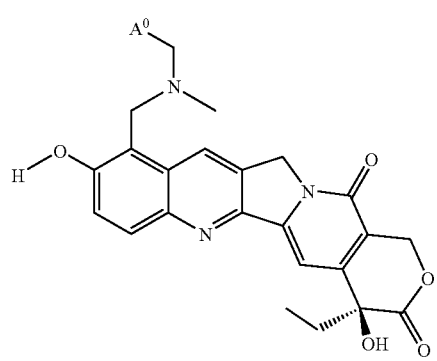
33
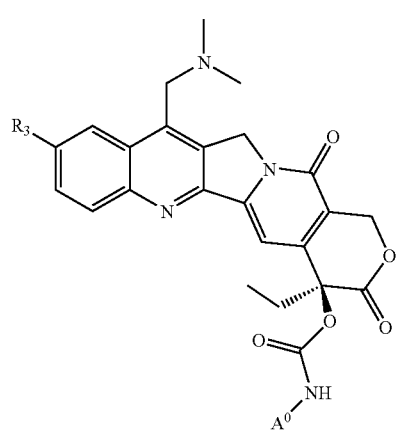
34
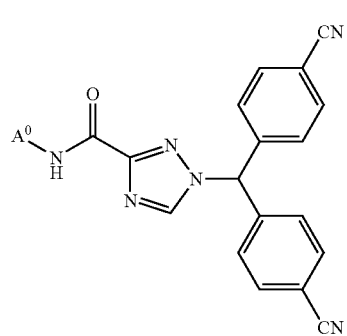
35
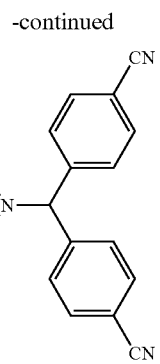
36
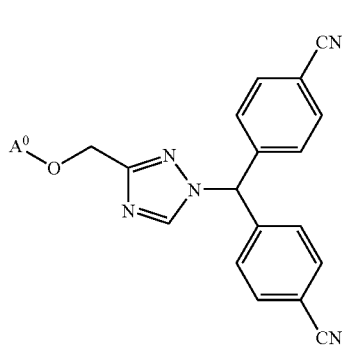
37
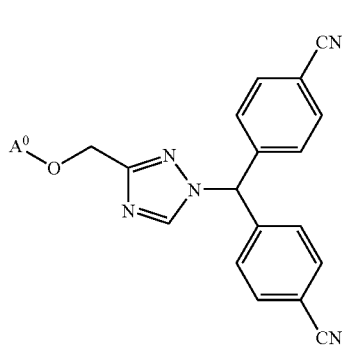
38
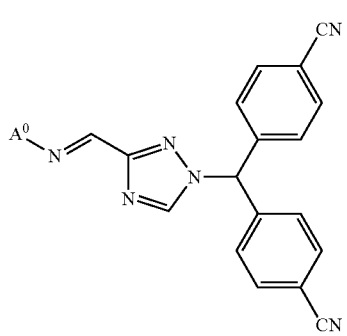
39

-continued
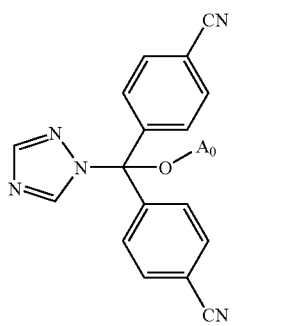
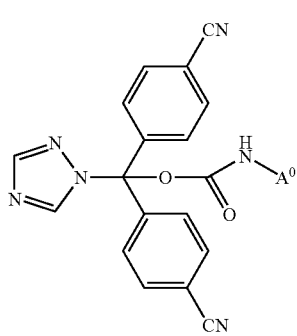
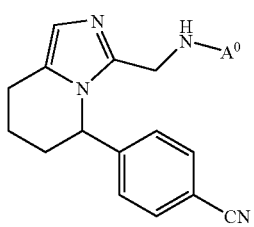
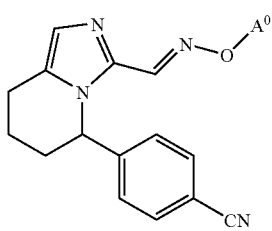
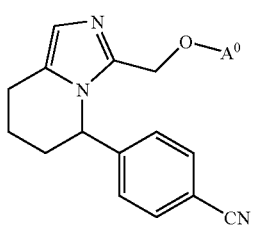
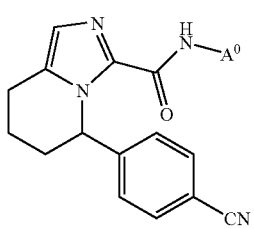
-continued
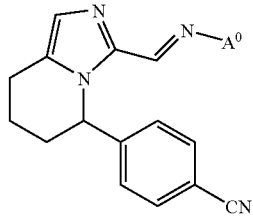
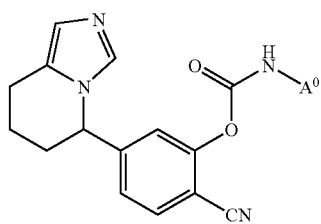
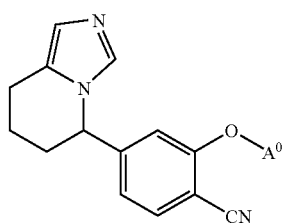
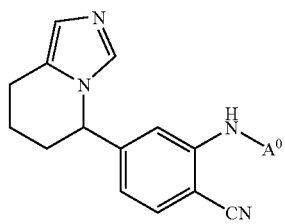
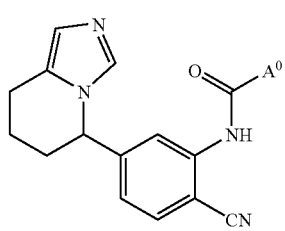

-continued
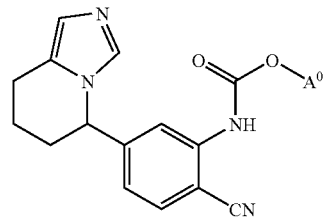
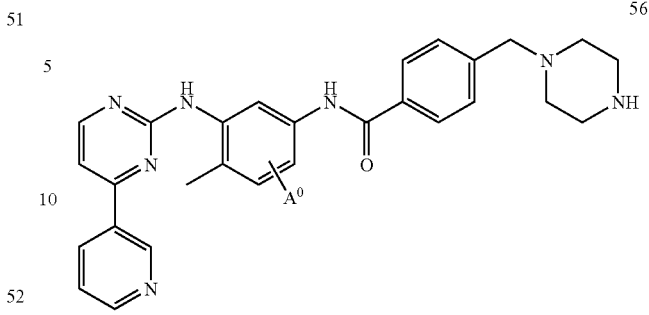
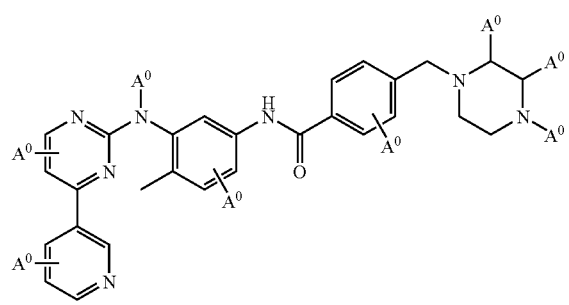
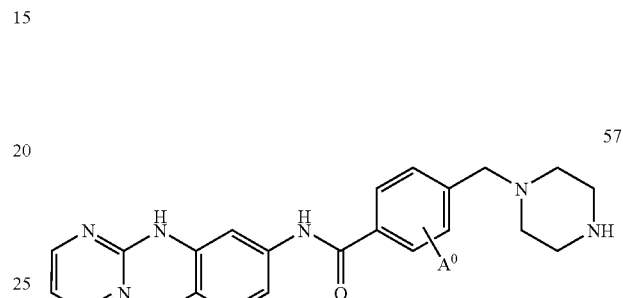
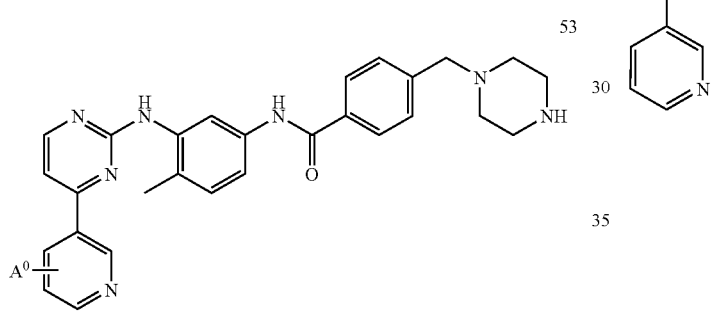
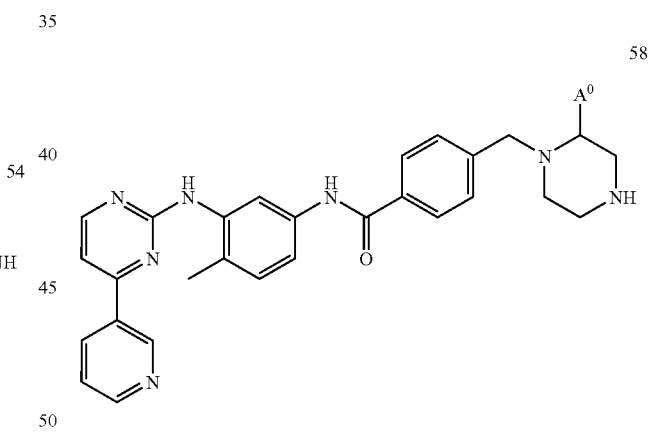
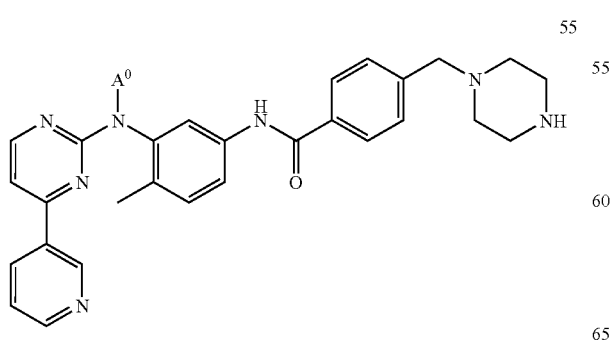
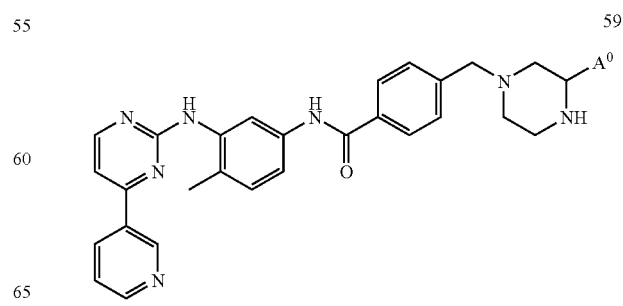

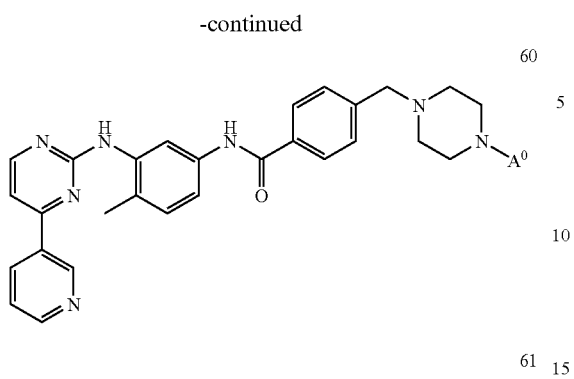
60
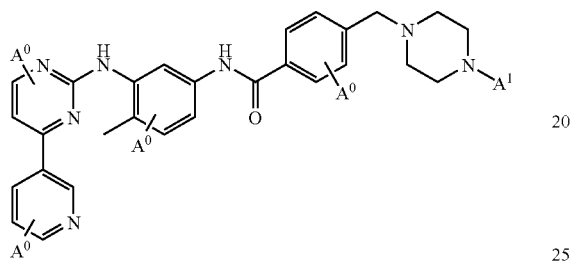
61
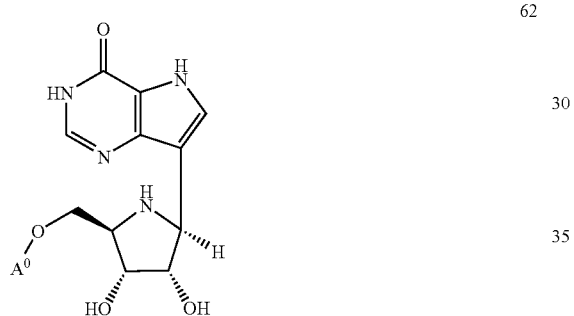
62
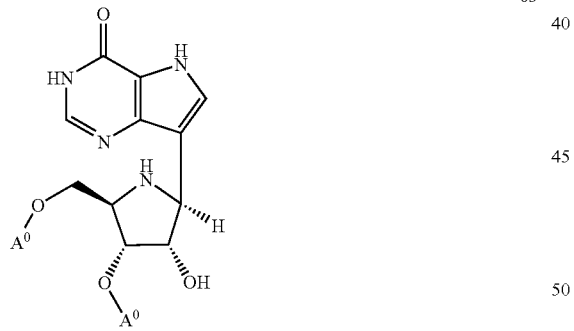
63
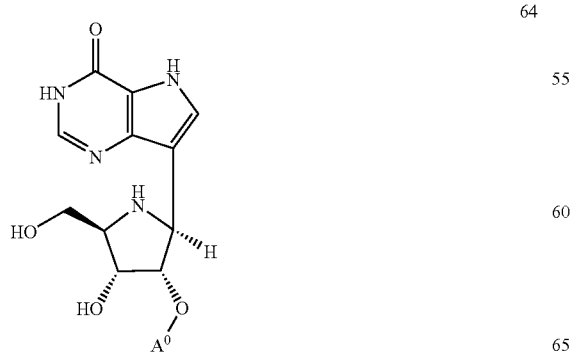
64
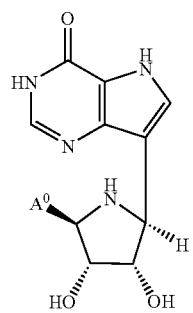
65
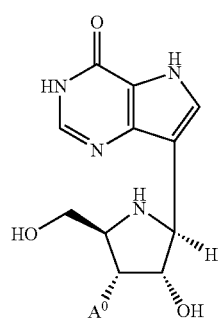
66
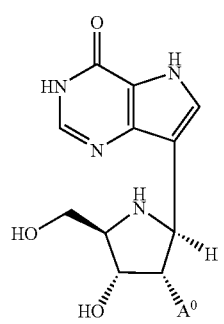
67
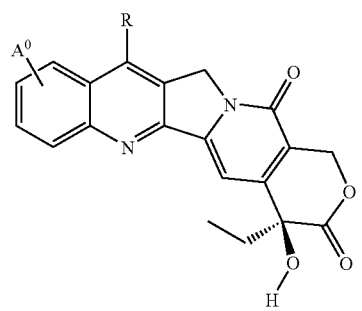
68

-continued
69 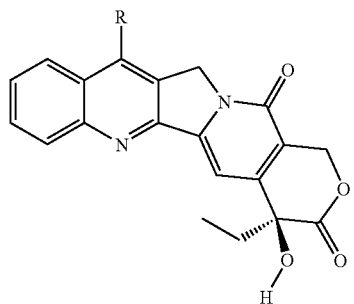
70 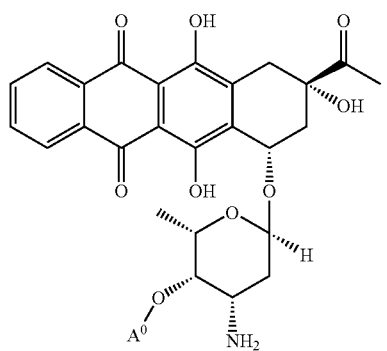
71 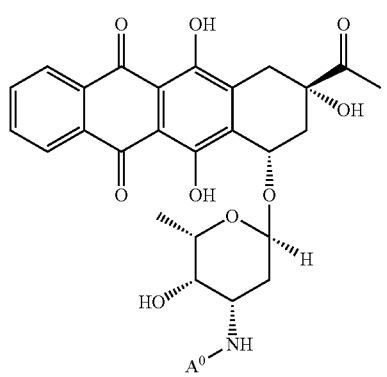
72 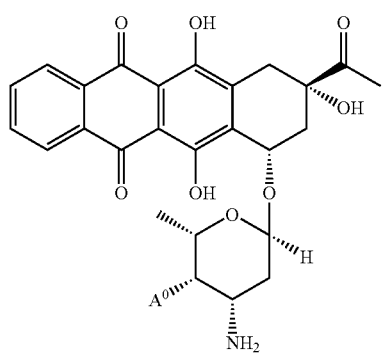
-continued
73 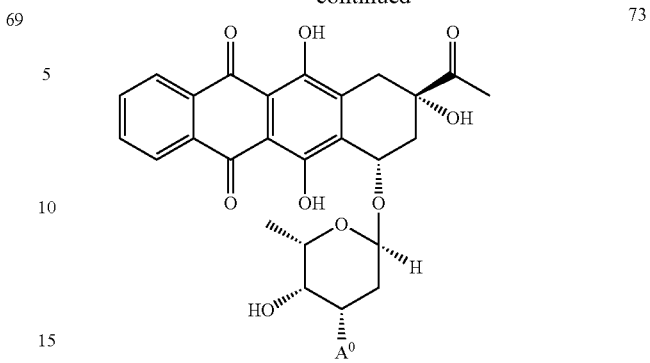
74 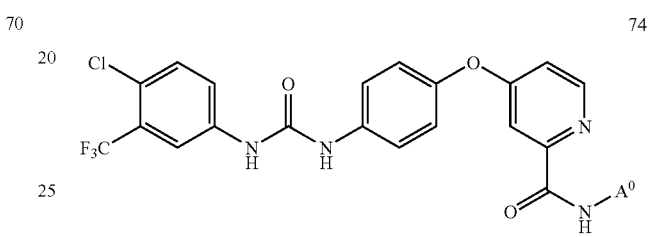
75 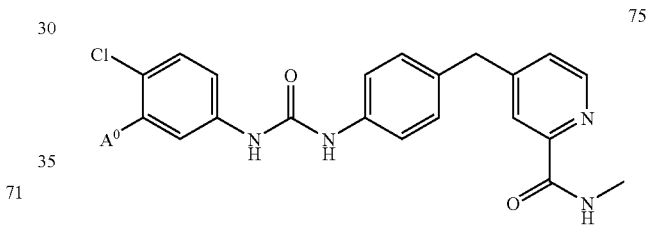
76 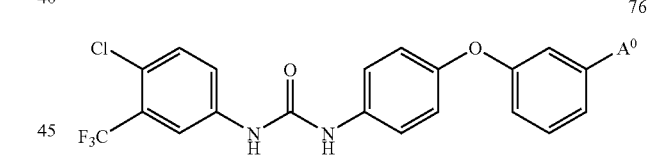
77 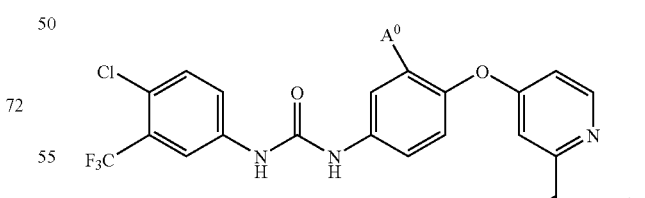
78 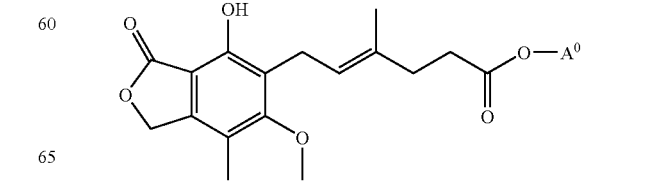

153 154
79
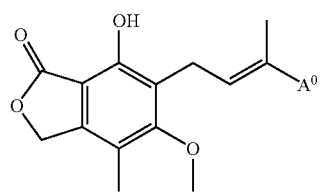
83
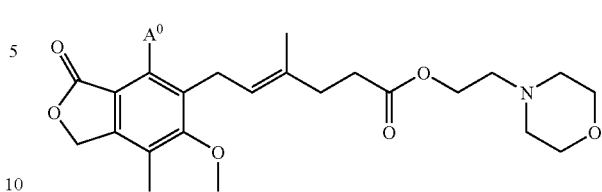
80
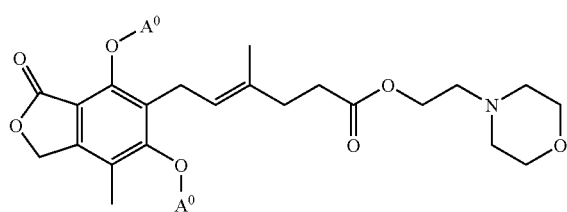
84
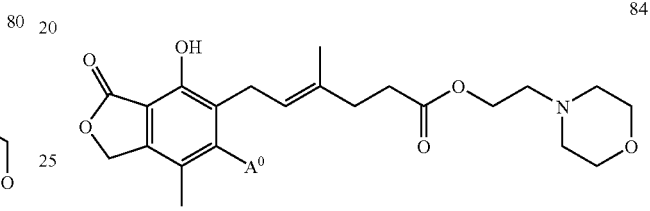
81
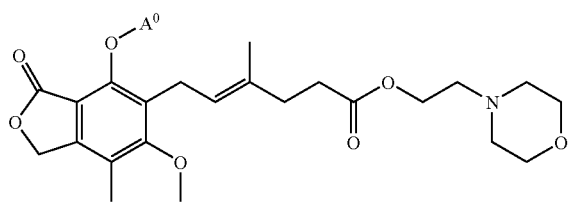
85
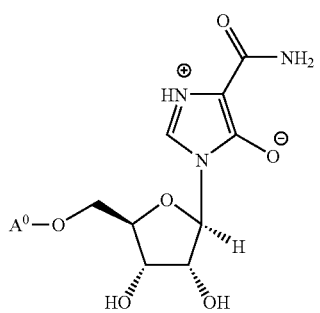
82
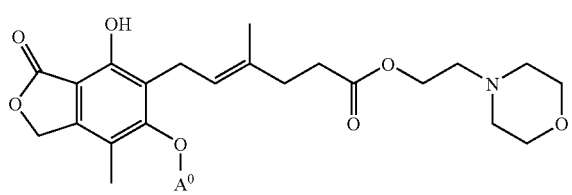
86
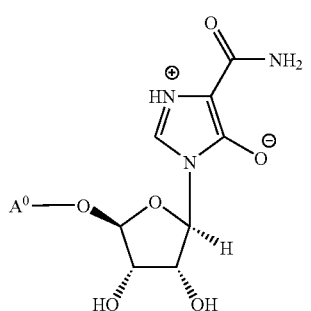

87
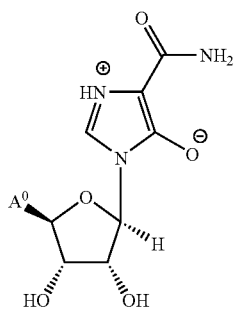
88
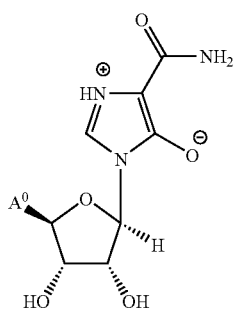
89
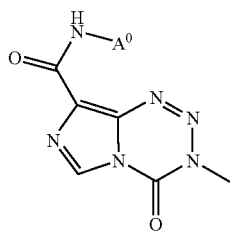
90
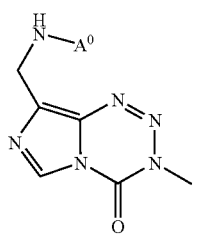
91
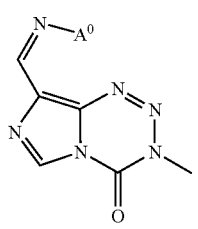
92
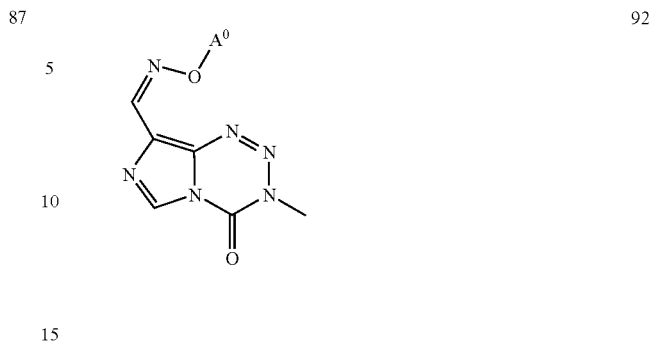
93
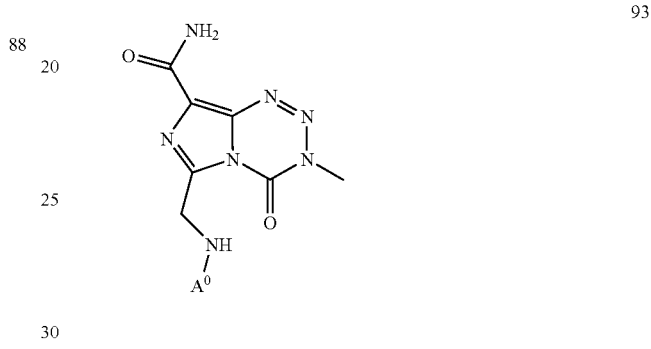
94
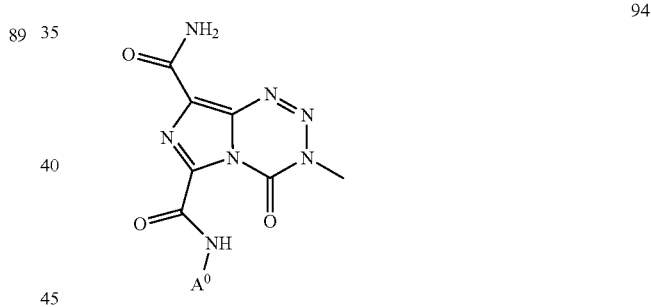
95
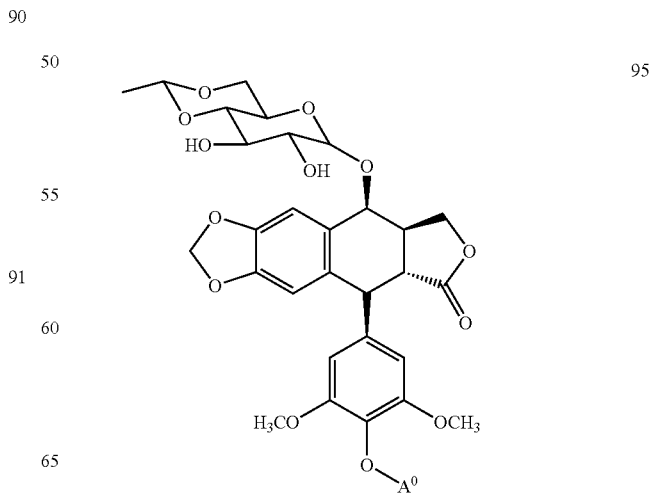

96
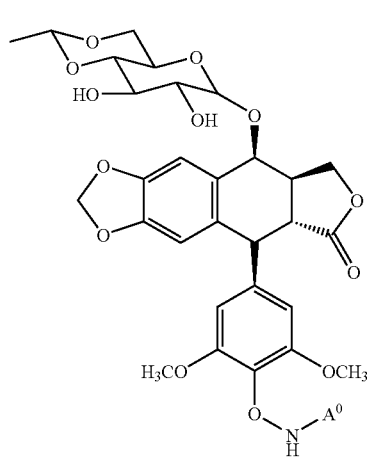
97
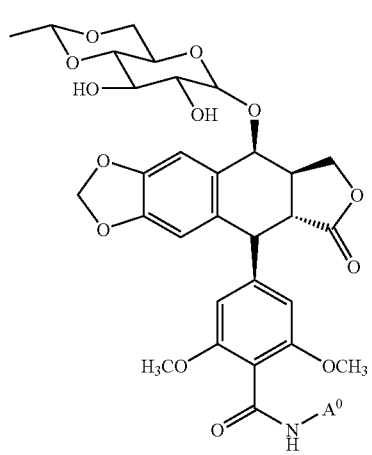
98
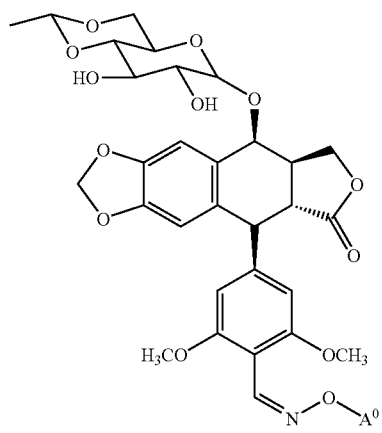
99
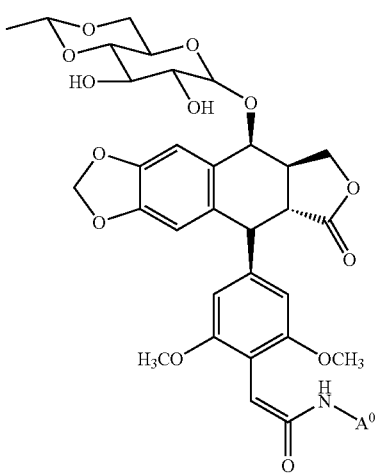
100
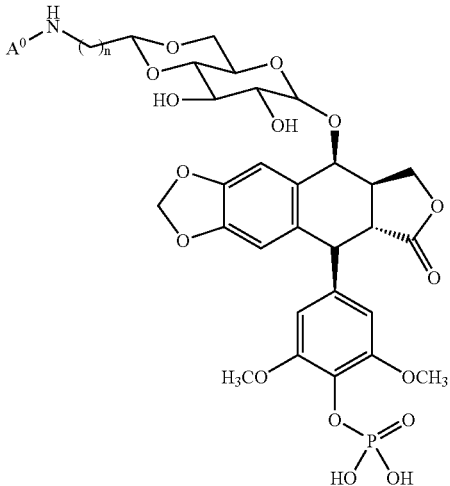
101
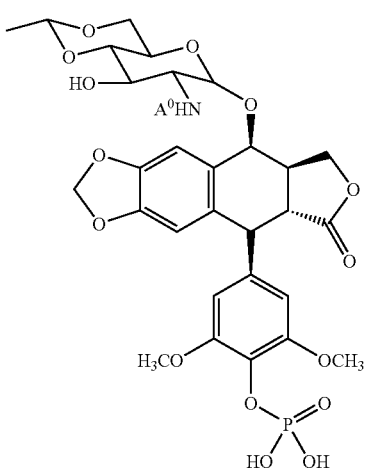

102
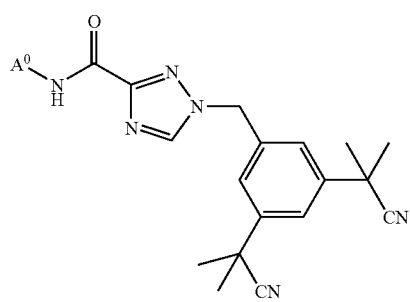
103
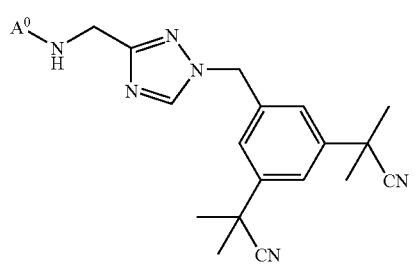
104
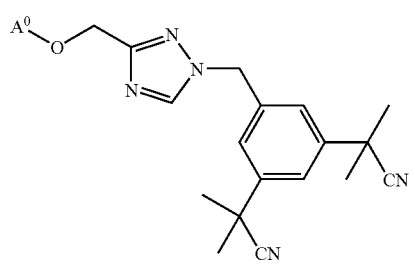
105
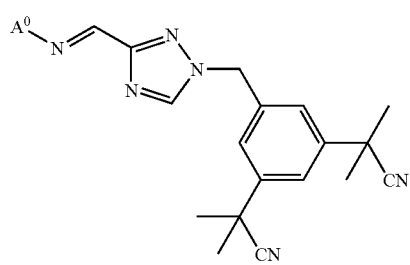
106
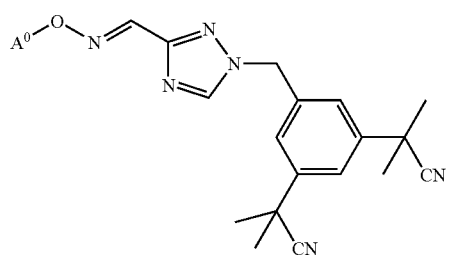
107
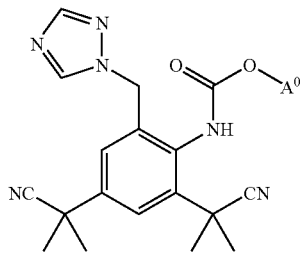
108
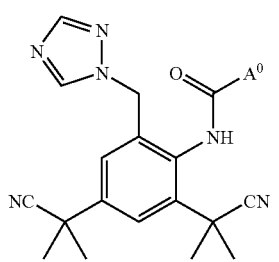
109
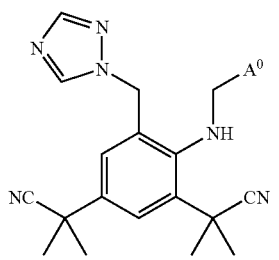
110
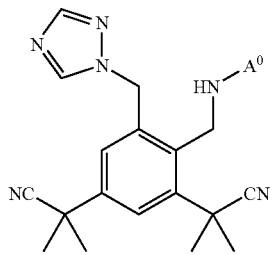

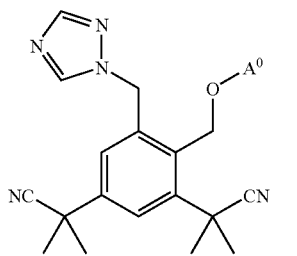
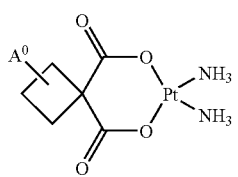
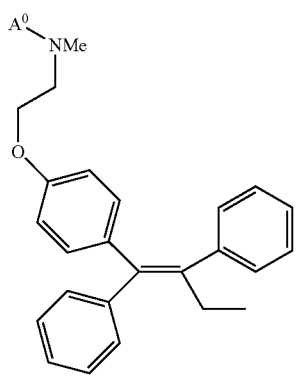
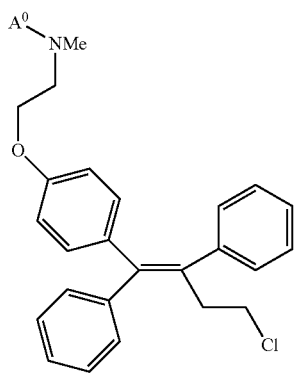
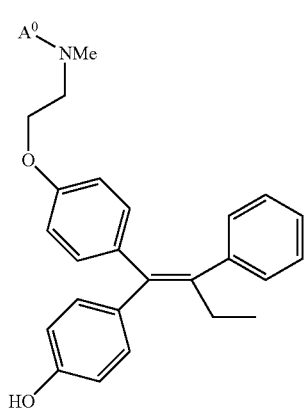
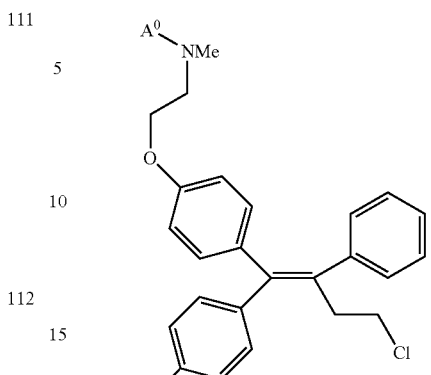
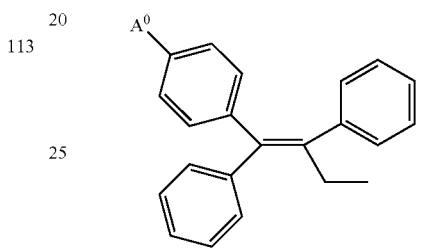
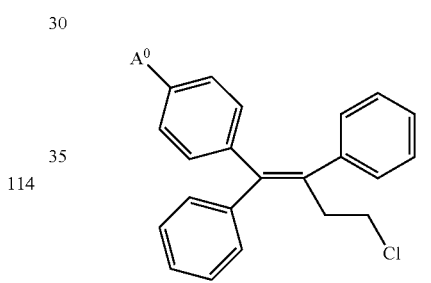
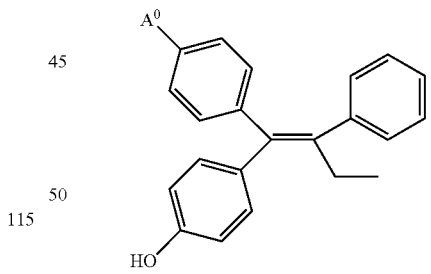
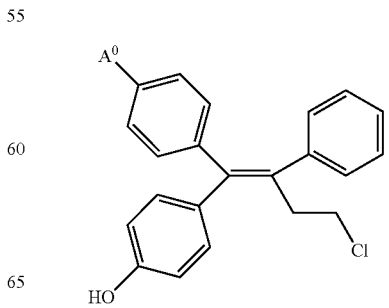

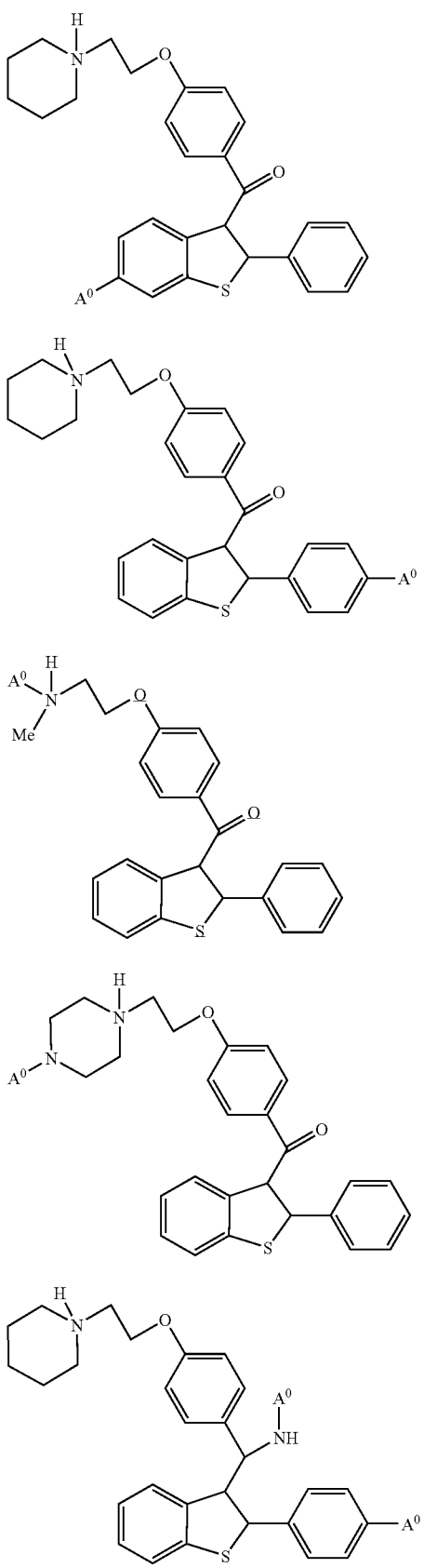

-continued
131
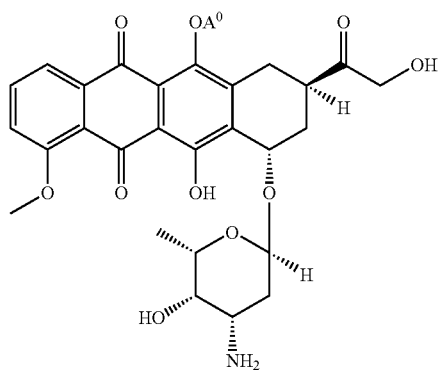
132
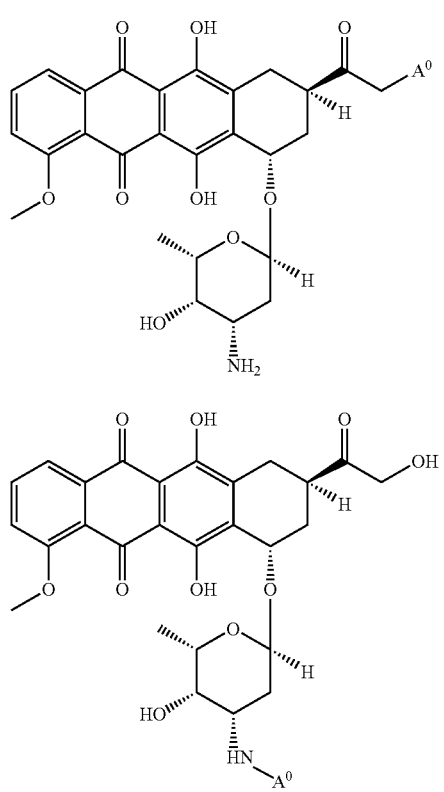
133
134
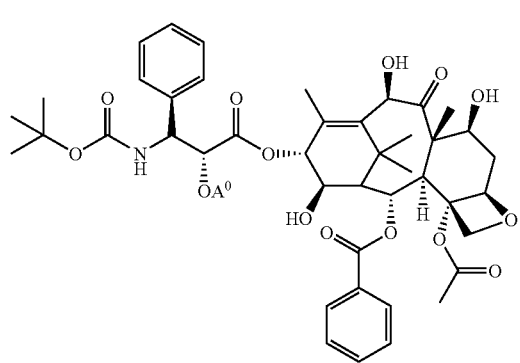
-continued
135
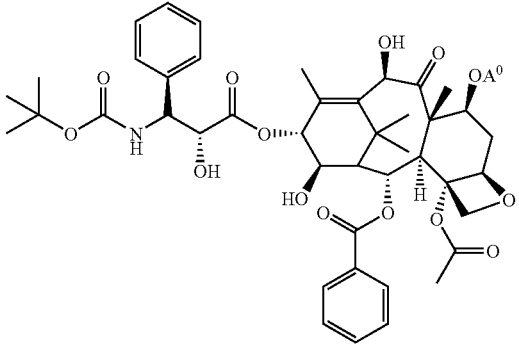
136
137
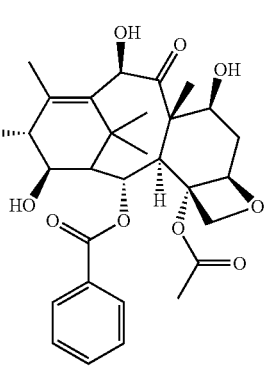

-continued
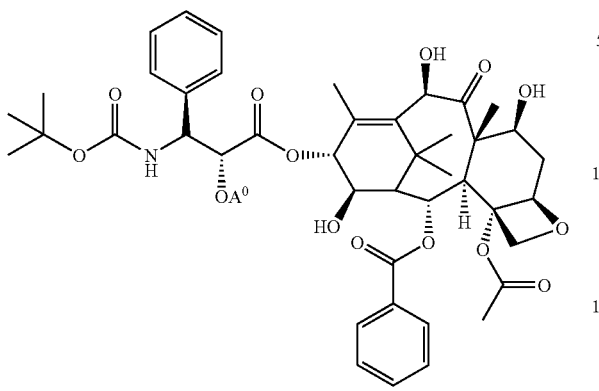
138
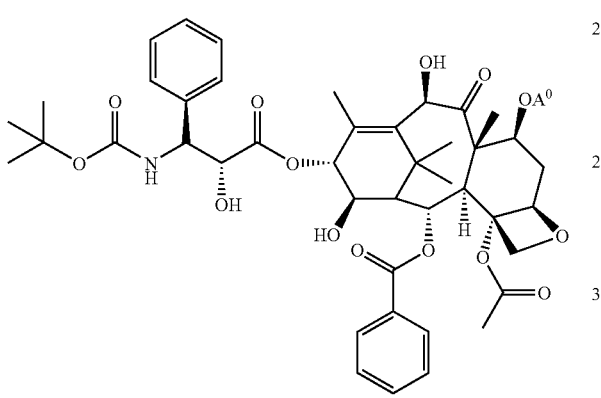
139
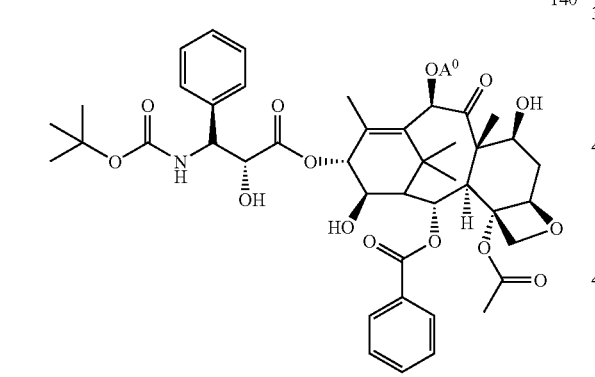
140
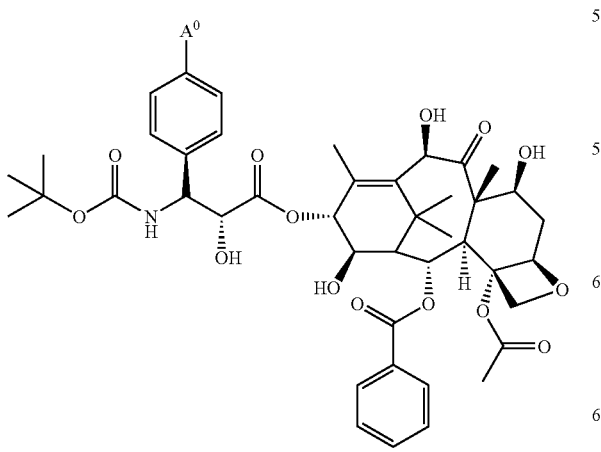
141
-continued
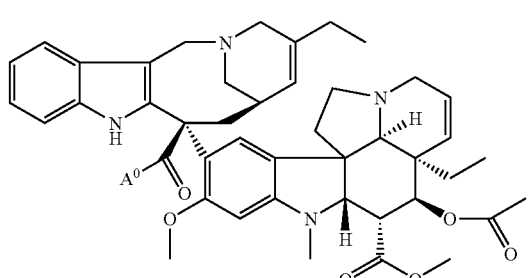
142
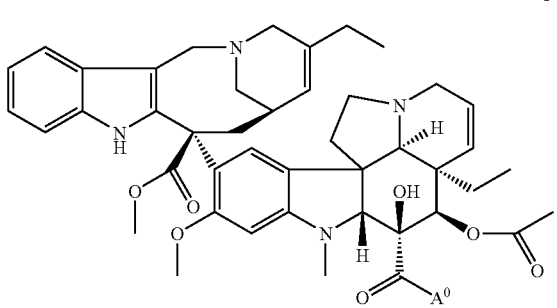
143
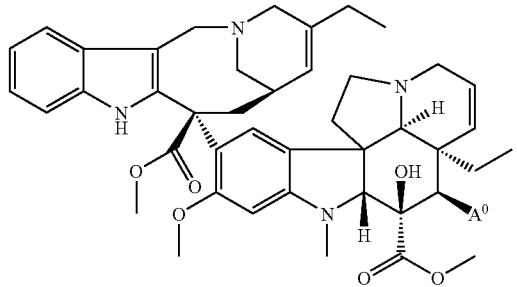
144
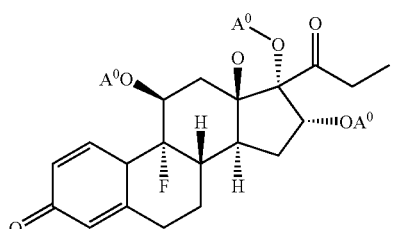
145
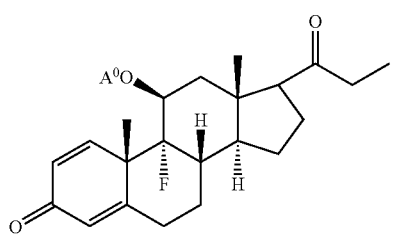
146

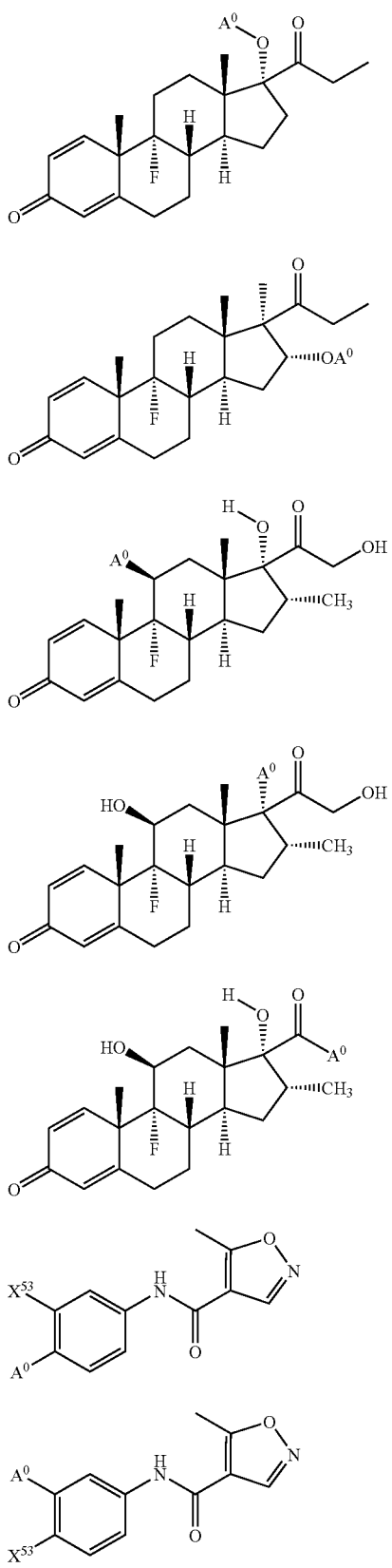
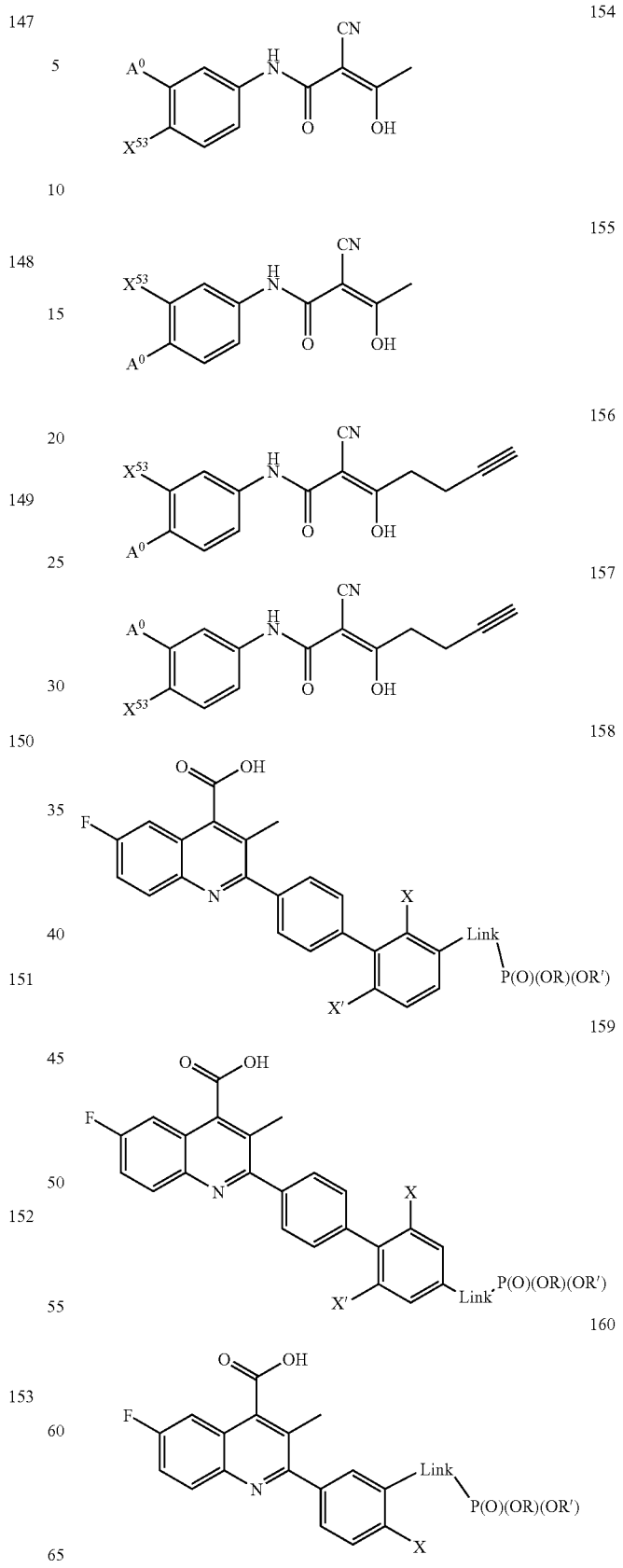

161
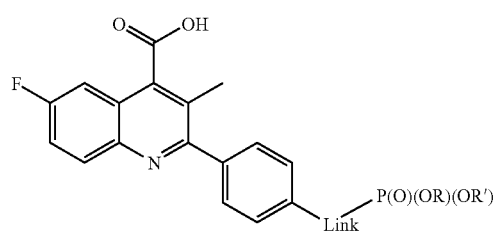
162
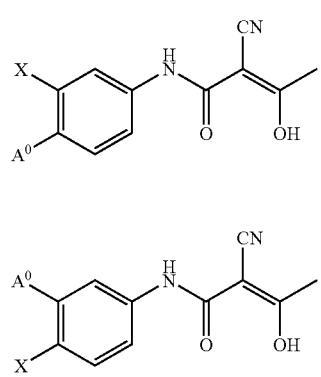
163
164
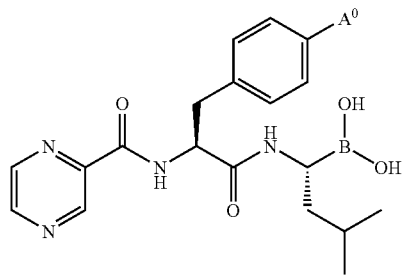
165
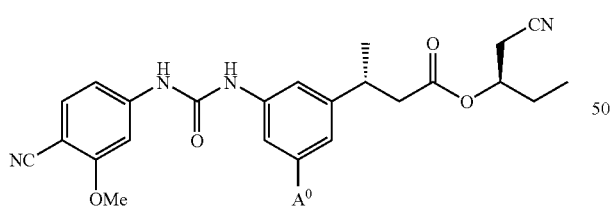
166
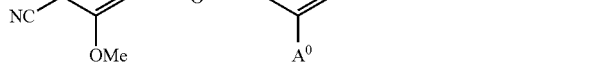
167
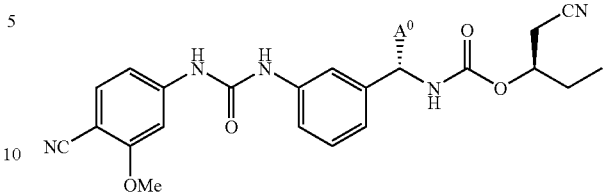
168
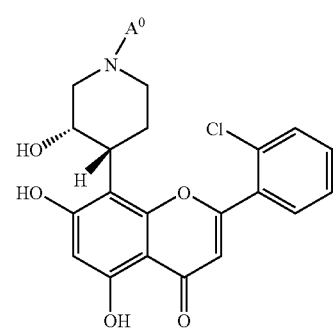
169
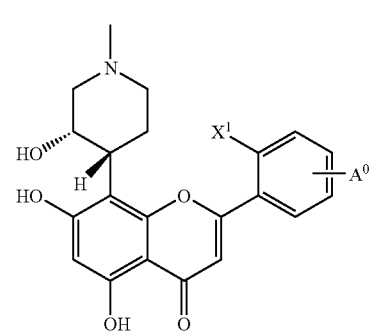
170
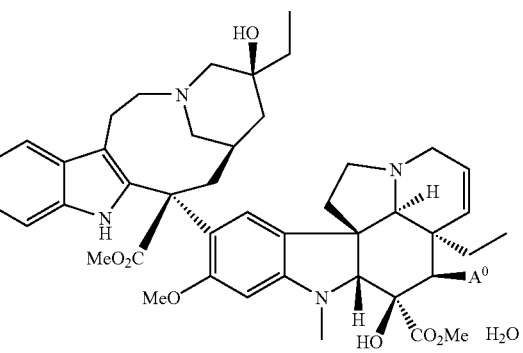

-continued
171
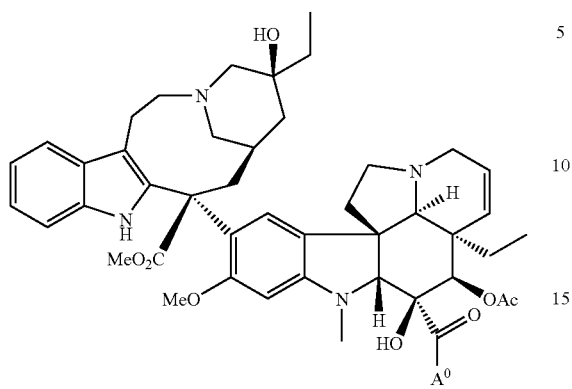
172
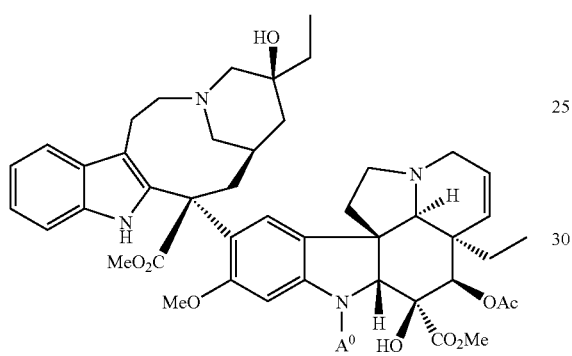
173
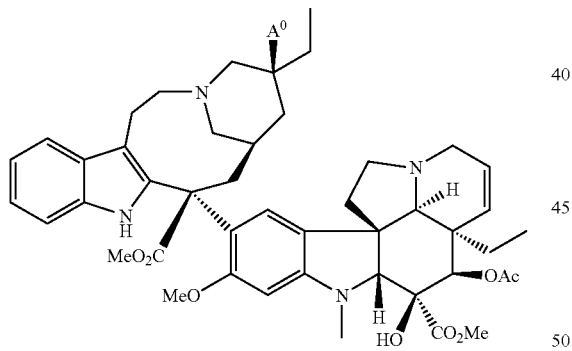
174
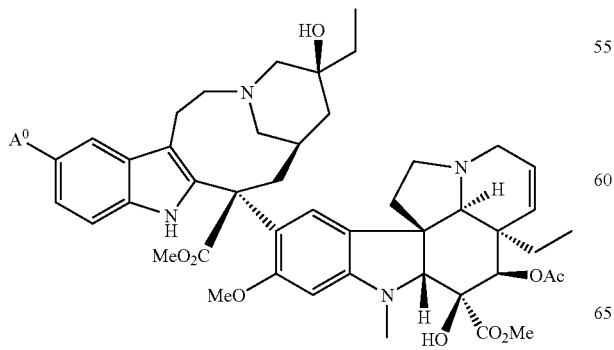
-continued
175
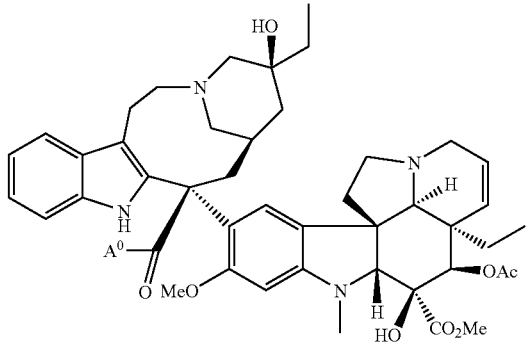
176
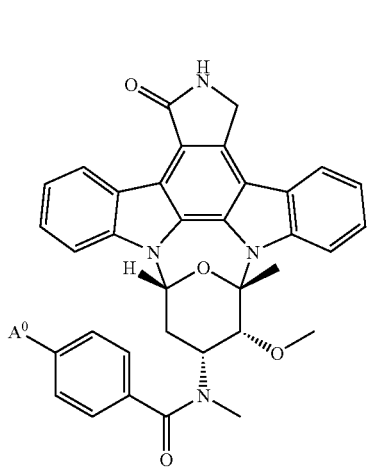
177
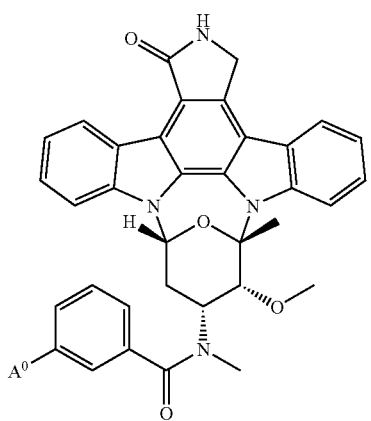

-continued
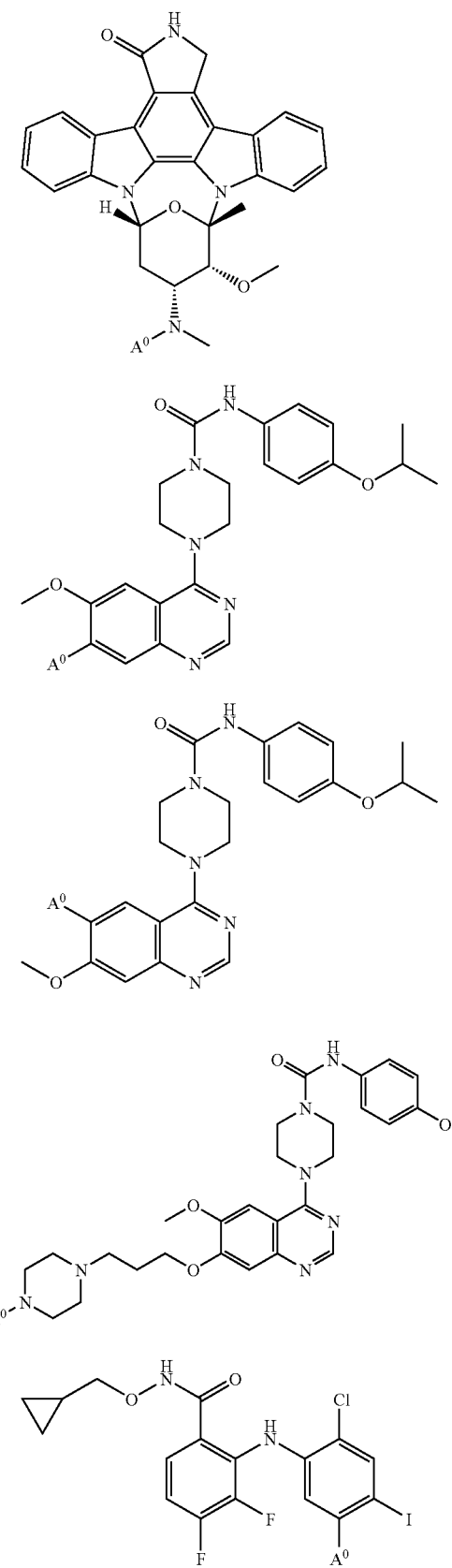
178
179
180
181
182
-continued
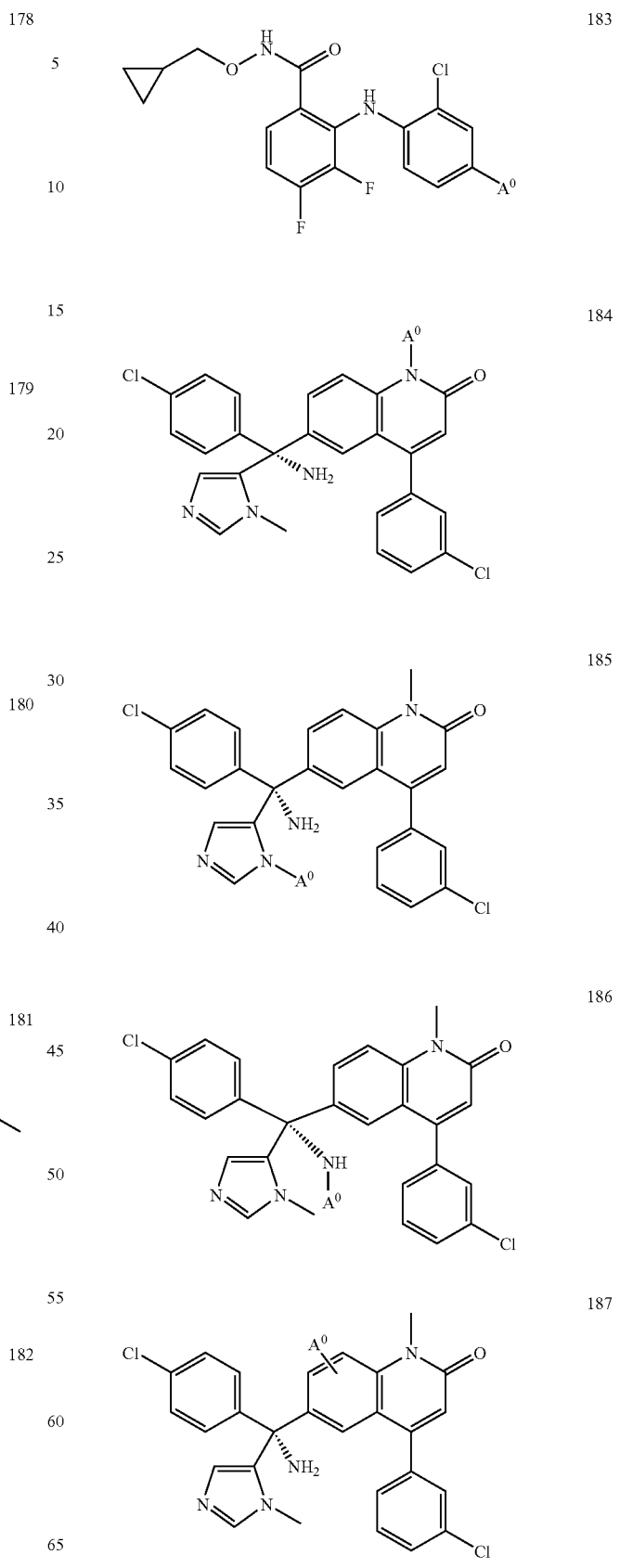
183
184
185
186
187

-continued
188
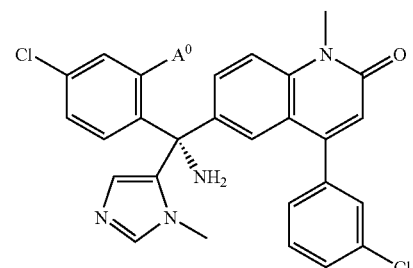
189
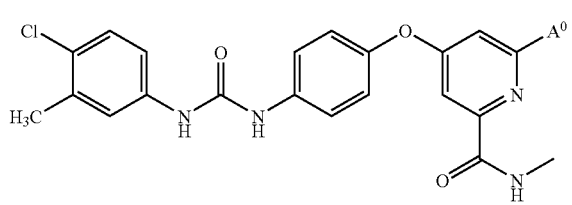
190
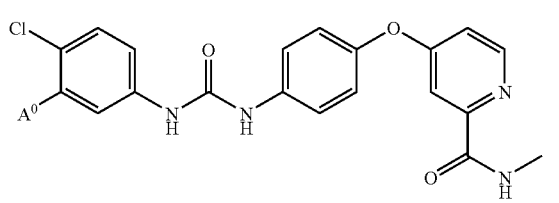
191
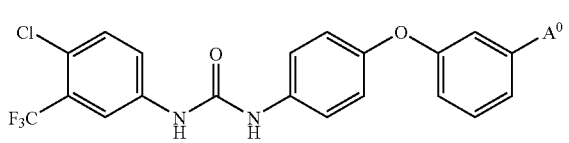
192
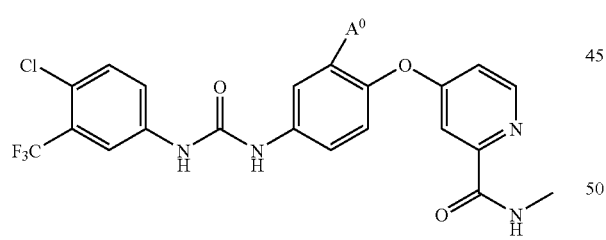
193
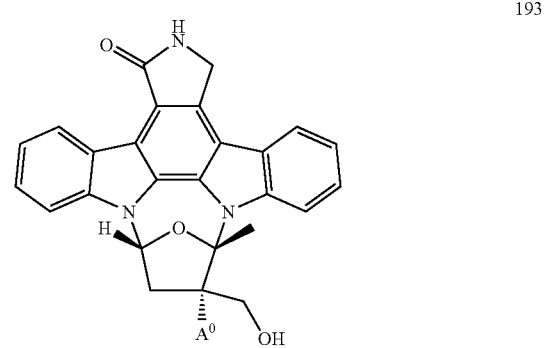
-continued
194
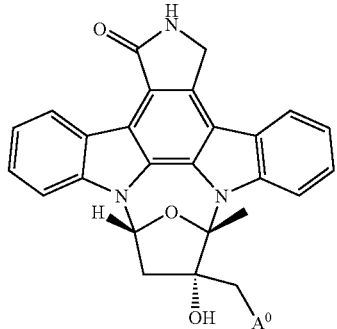
195
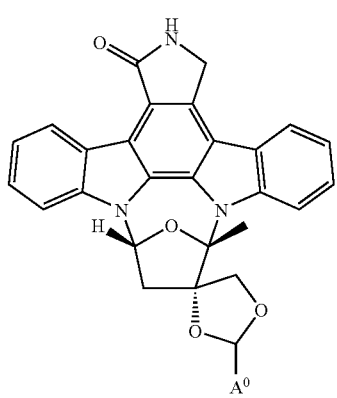
196
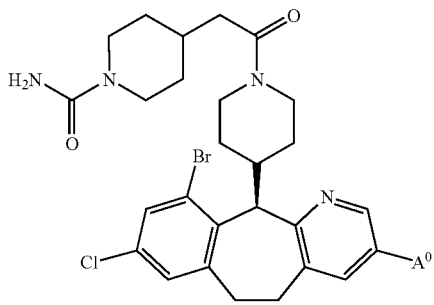
197
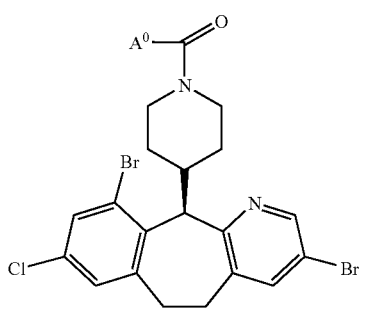

179 180
-continued -continued
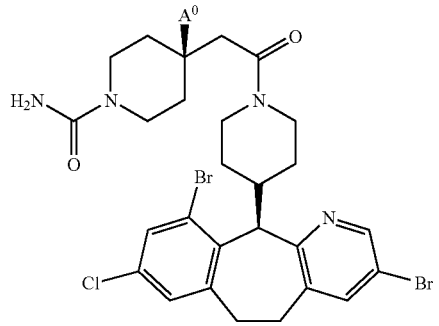
198
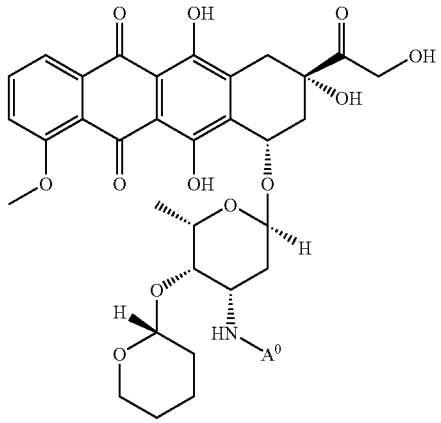
202
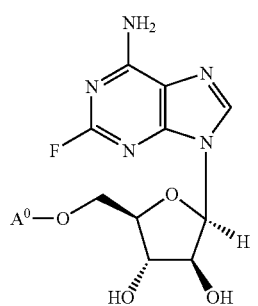
199 200
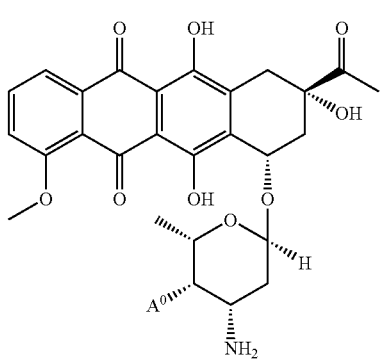
203
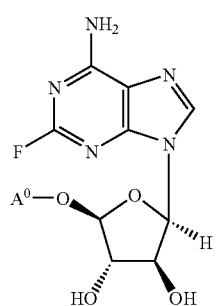
201
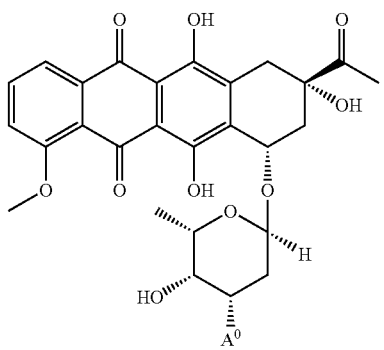
204

-continued
205 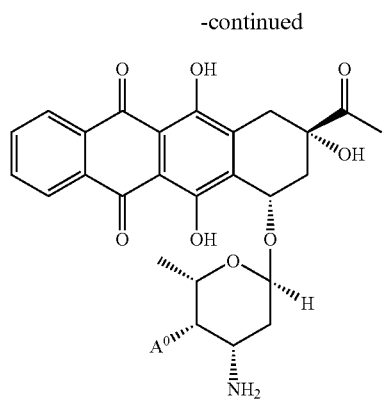
206 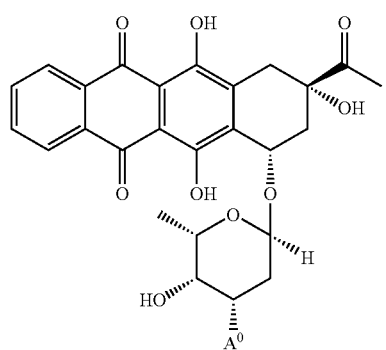
207 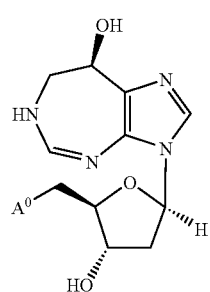
208 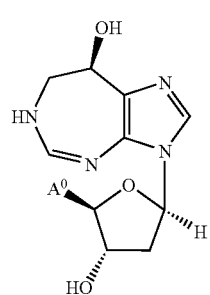
209 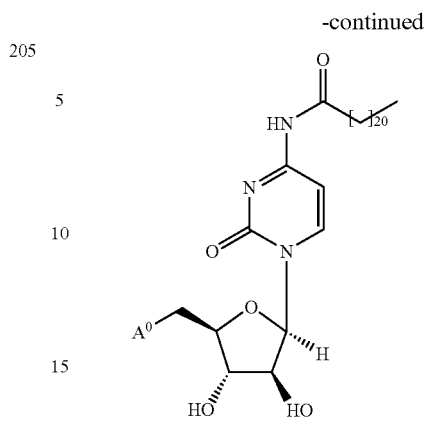
210
211 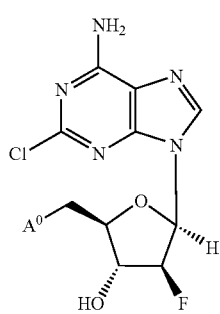

212
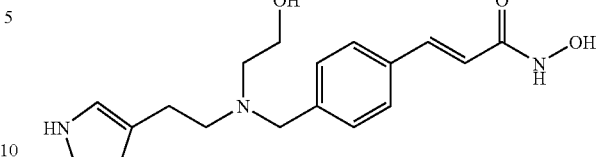
213
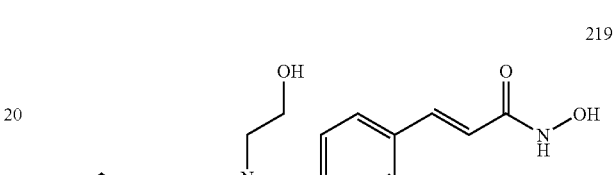
214
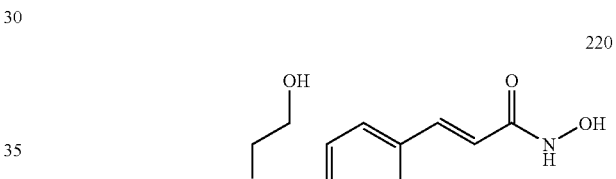
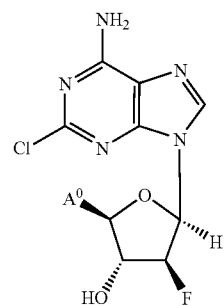
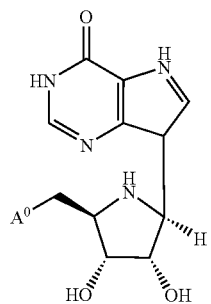
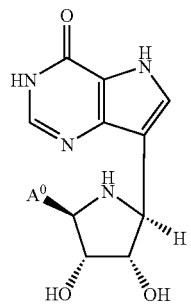
215
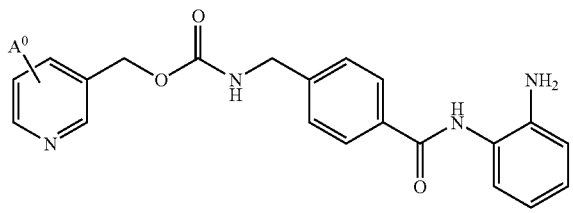
216
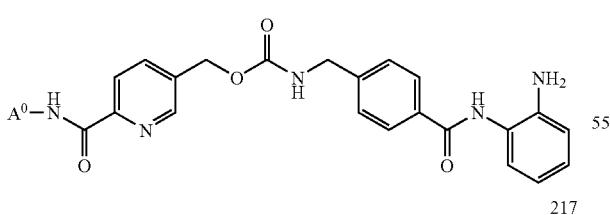
217
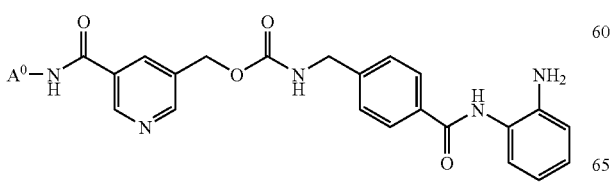
218
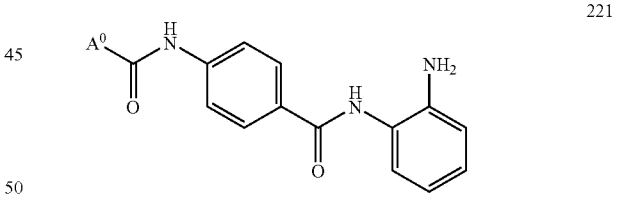
221
222
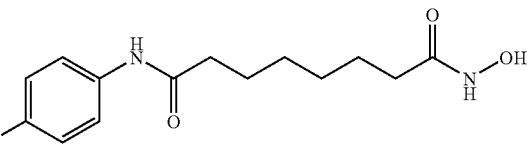
223
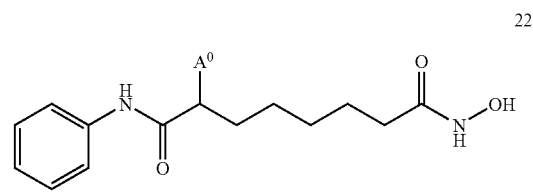

224

225

226

227

228

229

230

231
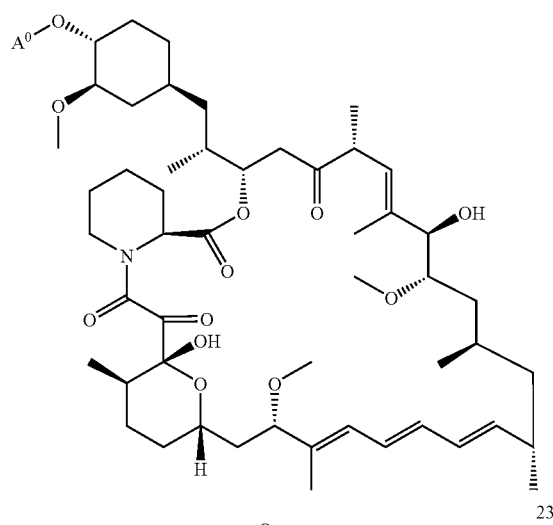
232
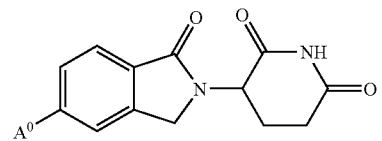
233
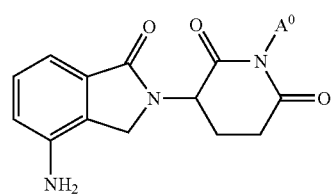
234
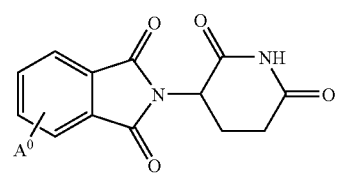
235
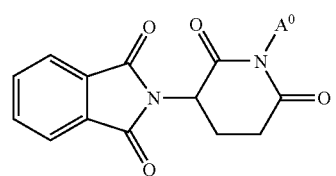
236
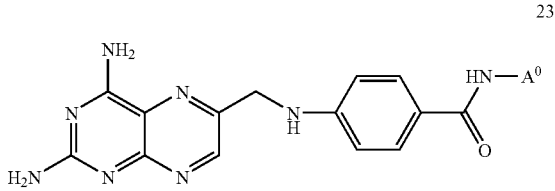
237
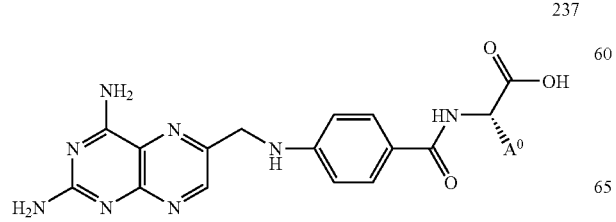
238
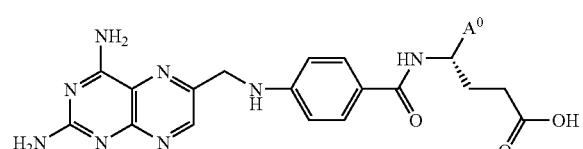
239
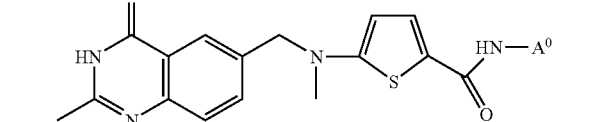
240
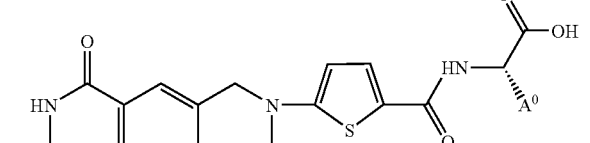
241
242
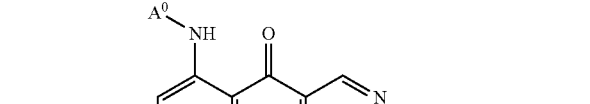
243
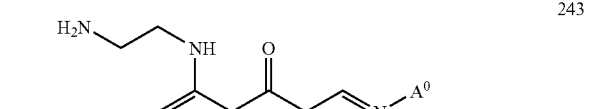
244
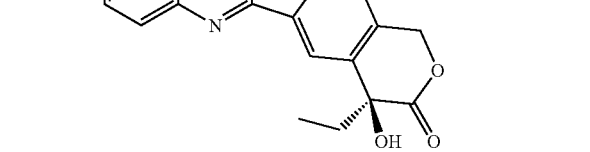

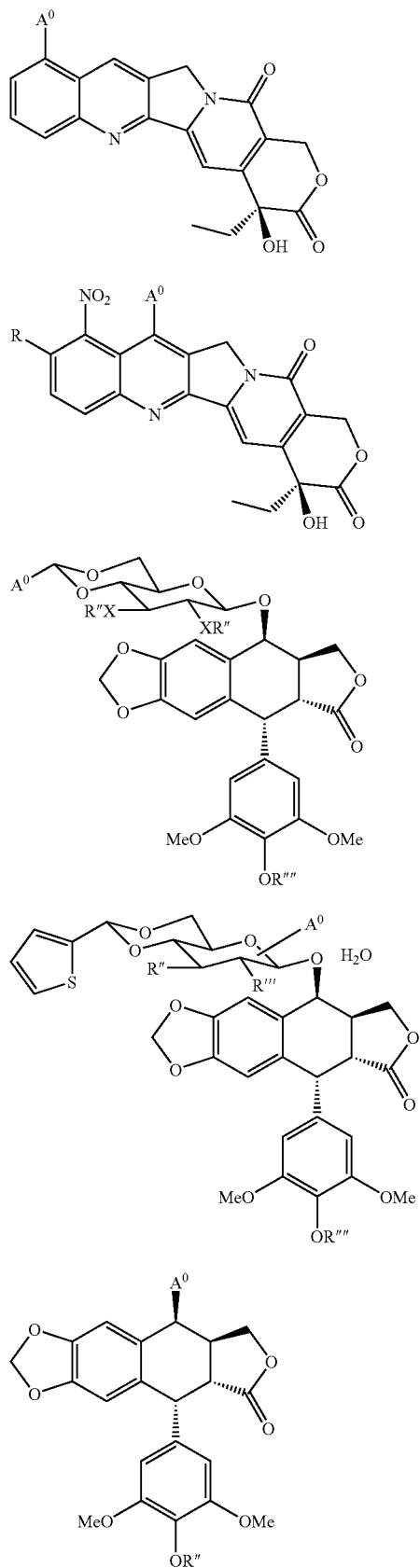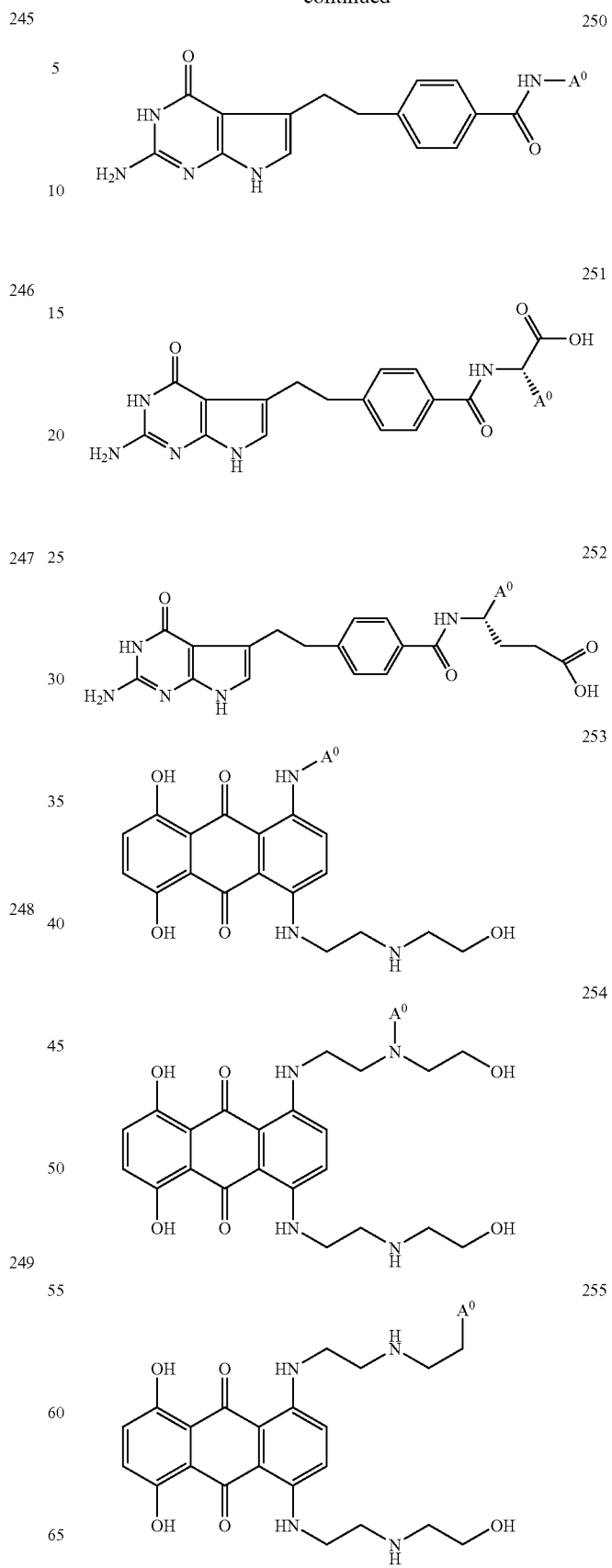

-continued
256
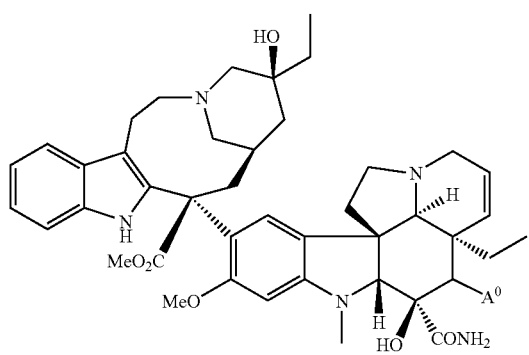
257
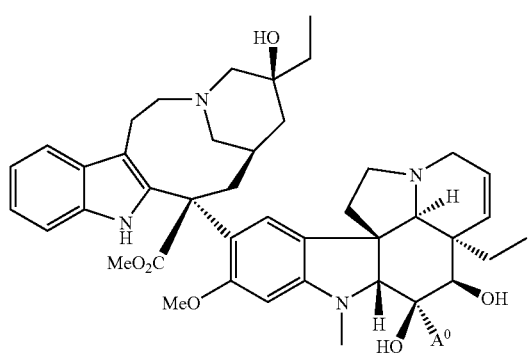
258
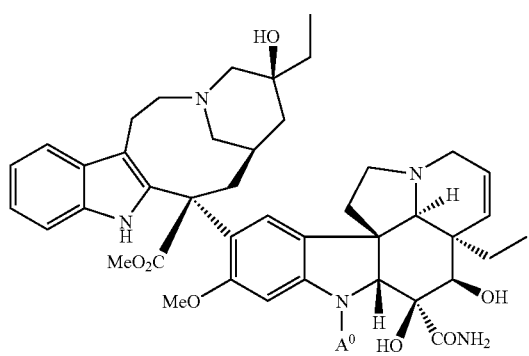
259
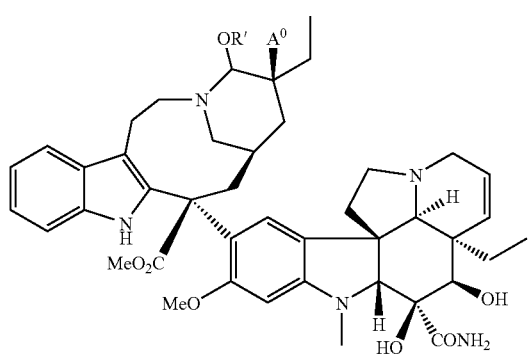
-continued
260
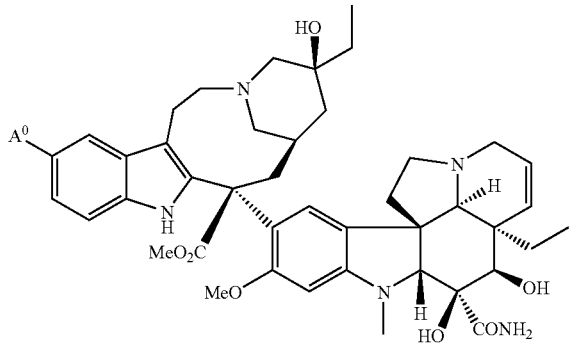
261
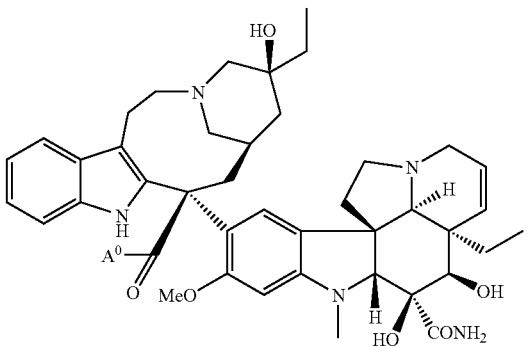
262
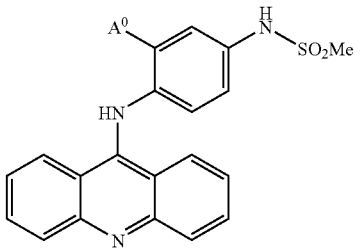
263
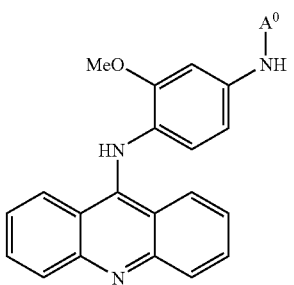

-continued
264
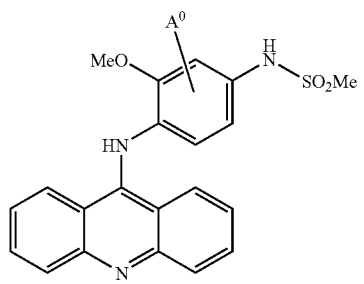
265
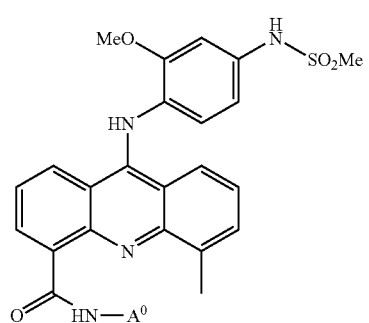
266
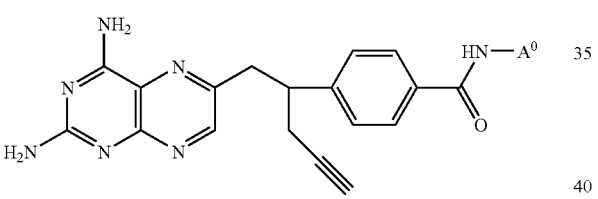
267
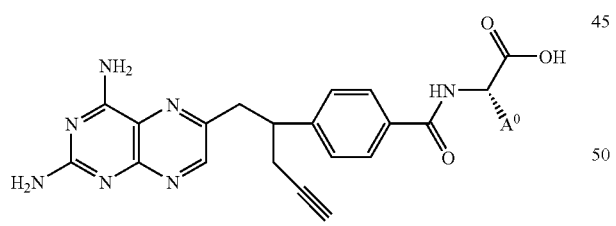
268
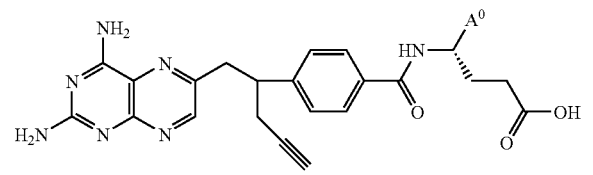
-continued
269
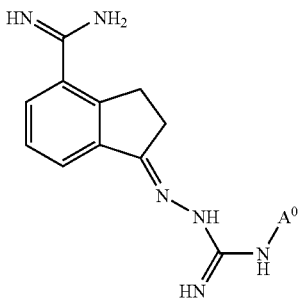
270
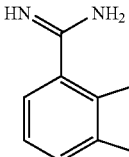
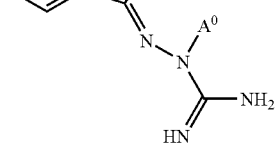
271
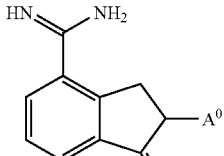
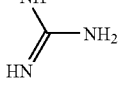
272
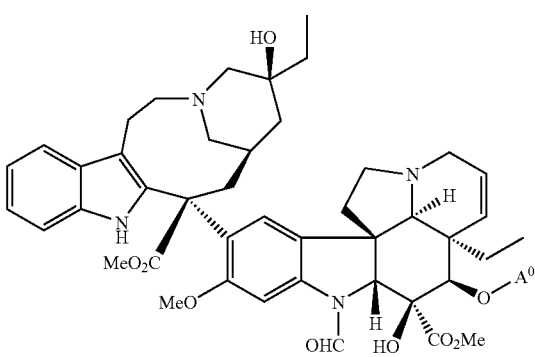

-continued
273
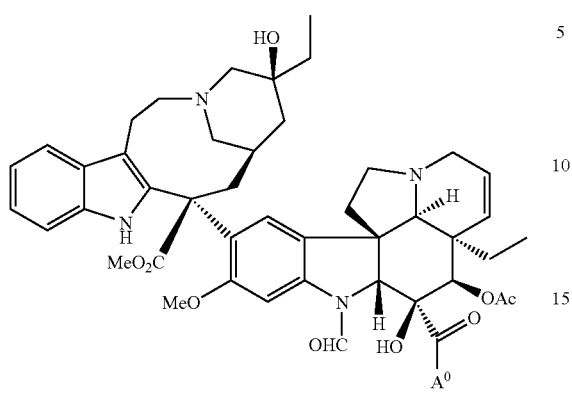
274
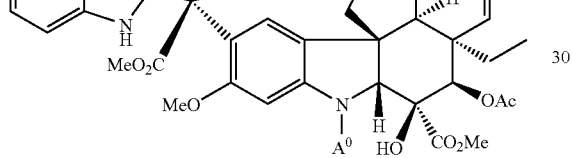
275
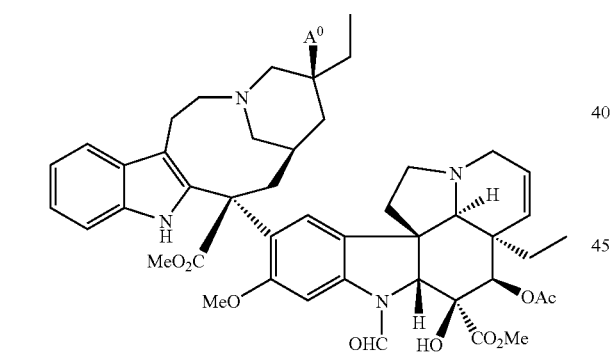
276
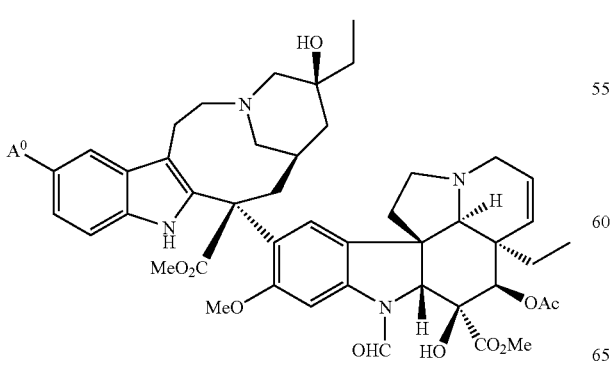
-continued
277
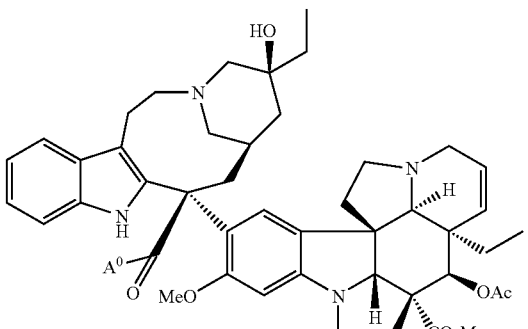
278
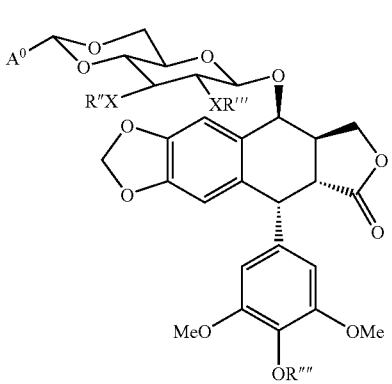
279
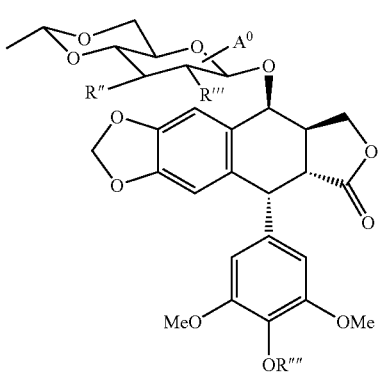
280
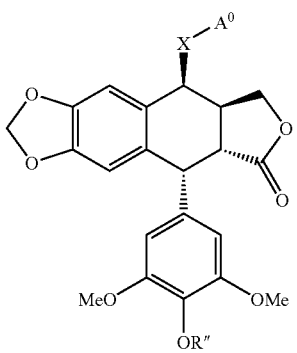

-continued
281 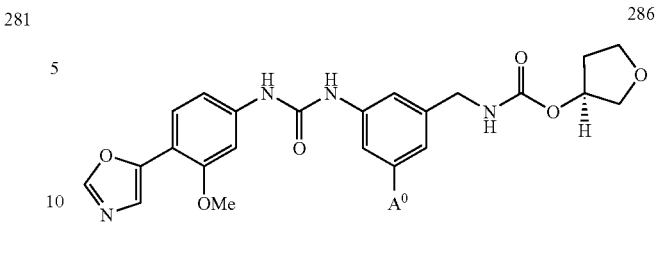
282 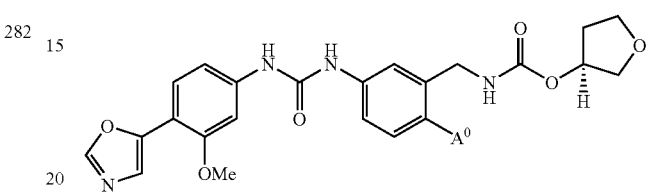
283 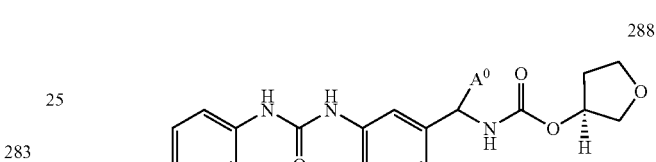
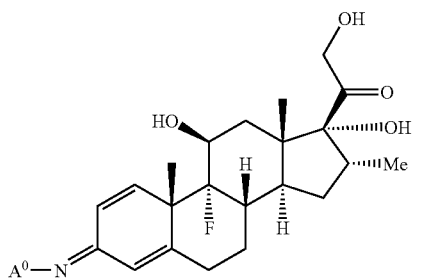
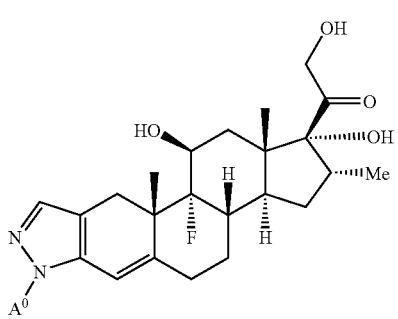
284 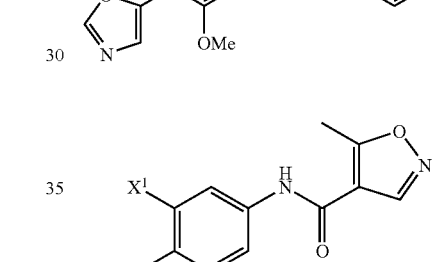
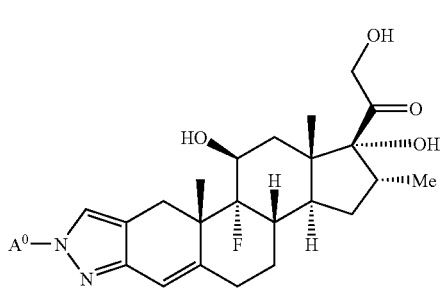
285 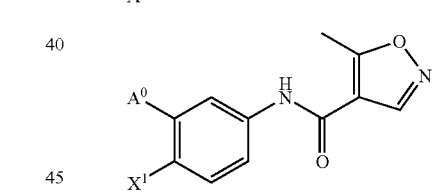
286
287
288
289
290
291
292
293
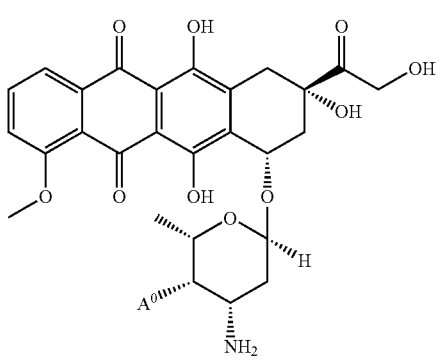
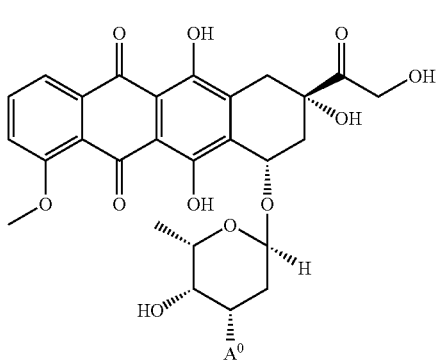
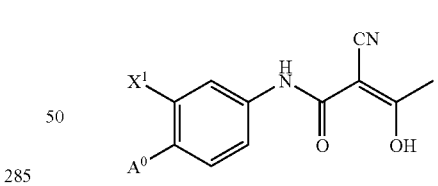
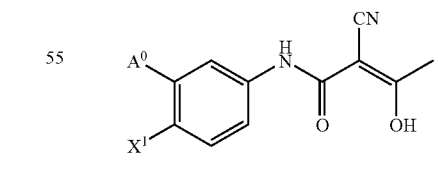
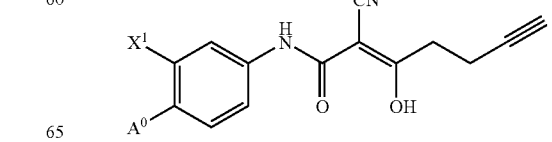

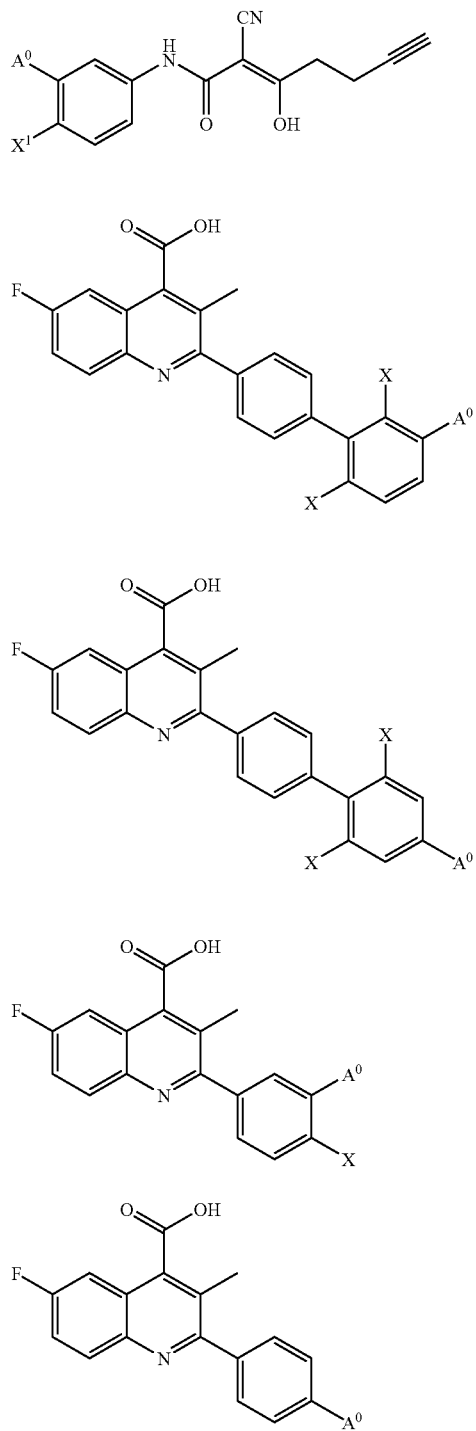
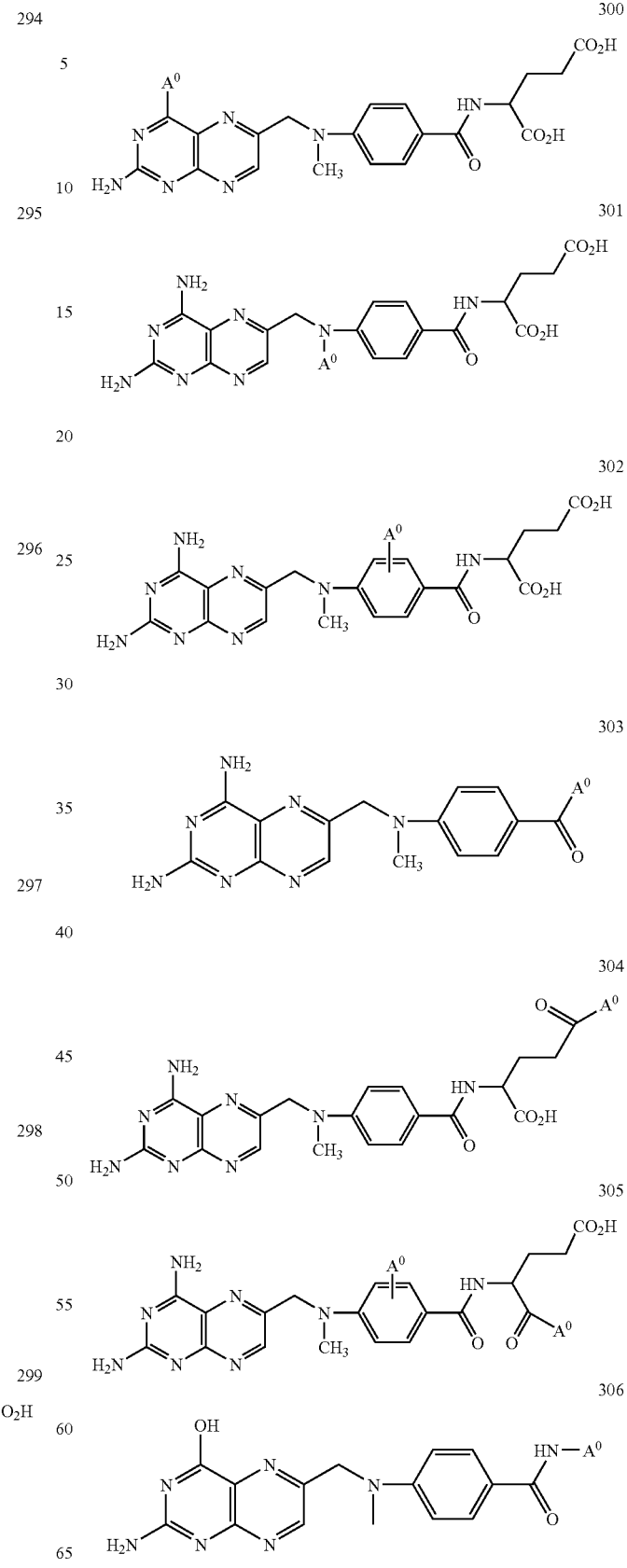

-continued
307
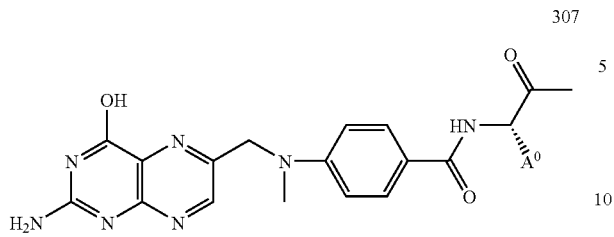
308
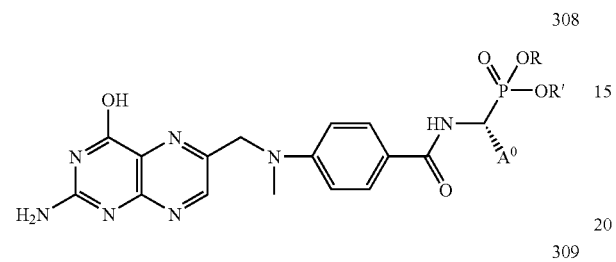
309
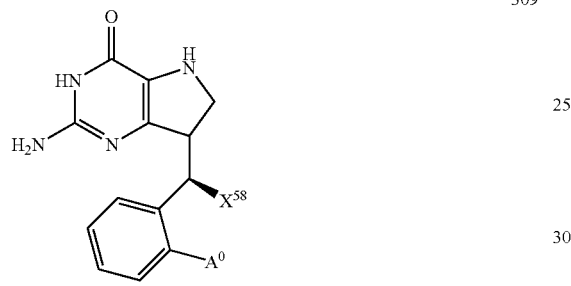
310
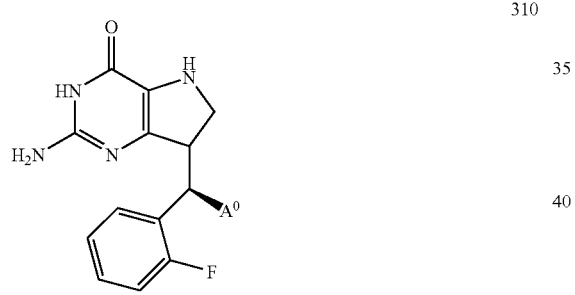
311
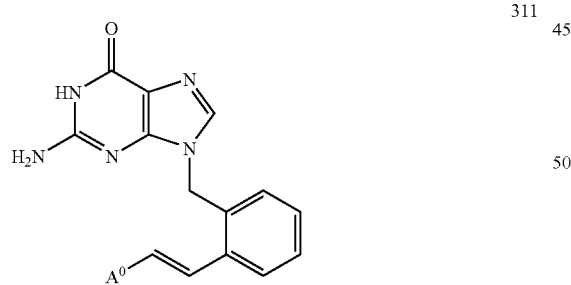
312
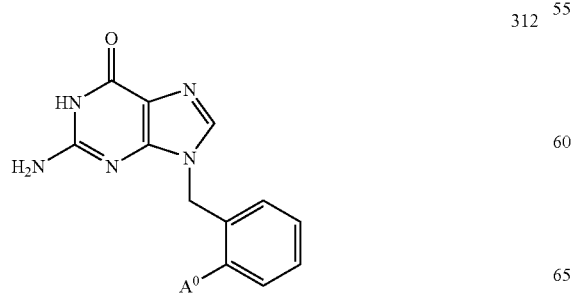
-continued
313
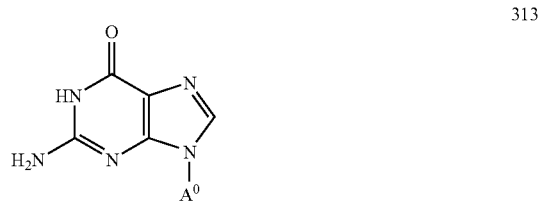
314
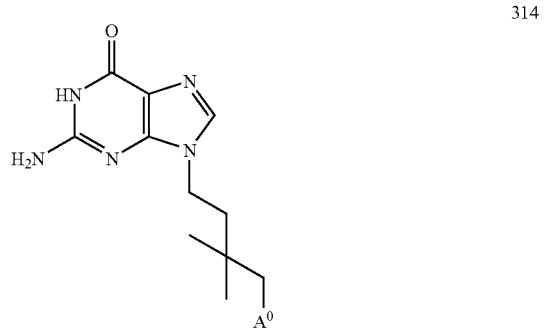
315
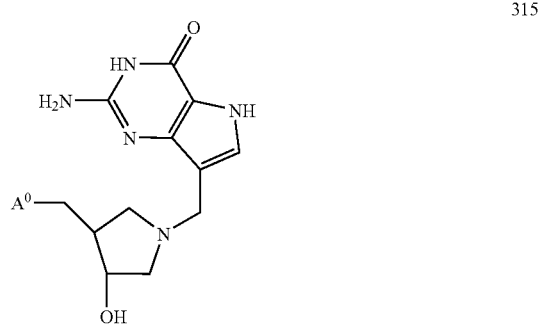
316
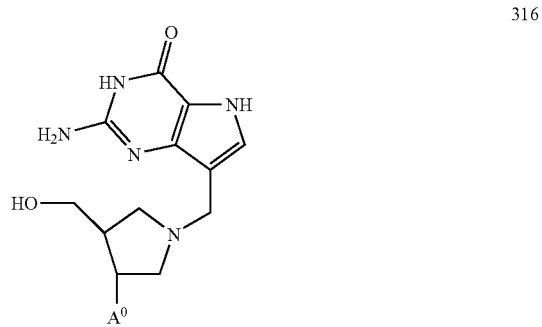
317
318
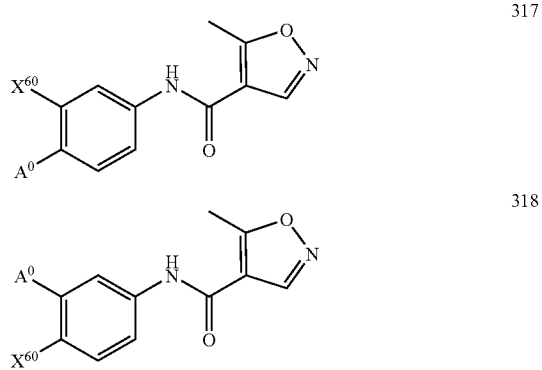

203          204
-continued          -continued
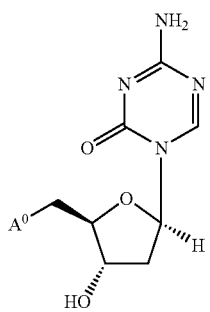
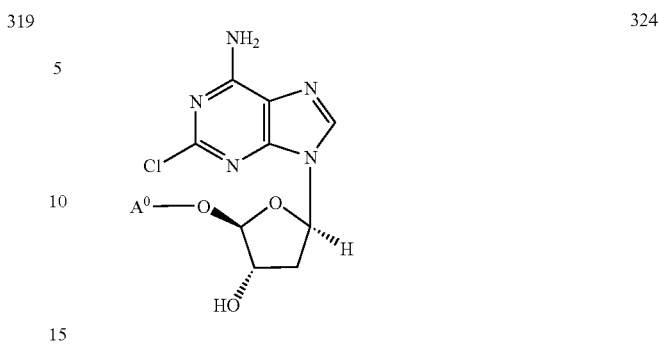
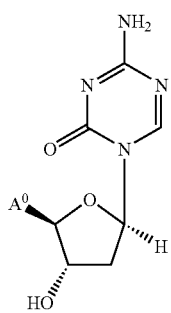
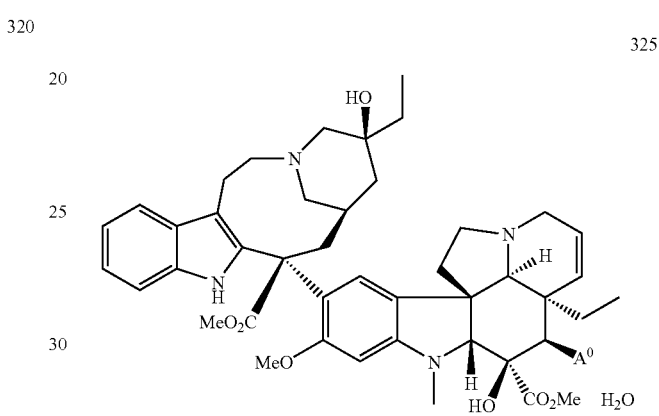
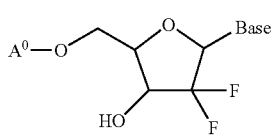
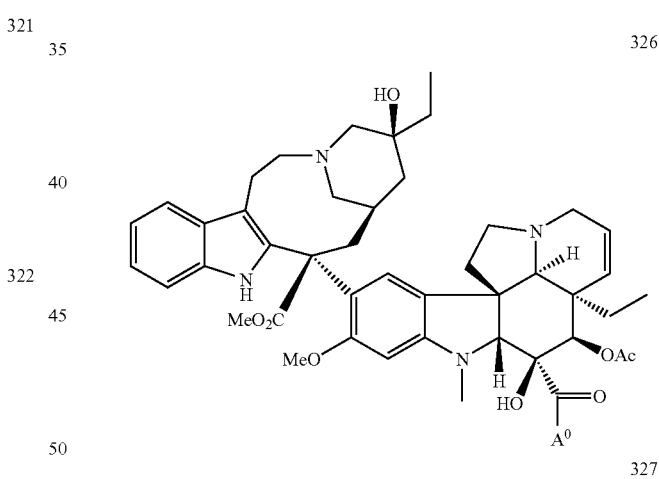
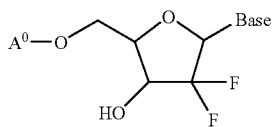
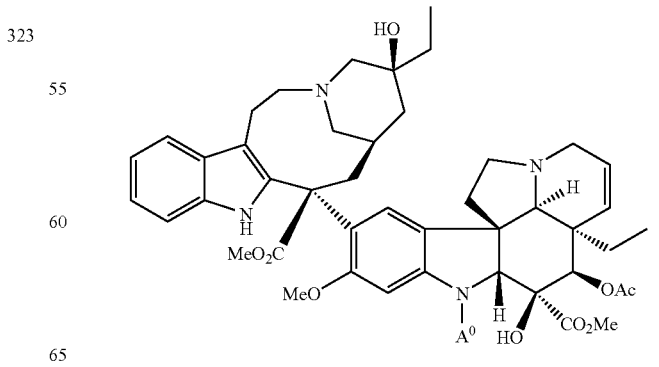
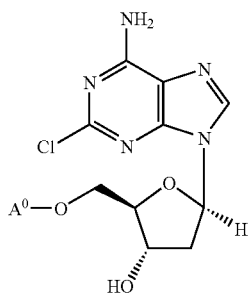

or a pharmaceutically acceptable salt thereof wherein:
$A^0$ is $A^1$;

$A^1$ is:

$$\left\{ \left[ Y^2 \left( \underset{R^2\ R^2}{\phantom{X}} \right)_{M12a} Y^2 \right]_{M12b} W^6 \right.$$

-continued $A^3$ is:

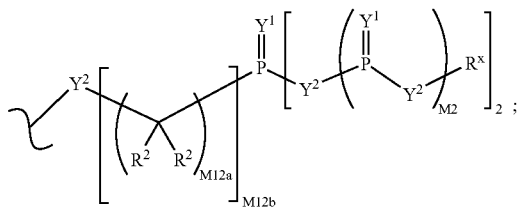

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $W^3$, a protecting group, or the formula:

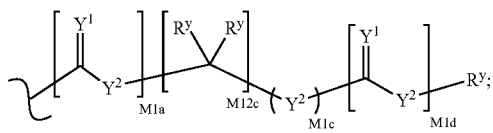

$R^y$ is independently H, $W^3$, $R^2$ or a protecting group;

$R^1$ is independently H or alkyl of 1 to 18 carbon atoms;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $-C(Y^1)R^5$, $-C(Y^1)W^5$, $-SO_2R^5$, or $-SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

3. A compound of any one of formulae 1-336 wherein:
$A^0$ is $A^1$;

$A^1$ is:

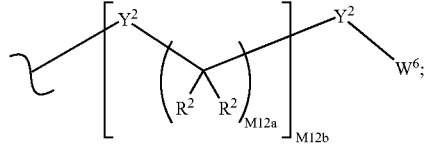

$A^3$ is:

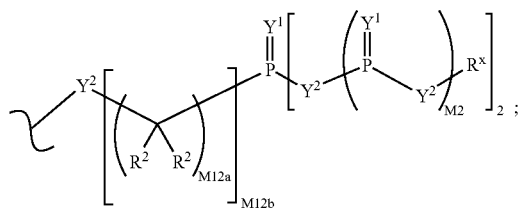

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $W^3$, a protecting group, or the formula:

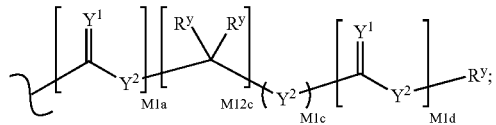

$R^y$ is independently H, $W^3$, $R^2$ or a protecting group;

$R^1$ is independently H or alkyl of 1 to 18 carbon atoms;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $-C(Y^1)R^5$, $-C(Y^1)W^5$, $-SO_2R^5$, or $-SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another specific embodiment, the invention provides a compound of the formula:

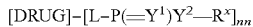

or a pharmaceutically acceptable salt thereof wherein,

DRUG is a compound of any one of 500-601;

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $W^3$, a protecting group, or the formula:

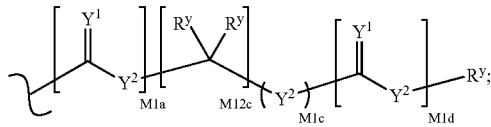

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, $-C(Y^1)R^5$, $-C(Y^1)W^5$, $-SO_2R^5$, or $-SO_2W^5$;

$W^5$ is carbocycle or heterocycle wherein $W^5$ is independently substituted with 0 to 3 $R^2$ groups;

M2 is 1, 2, or 3;

M1a, M1c, and M1d are independently 0 or 1;

M12c is 0, 1, 2, 3, 4, 5, 6, 7, 8, 9, 10, 11 or 12;

nn is 1, 2, or 3; and

L is a linking group.

In another specific embodiment, the invention provides a compound of which is a compound of the formula:

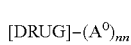

or a pharmaceutically acceptable salt thereof wherein,

DRUG is a compound of any one of formulae 500-601;

nn is 1, 2, or 3;

$A^0$ is $A^1$, $A^2$, or $W^3$ with the proviso that the compound includes at least one $A^1$;

$A^1$ is:

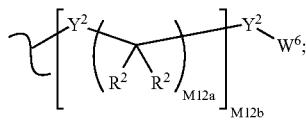

$A^2$ is:

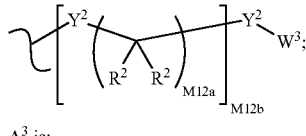

$A^3$ is:

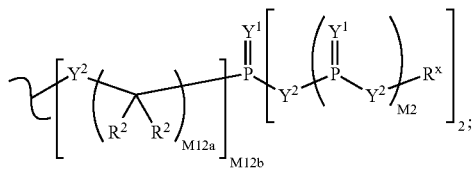

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $W^3$, a protecting group, or the formula:

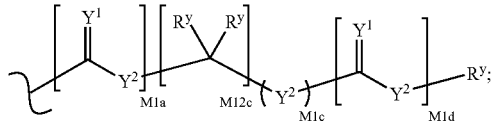

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $N(R^x)C(Y^1)OR^x$, or $-N(R^x)C(Y^1)(N(R^x)(R^x))$;

$R^{1d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or W;

$W^4$ is $R^5$, $-C(Y^1)R^5$, $-C(Y^1)W^5$, $-SO_2R^5$, or $-SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and
M12c is 0, 1, 2, 3, 4, 5, 6, 7, 8, 9, 10, 11 or 12.

In compounds of the invention $W^5$ carbocycles and $W^5$ heterocycles may be independently substituted with 0 to 3 $R^2$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

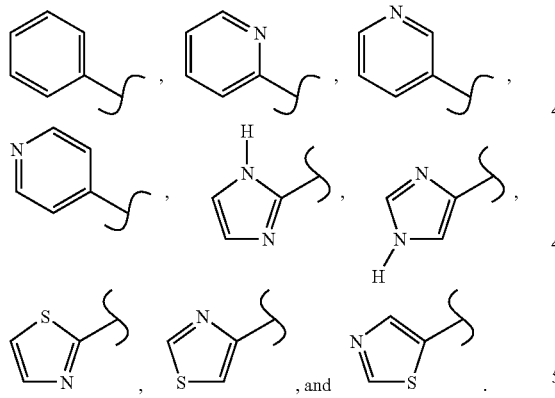

$W^5$ carbocycles and heterocycles may be independently substituted with 0 to 3 $R^2$ groups, as defined above. For example, substituted $W^5$ carbocycles include:

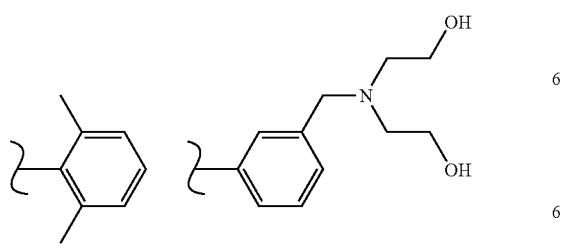

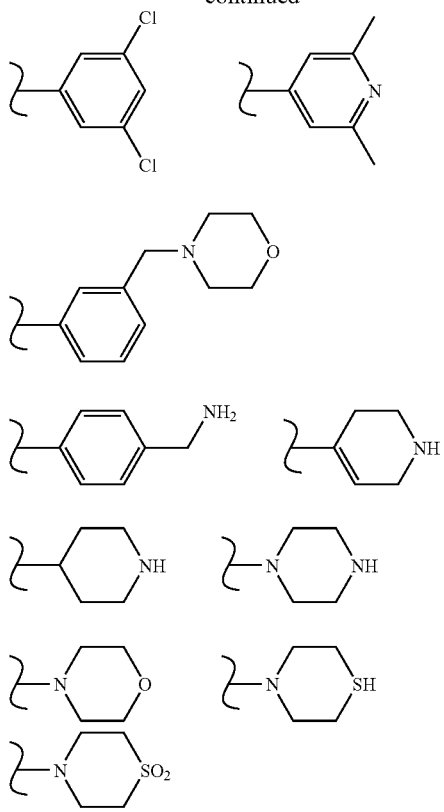

Examples of substituted phenyl carbocycles include:

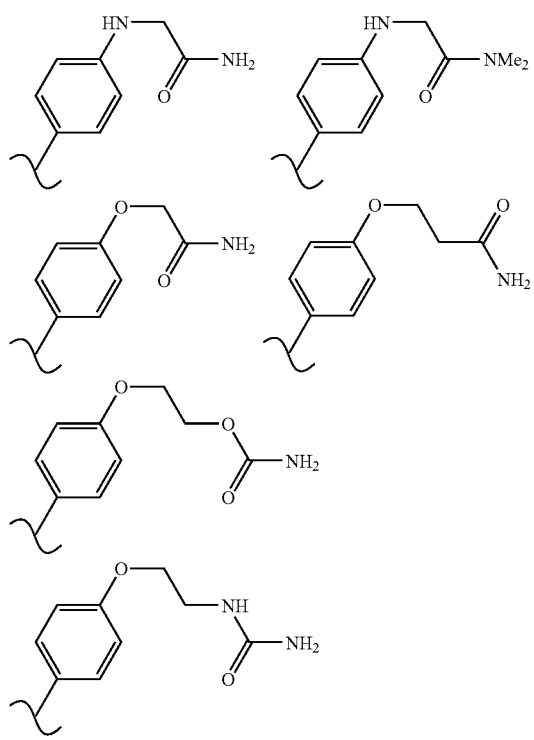

Conjugates of Formula I

In one embodiment, the invention provides a conjugate of Formula I:

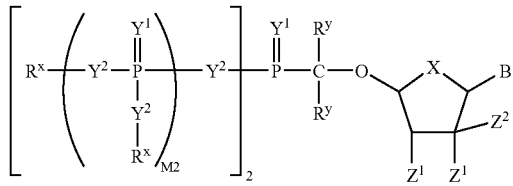

I or a pharmaceutically acceptable salt or solvate thereof;

wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo[3,4-D]pyrimidine;

X is selected from O, $C(R^y)_2$, $C=C(R^y)_2$, NR and S;

$Z^1$ is independently selected from H, OH, OR, $NR_2$, CN, $NO_2$, SH, SR, F, Cl, Br, and I;

$Z^2$ is selected from H, $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, and $C_1$-$C_8$ substituted alkynyl, $Y^1$ is independently O, S, NR, $^+N(O)(R)$, N(OR), $^+N(O)(OR)$, or N—$NR_2$;

$Y^2$ is independently a bond, O, $CR_2$, NR, $^+N(O)(R)$, N(OR), $^+N(O)(OR)$, N—$NR_2$, S, S—S, S(O), or $S(O)_2$;

M2 is 0, 1 or 2;

$R^y$ is independently H, F, Cl, Br, I, OH, R, —$C(=Y^1)R$, —$C(=Y^1)OR$, —$C(=Y^1)N(R)_2$, —$N(R)_2$, —$^+N(R)_3$, —SR, —S(O), —$S(O)_2R$, —S(O)(OR), —$S(O)_2(OR)$, —OC($=Y^1$), —OC($=Y^1$)OR, —OC($=Y^1$)(N(R)_2), —SC($=Y^1$), —SC($=Y^1$)OR, —SC($=Y^1$)(N(R)_2), —N(R)C($=Y^1$), —N(R)C($=Y^1$)OR, or —N(R)C($=Y^1$)N(R)_2, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2R$), arylsulfone (—$SO_2Ar$), arylsulfoxide (—SOAr), arylthio (—SAr), sulfonamide (—$SO_2NR_2$), alkylsulfoxide (—SOR), ester (—C(=O)OR), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, a protecting group (PG), or $W^3$; or when taken together, $R^y$ forms a carbocyclic ring of 3 to 7 carbon atoms;

$R^x$ is independently $R^y$, a protecting group, or the formula:

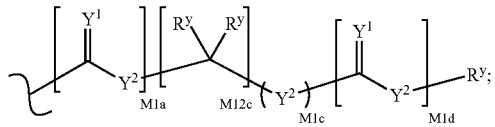

wherein:

M1a, M1c, and M1d are independently 0 or 1;

M12c is 0, 1, 2, 3, 4, 5, 6, 7, 8, 9, 10, 11 or 12; and

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, —$C(Y^1)R^y$, —$C(Y^1)W^5$, —$SO_2R^y$, or —$SO_2W^5$; and $W^5$ is a carbocycle or a heterocycle wherein $W^5$ is independently substituted with 0 to 3 $R^y$ groups.

For a conjugate of Formula I, in one specific embodiment, $C_1$-$C_8$ substituted alkyl, $C_1$-$C_8$ substituted alkenyl, $C_1$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, —$NH_2$, —$NH_3^+$, —NHR, —$NR^2$, —$NR_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —$SO_2R$, —$SO_2Ar$, —SOAr, —SAr, —$SO_2NR_2$, —SOR, —$CO_2R$, —C(=O)$NR_2$, 5-7 membered ring lactam, 5-7 membered ring lactone, —CN, —$N_3$, —$NO_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, phosphate, and a prodrug moiety.

For a conjugate of Formula I, in one specific embodiment, "protecting group" is selected from a carboxyl ester, a carboxamide, an aryl ether, an alkyl ether, a trialkylsilyl ether, a sulfonic acid ester, a carbonate, and a carbamate.

For a conjugate of Formula I, in one specific embodiment, $W^5$ is selected from the structures:

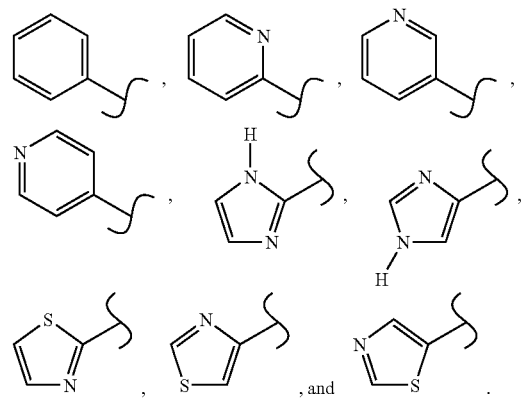

For a conjugate of Formula I, in one specific embodiment, X is O and $R^y$ is H.

For a conjugate of Formula I, in one specific embodiment, X is C=$CH_2$ and $R^y$ is H.

For a conjugate of Formula I, in one specific embodiment, $Z^1$ is OH.

For a conjugate of Formula I, in one specific embodiment, $Z^2$ is $C_1$-$C_8$ alkyl or $C_1$-$C_8$ substituted alkyl.

For a conjugate of Formula I, in one specific embodiment, $Z^2$ is $CH_3$.

In one specific embodiment, the conjugate of formula I has the following formula:

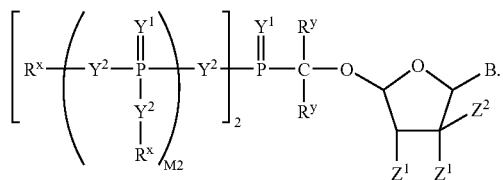

In one specific embodiment, the conjugate of formula I has the following formula:

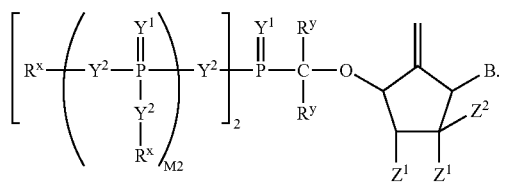

In one specific embodiment, the conjugate of formula I has the following formula:

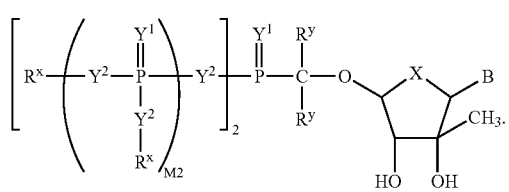

In one specific embodiment, the conjugate of formula I has the following formula:

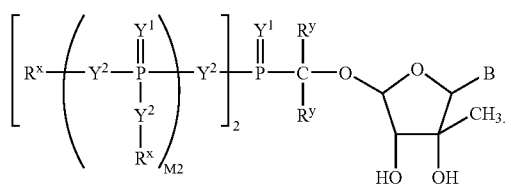

In one specific embodiment, the conjugate of formula I has the following formula:

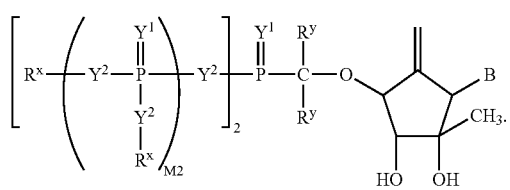

In one specific embodiment, the conjugate of formula I has the following formula:

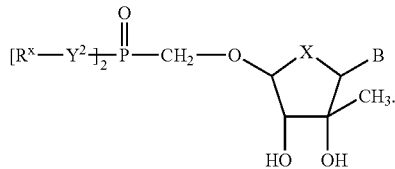

In one specific embodiment, the conjugate of formula I has the following formula:

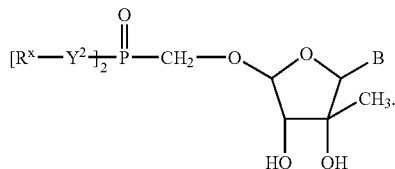

In one specific embodiment, the conjugate of formula I has the following formula:

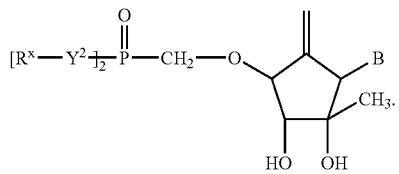

In one specific embodiment, the conjugate of formula I has the following formula:

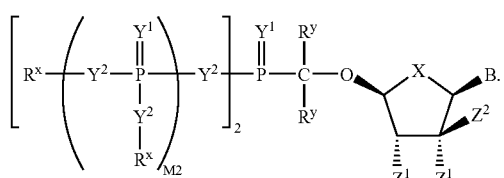

wherein, in a more specific embodiment, $Z^1$ is OH; $Z^2$ is $C_1$-$C_8$ alkyl or $C_1$-$C_8$ substituted alkyl; and $Z^2$ is $CH_3$.

In one specific embodiment, the conjugate of formula I has the following formula:

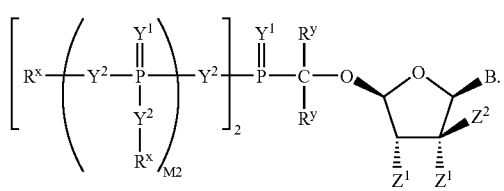

In one specific embodiment, the conjugate of formula I has the following formula:

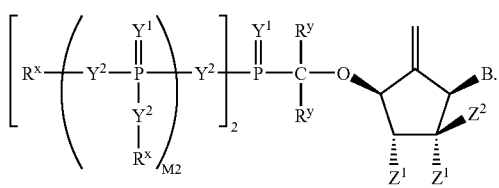

In one specific embodiment, the conjugate of formula I has the following formula:

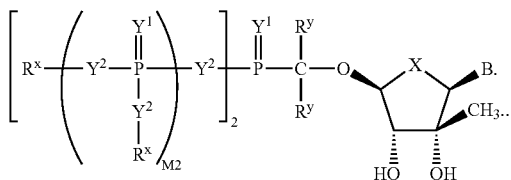

In one specific embodiment, the conjugate of formula I has the following formula:

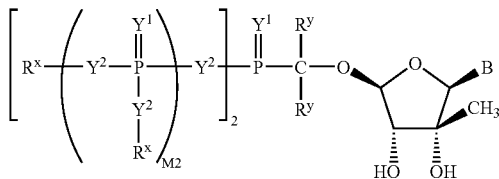

In one specific embodiment, the conjugate of formula I has the following formula:

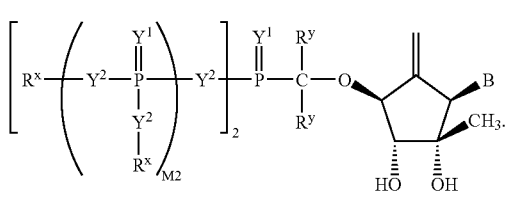

In one specific embodiment, the conjugate of formula I has the following formula:

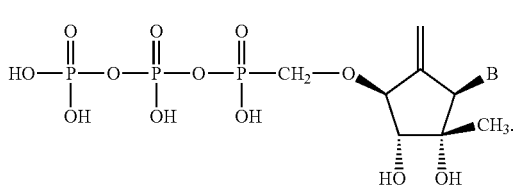

In one specific embodiment, the conjugate of formula I has the following formula:

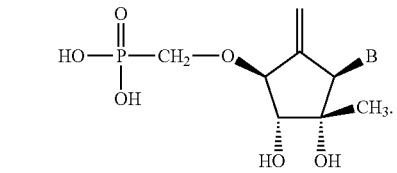

In one specific embodiment, the conjugate of formula I has the following formula:

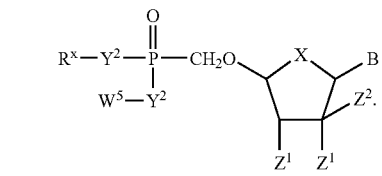

In one specific embodiment, the conjugate of formula I has the following formula:

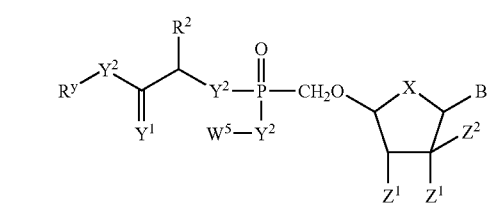

wherein $R^2$ is H or $C_1$-$C_8$ alkyl.

In one specific embodiment, the conjugate of formula I has the following formula:

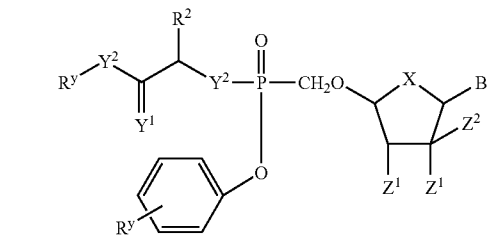

In one specific embodiment, the conjugate of formula I has the following formula:

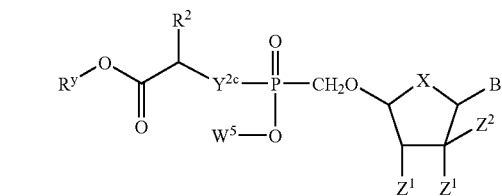

wherein $Y^{2c}$ is O, $N(R^y)$ or S.

In one specific embodiment, the conjugate of formula I has the following formula:

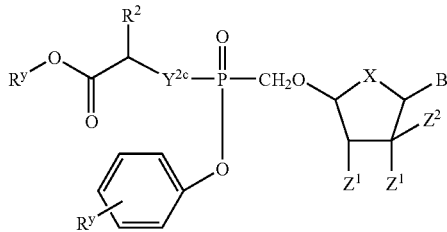

wherein, in a more specific embodiment, $Y^{2c}$ is O; $Y^{2c}$ is $N(CH_3)$; and $R^y$ is H or $C_1$-$C_8$ alkyl.

For a conjugate of Formula I, in one specific embodiment, the substituted triazole has the structure:

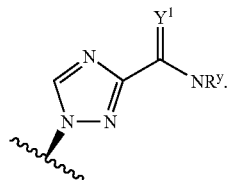

In one specific embodiment, the conjugate of Formula I is a conjugate of the following formula:

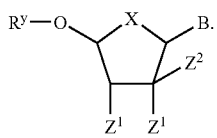

or a pharmaceutically acceptable salt or solvate thereof;

wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo[3,4-D]pyrimidine;

$Z^1$ is independently selected from H, OH, OR, $NR_2$, CN, $NO_2$, SH, SR, F, Cl, Br, and I;

$Z^2$ is selected from H, $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, and $C_1$-$C_8$ substituted alkynyl, $R^y$ is independently H, F, Cl, Br, I, OH, R, —C(=$Y^1$), —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$), —OC(=$Y^1$)OR, —OC(=$Y^1$)(N(R)$_2$), —SC(=$Y^1$), —SC(=$Y^1$)OR, —SC(=$Y^1$)(N(R)$_2$), —N(R)C(=$Y^1$), —N(R)C(=$Y^1$)OR, or —N(R)C(=$Y^1$)N(R)$_2$, amino (—NH$_2$), ammonium (—NH$_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—SO$_2$R), arylsulfone (—SO$_2$Ar), arylsulfoxide (—SOAr), arylthio (—SAr), sulfonamide (—SO$_2$NR$^2$), alkylsulfoxide (—SOR), ester (—C(=O)OR), amido (—C(=O)NR$_2$), 5-7 membered ring lactam, 5-7 membered ring lactone, nitrile (—CN), azido (—N$_3$), nitro (—NO$_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, a protecting group (PG), or $W^3$; or when taken together, $R^y$ forms a carbocyclic ring of 3 to 7 carbon atoms;

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, —C($Y^1$)$R^y$, —C($Y^1$)$W^5$, —SO$_2R^y$, or —SO$_2W^5$; and $W^5$ is a carbocycle or a heterocycle wherein $W^5$ is independently substituted with 0 to 3 $R^y$ groups.

In one specific embodiment, the conjugate of Formula I has the following formula:

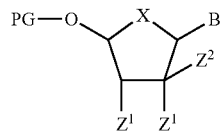

wherein PG is a protecting group selected from an ether-forming group, a thioether-forming group, an ester-forming group, a thioester-forming group, a silyl-ether forming group, an amide-forming group, an acetal-forming group, a ketal-forming group, a carbonate-forming group, a carbamate-forming group, a urea-forming group, an amino acid conjugate, and a polypeptide conjugate.

In one specific embodiment, the invention provides a conjugate of Formula I having one of the following formulae:

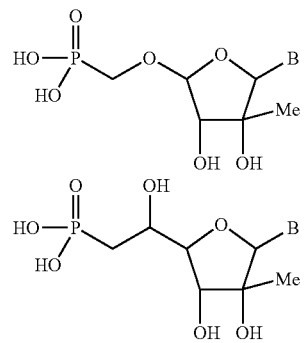

or a pharmaceutically acceptable salt or solvate thereof; wherein B is adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, or pyrazolo[3,4-D]pyrimidine. In an additional embodiment, the compound is isolated and purified.

In one specific embodiment, the invention provides a conjugate of Formula I hone of the following formulae:

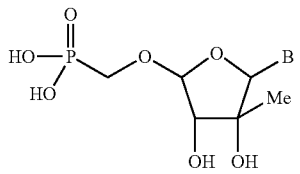

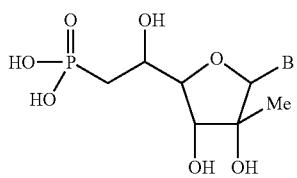

or a pharmaceutically acceptable salt or solvate thereof; wherein B is adenine, guanine, cytosine, uracil, thymine, 7-deazaadenine, 2,6-diaminopurine, 5-fluorocytosine, or c-propyl-2,6-diaminopurine. In an additional embodiment, the compound is isolated and purified.

In one specific embodiment, the invention provides a conjugate of Formula I having one of the following formulae:

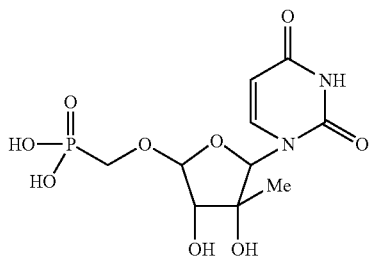

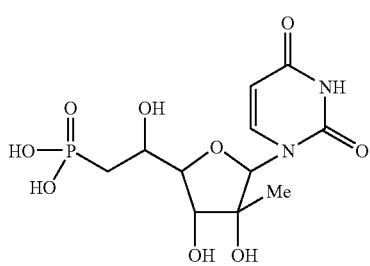

or a pharmaceutically acceptable salt or solvate thereof. In an additional embodiment, the compound is isolated and purified.

In one specific embodiment, the invention provides a conjugate of Formula I having one of the following formulae:

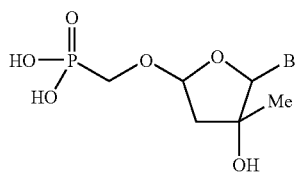

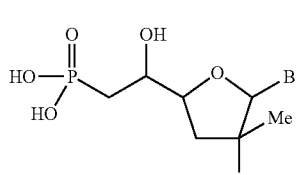

or a pharmaceutically acceptable salt or solvate thereof, wherein B is adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methyl indole, substituted triazole, or pyrazolo [3,4-D]pyrimidine. In an additional embodiment, the compound is isolated and purified.

In one specific embodiment, the invention provides a conjugate of Formula I having one of the following formulae:

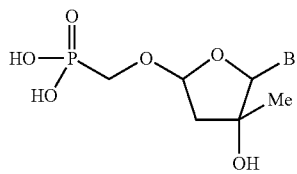

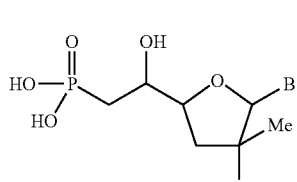

or a pharmaceutically acceptable salt or solvate thereof; wherein B is adenine, guanine, cytosine, uracil, thymine, 7-deazaadenine, 2,6-diaminopurine, 5-fluorocytosine, or c-propyl-2,6-diaminopurine. In an additional embodiment, the compound is isolated and purified.

In one specific embodiment, the invention provides a conjugate of Formula I having one of the following formulae:

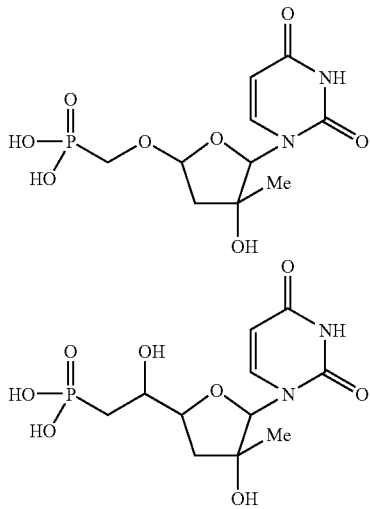

or a pharmaceutically acceptable salt or solvate thereof. In an additional embodiment, the compound is isolated and purified.

Conjugates of Formula II

In one embodiment, the invention provides a conjugate of Formula II:

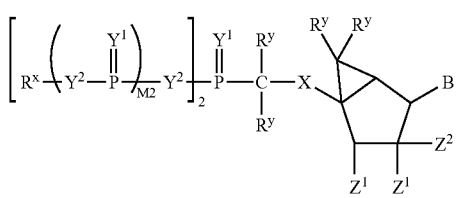

II or a pharmaceutically acceptable salt or solvate thereof, wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo[3,4-D]pyrimidine;

X is selected from O, $C(R^y)_2$, $OC(R^y)_2$, NR and S;

$Z^1$ is independently selected from H, OH, OR, $NR_2$, CN, $NO_2$, SH, SR, F, Cl, Br, and I;

$Z^2$ is selected from H, $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, and $C_1$-$C_8$ substituted alkynyl, $Y^1$ is independently O, S, NR, $^+N(O)(R)$, N(OR), $^+N(O)(OR)$, or N—$NR_2$;

$Y^2$ is independently a bond, O, $CR_2$, NR, $^+N(O)(R)$, N(OR), $^+N(O)(OR)$, N—$NR_2$, S, S—S, S(O), or $S(O)_2$;

M2 is 0, 1 or 2;

$R^y$ is independently H, F, Cl, Br, I, OH, R, —C(=$Y^1$), —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$), —OC(=$Y^1$)OR, —OC(=$Y^1$)(N(R)$_2$), —SC(=$Y^1$), —SC(=$Y^1$)OR, —SC(=$Y^1$)(N(R)$_2$), —N(R)C(=$Y^1$), —N(R)C(=$Y^1$)OR, or —N(R)C(=$Y^1$)N(R)$_2$, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2R$), arylsulfone (—$SO_2Ar$), arylsulfoxide (—SOAr), arylthio (—SAr), sulfonamide (—$SO_2NR_2$), alkylsulfoxide (—SOR), ester (—C(=O)OR), amido (—C(=O)NR$_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, a protecting group, or $W^3$; or when taken together, $R^y$ forms a carbocyclic ring of 3 to 7 carbon atoms;

$R^x$ is independently $R^y$, a protecting group, or the formula:

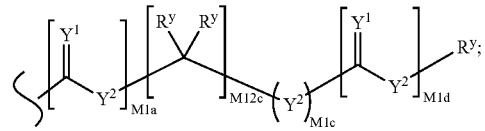

wherein:

M1a, M1c, and M1d are independently 0 or 1;

M12c is 0, 1, 2, 3, 4, 5, 6, 7, 8, 9, 10, or 12; and

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, —C($Y^1$)$R^y$, —C($Y^1$)$W^5$, —$SO_2R^y$, or —$SO_2W^5$; and $W^5$ is a carbocycle or a heterocycle wherein $W^5$ is independently substituted with 0 to 3 $R^y$ groups.

For a conjugate of Formula II, in one specific embodiment, $C_1$-$C_8$ substituted alkyl, $C_1$-$C_8$ substituted alkenyl, $C_1$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, —$NH_2$, —$NH_3^+$, —NHR, —$NR_2$, —$NR_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —$SO_2R$, —$SO_2Ar$, —SOAr, —SAr, —$SO_2NR_2$, —SOR, —$CO_2R$, —C(=O)NR$_2$, 5-7 membered ring lactam, 5-7 membered ring lactone, —CN, —$N_3$, —$NO_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, phosphate, and a prodrug moiety.

For a conjugate of Formula II, in one specific embodiment, "protecting group" is selected from a carboxyl ester, a carboxamide, an aryl ether, an alkyl ether, a trialkylsilyl ether, a sulfonic acid ester, a carbonate, and a carbamate.

For a conjugate of Formula II, in one specific embodiment, $W^5$ is selected from the structures:

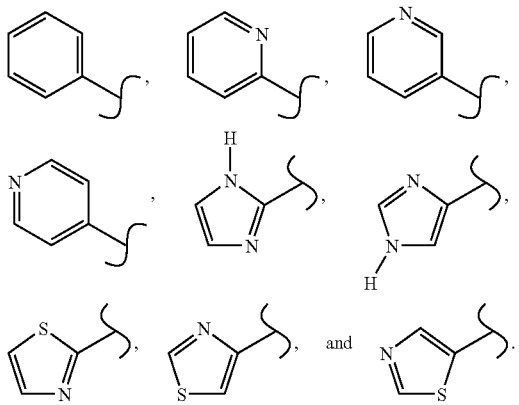

For a conjugate of Formula II, in one specific embodiment, X is O and $R^y$ is H.

In one specific embodiment, the conjugate of Formula II has the following formula:

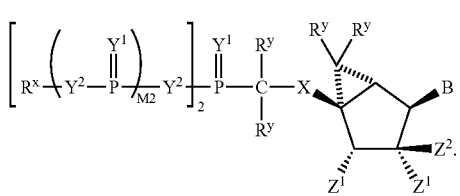

In one specific embodiment, the conjugate of Formula II has the following formula:

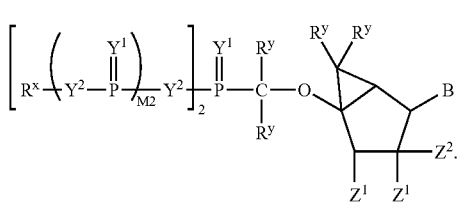

wherein, in a more specific embodiment, $Z^1$ is OH; and $Z^2$ is $CH_3$.

In one specific embodiment, the conjugate of Formula II has the following formula:

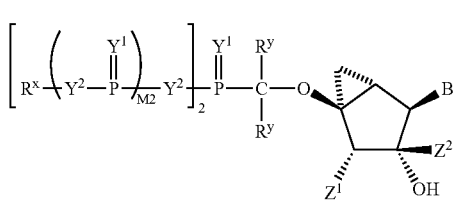

wherein, in a more specific embodiment, $Z^2$ is $C_1$-$C_8$ alkyl or $C_1$-$C_8$ substituted alkyl.

In one specific embodiment, the conjugate of Formula II has the following formula:

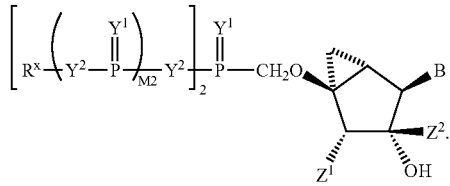

In one specific embodiment, the conjugate of Formula II has the following formula:

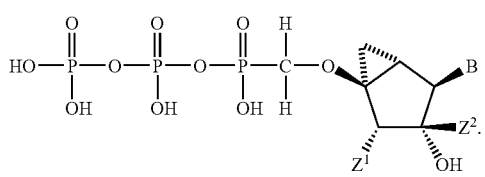

In one specific embodiment, the conjugate of Formula II has the following formula:

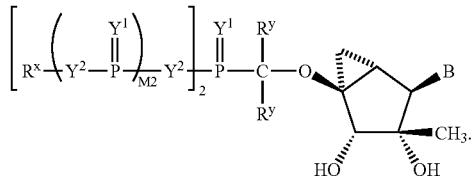

In one specific embodiment, the conjugate of Formula II has the following formula:

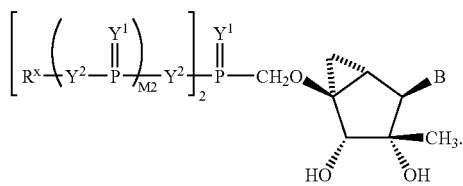

In one specific embodiment, the conjugate of Formula II has the following formula:

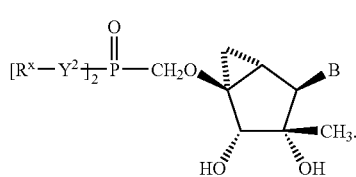

the conjugate of Formula II has the following formula:

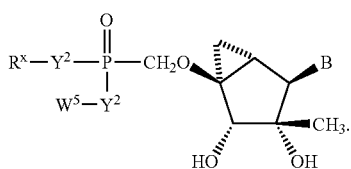

In one specific embodiment, the conjugate of Formula II has the following formula:

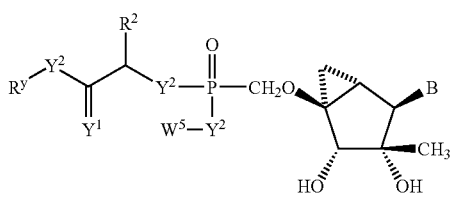

wherein $R^2$ is H or $C_1$-$C_8$ alkyl.

In one specific embodiment, the conjugate of Formula II has the following formula:

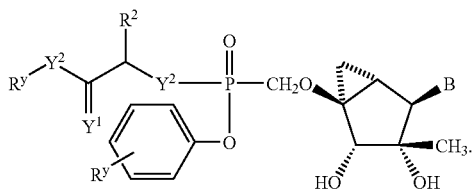

In one specific embodiment, the conjugate of Formula II has the following formula:

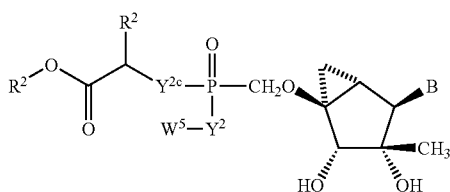

wherein $Y^{2c}$ is O, N($R^y$) or S.

In one specific embodiment, the conjugate of Formula II has the following formula:

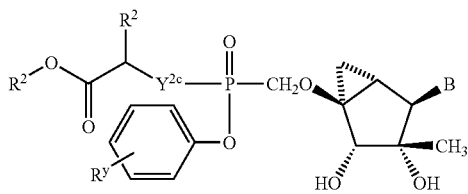

wherein, in a more specific embodiment, $Y^{2c}$ is O; $Y^{2c}$ is N(CH$_3$).

In one specific embodiment, the substituted triazole has the structure:

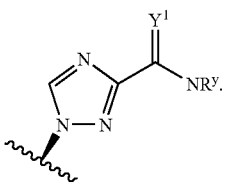

In one specific embodiment, the conjugate of Formula II has the following formula:

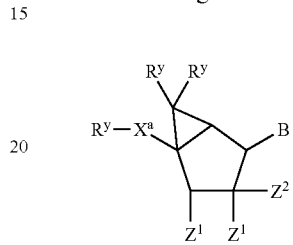

wherein:
B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo[3,4-D]pyrimidine;

$X^a$ is selected from O, NR and S;

$Z^1$ is independently selected from H, OH, OR, NR$_2$, CN, NO$_2$, SH, SR, F, Cl, Br, and I;

$Z^2$ is selected from H, $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, and $C_1$-$C_8$ substituted alkynyl, $R^y$ is independently H, F, Cl, Br, I, OH, R, —C(=Y$^1$), —C(=Y$^1$)OR, —C(=Y$^1$)N(R)$_2$, —N(R)$_2$, —$^+$N(R)$_3$, —SR, —S(O)R, —S(O)$_2$R, —S(O)(OR), —S(O)$_2$(OR), —OC(=Y$^1$), —OC(=Y$^1$)OR, —OC(=Y$^1$)(N(R)$_2$), —SC(=Y$^1$), —SC(=Y$^1$)OR, —SC(=Y$^1$)(N(R)$_2$), —N(R)C(=Y$^1$), —N(R)C(=Y$^1$)OR, or —N(R)C(=Y$^1$)N(R)$_2$, amino (—NH$_2$), ammonium (—NH$_3$$^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), ester (—C(=O)OR), amido (—C(=O)NR$_2$), 5-7 membered ring lactam, 5-7 membered ring lactone, nitrile (—CN), azido (—N$_3$), nitro (—NO$_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, a protecting group, or $W^3$; or when taken together, $R^y$ forms a carbocyclic ring of 3 to 7 carbon atoms;

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, —C($Y^1$)$R^y$, —C($Y^1$)$W^5$, —SO$_2$$R^y$, or —SO$_2$$W^5$; and $W^5$ is a carbocycle or a heterocycle wherein $W^5$ is independently substituted with 0 to 3 $R^y$ groups.

In one specific embodiment, the conjugate of Formula II has the following formula:

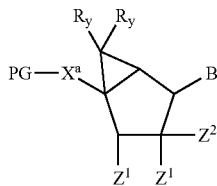

wherein PG is a protecting group selected from an ether-forming group, a thioether-forming group, an ester-forming group, a thioester-forming group, a silyl-ether forming group, an amide-forming group, an acetal-forming group, a ketal-forming group, a carbonate-forming group, a carbamate-forming group, a urea-forming group, an amino acid conjugate, and an olypeptide conjugate Conjugates of Formula III In one embodiment, the invention provides a conjugate of Formula III:

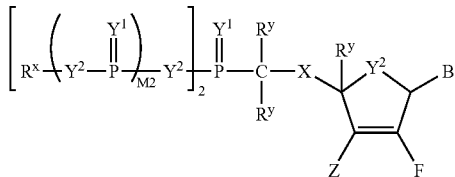

or a pharmaceutically acceptable salt or solvate thereof;

wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, O$^6$-methylguanine, N$^6$-methyladenine, O$^4$-methylthymine, 5,6-dihydrothymine, 5,6-dihydrouracil, 4-methylindole, substituted triazole, and pyrazolo[3,4-D]pyrimidine;

X is selected from O, C($R^y$)$_2$, OC($R^y$)$_2$, NR and S;

Z is independently selected from H, OH, OR, NR$_2$, CN, NO$_2$, SH, SR, F, Cl, Br, and I;

$Y^1$ is independently O, S, NR, $^+$N(O)(R), N(OR), $^+$N(O)(OR), or N—NR$_2$;

$Y^2$ is independently O, CR$_2$, NR, $^+$N(O)(R), N(OR), $^+$N(O)(OR), N—NR$_2$, S, S—S, S(O), or S(O)$_2$;

M2 is 0, 1 or 2;

$R^y$ is independently H, F, Cl, Br, I, OH, —C(=$Y^1$), —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$), —OC(=$Y^1$)OR, —OC(=$Y^1$)(N(R)$_2$), —SC(=$Y^1$), —SC(=$Y^1$)OR, —SC(=$Y^1$)(N(R)$_2$), —N(R)C(=$Y^1$), —N(R)C(=$Y^1$)OR, or —N(R)C(=$Y^1$)N(R)$_2$, amino (—NH$_2$), ammonium (—NH$_3$$^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), ester (—C(=O)OR), amido (—C(=O)NR$_2$), 5-7 membered ring lactam, 5-7 membered ring lactone, nitrile (—CN), azido (—N$_3$), nitro (—NO$_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, or $W^3$; or when taken together, $R^y$ forms a carbocyclic ring of 3 to 7 carbon atoms;

$R^x$ is independently $R^y$, a protecting group, or the formula:

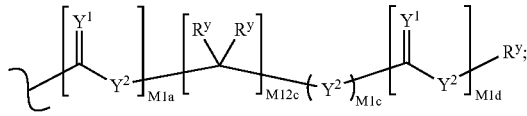

wherein:

M1a, M1c, and M1d are independently 0 or 1;

M12c is 0, 1, 2, 3, 4, 5, 6, 7, 8, 9, 10, 11 or 12; and

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, —C($Y^1$)$R^y$, —C($Y^1$)$W^5$, —SO$_2$$R^y$, or —SO$_2$$W^5$; and $W^5$ is a carbocycle or a heterocycle wherein $W^5$ is independently substituted with 0 to 3 $R^y$ groups.

For a conjugate of Formula II, in one specific embodiment, $C_1$-$C_8$ substituted alkyl, $C_1$-$C_8$ substituted alkenyl, $C_1$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, —NH$_2$, —NH$_3$$^+$, —NHR, —NR$_2$, —NR$_3$$^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, phosphate, and a prodrug moiety.

For a conjugate of Formula II, in one specific embodiment, "protecting group" is selected from a carboxyl ester, a carboxamide, an aryl ether, an alkyl ether, a trialkylsilyl ether, a sulfonic acid ester, a carbonate, and a carbamate.

In one specific embodiment, for a conjugate of Formula III, $W^5$ is selected from the structures:

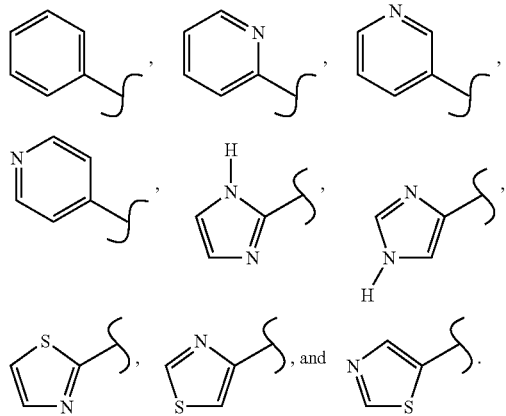

In one specific embodiment, for a conjugate of Formula III, X is O and each $R^y$ is H.

In one specific embodiment, the conjugate of Formula III is a resolved enantiomer having the structure:

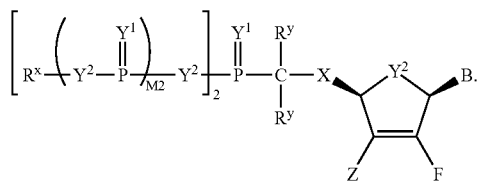

In one specific embodiment, the conjugate of Formula III is a resolved enantiomer having the structure:

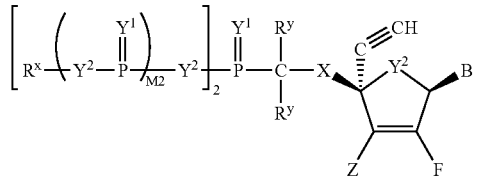

In one specific embodiment, the conjugate of Formula III has the following formula:

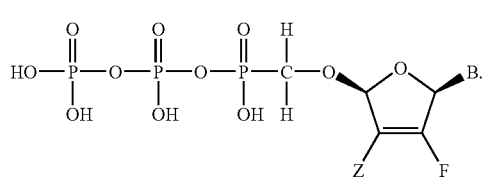

In one specific embodiment, the conjugate of Formula III has the following formula:

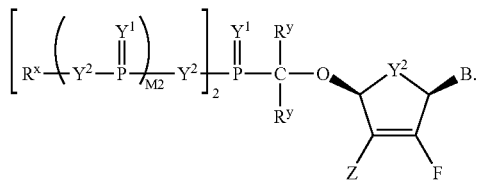

In one specific embodiment, the conjugate of Formula III has the following formula:

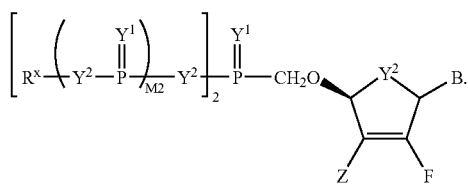

In one specific embodiment, the conjugate of Formula III has the following formula:

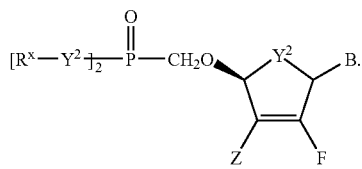

In one specific embodiment, the conjugate of Formula III has the following formula:

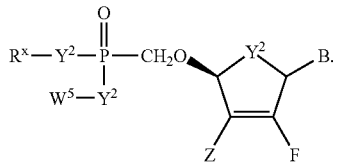

In one specific embodiment, the conjugate of Formula III has the following formula:

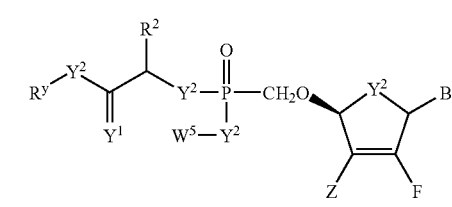

wherein $R^2$ is H or $C_1$-$C_8$ alkyl.

In one specific embodiment, the conjugate of Formula III has the following formula:

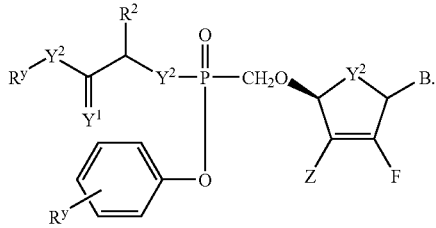

In one specific embodiment, the conjugate of Formula III has the following formula:

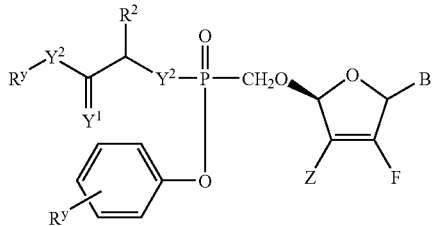

wherein in a more specific embodiment, Z is H and B is adenine.

In one specific embodiment, the conjugate of Formula III has the following formula:

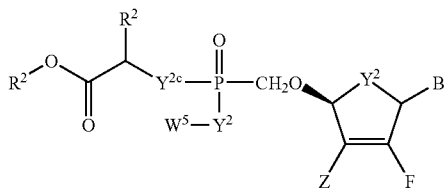

wherein $Y^{2c}$ is O, $N(R^y)$ or S.

In one specific embodiment, the conjugate of Formula III has the following formula:

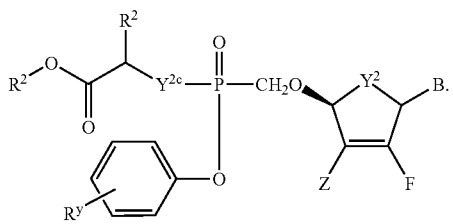

wherein, in a more specific embodiment, $Y^{2a}$ is O or $N(CH_3)$.

In one specific embodiment, for a conjugate of Formula III, substituted triazole has the structure:

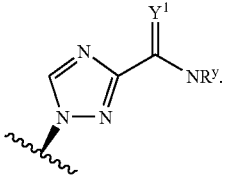

In one specific embodiment, the conjugate of Formula III has the following formula:

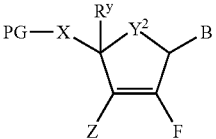

wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo[3,4-D]pyrimidine;

X is selected from O, $C(R^y)_2$, $OC(R^y)_2$, NR and S;

Z is independently selected from H, OH, OR, $NR_2$, CN, $NO_2$, SH, SR, F, Cl, Br, and I;

$Y^2$ is independently O, $CR_2$, NR, $^+N(O)(R)$, N(OR), $^+N(O)$(OR), N—$NR_2$, S, S—S, S(O), or $S(O)_2$;

$R^y$ is independently H, F, Cl, Br, I, OH, —$C(=Y^1)$, —$C(=Y^1)OR$, —$C(=Y^1)N(R)_2$, —$N(R)_2$, —$^+N(R)_3$, —SR, —S(O)R, —$S(O)_2R$, —S(O)(OR), —$S(O)_2(OR)$, —OC(=$Y^1$), —OC(=$Y^1$)OR, —OC(=$Y^1$)(N(R)_2), —SC(=$Y^1$), —SC(=$Y^1$)OR, —SC(=$Y^1$)(N(R)_2), —N(R)C(=$Y^1$), —N(R)C(=$Y^1$)OR, or —N(R)C(=$Y^1$)N(R)_2, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2R$), arylsulfone (—$SO_2Ar$), arylsulfoxide (—SOAr), arylthio (—SAr), sulfonamide (—$SO_2NR_2$), alkylsulfoxide (—SOR), ester (—C(=O)OR), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, or $W^3$; or when taken together, $R^y$ forms a carbocyclic ring of 3 to 7 carbon atoms;

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and PG is a protecting group selected from an ether-forming group, an ester-forming group, a silyl-ether forming group, an amide-forming group, an acetal-forming group, a ketal-forming group, a carbonate-forming group, a carbamate-forming group, an amino acid, and a polypeptide.

Linking Groups and Linkers

The invention provides conjugates that comprise an anti-cancer compound that is linked to one or more phosphonate groups either directly (e.g. through a covalent bond) or through a linking group (i.e. a linker). The nature of the linker is not critical provided it does not interfere with the ability of the phosphonate containing compound to function as a therapeutic agent. The phosphonate or the linker can be linked to the compound (e.g. a compound of Formula 500-601) at any synthetically feasible position on the compound by removing a hydrogen or any portion of the compound to provide an open valence for attachment of the phosphonate or the linker.

In one embodiment of the invention the linking group or linker (which can be designated "L") can include all or a portions of the group $A^0$, $A^1$, $A^2$, or $W^3$ described herein.

In another embodiment of the invention the linking group or linker has a molecular weight of from about 20 daltons to about 400 daltons.

In another embodiment of the invention the linking group or linker has a length of about 5 angstroms to about 300 angstroms.

In another embodiment of the invention the linking group or linker separates the DRUG and a $P(=Y^1)$ residue by about 5 angstroms to about 200 angstroms, inclusive, in length.

In another embodiment of the invention the linking group or linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In another embodiment of the invention the linking group or linker is of the formula W-A wherein A is ($C_1$-$C_{24}$)alkyl, ($C_2$-$C_{24}$)alkenyl, ($C_2$-$C_{24}$)alkynyl, ($C_3$-$C_8$)cycloalkyl, ($C_6$-$C_{10}$)aryl or a combination thereof, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or (C—$C_6$)alkyl.

In another embodiment of the invention the linking group or linker is a divalent radical formed from a peptide.

In another embodiment of the invention the linking group or linker is a divalent radical formed from an amino acid.

In another embodiment of the invention the linking group or linker is a divalent radical formed from poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

In another embodiment of the invention the linking group or linker is of the formula W—(CH$_2$)$_n$ wherein, n is between about 1 and about 10; and W is —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or ($C_1$-$C_6$)alkyl.

In another embodiment of the invention the linking group or linker is methylene, ethylene, or propylene.

In another embodiment of the invention the linking group or linker is attached to the phosphonate group through a carbon atom of the linker.

Intracellular Targeting

The phosphonate group of the compounds of the invention may cleave in vivo in stages after they have reached the desired site of action, i.e. inside a cell. One mechanism of action inside a cell may entail a first cleavage, e.g. by esterase, to provide a negatively-charged "locked-in" intermediate. Cleavage of a terminal ester grouping in a compound of the invention thus affords an unstable intermediate which releases a negatively charged "locked in" intermediate.

After passage inside a cell, intracellular enzymatic cleavage or modification of the phosphonate or prodrug compound may result in an intracellular accumulation of the cleaved or modified compound by a "trapping" mechanism. The cleaved or modified compound may then be "locked-in" the cell by a significant change in charge, polarity, or other physical property change which decreases the rate at which the cleaved or modified compound can exit the cell, relative to the rate at which it entered as the phosphonate prodrug. Other mechanisms by which a therapeutic effect are achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

In selected instances in which the drug is of the nucleoside type, such as is the case of zidovudine and numerous other antiretroviral agents, it is known that the drug is activated in vivo by phosphorylation. Such activation may occur in the present system by enzymatic conversion of the "locked-in" intermediate with phosphokinase to the active phosphonate diphosphate and/or by phosphorylation of the drug itself after its release from the "locked-in" intermediate as described above. In either case, the original nucleoside-type drug will be convened, via the derivatives of this invention, to the active phosphorylated species.

From the foregoing, it will be apparent that many different drugs can be derivatized in accord with the present invention. Numerous such drugs are specifically mentioned herein. However, it should be understood that the discussion of drug families and their specific members for derivatization according to this invention is not intended to be exhaustive, but merely illustrative.

Anti-cancer Compounds

The compounds of the invention include those with anti-cancer activity. In particular, the compounds include anti-cancer compounds. The compounds of the inventions bear one or more (e.g. 1, 2, 3, or 4) phosphonate groups, which may be a prodrug moiety.

Typically, compounds of the invention have a molecular weight of from about 400 amu to about 10,000 amu; in a specific embodiment of the invention, compounds have a molecular weight of less than about 5000 amu; in another specific embodiment of the invention, compounds have a molecular weight of less than about 2500 amu; in another specific embodiment of the invention, compounds have a molecular weight of less than about 1000 amu; in another specific embodiment of the invention, compounds have a molecular weight of less than about 800 amu; in another specific embodiment of the invention, compounds have a molecular weight of less than about 600 amu; and in another specific embodiment of the invention, compounds have a molecular weight of less than about 600 amu and a molecular weight of greater than about 400 amu.

The compounds of the invention also typically have a logD (polarity) less than about 5. In one embodiment the invention provides compounds having a logD less than about 4; in another one embodiment the invention provides compounds having a logD less than about 3; in another one embodiment the invention provides compounds having a logD greater than about −5; in another one embodiment the invention provides compounds having a logD greater than about −3; and in another one embodiment the invention provides compounds having a logD greater than about 0 and less than about 3.

In one specific embodiment the invention provides compounds that may fall within the generic definition of the term anti-cancer compound but which further comprise a phosphonate group, e.g., a phosphonate diester, phosphonamidate-ester prodrug, or a phosphondiamidate-ester (Jiang et al., U.S. 2002/0173490 A1).

Selected substituents within the compounds of the invention are present to a recursive degree. In this context, "recursive substituent" means that a substituent may recite another instance of itself. Because of the recursive nature of such substituents, theoretically, a large number may be present in any given claim. For example, $R^x$ contains a $R^y$ substituent. $R^y$ can be $R^2$, which in turn can be $R^3$. If $R^3$ is selected to be $R^{3c}$, then a second instance of $R^x$ can be selected. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$, $R^y$ and $R^3$ are all recursive substituents in certain claims. Typically, each of these may independently occur 20, 19, 18, 17, 16, 15, 14, 13, 12, 11, 10, 9, 8, 7, 6, 5, 4, 3, 2, 1, or 0, times in a given claim. More typically, each of these may independently occur 12 or fewer times in a given claim. More typically yet, $W^3$ will occur 0 to 8 times, $R^y$ will occur 0 to 6 times and $R^3$ will occur 0 to 10 times in a given claim. Even more typically, $W^3$ will occur 0 to 6 times, $R^y$ will occur 0 to 4 times and $R^3$ will occur 0 to 8 times in a given claim.

Recursive substituents are an intended aspect of the invention. One of ordinary skill in the art of medicinal chemistry understands the versatility of such substituents. To the degree that recursive substituents are present in an claim of the invention, the total number will be determined as set forth above.

Whenever a compound described herein is substituted with more than one of the same designated group, e.g., "$R^1$" or "$R^{6a}$" then it will be understood that the groups may be the same or different, i.e., each group is independently selected. Wavy lines indicate the site of covalent bond attachments to the adjoining groups, moieties, or atoms.

The term "anti-cancer compound" includes not only the generic disclosures cited above but also each and every species set forth therein. The phosphonate group may be a phosphonate prodrug moiety. The prodrug moiety may be sensitive to hydrolysis, such as, but not limited to, a pivaloyloxymethyl carbonate (POC) or POM group. Alternatively, the prodrug moiety may be sensitive to enzymatic potentiated cleavage, such as a lactate ester or a phosphonamidate-ester group.

The term "anti-cancer compound" also includes gefitinib, imatinib, erlotinib, vatalanib, fosteabine, camptosar, irinotecan, hycamtin, femara, letrozole, fadrozole, temozolomide, etopophos, anastrozole, arimidex, carboplatin, paraplatin, exemestane, atamestane, epirubicin, adriamycin, taxotere, taxol, vinorelbine, ospemifene, troglitazone, etoposide, everolimus, vincristine, sirolimus, raltitrexed (tomudex), aminopterin, alvocidib, bortezomib, VX-148, vinblastine, tipifarnib, mitoxantrone, vindesine, lonafarib, merimepodib, brequinar, amsacrine, CEP-701, decitabine, teniposide, midostaurin, MLN-518, PD-184352, emetrexed (ALIMTA), 10-propargyl-10-deaza-aminopterin (PDX), tacedinaline, thalidomide, TLK-286, pixantrone, pentostatin, enocitabine, clofarabine, BCX-1777, rubitecan, suberanilohydroxamic acid, revimid, MS-275, dexamethasone, LAQ-824, fludarabine, pirarubicin, teriflunomide, cerubidin HCL, idarubicin HCL, exatecan, sardomozide, adriamycin, methopterin, mizoribine, tamoxifen citrate/toremifine citrate, raloxifene hydrochloride, mycophenolate, dexamethasone, methotrexate, GLEEVEC, PNP-405, MDL-74428, 9-(3,3-dimethyl-5-phosphonopentyl)guanine, DADMe-IMMG, camptosar, idarubicin, leflunomide, BAY-43-9006, bicyclo nucleobase compounds, 2-fluoro, 2', 3' didehydro, 4' phosphonate nucleoside compounds, gemcitabine, cladribine, rofecoxib, ANA-245, and halobetasol propionate.

In one embodiment of the invention, the compound is not a kinase inhibitor, an IMPDH, a PMP, an anti-viral agent, or an autoimmune system enhancer. In another embodiment of the invention, the compound is not a compound of formula 501, 519, 597, 541, 518, 558, 591, 593, 592, 503, 504, 505, 506, 542, 544, 545, 546, 516, or 512.

Cellular Accumulation

In one embodiment, the invention is provides compounds capable of accumulating in human PBMC (peripheral blood mononuclear cells). PBMC refer to blood cells having round lymphocytes and monocytes. Physiologically, PBMC are critical components of the mechanism against infection. PBMC may be isolated from heparinized whole blood of normal healthy donors or buffy coats, by standard density gradient centrifugation and harvested from the interface, washed (e.g. phosphate-buffered saline) and stored in freezing medium. PBMC may be cultured in multi-well plates. At various times of culture, supernatant may be either removed for assessment, or cells may be harvested and analyzed (Smith R. et al (2003) *Blood* 102(7):2532-2540). The compounds of this claim may further comprise a phosphonate or phosphonate prodrug. More typically, the phosphonate or phosphonate prodrug can have the structure $A^3$ as described herein.

Typically, compounds of the invention demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In one embodiment of the invention the intracellular half-life of a metabolite of the compound in human PBMCs is improved when compared to an analog of the compound not having the phosphonate or phosphonate prodrug. In such claims, the metabolite may be generated intracellularly, e.g. generated within human PBMC. The metabolite may be a product of the cleavage of a phosphonate prodrug within human PBMCs. The phosphonate prodrug may be cleaved to form a metabolite having at least one negative charge at physiological pH. The phosphonate prodrug may be enzymatically cleaved within human PBMC to form a phosphonate having at least one active hydrogen atom of the form P—OH.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the iinvention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Treating Cancer

Another aspect of the invention relates to methods of treating cancer. Compositions of the invention may treat cancer, may act intermediates for such treatment or have other utilities as described below. The anti-cancer compounds will bind to locations on the surface or in a cavity of a cancer cell having a geometry unique to the anti-cancer compound. Compositions binding the anti-cancer compound may bind with varying degrees of reversibility. Those compounds binding substantially irreversibly are ideal candidates for use in this method of the invention. Once labeled, the substantially irreversibly binding compositions are useful as probes for the detection of cancer. Accordingly, the invention relates to methods of detecting cancer in a sample suspected of containing cancer comprising the steps of: treating a sample suspected of containing cancer with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention samples suspected of containing cancer include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing cancer. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of cancer after application of the composition can be observed by any method including direct and indirect methods of detecting cancer activity. Quantitative, qualitative, and semiquantitative methods of determining cancer activity are all contemplated. Typically one of the screening methods described above are applied, however, any other method such as observation of the physiological properties of a living organism are also applicable.

Organisms that contain cancer include mammals such as humans. The compounds of this invention are useful in the treatment or prophylaxis of cancer in animals or in man.

However, in screening compounds capable of treating cancer it should be kept in mind that the results of enzyme assays may not correlate with cell culture assays. Thus, a cell based assay should be the primary screening tool.

Screens for Anti-Cancer Compounds

Compositions of the invention are screened for activity against cancer by any of the conventional techniques for evaluating enzyme activity. Within the context of the invention, typically compositions are first screened for activity against cancer in vitro and compositions showing activity are then screened for activity in vivo. Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of cancerous infections as described below.

Formulations suitable for vaginal administration may be presented as p pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses) or against an active cancerous infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention are also used in combination with other active ingredients. Such combinations are selected based on the condition to be treated, cross-reactivities of ingredients and pharmaco-properties of the combination. For example, when treating cancer, the compositions of the invention can be combined with other chemotherapeutic agents. The second chemotherapeutic agent can be any suitable compound that has biological activity against one or more forms of cancer.

It is also possible to combine any compound of the invention with one or more other active ingredients in a unitary dosage form for simultaneous or sequential administration to an cancer patient. The combination therapy may be administered as a simultaneous or sequential regimen. When administered sequentially, the combination may be administered in two or more administrations. Second and third active ingredients in the combination may have chemotherapeutic activity and include any of the additional chemotherapeutic agents described herein. Exemplary active ingredients to be administered in combination with compounds of the invention are described below.

Suitable additional chemotherapeutic agents include, e.g., antracyclines (e.g., doxorubicin, daunorubicin, epirubicin, idarubicin, and mitoxantrone); (b) other DNA intercalators (e.g., actinomycins C, D, B, etc.; podophyllotoxins, and epipodophyllatoxins (etoposide, teniposide, ctoposide)); (c) alkylating agents (e.g., mechlorethamine, melphalan, cyclophosphamide, chlorambucil, ifosfamide, carmustine, lomustine, busulfan, dacarbazine, cisplatin, carboplatin, oxaliplatin, iproplatin, and tetraplatin); (d) hormonal agents (e.g., antiestrogens/estrogen antagonists (tamoxifen and other SERMs); LHRH agonists and antagonists (leuprolide acetate, goserelin, abarelix); aromatase inhibitors; and antiandrogens; (e) chemoprevention agents (e.g., NSAIDs and cis-retinoids); and (f) cell-cycle chemopreventative agents.

Alternatively, the additional chemotherapeutic agent can include, e.g., antineoplasts. Representative antineoplasts include, e.g., adjuncts (e.g., levamisole, gallium nitrate, granisetron, sargramostim strontium-89 chloride, filgrastim, pilocarpine, dexrazoxane, and ondansetron); androgen inhibitors (e.g., flutamide and leuprolide acetate); antibiotic derivatives (e.g., doxorubicin, bleomycin sulfate, daunorubicin, dactinomycin, and idarubicin); antiestrogens (e.g., tamoxifen citrate, analogs thereof, and nonsteroidal antiestrogens such as toremifene, droloxifene and roloxifene); antimetabolites (e.g., fludarabine phosphate, interferon alfa-2b recombinant, methotrexate sodium, plicamycin, mercaptopurine, and thioguanine); cytotoxic agents (e.g., doxorubicin, carmustine [BCNU], lomustine [CCNU], cytarabine USP, cyclophosphamide, estramucine phosphate sodium, altretamine, hydroxyurea, ifosfamide, procarbazine, mitomycin, busulfan, cyclophosphamide, mitoxantrone, carboplati, cisplati, cisplatin, interferon alfa-2a recombinant, paclitaxel, teniposide, and streptozoci); hormones (e.g., medroxyprogesterone acetate, estradiol, megestrol acetate, octreotide acetate, diethylstilbestrol diphosphate, testolactone, and goserelin acetate); immunomodulators (e.g., aldesleukin); nitrogen mustard derivatives (e.g., melphalan, chlorambucil, mechlorethamine, and thiotepa) and steroids (betamethasone sodium phosphate and betamethasone acetate).

Suitable additional chemotherapeutic agents include, e.g., alkylating agents, antimitotic agents, plant alkaloids, biologicals, topoisomerase I inhibitors, topoisomerase II inhibitors, and synthetics.

Representative alkylating agents include, e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864.

Representative antimitotic agents include, e.g., allocolchicine, Halichondrin B, colchicine, colchicine derivatives, dolastatin 10, maytansine, rhizoxin, paclitaxel derivatives, paclitaxel, thiocolchicine, trityl cysteine, vinblastine sulfate, and vincristine sulfate.

Representative plant alkaloids include, e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere.

Representative biologicals include, e.g., alpha interferon, BCG, G-CSF, GM-CSF, and interleukin-2.

Representative topoisomerase I inhibitors include, e.g., camptothecin, camptothecin derivatives, and morpholinodoxorubicin.

Representative topoisomerase II inhibitors include, e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16.

Representative synthetics include, e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium.

Alternatively, the additional chemotherapeutic agent can include tubulin-binding drugs and drugs that affect tubulin dynamics and function. This includes a variety of drugs that are chemically unrelated to vinca alkaloids and taxanes (e.g. CP-248 [a derivative of exisulind] and ILX-651). These drugs have distinctive effects on cells at G2M-phase and may have functionally independent effects on cells in G1 and/or S phase.

Alternatively, the additional chemotherapeutic agent can include selective apoptotic anti-cancer drugs (SAANDs), which include sulindac, aptosyn, CP-461, CP-248 and related sulindac derived compounds that inhibit one or more of the following isozymes of cyclic GMP phosphodiesterase (cGMP PDE): 1, 2, 5.

Alternatively, the additional chemotherapeutic agent can include drugs that inhibit proteosomes (bortezomib or Velcade). Proteosomes degrade many ubiquitinated proteins that have been marked for active destruction. Ubiquitinated proteins include many critical cell cycle regulatory molecules and molecules that regulate apoptosis at specific stages of the cell cycle. While proteosomes may degrade proteins throughout the cell cycle, the proteins that are degraded by proteosomes include some of the most critical cell cycle regulatory proteins. The so-called "cell cycle active rationale" may be applied to the treatment of diseases in various categories, including cancer, inflammatory/autoimmune diseases, and neurological diseases that involve disorderly cell cycle and/or apoptosis.

Alternatively, the additional chemotherapeutic agent can include drugs that inhibit heat shock protein 90 (HSP90), a 'chaperonin' that participates in the degradation of 'client' proteins in the ubiquitin mediated proteosome pathway. Several drugs seem to exert their antitumour effect by inhibiting the intrinsic ATPase activity of HSP90, resulting in degradation of HSP90 "client proteins" via the ubiquitin proteosome pathway. Examples include: geldanamycin, 17-allylamino geldanamycin, 17-demethoxygeldanamycin and radicicol.

Suitable cell-cycle dependent biological agents or schedule-dependent biological agents include drugs, proteins or other molecules that block, impede, or otherwise interfere with, cell cycle progression at the G1-phase, G1/S interface, S-phase, G2/M interface, or M-phase of the cell cycle. These drugs are cell cycle-dependent or schedule-dependent.

Specifically, suitable cell-cycle dependent biological agents or schedule-dependent biological agents include:

(1) Analogues of uridine nucleosides, analogues of thymidine nucleosides, and analogues of uridine and thymidine nucleosides. These compounds act at the S-phase in tumor cells, and possibly neovascular endothelial cells. These compounds include, e.g., 5-fluorodeoxyuridine (floxuridine, FUDR); 5-flurouracil (5-FU); prodrugs of 5-FU (e.g. capecitabine, 5'-deoxy-5-fluorouridine, ftorafur, flucytosine); bromodeoxyuridine; and iododexoyuridine.

(2) Modulators of fluoropyrimidines. These compounds act at the S-phase in tumor cells, and possibly neovascular endothelial cells. These compounds include, e.g., leurovorin, methotrexate and other folates; levamisole; acivicin; phosphonacetyl-L-aspartic acid (PALA); brequinar; 5-ethynyluracil; and uracil.

(3) Cytidine analogues and cytidine nucleoside analogues. These compounds act at the S-phase in tumor cells, and possibly neovascular endothelial cells. These compounds include, e.g., cytarabine (Ara-C, cytosine arabinoside); gemcitabine (2',2'-difluorodeoxycytidine); and 5-azacytidine.

(4) Purine analogues and purine nucleoside analogues. These compounds act at the S-phase in tumor cells, and possibly neovascular endothelial cells. These compounds include, e.g., 6-thioguanine; 6-mercaptopurine; azathioprine; adenosine arabinoside (Ara-A); 2',2'-difluorodeoxyguanosine; deoxycoformycin (pentostatin); cladribine (2-chlorodeoxyadenosine); and inhibitors of adenosine deaminase.

(5) Antifolates. These compounds act at the S-phase in tumor cells, and possibly neovascular endothelial cells. These compounds include, e.g., methotrexate; aminopterin; trimetrexate; edatrexate; N10-propargyl-5,8-dideazafolic acid (CB3717); ZD1694, 5,8-dideazaisofolic acid (IAHQ); 5,10-dideazatetrahydrofolic acid (DDATHF); 5-deazafolic acid (efficient substrate for FPGS); PT523 (N alpha-(4-amino-4-deoxypteroyl)-N delta-hemiphthaloyl-L-ornithine); 10-ethyl-10-deazaminopterin (DDATHF, lomatrexol); piritrexim; 10-EDAM; ZD1694; GW$^{1843}$; PDX (10-propargyl-10-deazaminopterin); multi-targeted folate (i.e. LY231514, permetrexed); any folate-based inhibitor of thymidylate synthase (TS); any folate-based inhibitor of dihydrofolate reductase (DHFR); any folate-based inhibitor of glycinamide ribonucleotide transformylase (GARTF); any inhibitor of folylpolyglutamate synthetase (FPGS); and any folate-based inhibitor of GAR formyl transferase (AICAR transformylase).

(6) Other antimetabolites. These compounds act at the S-phase in tumor cells, and possibly neovascular endothelial cells. These compounds include, e.g., hydroxyurea and polyamines.

(7) S-phase specific radiotoxins (deoxythymidine analogues). These compounds act at the S-phase in all cells undergoing DNA synthesis. The compounds are incorporated into chromosomal DNA during S-phase. These compounds include, e.g., [125I]-iododeoxyuridine; [123I]-iododeoxyuridine; [124I]-iododeoxyuridine; [80mBr]-iododeoxyuridine; [131I]-iododeoxyuridine; and [211At]-astatine-deoxyuridine.

(8) Inhibitors of enzymes involved in deoxynucleoside/deoxynucleotide metabolism. These compounds act at the S-phase in tumor cells, and possibly neovascular endothelial cells. These compounds include, e.g., inhibitors of thymidylate synthase (TS); inhibitors of dihydrofolate reductase (DHFR); inhibitors of glycinamide ribonucleotide transformylase (GARTF); inhibitors of folylpolyglutamate synthetase (FPGS); inhibitors of GAR formyl transferase (AICAR transformylase); inhibitors of DNA polymerases (DNA Pol; e.g. aphidocolin); inhibitors of ribonucleotide reductase (RNR); inhibitors of thymidine kinase (TK); and inhibitors of topoisomerase I enzymes (e.g. camptothecins, irinotecan [CPT-11, camptosar], topotecan, NX-211 [lurtotecan], rubitecan, etc.).

(9) DNA chain-terminating nucleoside analogues. These compounds act specifically on S-phase cells and are incorporated into chromosomal DNA during S-phase; terminate growing DNA strand. These compounds include, e.g., acyclovir; abacavir; valacyclovir; zidovudine (AZT); didanosine (ddI, dideoxycytidine); zalcitabine (ddC); stavudine (D4T); lamivudine (3TC); Any 2' 3'-dideoxy nucleoside analogue; and any 2' 3'-dideoxy nucleoside analogue that terminates DNA synthesis. These compounds include, e.g., inhibitors of growth factor receptor tyrosine kinases that regulate progression through the G1-phase, G1/S interface, or S-phase of the cell cycle (e.g. EGF receptors, HER-2 neu/c-erbB2 receptor, PDGF receptors, etc; [e.g. trastusumab, iressa, erbitux, tarceva]); inhibitors of non-receptor tyrosine kinases (e.g. c-src family of tyrosine kinases; [e.g. Gleevec]); inhibitors of serine-threonine kinases that regulate progression through the G1-phase, G1/S interface or S-phase of the cell cycle (e.g. G1 cyclin-dependent kinases, G1/S cyclin-dependent kinases, and S cyclin-dependent kinases [e.g. CDK2, CDK4, CDK5, CDK6]; mitogen-activated kinases; MAP kinase signaling pathway); inhibitors of G1-phase, G1/S interface or S-phase cyclins [e.g. cyclins D1, D2, D3, E, and A]); inhibitors of G-proteins and cGMP phosphodiesterases that positively regulate cell cycle progression at the G1-phase, G1/S interface or S-phase of the cell cycle; drugs that inhibit the induction of immediate early response transcription factors (e.g. N-terminal c-jun kinase, c-myc); and drugs that inhibit proteosomes that degrade 'negative' cell cycle regulatory molecules (e.g. p53, p27/Kip1; [e.g. bortezomib]).

(10) Cytokines, growth factors, anti-angiogenic factors and other proteins that inhibit cell cycle progression at the G1-phase or G1/S interface of the cell cycle. These compounds act at G1, G6/S or S-phase of the cell cycle in tumor cells, and in some cases, neovascular endothelial cells. These compounds include, e.g., interferons; interleukins; somatostatin and somatostatin analogues (octreotide, sandostatin LAR); and many anti-angiogenic factors inhibit cell proliferation of endothelial cells at the G1 or G1/S phases of the cell cycle.

(11) Drugs and compounds that inhibit cell cycle progression at the G2/M interface, or M-phase of the cell cycle. These compounds act at G2/M interface or M-phase of the cell cycle in tumor cells, and in some cases, neovascular endothelial cells. These compounds include, e.g., (a) microtubule-targeting drugs—taxanes (e.g., taxol, taxotere, epothilones, and other taxanes and derivatives); (b) microtubule-targeting drugs—vinca alkaloids (e.g., vinblastine, vincristine, vindesine; vinflunine, vinorelbine, vinzolidine, nocadazole, and colchicines); (c) microtubule-targeting drugs—others (e.g., estramustine, CP-248 and CP-461); (d) inhibitors of serine-threonine kinases that regulate progression through the G2/M interface or M-phase of the cell cycle (e.g., inhibitors of G2/M cyclin-dependent kinases (e.g. CDC2); inhibitors of M-phase cyclins (e.g. cyclin B) and any drug that blocks, impedes, or otherwise interferes with, cell cycle progression at the G2/M interface, or M-phase of the cell cycle).

(12) Radiopharmaceuticals useful in radiation therapy and/or diagnosis. A suitable class of radioisotopes decay by a nuclear disintegration process known as the "Auger Process" or "Auger Cascade". Auger emitting isotopes generate short acting electrons that efficiently cleave duplex DNA. Suitable Auger-emitting radionuclides include, e.g., 125-Iodine, 123-Iodine and 80m-Bromine. Suitable corresponding halogenated pryimidine and purine nucleosides include, e.g., 5-125Iodo-2'-deoxyuridine, 5-123Iodo-2'-deoxyuridine, 5-80mBromo-2'-deoxyuridine and 8-80mBromo-2'-guanidine.

Growth Factors

Many growth factors and cytokines have the capacity to stimulate malignant cells to traverse specific points in the cell cycle. For example, G-CSF or GM-CSF can stimulate leukemic blasts in acute myeloid leukemia to traverse the G1/S interface. This increases the cells' susceptibility to cell-cycle specific drugs, such as cytarabine. Similar strategies have been tested using EGF and cytotoxic drugs for solid tumors. In order to respond the the growth factor, cells must be at a specific stage of the cell cycle, e.g., at the G1/S interface. The continuous presence of a growth factor could be beneficial, because at any given time, only a subset of the blasts are at G1/S. Thus, the growth factors act in a cell cycle specific fashion. Similar logic can be applied to the use of hematopoietic growth factors used to treat neutropenia, anemia and thrombocytopenia.

As such, peptide/protein growth factors can be employed in the present invention to promote survival of normal non-malignant cell lineages. One benefit in using such substances is the ability to protect proliferating cells in bone marrow, skin, oral and gastrointestinal mucosa, and hair follicles.

Examples of substances within this category include, e.g., hematopoietic growth factors: G-CSF, GM-CSF, erythropoietin, thrombopoietin and biologically active derivatives of these peptides; keratinocyte growth factor (KGF) for mucositis; B-lymphocyte stimulating pepdie (BLys); platelet derived growth factor (PDGF), epithelial growth factor (EGF), TGF-alpha and related growth factors; interleukins (e.g. IL-2, IL-6); other cytokines, growth factors and peptides that stimulate proliferation of non-malignant cells that need to be protected.

Therapeutic Growth Factors/Cytokines

Some therapeutic growth factors/cytokines can inhibit cell proliferation of cancer cells and/or neovascular cells at specific stages of the cell cycle. For example, interferons, somatostatin, octreotide and analogues thereof, thrombospondin and troponin-I inhibit neovascular endothelial cell proliferation by reducing the rate at which the cells enter S-phase. As such, any one or more of these substances can be employed in the present invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-cancer activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but are substantially hydrolyzed to the parental drug in the digestive lumen, liver or other metabolic organ, or within cells in general.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

SCHEMES AND EXAMPLES

General aspects of these exemplary methods are described below and in the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Examples General Section

A number of exemplary methods for the preparation of compounds of the invention are provided herein, for example, in the Examples hereinbelow. These methods are intended to illustrate the nature of such preparations and are not intended to limit the scope of applicable methods. Certain compounds of the invention can be used as intermediates for the preparation of other compounds of the invention. For example, the interconversion of various phosphonate compounds of the invention is illustrated below.

Interconversions of the Phosphonates R-Link-P(O)(OR$^1$)$_2$, R-Link-P(O)(OR$^1$)(OH) and R-Link-P(O)(OH)$_2$.

The following Schemes 32-38 described the preparation of phosphonate esters of the general structure R-link-P(O)(OR$^1$)$_2$, in which the groups R$^1$ may be the same or different. The R$^1$ groups attached to a phosphonate ester, or to precursors thereto, may be changed using established chemical transformations. The interconversion reactions of phosphonates are illustrated in Scheme S32. The group R in Scheme 32 represents the substructure, i.e. the drug "scaffold, to which the substituent link-P(O)(OR$^1$)$_2$ is attached, either in the compounds of the invention, or in precursors thereto. At the point in the synthetic route of conducting a phosphonate interconversion, certain functional groups in R may be protected. The methods employed for a given phosphonate transformation depend on the nature of the substituent R$^1$, and of the substrate to which the phosphonate group is attached. The preparation and hydrolysis of phosphonate esters is described in *Organic Phosphorus Compounds*, G. M. Kosolapoff, L. Maeir, eds, Wiley, 1976, p. 9ff.

In general, synthesis of phosphonate esters is achieved by coupling a nucleophile amine or alcohol with the corresponding activated phosphonate electrophilic precursor. For example, chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med. Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I*, 1577). Chlorophosphonate species may also be generated in situ from corresponding cyclic phosphites (Silverburg, et al., (1996) *Tetrahedron lett.*, 37:771-774), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., (1988) *Tetrahedron lett.*, 29:5763-66).

Phosphonate prodrugs of the present invention may also be prepared from the free acid by Mitsunobu reactions (Mitsunobu, (1981) Synthesis, 1; Campbell, (1992) *J. Org. Chem.* 57:6331), and other acid coupling reagents including, but not limited to, carbodiimides (Alexander, et al, (1994) *Collect. Czech. Chem. Commun.* 59:1853; Casara et al, (1992) *Bioorg. Med. Chem. Lett.* 2:145; Ohashi et al, (1988) *Tetrahedron Lett.*, 29:1189), and benzotriazolyloxytris-(dimethylamino) phosphonium salts (Campagne et al (1993) *Tetrahedron Lett.* 34:6743).

Aryl halides undergo Ni$^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis et al (1987) *J. Am. Chem. Soc.* 109:2831; Lu et al (1987) Synthesis 726). In another method, aryl phosphonate esters are prepared from aryl phosphates under anionic rearrangement conditions (Melvin (1981) *Tetrahedron Lett.* 22:3375; Casteel et al (1991) *Synthesis*, 691). N-Alkoxy aryl salts with alkali met al derivatives of cyclic alkyl phosphonate provide general synthesis for heteroaryl-2-phosphonate linkers (Redmore (1970) *J. Org. Chem.* 35:4114). These above mentioned methods can also be extended to compounds where the W$^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethylcarbodiimide hydrochloride (EDCI) can also be utilized for the synthesis of cyclic phosphonate prodrugs.

The conversion of a phosphonate diester S32.1 into the corresponding phosphonate monoester S32.2 (Scheme 32, Reaction 1) is accomplished by a number of methods. For example, the ester S32.1 in which R$^1$ is an aralkyl group such as benzyl, is converted into the monoester compound S32.2 by reaction with a tertiary organic base such as diazabicyclooctane (DABCO) or quinuclidine, as described in *J. Org. Chem.* (1995) 60:2946. The reaction is performed in an inert hydrocarbon solvent such as toluene or xylene, at about 110° C. The conversion of the diester S32.1 in which R$^1$ is an aryl group such as phenyl, or an alkenyl group such as allyl, into the monoester S32.2 is effected by treatment of the ester S32.1 with a base such as aqueous sodium hydroxide in acetonitrile or lithium hydroxide in aqueous tetrahydrofuran. Phosphonate diesters S32.1 in which one of the groups R$^1$ is aralkyl, such as benzyl, and the other is alkyl, is converted into the monoesters S32.2 in which R$^1$ is alkyl by hydrogenation, for example using a palladium on carbon catalyst. Phosphonate diesters in which both of the groups R$^1$ are alkenyl, such as allyl, is converted into the monoester S32.2 in which R$^1$ is alkenyl, by treatment with chlorotris(triphenylphosphine) rhodium (Wilkinson's catalyst) in aqueous ethanol at reflux, optionally in the presence of diazabicyclooctane, for example by using the procedure described in *J. Org. Chem.* (1973) 38:3224, for the cleavage of allyl carboxylates.

The conversion of a phosphonate diester S32.1 or a phosphonate monoester S32.2 into the corresponding phosphonic acid S32.3 (Scheme 32, Reactions 2 and 3) can be effected by reaction of the diester or the monoester with trimethylsilyl bromide, as described in *J. Chem. Soc., Chem. Comm.*, (1979) 739. The reaction is conducted in an inert solvent such as, for example, dichloromethane, optionally in the presence of a silylating agent such as bis(trimethylsilyl)trifluoroacetamide, at ambient temperature. A phosphonate monoester S32.2 in which R$^1$ is aralkyl such as benzyl, is converted into the corresponding phosphonic acid S32.3 by hydrogenation over a palladium catalyst, or by treatment with hydrogen chloride in an ethereal solvent such as dioxane. A phosphonate monoester S32.2 in which R$^1$ is alkenyl such as, for example, allyl, is converted into the phosphonic acid S32.3 by reaction with Wilkinson's catalyst in an aqueous organic solvent, for example in 15% aqueous acetonitrile, or in aqueous ethanol, for example using the procedure described in *Helv. Chim. Acta*. (1985) 68:618. Palladium catalyzed hydrogenolysis of phosphonate esters S32.1 in which R$^1$ is benzyl is described in *J. Org. Chem.* (1959) 24:434. Platinum-catalyzed hydrogenolysis of phosphonate esters S32.1 in which R¹ is phenyl is described in *J. Am. Chem. Soc.* (1956) 78:2336.

The conversion of a phosphonate monoester S32.2 into a phosphonate diester S32.1 (Scheme 32, Reaction 4) in which the newly introduced R¹ group is alkyl, aralkyl, haloalkyl such as chloroethyl, or aralkyl is effected by a number of reactions in which the substrate S32.2 is reacted with a hydroxy compound R¹OH, in the presence of a coupling agent. Typically, the second phosphonate ester group is different than the first introduced phosphonate ester group, i.e. R¹ is followed by the introduction of R² where each of R¹ and R² is alkyl, aralkyl, haloalkyl such as chloroethyl, or aralkyl (Scheme 32, Reaction 4a) whereby S32.2 is converted to S32.1a. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester S32.2 to the diester S32.1 is effected by the use of the Mitsunobu reaction, as described above (Scheme 7). The substrate is reacted with the hydroxy compound R¹OH, in the presence of diethyl azodicarboxylate and a triarylphosphine such as triphenyl phosphine. Alternatively, the phosphonate monoester S32.2 is transformed into the phosphonate diester S32.1, in which the introduced R¹ group is alkenyl or aralkyl, by reaction of the monoester with the halide R¹Br, in which R¹ is as alkenyl or aralkyl. The alkylation reaction is conducted in a polar organic solvent such as dimethylformamide or acetonitrile, in the presence of a base such as cesium carbonate. Alternatively, the phosphonate monoester is transformed into the phosphonate diester in a two step procedure. In the first step, the phosphonate monoester S32.2 is transformed into the chloro analog RP(O)(OR¹)Cl by reaction with thionyl chloride or oxalyl chloride and the like, as described in *Organic Phosphorus Compounds*, G. M. Kosolapoff, L. Maeir, eds, Wiley, 1976, p. 17, and the thus-obtained product RP(O)(OR¹)Cl is then reacted with the hydroxy compound R¹OH, in the presence of a base such as triethylamine, to afford the phosphonate diester S32.1.

A phosphonic acid R-link-P(O)(OH)₂ is transformed into a phosphonate monoester RP(O)(OR¹)(OH) (Scheme 32, Reaction 5) by means of the methods described above of for the preparation of the phosphonate diester R-link-P(O)(OR¹)₂ S32.1, except that only one molar proportion of the component R¹OH or R¹Br is employed. Dialkyl phosphonates may be prepared according to the methods of: Quast et al (1974) *Synthesis* 490; Stowell et al (1990) *Tetrahedron Lett.* 3261; U.S. Pat. No. 5,663,159.

A phosphonic acid R-link-P(O)(OH)₂ S32.3 is transformed into a phosphonate diester R-link-P(O)(OR¹)₂ S32.1 (Scheme 32, Reaction 6) by a coupling reaction with the hydroxy compound R¹OH, in the presence of a coupling agent such as Aldrithiol-2 (Aldrich) and triphenylphosphine. The reaction is conducted in a basic solvent such as pyridine. Alternatively, phosphonic acids S32.3 are transformed into phosphonic esters S32.1 in which R¹ is aryl, by means of a coupling reaction employing, for example, dicyclohexylcarbodiimide in pyridine at ca 70° C. Alternatively, phosphonic acids S32.3 are transformed into phosphonic esters S32.1 in which R¹ is alkenyl, by means of an alkylation reaction. The phosphonic acid is reacted with the alkenyl bromide R¹Br in a polar organic solvent such as acetonitrile solution at reflux temperature, the presence of a base such as cesium carbonate, to afford the phosphonic ester S32.1.

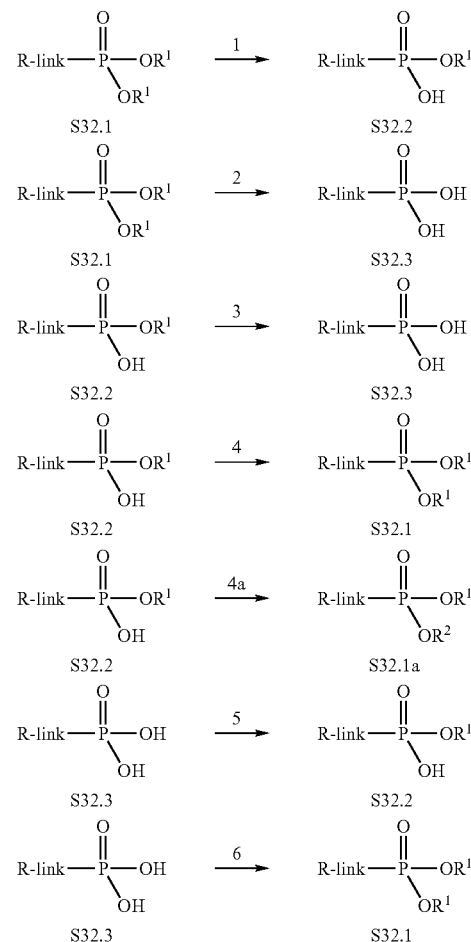

Scheme 32

Preparation of Phosphonate Carbamates.

Phosphonate esters may contain a carbamate linkage. The preparation of carbamates is described in *Comprehensive Organic Functional Group Transformations*, A. R. Katritzky, ed., Pergamon, 1995, Vol. 6, p. 416ff, and in *Organic Functional Group Preparations*, by S. R. Sandler and W. Karo, Academic Press, 1986, p. 260ff. The carbamoyl group may be formed by reaction of a hydroxy group according to the methods known in the art, including the teachings of Ellis, U.S. 2002/0103378 A1 and Hajima, U.S. Pat. No. 6,018,049.

Scheme 33 illustrates various methods by which the carbamate linkage is synthesized. As shown in Scheme 33, in the general reaction generating carbamates, an alcohol S33.1, is converted into the activated derivative S33.2 in which Lv is a leaving group such as halo, imidazolyl, benztriazolyl and the like, as described herein. The activated derivative S33.2 is then reacted with an amine S33.3, to afford the carbamate product S33.4. Examples 1-7 in Scheme 33 depict methods by which the general reaction is effected. Examples 8-10 illustrate alternative methods for the preparation of carbamates.

Scheme 33, Example 1 illustrates the preparation of carbamates employing a chloroformyl derivative of the alcohol S33.5. In this procedure, the alcohol S33.5 is reacted with phosgene, in an inert solvent such as toluene, at about 0° C., as described in *Org. Syn. Coll. Vol.* 3, 167, 1965, or with an equivalent reagent such as trichloromethoxy chloroformate, as described in *Org. Syn. Coll. Vol.* 6, 715, 1988, to afford the chloroformate S33.6. The latter compound is then reacted with the amine component S33.3, in the presence of an organic or inorganic base, to afford the carbamate S33.7. For example, the chloroformyl compound S33.6 is reacted with the amine S33.3 in a water-miscible solvent such as tetrahydrofuran, in the presence of aqueous sodium hydroxide, as described in *Org. Syn. Coll. Vol.* 3, 167, 1965, to yield the carbamate S33.7. Alternatively, the reaction is performed in dichloromethane in the presence of an organic base such as diisopropylethylamine or dimethylaminopyridine.

Scheme 33, Example 2 depicts the reaction of the chloroformate compound S33.6 with imidazole to produce the imidazolide S33.8. The imidazolide product is then reacted with the amine S33.3 to yield the carbamate S33.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in *J. Med. Chem.*, 1989, 32, 357.

Scheme 33 Example 3, depicts the reaction of the chloroformate S33.6 with an activated hydroxyl compound R"OH, to yield the mixed carbonate ester S33.10. The reaction is conducted in an inert organic solvent such as ether or dichloromethane, in the presence of a base such as dicyclohexylamine or triethylamine. The hydroxyl component R"OH is selected from the group of compounds S33.19-S33.24 shown in Scheme 33, and similar compounds. For example, if the component R"OH is hydroxybenztriazole S33.19, N-hydroxysuccinimide S33.20, or pentachlorophenol, S33.21, the mixed carbonate S33.10 is obtained by the reaction of the chloroformate with the hydroxyl compound in an ethereal solvent in the presence of dicyclohexylamine, as described in *Can. J. Chem.*, 1982, 60, 976. A similar reaction in which the component R"OH is pentafluorophenol S33.22 or 2-hydroxypyridine S33.23 is performed in an ethereal solvent in the presence of triethylamine, as described in *Syn.*, 1986, 303, and *Chem. Ber.* 118, 468, 1985.

Scheme 33 Example 4 illustrates the preparation of carbamates in which an alkyloxycarbonylimidazole S33.8 is employed. In this procedure, an alcohol S33.5 is reacted with an equimolar amount of carbonyl diimidazole S33.11 to prepare the intermediate S33.8. The reaction is conducted in an aprotic organic solvent such as dichloromethane or tetrahydrofuran. The acyloxyimidazole S33.8 is then reacted with an equimolar amount of the amine R'NH$_2$ to afford the carbamate S33.7. The reaction is performed in an aprotic organic solvent such as dichloromethane, as described in *Tet. Lett.*, 42, 2001, 5227, to afford the carbamate S33.7.

Scheme 33, Example 5 illustrates the preparation of carbamates by means of an intermediate alkoxycarbonylbenztriazole S33.13. In this procedure, an alcohol ROH is reacted at ambient temperature with an equimolar amount of benztriazole carbonyl chloride S33.12, to afford the alkoxycarbonyl product S33.13. The reaction is performed in an organic solvent such as benzene or toluene, in the presence of a tertiary organic amine such as triethylamine, as described in *Synthesis.*, 1977, 704. The product is then reacted with the amine R'NH$_2$ to afford the carbamate S33.7. The reaction is conducted in toluene or ethanol, at from ambient temperature to about 80° C. as described in *Synthesis.*, 1977, 704.

Scheme 33, Example 6 illustrates the preparation of carbamates in which a carbonate (R"O)$_2$CO, S33.14, is reacted with an alcohol S33.5 to afford the intermediate alkyloxycarbonyl intermediate S33.15. The latter reagent is then reacted with the amine R'NH$_2$ to afford the carbamate S33.7. The procedure in which the reagent S33.15 is derived from hydroxybenztriazole S33.19 is described in *Synthesis*, 1993, 908; the procedure in which the reagent S33.15 is derived from N-hydroxysuccinimide S33.20 is described in *Tet. Lett.*, 1992, 2781; the procedure in which the reagent S33.15 is derived from 2-hydroxypyridine S33.23 is described in *Tet. Lett.*, 1991, 4251; the procedure in which the reagent S33.15 is derived from 4-nitrophenol S33.24 is described in *Synthesis.* 1993, 103. The reaction between equimolar amounts of the alcohol ROH and the carbonate S33.14 is conducted in an inert organic solvent at ambient temperature.

Scheme 33, Example 7 illustrates the preparation of carbamates from alkoxycarbonyl azides S33.16. In this procedure, an alkyl chloroformate S33.6 is reacted with an azide, for example sodium azide, to afford the alkoxycarbonyl azide S33.16. The latter compound is then reacted with an equimolar amount of the amine R'NH$_2$ to afford the carbamate S33.7. The reaction is conducted at ambient temperature in a polar aprotic solvent such as dimethylsulfoxide, for example as described in *Synthesis.*, 1982, 404.

Scheme 33, Example 8 illustrates the preparation of carbamates by means of the reaction between an alcohol ROH and the chloroformyl derivative of an amine S33.17. In this procedure, which is described in *Synthetic Organic Chemistry*, R. B. Wagner, H. D. Zook, Wiley, 1953, p. 647, the reactants are combined at ambient temperature in an aprotic solvent such as acetonitrile, in the presence of a base such as triethylamine, to afford the carbamate S33.7.

Scheme 33, Example 9 illustrates the preparation of carbamates by means of the reaction between an alcohol ROH and an isocyanate S33.18. In this procedure, which is described in *Synthetic Organic Chemistry*, R. B. Wagner, H. D. Zook, Wiley, 1953, p. 645, the reactants are combined at ambient temperature in an aprotic solvent such as ether or dichloromethane and the like, to afford the carbamate S33.7.

Scheme 33, Example 10 illustrates the preparation of carbamates by means of the reaction between an alcohol ROH and an amine R'NH$_2$. In this procedure, which is described in *Chem. Lett.* 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate S33.7.

Scheme 33. Preparation of carbamates.

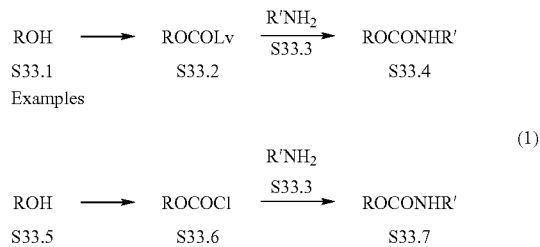

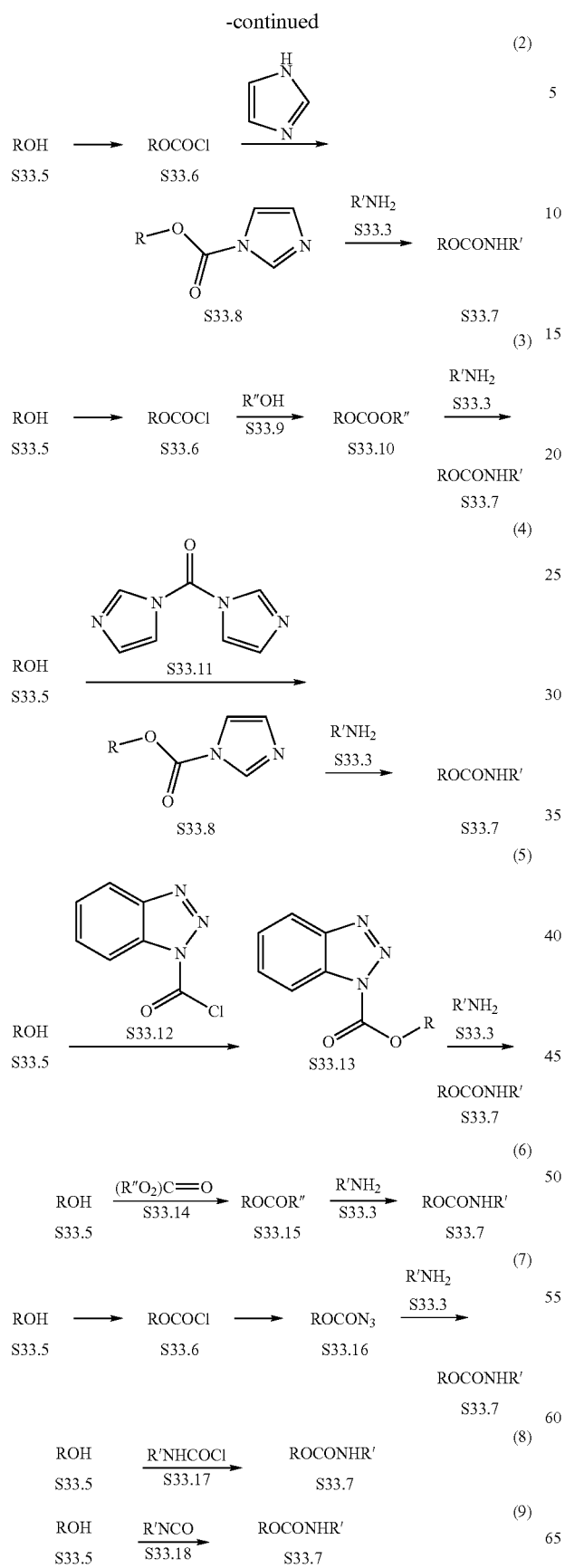

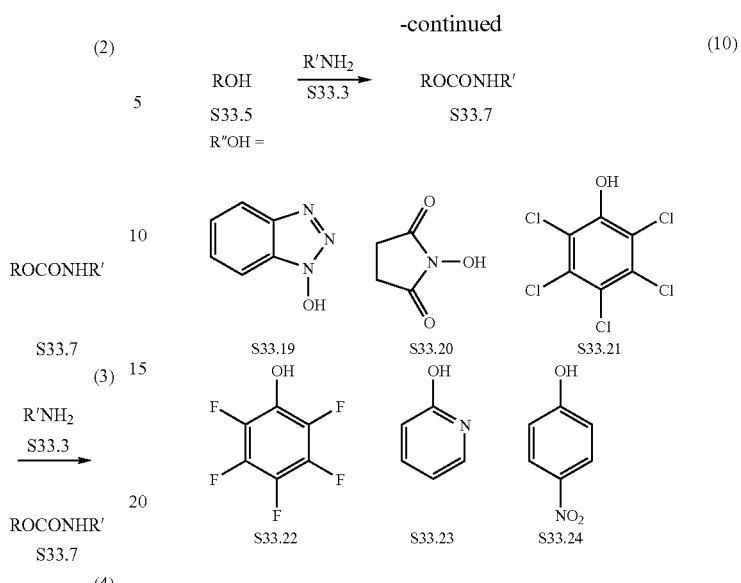

Preparation of Carboalkoxy-Substituted Phosphonate Bisamidates, Monoamidates, Diesters and Monoesters A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in *J. Gen. Chem. USSR*, 1983, 53, 480, *Zh. Obschei Khim.*, 1958, 28, 1063, or *J. Org. Chem.*, 1994, 59, 6144, or by reaction with oxalyl chloride, as described in *J. Am. Chem. Soc.*, 1994, 116, 3251, or *J. Org. Chem.*, 1994, 59, 6144, or by reaction with phosphorus pentachloride, as described in *J. Org. Chem.*, 2001, 66, 329, or in *J. Med. Chem.*, 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in *J. Chem. Soc., Chem. Comm.* (1991) 312, or *Nucleosides & Nucleotides* (2000) 19:1885. Activated sulfonyloxy derivatives are obtained by the reaction of phosphonic acids with trichloromethylsulfonyl chloride or with triisopropylbenzenesulfonyl chloride, as described in *Tet. Lett.* (1996) 7857, or *Bioorg. Med. Chem. Lett.* (1998) 8:663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in *J. Chem. Soc., Chem. Comm.* (1991) 312 or *Coll. Czech. Chem. Comm.* (1987) 52:2792. The use of ethyl dimethylaminopropyl carbodiimide for activation and coupling of phosphonic acids is described in *Tet. Lett.*, (2001) 42:8841, or *Nucleosides & Nucleotides* (2000) 19:1885.

A number of additional coupling reagents have been described for the preparation of amidates and esters from phosphonic acids. The agents include Aldrithiol-2, and PYBOP and BOP, as described in *J. Org. Chem.,* 1995, 60, 5214, and *J. Med. Chem.* (1997) 40:3842, mesitylene-2-sulfonyl-3-nitro-1,2,4-triazole (MSNT), as described in *J. Med. Chem.* (1996) 39:4958, diphenylphosphoryl azide, as described in *J. Org. Chem.* (1984) 49:1158, 1-(2,4,6-triisopropylbenzenesulfonyl-3-nitro-1,2,4-triazole (TPSNT) as described in *Bioorg. Med. Chem. Lett.* (1998) 8:1013, bromotris(dimethylamino)phosphonium hexafluorophosphate (BroP), as described in *Tet. Lett.,* (1996) 37:3997, 2-chloro-5,5-dimethyl-2-oxo-1,3,2-dioxaphosphinane, as described in *Nucleosides Nucleotides* 1995, 14, 871, and diphenyl chlorophosphate, as described in *J. Med. Chem.,* 1988, 31, 1305.

Phosphonic acids are converted into amidates and esters by means of the Mitsunobu reaction, in which the phosphonic acid and the amine or hydroxy reactant are combined in the presence of a triaryl phosphine and a dialkyl azodicarboxylate. The procedure is described in *Org. Lett.,* 2001, 3, 643, or *J. Med. Chem.,* 1997, 40, 3842.

Phosphonic esters are also obtained by the reaction between phosphonic acids and halo compounds, in the presence of a suitable base. The method is described, for example, in *Anal. Chem.,* 1987, 59, 1056, or *J. Chem. Soc. Perkin Trans., I,* 1993, 19, 2303, or *J. Med. Chem.,* 1995, 38, 1372, or *Tet. Lett.,* 2002, 43, 1161.

Schemes 34-37 illustrate the conversion of phosphonate esters and phosphonic acids into carboalkoxy-substituted phosphonbisamidates (Scheme 34), phosphonamidates (Scheme 35), phosphonate monoesters (Scheme 36) and phosphonate diesters, (Scheme 37). Scheme 38 illustrates synthesis of gem-dialkyl amino phosphonate reagents.

Scheme 34 illustrates various methods for the conversion of phosphonate diesters S34.1 into phosphonbisamidates S34.5. The diester S34.1, prepared as described previously, is hydrolyzed, either to the monoester S34.2 or to the phosphonic acid S34.6. The methods employed for these transformations are described above. The monoester S34.2 is converted into the monoamidate S34.3 by reaction with an aminoester S34.9, in which the group $R^2$ is H or alkyl; the group $R^{4b}$ is a divalent alkylene moiety such as, for example, $CHCH_3$, $CHCH_2CH_3$, $CH(CH(CH_3)_2)$, $CH(CH_2Ph)$, and the like, or a side chain group present in natural or modified aminoacids; and the group $R^{5b}$ is $C_1$-$C_{12}$ alkyl, such as methyl, ethyl, propyl, isopropyl, or isobutyl; $C_6$-$C_{20}$ aryl, such as phenyl or substituted phenyl; or $C_6$-$C_{20}$ arylalkyl, such as benzyl or benzyhydryl. The reactants are combined in the presence of a coupling agent such as a carbodiimide, for example dicyclohexyl carbodiimide, as described in *J. Am. Chem. Soc.,* (1957) 79:3575, optionally in the presence of an activating agent such as hydroxybenztriazole, to yield the amidate product S34.3. The amidate-forming reaction is also effected in the presence of coupling agents such as BOP, as described in *J. Org. Chem.* (1995) 60:5214, Aldrithiol, PYBOP and similar coupling agents used for the preparation of amides and esters. Alternatively, the reactants S34.2 and S34.9 are transformed into the monoamidate S34.3 by means of a Mitsunobu reaction. The preparation of amidates by means of the Mitsunobu reaction is described in *J. Med. Chem.* (1995) 38:2742. Equimolar amounts of the reactants are combined in an inert solvent such as tetrahydrofuran in the presence of a triaryl phosphine and a dialkyl azodicarboxylate. The thus-obtained monoamidate ester S34.3 is then transformed into amidate phosphonic acid S34.4. The conditions used for the hydrolysis reaction depend on the nature of the $R^1$ group, as described previously. The phosphonic acid amidate S34.4 is then reacted with an aminoester S34.9, as described above, to yield the bisamidate product S34.5, in which the amino substituents are the same or different. Alternatively, the phosphonic acid S34.6 may be treated with two different amino ester reagents simulataneously, i.e. S34.9 where $R^2$, $R^{4b}$ or $R^{5b}$ are different. The resulting mixture of bisamidate products S34.5 may then be separable, e.g. by chromatography.

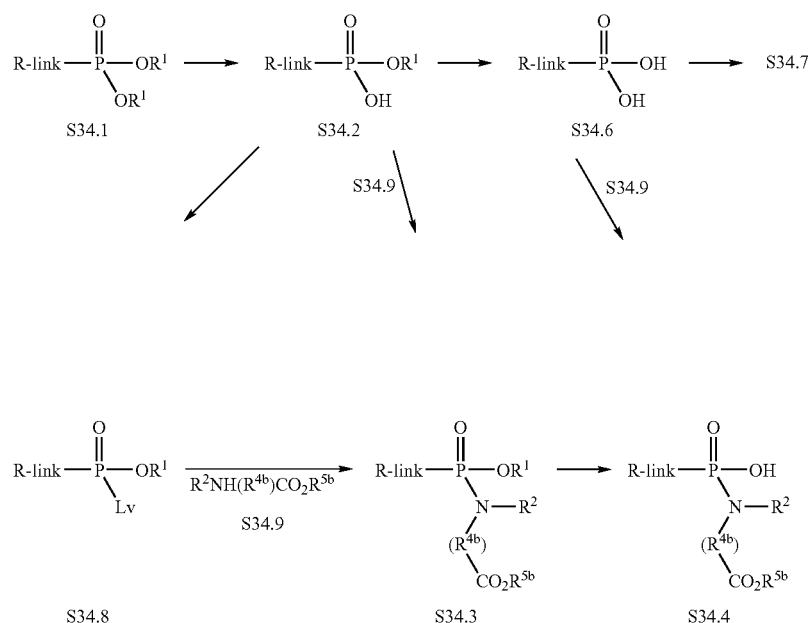

Scheme 34

-continued

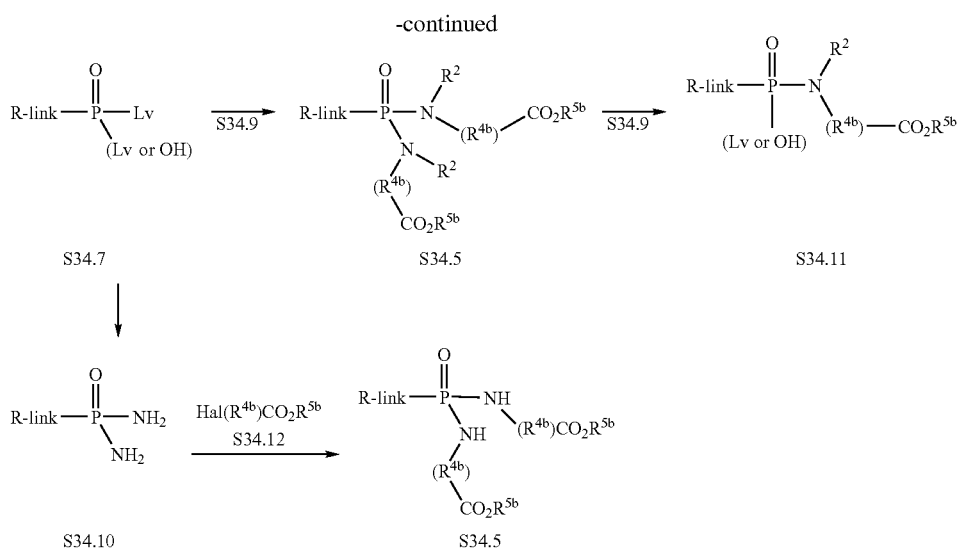

An example of this procedure is shown in Scheme 34, Example 1. In this procedure, a dibenzyl phosphonate S34.14 is reacted with diazabicyclooctane (DABCO) in toluene at reflux, as described in *J. Org. Chem.*, 1995, 60, 2946, to afford the monobenzyl phosphonate S34.15. The product is then reacted with equimolar amounts of ethyl alaninate S34.16 and dicyclohexyl carbodiimide in pyridine, to yield the amidate product S34.17. The benzyl group is then removed, for example by hydrogenolysis over a palladium catalyst, to give the monoacid product S34.18 which may be unstable according to J. Med. Chem. (1997) 40(23):3842. This compound S34.18 is then reacted in a Mitsunobu reaction with ethyl leucinate S34.19, triphenyl phosphine and diethylazodicarboxylate, as described in *J. Med. Chem.*, 1995, 38, 2742, to produce the bisamidate product S34.20.

Using the above procedures, but employing in place of ethyl leucinate S34.19 or ethyl alaninate S34.16, different aminoesters S34.9, the corresponding products S34.5 are obtained.

Alternatively, the phosphonic acid S34.6 is converted into the bisamidate S34.5 by use of the coupling reactions described above. The reaction is performed in one step, in which case the nitrogen-related substituents present in the product S34.5 are the same, or in two steps, in which case the nitrogen-related substituents can be different.

An example of the method is shown in Scheme 34, Example 2. In this procedure, a phosphonic acid S34.6 is reacted in pyridine solution with excess ethyl phenylalaninate S34.21 and dicyclohexylcarbodiimide, for example as described in *J. Chem. Soc., Chem. Comm.*, 1991, 1063, to give the bisamidate product S34.22.

Using the above procedures, but employing in place of ethyl phenylalaninate, different aminoesters S34.9, the corresponding products S34.5 are obtained.

As a further alternative, the phosphonic acid S34.6 is converted into the mono or bis-activated derivative S34.7, in which Lv is a leaving group such as chloro, imidazolyl, triisopropylbenzenesulfonyloxy etc. The conversion of phosphonic acids into chlorides S34.7 (Lv=Cl) is effected by reaction with thionyl chloride or oxalyl chloride and the like, as described in *Organic Phosphorus Compounds*, G. M. Kosolapoff, L. Maeir, eds, Wiley, 1976, p. 17. The conversion of phosphonic acids into monoimidazolides S34.7 (Lv=imidazolyl) is described in *J. Med. Chem.*, 2002, 45, 1284 and in *J. Chem. Soc. Chem. Comm.*, 1991, 312. Alternatively, the phosphonic acid is activated by reaction with triisopropylbenzenesulfonyl chloride, as described in *Nucleosides and Nucleotides*, 2000, 10, 1885. The activated product is then reacted with the aminoester S34.9, in the presence of a base, to give the bisamidate S34.5. The reaction is performed in one step, in which case the nitrogen substituents present in the product S34.5 are the same, or in two steps, via the intermediate S34.11, in which case the nitrogen substituents can be different.

Examples of these methods are shown in Scheme 34, Examples 3 and 5. In the procedure illustrated in Scheme 34, Example 3, a phosphonic acid S34.6 is reacted with ten molar equivalents of thionyl chloride, as described in *Zh. Obschei Khim.*, 1958, 28, 1063, to give the dichloro compound S34.23. The product is then reacted at reflux temperature in a polar aprotic solvent such as acetonitrile, and in the presence of a base such as triethylamine, with butyl serinate S34.24 to afford the bisamidate product S34.25.

Using the above procedures, but employing, in place of butyl serinate S34.24, different aminoesters S34.9, the corresponding products S34.5 are obtained.

In the procedure illustrated in Scheme 34, Example 5, the phosphonic acid S34.6 is reacted, as described in *J. Chem. Soc. Chem. Comm.*, 1991, 312, with carbonyl diimidazole to give the imidazolide S34.32. The product is then reacted in acetonitrile solution at ambient temperature, with one molar equivalent of ethyl alaninate S34.33 to yield the monodisplacement product S34.34. The latter compound is then reacted with carbonyl diimidazole to produce the activated intermediate S34.35, and the product is then reacted, under the same conditions, with ethyl N-methylalaninate S34.33a to give the bisamidate product S34.36.

Using the above procedures, but employing, in place of ethyl alaninate S34.33 or ethyl N-methylalaninate S34.33a, different aminoesters S34.9, the corresponding products S34.5 are obtained.

The intermediate monoamidate S34.3 is also prepared from the monoester S34.2 by first converting the monoester into the activated derivative S34.8 in which Lv is a leaving group such as halo, imidazolyl etc, using the procedures described above. The product S34.8 is then reacted with an aminoester S34.9 in the presence of a base such as pyridine, to give an intermediate monoamidate product S34.3. The latter compound is then converted, by removal of the $R^1$ group and coupling of the product with the aminoester S34.9, as described above, into the bisamidate S34.5.

An example of this procedure, in which the phosphonic acid is activated by conversion to the chloro derivative S34.26, is shown in Scheme 34, Example 4. In this procedure, the phosphonic monobenzyl ester S34.15 is reacted, in dichloromethane, with thionyl chloride, as described in *Tet. Letters.*, 1994, 35, 4097, to afford the phosphoryl chloride S34.26. The product is then reacted in acetonitrile solution at ambient temperature with one molar equivalent of ethyl 3-amino-2-methylpropionate S34.27 to yield the monoamidate product S34.28. The latter compound is hydrogenated in ethylacetate over a 5% palladium on carbon catalyst to produce the monoacid product S34.29. The product is subjected to a Mitsunobu coupling procedure, with equimolar amounts of butyl alaninate S34.30, triphenyl phosphine, diethylazodicarboxylate and triethylamine in tetrahydrofuran, to give the bisamidate product S34.31.

Using the above procedures, but employing, in place of ethyl 3-amino-2-methylpropionate S34.27 or butyl alaninate S34.30, different aminoesters S34.9, the corresponding products S34.5 are obtained.

The activated phosphonic acid derivative S34.7 is also converted into the bisamidate S34.5 via the diamino compound S34.10. The conversion of activated phosphonic acid derivatives such as phosphoryl chlorides into the corresponding amino analogs S34.10, by reaction with ammonia, is described in *Organic Phosphorus Compounds*, G. M. Kosolapoff, L. Maeir, eds, Wiley, 1976. The bisamino compound S34.10 is then reacted at elevated temperature with a haloester S34.12 (Hal=halogen, i.e. F, Cl, Br, I), in a polar organic solvent such as dimethylformamide, in the presence of a base such as 4,4-dimethylaminopyridine (DMAP) or potassium carbonate, to yield the bisamidate S34.5. Alternatively, S34.6 may be treated with two different amino ester reagents simulataneously, i.e. S34.12 where $R^{4b}$ or $R^{5b}$ are different. The resulting mixture of bisamidate products S34.5 may then be separable, e.g. by chromatography.

An example of this procedure is shown in Scheme 34, Example 6. In this method, a dichlorophosphonate S34.23 is reacted with ammonia to afford the diamide S34.37. The reaction is performed in aqueous, aqueous alcoholic or alcoholic solution, at reflux temperature. The resulting diamino compound is then reacted with two molar equivalents of ethyl 2-bromo-3-methylbutyrate S34.38, in a polar organic solvent such as N-methylpyrrolidinone at ca. 150° C., in the presence of a base such as potassium carbonate, and optionally in the presence of a catalytic amount of potassium iodide, to afford the bisamidate product S34.39.

Using the above procedures, but employing, in place of ethyl 2-bromo-3-methylbutyrate S34.38, different haloesters S34.12 the corresponding products S34.5 are obtained.

The procedures shown in Scheme 34 are also applicable to the preparation of bisamidates in which the aminoester moiety incorporates different functional groups. Scheme 34, Example 7 illustrates the preparation of bisamidates derived from tyrosine. In this procedure, the monoimidazolide S34.32 is reacted with propyl tyrosinate S34.40, as described in Example 5, to yield the monoamidate S34.41. The product is reacted with carbonyl diimidazole to give the imidazolide S34.42, and this material is reacted with a further molar equivalent of propyl tyrosinate to produce the bisamidate product S34.43.

Using the above procedures, but employing, in place of propyl tyrosinate S34.40, different aminoesters S34.9, the corresponding products S34.5 are obtained. The aminoesters employed in the two stages of the above procedure can be the same or different, so that bisamidates with the same or different amino substituents are prepared.

Scheme 35 illustrates methods for the preparation of phosphonate monoamidates.

In one procedure, a phosphonate monoester S34.1 is converted, as described in Scheme 34, into the activated derivative S34.8. This compound is then reacted, as described above, with an aminoester S34.9, in the presence of a base, to afford the monoamidate product S35.1.

The procedure is illustrated in Scheme 35, Example 1. In this method, a monophenyl phosphonate S35.7 is reacted with, for example, thionyl chloride, as described in *J. Gen. Chem.* USSR., 1983, 32, 367, to give the chloro product S35.8. The product is then reacted, as described in Scheme 34, with ethyl alaninate S3, to yield the amidate S35.10.

Using the above procedures, but employing, in place of ethyl alaninate S35.9, different aminoesters S34.9, the corresponding products S35.1 are obtained.

Alternatively, the phosphonate monoester S34.1 is coupled, as described in Scheme 34, with an aminoester S34.9 to produce the amidate S34.5. If necessary, the $R^1$ substituent is then altered, by initial cleavage to afford the phosphonic acid S35.2. The procedures for this transformation depend on the nature of the $R^1$ group, and are described above. The phosphonic acid is then transformed into the ester amidate product S35.3, by reaction with the hydroxy compound $R^3OH$, in which the group $R^3$ is aryl, heterocycle, alkyl, cycloalkyl, haloalkyl etc, using the same coupling procedures (carbodiimide, Aldrithiol-2, PYBOP, Mitsunobu reaction etc) described in Scheme 34 for the coupling of amines and phosphonic acids.

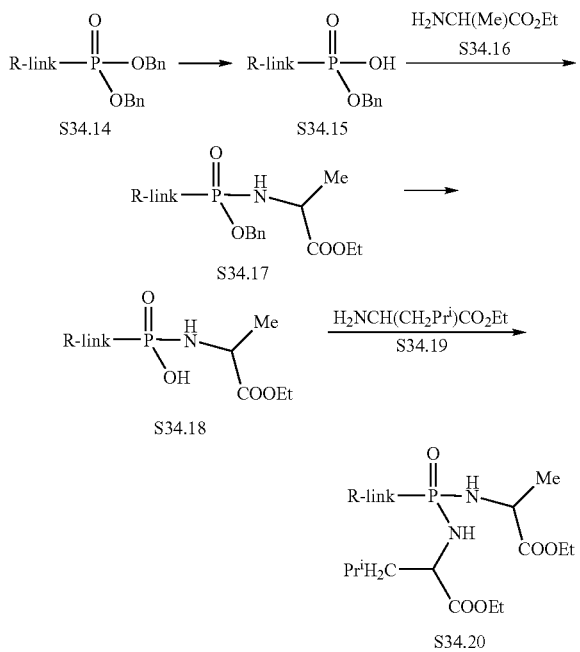

Scheme 34 Example 1

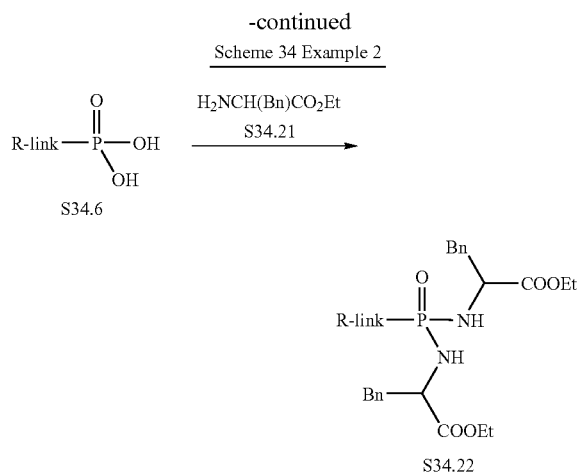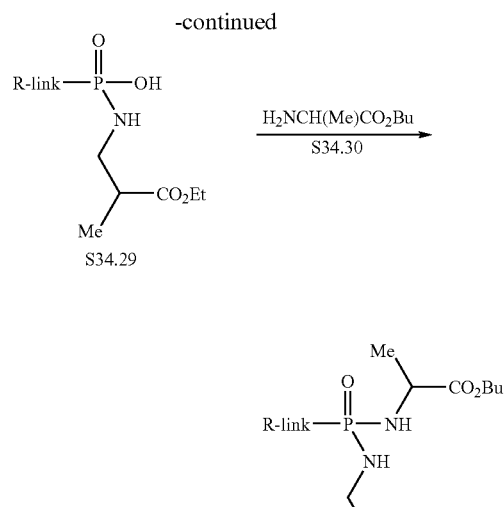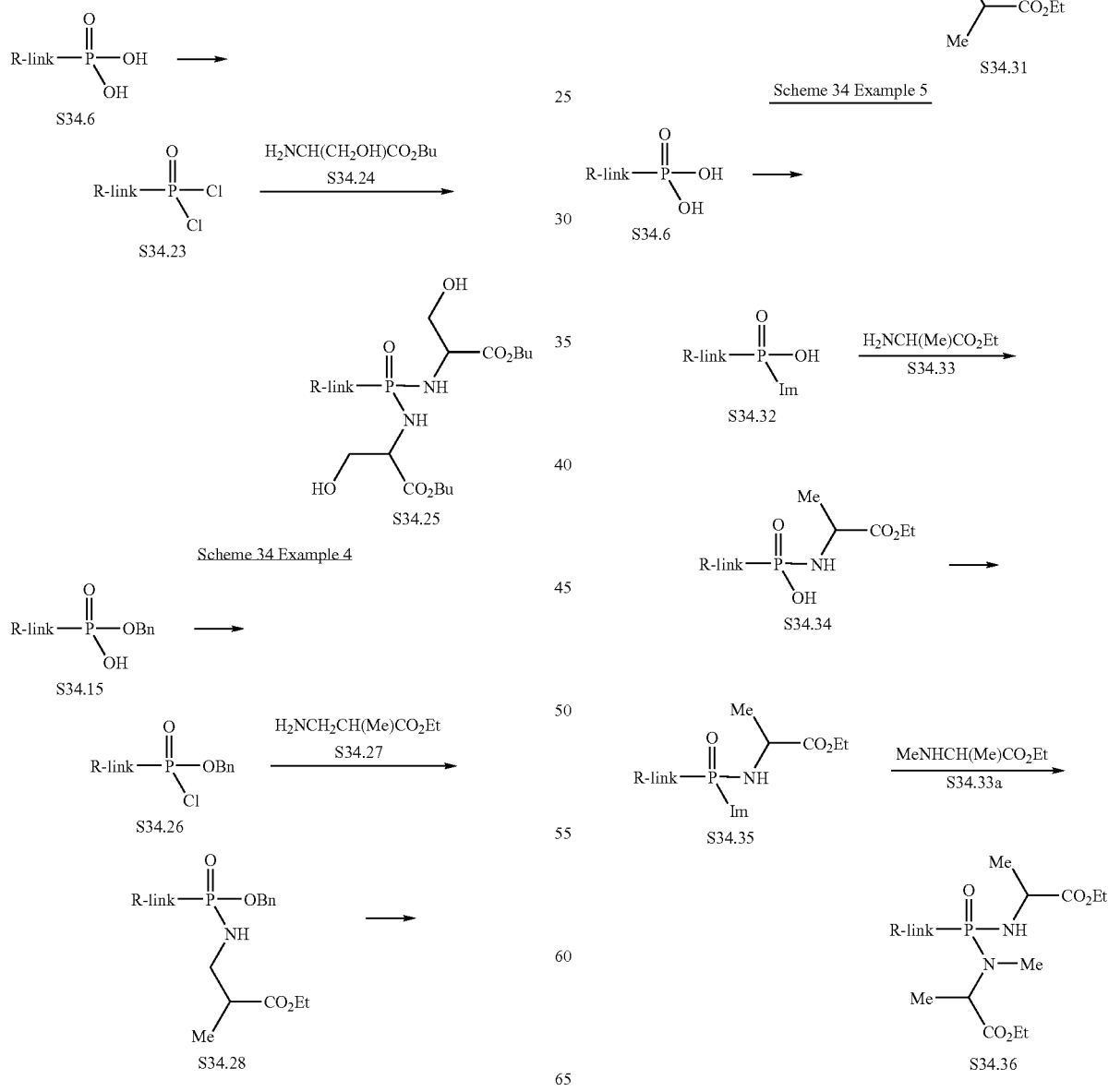

-continued
Scheme 34 Example 6

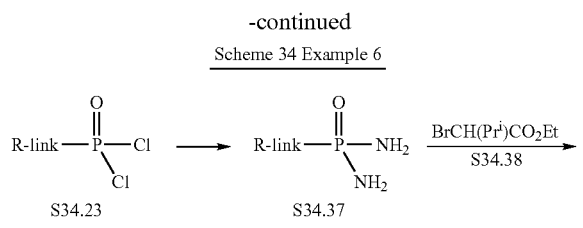

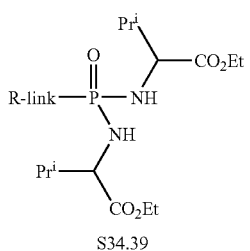

Scheme 34 Example 7

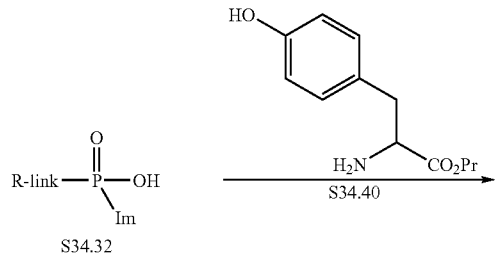

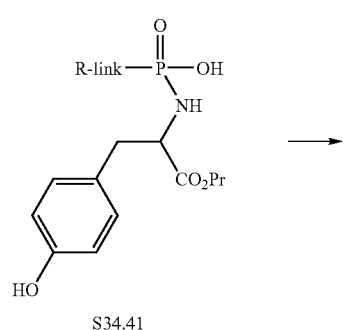

-continued

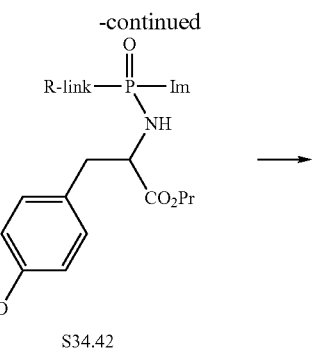

Examples of this method are shown in Scheme 35, Examples 1, 2 and 3. In the sequence shown in Example 2, a monobenzyl phosphonate S35.11 is transformed by reaction with ethyl alaninate, using one of the methods described above, into the monoamidate S35.12. The benzyl group is then removed by catalytic hydrogenation in ethylacetate solution over a 5% palladium on carbon catalyst, to afford the phosphonic acid amidate S35.13. The product is then reacted in dichloromethane solution at ambient temperature with equimolar amounts of 1-(dimethylaminopropyl)-3-ethylcarbodiimide and trifluoroethanol S35.14, for example as described in *Tet. Lett.,* 2001, 42, 8841, to yield the amidate ester S35.15.

In the sequence shown in Scheme 35, Example 3, the monoamidate S35.13 is coupled, in tetrahydrofuran solution at ambient temperature, with equimolar amounts of dicyclohexyl carbodiimide and 4-hydroxy-N-methylpiperidine S35.16, to produce the amidate ester product S35.17.

Using the above procedures, but employing, in place of the ethyl alaninate product S35.12 different monoacids S35.2, and in place of trifluoroethanol S35.14 or 4-hydroxy-N-methylpiperidine S35.16, different hydroxy compounds $R^3OH$, the corresponding products S35.3 are obtained.

Alternatively, the activated phosphonate ester S34.8 is reacted with ammonia to yield the amidate S35.4. The product is then reacted, as described in Scheme 34, with a haloester S35.5, in the presence of a base, to produce the amidate product S35.6. If appropriate, the nature of the $R^1$ group is changed, using the procedures described above, to give the product S35.3. The method is illustrated in Scheme 35, Example 4. In this sequence, the monophenyl phosphoryl chloride S35.18 is reacted, as described in Scheme 34, with ammonia, to yield the amino product S35.19. This material is then reacted in N-methylpyrrolidinone solution at 170° with butyl 2-bromo-3-phenylpropionate S35.20 and potassium carbonate, to afford the amidate product S35.21.

Using these procedures, but employing, in place of butyl 2-bromo-3-phenylpropionate S35.20, different haloesters S35.5, the corresponding products S35.6 are obtained.

The monoamidate products S35.3 are also prepared from the doubly activated phosphonate derivatives S34.7. In this procedure, examples of which are described in *Synlett.*, 1998, 1, 73, the intermediate S34.7 is reacted with a limited amount of the aminoester S34.9 to give the mono-displacement product S34.11. The latter compound is then reacted with the hydroxy compound R³OH in a polar organic solvent such as dimethylformamide, in the presence of a base such as diisopropylethylamine, to yield the monoamidate ester S35.3.

The method is illustrated in Scheme 35, Example 5. In this method, the phosphoryl dichloride S35.22 is reacted in dichloromethane solution with one molar equivalent of ethyl N-methyl tyrosinate S35.23 and dimethylaminopyridine, to generate the monoamidate S35.24. The product is then reacted with phenol S35.25 in dimethylformamide containing potassium carbonate, to yield the ester amidate product S35.26.

Using these procedures, but employing, in place of ethyl N-methyl tyrosinate S35.23 or phenol S35.25, the aminoesters 34.9 and/or the hydroxy compounds R³OH, the corresponding products S35.3 are obtained.

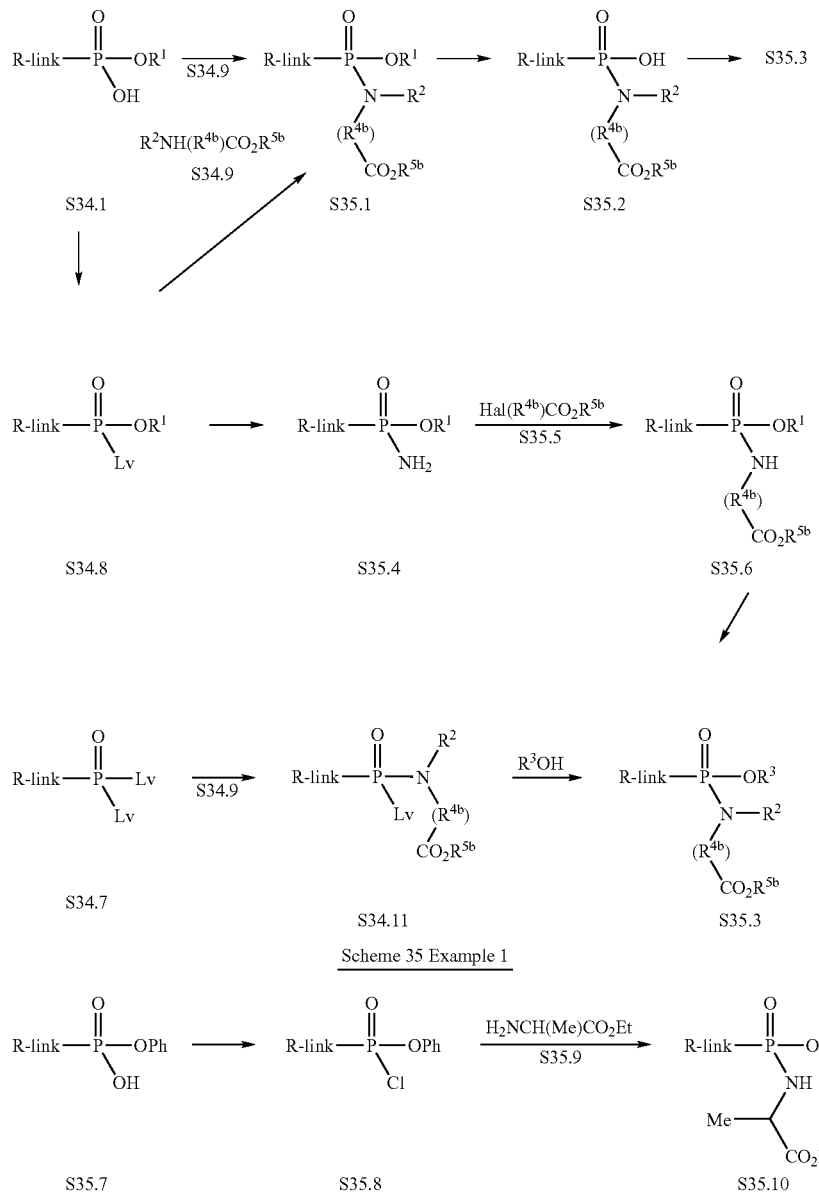

Scheme 35 Example 2

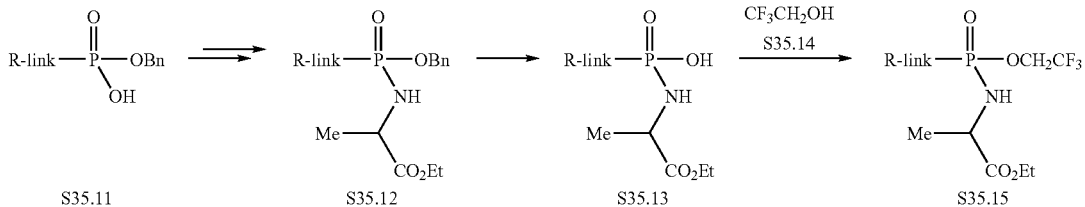

Scheme 35 Example 3

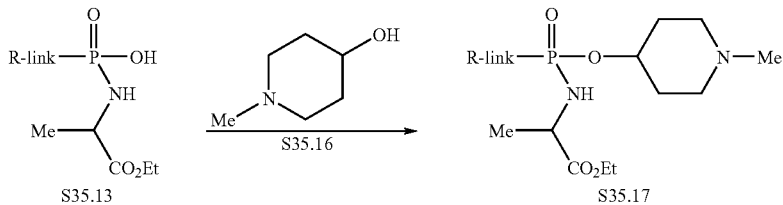

Scheme 35 Example 4

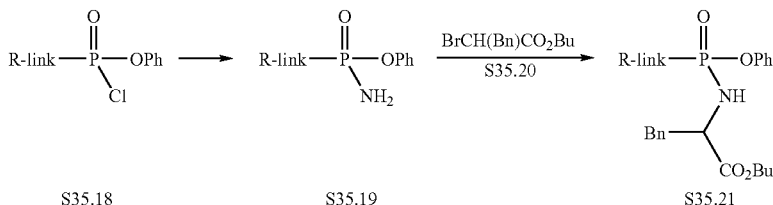

Scheme 35 Example 5

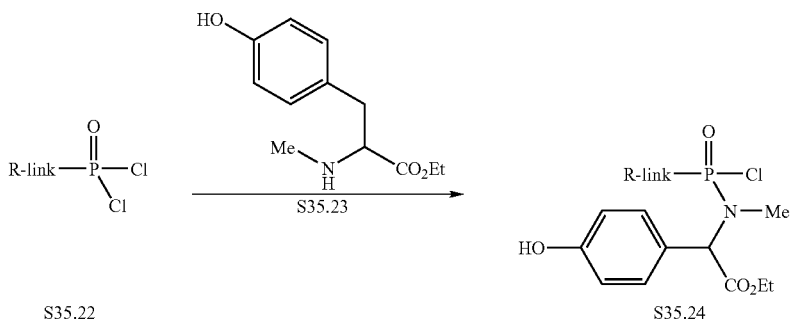

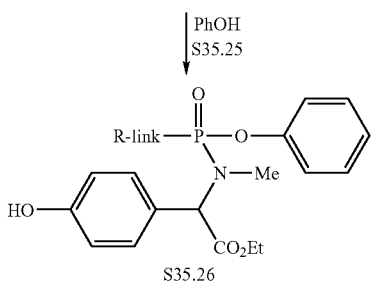

Scheme 36 illustrates methods for the preparation of carboalkoxy-substituted phosphonate diesters in which one of the ester groups incorporates a carboalkoxy substituent.

In one procedure, a phosphonate monoester S34.1, prepared as described above, is coupled, using one of the methods described above, with a hydroxyester S36.1, in which the groups $R^{4b}$ and $R^{5b}$ are as described in Scheme 34. For example, equimolar amounts of the reactants are coupled in the presence of a carbodiimide such as dicyclohexyl carbodiimide, as described in *Aust. J. Chem.*, 1963, 609, optionally in the presence of dimethylaminopyridine, as described in *Tet.*, 1999, 55, 12997. The reaction is conducted in an inert solvent at ambient temperature.

The procedure is illustrated in Scheme 36, Example 1. In this method, a monophenyl phosphonate S36.9 is coupled, in dichloromethane solution in the presence of dicyclohexyl carbodiimide, with ethyl 3-hydroxy-2-methylpropionate S36.10 to yield the phosphonate mixed diester S36.11.

Using this procedure, but employing, in place of ethyl 3-hydroxy-2-methylpropionate S36.10, different hydroxyesters S33.1, the corresponding products S33.2 are obtained.

The conversion of a phosphonate monoester S34.1 into a mixed diester S36.2 is also accomplished by means of a Mitsunobu coupling reaction with the hydroxyester S36.1, as described in *Org. Lett.*, 2001, 643. In this method, the reactants S34.1 and S36.1 are combined in a polar solvent such as tetrahydrofuran, in the presence of a triarylphosphine and a dialkyl azodicarboxylate, to give the mixed diester S36.2. The $R^1$ substituent is varied by cleavage, using the methods described previously, to afford the monoacid product S36.3. The product is then coupled, for example using methods described above, with the hydroxy compound $R^3OH$, to give the diester product S36.4.

The procedure is illustrated in Scheme 36, Example 2. In this method, a monoallyl phosphonate S36.12 is coupled in tetrahydrofuran solution, in the presence of triphenylphosphine and diethylazodicarboxylate, with ethyl lactate S36.13 to give the mixed diester S36.14. The product is reacted with tris(triphenylphosphine) rhodium chloride (Wilkinson catalyst) in acetonitrile, as described previously, to remove the allyl group and produce the monoacid product S36.15. The latter compound is then coupled, in pyridine solution at ambient temperature, in the presence of dicyclohexyl carbodiimide, with one molar equivalent of 3-hydroxypyridine S36.16 to yield the mixed diester S36.17.

Using the above procedures, but employing, in place of the ethyl lactate S36.13 or 3-hydroxypyridine, a different hydroxyester S36.1 and/or a different hydroxy compound $R^3OH$, the corresponding products S36.4 are obtained.

The mixed diesters S36.2 are also obtained from the monoesters S34.1 via the intermediacy of the activated monoesters S36.5. In this procedure, the monoester S34.1 is converted into the activated compound S36.5 by reaction with, for example, phosphorus pentachloride, as described in *J. Org. Chem.*, 2001, 66, 329, or with thionyl chloride or oxalyl chloride (Lv=Cl), or with triisopropylbenzenesulfonyl chloride in pyridine, as described in *Nucleosides and Nucleotides*, 2000, 19, 1885, or with carbonyl diimidazole, as described in *J. Med. Chem.*, 2002, 45, 1284. The resultant activated monoester is then reacted with the hydroxyester S36.1, as described above, to yield the mixed diester S36.2.

The procedure is illustrated in Scheme 36, Example 3. In this sequence, a monophenyl phosphonate S36.9 is reacted, in acetonitrile solution at 70° C., with ten equivalents of thionyl chloride, so as to produce the phosphoryl chloride S36.19. The product is then reacted with ethyl 4-carbamoyl-2-hydroxybutyrate S36.20 in dichloromethane containing triethylamine, to give the mixed diester S36.21.

Using the above procedures, but employing, in place of ethyl 4-carbamoyl-2-hydroxybutyrate S36.20, different hydroxyesters S36.1, the corresponding products S36.2 are obtained.

The mixed phosphonate diesters are also obtained by an alternative route for incorporation of the $R^3O$ group into intermediates S36.3 in which the hydroxyester moiety is already incorporated. In this procedure, the monoacid intermediate S36.3 is converted into the activated derivative S36.6 in which Lv is a leaving group such as chloro, imidazole, and the like, as previously described. The activated intermediate is then reacted with the hydroxy compound $R^3OH$, in the presence of a base, to yield the mixed diester product S36.4.

The method is illustrated in Scheme 36, Example 4. In this sequence, the phosphonate monoacid S36.22 is reacted with trichloromethanesulfonyl chloride in tetrahydrofuran containing collidine, as described in *J. Med. Chem.*, 1995, 38, 4648, to produce the trichloromethanesulfonyloxy product S36.23. This compound is reacted with 3-(morpholinomethyl)phenol S36.24 in dichloromethane containing triethylamine, to yield the mixed diester product S36.25.

Using the above procedures, but employing, in place of with 3-(morpholinomethyl)phenol S36.24, different alcohols $R^3OH$, the corresponding products S36.4 are obtained.

The phosphonate esters S36.4 are also obtained by means of alkylation reactions performed on the monoesters S34.1. The reaction between the monoacid S34.1 and the haloester S36.7 is performed in a polar solvent in the presence of a base such as diisopropylethylamine, as described in *Anal. Chem.*, 1987, 59, 1056, or triethylamine, as described in *J. Med. Chem.*, 1995, 38, 1372, or in a non-polar solvent such as benzene, in the presence of 18-crown-6, as described in *Syn. Comm.*, 1995, 25, 3565.

The method is illustrated in Scheme 36, Example 5. In this procedure, the monoacid S36.26 is reacted with ethyl 2-bromo-3-phenylpropionate S36.27 and diisopropylethylamine in dimethylformamide at 80° C. to afford the mixed diester product S36.28.

Using the above procedure, but employing, in place of ethyl 2-bromo-3-phenylpropionate S36.27, different haloesters S36.7, the corresponding products S36.4 are obtained.

Scheme 36

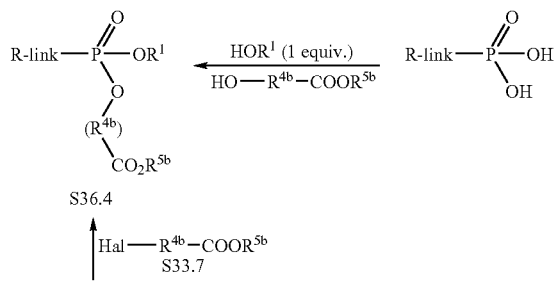

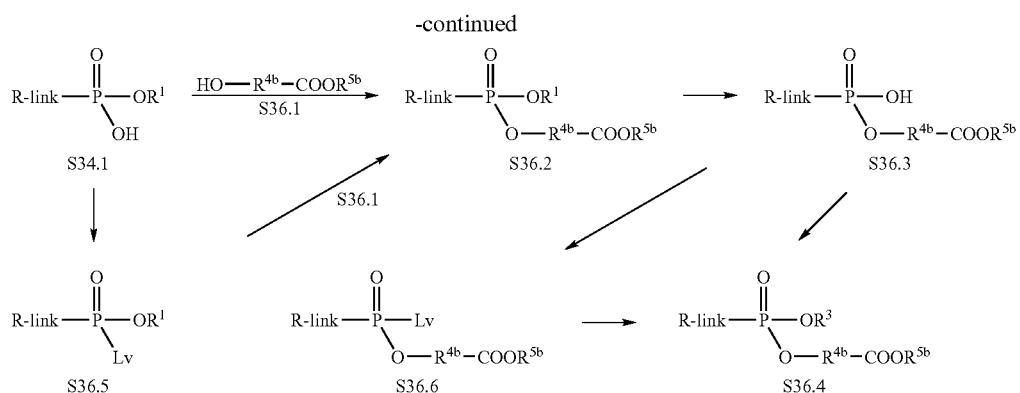
Scheme 36 Example 1
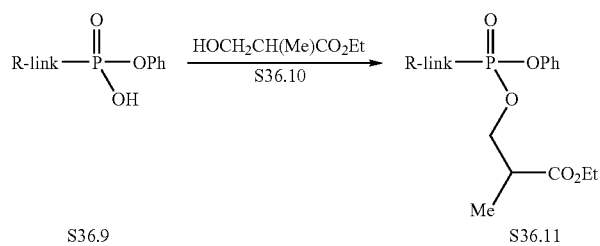
Scheme 36 Example 2
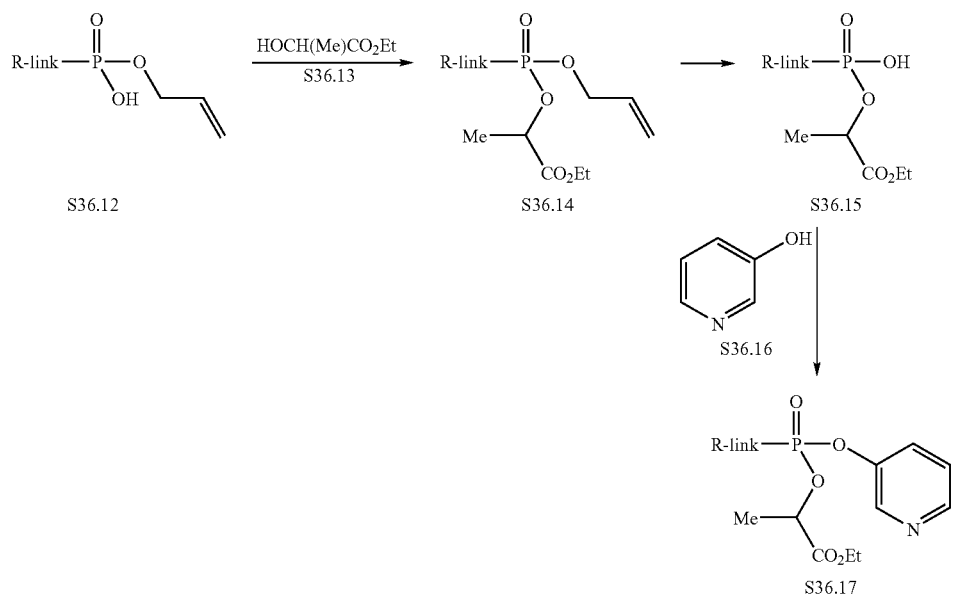
Scheme 36 Example 3
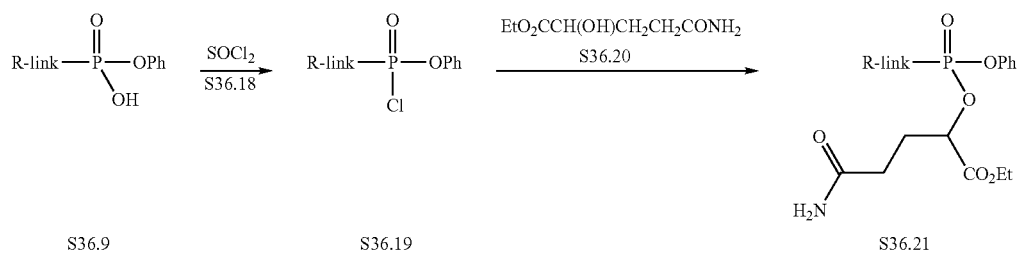

-continued
Scheme 36 Example 4

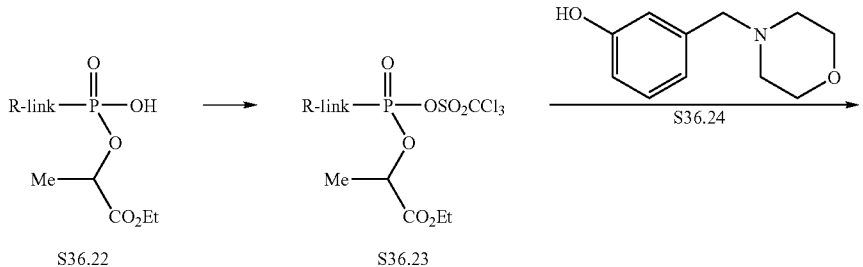

S36.22  S36.23

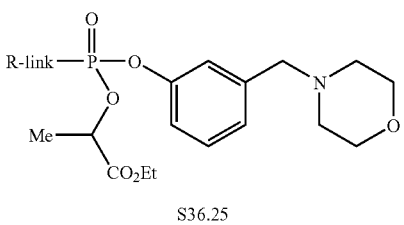

S36.25

Scheme 36 Example 5

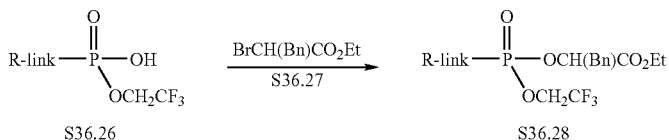

S36.26  S36.28

Scheme 37 illustrates methods for the preparation of phosphonate diesters in which both the ester substituents incorporate carboalkoxy groups.

The compounds are prepared directly or indirectly from the phosphonic acids S34.6. In one alternative, the phosphonic acid is coupled with the hydroxyester S37.2, using the conditions described previously in Schemes 34-36, such as coupling reactions using dicyclohexyl carbodiimide or similar reagents, or under the conditions of the Mitsunobu reaction, to afford the diester product S37.3 in which the ester substituents are identical.

This method is illustrated in Scheme 37, Example 1. In this procedure, the phosphonic acid S34.6 is reacted with three molar equivalents of butyl lactate S37.5 in the presence of Aldrithiol-2 and triphenyl phosphine in pyridine at ca. 70° C., to afford the diester S37.6.

Using the above procedure, but employing, in place of butyl lactate S37.5, different hydroxyesters S37.2, the corresponding products S37.3 are obtained.

Alternatively, the diesters S37.3 are obtained by alkylation of the phosphonic acid S34.6 with a haloester S37.1. The alkylation reaction is performed as described in Scheme 36 for the preparation of the esters S36.4.

This method is illustrated in Scheme 37, Example 2. In this procedure, the phosphonic acid S34.6 is reacted with excess ethyl 3-bromo-2-methylpropionate S37.7 and diisopropylethylamine in dimethylformamide at ca. 80° C., as described in *Anal. Chem.*, 1987, 59, 1056, to produce the diester S37.8.

Using the above procedure, but employing, in place of ethyl 3-bromo-2-methylpropionate S37.7, different haloesters S37.1, the corresponding products S37.3 are obtained.

The diesters S37.3 are also obtained by displacement reactions of activated derivatives S34.7 of the phosphonic acid with the hydroxyesters S37.2. The displacement reaction is performed in a polar solvent in the presence of a suitable base, as described in Scheme 36. The displacement reaction is performed in the presence of an excess of the hydroxyester, to afford the diester product S37.3 in which the ester substituents are identical, or sequentially with limited amounts of different hydroxyesters, to prepare diesters S37.3 in which the ester substituents are different.

The methods are illustrated in Scheme 37, Examples 3 and 4. As shown in Example 3, the phosphoryl dichloride S35.22 is reacted with three molar equivalents of ethyl 3-hydroxy-2-(hydroxymethyl)propionate S37.9 in tetrahydrofuran containing potassium carbonate, to obtain the diester product S37.10.

Using the above procedure, but employing, in place of ethyl 3-hydroxy-2-(hydroxymethyl)propionate S37.9, different hydroxyesters S37.2, the corresponding products S37.3 are obtained.

Scheme 37, Example 4 depicts the displacement reaction between equimolar amounts of the phosphoryl dichloride S35.22 and ethyl 2-methyl-3-hydroxypropionate S37.11, to yield the monoester product S37.12. The reaction is conducted in acetonitrile at 70° in the presence of diisopropylethylamine. The product S37.12 is then reacted, under the same conditions, with one molar equivalent of ethyl lactate S37.13, to give the diester product S37.14.

Using the above procedures, but employing, in place of ethyl 2-methyl-3-hydroxypropionate S37.11 and ethyl lactate S37.13, sequential reactions with different hydroxyesters S37.2, the corresponding products S37.3 are obtained.

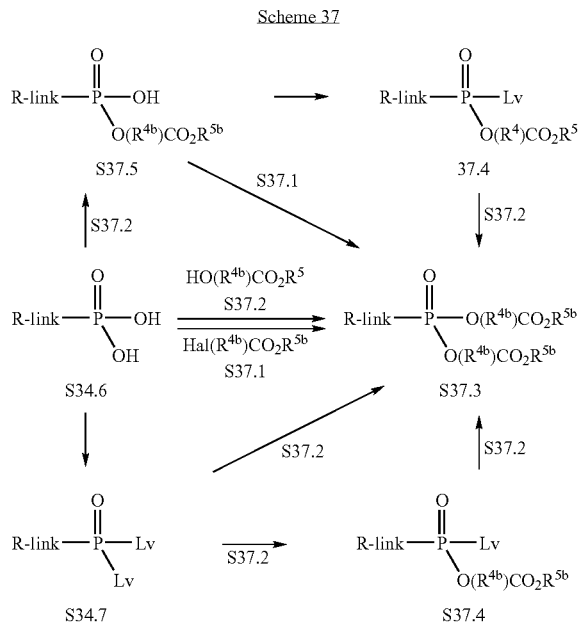

Scheme 37

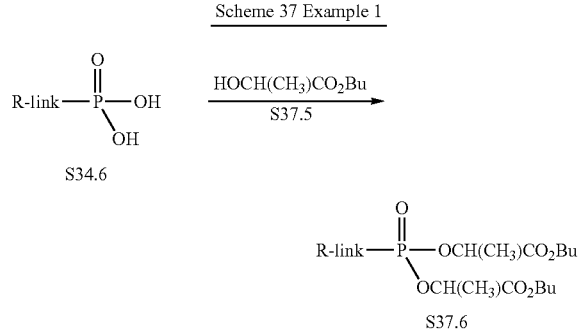

Scheme 37 Example 1

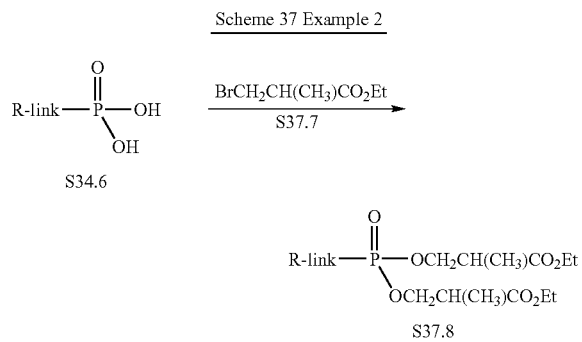

Scheme 37 Example 2

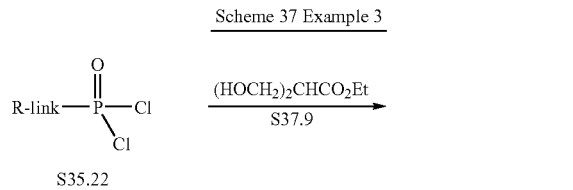

Scheme 37 Example 3

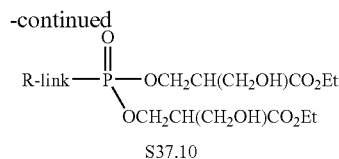

S37.10

Scheme 37 Example 4

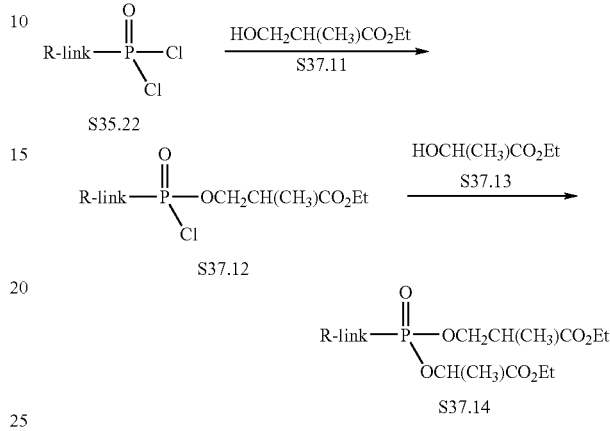

2,2-Dimethyl-2-aminoethylphosphonic acid intermediates can be prepared by the route in Scheme 5. Condensation of 2-methyl-2-propanesulfinamide with acetone give sulfinyl imine S38.11 (*J. Org. Chem.* 1999, 64, 12). Addition of dimethyl methylphosphonate lithium to S38.11 afford S38.12. Acidic methanolysis of S38.12 provide amine S38.13. Protection of amine with Cbz group and removal of methyl groups yield phosphonic acid S38.14, which can be converted to desired S38.15 (Scheme 38a) using methods reported earlier on. An alternative synthesis of compound S38.14 is also shown in Scheme 38b. Commercially available 2-amino-2-methyl-1-propanol is converted to aziridines S38.16 according to literature methods (*J. Org. Chem.* 1992, 57, 5813; *Syn. Lett.* 1997, 8, 893). Aziridine opening with phosphite give S38.17 (*Tetrahedron Lett.* 1980, 21, 1623). Reprotection) of S38.17 affords S38.14.

Scheme 38a

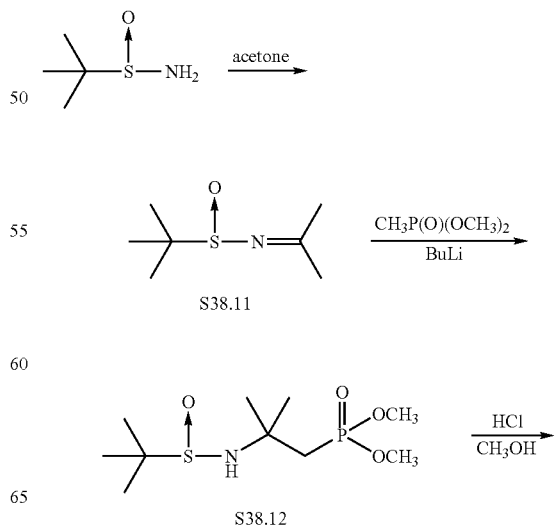

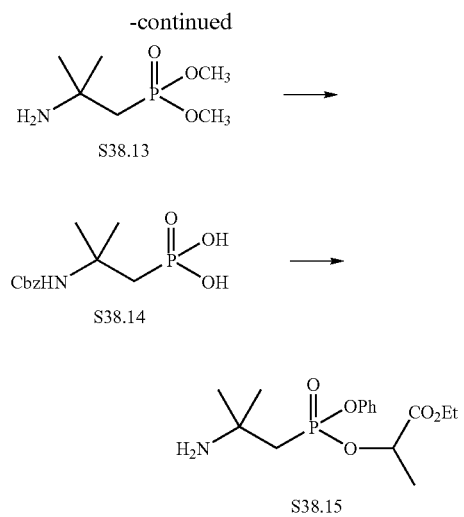
The invention will now be illustrated by the following non-limiting Examples.
EXAMPLES
Example 1
Preparation of Exemplary Compounds of the Present Invention -continued

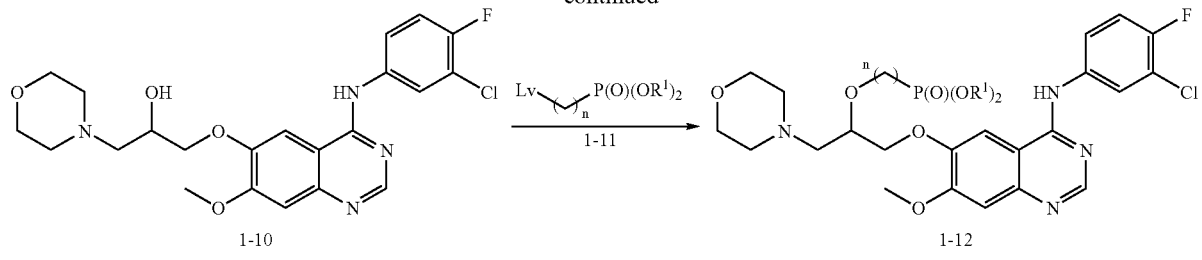

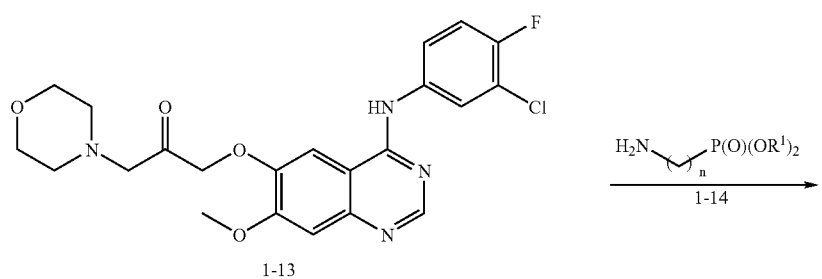

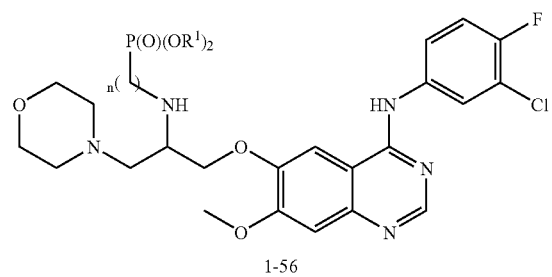

Schemes 1.1-1.3 illustrate the synthesis of target molecules of types 1-12 and 1-56, in which the link is a heteroatom and carbon chain. The preparation of 1-1 is described in U.S. Pat. No. 5,770,596. Diether 1-1 is converted into mono ether 1-2 as described in *Protective Groups in Organic Synthesis*, by T. W. Greene and P. G. M. Wuts, Wiley, Third Edition (1999) p. 246, or by the method described in U.S. Pat. No. 5,770,596. Preferably diether 1-1 in methanesulfonic acid is treated with L-methionine at reflux to give the phenol 1-2. Phenol 1-2 is then protected as the acetyl compound 1-3 and then converted to the chloride 1-4. These procedures are described in U.S. Pat. No. 5,770,596. The acetoxy compound is then treated with the aniline 1-5 to give the amine 1.6 followed by deprotection of the acetyl group to give 1-7 as described in U.S. Pat. No. 5,770,596. Treatment of 1-7 with epibromohydrin 1-8 (Aldrich) in DMF with potassium carbonate present then affords the epoxide 1-9. Treatment of epoxide 1-9 with morpholine in a non-protic solvent at reflux in the presence of a base such as triethylamine affords the alcohol 1-10. The alcohol 1-10 is treated with one equivalent of the phosphonate alkylating agent, in which Lv is a group such as mesyl, trifluoromethanesulfonyl, Br, I, Cl, tosyl etc, in the presence of base e.g. potassium or cesium carbonate in DMF, to give the ether 1-12, in which the link is an oxygen and carbon chain. Alternatively, the alcohol 1-10 is oxidized to the ketone 1-13 as described in *Comprehensive Organic Transformations*, by R. C. Larock, $2^{nd}$ Edition, (1999), p. 1234ff. Preferably the alcohol 1-10 is treated with Dess-martin periodinone to give the ketone 1-13. Ketone 1-13 is then reacted with an amino alkyl phosphonate 1-14 under reductive amination conditions to give the phosphonate 1-56 in which the link is a nitrogen and carbon chain. The preparation of amines by means of reductive amination procedures is described, for example, in *Comprehensive Organic Transformations*, by R. C. Larock, $2^{nd}$ edition, p. 835. In this procedure, the amine component and the aldehyde component are reacted together in the presence of a reducing agent such as, for example, borane, sodium cyanoborohydride or diisobutylaluminum hydride, to yield the amine product.

Scheme 1.2

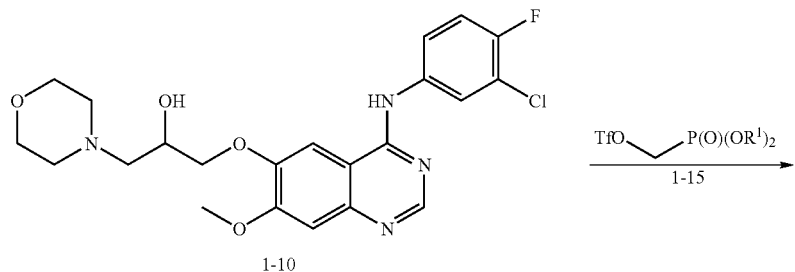

1-10

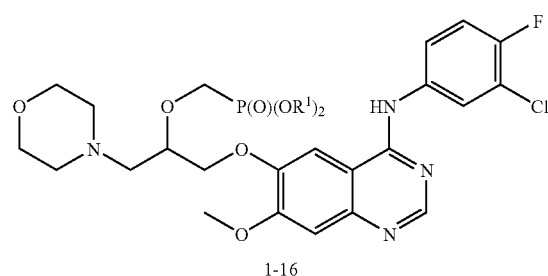

1-16

Scheme 1.3

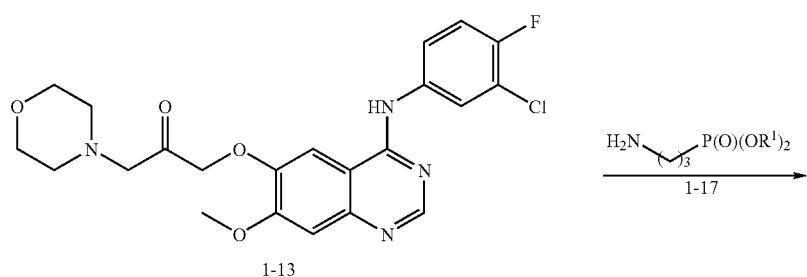

1-13

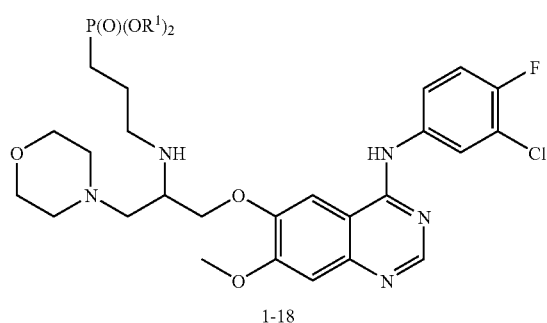

1-18

For example, the alcohol 1-10 is treated with triflate 1-15, prepared as described in *Tetrahedron Lett.* 1986, 27, 1497, and potassium carbonate in DMF, to give the ether 1-16. Alternatively, for example, the ketone 1-13 is treated with amine 1-17 (Acros) in methanol and then after a period of time sodium borohydride is added to give the amine 1-18. Using the above procedures, but employing, in place of the triflate 1-15, or the amine 1-17, phosphonates 1-11 and 1-14, respectively, the corresponding products 1-12 and 1-56 are obtained.

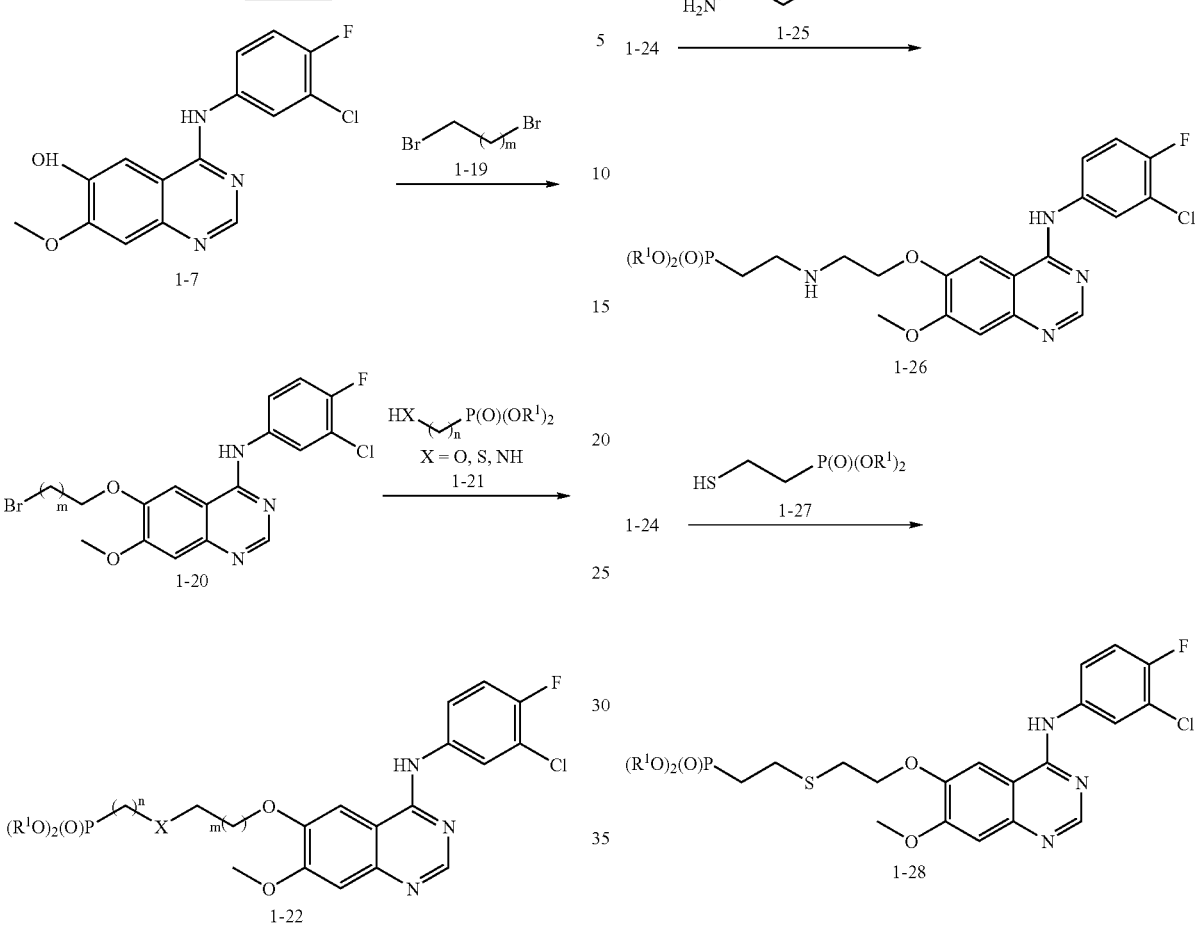

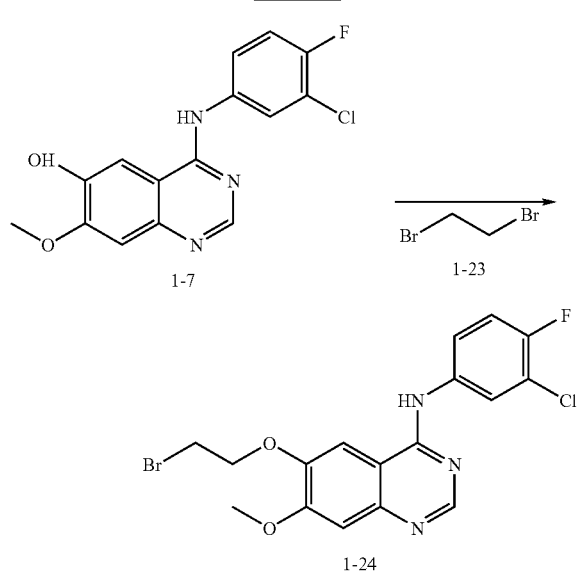

The reactions shown in Schemes 1.4-1.5 illustrate the preparation of the compounds 1-22 in which the phosphonate is linked through a carbon chain and a heteroatom. Phenol 1-7 (Schemes 1.1-1.3) is treated with dibromide 1-19 using the conditions described in Schemes 1.1-1.3 for the preparation of 1-9 from 1-7, to give bromide 1-20. Bromide 1-20 is then treated with the dialkyl hydroxy, thio or amino-substituted alkylphosphonate 1-21 to give the product 1-22. The reaction is performed in the presence of a base, in a polar aprotic solvent such as dioxan or N-methylpyrrolidinone. The base employed in the reaction depends on the nature of the reactant 1-21. For example, if X is O, a strong base such as, for example, lithium hexamethyldisilylazide or potassium tert. butoxide is employed. If X is S, NH or N-alkyl, an inorganic base such as cesium carbonate and the like is employed.

For example, 1-7 is treated with dibromoethane 1-23, as described in Schemes 1.1-1.3 to give the bromide 1-24. Bromide 1-24 is then treated with amine 1-25, prepared as described in *J. Org. Chem.* 2000, 65, 676, in DMF and potassium carbonate at ca 80° C. to give the phosphonate 1-26. Alternatively bromide 1-24 is then heated at reflux with an equimolar amount of a dialkyl 2-mercaptoethylphophonate 1-27, the preparation of which is described in *Aust. J. Chem.*, 1990, 43, 1123, in the presence of sodium carbonate, to afford the thioether product 1-28. Using the above procedures, but employing, in place of the dibromoethane 1-23, different dibromo compounds 1-19 and/or different alkyl phosphonates 1-21 in place of 1-25 or 1-27, the corresponding products 1-22 are obtained.

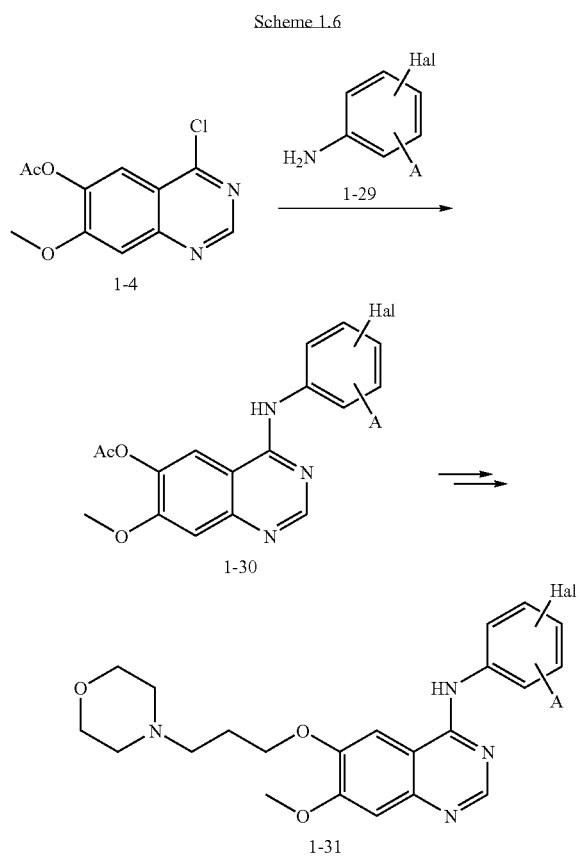

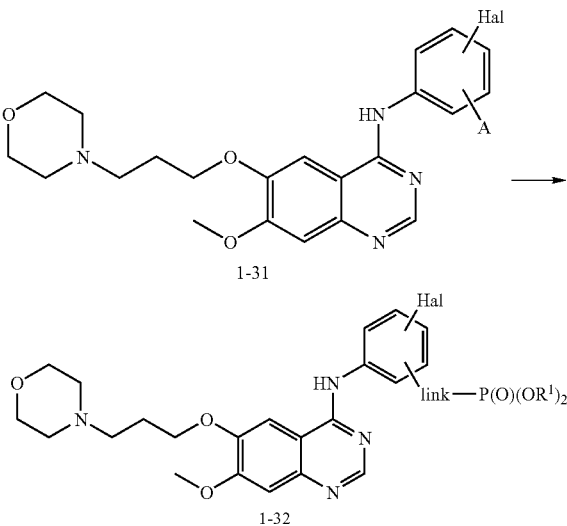

Scheme 1.6 illustrates the synthesis of target molecules 1-32, in which A is Br, Cl, [OH], [NH], or the group link-P(O)(OR$^1$)$_2$. The preparation of 1-4 is illustrated in Scheme 1.1. Treatment of chloride 1-4 with amine 1-29 in refluxing isopropanol gives amine 1-30. The preparation of 1-29 in which A is group link-P(O)(OR$^1$)$_2$ is described below in Schemes 1.8-1.12. Treatment of amine 1-30 according to conditions described in U.S. Pat. No. 5,770,599 then affords the final product 1-31.

The reactions shown in Scheme 1.6 illustrate the preparation of the compounds 1-31 in which the substituent A is either the group link-P(O)(OR$^1$)$_2$ or a precursor such as [OH], [SH], [NH], Br etc. Scheme 1.7 depicts the conversion of the compounds 1-31 in which A is [OH], [SH], [NH], Br etc, into the phosphonate esters 1-32. In this procedure, the compounds 1-31 are converted, using the procedures described in Schemes 1.1-1.6 into the compounds 1-32.

Schemes 1.8-1.12 describe the preparation of phosphonate-containing derivatives 1-29 which are employed in the preparation of the phosphonate ester intermediates 1-32.

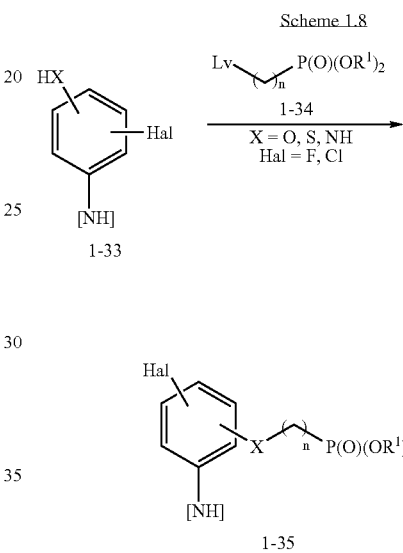

Schemes 1.8-1.10 illustrates the preparation of 1-29 in which the phosphonate is attached through a heteroatom e.g. O, S, or N, and a carbon linker. In this procedure an optionally protected aniline is reacted with an alkylphosphonate 1-34 in which Lv is a leaving group such as triflate, Br, Cl, Mesyl, etc, in the presence of a suitable base. The base required for this transformation depends on the nature of the heteroatom X. For example, if X is N or S, an excess of an inorganic base such as, for example, potassium carbonate, in the presence of an organic solvent such as dimethylformamide, is suitable. The reaction proceeds at from ambient temperature to about 80° C. to afford the displacement products 1-35. If X is O, an equimolar amount of a strong base, such as, for example, lithium hexamethyldisilylazide and the like, is employed, in the presence of a solvent such as tetrahydrofuran. Deprotection, of the amine group as described in *Protective Groups in*

Organic Synthesis, by T. W. Greene and P. G. M. Wuts, Wiley, Third Edition (1999), chapter 7, affords the amine 1-36.

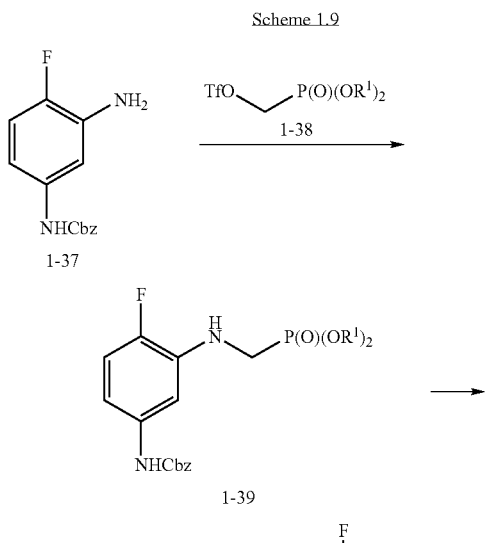

Scheme 1.9

For example, the diamine 1-37 (Aldrich), protected as the CBZ carbamate (*Protective Groups in Organic Synthesis*, by T. W. Greene and P. G. M. Wuts, Wiley, Third Edition (1999), page 531ff) is treated with an equimolar amount of triflate 1-38, the preparation of which is described in *Tetrahedron Lett.* 1986, 27, 1497, in dimethylformamide containing excess potassium carbonate, at about 60° C. to afford the phosphonate product 1-39. Deprotection by reduction over palladium on carbon in the presence of hydrogen then affords the amine 1-40.

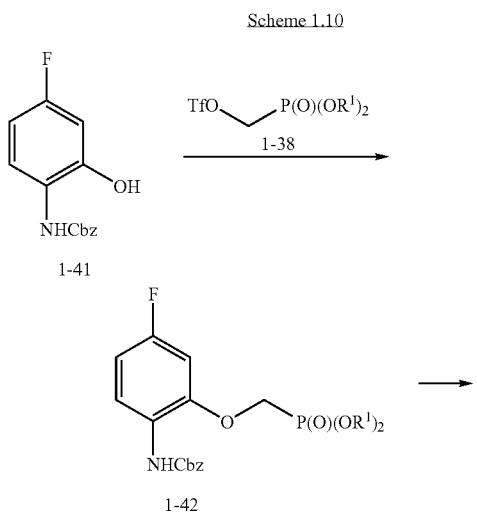

Scheme 1.10

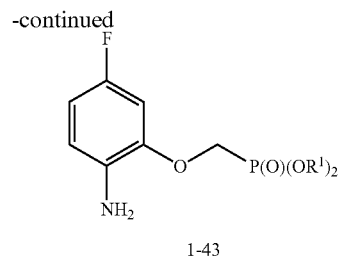

Alternatively, the aminophenol 1-41, protected as the CBZ carbamate as described above, is reacted with one equivalent of triflate 1-38 to give phosphonate 1-42. Removal of the CBZ group by catalytic reduction over palladium on carbon in the presence of hydrogen, as described above, then affords the amine 1-43.

Using the above procedures, but employing, in place of the aniline 1-37 or phenol 1-41, different anilines 1-33, and/or different alkylphosphonates 1-34, in place of 1-38, the corresponding products 1-36 are obtained.

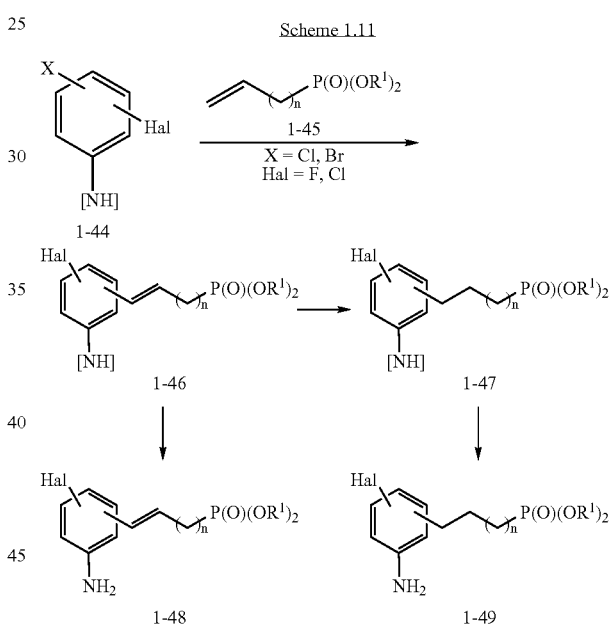

Scheme 1.11

Schemes 1.11-1.12 illustrates the preparation of 1-29 in which the phosphonate is attached through a unsaturated or saturated carbon linker. In this procedure, an optionally protected halo-substituted aniline 1-44 is coupled, by means of a palladium-catalyzed Heck reaction with a dialkyl alkenyl phosphonate 1-45, to afford the coupled product 1-46. The coupling of aryl halides with olefins by means of the Heck reaction is described, for example, in *Advanced Organic Chemistry*, by F. A. Carey and R. J. Sundberg, Plenum, (2001), p. 503ff, and in *Acc. Chem. Res.*, 1979, 12, 146. The aryl bromide and the olefin are coupled in a polar solvent such as dimethylformamide or dioxane, in the presence of a palladium(0) catalyst such as tetrakis(triphenylphosphine) palladium(0) or a palladium(II) catalyst such as palladium(II) acetate, and optionally in the presence of a base such as triethylamine or potassium carbonate, to afford the coupled product 1-46. Protection of anilines is described in *Protective Groups in Organic Synthesis*, by T. W. Greene and P. G. M.

Wuts, Wiley, Third Edition (1999), chapter 7. Preferably the aniline is treated with a BOC reagent such as BOC chloride, or BOC anhydride in the presence of DMAP and a base e.g. triethylamine to afford the protected aniline. Optionally, the product 1-46 can be reduced to afford the saturated phosphonate 1-47. Methods for the reduction of carbon-carbon double bonds are described, for example, in *Comprehensive Organic Transformations*, by R. C. Larock, VCH, (1989), page 6. The methods include catalytic reduction, and chemical reduction, the latter for example employing diborane or diimide.

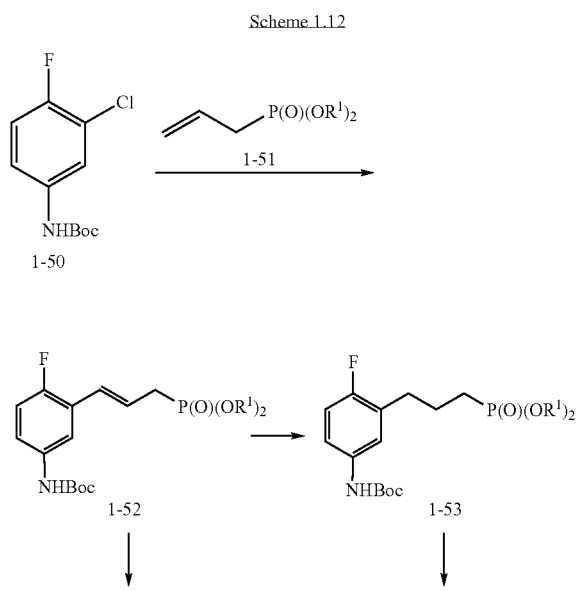

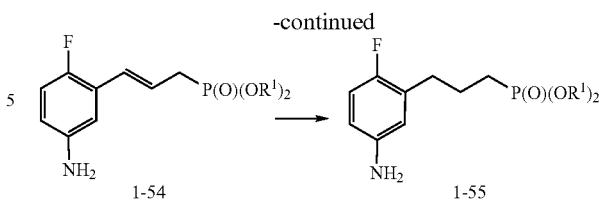

For example, BOC protected 3-chloro-4-fluoro aniline 1-50 (Aldrich) is reacted with a dialkyl propenyl phosphonate 1-51, the preparation of which is described in *J. Med. Chem.*, 1996, 39, 949, in the presence of bis(triphenylphosphine) palladium(II) chloride, as described in *J. Med. Chem.*, 1992, 35, 1371, to afford the coupled product 1-52. The BOC protection of the aniline is performed by treating the corresponding aniline with BOC anhydride in the presence of DMAP. The product 1-52 is reduced, for example by reaction with diimide, as described in *J. Org. Chem.* 1965, 30, 3965, to afford the saturated product 1-53. Boc removal by treatment of 1-52 and 1-53 with TFA in THF or dioxane affords the products 1-54 and 1-55 respectively. Using the above procedures, but employing, in place of the halo aniline compound 1-50, different anilines 1-44, and/or different phosphonates 1-45 the corresponding products 1-48 and 1-49 are obtained.

The procedures described for the introduction of phosphonate moieties (Schemes 1.1-1.12) are, with appropriate modifications known to one skilled in the art, transferable to different chemical substrates. Thus, the methods described above for the introduction of phosphonate groups onto 1-12, 1-56 and 1-22 are also applicable to the introduction of phosphonate moieties onto anilines 1-29 and vice versa.

Example 2

Preparation of Exemplary Compounds of the Present Invention

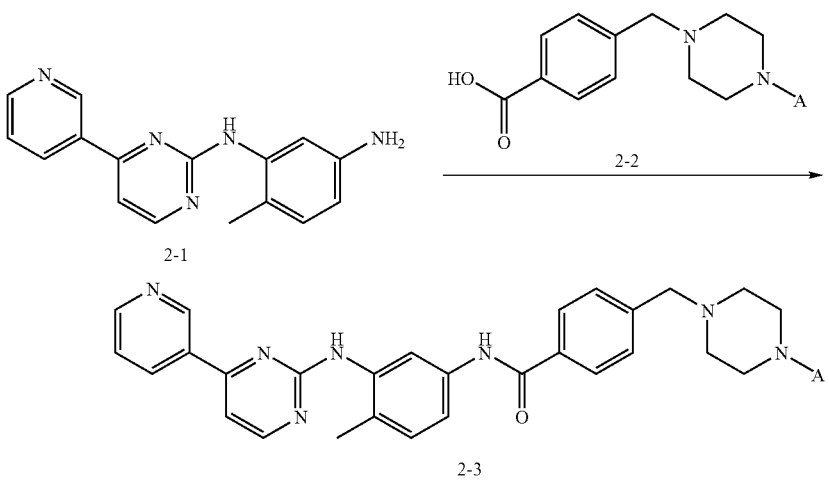

Scheme 2.2

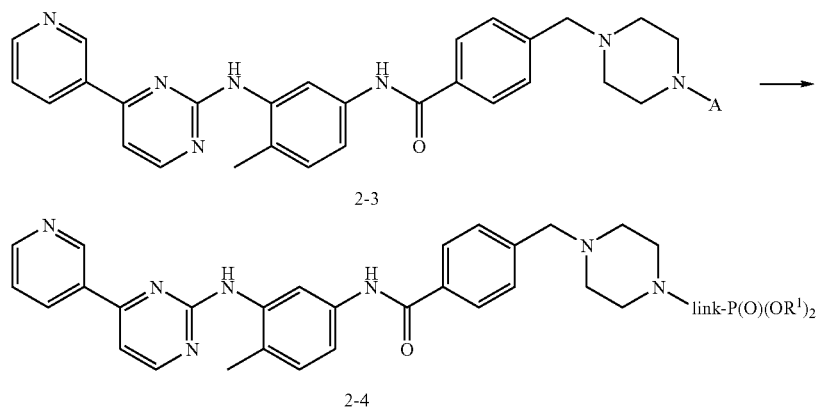

Scheme 2.1 illustrates the preparation of compounds 2-4 in which A is Br, I, [SH], [NH] etc or the group link-P(O)(OR$^1$)$_2$. The amine 2-1 is prepared as described in U.S. Pat. No. 5,521,84. Amine 2-1 is coupled with the acid 2-2 to give the amide 2-3. The preparation of amides from carboxylic acids and derivatives is described, for example, in *Organic Functional Group Preparations*, by S. R. Sandier and W. Karo, Academic Press, 1968, page 274. The carboxylic acid is reacted with the amine in the presence of an activating agent, such as, for example, dicyclohexylcarbodiimide or diisopropylcarbodiimide, optionally in the presence of, for example, hydroxybenztriazole, in a non-protic solvent such as, for example, pyridine, DMF or dichloromethane, to afford the amide.

Alternatively, the carboxylic acid may first be converted into an activated derivative such as the acid chloride or anhydride, and then reacted with the amine, in the presence of an organic base such as, for example, pyridine, to afford the amide.

The conversion of a carboxylic acid into the corresponding acid chloride is effected by treatment of the carboxylic acid with a reagent such as, for example, thionyl chloride or oxalyl chloride in an inert organic solvent such as dichloromethane. Preferably, the acid 2-2 is treated with oxalyl chloride in an inert solvent such as dichloromethane followed by the addition of a few drops of DMF and then treated with the amine 2-1 to give the amide 2-3. The acid, 2-2 is prepared according to Schemes 2.7-2.8 shown below.

The reactions shown in Scheme 2.1 illustrate the preparation of the compounds 2-3 in which the substituent A is either the group link-P(O)(OR$^1$)$_2$ or a precursor such as [OH], [SH], [NH], Br etc. Scheme 2.2 depicts the conversion of the compounds 2-3 in which A is [OH], [SH], [NH], Br etc, into the phosphonate esters 2-4. In this procedure, the compounds 2-3 are converted, using the procedures described below, Schemes 2.7-2.12, into the compounds 2-4.

Scheme 2.3

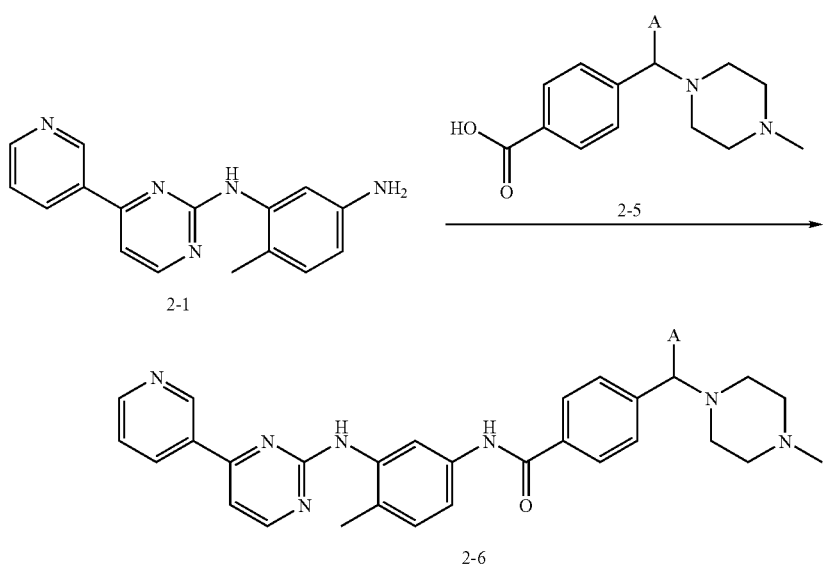

Scheme 2.4

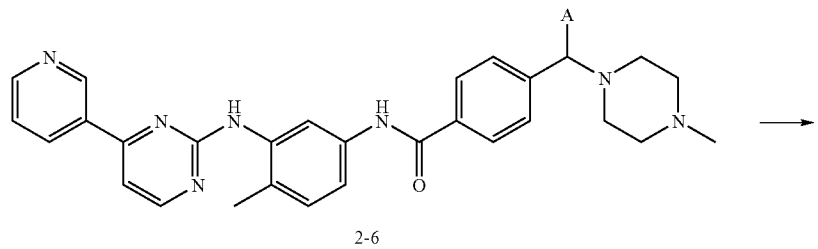

2-6

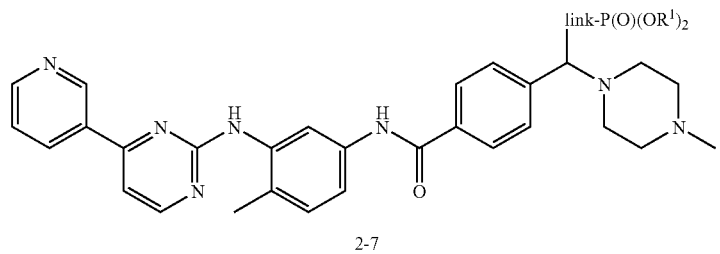

2-7

Scheme 2.3 illustrates the preparation of compounds 2-6 in which A is Br, I, [SH], [NH], etc., or the group link-P(O)(OR$^1$)$_2$. The amine 2-1 is treated with acid 2-5 as described above, Scheme 2.1, to give the amide 2-6. The preparation of acid 2-5 is described in Schemes 2.9-2.10 below.

The reactions shown in Scheme 2.3 illustrate the preparation of the compounds 2-6 in which the substituent A is either the group link-P(O)(OR$^1$)$_2$ or a precursor such as [OH], [SH], [NH], Br, etc. Scheme 2.4 depicts the conversion of the compounds 2-6 in which A is [OH], [SH], [NH], Br etc. into the phosphonate esters 2-7. In this procedure, the compounds 2-6 are converted, using the procedures described below, Schemes 2.7-2.12, into the compounds 2-7.

Scheme 2.5

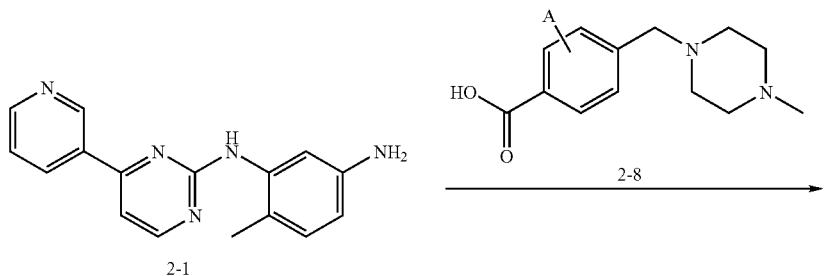

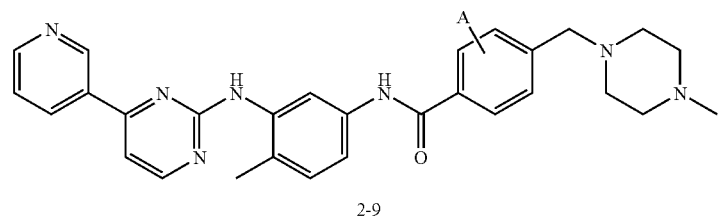

2-9

Scheme 2.6

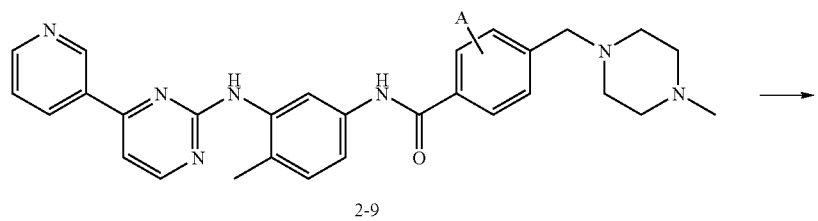

2-9

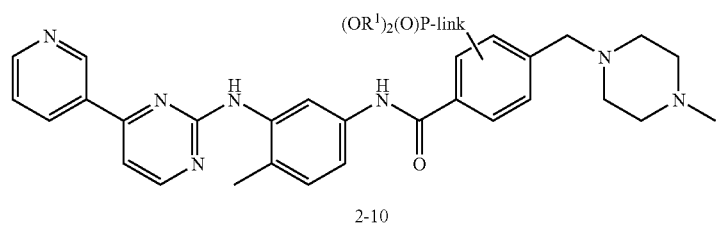

2-10

Schemes 2.5-2.6 illustrates the preparation of compounds 2-10 in which A is Br, I, [SH], [NH], etc., or the group link-P(O)(OR$^1$)$_2$. The amine 2-1 is treated with acid 2-8 as described above, Scheme 2.1, to give the amide 2-9. The preparation of acid 2-8 is described in Schemes 2.11-2.12 below.

The reactions shown in Schemes 2.5-2.6 illustrate the preparation of the compounds 2-9 in which the substituent A is either the group link-P(O)(OR$^1$)$_2$ or a precursor such as [OH], [SH], [NH], Br, etc. Scheme 2.6 depicts the conversion of the compounds 2-9 in which A is [OH], [SH], [NH], Br, etc., into the phosphonate esters 2-10. In this procedure, the compounds 2-9 are converted, using the procedures described below, Schemes 2.7-2.12, into the compounds 2-10.

Scheme 2.7

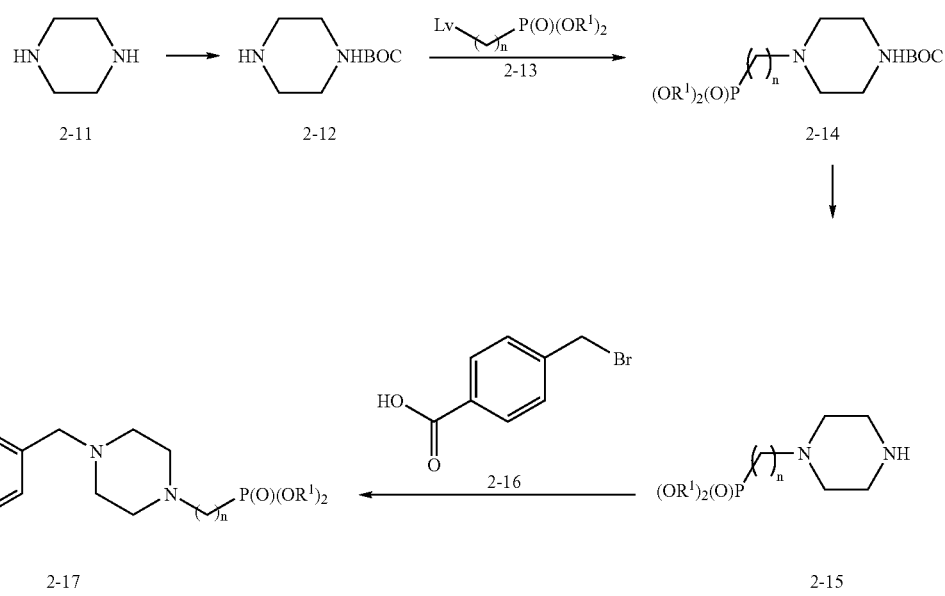

Scheme 2.8

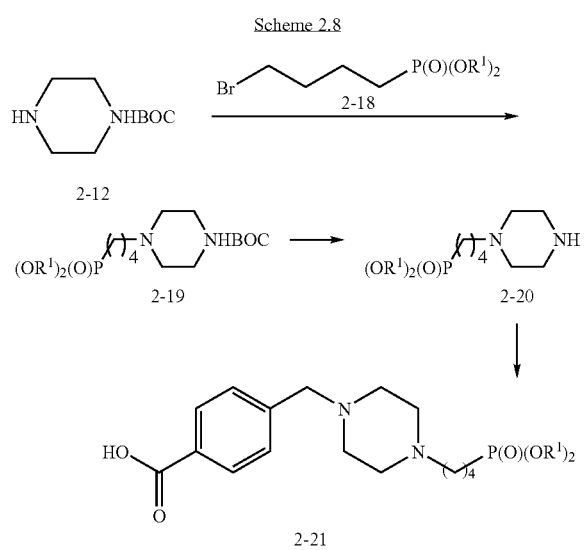

Schemes 2.7-2.8 describe the preparation of phosphonate-containing derivatives 2-2, in which A is Br, Cl, [OH], [NH], or the group link-$P(O)(OR^1)_2$ that are employed in the preparation of the phosphonate ester intermediates 2-4. Piperazine 2-11 is protected with a BOC group according to methods described in *Protective Groups in Organic Synthesis*, by T. W. Greene and P. G. M. Wuts, Wiley, Third Edition (1999) p. 518ff. Preferably piperazine is treated with 1 equivalent of BOC anhydride in methanol or DMF and one equivalent of triethylamine to give the BOC amine 2-12. Treatment of 2-12 with an alkylphosphonate 2-13 in which Lv is a leaving group such as triflate, Br, Cl, Mesyl, etc., in the presence of a suitable base, affords the product 2-14. The base required for this transformation is typically an inorganic base such as, for example, potassium carbonate, in the presence of an organic solvent such as dimethylformamide. The reaction proceeds at from ambient temperature to about 80° C. to afford the displacement products 2-14. Deprotection, of the BOC-amine group as described in *Protective Groups in Organic Synthesis*, by T. W. Greene and P. G. M. Wuts, Wiley, Third Edition (1999) p520ff., affords the amine 2-15. The amine 2-15 is then reacted with the acid 2-16 (Aldrich) in the presence of a base to give the product acid 2-17. For example, 2-12 prepared from piperazine as described above, is treated with bromophosphonate 2-18, prepared as described in *Syn.* 1999, 9, 909, and potassium carbonate in THF to give the amine 2-19. The BOC amine 2-19 is then deprotected by treatment with trifluoroacetic acid in dichloromethane to give the amine 2-20. The amine 2-20 is then reacted with the bromomethyl benzoic acid 2-16 in THF or dioxane in the presence of triethylamine, or aqueous potassium carbonate, to give the acid 2-21. Using the above procedures, but employing, in place of the bromo phosphonate compound 2-18, different phosphonates 2-13, the corresponding products 2-17 are obtained.

Scheme 2.9

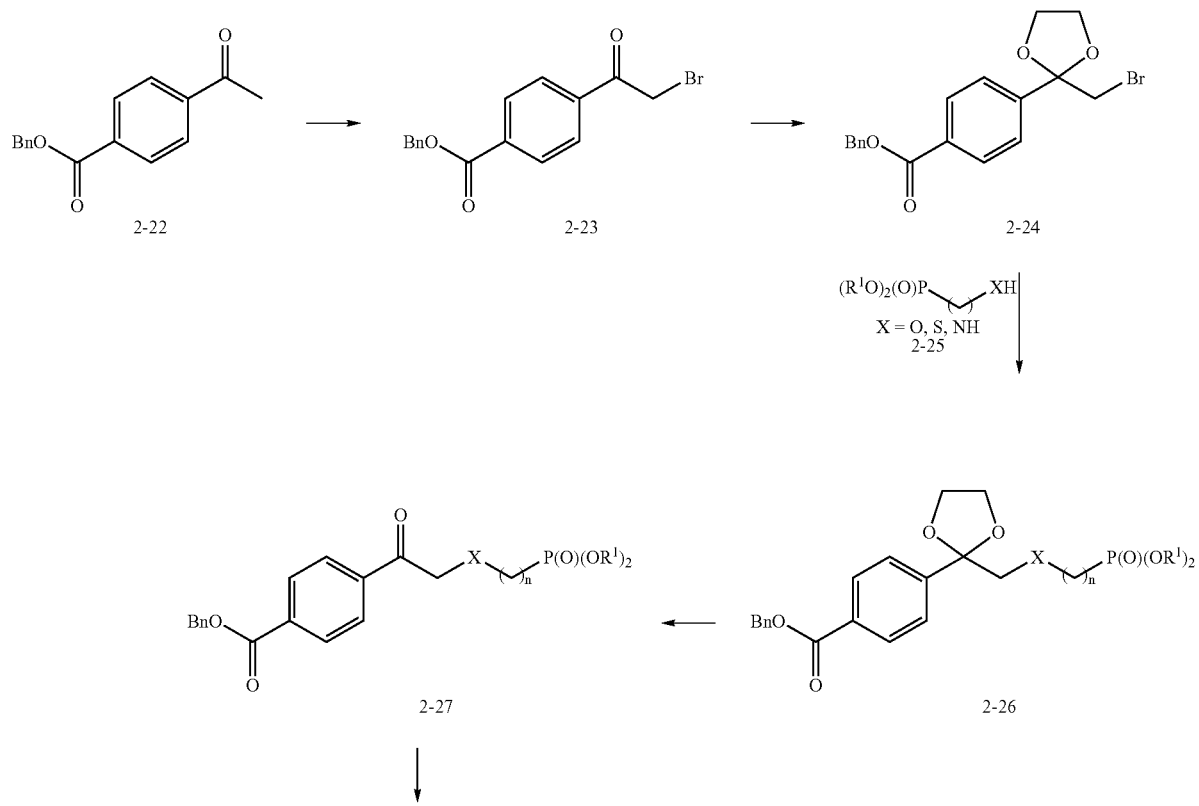

-continued

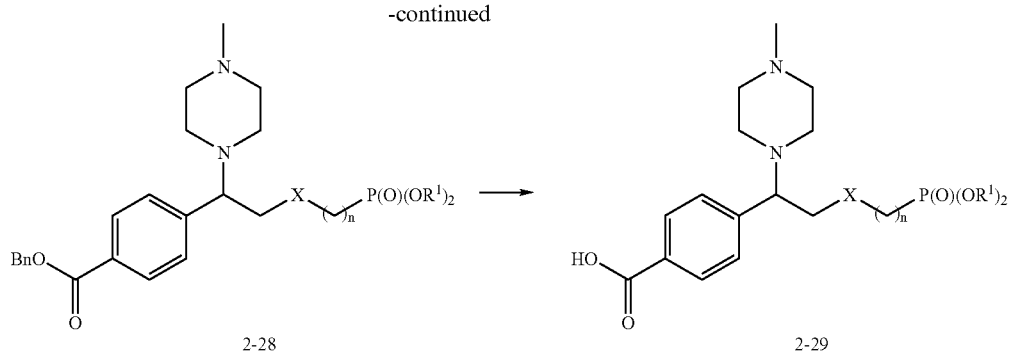

Schemes 2.9-2.10 describes the preparation of acids 2-5 in which the phosphonate is attached to the scaffold through a heteroatom and carbon linker. The benzyl protected ketone 2-22, prepared from the corresponding acid by treatment with benzyl alcohol in the presence of DCC and DMAP in DMF, as described in *Protective Groups in Organic Synthesis*, by T. W. Greene and P. G. M. Wuts, Wiley, Third Edition (1999), p. 373ff., is treated with a brominating agent to give the bromo ketone 2-23. Protection of the ketone as the cyclic dioxalone as described in T. W. Greene and P. G. M. Wuts, Wiley, Third Edition (1999), p. 312ff., gives 2-24. Dioxalone 2-24 is then treated with the dialkyl hydroxy, thio or amino-substituted alkylphosphonate 2-25 to give the dioxalone 2-26. The reaction is performed in the presence of a base, in a polar aprotic solvent such as dioxane or N-methylpyrrolidinone. The base employed in the reaction depends on the nature of the reactant 2-25.

For example, if X is O, a strong base such as, for example, lithium hexamethyldisilylazide or potassium tert. butoxide is employed. If X is S, NH or N-alkyl, an inorganic base such as cesium carbonate and the like is employed. Deprotection of the dioxalone as described in T. W. Greene and P. G. M. Wuts, Wiley, Third Edition (1999), p. 317ff., gives ketone 2-27 which is then treated under reductive amination conditions with N-methyl piperazine to give the amine 2-28. The preparation of amines by means of reductive amination procedures is described, for example, in *Comprehensive Organic Transformations*, by R. C. Larock, $2^{nd}$ edition, p. 835. In this procedure, the amine component and the aldehyde component are reacted together in the presence of a reducing agent such as, for example, borane, sodium cyanoborohydride or diisobutylaluminum hydride, to yield the amine product. Deprotection of the ester group as described in in T. W. Greene and P. G. M. Wuts, Wiley, Third Edition (1999) p. 373ff then affords the acid 2-29.

Scheme 2.10

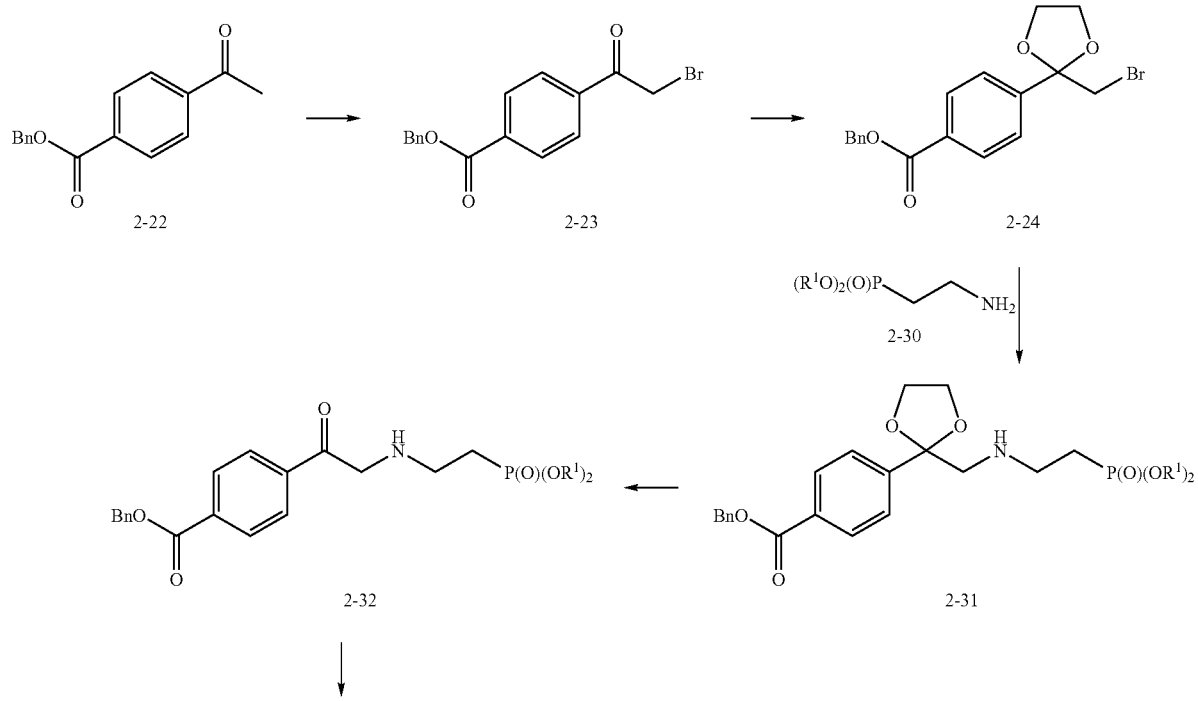

-continued

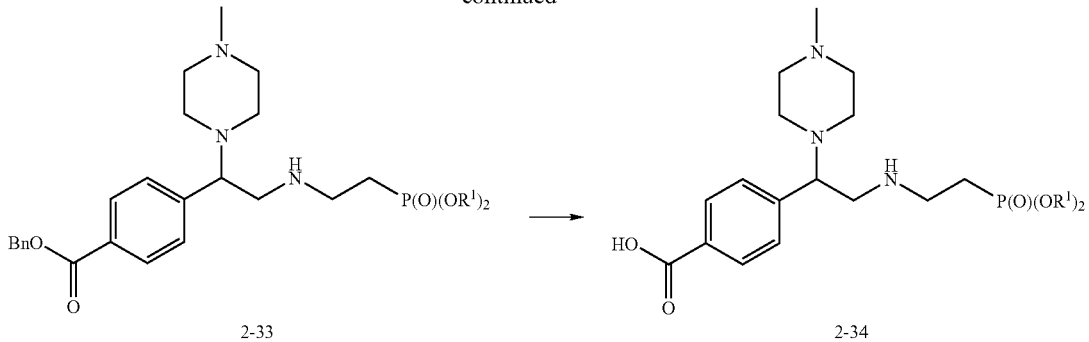

For example, 4-acetyl benzoic acid is treated with benzyl bromide in the presence of potassium carbonate in aqueous THF to give the ester 2-22. Treatment of the ester 2-22 with bromine in acetic acid, or NBS and AIBN in $CCl_4$ affords the bromide 2-23. Bromide 2-23 is then reacted with 1,2-ethane diol in toluene at reflux under a dean stark head with a catalytic amount of p-TsOH present to give the dioxalone 2-24. Dioxalone 2-24 is reacted with dialkyl 2-aminoethyl phosphonate 2-30, prepared as described in *J. Org. Chem.*, 2000, 65, 676, in dimethylformamide at about 80° C., in the presence of potassium carbonate, to afford the amine 2-31. Treatment of the dioxalone 2-31 with 1N hydrochloric acid in THF then yields the ketone 2-32. Ketone 2-32 is reacted with N-methyl piperazine in the presence of triethylamine followed 30 minutes later by the addition of sodiumcyano borohydride to give the amine 2-33. Removal of the benzyl ester by hydrolysis using sodium hydroxide in aqueous THF gives the acid 2-34. Using the above procedures, but employing, in place of the amino phosphonate compound 2-30, different phosphonates 2-25, the corresponding products 2-29 are obtained.

Scheme 2.11

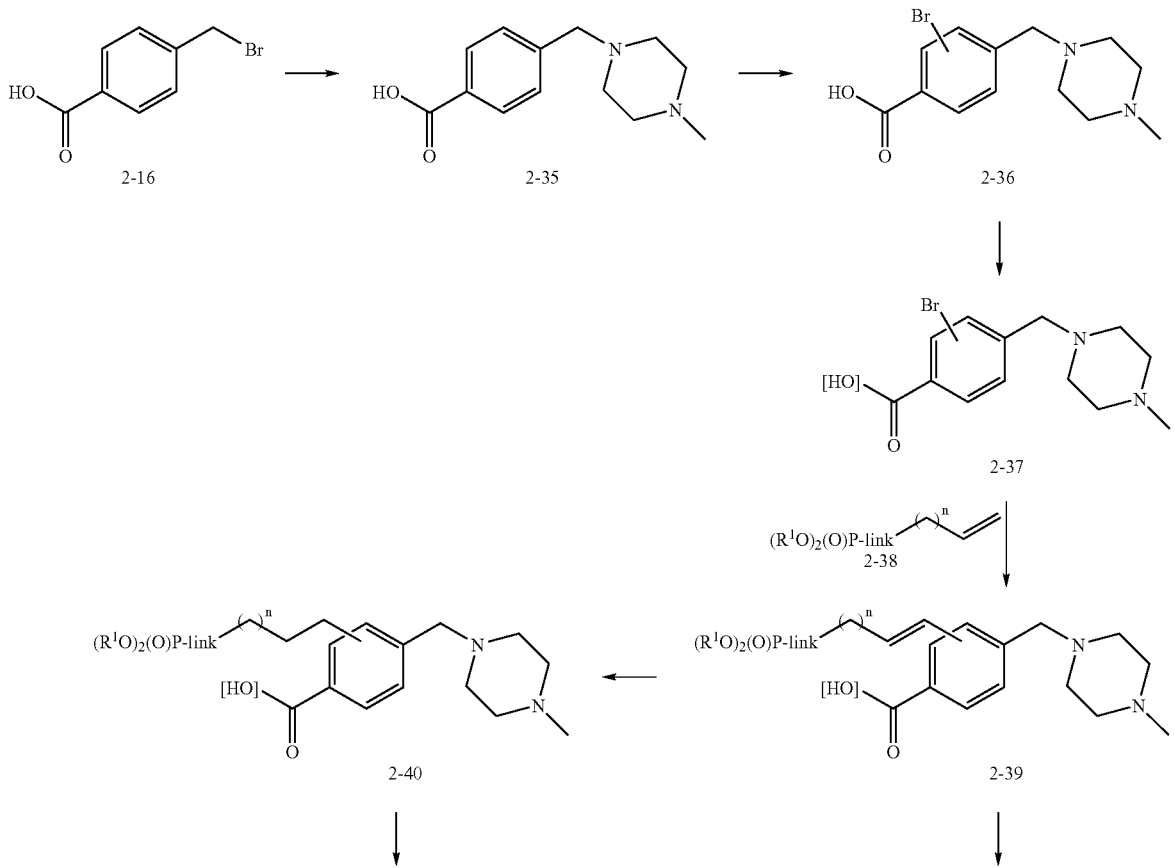

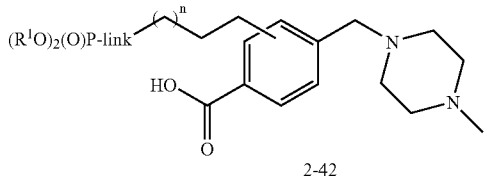

2-42

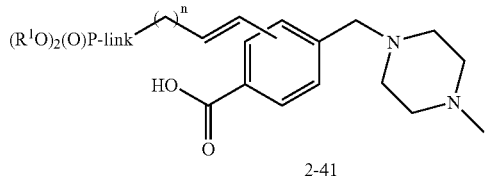

2-41

Schemes 2.11-2.12 illustrates the preparation of acid 2-8 in which the phosphonate is attached through a unsaturated or saturated carbon linker. In this procedure, the acid 2-16 (Aldrich) is treated with N-methyl piperazine as described in Schemes 2.7-2.8 for the preparation of 2-17, to give the acid 2-35. Acid 2-35 is then brominated with bromine or NBS to give the bromide 2-36. Bromide 2-36 is optionally protected as the benzyl or t-butyl ester, as described in *Protective Groups in Organic Synthesis*, by T. W. Greene and P. G. M. Wuts, Wiley, Third Edition (1999), page 373ff., to give 2-37. Ester 2-37 is then coupled, by means of a palladium-catalyzed Heck reaction with a dialkyl alkenyl phosphonate 2-38, to afford the coupled product 2-39. The coupling of aryl halides with olefins by means of the Heck reaction is described, for example, in *Advanced Organic Chemistry*, by F. A. Carey and R. J. Sundberg, Plenum, (2001), p. 503ff., and in *Acc. Chem. Res.*, 1979, 12, 146. The aryl bromide and the olefin are coupled in a polar solvent such as dimethylformamide or dioxane, in the presence of a palladium(0) catalyst such as tetrakis(triphenylphosphine) palladium(0) or a palladium(II) catalyst such as palladium(II) acetate, and optionally in the presence of a base such as triethylamine or potassium carbonate, to afford the coupled product 2-39. Optionally, the product 2-39 can be reduced to afford the saturated phosphonate 2-40. Methods for the reduction of carbon-carbon double bonds are described, for example, in *Comprehensive Organic Transformations*, by R. C. Larock, VCH, (1989), page 6. The methods include catalytic reduction, and chemical reduction, the latter for example employing diborane or diimide.

Scheme 2.12

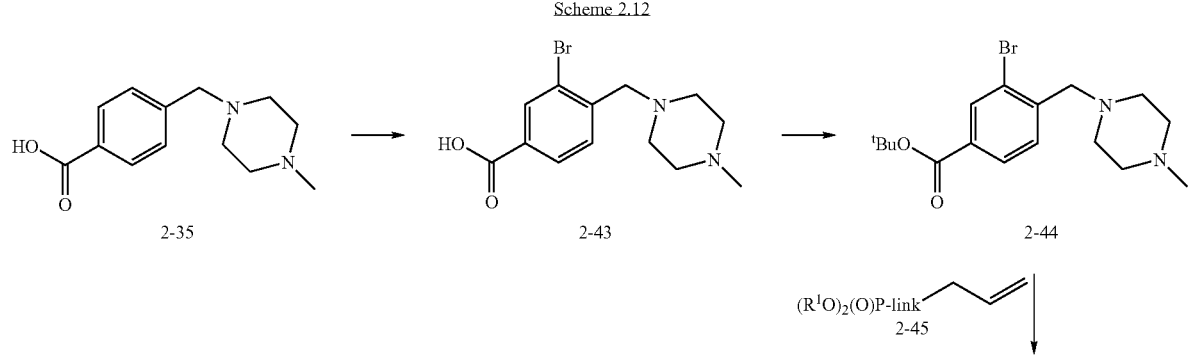

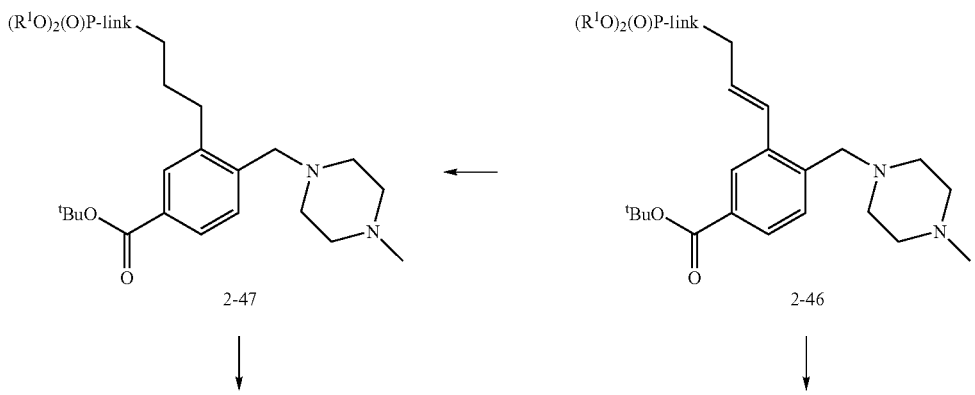

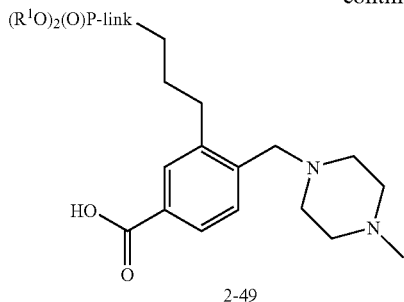

2-49

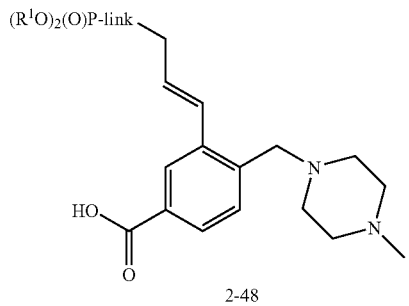

2-48

For example, amine 2-35 is then treated with NBS and AIBN in carbon tetrachloromethane at reflux to give the bromide 2-43. Bromide 2-43 is then reacted in t-butanol with DCC and DMAP to give the t-butyl ester 2-44. Ester 2-44 is then reacted with dialkyl propenyl phosphonate 2-45, the preparation of which is described in *J. Med. Chem.*, 1996, 39, 949, in the presence of bis(triphenylphosphine) palladium(II) chloride, as described in *J. Med. Chem.*, 1992, 35, 1371, to afford the coupled product 2-46. This product 2-46 is then treated with aqueous HCl in dioxane to give the acid 2-48. Optionally, the alkene 2-46 can be reduced by reaction with diimide, as described in *J. Org. Chem.*, 1965, 30, 3965, to afford the saturated product 2-47. Hydrolysis of the ester as described above through treatment with aqueous HCl in dioxane gives the acid 2-49. Using the above procedures, but employing, in place of the phosphonate compound 2-45, different phosphonates 2-38, the corresponding products 2-41 and 2-42 are obtained.

Example 3

Exemplary Compounds of the Present Invention

Scheme 3.1

Carbon

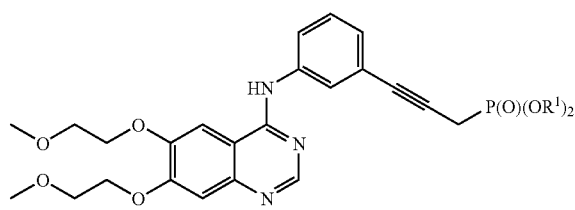

3-1

-continued

Heteroatom linked 3-2

3-3

Scheme 3.1 illustrates exemplary compounds of the present invention, wherein the phosphonate group can either be linked through a carbon atom, or a heteroatom, respectively.

Scheme 3.2

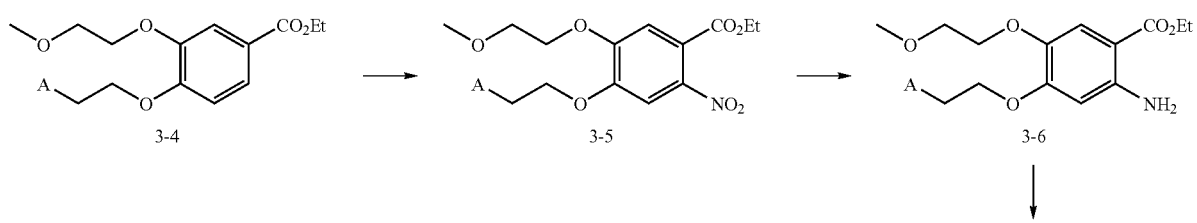

3-4   3-5   3-6

-continued

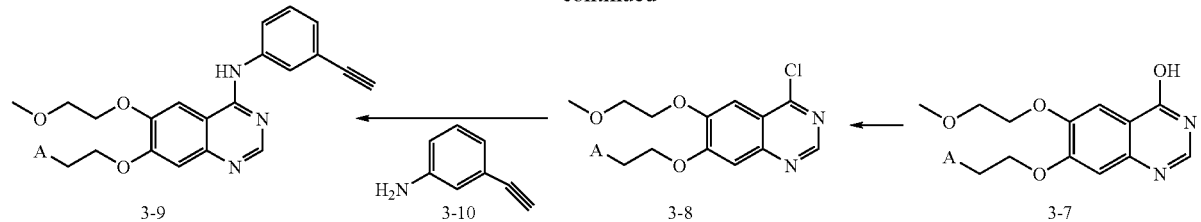

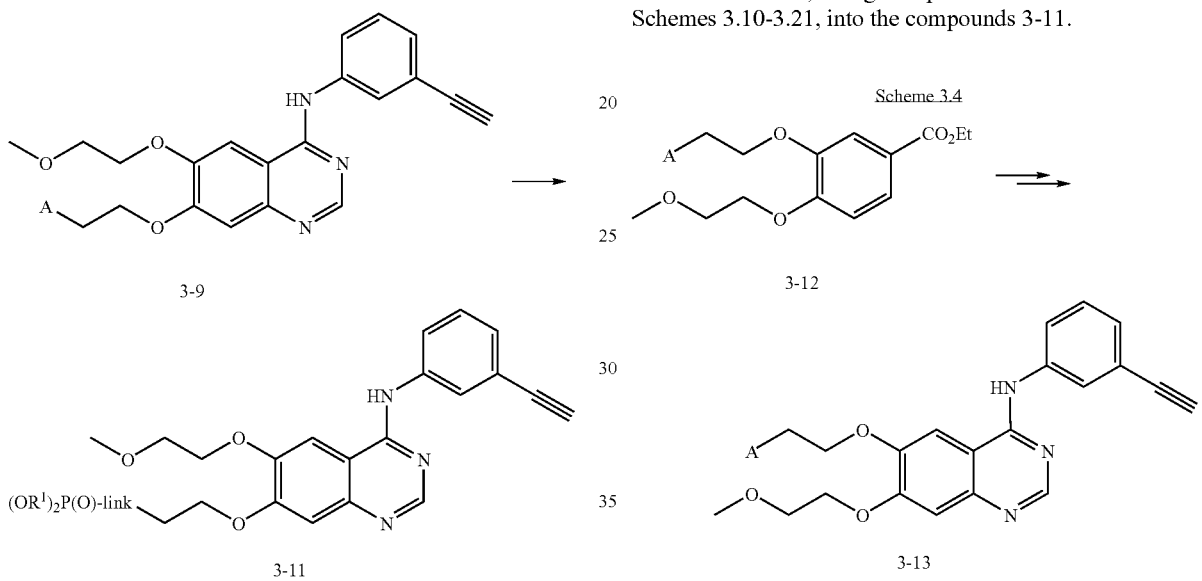

pounds 3-9 in which A is [OH], [SH], [NH], Br, etc., into the phosphonate esters 3-11. In this procedure, the compounds 3-9 are converted, using the procedures described below, Schemes 3.10-3.21, into the compounds 3-11.

Schemes 3.2-3.3 illustrates the synthesis of target molecules of type 3-11, in which A is Br, Cl, [OH], [NH], or the group link-P(O)(OR$^1$)$_2$. The preparation of 3-4, in which is A is a phosphonate is described below. Conversion of 3-4 into 3-9 in which A is methoxymethyl is described in EP 0817775 B1 and similar conditions can be used to prepare 3-9 in which A is the group link-P(O)(OR$^1$)$_2$. Nitration of the diether 3-4 gives nitro compound 3-5, which, followed by reduction under standard reducing conditions as described in *Comprehensive Organic Transformations*, by R. C. Larock, 2$^{nd}$ Edition, (1999), p821., affords the amine 3-6.

For example, 3-4 is treated with cold nitric acid in acetic acid, followed by catalytic hydrogenolysis of the nitro product in acidic ethanol over platinum oxide at high pressure to give the amine 3-6. The hydrochloride salt that is isolated is then heated at about 160° C. with ammonium formate and formamide to generate the quinazoline 3-7. The quianzoline is converted to the chloride, 3-8, as described in EP 0817775 B1. Preferably, the quinazoline, 3-7, is treated with oxalyl chloride in chloroform and DMF to give the chloride 3-8. Displacement of the chloride by the amine, 3-10, then affords the product 3-9. For example, heating the chloride 3-8 with 3-ethynyl-aniline in isopropanol at reflux gives 3-9.

The reactions shown in Scheme 3.2 illustrate the preparation of the compounds 3-9 in which the substituent A is either the group link-P(O)(OR$^1$)$_2$ or a precursor such as [OH], [SH], [NH], Br, etc. Scheme 3.3 depicts the conversion of the com-

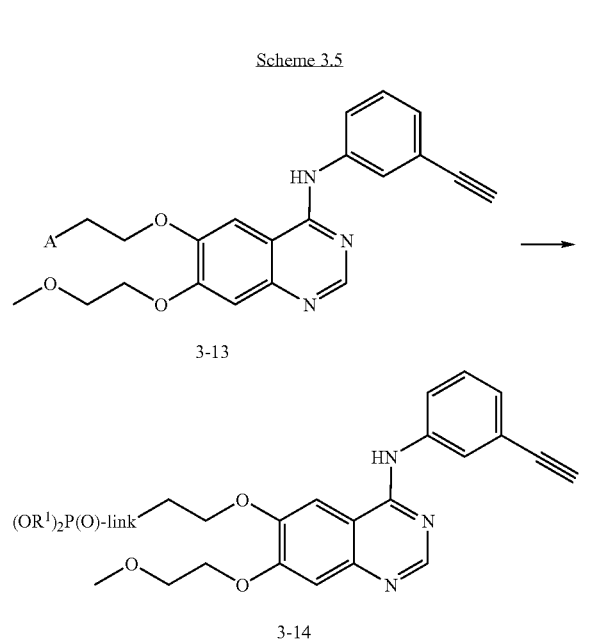

Schemes 3.4-3.5 illustrates the synthesis of target molecules of type 3-14, in which A is Br, Cl, [OH], [NH], or the group link-P(O)(OR$^1$)$_2$. Conversion of 3-12 into 3-13 is completed using the conditions described above, Scheme 3.2, for the conversion of 3-4 into 3-9. The preparation of 3-12, in which is A is a phosphonate is described below in Schemes 3.14-3.17.

The reaction shown in Scheme 3.4 illustrates the preparation of the compounds 3-13 in which the substituent A is either the group link-P(O)(OR$^1$)$_2$ or a precursor such as [OH], [SH], [NH], Br etc. Scheme 3.5 depicts the conversion of the compounds 3-13 in which A is [OH], [SH], [NH], Br etc, into the phosphonate esters 3-14. In this procedure, the compounds 3-13 are converted, using the procedures described below, Schemes 3.10-3.13, into the compounds 3-14.

Scheme 3.6

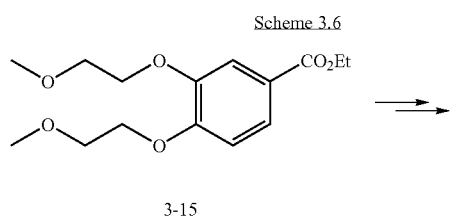

3-15

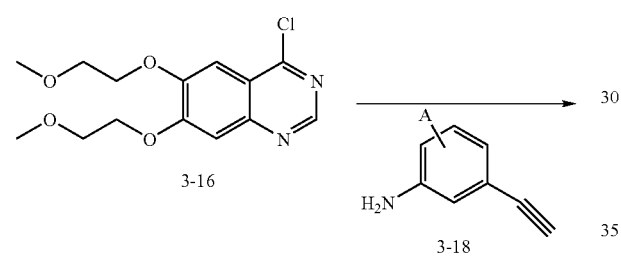

3-16  3-18

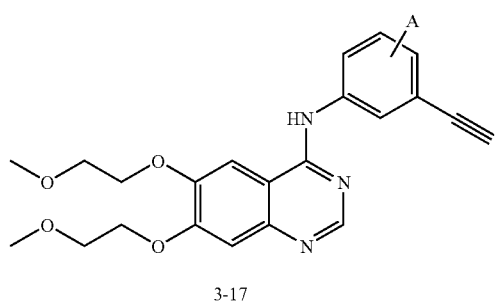

3-17

Scheme 3.7

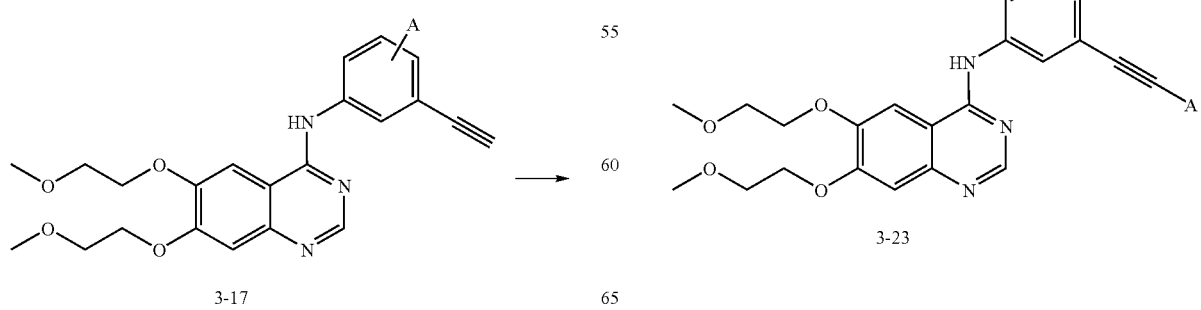

3-17

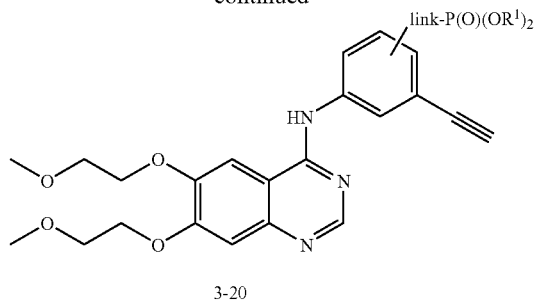

3-20

Schemes 3.6-3.7 illustrates the synthesis of target molecules of type 3-20, in which A is Br, Cl, [OH], [N], or the group link-P(O)(OR$^1$)$_2$. The preparation of 3-15 is described in EP 0817775 B1. Diether 3-15 is converted to the chloride 3-16 using conditions described in EP 0817775 B1 or as described above, Scheme 3.2. Treatment of chloride 3-16 with amine 3-18, in refluxing isopropanol gives 3-17. The preparation of 3-18, in which A is group link-P(O)(OR$^1$)$_2$ is shown below in Schemes 3.18-3.19.

The reactions shown in Scheme 3.6 illustrate the preparation of the compounds 3-17 in which the substituent A is either the group link-P(O)(OR$^1$)$_2$ or a precursor such as [OH], [SH], [NH], Br etc. Scheme 3.7 depicts the conversion of the compounds 3-17 in which A is [OH], [SH], [NH], Br etc, into the phosphonate esters 3-20. In this procedure, the compounds 3-17 are converted, using the procedures described below, Schemes 3.10-3.21, into the compounds 3-20.

Scheme 3.8

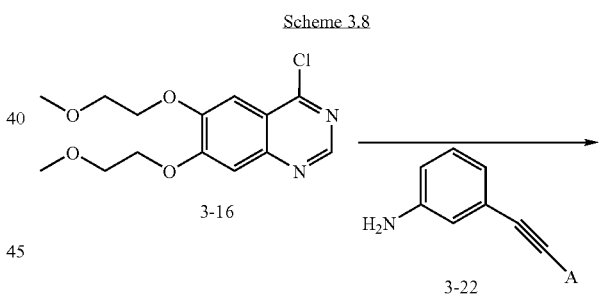

3-16  3-22

3-23

Scheme 3.9

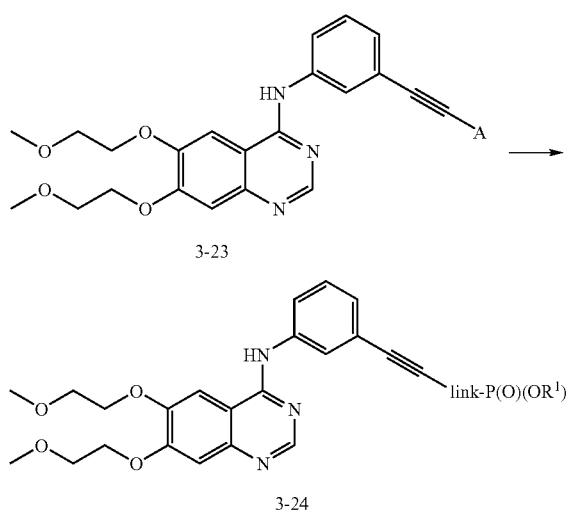

Schemes 3.8-3.9 illustrate the synthesis of target molecules of type 3-24, in which A is Br, Cl, [OH], [NH], or the group link-P(O)(OR$^1$)$_2$. The preparation of 3-16 is described in Scheme 3.6. Chloride 3-16 is converted to the amine 3-23 by treatment with amine 3-22 in refluxing isopropanol. The preparation of 3-22 in which A is group link-P(O)(OR$^1$)$_2$ is shown below in Schemes 3.20-3.21.

The reaction shown in Scheme 3.8 illustrates the preparation of the compounds 3-23 in which the substituent A is either the group link-P(O)(OR$^1$)$_2$ or a precursor such as [OH], [SH], [NH], Br, etc. Scheme 3.9 depicts the conversion of the compounds 3-23 in which A is [OH], [SH], [NH], Br, etc., into the phosphonate esters 3-24. In this procedure, the compounds 3-23 are converted, using the procedures described below in Schemes 3.10-3.21, into the compounds 3-24.

Scheme 3.10

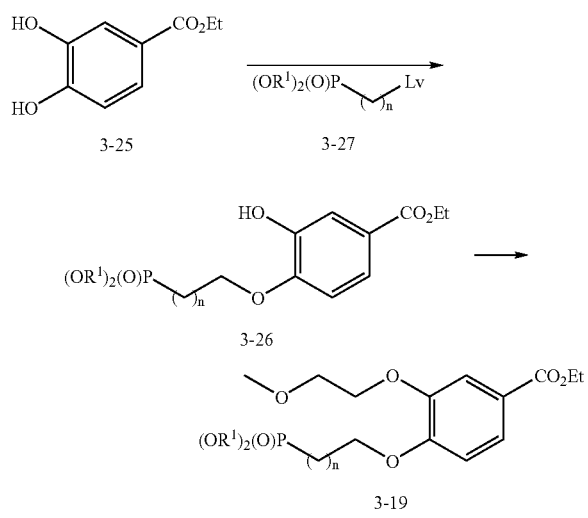

Scheme 3.11

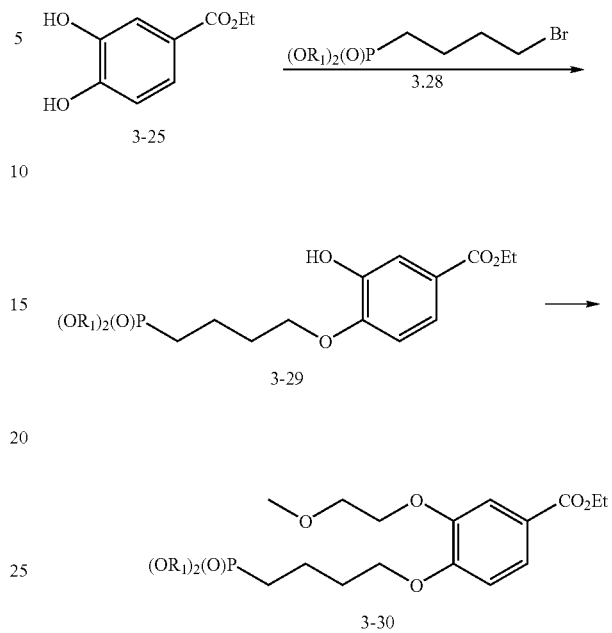

Schemes 3.10-3.13 describe the preparation of phosphonate-containing derivatives 3-19, 3-30, 3-69, 3-70 which are employed in the preparation of the phosphonate ester intermediates 3-11 (Scheme 3.3). The dihydroxybenzoic acid 3-25 is treated with one equivalent of the phosphonate alkylating agent, in which Lv is a leaving group such as mesyl, trifluoromethanesulfonyl, Br, I, Cl, tosyl, etc., in the presence of base as described in EP 0817775 B1, to give the ether 3-26. The ether is then subjected to the same alkylating conditions in the presence of 2-bromoethylmethyl ether (Aldrich) to give the diethers 3-19, 3-30, 3-69, and 3-70. For example, ester 3-25, prepared from the corresponding acid (Aldrich) by refluxing in concentrated HCl and ethanol in acetone, is treated with dialkyl 4-bromobutylphosphonate 3-28, prepared as described in *Syn.* 1999, 9, 909, potassium carbonate and tetrabutylammonium iodide to give the ether 3-29. Ether 3-29 is then treated with 2-bromoethylmethyl ether (Aldrich), potassium carbonate and tetrabutyl ammonium iodide to give the diether 3-30. Using the above procedures, but employing, in place of the bromobutylphosphonate 3-28, different phosphonates 3-27, and 3-37, the corresponding products 3-4, 3-19, 3-69, 3-70 are obtained.

Scheme 3.12

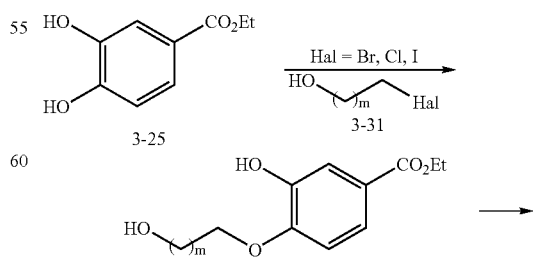

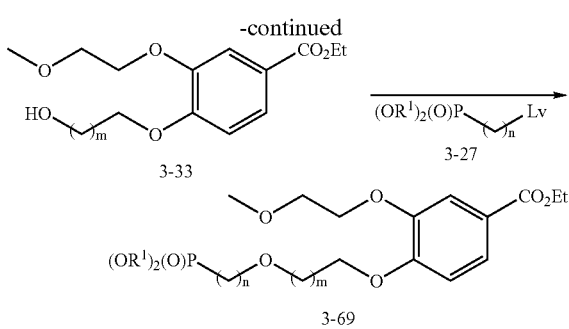

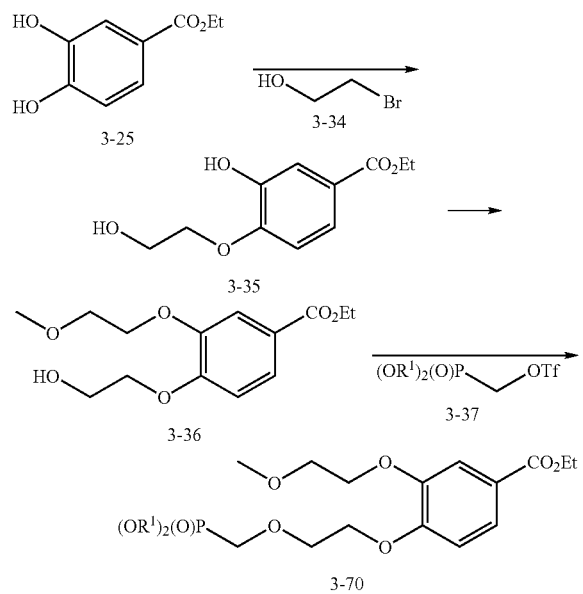

Schemes 3.12-3.13 also describe the preparation of phosphonate-containing derivatives 3-69, 3-70 which are employed in the preparation of the phosphonate ester intermediates 3-11 (Scheme 3.3). The dihydroxybenzoic acid 3-25, is treated with one equivalent of alcohol 3-31, as described in Schemes 3.10-3.11 to give ether 3-32. This ether 3-32 is then further treated with one equivalent of 2-bromoethylmethyl ether (Aldrich), and one equivalent of base as described in Schemes 3.10-3.11, to give the diether 3-33. Treatment with an phosphonate alkylating agent 3-27, in which Lv is a group such as mesyl, trifluoromethanesulfonyl, Br, I, Cl, tosyl, etc., in the presence of base then affords ether 3-69.

For example, 3-25 in acetone is treated with 2-bromoethanol, as described above in Scheme 3.10 for the preparation of 3-26 from 3-25, to give 3-35. Reaction with 2-bromoethylmethyl ether (Aldrich), and one equivalent of sodium hydride in DMF, then affords the diether 3-36. Reaction of diether 3-36 with triflate 3-37, prepared as described in *Tetrahedron Lett.* 1986, 27, 1497, and potassium carbonate in DMF, gives the ether 3-70. Using the above procedures, but employing, in place of the bromobutylphosphonate 3-28, different phosphonates 3-27, and in place of alcohol 3-34, different alcohols 3-31, the corresponding products 3-69 are obtained.

Schemes 3.14-3.17 describe the preparation of phosphonate-containing derivatives 3-12, 3-75, 3-76 which are employed in the preparation of the phosphonate ester intermediates 3-14 (Scheme 3.5).

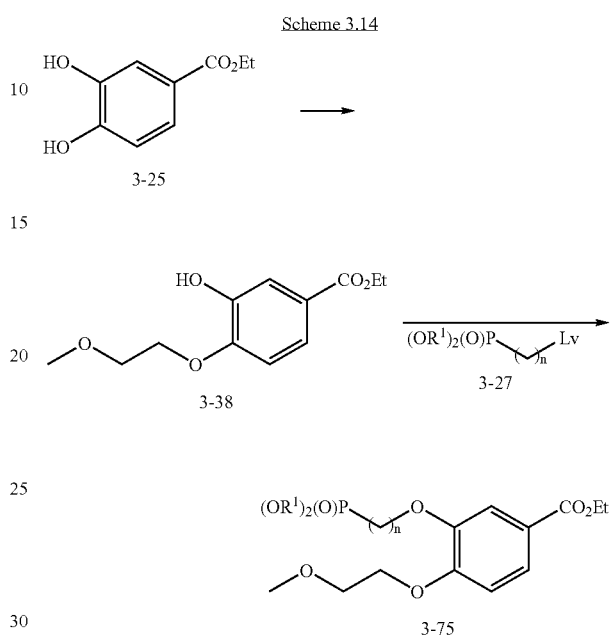

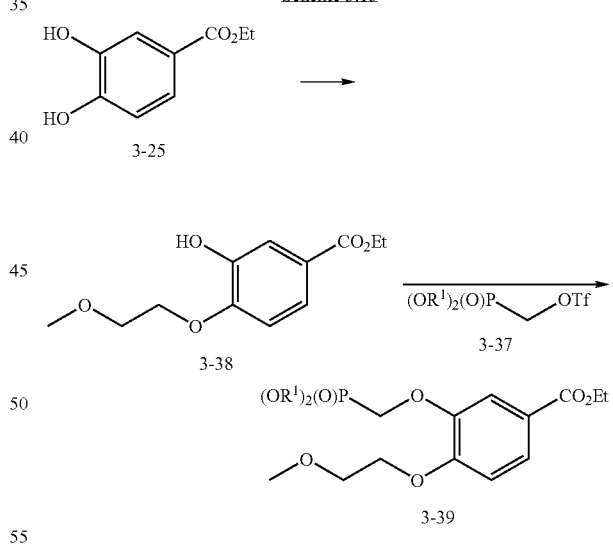

The dihydroxybenzoic acid 3-25 is first treated with 2-bromoethylmethyl ether (Aldrich), as described in Schemes 3.10-3.11 to give the ether 3-38. Ether 3-38 is then treated with one equivalent of the phosphonate alkylating agent, in which Lv is a group such as mesyl, trifluoromethanesulfonyl, Br, I, Cl, tosyl, etc., in the presence of base, as described in EP 0817775 B1, to give the ether 3-75. For example, ether 3-38 is treated with triflate 3-37, prepared as described in *Tetrahedron Lett.* 1986, 27, 1497, and potassium carbonate in DMF, to give the ether 3-39. Using the above procedures, but employing, in place of the phosphonate 3-37, different phosphonates 3-27, the corresponding products 3-75 are obtained.

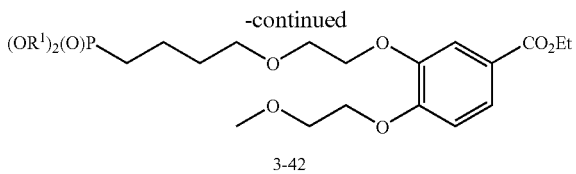

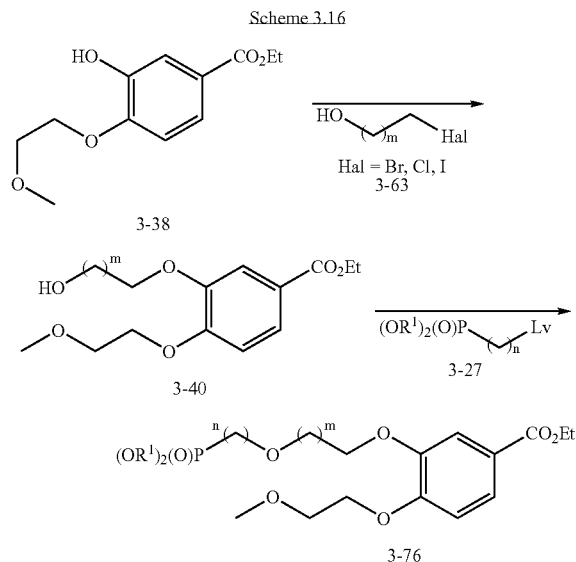

Schemes 3.16-3.17 describe the preparation of phosphonate-containing derivatives 3-76 which are employed in the preparation of the phosphonate ester intermediates 3-13 (Scheme 3.4). Ether 3-38 (Schemes 3.14-3.15) is reacted with 2-bromoethanol, as described above, Schemes 3.13, for the preparation of 3-35 from 3-25, to give 3-40. Treatment of diether 3-40 with an phosphonate alkylating agent 3-27, in which Lv is a group such as mesyl, trifluoromethanesulfonyl, Br, I, Cl, tosyl, etc., in the presence of base then affords ether 3-76. For example, 3-38 in acetone is treated 2-iodoethanol, 3-66, as described above, Schemes 3.13, for the preparation of 3-35 from 3-25, to give 3-41. Reaction with bromobutylphosphonate 3-28, as described above (Schemes 3.10-3.11) then affords 3-42. Using the above procedures, but employing, in place of the bromobutylphosphonate 3-28, different phosphonates 3-27, and in place of alcohol 3-66, different alcohols 3-63, the corresponding products 3-76 are obtained.

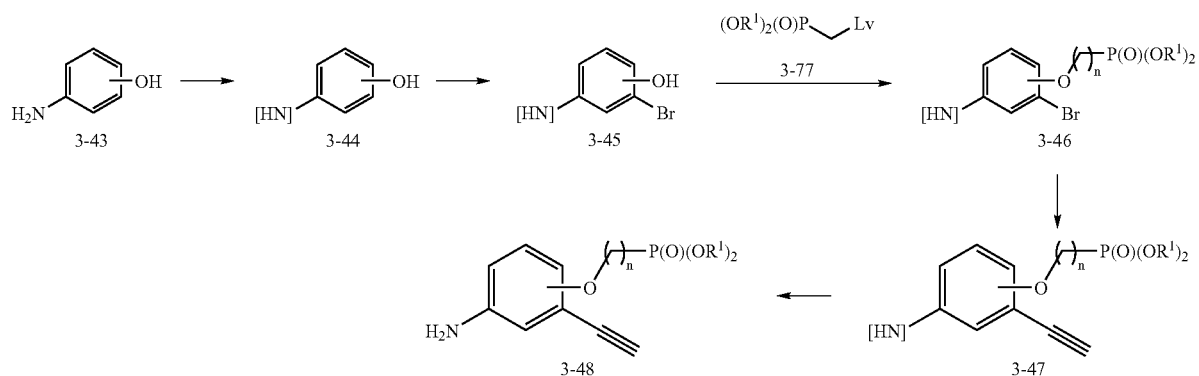

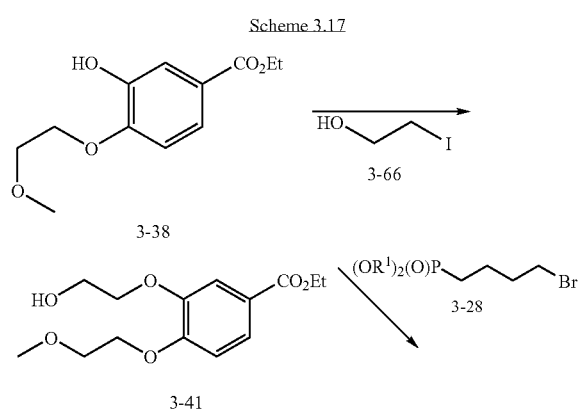

Schemes 3.18-3.19 describe the preparation of phosphonate-containing derivatives, which are employed in the preparation of the phosphonate ester intermediates 3-20 (Schemes 3.6-3.7). Aniline 3-43 is first protected using methods described in *Protective Groups in Organic Synthesis*, by T. W. Greene and P. G. M. Wuts, Wiley, Third Edition (1999), chapter 7. Bromination of 3-44 by treatment with bromine in acetic acid or NBS in tetrachloromethane at reflux, in the presence of AIBN then affords the bromophenol 3-45. Alkylation with a phosphonate alkylating agent 3-77 as described above, Schemes 3.10-3.11, then affords the phosphonate 3-46. Coupling with TMS acetylene by palladium mediated reaction affords the alkyne 3-47 which can then be deprotected using conditions described in *Protective Groups in Organic Synthesis*, by T. W. Greene and P. G. M. Wuts, Wiley, Third Edition (1999), chapter 7, gives the amine 3-48. The coupling of aryl halides with alkynes is described, for example, in *Comprehensive Organic Synthesis*, Eds. Trost and Fleming, Oxford, (1991), 3, part 2.4, page 521.

Scheme 3.19

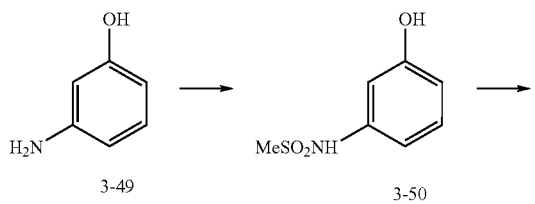

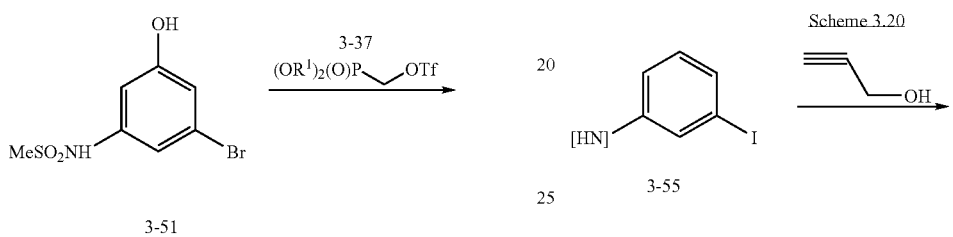

For example, 3-aminophenol, 3-49, is treated with one equivalent of mesyl chloride in the presence of pyridine to afford 3-50. The mesyl compound 3-50 is then treated with bromine in acetic acid to give the bromide 3-51. Bromide 3-51 is alkylated with 3-37 as described above (Schemes 3.12-3.13) to give the phosphonate 3-52. Treatment of 3-52 with TMS-acetylene in a polar solvent such as dimethylformamide or acetonitrile, in the presence of a palladium(0) catalyst such as tetrakis(triphenylphosphine)palladium(0) or a palladium(II) catalyst such as palladium(II) acetate, and optionally in the presence of a base such as triethylamine or potassium carbonate and copper (I) iodide, affords the coupled product 3-53. Deprotection of the mesyl group by treatment with potassium hydroxide in THF and water gives the amine 3-54. Using the above procedures, but employing, in place of the phosphonate 3-37, different phosphonates 3-77, and in place of alcohol 3-49, different alcohols 3-43, the corresponding products 3-48 are obtained.

Scheme 3.20

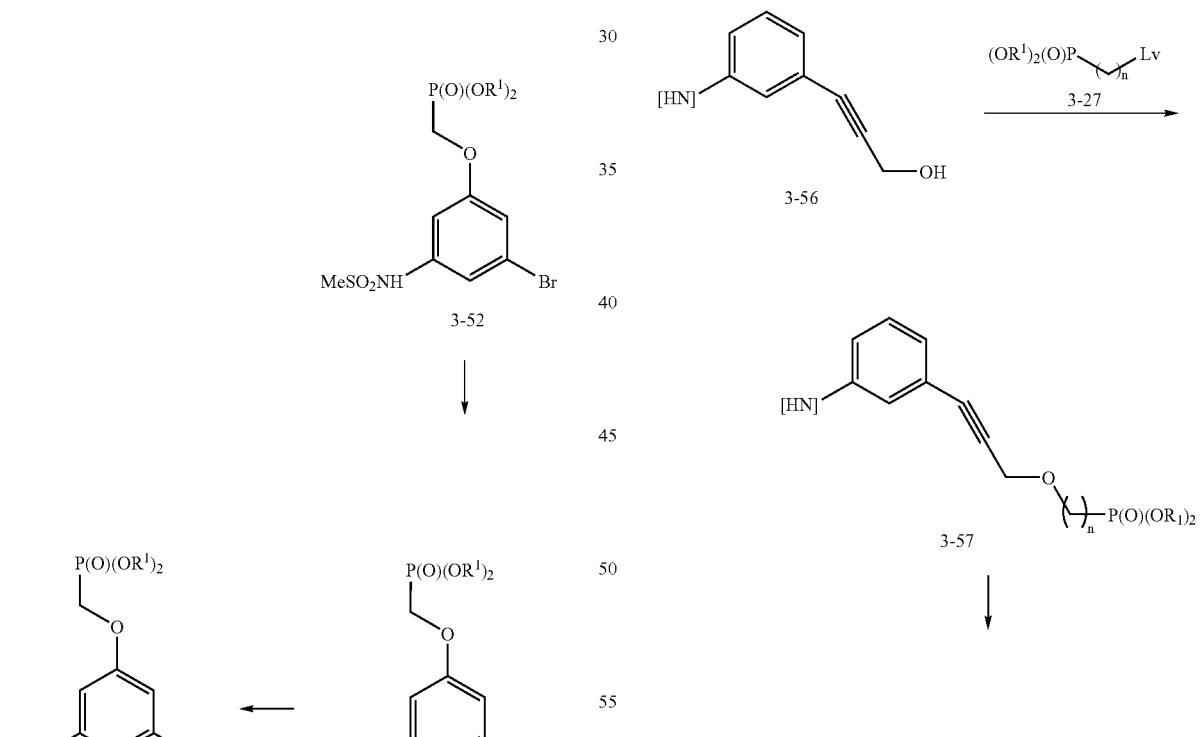

Schemes 3.20-3.21 describes the preparation of phosphonate-containing derivatives 3-58, which are employed in the preparation of the phosphonate ester intermediates 3-24 (Scheme 3.9). 3-Iodoaniline is first protected using methods described in *Protective Groups in Organic Synthesis*, by T. W. Greene and P. G. M. Wuts, Wiley, Third Edition (1999), chapter 7. Coupling with propargyl alcohol by palladium mediated reaction, as described above (Schemes 3.18-3.19) affords the alkyne 3-56. Alkylation with a phosphonate alkylating agent 3-27 as described above, Schemes 3.10-3.11, then affords the phosphonate 3-57. Finally, deprotection using conditions described in Protective Groups in Organic Synthesis, by T. W. Greene and P. G. M. Wuts, Wiley, Third Edition (1999), chapter 7, gives the amine 3-58.

Scheme 3.21

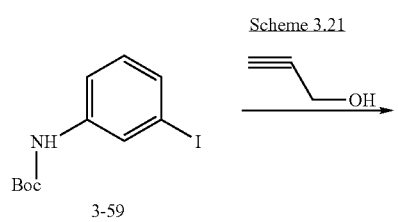

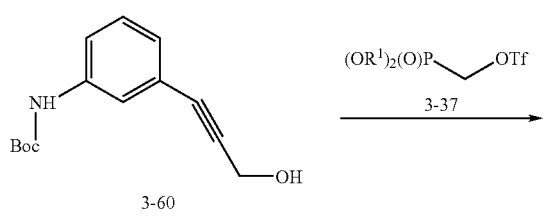

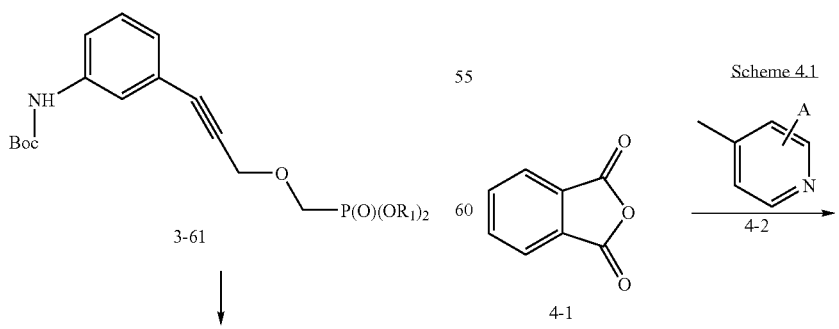

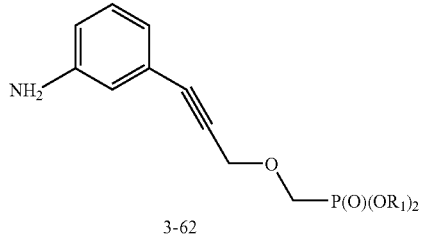

For example, 3-iodoaniline (Aldrich) is treated with BOC anhydride in the presence of pyridine and DMAP to afford 3-59. Treatment of 3-59 with propargyl alcohol in a polar solvent such as dimethylformamide or acetonitrile, in the presence of a palladium(0) catalyst such as tetrakis(triphenylphosphine) palladium(0) or a palladium(II) catalyst such as palladium(II) acetate, and optionally in the presence of a base such as triethylamine or potassium carbonate and copper (I) iodide, affords the coupled product 3-60. Alkylation of 3-60 with triflate 3-37, as described above, Schemes 3.12-3.13, then affords the phosphonate 3-61. Deprotection of the BOC group by treatment with TFA in THF or dioxane gives the amine 3-62. Using the above procedures, but employing, in place of the phosphonate 3-37, different phosphonates 3-27, and in place of iodoaniline 3-59, different anilines, 3-55, the corresponding products 3-58 are obtained.

The procedures described for the introduction of phosphonate moieties (Schemes 3.10-3.21) are, with appropriate modifications known to one skilled in the art, transferable to different chemical substrates. Thus, for example, the methods described above for the introduction of phosphonate groups onto the aryl rings of 3-18 and 3-48, are also applicable to the introduction of phosphonate moieties onto the alkynes 3-22 and 3-58, and vice versa.

Example 4

Exemplary Compounds of the Present Invention

-continued

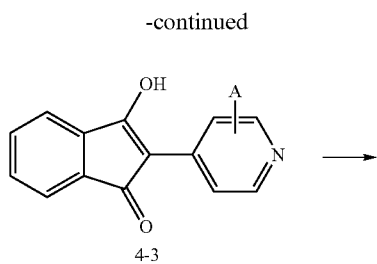
4-3

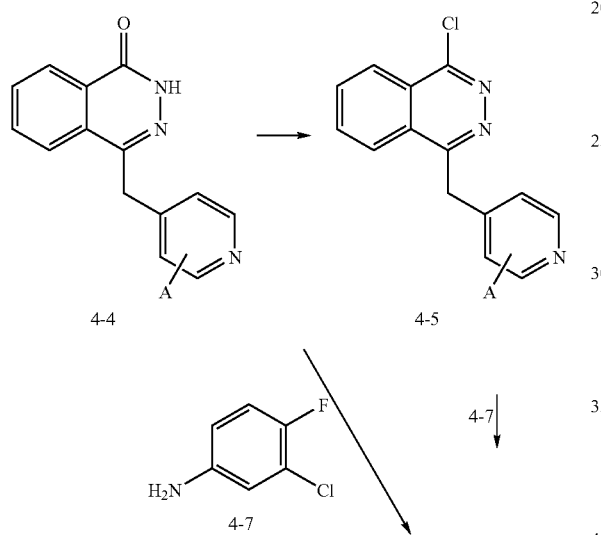

Scheme 4.1 illustrates the preparation of compounds 4-52 in which A is Br, I, [SH], [NH], etc., or the group link-P(O)(OR¹)₂. The preparation of these compounds follows procedures described in *J. Med. Chem.* 2000, 43, 12, 2310. The phthalic anhydride 4-1 is melted with a methylpyridine 4-2 in which A is Br, I, [SH], [NH], etc., or the group link-P(O)(OR¹)₂, under high temperature to give 4-3. The synthesis of 4-2 is described below. The product 4-3 on treatment with hydrazine in water and optionally ethanol, then rearranges to afford the ketone 4-4. Ketone 4-4 is then converted to the chloride 4-5 by treatment with a phosphorous oxychloride in an inert solvent such as acetontrile at about 50° C. The amine, 4-7, is introduced by heating the chloride 4-5 in the presence of the amine, optionally in a high boiling solvent such as xylenes or DMF to give the amine 4-6. Alternatively the pyridinone 4-4 can be directly converted to the product 4-6 in a one step procedure involving melting the aniline, 4-7, with the pyridinone in the presence of a dehydrating agent such as phosphorus pentoxide as described in *J. Med. Chem.* 2000, 43, 12, 2310.

Scheme 4.2

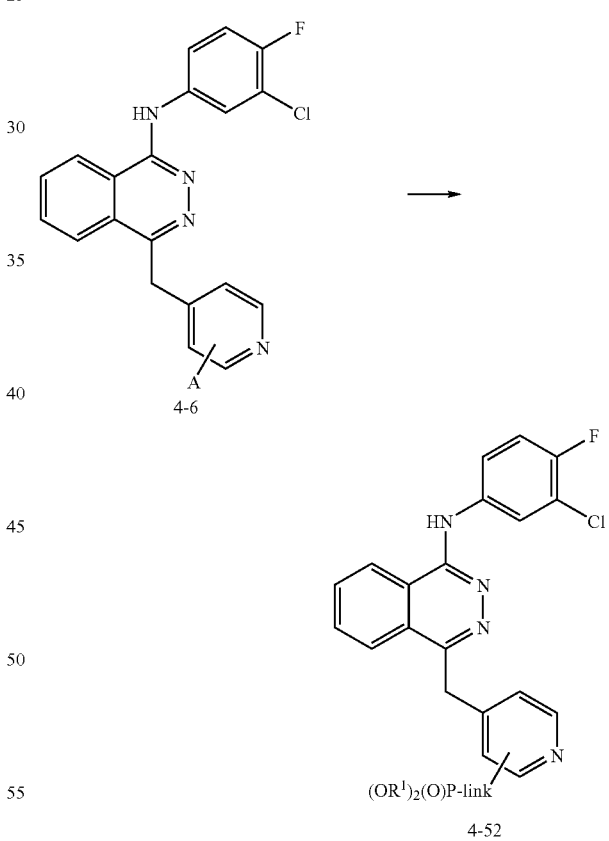

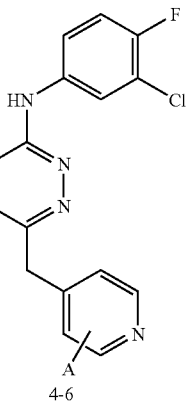
4-6

The reactions shown in Scheme 4.1 illustrate the preparation of the compounds 4-6 in which the substituent A is either the group link-P(O)(OR¹)₂ or a precursor such as [OH], [SH], [NH], Br etc. Scheme 4.2 depicts the conversion of the compounds 4-6 in which A is [OH], [SH], [NH], Br, etc., into the phosphonate esters 4-52. In this procedure, the compounds 4-6 are converted, using the procedures described below, Schemes 4.5-4.15, into the compounds 4-52.

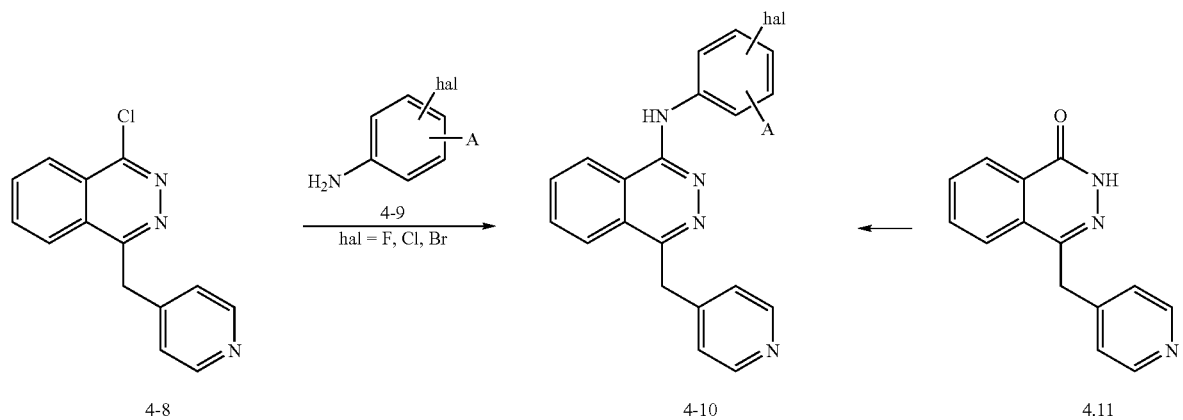

Scheme 4.3

Scheme 4.3 illustrates the preparation of compounds 4-12 in which A is Br, I, [SH], [NH], etc., or the group link-P(O)(OR$^1$)$_2$. The chloride 4-8, described in *J. Med. Chem.* 2000, 43, 12, 2310, is treated with an aniline 4-9, in which A is Br, I, [SH], [NH], etc., or the group link-P(O)(OR$^1$)$_2$, as described above in Scheme 4.1, to give amine 4-10. Alternatively the pyridinone 4-11, described in *J. Med. Chem.* 2000, 43, 12, p2310 is treated with an aniline 4-9 in which A is Br, I, [SH], [NH] etc or the group link-P(O)(OR$^1$)$_2$ as described above, Scheme 4.1, to give amine 4-10.

The reactions shown in Scheme 4.3 illustrate the preparation of the compounds 4-10 in which the substituent A is either the group link-P(O)(OR$^1$)$_2$ or a precursor such as [OH], [SH], [NH], Br etc. Scheme 4.4 depicts the conversion of the compounds 4-10 in which A is [OH], [SH], [NH], Br etc, into the phosphonate esters 4-12. In this procedure, the compounds 4-10 are converted, using the procedures described below, Schemes 4.5-4.15, into the compounds 4-12.

Schemes 4.5-4.10 describe the preparation of phosphonate-containing derivatives 4-2, in which A is Br, Cl, [OH], [NH], and the group link-P(O)(OR$^1$)$_2$, which are employed in the preparation of the phosphonate ester intermediates 4-52.

Scheme 4.4

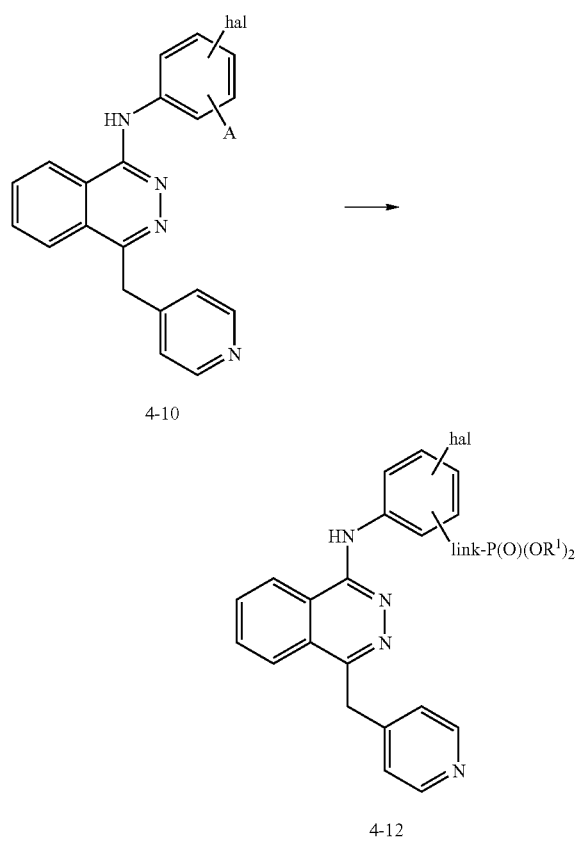

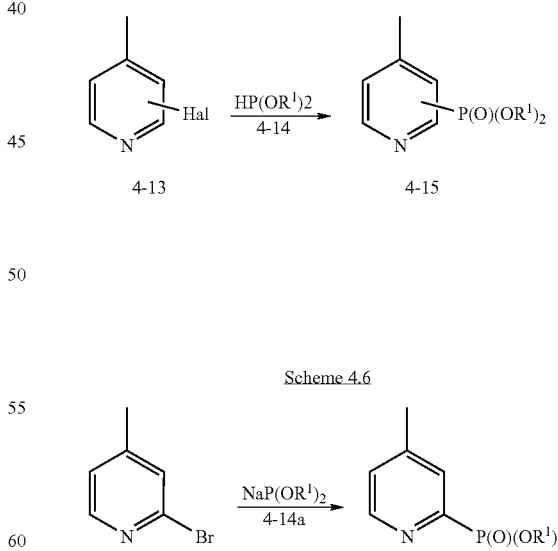

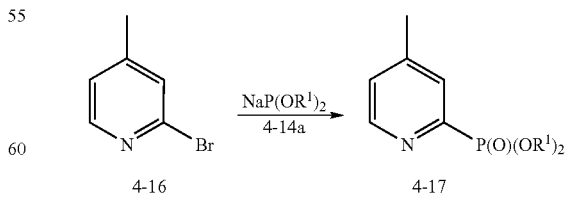

Schemes 4.5-4.6 describes the preparation of 4-2 (Scheme 4.1) in which the phosphonate is attached directly to the ring. The halo pyridine 4-13 is treated with a dialkyl phosphite 4-14 to give the phosphonate 4-15. The coupling reaction is conducted in the presence of a palladium (0) catalyst, for example as described in *J. Med. Chem.*, 1992, 35, 1371. For example 2-bromo-4-methyl pyridine (Aldrich) 4-16 is reacted with an equimolar amount of a dialkyl sodium phosphite 4-14a, in the presence of tetrakis(triphenylphosphine) palladium(0) and triethylamine, in toluene at reflux, to yield the phosphonate 4-17. Using the above procedures, but employing, in place of the halo pyridine compound 4-16, different pyridines 4-13, and/or different dialkyl sodium phosphites 4-14 the corresponding products 4-15 are obtained.

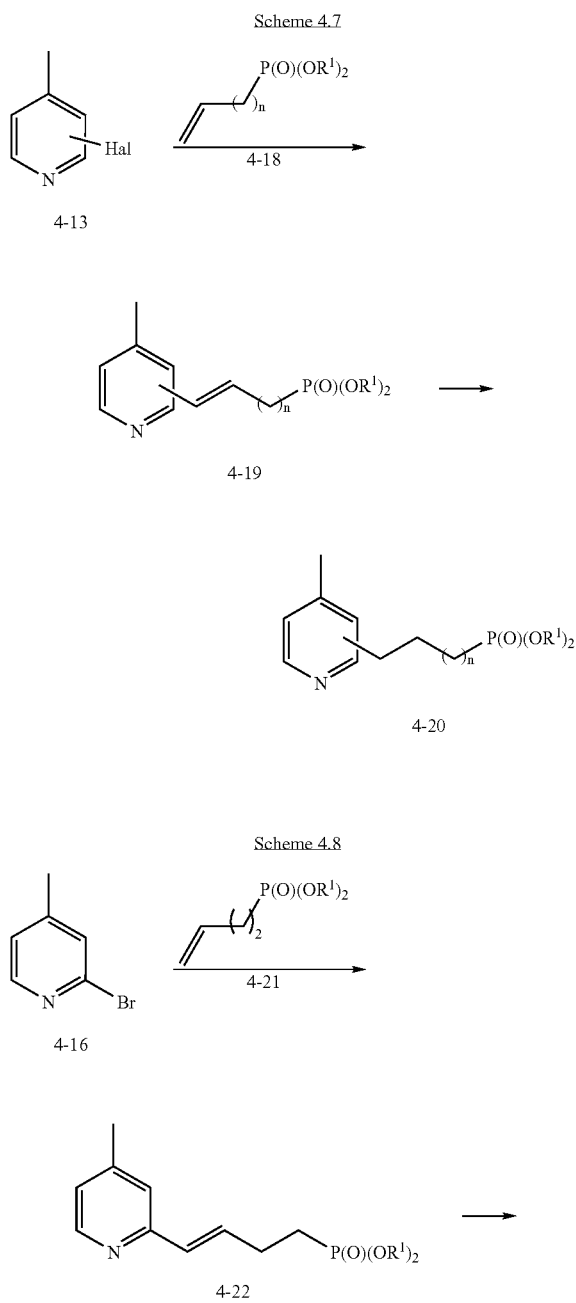

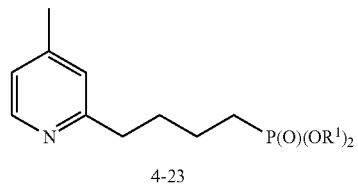

Schemes 4.7-4.8 illustrates the preparation of 4-2 in which the phosphonate is attached through a unsaturated or saturated carbon linker. In this procedure, a halo-substituted pyridine 4-13 is coupled, by means of a palladium-catalyzed Heck reaction with a dialkyl alkenyl phosphonate 4-18. The coupling of aryl halides with olefins by means of the Heck reaction is described, for example, in *Advanced Organic Chemistry*, by F. A. Carey and R. J. Sundberg, Plenum, (2001), p. 503ff., and in *Acc. Chem. Res.*, 1979, 12, 146. The aryl bromide and the olefin are coupled in a polar solvent such as dimethylformamide or dioxane, in the presence of a palladium(0) catalyst such as tetrakis(triphenylphosphine)palladium(0) or a palladium(II) catalyst such as palladium(II) acetate, and optionally in the presence of a base such as triethylamine or potassium carbonate, to afford the coupled product 4-19. Optionally, the product 4-19 can be reduced to afford the saturated phosphonate 4-20. Methods for the reduction of carbon-carbon double bonds are described, for example, in Comprehensive Organic Transformations, by R. C. Larock, VCH, (1989), p. 6. The methods include catalytic reduction, and chemical reduction, the latter for example employing diborane or diimide.

For example, 2-bromo-4-methylpyridine 4-16 is reacted with a dialkyl butenyl phosphonate 4-21, the preparation of which is described in *J. Med. Chem.*, 1996, 39, 949, in the presence of bis(triphenylphosphine) palladium(II) chloride, as described in *J. Med. Chem.*, 1992, 35, 1371, to afford the coupled product 4-22. Optionally, the product 4-22 is reduced, for example by reaction with diimide, as described in *J. Org. Chem.*, 1965, 30, 3965, to afford the saturated product 4-23. Using the above procedures, but employing, in place of the halo pyridine compound 4-16, different pyridines 4-13, and/or different phosphonates 4-18 the corresponding products 4-19 and 4-20 are obtained.

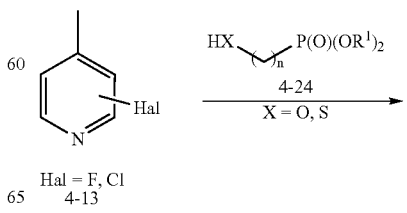

-continued

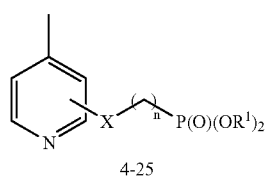
4-25

Scheme 4.11

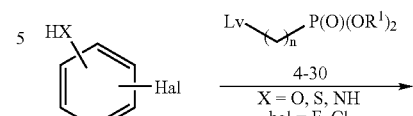
4-30
X = O, S, NH
hal = F, Cl

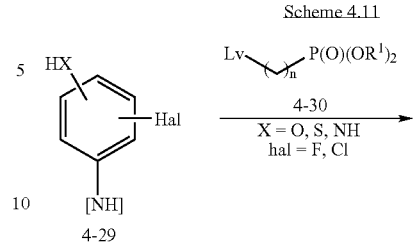
4-29

Scheme 4.10

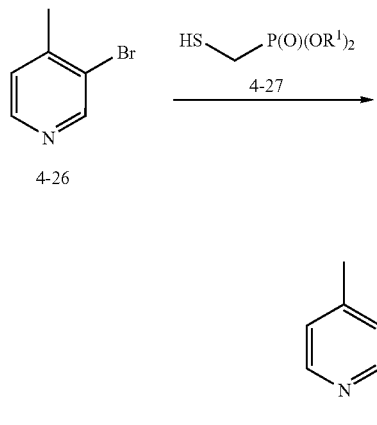
4-26
4-27
4-28

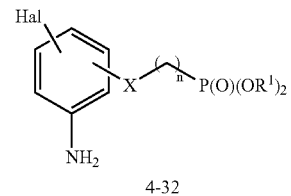
4-31

Schemes 4.9-4.10 illustrates the preparation of 4-2 in which the phosphonate is attached through a heteroatom e.g. O, S or N, and a carbon chain. In this procedure, a halo-substituted pyridine 4-13 is reacted with a dialkyl hydroxy- or thio-alkylphosphonate 4-24. The preparation of alkoxypyridines by the reaction of alkoxides with halopyridines is described, for example, in *J. Am. Chem. Soc.*, 1960, 82, 4414. The preparation of pyridine thioethers by reaction of halopyridines with thiols is described, for example, in *Chemistry of Heterocyclic Compounds, Pyridine and its derivatives*, E. Klingsberg, Ed., part 4, page 358. The alcohols and thiols are transformed into metal salts, for example sodium or potassium salts, and then reacted with the halopyridine substrates at elevated temperatures, optionally in the presence of copper powder catalyst, to afford the ether or thioether products 4-25. For example, a tetrahydrofuran solution of 3-bromo-4-methylpyridine 4-26 (Aldrich) is heated at reflux with an equimolar amount of a dialkyl 2-mercaptoethylphophonate 4-27, the preparation of which is described in Aust. J. Chem., 43, 1123, (1990), in the presence of sodium carbonate, to afford the thioether product 4-28. Using the above procedures, but employing, in place of the halopyridines 4-26, different halopyridines 4-13, and/or different hydroxy or thio-alkyl phosphonates 4-24, the corresponding products 4-25 are obtained.

Schemes 4.11-4.15 describe the preparation of phosphonate-containing derivatives 4-10, in which A is Br, Cl, [OH], [NH], and the group link-P(O)(OR$^1$)$_2$ which are employed in the preparation of the phosphonate ester intermediates 4-12 (Schemes 4.3-4.4).

4-32

Schemes 4.11-4.13 illustrates the preparation of 4-9 (Scheme 4.3) in which the phosphonate is attached through a heteroatom e.g. O, S, or N, and a carbon linker. In this procedure an optionally protected aniline is reacted with an alkylphosphonate 4-30 in which Lv is a leaving group such as triflate, Br, Cl, Mesyl, etc, in the presence of a suitable base. The base required for this transformation depends on the nature of the heteroatom X. For example, if X is N or S, an excess of an inorganic base such as, for example, potassium carbonate, in the presence of an organic solvent such as dimethylformamide, is suitable. The reaction proceeds at from ambient temperature to about 80° C. to afford the displacement products 4-31. If X is O, an equimolar amount of a strong base, such as, for example, lithium hexamethyldisilylazide and the like, is employed, in the presence of a solvent such as tetrahydrofuran. Deprotection, of the amine group as described in *Protective Groups in Organic Synthesis*, by T. W. Greene and P. G. M. Wuts, Wiley, Third Edition (1999) chapter 7, then affords the amine 4-32.

Scheme 4.12

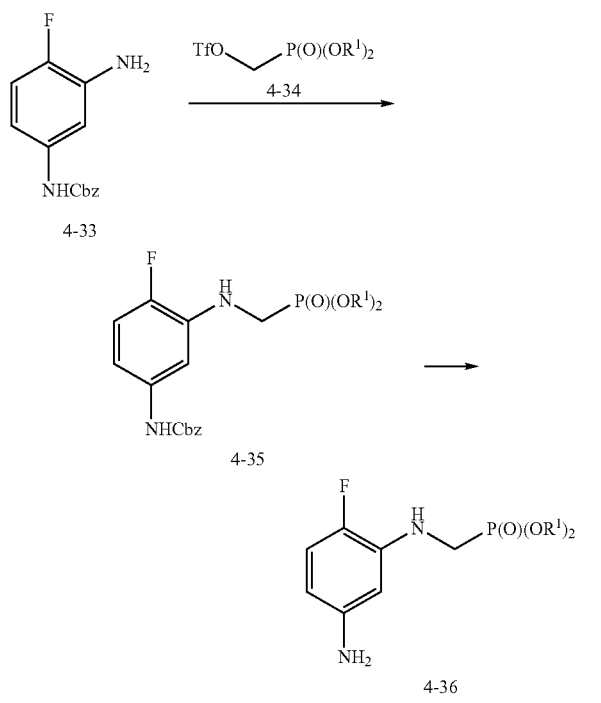

Scheme 4.13

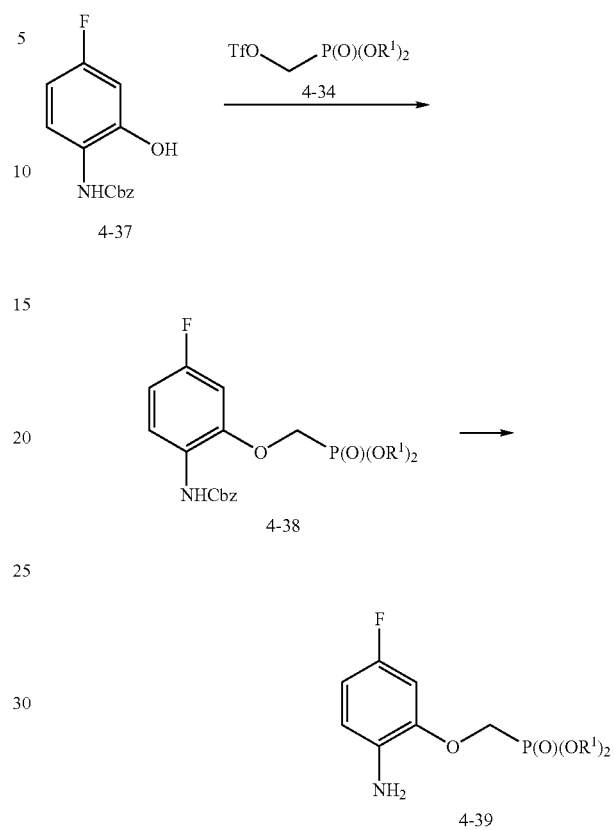

For example, the diamine 4-33 (Aldrich), mono-protected as the CBZ carbamate as described in *Protective Groups in Organic Synthesis*, by T. W. Greene and P. G. M. Wuts, Wiley, Third Edition (1999), 531ff, is treated with an equimolar amount of triflate 4-34, the preparation of which is described in *Tetrahedron Lett.* 1986, 27, 1497, in dimethylformamide containing excess potassium carbonate, at ca 60° C. to afford the phosphonate product 4-35. Deprotection by reduction over palladium on carbon in the presence of hydrogen then affords the amine 4-36. Using the above procedures, but employing, in place of the aniline 4-33, different anilines 4-29, and/or different alkylphosphonates 4-30, the corresponding products 4-32 are obtained.

Alternatively, the aminophenol 4-37, protected as the CBZ carbamate as described above, is reacted with one equivalent of an alkylphosphonate 4-34, as described above, to give phosphonate 4-38. Removal of the CBZ group by catalytic reduction over palladium on carbon in the presence of hydrogen then affords the amine 4-39.

Scheme 4.14

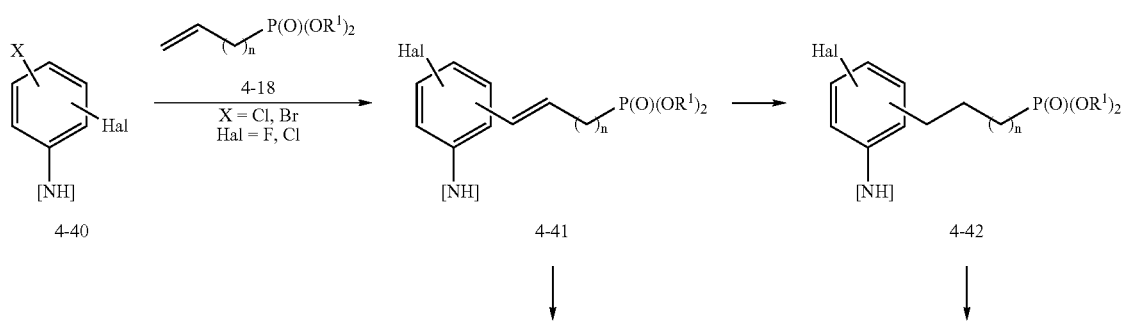

-continued

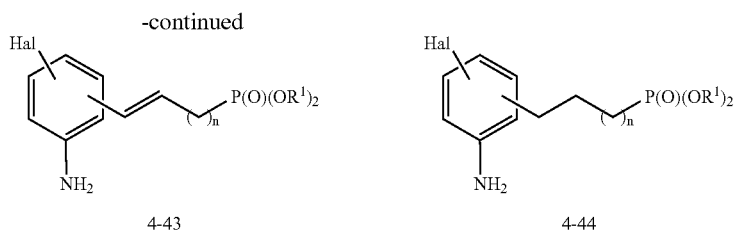

4-43

4-44

Schemes 4.14-4.15 illustrates the preparation of 4-9 in which the phosphonate is attached through a unsaturated or saturated carbon linker. In this procedure, an optionally protected halo-substituted aniline 4-40 is coupled, by means of a palladium-catalyzed Heck reaction with a dialkyl alkenyl phosphonate 4-18, as described above (Schemes 4.7-4.8), to afford the coupled product 4-41. Protection of anilines is described in *Protective Groups in Organic Synthesis*, by T. W. Greene and P. G. M. Wuts, Wiley, Third Edition (1999), chapter 7. Preferably the aniline is treated with a BOC reagent such as BOC chloride, or BOC anhydride in the presence of DMAP and a base, e.g., triethylamine, to afford the protected aniline.

Optionally, the coupled product 4-41 can be reduced, as described above (Schemes 4.7-4.8) to afford the saturated phosphonate 4-42. Removal of the protecting groups, as described in *Protective Groups in Organic Synthesis*, by T. W. Greene and P. G. M. Wuts, Wiley, Third Edition (1999) chapter 7, affords the anilines 4-43 and 4-44.

35, 1371, to afford the coupled product 4-47. The BOC protection of the aniline is performed by treating the aniline with BOC anhydride in the presence of DMAP. The product 4-47 is reduced, for example by reaction with diimide, as described in *J. Org. Chem.*, 1965, 30, 3965, to afford the saturated product 4-48. Treatment of 4-47 and 4-48 with TFA in THF or dioxane, affords the products 4-49 and 4-50 respectively. Using the above procedures, but employing, in place of the halo pyridine compound 4-45, different pyridines 4-40, and/or different phosphonates 4-18 the corresponding products 4-43 and 4-44 are obtained.

The procedures described for the introduction of phosphonate moieties (Schemes 4.5-4.15) are, with appropriate modifications known to one skilled in the art, transferable to different chemical substrates. Thus, the methods described above for the introduction of phosphonate groups onto the pyridyl ring of 4-2 are applicable to the introduction of phosphonate moieties onto the aniline 4-9 and the reverse is also true.

Example 5

Preparation of Exemplary Compounds of the Present Invention

Scheme 4.15

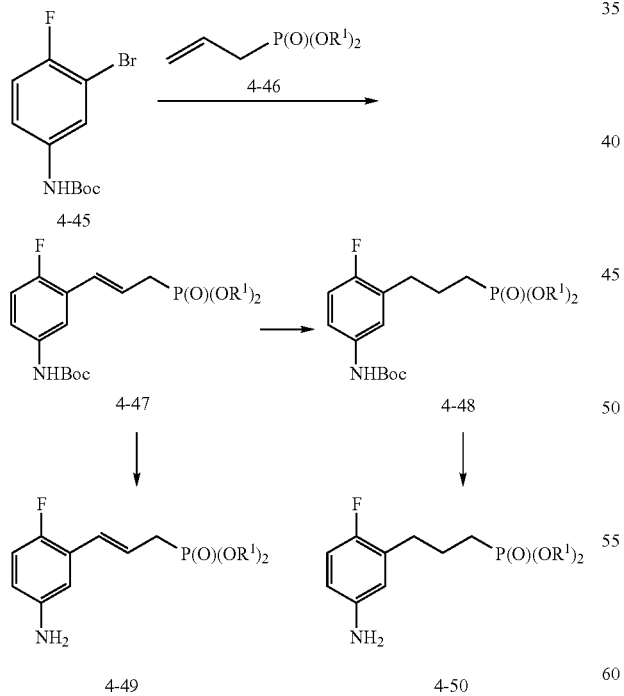

Scheme 5.1

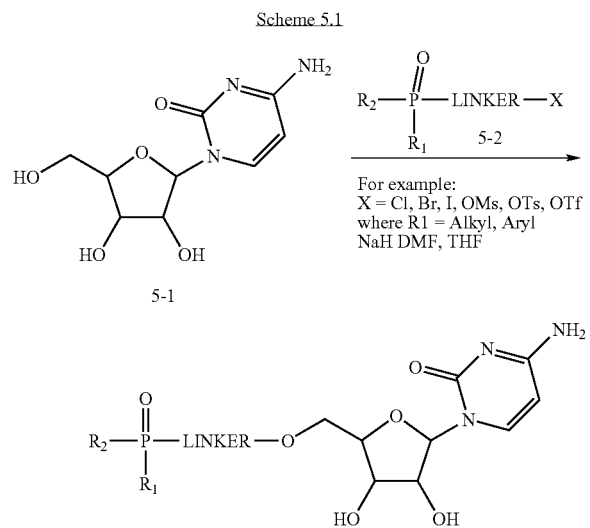

For example: 
X = Cl, Br, I, OMs, OTs, OTf 
where R1 = Alkyl, Aryl 
NaH DMF, THF For example, BOC protected 3-bromo-4-fluoro aniline 4-45 (Aldrich) is reacted with a dialkyl propenyl phosphonate 4-46, the preparation of which is described in *J. Med. Chem.*, 1996, 39, 949, in the presence of bis(triphenylphosphine) palladium(II) chloride, as described in *J. Med. Chem.*, 1992, R1 = H, alkyl, aryl, haloalkyl, alkenyl, aralyl, aryl
R2 = H, alkyl, aryl, haloalkyl, alkenyl, aralyl, aryl

Scheme 5.2

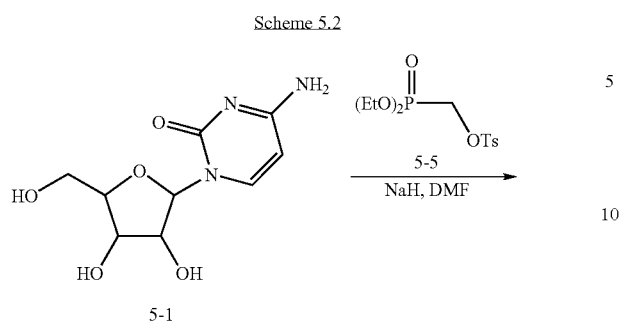

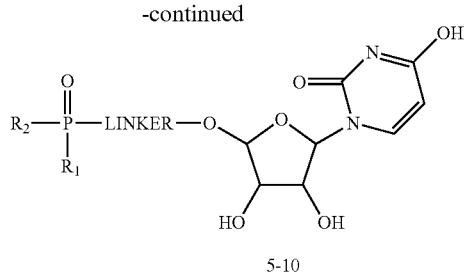

R1 = H, alkyl, aryl, haloalkyl, alkenyl, aralyl, aryl
R2 = H, alkyl, aryl, haloalkyl, alkenyl, aralyl, aryl

Scheme 5.4

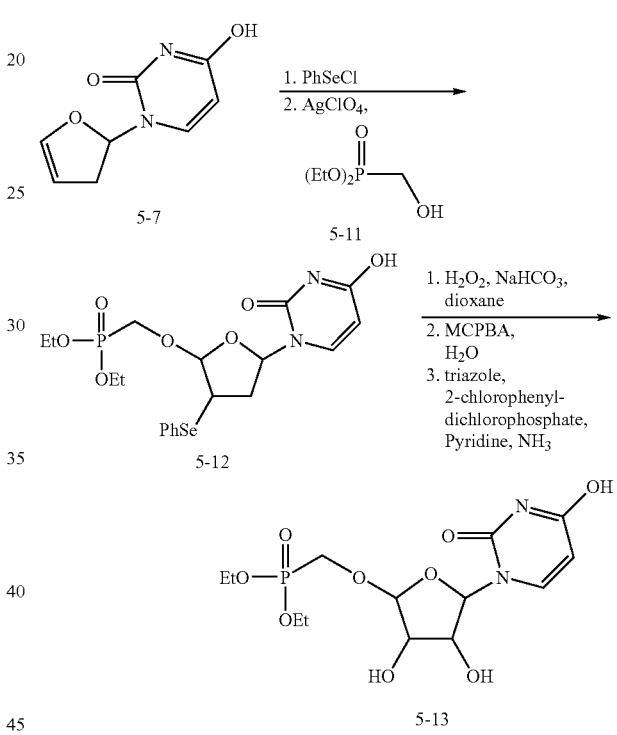

The desired phosphonate substituted analogs for conversion into the prodrugs are prepared by reaction of arabinofuranosylcytosine, 5-1 (obtained as described in U.S. Pat. No. 3,116,282, col. 26 line 0.65 to col. 28 line 25) with the respective alkylating reagents, 5-2. Schemes 5.1-5.2 shows the preparation of phosphonate linkage to 5-1 through the 5' hydroxyl group. Triol 5-1 is dissolved in a solvent such as DMF, THF and is treated with a phosphonate reagent bearing a leaving group, for example, bromine, mesyl, tosyl, or trifluoromethanesulfonyl in the presence of a suitable organic or inorganic base.

For example, 5-1 dissolved in DMF, is treated with 8 equivalents of sodium hydride and two equivalents of (toluene-4-sulfonylmethyl)-phosphonic acid diethyl ester 5-5, prepared according to the procedures in *J. Org. Chem.* 1996, 61, 7697, to give phosphonate 5-6 in which the linkage is a methylene group. Using the above procedure but employing different phosphonate reagents 5-2 in place of 5-5 the corresponding products 5-3 bearing different linking groups are obtained.

Scheme 5.3

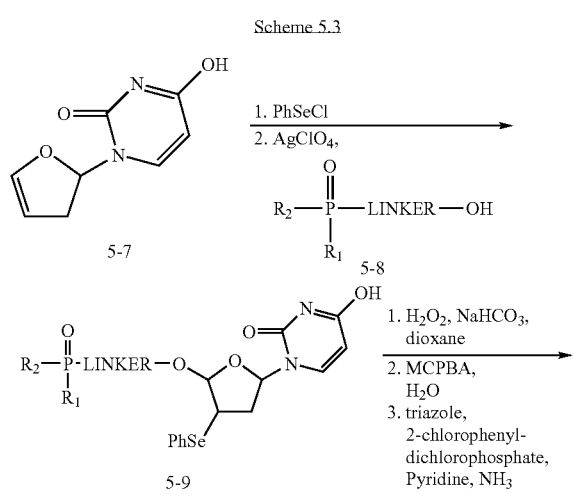

The desired phosphonate substituted analogs for conversion into the prodrugs are prepared by first reacting glycal 5-7 (obtained as described in *J. Am. Chem. Soc.* 1972, 94, 3213) with phenylselenyl chloride followed by treatment with the respective phosphonate alcohols 5-8 in the presence of silver perchlorate (*J. Org. Chem.* 1991, 56, 2642-2647). Oxidation of the resulting chloride using hydrogen peroxide followed by dihydroxylation of the resulting double bond with MCPBA and water generates the anti-diol (*Synth. Commun.* 1989, 19, 1939) which upon aminolysis of uracil using triazole, 2-chlorophenyldichlorophosphate, pyridine and ammonia (*Bioorg. Med. Chem. Lett.* 1997, 7, 2567) provides the desired product 5-3. Alternatively, the anti-diol can be accessed through an osmium tetroxide oxidation followed by selective protection and inversion using Mitsunobu conditions.

Schemes 5.3-5.4 show the introduction of different phosphonate linkages. For example, 5-7 dissolved in CH$_2$Cl$_2$, is treated with one equivalent of phenyl selenyl chloride at −70° C. followed by silver perchlorate in the presence of diethyl (hydroxymethyl) phosphonate to generate 5-12. The phosphonate is transformed into the desired analog by first oxidation with hydrogen peroxide, followed by an MCPBA oxidation and finally conversion of uracil to cytosine to the desired product 5-13. Using the above procedure but employing different phosphonate reagents 5-8 in place of 5-11 the corresponding products 5-10 bearing different linking groups are obtained. In some cases conversions to desired prodrugs may require the use of suitable protecting groups for the amino group of cytosine as well as the diol. Other bases could also be used to generate similar analogs of both 5-3 and 5-10 classes.

Example 6

Preparation of Exemplary Compounds of the Present Invention

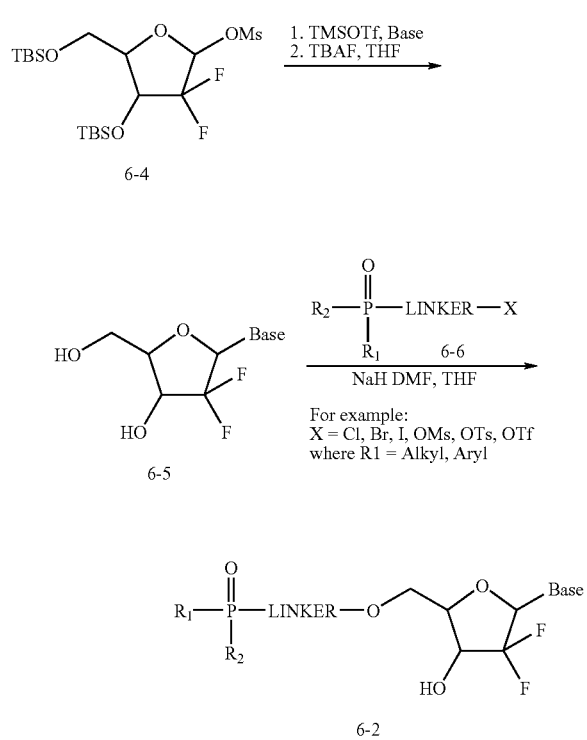

R1 = H, alkyl, aryl, haloalkyl, alkenyl, aralyl, aryl
R2 = H, alkyl, aryl, haloalkyl, alkenyl, aralyl, aryl
Bases = thymine, adenine, guanine, cytosine, uracil, inosine, diaminopurine.
Basess requiring protecting groups are to be suitably protected using protecting groups and conditions well known to thoses skilled in the art Representative compounds of the invention can be prepared as illustrated above. The desired phosphonate substituted analogs are prepared by reaction of intermediate 6-5 (obtained as described in U.S. Pat. No. 5,464,826) with the respective alkylating reagents 6-6. Illustrated above is the preparation of phosphonate linkage to 2'2'-difluoronucleosides through the 5'-hydroxyl group. The appropriately protected base as described in U.S. Pat. No. 5,464,826 is dissolved in a solvent such as DMF, THF and is treated with a phosphonate reagent bearing a leaving group, for example, bromine, mesyl, tosyl, or trifluoromethanesulfonyl in the presence of a suitable organic or inorganic base.

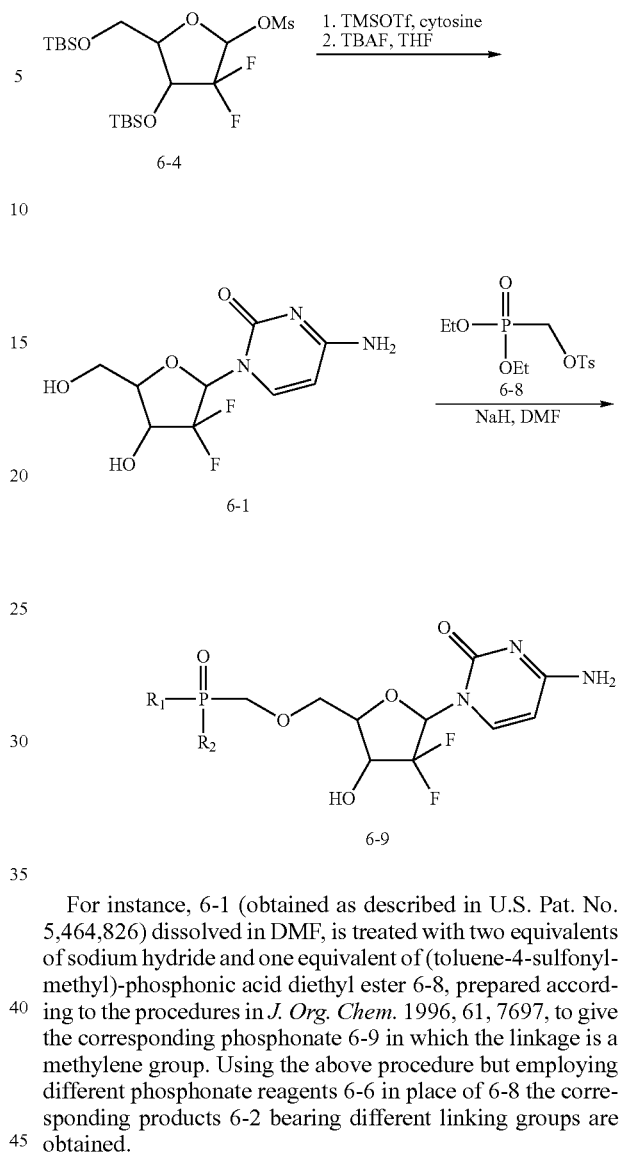

For instance, 6-1 (obtained as described in U.S. Pat. No. 5,464,826) dissolved in DMF, is treated with two equivalents of sodium hydride and one equivalent of (toluene-4-sulfonyl-methyl)-phosphonic acid diethyl ester 6-8, prepared according to the procedures in *J. Org. Chem.* 1996, 61, 7697, to give the corresponding phosphonate 6-9 in which the linkage is a methylene group. Using the above procedure but employing different phosphonate reagents 6-6 in place of 6-8 the corresponding products 6-2 bearing different linking groups are obtained.

Example 7

Preparation of Exemplary Compounds of the Present Invention

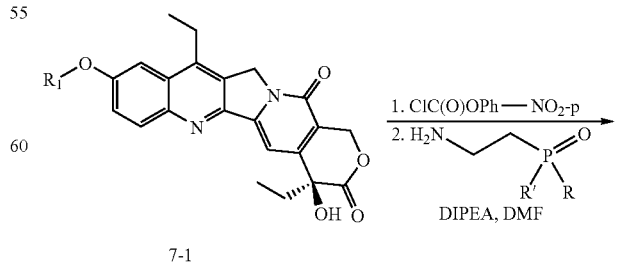

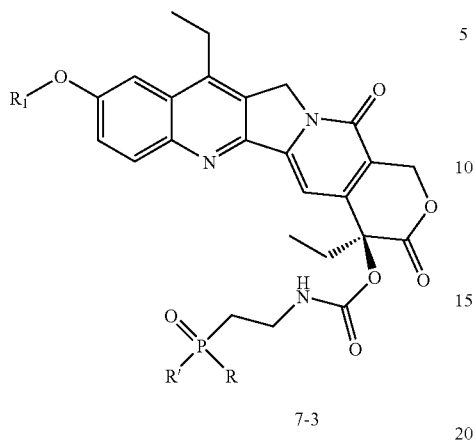

7-3

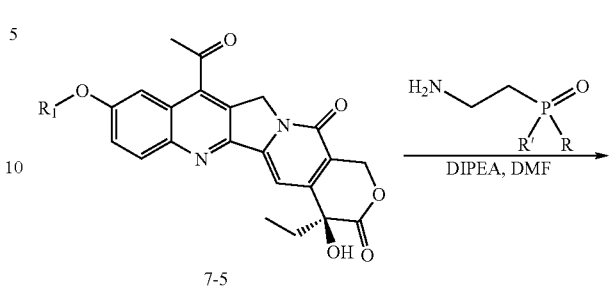

7-5

$R_1 =$ 

7-2

Compound 7-3 (X=—CH$_2$CH$_2$—) is prepared as outlined in Scheme 7.1. Camptosar (U.S. Pat. No. 4,604,463) is activated with p-nitrophenyl chloroformate in DMF and triethyl amine, followed by reaction with an aminophosphonate to furnish compound 7-3.

Scheme 7.2

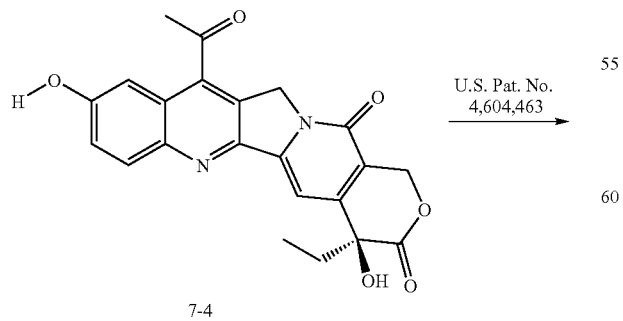

7-4

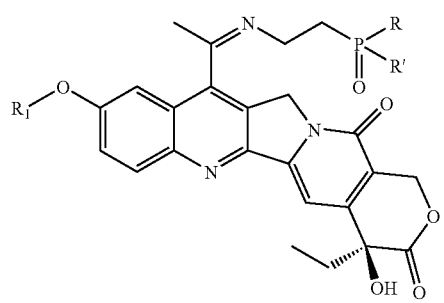

7-6

$R_1 =$ 

7-21

Compound 7-4 is obtained by a published procedure (*J. Chem. Soc. Perkin Trans.* 2, 1972, 2035). Activation of the 10-OH of 7-4, followed by reaction with amine 7-21 (as its acid chloride) gives 7-5 (U.S. Pat. No. 4,604,463). Compound 7-6 is prepared by refluxing 7-5 and an aminoethylphosphonate in DMF and DIPEA.

Scheme 7.3
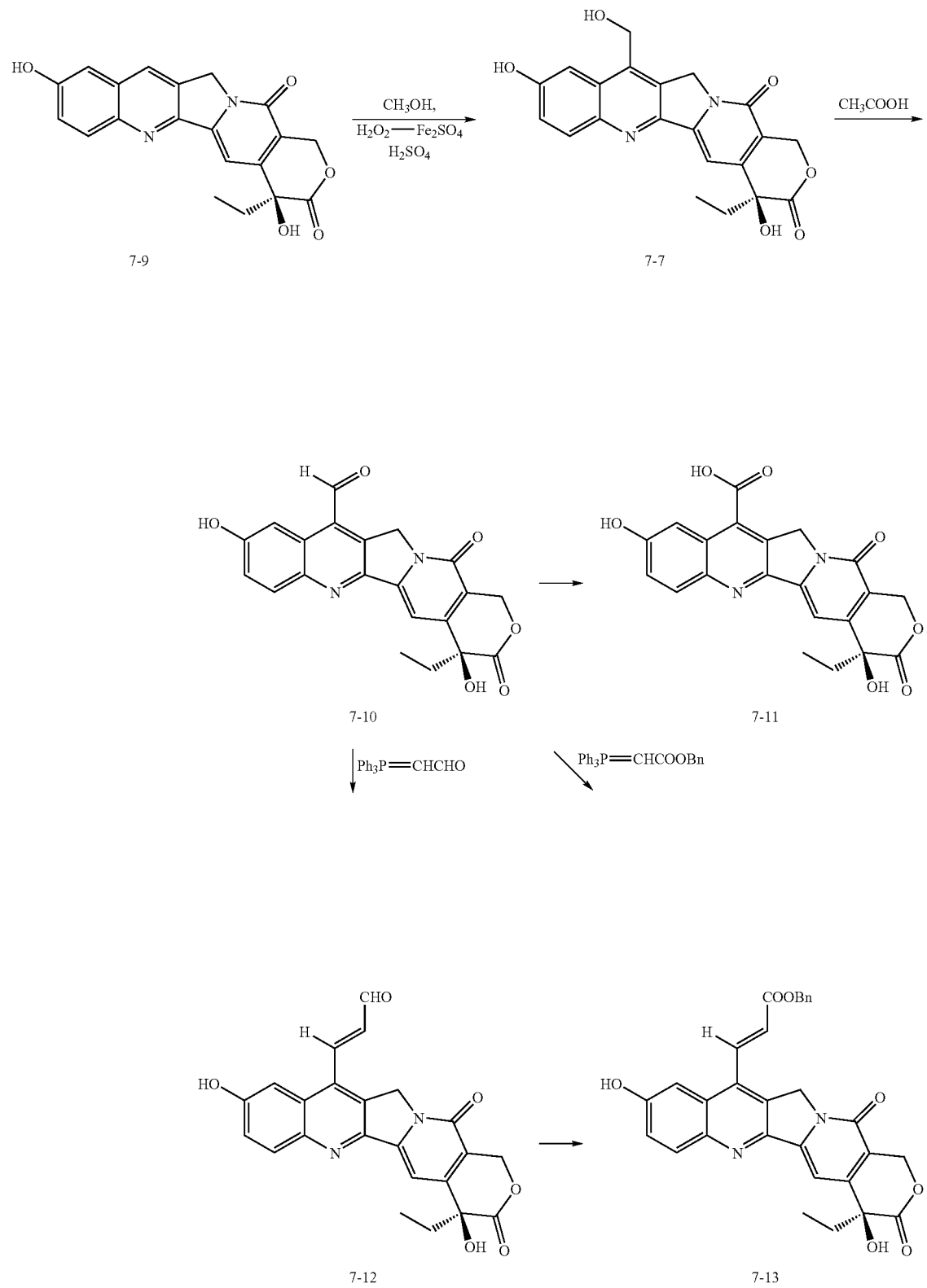

349

A key intermediate is 7-hydroxymethyl-10-hydroxycamptothecin 7-7, which is prepared according to Dallavele, S. et al. (*J. Med. Chem.* 2000, 43, 3963-3969). 7-Aldehyde derivative 7-10 is prepared by refluxing 7-7 in glacial acetic acid. Further oxidation of 7-10 gives acid 7-11. Treating 7-10 with triphenylphosphoranylidene acetaldehyde, and t-butoxycarbonylmethylene triphenylphosphorane gives 7-12 and 7-13, respectively. (*J. Med. Chem.* 2000, 43, 3963).

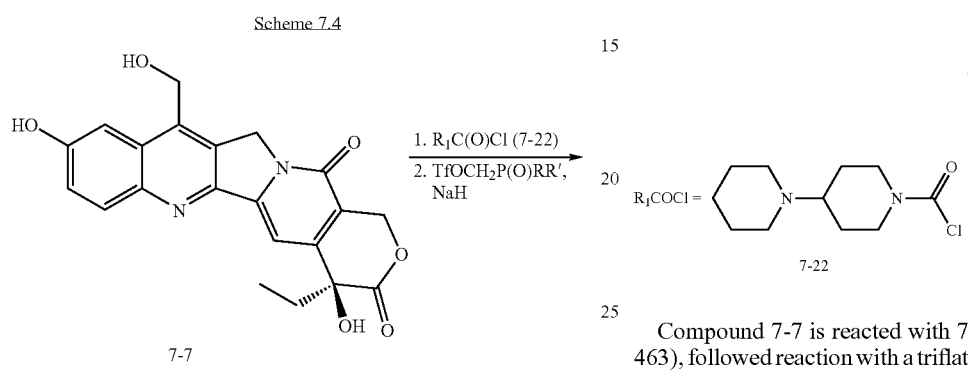

Scheme 7.4

350

-continued

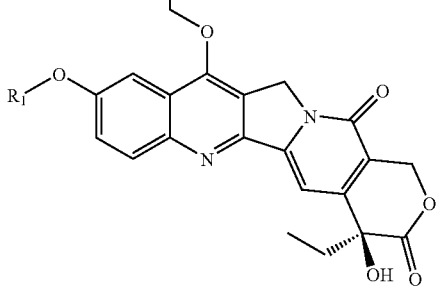

Compound 7-7 is reacted with 7-22 (U.S. Pat. No. 4,604,463), followed reaction with a triflated phosphonate and NaH, to give compound 7-8.

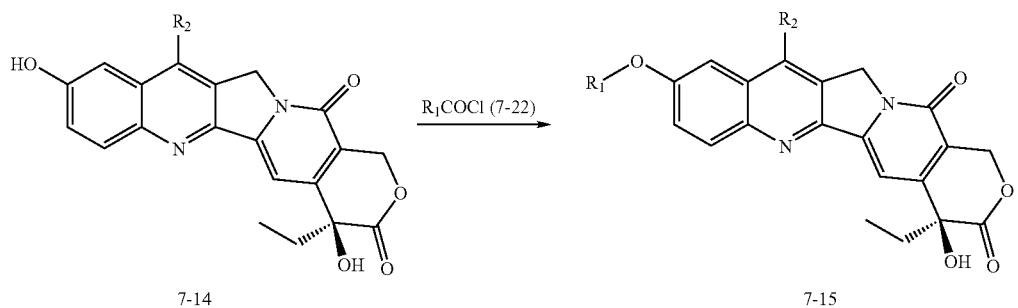

Scheme 7.5

7-10: $R_2 = $ —CHO
7-11: $R_2 = $ —COOH
7-12: $R_2 = $ —CH=CHCHO
7-13: $R_2 = $ —CH=CHCOOBn a: $R_2 = $ —CHO
b: $R_2 = $ —COOH
c: $R_2 = $ —CH=CHCHO
d: $R_2 = $ —CH=CHCOOBn

1. $H_2$, 10% Pd/C
2. $NH_2CH_2CH_2P(O)RR'$
   BOP reagent

1. $NH_2CH_2CH_2P(O)RR'$
   $NaBH_3CN$, HOAc
2. $H_2$, 10% Pd/C $NH_2CH_2CH_2P(O)RR'$
BOP reagent $NH_2CH_2CH_2P(O)RR'$
$NaBH_3CN$, HOAc -continued

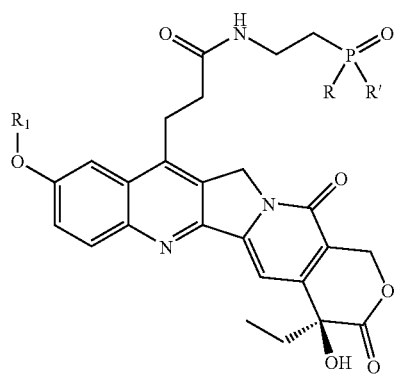

7-16
(from 7-15d)

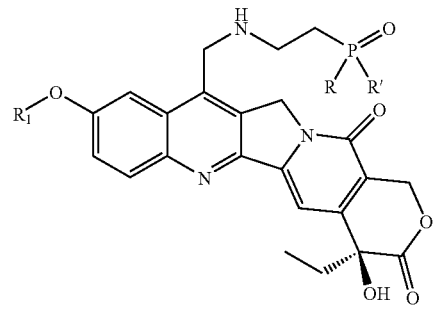

7-19
(from 7-15a)

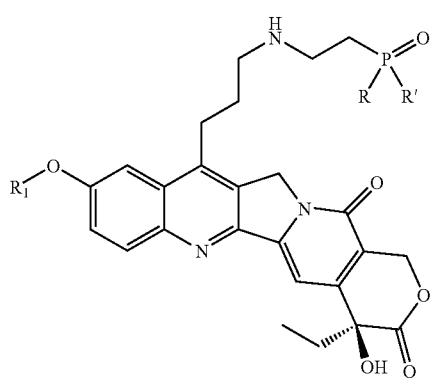

7-17
(from 7-15c)

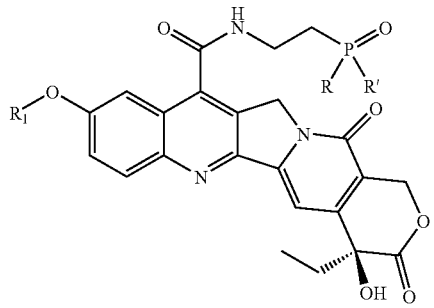

7-18
(from 7-15b)

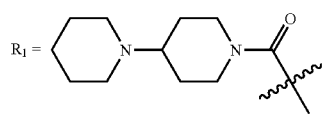

7-23

Syntheses of 7-19, 7-18, 7-17, and 7-16 are illustrated in Scheme 7.5. Aldehyde 7-10, acid 7-11, extended aldehyde 7-12, and ester 7-13 (compounds 7-14) are reacted with 7-22 to furnish 7-15a, 7-15b, 7-15c, and 7-15d. Compound 7-19 is prepared by reductive amination of 7-15a with aminoethylphosphonate, NaBH$_3$CN, and AcOH. Compound 7-15b is activated with BOP reagent, then reacts with aminoethylphosphonate to give compound 7-18. Reductive amination of 7-15c with aminoethylphosphonate, followed by hydrogenation in the presence of 10% Pd/C furnishes desired 7-17. Hydrogenation of 7-15d, followed by treating with aminoethylphosphonate in the presence of coupling agent e.g, BOP reagent. DIC give the desired product 7-16.

Further manipulations can be performed on the phosphonate moiety prior to the final deprotection. These types of transformations are more extensively described in the phosphonate interconversion section herein.

Example 8

Preparation of Exemplary Compounds of the Present Invention

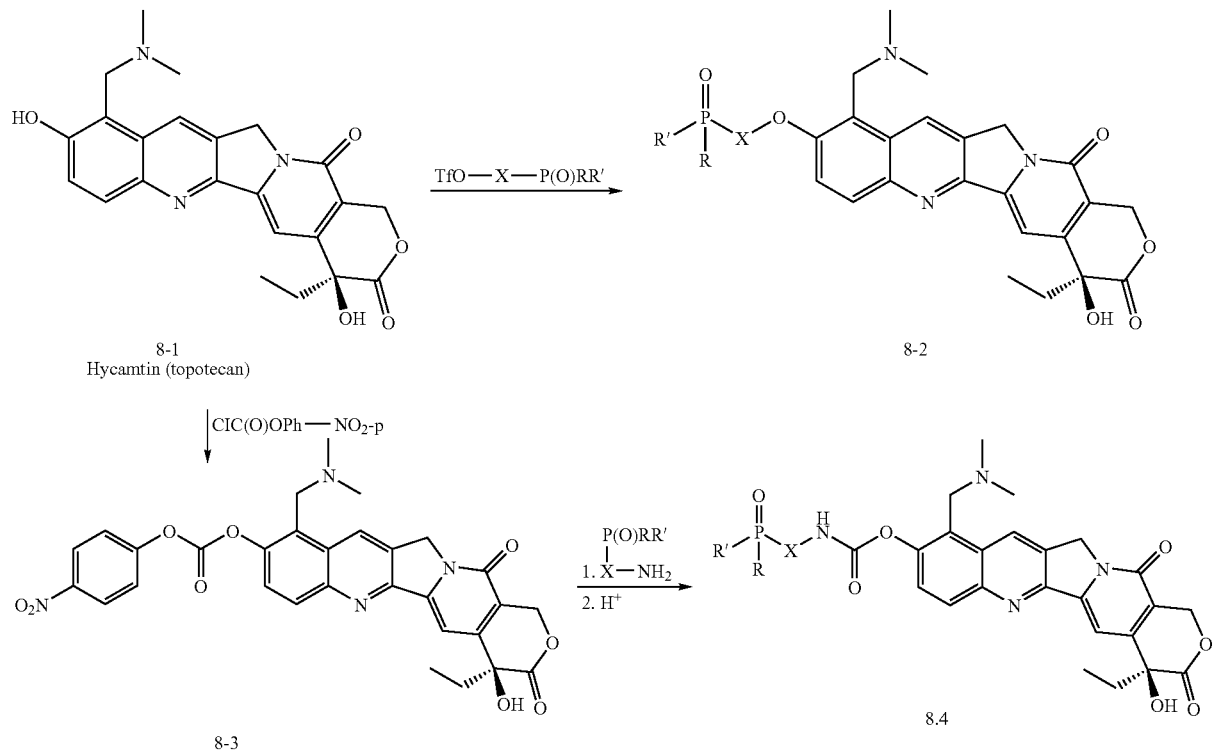

Scheme 8.1

Derivatives of hycamtin at C-10 and O-20 are readily prepared from hycamtin (topotecan) (U.S. Pat. No. 5,004,758), as illustrated in Schemes 8.1-8.5. Hycamtin is reacted with appropriate triflated phosphonate to yield analogs of 8-2. Activation of hycamtin with p-nitrophenyl chloroformate, followed by reaction with appropriate aminophosphonate nucleophile furnishes the desired analog 8-4 containing a carbamate linkage.

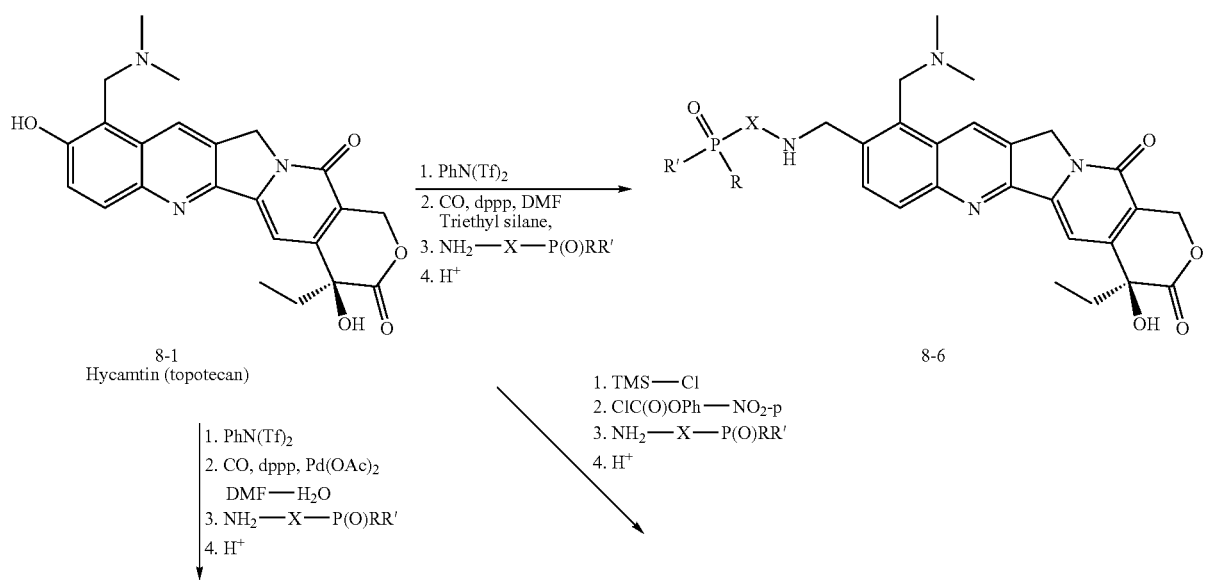

Scheme 8.2

-continued

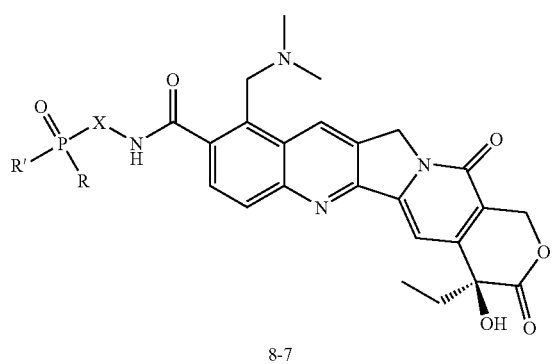
8-7

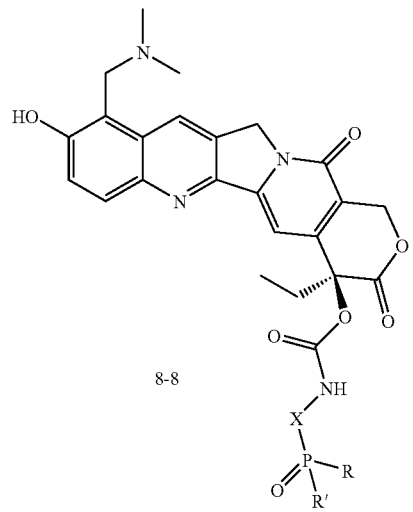
8-8

Conversion of OH group at C-10 to Triflate derivative, followed by CO insertion, and then reaction with aminophosphonate to give analog 8-7. The triflate is converted to an aldehyde by CO insertion, followed by reductive amination with aminophosphonate to give analogs of 8-6. Protection of OH at C-10 and activation of OH-20, followed by reaction with an aminophosphonate furnishes the desired analogs of 8-8.

Scheme 8.3

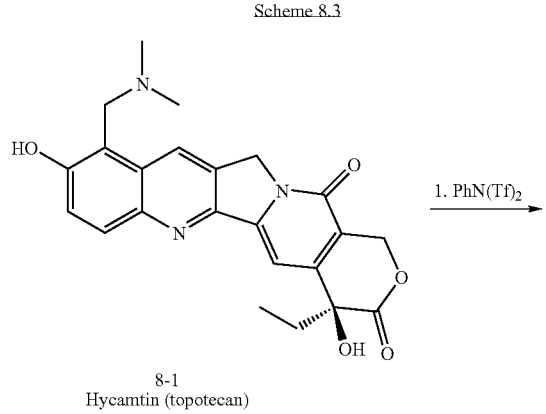
8-1
Hycamtin (topotecan)

1. PhN(Tf)$_2$

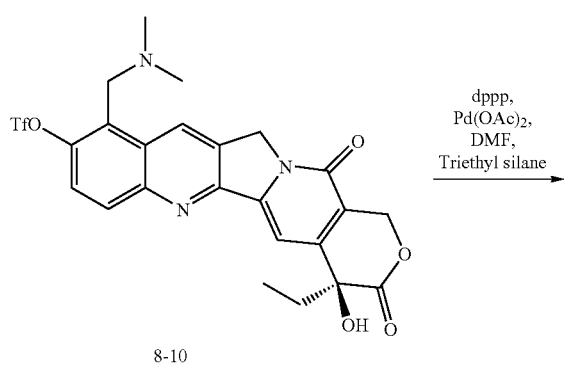
8-10 dppp, Pd(OAc)$_2$, DMF, Triethyl silane

-continued

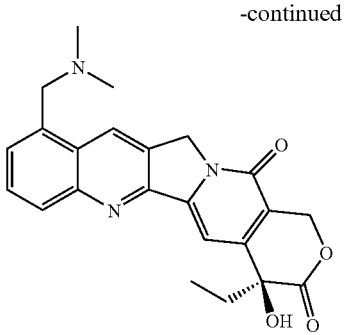
8-11

1. ClC(O)OPh—NO$_2$-p
2. NH$_2$—X—P(O)RR'
3. H$^+$

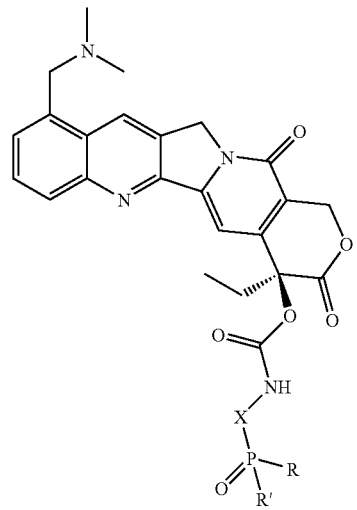
8-12

Scheme 8.4

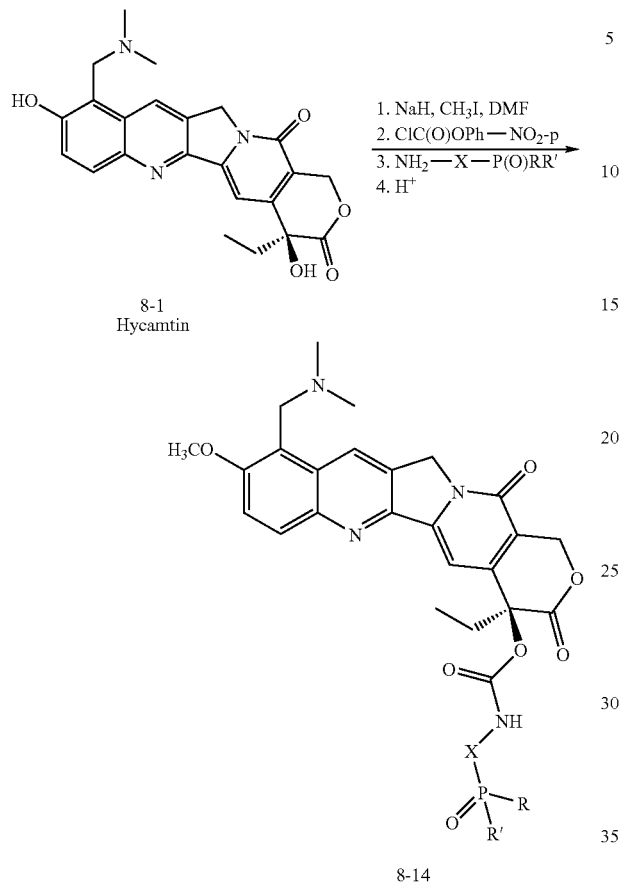

Scheme 8.5

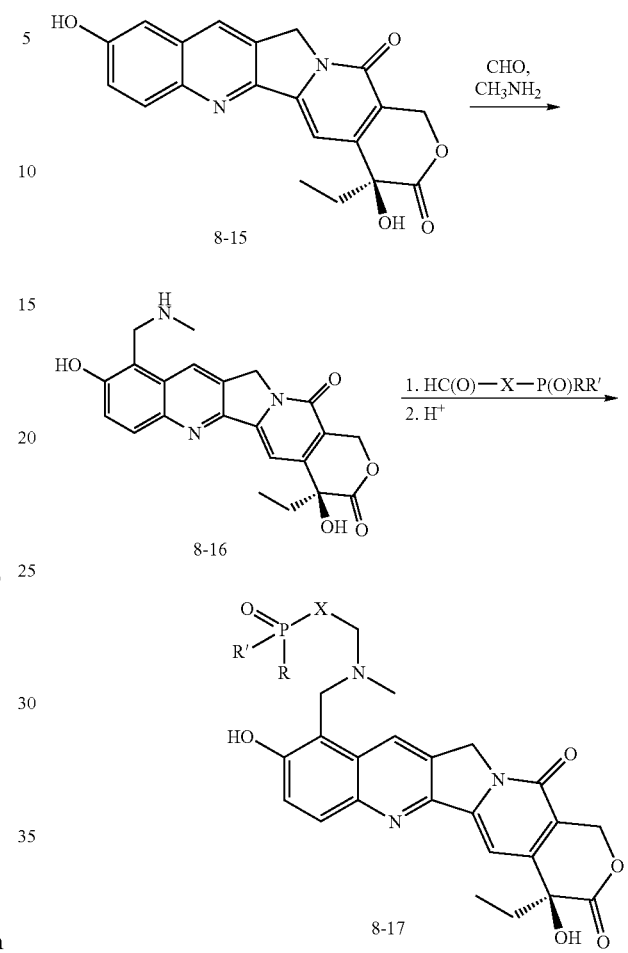

Analogs 8-12 are synthesized from Pd-catalyzed reduction of triflated 8-10, followed by activation of O-20 with p-nitrophenyl chloroformate, and reaction with an aminophosphonate. Methylation of hycamtin by treating hycamtin with NaH, CH₃I in DMF affords 10-OCH₃ hycamtin. Analogs 8-14 are furnished from OCH₃ hycamtin derivative in the same manner as 8-12.

Preparation of analogs 8-17 is performed by reaction of 10-hydroxycamprtothecin with paraformaldehyde, methylamine and acetic acid, followed by reductive amination with an aldehyde-phosphonate.

Scheme 8.6

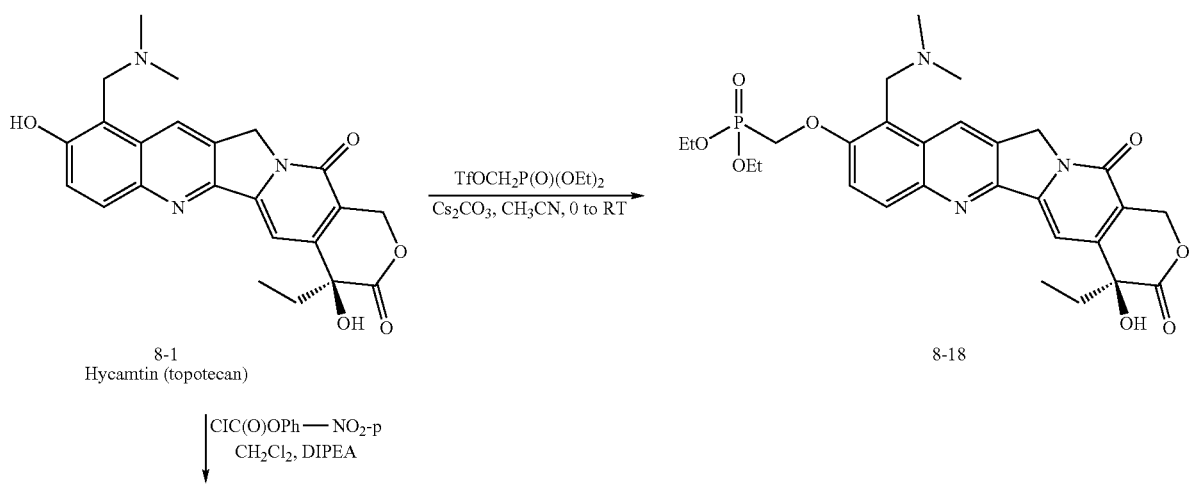

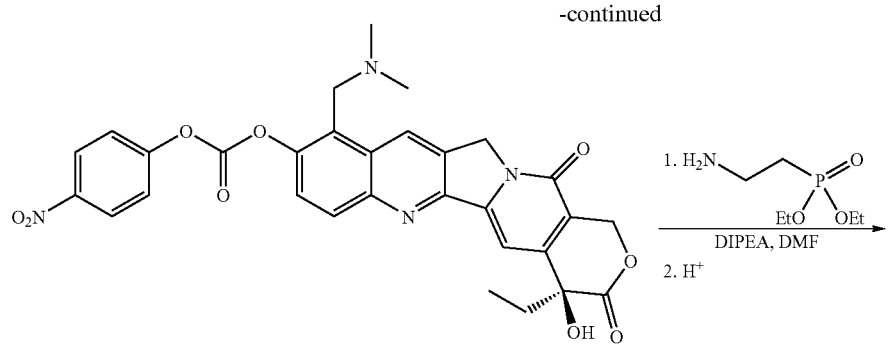
8-19
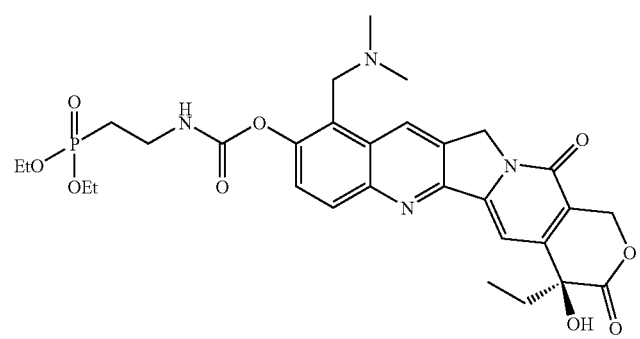
8-20
As depicted in Scheme 8.6, hycamtin is reacted with diethylphosphonate in the presence of $Cs_2CO_3$ in acetonitrile to afford compound 8-18. Activation of OH-10 by reaction with p-nitrophenyl chloroformate in $CH_2Cl_2$ in the presence of DIPEA, followed by reaction aminophonate furnishes carbamate 8-20.
Scheme 8.7
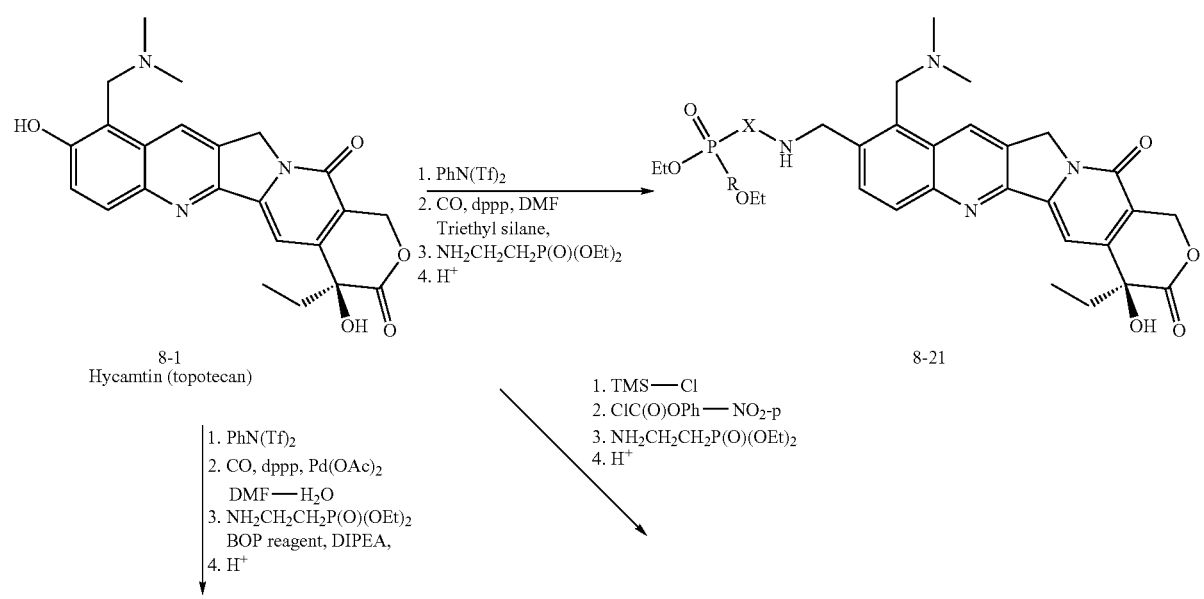

-continued

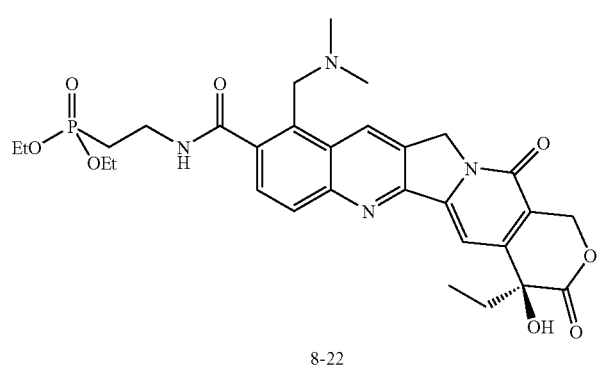
8-22

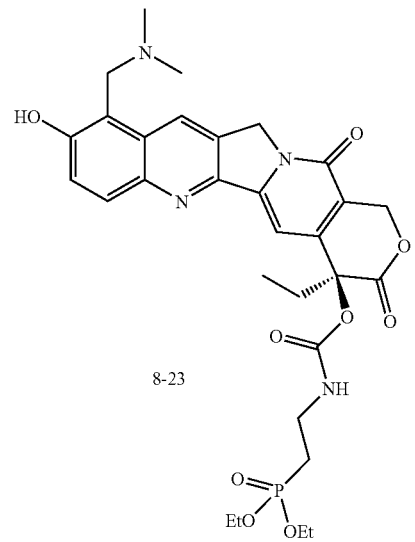
8-23

As shown in Scheme 8.7, tirflation of the 10-OH of hycamtin (*J. Am. Chem. Soc.*, 1984, 106, 7500), followed by CO insertion gives the aldehyde intermediate. (*J. Org. Chem.* 1999, 64, 178). Reductive amination of aldehyde with aminophosphonate, followed by acid treatment, produces amine 8-21. Triflation and CO insertion of hycamtin gives the carboxylic acid, (*J. Org. Chem.* 1994, 59, 6683). The resulting carboxylic acid is activated with BOP-reagent, followed by reaction with aminophosphonate in the presence of DIPEA to produce compound 8-22. Protection of the 10-OH with TMS-Cl, activation of the 20-OH with p-nitrophenyl chloroformate, followed by reaction with an aminophosphonate furnishes phosphonate 8-23.

Scheme 8.8

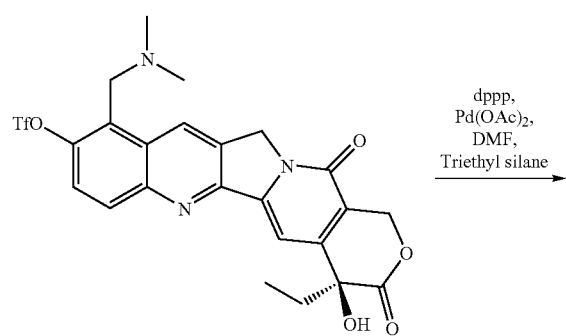

-continued 8-24

Syntheses of 8-24 and 8-25 (see 8-12 and 8-14) are described in Schemes 8.8 and 8.9. Dehyroxylation of 8-10 is performed in DMF with dppp, Pd(OAc)$_2$, and Et$_3$SiH to yield 8-11. Compound 8-24 is prepared from 8-11 by activation with p-nitrophenyl chloroformate, followed by coupling with aminophosphonate and acid work up.

Scheme 8.9

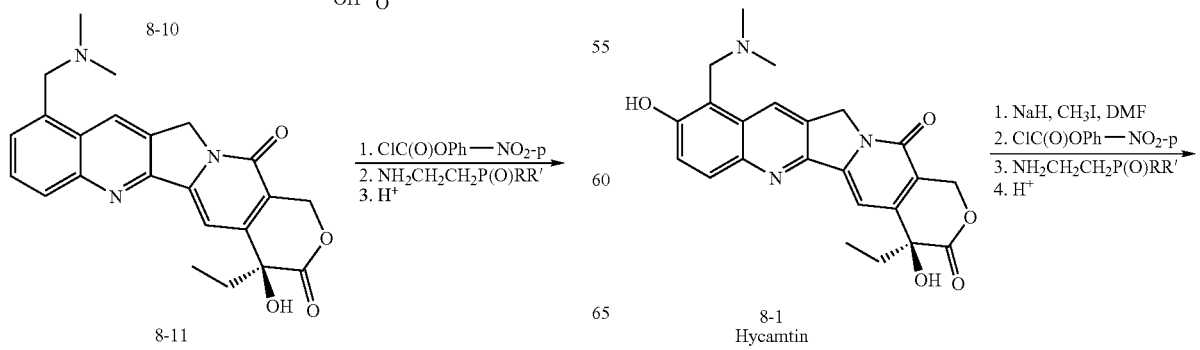

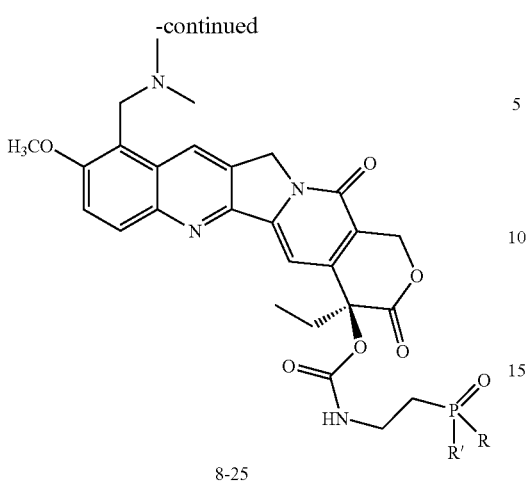

8-25

Hycamtin is treated with NaH in DMF, and reacts with CH$_3$I to give 10-methoxy derivative (Scheme 8.9). This 10-methoxy intermediate is activated with p-nitrophenyl chloroformate, followed by reaction with aminophosphonate and acid work up to furnish desired phosphonate 8-25.

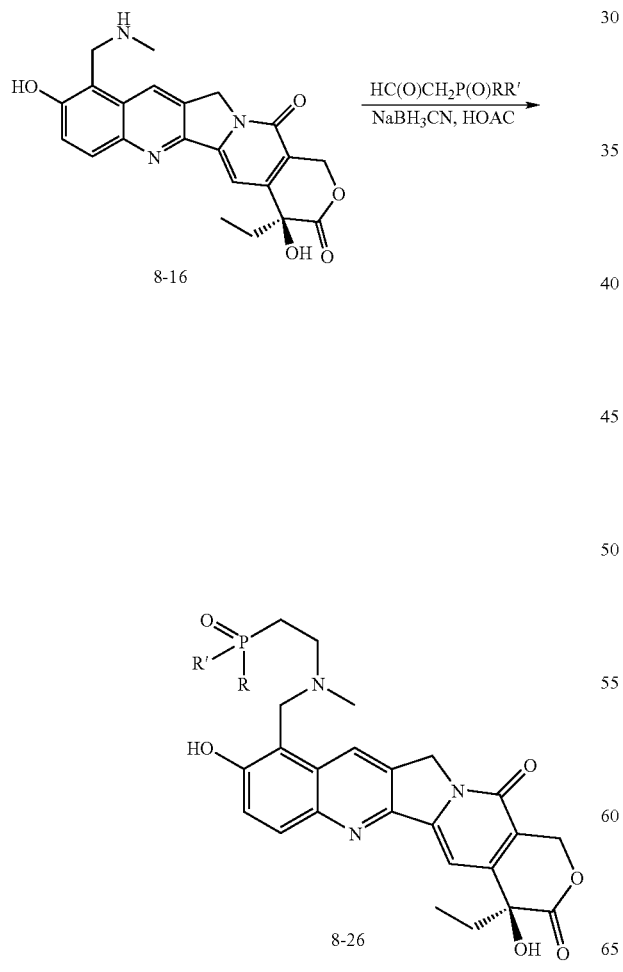

Scheme 8.10 describes the synthesis of compound 8-26 (an example of analogs 8-17), reductive amination of 9-methylaminomethyl-10-hydroxycamptothecin 8-16 (prepared as hycamtin described in U.S. Pat. No. 5,004,758, using methylamine instead of dimethylamine) with phosphonate with aldehyde functional group gives desired product 8-26. Further manipulations can be performed on the phosphonate moiety prior to the final deprotection. These types of transformations are more extensively described in the phosphonate interconversion section herein.

Example 9

Preparation of Exemplary Compounds of the Present Invention

Scheme 9.1

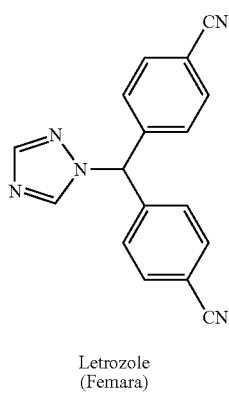

Letrozole
(Femara)

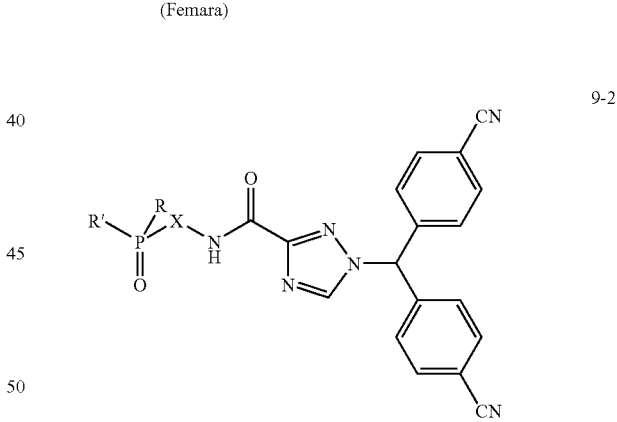

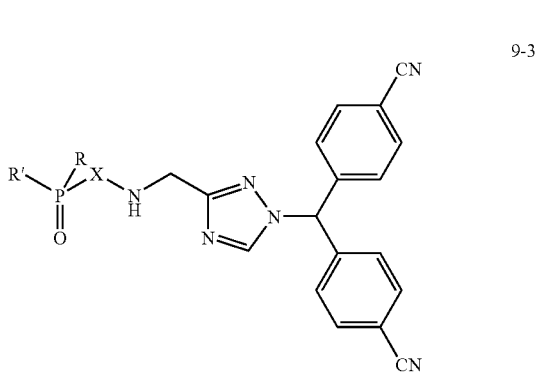

-continued 9-4
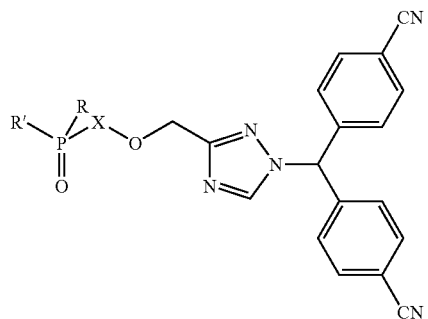

9-5
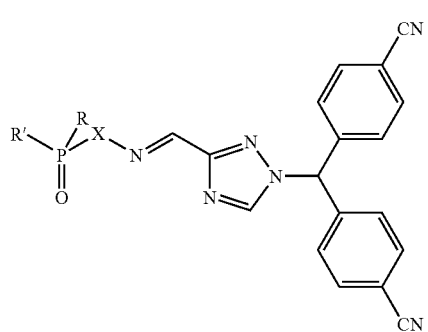

9-6
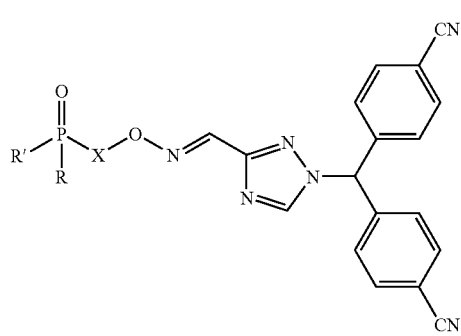

9-7
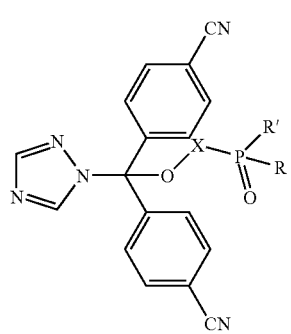

-continued 9-8
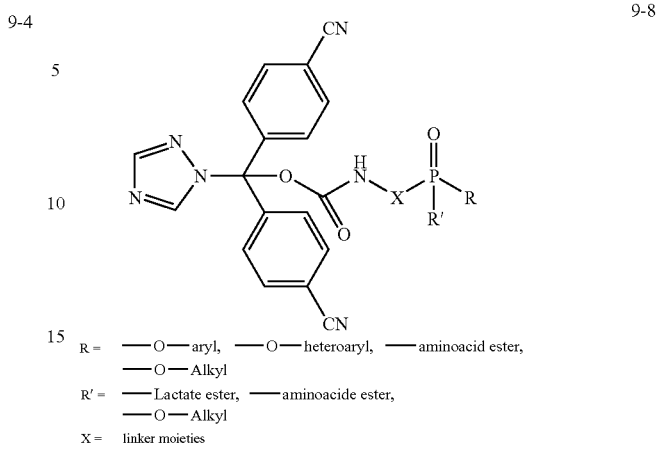

R = —O—aryl, —O—heteroaryl, —aminoacid ester,
   —O—Alkyl
R' = —Lactate ester, —aminoacide ester,
   —O—Alkyl
X = linker moieties Exemplary compounds of the invention are illustrated above.

Scheme 9.2

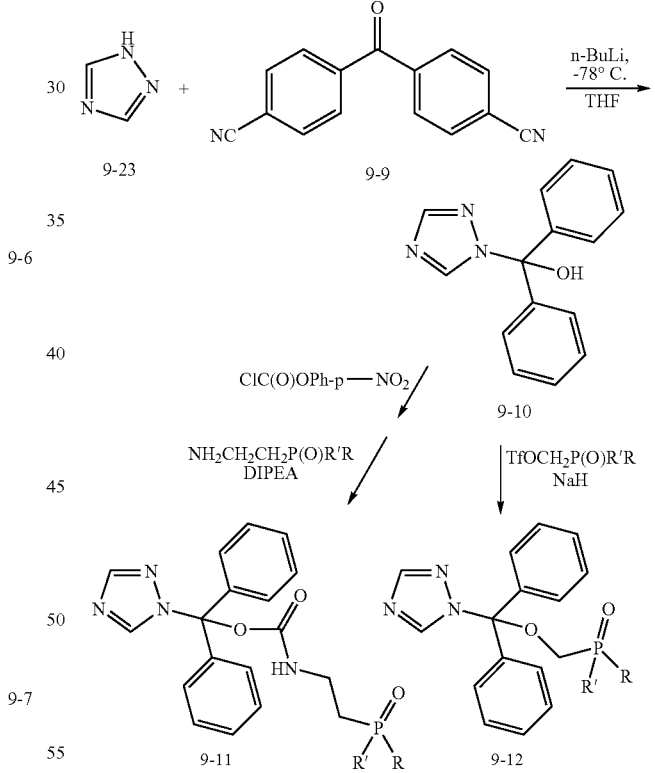

Syntheses of examples of analogs 9-2 to 9-8 are illustrated in Schemes 9.2, 9.3 and 9.4. Reaction of ketone 9-9 (*Chem. Lett.* 1980, 51) and 1,2,4-triazole with n-BuLi in THF at −78° C. gives alcohol 9-10. Compound 9-10 is reacted with triflated phosphonate and NaH, to yield 9-12, an example of 9-7, where X=—$CH_2$—. Compound 9-10 is activated with p-nitrophenyl chloroformate, followed by reaction with aminoethylphosphonate in the presence of diisopropylethylamine (DIPEA) to furnish the desired produce 9-11, an example of analogs 9-8, where X=—$CH_2CH_2$—.

Scheme 9.3
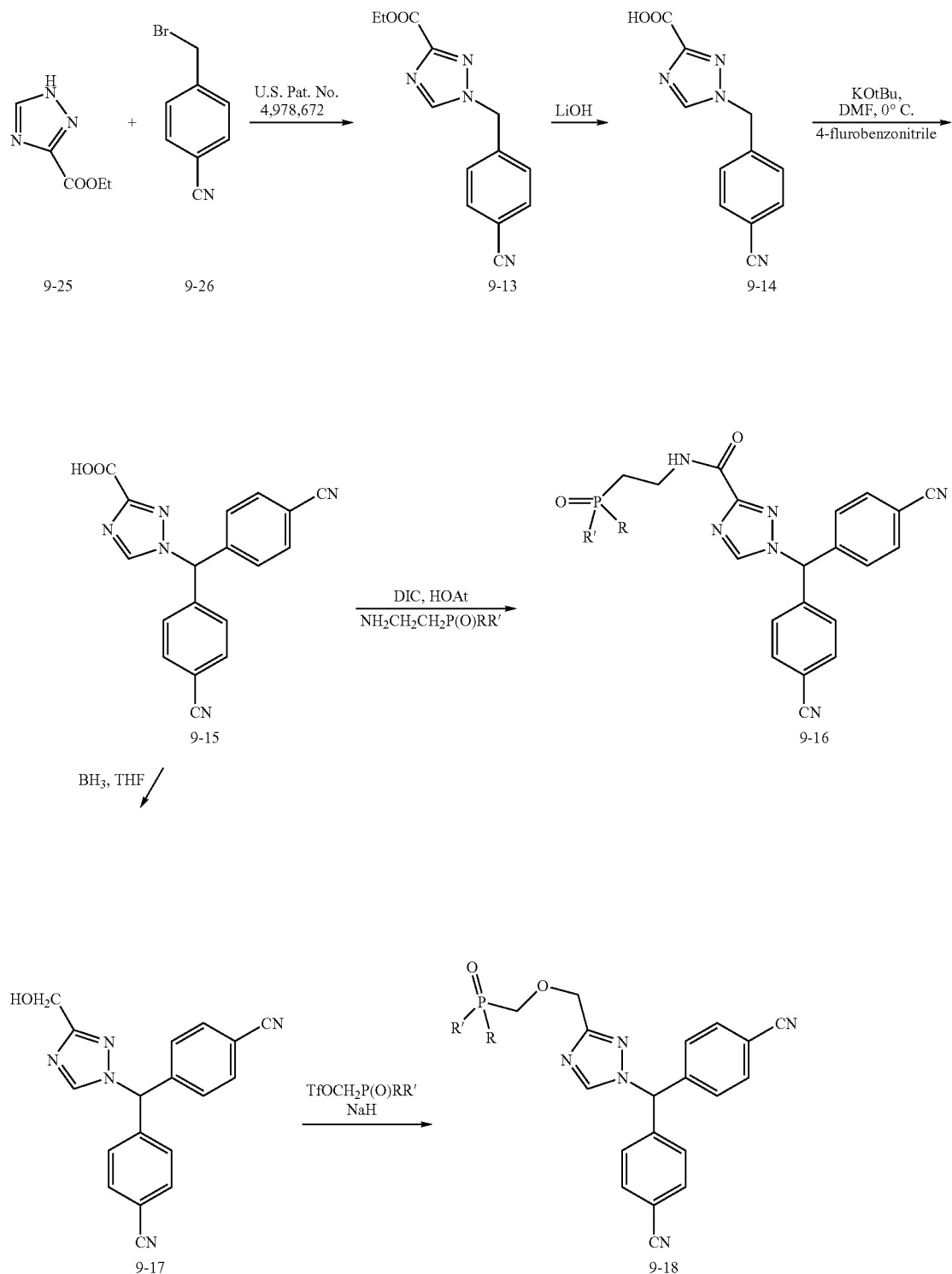

For example, 1,2,4-tetrazole ester derivative is stirred with alpha-bromo-4-tolunirile in CH₂Cl₂ to finish 9-13 (U.S. Pat. No. 4,978,672). Compound 9-13 is first saponified with LiOH to generate acid 9-14. The acid is reacted with 154-fluorbenzonitrile according to procedure described in U.S. Pat. No. 4,978,672 to give the key intermediate 9-15. Reaction of 9-15, DIC, HOAt, and aminoethylphosphonate furnishes 9-16, an example of analogs 9-2, where X=—CH₂CH₂—. Reduction of 9-15 with borane in THF, followed by reacting with triflated phosphonate and NaH gives the desired product 9-18, an example of analogs 9-4, where X=—CH₂CH₂—.

Oxidization of 9-17 with MnO₂ affords aldehyde derivative 9-19. Treatment 9-19 with aminoethylphosphonate generates 9-22, an example of analogs 9-5, where X=—CH₂CH₂—. Aldehyde 9-19 is reacted with hydroxyamine, followed by reacting with triflated phosphonate to furnish 9-21, an example of analogs 9-6, where X=—CH₂CH₂—. Compound 9-20 is obtained by reductive amination of 9-19 with an aminoethylphosphonate, NaBH₃CN, and AcOH.

Further manipulations can be performed on the phosphonate moiety prior to the final deprotection. These types of

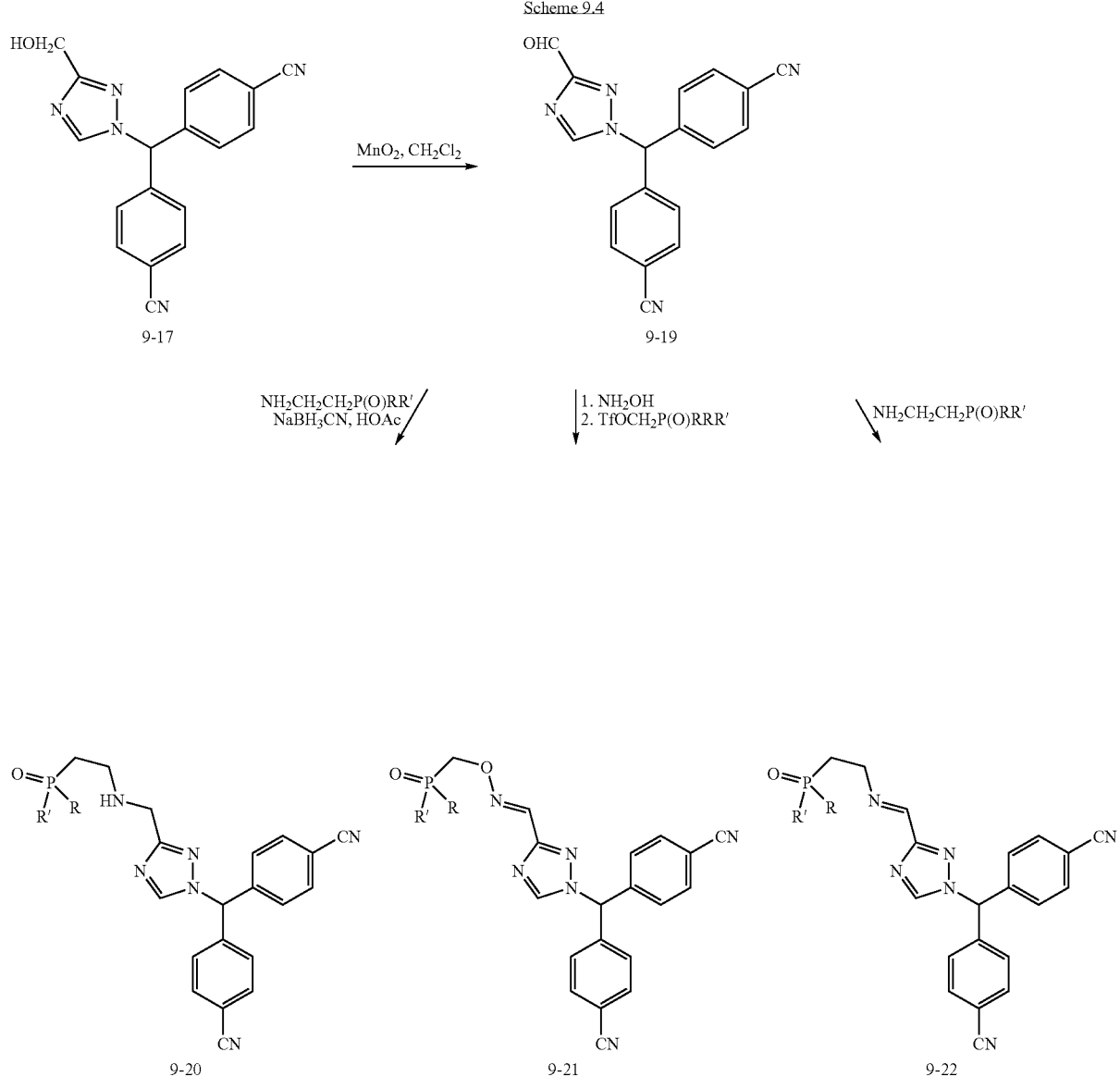

Example 10
Preparation of Exemplary Compounds of the Present Invention
Scheme 10.1
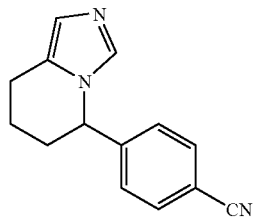
Fadrozole
10-1
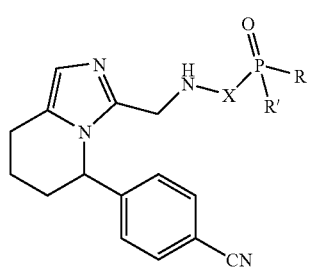
10-2
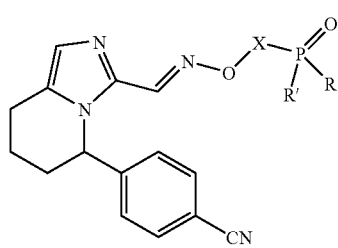
10-3
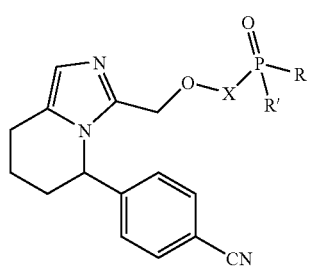
10-4
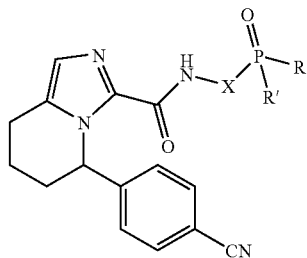
10-5
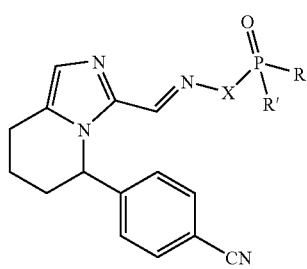
10-6
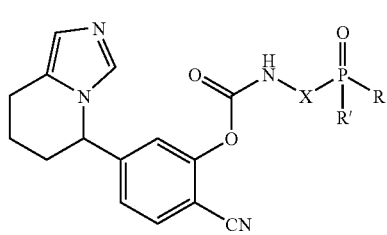
10-7
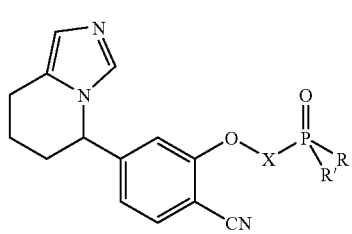
10-8

-continued

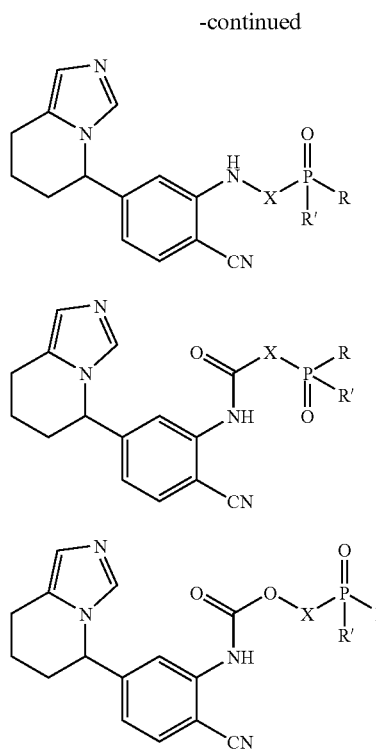

R = —O—aryl, —O—heteroaryl, -aminoacid ester, —O—Alkyl
R' = -Lactate ester, -aminoacid ester, —O—Alkyl
X = linker moieties Exemplary compounds of the invention are illustrated above. Syntheses of new compounds containing phosphonate with various linker X are illustrated in Schemes 10.2, 10.3 and 10.4. Examples are synthesized as depicted in Schemes 10.2, 10.3 and 10.4.

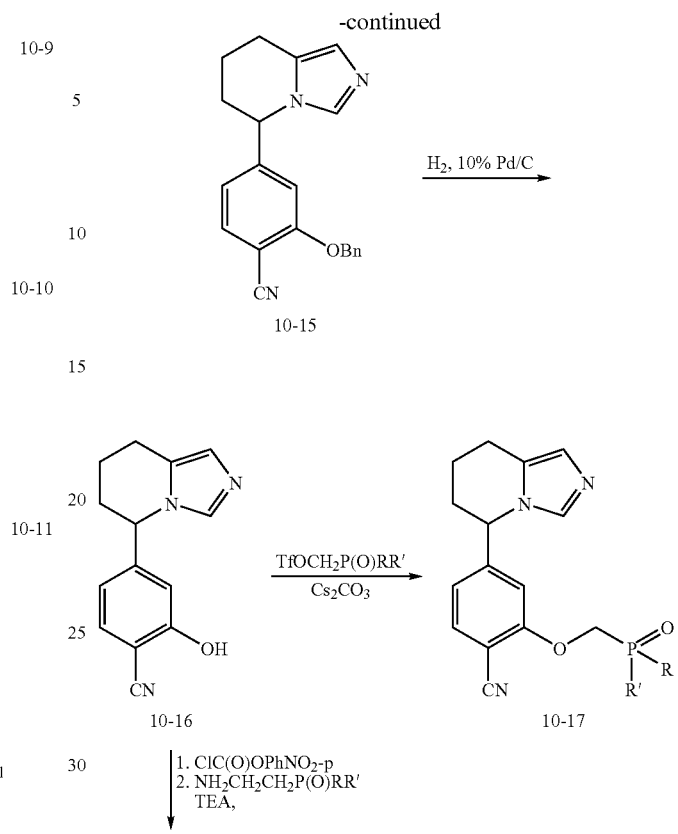

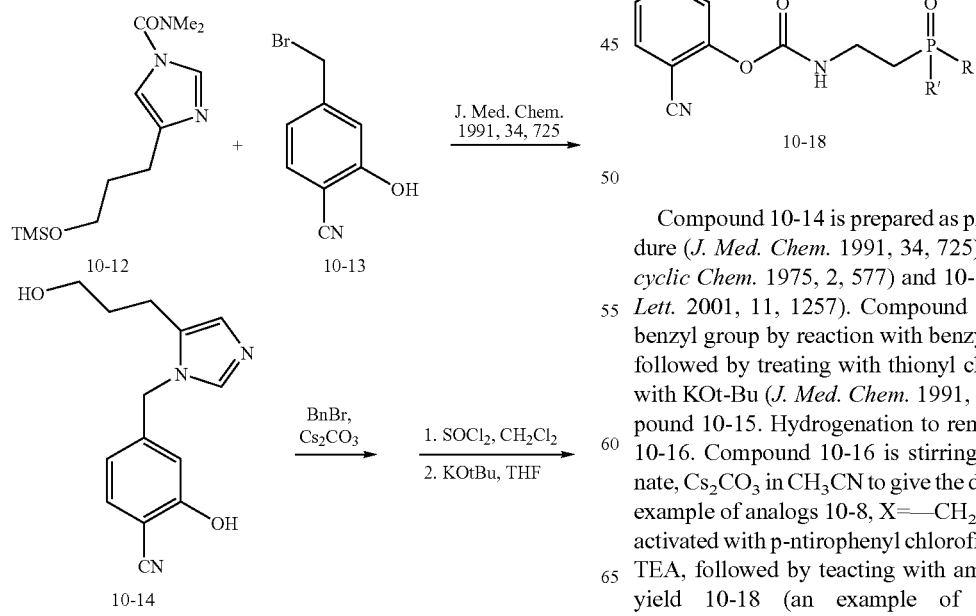

Compound 10-14 is prepared as previous published procedure (*J. Med. Chem.* 1991, 34, 725) from 10-12 (*J. Heterocyclic Chem.* 1975, 2, 577) and 10-13 (*Bioorg. Med. Chem. Lett.* 2001, 11, 1257). Compound 10-14 is protected with benzyl group by reaction with benzyl bromide and $Cs_2CO_3$, followed by treating with thionyl chloride, then cyclization with KOt-Bu (*J. Med. Chem.* 1991, 34, 725) to furnish compound 10-15. Hydrogenation to remove benzyl group gives 10-16. Compound 10-16 is stirring with triflated phosphonate, $Cs_2CO_3$ in $CH_3CN$ to give the desired product 10-17 (an example of analogs 10-8, X=—$CH_2$—). Compound 10-16 is activated with p-ntirophenyl chlorofromate in the presence of TEA, followed by teacting with aminoethylphosphonate to yield 10-18 (an example of analogs 10-7, where X=—$CH_2CH_2$—).

Scheme 10.3

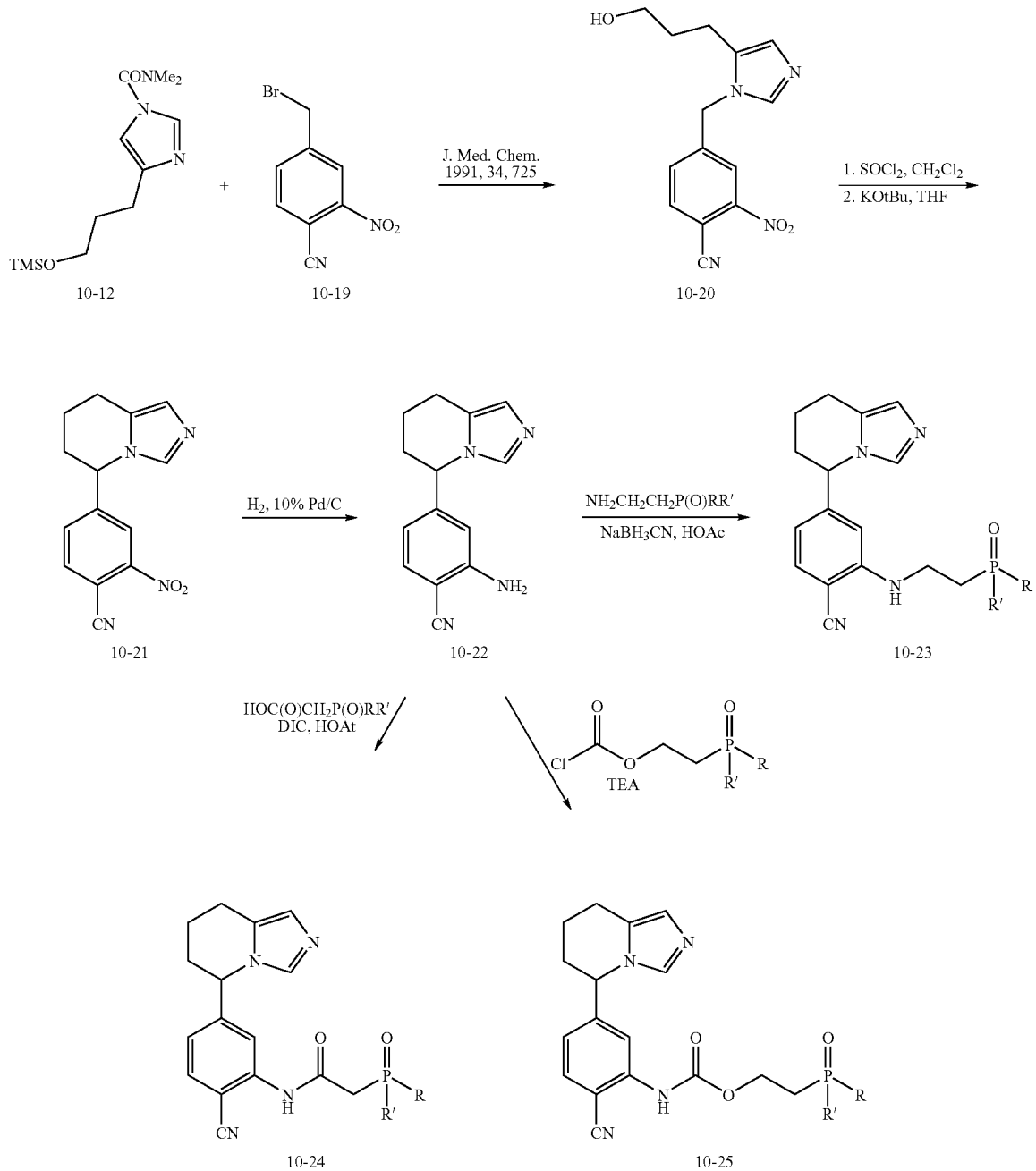

Compound 10-20 is prepared in the same fashion as compound 10-14, from 10-12 and 10-19. Compound 10-21 is synthesized according to the procedure described above for 10-15, followed by hydrogenation in the presence of 10% Pd/C to furnish the key intermediate 10-22. Reductive amination of 10-22 with aldehyde phosphonate, NaBH$_3$CN, and AcOH gives desired product 10-23 (an example of analogs 10-9, where X=—CH$_2$CH$_2$—). Compound 10-22 is reacted with phosphonate chloroformate in the presence of TEA to give product 10-25 (an example of analogs 10-11, where X=—CH$_2$CH$_2$—). Example of analogs $10^{-10}$ (where X=—CH$_2$—), compound of 10-24 is furnished by reaction 10-22 with phosphonate carboxylic acid and DIC. Formylation of fadrozole with n-BuLi, DMF gives intermediate aldehyde 10-26 (J. Med. Chem. 2000, 43, 2165). Further oxidation of 10-26 to give acid, followed by reaction with aminoethylphosphonate, DIC, and HOAt furnishes the desired product 10-31 (an example of analogs 10-5, where X=—CH$_2$CH$_2$—). Reductive amination of 10-26 with aldehyde phosphonate, NaBH$_3$CN, and AcOH give desired product 10-27 (an example of analogs 10-2, where X=—CH$_2$CH$_2$—). Treating 10-26 with aminoethylphosphonate yield 10-30 (an example of analogs 10-6, where X=—CH$_2$CH$_2$—).

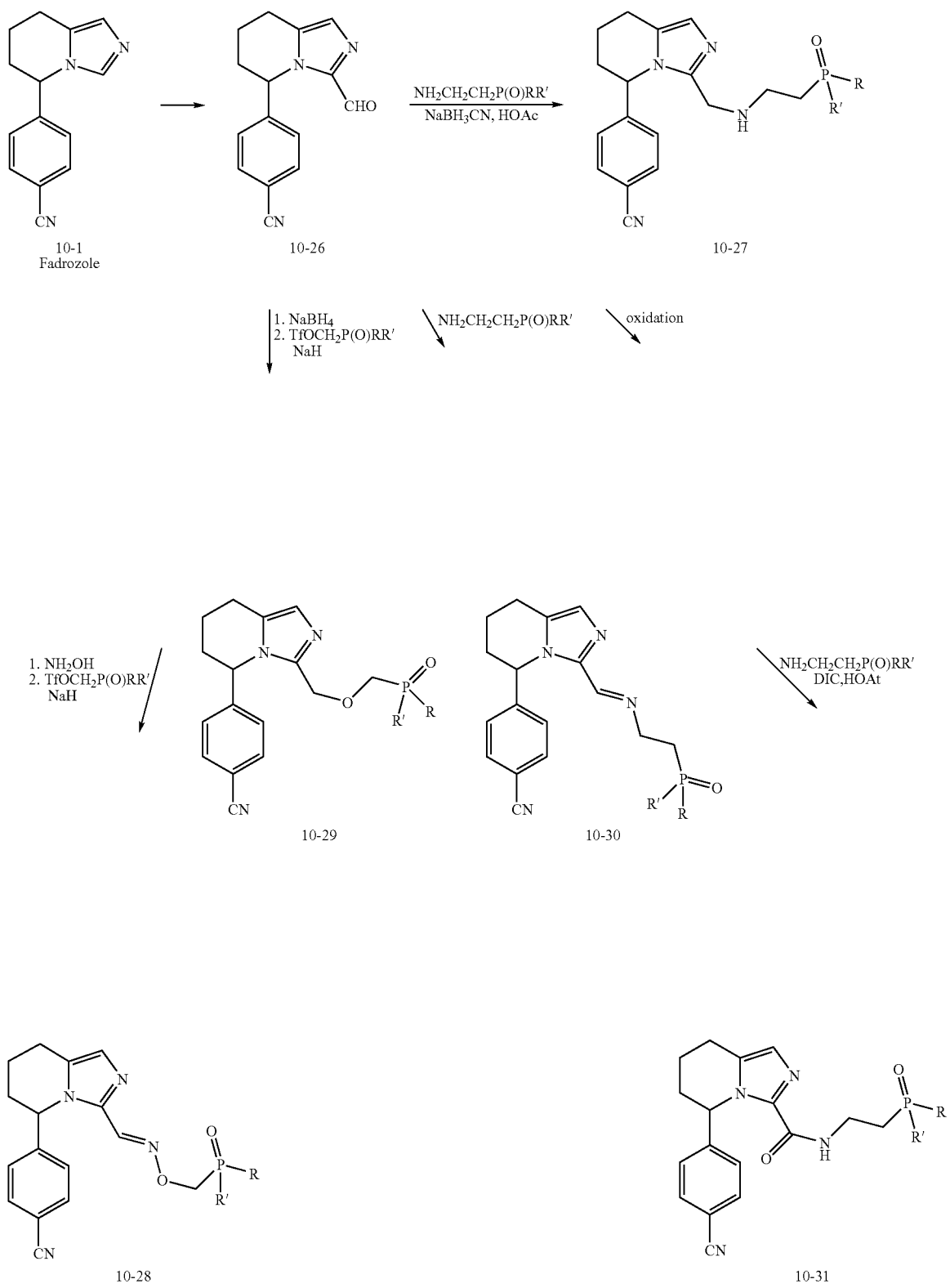

Reduction of 10-26 with NaBH$_4$ generates alcohol derivative, followed by reaction with triflated phosphonate and NaH to provide product 10-29 (an example of analogs 10-4, where X=—CH$_2$—). The condensation between compound 10-26 and hydroxyamine in the presence of TEA to give the oxime. The alkylation of the oxime with a triflated phosphonate and NaH furnishes the desired compound 10-28 (an example of analogs 10-3, where X=—CH$_2$—).

Further manipulations can be performed on the phosphonate moiety prior to the final deprotection. These types of transformations are more extensively described in the phosphonate interconversion section herein.

Example 11

Preparation of Exemplary Compounds of the Present Invention

Scheme 11.1

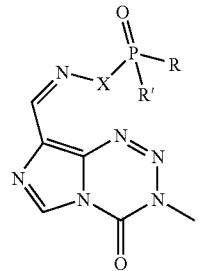

11-1

Temozolomide

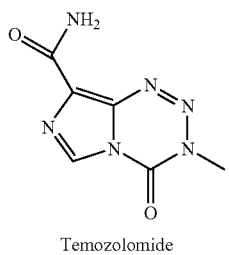

11-2

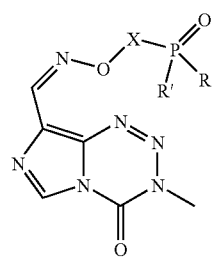

11-3

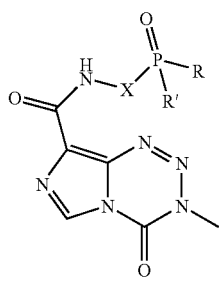

-continued

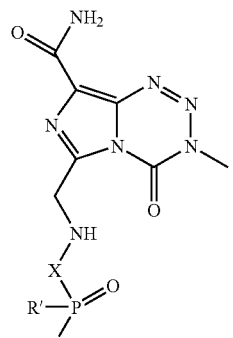

11-4

11-5

11-6

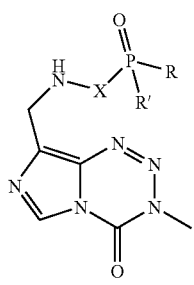

11-7

R = —O—aryl, —O—heteroaryl, -aminoacid ester, —O—Alkyl
R' = -Lactate ester, -aminoacid ester, —O—Alkyl
X = linker moieties Exemplary compounds of the invention are illustrated above.

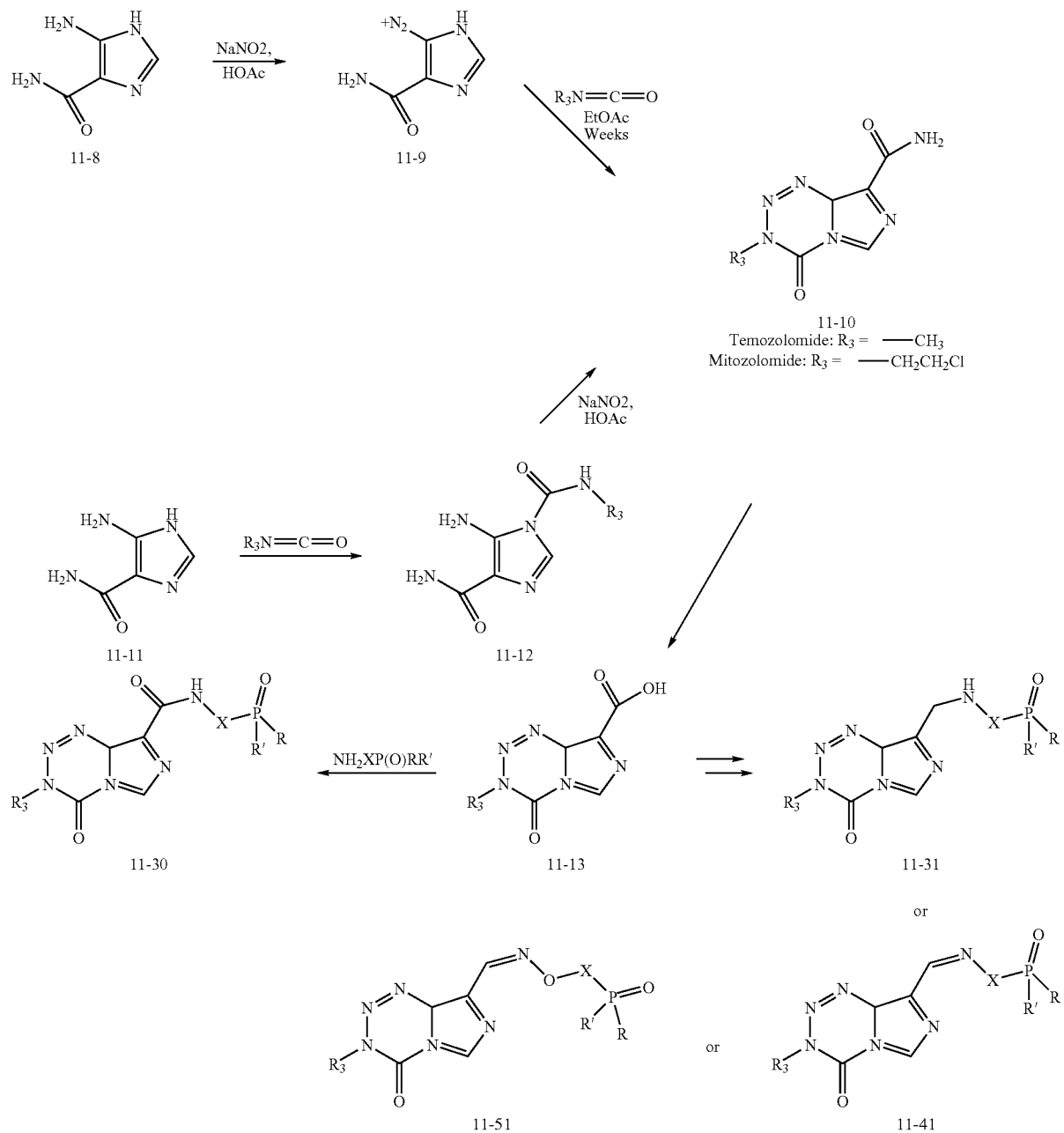

Scheme 11.2

Temozolomide, mitozolomide and their derivatives have been synthesized by several different synthetic routes (Scheme 11.2). 5-Aminoimidazole-4-carbozamide is reacted with alkyl isocyanate to give the 1-(N-alkylcarbamoyl) derivative. This derivative is treated with sodium nitrite to generate 11-10 (J. Org. Chem. 1997, 62, 7288). Alternatively, 5-aminoimidazole-4-carbozamide is treated with sodium nitrite to generate a diazonium salt, followed by the reaction with alkyl isocyanate to furnish amide 11-10 (U.S. Pat. No. 5,260,291). Hydrolysis conditions can be selected to hydrolyzed amide 11-10 to acid 11-13 (J. Med. Chem. 1990, 33, 1393). The acid 11-13 is converted to an aldehyde, followed by reductive amination with an aminophosphonate to furnish analogs 11-31, by the reaction with an aminophosphonate to give analog 11-41, and reaction with hydroxylamine, triflate phosphonate to give 11-51. Compound 11-13 is reacted with an aminophosphonate and a coupling agent to give analogs 11-30. Compounds 11-15, 11-17, 11-18, and 11-19, which are examples of 11-30, 11-51, 11-41, and 11-31, respectively, can be prepared as illustrated below (Scheme 11.3).

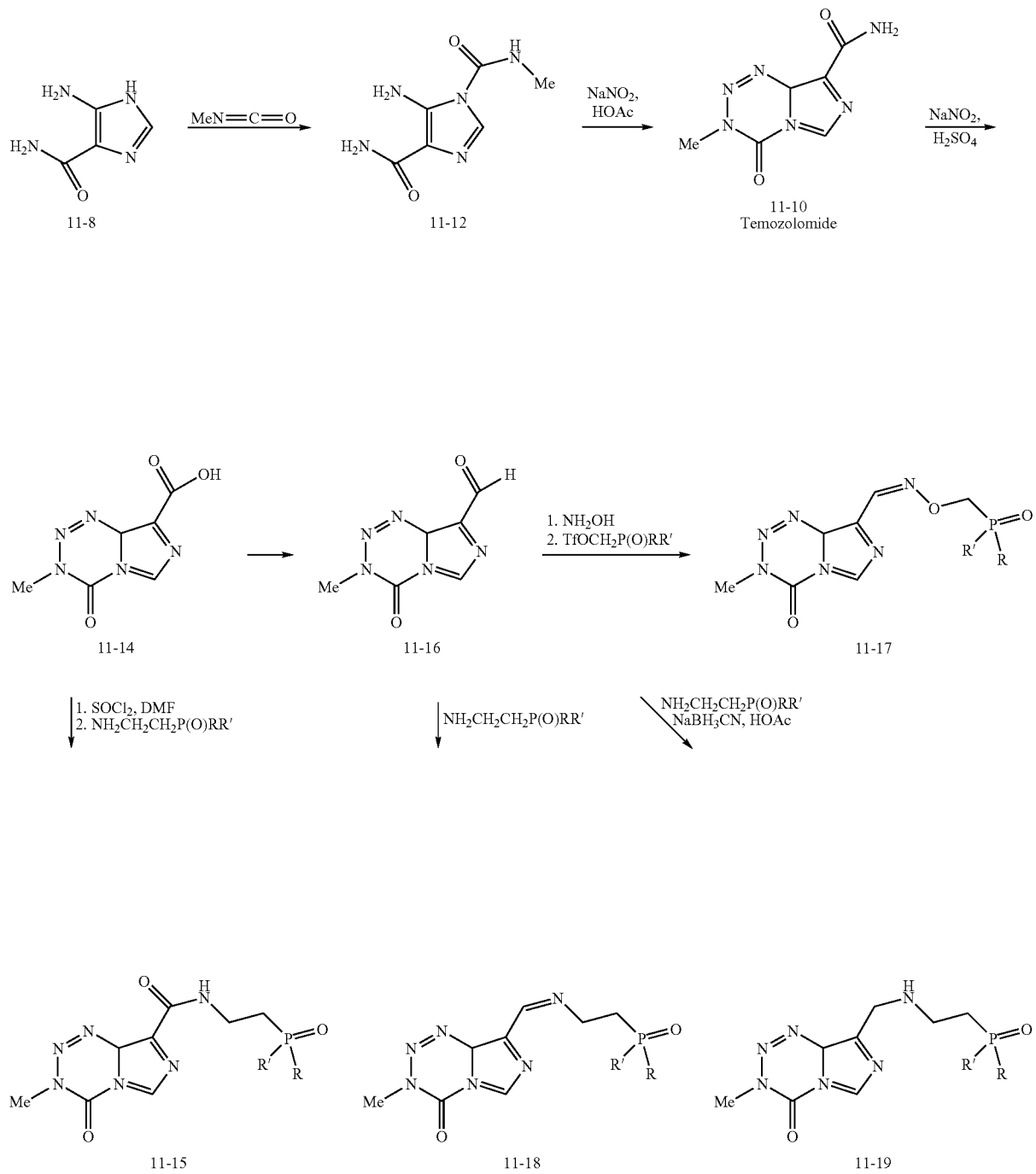

Scheme 11.3

Temozolomide 11-10 is prepared stepwise, from the reaction of 5-aminoimidazole-4-carbozamide with methyl isocyanate in acetonitrile, followed by the nitrosoation with sodium nitrite in 50% acetic acid, and cyclization to give 11-10 (J. Org. Chem. 1997, 63, 7288). Temozolomide is converted to acid 11-14, by the reaction of 11-10 with sodium nitrite in concentrated sulfuric acid. The acid chloride is obtained by treating acid 11-14 with thionyl chloride and a catalytic amount of DMF (J. Med. Chem. 1990, 33, 1393).

The reaction of the acid chloride with an aminoethyl phosphonate affords 11-15. The acid chloride can be reacted with a hydroxymethylamine, followed by reduction with DIBAL in THF to give aldehyde 11-16. The aldehyde is further reacted with aminoethyl phosphonate, and reductively aminated with an aminoethyl phosphonate, $NaBH_3CN$, and AcOH to give 11-18, and 11-19, respectively. Aldehyde 11-16 can be reacted with hydroxylamine hydrochloride in the presence of TEA followed by reaction with a triflated phosphonate and NaH to generate 11-17.

Scheme 11.4

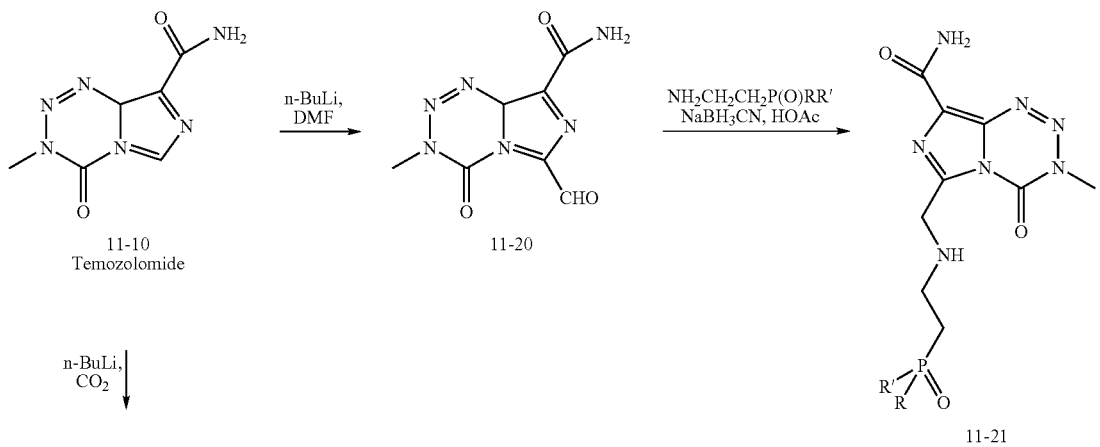

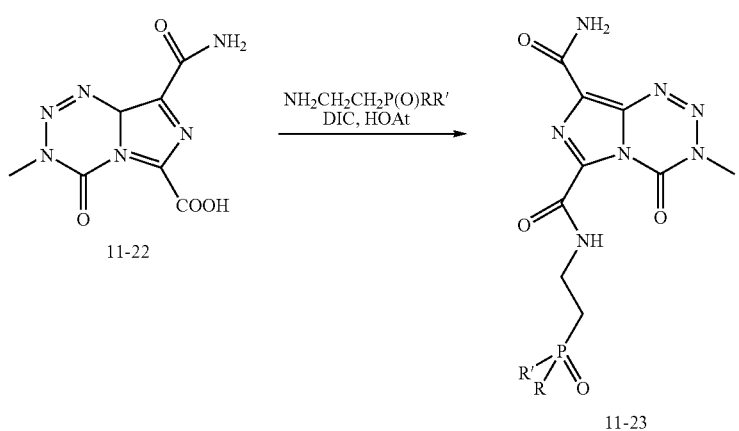

Compound 11-21 and 11-23, which are examples of analogs 11-6 and 11-7, are synthesized as illustrated above in Scheme 11.4. Compound 11-10 is lithiated with n-BuLi in THF at −78° C., followed by reaction with DMF, to give aldehyde derivative 11-20. The reductive amination of aldehyde 11-20 with aninoethylphosphonate, NaBH$_3$CN, AcOH affords the desired product 11-21 (an example of analog of 11-6, where X=—CH$_2$CH$_2$—). Temozolomide 11-10 can also be lithiated with n-BuLi in THF, followed by the reaction with CO$_2$ to afford acid derivative 11-22. Acid 11-22 is reacted with an aninoethyl phosphonate in the presence of coupling agents, e.g., DIC, HOAt, to furnish the desired product 11-23 (an example of analog of 11-7, where X=—CH$_2$CH$_2$—). Further manipulations can be performed on the phosphonate moiety prior to the final deprotection. These types of transformations are more extensively described in the phosphonate interconversion section herein.

Example 12
Preparation of Exemplary Compounds of the Present Invention
Scheme 12.1
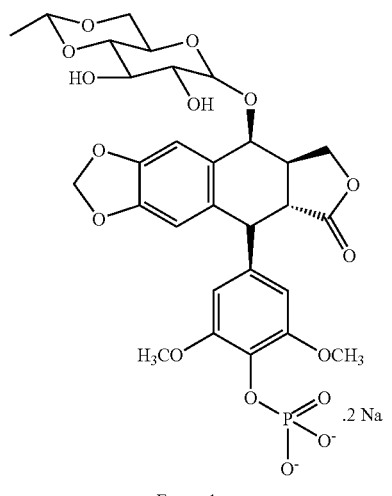
Etopophos
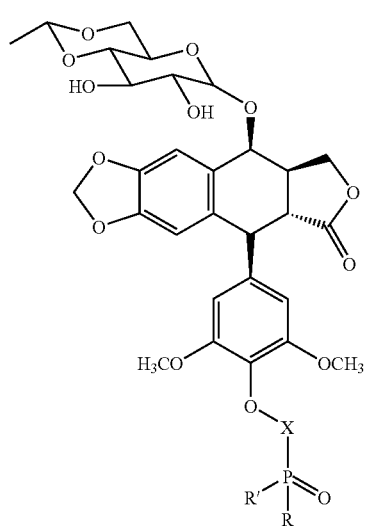
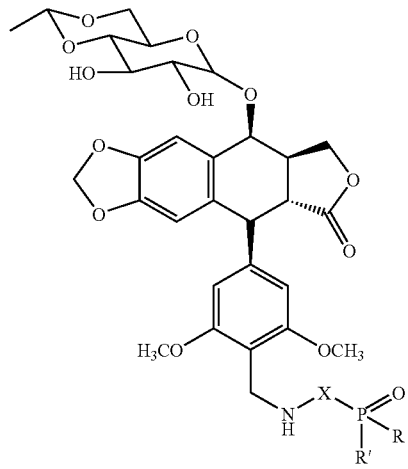
-continued
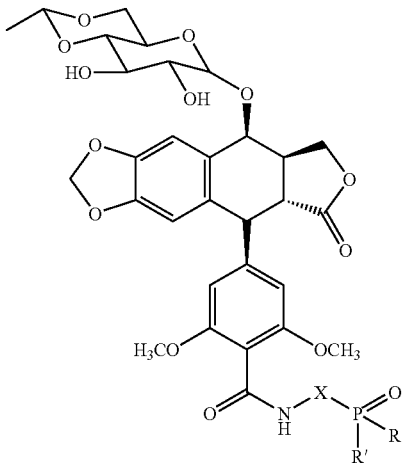
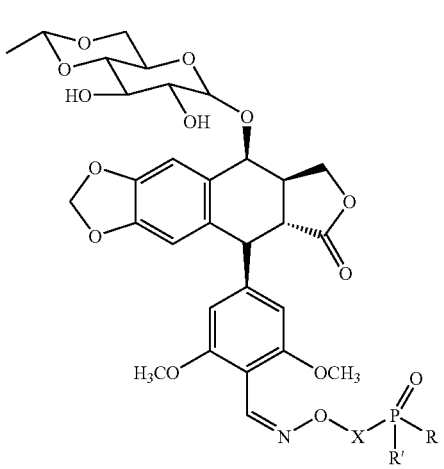
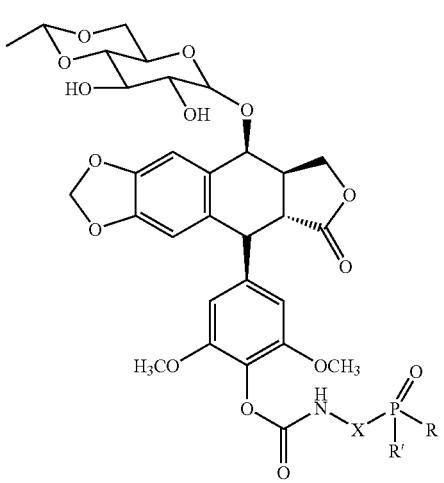

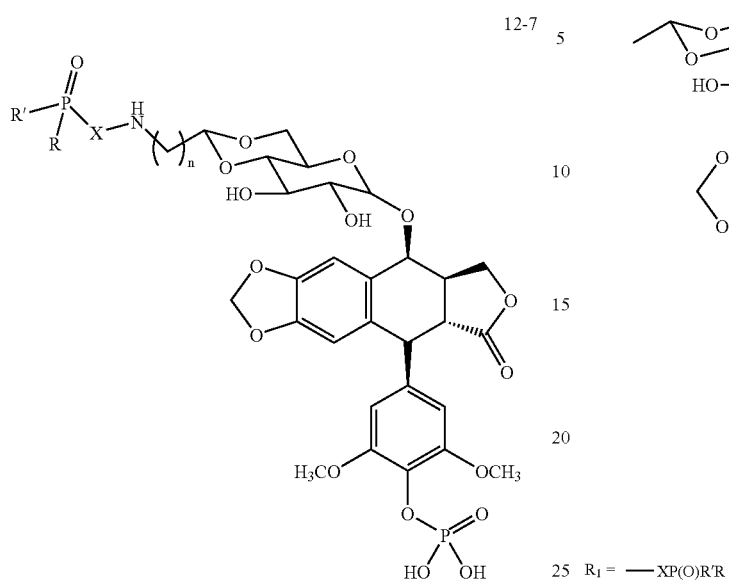
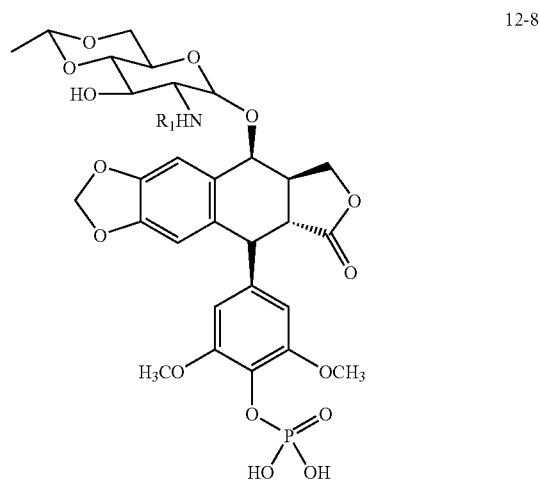
R₁ = —XP(O)R'R
R = —O—aryl, —O—heteroaryl, -aminoacid ester, —O—Alkyl
R' = -Lactate ester, -aminoacid ester, —O—Alkyl
X = linker moieties
Exemplary compounds of the invention are illustrated above.
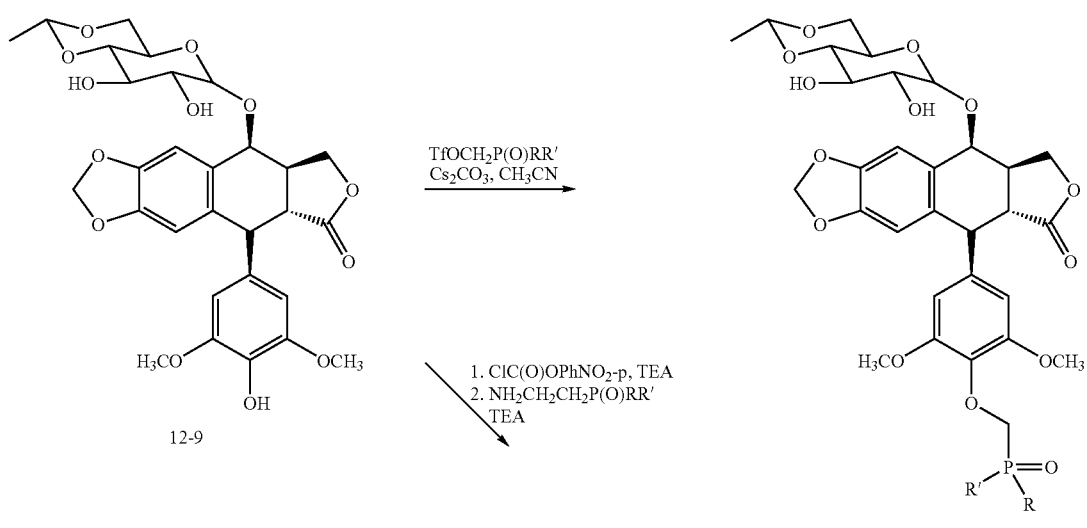

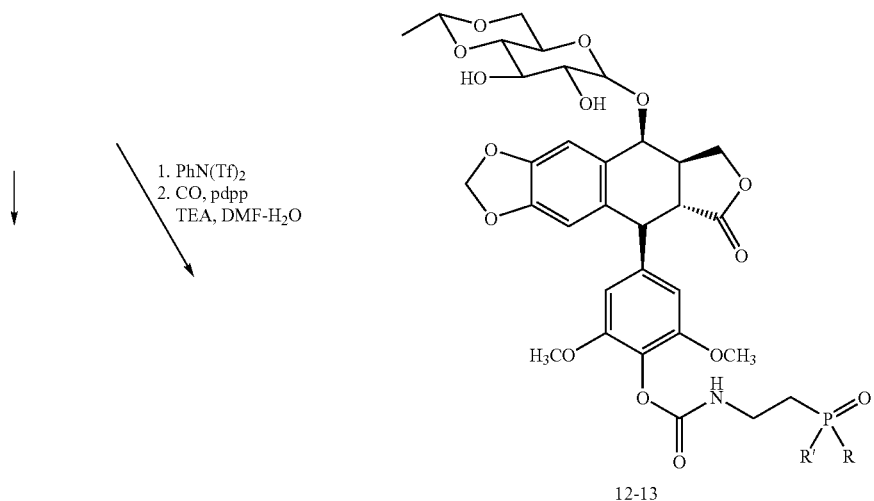
12-13
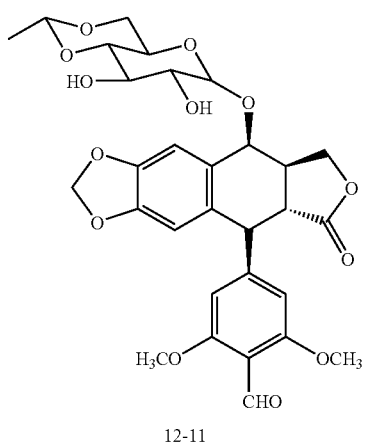
12-11
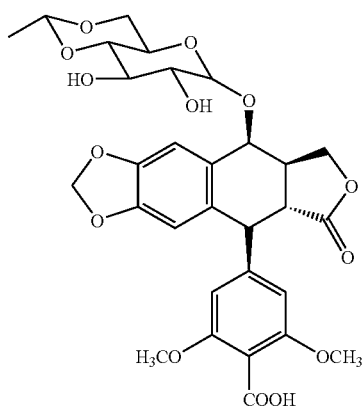
12-12
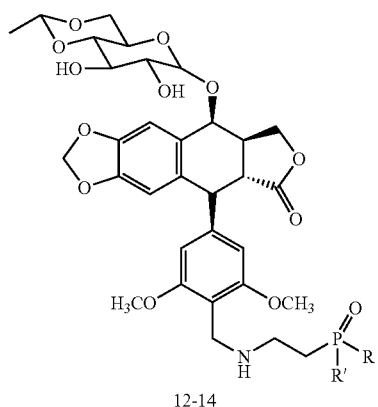
12-14
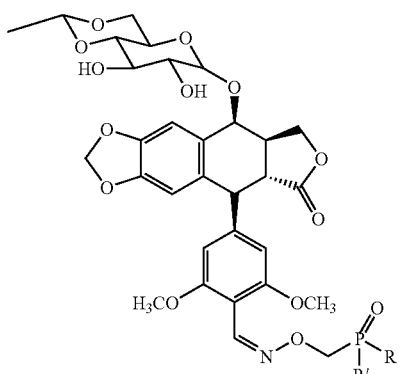
12-15
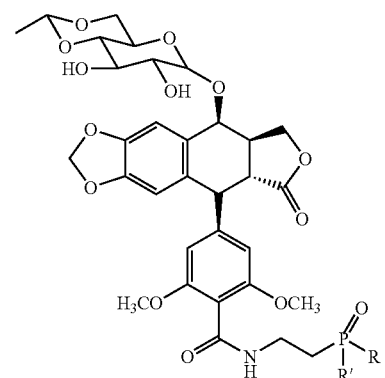
12-16

Syntheses of compounds, 12-10, 12-14, 12-16, 12-15, and 12-13, containing phosphonate moieties, which are examples of analogs 12-2 (X=—CH$_2$—), 12-3 (X=—CH$_2$CH$_2$—), 12-4 (X=—CH$_2$CH$_2$—), 12-5 (X=—CH$_2$—), and 12-6 (X=—CH$_2$CH$_2$—), respectively, are illustrated above in Scheme 12-2. Etoposide is obtained as previous described procedure (U.S. Pat. No. 3,408,441). Etoposide is reacted with triflated phosphonate with Cs$_2$CO$_3$ in acetonitrile to afford phosphonate 12-10. Etoposide is activated with p-nitrophenyl chloroformate, followed by reaction with aminoethyl phosphonate in the presence of TEA to give 12-13. Triflation of 12-9 with PhN(Tf)$_2$, followed by the CO insertion in the presence of Pd(OAc)$_2$, pdpp, TEA in DMF-H$_2$O gives carboxylic acid derivative 12-12. Compound 12-12 is reacted with an aminoethyl phosphonate, DIC, and HOAt to afford 12-16. Triflation of etoposide, followed CO insertion in the presence of Pd(OAc)$_2$, pdpp, TEA, and triethyl silane in DMF gives aldehyde intermediate 12-11. Aldehyde 12-11 is reacted with hydroxylamine hydrochloride and diisopropylethyl amine (DIPEA), followed by the reaction with a triflated phosphonate and NaH to furnish phosphonate 12-15. The reductive amination of 12-11 with an aminoethyl phosphonate, NaBH$_3$CN, and AcOH affords the desired compound 12-14.

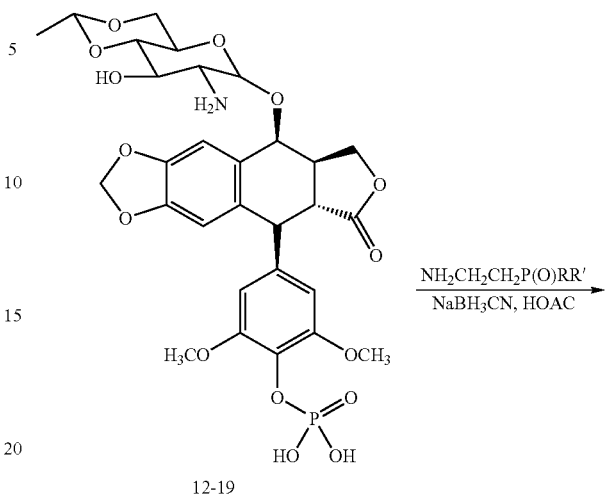

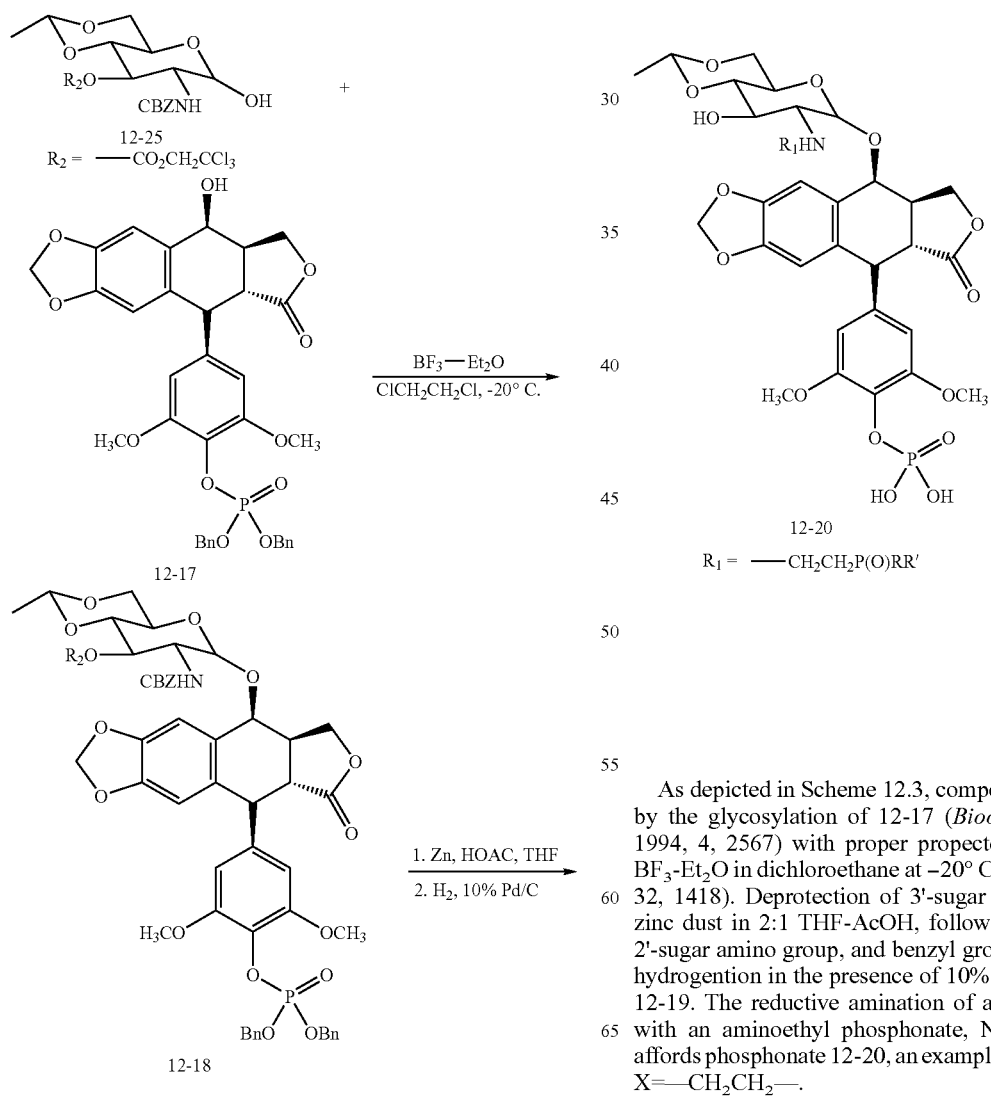

As depicted in Scheme 12.3, compound 12-18 is prepared by the glycosylation of 12-17 (*Bioorg. Med. Chem. Lett.* 1994, 4, 2567) with proper propected β-d-glucopyranose, BF$_3$-Et$_2$O in dichloroethane at −20° C. (*J. Med. Chem.* 1989, 32, 1418). Deprotection of 3'-sugar hydroxyl group using zinc dust in 2:1 THF-AcOH, followed the deprotection of 2'-sugar amino group, and benzyl groups of phosphosate by hydrogention in the presence of 10% Pd/C gives free amine 12-19. The reductive amination of amine derivative 12-19 with an aminoethyl phosphonate, NaBH$_3$CN, and AcOH affords phosphonate 12-20, an example of analog 12-8, where X=—CH$_2$CH$_2$—.

Scheme 12.4

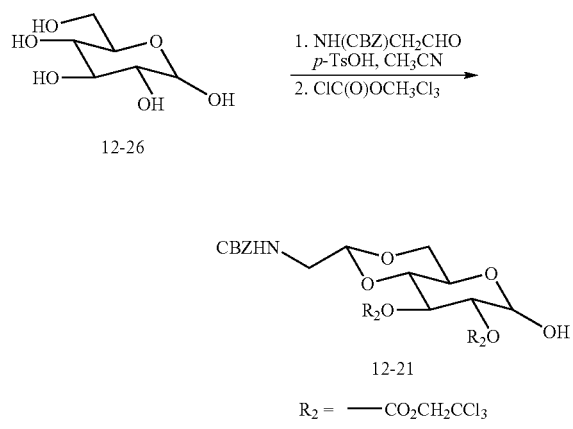

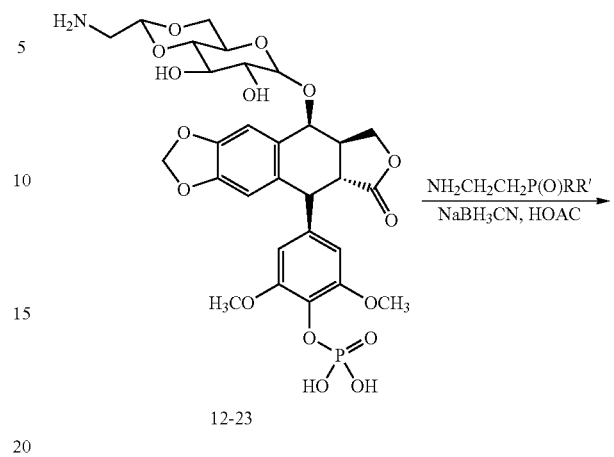

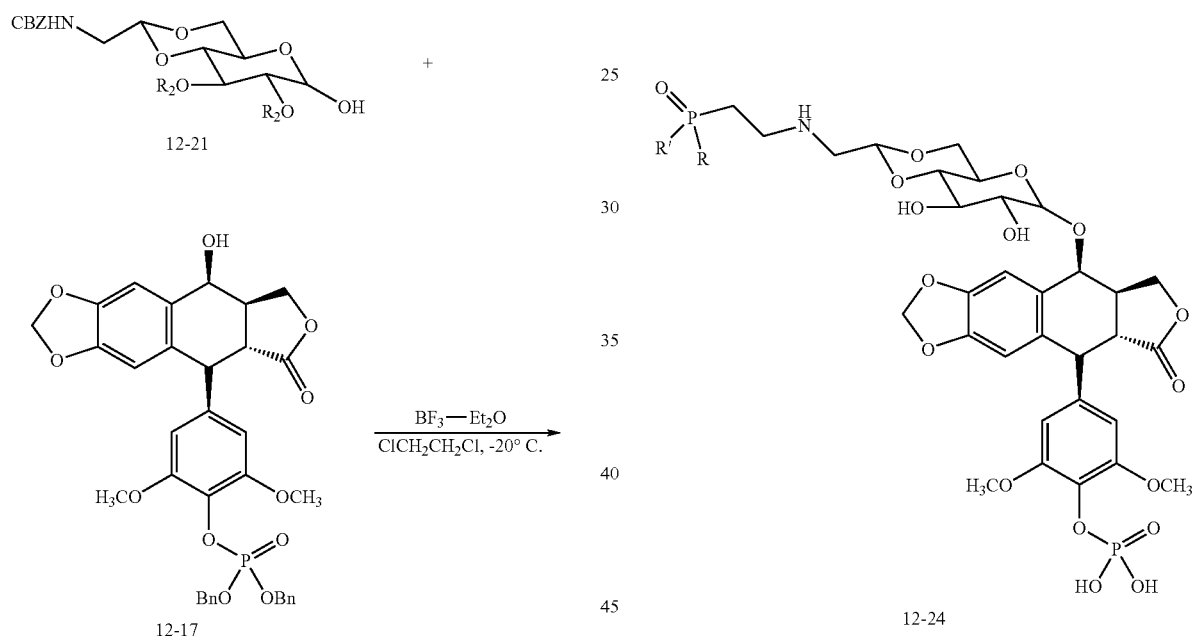

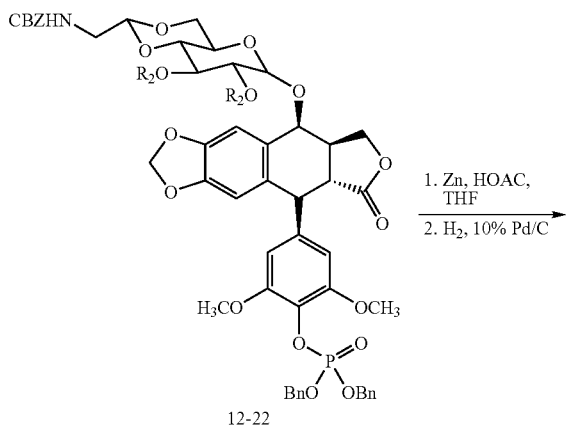

As in Scheme 12.4, compound 12-21 is prepared by the described procedure in *Bioor. Med. Chem. Lett.* 2001, 11, 2667 and *J. Med. Chem.* 1999, 42, 4640. Compound 12-22 is furnished by the glycosylation of 12-17 with 12-21, $BF_3$-$Et_2O$ in dichloroethane at −20° C. (*J. Med. Chem.* 1989, 32, 1418). Deprotection of 2'- and 3'-sugar hydroxyl group using zinc dust in 2:1 THF-AcOH, followed the deprotection of the CBZ-group of the terminal amino group and benzyl groups of phosphate by hydrogenation in the presence of 10% Pd/C gives free amine 12-23. The reductive amination of amine 12-23 with an animoethyl phosphonate, $NaBH_3CN$, and AcOH affords the desired compound 12-24, an example of analog 12-7, where X=—$CH_2CH_2$—, and n=1. Further manipulations can be performed on the phosphonate moiety prior to the final deprotection. These types of transformations are more extensively described in the phosphonate interconversion section herein.
Example 13
Preparation of Exemplary Compounds of the Present Invention
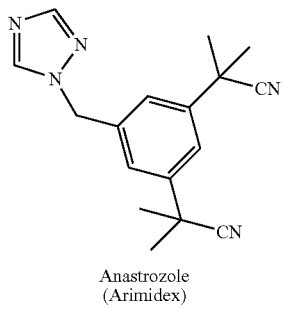
Scheme 13.1
Anastrozole (Arimidex) 13-1
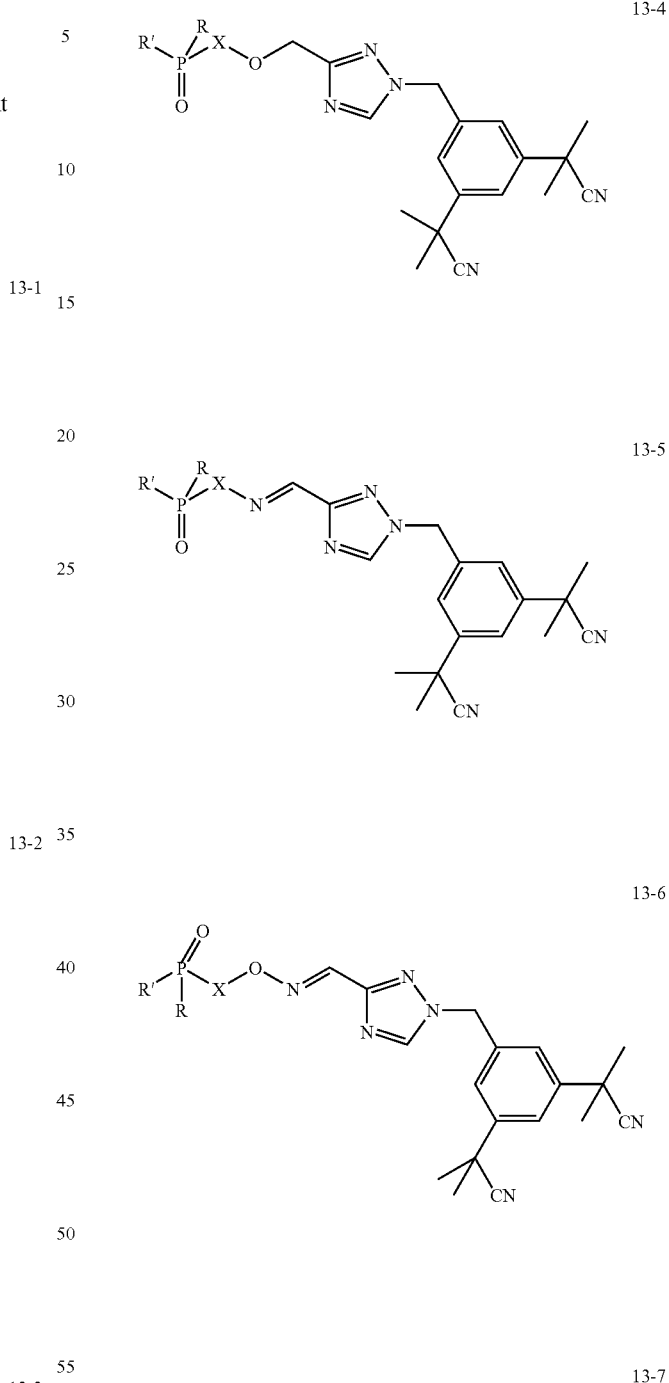
13-4
13-5
13-6
13-7

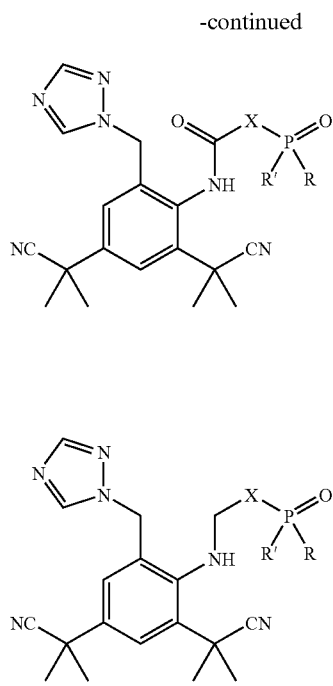
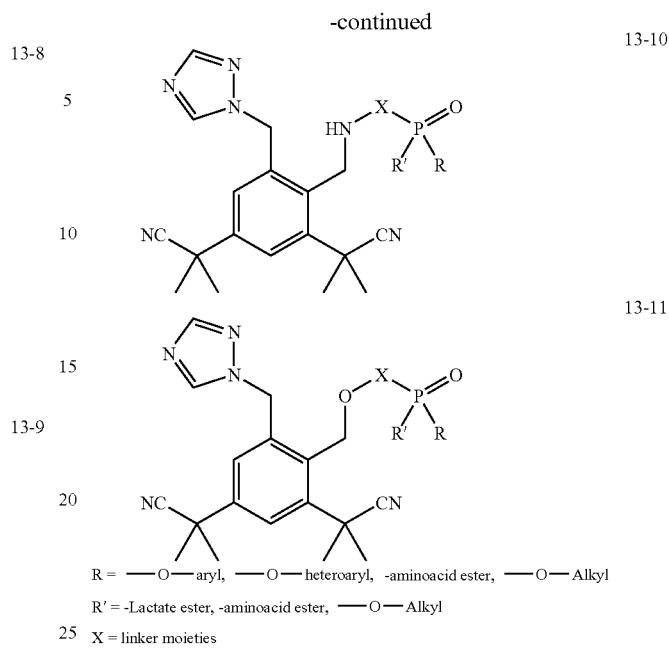
R = —O—aryl, —O—heteroaryl, -aminoacid ester, —O—Alkyl
R' = -Lactate ester, -aminoacid ester, —O—Alkyl
X = linker moieties
Exemplary compounds of the invention are illustrated above. Analogs 13-15, 13-16, and 13-9 are prepared as outlined in Scheme 13.2.
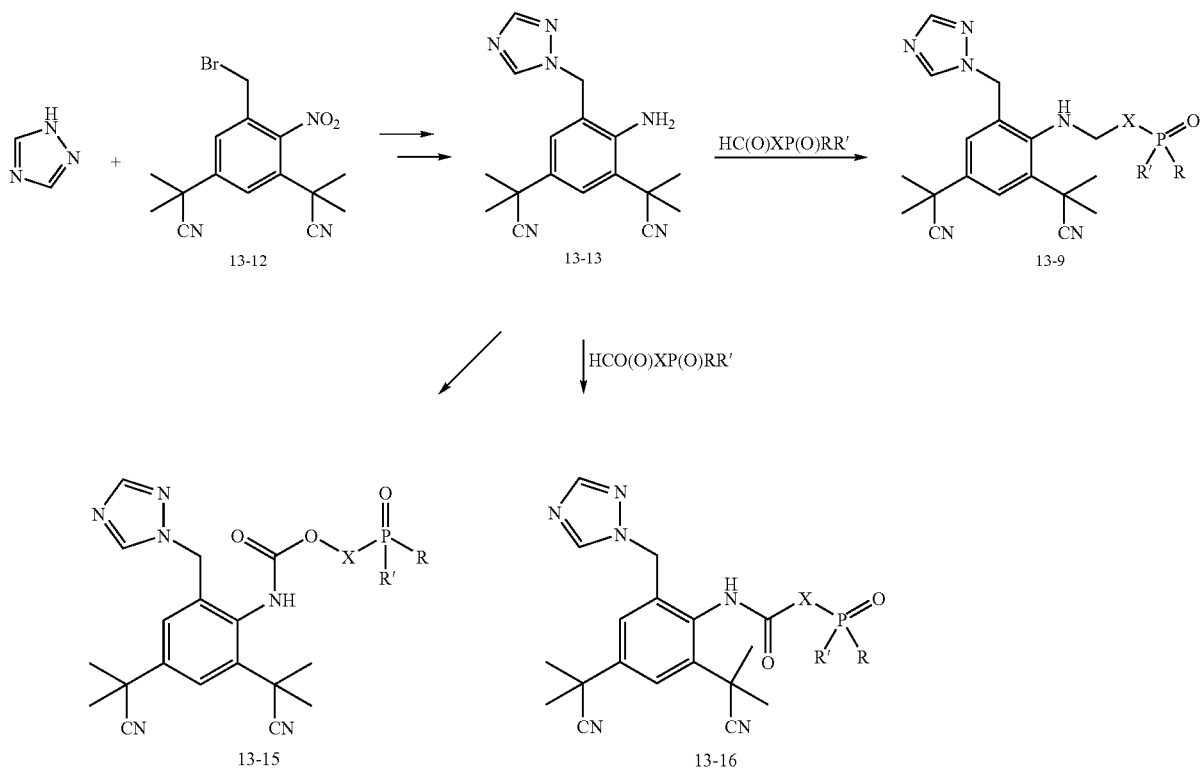

Scheme 13.3

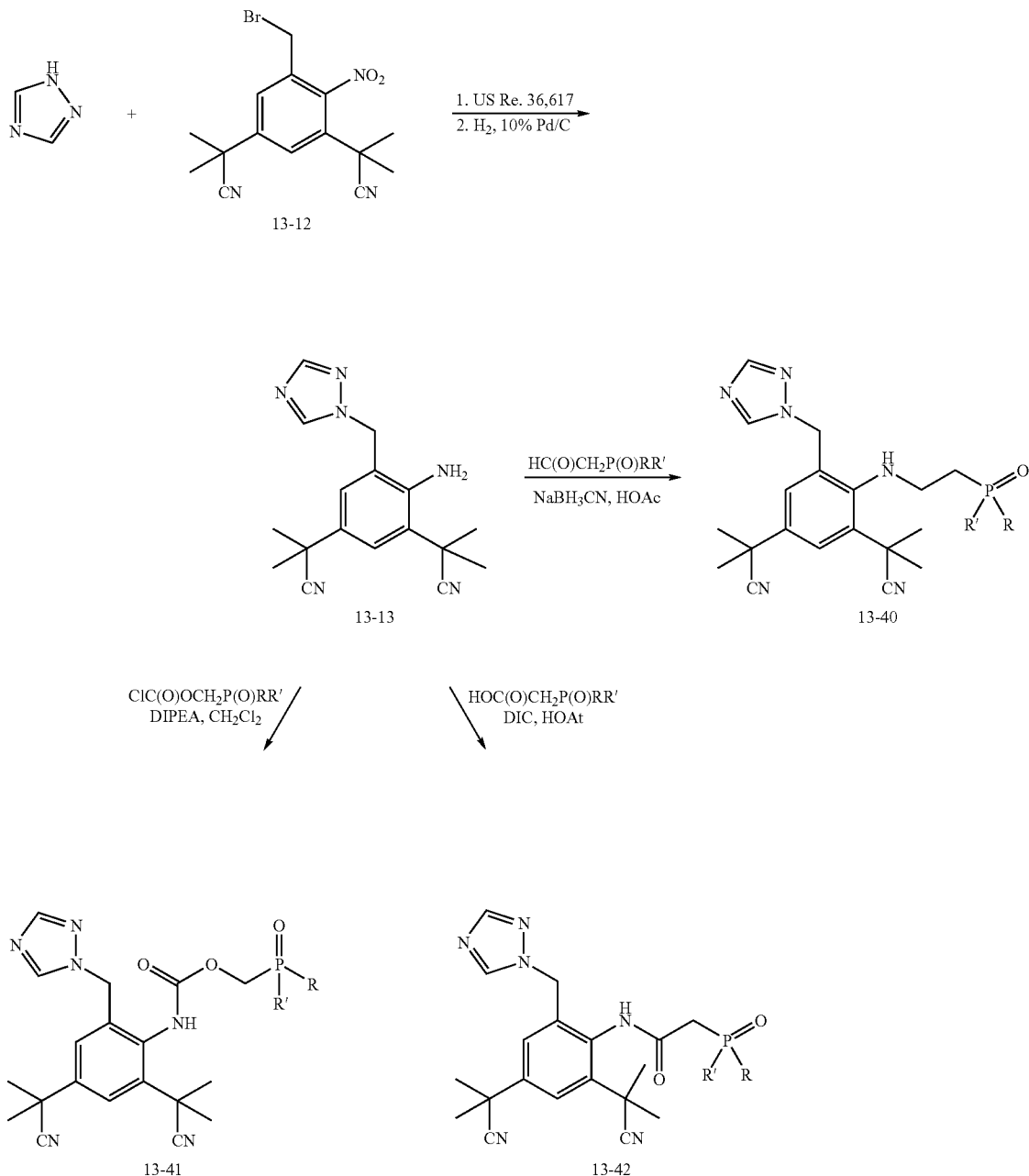

Compound 13-13 is a precursor of analogs 13-15, 13-16, and 13-9. Syntheses of examples are illustrated in Scheme 13.3. Compound 13-13 is synthesized according to procedure described in U.S. Pat. No. Re. 36,617, by alkylation of triazole with benzyl bromide 13-12, followed by hydrogenation of the $NO_2$ group in the presence of 10% Pd/C. The reductive amination of 13-13 with an aldehyde phosphonate, $NaBH_3CN$, and AcOH yields 13-40 (an example of 13-9, where X=—$CH_2$—). A solution of 13-13, carboxylic phosphonate, DIC, HOAt is stirred at room temperature generates product 13-42 (an example of 13-8 and 13-16, X=—$CH_2$—). Activation of the hydroxymethylphosphonate with phosgene, followed by reaction with amine 13-13 in the presence of diisopropylethyl amine in $CH_2Cl_2$ affords 13-41 (an example of 13-7 and 13-15, where X=—$CH_2$—).

Scheme 13.4
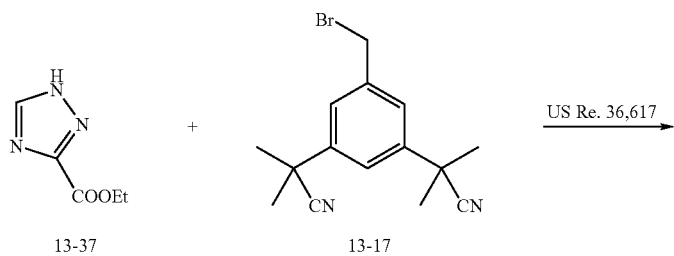
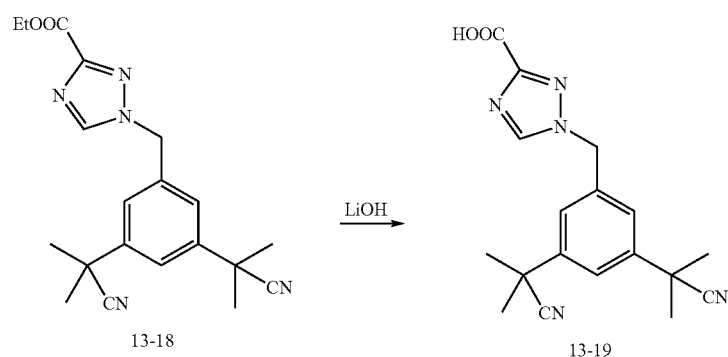
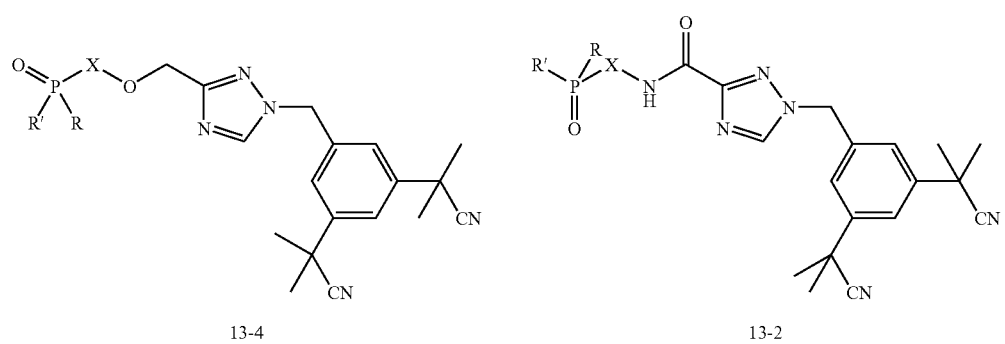

Analogs 13-2 and 13-4 are prepared as outlined in Scheme 13.4. Compound 13-18 is prepared as described procedure (U.S. Pat. No. Re. 36,617). Ester 13-18 is saponified to give acid 13-19, which is the key precursor of analogs 13-2 and 13-4.

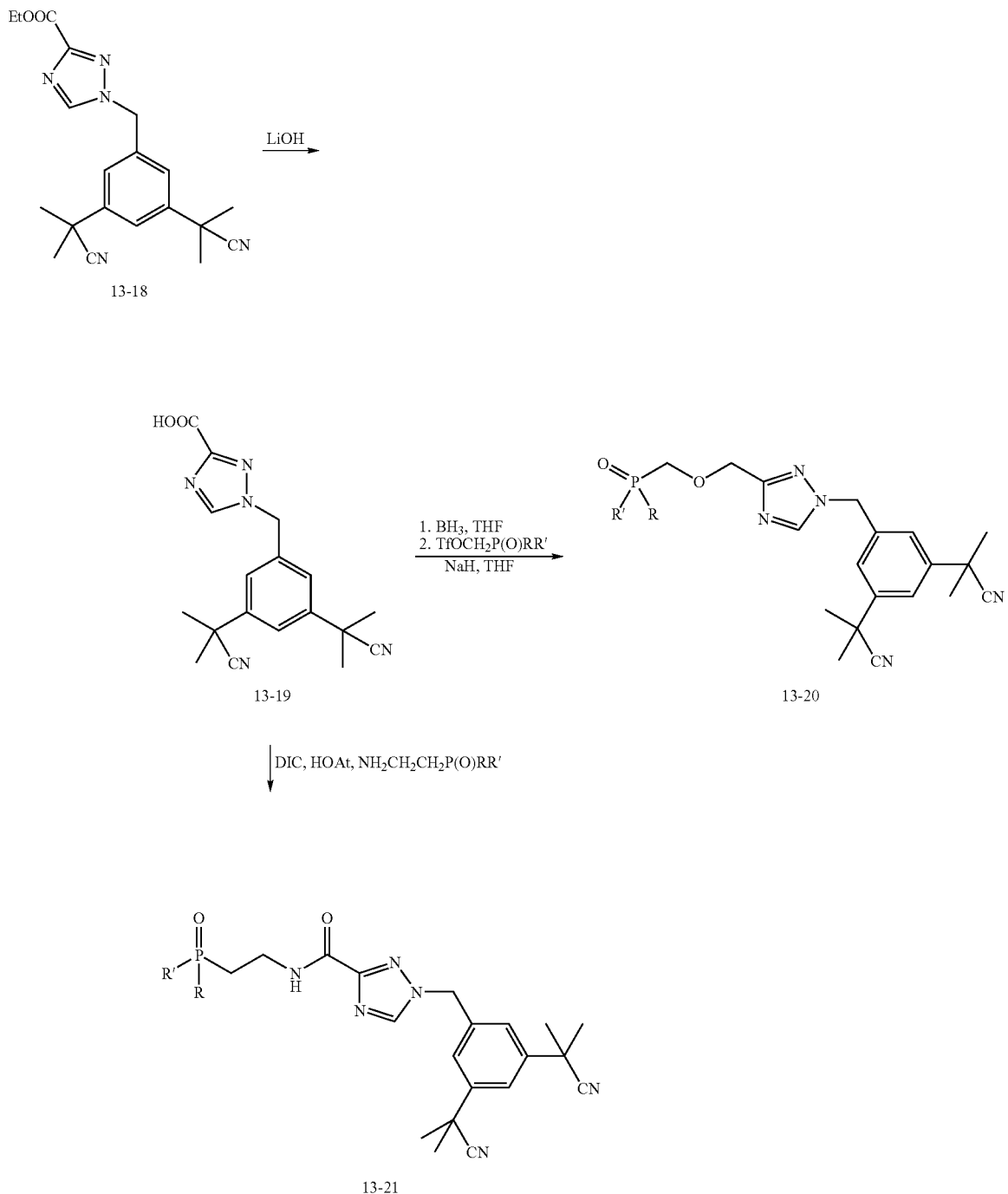

As depicted in Scheme 13.5, compound 13-18 is first saponified with LiOH, gives 13-19. Compound 13-19 is reacted with aminoethyl phosphonate in the presence of coupling reagent DIC, HOAt to furnish 13-21 (an example of 13-2, where X=—CH$_2$—). Acid 13-19 is reduced to alcohol with BH$_3$-THF, followed by the reaction with triflated phosphonate, NaH in THF at RT to furnish 13-20 (an example of 13-4, where X=—CH$_2$—).

Scheme 13.6
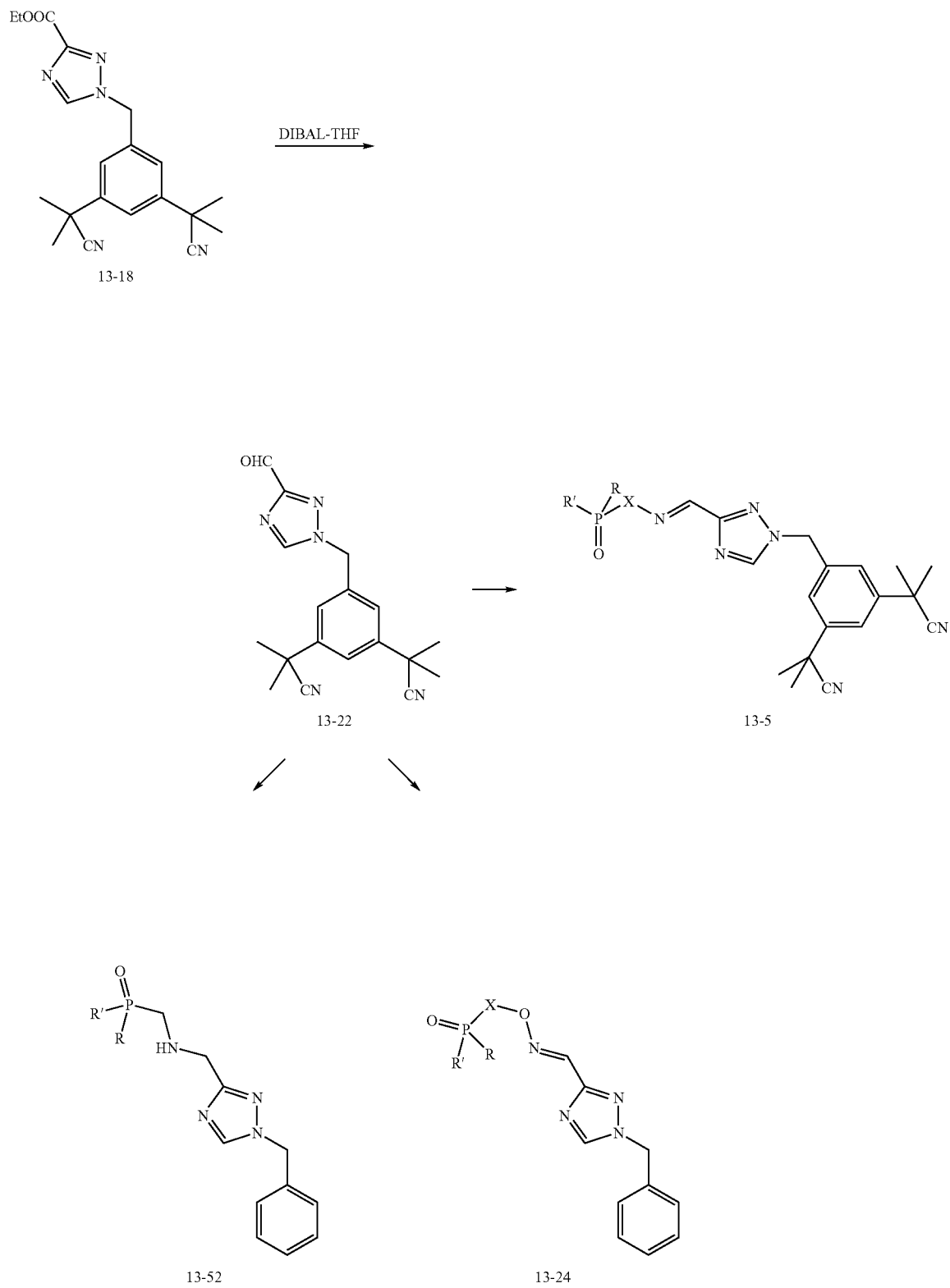

Compound 13-22 is obtained from the reduction of ester 13-18. Aldehyde derivative 13-22 is an important intermediate for analogs 13-5 and 13-24. (Scheme 13.6).

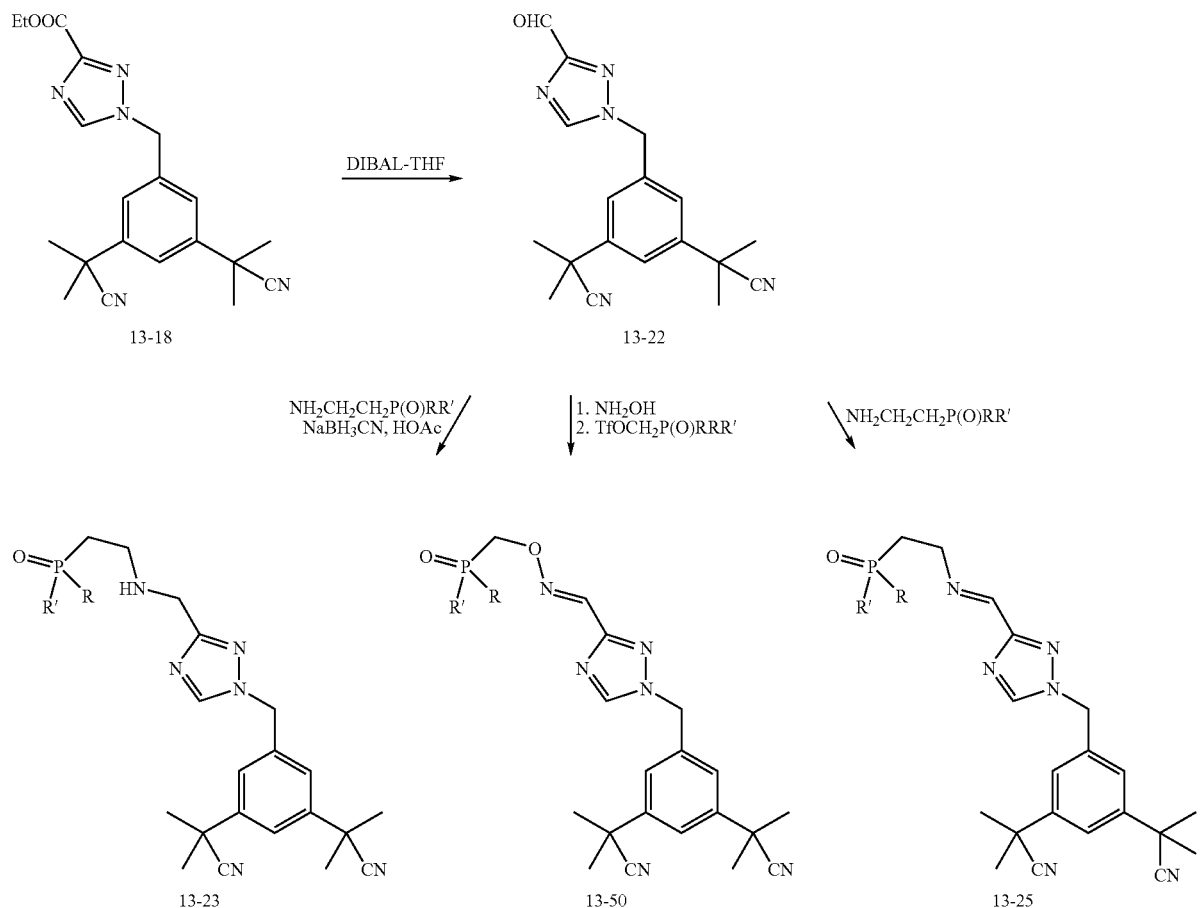

As shown in Scheme 13.7, aldehyde 13-22 is reacted with aminoethylphosphonate to afford the desired product 13-25 (an example of 13-3 and 13-52, where X=—CH₂CH₂—). Aldehyde 13-22 is reacted with hydroxylamine, followed by the reaction with triflated phosphonate to furnish 13-50 (an example of analogs 13-6 and 13-24, where X=—CH₂CH₂—). Compound 13-23 is obtained by the reductive amination of 13-22 and aminoethylphosphonate, NaBH₃CN, AcOH.

-continued

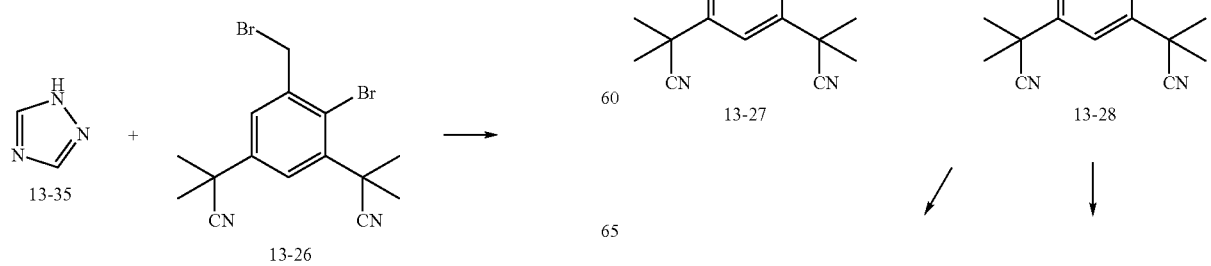

-continued

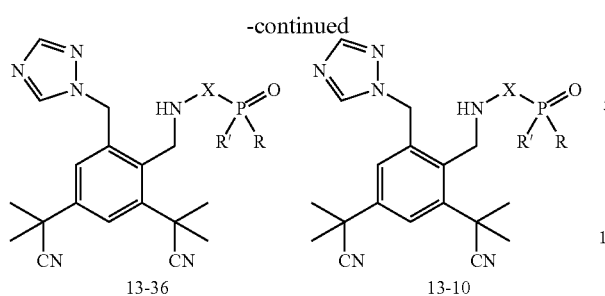

13-36                    13-10

Bromo derivative 13-27 is prepared by the described procedure for anastrozole (U.S. Pat. No. Re. 36,617). Compound 13-27 is reacted with Grignard reagent R²MgBr, or R²CH=CH₂ in the presence of a Pd catalyst, to give the vinyl derivative, followed by ozonolysis to furnish aldehyde 13-28. Aldehyde 13-28 is converted to analogs 13-36 and 13-10 using the procedures described in Schemes 13.6 and 13.7.

Scheme 13.9

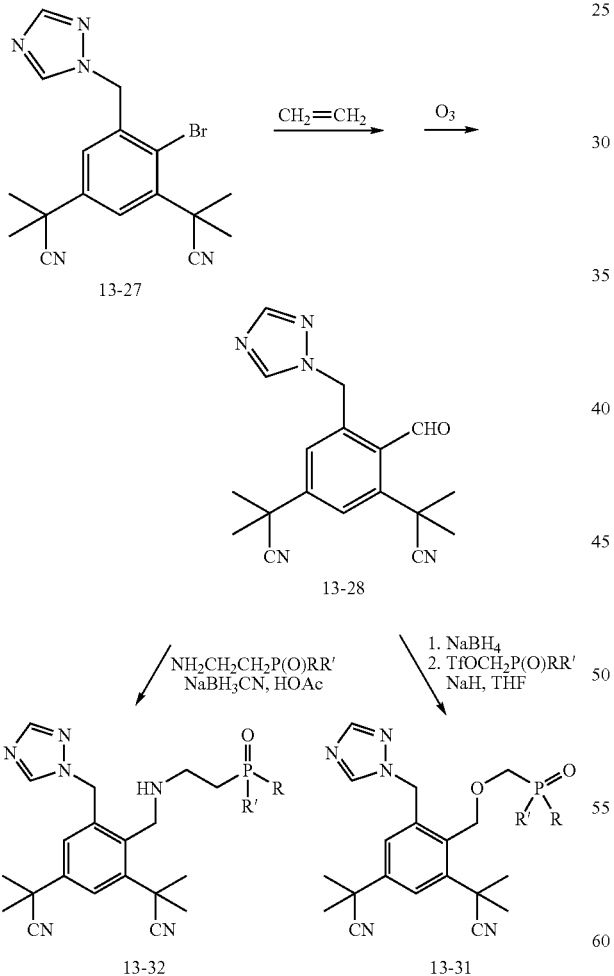

As shown in Scheme 13.9, compound 13-27 is coupled with CH₂=CH₂ in the presence of Pd(OAc)₂, n-Bu₃P, K₂CO₃ in DMF at 100° C. (*Tetrahedron Lett.* 2002, 43, 3401), followed by ozonolysis to furnish aldehyde 13-28. The reductive amination of 13-28 with animoethyl phosphonate, NaBH₃CN, AcOH gives desired product 13-32 (an example of analogs 13-10 and 13-36, where X=—CH₂CH₂—). Reduction of the aldehyde using NaBH₄ gives an alcohol derivative. Reaction of the alcohol derivative with NaH and a triflated phosphonate in THF generates compound 13-31 (an example of analogs 13-11 and 13-10, where X=—CH₂—).

Further manipulations can be performed on the phosphonate moiety prior to the final deprotection. These types of transformations are more extensively described in the phosphonate interconversion section herein.

Example 14

Preparation of Exemplary Compounds of the Present Invention

Scheme 14.1

14-1

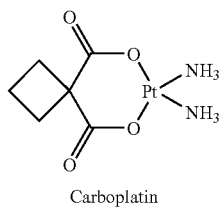

Carboplatin 14-2

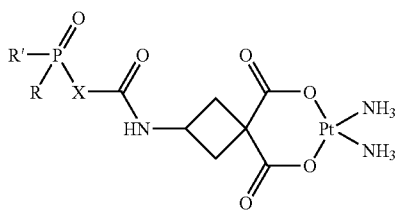

14-3

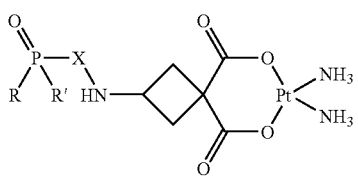

14-4

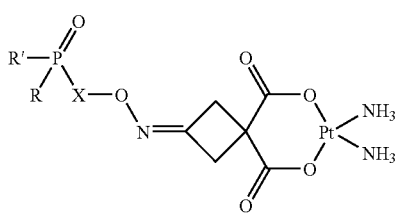

-continued

14-5

14-8
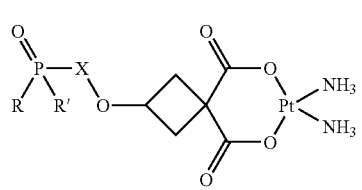
14-6
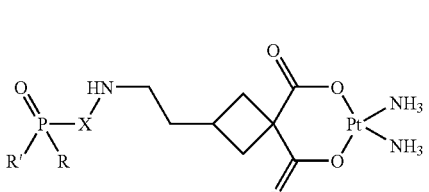
14-9
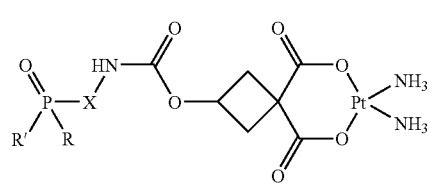
14-7
R = —O—aryl, —O—heteroaryl, -aminoacid ester, —O—Alkyl
R' = -Lactate ester, -aminoacid ester, —O—Alkyl
X = linker moieties
Exemplary compounds of the invention are illustrated above.
Scheme 14.2
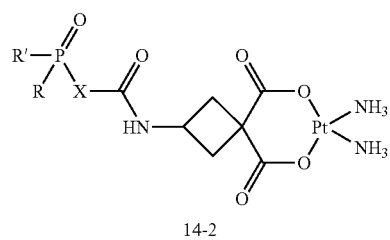
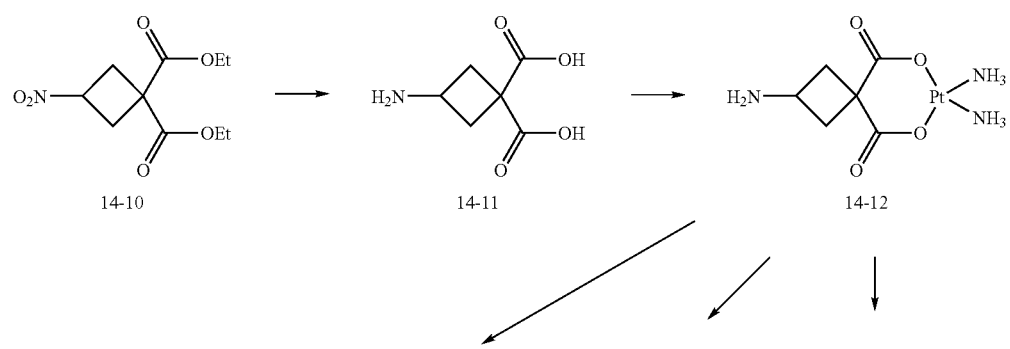

Syntheses of new compounds containing phosphonate are illustrated in Scheme 14.2. Diethyl 3-nitrocyclobutane-1,1-dicarboxylate (*J. Org. Chem.* 1989, 54, 2869) is readily converted to the 3-amino derivative in 2 steps. Compound 14-12 is obtained from the reaction between 3-aminocyclobutane-1,1-dicarboxylic acid sodium salt and $PtCl_2(NH_3)_2$ (U.S. Pat. No. 4,625,927). Compound 14-12 is readily converted to analogs 14-2, 14-3, and 14-5 by reaction with the proper phosphonate in one or two steps.

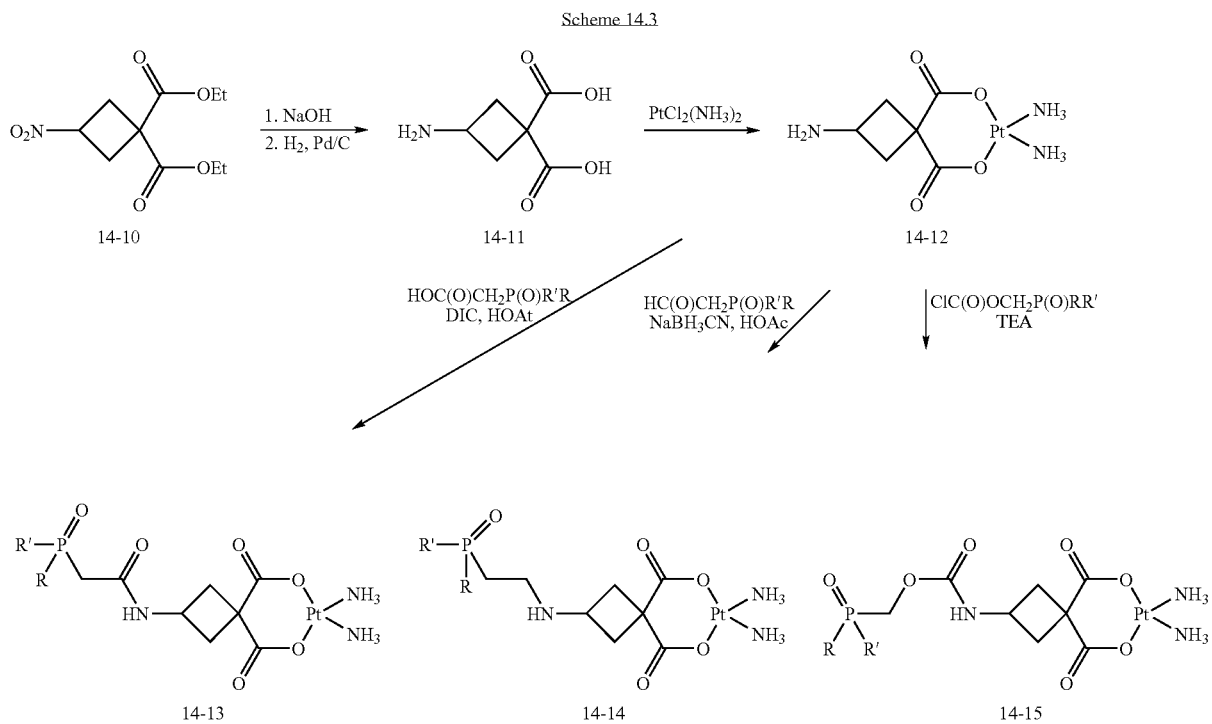

As outlined in Scheme 14.3, 3-amino-1,1-dicarboxylic acid is obtained from 3-nitro derivative in 2 steps; first saponification with NaOH, then hydrogenation in the presence of 10% Pd/C. This dicarboxylic acid is first converted to its disodium salt, then is reacted with $PtCl_2(NH_3)_2$ according to the previously reported procedure (U.S. Pat. No. 4,657,729) to give carboplatin analog 14-12. The reaction between 14-12 and phosphonate carboxylic acid, HOAt, and DIC gives 14-13 (an example of 14-2, where $X=\!\!=\!\!CH_2\!\!-\!\!$). The reductive amination of 14-12 with aldehyde phosphonate, $NaBH_3CN$, and AcOH affords the desired compound 14-14 (an example of 14-3, where $X=\!\!=\!\!CH_2CH_2\!\!-\!\!$). The hydroxymethyl phosphonate is activated with triphosgene to form chloroformate derivative, which is reacted with compound 14-12 in the presence of TEA to furnish the desired product 14-15 (an example of 14-5, where $X=\!\!=\!\!CH_2\!\!-\!\!$).

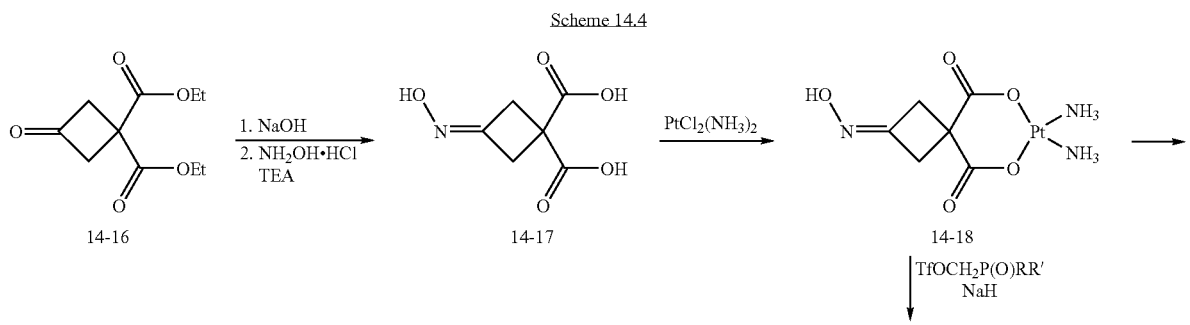

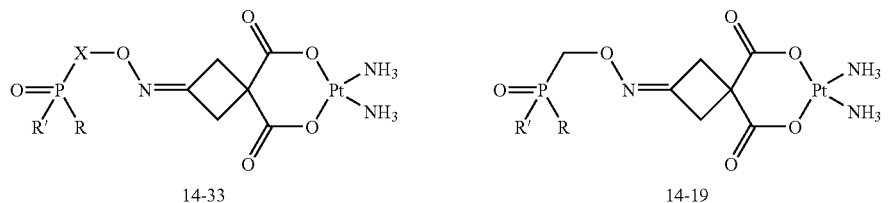

14-33          14-19

Diethyl 3-oxocyclobutane-1,1-dicarboxylate (*J. Med. Chem.* 1990, 33, 2905) is saponified with sodium hydroxide, then reacted with hydroxylamine hydrochloride in the presence of TEA to yield the oxime intermediate 14-17. The oxime dicarboxylic acid is treated with sodium hydroxide (to form the disodium salt), then is reacted with $PtCl_2(NH_3)_2$ according to previous reported procedure (U.S. Pat. No. 4,657,729) to give carboplatin derivative 14-18. Compound 14-18 is readily converted to analog 14-33. An example of 14-4, phosphonate 14-19 is prepared by treating 14-12 with NaH and a triflated phosphonate (Scheme 14.4).

Scheme 14.5

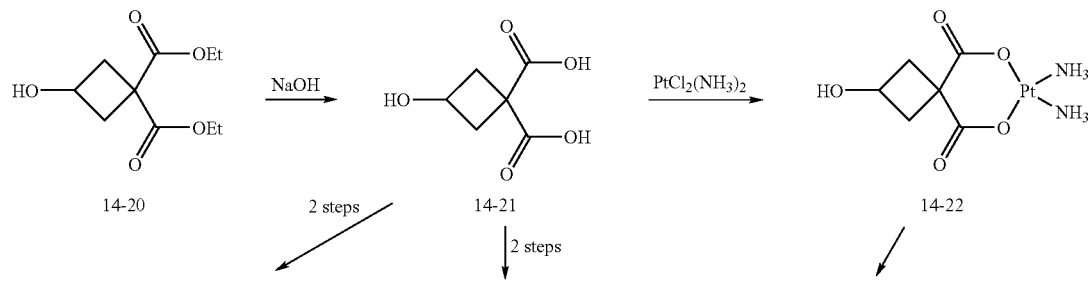

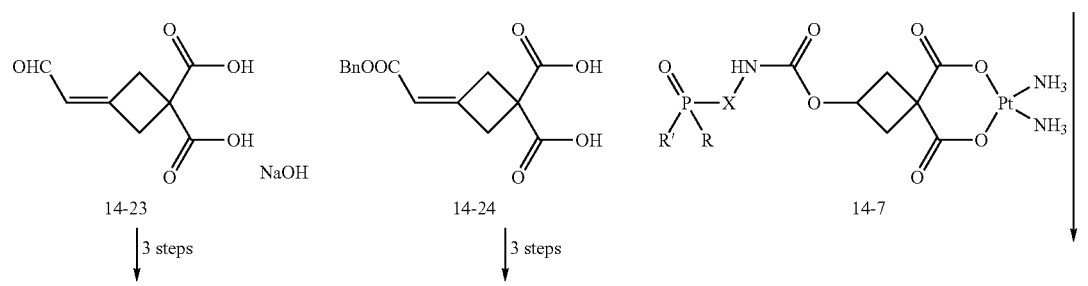

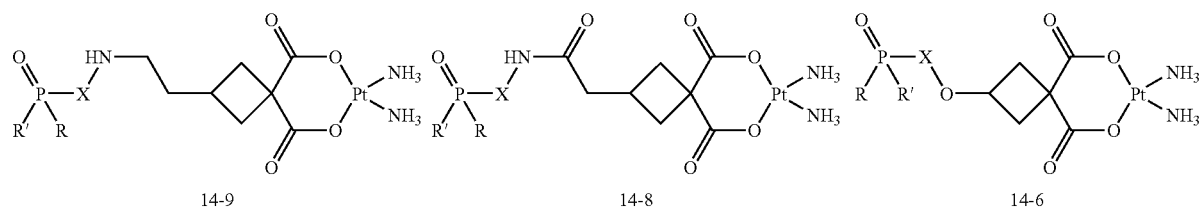

In Scheme 14.5, diethyl 3-hydroxycyclobutane-1,1-dicarboxylate (*J. Med. Chem.* 1990, 33, 2905) is saponified with sodium hydroxide and the disodium salt of the dicarboxylic acid is reacted with $PtCl_2(NH_3)_2$ according to the previously reported procedure (U.S. Pat. No. 4,657,729) to afford the 3-hydroxy carboplatin analog 14-22. This analog is readily converted to 14-6 by the reaction with a triflated phosphonate. Hydroxyl 14-22 is converted to analog 14-7 by the activation of the hydroxyl group, followed by reaction with an aminophosphonate. 3-Hydroxycyclobutane-1,1-dicarboxylic acid 14-21 is oxidized to its 3-oxo derivative and can be further converted to 14-23 and 14-24. Compound 14-23 is reacted with $PtCl_2(NH_3)_2$ according to the previously reported procedure (U.S. Pat. No. 4,657,729), followed by hydrogenation and the reductive amination to furnish 14-9. Compound 14-24 is converted to 14-8 in 3 steps, by hydrogenation, carboplatin formation, and reaction with an aminophosphonate.

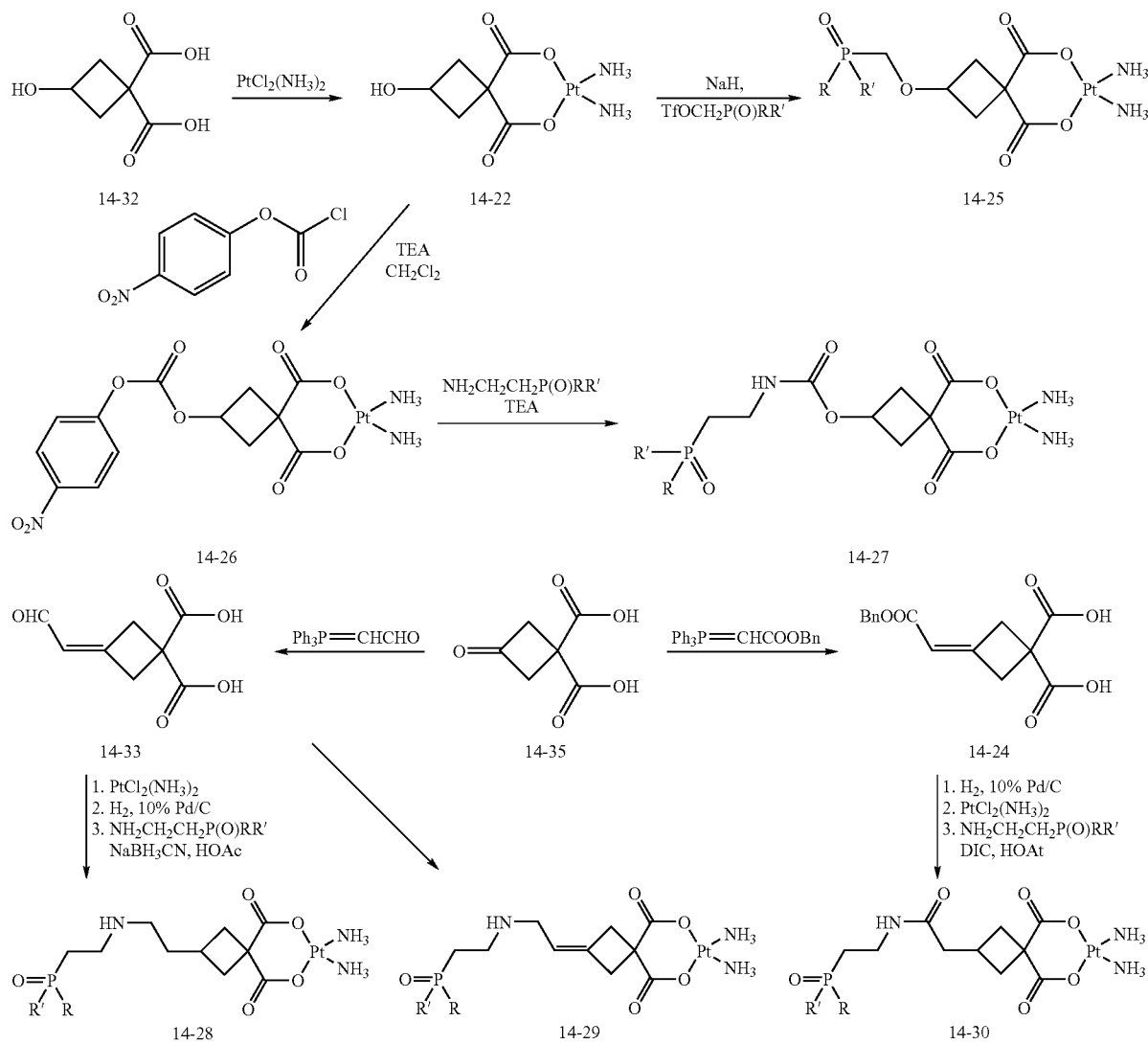

Scheme 14.6

As depicted in Scheme 14.6, diethyl 3-hydroxycyclobutane-1,1-dicarboxylate (*J. Med. Chem.* 1990, 33, 2905) is saponified with sodium hydroxide. This dicarboxylic acid disodium salt is reacted with $PtCl_2(NH_3)_2$ according to previous reported procedure (U.S. Pat. No. 4,657,729) gives the 3-hydroxy carboplatin analog 14-22. This analog is readily to convert to 14-25 (an example of 14-6, where X=—$CH_2$—) by the reaction with NaH and a triflated phosphonate. The activation of the hydroxyl group with p-nitrophenyl chlorofor mate gives 14-26. The activated acid derivative 14-26 is reacted with aminoethyl phosphonate in the presence of TEA to afford the desired product 14-27 (an example of 14-7, where X=—CH$_2$CH$_2$—). 3-Oxocyclobutane-1,1-dicarobxylic acid 14-35 is reacted with Ph$_3$P=CHCHO or PH$_3$P=CHCOOBn in CH$_2$Cl$_2$ to afford 14-33 and 14-24, respectively. The disodium salt of compound 14-33 is reacted with PtCl$_2$(NH$_3$)$_2$ to form a carboplatin derivative, followed by hydrogenation in the presence of 10% Pd/C to reduce the double bond, and reductive amination with aminoethyl phosphonate, NaBH$_3$CN, and AcOH affords the desired 14-28 (an example of 14-9, where X=—CH$_2$CH$_2$—). The disodium salt of compound 14-33 is reacted with PtCl$_2$(NH$_3$)$_2$ followed by the reductive amination with aminoethyl phosphonate, NaBH$_3$CN, and AcOH to furnish 14-29 (an unsaturated analog of 14-28). Compound 14-30 is synthesized from 14-24 by the hydrogenation in the presence of 10% Pd/C followed by the reaction with PtCl$_2$(NH$_3$)$_2$, and the reaction with aminoethyl phosphonate, DIC, AcOH (an example of 14-8, where X=—CH$_2$CH$_2$—).

Further manipulations can be performed on the phosphonate moiety prior to the final deprotection. These types of transformations are more extensively described in the phosphonate interconversion section herein.

Example 15

Preparation of Exemplary Compounds of te Present Invention

Scheme 15.1

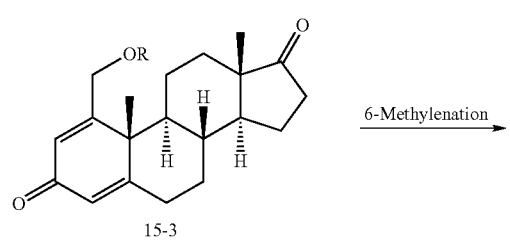

(Exemestane)

15-1

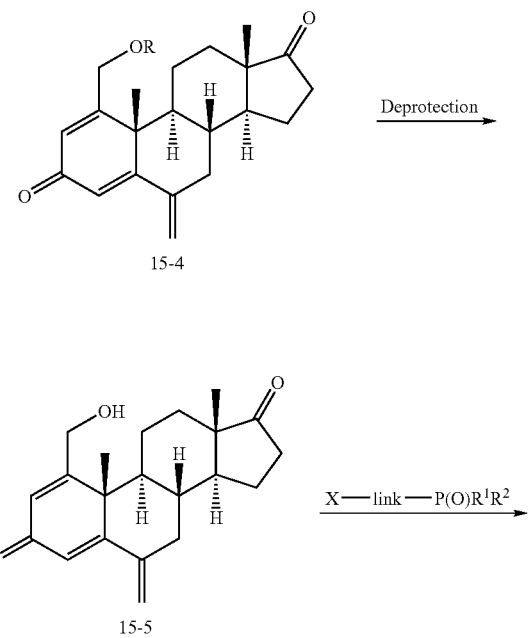

Phosphonate analogs 15-2 are readily prepared from 1-alkanoyloxymethyl steroid 15-3 (U.S. Pat. No. 4,591,585), as illustrated in Scheme 15.2. The introduction of methylene group at position 6 can be accomplished according to the method reported in literature (*Synthesis* 1982, 34). Hydrolysis of 15-4 affords the 1-hydroxymethyl steroid 15-5. Alkylation of 15-5 with the phosphonate reagent affords desired compounds 15-2.

Scheme 15.2

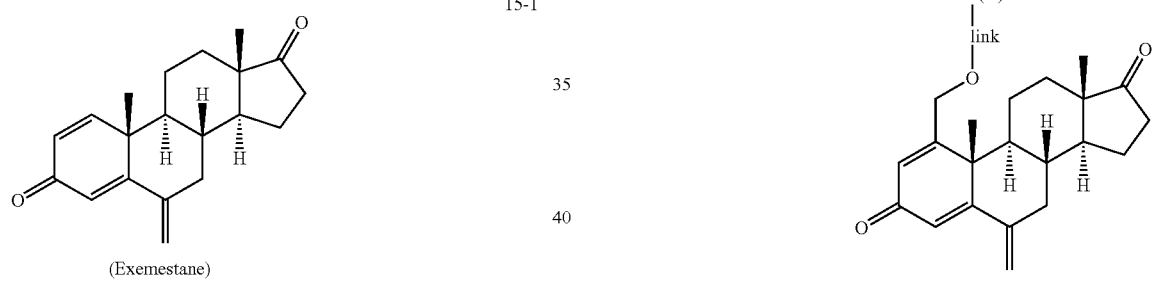

Scheme 15.3

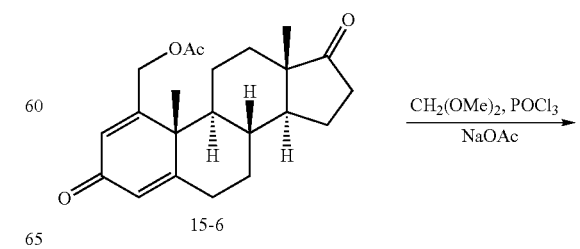

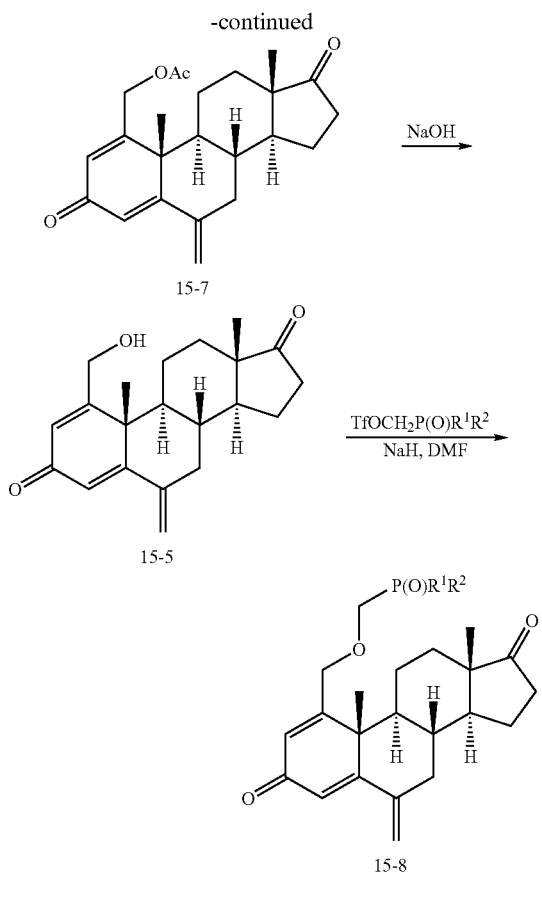

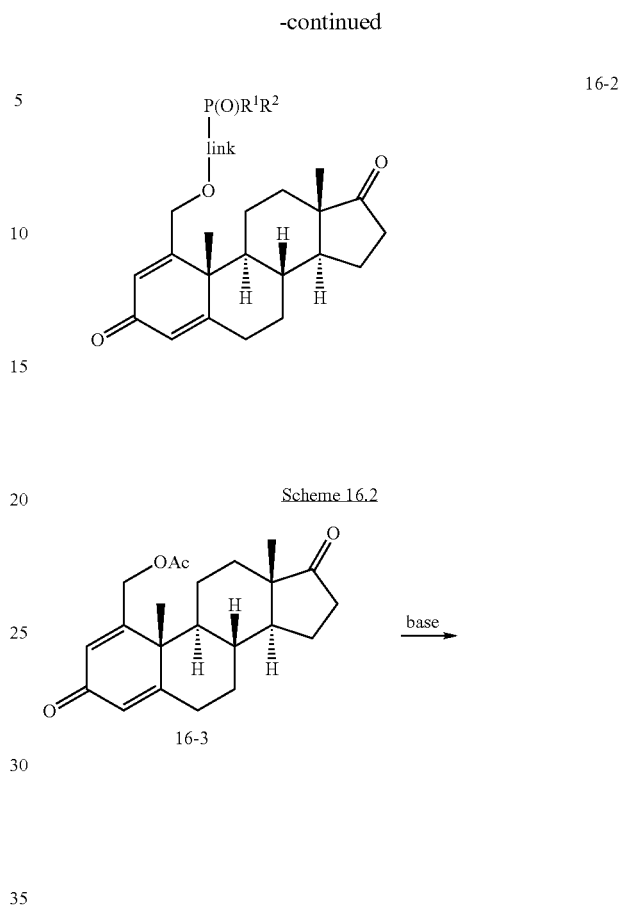

Scheme 15.3 shows an example for the preparation of a phosphonate analog of exemestane. 1-Acetyloxymethyl steroid 15-6 is treated with formaldehyde acetal, phosphorus oxychloride and sodium acetate in chloroform to give 6-methylene compound 15-7. Hydrolysis of 15-7 with sodium hydroxide give 1-hydroxymethyl steroid 15-5. Alkylation of 15-5 with phosphonate triflate afford desired product 15-8.

Further manipulations can be performed on the phosphonate moiety prior to the final deprotection. These types of transformations are more extensively described in the phosphonate interconversion section herein.

Example 16

Preparation of Exemplary Compounds of the Present Invention

Scheme 16.1

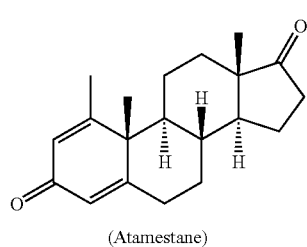

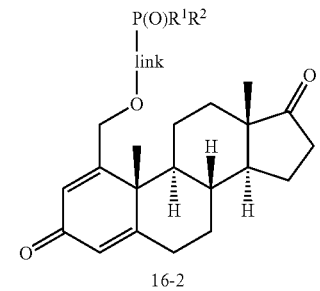

Phosphonate analogs 16-2 are readily prepared from 1-acetyloxymethyl steroid 16-3 (U.S. Pat. No. 4,591,585), as illustrated in Scheme 16.2. Hydrolysis of 16-3 give 1-hydroxymethyl steroid 16-4. Alkylation of 16-4 with the phosphonate reagent affords desired compounds 16-2.

Example 17

Preparation of Exemplary Compounds of the Present Invention

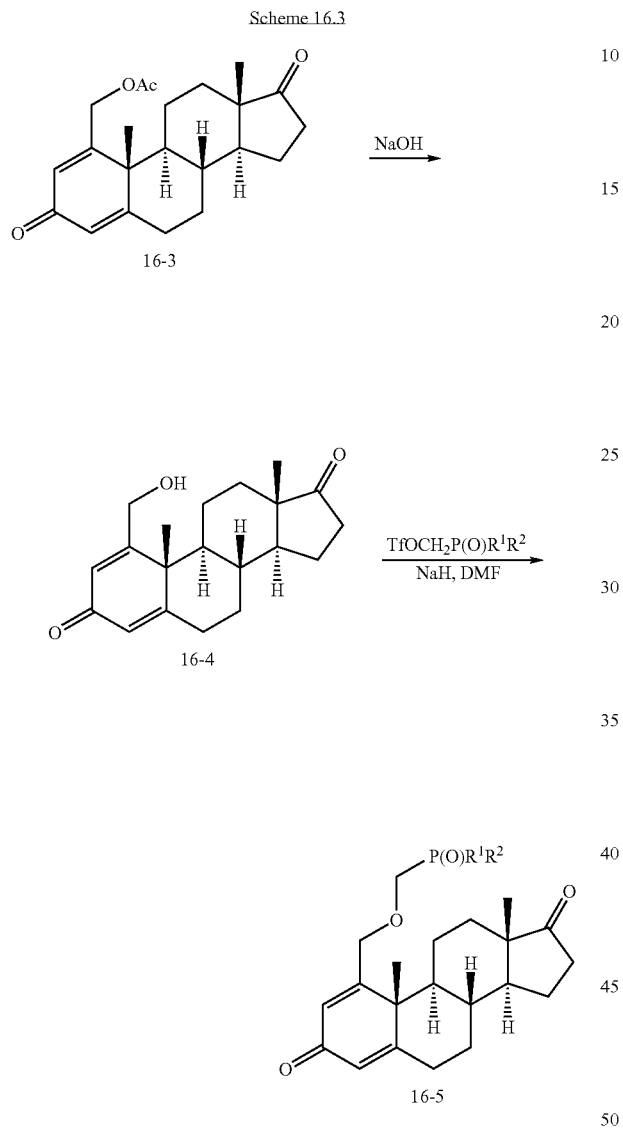

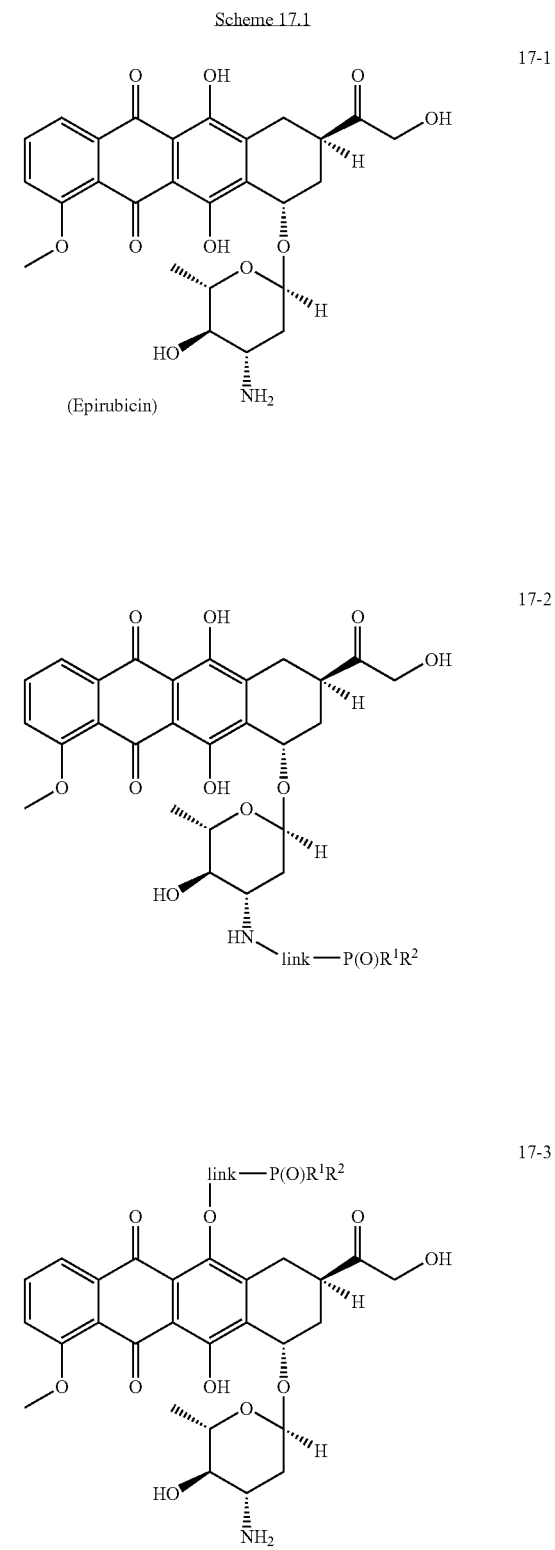

Scheme 16.3 shows an example for preparation of phosphonate analog of atamestane. 1-Acetyloxymethyl steroid 16-3 is hydrolized with sodium hydroxide to give 1-hydroxymethyl steroid 16-4. Alkylation of 16-4 with a phosphonate triflate afford desired product 16-5.

Further manipulations can be performed on the phosphonate moiety prior to the final deprotection. These types of transformations are more extensively described in the phosphonate interconversion section herein.

-continued

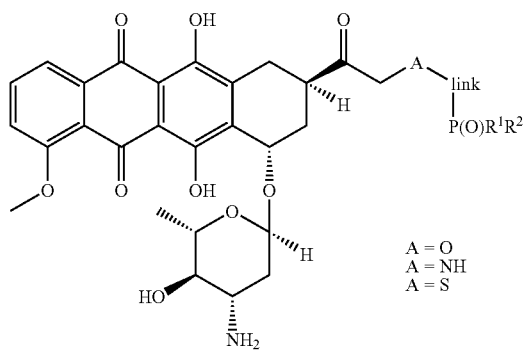

17-4

A = O
A = NH
A = S

Exemplary compounds of the invention are illustrated above.

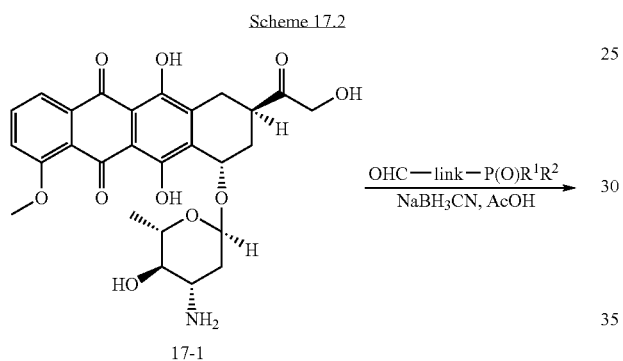

17-1

17-2

As illustrated in Scheme 17.4, phosphonate analogs of type 17-3 are readily prepared from protected epirubicin 17-6 (accessible by the methods reported in *J. Org. Chem.* 1997, 42, 3653) via alkylation with appropriate phosphonate reagent.

As illustrated in Scheme 17.2, phosphonate analogs of type 17-2 are readily prepared from epirubicin (17-1) via reductive alkylation of the amine with phosphonate aldehydes.

For example (Scheme 17.3), reductive alkylation of epirubicin 17-1 with aldehyde 17-15 (*Synth. Commun.* 1992, 22, 2219) give desired compound 17-5.

As illustrated in Scheme 17.4, phosphonate analogs of type 17-3 are readily prepared from protected epirubicin 17-6 (accessible by the methods reported in *J. Org. Chem.* 1997, 42, 3653) via alkylation with appropriate phosphonate reagent.

Scheme 17.5

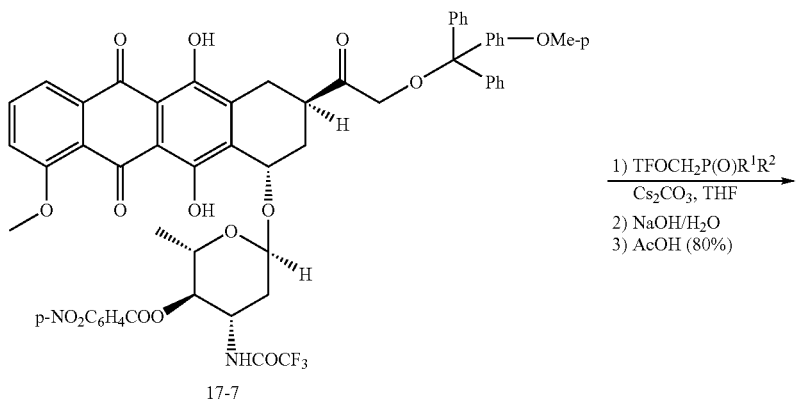

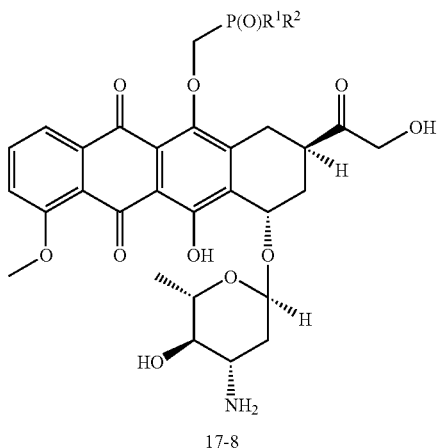

For example (Scheme 17.5), alkylation of tri-protected epirubicin 17-7 with phosphonate triflate, followed by basic (0.1N sodium hydroxide) and acidic (80% acetic acid) deprotection, afford compound 17-8.

Scheme 17.6

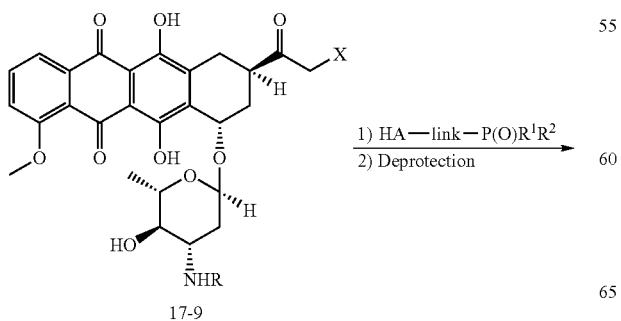

-continued

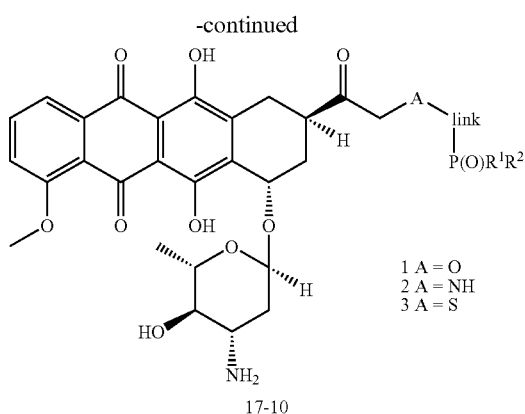

As illustrated in Scheme 17.6, phosphonate analogs of type 17-4 are readily prepared from epirubicin intermediate 17-9

(accessible by the methods reported in *J. Med. Chem.* 1985, 28, 1223) via a displacement of the leaving group X with appropriate nucleophiles.

Scheme 17.7

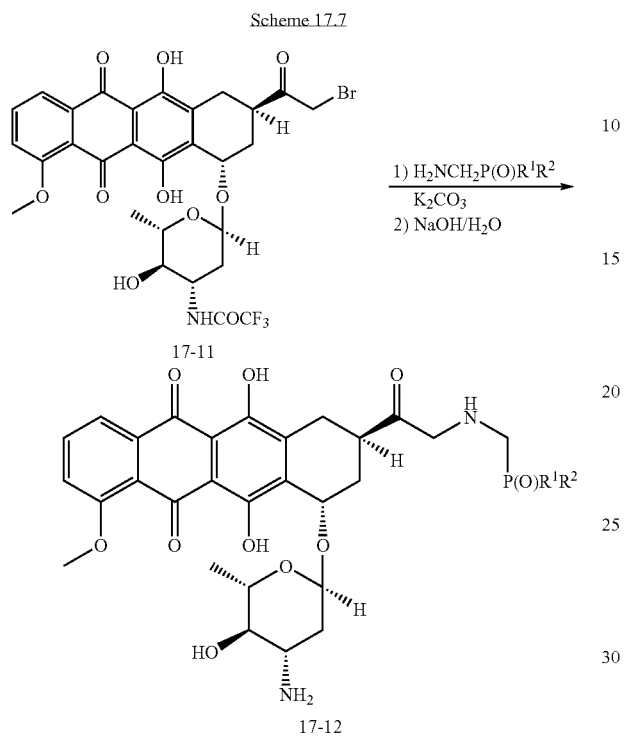

For example (Scheme 17.7), reaction of bromide 17-11 with phosphonate amine, followed by a deprotection, affords desired product 17-12.

Further manipulations can be performed on the phosphonate moiety prior to the final deprotection. These types of transformations are more extensively described in phosphonate interconversion section herein.

Example 18

Preparation of Exemplary Compounds of the Present Invention

Scheme 18.1

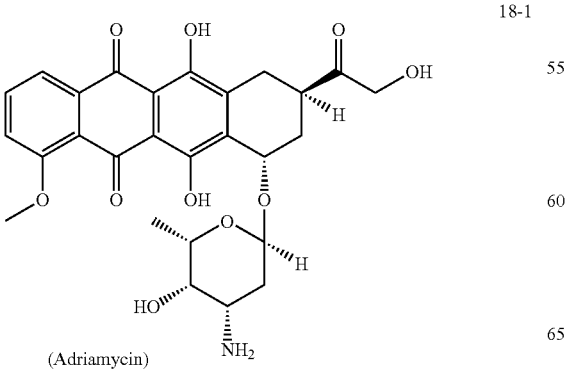

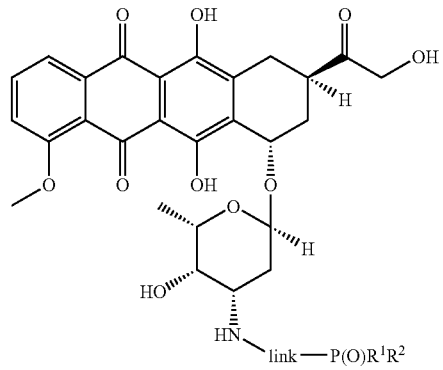

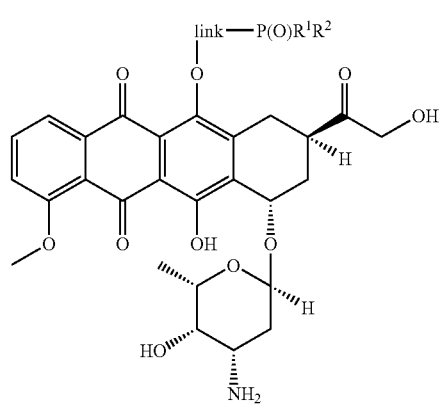

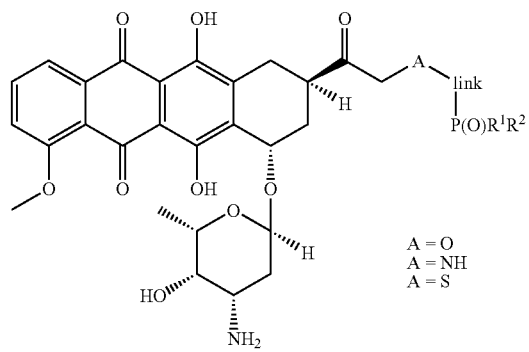

Exemplary compounds of the invention are illustrated above.

Scheme 18.2

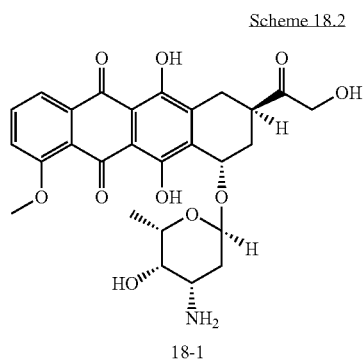

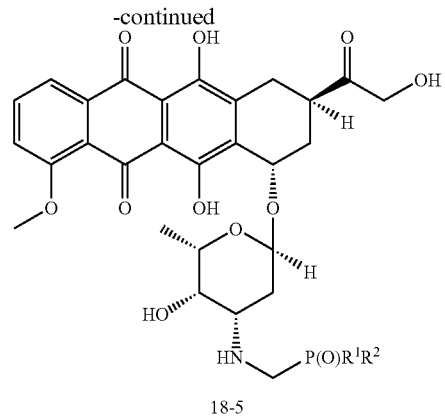

18-5

For example (Scheme 18.3), reductive alkylation of adriamycin 18-1 with aldehyde 18-15 (*Synth. Commun.* 1992, 22, 2219) give desired compound

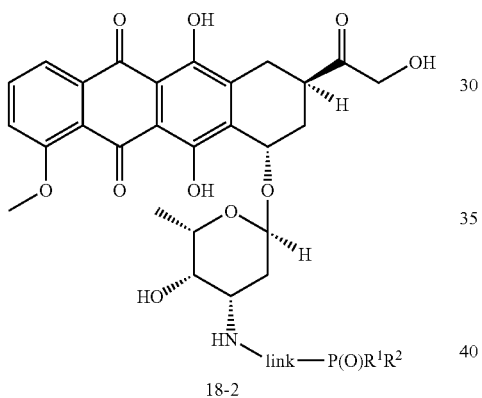

18-2

Scheme 18.4

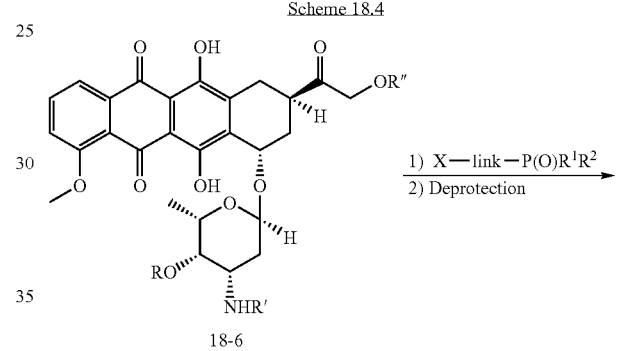

18-6

As illustrated in Scheme 18.2, phosphonate analogs of type 18-2 are readily prepared from adriamycin 18-1 via reductive alkylation of the amine with phosphonate aldehydes.

Scheme 18.3

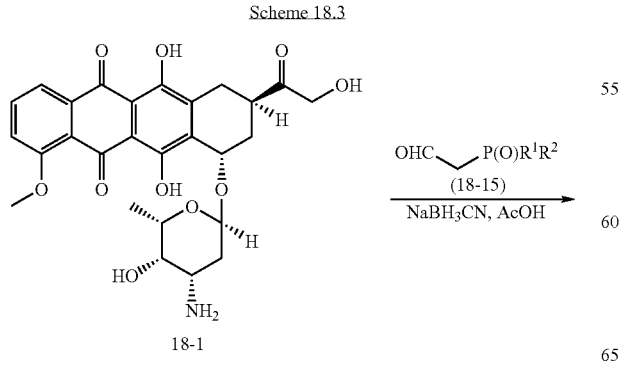

18-1

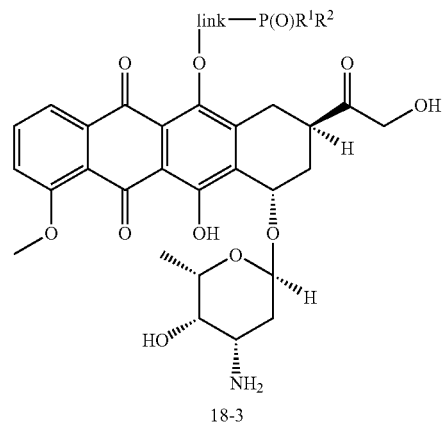

18-3

As illustrated in Scheme 18.4, phosphonate analogs of type 18-3 are readily prepared from protected adriamycin 18-6 (*J. Org. Chem.* 1997, 42, 3653) via alkylation with appropriate phosphonate reagent.

Scheme 18.5

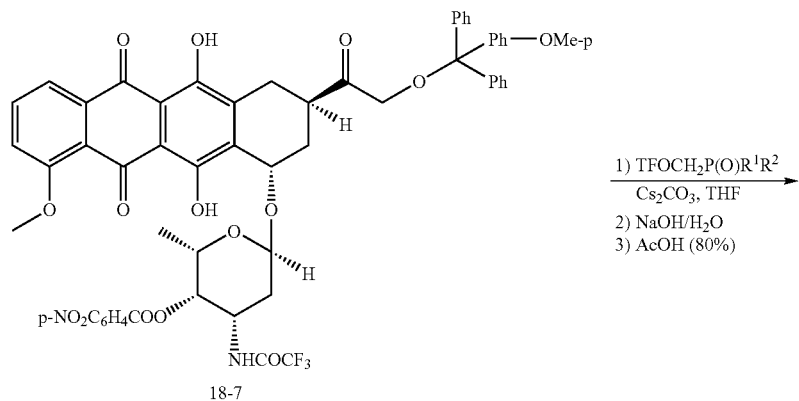

1) TFOCH₂P(O)R¹R²
   Cs₂CO₃, THF
2) NaOH/H₂O
3) AcOH (80%)

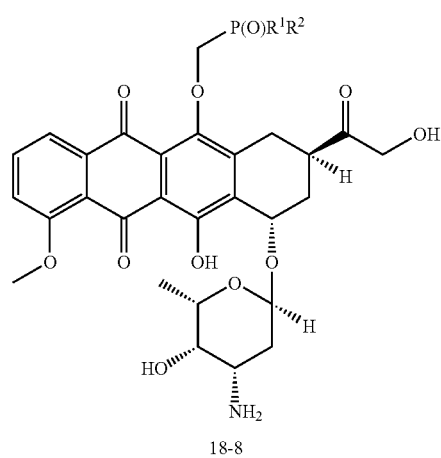

For example (Scheme 18.5), alkylation of tri-protected adriamycin 18-7 with phosphonate triflate, followed by basic (0.1N sodium hydroxide) and acidic (80% acetic acid) deprotection, afford compound 18-8.

Scheme 18.6

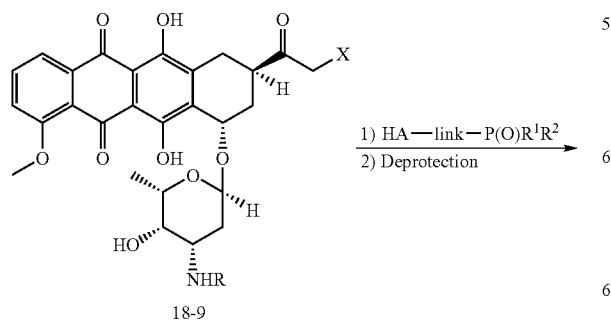

1) HA—link—P(O)R¹R²
2) Deprotection

-continued

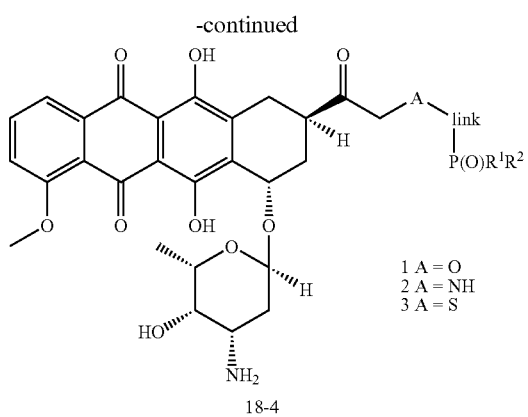

1 A = O
2 A = NH
3 A = S

As illustrated in Scheme 18.6, phosphonate analogs of type 18-4 are readily prepared from adriamycin intermediate 18-9

(*J. Med. Chem.* 1985, 28, 1223) via a displacement of the leaving group X with appropriate nucleophiles.

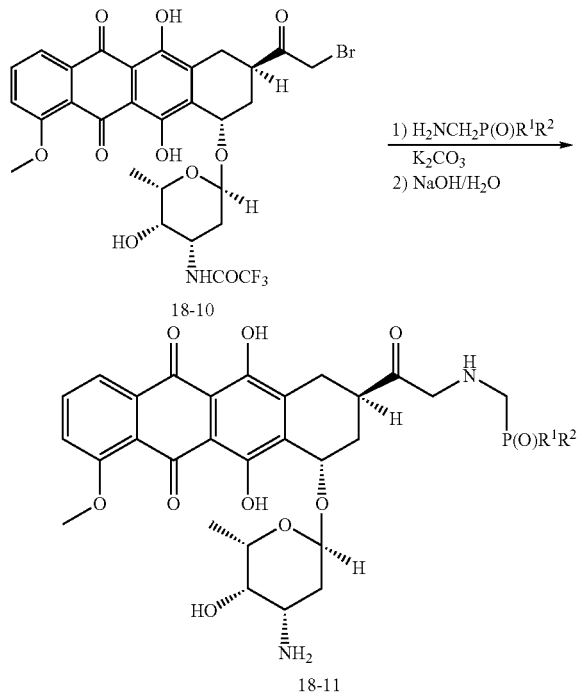

For example (Scheme 18.7), reaction of bromide 18-10 with phosphonate amine, followed by a deprotection, affords desired product 18-11.

Further manipulations can be performed on the phosphonate moiety prior to the final deprotection. These types of transformations are more extensively described in phosphonate interconversion section herein.

Example 19

Preparation of Exemplary Compounds of the Present Invention

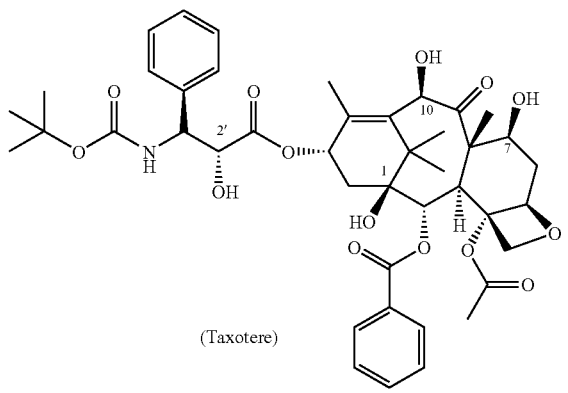

-continued

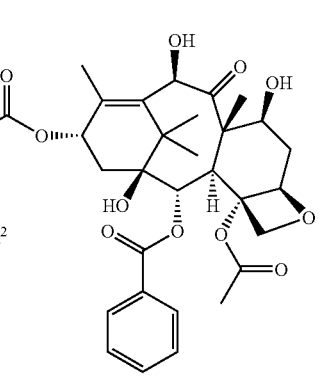

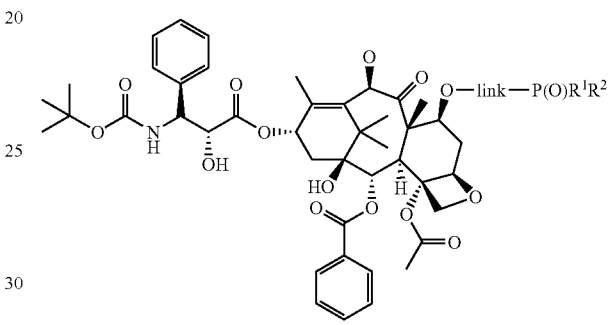

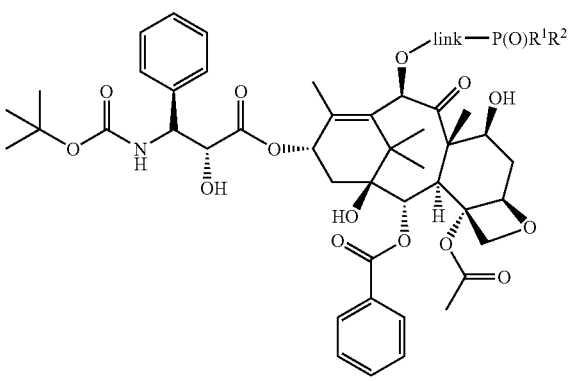

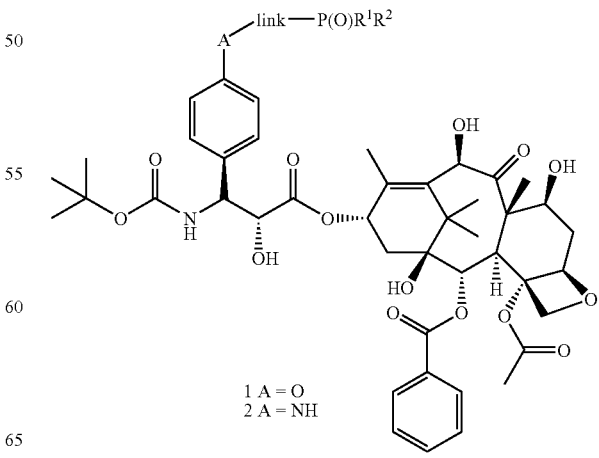

Exemplary compounds of the invention are illustrated above. Analogs of type 19-2, 19-3 and 19-4 are readily prepared from taxotere 19-1.

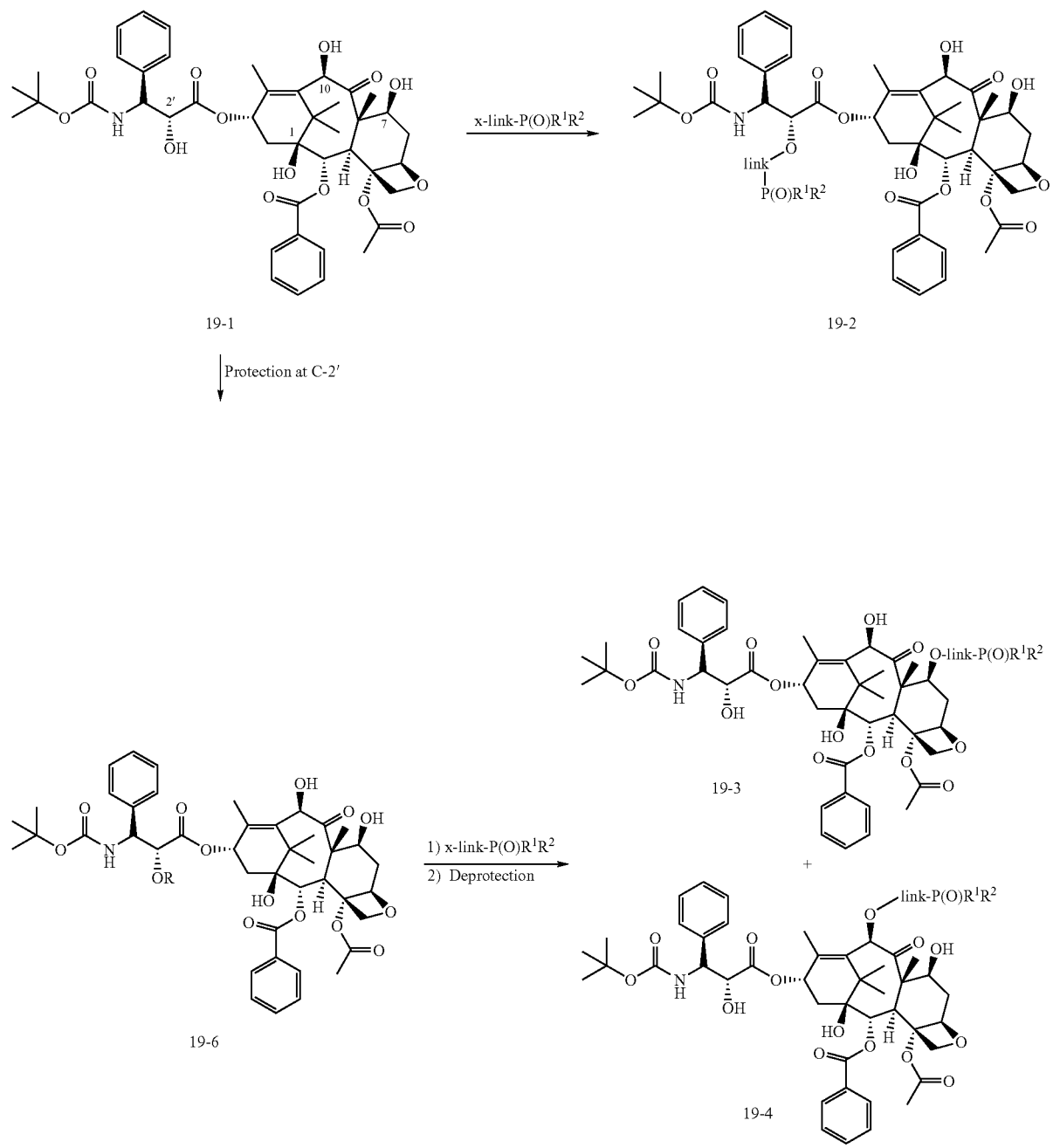

Direct alkylation of 19-1 with the phosphonate reagents give analogs of type 19-2 as major products (*Tetrahedron* 1993, 49, 2805). Selective protection of taxotere position at C-2' (*J. Org. Chem.* 1995, 60, 761) give 19-6, which are then alkylated with the phosphonate reagents, followed by deprotection, to afford analogs of type 19-3 and 19-4.

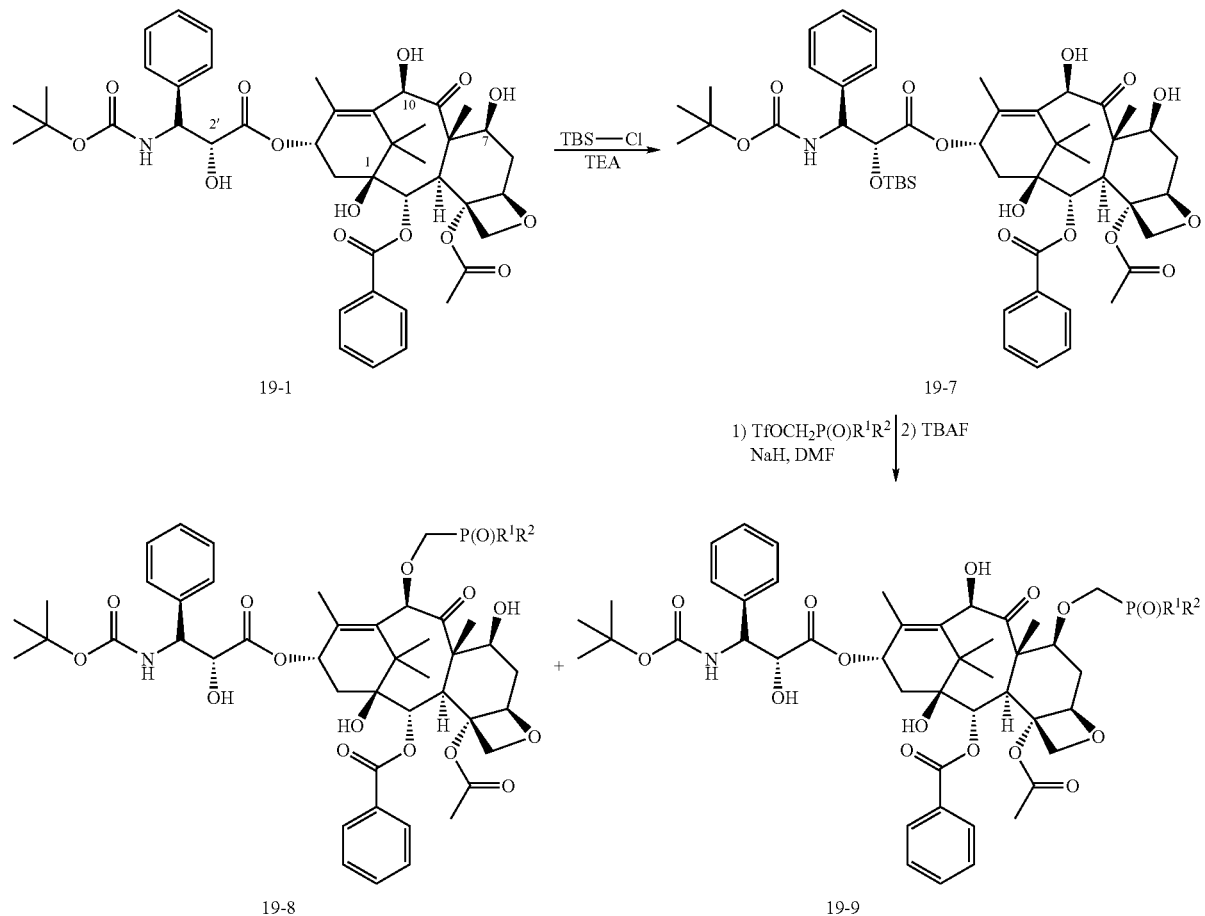

Scheme 19.3

For example (Scheme 19.3), treatment of taxotere 19-1 with tert-butyldimethylsilyl chloride and triethylamine in DMF give mono-TBS protected taxotere 19-7. Alkylation of 19-7 with phosphonate triflate, followed by deprotection with tetrabutylammonium fluoride, afford desired product 19-9 and 19-8. Direct alkylation of taxotere 19-1 with phosphonate triflate can afford analogs of type 19-2.

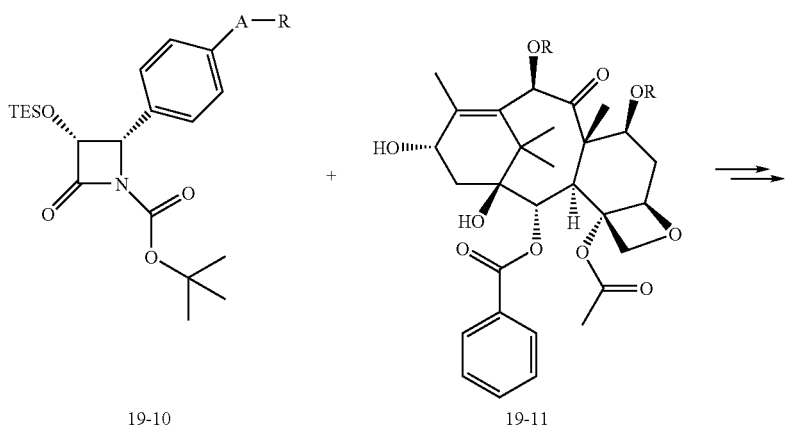

Scheme 19.4

-continued
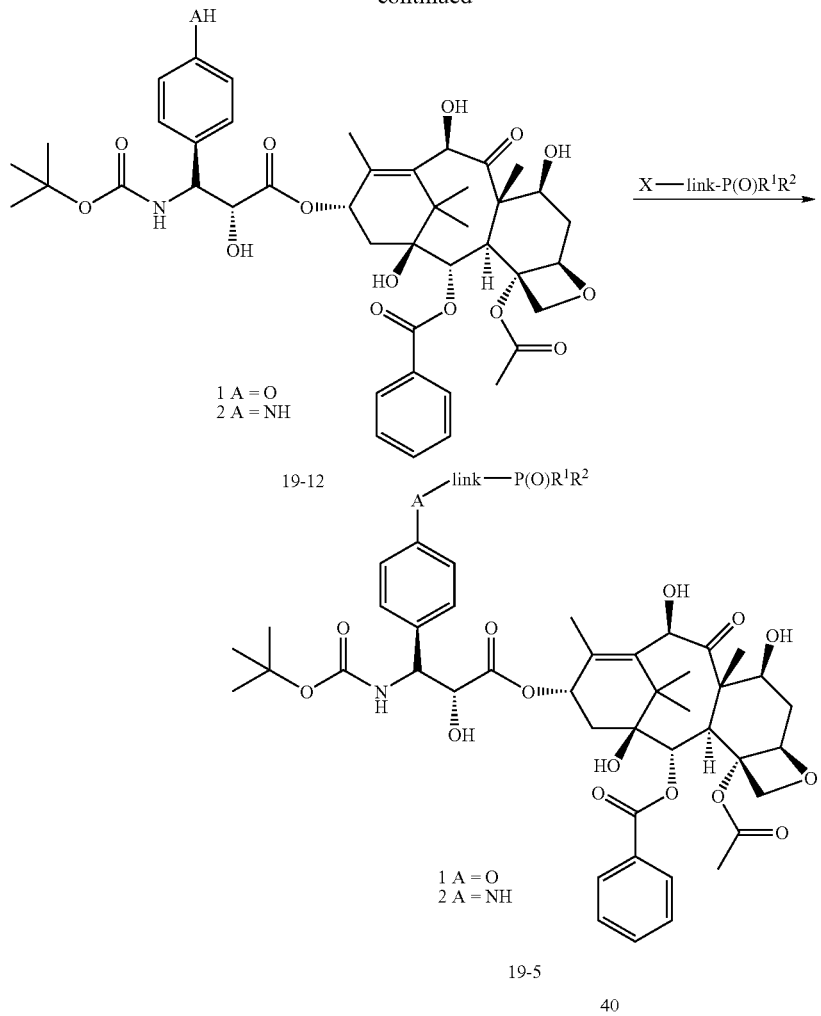
19-12
19-5
As illustrated in Scheme 19.4, analogs of type 19-5 can be obtained from taxotere analogs 19-12, which are accessible from β-lactam 19-10 and baccatin III (19-11) according to the methods reported in literature (*Bioorg. Med. Chem. Lett.* 1994, 4, 479; *Synlett* 1992, 761).
Scheme 19.5
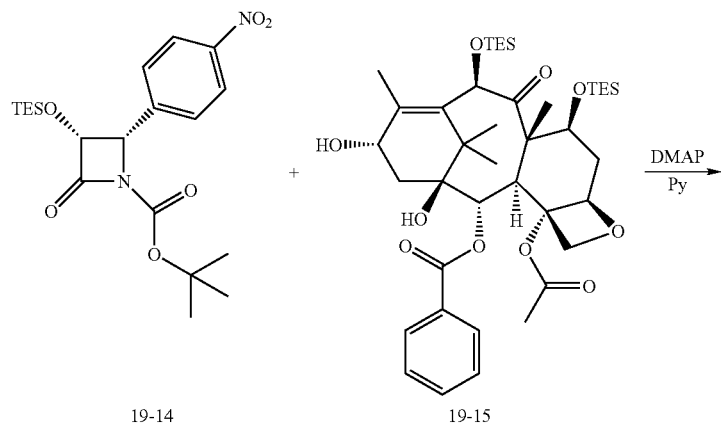
19-14        19-15

-continued

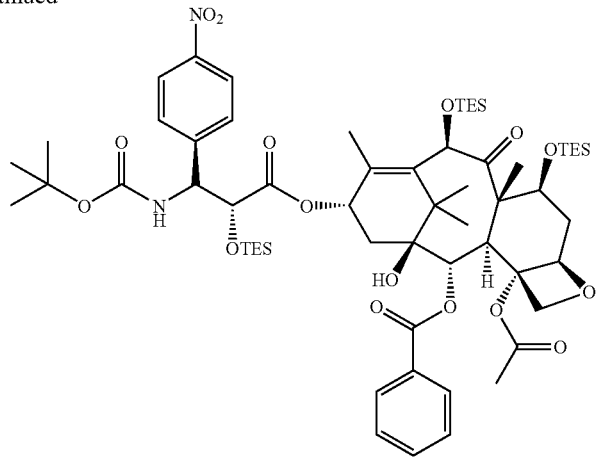

19-16

Zn/AcOH ↓

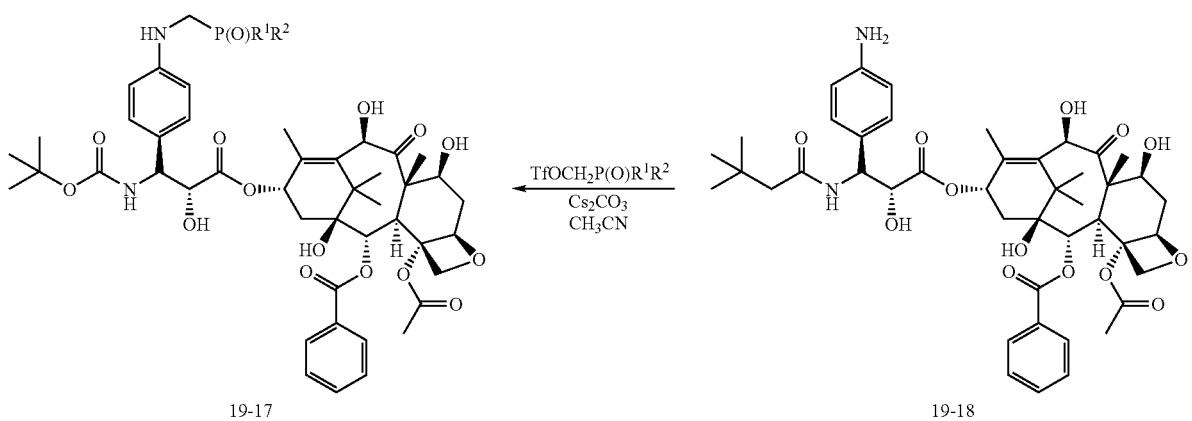

19-17     19-18

For example (Scheme 19.5), using 4-nitrobenzaldehyde (in place of benzaldehyde) as starting material, β-Lactam 19-14 is prepared by literature procedure (*Synlett* 1992, 761). Reaction of 19-14 with baccatin III 19-15 in the presence of 4-dimethylaminopyridine affords compound 19-16. Reduction of 19-16 with zinc in acetic acid affords amino compound 19-18. Alkylation of 19-18 with a phosphonate triflate reagent produces desired compound 19-17.

Further manipulations can be performed on the phosphonate moiety prior to the final deprotection. These types of transformations are more extensively described in the phosphonate interconversion section herein.

Example 20

Preparation of Exemplary Compounds of the Present Invention

Scheme 20.1

20-1

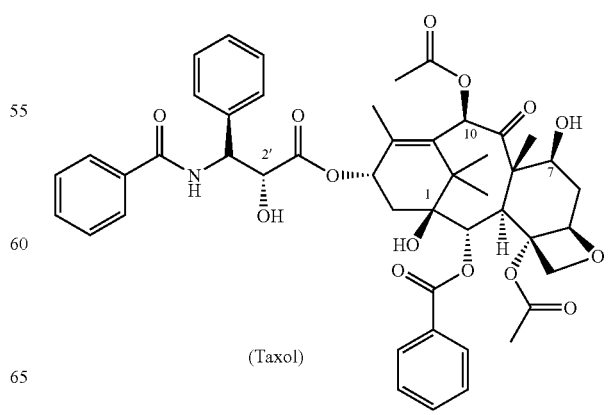

(Taxol)

-continued 20-2

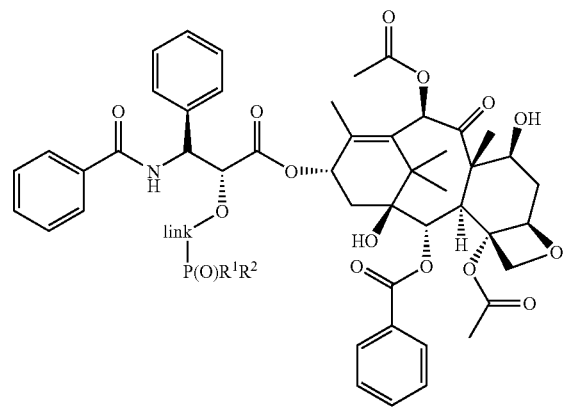

20-5

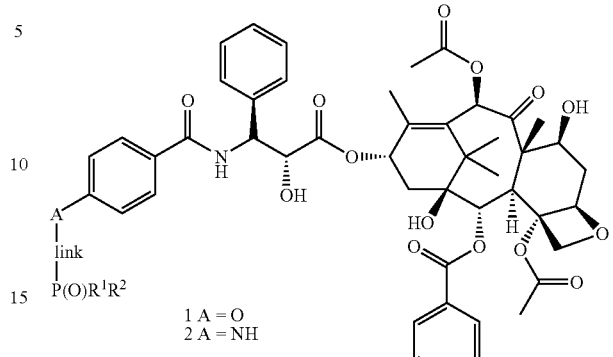

1 A = O
2 A = NH 20-3

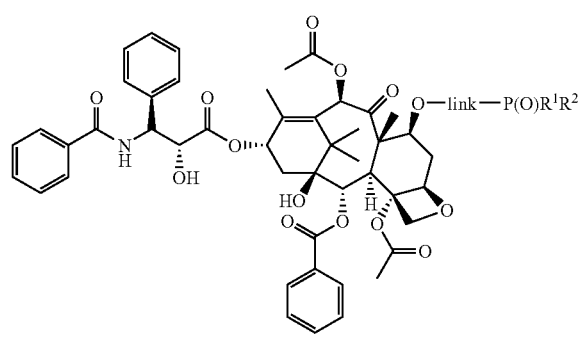

20-6

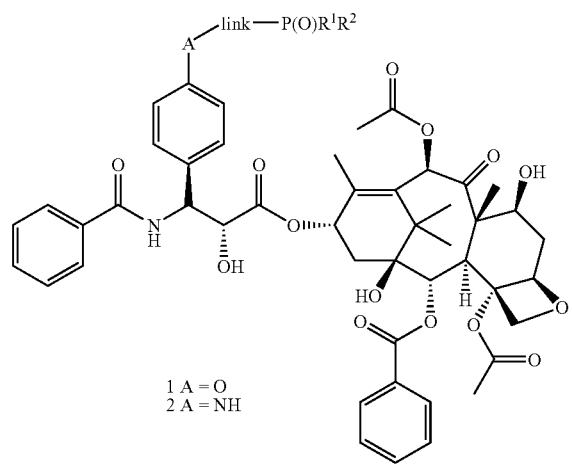

1 A = O
2 A = NH 20-4

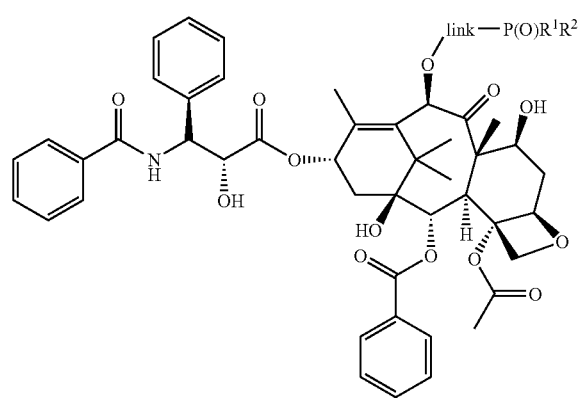

Further manipulations can be performed on the phosphonate moiety prior to the final deprotection. These types of transformations are more extensively described in the following section.

As illustrated in Scheme 20.2, phosphonate analogs of type 20-2, 20-3 and 20-4 are readily prepared from taxol 20-1. Direct alkylation of 20-1 with the phosphate reagents gives analogs of type 20-2 as major products (*Tetrahedron*, (1993), 49, 2805). Selection protection of taxol at C-2' position (*J. Org. Chem.* (1995), 60, 761) give 7, which are then alkylated with the phosphonate reagents, followed by deprotection, to afford analogs of type 20-3. Full protection of taxol at position C-2' and C-7 give 20-8, then the C-10 hydroxyl of 20-8 is revealed and alkylated with the phosphonate reagents, followed by deprotection, to furnish analogs of type 20-4. For example (Scheme 20.3), treatment of taxol 20-1 with excess of tert-butyldimethylsilyl chloride and triethylamine in DMF give bis-TBS protected taxol 8a. Treatment of 8a with hydrazine in ethanol gives compound 20-11 (*J. Org. Chem.* (1995), 60, 761). Alkylation of 20-11 with phosphonate triflate, followed by deprotection with tetrabutylammonium fluoride, afford desired product 20-10.

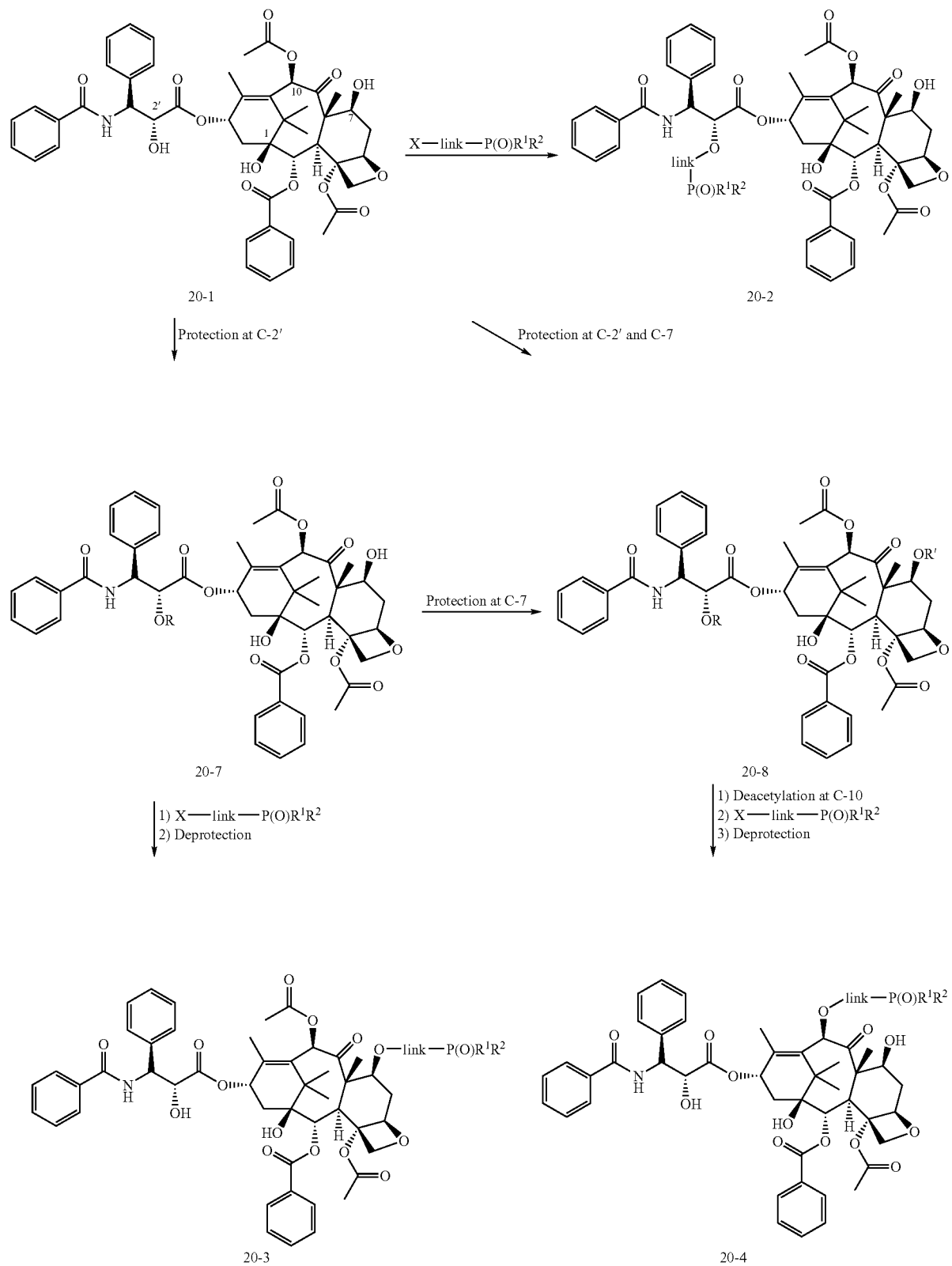

Scheme 20.3

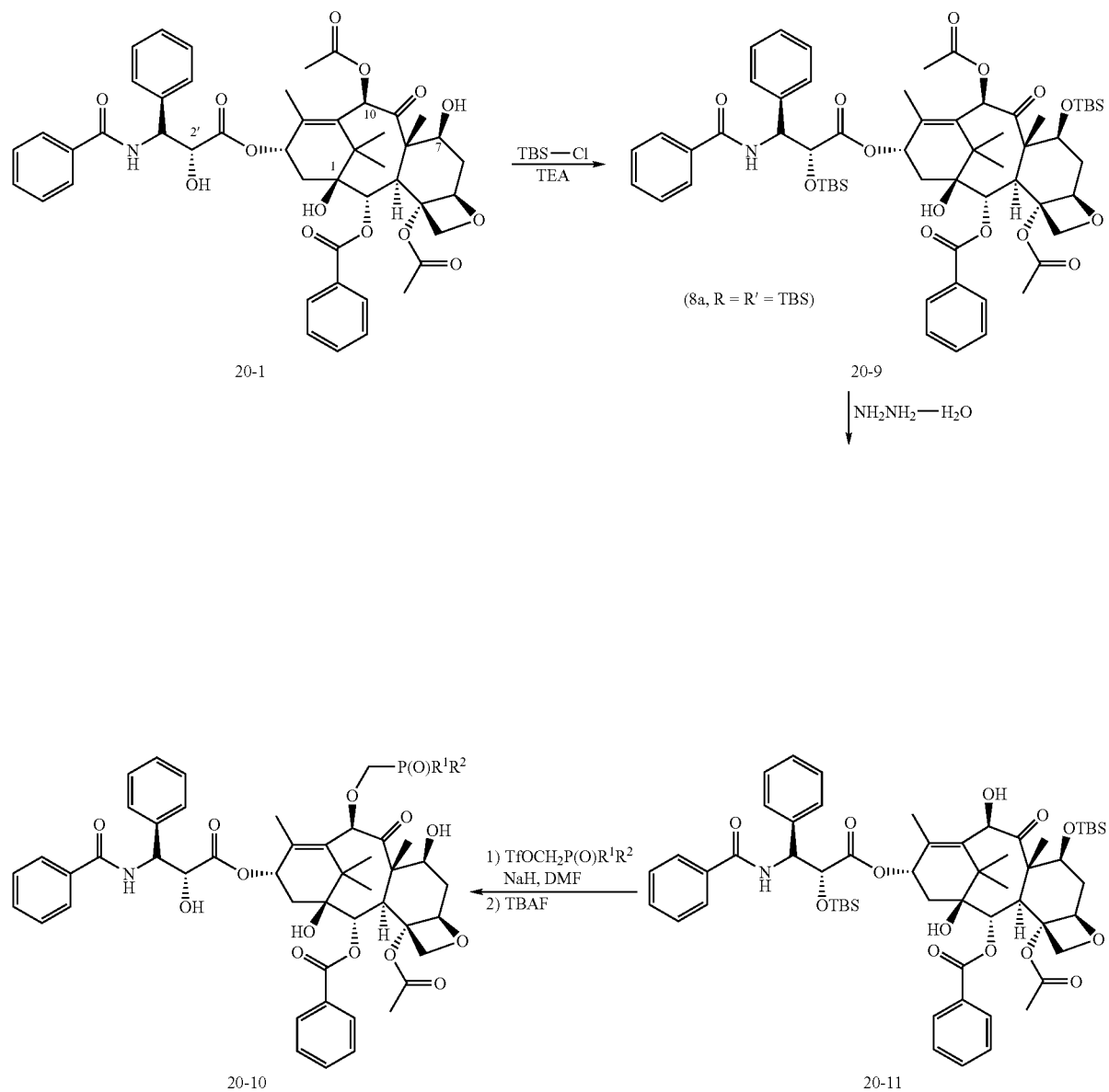

As illustrated in Scheme 20.4, analogs of type 20-5 can be obtained from taxol analogs 20-14, which are accessible from β-lactam 20-12 and baccatin III (20-13, 20-16) according to the methods reported in literature (*Bioorg. Med. Chem. Lett.* (1994), 4, 479; *Synlett.* (1992), 761). For example (Scheme 20.5), using 4-nitrobenzoyl chloride (instead of benzoyl chloride) as starting material, β-Lactam 20-15 is prepared by literature procedure (*Synlett*. (1992), 761). Reaction of 20-15 with baccatin III in the presence of 4-dimethylaminopyridine give compound 20-17. Reduction of 20-17 with zinc in acetic acid affords amino compound 20-19. Alkylation of 20-19 with phosphonate triflate reagent produces desired compound 20-18.

Scheme 20.4
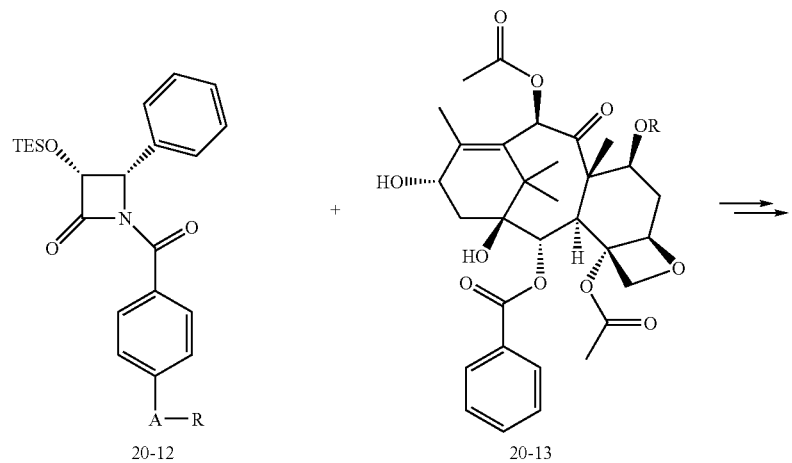
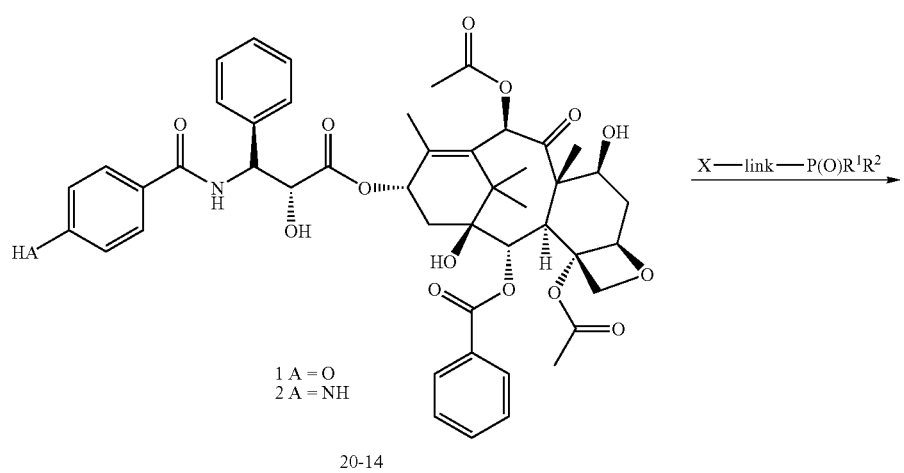
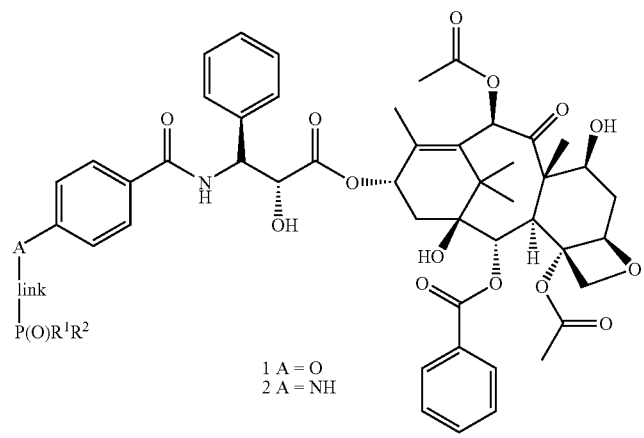

Scheme 20.5
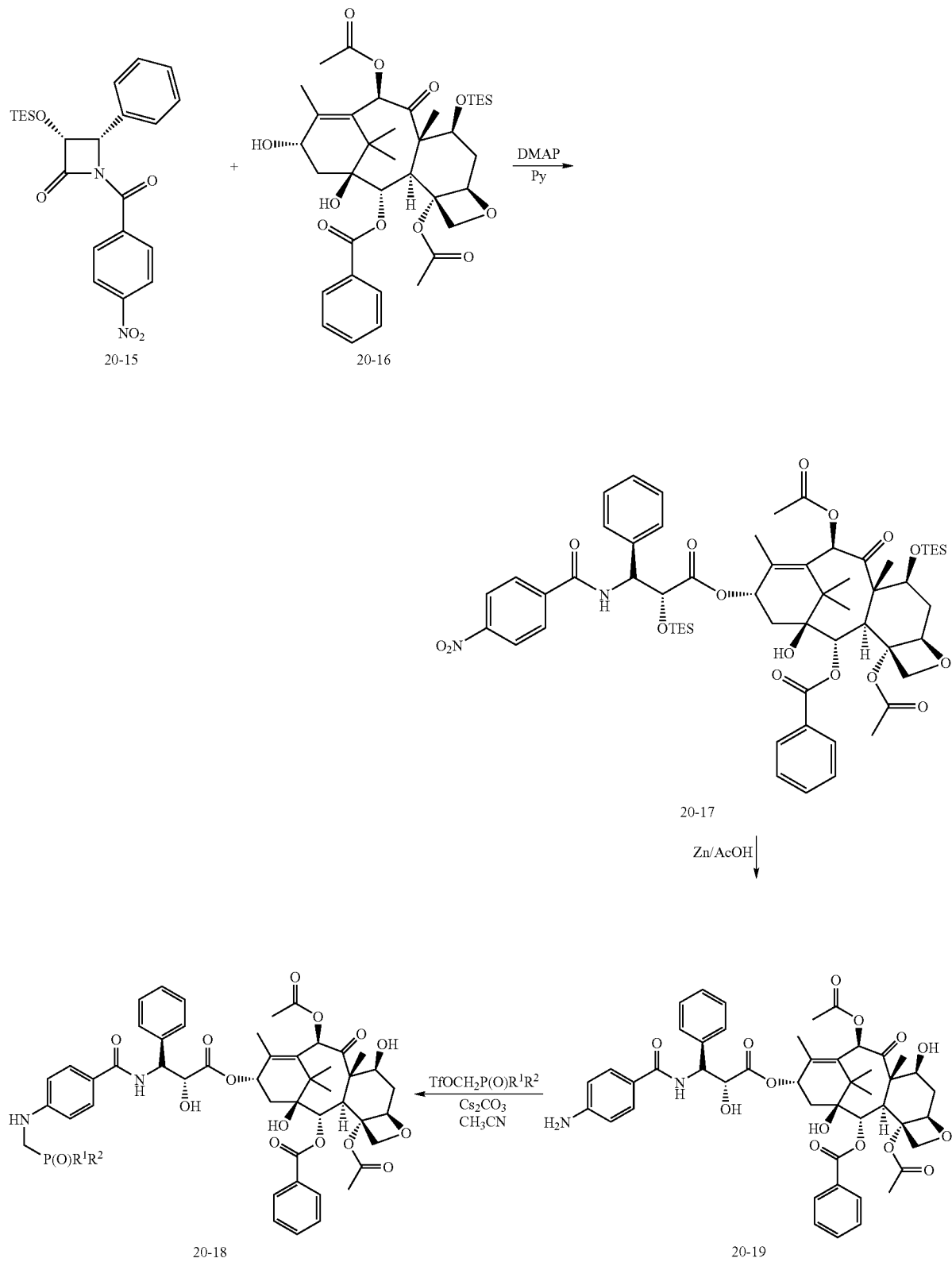

As shown in Scheme 20.6 and Scheme 20.7, analogs of type 20-6 can be prepared in the same fashion as type 20-5.
Scheme 20.6
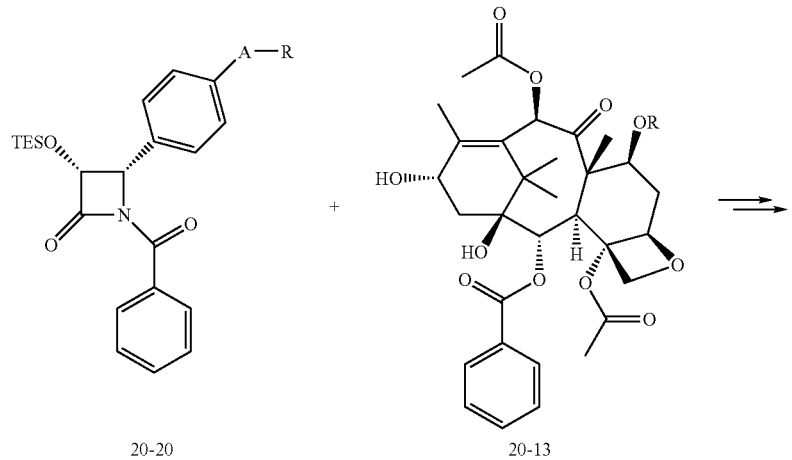
20-20 + 20-13 →
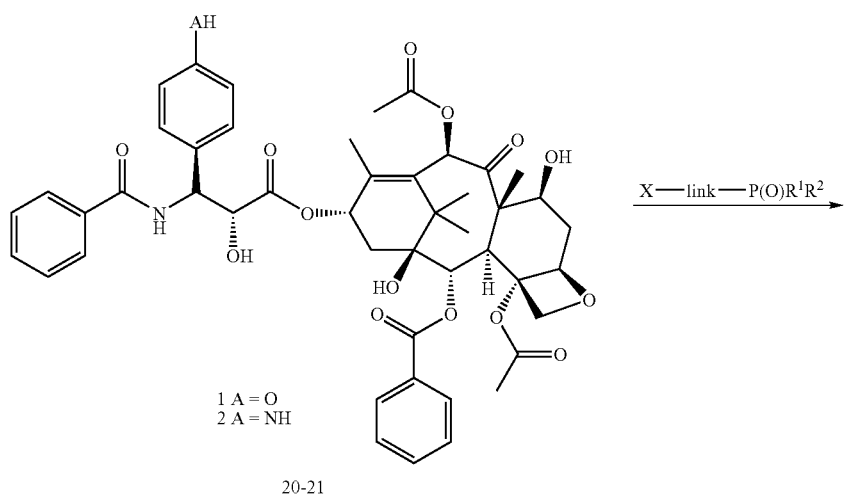
1 A = O
2 A = NH
20-21
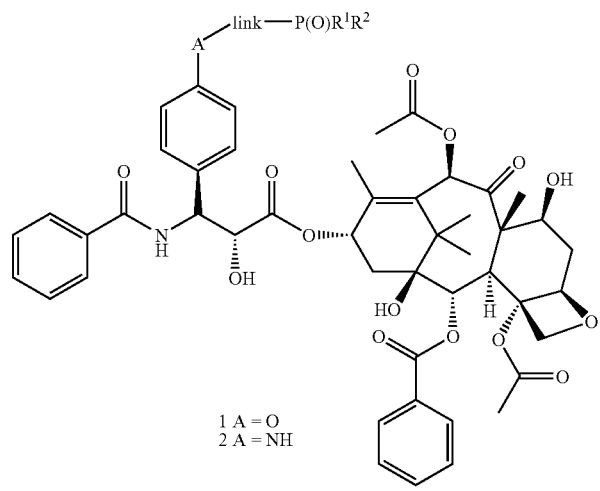
1 A = O
2 A = NH
20-6

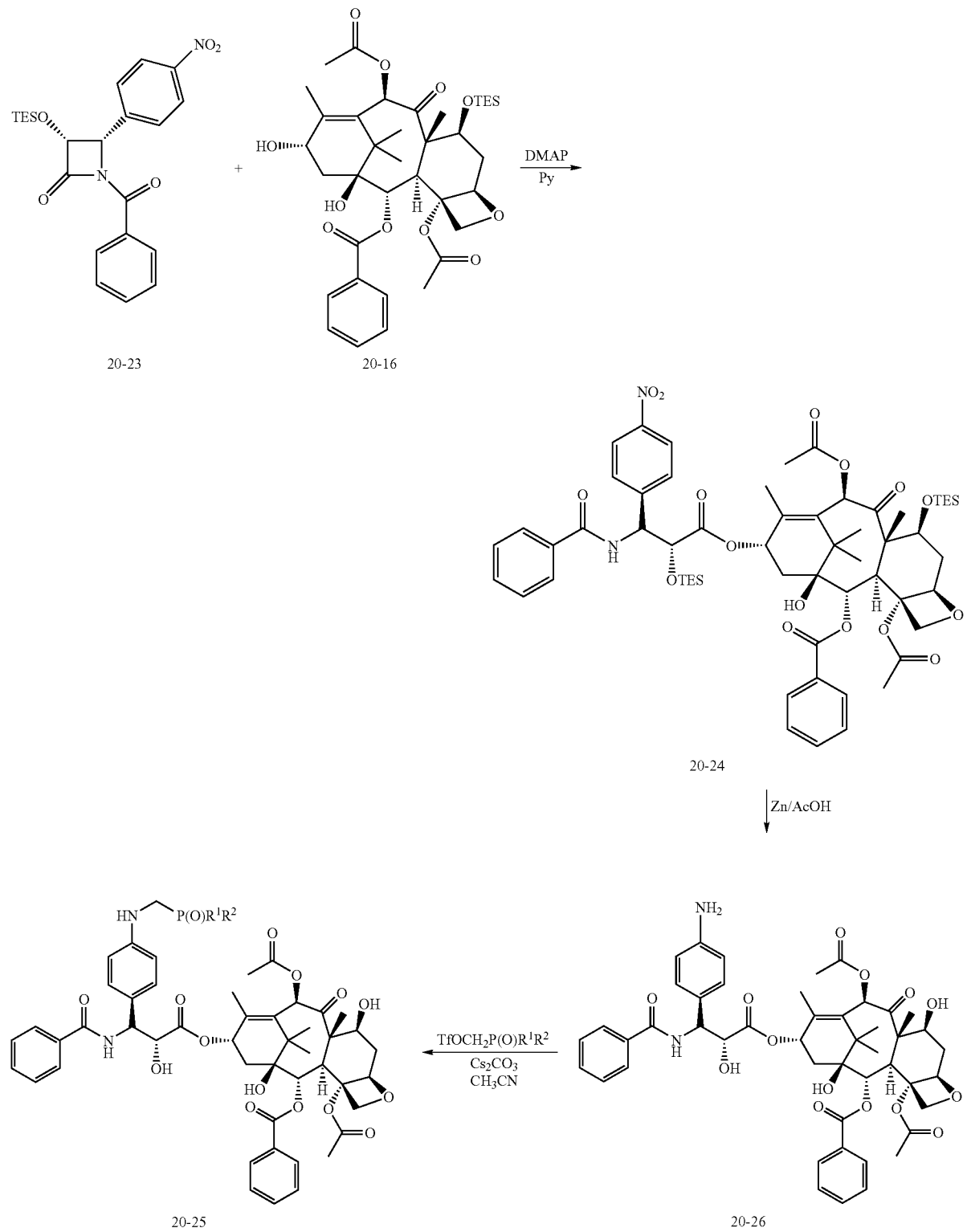

Example 21

Preparation of Exemplary Compounds of the Present Invention

Scheme 21.1

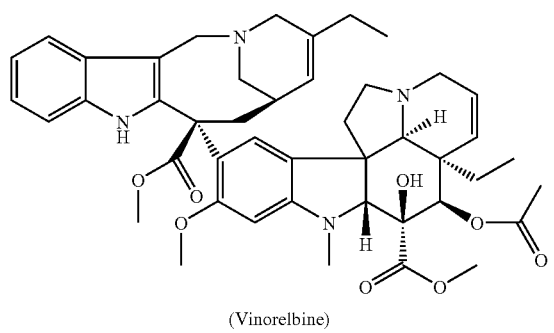

Further manipulations are performed on the phosphonate moiety prior to the final deprotection. These types of transformations are more extensively described in the following section.

As illustrated in Scheme 21.2, the strategy for the synthesis of phosphonate analogs of type 21-2 is first to introduce the phosphonate moiety into catharanthine 21-5 to give 21-7, which then is connected to vindoline 21-10 and converted into final compounds 21-2 using the same methods used in the synthesis of vinorelbine (Bioorg. Med. Chem. Lett. (2002), 12, 505; *Tetrahedron* (1980), 36, 3053).

Scheme 21.2

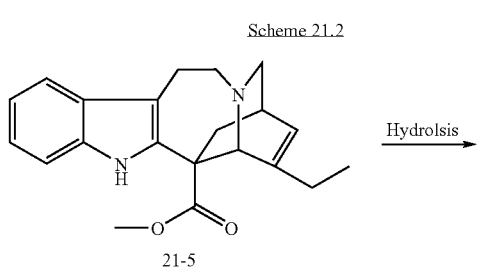
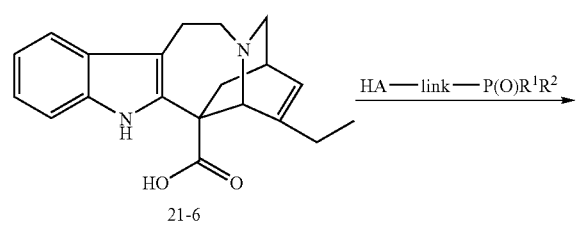
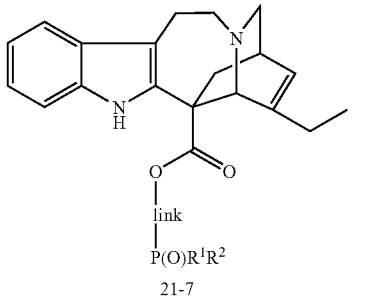
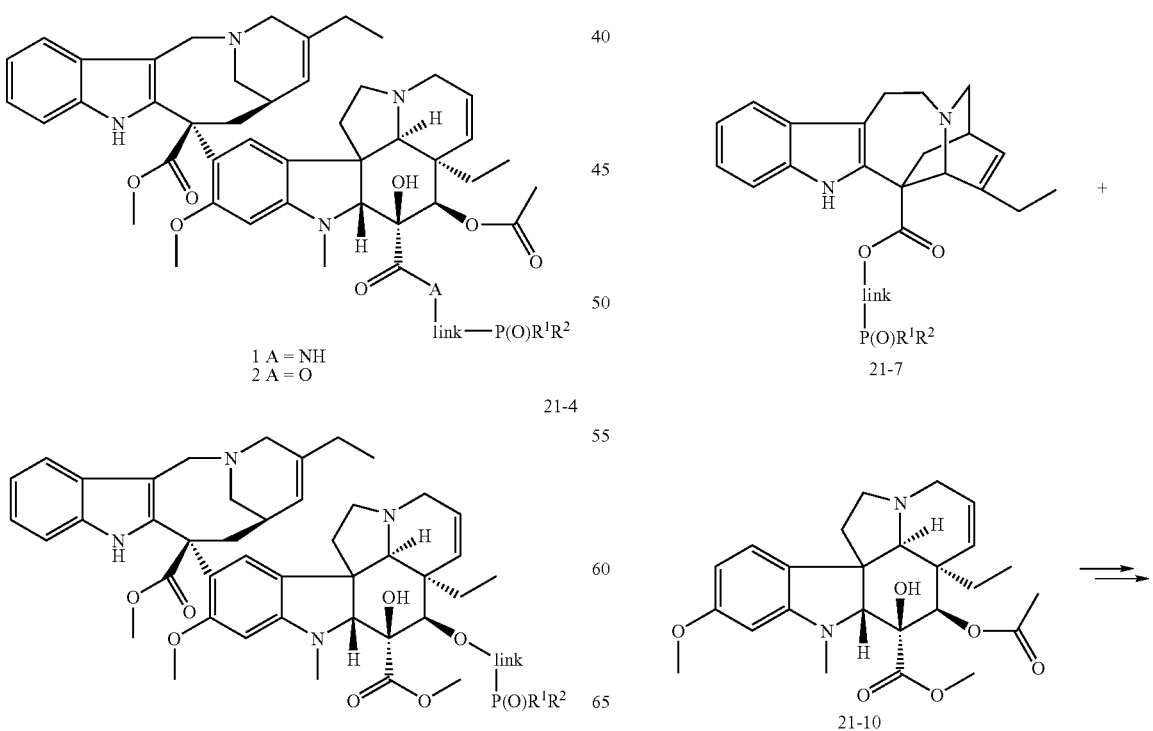

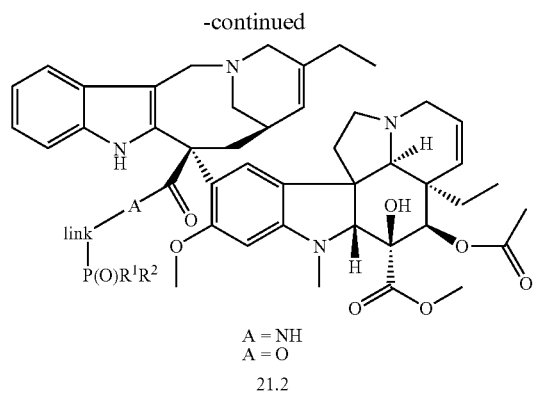

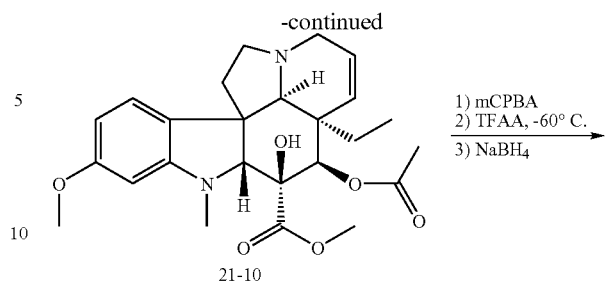

For example (Scheme 21.3), catharanthine 21-5 is hydrolyzed with sodium hydroxide to give 21-6. Coupling of 21-6 with phosphonate amine affords 21-9. The conversion of 21-9 and vindoline 21-10 into compound 21-11 is accomplished by sequential treatments of 3-chloroperoxybenzoic acid (mCPBA), trifluoroacetic anhydride (TFAA) and sodium borohydride. Treatment of 21-11 with N-bromosuccinimide (NBS), followed by silver tetrafluoroborate, affords desired compound 21-12.

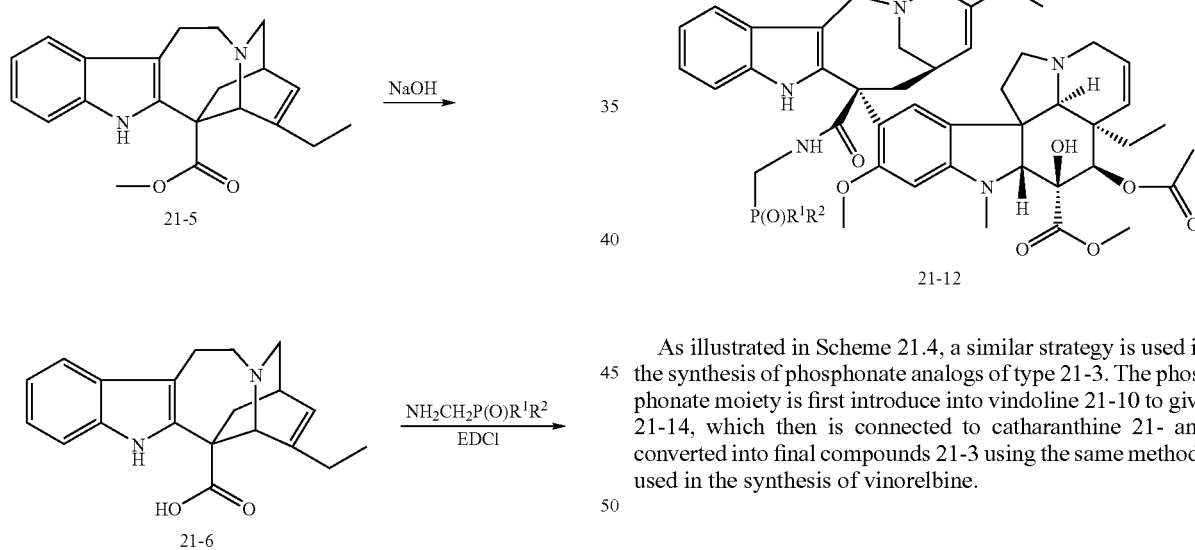

As illustrated in Scheme 21.4, a similar strategy is used in the synthesis of phosphonate analogs of type 21-3. The phosphonate moiety is first introduce into vindoline 21-10 to give 21-14, which then is connected to catharanthine 21- and converted into final compounds 21-3 using the same methods used in the synthesis of vinorelbine.

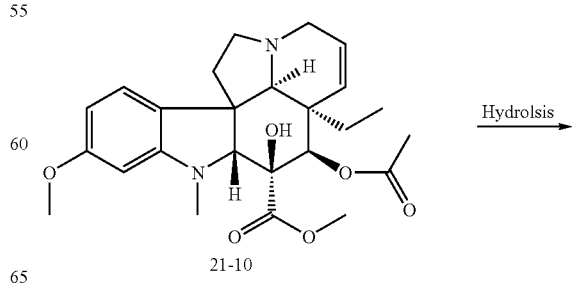

-continued
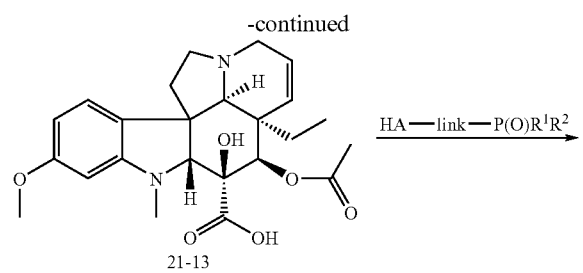
21-13
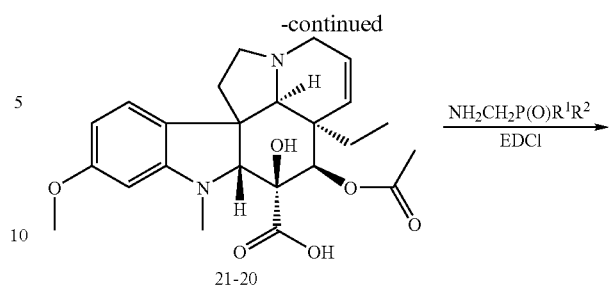
21-20
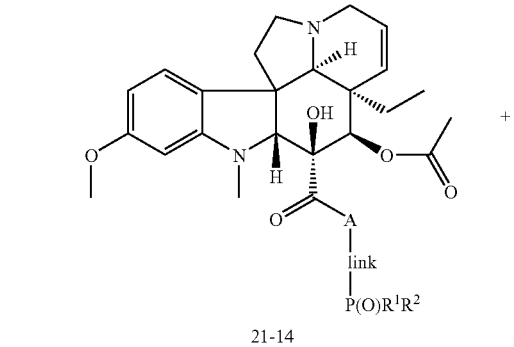
21-14
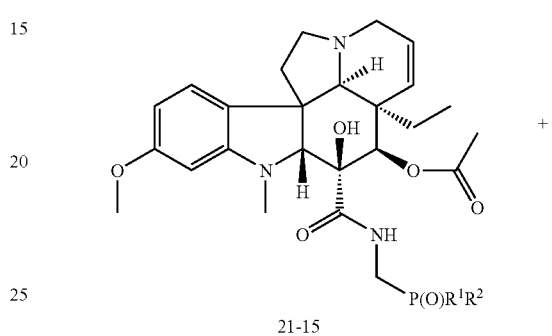
21-15
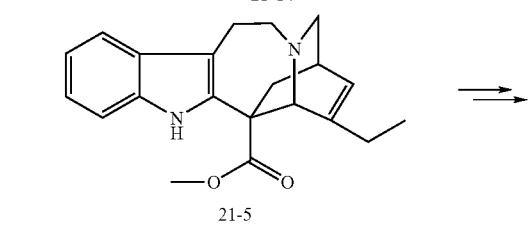
21-5
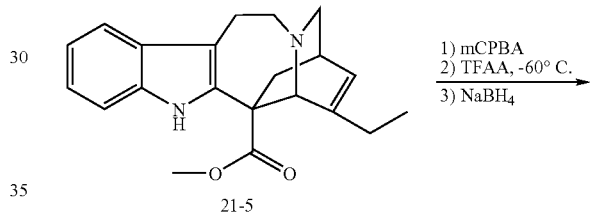
21-5
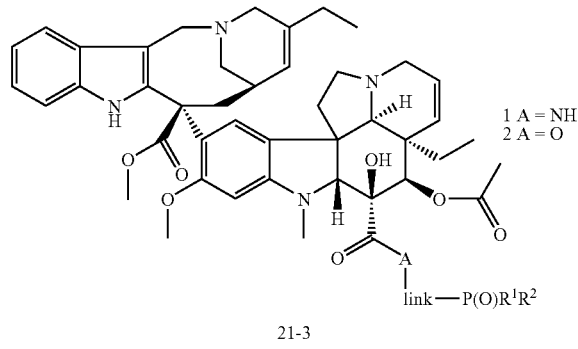
21-3
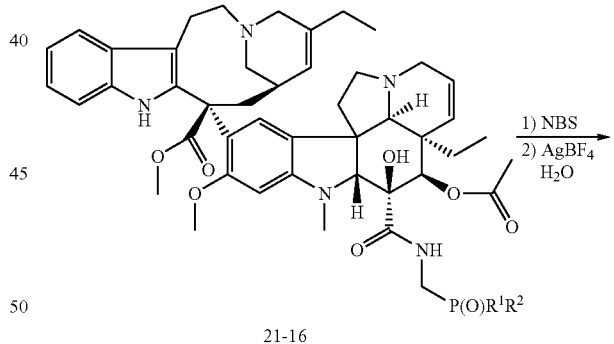
21-16
For example (Scheme 21.5), hydrolysis of vindoline 21-10 with sodium hydroxide, followed by reprotection of the hydroxyl, gives 21-20. Coupling of 21-20 with phosphonate amine affords 21-15. Finally, 21-15 and 21-5 are converted to desired product 21-17 in the same manner as described above.
Scheme 21.5
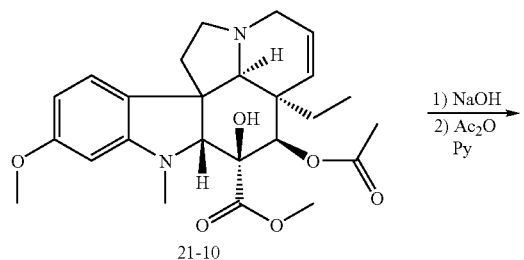
21-10
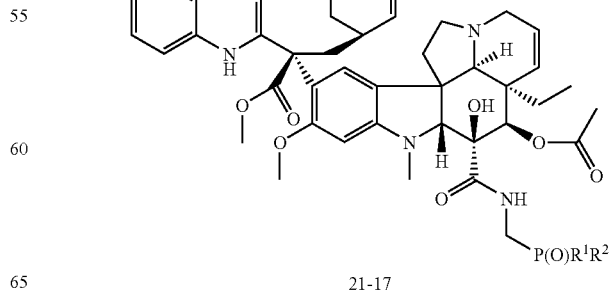
21-17

As illustrated in Scheme 21.6, phosphonate analogs of type 21-4 are readily prepared from vinorelbine 21-1. Hydrolysis of 21-1 gives 21-18, which is then alkylated with phosphonate reagents to afford analogs of type 21-4.

For example (Scheme 21.7), treatment of 21-1 with sodium methoxide in anhydrous methanol results in compound 21-18. Alkylation of 21-18 with phosphonate triflate in the presence of sodium hydride affords desired compound 21-19.

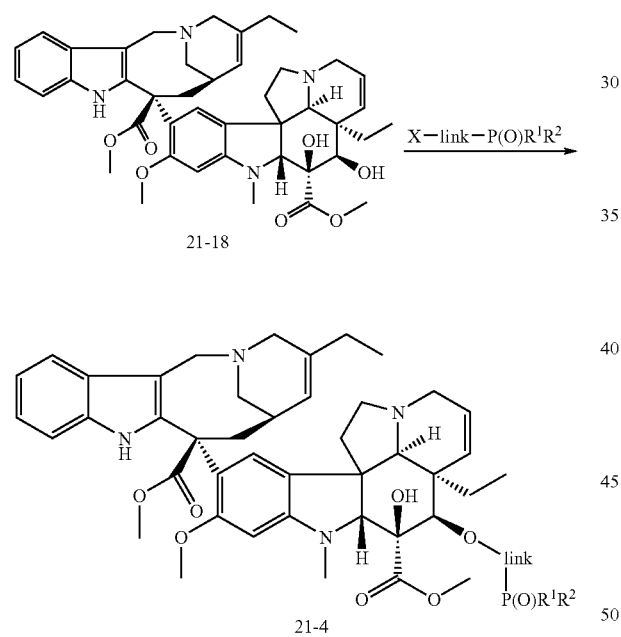

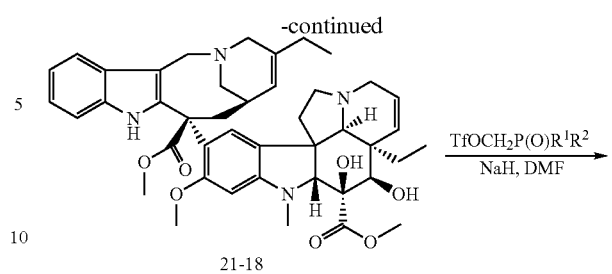

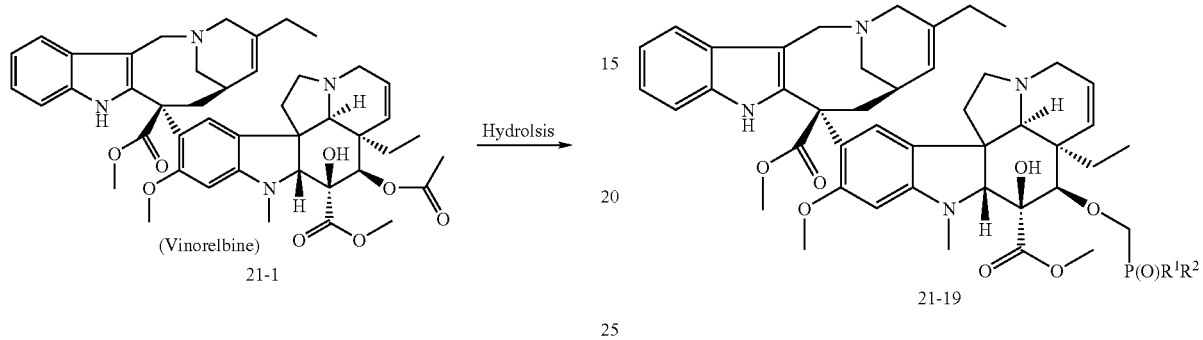

Example 22

Preparation of Exemplary Compounds of the Present Invention

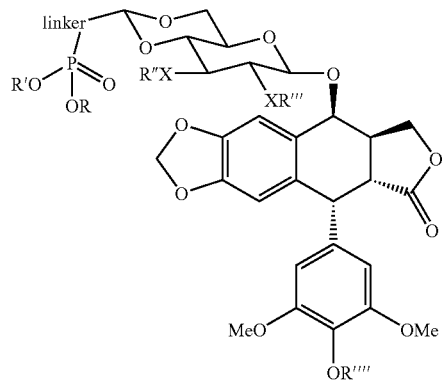

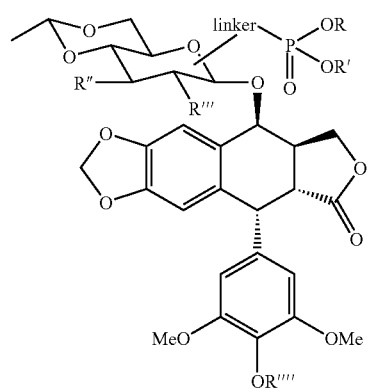

-continued
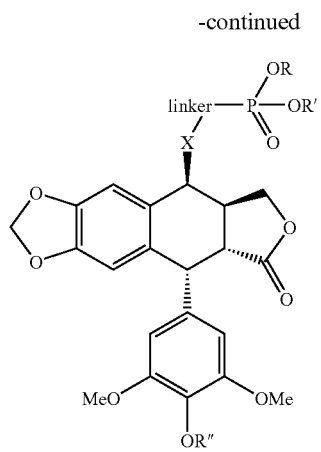
22-3
Compounds such as these can be made according to the general route outlined in Schemes 22.2-22.3, with examples depicted in Schemes 22.4-22.6.
Scheme 22.2: Modification of the sugar substituent
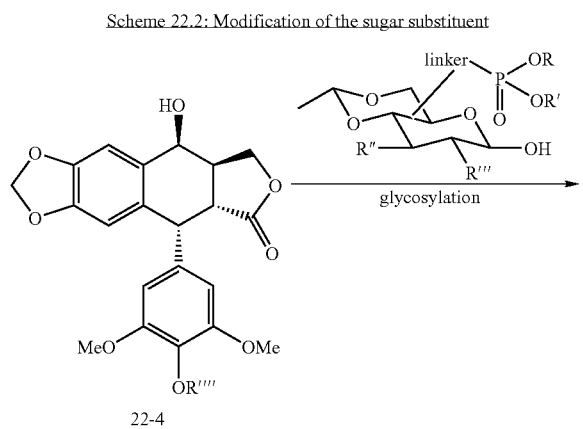
22-4
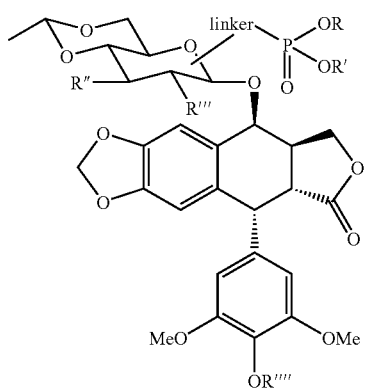
22-5
Scheme 22.3: Attachment to the epi-podophyllotoxin core
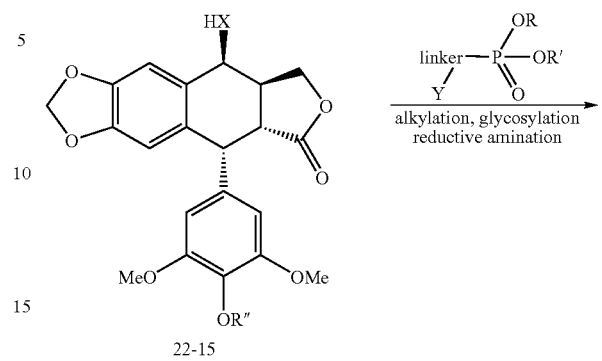
22-15
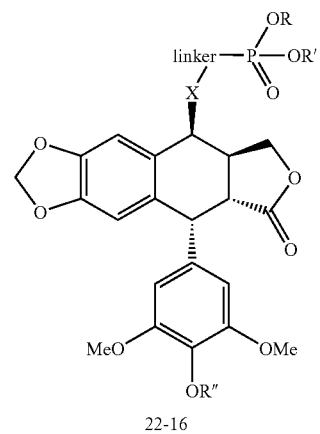
22-16
Scheme 22.4: Modification of the 4,6 glucose acetal moiety
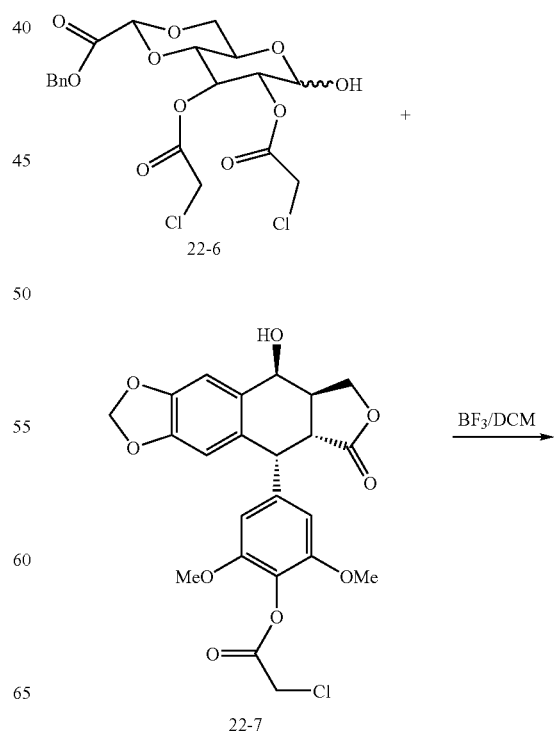
22-6
22-7

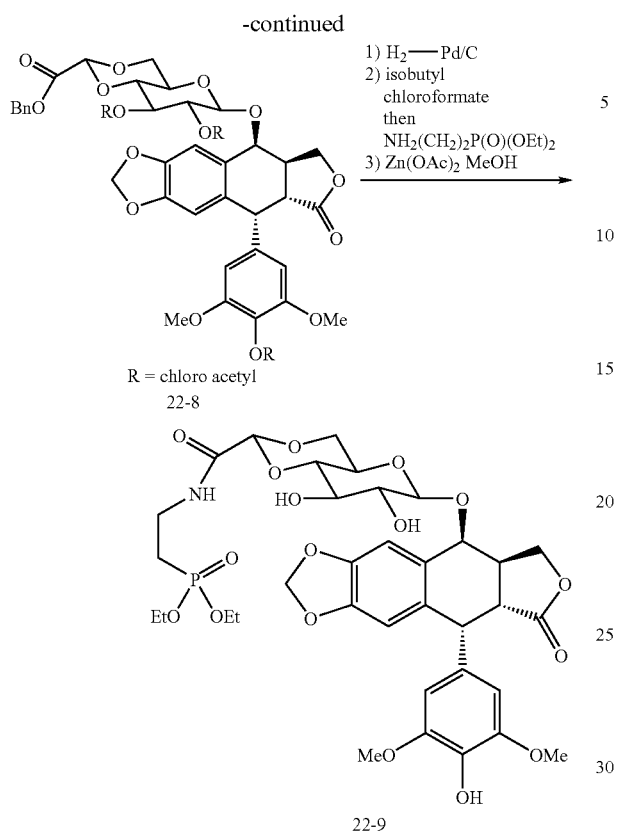

R = chloro acetyl
22-8

22-9

The glucose derived starting material is synthesized from glucose and benzyl glyoxylate (*J. Org. Chem.*, (2002), 67, 5408-5411) according to the methods described in *Chem. Lett.*, (1987), 799-802. The glycosidation reaction is performed with 4'chloroacetyl protected epipodophyllotoxin (described in the reference above) under catalysis of boron trifluoride (described in the reference above). The product of this reaction is dissolved in an organic solvent such as ethyl acetate and is hydrogenated in the presence of Pd/C under an atmosphere of hydrogen. The crude reaction mixture is filtered through Celite and the solvent is removed in vacuo. The crude reaction product is dissolved in an organic solvent such as DMF or chloroform and is then treated at a temperature of ~–10° C. with a tertiary amine base such as diisopropylethylamine (DIEA) and isobutyl chloroformate. After the activation is complete, 2-aminoethylphosphonic acid diethyl ester is added. After all starting material is consumed the reaction mixture is washed with aqueous 0.1 M HCl and aqueous bicarbonate solution. After drying and removal of the solvent the crude product of the coupling is obtained. Further purification is achieved by chromatography. The material is dissolved in an organic solvent such as methanol and is treated with zinc acetate at reflux temperature. At the end of the reaction, the mixture is cooled to room temperature and the solvent is removed in vacuo. The crude reaction product is dissolved in an organic solvent such as chloroform and the solution is washed with aqueous 0.1 M HCl and aqueous bicarbonate solution. After drying and removal of the solvent the crude final product is obtained. Further purification is achieved by chromatography.

Scheme 22.5: Modifications of the glucose core

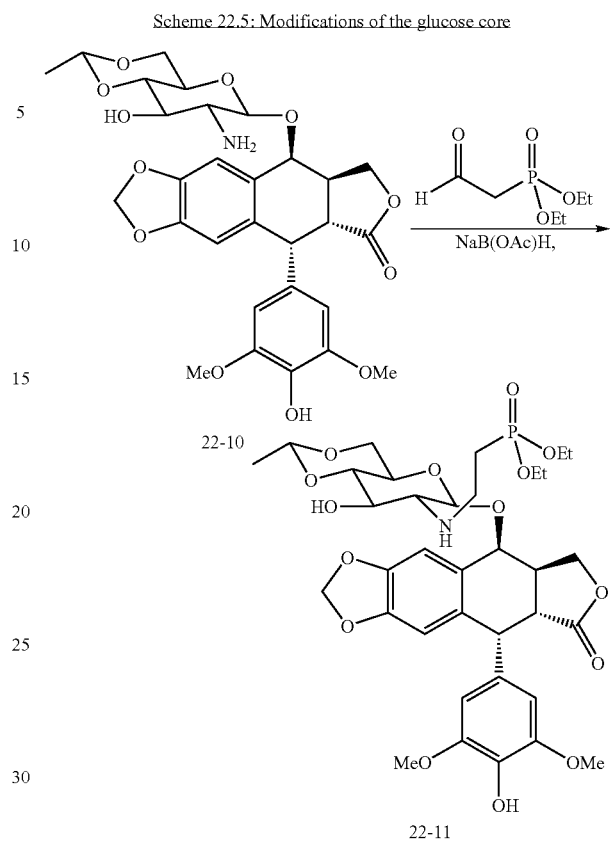

22-10

22-11

The starting material (synthesis according to *Chem. Lett.*, (1987), 799-804) is treated in an organic solvent such as DCM or THF with diethyl phosphonato ethyl carbaldehyde and sodium triacetoxyborohydride as described in *J. Org. Chem*, (1996), 61, 3849-3862. The reaction is quenched with aqueous sodium bicarbonate and the product is extracted with an organic solvent such as ethyl acetate. Further purification is achieved by chromatography.

Scheme 22.6: Attachment to the epi-podophyllotoxin core

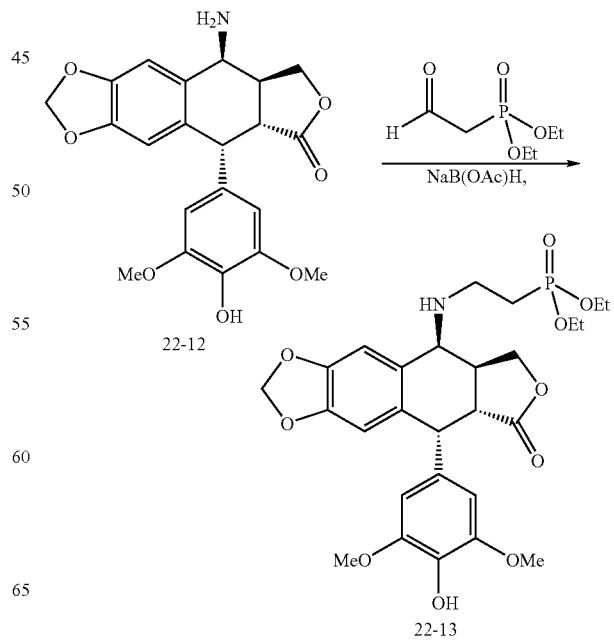

22-12

22-13

The amine containing starting material (obtained as described in *J. Med. Chem.*, (1991), 34, 3346-3350.) is treated in an organic solvent such as DCM or THF with diethylphosphonato-ethylcarbaldehyde and sodium triacetoxyborohydride as described in *J. Org. Chem*, (1996), 61, 3849-3862. The reaction is quenched with aqueous sodium bicarbonate and the product is T extracted with an organic solvent such as ethyl acetate. Further purification is achieved by chromatography.

All final products are converted to the corresponding 4' phosphate analogs via treatment of these compounds with phosphoryl trichloride in an organic solvent such as MeCN in the presence of an tertiary organic amine base such as DIEA, followed by treatment with aqueous bicarbonate solution as described in *Bioorg. Med. Chem. Lett.*, (1994), 21, 2567-2572. Final purification is achieved by chromatography.

Example 23

Preparation of Exemplary Compounds of the Present Invention

Compounds such as these are made according to the general route outlined in Schemes 23.1-23.6, with examples depicted in Schemes 23.7-23.12.

Scheme 23.1: Modification at C4

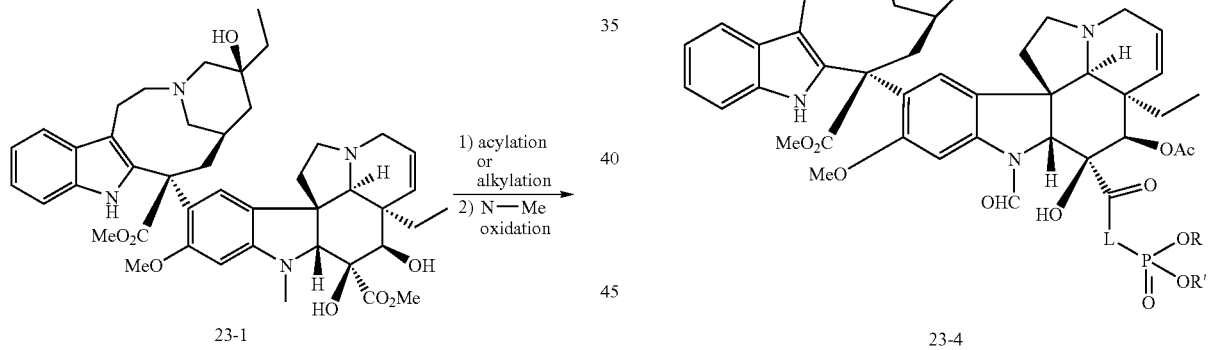

Scheme 23.2: Attachment to C23

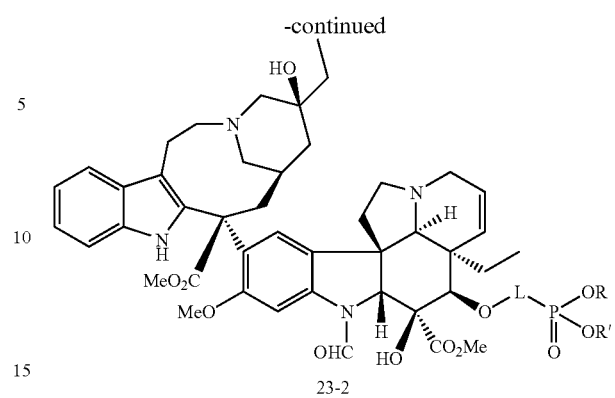

Scheme 23.3: Attachment to N1

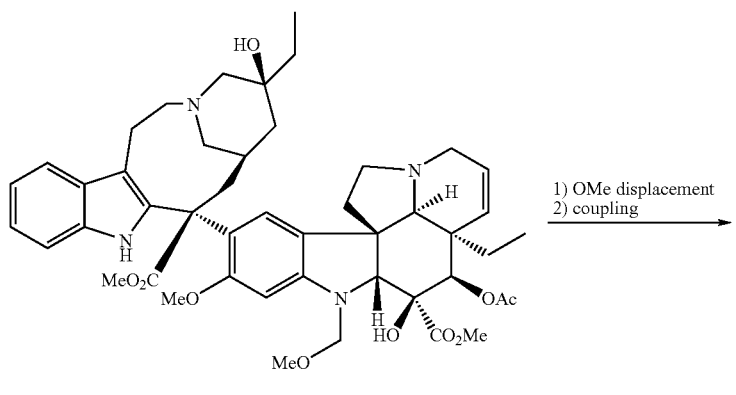

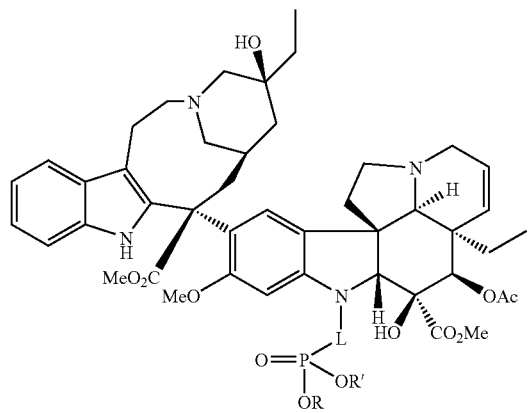
23-6
Scheme 23.4: Attachment to C4'
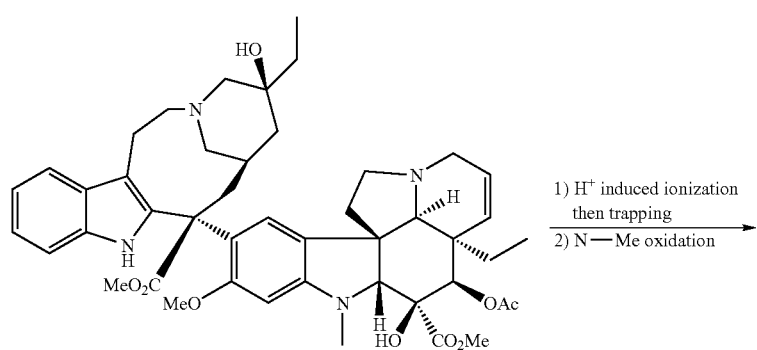
1) H+ induced ionization then trapping
2) N—Me oxidation
23-7
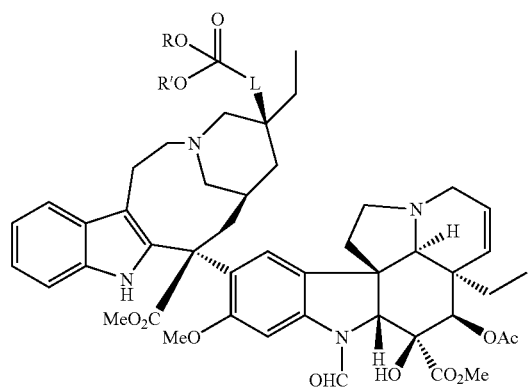
23-8

Scheme 23.5: Attachment to C12'
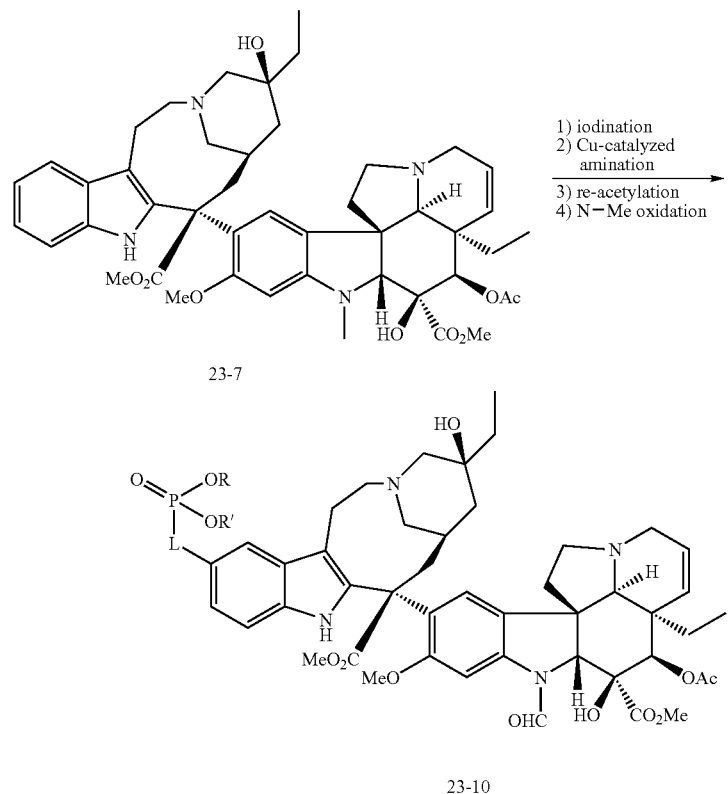
1) iodination
2) Cu-catalyzed amination
3) re-acetylation
4) N—Me oxidation
23-7
23-10
Scheme 23.6: Attachment to C22'
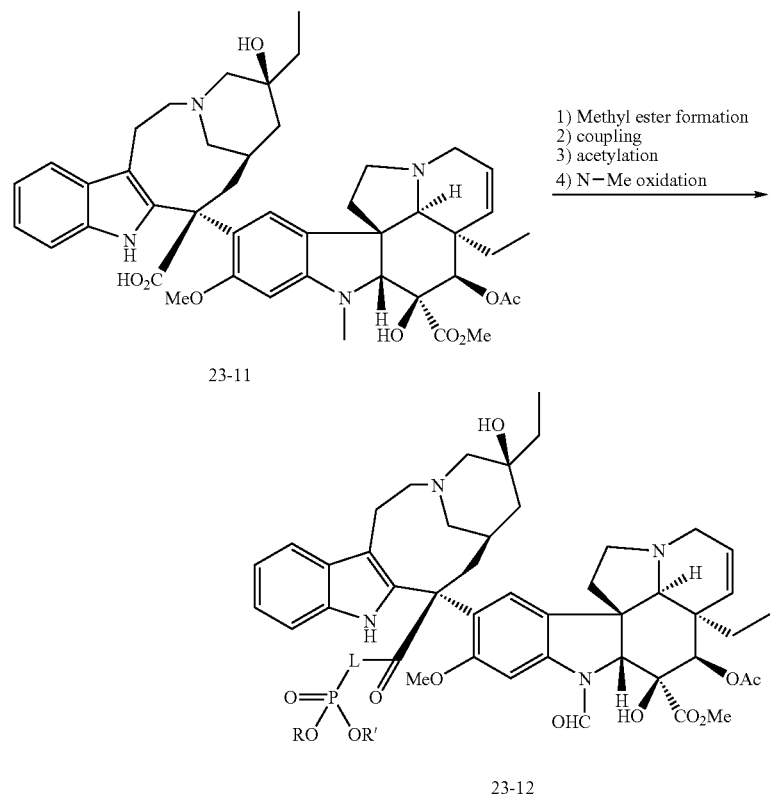
1) Methyl ester formation
2) coupling
3) acetylation
4) N—Me oxidation
23-11
23-12

Scheme 23.7: Attachment to C4

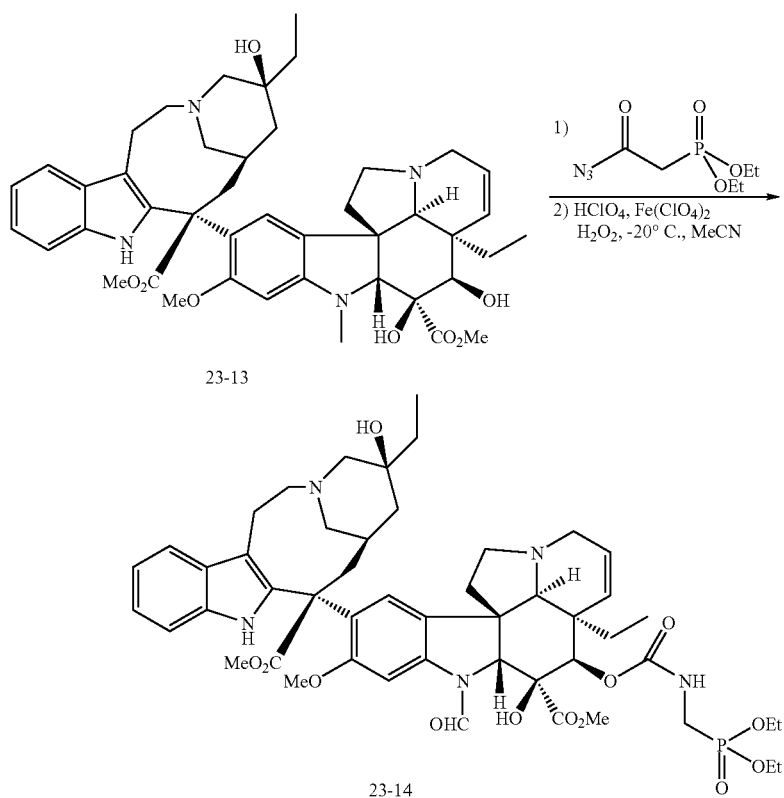

2-Diethyl phosphonatoacetic acid dissolved in an organic solvent such as benzene, tetrahydrofuran (THF), or chloroform, is combined with a tertiary amine base such as diisopropylethylamine (DIEA) and diphenyl phosphorazidate (1.2 equiv) and is stirred at room temperature according to *J. Med. Chem.*, (1991), 34, 1001-1018. After the acyl azide has been formed, 4-deacetylvinblastine (prepared from vinblastine according to *J. Med. Chem.*, (2002), 45, 4706-4715) is added, and the reaction mixture is heated to ~80° C. for ~4 hrs (*Biochemistry* (2002), 41, 14010-14018). The reaction mixture is cooled to room temperature and is washed with aqueous hydrochloric acid (HCl) (1N) and aqueous bicarbonate solution and dried. Removal of the solvents yields the crude product. Further purification is achieved by chromatography.

The product of this step is dissolved in an organic solvent such as acetonitrile and the solution is cooled to −20° C. A strong inorganic acid such as perchloric acid (2 equiv) is added, followed by ferrous perchlorate and hydrogen peroxide (excess), according to Pearce, "Medicinal Chemistry of Bisindole Alkaloids from Catharanthus", in *The Alkaloids*, Vol. 37, 145, Academic Press San Diego, (1990). At the end of the reaction aqueous ammonium hydroxide is added and the reaction mixture is extracted with an organic solvent such as dichloromethane (DCM). Removal of solvents in vacuo yields the crude product. Further purification is achieved by chromatography.

Scheme 23.8: Attachment to C23

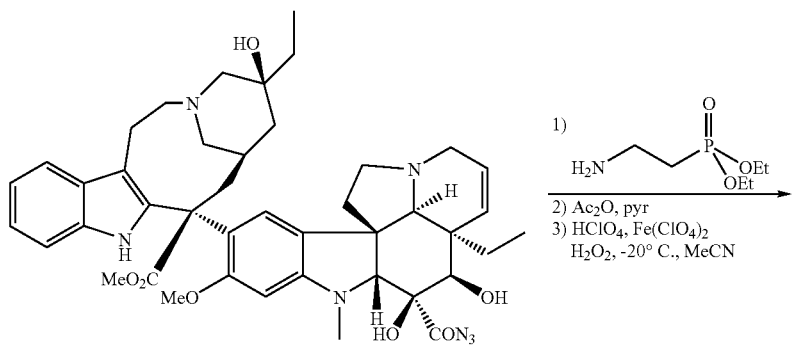

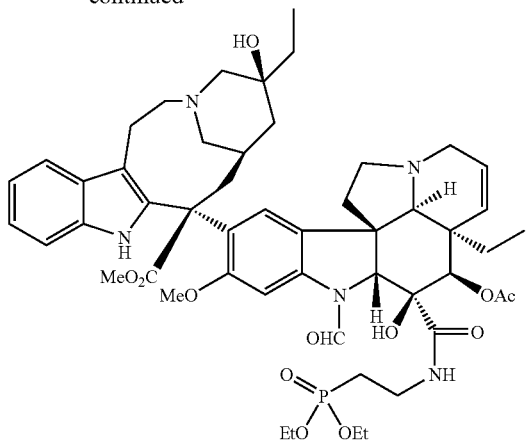

23-16

The starting material (synthesis published in *J. Med. Chem.*, (1978), 21, 88-96; from vinblastine) is treated in an organic solvent such as DCM or THF with 2-aminoethylphosphonic acid diethyl ester at room temperature, according to the procedure described in *J. Med. Chem*, (1979), 22, 391-400. At the end of the reaction, the solution is washed with water, aqueous bicarbonate and water, and is dried. Evaporation of solvents yields the crude product. Further purification is achieved by chromatography.

The product of this step is dissolved in an organic solvent such as DCM or THF. Pyridine is added, followed by acetic anhydride, and the reaction is stirred at room temperature according to *J. Med. Chem.*, (1979), 22, 391-400. At the end of the reaction, methanol is added and the solvents are removed in vacuo. The crude material is dissolved in an organic solvent such as DCM, washed with water and aqueous bicarbonate solution and dried. Removal of the solvents in vacuo yields the crude product. Further purification is achieved by chromatography.

The product of this step is dissolved in an organic solvent such as acetonitrile and the solution is cooled to –20° C. A strong inorganic acid such as perchloric acid (2 equiv) is added, followed by ferrous perchlorate and excess hydrogen peroxide, according to Pearce, "Medicinal Chemistry of Bisindole Alkaloids from Catharanthus", in *The Alkaloids*, Vol. 37, 145, Academic Press San Diego, (1990). At the end of the reaction aqueous ammonium hydroxide is added and the reaction mixture is extracted with an organic solvent such as DCM. Removal of solvents in vacuo yields the crude product. Further purification is achieved by chromatography.

Scheme 23.9: Attachment to N1

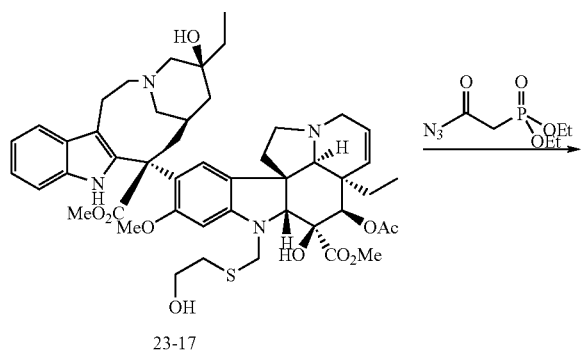

23-17

-continued

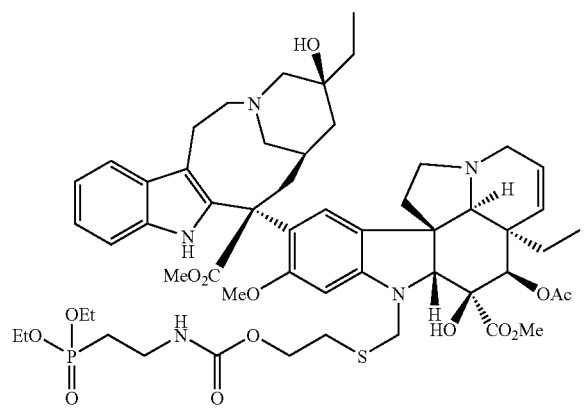

23-18

2-Diethyl phosphonatoacetic acid is dissolved in an organic solvent such as benzene, THF, or chloroform, and is combined with a tertiary amine base such as diisopropylethylamine (DIEA) and diphenyl phosphorazidate (1.2 equiv) and is stirred at room temperature, according to *J. Med. Chem.*, (1991), 34, 1001-1018. After the acyl azide has been formed, N-1-(β-hydroxyethylthiomethyl)vinblastine (prepared according to Pearce, "Medicinal Chemistry of Bisindole Alkaloids from Catharanthus", in The Alkaloids, Vol. 37, 145, Academic Press San Diego, (1990), from vinblastine via $CrO_3$-mediated oxidation in the presence of methanol and subsequent methoxy displacement with β-hydroxy thioethanol) is added, and the reaction mixture is heated to 80° C. for ~4 hrs (*Biochemistry* (2002), 41, 14010-14018). The reaction mixture is cooled to room temperature, washed with aqueous HCl (1N) and aqueous bicarbonate solution, and dried. Removal of the solvents yields the crude product. Further purification is achieved by chromatography.

Scheme 23.10: Attachment to C4'

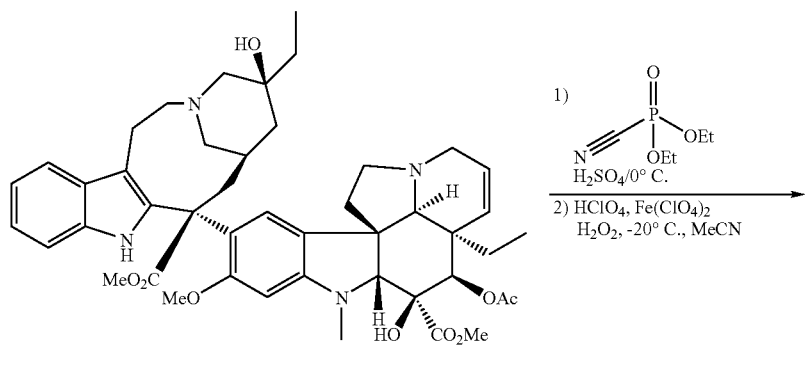

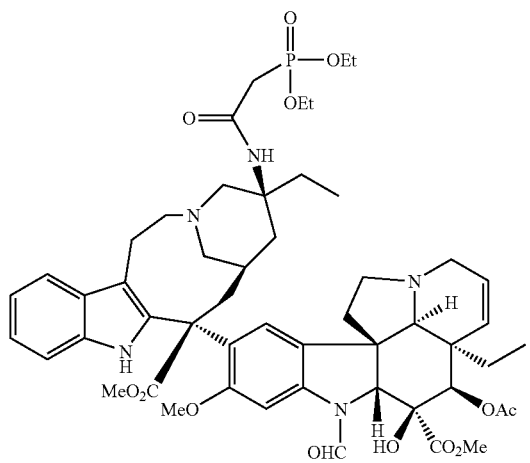

23-21

Vinblastine and diethyl (cyanomethyl)phosphonate (commercially available) are dissolved in conc. sulfuric acid at a temperature of 0° C., according to a procedure from Pearce, "Medicinal Chemistry of Bisindole Alkaloids from Catharanthus", in *The Alkaloids*, Vol. 37, 145, Academic Press San Diego, (1990) (described for acetonitrile). When the starting material is consumed the reaction mixture is carefully diluted with water and further neutralized. The crude reaction mixture is extracted with an organic solvent such as DCM. The combined organic extracts are washed aqueous bicarbonate solution and dried. Removal of the solvents yields the crude product. Further purification is achieved by chromatography.

The product of this step is dissolved in an organic solvent such as acetonitrile and the solution is cooled to −20° C. A strong inorganic acid such as perchloric acid (2 equiv) is added, followed by ferrous perchlorate and excess hydrogen peroxide, according to Pearce, "Medicinal Chemistry of Bisindole Alkaloids from Catharanthus", in *The Alkaloids*, Vol. 37, 145, Academic Press San Diego, (1990). At the end of the reaction aqueous ammonium hydroxide is added and the reaction mixture is extracted with an organic solvent such as DCM. Removal of solvents in vacuo yields the crude product. Further purification is achieved by chromatography.

Scheme 23.11: Attachment to 12'

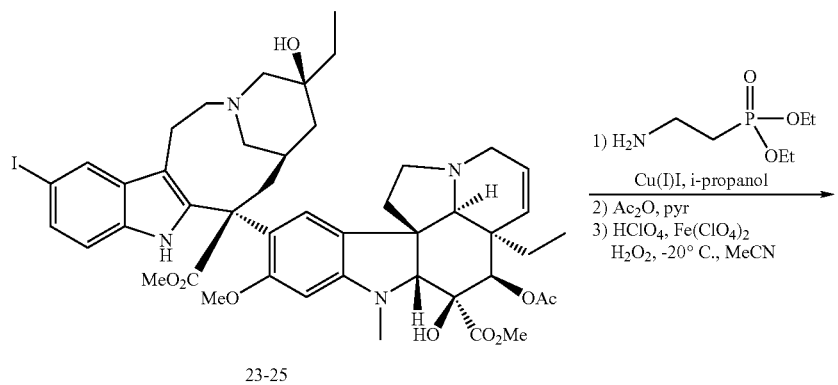

23-25

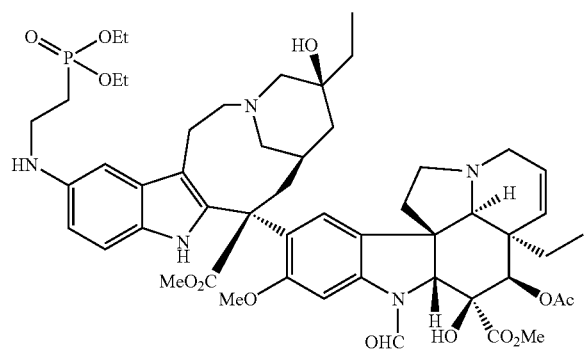

23.19

C12'-Iodo-vinblastine (prepared according to Pearce, "Medicinal Chemistry of Bisindole Alkaloids from Catharanthus", in *The Alkaloids*, Vol. 37, 145, Academic Press San Diego, (1990), by iodination of vinblastine with ferrous perchlorate, tetra(n-propyl)ammonium periodinate and a catalytic amount of ruthenium dioxide) is added to a mixture of copper(I) iodide and potassium phosphate and 2-aminoethylphosphonic acid diethyl ester (commercially available). The reaction mixture is heated under an inert gas atmosphere to ~80° C., according to a procedure from Buchwald in *Org. Lett.*, (2002), 4, 581-584. At the end of the reaction the material is cooled to room temperature and the solvent is removed in vacuo. The crude reaction mixture is extracted with an organic solvent such as DCM. The combined organic extracts are washed with aqueous bicarbonate solution and dried. Removal of the solvents yields the crude product. Further purification is achieved by chromatography. The product of this step is dissolved in an organic solvent such as DCM or THF. Pyridine is added, followed by acetic anhydride, and the reaction is stirred at room temperature according to *J. Med. Chem.*, (1979), 22, 391-400. At the end of the reaction, methanol is added and the solvents are removed in vacuo. The crude material is dissolved in an organic solvent such as DCM and is washed with water and aqueous bicarbonate solution and is dried. Removal of the solvents in vacuo yields the crude product. Further purification is achieved by chromatography.

The product of this step is dissolved in an organic solvent such as acetonitrile and the solution is cooled to −20° C. A strong inorganic acid such as perchloric acid (3 equiv) is added, followed by ferrous perchlorate and excess hydrogen peroxide, according to Pearce, "Medicinal Chemistry of Bisindole Alkaloids from Catharanthus", in *The Alkaloids*, Vol. 37, 145, Academic Press San Diego, (1990). At the end of the reaction aqueous ammonium hydroxide is added and the reaction mixture is extracted with an organic solvent such as DCM. Removal of solvents in vacuo yields the crude product. Further purification is achieved by chromatography.

Scheme 23.12: Attachment to 22'

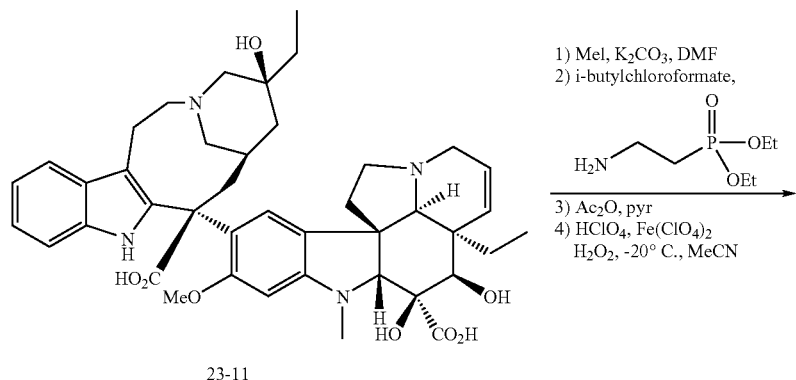

23-11

1) MeI, $K_2CO_3$, DMF
2) i-butylchloroformate, $H_2N\diagdown\diagup P(=O)(OEt)_2$ 3) $Ac_2O$, pyr
4) $HClO_4$, $Fe(ClO_4)_2$
   $H_2O_2$, -20° C., MeCN

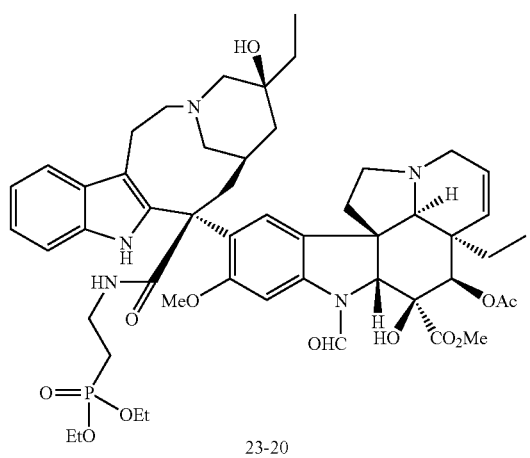

23-20

The starting material (prepared according to Pearce, "Medicinal Chemistry of Bisindole Alkaloids from Catharanthus", in *The Alkaloids*, Vol. 37, 145, Academic Press San Diego, (1990), by exhaustive hydrolysis of vinblastine in NaOH (5N) under refluxing conditions) is dissolved in an organic solvent such as dimethylformamide (DMF) at room temperature. Methyl iodide (1 equiv) is added, followed by potassium carbonate. Stirring at room temperature is continued. At the end of the reaction, the reaction is filtered and the solvent is removed in vacuo. The desired C24 methyl ester is purified by chromatography. The product of step 1 is dissolved in an organic solvent such as DCM or DMF and the solution is cooled to −10° C. A tertiary amine base such as DIEA is added, followed by a coupling reagent such as isobutylchloroformate. Stirring at −10° C. is continued until the activation is complete. Aminoethylphosphonic acid diethyl ester is added and stirring with slow warming to 0° C. is continued. At the end of the reaction, the solution is warmed to room temperature and the solvent is removed in vacuo. The product is further purified by chromatography. The product of this step is dissolved in an organic solvent such as DCM or THF. Pyridine is added, followed by acetic anhydride, and the reaction is stirred at room temperature according to *J. Med. Chem.*, (1979), 22, 391-400. At the end of the reaction, methanol is added and the solvents are removed in vacuo. The crude material is dissolved in an organic solvent such as DCM, washed with water and aqueous bicarbonate solution, and dried. Removal of the solvents in vacuo yields the crude product. Further purification is achieved by chromatography.

The product of this step is dissolved in an organic solvent such as acetonitrile and the solution is cooled to −20° C. A strong inorganic acid such as perchloric acid (2 equiv) is added, followed by ferrous perchlorate and excess hydrogen peroxide, according to Pearce, "Medicinal Chemistry of Bisindole Alkaloids from Catharanthus", in *The Alkaloids*, Vol. 37, 145, Academic Press San Diego, (1990). At the end of the reaction aqueous ammonium hydroxide is added and the reaction mixture is extracted with an organic solvent such as DCM. Removal of solvents in vacuo yields the crude product. Further purification is achieved by chromatography.

Example 24

Preparation of Exemplary Compounds of the Present Invention

Compounds of the invention can be prepared according to the general route outlined in Schemes 24.1 and 24.3, with examples depicted in Schemes 24.2 and 24.4.

Scheme 24.1

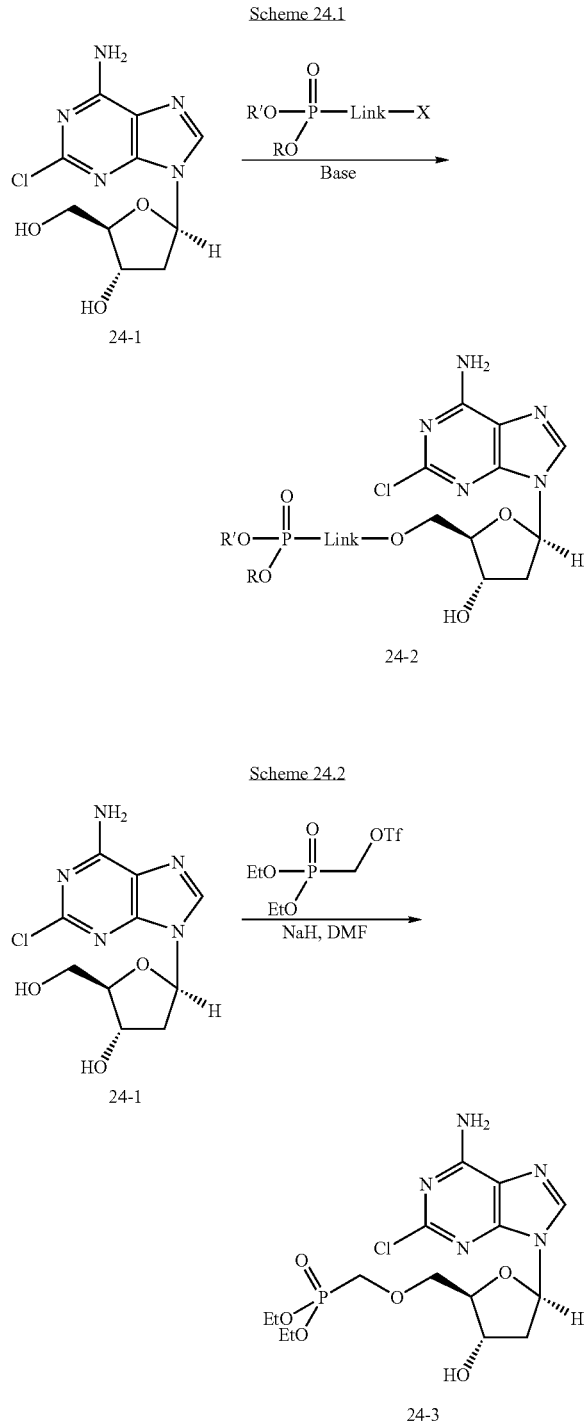

Scheme 24.2

Scheme 24.3

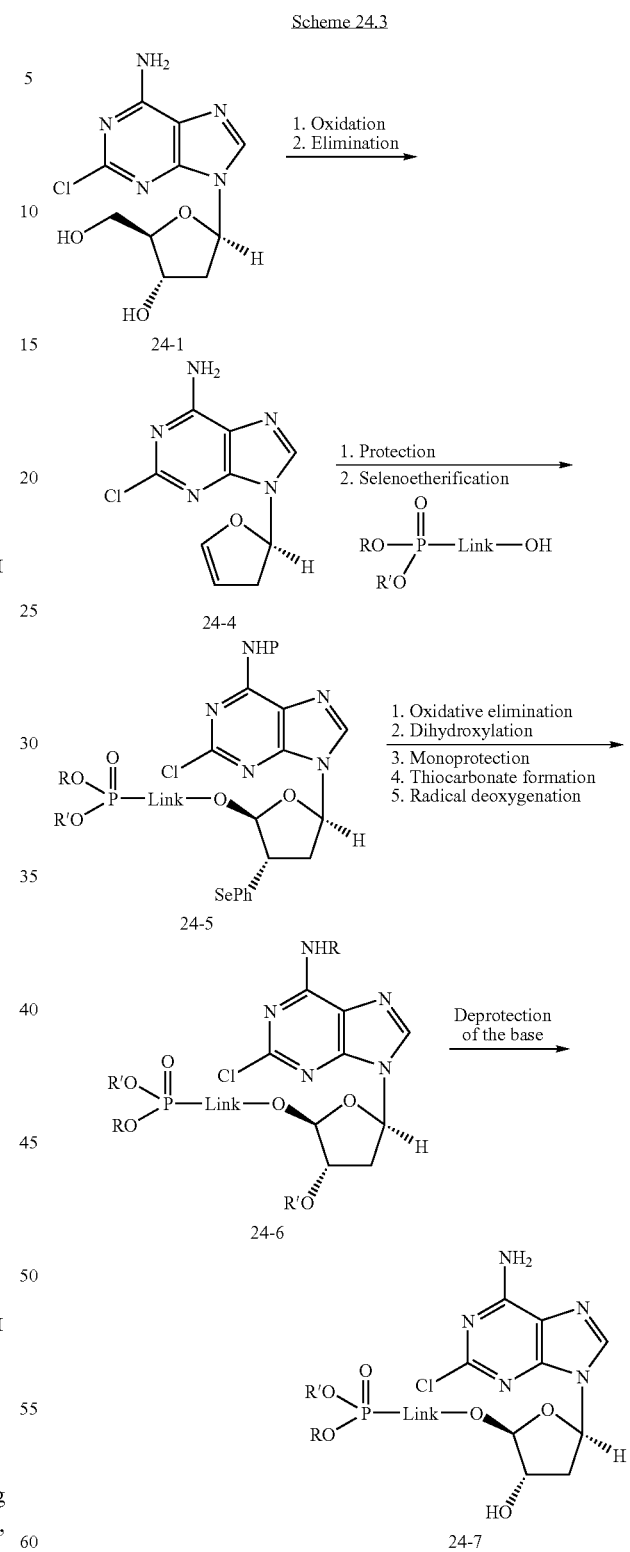

The 2-chloro-2'-deoxyadenosine 24-1 (prepared according to the procedure of Ikehara, M. et al., *J. Am. Chem. Soc.*, (1963), 85, 2344, also see Ikehara, M. et al., *J. Am. Chem. Soc.*, (1965), 87, 3, 606) can be treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester 24-2, 24-3.

The preparation of compound 24-7, 24-13 is described in Scheme 24.3. Compound 24-1 (2-chloro-2'-deoxyadenosine) can be prepared as described in Ikehara, M. et al., *J. Am. Chem. Soc.*, (1963), 85, 2344; see also Ikehara, M. et al., *J. Am. Chem. Soc.*, (1965), 87, 3, 606. Oxidation of the 5'-OH followed by elimination provides glycal 24-4 (see the procedure of Zemlicka J. et al., *J. Am. Chem. Soc.,* (1972), 94, 9, 3213). Protection of the chloroadenine at the 6 position followed by selenoetherification provides the protected phosphonate 24-5, 24-10 (Kim, C. et al., *J. Org. Chem.*, (1991), 56, 2642). Oxidative elimination of the phenylselenide (as described in Kim, C. et al., *J. Org. Chem.*, (1991), 56, 2642) followed by stereoselective dihydroxylation provides the diol which can then be converted to the 3' monoprotected sugar. Acylation of the 2' alcohol with phenyl chlorothionoformate provides the precursor for Robins deoxygenation. Subsequent deoxygenation provides compound 24-6, 24-12 (Metteucci, M. D. et al., *Tetrahedron Lett.*, (1987), 28, 22, 2469, see also Robins, M. J. et al., *J. Org. Chem.*, (1995), 60, 7902). Finally, the protecting groups are removed.

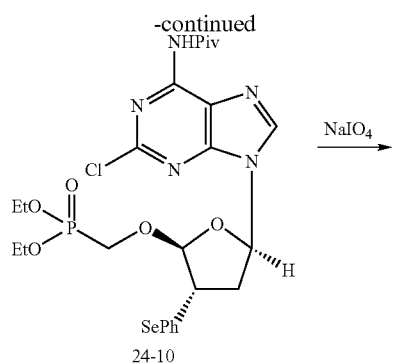

24-10

Scheme 24.4

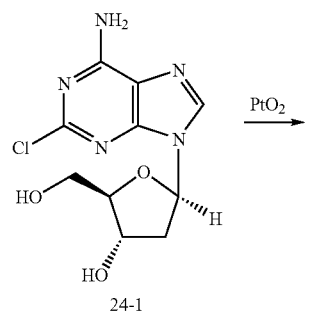

24-1

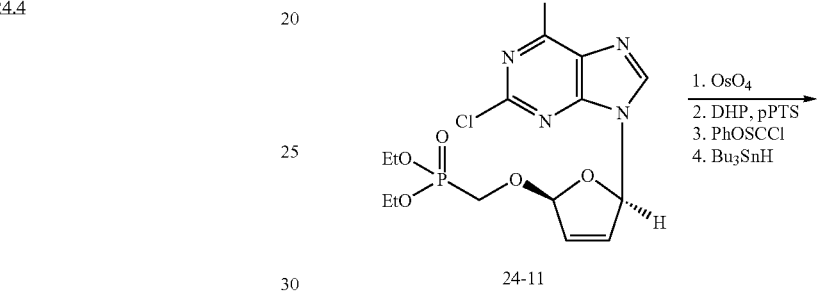

24-11

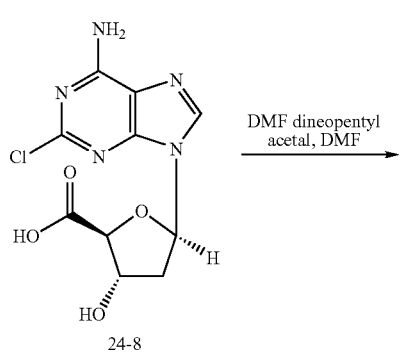

24-8

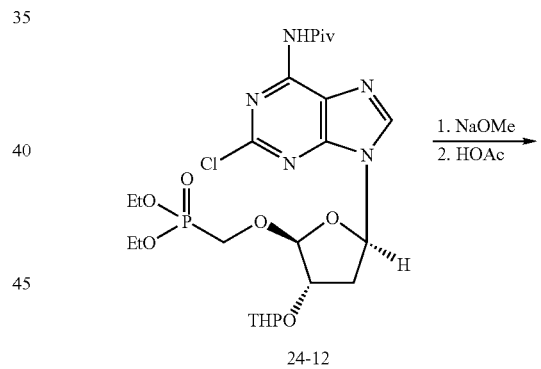

24-12

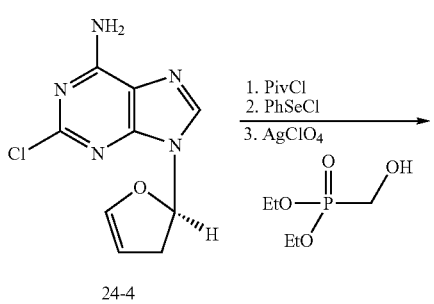

24-4

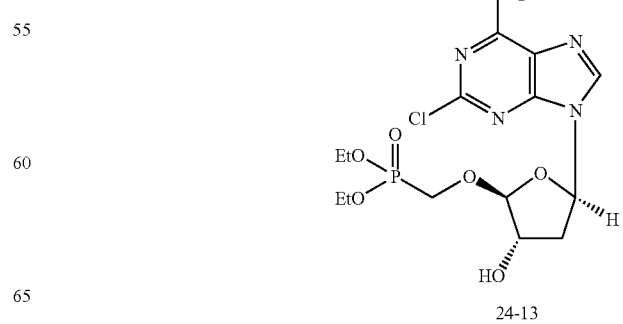

24-13

Specifically, 2-chloro-2'-deoxyadenosine, compound 24-1 can be oxidized with $PtO_2$ to provide carboxylic acid 24-8. Decarboxylative elimination is achieved using dimethylformamide dineopentyl acetal in DMF at high temperature (Zemlicka J. et al., *J. Am. Chem. Soc.*, (1972), 94, 9, 3213). Once the furanoid glycal 24-4 is in hand, it is first protected at the 6-position of the 2-chloroadenosine using PivCl conditions as described in Greene, T., Protective groups in organic synthesis, Wiley-Interscience, 1999. Treatment of the protected glycal with silver perchlorate in the presence of diethyl (hydroxymethyl)phosphonate (Phillion, D. et al., Tetrahedron Lett., 1986, 27, 1477) provides the phosphonate 24-5, 24-10 (Kim, C. et al., *J. Org. Chem.*, (1991), 56, 2642). Oxidative elimination of the selenide followed by dihydroxylation using osmium tetraoxide provides a diol which can be monoprotected at the 3' position using a THP group. Further acylation of the 2' alcohol with phenyl chlorothionoformate provides the precursor for Robins deoxygenation, performed with tributyltin hydride, to give compound 24-6, 24-12 (Metteucci, M. D. et al., *Tetrahedron Lett.*, (1987), 28, 22, 2469, also see Robins, M. J. et al., *J. Org. Chem.*, (1995), 60, 7902). Deprotection of the pivaloyl group by treatment with sodium methoxide (Greene, T., Protective groups in organic synthesis, Wiley-Interscience, (1999)) is followed by a final deprotection of the THP group in acetic acid.

Example 25

Preparation of Exemplary Compounds of the Present Invention

Compounds such as these can be made according to the general route outlined in Schemes 25.1-25.5, with specific examples depicted in Schemes 25.2-25.5. Final compounds, be they diastereoisomers or enantiomers, may be purified by chromatographic means.

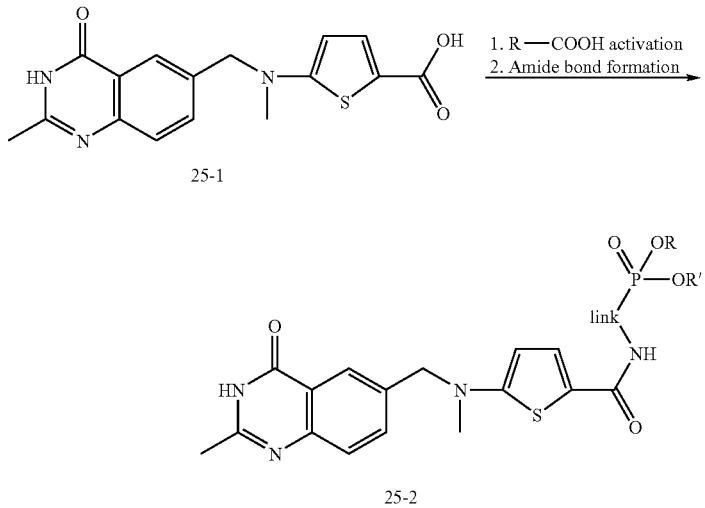

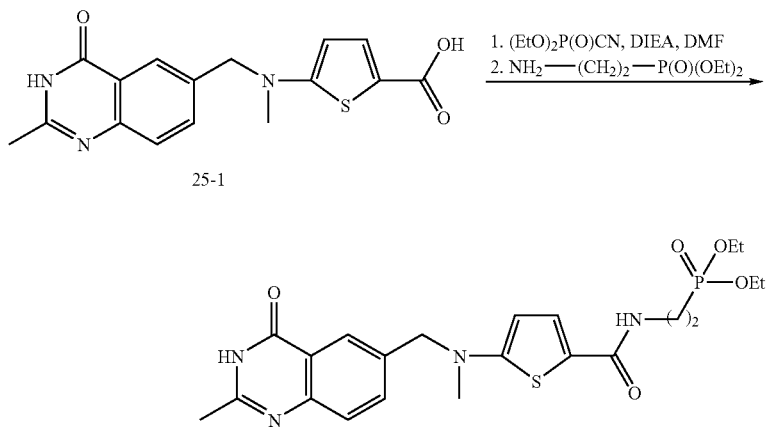

The starting carboxylic acid can be treated in a solvent such as dimethylformamide (DMF) or N-methylpyrrolidinone (NMP) with a coupling reagent such as diethyl cyanophosphonate or isobutyl chloroformate and a base such as diisopropylethylamine (DIEA) at room temperature (*J. Med. Chem.*, (1982), 25, 960-964 and *J. Med. Chem.*, (1984), 27, 600-604). When the activation is complete, 2-aminoethylphosphonic acid diethyl ester (commercially available) is added. After consumption of the activated species is observed the solvent is removed in vacuo and the product is isolated via chromatography. Alternatively, the product can be isolated through precipitation from the reaction solution with an organic solvent like diethyl ether or the like.

27, 600-604). When the activation is complete, (2-aminoethylsulfanylmethyl)-phosphonic acid diethyl ester (made by base-catalyzed coupling of 2-aminoethanethiol with diethyl phosphonomethyltriflate, prepared according to *Tetrahedron Lett.*, (1986), 27, 1477) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The intermediate is then dissolved in a mixture of water, DMF, and acetic acid and is treated with Scheme 25.3:

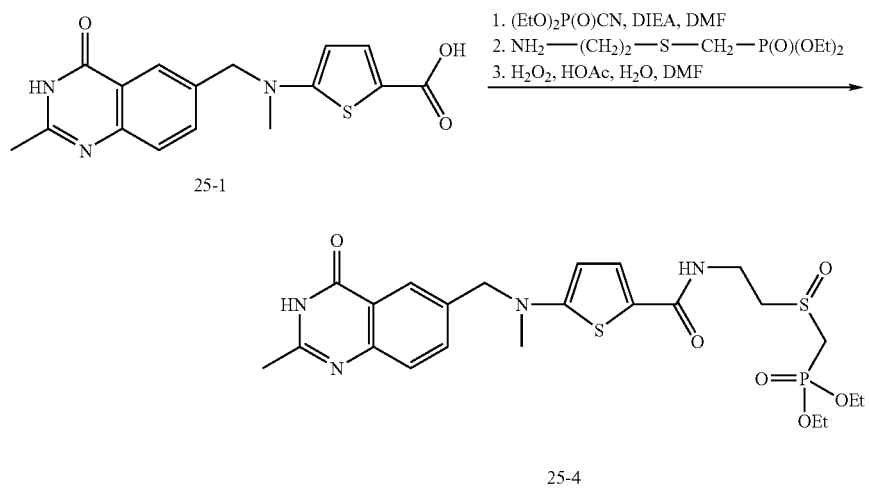

The starting carboxylic acid can be treated in a solvent such as DMF or NMP with a coupling reagent such as diethyl cyanophosphonate or isobutyl chloroformate and a base such as diisopropylethylamine (DIEA) at room temperature (*J. Med. Chem.*, (1982), 25, 960-964 and *J. Med. Chem.*, (1984), hydrogen peroxide solution (excess). After removal of the solvents the product is isolated via chromatography. Alternatively, the product can be isolated through precipitation from the reaction solution with an organic solvent like diethyl ether or the like.

Scheme 25.4:

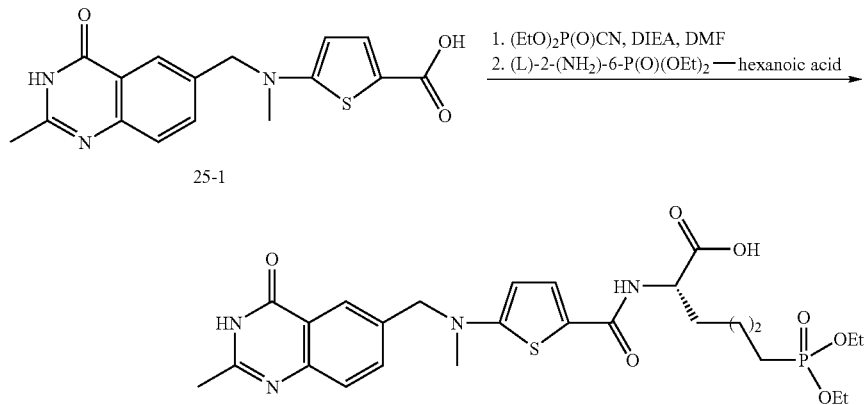

The starting carboxylic acid can be treated in a solvent such as DMF or NMP with a coupling reagent such as diethyl cyanophosphonate or isobutyl chloroformate and a base such as DIEA at room temperature (*J. Med. Chem.*, (1982), 25, 960-964 and *J. Med. Chem.*, (1984), 27, 600-604.). When the activation is complete, (L)-2-amino-6-(diethylphosphonato)-hexanoic acid is added. After consumption of the activated species is observed the solvent is removed in vacuo and the product is isolated via chromatography. Alternatively, the product can be isolated through precipitation from the reaction solution with an organic solvent like diethyl ether or the like.

species is observed the solvent is removed in vacuo and the intermediate is isolated via chromatography. Alternatively, the intermediate can be isolated through precipitation from the reaction solution with an organic solvent like diethyl ether or the like. The crude intermediate is then dissolved in DMF and treated with trifluoroacetic acid (TFA). The product is isolated via chromatography after removal of the solvents. Alternatively, the product can be isolated through precipitation form the reaction solution with an organic solvent like diethyl ether or the like.

Scheme 25.5:

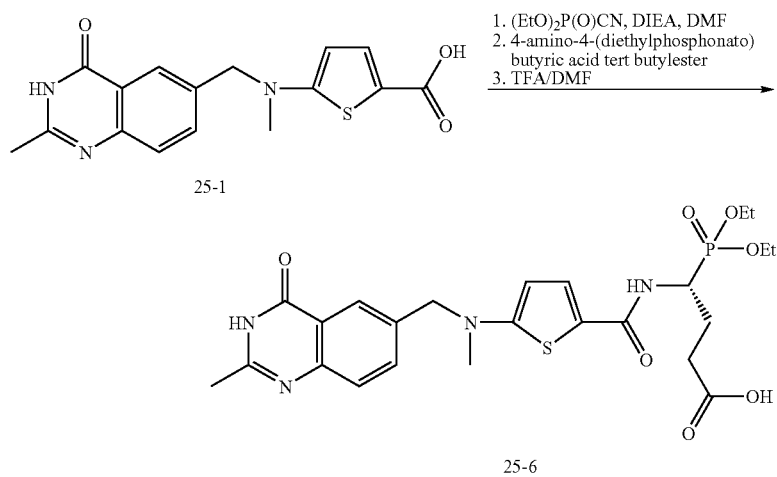

The starting carboxylic acid can be treated in a solvent such as DMF or NMP with a coupling reagent such as diethyl cyanophosphonate or isobutyl chloroformate and a base such as DIEA at room temperature (*J. Med. Chem.*, (1982), 25, 960-964 and *J. Med. Chem.*, (1984), 27, 600-604). When the activation is complete, 4-amino-4-(diethylphosphonato)-butyric acid tert butylester (*J. Am. Chem. Soc.*, (1995), 117, 10879-10888) is added. After consumption of the activated Example 26

Preparation of Exemplary Compounds of the Present Invention

Compounds such as these can be made according to the general route outlined in Schemes 26.1-26.5, with specific examples depicted in Schemes 2-4. Final compounds, be they diastereoisomers or enantiomers, may be purified by chromatographic means.

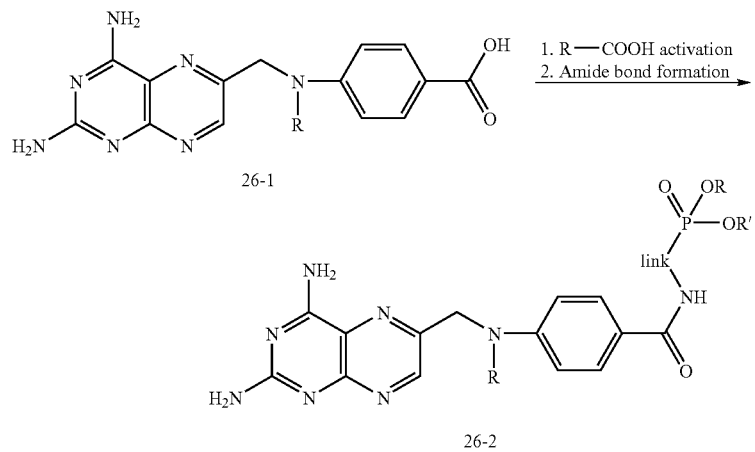

In case a direct coupling to aminopterin is hampered by the presence of a free secondary amine in the starting material (R=H), this entity is temporarily protected either with a tert-butoxycarbonyl group (R=Boc) or benzyloxycarbonyl (R=Cbz or Z) according to standard procedures (Green Wutts: Protective groups in organic chemistry)

added. After consumption of the activated species is observed the solvent is removed in vacuo and the product is isolated via chromatography. Alternatively, the product can be isolated through precipitation from the reaction solution with an organic solvent such as diethyl ether or the like.

Scheme 26.2:

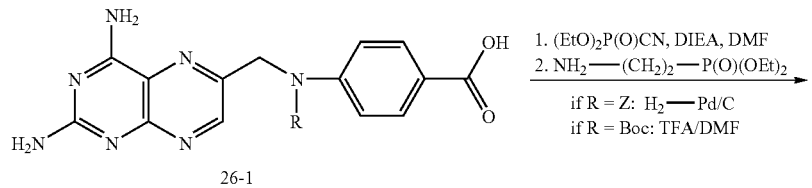

26-1

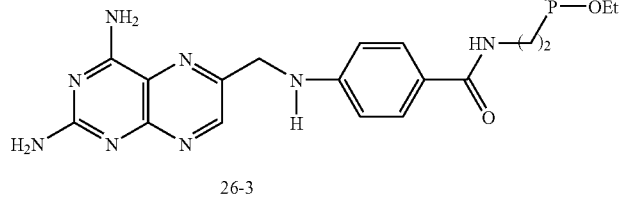

26-3

The starting carboxylic acid can be treated in a solvent such as dimethylformamide (DMF) or N-methylpyrrolidinone (NMP) with a coupling reagent such as diethyl cyanophosphonate or isobutyl chloroformate and a base such as diisopropylethylamine (DIEA) at room temperature (*J. Med. Chem.*, (1982), 25, 960-964 and *J. Med. Chem.*, (1984), 27, 600-604). When the activation is complete, 2-aminoethylphosphonic acid diethyl ester (commercially available) is In case R=Z: The compound is dissolved in an organic solvent like DMF or NMP and a catalytic amount of Pd/C is added. The reaction mixture is stirred under an atmosphere of hydrogen until the starting material is consumed. The Pd/C is removed by filtration and the solvent is evaporated in vacuo. The product is isolated via chromatography. Alternatively, the product can be isolated through precipitation from the reaction solution with an organic solvent such as diethyl ether or the like.

Scheme 26.3:

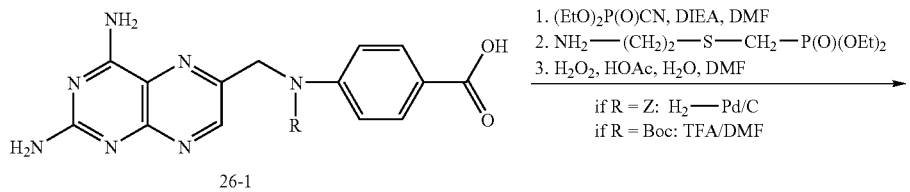

26-1

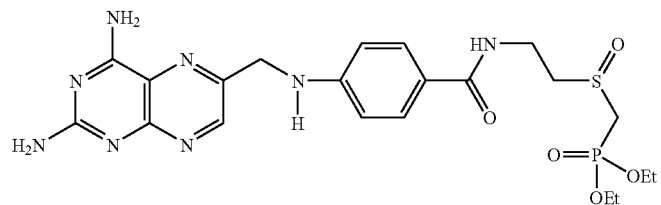

26-4

The starting carboxylic acid can be treated in a solvent such as DMF or NMP with a coupling reagent such as diethyl cyanophosphonate or isobutyl chloroformate and a base such as diisopropylethylamine (DIEA) at room temperature (*J. Med. Chem.*, (1982), 25, 960-964 and *J. Med. Chem.*, (1984), 27, 600-604). When the activation is complete, (2-aminoethylsulfanylmethyl)-phosphonic acid diethyl ester (made by base-catalyzed coupling of 2-aminoethanethiol with diethyl phosphonomethyltriflate, prepared according to *Tetrahedron Lett.*, (1986), 27, 1477) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The intermediate is then dissolved in a mixture of water, DMF, and acetic acid and is treated with hydrogen peroxide solution (excess). After removal of the solvents the product is isolated via chromatography. Alternatively, the product can be isolated through precipitation from the reaction solution with an organic solvent like diethyl ether or the like.

In case R=Z: The compound is dissolved in an organic solvent like DMF or NMP and a catalytic amount of Pd/C is added. The reaction mixture is stirred under an atmosphere of hydrogen until the starting material is consumed. The Pd/C is removed by filtration and the solvent is evaporated in vacuo. The product is isolated via chromatography. Alternatively, the product can be isolated through precipitation from the reaction solution with an organic solvent such as diethyl ether or the like.

Scheme 26.4:

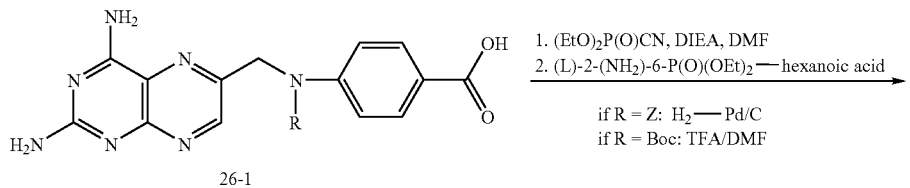

26-1

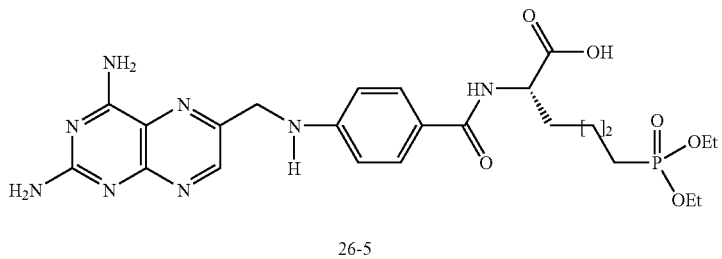

26-5

The starting carboxylic acid can be treated in a solvent such as DMF or NMP with a coupling reagent such as diethyl cyanophosphonate or isobutyl chloroformate and a base such as DIEA at room temperature (*J. Med. Chem.*, (1982), 25, 960-964 and *J. Med. Chem.*, (1984), 27, 600-604.). When the activation is complete, (L)-2-amino-6-(diethylphosphonato)-hexanoic acid is added. After consumption of the activated species is observed the solvent is removed in vacuo and the product is isolated via chromatography. Alternatively, the product can be isolated through precipitation from the reaction solution with an organic solvent such as diethyl ether or the like.

In case R=Z: The compound is dissolved in an organic solvent like DMF or NMP and a catalytic amount of Pd/C is added. The reaction mixture is stirred under an atmosphere of hydrogen until the starting material is consumed. The Pd/C is removed by filtration and the solvent is evaporated in vacuo. The product is isolated via chromatography. Alternatively, the product can be isolated through precipitation from the reaction solution with an organic solvent such as diethyl ether or the like.

Scheme 26.5:

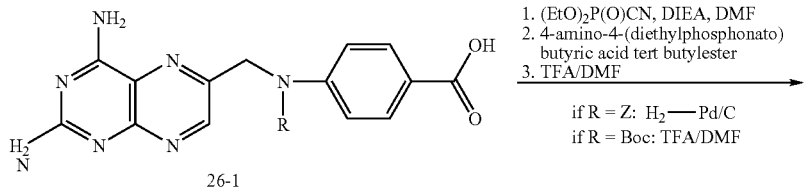

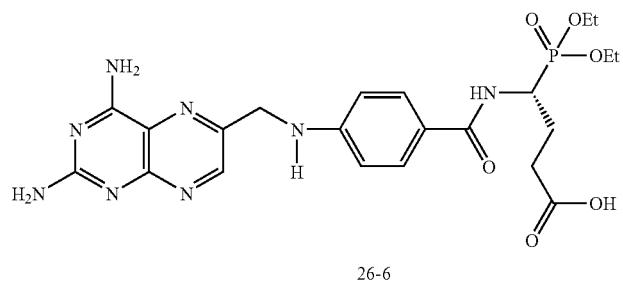

The starting carboxylic acid can be treated in a solvent such as DMF or NMP with a coupling reagent such as diethyl cyanophosphonate or isobutyl chloroformate and a base such as DIEA at room temperature (*J. Med. Chem.*, (1982), 25, 960-964 and *J. Med. Chem.*, (1984), 27, 600-604). When the activation is complete, 4-amino-4-(diethylphosphonato)-butyric acid tert butylester (*J. Am. Chem. Soc.*, (1995), 117, 10879-10888) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The crude intermediate is then dissolved in DMF and treated with TFA (excess). The product is isolated via chromatography after removal of the solvents. Alternatively, the product can be isolated through precipitation form the reaction solution with an organic solvent such as diethyl ether or the like.

In case R=Z: The compound is dissolved in an organic solvent like DMF or NMP and a catalytic amount of Pd/C is added. The reaction mixture is stirred under an atmosphere of hydrogen until the starting material is consumed. The Pd/C is removed and the solvent is evaporated in vacuo. The product is isolated via chromatography. Alternatively, the product can be isolated through precipitation from the reaction solution with an organic solvent such as diethyl ether or the like.

Example 27

Preparation of Exemplary Compounds of the Present Invention

Compounds such as these can be made according to the general routes outlined in Schemes 27.1 and 27.3, with exemplifications in Scheme 27.2 and Schemes 27.4-27.6.

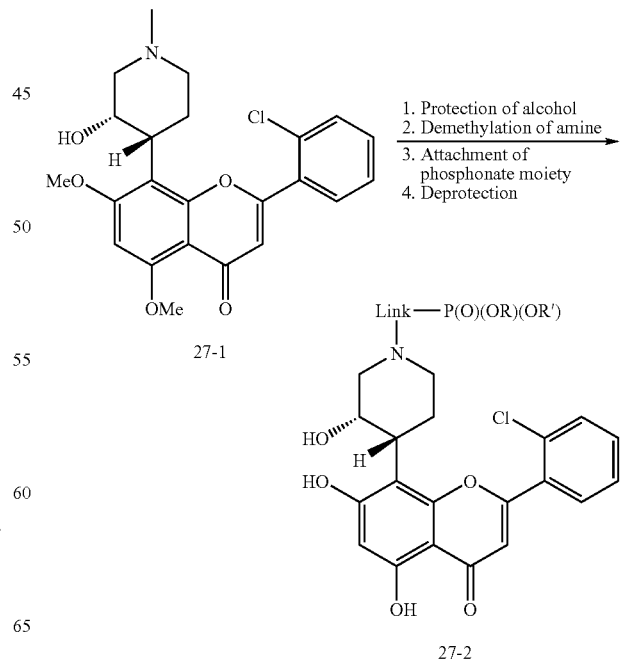

The bis-anisole derivative of flavopiridol (see *Bioorg Med. Chem. Lett.*, (2000), 10, 1037) serves as an ideal starting point for attachment of a phosphonate moiety to the piperidine nitrogen. Following protection of the alcohol, the tertiary amine is demethylated and derivatized with the reagent of choice. Removal of the methyl ethers and the protecting group on the alcohol gives the desired analogs.

An example of an alvocidib analog with a phosphonate moiety linked to the piperidine nitrogen in this manner is illustrated in Scheme 27.2.

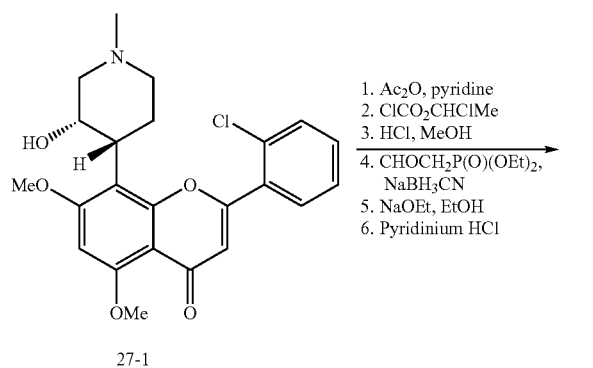

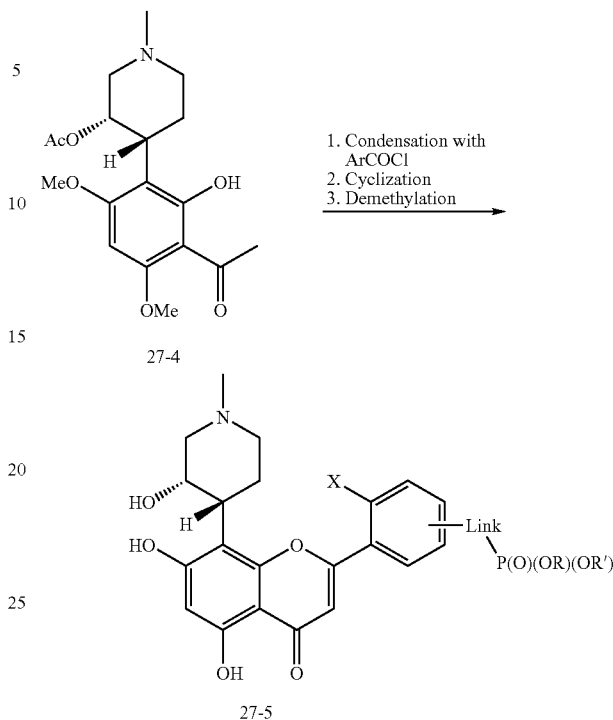

The 2-hydroxyacetophenone (see *Bioorg. Med. Chem. Lett.*, (2000), 10, 1037) is treated with a suitable phosphonate-bearing benzoyl chloride derivative. The flavone ring system is formed by cyclization, and the methyl groups are removed.

Such a synthesis is exemplified in Scheme 27.4.

The alcohol is protected as the acetate under standard conditions (see Greene, T., Protective groups in organic synthesis, Wiley-Interscience, (1999)). Demethylation of the N-methylpiperidine is achieved through reaction with α-chloroethyl chloroformate in the presence of a base such as N,N-diisopropylethylamine (DIEA) followed by brief heating in acidic methanol. The liberated secondary amine is condensed with (2-oxo-ethyl)-phosphonic acid diethyl ester under reductive conditions such as those achieved through the use of sodium cyanoborohydride in a solvent such as methanol or dimethylformamide (see *Tet. Lett.* (1990), 31, 5595). The alcohol is de-acetylated by treatment with sodium ethoxide in ethanol. Finally, bis-demethylation is achieved by heating with pyridinium hydrochloride (see *Bioorg. Med. Chem. Lett.*, (2000), 10, 1037).

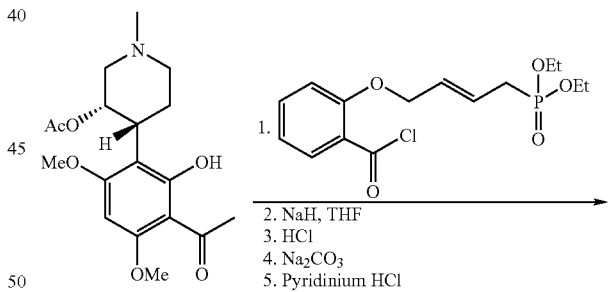

Condensation with [4-(2-chlorocarbonyl-phenoxy)-but-2-enyl]-phosphonic acid diethyl ester (synthesis below) is followed by successive treatment with sodium hydride, hydrochloric acid and sodium carbonate, generating the 5,7-dimethoxyflavone. Demethylation to provide the 5,7-dihydroxyflavone final product is achieved as in Scheme 27.2 (see *Bioorg. Med. Chem. Lett.*, (2000), 10, 1037).

Scheme 27.5

Synthesis of [4-(2-chlorocarbonyl-phenoxy)-but-2-enyl]-phosphonic acid diethyl ester

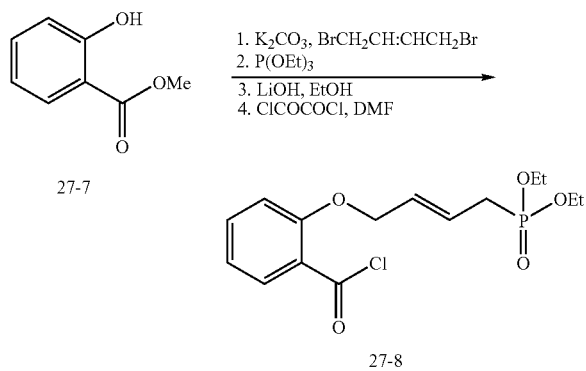

Salicylic acid methyl ester is treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the mono-alkylated product is isolated by chromatography. The resulting monobromide is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. The methyl ester is saponified with lithium hydroxide and the acid chloride generated by treatment with oxalyl chloride in a solvent such as dichloromethane in the presence of a catalytic amount of dimethylformamide.

A synthesis of another suitable acid chloride is exemplified below.

Scheme 27.6

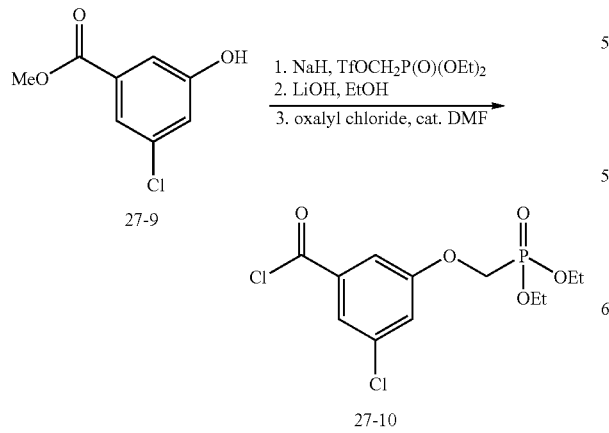

The phenol is treated in a solvent such as tetrahydrofuran or dimethylformamide with a base such as sodium hydride.

When bubbling ceases, diethyl phosphonomethyltriflate (prepared according to *Tetrahedron Lett.*, (1986), 27, 1477) is added, yielding the desired phosphonate diester.

Similarly, a reagent suitable for generating an analog with a phosphonate moiety attached to the 4-position of the phenyl ring at the flavone 2-position may be generated from 4-hydroxybenzoic acid methyl ester.

Example 28

Preparation of Exemplary Compounds of the Present Invention

Reduction of the dose and/or improvement of efficacy are achieved by the use of pro-drugs of analogs of vinblastine which, upon cleavage inside the target cell, give rise to an agent with an increased intracellular half-life. Such compounds are described below.

Scheme 28.1

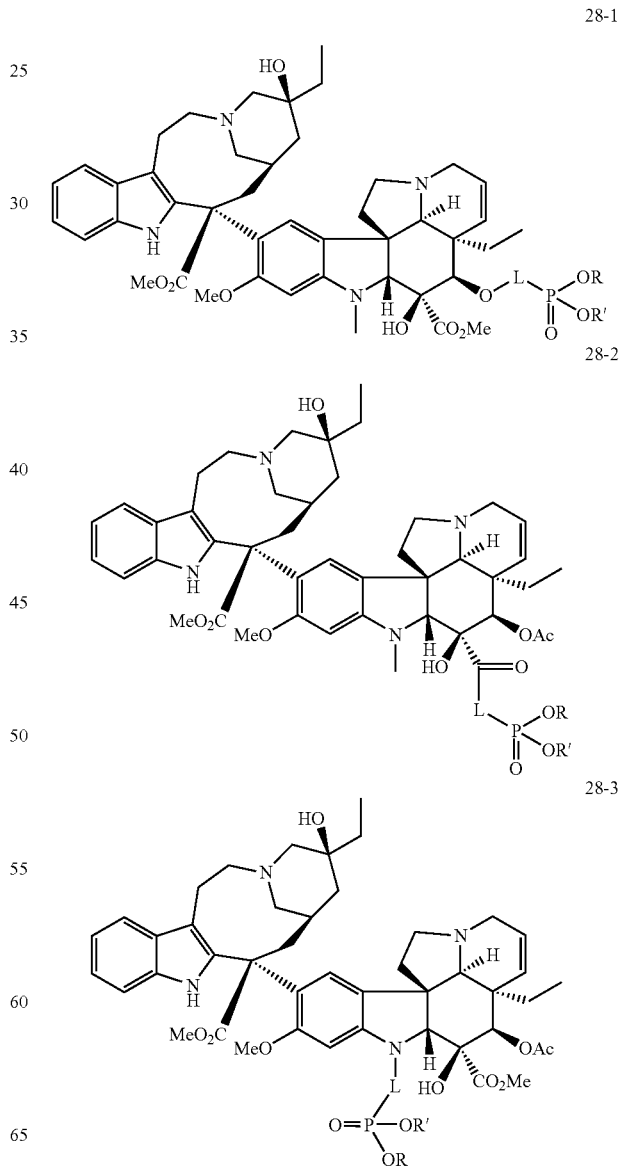

-continued
28-4
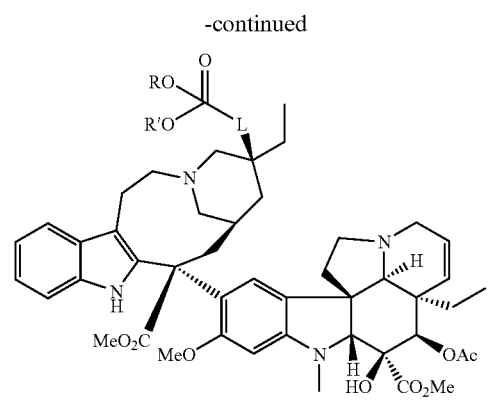
28-5
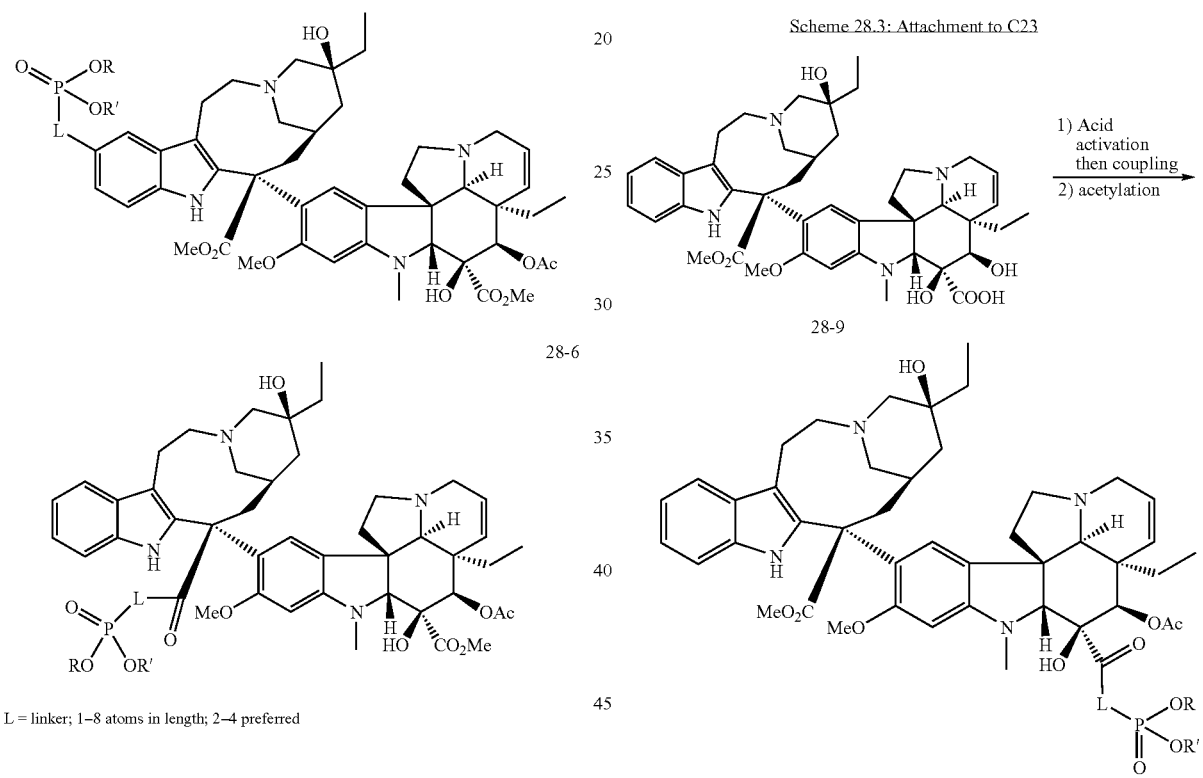
28-6
L = linker; 1–8 atoms in length; 2–4 preferred
Compounds such as these can be made according to the general route outlined in Schemes 28.2-28.7, with examples depicted in Schemes 28.8-28.13.
Scheme 28.2: Modification at C4
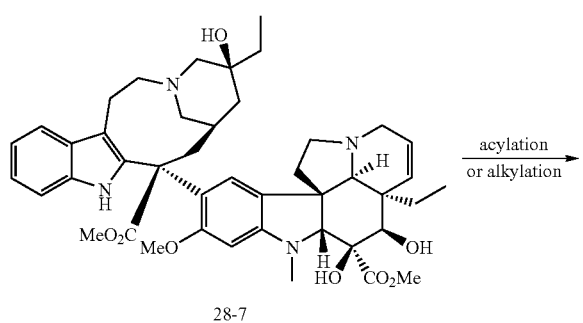
28-7
-continued
28-8
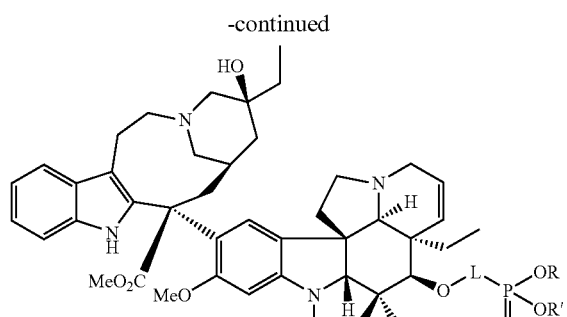
Scheme 28.3: Attachment to C23
28-9
1) Acid activation then coupling
2) acetylation
28-10
Scheme 28.4: Attachment to N1
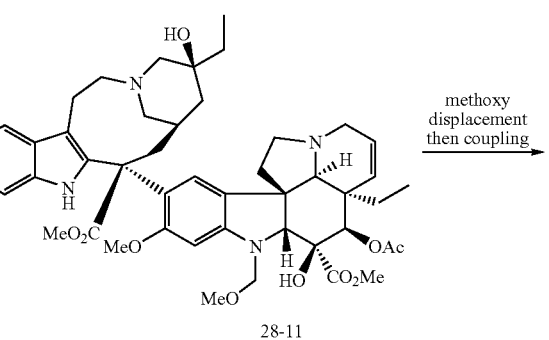
28-11
methoxy displacement then coupling -continued
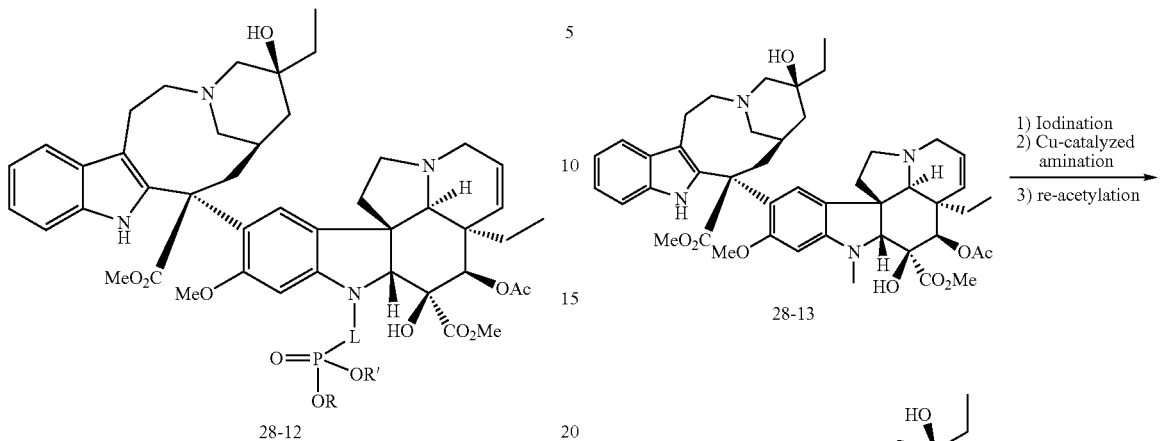
28-12
Scheme 28.5: Attachment to C4'
28-13
28-14
Scheme 28.6: Attachment to C12'
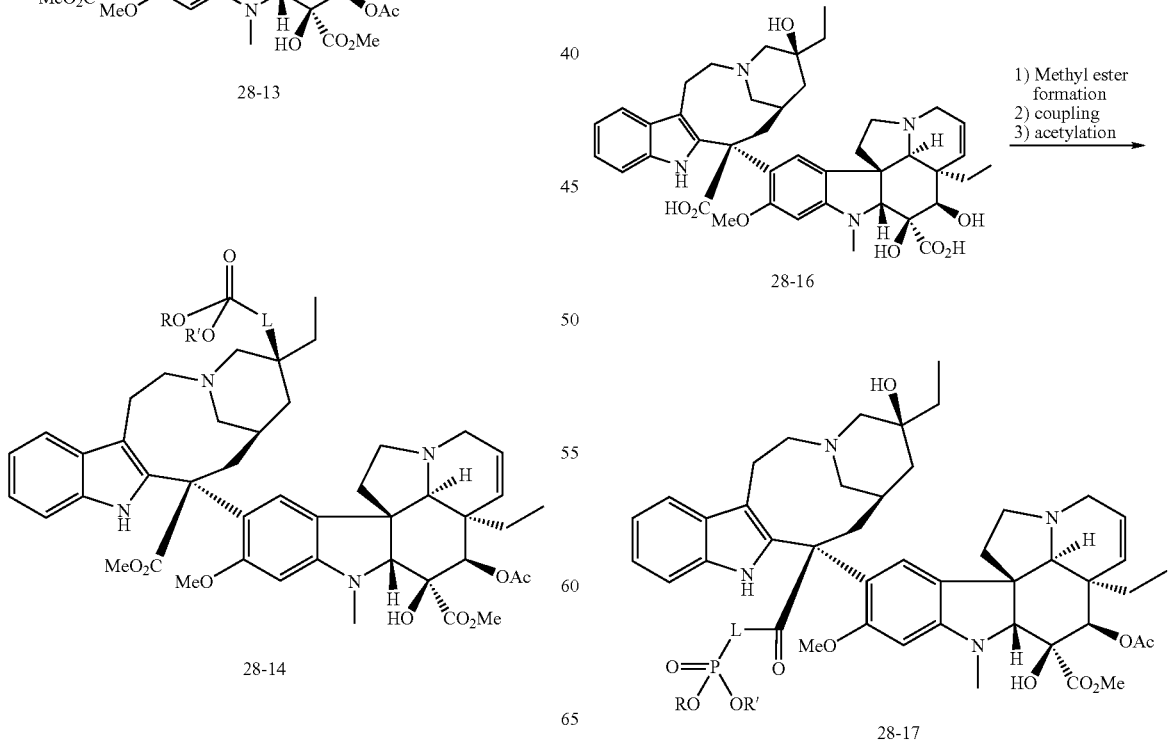
28-13
1) Iodination
2) Cu-catalyzed amination
3) re-acetylation
28-15
Scheme 28.7: Attachment to C22'
28-16
1) Methyl ester formation
2) coupling
3) acetylation
28-17

Scheme 28.8: Attachment to C4

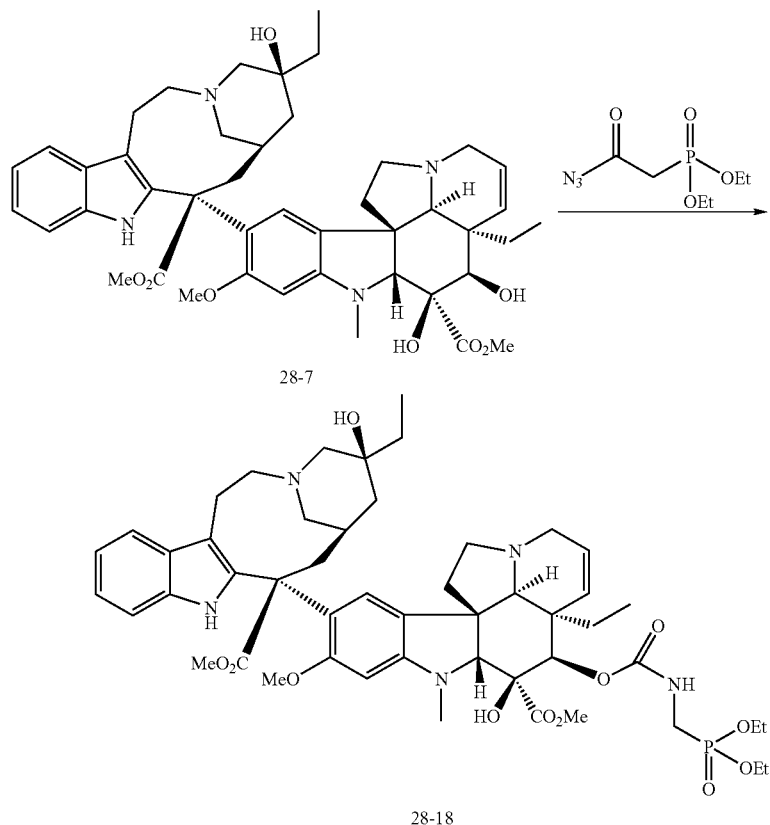

2-Diethyl phosphonatoacetic acid is dissolved in an organic solvent such as benzene, tetrahydrofuran (THF), or chloroform, and is combined with a tertiary amine base such as diisopropylethylamine (DIEA) and diphenyl phosphorazidate (1.2 equiv) and is stirred at room temperature, according to *J. Med. Chem.*, (1991), 34, 1001-1018. After the acyl azide has been formed, 4-deacetyl vinblastine (prepared according to *J. Med. Chem.*, (2002), 45, 4706-4715 from vinblastine) is added and the reaction mixture is heated to ~80° C. for ~4 hours (*Biochemistry*, (2002), 41, 14010-14018). The reaction mixture is cooled to room temperature and is washed with aqueous hydrochloric acid (HCl) (1N) and aqueous bicarbonate solution and dried. Removal of the solvents yields the crude product. Further purification is achieved by chromatography.

Scheme 28.39: Attachment to C23

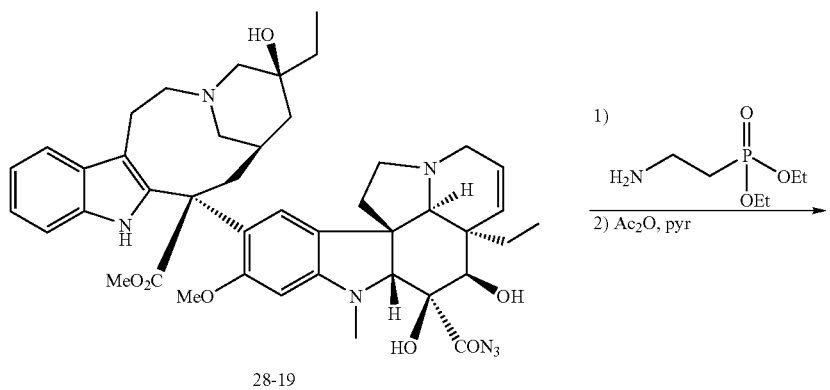

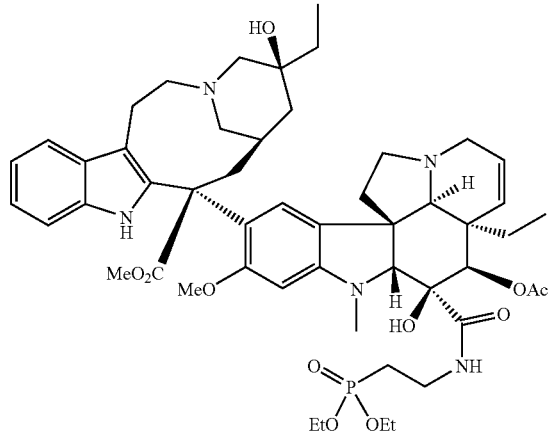

28-20

The starting material (synthesis published in *J. Med. Chem.*, (1978), 21, 88-96; from vinblastine) is treated in an organic solvent such as dichloromethane (DCM) or THF with 2-aminoethylphosphonic acid diethyl ester at room temperature, according to the procedure described in *J. Med. Chem*, (1979), 22, 391-400. At the end of the reaction, the solution is washed with water, aqueous bicarbonate and water, and is dried. Evaporation of solvents yields the crude product. Further purification is achieved by chromatography.

The product of this step is dissolved in an organic solvent such as DCM or THF. Pyridine is added followed by acetic anhydride and the reaction is stirred at room temperature, according to *J. Med. Chem.*, (1979), 22, 391-400. At the end of the reaction, methanol is added and the solvents are removed in vacuo. The crude material is dissolved in an organic solvent such as DCM and is washed with water and aqueous bicarbonate solution and is dried. Removal of the solvents in vacuo yields the crude product. Further purification is achieved by chromatography.

Scheme 28.10: Attachment to N1

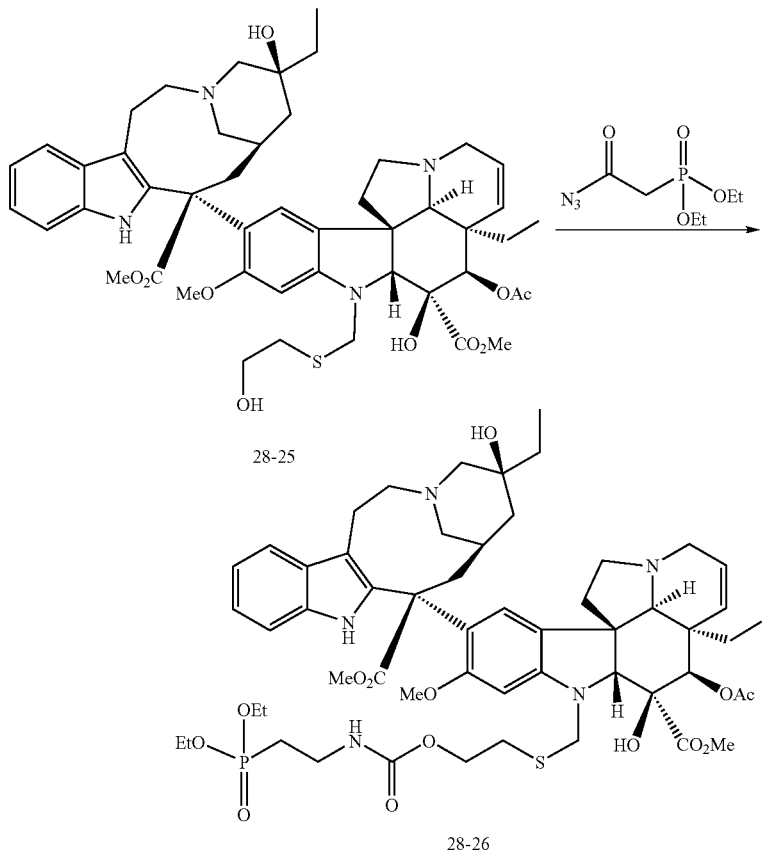

28-25

28-26

2-Diethyl phosphonatoacetic acid is dissolved in an organic solvent such as benzene, THF, or chloroform, and is combined with a tertiary amine base such as diisopropylethylamine (DIEA) and diphenyl phosphorazidate (1.2 equiv) and stirred at room temperature, according to *J. Med. Chem.*, (1991), 34, 1001-1018. After the acyl azide has been formed, N-1-(β-hydroxyethylthiomethyl)vinblastine (prepared according to Pearce, "Medicinal Chemistry of Bisindole Alkaloids from Catharanthus", in *The Alkaloids* Vol. 37, 145, Academic Press San Diego, (1990), from vinblastine, via $CrO_3$-mediated oxidation in the presence of methanol and consecutive methoxy displacement with β-hydroxy thioethanol) is added, and the reaction mixture is heated to ~80° C. for ~4 hrs (*Biochemistry* (2002), 41, 14010-14018). The reaction mixture is cooled to room temperature and is washed with aqueous HCl (1N) and aqueous bicarbonate solution and dried. Removal of the solvents yields the crude product. Further purification is achieved by chromatography.

Scheme 28.11: Attachment to C4'

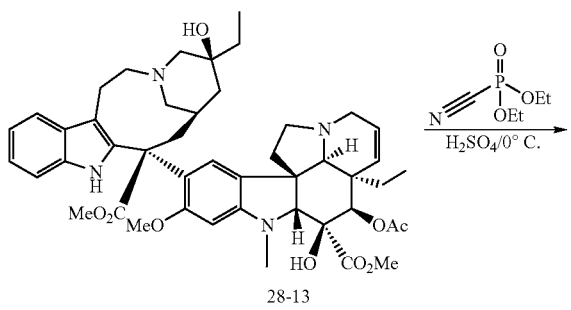

28-13

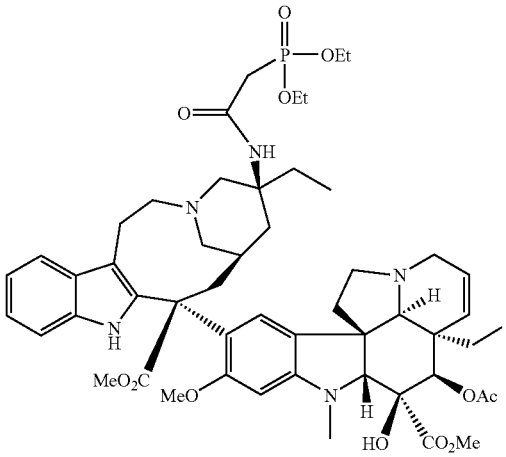

28-27

Vinblastine and diethyl cyanomethylphosphonate (commercially available) are dissolved in conc. sulfuric acid at a temperature of ~0° C., according to a procedure from Pearce, "Medicinal Chemistry of Bisindole Alkaloids from Catharanthus" in *The Alkaloids* Vol. 37, 145, Academic Press San Diego, (1990). When the starting material is consumed, the reaction mixture is carefully diluted with water and further neutralized. The crude reaction mixture is extracted with an organic solvent such as DCM. The combined organic extracts are washed with aqueous bicarbonate solution and dried. Removal of the solvents yields the crude product. Further purification is achieved by chromatography.

Scheme 28.11: Attachment to C4'

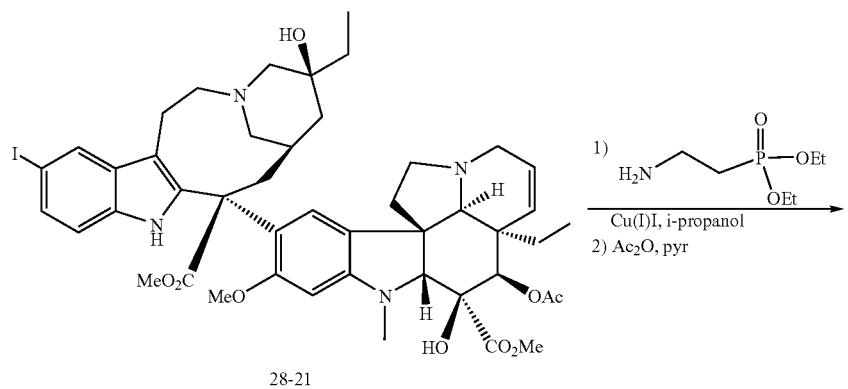

28-21

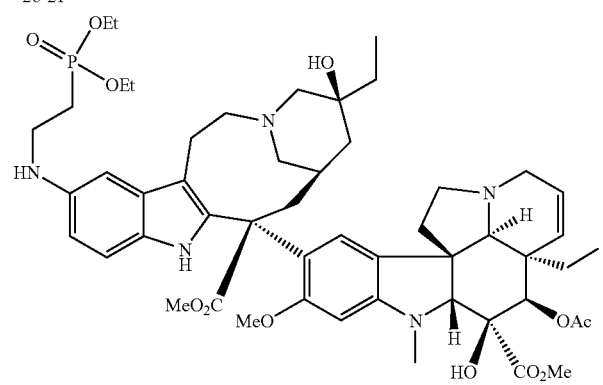

28-22

C12'-Iodo-vinblastine (prepared according to Pearce, "Medicinal Chemistry of Bisindole Alkaloids from Catharanthus", in *The Alkaloids* Vol. 37, 145, Academic Press San Diego, (1990), by iodination of vinblastine with ferrous perchlorate, tetra(n-propyl)ammonium periodinate and a catalytic amount of ruthenium dioxide) is added to a mixture of copper(I) iodide and potassium phosphate and 2-aminoethylphosphonic acid diethyl ester (commercially available). The reaction mixture is heated under an inert gas atmosphere to ~80° C., according to a procedure from Buchwald in *Org. Lett.*, (2002), 4, 581-584. At the end of the reaction the material is cooled to room temperature and the solvent is removed in vacuo. The crude reaction mixture is extracted with an organic solvent such as DCM. The combined organic extracts are washed with aqueous bicarbonate solution and dried. Removal of the solvents yields the crude product. Further purification is achieved by chromatography. The product of this step is dissolved in an organic solvent such as DCM or THF. Pyridine is added, followed by acetic anhydride, and the reaction is stirred at room temperature according to *J. Med. Chem.*, (1979), 22, 391-400. At the end of the reaction, methanol is added and the solvents are removed in vacuo. The crude material is dissolved in an organic solvent such as DCM and washed with water and aqueous bicarbonate solution and dried. Removal of the solvents in vacuo yields the crude product. Further purification is achieved by chromatography.

thus", in *The Alkaloids* Vol. 37, 145, Academic Press San Diego, (1990), by exhaustive hydrolysis of vinblastine in NaOH (5N) under refluxing conditions) is dissolved in an organic solvent such as dimethylformamide (DMF) at room temperature. Methyl iodide (1 equiv) is added, followed by potassium carbonate. Stirring at room temperature is continued. At the end of the reaction, the reaction is filtered and the solvent is removed in vacuo. The desired C24 methyl ester is purified by chromatography. The product of step 1 is dissolved in an organic solvent such as DCM or DMF and the solution is cooled to −10° C. A tertiary amine base such as DIEA is added, followed by a coupling reagent such as isobutylchloroformate. Stirring at −10° C. is continued until the activation is complete. Aminoethylphosphonic acid diethyl ester is added and stirring with slow warming to 0° C. is continued. At the end of the reaction, the solution is warmed to room temperature and the solvent is removed in vacuo. The product is further purified by chromatography. The product of this step is dissolved in an organic solvent such as DCM or THF. Pyridine is added, followed by acetic anhydride, and the reaction is stirred at room temperature according to *J. Med. Chem.*, (1979), 22, 391-400. At the end of the reaction, methanol is added and the solvents are removed in vacuo. The crude material is dissolved in an organic solvent such as DCM and washed with water and aqueous bicarbonate solution and

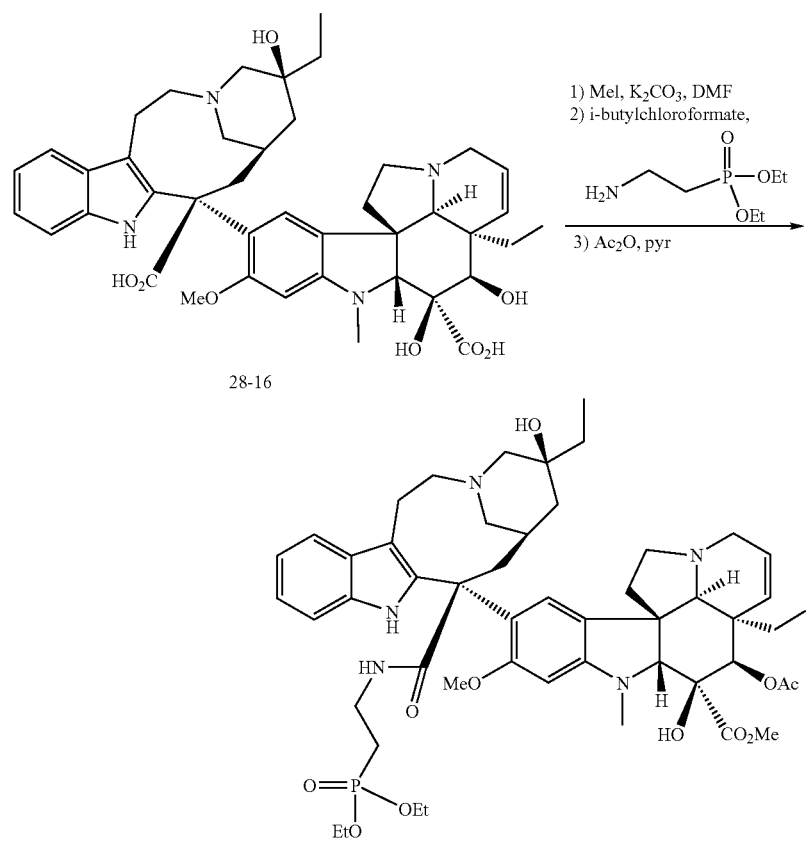

The starting material (prepared according to Pearce, "Medicinal Chemistry of Bisindole Alkaloids from Catharandried. Removal of the solvents in vacuo yields the crude product. Further purification is achieved by chromatography.

Example 29

Preparation of Exemplary Compounds of the Present Invention

Reduction of the dose and/or improvement of efficacy are achieved by the use of pro-drugs of analogs of tipifarnib which, upon cleavage inside the target cell, give rise to an agent with an increased intracellular half-life. Such compounds are described below.

Scheme 29.1

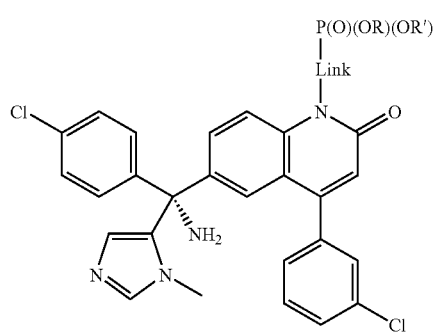

29-1

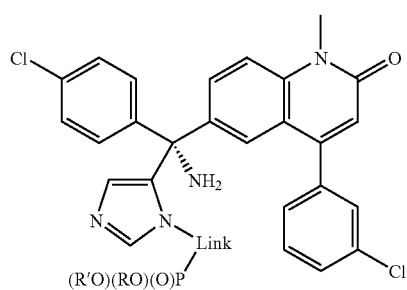

29-2

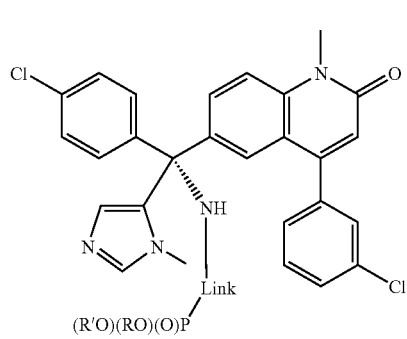

29-3

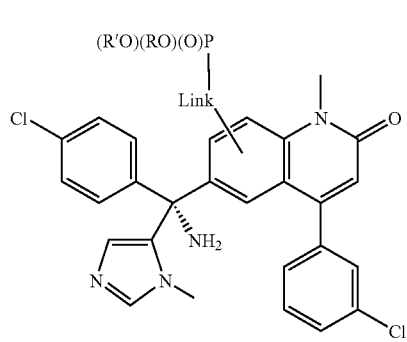

29-4

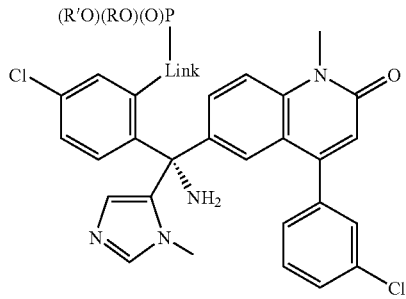

29-5

Link is 1–8 atoms, with 2–6 preferred

Compounds such as these can be made according to the general routes outlined in Schemes 29.2, 29.4, 29.6, 29.8 and 29.10, with specific exemplifications illustrated in Schemes 29.3, 29.5, 29.7, 29.9 and 29.11.

Scheme 29.2

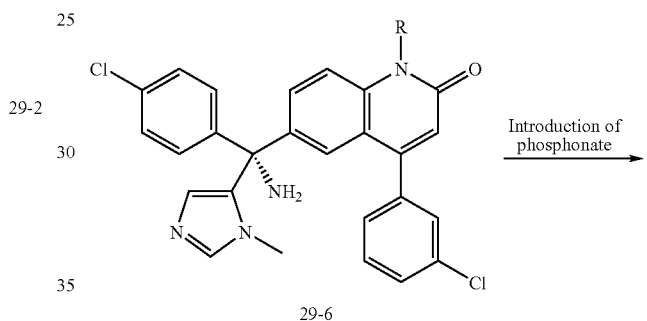

29-6

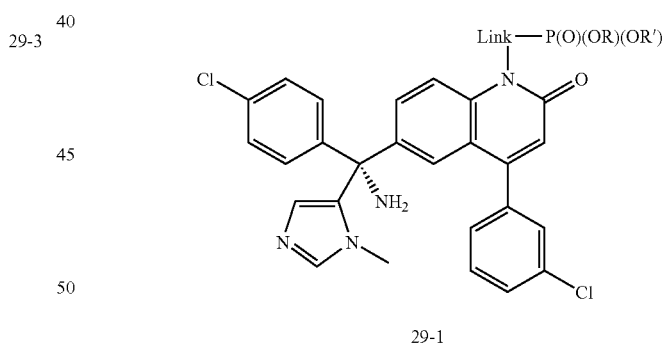

29-1

Scheme 29.3

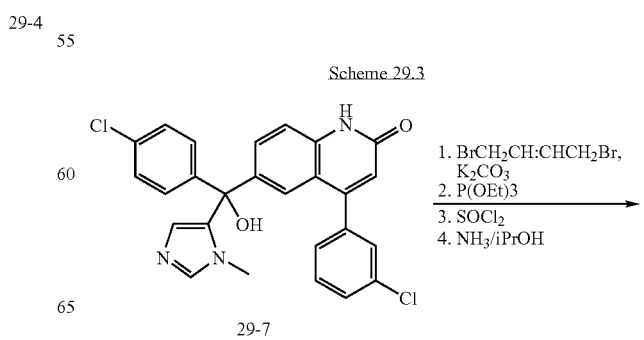

29-7

1. BrCH₂CH:CHCH₂Br, K₂CO₃
2. P(OEt)₃
3. SOCl₂
4. NH₃/iPrOH

-continued

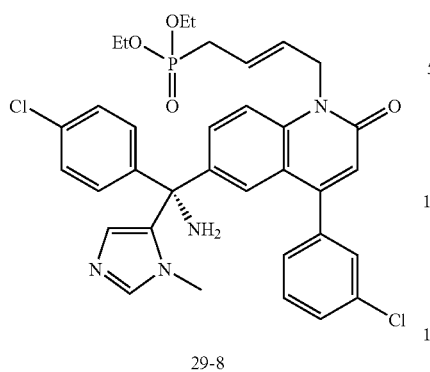

29-8

The quinolone (see U.S. Pat. No. 5,968,952) is treated in a solvent such as dimethylformamide (DMF) or tetrahydrofuran (THF) with a base such as potassium carbonate. E-1,4-dibromobutene is added in excess. After quenching the reaction with aqueous ammonium chloride and extracting the product with an organic solvent such as ethyl acetate, the mono-alkylated product is isolated by chromatography. The bromide is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. Subsequently, the tertiary alcohol is converted via the chloride to the amine using methods described in *Bioorg. Med. Chem. Lett.*, (2003), 13, 1543. The desired enantiomer is isolated by chromatography or by classical resolution using a chiral acid such as camphor sulfonic acid.

Scheme 29.4

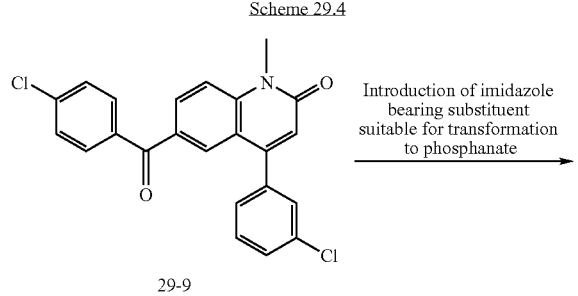

29-9

Introduction of imidazole bearing substituent suitable for transformation to phosphanate

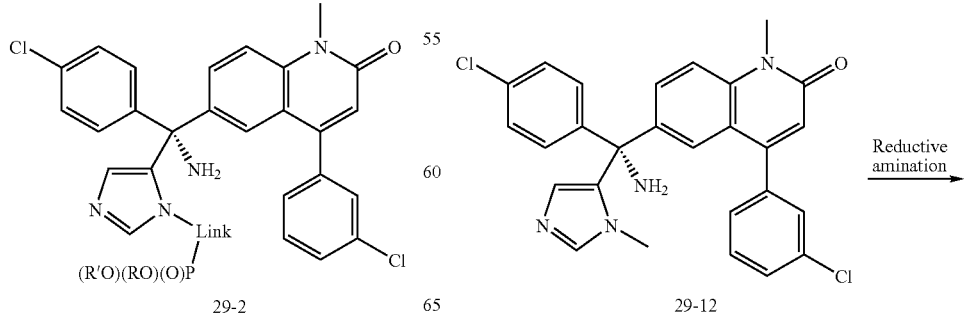

29-2

Scheme 29.5

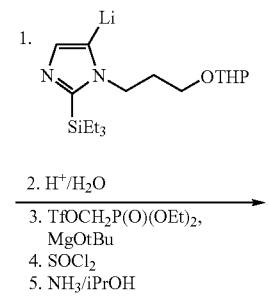

29-9

1. <image showing lithiated imidazole with SiEt₃, OTHP>
2. H⁺/H₂O
3. TfOCH₂P(O)(OEt)₂, MgOtBu
4. SOCl₂
5. NH₃/iPrOH

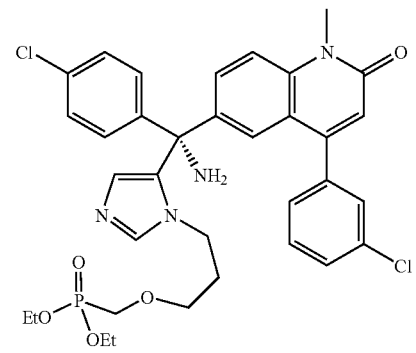

29-11

The N-methylquinolone (see U.S. Pat. No. 5,968,952, made by treating the starting material in Scheme 29.3 with methyl iodide and potassium carbonate in a solvent such as DMF) is treated with the lithiated imidazole shown (made from 1-(3-tetrahydropyranyloxy)propyl)imidazole by successive treatment with n-butyl lithium, chlorotriethylsilane, and n-butyl lithium; see in *Bioorg. Med. Chem. Lett.*, (2003), 13, 1543). After hydrolysis of the ether protecting group, the liberated primary alcohol is treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester. Subsequently, the tertiary alcohol is converted via the chloride to the amine using methods described in *Bioorg. Med. Chem. Lett.*, (2003), 13, 1543. The desired enantiomer is isolated by chromatography or by classical resolution using a chiral acid such as camphor sulfonic acid.

Scheme 29.6

Reductive amination 29-12

-continued

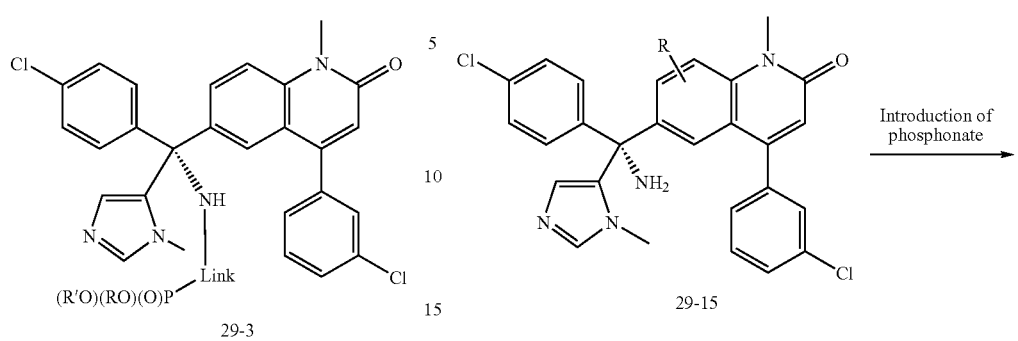

29-3

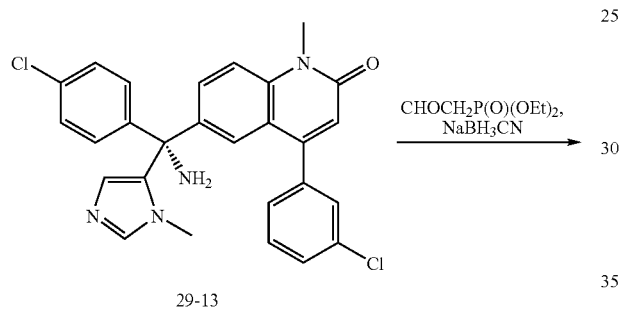

29-13

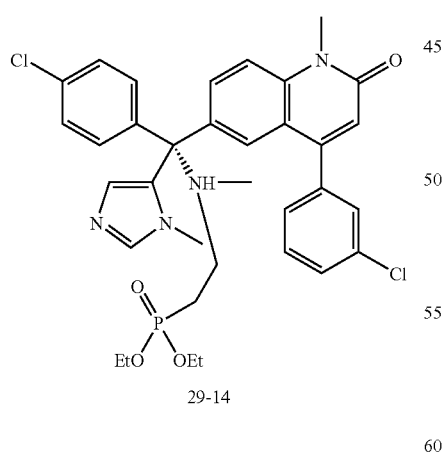

29-14

The primary amine is condensed with (2-oxo-ethyl)-phosphonic acid diethyl ester under reductive conditions such as those achieved through the use of sodium cyanoborohydride in a solvent such as methanol or dimethylformamide (see *Tet. Lett.* (1990) 31, 5595).

Scheme 29.8

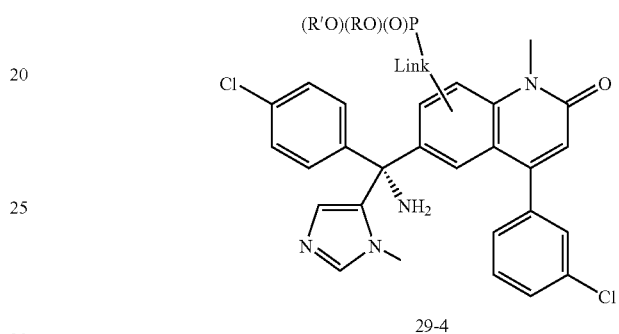

29-15

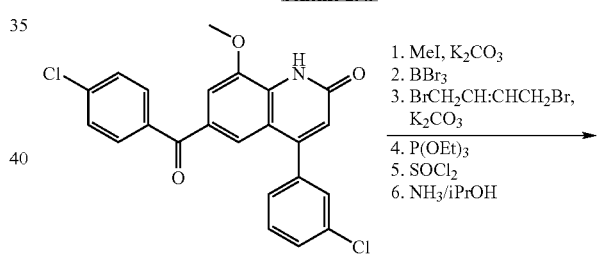

29-4

Scheme 29.9

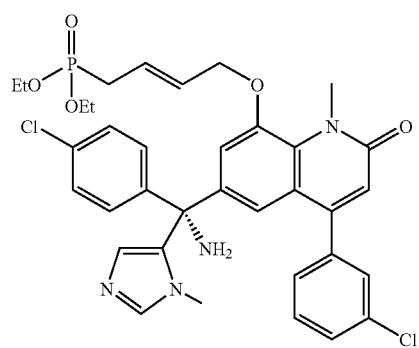

29-16

1. MeI, K₂CO₃
2. BBr₃
3. BrCH₂CH:CHCH₂Br, K₂CO₃
4. P(OEt)₃
5. SOCl₂
6. NH₃/iPrOH 29-17

The quinolone (see *Bioorg. Med. Chem. Lett.*, (2003), 13, 1543) is N-methylated under standard conditions such as by treatment with iodomethane and potassium carbonate in DMF, and treatment with boron tribromide liberates the phenol. This is alkylated as in Scheme 29.3 above, and the subsequent steps are also analogous.

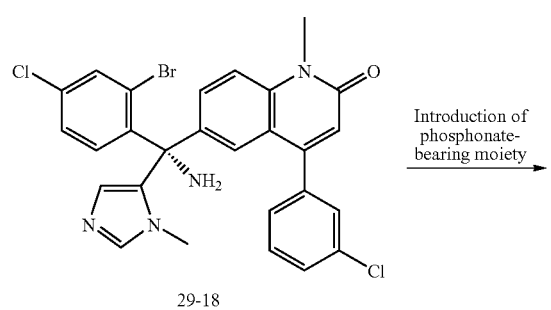

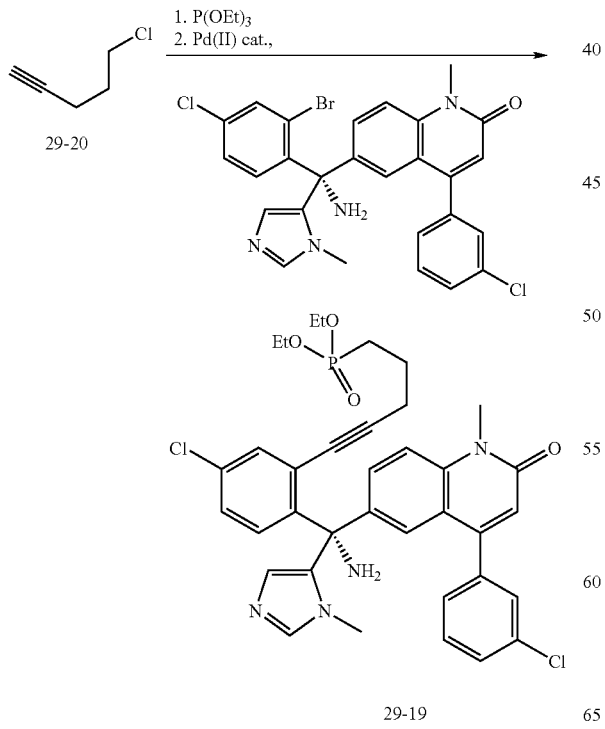

5-Chloro-1-pentyne is treated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. This acetylene is coupled with the bromo-containing analog of tipifarnib shown (made as in *Bioorg. Med. Chem. Lett.*, (2003), 13, 1543, but starting from 2-bromo-4-chloro-4'-nitrobenzophenone) under conditions such as those pioneered by Sonagashira (Sonagashira, K.; Tohda, Y.; Hagihara, N. *Tetrahedron Lett.*, (1975), 4467).

Further manipulations can be performed on the phosphonate moiety prior to the final deprotection. These types of transformations are more extensively described in the following section.

Example 30

Preparation of Exemplary Compounds of the Present Invention

Compounds of the invention can be prepared as generally described in Schemes 30.1-30.3, with examples depicted in Schemes 30.4-30.6.

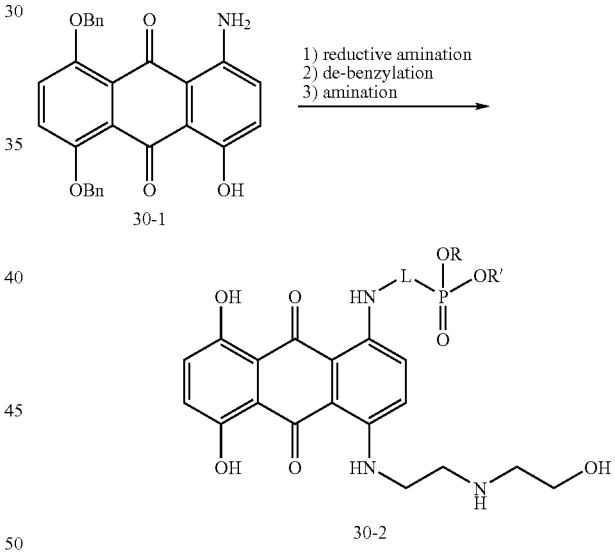

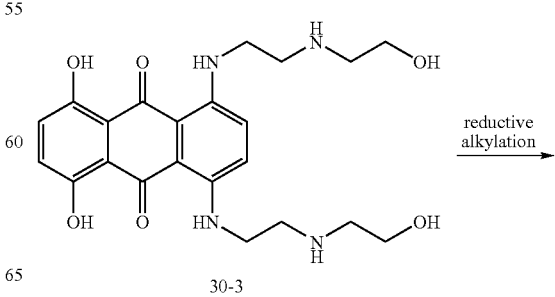

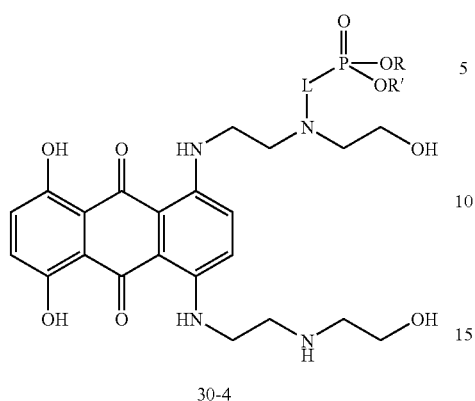

30-4

Scheme 30.3: Chain extension

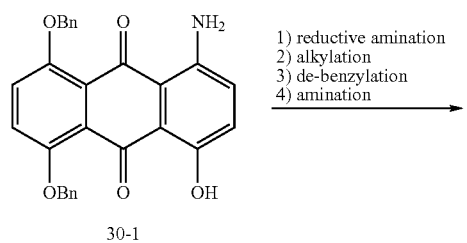

30-1

1) reductive amination
2) alkylation
3) de-benzylation
4) amination

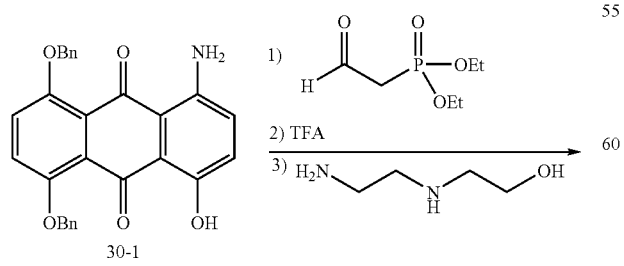

30-5

Scheme 30.4: Replacement of one amino substituent

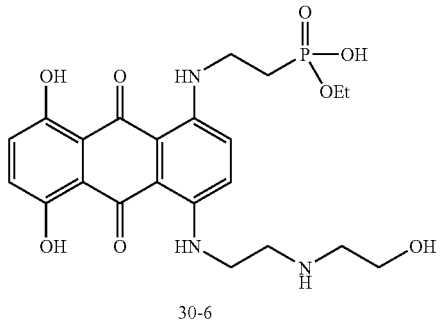

30-6

The starting material (synthesis described in *J. Med. Chem.*, (1999), 42, 3494-3501) is treated in an organic solvent such as tetrahydrofuran (THF) or dichloromethane (DCM) with diethyl phosphonato ethyl carbaldehyde (1 equiv.) and sodium triacetoxyborohydride as described in *J. Org. Chem*, (1996), 61, 3849-3862. The reaction is quenched with aqueous sodium bicarbonate and the product is extracted with an organic solvent such as ethyl acetate. Drying and removal of the solvent yields the crude product. Further purification is achieved by chromatography.

The product of this step is dissolved in trifluoroacetic acid (TFA) and is stirred at room temperature, according to *J. Med. Chem.*, (1999), 42, 3494-3501. At the end of the reaction, benzene is added and the solvents are removed in vacuo. The crude material is sufficiently pure for the next step.

The crude material is dissolved in a mixture of N,N,N',N' tetramethylethylenediamine, water and N-(β-hydroxyethyl)-N-(β-aminoethyl) amine, and the mixture is heated to reflux for several hours, according to a procedure from *J. Med. Chem.*, (1999), 42, 3494-3501. At the end of the reaction, chloroform is added and the reaction mixture is washed with diluted aqueous hydrochloric acid and water and is dried. Removal of the solvents yields the crude product. Further purification is achieved by chromatography.

Scheme 30.5: Attachment at one secondary alkyl amine

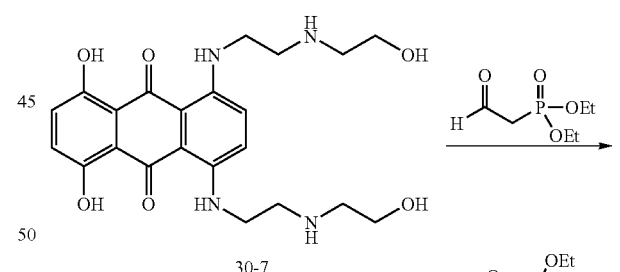

30-7

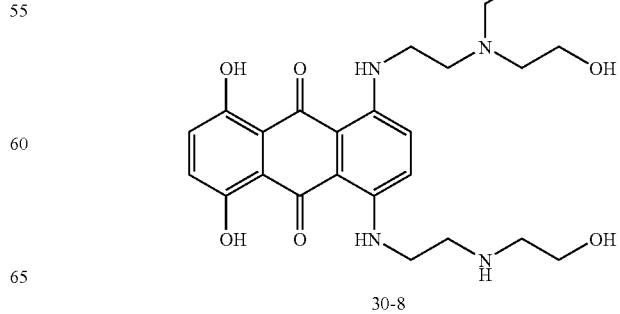

30-8

Mitoxantrone is treated in an organic solvent such as THF or DCM with diethyl phosphonato ethyl carbaldehyde (1 equiv.) and sodium triacetoxyborohydride as described in *J. Org. Chem*, (1996), 61, 3849-3862. The reaction is quenched with aqueous sodium bicarbonate and the product is extracted with an organic solvent such as ethyl acetate. Drying and removal of the solvent yields the crude product. Further purification is achieved by chromatography.

Scheme 30.6: Chain extension

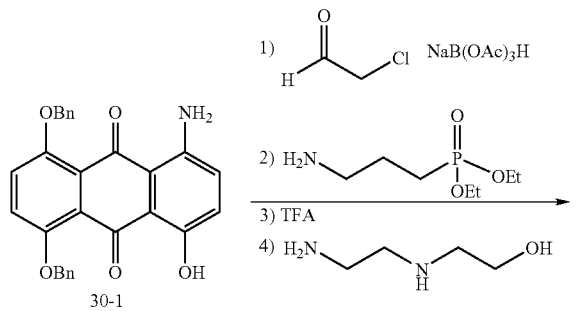

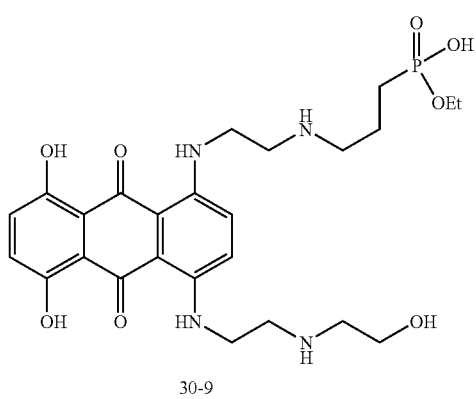

The starting material (synthesis described in *J. Med. Chem.*, (1999), 42, 3494-3501) is treated in an organic solvent such as THF or DCM with chloroacetaldehyde (1 equiv.) and sodium triacetoxyborohydride as described in *J. Org. Chem*, (1996), 61, 3849-3862. The reaction is quenched with aqueous sodium bicarbonate and the product is extracted with an organic solvent such as ethyl acetate. Drying and removal of the solvent yields the crude product. Further purification is achieved by chromatography.

The product of this step is dissolved in an organic solvent such as dimethylformamide or acetonitrile. 3-Aminopropyl phosphonic acid diethyl ester is added, followed by potassium carbonate and sodium iodide. The reaction mixture is heated to an elevated temperature of ~50-60° C. At the end of the reaction, the mixture is cooled to room temperature. Chloroform is added and the reaction mixture is washed with diluted aqueous hydrochloric acid and water. Drying and removal of the solvents yields the crude product. Further purification is achieved by chromatography.

The product of this step is dissolved in trifluoroacetic acid (TFA) and is stirred at room temperature, according to *J. Med. Chem.*, (1999), 42, 3494-3501. At the end of the reaction, benzene is added and the solvents are removed in vacuo. The crude material is sufficiently pure for the next step.

The crude material is dissolved in a mixture of N,N,N',N'-tetramethylethylenediamine, water, and N-(β-hydroxyethyl)-N-(β-aminoethyl) amine, and the mixture is heated to reflux for several hours, according to a procedure from *J. Med. Chem.*, (1999), 42, 3494-3501. At the end of the reaction, chloroform is added and the reaction mixture is washed with diluted aqueous hydrochloric acid and water and is dried. Removal of the solvents yields the crude product. Further purification is achieved by chromatography.

Further manipulations can be performed on the phosphonate moiety prior to the final deprotection. These types of transformations are more extensively described in the following section.

Example 31

Preparation of Exemplary Compounds of the Present Invention

Compounds of the invention can generally be prepared as described in Schemes 31.1-31.6, with examples depicted in Schemes 31.7-31.12.

Scheme 31.1: Modification at C4

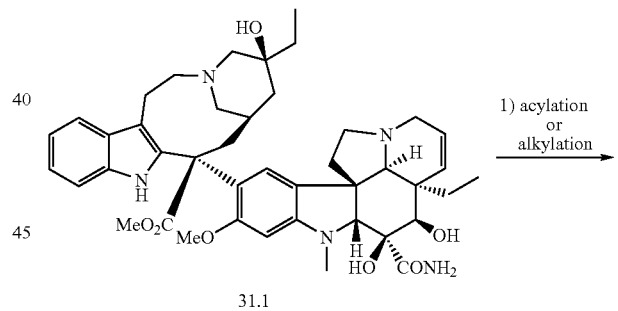

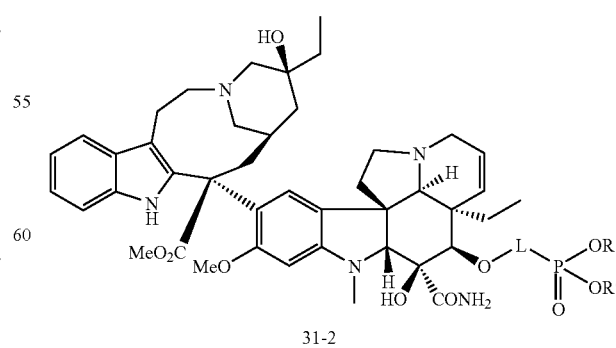

Scheme 31.2: Attachment to C23
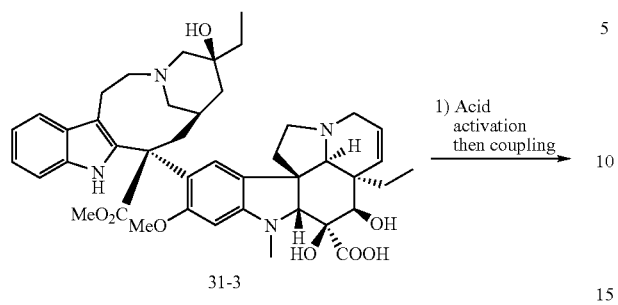
Scheme 31.4: Attachment to C4'
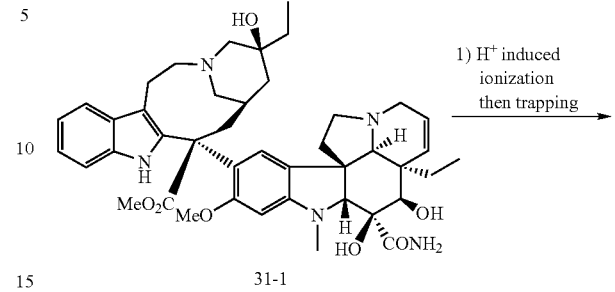
Scheme 31.3: Attachment to N1
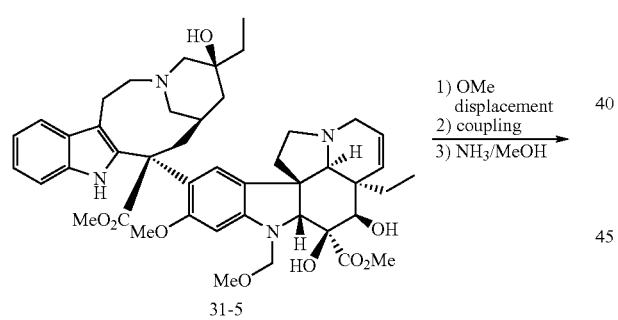
Scheme 31.5: Attachment to C12'
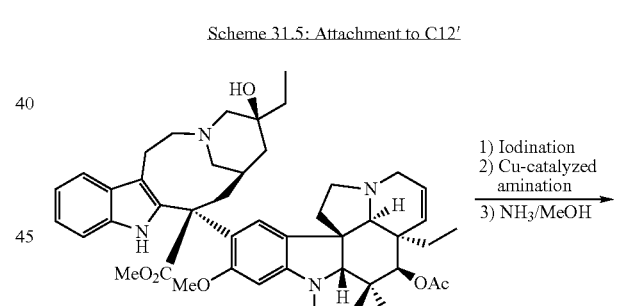

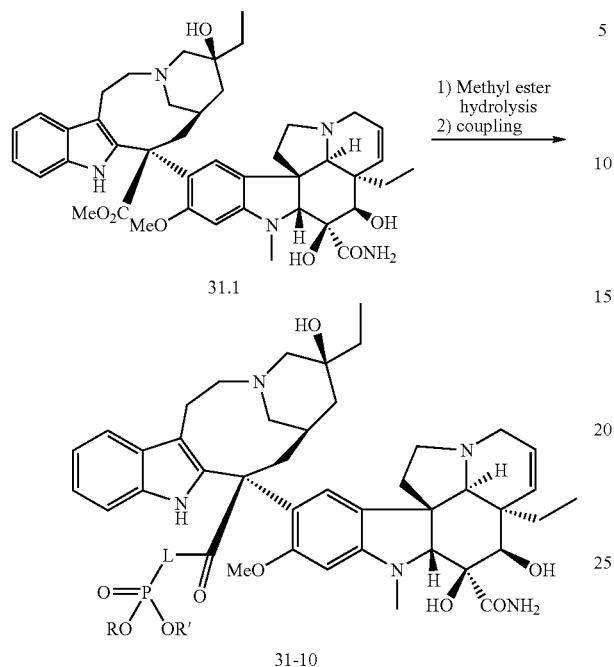
Scheme 31.6: Attachment to C22'
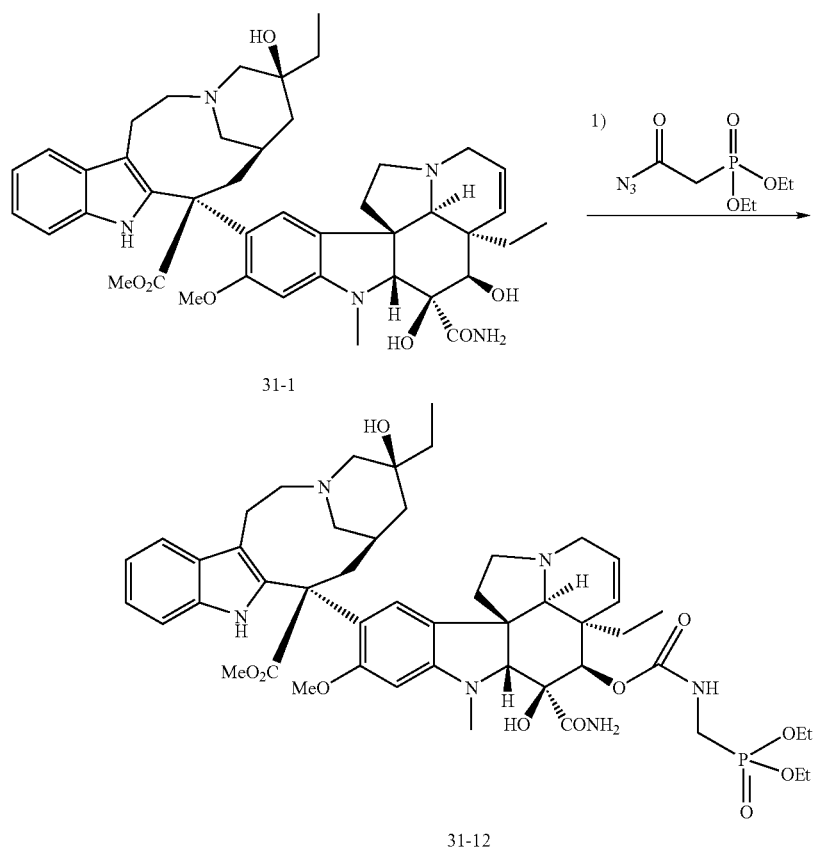
Scheme 31.7: Attachment to C4

2-Diethyl phosphonatoacetic acid is dissolved in an organic solvent such as benzene, tetrahydrofuran (THF), or chloroform, is combined with a tertiary amine base such as diisopropylethylamine (DIEA) and diphenyl phosphorazidate (1.2 equiv) and is stirred at room temperature according to *J. Med. Chem.*, (1991), 34, 1001-1018. After the acyl azide has been formed, vindesine is added and the reaction mixture is heated to ~80° C. for ~4 hrs (*Biochemistry* (2002), 41, 14010-14018). The reaction mixture is cooled to room temperature, washed aqueous HCl (1N) and aqueous bicarbonate solution and dried. Removal of the solvents yields the crude product. Further purification is achieved by chromatography.

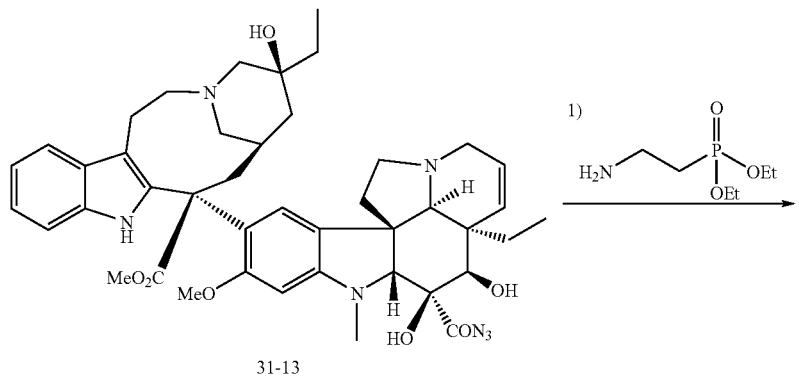

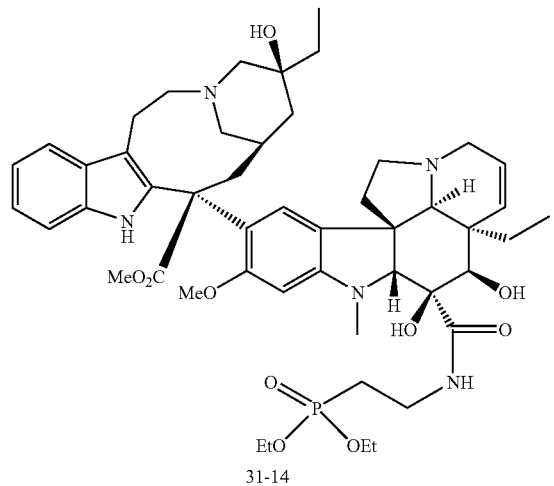

The starting material (synthesis published in *J. Med. Chem.*, (1978), 21, 88-96; from vinblastine) is treated in an organic solvent such as dichloromethane (DCM) or THF with 2-aminoethylphosphonic acid diethyl ester at room temperature, according to the procedure described in *J. Med. Chem*, (1979), 22, 391-400. At the end of the reaction, the solution is washed with water, aqueous bicarbonate and water, and is dried. Evaporation of solvents yields the crude product. Further purification is achieved by chromatography.

Scheme 31.9: Attachment to N1

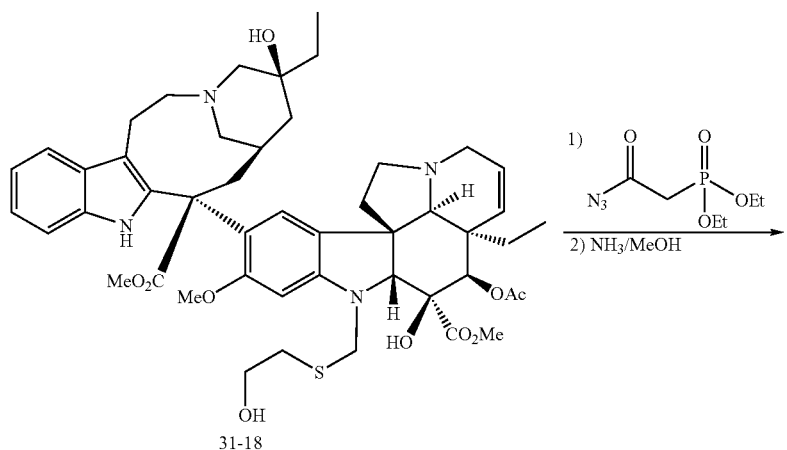

31-18

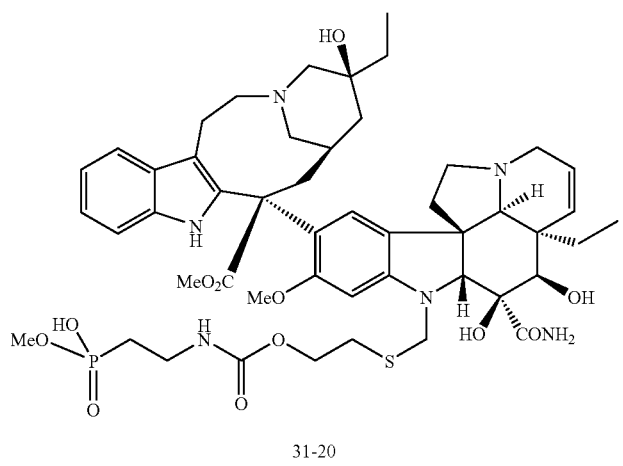

31-20

2-Diethyl phosphonatoacetic acid is dissolved in an organic solvent such as benzene, THF, or chloroform, and is combined with a tertiary amine base such as diisopropylethylamine (DIEA) and diphenyl phosphorazidate (1.2 equiv) and stirred at room temperature according to *J. Med. Chem.*, (1991), 34, 1001-1018. After the acyl azide has been formed, N-1-(β-hydroxyethylthiomethyl)vinblastine (prepared according to Pearce, "Medicinal Chemistry of Bisindole Alkaloids from Catharanthus", in *The Alkaloids*, Vol. 37, 145, Academic Press San Diego, (1990), from vinblastine via $CrO_3$-mediated oxidation in the presence of methanol and subsequent methoxy displacement with β-hydroxythioethanol) is added, and the reaction mixture is heated to ~80° C. for ~4 hrs (*Biochemistry* (2002), 41, 14010-14018). The reaction mixture is cooled to room temperature, washed with aqueous hydrochloric acid (HCl) (1N) and aqueous bicarbonate solution, and dried. Removal of the solvents yields the crude product. Further purification is achieved by chromatography.

The product of this step is dissolved in an anhydrous organic solvent such as methanol and dry liquid ammonia is added. The reaction mixture is heated in sealed reaction vessel to an elevated temperature of ~100° C., according to a procedure from *J. Med. Chem.*, (1978), 21, 88-96. At the end of the reaction, the mixture is cooled to room temperature and the solvents are removed in vacuo. Further purification is achieved by chromatography.

Scheme 31.10: Attachment to C4'

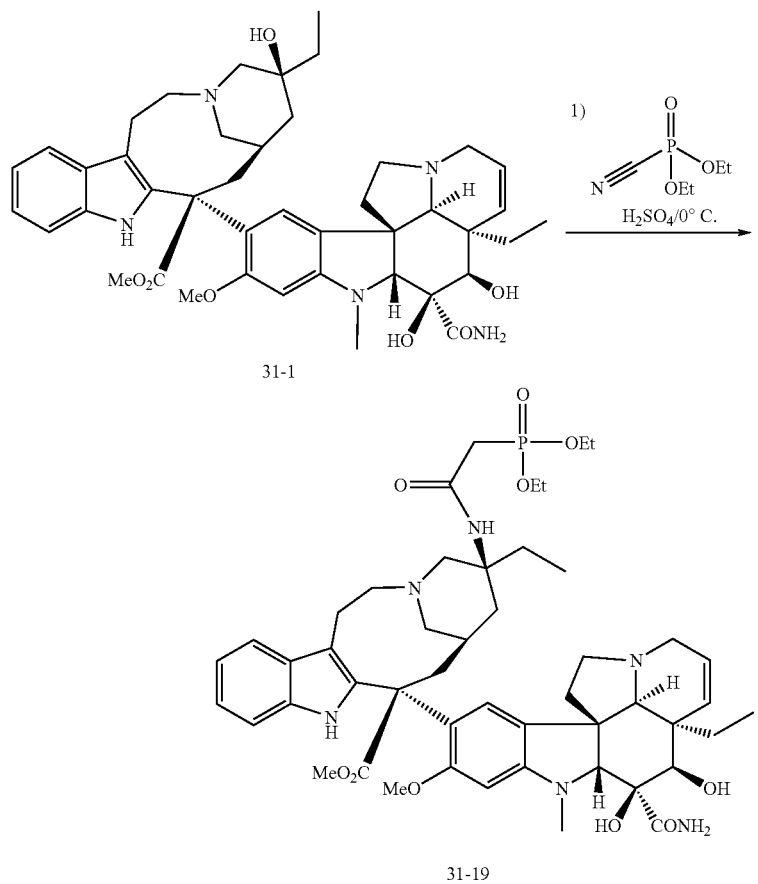

Vindesine and diethyl (cyanomethyl)phosphonate (commercially available) are dissolved in conc. sulfuric acid at a temperature of ~0° C., according to a procedure from Pearce, "Medicinal Chemistry of Bisindole Alkaloids from Catharanthus", in *The Alkaloids*, Vol. 37, 145, Academic Press San Diego, (1990) (described for acetonitrile). When the starting material is consumed the reaction mixture is carefully diluted with water and further neutralized. The crude reaction mixture is extracted with an organic solvent such as DCM. The combined organic extracts are washed with aqueous bicarbonate solution and dried. Removal of the solvents yields the crude product. Further purification is achieved by chromatography.

Scheme 31.11: Attachment to 12'

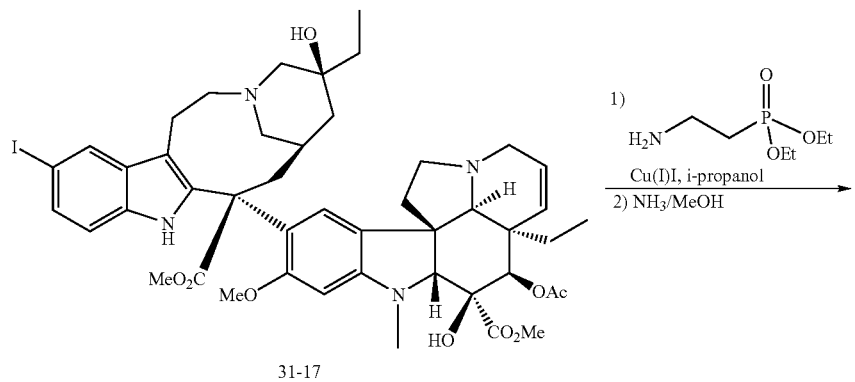

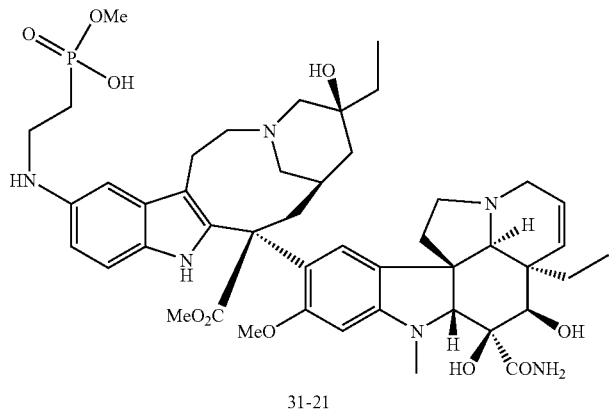

31-21

C12'-Iodo-vinblastine (prepared according to Pearce, "Medicinal Chemistry of Bisindole Alkaloids from Catharanthus", in *The Alkaloids*, Vol. 37, 145, Academic Press, San Diego, (1990), by iodination of vinblastine with ferrous perchlorate, tetra(n-propyl)ammonium periodinate and a catalytic amount of ruthenium dioxide) is added to a mixture of copper(I) iodide and potassium phosphate and 2-aminoethyl phosphonic acid diethyl ester (commercially available). The reaction mixture is heated under an inert gas atmosphere to ~80° C., according to a procedure from Buchwald in *Org. Lett.*, (2002), 4, 581-584. At the end of the reaction the material is cooled to room temperature and the solvent is removed in vacuo. The crude reaction mixture is extracted with an organic solvent such as DCM. The combined organic extracts are washed with aqueous bicarbonate solution and dried. Removal of the solvents yields the crude product. Further purification is achieved by chromatography.

The product of this step is dissolved in an anhydrous organic solvent such as methanol and dry liquid ammonia is added. The reaction mixture is heated in sealed reaction vessel to an elevated temperature of 100° C., according to a procedure from *J. Med. Chem.*, (1978), 21, 88-96. At the end of the reaction the mixture is cooled to room temperature and the solvents are removed in vacuo. Further purification is achieved by chromatography.

Scheme 31.12: Attachment to 22'

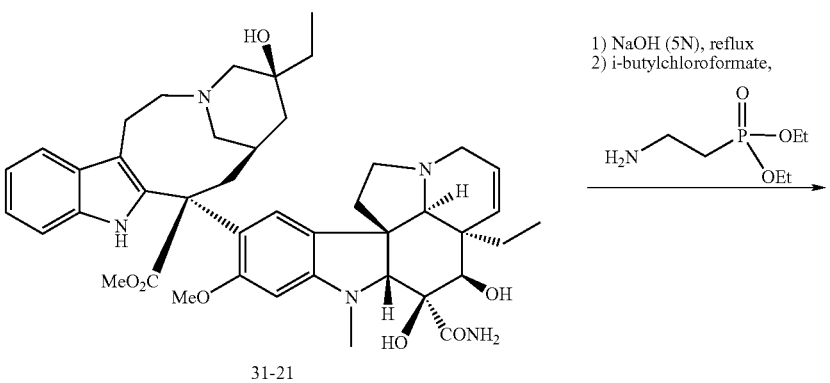

31-21

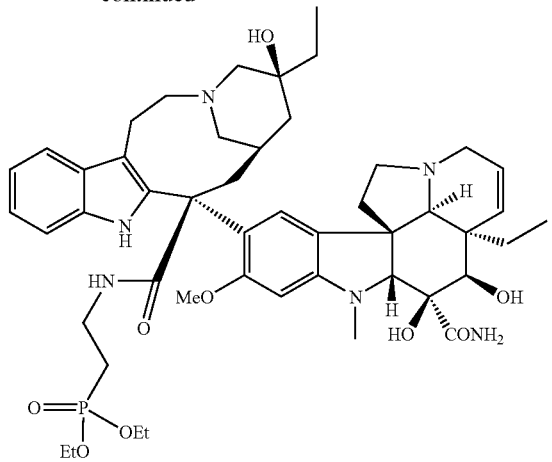

31-15

Vindesine is suspended in aqueous sodium hydroxide (5N) and is heated to reflux for several hours, according to Pearce, "Medicinal Chemistry of Bisindole Alkaloids from Catharanthus", in *The Alkaloids*, Vol. 37, 145, Academic Press, San Diego, (1990) (described for vinblastine). At the end of the reaction, water is added and the reaction mixture is extracted with an organic solvent such as DCM or chloroform. The combined organic extracts are washed with brine and are dried. Removal of the solvent in vacuo yields the crude acid. Further purification is achieved by chromatography. The product of step 1 is dissolved in an organic solvent such as DCM or dimethylformamide and the solution is cooled to −10° C. A tertiary amine base such as DIEA is added, followed by a coupling reagent such as iso-butylchloroformate. Stirring at −10° C. is continued until the activation is complete. Aminoethylphosphonic acid diethyl ester is added and stirring with slow warming to 0° C. is continued. At the end of the reaction, the solution is warmed to room temperature and the solvent is removed in vacuo. The product is further purified by chromatography.

Example 32

Preparation of Exemplary Compounds of the Present Invention

Scheme 32.1

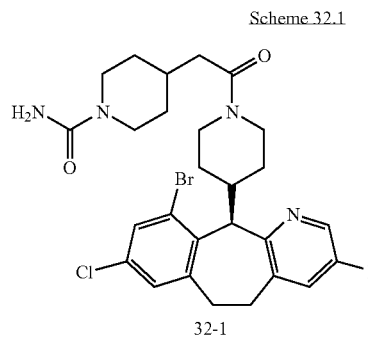

32-1

Direct introduction of phosphonate moiety

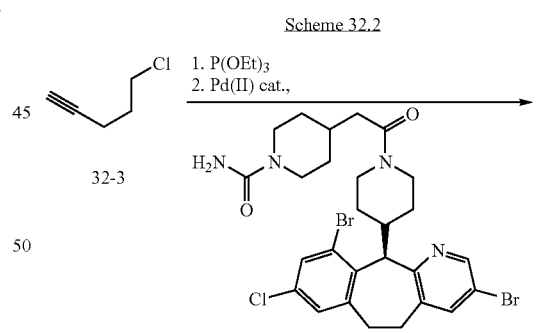

32-2

Scheme 32.2

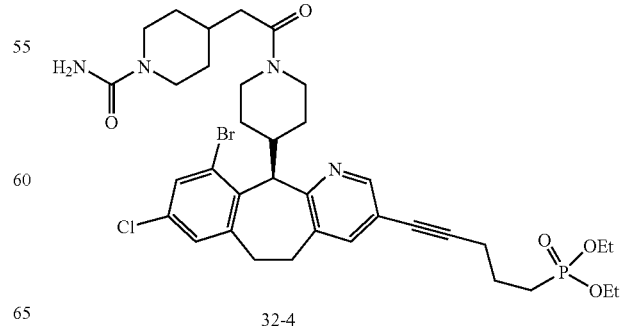

32-4

5-Chloro-1-pentyne is treated with triethylphosphite in a solvent such as toluene (or other Arbuzov reaction conditions: see Engel, R., Synthesis of carbon-phosphorus bonds, CRC press (1988) to generate the diethyl ester of the desired phosphonic acid. This acetylene is coupled with lonafarnib under conditions such as those pioneered by Sonagashira (Sonogashira, K.; Tohda, Y.; Hagihara, N. *Tetrahedron Lett.*, (1975), 4467).

Scheme 32.3

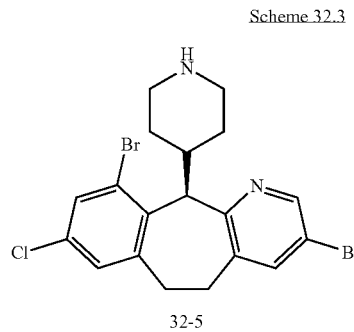

32-5

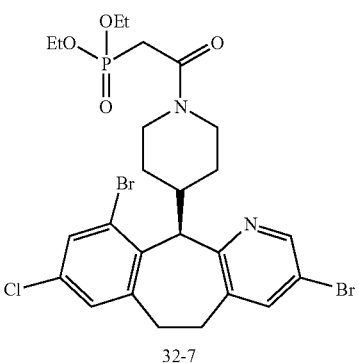

32-7

The piperazine shown (see *J. Med. Chem.*, (1998), 41, 4890) is acylated with an activated diethylphosphonoacetic acid to provide the desired amide linker compound, according to a procedure such as those reported in *J. Med. Chem.*, (1982), 25, 960-964 and *J. Med. Chem.*, (1984), 27, 600-604. The activated diethylphosphonoacetic acid is obtained by treatment in a solvent such as dimethylformamide with a coupling reagent such as diethyl cyanophosphonate and a base such as diisopropylethylamine at room temperature.

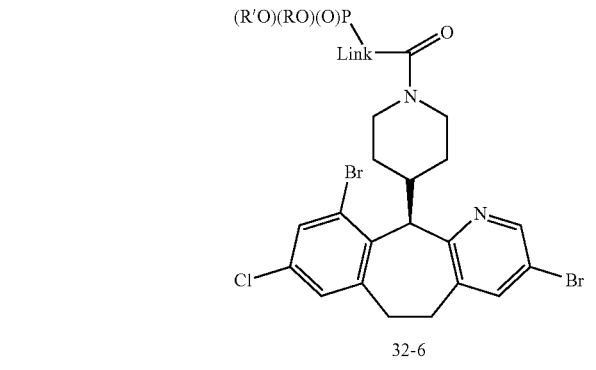

32-6

Scheme 32.5

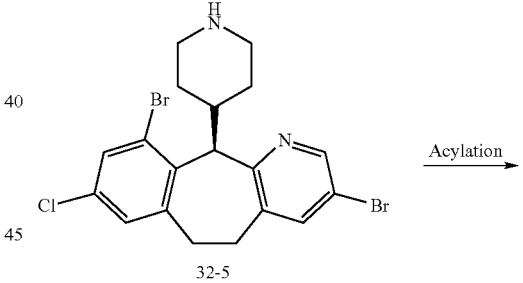

32-5

Scheme 32.4

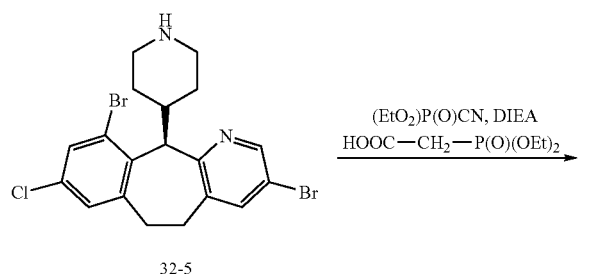

32-5

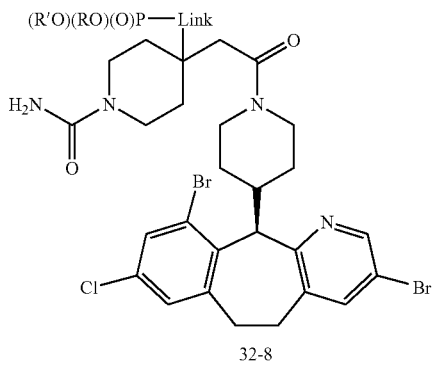

32-8

Scheme 32.6

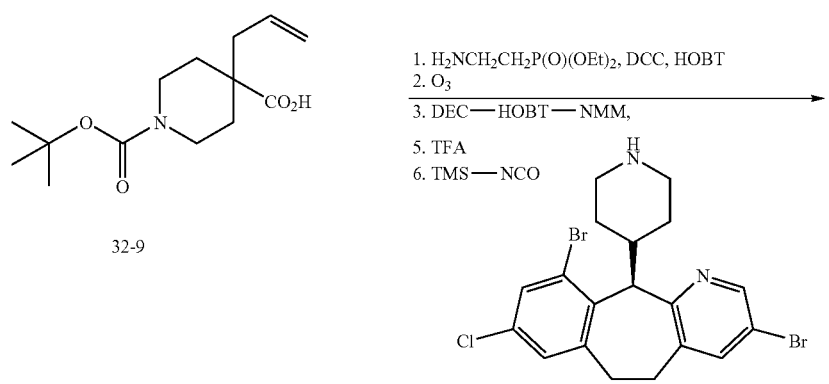

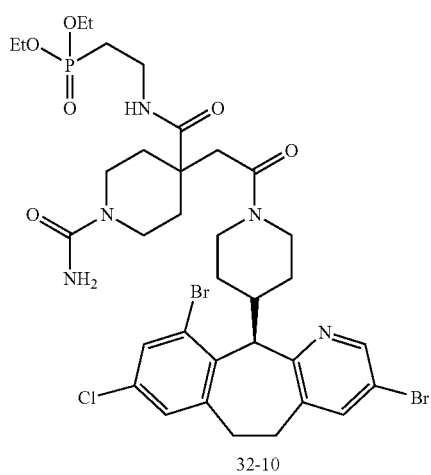

4-Allyl-piperidine-1,4-dicarboxylic acid mono-tert-butyl ester is coupled with 2-aminoethylphosphonic acid diethyl ester (commercially available) using standard reagents for the formation of a secondary amide such as dicyclohexylcarbodiimide (DCC) and hydroxybenztriazole (HOBT), in a solvent such as dimethylformamide. The olefin is oxidized with ozone to produce the carboxylic acid, which is then coupled with the piperidine reagent shown (see *J. Med. Chem.*, (1998), 41, 4890). Finally, the piperidine nitrogen is deprotected under standard conditions with trifluoroacetic acid, and the primary urea formed as described in see *J. Med. Chem.*, (1998), 41, 4890.

Scheme 32.7

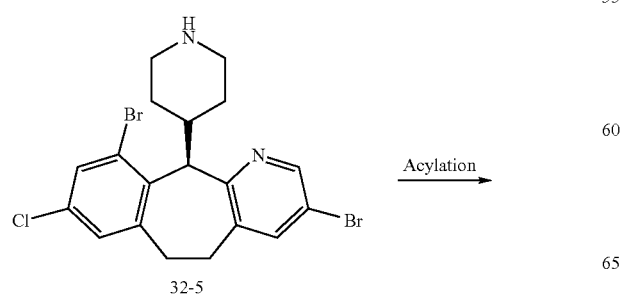

-continued

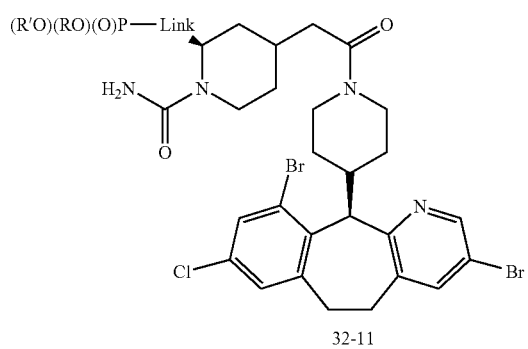

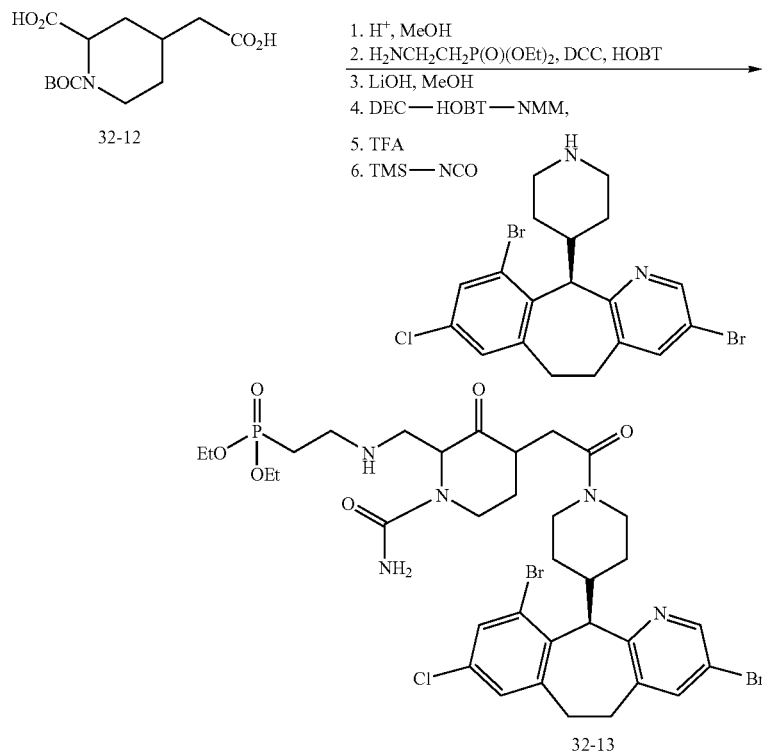

4-Carboxymethyl-piperidine-1,2-dicarboxylic acid 1-tert-butyl ester (commercially available) is mono-protected by treatment with acidic methanol. The remaining acid is coupled with 2-aminoethylphosphonic acid diethyl ester (commercially available) using standard reagents for the formation of a secondary amide such as dicyclohexylcarbodiimide (DCC) and hydroxybenztriazole (HOBT), in a solvent such as dimethylformamide. The methyl ester is then saponified and coupled to the piperazine shown (see *J. Med. Chem.*, (1998), 41, 4890). Finally, the piperidine nitrogen is deprotected under standard conditions with trifluoroacetic acid, and the primary urea formed as described in see *J. Med. Chem.*, (1998), 41, 4890.

Example 33

Preparation of Exemplary Compounds of the Present Invention

Compounds such as these can be made according to the general route outlined in Schemes 33.1-33.4, with examples depicted in Schemes 33.5-33.8.

Scheme 33.1: Modification of the phenol substituent

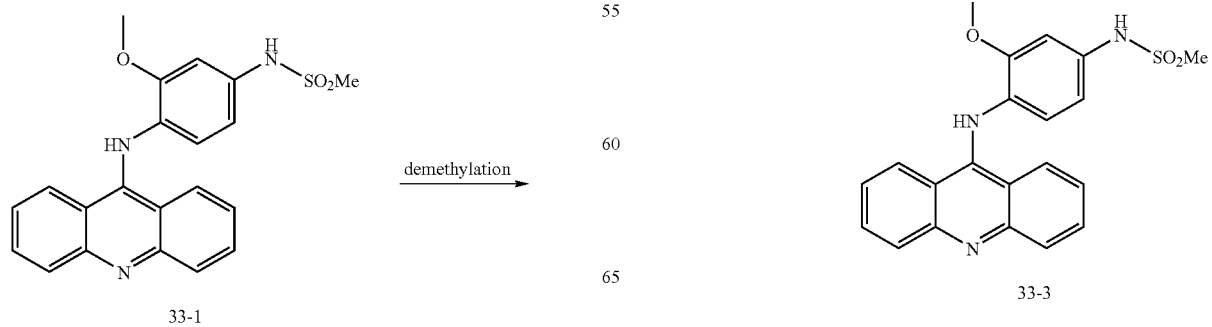

-continued

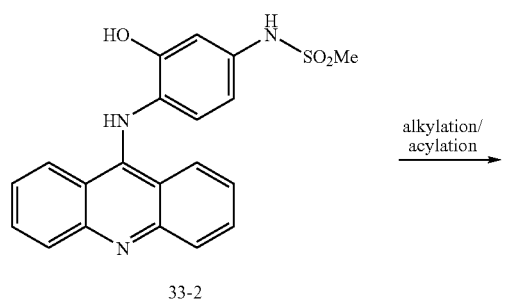

Scheme 33.2: Modification of the amine substituent
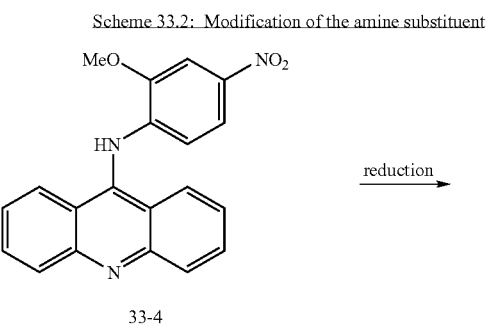
33-4
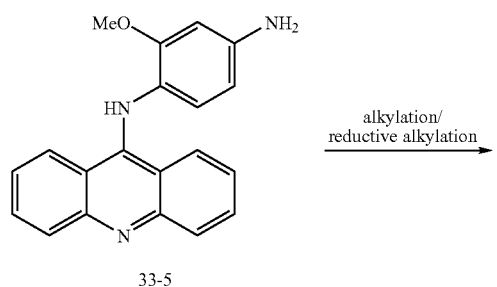
33-5
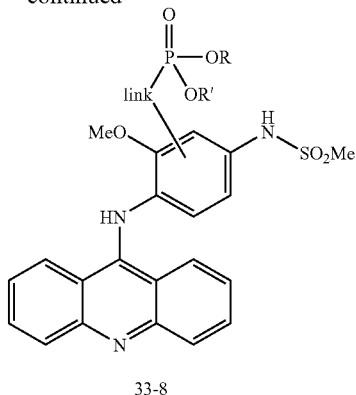
33-8
Scheme 33.4: Modifications at the acridine core
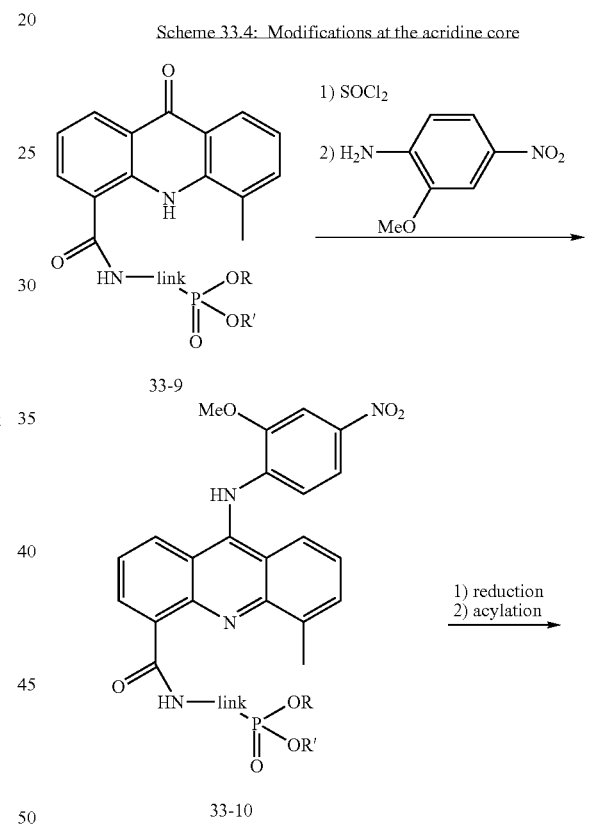
33-9
33-10
33-11
Scheme 33.3: Introduction of a further substituent
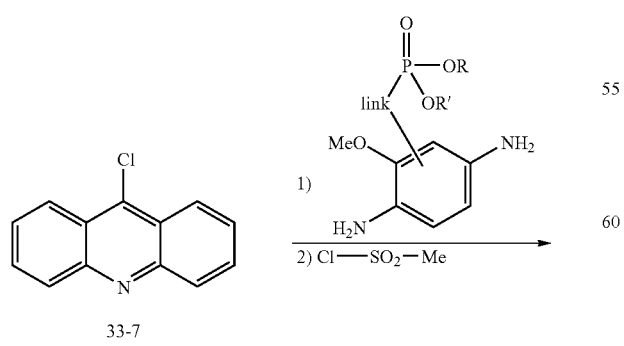
33-7

Scheme 33.5

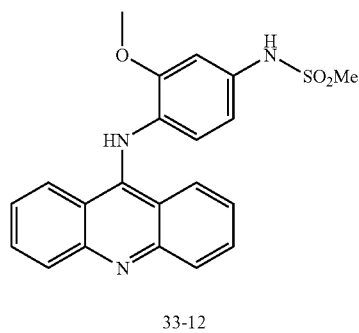

33-12

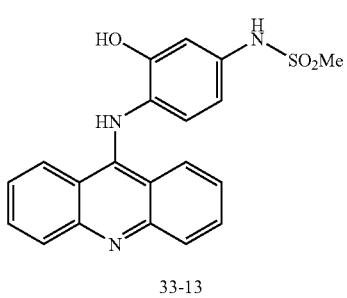

33-13

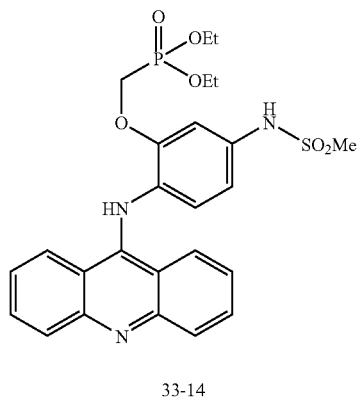

33-14

Amsacrine can be treated in a solvent such as dimethylformamide (DMF), acetonitrile (MeCN), or dichloromethane (DCM) with excess iodotrimethylsilane, as described in *Synthesis*, (1985), 274. After quenching the reaction with aqueous sodium bicarbonate and extracting the product with an organic solvent such as ethyl acetate, the free alcohol can be further purified by chromatography. This material is then treated with tert-butoxycarbonyl anhydride in an organic solvent such as DMF and in the presence of a tertiary amine base such as pyridine (Green and Wutts: Protective Groups in Organic chemistry). The solvent is removed in vacuo and the product is further purified by chromatography. The alkoxide anion is then generated via treatment with sodium hydride (NaH) (1 equiv) in an organic solvent such as THF or DMF, and this is then treated with diethyl phosphonomethyltriflate (prepared according to *Tetrahedron Lett.*, (1986), 27, 1477). When the starting material is consumed, the reaction is quenched with water and the product is extracted with an organic solvent such as ethyl acetate. A final chromatographic purification may be included. The tert-butoxycarbonyl protecting group is removed with trifluoroacetic acid (TFA) in DCM according to standard procedures (Green and Wutts: Protective Groups in Organic chemistry).

Scheme 33.6

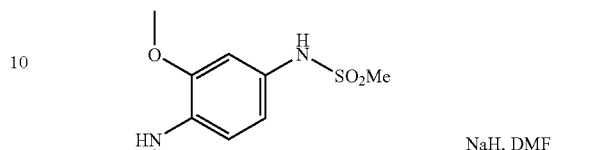

33-12

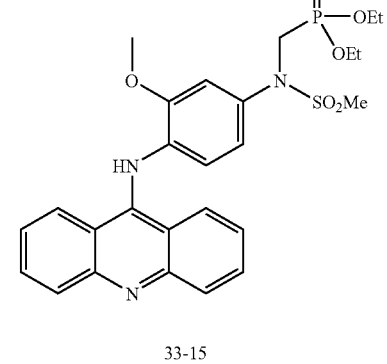

33-15

Amsacrine is deprotonated by treatment with NaH (1 equiv) in an organic solvent such as tetrahydrofuran (THF), and is then treated with diethyl phosphonomethyltriflate (prepared according to *Tetrahedron Lett.*, (1986), 27, 1477) according to a procedure such as that reported in *J. Med. Chem.*, (2000), 43, 489. When the starting material has been consumed, the reaction is quenched with water and the product is extracted with an organic solvent such as ethyl acetate. A final chromatographic purification may be included.

Scheme 33.7

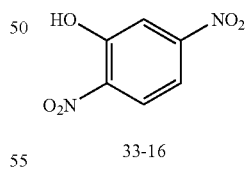

33-16

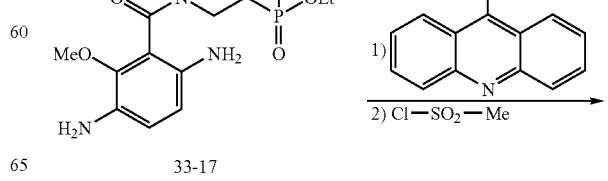

33-17

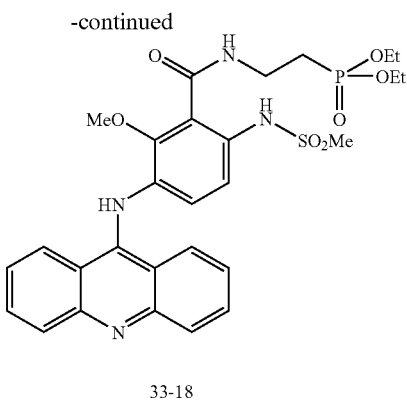

33-18

2,5-Dinitrophenol is converted to the sodium salt in an appropriate organic solvent such as THF, by treatment with NaH. The salt is then reacted with carbon dioxide under Kolbe Schmitt conditions (*J. Chem. Soc.* (1954), 3145). The carboxylic acid product is then activated with a suitable coupling reagent such as isobutyl chloroformate in an organic solvent such as DMF and in the presence of a tertiary amine base such as N,N-diisopropylethylamine (DIEA) at reduced temperatures of ~-10° C. The activated intermediate is then reacted with 2-aminoethylphosphonic acid diethyl ester and the reaction mixture is allowed to warm to 0° C. and then to room temperature. The solvent is removed in vacuo, and the crude material is dissolved in an organic solvent such as ethyl acetate and washed with diluted hydrochloric acid. The product is purified, as necessary, by chromatography. The material is dissolved in an organic solvent such as THF and is treated with sodium carbonate and methyl iodide or dimethylsulfate. After the reaction is complete, the solids are removed by filtration and the filtrate is concentrated in vacuo. The product is purified, as necessary, by chromatography. This material is then dissolved in a solvent such as ethyl acetate or DMF and is hydrogenated with the aid of Pd/C under an atmosphere of hydrogen. The crude reaction mixture is filtered through Celite and the solvent is removed in vacuo. In case the product purity is not sufficient, further purification can be achieved by chromatography. The amine is then reacted in an organic solvent such as DMF in the presence of a tertiary amine base such as DIEA with 9-chloroacridine according to *J. Med. Chem.* (1999), 42, 4741-4748. The solvent is removed in vacuo and the crude material is purified by chromatography. The product is then treated with methanesulfonyl chloride in an organic solvent such as DCM or THF in the presence of a tertiary amine base like DIEA. After removal of the solvent, the final product is isolated by chromatography.

Scheme 33.8

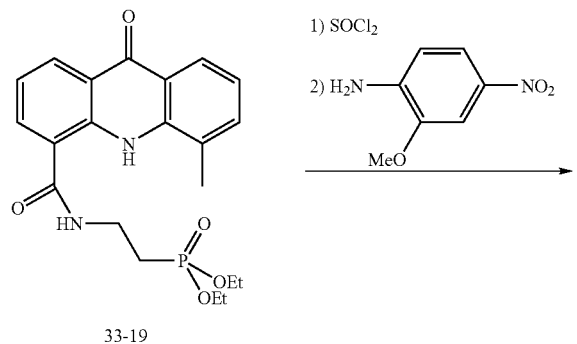

33-19

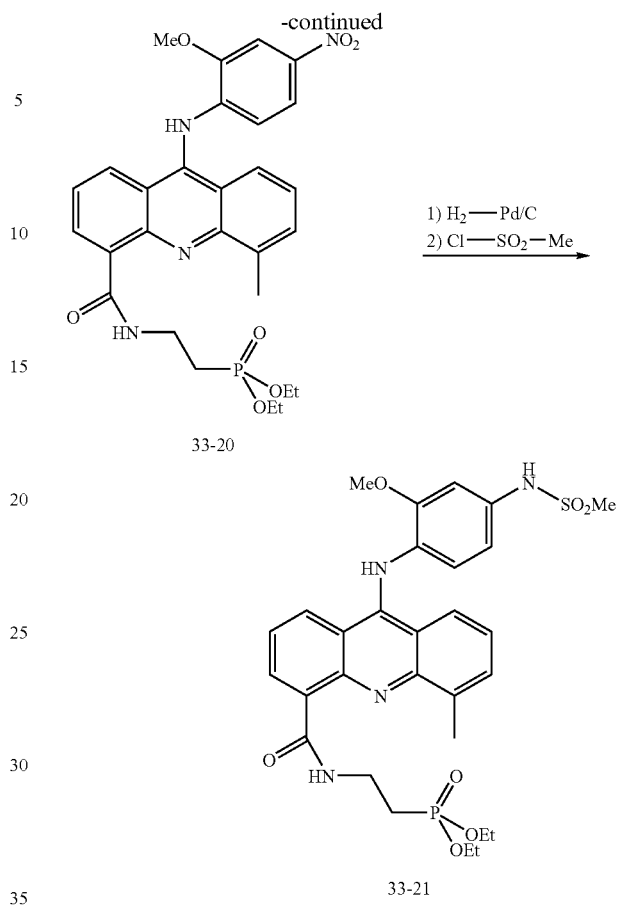

33-20

33-21

The starting material in Scheme 33.8 is available according to *J. Med. Chem.* (1999), 42, 4741-4748 via the reaction of the 9-oxoacrididan-4-methyl-5-carboxylic acid chloride and 2-aminoethylphosphonic acid diethyl ester. This material is then treated with thionyl chloride to yield the corresponding 9-chloroacridine derivative as described in the above reference. The crude material is then dissolved in an organic solvent such as chloroform, DCM, or THF and treated with 2-methoxy-4-nitroaniline. The crude product is isolated via precipitation and can be further purified by chromatography. This material is dissolved in an organic solvent such as DMF and is reduced in the presence of Pd/C under an atmosphere of hydrogen. After filtration of the reaction mixture through Celite, the solvent is removed in vacuo. The product can be purified further by chromatography. This material is then dissolved in an organic solvent such as THF or chloroform and is treated with methanesulfonyl chloride in the presence of a tertiary amine base such as DIEA. After removal of the solvent, the final product is isolated by chromatography.

Example 34

Preparation of Exemplary Compounds of the Present Invention

Compounds such as these can be made according to the general routes outlined in Schemes 34.1-34.3, with examples depicted in Schemes 34.4-34.6.

Scheme 34.1
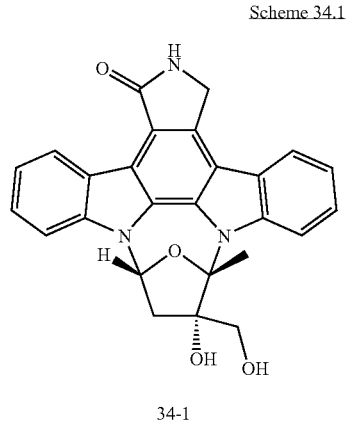
34-1
1. Protection of amide and primary alcohol
2. Alkylation of tertiary alcohol
3. Deprotection
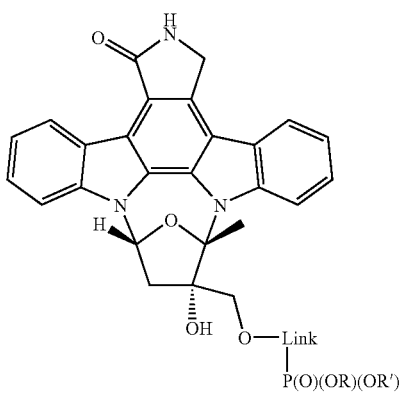
34-3
Scheme 34.3
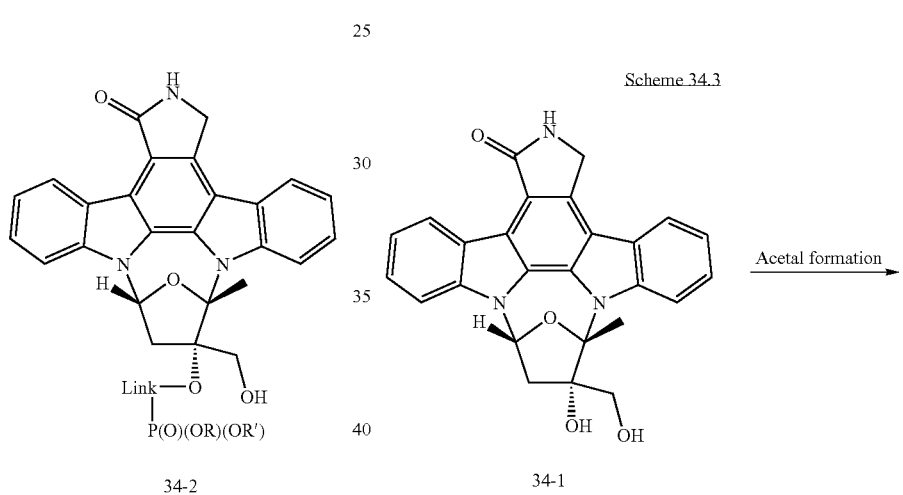
34-1 → Acetal formation → 34-4
Scheme 34.2
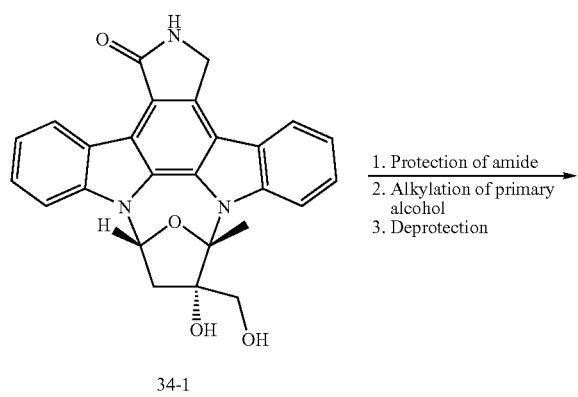
34-1
1. Protection of amide
2. Alkylation of primary alcohol
3. Deprotection
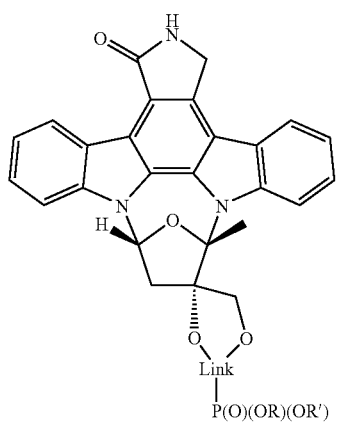

Scheme 34.4

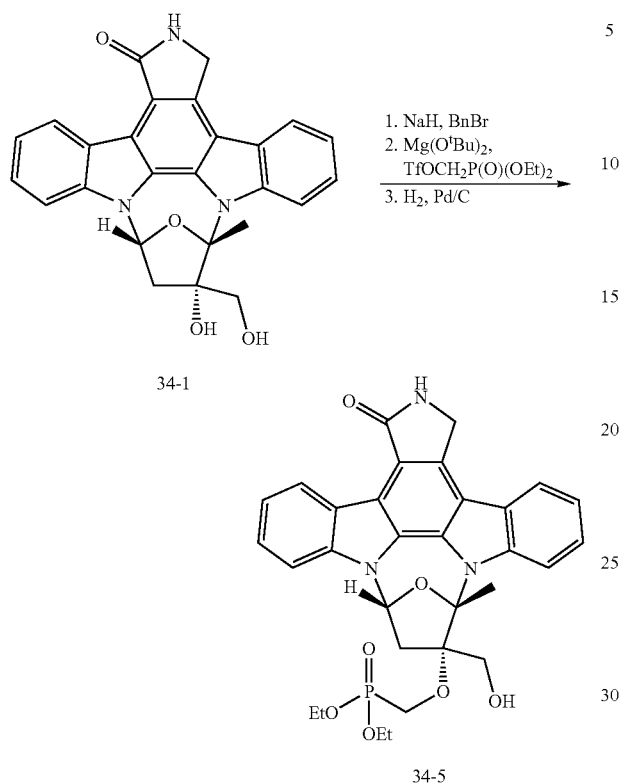

CEP-701 can be treated in a solvent such as dimethylformamide or tetrahydrofuran with two equivalents of a base such as sodium hydride. When bubbling ceases, benzyl bromide is added in excess, yielding the doubly-protected intermediate. After further treatment with a base such as magnesium tert-butoxide, diethyl phosphonomethyltriflate (prepared according to *Tetrahedron Lett.*, (1986), 27, 1477) is added, yielding the desired phosphonate diester. Final deprotection by hydrogenation over a catalyst such as palladium on charcoal in a solvent such as methanol as described in Greene, T., Protective groups in organic synthesis, Wiley-Interscience, (1999), provides the desired product.

Scheme 34.5

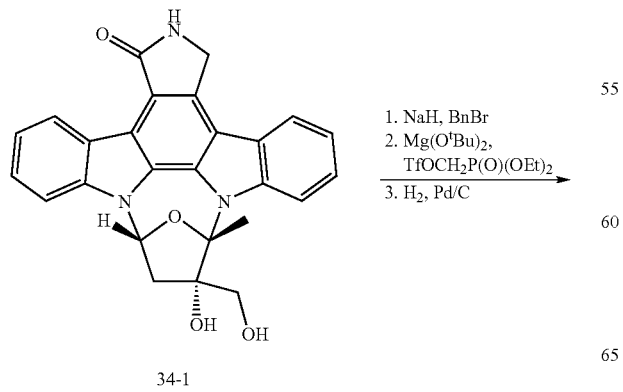

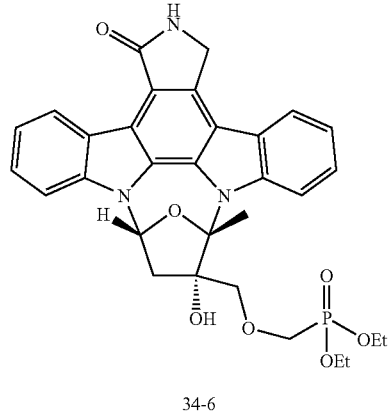

CEP-701 can be treated in a solvent such as dimethylformamide or tetrahydrofuran with one equivalent of a base such as sodium hydride or cesium carbonate. Benzyl bromide is added, yielding the N-benzylated product. After further treatment with a base such as magnesium tert-butoxide, diethyl phosphonomethyltriflate is added, yielding the desired phosphonate diester. Final deprotection by hydrogenation over a catalyst such as palladium on charcoal in a solvent such as methanol utilizing the method described in Greene (see above) provides the desired product.

Scheme 34.6

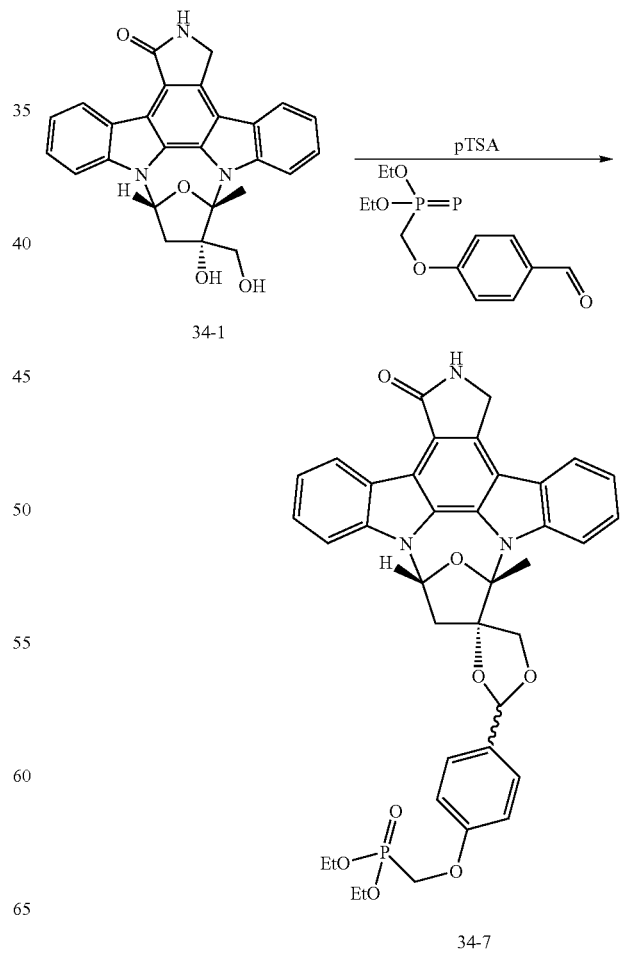

(4-Formyl-phenoxymethyl)-phosphonic acid diethyl ester is generated by treatment of 4-hydroxybenzaldehyde, in a solvent such as dimethylformamide or tetrahydrofuran, with a base such as sodium hydride and diethyl phosphonomethyltriflate. The product is condensed with CEP-701 in a solvent such as toluene, in the presence of a catalytic amount of p-toluenesulfonic acid, with azeotropic removal of the water so formed, yielding the desired acetal.

Further manipulations can be performed on the phosphonate moiety prior to the final deprotection

Example 35

Preparation of Exemplary Compounds of the Present Invention

Compounds such as these can be made according to the general route outlined in Schemes 35.1 and 35.3, with examples depicted in Schemes 35.2 and 35.4.

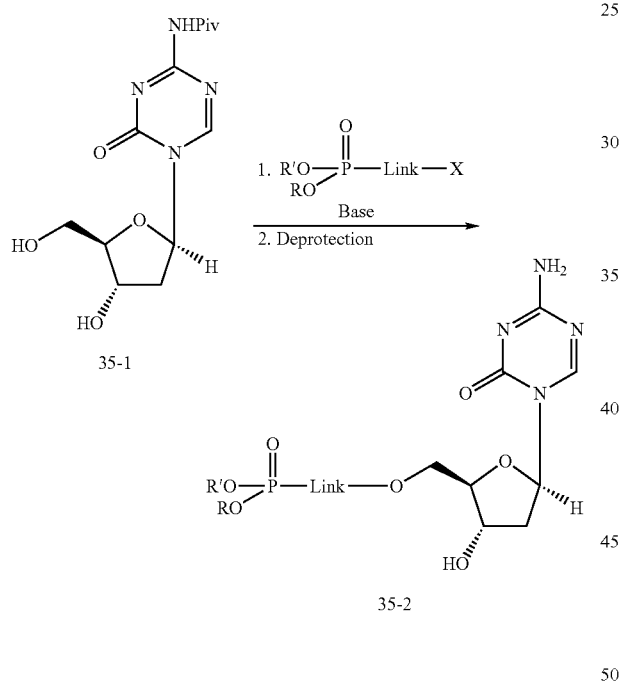

The appropriately protected 5-aza-2'-deoxycytidine, prepared according to the procedure of Winkley, M. W., Robins, R. K., *J. Org. Chem.*, (1970), 35, 2, 491 (see also Ben-Hattar J., Jiricny, J. *J. Org. Chem.*, (1986), 51, 3211), can be treated in a solvent such as tetrahydrofuran or dimethylformamide with a base such as sodium hydride. Formation of the pivaloyl compound 35-1 can be accomplished by protecting 5-aza-2'-deoxycytidine with a pivaloyl group (Greene, T., Protective groups in organic synthesis, Wiley-Interscience, (1999)). When bubbling ceases, diethyl phosphonomethyltriflate (prepared according to *Tetrahedron Lett.*, (1986), 27, 1477) is added, yielding the protected product. The pivaloyl group can be removed with sodium ethoxide to provide the desired phosphonate diester 35-2, 35-3.

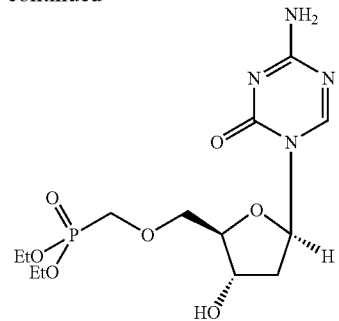

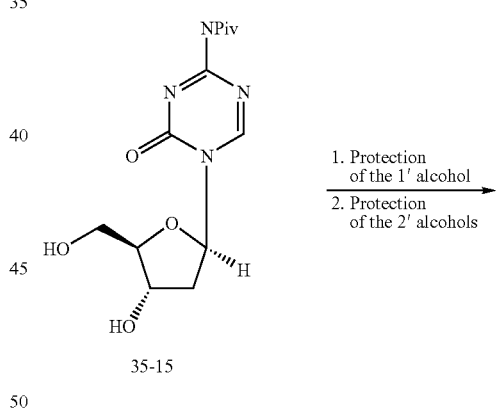

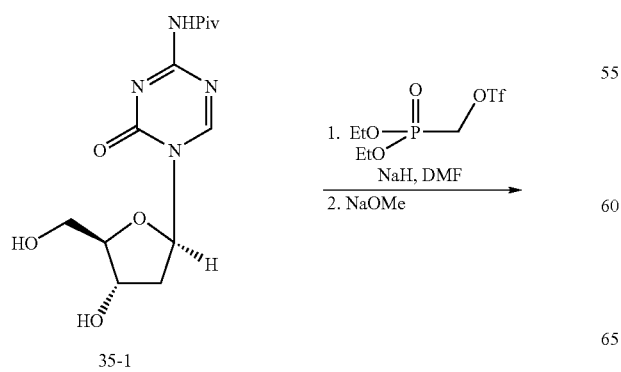

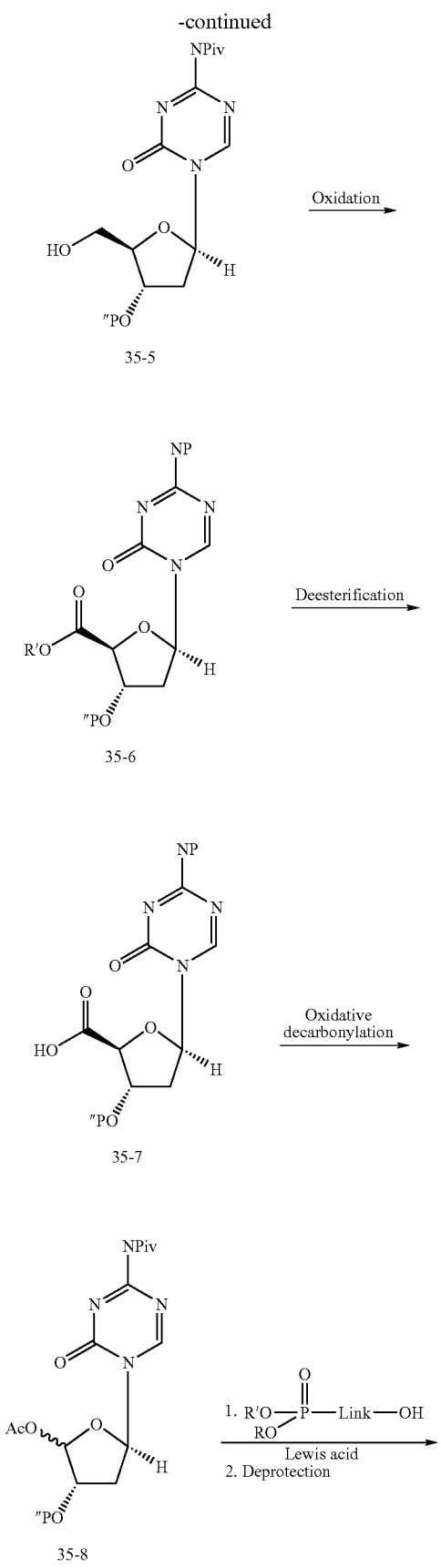

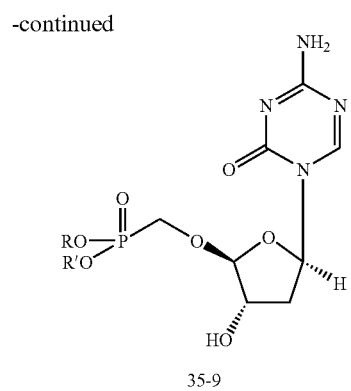

The preparation of compound 35-9 is described in Scheme 35.3. Compound 35-15 may be the pivaloyl protected 5-aza-2′-deoxycytidine which is described in Winkley, M. W., Robins, R. K., *J. Org. Chem.*, (1970), 35, 2, 491 and Ben-Hattar J., Jiricny, J., *J. Org. Chem.*, (1986), 51, 3211. Protection of the 5′ hydroxyl group followed by protection of 2′ alcohol provides compound 35-4. Removal of the 5′ protecting group provides the free primary alcohol. Corey's one-step oxidation procedure (Corey, E. J. et al., *J. Org. Chem.*, (1984), 49, 4735) can be utilized to transform the primary alcohol to the ester 35-6. Deesterification, followed by oxidative decarbonylation using a modified Hunsdiecker reaction (Chu, C. K. et al., *Tetrahedron Lett.*, (1991), 32, 3791) converts 35-7 to the acetate 35-8. The stereochemistry of the Vorbruggen glycosylation under Lewis acid conditions is controlled by protecting group participation at the 4′ position. A final deprotection provides the desired pro-drug 35-9.

Scheme 35.4

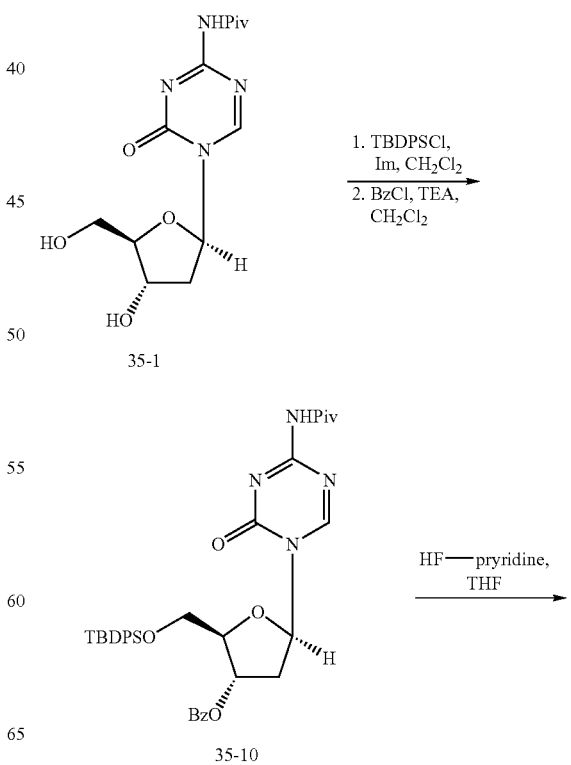

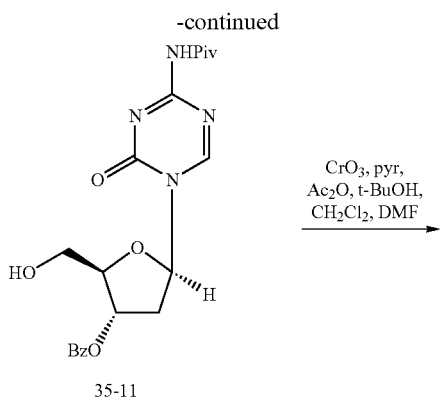

35-11

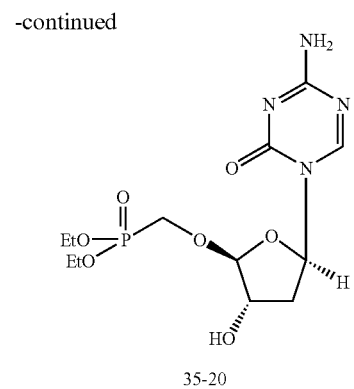

35-20

Specifically, compound 35-1 prepared by protection of 5-aza-2'-deoxycytidine (prepared as in Winkley, M. W., Robins, R. K., *J. Org. Chem.*, (1970), 35, 2, 491 and Ben-Hattar J., Jiricny, J. *J. Org. Chem.*, (1986), 51, 3211 using pivaloyl chloride, can be protected with a tert-butyldiphenylsilyl (TBDPS) group to provide the 5'-O-TBDPS analog. Further protection of the 3' alcohol with the benzoyl group provides compound 35-10 (Teng, K., Cook, D. *J. Org. Chem.* (1994), 59, 278). Exposure of the fully protected compound 35-10 to HF-pyridine reagent selectively deprotects the 5' hydroxyl group, which is then oxidized to the t-butyl ester using the Corey-Samuelsson oxidation (Corey, E. J., Samuelsson, B. *J. Org. Chem.*, (1984), 49, 4735). Deesterification of the oxidized product using trifluoroacetic acid (TFA) provides compound 35-12. Oxidative decarboxylation using a modified Hunsdiecker reaction (Chu, C. K. et al., *Tetrahedron Lett.*, (1991), 32, 3791) converts the free acid to the acetate 35-13 which may be a mixture of anomers at 5'. While separation of the anomers may be achieved by column chromatography, it is not necessary to do so. The stereochemical outcome of a Vorbruggen glycosylation is controlled by the stereochemistry of the 4'-benzoyl group due to anchimeric assistance, rendering separation of the isomers is unnecessary. Vorbruggen glycosylation using hydroxymethylphosphonic acid diethyl ester proceeds to provide the protected phosphonate. Final saponification to remove the pivaloate and the benzoate groups completes the synthesis of compound 35-20 (Greene, T., Protective groups in organic synthesis, Wiley-Interscience, (1999)).

Example 36

Preparation of Exemplary Compounds of the Present Invention

Compounds such as these can be made according to the general route outlined in Schemes 36.1-36.2, with examples depicted in Schemes 36.3-36.5.

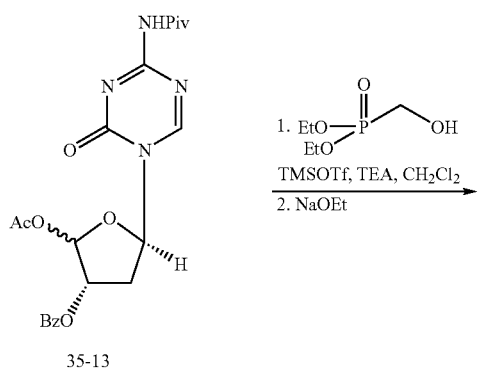

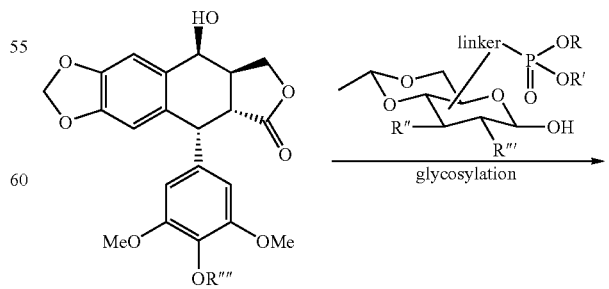

Scheme 36.1: Modification of the sugar substituent 36-1

-continued

Scheme 36.2: Attachment to the epi-podophyllotoxin core

Scheme 36.3: Modification of the 4,6 glucose-acetal moiety

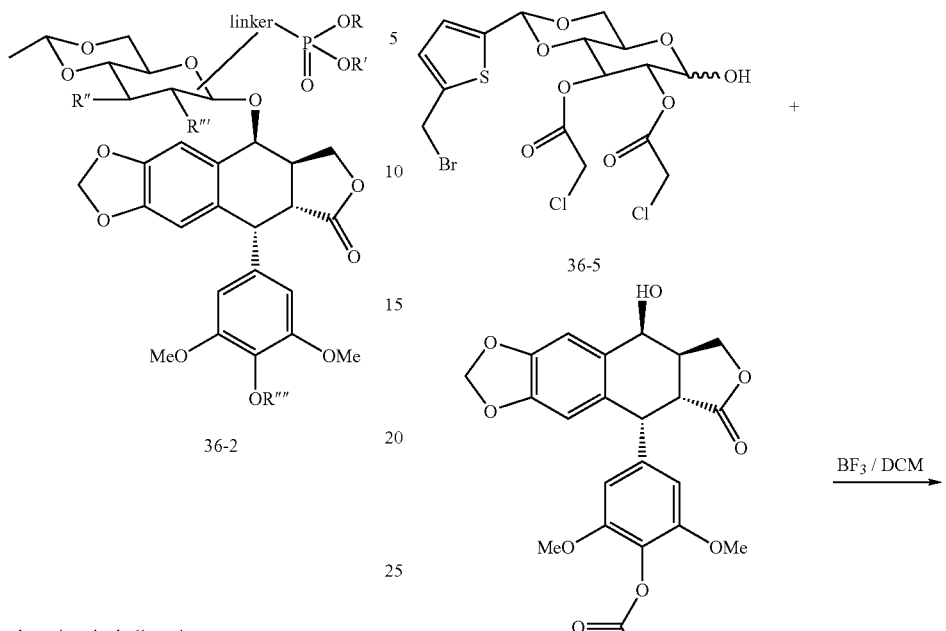
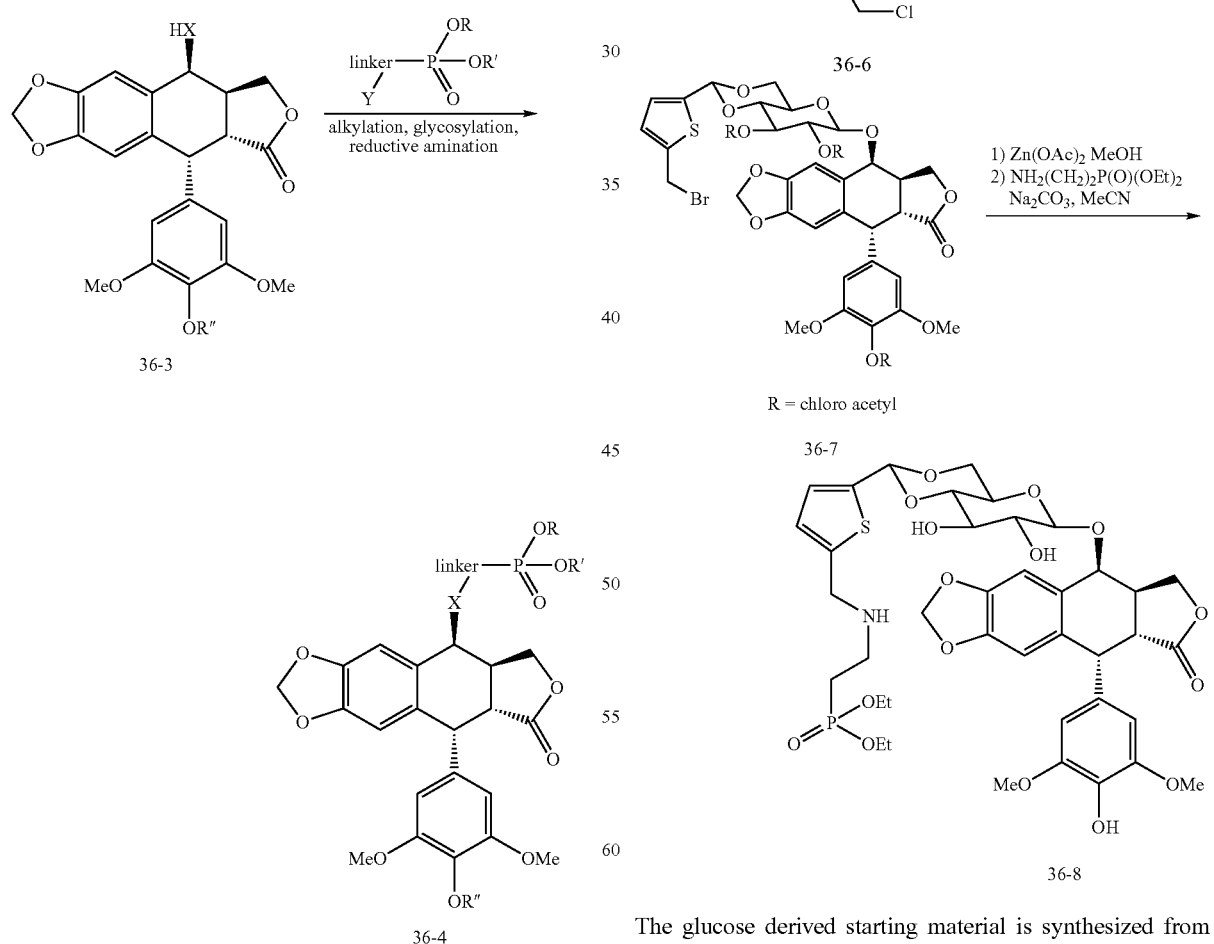

R = chloro acetyl

The glucose derived starting material is synthesized from glucose and 5-bromomethylthiophene-2-carbaldehyde (available from 5-methylthiophene-2-carboxaldehyde and N-bromosuccinimide using a procedure from Organikum, 17th edition, page 167) according to the methods described in Chem. Lett., (1987), 799-802. The glycosidation reaction is performed with 4'-chloroacetyl-protected epipodophyllotoxin (described in the reference above) under catalysis of boron trifluoride (described in the reference above). The product of this reaction is dissolved in an organic solvent such as methanol and is treated with zinc acetate at reflux temperature. At the end of the reaction, the mixture is cooled to room temperature and the solvent is removed in vacuo. The crude reaction product is dissolved in an organic solvent such as chloroform and the solution is washed with aqueous 0.1 M HCl and aqueous bicarbonate solution. After drying and removal of the solvent the crude product is obtained. Further purification is achieved by chromatography. The crude reaction product is dissolved in an organic solvent such as dimethylformamide (DMF) or chloroform and is then treated at a temperature of ~40° C. with a base such as sodium carbonate and is reacted with aminoethyldiethylphosphonate. After all starting material is consumed the reaction mixture is washed with aqueous 0.1 M HCl and aqueous bicarbonate solution. After drying and removal of the solvent the crude product of the reaction is obtained. Further purification is achieved by chromatography.

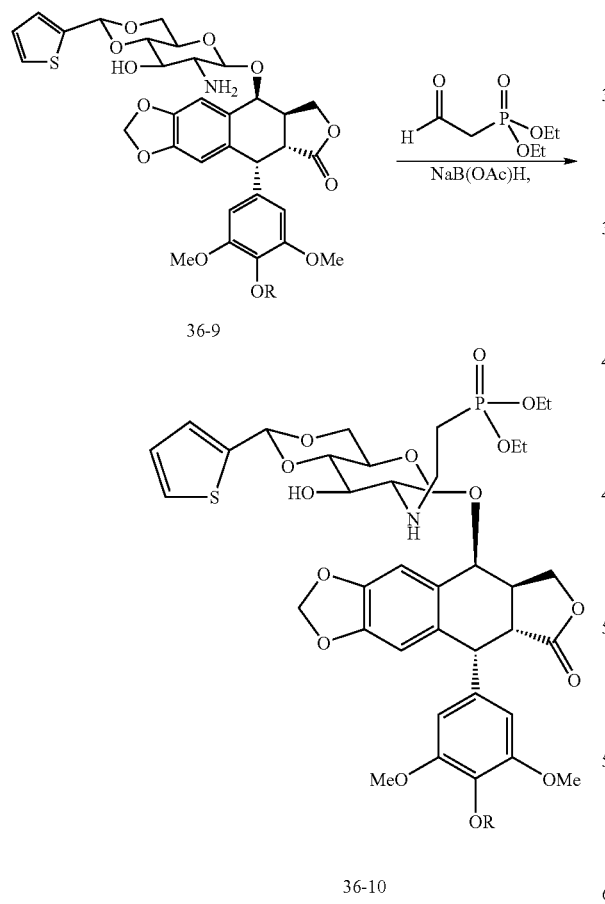

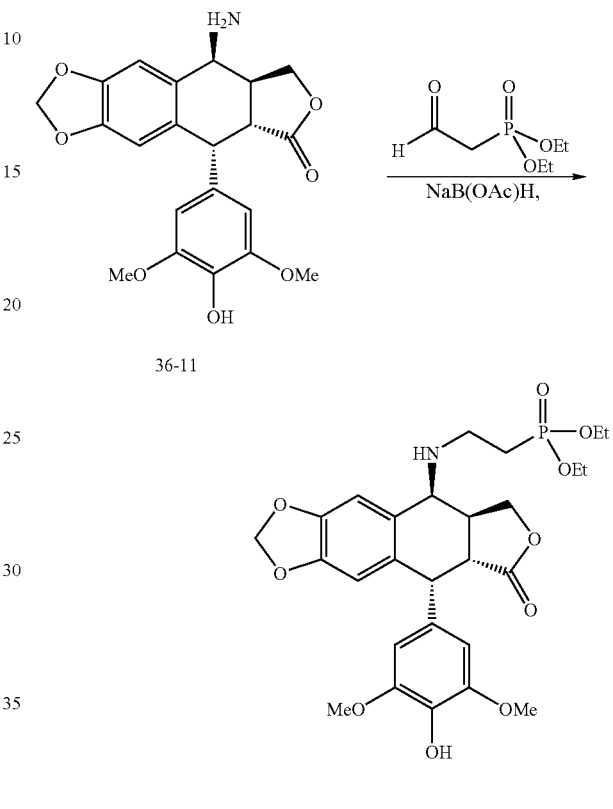

sodium triacetoxyborohydride as described in *J. Org. Chem*, (1996), 61, 3849-3862. The reaction is quenched with aqueous sodium bicarbonate and the product is extracted with an organic solvent such as ethyl acetate. Further purification is achieved by chromatography.

The amine-containing starting material (obtained as described in *J. Med. Chem.*, (1991), 34, 3346-3350) is treated in an organic solvent such as THF or DCM with diethyl phosphonatoethylcarbaldehyde and sodium triacetoxyborohydride as described in *J. Org. Chem*, (1996), 61, 3849-3862. The reaction is quenched with aqueous sodium bicarbonate and the product is extracted with an organic solvent such as ethyl acetate. Further purification is achieved by chromatography.

All final products are converted to the corresponding 4'-phosphate analogs via treatment of these compounds with phosphoryl trichloride in an organic solvent such as acetonitrile in the presence of an tertiary organic amine base such as N,N-diisopropylethylamine, followed by treatment with aqueous bicarbonate solution as described in *Bioorg. Med. Chem. Lett.*, (1994), 21, 2567-2572. Final product purification is achieved by chromatography.

The starting material (synthesis according to *Chem. Lett.*, (1987), 799-804; from glucosamine and thiophene-2-carbaldehyde—commercially available) is treated in an organic solvent such as dichloromethane (DCM) or tetrahydrofuran (THF) with diethyl phosphonatoethylcarbaldehyde and Example 37

Preparation of Exemplary Compounds of the Present Invention

Compounds such as these can be made according to the general routes outlined in Schemes 37.1-37.5.

Scheme 37.1

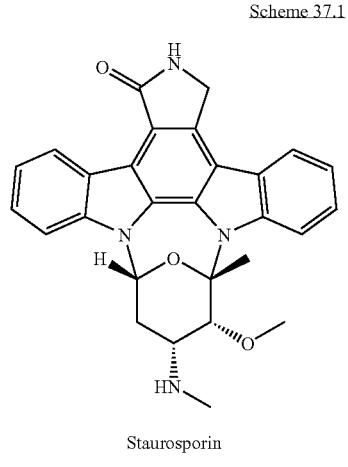

Staurosporin
37-1

↓ acylation

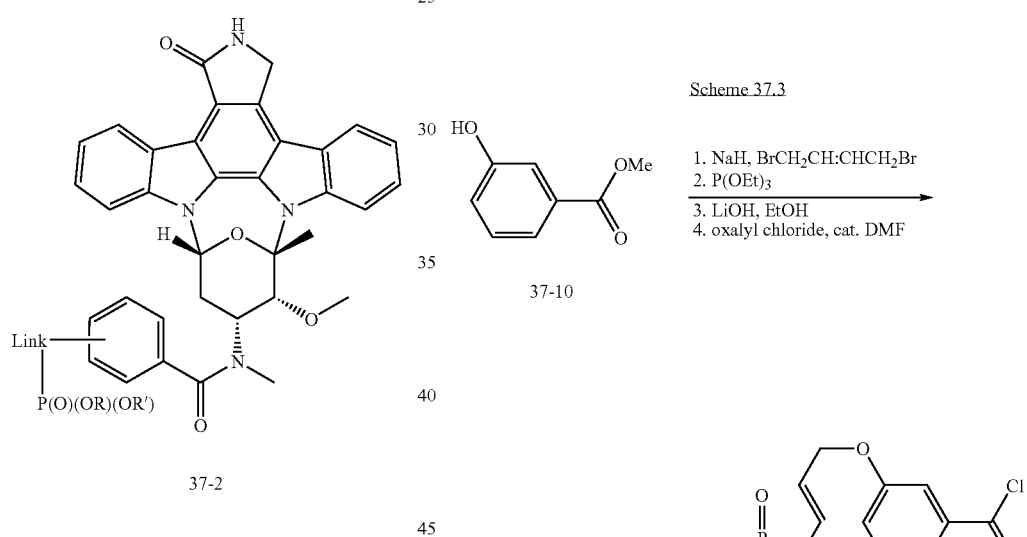

37-2

Staurosporin is acylated with activated benzoic acid derivatives such as benzoyl chlorides in a solvent such as chloroform, in the presence of a base such as N,N-diisopropylethylamine (DIEA) (*Bioorg. Med. Chem. Lett.*, (1994), 4, 399). Examples of benzoyl chlorides for use in the synthesis of suitable phosphonate-containing midostaurin analogs are illustrated in Schemes 37.2-37.3 below.

Scheme 37.2

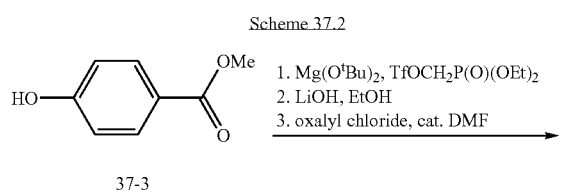

1. Mg(O$^t$Bu)$_2$, TfOCH$_2$P(O)(OEt)$_2$
2. LiOH, EtOH
3. oxalyl chloride, cat. DMF 37-3

→

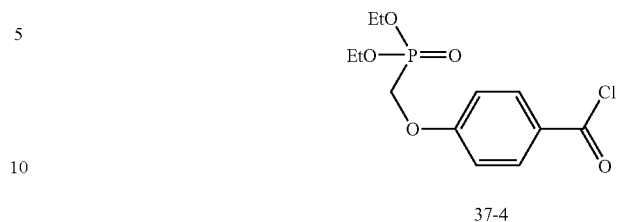

37-4

4-Hydroxybenzoic acid methyl ester is treated with magnesium tert-butoxide and diethyl phosphonomethyltriflate (prepared according to *Tetrahedron Lett.*, (1986), 27, 1477) in a solvent such as tetrahydrofuran. The resulting 4-(diethoxyphosphorylmethoxy)benzoic acid methyl ester is saponified with lithium hydroxide in ethanol, and the acid chloride is generated from the benzoic acid by reaction with oxalyl chloride in a solvent such as dichloromethane, catalyzed by dimethylformamide.

Scheme 37.3

HO—[benzene]—C(O)OMe 37-10

1. NaH, BrCH$_2$CH:CHCH$_2$Br
2. P(OEt)$_3$
3. LiOH, EtOH
4. oxalyl chloride, cat. DMF

→

[structure 37-5: EtO-P(O)(OEt)-CH$_2$-CH=CH-CH$_2$-O-phenyl-C(O)Cl]

37-5

3-Hydroxybenzoic acid methyl ester is treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the monoalkylated product is isolated by chromatography. The bromide is heated with triethylphosphite in a solvent such as toluene (or other Arbuzov reaction conditions: see Engel, R., Synthesis of carbon-phosphorus bonds, CRC press, 1988) to generate 3-[4-(diethoxy-phosphoryl)-but-2-enyloxy]-benzoic acid methyl ester. The remaining steps are similar to those described in Scheme 37.2.

Scheme 37.4

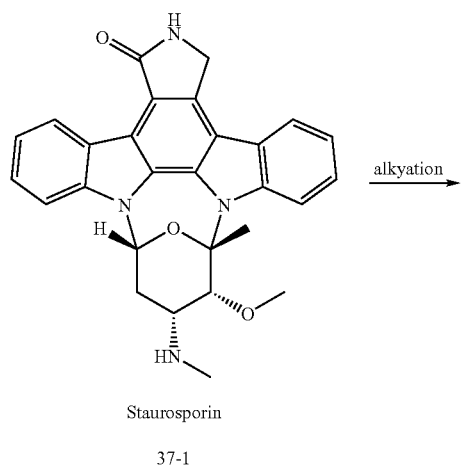

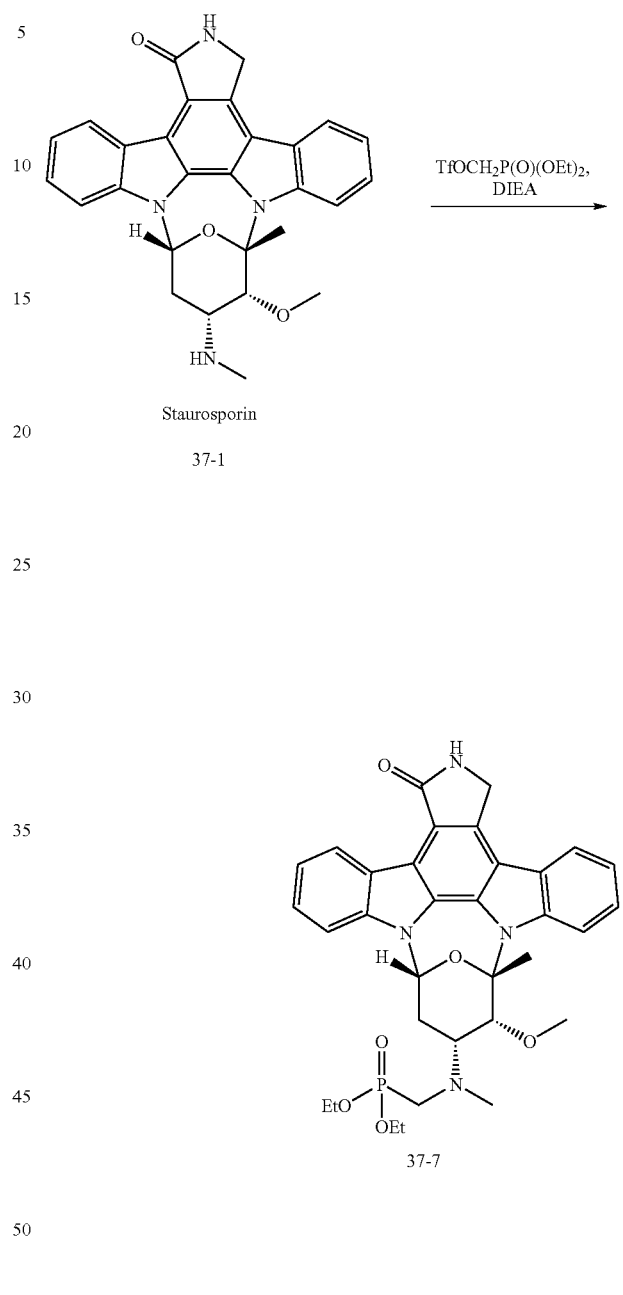

Alkylations on the secondary amine of staurosporine have been carried out under a variety of standard conditions: see *Bioorg. Med. Chem. Lett.*, (1994), 4, 399. An example of the synthesis of a phosphonate-containing alkyl derivative is shown in Scheme 37.5.

Staurosporin is alkylated with diethyl phosphonomethyl-triflate in the presence of a base such as DIEA.

Example 38

Preparation of Exemplary Compounds of the Present Invention

Compounds of the invention can be prepared as generally described in Schemes 38.1 and 38.4 and Schemes 38.2, 38.3 and 38.5.

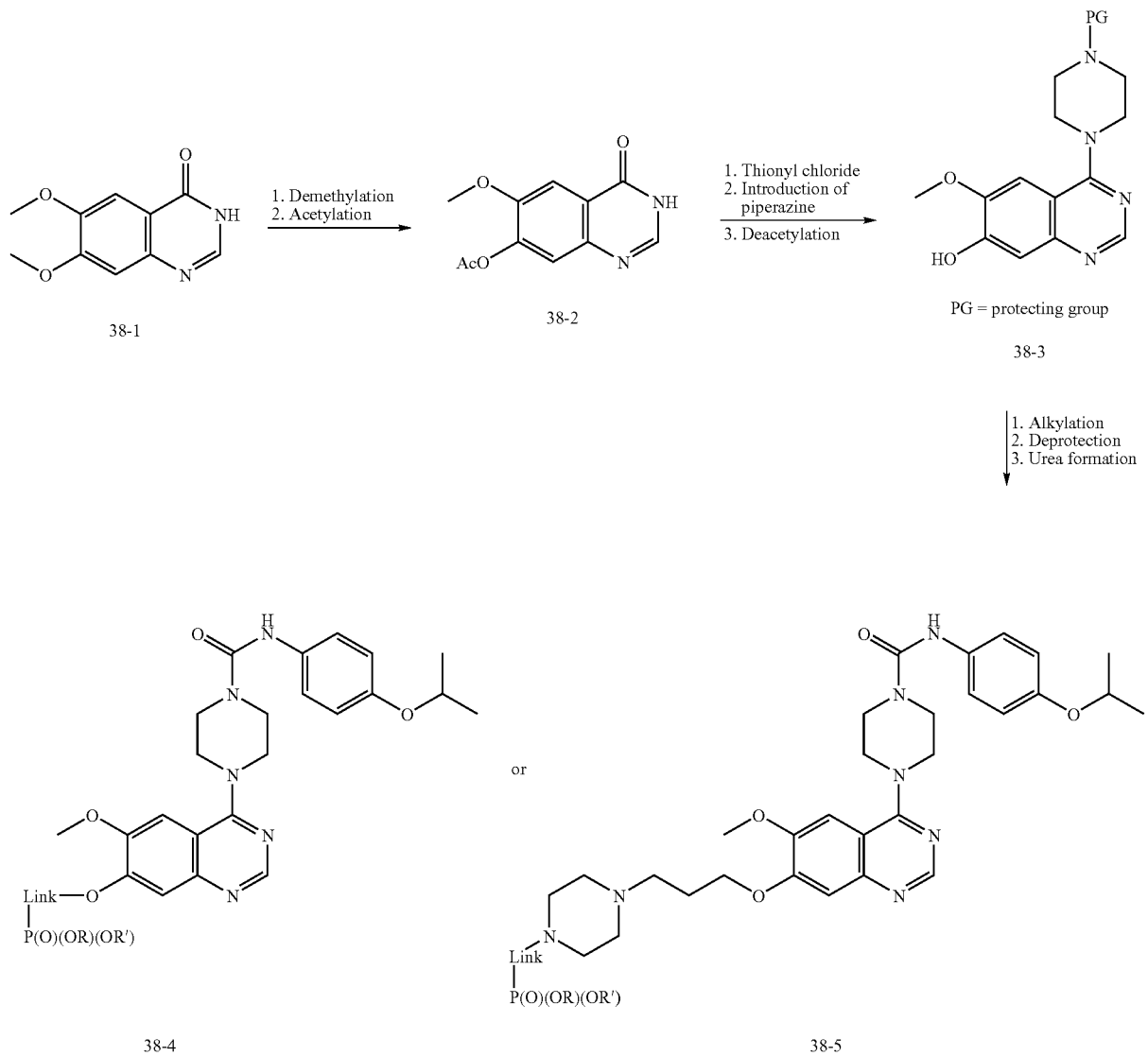
Introduction of the phosphonate-bearing entity at the quinazoline 7-position is most conveniently achieved by alkylation of a suitably-protected 4-piperazinylquinazoline, prior to urea formation.
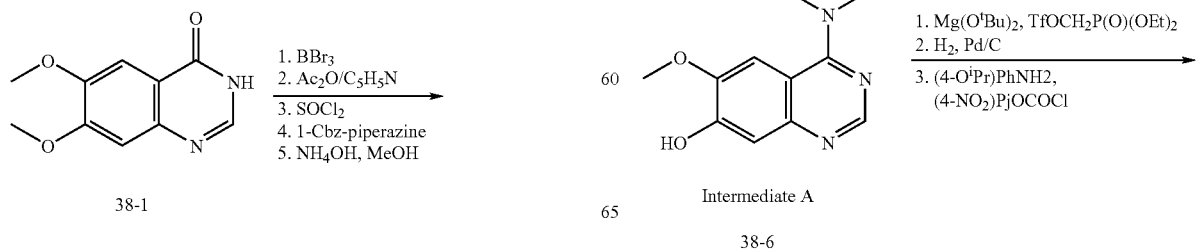

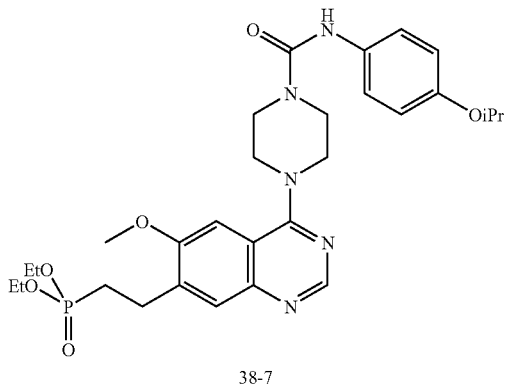

38-7

6,7-Dimethoxy-3,4-dihydroquinazolin-4-one is reacted with boron tribromide to give a mixture of mono-demethylated products. Although these may be separated by chromatography at this stage, the separation may be more conveniently achieved on the mixture of acetates that arises from reaction with and acetylating reagent such as acetyl chloride in the presence of a base such as pyridine. The desired isomer is reacted with thionyl chloride (see *Bioorg. Med. Chem. Lett.*, (2001), 11, 1911) and the resulting 4-chloroquinazoline is treated with piperazine-1-carboxylic acid benzyl ester. The acetyl protecting group is removed under standard conditions such as by treatment with ammonia in methanol (see Greene, T., Protective groups in organic synthesis, Wiley-Interscience, (1999)) to generate Intermediate A.

Upon treatment with a base such as magnesium tert-butoxide and diethyl phosphonomethyltriflate (prepared according to *Tetrahedron Lett.*, (1986), 27, 1477), the phosphonate-bearing moiety is introduced at the quinazoline 7-position. Thereafter, removal of the benzyl carbamate protecting group by hydrogenation over a catalyst such as palladium on charcoal in a solvent such as methanol (see Greene, ibid) and condensation with 4-isopropoxyaniline (commercially available) and 4-nitrophenyl chloroformate provides the desired compound.

Scheme 38.3

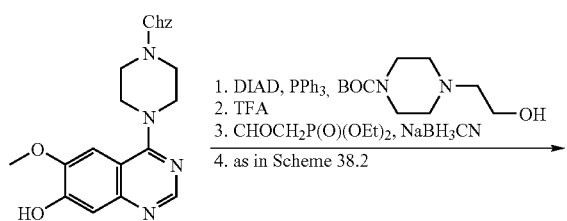

Intermediate A
38-6

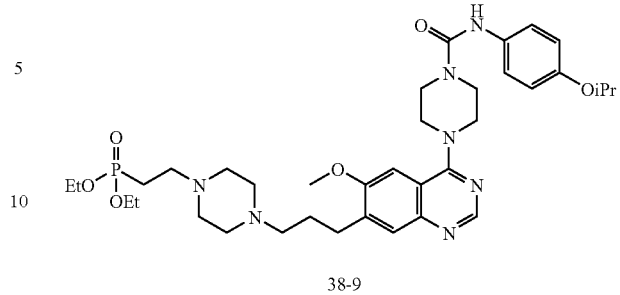

38-9

Intermediate A may be alkylated on the phenol by reaction with 4-(2-hydroxy-ethyl)-piperazine-1-carboxylic acid tert-butyl ester in the presence of an azodicarboxylate diester such as diisopropyl azodicarboxylate and triphenylphosphine, as described by Mitsunobu (*Bull. Chem. Soc. Japan.*, (1971), 44, 3427). Following deprotection with trifluoroacetic acid, the liberated secondary amine is condensed with (2-oxo-ethyl)-phosphonic acid diethyl ester under reductive conditions such as those achieved through the use of sodium cyanoborohydride in a solvent such as methanol or dimethylformamide (see *Tet. Lett.* (1990), 31, 5595). The remaining steps are similar to those described in Scheme 38.2.

Scheme 38.4

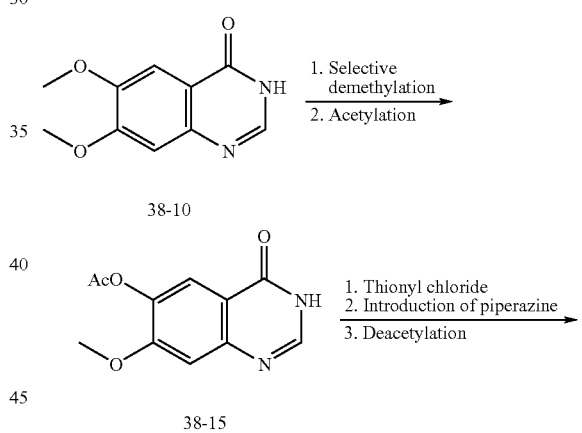

38-10

1. Selective demethylation
2. Acetylation 38-15

1. Thionyl chloride
2. Introduction of piperazine
3. Deacetylation

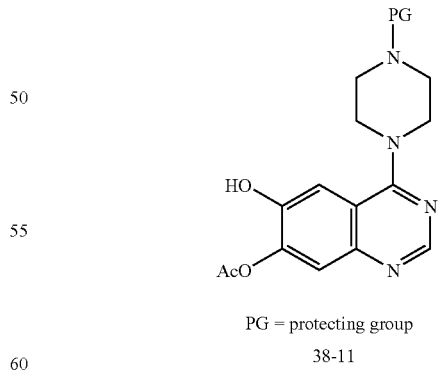

PG = protecting group
38-11

1. Alkylation
2. Deprotection
3. Urea formation

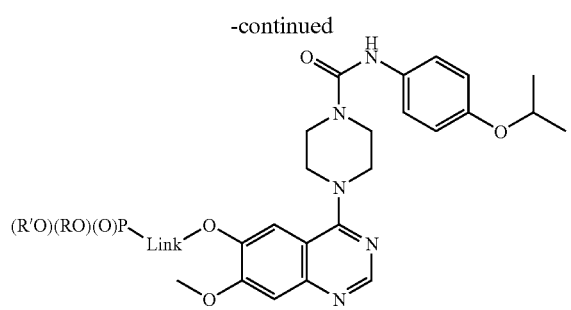

38-12

The route is similar to that shown in Schemes 38.1-38.3, but exploits a selective demethylation at the 6-position of 6,7-dimethoxy-3,4-dihydroquinazolin-4-one (see *Bioorg. Med. Chem. Lett.*, (2001), 11, 1911). A specific example of such a synthesis is shown in Scheme 38.5.

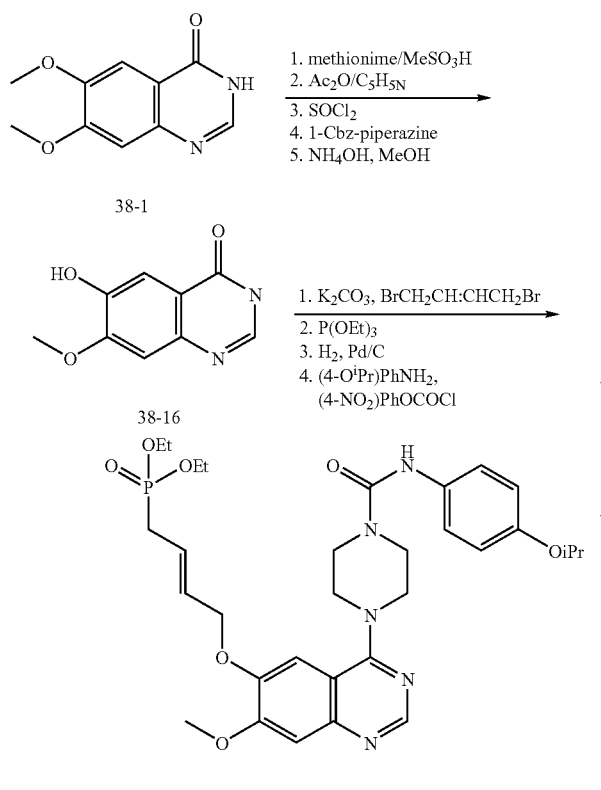

Scheme 38.5

38-17

Following the selective demethylation, the steps are similar to those discussed in previous examples up to the point where a phenol is alkylated. In this example, however, the alkylation is performed with E-1,4-dibromobutene, and the monobromide product is reacted with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. Thereafter, the steps are again similar to those described in previous examples.

Example 39

Preparation of Exemplary Compounds of the Present Invention

Compounds of the invention can be prepared as generally described in Schemes 39.1 and 39.3, with exemplifications in Schemes 39.2 and 39.4.

Scheme 39.1

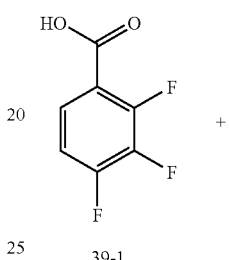

39-1

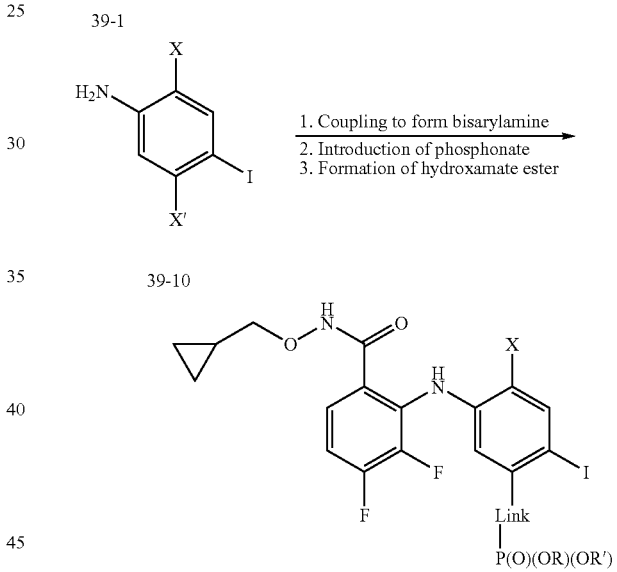

39-2

The coupling of an aniline with 2,3,4-trifluorobenzoic acid is performed in the presence of a large excess of a base such as lithium diisopropylamide in a solvent such as tetrahydrofuran, and at temperatures at or below ambient, as described in patent application WO 2001-U.S. Pat. No. 22,948. The subsequent introduction of a phosphonate moiety may be achieved by a variety of means, such as those illustrated Scheme 39.2 below. Thereafter, the hydroxamic ester is generated by treatment of the benzoic acid with O-(tetrahydro-2H-pyran-2-yl)hydroxylamine and diisopropylethylamine in the presence of a coupling reagent such as benzotriazole-1-yl-oxy-tris-pyrrolidino-phosphonium hexafluorophosphate (PyBOP) in a solvent such as tetrahydrofuran or dichloromethane, as described in patent application WO 2000-U.S. Pat. No. 18,347 20000705, followed by treatment with ethanolic hydrochloric acid.

Scheme 39.2

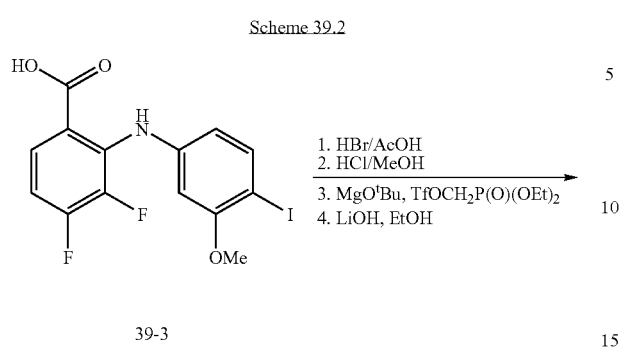

39-3

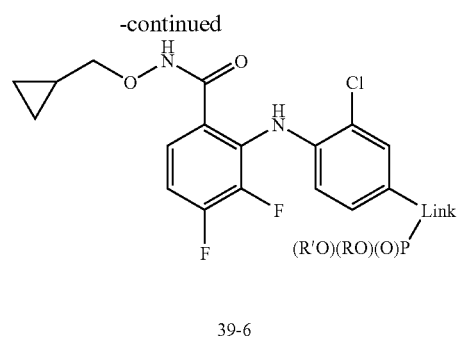

39-6

The iodo substituent present in PD-184352 may be used for the introduction of a phosphonate-bearing moiety, as illustrated in Scheme 39.4 below.

Scheme 39.4

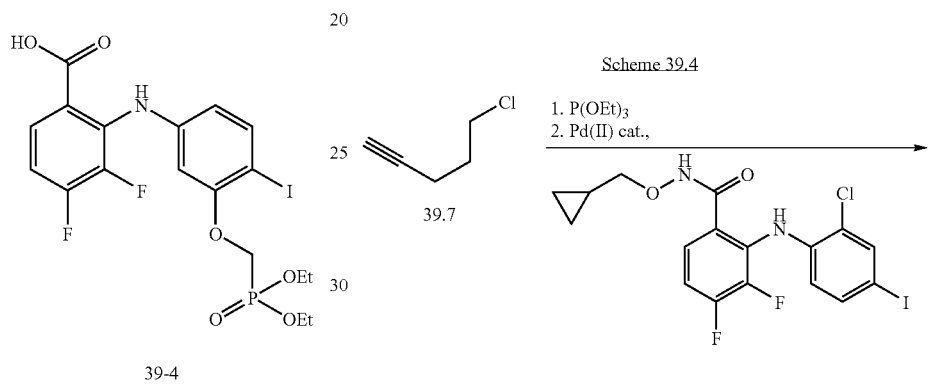

39-8

5-Chloro-1-pentyne is treated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. This acetylene is coupled with 39.5 under conditions such as those pioneered by Sonagashira (Sonagashira, K.; Tohda, Y.; Hagihara, N. *Tetrahedron Lett.*, (1975), 4467).

39-4

Having coupled 2,3,4-trifluorobenzoic acid with 2-iodo-5-nitroanisole (commercially available), the methyl ether is removed under standard conditions such as by treatment with hydrobromic acid in acetic acid (see Greene, T., Protective groups in organic synthesis, Wiley-Interscience, (1999)). The benzoic acid is esterified by dissolution in acidic methanol. The phenol is then treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester. Saponification of the benzoic acid (ready for coupling to form the hydroxamate ester—see Scheme 39.1) is achieved with lithium hydroxide in a solvent such as tetrahydrofuran or ethanol.

Scheme 39.3

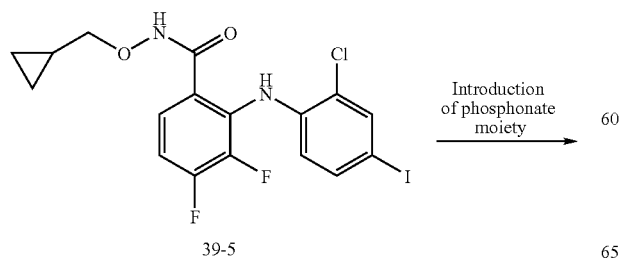

39-5

Introduction of phosphonate moiety

Example 40

Preparation of Exemplary Compounds of the Present Invention

Compounds can be prepared as generally described in Schemes 40.1-40.5, with specific examples depicted in Schemes 40.2-40.4. Final compounds, be they diastereoisomers or enantiomers, may be purified by chromatographic means.

Scheme 40.1: General access to all compound classes

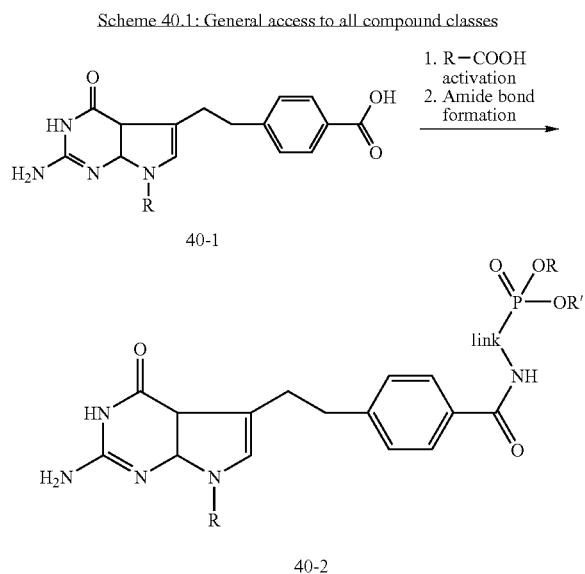

In case a direct coupling to aminopterin is hampered by the presence of a free secondary amine in the starting material (R=H), this entity will be temporarily protected either with a tert-butoxycarbonyl group (R=Boc) or benzyloxycarbonyl (R=Cbz or Z) according to standard procedures (Green Wutts: Protective groups in organic chemistry).

The starting carboxylic acid can be treated in a solvent such as dimethylformamide (DMF) or N-methylpyrrolidinone (NMP) with a coupling reagent such as diethyl cyanophosphonate or isobutyl chloroformate and a base such as diisopropylethylamine (DIEA) at room temperature (*J. Med. Chem.*, (1982), 25, 960-964 and *J. Med. Chem.*, (1984), 27, 600-604). When the activation is complete, 2-aminoethylphosphonic acid diethyl ester (commercially available) is added. After consumption of the activated species is observed the solvent is removed in vacuo and the product is isolated via chromatography. Alternatively, the product can be isolated through precipitation from the reaction solution with an organic solvent such as diethyl ether or the like.

When R=Z, the compound is dissolved in an organic solvent like DMF or NMP and a catalytic amount of Pd/C is added. The reaction mixture is stirred under an atmosphere of hydrogen until the starting material is consumed. The Pd/C is removed and the solvent is evaporated in vacuo. The product is isolated via chromatography. Alternatively, the product can be isolated through precipitation from the reaction solution with an organic solvent such as diethyl ether or the like.

Scheme 40.2: Specific example for class A

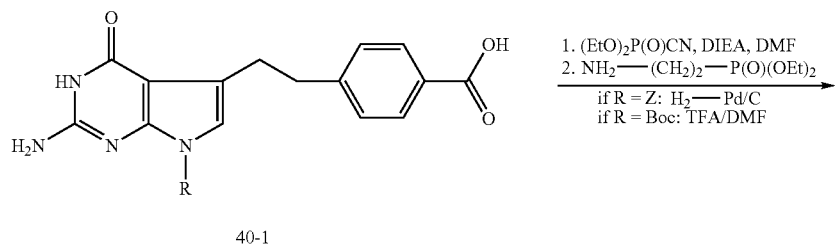

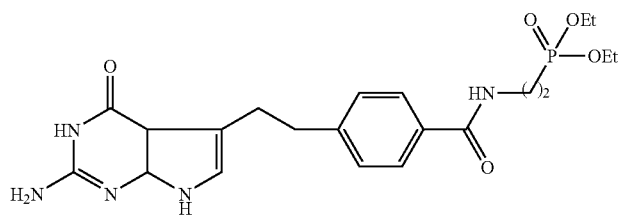

Scheme 40.3: Second specific example for class A

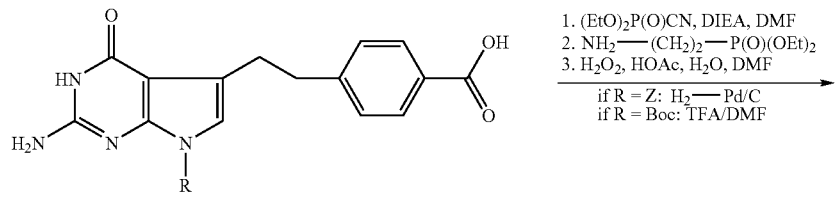

40-1

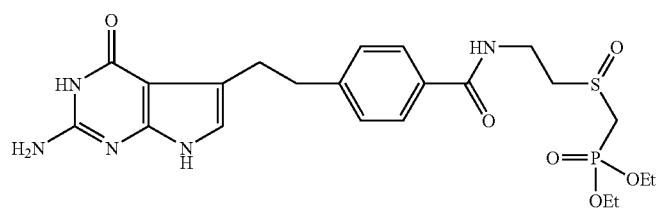

40-4

The starting carboxylic acid can be treated in a solvent such as DMF or NMP with a coupling reagent such as diethyl cyanophosphonate or isobutyl chloroformate and a base such as diisopropylethylamine (DIEA) at room temperature (*J. Med. Chem.*, (1982), 25, 960-964 and *J. Med. Chem.*, (1984), 27, 600-604). When the activation is complete, (2-aminoethylsulfanylmethyl)-phosphonic acid diethyl ester (made by base-catalyzed coupling of 2-aminoethanethiol with diethyl phosphonomethyltriflate, prepared according to *Tetrahedron Lett.*, (1986), 27, 1477) is added. After consumption of the activated species is observed the solvent is removed in vacuo and the intermediate is isolated via chromatography. Alternatively, the intermediate can be isolated through precipitation from the reaction solution with an organic solvent such as diethyl ether or the like. The intermediate is then dissolved in a mixture of water, DMF, and acetic acid and is treated with hydrogen peroxide solution (excess). After removal of the solvents the product is isolated via chromatography. Alternatively, the product can be isolated through precipitation from the reaction solution with an organic solvent such as diethyl ether or the like.

When R=Z, the compound is dissolved in an organic solvent like DMF or NMP and a catalytic amount of Pd/C is added. The reaction mixture is stirred under an atmosphere of hydrogen until the starting material is consumed. The Pd/C is removed and the solvent is evaporated in vacuo. The product is isolated via chromatography. Alternatively, the product can be isolated through precipitation from the reaction solution with an organic solvent such as diethyl ether or the like.

Scheme 40.4

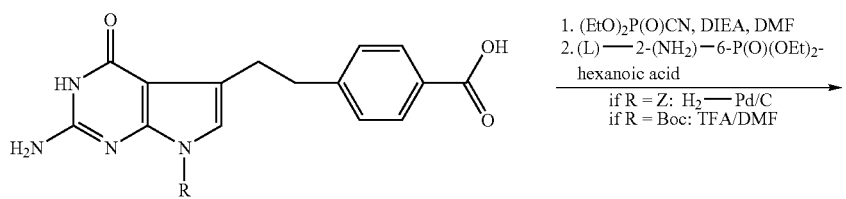

40-1

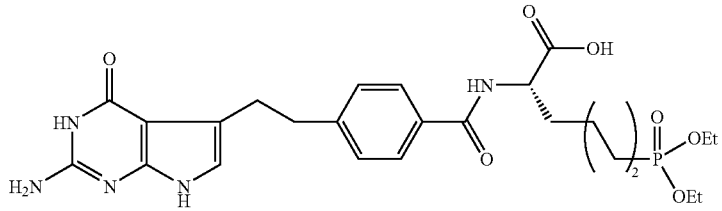

40-5

The starting carboxylic acid can be treated in a solvent such as DMF or NMP with a coupling reagent such as diethyl cyanophosphonate or isobutyl chloroformate and a base such as DIEA at room temperature (*J. Med. Chem.*, (1982), 25, 960-964 and *J. Med. Chem.*, (1984), 27, 600-604.). When the activation is complete, (L)-2-amino-6-(diethylphosphonato)-hexanoic acid is added. After consumption of the activated species is observed the solvent is removed in vacuo and the product is isolated via chromatography. Alternatively, the product can be isolated through precipitation from the reaction solution with an organic solvent such as diethyl ether or the like.

When R=Z, the compound is dissolved in an organic solvent like DMF or NMP and a catalytic amount of Pd/C is added. The reaction mixture is stirred under an atmosphere of hydrogen until the starting material is consumed. The Pd/C is removed and the solvent is evaporated in vacuo. The product is isolated via chromatography. Alternatively, the product can be isolated through precipitation from the reaction solution with an organic solvent such as diethyl ether or the like.

species is observed the solvent is removed in vacuo and the intermediate is isolated via chromatography. Alternatively, the intermediate can be isolated through precipitation from the reaction solution with an organic solvent like diethyl ether or the like. The crude intermediate is then dissolved in DMF and treated with TFA (excess). The product is isolated via chromatography after removal of the solvents. Alternatively, the product can be isolated through precipitation form the reaction solution with an organic solvent such as diethyl ether or the like.

When R=Z, the compound is dissolved in an organic solvent like DMF or NMP and a catalytic amount of Pd/C is added. The reaction mixture is stirred under an atmosphere of hydrogen until the starting material is consumed. The Pd/C is removed and the solvent is evaporated in vacuo. The product is isolated via chromatography. Alternatively, the product can be isolated through precipitation from the reaction solution with an organic solvent such as diethyl ether or the like.

Scheme 40.5

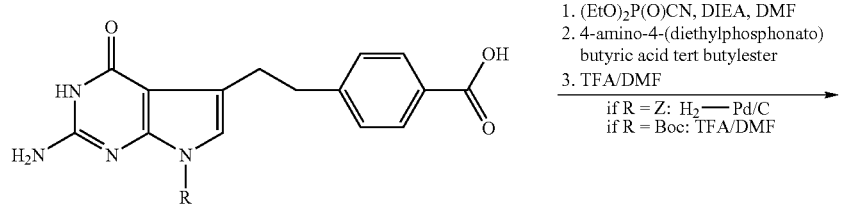

1. $(EtO)_2P(O)CN$, DIEA, DMF
2. 4-amino-4-(diethylphosphonato) butyric acid tert butylester
3. TFA/DMF if R = Z: $H_2$ — Pd/C
if R = Boc: TFA/DMF 40-1

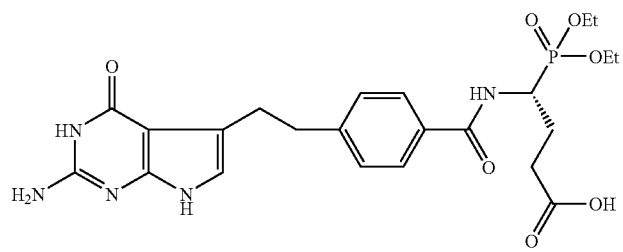

40-6

The starting carboxylic acid can be treated in a solvent such as DMF or NMP with a coupling reagent such as diethyl cyanophosphonate or isobutyl chloroformate and a base such as DIEA at room temperature (*J. Med. Chem.*, (1982), 25, 960-964 and *J. Med. Chem.*, (1984), 27, 600-604). When the activation is complete, 4-amino-4-(diethylphosphonato)-butyric acid tert butylester (*J. Am. Chem. Soc.*, (1995), 117, 10879-10888) is added. After consumption of the activated Example 41

Preparation of Exemplary Compounds of the Present Invention

Compounds of the invention can be made according to the general route outlined in Scheme 41.1-41.5, with specific examples depicted in Schemes 41.2-41.4. Final compounds, be they diastereoisomers or enantiomers, may be purified by chromatographic means.

Scheme 41.1: General access to compounds of the invention

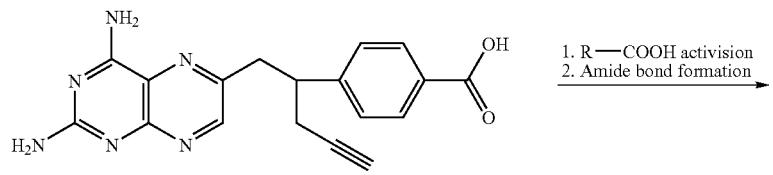

41-1

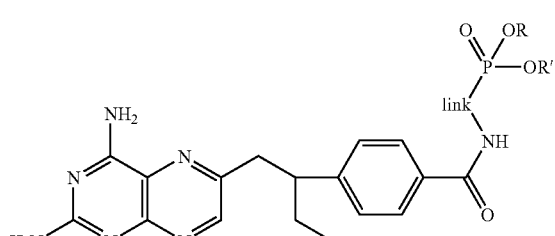

41-2

Scheme 41.2:

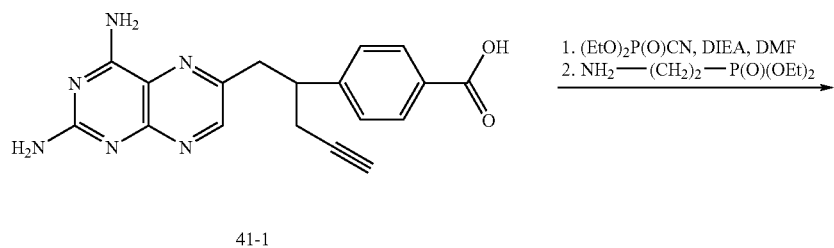

41-1

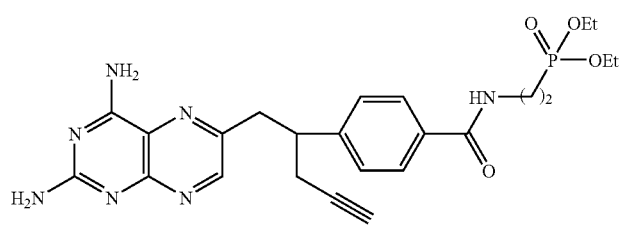

41-4

The starting carboxylic acid can be treated in a solvent such as DMF or NMP with a coupling reagent such as diethyl cyanophosphonate or isobutyl chloroformate and a base such as diisopropylethylamine (DIEA) at room temperature (*J. Med. Chem.*, (1982), 25, 960-964 and *J. Med. Chem.*, (1984), 27, 600-604). When the activation is complete, 2-aminoethylphosphonic acid diethyl ester (commercially available) is added. After consumption of the activated species is observed the solvent is removed in vacuo and the product is isolated via chromatography. Alternatively, the product can be isolated through precipitation from the reaction solution with an organic solvent like diethyl ether or the like.

Scheme 41.3:

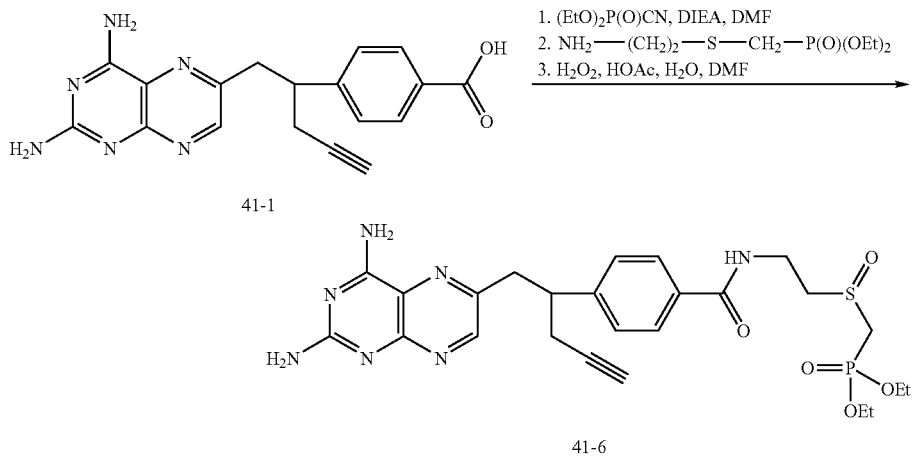

The starting carboxylic acid can be treated in a solvent such as DMF or NMP with a coupling reagent such as diethyl cyanophosphonate or isobutyl chloroformate and a base such as diisopropylethylamine (DIEA) at room temperature (*J. Med. Chem.*, (1982), 25, 960-964 and *J. Med. Chem.*, (1984), 27, 600-604). When the activation is complete, (2-amino-ethylsulfanylmethyl)-phosphonic acid diethyl ester (made by base-catalyzed coupling of 2-aminoethanethiol with diethyl phosphonomethyltriflate, prepared according to *Tetrahedron Lett.*, (1986), 27, 1477) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The intermediate is then dissolved in a mixture of water, DMF, and acetic acid and is treated with hydrogen peroxide solution (excess). After removal of the solvents the product is isolated via chromatography. Alternatively, the product can be isolated through precipitation from the reaction solution with an organic solvent like diethyl ether or the like.

Scheme 41.4:

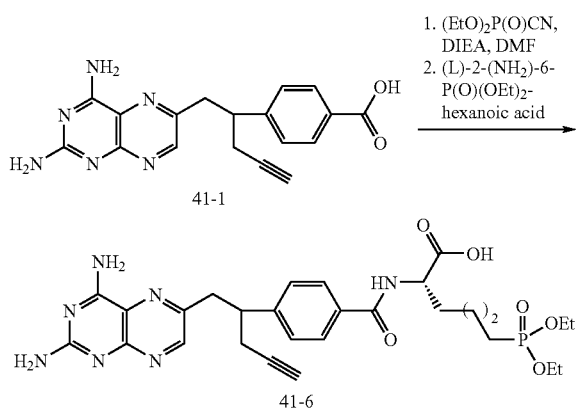

The starting carboxylic acid can be treated in a solvent such as DMF or NMP with a coupling reagent such as diethyl cyanophosphonate or isobutyl chloroformate and a base such as DIEA at room temperature (*J. Med. Chem.*, (1982), 25, 960-964 and *J. Med. Chem.*, (1984), 27, 600-604.). When the activation is complete, (L)-2-amino-6-(diethylphosphonato)-hexanoic acid is added. After consumption of the activated species is observed the solvent is removed in vacuo and the product is isolated via chromatography. Alternatively, the product can be isolated through precipitation from the reaction solution with an organic solvent like diethyl ether or the like.

Scheme 41.5:

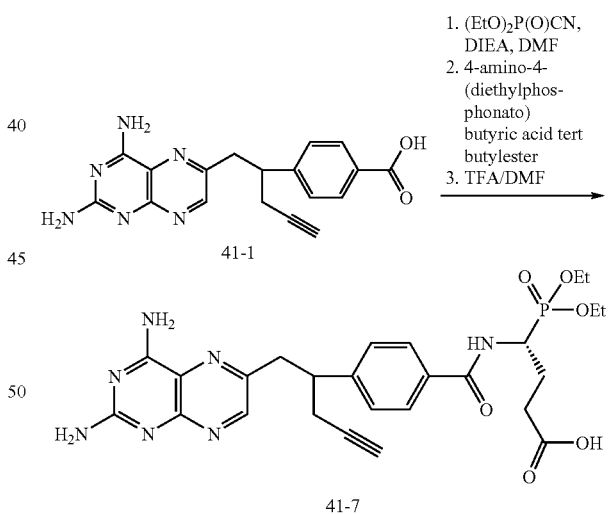

The starting carboxylic acid can be treated in a solvent such as DMF or NMP with a coupling reagent such as diethyl cyanophosphonate or isobutyl chloroformate and a base such as DIEA at room temperature (*J. Med. Chem.*, (1982), 25, 960-964 and *J. Med. Chem.*, (1984), 27, 600-604). When the activation is complete, 4-amino-4-(diethylphosphonato)-butyric acid tert butylester (*J. Am. Chem. Soc.*, (1995), 117, 10879-10888) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The crude intermediate is then dissolved in DMF and treated with TFA (excess). The product is isolated via chromatography after removal of the solvents. Alternatively, the product can be isolated through precipitation form the reaction solution with an organic solvent like diethyl ether or the like

Example 42

Preparation of Exemplary Compounds of the Present Invention

Compounds of the invention can be prepared as generally described in Scheme 42.1, with an example depicted in Scheme 42.2.

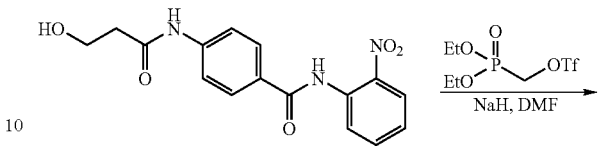

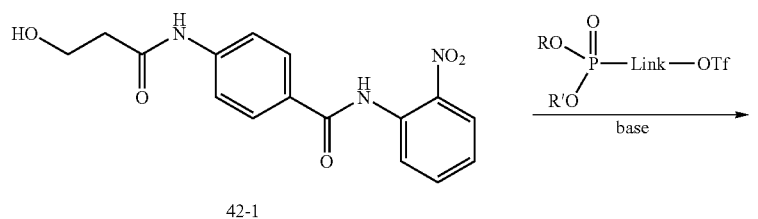

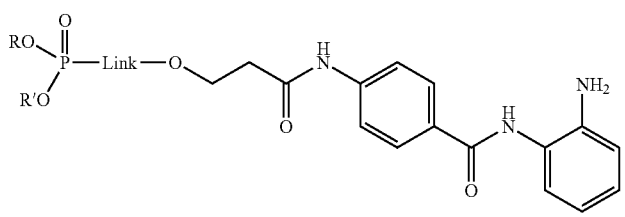

Preparation of a specific pro-drug of tacedinaline is shown in Scheme 42.1. The synthesis is planned so that attachment of the pro-drug moiety is performed late in the synthesis. Reduction of the nitro group allows for completion of the synthesis. A number of methods are reported in literature for such a reduction; hydrogenation, Raney Nickel and tin chloride dihydrate are a few of these (Suzuki, T. et al., *J. Med. Chem.*, (1999), 42, 3001).

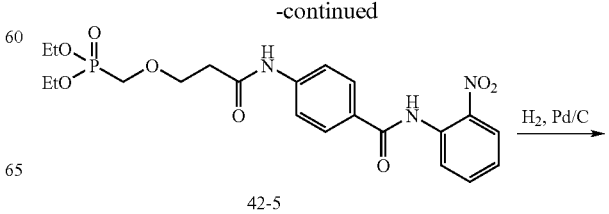

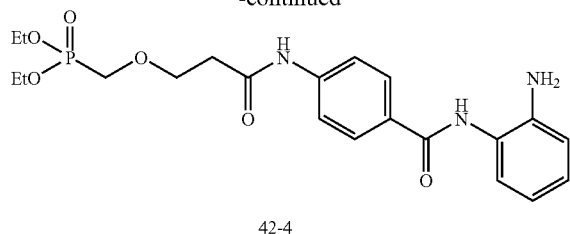

42-4

Preparation of a specific pro-drug linked tacedinaline is shown in Scheme 42.2 in more detail. Compound 42-1 can be prepared according to U.S. Pat. No. 5,137,918. Compound 42-1 is treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester 42-2, 42-5. Reduction of the nitro group is accomplished by hydrogenation or Raney Nickel conditions to provide the desired pro-drug.

Example 43

Preparation of Exemplary Compounds of the Present Invention

Compounds of the invention can be prepared as generally described in Scheme 43.1, with examples depicted in Scheme 43.2.

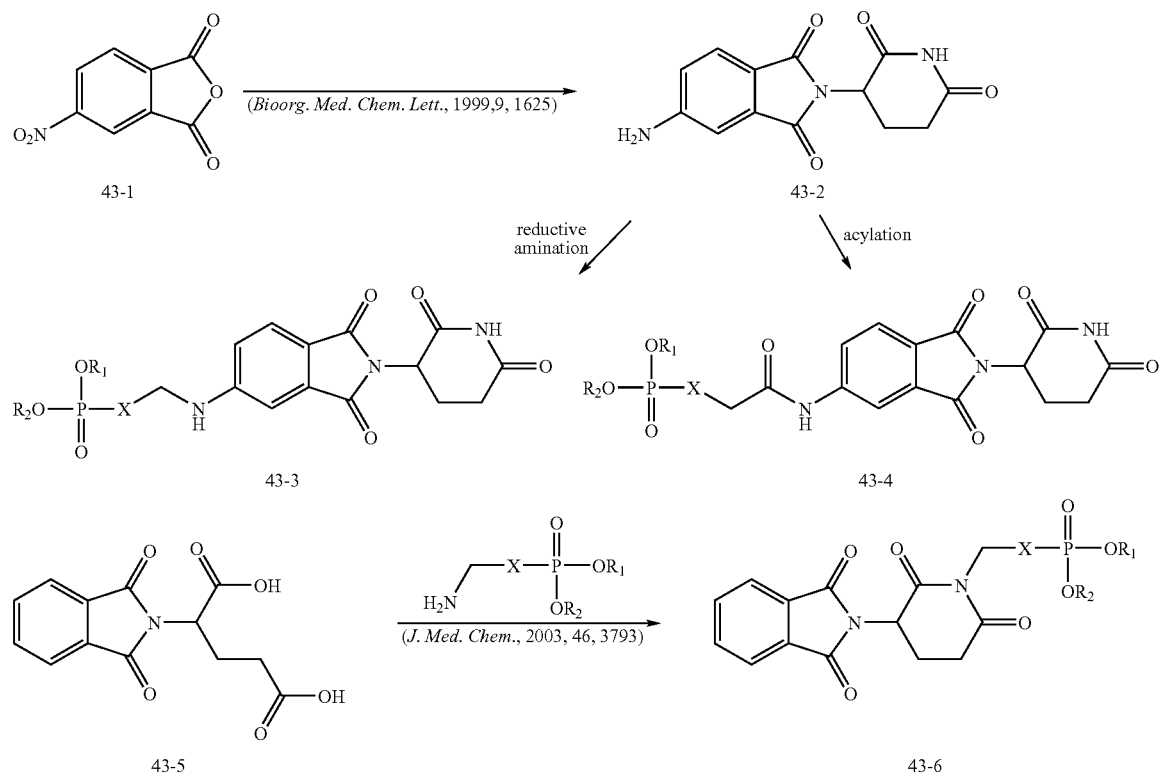

X = 0 to 4 atoms spacer

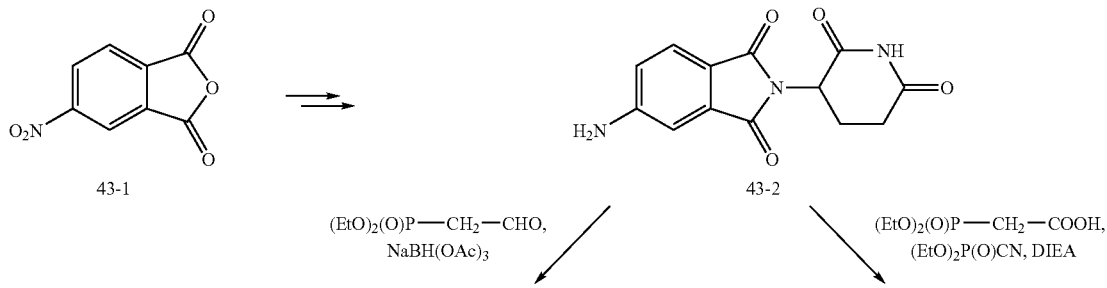

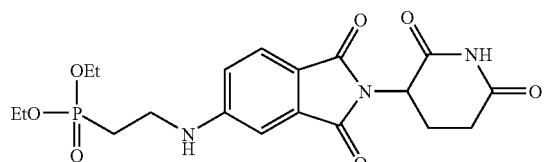

43-7

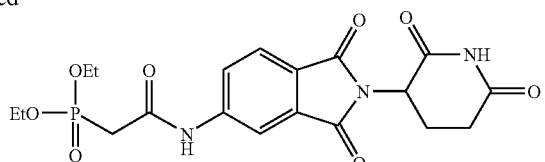

43-8

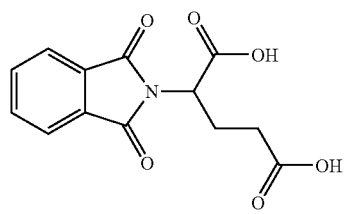

43-5

NH₂—CH₂CH₂—P(O)(OEt)₂
DCC, HOBt, Et₃N
→

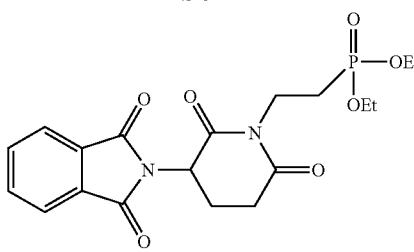

43-9

5-Nitro-isobenzofuran-1,3-dione (commercially available) is converted to 5-amino-2-(2,6-dioxo-piperidin-3-yl)-isoindole-1,3-dione following the procedures reported in *Bioorg. Med. Chem. Lett.*, (1999), 9, 1625. This amine intermediate is subjected to a reductive amination with diethylphosphonoacetaldehyde (obtained from ozonolysis of diethyl allylphosphonate) in the presence of a reducing agent such as sodium triacetoxyborohydride to generate the desired amine linker analog (*J. Org. Chem.*, (1996), 61, 3849). Alternatively, the amine is acylated with an activated diethylphosphonoacetic acid to provide the desired amide linker compound, according to a procedure such as those reported in *J. Med. Chem.*, (1982), 25, 960 and *J. Med. Chem.*, (1984), 27, 600. The activated diethylphosphonoacetic acid can be obtained by treatment in a solvent such as dimethylformamide with a coupling reagent such as diethyl cyanophosphonate and a base such as diisopropylethylamine at room temperature.

2-(1,3-Dioxo-1,3-dihydro-isoindol-2-yl)-pentanedioic acid (commercially available) is treated in a solvent such as acetonitrile with triethylamine, 1-hydroxybenzotriazole, 4-methoxybenzylamine, and 1,3-dicyclohexylcarbodiimide. After the reaction is complete, the solvent is removed and the residue is purified by chromatography to generate the desired analog, according to a procedure such as that reported in *J. Med. Chem.*, (2003), 46, 3793.

Example 44

Preparation of Exemplary Compounds of the Present Invention

Compounds of the invention can be prepared as generally described in Scheme 44.1, with an example depicted in Scheme 44.2.

Scheme 44.1

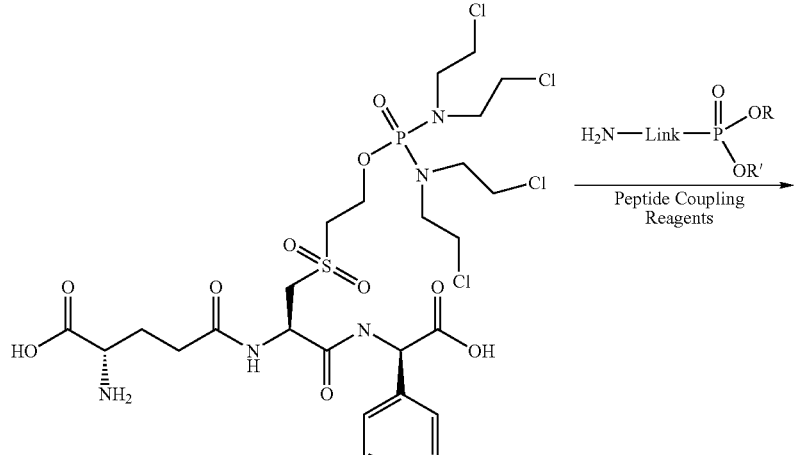

44-1

-continued
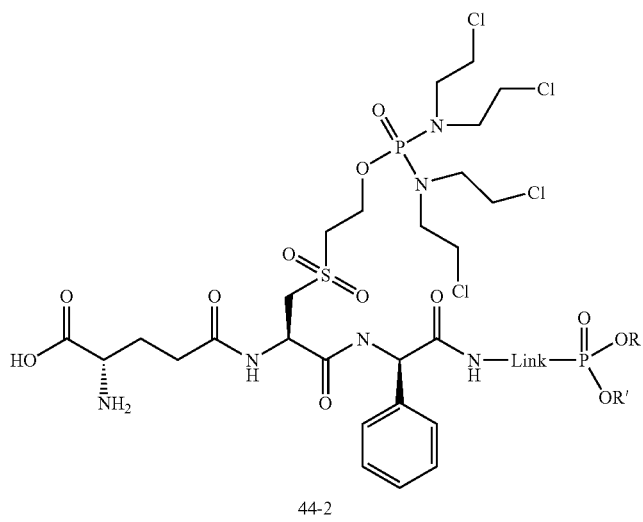
44-2
Scheme 44.2
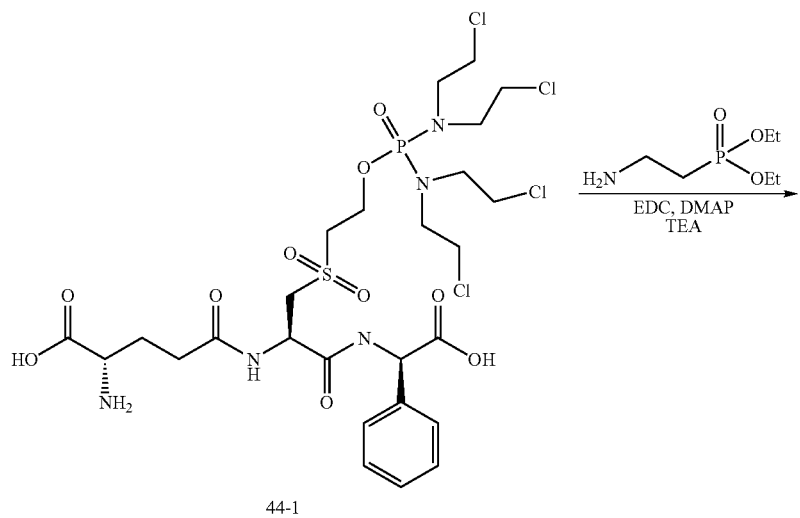
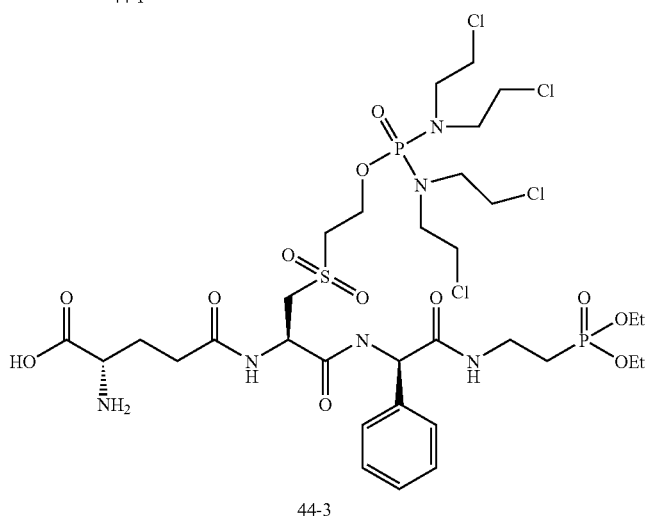
44-3

Synthesis of the pro-drug of TLK-286 is shown in Schemes 44.1 and 44.2. With two carboxylic acids present in the pro-drug moiety, mixtures of coupled product are separated by HPLC, to provide the desired product. Aminoethyl diethyl phosphonate is commercially available from Fluka as the oxalate salt which can be freed using triethyl amine in the reaction medium. Peptide coupling reactions are typically run in dimethylformamide (DMF) with addition of dichloromethane. Carbodiimide coupling reagents may be used in the presence of dimethylaminopyridine to speed up the reaction. Prevention of racemization may be achieved using hydroxybenztriazole (HOBt).

Example 45

Preparation of Exemplary Compounds of the Present Invention

Compounds of the invention can be prepared as generally described in Schemes 45.1-45.2, with examples depicted in Scheme 45.3.

Scheme 45.1: Modification of one aminoethyl substituent

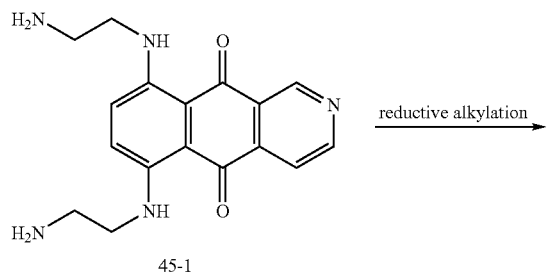

reductive alkylation 45-1

45-2

Scheme 45.2: Quaternization at the pyridine moiety

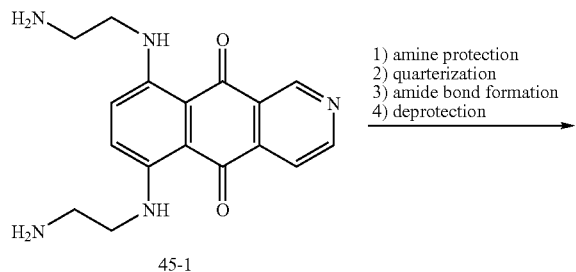

1) amine protection
2) quarterization
3) amide bond formation
4) deprotection 45-1

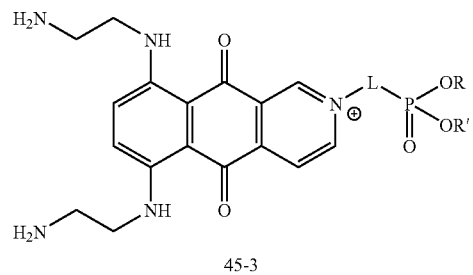

45-3

Scheme 45.3: Modification at the aminoethyl substituent

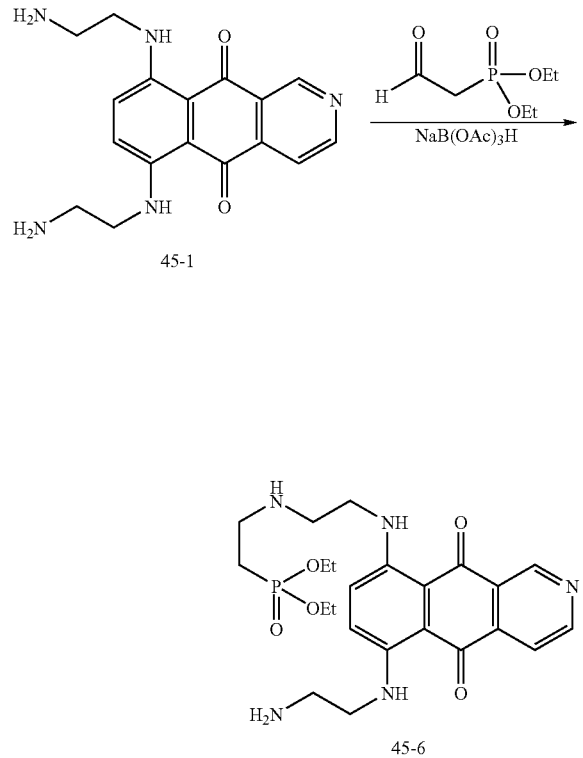

45-1

45-6

Pixantrone is treated in an organic solvent such as tetrahydrofuran (THF) or dichloromethane (DCM) with (2-oxoethyl)phosphonic acid diethyl ester (1 equiv.) and sodium triacetoxyborohydride, as described in *J. Org. Chem*, (1996), 61, 3849-3862. The reaction is quenched with aqueous sodium bicarbonate and the product is extracted with an organic solvent such as ethyl acetate. Separation of the product, the other regioisomer, and bis-alkylated material is achieved by chromatography.

Scheme 45.4: Modifications of the pyridine moiety

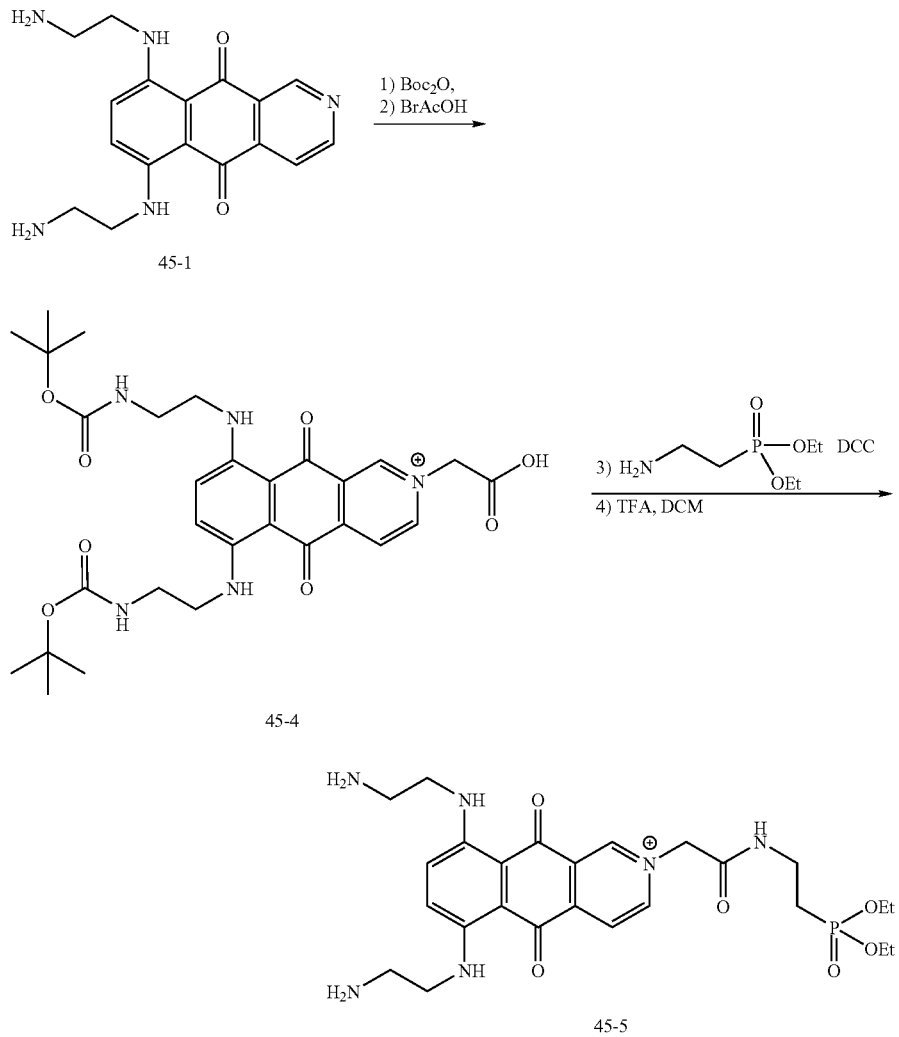

Pixantrone is dissolved in an organic solvent such as dimethylformamide (DMF), THF, or chloroform and is treated with tert-butoxycarbonyl anhydride according to standard literature procedures (Greene, T. W.: Protective groups in organic chemistry, Wiley-Interscience, (1999). The solvents are removed in vacuo. The crude material is dissolved in an organic solvent such as chloroform and the solution is washed with aqueous 0.1 N HCl and aqueous bicarbonate solution. The solution is dried and the solvent is removed in vacuo. As needed the product is further purified by chromatography. The product of step 1 is dissolved in an organic solvent such as DMF, and bromoacetic acid (1 equiv.) is added. The solution is heated at an elevated temperature such as 50-70° C. under an atmosphere of an inert gas like nitrogen. When the reaction is complete, the solvent is removed in vacuo and the product is further purified by chromatography. This material is dissolved in an organic solvent such as chloroform or DMF and is reacted with 2-aminoethylphosphonic acid diethyl ester (commercially available) in the presence of a coupling reagent such as dicyclohexylcarbodiimide (DCC), an organic tertiary amine base such as diisopropylethylamine (DIEA), and a catalytic amount of N,N-dimethylaminopyridine (DMAP). At the end of the reaction, the reaction mixture is filtered and the solvent is removed in vacuo. The crude material is dissolved in DCM and treated with trifluoroacetic acid at room temperature according to the standard (Greene, T. W.: Protective groups in organic chemistry, Wiley-Interscience (1999). At the end of the reaction the solvents are removed in vacuo to yield the crude final product, which is further purified by chromatography.

Example 46

Preparation of Exemplary Compounds of the Present Invention

Compounds of the invention can be prepared as generally described in Schemes 46.1 and 46.3, with examples depicted in Schemes 46.2 and 46.4.

Scheme 46.1

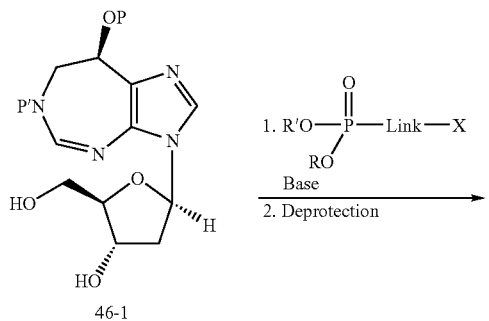

Scheme 46.2

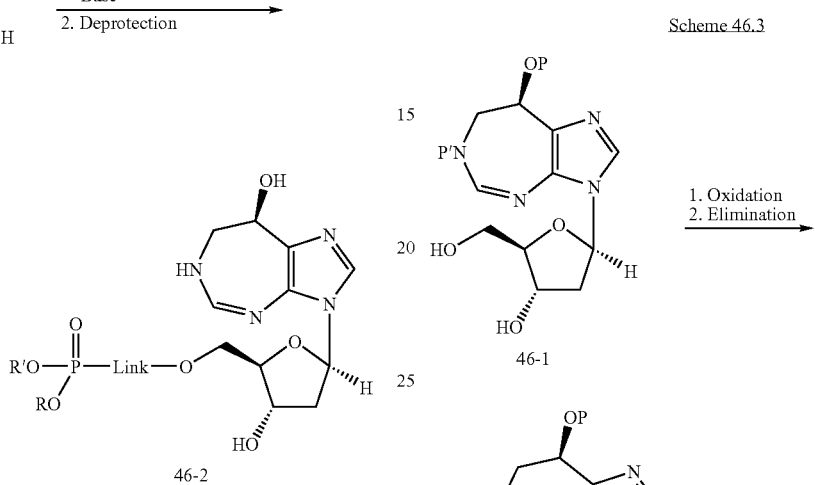

The appropriately protected 2'-deoxycoformycin prepared according to U.S. Pat. No. 3,923,785 (also reported in Chan, E. et al., *J. Org. Chem.*, (1982), 47, 3457) can be treated in a solvent such as tetrahydrofuran or dimethylformamide with a base such as sodium hydride. Formation of the fully protected compound 46-1, 46-3 can be accomplished utilizing (8R)-6-(t-butoxycarbonyl)-8-[(t-butyldimethylsilyl)oxy]-3,6,7,8-tetrahedroimidazo[4,5-d]-[1,3]diazapine, prepared by Truong, T. V. et al. *J. Org. Chem.* (1993), 58, 6090, through the Vorbruggen glycosylation reaction as described in Chan, E. et al., *J. Org. Chem.*, (1982), 47, 3457. When bubbling ceases, diethyl phosphonomethyltriflate (prepared according to *Tetrahedron Lett.*, (1986), 27, 1477) is added, yielding the desired phosphonate diester 46-1, 46-3.

Scheme 46.3

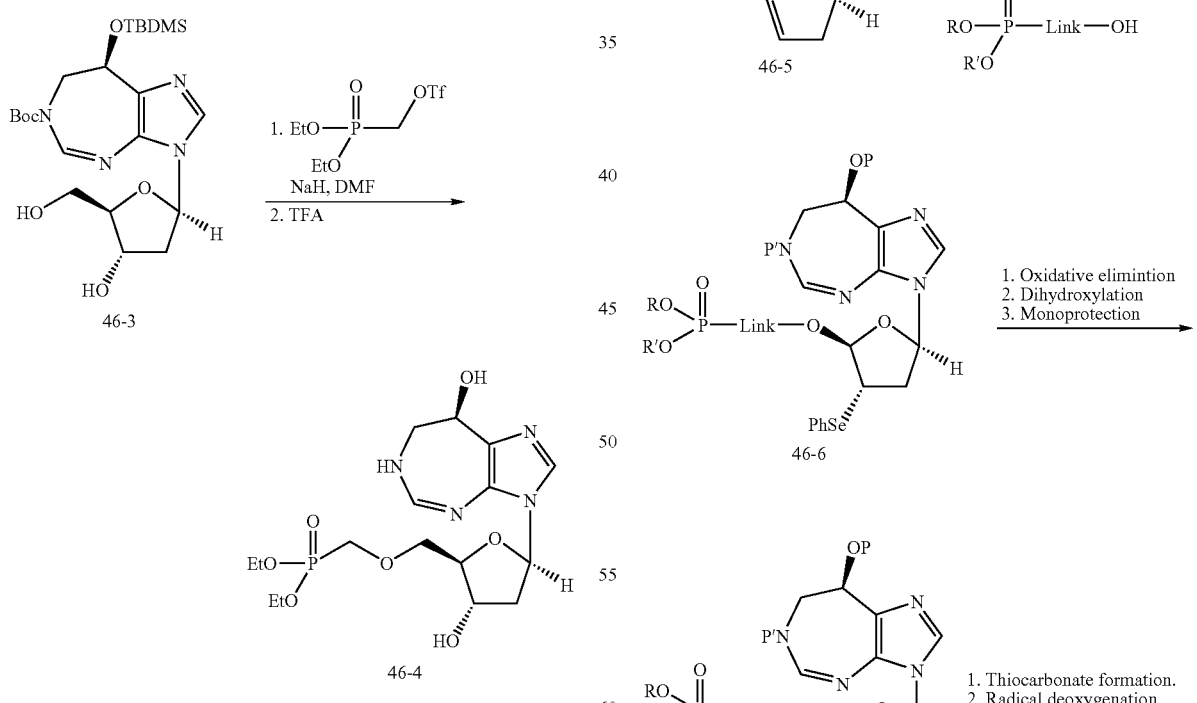

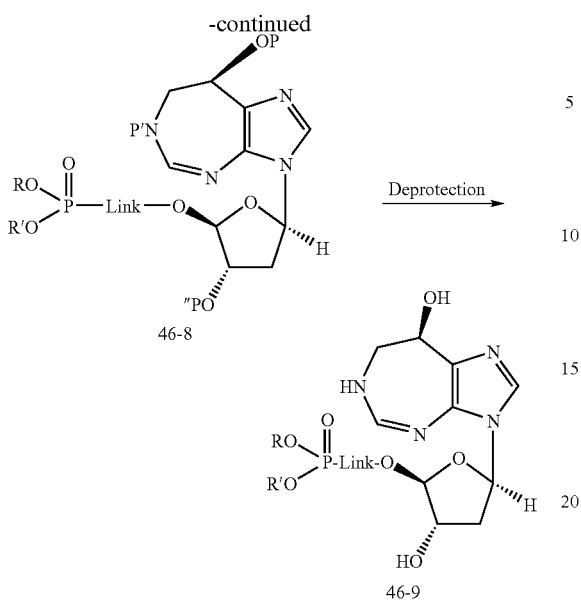

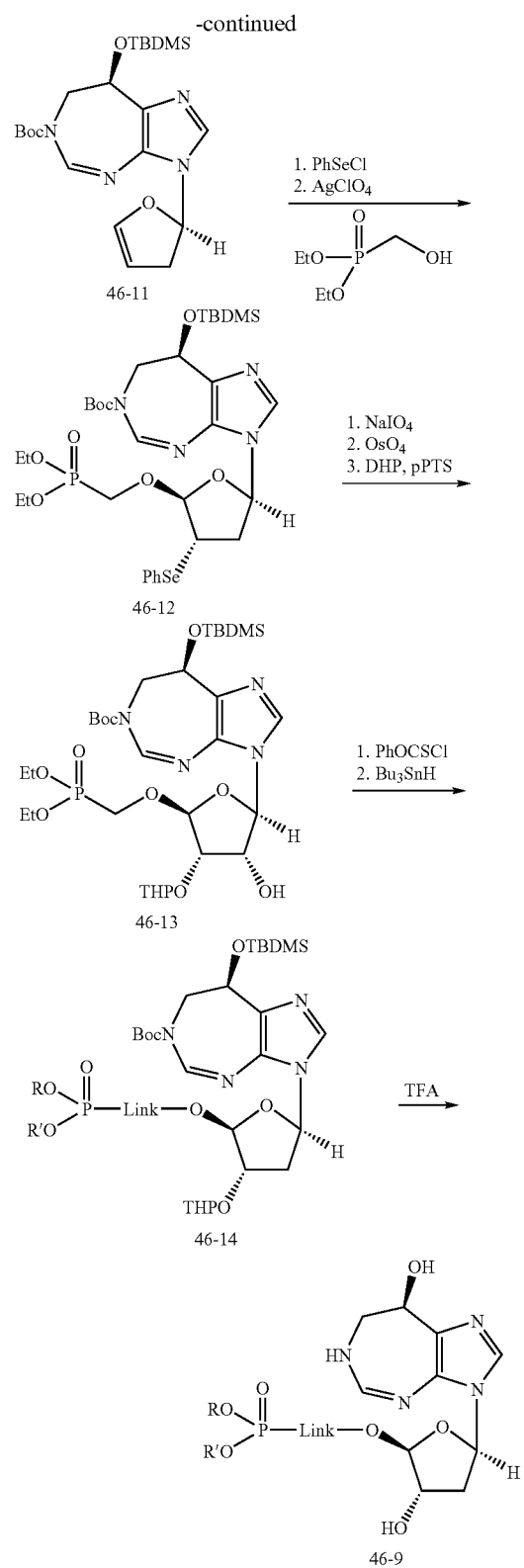

The preparation of compound 46-9 is described in Scheme 46.3. Compound 46-1, (8-(tert-butyl-dimethyl-silanyloxy)-3-(4-hydroxy-5-hydroxymethyl-tetrahydro-furan-2-yl)-7,8-dihydro-3H-imidazo[4,5-d][1,3]diazepine-6-carboxylic acid tert-butyl ester) can be prepared as described in Truong, T. V. et al. *J. Org. Chem.*, (1993), 58, 6090 and Chan, E. et al., *J. Org. Chem.*, (1982), 47, 3457. Oxidation of the 5'-OH followed by elimination of the carboxylic acid provides glycal 46-5 (see the procedure of Zemlicka J. et al., *J. Am. Chem. Soc.*, (1972), 94, 9, 3213). Selenoetherification provides the protected phosphonate 46-6 (Kim, C. et al., *J. Org. Chem.*, (1991), 56, 2642). Oxidative elimination of the phenylselenide (as described in Kim, C. et al., *J. Org. Chem.*, (1991), 56, 2642) followed by stereoselective dihydroxylation provides the diol, which can then be converted to a monotetrahydropyran protected compound 46-7. Acylation of the 2' alcohol with phenyl chlorothionoformate provides the precursor for Robins deoxygenation. Subsequent deoxygenation provides compound 46-8 (Metteuci, M. D. et al. *Tetrahedron Lett.*, (1987), 28, 22, 2459, also see Robins, M. J. et al. *J. Org. Chem.*, (1995), 60, 7902). The order of formation of the 3' protected alcohol and thiocarbonate formation can also be reversed if the first protection proceeds exclusively at the 2' position. In that case, the 2' thiocarbonate is formed first, followed by protection of the 3' hydroxyl group and a final Robins deoxygenation. Trifluoroacetic acid (TFA)-mediated deprotection removed all three protecting groups to provide compound 46-9.

Scheme 46.4

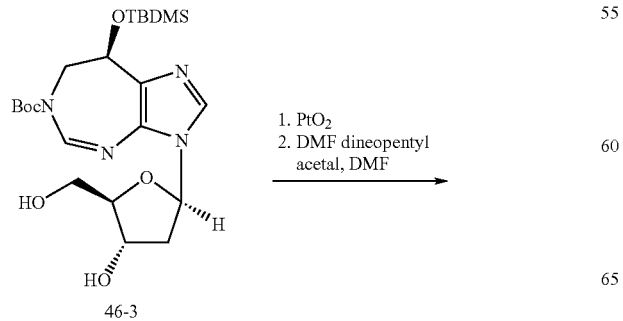

Specifically, compound 46-3 (Truong, T. V. et al., *J. Org. Chem.*, (1993), 58, 6090 and Chan, E. et al., *J. Org. Chem.*, (1982), 47, 3457) is oxidized with $PtO_2$ to provide carboxylic acid 2.2. Decarboxylative elimination is achieved using dimethylformamide dineopentyl acetal in DMF at high temperature (Zemlicka J. et al., *J. Am. Chem. Soc.*, (1972), 94, 9, 3213). Once the furanoid glycal 46-11 is in hand, it is treated with phenylselenyl chloride to perform the selenoetherification followed by treatment with silver perchlorate in the presence of diethyl(hydroxymethyl)phosphonate (Phillion, D. et al., *Tetrahedron Lett.*, (1986), 27, 1477) to give phosphonate 46-12 (Kim, C. et al., *J. Org. Chem.*, (1991), 56, 2642). Oxidative elimination of the selenide followed by dihydroxylation using osmium tetraoxide provides a diol, which is converted to the mono-protected tetrahydropyranyl ether compound 46-13. Acylation of the 2' alcohol with phenyl chlorothionoformate provides the precursor for Robins deoxygenation, which is performed with tributyltin hydride to give compound 46-14 (Metteuci, M. D. et al., *Tetrahedron Lett.*, (1987), 28, 22, 2459, also see Robins, M. J. et al., *J. Org. Chem.*, (1995), 60, 7902). Removal of all the protecting groups is achieved using TFA to give compound 46-9 (Greene, T., Protective groups in organic synthesis, Wiley-Interscience, (1999)).

Example 47

Preparation of Exemplary Compounds of the Present Invention

Compounds such as these can be made according to the general routes outlined in Schemes 47.1 and 47.3, with examples depicted in Schemes 47.2 and 47.4.

Scheme 47.1

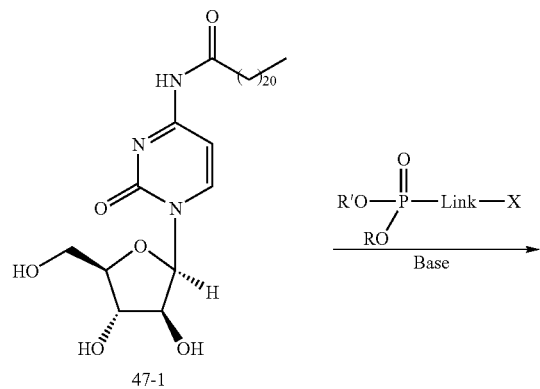

Scheme 47.2

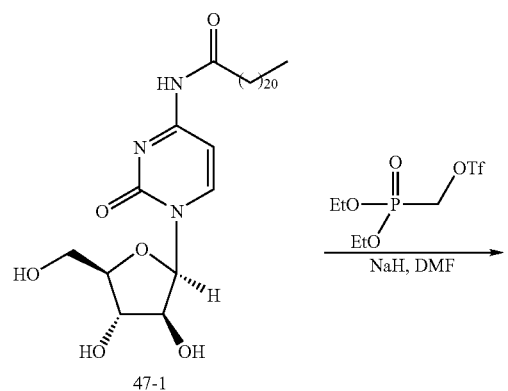

The N-(1-β-D-arabinofuranosyl-1,2-dihydro-2-oxo-4-pyrimidinyl)docosanamide (U.S. Pat. No. 3,991,045, also see Akiyama, M. et al., *Chem. Pharm. Bull.*, (1978), 26, 3, 981) is treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester 47-2, 47-3.

Scheme 47.3

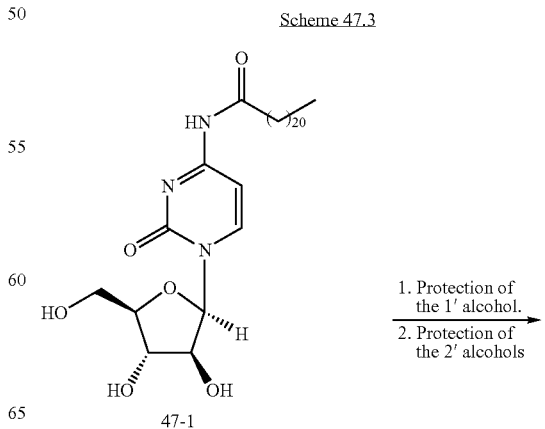

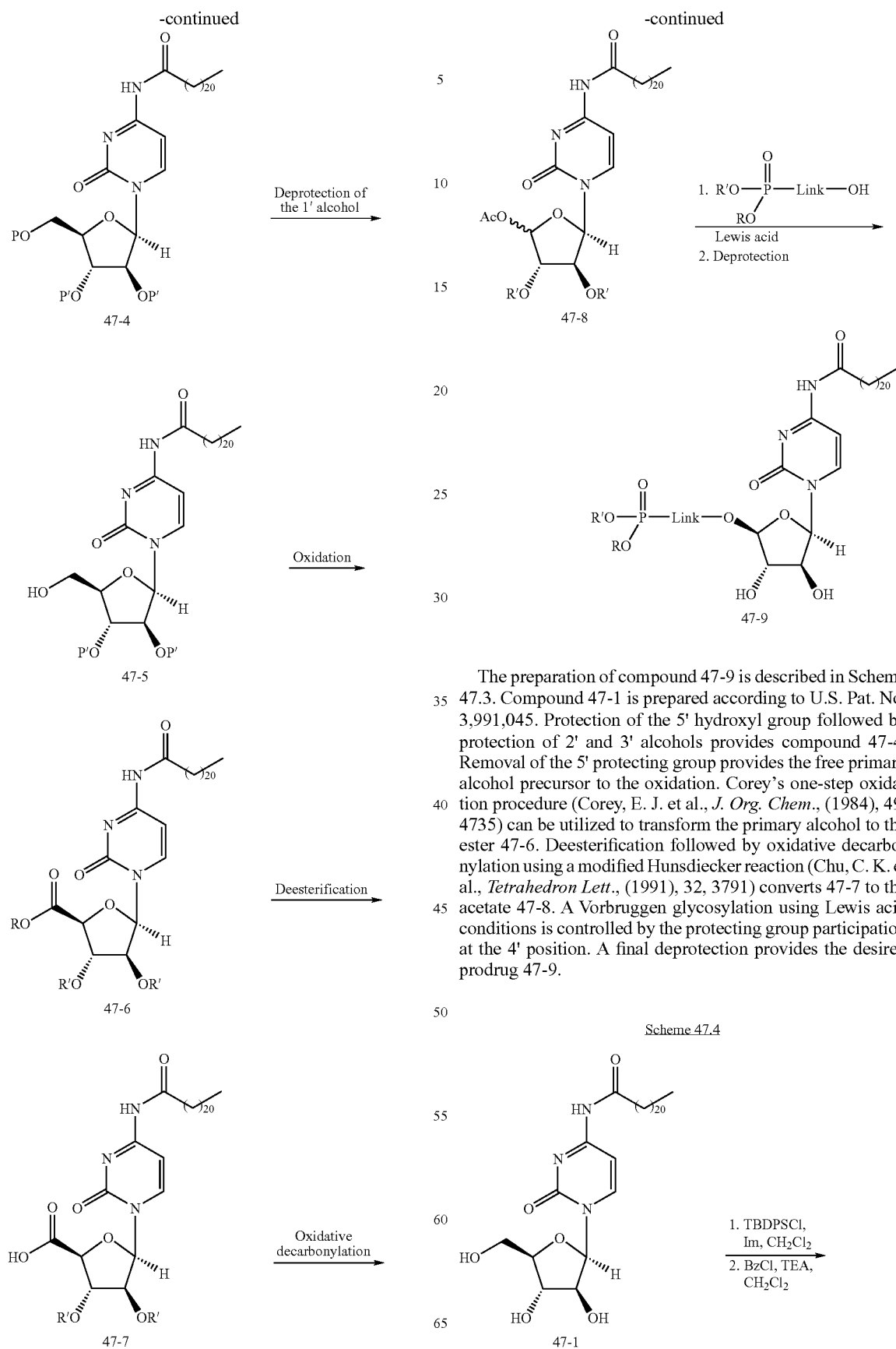

The preparation of compound 47-9 is described in Scheme 47.3. Compound 47-1 is prepared according to U.S. Pat. No. 3,991,045. Protection of the 5' hydroxyl group followed by protection of 2' and 3' alcohols provides compound 47-4. Removal of the 5' protecting group provides the free primary alcohol precursor to the oxidation. Corey's one-step oxidation procedure (Corey, E. J. et al., *J. Org. Chem.*, (1984), 49, 4735) can be utilized to transform the primary alcohol to the ester 47-6. Deesterification followed by oxidative decarbonylation using a modified Hunsdiecker reaction (Chu, C. K. et al., *Tetrahedron Lett.*, (1991), 32, 3791) converts 47-7 to the acetate 47-8. A Vorbruggen glycosylation using Lewis acid conditions is controlled by the protecting group participation at the 4' position. A final deprotection provides the desired prodrug 47-9.

Scheme 47.4

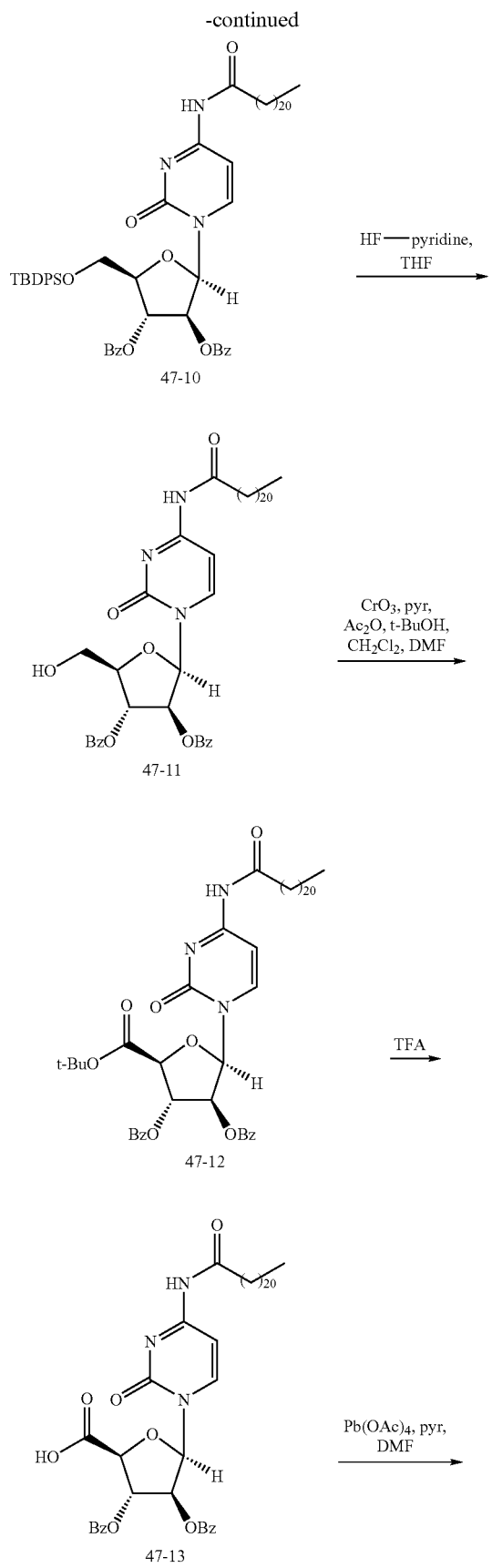

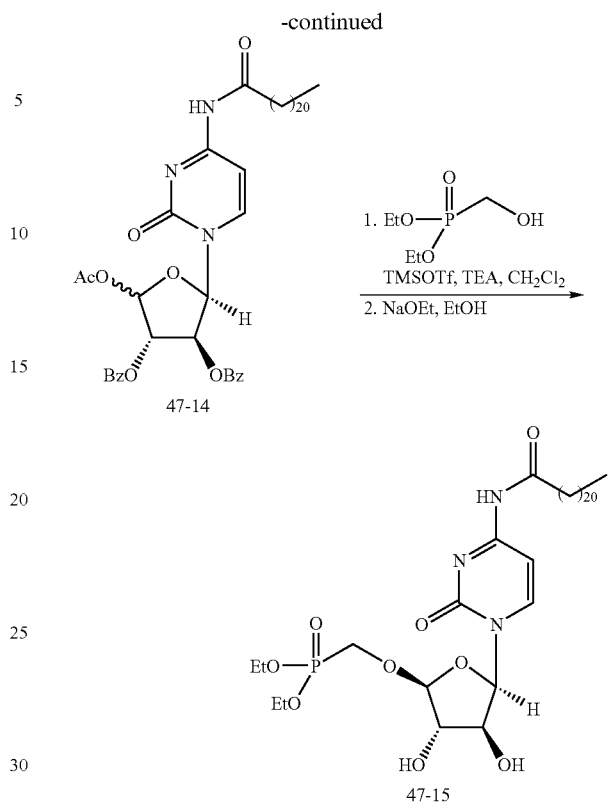

Specifically, compound 47-1, N-(1-β-D-arabinofuranosyl-1,2-dihydro-2-oxo-4-pyrimidinyl)docosanamide (U.S. Pat. No. 3,991,045) is selectively protected with a tert-butyldiphenylsilyl (TBDPS) group to provide the 5'-O-TBDPS analog. Further protection of the 3' and 4' alcohols as benzoate esters provides compound 47-10 (Teng, K., Cook, D. *J. Org. Chem.*, (1994), 59, 278). Exposure of the fully protected compound 47-10 to HF-pyridine reagent selectively deprotects the 5' hydroxyl group which can then be oxidized to the t-butyl ester using the Corey-Samuelsson oxidation (Corey, E. J., Samuelsson, B. *J. Org. Chem.*, (1984), 49, 4735). Deesterification of the oxidized product using trifluoroacetic acid provides compound 47-13. Oxidative decarboxylation using a modified Hunsdiecker reaction (Chu, C. K. et al., *Tetrahedron Lett.*, (1991), 32, 3791) converts the free acid to the acetate 47-14 which may be a mixture of anomers at 5'. While separation of the anomers may be achieved by column chromatography, it is not necessary to do so. The stereochemical outcome of a Vorbruggen glycosylation is controlled by the stereochemistry of the 4'-benzoyl group due to anchimeric assistance, rendering separation of the isomers is unnecessary. Vorbruggen glycosylation using hydroxymethylphosphonic acid diethyl ester proceeds to provide the protected phosphonate. A final deprotection using hydrolysis conditions completes the synthesis of compound 47-15.

Example 48

Preparation of Exemplary Compounds of the Present Invention

Compounds such as these are made according to the general route outlined in Schemes 48.1 and 48.3, with examples depicted in Schemes 48.2 and 48.4.

Scheme 48.1

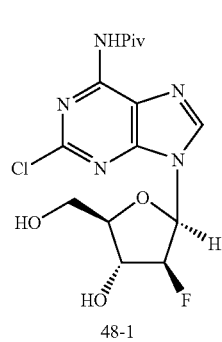
48-1

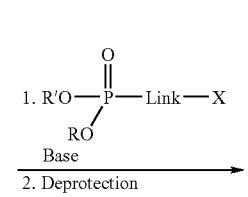

1. R'O—P(=O)(OR)—Link—X
   Base
2. Deprotection

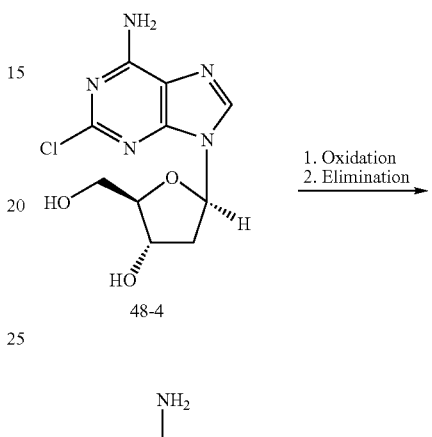
48-2

Scheme 48.2

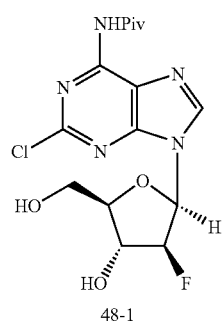
48-1

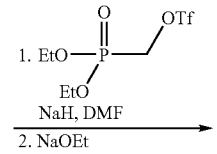

1. EtO—P(=O)(OEt)—CH₂—OTf
   NaH, DMF
2. NaOEt 48-3

The appropriately protected 2-chloro-9-(2-deoxy-2-fluoro-β-D-arabinofuranosyl)-9H-purin-6-amine 48-1, prepared according to U.S. Pat. No. 5,034,518 (also described in WO 03011877) is treated in a solvent such as tetrahydrofuran or dimethylformamide with a base such as sodium hydride. Formation of the pivaloyl compound 48-1 is accomplished by protecting 2-chloro-9-(2-deoxy-2-fluoro-β-D-arabinofuranosyl)-9H-purin-6-amine with a pivaloyl group (Greene, T., Protective groups in organic synthesis, Wiley-Interscience, (1999)). When bubbling ceases, diethyl phosphonomethyltriflate (prepared according to *Tetrahedron Lett.*, (1986), 27, 1477) is added, yielding the protected product 48-2, 48-3. The pivaloyl group is removed with sodium ethoxide to provide the desired phosphonate diester 48-2, 48-3.

Scheme 48.3

48-4

1. Oxidation
2. Elimination 48-5

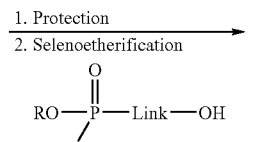
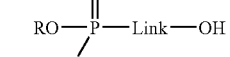

1. Protection
2. Selenoetherification

RO—P(=O)(OR')—Link—OH

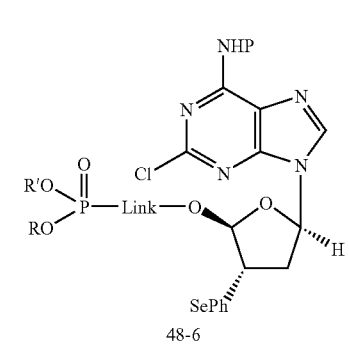
48-6

1. Oxidative elimintion
2. Dihydroxylation
3. 2' protection
4. 3' protection
5. 2' deprotection

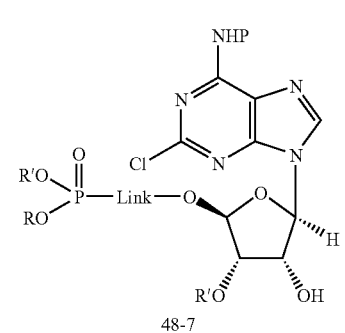
48-7

1. DAST, CH₂Cl₂
   pyridine
2. Deprotection of the base and the 3' alcohol

-continued

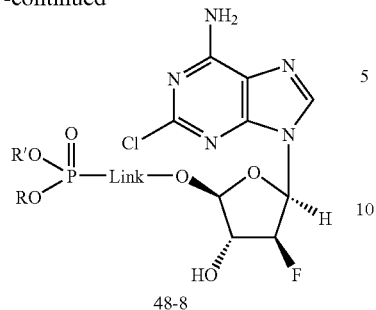
48-8

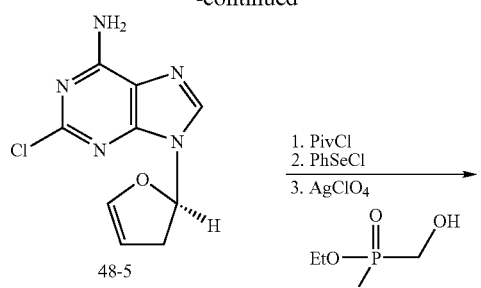
48-5

The preparation of compound 48-8 is described in Scheme 48.3. Compound 48-4,9-(2-deoxy-α-D-ribofuranosyl)-2-fluoroadenine, is prepared as described in Montgomery, J. et al., *J. Med. Chem.*, (1969), 12, 3, 498. Oxidation of the 5'-OH followed by elimination provides glycal 48-5 (see the procedure of Zemlicka J. et al., *J. Am. Chem. Soc.*, (1972), 94, 9, 3213). Protection of the chloroadenine at the 6 position followed by selenoetherification provides the protected phosphonate 48-6 (Kim, C. et al., *J. Org. Chem.*, (1991), 56, 2642). Oxidative elimination of the phenylselenide (as described in Kim, C. et al., *J. Org. Chem.*, (1991), 56, 2642) followed by stereoselective dihydroxylation provides the diol which can then be converted to the 2' protected alcohol. Protection of the 3' alcohol followed by removal of the protecting group at the 2' hydroxyl group provides compound 48-7. Fluorination and inversion of the stereochemistry at the 2' position can be simultaneously achieved by exposing the compound to dimethylaminosulfur trifluoroide (DAST) and pyridine (Pankiewicz, K. W. et al., *J. Org. Chem.*, (1992), 57, 553, also see Pankiewicz, K. W. et al., *J. Org. Chem.*, (1992), 57, 7315). Finally, the protecting groups are removed to provide compound 48-8.

Scheme 48.4

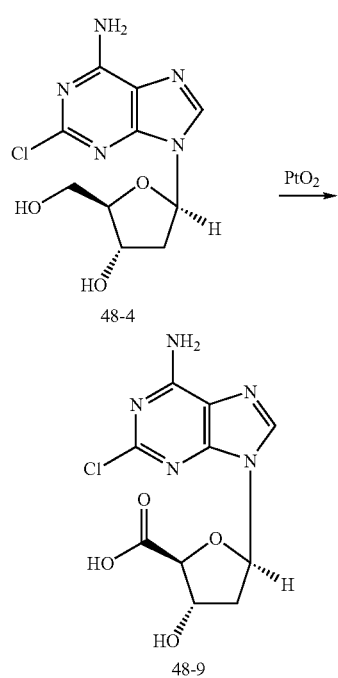

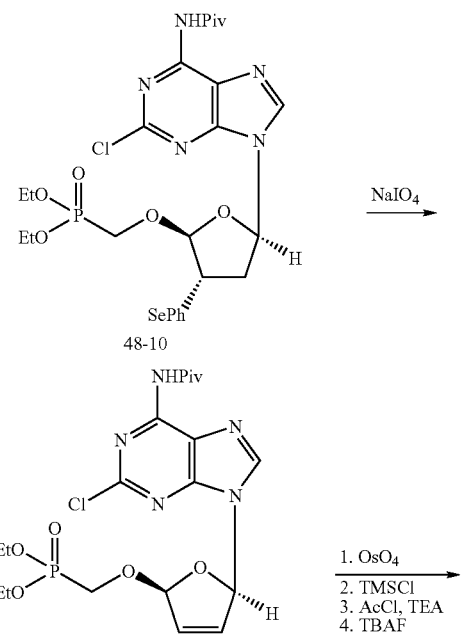

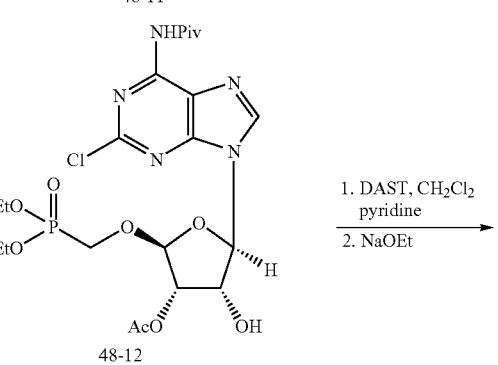

Specifically, 9-(2-deoxy-α-D-ribofuranosyl)$_2$-fluoroadenine, compound 48-4 (Montgomery, J. et al., *J. Med. Chem.*, (1969), 12, 3, 498), is oxidized with PtO$_2$ to provide carboxylic acid 48-9. Decarboxylative elimination is achieved using dimethylformamide dineopentyl acetal in dimethylformamide at high temperature (Zemlicka J. et al., *J. Am. Chem. Soc.*, (1972), 94, 9, 3213). Once the furanoid glycal 48-5 is in hand, it is first protected at the 6-position of the 2-chloroadenosine with pivaloyl chloride, using conditions as described in Greene, T., Protective groups in organic synthesis, Wiley-Interscience, (1999). Treatment of the protected glycal with silver perchlorate in the presence of diethyl(hydroxymethyl)phosphonate (Phillion, D. et al., Tetrahedron Lett., (1986), 27, 1477) provides the phosphonate 48-10 (Kim, C. et al., *J. Org. Chem.*, (1991), 56, 2642). Oxidative elimination of the selenide followed by dihydroxylation using osmium tetraoxide provides a diol which can be turned into a mono protected acetate 48-12 by first silylating at the 2'-OH group, followed by protection of the 3' alcohol with an acetate group and subsequent deprotection of the silyl group. Conversion of the 2' alcohol to the 2' fluoride with the opposite stereochemistry can be performed with DAST (Pankiewicz, K. W. et al., *J. Org. Chem.*, (1992), 57, 553, also see Pankiewicz, K. W. et al., *J. Org. Chem.*, (1992), 57, 7315). Conditions that deprotect the pivaloyl group (Greene, T., Protective groups in organic synthesis, Wiley-Interscience, (1999)) also remove the 3' acetate to provide compound 48-13.

Example 49

Preparation of Exemplary Compounds of the Present Invention

Representative compounds of the invention can be made according to the general route outlined in Schemes 49.1 and 49.3, with examples depicted in Schemes 49.2 and 49.4.

Scheme 49.1

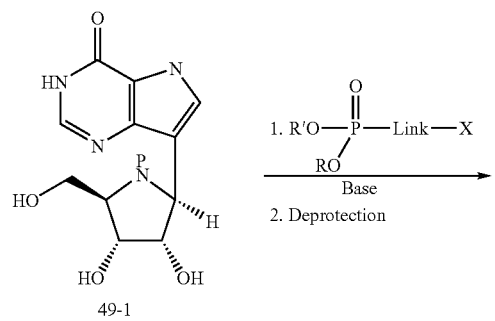

49-1

Scheme 49.2

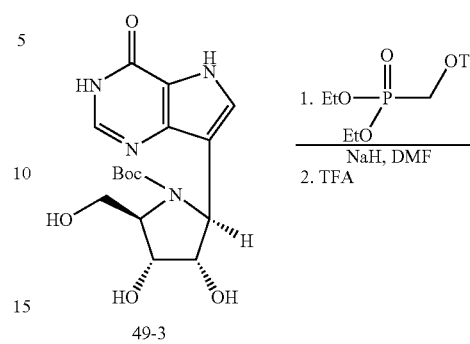

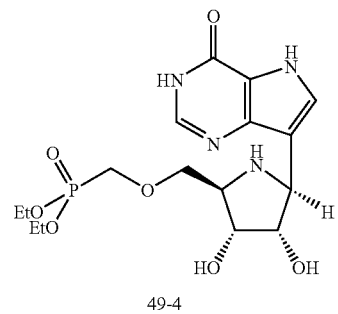

The Boc-protected (1S)-1-(9-deazaguanin-9-yl)-1,4-dideoxy-1,4-imino-D-ribitol, compound 49-1, 49-3, is prepared by stirring the (1S)-1-(9-deazaguanin-9-yl)-1,4-dideoxy-1,4-imino-D-ribitol (WO 9,919,338 and Evans, G. B. et al., *Tetrahedron*, (2000), 56, 3053, also reported in Evans, G. B. et al., *J. Med. Chem.* (2003), 46, 3412) with BOC anhydride as described in Greene, T., Protective groups in organic synthesis, Wiley-Interscience, (1999). Compound 49-1, 49-3 is then treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester 49-2, 49-4 after deprotection of the BOC group using trifluoroacetic acid (TFA).

Scheme 49.3

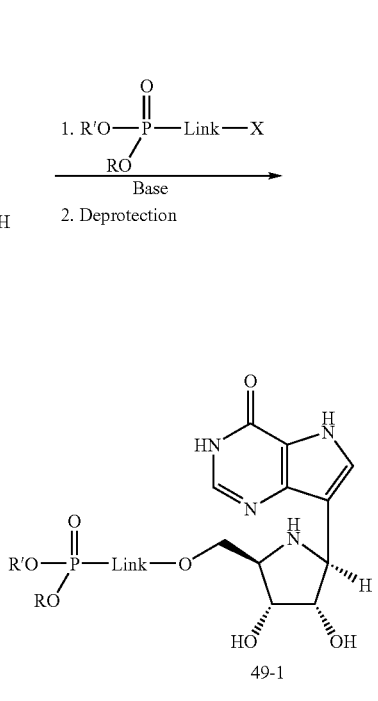

Oxidative elimination of the phenylselenide (as described in Kim, C. et al., *J. Org. Chem.*, (1991), 56, 2642) followed by stereoselective dihydroxylation provides the desired diol 49-9. Finally, the protecting group is removed.

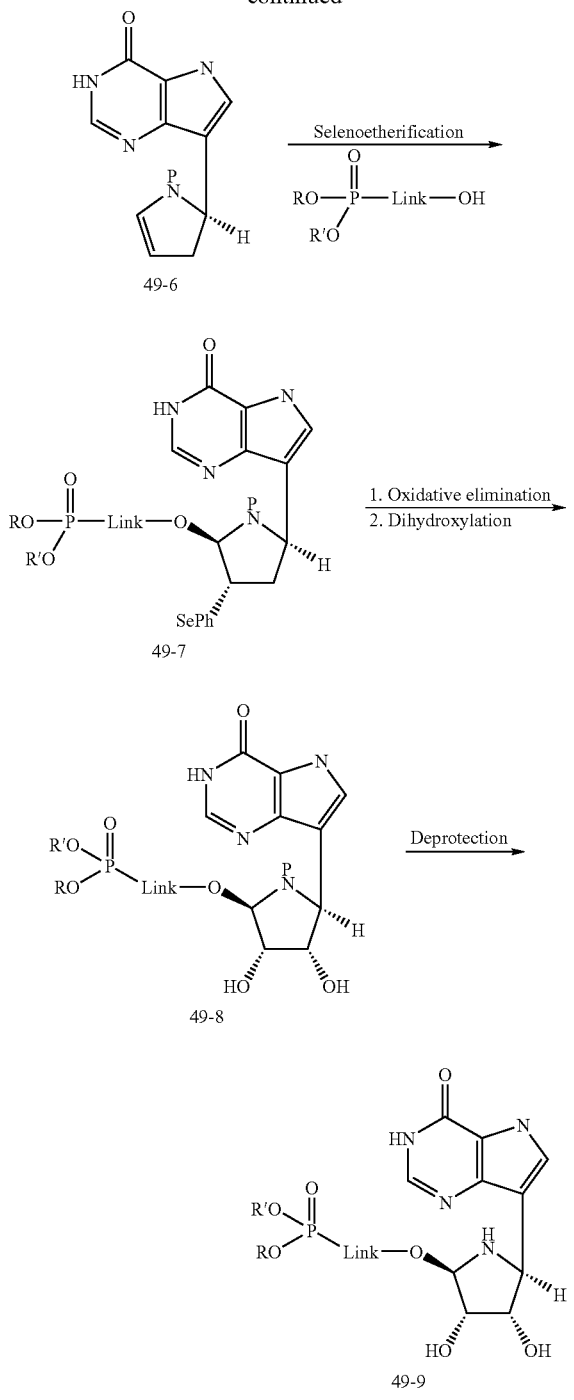

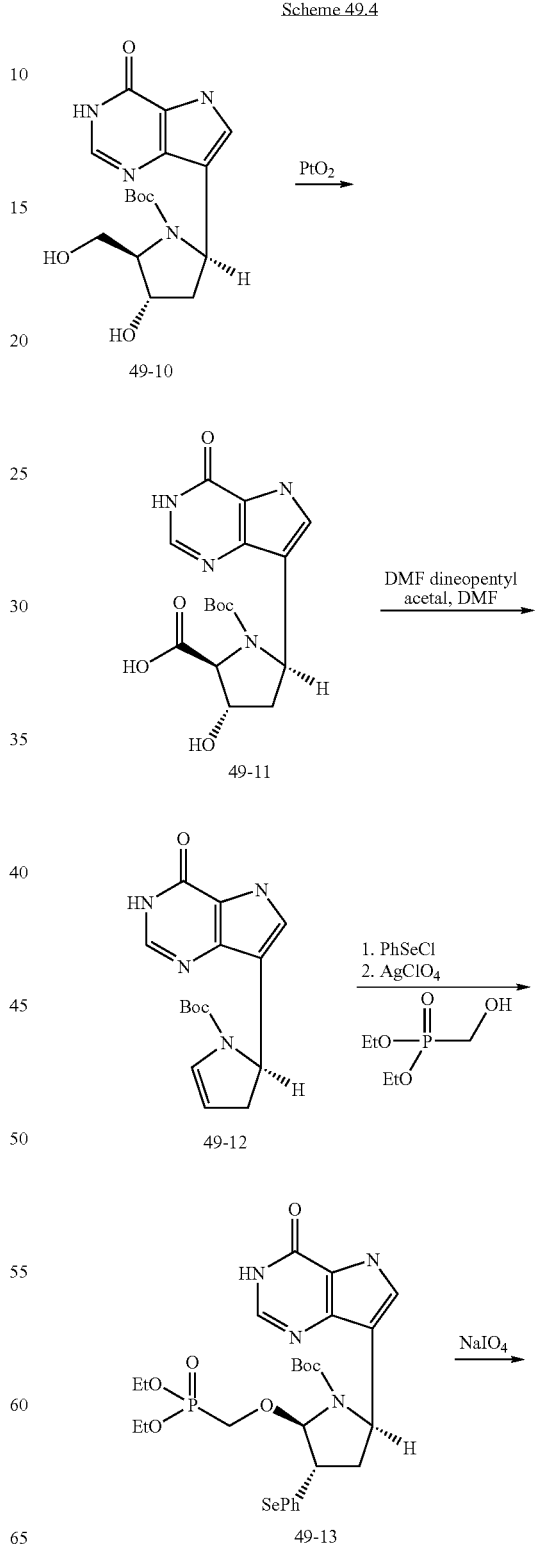

The preparation of compound 49-16 is described in Scheme 49.3. Deprotected compound 49-5 ((1R)-1-(9-deazahypoxanthin-9-yl)-1,2,4-trideoxy-1,4-imino-D-erythro-pentitol, as the hydrochloride salt) is prepared as described in Evans, G. B. et al., *Tetrahedron*, (2000), 56, 3053, using di-t-butyl dicarbonate in dichloromethane. Oxidation of the 5'-OH followed by elimination provides glycal 49-6 (see the procedure of Zemlicka J. et al., *J. Am. Chem. Soc.*, (1972), 94, 9, 3213). Selenoetherification provides the protected phosphonate 49-7 (Kim, C. et al., *J. Org. Chem.*, (1991), 56, 2642).

625

-continued

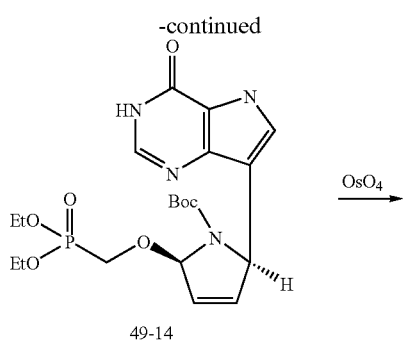

49-14

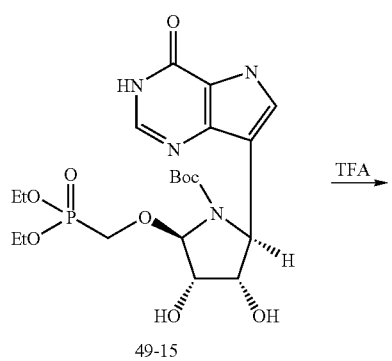

49-15

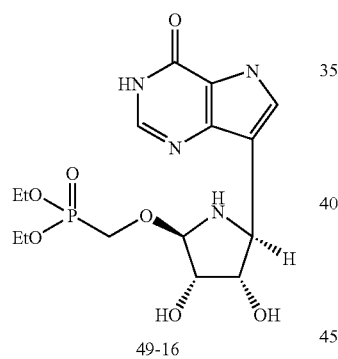

49-16

Specifically, (1R)-1-(9-deazahypoxanthin-9-yl)-1,2,4-trideoxy-1,4-imino-D-erythro-pentitol, prepared as the HCl salt as described in Evans, G. B. et al., *Tetrahedron*, (2000), 56, 3053, is first protected and then oxidized with $PtO_2$ to provide carboxylic acid 49-11. Decarboxylative elimination is achieved using dimethylformamide dineopentyl acetal in dimethylformamide at high temperature (Zemlicka J. et al., *J. Am. Chem. Soc.*, (1972), 94, 9, 3213). Selenoetherification followed by treatment of the protected glycal with silver perchlorate in the presence of diethyl(hydroxymethyl)phosphonate (Phillion, D. et al., Tetrahedron Lett., 1986, 27, 1477) provides the phosphonate 49-13 (Kim, C. et al., *J. Org. Chem.*, (1991), 56, 2642). Oxidative elimination of the selenide followed by dihydroxylation using osmium tetraoxide provides diol 49-15. Removal of the amine protecting group, according to the procedure of Greene, T., Protective groups in organic synthesis, Wiley-Interscience, (1999), provides compound 49-16.

626

Example 50

Preparation of Exemplary Compounds of the Present Invention

Scheme 50.1

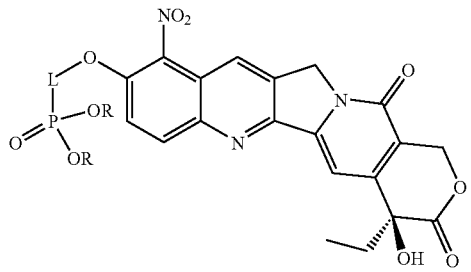

50-1

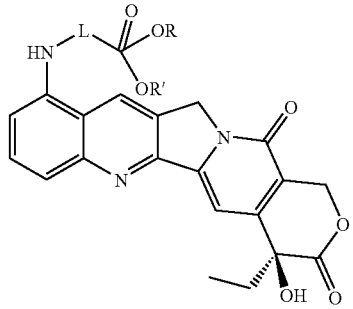

50-2

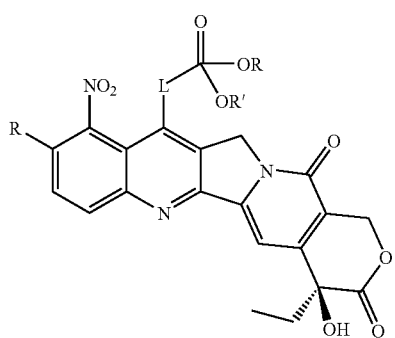

50-3

R = H
R = OH

L = linker
Linker is 1-8 atoms in length, with 2-6 atoms preferred

Compounds of the invention can be made according to the general route outlined in Schemes 50.2-50.4, with examples depicted in Schemes 50.5-50.7.

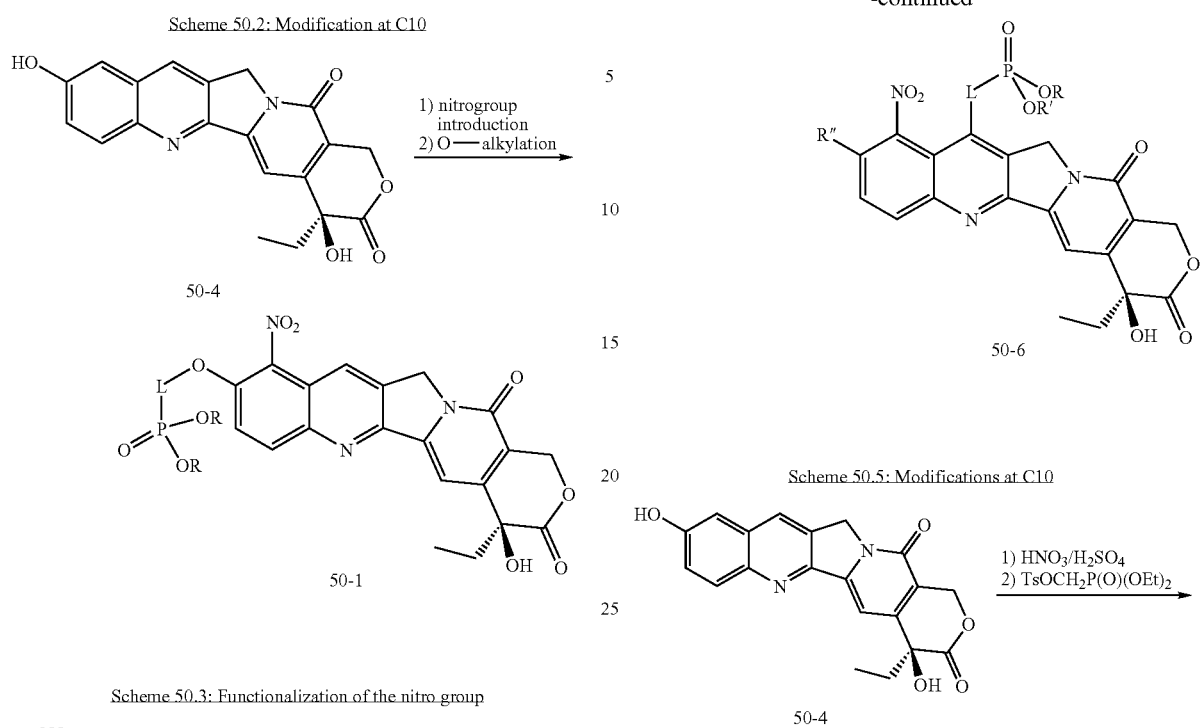

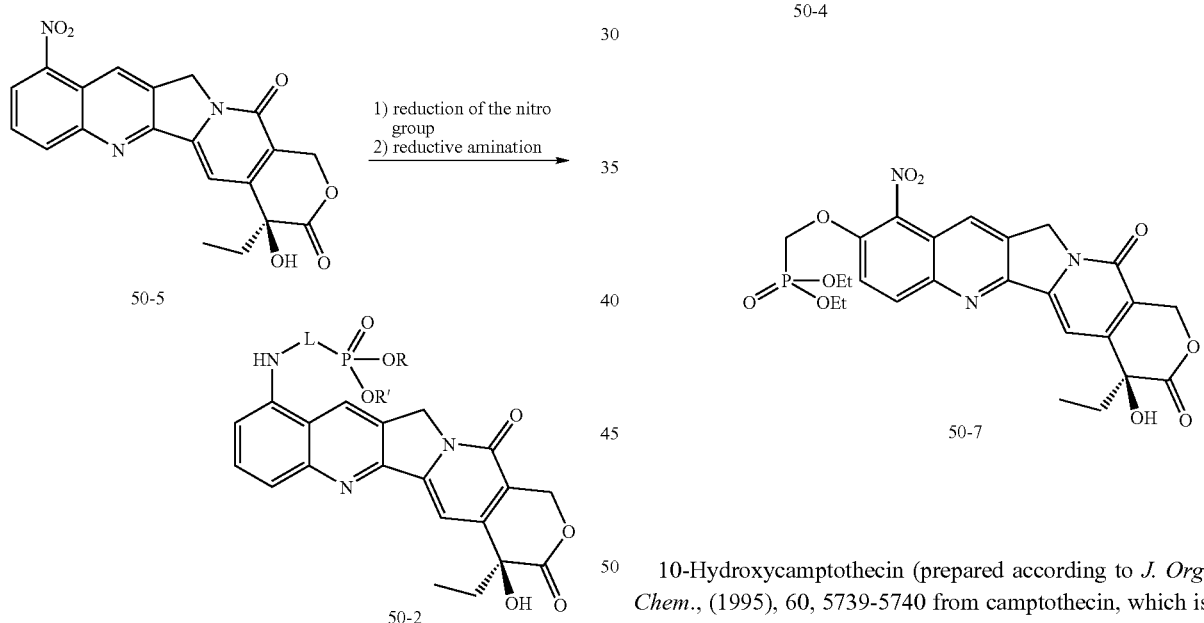

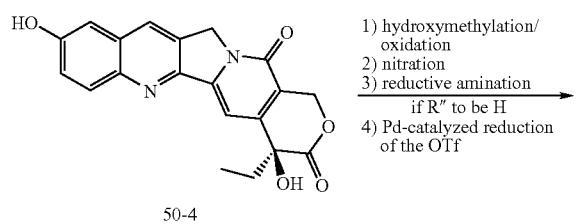

10-Hydroxycamptothecin (prepared according to *J. Org. Chem.*, (1995), 60, 5739-5740 from camptothecin, which is commercially available) is dissolved in mixture of sulfuric acid and nitric acid under ice cooling. At the end of the reaction, the crude reaction solution is poured onto ice. The precipitate is collected and washed with water, cold ethanol, and diethyl ether. As needed the product is further purified by recrystallization (*J. Med. Chem.*, (2001), 44, 1594-602). The product of step 1 is dissolved in an organic solvent such as tetrahydrofuran (THF), acetonitrile, or dimethylformamide (DMF) and is treated with a base such as sodium hydride. When bubbling ceases, diethyl phosphonomethyltriflate (prepared according to *Tetrahedron Lett.*, (1986), 27, 1477) is added, yielding the desired phosphonate ester. The product is further purified by chromatography.

Scheme 50.6: Modifications of the nitro group at C9

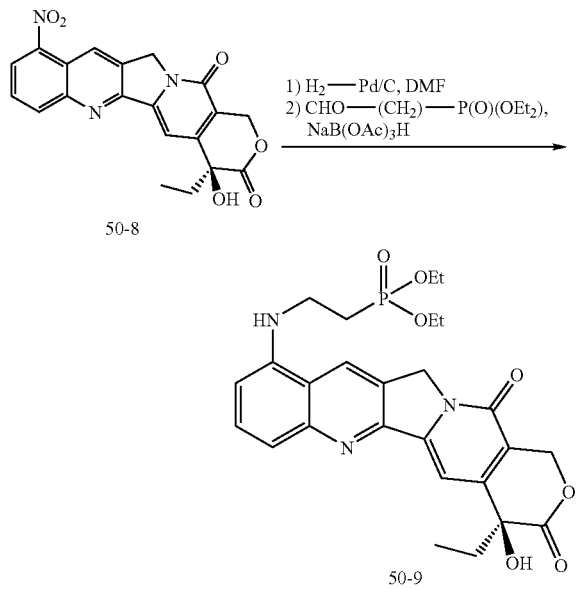

Rubetican is dissolved in an organic solvent such as DMF or ethyl acetate and is hydrogenated in the presence of Pd/C under an atmosphere of hydrogen. At the end of the reaction, the crude suspension is filtered through Celite and the solvent is removed in vacuo. As needed the product is further purified by chromatography. The product of step 1 is dissolved in an organic solvent such as THF, acetonitrile, or DMF and is treated with (2-oxoethyl)phosphonic acid diethyl ester (1 equiv.) and sodium triacetoxyborohydride as described in *J. Org. Chem*, (1996), 61, 3849-3862. The reaction is quenched with aqueous sodium bicarbonate and the product is collected as the resultant precipitate. The product is further purified by chromatography.

Scheme 50.7: Modification at C7

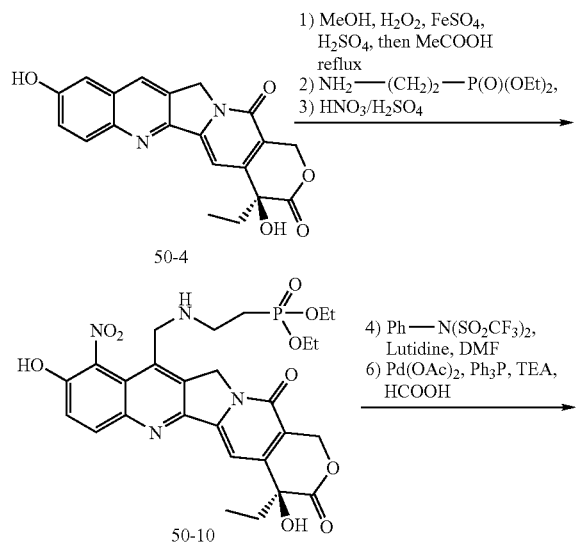

-continued

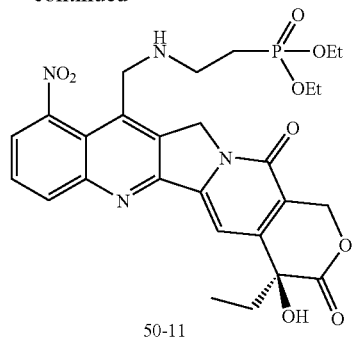

10-Hydroxycamptothecin is converted to the corresponding C7 aldehyde according to literature protocols (*J. Med. Chem.*, (2000), 43, 3963-3969). The product of this step is dissolved in an organic solvent such as THF, acetonitrile, or DMF and is treated with aminoethylphosphonic acid diethyl ester (1 equiv.) and sodium triacetoxyborohydride as described in *J. Org. Chem*, (1996), 61, 3849-3862. The reaction is quenched with aqueous sodium bicarbonate and the product is purified by chromatography. The product of this step is dissolved in mixture of sulfuric acid and nitric acid under ice cooling. At the end of the reaction, the crude reaction solution is poured onto ice. The precipitate is collected and washed with water, cold ethanol, and diethyl ether. As needed the product is further purified by recrystallization (*J. Med. Chem.*, (2001), 44, 1594-602).

Further conversion to the C10 reduced product (according to *J. Med. Chem.*, (1991), 34, 98-107).

The free C10 hydroxy compound synthesized above is dissolved in an organic solvent such as DMF under an inert gas atmosphere. A tertiary organic amine base such as 2,6 lutidine is added, followed by N-phenyltrifluoromethanesulfonimide. The reaction mixture is stirred at room temperature over night. When all starting material is consumed, a second tertiary organic amine base such as triethylamine is added followed by a palladium (II) species such as Pd(OAc)$_2$ and a phosphine such as triphenylphosphine, and concentrated formic acid. The reaction mixture is heated to an elevated temperature of approximately 60° C. At the end of the reaction, the solvent is removed in vacuo and the crude product is triturated with a small amount of water and dried. The product is further purified by chromatography.

Example 51

Preparation of Exemplary Compounds of the Present Invention

Reduction of the dose and/or improvement of efficacy are achieved by the use of pro-drugs of analogs of BAY-43-9006 which, upon cleavage inside the target cell, give rise to agents with increased intracellular half-lives. Such compounds are described below.

Scheme 51.1

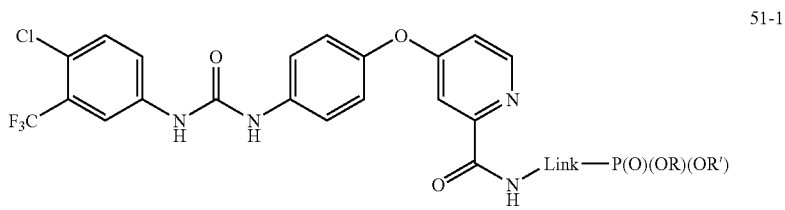

51-1

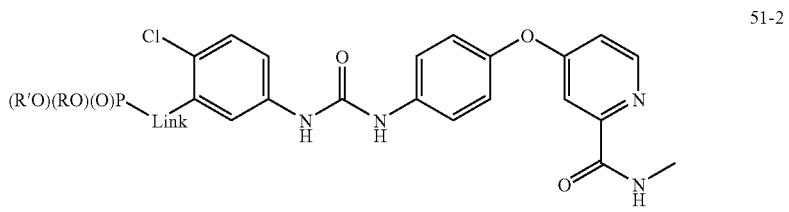

51-2

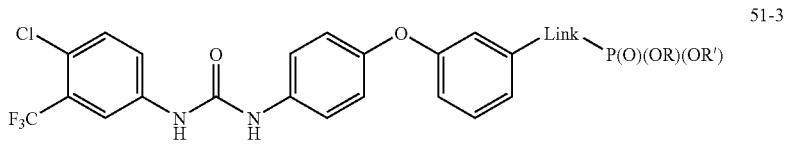

51-3

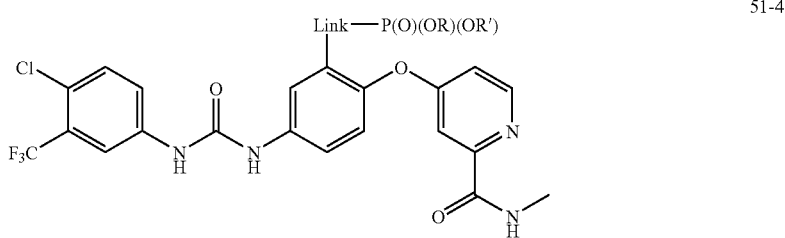

51-4

Link = 1-8 atoms, with 2-6 preferred

Compounds such as these are made according to the general routes outlined in Schemes 51.2, 51.4, 51.6 and 51.8, with specific examples exemplified in Schemes 51.3, 51.5, 51.7 and 51.9.

Scheme 51.2

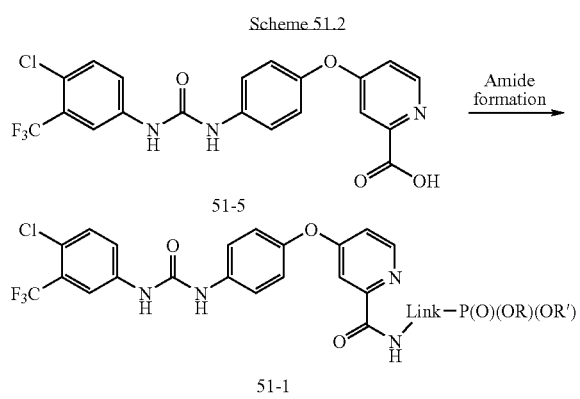

Scheme 51.3

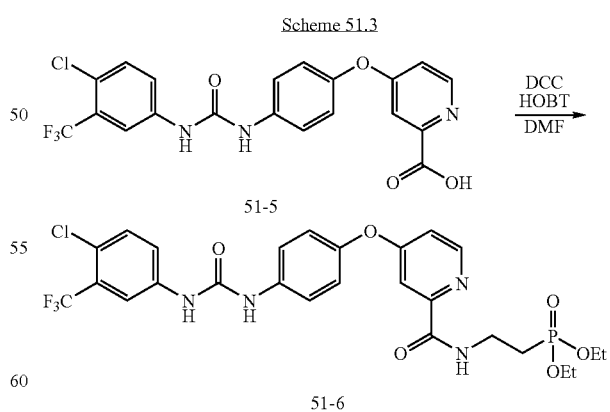

The acid is coupled with 2-aminoethylphosphonic acid diethyl ester (commercially available) using standard reagents for the formation of a secondary amide such as dicyclohexylcarbodiimide (DCC) and hydroxybenztriazole (HOBT), in a solvent such as dimethylformamide.

Scheme 51.4

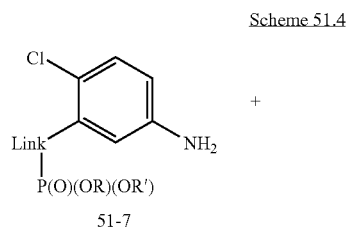

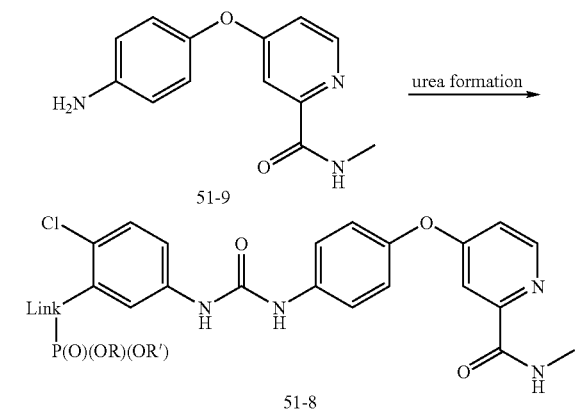

An aniline bearing a phosphonate moiety is coupled with 4-(4-aminophenoxy)-pyridine-2-carboxylic acid methylamide (U.S. Patent No. 2002/0165394) in the presence of a reagent such as phosgene, in a solvent such as toluene to form a urea (see *Bioorg. Med. Chem. Lett.*, (2001), 11, 2775).

4-(4-Aminophenoxy)-pyridine-2-carboxylic acid methylamide is formed by alkylation of (4-hydroxypridine-2-carboxylic acid methylamide with 4-fluoronitrobenzene with a base such as cesium carbonate in a solvent such as dimethylformamide, followed by reduction of the nitro group with tin(II) chloride in a solvent such as ethanol.

The synthesis of a suitable phosphonate-bearing aniline is illustrated in Scheme 51.5.

Scheme 51.5

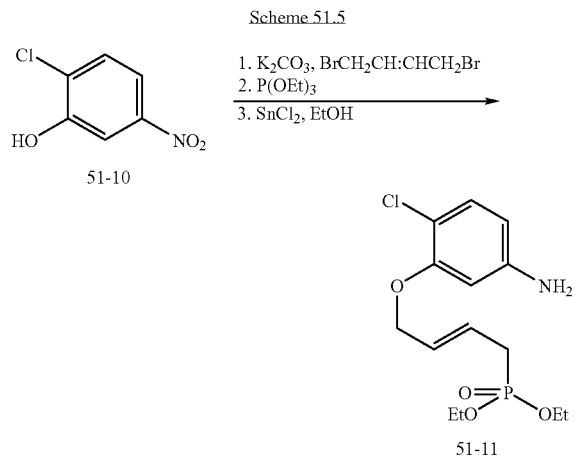

2-Chloro-5-nitrophenol is alkylated with an excess of E-1,4-dibromobutene in a solvent such as dimethylformamide in the presence of a base such as potassium carbonate. The monobromide product is heated with triethylphosphite in a solvent such as toluene (or other Arbuzov reaction conditions: see Engel, R., Synthesis of carbon-phosphorus bonds, CRC press, 1988). Finally, the nitro group is reduced with tin(II) chloride in a solvent such as ethanol.

Scheme 51.6

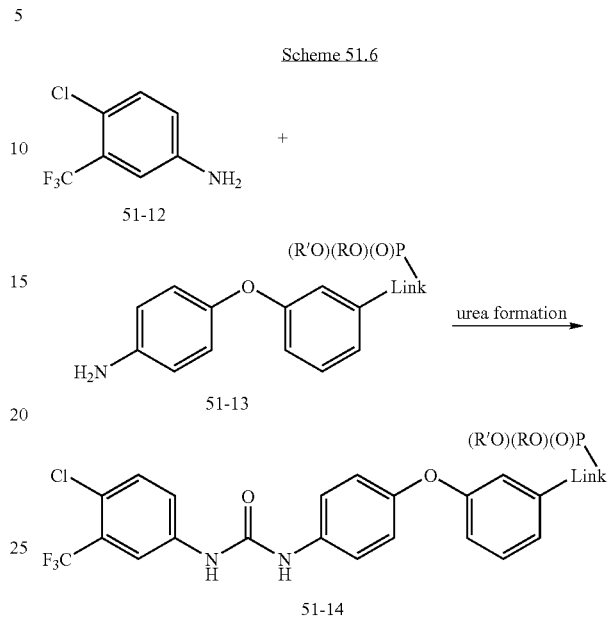

4-Chloro-3-trifluoromethylaniline is coupled with a 4-phenoxy-substituted aniline bearing a phosphonate moiety in a manner similar to that shown in Scheme 51.4 to form a urea. The synthesis of a suitable phosphonate-bearing aniline is illustrated in Scheme 51.7.

Scheme 51.7

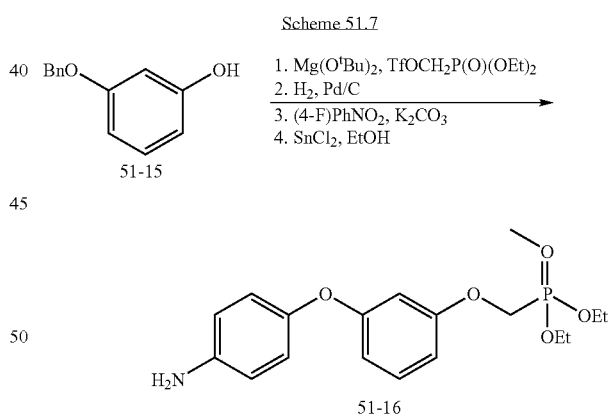

(3-Benzyloxy)phenol is treated with magnesium t-butoxide and diethyl phosphonomethyltriflate (prepared according to *Tetrahedron Lett.*, (1986), 27, 1477) in a solvent such as tetrahydrofuran. The benzyl group is removed by hydrogenation over a catalyst such as palladium on charcoal in a solvent such as methanol as described in Greene, T., Protective groups in organic synthesis, Wiley-Interscience, (1999), and the resulting phenol is alkylated with 4-fluoronitrobenzene with a base such as potassium carbonate in a solvent such as dimethylformamide. Finally, the nitro group is reduced as in Scheme 51.5.

Scheme 51.8

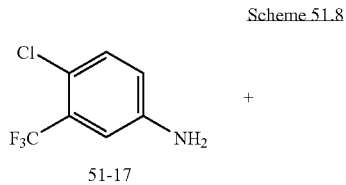

51-17

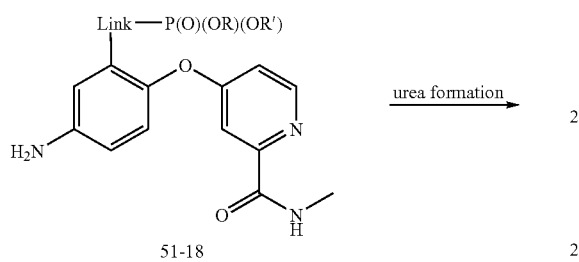

51-18 urea formation →

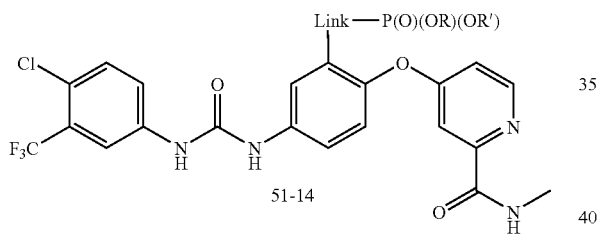

51-14

4-Chloro-3-trifluoromethylaniline is coupled with a 4-phenoxy-substituted aniline bearing a phosphonate moiety in a manner similar to that shown in Scheme 51.4 to form a urea. The synthesis of a suitable phosphonate-bearing aniline is illustrated in Scheme 51.9.

Scheme 51.9

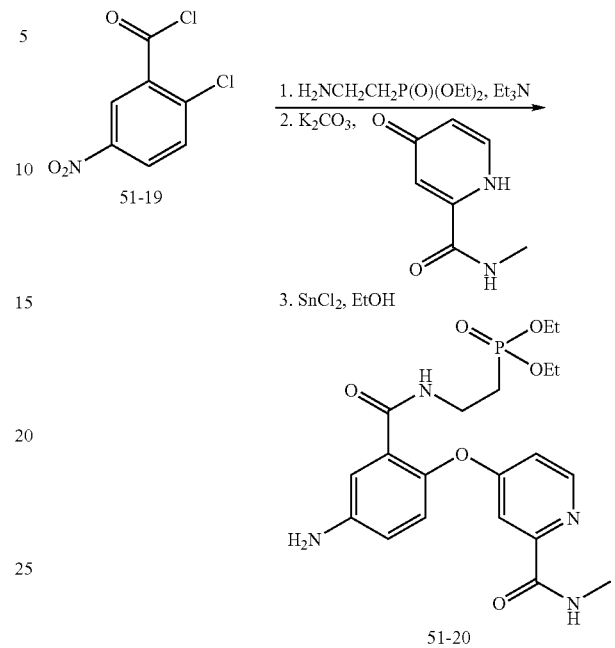

51-19

51-20

2-Chloro-5-nitrobenzoyl chloride is reacted with 2-aminoethylphosphonic acid diethyl ester. Thereafter, displacement of the chloride by reaction with 4-oxo-1,4-dihydro-pyridine-2-carboxylic acid methylamide in the presence of a base such as potassium carbonate in a solvent such as tetrahydrofuran generates the biaryl ether motif, and reduction of the nitro group as in previous examples reveals the aniline ready for coupling in the urea-forming step.

Example 52

Preparation of Exemplary Compounds of the Present Invention

Reduction of the dose and/or improvement of efficacy are achieved by the use of pro-drugs of analogs of SAHA which, upon cleavage inside the target cell, give rise to agents with increased intracellular half-lives. Such phosphonate pro-drug compounds are described below.

Scheme 52.1

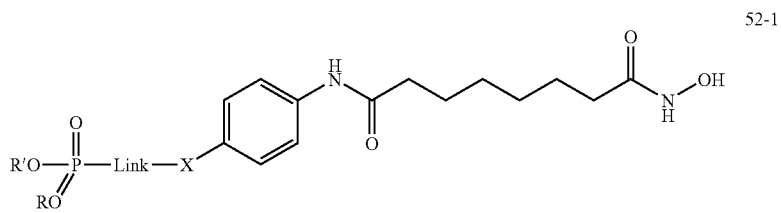

52-1

-continued
52-2
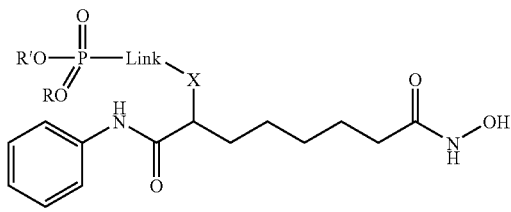
52-3
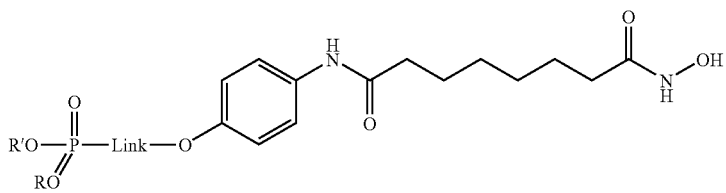
52-4
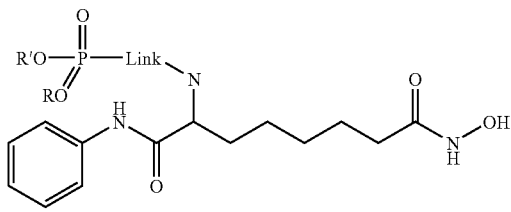
Compounds such as these are made according to the general route outlined in Schemes 52.2 and 52.4, with specific examples depicted in Schemes 52.3 and 52.5.
Scheme 52.2
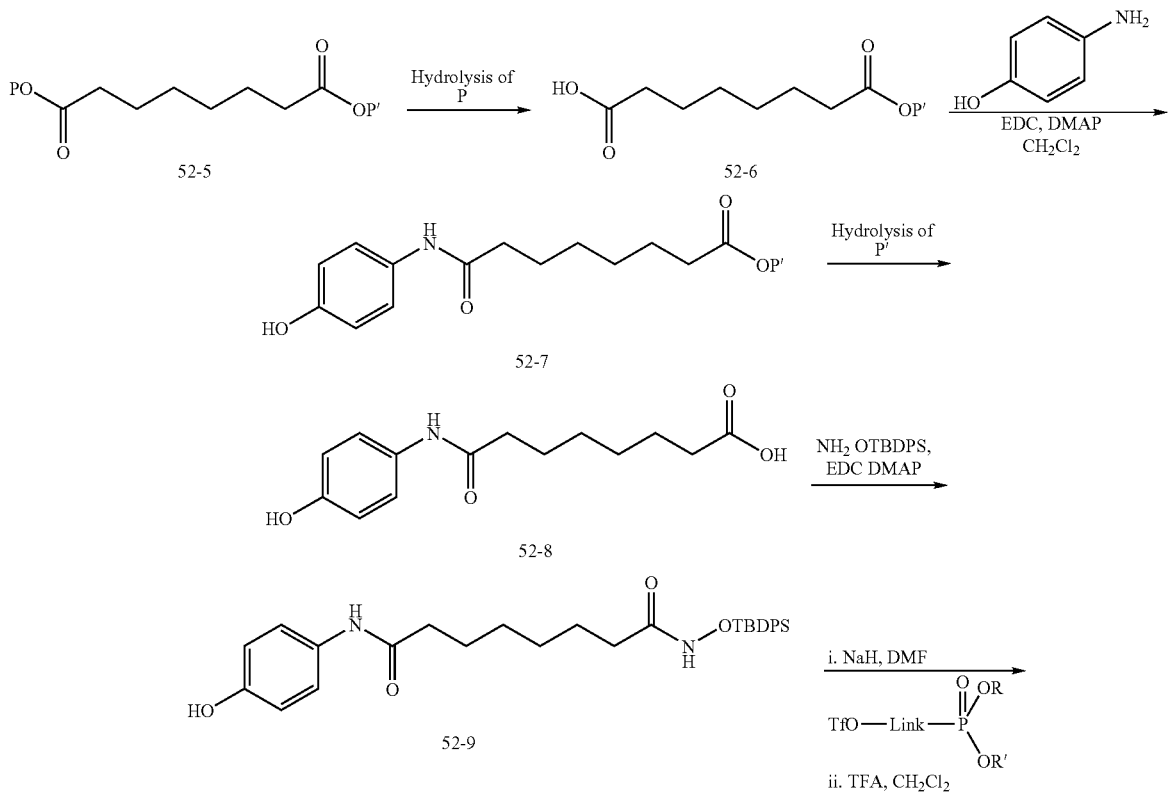

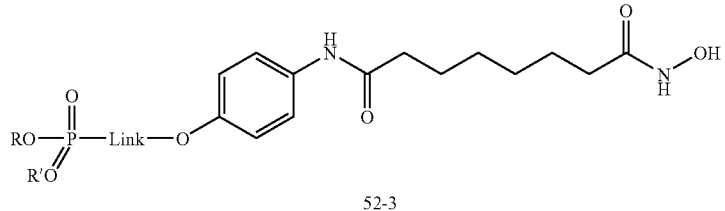

52-3

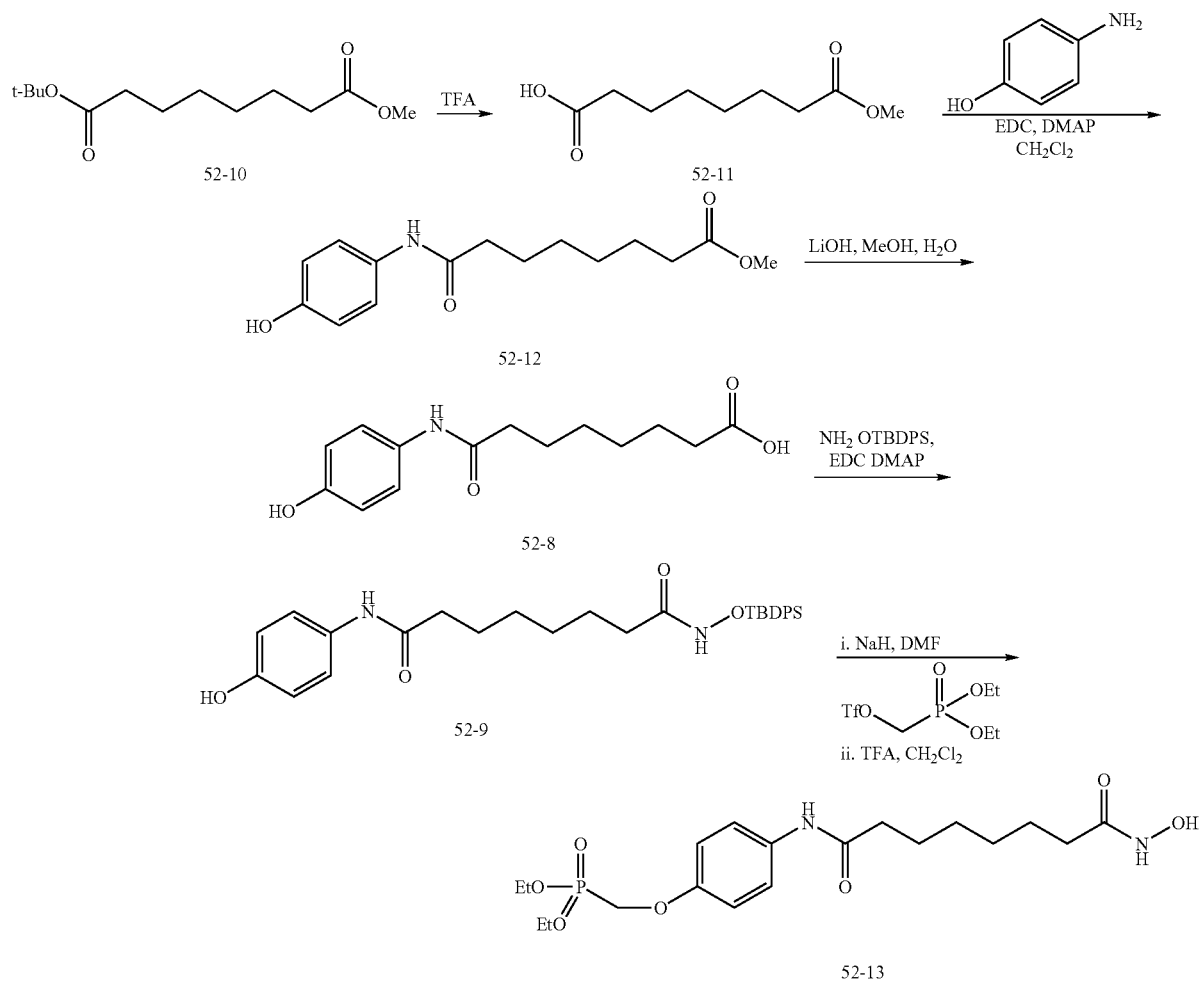

The synthesis of pro-drug 52-3, 52-13 is shown in Scheme 52.2 (WO 118,171 and WO 03,032,921). A differentially-protected octanedioic acid (reported in U.S. Pat. No. 23,232) can be monodeprotected to provide 52-6, 52-11. Coupling of the monoacid with 4-aminophenol using standard peptide coupling conditions provides compound 52-7, 52-12. Hydrolysis of the remaining ester, followed by formation of the protected hydroxamide, gives compound 52-9. The phenolic moiety is utilized for attachment of the pro-drug unit late in the synthesis.

Specifically, octanedioic acid tert-butyl ester methyl ester is monodeprotected using trifluoroacetic acid (TFA) to provide compound 52-6, 52-11. Coupling of the free acid to 4-(methylamino)phenol (Nag, A. et al., *Indian J. Chem. Sect. B.*, (1989), 64, 1 as well as U.S. Pat. No. 2,397,911) provides amide 52-7, 52-12. Hydrolysis of the methyl ester can be achieved using LiOH to give the acid 52-8. Formation of the TBDPS-protected hydroxamic acid is performed by peptide coupling conditions using TBDPSO-NH$_2$, a carbodiimide such as EDC, and N-N-dimethylaminopyridine to form compound 52-9. Phenol 52-9 can be treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the protected phosphonate diester 52-3, 52-13. Removal of the TBDPS group can be achieved using TFA to yield compound 52-3, 52-13.

Scheme 52.4

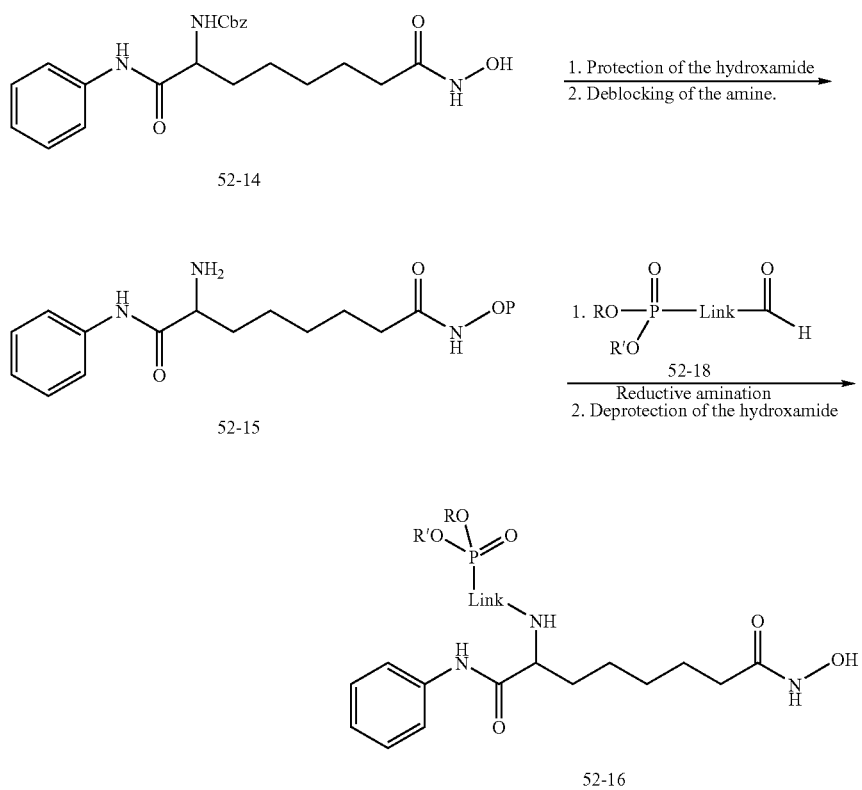

Compound 52-4, 52-16, 52-17 can be prepared from the advanced intermediate 52-14 reported in WO 0118171. Protection of the hydroxamide followed by removal of the Cbz group provides compound 52-15, 52-19. A reductive amination using aldehyde 52-18, 52-20 (from Digital Specialty Chemicals), followed by removal of the protecting group at the hydroxamide provides pro-drug 52-4, 52-16, 52-17.

Scheme 52.5

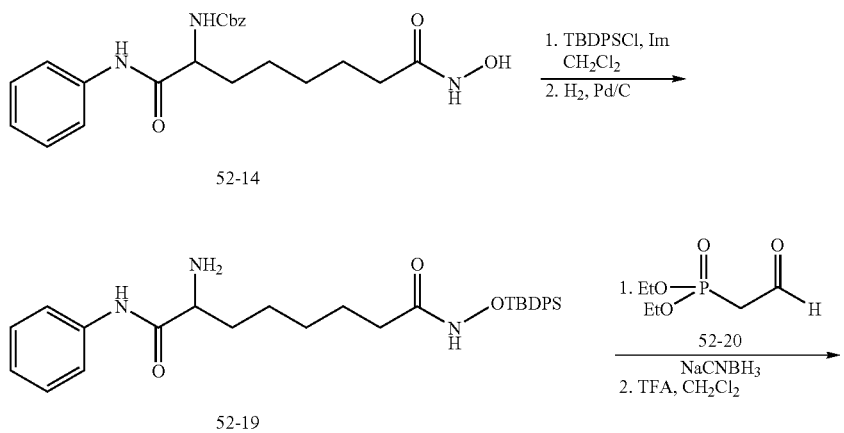

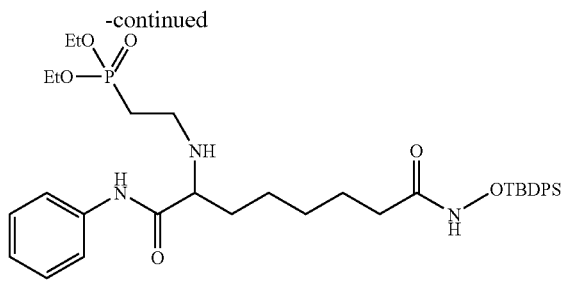

52-17

The Cbz protected 52-14 can be prepared as described in WO 0118171. Blocking the hydroxamide using TBDPS (Greene, T., Protective groups in organic synthesis, Wiley-Interscience, (1999)) followed by removal of the Cbz group provides compound 52-15, 52-19. The free amine of 52-15, 52-19 can undergo a reductive amination with aldehyde 52-18, 52-20, available from Digital Specialty Chemicals (also reported in Olson, G. L. et al., J. Med. Chem., (1995), 38, 15, 2866) to form the pro-drug 52-4, 52-16, 52-17.

Example 53

Preparation of Exemplary Compounds of the Present Invention

Reduction of the dose and/or improvement of efficacy are achieved by the use of pro-drugs of analogs of thalidomide which, upon cleavage inside the target cell, give rise to agents with increased intracellular half-lives. Such compounds are described below.

Scheme 53.1

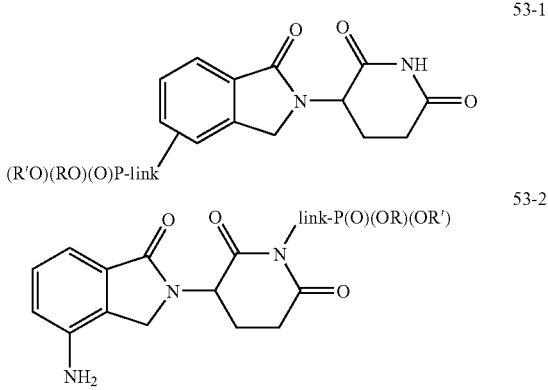

link includes 1 or more atoms; 2 or more is preferred

Compounds such as these are made according to the general routes outlined in Scheme 53.2, with examples depicted in Scheme 53.3.

Scheme 53.2

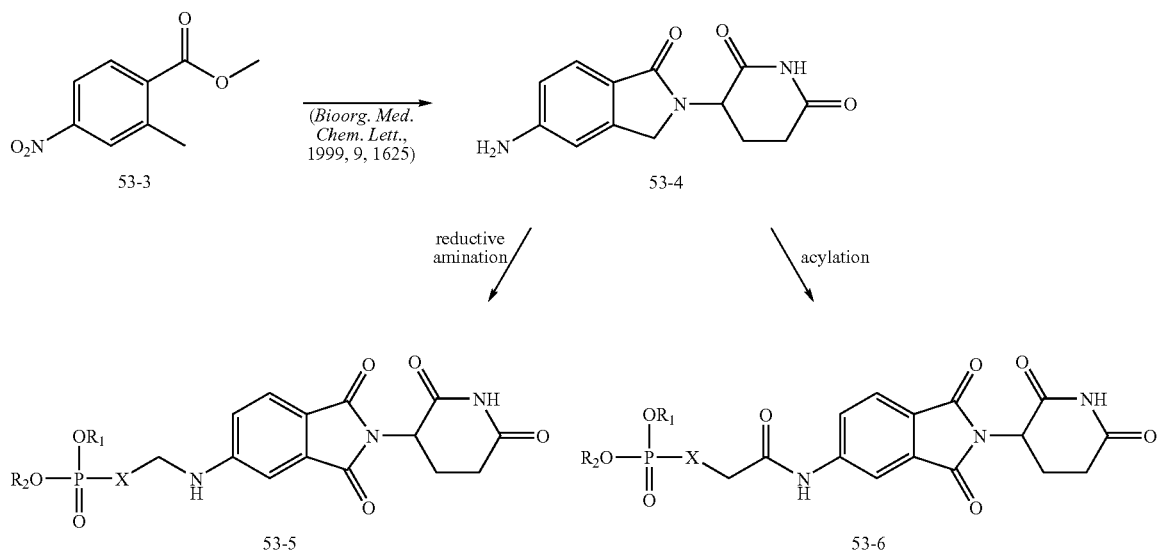

-continued
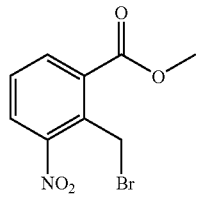 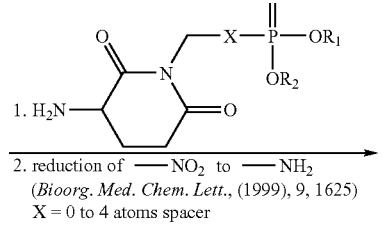 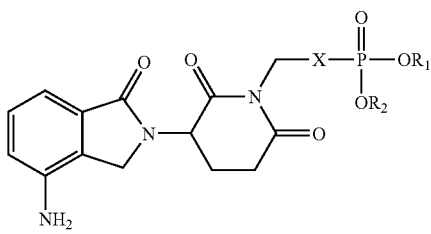
53-7
1. H₂N-
2. reduction of —NO₂ to —NH₂
(*Bioorg. Med. Chem. Lett.*, (1999), 9, 1625)
X = 0 to 4 atoms spacer
53-8
Scheme 53.3
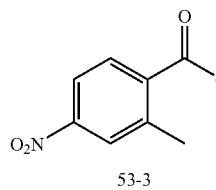 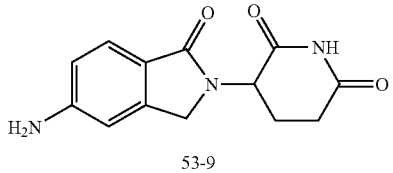
53-3
53-9
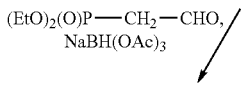 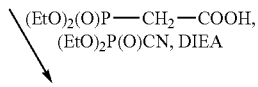
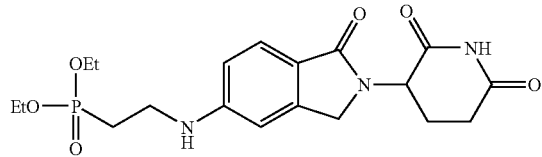 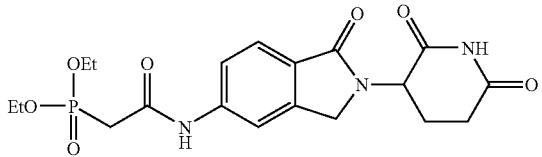
53-10
53-11
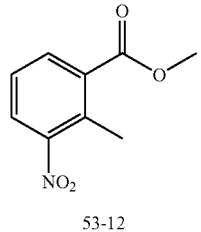 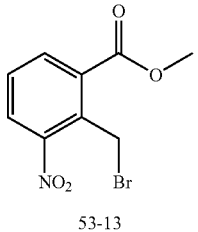 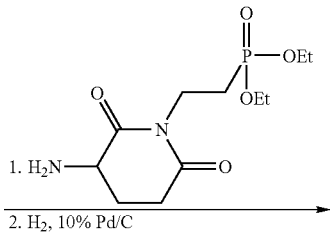
53-12
NBS
53-13
1. H₂N-
2. H₂, 10% Pd/C
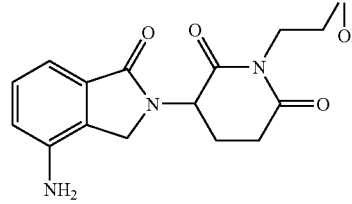
53-14

2-Methyl-4-nitrobenzoic acid methyl ester (commercially available) is converted to 3-(5-amino-1-oxo-1,3-dihydro-isoindol-2-yl)-piperidine-2,6-dione, following the procedures reported in *Bioorg. Med. Chem. Lett.*, (1999), 9, 1625. This amine intermediate is subjected to a reductive amination with diethylphosphonoacetaldehyde (obtained from ozonolysis of diethyl allylphosphonate) in the presence of a reducing agent such as sodium triacetoxyborohydride to generate the desired amine linker analog (*J. Org. Chem.*, (1996), 61, 3849). Alternatively, the amine is acylated with an activated diethylphosphonoacetic acid to provide the desired amide linker compound, according to a procedure such as those reported in *J. Med. Chem.*, (1982), 25, 960 and *J. Med. Chem.*, (1984), 27, 600. The activated diethylphosphonoacetic acid can be obtained by treatment in a solvent such as dimethylformamide with a coupling reagent such as diethyl cyanophosphonate and a base such as diisopropylethylamine at room temperature.

2-Methyl-3-nitrobenzoic acid methyl ester (commercially available) is treated in a solvent such as carbon tetrachloride with N-bromosuccinimide under light to produce 2-bromomethyl-3-nitrobenzoic acid methyl ester. This benzylic bromide is treated in a solvent such as dimethylformamide with [2-(3-amino-2,6-dioxo-piperidin-1-yl)-ethyl]-phosphonic acid diethyl ester (for the preparation of this compound, see below) in the presence of a base such as triethylamine. The coupled product is then reduced by hydrogenation (*Bioorg. Med. Chem. Lett.*, (1999), 9, 1625) to afford the desired analog. [2-(3-amino-2,6-dioxo-piperidin-1-yl)-ethyl]-phosphonic acid diethyl ester is obtained according to a procedure such as that reported in *J. Med. Chem.*, (2003) 46, 3793. Accordingly, benzyloxycarbonyl-protected glutaric acid is treated in a solvent such as acetonitrile with triethylamine, 1-hydroxybenzotriazole, diethyl 2-aminoethylphosphonate and 1,3-dicyclohexylcarbodiimide. After the reaction is complete, the solvent is removed and the residue is purified by chromatography to generate the cyclic product, which is subjected to hydrogen in the presence of palladium catalysis to afford the desired intermediate.

Example 54

Preparation of Exemplary Compounds of the Present Invention

Reduction of the dose and/or improvement of efficacy are achieved by the use of pro-drugs of analogs of MS-275 which, upon cleavage inside the target cell, gives rise to agents with increased intracellular half-lives. Such phosphonate pro-drug compounds are described below.

Scheme 54.1

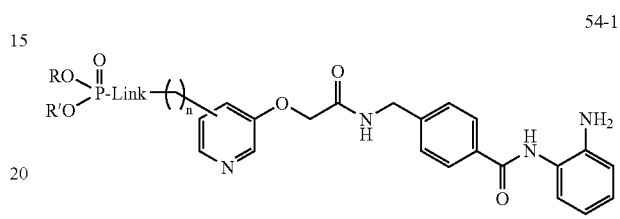

A general structure of a pro-drug.

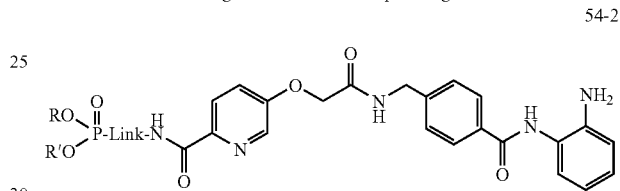

Link = 1-8 atoms, with 2-6 preferred

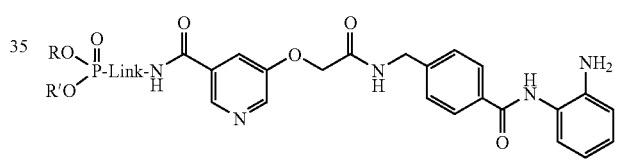

Specific pro-drug attached through ortho or meta positions of the pyridinium ring.

Compounds such as these are made according to the general route outlined in Scheme 54.2, with an example depicted in Scheme 54.3.

Scheme 54.2

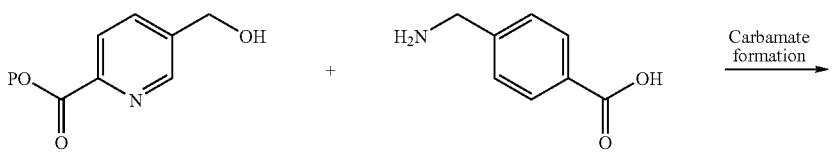

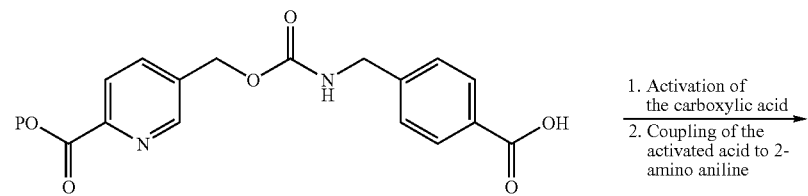

-continued

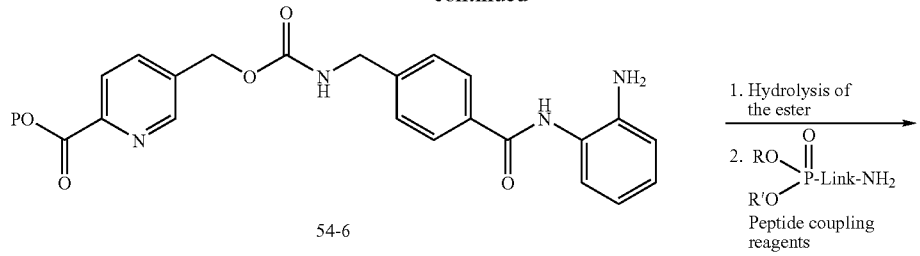

54-6

1. Hydrolysis of the ester
2. RO\\P(O)(OR')-Link-NH$_2$

Peptide coupling reagents

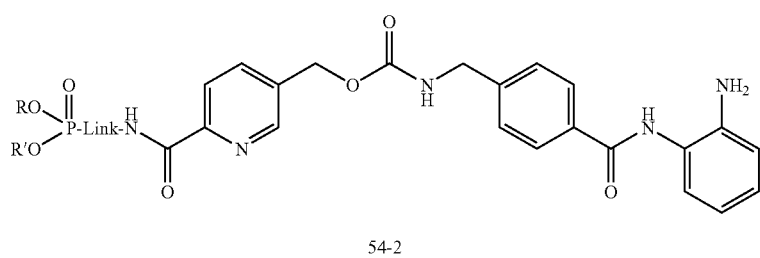

54-2

Preparation of a pro-drug of MS-275 is shown in Scheme 54.2. Compound 54-4 (prepared according to CH 569714 as well as Chem Abstr. 78, 16049) is transformed to the carbamate 54-5 through activation of the alcohol by formation of a carbonyl imidazole intermediate, followed by addition of 4-(aminomethyl)benzoic acid. Subsequent coupling of the carboxylic acid of 54-5 with 2-aminoaniline proceeds to provide compound 54-6. Hydrolysis of the ester followed by coupling of the acid with the amino phosphonate pro-drug completes the synthesis of pro-drug 54-2.

Scheme 54.3

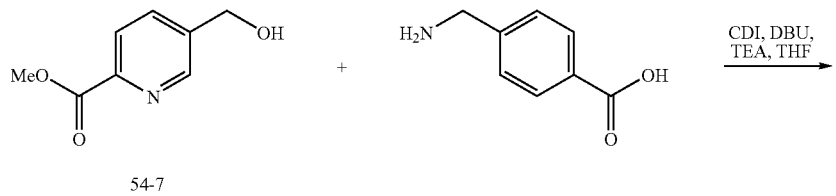

54-7

CDI, DBU, TEA, THF

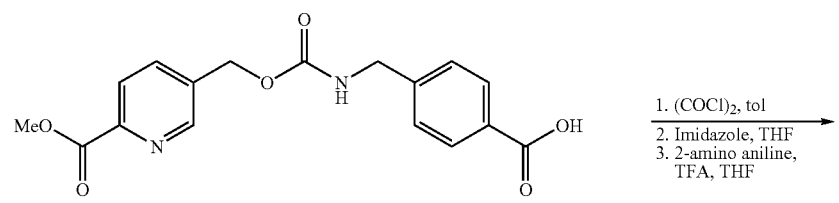

54-8

1. (COCl)$_2$, tol
2. Imidazole, THF
3. 2-amino aniline, TFA, THF

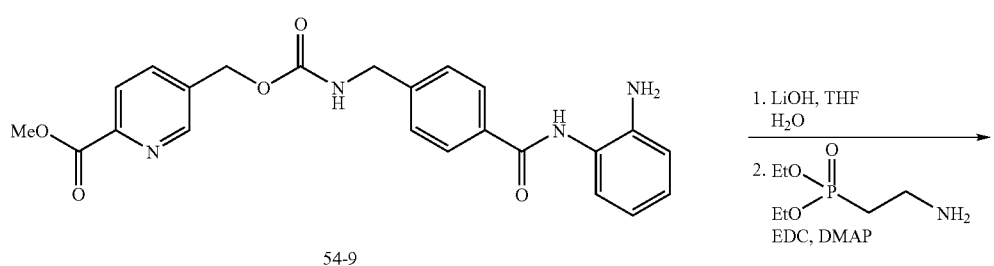

54-9

1. LiOH, THF H$_2$O
2. EtO\\P(O)(OEt)-CH$_2$CH$_2$-NH$_2$
   EDC, DMAP

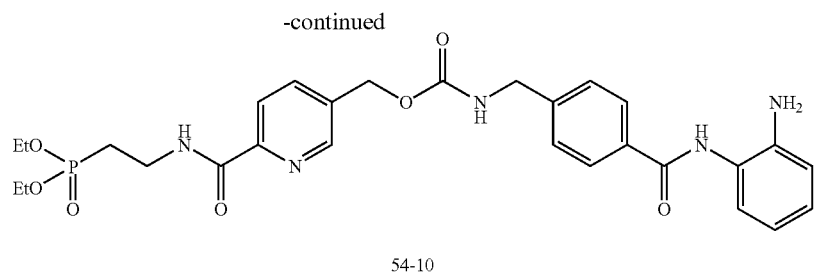

54-10

Preparation of the pro-drug linked MS-275 is shown in Scheme 54.3 in more detail. Compound 54-7 is prepared according to reported methods (CH 569714 as well as Chem Abstr. 78, 16049). Condensation of 54-7 with 4-(aminomethyl)benzoic acid (from Aldrich) using 1,1'-carbonyldiimidazole gives carboxylic acid 54-8 (Suzuki, T. et al., *J. Med. Chem.*, (1999), 42, 3001). Acid 54-8 is converted into acyl chloride by treatment with oxalyl chloride, followed by reaction with imidazole to form the acylimidazole intermediate. This is then reacted with 2-aminoaniline in the presence of trifluoroacetic acid (TFA) to form 54-9. Hydrolysis of the methyl ester followed by coupling with diethyl aminoethylphosphonate (from Fluka) gives pro-drug 54-10.

Formation of the pro-drug 54-3 follows analogous procedures to those described above. The starting material, 5-hydroxymethylnicotinic acid methyl ester, can be prepared according to Hemel J. V. et al., *Nucleosides Nucleotides*, (1996), 15, 1203. The subsequent steps are as shown in Scheme 54.3.

Example 55

Preparation of Exemplary Compounds of the Present Invention

Representative compounds of the invention are made according to the general route outlined in Scheme 55.1, with an example depicted in Scheme 55.2.

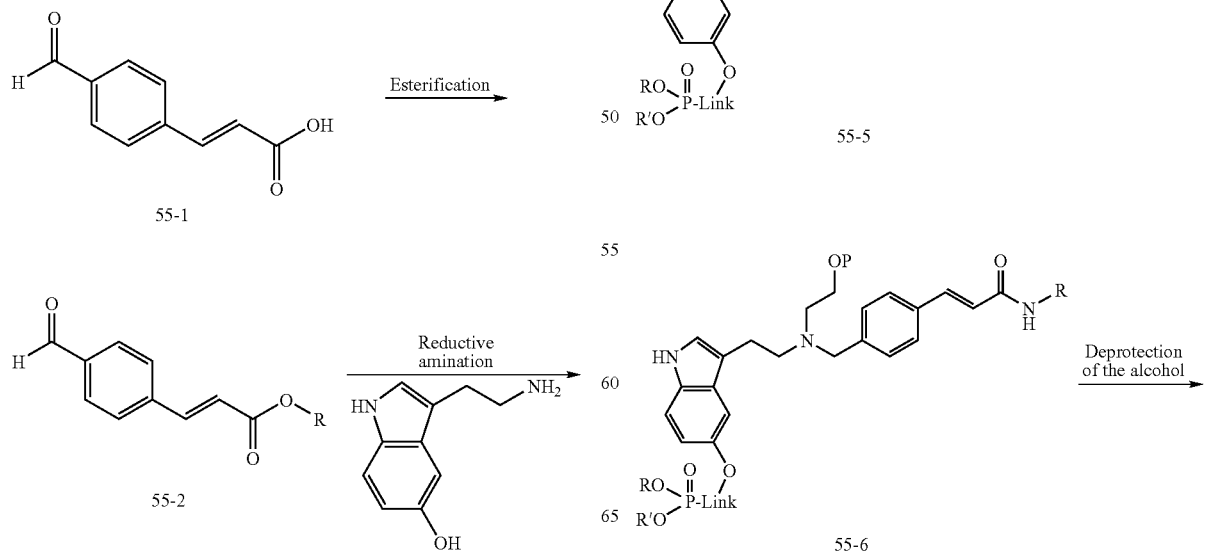

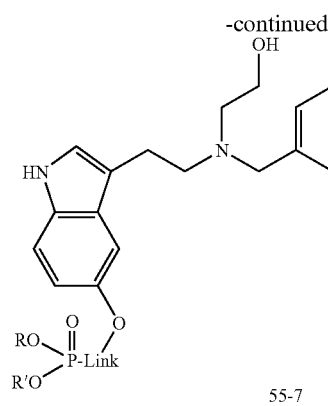

55-7

Preparation of pro-drug 55-7 is shown in Scheme 55.1. Compound 55-1, 4-formylcinnamic acid is first esterified to provide aldehyde 55-2 (WO 03039599). The aldehyde undergoes a reductive amination with 3-(2-aminoethyl)-1H-indol-5-ol (available from Aldrich) to provide compound 55-3. Alkylation of the secondary amine in 55-3 using a protected 2-bromoethanol provides compound 55-4. Phenol 55-4 can be treated in a solvent such as tetrahydrofuran or dimethylformamide with a base such as sodium hydride. When bubbling ceases, a dialkyl phosphonate such as diethyl phosphonomethyltriflate (prepared according to *Tetrahedron Lett.*, (1986), 27, 1477) is added, yielding the desired phosphonate diester 55-5. Formation of the N-hydroxy amide is performed using hydroxylamine in base to provide compound 55-6. Final removal of the protecting group on the primary alcohol provides the pro-drug 55-7.

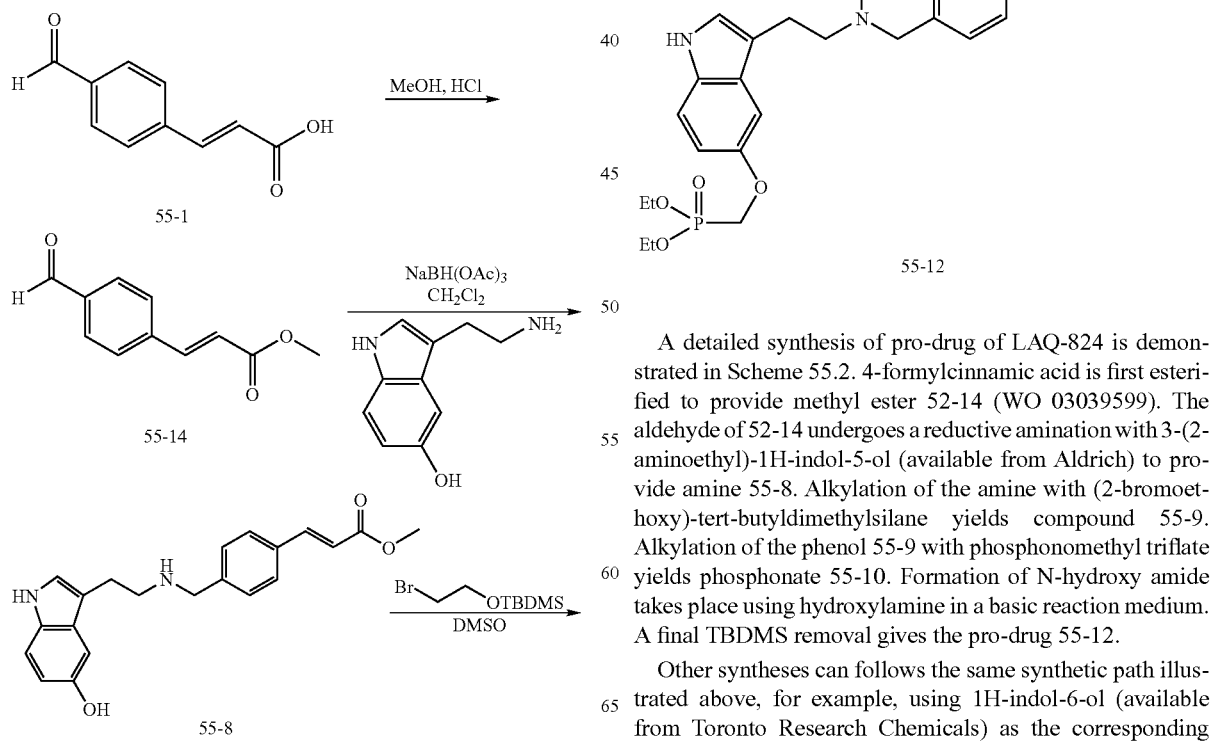

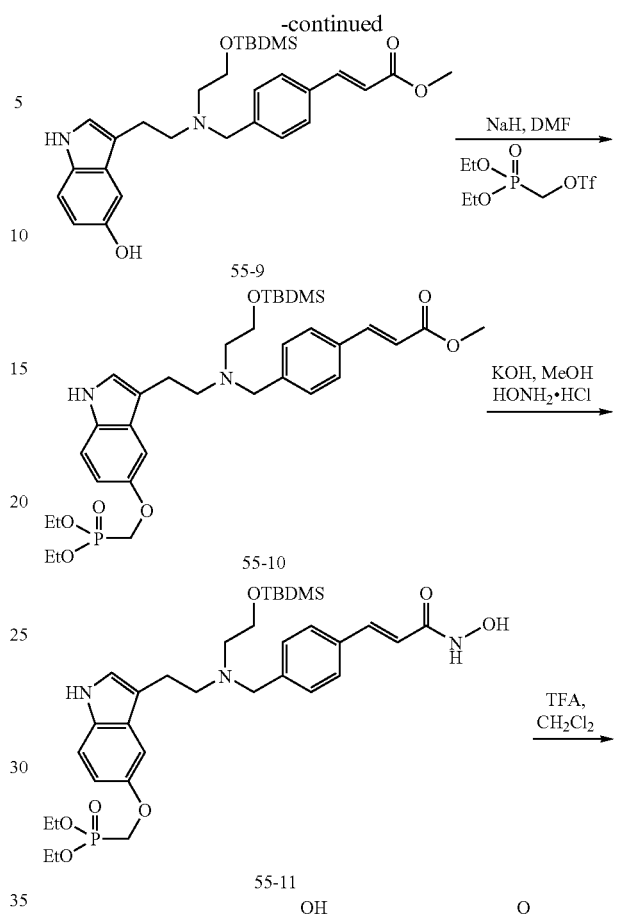

A detailed synthesis of pro-drug of LAQ-824 is demonstrated in Scheme 55.2. 4-formylcinnamic acid is first esterified to provide methyl ester 52-14 (WO 03039599). The aldehyde of 52-14 undergoes a reductive amination with 3-(2-aminoethyl)-1H-indol-5-ol (available from Aldrich) to provide amine 55-8. Alkylation of the amine with (2-bromoethoxy)-tert-butyldimethylsilane yields compound 55-9. Alkylation of the phenol 55-9 with phosphonomethyl triflate yields phosphonate 55-10. Formation of N-hydroxy amide takes place using hydroxylamine in a basic reaction medium. A final TBDMS removal gives the pro-drug 55-12.

Other syntheses can follows the same synthetic path illustrated above, for example, using 1H-indol-6-ol (available from Toronto Research Chemicals) as the corresponding starting material.

Example 56

Preparation of Exemplary Compounds of the Present Invention

Compounds such as these can be made according to the general route outlined in Schemes 56.1 and 56.3, with examples depicted in Schemes 56.2 and 56.4.

The arabinofuranosyl-2-fluoroadenine 56-1 (prepared according to the procedure of Montgomery, J. et al., *J. Med. Chem.*, (1969), 12, 3, 498) is treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester 56.2.

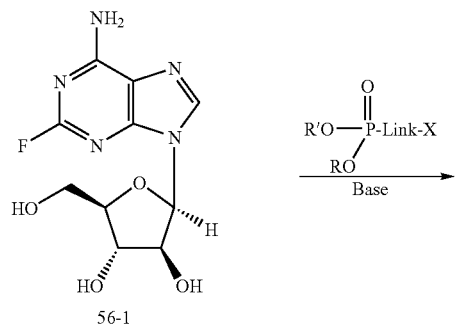

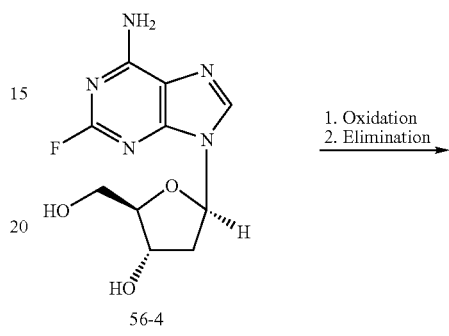

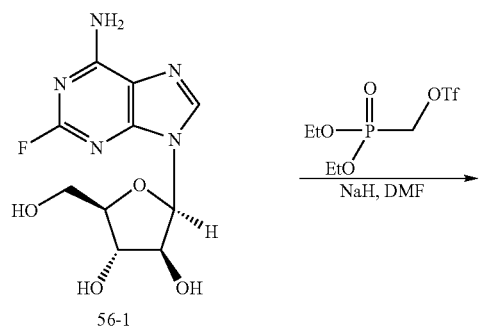

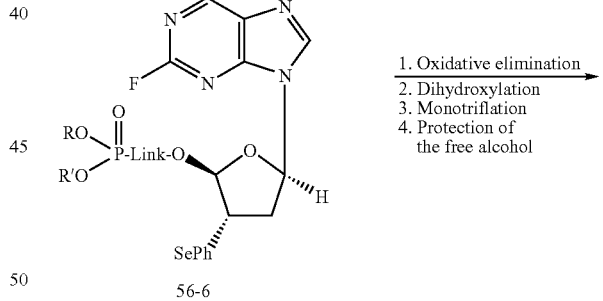

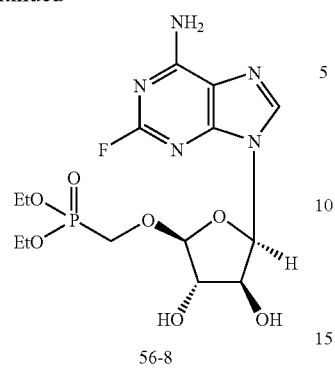

56-8

Preparation of compound 56-8 is described in Scheme 56.3. Compound 56-4 (9-(2-deoxy-α-D-ribofuranosyl)$_2$-fluoroadenine) is prepared as described in Montgomery, J. et. al., *J. Med. Chem.*, (1969), 12, 3, 498 as well as U.S. Pat. No. 4,210,745. Oxidation of the 5'-OH followed by elimination provides glycal 56-5 (see the procedure of Zemlicka J. et al., *J. Am. Chem. Soc.*, (1972), 94, 9, 3213). Protection of the fluoroadenine at the 6 position followed by selenoetherification provides the protected phosphonate 56-6 (Kim, C. et al., *J. Org. Chem.*, (1991), 56, 2642). Oxidative elimination of the phenylselenide (as described in Kim, C. et al., *J. Org. Chem.*, (1991), 56, 2642) followed by stereoselective dihydroxylation provides the diol which is converted to a monotriflate. Protection of the 3' alcohol provides compound 56-7. Conversion of the stereochemistry at the 2' position is achieved by exposing the compound to LiOAc to provide the protected desired stereoisomer of the product. Finally, the protecting groups are removed.

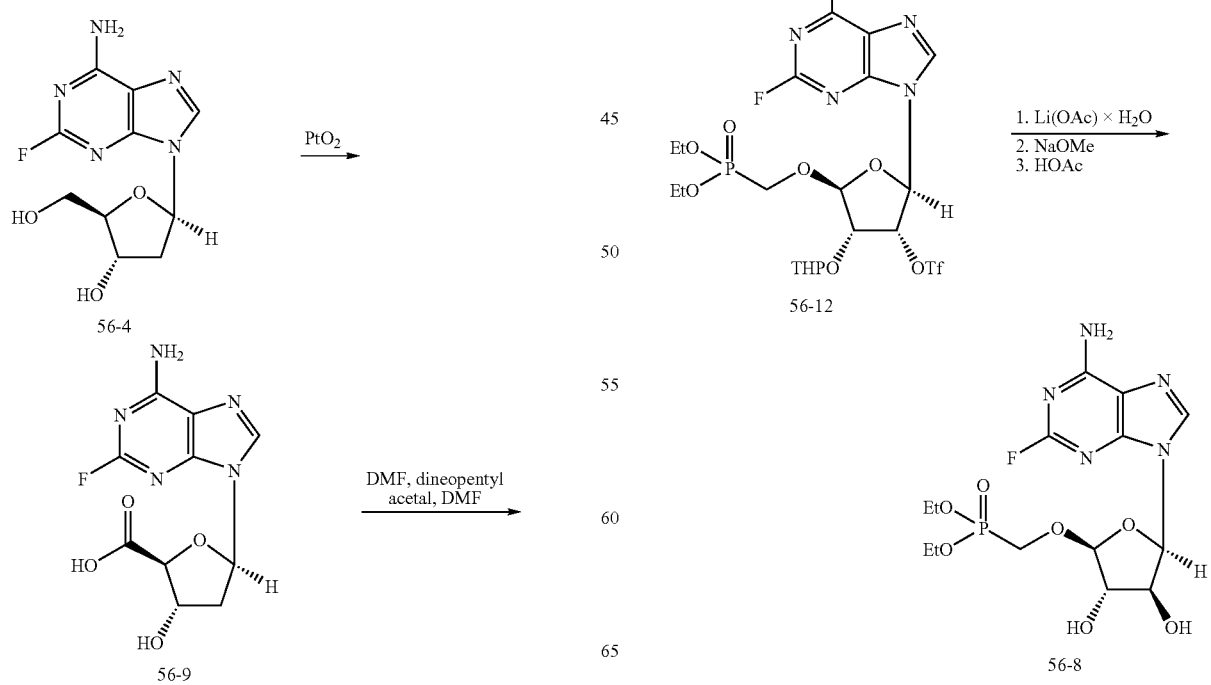

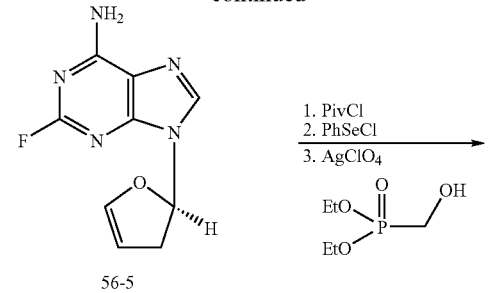

Specifically, 9-(2-deoxy-α-D-ribofuranosyl)₂-fluoroadenine, compound 56-4, (Montgomery, J. et. al., *J. Med. Chem.*, (1969), 12, 3, 498 as well as U.S. Pat. No. 4,210,745) is oxidized with PtO₂ to provide carboxylic acid 56-9. Decarboxylative elimination is achieved using dimethylformamide dineopentyl acetal in DMF at high temperature (Zemlicka J. et al., *J. Am. Chem. Soc.*, (1972), 94, 9, 3213). Once the furanoid glycal 56-5 is in hand, it is first protected at the 6-position of the 2-fluoroadenosine using PivCl conditions as described in Greene, T., Protective groups in organic synthesis, Wiley-Interscience, (1999). Treatment of the protected glycal with silver perchlorate in the presence of diethyl(hydroxylmethyl)phosphonate (Phillion, D. et al., Tetrahedron Lett., 1986, 27, 1477) provides the phosphonate 56.10 (Kim, C. et al., *J. Org. Chem.*, (1991), 56, 2642). Oxidative elimination of the selenide followed by dihydroxylation using osmium tetraoxide provides a diol which can be turned into a mono protected triflate 56-12. Reversal of configuration of the 2' alcohol can be achieved by replacement of the triflate with an acetate group. Deprotection of the pivaloyl group (Greene, T., Protective groups in organic synthesis, Wiley-Interscience, (1999)) removes the newly installed 2' acetate as well. A final deprotection of the THP group can be achieved in acidic media.

Example 57

Preparation of Exemplary Compounds of the Present Invention

Compounds of the invention is prepared as generally described in Scheme 57.1, with an example depicted in Scheme 57.2.

Scheme 57.1

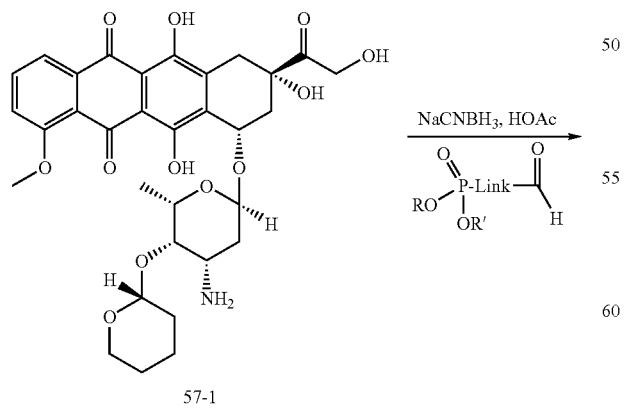

57-1

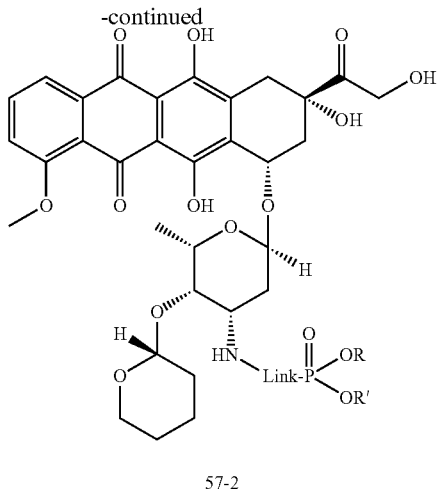

57-2

Scheme 57-2

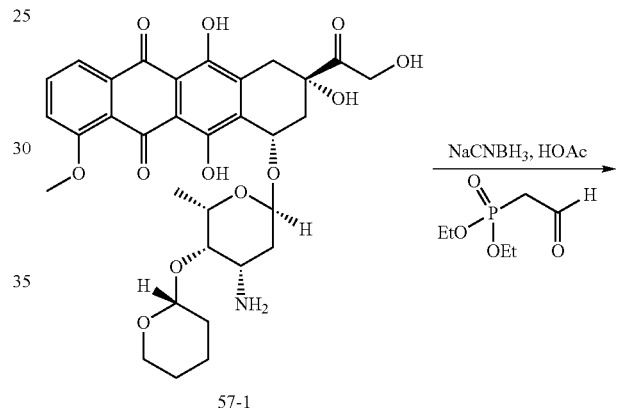

57-1

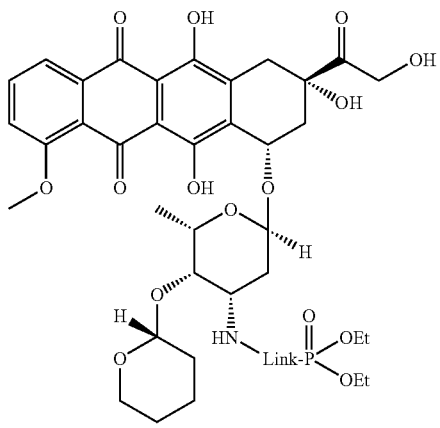

57-3

Preparation of the compound is achieved via reductive amination of a phosphonate-containing aldehyde using Pirarubicin itself. Such aldehydes can be prepared according to *Synth. Commun.* (1992), 22, 2219.

Example 58
Preparation of Exemplary Compounds of the Present Invention
Compounds of the invention are prepared as generally descibed in the following Schemes.
Scheme 58.1
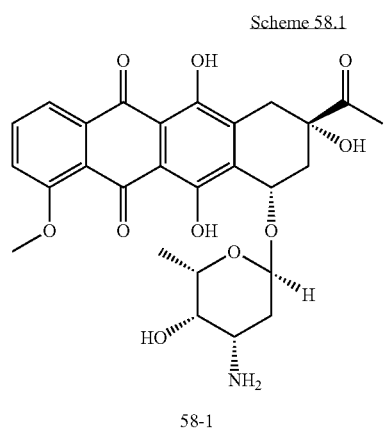
58-1
Protection of the amine →
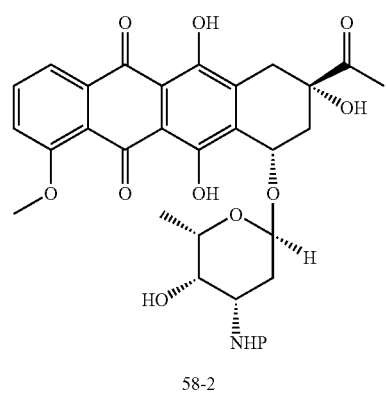
58-2
Alkylation
$$\underset{RO}{\overset{O}{\underset{OR'}{P}}}\text{-Link}\overset{X}{}$$
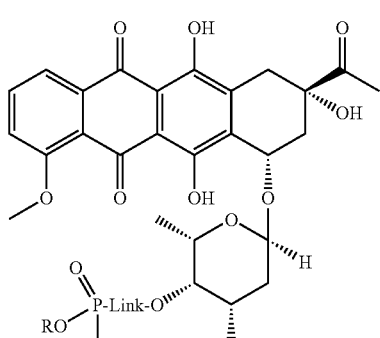
58-3
Deprotection of the amine →
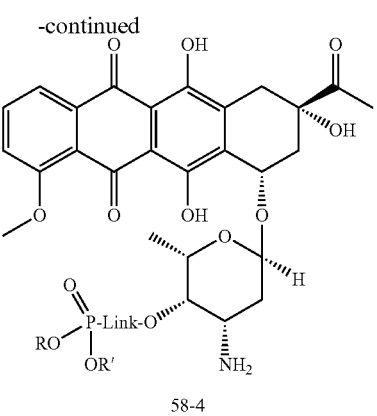
58-4
Scheme 58.2
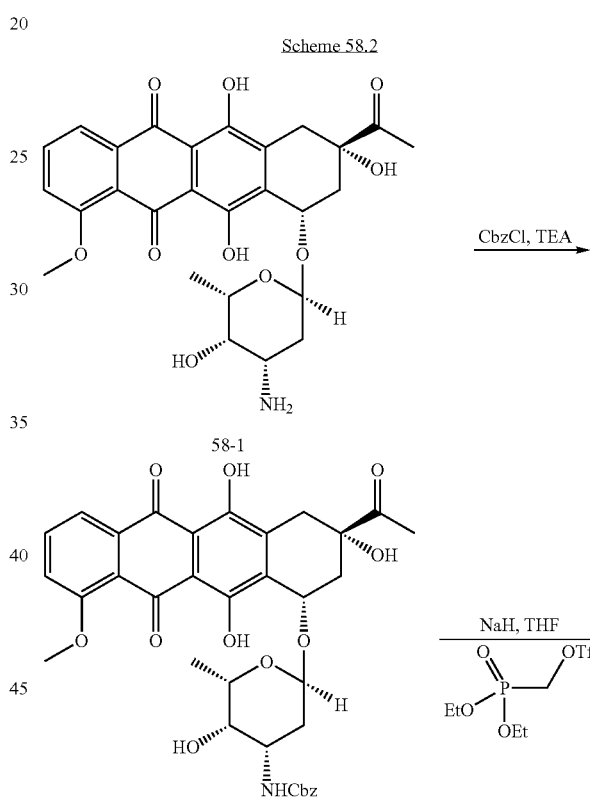
1. H₂, Pd/C →

-continued

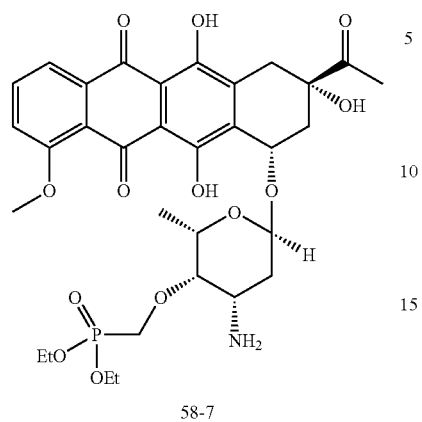

58-7

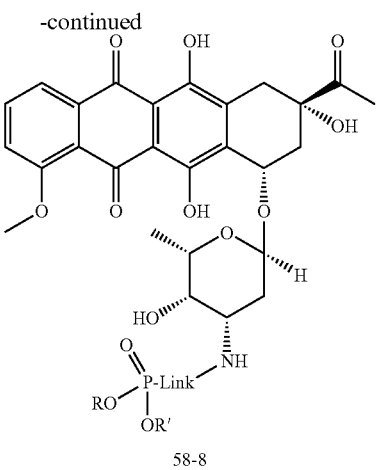

58-8

Daunorubicin is protected on the aminosugar moiety using a Cbz protecting group as described in Greene, T., Protective groups in organic synthesis, Wiley-interscience publication, (1999) to generate 58-7. The alcohol is treated in a solvent such as dichloromethane, tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester 58-6 after purification. Final deprotection by hydrogenation over a catalyst such as palladium on charcoal condition in a solvent such as methanol utilizing the method of Greene et. al. provides the desired product.

Alkyl derivatives of the aminosugar nitrogen have been reported (Farquhar, D. et. al., *J. Med. Chem.*, (1998), 41, 6, 965). Attachment of the phosphonate prodrug moiety onto this amine via alkylation is shown in Scheme 58.3. A specific example of the preparation of 58-9 is provided in Scheme 58.4.

Scheme 58.3

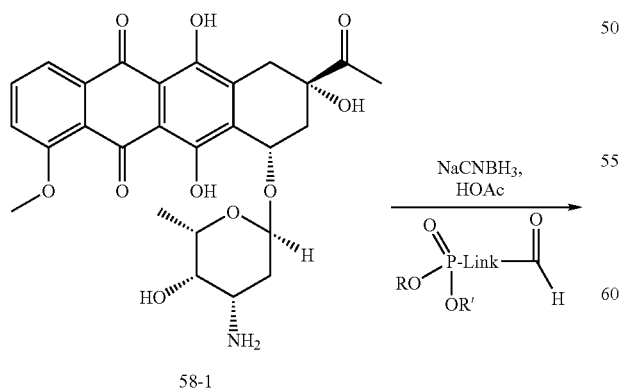

58-1

Scheme 58.4

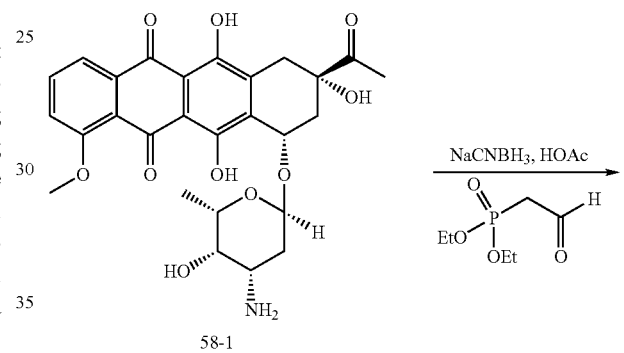

58-1

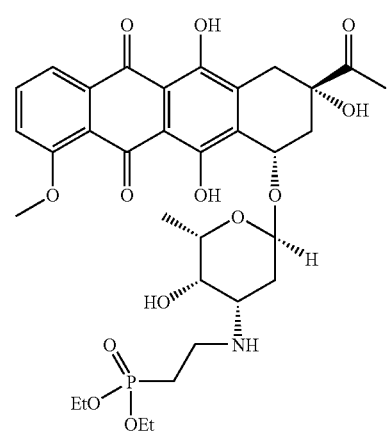

58-9

Preparation of the prodrug 58-9 is achieved via reductive amination of a phosphonate-containing aldehyde using Daunorubicin itself. Such aldehydes are prepared according to *Synth. Commun.* (1992), 22, 2219.

Further manipulations may be performed on the phosphonate moiety prior to the final deprotection. These types of transformations are more extensively described below.

Example 59
Preparation of Exemplary Compounds of the Present Invention
Representative compounds of formulae 59-4, 59-7 can be made according to the general route outlined in Scheme 59.1, with an example depicted in Scheme 59.2.
Scheme 59.1
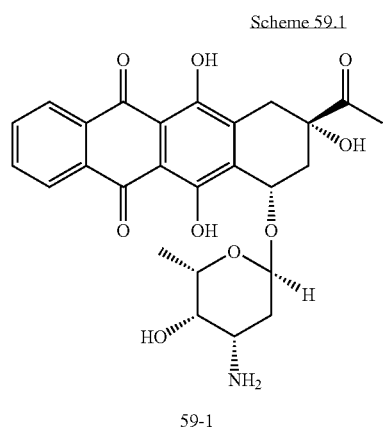
59-1
→ Protection of the amine →
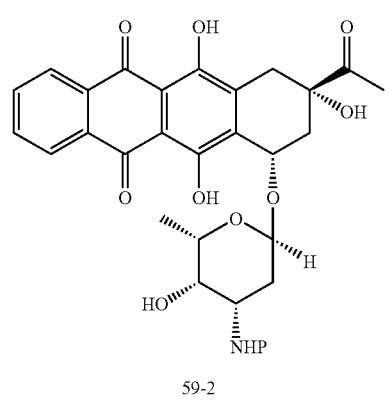
59-2
→ Alkylation
$\underset{RO}{\overset{O}{\underset{OR'}{P}}}\text{-Link-X}$ →
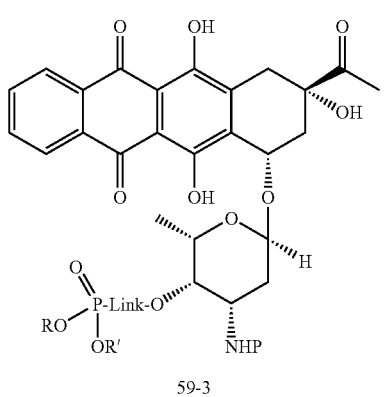
59-3
→ Deprotection of the amine →
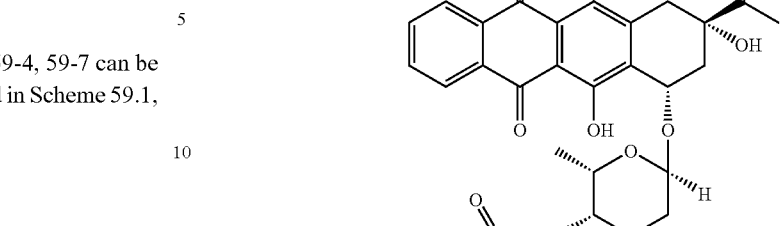
59-4
Scheme 59.2
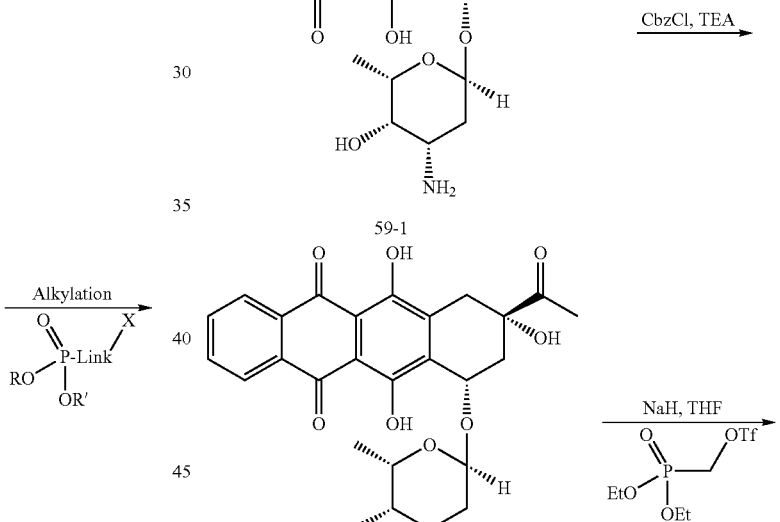

-continued

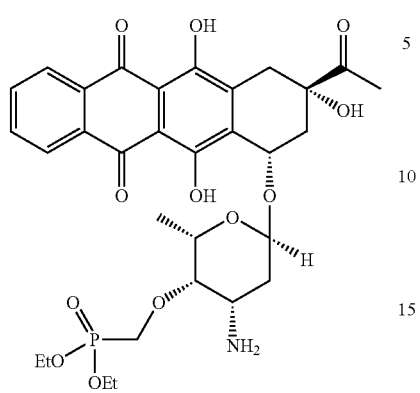

59-7

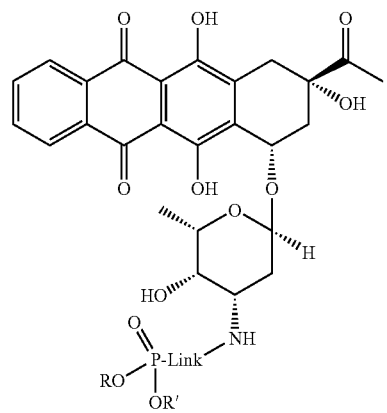

59-8

Idarubicin is protected on the aminosugar moiety using a Cbz protecting group as described in Greene, T., Protective groups in organic synthesis, Wiley-interscience publication, (1999) to generate 59-5. The alcohol is treated in a solvent such as dichloromethane, tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester 59-6 after purification. Final deprotection by hydrogenation over a catalyst such as palladium on charcoal condition in a solvent such as methanol utilizing the method of Greene et. al. provides the desired product.

Alkyl derivatives of the aminosugar nitrogen have been reported (Farquhar, D. et. al., *J. Med. Chem.*, (1998), 41, 6, 965). Attachment of the phosphonate prodrug moiety onto this amine via alkylation is shown in Scheme 59.3. A specific example of the preparation of 59-9 is provided in Scheme 59.4.

Scheme 59.3

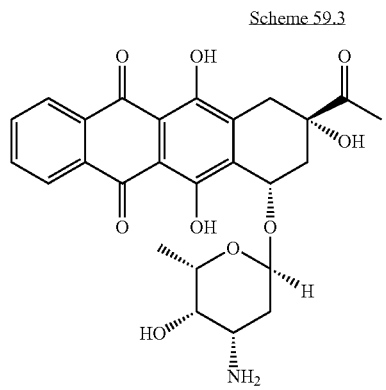

59-1

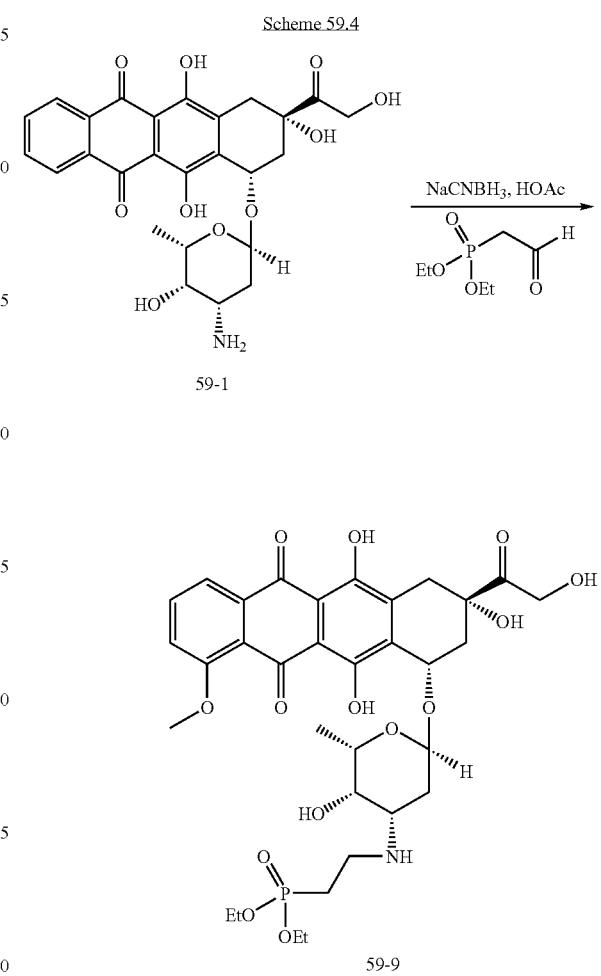

Preparation of the prodrug 59-9 is achieved via reductive amination of a phosphonate-containing aldehyde using Idarubicin itself. Such aldehydes are prepared according to *Synth. Commun.* (1992), 22, 2219.

Example 60

Preparation of Exemplary Compounds of the Present Invention

Representative compounds of the invention can be made according to the general route outlined in Schemes 60.1-60.3, with examples depicted in Schemes 60.4-60.6.

Scheme 60.1: Modification at C7

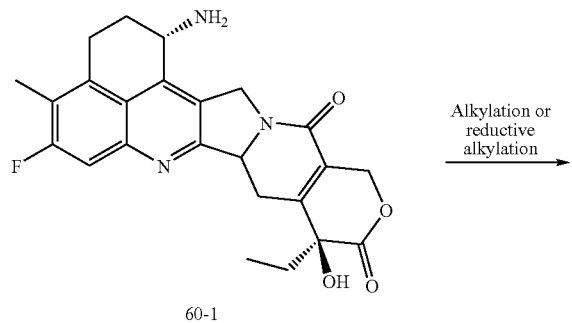

60-1

Alkylation or reductive alkylation →

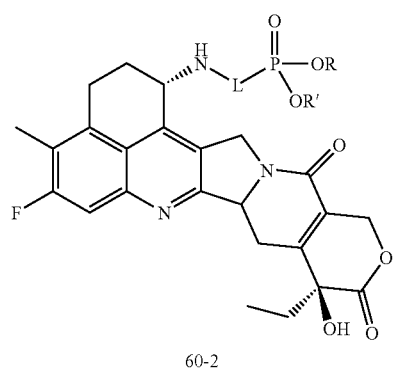

60-2

Scheme 60.2: Functionalization of the nitro group

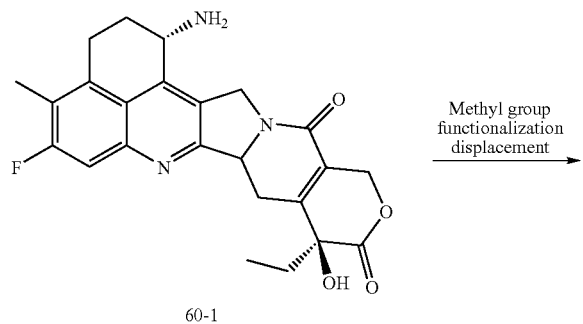

60-1

Methyl group functionalization displacement →

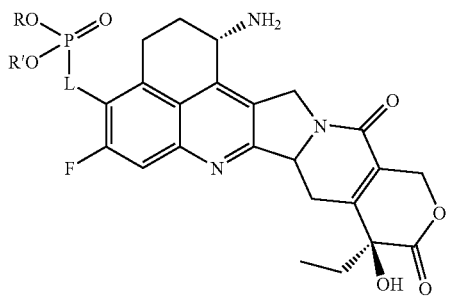

60-3

Scheme 60.3: Modification at C10

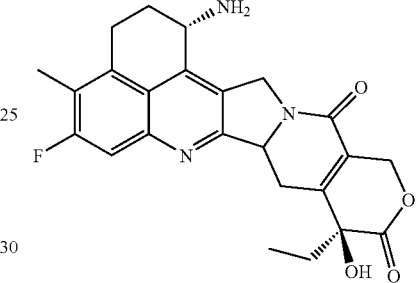

60-1

Fluoride displacement →

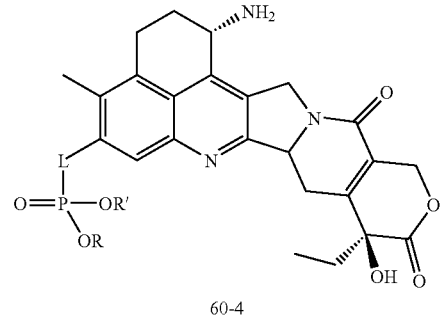

60-4

Scheme 60.4: Modification at C7

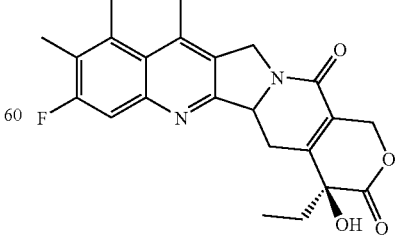 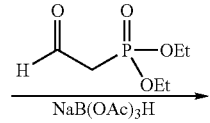

60-1

NaB(OAc)₃H

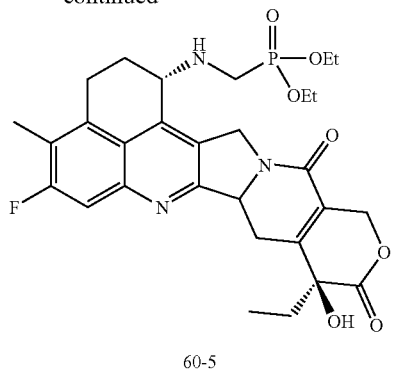

60-5

Exatecan is dissolved in an organic solvent such as tetrahydrofuran (THF), acetonitrile, or dimethylformamide (DMF) and is treated (2-oxo-ethyl)-phosphonic acid diethyl ester (1 equiv.) and sodium triacetoxyborohydride as described in *J. Org. Chem*, ((1996)), 61, 3849-3862. The reaction is quenched with aqueous sodium bicarbonate and the product is extracted with an organic solvent such as ethyl acetate. The product is further purified by chromatography.

Scheme 60.5: Modifications of the nitro group C9

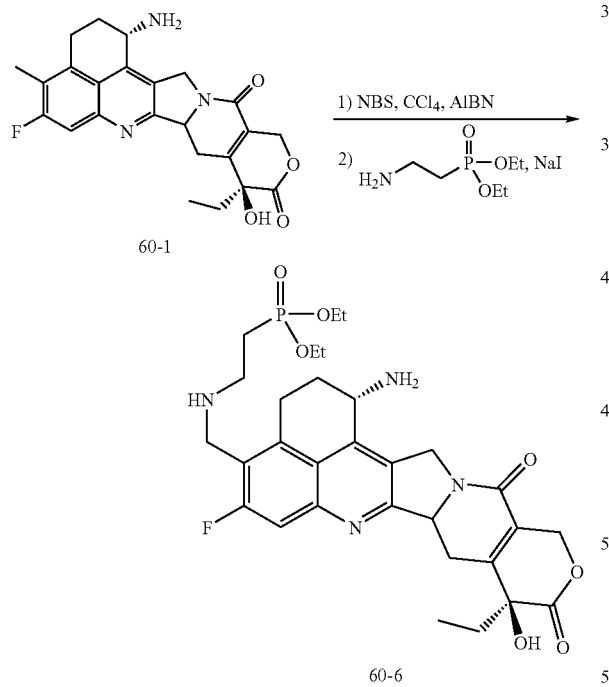

60-1

60-6

Exatecan is dissolved in an organic solvent such as carbon tetrachloride. N-Bromo succinimide (NBS) is added followed by azobisisobutyronitrile (AIBN), according to a procedure from Organikum, 17$^{th}$ edition, Deutscher Verlag der Wissenschaften, (1988), 167. The reaction is heated to reflux temperature for a few hours. At the end of the reaction the mixture is cooled to room temperature. The reaction is filtered and the solvent is removed in vacuo, yielding the crude product. Further separation from regioisomeric products is achieved by chromatography.

The product of step 1 is dissolved in an organic solvent such as acetonitrile or DMF and is treated with aminoethylphosphonic acid diethyl ester (excess), sodium iodide (1 equiv), and sodium carbonate (1 equiv). The reaction mixture is heated to an elevated temperature of 50-60° C. At the end of the reaction, the mixture is cooled to room temperature and is filtered. The crude reaction product is dissolved in an organic solvent such as dichloromethane (DCM), chloroform or benzene and the solution is washed with aqueous hydrochloric acid (HCl) (0.1N), and dried. Filtration and removal of the solvent in vacuo yields the crude product. The product is further purified by chromatography.

Scheme 60.6: Modifications at C10

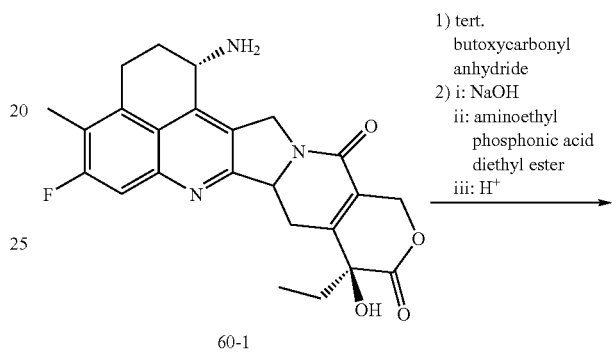

60-1

60-7

Exatecan is dissolved in an organic solvent such as DMF, DCM, or acetonitrile. Tert. butoxycarbonyl anhydride is added, followed by a catalytic amount of 4-dimethylaminopyridine (DMAP) (Green and Wuts, Protective Groups in Organic Synthesis, Wiley and Sons, NY, (1999)). Stirring at room temperature is continued. At the end of the reaction, water is added and the crude reaction mixture is extracted with an organic solvent such as DCM or chloroform and dried. Removal of the solvents yields the crude product. Further purification is achieved by chromatography.

The product of step 1 is dissolved in an organic solvent such as THF, DMF, or chloroform and is treated with aqueous sodium hydroxide (NaOH). Stirring at room temperature is continued until conversion to the opened lactone is observed. The solvent is removed in vacuo and the crude material is dissolved in an organic solvent such as methanol or DMF. Aminoethylphosphonic acid diethyl ester is added and the reaction is heated to reflux for an extended period of time, according to a modification of the procedure from *J. Am. Chem. Soc.*, (1957), 79, 385-391. At the end of the reaction, the mixture is cooled to room temperature and is acidified with aqueous HCl. Stirring is continued until formation of the lactone is observed, according to *J. Am. Chem. Soc.*, (1966), 88, 3888-3890. The solvents are removed in vacuo and the mixture is partitioned between an organic solvent such as chloroform or DCM and aqueous HCl (0.1N). The organic layer is isolated and the solvent is removed in vacuo. The crude material is dissolved in an organic solvents such as DCM or chloroform and is treated with trifluoroacetic acid (TFA) (Green and Wuts, Protective Groups in Organic Synthesis, Wiley and Sons, NY, (1999)). At the end of the reaction, solid sodium bicarbonate is added and the reaction is filtered. The solvents are removed in vacuo. Further product purification is achieved by chromatography.

Example 61

Preparation of Exemplary Compounds of the Present Invention

Representative compounds of the invention can be made according to the general route outlined in Schemes 61.1-61.3, with examples depicted in Schemes 61.4-61.6.

Scheme 61.1: Modification at the ω guanidine nitrogen

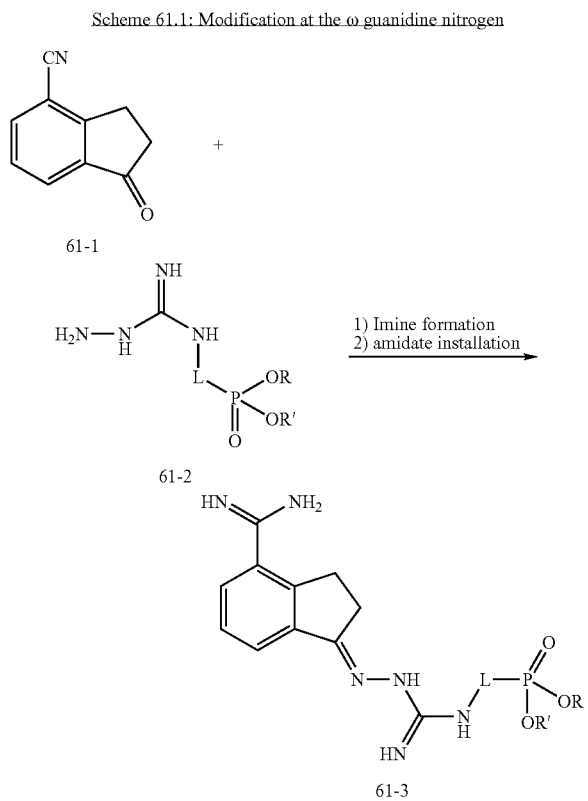

Scheme 61.2: Modification at the α guanidine nitrogen

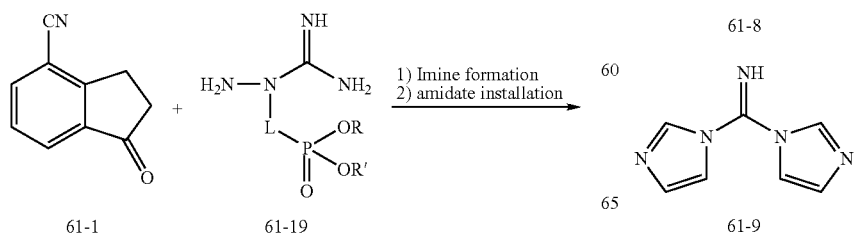

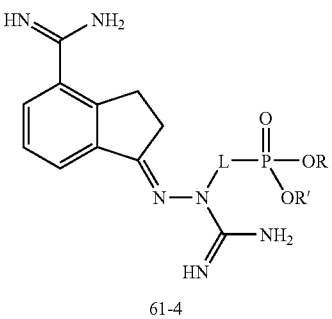

Scheme 61.3: Attachment to C2

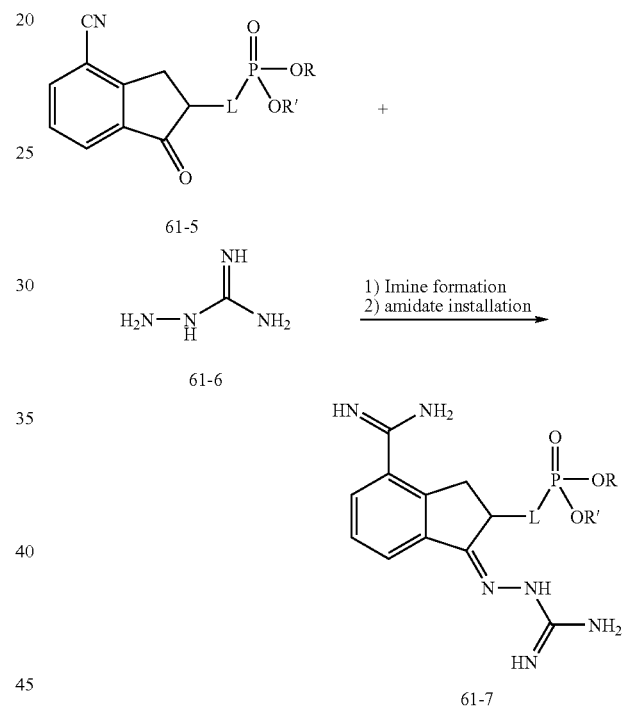

Scheme 61.4: Modification at the ω guanidine nitrogen

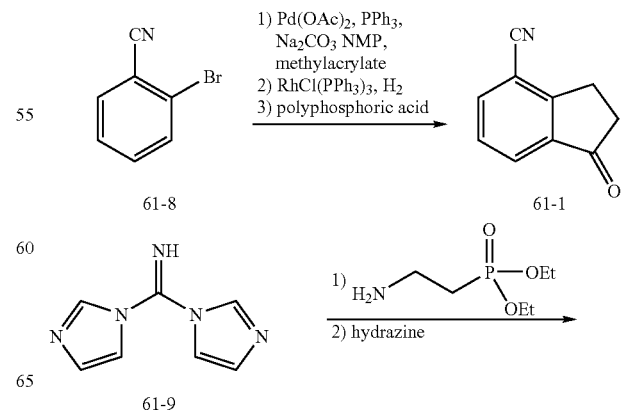

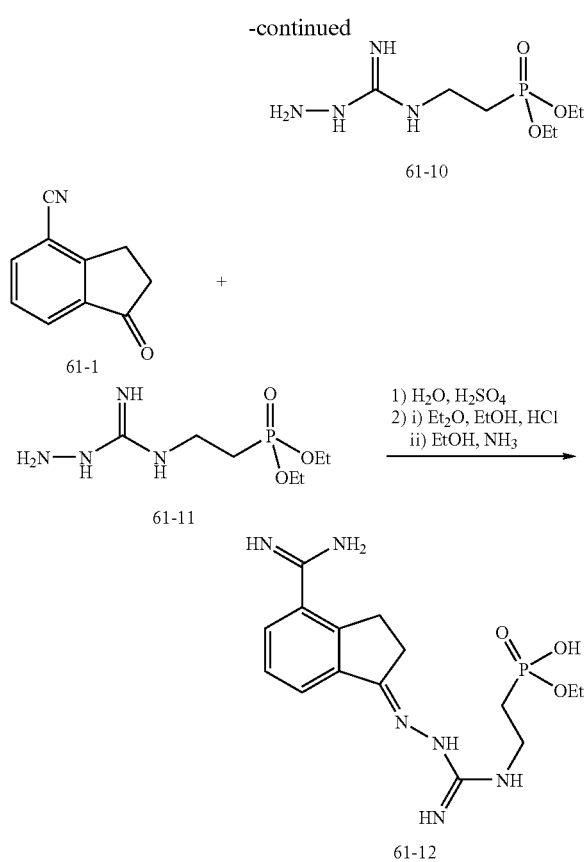

Synthesis of the Aromatic Starting Material (1):

2-Cyanophenylbromide (commercially available) is dissolved in an organic solvent such as N-methylpyrrolidinone (NMP) or dimethylformamide (DMF), under an inert gas atmosphere. Sodium carbonate, triphenylphosphine, and methyl acrylate are added, followed by palladium (II) acetate (Pd(OAc)$_2$). The reaction mixture is heated to an elevated temperature of ~100-140° C., according to procedures from *Chem. Rev.*, (2000), 100, 3009. At the end of the reaction, the reaction mixture is cooled to room temperature, and filtered through Celite. Removal of solvents yields the crude product. Further purification is achieved by chromatography.

The crude material from step one is dissolved in a mixture of organic solvents such as benzene and ethanol under an inert gas atmosphere. Wilkinson's catalyst [RhCl(PPh$_3$)$_3$] is added and the reaction mixture is placed under an hydrogen atmosphere of ~60-80 psi and is heated to an elevated temperature of ~60° C., according to the procedure described in *J. Org. Chem.*, (1969), 34, 3684-3685. At the end of the reaction, the reaction mixture is cooled to room temperature and the solvents are removed in vacuo. The crude material is triturated with diethylether, and the catalyst is removed by filtration through Celite. Removal of the solvent yields the crude material. Further purification is achieved by chromatography.

The crude material of step 2 is dissolved is dissolved in polyphosphoric acid and is heated to an elevated temperature of ~90° C. under an inter gas atmosphere, according to a procedure from *Org. Lett.*, (2001), 3, 279-281. At the end of the reaction, the mixture is cooled to room temperature and is poured onto ice and extracted with an organic solvent such as diethylether. The combined organic extracts are washed with brine and dried. Removal of the solvent yields the crude product. Further purification is achieved by chromatography.

Synthesis of the Guanidine Derivative (2):

Di(imidazol-1-yl)methanimine is dissolved in an organic solvent such as tetrahydrofuran (THF), and is reacted with 2-aminoethyl phosphonic acid diethyl ester at room temperature, according to the procedure described in *J. Org. Chem.*, (2002), 67, 7553-7556. At the end of the reaction, water is added and the product is extracted with an organic solvent such as dichloromethane (DCM). The combined organic layers are washed with saturated aqueous ammonium chloride solution, water and brine, and dried. Removal of the solvents yields the crude material. Further purification is achieved by chromatography.

The product of this step is dissolved in an organic solvent such as DMF and reacted with hydrazine at an elevated temperature of ~100° C. in a sealed vessel, according to a slightly modified procedure from the reference cited above. At the end of the reaction, the mixture is cooled to room temperature and water is added. The product is extracted with an organic solvent such as DCM. The combined organic layers are washed with saturated aqueous ammonium chloride solution, water and brine, and dried. Removal of the solvents yields the crude material. Further purification is achieved by chromatography.

Final Elaboration (3):

The products of reaction sequence (1) and (2) are dissolved in an organic solvent such as ethanol and treated with a catalytic amount of concentrated sulfuric acid. This mixture is heated to reflux for a minimal amount of time, as described in *J. Med. Chem.*, (1993), 36, 46-54. The reaction mixture is cooled to room temperature and the solvent is removed in vacuo. The product is dissolved in an organic solvent such as ethylacetate or chloroform and is washed with water. The organic layer is dried and the solvent is removed in vacuo. Further purification is achieved by chromatography.

The product of this step is dissolved in a mixture of organic solvents such as diethyl ether and ethanol. The solution is saturated with hydrochloric acid gas at 0° C. and is kept at this temperature for an extended period of time. At the end of the reaction product precipitation is induced by the addition of diethyl ether. The precipitate is collected and dried in vacuo. The crude material is dissolved in an organic solvent such as ethanol and ammonium saturated ethanol is added. The mixture is heated to an elevated temperature of ~70° C. for several hours. At the end of the reaction, the mixture is cooled to room temperature and the solvents are removed in vacuo: The product is further purified either by recrystallization from ethanol/diethylether mixtures or by chromatography.

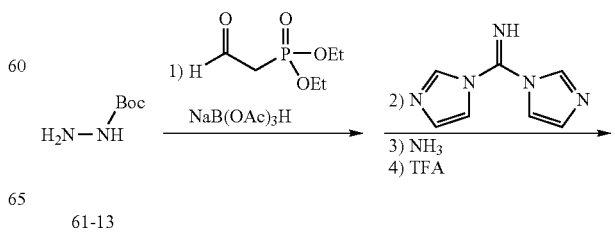

Scheme 61.5: Modification at the α guanidine nitrogen 61-13

-continued

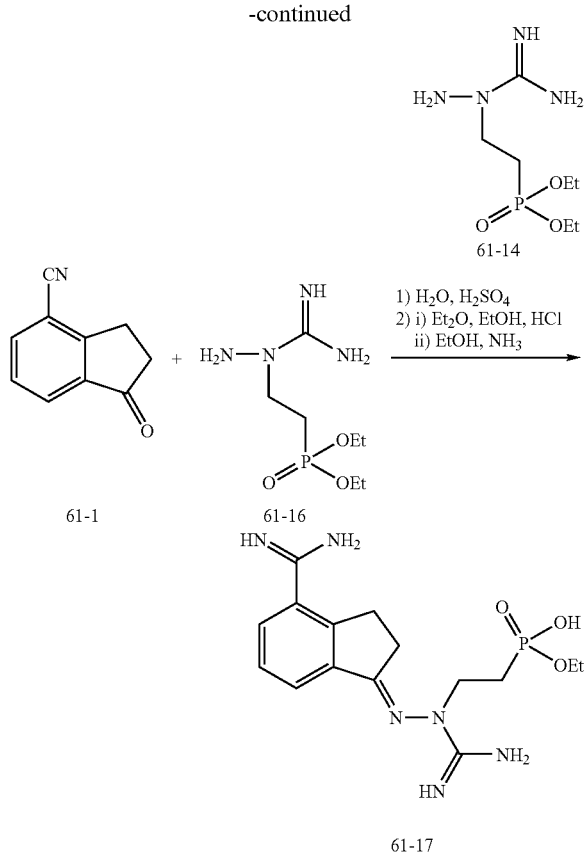

The product of this step is dissolved in an organic solvent such as DCM and is treated with trifluoroacetic acid (TFA), according to a procedure from Green and Wuts, Protective Groups in Organic Synthesis. At the end of the reaction sodium bicarbonate is added and the reaction mixture is filtered. Removal of the solvents in vacuo yields the crude product. Further purification is achieved by chromatography.

Final Elaboration (3):

The products of the above reactions are dissolved in an organic solvent such as ethanol and treated with a catalytic amount of concentrated sulfuric acid. This mixture is heated to reflux for a minimal amount of time, according to the procedure described in *J. Med. Chem.*, (1993), 36, 46-54. The reaction mixture is cooled to room temperature and the solvent is removed in vacuo. The product is dissolved in an organic solvent such as ethyl acetate or chloroform and is washed with water. The organic layer is dried and the solvent is removed in vacuo. Further purification is achieved by chromatography.

The product of this step is dissolved in a mixture of organic solvents such as diethyl ether and ethanol. The solution is saturated with hydrochloric acid gas at 0° C. and is kept at 0° C. for an extended period of time. At the end of the reaction product precipitation is induced by the addition of diethylether. The precipitate is collected and dried in vacuo. The crude material is dissolved in an organic solvent such as ethanol and ammonium saturated ethanol is added. The mixture is heated to an elevated temperature of ~70° C. for several hours. At the end of the reaction, the mixture is cooled to room temperature and the solvents are removed in vacuo. The product is further purified either by recrystallization from ethanol/diethyl ether mixtures or by chromatography.

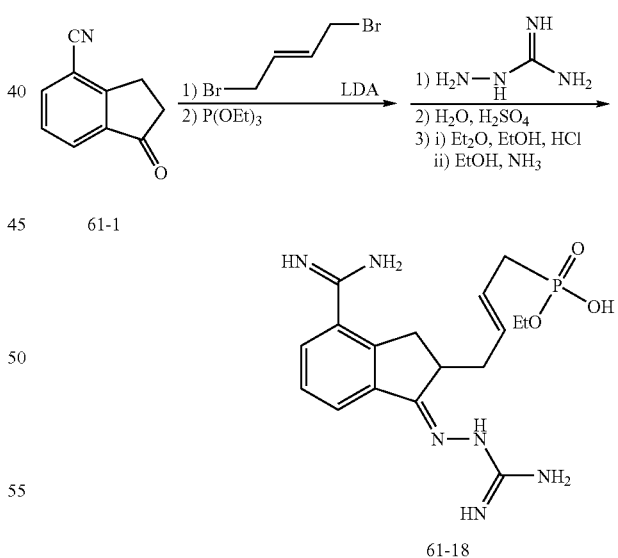

Synthesis of the Guanidine Derivative (1).

Tert. butyl carbazate (commercially available) is treated in an organic solvent such as DCM or THF with diethyl phosphonatoethylcarbaldehyde and sodium triacetoxyborohydride as described in *J. Org. Chem*, (1996), 61, 3849-3862. The reaction is quenched with aqueous sodium bicarbonate and the product is extracted with an organic solvent such as ethyl acetate. Further purification is achieved by chromatography.

The product of this step is dissolved in an organic solvent such as THF, and is reacted with di(imidazol-1-yl)methanimine, according to the procedure described in *J. Org. Chem.*, (2002), 67, 7553-7556. At the end of the reaction, water is added and the product is extracted with an organic solvent such as DCM. The combined organic layers are washed with saturated aqueous ammonium chloride solution, water, brine and are dried. Removal of the solvents yields the crude material. Further purification is achieved by chromatography.

The product of this step is dissolved in an organic solvent such as DMF and reacted with ammonia at an elevated temperature of ~100° C. in a sealed vessel, according to a slightly modified procedure from the reference cited above. At the end of the reaction, the mixture is cooled to room temperature and water is added. The product is extracted with an organic solvent such as DCM. The combined organic layers are washed with saturated aqueous ammonium chloride solution, water and brine, and are dried. Removal of the solvents yields the crude material. Further purification is achieved by chromatography.

The product of sequence (1) in Scheme 61.4 is dissolved in an organic solvent such as THF and the solution is cooled to −78° C. Lithium diisopropylamide solution is added, and the reaction mixture is stirred for a few minutes. When the deprotonation is complete, E-1,4 dibromobutene is added in excess and the reaction is allowed to warm to room temperature. The reaction is quenched with aqueous ammonium chloride solution and the product is extracted with an organic solvent such as ethyl acetate or chloroform. Drying and removal of solvents yields the crude product. Further purification is achieved by chromatography.

The product of this step is heated with triethylphosphite in an organic solvent such as toluene to an elevated temperature of ~110° C., according to procedures outlined in Engel, R., Synthesis of carbon phosphorus bonds, CRC press (1988). At the end of the reaction, the mixture is cooled to room temperature and the solvents are removed in vacuo, yielding the crude product. Further purification is achieved by chromatography.

The product of this reaction and aminoguanidine are dissolved in an organic solvent such as ethanol and treated with a catalytic amount of concentrated sulfuric acid. This mixture is heated to reflux for a minimal amount of time, according to a procedure from *J. Med. Chem.*, (1993), 36, 46-54. The reaction mixture is cooled to room temperature and the solvent is removed in vacuo. The product is dissolved in an organic solvent such as ethyl acetate or chloroform and is washed with water. The organic layer is dried and the solvent is removed in vacuo. Further purification is achieved by chromatography.

The product of this step is dissolved in a mixture of organic solvents such as diethyl ether and ethanol. The solution is saturated with hydrochloric acid gas at 0° C. and is kept at 0° C. for an extended period of time. At the end of the reaction, product precipitation is induced by the addition of diethyl ether. The precipitate is collected and dried in vacuo. The crude material is dissolved in an organic solvent such as ethanol and ammonium saturated ethanol is added. The mixture is heated to an elevated temperature of 70° C. for several hours. At the end of the reaction, the mixture is cooled to room temperature and the solvents are removed in vacuo. The product is further purified either by recrystallization from ethanol/diethyl ether mixtures or by chromatography.

Further manipulations are performed on the phosphonate moiety prior to the final deprotection. These types of transformations are more extensively described in the following section.

Example 62

Preparation of Exemplary Compounds of the Present Invention

Representative compounds of formulae 62-4, 62-7 are made according to the general route outlined in Scheme 62.1, with an example depicted in Scheme 62.2.

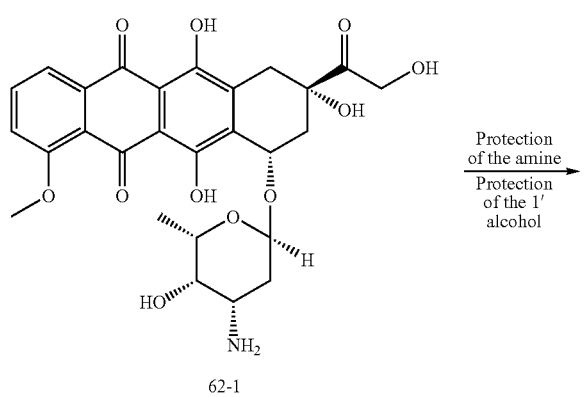

Scheme 62.1

62-1

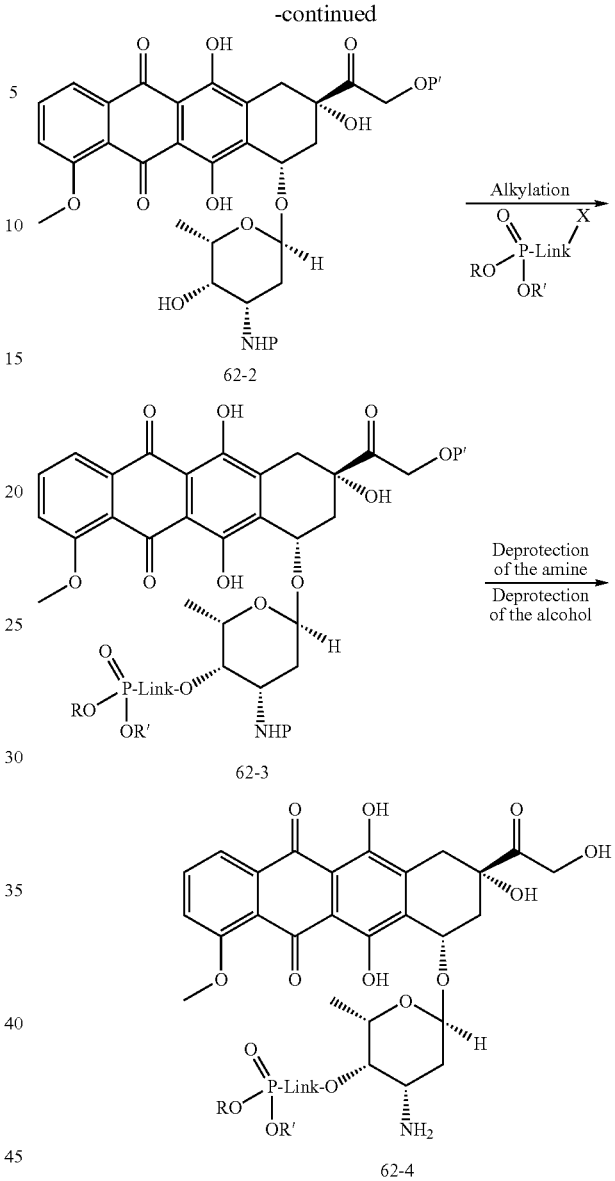

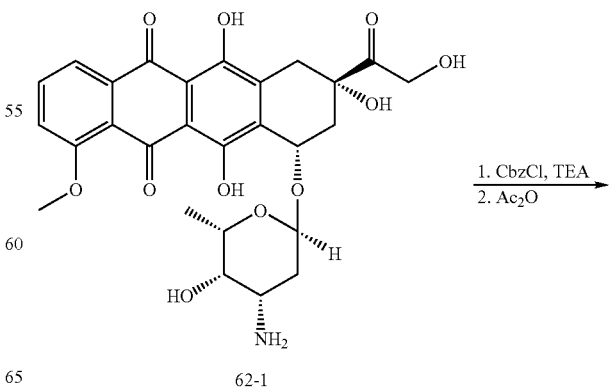

Scheme 62.2

62-1

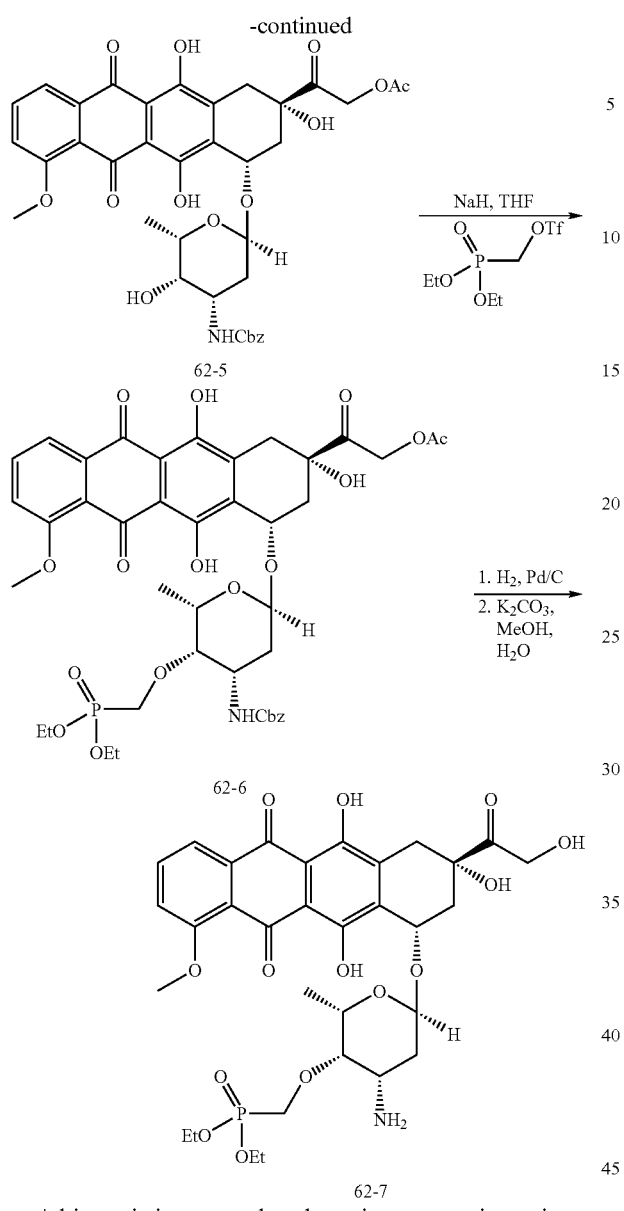

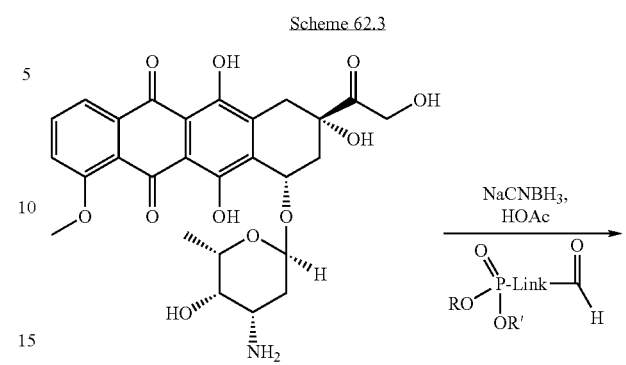

Scheme 62.3

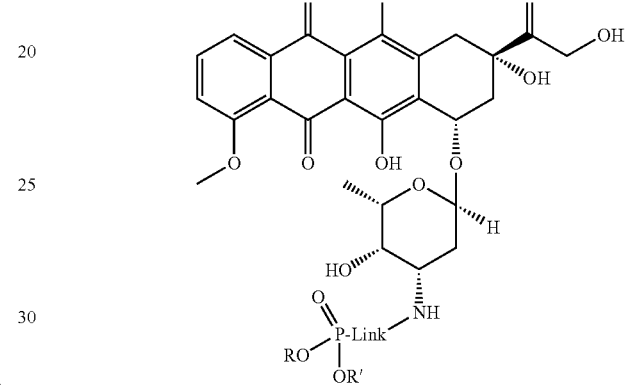

Adriamycin is protected on the aminosugar moiety using a Cbz protecting group as described in Greene, T., Protective groups in organic synthesis, Wiley-interscience publication, (1999). Protection of the primary alcohol to prepare 62-5 using the acetate protecting group has been described (U.S. Pat. No. 4,303,785). The alcohol is treated in a solvent such as dichloromethane, tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester 62-6 after purification. Final deprotection by hydrogenation over a catalyst such as palladium on charcoal condition in a solvent such as methanol utilizing the method of Greene et al. followed by exposure of the compound to potassium carbonate provides the desired product.

Alkyl derivatives of the aminosugar nitrogen have been reported (Farquhar, D. et. al., *J. Med. Chem.*, (1998), 41, 6, 965). Attachment of the phosphonate prodrug moiety onto this amine via alkylation is shown in Scheme 623. A specific example of the preparation of 62-9 is provided in Scheme 62.4.

Scheme 62.4

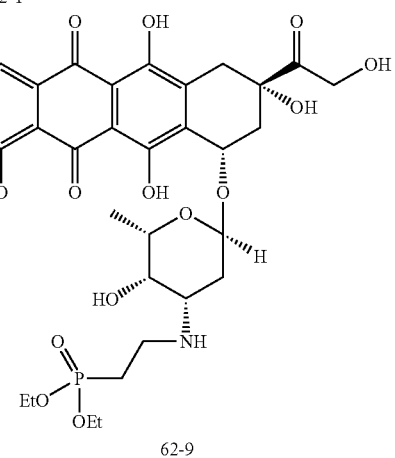

Preparation of the prodrug 62-9 is achieved via reductive amination of a phosphonate-containing aldehyde using Adriamycin itself. Such aldehydes are prepared according to *Synth. Commun.* (1992), 22, 2219.

Example 63

Preparation of Exemplary Compounds of the Present Invention

Background and Utility of Scaffold Compound

Certain triaryl ethylenes are useful in the treatment of hypercholesterolemia and osteoporosis by acting as selective estrogen receptor modulators. One such derivative, Ospemifene, is described in WO01/36360 page 3 line 5. The present invention provides novel analogs of Ospemifene, 63-1. Such novel Ospemifene analogs, as described by structures 63-2, 63-3, and 63-4, possess all the utilities of AGI-1067 and optionally provide cellular accumulation as set forth below.

Method of Making New Compound:

The synthesis of Ospemifene, 63-1 is described in WO01/36360. As shown in Schemes 63.1-63.2, compound 63-1 is treated with a dialkylphosphonoalkyltrifluromethylsulphonate in a solvent such as pyridine or a non basic solvent such as dichloromethane containing a base such as triethylamine to furnish the ether of 63-1. The alkyl groups are removed from the phosphonate moiety with trimethylsilylbromide in a solvent such as DMF or acetonitrile and the resulting compound is converted to the desired prodrug 63-2, 63-3, 63-4 using the methods of phosphonate ester and amidate formation described below.

Scheme 63.2 describes the synthesis of a compound 63-9, a particular member of the general class of compounds described by the structure 63-2, 63-3, 63-4. Compound 63-1 is treated with diethylphosphonomethyltrifluorosulphonate, 63-5, in pyridine to yield the ether 63-6. Compound 63-6 is treated with trimethylsilylbromide in acetonitrile to yield the free phophonic acid 63-7. Compound 63-7 is then treated with dicyclohexylcarbodiimide and phenol in DMF to yield the monophenol ester 63-8, which is then condensed with the isopropylester of alanine using aldrithiol and triphenylphosphine in DMF to yield the desired prodrug 63-9

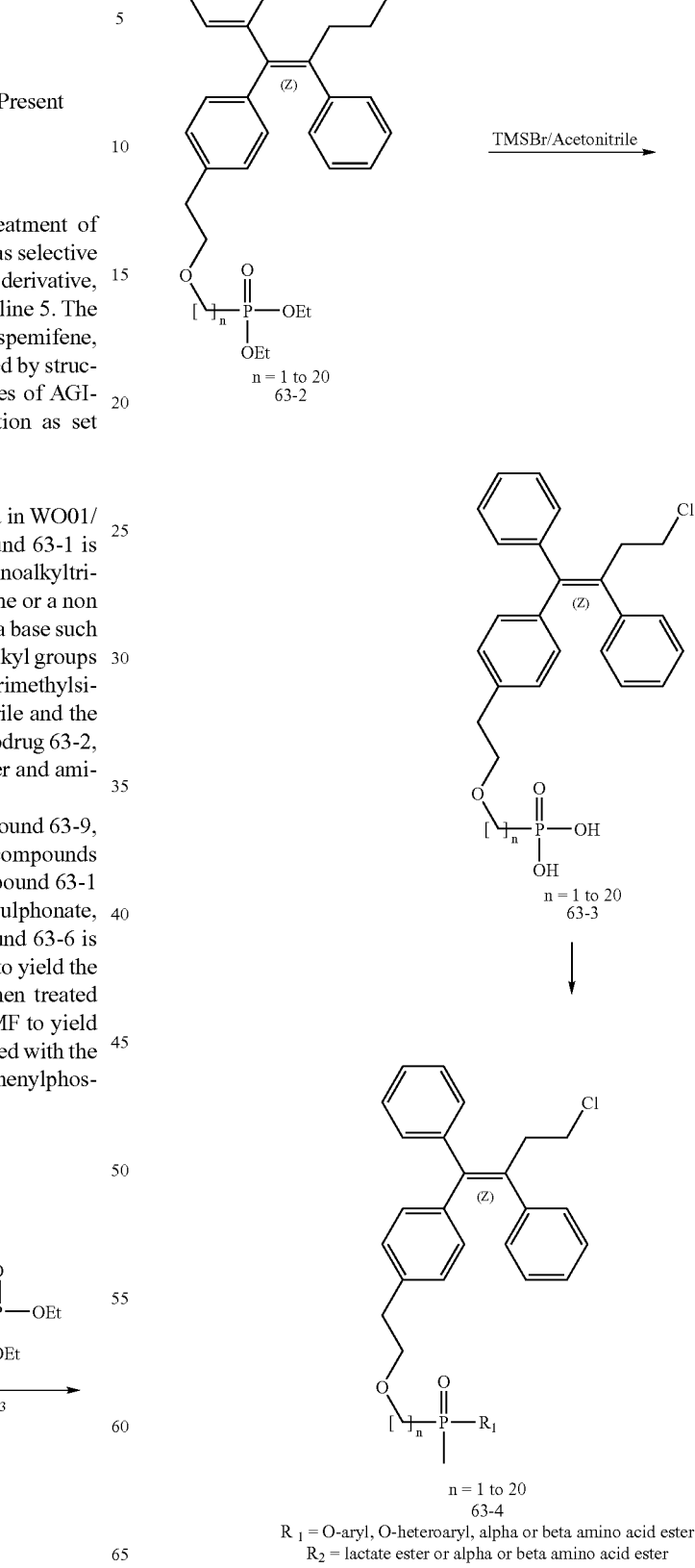

Example 64

Preparation of Exemplary Compounds of the Present Invention

Synthetic sequences to examples of such phosphonates are described in Scheme 64.1.

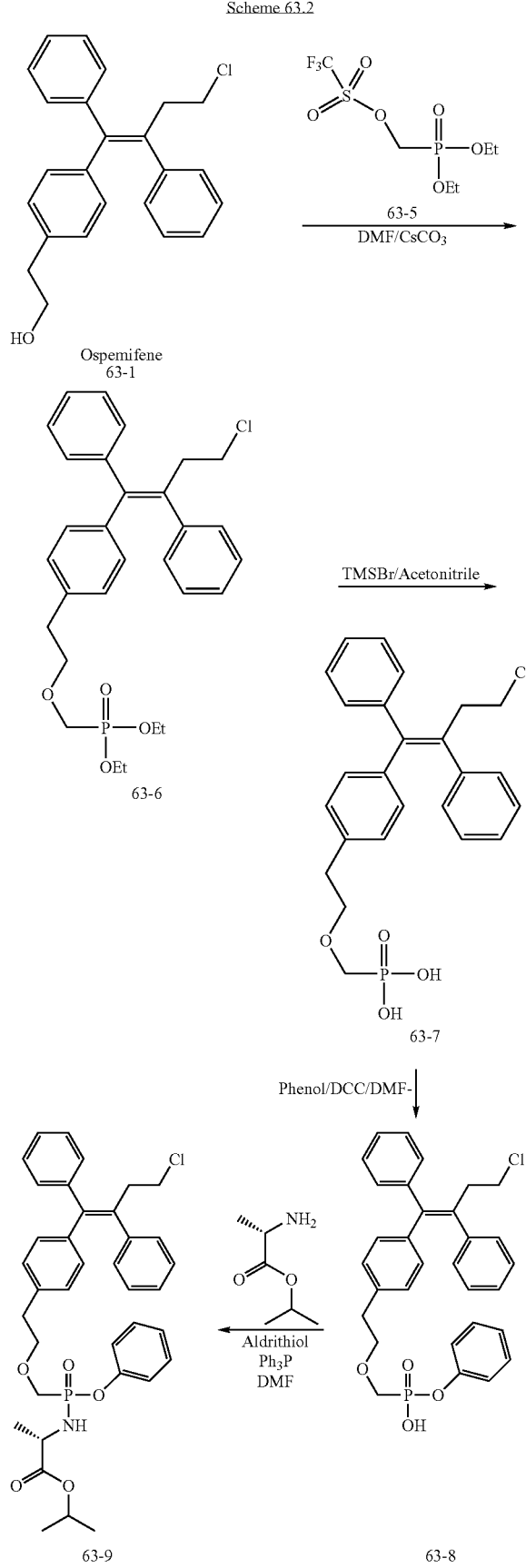

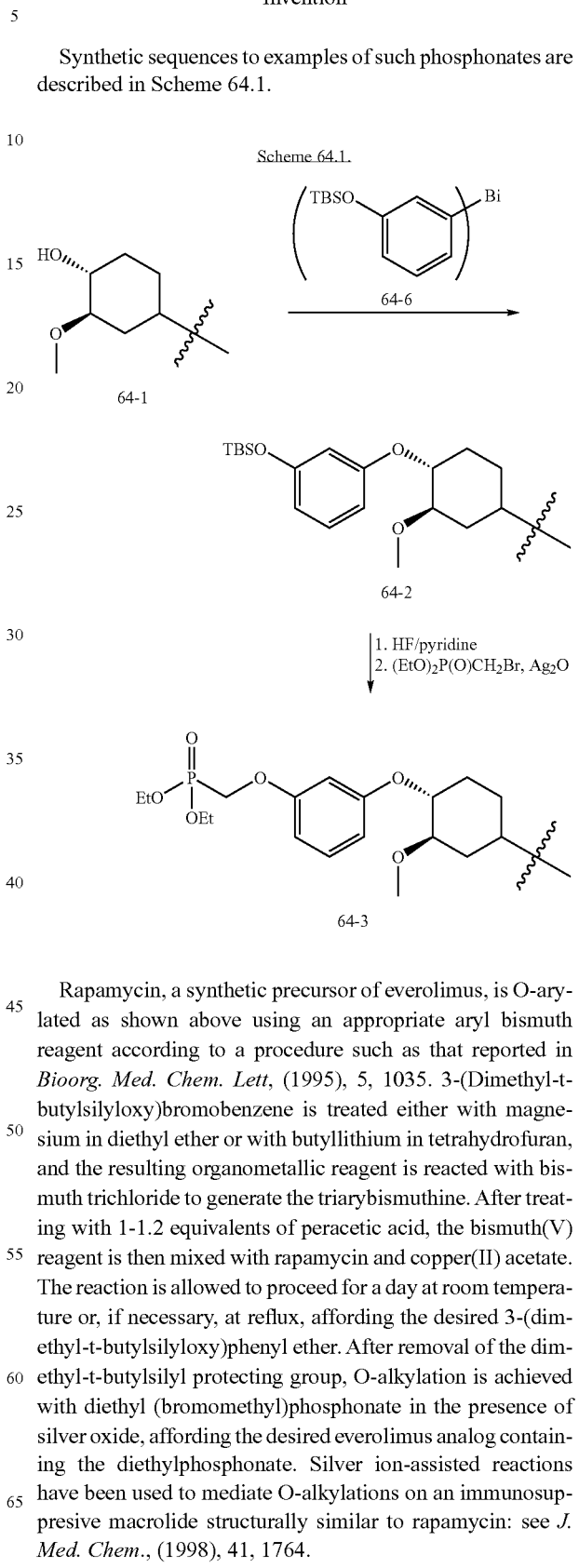

Rapamycin, a synthetic precursor of everolimus, is O-arylated as shown above using an appropriate aryl bismuth reagent according to a procedure such as that reported in *Bioorg. Med. Chem. Lett*, (1995), 5, 1035. 3-(Dimethyl-t-butylsilyloxy)bromobenzene is treated either with magnesium in diethyl ether or with butyllithium in tetrahydrofuran, and the resulting organometallic reagent is reacted with bismuth trichloride to generate the triarybismuthine. After treating with 1-1.2 equivalents of peracetic acid, the bismuth(V) reagent is then mixed with rapamycin and copper(II) acetate. The reaction is allowed to proceed for a day at room temperature or, if necessary, at reflux, affording the desired 3-(dimethyl-t-butylsilyloxy)phenyl ether. After removal of the dimethyl-t-butylsilyl protecting group, O-alkylation is achieved with diethyl (bromomethyl)phosphonate in the presence of silver oxide, affording the desired everolimus analog containing the diethylphosphonate. Silver ion-assisted reactions have been used to mediate O-alkylations on an immunosuppresive macrolide structurally similar to rapamycin: see *J. Med. Chem.*, (1998), 41, 1764.

Scheme 64.2.

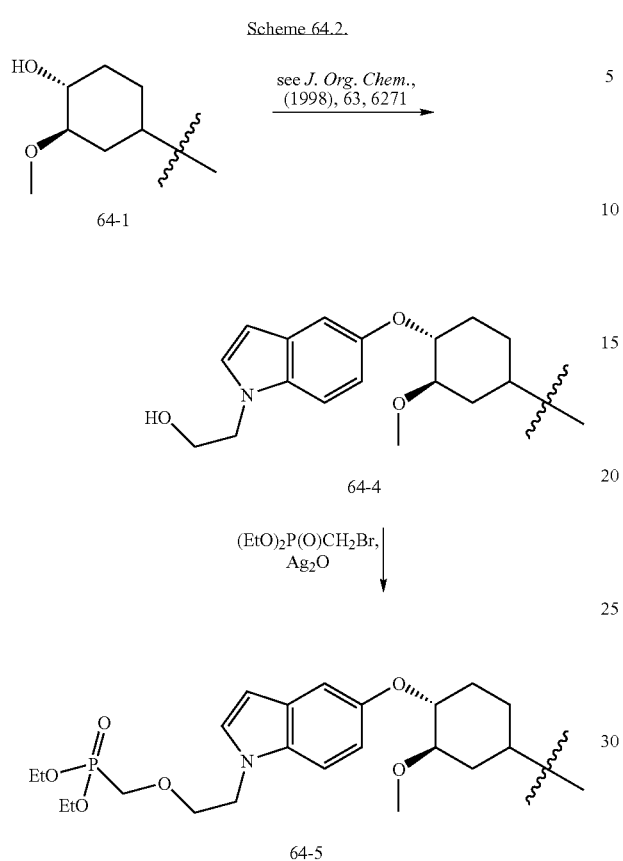

A phosphonate derivative of everolimus indolyl ether is prepared as depicted in Scheme 64.2, in a similar manner to the previous example with the exception that the key triindolylbismuthine intermediate is obtained from 5-bromoindole following the procedure described in *J. Org. Chem.* (1998), 63, 6721.

Example 65

Preparation of Exemplary Compounds of the Present Invention

Synthetic sequences to examples of such phosphonates are described in Scheme 65.1.

Scheme 65.1.

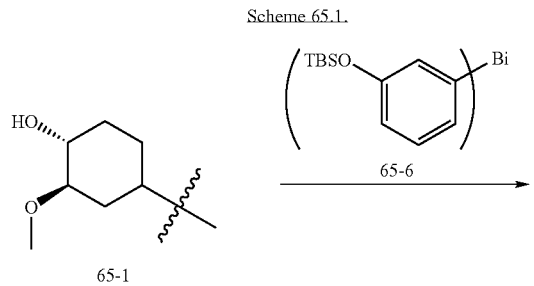

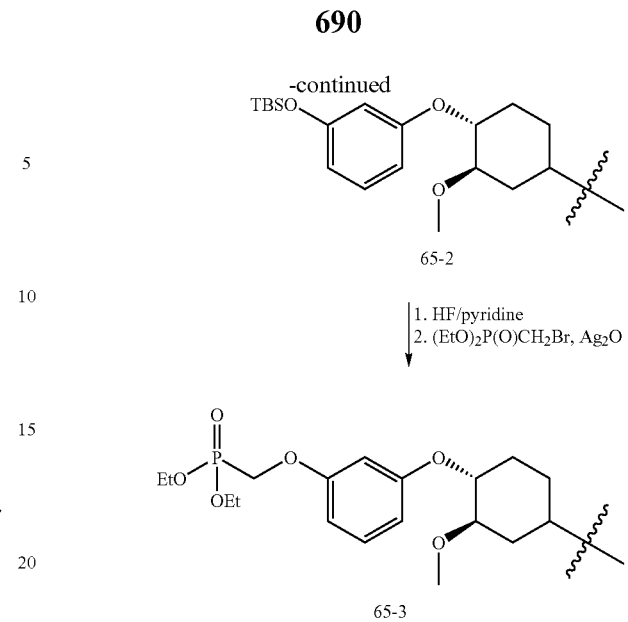

Sirolimus is O-arylated as shown above using an appropriate aryl bismuth reagent according to a procedure such as that reported in *Bioorg. Med. Chem. Lett*, (1995), 5, 1035. 3-(dimethyl-t-butylsilyloxy)bromobenzene is treated either with magnesium in diethyl ether or with butyllithium in tetrahydrofuran, and the resulting organometallic reagent is reacted with bismuth trichloride to generate the triarybismuthine. After treating with 1-1.2 equivalents of peracetic acid, the bismuth(V) reagent is then mixed with sirolimus and copper (II) acetate. The reaction is allowed to proceed for a day at room temperature or, if necessary, at reflux, affording the desired 3-(dimethyl-t-butylsilyloxy)phenyl ether. After removal of the dimethyl-t-butylsilyl protecting group, O-alkylation is achieved with diethyl (bromomethyl)phosphonate in the presence of silver oxide, affording the desired sirolimus analog containing the diethylphosphonate. Silver ion-assisted reactions have been used to mediate O-alkylations on an immunosuppresive macrolide structurally similar to sirolimus: see *J. Med. Chem.*, (1998), 41, 1764.

Scheme 65.2.

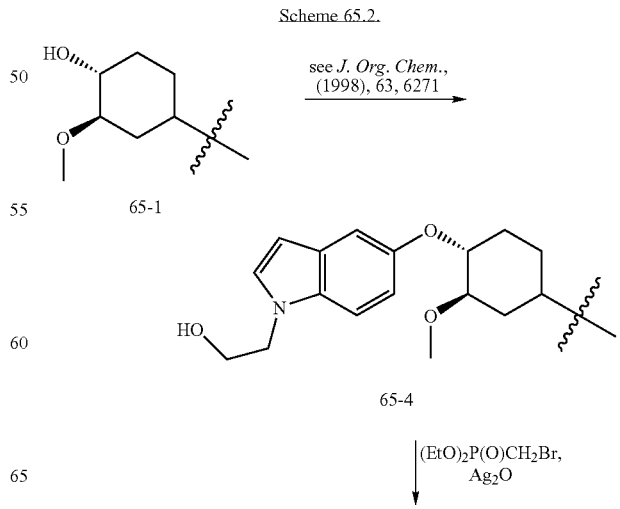

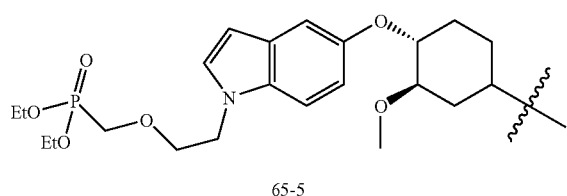

65-5

A phosphonate derivative of sirolimus indolyl ether is prepared as depicted in Scheme 65.2, in a similar manner to the previous example with the exception that the key triindolyl-bismuthine intermediate is obtained from 5-bromoindole following the procedure described in *J. Org. Chem.* (1998), 63, 6721.

Example 66

Preparation of Exemplary Compounds of the Present Invention

Synthetic methodology towards compounds such as these is described in WO 09/613,266, according to the general routes outlined in Schemes 66.1-66.3.

Scheme 66.1

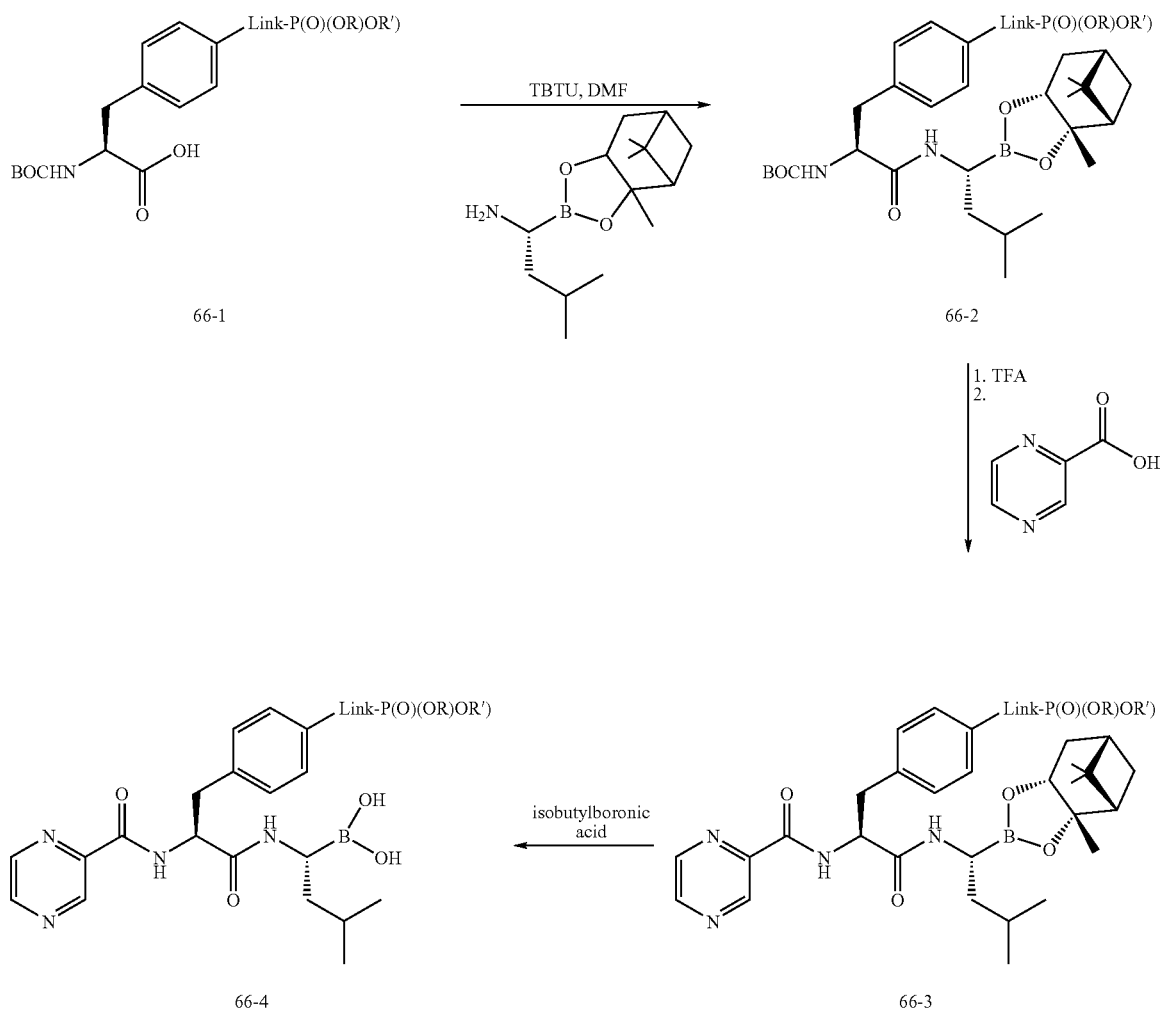

Examples of the synthesis of suitable phosphonate-containing phenylalanine derivatives are shown below.

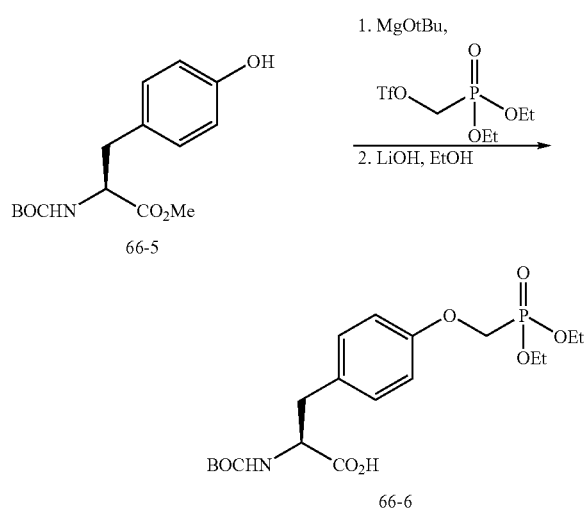

Scheme 66.2

The protected tyrosine derivative can be treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester. Subsequent selective hydrolysis of the carboxylate ester using a source of hydroxide ion such as lithium hydroxide in a solvent such as ethanol provides the phosphonate-containing reagent in a form suitable for use in the synthesis of bortezomib analogs.

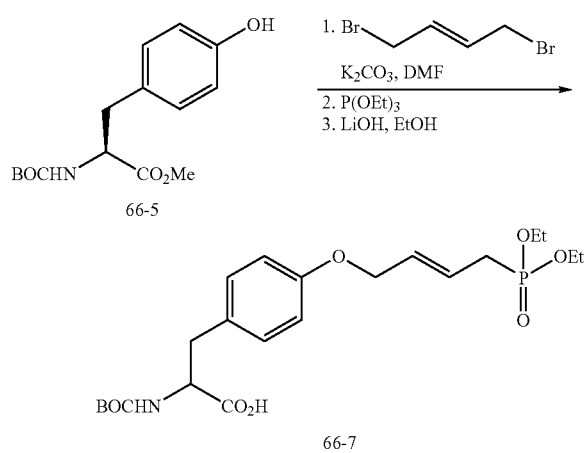

Scheme 66.3

The protected tyrosine derivative can be treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the mono-alkylated product is isolated by chromatography. This is then heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. Subsequent selective hydrolysis of the carboxylate ester using a source of hydroxide ion such as lithium hydroxide in a solvent such as ethanol provides the phosphonate-containing reagent in a form suitable for use in the synthesis of bortezomib analogs.

Example 67

Preparation of Exemplary Compounds of the Present Invention

Reduction of the dose and/or improvement of efficacy is achieved by the use of pro-drugs of analogs of VX-148 which, upon cleavage inside the target cell, give rise to an agent with an increased intracellular half-life. Such compounds are described below.

Scheme 67.1

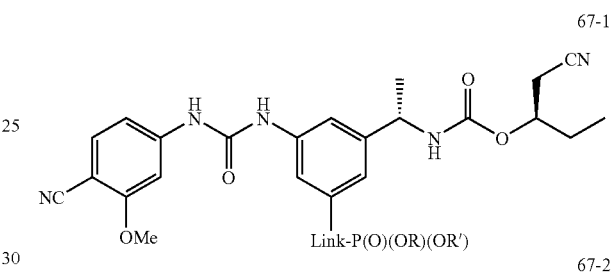

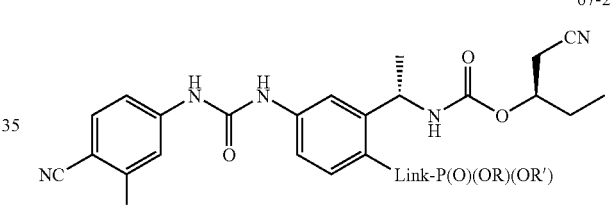

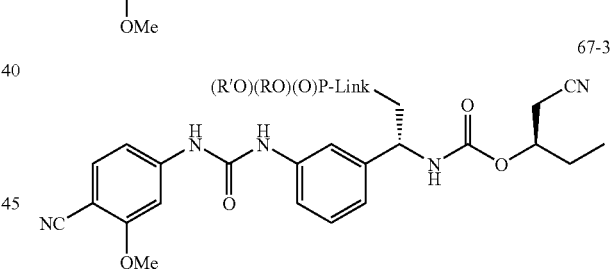

Link includes 0-8 atoms; 2-6 is preferred

Compounds such as these can be made according to the general routes outlined in Schemes 67.2, 67.4 and 67.5, with syntheses of suitable reagents depicted in Schemes 67.3 and 67.6.

Scheme 67.2

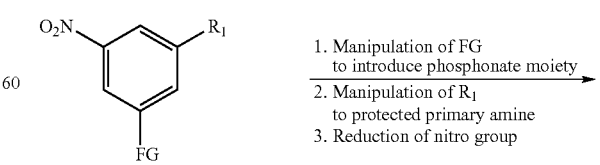

$R_1$ = 1-carbon substituent;
FG = functional group 67-4

-continued

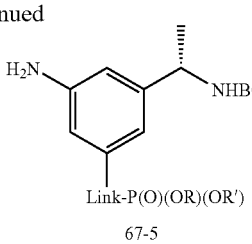
67-5
A 3,5-difunctionalized nitrobenzene derivative provides a suitable starting point for a reagent that contains a phosphonate moiety linked to the phenyl ring at the desired position, ready for incorporation into the fully-crafted VX-148 analog using methods developed for the parent compound.
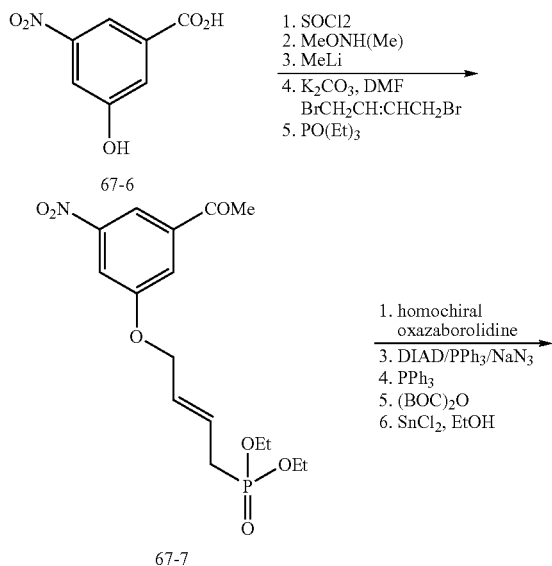

Scheme 67.3

67-6

67-7

67-8

3-Hydroxy-5-nitro-benzoic acid is heated briefly in thionyl chloride to generate the acid chloride. This is then condensed with O,N-dimethyl-hydroxylamine in the presence of a base such as triethylamine to produce the Weinreb amide which, upon reaction with methyl lithium, gives the acetophenone derivative. This is then treated with a base such as potassium carbonate in a dipolar aprotic solvent such as dimethylformamide, in the presence of an excess of E-1,4-dibromobutene. The monobromide is isolated by chromatography and then subjected to treatment with triethylphosphite in a solvent such as toluene (or other Arbuzov reaction conditions: see Engel, R., Synthesis of carbon-phosphorus bonds, CRC press, (1988)) to generate the desired phosphonate diethyl ester. Thereafter, the carbonyl of the acetophenone is reduced enantioselectively using an appropriate homochiral oxazaborolidine such as that described by Corey (*J. Am. Chem. Soc*., (1987), 109, 5551), and the resulting alcohol is displaced by azide using a method such as that described by Mitsunobu (*Bull. Chem. Soc. Japan*., (1971), 44, 3427). The azide is reduced to the amine under Staudinger conditions (*Helv. Chim. Act*., (1919), 2, 635) and protected as the t-butyl carbonate. Finally, the desired aniline is generated by tin (II)-mediated reduction of the nitrobenzene.

Scheme 67.4.

$R_1$ = 1-carbon substituent; FG = functional group 67-9

67-10

Reagents suitable for use in the synthesis of phosphonate analogs are made by routes analogous to that shown in Scheme 67.3, starting from 2-hydroxy-5-nitro-benzoic acid.

Scheme 67.5.

$R_1$ = 1-carbon substituent 67-11

67-12

-continued

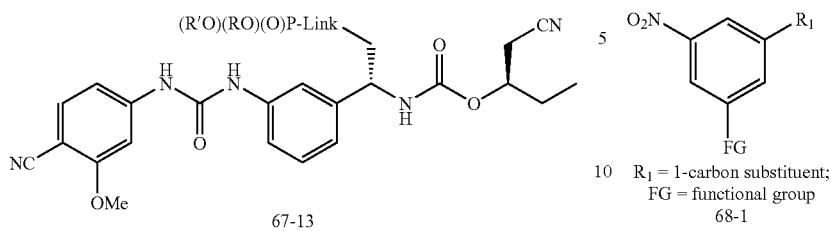

67-13

An example of the synthesis of a suitable reagent for coupling reactions as in U.S. Pat. No. 6,054,472 and U.S. Pat. No. 6,344,465 is illustrated in Scheme 67.6 below.

Scheme 67.6

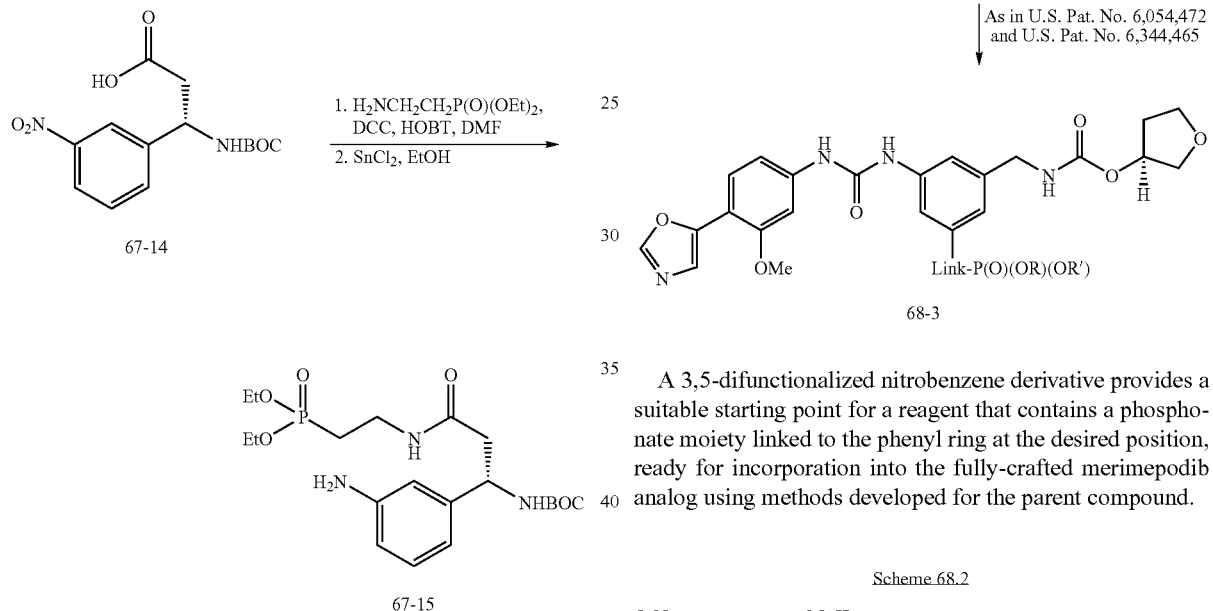

3-tert-Butoxycarbonylamino-3-(3-nitro-phenyl)-propionic acid (commercially available) is coupled with 2-aminoethylphosphonic acid diethyl ester (commercially available) using standard reagents for the formation of a secondary amide such as dicyclohexylcarbodiimide (DCC) and hydroxybenztriazole (HOBT), in a solvent such as dimethylformamide. Subsequent reduction of the nitro group proceeds in a fashion similar to that described in Scheme 67.3.

Example 68

Preparation of Exemplary Compounds of the Present Invention

Compounds such as these can be made according to the general routes outlined in Schemes 68.1, 68.3 and 68.4, with syntheses of suitable reagents depicted in Schemes 68.2 and 68.5.

Scheme 68.1.

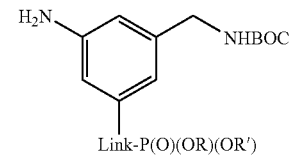

68-1

$R_1$ = 1-carbon substituent;
FG = functional group

1. Manipulation of FG to introduce phosphonate moiety
2. Manipulation of $R_1$ to protected primary amine
3. Reduction of nitro group

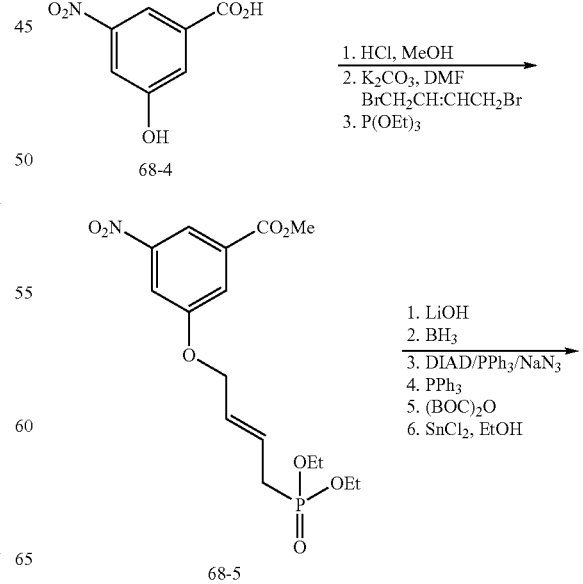

68-2

As in U.S. Pat. No. 6,054,472 and U.S. Pat. No. 6,344,465

68-3

A 3,5-difunctionalized nitrobenzene derivative provides a suitable starting point for a reagent that contains a phosphonate moiety linked to the phenyl ring at the desired position, ready for incorporation into the fully-crafted merimepodib analog using methods developed for the parent compound.

Scheme 68.2

68-4

1. HCl, MeOH
2. $K_2CO_3$, DMF
   $BrCH_2CH:CHCH_2Br$
3. $P(OEt)_3$ 68-5

1. LiOH
2. $BH_3$
3. DIAD/$PPh_3$/$NaN_3$
4. $PPh_3$
5. $(BOC)_2O$
6. $SnCl_2$, EtOH

-continued

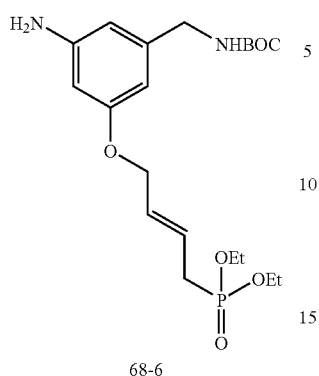

68-6

3-Hydroxy-5-nitro-benzoic acid is heated briefly in acidic methanol to generate the methyl ester. This is then treated with a base such as potassium carbonate in a dipolar aprotic solvent such as dimethylformamide, in the presence of an excess of E-1,4-dibromobutene. The monobromide is isolated by chromatography and then subjected to treatment with triethylphosphite in a solvent such as toluene (or other Arbuzov reaction conditions: see Engel, R., Synthesis of carbon-phosphorus bonds, CRC press (1988)) to generate the desired phosphonate diethyl ester. Thereafter, the benzoate ester is saponified and reduced, and the resulting alcohol displaced by azide using a method such as that described by Mitsunobu (*Bull. Chem. Soc. Japan.*, (1971), 44, 3427). The azide is reduced to the amine under Staudinger conditions (*Helv. Chim. Act.*, (1919), 2, 635) and protected as the t-butyl carbonate. Finally, the desired aniline is generated by tin (II)-mediated reduction of the nitrobenzene.

Scheme 68.3.

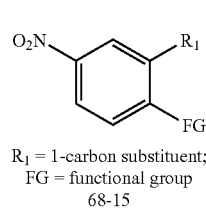

$R_1$ = 1-carbon substituent;
FG = functional group
68-15

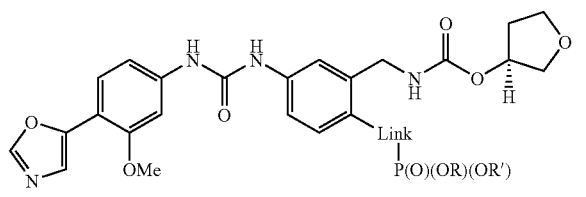

68-7

Reagents suitable for use in the synthesis of phosphonate analogs of Type II may be made by routes analogous to that shown in Scheme 68.2, starting from 2-hydroxy-5-nitro-benzoic acid.

Scheme 68.4. General route to Type III analogs

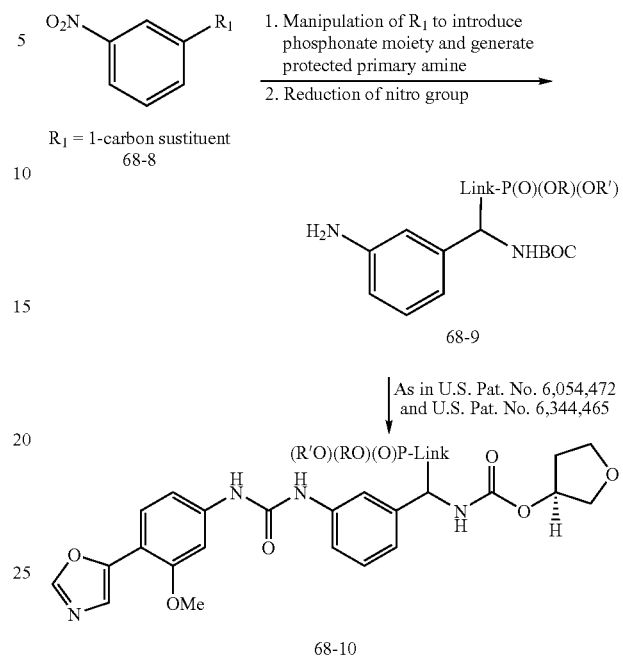

$R_1$ = 1-carbon sustituent
68-8

1. Manipulation of $R_1$ to introduce phosphonate moiety and generate protected primary amine
2. Reduction of nitro group 68-9

As in U.S. Pat. No. 6,054,472 and U.S. Pat. No. 6,344,465

68-10

An example of the synthesis of a suitable reagent for coupling reactions as in U.S. Pat. No. 6,054,472 and U.S. Pat. No. 6,344,465 is illustrated in Scheme 68.5 below.

Scheme 68.5

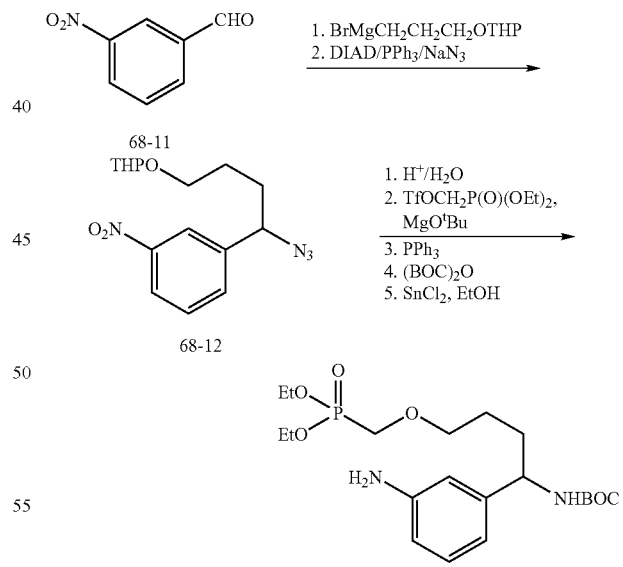

68-11

1. BrMgCH$_2$CH$_2$CH$_2$OTHP
2. DIAD/PPh$_3$/NaN$_3$ 68-12

1. H$^+$/H$_2$O
2. TfOCH$_2$P(O)(OEt)$_2$, MgO$^t$Bu
3. PPh$_3$
4. (BOC)$_2$O
5. SnCl$_2$, EtOH 68-13

3-Nitrobenzaldehyde reacts with a Grignard reagent to introduce a tether bearing a protected alcohol and simultaneously to generate a benzylic alcohol, as shown. The alcohol is displaced by an azide in a manner similar to that described for Scheme 68.2. After deprotection, the liberated alcohol is alkylated with diethyl phosphonomethyltriflate (prepared according to *Tetrahedron Lett.*, (1986), 27, 1477) using a base such as magnesium tert-butoxide in a solvent such as tetrahydrofuran. Subsequent transformations of the azide and nitro groups proceed in a fashion similar to that described in Scheme 68.2.

Example 69

Preparation of Exemplary Compounds of the Present Invention

Synthetic methodology towards compounds such as these is based on methods described by Batt et al, *Bioorg. Med. Chem. Lett.*, (1995), 5, 1549. A typical general route is outlined in Scheme 69.1.

Scheme 69.1

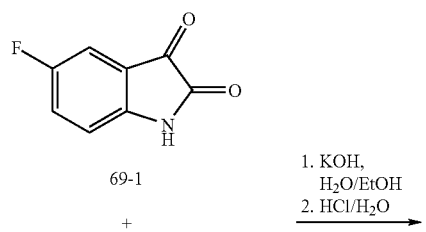
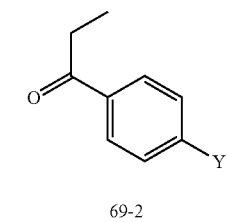
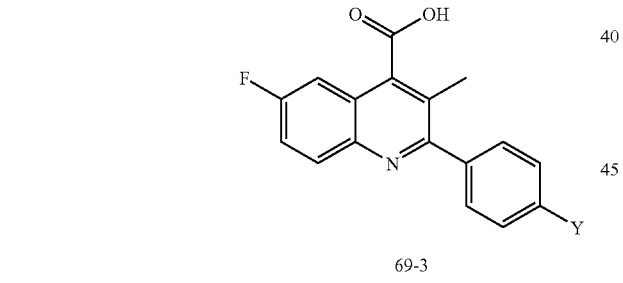
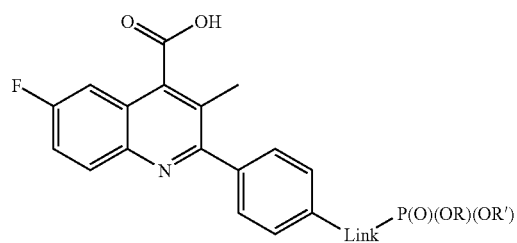

Examples of the synthesis of suitable phosphonate-containing analogs are shown below.

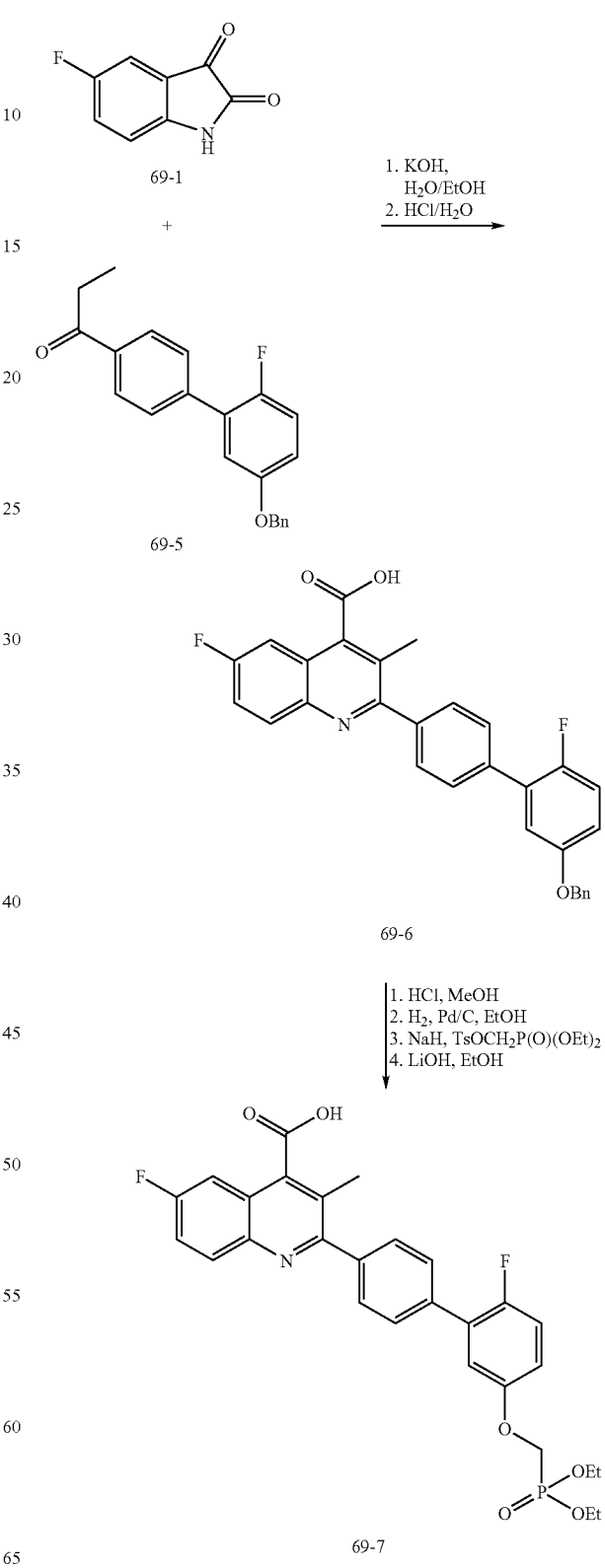

The initial Pfitzinger condensation is classically achieved in a single step using potassium hydroxide with acidic work-up, as shown. Alternatively, the initial aldol condensation may be performed using diethylamine in ethanol, and the quinoline ring may be formed is a second step mediated by an acid such as hydrochloric acid in a solvent such as 1,4-dioxane. Following removal of the benzyl protecting group via hydrogenation, the phenol can be treated in a solvent such as tetrahydrofuran or dimethylformamide with a base such as sodium hydride. When bubbling ceases, diethyl phosphonomethyltriflate (prepared according to *Tetrahedron Lett.*, (1986), 27, 1477) is added, yielding the desired phosphonate diester. The carboxylate is deprotected by treatment with lithium hydroxide in ethanol.

The synthesis is similar to that depicted in Scheme 69.2 except that, following deprotonation of the phenol, E-1,4-dibromobutene is added in excess. After quenching the reaction with aqueous ammonium chloride and extracting the product with an organic solvent such as ethyl acetate, the mono-alkylated product is isolated by chromatography. The resulting bromide is heated with triethylphosphite in a solvent such as toluene to generate the diethyl ester of the desired phosphonic acid, and the carboxylic acid is deprotected as before.

Example 70

Preparation of Exemplary Compounds of the Present Invention

The structures of Dexamethasone 70-1 (U.S. Pat. No. 3,007,923) and the phosphonate esters 70-4 are shown in Scheme 70.1, in which the substituent $R^1$ is H, alkyl, alkenyl, aryl or aralkyl. The compounds 70-4 incorporate a phosphonate moiety $(R^1O)_2P(O)$ connected to the nucleus by means of a variable linking group, designated as "link" in the attached structures.

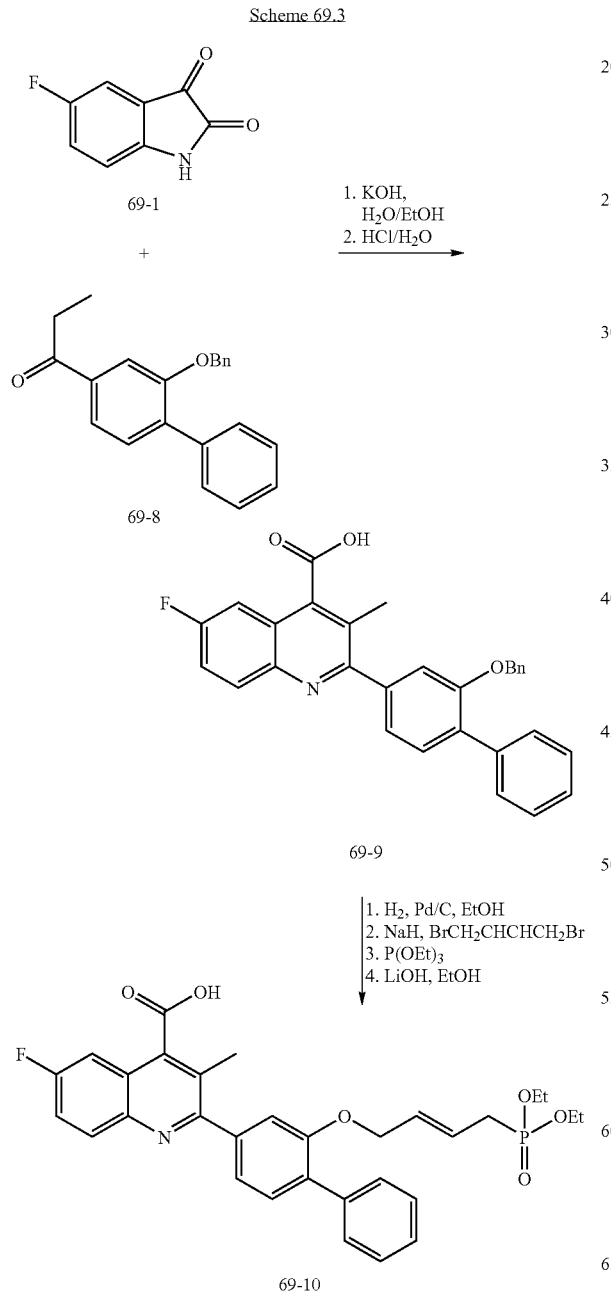

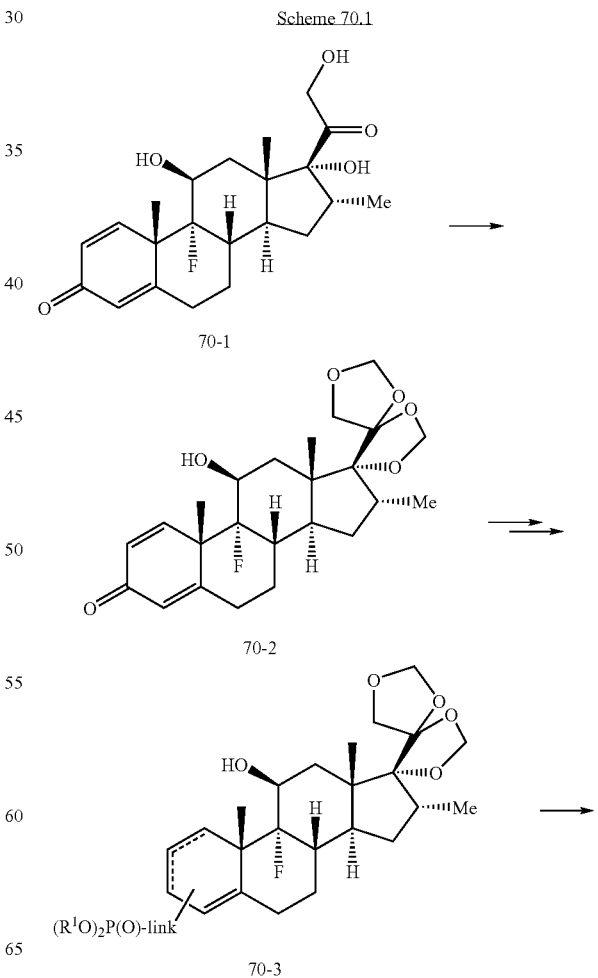

-continued

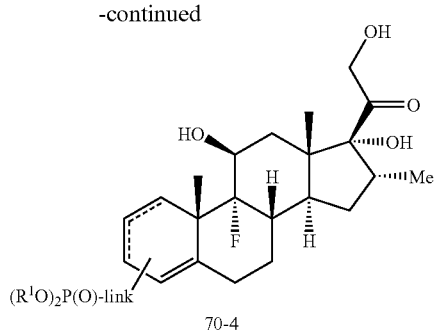

70-4

Schemes 70.2-70.12 illustrate the syntheses of the phosphonate compounds of this invention and of the intermediate compounds useful for their synthesis.

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, (1972), p. 375ff. Reactive substituents which may be protected are shown in the accompanying schemes as, for example, [OH], [O], etc. For example, Scheme 70.1 depicts a protection-deprotection sequence in which the steroid side-chain is protected as a bis-methylenedioxy (BMD) moiety. In this sequence, Dexamethasone 70-1 is reacted with paraformaldehyde and an acid catalyst such as hydrochloric acid, as described in Protective Groups in Organic Synthesis, by T. W. Greene and P. G. M. Wuts, Wiley, Second Edition (1990), p. 223, to yield the BMD derivative 70-2. The phosphonate moiety is then introduced, using the procedures described below, to produce the phosphonate ester 70-3. The BMD moiety is then hydrolyzed, for example by treatment with 50% aqueous acetic acid, as described in Protective Groups in Organic Synthesis, by T. W. Greene and P. G. M. Wuts, Wiley, Second Edition (1990), p. 223, to afford the triol 70-4.

Preparation of the Phosphonate Esters 70-7, 70-14, 70-18, 70-20, 70-120, 70-22, and 70-27.

Schemes 70.2-70.6 depicts the preparation of phosphonates in which the phosphonate is attached by means of an imino or iminoxy group and a variable carbon chain. In this procedure, the BMD-protected derivative 70-2 is reacted with an amine or hydroxylamine 70-5, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime. The preparation of oximes of steroidal 3-ketones is described in Anal. Bioch., 1978, 86, 133. and in J. Mass. Spectrom., (1995), 30, 497. The BMD-protected side-chain compound 70-6 is then converted, as described in Scheme 70.1, into the triol 70-7.

Schemes 70.2-70.6 also illustrates the preparation of hydroxylamine ethers incorporating a phosphonate group. In this procedure, a phosphonate 70-8, in which Lv is a leaving group such as bromo or trifluoromethylsulfonyloxy, is reacted with BOC-hydroxylamine 70-9 (Aldrich) to produce the ether 70-10. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 70-11.

Scheme 70.2. Phosphonates A2.

Method

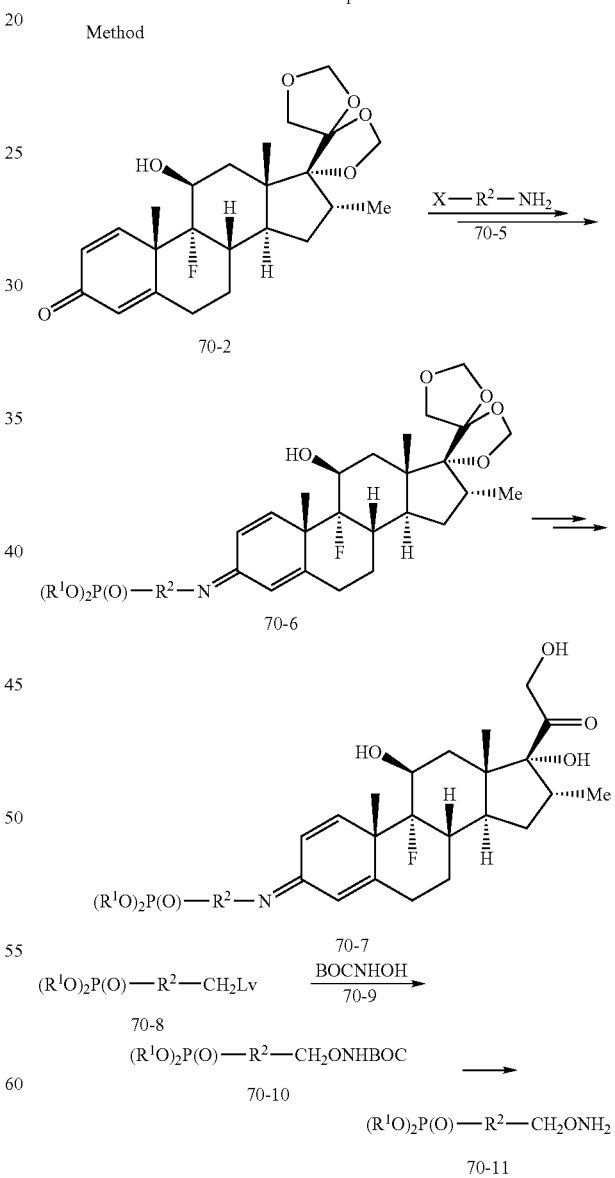

Scheme 70.3 illustrates the preparation of phosphonates 70-14 in which the phosphonate is attached by means of an iminoxy group. In this procedure, the substrate 70-2 is reacted with a dialkyl phosphonomethyl hydroxylamine 70-12, prepared as described above from a dialkyl trifluoromethylsulfonyloxymethyl phosphonate (Tet. Lett., 1986, 27, 1477) and BOC-hydroxylamine, to afford the oxime 70-13 which is deprotected to afford the triol 70-14. The oxime forming reaction is performed at ambient temperature in ethanol-acetic acid solution between equimolar amounts of the reactants. Using the above procedures, but employing, in place of the hydroxylamine ether 70-12, different oxime ethers 70-5, the corresponding products 70-7 are obtained.

Scheme 70.4 illustrates the preparation of compounds 70-18, 70-20, and 70-180 in which the phosphonate group is attached by means of a pyridyl methoxy group. In this procedure, the dienone 70-2 is reacted, as described above, with O-(3-bromo-5-pyridylmethyl)hydroxylamine 70-15, prepared as described above from 3-bromo-5-bromomethylpyridine (WO 95/28400), to give, after deprotection of the sidechain, the oxime 70-16. The product is then reacted, in the presence of a palladium catalyst, with a dialkyl phosphite 70-17 to afford the phosphonate 70-18. The preparation of arylphosphonates by means of a coupling reaction between aryl bromides and dialkyl phosphites is described in J. Med. Chem., 35, 1371, (1992). The reaction is performed in an inert solvent such as toluene, in the presence of a base such as triethylamine and a catalytic amount of tetrakis(triphenylphosphine)palladium(0).

Alternatively, the bromo compound 70-16 is coupled with a dialkyl vinylphosphonate 70-19 (Aldrich) to afford the phosphonate 70-20. The coupling of aryl halides with olefins by means of the Heck reaction is described, for example, in Advanced Organic Chemistry, by F. A. Carey and R. J. Sundberg, Plenum, (2001), p. 503ff and in Acc. Chem. Res., 12, 146, (1979). The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the styrenoid double bond present in the product 70-20 is reduced, for example by reaction with diimide, to produce the saturated analog 70-120. The reduction of olefinic bonds is described in Comprehensive Organic Transformations, by R. C. Larock, VCH, (1989), p. 6ff. The transformation is effected by means of catalytic hydrogenation, for example using a palladium on carbon catalyst and hydrogen or a hydrogen donor, or by the use of diimide or diborane.

Using the above procedures, but employing, in place of the bromopyridyloxy reagent 70-15, different bromo-substituted aryl or heteroaryl alkoxy hydroxylamines, and/or different dialkyl alkenyl phosphonates, the products analogous to the compounds 70-18, 70-20 and 70-120 are obtained.

Scheme 70.3

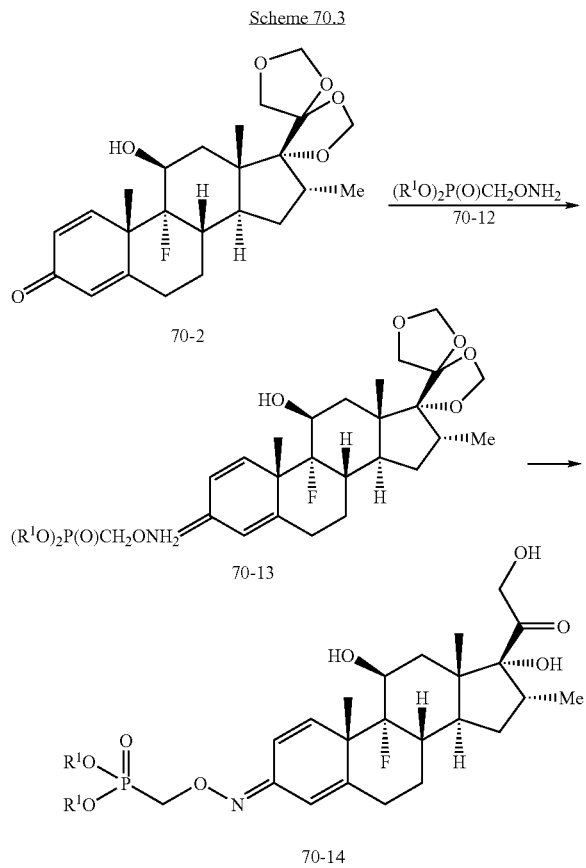

Scheme 70.4

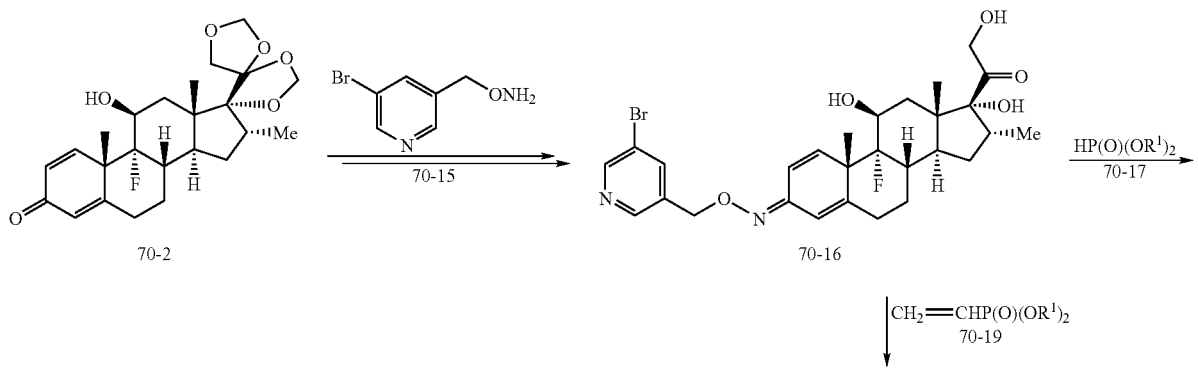

-continued

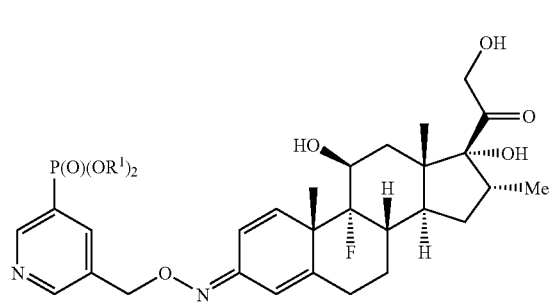

70-18

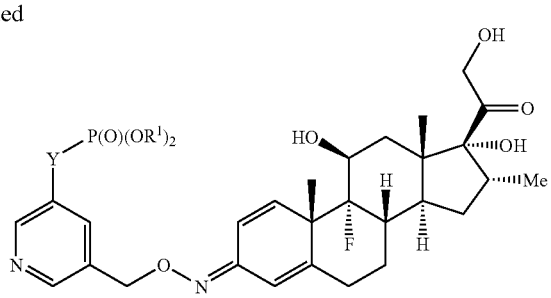

70-20 Y = CH=CH
70-120 Y = (CH₂)₂

Scheme 70.5 depicts the preparation of phosphonates 70-22 in which the phosphonate is attached by means of an imino group. In this procedure, the substrate 70-2 is reacted with a dialkyl 2-aminophenyl phosphonate 70-21, (Syn., (1999), 1368) to give, after deprotection, the imine product 70-22. The reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions.

Using the above procedures, but employing, in place of the 2-aminophenyl phosphonate 70-21 different amino-substituted aryl or heteroaryl phosphonates, products analogous to 70-22 are obtained.

Scheme 70.5

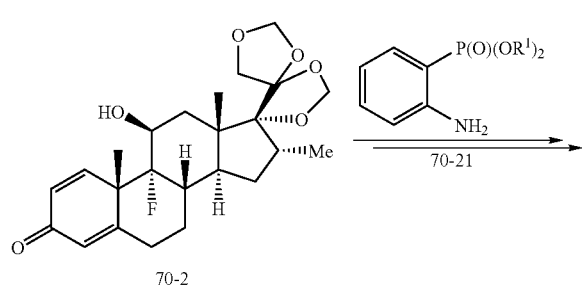

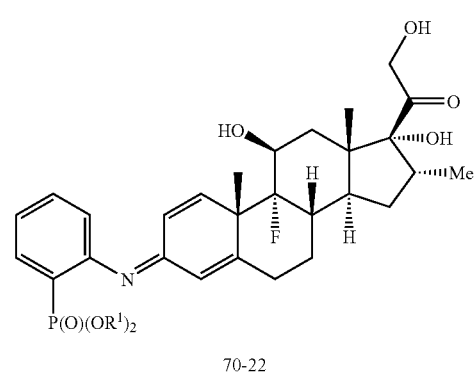

70-22

Scheme 70.6 illustrates the preparation of phosphonates 70-27 in which the phosphonate is attached by means of an oximino group and an amide linkage. In this procedure, the dienone 70-2 is reacted with O-(2-carboxyethyl)hydroxylamine 70-23 (J. Med. Chem., 1990, 33, 1423) to yield the oxime 70-24. The reaction of steroidal 1,4-dien-3-ones with substituted hydroxylamines is described in J. Steroid Bioch., (1976), 7, 795; the reaction is performed between equimolar amounts of the reactants in a polar organic solvent such as pyridine or methanol, optionally in the presence of acetic acid or sodium acetate. The oxime is then reacted with a dialkyl aminomethyl phosphonate 70-25 (AsInEx), to yield the amide oxime 70-26. The preparation of amides from carboxylic acids and derivatives is described, for example, in Organic Functional Group Preparations, by S. R. Sandler and W. Karo, Academic Press, (1968), p. 274, and Comprehensive Organic Transformations, by R. C. Larock, VCH, (1989), p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid is first converted into an activated derivative such as the acid chloride, anhydride, mixed anhydride, imidazolide and the like, and then reacted with the amine, in the presence of an organic base such as, for example, pyridine, to afford the amide. The conversion of a carboxylic acid into the corresponding acid chloride is effected by treatment of the carboxylic acid with a reagent such as, for example, thionyl chloride or oxalyl chloride in an inert organic solvent such as dichloromethane, optionally in the presence of a catalytic amount of dimethylformamide.

The amide product 70-26 is then converted, as described in Scheme 70.1, into the triol 70-27.

Using the above procedures, but employing, in place of the hydroxylamine 70-25, different carboxy-substituted hydroxylamines, and/or different amino-substituted phosphonates, the products analogous to 70-27 are obtained.

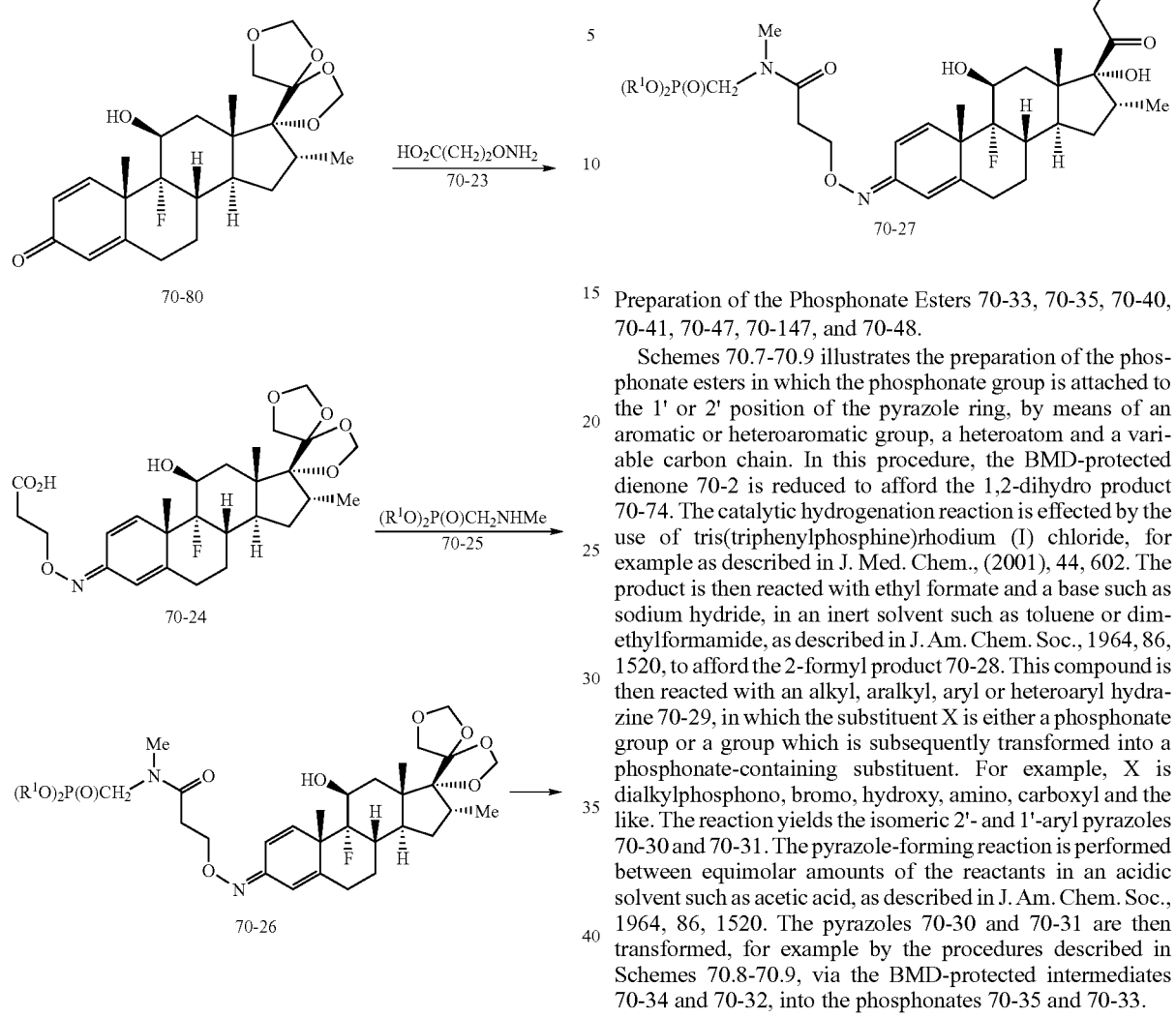

Preparation of the Phosphonate Esters 70-33, 70-35, 70-40, 70-41, 70-47, 70-147, and 70-48.

Schemes 70.7-70.9 illustrates the preparation of the phosphonate esters in which the phosphonate group is attached to the 1' or 2' position of the pyrazole ring, by means of an aromatic or heteroaromatic group, a heteroatom and a variable carbon chain. In this procedure, the BMD-protected dienone 70-2 is reduced to afford the 1,2-dihydro product 70-74. The catalytic hydrogenation reaction is effected by the use of tris(triphenylphosphine)rhodium (I) chloride, for example as described in J. Med. Chem., (2001), 44, 602. The product is then reacted with ethyl formate and a base such as sodium hydride, in an inert solvent such as toluene or dimethylformamide, as described in J. Am. Chem. Soc., 1964, 86, 1520, to afford the 2-formyl product 70-28. This compound is then reacted with an alkyl, aralkyl, aryl or heteroaryl hydrazine 70-29, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 70-30 and 70-31. The pyrazole-forming reaction is performed between equimolar amounts of the reactants in an acidic solvent such as acetic acid, as described in J. Am. Chem. Soc., 1964, 86, 1520. The pyrazoles 70-30 and 70-31 are then transformed, for example by the procedures described in Schemes 70.8-70.9, via the BMD-protected intermediates 70-34 and 70-32, into the phosphonates 70-35 and 70-33.

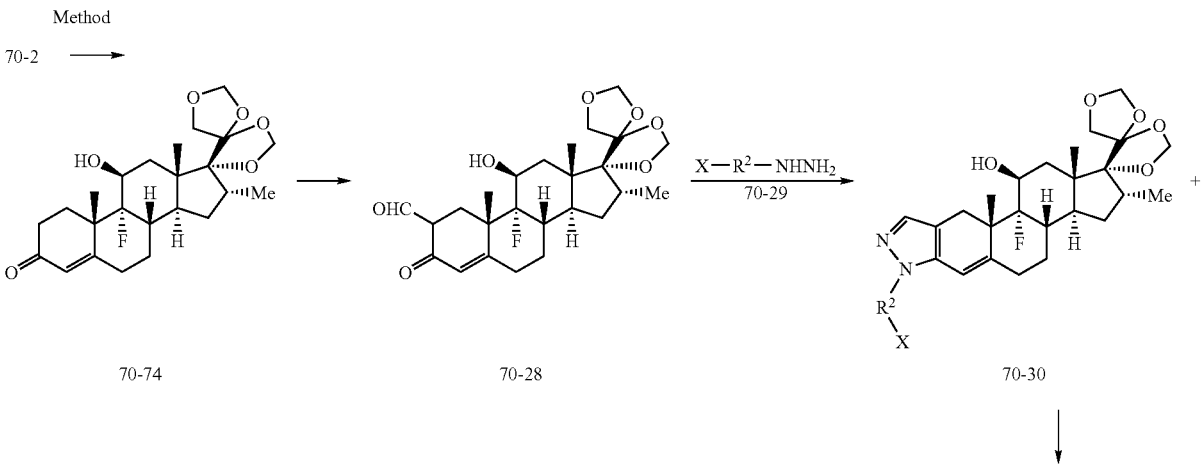

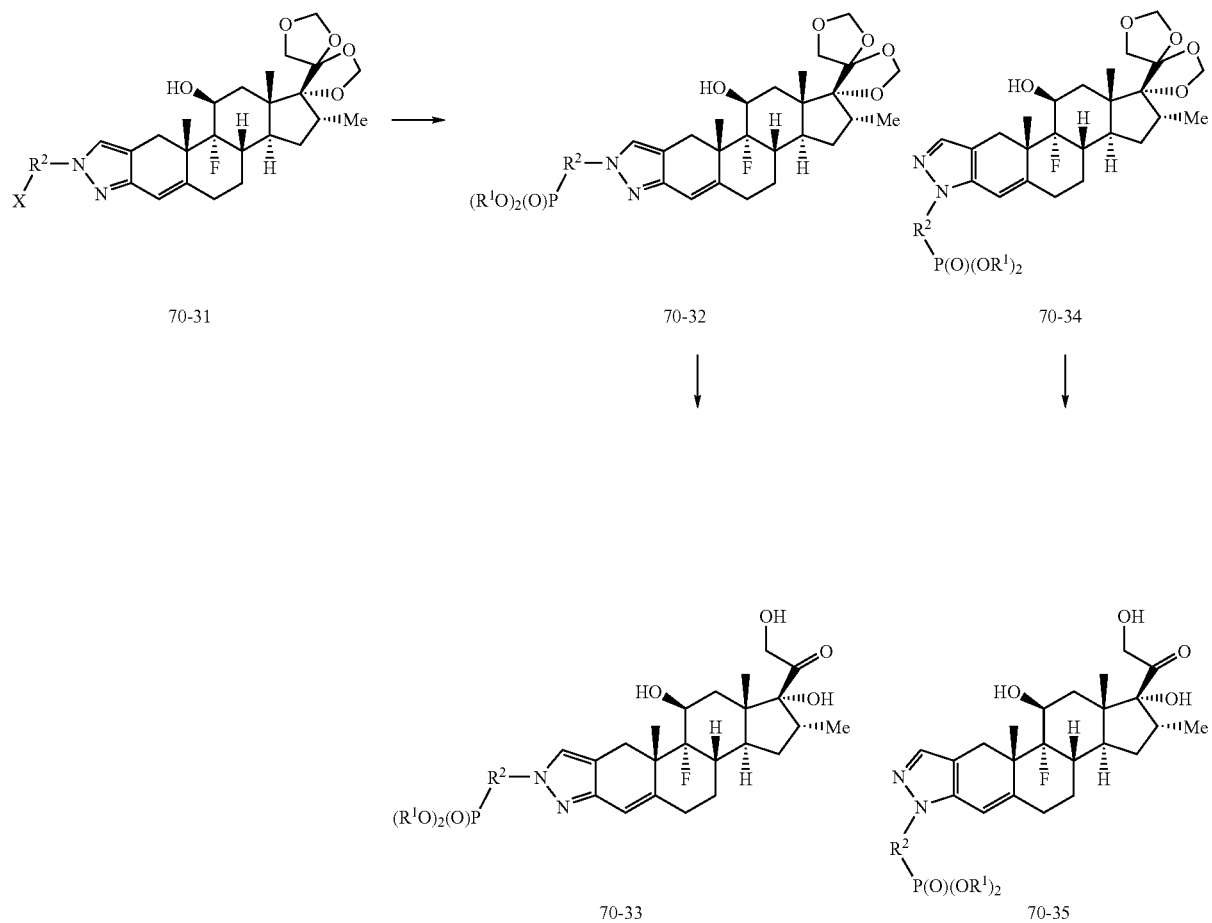

Scheme 70.8 illustrates the preparation of phosphonates and in which the phosphonate is attached by means of a phenyl ring and an alkoxy or an acetylenic linkage. In this procedure, the ketoaldehyde 70-28 is reacted, as described above, with 3-hydroxyphenylhydrazine 70-36 (Japanese patent JP 03011081) to give the pyrazoles 70-70 and 70-37. The 2'-substituted isomer 70-70 is then reacted in dichloromethane solution at ambient temperature with one molar equivalent of trifluoromethylsulfonyl chloride and dimethylaminopyridine, to yield the triflate 70-39. The product is then reacted in toluene solution with a dialkyl propynyl phosphonate 70-71 (Syn (1999), 2027), triethylamine and a catalytic amount of tetrakis(triphenylphosphine)palladium (0), to give the acetylenic product 70-73. The palladium-catalyzed coupling reaction of aryl triflates with terminal acetylenes is described in WO 0230930. The BMD protecting group is then removed to yield the triol 70-41.

Alternatively, the 1'-substituted pyrazole 70-37 is reacted, in a Mitsonobu reaction, with a dialkyl 2-hydroxyethyl phosphonate 70-72 (Epsilon) to afford the ether 70-38. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, (2001), p. 153-4 and in Org. React., (1992), 42, 335. The phenol and the alcohol component are reacted together in an aprotic solvent such as, for example, tetrahydrofuran, in the presence of a dialkyl azodicarboxylate and a triarylphosphine, to afford the ether or thioether products. The procedure is also described in Org. React., (1992), 42, 335-656. The product 70-38 is then deprotected to give the triol 70-40.

Using the above procedures, but employing different acetylenic or hydroxyl-substituted phosphonates, the products analogous to 70-41 and 70-40 are obtained. The functionalization procedures are interchangeable between the pyrazole substrates 70-70 and 70-37.

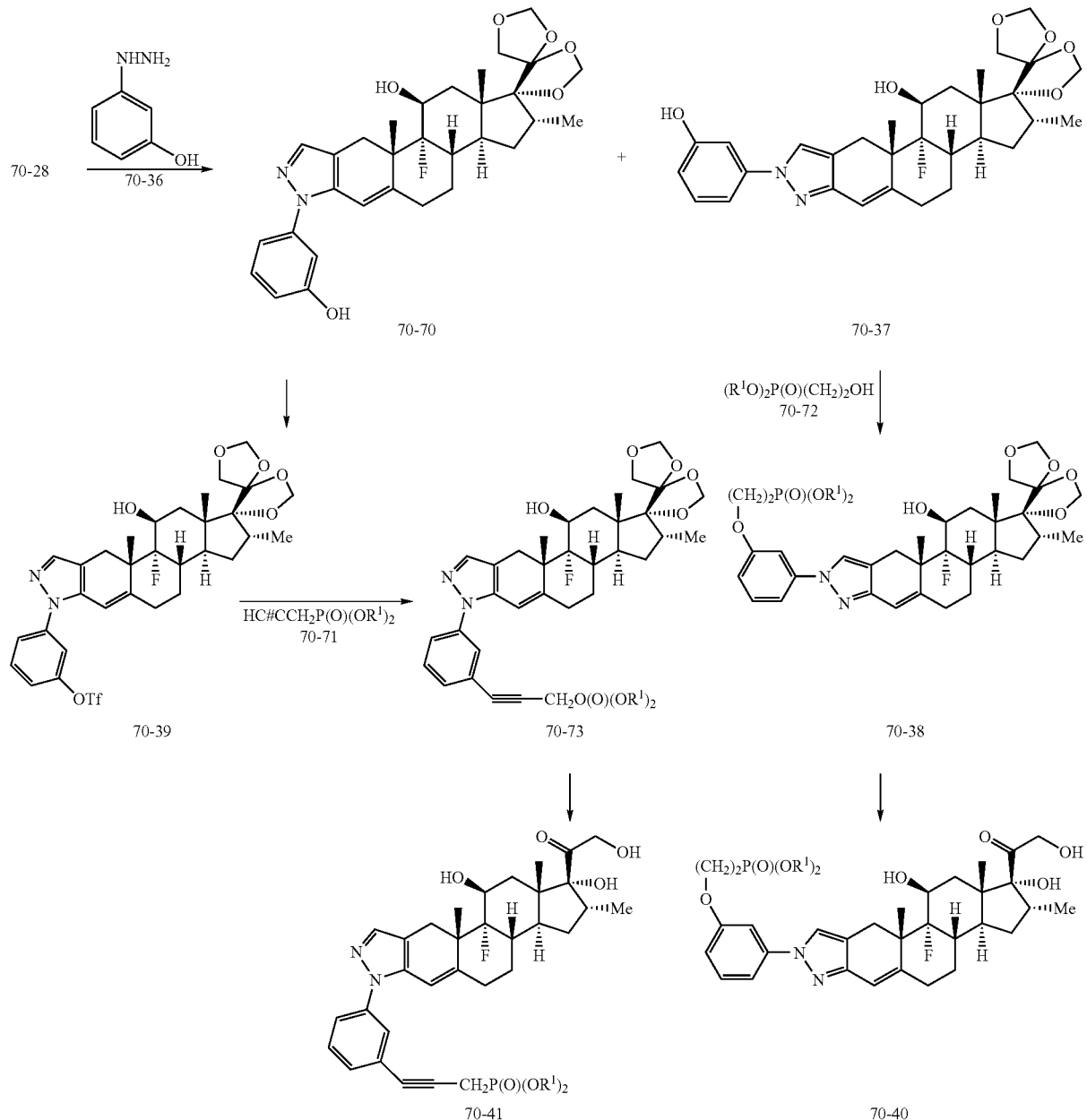

Scheme 70.9 illustrates the preparation of the phosphonates in which the phosphonate group is attached by means of a benzyl group or a benzyl group and a saturated or unsaturated carbon chain. In this procedure, the ketoaldehyde 70-28 is reacted, as described above, with 3-bromobenzyl hydrazine 70-75 (U.S. Pat. No. 4,370,339) to produce the pyrazoles 70-42 and 70-43. The 1'-substituted isomer 70-42 is coupled, in the presence of a palladium catalyst, with a dialkyl vinylphosphonate 70-76 (Aldrich) to give the phosphonate 70-46. The product is then deprotected to afford the triol 70-47. Optionally, the styrenoid double bond present in the product 70-47 is reduced, as described above, to produce the saturated analog 70-147.

Alternatively, the 2'-substituted pyrazole 70-43 is coupled, in the presence of a palladium catalyst, with a dialkyl phosphite to prepare the phosphonate 70-44 which is deprotected to give the triol 70-48. The preparation of arylphosphonates by means of a coupling reaction between aryl bromides and dialkyl phosphites is described in J. Med. Chem., 35, 1371, (1992). This reaction is performed in an inert solvent such as toluene, in the presence of a base such as triethylamine and tetrakis(triphenylphosphine)palladium(0).

Using the above procedures, but employing, in place of the bromobenzyl reagent 70-75, different bromo-substituted aralkyl, aryl or heteroaryl alkoxy hydrazines, and/or different dialkyl alkenyl phosphonates, the products analogous to the compounds 70-47, 70-147 and 70-48 are obtained.

Scheme 70.9

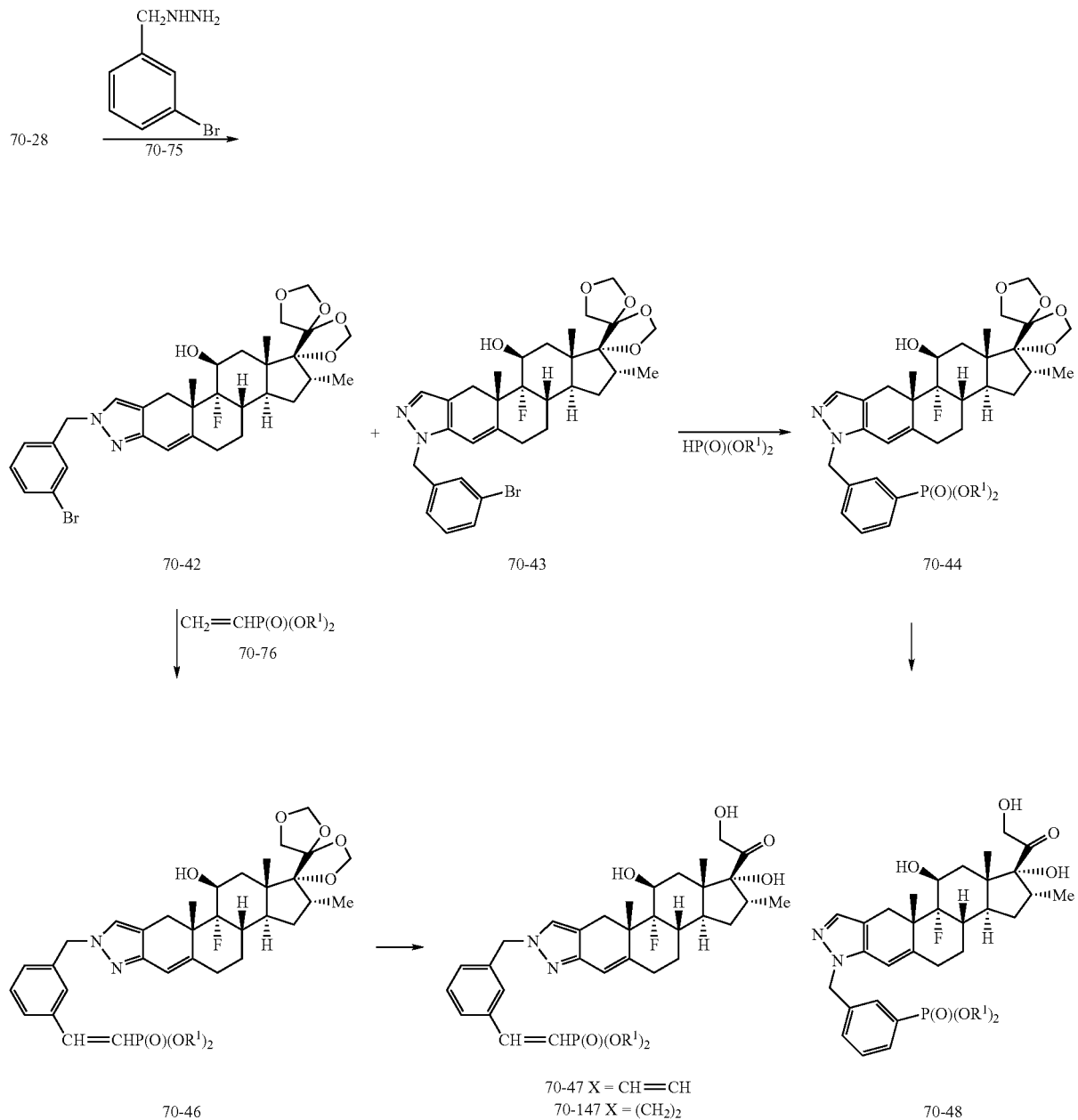

Schemes 70.10-70.12 depicts the preparation of the phosphonate esters in which the phosphonate group is attached by means of a variable carbon linkage. In this procedure, the ketoaldehyde 70-28 is reacted with hydrazine, to afford the pyrazole derivative 70-49. The reaction of steroidal 2-formyl-3-ketones with hydrazine is described in J. Am. Chem. Soc, 1964, 86, 1520. The reaction is performed in acetic acid at ambient temperature. The pyrazole product is then reacted with a bromomethyl compound 70-77, in which $R^2$ and X are as defined above, to yield the alkylation products 70-50 and 70-51. The alkylation of substituted pyrazoles is described, for example, in Heterocyclic Chemistry, by T. L. Gilchrist, Longman, (1992), p. 309. The reaction is performed between equimolar amounts of the substrates in a polar solvent such as dimethylformamide or tetrahydrofuran, in the presence of a base such as dimethylaminopyridine, lithium hexamethyldisilazide and the like. The products 70-50 and 70-51 are, except in cases where X is dialkylphosphono, converted into the phosphonates 70-52 and 70-53, using the procedures described herein, and deprotection then affords the triols 70-54 and 70-55.

Scheme 70.10. Phosphonates M3 and M4.
Method
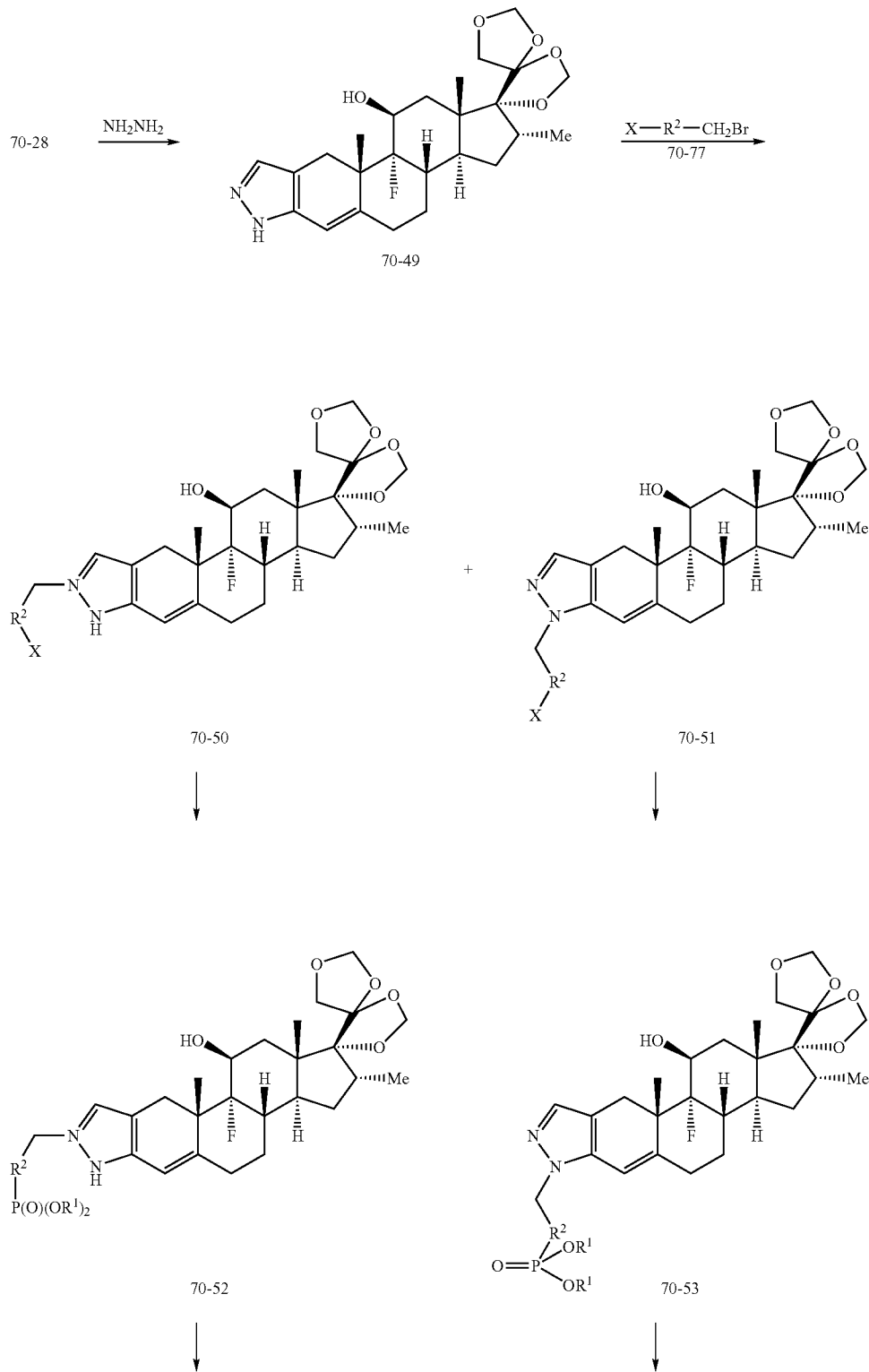

-continued
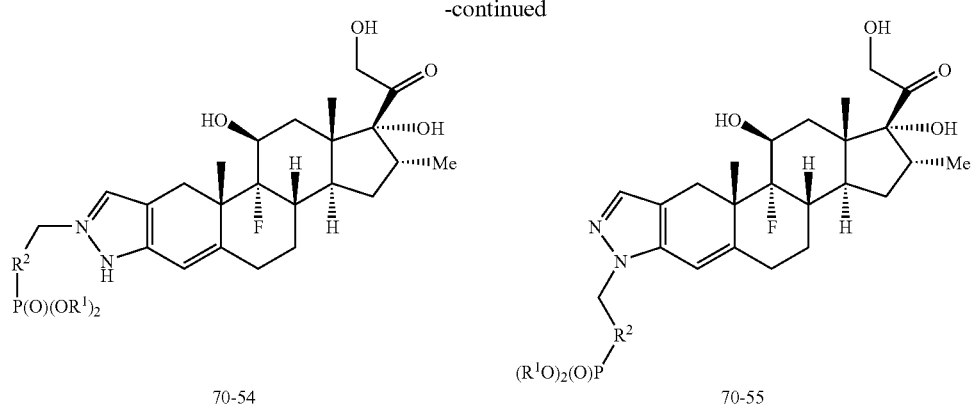
70-54
70-55
As shown in Scheme 70.11, the pyrazole 70-49 is reacted, as described above, with one molar equivalent of a dialkyl bromoacetonyl phosphonate 70-78 (Tet., 1978, 34, 649) to give the alkylated pyrazoles 70-82 and 70-83. Deprotection then yields the triols 70-84 and 70-85.
Scheme 70.11
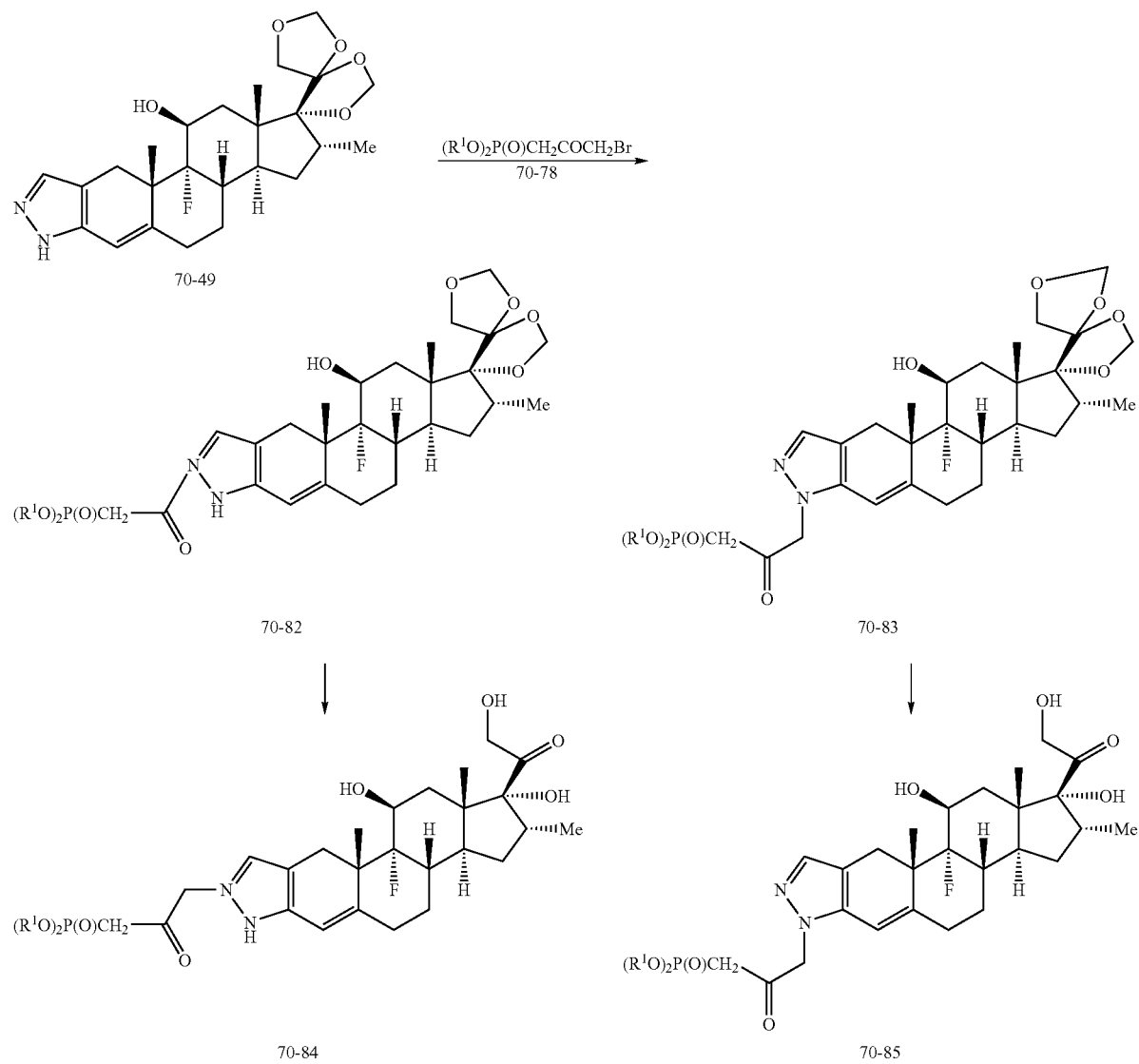

As shown in Scheme 70.12, the pyrazole 70-49 is reacted, as described above, with 1,4-bis(bromomethyl)benzene 70-86 to give the pyrazoles 70-87 and 70-56. The products are subjected to an Arbuzov reaction, in which the bromomethyl substituent is converted into the dialkyl phosphonomethyl substituent, by reaction with a trialkyl phosphite at 120°, to prepare, after deprotection of the side chain, the phosphonates 70-57 and 70-58. The Arbuzov reaction is described in Handb. Organophosphorus Chem., (1992), 115-72. In the procedure, the substrate is heated at from 60° to about 160° with a five to fifty-fold molar excess of the trialkyl phosphite.

Using the above procedures, but employing, in place of the dibromide 70-86, different dibromides, the products analogous to 70-57 and 70-58 are obtained.

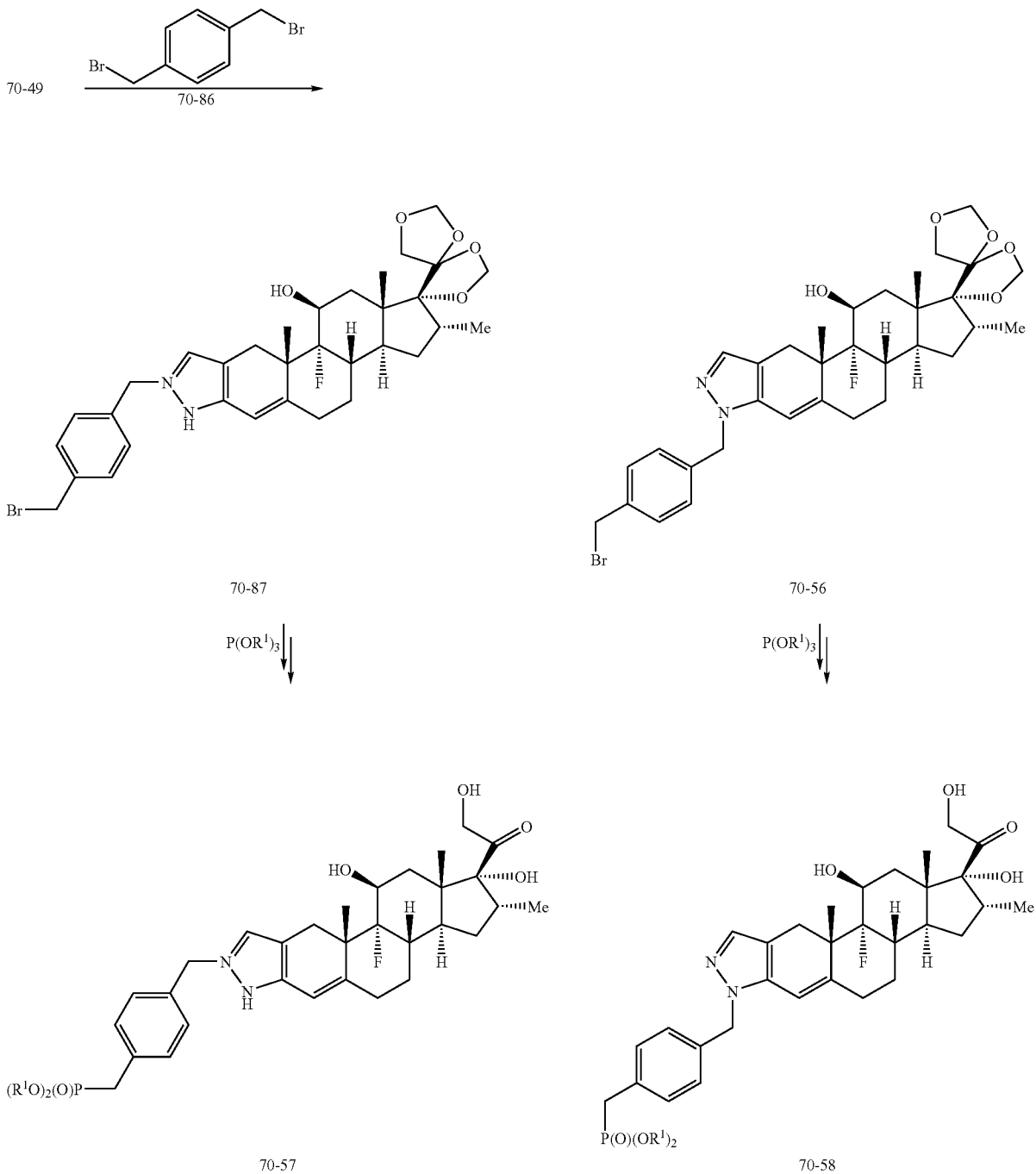

Scheme 70.12

Example 72
Preparation of Exemplary Compounds of the Present Invention
Synthetic methodology towards compounds such as these is described by Westwood et al, J. Med. Chem., (1996), 39, 4608-4621, according to the general routes outlined in Scheme 72.1.
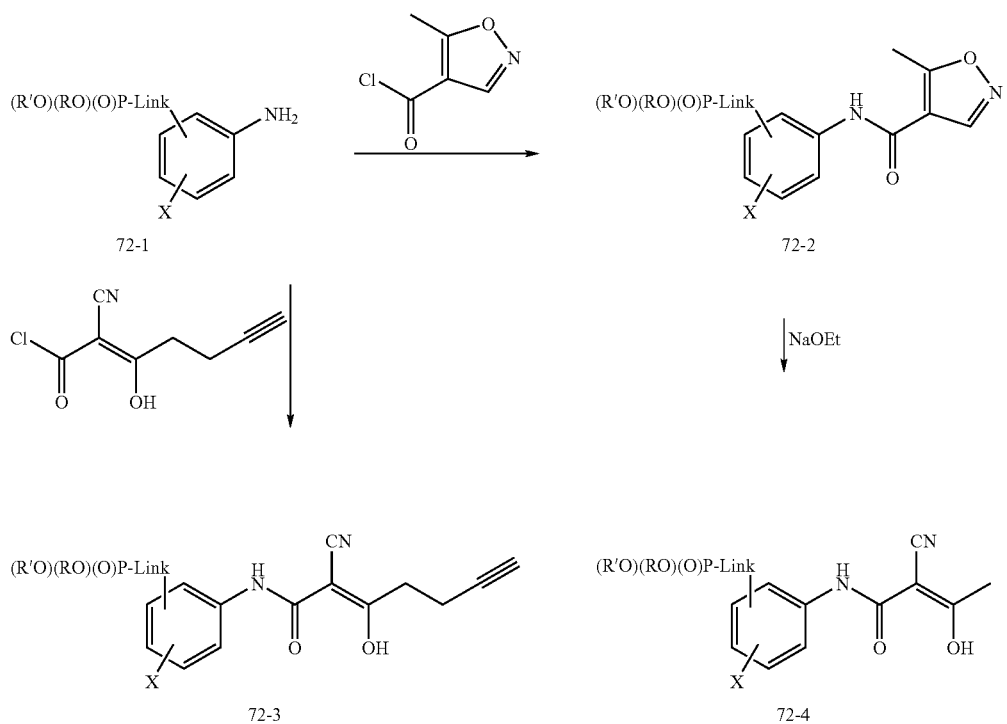
Examples of the synthesis of suitable phosphonate-containing anilines are shown below.
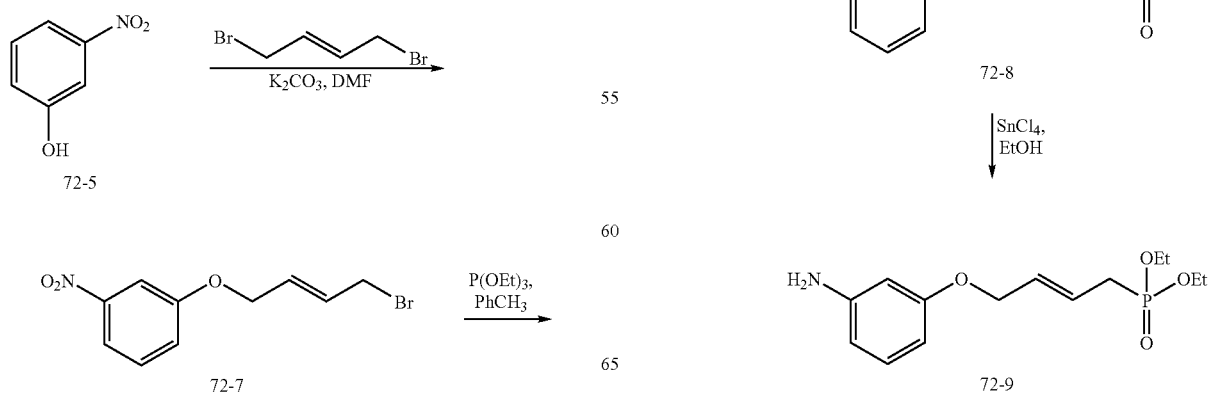

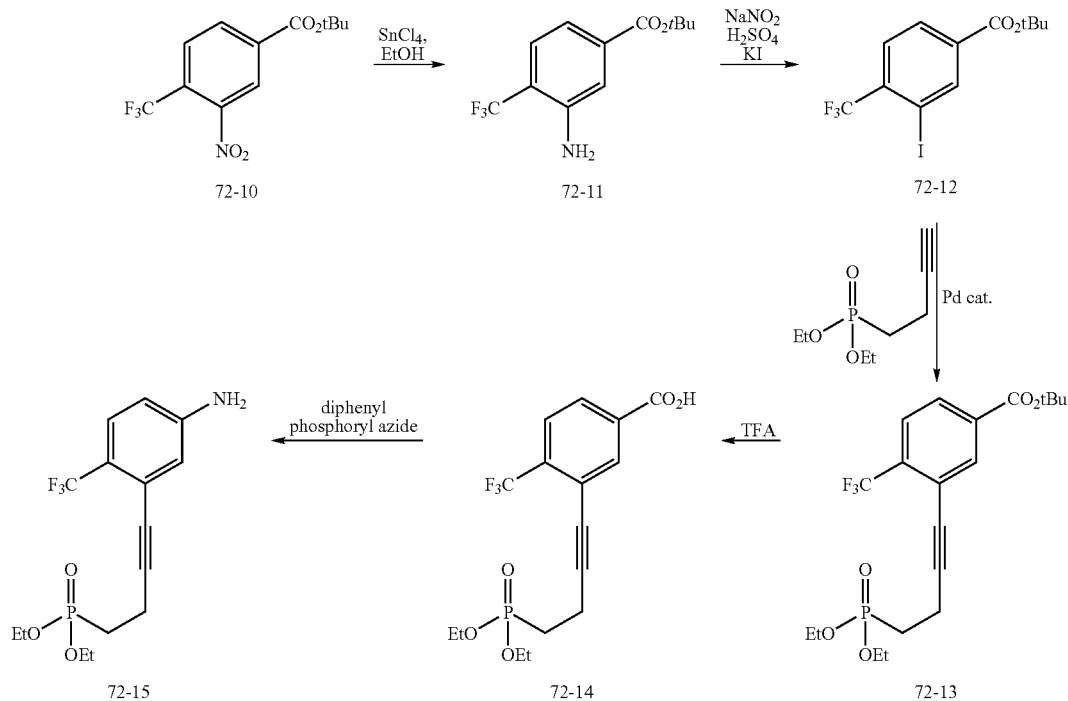
Scheme 72.3
Example 73
Preparation of Exemplary Compounds of the Present Invention
Compounds of the invention can be prepared as generally described by Westwood et al, *J. Med. Chem.*, (1996), 39, 4608-4621, according to the general route outlined in Scheme 73.1.
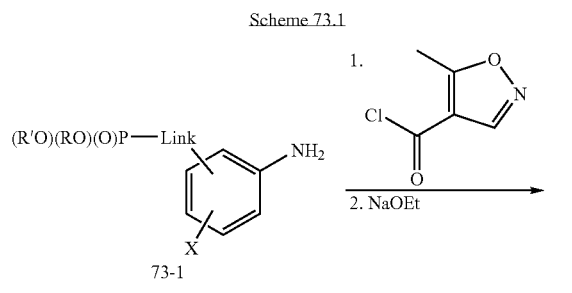
Scheme 73.1
Examples of the synthesis of suitable phosphonate-containing anilines are shown below.
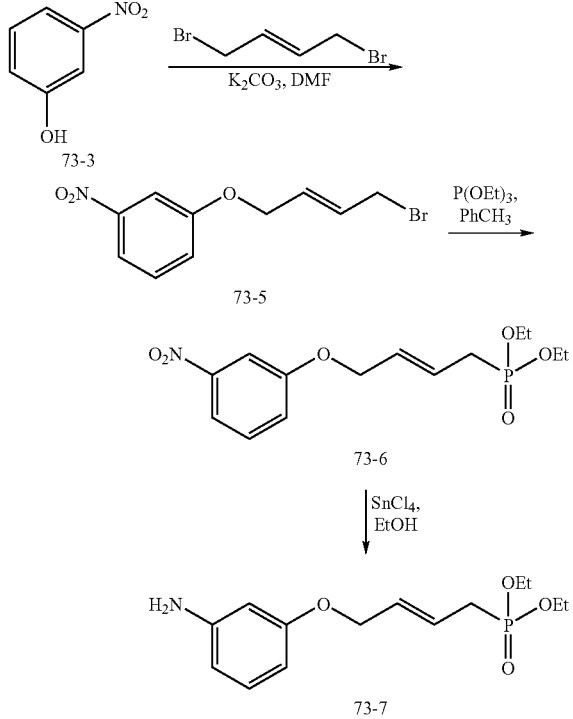
Scheme 73.2

3-Nitrophenol is alkylated with E-1,4-dibromobutene and the resulting monobromide is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. Finally, the desired aniline is generated by tin (II)-mediated reduction of the nitrobenzene.

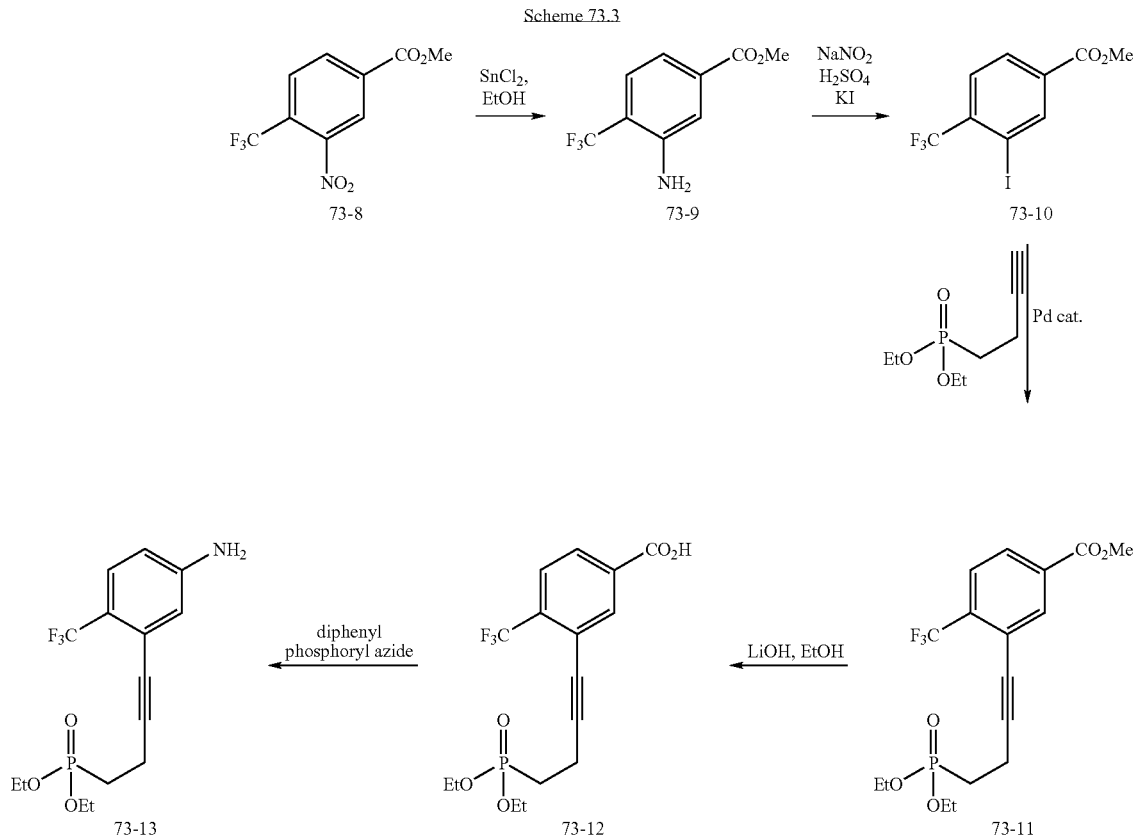

The methyl ester of 3-nitro-4-trifluoromethylbenzoic acid is treated with tin (II) chloride to produce the aniline. The 3-iodobenzoic acid is generated by diazotization and treatment with potassium iodide. A diethylphosphonate ester is attached via an acetylene linker using palladium catalysis, and after saponification of the benzoate ester, Curtius rearrangement of the acyl azide reveals an aniline suitable for incorporation into the synthesis of teriflunomide analogs.

Example 74

Preparation of Exemplary Compounds of the Present Invention

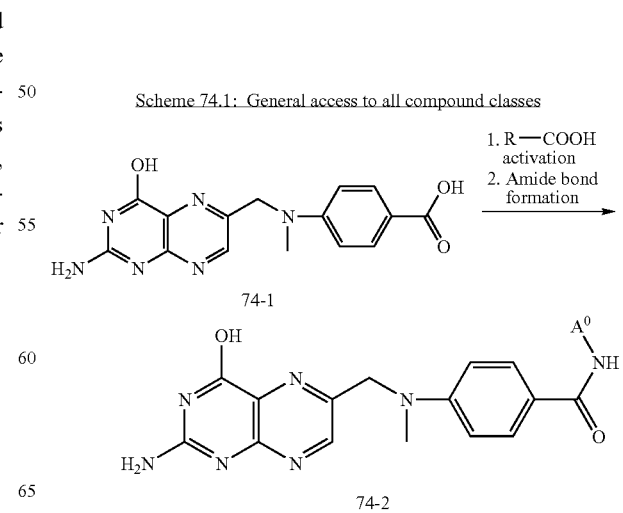

Scheme 74.2: Specific example for Formula M1

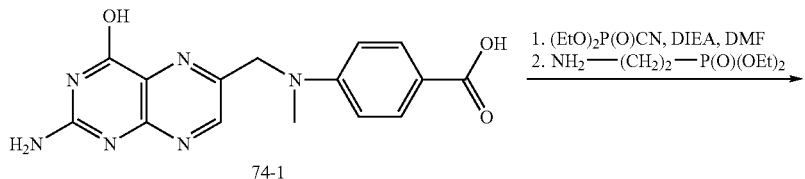

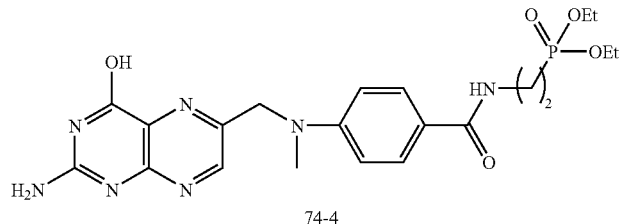

The starting carboxylic acid, synthesized according to *J. Am. Chem. Soc.*, (1948), 70, 1922-1926, is treated in a solvent such as DMF or NMP with a coupling reagent such as diethyl cyanophosphonate or isobutyl chloroformate and a base such as diisopropylethylamine (DIEA) at room temperature (*J. Med. Chem.*, (1982), 25, 960-964 and *J. Med. Chem.*, (1984), 27, 600-604). When the activation is complete, 2-aminoethylphosphonic acid diethyl ester (commercially available) is added. After consumption of the activated species is observed the solvent is removed in vacuo and the product is isolated via chromatography. Alternatively, the product can be isolated through precipitation from the reaction solution with an organic solvent like diethyl ether or the like.

*Chem.*, (1982), 25, 960-964 and *J. Med. Chem.*, (1984), 27, 600-604). When the activation is complete, (2-amino-ethyl-sulfanylmethyl)-phosphonic acid diethyl ester (made by base-catalyzed coupling of 2-aminoethanethiol with diethyl phosphonomethyltriflate, prepared according to *Tetrahedron Lett.*, (1986), 27, 1477) is added. After consumption of the activated species is observed the solvent is removed in vacuo and the intermediate is isolated by chromatography. Alternatively, the intermediate can be isolated through precipitation from the reaction solution with an organic solvent like diethyl ether or the like. The intermediate is then dissolved in a mixture of water, DMF, and acetic acid and is treated with hydrogen peroxide solution (excess). After removal of the Scheme 74.3:

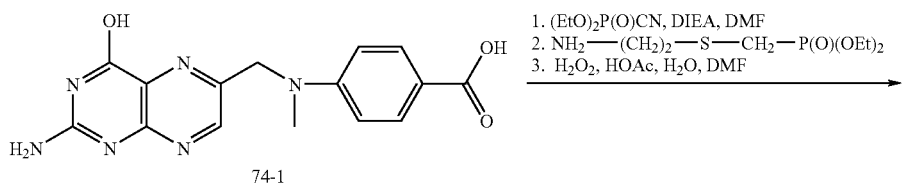

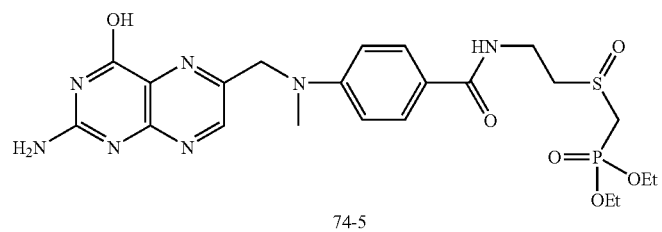

The starting carboxylic acid is treated in a solvent such as DMF or NMP with a coupling reagent such as diethyl cyanophosphonate or isobutyl chloroformate and a base such as diisopropylethylamine (DIEA) at room temperature (*J. Med.* solvents the product is isolated by chromatography. Alternatively, the product can be isolated through precipitation from the reaction solution with an organic solvent like diethyl ether or the like.

Scheme 74.4:

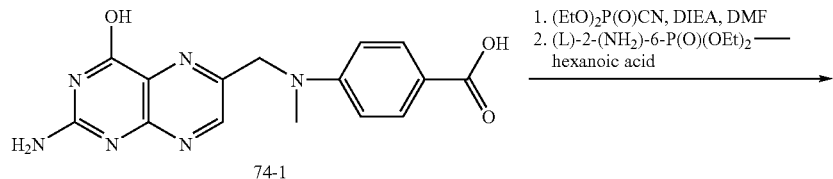

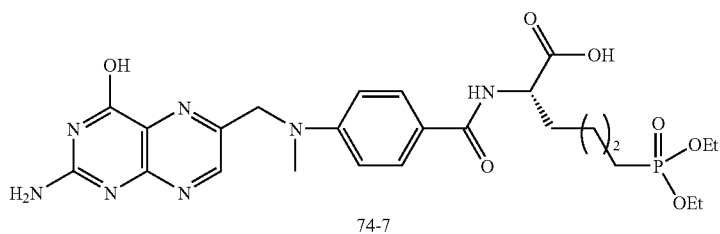

74-7

The starting carboxylic acid is treated in a solvent such as DMF or NMP with a coupling reagent such as diethyl cyanophosphonate or isobutyl chloroformate and a base such as DIEA at room temperature (*J. Med. Chem.*, (1982), 25, 960-964 and *J. Med. Chem.*, (1984), 27, 600-604.). When the activation is complete, (L)-2-amino-6-(diethylphosphonato)-hexanoic acid is added. After consumption of the activated species is observed the solvent is removed in vacuo and the product is isolated by chromatography. Alternatively, the product can be isolated through precipitation from the reaction solution with an organic solvent like diethyl ether or the like.

DIEA at room temperature (*J. Med. Chem.*, (1982), 25, 960-964 and *J. Med. Chem.*, (1984), 27, 600-604). When the activation is complete, 4-amino-4-(diethylphosphonato)-butyric acid tert butylester (*J. Am. Chem. Soc.*, (1995), 117, 10879-10888) is added. After consumption of the activated species is observed the solvent is removed in vacuo and the intermediate is isolated by chromatography. Alternatively, the intermediate can be isolated through precipitation from the reaction solution with an organic solvent like diethyl ether or the like. The crude intermediate is then dissolved in DMF and treated with TFA (excess). The product is isolated by chromatography after removal of the solvents. Alternatively, the Scheme 74.5:

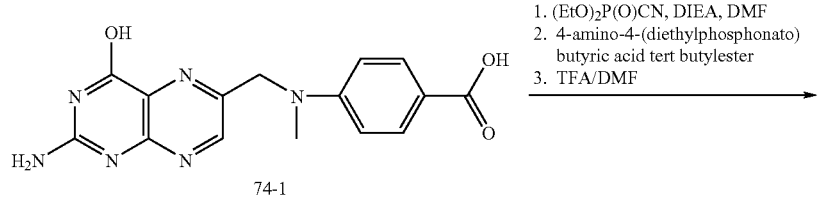

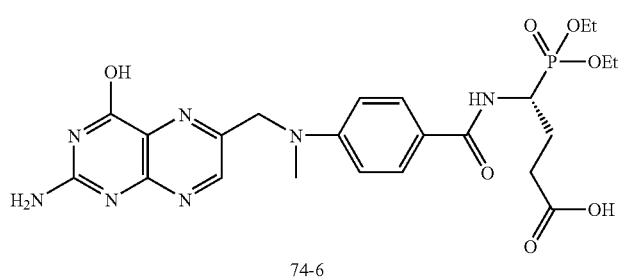

74-6

The starting carboxylic acid is treated in a solvent such as DMF or NMP with a coupling reagent such as diethyl cyanophosphonate or isobutyl chloroformate and a base such as product can be isolated through precipitation form the reaction solution with an organic solvent like diethyl ether or the like.

Example 75

Preparation of Exemplary Compounds of the Present Invention

The phosphorus containing merimepodib analog 75-2 is synthesized from parent compounds by alkylation. Merimepodib 75-1 is obtained by the procedure as described in U.S. Pat. No. 6,054,472 and U.S. Pat. No. 6,344,465. Schemes 75.1-75.2 shows the procedure for the synthesis of 75-2 and 75-4. Methoxy group of merimepodib 75-1 is demethylated to phenolic OH using a suitable reagent, such as boron tribromide. The phosphonate moiety is introduced to the phenolic OH in a suitable aprotic solvent such as, DMF and is then treated with the phosphonate reagent 75-40, 75-41, bearing a leaving group, for example, bromine, mesyl, tosyl, or trifluoromethanesulfonyl, in the presence of a suitable organic or inorganic base.

Scheme 75.1

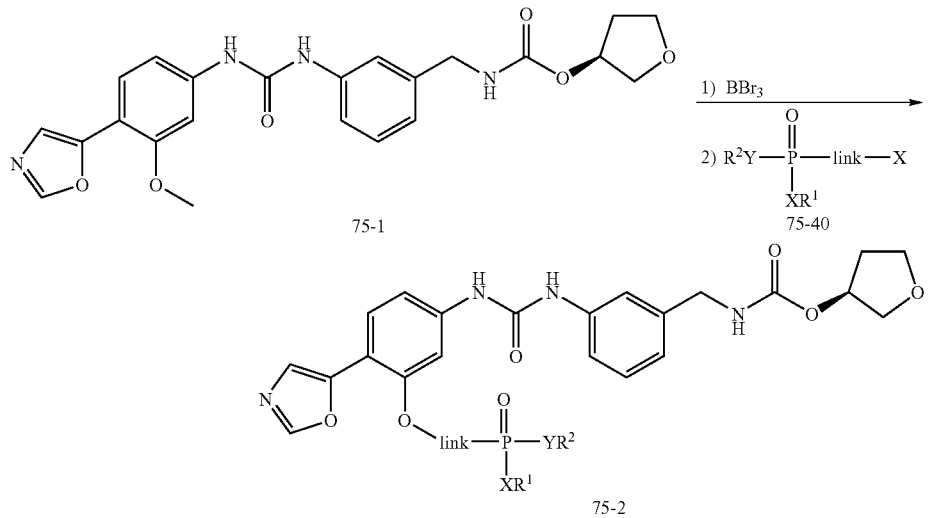

For example, a solution of 75-1 in dichloromethane is treated with boron tribromide to obtain the demethylated compound 75-3. Compound 75-3 is then treated with cesium carbonate and one equivalent of (trifluoromethanesulfonyloxy)methylphosphonic acid diethyl ester 75-41 to give merimepodib-phosphonate 75-4 in which the linkage is a methylene group as shown in Scheme 75.2. Using the above procedure but employing different phosphonate reagents 75-40 the corresponding products 75-2 bearing different linking group can be obtained.

Scheme 75.2

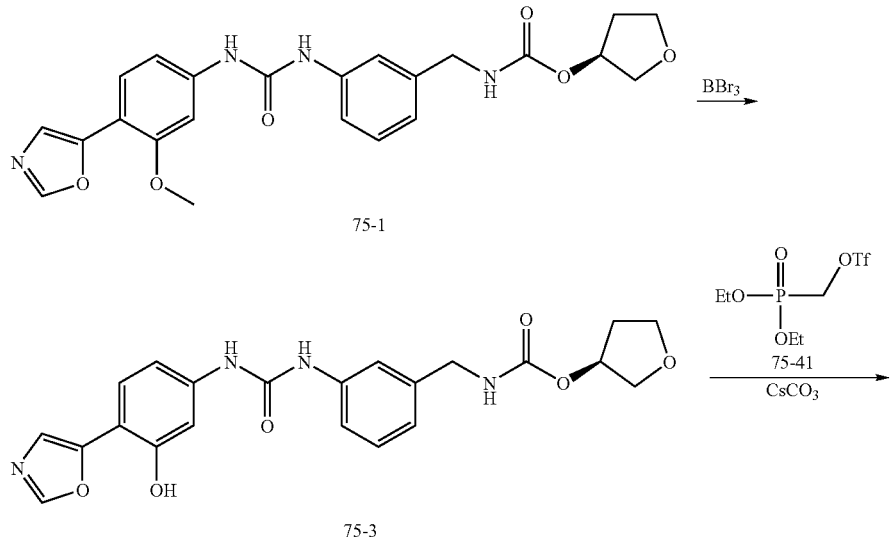

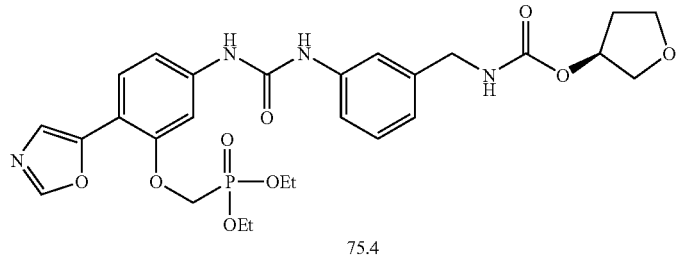

75.4

Synthesis of merimepodib analogs 75-2, 75-12 and 75-13 is shown in Schemes 75.3-75.4. The imidazole containing intermediate 75-7 is synthesized from an aldehyde 75-6 by the procedure of Shih in *Tetrahedron Lett.* (1993), 34, 595. Compound 75-6 is prepared by a two-step procedure described in U.S. Pat. No. 5,807,876, U.S. Pat. No. 6,054,472, and U.S. Pat. No. 6,344,465. The imidazole is protected using suitable reagent, for example 2-(trimethylsilyl)ethyoxymethyl (SEM) chloride, and the compound 75-8 is converted to 75-10 by the similar procedure described for the synthesis of 75-1 in U.S. Pat. No. 6,054,472 and U.S. Pat. No. 6,344,465. After the protecting group on the imidazole of 75-10 is removed, the phosphonate containing moiety is introduced to the imidazole as shown in Schemes 75.4.

Scheme 75.3

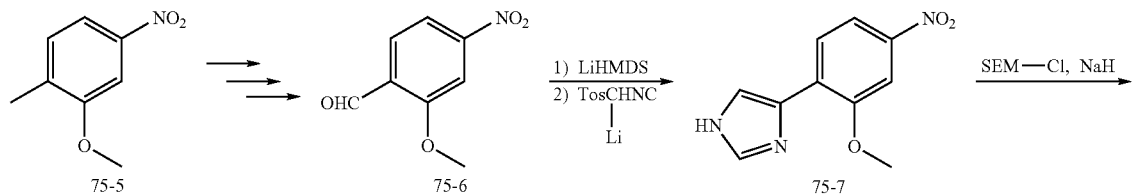

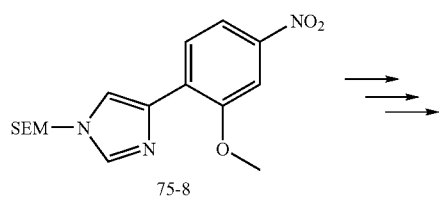

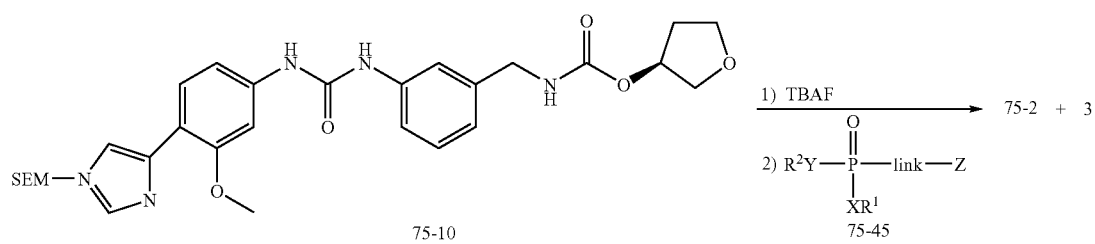

For example, compound 75-10 is treated with tetrabutylammonium fluoride in THF in reflux condition and the resulting 75-11 is alkylated with 75-41, 75-42 using sodium hydride as a base to obtain two isomers 75-12 and 75-13, which are separated by chromatography.

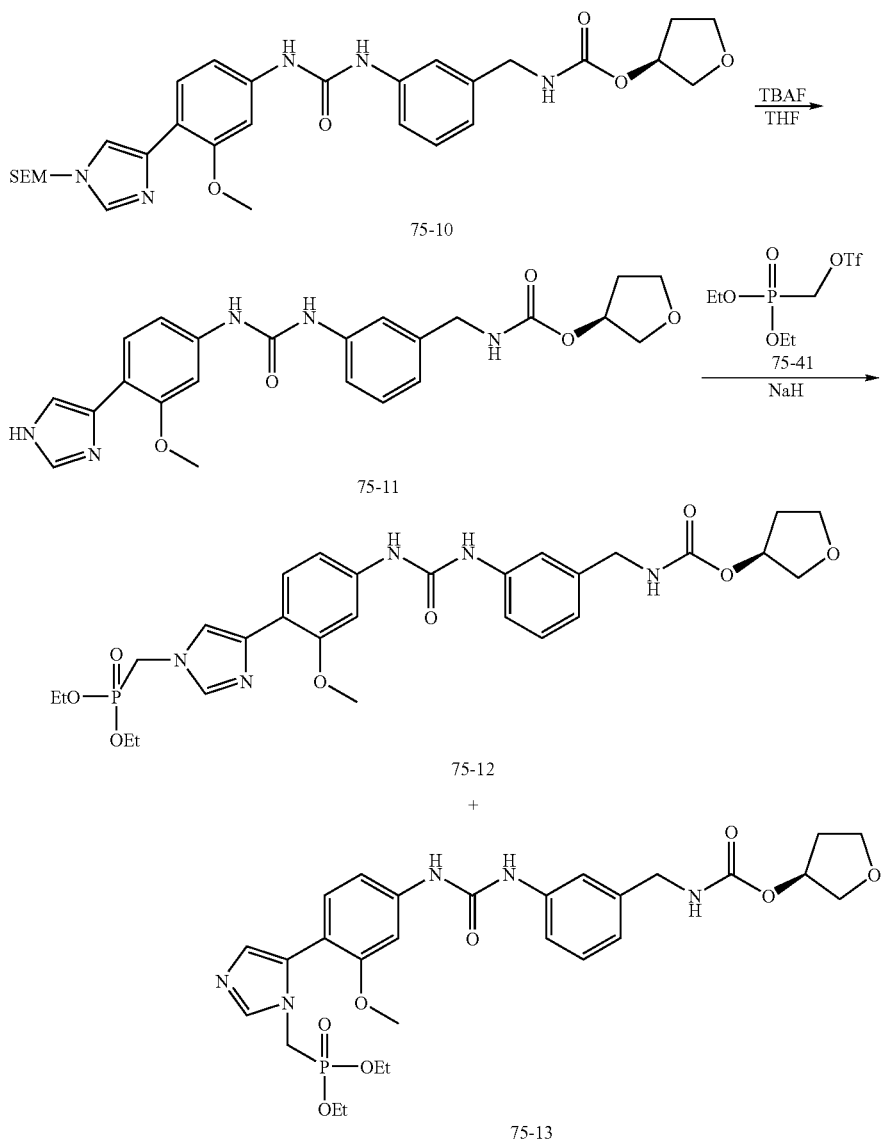

Schemes 75.5-75.6 shows the preparation of merimepodib analog 75-17. Tetrasubstituted benzene derivatives are obtained by literature procedures (Ichikawa and Ichibagase *Yakugaku Zasshi* (1963), 83, 103; Norio, A. et al. *Tetrahedron Lett*. (1992), 33(37), 5403). After the phenolic OH is protected with a suitable protecting group, for example benzyl group, the compound 75-16 is synthesized by the same procedure of the synthesis of 75-1 as described in U.S. Pat. No. 6,054,472, and U.S. Pat. No. 6,344,465. After the protecting group is removed, the phosphonate containing moiety is introduced to the phenolic OH using the phosphonate reagent 75-45, bearing a suitable leaving group.

For example, a solution of 75-18, which is obtained by the procedure of Norio et al. (*Tetrahedron Lett*. (1992), 33(37), 5403), is treated with sodium hydride and one equivalent of benzyl bromide in DMF to get 75-19. Compound 75-19 is converted to 75-20 by a series of steps reported in U.S. Pat. No. 6,054,472, and U.S. Pat. No. 6,344,465 for the synthesis of 75-1 from 75-6. After the benzyl protecting group of 75-20 is removed by catalytic hydrogenation, a phosphonate bearing moiety is attached by alkylation of the resulting phenol in DMF using sodium hydride and one equivalent of (trifluoromethanesulfonyloxy)methylphosphonic acid diethyl ester 75-42 to give 75-21.

Scheme 75.5
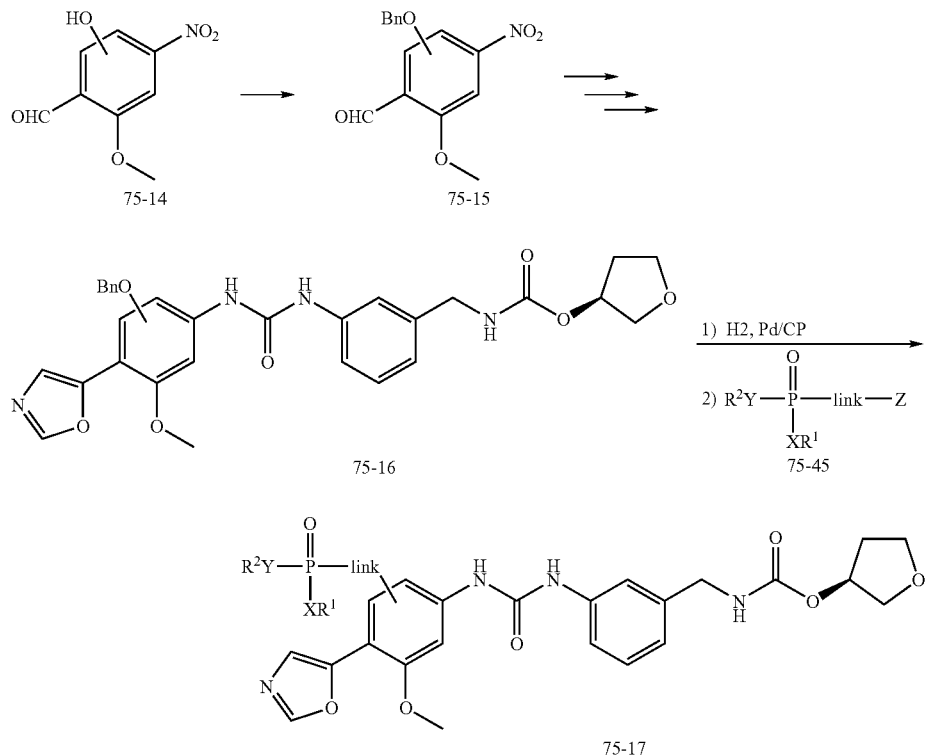
Scheme 75.6
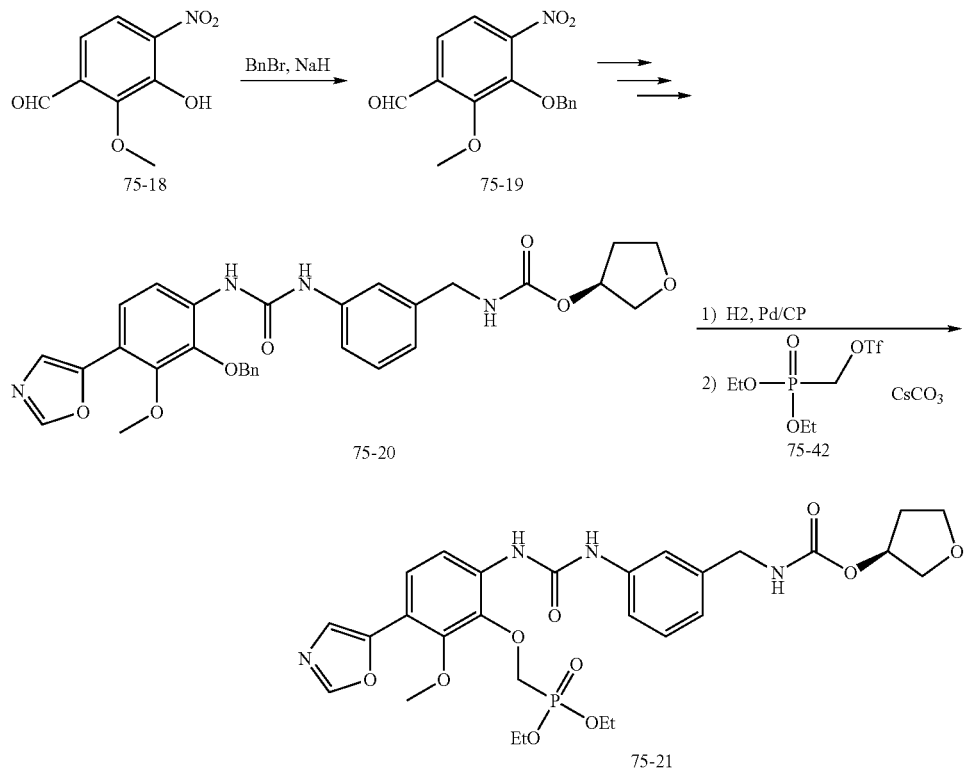

Synthesis of merimepodib analog 75-26 is shown in Schemes 75.7-75.8. Compound 75-22, an intermediate in the synthesis of 75-1, is treated with carbonyldiimidazole or triphosgene followed by the compound 75-23, which has an handle to attach phosphonate moiety. Compound 75-23 bearing an extra substituent is synthesized from the tri subatituted phenol with a cyano and a nitro groups, which is either commercially available or by literature procedures (Zolfigol, M. A. et. al. *Indian J. Chem. Sect. B* (2001), 40, 1191; De Jongh, R. O. et al. *Rec. Trav. Chim. Pays-Bas* (1968), 87, 1327). The resulting 75-24 is converted to 75-25 using the procedure described in U.S. Pat. No. 6,054,472, and U.S. Pat. No. 6,344,465 for the synthesis of 75-1. The phosphonate moiety of 75-26 is attached after deprotection of the benzyl group of 75-25.

For example, the bromine substituent of compound 75-27 is substituted with cyano group by the procedure of De Jongh, R. O. et al. (*Rec. Trav. Chim. Pays-Bas* (1968), 87, 1327) and the methoxy group is converted to benzyloxy group as a protecting group, which affords compound 75-28. After selective reduction of cyano to aminomethyl group by borane, the amino group is protected with Boc group and then the reduction of the nitro group using tin (II) chloride generates compound 75-29. This substituted aniline 75-29 is then treated with a reaction mixture of the compound 75-22 and carbonyldiimidazole, as described for the synthesis of 75-1 in U.S. Pat. No. 6,054,472, and U.S. Pat. No. 6,344,465, to form the urea 75-30. Compound 75-30 is easily converted to 75-31, analog of 75-1 bearing benzyloxy group. Deprotection of the benzyl group using catalytic hydrogenation followed by attachment of a phosphonate moiety using 75-41, 75-42 in the presence of cesium carbonate produces 75-32.

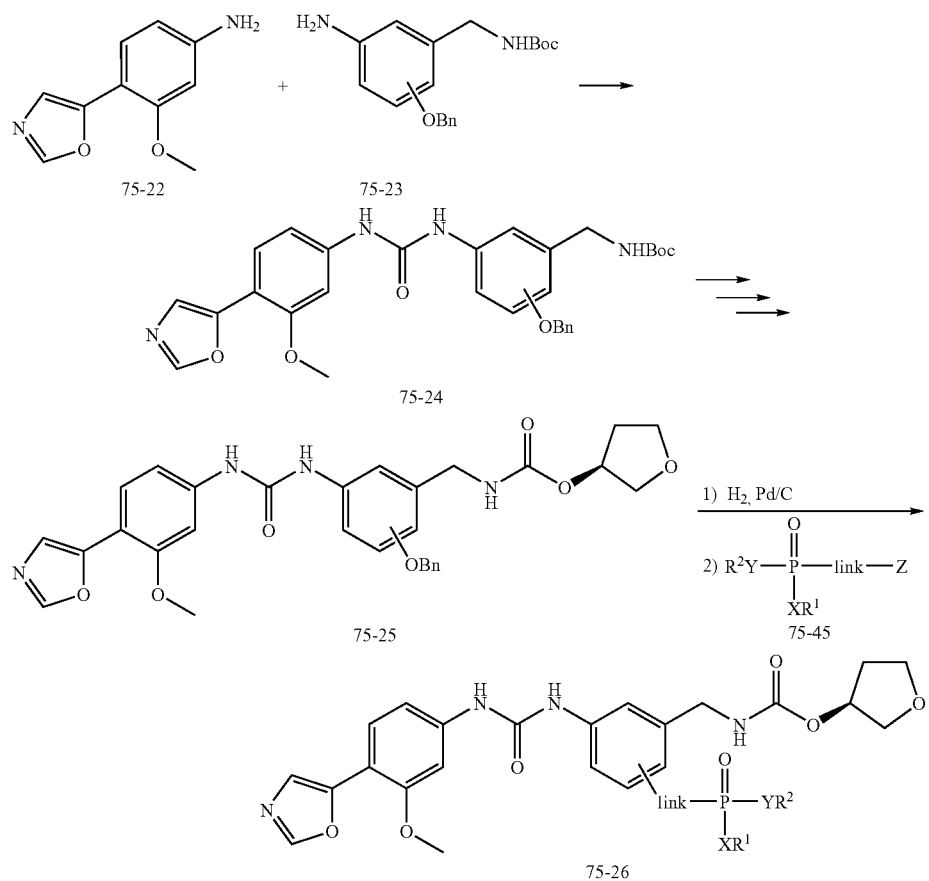

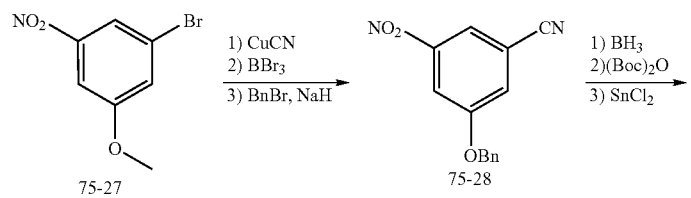

-continued

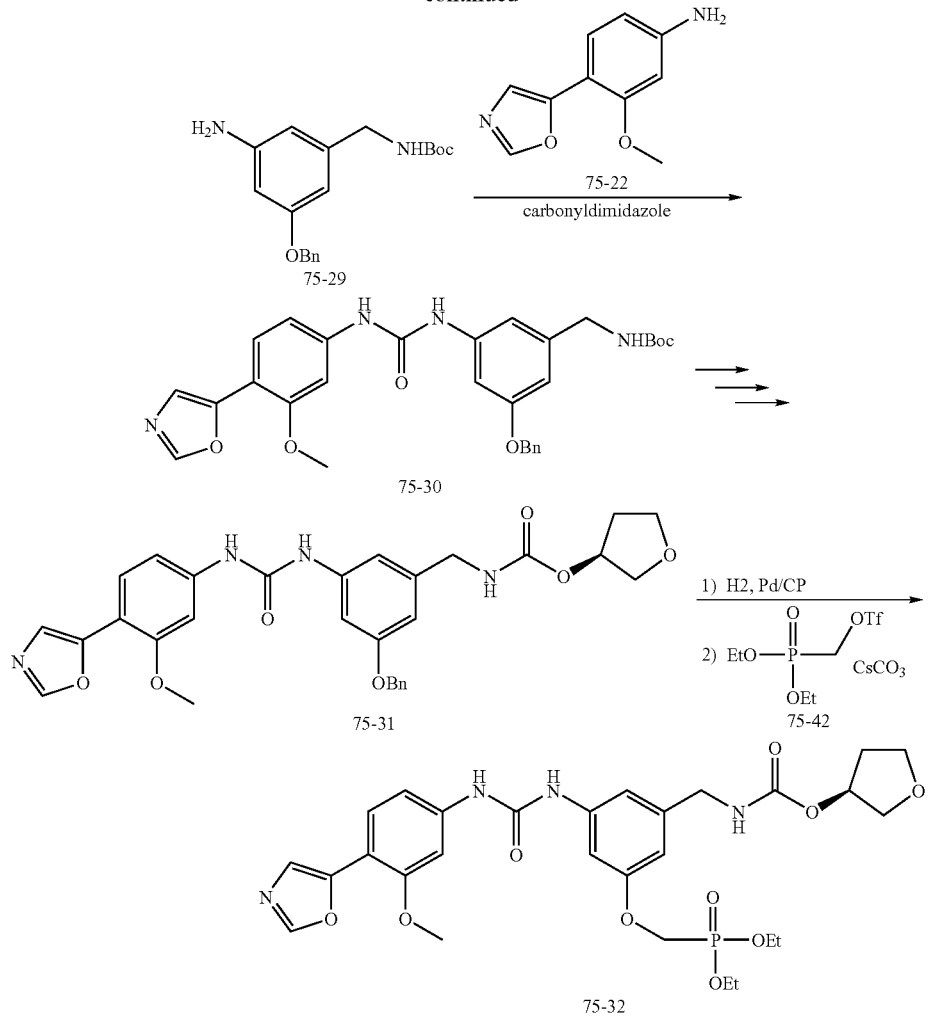

Example 76

Preparation of Exemplary Compounds of the Present Invention

Preparation of Phosphonate Prodrugs of Tamoxifen and Toremifene Citrate

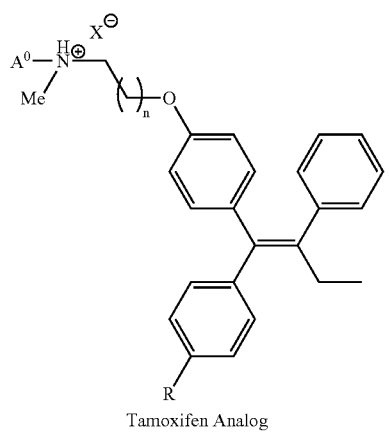

Tamoxifen Analog

-continued

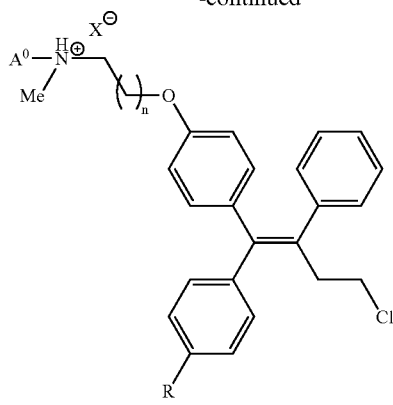

Toremifene Analog

A number of analogs of tamoxifen have been prepared and tested. A high degree of flexibility is observed at the aminoethyl portion of the compound toward substitution (Meegan et al. *Anti-Cancer Drug Design*, (2001), 16, 57). Based on the available SAR, this position is chosen as one handle for attachment of the prodrug moiety. A large number of analogs of tamoxifen have been reported, many having favorable profiles. For a review on a number of tamoxifen analogs, see Meegan, M. J., Lloyd, D. G., *Current Medicinal Chemistry*, (2003), 10, 181. Considering that these analogs are similar to tamoxifen, the prodrug approach on the same site as tamoxifen can be applied to them. A number of additional sites on the tamoxifen core are available for attachment of the prodrug group. Considering the scale up methods that are well established for tamoxifen, attachment of prodrug through the amino ethanol group on the B ring is one option. The original synthesis of tamoxifen (Harper et al., GB1064629 and Harper et al., GB1013907) has been modified recently (Smyth, T. P., Corby, B. W., *Organic Process Research & Development*, (1997), 1, 264). This new method was developed for large scale preparation. Additionally, installation of the amino ethyl group attached to the B ring is performed late in the synthesis which is advantageous for one prodrug synthesis.

Scheme 76.1
(all compound numbers in this scheme refer only to this Example)

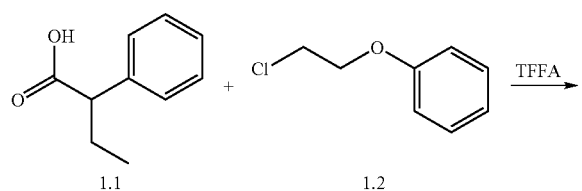

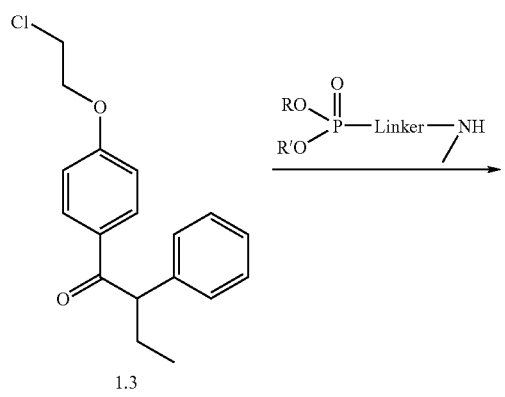

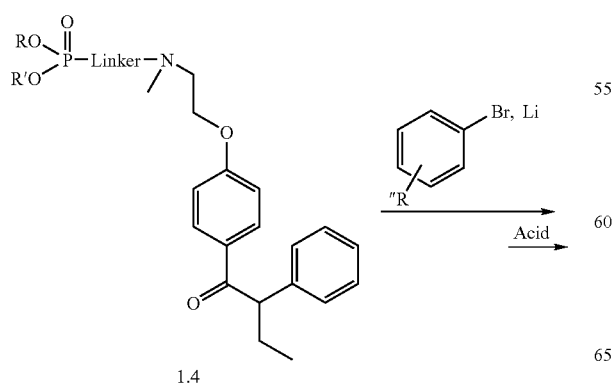

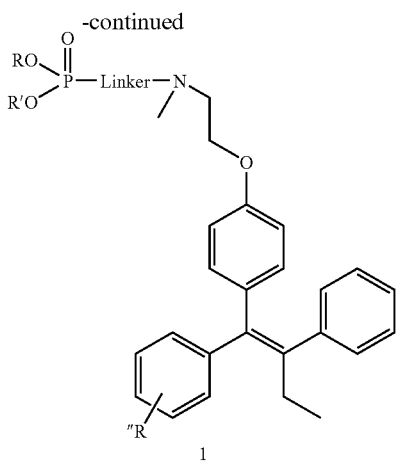

-continued

Synthesis of compounds such as phosphonate 1 (of Scheme 76.1) are illustrated above. Compounds 1.1 and 1.2 (of Scheme 76.1) are condensed using trifluoroacetic anhydride as described in Smyth et al., *Organic Process Research & Development*, (1997), 1, 264. Replacement of the halogen with amino-linker-phosphonate provides compound 1.4 (in Scheme 76.1). A final Grignard reaction to introduce the last aromatic group, followed by dehydration in acidic medium provides compound 1 (of Scheme 76.1). The order of the last two steps can be switched. First, a Grignard reaction can be performed to install the tetrasubstituted olefin followed by displacement of halogen (McCague R., *J. Chem. Res.*, 1986, 0771). The final product is a mixture of cis and trans isomers which are separated by crystallization. Also, further diversity onto the aromatic A ring is incorporated by choice of substitutions attached to the arylbromide that is used in the Grignard reaction.

Scheme 76.2
(all compound numbers in this scheme refer only to this Example)

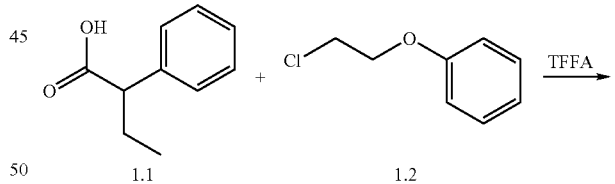

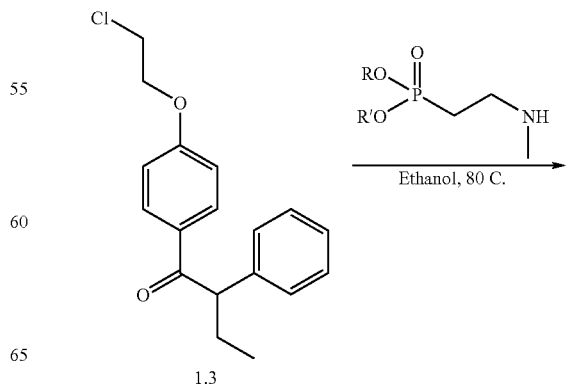

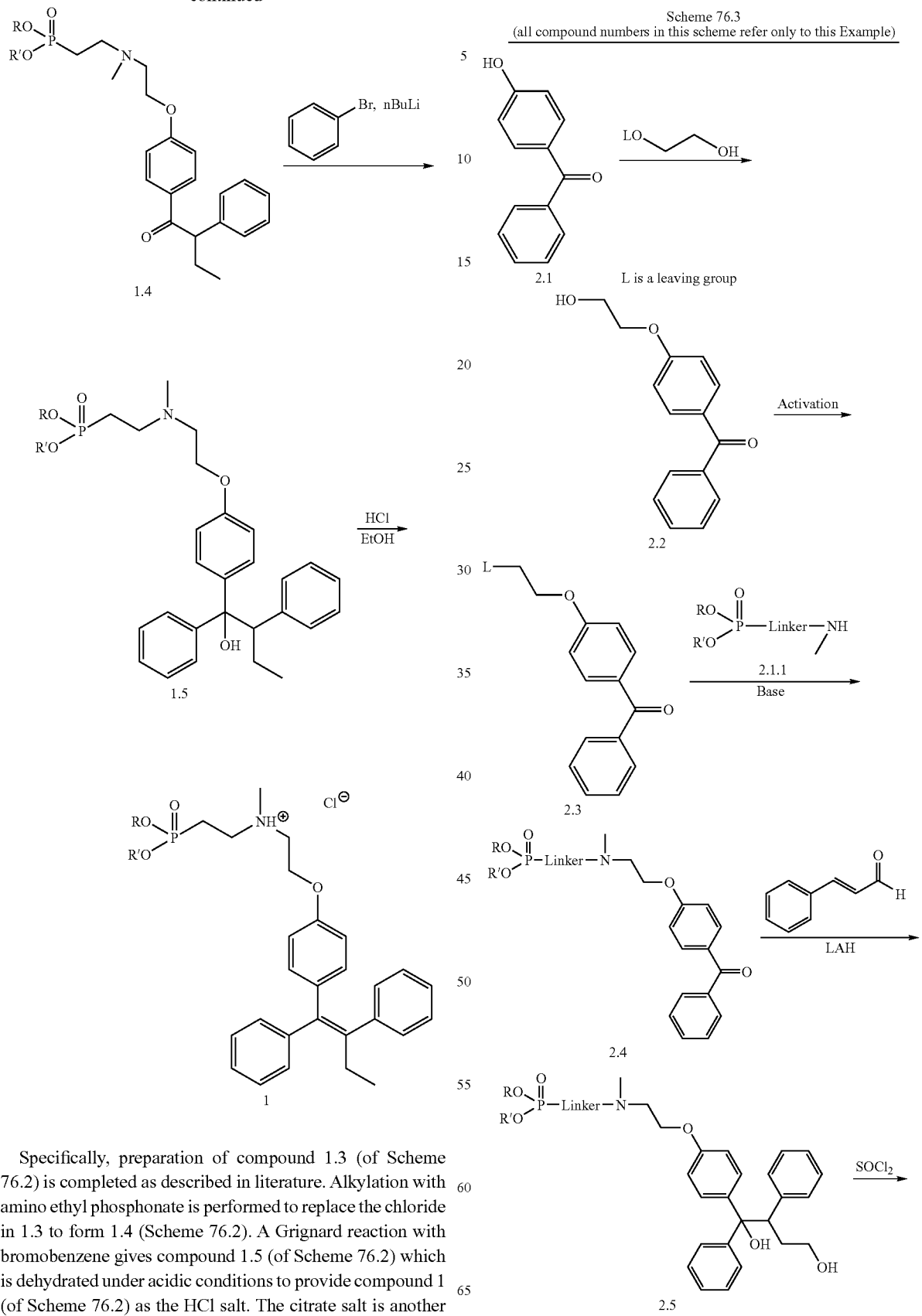

Specifically, preparation of compound 1.3 (of Scheme 76.2) is completed as described in literature. Alkylation with amino ethyl phosphonate is performed to replace the chloride in 1.3 to form 1.4 (Scheme 76.2). A Grignard reaction with bromobenzene gives compound 1.5 (of Scheme 76.2) which is dehydrated under acidic conditions to provide compound 1 (of Scheme 76.2) as the HCl salt. The citrate salt is another useful compound. Other salts can also be generated.

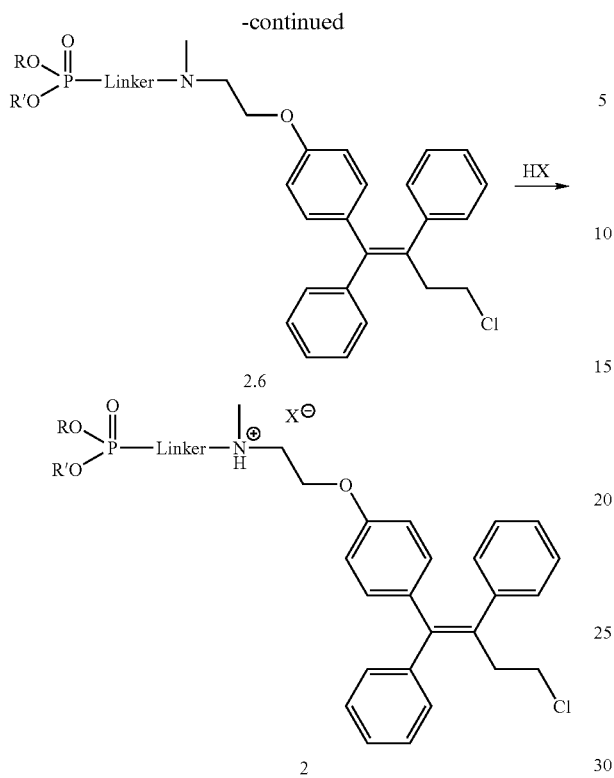

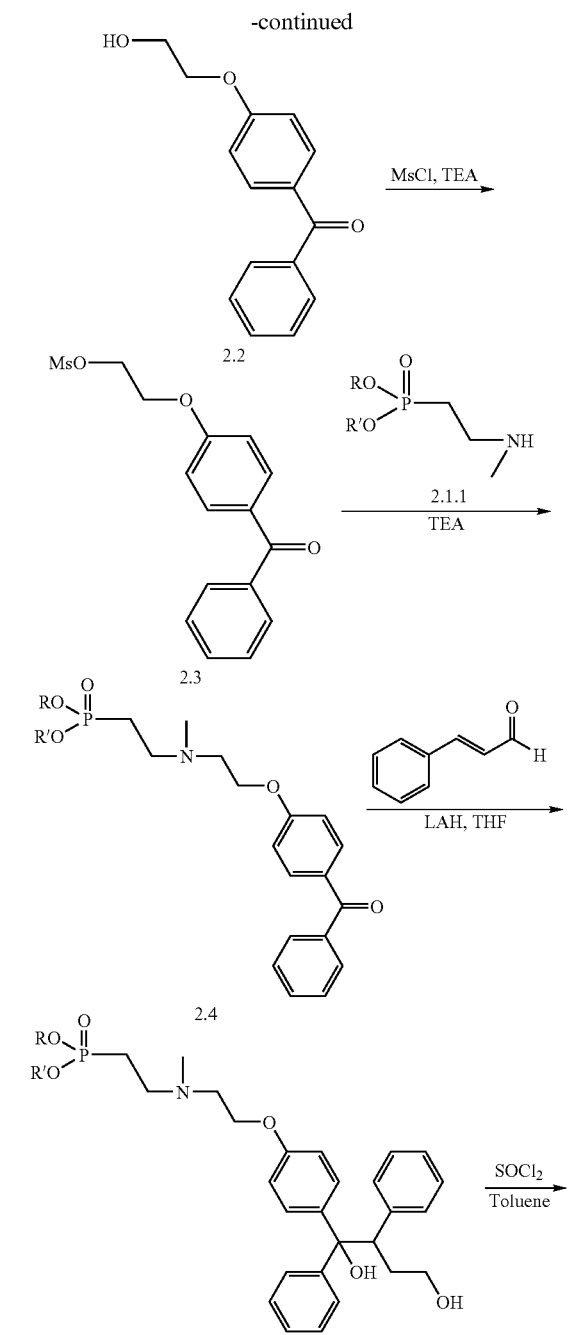

Syntheses of a number of analogs of toremifene are described in detail in U.S. Pat. No. 4,696,949. Synthesis of prodrugs of toremifene is shown above in Scheme 76.3. The prodrug is installed early in the synthesis. It is possible to protect the 4-hydroxy benzophenone initially and remove the protecting group near the end of the synthetic sequence. In that case, the prodrug group is installed near the end of the synthesis. The preparation shown in Scheme 76.3 utilizes 4-hydroxy benzophenone as the starting materials. A two carbon linker is attached and subsequently activated toward synthesis of compound 2.3 (of Scheme 76.3). Introduction of the aminophosphonate 2.1.1 (of Scheme 76.3) at this stage completes the left half of the molecule. Addition of cinnamaldehyde to lithium aluminium hydride followed by the benzophenone 2.4 yields diol 2.5 (both of Scheme 76.3). Dehydration of 2.5 and conversion of the 4-OH to chloride is performed by addition of thionyl chloride to provide compound 2.6 (of Scheme 76.3). Final product 2 (Scheme 76.3) is prepared by formation of the desired salt.

Scheme 76.4
(all compound numbers in this scheme refer only to this Example)

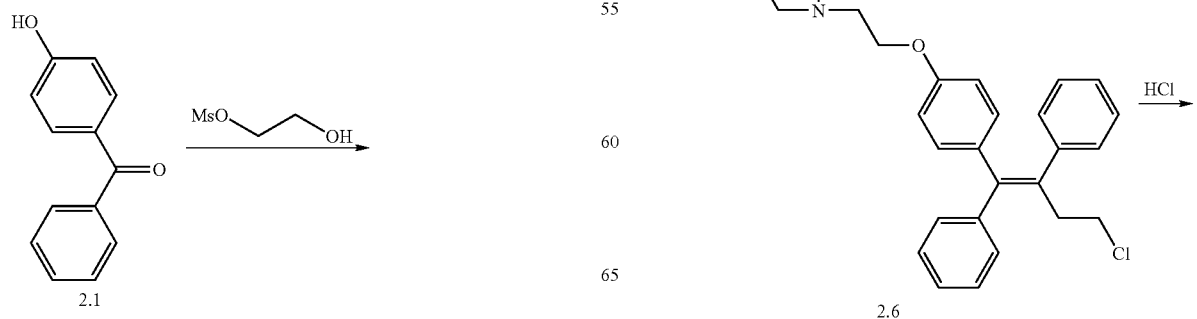

-continued

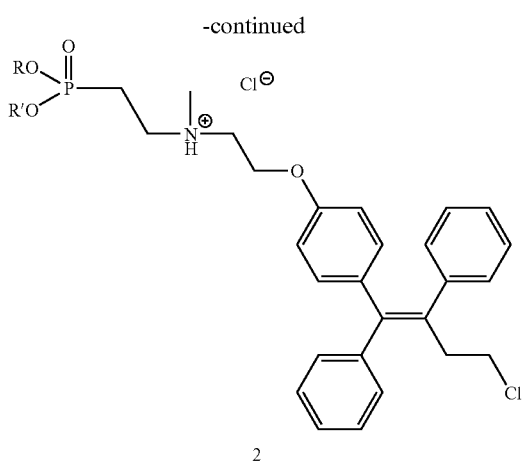

2

Specifically, 4-hydroxy benzophenone is reacted with 1-mesyl ethane diol to yield 2.2 (of Scheme 76.4) in CH$_2$Cl$_2$. Activation of alcohol 2.2 (Scheme 76.4) to mesylate 2.3 (Scheme 76.4) is performed using mesyl chloride in CH$_2$Cl$_2$ using TEA as a scavenger. Alkylation of mesylate 2.3 with the N-methyl amino ethyl phosphonate 2.1.1 (of Scheme 76.4) in EtOH at 80° C. proceeds well to provide compound 2.4 (Scheme 76.4). Addition of 2.4 (1 equivalent) to a mixture of cinnamaldehyde (1 equivalent) and lithium aluminum hydride (0.55 equivalent) in THF yields compound 2.5 (of Scheme 76.4) after 30 minutes of stirring at room temperature. Dehydration of 2.5 (Scheme 76.4) using thionyl chloride in toluene is complete after 3 hours at 80° C. to provide compound 2.6 (Scheme 76.4). A variety of salts can be prepared subsequently. The citrate salt of toremifene is one exemplary compound. Further modification of the phosphonate prodrug can be performed to the phosphonate diester, bisamidate, or monoamidate as illustrated above.

Example 77

Preparation of Exemplary Compounds of the Present Invention

Preparation of Phosphonate Prodrugs of Raloxifene Hydrochloride

Many structural modifications of raloxifene have been investigated and the SAR of this group of drugs is well established. In brief, the hydroxyl substituents of aryl rings of raloxifene are predictably critical to the potent activity of the compound. The C-60H is positioned to bind to the ER residue pair Arg 394/Glu 343 in the same way as the 3-OH of estradiol. Also, the 4'-OH, which mimics the 17β-OH of estradiol, binds with the His 524 as demonstrated by crystal structure studies (Anzo, et al., *J. Natl. Cancer Inst.*, (1996), 88, 123). The amine of the piperidine ring is also important in binding to the aspartate 351 of the estrgen receptor. This amine also plays a role in tissue specificity. However, a number of N,N-dialkyl analogs of raloxifene show equipotent activity to the parent compound. Therefore, substitution of the prodrug group at that terminus of the compound is a preferred embodiment of this work.

Three types of substitutions are set forth herein. Two are variations of attachement of prodrug to the tertiary amine region (Scheme 77.1). Another attachment site on the raloxifene is the carbonyl position. Considering this carbonyl moiety can be easily substituted with a simple oxygen, this position can be used as a potential handle for the phosphonate prodrugs (Palkowitz, et al., *J. Med. Chem.*, (1997), 40, 10, 1407).

The first phosphonate prodrug is prepared following the general Schemes 77.2-77.3. An appropriately protected diol is attached on to the phenolic position of 4-hydroxyl benzoic acid methyl ester by Williamson ether synthesis methods. Removal of the protecting group generated compound 77-5. Turning the hydroxyl group into an appropriate leaving group, such as mesyl, bromide of trifluoromethylsulfonyl, followed by addition of amino phosphonate prodrug moiety gives compound 77-6, 77-50. Releasing the methyl ester, followed by activation of the acid by formation of the acid chloride proceeds as reported in literature (Jones, et al. *J. Med. Chem.*, 1984, 27, 1057). Friedal-Crafts aroylation with compound 77-7, 77-33, 77-25 which is the product of a rearrangement (Kost et al., *Zh. Org. Khim*, 1970, 6, 1503), (Jones, C. D., EP 0062503) goes smoothly to provide the protected desired compound. Final deprotection provides compound 77-9. Different salts can be prepared to assist the solubility of the final compound.

A particular example of the general route above is shown in Scheme 77.3. Compound 77-4 is alkylated with the TMS protected diol 77-23 using K$_2$CO$_3$ in DMF. Removal of the silyl protecting group proceeds cleanly with TFA to provide precursor 77-5. Activation of 77-5 by formation of the mesylate using MsCl and TEA in CH$_2$Cl$_2$, followed by addition of the amino ethyl phosphonate 77-22, 77-32 proceeds well to generate amine 77-6, 77-50. Removal of the methyl ester protecting group of 77-6, 77-50 followed by one-pot two step reactions of Friedal-Crafts aroylation-deprotection using thioethanol proceeds very well to generate HCl salt of the final compound 77-10, 77-35.

Generation of the piperazyl phosphonate prodrug is performed the same way as for compound 77-10, 77-35. Synthesis of 77-24, 77-40 proceeds using a mono protected piperazine and the 2-hydroxyethyl phosphonate. Subsequent steps in the synthesis are as described in Schemes 77.2-77.3. Specifically, addition of 77-24, 77-40 to 77-5 in CH$_2$Cl$_2$ using TEA as a scavenger gives 77-12, 77-42. Deprotection of the methyl ester, activation of the acid with thionyl chloride and the Friedal-Crafts aroylation proceed as before. Compound 77-15, 77-16 is generated by in situ deprotection of the methyl ethers using triethylsilane. Converting the final product into a bis-HCl salt improves solubility.

Generation of phosphonate prodrug 77-18, 77-19 is accomplished from commercial Raloxifene Hydrochloride. A reductive amination with an aminophosphonate generates the desired product. The reaction is carried out using 77-15, 77-16 equivalents of sodium cyanoborohydride in CH$_2$Cl$_2$. The two enantiomers generated are separated by chiral chromatography.

Scheme 77.1
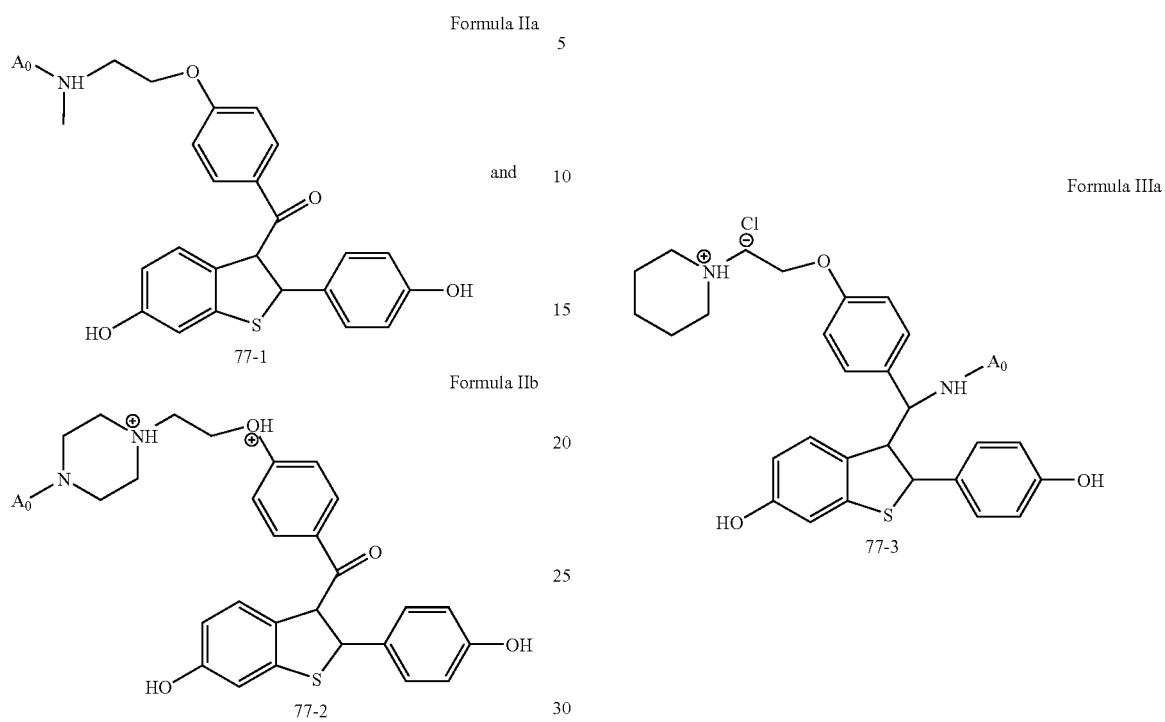
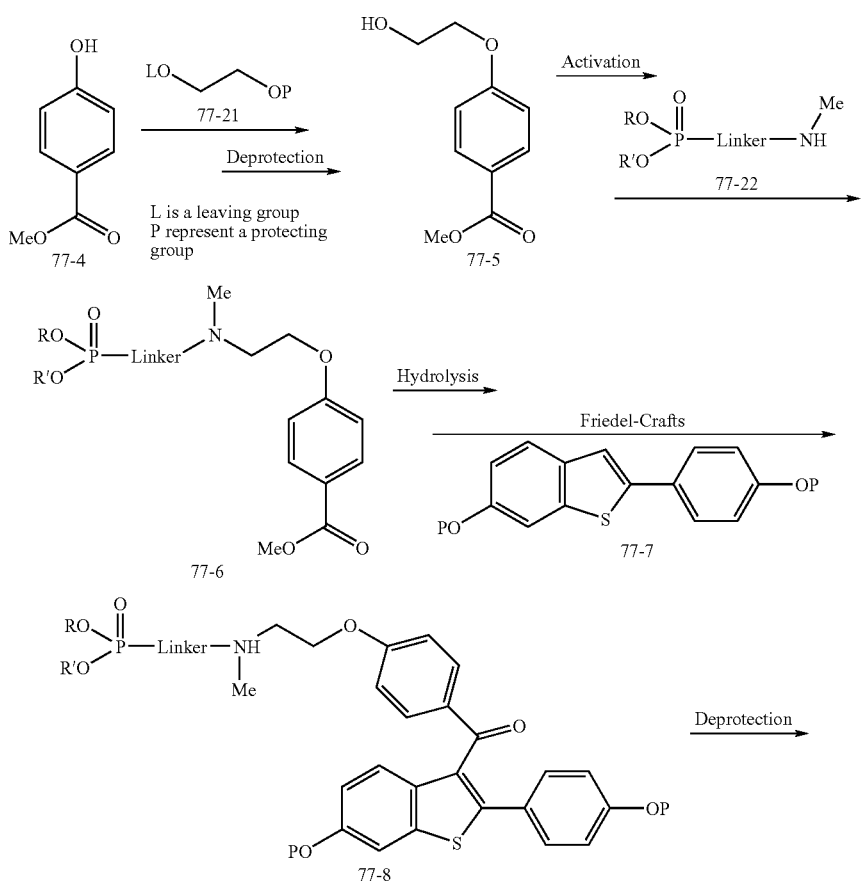

-continued
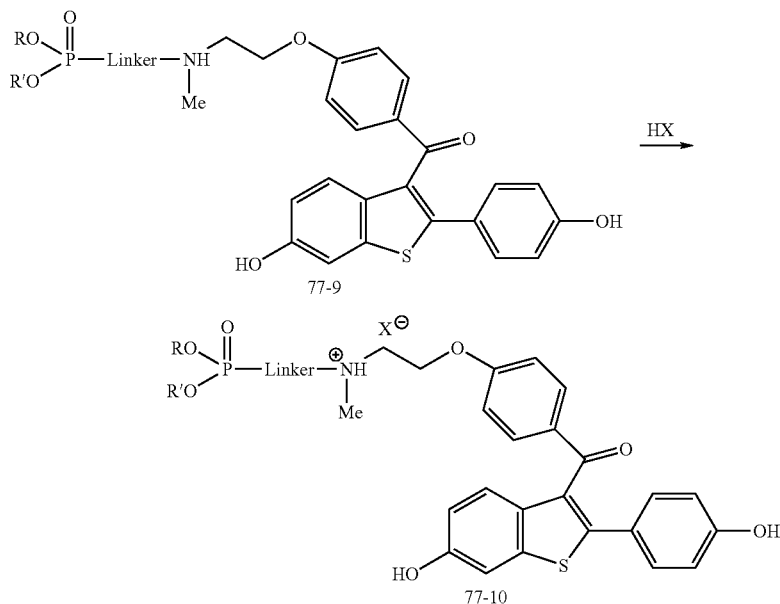
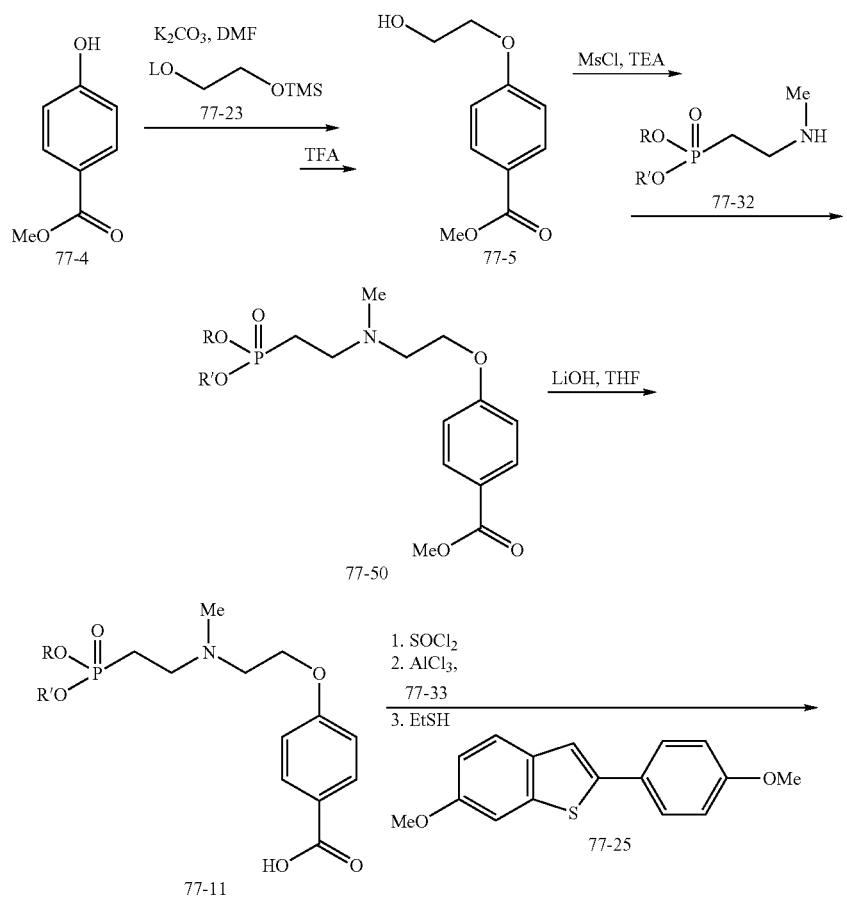

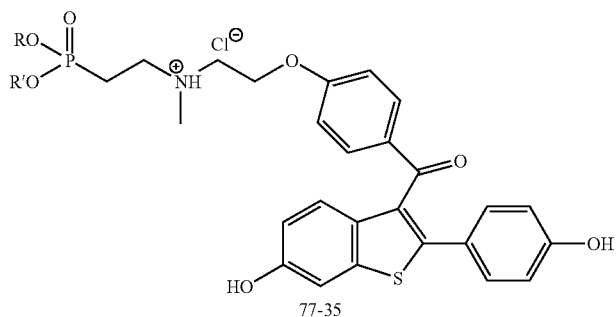
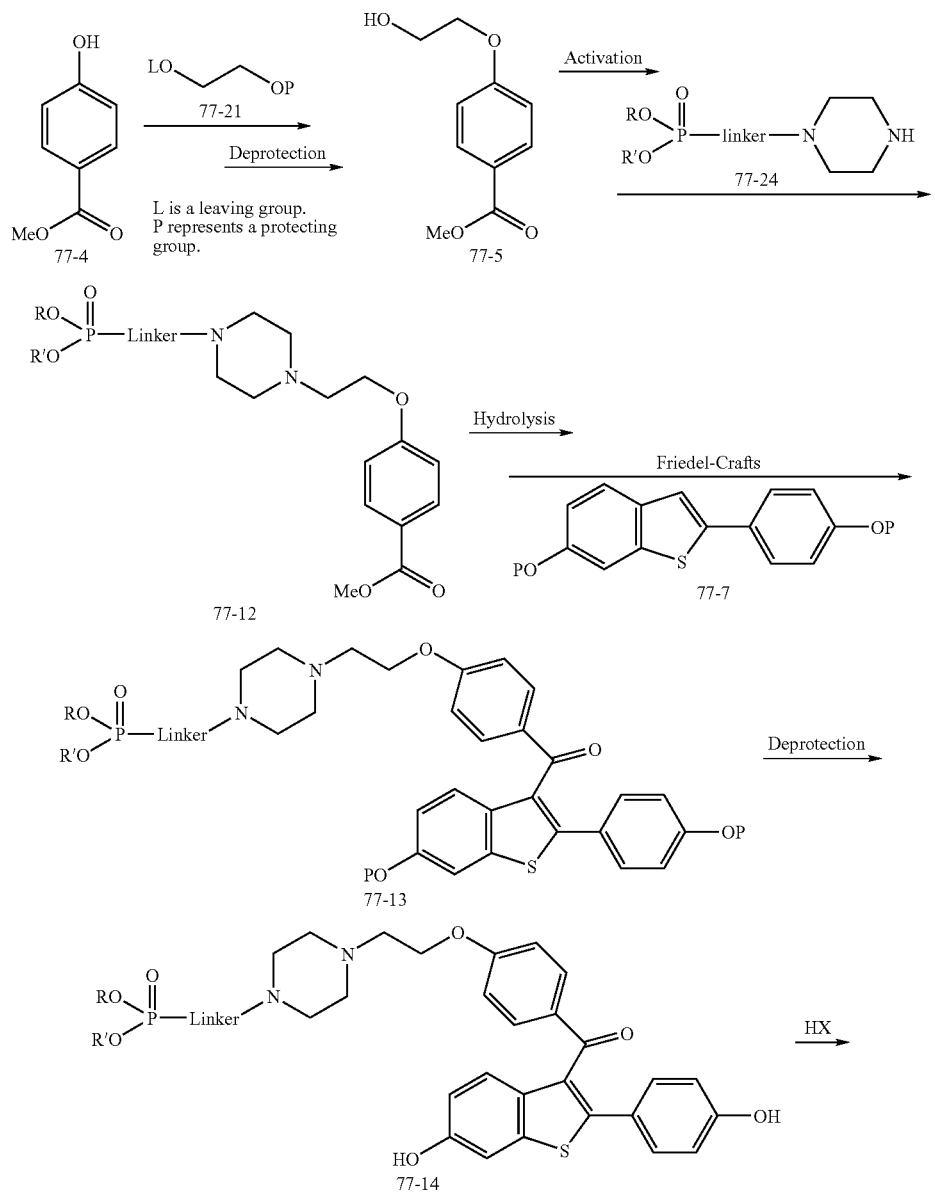

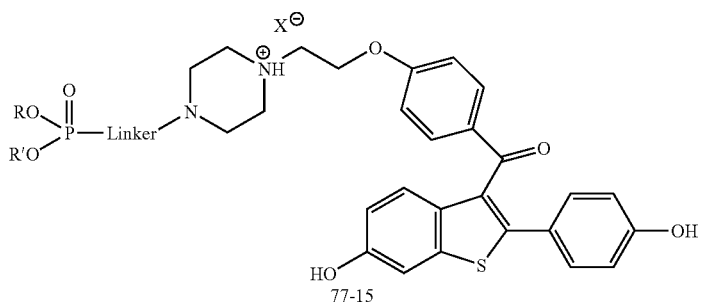
77-15
Scheme 77.5
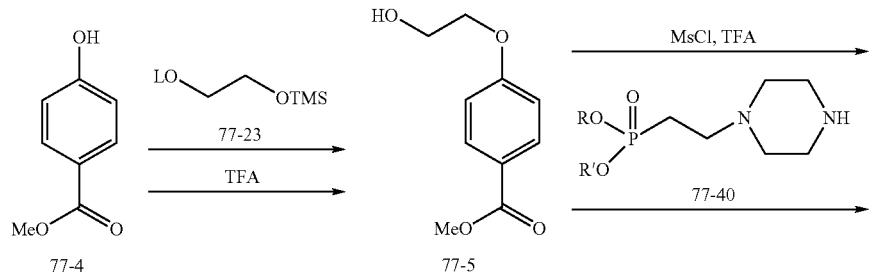
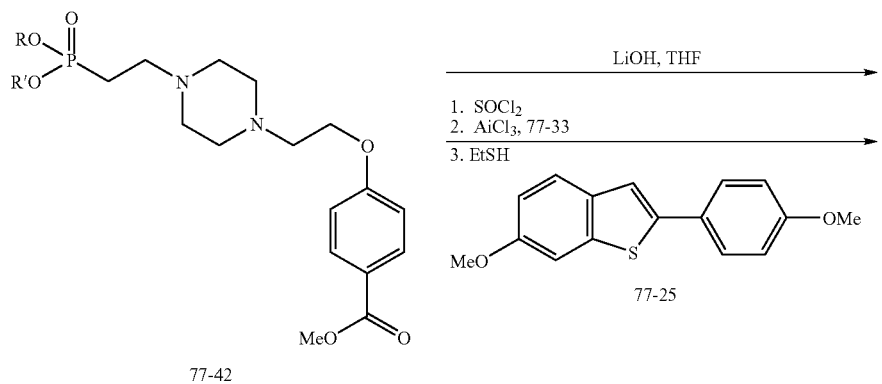
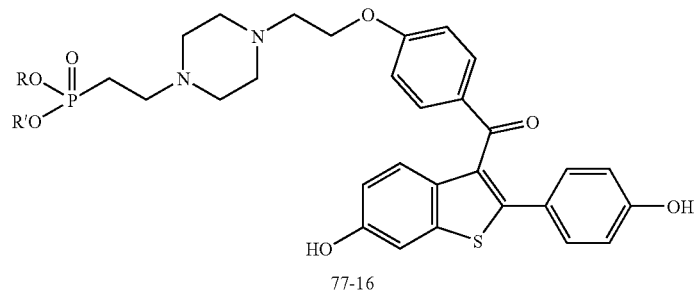
77-16

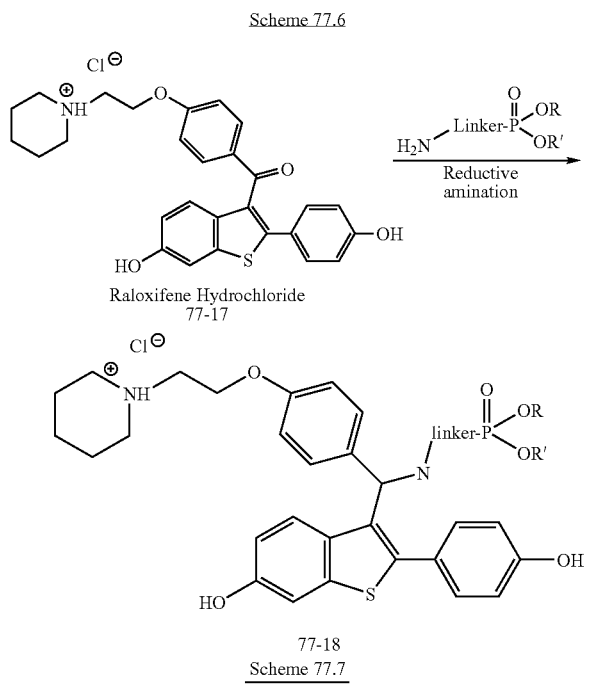

Example 78

Preparation of Exemplary Compounds of the Present Invention

Preparation of Phosphonate Prodrugs of Mycophenolate Mofetil

Three regions of mycophenolate mofetil are utilized for the attachment of the phosphonate prodrug onto mycophenolic acid as demonstrated by compounds 78-1 to 78-4 (Scheme 78.1). Also, the carboxylic acid is replaced with a phosphonic acid which is part of the prodrug moiety as in compound 78-3.

The morpholino ethyl moiety which serves as prodrug to improve bioavailability is replaced with the phosphonate prodrug handle as shown in Schemes 78.2-78.3. Mycophenolic acid is commercially available, e.g., from Sigma Chemical Company, St. Louis, Mo. Activation of the carboxylic acid 78-5 in the presence of the free phenol followed by addition of an alcohol carrying the phosphonate group results in the formation of the desired product (U.S. Pat. No. 4,786,637). Specifically, mycophenolic acid 78-5 is dissolved in dichloromethane. Thionyl chloride is added followed by a catalytic amount of DMF. The reaction mixture is stirred at room temperature for 3 hours, after which the volatile components are removed under vacuum. The phosphonate-alcohol is dissolved in dichloromethane and chilled to 4° C. on an ice bath. The mycophenolic acid chloride 78-7 is dissolved in dichloromethane and added to the chilled solution. After stirring for 90 minutes at 4° C., the reaction mixture is washed with water and then with aqueous sodium bicarbonate. The organic solution is dried and evaporated to yield the phosphonate prodrug 78-6, 78-8.

The C-4 phenol position provides a reactive handle for further analogs (Schemes 78.4-78.5). Once the carboxylic acid is blocked by morpholino ethyl, such as in compound 78-9, or a phosphonate prodrug as in compound 78-6, 78-8, the phenol is alkylated under basic conditions. Bases such as pyridine, potassium carbonate, or triethylamine are utilized. Leaving groups such as trifluoromethylsulfonate, mesylate, bromide, or iodide are attached to the phosphonate prodrug subunit and reacted in the presence of base with compound 78-9. Compound 78-2, 78-45 can either be used directly, or in the form of a salt. Among the number of salts that can be prepared, chloride and bisulfate salts are of particular interest.

Preparation of compound 78-10, 78-11 is outlined in more detail in Scheme 78.5. Compound 78-7 is prepared as described in Scheme 78.3. A solution of morpholino ethanol in dichloromethane is cooled to 4° C. The mycophenolic acid chloride 78-7 is dissolved in dichloromethane and added to the cooled solution. Stirring this solution for 90 minutes gives compound 78-9. The reaction mixture is washed with water and dried with sodium sulfate. Removal of the solvent provides compound 78-9. Alkylation at the phenolic position of 78-9 is achieved by suspending the compound in pyridine. Triflate 78-30 is added to the solution and the mixture is stirred at room temperature for 90 minutes. The reaction mixture is poured into water and the product is extracted with ethyl acetate. Removal of the organic layer provides compound 78-2, 78-45. Hydrochloride salt of 78-2, 78-45 is also prepared. Compound 78-2, 78-45 is dissolved in isopropanol and the solution is added to a mixture of hydrogen chloride in isopropanol. The hydrochloride salt 78-10, 78-11 is collected by filtration and dried under vacuum.

The carboxylic acid of mycophenolic acid is replaced with a phosphonic acid which serves as the prodrug handle as well. In order to remove the carboxylic acid containing side chain, the acid chloride 78-7 is converted to ester 78-13, 78-33. Protection of the phenol with a silyl group, followed by dihydroxylation and cleavage of the diol generates aldehyde 78-15, 78-19 (Pankiewicz, et al., J. Med. Chem., (2002), 45, 703), (Patterson et al., U.S. Pat. No. 5,444,072) (Schemes 78.6-78.7). A wittig reaction with ylide 78-50, 78-31 carrying an appropriately protected phosphonate provides the desired compound 78-16, 78-20. Final deprotection yields compound 78-17.

Mycophenolate ester 78-13, 78-33 is prepared by stirring the acid chloride 78-7 with MeOH. Then, the phenol position of mycophenolate ester is protected by a silyl group such as TBS to provide compound 78-14, 78-18. Once the phenol position is protected, dihydroxylation using osmium tetraoxide followed by periodinate cleavage provides aldehyde 78-15, 78-19. Aldehyde 78-15, 78-19 and excess of the ylide 78-50, 78-31 are heated in benzene at reflux for 24 hours. The reaction mixture is concentrated and the residue is purified by column chromatography to provide olefin 78-16, 78-20 (Pankiewics et al., *J. Med. Chem.*, (2002), 45, 703). A final deprotection using HF-pyridine yields the final product 78-17.

Another attachment point of the compound is unmasked after demethylation of mycophenolate ester 78-9 (Schemes 78.8-78.9). For this purpose, 4-OH is masked with a protecting group such as a silyl group. Once the 6-MeO is demethylated and alkylated, the protecting group at position 4 is removed to reveal the final product. The morphonyl ethanol group is installed early and carried through the alkylation steps. A different group serving the role of the protecting group is installed initially and removed later. In that case, the last step is the formation of the morpholinoethyl ester prodrug.

Synthesis of compound 78-4 is shown in Scheme 78.9. Phenol 78-9 is protected with TBS group in $CH_2Cl_2$ using imidazole as base. Demethylation is performed using thiolate nucleophiles to generate compound 78-26, 78-22. A variety of other methods are also available in literature as described in protective groups in organic synthesis by Greene and Wuts. Alklation of the 6-OH using a triflate of the phosphonate prodrug proceeds well using $K_2CO_3$ or TEA. Final deprotection to remove the TBS group provides product 78-27, 78-24.

Further manipulations can be performed on the phosphonate moiety prior to the final deprotection. These types of transformations are more extensively described in the following section.

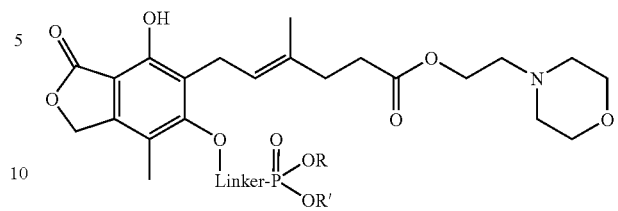

Scheme 78.2

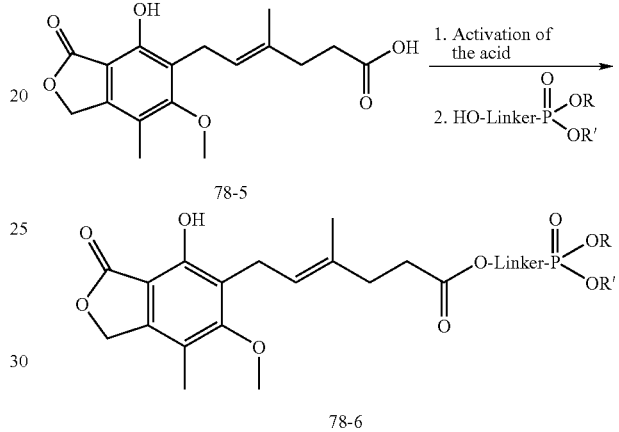

Scheme 78.3

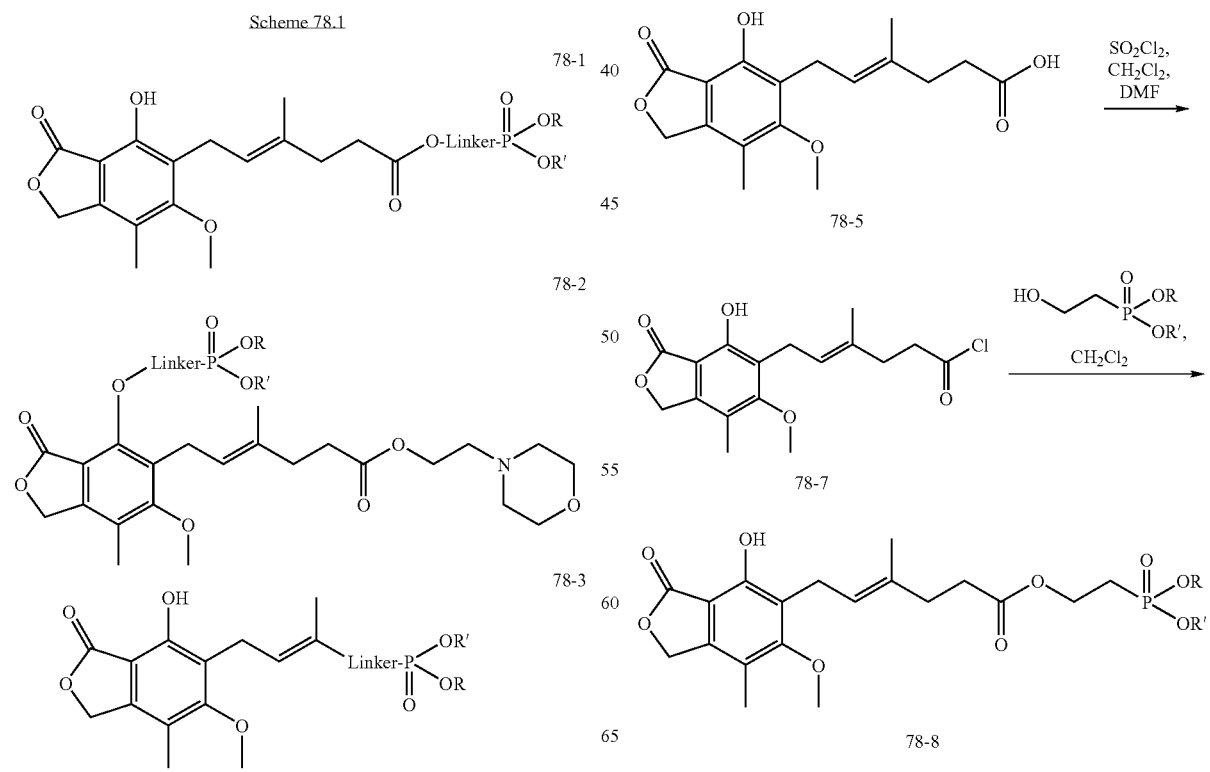

Scheme 78.4
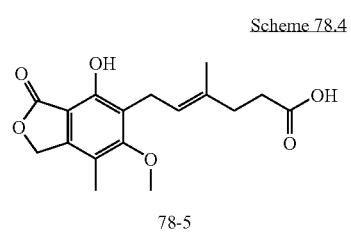
78-5
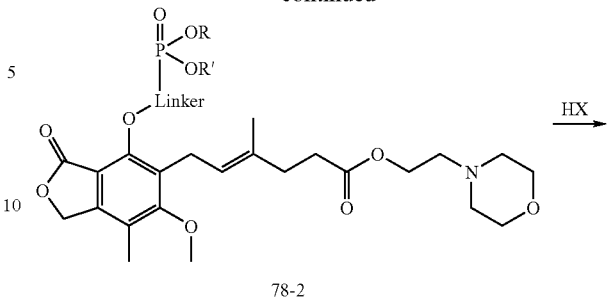
78-2
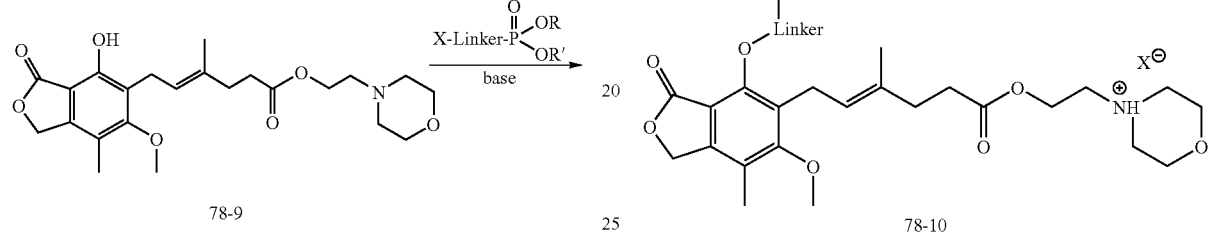
78-9 → 78-10
Scheme 78.5
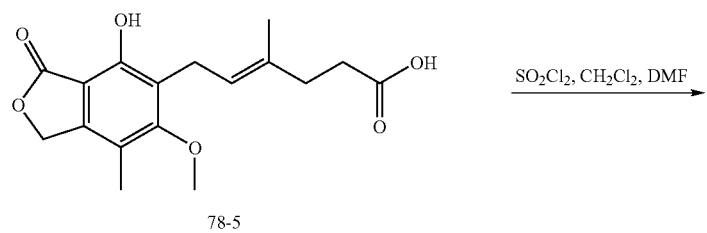
78-5
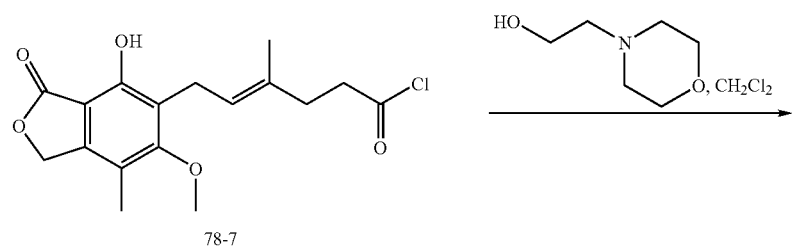
78-7
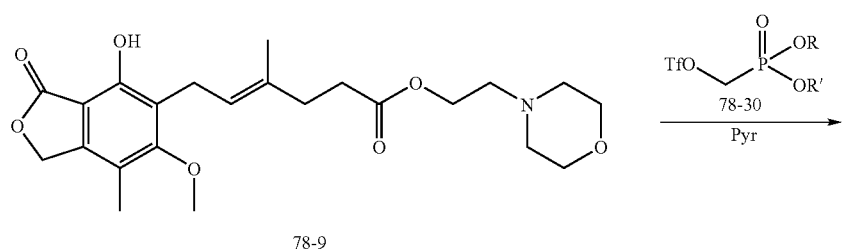
78-9

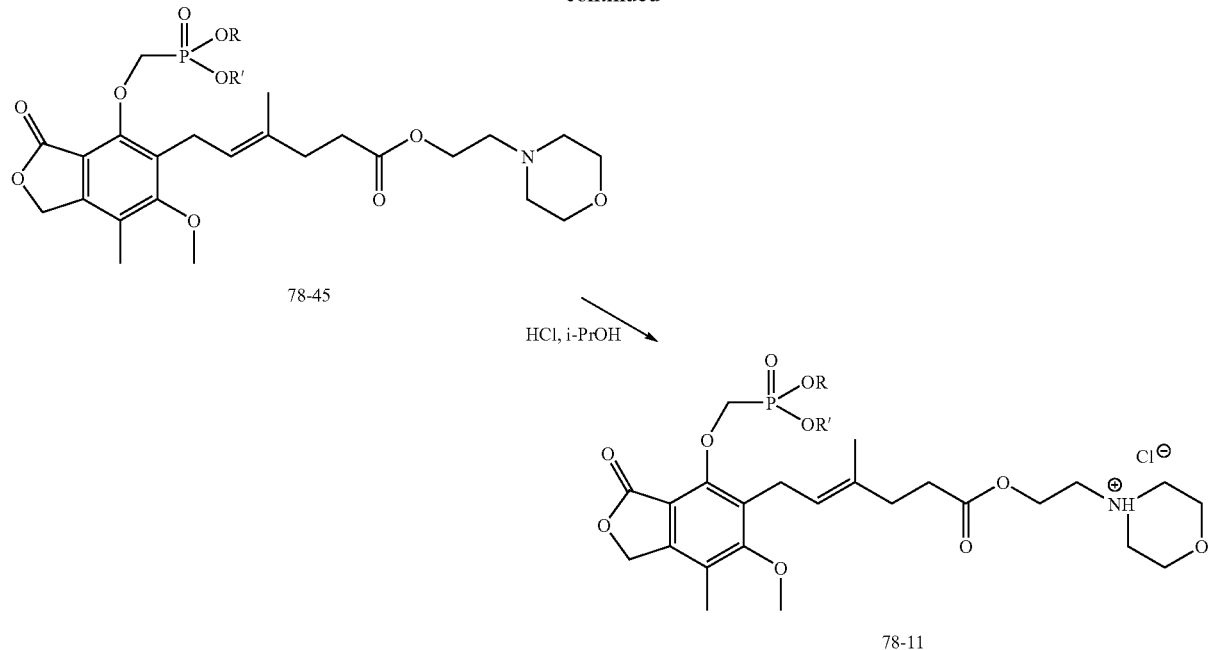
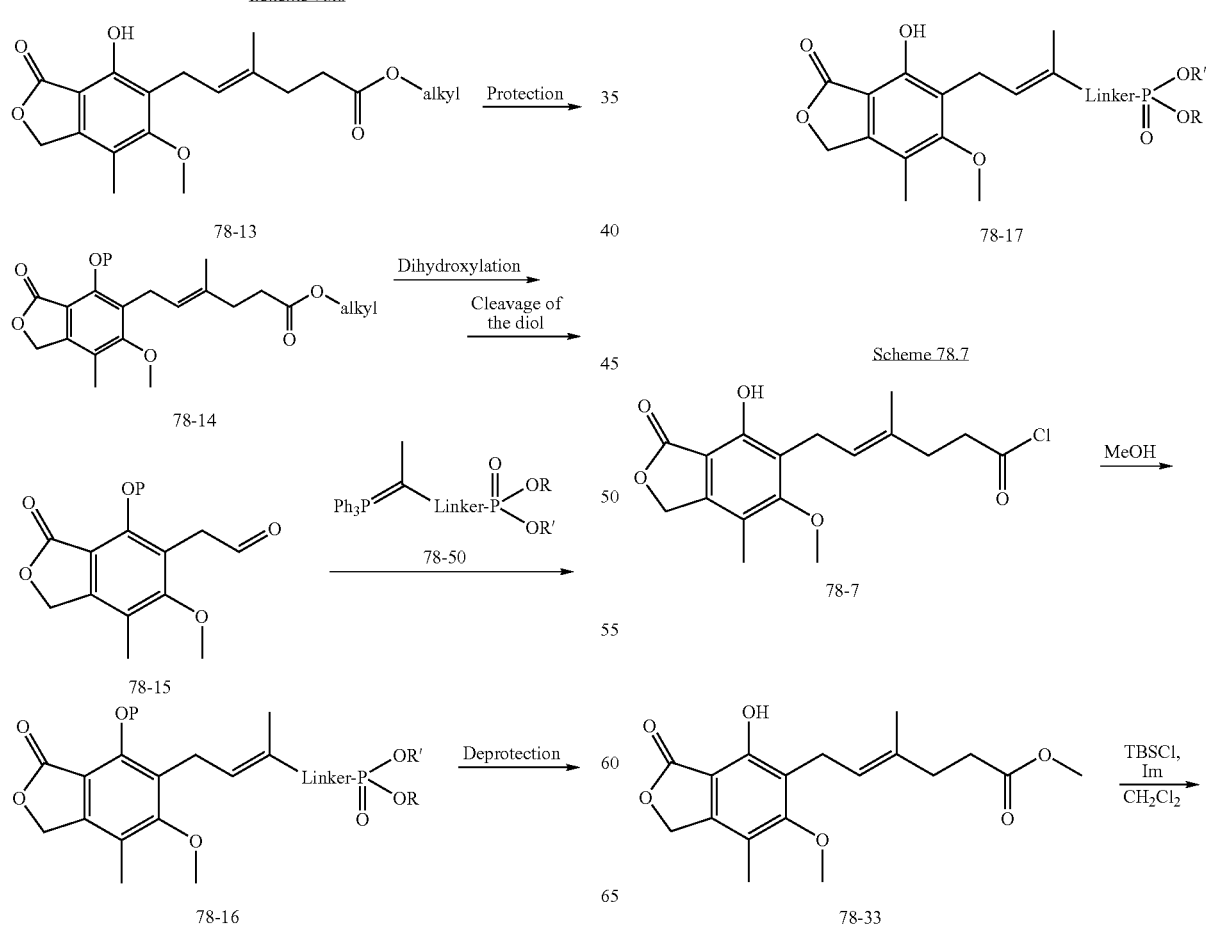

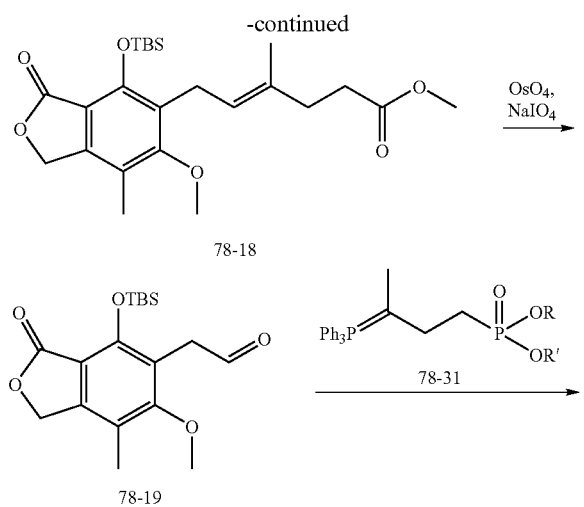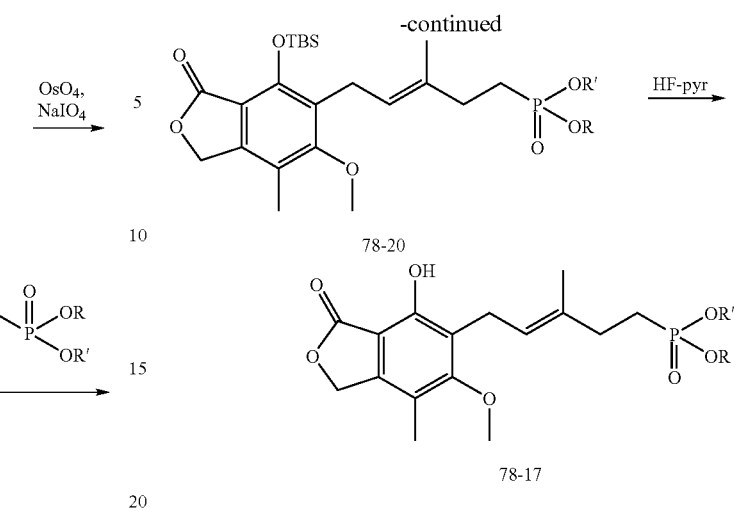
Scheme 78.8
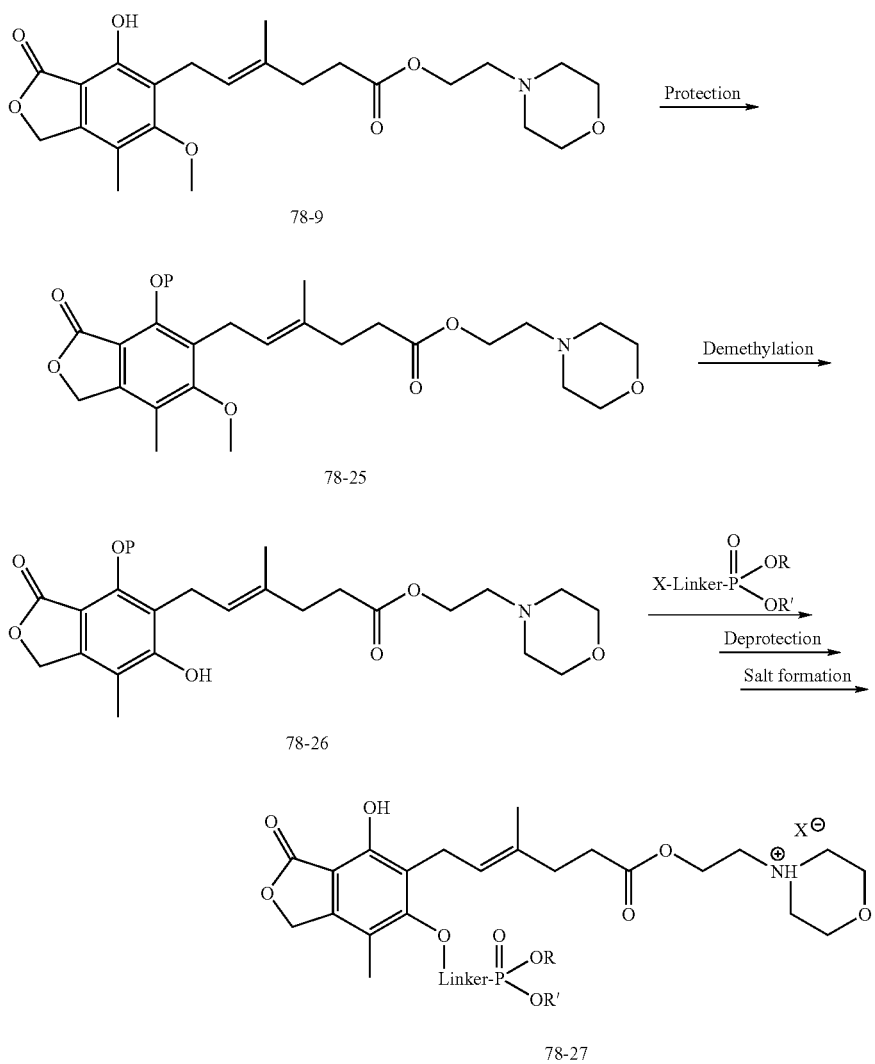

Scheme 78.9
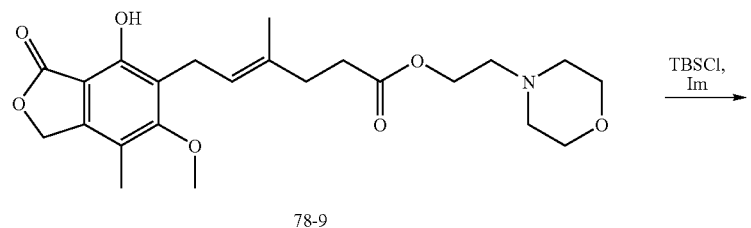
78-9
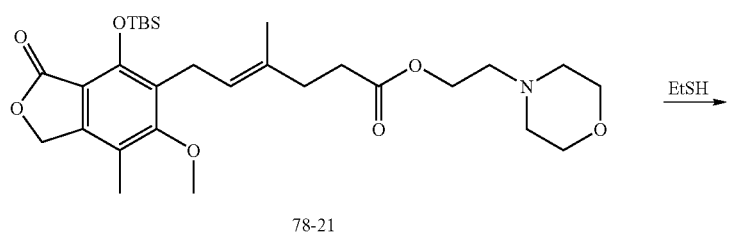
78-21
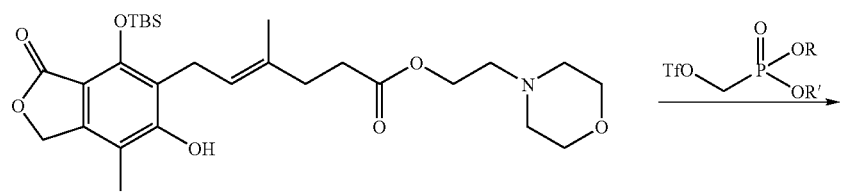
78-22
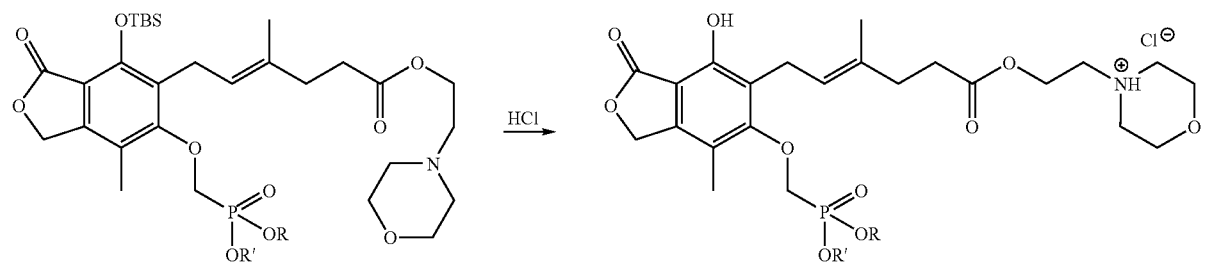
78-23            78-24

Example 79

Preparation of Exemplary Compounds of the Present Invention

Derivatization at the C-21 hydroxy group is accomplished through alkylation of dexamethasone 79-1 with the appropriate phosphonate, furnishing analogs of the type 79-2. (Scheme 79.1)

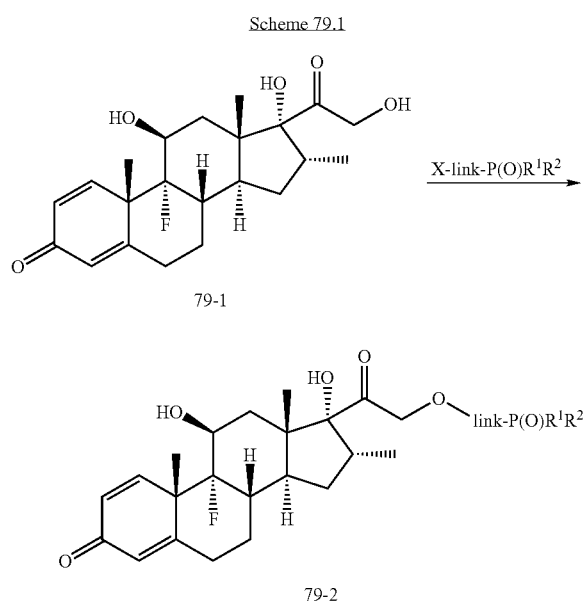

After sodium hydride extraction of the primary hydroxy proton in 79-1, diethyl phosphonate triflate is added to afford ether 79-3. (Scheme 79.2)

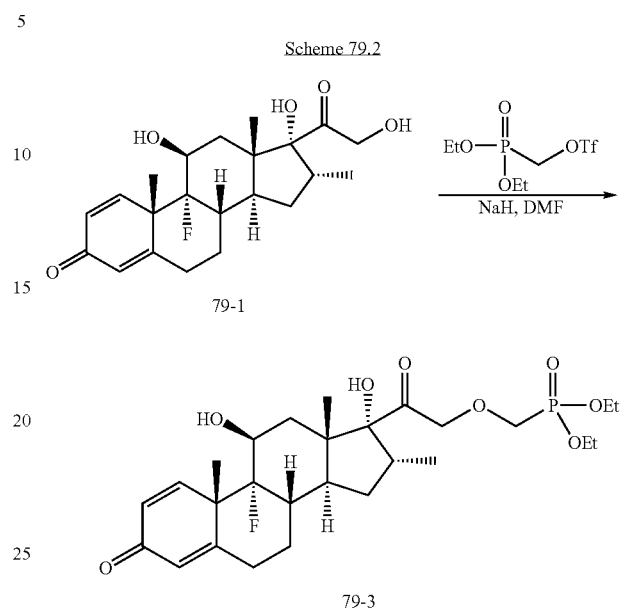

Phosphonate appendages linked to the C-11 hydroxy group are attained from utilizing protecting groups on dexamethasone 79-1. (Scheme 79.3) Following protection of the primary hydroxy group, protected intermediate 79-4 is alkylated at the more exposed C-11 hydroxy site. Final deprotection provides the desired product 79-6.

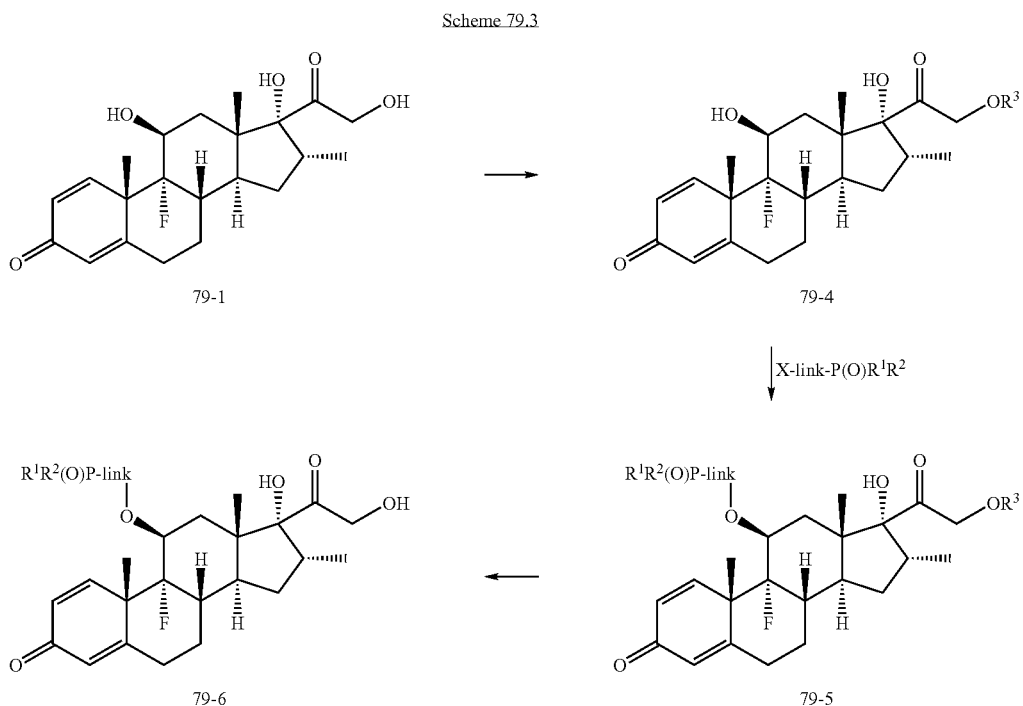

Dexamethasone 79-1 is protected as its silyl ether using the standard TBSCl and imidazole conditions. (*J. Am. Chem. Soc.* 1972, 94, 6190) (Scheme 79.4) After alkylating with the diethyl phosphonate triflate, the resulting intermediate 79-8 is treated with TBAF to give the diol 79-9.

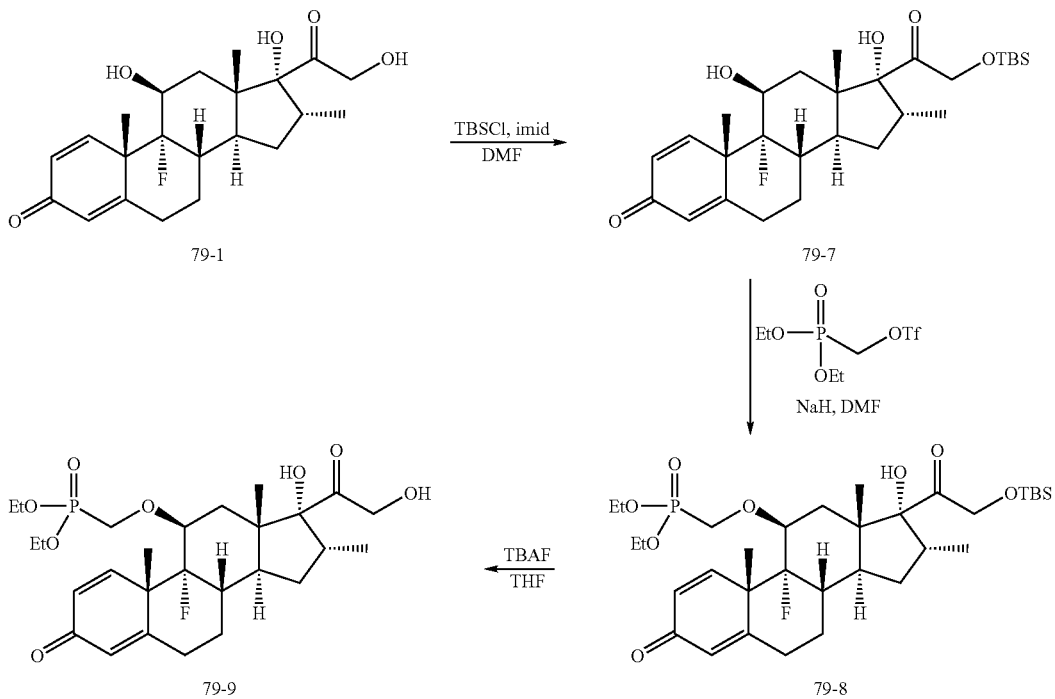

Synthesis of C-21 phosphonate analogs of the type 79-12 is shown in Scheme 79.5. Protection this time of dexamehtasone 79-1 at the two less hindered sites furnishes alcohol 79-10, which is alkylated at the only exposed hydroxy group with the appropriate phosphonate. Removal of the protecting groups completes the construction of analog 79-12.

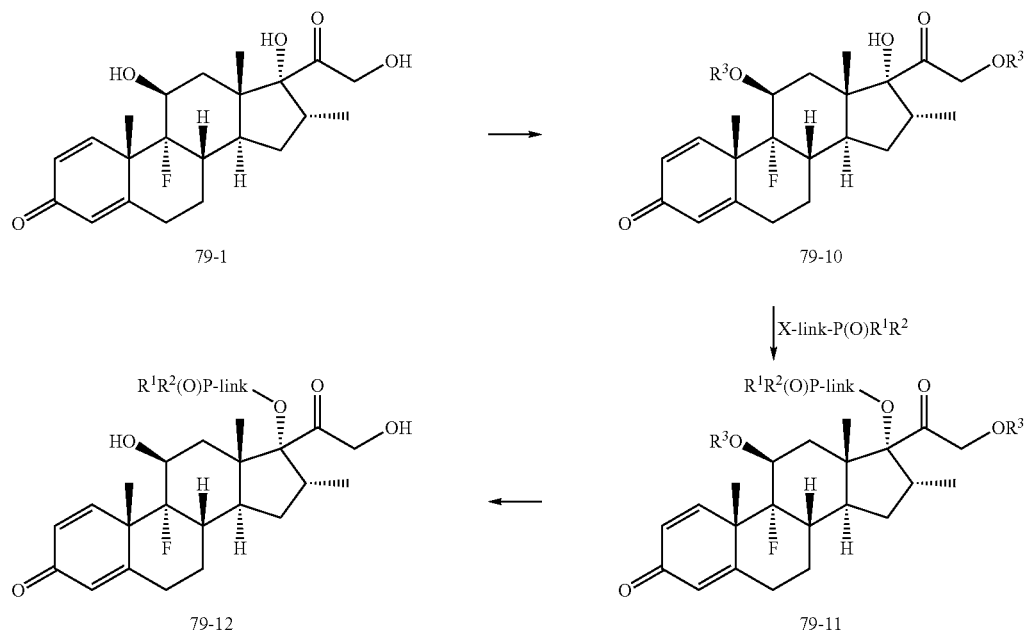

Again dexamethasone 79-1 is protected as its TBS ether; however, harsher conditions are used for bis-protection. (Scheme 79.6) After alkylating with the diethyl phosphonate triflate, the resulting intermediate 79-14 is treated with TBAF to give the desired phosphonate 79-15.

Scheme 79.6

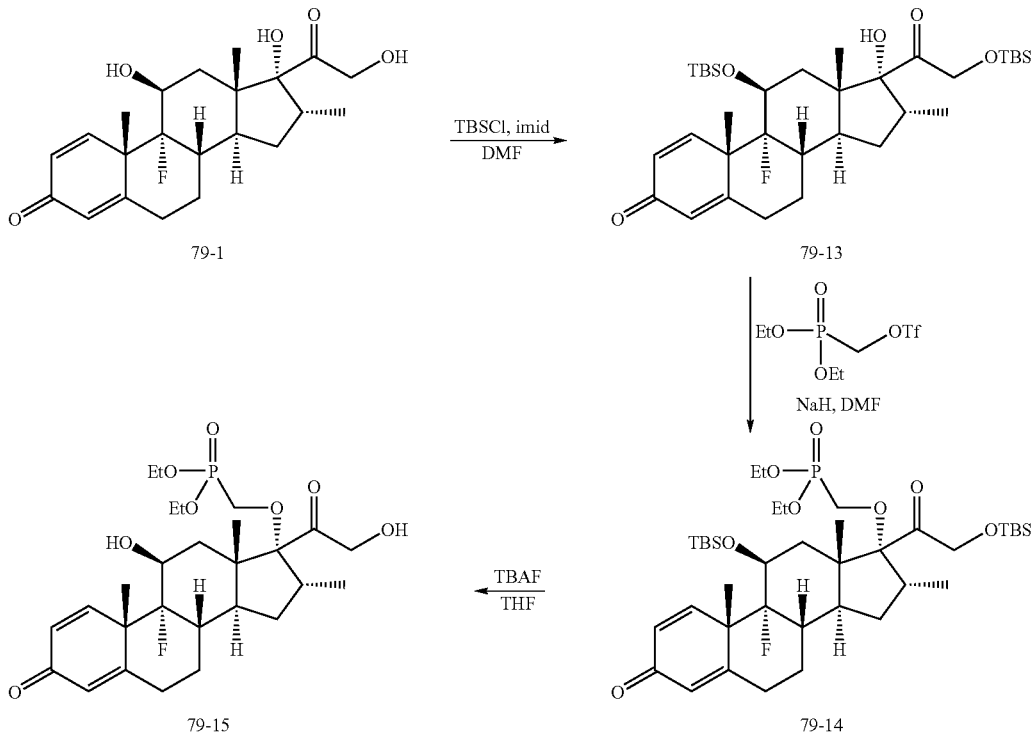

Example 81

Preparation of Exemplary Compounds of the Present Invention

Experimental Results for Pro-drugs of Phosphonate-containing PNP Inhibitors

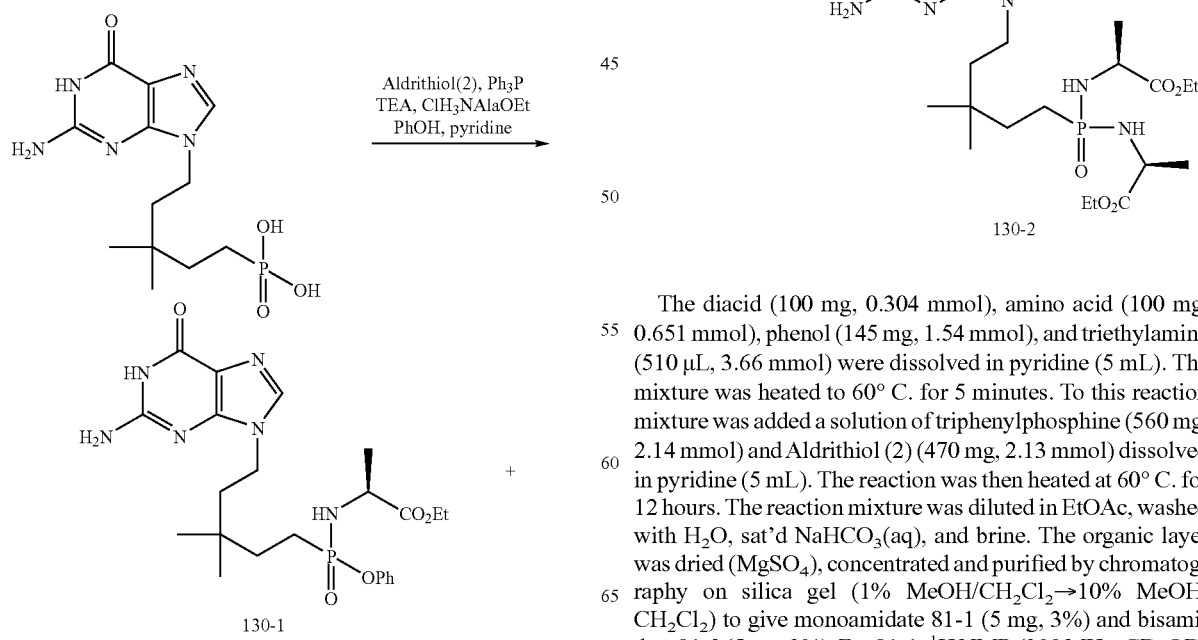

The diacid (100 mg, 0.304 mmol), amino acid (100 mg, 0.651 mmol), phenol (145 mg, 1.54 mmol), and triethylamine (510 μL, 3.66 mmol) were dissolved in pyridine (5 mL). The mixture was heated to 60° C. for 5 minutes. To this reaction mixture was added a solution of triphenylphosphine (560 mg, 2.14 mmol) and Aldrithiol (2) (470 mg, 2.13 mmol) dissolved in pyridine (5 mL). The reaction was then heated at 60° C. for 12 hours. The reaction mixture was diluted in EtOAc, washed with $H_2O$, sat'd $NaHCO_3$(aq), and brine. The organic layer was dried ($MgSO_4$), concentrated and purified by chromatography on silica gel (1% $MeOH/CH_2Cl_2 \rightarrow$ 10% $MeOH/CH_2Cl_2$) to give monoamidate 81-1 (5 mg, 3%) and bisamidate 81-2 (5 mg, 3%). For 81-1: $^1H$ NMR (300 MHz, $CD_3OD$)

δ 7.78 (1H, m), 7.35 (2H, m), 7.20 (3H, m), 4.18-3.95 (5H, m), 2.24-1.90 (2H, m), 1.87-1.62 (4H, m), 1.38-1.18 (6H, m), 1.02 (6H, m); $^{31}$P NMR (121 MHz, CD$_3$OD) δ 36.3, 35.3; LC-MS (method: 0.5 min 95% H$_2$O/5% MeCN→5 min 0% H$_2$O/100% MeCN, rt=2.18 min. MS calc'd for C$_{23}$H$_{34}$N$_6$O$_5$P (MH$^+$): 505.2. Found 505.2. For 81-2: $^1$H NMR (300 MHz, CD$_3$OD) δ 7.77 (1H, s), 4.23-3.92 (8H, m), 2.04-1.50 (6H, m), 1.42 (3H, d), 1.40 (3H, d), 1.28 (3H, t), 1.22 (3H, t), 1.02 (3H, s), 1.01 (3H, s); $^{31}$P NMR (121 MHz, CD$_3$OD) δ 33.9; LC-MS (method: 0.5 min 95% H$_2$O/5% MeCN→5 min 0% H$_2$O/100% MeCN, rt=1.79 min. MS calc'd for C$_{22}$H$_{39}$N$_7$O$_6$P (MH$^+$): 528.3. Found 528.3.

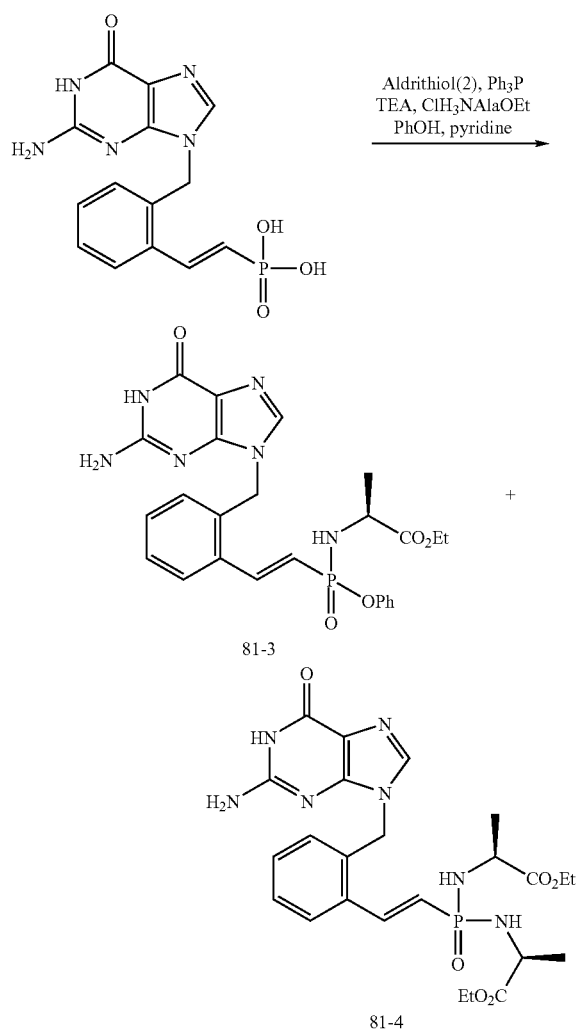

The diacid (25 mg, 0.072 mmol), amino acid (25 mg, 0.16 mmol), phenol (38 mg, 0.40 mmol), and triethylamine (127 µL, 0.911 mmol) were dissolved in pyridine (1.25 mL). The mixture was heated to 60° C. for 5 minutes. To this reaction mixture was added a solution of triphenylphosphine (140 mg, 0.534 mmol) and Aldrithiol (2) (119 mg, 0.540 mmol) dissolved in pyridine (1.25 mL). The reaction was then heated at 60° C. for 12 hours. Another batch of diacid (12 mg, 0.035 mmol) was treated as described above. The reaction mixtures from both batches were combined and diluted in EtOAc, washed with H$_2$O, sat'd NaHCO$_3$(aq) and brine. The organic layer was dried (MgSO$_4$), concentrated and purified by chromatography on silica gel (1% MeOH/CH$_2$Cl$_2$→10% MeOH/ CH$_2$Cl$_2$). to give monoamidate 81-3 (3 mg, 8%) and bisamidate 81-4 (8 mg, 20%). For 81-3: $^1$H NMR (300 MHz, CD$_3$OD) δ 8.38-8.08 (1H, m), 7.78-7.60 (2H, m), 7.50-7.18 (8H, m), 6.67-6.05 (1H, m), 5.60-5.30 (2H, m), 4.63 (1H, bs), 4.25-3.95 (3H, m), 1.37 (3H, m), 1.18 (3H, m); $^{31}$P NMR (121 MHz, CD$_3$OD) δ 21.5, 20.2; LC-MS (method: 0.5 min 95% H$_2$O/5% MeCN→5 min 0% H$_2$O/100% MeCN, rt=1.98 min. MS calc'd for C$_{25}$H$_{28}$N$_6$O$_5$P (MH$^+$): 523.2. Found 523.2. For 81-4: $^1$H NMR (300 MHz, CD$_3$OD) δ 8.15 (1H, dd), 7.72 (1H, s), 7.67 (1H, m), 7.39 (2H, m), 7.28 (1H, m), 6.44 (1H, dd), 5.40 (2H, s), 4.23-3.90 (6H, m), 1.42 (6H, m), 1.27 (3H, t), 1.18 (3H, t); $^{31}$P NMR (121 MHz, CD$_3$OD) δ 19.7; LC-MS (method: 0.5 min 95% H$_2$O/5% MeCN 5 min 0% H$_2$O/100% MeCN, rt=1.86 min. MS calc'd for C$_{24}$H$_{33}$N$_7$O$_6$P (MH$^+$): 546.2. Found 546.2.

Pro-drug Cleavage Assays

Isolation of PBMC Extracts:

Fresh human PBMCs were obtained from patients undergoing leukophoresis; cells were shipped in plasma and processed within 26 h of draw. Purification was achieved using the Ficoll-Paque method: PBMC cells were harvested by centrifugation at 1200×g for 5 minutes and washed three times by re-suspension in RBC lysis buffer (155 mM NH$_4$Cl, 0.1 mM EDTA, 10 mM KHCO$_3$). Washed cells were suspended in lysis buffer (0.2×10$^9$ cells in 1 ml of 10 mM Tris, pH 7.4, 150 mM NaCl, 20 mM CaCl$_2$, 1 mM DTT and 1% NP40) and incubated on ice for 20 minutes. The PBMC crude extract was centrifuged at 1000×g for 30 min to remove unlysed cells and the supernatant at 100,000 X g for 1 h. The 100,000×g supernatant (PBMC Extract: P0) was harvested, snap frozen in liquid nitrogen and stored at –70° C.

Protocol for Measurement of Cleavage of Prodrugs by PBMC Extracts:

Reaction mixtures contained 25 mM MesNa (pH 6.5), 100 mM NaCl, 1 mM DTT, 0.1% NP-40, 30 µM substrate, and varying amounts of enzyme in a final volume of 100 µl. The enzymatic reaction is performed at 37° C. for 10-120 minutes and stopped at 3-4 individual time points by adding 180 µl of ice cold methanol. Samples are incubated at –20° C. for 30 min, and centrifuged 13,000 RPM for 30 min (at 4° C.). The supernatant is transferred to a 96 well plate and evaporated under vacuum using a speedvac. The precipitate is dissolved in 100 µl of 20 mM CH$_3$COONH$_4$+ 5% AcCN. The disappearance of pro-drug is measured by HPLC, monitoring at 260 nm. The specific activity of the PBMC Extract against the prodrugs tested is defined as: v (cleavage rate)/µg protein=pmoles/min/µg.

Results

| Compound | Human PBMC extract specific activity (pmol/min/µg) |
|---|---|
| 81-1 | 3.48 |
| 81-2 | 0.65 |
| 81-3 | 4.9 |
| 81-4 | 0.38 |

Example 82

Preparation of Exemplary Compounds of the Present Invention

A series of inhibitors of PNP are rationally designed to mimic the transition state of the enzyme. This class as a whole is called the Immucillins. Depending on the enzyme that is used for the rational design of inhibitors, slightly different structures were proposed and synthesized. A highly potent analog inhibiting the PNP enzyme from *Mycobacterium tuberculosis* (MtPNP) called DADMe-ImmG, structure below, was prepared recently (Lewandowics A. et al., *Biochemistry*, (2003), 42, 6057).

Scheme 82.1

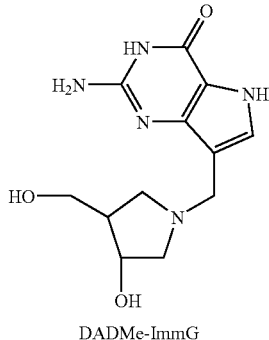

DADMe-ImmG

Reduction of the dose and/or improvement of efficacy is achieved by the use of pro-drugs DADMe-ImmG that, upon cleavage inside the target cell, give rise to agents with increased intracellular half-lives. Such phosphonates pro-drug compounds are shown below (Scheme 82.2).

Scheme 82.2:

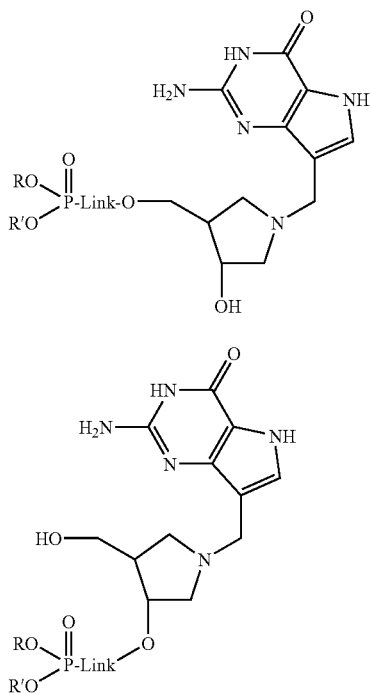

General structure of prodrugs of DADMe

Compounds such as 82-1 is made according to the general route outlined in Scheme 82.3, with an example depicted in Scheme 82.4.

Scheme 82.3

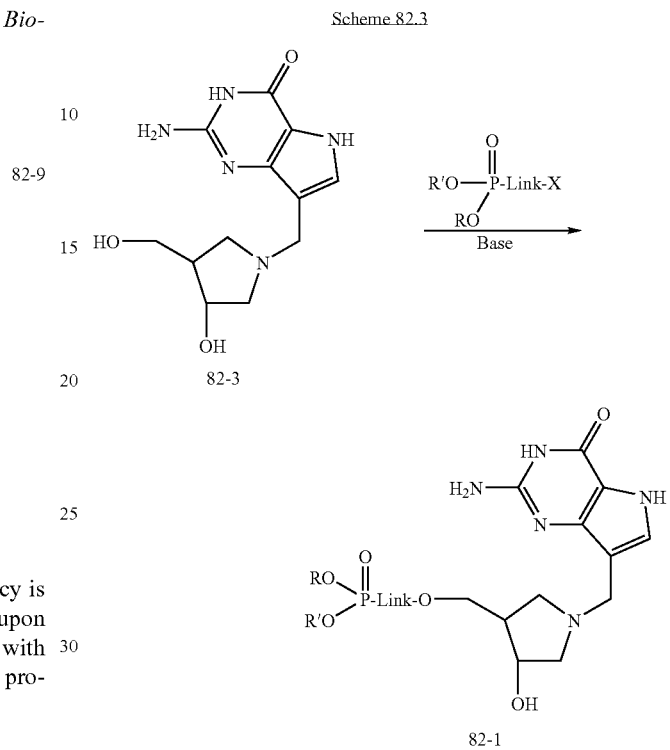

Scheme 82.4

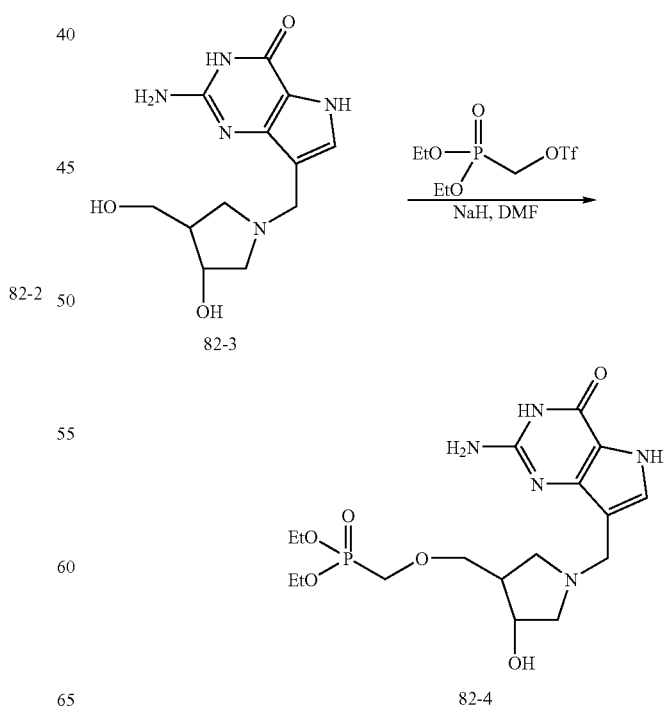

Preparation of DADMe-ImmG is reported in Lewandowics A. et al., *Biochemistry*, (2003), 42, 6057. The tertiary nitrogen of the ring may not interfere with the alkylation of the secondary alcohol and in that case does not need to be protected, although standard protection and deprotection protocols as described in Greene, T. Protective groups in organic synthesis, Wiley-Interscience, (1999) may be used if necessary. Reaction of the primary alcohol 82-3 with base followed by addition of the appropriately activated phosphonate yields the protected product. Global deprotection yields the desired phosphonate 82-4.

Compounds such as 82-2 is made according to the general route outlined in Scheme 82.5, with an example depicted in Scheme 82.6.

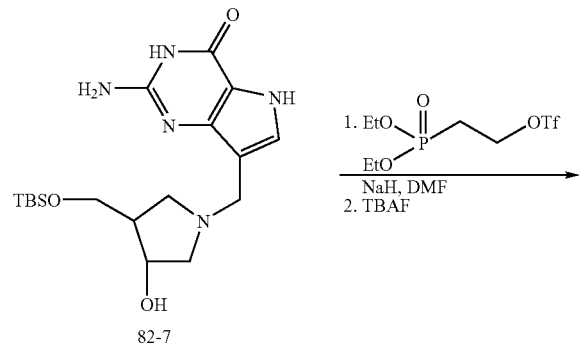

Scheme 82.6

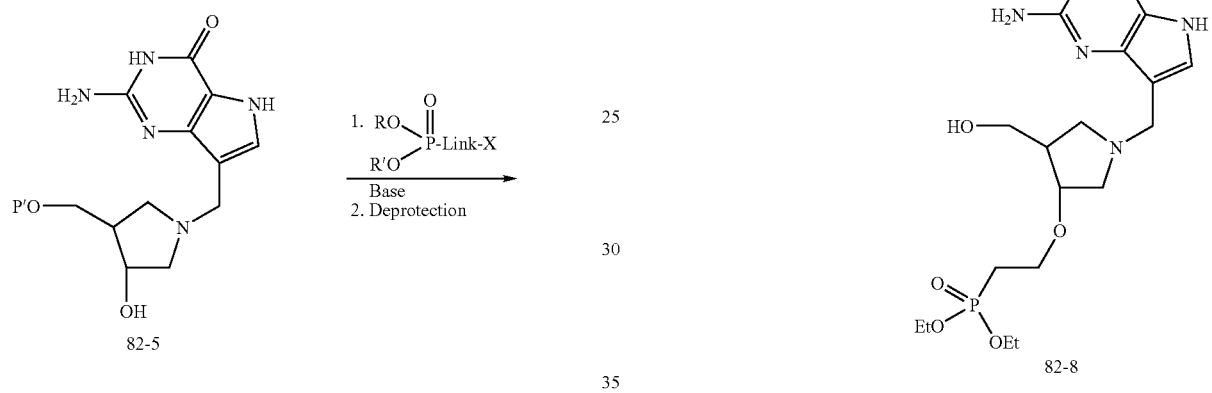

Scheme 82.5

Specifically, the protected DADMe derivative can be treated with treated in a solvent such as tetrahydrofuran or dimethylformamide with a base such as sodium hydride. When bubbling ceases, diethyl phosphonoethylltriflate (prepared according to *Tetrahedron Lett.*, (1986), 27, 1477) is added, yielding the desired phosphonate ester. Removal of the protecting group can be performed as described in Greene, T., Protective groups in organic synthesis, Wiley-Interscience, (1999) to provide the desired phosphonate ester.

Example 83

Preparation of Exemplary Compounds of the Present Invention

Scheme 83.1

Parent molecule:

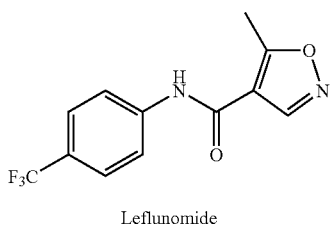

83-1

Leflunomide

Preparation of DADMe-ImmG is reported in Lewandowics A. et al., *Biochemistry*, (2003), 42, 6057. Blocking of the primary alcohol can be achieved by methods described in Greene, T., Protective groups in organic synthesis, Wiley-Interscience, (1999). Reaction of the secondary alcohol in base followed by addition of the appropriately activated phosphonate yields the protected desired product. Deprotection yields the desired phosphonate.

Active metabolite

General target structures:

link includes 1 or more atoms; 2-8 is preferred

A synthetic scheme towards specific targets 83-8 and 83-9 is outlined below:

Scheme 83.2

Target 83-8

Target 83-9

Reference for these reactions: *J. Med. Chem.* (1996), 39, 4608

Additional Compounds: The synthesis of targets 83-13 and 83-14 is set forth below.

Scheme 83.3

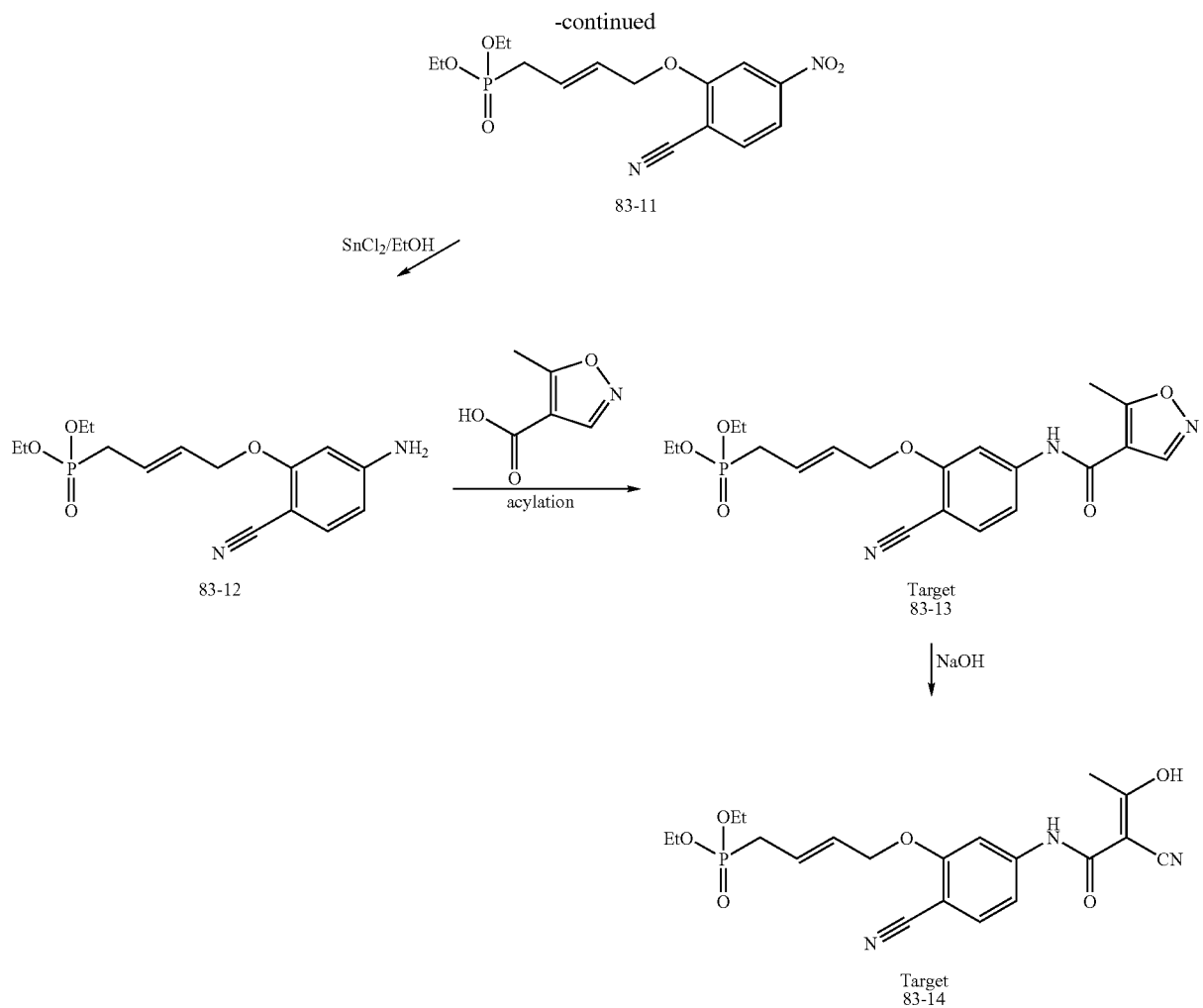

Example 84

Preparation of Exemplary Compounds of the Present Invention

Leflunomide (structure below, together with its active metabolite) (see U.S. Pat. No. 4,284,786) is a derivative of isoxazole that inhibits various T-lymphocyte functions through the inhibition of dihydroorotate dehydrogenase (Copeland et al, Biochem., (1996), 35, 1270).

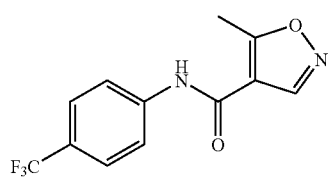

Leflunomide

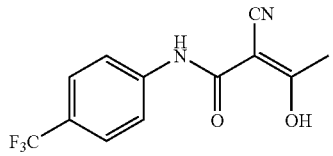

A771726 (active metabolite)

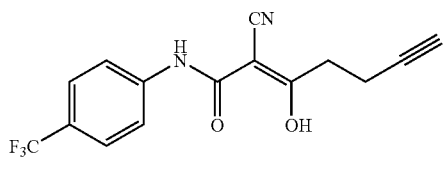

FK778 (MNA-715)

The active metabolite of leflunomide (A771726, also known as teriflunomide, see U.S. Pat. No. 6,288,098) has a very long half-life in humans, and this is a cause for concern given the side effects that have been noted for the compound, which include skin rash, pruritus, diarrhea, abdominal pain, nausea, vomiting, weight loss, hypertension, dizziness, and reversible alopecia. More serious adverse events that have also been reported include several cases of pleural involvement, vasculitis and hepatotoxicity. Rare cases of Stevens-Johnson syndrome and toxic epidermal necrolysis have also been described.

Reduction of the dose and improvement of efficacy is achieved by the use of pro-drugs of analogs of leflunomide or its metabolite which, upon cleavage inside the target cell, give rise to an agent with an increased intracellular half-life. The same concepts are applicable to FK778 (MNA-715) (see U.S. Pat. No. 5,308,865), an agent with a similar mode of action. Such compounds are described below.

Scheme 84.2

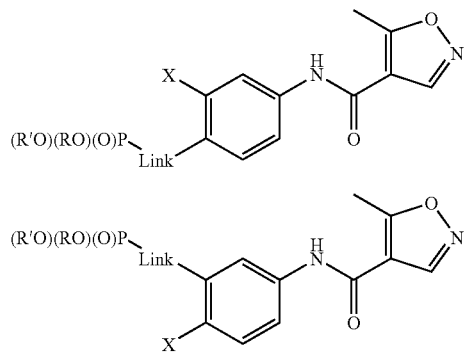

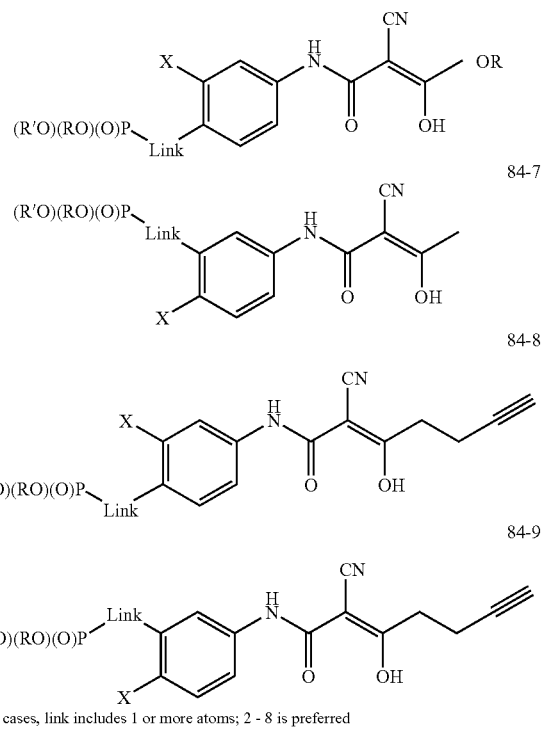

In all cases, link includes 1 or more atoms; 2 - 8 is preferred

Synthetic methodology towards compounds such as these is described by Westwood et al, J. Med. Chem., (1996), 39, 4608-4621, according to the general routes outlined in Schemes 84.3-84.5.

Scheme 84.3

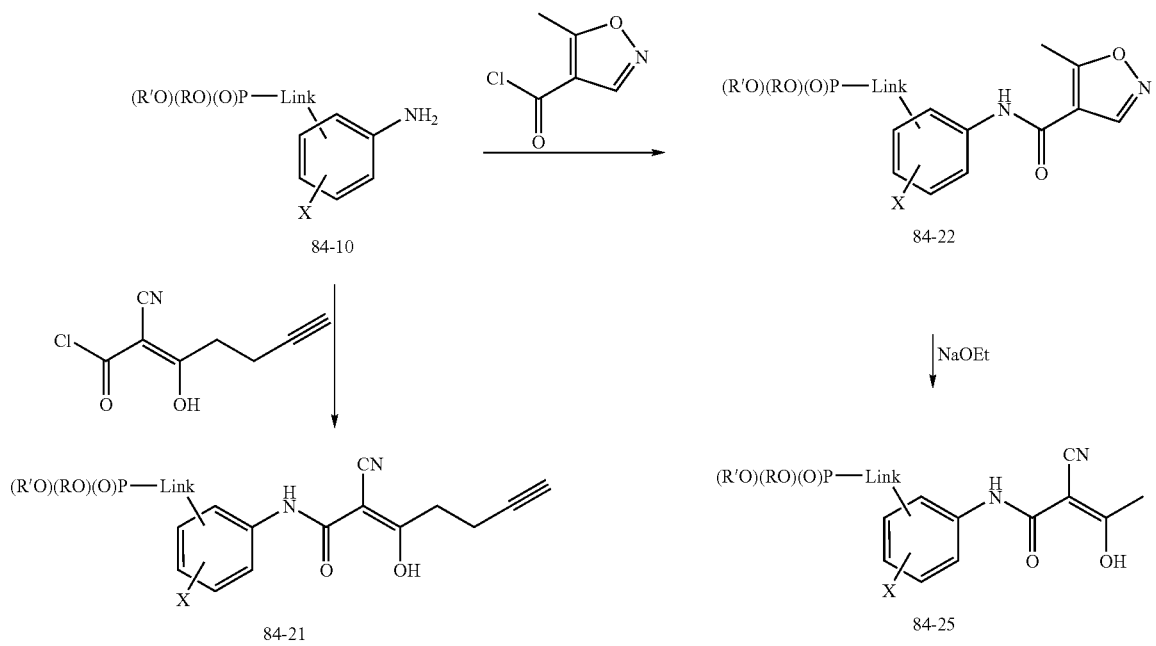

Examples of the synthesis of suitable phosphonate-containing anilines are shown below.
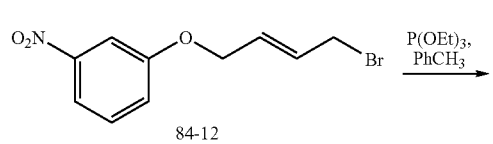
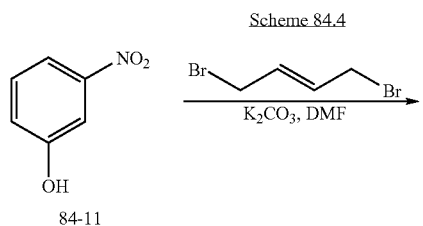
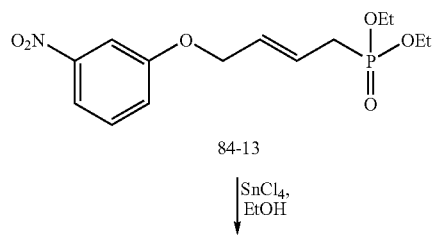
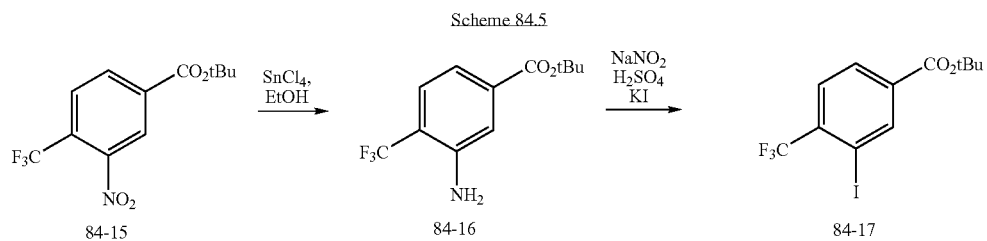
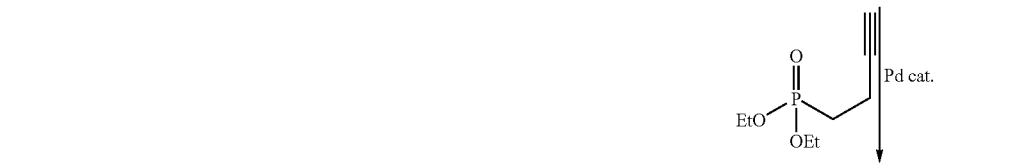
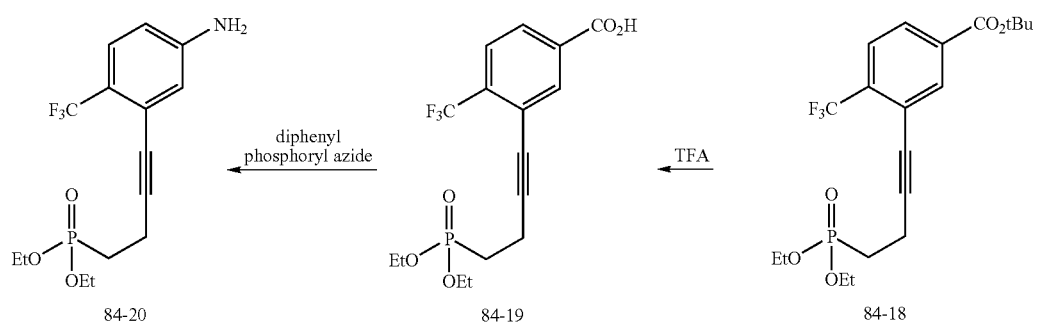

Example 85

Preparation of Exemplary Compounds of the Present Invention

Brequinar (structure below; see U.S. Pat. No. 4,680,299 and U.S. Pat. No. 5,032,597) is an inhibitor of dihydroorotate dehydrogenase (*Biochemical Pharmacology* 1990, 40, 709-714).

Scheme 85.1

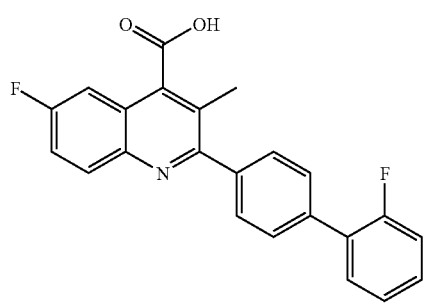

85-1

The compound has been investigated clinically as an immunosuppressant or as an anti-cancer agent, but its efficacy has been disappointing, possibly due to a narrow therapeutic window arising from an excessively long half-life that precludes higher dosing.

These problems are addressed by the use of pro-drugs of analogs of brequinar as well as other quinoline inhibitors of dihydroorotate dehydrogenase which, upon cleavage inside the target cell, give rise to an active entity with a sustained intracellular half-life relative to plasma levels. The therapeutic index of such agents might be significantly improved over brequinar itself. Such compounds are described below.

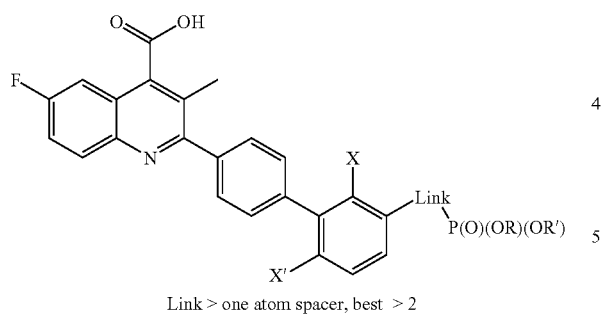

85-2

Link > one atom spacer, best > 2

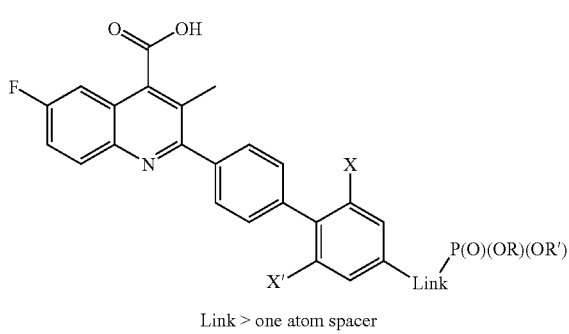

85-3

Link > one atom spacer

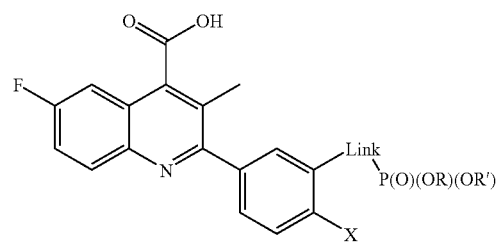

85-4

Link > one atom spacer, best > 2

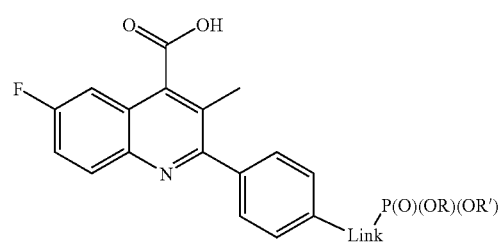

85-5

Link > one atom spacer, best = 3 or greater

X, X' = H, F, Cl, CF₃, CN, Me, tBu
In all cases, link includes 1 or more atoms; 2 - 8 is preferred Synthetic methodology towards compounds such as these is based on methods described by Batt et al, *Bioorg. Med. Chem. Lett.*, (1995), 5, 1549. A typical general route is outlined in Schemes 85.3-85.5.

Scheme 85.3

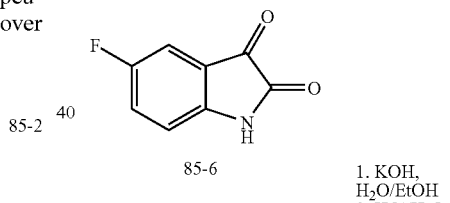

85-6

+

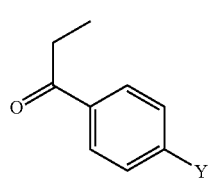

85-7

1. KOH, H₂O/EtOH
2. HCl/H₂O

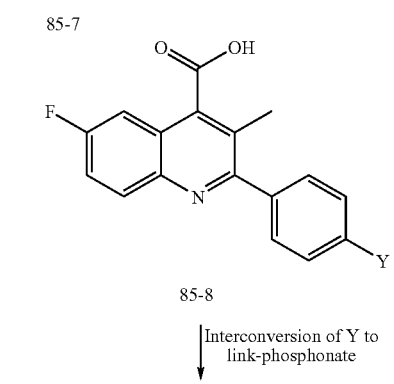

85-8

Interconversion of Y to link-phosphonate

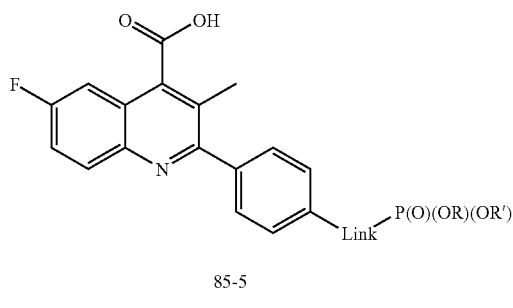
85-5
Examples of the synthesis of suitable phosphonate-containing analogs are shown below.
Scheme 85.4
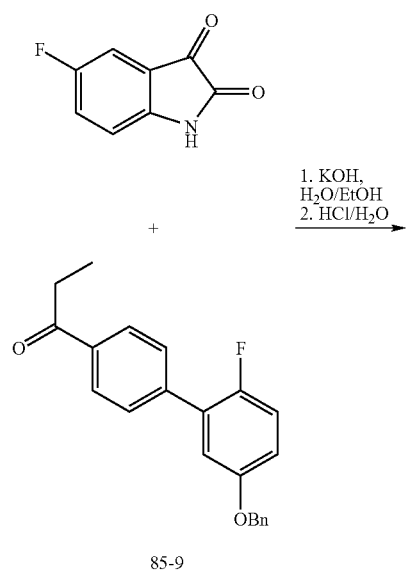
85-9
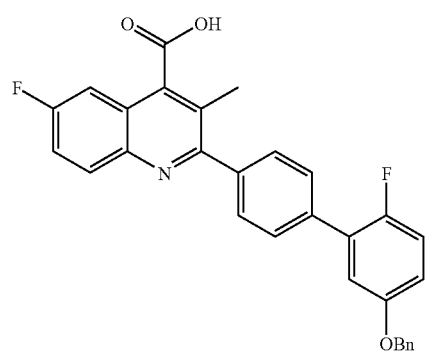
85-10
1. H2, Pd/C, EtOH
2. NaH(>2eq), TsOCH2P(O)(OEt)2
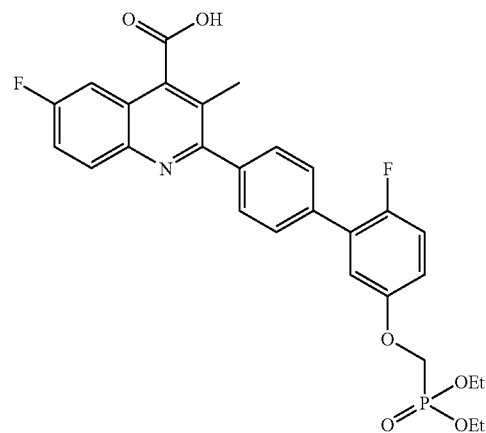
85-11
Scheme 85.5
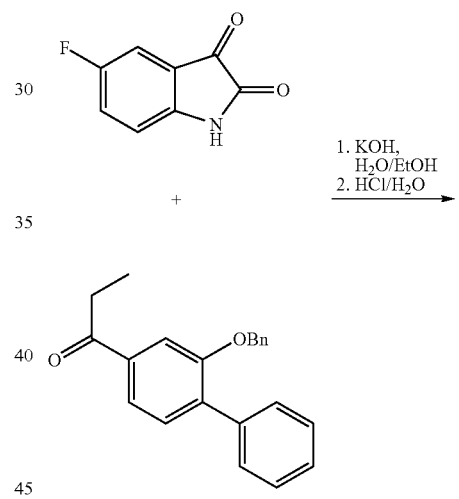
85-12
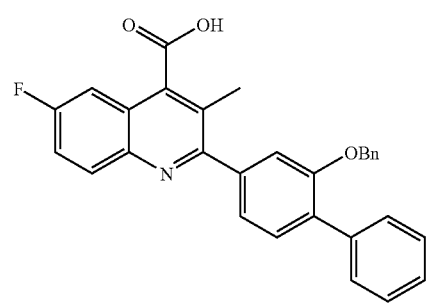
85-13
1. H2, Pd/C, EtOH
2. NaH (>2eq), BrCH2CHCHCH2Br
3. P(OEt)3

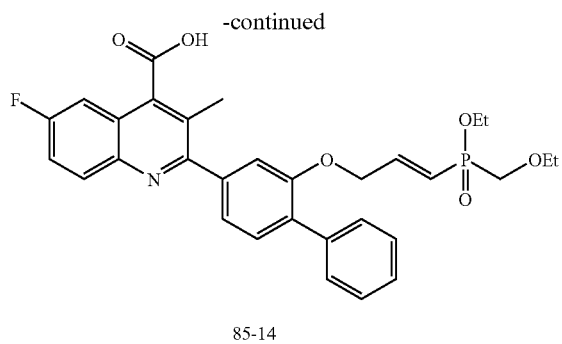

85-14

Example 86

Preparation of Exemplary Compounds of the Present Invention

Scheme 86.1:
(2-{4-[(2,4-Diamino-pteridin-6-ylmethyl)-methyl-amino]-benzoylamino}-methyl)-phosphonic acid diethyl ester

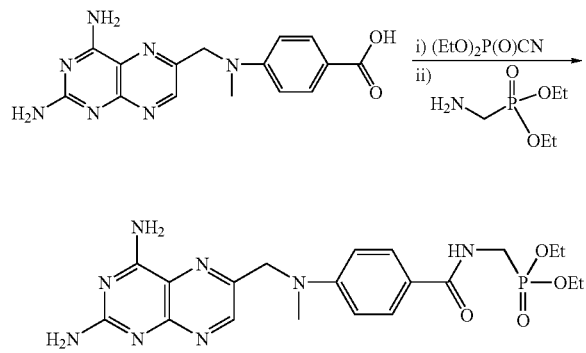

To a solution of 4-[(2,4-diamino-pteridin-6-ylmethyl)-methyl-amino]-benzoic acid hemihydrochloride dihydrate (67.0 mg, 177 μmol) in DMF (3.0 mL) was added diethyl cyanophosphonate (34.8 μL, 230 μmol) and diisopropylethylamine (Hunig's Base, DIEA, 30.4 μL, 177 μmol). The solution was stirred at ambient temperature for 4 hours when diethyl(aminomethyl)-phosphonate (45.4 mg, 177 μmol) was added. The solution was stirred for 4 additional hours, when complete consumption of the starting materials was observed. The reaction was worked up by removal of the solvent in vacuo and purifying the residue by silica gel chromatography using MeOH—$CH_2Cl_2$ (10-30%). The product collected from this chromatography step was sufficiently pure to be carried on to the next reaction. A small amount of the product (20 mg) was repurified by RP HPLC on $C_{18}$ column using $H_2O$/acetonitrile (2-95%) to provide 12.9 mg (76%) of the pure product. $^1$H NMR (300 MHz, DMSO-$d_6$) δ 1.19 (t, 6H, J=7.2 Hz), 3.21 (s, 3H), 3.70 (m, 2H), 4.00 (q, 4H, J=7.2 Hz), 4.81 (s, 2H), 6.81 (d, 2H, J=9 Hz), 7.71 (d, 2H, J=9 Hz), 8.40 (br s, 1H), 8.61 (s, 1H). $^{31}$P (121.4 MHz, DMSO-$d_6$) δ 23.4. MS (m/z) 475.2 [M+H]$^+$, 597.2 [M+Na]$^+$.

Scheme 86.2:
(2-{4-](2,4-Diamino-pteridin-6-ylmethyl)-methyl-amino]-benzoylamino}-methyl)-phosphonic acid

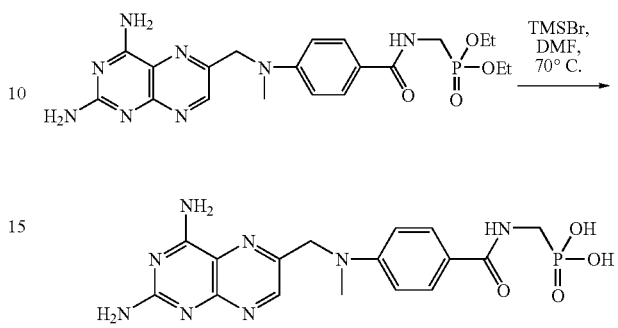

To a solution of crude (2-{4-[(2,4-Diamino-pteridin-6-yl-methyl)-methyl-amino]-benzoylamino}-ethyl)-phosphonic acid diethyl ester post silica column chromatography (60 mg, 126 μmol) in dry DMF (0.90 mL) was added trimethylsilyl bromide (bromotrimethylsilane, TMSBr, 130.6 μL, 1,010 μmol) at ambient temperature. The solution was then heated at 70° C. for 4.0 hours, after which the reaction mixture was allowed to cool to room temperature. The solvent volume was reduced to ~700 μL in vacuo and diluted with $H_2O$ (100 μL). This solution was purified by RP HPLC on $C_{18}$ column using $H_2O$/acetonitrile (2-95%) to provide 26.8 mg (51%) of the desired compound as a yellow solid. $^1$H NMR (300 MHz, DMSO-$d_6$) δ 3.18 (s, 3H), 3.50 (m, 2H), 4.77 (s, 2H), 6.79 (d, 2H, J=9 Hz), 7.79 (d, 2H, J=9 Hz), 8.07 (br s, 1H), 8.56 (s, 1H); MS (m/z) 419.2 [M+H]$^+$.

Scheme 86.3:
(2-{4-[(2,4-Diamino-pteridin-6-ylmethyl)-methyl-amino]-benzoylamino}-ethyl)-phosphonic acid diethyl ester

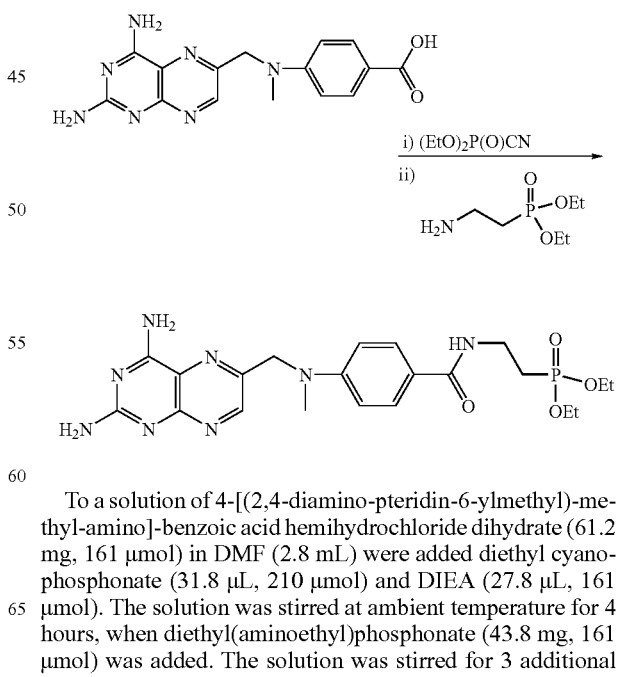

To a solution of 4-[(2,4-diamino-pteridin-6-ylmethyl)-methyl-amino]-benzoic acid hemihydrochloride dihydrate (61.2 mg, 161 μmol) in DMF (2.8 mL) were added diethyl cyanophosphonate (31.8 μL, 210 μmol) and DIEA (27.8 μL, 161 μmol). The solution was stirred at ambient temperature for 4 hours, when diethyl(aminoethyl)phosphonate (43.8 mg, 161 μmol) was added. The solution was stirred for 3 additional hours, by which time complete consumption of the starting materials was observed. The reaction was worked up by removal of the solvent in vacuo and purifying the residue by silica gel chromatography using MeOH—CH$_2$Cl$_2$ (10-30%). The product collected from this chromatography step was sufficiently pure to be carried on to the next reaction. A small amount of the product (32 mg) was re-purified by RP HPLC on C$_{18}$ column using H$_2$O/acetonitrile (2-95%) to provide 19 mg (70%) of the pure product. $^1$HNMR (300 MHz, DMSO-d$_6$) δ 1.21 (t, 6H, J=7 Hz), 1.95-2.05 (m, 2H), 3.20 (s, 3H), 3.13-3.22 (m, 2H), 3.98 (appt septet, 4H, J=7 Hz), 4.79 (s, 2H), 6.80 (d, 2H, J=9 Hz), 7.65 (d, 2H, J=9 Hz), 8.20 (br s, 1H), 8.60 (s, 1H). $^{31}$P (121.4 MHz, DMSO-d$_6$) δ 28.9. MS (m/z) 489.2 [M+H]$^+$, 511.2 [M+Na]$^+$.

Scheme 86.4:
(2-{4-[(2,4-Diamino-pteridin-6-ylmethyl)-methyl-amino]-benzoylamino}-ethyl)-phosphonic acid

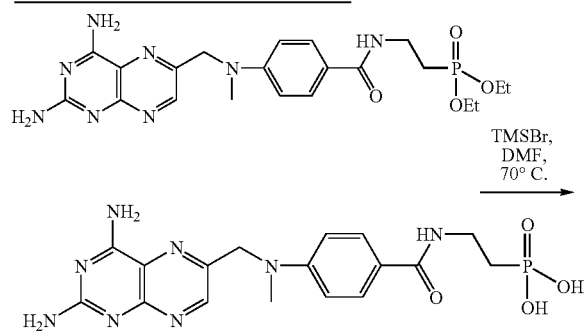

To a solution of crude (2-{4-[(2,4-diamino-pteridin-6-yl-methyl)-methyl-amino]-benzoylamino}-ethyl)-phosphonic acid diethyl ester post silica column chromatography (61 mg, 125 µmol) in dry DMF (1.00 mL) was added TMSBr (129.0 µL, 999.2 mmol) at ambient temperature. The solution was then heated at 70° C. for 5.5 hours, when LCMS analysis demonstrated the reaction to be 90% complete. The reaction mixture was allowed to cool to room temperature and stirred for an additional 12 hours. The reaction was worked up by removal of the solvent in vacuo and dissolving the residue in DMF/H$_2$O (800 µL, 1:1) and 1N aqueous NaOH (15 µL). The product was purified by RP HPLC on C$_{18}$ column using H$_2$O/acetonitrile (2-95%) to provide 29 mg (53%) of the desired compound as a yellow solid. $^1$H NMR (300 MHz, DMSO-d$_6$) δ 1.67-1.85 (m, 2H), 3.19 (s, 3H), 3.25-3.40 (m, 2H), 4.76 (s, 2H), 6.71 (br s, 2H), 5.80 (d, 2H, J=9 Hz), 7.64 (d, 2H, J=9 Hz), 7.73 (br s, 2H), 8.15 (br s, 1H), 8.56 (s, 1H). $^{31}$P (121.4 MHz, DMSO-d$_6$) δ 23.0. MS (m/z) 431.3 [M−H]$^−$.

Scheme 86.5:
(2-{4-[(2,4-Diamino-pteridin-6-ylmethyl)-methyl-amino]-benzoylamino}-propyl)-phosphonic acid diethyl ester

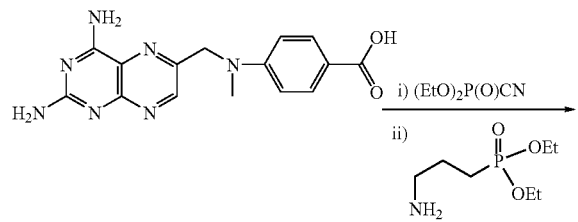

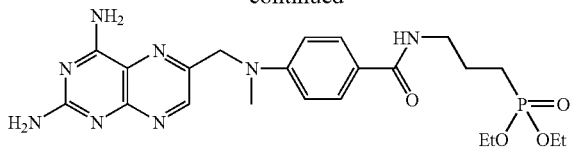

To a solution of 4-[(2,4-diamino-pteridin-6-ylmethyl)-methyl-amino]-benzoic acid hemihydrochloride dihydrate (61.2 mg, 161 mmol) in DMF (2.8 mL) were added diethyl cyanophosphonate (31.8 µL, 210 µmol) and DIEA (27.8 µL, 161 µmol). The solution was stirred at ambient temperature for 3 hours, when diethyl(aminopropyl)phosphonate (34.9 mg, 122.6 µmol) was added. The solution was stirred for 2 additional hours, whereupon complete consumption of the starting materials was observed. The reaction was worked up by removal of the solvent in vacuo and purifying the residue by silica gel chromatography using MeOH—CH$_2$Cl$_2$ (10-30%). The product (65.5 mg) collected from this chromatography step was sufficiently pure to be carried on to the next reaction. A small amount (32.8 mg) was re-purified by RP HPLC on C$_{18}$ column using H$_2$O/acetonitrile (2-95%) to provide 23.2 mg (75%) of the pure product. $^1$H NMR (300 MHz, DMSO-d$_6$) δ 1.20 (t, 6H, J=7.2 Hz), 1.64-1.75 (m, 4H), 3.22 (s, 3H), 3.41 (m, 2H), 3.98 (appt septet, 4H, J=7.2 Hz), 4.85 (s, 2H), 6.79 (d, 2H, J=9 Hz), 7.68 (d, 2H, J=9 Hz), 8.17 (br s, 1H), 8.70 (s, 1H); $^{31}$P (121.4 MHz, DMSO-d$_6$) δ 31.9; MS (m/z) 503.2 [M+H]$^+$.

Scheme 86.6:
(2-{4-[(2,4-Diamino-pteridin-6-ylmethyl)-methyl-amino]-benzoylamino}-propyl)-phosphonic acid

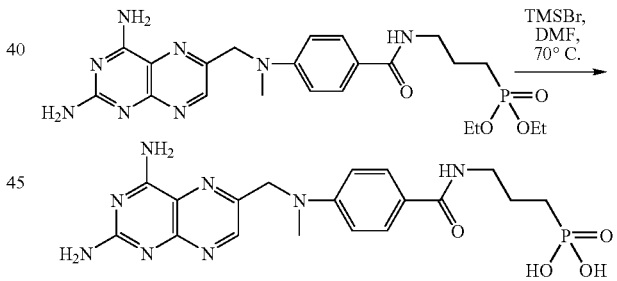

To a solution of crude (2-{4-[(2,4-diamino-pteridin-6-yl-methyl)-methyl-amino]-benzoylamino}-propyl)-phosphonic acid diethyl ester post silica column chromatography (32.2 mg, 66.2 µmol) in dry DMF (0.50 mL) was added TMSBr (68.0 µL, 529.6 µmol) at ambient temperature. The solution was then heated at 70° C. for 1.0 hour, when LCMS analysis demonstrated the reaction to be complete. The reaction mixture was allowed to cool to room temperature, and water (60 µL) and methanol (60 µL) were added. The crude reaction mixture was purified by RP HPLC on C$_{18}$ column using H$_2$O/acetonitrile (2-95%) to provide 11.2 mg (38%) of the desired compound as a yellow solid. $^1$H NMR (300 MHz, DMSO-d$_6$) δ 1.50 (m, 2H), 1.61 (m, 2H), 3.22 (s, 3H), 3.25-3.40 (m, 2H), 4.84 (s, 2H), 6.80 (d, 2H, J=9 Hz), 7.69 (d, 2H, J=9 Hz), 8.20 (br s, 1H), 8.69 (s, 1H). $^{31}$P (121.4 MHz, DMSO-d$_6$) δ 26.3. MS (m/z) 447.3 [M−H]$^−$.

Scheme 86.7:
2-[(2-{4-[(2,4-diaminopteridin-6-ylmethyl)methyl-amino]benzoylamino}-ethyl)phenoxyphoyloxy]propionic acid ethyl ester [diastereomeric mixture at phosphorus]

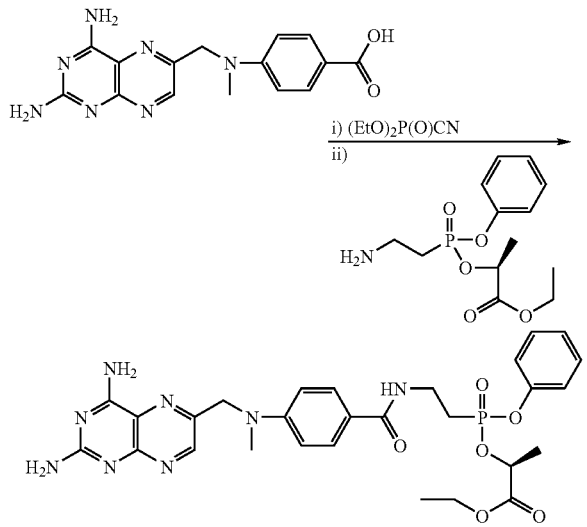

To a solution of 4-[(2,4-diamino-pteridin-6-ylmethyl)-methyl-amino]-benzoic acid hemihydrochloride dihydrate (60.0 mg, 158.3 µmol) in DMF (2.5 mL) were added diethyl cyanophosphonate (31.2 µL, 205.7 µmol) and DIEA (81.8 µL, 474.9 µmol). The solution was stirred at ambient temperature for 3.5 hours, when a solution of (S)-2-[(2-aminoethyl)phenoxyphosphinoyloxy]-propionic acid ethyl ester mono acetic acid salt (57.1 mg, 158.3 µmol; mixture of diastereomers at phosphorus) in DMF (200 µL) was added. The solution was stirred for 1.5 additional hours, whereupon complete consumption of the starting materials was observed. The solvent was removed in vacuo and the crude material was purified by silica gel chromatography using MeOH—CH$_2$Cl$_2$ (10-30%). A small amount of the product (24.8 mg) was repurified by RP HPLC on C$_{18}$ column using H$_2$O/acetonitrile (2-95%) to provide 15.8 mg (65%) of the pure product. $^1$H NMR (300 MHz, DMSO-d$_6$) δ 1.17-1.27 (m, 3H), 1.32 (d, 2H, J=7.5 Hz), 1.42 (d, 1H, J=7.5 Hz) 2.27 (m, 2H), 3.19 (s, 3H), 3.53 (m, 2H), 4.08-4.14 (m, 2H), 4.77 (s, 2H), 4.98 (m, 1H), 6.72 (br s, 1H), 6.81 (d, 2H, J=9 Hz), 7.21 (m, 3H), 7.36 (m, 2H), 7.66 (d, 2H, J=9 Hz), 8.26 (br s, 1H), 8.56 (s, 1H); $^{31}$P (121.4 MHz, DMSO-d$_6$) δ 26.6, 27.4. MS (m/z) 609.2 [M+H]$^+$.

Scheme 86.8:
2-[(2-{4-[(2,4-diaminopteridin-6-ylmethyl)methyl-amino]benzoylamino}-ethyl)phenoxyphospinoyloxy]-propoxy acid [diastereomeric mixture at phosphorus]

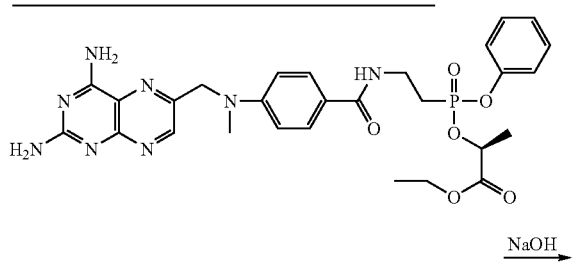

-continued

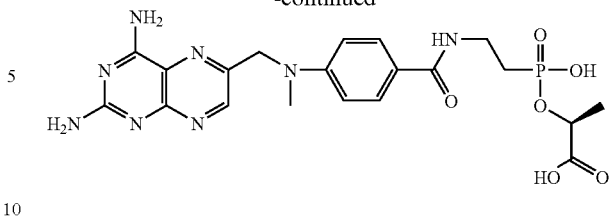

To a solution of 2-[(2-{4-[(2,4-diaminopteridin-6-ylmethyl)methyl-amino]benzoylamino}ethyl)phenoxy-phosphinoyloxy]propionic acid ethyl ester (mixture of diastereomers at phosphorus; 40.0 mg, 65.7 µmol) in DMF (0.4 mL), acetonitrile (0.2 mL) and water (0.2 mL) was added aqueous sodium hydroxide (1 N, 131.4 µL). The solution was stirred at ambient temperature for 4 hours. The solvents were removed in vacuo and the crude product was purified by RP HPLC on C$_{18}$ column using H$_2$O/acetonitrile (2-95%) to provide 23.7 mg (71.3%) of the pure product. $^1$H NMR (300 MHz, DMSO-d$_6$) δ 1.30 (d, 2H, J=6.9 Hz), 1.79 (m, 2H), 3.21 (s, 3H), 3.37 (m, 2H), 4.61 (m, 1H), 4.81 (s, 2H), 6.79 (d, 2H, J=8.7 Hz), 7.64 (d, 2H, J=9.7 Hz), 8.25 (br s, 1H), 8.63 (s, 1H); $^{31}$P (121.4 MHz, DMSO-d$_6$) δ 25.1. MS (m/z) 505.2 [M+H]$^+$.

Scheme 86.9:
2-[(2-{4-[(2,4-diaminopteridin-6-ylmethyl)methylamino]-benzoy-almino}ethyl)phenoxyphosphinoyloxy]propionic acid ethyl ester [diastereomerically pure at phosphorus]

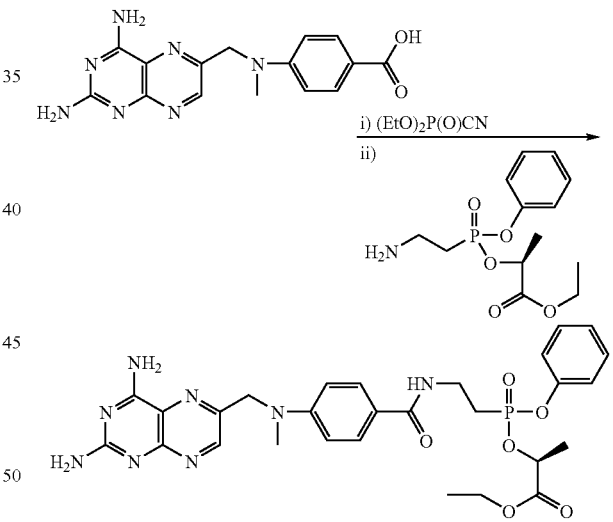

To a solution of 4-[(2,4-diaminopteridin-6-ylmethyl)-methyl-amino]benzoic acid hemihydrochloride dihydrate (101.9 mg, 268.9 µmol) in DMF (3.3 mL) were added diethyl cyanophosphonate (53.0 µL, 349.5 µmol) and DIEA (138.0 µL, 806.7 µmol). The solution was stirred at ambient temperature for 2.5 hours, whereupon (S)-2-[(2-aminoethyl)phenoxyphosphinoyloxy]-propionic acid ethyl ester mono acetic acid salt (diastereomerically pure at phosphorus; 268.9 µmol) in DMF (500 µL) was added. The solution was stirred for 30 additional minutes, whereupon complete consumption of the starting materials was observed. The solvent was removed in vacuo and the crude material was purified by silica gel chromatography using MeOH—CH$_2$Cl$_2$ (10-30%). A small amount of the product (40.0 mg) was repurified by RP HPLC on $C_{18}$ column using $H_2O$/acetonitrile (2-95%) to provide 28.7 mg (75.1%) of the pure product. $^1$H NMR (300 MHz, DMSO-$d_6$) δ 1.15 (t, 3H, J=7.2 Hz), 1.44 (d, 3H, J=6.9 Hz), 2.26 (m, 2H), 3.23 (s, 3H), 3.51 (m, 2H), 4.09 (q, 2H, J=7.2 Hz), 4.86 (s, 2H), 5.01 (m, 1H), 6.81 (d, 2H, J=9.3 Hz), 7.21 (m, 3H), 7.35 (m, 2H), 7.68 (d, 2H, J=9.3 Hz), 8.29 (br s, 1H), 8.71 (s, 1H); $^{31}$P (121.4 MHz, DMSO-$d_6$) δ 26.6. MS (m/z) 609.2 [M+H]$^+$.

Scheme 86.10:
2-[(2-{4-[(2,4-diaminopteridin-6-ylmethyl)methylamino]benzoylamino}-ethyl)-phenoxyphosphinoyloxy]propionic acid ethyl ester [diastereomerically pure at phosphorus]

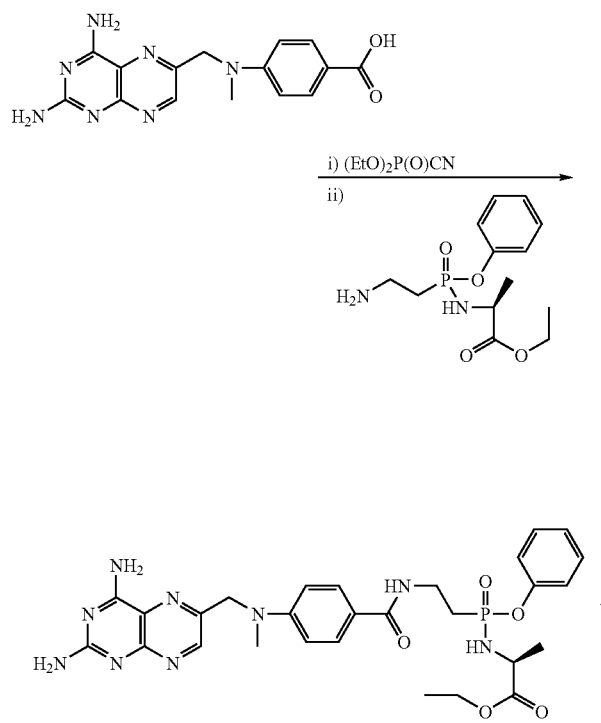

To a solution of 4-[(2,4-diamino-pteridin-6-ylmethyl)-methyl-amino]-benzoic acid hemihydrochloride dihydrate (39.6 mg, 104.0 μmol) in DMF (1.2 mL) were added diethyl cyanophosphonate (20.6 μL, 136.1 μmol) and DIEA (36.0 μL, 209.4 μmol). The solution was stirred at ambient temperature for 3 hours, when (S)-2-[(2-aminoethyl)phenoxyphosphinoylamino]propionic acid ethyl ester mono acetic acid salt (mixture of diastereomers at phosphorus; 104.0 μmol) in DMF (200 μL) was added. The solution was stirred for 30 minutes when complete consumption of the starting materials was observed. An aliquot (66%) of the reaction was purified by silica gel chromatography using MeOH—$CH_2Cl_2$ (10-30%), yielding 27.2 mg of crude product. A small amount of the product (10 mg) was repurified by RP HPLC on $C_{18}$ column using $H_2O$/acetonitrile (2-95%) to provide 4.2 mg (26%) of the pure product. $^1$H NMR (300 MHz, DMSO-$d_6$) δ 1.11 (t, 3H, J=6.9 Hz), 1.18 (d, 3H, J=7.2 Hz), 2.06-2.17 (m, 2H), 3.20 (s, 3H), 3.51 (m, 2H), 3.88 (m, 1H), 4.02 (m, 2H), 4.79 (s, 2H), 5.61 (m, 1H), 6.80 (d, 2H, J=9 Hz), 6.98 (br s, 1H), 7.18 (m, 3H), 7.32 (m, 2H), 7.67 (d, 2H, J=9 Hz), 8.20 (br s, 1H), 8.59 (s, 1H) $^{31}$P (121.4 MHz, DMSO-$d_6$) δ 29.5, 30.1. MS (m/z) 608.2 [M+H]$^+$.

Scheme 86.11:
2-{4-[(2,4-Diamino-pteridin-6-ylmethyl)-methyl-amino]-benzoylamino}-6-(diethoxy-phosphoryl)-hexanoic acid

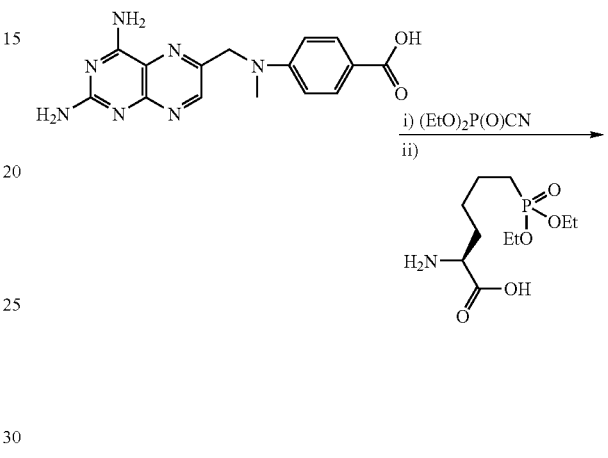

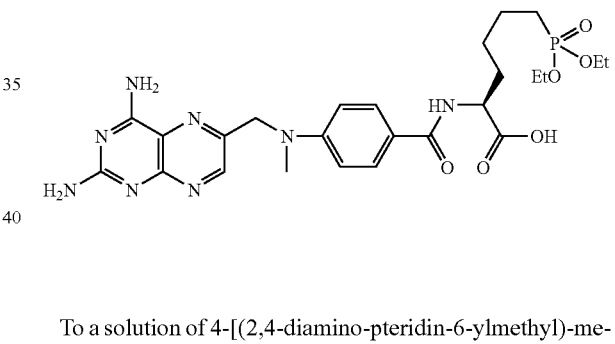

To a solution of 4-[(2,4-diamino-pteridin-6-ylmethyl)-methyl-amino]-benzoic acid hemihydrochloride dihydrate (63.0 mg, 166.2 μmol) in DMF (2.8 mL) were added diethyl cyano phosphonate (30.8 μL, 199.4 μmol) and DIEA (85.8 μL, 498.6 μmol). The solution was stirred at ambient temperature for 3.5 hours when (L)-2-amino-6-diethylphosphonatohexanoic acid (44.3 mg, 166.2 μmol) was added. The solution was stirred for 48 additional hours. The reaction was worked up by removal of the solvent in vacuo and purifying the residue by silica gel chromatography using MeOH—$CH_2Cl_2$ (10-30%). The product (87 mg) collected from this chromatography step was sufficiently pure to be carried on to the next reaction. An aliquot of the product (51.0 mg) was repurified by RP HPLC on $C_{18}$ column using $H_2O$/acetonitrile (2-95%) to provide 24.7 mg (44%) of the pure product. $^1$H NMR (300 MHz, DMSO-$d_6$) δ 1.18 (t, 6H, J=6.9 Hz), 1.42 (m, 4H), 1.65 (m, 4H), 3.20 (s, 3H), 3.92 (m, 4H), 4.29 (m, 1H), 4.78 (s, 2H), 6.72 (br s, 1H), 6.81 (d, 2H, J=9 Hz), 7.73 (d, 2H, J=9 Hz), 8.14 (d, 1H, J=7.8 Hz), 8.56 (s, 1H); $^{31}$P (121.4 MHz, DMSO-$d_6$) δ 31.8; MS (m/z) 574.3 [M]$^+$.

Scheme 86.12:
2-{4-[(2,4-Diaminopteridin-6-ylmethyl)
methylamino]-benzoylamino}-6-
(phosphoryl)hexanoic acid

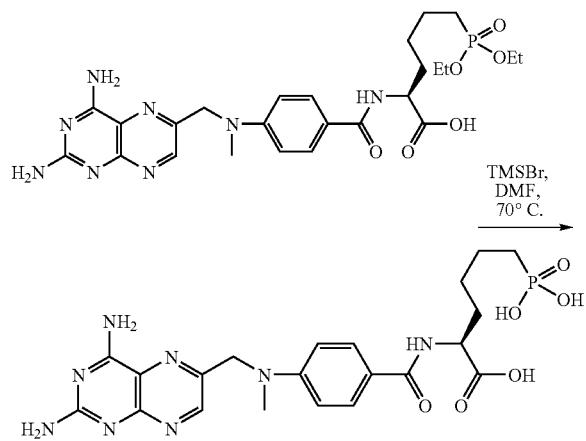

To a solution of crude (2-{4-[(2,4-diamino-pteridin-6-yl-methyl)-methyl-amino]-benzoylamino})-2' (L)-(6'-(phosphonic acid diethyl ester)hexanoic acid) post silica column chromatography (20 mg, 34.6 μmol) in dry DMF (0.60 mL) was added TMSBr (18.0 μL, 139.2 μmol) at ambient temperature. The solution was then heated at 70° C. for 18 hours, after which the reaction mixture was allowed to cool to room temperature. The solvent was removed in vacuo and dissolved in DMF (400 μL) and water (60 μL). This solution was purified by RP HPLC on $C_{18}$ column using $H_2O$/acetonitrile (2-95%) to provide 8.9 mg (49%) of the product as a yellow solid. $^1$H NMR (300 MHz, DMSO-$d_6$) δ 1.45 (m, 6H), 1.75 (m, 2H), 3.20 (s, 3H), 4.25 (m, 1H), 4.77 (s, 2H), 6.62 (br s, 1H), 6.80 (d, 2H, J=8.7 Hz), 7.73 (d, 2H, J=8.7 Hz), 8.14 (br s, 1H), 8.55 (s, 1H); MS (m/z) 519.2 $[M+H]^+$.

Scheme 86.13:
2-{4-[(2,4-Diamino-pteridin-6-ylmethyl)-methyl-amino]-
benzoylamino}-6'-(mono phenyl-phosphonate)
hexanoic acid

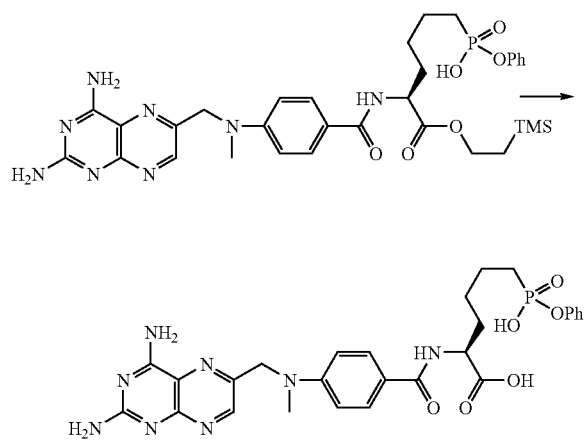

The ethyl-TMS ester is hydrolyzed under suitable conditions to provide the corresponding acid of the invention.

The intermediate 2-{4-[(2,4-Diamino-pteridin-6-ylm-ethyl)-methyl-amino]-benzoylamino}-6'-(mono phenyl-phosphonate)-hexanoic acid TMS ethanol ester can be prepared as follows.

a. (L)-2-Cbz-Amino-hexanoic acid-6-phosphonic acid

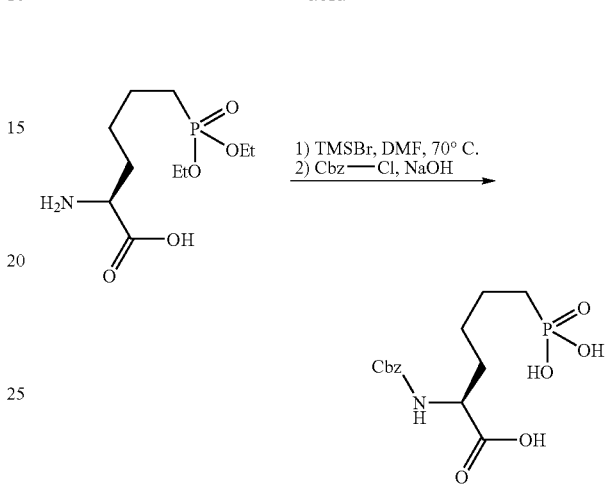

To a suspension of (L)-2-amino-6-(diethoxyphosphonyl) hexanoic acid (106 mg, 396.8 μmol) in dry DMF (2.00 mL) was added TMSBr (307.0 μL, 2,381.0 μmol) at ambient temperature. The solution was then heated at 70° C. for 2 hours, after which the reaction mixture was allowed to cool to room temperature. The solvent was removed in vacuo. The crude material was dissolved in water (0.25 mL) and NaOH (1-N, 2.50 mL). Benzyl chloroformate (79.3 μL, 555.5 μmol) was added and stirring at room temperature was continued. After 2 hours, the solution was washed with ether (2 mL) and the aqueous layer was acidified with aqueous HCl to pH 1. The aqueous layer was extracted with EtOAc (3×5 mL). The combined organic extracts were dried over sodium sulfate. Filtration and evaporation of solvents yielded a crude product, which was sufficiently pure for further transformations. $^1$H NMR (300 MHz, DMSO-$d_6$) δ 1.42-1.65 (m, 8H), 3.90 (m, 1H), 5.02 (s, 2H), 7.32 (s, 5H), 7.55 (m, 1H), 7.94 (s, 1H); $^{31}$P (121.4 MHz, DMSO-$d_6$) δ 26.5; MS (m/z) 345.6 $[M+H]^+$.

b. (L)-2-Amino-hexanoic acid 2' TMS ethyl ester-6-phosphonic acid mono phenyl ester

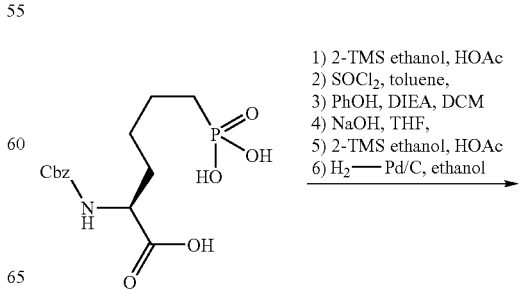

809

-continued

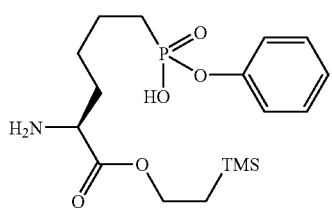

To a solution of (L)-2-Cbz-amino-hexanoic acid-6-phosphonic acid (137.3 mg, 397.9 μmol) in 2-TMS ethanol (2.5 mL) was added acetyl chloride (50 μL). Stirring at room temperature was continued. After 22 hours complete conversion was observed. The solvents were removed in vacuo. The crude material was sufficiently pure for the next step.

One half of the crude material (198.9 μmol) was dissolved in toluene (3.0 mL) at room temperature. Thionyl chloride (167.2 mg, 1,416.0 μmol) was added and the reaction mixture was heated at 70° C. (oil bath). After 4 hours, the reaction was cooled to room temperature and the solvent was removed in vacuo. The crude material was re-dissolved in methylene chloride (2.0 mL) and a solution of phenol (36.6 mg, 389.0 μmol) and DIEA (67.0 μL, 389.0 μmol) in methylene chloride (1.0 mL) was added. Stirring at room temperature was continued. After 4 hrs the solvents were removed in vacuo.

The crude material was dissolved in tetrahydrofuran (THF) (3.0 mL) and aqueous sodium hydroxide solution (1N, 0.885 mL) was added. Stirring at room temperature was continued. After 14 hours the solvent was removed in vacuo to provide the crude phosphonate mono phenyl ester (63.8 mg). This material was dissolved in 2-TMS ethanol (1.0 mL) and acetyl chloride (20 μL) was added. Stirring at room temperature was continued. After 22 hours complete conversion to the carboxylate ester was observed. The solvents were removed in vacuo. The material was sufficiently pure for the next step.

One half of the crude material (75 μmol) was dissolved in ethanol (1.5 mL). Pd/C (5%, 20 mg) was added and the reaction was placed under an atmosphere of hydrogen gas. After 1.5 hours Celite was added and the crude reaction mixture was filtered through Celite. The solvents were removed in vacuo and the crude material was used in the next step without further purification.

810 c. 2-{4-[(2,4-diamino-pteridin-6-ylmethyl)-methyl-amino]-benzoylamino}-6'-(mono phenyl-phosphonate)-hexanoic acid TMS ethanol ester

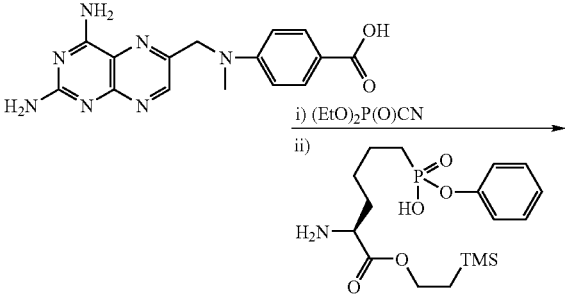

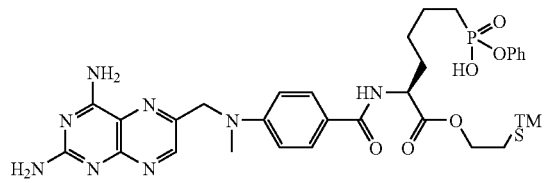

To a solution of 4-[(2,4-diamino-pteridin-6-ylmethyl)-methyl-amino]-benzoic acid hemihydrochloride dihydrate (22.7 mg, 60.0 μmol) in DMF (0.80 mL) were added diethyl cyano phosphonate (12.4 μL, 78.0 μmol) and DIEA (31.0 μL, 180.0 μmol). The solution was stirred at ambient temperature for one hour when (L)-2-amino-6-monophenoxyphosphonato-hexanoic acid 2' TMS ethyl ester (70.5 μmol), suspended in DMF (0.2 mL), was added. The solution was stirred for 3.5 additional hours. The crude reaction mixture was purified by RP HPLC on $C_{18}$ column using $H_2O$/acetonitrile (5-95%) to provide 19.4 mg (46%) of 2-{4-[(2,4-diamino-pteridin-6-yl-methyl)-methyl-amino]-benzoylamino}-6'-(mono phenyl-phosphonate)-hexanoic acid TMS ethanol ester. $^1$H NMR (300 MHz, DMSO-$d_6$) δ 0.0 (s, 9H), 0.91 (t, 2H, J=8.1 Hz), 1.42-1.53 (m, 4H), 1.67-1.76 (m, 4H), 3.24 (s, 3H), 4.10 (t, 2H, J=8.1 Hz), 4.29 (m, 1H), 4.86 (s, 2H), 6.81 (d, 2H, J=9 Hz), 7.12 (m, 3H), 7.31 (m, 2H), 7.74 (d, 2H, J=9 Hz), 8.14 (d, 1H, J=7.8 Hz), 8.71 (s, 1H); $^{31}$P (121.4 MHz, DMSO-$d_6$) δ 26.2; MS (m/z) 695.2 [M]$^+$.

Scheme 86.14:
2-{4-[2,4-Diamino-pteridin-6-ylmethyl)methylamino]-benzoylamino}-6'-(mono phenyl mono (S) ethyl lactate-phosphonate)hexanoic acid

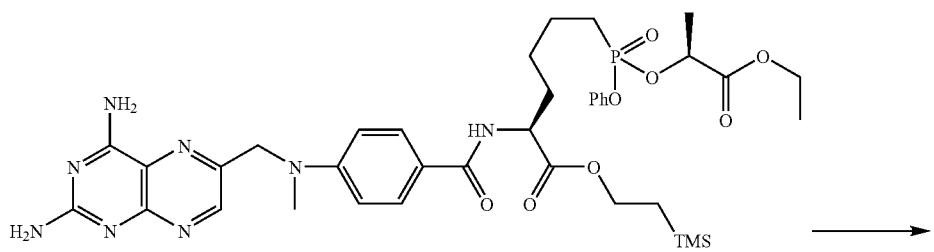

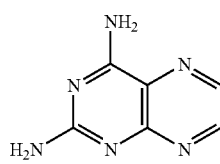

The ethyl-TMS ester is hydrolyzed under suitable conditions to provide the corresponding acid of the invention.

The intermediate 2-{4-[(2,4-diamino-pteridin-6-ylmethyl)-methyl-amino]-benzoylamino}-6'-(mono phenyl mono (S) ethyl lactate-phosphonate)-hexanoic acid TMS ethanol ester can be prepared as follows.

2-{4-[(2,4-Diamino-pteridin-6-ylmethyl)-methyl-amino]-benzoylamino}-6'-(mono phenyl mono (S) ethyl lactate-phosphonate)-hexanoic acid TMS ethanol ester

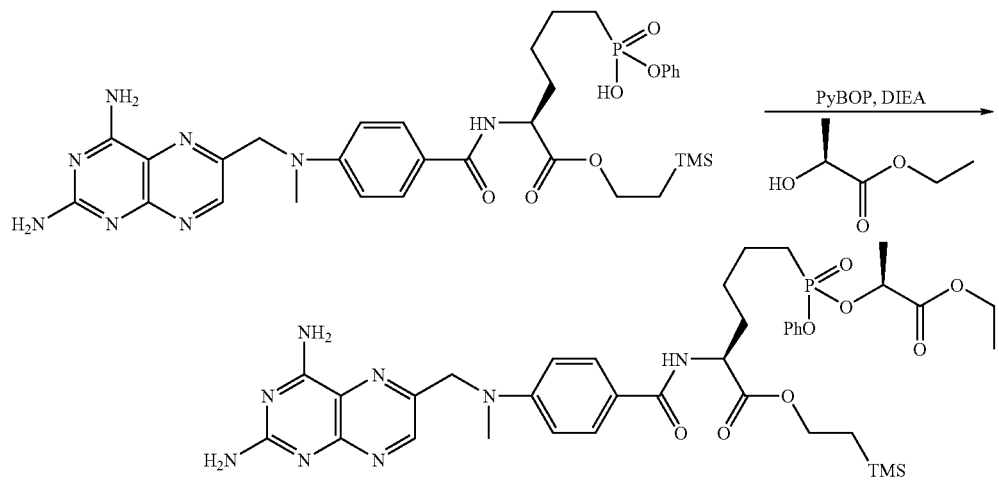

To a solution of 2-{4-[(2,4-diamino-pteridin-6-ylmethyl)-methyl-amino]-benzoylamino}-6'-(mono phenyl-phosphonate)-hexanoic acid TMS ethanol ester (14.5 mg, 20.8 μmol, Example 225) in DMF (0.70 mL) was added PyBOP (32.4 mg, 62.4 μmol), DIEA (21.4 mg, 166.4 μmol) and (S) ethyl lactate (19.6 mg, 166.4 μmol). The reaction mixture was stirred at room temperature for one hour. The crude reaction mixture was purified by RP HPLC on $C_{18}$ column using $H_2O$/acetonitrile (5-95%) to provide 13.5 mg (81%) of the pure product as a mixture of diastereomers at phosphorus (~4:1). $^1H$ NMR (300 MHz, $CDCl_3$) δ 0.0 (s, 9H), 1.02 (t, 2H, J=8.7 Hz), 1.23 (t, 3H, J=9.3 Hz), 1.35 (d, 2.4H, J=6.6 Hz), 1.42-1.53 (m, 4.6H), 1.67-1.86 (m, 4H), 3.14 (s, 3H), 4.03-4.27 (m, 4H), 4.71 (br s, 3H), 4.98 (m, 0.8H), 5.10 (m, 0.2H), 6.57 (d, 2H, J=7.5 Hz), 7.00 (m, 1H), 7.16 (m, 3H), 7.30 (m, 2H), 7.63 (d, 2H, J=7.5 Hz), 8.43 (s, 1H); $^{31}P$ (121.4 MHz, DMSO-$d_6$) δ 30.5, 29.2; MS (m/z) 795.2 $[M]^+$.

Example 87

Preparation of Exemplary Compounds of the Present Invention

A recent PNP inhibitor PNP-405 (also described as PNU-405) was disclosed in the ACS meeting, (2000). This compound inhibits purine nucleotide phosphorylase with an $IC_{50}$ of 20 nM (structure below).

Scheme 87.1

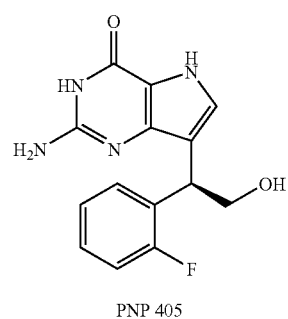

PNP 405

87-1

Reduction of the dose and/or improvement of efficacy is achieved by the use of pro-drugs PNP-405 that, upon cleavage inside the target cell, give rise to agents with increased intracellular half-lives. Such phosphonates pro-drug compounds are shown below (Scheme 87.2).

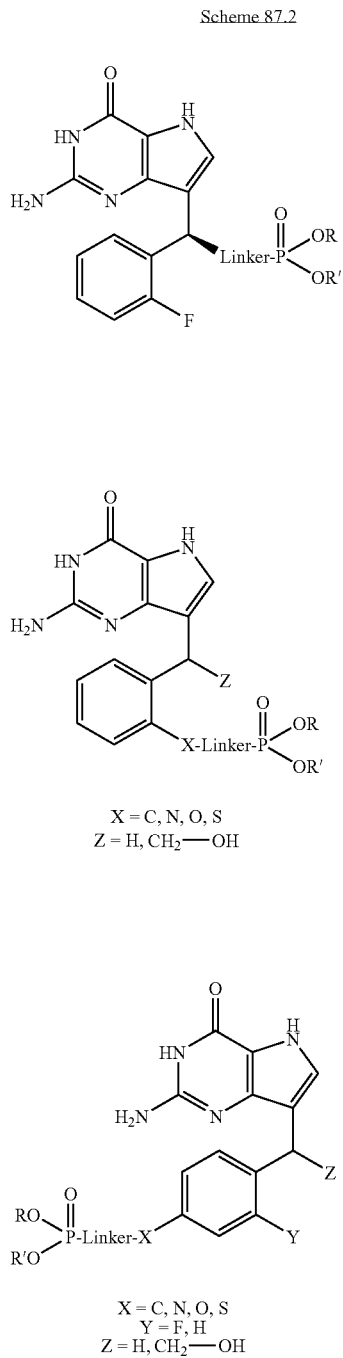

In all cases, linker is 0-8 and preferably 1-6 atoms

Compounds such as 87-2, 87-5 are made according to the general route outlined in Scheme 87.3, with an example depicted in Scheme 87.4.

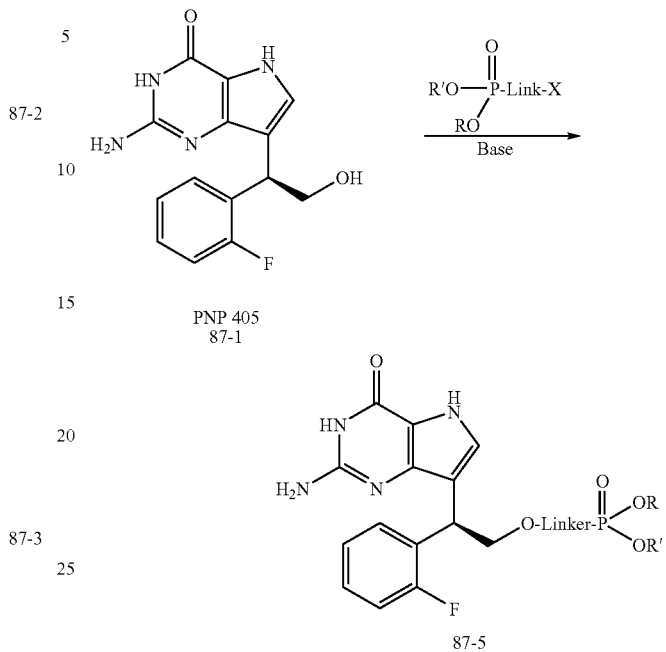

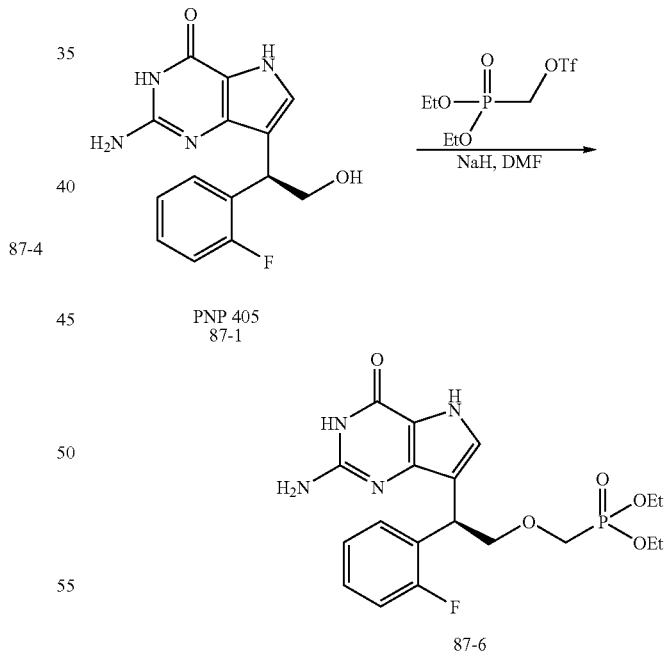

PNP-405 is prepared according to the method of Littler, B. J. et al., 7$^{th}$ International Conference on Organic Process Research and Development, New Orleans, La., March 16-19, (2003). PNP-405 is treated in a solvent such as tetrahydrofuran or dimethylformamide with a base such as sodium hydride. When bubbling ceases, diethyl phosphonomethyltriflate (prepared according to *Tetrahedron Lett*., (1986), 27, 1477) is added, to provide compound 87-6 as the desired product.

Compounds of Scheme 87.2 where X=O, Z=CH₂OH), can be prepared according to the procedure of Littler, B. J. et al., 7$^{th}$ International Conference on Organic Process Research and Development, New Orleans, La., March 16-19, (2003) (Schemes 87.5 and 87.6). The starting material, 2-benzyloxyphenylacetic acid (provided by Avocado) can be acylated via the mixed anhydride with the oxazolidinone shown at 80-85° C., with triethylamine as base. A low-temperature alkylation with bromoacetonitrile results in the formation of compound 87-9 with good diastereomeric ratio. Removal of the chiral auxiliary under reductive conditions yields compound 87-10 without racemization. Protection of the resulting alcohol with the trityl group provides compound 87-11. Subsequent pyrrole ring construction as well as cyclo-guanidinylation reaction to prepare the six-membered 2-aminopyrimidone ring can be prepared as illustrated in Scheme 87.6.

Scheme 87.5:

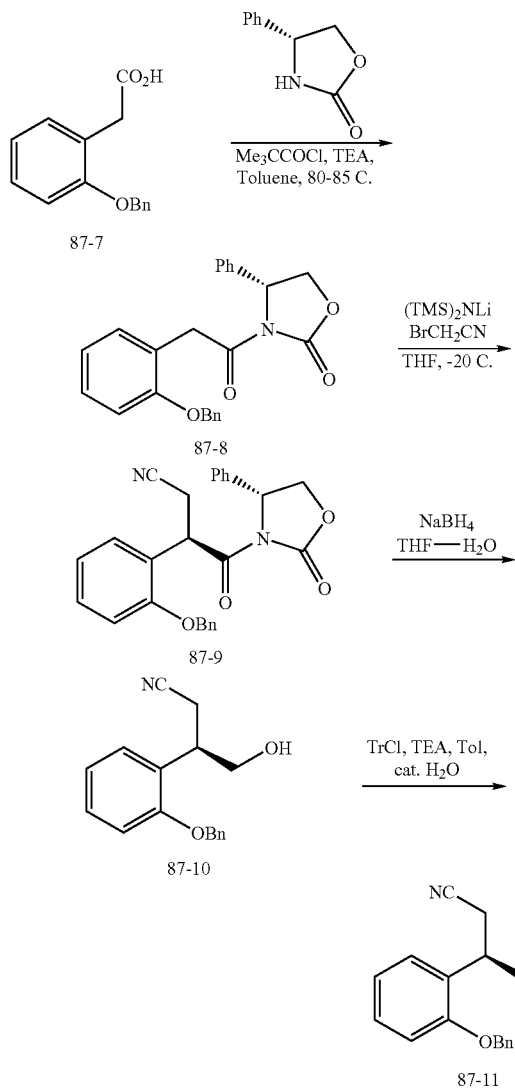

87-7

87-8

87-9

87-10

87-11

Compounds of Schemes 87.2 (where X=O, Z=H) can be prepared according to the general route illustrated above. The starting material, 3-(2-Benzyloxy-phenyl)-propionitrile, is available by Lewis acid-mediated reaction of phenol with acrylonitrile according to U.S. Pat. No. 2,789,995, published in 1954. Intermediate 87-11 can follow the same synthetic steps as outlined here to provide of compounds of Schemes 87.1 and 87.1.

Pyrrole ring construction can be completed in three steps from 3-(2-Benzyloxy-phenyl)-propionitrile. Formation of 3-hydroxy-acrylonitrile 87-13 can be achieved by exposure of 87-12 to LDA and ethyl formate. Condensation of this product with 2-Amino-malonic acid diethyl ester in EtOH and sodium acetate yields compound 87-14 which undergoes a decarboxylative cyclization in the basic medium of NaOH and EtOH to provide pyrrole 87-15. In some syntheses, the trityl protecting group on the benzylic alcohol is removed at this stage. Subsequently, guanidinylation reaction using cyanamide provides compound 87-16 which, upon treatment with sodium hydroxide, cyclizes to form the 2-aminopyrimidone ring (compound 87-17). Removal of the phenolic protecting group under hydrogenolysis conditions provides the free phenol, which is used as the attachment site for the pro-drug group. A variety of linkers may be utilized to attach the pro-drug moiety to the backbone molecule. A particular example in which diethyl phosphonomethyltriflate is used as the starting materials is illustrated below. Therefore, compound 87-18 is treated in a solvent such as tetrahydrofuran or dimethylformamide with a base such as sodium hydride or cesium carbonate. When bubbling ceases, diethyl phosphonomethyltriflate (prepared according to *Tetrahedron Lett.*, (1986), 27, 1477) is added, to provide compounds of Scheme 87.2.

Scheme 87.6:

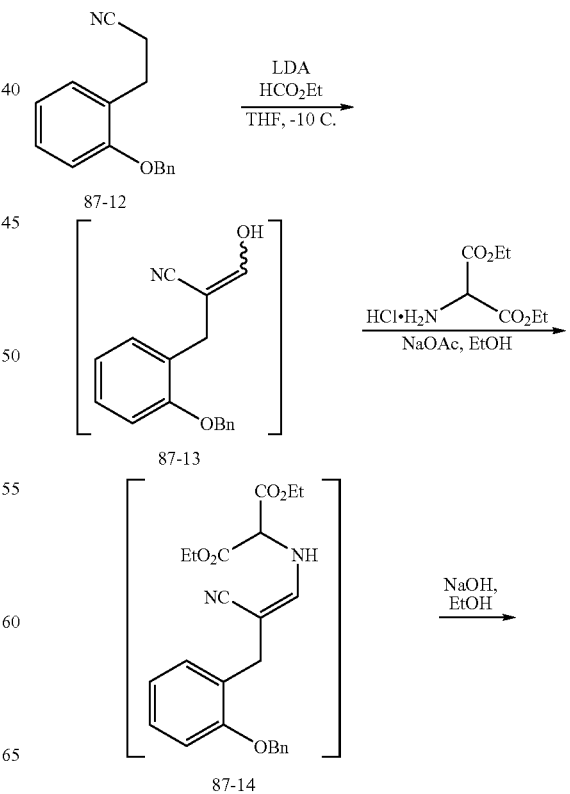

87-12

87-13

87-14

817

-continued

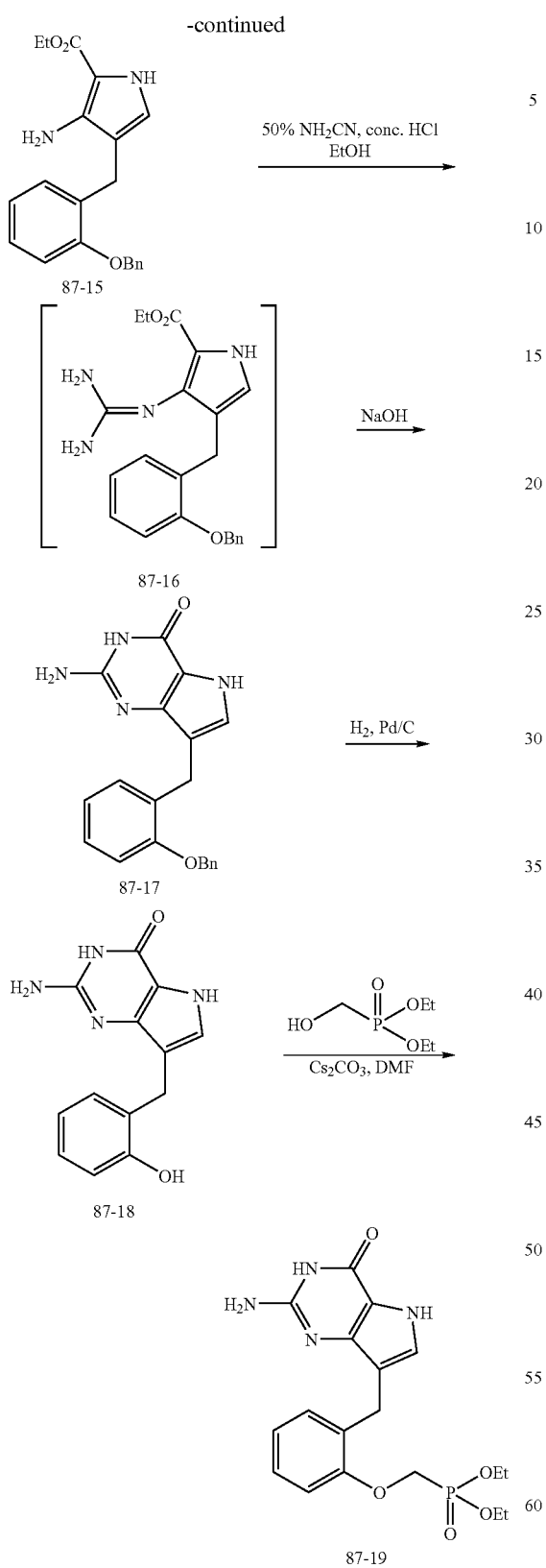

818 to that demonstrated in Scheme 87.7, intermediate 87-24 can be prepared (Scheme 87.7). Proceeding with the sequence shown in Schemes 87.6, 87-24 can be transformed to the desired products of Scheme 87.2.

Scheme 87.7:

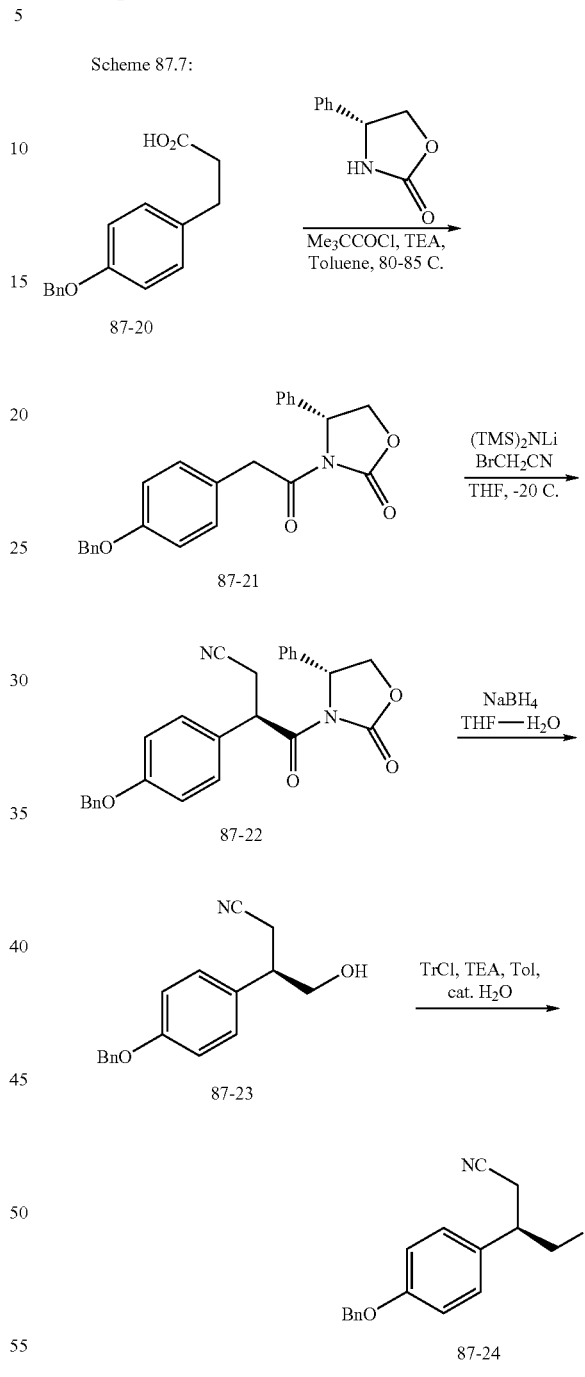

Compounds of Schemes 87.2 (where X=O, Y=H, Z=CH$_2$OH) can be prepared from 4-benzyloxyphenylacetic acid (available from Aldrich). Following a similar sequence Example 88

Preparation of Exemplary Compounds of the Present Invention

The phosphorus containing thiazolidinedione derivative 88-2 is synthesized from parent compounds by alkylation. The parent compound 88-1 is obtained by the procedure as described in U.S. Pat. No. 4,572,912. Scheme 88.1 shows the attachment of the phosphonate linkage to the phenolic OH of 88-1 to give compounds of formula 88-2. Compound 88-1 is dissolved in a suitable aprotic solvent such as, DMF and is then treated with the phosphonate reagent (88-30), bearing a leaving group, for example, bromine, mesyl, tosyl, or trifluoromethanesulfonyl, in the presence of a suitable organic or inorganic base. In the schemes of this Example, $A^o$-LG refers to a phosphonate compound as described is this specification that is attached to a leaving groups, such as, for example, a halogen, a triflate, a mesylate, or a toluenesulfonate.

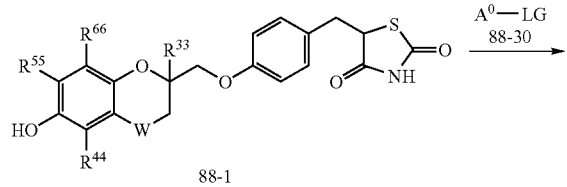

Scheme 88.1

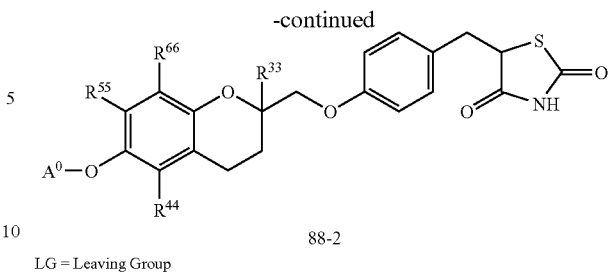

LG = Leaving Group

For example, a solution of 88-3 in DMF is treated with cesium carbonate and one equivalent of (trifluoromethanesulfonyloxy)methylphosphonic acid diethyl ester 88-18, 88-25 to give troglitazone-phosphonate 88-4 in which the linkage is a methylene group as shown in Scheme 88.2. Using the above procedure but employing a different 88-1 and phosphonate reagents 88-30, 88-40, the corresponding products 88-2 bearing different substituents and linking groups can be obtained.

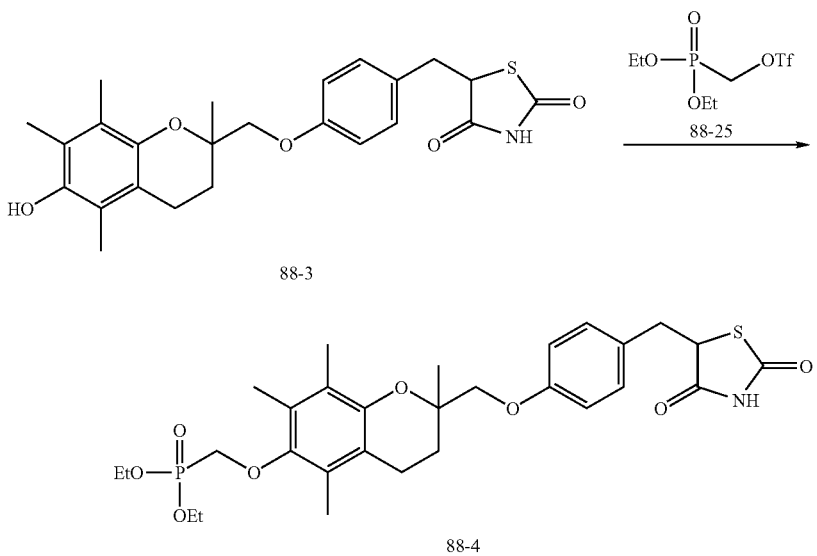

Scheme 88.3 shows the preparation of phosphorus containing thiazolidinedione derivative of type 88-7, 88-20. The parent compound 88-5 is obtained by the procedure as described in U.S. Pat. No. 4,572,912. The phenolic OH and thiazolidinedione unit are protected with suitable protecting group, for example SEM group, and the hydroxyl group at C4 position of chroman alcohol analogs is generated by reduction of the carbonyl group, using suitable reducing agent, for example sodium borohydride. The alcohol 88-6 is then treated with suitable chloroformate ester, for example phenyl chloroformate or p-nitrophenyl chloroformate, or carbonate, such as bis(p-nitrophenyl)carbonate to generate an active carbonate. The resulting active carbonate is reacted with phosphonate reagents bearing amino group 88-35 and subsequent deprotection of protecting groups produces the phosphonates of type 88-7, 88-20.

Scheme 88.3

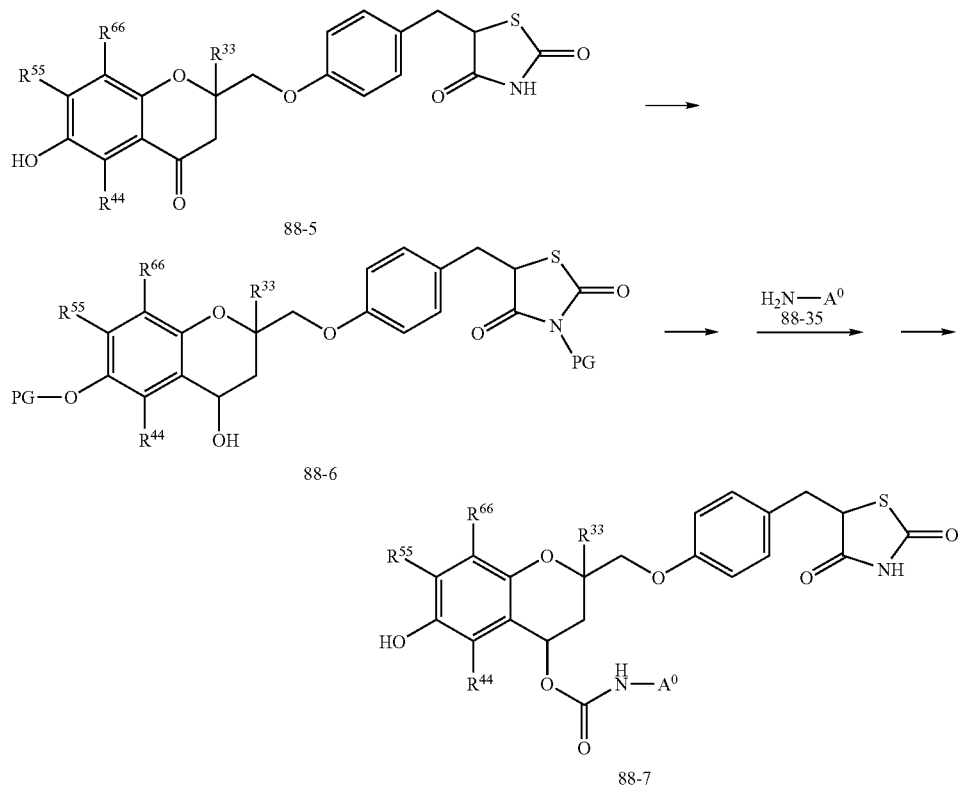

For example, a solution of 88-8 in THF is treated with diisopropylethylamine and two equivalent of 2-(trimethylsilyl)ethoxymethyl chloride to protect the phenolic OH and thiazolidinedione unit. A solution of the protected product in methanol is then reduced using sodium borohydride to obtain the alcohol 88-9. The alcohol 88-9 is treated with phenyl chloroformate to provide phenyl carbonate, which is reacted with 2-aminoethylphosphonate diethyl ester 88-12, to obtain protected phosphonate derivative, which is deprotected by tetrabutylammonium fluoride in THF to result 88-10. Using the above procedure but employing different 88-5 and phosphonate reagents 88-35 the corresponding products 88-7, 88-20 bearing different substituents and linking groups can be obtained.

Scheme 88.4

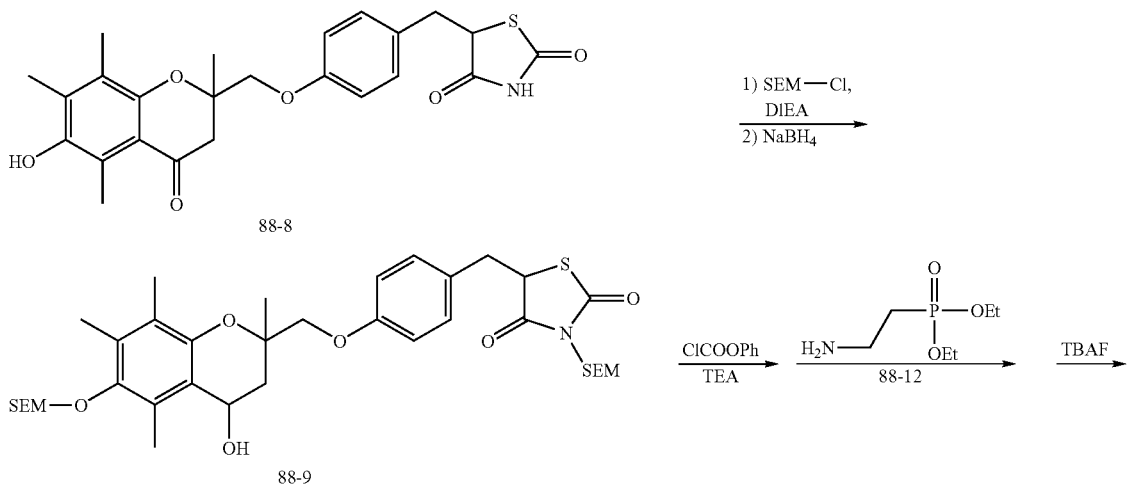

-continued

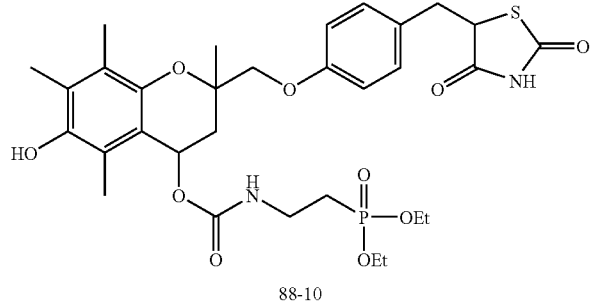

88-10

Scheme 88.5 shows the preparation of phosphorus a containing thiazolidinedione derivative. Thiazolidinedione with phosphorus containing moiety 88-13 is generated by the alkylation of thiazolidinedione 88-11 in a suitable aprotic solvent such as, DMF and is then treated with the phosphonate reagent 88-30, 88-40, bearing a leaving group, for example, bromine, mesyl, tosyl, or trifluoromethanesulfonyl, in the presence of a suitable organic or inorganic base. Compound 88-13 is then reacted with benzaldehyde 88-14 with protected phenol at the para position. The protecting group $R^{88}$ can be any protecting group for phenolic OH, for example alkoxyalkyl groups, such as the methoxymethyl group; aralkyl groups, such as the benzyl group; the 2-tetrahydropyranyl group; and acyl groups, such as the acetyl or benzoyl groups, preferably benzyl group. The reaction is carried out in an aprotic solvent, such as toluene, suitably at an elevated temperature, such as the reflux temperature of the solvent, and preferably in the presence of a suitable catalyst, such as piperidinium acetate or benzoate. Favorably, the water produced in the reaction is removed from the reaction mixture, for example by means of a Dean and Stark apparatus. The reduction of 88-15 to 88-16 is accomplished by catalytic reduction with suitable catalysts, such as palladium on carbon catalysts, preferably a 10% palladium on charcoal catalyst. (U.S. Pat. No. 6,288,095) The coupling of 88-16 with chroman alcohol homolog 88-17, which is obtained by the procedure described in J. American Oil Chemical Society (1974), 51, 200 or in U.S. Pat. No. 4,572,912, and in which the alcoholic functional groups are suitably protected as described in U.S. Pat. No. 4,572,912, is done using Mitsunobu condition.

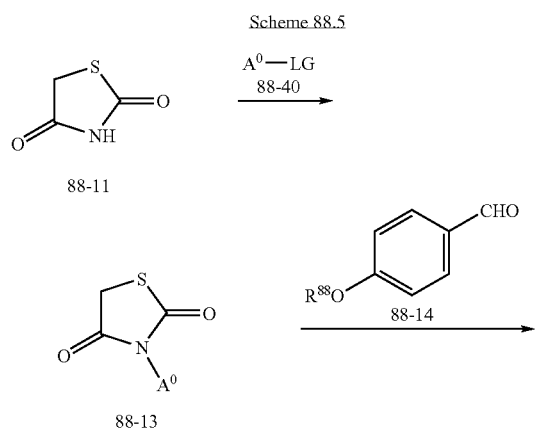

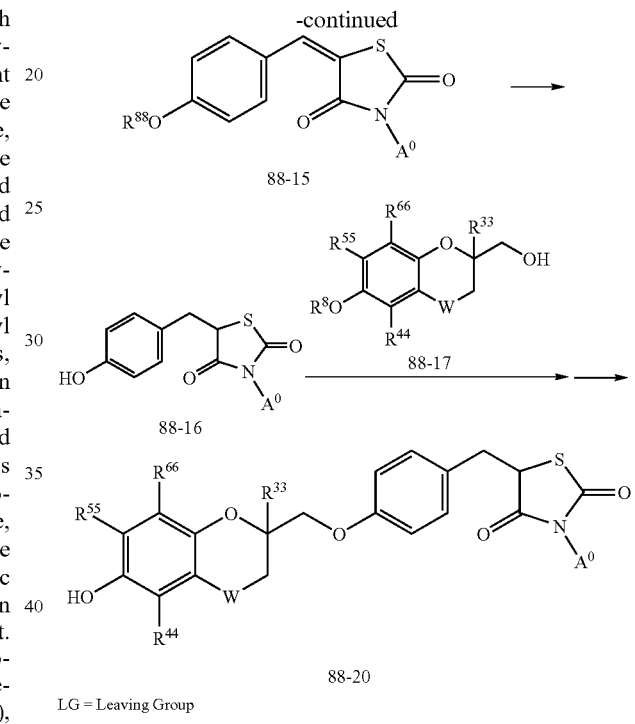

LG = Leaving Group

For example, a solution of 88-11 in DMF is treated with sodium hydride and one equivalent of (trifluoromethanesulfonyloxy)methylphosphonic acid diethyl ester 88-18, 88-25 to give thiazolidinedione-phosphonate 88-19 in which the linkage is a methylene group as shown in Scheme 88.6. The thiazolidinedione-phosphonate 88-19 is then reacted with the benzaldehyde 88-20 bearing benzyloxy substituent in toluene in reflux condition in the presence of catalytic piperidinium acetate with Dean-Stark apparatus, which results 88-21. The reduction of 88-21 in dioxane by catalytic hydrogenation in the presence of 10% palladium on charcoal provides 88-22. The reaction between 88-22 and chroman alcohol analogs 88-23 in the presence of diethyl azodicarboxylate and triphenylphosphine followed by deprotection of SEM group by TBAF provides 88-24. Using the above procedure but employing different chroman alcohol analogs and phosphonate reagents 88-30, 88-40 the corresponding products 88-2 bearing different substituents and linking groups are obtained.

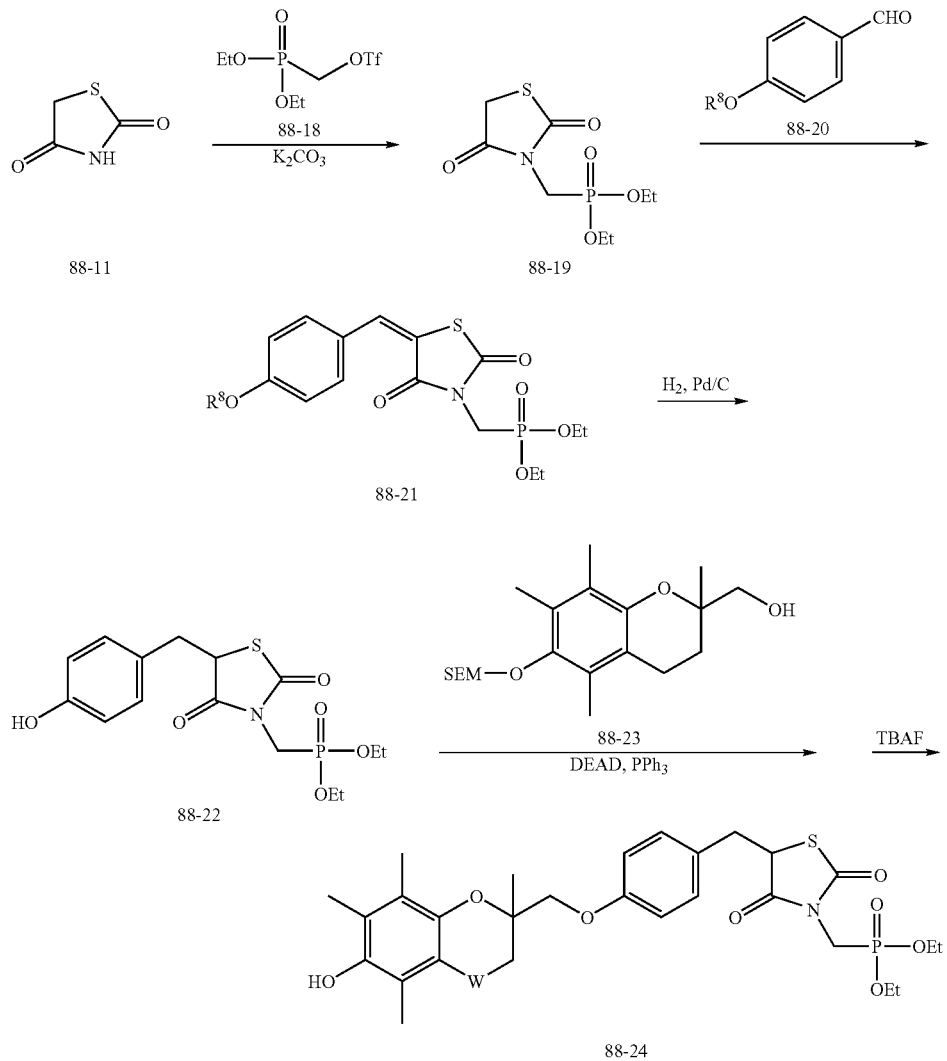

Example 89

Preparation of Exemplary Compounds of the Present Invention

Schemes K2-K4 illustrate the syntheses of phosphonate compounds of the invention, K2-K4, and of the intermediate compounds necessary for their synthesis.

Protection of Reactive Substituents.

Depending on the reaction conditions employed, it may be necessary to protect certain reactive substituents from unwanted reactions by protection before the described sequence is reacted, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

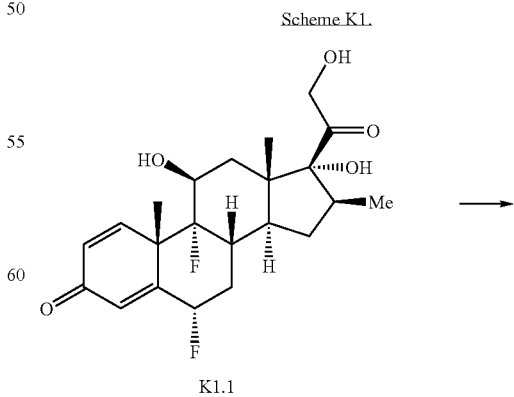

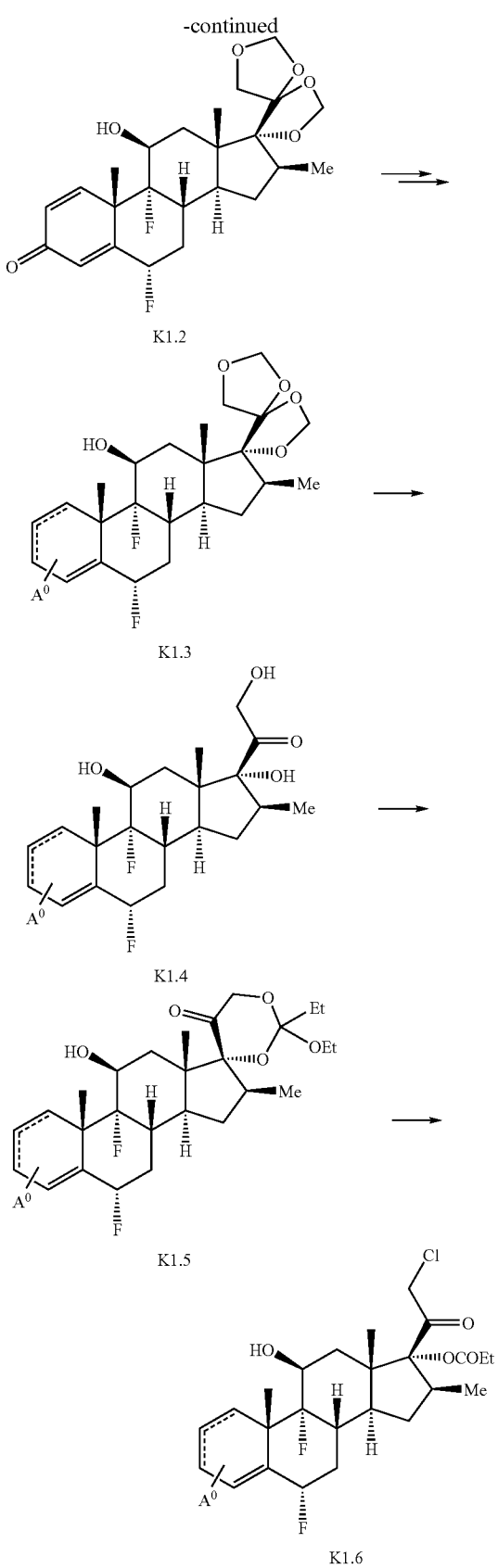

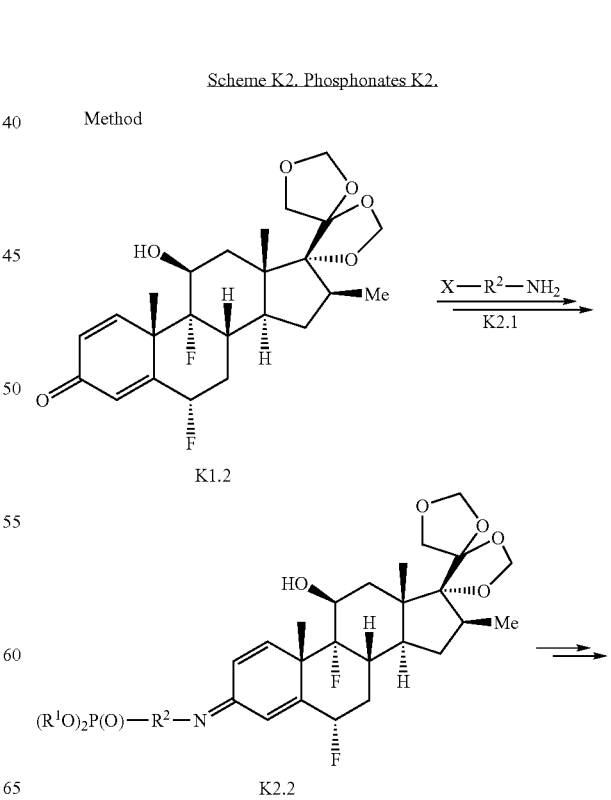

bis-methylenedioxy (BMD) moiety. In this sequence, 6α,9α-difluoro-16β-methyl-11β,17α,21-trihydroxypregn-1,4-dien-3,21-dione K1.1 (U.S. Pat. No. 4,619,921) is reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative K1.2. The phosphonate moiety is then introduced, using the procedures described below, to produce the phosphonate ester K1.3. The BMD moiety is then hydrolyzed, for example by treatment with 50% aqueous acetic acid, as described in Protective Groups in Organic Synthesis, by T. W. Greene and P. G. M. Wuts, Wiley, Second Edition 1990, p. 223, to afford the triol K1.4. The latter compound is then converted into the 17,21-cyclic orthoester K1.5 using the procedure described in Chem. Pharm. Bull., 1986, 34, 1613. The substrate is reacted in dimethylformamide at 70° C. with two molar equivalents of triethyl orthopropionate and a catalytic amount of p-toluenesulfonic acid. The product is then reacted with an excess of trimethylsilyl chloride in dimethylformamide at ambient temperature to produce the 21-chloro 17-propionate product K1.6.

Alternatively, the substrate K1.4 is converted into the product K1.6 by means of the method described in *J. Med. Chem.*, (1987), 30: 1581. In this procedure, the 21-hydroxy group is activated by conversion to the 21-mesylate, by reaction with mesyl chloride in pyridine; the mesylate group is then displaced to yield the 21-chloro intermediate, by reaction with lithium chloride in dimethylformamide, and the 17-hydroxyl group is esterified to give the 21-chloro-17-propionate derivative K1.6. The selective acylation of the 17α hydroxyl group in the presence of an 11β hydroxyl group is described in *J. Med. Chem.*, (1987), 30: 1581.

Preparation of the Phosphonate Esters K2

Scheme K2. Phosphonates K2.

Method

For example, Scheme K1 depicts a protection-deprotection sequence in which the steroid side-chain is protected as a -continued

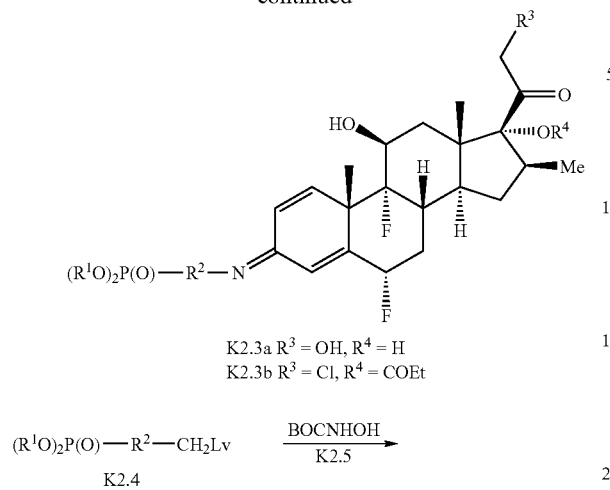

K2.3a R³ = OH, R⁴ = H
K2.3b R³ = Cl, R⁴ = COEt $(R^1O)_2P(O)-R^2-CH_2Lv$  $\xrightarrow{\text{BOCNHOH}}_{\text{K2.5}}$
K2.4

$(R^1O)_2P(O)-R^2-CH_2ONHBOC$ →
K2.6

$(R^1O)_2P(O)-R^2-CH_2ONH_2$
K2.7

Scheme K2 depicts the preparation of phosphonates K12 in which the phosphonate is attached by means of an imino or iminoxy group and a variable carbon chain. In this procedure, the BMD-protected derivative K1.2 is reacted with an amine or hydroxylamine K2.1, in which R² is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime. The preparation of oximes of steroidal 3-ketones is described in *Anal. Bioch.*, (1978), 86, 133. and in *J. Mass. Spectrom.*, (1995), 30, 497. The BMD-protected side-chain compound K12.2 is then converted into the triol K2.3a, and then to the 21-chloro 17 propionate product K2.3b, as described in Scheme K1.

Scheme K12 also illustrates the preparation of hydroxylamine ethers incorporating a phosphonate group. In this procedure, a phosphonate K12.4, in which Lv is a leaving group such as bromo or trifluoromethylsulfonyloxy, is reacted with BOC-hydroxylamine K12.5 (Aldrich) to produce the ether K12.6. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether K12.7.

Scheme K2

Example 89-A

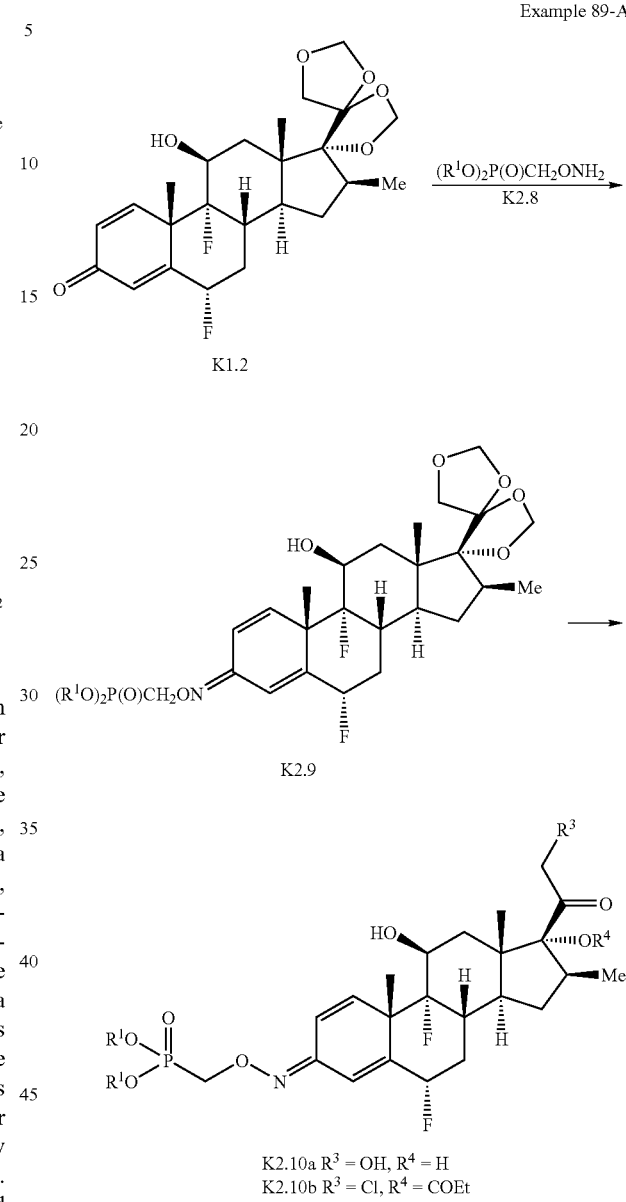

Scheme K2, Example 89-A illustrates the preparation of phosphonates K2 in which the phosphonate is attached by means of an iminoxy group. In this procedure, the substrate K1.2 is reacted with a dialkyl phosphonomethyl hydroxylamine K2.8, prepared as described above from a dialkyl trifluoromethylsulfonyloxymethyl phosphonate (*Tet. Lett.* 27:1477 (1986)) and BOC-hydroxylamine, to afford the oxime K2.9. Deprotection then affords the triol K2.10a from which the 21-chloro 17-propionate compound K2.10b is prepared. The oxime forming reaction is performed at ambient temperature in ethanol-acetic acid solution between equimolar amounts of the reactants.

Using the above procedures, but employing, in place of the hydroxylamine ether K2.8, different oxime ethers K2.1, the corresponding products K2.3b are obtained.

Scheme K2

Example 89-B

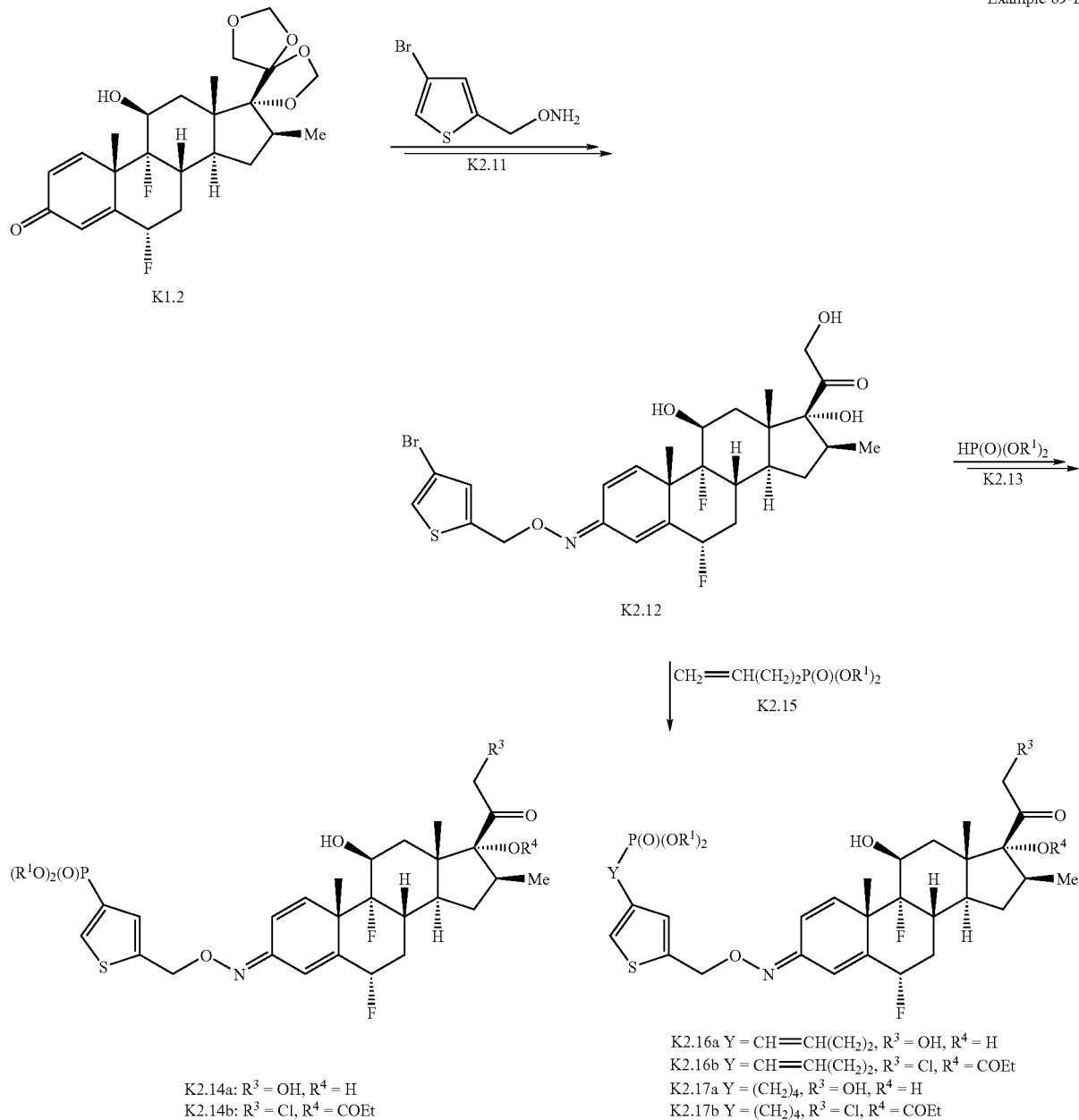

Scheme K2, Example 89-B illustrates the preparation of compounds K2 in which the phosphonate group is attached by means of a thienylmethoxy oxime group. In this procedure, the dienone K1.2 is reacted, as described above, with O-(4-bromo-2-thienylmethoxy)hydroxylamine K2.11, prepared as described above from 4-bromo-2-bromomethylthiophene (WO 9420456) and BOC-protected hydroxylamine, to give, after deprotection of the side-chain, the oxime K2.12. The product is then reacted, in the presence of a palladium catalyst, with a dialkyl phosphite K2.13 to afford the phosphonate K2.14a. The preparation of arylphosphonates by means of a coupling reaction between aryl bromides and dialkyl phosphites is described in *J. Med. Chem.* 35:1371 (1992). The reaction is performed in an inert solvent such as toluene, in the presence of a base such as triethylamine and a catalytic amount of tetrakis(triphenylphosphine)palladium (0). The 21-hydroxy compound K2.14a is then converted, as described in Scheme K1, into the 21-chloro 17-propionate derivative K2.14b.

Alternatively, the bromo compound K2.12 is coupled with a dialkyl butenyl phosphonate K2.15 (*Org. Lett.* 3:217 (2001)) to afford the phosphonate K2.16a. The coupling of aryl halides with olefins by means of the Heck reaction is described, for example, in F. A. Carey and R. J. Sundberg, *Advanced Organic Chemistry* 503ff (Plenum, 2001) and in *Acc. Chem. Res.* 12:146 (1979). The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the double bond present in the product K2.16a is reduced, for example by reaction with diimide, to produce the saturated analog K2.17a. The reduction of olefinic bonds is described in R. C. Larock, *Comprehensive Organic Transformations* 6ff (VCH 1989). The transformation is effected by means of catalytic hydrogenation, for example using a palladium on carbon catalyst and hydrogen or a hydrogen donor, or by the use of diimide or diborane. The products K2.16a and K2.17a are then converted into the 21-chloro 17-propionate analogs K2.16b and K2.17b.

Using the above procedures, but employing, in place of the bromothienylmethoxy reagent K2.11, different bromo-substituted aryl or heteroaryl alkoxy hydroxylamines, and/or different dialkyl alkenyl phosphonates, the products analogous to the compounds K2.14b, K2.16b and K2.17b are obtained.

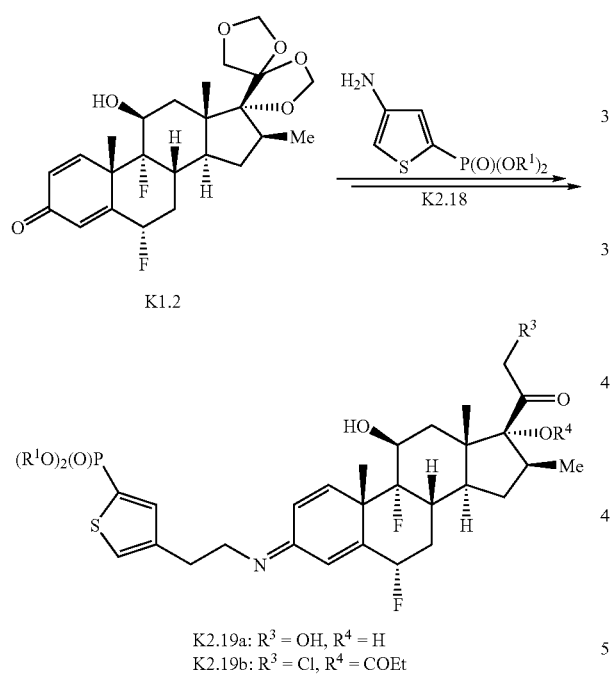

Scheme K2, Example 89-C depicts the preparation of phosphonates K2 in which the phosphonate is attached by means of an imino group. In this procedure, the substrate K1.2 is reacted with a dialkyl 4-amino-2-thienyl phosphonate K2.18, prepared by the palladium-catalyzed coupling, as described above, between 4-amino-2-bromothiophene (*Tet.* 43:3295 (1987)) and a dialkyl phosphite, to give, after deprotection, the imine product K2.19a. The imine forming reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions. The product is then converted into the 21-chloro 17-propionate compound K2.19b.

Using the above procedures, but employing, in place of the 4-aminothienyl phosphonate K2.18 different amino-substituted aryl or heteroaryl phosphonates, products analogous to K2.19b are obtained.

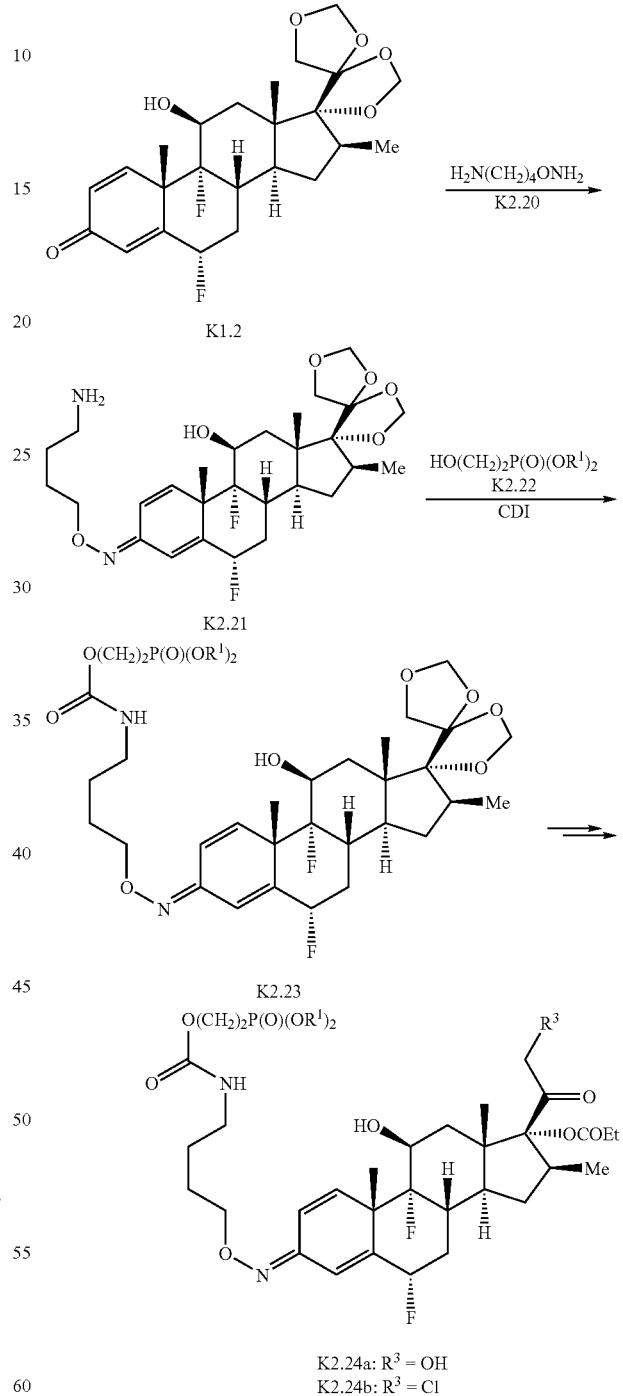

Scheme K2, Example 89-D illustrates the preparation of phosphonates K2 in which the phosphonate is attached by means of an oximino group and an amide linkage. In this procedure, the dienone K1.2 is reacted with O-(4-aminobutyl)hydroxylamine K2.20 (*Pol. J. Chem.* 55:1163 (1981)) to yield the oxime K2.21. The reaction of steroidal 1,4-dien-3-ones with substituted hydroxylamines is described in *J. Steroid Bioch.* 7:795 (1976); the reaction is performed between equimolar amounts of the reactants in a polar organic solvent such as pyridine or methanol, optionally in the presence of acetic acid or sodium acetate. The product is then coupled with a dialkyl 2-hydroxyethyl phosphonate K2.22 (Epsilon) and carbonyl diimidazole, to yield the carbamate oxime K2.23. The preparation of carbamates is described in A. R. Katritzky, Comprehensive Organic Functional Group Transformations, 6:416ff (Pergamon, 1995), and in S. R. Sandier and W. Karo, Organic Functional Group Preparations, 260ff (Academic Press, 1986). In the procedure, the amine is reacted in an inert aprotic solvent such as dichloromethane or tetrahydrofuran, with phosgene or a functional equivalent thereof, such as carbonyl diimidazole, triphosgene, pentafluorophenyl carbonate and the like, to afford the corresponding activated acylamine. The latter compound is then reacted with an alcohol to yield the carbamate. The carbamate product K2.23 is then converted, as described in Scheme K1, into the 21-chloro 17-propionate product K2.24b.

Using the above procedures, but employing, in place of the hydroxylamine K2.22, different amino-substituted hydroxylamines, and/or different hydroxy-substituted phosphonates, the products analogous to K2.24b are obtained.

Preparation of the Phosphonate Esters K3 and K4.

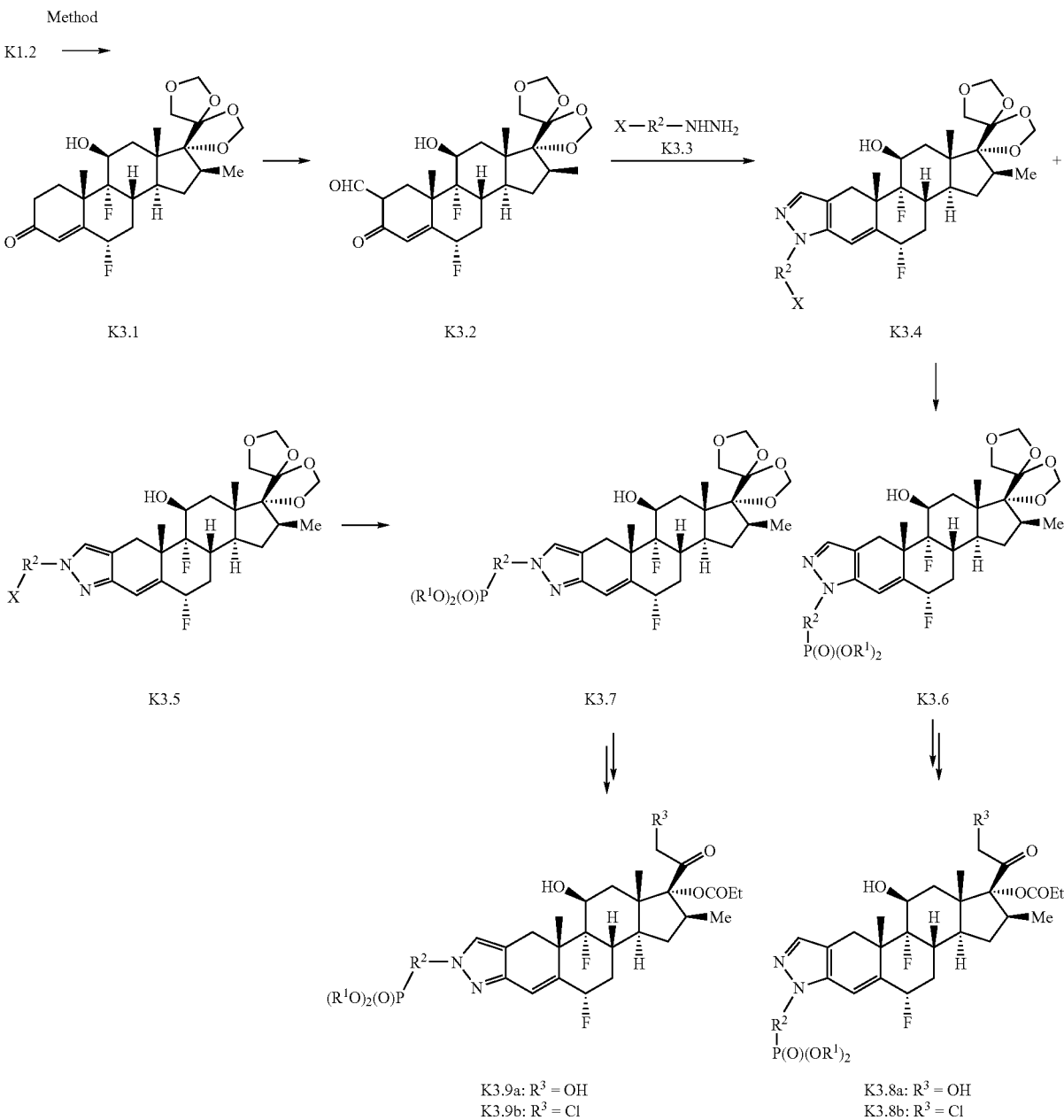

Scheme K3. Phosphonates K3 and K4.

Scheme K13 illustrates the preparation of the phosphonate esters K13 and K4 in which the phosphonate group is attached to the 1' or 2' position of the pyrazole ring, by means of an aromatic or heteroaromatic group, a heteroatom and/or a variable carbon chain. In this procedure, the BMD-protected dienone K1.2 is reduced to afford the 1,2-dihydro product K13.1. The catalytic hydrogenation reaction is effected by the use of tris(triphenylphosphine)rhodium (I) chloride, for example as described in *J. Med. Chem.* 44:602 (2001). The product is then reacted with ethyl formate and a base such as sodium hydride, in an inert solvent such as toluene or dimethylformamide, as described in *J. Am. Chem. Soc.* 86:1520 (1964), to afford the 2-formyl product K13.2. This compound is then reacted with an alkyl, aralkyl, aryl or heteroaryl hydrazine K13.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles K13.4 and K13.5. The pyrazole-forming reaction is performed between equimolar amounts of the reactants in an acidic solvent such as acetic acid, as described in *J. Am. Chem. Soc.* 86:1520 (1964). The pyrazoles K13.4 and K13.5 are then transformed, for example by the procedures described in Examples 89-E and 89-F, via the BMD-protected intermediates K13.6 and K13.7, into the 21-chloro 17-propionate phosphonates K13.8b and K3.9b.

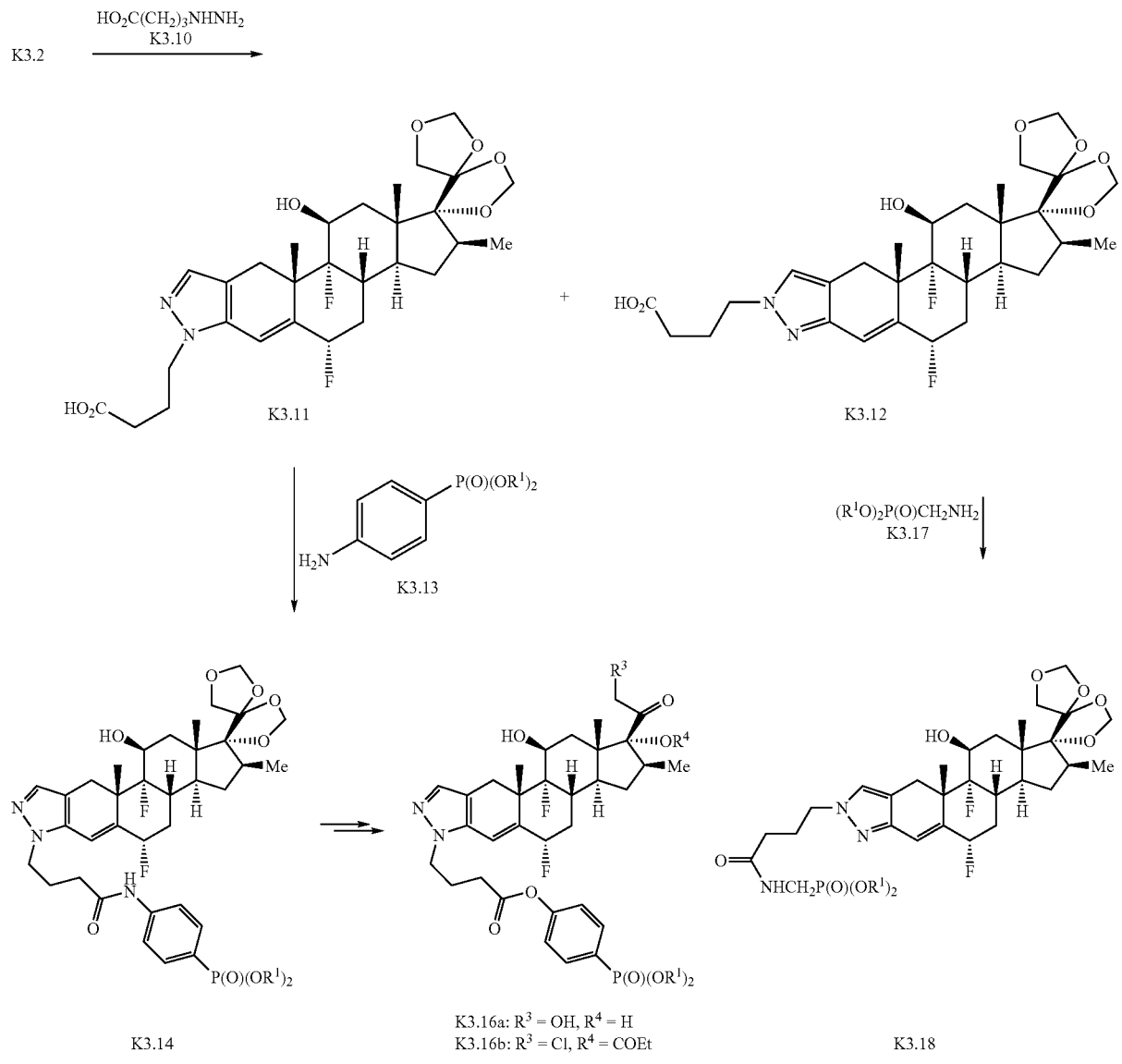

Scheme K3, Example 89-E

-continued

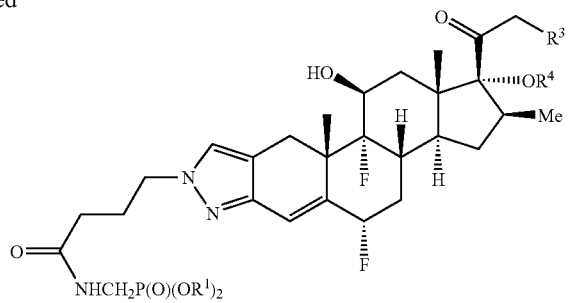

K3.19a: $R^3$ = OH, $R^4$ = H
K3.19b: $R^3$ = Cl, $R^4$ = COEt

Scheme K3, Example 89-E illustrates the preparation of phosphonates K3 and K4 in which the phosphonate is attached by means of an amide linkage. In this procedure, the ketoaldehyde K3.2 is reacted, as described above, with 3-carboxypropyl hydrazine K3.10 (Ind. J. Exp. Biol. 32:218 (1994)) to give the pyrazoles K3.11 and K3.12. The 2'-substituted isomer K3.11 is then reacted in dimethylformamide solution at ambient temperature with one molar equivalent of a dialkyl 4-aminophenyl phosphonate K3.13 (Epsilon) and dicyclohexyl carbodiimide, to yield the amide K3.14. The preparation of amides from carboxylic acids and derivatives is described, for example, in S. R. Sandler and W. Karo, Organic Functional Group Preparations, 274 (Academic Press, 1968), and R. C. Larock, Comprehensive Organic Transformations, 972ff (VCH, 1989). The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide.

The BMD protecting group is then removed and the product is converted into the 21-chloro 17-propionate product K3.16b.

Alternatively, the 1'-substituted pyrazole K3.12 is coupled, as described above, with a dialkyl aminomethyl phosphonate K3.17 (Interchim), to afford the amide K3.18. The product K3.18 is then deprotected to give the triol K3.19a, and the latter compound is transformed into the 21-chloro 17-propionate K3.19b.

Using the above procedures, but employing different amino-substituted phosphonates, and/or different carboxy-substituted hydrazines, the products analogous to K3.16b and K3.19b are obtained. The functionalization procedures are interchangeable between the pyrazole substrates K3.11 and K3.12.

Scheme K3 Example 89-F

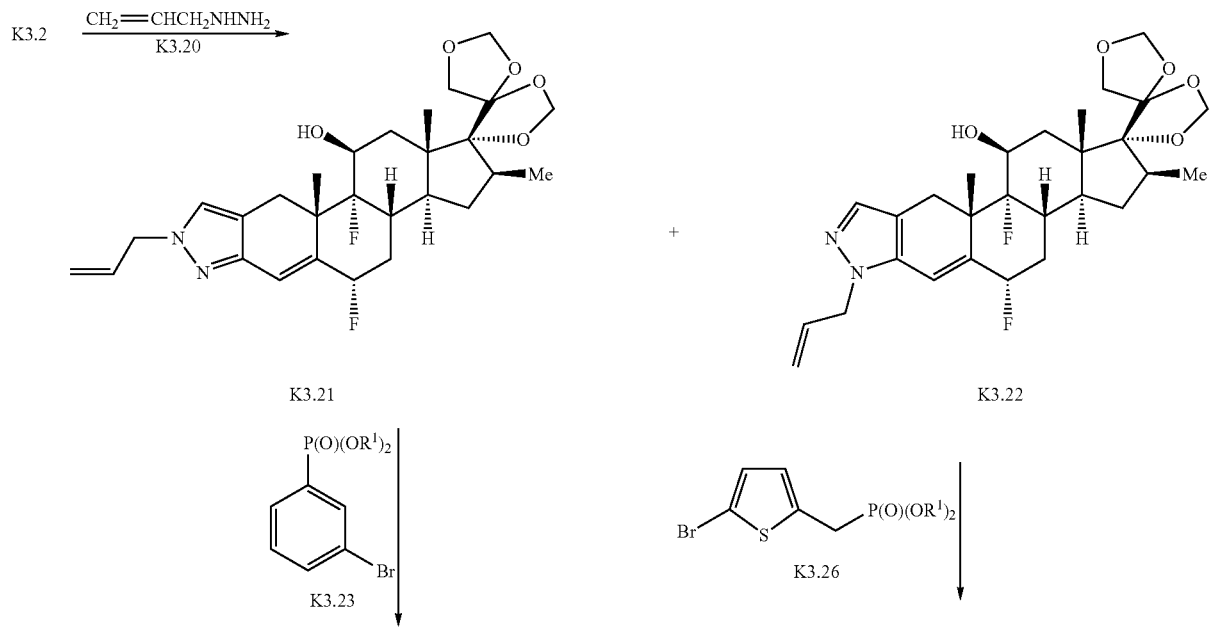

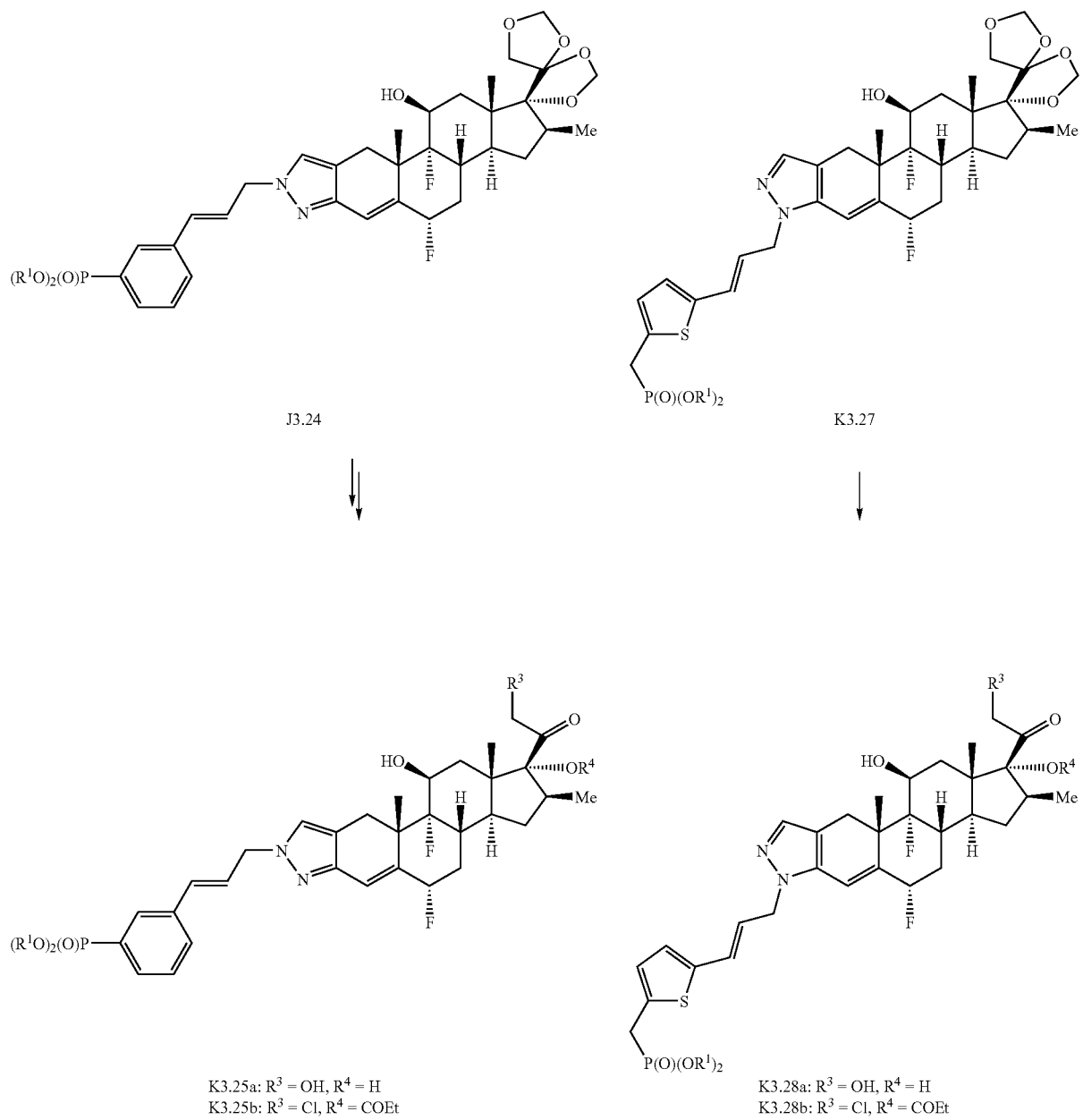

K3.25a: R³ = OH, R⁴ = H
K3.25b: R³ = Cl, R⁴ = COEt

K3.28a: R³ = OH, R⁴ = H
K3.28b: R³ = Cl, R⁴ = COEt

Scheme K3, Example 89-F illustrates the preparation of the phosphonates K3 and K4 in which the phosphonate group is attached by means of an aryl ring and a propenyl linkage. In this procedure, the ketoaldehyde K3.2 is reacted, as described above, with allyl hydrazine K3.20 (*Zh. Org. Khim.*, 3:983 (1967)) to produce the pyrazoles K3.21 and K3.22. The 1'-substituted isomer K3.21 is coupled, as described in Scheme K2, with a dialkyl 3-bromophenyl phosphonate K3.23 (Epsilon) to give the phosphonate K3.24. The product is then deprotected to afford the triol K3.25a which is converted into the 21-chloro 17-propionate compound K3.25b.

Alternatively, the 2'-substituted pyrazole K3.22 is coupled, as described above, with a dialkyl 5-bromo-2-thienyl phosphonate K3.26 (*Syn.*, 455 (2003)) to prepare the phosphonate K3.27 which is deprotected, and the product is converted into the 21-chloro 17-propionate analog K3.28b.

Using the above procedures, but employing, in place of the propenyl hydrazine K3.20, different alkenyl hydrazines, and/ or different dialkyl bromo-substituted phosphonates, the products analogous to the compounds K3.25b and K3.28b are obtained.

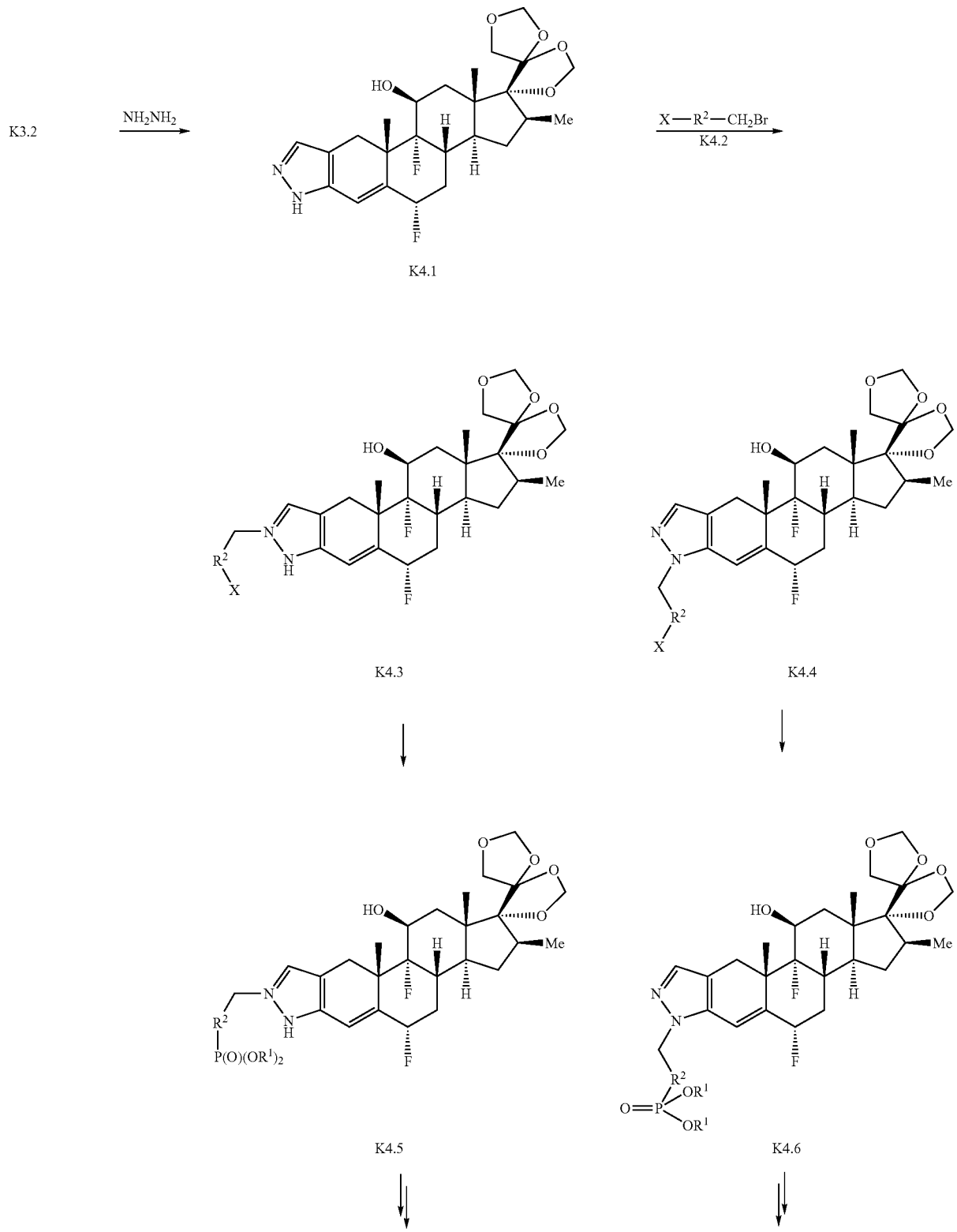
Scheme K4. Phosphonates K3 and K4.

-continued

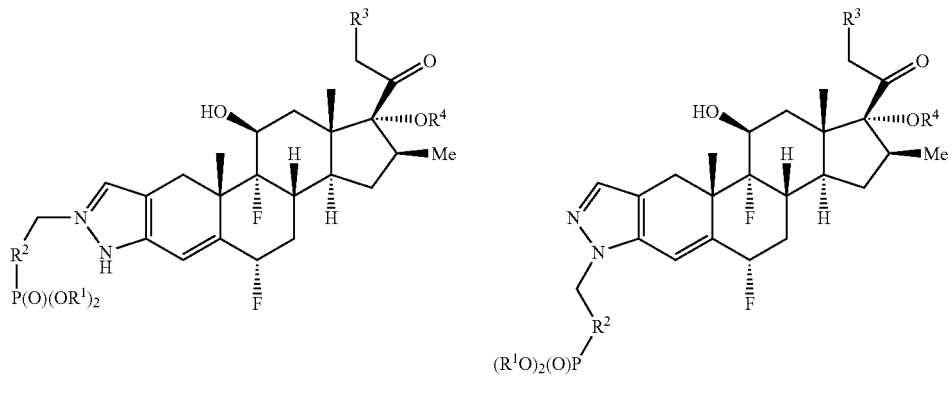

K4.7a: R³ = OH, R⁴ = H
K4.7b: R³ = Cl, R⁴ = COEt

K4.8a: R³ = OH, R⁴ = H
K4.8b: R³ = Cl, R⁴ = COEt

Scheme K4 depicts the preparation of the phosphonate esters K3 and K4 in which the phosphonate group is attached by means of a variable carbon linkage. In this procedure, the ketoaldehyde K3.2 is reacted with hydrazine, to afford the pyrazole derivative K4.1. The reaction of steroidal 2-formyl-3-ketones with hydrazine is described in *J. Am. Chem. Soc,* 86:1520 (1964). The reaction is performed in acetic acid at ambient temperature. The pyrazole product is then reacted with a bromomethyl compound K4.2, in which $R^2$ and X are as defined above, to yield the alkylation products K4.3 and K4.4. The alkylation of substituted pyrazoles is described, for example, in T. L. Gilchrist, Heterocyclic Chemistry, 309 (Longman, 1992). The reaction is performed between equimolar amounts of the substrates in a polar solvent such as dimethylformamide or tetrahydrofuran, in the presence of a base such as dimethylaminopyridine, lithium hexamethyldisilazide and the like. The products K4.3 and K4.4 are, except in cases where X is dialkylphosphono, converted into the phosphonates K4.5 and K4.6, using the procedures described herein, and deprotection/chlorination/acylation then affords the 21-chloro 17-propionate compounds K4.7b and K4.8b.

Scheme K4
Example 89-G

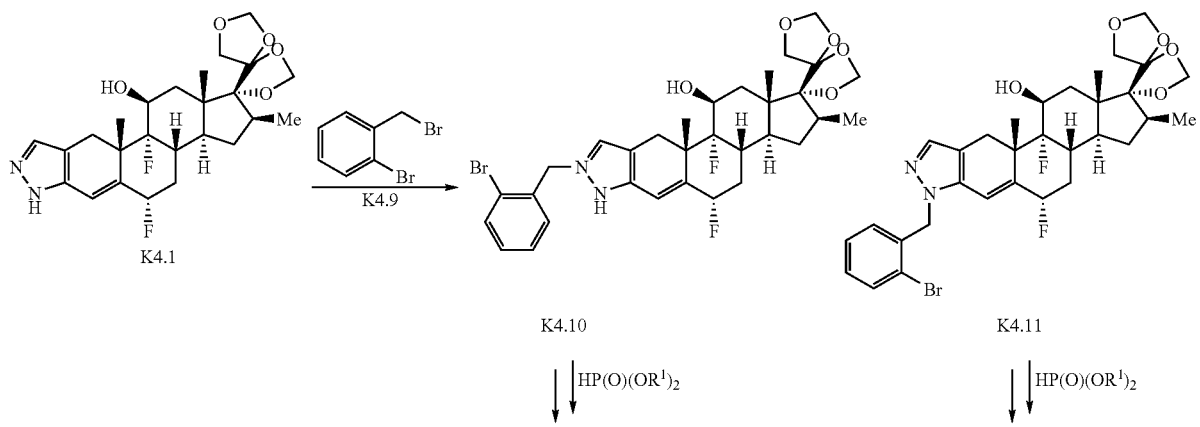

-continued

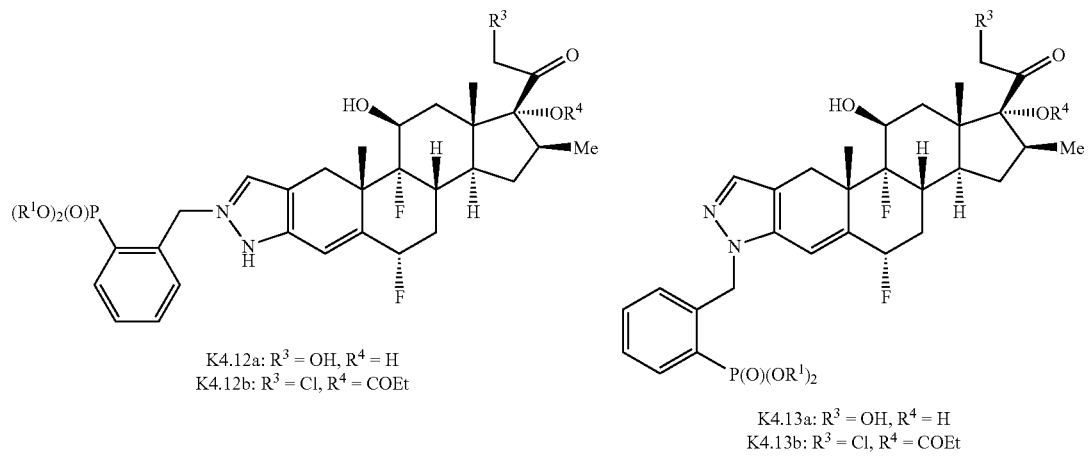

K4.12a: R³ = OH, R⁴ = H
K4.12b: R³ = Cl, R⁴ = COEt

K4.13a: R³ = OH, R⁴ = H
K4.13b: R³ = Cl, R⁴ = COEt

As shown in Scheme K4, Example 89-G, the pyrazole K4.1 is reacted with 2-bromobenzyl bromide K4.9 to give the pyrazoles K4.10 and K4.11. The products are then coupled, as described above, with a dialkyl phosphite, to afford after side-chain deprotection and modification, as described above, the 21-chloro 17 propionates K4.12b and K4.13b.

Scheme K4. Example 89-H

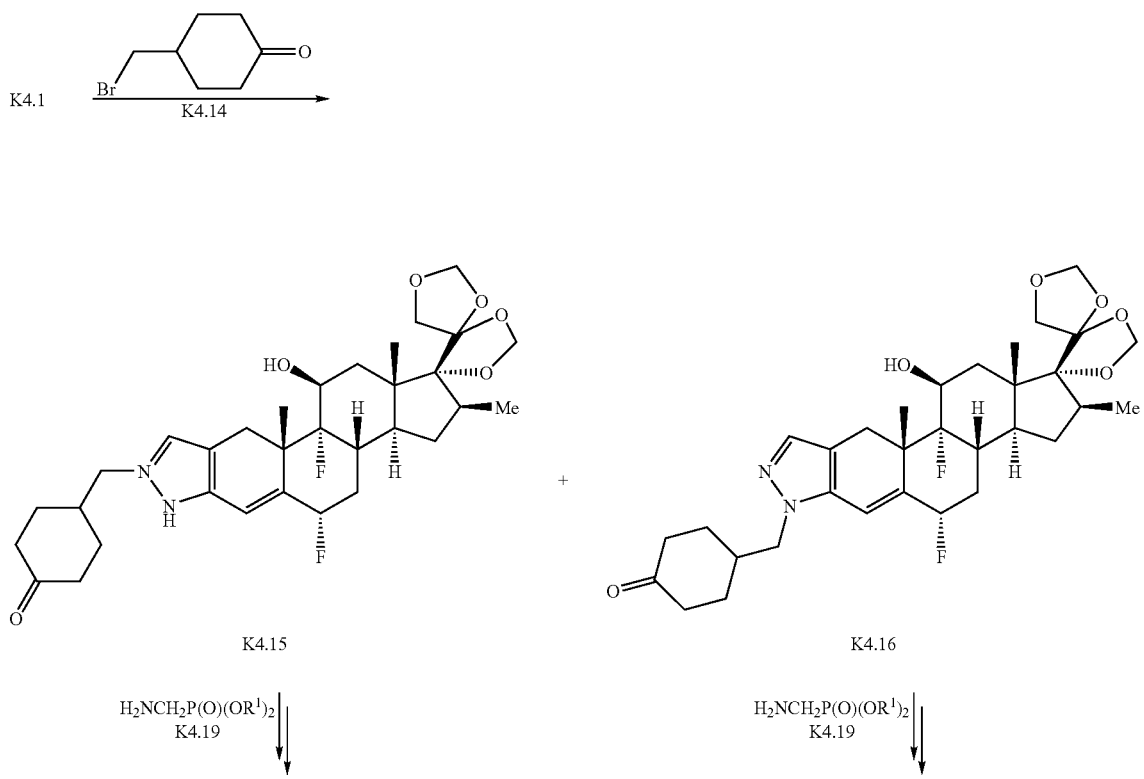

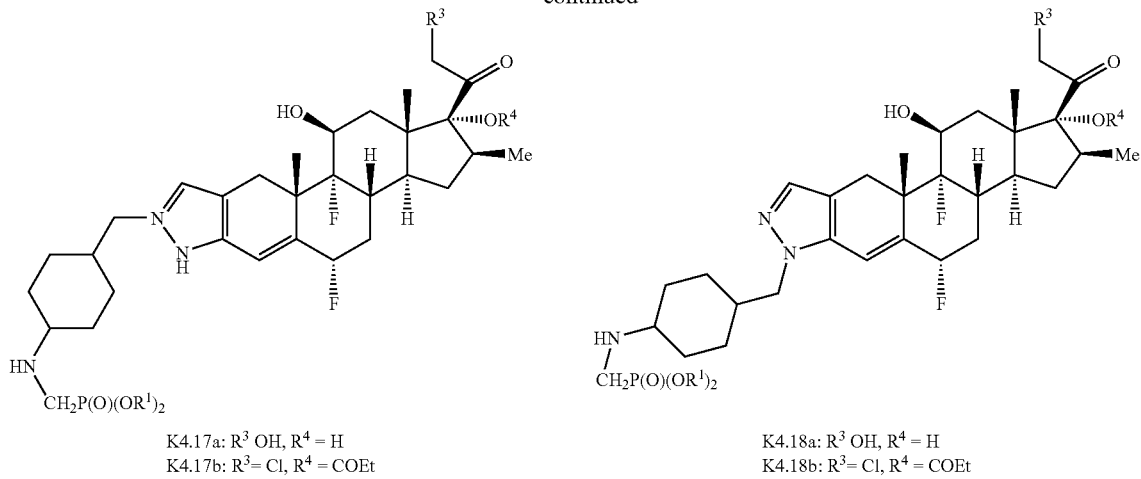

K4.17a: R³ OH, R⁴ = H
K4.17b: R³= Cl, R⁴ = COEt

K4.18a: R³ OH, R⁴ = H
K4.18b: R³= Cl, R⁴ = COEt

As shown in Scheme K4, Example 89-H, the pyrazole K4.1 is reacted in tetrahydrofuran solution, as described above, with 4-bromomethyl cyclohexanone K4.14 (WO 9737959) to give the alkylation products K4.14 and K4.15. The 1'-substituted isomer K4.15 is then reacted, in a reductive amination reaction, with a dialkyl aminomethyl phosphonate K.19 (Interchim) and sodium cyanoborohydride, to yield, after deprotection and side-chain modification, the 21-chloro 17-propionate K4.17b.

The preparation of amines by means of reductive amination procedures is described, for example, in R. C. Larock, Comprehensive Organic Transformations, 421 (VCH, 1989), and in F. A. Carey and R. J. Sundberg, Advanced Organic Chemistry, Part B, 269 (Plenum, 2001). In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in *J. Org. Chem.*, 55:2552 (1990).

The 2'-substituted pyrazole K4.16 is subjected to the same series of reaction to give the amine phosphonate K4.18b.

Using the above procedures, but employing different bromomethyl-substituted aldehydes or ketones, and/or different amino-substituted phosphonates, the products analogous to K4.17b and K4.18b are obtained.

Example 90

Preparation of Exemplary Compounds of the Present Invention

Schemes 1 and 2 illustrate syntheses of phosphonate compounds of this invention, M1 and M2, and of intermediate compounds necessary for their synthesis.

Protection of Reactive Substituents

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in T. W. Greene and P. G. M. Wuts, *Protective Groups in Organic Synthesis* (Second Edition, Wiley, 1991). The protection and deprotection of steroidal ketones is described in J. Fried and J. A. Edwards, *Organic Reactions in Steroid Chemistry*, Vol. 1 375ff (van Nostrand Reinhold, 1972). Reactive substituents which may be protected are shown in the accompanying schemes as, for example, [OH], [O], etc.

Preparation of the Phosphonate Esters M1

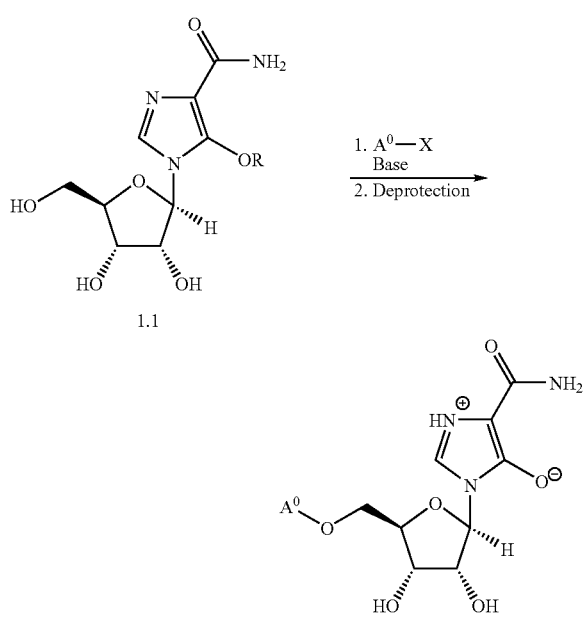

Scheme 1

Scheme 1 depicts the preparation of phosphonates M1 (Compound 1 in Scheme 1). Scheme 1, Example 90-A depicts an example of Scheme 1. In Scheme 1, Example 90-A, the 5-hydroxy-1-β-D-ribofuranosyl-1H-imidazole-4-carboxamide 1.1 (prepared according to U.S. Pat. No. 3,888,843) can be treated in a solvent such as tetrahydrofuran or dimethylformamide with a base such as sodium hydride. When bubbling ceases, diethyl phosphonomethyltriflate (prepared according to *Tetrahedron Lett.*, 1986, 27, 1477) is added, yielding the desired phosphonate diester 1.

Preparation of the Phosphonate Esters M2

Scheme 2 illustrates the preparation of the phosphonate esters M2 (Compound 2 in Scheme 2). Compound 2.1, 5-hydroxy-1-(4-hydroxy-5-hydroxymethyl-tetrahydro-furan-2-ylmethyl)-1H-imidazole-4-carboxylic acid amide can be prepared by addition of the imidazole base (JP Kokai 76 88965) onto the 3,5-bis-protected 2-deoxy-D-erythro-pentofuranosyl chloride (Hayashi, M. et al., *Chem. Pharm. Bull.*, 1975, 23, 1, 245; Montgomery, J. A. et al., *J. Med. Chem.*, 1969, 12, 3, 498; and Iwamoto, R. H. et al., *J. Med. Chem.*, 1963, 6, 684). Compound 2.1 is then protected on the imidazol-4-ol. Oxidation of the 5'-OH followed by elimination provides glycal 2.3 (see the procedure of Zemlicka J. et al., *J. Am. Chem. Soc.*, 1972, 94, 9, 3213). Selenoetherification provides the protected phosphonate 2.4 (Kim, C. et al., *J. Org. Chem.*, 1991, 56, 2642). Oxidative elimination of the phenylselenide (as described in Kim, C. et al., *J. Org. Chem.*, 1991, 56, 2642) followed by stereoselective dihydroxylation provides the diol 2.6. Finally, the protecting group is removed to provide compound 2.

Scheme 2, Example 90-C

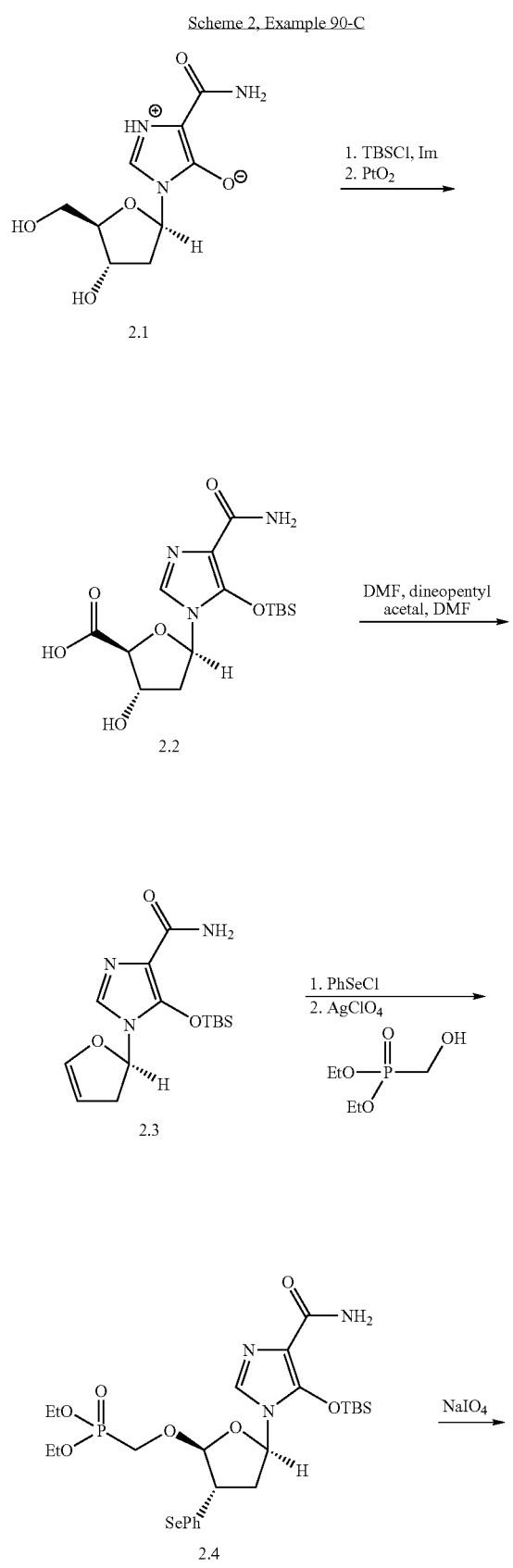

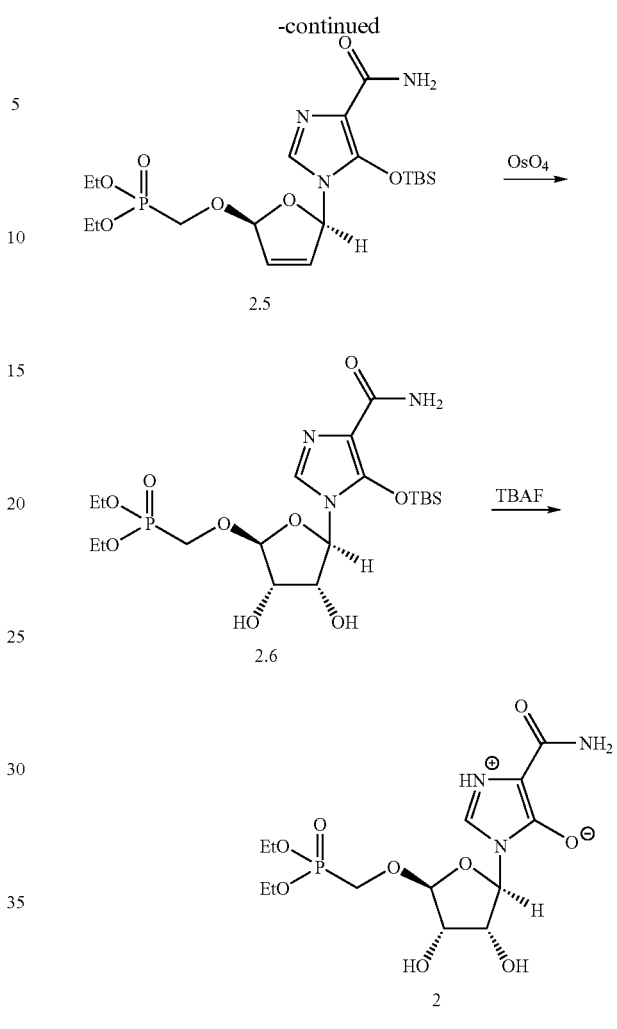

Scheme 2, Example 90-C illustrates the preparation of the phosphonates M2 (Compound 2 in this example). Specifically, compound 2.1, 5-hydroxy-1-(4-hydroxy-5-hydroxymethyl-tetrahydrofuran-2-ylmethyl)-1H-imidazole-4-carboxylic acid amide, which can be prepared by addition of the imidazole base (JP Kokai 76 88965; also Schipper, E. et al., *J. Am. Chem. Soc.*, 1952, 74, 350) onto the 3,5-bis-protected 2-deoxy-D-erythro-pentofuranosyl chloride (Hayashi, M. et al., *Chem. Pharm. Bull.*, 1975, 23, 1, 245; Montgomery, J. A. et al., *J. Med. Chem.*, 1969, 12, 3, 498; and Iwamoto, R. H. et al., *J. Med. Chem.*, 1963, 6, 684) is first protected using a TBS group. Subsequent oxidation with $PtO_2$ proceeds to provide carboxylic acid 2.2. Decarboxylative elimination is achieved using dimethylformamide dineopentyl acetal in DMF at high temperature (Zemlicka J. et al., *J. Am. Chem. Soc.*, 1972, 94, 9, 3213). Once the furanoid glycal 2.3 is in hand, it is treated with silver perchlorate in the presence of diethyl(hydroxylmethyl)phosphonate (Phillion, D. et al., *Tetrahedron Lett.*, 1986, 27, 1477) to provide the phosphonate 2.4 (Kim, C. et al., *J. Org. Chem.*, 1991, 56, 2642). Oxidative elimination of the selenide followed by dihydroxylation using osmium tetraoxide provides a diol with the desired stereochemistry. Deprotection of the TBS group can be achieved using TBAF to provide compound 2.

Example 91
Preparation of Exemplary Compounds of the Present Invention
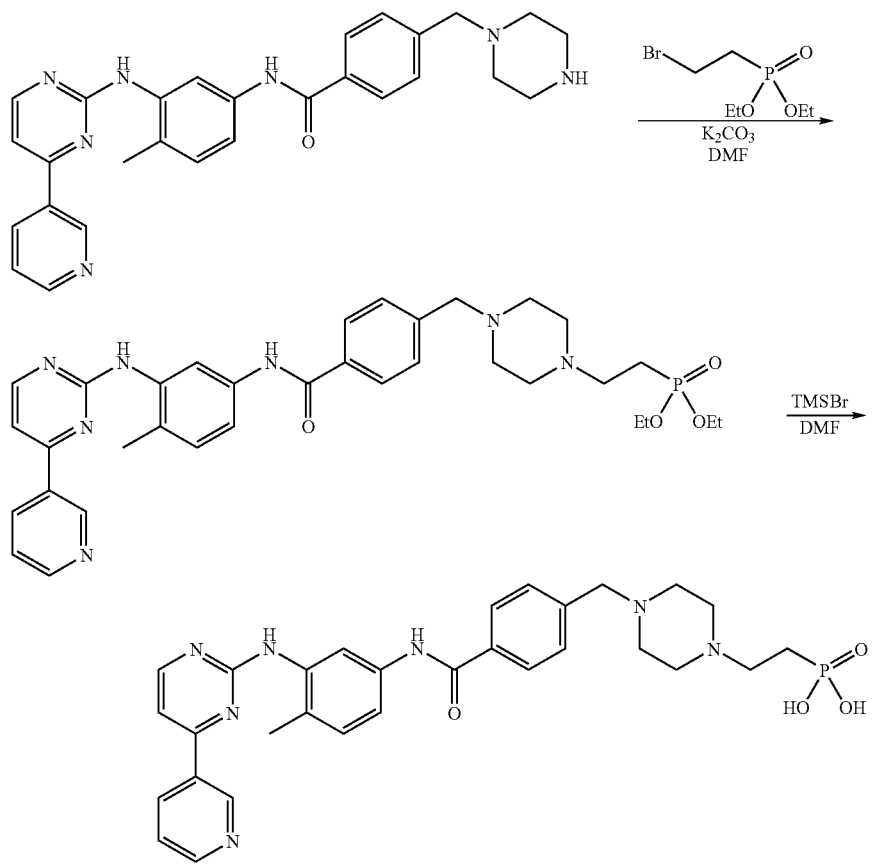
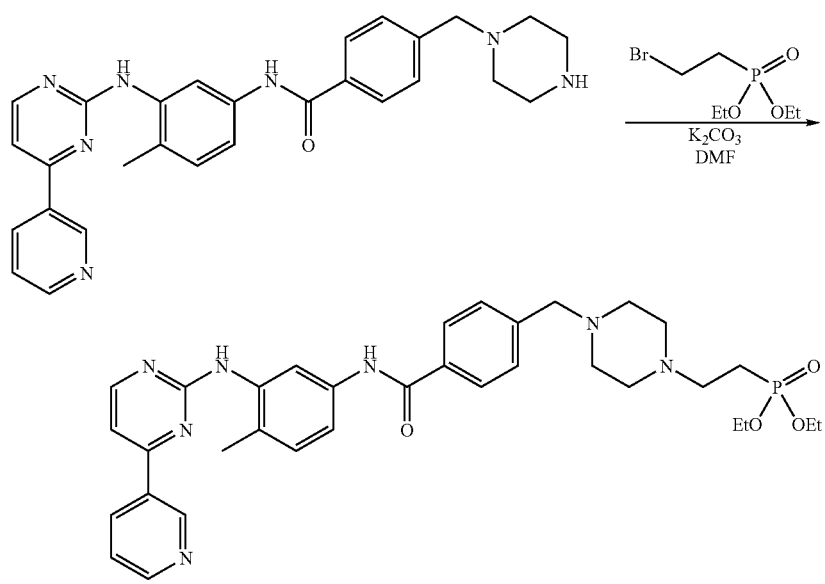
Scheme I

Example 91-A

[2-(4-{4-[4-Methyl-3-(4-pyridin-3-yl-pyrimidin-2-ylamino)-phenylcarbamoyl]-benzyl}-piperazin-1-yl)-ethyl]-phosphonic acid diethyl ester A mixture of N-[4-methyl-3-(4-pyridin-3-yl-pyrimidin-2-ylamino)-phenyl]-4-piperazin-1-ylmethyl-benzamide (30 mg, 0.06 mmol, Zimmermann et al., *Bioorg. Med. Chem. Lett.* 1996, 6, 1221), diethyl 2-bromoethylphosphonate (30 μL, 0.12 mmol) and K$_2$CO3 (20 mg, 0.16 mmol) in 2.5 mL of DMF was heated at 110° C. for 8 hours when most of the starting materials were consumed as judged by LCMS analysis. The solid material was filtered off. The filtrate was diluted with water and then extracted with EtOAc. The organic layer was dried over Na$_2$SO$_4$ and concentrated to dryness. The crude material was purified by silica gel chromatography using 10% MeOH/CH$_2$Cl$_2$ to provide 28 mg (55%) of the desired product. $^1$H NMR (300 MHz, CDCl$_3$) δ 1.32 (t, 6H), 1.92-20.3 (m, 4H), 2.35 (s, 3H), 2.5 (bs, 6H), 2.64 (m, 2H), 3.56 (s, 2H), 4.05-4.14 (m, 4H), 7.07(s, 1H), 7.18 (d, 2H, J=5 Hz), 7.30 (dd, 1H, J=6, 8 Hz), 7.33-7.45 (m, 3H), 7.84 (d, 2H, J=8 Hz), 8.01 (s, 1H), 8.51 (dd, 2H, J=4, 9 Hz), 8.58 (d, 1H, J=2 Hz), 8.70 (dd, 1H, J=2, 5 Hz), 9.25 (s, 1H); $^{31}$P (121.4 MHz, CDCl$_3$) δ 30.5; MS (m/z) 644 [M+H]$^+$.

Example 91-B

[2-(4-{4-[4-Methyl-3-(4-pyridin-3-yl-pyrimidin-2-ylamino)-phenylcarbamoyl]-benzyl}-piperazin-1-yl)-ethyl]-phosphonic acid To a solution of [2-(4-{4-[4-methyl-3-(4-pyridin-3-yl-pyrimidin-2-ylamino)-phenylcarbamoyl]-benzyl}-piperazin-1-yl)-ethyl]-phosphonic acid diethyl ester (8 mg, 0.012 mmol) in DMF (1 mL) was added TMSBr (15 μL, 0.12 mmol) at room temperature. The reaction was allowed to proceed at room temperature for 14 hours. Another portion of TMSBr (20 μL) was added and heated at 110° C. for 12 hours when completion of the reaction was detected by LCMS. The reaction was cooled down to room temperature and quenched with addition of MeOH. The reaction mixture was dried under reduced pressure and the residue was purified by RP HPLC using a C18 column with a gradient of H$_2$O—Acetonitrile (5-100%) over 20 minutes to provide 4.2 mg (50%) of the product as mono-TFA salt. $^1$H NMR (300 MHz, CD$_3$OD) δ 1.80-1.84 (m, 2H), 2.08-2.02 (m, 2H), 2.23 (s, 3H), 3.07 (bs, 4H), 3.30-3.32 (2H, possible overlap with solvent), 3.89 (m, 2H), 4.01 (s, 2H), 6.87 (s, 1H), 7.23-7.3 (m, 3H), 7.52-7.60 (m, 3H), 8.01 (d, 2H, J=8 Hz), 8.08 (dd, 1H, J=2, 5 Hz), 8.30 (s, 1H), 8.58 (d, 1H, J=5 Hz), 8.89 (d, 1H, J=2 Hz), 9.22 (dd, 1H, J=2, 5 Hz), 9.63 (s, 1H); $^{31}$P (121.4 MHz, CD$_3$OD) δ 21.9; MS (m/z) 588 [M+H]$^+$.

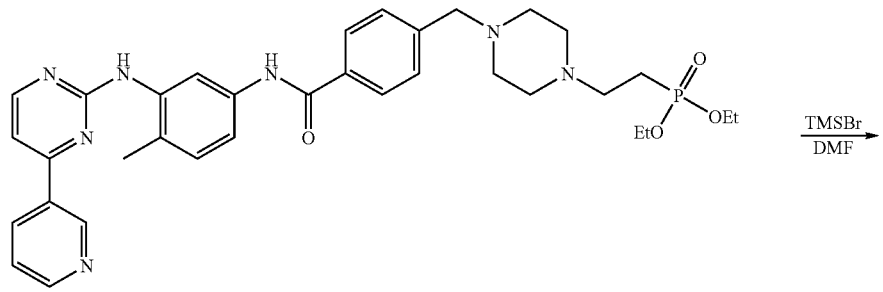

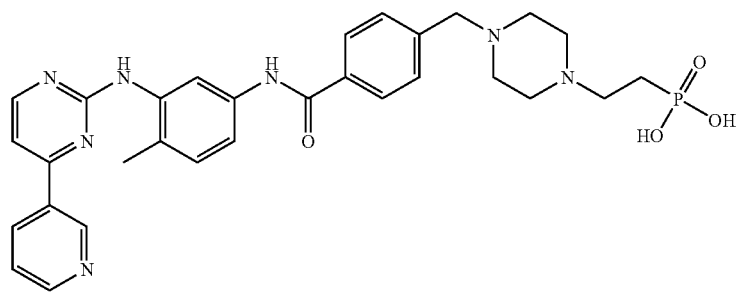

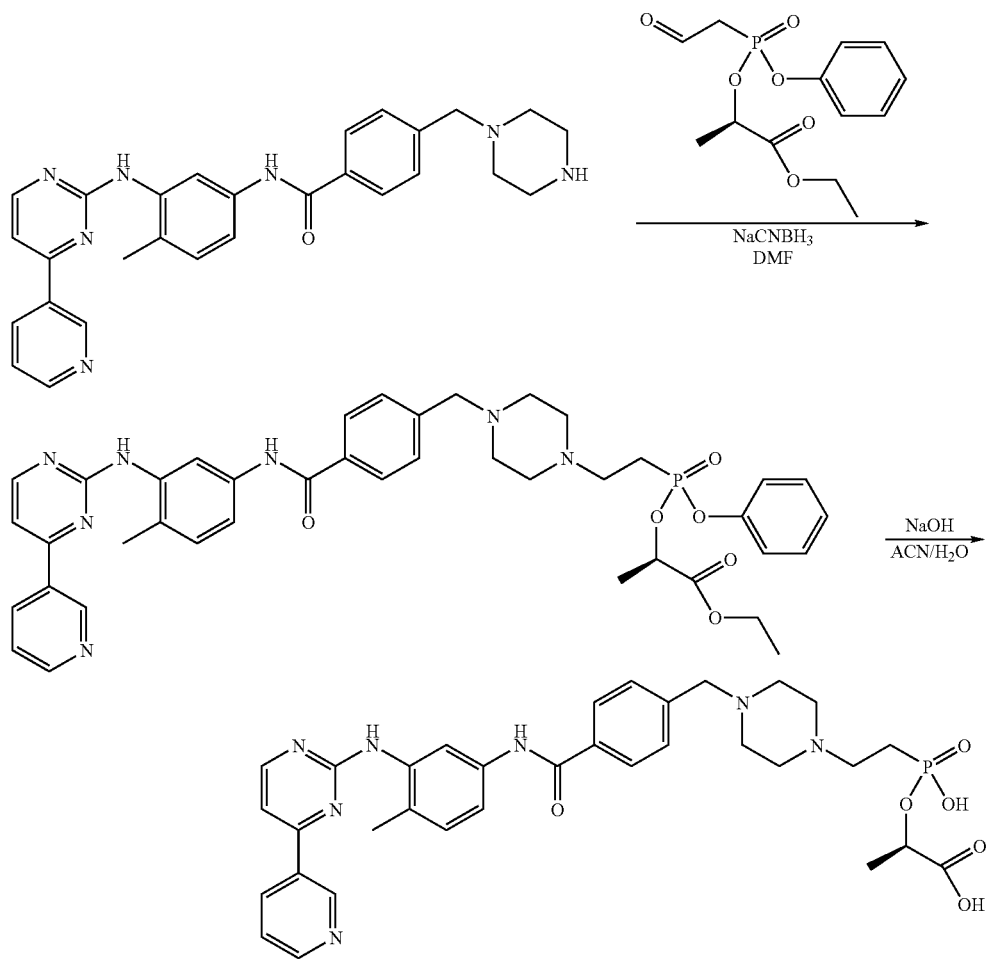
Scheme II
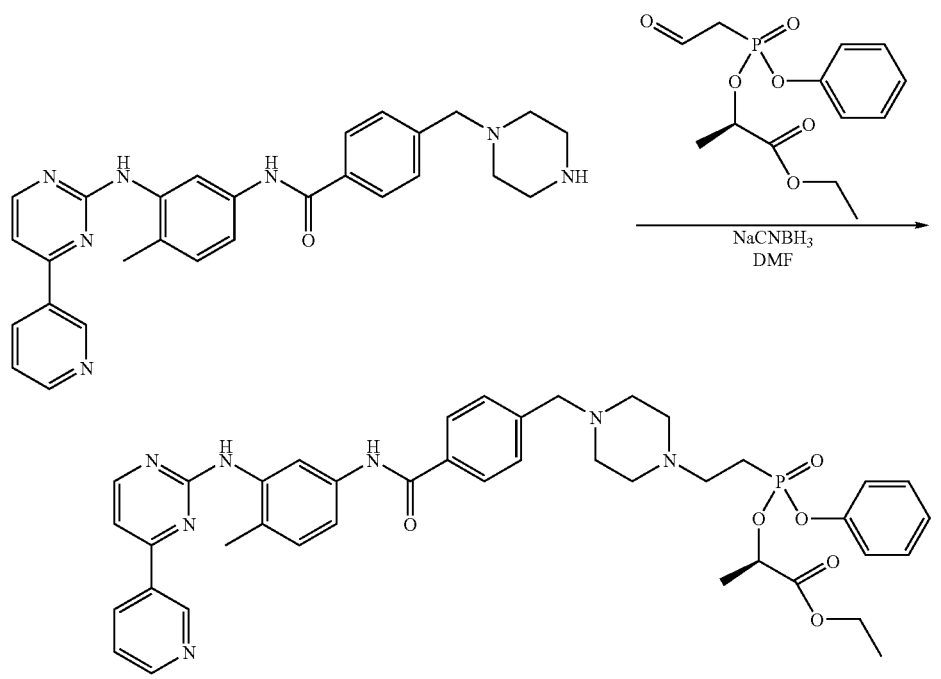

Example 91-C

2-{[2-(4-{4-[4-Methyl-3-(4-pyridin-3-yl-pyrimidin-2-ylamino)-phenylcarbamoyl]-benzyl}-piperazin-1-yl)-ethyl]-phenoxy-phosphinoyloxy}-propionic acid ethyl ester A solution of N-[4-methyl-3-(4-pyridin-3-yl-pyrimidin-2-ylamino)-phenyl]-4-piperazin-1-ylmethyl-benzamide (20 mg, 0.04 mmol) and 2-[(2-oxo-ethyl)-phenoxy-phosphinoyloxy]-propionic acid ethyl ester (60 mg, 0.2 mmol) in 1% Acetic Acid/DMF (1.5 mL) solution was stirred at room temperature for 7 hours followed by an addition of NaCNBH$_3$ (30 mg, 0.24 mmol). The resulting mixture was stirred for additional 30 min when completion of the reaction was observed by LCMS. After evaporation of solvent, the residue was taken up in CH$_2$Cl$_2$ and then extracted with saturated aqueous NaHCO$_3$ The organic extracts were dried in vacuo and the residue was purified by silica gel chromatography using MeOH—CH$_2$Cl$_2$ (7%) to afford 8 mg (26%) of the product. $^{31}$P NMR (121.4 MHz, CDCl$_3$) δ 27.2, 28.6; MS (m/z) 764 [M+H]$^+$.

Example 91-D

2-{Hydroxy-[2-(4-{4-[4-methyl-3-(4-pyridin-3-yl-pyrimidin-2-ylamino)-phenylcarbamoyl]-benzyl}-piperazin-1-yl)-ethyl]-phosphinoyloxy}-propionic acid To a solution of 2-{[2-(4-{4-[4-methyl-3-(4-pyridin-3-yl-pyrimidin-2-ylamino)-phenylcarbamoyl]-benzyl}-piperazin-1-yl)-ethyl]-phenoxy-phosphinoyloxy}-propionic acid ethyl ester (6 mg, 0.008 mmol) in 2:1 acetonitrile/water (0.3 mL) was added 1N NaOH (50 µL, 0.048 mmol). The solution was allowed to stir at room temperature for 1 hour when completion of the reaction was observed by LCMS. The reaction was acidified by 1N HCl (50 µL) solution and purified by RP HPLC using a C18 column with a gradient of H$_2$O—Acetonitrile (5-100%) over 20 minutes to provide 2 mg (38%) of the product. $^1$H NMR (300 MHz, CD$_3$OD) δ 1.51 (d, 3H, J=7 Hz), 2.04 (m, 2H), 2.33 (s, 3H), 2.96 (bs, 4H), 3.31 (m, 2H), 3.4 (bs, 4H), 3.89 (s, 2H), 4.88 (1H, possible overlap with solvent), 7.30 (m, 2H), 7.48-7.57 (m, 4H), 7.96-7.99 (m, 4H), 8.32 (s, 1H), 8.56 (d, 1H, J=5 Hz), 8.86 (d, 1H, J=2 Hz), 9.10 (dd, 1H, J=2, 5 Hz), 9.59 (s, 1H); $^{31}$P (121.4 MHz, CD$_3$OD) δ 20.0; MS (m/z) 660 [M+H]$^+$.

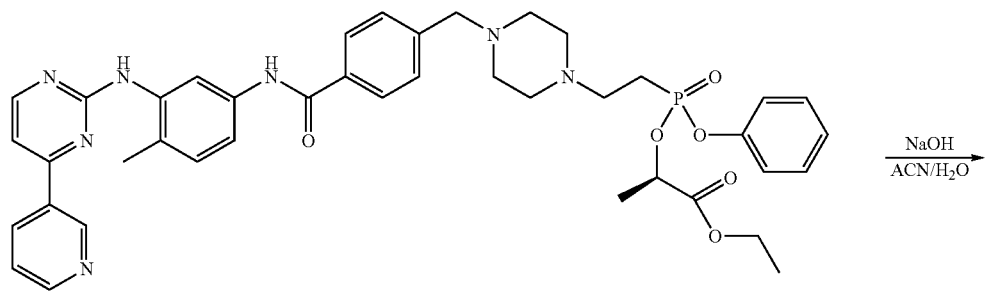

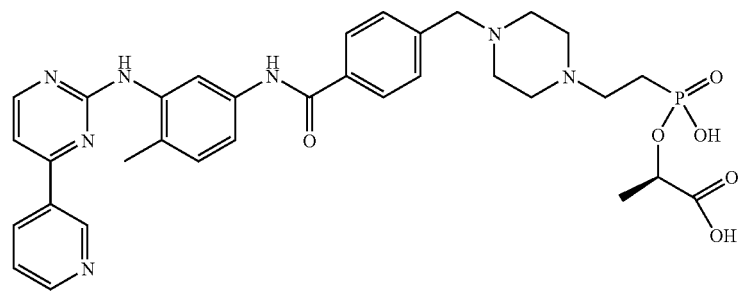

863
Example 92
Preparation of Exemplary Compounds of the Present Invention
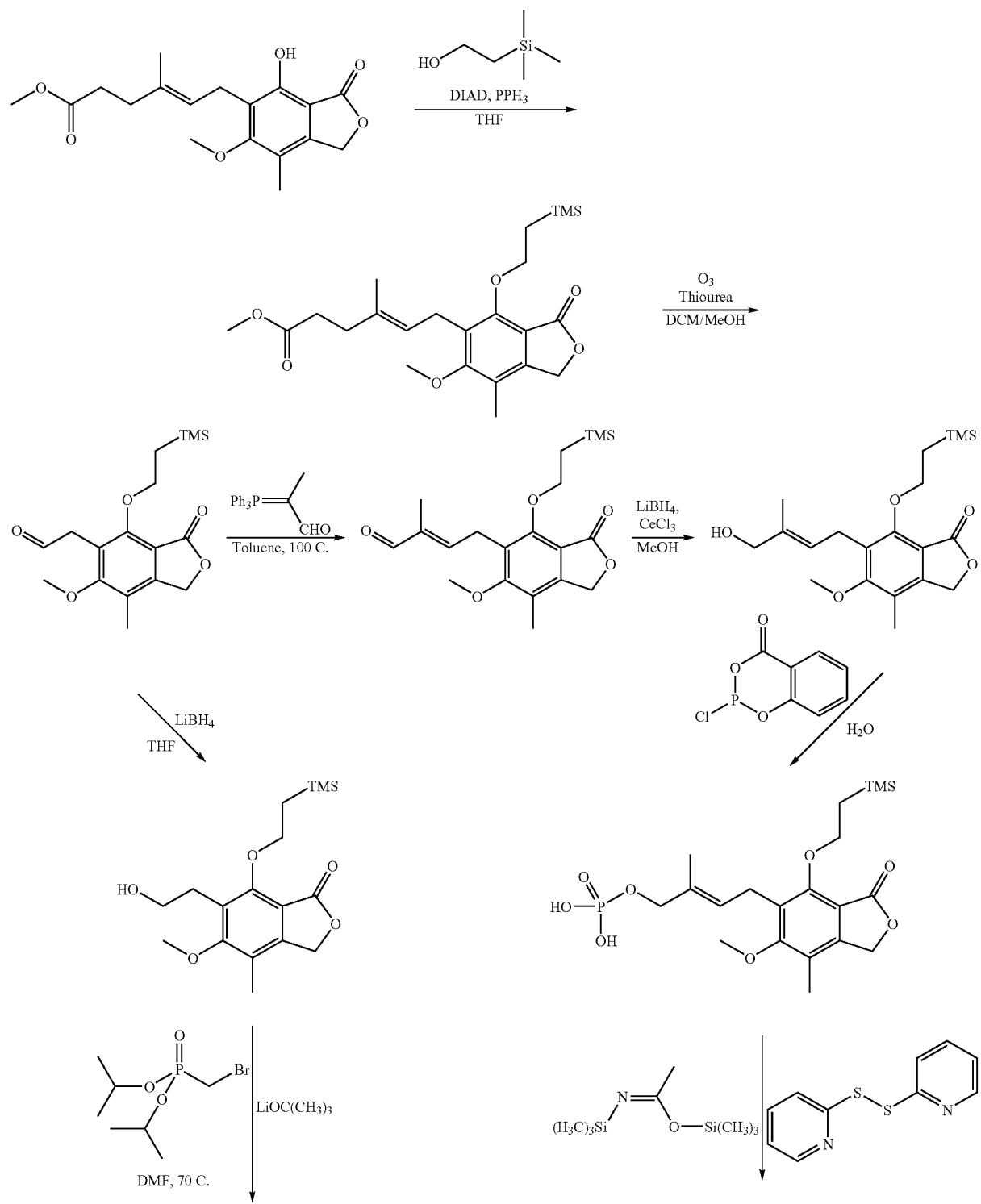

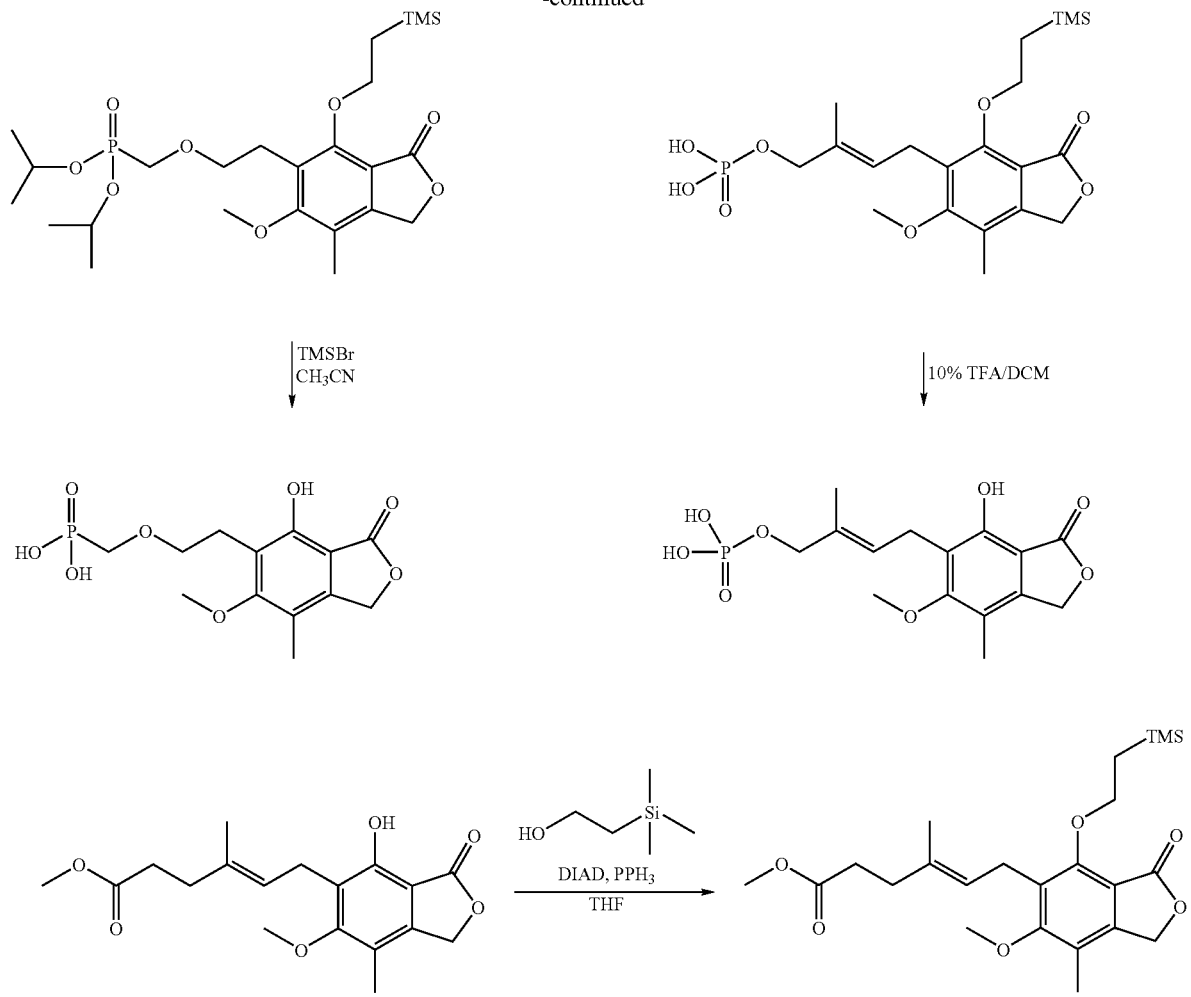

Example 92-A

6-[6-Methoxy-7-methyl-3-oxo-4-(2-trimethylsilanyl-ethoxy)-1,3-dihydro-isobenzofuran-5-yl]-4-methyl-hex-4-enoic acid methyl ester To a solution of 6-(4-hydroxy-6-methoxy-7-methyl-3-oxo-1,3-dihydro-isobenzofuran-5-yl)-4-methyl-hex-4-enoic acid methyl ester (222 mg, 0.66 mmol), PPh$_3$ (260 mg, 0.996 mmol), and diethyl azodicarboxylate (173 mg, 0.996 mmol) in THF (3 mL) at 0° C. was added a solution of trimethylsilyl ethanol (142 μL, 0.996 mmol) in THF (3 mL). The resulting yellow solution was allowed to warm up to room temperature and stirred overnight. The reaction was worked up by concentrating the solution to dryness and addition of ether and hexanes. Triphenylphosphine oxide was removed by filtration and the filtrate was concentrated and purified by silica gel chromatography to provide 248 mg of the desired product as a clear oil. $^1$H NMR (300 MHz, CDCl$_3$) δ 0.03 (s, 9H), 1.18-1.30 (m, 2H), 1.81 (s, 3H), 2.18 (s, 3H), 2.25-2.33 (m, 2H), 2.37-2.45 (m, 2H), 3.42 (d, 2H, J=7 Hz), 3.62 (s, 3H), 3.77 (s, 3H), 4.25-4.35 (m, 2H), 5.13 (s, 2H), 5.12-5.22 (m, 1H).

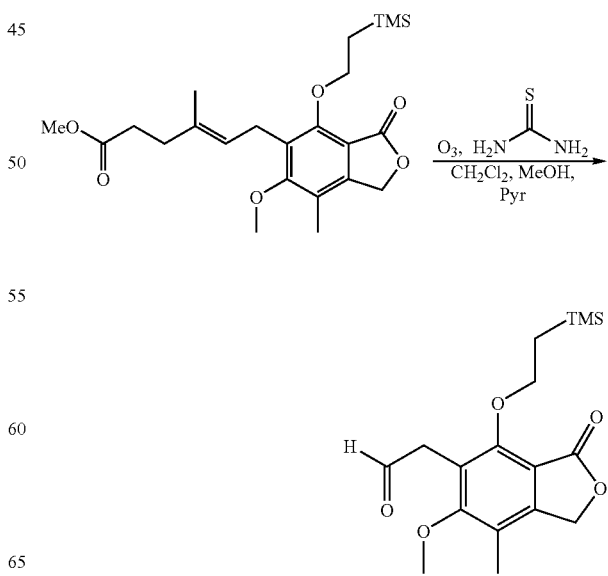

Example 92-B

[6-Methoxy-7-methyl-3-oxo-4-(2-trimethylsilanyl-ethoxy)-1,3-dihydro-isobenzofuran-5-yl]-acetaldehyde A solution of 6-[6-methoxy-7-methyl-3-oxo-4-(2-trimethylsilanyl-ethoxy)-1,3-dihydro-isobenzofuran-5-yl]-4-methyl-hex-4-enoic acid methyl ester (618 mg, 1.42 mmol) in MeOH (10 mL), $CH_2Cl_2$ (10 mL) and pyridine (50 µL, 0.618 mmol) was cooled to −70° C. using a dry ice/acetone bath according to the procedure of Smith, D. B. et al., *J. Org. Chem.*, 1996, 61, 6, 2236. A stream of ozone was bubbled through the reaction via a gas dispersion tube until the reaction became blue in color (15 minutes). The ozone line was replaced with a stream of nitrogen and bubbling continued for another 15 minutes when the blue color disappeared. To this solution at −70° C. was added thiourea (75.7 mg, 0.994 mmol) in one portion, and the cooling bath was removed. The reaction was allowed to warm to room temperature and stirred for 15 hours. The reaction was worked up by filtration to remove solid thiourea S-dioxide, and then partitioned between $CH_2Cl_2$ and water. The organic layer was removed. The aqueous layer was washed with $CH_2Cl_2$ one more time and the organic extracts were combined. The organic layer was washed with aqueous 1N HCl, saturated $NaHCO_3$ and brine. The organic extracts were dried in vacuo and the residue was purified to by silica gel chromatography to afford 357 mg (75%) of the product as a white solid. $^1$H NMR (300 MHz, $CDCl_3$) δ −0.01 (s, 9H), 1.05-1.15 (m, 2H), 2.15 (s, 3H), 3.69 (s, 3H), 3.78 (d, 2H, J=1 Hz), 4.27-4.39 (m, 2H), 5.11 (s, 2H), 9.72 (d, 1H, J=1 Hz).

Example 92-C

4-[6-Methoxy-7-methyl-3-oxo-4-(2-trimethylsilanyl-ethoxy)-1,3-dihydro-isobenzofuran-5-yl]-2-methyl-but-2-enal

[6-Methoxy-7-methyl-3-oxo-4-(2-trimethylsilanyl-ethoxy)-1,3-dihydro-isobenzofuran-5-yl]-acetaldehyde (70 mg, 0.21 mmol) in toluene (2 mL) was heated at 100° C. with 2-(triphenylphosphanylidene)-propionaldehyde (72.9 mg, 0.23 mmol) overnight. A second portion of 2-(triphenyl-phosphanylidene)-propionaldehyde (33 mg, 0.11 mmol) was added and the reaction mixture was heated for an additional day. After concentration, the residue was purified by silica gel chromatography to provide 54 mg (83%) of the desired product as a pale yellow oil. $^1$H NMR (300 MHz, $CDCl_3$) δ 0.00 (s, 9H), 1.10-1.21 (m, 2H), 1.87 (s, 3H), 2.16 (s, 3H), 3.67-3.76 (m, 2H), 3.74 (s, 3H), 4.27-4.39 (m, 2H), 5.11 (s, 2H), 6.40-6.48 (m, 1H), 9.2 (s, 1H).

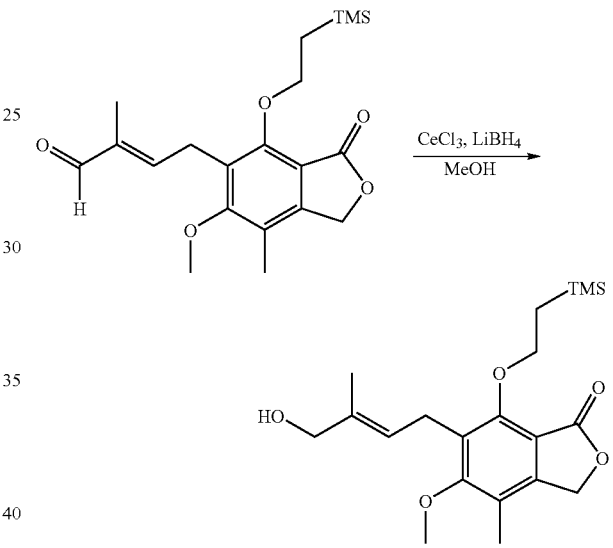

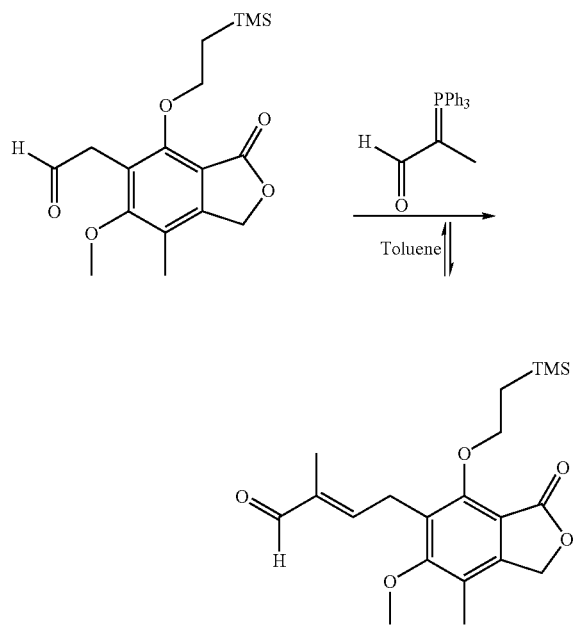

Example 92-D 6-(4-Hydroxy-3-methyl-but-2-enyl)-5-methoxy-4-methyl-7-(2-trimethylsilanyl-ethoxy)-3H-isobenzofuran-1-one A solution of 4-[6-methoxy-7-methyl-3-oxo-4-(2-trimethylsilanyl-ethoxy)-1,3-dihydro-isobenzofuran-5-yl]-2-methyl-but-2-enal (103 mg, 0.27 mmol) in methanol (5 mL) was cooled to 0° C. A solution of $CeCl_3$ (0.68 mL, MeOH: $H_2O$, 9:1) was added, followed by $LiBH_4$ (0.14 mL, 0.28 mmol of a 2M solution in THF). The ice bath was removed and the reaction mixture was allowed to warm to room temperature. The reaction mixture was stirred for an additional 40 minutes whereupon TLC indicated complete consumption of starting aldehyde. The reaction was worked up by addition of aqueous 1N HCl (0.5 mL) and the product was extracted with $CH_2Cl_2$. The organic layer was washed with saturated aqueous sodium bicarbonate solution and brine. The organic layer was concentrated under reduced pressure and the residue was purified by silica gel chromatography to provide 100 mg (97%) of the product as a clear liquid. $^1$H NMR (300 MHz, $CDCl_3$) δ 0.00 (s, 9H), 1.20 (dd, 2H, J=7, 8 Hz), 1.81 (s, 3H), 2.13 (s, 3H), 3.38-3.50 (m, 2H), 3.74 (s, 3H), 3.95 (s, 2H), 4.27 (dd, 2H, J=7, 8 Hz), 5.08 (s, 2H), 5.17-5.44 (m, 1H).

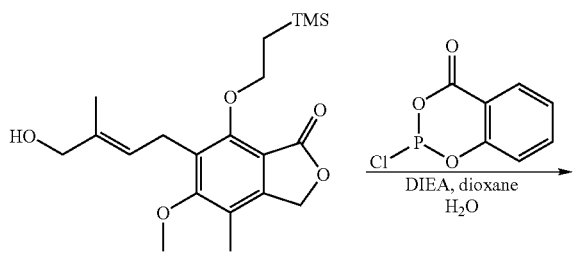

1989, 45, 12, 3889. After 10 minutes, another portion of 2-chloro-4H-1,3,2-benzodioxaphosphorin-4-one (40 mg, 0.20 mmol) and DIEA (35 μL, 0.20 mmol) were added. The reaction was allowed to proceed at room temperature for an additional hour, after which it was quenched by the addition of H$_2$O. The solution was stirred for another 10 minutes and concentrated in vacuo to a small volume. The product was triturated with diethyl ether and coevaporated from acetonitrile (4×10 mL) to provide the product. $^1$H NMR (300 MHz, CDCl$_3$) δ 0.03 (s, 9H), 1.08-1.30 (m, 2H), 1.84 (br s, 3H), 2.17 (s, 3H), 3.46 (br s, 2H), 3.76 (s, 3H), 4.21-4.39 (m, 4H), 5.12 (s, 2H), 5.43-5.60 (m, 1H), 7.83 (br s, 1H); $^{31}$P (121.4 MHz, CDCl$_3$) δ 7.22; MS (m/z) 441 [M−H]$^-$.

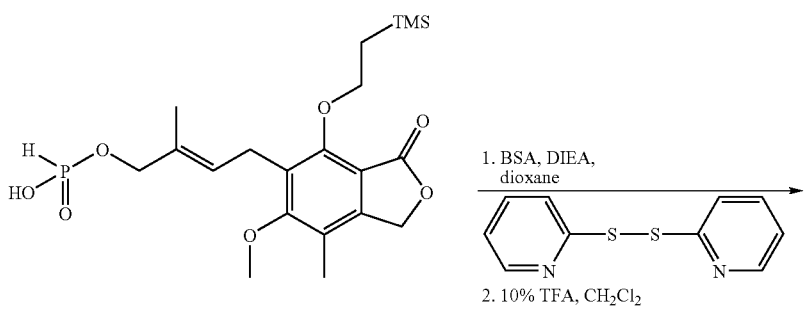

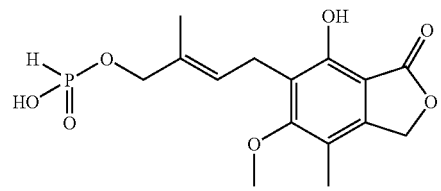

Example 92-F

Phosphoric acid mono-{4-[6-methoxy-7-methyl-3-oxo-4-(2-trimethylsilanyl-ethoxy)-1,3-dihydro-isobenzofuran-5-yl]-2-methyl-but-2-enyl}ester A solution of phosphorous acid mono-{4-[6-methoxy-7-methyl-3-oxo-4-(2-trimethylsilanyl-ethoxy)-1,3-dihydro-isobenzofuran-5-yl]-2-methyl-but-2-enyl}ester (27 mg, 0.06 mmol) in dioxane (1 mL) was stirred with DIEA (21 μL, 0.12 mmol) and N,O-bis(trimethylsilyl)acetamide (29 μL, 0.12 mmol) at room temperature for 3 hours. To the reaction solution was added 2,2'-dipyridyldisulfide (16 mg, 0.072 mmol) and the mixture was allowed to stir for an additional 2 hours at room temperature. The reaction mixture was diluted by addition of H$_2$O and the solution was stirred for 2 more hours when it was concentrated. The residue was dissolved in a solution of 10% TFA/CH$_2$Cl$_2$ and stirred at room temperature for 9 hours. The reaction mixture was dried under reduced pressure and the product was purified by reverse-phase HPLC to provide the desired product as a white solid. $^1$H NMR (300 MHz, CD$_3$OD) δ 1.87 (s, 3H), 2.16 (s, 3H), 3.47 (d, 2H, J=7 Hz), 3.79 (s, 3H), 4.28 (d, 2H, J=6 Hz), 5.26 (s, 2H), 5.50-5.61 (m, 1H); $^{31}$P (121.4 MHz, CD$_3$OD) δ 0.50; MS (m/z) 357 [M−H]$^-$.

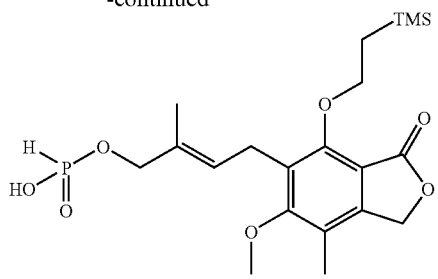

Example 92-E

Phosphorous acid mono-{4-[6-methoxy-7-methyl-3-oxo-4-(2-trimethylsilanyl-ethoxy)-1,3-dihydro-isobenzofuran-5-yl]-2-methyl-but-2-enyl}ester To a solution of 6-(4-hydroxy-3-methyl-but-2-enyl)-5-methoxy-4-methyl-7-(2-trimethylsilanyl-ethoxy)-3H-isobenzofuran-1-one (75 mg, 0.20 mmol) and DIEA (49 μL, 0.28 mmol) in dioxane (2 mL) was added 2-chloro-4H-1,3, 2-benzodioxaphosphorin-4-one (56.7 mg, 0.28 mmol) according the procedure of Shadid, B. et al., *Tetrahedron*,

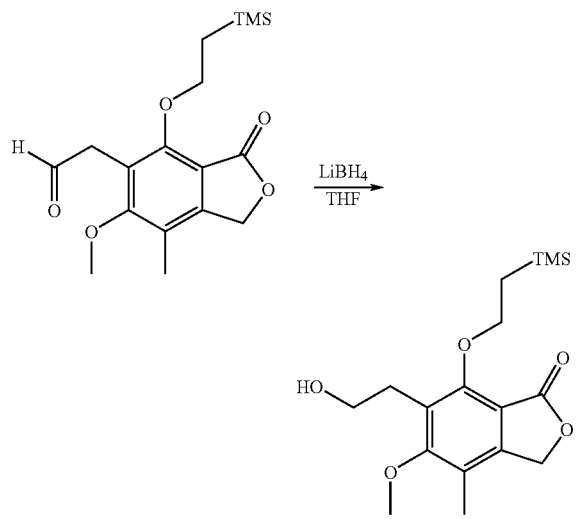

Example 92-G 6-(2-Hydroxy-ethyl)-5-methoxy-4-methyl-7-(2-trimethylsilanyl-ethoxy)-3H-isobenzofuran-1-one To a solution of [6-methoxy-7-methyl-3-oxo-4-(2-trimethylsilanyl-ethoxy)-1,3-dihydro-isobenzofuran-5-yl]-acetaldehyde (97 mg, 0.29 mmol) in THF (5 mL) was added an aliquot of a 2 M LiBH$_4$ in THF (150 μL, 0.300 mmol). The reaction mixture was stirred at room temperature for 1 hour when complete consumption of the starting materials was observed by TLC. The reaction mixture was worked up by addition of an aqueous 1N HCl solution and extraction with EtOAc. The organic layer was dried in vacuo and the residue was purified by silica gel chromatography to provide the product. $^1$H NMR (300 MHz, CDCl$_3$) δ 0.00 (s, 9H), 1.20 (dd, 2H, J=7, 9 Hz), 2.07 (br s, 1H), 2.14 (s, 3H), 2.97 (t, 2H, J=6 Hz), 3.76 (t, 2H, J=6 Hz), 3.77 (s, 3H), 4.32 (dd, 2H, J=7, 8 Hz), 5.08 (s, 2H).

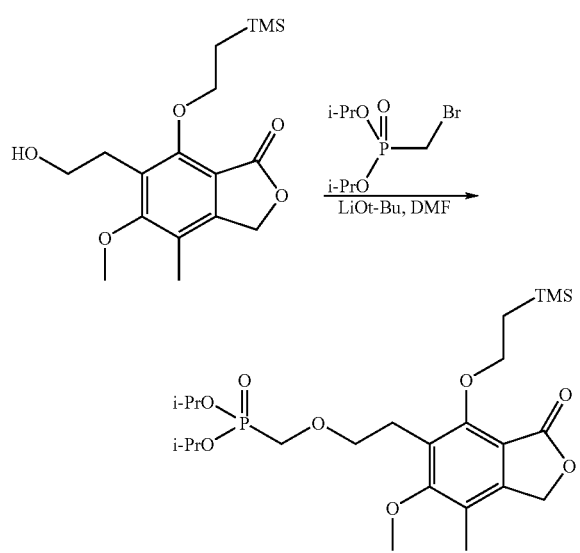

Example 92-H

{2-[6-Methoxy-7-methyl-3-oxo-4-(2-trimethylsilanyl-ethoxy)-1,3-dihydro-isobenzofuran-5-yl]-ethoxymethyl}-phosphonic acid diisopropyl ester A mixture of 6-(2-hydroxy-ethyl)-5-methoxy-4-methyl-7-(2-trimethylsilanyl-ethoxy)-3H-isobenzofuran-1-one (79 mg, 0.23 mmol) was heated with bromomethylphosphonic acid diisopropyl ester (120 mg, 0.46 mmol) in the presence of lithium t-butoxide (22 mg, 0.27 mmol) in DMF (2 mL) at 70° C. overnight. The reaction mixture was purified by reverse-phase HPLC to provide the desired product. $^1$H NMR (300 MHz, CDCl$_3$) δ 0.00 (s, 9H), 1.13-1.25 (m, 2H), 1.26 (t, 12H, J=6 Hz), 2.12 (s, 3H), 2.98 (t, 2H, J=7 Hz), 3.60-3.73 (m, 4H), 3.77 (s, 3H), 4.05-4.16 (m, 2H), 4.62-4.74 (m, 2H), 5.07 (s, 2H); MS (m/z) 539 [M+Na]$^+$.

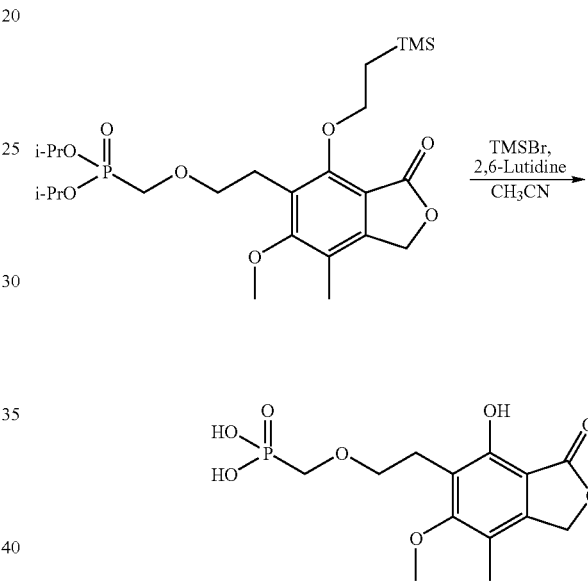

Example 92-I

[2-(4-Hydroxy-6-methoxy-7-methyl-3-oxo-1,3-dihydro-isobenzofuran-5-yl)-ethoxymethyl]-phosphonic acid To a solution of {2-[6-methoxy-7-methyl-3-oxo-4-(2-trimethylsilanyl-ethoxy)-1,3-dihydro-isobenzofuran-5-yl]-ethoxymethyl}-phosphonic acid diisopropyl ester (7.5 mg, 0.014 mmol) in acetonitrile (2 mL) and 2,6-lutidine (25 μL, 0.21 mmol) was added trimethylsilyl bromide (27 μL, 0.21 mmol) at room temperature. The reaction was allowed to proceed for 18 hours when completion of the reaction was indicated by LCMS. The reaction was quenched by addition of MeOH and concentration. The residue was purified by reverse-phase HPLC using a C18 column. The collected product was dispensed in a solution of 10% TFA/CH$_2$Cl$_2$ to assure complete cleavage of the TMSE group. The reaction mixture was lyophilized to provide the desired product. $^1$H NMR (300 MHz, CD$_3$OD) δ 2.12 (s, 3H), 2.98 (t, 2H, J=7 Hz), 3.66-3.76 (m, 4H), 3.78 (s, 3H), 5.21 (s, 2H); MS (m/z) 331 [M−H]$^-$.

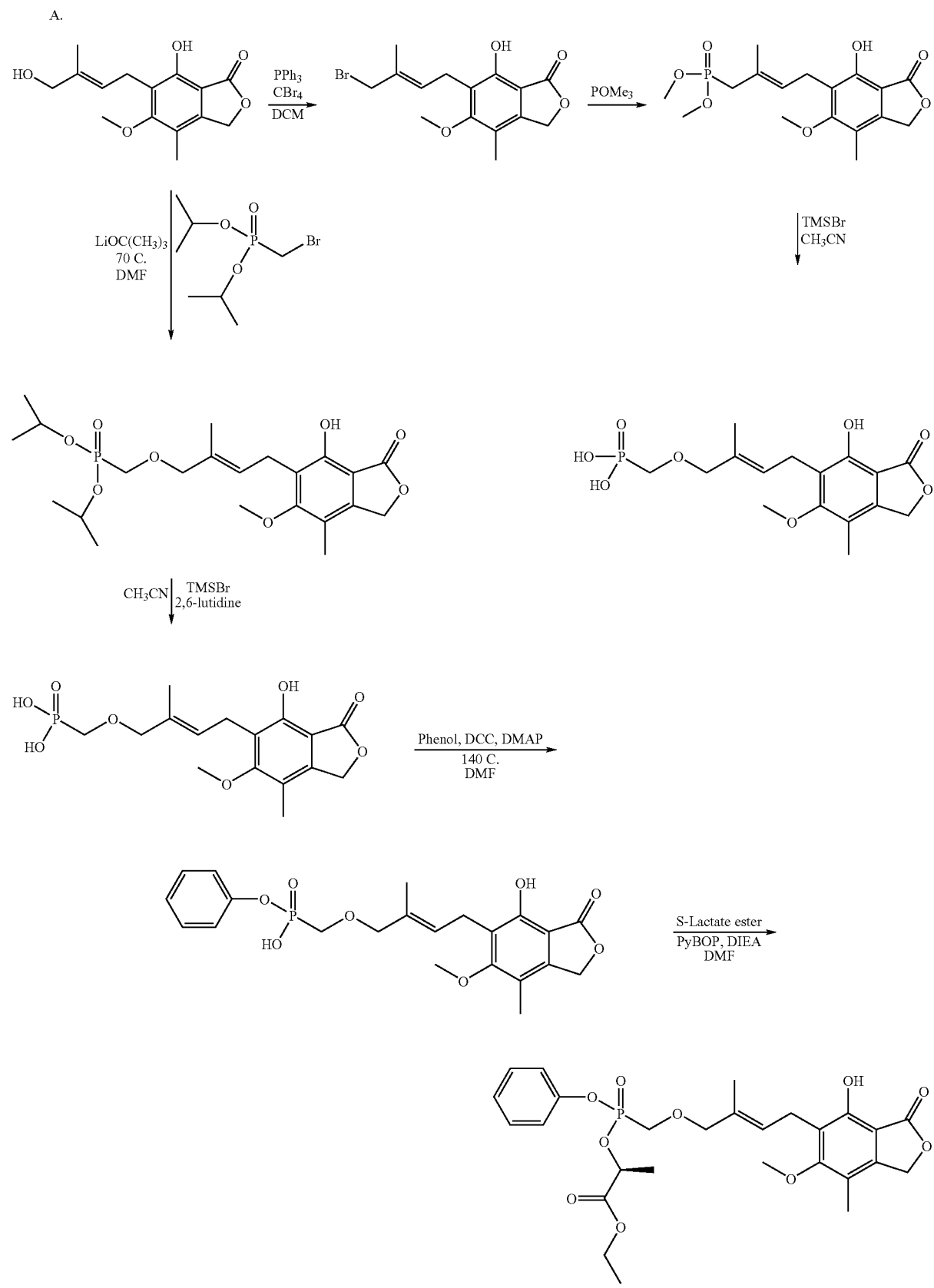
Scheme II

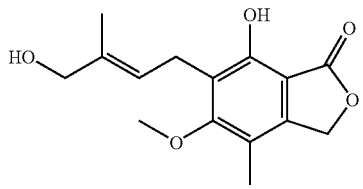

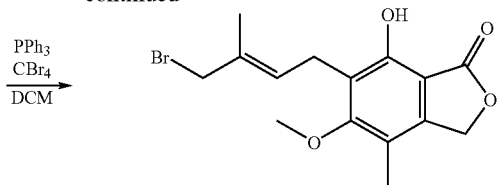

Example 92-J 6-(4-Bromo-3-methyl-but-2-enyl)-7-hydroxy-5-methoxy-4-methyl-3H-isobenzofuran-1-one Polymer-supported triphenylphosphine (3 mmol/g, 0.5 g) was soaked in dichloromethane (10 mL) for 1 h. 7-Hydroxy-6-(4-hydroxy-3-methyl-but-2-enyl)-5-methoxy-4-methyl-3H-isobenzofuran-1-one (100 mg, 0.36 mmol) and carbon tetrabromide (143 mg, 0.43 mmol) were sequentially added and the mixture was shaken for 1 h at room temperature. More carbon tetrabromide (143 mg, 0.43 mmol) was added and the mixture was shaken further for 1 h. The mixture was filtered and the filtrate was concentrated. The residue was chromatographed on silica gel (0% to 60% ethyl acetate/hexanes) to afford 6-(4-bromo-3-methyl-but-2-enyl)-7-hydroxy-5-methoxy-4-methyl-3H-isobenzofuran-1-one as an oil (52 mg, 42%); $^1$H NMR (300 MHz, CDCl$_3$) δ 1.95 (s, 3H), 2.16 (s, 3H), 3.44 (d, J=7.2, 2H), 3.78 (s, 3H), 3.98 (s, 2H), 5.21 (s, 2H), 5.68 (t, J=7.2 Hz, 1H), 7.71 (brs, 1H).

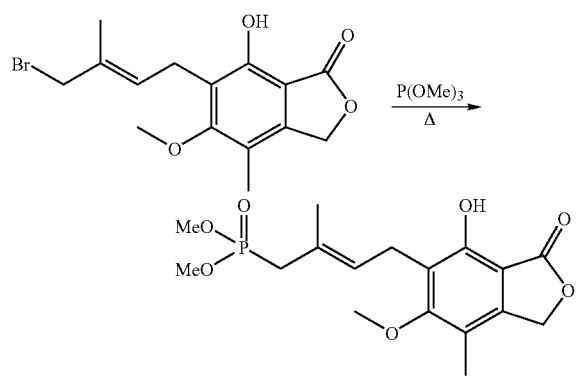

Example 92-K

[4-(4-Hydroxy-6-methoxy-7-methyl-3-oxo-1,3-dihydro-isobenzofuran-5-yl)-2-methyl-but-2-enyl]-phosphonic acid dimethyl ester A solution of 6-(4-bromo-3-methyl-but-2-enyl)-7-hydroxy-5-methoxy-4-methyl-3H-isobenzofuran-1-one (33 mg, 0.097 mmol) in trimethyl phosphite (1.0 mL, 8.5 mmol) was heated to 100° C. for 1 hour, whereupon complete reaction was indicated by LCMS. The reaction was worked up by removal of the excess of trimethyl phosphite under reduced pressure and the residue was purified by silica gel chromatography using EtOAc-hexanes (20-100%) to provide 20 mg (60%) of the desired product. $^1$H NMR (300 MHz, CDCl$_3$) δ 1.90 (s, 3H), 2.09 (s, 3H), 2.48 (d, 2H, J=22 Hz), 3.38 (t, 2H, J=6 Hz), 3.64 (d, 6H, J=11 Hz), 3.72 (s, 3H), 5.14 (s, 2H), 5.33 (q, 1H, J=6 Hz), 7.65 (br s, 1H); MS (m/z) 371 [M+H]$^+$.

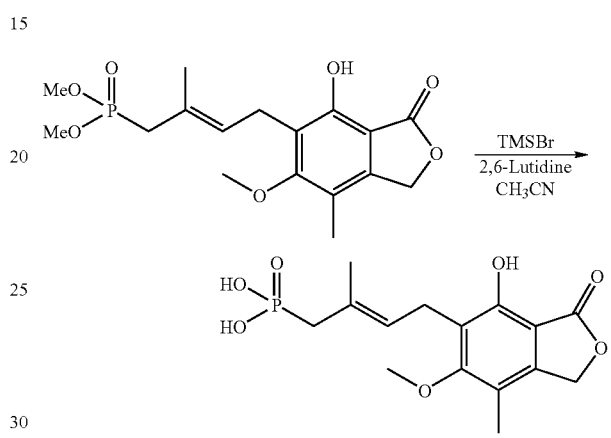

[4-(4-Hydroxy-6-methoxy-7-methyl-3-oxo-1,3-dihydro-isobenzofuran-5-yl)-2-methyl-but-2-enyl]-phosphonic acid (LC-2095-49): To a solution of [4-(4-hydroxy-6-methoxy-7-methyl-3-oxo-1,3-dihydro-isobenzofuran-5-yl)-2-methyl-but-2-enyl]-phosphonic acid dimethyl ester (18 mg, 0.049 mmol) in acetonitrile (2 mL) was added TMSBr (63 µL, 0.49 mmol) and 2,6-lutidine (85 µL, 0.73 mmol) at 0° C. The reaction solution was allowed to warm up to ambient temperature. The solution was stirred at room temperature for 2 hours when completion of the reaction was observed by LCMS. The reaction was cooled down to 0° C. and quenched with addition of MeOH. The reaction mixture was dried under reduced pressure and the residue was purified by RP HPLC using a C18 column with a gradient of H$_2$O-acetonitrile (5-0%) over 20 minutes to provide 12.2 mg (73%) of the product. $^1$H NMR (300 MHz, CD$_3$OD) δ 1.95 (s, 3H), 2.15 (s, 3H), 2.48 (d, 2H, J=22 Hz), 3.44 (t, 2H, J=6 Hz), 3.79 (s, 3H), 5.24 (s, 2H), 5.38 (q, 1H, J=7 Hz), 6.87 (br s, 1H); MS (m/z) 341 [M−H]$^−$.

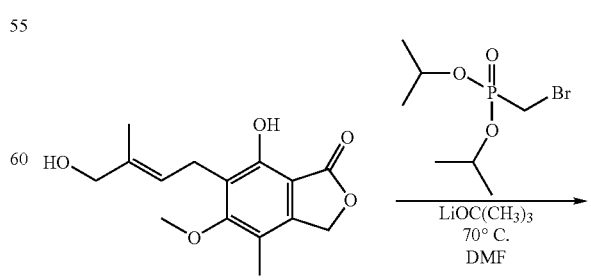

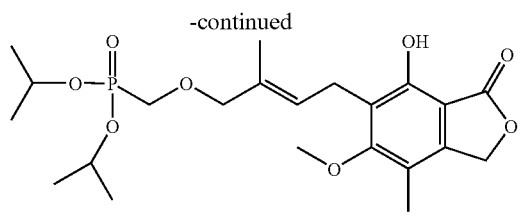

[4-(4-Hydroxy-6-methoxy-7-methyl-3-oxo-1,3-dihydro-isobenzofuran-5-yl)-2-methyl-but-2-enyloxymethyl]-phosphonic acid diisopropyl ester: A mixture of 7-hydroxy-6-(4-hydroxy-3-methyl-but-2-enyl)-5-methoxy-4-methyl-3H-isobenzofuran-1-one (50 mg, 0.18 mmol, Pankiewicz et al., *J. Med. Chem.* 2002, 45, 703), diisopropyl bromomethylphosphonate (93 mg, 0.36 mmol) and lithium t-butoxide (1M in THF, 0.54 mL) in DMF (3 mL) was heated at 70° C. for 5 h. The reaction was quenched with 1N HCl. The mixture was poured into 5% aqueous lithium chloride, extracted with ethyl acetate, and concentrated. The residue was purified by chromatography on silica gel, affording [4-(4-hydroxy-6-methoxy-7-methyl-3-oxo-1,3-dihydro-isobenzofuran-5-yl)-2-methyl-but-2-enyloxymethyl]-phosphonic acid diisopropyl ester as an oil (25 mg, 32%); $^1$H NMR (300 MHz, CDCl$_3$) δ 1.25 (m, 12H), 1.79 (s, 3H), 2.05 (s, 3H), 3.37 (d, J=6.6 Hz, 2H), 3.58 (d, 2H), 3.77 (s, 3H), 3.97 (m, 2H), 4.68 (m, 2H), 5.19 (s, 2H), 5.45 (t, J=6.6 Hz, 1H), 7.83 (s, 1H).

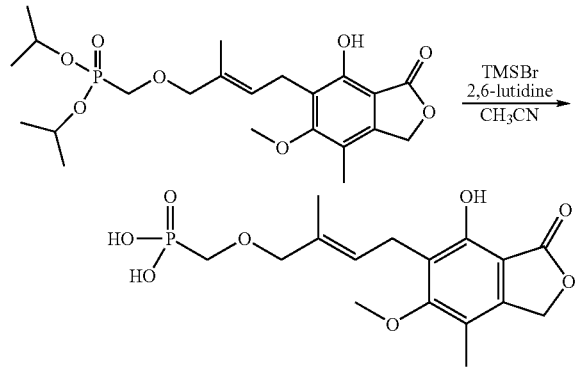

Example 92-L

[4-(4-Hydroxy-6-methoxy-7-methyl-3-oxo-1,3-dihydro-isobenzofuran-5-yl)-2-methyl-but-2-enyloxymethyl]-phosphonic acid To a solution of [4-(4-hydroxy-6-methoxy-7-methyl-3-oxo-1,3-dihydro-isobenzofuran-5-yl)-2-methyl-but-2-enyloxymethyl]-phosphonic acid diisopropyl ester (25 mg, 0.055 mmol) and 2,6-lutidine (0.18 mL, 1.65 mmol) in acetonitrile was added trimethylsilyl bromide (0.126 mL, 1.1 mmol) at 0° C. The mixture was allowed to warm to room temperature and stirred for 4 h. The reaction was quenched with methanol at 0° C., and the resulting mixture was concentrated. The residue was purified by preparative reverse-phase HPLC to afford, after removal of the solvent, [4-(4-hydroxy-6-methoxy-7-methyl-3-oxo-1,3-dihydro-isobenzofuran-5-yl)-2-methyl-but-2-enyloxymethyl]-phosphonic acid as an oil (17 mg, 83%); $^1$H NMR (300 MHz, CD$_3$OD) δ 1.81 (s, 3H), 2.06 (s, 3H), 3.40 (d, J=6.6 Hz, 2H), 3.50 (d, 2H), 3.77 (s, 3H), 3.97 (s, 2H), 5.20 (s, 2H), 5.47 (t, J=6.6 Hz, 1H); MS (m/z) 371 [M−H]$^-$.

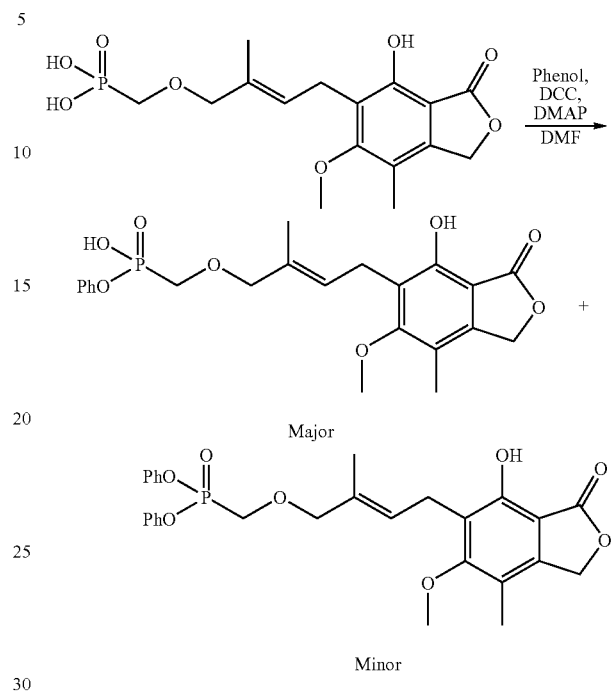

Example 92-M

[4-(4-Hydroxy-6-methoxy-7-methyl-3-oxo-1,3-dihydro-isobenzofuran-5-yl)-2-methyl-but-2-enyloxymethyl]-phosphonic acid monophenyl ester and [4-(4-Hydroxy-6-methoxy-7-methyl-3-oxo-1,3-dihydro-isobenzofuran-5-yl)-2-methyl-but-2-enyloxymethyl]-phosphonic acid diphenyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid (49 mg, 0.13 mmol) in DMF (0.4 mL) and phenol (62 mg, 0.65 mmol) was added dicyclohexyl carbodiimide (107 mg, 0.52 mmol) and DMAP (8 mg, 0.065 mmol) in DMF (0.6 mL), slowly at 0° C. The reaction was allowed to warm to room temperature and heated to 140° C. for 10 hours. After cooling to room temperature the mixture was filtered and extracted with aqueous 1N NaOH solution. The aqueous layer was acidified with aqueous 1N HCl and extracted with EtOAc. The organic layer was dried over Na$_2$SO$_4$ and concentrated to dryness. The residue was purified by reverse-phase HPLC to provide 18.5 mg of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (major product) as a pale yellow solid and 4.1 mg of [4-(4-hydroxy-6-methoxy-7-methyl-3-oxo-1,3-dihydro-isobenzofuran-5-yl)-2-methyl-but-2-enyloxymethyl]-phosphonic acid diphenyl ester (minor product) also as a pale yellow solid. Major product: $^1$H NMR (300 MHz, CD$_3$OD) δ 1.82 (s, 3H), 2.16 (s, 3H), 3.46 (d, 2H, J=7 Hz), 3.70 (d, 2H, J=8 Hz), 3.77 (s, 3H), 3.96 (s, 2H), 5.25 (s, 2H), 5.52 (t, 1H, J=8 Hz), 7.10-7.21 (m, 3H), 7.30 (t, 2H, J=8 Hz); $^{31}$P (121.4 MHz, CD$_3$OD) δ 17.3; MS (m/z) 449.0 [M+H]$^+$, 471.2 [M+Na]$^+$. Minor product: $^1$H NMR (300 MHz, CD$_3$OD) δ 1.82 (s, 3H), 2.15 (s, 3H), 3.47 (d, 2H, J=7 Hz), 3.77 (s, 3H), 3.98-4.06 (m, 4H), 5.25 (s, 2H), 5.50-5.61 (m, 1H), 7.10-7.25 (m, 6H), 7.30-7.41 (m, 4H); $^{31}$P (121.4 MHz, CD$_3$OD) δ 16.3; MS (m/z) 525.2 [M+H]$^+$, 547.2 [M+Na]$^+$.

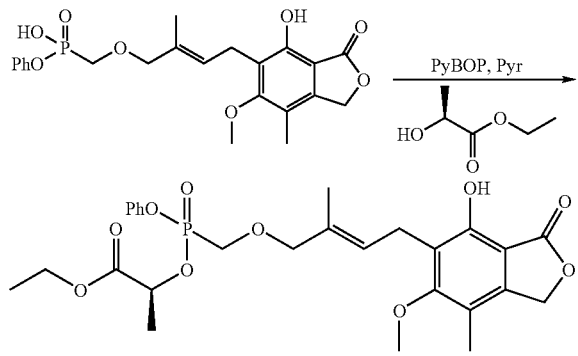

Example 92-N

2-{[4-(4-Hydroxy-6-methoxy-7-methyl-3-oxo-1,3-dihydro-isobenzofuran-5-yl)-2-methyl-but-2-enyloxymethyl]-phenoxy-phosphinoyloxy}-propionic acid ethyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (18.5 mg, 0.040 mmol) and ethyl (S)-(−)-lactate (47 µL, 0.400 mmol) in pyridine (0.5 mL) was added PyBOP (32 mg, 0.060 mmol). The solution was stirred at room temperature for 1 hour, when an additional portion of PyBOP (21 mg, 0.040 mmol) was added. The solution was stirred for another hour and concentrated. The residue was purified by HPLC to provide 7.5 mg of the desired product as a clear oil. $^1$H NMR (300 MHz, CD$_3$OD) δ 1.22 and 1.25 (t, 3H, J=7 Hz), 1.42 and 1.50 (d, 3H, J=7 Hz), 1.82 and 1.83 (s, 3H), 2.16 (s, 3H), 3.47 (d, 2H, J=7 Hz), 3.78 (s, 3H), 3.89 (d, 1H, J=8 Hz), 3.93-4.02 (m, 3H), 4.10-4.22 (m, 2H), 4.94-5.08 (m, 1H), 5.25 (s, 2H), 5.50-5.60 (m, 1H), 7.15-7.27 (m, 3H), 7.33-7.41 (m, 2H); $^{31}$P (121.4 MHz, CD$_3$OD) δ 18.9, 20.3; MS (m/z) 549.2 [M+H]$^+$, 571.3 [M+Na]$^+$.

Scheme III

B.

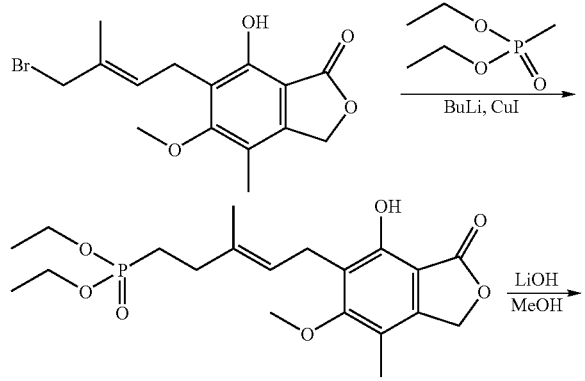

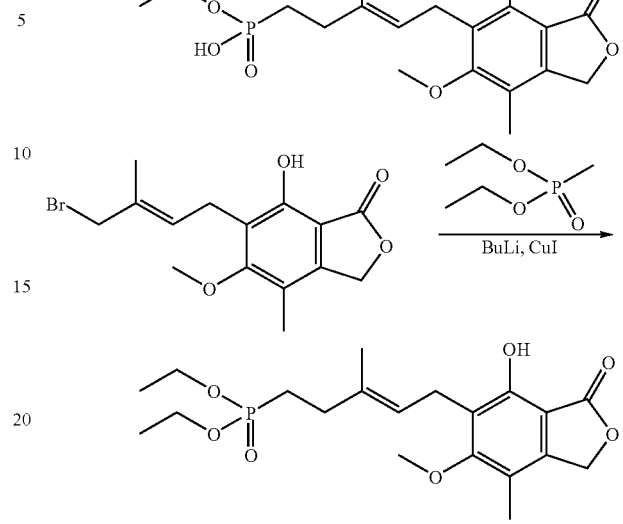

Example 92-O

[5-(4-Hydroxy-6-methoxy-7-methyl-3-oxo-1,3-dihydro-isobenzofuran-5-yl)-3-methyl-pent-3-enyl]-phosphonic acid diethyl ester Butyl lithium (1.6 M in hexanes, 1 mL) was added to an equal volume of THF at −20° C. A solution of diethyl methylphosphonate (220 mg, 1.45 mmol) in THF (1 mL) was then added dropwise and the mixture was stirred for 30 min. After cooling to −60° C., the solution was transferred via a cannula to a vial containing copper (I) iodide (276 mg, 1.45 mmol), and the resulting mixture was stirred for 1 h at −30° C. A solution of 6-(4-bromo-3-methyl-but-2-enyl)-7-hydroxy-5-methoxy-4-methyl-3H-isobenzofuran-1-one (50 mg, 0.15 mmol) in THF (1 mL) was added, and the mixture was allowed to warm to 0° C. for 2 h before saturated aqueous ammonium chloride was added. The reaction mixture was acidified with 2 N HCl and extracted with ethyl acetate. The ethyl acetate extract was concentrated and the residue was chromatographed on silica gel (40% to 100% ethyl acetate/hexanes), affording [5-(4-hydroxy-6-methoxy-7-methyl-3-oxo-1,3-dihydro-isobenzofuran-5-yl)-3-methyl-pent-3-enyl]-phosphonic acid diethyl ester as an oil (27 mg, contaminated with the starting diethyl methylphosphonate); $^1$H NMR (300 MHz, CDCl$_3$) δ 1.32 (m, 6H), 1.8-1.9 (m, 5H), 2.18 (s, 3H), 2.25 (m, 2H), 3.42 (d, J=7.2, 2H), 3.78 (s, 3H), 4.15 (m, 4H), 5.21 (s, 2H), 5.24 (t, J=7.2 Hz, 1H), 7.65 (s, 1H).

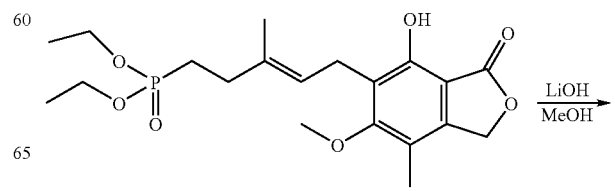

-continued

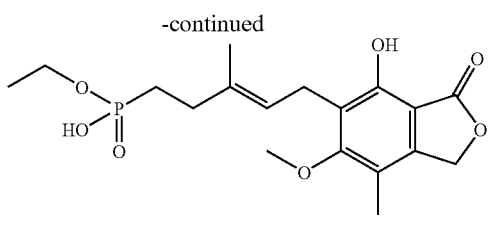

Example 92-P

[5-(4-Hydroxy-6-methoxy-7-methyl-3-oxo-1,3-dihydro-isobenzofuran-5-yl)-3-methyl-pent-3-enyl]-phosphonic acid monoethyl ester A mixture of [5-(4-hydroxy-6-methoxy-7-methyl-3-oxo-1,3-dihydro-isobenzofuran-5-yl)-3-methyl-pent-3-enyl]-phosphonic acid diethyl ester (27 mg, 0.066 mmol), LiOH (200 mg), MeOH (3 mL) and water (1 mL) was stirred at 70° C. for 4 h. After cooling, the reaction solution was acidified with 2 N HCl, mixed with brine, and extracted with ethyl acetate/acetonitrle. The organic extract was concentrated and the residue was purified by preparative reverse-phase HPLC (acetonitrile and 0.1% aqueous $CF_3COOH$), affording [5-(4-hydroxy-6-methoxy-7-methyl-3-oxo-1,3-dihydro-isobenzofuran-5-yl)-3-methyl-pent-3-enyl]-phosphonic acid monoethyl ester (7 mg, 28%); $^1$H NMR (300 MHz, $CD_3OD$) δ 1.28 (t, J=6.9, 3H), 1.7-1.9 (m, 5H), 2.20 (s, 3H), 2.2-2.3 (m, 2H), 3.41 (d, J=6.6 Hz, 2H), 3.80 (s, 3H), 4.02 (m, 2H), 5.2-5.3 (m, 3H).

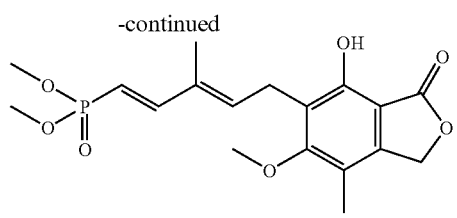

Example 92-Q

[5-(4-Hydroxy-6-methoxy-7-methyl-3-oxo-1,3-dihydro-isobenzofuran-5-yl)-3-methyl-penta-1,3-dienyl]-phosphonic acid dimethyl ester To a solution of tetramethylmethylene diphosphonate (102 mg, 0.44 mmol) in THF (2.5 mL) was added a solution of sodium bis(trimethysilyl)amide in THF (1.0 M, 0.44 mL). After stirring for 30 minutes, a solution of 4-(4-hydroxy-6-methoxy-7-methyl-3-oxo-1,3-dihydro-isobenzofuran-5-yl)-2-methyl-but-2-enal (30 mg, 0.11 mmol, Pankiewicz, et al., *J. Med. Chem.* 45, 703) in THF (2.5 mL) was added and stirring was continued for an additional 15 minutes. The reaction was quenched with saturated aqueous ammonium chloride. The mixture was extracted with ethyl acetate. After evaporation of solvent, the residue was purified by chromatography on silica gel eluting with ethyl acetate (50% to 100%)/hexanes, affording [5-(4-hydroxy-6-methoxy-7-methyl-3-oxo-1,3-dihydro-isobenzofuran-5-yl)-3-methyl-penta-1,3-dienyl]-phosphonic acid dimethyl ester (30 mg, 71%) as an oil; $^1$H NMR (300 MHz, $CDCl_3$) δ 1.80 (s, 3H), 2.04 (s, 3H), 3.45 (d, J=6.6 Hz, 2H), 3.76 (s, 3H), 3.88 (d, 6H), 5.20 (s, 3H), 5.55 (m, 1H), 5.95 (m, 1H), 7.05 (m, 1H), 7.65 (s, 1H).

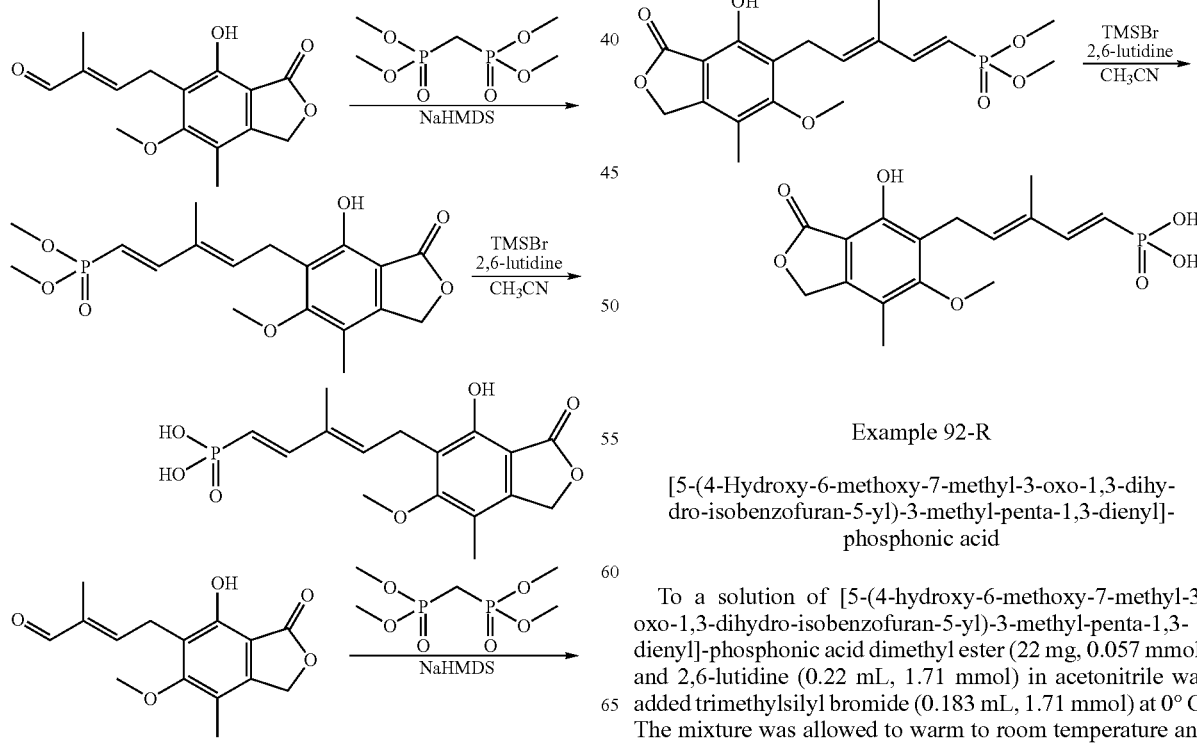

Example 92-R

[5-(4-Hydroxy-6-methoxy-7-methyl-3-oxo-1,3-dihydro-isobenzofuran-5-yl)-3-methyl-penta-1,3-dienyl]-phosphonic acid To a solution of [5-(4-hydroxy-6-methoxy-7-methyl-3-oxo-1,3-dihydro-isobenzofuran-5-yl)-3-methyl-penta-1,3-dienyl]-phosphonic acid dimethyl ester (22 mg, 0.057 mmol) and 2,6-lutidine (0.22 mL, 1.71 mmol) in acetonitrile was added trimethylsilyl bromide (0.183 mL, 1.71 mmol) at 0° C. The mixture was allowed to warm to room temperature and stirred for 1 h. The reaction was quenched with methanol at 0°

C., and the resulting mixture was concentrated. The residue was purified by preparative reverse-phase HPLC to afford, after removal of the solvent, [5-(4-hydroxy-6-methoxy-7-methyl-3-oxo-1,3-dihydro-isobenzofuran-5-yl)-3-methyl-penta-1,3-dienyl]-phosphonic acid as a solid (13 mg, 65%); $^1$H NMR (300 MHz, CD$_3$OD) δ 1.91 (s, 3H), 2.10 (s, 3H), 3.55 (d, J=6.6 Hz, 2H), 3.75 (s, 3H), 5.2 (s, 2H), 5.6-5.8 (m, 2H), 6.9 (m, 1H).
III.
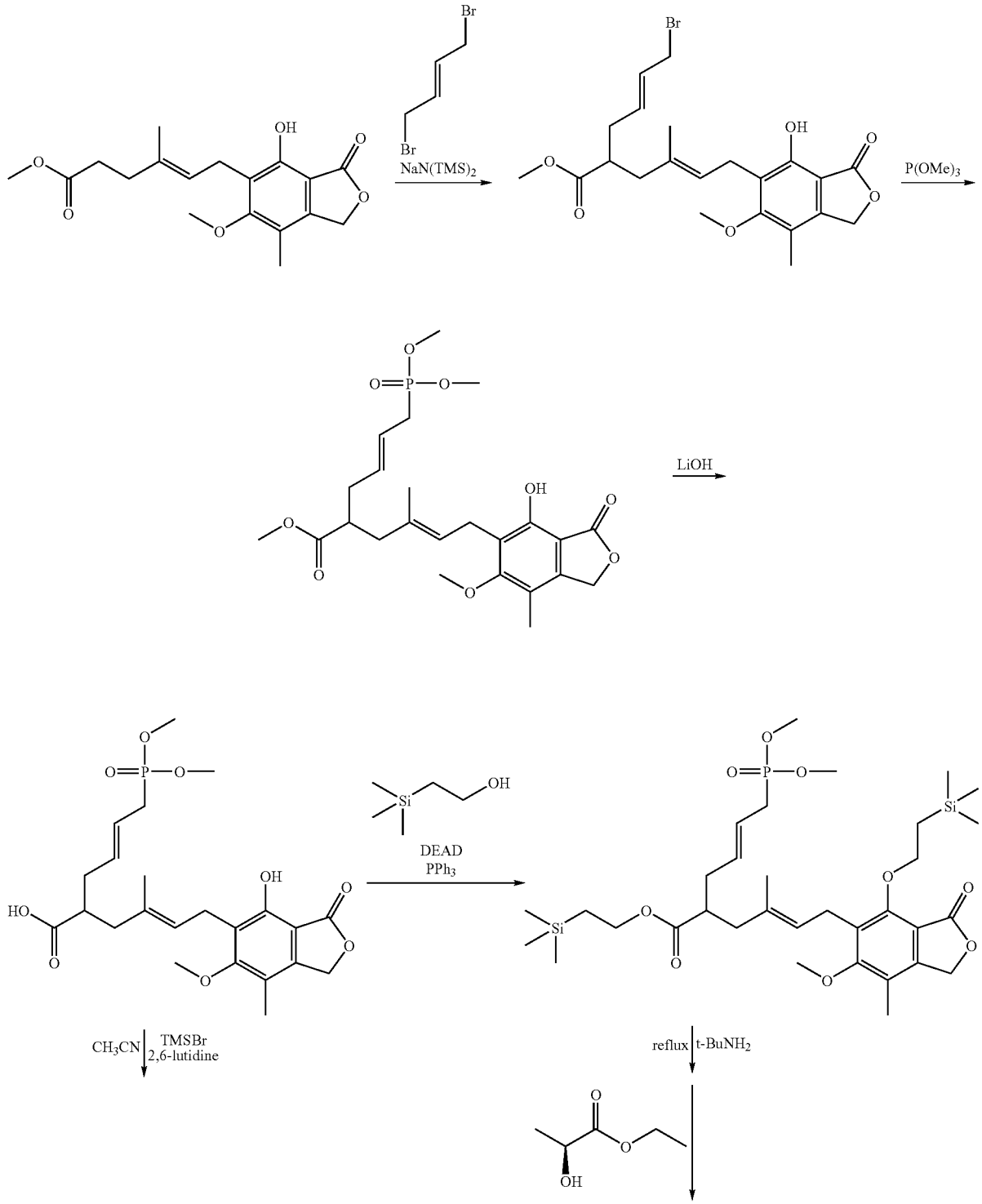

-continued

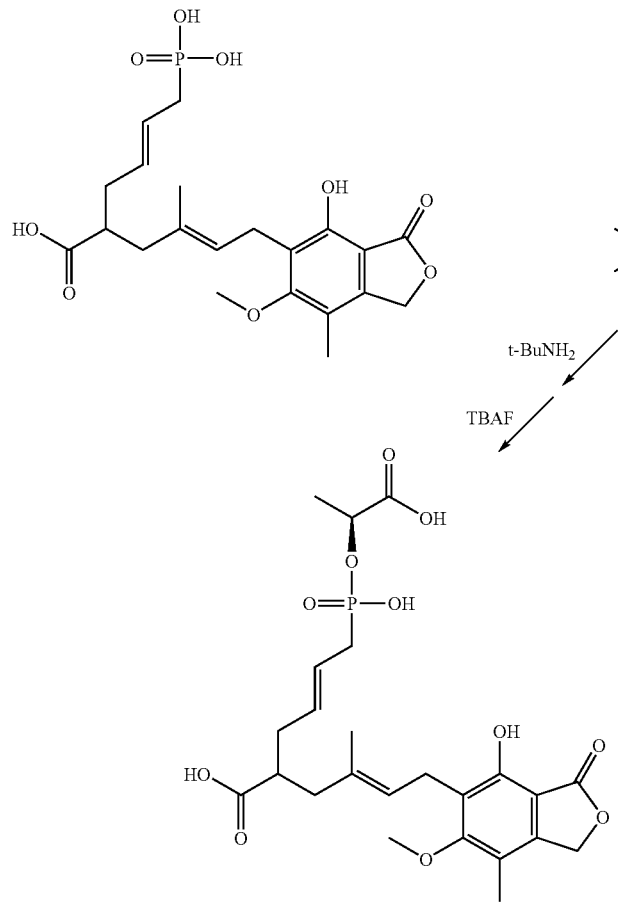

Scheme I

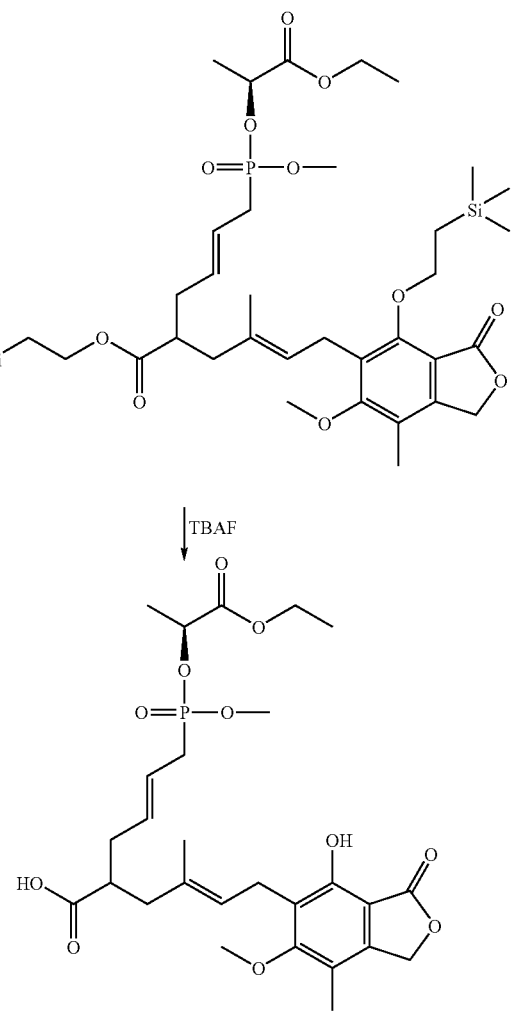

Example 92-S

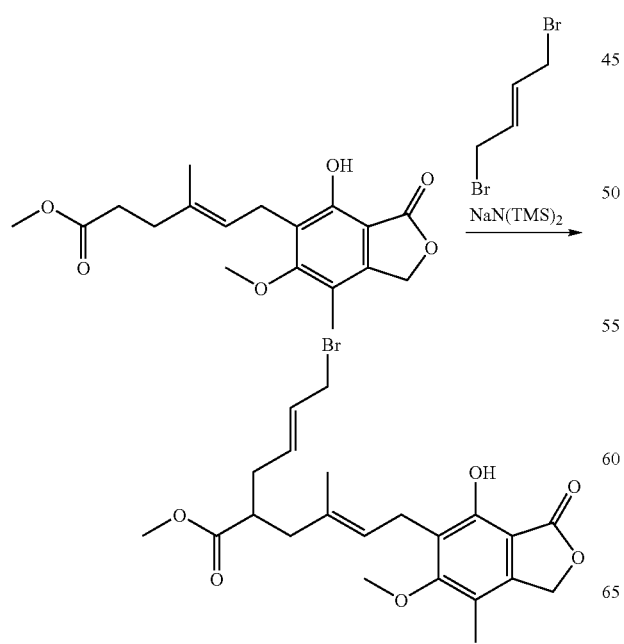

2-(4-Bromo-but-2-enyl)-6-(4-hydroxy-6-methoxy-7-methyl-3-oxo-1,3-dihydro-isobenzofuran-5-yl)-4-methyl-hex-4-enoic acid methyl ester To a cooled (−78° C.) solution of mycophenolic acid methyl ester (138 mg, 0.41 mmol) in THF (2.5 mL) was added a THF solution of sodium bis(trimethysilyl)amide (1.0 M, 0.98 mL). After stirring for 30 minutes, a solution of 1,4-dibromo-2-butene (950 mg, 4.1 mmol) in THF (2.5 mL) was added and stirring was continued for 10 min. The resulting mixture was warmed to −30° C. and stored at this temperature for 16 h. The reaction was quenched with saturated aqueous ammonium chloride. The mixture was extracted with ethyl acetate to give, after evaporation of the solvent, a residue which was purified by chromatography on silica gel, eluting with ethyl acetate (0% to 40%)/hexanes, affording 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester (150 mg, 78%) as an oil; $^1$H NMR (300 MHz, CDCl$_3$) δ 1.75 (s, 3H), 2.0-2.4 (m, 8H), 2.62 (m, 1H), 3.37 (d, J=6.6 Hz, 2H), 3.58 (s, 3H), 3.76 (s, 3H), 3.88 (d, J=4.8 Hz, 2H), 5.1-5.3 (m, 3H), 5.67 (brs, 2H), 7.67 (s, 1H).

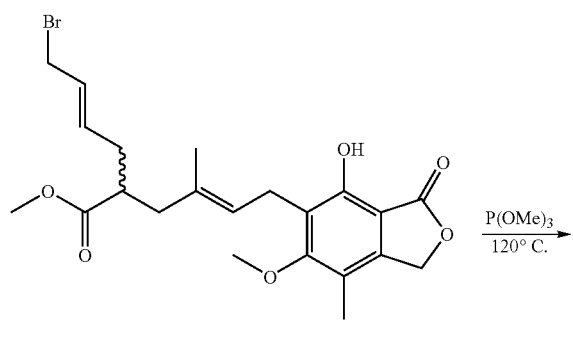

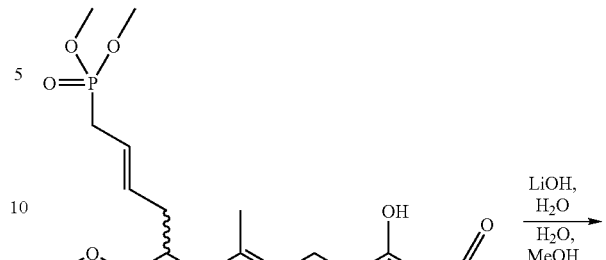

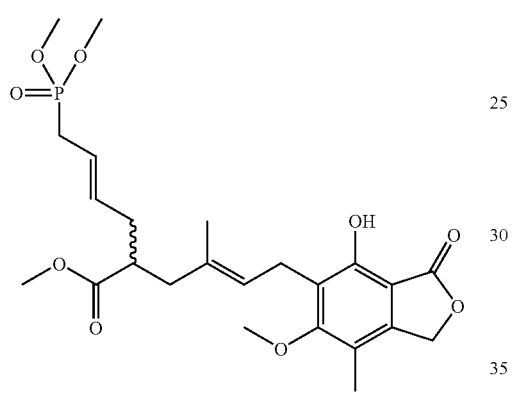

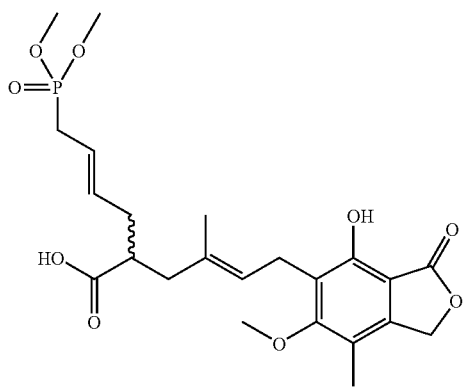

Example 92-T

2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester Under a $N_2$ atmosphere, a solution of 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester (490 mg, 1.05 mmol) in trimethyl phosphite (2.5 mL, 21.1 mmol) was heated at 120° C. for 1 hour. The reaction was allowed to cool to room temperature. The reaction mixture was worked up by removal of the solvent in vacuo followed by chromatography using EtOAc-hexanes to provide 460 mg (88%) of the product as an oil. $^1$H NMR (300 MHz, $CDCl_3$) δ 1.77 (s, 3H), 2.081-2.31 (m, 4H), 2.15 (s, 3H), 2.52 (d, 1H, J=22 Hz), 2.54 (d, 1H, J=22 Hz), 2.55-2.63 (m, 1H), 3.36 (d, 2H, J=7 Hz), 3.57 (s, 3H), 3.72 (d, 6H, J=11 Hz), 3.76 (s, 3H), 5.20 (s, 2H), 5.20-5.26 (m, 1H), 5.36-5.56 (m, 2H), 7.69 (s, 1H); $^{31}$P (121.4 MHz, $CDCl_3$) δ 30.1; MS (m/z) 497.2 [M+H]$^+$, 519.2 [M+Na]$^+$.

Example 92-U

2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester (460 mg, 0.927 mmol) in a solution of 1:1:2 of $H_2O$/MeOH/THF (8 mL) was stirred with $LiOH·H_2O$ (78 mg, 1.86 mmol) at ambient temperature for 12 hours. A second batch of $LiOH·H_2O$ (40 mg, 0.952 mmol) was added. The reaction mixture was stirred at room temperature for another 16 hours, after which no further progress was observed. The reaction was quenched by addition of a saturated aqueous solution of $NH_4Cl$. The organic layer was removed in vacuo and the product was extracted with EtOAc from the aqueous layer, which had been acidified by addition of 5 drops of 2 N HCl. The product was further purified by chromatography to provide the desired product. $^1$H NMR (300 MHz, $CDCl_3$) δ 1.79 (s, 3H), 2.08-2.38 (m, 4H), 2.15 (s, 3H), 2.53 (d, 1H, J=22 Hz), 2.60 (d, 1H, J=22 Hz), 2.57-2.64 (m, 1H), 3.38 (d, 2H, J=7 Hz), 3.72 (d, 6H, J=11 Hz) 3.76 (s, 3H), 5.20 (s, 2H), 5.27 (t, 1H, J=6 Hz), 5.36-5.63 (m, 2H); $^{31}$P (121.4 MHz, $CDCl_3$) δ 30.5; MS (m/z) 481.2 [M−H]$^-$.

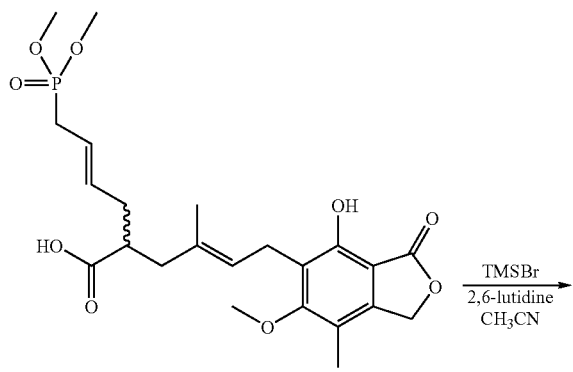

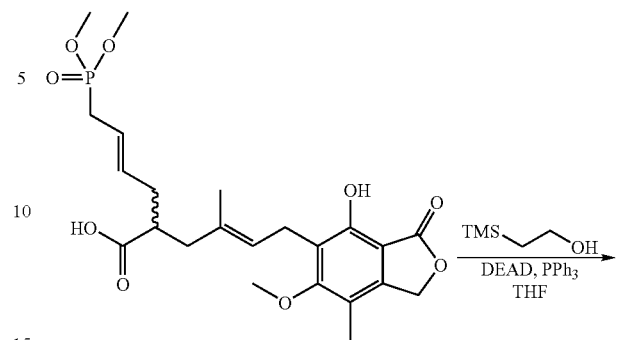

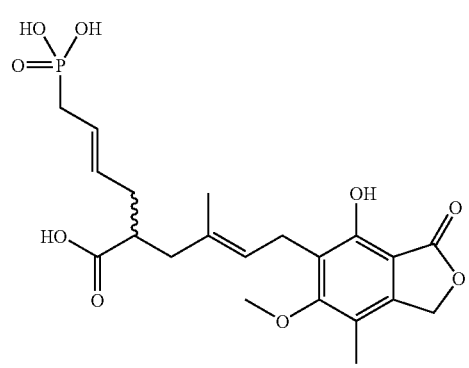

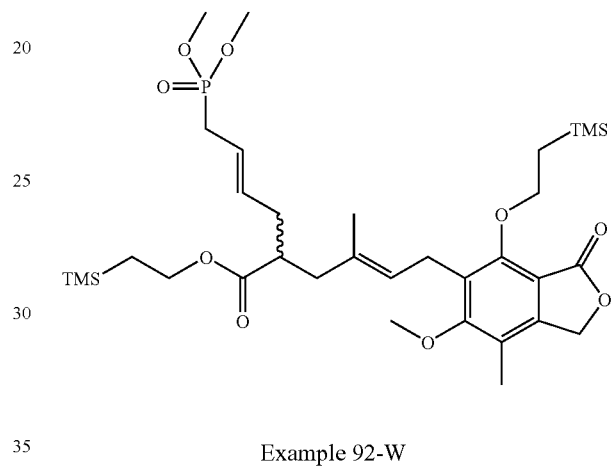

Example 92-W

2-[4-(Dimethoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester Example 92-V 2-[4-(2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid To a solution of 2-[4-(dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid (25 mg, 0.052 mmol) in acetonitrile (2 mL) was added 2,6-lutidine (60 μL, 0.52 mmol) and TMSBr (67 μL, 0.52 mmol). The reaction was allowed to proceed for 45 minutes when it was completed as judged by LCMS. The reaction mixture was concentrated under reduced pressure and quenched with an aqueous NaOH solution (1 mL). The product was purified by reverse-phase HPLC on a C18 column to provide 14.2 mg (60%) of the product as a solid. $^1$H NMR (300 MHz, CD$_3$OD) δ 1.81 (s, 3H), 2.081-2.31 (m, 4H), 2.16 (s, 3H), 2.45 (d, 1H, J=22 Hz), 2.47 (d, 1H, J=22 Hz), 2.55-2.63 (m, 1H), 3.38 (d, 2H, J=7 Hz), 3.77 (s, 3H), 5.25 (s, 2H), 5.20-5.36 (m, 1H), 5.36-5.56 (m, 2H); $^{31}$P (121.4 MHz, CD$_3$OD) δ 25.4; MS (m/z) 453 [M−H]$^-$.

A solution of 2-[4-(dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid (160 mg, 0.332 mmol) and trimethylsilylethanol (160 mg, 1.36 mmol) in THF (8.00 mL) was stirred with triphenylphosphine (345 mg, 1.33 mmol). To this solution was added diethyl azodicarboxylate (230 μL, 1.33 mmol) at 0° C. The mixture was allowed to warm to room temperature and stirred for 16 hours. Additional triphenylphosphine (180 mg, 0.692 mmol), trimethylsilylethanol (160 mg, 1.36 mmol), and diethyl azodicarboxylate (115 μL, 0.665 mmol) were added and the reaction mixture was stirred for another 1 day at room temperature. The reaction was worked up by removing the solvents in vacuo and purifying the residue by silica gel chromatography to provide 192 mg (85%) of the product as a clear oil. $^1$H NMR (300 MHz, CDCl$_3$) δ 0.03 (s, 9H), 0.05 (s, 9H), 0.93-0.96 (m, 2H), 1.20-1.29 (m, 2H), 1.78 (s, 3H), 2.01-2.32 (m, 4H), 2.17 (s, 3H), 2.51 (d, 1H, J=22 Hz), 2.58 (d, 1H, J=22 Hz), 2.50-2.60 (m, 1H), 3.37 (d, 2H, J=7 Hz), 3.72 (d, 6H, J=11 Hz), 3.76 (s, 3H), 4.08 (appt t, 2H, J=8 Hz), 4.30 (appt t, 2H, J=8 Hz), 5.12 (s, 2H), 5.15-5.25 (m, 1H), 5.36-5.63 (m, 2H); $^{31}$P (121.4 MHz, CDCl$_3$) δ 29.3; MS (m/z) 705.3 [M+Na]$^+$.

Example 92-X

2-[4-(Hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester

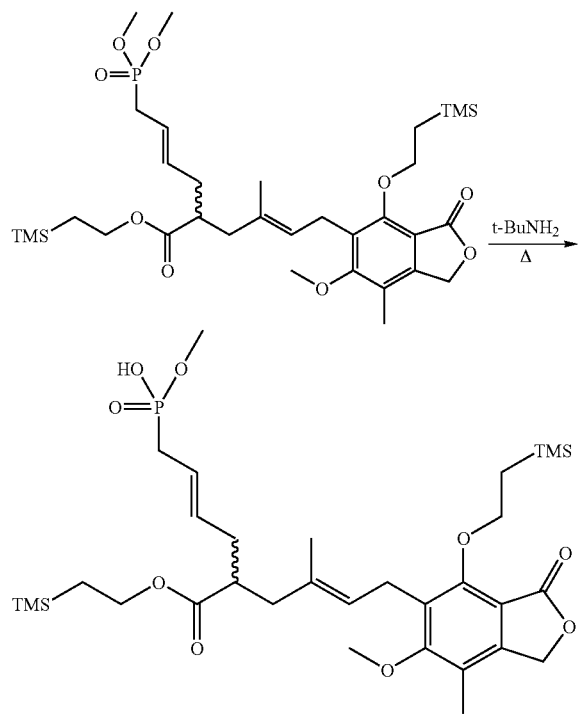

A mixture of 2-[4-(dimethoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (184 mg, 0.270 mmol) in tert-butylamine (2.8 mL, 27 mmol) was heated at 60° C. for 24 hours. The solution was allowed to cool down to room temperature and concentrated. The residue was purified by silica gel column chromatography using MeOH/CH$_2$Cl$_2$ (0-30%) to provide 75 mg of the product as a clear oil. $^1$H NMR (300 MHz, CDCl$_3$) δ 0.01 (s, 9H), 0.04 (s, 9H), 0.89 (appt t, 2H, J=9 Hz), 1.23 (appt t, 2H, J=9 Hz), 1.77 (s, 3H), 2.01-2.31 (m, 4H), 2.17 (s, 3H), 2.36 (d, 1H, J=22 Hz), 2.38 (d, 1H, J=22 Hz), 2.52 (septet, 1H, J=9 Hz), 3.39 (d, 2H, J=7 Hz), 3.51 (d, 3H, J=11 Hz), 4.01-4.08 (m, 2H), 4.30 (dd, 2H, J=8, 9 Hz), 5.11 (s, 2H), 5.19 (br t, 1H, J=6 Hz), 5.33-5.56 (m, 2H), 8.49 (br s, 1H); $^{31}$P (121.4 MHz, CDCl$_3$) δ 22.1; MS (m/z) 667.4 [M+Na]$^+$.

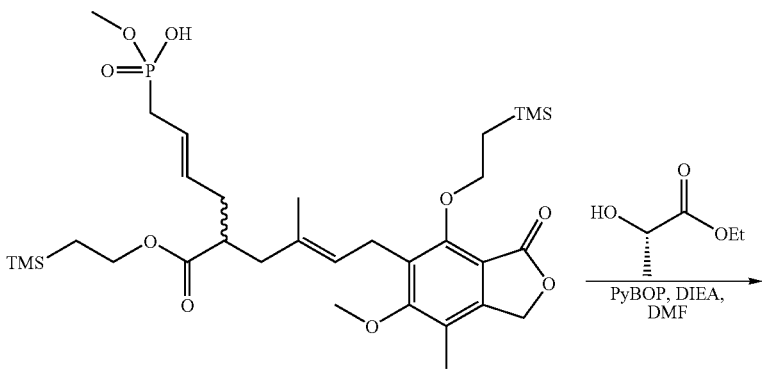

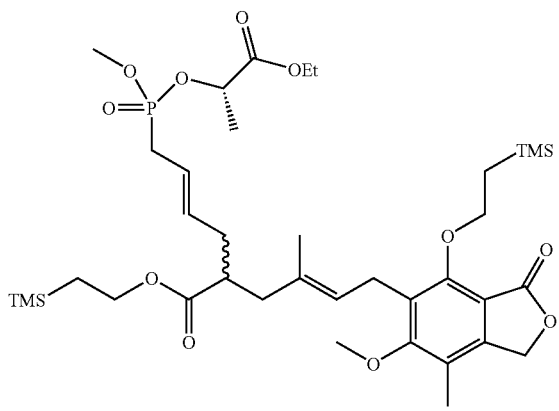

Example 92-Y

2-{4-[(1-Ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (67 mg, 0.10 mmol), PyBOP (234 mg, 0.450 mmol) in DMF (1.5 mL) was stirred with ethyl (S)-(−)-lactate (53 mg, 0.45 mmol) and DIEA (174 µL, 1.00 mmol) at ambient temperature for 1 hour when complete consumption of the starting materials was observed. The reaction was worked up by addition of saturated aqueous sodium chloride and ethyl acetate. The organic layer was separated and washed with 5% aqueous solution of lithium chloride. The organic layer was dried in vacuo and the residue was purified by silica gel chromatography using MeOH—$CH_2Cl_2$ (0-20%) to provide 57 mg (74%) of the desired product as a clear oil. $^1$H NMR (300 MHz, $CDCl_3$) δ 0.02 (s, 9H), 0.05 (s, 9H), 0.88-0.94 (m, 2H), 1.20-1.30 (m, 2H), 1.29 (t, 3H, J=7 Hz), 1.45 (d, 3H, J=7 Hz), 1.78 (s, 3H), 2.01-2.31 (m, 4H), 2.17 (s, 3H), 2.50-2.58 (m, 1H), 2.65 (d, 1H, J=22 Hz), 2.67 (d, 1H, J=22 Hz), 3.39 (d, 2H, J=7 Hz), 3.69 and 3.77 (d, 3H, J=11 Hz), 3.76 (s, 3H), 4.07 (appt t, 2H, J=7 Hz), 4.20 (dq, 2H, J=3, 7 Hz), 4.29 (appt t, 2H, J=9 Hz), 4.85-4.99 (m, 1H), 5.12 (s, 2H), 5.19 (br t, 1H, J=6 Hz), 5.33-5.61 (m, 2H); $^{31}$P (121.4 MHz, $CDCl_3$) δ 28.9, 29.9; MS (m/z) 791.4 [M+Na]$^+$.

Example 92-Z

2-{4-[(1-Ethoxycarbonyl-ethoxy)-methoxy-phosphoryl]-but-2-enyl}-6-(4-hydroxy-6-methoxy-7-methyl-3-oxo-1,3-dihydro-isobenzofuran-5-yl)-4-methyl-hex-4-enoic acid A solution of 2-{4-[(1-ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (14 mg, 0.018 mmol) in THF (1 mL) was stirred with a 1M solution of TBAF in THF (55 µL, 0.055 mmol) for 1 hour. The reaction mixture was worked up by concentrating the reaction mixture in vacuo and extracting the product from an aqueous 1N HCl solution with EtOAc. The organic layer was washed with brine and dried. The product was purified by silica gel column chromatography EtOH-EtOAc (0-10%). Further purification was performed by dissolving the product in $CH_2Cl_2$ and passing the compound through a 13 mm Acrodisc syringe filter with a 0.45 µm Nylon membrane to provide 8 mg (77%) of the product. $^1$H NMR (300 MHz, $CDCl_3$) 0.92 (t, 3H, J=7 Hz), 1.30 (d, 3H, J=8 Hz), 1.79 (s, 3H), 2.10-2.39 (m, 4H), 2.15 (s, 3H), 2.53 (d, 1H, J=8 Hz), 2.65 (d, 1H, J=22 Hz), 2.68 (d, 1H, J=22 Hz), 3.38 (d, 2H, J=7 Hz), 3.70 and 3.74 (d, 3H, J=11 Hz), 3.76 (s, 3H), 4.07 (m, 2H), 4.96 (dq, 1H, J=7 Hz), 5.20 (s, 2H), 5.27 (br t, 1H, J=7 Hz), 5.33-5.55 (m, 2H), 7.51-7.56 (m, 1H), 7.68-7.74 (m, 1H); $^{31}$P (121.4 MHz, $CDCl_3$) δ 29.0, 30.1; MS (m/z) 569.2 [M+H]$^+$, 591.3 [M+Na]$^+$.

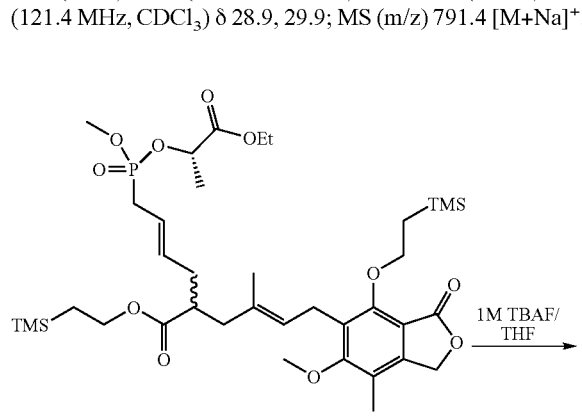

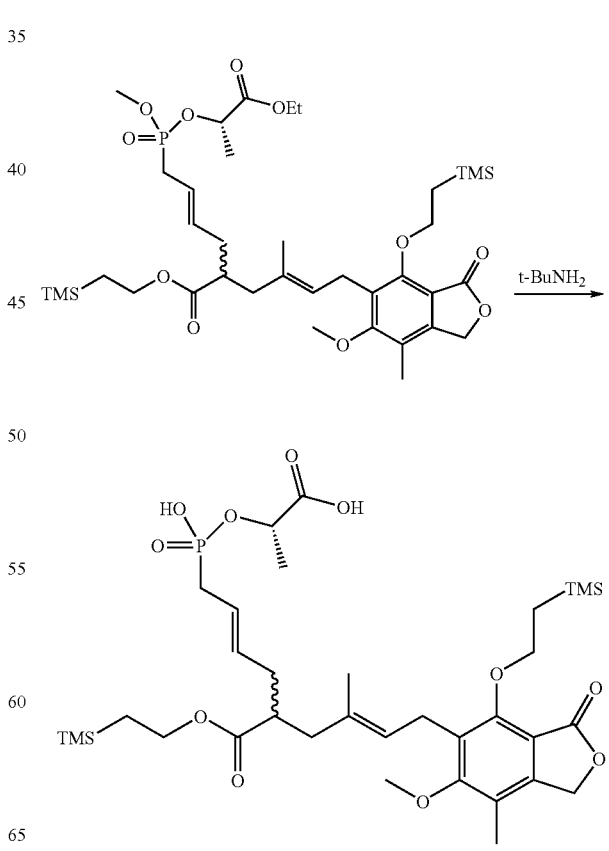

Example 92-AA

2-{4-[(1-Carboxy-ethoxy)-hydroxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-{4-[(1-ethoxycarbonyl-ethoxy)-methoxyphosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanylethyl ester (12 mg, 0.016 mmol) in tert-butylamine (1 mL, 9.6 mmol) was heated at 65° C. for 16 hours. The solution was allowed to cool down to room temperature and concentrated to provide the crude product as an oil. $^1$H NMR (300 MHz, CDCl$_3$) 0.03 (s, 9H), 0.04 (s, 9H), 0.86-0.98 (m, 2H), 1.22-1.33 (m, 2H), 1.50 (d, 3H, J=7 Hz), 1.78 (s, 3H), 2.05-2.30 (m, 4H), 2.10 (s, 3H), 2.48-2.63 (m, 3H), 3.40 (d, 2H, J=7 Hz), 3.76 (s, 3H), 4.08 (appt t, 2H, J=9 Hz), 4.25-4.33 (m, 2H), 4.75-4.84 (m, 1H), 5.13 (s, 2H), 5.15-5.23 (m, 1H), 5.33-5.55 (m, 2H); $^{31}$P (121.4 MHz, CDCl$_3$) δ 28.9; MS (m/z) 725.3 [M−H]$^−$.

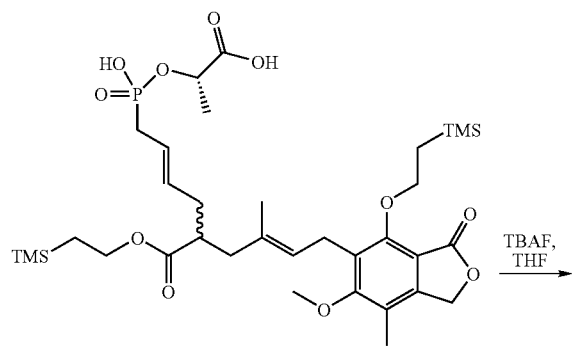

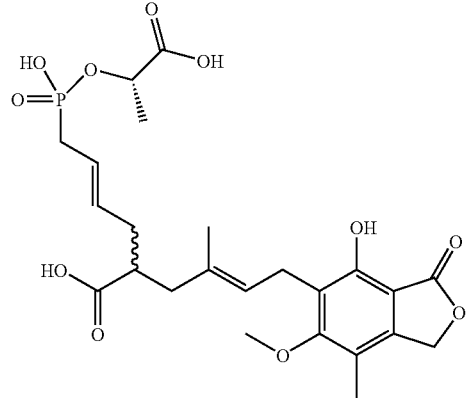

Example 92-AB

2-{4-[(1-Carboxy-ethoxy)-hydroxy-phosphoryl]-but-2-enyl}-6-(4-hydroxy-6-methoxy-7-methyl-3-oxo-1,3-dihydro-isobenzofuran-5-yl)-4-methyl-hex-4-enoic acid A solution of crude 2-{4-[(1-carboxy-ethoxy)-hydroxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (AC-2101-59) and tetrabutylammonium fluoride in THF (1M, 54 μL, 0.054 mmol) was stirred with THF (1 mL) for 2 hours at ambient temperature when an extra amount of tetrabutylammonium fluoride in THF (54 μL, 0.054 mmol) was added. The reaction was stirred for an additional 16 hours when the reaction was complete. The reaction mixture was concentrated in vacuo and the product was purified by reverse-phase HPLC using a Phenomenex Synergi 5μ Hydro RP 80 A column (50×21.2 mm) with eluents of H$_2$O, 0.1% TFA-CH$_3$CN, 0.1% TFA to provide the product (8.0 mg) as a clear oil. $^1$H NMR (300 MHz, CDCl$_3$) 1.51 (d, 3H, J=7 Hz), 1.79 (s, 3H), 2.05-2.40 (m, 4H), 2.11 (s, 3H), 2.49-2.71 (m, 3H), 3.38 (d, 2H, J=6 Hz), 3.76 (s, 3H), 4.85 (br s, 1H), 5.20 (s, 2H), 5.21-5.30 (m, 1H), 5.33-5.63 (m, 2H); $^{31}$P (121.4 MHz, CDCl$_3$) δ 27.7; MS (m/z) 525.2 [M−H]$^−$.

Scheme II

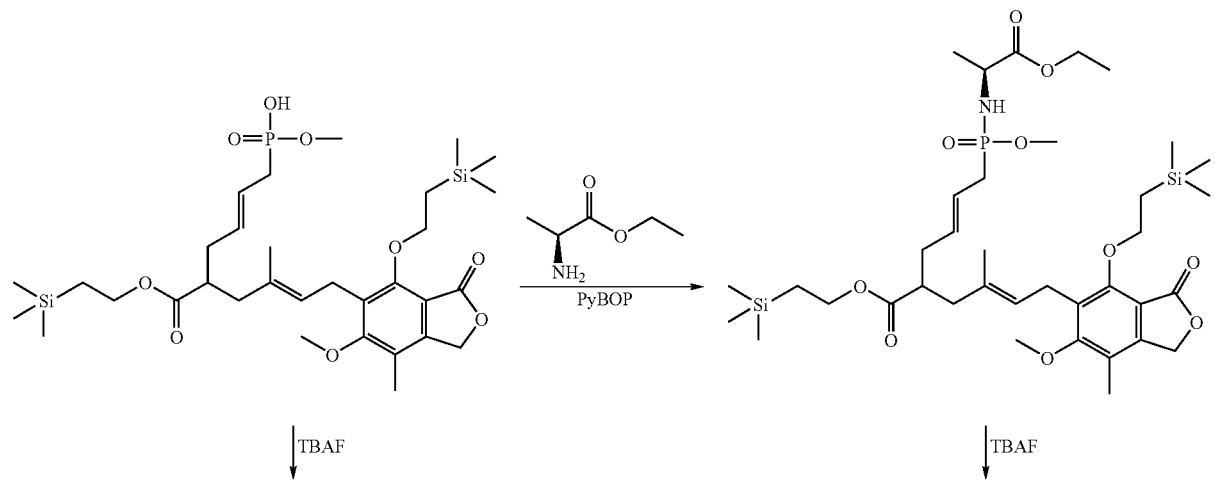

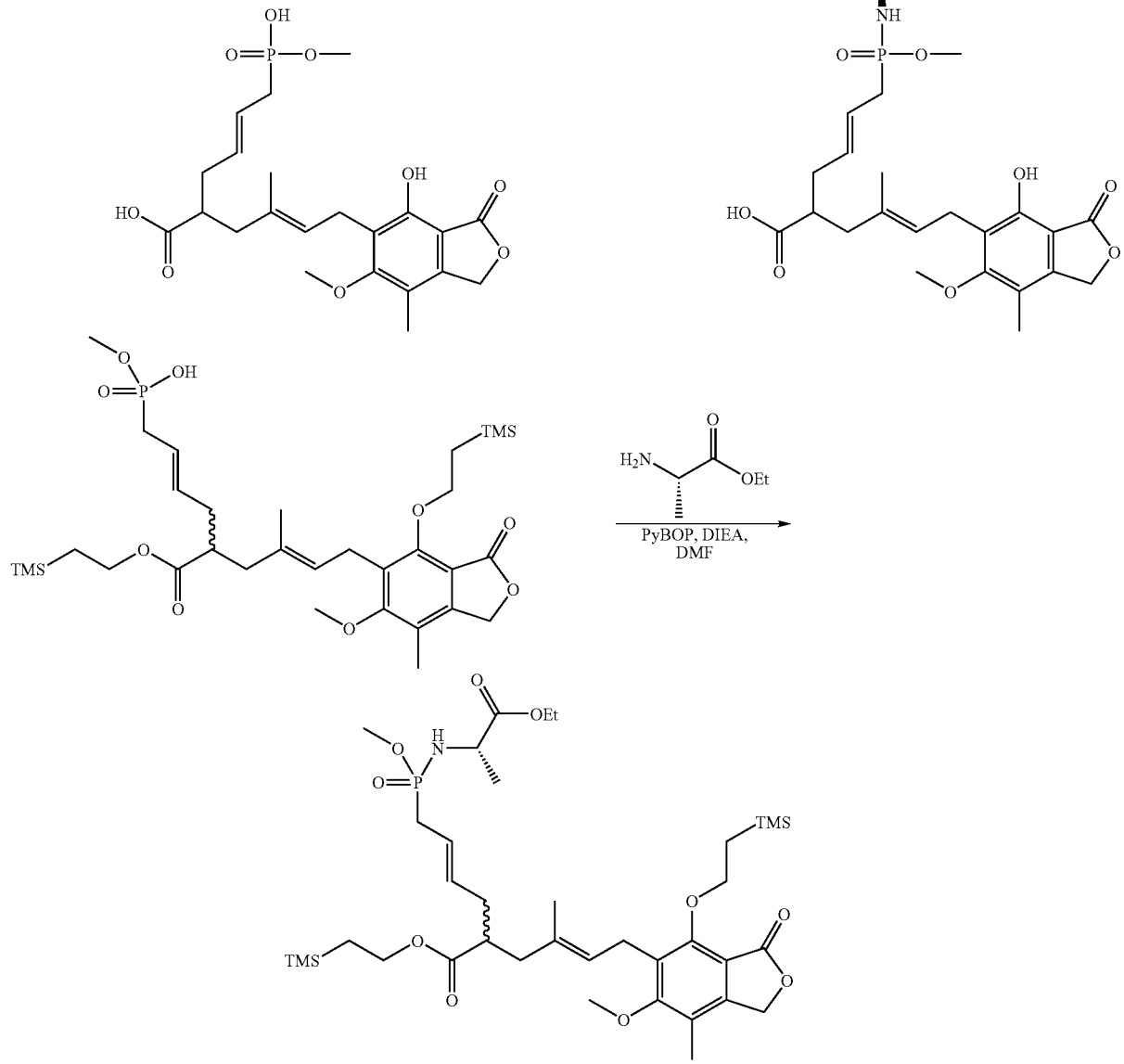

Example 92-AC 2-f{4-[(1-Ethoxycarbonyl-ethylamine)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (20 mg, 0.030 mmol), PyBOP (62.4 mg, 0.120 mmol) in DMF (1.0 mL) was stirred with L-alanine ethyl ester hydrochloride (18 mg, 0.12 mmol) and DIEA (26 μL, 0.15 mmol) at ambient temperature for 1 hour when complete consumption of the starting materials was observed. The reaction was worked up by addition of water until the reaction solution became cloudy. A minimum amount of DMF was added until the reaction became clear again. The reaction mixture was filtered through Acrodisc (13 mm syringe filter with a 0.45 μm Nylon membrane) and purified by reverse-phase HPLC using a Phenomenex Synergi 5μ Hydro RP 80 A column (50×21.2 mm), eluting with water and acetonitrile. The fractions containing the product were pooled together and dried in vacuo to remove the acetonitrile. The aqueous layer was saturated with sodium chloride and extracted with EtOAc and acetonitrile to provide 7.2 mg of the product. $^1$H NMR (300 MHz, CDCl$_3$) δ 0.03 (s, 9H), 0.05 (s, 9H), 0.923 (appt t, 2H, J=8 Hz), 1.18-1.31 (m, 5H), 1.41 (t, 3H, J=7 Hz), 1.78 (s, 3H), 2.03-2.36 (m, 4H), 2.18 (s, 3H), 2.43-2.63 (m, 3H), 3.10-3.30 (m, 1H), 3.40 (d, 2H, J=7 Hz), 3.62 and 3.65 (d, 3H, J=11 Hz), 3.76 (s, 3H), 4.03-4.12 (m, 2H), 4.20 (dq, 2H, J=2, 7 Hz), 4.29 (appt t, 2H, J=8 Hz), 5.12 (s, 2H), 5.18-5.28 (m, 1H), 5.33-5.67 (m, 2H); $^{31}$P (121.4 MHz, CDCl$_3$) δ 30.4, 31.2; MS (m/z) 790.4 [M+Na]$^+$.

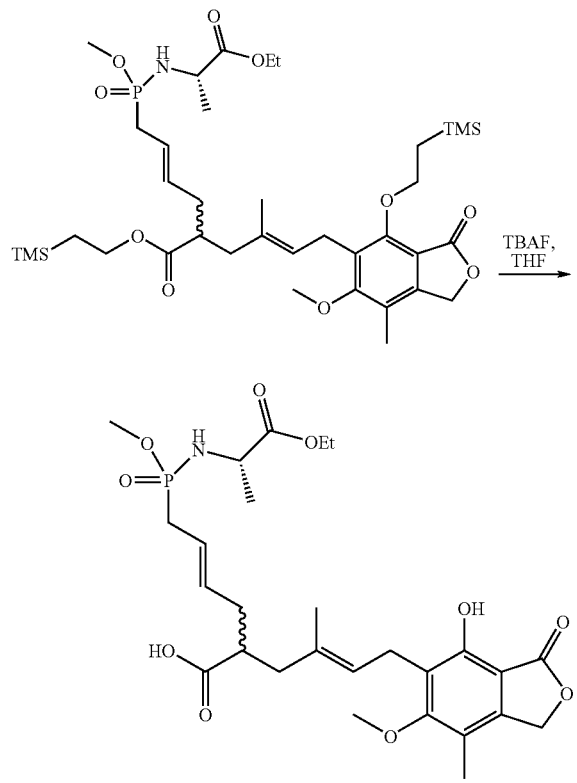

Example 92-AD

2-{4-[(1-Ethoxycarbonyl-ethylamine)-methoxy-phosphoryl]-but-2-enyl}-6-(4-hydroxy-6-methoxy-7-methyl-3-oxo-1,3-dihydro-isobenzofuran-5-yl)-4-methyl-hex-4-enoic acid To a solution of 2-{4-[(1-ethoxycarbonyl-ethylamine)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (7.2 mg, 9.38 mmol) in THF (1 mL) was added TBAF (40 μL, 1M solution in THF) at room temperature. The reaction mixture was stirred for 20 minutes when the starting materials were completely converted to the desired products as observed by LCMS. The reaction mixture was dried in vacuo and re-dissolved in DMF. The product was purified by RP HPLC using a Phenomenex Synergi 5μ Hydro RP 80 A column (50×21.2 mm) with eluents of H$_2$O—CH$_3$CN. The fractions containing the desired product were pooled and further purified on Dowex 50WX8-400 packed on a 4.5 cm×2 cm column to elute the sodium salt at H$_2$O— MeOH (1:1) to provide 3.2 mg of the desired product. $^1$H NMR (300 MHz, CD$_3$OD) δ 1.26 (dd, 3H, J=4, 7 Hz), 1.37 (t, 3H, J=8 Hz), 1.80 (s, 3H), 2.00-2.22 (m, 4H), 2.10 (s, 3H), 2.25-2.60 (m, 3H), 3.37 (d, 2H, J=7 Hz), 3.60 and 3.65 (d, 3H, J=11 Hz), 3.74 (s, 3H), 3.83-3.96 (m, 1H), 4.18 (q, 2H, J=8 Hz), 5.15 (s, 2H), 5.25-5.42 (m, 2H), 5.55-5.69 (m, 1H); $^{31}$P (121.4 MHz, CD$_3$OD) δ 33.8, 34.2; MS (m/z) 568.2 [M+H]$^+$, 590.3 [M+Na]$^+$.

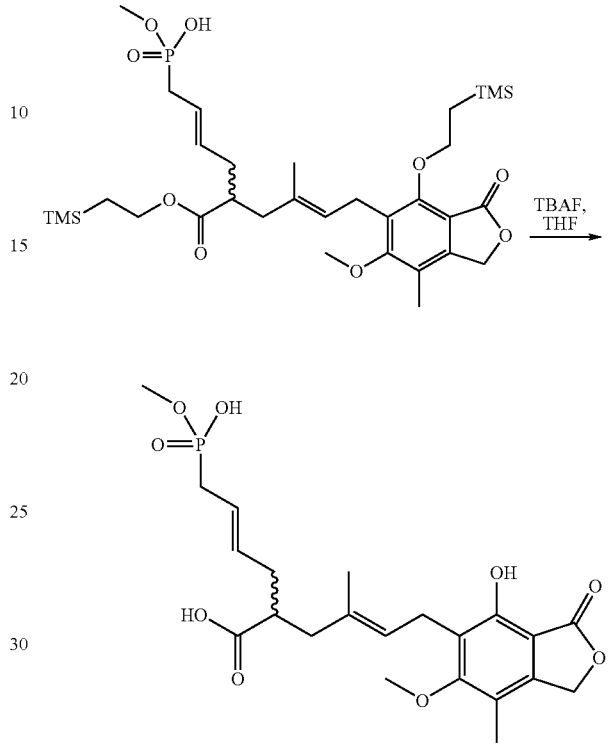

Example 92-AE 6-(4-Hydroxy-6-methoxy-7-methyl-3-oxo-1,3-dihydro-isobenzofuran-5-yl)-2-[4-(hydroxy-methoxy-phosphoryl)-but-2-enyl]-4-methyl-hex-4-enoic acid To a solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanylethyl ester (11 mg, 0.016 mmol) in THF (1 mL) was added TBAF (50 μL, 1M solution in THF) at room temperature. The solution was stirred for 16 hours and concentrated. The solution was dried under reduced pressure and re-suspended in DMF (0.8 mL) and water (0.25 mL). The solution was filtered through Acrodisc (13 mm syringe filter with a 0.45 μm Nylon membrane) and purified by RP HPLC using a Phenomenex Synergi 5μ Hydro RP 80 A column (50×21.2 mm) with eluents of H$_2$O, 0.1% TFA-CH$_3$CN, 0.1% TFA. The product from the column was subjected to ion exchange chromatography (Sodium salt form of Dowex 50WX8-400) using a 2×4.5 cm column eluting with H$_2$O-MeOH (1:1) to provide 7.5 mg of the desired product as an oil. $^1$H NMR (300 MHz, CDCl$_3$) 1.80 (s, 3H), 2.01-2.29 (m, 5H), 2.11 (s, 3H), 2.35 (d, 2H, J=22 Hz), 3.38 (d, 2H, J=7 Hz), 3.53 (d, 3H, J=11 Hz), 3.75 (s, 3H), 5.19 (s, 2H), 5.26 (t, 1H, J=6 Hz), 5.43-5.54 (m, 2H); 3"P (121.4 MHz, CDCl$_3$) δ 23.5; MS (m/z) 469.2 [M+H]$^+$, 491.3 [M+Na]$^+$.

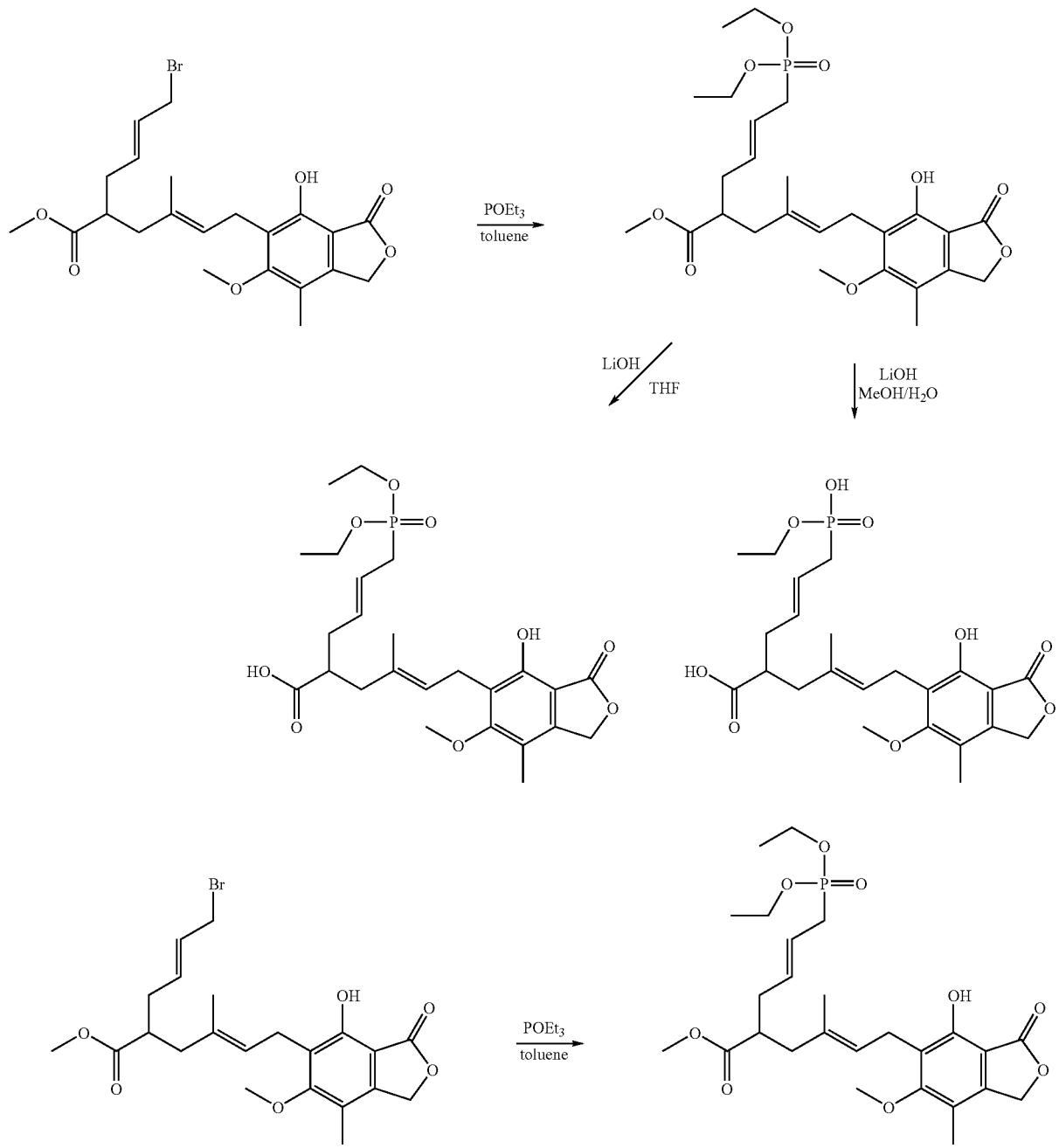

Scheme III

Example 92-AF

2-[4-(Diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester A solution of 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester (140 mg, 0.30 mmol) and triethylphosphite (600 mg, 3.6 mmol) in toluene (30 mL) was stirred at reflux for 20 h. The mixture was concentrated and chromatographed on silica gel eluting with ethyl acetate (60% to 100%)/hexanes, affording 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester as an oil (70 mg, 43%); $^1$H NMR (300 MHz, CDCl$_3$) δ 1.27 (m, 6H), 1.79 (s, 3H), 2.0-2.7 (m, 8H), 3.37 (d, J=6.6 Hz), 3.52 (s, 3H), 3.75 (s, 3H), 4.08 (m, 4H), 5.20 m, 3H), 5.45 (m, 2H).

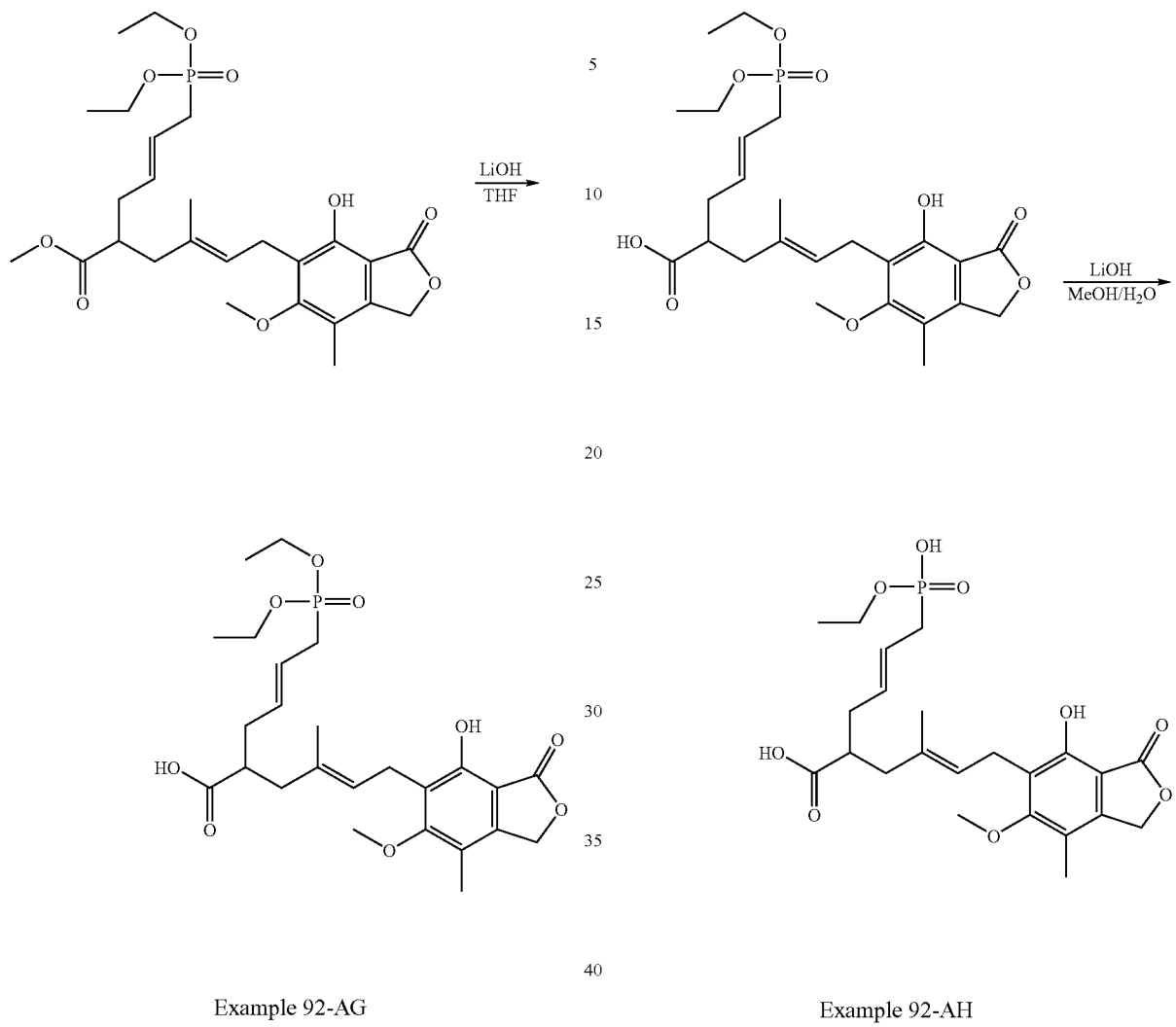

Example 92-AG

2-[4-(Diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid A mixture of 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester (33 mg, 0.063 mmol) and lithium hydroxide (44 mg) in a mixed solvent of THF (6 mL) and water (1 mL) was stirred at room temperature for 6 h. The organic solvent was removed and the residue was partitioned between ethyl acetate and 5% aqueous sodium bicarbonate. The aqueous layer was acidified with 2 N HCl and extracted with ethyl acetate. The ethyl acetate extract was concentrated, affording 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid as an oil (30 mg, 100%); $^1$H NMR (300 MHz, CDCl$_3$) δ 1.27 (m, 6H), 1.79 (s, 3H), 2.0-2.7 (m, 8H), 3.37 (d, J=6.6 Hz), 3.75 (s, 3H), 4.08 m, 4H), 5.19 (s, 2H), 5.25 (m, 1H), 5.44 (m, 1H), 5.55 (m, 1H), 5.45 (m, 2H).

Example 92-AH

2-[4-(Ethoxy-hydroxy-phosphoryl)-but-2-enyl]-6-(4-hydroxy-6-methoxy-7-methyl-3-oxo-1,3-dihydro-isobenzofuran-5-yl)-4-methyl-hex-4-enoic acid A mixture of 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester (25 mg, 0.048 mmol) and lithium hydroxide (200 mg) in a mixed solvent of methanol (3 mL) and water (1 mL) was stirred at 70° C. for 2 h. The organic solvent was removed and then acidified with 2N HCl and extracted with ethyl acetate/acetonitrile. The organic extract was concentrated and the residue was purified by preparative reverse-phase HPLC (acetonitrile and 0.1% aqueous CF$_3$COOH), affording 22-[4-(ethoxy-hydroxy-phosphoryl)-but-2-enyl]-6-(4-hydroxy-6-methoxy-7-methyl-3-oxo-1,3-dihydro-isobenzofuran-5-yl)-4-methyl-hex-4-enoic acid as an oil (15 mg, 89%); $^1$H NMR (300 MHz, CD$_3$OD) δ 1.25 (t, J=6.9 Hz, 3H), 1.81 (s, 3H), 2.1-2.6 (m, 8H), 3.40 (d, J=6.6 Hz, 2H), 3.77 (s, 3H), 3.97 (m, 2H), 5.1-5.3 (m, 3H), 5.67 (brs, 2H).

Example 93

Preparation of Exemplary Compounds of the Present Invention

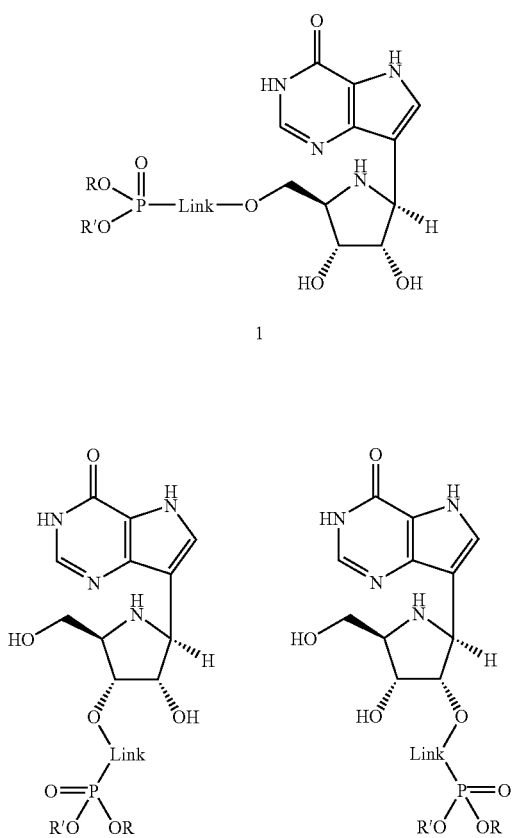

Figure 1

Link is 1-8 atoms in length, with 2-6 atoms preferred

Compounds such as 1 can be made according to the general route outlined in Scheme 1, with an example depicted in Scheme 2.

Scheme 1:

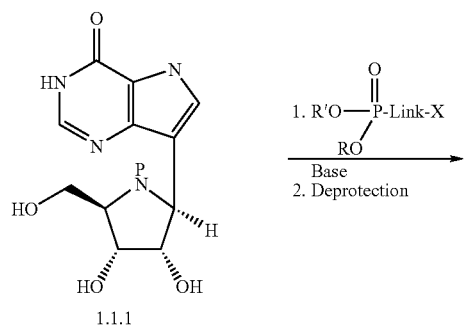

Scheme 2:

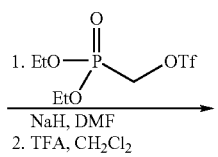

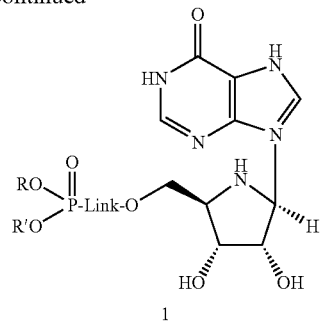

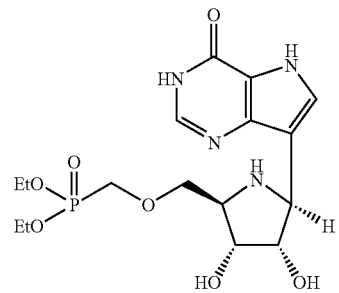

The Boc-protected (1S)-1-(9-deazaguanin-9-yl)-1,4-dideoxy-1,4-imino-D-ribitol, compound 1.1.1, is prepared by stirring the (1S)-1-(9-deazaguanin-9-yl)-1,4-dideoxy-1,4-imino-D-ribitol (WO 9,919,338 and Evans, G. B. et al., Tetrahedron, 2000, 56, 3053, also reported in Evans, G. B. et al., J. Med. Chem. 2003, 46, 3412) with BOC anhydride as described in Greene, T., Protective groups in organic synthesis, Wiley-Interscience, 1999. Compound 1.1.1 is then treated in a solvent such as tetrahydrofuran or dimethylformamide with a base such as sodium hydride. When bubbling ceases, diethyl phosphonomethyltriflate (prepared according to Tetrahedron Lett., 1986, 27, 1477) is added, yielding the desired phosphonate 1 after deprotection of the BOC group using trifluoroacetic acid (TFA).

Compounds such as 2 and 3 can be made according to the general route outlined in Scheme 3, with an example depicted in Scheme 4.

Scheme 3:

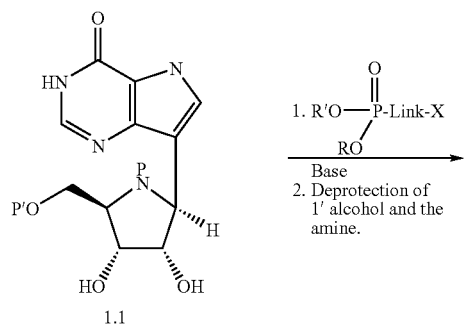

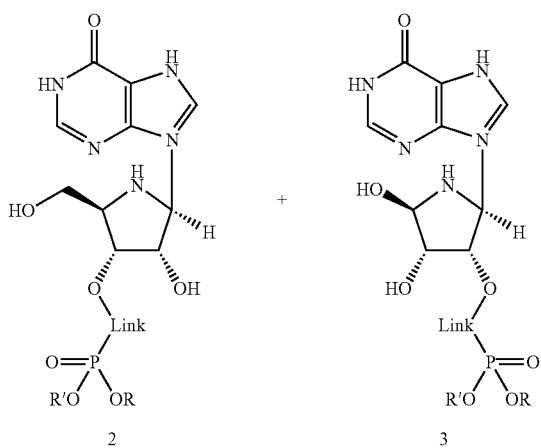

Scheme 4:

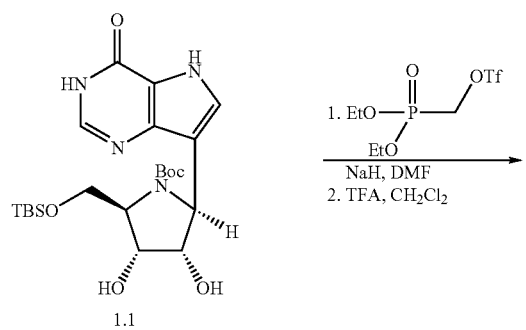

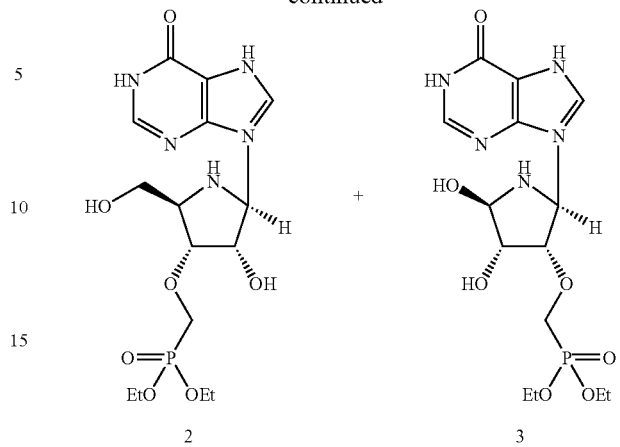

The Boc-protected (1S)-1-(9-deazaguanin-9-yl)-1,4-dideoxy-1,4-imino-D-ribitol, compound 1.1, is prepared by stirring the (1S)-1-(9-deazaguanin-9-yl)-1,4-dideoxy-1,4-imino-D-ribitol (WO 9,919,338 and Evans, G. B. et al., *Tetrahedron*, 2000, 56, 3053, also reported in Evans, G. B. et al., *J. Med. Chem.* 2003, 46, 3412) with BOC anhydride as described in Greene, T., Protective groups in organic synthesis, Wiley-Interscience, 1999. Subsequent protection of the primary alcohol using a TBS group can be achieved using TBSCl and imidazole in solvents such as $CH_2Cl_2$ as described in Greene, T. Protective groups in organic synthesis, Wiley-Interscience, 1999 to provide compound 1.1. Compound 1.1 is then treated in a solvent such as tetrahydrofuran or dimethylformamide with a base such as sodium hydride. When bubbling ceases, diethyl phosphonomethyltriflate (prepared according to *Tetrahedron Lett.*, 1986, 27, 1477) is added, yielding a mixture of the desired phosphonate diester 2 and 3 after deprotection of the BOC group using trifluoroacetic acid (TFA). Compounds 2 and 3 can be also prepared via a more complicated 2' OH protected analog of 1.1 followed by alkylation using the diethyl phosphonomethyltriflate to provide compound 2 exclusively. Compound 3 can also be prepared by installation of a different protecting group at the 3' OH position, followed by deprotection of 2' OH and alkylation with diethyl phosphonomethyltriflate at the 2' center followed by global deprotection.

Example 94

Preparation of Exemplary Compounds of the Present Invention

IV. Parent Molecule:

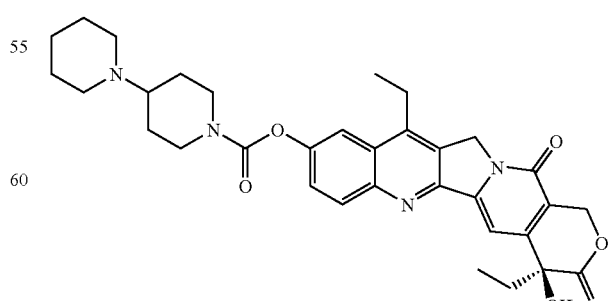

Camptosar

General Target Structures:

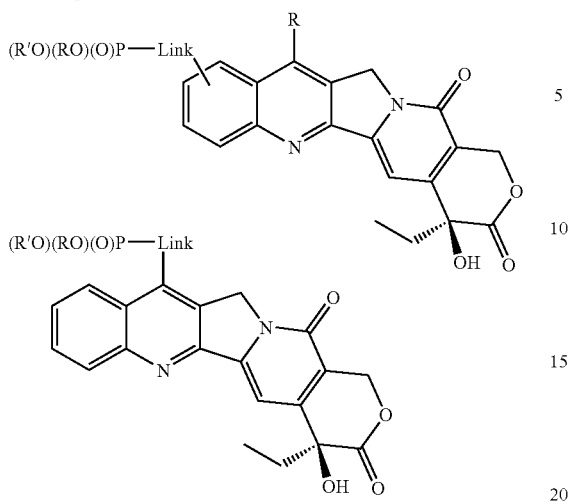

Linker is 1-8 atoms in length, with 2-6 atoms preferred

A synthetic scheme towards a specific target I is outlined below:

Scheme 1

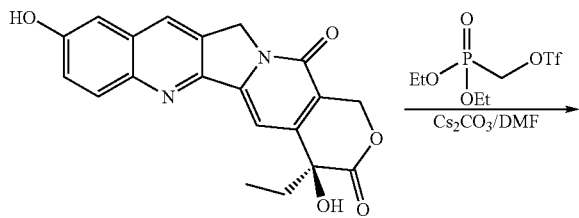

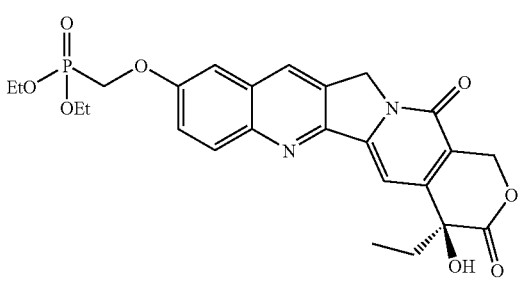

Target I

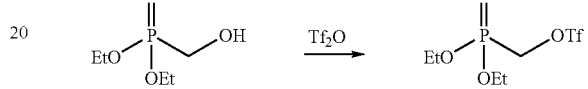

Recommended procedure for O-alkylation: mix the phenol and $Cs_2CO_3$ (ca. 1:1.2) in DMF and stir well for 30 min at 0° C. Add the triflate (1.2 eq.). The reaction should be complete within an hour.

Experimental for the trifluoromethanesulfonyloxymethylphosphonate will be provided separately.

Additional Compounds: The following target II will be prepared after an initial biological evaluation of the target I.

Scheme 2

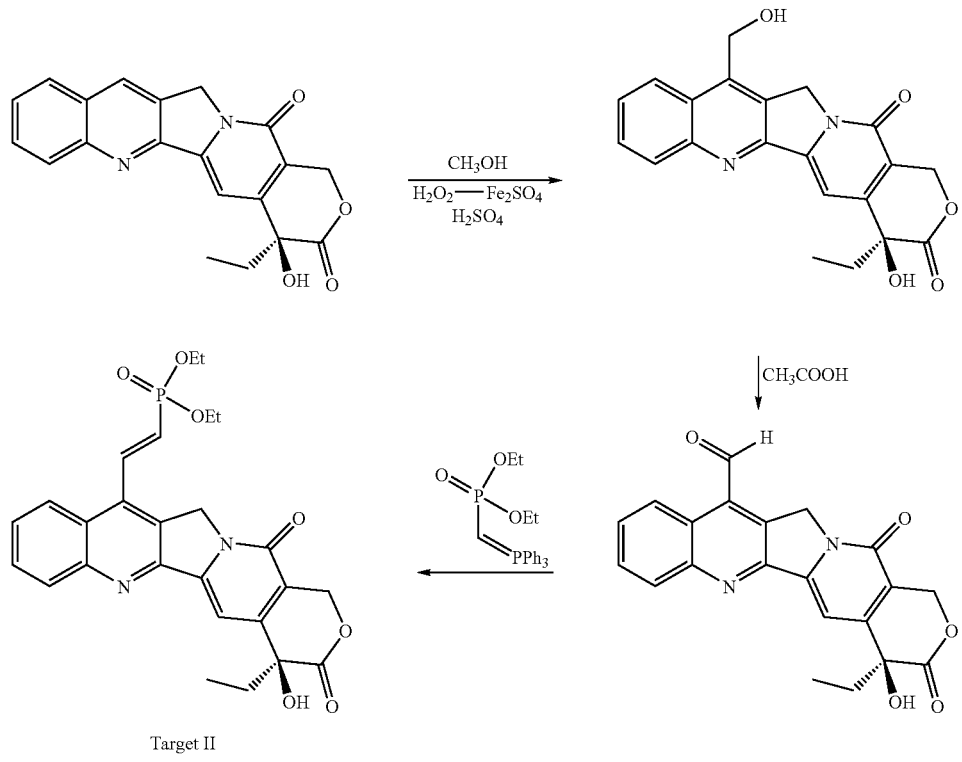

Target II

Reference for camptothecin-7-aldehyde: *Chem. Pharm. Bull.* 1991, 39, 2574. Reference for reactions of Wittig ylides with the camptothecin aldehyde: *J. Med. Chem.* 2000, 43, 3963.

Example 95

Preparation of Exemplary Compounds of the Present Invention

V. Parent Molecule:

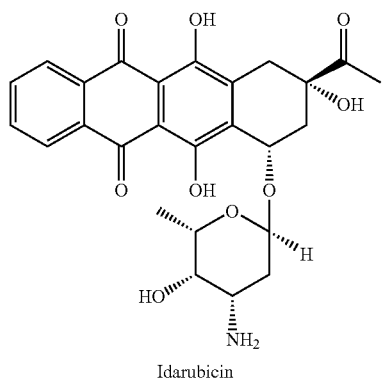

Idarubicin

General Target Structures:

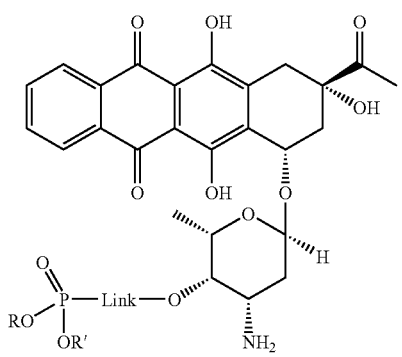

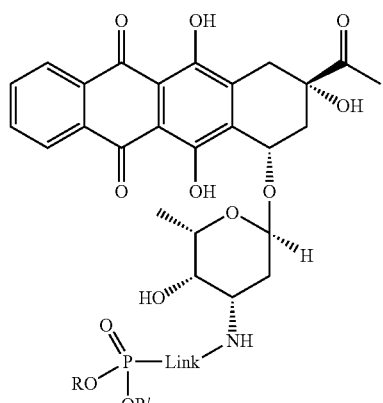

Links is 1-8 atoms in length, with 2-6 atoms preferred

A synthetic scheme towards a specific target I is outlined below:

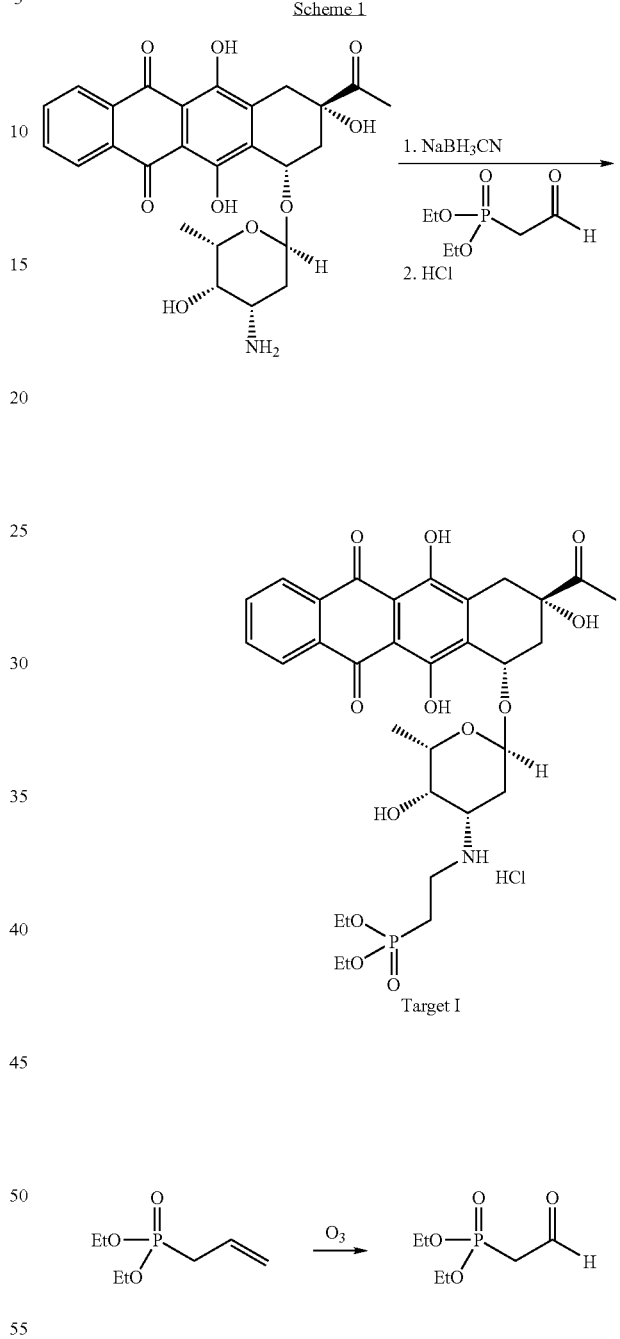

Reference of reductive amination of anthracyclines: *J. Med. Chem.* 1998, 41, 965.

Experimental for the aldehyde intermediate from the allyl phosphonate will be provided.

Additional Compounds: The following two targets II and III will be prepared after an initial biological evaluation of the target I.

913     914
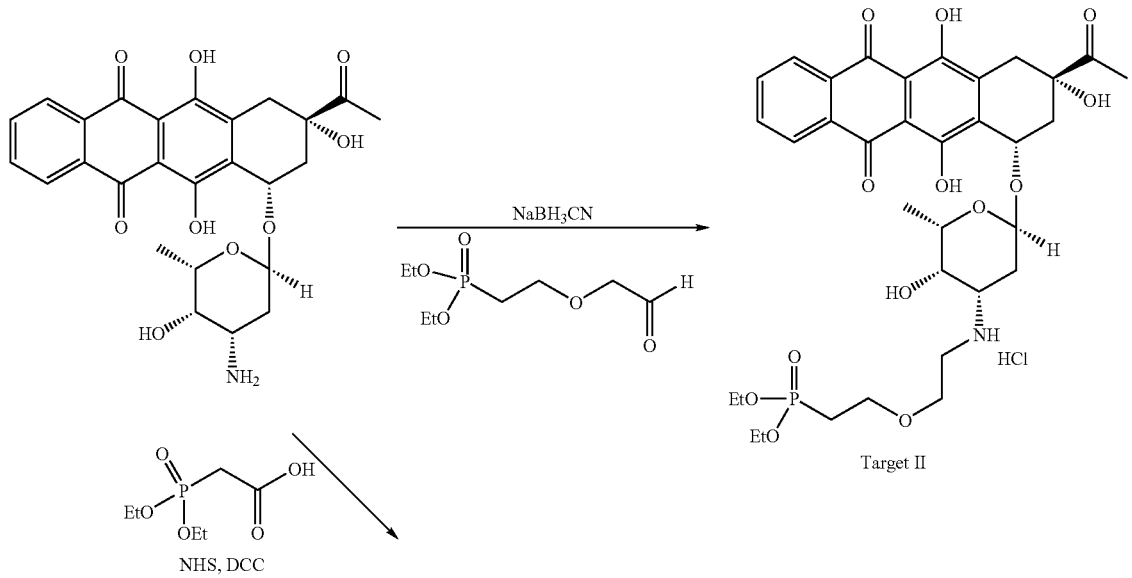
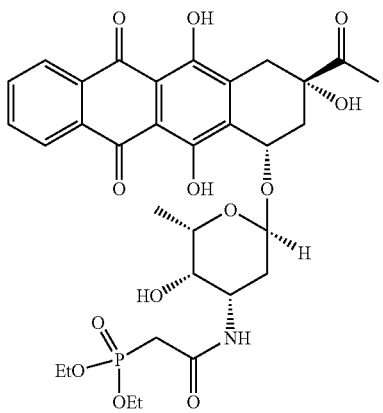
Target III
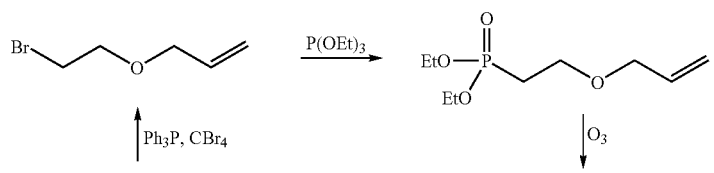
Reference for N-acylation of anthracyclines: *J. Med. Chem.* 1980, 23, 1166

Example 96
Preparation of Exemplary Compounds of the Present Invention
Parent Molecule:
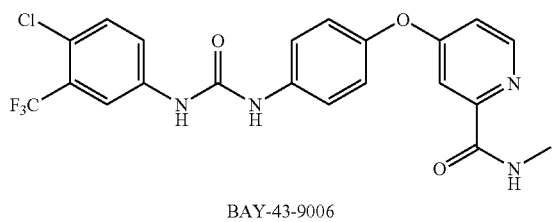
BAY-43-9006
Target Classes:
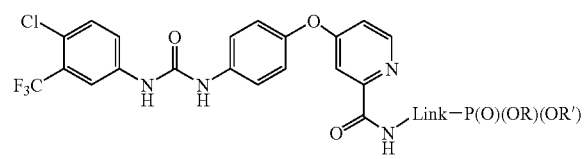
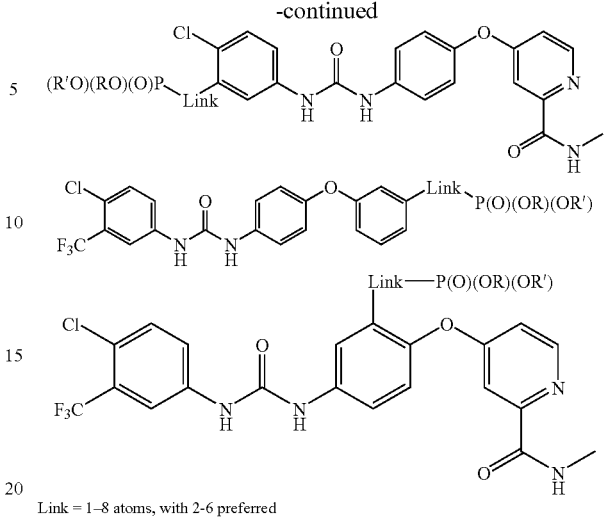
Link = 1–8 atoms, with 2–6 preferred
A synthetic scheme towards specific targets I and II is outlined below.
Scheme 1
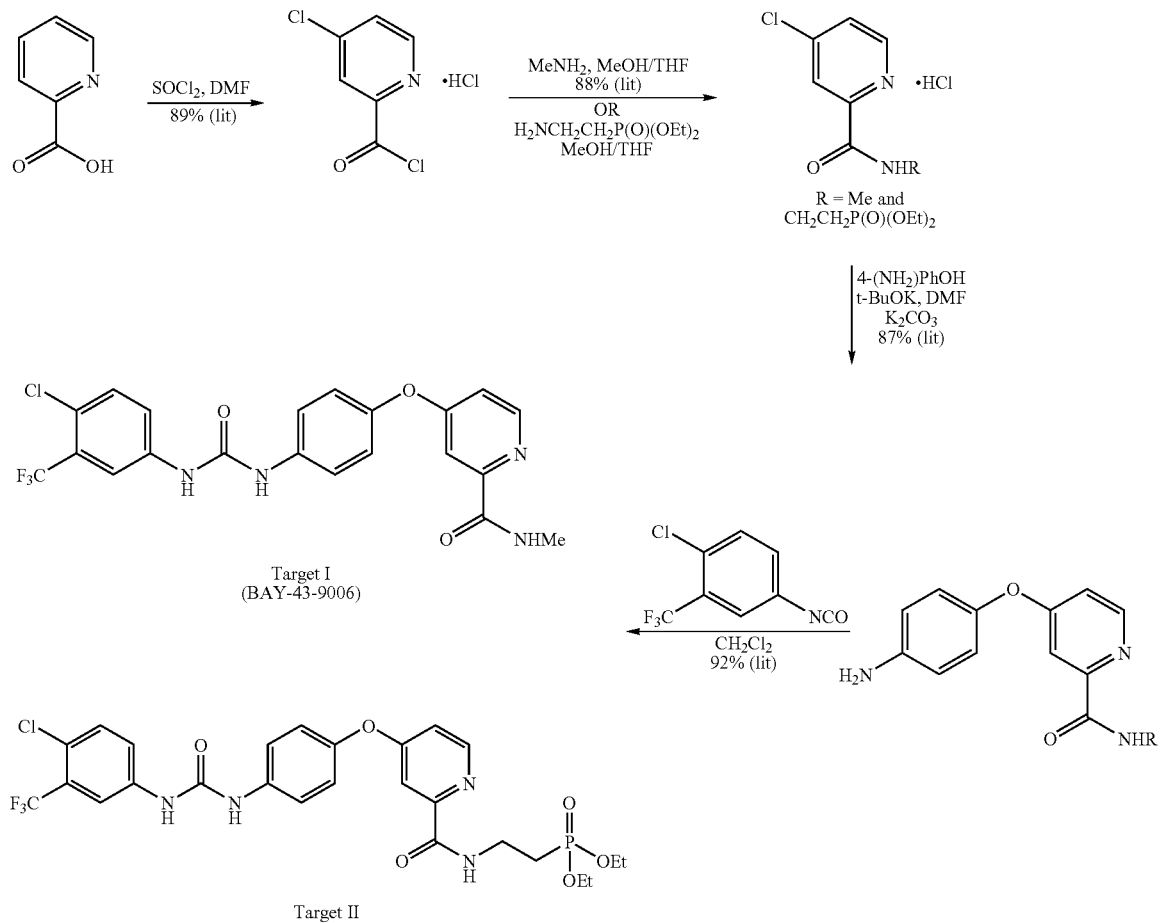

Reference for synthesis of target I: Org. Pro. Res. Dev. web publication will be provided.

Additional Compounds: The following targets III and IV will be prepared after an initial biological evaluation of the targets I and II.

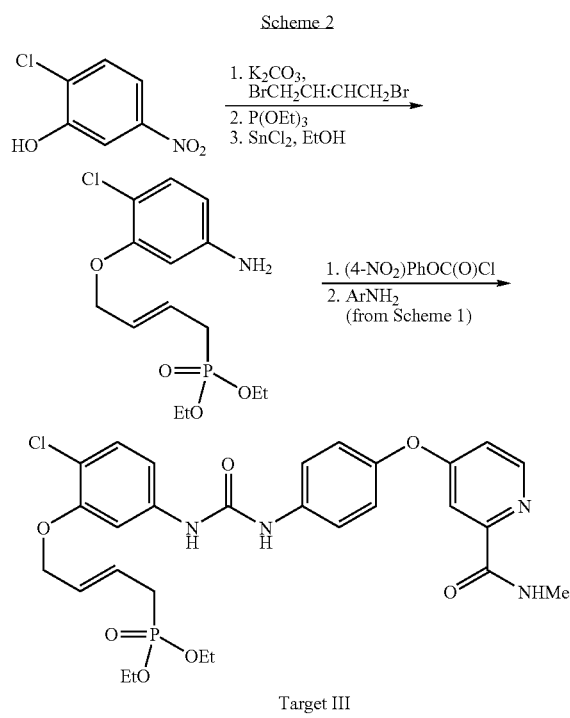

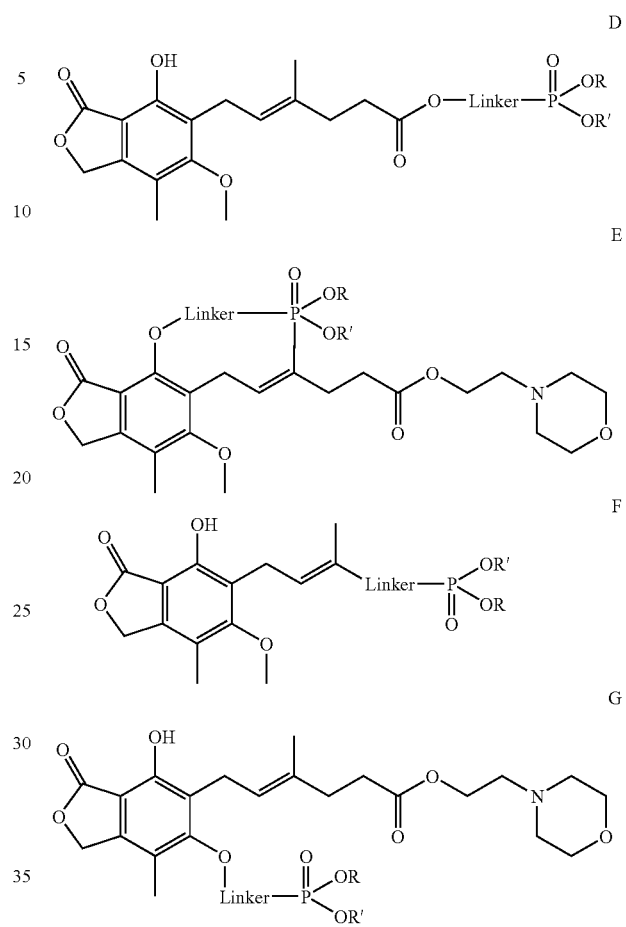

For example, three regions of mycophenolate mofetil can be utilized for the attachment of the phosphonate prodrug as demonstrated by compounds D, E, and G shown above. Also, the carboxylic acid can be replaced with a phosphonic acid as in compound F.

Example 201

Preparation of Representative Compounds of Formula 204

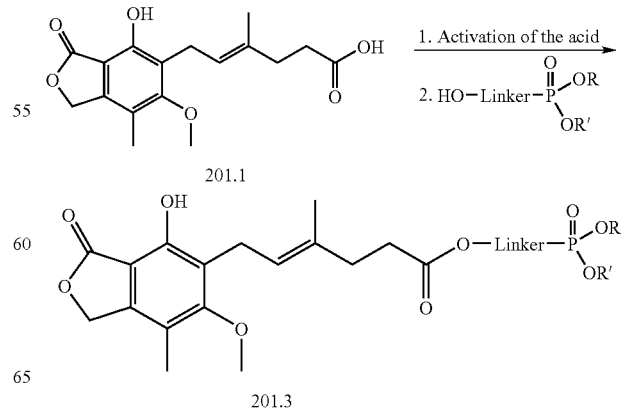

Mycophenolate

Representative compounds of the invention having the following formulae can be prepared as described in Examples 201-204.

Representative compounds of the invention can be prepared as illustrated above. The morpholino ethyl moiety can serve as a prodrug functionality to improve bioavailability and can be replaced with the phosphonate prodrug handle as shown above. Mycophenolic acid is commercially available, e.g., from Sigma Chemical Company, St. Louis, Mo. Activation of the carboxylic acid 201.1 in the presence of the free phenol, followed by addition of an alcohol carrying the phosphonate group, results in the formation of the desired product 201.3 (U.S. Pat. No. 4,786,637). A specific compound of the invention can be prepared as follows.

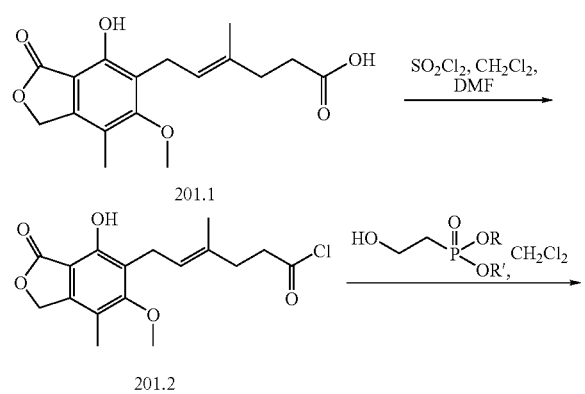

-continued

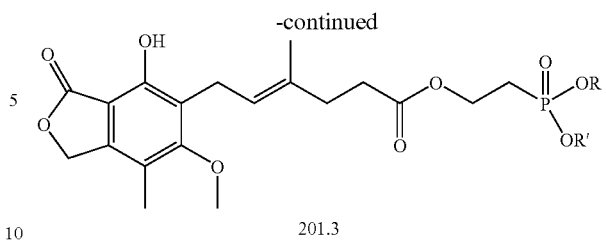

201.3

Mycophenolic acid 201.1 is dissolved in dichloromethane. Thionyl chloride is added followed by a catalytic amount of DMF. The reaction mixture is stirred at room temperature for 3 hours, after which the volatile components are removed under vacuum. The phosphonate-alcohol is dissolved in dichloromethane and chilled to about 4° C. on an ice bath. The mycophenolic acid chloride 201.2 is dissolved in dichloromethane and added to the chilled solution. After stirring for 90 minutes at about 4° C., the reaction mixture is washed with water and then with aqueous sodium bicarbonate. The organic solution is dried and evaporated to yield the phosphonate 201.3.

Example 202

Preparation of Representative Compounds of Formula 207

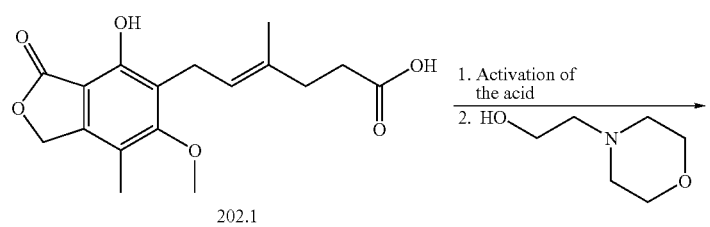

202.1

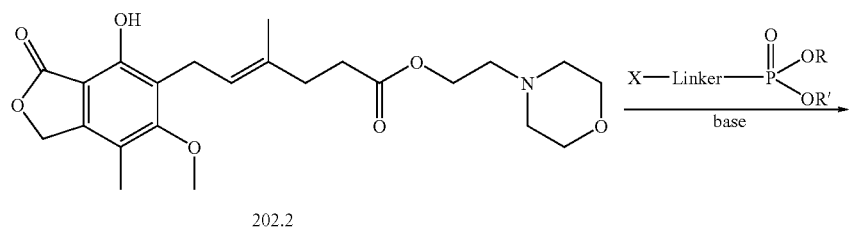

202.2

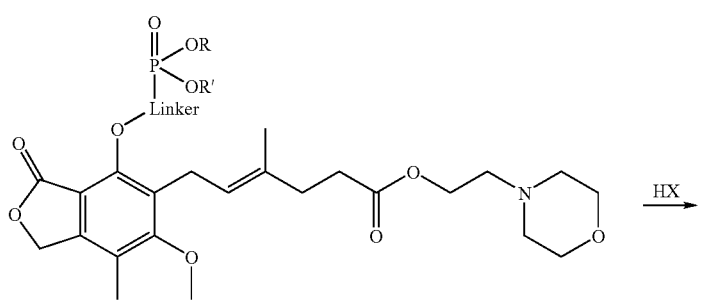

202.3

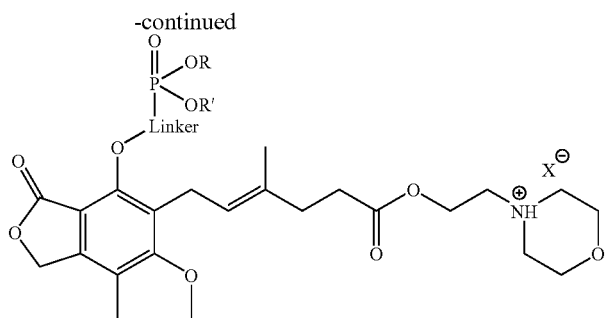

202.4

Representative compounds of the invention can be prepared as illustrated above. The C-4 phenol position provides a reactive handle for further analogs as illustrated above. Once the carboxylic acid of 202.1 is blocked by morpholino ethyl, such as in compound 202.2 the phenol can be alkylated under basic conditions. Bases such as pyridine, potassium carbonate, or triethylamine are utilized. Leaving groups such as trifluoromethylsulfonate, mesylate, bromide, or iodide are attached to the phosphonate prodrug subunit and reacted, in the presence of base, with compound 202.2. Compound 2023 can either be used directly, or in the form of a salt, compound 202.4. Among the large number of salts that can be prepared, chloride and bisulfate salts are one particular embodiment of the invention. A specific compound of the invention can be prepared as follows.

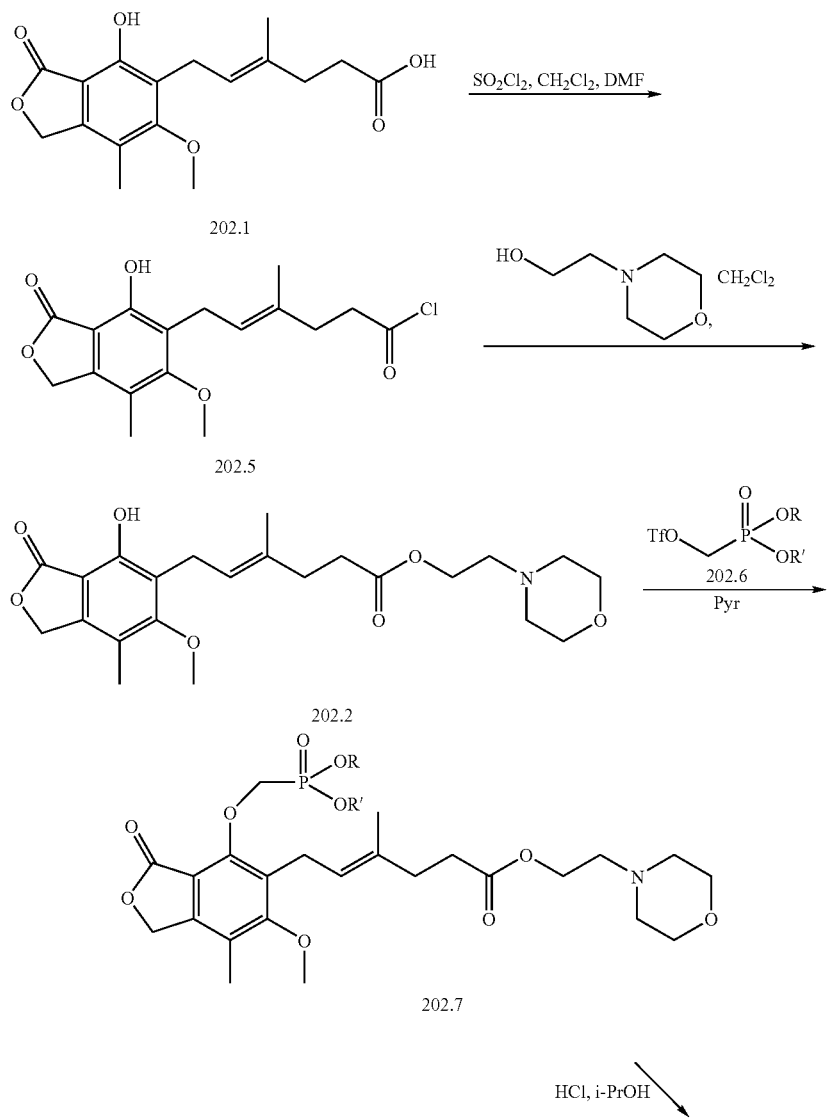

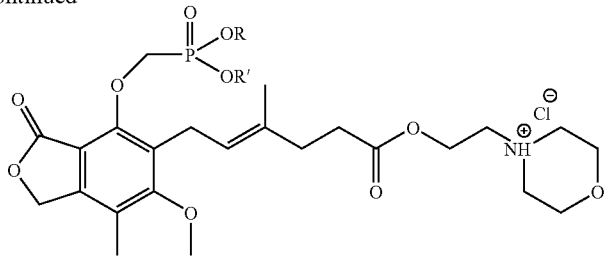

202.8

Compound 202.5 is prepared similar to compound 201.2 (described in Example 201). A solution of morpholino ethanol in dichloromethane is cooled to about 4° C. The mycophenolic acid chloride 202.5 is dissolved in dichloromethane and added to the cooled solution. Stirring this solution for about 90 minutes gives compound 202.2. The reaction mixture is washed with water and dried with sodium sulfate. Removal of the solvent provides isolated compound 202.2. Alkylation at the phenolic position of 202.2 is achieved by suspending the compound in pyridine. Triflate 202.6 is added to the solution and the mixture is stirred at room temperature for about 90 minutes. The reaction mixture is poured into water and the product is extracted with ethyl acetate. Removal of the organic layer provides compound 202.7. Hydrochloride salt of 202.7 can optionally be prepared. Compound 202.7 is dissolved in isopropanol and the solution is added to a mixture of hydrogen chloride in isopropanol. The hydrochloride salt 202.8 is collected by filtration and dried under vacuum.

Example 203

Preparation of Representative Compounds of Formula 205

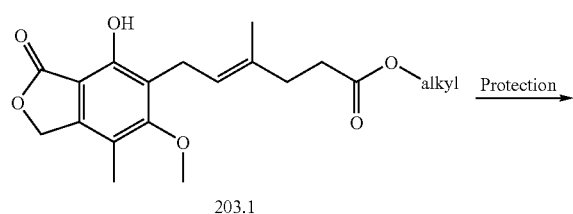

203.1

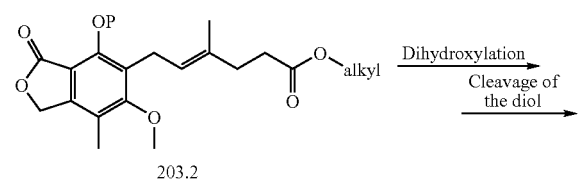

203.2

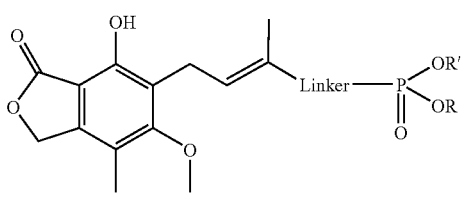

203.3

203.5

203.6

Representative compounds of the invention can be prepared as illustrated above. The carboxylic acid of mycophenolic acid can be replaced with a phosphonic acid that may also serves as a prodrug handle. In order to remove the carboxylic acid containing side chain, the acid chloride 202.5 (prepared in Example 202) is converted to ester 203.1. Protection of the phenol with a silyl group, followed by dihydroxylation and cleavage of the diol generates aldehyde 203.3 (Pankiewicz, et al., *J. Med. Chem.*, 2002, 45, 703), (Patterson et al., U.S. Pat. No. 5,444,072) (Example 20). A Wittig reaction with ylide 203.4 carrying an appropriately protected phosphonate provides the desired compound 203.5. Final deprotection yields compound 203.6. A specific compound of the invention can be prepared as follows.

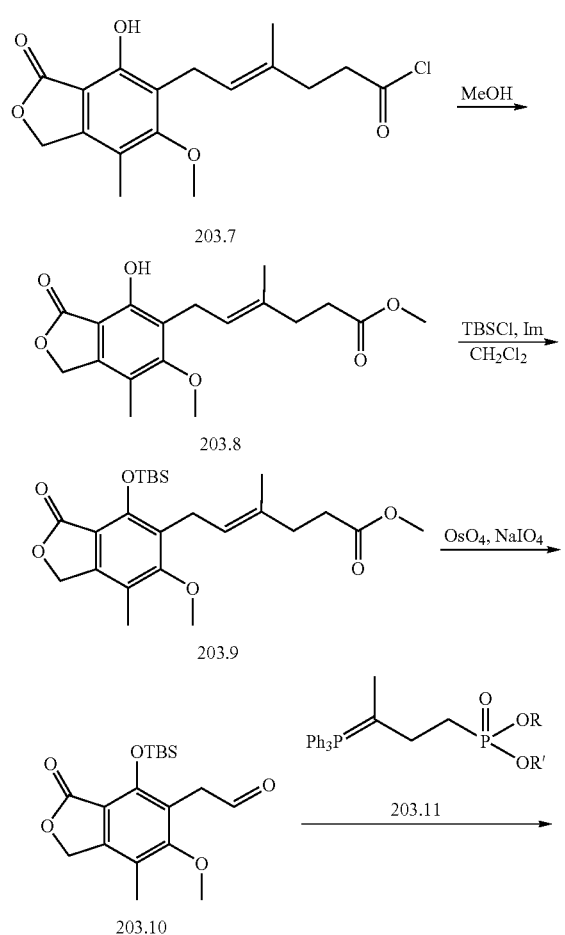
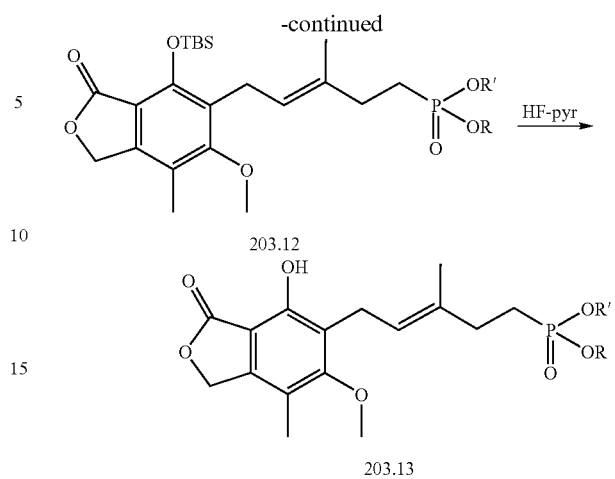

Mycophenolate ester 203.8 can simply be prepared by stirring the acid chloride 203.7 with MeOH. Then, the phenol position of mycophenolate ester is protected by a silyl group such as TBS to provide compound 203.9. Once the phenol position is protected, dihydroxylation using osmium tetraoxide followed by periodinate cleavage provides aldehyde 203.10. Aldehyde 203.10 and excess of the ylide 203.11 are heated in benzene at reflux for about 24 hours. The reaction mixture is concentrated and the residue is purified by column chromatography to provide olefin 203.12 (Pankiewics et al., *J. Med. Chem.*, 2002, 45, 703). A final deprotection using HF-pyridine yields the final product 203.13.

Example 204

Preparation of Representative Compounds of Formula 208

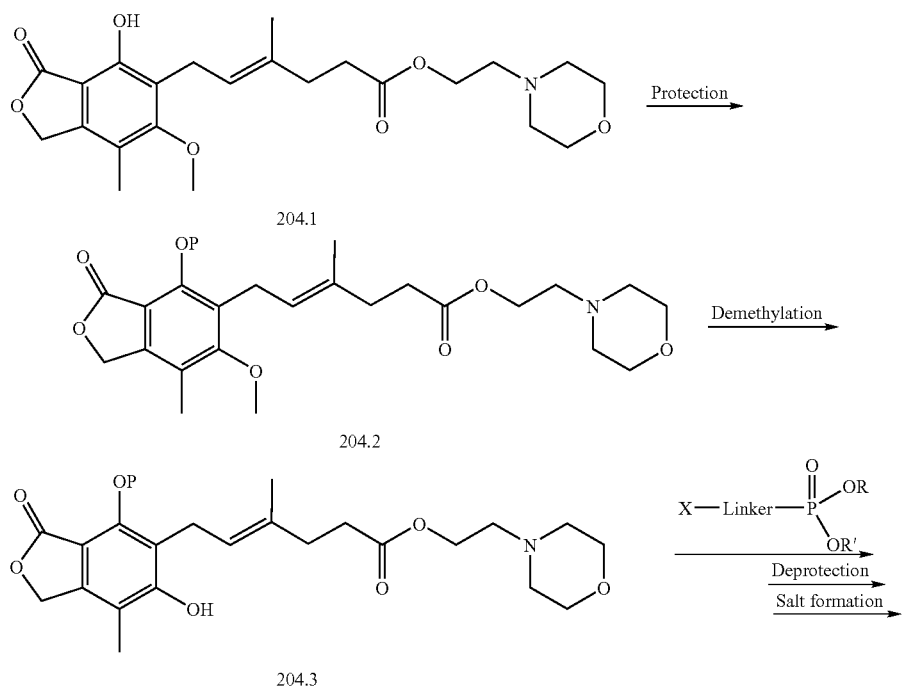

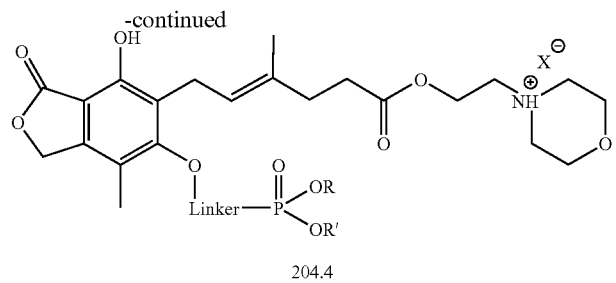

204.4

Representative compounds of the invention can be prepared as illustrated above. Another attachement point of the compound can be unmasked after demethylation of mycophenolate ester 204.2 as illustrated above. For this purpose, the 4-OH needs to be masked with a protecting group (P) such as a silyl group. Once the 6-MeO is demethylated and alkylated, the protecting group at position 4 is removed to reveal the final product 204.4. The morphonyl ethanol group is installed early and carried through the alkylation steps. A different protecting group may be installed initially and removed later. In such the latter type of synthesis, the last step is the formation of the morpholinoethyl ester prodrug. A specific compound of the invention can be prepared as described below.

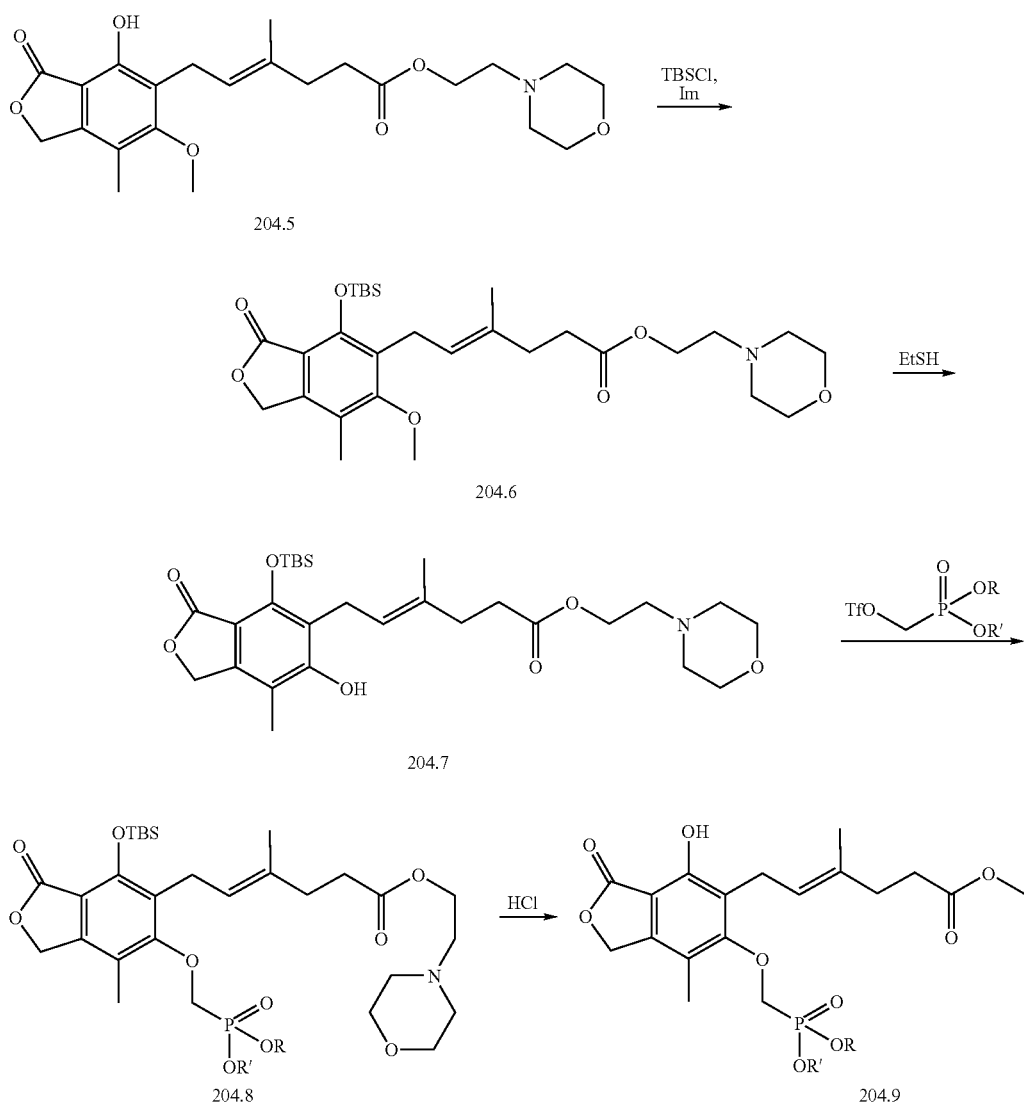

Phenol 204.5 is protected with TBS group in $CH_2Cl_2$ using imidazole as base to yield 204.6. Demethylation is performed using thiolate nucleophiles to generate compound 204.7. A variety of other methods are also available in literature as described in *Protective Groups in Organic Synthesis* by Greene and Wuts. Alklation of the 6-OH using a triflate of the phosphonate proceeds well using $K_2CO_3$ or TEA to provide 204.8. Final deprotection to remove the TBS group provides product 204.9.

Example 251

Preparation of Representative Compounds of the Invention

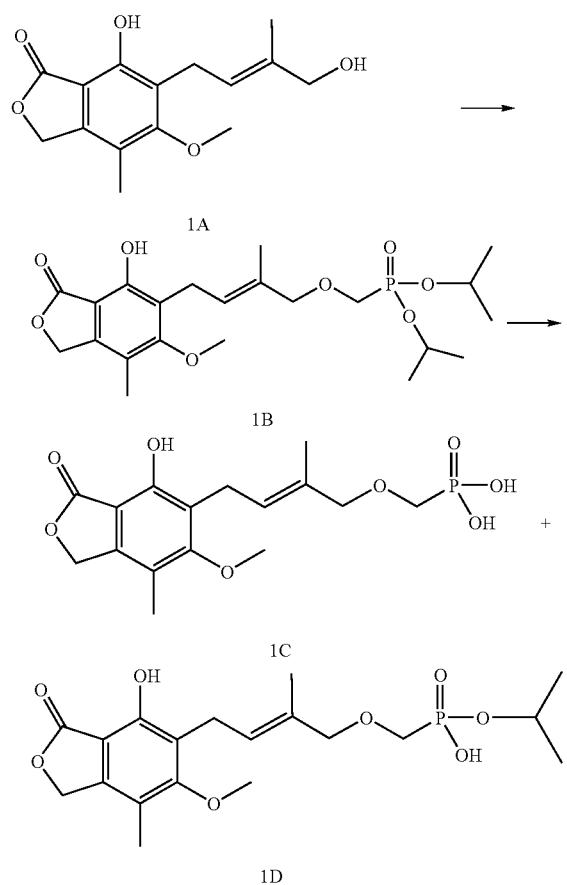

Representative compounds of the invention can be prepared as illustrated above.

[4-(4-Hydroxy-6-methoxy-7-methyl-3-oxo-1,3-dihydro-isobenzofuran-5-yl)-2-methyl-but-2-enyloxymethyl]-phosphonic acid diisopropyl ester A mixture of 7-hydroxy-6-(4-hydroxy-3-methyl-but-2-enyl)-5-methoxy-4-methyl-3H-isobenzofuran-1-one 1A (50 mg, 0.18 mmol, Pankiewicz et al., *J. Med. Chem.*, 45, 703), diisopropyl bromomethylphosphonate (93 mg, 0.36 mmol) and lithium t-butoxide (1M in THF, 0.54 mL) in DMF (3 mL) was heated at 70° C. for 5 hours. The reaction was quenched with 1N HCl. The mixture was poured into 5% aqueous lithium chloride, extracted with ethyl acetate, and concentrated. The residue was purified by chromatography on silica gel, affording [4-(4-hydroxy-6-methoxy-7-methyl-3-oxo-1,3-dihydro-isobenzofuran-5-yl)-2-methyl-but-2-enyloxymethyl]-phosphonic acid diisopropyl ester 1B (25 mg, 32%); $^1$H NMR (300 MHz, $CDCl_3$) δ1.25 (m, 12H), 1.79 (s, 3H), 2.05 (s, 3H), 3.37 (d, J=6.6 Hz, 2H), 3.58 (d, 2H), 3.77 (s, 3H), 3.97 (m, 2H), 4.68 (m, 2H), 5.19 (s, 2H), 5.45 (t, J=6.6 Hz, 1H), 7.83 (s, 1H) ppm.

[4-(4-Hydroxy-6-methoxy-7-methyl-3-oxo-1,3-dihydro-isobenzofuran-5-yl)-2-methyl-but-2-enyloxymethyl]-phosphonic acid and [4-(4-Hydroxy-6-methoxy-7-methyl-3-oxo-1,3-dihydro-isobenzofuran-5-yl)-2-methyl-but-2-enyloxymethyl]-phosphonic acid monoisopropyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid diisopropyl ester 1B (25 mg, 0.055 mmol) and 2,6-lutidine (0.18 mL, 1.65 mmol) in acetonitrile was added trimethylsilyl bromide (0.126 mL, 1.1 mmol) at 0° C. The mixture was allowed to warm to room temperature and stirred for 4 hours. The reaction was quenched with methanol at 0° C., and the resulting mixture was concentrated. The residue was purified by preparative reverse-phase HPLC to afford, after removal of the solvent, [4-(4-hydroxy-6-methoxy-7-methyl-3-oxo-1,3-dihydro-isobenzofuran-5-yl)-2-methyl-but-2-enyloxymethyl]-phosphonic acid 1C as an oil (17 mg, 83%); $^1$H NMR (300 MHz, $CD_3OD$) δ 1.81 (s, 3H), 2.06 (s, 3H), 3.40 (d, J=6.6 Hz, 2H), 3.50 (d, 2H), 3.77 (s, 3H), 3.97 (s, 2H), 5.20 (s, 2H), 5.47 (t, J=6.6 Hz, 1H) and [4-(4-hydroxy-6-methoxy-7-methyl-3-oxo-1,3-dihydro-isobenzofuran-5-yl)-2-methyl-but-2-enyloxymethyl]-phosphonic acid monoisopropyl ester 1D as an oil (2 mg, 7%); $^1$H NMR (300 MHz, $CD_3OD$) δ 1.23 (d, 6H), 1.81 (s, 3H), 2.08 (s, 3H), 3.40 (d, J=6.6 Hz, 2H), 3.50 (d, 2H), 3.77 (s, 3H), 3.90 (s, 2H), 4.50 (m, 1H), 5.20 (s, 2H), 5.47 (t, J=6.6 Hz, 1H) ppm.

Example 252

Preparation of Representative Compounds of the Invention

Representative compounds of the invention can be prepared as illustrated below.

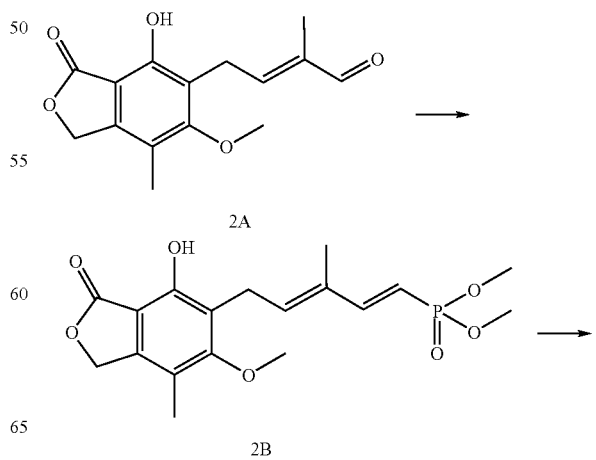

-continued

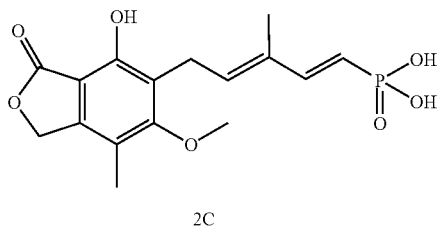

2C

[5-(4-Hydroxy-6-methoxy-7-methyl-3-oxo-1,3-dihydro-isobenzofuran-5-yl)-3-methyl-penta-1,3-dienyl]-phosphonic acid dimethyl ester To a solution of tetramethylmethylene diphosphonate (102 mg, 0.44 mmol) in THF (2.5 mL) was added a THF solution of sodium bis(trimethysilyl)amide (1.0 M, 0.44 mL). After stirring for 30 minutes, a solution of 4-(4-hydroxy-6-methoxy-7-methyl-3-oxo-1,3-dihydro-isobenzofuran-5-yl)-2-methyl-but-2-enal 2A (30 mg, 0.11 mmol, Pankiewicz et al., *J. Med. Chem.*, 45, 703) in THF (2.5 mL) was added, and stirring was continued for an additional 15 minutes. The reaction was quenched with saturated aqueous ammonium chloride. The mixture was extracted with ethyl acetate. After evaporation of solvent, the residue was purified by chromatography on silica gel eluting with ethyl acetate (50% to 100%)/hexanes, affording [5-(4-hydroxy-6-methoxy-7-methyl-3-oxo-1,3-dihydro-isobenzofuran-5-yl)-3-methyl-penta-1,3-dienyl]-phosphonic acid dimethyl ester 2B (30 mg, 71%) as an oil; $^1$H NMR (300 MHz, CDCl$_3$) δ 1.80 (s, 3H), 2.04 (s, 3H), 3.45 (d, J=6.6 Hz, 2H), 3.76 (s, 3H), 3.88 (d, 6H), 5.20 (s, 3H), 5.55 (m, 1H), 5.95 (m, 1H), 7.05 (m, 1H), 7.65 (s, 1H) ppm.

[5-(4-Hydroxy-6-methoxy-7-methyl-3-oxo-1,3-dihydro-isobenzofuran-5-yl)-3-methyl-penta-1,3-dienyl]-phosphonic acid To a solution of [5-(4-hydroxy-6-methoxy-7-methyl-3-oxo-1,3-dihydro-isobenzofuran-5-yl)-3-methyl-penta-1,3-dienyl]-phosphonic acid dimethyl ester 2B (22 mg, 0.057 mmol) and 2,6-lutidine (0.22 mL, 1.71 mmol) in acetonitrile was added trimethylsilyl bromide (0.183 mL, 1.71 mmol) at 0° C. The mixture was allowed to warm to room temperature and stirred for 1 hour. The reaction was quenched with methanol at 0° C., and the resulting mixture was concentrated. The residue was purified by preparative reverse-phase HPLC to afford, after removal of the solvent, [5-(4-hydroxy-6-methoxy-7-methyl-3-oxo-1,3-dihydro-isobenzofuran-5-yl)-3-methyl-penta-1,3-dienyl]-phosphonic acid 2C as a solid (13 mg, 65%); $^1$H NMR (300 MHz, CD$_3$OD) δ 1.91 (s, 3H), 2.10 (s, 3H), 3.55 (d, J=6.6 Hz, 2H), 3.75 (s, 3H), 5.2 (s, 2H), 5.6-5.8 (m, 2H), 6.9 (m, 1H) ppm.

Example 253

Preparation of Representative Compounds of the Invention

Representative compounds of the invention can be prepared as illustrated below.

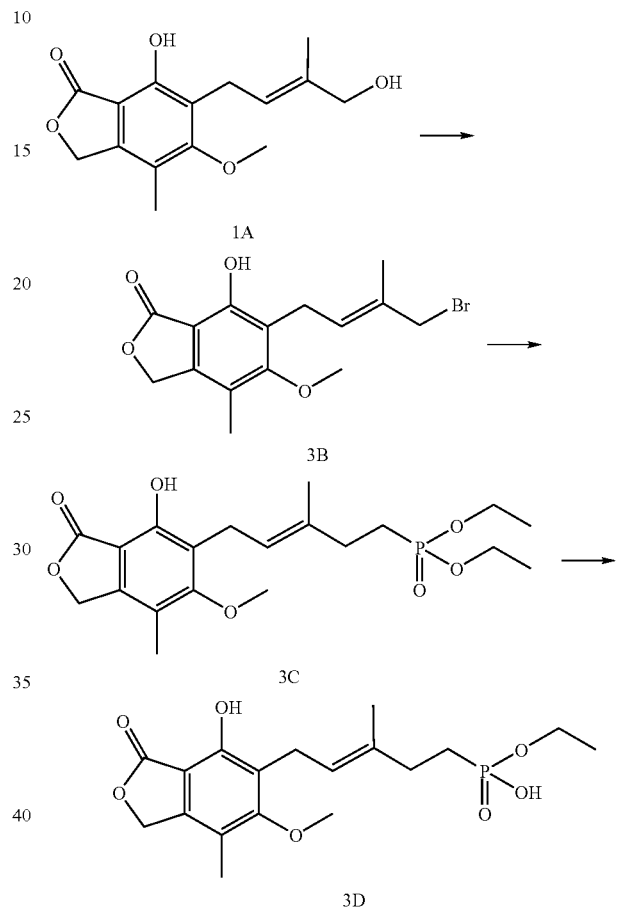

6-(4-Bromo-3-methyl-but-2-enyl)-7-hydroxy-5-methoxy-4-methyl-3H-isobenzofuran-1-one Polymer-supported triphenylphosphine (3 mmol/g, 0.5 g) was soaked in dichloromethane (10 mL) for 1 hour 7-Hydroxy-6-(4-hydroxy-3-methyl-but-2-enyl)-5-methoxy-4-methyl-3H-isobenzofuran-1-one 1A (100 mg, 0.36 mmol) and carbon tetrabromide (143 mg, 0.43 mmol) were sequentially added and the mixture was shaken for 1 hour at room temperature. More carbon tetrabromide (143 mg, 0.43 mmol) was added and the mixture was shaken further for 1 hour. The mixture was filtered and the filtrate was concentrated. The residue was chromatographed on silica gel (0% to 60% ethyl acetate/hexanes) to afford 6-(4-bromo-3-methyl-but-2-enyl)-7-hydroxy-5-methoxy-4-methyl-3H-isobenzofuran-1-one 3B as an oil (52 mg, 42%); $^1$H NMR (300 MHz, CDCl$_3$) δ 1.95 (s, 3H), 2.16 (s, 3H), 3.44 (d, J=7.2 Hz, 2H), 3.78 (s, 3H), 3.98 (s, 2H), 5.21 (s, 2H), 5.68 (t, J=7.2 Hz, 1H), 7.71 (brs, 1H) ppm.

[5-(4-Hydroxy-6-methoxy-7-methyl-3-oxo-1,3-dihydro-isobenzofuran-5-yl)-3-methyl-pent-3-enyl]-phosphonic acid diethyl ester n-Butyl lithium (1.6 M in hexanes, 1 mL) was added to an equal volume of THF at −20° C. A solution of diethyl methylphosphonate (220 mg, 1.45 mmol) in THF (1 mL) was then added dropwise and the solution was stirred for 30 minutes. After cooling at −60° C., the solution was transferred via a cannula to a vial containing copper (I) iodide (276 mg, 1.45 mmol), and the resulting mixture was stirred for 1 hour at −30° C. A solution of 6-(4-bromo-3-methyl-but-2-enyl)-7-hydroxy-5-methoxy-4-methyl-3H-isobenzofuran-1-one 3B (50 mg, 0.15 mmol) in THF (1 mL) was added and the mixture was allowed to warm to 0° C. for 2 hours before saturated aqueous ammonium chloride was added. The reaction mixture was acidified with 2 N HCl and extracted with ethyl acetate. The ethyl acetate extract was concentrated and the residue was chromatographed on silica gel (40% to 100% ethyl acetate/hexanes), affording [5-(4-hydroxy-6-methoxy-7-methyl-3-oxo-1,3-dihydro-isobenzofuran-5-yl)-3-methyl-pent-3-enyl]-phosphonic acid diethyl ester 3C as an oil (27 mg, contaminated with the starting diethyl methylphosphonate); $^1$H NMR (300 MHz, CDCl$_3$) δ 1.32 (m, 6H), 1.8-1.9 (m, 5H), 2.18 (s, 3H), 2.25 (m, 2H), 3.42 (d, J=7.2 Hz, 2H), 3.78 (s, 3H), 4.15 (m, 4H), 5.21 (s, 2H), 5.24 (t, J=7.2 Hz, 1H), 7.65 (s, 1H) ppm.

[5-(4-Hydroxy-6-methoxy-7-methyl-3-oxo-1,3-dihydro-isobenzofuran-5-yl)-3-methyl-pent-3-enyl]-phosphonic acid monoethyl ester A mixture of [5-(4-hydroxy-6-methoxy-7-methyl-3-oxo-1,3-dihydro-isobenzofuran-5-yl)-3-methyl-pent-3-enyl]-phosphonic acid diethyl ester 3C (27 mg, 0.066 mmol), LiOH (200 mg), MeOH (3 mL) and water (1 mL) was stirred at 70° C. for 4 hours. After cooling, the reaction solution was acidified with 2 N HCl, mixed with brine, and extracted with ethyl acetate/acetonitrle. The organic extract was concentrated and the residue was purified by preparative reverse-phase HPLC (acetonitrile and 0.1% aqueous CF$_3$COOH), affording [5-(4-hydroxy-6-methoxy-7-methyl-3-oxo-1,3-dihydro-isobenzofuran-5-yl)-3-methyl-pent-3-enyl]-phosphonic acid monoethyl ester 3D (7 mg, 28%); $^1$H NMR (300 MHz, CD$_3$OD) δ 1.28 (t, J=6.9 Hz, 3H), 1.7-1.9 (m, 5H), 2.20 (s, 3H), 2.2-2.3 (m, 2H), 3.41 (d, J=6.6 Hz, 2H), 3.80 (s, 3H), 4.02 (m, 2H), 5.2-5.3 (m, 3H) ppm.

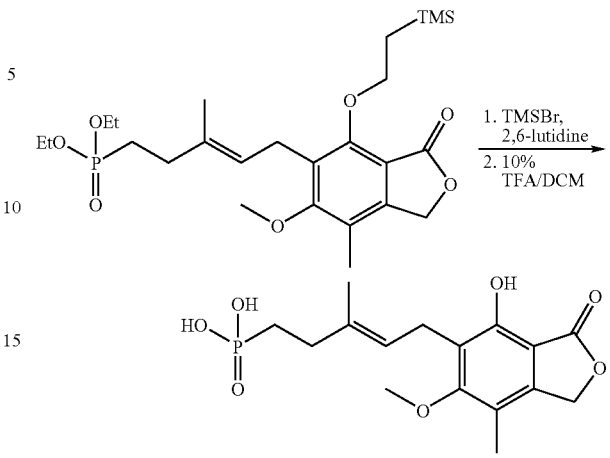

[5-(4-Hydroxy-6-methoxy-7-methyl-3-oxo-1,3-dihydro-isobenzofuran-5-yl)-3-methyl-pent-3-enyl]-phosphonic acid To a solution of {5-[6-Methoxy-7-methyl-3-oxo-4-(2-trimethylsilanyl-ethoxy)-1,3-dihydro-sobenzofuran-5-yl]-3-methyl-pent-3-enyl}-phosphonic acid diethyl ester (20 mg, 0.039 mmol) in DMF (0.5 mL) and DCM (0.5 mL) was added TMSBr (50.5 μL, 0.39 mmol) followed by 2,6-lutidine (45.3 μL, 0.39 mmol). The reaction was allowed to proceed for one hour when it was complete, as judged by LCMS. The reaction mixture was quenched with MeOH and concentrated to dryness. The residue was purified by preparative reverse-phase HPLC. The fraction containing the desired product was concentrated and treated with 10% TFA/DCM for 5 minutes. After concentration, the residue was purified by preparative reverse-phase HPLC to provide 7 mg (50%) of [5-(4-Hydroxy-6-methoxy-7-methyl-3-oxo-1,3-dihydro-isobenzofuran-5-yl)-3-methyl-pent-3-enyl]-phosphonic acid as a solid. $^1$H NMR (300 MHz, CD$_3$OD) δ 1.66-1.78 (m, 5H), 2.10 (s, 3H), 2.16-2.22 (m, 2H), 3.34 (d, J=7.2 Hz, 2H), 3.72 (s, 3H), 5.16 (s, 2H), 5.20 (t, J=7.2 Hz, 1H) ppm; $^{31}$P (121.4 MHz, CD$_3$OD) δ 31.57 ppm; MS (m/z) 355 [M−H]$^-$, 357 [M+H]$^+$.

Example 254

Preparation of Representative Compounds of the Invention

Representative compounds of the invention can be prepared as illustrated below.

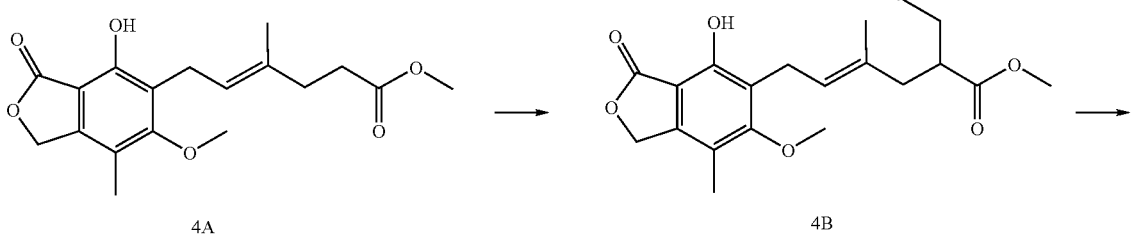

-continued

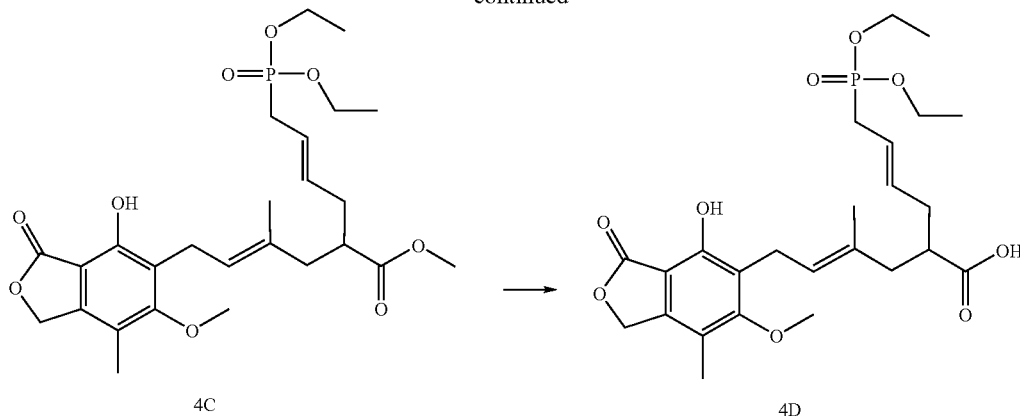

4C

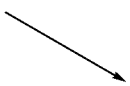

4D

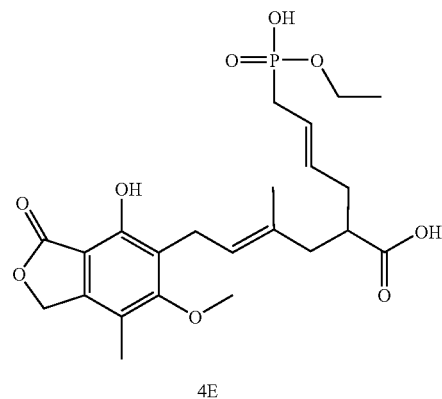

4E 2-(4-Bromo-but-2-enyl)-6-(4-hydroxy-6-methoxy-7-methyl-3-oxo-1,3-dihydro-isobenzofuran-5-yl)-4-methyl-hex-4-enoic acid methyl ester To a cooled (−78° C.) solution of mycophenolic acid methyl ester 4A (138 mg, 0.41 mmol) in THF (2.5 mL) was added a THF solution of sodium bis(trimethysilyl)amide (1.0 M, 0.98 mL). After stirring for 30 minutes, a solution of 1,4-dibromo-2-butene (950 mg, 4.1 mmol) in THF (2.5 mL) was added and stirring was continued for 10 minutes. The resulting mixture was warmed to −30° C. and stored at this temperature for 16 hours. The reaction was quenched with saturated aqueous ammonium chloride. The mixture was extracted with ethyl acetate to give, after evaporation of the solvent, a residue that was purified by chromatography on silica gel eluting with ethyl acetate (0% to 40%)/hexanes, affording 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester 4B (150 mg, 78%) as an oil; $^1$H NMR (300 MHz, CDCl$_3$) δ 1.75 (s, 3H), 2.0-2.4 (m, 8H), 2.62 (m, 1H), 3.37 (d, J=6.6 Hz, 2H), 3.58 (s, 3H), 3.76 (s, 3H), 3.88 (d, J=4.8 Hz, 2H), 5.1-5.3 (m, 3H), 5.67 (brs, 2H), 7.67 (s, 1H) ppm.

2-[4-(Diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester A solution of 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester 4B (140 mg, 0.30 mmol) and triethylphosphite (600 mg, 3.6 mmol) in toluene (30 mL) was stirred at reflux for 20 hours. The mixture was concentrated and chromatographed on silica gel eluting with ethyl acetate (60% to 100%)/hexanes, affording 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester 4C as an oil (70 mg, 43%); $^1$H NMR (300 MHz, CDCl$_3$) δ 1.27 (m, 6H), 1.79 (s, 3H), 2.0-2.7 (m, 8H), 3.37 (d, J=6.6 Hz), 3.52 (s, 3H), 3.75 (s, 3H), 4.08 (m, 4H), 5.20 m, 3H), 5.45 (m, 2H) ppm.

2-[4-(Diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid A mixture of 2-[4-(diethoxy-phosphoryl)-but-2-enyl]-6-(4-hydroxy-6-methoxy-7-methyl-3-oxo-1,3-dihydroisobenzofuran-5-yl)-4-methyl-hex-4-enoic acid methyl ester 4C (33 mg, 0.063 mmol) and lithium hydroxide (44 mg) in a mixture of THF (6 mL) and water (1 mL) was stirred at room temperature for 6 hours. The organic solvent was removed and the residue was partitioned between ethyl acetate and 5% aqueous sodium bicarbonate. The aqueous layer was acidified with 2 N HCl and extracted with ethyl acetate. The ethyl acetate extract was concentrated, affording 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 4D as an oil (30 mg, 100%); $^1$H NMR (300 MHz, CDCl$_3$) δ 1.27 (m, 6H), 1.79 (s, 3H), 2.0-2.7 (m, 8H), 3.37 (d, J=6.6 Hz), 3.75 (s, 3H), 4.08 (m, 4H), 5.19 (s, 2H), 5.25 (m, 1H), 5.44 (m, 1H), 5.55 (m, 1H), 5.45 (m, 2H) ppm.

2-[4-(Ethoxy-hydroxy-phosphoryl)-but-2-enyl]-6-(4-hydroxy-6-methoxy-7-methyl-3-oxo-1,3-dihydro-isobenzofuran-5-yl)-4-methyl-hex-4-enoic acid A mixture of 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester 4C (25 mg, 0.048 mmol) and lithium hydroxide (200 mg) in a mixture of methanol (3 mL) and water (1 mL) was stirred at 70° C. for 2 hours. The organic solvent was evaporated and the residue acidified with 2N HCl and extracted with ethyl acetate/acetonitrile. The organic extract was concentrated, and the residue was purified by preparative reverse-phase HPLC (acetonitrile and 0.1% aqueous CF$_3$COOH), affording 2-[4-(ethoxy-hydroxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 4E as an oil (15 mg, 89%); $^1$H NMR (300 MHz, CD$_3$OD) δ 1.25 (t, J=6.9 Hz, 3H), 1.81 (s, 3H), 2.1-2.6 (m, 8H), 3.40 (d, J=6.6 Hz, 2H), 3.77 (s, 3H), 3.97 (m, 2H), 5.1-5.3 (m, 3H), 5.67 (brs, 2H) ppm.

2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester Under a N$_2$ atmosphere, a solution of 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester (490 mg, 1.05 mmol) in trimethylphosphite (2.5 mL, 21.1 mmol) was heated at 120° C. for 1 hour. The reaction was allowed to cool to room temperature. The reaction mixture was worked up by removal of the solvent in vacuo followed by chromatography using EtOAc-hexanes to provide 460 mg (88%) of the product as an oil. $^1$H NMR (300 MHz, CDCl$_3$) δ 1.77 (s, 3H), 2.081-2.31 (m, 4H), 2.15 (s, 3H), 2.52 (d, 1H, J=22 Hz), 2.54 (d, 1H, J=22 Hz), 2.55-2.63 (m, 1H), 3.36 (d, 2H, J=7 Hz), 3.57 (s, 3H), 3.72 (d, 6H, J=11 Hz), 3.76 (s, 3H), 5.20 (s, 2H), 5.20-5.26 (m, 1H), 5.36-5.56 (m, 2H), 7.69 (s, 1H) ppm; $^{31}$P (121.4 MHz, CDCl$_3$) δ 30.1 ppm; MS (m/z) 497.2 [M+H]$^+$, 519.2 [M+Na]$^+$.

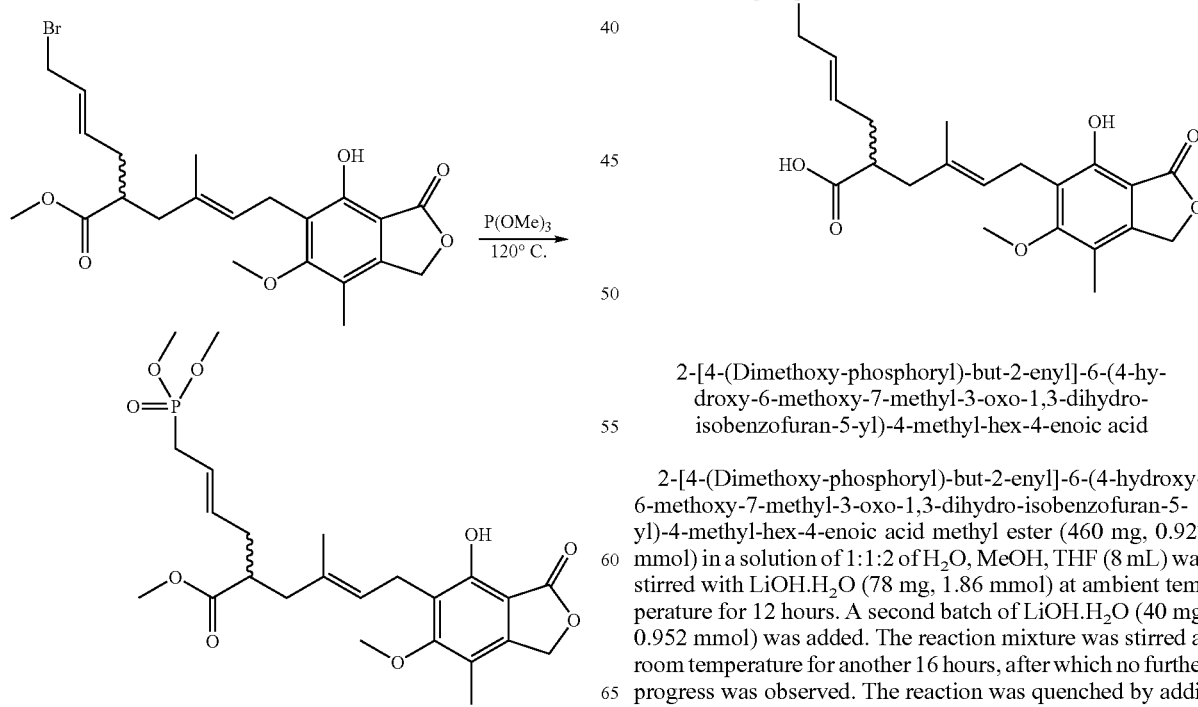

2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester (460 mg, 0.927 mmol) in a solution of 1:1:2 of H$_2$O, MeOH, THF (8 mL) was stirred with LiOH.H$_2$O (78 mg, 1.86 mmol) at ambient temperature for 12 hours. A second batch of LiOH.H$_2$O (40 mg, 0.952 mmol) was added. The reaction mixture was stirred at room temperature for another 16 hours, after which no further progress was observed. The reaction was quenched by addition of a saturated aqueous solution of NH$_4$Cl. The organic layer was removed in vacuo and the product was extracted with EtOAc from the aqueous layer, which had been acidified by addition of 5 drops of 2 N HCl. The product was further purified by chromatography to provide the desired product. $^1$H NMR (300 MHz, CDCl$_3$) δ 1.79 (s, 3H), 2.08-2.38 (m, 4H), 2.15 (s, 3H), 2.53 (d, 1H, J=22 Hz), 2.60 (d, 1H, J=22 Hz), 2.57-2.64 (m, 1H), 3.38 (d, 2H, J=7 Hz), 3.72 (d, 6H, J=11 Hz) 3.76 (s, 3H), 5.20 (s, 2H), 5.27 (t, 1H, J=6 Hz), 5.36-5.63 (m, 2H) ppm; $^{31}$P (121.4 MHz, CDCl$_3$) δ 30.5 ppm; MS (m/z) 481.2 [M−H]$^-$.

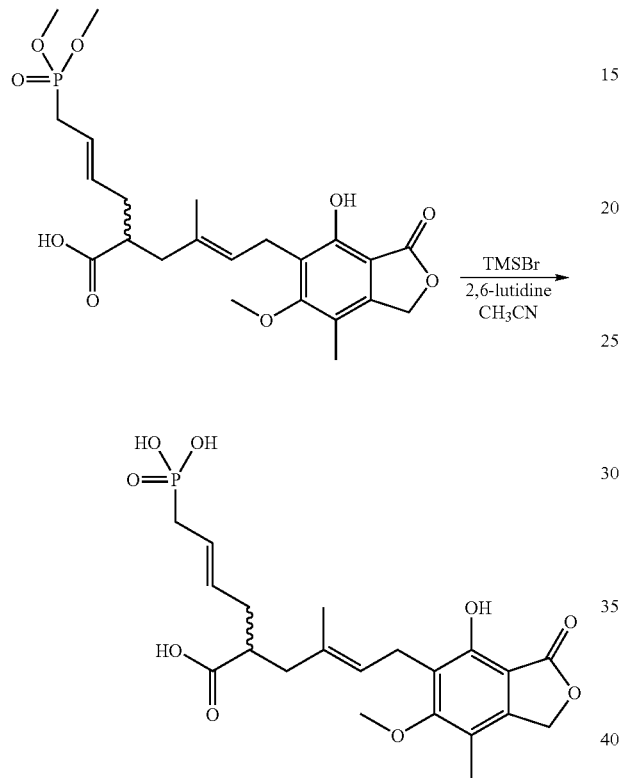

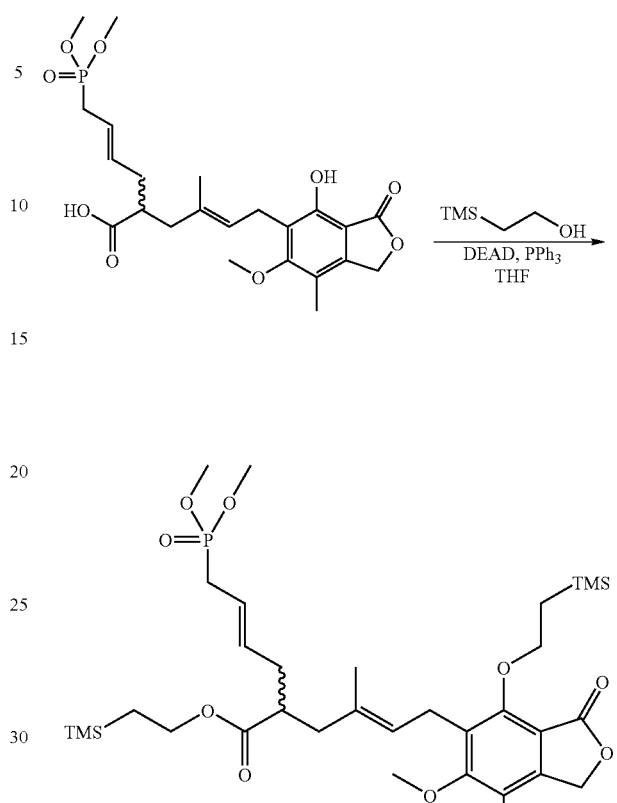

2-[4-(2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid To a solution of 2-[4-(dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid (25 mg, 0.052 mmol) in acetonitrile (2 mL) was added 2,6-lutidine (60 μL, 0.52 mmol) and TMSBr (67 μL, 0.52 mmol). The reaction was allowed to proceed for 45 minutes when it was completed as judged by LCMS. The reaction mixture was concentrated under reduced pressure and quenched with an aqueous NaOH solution (1 mL). The product was purified by RP HPLC (using a C18 column with a gradient of H$_2$O, 0.1% TFA-acetonitrile, 0.1% TFA) to provide 14.2 mg (60%) of the product as a solid. $^1$H NMR (300 MHz, CD$_3$OD) δ 1.81 (s, 3H), 2.081-2.31 (m, 4H), 2.16 (s, 3H), 2.45 (d, 1H, J=22 Hz), 2.47 (d, 1H, J=22 Hz), 2.55-2.63 (m, 1H), 3.38 (d, 2H, J=7 Hz), 3.77 (s, 3H), 5.25 (s, 2H), 5.20-5.36 (m, 1H), 5.36-5.56 (m, 2H) ppm; $^{31}$P (121.4 MHz, CD$_3$OD) δ 25.4 ppm; MS (m/z) 453 [M−H]$^-$.

2-[4-(Dimethoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-[4-(dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid (160 mg, 0.332 mmol) and trimethylsilylethanol (160 mg, 1.36 mmol) in THF (8.00 mL) was stirred with triphenylphosphine (345 mg, 1.33 mmol). To this solution was added diethyl azodicarboxylate (230 μL, 1.33 mmol) at 0° C. The mixture was allowed to warm to room temperature and stirred for 16 hours. Additional triphenylphosphine (180 mg, 0.692 mmol), trimethylsilylethanol (160 mg, 1.36 mmol), and diethyl azodicarboxylate (115 μL, 0.665 mmol) were added and the reaction mixture was stirred for another 1 day at room temperature. The reaction was worked up by removing the solvents in vacuo and purifying the residue by silica gel chromatography to provide 192 mg (85%) of the product as a clear oil. $^1$H NMR (300 MHz, CDCl$_3$) δ 0.03 (s, 9H), 0.05 (s, 9H), 0.93-0.96 (m, 2H), 1.20-1.29 (m, 2H), 1.78 (s, 3H), 2.01-2.32 (m, 4H), 2.17 (s, 3H), 2.51 (d, 1H, J=22 Hz), 2.58 (d, 1H, J=22 Hz), 2.50-2.60 (m, 1H), 3.37 (d, 2H, J=7 Hz), 3.72 (d, 6H, J=11 Hz), 3.76 (s, 3H), 4.08 (appt t, 2H, J=8 Hz), 4.30 (appt t, 2H, J=8 Hz), 5.12 (s, 2H), 5.15-5.25 (m, 1H), 5.36-5.63 (m, 2H) ppm; $^{31}$P (121.4 MHz, CDCl$_3$) δ 29.3 ppm; MS (m/z) 705.3 [M+Na]$^+$.

941

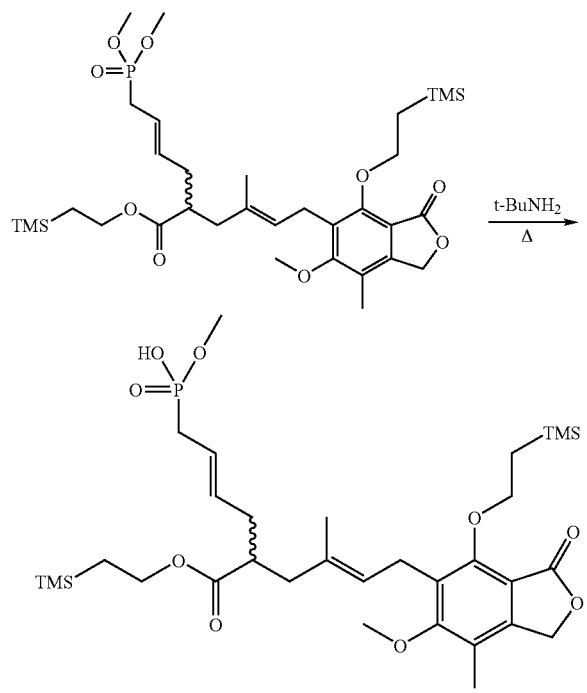

942

2-[4-(Hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A mixture of 2-[4-(dimethoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (184 mg, 0.270 mmol) in tert-butylamine (2.8 mL, 27 mmol) was heated at 60° C. for 24 hours. The solution was allowed to cool to room temperature and concentrated. The residue was purified by silica gel column chromatography using MeOH/CH$_2$Cl$_2$ (0-30%) to provide 75 mg of the product as a clear oil. $^1$H NMR (300 MHz, CDCl$_3$) δ 0.01 (s, 9H), 0.04 (s, 9H), 0.89 (appt t, 2H, J=9 Hz), 1.23 (appt t, 2H, J=9 Hz), 1.77 (s, 3H), 2.01-2.31 (m, 4H), 2.17 (s, 3H), 2.36 (d, 1H, J=22 Hz), 2.38 (d, 1H, J=22 Hz), 2.52 (septet, 1H, J=9 Hz), 3.39 (d, 2H, J=7 Hz), 3.51 (d, 3H, J=11 Hz), 4.01-4.08 (m, 2H), 4.30 (dd, 2H, J=8, 9 Hz), 5.11 (s, 2H), 5.19 (br t, 1H, J=6 Hz), 5.33-5.56 (m, 2H), 8.49 (br s, 1H) ppm; $^{31}$P (121.4 MHz, CDCl$_3$) δ 22.1 ppm; MS (m/z) 667.4 [M+Na]$^+$.

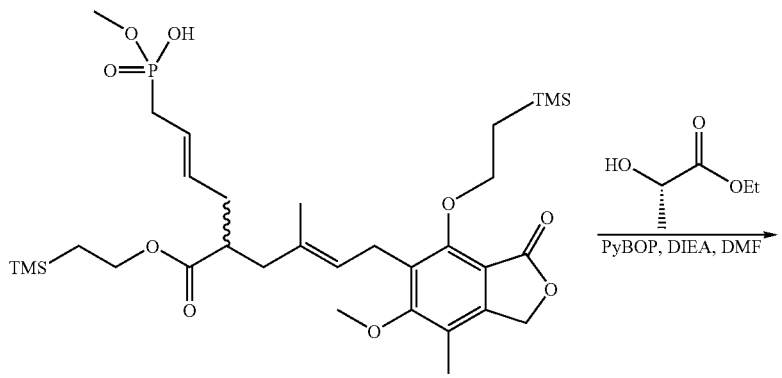

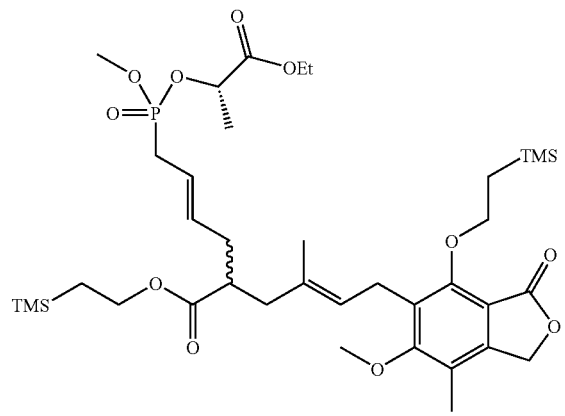

943

2-{4-[(1-Ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (67 mg, 0.10 mmol) and PyBOP (234 mg, 0.450 mmol) in DMF (1.5 mL) was stirred with ethyl (S)-(−)-lactate (53 mg, 0.45 mmol) and DIEA (174 μL, 1.00 mmol) at ambient temperature for 1 hour, when complete consumption of the starting materials was observed. The reaction was worked up by addition of saturated aqueous sodium chloride and ethyl acetate. The organic layer was separated and washed with 5% aqueous solution of lithium chloride. The organic layer was dried in vacuo and the residue was purified by silica gel chromatography using MeOH—$CH_2Cl_2$ (0-20%) to provide 57 mg (74%) of the desired product as a clear oil. $^1$H NMR (300 MHz, $CDCl_3$) δ 0.02 (s, 9H), 0.05 (s, 9H), 0.88-0.94 (m, 2H), 1.20-1.30 (m, 2H), 1.29 (t, 3H, J=7 Hz), 1.45 (d, 3H, J=7 Hz), 1.78 (s, 3H), 2.01-2.31 (m, 4H), 2.17 (s, 3H), 2.50-2.58 (m, 1H), 2.65 (d, 1H, J=22 Hz), 2.67 (d, 1H, J=22 Hz), 3.39 (d, 2H, J=7 Hz), 3.69 and 3.77 (d, 3H, J=11 Hz), 3.76 (s, 3H), 4.07 (appt t, 2H, J=7 Hz), 4.20 (dq, 2H, J=3, 7 Hz), 4.29 (appt t, 2H, J=9 Hz), 4.85-4.99 (m, 1H), 5.12 (s, 2H), 5.19 (br t, 1H, J=6 Hz), 5.33-5.61 (m, 2H) ppm; $^{31}$P (121.4 MHz, $CDCl_3$) δ 28.9, 29.9 ppm; MS (m/z) 791.4 [M+Na]$^+$.

944

2-{4-[(1-Ethoxycarbonyl-ethoxy)-methoxy-phosphoryl]-but-2-enyl}-6-(4-hydroxy-6-methoxy-7-methyl-3-oxo-1,3-dihydro-isobenzofuran-5-yl)-4-methyl-hex-4-enoic acid A solution of 2-{4-[(1-ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (14 mg, 0.018 mmol) in THF (1 mL) was stirred with a 1M solution of TBAF in THF (55 μL, 0.055 mmol) for 1 hour. The reaction mixture was concentrated, acidified with 1N HCl and extracted with EtOAc. The organic layer was washed with brine and dried. The product was purified by silica gel column chromatography EtOH-EtOAc (0-10%). Further purification was performed by dissolving the product in $CH_2Cl_2$ and passing the compound through a 13 mm Acrodisc syringe filter with a 0.45 μm Nylon membrane to provide 8 mg (77%) of the product. $^1$H NMR (300 MHz, $CDCl_3$) δ 0.92 (t, 3H, J=7 Hz), 1.30 (d, 3H, J=8 Hz), 1.79 (s, 3H), 2.10-2.39 (m, 4H), 2.15 (s, 3H), 2.53 (d, 1H, J=8 Hz), 2.65 (d, 1H, J=22 Hz), 2.68 (d, 1H, J=22 Hz), 3.38 (d, 2H, J=7 Hz), 3.70 and 3.74 (d, 3H, J=11 Hz), 3.76 (s, 3H), 4.07 (m, 2H), 4.96 (dq, 1H, J=7 Hz), 5.20 (s, 2H), 5.27 (br t, 1H, J=7 Hz), 5.33-5.55 (m, 2H), 7.51-7.56 (m, 1H), 7.68-7.74 (m, 1H) ppm; $^{31}$P (121.4 MHz, $CDCl_3$) δ 29.0, 30.1 ppm; MS (m/z) 569.2 [M+H]$^+$, 591.3 [M+Na]$^+$.

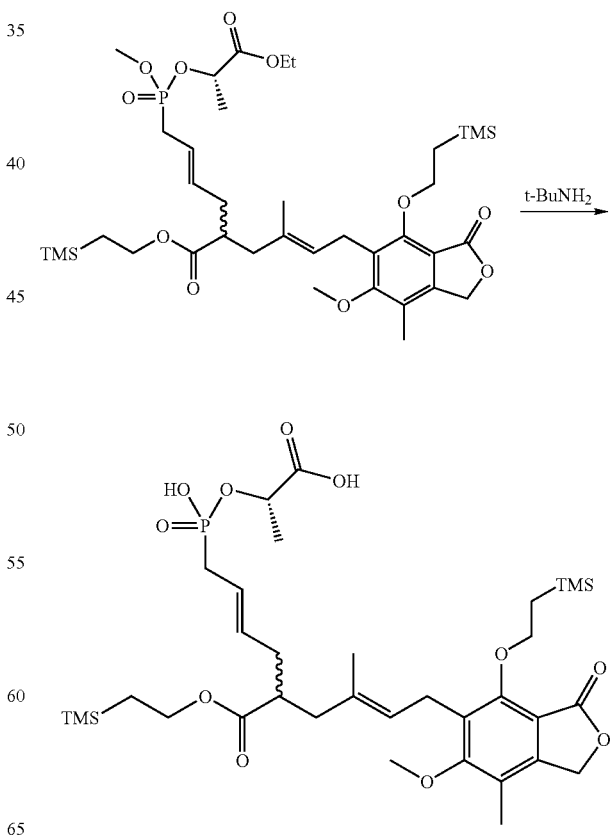

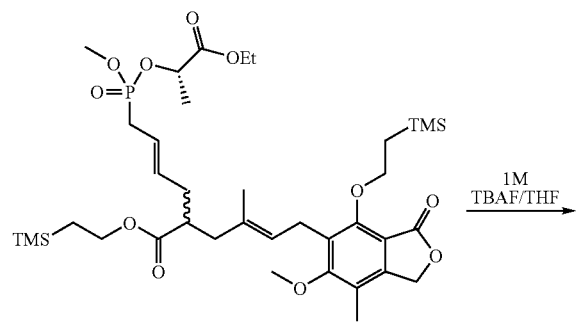

2-{4-[(1-Carboxy-ethoxy)-hydroxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-{4-[(1-ethoxycarbonyl-ethoxy)-methoxyphosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanylethyl ester (12 mg, 0.016 mmol) in tert-butylamine (1 mL, 9.6 mmol) was heated at 65° C. for 16 hours. The solution was allowed to cool to room temperature and concentrated to provide the crude product as an oil. $^1$H NMR (300 MHz, CDCl$_3$) δ 0.03 (s, 9H), 0.04 (s, 9H), 0.86-0.98 (m, 2H), 1.22-1.33 (m, 2H), 1.50 (d, 3H, J=7 Hz), 1.78 (s, 3H), 2.05-2.30 (m, 4H), 2.10 (s, 3H), 2.48-2.63 (m, 3H), 3.40 (d, 2H, J=7 Hz), 3.76 (s, 3H), 4.08 (appt t, 2H, J=9 Hz), 4.25-4.33 (m, 2H), 4.75-4.84 (m, 1H), 5.13 (s, 2H), 5.15-5.23 (m, 1H), 5.33-5.55 (m, 2H) ppm; $^{31}$P (121.4 MHz, CDCl$_3$) δ 28.9 ppm; MS (m/z) 725.3 [M−H]$^-$.

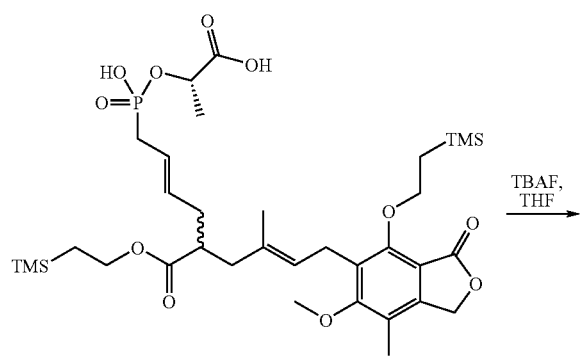

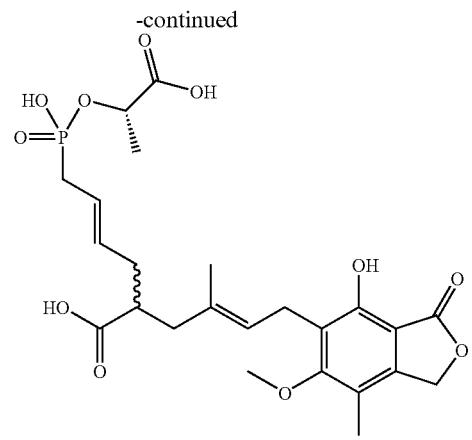

2-{4-[(1-Carboxy-ethoxy)-hydroxy-phosphoryl]-but-2-enyl}-6-(4-hydroxy-6-methoxy-7-methyl-3-oxo-1,3-dihydro-isobenzofuran-5-yl)-4-methyl-hex-4-enoic acid A solution of crude 2-{4-[(1-carboxy-ethoxy)-hydroxyphosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (AC-2101-59) and tetrabutylammonium fluoride in THF (1M, 54 μL, 0.054 mmol) was stirred with THF (1 mL) for 2 hours at ambient temperature, when more tetrabutylammonium fluoride in THF (54 μL, 0.054 mmol) was added. The reaction was stirred for an additional 16 hours, by which time the reaction was complete. The reaction mixture was concentrated in vacuo and the product was purified by RP HPLC using a Phenomenex Synergi 5μ Hydro RP 80 A column (50×21.2 mm) with eluents of H$_2$O, 0.1% TFA-CH$_3$CN, 0.1% TFA to provide the product (8.0 mg) as a clear oil. $^1$H NMR (300 MHz, CDCl$_3$) δ 1.51 (d, 3H, J=7 Hz), 1.79 (s, 3H), 2.05-2.40 (m, 4H), 2.11 (s, 3H), 2.49-2.71 (m, 3H), 3.38 (d, 2H, J=6 Hz), 3.76 (s, 3H), 4.85 (br s, 1H), 5.20 (s, 2H), 5.21-5.30 (m, 1H), 5.33-5.63 (m, 2H) ppm; $^{31}$P (121.4 MHz, CDCl$_3$) δ 27.7 ppm; MS (m/z) 525.2 [M−H]$^-$.

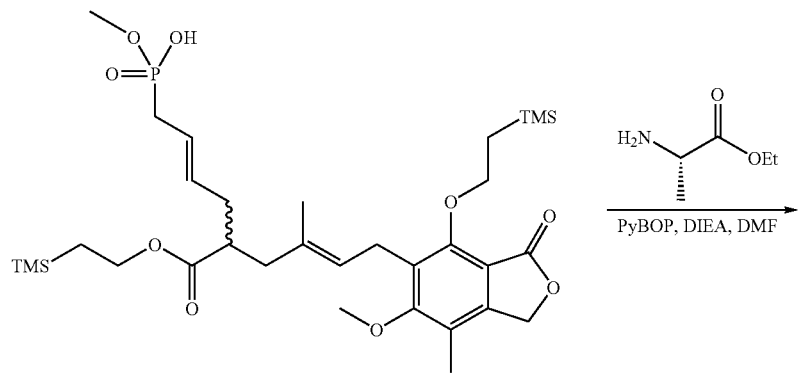

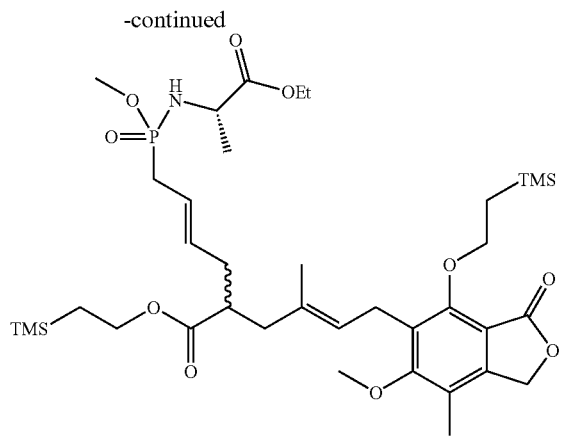

2-{4-[(1-Ethoxycarbonyl-ethylamine)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (20 mg, 0.030 mmol), PyBOP (62.4 mg, 0.120 mmol) in DMF (1.0 mL) was stirred with L-alanine ethyl ester hydrochloride (18 mg, 0.12 mmol) and DIEA (26 μL, 0.15 mmol) at ambient temperature for 1 hour, when complete consumption of the starting materials was observed. The reaction was worked up by addition of water until the reaction solution became cloudy. DMF was added dropwise until the mixture became clear again. The reaction mixture was filtered through Acrodisc (13 mm syringe filter with a 0.45 μm Nylon membrane) and purified by RP HPLC using a Phenomenex Synergi 5μ Hydro RP 80 A column (50×21.2 mm), eluting with water and acetonitrile. The fractions containing the product were pooled together and concentrated in vacuo to remove the acetonitrile. The remaining solution was saturated with sodium chloride and extracted with EtOAc and acetonitrile to provide 7.2 mg of the product. $^1$H NMR (300 MHz, CDCl$_3$) δ 0.03 (s, 9H), 0.05 (s, 9H), 0.923 (appt t, 2H, J=8 Hz), 1.18-1.31 (m, 5H), 1.41 (t, 3H, J=7 Hz), 1.78 (s, 3H), 2.03-2.36 (m, 4H), 2.18 (s, 3H), 2.43-2.63 (m, 3H), 3.10-3.30 (m, 1H), 3.40 (d, 2H, J=7 Hz), 3.62 and 3.65 (d, 3H, J=11 Hz), 3.76 (s, 3H), 4.03-4.12 (m, 2H), 4.20 (dq, 2H, J=2, 7 Hz), 4.29 (appt t, 2H, J=8 Hz), 5.12 (s, 2H), 5.18-5.28 (m, 1H), 5.33-5.67 (m, 2H) ppm; $^{31}$P (121.4 MHz, CDCl$_3$) δ 30.4, 31.2 ppm; MS (m/z) 790.4 [M+Na]$^+$.

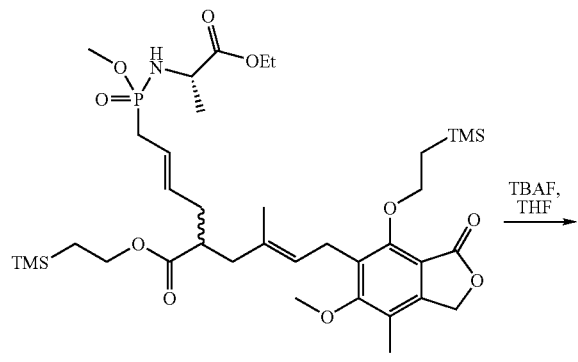

TBAF, THF →

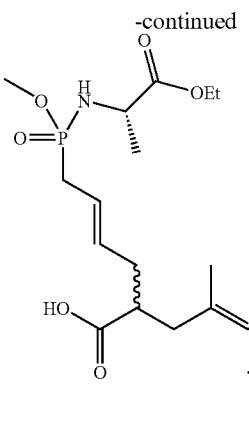

2-{4-[(1-Ethoxycarbonyl-ethylamine)-methoxy-phosphoryl]-but-2-enyl}-6-(4-hydroxy-6-methoxy-7-methyl-3-oxo-1,3-dihydro-isobenzofuran-5-yl)-4-methyl-hex-4-enoic acid To a solution of 2-{4-[(1-ethoxycarbonyl-ethylamine)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (7.2 mg, 9.38 mmol) in THF (1 mL) was added TBAF (40 μL, 1M solution in THF) at room temperature. The reaction mixture was stirred for 20 minutes, when the starting material was completely converted to the desired product as judged by LCMS. The reaction mixture was dried in vacuo and re-dissolved in DMF. The product was purified by RP HPLC using a Phenomenex Synergi 5μ Hydro RP 80 A column (50×21.2 mm) with eluents of H$_2$O—CH$_3$CN. The fractions containing the desired product were pooled and further purified on Dowex 50WX8-400 packed on a 4.5 cm×2 cm column to elute the sodium salt at H$_2$O— MeOH (1:1), providing 3.2 mg of the desired product. $^1$H NMR (300 MHz, CD$_3$OD) δ 1.26 (dd, 3H, J=4, 7 Hz), 1.37 (t, 3H, J=8 Hz), 1.80 (s, 3H), 2.00-2.22 (m, 4H), 2.10 (s, 3H), 2.25-2.60 (m, 3H), 3.37 (d, 2H, J=7 Hz), 3.60 and 3.65 (d, 3H, J=11 Hz), 3.74 (s, 3H), 3.83-3.96 (m, 1H), 4.18 (q, 2H, J=8 Hz), 5.15 (s, 2H), 5.25-5.42 (m, 2H), 5.55-5.69 (m, 1H) ppm; $^{31}$P (121.4 MHz, CD$_3$OD) δ 33.8, 34.2 ppm; MS (m/z) 568.2 [M+H]$^+$, 590.3 [M+Na]$^+$.

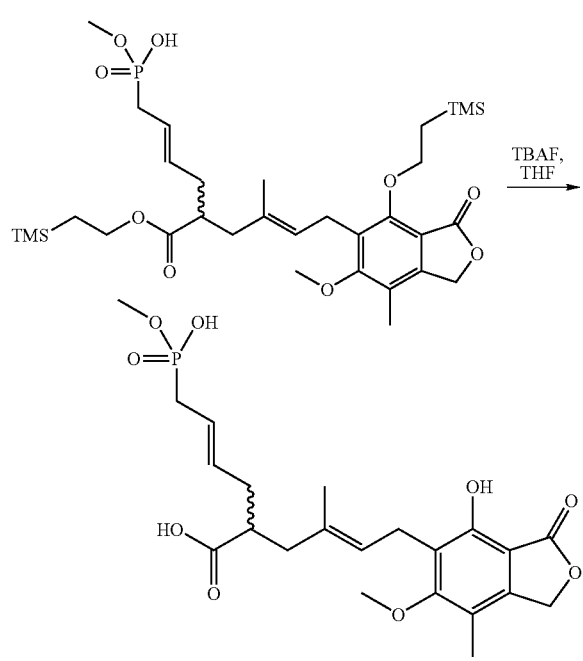

6-(4-Hydroxy-6-methoxy-7-methyl-3-oxo-1,3-dihydro-isobenzofuran-5-yl)-2-[4-(hydroxy-methoxy-phosphoryl)-but-2-enyl]-4-methyl-hex-4-enoic acid To a solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanylethyl ester (11 mg, 0.016 mmol) in THF (1 mL) was added TBAF (50 µL, 1M solution in THF) at room temperature. The solution was stirred for 16 hours and concentrated. The solution was dried under reduced pressure and re-suspended in DMF (0.8 mL) and water (0.25 mL). The solution was filtered through Acrodisc (13 mm syringe filter with a 0.45 µm Nylon membrane) and purified by RP HPLC using a Phenomenex Synergi 5µ Hydro RP 80 A column (50×21.2 mm) with eluents of $H_2O$, 0.1% TFA-$CH_3CN$, 0.1% TFA. The product from the column was subjected to ion exchange chromatography (Sodium salt form of Dowex 50WX8-400) using a 2×4.5 cm column eluting with $H_2O$-MeOH (1:1) to provide 7.5 mg of the desired product as an oil. $^1H$ NMR (300 MHz, $CDCl_3$) δ 1.80 (s, 3H), 2.01-2.29 (m, 5H), 2.11 (s, 3H), 2.35 (d, 2H, J=22 Hz), 3.38 (d, 2H, J=7 Hz), 3.53 (d, 3H, J=11 Hz), 3.75 (s, 3H), 5.19 (s, 2H), 5.26 (t, 1H, J=6 Hz), 5.43-5.54 (m, 2H) ppm; $^{31}P$ (121.4 MHz, $CDCl_3$) δ 23.5 ppm; MS (m/z) 469.2 $[M+H]^+$, 491.3 $[M+Na]^+$.

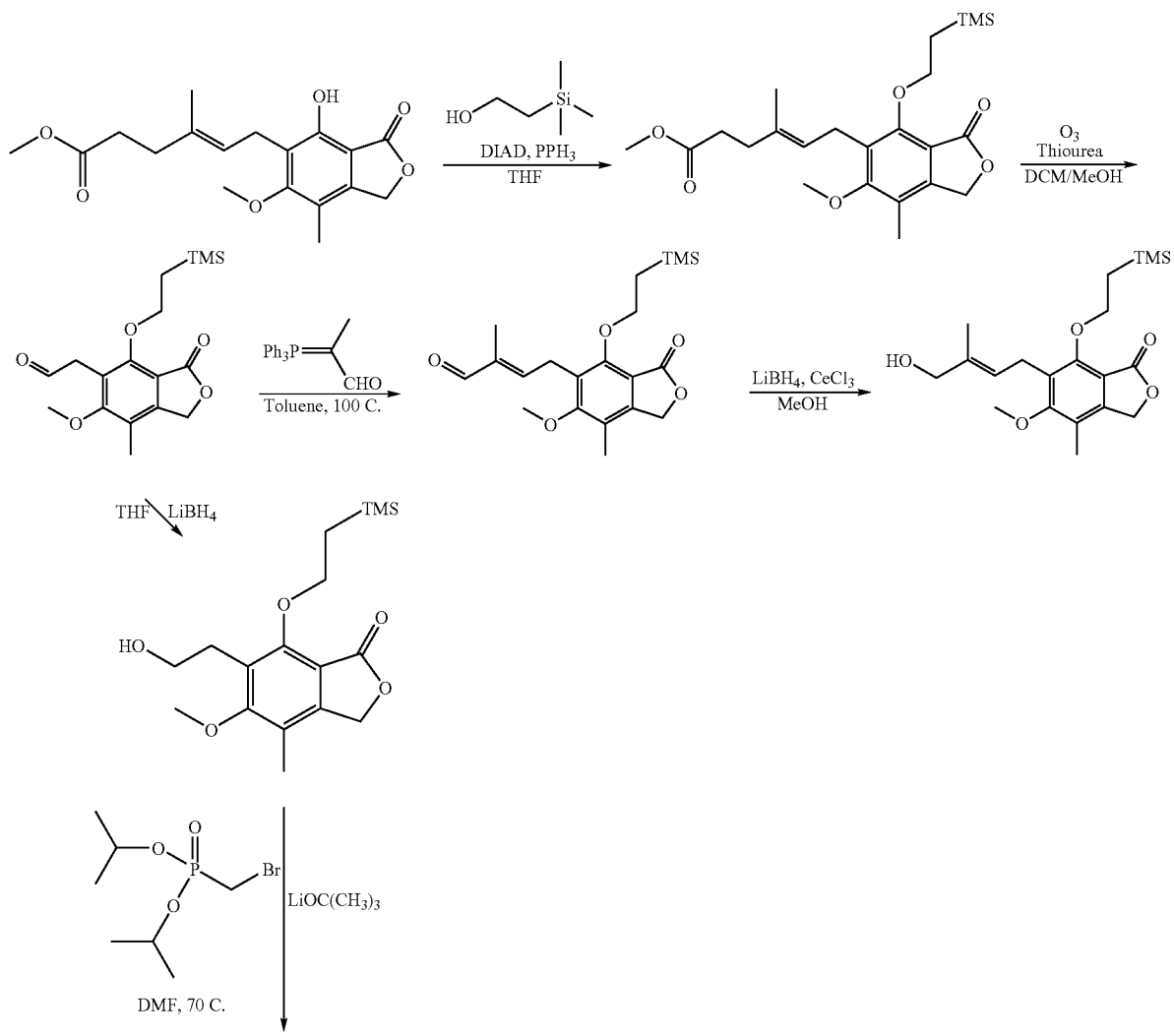

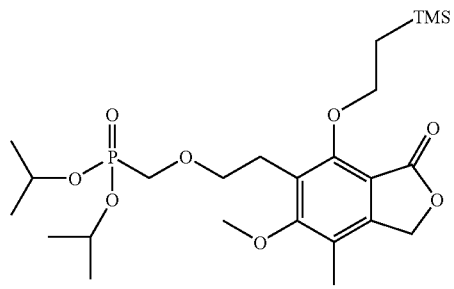

↓ TMSBr
CH₃CN

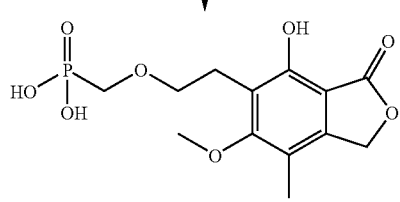

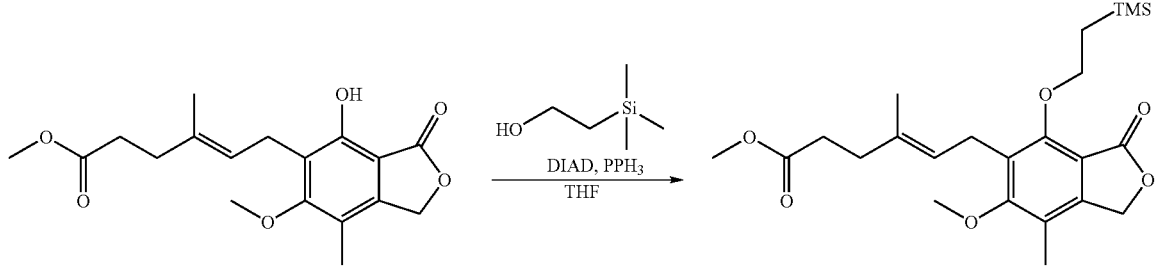

6-[6-Methoxy-7-methyl-3-oxo-4-(2-trimethylsilanyl-ethoxy)-1,3-dihydro-isobenzofuran-5-yl]-4-methyl-hex-4-enoic acid methyl ester To a solution of 6-(4-hydroxy-6-methoxy-7-methyl-3-oxo-1,3-dihydro-isobenzofuran-5-yl)-4-methyl-hex-4-enoic acid methyl ester (222 mg, 0.66 mmol), triphenylphosphine (260 mg, 0.996 mmol), and diethyl azodicarboxylate (173 mg, 0.996 mmol) in THF (3 mL) at 0° C. was added a solution of 2-trimethylsilylethanol (142 µL, 0.996 mmol) in THF (3 mL). The resulting yellow solution was allowed to warm to room temperature and stirred overnight. The reaction was concentrated to dryness and ether and hexanes were added. Triphenylphosphine oxide was removed by filtration and the filtrate was concentrated and purified by silica gel chromatography to provide 248 mg of the desired product as a colorless oil. $^1$H NMR (300 MHz, CDCl₃) δ 0.03 (s, 9H), 1.18-1.30 (m, 2H), 1.81 (s, 3H), 2.18 (s, 3H), 2.25-2.33 (m, 2H), 2.37-2.45 (m, 2H), 3.42 (d, 2H, J=7 Hz), 3.62 (s, 3H), 3.77 (s, 3H), 4.25-4.35 (m, 2H), 5.13 (s, 2H), 5.12-5.22 (m, 1H) ppm.

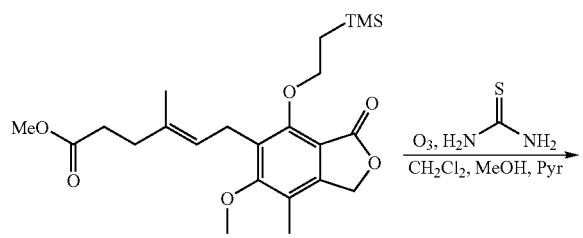

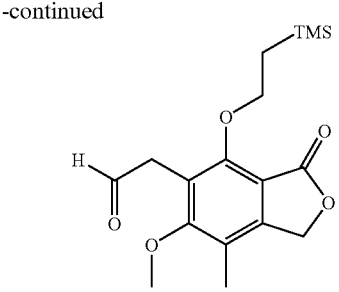

[6-Methoxy-7-methyl-3-oxo-4-(2-trimethylsilanyl-ethoxy)-1,3-dihydro-isobenzofuran-5-yl]-acetaldehyde A solution of 6-[6-methoxy-7-methyl-3-oxo-4-(2-trimethylsilanyl-ethoxy)-1,3-dihydro-isobenzofuran-5-yl]-4-methyl-hex-4-enoic acid methyl ester (618 mg, 1.42 mmol) in MeOH (10 mL), CH₂Cl₂ (10 mL) and pyridine (50 µL, 0.618 mmol) was cooled to −70° C. using a dry ice/acetone bath according to the procedure of Smith, D. B. et al., *J. Org. Chem.*, 1996, 61, 6, 2236. A stream of ozone was bubbled through the reaction via a gas dispersion tube until the reaction became blue in color (15 minutes). The ozone line was replaced with a stream of nitrogen and bubbling continued for another 15 minutes, by which time the blue color had disappeared. To this solution, thiourea (75.7 mg, 0.994 mmol) was added in one portion at −70° C., and the cooling bath was removed. The reaction was allowed to warm to room temperature and stirred for 15 hours. The reaction was worked up by filtration to remove solid thiourea S-dioxide, and then partitioned between CH$_2$Cl$_2$ and water. The organic layer was removed. The aqueous layer was washed with CH$_2$Cl$_2$ one more time, and the organic extracts were combined. The organic layer was washed with aqueous 1N HCl, saturated NaHCO$_3$ and brine. The organic extracts were dried in vacuo and the residue was purified to by silica gel chromatography to afford 357 mg (75%) of the product as a white solid. $^1$H NMR (300 MHz, CDCl$_3$) δ −0.01 (s, 9H), 1.05-1.15 (m, 2H), 2.15 (s, 3H), 3.69 (s, 3H), 3.78 (d, 2H, J=1 Hz), 4.27-4.39 (m, 2H), 5.11 (s, 2H), 9.72 (d, 1H, J=1 Hz) ppm.

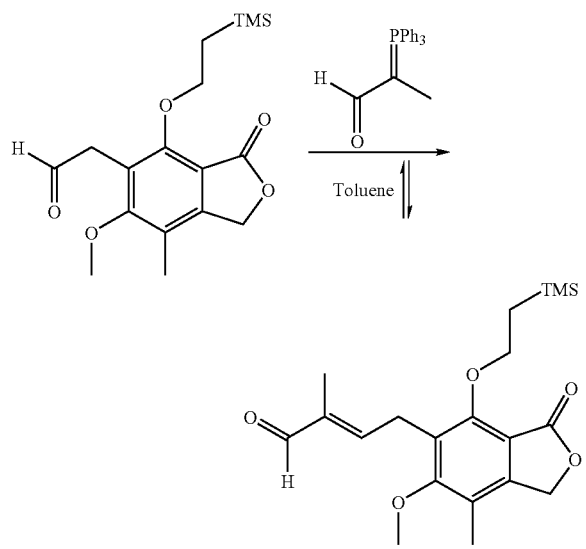

4-[6-Methoxy-7-methyl-3-oxo-4-(2-trimethylsilanyl-ethoxy)-1,3-dihydro-isobenzofuran-5-yl]-2-methyl-but-2-enal

[6-Methoxy-7-methyl-3-oxo-4-(2-trimethylsilanyl-ethoxy)-1,3-dihydro-isobenzofuran-5-yl]-acetaldehyde (70 mg, 0.21 mmol) in toluene (2 mL) was heated at 100° C. with 2-(triphenyl-phosphanylidene)-propionaldehyde (72.9 mg, 0.23 mmol) overnight. A second portion of 2-(triphenyl-phosphanylidene)-propionaldehyde (33 mg, 0.11 mmol) was added and the reaction mixture was heated for an additional day. After concentration, the residue was purified by silica gel chromatography to provide 54 mg (83%) of the desired product as a pale yellow oil. $^1$H NMR (300 MHz, CDCl$_3$) δ 0.00 (s, 9H), 1.10-1.21 (m, 2H), 1.87 (s, 3H), 2.16 (s, 3H), 3.67-3.76 (m, 2H), 3.74 (s, 3H), 4.27-4.39 (m, 2H), 5.11 (s, 2H), 6.40-6.48 (m, 1H), 9.2 (s, 1H) ppm.

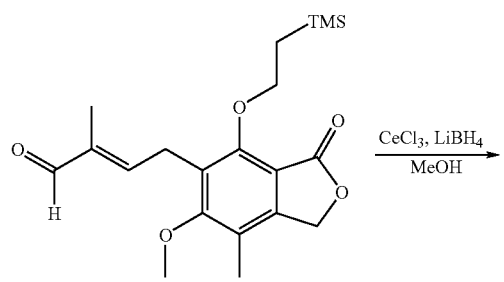

6-(4-Hydroxy-3-methyl-but-2-enyl)-5-methoxy-4-methyl-7-(2-trimethylsilanyl-ethoxy)-3H-isobenzofuran-1-one A solution of 4-[6-methoxy-7-methyl-3-oxo-4-(2-trimethylsilanyl-ethoxy)-1,3-dihydro-isobenzofuran-5-yl]-2-methyl-but-2-enal (103 mg, 0.27 mmol) in methanol (5 mL) was cooled to 0° C. A solution of CeCl$_3$ (0.68 mL, MeOH: H$_2$O, 9:1) was added, followed by LiBH$_4$ (0.14 mL, 0.28 mmol of a 2M solution in THF). The ice bath was removed and the reaction mixture was allowed to warm to room temperature. The reaction mixture was stirred for an additional 40 minutes whereupon TLC indicated complete consumption of starting aldehyde. The reaction was worked up by addition of aqueous 1N HCl (0.5 mL) and the product was extracted with CH$_2$Cl$_2$. The organic layer was washed with saturated aqueous sodium bicarbonate solution and brine. The organic layer was concentrated under reduced pressure and the residue was purified by silica gel chromatography to provide 100 mg (97%) of the product as a clear liquid. $^1$H NMR (300 MHz, CDCl$_3$) δ 0.00 (s, 9H), 1.20 (dd, 2H, J=7, 8 Hz), 1.81 (s, 3H), 2.13 (s, 3H), 3.38-3.50 (m, 2H), 3.74 (s, 3H), 3.95 (s, 2H), 4.27 (dd, 2H, J=7, 8 Hz), 5.08 (s, 2H), 5.17-5.44 (m, 1H) ppm.

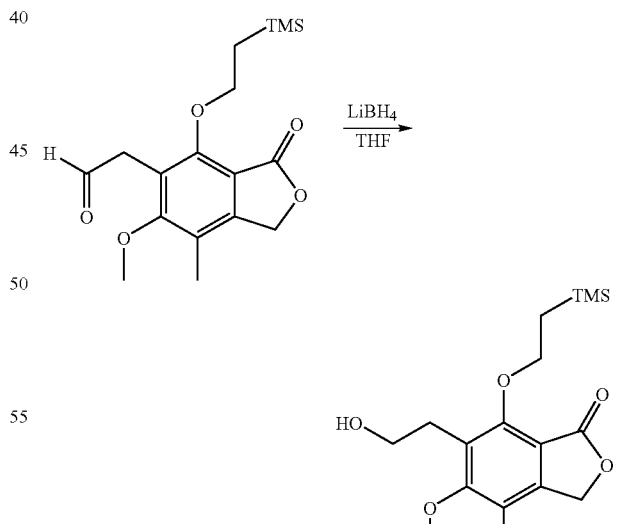

6-(2-Hydroxy-ethyl)-5-methoxy-4-methyl-7-(2-trimethylsilanyl-ethoxy)-3H-isobenzofuran-1-one To a solution of [6-methoxy-7-methyl-3-oxo-4-(2-trimethylsilanyl-ethoxy)-1,3-dihydro-isobenzofuran-5-yl]-acetaldehyde (97 mg, 0.29 mmol) in THF (5 mL) was added an aliquot of a 2 M LiBH$_4$ in THF (150 μL, 0.300 mmol). The reaction mixture was stirred at room temperature for 1 hour when complete consumption of the starting materials was observed by TLC. The reaction mixture was worked up by addition of an aqueous 1N HCl solution and extraction with EtOAc. The organic layer was dried in vacuo and the residue was purified by silica gel chromatography to provide the product. $^1$H NMR (300 MHz, CDCl$_3$) δ 0.00 (s, 9H), 1.20 (dd, 2H, J=7, 9 Hz), 2.07 (br s, 1H), 2.14 (s, 3H), 2.97 (t, 2H, J=6 Hz), 3.76 (t, 2H, J=6 Hz), 3.77 (s, 3H), 4.32 (dd, 2H, J=7, 8 Hz), 5.08 (s, 2H) ppm.

Example 255

Preparation of Representative Compounds of the Invention

Representative compounds of the invention can be prepared as illustrated below.

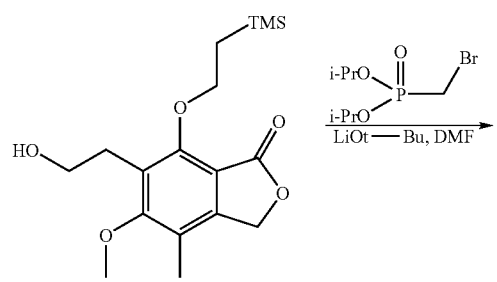

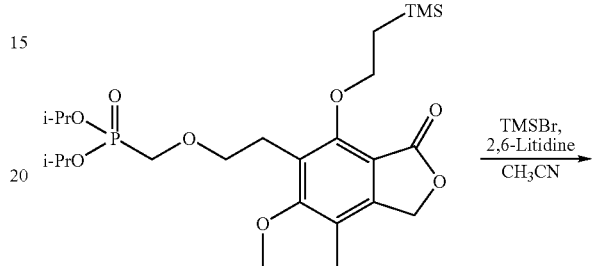

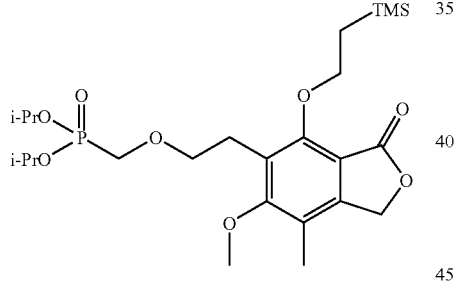

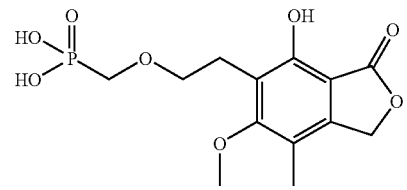

{2-[6-Methoxy-7-methyl-3-oxo-4-(2-trimethylsilanyl-ethoxy)-1,3-dihydro-isobenzofuran-5-yl]-ethoxymethyl}-phosphonic acid diisopropyl ester A mixture of 6-(2-hydroxy-ethyl)-5-methoxy-4-methyl-7-(2-trimethylsilanyl-ethoxy)-3H-isobenzofuran-1-one (79 mg, 0.23 mmol) was heated with bromomethylphosphonic acid diisopropyl ester (120 mg, 0.46 mmol) in the presence of lithium t-butoxide (22 mg, 0.27 mmol) in DMF (2 mL) at 70° C. overnight. The reaction mixture was purified by RP HPLC (acetonitrile and 0.1% aqueous CF$_3$COOH) to provide the desired product. $^1$H NMR (300 MHz, CDCl$_3$) δ 0.00 (s, 9H), 1.13-1.25 (m, 2H), 1.26 (t, 12H, J=6 Hz), 2.12 (s, 3H), 2.98 (t, 2H, J=7 Hz), 3.60-3.73 (m, 4H), 3.77 (s, 3H), 4.05-4.16 (m, 2H), 4.62-4.74 (m, 2H), 5.07 (s, 2H) ppm; MS (m/z) 539 [M+Na]$^+$.

[2-(4-Hydroxy-6-methoxy-7-methyl-3-oxo-1,3-dihydro-isobenzofuran-5-yl)-ethoxymethyl]-phosphonic acid To a solution of {2-[6-methoxy-7-methyl-3-oxo-4-(2-trimethylsilanyl-ethoxy)-1,3-dihydro-isobenzofuran-5-yl]-ethoxymethyl}-phosphonic acid diisopropyl ester (7.5 mg, 0.014 mmol) in acetonitrile (2 mL) and 2,6-lutidine (25 μL, 0.21 mmol) was added trimethylsilyl bromide (27 μL, 0.21 mmol) at room temperature. The reaction was allowed to proceed for 18 hours when completion of the reaction was indicated by LCMS. The reaction was quenched by addition of MeOH and concentration. The residue was purified by RP-HPLC using a C18 column. The collected product was dissolved in a solution of 10% TFA/CH$_2$Cl$_2$ to assure complete deprotection. The reaction mixture was lyophilized to provide the desired product. $^1$H NMR (300 MHz, CD$_3$OD) δ 2.12 (s, 3H), 2.98 (t, 2H, J=7 Hz), 3.66-3.76 (m, 4H), 3.78 (s, 3H), 5.21 (s, 2H) ppm; MS (m/z) 331 [M−H]$^−$.

957
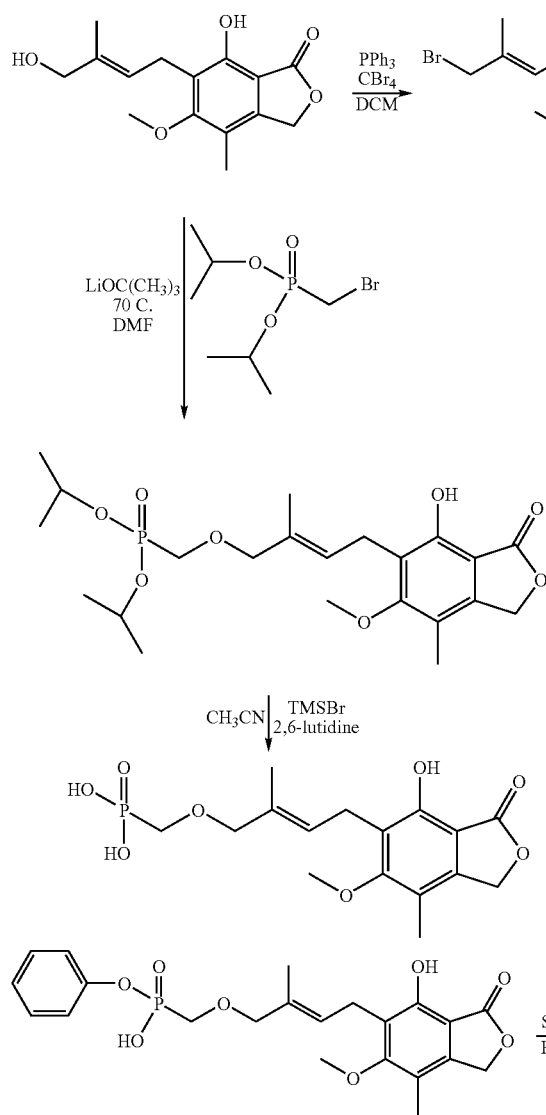
958
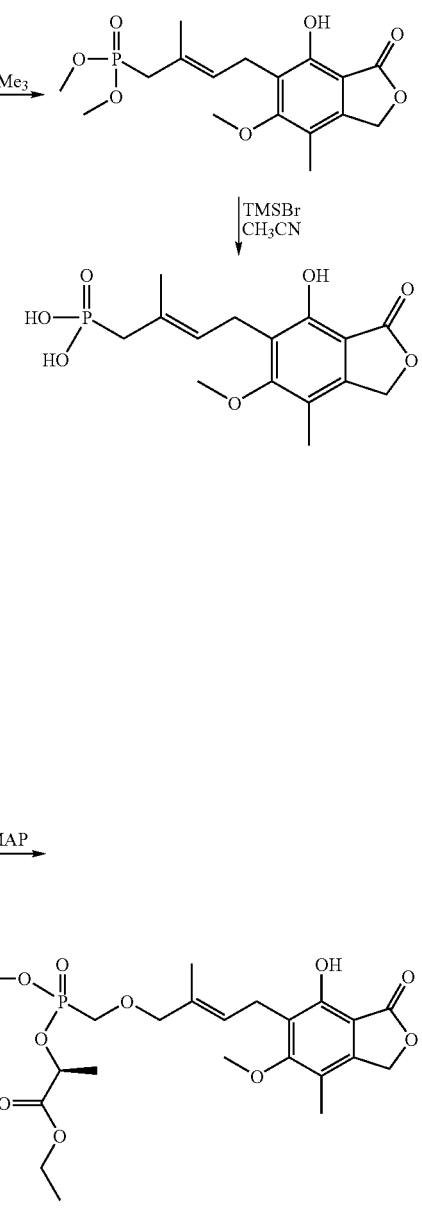
Example 256
Preparation of Representative Compounds of the Invention
Representative compounds of the invention can be prepared as illustrated below.
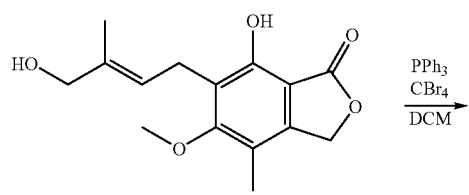
-continued
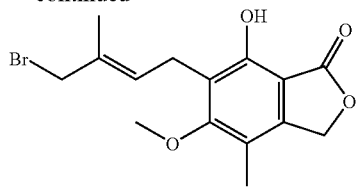
6-(4-Bromo-3-methyl-but-2-enyl)-7-hydroxy-5-methoxy-4-methyl-3H-isobenzofuran-1-one
Polymer-supported triphenylphosphine (3 mmol/g, 0.5 g) was soaked in dichloromethane (10 mL) for 1 hour 7-Hydroxy-6-(4-hydroxy-3-methyl-but-2-enyl)-5-methoxy-4- methyl-3H-isobenzofuran-1-one (100 mg, 0.36 mmol) and carbon tetrabromide (143 mg, 0.43 mmol) were added sequentially and the mixture was shaken for 1 hour at room temperature. More carbon tetrabromide (143 mg, 0.43 mmol) was added and the mixture was shaken further for 1 hour The mixture was filtered and the filtrate was concentrated. The residue was chromatographed on silica gel (0% to 60% ethyl acetate/hexanes) to afford 6-(4-bromo-3-methyl-but-2-enyl)-7-hydroxy-5-methoxy-4-methyl-3H-isobenzofuran-1-one as an oil (52 mg, 42%); $^1$H NMR (300 MHz, CDCl$_3$) δ 1.95 (s, 3H), 2.16 (s, 3H), 3.44 (d, J=7.2, 2H), 3.78 (s, 3H), 3.98 (s, 2H), 5.21 (s, 2H), 5.68 (t, J=7.2 Hz, 1H), 7.71 (brs, 1H) ppm.

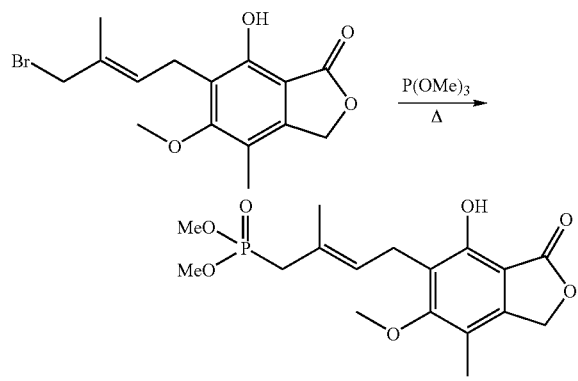

[4-(4-Hydroxy-6-methoxy-7-methyl-3-oxo-1,3-dihydro-isobenzofuran-5-yl)-2-methyl-but-2-enyl]-phosphonic acid dimethyl ester A solution of 6-(4-bromo-3-methyl-but-2-enyl)-7-hydroxy-5-methoxy-4-methyl-3H-isobenzofuran-1-one (33 mg, 0.097 mmol) in trimethylphosphite (1.0 mL, 8.5 mmol) was heated to 100° C. for 1 hour, whereupon complete reaction was indicated by LCMS. The reaction was worked up by removal of the excess reagent under reduced pressure and the residue was purified by silica gel chromatography using EtOAc-hexanes (20-100%) to provide 20 mg (60%) of the desired product. $^1$H NMR (300 MHz, CDCl$_3$) δ 1.90 (s, 3H), 2.09 (s, 3H), 2.48 (d, 2H, J=22 Hz), 3.38 (t, 2H, J=6 Hz), 3.64 (d, 6H, J=11 Hz), 3.72 (s, 3H), 5.14 (s, 2H), 5.33 (q, 1H, J=6 Hz), 7.65 (br s, 1H) ppm; MS (m/z) 371 [M+H]$^+$.

Example 257

Preparation of Representative Compounds of the Invention

Representative compounds of the invention can be prepared as illustrated below.

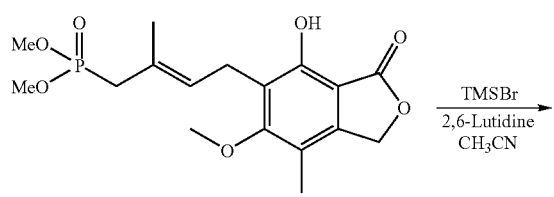

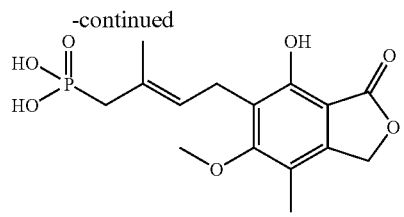

[4-(4-Hydroxy-6-methoxy-7-methyl-3-oxo-1,3-dihydro-isobenzofuran-5-yl)-2-methyl-but-2-enyl]-phosphonic acid To a solution of [4-(4-hydroxy-6-methoxy-7-methyl-3-oxo-1,3-dihydro-isobenzofuran-5-yl)-2-methyl-but-2-enyl]-phosphonic acid dimethyl ester (18 mg, 0.049 mmol) in acetonitrile (2 mL) was added TMSBr (63 μL, 0.49 mmol) and 2,6-lutidine (85 μL, 0.73 mmol) at 0° C. The reaction solution was allowed to warm to room temperature and stirred for 2 hours when completion of the reaction was observed by LCMS. The reaction was cooled to 0° C. and quenched by the addition of MeOH. The reaction mixture was concentrated under reduced pressure and the residue was purified by RP HPLC using a C18 column with a gradient of H$_2$O-acetonitrile (5-0%) over 20 minutes to provide 12.2 mg (73%) of the product. $^1$H NMR (300 MHz, CD$_3$OD) δ 1.95 (s, 3H), 2.15 (s, 3H), 2.48 (d, 2H, J=22 Hz), 3.44 (t, 2H, J=6 Hz), 3.79 (s, 3H), 5.24 (s, 2H), 5.38 (q, 1H, J=7 Hz), 6.87 (br s, 1H) ppm; MS (m/z) 341 [M−H]$^−$.

Example 258

Preparation of Representative Compounds of the Invention

Representative compounds of the invention can be prepared as illustrated below.

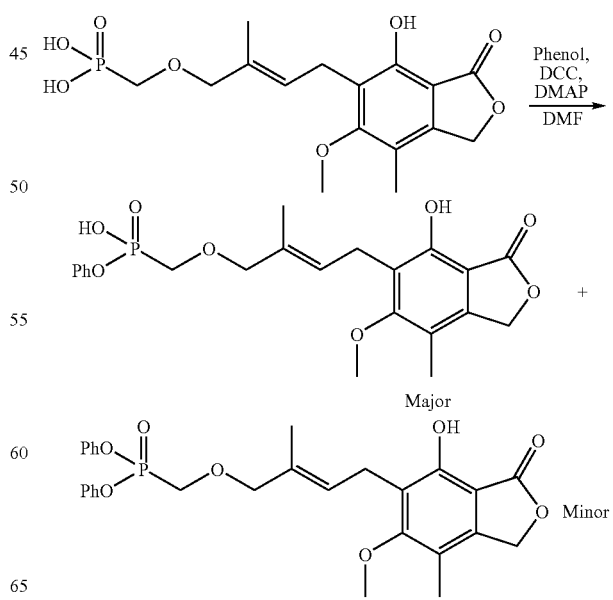

[4-(4-Hydroxy-6-methoxy-7-methyl-3-oxo-1,3-dihydro-isobenzofuran-5-yl)-2-methyl-but-2-enyloxymethyl]-phosphonic acid monophenyl ester and [4-(4-Hydroxy-6-methoxy-7-methyl-3-oxo-1,3-dihydro-isobenzofuran-5-yl)-2-methyl-but-2-enyloxymethyl]-phosphonic acid diphenyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid (49 mg, 0.13 mmol) in DMF (0.4 mL) and phenol (62 mg, 0.65 mmol) was added dicyclohexyl carbodiimide (107 mg, 0.52 mmol) and DMAP (8 mg, 0.065 mmol) in DMF (0.6 mL), slowly at 0° C. The reaction was allowed to warm to room temperature and heated to 140° C. for 10 hours. After cooling to room temperature the mixture was filtered and extracted with aqueous 1N NaOH solution. The aqueous layer was acidified with aqueous 1N HCl and extracted with EtOAc. The organic layer was dried over $Na_2SO_4$ and concentrated to dryness. The residue was purified by RP HPLC to provide 18.5 mg of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (major product, Example 8) as a pale yellow solid and 4.1 mg of [4-(4-hydroxy-6-methoxy-7-methyl-3-oxo-1,3-dihydro-isobenzofuran-5-yl)-2-methyl-but-2-enyloxymethyl]-phosphonic acid diphenyl ester (minor product) also as a pale yellow solid. Major product: $^1$H NMR (300 MHz, $CD_3OD$) δ 1.82 (s, 3H), 2.16 (s, 3H), 3.46 (d, 2H, J=7 Hz), 3.70 (d, 2H, J=8 Hz), 3.77 (s, 3H), 3.96 (s, 2H), 5.25 (s, 2H), 5.52 (t, 1H, J=8 Hz), 7.10-7.21 (m, 3H), 7.30 (t, 2H, J=8 Hz) ppm; $^{31}$P (121.4 MHz, $CD_3OD$) δ 17.3 ppm; MS (m/z) 449.0 [M+H]$^+$, 471.2 [M+Na]$^+$. Minor product: $^1$H NMR (300 MHz, $CD_3OD$) δ 1.82 (s, 3H), 2.15 (s, 3H), 3.47 (d, 2H, J=7 Hz), 3.77 (s, 3H), 3.98-4.06 (m, 4H), 5.25 (s, 2H), 5.50-5.61 (m, 1H), 7.10-7.25 (m, 6H), 7.30-7.41 (m, 4H) ppm; $^{31}$P (121.4 MHz, $CD_3OD$) δ 16.3 ppm; MS (m/z) 525.2 [M+H]$^+$, 547.2 [M+Na]$^+$.

Example 259

Preparation of Representative Compounds of the Invention

Representative compounds of the invention can be prepared as illustrated below.

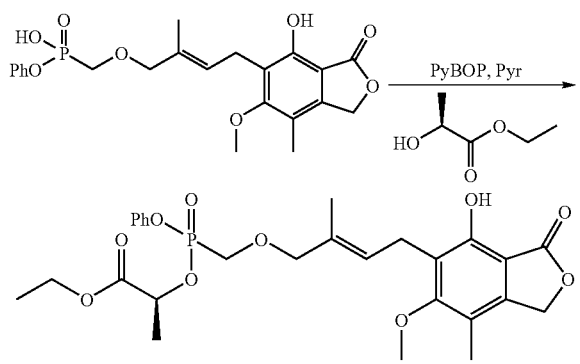

2-{[4-(4-Hydroxy-6-methoxy-7-methyl-3-oxo-1,3-dihydro-isobenzofuran-5-yl)-2-methyl-but-2-enyloxymethyl]-phenoxy-phosphinoyloxy}-propionic acid ethyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (18.5 mg, 0.040 mmol) and ethyl (S)-(−)-lactate (47 μL, 0.400 mmol) in pyridine (0.5 mL) was added PyBOP (32 mg, 0.060 mmol). The solution was stirred at room temperature for 1 hour, when an additional portion of PyBOP (21 mg, 0.040 mmol) was added. The solution was stirred for another hour and concentrated. The residue was purified by HPLC to provide 7.5 mg of the desired product as a clear oil. $^1$H NMR (300 MHz, $CD_3OD$) δ 1.22 and 1.25 (t, 3H, J=7 Hz), 1.42 and 1.50 (d, 3H, J=7 Hz), 1.82 and 1.83 (s, 3H), 2.16 (s, 3H), 3.47 (d, 2H, J=7 Hz), 3.78 (s, 3H), 3.89 (d, 1H, J=8 Hz), 3.93-4.02 (m, 3H), 4.10-4.22 (m, 2H), 4.94-5.08 (m, 1H), 5.25 (s, 2H), 5.50-5.60 (m, 1H), 7.15-7.27 (m, 3H), 7.33-7.41 (m, 2H) ppm; $^{31}$P (121.4 MHz, $CD_3OD$) δ 18.9, 20.3 ppm (diastereomers at phosphorus); MS (m/z) 549.2 [M+H]$^+$, 571.3 [M+Na]$^+$.

Example 260

Preparation of Representative Compounds of the Invention

Representative compounds of the invention can be prepared as illustrated below.

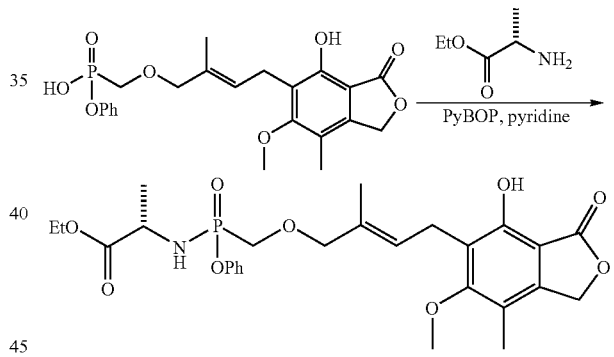

2-{[4-(4-Hydroxy-6-methoxy-7-methyl-3-oxo-1,3-dihydro-isobenzofuran-5-yl)-2-methyl-but-2-enyloxymethyl]-phenoxy-phosphinoylamino}-propionic acid ethyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (20 mg, 0.045 mmol) and L-alanine ethyl ester hydrochloride (68.5 mg, 0.45 mmol) in pyridine (1.0 mL) was added PyBOP (70 mg, 0.14 mmol). After stirring overnight, the mixture was concentrated and the residue purified by RP HPLC using a C18 column with a gradient of $H_2O$, 0.1% TFA-acetonitrile, 0.1% TFA to provide 3.6 mg of the product as a colorless gel. $^1$H NMR (300 MHz, $CD_3OD$) δ 1.17-1.3 (m, 6H), 1.8-1.9 (m, 3H), 2.16 (s, 3H), 3.17 (m, 1H), 3.47 (d, 2H), 3.72-3.8 (m, 5H), 3.92-4.2 (m, 4H), 5.25 (s, 2H), 5.54 (m, 1H), 7.18 (m, 3H), 7.33 (m, 2H) ppm; $^{31}$P (121.4 MHz, $CD_3OD$) δ 24.1, 25.0 ppm (diastereomers at phosphorus); MS (m/z) 546.2 [M−H]$^+$.

Example 261

Preparation of Representative Compounds of the Invention

Representative compounds of the invention can be prepared as illustrated below.

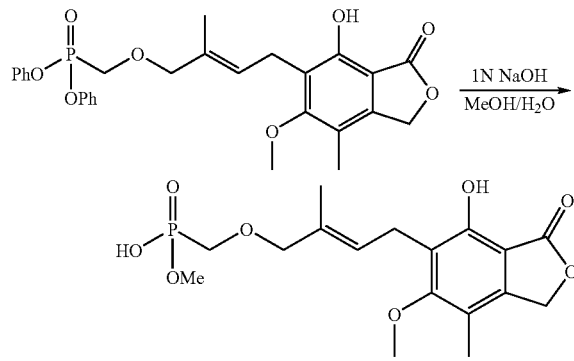

[4-(4-Hydroxy-6-methoxy-7-methyl-3-oxo-1,3-dihydro-isobenzofuran-5-yl)-2-methyl-but-2-enyloxymethyl]-phosphonic acid monomethyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid diphenyl ester (53 mg, 0.1 mmol) in methanol (0.5 mL) was added an aqueous solution of 1N NaOH (300 μL). After stirring overnight, the mixture was concentrated and the residue purified by RP HPLC using a C18 column with a gradient of $H_2O$, 0.1% TFA-acetonitrile, 0.1% TFA to provide 5 mg of the product as a colorless gel, together with the phosphonic acid monophenyl ester (7 mg) and the phosphonic acid dimethyl ester (14.5 mg). $^1$H NMR (300 MHz, $CD_3OD$) δ 1.84 (s, 3H), 2.16 (s, 3H), 3.47 (d, 2H, J=7 Hz), 3.6 (d, 2H, J=12 Hz), 3.75 (d, 3H, J=11 Hz), 3.79 (s, 3H), 3.94 (s, 2H), 5.26 (s, 2H), 5.53 (t, 1H, J=7 Hz) ppm; $^{31}$P (121.4 MHz, $CD_3OD$) δ 21.5 ppm; MS (m/z) 385.2 [M−H]$^+$, 387.1 [M+H]$^+$.

Example 262

Preparation of Representative Compounds of the Invention

Representative compounds of the invention can be prepared as illustrated below.

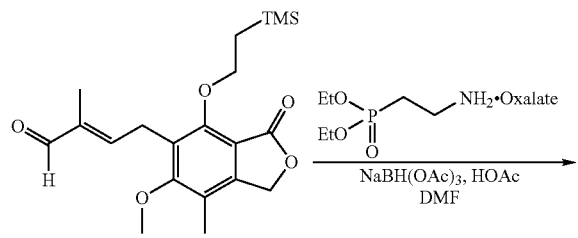

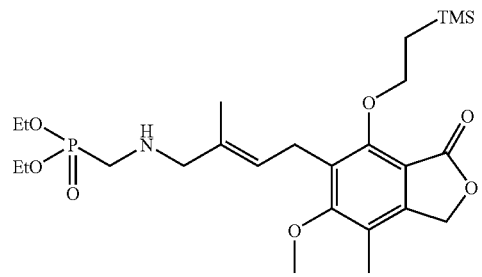

(2-{4-[6-Methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester To a solution of 4-[6-methoxy-7-methyl-3-oxo-4-(2-trimethylsilanyl-ethoxy)-1,3-dihydro-isobenzofuran-5-yl]-2-methyl-but-2-enal (84 mg, 0.22 mmol), (2-amino-ethyl)-phosphonic acid diethyl ester oxalate (91 mg, 0.33 mmol), and sodium triacetoxyborohydride (93 mg, 0.44 mmol) in DMF (1.5 mL) was added acetic acid (60 μL, 1.0 mmol) at room temperature. The solution was stirred for 2 days when it was quenched by addition of saturated aqueous sodium bicarbonate solution and EtOAc. The organic layer was separated and concentrated under reduced pressure. The residue was purified by RP HPLC using a C18 column with a gradient of $H_2O$, 0.1% TFA-acetonitrile, 0.1% TFA to provide 115 mg (96%) of the product as an oil. $^1$H NMR (300 MHz, $CDCl_3$) δ 0.04 (s, 9H), 1.16-1.27 (m, 2H), 1.34 (t, 6H, J=7 Hz), 1.94 (s, 3H), 2.18 (s, 3H), 2.20-2.31 (m, 2H), 3.13-3.31 (m, 2H), 3.48 (d, 2H, J=7 Hz), 3.54 (s, 2H), 3.78 (s, 3H), 4.14 (pent, 4H, J=7 Hz), 4.30-4.37 (m, 2H), 5.13 (s, 2H), 5.65 (t, 1H, J=7 Hz), 6.23 (br s, 2H) ppm; $^{31}$P (121.4 MHz, $CDCl_3$) δ 27.8 ppm; MS (m/z) 542.3 [M+H]$^+$, 564.2 [M+Na]$^+$.

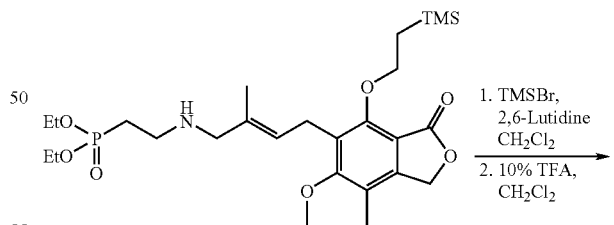

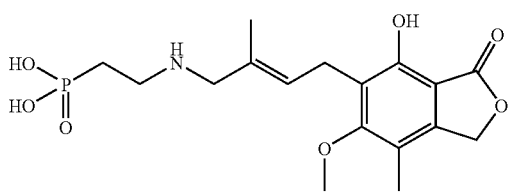

{2-[4-(4-Hydroxy-6-methoxy-7-methyl-3-oxo-1,3-dihydro-isobenzofuran-5-yl)-2-methyl-but-2-enylamino]-ethyl}-phosphonic acid A solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (30 mg, 0.055 mmol), TMSBr (72 μL, 0.55 mmol), and 2,6-lutidine (64 μL, 0.55 mmol) was stirred in CH$_2$Cl$_2$ (1 mL) and DMF (0.5 mL) for 1 hour at ambient temperature. The reaction mixture was purified by RP HPLC using a C18 column with a gradient of H$_2$O, 0.1% TFA-acetonitrile, 0.1% TFA to provide 7.8 mg of the product as a white solid. $^1$H NMR (300 MHz, CD$_3$OD) δ 1.96 (s, 3H), 1.95-2.07 (m, 2H), 2.16 (s, 3H), 3.10-3.24 (m, 2H), 3.51 (d, 2H, J=7 Hz), 3.57 (s, 2H), 3.81 (s, 3H), 5.25 (s, 2H), 5.73 (t, 1H, J=7 Hz) ppm; $^{31}$P (121.4 MHz, CD$_3$OD) δ 20.2 ppm; $^{19}$F NMR (282.6 MHz, CD$_3$OD) δ −74.0 ppm; MS (m/z) 386.3 [M+H]$^+$.

Example 263

Preparation of Representative Compounds of the Invention

Representative compounds of the invention can be prepared as illustrated below.

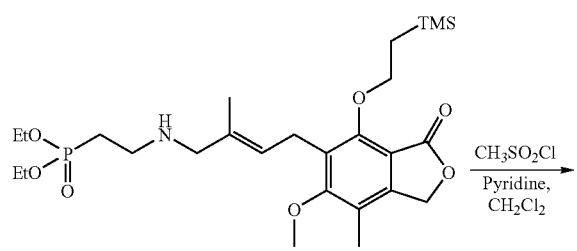

[2-(Methanesulfonyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester A solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (45 mg, 0.092 mmol) in CH$_2$Cl$_2$ (0.5 mL) was stirred with methanesulfonyl chloride (21 μL, 0.28 mmol) and pyridine (45 μL, 0.55 mmol) at ambient temperature overnight. The reaction was quenched by addition of 2 drops of water. The reaction mixture was concentrated and purified by RP HPLC using a C18 column with a gradient of H$_2$O, 0.1% TFA-acetonitrile, 0.1% TFA to provide 36 mg of the product (63%) as a clear gel. $^1$H NMR (300 MHz, CDCl$_3$) δ 0.05 (s, 9H), 1.18-1.29 (m, 2H), 1.29 (t, 6H, J=7 Hz), 1.85 (s, 3H), 2.00-2.13 (m, 2H), 2.19 (s, 3H), 2.85 (s, 3H), 3.32-3.43 (m, 2H), 3.47 (d, 2H, J=7 Hz), 3.69 (s, 2H), 3.79 (s, 3H), 4.05 (pent, 4H, J=7 Hz), 4.30-4.37 (m, 2H), 5.13 (s, 2H), 5.45 (t, 1H, J=7 Hz) ppm; $^{31}$P (121.4 MHz, CD$_3$Cl) δ 27.5 ppm; MS (m/z) 642.2 [M+Na]$^+$.

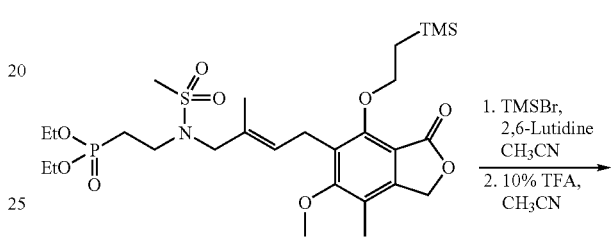

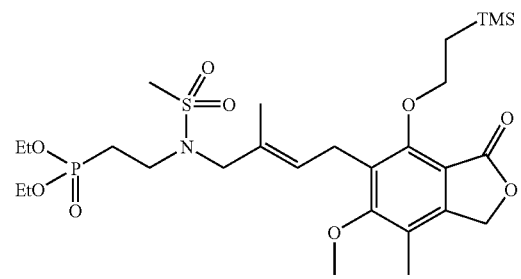

(2-{[4-(4-Hydroxy-6-methoxy-7-methyl-3-oxo-1,3-dihydro-isobenzofuran-5-yl)-2-methyl-but-2-enyl]-methanesulfonyl-amino}-ethyl)phosphonic acid A solution of [2-(methanesulfonyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester (18 mg, 0.029 mmol) in acetonitrile (0.5 mL) was stirred with TMSBr (38 μL, 0.29 mmol) and 2,6-lutidine (34 μL, 0.29 mmol) for 2 hours at room temperature. The reaction was worked up by addition of EtOAc and aqueous 1N HCl. The organic layer was washed with brine and the solvent was removed in vacuo. The residue was suspended in a solution of 10% TFA-CH$_2$Cl$_2$ for 10 minutes before it was dried to provide 9.9 mg of the desired product (73%) as a white solid. $^1$H NMR (300 MHz, DMSO-d6) δ 1.76 (s, 3H), 1.76-1.88 (m, 2H), 2.10 (s, 3H), 2.87 (s, 3H), 3.24-3.35 (m, 2H), 3.39 (d, 2H, J=7 Hz), 3.65 (s, 2H), 3.75 (s, 3H), 5.22 (s, 2H), 5.41-5.48 (m, 1H) ppm; $^{31}$P (121.4 MHz, DMSO-d6) δ 21.4 ppm; MS (m/z) 464.1 [M+H]$^+$.

Example 264

Preparation of Representative Compounds of the Invention

Representative compounds of the invention can be prepared as illustrated below.

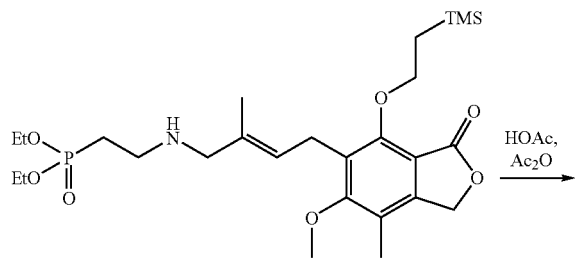

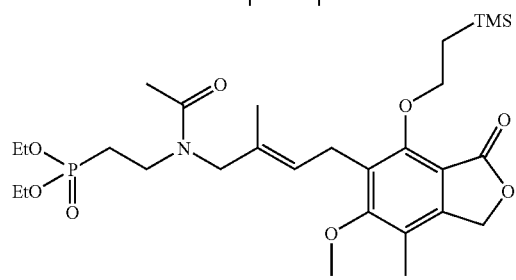

[2-(Acetyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester To a solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (32 mg, 0.059 mmol) in acetic acid (0.5 mL) was added acetic anhydride (0.5 mL). The solution was stirred at room temperature for 90 minutes when it was quenched by addition of 2 drops of water. The solution was dried in vacuo and the residue was purified by RP HPLC using a C18 column with a gradient of $H_2O$, 0.1% TFA-acetonitrile, 0.1% TFA to provide 28 mg of the product (81%) as a clear gel. The NMR data of this compound shows two rotamers in a ratio of 70:30. $^1$H NMR (300 MHz, CDCl$_3$) δ 0.05 (s, 9H), 1.17-1.27 (m, 2H), 1.30 and 1.31 (t, 6H, J=7 Hz), 1.70-1.79 (m, 2H), 1.76 (s, 3H), 2.00 (s, 3H), 2.18 (s, 3H), 3.40-3.52 (m, 2H), 3.46 (d, 2H, J=7 Hz), 3.77 (s, 3H), 3.79 and 3.93 (s, 3H), 4.07 (pent, 4H, J=7 Hz), 4.27-4.35 (m, 2H), 5.13 (s, 2H), 5.22-5.30 (m, 1H) ppm; $^{31}$P (121.4 MHz, CDCl$_3$) δ 27.5 and 28.9 ppm; MS (m/z) 584.1 [M+H]$^+$, 606.2 [M+Na]$^+$.

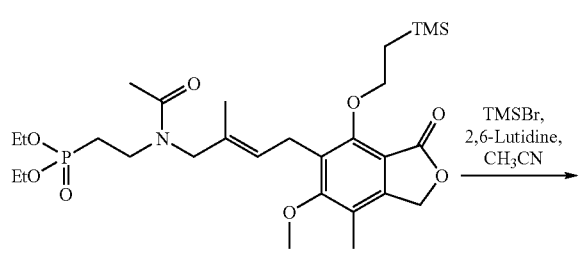

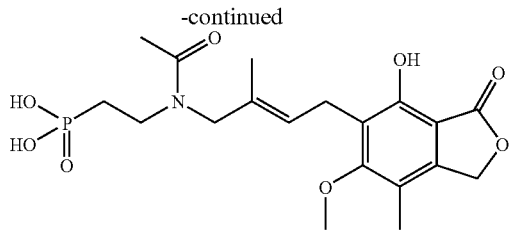

(2-{Acetyl-[4-(4-hydroxy-6-methoxy-7-methyl-3-oxo-1,3-dihydro-isobenzofuran-5-yl)-2-methyl-but-2-enyl]-amino}-ethyl)-phosphonic acid To a solution of [2-(acetyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester (14 mg, 0.024 mmol) in acetonitrile (0.5 mL) was added TMSBr (31 µL, 0.24 mmol) and 2,6-lutidine (28 µL, 0.24 mmol). The solution was stirred at room temperature for 1 hour. The reaction was quenched by addition of methanol and aqueous 1N HCl. The product was extracted with EtOAc. The combined organic extracts were dried over Na$_2$SO$_4$ and concentrated in vacuo. The product was purified by RP HPLC using a C18 column with a gradient of $H_2O$, 0.1% TFA-acetonitrile, 0.1% TFA to provide 5.4 mg of the product (53%) as a white solid. The NMR data of this compound shows two rotamers. $^1$H NMR (300 MHz, CDCl$_3$) δ 1.67 and 1.73 (s, 3H), 1.85-2.12 (m, 5H), 2.13 (s, 3H), 3.30-3.61 (m, 4H), 3.75 (s, 3H), 3.76 (br s, 2H), 5.17 (s, 2H), 5.31 (br s, 1H) ppm; $^{31}$P (121.4 MHz, CDCl$_3$) δ 27.5 and 28.8 ppm; MS (m/z) 428.2 [M+H]$^+$, 450.2 [M+Na]$^+$.

Example 265

Preparation of Representative Compounds of the Invention

Representative compounds of the invention can be prepared as illustrated below.

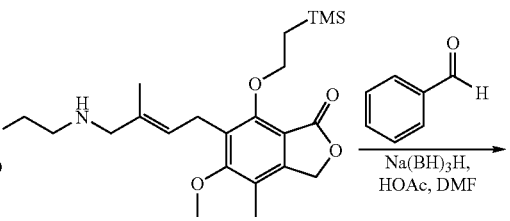

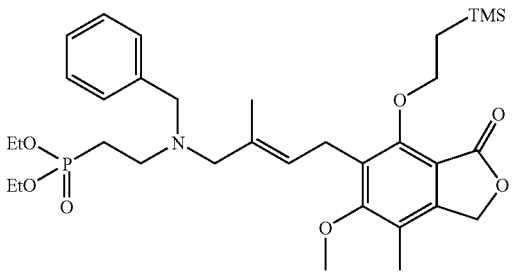

[2-(Benzyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester A solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (30 mg, 0.055 mmol), benzaldehyde (5.6 μL, 0.055 mmol), and sodium triacetoxyborohydride (23 mg, 0.11 mmol) was stirred with acetic acid (15.7 μL, 0.28 mmol) in DMF (0.5 mL) at room temperature over night. The reaction was quenched with a 10% aqueous Na$_2$CO$_3$ solution and the product was extracted with EtOAc. The organic layer was dried and concentrated under reduced pressure. The product was purified purified by RP HPLC using a C18 column with a gradient of H$_2$O, 0.1% TFA-acetonitrile, 0.1% TFA to provide 15 mg of the product (43%) as a clear gel. $^1$H NMR (300 MHz, CDCl$_3$) δ 0.02 (s, 9H), 1.18-1.25 (m, 2H), 1.24 (t, 6H, J=7 Hz), 1.86 (s, 3H), 1.88-2.02 (m, 2H), 2.16 (s, 3H), 2.65-2.74 (m, 2H), 3.93 (s, 2H), 3.46 (br d, 4H, J=7 Hz), 3.76 (s, 3H), 4.00 (pent, 4H, J=7 Hz), 4.25-4.34 (m, 2H), 5.11 (s, 2H), 5.34-5.43 (m, 1H), 7.18-7.33 (m, 5H) ppm; $^{31}$P (121.4 MHz, CDCl$_3$) δ 30.9 ppm; MS (m/z) 632.4 [M+H]$^+$, 654.3 [M+Na]$^+$.

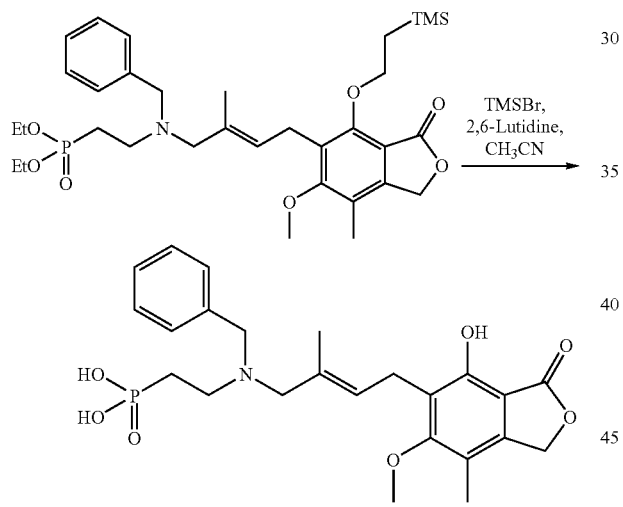

(2-{Benzyl-[4-(4-hydroxy-6-methoxy-7-methyl-3-oxo-1,3-dihydro-isobenzofuran-5-yl)-2-methyl-but-2-enyl]-amino}-ethyl)-phosphonic acid A solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (15 mg, 0.024 mmol) in acetonitrile (0.5 mL) was treated with TMSBr (31 μL, 0.24 mmol) and 2,6-lutidine (28 μL, 0.24 mmol). The solution was stirred at ambient temperature for 1 hour, when it was quenched with methanol. The solvent was removed under reduced pressure and the residue was purified by RP HPLC using a C18 column with a gradient of H$_2$O, 0.1% TFA-acetonitrile, 0.1% TFA to provide 11 mg of the product (93%) as a white solid. $^1$H NMR (300 MHz, CD$_3$OD) δ 1.89 (s, 3H), 2.03-2.15 (m, 2H), 2.14 (s, 3H), 3.30-3.47 (m, 2H), 3.50 (br s, 2H), 3.62 (br s, 2H), 3.79 (s, 3H), 4.28 (s, 2H), 5.23 (s, 2H), 5.76 (br s, 1H), 7.46 (br s, 5H) ppm; $^{31}$P (121.4 MHz, CDCl$_3$) δ 20.1 ppm; MS (m/z) 476.3 [M+H]$^+$, 498.3 [M+Na]$^+$.

Example 266

Preparation of Representative Compounds of the Invention

Representative compounds of the invention can be prepared as illustrated below.

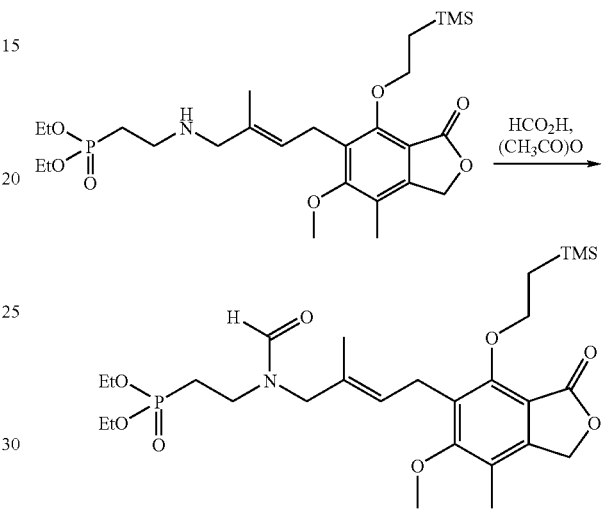

[2-(Formyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester To a solution of (2-{4-[6-Methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (74 mg, 0.14 mmol) in formic acid (1 mL) was added formic anhydride (1 mL) and the solution was stirred at room temperature for 1 hour. The reaction mixture was concentrated and the crude product carried onto the next step. The NMR data of this compound shows two rotamers with the ratio of 70:30. $^1$H NMR (300 MHz, CDCl$_3$) δ 0.05 (s, 9H), 1.18-1.28 (m, 2H), 1.28 and 1.30 (t, 6H, J=7 Hz), 1.74 (s, 3H), 1.84-2.08 (m, 2H), 2.19 (s, 3H), 3.34-3.45 (m, 2H), 3.47 (d, 2H, J=7 Hz), 3.72 and 3.87 (s, 2H), 3.78 and 3.79 (s, 3H), 4.06 and 4.07 (pent, 4H, J=7 Hz), 4.26-4.37 (m, 2H), 5.13 (s, 2H), 5.30-5.46 (m, 1H), 8.03 and 8.19 (s, 1H) ppm; $^{31}$P (121.4 MHz, CDCl$_3$) δ 27.5 and 28.1 ppm; MS (m/z) 570.1 [M+H]$^+$, 592.2 [M+Na]$^+$.

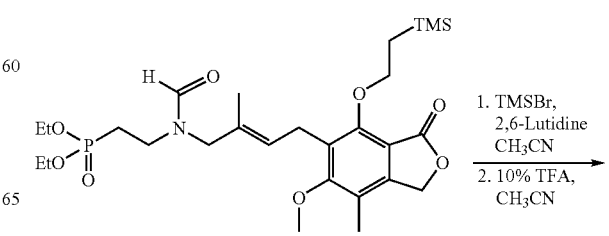

-continued

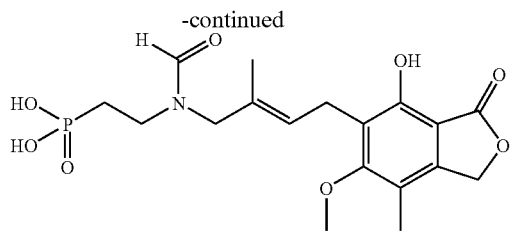

(2-{Formyl-[4-(4-hydroxy-6-methoxy-7-methyl-3-oxo-1,3-dihydro-isobenzofuran-5-yl)-2-methyl-but-2-enyl]-amino}-ethyl)-phosphonic acid To a solution of crude [2-(formyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester (78 mg, 0.14 mmol) in acetonitrile (1 mL) was added TMSBr (177 μL, 1.4 mmol) and 2,6-lutidine (163 μL, 1.4 mmol). The solution was stirred at room temperature for 1 hour when it was quenched by addition of methanol and 1N aqueous HCl. The product was extracted with EtOAc and purified by RP HPLC using a C18 column with a gradient of $H_2O$, 0.1% TFA-acetonitrile, 0.1% TFA to provide 29 mg of the product as a white solid. The NMR data of this compound shows two rotamers with the ratio of approximately 70:30. $^1$H NMR (300 MHz, $CD_3OD$) δ 1.62 and 1.64 (s, 3H), 1.83-1.98 (m, 2H), 2.16 (s, 3H), 3.38-3.55 (m, 4H), 3.78 (s, 3H), 3.80 and 3.91 (s, 2H), 5.22 (s, 2H), 5.39-5.52 (m, 1H), 8.03 and 8.18 (s, 1H) ppm; MS (m/z) 414.2 [M+H]$^+$, 436.2 [M+Na]$^+$.

Example 267

Preparation of Representative Compounds of the Invention

Representative compounds of the invention can be prepared as illustrated below.

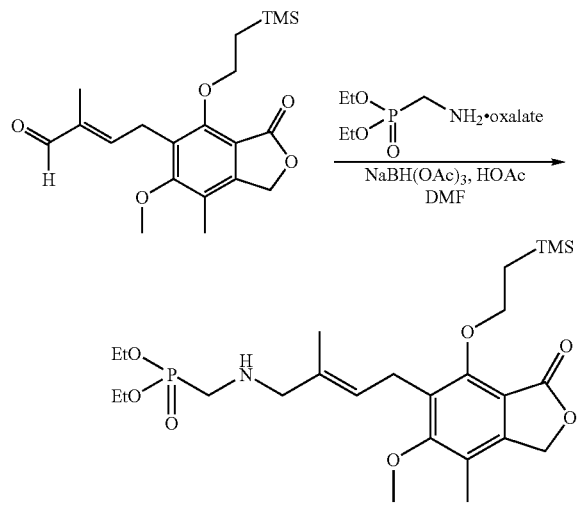

({4-[6-Methoxy-7-methyl-3-oxo-4-(2-trimethylsilanyl-ethoxy)-1,3-dihydro-isobenzofuran-5-yl]-2-methyl-but-2-enylamino}-methyl)-phosphonic acid diethyl ester To a solution of 4-[6-methoxy-7-methyl-3-oxo-4-(2-trimethylsilanyl-ethoxy)-1,3-dihydro-isobenzofuran-5-yl]-2-methyl-but-2-enal (500 mg, 1.33 mmol), (2-aminomethyl) phosphonic acid diethyl ester oxalate (376 mg, 1.46 mmol), sodium triacetoxyborohydride (563 mg, 2.66 mmol) in DMF (10 mL) was added acetic acid (380 μL, 6.65 mmol) at room temperature. The solution was stirred overnight when it was quenched by addition of saturated aqueous sodium bicarbonate solution and EtOAc. The organic layer was separated and concentrated under reduced pressure. The residue was purified by silica gel chromatography to provide 500 mg (71%) of the product as an oil. $^1$H NMR (300 MHz, $CDCl_3$) δ 0.00 (s, 9H), 1.13-1.23 (m, 2H), 1.25 and 1.27 (t, 6H, J=7 Hz), 1.65-1.75 (m, 2H), 1.77 (s, 3H), 2.13 (s, 3H), 2.80 (s, 1H), 3.14 (s, 2H), 3.41 (d, 2H, J=7 Hz), 3.73 (s, 3H), 4.08 and 4.09 (pent, 4H, J=7 Hz), 4.20-4.30 (m, 2H), 5.08 (s, 2H), 5.30 (t, 1H, J=7 Hz) ppm; $^{31}$P (121.4 MHz, $CDCl_3$) δ 26.5 ppm; MS (m/z) 528.1 [M+H]$^+$, 550.2 [M+Na]$^+$.

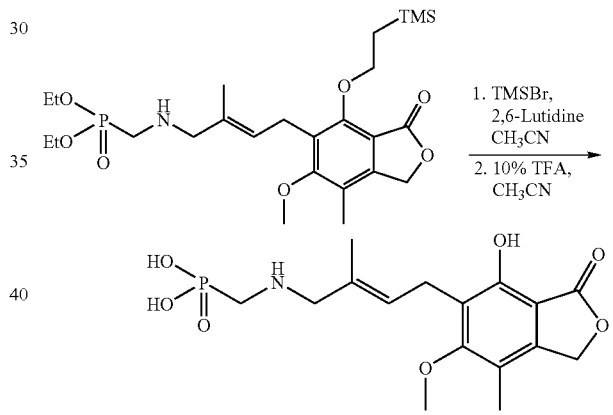

{[4-(4-Hydroxy-6-methoxy-7-methyl-3-oxo-1,3-dihydro-isobenzofuran-5-yl)-2-methyl-but-2-enylamino]-methyl}-phosphonic acid To a solution of ({4-[6-methoxy-7-methyl-3-oxo-4-(2-trimethylsilanyl-ethoxy)-1,3-dihydro-isobenzofuran-5-yl]-2-methyl-but-2-enylamino}-methyl)-phosphonic acid diethyl ester (20 mg, 0.038 mmol) in DMF (0.5 mL) was added TMSBr (49 μL, 0.38 mmol) and 2,6-lutidine (44 μL, 0.38 mmol). The solution was stirred at room temperature for 1 hour when it was quenched by addition of methanol. The product was purified by RP HPLC using a C18 column with a gradient of $H_2O$, 0.1% TFA-acetonitrile, 0.1% TFA to provide 5.6 mg of the product as a white solid. $^1$H NMR (300 MHz, $CD_3OD$ and $CDCl_3$) δ 1.93 (s, 3H), 2.13 (s, 3H), 2.94 (br d, 2H, J=11 Hz), 3.42-3.53 (m, 2H), 3.60 (s, 2H), 3.78 (s, 3H), 5.22 (s, 2H), 5.71 (br s, 1H) ppm; $^{31}$P (121.4 MHz, $CDCl_3$) δ 8.5 ppm; MS (m/z) 372.2 [M+H]$^+$, 743.2 [2M+H]$^+$.

Example 268

Preparation of Representative Compounds of the Invention

Representative compounds of the invention can be prepared as illustrated below.

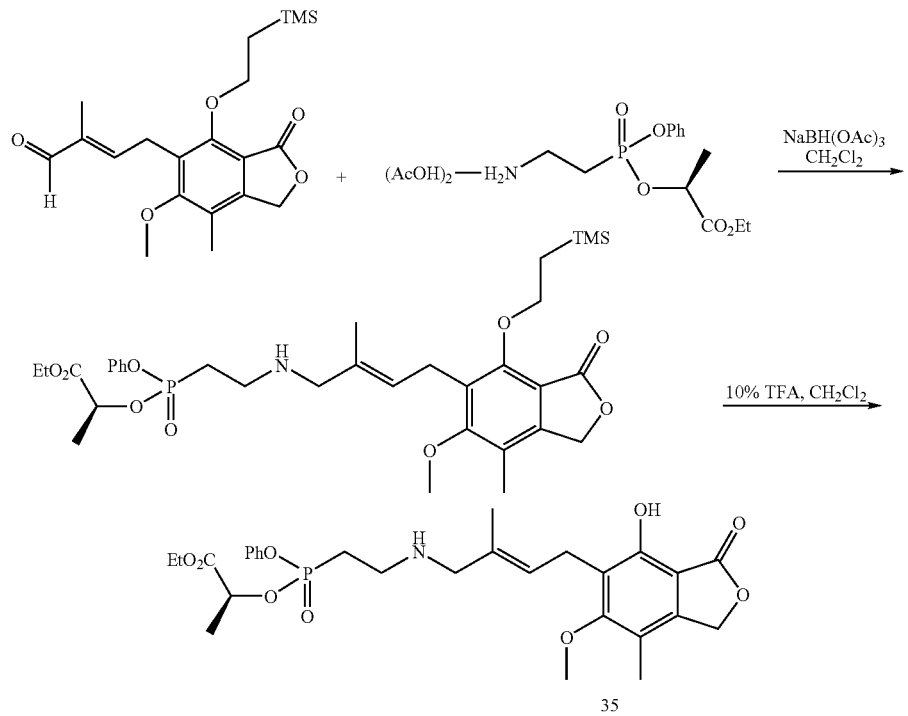

2-({2-[4-(4-Hydroxy-6-methoxy-7-methyl-3-oxo-1, 3-dihydro-isobenzofuran-5-yl)-2-methyl-but-2-enylamino]-ethyl}-phenoxy-phosphinoyloxy)-propionic acid ethyl ester A solution of 4-[6-methoxy-7-methyl-3-oxo-4-(2-trimethylsilanyl-ethoxy)-1,3-dihydro-isobenzofuran-5-yl]-2-methyl-but-2-enal (188 mg, 0.5 mmol) was stirred with 2-[(2-aminoethyl)phenoxy-phosphinoyloxy]-propionic acid ethyl ester acetic acid salt (315.8 mg, 0.75 mmol) in CH$_2$Cl$_2$ (3 mL) for 2 hours at ambient temperature. Sodium triacetoxyborohydride (159 mg, 0.75 mmol) was added to the solution and the reaction was allowed to proceed for 1 hour. The reaction was quenched by addition of a saturated aqueous solution of NaHCO$_3$ and the product was extracted with EtOAc. The organic layer was removed under reduced pressure and the residue was resuspended in a 10% TFA/CH$_2$Cl$_2$ for 1 hour. The reaction mixture was concentrated and the product was purified by RP HPLC using a C18 column with a gradient of H$_2$O, 0.1% TFA-acetonitrile, 0.1% TFA to provide 198 mg of the product as a white solid. The NMR data of this compound shows two diastereomers at phosphorus in a ratio of approximately 45:55. $^1$H NMR (300 MHz, CD$_3$OD) δ 1.23 and 1.24 (t, 3H, J=7 Hz), 1.38 and 1.52 (d, 3H, J=7 Hz), 1.97 and 1.98 (s, 3H), 2.14 (s, 3H), 2.44-2.66 (m, 2H), 3.31-3.48 (m, 2H), 3.51 (d, 2H, J=7 Hz), 3.66 (d, 2H, J=5 Hz), 3.80 (s, 3H), 4.10-4.27 (m, 2H), 4.90-5.10 (m, 1H), 5.20 (s, 2H), 5.73-5.82 (m, 1H), 7.15-7.27 (m, 3H), 7.35-7.45 (m, 2H) ppm; $^{31}$P (121.4 MHz, CD$_3$OD) δ 22.6, 24.3 ppm; MS (m/z) 561.9 [M+H]$^+$.

Example 269

Preparation of Representative Compounds of the Invention

Representative compounds of the invention can be prepared as illustrated below.

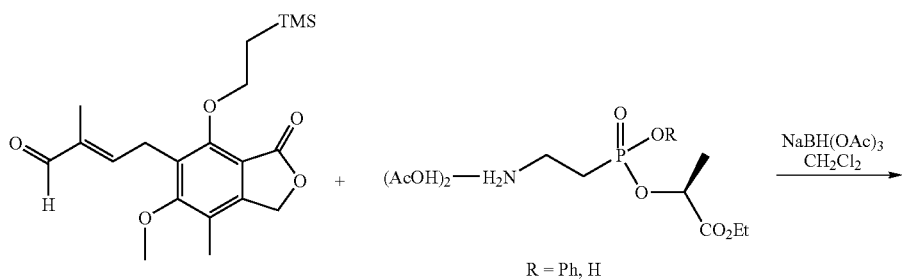

R = Ph, H

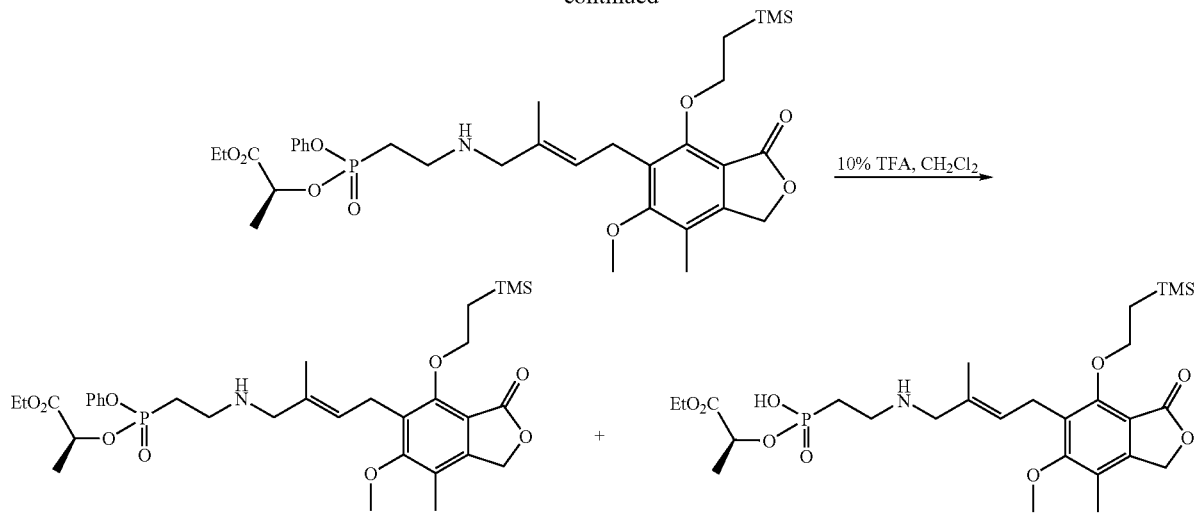

2-[Hydroxy-(2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphinoyloxy]-propionic acid ethyl ester A solution of 4-[6-methoxy-7-methyl-3-oxo-4-(2-trimethylsilanyl-ethoxy)-1,3-dihydro-isobenzofuran-5-yl]-2-methyl-but-2-enal (38 mg, 0.1 mmol) was stirred with 2-[(2-aminoethyl)-phenoxy-phosphinoyloxy]-propionic acid ethyl ester acetic acid (63 mg, 0.15 mmol) in CH$_2$Cl$_2$ (1 mL) for 2 hours at ambient temperature. Sodium triacetoxyborohydride (32 mg, 0.15 mmol) was added to the solution and the reaction was allowed to proceed for 1 hour. The reaction was quenched by addition of a saturated aqueous solution of NaHCO$_3$ and the product was extracted with EtOAc. The organic layer was removed under reduced pressure and the residue was re-suspended in 10% TFA/CH$_2$Cl$_2$ for 1 hour. The reaction mixture was concentrated and the product was purified by RP HPLC using a C18 column with a gradient of H$_2$O, 0.1% TFA-acetonitrile, 0.1% TFA to provide 15 mg of the product (154-2). $^1$H NMR (300 MHz, CDCl$_3$) δ 0.04 (s, 9H), 1.15-1.24 (m, 2H), 1.26 (t, 3H, J=7 Hz), 1.48 (d, 3H, J=7 Hz), 1.93 (s, 3H), 2.10-2.25 (m, 2H), 2.18 (s, 3H), 3.10-3.31 (m, 2H), 3.48 (d, 2H, J=7 Hz), 3.48-3.61 (m, 2H), 3.77 (s, 3H), 4.04-4.21 (m, 2H), 4.29-4.40 (m, 2H), 4.81-4.92 (m, 1H), 5.13 (s, 2H), 5.64 (t, 1H, J=7 Hz), 8.70-9.11 (m, 3H) ppm; $^{31}$P (121.4 MHz, CDCl$_3$) δ 21.9 ppm; MS (m/z) 586.3 [M+H]$^+$, 1171.4 [2M+H]$^+$.

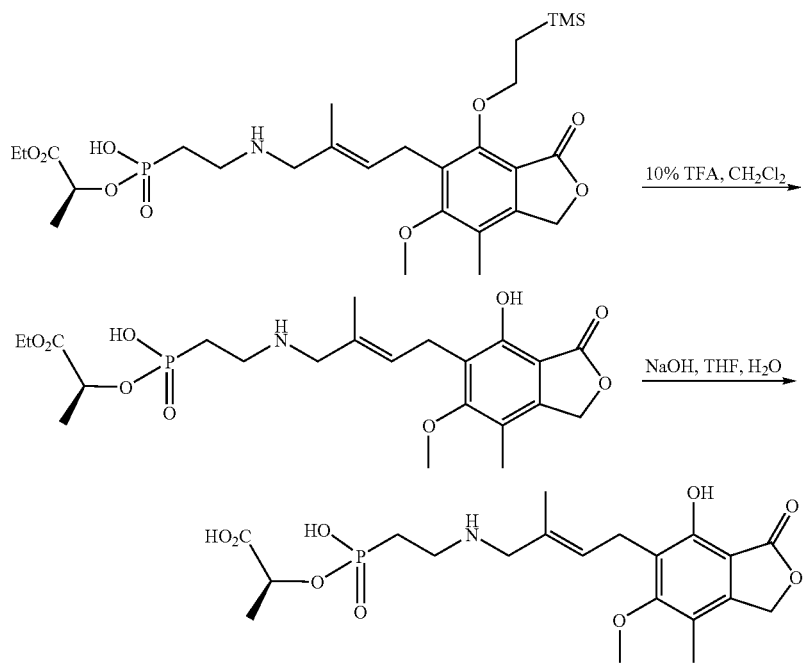

2-(Hydroxy-{2-[4-(4-hydroxy-6-methoxy-7-methyl-3-oxo-1,3-dihydro-isobenzofuran-5-yl)-2-methyl-but-2-enylamino]-ethyl}-phosphinoyloxy)-propionic acid A solution of 2-[hydroxy-(2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphinoyloxy]-propionic acid ethyl ester (15 mg, 0.026 mmol) in 10% TFA-CH$_2$Cl$_2$ (1 mL) was stirred at ambient temperature for 10 minutes. The reaction was worked up by removal of the solvent. The residue was dissolved in THF (0.5 mL) and water (0.4 mL) and 1N aqueous NaOH solution (0.1 mL) was added. The solution was stirred at room temperature for 20 minutes when it was acidified with 1N aqueous HCl solution. The resulting solution was purified by RP HPLC using a C18 column with a gradient of H$_2$O, 0.1% TFA-acetonitrile, 0.1% TFA to provide 6.8 mg of the product as a white solid. $^1$H NMR (300 MHz, CDCl$_3$) δ 1.38 (d, 3H, J=7 Hz), 1.91 (s, 3H), 2.13 (s, 3H), 2.12-2.28 (m, 2H), 3.12-3.33 (m, 2H), 3.41 (d, 2H, J=6 Hz), 3.56 (br s, 2H), 3.75 (s, 3H), 4.71-4.88 (m, 1H), 5.16 (s, 2H), 5.58-5.71 (m, 1H), 7.88 (br s, 3H), 8.60 (br s, 1H), 8.78 (br s, 1H) ppm; $^{31}$P (121.4 MHz, CDCl$_3$) δ 22.0 ppm; MS (m/z) 458.3 [M+H]$^+$, 480.3 [M+Na]$^+$.

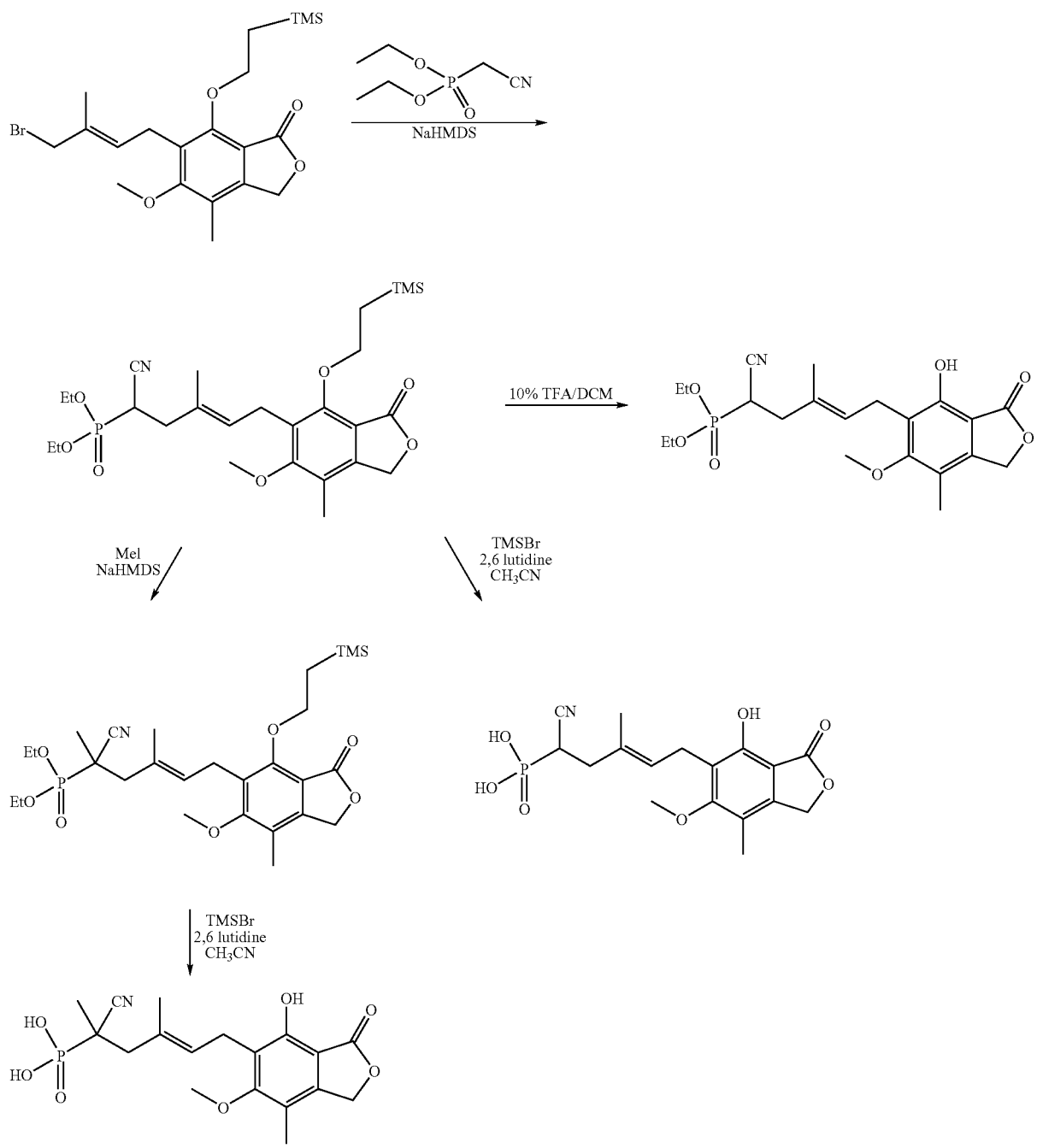

Example 270

Preparation of Representative Compounds of the Invention

Representative compounds of the invention can be prepared as illustrated below.

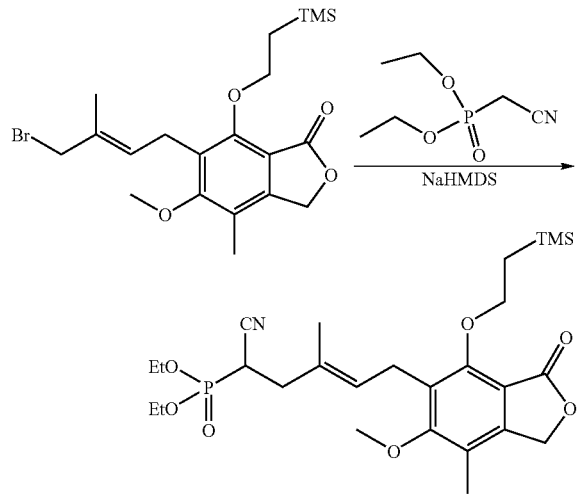

{1-Cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester To a solution of diethyl cyanomethylphosphonate (241 mg, 1.38 mmol) in THF (1 mL) was added a THF solution of sodium bis(trimethysilyl)amide (1.0 M, 1.13 mL, 1.15 mmol). After stirring for 30 minutes, the solution was added dropwise to a solution of 6-(4-bromo-3-methyl-but-2-enyl)-7-hydroxy-5-methoxy-4-methyl-3H-isobenzofuran-1-one (100 mg, 0.23 mmol) in THF (1 mL). The resulting mixture was allowed to stir at room temperature for one hour before saturated aqueous ammonium chloride was added. The reaction mixture was extracted with ethyl acetate. The organic layer was dried over sodium sulfate and concentrated to dryness. The residue was purified by silica gel column chromatography, affording 110 mg (90%) of the desired product. $^1$H NMR (300 MHz, CDCl$_3$) δ 0.04 (s, 9H), 1.24 (dd, J=7, 8 Hz, 2H), 1.36 (t, 6H), 1.86 (s, 3H), 2.17 (s, 3H), 2.43-2.57 (m, 2H), 3.04-3.17 (m, 1H), 3.47 (d, J=7.2 Hz, 2H), 3.79 (s, 3H), 4.12-4.37 (m, 6H), 5.13 (s, 2H), 5.44 (t, J=7.2 Hz, 1H) ppm; $^{31}$P (121.4 MHz, CDCl$_3$) δ 18.18 ppm; MS (m/z) 560 [M+Na]$^+$.

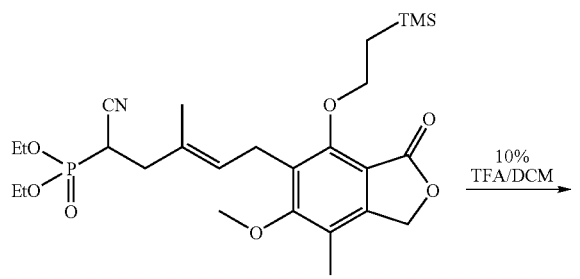

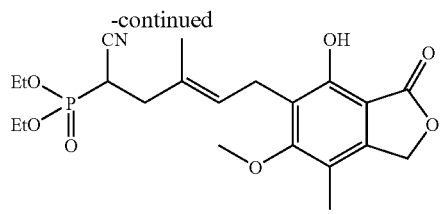

[1-Cyano-5-(4-hydroxy-6-methoxy-7-methyl-3-oxo-1,3-dihydro-isobenzofuran-5-yl)-3-methyl-pent-3-enyl]-phosphonic acid diethyl ester {1-Cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (25 mg, 0.047 mmol) was dissolved in a solution of 10% TFA/CH$_2$Cl$_2$ (5 mL) and stirred at room temperature for 2 hours. The reaction mixture was dried under reduced pressure and the product was purified by RP-HPLC to provide 16 mg (80%) of the desired product as a white solid. $^1$H NMR (300 MHz, CDCl$_3$) δ 1.38 (t, 6H), 1.86 (s, 3H), 2.15 (s, 3H), 2.40-2.58 (m, 2H), 3.01-3.14 (m, 1H), 3.45 (d, J=7.2 Hz, 2H), 3.79 (s, 3H), 4.18-4.30 (m, 4H), 5.21 (s, 2H), 5.48 (t, J=7.2 Hz, 1H) ppm; $^{31}$P (121.4 MHz, CDCl$_3$) δ 18.09 ppm; MS (m/z) 436 [M−H]$^−$, 438 [M+H]$^+$.

Example 271

Preparation of Representative Compounds of the Invention

Representative compounds of the invention can be prepared as illustrated below.

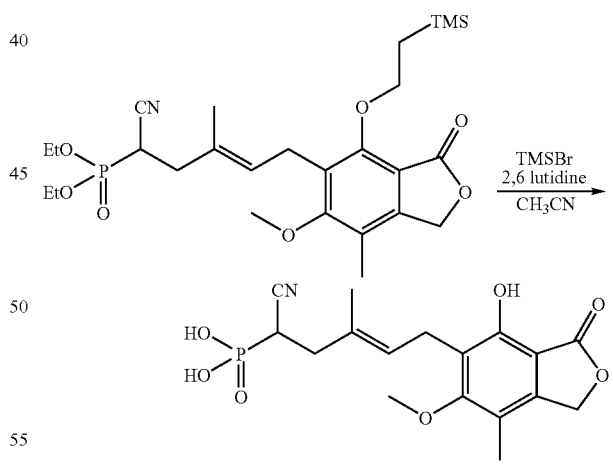

[1-Cyano-5-(4-hydroxy-6-methoxy-7-methyl-3-oxo-1,3-dihydro-isobenzofuran-5-yl)-3-methyl-pent-3-enyl]-phosphonic acid To a solution of {1-cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (35 mg, 0.065 mmol) in acetonitrile (2 mL) was added TMSBr (180 μL, 1.38 mmol) and 2,6-lutidine (160 μL, 1.38 mmol).

The reaction solution was allowed stir at room temperature for one hour before quenching with MeOH. The reaction mixture was dried under reduced pressure and the residue was purified by RP HPLC using a C18 column with a gradient of H₂O, 0.1% TFA-acetonitrile, 0.1% TFA to provide 15 mg (60%) of the desired product. ¹H NMR (300 MHz, CD₃OD) δ 1.86 (s,3H), 2.15 (s, 3H), 2.38-2.57 (m, 2H), 3.17-3.28 (m, 1H), 3.44 (d, J=7.2 Hz, 2H), 3.80 (s, 3H), 5.25 (s, 2H), 5.47 (t, J=7.2 Hz, 1H) ppm; ³¹P (121.4 MHz, CD₃OD) δ 15.28 ppm; MS (m/z) 380 [M−H]⁻, 382 [M+H]⁺.

Example 272

Preparation of Representative Compounds of the Invention

Representative compounds of the invention can be prepared as illustrated below.

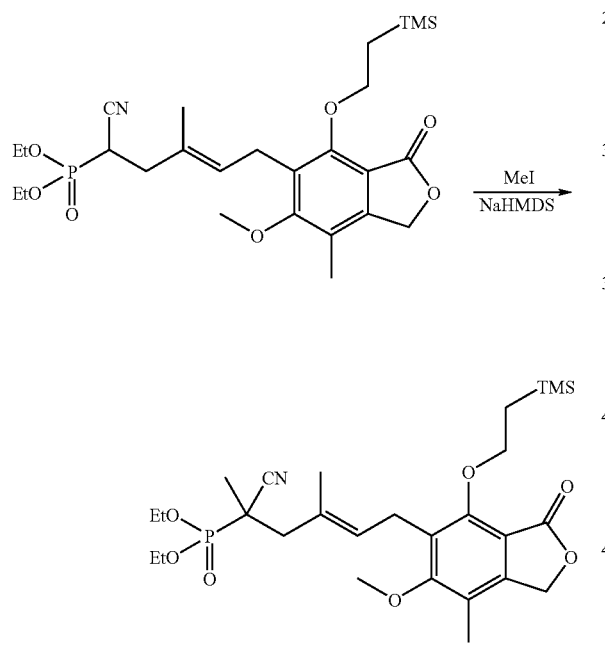

{1-Cyano-5-[6-methoxy-7-methyl-3-oxo-4-(2-trimethylsilanyl-ethoxy)-1,3-dihydro-isobenzofuran-5-yl]-1,3-dimethyl-pent-3-enyl}-phosphonic acid diethyl ester To a solution of {1-cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (45 mg, 0.084 mmol) in THF (0.5 mL) was added sodium bis(trimethysilyl)amide (1.0 M, 1.13 mL, 1.15 mmol). After stirring for 20 minutes, iodomethane (52 µL, 0.84 mmol) was added dropwise and the resulting mixture was allowed to stir at room temperature for 2 hours. The reaction mixture was quenched with saturated aqueous ammonium chloride and extracted with ethyl acetate. The organic layer was dried over sodium sulfate and concentrated to dryness. The residue was purified by RP HPLC using a C18 column with a gradient of H₂O, 0.1% TFA-acetonitrile, 0.1% TFA to afford 6.6 mg (23%) of the desired product. ¹H NMR (300 MHz, CDCl₃) δ 0.00 (s, 9H), 1.16 (dd, J=7, 8 Hz, 2H), 1.31 (t, 6H), 1.38 (d, 3H), 1.92 (s,3H), 2.17 (s, 3H), 2.23 (m, 1H), 2.65 (m, 1H), 3.30-3.42 (m, 2H), 3.73 (s, 3H), 4.14-4.27 (m, 6H), 5.08 (s, 2H), 5.28 (t, J=7.2 Hz, 1H) ppm; ³¹P (121.4 MHz, CDCl₃) δ 22.26 ppm; MS (m/z) 574 [M+Na]⁺.

[1-Cyano-5-(4-hydroxy-6-methoxy-7-methyl-3-oxo-1,3-dihydro-isobenzofuran-5-yl)-1,3-dimethyl-pent-3-enyl]-phosphonic acid To a solution of {1-cyano-5-[6-methoxy-7-methyl-3-oxo-4-(2-trimethylsilanyl-ethoxy)-1,3-dihydro-isobenzofuran-5-yl]-1,3-dimethyl-pent-3-enyl}-phosphonic acid diethyl ester (18 mg, 0.04 mmol) in DMF (0.5 mL) and DCM (0.5 mL) was added TMSBr (51 µL, 0.4 mmol) and 2,6-lutidine (46 µL, 0.4 mmol). The reaction solution was allowed stir at room temperature overnight before quenching with MeOH. The reaction mixture was dried under reduced pressure and the residue was purified by RP HPLC using a C18 column with a gradient of H₂O, 0.1% TFA-acetonitrile, 0.1% TFA to provide 4.5 mg (33%) of the desired product. ¹H NMR (300 MHz, CD₃OD) δ 1.37 (d, 3H), 1.87 (s, 3H), 2.13 (s, 3H), 2.26 (m, 1H), 2.64 (m, 1H), 3.39 (m, 2H), 3.75 (s,3H), 5.18 (s, 2H), 5.34 (m, 1H) ppm; ³¹P (121.4 MHz, CD₃OD) δ 21.47 ppm; MS (m/z) 422 [M−H]⁻, 424 [M+H]⁺.

983 984
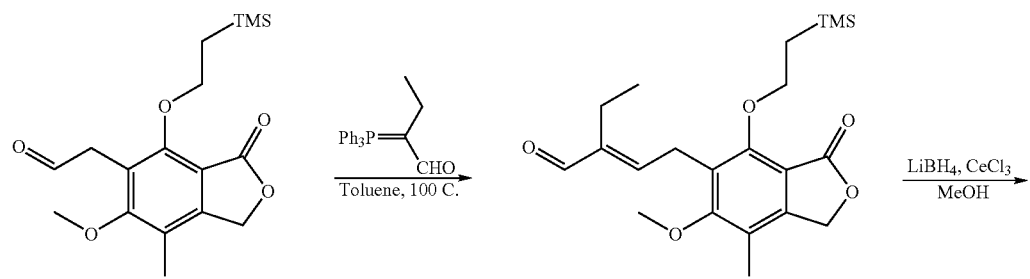
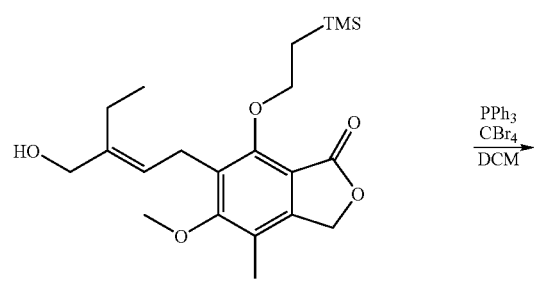
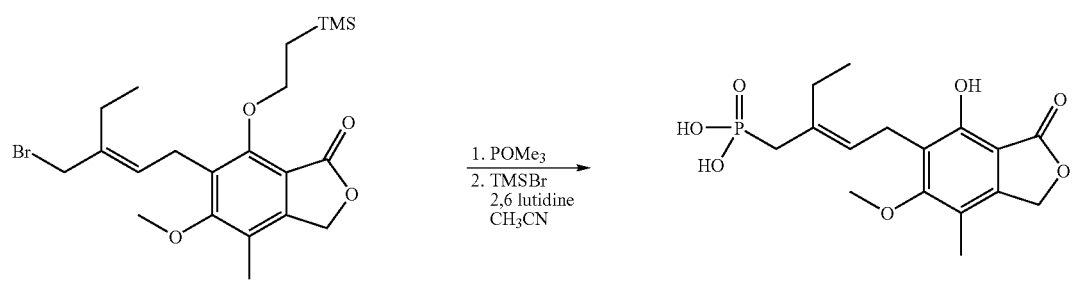
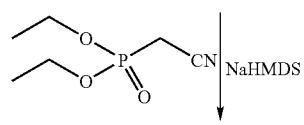
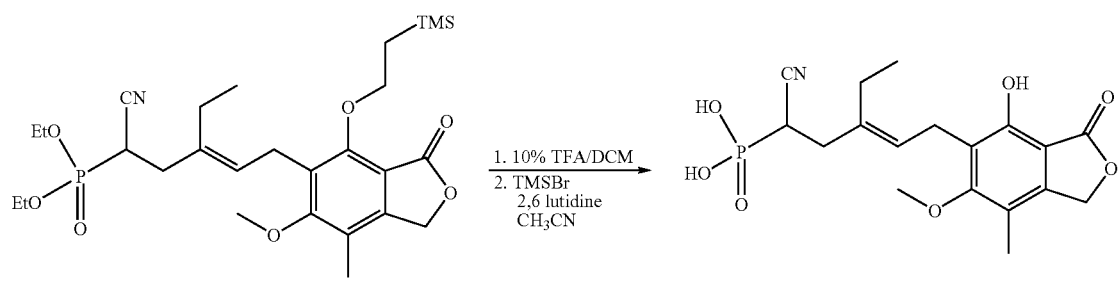

Example 273

Preparation of Representative Compounds of the Invention

Representative compounds of the invention can be prepared as illustrated below.

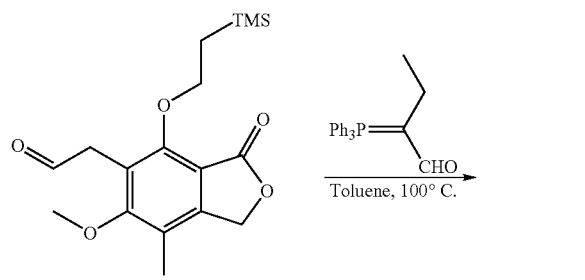

2-Ethyl-4-[6-methoxy-7-methyl-3-oxo-4-(2-trimethylsilanyl-ethoxy)-1,3-dihydro-isobenzofuran-5-yl]-but-2-enal A solution of [6-methoxy-7-methyl-3-oxo-4-(2-trimethylsilanyl-ethoxy)-1,3-dihydro-isobenzofuran-5-yl]-acetaldehyde (1.5 g, 4.46 mmol) in toluene (14 mL) was heated at 100° C. with 2-(triphenyl-phosphanylidene)-butyraldehyde (1.68 g, 5.35 mmol) overnight. A second portion of 2-(triphenyl-phosphanylidene)-butyraldehyde (495 mg, 1.49 mmol) was added and the reaction mixture was heated for an additional day. After concentration, the residue was purified by silica gel chromatography to provide 1.3 g (83%) of the desired product as oil. $^1$H NMR (300 MHz, CDCl$_3$) δ 0.01 (s, 9H), 1.03 (t, 3H), 1.10-1.21 (m, 2H), 2.15 (s, 3H), 2.15-2.44 (m, 2H), 3.67-3.76 (m, 2H), 3.74 (s, 3H), 4.31-4.36 (m, 2H), 5.10 (s, 2H), 6.34-6.38 (m, 1H), 9.28 (s, 1H) ppm.

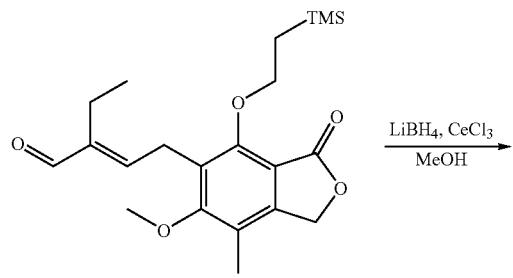

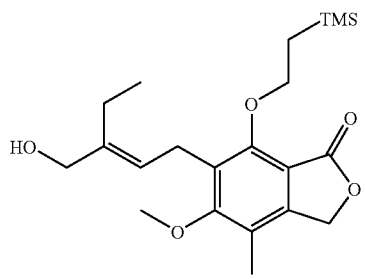

6-(3-Hydroxymethyl-pent-2-enyl)-5-methoxy-4-methyl-7-(2-trimethylsilanyl-ethoxy)-3H-isobenzofuran-1-one A solution of 2-ethyl-4-[6-methoxy-7-methyl-3-oxo-4-(2-trimethylsilanyl-ethoxy)-1,3-dihydro-isobenzofuran-5-yl]-but-2-enal (1.3 g, 3.30 mmol) in methanol (10 mL) and THF (10 mL) was cooled to 0° C. A solution of CeCl$_3$ (8.25 mL, 0.4M, MeOH: H$_2$O, 9:1) was added, followed by LiBH$_4$ (1.66 mL, 3.30 mmol of a 2M solution in THF). The ice bath was removed and the reaction mixture was allowed to warm to room temperature. The reaction mixture was stirred for an additional 40 minutes, whereupon TLC indicated complete consumption of starting aldehyde. The reaction was worked up by addition of aqueous 1N HCl and the product was extracted with EtOAc. The organic layer was washed with saturated aqueous sodium bicarbonate solution and brine. The organic layer was concentrated under reduced pressure and the residue was purified by silica gel chromatography to provide 948 mg (73%) of the product as colorless oil. $^1$H NMR (300 MHz, CDCl$_3$) δ 0.00 (s, 9H), 1.07 (t, 3H), 1.20 (dd, 2H, J=7, 8 Hz), 2.13 (s, 3H), 2.38-2.50 (m, 2H), 3.77 (s, 3H), 3.99 (s, 2H), 4.27 (dd, 2H, J=7, 8 Hz), 5.08 (s, 2H), 5.34 (t, J=7.2 Hz, 1H) ppm.

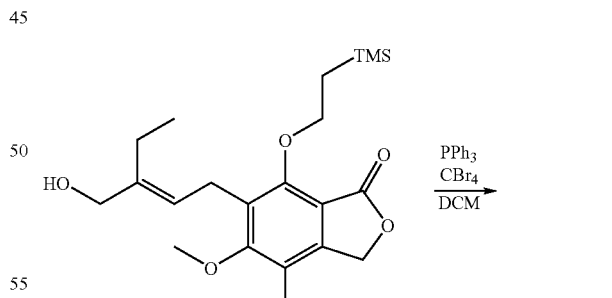

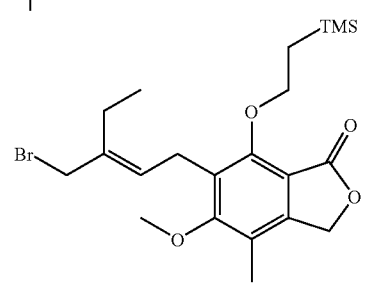

6-(3-Bromomethyl-pent-2-enyl)-5-methoxy-4-methyl-7-(2-trimethylsilanyl-ethoxy)-3H-isobenzofuran-1-one Polymer-supported triphenylphosphine (3 mmol/g, 0.66 g) was soaked in dichloromethane (6 mL) for 1 hour 6-(3-Hydroxymethyl-pent-2-enyl)-5-methoxy-4-methyl-7-(2-trimethylsilanyl-ethoxy)-3H-isobenzofuran-1-one (260 mg, 0.66 mmol) and carbon tetrabromide (657 mg, 1.98 mmol) were added sequentially and the mixture was shaken for 1 hour at room temperature. The mixture was filtered and the filtrate was concentrated. The residue was purified by silica gel chromatography to provide 233 mg (77%) of the product as a white solid. $^1$H NMR (300 MHz, CDCl$_3$) δ 0.00 (s, 9H), 1.08 (t, 3H), 1.20 (dd, 2H, J=7, 8 Hz), 2.14 (s, 3H), 2.35-2.43 (m, 2H), 3.44 (d, J=7.2, 2H), 3.73 (s, 3H), 3.95 (s, 2H), 4.27 (dd, 2H, J=7, 8 Hz), 5.08 (s, 2H), 5.53 (t, J=7.2 Hz, 1H) ppm.

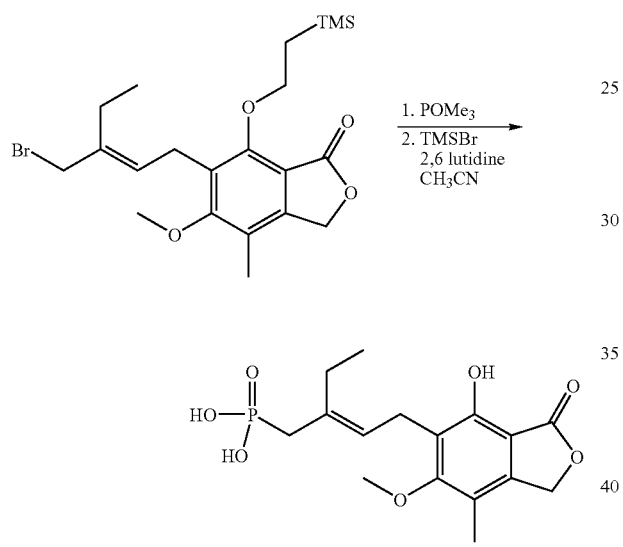

[2-Ethyl-4-(4-hydroxy-6-methoxy-7-methyl-3-oxo-1,3-dihydro-isobenzofuran-5-yl)-but-2-enyl]-phosphonic acid A solution of 6-(3-bromomethyl-pent-2-enyl)-5-methoxy-4-methyl-7-(2-trimethylsilanyl-ethoxy)-3H-isobenzofuran-1-one (230 mg, 0.5 mmol) in trimethylphosphite (1.5 mL, 12.75 mmol) was heated to 100° C. for 4 hours. The reaction was worked up by removal of excess trimethylphosphite under reduced pressure. The residue was dissolved in acetonitrile (1 mL) and TMSBr (646 μL, 5.0 mmol) and 2,6-lutidine (580 μL, 5.0 mmol) were added at 0° C. The reaction solution was allowed to warm to room temperature and stirred for 4 hours. The reaction was cooled to 0° C. and quenched with addition of MeOH. The reaction mixture was dried under reduced pressure and the residue was purified by RP HPLC using a C18 column with a gradient of H$_2$O, 0.1% TFA-acetonitrile, 0.1% TFA to provide 77 mg (58%) of the product. $^1$H NMR (300 MHz, CD$_3$OD) δ 1.08 (t, 3H), 2.16 (s, 3H), 2.43 (m, 2H), 2.48 (d, 2H, J=22 Hz), 3.46 (t, 2H, J=6 Hz), 3.79 (s, 3H), 5.25 (s, 2H), 5.38 (q, 1H, J=7 Hz) ppm.; $^{31}$P (121.4 MHz, CD$_3$OD) δ 25.65 ppm.; MS (m/z) 355 [M−H]$^-$, 357 [M+H]$^+$.

Example 274

Preparation of Representative Compounds of the Invention

Representative compounds of the invention can be prepared as illustrated below.

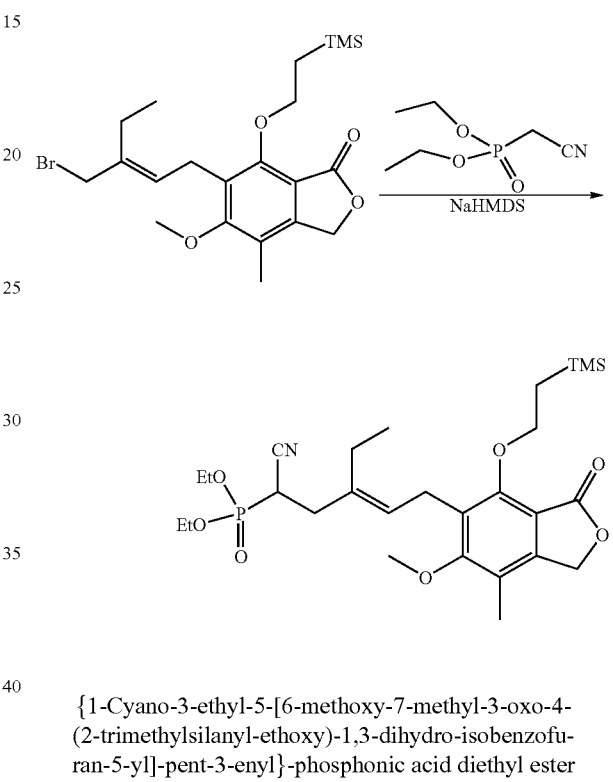

{1-Cyano-3-ethyl-5-[6-methoxy-7-methyl-3-oxo-4-(2-trimethylsilanyl-ethoxy)-1,3-dihydro-isobenzofuran-5-yl]-pent-3-enyl}-phosphonic acid diethyl ester To a solution of diethyl cyanomethylphosphonate (233 mg, 1.32 mmol) in THF (1 mL) was added a THF solution of sodium bis(trimethysilyl)amide (1.0 M, 1.21 mL, 1.21 mmol). After stirring for 30 minutes, the solution was added dropwise to a solution of 6-(3-bromomethyl-pent-2-enyl)-5-methoxy-4-methyl-7-(2-trimethylsilanyl-ethoxy)-3H-isobenzofuran-1-one (100 mg, 0.22 mmol) in THF (1 mL). The resulting mixture was allowed to stir at room temperature overnight before saturated aqueous ammonium chloride was added. The reaction mixture was extracted with ethyl acetate. The organic layer was dried over sodium sulfate and concentrated to dryness. The residue was purified by preparative reverse-phase HPLC, affording 51 mg (42%) of the desired product. $^1$H NMR (300 MHz, CDCl$_3$) δ 0.04 (s, 9H), 1.07 (t, 3H), 1.24 (dd, 2H, J=7, 8 Hz), 1.36 (t, 6H), 2.12 (m, 1H), 2.18 (s, 3H), 2.35-2.47 (m, 2H), 2.67 (m, 1H), 3.00-3.14 (m, 1H), 3.44 (d, J=7.2, 2H), 3.79 (s, 3H), 4.12-4.37 (m, 6H), 5.13 (s, 2H), 5.38 (t, J=7.2 Hz, 1H) ppm; $^{31}$P (121.4 MHz, CDCl$_3$) δ 18.26 ppm; MS (m/z) 574 [M+Na]$^+$.

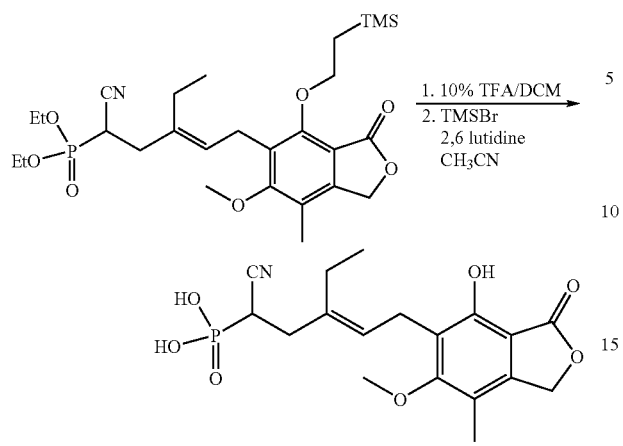

[1-Cyano-3-ethyl-5-(4-hydroxy-6-methoxy-7-methyl-3-oxo-1,3-dihydro-isobenzofuran-5-yl)-pent-3-enyl]-phosphonic acid {1-Cyano-3-ethyl-5-[6-methoxy-7-methyl-3-oxo-4-(2-trimethylsilanyl-ethoxy)-1,3-dihydro-isobenzofuran-5-yl]-pent-3-enyl}-phosphonic acid diethyl ester (19.5 mg, 0.035 mmol) was dissolved in a solution of 10% TFA/CH$_2$Cl$_2$ (2 mL) and stirred at room temperature for 10 minutes. The reaction mixture was dried under reduced pressure and purified by RP-HPLC to provide 9.5 mg (61%) of the desired product. This material was dissolved in DMF (0.5 mL) and DCM (0.5 mL) and TMSBr (27 μL, 0.2 mmol) and 2,6-lutidine (23 μL, 0.2 mmol) were added. The reaction solution was allowed stir at room temperature overnight before quenching with MeOH. The reaction mixture was dried under reduced pressure and the residue was purified by RP HPLC using a C18 column with a gradient of H$_2$O, 0.1% TFA-acetonitrile, 0.1% TFA to provide 5.1 mg (65%) of the desired product as a white solid. $^1$H NMR (300 MHz, CD$_3$OD) δ 1.10 (t,3H), 2.16 (s, 3H), 2.23-2.52 (m, 3H), 2.67 (m, 1H), 3.05-3.20 (m, 1H), 3.48 (d, J=7.2, 2H), 3.81 (s, 3H), 5.26 (s, 2H), 5.43 (t, J=7.2 Hz, 1H) ppm; $^{31}$P (121.4 MHz, CD$_3$OD) δ 14.18 ppm; MS (m/z) 394 [M−H]$^-$, 396 [M+H]$^+$.

Example 275

Preparation of Representative Compounds of the Invention

Representative compounds of the invention can be prepared as illustrated below.

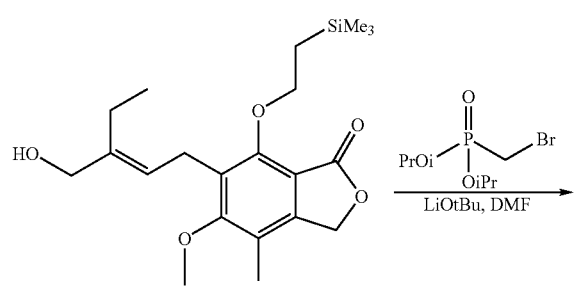

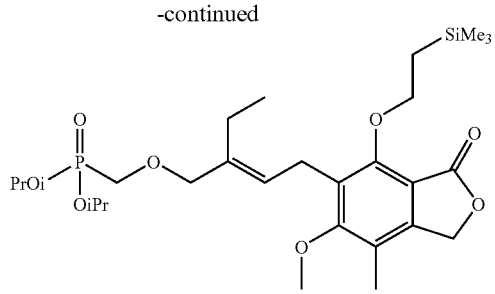

{2-Ethyl-4-[6-methoxy-7-methyl-3-oxo-4-(2-trimethylsilanyl-ethoxy)-1,3-dihydro-isobenzofuran-5-yl]-but-2-enyloxymethyl}-phosphonic acid diisopropyl ester To a solution of bromomethylphosphonate diisopropyl ester (680 mg, 2.62 mmol) and 6-(3-hydroxymethyl-pent-2-enyl)-5-methoxy-4-methyl-7-(2-trimethylsilanyl-ethoxy)-3H-isobenzofuran-1-one (688 mg, 1.75 mmol) in DMF (3 mL) was added lithium t-butoxide (11.0M in THF; 2.6 mL). The reaction was heated at 70° C. for 2 hours. After cooling to ambient temperature, more bromomethylphosphonate diisopropyl ester (680 mg, 2.62 mmol) and lithium t-butoxide (1.0M in THF; 2.6 mL) were added. The reaction mixture was heated at 70° C. for a further hour, cooled, poured into a solution of lithium chloride (5% aqueous) and extracted with ethyl acetate. The organic extract was dried and the product was purified by chromatography on silica gel, eluting with hexane-ethyl acetate to provide 347 mg (35%) of the product as a colorless oil. $^1$H NMR (300 MHz, CDCl$_3$) δ 0.04 (s, 9H), 1.09 (t, 3H, J=7.5 Hz), 1.20-1.26 (m, 2H), 1.31 (t, 12H, J=6 Hz), 2.18 (s, 3H), 2.29 (q, 2H, J=7.5 Hz), 3.5 (m, 2H), 3.59 (d, 2H, J=8.7 Hz), 3.78 (s, 3H), 3.98 (s, 2H), 4.28-4.35 (m, 2H), 4.6-4.8 (m, 2H), 5.13 (s, 2H), 5.4 (t, 1H, J=7 Hz) ppm; $^{31}$P (121.4 MHz, CDCl$_3$) δ 20.26 ppm; MS (m/z) 593.3 [M+Na]$^+$.

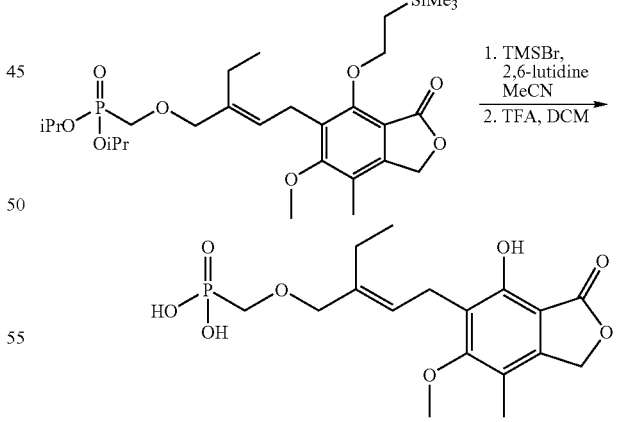

[2-Ethyl-4-(4-hydroxy-6-methoxy-7-methyl-3-oxo-1,3-dihydro-isobenzofuran-5-yl)-but-2-enyloxymethyl]-phosphonic acid To a solution of {2-ethyl-4-[6-methoxy-7-methyl-3-oxo-4-(2-trimethylsilanyl-ethoxy)-1,3-dihydro-isobenzofuran-5-yl]-but-2-enyloxymethyl}-phosphonic acid diisopropyl ester (347 mg, 0.61 mmol) in acetonitrile (5 mL) was added 2,6-lutidine (0.71 mL, 6.1 mmol) and bromotrimethylsilane (0.786 mL, 6.1 mmol). The mixture was stirred at room temperature for 3 hours, quenched with methanol (5 mL), concentrated, and partitioned between ethyl acetate and 1N HCl (aqueous). The organic layer was concentrated to give the free phosphonic acid as a colorless oil (205 mg, 70%). This material (20 mg) was dissolved in a solution of trifluoroacetic acid (0.3 mL) and dichloromethane (2.7 mL) and stirred for 30 minutes at ambient temperature. After concentration, the residue was purified by RP HPLC using a C18 column with a gradient of $H_2O$, 0.1% TFA-acetonitrile, 0.1% TFA to provide the product, after lyophilization, as a white solid (10 mg). $^1$H NMR (300 MHz, $CDCl_3$) δ 1.007 (t, 3H, J=7.5 Hz), 2.13 (s, 3H), 2.32 (q, 2H, J=7.5 Hz), 3.41 (d, 2H, J=6.3 Hz), 3.56 (d, 2H, J=9 Hz), 3.75 (s, 3H), 3.95 (s, 2H), 5.16 (s, 2H), 5.43 (t, 1H, J=6.3 Hz) ppm; $^{31}$P (121.4 MHz, $CDCl_3$) δ 22.8 ppm; MS (m/z) 385.2 $[M-H]^+$, 387.1 $[M+H]^+$.

Example 276

Preparation of Representative Compounds of the Invention

Representative compounds of the invention can be prepared as illustrated below.

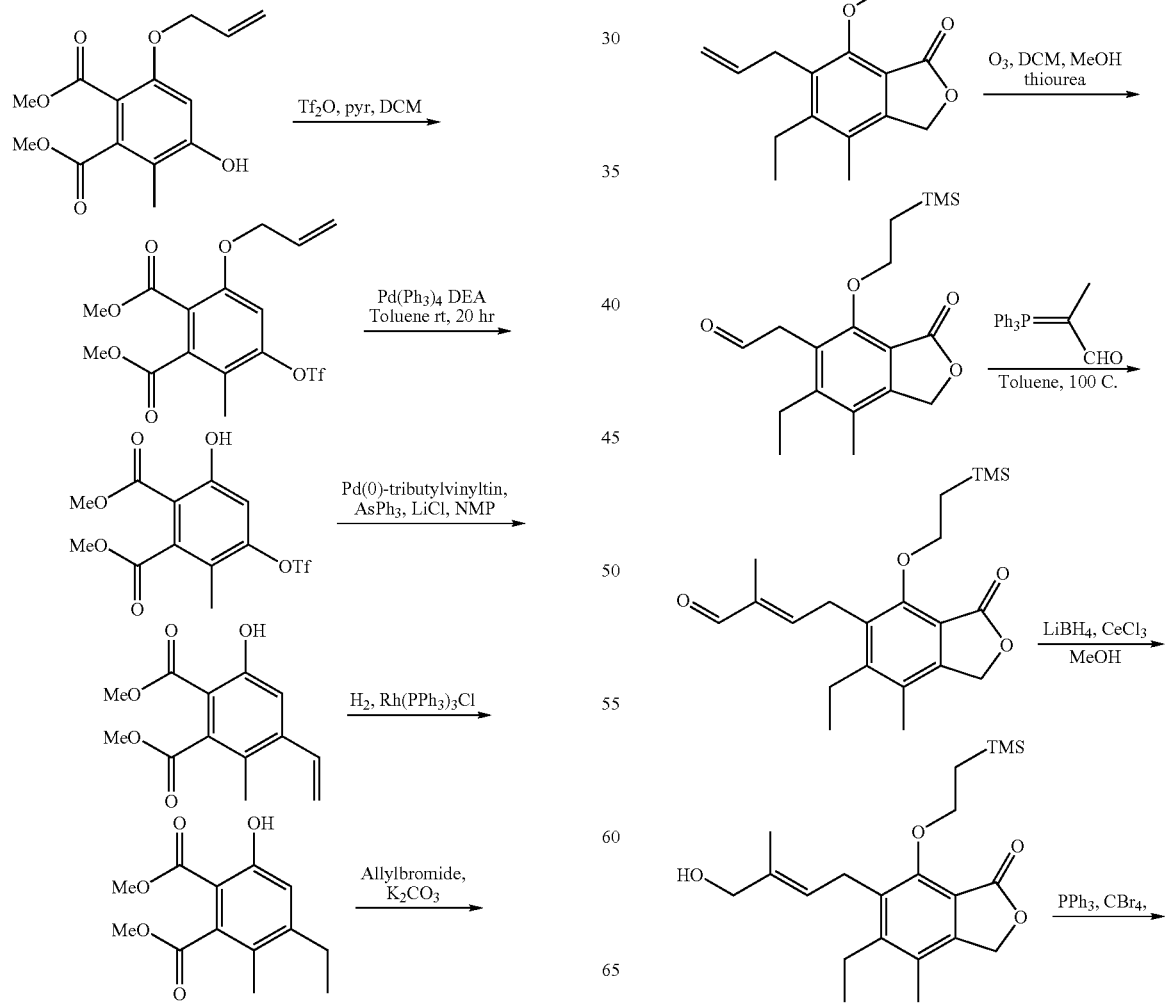

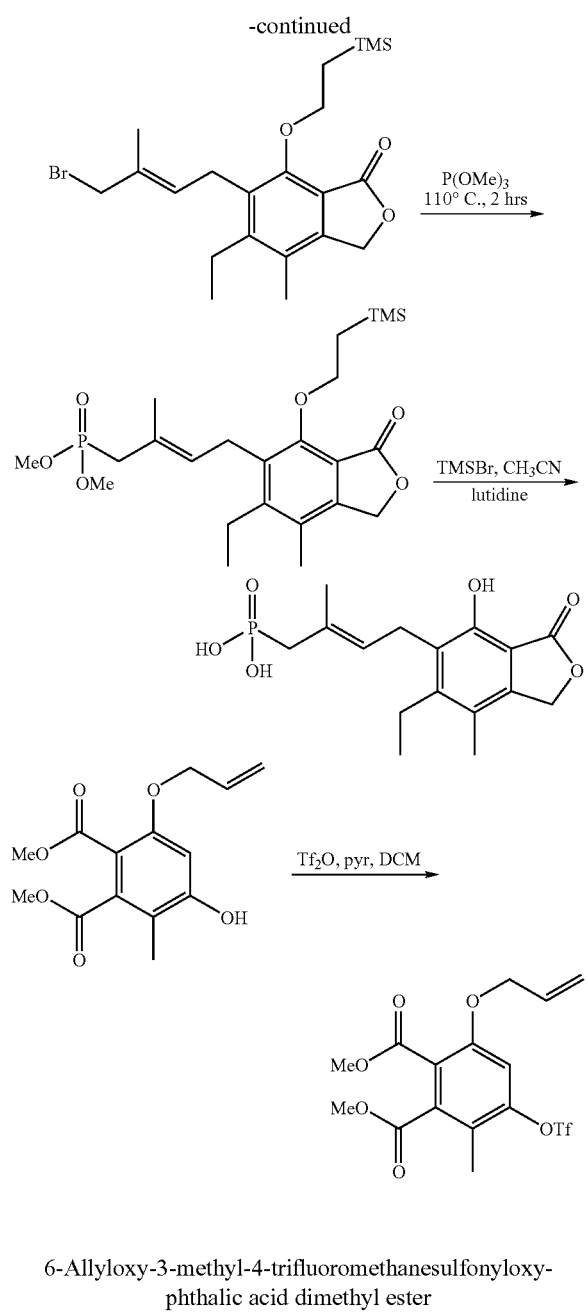

6-Allyloxy-3-methyl-4-trifluoromethanesulfonyloxy-phthalic acid dimethyl ester

To a solution of 6-allyloxy-4-hydroxy-3-methyl-phthalic acid dimethyl ester (8.06 g, 28.8 mmol) [synthesized according to: J. W. Patterson, *Tetrahedron*, 1993, 49, 4789-4798] and pyridine (11.4 g, 144.0 mmol) in dichloromethane (DCM) (20 mL) at 0° C. was added triflic anhydride (12.19 g, 43.2 mmol). The reaction was stirred at 0° C. for 2 hours after which additional triflic anhydride (3 mL) was added. Stirring at 0° C. was continued for an additional hour. The reaction mixture was poured into a mixture of DCM and HCl (1N). The layers were separated and the aqueous layer was extracted with DCM. The combined organic layers were dried over sodium sulfate. Filtration and evaporation of solvents in vacuo yielded a crude product, which was purified by silica gel chromatography to provide 8.39 g of the product as an oil. $^1$H NMR (300 MHz, CDCl$_3$): δ=2.32 (s, 3H), 3.89 (s, 6H), 4.60 (m, 2H), 5.33 (d, J=9.3 Hz, 1H), 5.41 (d, J=18.6 Hz, 1H), 5.95 (m, 1H), 6.95 (s, 1H) ppm; $^{19}$F NMR (282 MHz, CDCl$_3$): δ=−74 ppm.

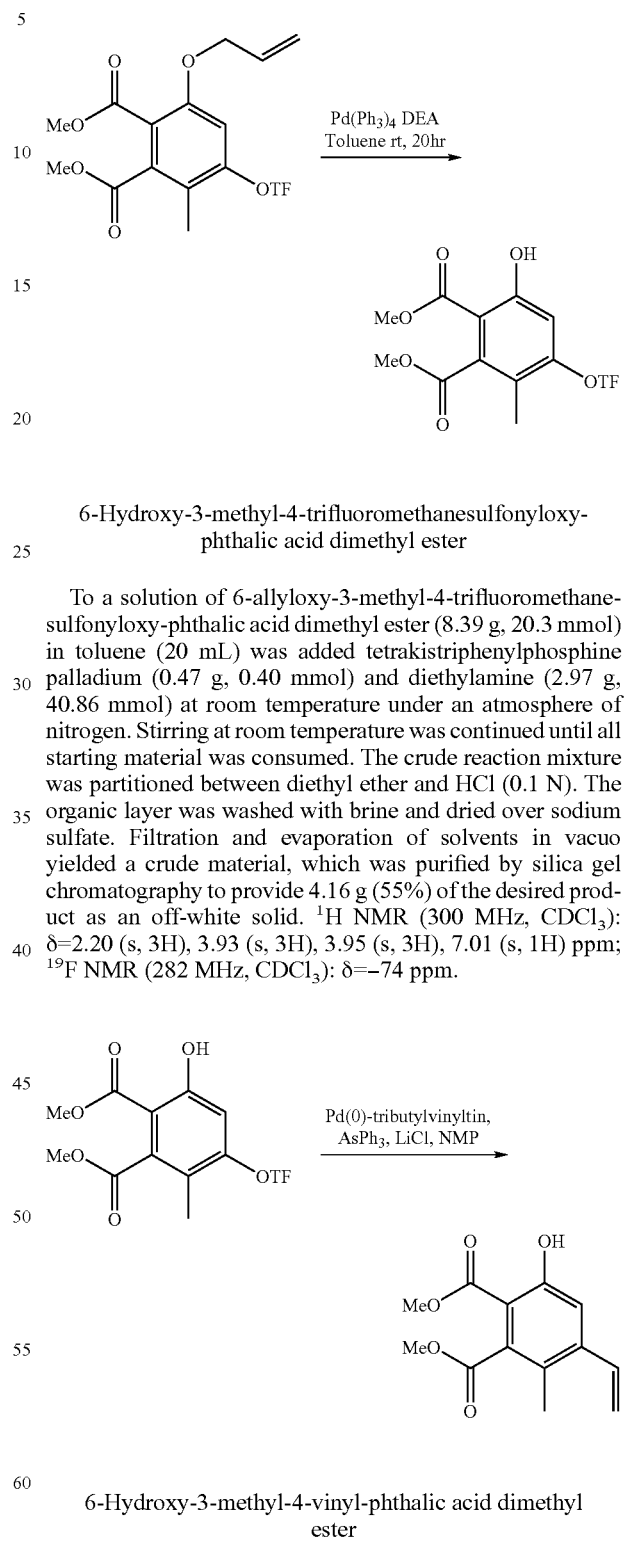

6-Hydroxy-3-methyl-4-trifluoromethanesulfonyloxy-phthalic acid dimethyl ester

To a solution of 6-allyloxy-3-methyl-4-trifluoromethane-sulfonyloxy-phthalic acid dimethyl ester (8.39 g, 20.3 mmol) in toluene (20 mL) was added tetrakistriphenylphosphine palladium (0.47 g, 0.40 mmol) and diethylamine (2.97 g, 40.86 mmol) at room temperature under an atmosphere of nitrogen. Stirring at room temperature was continued until all starting material was consumed. The crude reaction mixture was partitioned between diethyl ether and HCl (0.1 N). The organic layer was washed with brine and dried over sodium sulfate. Filtration and evaporation of solvents in vacuo yielded a crude material, which was purified by silica gel chromatography to provide 4.16 g (55%) of the desired product as an off-white solid. $^1$H NMR (300 MHz, CDCl$_3$): δ=2.20 (s, 3H), 3.93 (s, 3H), 3.95 (s, 3H), 7.01 (s, 1H) ppm; $^{19}$F NMR (282 MHz, CDCl$_3$): δ=−74 ppm.

6-Hydroxy-3-methyl-4-vinyl-phthalic acid dimethyl ester

To a solution of 6-hydroxy-3-methyl-4-trifluoromethane-sulfonyloxy-phthalic acid dimethyl ester (2.17 g, 5.85 mmol) in N-methylpyrolidinone (15 mL) was added lithium chloride (743 mg, 17.5 mmol) and triphenylarsine (179 mg, 0.585 mmol). Tributylvinyltin (2.04 g, 6.43 mmol) was added followed by tris(tribenzylideneacetone)dipalladium(0)-chloroform adduct (90 mg, 0.087 mmol). The reaction was placed under an atmosphere of nitrogen and heated at 60° C. for 18 hours. The reaction was cooled to room temperature and poured onto a mixture of ice (20 g), EtOAc (40 mL), and potassium fluoride (1 g). Stirring was continued for 1 hour. The aqueous layer was extracted with EtOAc and the organic extracts filtered through Celite. The combined organic layers were washed with water and dried over sodium sulfate. Filtration and evaporation of solvents in vacuo yielded a crude material, which was purified by silica gel chromatography to provide 1.27 g (87%) of the product as an off-white solid. $^1$H NMR (300 MHz, CDCl$_3$): δ=2.16 (s, 3H), 3.91 (s, 3H), 3.92 (s, 3H), 5.46 (dd, J=11.1, 1.2 Hz, 1H), 5.72 (dd, J=17.1, 0.9 Hz, 1H), 6.86 (dd, J=17.1, 11.1 Hz, 1H), 7.14 (s, 1H), 10.79 (s, 1H) ppm.

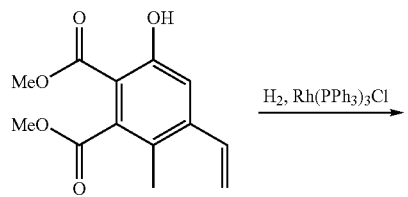

4-Ethyl-6-hydroxy-3-methyl-phthalic acid dimethyl ester

6-Hydroxy-3-methyl-4-vinyl-phthalic acid dimethyl ester (1.27 g, 5.11 mmol) was dissolved in benzene (10 mL) and EtOAc (10 mL). Tristriphenylphosphine rhodium chloride (150 mg) was added and the reaction was placed under an atmosphere of hydrogen. Stirring at room temperature was continued. After 14 hours, the solvents were removed in vacuo and the crude material was purified by silica gel chromatography to provide 1.14 g (88%) of the desired product as an off-white solid. $^1$H NMR (300 MHz, CDCl$_3$): δ=1.19 (t, J=7.8 Hz, 3H), 2.10 (s, 3H), 2.60 (q, J=7.8 Hz, 2H), 3.89 (s, 6H), 6.87 (s, 1H), 10.79 (s, 1H) ppm.

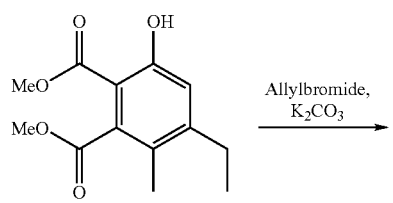

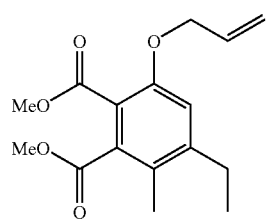

1 6-Allyloxy-4-ethyl-3-methyl-phthalic acid dimethyl ester

4-Ethyl-6-hydroxy-3-methyl-phthalic acid dimethyl ester (1.01 g, 4.02 mmol) was dissolved in DMF (5 mL). Potassium carbonate (3.33 g, 24.14 mmol) was added, followed by allylbromide (2.92 g, 24.14 mmol). The suspension was heated at 60° C. After 14 hours, the reaction was cooled to room temperature and filtered. The solvents were removed in vacuo and the crude material was purified by silica gel chromatography to provide 0.976 g (83%) of the desired product as a colorless oil. $^1$H NMR (300 MHz, CDCl$_3$): δ=1.16 (t, J=7.2 Hz, 3H), 2.20 (s, 3H), 2.62 (q, J=7.2 Hz, 2H), 3.83 (s, 3H), 3.84 (s, 3H), 4.57 (m, 2H), 5.26 (dd, J=9.3, 1.5 Hz, 1H), 5.41 (dd, J=13.5, 1.5 Hz, 1H), 5.98 (m, 1H), 6.82 (s, 1H) ppm.

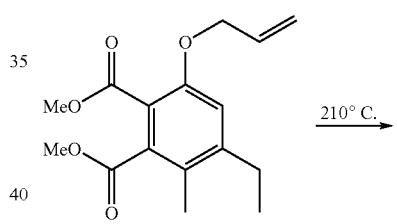

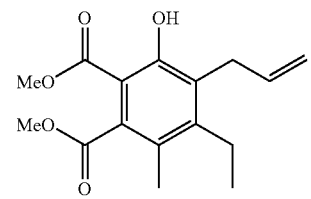

4-Allyl-5-ethyl-3-hydroxy-6-methyl-phthalic acid dimethyl ester

6-Allyloxy-4-ethyl-3-methyl-phthalic acid dimethyl ester (1.25 g, 4.28 mmol) was heated at 210° C. under an atmosphere of nitrogen. After 14 hours, the reaction was cooled to room temperature. The crude material was purified by silica gel chromatography to provide 0.971 g (77%) of the desired product as a colorless oil. $^1$H NMR (300 MHz, CDCl$_3$): δ=1.14 (t, J=7.8 Hz, 3H), 2.17 (s, 3H), 2.68 (q, J=7.8 Hz, 2H), 3.49 (m, 2H), 3.86 (s, 3H), 3.89 (s, 3H), 4.89-5.01 (m, 2H), 5.93 (m, 1H), 11.22 (s, 1H) ppm.

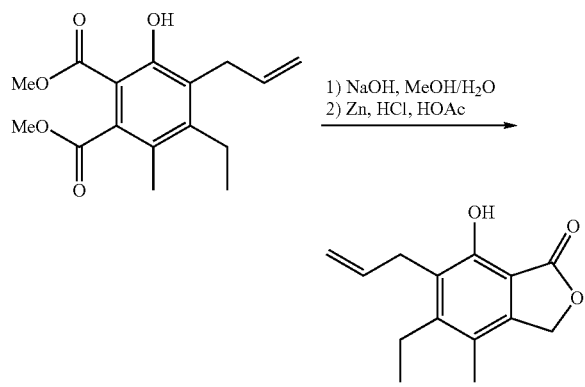

5 6-Allyl-5-ethyl-7-hydroxy-4-methyl-3H-isobenzo-furan-1-one

4-Allyl-5-ethyl-3-hydroxy-6-methyl-phthalic acid dimethyl ester (0.971 g, 3.32 mmol) was dissolved in MeOH (8 mL) at room temperature. A solution of sodium hydroxide (0.798 g, 19.95 mmol) in water (10 mL) was added and the suspension was heated at 55° C. After 16 hours, the reaction was cooled to room temperature and washed with diethyl ether. The aqueous layer was acidified (1N HCl) and the suspension was extracted with EtOAc. The combined organic layers were dried over sodium sulfate. Filtration and evaporation of solvents in vacuo yielded the desired bis acid as a white solid (0.846 g, 98%, M$^+$=263). The bis acid was dissolved in acetic acid (6 mL) and HCl (conc., 1.5 mL). The reaction was heated at 80° C. Zn dust (0.635 g, 9.72 mmol, each) was added in portions every hour for 7 hours. Stirring at 80° C. was continued for additional 10 hours. The reaction was cooled to room temperature, and water was added. The resultant suspension was extracted with EtOAc. The combined organic extracts were washed with sodium bicarbonate solution and dried over sodium sulfate. Filtration and evaporation of solvents in vacuo yielded the crude product, which was purified by silica gel chromatography to provide 0.375 g (50%) of the product as a white solid. $^1$H NMR (300 MHz, CDCl$_3$): δ=1.14 (t, J=7.5 Hz, 3H), 2.18 (s, 3H), 2.71 (q, J=7.5 Hz, 2H), 3.49 (m, 2H), 4.95 (d, J=17.1 Hz, 1H), 5.02 (d, J=10.2 Hz, 1H), 5.23 (s, 2H), 5.98 (m, 1H), 7.66 (s, 1H) ppm.

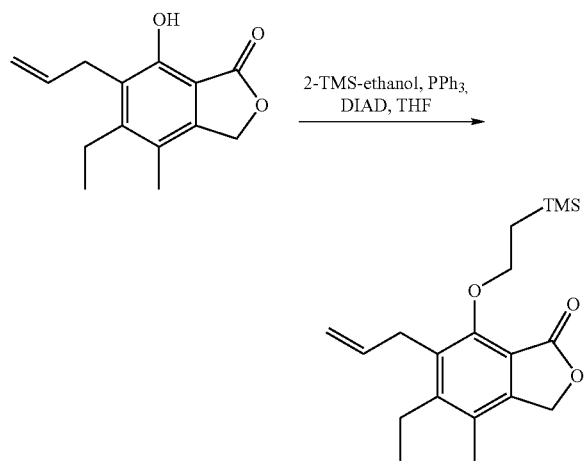

5 6-Allyl-5-ethyl-4-methyl-7-(2-trimethylsilanyl-ethoxy)-3H-isobenzofuran-1-one To a solution of 6-allyl-5-ethyl-7-hydroxy-4-methyl-3H-isobenzofuran-1-one (199 mg, 0.857 mmol), PPh$_3$ (337 mg, 1.286 mmol), and 2-trimethylsilylethanol in THF (3 mL) at 0° C. was added diisopropyl azodicarboxylate (259 mg, 1.286 mmol). The resulting yellow solution was allowed to warm to room temperature and stirred for one hour. The solvent was removed in vacuo and the crude material was dissolved in diethyl ether (3 mL). Hexanes (1.5 mL) were added. Triphenylphosphine oxide was removed by filtration and the filtrate was concentrated and purified by silica gel chromatography to provide the desired product (261 mg, 92%) as a clear oil. $^1$H NMR (300 MHz, CDCl$_3$): δ=0.04 (s, 9H), 1.15 (t, J=7.8 Hz, 3H), 1.25 (m, 2H), 2.20 (s, 3H), 2.73 (q, J=7.8 Hz, 2H), 3.54 (m, 2H), 4.28 (m, 2H), 4.95 (d, J=17.1 Hz, 1H), 5.02 (d, J=10.2 Hz, 1H), 5.15 (s, 2H), 5.95 (m, 1H) ppm.

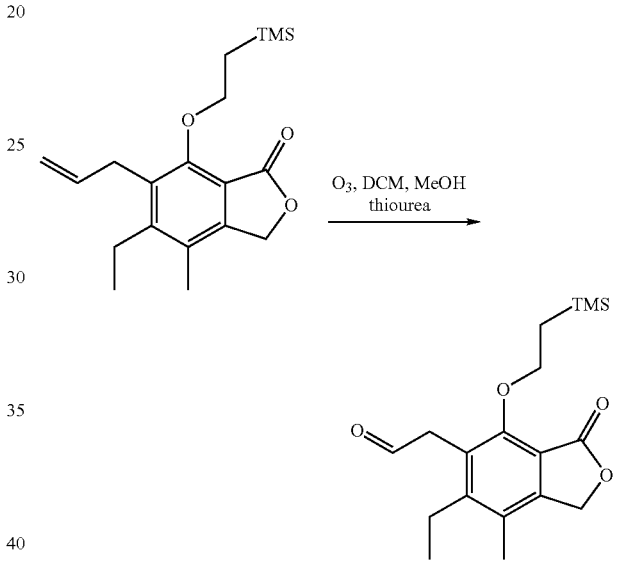

[6-Ethyl-7-methyl-3-oxo-4-(2-trimethylsilanyl-ethoxy)-1,3-dihydro-isobenzofuran-5-yl]-acetaldehyde A solution of 6-allyl-5-ethyl-4-methyl-7-(2-trimethylsilanyl-ethoxy)-3H-isobenzofuran-1-one (261 mg, 0.788 mmol) in MeOH (5 mL), CH$_2$Cl$_2$ (5 mL) and pyridine (50 μL) was cooled to −78° C. using a dry ice/acetone bath according to the procedure of Smith, D. B. et al., *J. Org. Chem.*, 1996, 61, 6, 2236. A stream of ozone was bubbled through the reaction via a gas dispersion tube until the reaction became blue in color (15 minutes). The ozone line was replaced with a stream of nitrogen and bubbling continued for another 15 minutes, by which time the blue color had disappeared. To this solution, at −78° C., was added thiourea (59.9 mg, 0.788 mmol) in one portion, and the cooling bath was removed. The reaction was allowed to warm to room temperature and stirred for 15 hours. The reaction mixture was filtered and then partitioned between CH$_2$Cl$_2$ and water. The aqueous layer was extracted with CH$_2$Cl$_2$ one more time and the organic extracts were combined, washed with aqueous 1N HCl, saturated NaHCO$_3$ and brine and dried over sodium sulfate. Filtration and evaporation of solvents in vacuo yielded the crude product, which was purified by silica gel chromatography to afford 181 mg (69%) of the product as a white solid. $^1$H NMR (300 MHz, CDCl₃): δ=0.04 (s, 9H), 1.11 (t, J=7.5 Hz, 3H), 1.19 (m, 2H), 2.21 (s, 3H), 2.66 (q, J=7.5 Hz, 2H), 3.90 (s, 2H), 4.36 (m, 2H), 5.18 (s, 2H), 9.71 (s, 1H) ppm.

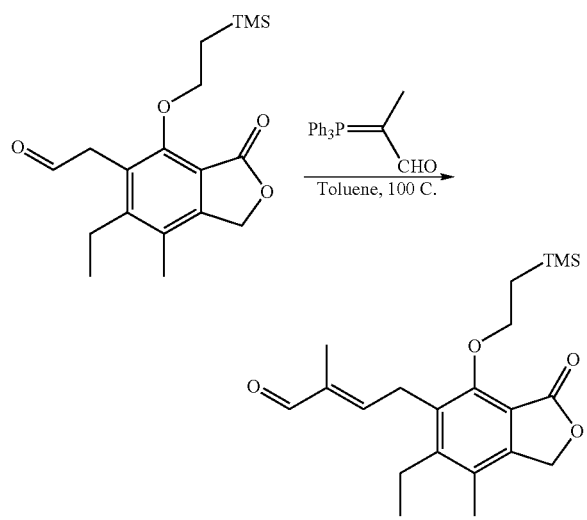

4-[6-Ethyl-7-methyl-3-oxo-4-(2-trimethylsilanyl-ethoxy)-1,3-dihydro-isobenzofuran-5-yl]-2-methyl-but-2-enal

[6-Ethyl-7-methyl-3-oxo-4-(2-trimethylsilanyl-ethoxy)-1,3-dihydro-isobenzofuran-5-yl]-acetaldehyde (90 mg, 0.269 mmol) and 2-(triphenyl-phosphorylidene)-propionaldehyde (72.9 mg, 0.23 mmol) in toluene (3 mL) were heated at 100° C. After 15 hours, a second portion of 2-(triphenyl-phosphanylidene)-propionaldehyde (33 mg, 0.11 mmol) was added and the reaction mixture was heated for additional 9 hours. The toluene was removed in vacuo, and the residue was purified by silica gel chromatography to provide 77.6 mg (77%) of the desired product as a pale yellow oil. ¹H NMR (300 MHz, CDCl₃): δ=0.03 (s, 9H), 1.15 (t, J=7.5 Hz, 3H), 1.21 (m, 2H), 1.93 (s, 3H), 2.21 (s, 3H), 2.71 (q, J=7.5 Hz, 2H), 3.82 (d, J=6.9 Hz, 2H), 4.34 (m, 2H), 5.18 (s, 2H), 6.38 (m, 1H), 9.35 (s, 1H) ppm.

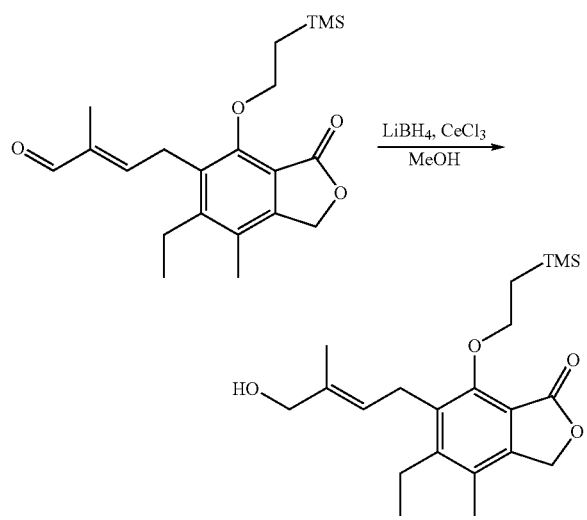

5-Ethyl-6-(4-hydroxy-3-methyl-but-2-enyl)-4-methyl-7-(2-trimethylsilanyl-ethoxy)-3H-isobenzofuran-1-one 4-[6-Ethyl-7-methyl-3-oxo-4-(2-trimethylsilanyl-ethoxy)-1,3-dihydro-isobenzofuran-5-yl]-2-methyl-but-2-enal (77.6 mg, 0.207 mmol) was dissolved in MeOH (4 mL). A solution of CeCl₃ (51.1 mg, 0.207 mmol) in MeOH/water (9/1, 0.66 mL) was added and the solution was cooled to 0° C. A solution of lithium borohydride in THF (2M, 0.105 mL) was added dropwise. After 15 minutes, the reaction was quenched with 1N HCl (0.5 mL). The MeOH was removed in vacuo and the crude material was partitioned between DCM and water. The aqueous layer was extracted with DCM and the combined organic layers were washed with sodium bicarbonate solution and dried over sodium sulfate. Filtration and evaporation of solvents yielded a crude oil, which was purified by silica gel chromatography to provide 57.2 mg (73%) of the desired product. ¹H NMR (300 MHz, CDCl₃): δ=0.04 (s, 9H), 1.15 (t, J=7.8 Hz, 3H), 1.26 (m, 2H), 1.86 (s, 3H), 2.19 (s, 3H), 2.72 (q, J=7.8 Hz, 2H), 3.52 (d, J=6.3 Hz, 2H), 3.99 (s, 2H), 4.34 (m, 2H), 5.14 (s, 2H), 5.32 (m, 1H) ppm.

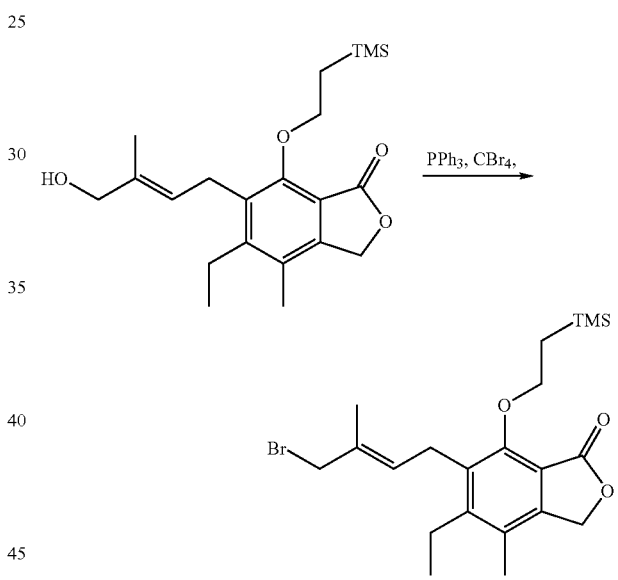

6-(4-Bromo-3-methyl-but-2-enyl)-5-ethyl-4-methyl-7-(2-trimethylsilanyl-ethoxy)-3H-isobenzofuran-1-one 5-Ethyl-6-(4-hydroxy-3-methyl-but-2-enyl)-4-methyl-7-(2-trimethylsilanyl-ethoxy)-3H-isobenzofuran-1-one (57.2 mg, 0.152 mmol) was dissolved in DCM (3.5 mL). Polymer-bound triphenylphosphine (3 mmol/g, 152.1 mg) was added and the mixture was mechanically stirred at room temperature. Carbon tetrabromide (151.3 mg, 0.456 mmol) was added and the solution was stirred at room temperature. After 2 hours, the reaction was filtered and the solvent was removed in vacuo. The crude material was purified by silica gel chromatography to provide 58.0 mg (87%) of the desired product. ¹H NMR (300 MHz, CDCl₃): δ=0.04 (s, 9H), 1.15 (t, J=7.8 Hz, 3H), 1.25 (m, 2H), 1.95 (s, 3H), 2.20 (s, 3H), 2.70 (q, J=7.8 Hz, 2H), 3.52 (d, J=6.3 Hz, 2H), 3.94 (s, 2H), 4.28 (m, 2H), 5.14 (s, 2H), 5.50 (m, 1H) ppm.

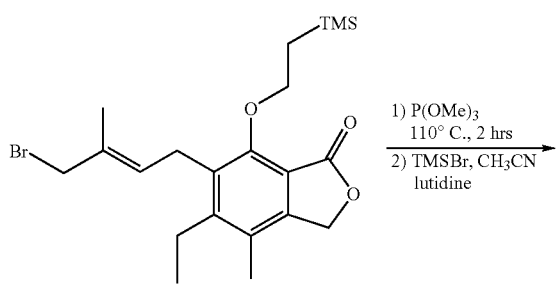

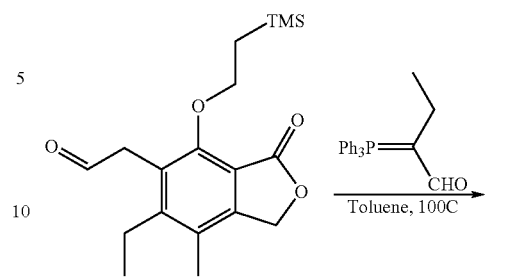

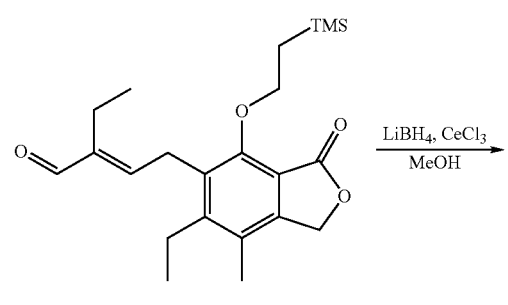

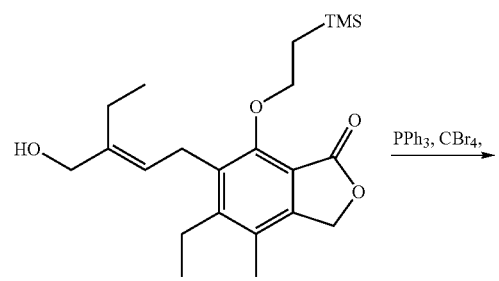

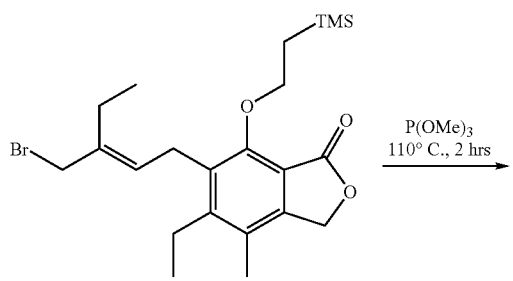

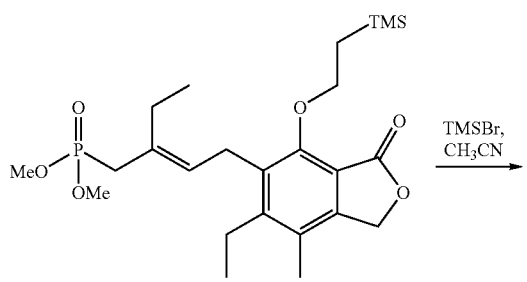

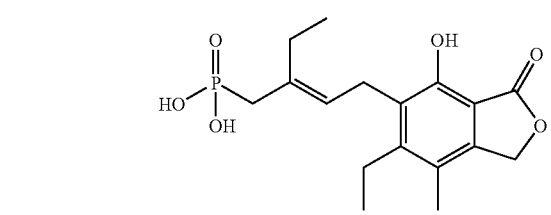

{4-[6-Ethyl-7-methyl-3-oxo-4-(2-trimethylsilanyl-ethoxy)-1,3-dihydro-isobenzofuran-5-yl]-2-methyl-but-2-enyl}-phosphonic acid A solution of 4-[6'-ethyl-7'-methyl-3'-oxo-4'-(2"-trimethylsilanyl-ethoxy)-1',3'-dihydro-isobenzofuran-5'-yl]-2-methyl-but-2-enyl bromide (58 mg, 0.132 mmol) in trimethylphosphite (0.8 mL) was heated at 110° C. After 2 hours the reaction was complete. The reaction was cooled to room temperature and the excess trimethylphosphite was removed in vacuo. The crude material was used in the next step without further purification.

The crude product of the Arbuzov reaction was dissolved in MeCN (0.8 mL). Trimethylsilyl bromide (202.2 mg, 1.321 mmol) was added and the reaction was stirred at room temperature. After 15 minutes, lutidine (155.7 mg, 1.453 mmol) was added and stirring at room temperature was continued. After 2 hours, additional trimethylsilyl bromide (202.2 mg, 1.321 mmol) was added and stirring at room temperature was continued. After 4 hours, the reaction was quenched with MeOH (2 mL). The solvents were evaporated in vacuo, and the crude material was purified by RP-HPLC (eluent: water/MeCN). The product-containing fractions were combined and lyophilized to yield 2.3 mg (5.1%) of the free phosphonic acid. $^1$H NMR (300 MHz, DMSO-d6): δ=1.07 (t, J=7.5 Hz, 3H), 1.84 (s, 3H), 2.14 (s, 3H), 2.64 (q, J=7.5 Hz, 2H), 3.34 (m, 4H), 5.06 (m, 1H), 5.25 (s, 2H) ppm; $^{31}$P NMR (121 MHz, DMSO-d6): δ=22.19 ppm; MS=341 [M$^+$+1].

Example 277

Preparation of Representative Compounds of the Invention

Representative compounds of the invention can be prepared as illustrated below.

1003

-continued

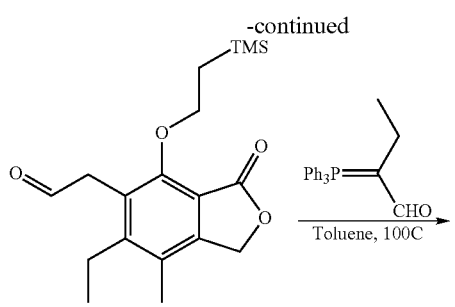

[2-Ethyl-4-[6-ethyl-7-methyl-3-oxo-4-(2-trimethylsilanyl-ethoxy)-1,3-dihydro-isobenzofuran-5-yl]-but-2-enal

[6-Ethyl-7-methyl-3-oxo-4-(2-trimethylsilanyl-ethoxy)-1,3-dihydro-isobenzofuran-5-yl]-acetaldehyde (90 mg, 0.269 mmol) and 2-(triphenyl-phosphorylidene)-butyraldehyde (98.4 mg, 0.296 mmol) in toluene (3 mL) were heated at 100° C. After 15 hours, a second portion of 2-(triphenyl-phosphanylidene)-butyraldehyde (98.4 mg, 0.296 mmol) was added and the reaction mixture was heated for additional 33 hours. After concentration, the residue was purified by silica gel chromatography to provide 50.3 mg (48%) of the desired product as a pale yellow oil.

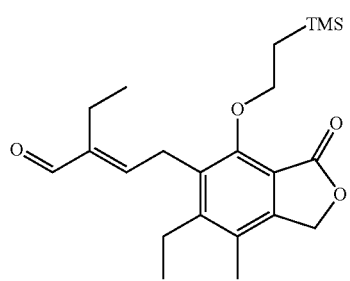

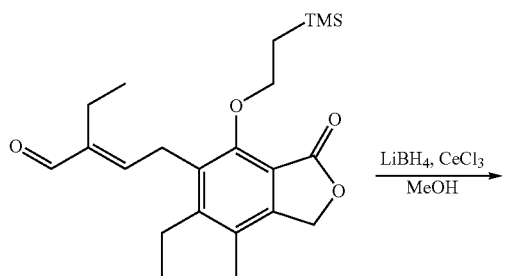

1004

5-Ethyl-6-(3-hydroxymethyl-pent-2-enyl)-4-methyl-7-(2-trimethylsilanyl-ethoxy)-3H-isobenzofuran-1-one 2-Ethyl-4-[6-ethyl-7-methyl-3-oxo-4-(2-trimethylsilanyl-ethoxy)-1,3-dihydro-isobenzofuran-5-yl]-but-2-enal (50.3 mg, 0.129 mmol) was dissolved in MeOH (3 mL). A solution of $CeCl_3$ (31.9 mg, 0.129 mmol) in MeOH/water (9/1, 0.66 mL) was added and the solution was cooled to 0° C. A solution of lithium borohydride in THF (2M, 0.065 mL) was added dropwise. After 10 minutes, the reaction was quenched with 1N HCl (0.5 mL). The methanol was removed in vacuo and the crude material was partitioned between DCM and water. The aqueous layer was extracted with DCM and the combined organic layers were washed with sodium bicarbonate solution and were dried over sodium sulfate. Filtration and evaporation of solvents in vacuo yielded a crude oil, which was purified by silica gel chromatography to provide 35.4 mg (70%) of the desired product. $^1$H NMR (300 MHz, $CDCl_3$): δ=0.04 (s, 9H), 1.10-1.19 (m, 6H), 1.26 (m, 2H), 2.19 (s, 3H), 2.32 (q, J=7.5 Hz, 2H), 2.72 (q, J=7.5 Hz, 2H), 3.54 (d, J=6.6 Hz, 2H), 4.05 (s, 2H), 4.26 (m, 2H), 5.14 (s, 2H), 5.27 (m, 1H) ppm.

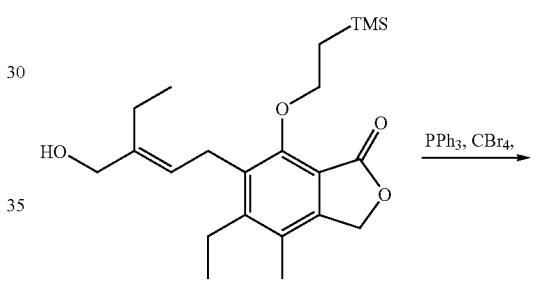

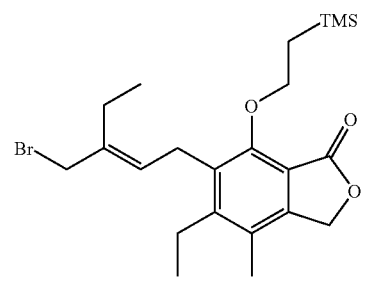

6-(3-Bromomethyl-pent-2-enyl)-5-ethyl-4-methyl-7-(2-trimethylsilanyl-ethoxy)-3H-isobenzofuran-1-one 5-Ethyl-6-(3-hydroxymethyl-pent-2-enyl)-4-methyl-7-(2-trimethylsilanyl-ethoxy)-3H-isobenzofuran-1-one (35.4 mg, 0.090 mmol) was dissolved in DCM (3.0 mL). Polymer-bound triphenylphosphine (3 mmol/g, 90.7 mg) was added, and the mixture was mechanically stirred at room temperature. Carbon tetrabromide (90.2 mg, 0.272 mmol) was added and the solution was stirred at room temperature. After 2 hours, the reaction was filtered and the solvent was removed in vacuo. The crude material was purified by silica gel chromatography to provide 32.0 mg (78%) of the desired product. The material was used in the next step without further characterization.

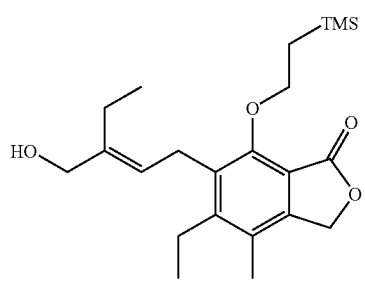

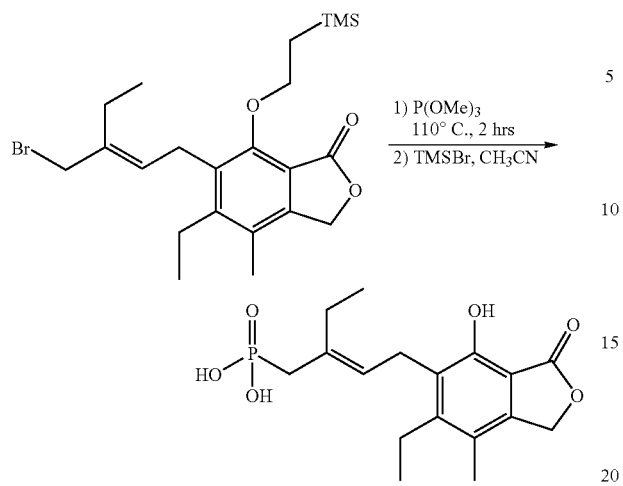

[2-Ethyl-4-(6-ethyl-4-hydroxy-7-methyl-3-oxo-1,3-dihydro-isobenzofuran-5-yl)-but-2-enyl]-phosphonic acid A solution of 6-(3-bromomethyl-pent-2-enyl)-5-ethyl-4-methyl-7-(2-trimethylsilanyl-ethoxy)-3H-isobenzofuran-1-one (32 mg, 0.070 mmol) in trimethylphosphite (0.8 mL) was heated at 110° C. After 2 hours, the reaction was complete. The reaction was cooled to room temperature and the excess trimethylphosphite was removed in vacuo. The crude material was used in the next step without further purification.

The crude product of the Arbuzov reaction was dissolved in MeCN (0.8 mL). Trimethylsilyl bromide (108.0 mg, 0.706 mmol) was added and the reaction was stirred at room temperature. After 2 hours, a second batch of trimethysilyl bromide (108.0 mg, 0.706 mmol) was added. After 3 hours, the reaction was quenched with MeOH (2 mL). The solvents were evaporated in vacuo and the crude material was purified by RP-HPLC (eluent: water/MeCN). The product-containing fractions were combined and lyophilized to yield 15.7 mg (63%) of the product. $^1$H NMR (300 MHz, DMSO-d6): δ=0.98-1.09 (m, 6H), 2.10 (s, 3H), 2.30 (m, 2H), 2.64 (q, J=7.5 Hz, 2H), 3.38 (m, 4H), 5.03 (m, 1H), 5.25 (s, 2H) ppm; $^{31}$P NMR (121 MHz, DMSO-d6): δ=22.26 ppm; MS=355 [M$^+$+1].

Example 278

Preparation of Representative Compounds of the Invention

Representative compounds of the invention can be prepared as illustrated below.

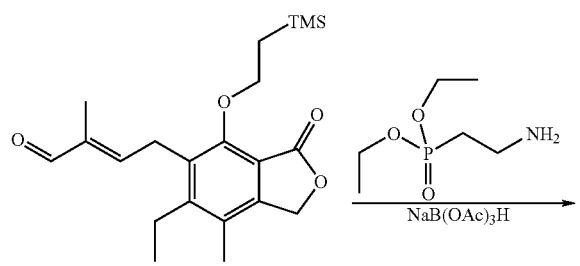

-continued (2-{4-[6-Ethyl-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester 4-[6-Ethyl-7-methyl-3-oxo-4-(2-trimethylsilanyl-ethoxy)-1,3-dihydro-isobenzofuran-5-yl]-2-methyl-but-2-enal (19.7 mg, 0.052 mmol) and aminoethylphosphonic acid diethylesteroxalate salt (15.6 mg, 0.057 mmol) were dissolved in DMF (0.5 mL). Acetic acid (15.7 mg, 0.263 mmol) was added, followed by sodium triacetoxyborohydride (22.3 mg, 0.105 mmol). After 4 hours, the crude reaction mixture was purified by RP-HPLC (eluent: water/MeCN) to provide 27.7 mg (97%) of the desired product after lyophilization. $^1$H NMR (300 MHz, CDCl$_3$): δ=0.04 (s, 9H), 1.14 (t, J=7.5 Hz, 3H), 1.26 (m, 2H), 1.30 (t, J=7.2 Hz, 6H), 1.95 (s, 3H), 2.19 (s, 3H), 2.23 (m, 2H), 2.68 (q, J=7.5 Hz, 2H), 3.18 (m, 2H), 3.53 (s, 2H), 4.13 (m, 4H), 4.28 (m, 2H), 5.15 (s, 2H), 5.51 (m, 1H) ppm; $^{31}$P NMR (121 MHz, CDCl$_3$): δ=27.39 ppm; MS=540 [M$^+$+1].

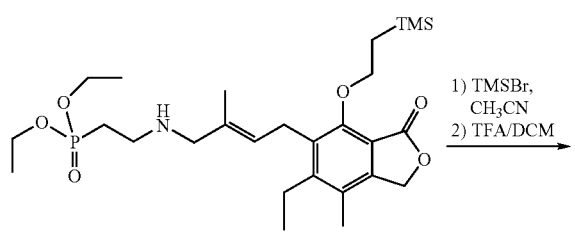

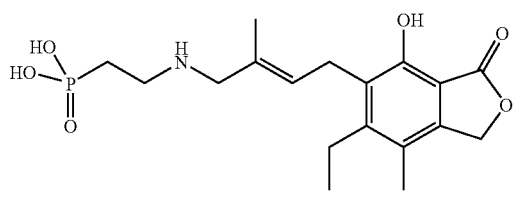

{2-[4-(6-Ethyl-4-hydroxy-7-methyl-3-oxo-1,3-dihydro-isobenzofuran-5-yl)-2-methyl-but-2-enylamino]-ethyl}-phosphonic acid (2-{4-[6-Ethyl-7-methyl-3-oxo-4-(2-trimethylsilanylethoxy)-1,3-dihydro-isobenzofuran-5-yl]-2-methyl-but-2-enylamino}-ethyl)-phosphonic acid diethyl ester (27.7 mg, 0.051 mmol) was dissolved in DMF (0.5 mL) and DCM (0.5 mL). Trimethylsilyl bromide (78.3 mg, 0.512 mmol) was added and the reaction was stirred at room temperature. After 20 hours, the reaction was quenched with MeOH (0.3 mL). The solvents were evaporated in vacuo and the crude material was purified by RP-HPLC (eluent: water/MeCN). The product-containing fractions were combined and lyophilized to yield 14.2 mg (57%) of the free phosphonic acid [MS: 484 M$^+$+1].

The material was dissolved in DCM (0.5 mL). TFA (0.05 mL) was added and stirring at room temperature was continued. After 20 minutes, the solvents were removed in vacuo and the crude material was purified by RP-HPLC (eluent: water/MeCN*0.1% TFA). The product-containing fractions were combined and lyophilized to yield 7.6 mg (52%) of the product as the TFA salt. $^1$H NMR (300 MHz, DMSO-d6): δ=1.07 (t, J=7.5 Hz, 3H), 1.84 (s, 3H), 1.90 (m, 2H), 2.11 (s, 3H), 2.63 (q, J=7.5 Hz, 2H), 2.99 (m, 2H), 3.43 (d, J=6.3 Hz, 2H), 3.51 (s, 2H), 5.26 (s, 2H), 5.45 (m, 1H) ppm; $^{31}$P NMR (121 MHz, DMSO-d6): δ=20.02 ppm; MS=384 [M$^+$+1].

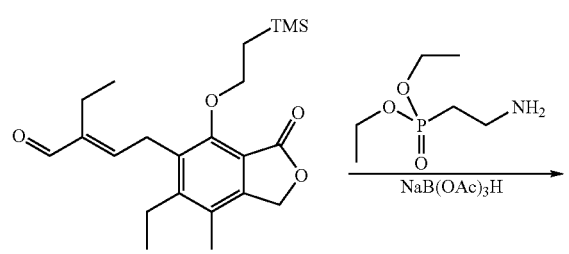

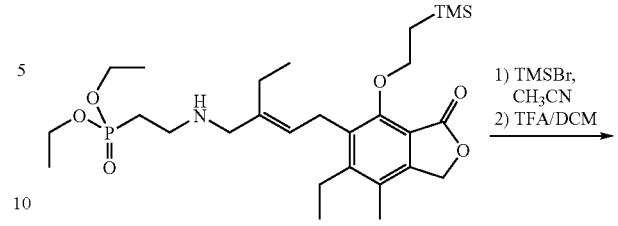

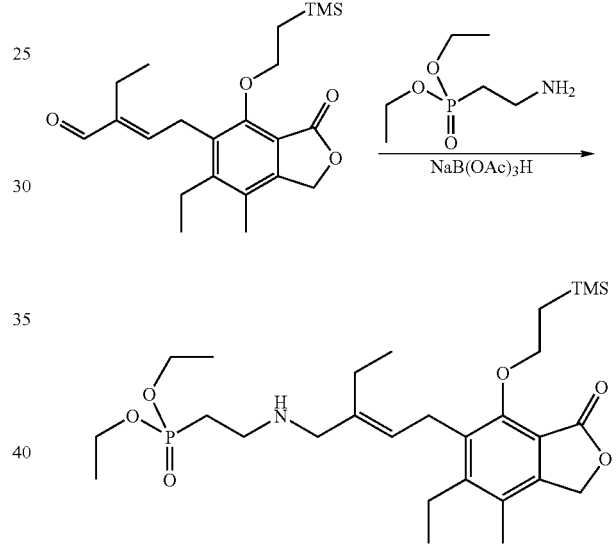

(2-{2-Ethyl-4-[6-ethyl-7-methyl-3-oxo-4-(2-trimethylsilanyl-ethoxy)-1,3-dihydro-isobenzofuran-5-yl]-but-2-enylamino}-ethyl)-phosphonic acid diethyl ester 2-Ethyl-4-[6-ethyl-7-methyl-3-oxo-4-(2-trimethylsilanylethoxy)-1,3-dihydro-isobenzofuran-5-yl]-but-2-enal (26.6 mg, 0.068 mmol) and aminoethylphosphonic acid diethylester oxalate salt (20.4 mg, 0.075 mmol) were dissolved in DMF (0.8 mL). Acetic acid (20.5 mg, 0.342 mmol) was added, followed by sodium triacetoxyborohydride (27.6 mg, 0.137 mmol). After 8 hours, the crude reaction mixture was purified by RP-HPLC (eluent: water/MeCN) to provide 24.9 mg (65%) of the desired product after lyophilization. $^1$H NMR (300 MHz, CDCl$_3$): δ=0.05 (s, 9H), 1.10-1.24 (m, 8H), 1.35 (t, J=7.5 Hz, 6H), 2.19 (s, 3H), 2.23 (m, 2H), 2.35 (q, J=7.8 Hz, 2H), 2.70 (q, J=7.2 Hz, 2H), 3.25 (m, 2H), 3.56 (m, 4H), 4.15 (m, 4H), 4.29 (m, 2H), 5.15 (s, 2H), 5.47 (m, 1H) ppm; $^{31}$P NMR (121 MHz, CDCl$_3$): δ=27.71 ppm; MS=554 [M$^+$+1].

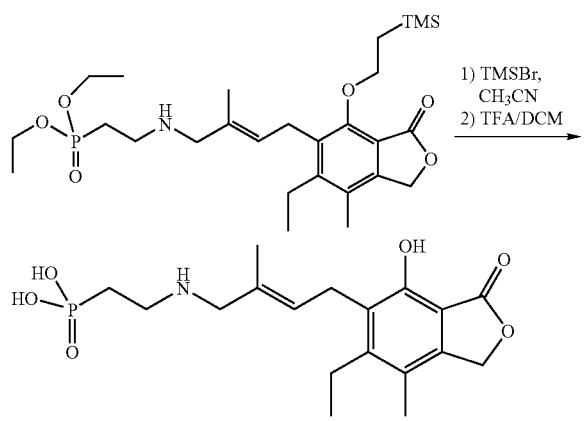

{2-[2-Ethyl-4-(6-ethyl-4-hydroxy-7-methyl-3-oxo-1,3-dihydro-isobenzofuran-5-yl)-but-2-enylamino]-ethyl}-phosphonic acid (2-{2-Ethyl-4-[6-ethyl-7-methyl-3-oxo-4-(2-trimethylsilanyl-ethoxy)-1,3-dihydro-isobenzofuran-5-yl]-but-2-enylamino}-ethyl)-phosphonic acid diethyl ester (24.9 mg, 0.045 mmol) was dissolved in DMF (0.5 mL) and DCM (0.5 mL). Trimethylsilyl bromide (68.7 mg, 0.449 mmol) was added and the reaction was stirred at room temperature. After 20 hours, the reaction was quenched with MeOH (0.15 mL). The solvents were evaporated in vacuo and the crude material was purified by RP-HPLC (eluent: water/MeCN). The product-containing fractions were combined and lyophilized to yield 8.0 mg of the free phosphonic acid [MS: 498 M$^+$+1].

This material was dissolved in DCM (0.5 mL). TFA (0.05 mL) was added, and stirring at room temperature was continued. After 20 minutes, the solvents were removed in vacuo and the crude material was purified by RP-HPLC (eluent: water/MeCN*0.1% TFA). The product-containing fractions were combined and lyophilized to yield 4.4 mg (54%) of the product as the TFA salt. $^1$H NMR (300 MHz, DMSO-d6): δ 1.05 (m, 6H), 1.60 (m, 2H), 2.10 (s, 3H), 2.67 (q, J=7.5 Hz, 2H), 2.63 (q, J=6.9 Hz, 2H), 2.93 (m, 2H), 3.45 (m, 4H), 5.24 (s, 2H), 5.36 (m, 1H) ppm.; $^{31}$P NMR (121 MHz, DMSO-d6): δ 16.93 ppm; MS=398 [M$^+$+1].

Example 279

Preparation of Representative Compounds of the Invention

Representative compounds of the invention can be prepared as illustrated below.

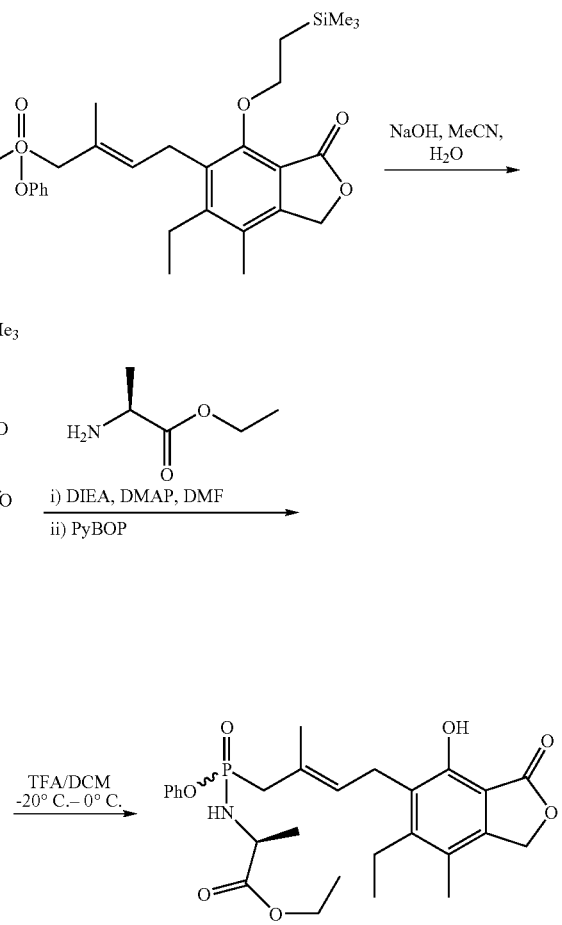

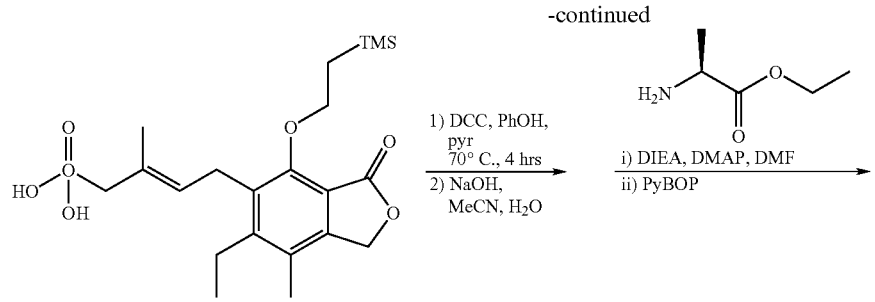

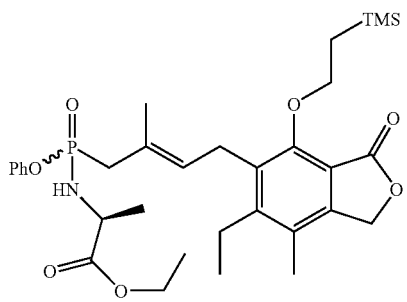

2-({4-[6-Ethyl-7-methyl-3-oxo-4-(2-trimethylsilanyl-ethoxy)-1,3-dihydro-isobenzofuran-5-yl]-2-methyl-but-2-enyl}-phenoxy-phosphinoylamino)-propionic acid ethyl ester 4-[6'-ethyl-7'-methyl-3'-oxo-4'-(2''-trimethylsilanylethoxy)-1',3'-dihydro-isobenzofuran-5'-yl]-2-methyl-but-2-en-phosphonic acid (44.8 mg, 0.101 mmol), dicyclohexylcarbodiimide (52.6 mg, 0.254 mmol), and phenol (95.8 mg, 1.018 mmol) were dissolved in pyridine (0.3 mL) and heated at 70° C. for 4 hours. The reaction mixture was cooled to room temperature and the pyridine was removed in vacuo. The crude material was partitioned between DCM and HCl (0.1N). The aqueous layer was extracted with DCM and the combined organic layers were dried over sodium sulfate. Filtration and evaporation of solvents in vacuo yielded a crude material, which was used in the next step without further purification.

The crude material was dissolved in MeCN (0.8 mL) and water (0.3 mL). Aqueous sodium hydroxide solution (2N, 0.8 mL) was added in portions (0.2 mL). After all starting material was consumed, the organic solvent was removed in vacuo and the crude material was partitioned between chloroform and aqueous HCl (1N). The aqueous layer was extracted with chloroform. The combined organic layers were dried over sodium sulfate. Filtration and evaporation of solvents yielded the crude product as a mixture of mono phenyl ester and the symmetrical anhydride.

The crude material of the previous step and ethyl (L)-alanine hydrochloride salt (78.1 mg, 0.509 mmol) were dissolved in DMF (0.4 mL). DMAP (1.2 mg, catalytic) was added, followed by diisopropylethylamine (131.3 mg, 1.018 mmol). Stirring at room temperature was continued. After 20 minutes, complete conversion of the anhydride was observed. After 2 hours, PyBOP (101 mg, 0.202 mmol) was added and stirring at room temperature was continued. The reaction was filtered and the crude reaction solution was purified by RP-HPLC (eluent: water/MeCN). The product-containing fractions were combined and lyophilized to yield the product (15.7 mg, 25% over three steps) as a white powder. $^1$H NMR (300 MHz, CDCl$_3$): δ=0.03 (s, 9H), 1.13-1.28 (m, 8H), 2.03 (s, 3H), 2.19 (s, 3H), 2.62-2.74 (m, 4H), 3.38 (m, 1H), 3.53 (t, J=6.3 Hz, 2H), 4.03 (m, 3H), 4.30 (m, 2H), 5.14 (s, 2H), 5.31 (m, 1H), 7.11-7.17 (m, 3H), 7.25-7.30 (m, 2H) ppm; $^{31}$P NMR (121 MHz, CDCl$_3$): δ=27.04, 27.73 ppm; MS=615 [M$^+$+1].

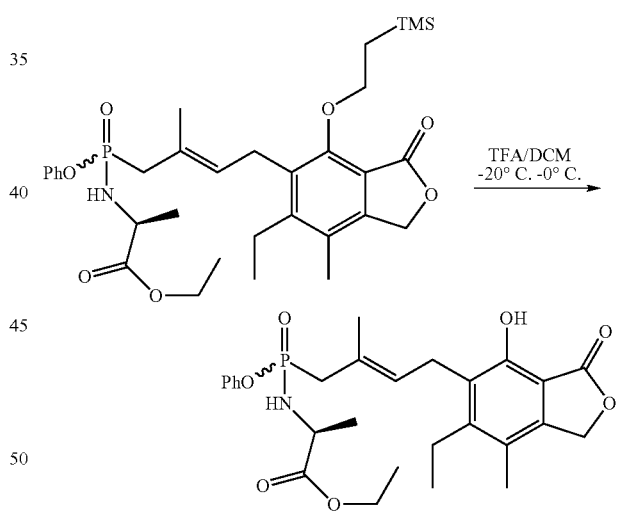

2-{[4-(6-Ethyl-4-hydroxy-7-methyl-3-oxo-1,3-dihydro-isobenzofuran-5-yl)-2-methyl-but-2-enyl]-phenoxy-phosphinoylamino}-propionic acid ethyl ester 2-({4-[6-Ethyl-7-methyl-3-oxo-4-(2-trimethylsilanyl-ethoxy)-1,3-dihydro-isobenzofuran-5-yl]-2-methyl-but-2-enyl}-phenoxy-phosphinoylamino)-propionic acid ethyl ester (7.5 mg, 0.012 mmol) was dissolved in TFA/DCM (10%, 0.3 mL) at −20° C. The reaction mixture was warmed to 0° C. and stirred at this temperature for 45 minutes. Pyridine (0.09 mL) was added the solvents were removed in vacuo. The crude material was purified by RP-HPLC (eluent: water/MeCN). The product-containing fractions were combined and lyophilized, yielding a white powder (5.5 mg, 87%). $^1$H NMR (300 MHz, CDCl$_3$): δ=1.12-1.29 (m, 6H), 2.03 (s, 3H), 2.17 (s, 3H), 2.65-2.74 (m, 4H), 3.38 (m, 1H), 3.53 (t, J=6.3 Hz, 2H), 4.03 (m, 3H), 5.22 (s, 2H), 5.36 (m, 1H), 7.11-7.16 (m, 3H), 7.24-7.30 (m, 2H), 7.72 (m, 1H) ppm; $^{31}$P NMR (121 MHz, CDCl$_3$): δ=27.11, 27.57 ppm; MS=515 [M$^+$+1].
Example 280
Preparation of Representative Compounds of the Invention
Representative compounds of the invention can be prepared as illustrated below.
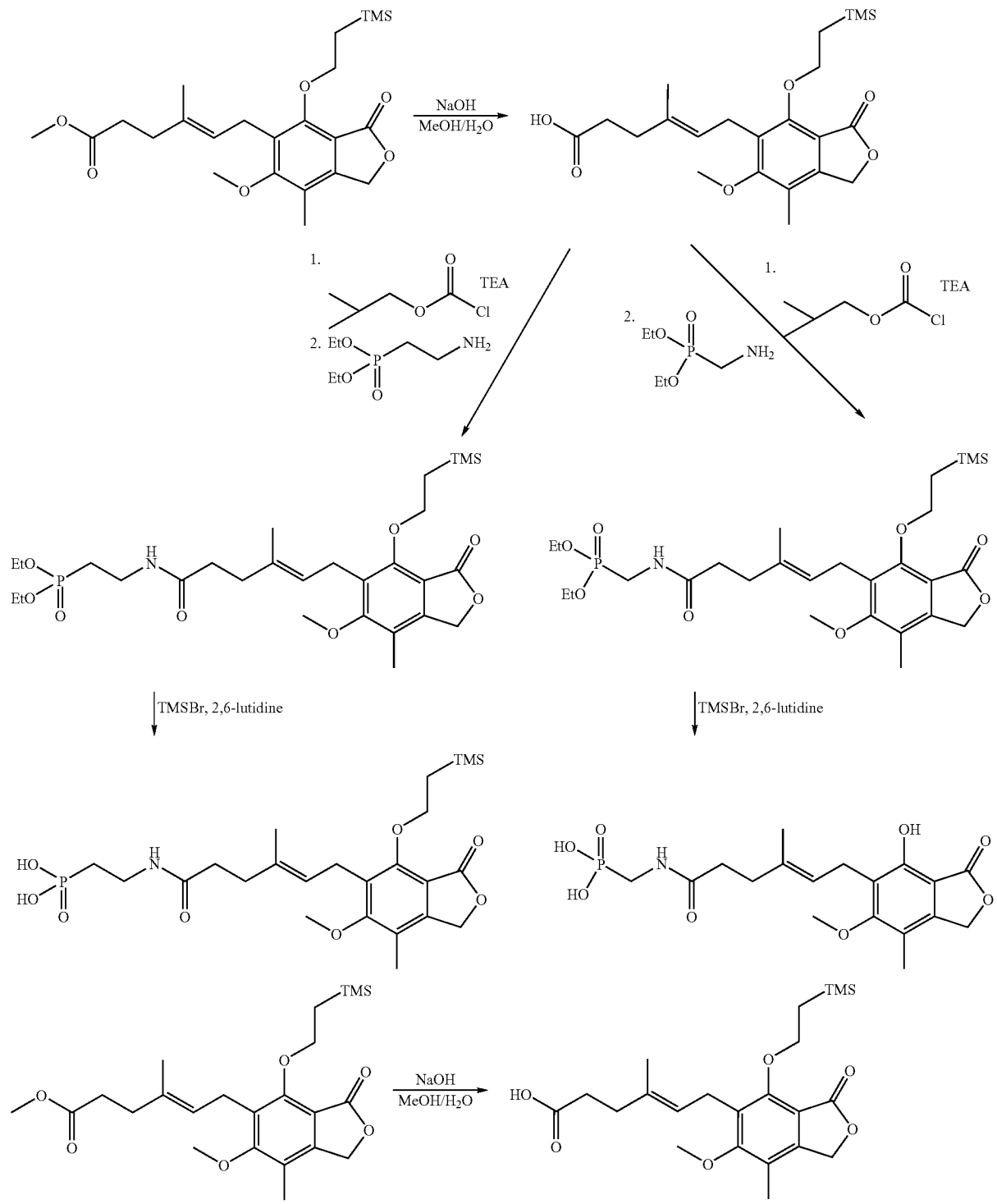

6-[6-Methoxy-7-methyl-3-oxo-4-(2-trimethylsilanyl-ethoxy)-1,3-dihydro-isobenzofuran-5-yl]-4-methyl-hex-4-enoic acid A mixture of 6-[6-methoxy-7-methyl-3-oxo-4-(2-trimethylsilanyl-ethoxy)-1,3-dihydro-isobenzofuran-5-yl]-4-methyl-hex-4-enoic acid methyl ester (1.5 g, 3.45 mmol) and sodium hydroxide (552 mg) in a mixture of methanol (20 mL) and water (7 mL) was stirred at room temperature for one hour. The solution was acidified with 1N HCl. The precipitate was collected by suction filtration and washed with water to give the desired product (1.2 g, 83%). $^1$H NMR (300 MHz, CDCl$_3$) δ 0.02 (s, 9H), 1.15-1.22 (m, 2H), 1.76 (s, 3H), 2.13 (s, 3H), 2.12-2.28 (m, 2H), 2.35-2.41 (m, 2H), 3.37 (d, 2H, J=7 Hz), 3.71 (s, 3H), 4.22-4.28 (m, 2H), 5.07 (s, 2H), 5.13-5.17 (m, 1H) ppm; MS (m/z) 419.3 [M−H]$^-$, 443.2 [M+Na]$^+$.

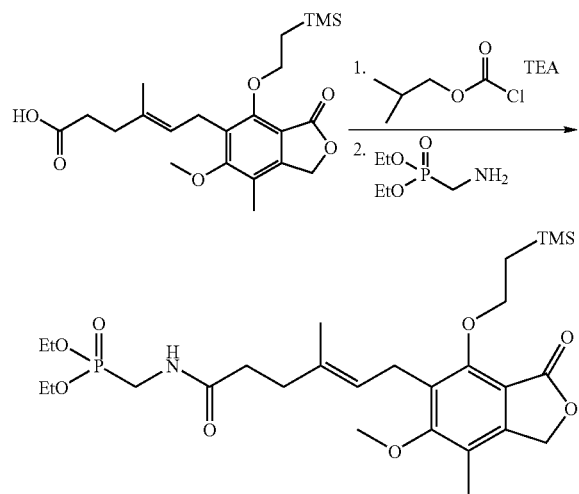

({6-[6-Methoxy-7-methyl-3-oxo-4-(2-trimethylsilanyl-ethoxy)-1,3-dihydro isobenzofuran-5-yl]-4-methyl-hex-4-enoylamino}-methyl)-phosphonic acid diethyl ester To a solution of 6-[6-methoxy-7-methyl-3-oxo-4-(2-trimethylsilanyl-ethoxy)-1,3-dihydro-isobenzofuran-5-yl]-4-methyl-hex-4-enoic acid (50 mg, 0.12 mmol) in THF (1 mL) was added isobutyl chloroformate (17 µL, 0.13 mmol) and triethylamine (50 µL, 0.36 mmol) at 0° C. After stirring at 0° C. for 2 hours, diethyl (aminomethyl) phosphonate oxalate (62 mg, 0.26 mmol) was added and stirring was continued at room temperature for 20 minutes. After removal of solvent, the residue was purified by preparative reverse-phase HPLC to afford 54.8 mg (81%) of the desired product. $^1$H NMR (300 MHz, CDCl$_3$) δ 0.03 (s, 9H), 1.15-1.22 (m, 2H), 1.31 (t, 6H), 1.81 (s, 3H), 2.18 (s, 3H), 2.30 (m, 4H), 3.41 (d, 2H, J=7 Hz), 3.65 (dd, 2H, J=6, 12 Hz), 3.77 (s, 3H), 3.77-4.16 (m, 4H), 4.26-4.32 (m, 2H), 5.12 (s, 2H), 5.17-5.19 (m, 1H), 5.86 (bs, 1H) ppm; $^{31}$P (121.4 MHz, CDCl$_3$) δ 23.01 ppm; MS (m/z) 568 [M−H]$^-$, 592 [M+Na]$^+$.

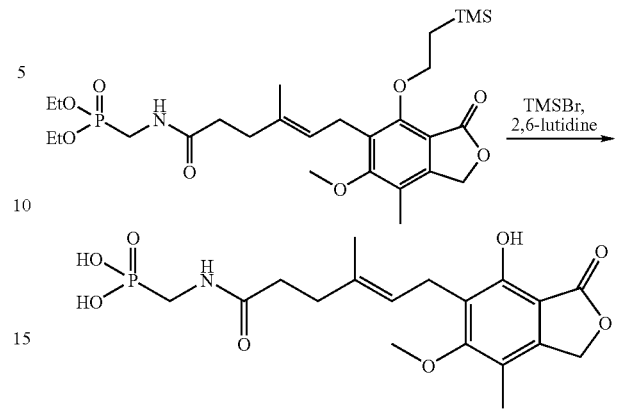

{[6-(4-Hydroxy-6-methoxy-7-methyl-3-oxo-1,3-dihydro-isobenzofuran-5-yl)-4-methyl-hex-4-enoylamino]-methyl}-phosphonic acid To a solution of ({6-[6-methoxy-7-methyl-3-oxo-4-(2-trimethylsilanyl-ethoxy)-1,3-dihydro-isobenzofuran-5-yl]-4-methyl-hex-4-enoylamino}-methyl)-phosphonic acid diethyl ester (40 mg, 0.07 mmol) in acetonitrile (1 mL) was added TMSBr (91 µL, 0.7 mmol) followed by 2,6-lutidine (81.5 µL, 0.7 mmol). The reaction was allowed to proceed overnight when it was completed as judged by LCMS. The reaction mixture was quenched with MeOH and concentrated to dryness. The residue was purified by preparative reverse-phase HPLC to afford 2.6 mg (9%) of desired product as a white solid. $^1$H NMR (300 MHz, CD$_3$OD) δ 1.67 (s, 3H), 2.17 (m, 5H), 2.30-2.46 (m, 2H), 2.80-2.86 (m, 2H), 3.55 (m, 2H), 3.82 (s, 3H), 5.26 (s, 3H) ppm; $^{31}$P (121.4 MHz, CD$_3$OD) δ 10.27 ppm; MS (m/z) 412 [M−H]$^-$, 414 [M+H]$^+$.

Example 281

Preparation of Representative Compounds of the Invention

Representative compounds of the invention can be prepared as illustrated below.

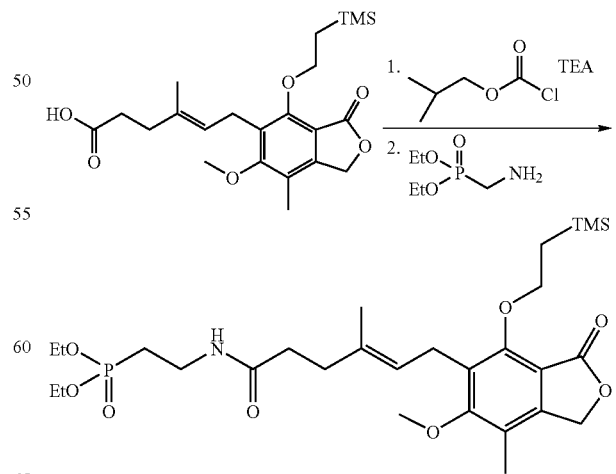

1017

(2-{6-[6-Methoxy-7-methyl-3-oxo-4-(2-trimethylsilanyl-ethoxy)-1,3-dihydro-isobenzofuran-5-yl]-4-methyl-hex-4-enoylamino}-ethyl)-phosphonic acid diethyl ester To a solution of 6-[6-methoxy-7-methyl-3-oxo-4-(2-trimethylsilanyl-ethoxy)-1,3-dihydro-isobenzofuran-5-yl]-4-methyl-hex-4-enoic acid (50 mg, 0.12 mmol) in THF (1 mL) was added isobutyl chloroformate (17 μL, 0.13 mmol) and triethylamine (50 μL, 0.36 mmol) at 0° C. After stirring at 0° C. for 2 hours, diethyl (aminoethyl) phosphonate oxalate (62 mg, 0.26 mmol) was added and stirred at room temperature was continued for one hour. After removal of solvent, the residue was purified by preparative reverse-phase HPLC to afford 37 mg (54%) of the desired product as a white solid. $^1$H NMR (300 MHz, CDCl$_3$) δ 0.03 (s, 9H), 1.15-1.22 (m, 2H), 1.31 (t, 6H), 1.81 (s, 3H), 1.85-1.93 (m,2H), 2.18 (s, 3H), 2.30 (m, 4H), 3.41 (d, 2H, J=7 Hz), 3.48-3.54 (m, 2H), 3.77 (s, 3H), 3.77-4.16 (m, 4H), 4.26-4.32 (m,2H), 5.12 (s, 2H), 5.17-5.19 (m, 1H), 6.30 (bs, 1H) ppm; $^{31}$P (121.4 MHz, CDCl$_3$) δ 29.91 ppm; MS (m/z) 584 [M+H]$^+$.

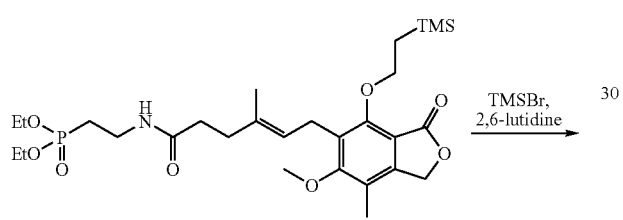

1018

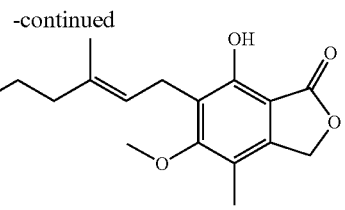

{2-[6-(4-Hydroxy-6-methoxy-7-methyl-3-oxo-1,3-dihydro-isobenzofuran-5-yl)-4-methyl-hex-4-enoylamino]-ethyl}-phosphonic acid To a solution of (2-{6-[6-methoxy-7-methyl-3-oxo-4-(2-trimethylsilanyl-ethoxy)-1,3-dihydro-isobenzofuran-5-yl]-4-methyl-hex-4-enoylamino}-ethyl)-phosphonic acid diethyl ester (36.6 mg, 0.063 mmol) in acetonitrile (1 mL) was added TMSBr (81 μL, 0.63 mmol) followed by 2,6-lutidine (73 μL, 0.63 mmol). The reaction was allowed to proceed overnight, when it was completed as judged by LCMS. The reaction mixture was quenched with MeOH and concentrated to dryness. The residue was purified by preparative reverse-phase HPLC to afford 5.8 mg (29%) of desired product as a white solid. $^1$H NMR (300 MHz, CD$_3$OD) δ 1.80 (s, 3H), 2.14 (m, 5H), 2.25 (m, 4H), 3.35 (m, 2H), 3.38-3.38 (m, 2H), 3.75 (s, 3H), 5.23 (s, 3H) ppm; $^{31}$P (121.4 MHz, CD$_3$OD) δ 26.03 ppm; MS (m/z) 426 [M−H]$^−$, 428 [M+H]$^+$.

Example 282

Preparation of Representative Compounds of the Invention

Representative compounds of the invention can be prepared as illustrated below.

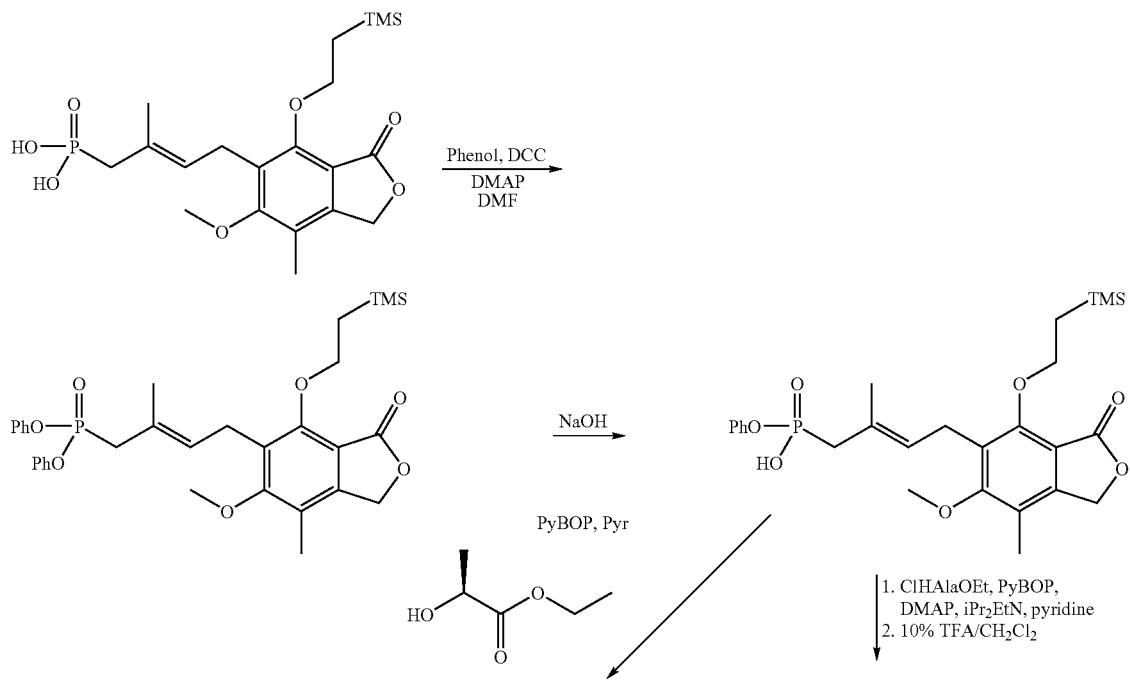

-continued

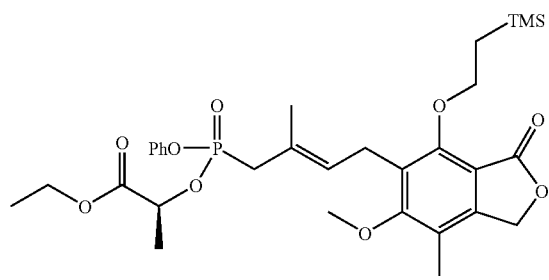

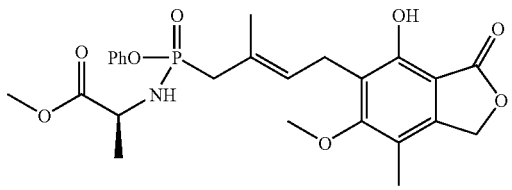

10% TFA/DCM

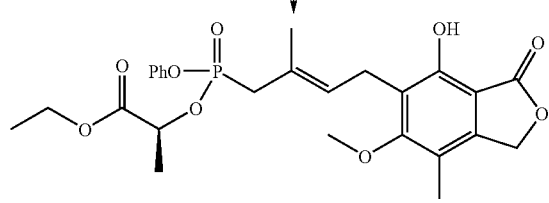

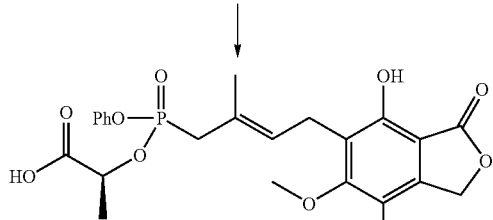

Phenol, DCC
DMAP
DMF

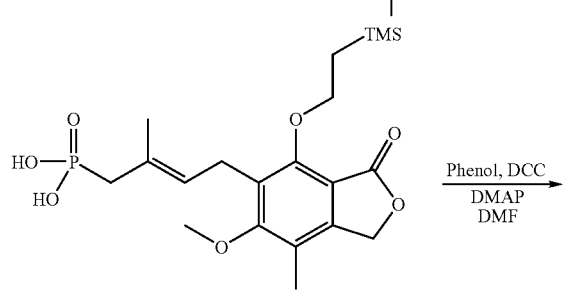

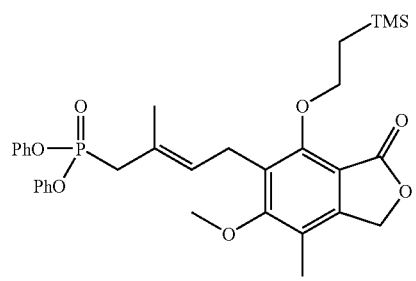

{4-[6-Methoxy-7-methyl-3-oxo-4-(2-trimethylsilanyl-ethoxy)-1,3-dihydro-isobenzofuran-5-yl]-2-methyl-but-2-enyl}-phosphonic acid diphenyl ester To a solution of [{4-[6-methoxy-7-methyl-3-oxo-4-(2-trimethylsilanyl-ethoxy)-1,3-dihydro-isobenzofuran-5-yl]-2-methyl-but-2-enyl}-phosphonic acid (260 mg, 0.59 mmol) in DMF (6 mL) and phenol (555 mg, 5.9 mmol) was added dicyclohexyl carbodiimide (1.21 g, 5.9 mmol) and DMAP (36 mg, 0.295 mmol). The reaction mixture was heated to 140° C. for 30 minutes. After cooling to room temperature, the mixture was partitioned between EtOAc/Hexane (1:1) and 5% aqueous LiCl solution. The organic layer was washed with 5% aqueous LiCl solution repeatedly, then dried over Na$_2$SO$_4$. After removal of solvent, the residue was purified by silica gel chromatography to provide 75 mg (21%) of the desired product. MS (m/z) 617 [M+Na]$^+$.

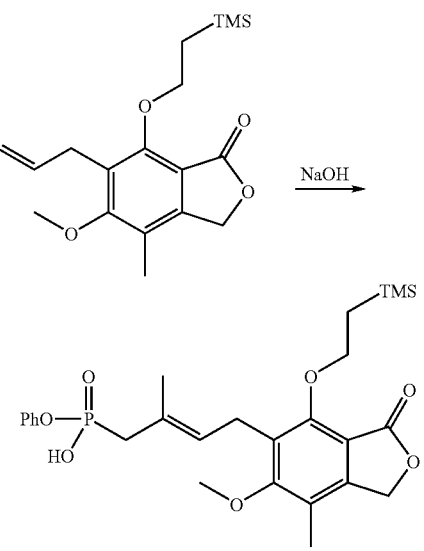

NaOH

{4-[6-Methoxy-7-methyl-3-oxo-4-(2-trimethylsila-nyl-ethoxy)-1,3-dihydro-isobenzofuran-5-yl]-2-me-thyl-but-2-enyl}-phosphonic acid monophenyl ester To a solution of {4-[6-methoxy-7-methyl-3-oxo-4-(2-tri-methylsilanyl-ethoxy)-1,3-dihydro-isobenzofuran-5-yl]-2-methyl-but-2-enyl}-phosphonic acid diphenyl ester (75 mg, 0.126 mmol) in THF (5 mL) was added 1N NaOH (0.1 mL) solution. The mixture was allowed to stir at room temperature for 16 hours. EtOAc was added and the resulting mixture was washed with 1H HCl. The organic layer was concentrated to dryness and the residue was purified by RP HPLC using a C18 column with a gradient of H$_2$O, 0.1% TFA-acetonitrile, 0.1% TFA to provide 24.8 mg (38%) of the desired product. MS (m/z) 517 [M−H]$^-$, 541 [M+Na]$^+$.

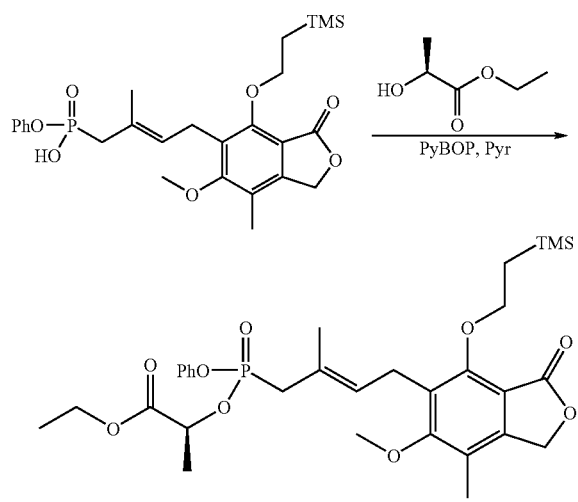

2-({4-[6-Methoxy-7-methyl-3-oxo-4-(2-trimethylsi-lanyl-ethoxy)-1,3-dihydro-isobenzofuran-5-yl]-2-methyl-but-2-enyl}-phenoxy-phosphinoyloxy)-pro-pionic acid ethyl ester To a solution of {4-[6-methoxy-7-methyl-3-oxo-4-(2-tri-methylsilanyl-ethoxy)-1,3-dihydro-isobenzofuran-5-yl]-2-methyl-but-2-enyl}-phosphonic acid monophenyl ester (25 mg, 0.048 mmol) and ethyl (S)-(−)-lactate (34 mg, 0.288 mmol) in pyridine (1 mL) was added PyBOP (125 mg, 0.24 mmol). The solution was stirred at room temperature for 16 hours and concentrated. The residue was purified by RP HPLC using a C18 column with a gradient of H$_2$O, 0.1% TFA-acetonitrile, 0.1% TFA to provide 24 mg (83%) of the desired product. MS (m/z) 641 [M+Na]$^+$.

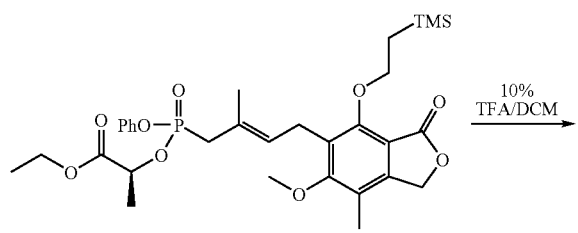

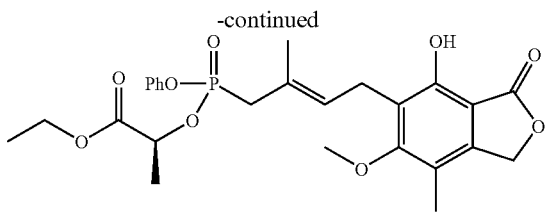

2-{[4-(4-Hydroxy-6-methoxy-7-methyl-3-oxo-1,3-dihydro-isobenzofuran-5-yl)-2-methyl-but-2-enyl]-phenoxy-phosphinoyloxy}-propionic acid ethyl ester To a solution of 2-({4-[6-methoxy-7-methyl-3-oxo-4-(2-trimethylsilanyl-ethoxy)-1,3-dihydro-isobenzofuran-5-yl]-2-methyl-but-2-enyl}-phenoxy-phosphinoyloxy)-propionic acid ethyl ester (24 mg, 0.039 mmol) in DCM (1 mL) was added TFA (0.5 mL) and the mixture was stirred at room temperature for 10 minutes. The reaction mixture was dried under reduced pressure and the residue was purified by RP-HPLC to provide 18 mg (90%) of the desired product as a clear oil. $^1$H NMR (300 MHz, CDCl$_3$) δ 1.18-1.34 (m, 3H), 1.36-1.48 (dd,3H), 2.02 (m, 3H), 2.17 (s, 3H), 2.78-2.98 (dd, 2H), 3.45 (m, 2H), 3.79 (s, 3H), 4.05-4.25 (m, 2H), 4.97 (m, 1H), 5.21 (s, 2H), 5.48 (t, J=7.2 Hz, 1H), 7.05-7.18 (m, 5H) ppm; $^{31}$P (1121.4 MHz, CDCl$_3$) δ 24.59, 26.13 ppm; MS (m/z) 517 [M−H], 519 [M+H]$^+$.

Example 283

Preparation of Representative Compounds of the Invention

Representative compounds of the invention can be pre-pared as illustrated below.

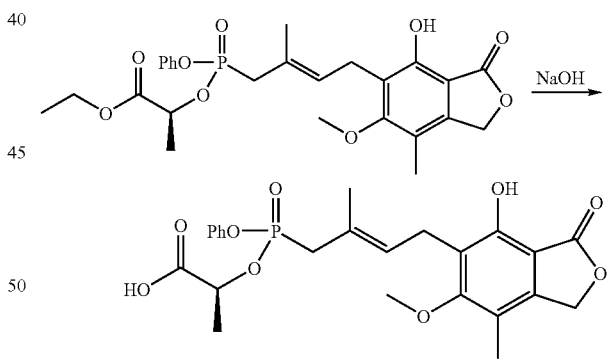

2-{[4-(4-Hydroxy-6-methoxy-7-methyl-3-oxo-1,3-dihydro-isobenzofuran-5-yl)-2-methyl-but-2-enyl]-phenoxy-phosphinoyloxy}-propionic acid To a solution of 2-{[4-(4-hydroxy-6-methoxy-7-methyl-3-oxo-1,3-dihydro-isobenzofuran-5-yl)-2-methyl-but-2-enyl]-phenoxy-phosphinoyloxy}-propionic acid ethyl ester (10 mg, 0.019 mmol) in THF (3 mL) was added 1N NaOH (232 μL), and the mixture was stirred at room temperature for 1 hour. The reaction mixture was dried under reduced pressure and the residue was purified by RP-HPLC to provide 6 mg (77%) of the desired product as a clear oil. $^1$H NMR (300

MHz, CD$_3$OD) δ 1.41 (d, J=7 Hz, 3H), 1.97 (s, 3H), 2.16 (s, 3H), 2.59 (d, J=22 Hz, 2H), 3.45 (m, 2H), 3.79 (s, 3H), 4.83 (m, 1H), 5.26 (s, 2H), 5.43 (t, J=7.2 Hz, 1H) ppm; $^{31}$P (121.4 MHz, CD$_3$OD) δ 27.02 ppm; MS (m/z) 413 [M−H], 415 [M+H]$^+$.

Example 284

Preparation of Representative Compounds of the Invention

Representative compounds of the invention can be prepared as illustrated below.

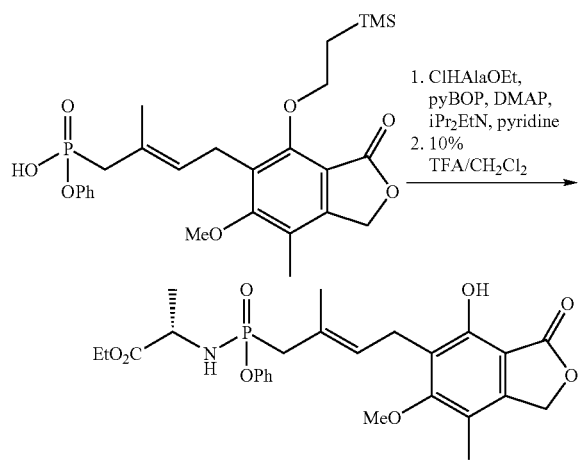

2-{[4-(4-Hydroxy-6-methoxy-7-methyl-3-oxo-1,3-dihydro-isobenzofuran-5-yl)-2-methyl-but-2-enyl]-phenoxy-phosphinoylamino}-propionic acid ethyl ester {4-[6-methoxy-7-methyl-3-oxo-4-(2-trimethylsilanyl-ethoxy)-1,3-dihydro-isobenzofuran-5-yl]-2-methyl-but-2-enyl}-phosphonic acid monophenyl ester (1 g, ~1.9 mmol) was combined with pyBOP (2 g, 4 mmol) and DMAP (120 mg, 0.96 mmol). A solution of L-alanine ethyl ester hydrochloride salt (2.9 g, 19 mmol) and diisopropylethylamine (6.7 mL, 38 mmol) in pyridine (5 mL) was added to the monoacid mixture and the reaction was stirred at room temperature for 12 hours. The reaction mixture was then concentrated and purified twice by column chromatography (1% MeOH/CH$_2$Cl$_2$ 3% MeOH/CH$_2$Cl$_2$). The resulting oil was dissolved in a vigorously-stirred solution of 10% TFA/CH$_2$Cl$_2$ (30 mL) at −40° C. The reaction was gradually warmed to 0° C. After about 3 hours, the reaction was complete. Pyridine (4.5 mL) was added, and the reaction mixture was concentrated. The product was purified by preparative TLC (5% MeOH/CH$_2$Cl$_2$) and concentrated to give 210 mg (21%) of the desired product as a light yellow oil. $^1$H NMR (300 MHz, CDCl$_3$) δ 7.83-7.70 (m, 1H), 7.30-7.20 (m, 2H), 7.18-7.03 (m, 3H), 5.60-5.35 (m, 1H), 5.21 (s, 2H), 4.17-3.95 (m, 3H), 3.79 (s, 3H), 3.60-3.40 (m, 3H), 2.80-2.60 (m, 2H), 2.17 (m, 3H), 2.01 (m, 3H), 1.30-1.10 (m, 6H) ppm; $^{31}$P NMR (121 MHz, CDCl$_3$) δ 28.0, 27.5 ppm; MS (m/z) 516 [M−H]$^-$.

Example 285

Preparation of Representative Compounds of the Invention

Representative compounds of the invention can be prepared as illustrated below.

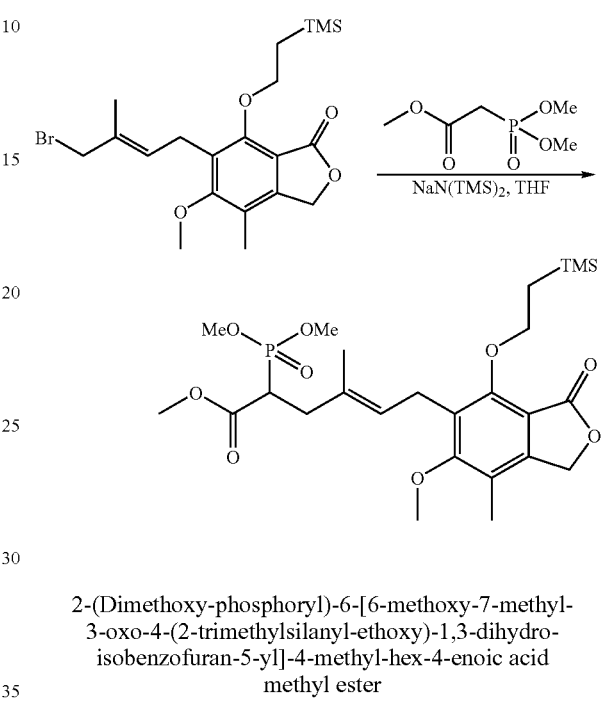

2-(Dimethoxy-phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester To a solution of trimethylphosphonoacetate (63 μL, 0.39 mmol) in THF (1 mL) was added NaN(TMS)$_2$ (0.39 mmol, 0.39 mL) at ambient temperature. After 30 minutes, a solution of 6-(4-bromo-3-methyl-but-2-enyl)-5-methoxy-4-methyl-7-(2-trimethylsilanyl-ethoxy)-3H-isobenzofuran-1-one (69 mg, 0.156 mmol) in THF (1 mL) was added. The reaction mixture was stirred for 2 hours, when a precipitate was observed. The reaction mixture was worked up by addition of a saturated aqueous solution of ammonium chloride and extraction of the product with EtOAc. The organic extract was dried and the product was purified using silica gel chromatography with 0-100% EtOAc-Hexanes to provide 40 mg of the desired product as a colorless oil. $^1$H NMR (300 MHz, CDCl$_3$) δ 0.05 (s, 9H), 1.20-1.26 (m, 2H), 1.79 (s, 3H), 2.17 (s, 3H), 2.42-2.72 (m, 2H), 3.19 (ddd, 1H, J=4, 12, 23 Hz), 3.39 (d, 2H, J=7 Hz), 3.62 (s, 3H), 3.75 (s, 3H), 3.77-3.84 (m, 6H), 4.27-4.34 (m, 2H), 5.12 (s, 2H), 5.24 (t, 1H, J=7 Hz) ppm; $^{31}$P (121.4 MHz, CDCl$_3$) δ 25.1 ppm; MS (m/z) 565.2 [M+Na]$^+$.

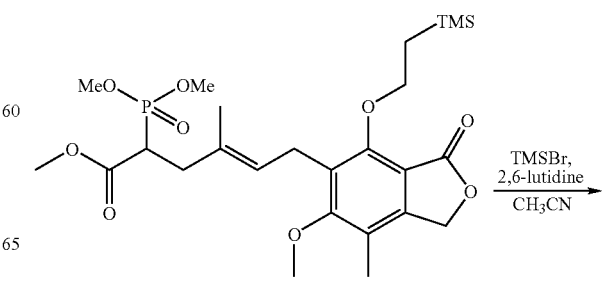

-continued

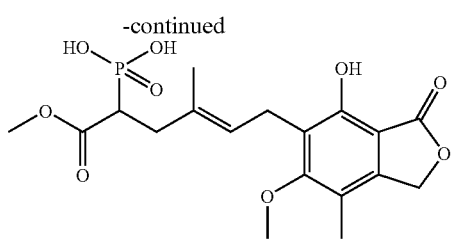

6-(4-Hydroxy-6-methoxy-7-methyl-3-oxo-1,3-dihydro-isobenzofuran-5-yl)-4-methyl-2-phosphono-hex-4-enoic acid methyl ester To a solution of 2-(dimethoxy-phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester (30 mg, 0.055 mmol) in acetonitrile (2 mL) was added trimethylsilyl bromide (0.18 mL). After 10 minutes, 2,6-lutidine (0.16 mL) was added to the reaction at ambient temperature. The reaction was allowed to proceed for 16 hours before it was concentrated to dryness. The residue was resuspended in a solution of DMF:H$_2$O (8:2, 1 mL) and purified by RP HPLC using a C18 column with a gradient of H$_2$O, 0.1% TFA-acetonitrile, 0.1% TFA to provide 18 mg of the product as a white powder. $^1$H NMR (300 MHz, CD$_3$OD) δ 1.81 (s, 3H), 2.16 (s, 3H), 2.40-2.49 (m, 1H), 2.63 (dt, 1H, J=6, 17 Hz), 3.07 (ddd, 1H, J=4, 12, 23 Hz), 3.38 (3, 2H, J=7 Hz), 3.52 (s, 3H), 3.77 (s, 3H), 5.25 (s, 2H), 5.28 (t, 1H, J=7 Hz) ppm; $^{31}$P (121.4 MHz, CDCl$_3$) δ 19.5 ppm; MS (m/z) 415.2 [M+H]$^+$, 437.2 [M+Na]$^+$.

Example 286

Preparation of Representative Compounds of the Invention

Representative compounds of the invention can be prepared as illustrated below.

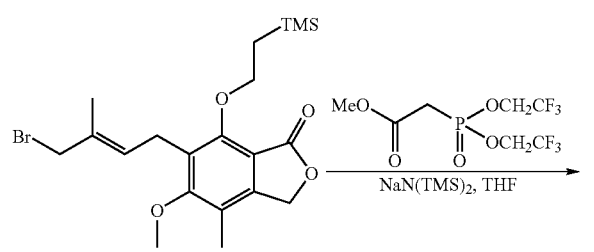

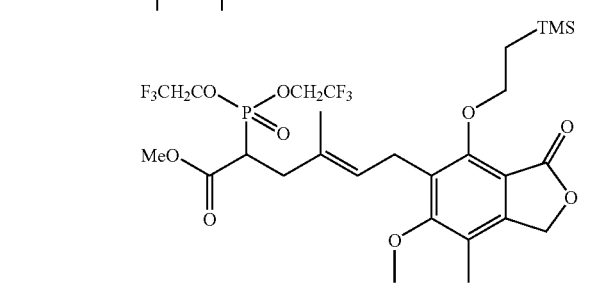

2-(Bis-(2,2,2-trifluoroethoxy)phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester To a solution of [bis-(2,2,2-trifluoro-ethoxy)-phosphoryl]-acetic acid methyl ester (186 μL, 0.88 mmol) in anhydrous THF (2 mL) was added a solution of 1N NaN(TMS)$_2$ in THF (0.88 mL, 0.88 mmol). The solution was stirred at room temperature for 30 minutes, whereupon a solution of 6-(4-bromo-3-methyl-but-2-enyl)-5-methoxy-4-methyl-7-(2-trimethylsilanyl-ethoxy)-3H-isobenzofuran-1-one (98 mg, 0.22 mmol) in THF (1 mL) was added. The reaction mixture was stirred overnight when a precipitate was observed. The reaction mixture was worked up by addition of a saturated aqueous solution of ammonium chloride and extraction of the product with EtOAc. The organic extract was dried and the product was purified by RP HPLC using a C18 column with a gradient of H$_2$O, 0.1% TFA-acetonitrile, 0.1% TFA to provide 72 mg (48%) of the product as a colorless oil. $^1$H NMR (300 MHz, CDCl$_3$) δ 0.05 (s, 9H), 1.22 (t, 3H, J=7 Hz), 1.81 (s, 3H), 2.18 (s, 3H), 2.5-2.7 (m, 2H), 3.3 (ddd, 1H, J=4, 12, 23 Hz), 3.40 (d, 2H, J=7 Hz), 3.65 (s, 3H), 3.76 (s, 3H), 4.29-5.13 (m, 6H), 5.13 (s, 2H), 5.28 (t, 1H, J=7 Hz) ppm; MS (m/z) 701.2 [M+Na]$^+$.

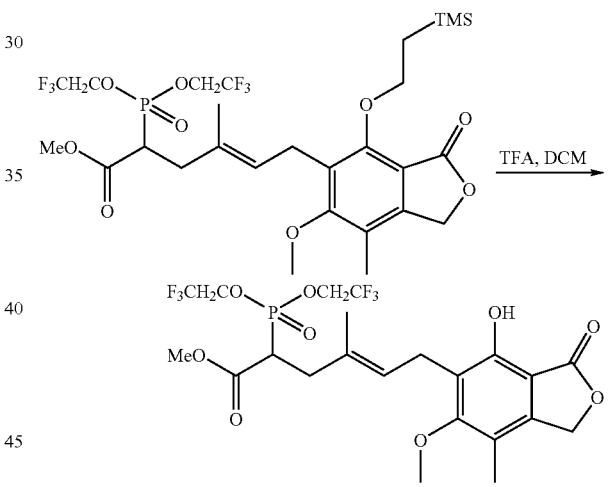

2-(Bis-(2,2,2-trifluoroethoxy)phosphoryl)-6-[6-methoxy-7-methyl-3-oxo-4-(2-hydroxyoxy)-1,3-dihydro-isobenzofuran-5-yl]-4-methyl-hex-4-enoic acid methyl ester

[2-(Bis-(2,2,2-trifluoroethoxy)phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester (70 mg) was dissolved in a solution of 10% trifluoroacetic acid in dichloromethane (5 mL). After 10 minutes, the mixture was concentrated and the product was purified by RP HPLC using a C18 column with a gradient of H$_2$O, 0.1% TFA-acetonitrile, 0.1% TFA to provide 45 mg (75%) of the product as a colorless oil. $^1$H NMR (300 MHz, CDCl$_3$) δ 1.81 (s, 3H), 2.16 (s, 3H), 2.5-2.7 (m, 2H), 3.3 (ddd, 1H), 3.38 (d, 2H, J=7 Hz), 3.65 (s, 3H), 3.77 (s, 3H), 4.33-4.43 (m, 4H), 5.21 (s, 2H), 5.33 (t, 1H, J=7 Hz) ppm; $^{31}$P (121.4 MHz, CDCl$_3$) δ 25.8 ppm; MS (m/z) 601.2 [M+Na]$^+$.

Example 287

Preparation of Representative Compounds of the Invention

Representative compounds of the invention can be prepared as illustrated below.

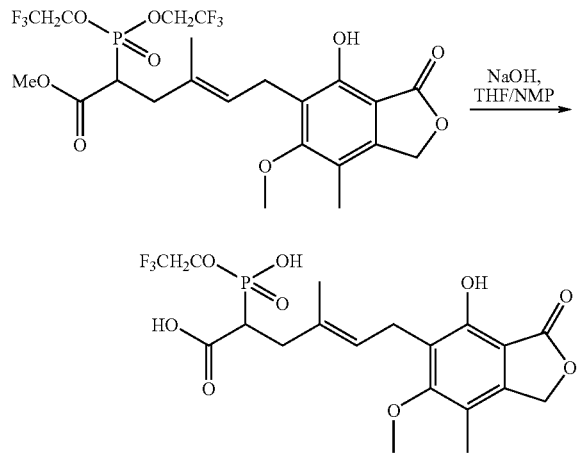

6-(4-Hydroxy-6-methoxy-7-methyl-3-oxo-1,3-dihydro-isobenzofuran-5-yl)-2-[hydroxy-(2,2,2-trifluoro-ethoxy)-phosphoryl]-4-methyl-hex-4-enoic acid To a solution of [bis-(2,2,2-trifluoro-ethoxy)-phosphoryl]-acetic acid methyl ester (186 μL, 0.88 mmol) in anhydrous THF (0.5 mL) was added a solution of 1N NaOH (aqueous; 0.06 mL) and N-methylpyrrolidinone (0.2 mL). After 6.5 hours, another aliquot of 1N NaOH (0.06 mL) was added and the mixture was stirred overnight. After concentration, the residue was suspended in DMF (<1 mL), neutralized with a few drops of TFA and purified by RP HPLC using a C18 column with a gradient of $H_2O$, 0.1% TFA-acetonitrile, 0.1% TFA to provide 5.6 mg (72%) of the product as a white powder after lyophilization. $^1$H NMR (300 MHz, $CD_3OD$) δ 1.83 (s, 3H), 2.16 (s, 3H), 2.43-2.51 (m, 1H), 2.59-2.70 (m, 1H), 3.13 (ddd, 1H), 3.40 (d, 2H), 3.76 (s, 3H), 4.36-4.47 (m, 2H), 5.25 (s, 2H), 5.34 (t, 1H, J=7 Hz) ppm; MS (m/z) 505.2 [M+Na]$^+$.

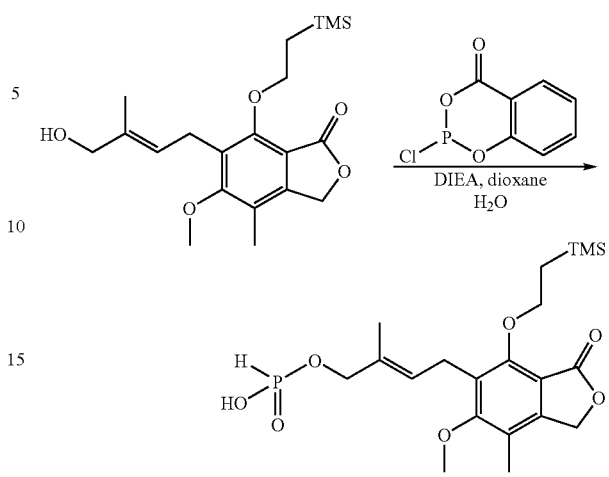

Example 288

Preparation of Representative Compounds of the Invention

Representative compounds of the invention can be prepared as illustrated below.

Phosphorous acid mono-{4-[6-methoxy-7-methyl-3-oxo-4-(2-trimethylsilanyl-ethoxy)-1,3-dihydro-isobenzofuran-5-yl]-2-methyl-but-2-enyl}ester To a solution of 6-(4-hydroxy-3-methyl-but-2-enyl)-5-methoxy-4-methyl-7-(2-trimethylsilanyl-ethoxy)-3H-isobenzofuran-1-one (75 mg, 0.20 mmol) and DIEA (49 μL, 0.28 mmol) in dioxane (2 mL) was added 2-chloro-4H-1,3,2-benzodioxaphosphorin-4-one (56.7 mg, 0.28 mmol) according the procedure of Shadid, B. et al., *Tetrahedron*, 1989, 45, 12, 3889. After 10 minutes, another portion of 2-chloro-4H-1,3,2-benzodioxaphosphorin-4-one (40 mg, 0.20 mmol) and DIEA (35 μL, 0.20 mmol) were added. The reaction was allowed to proceed at room temperature for an additional hour, after which it was quenched by the addition of $H_2O$. The solution was stirred for another 10 minutes and concentrated in vacuo to a small volume. The product was triturated with diethyl ether and coevaporated from acetonitrile (4×10 mL) to provide the product. $^1$H NMR (300 MHz, $CDCl_3$) δ 0.03 (s, 9H), 1.08-1.30 (m, 2H), 1.84 (br s, 3H), 2.17 (s, 3H), 3.46 (br s, 2H), 3.76 (s, 3H), 4.21-4.39 (m, 4H), 5.12 (s, 2H), 5.43-5.60 (m, 1H), 7.83 (br s, 1H); $^{31}$P (121.4 MHz, $CDCl_3$) δ 7.22; MS (m/z) 441 [M−H]$^−$.

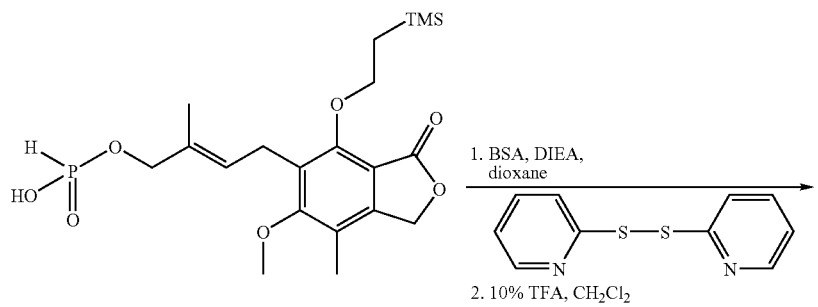

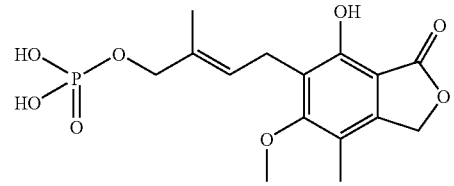

Example 289

Preparation of Representative Compounds of the Invention

Representative compounds of the invention can be prepared as illustrated below.

Phosphoric acid mono-{4-[6-methoxy-7-methyl-3-oxo-4-(2-trimethylsilanyl-ethoxy)-1,3-dihydro-isobenzofuran-5-yl]-2-methyl-but-2-enyl}ester A solution of phosphorous acid mono-{4-[6-methoxy-7-methyl-3-oxo-4-(2-trimethylsilanyl-ethoxy)-1,3-dihydro-isobenzofuran-5-yl]-2-methyl-but-2-enyl}ester (27 mg, 0.06 mmol) in dioxane (1 mL) was stirred with DIEA (21 µL, 0.12 mmol) and N,O-bis(trimethylsilyl)acetamide (29 µL, 0.12 mmol) at room temperature for 3 hours. To the reaction solution was added 2,2'-dipyridyldisulfide (16 mg, 0.072 mmol) and the mixture was allowed to stir for an additional 2 hours at room temperature. The reaction mixture was diluted by addition of $H_2O$ and the solution was stirred for 2 more hours when it was concentrated. The residue was dissolved in a solution of 10% TFA/$CH_2Cl_2$ and stirred at room temperature for 9 hours. The reaction mixture was dried under reduced pressure and the product was purified by reverse-phase HPLC to provide the desired product as a white solid. $^1$H NMR (300 MHz, $CD_3OD$) δ 1.87 (s, 3H), 2.16 (s, 3H), 3.47 (d, 2H, J=7 Hz), 3.79 (s, 3H), 4.28 (d, 2H, J=6 Hz), 5.26 (s, 2H), 5.50-5.61 (m, 1H); $^{31}$P (121.4 MHz, $CD_3OD$) δ 0.50; MS (m/z) 357 [M–H]$^-$.

Example 290

Specific Embodiments of the Invention

Several compounds of the invention are presented below

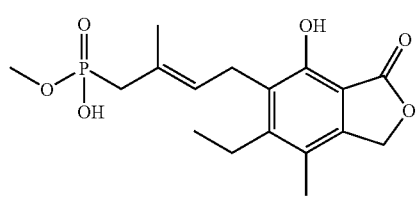

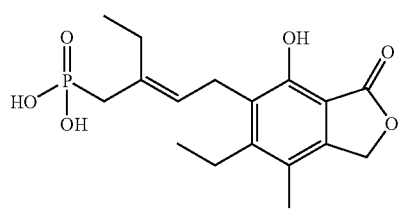

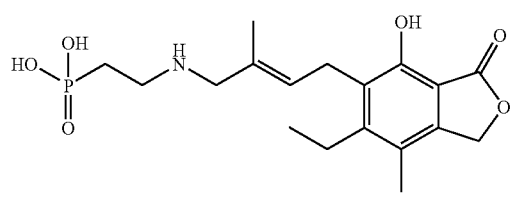

Example 291

Preparation of Representative Compounds of the Invention

Additional representative compounds of the invention, and intermediates thereof, can be prepared according to the methods presented below.

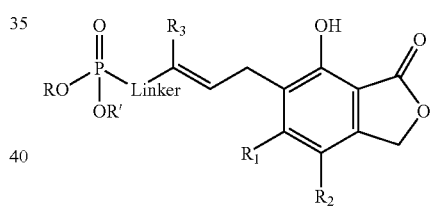

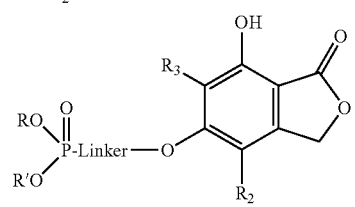

Linker = 0–8 atoms, preferably 1–6;
$R_1$ = OMe, OEt, vinyl, Et, cyclopropyl, NHMe, NHCHO
$R_2$ = Me, Cl, $CF_3$
$R_3$ = H, Me, cyclopropyl, Et, vinyl, $CF_3$
$R_4$ = H, Cl, Me, Et, cyclopropyl, vinyl, allyl, 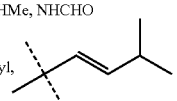

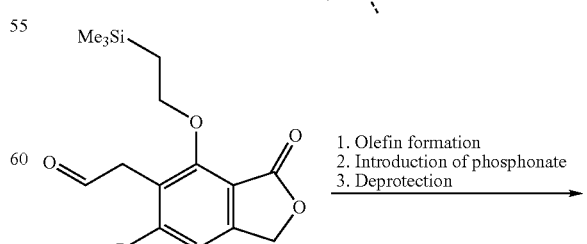

1. Olefin formation
2. Introduction of phosphonate
3. Deprotection

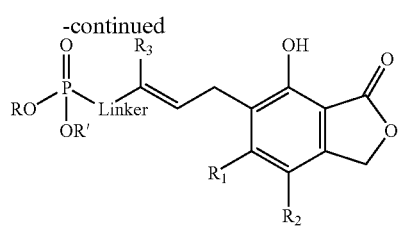

Synthesis of Phenacetaldehydes with Variants at $R_1$, $R_2$

The parent compound ($R_1$=OMe; $R_2$=Me) is accessible by semi-synthesis from mycophenolic acid as follows:

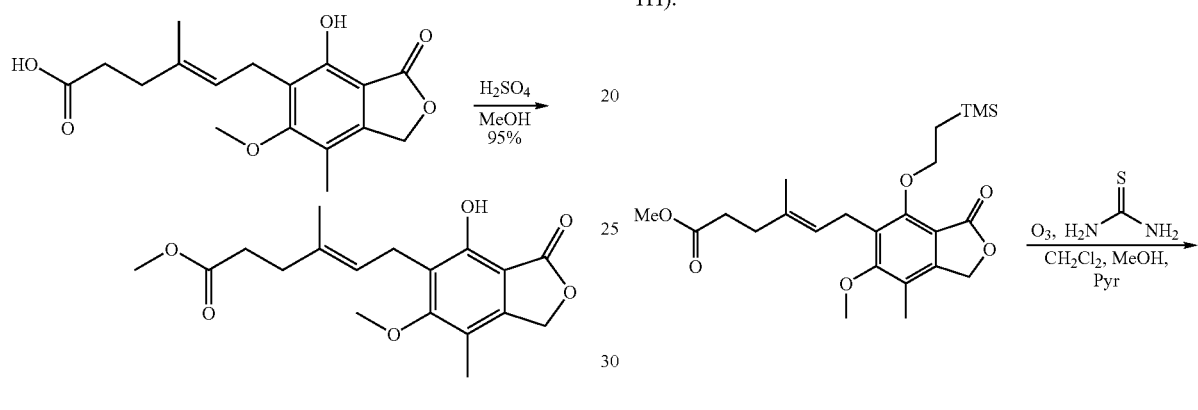

To a solution of mycophenolic acid (500 g, 1.56 mol) in MeOH (4 L) under nitrogen atmosphere was added sulfuric acid (10 mL) dropwise, and the suspension was stirred at room temperature. After 2 hours, the reaction became homogeneous, and soon thereafter a precipitate was formed. The reaction was allowed to stir at room temperature for 10 hours, at which time TLC indicated complete reaction. The reaction was cooled in an ice bath to 10° C. and then filtered using a Buchner funnel. The filter cake was washed with ice cold methanol (750 mL) followed by hexanes (750 mL) and then dried to give 497 g (95%) of the desired product as a solid: $^1$H NMR (300 MHz, CDCl$_3$) δ, 1.81 (s, 3H), 2.18 (s, 3H), 2.15 (s, 3H), 2.37-2.50 (m, 4H), 3.38 (d, 2H, J=7 Hz), 3.62 (s, 3H), 3.77 (s, 3H), 5.13 (s, 2H), 5.22 (m, 1H), 7.17 (s, 1H).

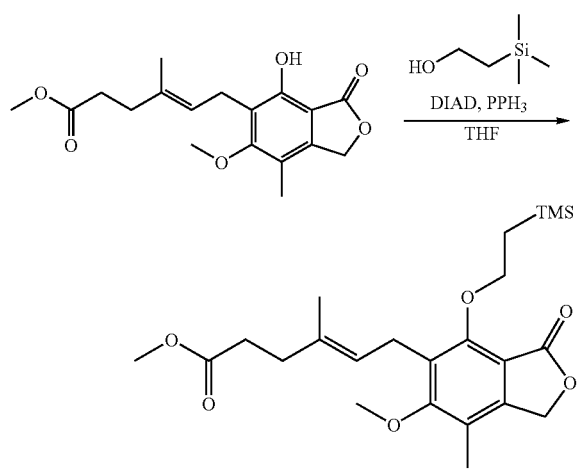

To a solution (3.99 g, 11.9 mmol), PPh$_3$ (4.68 g, 17.9 mmol), and diisopropyl azodicarboxylate (3.46 mL, 17.9 mmol) in THF (60 mL) at 0° C. was added a solution of 2-trimethylsilylethanol (2.05 mL, 14.3 mmol) in THF (20 mL). The resulting yellow solution was allowed to warm to room temperature and stirred for 4 hours. The reaction was worked up by concentrating the solution to dryness and addition of ether and hexanes. Triphenylphosphine oxide was removed by filtration and the filtrate was concentrated and purified by silica gel chromatography to provide 4.8 g (100%) as a clear oil: $^1$H NMR (300 MHz, CDCl$_3$) δ 0.03 (s, 9H), 1.18-1.30 (m, 2H), 1.81 (s, 3H), 2.18 (s, 3H), 2.25-2.33 (m, 2H), 2.37-2.45 (m, 2H), 3.42 (d, 2H, J=7 Hz), 3.62 (s, 3H), 3.77 (s, 3H), 4.25-4.35 (m, 2H), 5.13 (s, 2H), 5.12-5.22 (m, 1H).

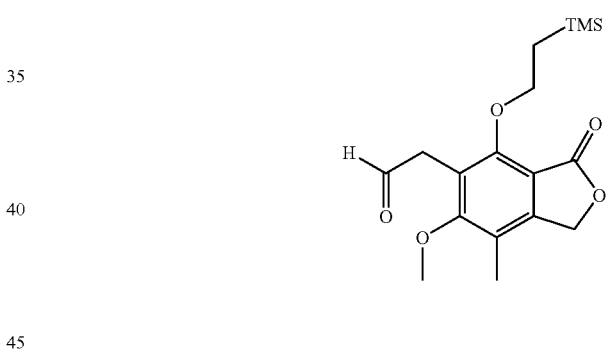

A solution (9.6 g, 22 mmol) in MeOH (90 mL), CH$_2$Cl$_2$ (90 mL) and pyridine (0.7 mL) was cooled to −70° C. using a dry ice/acetone bath. A stream of ozone was bubbled through the reaction via a gas dispersion tube until the reaction became blue in color (1.5 hours). The ozone line was replaced with a stream of nitrogen and bubbling continued for another 30 minutes, by which time the blue color had disappeared. To this solution at −70° C. was added thiourea (1.2 g, 15.4 mmol) in one portion, and the cooling bath was removed. The reaction was allowed to warm to room temperature and stirred for 15 hours. The reaction was worked up by filtration to remove solid thiourea S-dioxide, and then partitioned between CH$_2$Cl$_2$ and water. The organic layer was removed. The aqueous layer was washed with CH$_2$Cl$_2$ and the organic extracts were combined, washed with aqueous 1N HCl, saturated NaHCO$_3$ and brine, and dried in vacuo. The residue was purified by silica gel chromatography to afford 7.3 g (99%) as a white solid: $^1$H NMR (300 MHz, CDCl$_3$) δ −0.01 (s, 9H), 1.05-1.15 (m, 2H), 2.15 (s, 3H), 3.69 (s, 3H), 3.78 (d, 2H, J=1 Hz), 4.27-4.39 (m, 2H), 5.11 (s, 2H), 9.72 (d, 1H, J=1 Hz).

$R^1$ Variants

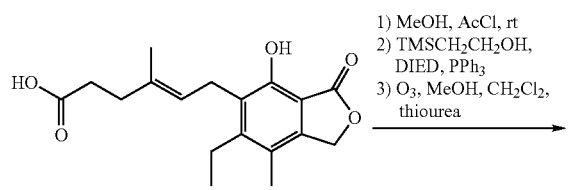

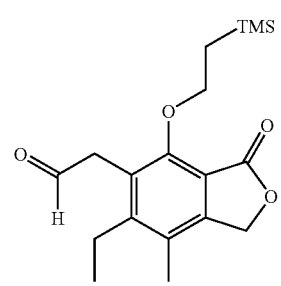

The starting material, synthesized according to *J. Med. Chem.*, 1996, 39, 4181-4196, is transformed to the desired aldehyde using methods analogous to those described above.

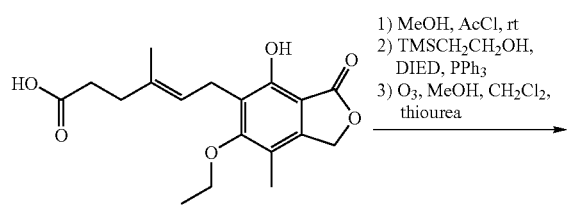

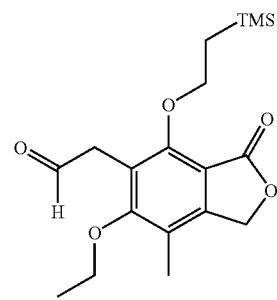

The starting material, synthesized according to *J. Med. Chem.*, 1996, 39, 4181-4196, is transformed to the desired aldehyde using methods analogous to those described above.

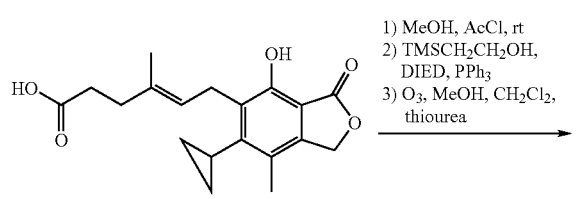

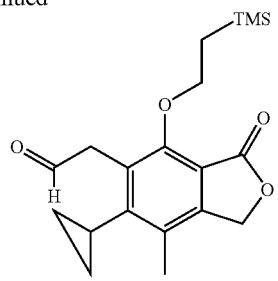

The starting material, synthesized according to *J. Med. Chem.*, 1996, 39, 4181-4196, is transformed to the desired aldehyde using methods analogous to those described above.

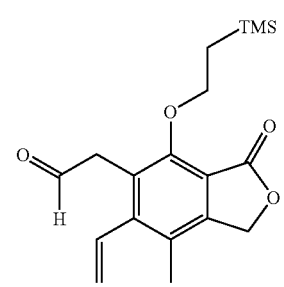

The aldehyde is dissolved in an organic solvent such as methanol and sodium borohydride is added. At the end of the reaction, aqueous HCl solution is added and the solvent is removed in vacuo. Further purification is achieved by chromatography.

The resulting alcohol is dissolved in an organic solvent such as dichloromethane (DCM). Pyridine and acetic anhydride are added and stirring at room temperature is continued. At the end of the reaction additional DCM is added and the solution is washed with aqueous HCl solution, aqueous sodium bicarbonate solution, and dried over sodium sulfate. Filtration and evaporation of the solvent in vacuo gives the crude product. Further purification is achieved by chromatography.

The acetate is dissolved in DCM and bromine is added, according to a procedure from *J. Med. Chem.*, 1996, 39, 4181-4196. At the end of the reaction, additional DCM is added and the solution is washed with aqueous sodium thiosulfate solution and brine. The organic layer is dried over sodium sulfate. Filtration and evaporation of solvents yields the crude material. Further purification is achieved by chromatography.

The product of the previous step, lithium chloride, triphenylarsine, tributylvinyltin, and tris(dibenzylideneacetone) dipalladium(0)-chloroform adduct are heated in an organic solvent such as N-methylpyrrolidinone at an elevated temperature of approximately 55° C., according to a procedure from *J. Med. Chem.*, 1996, 39, 4181-4196. At the end of the reaction, the mixture is cooled to room temperature and poured into a mixture of ice, potassium fluoride, water, and ethyl acetate. Stirring is continued for one hour. The suspension is filtered through Celite and extracted with ethyl acetate. The combined organic extracts are dried over sodium sulfate. The solvents are removed in vacuo and the crude material is further purified by chromatography.

The product of the previous step is dissolved in an organic solvent such as DCM or THF. 1,1,1-tris(acyloxy)-1,1-dihydro-1,2benziodoxol-3-(1H)-one (Dess-Martin reagent) is added and the solution is stirred at room temperature, according to a procedure from *J. Org. Chem.*, 1984, 48, 4155-4156. At the end of the reaction diethyl ether is added, followed by aqueous sodium hydroxide solution. The layers are separated and the organic layer is washed with aqueous sodium hydroxide solution, water, and dried over sodium sulfate. Filtration and evaporation of solvents yields the crude product. Further purification is achieved by chromatography.

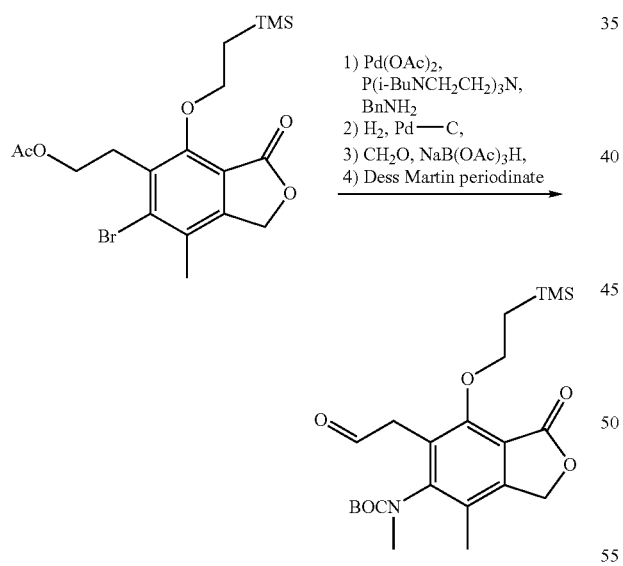

The starting material is dissolved in an organic solvent such as toluene. P(isobutylNCH$_2$CH$_2$)$_3$N, palladium(II)acetate, sodium tert. butoxide, and benzylamine are added and the mixture was heated at 80° C., according to a procedure from *J. Org. Chem.*, 2003, 68, 452-459. At the end of the reaction, the mixture is cooled to room temperature and the solvents are removed in vacuo. The crude material is purified by chromatography. Any residual acetate is removed by brief treatment with methanolic sodium methoxide.

The benzyl-protected aniline is dissolved in an organic solvent such as DMF. Palladium on carbon is added and the reaction mixture is placed under an atmosphere of hydrogen. At the end of the reaction, the mixture is filtered through Celite. The solvents are removed in vacuo. Further purification is achieved by chromatography.

The resulting primary aniline is dissolved in an organic solvent such as THF, acetonitrile, or DMF and is treated with formaldehyde and sodium triacetoxyborohydride as described in *J. Org. Chem*, 1996, 61, 3849-3862. The reaction is quenched with aqueous sodium bicarbonate and the product is extracted with an organic solvent such as ethyl acetate. The crude material is treated with di-t-butyl dicarbonate in an organic solvent such as dimethylformamide and aqueous sodium hydroxide. The resulting carbamate is purified by chromatography.

The primary alcohol product is dissolved in an organic solvent such as DCM or THF. 1,1,1-tris(acyloxy)-1,1-dihydro-1,2benziodoxol-3-(1H)-one (Dess-Martin reagent) is added and the solution is stirred at room temperature, according to a procedure from *J. Org. Chem.*, 1984, 48, 4155-4156. At the end of the reaction diethyl ether is added, followed by aqueous sodium hydroxide solution. The layers are separated and the organic layer is washed with aqueous sodium hydroxide solution, water, and dried over sodium sulfate. Filtration and evaporation of solvents yields the crude product. Further purification is achieved by chromatography.

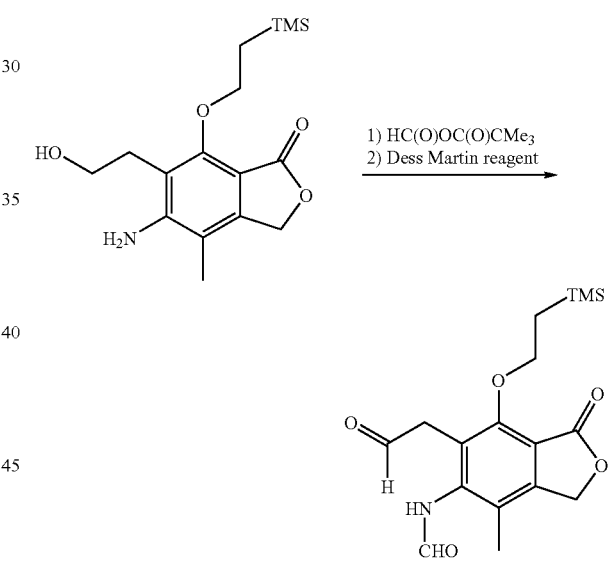

The starting material is dissolved in an organic solvent such as DCM or THF and is treated with the mixed anhydride of formic and pivalic acids, according to a procedure from *Rec. Trav. Chem. Pay-Bas*, 1982, 101, 460. At the end of the reaction, the solvent and all volatiles are removed in vacuo and the crude product is further purified by chromatography.

The product is dissolved in an organic solvent such as DCM or THF. 1,1,1-Tris(acyloxy)-1,1-dihydro-1,2-benziodoxol-3-(1H)-one (Dess-Martin reagent) is added and the solution was stirred at room temperature, according to a procedure from *J. Org. Chem.*, 1984, 48, 4155-4156. At the end of the reaction diethyl ether is added, followed by aqueous sodium hydroxide solution. The layers are separated and the organic layer is washed with aqueous sodium hydroxide solution, water, and dried over sodium sulfate. Filtration and evaporation of solvents yields the crude product. Further purification is achieved by chromatography.

R² Variants

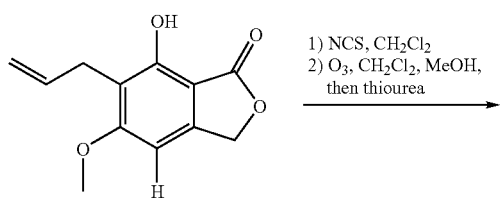

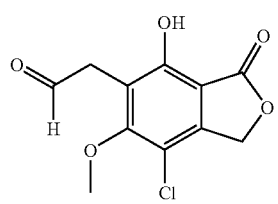

The starting material is dissolved in an organic solvent such as DMF and reacted with N-chlorosuccinimide, according to a procedure from *J. Med. Chem.*, 1996, 39, 4181-4196. After the starting material is consumed the reaction mixture is poured into water and the product is extracted with diethyl ether. The combined organic layers are dried over sodium sulfate. Filtration and evaporation of the solvent yields a crude reaction product.

The product of step one is dissolved in a mixture of organic solvents such as methanol, DCM, and pyridine. The solution is cooled to −78° C. and ozone is bubbled into the solution until a blue color persists. The excess ozone is removed with a nitrogen stream. The reaction mixture is warmed to room temperature and thiourea is added. Stirring at room temperature is continued. The reaction mixture is filtered and partitioned between DCM and water. The aqueous layer is extracted with DCM and the combined organic layers are washed with HCl (1 N), saturated aqueous sodium bicarbonate solution and brine. The solution is dried over sodium sulfate. Filtration and evaporation of the solvents yields the crude aldehyde. Further purification is achieved by chromatography.

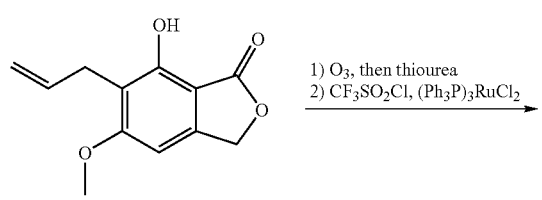

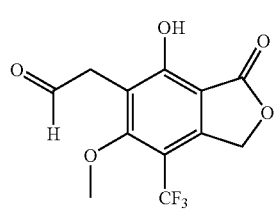

The starting material is dissolved in a mixture of organic solvents such as methanol, DCM, and pyridine. The solution is cooled to −78° C. and ozone is bubbled into the solution until a blue color persists. The excess ozone is removed with a nitrogen stream. The reaction mixture is warmed to room temperature and thiourea is added. Stirring at room temperature is continued. The reaction mixture is filtered and partitioned between DCM and water. The aqueous layer is extracted with DCM and the combined organic layers are washed with HCl (1 N), saturated aqueous sodium bicarbonate solution, and brine. The solution is dried over sodium sulfate. Filtration and evaporation of the solvents yields the crude aldehyde. Further purification is achieved by chromatography.

The product of step one is dissolved in an organic solvent such as benzene. Trifluoromethanesulfonyl chloride and dichlorotris(triphenylphosphine)rhuthenium are added and the solution is degassed. The reaction mixture is heated at 120° C., according to a procedure from *J. Chem. Soc., Perkin Trans.* 1, 1994, 1339-1346. At the end of the reaction the mixture is cooled to room temperature and the solvent is removed in vacuo. Further product purification is achieved by chromatography.

Synthesis of Olefins and Linkers to Phosphonates

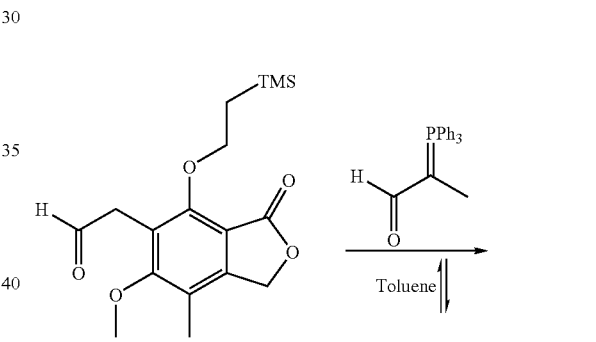

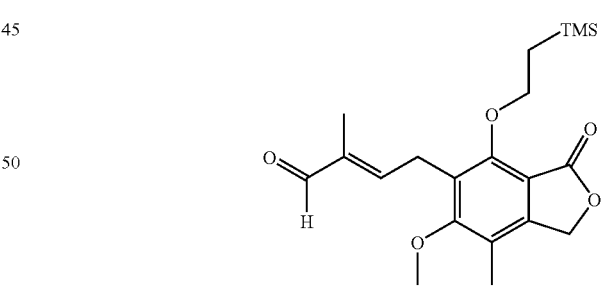

The phenacetaldehyde (5.3 g, 15.8 mmol) in toluene (50 mL) was heated at 100° C. with 2-(triphenyl-phosphanylidene)-propionaldehyde (6.8 g, 20.5 mmol) overnight. After concentration, the residue was purified by silica gel chromatography to provide 4.24 g (72%) of the unsaturated aldehyde as a pale yellow solid. $^1$H NMR (300 MHz, CDCl$_3$) δ 0.00 (s, 9H), 1.10-1.21 (m, 2H), 1.87 (s, 3H), 2.16 (s, 3H), 3.67-3.76 (m, 2H), 3.74 (s, 3H), 4.27-4.39 (m, 2H), 5.11 (s, 2H), 6.40-6.48 (m, 1H), 9.2 (s, 1H).

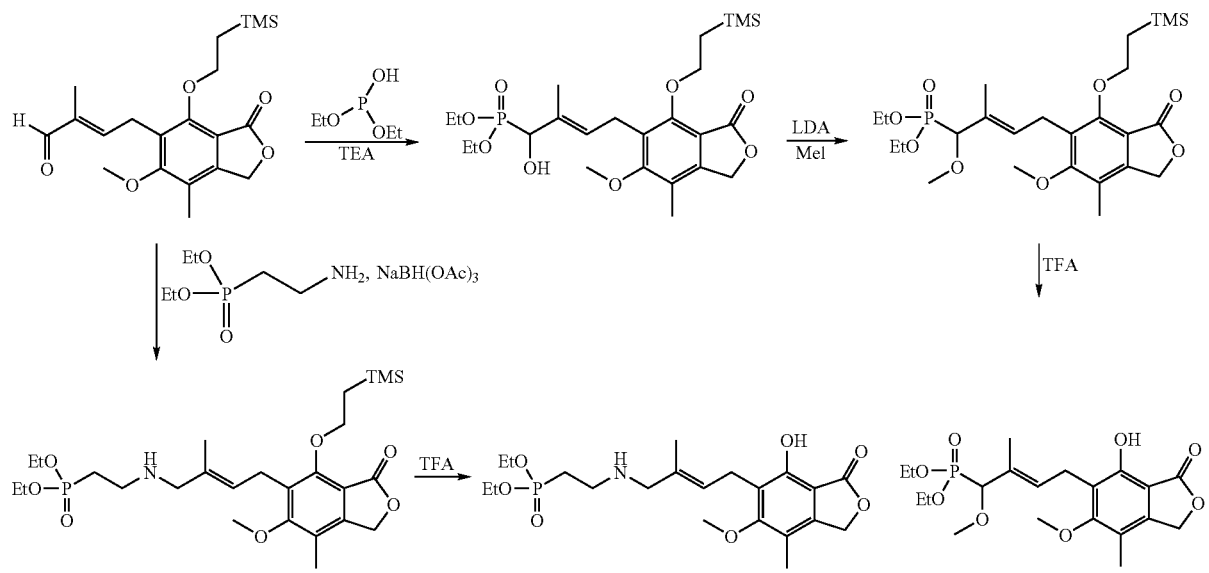

The trimethylsilyethyl protected aldehyde is treated with diethylphosphite in a solvent such as acetonitrile in the presence of a base such as triethylamine to afford the hydroxy phosphonate, according to a procedure such as that reported in *Tetrahedron*, 1995, 51, 2099. The hydroxy phosphonate is O-akylated and then the protecting group is removed by treatment with either trifluoroacetic acid or tetrabutylammonium fluoride to generate the desired methoxy phosphonate analog.

Alternatively, the aldehyde is mixed with diethyl (2-aminoethyl)phosphonate and treated with a reducing agent such as sodium triacetoxyborohydride to generate the amino phosphonate analog.

a 2M solution in THF). The ice bath was removed and the reaction mixture was allowed to warm to room temperature. The reaction mixture was stirred for an additional 40 minutes whereupon TLC indicated complete consumption of starting aldehyde. The reaction was worked up by addition of aqueous 1N HCl (0.5 mL) and the product was extracted with $CH_2Cl_2$. The organic layer was washed with saturated aqueous sodium bicarbonate solution and brine. The organic layer was concentrated under reduced pressure and the residue was purified by silica gel chromatography to provide 100 mg (97%) of the product as a clear liquid. $^1$H NMR (300 MHz, $CDCl_3$) δ 0.00 (s, 9H), 1.20 (dd, 2H, J=7, 8 Hz), 1.81 (s, 3H), 2.13 (s, 3H), 3.38-3.50 (m, 2H), 3.74 (s, 3H), 3.95 (s, 2H), 4.27 (dd, 2H, J=7, 8 Hz), 5.08 (s, 2H), 5.17-5.44 (m, 1H).

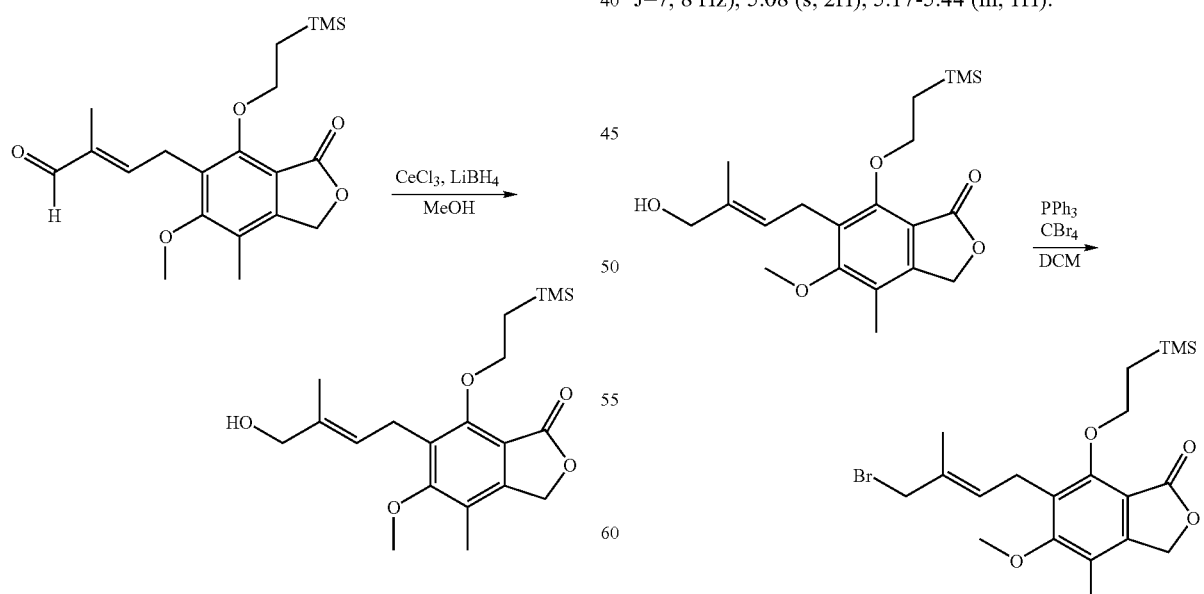

A solution of 4-[6-methoxy-7-methyl-3-oxo-4-(2-trimethylsilanyl-ethoxy)-1,3-dihydro-isobenzofuran-5-yl]-2-methyl-but-2-enal (103 mg, 0.27 mmol) in methanol (5 mL) was cooled to 0° C. A solution of $CeCl_3$ (0.68 mL, MeOH: $H_2O$, 9:1) was added, followed by $LiBH_4$ (0.14 mL, 0.28 mmol of Polymer-supported triphenylphosphine is soaked in DCM for 1 hour. The allylic alcohol and carbon tetrabromide are sequentially added. When the reaction is complete, the mixture is filtered and the filtrate concentrated. The bromide is purified as necessary by chromatography.

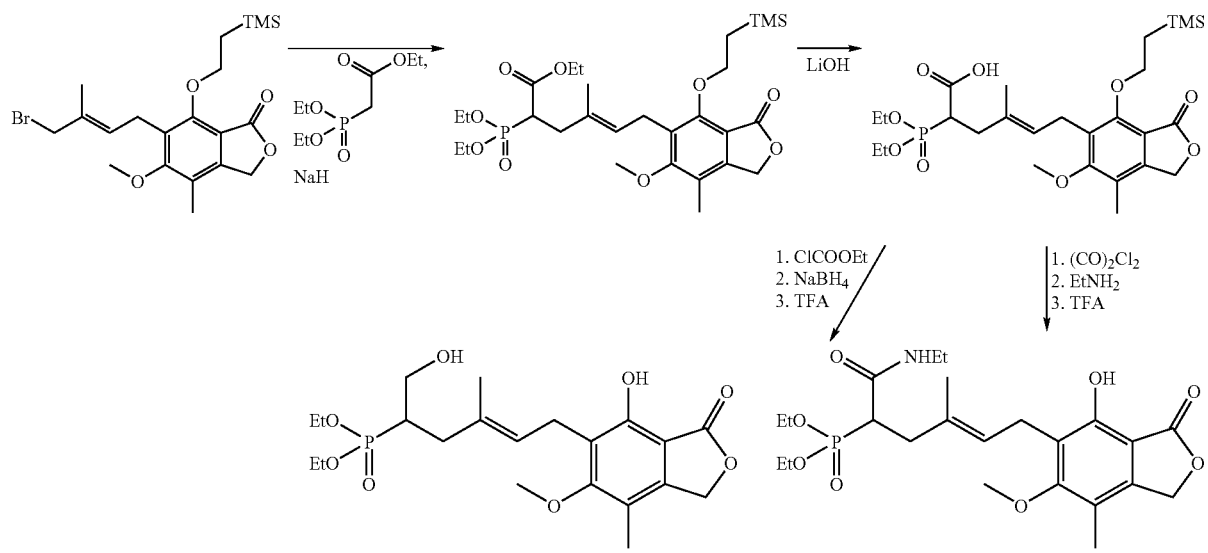

The allylic bromide is treated in an inert organic solvent such as dimethylformamide with an alkali metal salt of ethyl diethoxyphosphorylacetate (prepared by reacting ethyl diethoxyphosphorylacetate with sodium hexamethyldisilazide or sodium hydride) to afford the ethoxycarbonyl phosphonate, according to a procedure such as that described in WO 9522538. The carboxylic ester group is converted to both the carboxylic amide and the hydroxymethyl groups according to the methods conventionally utilized for amide formations and ester reductions. For example, the carboxylic ester is saponified with aqueous lithium hydroxide. The acid is activated with ethyl chloroformate and reduced with sodium borohydride to generate, after removal of the protecting group, the hydroxymethyl phosphonate analog. The acid is also converted to its acyl chloride and then reacted with ethylamine to afford the amide analog.

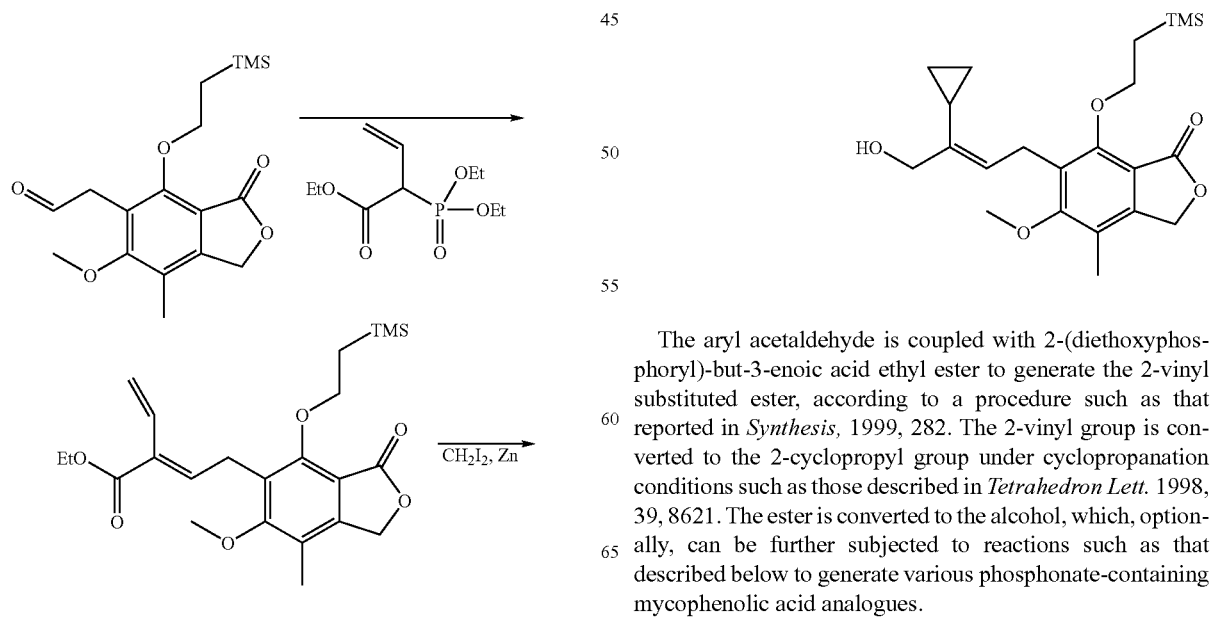

The aryl acetaldehyde is coupled with 2-(diethoxyphosphoryl)-but-3-enoic acid ethyl ester to generate the 2-vinyl substituted ester, according to a procedure such as that reported in *Synthesis,* 1999, 282. The 2-vinyl group is converted to the 2-cyclopropyl group under cyclopropanation conditions such as those described in *Tetrahedron Lett.* 1998, 39, 8621. The ester is converted to the alcohol, which, optionally, can be further subjected to reactions such as that described below to generate various phosphonate-containing mycophenolic acid analogues.

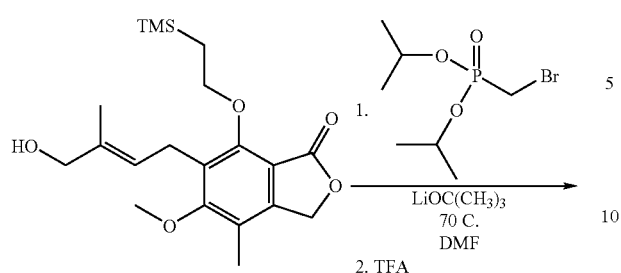

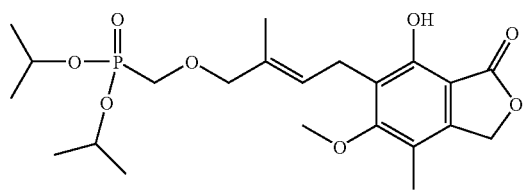

The allylic alcohol is treated with bromomethylphosphonic acid diisopropyl ester in the presence of a base such as lithium t-butoxide in a solvent such as dimethylformamide. The phenol protecting group is then removed by treatment with trifluoroacetic acid.

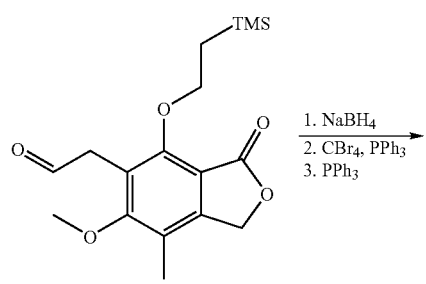

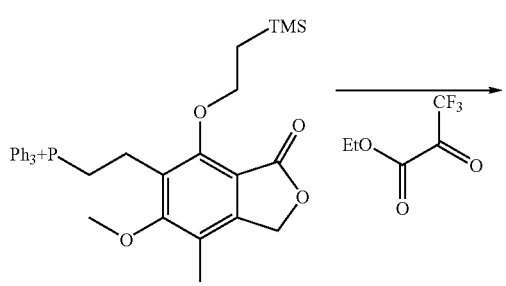

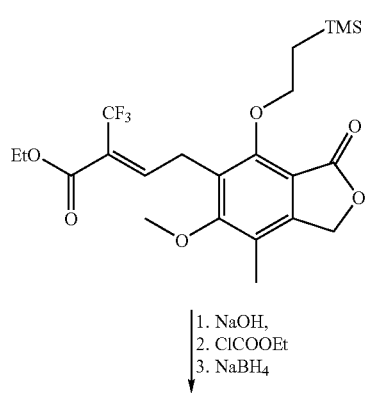

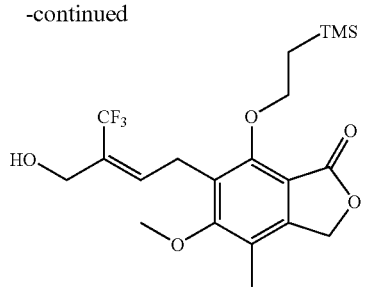

The phenacetaldehyde can alternatively be converted to the allyl phosphonium salt, according to a procedure such as that reported in *J. Org. Chem.* 1987, 52, 849. The phosphonium salt is then treated with the commercially available 3,3,3-trifluoro-2-oxo-propionic acid ethyl ester and a base such as sodium hydride to generate the 2-trifluoromethyl substituted ester. The ester is converted to the alcohol, which, optionally, can be further subjected to reactions described earlier to generate mycophenolic acid analogues with various side chains containing the phosphonate group.

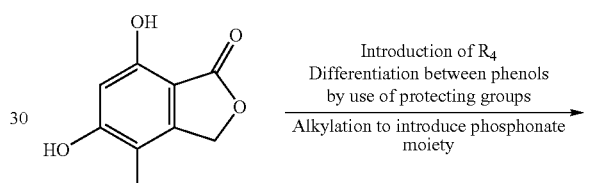

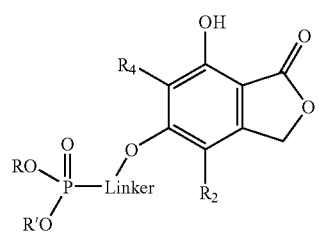

Introduction of R⁴ Variants

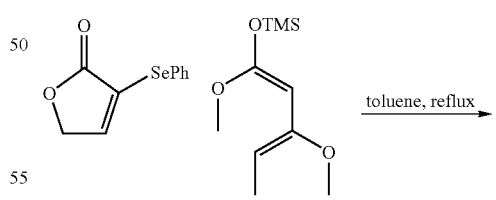

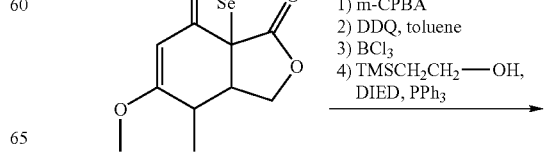

-continued

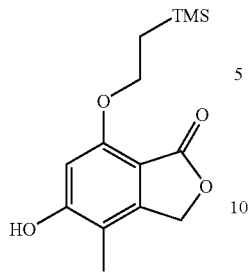

The enone (synthesis reviewed in *Tetrahedron*, 1985, 41, 4881-4889) and the diene (*Chem. Pharm. Bull.*, 1989, 37, 2948-2951) are dissolved in an organic solvent such as toluene, stirred at room temperature for 24 hours and heated to reflux for additional 5 hours, according to a procedure from *J. Med. Chem.*, 1996, 39, 4181-4196. The reaction mixture is cooled to room temperature and the solvent removed in vacuo. The crude reaction product is further purified by chromatography.

The product of step one is dissolved in an organic solvent such as DCM and m-chloroperbenzoic acid is added, according to a procedure from *J. Med. Chem.*, 1996, 39, 4181-4196. At the end of the reaction, the solution is poured into aqueous sodium hydrogen sulfite solution. The organic layer is washed with saturated aqueous sodium bicarbonate solution and is dried over sodium sulfate. Filtration and evaporation of solvents yields the crude product.

The crude product is dissolved in an organic solvent such as toluene and treated with dichlorodicyanoquinone (DDQ), according to a procedure from *J. Med. Chem.*, 1996, 39, 4181-4196. At the end of the reaction the solvent is removed in vacuo and the crude material is further purified by chromatography.

The product is dissolved in an organic solvent such as DCM and treated with boron trichloride at reflux temperature, according to a modified procedure from *J. Med. Chem.*, 1996, 39, 46-55. At the end of the reaction the solution is washed with aqueous HCl solution. The solution is dried over sodium sulfate. Removal of the solvent yields the crude reaction product. Further purification is achieved by chromatography.

The product of the previous step and triphenylphosphine are dissolved in an organic solvent such as tetrahydrofuran (THF). Diisopropylazodicarboxylate (DIAD) is added dropwise at 0° C. Stirring is continued. A solution of 2-trimethylsilyl ethanol in THF is added and stirring is continued. At the end of the reaction, the solvent is removed in vacuo. The crude reaction solid is extracted with a mixture of organic solvents such as hexanes and diethylether. The washings are combined and the solvents removed in vacuo. The desired product is further purified and separated from the undesired regioisomer by chromatography.

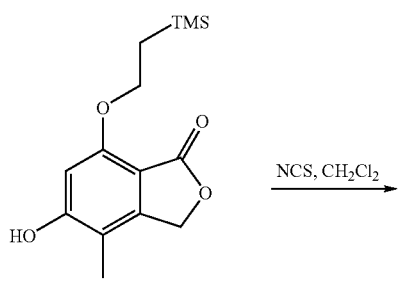

-continued

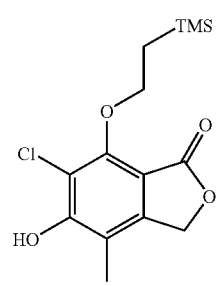

The starting material is dissolved in an organic solvent such as dimethylformamide (DMF) and reacted with N-chlorosuccinimide, according to a procedure from *J. Med. Chem.*, 1996, 39, 4181-4196. After the starting material is consumed the reaction mixture is poured into water and the product is extracted with diethyl ether. The combined organic layers are dried over sodium sulfate. Filtration and evaporation of the solvents yields the crude product. Further purification is achieved by chromatography.

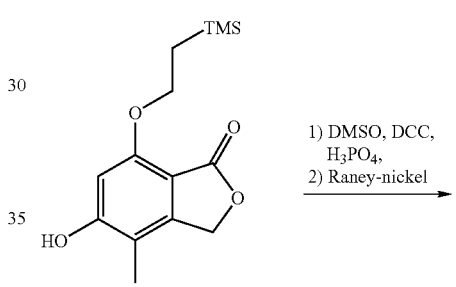

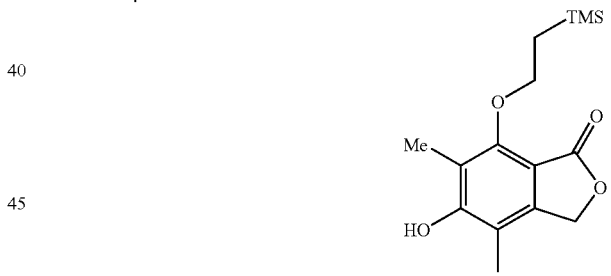

The starting material is dissolved in an organic solvent such as benzene and reacted with dimethyl sulfoxide (DMSO), dicyclohexylcarbodiimide (DCC), and orthophosphoric acid according to a procedure from *J. Am. Chem. Soc.*, 1966, 88, 5855-5866. At the end of the reaction, the suspension is filtered and the organic layer washed with aqueous sodium bicarbonate solution and dried over sodium sulfate. Filtration and evaporation of solvents yields the crude material. Further purification is achieved by chromatography.

The product of step one is dissolved in an organic solvent such as DCM or THF and treated with Raney nickel, according to procedures reviewed in *Chem. Rev.*, 1962, 62, 347-404. When all starting material is consumed, the reaction is filtered and the solvent removed in vacuo. Further purification is achieved by chromatography.

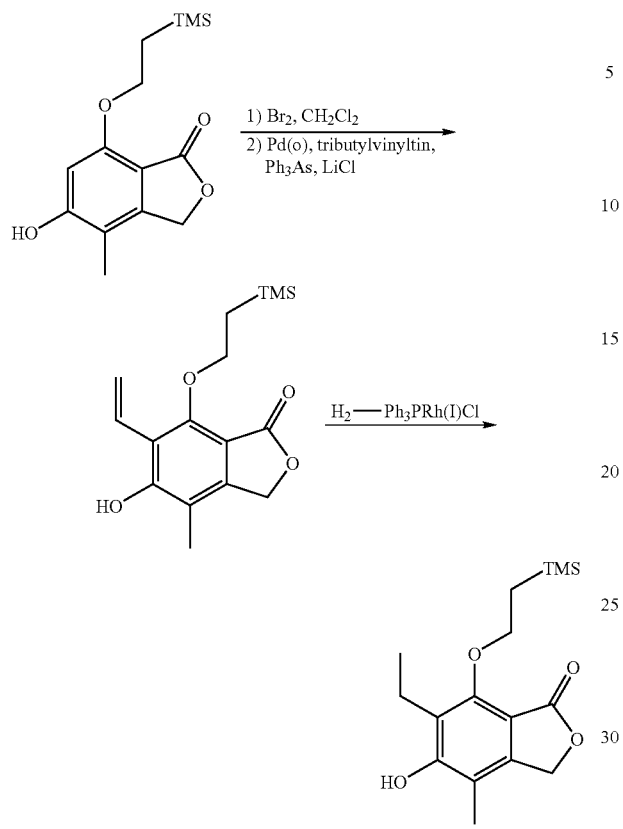

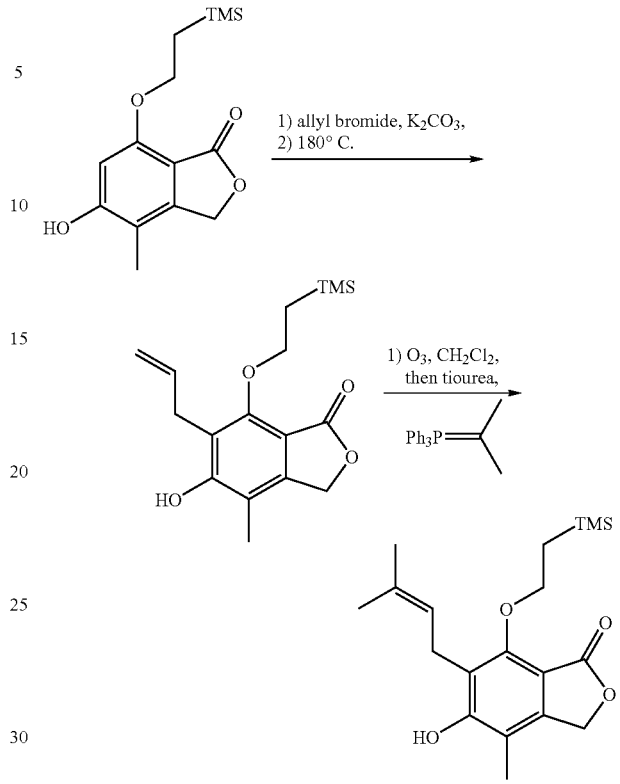

The starting material is dissolved in an organic solvent such as DCM and bromine is added, according to a procedure from *J. Med. Chem.*, 1996, 39, 4181-4196. At the end of the reaction, additional DCM is added and the solution washed with aqueous sodium thiosulfate solution and brine. The organic layer is dried over sodium sulfate. Filtration and evaporation of solvents yields the crude material. Further purification is achieved by chromatography on silica gel.

The starting material, lithium chloride, triphenylarsine, tributylvinyltin, and tris(dibenzylideneacetone)dipalladium (0)-chloroform adduct are heated in an organic solvent such as N-methylpyrrolidinone at an elevated temperature of approximately 55° C., according to a procedure from *J. Med. Chem.*, 1996, 39, 4181-4196. At the end of the reaction, the mixture is cooled to room temperature and poured into a mixture of ice, potassium fluoride, water, and ethyl acetate. Stirring is continued for 1 hour. The suspension is filtered through Celite and extracted with ethyl acetate. The combined organic extracts are dried over sodium sulfate. The solvents are removed in vacuo and the crude material is further purified by chromatography.

The product of step two is dissolved in a mixture of organic solvents such as benzene and ethyl acetate. Tris(triphenylphosphine)rhodium(I) chloride is added and the reaction is placed under an atmosphere of hydrogen, according to a procedure from *J. Med. Chem.*, 1996, 39, 4181-4196. The solvents are removed in vacuo and the crude reaction is filtered through silica gel. Further purification is achieved by chromatography.

The starting material is dissolved in an organic solvent such as DMF. Potassium carbonate and allyl bromide are added and stirring at room temperature is continued, according to a procedure from *J. Med. Chem.*, 1996, 39, 4181-4196. After all the starting material is consumed, aqueous HCl solution and diethyl ether are added and the organic layer is collected and the solvent is removed in vacuo.

The crude material is dissolved in N,N diethylaniline and the reaction mixture is heated at an elevated temperature of ca. 180° C. At the end of the reaction, the mixture is cooled to room temperature and poured into a mixture of aqueous HCl (2N) and ethyl actetate. The organic layer is washed with aqueous HCl (2N) and dried over sodium sulfate. Filtration and removal of the solvents yields the crude product. Further purification is achieved by chromatography.

The product of step 2 is dissolved in a mixture of organic solvents such as methanol, DCM, and pyridine. The solution is cooled to −78° C. and ozone is bubbled into the solution until a blue color persists. The excess ozone is removed with a nitrogen stream. The reaction mixture is warmed to room temperature and thiourea is added. Stirring at room temperature is continued. The reaction mixture is filtered and partitioned between DCM and water. The aqueous layer is extracted with DCM and the combined organic layers are washed with HCl (1 N), saturated aqueous sodium bicarbonate solution and brine. The solution is dried over sodium sulfate. Filtration and evaporation of the solvents yields the crude aldehyde. Further purification is achieved by chromatography.

The aldehyde is dissolved in an organic solvent such as THF and is reacted with triphenylphosphonium sec.propyl bromide and potassium tert.butoxide, according to procedures reviewed in *Chem. Rev.*, 1989, 89, 863-927. At the end of the reaction, the solvent is removed in vacuo and the crude material purified by chromatography.

Introduction of Linkers to Phosphonates

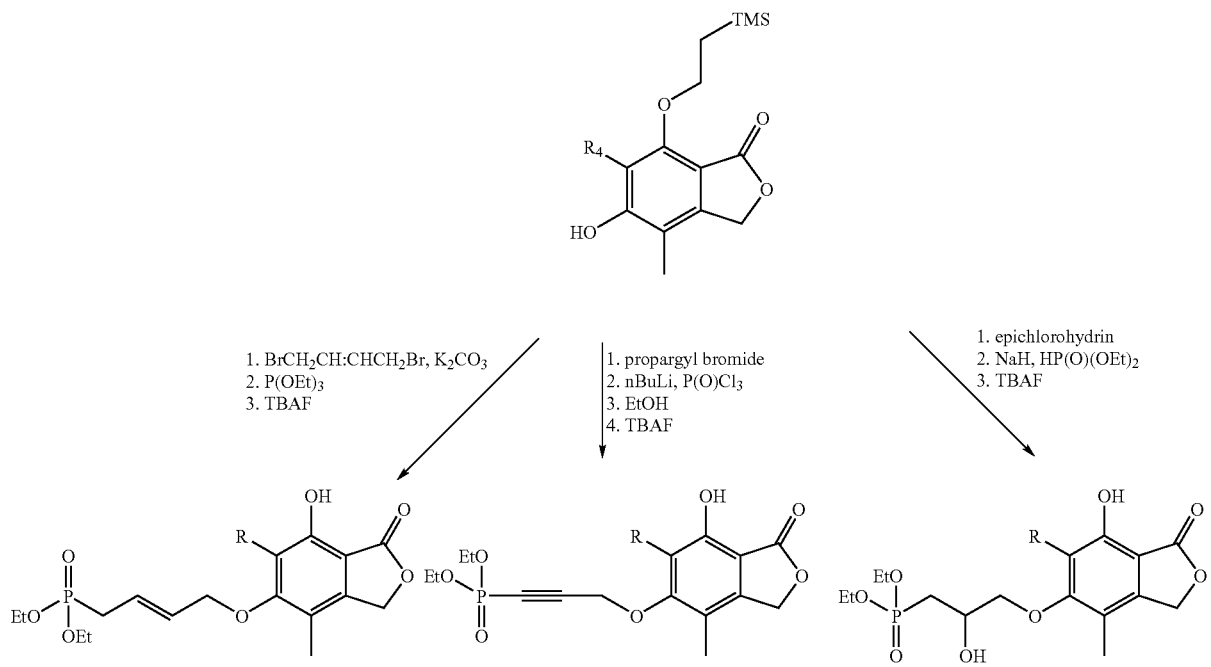

The phenols shown herein may optionally be alkylated with the reagent of choice. Optionally, the phosphonate moiety will be part of such a reagent. Alternatively, it will be introduced in a subsequent step by a variety of means, of which three are illustrated above. For example, an alkyl halide may be heated with triethylphosphite in a solvent such as toluene (or other Arbuzov reaction conditions: see Engel, R., "Synthesis of Carbon-phosphorus Bonds," CRC press, 1988). Alternatively, an epoxide may be reacted with the anion of a dialkyl phosphinate. In a further example, the phosphonate reagent may be the electrophile, e.g., an acetylide anion may be condensed with phosphorus oxychloride and the intermediate dichlorophosphonate quenched with ethanol to generate the diethyl ester of the desired phosphonic acid.

Example 316

Preparation of an Additional Representative Mycophenolate Compound of the Invention A specific compound of the invention can be prepared as follows.

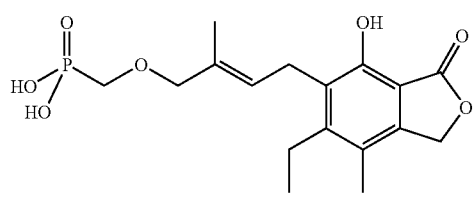

[4-(6-Ethyl-4-hydroxy-7-methyl-3-oxo-1,3-dihydro-isobenzofuran-5-yl)-2-methyl-but-2-enyloxymethyl]-phosphonic acid This product was prepared using methods similar to those described herein, e.g., in Examples 251 and 276. MS (negative mode): 369.3 [$M^+-1$].

Example 317

Preparation of an Additional Representative Mycophenolate Compound of the Invention A specific compound of the invention can be prepared as follows.

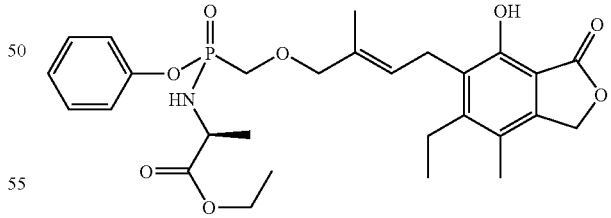

2-{[4-(6-Ethyl-4-hydroxy-7-methyl-3-oxo-1,3-dihydro-isobenzofuran-5-yl)-2-methyl-but-2-enyloxymethyl]-phenoxy-phosphinoylamino}-propionic acid ethyl ester Using methods similar to those described herein, e.g., in Example 261, the desired product was prepared, starting from Example 316. MS (positive mode): 546.3 [$M^++1$] & 568.3 [$M^++Na$].

Example 318

Preparation of an Additional Representative Mycophenolate Compound of the Invention A specific compound of the invention can be prepared as follows:

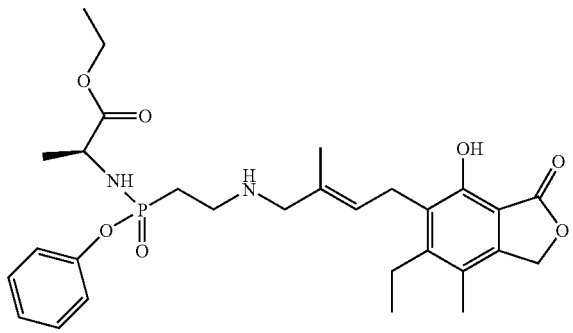

2-({2-[4-(6-Ethyl-4-hydroxy-7-methyl-3-oxo-1,3-dihydro-isobenzofuran-5-yl)-2-methyl-but-2-enylamino]-ethyl}-phenoxy-phosphinoylamino)-propionic acid ethyl ester This product was prepared using methods analogous to those described herein, e.g., in Examples 268 and 316, using 2-[(2-amino-ethyl)-phenoxy-phosphinoylamino]-propionic acid ethyl ester in the reductive amination step. MS (positive mode): 559.4 [M$^+$+1] & 581.3 [M$^+$+Na].

Example 319

Preparation of an Additional Representative Mycophenolate Compound of the Invention A specific compound of the invention can be prepared as follows:

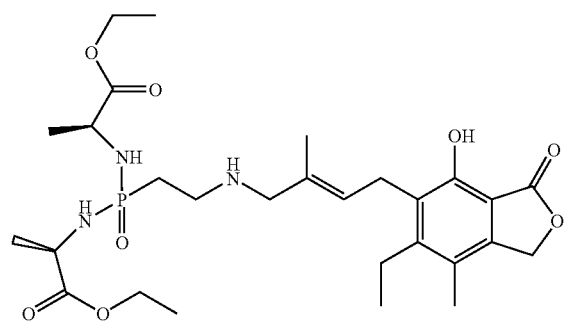

2-((1-Ethoxycarbonyl-ethylamino)-{2-[4-(6-ethyl-4-hydroxy-7-methyl-3-oxo-1,3-dihydro-isobenzofuran-5-yl)-2-methyl-but-2-enylamino]-ethyl}-phosphinoylamino)-propionic acid ethyl ester This product was prepared by methods analogous to those described herein, e.g., in Example 318, using 2-[(2-aminoethyl)-(1-ethoxycarbonyl-ethylamino)-phosphinoylamino]-propionic acid ethyl ester in the reductive amination step. MS (positive mode): 582.4 [M$^+$+1] & 604.3 [M$^+$+Na].

Example 330

Synthesis of Exemplary Compounds of the Invention

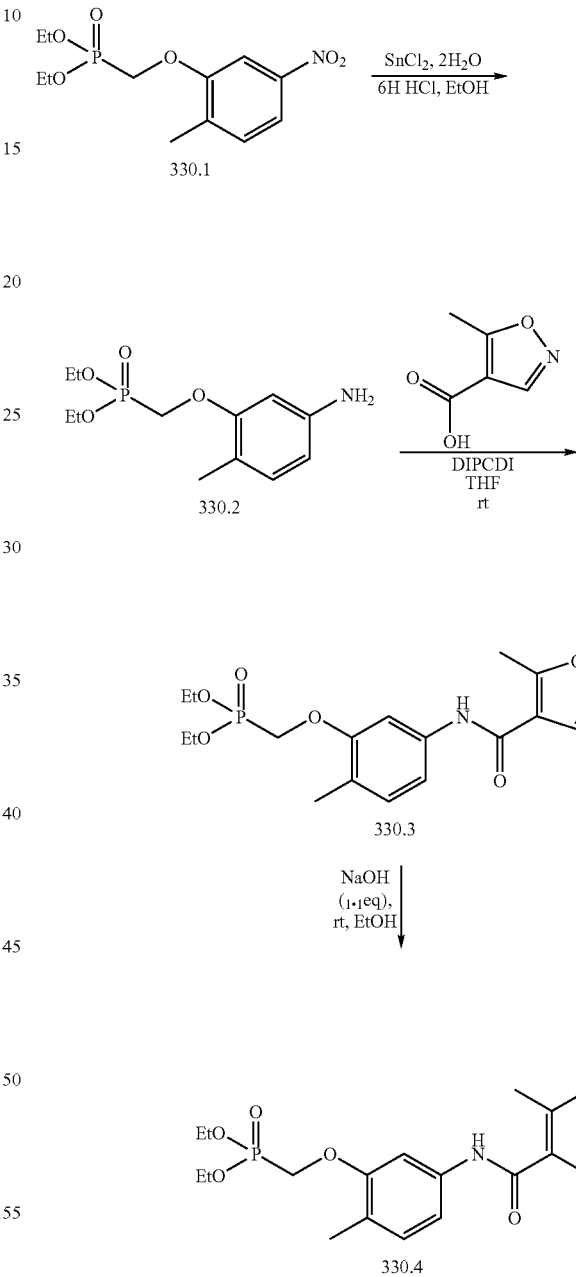

A representative compound of the invention 330.4 can be prepared as illustrated above and as described below.

Compound 330.3 (250 mg, 0.65 mmol) was dissolved in 10 mL of absolute ethanol (15 mL) under an argon atmosphere. Following the addition of NaOH (29 mg, 0.72 mmol), the reaction mixture was stirred overnight at room temperature. TLC (CHCl$_3$/MeOH, 9:1) showed completion of reaction. The reaction mixture was concentrated to a solid and dissolved in ethyl acetate (20 mL). The solution was washed with deionized water (2×10 mL) and dried over $Na_2SO_4$. Concentration gave a solid that was purified by silica gel column chromatography ($CHCl_3$/MeOH, 4:1), affording pure compound 330.4 as a solid (188 mg, 75%). ESI-MS m/z 383 [M+H]$^+$. $^1$H NMR (300 MHz, DMSO-$d_6$): δ 7.32 (1H, s, ArH), 6.96 (2H, s, ArH), 4.31 (2H, d, J=9.9 Hz, OCH$_2$), 4.18-4.08 (4H, m, 2×OCH$_2$), 2.08 (3H, s, CH$_3$), 2.00 (3H, s, CH$_3$), 1.26 (6H, t, J=7.0 Hz, CH$_3$). $^{31}$P NMR (121.7 MHz, DMSO-$d_6$/external $H_3PO_4$) δ ppm 20.0-20.4 (m); HPLC: 93% pure (Sphereclone 5 μL, $H_2O$: MeCN, 20 min linear from 10-90% MeCN, 1.0 mL/min).

The intermediate compound 330.3 was prepared as follows.

a. Synthesis of Compound 330.1. 2-Methyl-5-nitrophenol (2.00 g, 13.05 mmol) was dissolved in dry DMF (10 mL) under argon atmosphere and cooled to 0° C. Diethylphosponomethyl-O-triflate (4.70 gm, 15.66 mmol) and cesium carbonate (6.38 gm, 19.58 mmol) were added sequentially. The reaction mixture was stirred at 0° C. for 4 hrs. TLC (cyclohexane/EtOAc, 1:1) showed completion of reaction. Deionized water (15 mL) was added and the mixture was extracted with EtOAC (2×50 mL). The organic layer was washed with 1N HCl (20 mL) followed by water (2×20 mL), dried over $Na_2SO_4$ and concentrated to a semi-solid. Purification by silica gel column chromatography (cyclohexane/EtOAc, 1: 1) afforded pure compound 330.1 as an oil (3.86 g, 97%). ESI-MS m/z 304 [M+H]$^+$.

b. Synthesis of Compound 330.2. Compound 330.1 (2.8 g, 9.24 mmol) was dissolved in 15 mL of absolute ethanol (15 mL) and 6N HCl (2 mL) under an argon atmosphere. Following the addition of $SnCl_2.2H_2O$ (5.26 g, 27.72 mmols), the reaction mixture was stirred overnight at room temperature. TLC ($CHCl_3$/MeOH, 9:1) showed completion of reaction. The mixture was concentrated to a semi-solid and dissolved in ethyl acetate (30 mL). The ethyl acetate layer was washed with deionized water (10 mL) and satd. $NaHCO_3$ (10 mL) and dried over $Na_2SO_4$. Concentration gave a solid that was used without purification. ESI-MS m/z 274 [M+H]$^+$.

c. Synthesis of Compound 330.3. Crude compound K-105-48 (900 mg, 3.38 mmol) was dissolved in 15 mL of dry THF (15 mL) under an argon atmosphere. Following the addition of 5-methylisoxazole-4-carboxylic acid (381 mg, 3.00 mmol) and diisopropyl carbodiimide (511 μL, 3.30 mmol), the reaction mixture was stirred 6 h at room temperature. TLC ($CHCl_3$/MeOH, 9:1) showed completion of reaction. The reaction mixture was filtered and the filtrate concentrated to give a solid, which was dissolved in ethyl acetate (25 mL). The solution was washed with deionized water (2×10 mL) and dried over $Na_2SO_4$. Concentration gave a solid that was purified by silica gel column chromatography ($CHCl_3$/MeOH, 95:5) to afford pure compound 330.3 as light yellow solid (680 mg, 55%). ESI-MS m/z 383 [M+H]$^+$. $^1$H NMR (300 MHz, CDCl$_3$): δ 7.11 (1H, s, ArH), 7.06 (2H, s, ArH), 4.29-4.20 (4H, m, OCH$_2$), 4.14 (2H, d, J=10.4 Hz, OCH$_2$), 2.76 (3H, s, CH$_3$), 2.14 (3H, s, CH$_3$), 1.37 (6H, t, J=7.0 Hz, CH$_3$). $^{31}$P NMR (121.7 MHz, DMSO-$d_6$/external $H_3PO_4$) 6; ppm 19.7-20.0 (m); HPLC: 98% pure (Sphereclone 5 μL, $H_2O$: MeCN, 20 min linear from 10-90% MeCN, 1.0 mL/min).

Example 331

Synthesis of Representative Prednisone Compounds of the Invention

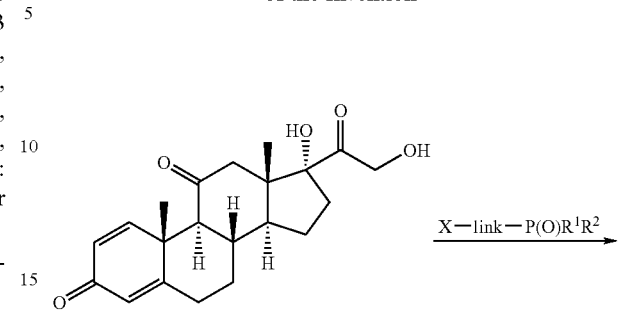

331.1

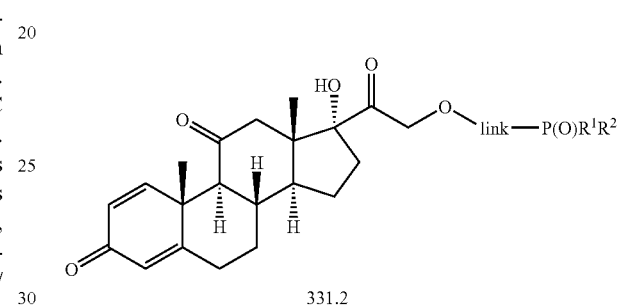

331.2

Representative compounds of the invention can be prepared as illustrated above. Derivatization at the C-21 hydroxy group is accomplished through alkylation of prednisone 331.1 with the appropriate phosphonate to provide compounds of the invention 331.2. A specific compound of the invention can be prepared as follows.

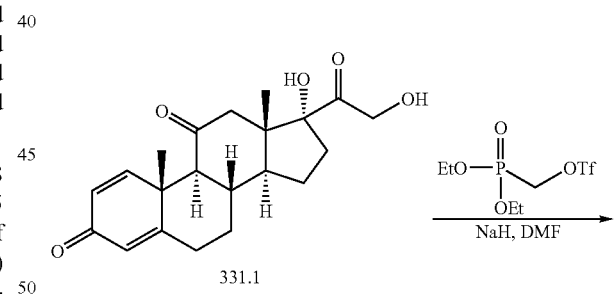

331.1

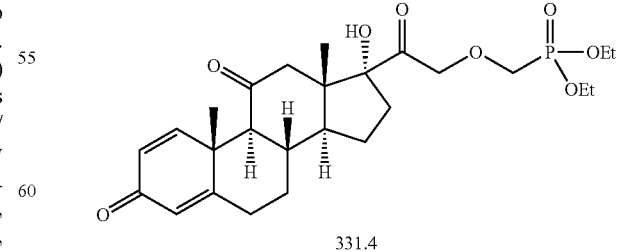

331.4

After sodium hydride extraction of the primary hydroxy proton in 331.1, diethyl phosphonate triflate is added to afford ether 331.4.

Example 332

Synthesis of Representative Prednisone Compounds of the Invention

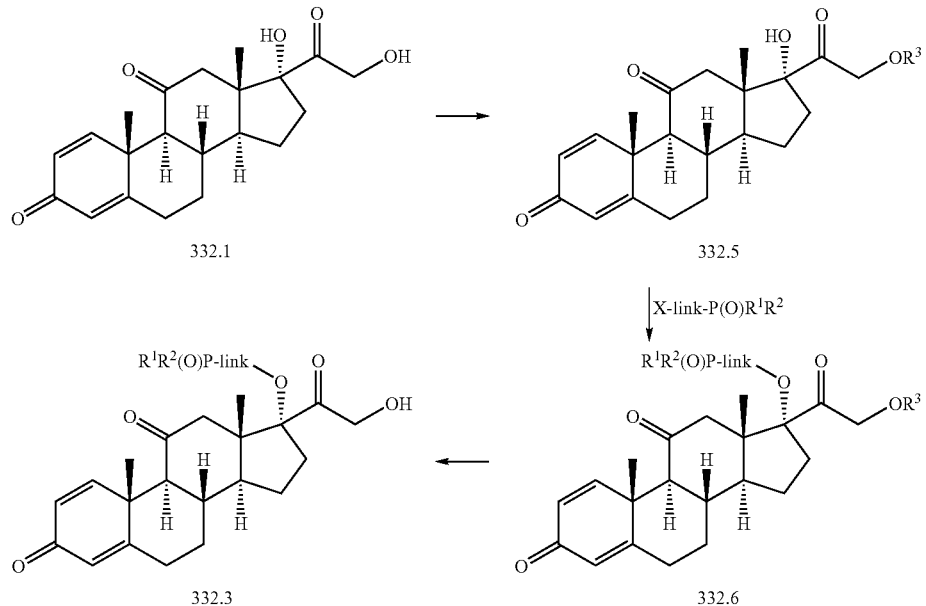

Representative compounds of the invention 332.3 can be prepared as illustrated above. Protection of prednisone 332.1 at the less hindered primary site furnishes alcohol 332.5, which is alkylated at the exposed hydroxy group with the appropriate phosphonate to provide 332.6. Removal of the protecting group completes the construction of analog 332.3. A specific compound can be prepared as follows.

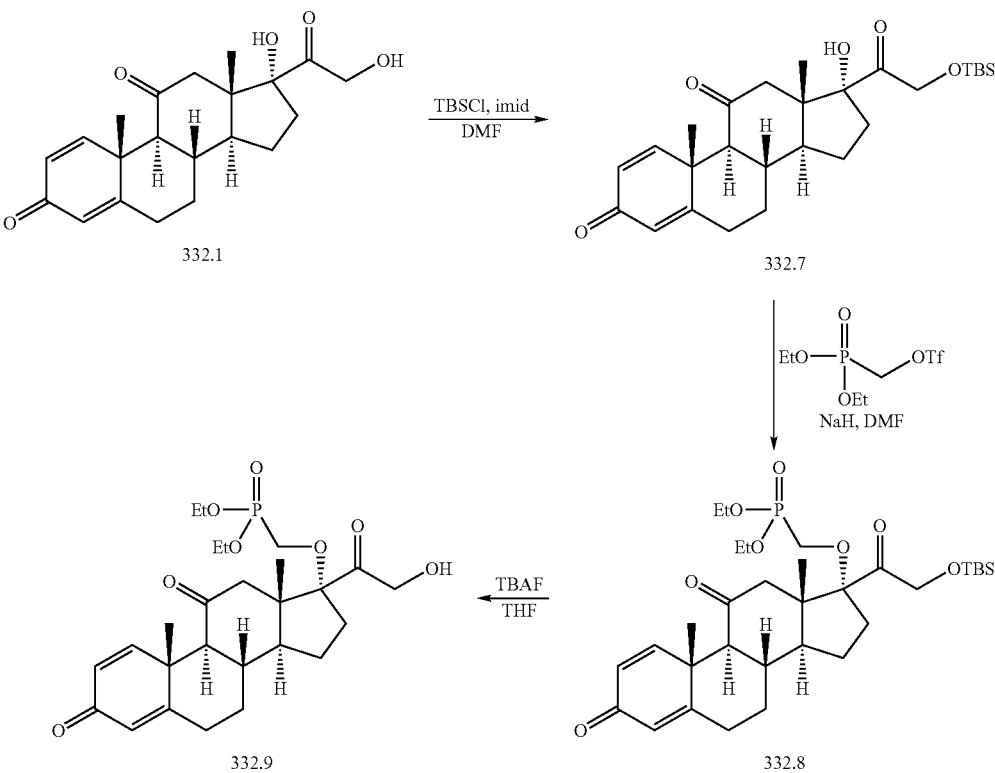

Prednisone 332.1 is mono-protected as its TBS ether 332.7. After alkylating with the diethyl phosphonate triflate, the resulting intermediate 332.8 is treated with TBAF to give the desired phosphonate 332.9.

Example 500

Synthesis of Exemplary Compounds of the Invention

Preparation of (2-{4-[(2,4-Diamino-pteridin-6-ylm-ethyl)-methyl-amino]-benzoylamino}-methyl)-phosphonic acid diethyl ester To a solution of 4-[(2,4-diamino-pteridin-6-ylmethyl)-methyl-amino]-benzoic acid hemihydrochloride dihydrate (67.0 mg, 177 μmol) in DMF (3.0 mL) was added diethyl cyanophosphonate (34.8 μL, 230 μmol) and diisopropylethylamine (Hunig's Base, DIEA, 30.4 μL, 177 μmol). The solution was stirred at ambient temperature for 4 hours when diethyl(aminomethyl)phosphonate oxalate (45.4 mg, 177 μmol) was added. The solution was stirred for 4 additional hours, when complete consumption of the starting materials was observed. The reaction was worked up by removal of the solvent in vacuo and purifying the residue by silica gel chromatography using MeOH—$CH_2Cl_2$ (10-30%). The product collected from this chromatography step was sufficiently pure to be carried on to the next reaction. A small amount of the product (20 mg) was repurified by RP HPLC on $C_{18}$ column using $H_2O$/acetonitrile (2-95%) to provide 12.9 mg (76%) of the pure product. $^1H$ NMR (300 MHz, DMSO-$d_6$) δ 1.19 (t, 6H, J=7.2 Hz), 3.21 (s, 3H), 3.70 (m, 2H), 4.00 (q, 4H, J=7.2 Hz), 4.81 (s, 2H), 6.81 (d, 2H, J=9 Hz), 7.71 (d, 2H, J=9 Hz), 8.40 (br s, 1H), 8.61 (s, 1H). $^{31}P$ (121.4 MHz, DMSO-$d_6$) δ 23.4. MS (m/z) 475.2 [M+H]$^+$, 597.2 [M+Na]$^+$.

Example 501

Synthesis of Exemplary Compounds of the Invention

Preparation of (2-{4-[(2,4-Diamino-pteridin-6-ylm-ethyl)-methyl-amino]-benzoylamino}-methyl)-phosphonic acid To a solution of crude (2-{4-[(2,4-Diamino-pteridin-6-yl-methyl)-methyl-amino]-benzoylamino}-ethyl)-phosphonic acid diethyl ester post silica column chromatography (60 mg, 126 μmol) in dry DMF (0.90 mL) was added trimethylsilyl bromide (bromotrimethylsilane, TMSBr, 130.6 μL, 1,010 μmol) at ambient temperature. The solution was then heated at 70° C. for 4.0 hours, after which the reaction mixture was allowed to cool to room temperature. The solvent volume was reduced to ~700 μL in vacuo and diluted with $H_2O$ (100 μL). This solution was purified by RP HPLC on $C_{18}$ column using $H_2O$/acetonitrile (2-95%) to provide 26.8 mg (51%) of the desired compound as a yellow solid. $^1H$ NMR (300 MHz, DMSO-$d_6$) δ 3.18 (s, 3H), 3.50 (m, 2H), 4.77 (s, 2H), 6.79 (d, 2H, J=9 Hz), 7.79 (d, 2H, J=9 Hz), 8.07 (br s, 1H), 8.56 (s, 1H); MS (m/z) 419.2 [M+H]$^+$.

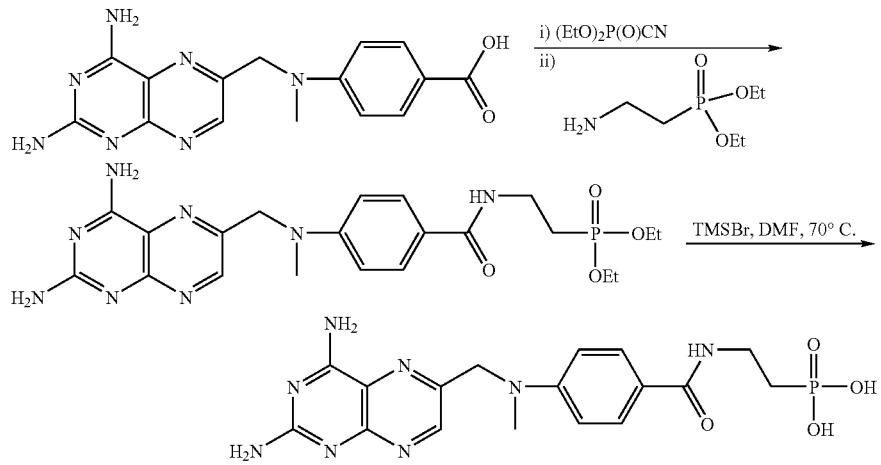

Example 502

Synthesis of Exemplary Compounds of the Invention

Preparation of (2-{4-[(2,4-Diamino-pteridin-6-ylm-ethyl)-methyl-amino]-benzoylamino}-ethyl)-phosphonic acid diethyl ester To a solution of 4-[(2,4-diamino-pteridin-6-ylmethyl)-methyl-amino]-benzoic acid hemihydrochloride dihydrate (61.2 mg, 161 μmol) in DMF (2.8 mL) were added diethyl cyanophosphonate (31.8 μL, 210 μmol) and DIEA (27.8 μL, 161 μmol). The solution was stirred at ambient temperature for 4 hours, when diethyl(aminoethyl)phosphonate oxalate (43.8 mg, 161 μmol) was added. The solution was stirred for 3 additional hours, by which time complete consumption of the starting materials was observed. The reaction was worked up by removal of the solvent in vacuo and purifying the residue by silica gel chromatography using MeOH—$CH_2Cl_2$ (10-30%). The product collected from this chromatography step was sufficiently pure to be carried on to the next reaction. A small amount of the product (32 mg) was re-purified by RP HPLC on $C_{18}$ column using $H_2O$/acetonitrile (2-95%) to provide 19 mg (70%) of the pure product. $^1H$ NMR (300 MHz, DMSO-$d_6$) δ 1.21 (t, 6H, J=7 Hz), 1.95-2.05 (m, 2H), 3.20 (s, 3H), 3.13-3.22 (m, 2H), 3.98 (appt septet, 4H, J=7 Hz), 4.79 (s, 2H), 6.80 (d, 2H, J=9 Hz), 7.65 (d, 2H, J=9 Hz), 8.20 (br s, 1H), 8.60 (s, 1H). $^{31}$P (121.4 MHz, DMSO-d$_6$) δ 28.9. MS (m/z) 489.2 [M+H]$^+$, 511.2 [M+Na]$^+$.

Example 503

Synthesis of Exemplary Compounds of the Invention

Preparation of (2-{4-[(2,4-Diamino-pteridin-6-ylmethyl)-methyl-amino]-benzoylamino}-ethyl)-phosphonic acid To a solution of crude (2-{4-[(2,4-diamino-pteridin-6-ylmethyl)-methyl-amino]-benzoylamino}-ethyl)-phosphonic acid diethyl ester post silica column chromatography (61 mg, 125 μmol) in dry DMF (1.00 mL) was added TMSBr (129.0 μL, 999.2 μmol) at ambient temperature. The solution was then heated at 70° C. for 5.5 hours, when LCMS analysis demonstrated the reaction to be 90% complete. The reaction mixture was allowed to cool to room temperature and stirred for an additional 12 hours. The reaction was worked up by removal of the solvent in vacuo and dissolving the residue in DMF/H$_2$O (800 μL, 1:1) and 1N aqueous NaOH (15 μL). The product was purified by RP HPLC on C$_{18}$ column using H$_2$O/acetonitrile (2-95%) to provide 29 mg (53%) of the desired compound as a yellow solid. $^1$H NMR (300 MHz, DMSO-d$_6$) δ 1.67-1.85 (m, 2H), 3.19 (s, 3H), 3.25-3.40 (m, 2H), 4.76 (s, 2H), 6.71 (br s, 2H), 5.80 (d, 2H, J=9 Hz), 7.64 (d, 2H, J=9 Hz), 7.73 (br s, 2H), 8.15 (br s, 1H), 8.56 (s, 1H). $^{31}$P (121.4 MHz, DMSO-d$_6$) δ 23.0. MS (m/z) 431.3 [M−H]$^-$.

μmol). The solution was stirred at ambient temperature for 3 hours, when diethyl(aminopropyl)phosphonate oxalate (34.9 mg, 122.6 μmol) was added. The solution was stirred for 2 additional hours, whereupon complete consumption of the starting materials was observed. The reaction was worked up by removal of the solvent in vacuo and purifying the residue by silica gel chromatography using MeOH—CH$_2$Cl$_2$ (10-30%). The product (65.5 mg) collected from this chromatography step was sufficiently pure to be carried on to the next reaction. A small amount (32.8 mg) was re-purified by RP HPLC on C$_{18}$ column using H$_2$O/acetonitrile (2-95%) to provide 23.2 mg (75%) of the pure product. $^1$H NMR (300 MHz, DMSO-d$_6$) δ 1.20 (t, 6H, J=7.2 Hz), 1.64-1.75 (m, 4H), 3.22 (s, 3H), 3.41 (m, 2H), 3.98 (appt septet, 4H, J=7.2 Hz), 4.85 (s, 2H), 6.79 (d, 2H, J=9 Hz), 7.68 (d, 2H, J=9 Hz), 8.17 (br s, 1H), 8.70 (s, 1H); $^{31}$P (121.4 MHz, DMSO-d$_6$) δ 31.9; MS (m/z) 503.2 [M+H]$^+$.

Example 505

Synthesis of Exemplary Compounds of the Invention

Preparation of (2-{4-[(2,4-Diamino-pteridin-6-ylmethyl)-methyl-amino]-benzoylamino}-propyl)-phosphonic acid To a solution of crude (2-{4-[(2,4-diamino-pteridin-6-ylmethyl)-methyl-amino]-benzoylamino}-propyl)-phosphonic acid diethyl ester post silica column chromatography (32.2 mg, 66.2 μmol) in dry DMF (0.50 mL) was added

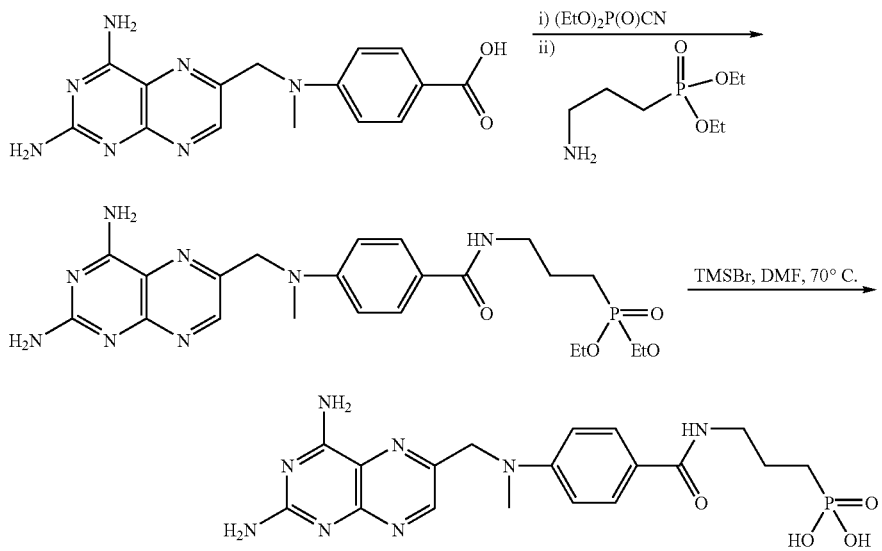

Example 504

Synthesis of Exemplary Compounds of the Invention

Preparation of (2-{4-[(2,4-Diamino-pteridin-6-ylmethyl)-methyl-amino]-benzoylamino}-propyl)-phosphonic acid diethyl ester To a solution of 4-[(2,4-diamino-pteridin-6-ylmethyl)-methyl-amino]-benzoic acid hemihydrochloride dihydrate (61.2 mg, 161 μmol) in DMF (2.8 mL) were added diethyl cyanophosphonate (31.8 μL, 210 μmol) and DIEA (27.8 μL, 161

TMSBr (68.0 μL, 529.6 μmol) at ambient temperature. The solution was then heated at 70° C. for 1.0 hour, when LCMS analysis demonstrated the reaction to be complete. The reaction mixture was allowed to cool to room temperature, and water (60 μL) and methanol (60 μL) were added. The crude reaction mixture was purified by RP HPLC on C$_{18}$ column using H$_2$O/acetonitrile (2-95%) to provide 11.2 mg (38%) of the desired compound as a yellow solid. $^1$H NMR (300 MHz, DMSO-d$_6$) δ 1.50 (m, 2H), 1.61 (m, 2H), 3.22 (s, 3H), 3.25-3.40 (m, 2H), 4.84 (s, 2H), 6.80 (d, 2H, J=9 Hz), 7.69 (d, 2H, J=9 Hz), 8.20 (br s, 1H), 8.69 (s, 1H). $^{31}$P (121.4 MHz, DMSO-d$_6$) δ 26.3. MS (m/z) 447.3 [M−H]$^-$.

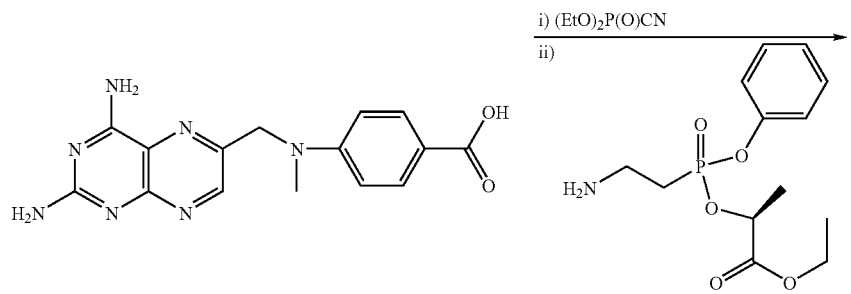

Example 506

Synthesis of Exemplary Compounds of the Invention

Preparation of 2-[(2-{4-[(2,4-diaminopteridin-6-ylmethyl)methylamino]benzoylamino}ethyl)-phenoxyphosphinoyloxy]propionic acid ethyl ester [diastereomeric mixture at phosphorus]

To a solution of 4-[(2,4-diamino-pteridin-6-ylmethyl)-methyl-amino]-benzoic acid hemihydrochloride dihydrate (60.0 mg, 158.3 µmol) in DMF (2.5 mL) were added diethyl cyanophosphonate (31.2 µL, 205.7 µmol) and DIEA (81.8 µL, 474.9 µmol). The solution was stirred at ambient temperature for 3.5 hours, when a solution of (S)-2-[(2-aminoethyl)phenoxyphosphinoyloxy]propionic acid ethyl ester mono acetic acid salt (57.1 mg, 158.3 µmol; mixture of diastereomers at phosphorus) in DMF (200 µL) was added. The solution was stirred for 1.5 additional hours, whereupon complete consumption of the starting materials was observed. The solvent was removed in vacuo and the crude material was purified by silica gel chromatography using MeOH—$CH_2Cl_2$ (10-30%). A small amount of the product (24.8 mg) was repurified by RP HPLC on $C_{18}$ column using $H_2O$/acetonitrile (2-95%) to provide 15.8 mg (65%) of the pure product. $^1$H NMR (300 MHz, DMSO-$d_6$) δ 1.17-1.27 (m, 3H), 1.32 (d, 2H, J=7.5 Hz), 1.42 (d, 1H, J=7.5 Hz) 2.27 (m, 2H), 3.19 (s, 3H), 3.53 (m, 2H), 4.08-4.14 (m, 2H), 4.77 (s, 2H), 4.98 (m, 1H), 6.72 (br s, 1H), 6.81 (d, 2H, J=9 Hz), 7.21 (m, 3H), 7.36 (m, 2H), 7.66 (d, 2H, J=9 Hz), 8.26 (br s, 1H), 8.56 (s, 1H); $^{31}$P (121.4 MHz, DMSO-$d_6$) δ 26.6, 27.4. MS (m/z) 609.2 [M+H]$^+$.

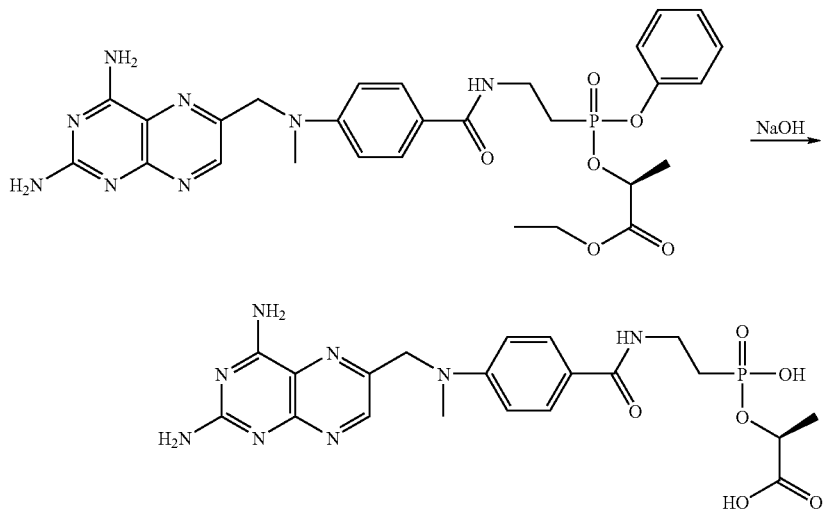

Example 507

Synthesis of Exemplary Compounds of the Invention

Preparation of 2-[(2-{4-[(2,4-diaminopteridin-6-ylmethyl)methylamino]benzoylamino}ethyl)-phenoxyphosphinoyloxy]propionic acid [diastereomeric mixture at phosphorus]

To a solution of 2-[(2-{4-[(2,4-diaminopteridin-6-ylmethyl)methylamino]benzoylamino}ethyl)phenoxy-phosphinoyloxy]propionic acid ethyl ester (mixture of diastereomers at phosphorus; 40.0 mg, 65.7 μmol) in DMF (0.4 mL), acetonitrile (0.2 mL) and water (0.2 mL) was added aqueous sodium hydroxide (1 N, 131.4 μL). The solution was stirred at ambient temperature for 4 hours. The solvents were removed in vacuo and the crude product was purified by RP HPLC on $C_{18}$ column using $H_2O$/acetonitrile (2-95%) to provide 23.7 mg (71.3%) of the pure product. $^1$H NMR (300 MHz, DMSO-$d_6$) δ 1.30 (d, 2H, J=6.9 Hz), 1.79 (m, 2H), 3.21 (s, 3H), 3.37 (m, 2H), 4.61 (m, 1H), 4.81 (s, 2H), 6.79 (d, 2H, J=8.7 Hz), 7.64 (d, 2H, J=9.7 Hz), 8.25 (br s, 1H), 8.63 (s, 1H); $^{31}$P (121.4 MHz, DMSO-$d_6$) δ 25.1. MS (m/z) 505.2 [M+H]$^+$.

Example 508

Synthesis of Exemplary Compounds of the Invention

Preparation of 2-[(2-{4-[(2,4-diaminopteridin-6-ylmethyl)methylamino]benzoylamino}ethyl)-phenoxyphosphinoyloxy]propionic acid ethyl ester [diastereomerically pure at phosphorus]

To a solution of 4-[(2,4-diaminopteridin-6-ylmethyl)-methyl-amino]benzoic acid hemihydrochloride dihydrate (101.9 mg, 268.9 μmol) in DMF (3.3 mL) were added diethyl cyanophosphonate (53.0 μL, 349.5 μmol) and DIEA (138.0 μL, 806.7 μmol). The solution was stirred at ambient temperature for 2.5 hours, whereupon (S)-2-[(2-aminoethyl)phenoxyphosphinoyloxy]propionic acid ethyl ester mono acetic acid salt (diastereomerically pure at phosphorus; 268.9 μmol) in DMF (500 μL) was added. The solution was stirred for 30 additional minutes, whereupon complete consumption of the starting materials was observed. The solvent was removed in vacuo and the crude material was purified by silica gel chromatography using MeOH—$CH_2Cl_2$ (10-30%). A small amount of the product (40.0 mg) was repurified by RP HPLC on $C_{18}$ column using $H_2O$/acetonitrile (2-95%) to provide 28.7 mg (75.1%) of the pure product. $^1$H NMR (300 MHz, DMSO-$d_6$) δ 1.15 (t, 3H, J=7.2 Hz), 1.44 (d, 3H, J=6.9 Hz),

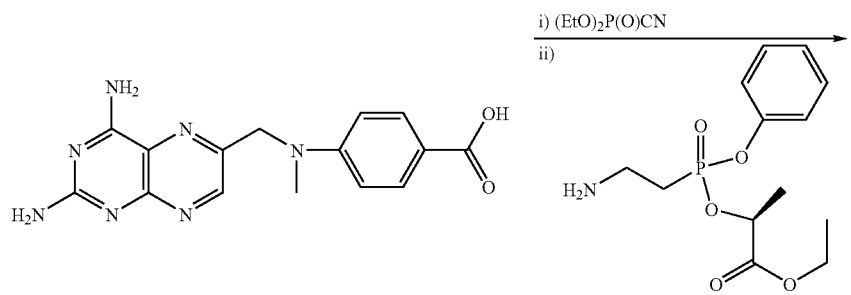

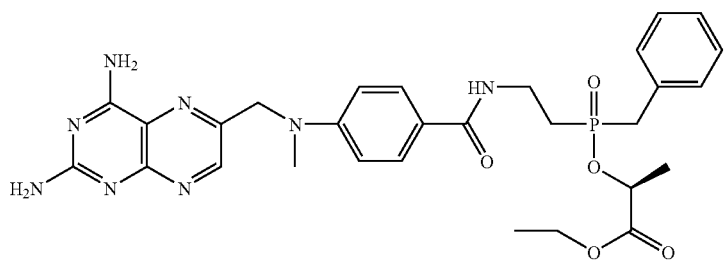

2.26 (m, 2H), 3.23 (s, 3H), 3.51 (m, 2H), 4.09 (q, 2H, J=7.2 Hz), 4.86 (s, 2H), 5.01 (m, 1H), 6.81 (d, 2H, J=9.3 Hz), 7.21 (m, 3H), 7.35 (m, 2H), 7.68 (d, 2H, J=9.3 Hz), 8.29 (br s, 1H), 8.71 (s, 1H); $^{31}$P (121.4 MHz, DMSO-$d_6$) δ 26.6. MS (m/z) 609.2 [M+H]$^+$.

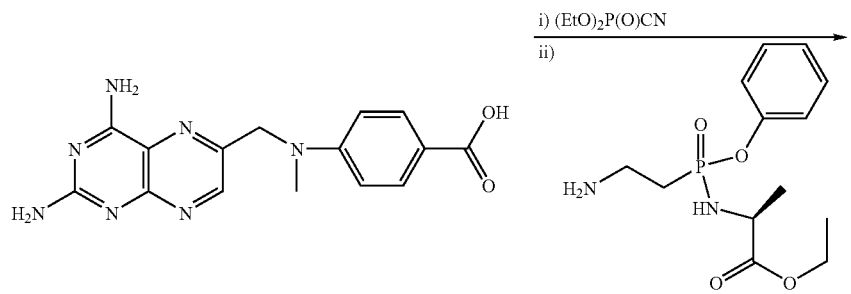

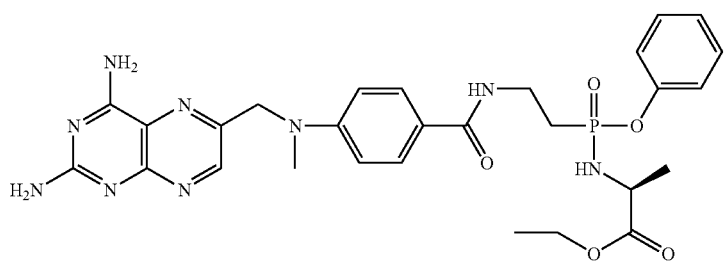

Example 509

Synthesis of Exemplary Compounds of the Invention

Preparation of 2-[(2-{4-[(2,4-diaminopteridin-6-ylmethyl)methylamino]benzoylamino}ethyl)-phenoxyphosphinoylamino]propionic acid ethyl ester (mixture of diastereomers at phosphorus)

To a solution of 4-[(2,4-diamino-pteridin-6-ylmethyl)-methyl-amino]-benzoic acid hemihydrochloride dihydrate (39.6 mg, 104.0 mmol) in DMF (1.2 mL) were added diethyl cyanophosphonate (20.6 μL, 136.1 μmol) and DIEA (36.0 μL, 209.4 μmol). The solution was stirred at ambient temperature for 3 hours, when (S)-2-[(2-aminoethyl)phenoxyphosphinoylamino]propionic acid ethyl ester mono acetic acid salt (mixture of diastereomers at phosphorus; 104.0 μmol) in DMF (200 μL) was added. The solution was stirred for 30 minutes when complete consumption of the starting materials was observed. An aliquot (66%) of the reaction was purified by silica gel chromatography using MeOH—$CH_2Cl_2$ (10-30%), yielding 27.2 mg of crude product. A small amount of the product (10 mg) was repurified by RP HPLC on $C_{18}$ column using $H_2O$/acetonitrile (2-95%) to provide 4.2 mg (26%) of the pure product. $^1$H NMR (300 MHz, DMSO-$d_6$) δ 1.11 (t, 3H, J=6.9 Hz), 1.18 (d, 3H, J=7.2 Hz), 2.06-2.17 (m, 2H), 3.20 (s, 3H), 3.51 (m, 2H), 3.88 (m, 1H), 4.02 (m, 2H), 4.79 (s, 2H), 5.61 (m, 1H), 6.80 (d, 2H, J=9 Hz), 6.98 (br s, 1H), 7.18 (m, 3H), 7.32 (m, 2H), 7.67 (d, 2H, J=9 Hz), 8.20 (br s, 1H), 8.59 (s, 1H) $^{31}$P (121.4 MHz, DMSO-$d_6$) δ 29.5, 30.1. MS (m/z) 608.2 [M+H]$^+$.

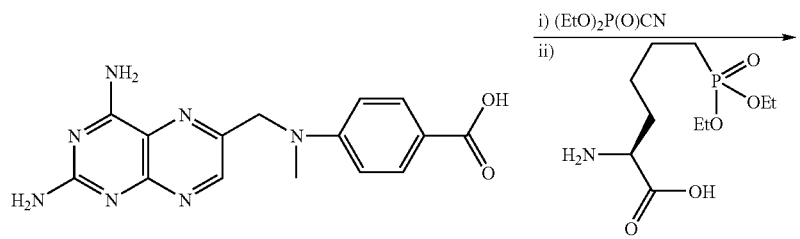

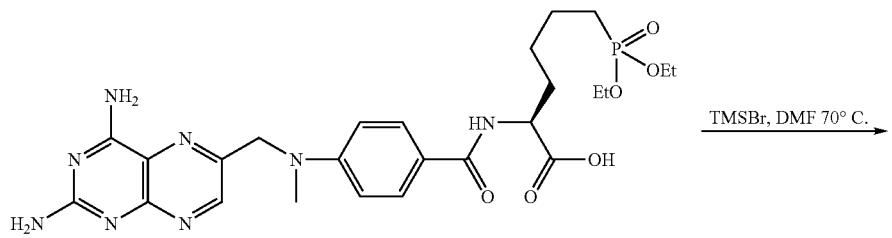

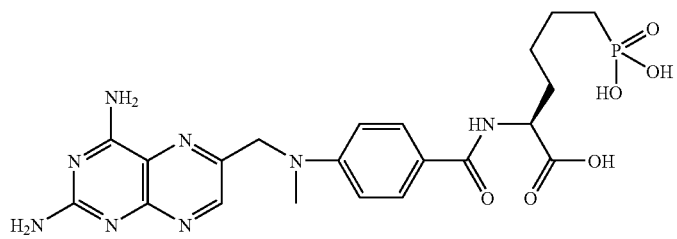

Example 510

Synthesis of Exemplary Compounds of the Invention

Preparation of 2-{4-[(2,4-Diamino-pteridin-6-ylmethyl)-methyl-amino]-benzoylamino}-6-(diethoxyphosphoryl)-hexanoic acid To a solution of 4-[(2,4-diamino-pteridin-6-ylmethyl)-methyl-amino]-benzoic acid hemihydrochloride dihydrate (63.0 mg, 166.2 μmol) in DMF (2.8 mL) were added diethyl cyano phosphonate (30.8 μL, 199.4 μmol) and DIEA (85.8 μL, 498.6 μmol). The solution was stirred at ambient temperature for 3.5 hours when (L)-2-amino-6-diethylphosphonatohexanoic acid (44.3 mg, 166.2 μmol) was added. The solution was stirred for 48 additional hours. The reaction was worked up by removal of the solvent in vacuo and purifying the residue by silica gel chromatography using MeOH—$CH_2Cl_2$ (10-30%). The product (87 mg) collected from this chromatography step was sufficiently pure to be carried on to the next reaction. An aliquot of the product (51.0 mg) was repurified by RP HPLC on $C_{18}$ column using $H_2O$/acetonitrile (2-95%) to provide 24.7 mg (44%) of the pure product. $^1$H NMR (300 MHz, DMSO-$d_6$) δ 1.18 (t, 6H, J=6.9 Hz), 1.42 (m, 4H), 1.65 (m, 4H), 3.20 (s, 3H), 3.92 (m, 4H), 4.29 (m, 1H), 4.78 (s, 2H), 6.72 (br s, 1H), 6.81 (d, 2H, J=9 Hz), 7.73 (d, 2H, J=9 Hz), 8.14 (d, 1H, J=7.8 Hz), 8.56 (s, 1H); $^{31}$P (121.4 MHz, DMSO-$d_6$) δ 31.8; MS (m/z) 574.3 [M]$^+$.

Example 511

Synthesis of Exemplary Compounds of the Invention

Preparation of 2-{4-[(2,4-Diaminopteridin-6-ylmethyl)methylamino]benzoylamino}-6-(phosphoryl) hexanoic acid To a solution of crude (2-{4-[(2,4-diamino-pteridin-6-ylmethyl)-methyl-amino]-benzoylamino})-2' (L)-(6'-(phosphonic acid diethyl ester)hexanoic acid) post silica column chromatography (20 mg, 34.6 μmol) in dry DMF (0.60 mL) was added TMSBr (18.0 μL, 139.2 μmol) at ambient temperature. The solution was then heated at 70° C. for 18 hours, after which the reaction mixture was allowed to cool to room temperature. The solvent was removed in vacuo and dissolved in DMF (400 μL) and water (60 μL). This solution was purified by RP HPLC on $C_{18}$ column using $H_2O$/acetonitrile (2-95%) to provide 8.9 mg (49%) of the product as a yellow solid. $^1$H NMR (300 MHz, DMSO-$d_6$) δ 1.45 (m, 6H), 1.75 (m, 2H), 3.20 (s, 3H), 4.25 (m, 1H), 4.77 (s, 2H), 6.62 (br s, 1H), 6.80 (d, 2H, J=8.7 Hz), 7.73 (d, 2H, J=8.7 Hz), 8.14 (br s, 1H), 8.55 (s, 1H); MS (m/z) 519.2 [M+H]$^+$.

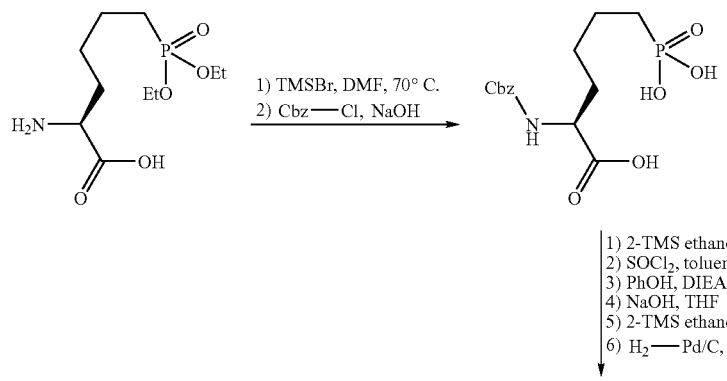

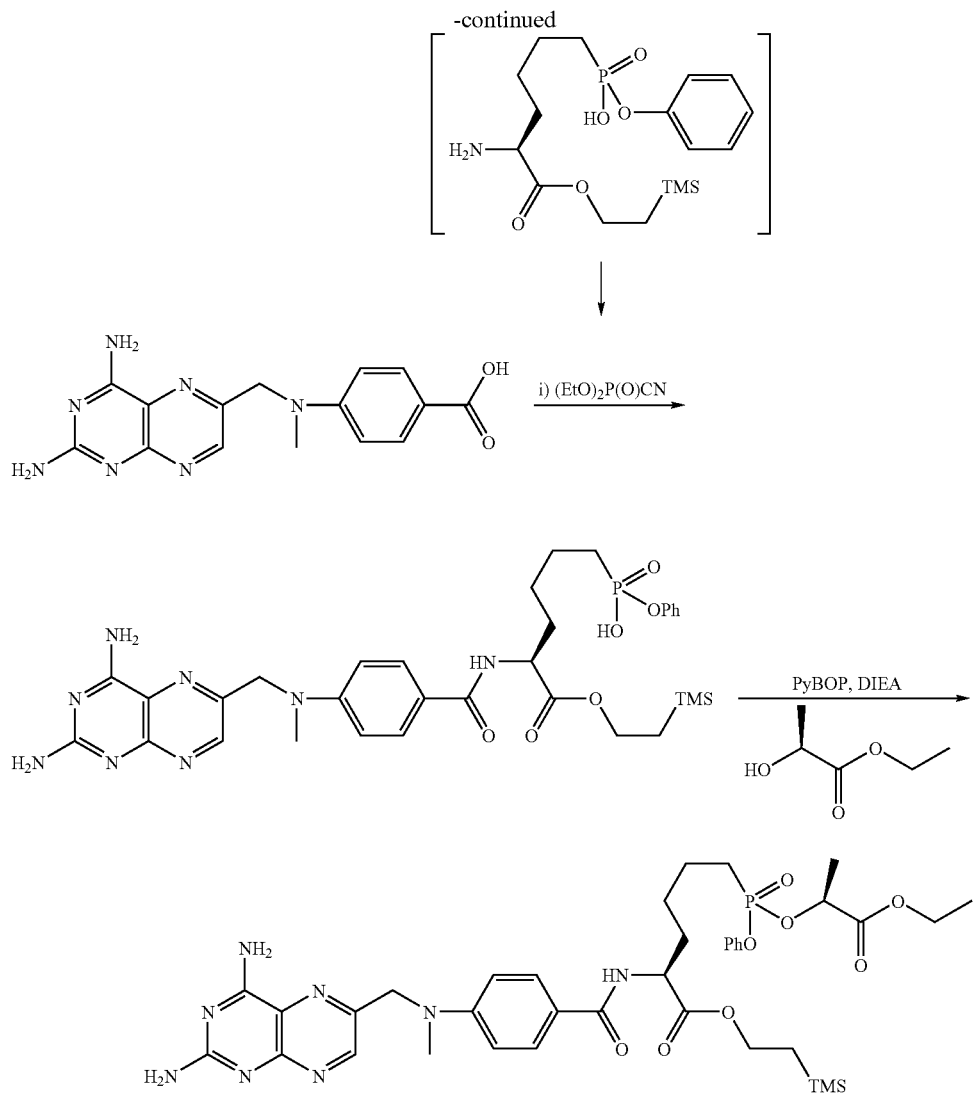

Example 512

Synthesis of Exemplary Compounds of the Invention

Preparation of (L)-2-Cbz-Amino-hexanoic acid-6-phosphonic acid

To a suspension of (L)-2-amino-6-(diethoxyphosphonyl)hexanoic acid (106 mg, 396.8 μmol) in dry DMF (2.00 mL) was added TMSBr (307.0 μL, 2,381.0 μmol) at ambient temperature. The solution was then heated at 70° C. for 2 hours, after which the reaction mixture was allowed to cool to room temperature. The solvent was removed in vacuo. The crude material was dissolved in water (0.25 mL) and NaOH (1-N, 2.50 mL). Benzyl chloroformate (79.3 μL, 555.5 μmol) was added and stirring at room temperature was continued. After 2 hours, the solution was washed with ether (2 mL) and the aqueous layer was acidified with aqueous HCl to pH 1. The aqueous layer was extracted with EtOAc (3×5 mL). The combined organic extracts were dried over sodium sulfate. Filtration and evaporation of solvents yielded a crude product, which was sufficiently pure for further transformations. $^1$H NMR (300 MHz, DMSO-$d_6$) δ 1.42-1.65 (m, 8H), 3.90 (m, 1H), 5.02 (s, 2H), 7.32 (s, 5H), 7.55 (m, 1H), 7.94 (s, 1H); $^{31}$P (121.4 MHz, DMSO-$d_6$) δ 26.5; MS (m/z) 345.6 [M+H]$^+$.

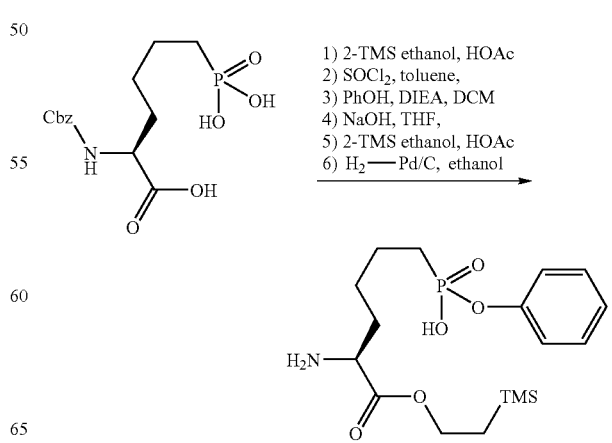

Example 513

Synthesis of Exemplary Compounds of the Invention

Preparation of (L)-2-Amino-hexanoic acid 2' TMS ethyl ester-6-phosphonic acid mono phenyl ester To a solution of (L)-2-Cbz-amino-hexanoic acid-6-phosphonic acid (137.3 mg, 397.9 µmol) in 2-TMS ethanol (2.5 mL) was added acetyl chloride (50 µL). Stirring at room temperature was continued. After 22 hours complete conversion was observed. The solvents were removed in vacuo. The crude material was sufficiently pure for the next step.

One half of the crude material (198.9 µmol) was dissolved in toluene (3.0 mL) at room temperature. Thionyl chloride (167.2 mg, 1,416.0 µmol) was added and the reaction mixture was heated at 70° C. (oil bath). After 4 hours, the reaction was cooled to room temperature and the solvent was removed in vacuo. The crude material was re-dissolved in methylene chloride (2.0 mL) and a solution of phenol (36.6 mg, 389.0 µmol) and DIEA (67.0 µL, 389.0 µmol) in methylene chloride (1.0 mL) was added. Stirring at room temperature was continued. After 4 hrs the solvents were removed in vacuo.

The crude material was dissolved in tetrahydrofuran (THF) (3.0 mL) and aqueous sodium hydroxide solution (1N, 0.885 mL) was added. Stirring at room temperature was continued. After 14 hours the solvent was removed in vacuo to provide the crude phosphonate mono phenyl ester (63.8 mg). This material was dissolved in 2-TMS ethanol (1.0 mL) and acetyl chloride (20 µL) was added. Stirring at room temperature was continued. After 22 hours complete conversion to the carboxylate ester was observed. The solvents were removed in vacuo. The material was sufficiently pure for the next step.

One half of the crude material (75 µmol) was dissolved in ethanol (1.5 mL). Pd/C (5%, 20 mg) was added and the reaction was placed under an atmosphere of hydrogen gas. After 1.5 hours Celite was added and the crude reaction mixture was filtered through Celite. The solvents were removed in vacuo and the crude material was used in the next step without further purification.

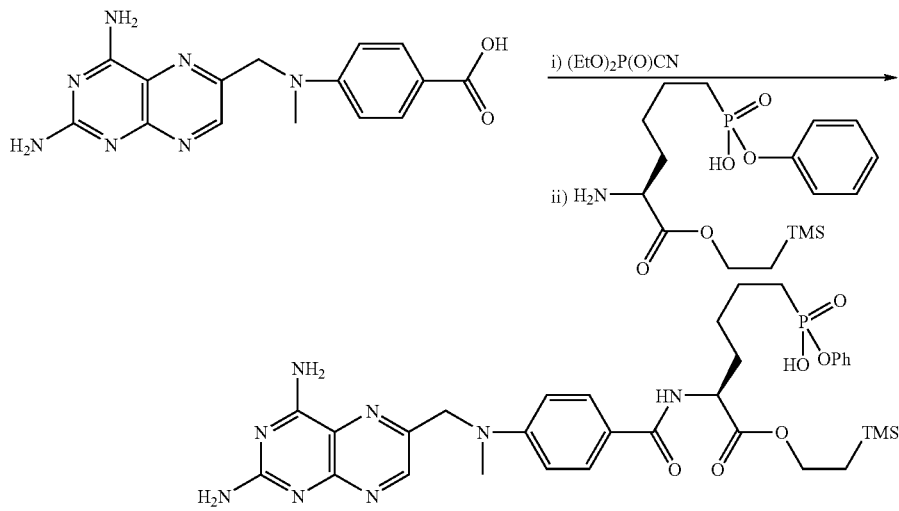

Example 514

Synthesis of Exemplary Compounds of the Invention

Preparation of 2-{4-[(2,4-Diamino-pteridin-6-ylmethyl)-methyl-amino]-benzoylamino}-6'-(mono phenyl-phosphonate)-hexanoic acid TMS ethanol ester To a solution of 4-[(2,4-diamino-pteridin-6-ylmethyl)-methyl-amino]-benzoic acid hemihydrochloride dihydrate (22.7 mg, 60.0 µmol) in DMF (0.80 mL) were added diethyl cyano phosphonate (12.4 µL, 78.0 µmol) and DIEA (31.0 µL, 180.0 mmol). The solution was stirred at ambient temperature for one hour when (L)-2-amino-6-monophenoxyphosphonato-hexanoic acid 2' TMS ethyl ester (70.5 µmol), suspended in DMF (0.2 mL), was added. The solution was stirred for 3.5 additional hours. The crude reaction mixture was purified by RP HPLC on $C_{18}$ column using $H_2O$/acetonitrile (5-95%) to provide 19.4 mg (46%) of the pure product. $^1$H NMR (300 MHz, DMSO-$d_6$) δ 0.0 (s, 9H), 0.91 (t, 2H, J=8.1 Hz), 1.42-1.53 (m, 4H), 1.67-1.76 (m, 4H), 3.24 (s, 3H), 4.10 (t, 2H, J=8.1 Hz), 4.29 (m, 1H), 4.86 (s, 2H), 6.81 (d, 2H, J=9 Hz), 7.12 (m, 3H), 7.31 (m, 2H), 7.74 (d, 2H, J=9 Hz), 8.14 (d, 1H, J=7.8 Hz), 8.71 (s, 1H); $^{31}$P (121.4 MHz, DMSO-$d_6$) δ 26.2; MS (m/z) 695.2 [M]$^+$.

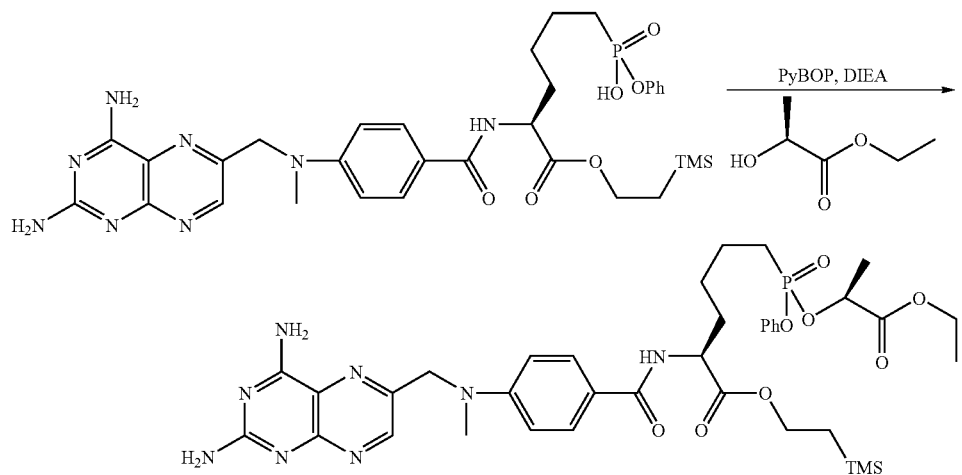

Example 515

Synthesis of Exemplary Compounds of the Invention

Preparation of 2-{4-[(2,4-Diamino-pteridin-6-ylmethyl)-methyl-amino]-benzoylamino}-6'-(mono phenyl mono (S) ethyl lactate-phosphonate)-hexanoic acid TMS ethanol ester To a solution of 2-{4-[(2,4-diamino-pteridin-6-ylmethyl)-methyl-amino]-benzoylamino}-6'-(mono phenyl-phosphonate)-hexanoic acid TMS ethanol ester (14.5 mg, 20.8 µmol) in DMF (0.70 mL) was added PyBOP (32.4 mg, 62.4 µmol), DIEA (21.4 mg, 166.4 µmol) and (S) ethyl lactate (19.6 mg, 166.4 µmol). The reaction mixture was stirred at room temperature for one hour. The crude reaction mixture was purified by RP HPLC on $C_{18}$ column using $H_2O$/acetonitrile (5-95%) to provide 13.5 mg (81%) of the pure product as a mixture of diastereomers at phosphorus (4:1). $^1H$ NMR (300 MHz, CDCl$_3$) δ 0.0 (s, 9H), 1.02 (t, 2H, J=8.7 Hz), 1.23 (t, 3H, J=9.3 Hz), 1.35 (d, 2.4H, J=6.6 Hz), 1.42-1.53 (m, 4.6H), 1.67-1.86 (m, 4H), 3.14 (s, 3H), 4.03-4.27 (m, 4H), 4.71 (br s, 3H), 4.98 (m, 0.8H), 5.10 (m, 0.2H), 6.57 (d, 2H, J=7.5 Hz), 7.00 (m, 1H), 7.16 (m, 3H), 7.30 (m, 2H), 7.63 (d, 2H, J=7.5 Hz), 8.43 (s, 1H); $^{31}P$ (121.4 MHz, DMSO-d$_6$) δ 30.5, 29.2; MS (m/z) 795.2 [M]$^+$.

Example 516

Synthesis of Exemplary Compounds of the Invention

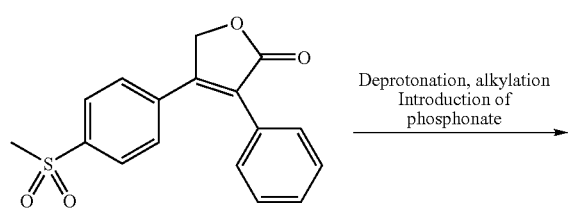 Deprotonation, alkylation Introduction of phosphonate

-continued

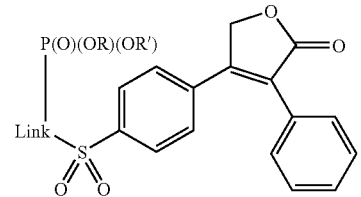

Compounds of the invention can generally be prepared as illustrated above. For example, a specific compound of the invention can be prepared as follows.

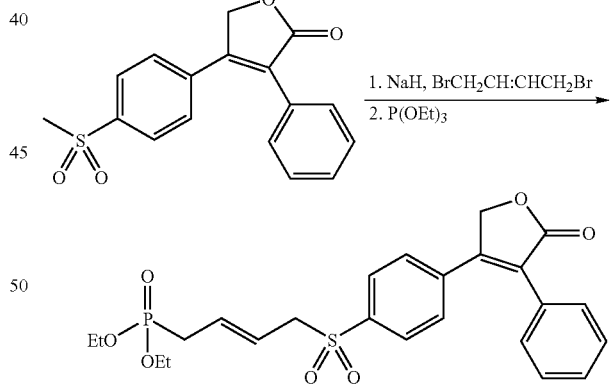

Rofecoxib is treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the mono-alkylated product is isolated by chromatography. The bromide so formed is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid.

Example 517

Synthesis of Exemplary Compounds of the Invention

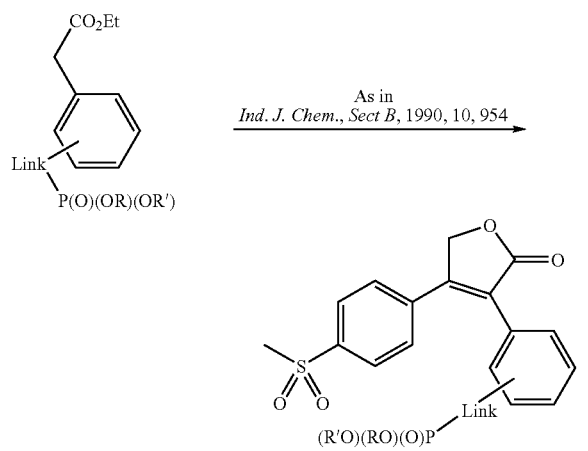

Compounds of the invention can generally be prepared as illustrated above (see also, *Ind. J. Chem., Sect B,* 1990, 10, 954.) A specific intermediate useful in the above process can be prepared as follows.

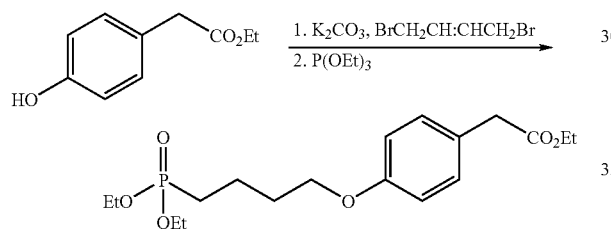

Ethyl 4-hydroxyphenylacetate is treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the monoalkylated product is isolated by chromatography. The bromide so formed is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid.

Example 518

Synthesis of Exemplary Compounds of the Invention

Scheme 518-1

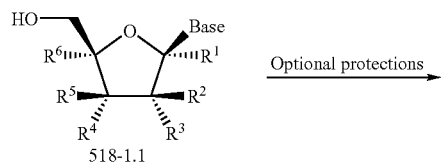

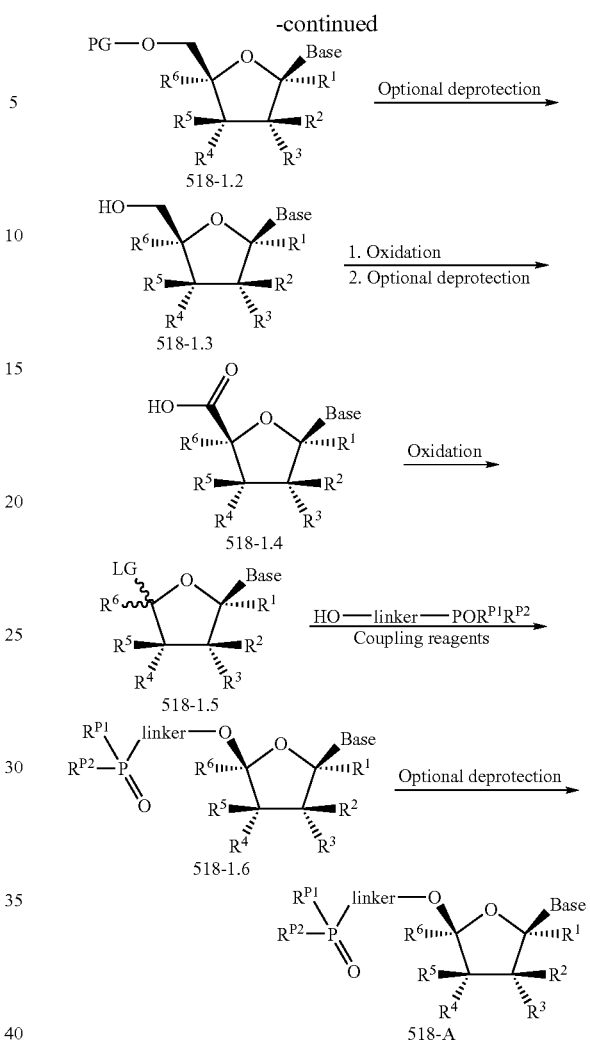

Appropriate oxidant(s) can convert the primary alcohol (5'-hydroxy) shown in 518-1.3 to a carboxylic acid or its corresponding ester. In the case of an ester, an additional deprotection step will give the carboxylic acid, 518-1.4. A variety of oxidation procedures exist in the literature and can be utilized here. These include but are not limited to the following methods: (i) pyridinium dichromate in $Ac_2O$, t-BuOH, and dichloromethane producing the t-butyl ester, followed by a deprotection using reagent such as trifluoroacetic acid to convert the ester to the corresponding carboxylic acid (see Classon, et al, *Acta Chem. Scand. Ser. B;* 39; 1985; 501-504. Cristalli, et al; *J. Med. Chem.;* 31; 1988; 1179-1183.); (ii) iodobenzene diacetate and 2,2,6,6-tetramethyl-1-piperidinyloxy, free radical (TEMPO) in acetonitrile, producing the carboxylic acid (See Epp, et al; *J. Org. Chem.* 64; 1999; 293-295. Jung et al; *J. Org. Chem.;* 66; 2001; 2624-2635.); (iii) sodium periodate, ruthenium(III) chloride in chloroform producing the carboxylic acid (see Kim, et al, *J. Med. Chem.* 37; 1994; 4020-4030. Homma, et al; *J. Med. Chem.;* 35; 1992; 2881-2890); (iv) chromium trioxide in acetic acid producing the carboxylic acid (see Olsson et al; *J. Med. Chem.;* 29; 1986; 1683-1689. Gallo-Rodriguez et al; *J. Med. Chem.;* 37; 1994; 636-646); (v) potassium permanganate in aqueous potassium hydroxide producing the carboxylic acid (see Ha, et al; *J. Med. Chem.;* 29; 1986; 1683-1689.

Franchetti, et al; *J. Med. Chem.;* 41; 1998; 1708-1715.) (vi) nucleoside oxidase from *S. maltophilia* to give the carboxylic acid (see Mahmoudian, et al; *Tetrahedron;* 54; 1998; 8171-8182.)

The preparation of 518-1.5 from 518-1.4 using lead(IV) tetraacetate (LG=OAc) was described by Teng et al; *J. Org. Chem.;* 59; 1994; 278-280 and Schultz, et al; *J. Org. Chem.;* 48; 1983; 3408-3412. When lead(IV) tetraacetate is used together with lithium chloride (see Kochi, et al; *J. Am. Chem. Soc.;* 87; 1965; 2052), the corresponding chloride is obtained (1.5, LG=Cl). Lead(IV) tetraacetate in combination with N-chlorosuccinimide can produce the same product (1.5, LG=Cl) (see Wang, et al; *Tet. Asym.;* 1; 1990; 527 and Wilson et al; *Tet. Asym.;* 1; 1990; 525). Alternatively, the acetate leaving group (LG) can also be converted to other leaving group such as bromide by treatment of trimethylsilyl bromide to give 518-1.5 ((see Spencer, et al; *J. Org. Chem.;* 64; 1999; 3987-3995).

The coupling of 518-1.5 (LG=OAc) with a variety of nucleophiles were described by Teng et al; *Synlett;* 1996; 346-348 and U.S. Pat. No. 6,087,482; Column 54 line 64 to Column 55 line 20. Specifically, the coupling between 518-1.5 and diethyl hydroxymethylphosphonate in the presence of trimethylsilyl trifluoromethanesulfonate (TMS-OTf) was described. It can be envisioned that other compounds with the general structure of HO-linker-POR$^{P1}$R$^{P2}$ can also be used so long as the functional groups in these compounds are compatible with the coupling reaction conditions. There are many examples in the published literature describing the coupling of 518-1.5 (LG=halogen) with a variety of alcohols. The reactions can be facilitated with a number of reagents, such as silver(I) salts (see Kim et al; *J. Org. Chem.;* 56; 1991; 2642-2647, Toikka et al; *J. Chem. Soc. Perkins Trans.* 1; 13; 1999; 1877-1884), mercury(II) salts (see Veeneman et al; *Recl. Trav. Chim. Pays*-Bas, 106; 1987; 129-131), boron trifluoride diethyl etherate (see Kunz et al; *Hel. Chim Acta;* 68; 1985; 283-287), Tin(II) chloride (see O'Leary et al; *J. Org. Chem.;* 59; 1994; 6629-6636), alkoxide (see Shortnacy-Fowler et al; *Nucleosides Nucleotides;* 20; 2001; 1583-1598), and iodine (see Kartha et al; *J. Chem. Soc. Perkins Trans.* 1; 2001; 770-772). These methods can be selectively used in conjunction with different methods in forming 518-1.5 with various leaving groups (LG) to produce 518-1.6.

The introduction and removal of protecting groups from a compound is a commonly practiced art in organic synthesis. Many sources of information of the art are available in the published literature, e.g. Greene and Wuts, *Protecting Groups in Organic Synthesis,* 3$^{rd}$ Ed., John Wiley & Sons, Inc., 1999. The main purpose is to temporarily transform a functional group so that it will survive a set of subsequent reaction procedures. Afterwards, the original functional group can be restored by a preconceived deprotection procedure. Therefore, the transformations from 518-1.1 to 518-1.2, from 518-1.2 to 518-1.3, and from 518-1.6 to 518-A are intended to allow the core components of the transformations (from 518-1.3 to 518-1.6) to occur while preserving the functional groups already exist in the compound structures.

The 5'-hydroxyl group of ribavirin (518-2) can be selectively protected by an appropriate protecting group. The product, 518-3, can be treated with benzoyl chloride, an appropriate base, in the presence of catalytic amount of 4-dimethylaminopyridine, to convert 2'- and 3'-hydroxyl groups to their corresponding benzoyl esters, 518-4. The 5'-hydroxyl group can be selectively-deprotected to give 518-5. Following procedure described for analogous compound in U.S. Pat. No. 6,087,482, FIG. 2, 518-4 can be converted to 518-7 in a three-step sequence. Treating 518-7 with a coupling agent, such as trimethylsilyl trifluoromethanesulfonate, in the presence of an appropriate alcohol containing a phosphonate group can produce 518-8. Lastly, treating 518-8 with aqueous sodium hydroxide can deprotect the 2'- and 3'-hydroxyl groups to give 518-1. It is important to point out that R$^{P1}$ and R$^{P2}$ in 518-8 and 518-1 do not need to be the same.

A variety of compounds of the general structure 518-1.1 can either be prepared using procedures described in the literature, or be purchased from commercial sources. The following are good sources for information on the art of preparing a variety of compounds of the general structure 518-1.1, Townsend, Chemistry of Nucleosides and Nucleotides, Plenum Press, 1994; and Vorbruggen and Ruh-Pohlenz, *Handbook of Nucleoside Synthesis,* John Wiley & Sons, Inc., 2001. Some exemplary precursors, starting materials and their commercial sources include:

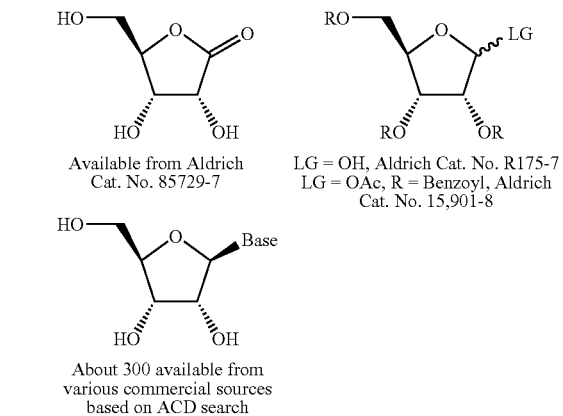

Available from Aldrich Cat. No. 85729-7

LG = OH, Aldrich Cat. No. R175-7
LG = OAc, R = Benzoyl, Aldrich Cat. No. 15,901-8

About 300 available from various commercial sources based on ACD search

Compound 518-2.1 in Scheme 518-2 is prepared using method described (WO 01/90121, page 115, table). The 5'-hydroxyl in 518-2.1 is protected as t-butyldimethylsilyl (TBDMS) ether. The 2'- and 3'-hydroxyl groups can be protected as benzoyl (Bz) esters to give 518-2.2. The 5'-hydroxyl can then be deprotected to give 518-2.3. Oxidation using iodobenzene diacetate and 2,2,6,6-tetramethyl-1-piperidinyloxy, free radical (TEMPO) convert the primary alcohol to the corresponding acid 518-2.4. Further oxidation of 518-2.4 using lead tetraacetate can produce 518-2.5. Coupling between 518-2.5 and diethyl hydroxymethylphosphonate (available from Sigma-Aldrich, Cat. No. 39,262-6) effected by T-MS-OTf can afford 518-2.6. Treating 518-2.6 with TMS-Br converts the phosphodiester to the corresponding phosphonic acid 518-2.7. Deprotection of the 2'- and 3'-hydroxyl gives 518-2.8 as an example of the generic structure 518-A, where Base is an adenine, R$^1$, R$^5$, and R$^6$ are hydrogen, R$^2$ is methyl group, R$^3$ and R$^4$ are hydroxyl groups, linker is a methylene group, and R$^{P1}$ and R$^{P2}$ are both hydroxyl groups.

Scheme 518-2

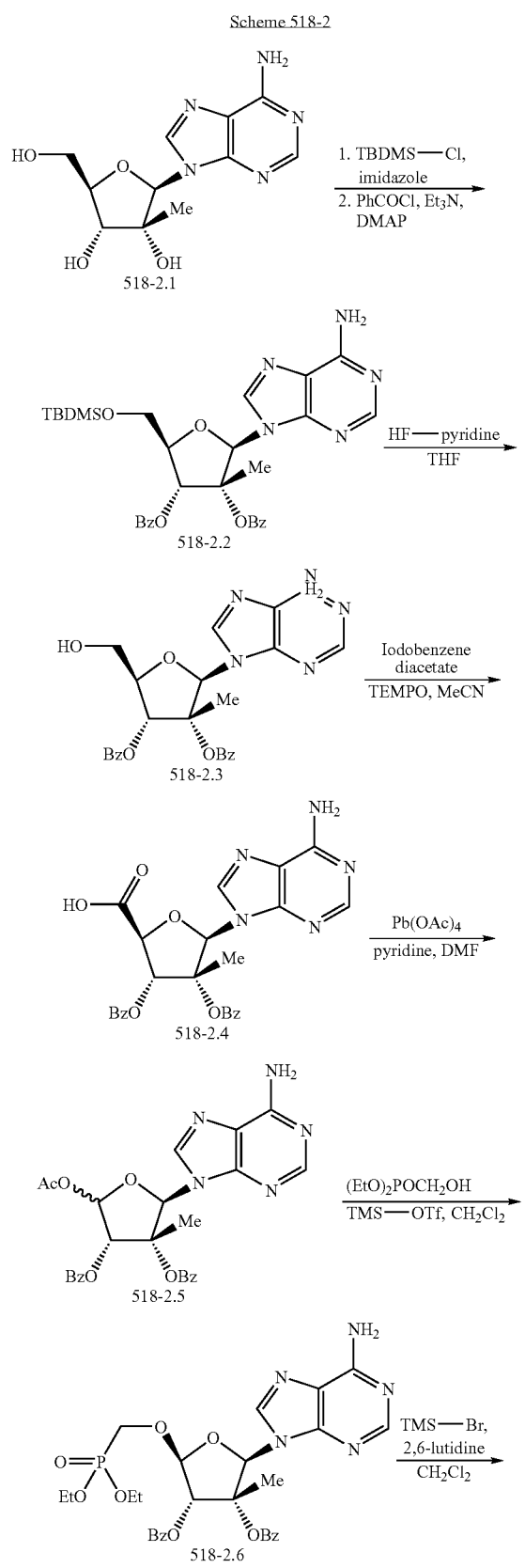

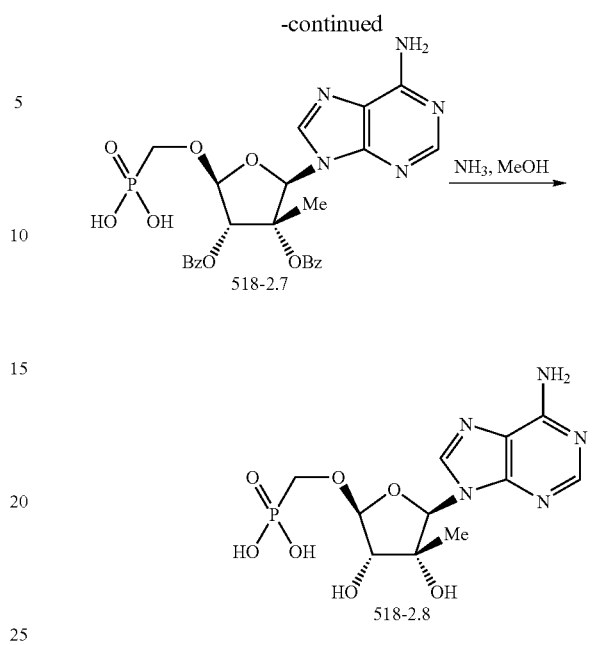

The phosphonic acids in 518-2.7 and 518-2.8 are used as examples for illustration purpose. Other forms of phosphonates can be access via the phosphonic acid, or other forms, such as the corresponding diesters. See section INTERCONVERSIONS OF PHOSPHONATES for details.

Many compounds of the generic structure 518-1.1 with the sugar moiety in its L-configuration are either commercially available or can be prepared by procedures described in the published literature. The opposite D-configuration enantiomers of the L-nucleoside analogs previously discussed can be prepared from the precursors that are the opposite enantiomers of 518-3.1, 518-3.2, and 518-3.3. Scheme 518-3 describes the preparation of the opposite enantiomers of 518-3.1, 518-3.2, and 518-3.3.

Scheme 518-3

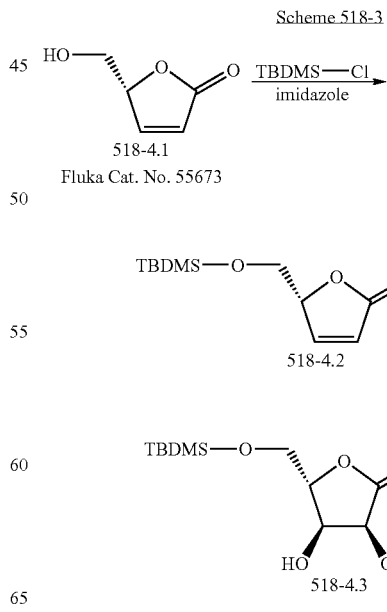

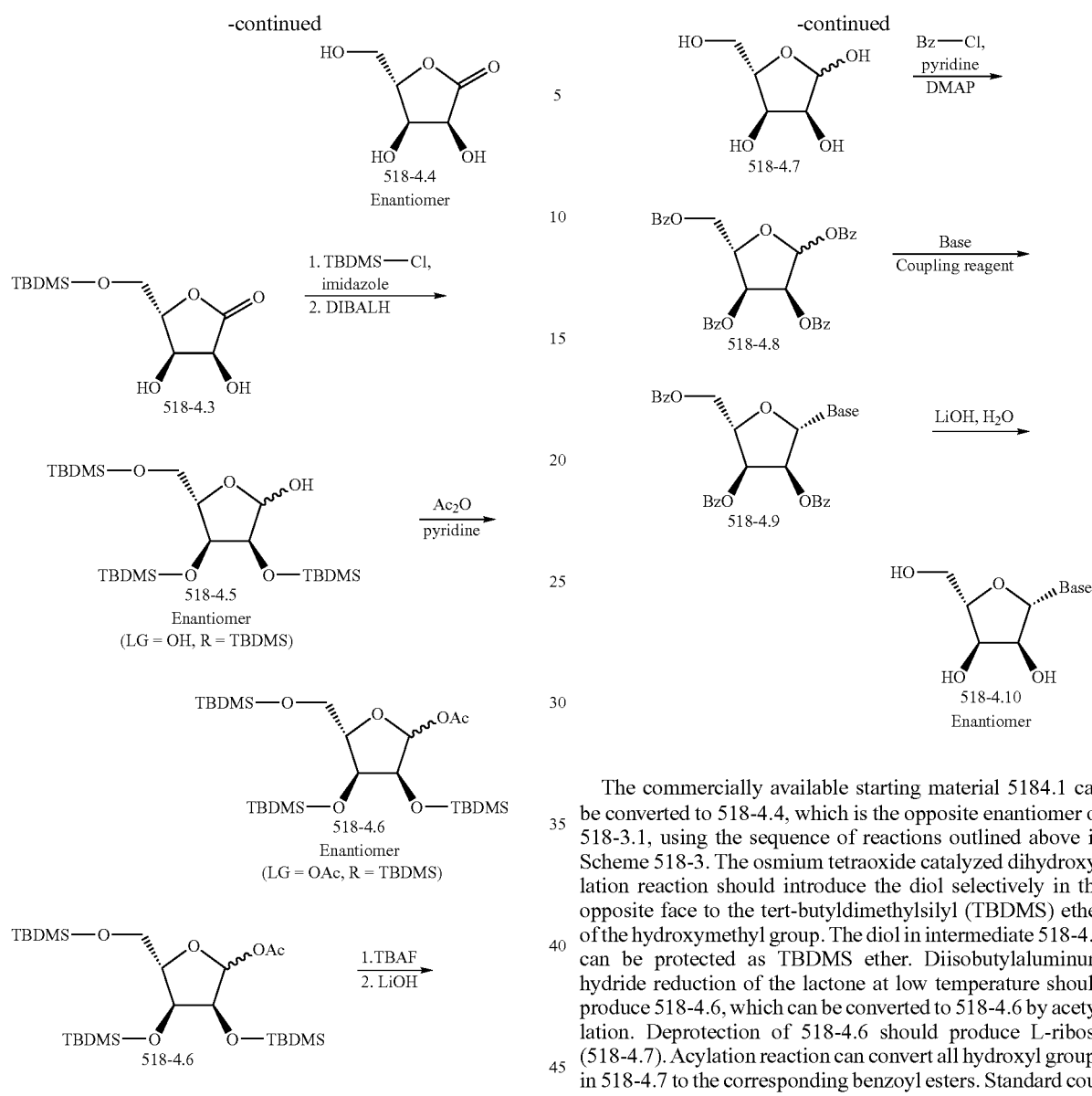

The commercially available starting material 5184.1 can be converted to 518-4.4, which is the opposite enantiomer of 518-3.1, using the sequence of reactions outlined above in Scheme 518-3. The osmium tetraoxide catalyzed dihydroxylation reaction should introduce the diol selectively in the opposite face to the tert-butyldimethylsilyl (TBDMS) ether of the hydroxymethyl group. The diol in intermediate 518-4.3 can be protected as TBDMS ether. Diisobutylaluminum hydride reduction of the lactone at low temperature should produce 518-4.6, which can be converted to 518-4.6 by acetylation. Deprotection of 518-4.6 should produce L-ribose (518-4.7). Acylation reaction can convert all hydroxyl groups in 518-4.7 to the corresponding benzoyl esters. Standard coupling reactions with a variety of nucleobases should produce 518-4.10, which is the opposite enantiomer of 518-3.3.

Scheme 518-4

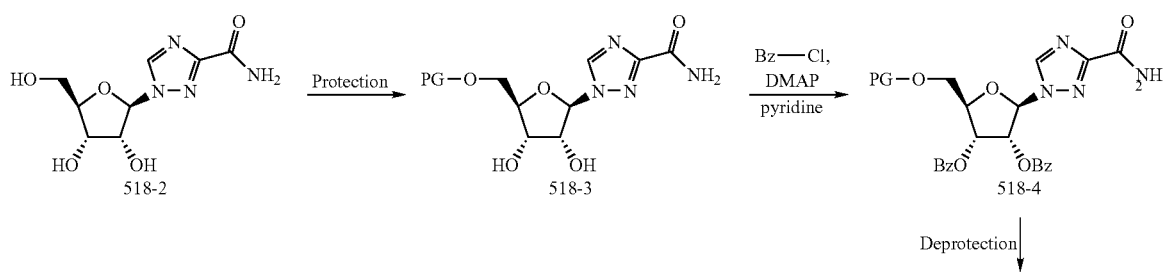

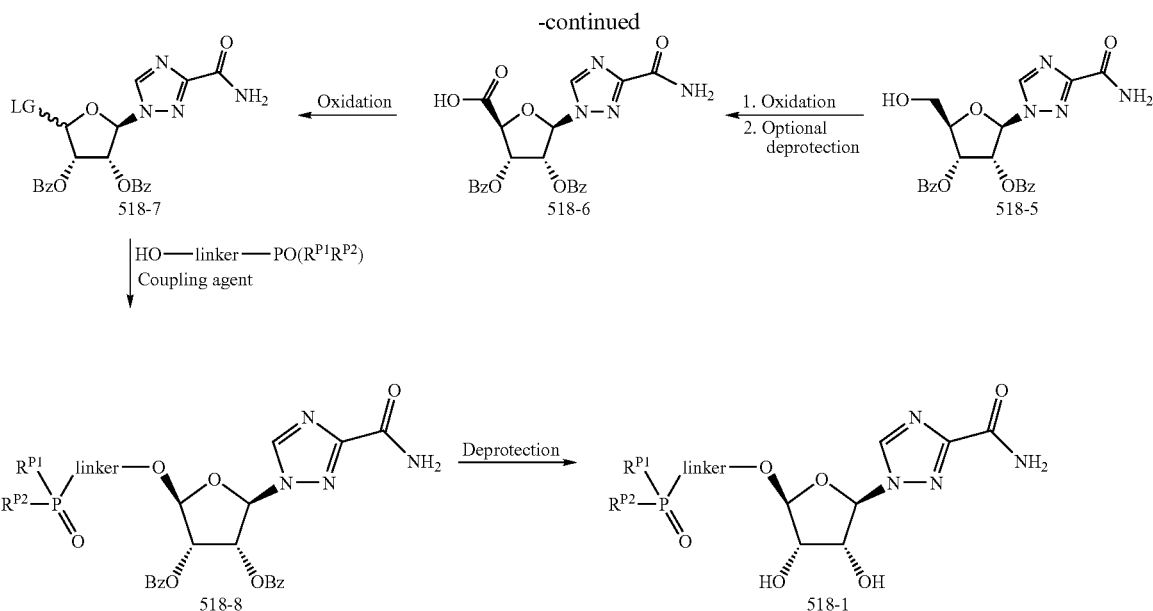
The synthesis of 3-cyano-1-(2,3,5-tri-O-acetyl-β-D-ribofuranosyl)-1,2,4-triazole (518-2) is described in U.S. 2002/0156030 A1, page 6, paragraph 0078 to paragraph 0079. Using this starting material, one can synthesize carboxamide compound 518-1 (Scheme 518-4) or formamidine compound 518-1 (Scheme 518-5) using the sequences of chemical transformations outlined in Schemes 518-4 and 518-5, respectively.
Scheme 518-5
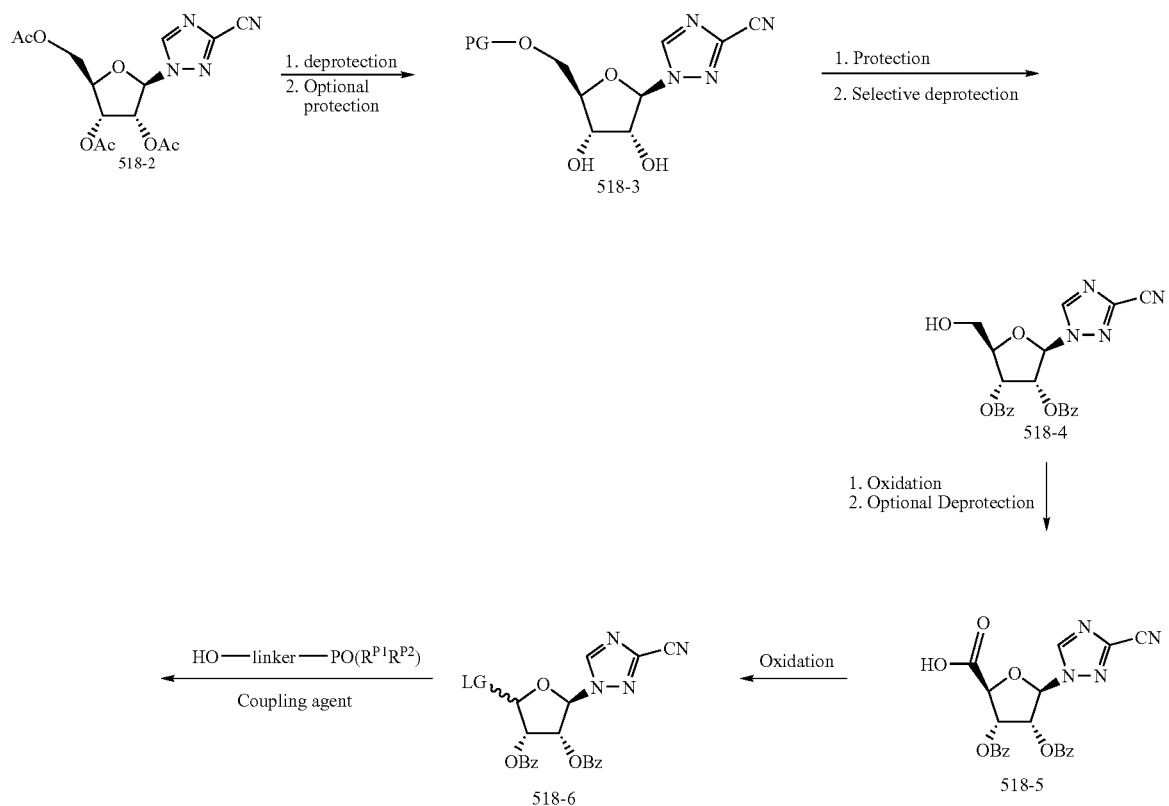

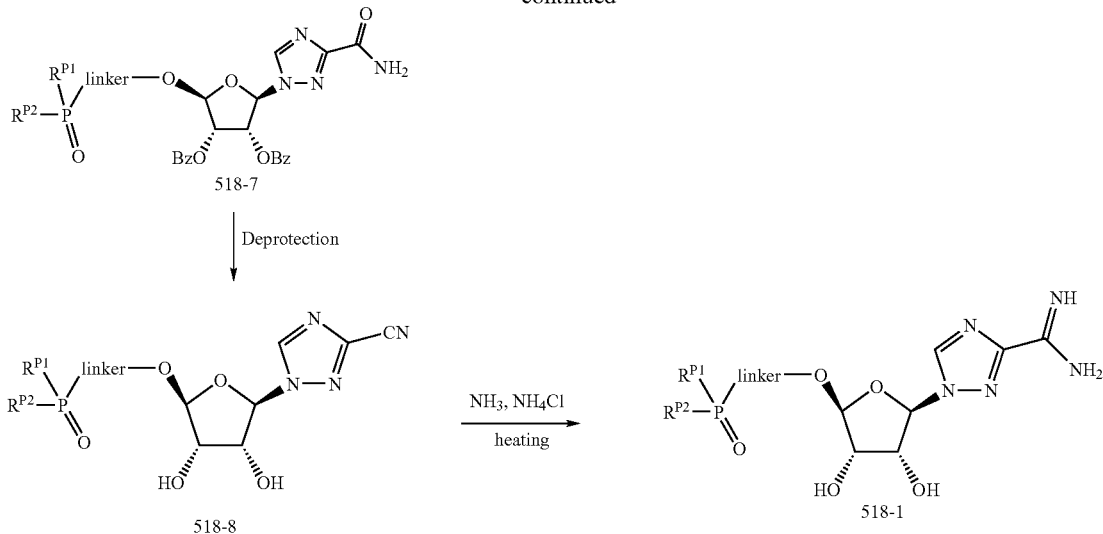

Appropriate protection, deprotection procedures (See Greene and Wuts, (1999) *Protective Groups in Organic Synthesis*,) can be employed to prepare 518-3, in which the 5'-hydroxyl group is protected, while the 2', and 3'-hydroxyl groups are not (Schemes 518-4 and 518-5). Subsequent protection, depretection procedures can introduce protecting groups such as benzoyl group to the 2'- and 3'-hydroxyl, and leave the 5'-hydroxyl group unprotected as in 518-4. Oxidation can convert the primary alcohol in 518-4 to the corresponding carboxylic acid or its ester. An optional deprotection of the ester can give the acid 518-5 as product. Further oxidation using oxidant such as lead tetraacetate can convert 518-5 to 518-6, in which the leaving group is an acetate. Treating 518-6 with an alcohol containing a phosphonate moiety in the presence of appropriate coupling agent, such as trimethylsilyl trifluoromethanesulfonate, will give 518-8 as product. Finally, treating 518-8 with the procedure described in U.S. 2002/0156030 A1, page 6, paragraph 0081, should give 518-1 as product. It is important to point out that $R^{P1}$ and $R^{P2}$ in 518-7, 518-8 and 518-1 do not need to be the same.

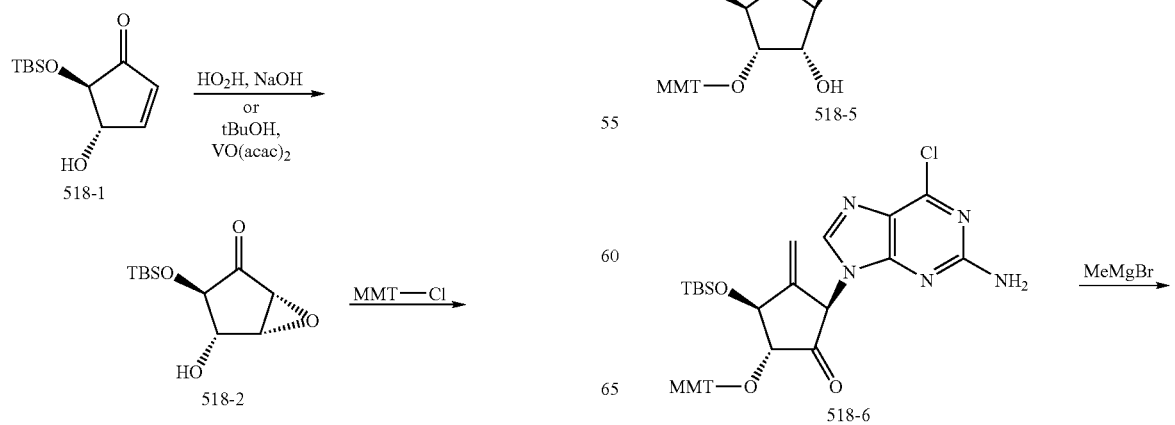

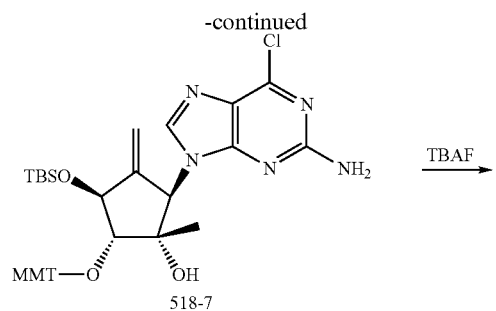

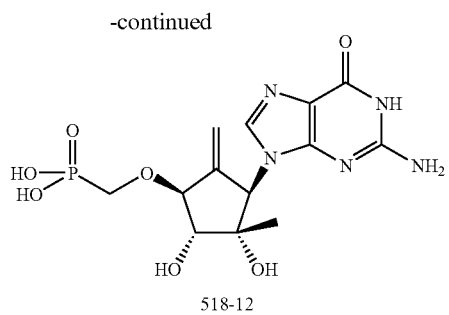

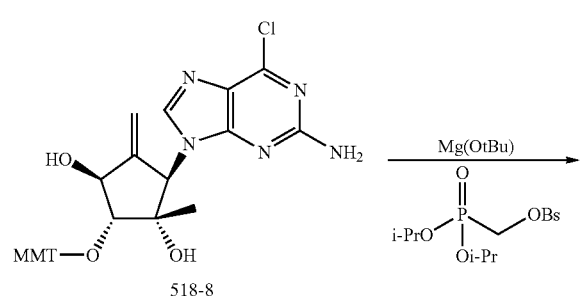

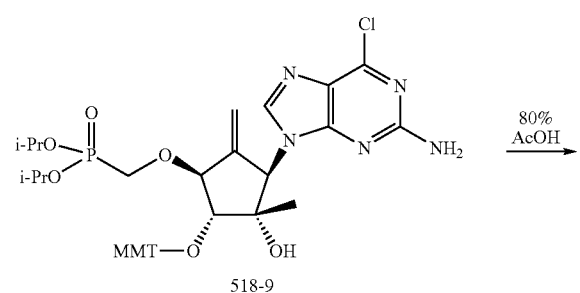

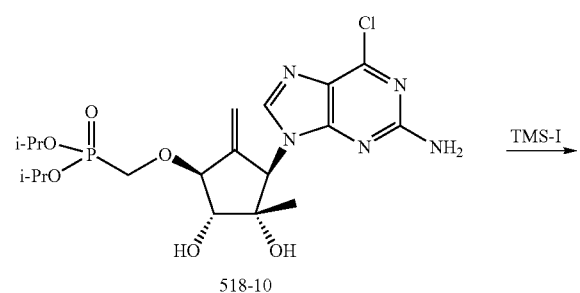

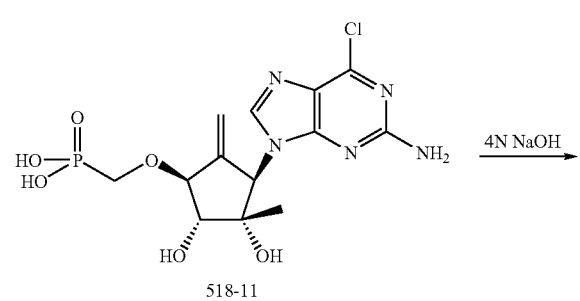

A solution of tert-butyl hydroperoxide (t-BuOOH) in benzene (68%, 3 eq) is added dropwise to a solution of allylic alcohol 518-1 (synthesized as described in *Tet. Letters* (1997) 38:2355-58) and VO(acac)$_2$ in benzene (final concentration 0.1 M) at room temperature (Scheme 518-6). After 1 h of stirring at room temperature, saturated aqueous Na$_2$S$_2$O$_3$ is added to the reaction mixture. The resulting solution is extracted with EtOAc, washed with H$_2$O, and dried over sodium sulfate. After removal of solvent, the crude product 518-2 is purified by column chromatography on silica.

Epoxide 518-2 and p-anisylchlorodiphenylmethane (1.5 eq) is dissolved in anhydrous pyridine (0.17 M) and stirred at 25° C. for 2d. Solvents were removed under reduced pressure and the residue dissolved in EtOAc. The organics were washed with water, saturated aqueous NaHCO$_3$, and dried over sodium sulfate. After removal of solvent, the crude product 518-3 is purified by column chromatography on silica.

To a solution of methyltriphenylphosphonium bromide (2 eq) in anhydrous THF at −78° C. is added n-butyllithium (2.2 eq). The solution is allowed to warm to room temperature and stirred for 20 min. After recooling to −78° C., this solution is added to fully protected epoxide 518-3 in THF (final concentration 0.06 M). The reaction mixture is allowed to warm to room temperature and stirred for 12 h at which point H$_2$O is added and extracted with diethyl ether. The combined organics were dried over sodium sulfate. After removal of solvent, the crude product 518-4 is purified by column chromatography on silica.

Sodium hydride (1 eq) and 2-amino-4-chloro-7H pyrrolo[2,3-d]pyrimidine (1 eq) were dissolved in anhydrous DMF (0.06 M) and stirred at 120° C. for 10 min. A solution of 518-4 in DMF is then added and the reaction mixture is stirred 12 h at 120° C. at which point the solvents were evaporated under reduced pressure. The residue is dissolved in CH$_2$Cl$_2$, washed with H$_2$O, and dried over sodium sulfate. After removal of solvent, the crude product 518-5 is purified by column chromatography on silica.

Compound 518-5 is dissolved in dichloromethane and added to a solution of 1,1,1-tris(acetyloxy)-1,1-dihydro-1,2-benziodoxol-3-(1H)-one (Aldrich, Dess-Martin periodinane, 4 eq) in dichloromethane (final concentration 0.06 M). The reaction mixture is stirred at room temperature for 4 d at which point it is diluted with EtOAc and poured into a solution of sodium thiosulfate in saturated aqueous sodium bicarbonate solution. The organic layer is separated and dried over sodium sulfate. After removal of solvent, the crude product 518-6 is purified by column chromatography on silica.

A solution of ketone 518-6 in anhydrous THF is added to a solution of methylmagnesium bromide (4 eq) in anhydrous THF (0.1 M) at −78° C. The reaction mixture is stirred for 12 h at −60° C. at which point the reaction is quenched with saturated aqueous NH₄Cl solution. The mixture is filtered over celite and washed with EtOAc. The combined organics were washed with saturated aqueous NH₄Cl, water and dried over sodium sulfate. After removal of solvent, the crude product is purified by column chromatography on silica.

A solution of alcohol 518-7 in anhydrous THF (0.06 M) is treated with a solution of tetrabutylammonium fluoride (1.5 eq) in THF at room temperature. The reaction mixture is stirred for 3 h at which point the solvents were evaporated. The crude desilylated diol 518-8 is purified by column chromatography on silica.

To a solution of diol 518-8 and benzenesulfonic acid diisopropoxy-phosphorylmethyl ester (1.2 eq) in anhydrous DMF (0.1 M) is added magnesium tert-butoxide (1 eq). The reaction mixture is heated to 80° C. for 12 h. After cooling to room temperature, 1 N citric acid is added and extracted with EtOAc. The organics were neutralized with saturated aqueous NaHCO₃, washed with saturated aqueous NaCl, and dried over sodium sulfate. After removal of solvent, the crude product 518-9 is purified by column chromatography on silica.

Compound 518-9 is dissolved in 80% acetic acid and stirred 12 h at room temperature. After removal of solvent, the crude product 518-10 is purified by column chromatography on silica.

Phosphonate ester 518-10 and 2,6-lutidine (8 eq) is dissolved in CH₃CN and treated with trimethylsilyliodide (8 eq). After stirring for 3 h at room temperature, triethylamine (8 eq) is added followed by methanol. After removal of solvent, the crude product 518-11 is purified by column chromatography on silica.

Phosphonic diacid 518-11 is dissolved in 1,4-dioxane and treated with 4 N NaOH and heated to 100° C. for 4 h. After cooling to room temperature, the reaction mixture is neutralized with 4N HCl. After removal of solvent, the crude product is purified by column chromatography on silica to provide 518-12.

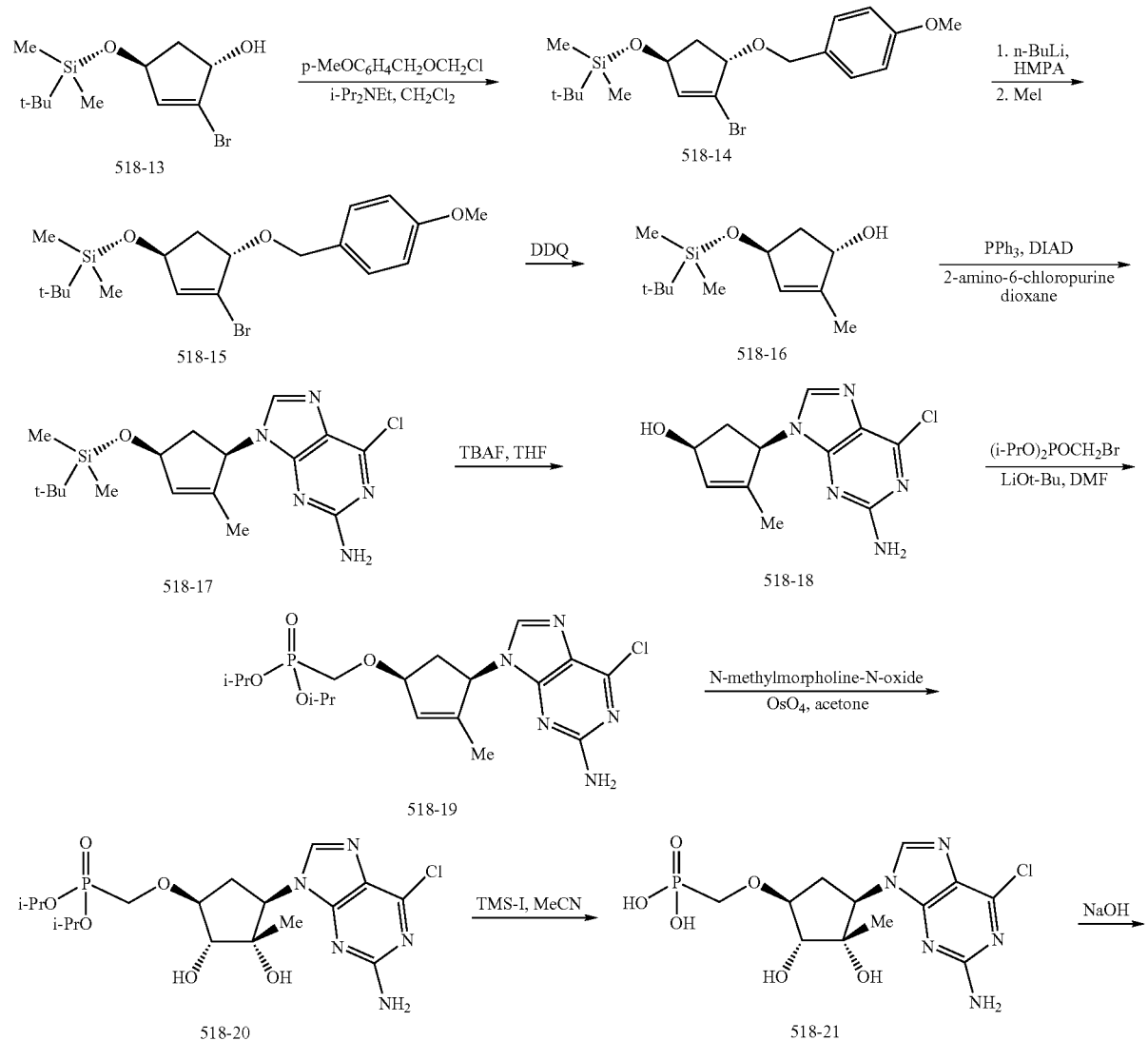

Scheme 518-7

-continued

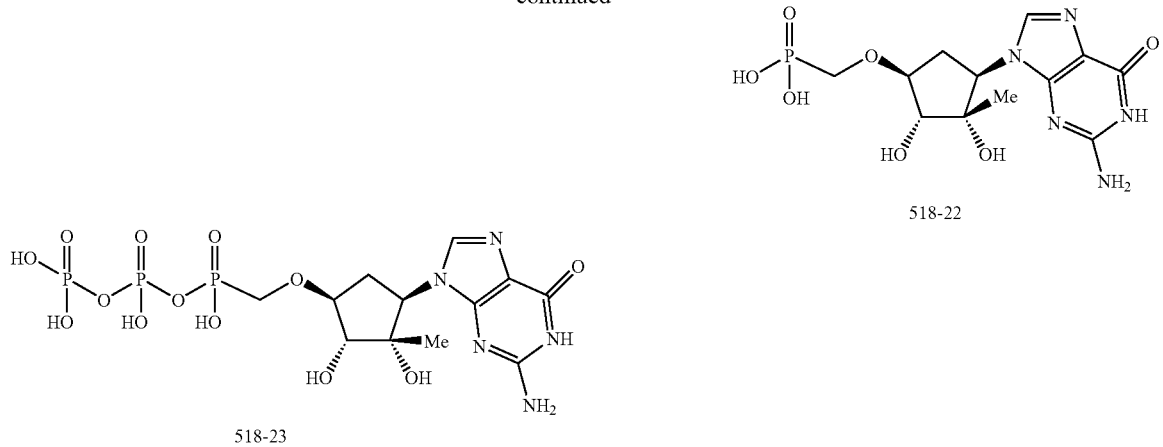

518-22

518-23

Compound 518-13 (Paquette et al *J. Org. Chem.* (1997) 62:1730-1736) is treated with p-methoxybenzyl bromide (1.5 eq.), sodium hydride (1.4 eq) in dry DMF at room temperature (Scheme 518-7). The reaction is monitor by TLC for the disappearance of 518-13. The reaction is quenched by the addition of a saturated aqueous solution of ammonium chloride. Extraction by diethyl ether affords a crude product, which can be purified by silica gel chromatography to give 518-14.

A solution of 518-14 in THF is added dropwise to a solution of n-BuLi (1.2 eq) in THF cooled at −78° C. under a nitrogen atmosphere. The solution is stirred for 1 h at −78° C. Excess of HMPA (1.4 eq) is added. After 10 min, a solution of MeI (5 eq) in THF is added. After another 5 h at −78° C., 20% aqueous $NaH_2PO_4$ is added, and the mixture is warmed to room temperature. Extraction with diethyl ether gives a crude product, which is purified by silica gel chromatography to give 518-15.

Dichlorodicyanoquinone (DDQ) is added to a mixture of compound 518-15 in dichloromethane and water. After stirring at room temperature for 2 h. The mixture is extracted with dichloromethane to give a crude product, which is purified by silica gel chromatography to give 518-16.

To a solution of 518-16 in dioxane, is added triphenylphosphine (2 eq.), 2-amino-6-chloropurine (2 eq) at room temperature. Diisopropyl azodicarboxylate (2 eq, DIAD) is added dropwise via syringe. The mixture is stirred at room temperature for another 3 h. Water is added to quench the reaction. Extraction with ethyl acetate gives a crude product, which is purified by silica gel chromatography to give 518-17.

Alternatively, a nucleobase may be added by the methods described in Crimmins, M. T. (1998) *Tetrahedron* 54:9229-9272, such as palladium coupling to a cyclopentyl acetate.

To a solution of compound 518-17 in THF is added a 1 M solution of tetrabutylammonium fluoride (1.2 eq, TBAF) at room temperature. After another few hours, a saturated solution of ammonium chloride is added. Extraction with ethyl acetate gives a crude product, which is purified by silica gel chromatography to give 518-18.

Compound 518-18, diethyl bromomethylphosphonate (1.5 eq), and lithium t-butoxide (1.5 eq) are added to DMF sequentially. The mixture is stirred at 80° C. for several hours. After the mixture is cooled to room temperature, a 1 M solution of $KH_2PO_4$ is added. Extraction with ethyl acetate gives a crude product, which is purified by silica gel chromatography to give 518-19.

To a solution of 518-19 in acetone, is added N-methylmorpholine N-oxide (2 eq) and osmium tetraoxide (0.2 eq). The mixture is stirred at room temperature for 16 h. A 1 M aqueous solution of sodium sulfite is added. After stirring at room temperature for another hour, the mixture is evaporated to remove most of acetone. The aqueous residue is frozen and lyophilized to give a crude product, which is purified by reversed phase HPLC to give 518-20.

Iodotrimethylsilane (8 eq, TMS-1) is added to a mixture of 518-20, 2,6-lutidine (8 eq) and acetonitrile. After stirring at room temperature for 2 h, the mixture is poured onto ice. The mixture is then frozen and lyophilized to give a residue, which is purified by reversed phase HPLC to give 518-21.

518-21 is dissolved in 4 N aqueous NaOH and refluxed for several hours. The mixture is cooled to room temperature, neutralized with 4 N HCl, and purified with reversed phase HPLC to give 518-22.

Compound 518-22 can be converted to the corresponding diphosphophosphonate 518-23, and prodrugs using known procedures.

Scheme 518-8

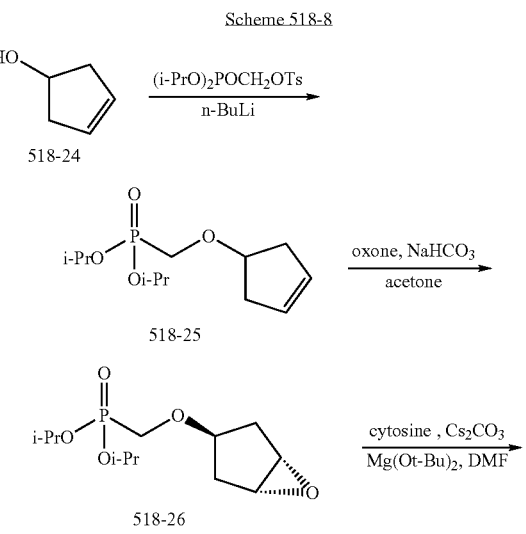

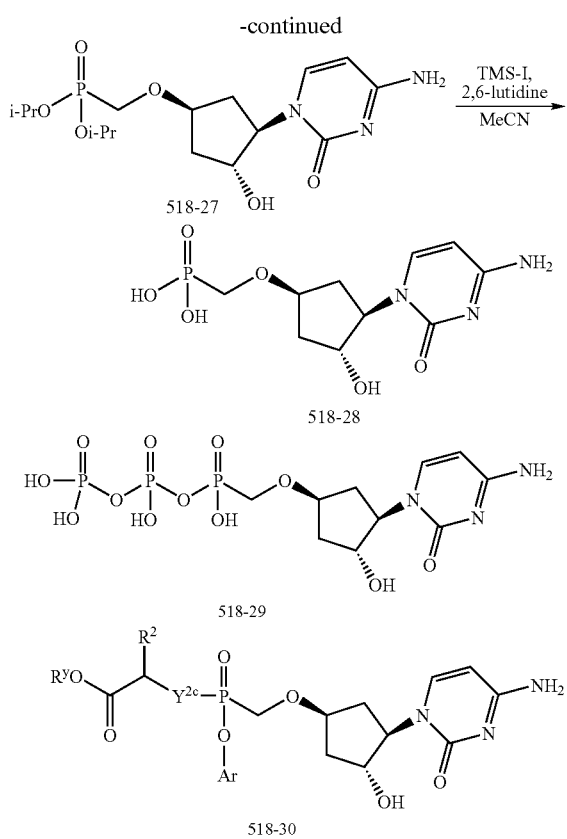

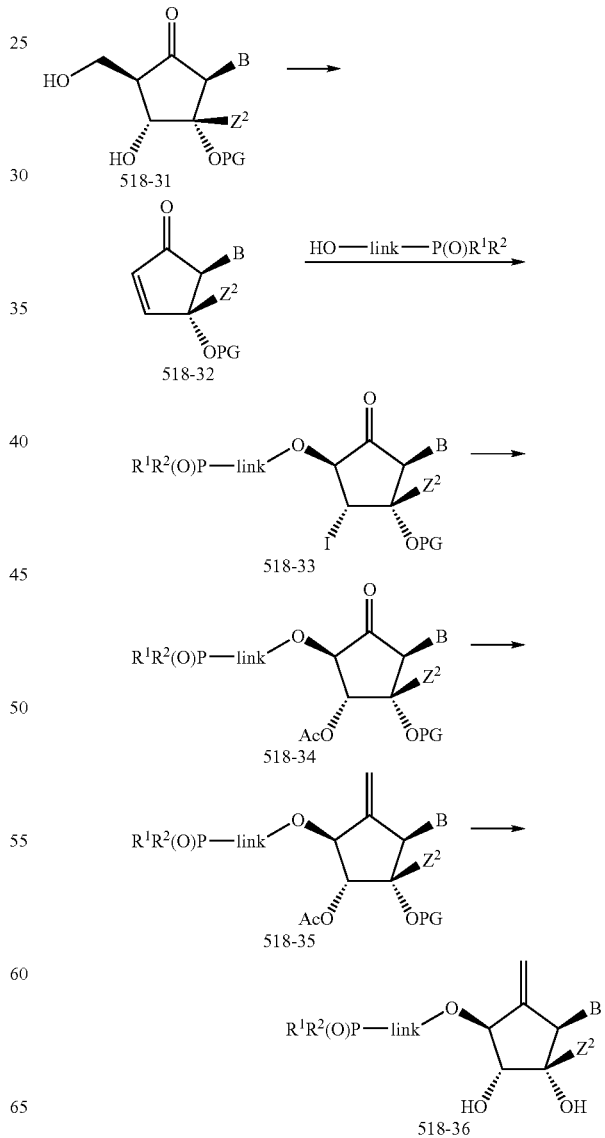

The conversion from 518-27 to 518-28 is described in Scheme 518-2 above. The conversion of 518-28 to the corresponding diphosphophosphonate 518-29 and phosphorus prodrugs, e.g. 518-30 can be accomplished using procedures described herein.

Cyclopentyl intermediate 518-31 may be prepared by procedures analogous to those described in U.S. Pat. No. 5,206,244 and U.S. Pat. No. 5,340,816 (Scheme 518-4). Diol 518-31 is converted to cyclopentenone 518-32 and treated with IBr in the presence of the appropriate phosphonate alcohol to give 518-33. Iodide 518-33 is displaced with inversion to give cyclopentanone intermediate 518-34. Nysted methylenation (U.S. Pat. No. 3,865,848; *Aldrichim. Acta* (1993) 26:14) provides exocyclic methylene 518-35, which may be deprotected to give 518-36.

Cyclopentanone 518-34 may be a versatile intermediate to form other compounds of the invention by reduction to cyclopentyl 518-37, or Wittig or Grubb olefination to alkenyl 518-38.

3-Cyclopenten-1-ol 518-24 (108 uL, 1.2 mmol, 1.2 eq) is dissolved in 5 mL of dry THF (Scheme 518-8). The solution is cooled to 0° C. A 1.35 M solution of n-BuLi (0.89 mL, 1.2 mmol, 1.2 eq) is added via syringe. After 10 min, diisopropylphosphonomethyl p-toluenesulfonate (350 mg, 1.0 mmol, 1.0 eq) is added. The mixture is stirred in a 45° C. bath for 3.5 h. The reaction is quenched with a pH 7 aqueous phosphate buffer. Extraction with diethyl ether gave a crude product, which is purified by silica gel chromatography (eluted with 45% ethyl acetate in hexane) to give 178 mg of 518-25 (68%).

To a solution of 518-25 (168 mg, 0.69 mmol, 1 eq) in 12 mL of acetone, is added 273 mg of NaHCO$_3$ in 8 mL of water. The mixture is then cooled to 0° C. Oxone (519 mg, 0.85 mmol, 1.3 eq) in 4 mL of water is added over 5 min in portions. The mixture is stirred vigorously for 2.5 h. The mixture is then evaporated in vacuo to remove most of the acetone. The aqueous residue is extracted with ethyl acetate to give a crude product, which is purified by silica gel chromatography to give 518-26 as a clear oil.

To a solution of 518-26 (21 mg, 0.076 mmol, 1.0 eq) in 0.25 mL of DMF, is added cytosine (13 mg, 1.5 eq) and cesium carbonate (6 mg, 0.25 eq) and magnesium t-butoxide. The mixture is heated to 140-° C. for several hours. After cooling to room temperature, the reaction mixture is purified by reversed phase HPLC to give 12.5 mg of 518-27 (42%). $^1$H NMR (CDCl$_3$): δ 9.60 (br s, 1H), 8.96 (br s, 1H), 7.87 (d, 1H), 6.21 (d, 1H), 4.84 (m, 1H), 4.78 (m, 2H), 4.43 (m, 1H), 4.08 (s, 1H), 3.72 (m, 2H), 2.82 (m, 1H), 2.33 (m, 1H), 1.83 (m, 2H), 1.38 (m, 12H) ppm.

Alternatively, the methods in WO 03/105770 can be applied to add a nucleobase with a nucleophilic amine to a cycopentyl epoxide.

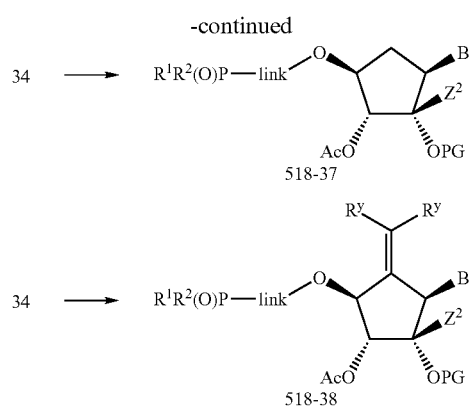

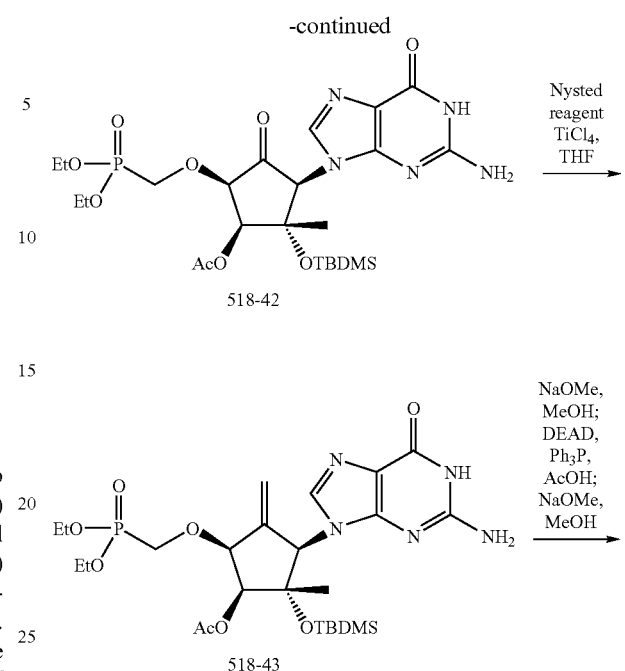

Scheme 518-10 shows intermediate 518-39 is converted to guanosyl cyclopentenone 518-40 (*J. Am. Chem. Soc.* (1972) 94:3213), then treated with IBr and diethyl phosphomethanol to furnish iodide 518-41 (*J. Org. Chem.* (1991) 56:2642) Nucleophilic substitution with AgOAc affords acetate 518-42. After methylenation using the procedure of Nysted (U.S. Pat. No. 3,865,848; *Aldrichim. Acta* 1993, 26, 14), to give 518-43, the acetate group is removed by the addition of sodium methoxide and the resulting alcohol is inverted by the Mitsunobo protocol, and a second acetate deprotection produces 518-44. Desilylation with tetra-butylammonium fluoride (TBAF) of 518-44 will yield 518-45.

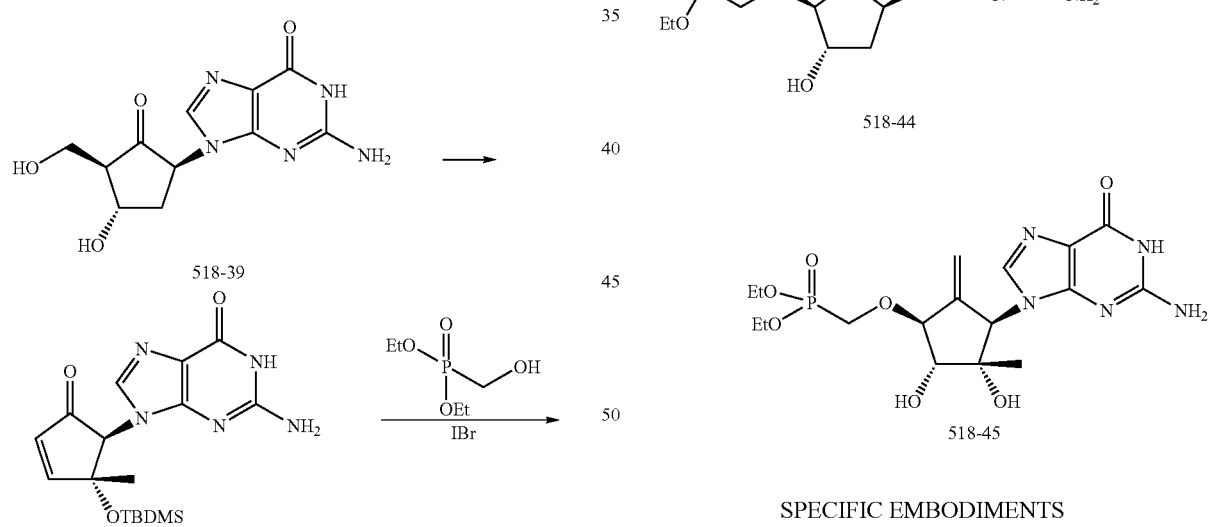

SPECIFIC EMBODIMENTS

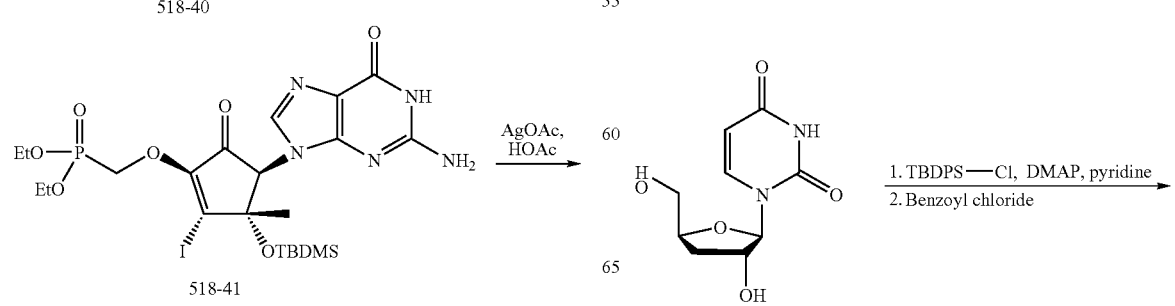

-continued

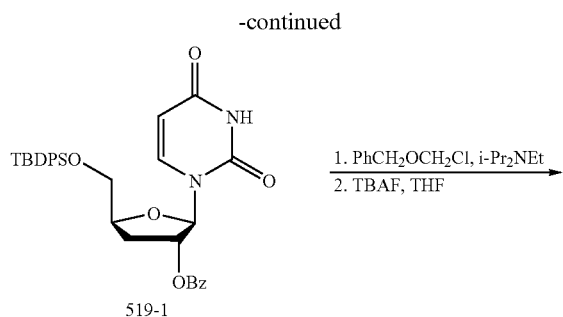
519-1

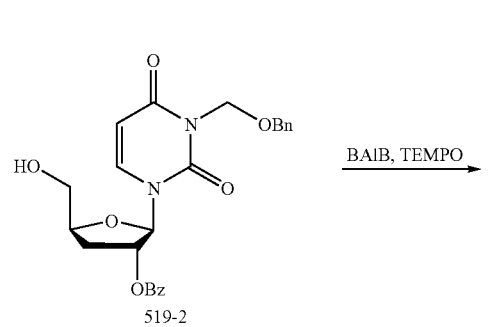
519-2

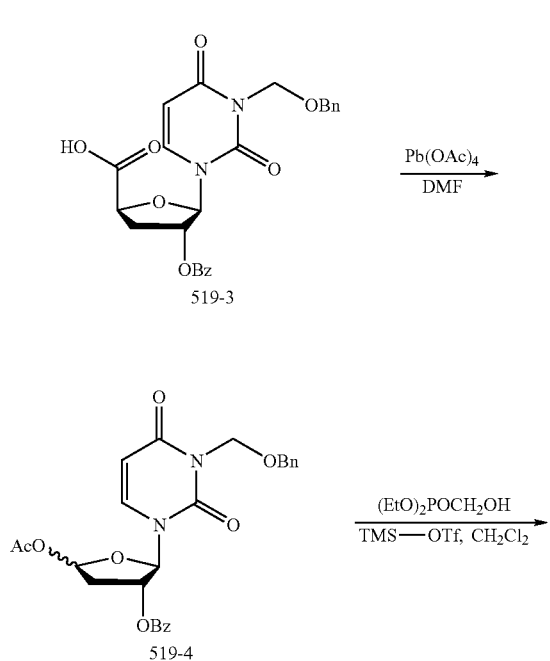
519-3

519-4

519-5a

-continued

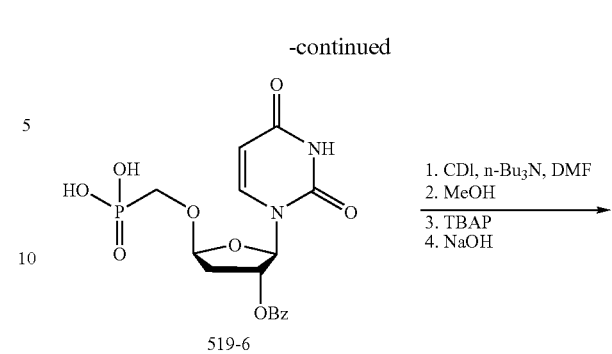
519-6

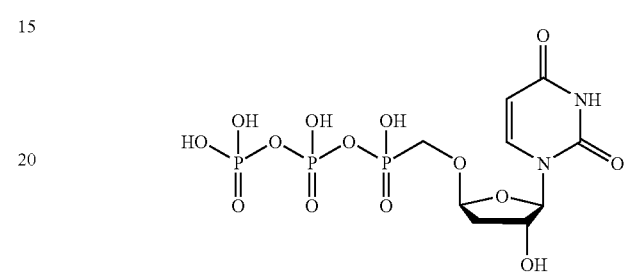
519-7

Example 519

Synthesis of Exemplary Compounds of the Invention

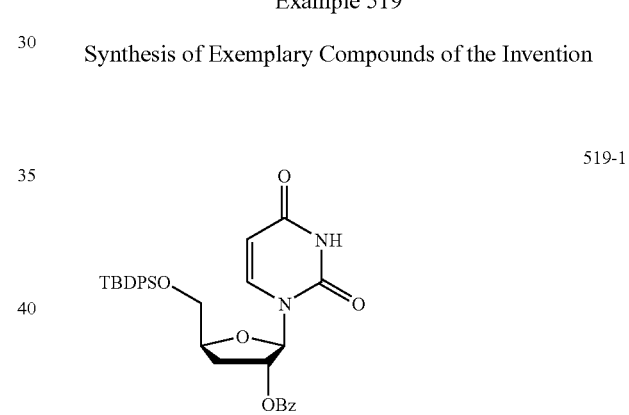
519-1

Synthesis of 519-1: To a solution of 3'-deoxyuridine (995 mg, 4.36 mmol) in 8 mL of anhydrous pyridine was added t-butyldiphenylsilyl chloride (TBDPS-Cl, 1.38 g, 5.01 mmol), and 4-dimethylaminopyridine (DMAP, 27 mg, 0.22 mmol). The mixture was stirred at 23 C for 14 h and then cooled to 0 C in a ice-water bath. To this mixture was added benzoyl chloride (735 mg, 0.61 mL, 5.2 mmol). The mixture was warmed to 23° C. and stirred for another 2 h. The mixture was concentrated in vacuo to give a paste, which was partitioned between water and ethyl acetate. The aqueous later was extracted once with ethyl acetate. The combined ethyl acetate layer was washed sequentially with 1 M aqueous citric acid, saturated sodium bicarbonate, and brine. It was dried over anhydrous sodium sulfate and concentrated in vacuo to give a crude product as a yellow oil. Purification by silica gel chromatography (15-65% ethyl acetate in hexane) gave a colorless oil. Yield 1.35 g (54%). $^1$H NMR (DMSO-d6): δ 11.38 (s, 1H), 8.01 (d, J=7.9 Hz, 2H), 7.77 (d, J=8.2 Hz, 1H), 7.70-7.40 (m, 13H), 5.99 (s, 1H), 5.58 (m, 1H), 7.34 (d, J=8.2 Hz, 1H), 4.47 (m, 1H), 4.03 (m, 1H), 3.84 (m, 1H), 2.43 (m, 1H), 2.21 (m, 1H), 1.03 (s, 9H) ppm. MS (m/z) 571.1 (M+H$^+$), 593.3 (M+Na$^+$).

Example 520

Synthesis of Exemplary Compounds of the Invention

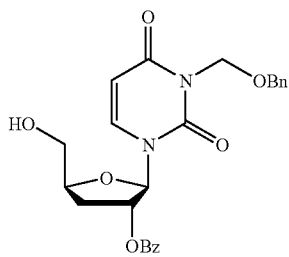

520-2

Synthesis of 520-2: To a solution of 519-1 (1.31 g, 2.3 mmol) in 5 mL of anhydrous N,N-dimethylformamide was added benzyl chloromethyl ether (0.54 g, 3.45 mmol), N,N-diisopropylethylamine (446 mg, 0.60 mL, 3.45 mmol). The mixture was stirred at 23° C. for 4 h. Water was added. The mixture was extracted with ethyl acetate. The organic layer was washed sequentially with 1 M aqueous citric acid, saturated sodium bicarbonate, and brine. It was dried over anhydrous sodium sulfate and concentrated in vacuo to give a crude product as a yellow oil, which was used in the next step without further purification.

The crude product obtained above was dissolved in 9 mL of THF. The solution was cooled to 0 C. A 1 M solution of TBAF (4.6 mL, 4.6 mmol) was added via syringe. The mixture was warmed to 23° C. and stirred for another 2 h. An additional 2.3 mL of 1 M TBAF was added. The mixture was stirred for another 2 h at 23 C. Saturated aqueous ammonium chloride was added to the solution. The mixture was evaporated in vacuo to remove most of THF. The aqueous phase was extracted with ethyl acetate. The aqueous layer was washed with brine. It was then dried over anhydrous sodium sulfate and concentrated in vacuo to give a crude product as a yellow oil. Purification by silica gel chromatography (30-80% ethyl acetate in hexane) gave a white solid. Yield of 520-2: 805 mg (77% for two steps). $^1$H NMR (DMSO-d6): δ 8.04 (m, 3H), 7.67 (t, J=7.3 Hz, 1H), 7.55 (t, J=7.6 Hz, 2H), 7.30 (m, 5H), 5.98 (s, 1H), 5.78 (d, J=7.9 Hz, 1H), 5.55 (m, 1H), 5.31 (s, 2H), 5.22 (m, 1H), 4.57 (s, 2H), 4.41 (m, 1H), 3.80 (m, 1H), 3.60 (m, 1H), 2.31 (m, 1H), 2.15 (m, 1H) ppm. MS (m/z) 453.1 (M+H$^+$), 475.3 (M+Na$^+$).

Example 521

Synthesis of Exemplary Compounds of the Invention

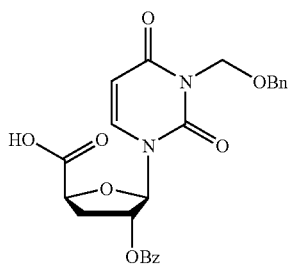

521-3

Synthesis of 521-3: To a solution of 520-2 (800 mg, 1.77 mmol) in 3.5 mL of a 1:1 mixture of acetonitrile/water was added iodobenzene diacetate (1.25 g, 3.89 mmol), and TEMPO (55 mg, 0.35 mmol). The mixture was stirred at 23° C. for 14 h. The mixture was then froze in a −78° C. bath and lyophilized to give a solid residue. This residue was purified by silica gel chromatography (0-15% methanol in dichloromethane). Product 521-3 was obtained as a white solid. Yield: 735 mg (89%). $^1$H NMR (DMSO-d6): δ 8.13 (d, J=7.6 Hz, 1H), 8.03 (d, J=7.7 Hz, 2H), 7.68 (m, 1H), 7.58 (t, J=7.0 Hz, 2H), 7.29 (m, 5H), 6.04 (s, 1H), 5.85 (d, J=8.3 Hz, 1H), 5.62 (m, 1H), 5.31 (s, 2H), 4.87 (m, 1H), 4.58 (s, 2H), 2.40-2.20 (m, 2H) ppm. MS (m/z) 467.1 (M+H$^+$), 489.3 (M+Na$^+$).

Example 522

Synthesis of Exemplary Compounds of the Invention

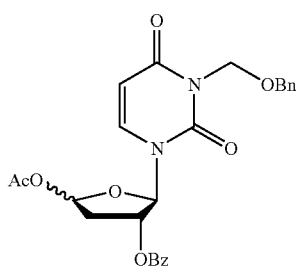

522-4

Synthesis of 522-4: To a deoxygenated solution of 521-3 (730 mg, 1.57 mmol) and pyridine (0.51 mL, 6.26 mmol) in 7 mL of anhydrous DMF, was added lead tetraacetate (3.47 g, 7.83 mmol). The mixture was stirred at 23° C. for 14 h shielded from light. The mixture was diluted with 15 mL of ethyl acetate and 10 mL of water. This mixture filtered through a pad of Celite and separated. The aqueous phase was extracted with another 10 mL of ethyl acetate. The combined ethyl acetate extract was washed with brine, dried over sodium sulfate, and evaporated in vacuo to give the crude product as an oil. The crude product 522-4 was purified by silica gel chromatography (10-50% ethyl acetate in hexane). Products of two diastereomers were obtained as a white foam. Yield: 400 mg (53%). $^1$H NMR (DMSO-d6): δ 8.01 (m, 2H), 7.82-7.63 (m, 2H), 7.57 (m, 2H), 7.31 (m, 5H), 6.58 (m, 1H), 6.17 (m, 1H), 5.83 (m, 1H), 5.65 (m, 1H), 5.31 (s, 2H), 4.59 (s, 2H), 2.76 and 2.28 (m, 1H), 2.10 (m, 1H), 2.07 (s, 3H) ppm. MS (m/z) 481.0 (M+H$^+$), 503.3 (M+Na$^+$).

Example 523

Synthesis of Exemplary Compounds of the Invention

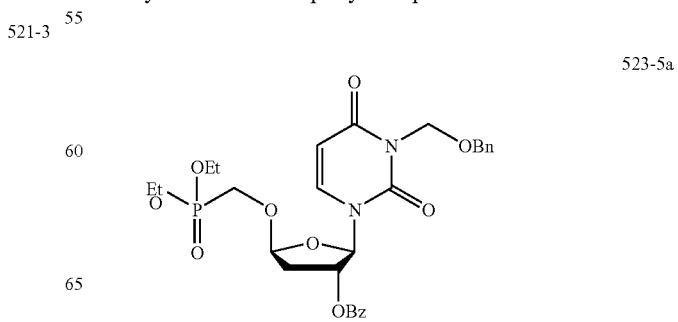

523-5a

-continued

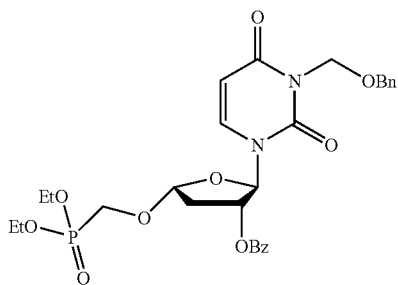

523-5b

Synthesis of 523-5a: To a solution of 522-4 (300 mg, 0.63 mmol) in 6 mL of anhydrous dichloromethane was added diethyl hydroxymethylphosphonate (0.37 mL, 2.5 mmol), followed by trimethylsilyl trifluoromethanesulfonate (0.34 mL, 1.88 mmol). The mixture was stirred at 23° C. for 6 h. Triethylamine (0.44 mL, 3.15 mmol) was added, followed by water. The mixture was extracted with ethyl acetate. The organic layer was washed with 1 M aqueous citric acid, saturated sodium bicarbonate, and brine. It was then dried over anhydrous sodium sulfate, and evaporated in vacuo to give a residue. This crude product was purified by silica gel chromatography (75-95% ethyl acetate in hexane) to give two products, which were diastereomers of each other shown above (523-5a and 523-5b). Yield of 523-5a: 53 mg (14%). Yield of 523-5b: 129 mg (35%).

Analytical data for 5a: $^1$H NMR (Acetonitrile-d3): δ 8.04 (d, J=7.0 Hz, 2H), 7.77 (d, J=7.9 Hz, 1H), 7.69 (t, J=7.5 Hz, 1H), 7.53 (m, 2H), 7.33 (m, 5H), 6.38 (d, J=4.0 Hz, 1H), 5.80 (d, J=8.2 Hz, 1H), 5.63 (m, 1H), 5.52 (m, 1H), 5.41 (s, 2H), 4.64 (s, 2H), 4.17 (m, 4H), 4.08 (dd, J=13.8, 10.1 Hz, 1H), 3.92 (dd, J=13.7, 9.5 Hz, 1H), 2.66-2.42 (m, 2H), 1.35 (t, J=7.0 Hz, 6H) ppm. MS (m/z) 589.2 (M+H$^+$), 611.3 (M+Na$^+$). Stereochemistry of 523-5a was confirmed by additional 2D NMR experiments.

Analytical data for 523-5b: $^1$H NMR (Acetonitrile-d3): δ 8.08 (d, J=7.3 Hz, 2H), 7.69 (t, J=7.5 Hz, 1H), 7.55 (m, 2H), 7.43 (d, J=8.2 Hz, 1H), 7.36 (m, 5H), 6.11 (d, J=2.4 Hz, 1H), 5.77 (d, J=8.3 Hz, 1H), 5.57 (m, 2H), 5.41 (s, 2H), 4.66 (s, 2H), 4.12 (m, 5H), 3.88 (dd, J=14.0, 5.2 Hz, 1H), 2.82 (m, 1H), 2.25 (m, 1H), 1.27 (t, J=7.0 Hz, 6H) ppm. MS (m/z) 589.0 (M+H$^+$), 611.2 (M+Na$^+$).

Example 524

Synthesis of Exemplary Compounds of the Invention

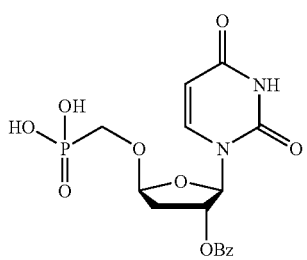

524-6

Synthesis of 524-6: To a solution of 523-5a (110 mg, 0.19 mmol) in in 3 mL of acetonitrile was added 2,6-lutidine (0.43 mL, 3.74 mmol), followed by iodotrimethylsilane (0.53 mL, 3.74 mmol). After stirring at 23 C for 30 min, the mixture was heated to 40° C. and stirred at that temperature for another 4 h. The reaction mixture was cooled to 23° C. Triethylamine (0.52 mL, 3.74 mmol) was added, followed by water (10 mL). The aqueous mixture was extracted twice with 5 mL of diethyl ether. The resulting aqueous solution was frozen in a −78° C. bath and was lyophilized to give a yellow solid. This crude product was purified by reversed phase HPLC to give 524-6 as a light yellow solid. Yield 26 mg (34%). MS (m/z) 411.3 (M−H$^−$).

Example 525

Synthesis of Exemplary Compounds of the Invention

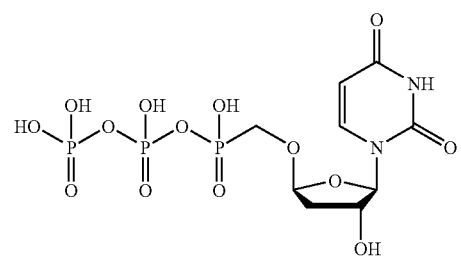

525-7

Synthesis of 525-7: Phosphonate 524-6 (12 mg, 0.029 mmol), carbonyldiimidazole (47 mg, 0.29 mmol), and tri-n-butylamine (5.4 mg, 0.029 mmol) were dissolved in 0.3 mL of anhydrous dimethylformamide (DMF). The mixture was stirred at 23° C. for 4 h. MeOH (0.020 mL) was added and the mixture was stirred for another 30 min. A solution of tributylammonium pyrophosphate (159 mg, 0.29 mmol) in 0.63 mL of anhydrous DMF was added. The resulting mixture was stirred at 23° C. for 14 h. The mixture was evaporated in vacuo to remove most of the DMF. The residue was dissolved in 5 mL of water and was purified by ion-exchange chromatography (DEAE-cellulose resin, 0-50% triethylammonium bicarbonate in water) to give a white solid, which was used directly in the next reaction.

The product obtained above was dissolved in 2 mL of water. A 0.3 mL of a 1 M solution of sodium hydroxide in water was added. The mixture was stirred at 23° C. for 40 min. Acetic acid was added to adjust the pH of the solution to 5. The solution was diluted with water and purified with an ion-exchange column (DEAE-cellulose resin, 0-50% triethylammonium bicarbonate in water) to give diphosphophosphonate 525-7 as a white solid, which is the triethylammonium salt of the structure shown above. Yield 10 mg (45% for two steps). $^1$H NMR (D$_2$O): δ 7.79 (d, J=7.6 Hz, 1H), 5.89 (m, 1H), 5.85 (d, J=7.6 Hz, 1H), 5.41 (m, 1H), 4.49 (m, 1H), 4.02-3.65 (m, 2H), 3.06 (m, 18H), 2.20 (m, 2H), 1.14 (m, 27H) ppm. $^{31}$P NMR (D$_2$O): δ 7.46 (d, 1P), −9.45 (d, 1P), −23.11 (t, 1P) ppm. MS (m/z) 467.0 (M−H$^−$).

Example 526

Synthesis of Exemplary Compounds of the Invention

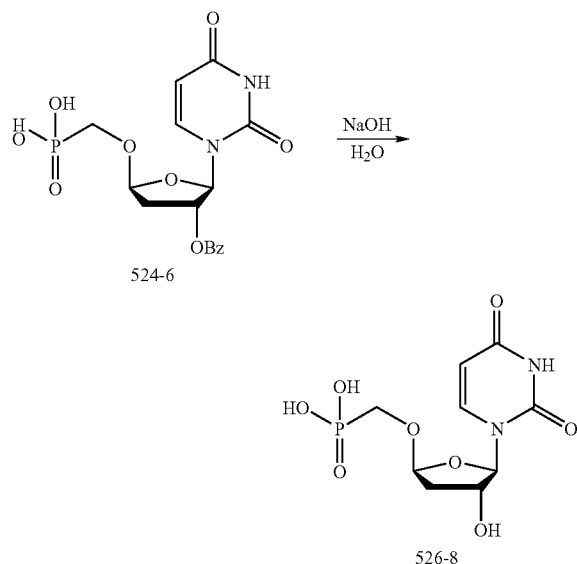

Synthesis of 526-8: To a solution of 524-6 (16 mg, 0.039 mmol) in 0.4 mL of water was added NaOH (7.8 mg, 0.19 mmol). The solution was stirred at 23° C. for 1 h. Acetic acid (0.012 mL) was added to the solution. The mixture was then purified by reversed phase HPLC (eluted with 100% water) to give 4.6 mg of 526-8 as a white solid (38% yield). $^1$H NMR (D$_2$O): δ 7.83 (d, J=8.3 Hz, 1H), 5.86 (d, J=3.4 Hz, 1H), 5.82 (d, J=7.9 Hz, 1H), 4.48 (m, 1H), 3.68 (m, 1H), 3.37 (m, 1H), 2.16 (m, 2H) ppm. $^{31}$P NMR (D$_2$O): δ 12.60 (s, 1P) ppm. MS (m/z) 615.1 (2M-H$^-$).

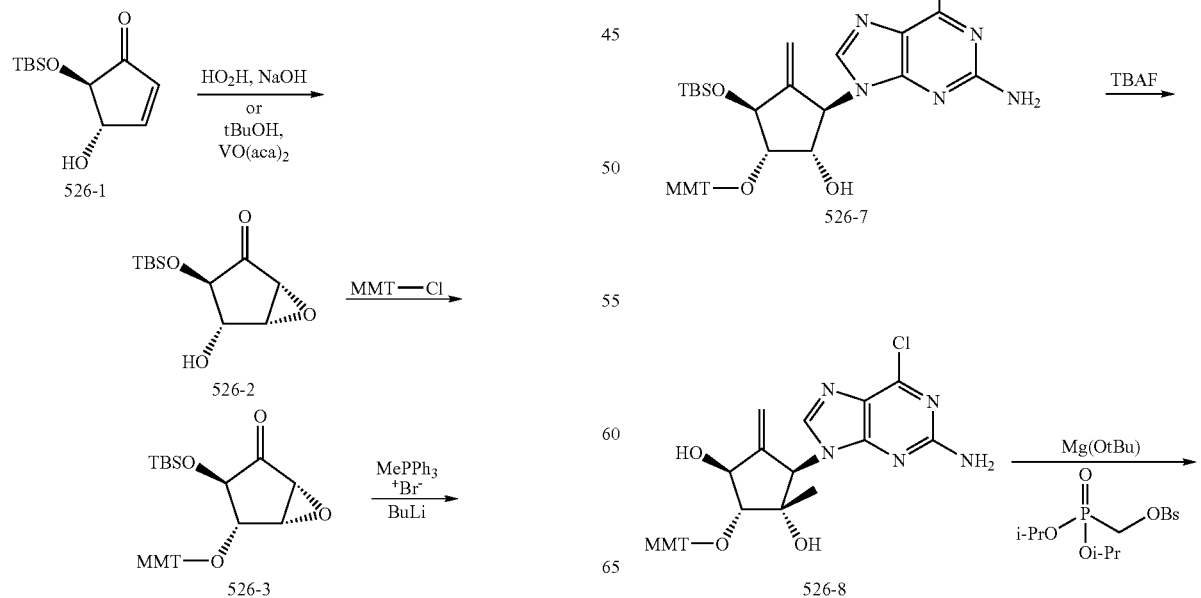

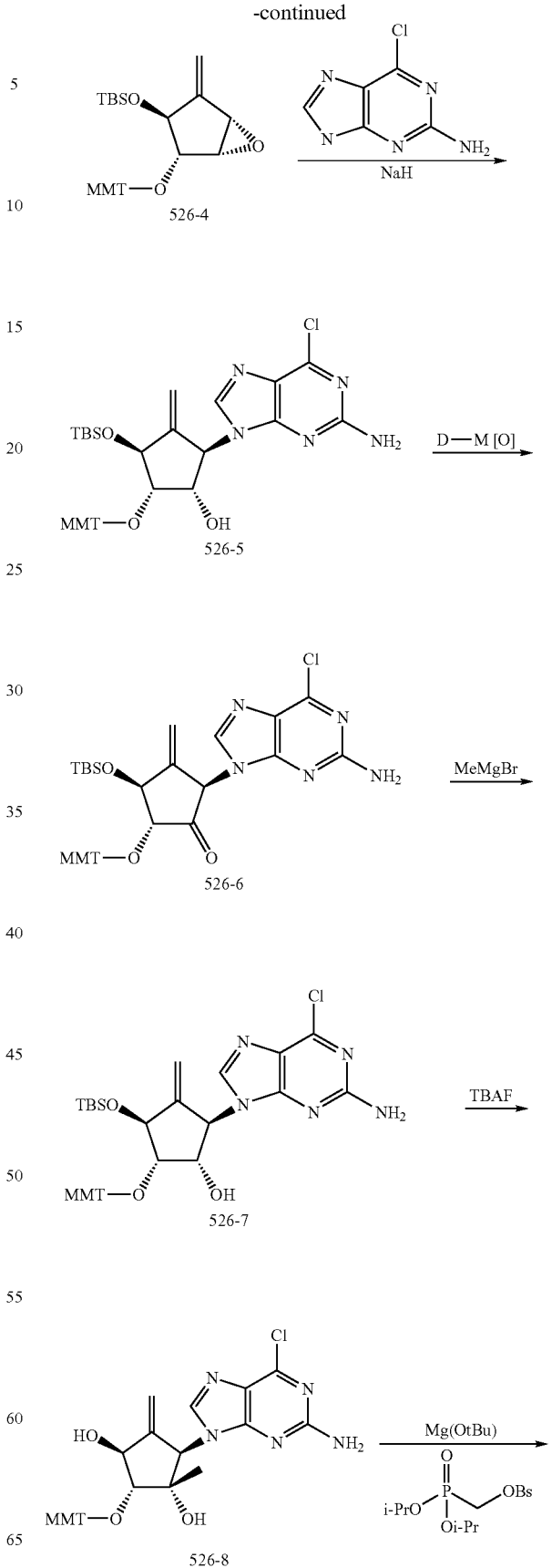

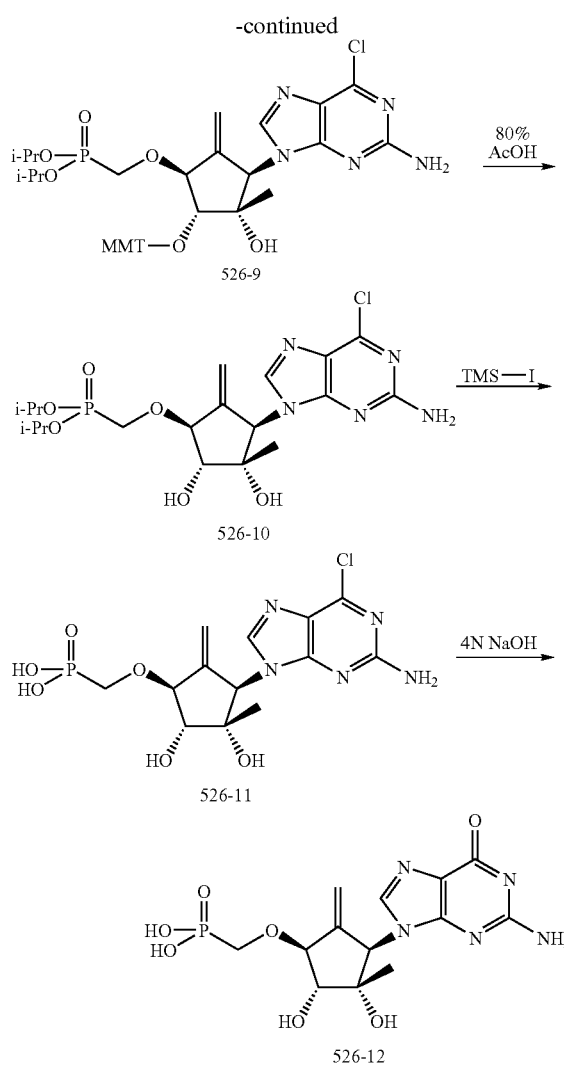

A solution of tert-butyl hydroperoxide (t-BuOOH) in benzene (68%, 3 eq) is added dropwise to a solution of allylic alcohol 526-1 (synthesized as described in *Tet. Lett.*, 38: 2355 (1997)) and VO(acac)$_2$ in benzene (final concentration 0.1 M) at room temperature (Scheme 526-1). After 1 h of stirring at room temperature, saturated aqueous Na$_2$S$_2$O$_3$ is added to the reaction mixture. The resulting solution is extracted with EtOAc, washed with H$_2$O, and dried over sodium sulfate. After removal of solvent, the crude product 526-2 is purified by column chromatography on silica.

Epoxide 526-2 and p-anisylchlorodiphenylmethane (1.5 eq) is dissolved in anhydrous pyridine (0.17 M) and stirred at 25° C. for 2d. Solvents were removed under reduced pressure and the residue dissolved in EtOAc. The organics were washed with water, saturated aqueous NaHCO$_3$, and dried over sodium sulfate. After removal of solvent, the crude product 526-3 is purified by column chromatography on silica.

To a solution of methyltriphenylphosphonium bromide (2 eq) in anhydrous THF at −78° C. is added n-butyllithium (2.2 eq). The solution is allowed to warm to room temperature and stirred for 20 min. After recooling to −78° C., this solution is added to fully protected epoxide 526-3 in THF (final concentration 0.06 M). The reaction mixture is allowed to warm to room temperature and stirred for 12 h at which point H$_2$O is added and extracted with diethyl ether. The combined organics were dried over sodium sulfate. After removal of solvent, the crude product 526-4 is purified by column chromatography on silica.

Sodium hydride (1 eq) and 2-amino-4-chloro-7H pyrrolo[2,3-d]pyrimidine (1 eq) were dissolved in anhydrous DMF (0.06 M) and stirred at 120° C. for 10 min. A solution of 526-4 in DMF is then added and the reaction mixture is stirred 12 h at 120° C. at which point the solvents were evaporated under reduced pressure. The residue is dissolved in CH$_2$Cl$_2$, washed with H$_2$O, and dried over sodium sulfate. After removal of solvent, the crude product 526-5 is purified by column chromatography on silica.

Compound 526-5 is dissolved in dichloromethane and added to a solution of 1,1,1-tris(acetyloxy)-1,1-dihydro-1,2-benziodoxol-3-(1H)-one (Aldrich, Dess-Martin periodinane, 4 eq) in dichloromethane (final concentration 0.06 M). The reaction mixture is stirred at room temperature for 4 d at which point it is diluted with EtOAc and poured into a solution of sodium thiosulfate in saturated aqueous sodium bicarbonate solution. The organic layer is separated and dried over sodium sulfate. After removal of solvent, the crude product 6 is purified by column chromatography on silica.

A solution of ketone 526-6 in anhydrous THF is added to a solution of methylmagnesium bromide (4 eq) in anhydrous THF (0.1 M) at −78° C. The reaction mixture is stirred for 12 h at −60° C. at which point the reaction is quenched with saturated aqueous NH$_4$Cl solution. The mixture is filtered over celite and washed with EtOAc. The combined organics were washed with saturated aqueous NH$_4$Cl, water and dried over sodium sulfate. After removal of solvent, the crude product 526-7 is purified by column chromatography on silica.

A solution of alcohol 7 in anhydrous THF (0.06 M) is treated with a solution of tetrabutylammonium fluoride (1.5 eq) in THF at room temperature. The reaction mixture is stirred for 3 h at which point the solvents were evaporated. The crude desilylated diol 526-8 is purified by column chromatography on silica.

To a solution of diol 526-8 and benzenesulfonic acid diisopropoxy-phosphorylmethyl ester (1.2 eq) in anhydrous DMF (0.1 M) is added magnesium tert-butoxide (1 eq). The reaction mixture is heated to 80° C. for 12 h. After cooling to room temperature, 1 N citric acid is added and extracted with EtOAc. The organics were neutralized with saturated aqueous NaHCO$_3$, washed with saturated aqueous NaCl, and dried over sodium sulfate. After removal of solvent, the crude product 526-9 is purified by column chromatography on silica.

Compound 526-9 is dissolved in 80% acetic acid and stirred 12 h at room temperature. After removal of solvent, the crude product 526-10 is purified by column chromatography on silica.

Phosphonate ester 526-10 and 2,6-lutidine (8 eq) is dissolved in CH$_3$CN and treated with trimethylsilyliodide (8 eq). After stirring for 3 h at room temperature, triethylamine (8 eq) is added followed by methanol. After removal of solvent, the crude product 526-11 is purified by column chromatography on silica.

Phosphonic diacid 526-11 is dissolved in 1,4-dioxane and treated with 4 N NaOH and heated to 100° C. for 4 h. After cooling to room temperature, the reaction mixture is neutralized with 4N HCl. After removal of solvent, the crude product is purified by column chromatography on silica to provide 526-12.

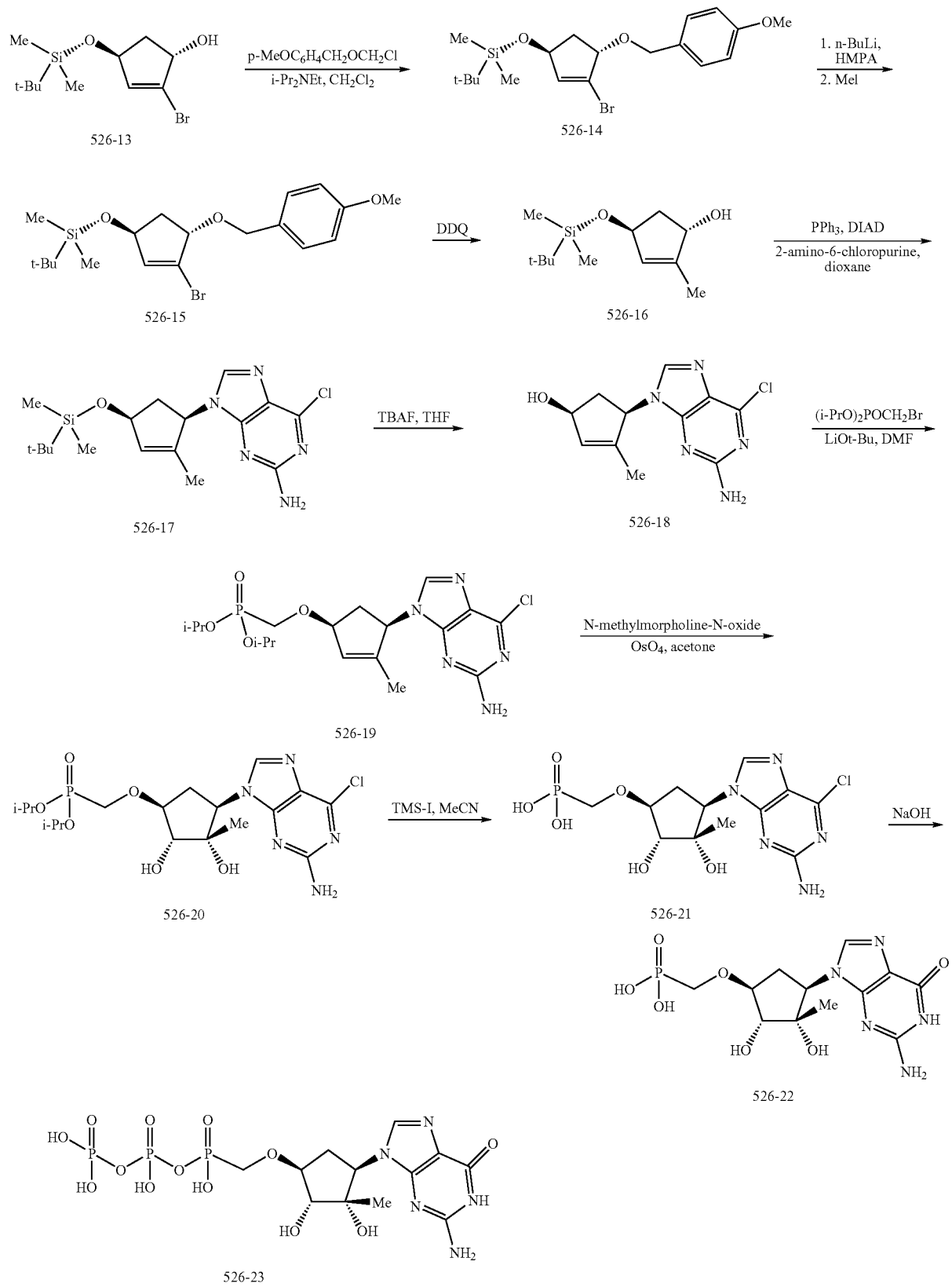
Scheme 526-2

Compound 526-13 (Paquette et al in *J. Org. Chem.* (1997) 62:1730-1736) is treated with p-methoxybenzyl bromide (1.5 eq.), sodium hydride (1.4 eq) in dry DMF at room temperature (Scheme 526-2). The reaction is monitor by TLC for the disappearance of 526-13. The reaction is quenched by the addition of a saturated aqueous solution of ammonium chloride. Extraction by diethyl ether affords a crude product, which can be purified by silica gel chromatography to give 526-14.

A solution of 526-14 in THF is added dropwise to a solution of n-BuLi (1.2 eq) in THF cooled at −78° C. under a nitrogen atmosphere. The solution is stirred for 1 h at −78° C. Excess of HMPA (1.4 eq) is added. After 10 min, a solution of MeI (5 eq) in THF is added. After another 5 h at −78° C., 20% aqueous $NaH_2PO_4$ is added, and the mixture is warmed to room temperature. Extraction with diethyl ether gives a crude product, which is purified by silica gel chromatography to give 526-15.

Dichlorodicyanoquinone (DDQ) is added to a mixture of compound 526-15 in dichloromethane and water. After stirring at room temperature for 2 h. The mixture is extracted with dichloromethane to give a crude product, which is purified by silica gel chromatography to give 526-16.

To a solution of 526-16 in dioxane, is added triphenylphosphine (2 eq.), 2-amino-6-chloropurine (2 eq) at room temperature. Diisopropyl azodicarboxylate (2 eq, DIAD) is added dropwise via syringe. The mixture is stirred at room temperature for another 3 h. Water is added to quench the reaction. Extraction with ethyl acetate gives a crude product, which is purified by silica gel chromatography to give 526-17.

To a solution of compound 526-17 in THF is added a 1 M solution of tetrabutylammonium fluoride (1.2 eq, TBAF) at room temperature. After another few hours, a saturated solution of ammonium chloride is added. Extraction with ethyl acetate gives a crude product, which is purified by silica gel chromatography to give 526-18.

Compound 526-18, diethyl bromomethylphosphonate (1.5 eq), and lithium t-butoxide (1.5 eq) are added to DMF sequentially. The mixture is stirred at 80° C. for several hours. After the mixture is cooled to room temperature, a 1 M solution of $KH_2PO_4$ is added. Extraction with ethyl acetate gives a crude product, which is purified by silica gel chromatography to give 526-19.

To a solution of 526-19 in acetone, is added N-methylmorpholine N-oxide (2 eq) and osmium tetraoxide (0.2 eq). The mixture is stirred at room temperature for 16 h. A 1 M aqueous solution of sodium sulfite is added. After stirring at room temperature for another hour, the mixture is evaporated to remove most of acetone. The aqueous residue is frozen and lyophilized to give a crude product, which is purified by reversed phase HPLC to give 526-20.

Iodotrimethylsilane (8 eq, TMS-I) is added to a mixture of 526-20, 2,6-lutidine (8 eq) and acetonitrile. After stirring at room temperature for 2 h, the mixture is poured onto ice. The mixture is then frozen and lyophilized to give a residue, which is purified by reversed phase HPLC to give 526-21.

526-21 is dissolved in 4 N aqueous NaOH and refluxed for several hours. The mixture is cooled to room temperature, neutralized with 4 N HCl, and purified with reversed phase HPLC to give 526-22.

Compound 526-22 can be converted to the corresponding diphosphophosphonate 526-23, and prodrugs using known procedures.

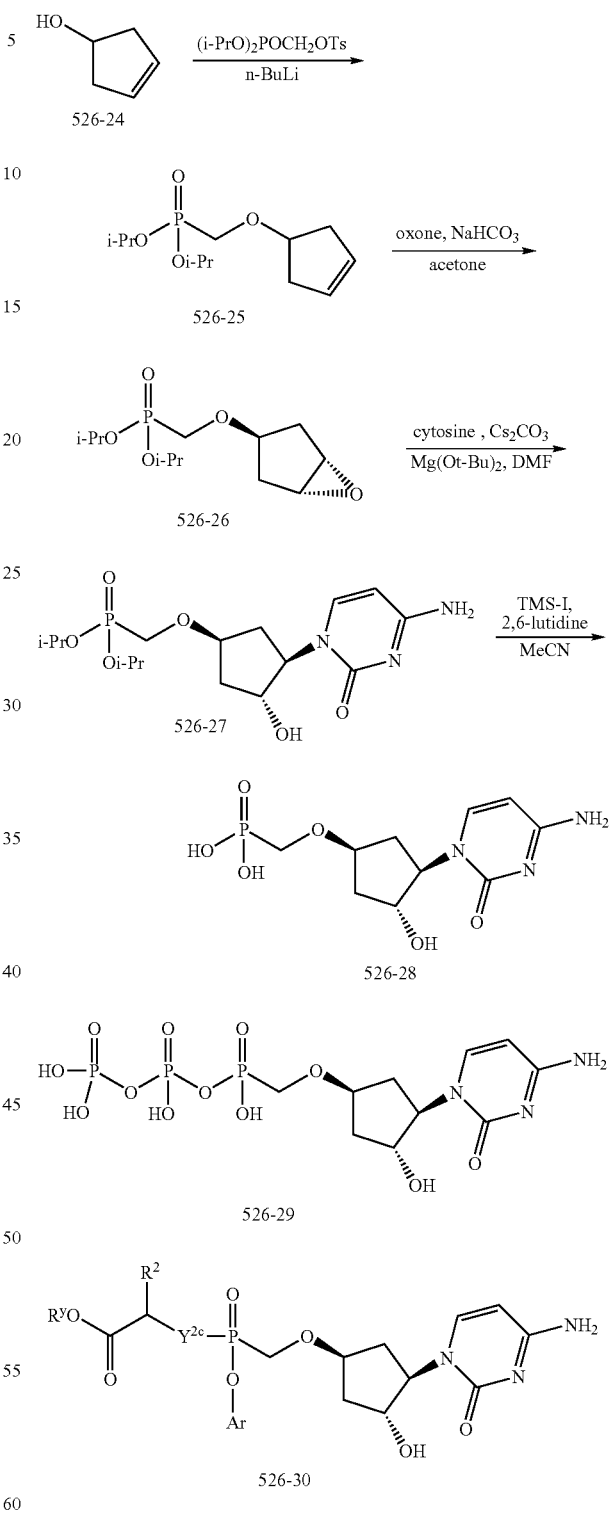

3-Cyclopenten-1-ol 526-24 (108 uL, 1.2 mmol, 1.2 eq) is dissolved in 5 mL of dry THF The solution is cooled to 0° C. A 1.35 M solution of n-BuLi (0.89 mL, 1.2 mmol, 1.2 eq) is added via syringe. After 10 min, diisopropylphosphonomethyl p-toluenesulfonate (350 mg, 1.0 mmol, 1.0 eq) is added. The mixture is stirred in a 45° C. bath for 3.5 h. The reaction is quenched with a pH 7 aqueous phosphate buffer. Extraction with diethyl ether gave a crude product, which is purified by silica gel chromatography (eluted with 45% ethyl acetate in hexane) to give 178 mg of 526-25 (68%).

To a solution of 526-25 (168 mg, 0.69 mmol, 1 eq) in 12 mL of acetone, is added 273 mg of NaHCO$_3$ in 8 mL of water. The mixture is then cooled to 0° C. Oxone (519 mg, 0.85 mmol, 1.3 eq) in 4 mL of water is added over 5 min in portions. The mixture is stirred vigorously for 2.5 h. The mixture is then evaporated in vacuo to remove most of the acetone. The aqueous residue is extracted with ethyl acetate to give a crude product, which is purified by silica gel chromatography to give 526-26 as a clear oil.

To a solution of 526-26 (21 mg, 0.076 mmol, 1.0 eq) in 0.25 mL of DMF, is added cytosine (13 mg, 1.5 eq) and cesium carbonate (6 mg, 0.25 eq) and magnesium t-butoxide. The mixture is heated to 140° C. for several hours. After cooling to room temperature, the reaction mixture is purified by reversed phase HPLC to give 12.5 mg of 526-27 (42%). $^1$H NMR (CDCl$_3$): δ 9.60 (br s, 1H), 8.96 (br s, 1H), 7.87 (d, 1H), 6.21 (d, 1H), 4.84 (m, 1H), 4.78 (m, 2H), 4.43 (m, 1H), 4.08 (s, 1H), 3.72 (m, 2H), 2.82 (m, 1H), 2.33 (m, 1H), 1.83 (m, 2H), 1.38 (m, 12H) ppm.

The conversion from 526-27 to 526-28 is described in Scheme 526-2 above. The conversion of 526-28 to the corresponding diphosphophosphonate 526-29 and phosphorus prodrugs, e.g. 526-30 can be accomplished using procedures described herein.

Cyclopentyl intermediate 526-31 may be prepared by procedures analogous to those described in U.S. Pat. No. 5,206,244 and U.S. Pat. No. 5,340,816 (Scheme 526-4). Diol 526-31 is converted to cyclopentenone 526-32 and treated with IBr in the presence of the appropriate phosphonate alcohol to give 526-33. Iodide 526-33 is displaced with inversion to give cyclopentanone intermediate 526-34. Nysted methylenation (U.S. Pat. No. 3,865,848; *Aldrichim. Acta* (1993) 26:14) provides exocyclic methylene 526-35, which may be deprotected to give 526-36.

Cyclopentanone 526-34 may be a versatile intermediate to form other compounds of the invention by reduction to cyclopentyl 526-37, or Wittig or Grubb olefination to alkenyl 526-38.

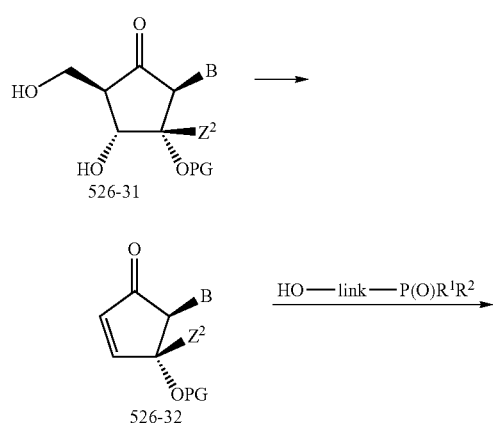

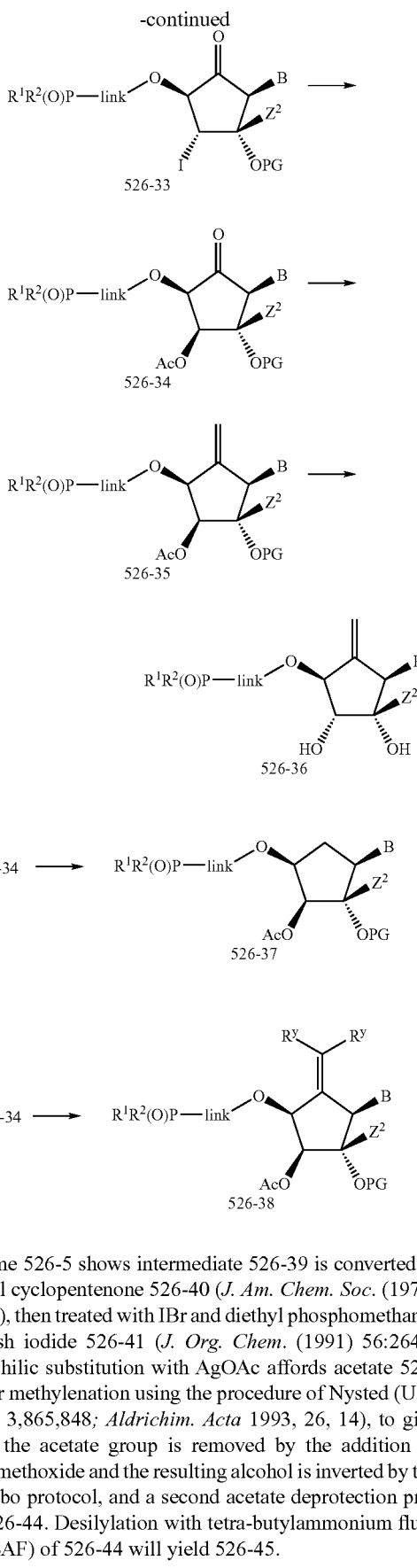

Scheme 526-5 shows intermediate 526-39 is converted to guanosyl cyclopentenone 526-40 (*J. Am. Chem. Soc.* (1972) 94:3213), then treated with IBr and diethyl phosphomethanol to furnish iodide 526-41 (*J. Org. Chem.* (1991) 56:2642) Nucleophilic substitution with AgOAc affords acetate 526-42. After methylenation using the procedure of Nysted (U.S. Pat. No. 3,865,848; *Aldrichim. Acta* 1993, 26, 14), to give 526-43, the acetate group is removed by the addition of sodium methoxide and the resulting alcohol is inverted by the Mitsunobo protocol, and a second acetate deprotection produces 526-44. Desilylation with tetra-butylammonium fluoride (TBAF) of 526-44 will yield 526-45.

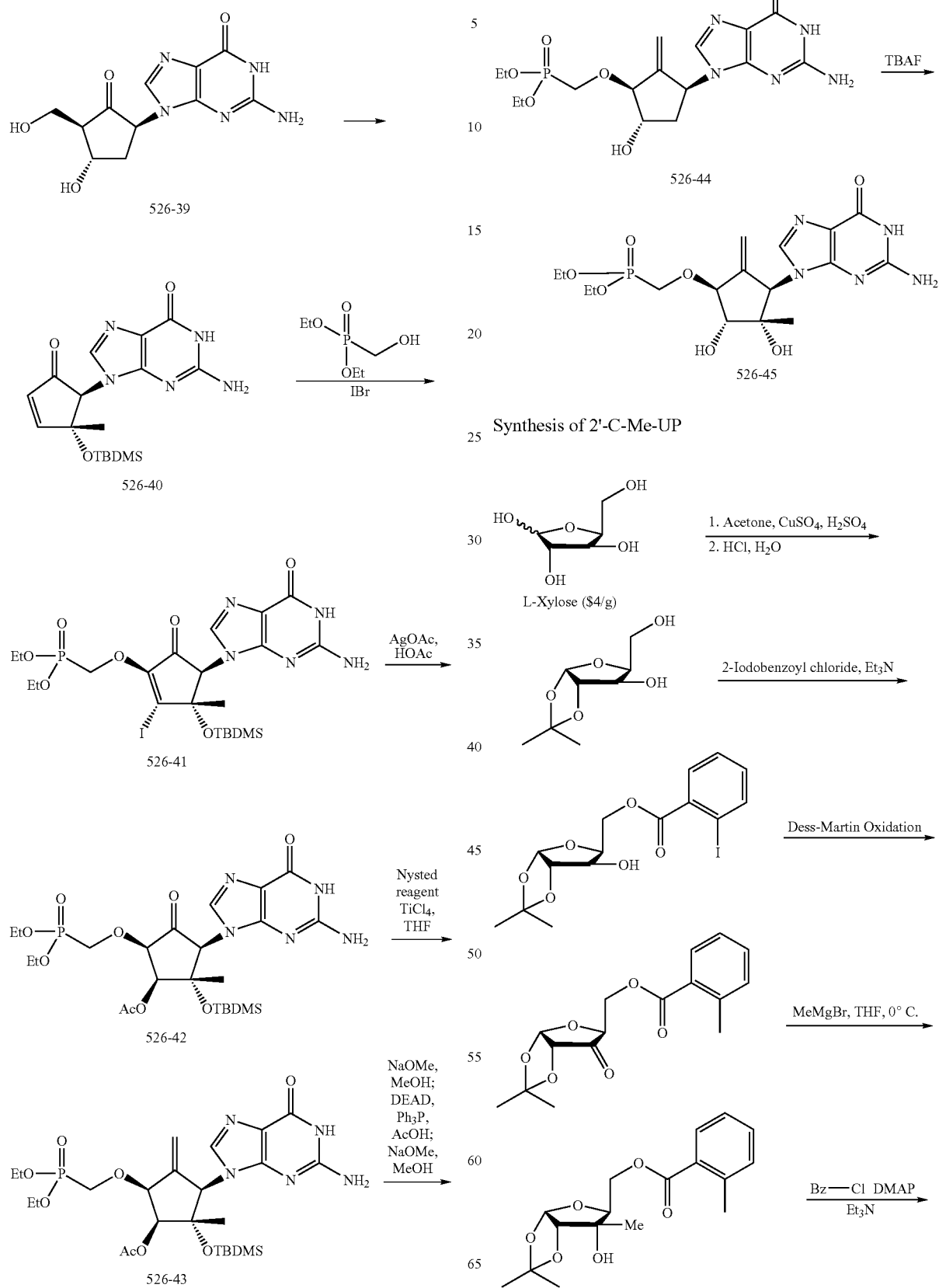
Scheme 526-5
Synthesis of 2'-C-Me-UP

1115

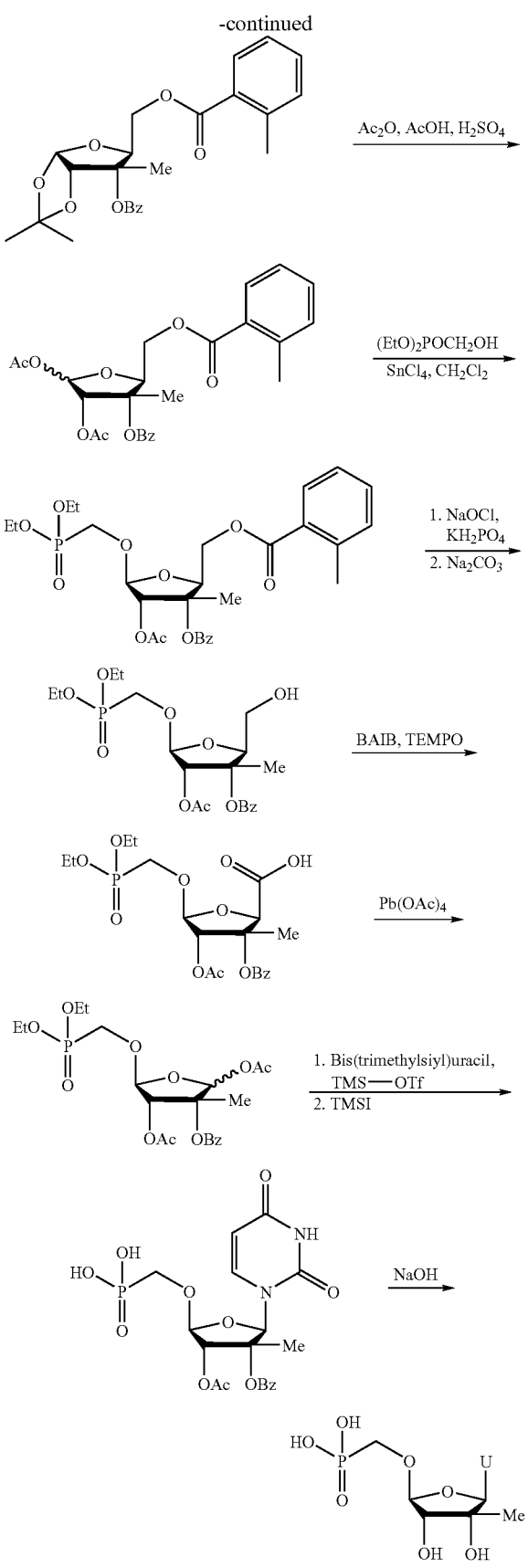

1116

Example 527

Synthesis of Exemplary Compounds of the Invention

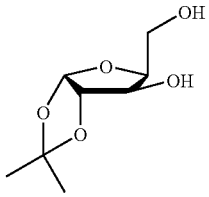

527-1

Synthesis of Compound 527-1: L-Xylose (36.2 g) and anhydrous CuSO$_4$ were placed in a 500 mL round bottomed flask. Acetone (220 mL) was added. To this slurry stirred at room temperature was added 3.6 mL of 96% sulfuric acid. The mixture was stirred for another 24 h at room temperature under a nitrogen atmosphere. The mixture is filtered to remove solid material. The solids were washed with 50 mL of acetone. To the combined filtrate was added 25.3 mL of conc. ammonium hydroxide. The precipitates were removed by filtration. The filtrate was evaporated in vacuo to give an oil, which was co-evaporated twice with absolute ethanol to give a yellow oil. The above crude product was stirred with 160 mL of 0.06 M aqueous HCl vigorously at room temperature for 2.5 h. The reaction mixture was homogeneous at the end of the reaction. Solid NaHCO$_3$ (3.26 g) was added in portions. After gas evolution had stopped, the mixture was filtered. The filtrate was frozen and lyophilized overnight to give a syrup, which was dissolved in ethyl acetate and dried over anhydrous Na2SO4 to give the desired diol as a yellow oil. Proton NMR showed the product to be >95% pure. Yield of this crude product: 44.5 g (96%). $^1$H NMR (DMSO-d$_6$, 300 MHz): δ 5.79 (d, J=3.6 Hz, 1H), 5.13 (d, J=4.9 Hz, 1H), 4.61 (t, J=5.6 Hz, 1H), 4.36 (d, J=3.6 Hz, 1H), 4.10-3.91 (m, 2H), 3.60 (m, 1H), 3.51 (m, 1H), 1.37 (s, 3H), 1.22 (s, 3H) ppm

Example 528

Synthesis of Exemplary Compounds of the Invention

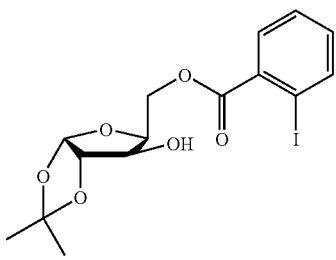

528-2

Synthesis of Compound 528-2: 1,2-O-isopropylidene-L-xylose (5 g, 26.3 mmol, 1.0 eq.) and 2-iodobenzoyl chloride (7.01 g, 26.3 mmol) were dissolved in anhydrous dichloromethane (25 mL). The solution was cooled in an ice-water bath. Triethylamine (3.85 mL, 27.6 mmol, 1.05 eq.) was added dropwise via syringe. The mixture was stirred at 0° C. for 30 min and slowly warmed to room temperature over 1 h.

Water was added to the reaction mixture. The mixture was washed with 1 M aqueous HCl. The aqueous wash was extracted with 20 mL of dichloromethane. The combined organic extract was washed with a mixture of 20 mL of brine and 5 mL of saturated aqueous sodium bicarbonate. The organic layer was dried over anhydrous $Na_2SO_4$, filtered, and concentrated in vacuo to give a brown oil. This crude product was purified by silica gel chromatography (eluted with 0-50% EtOAc in hexane) to give the desired mono-ester as a yellow oil. Yield: 7.6 g (69%). $^1H$ NMR (DMSO-$d_6$, 300 MHz): δ 8.02 (d, J=7.3 Hz, 1H), 7.73 (dd, J=7.8, 1.7 Hz, 1H), 7.52 (t, J=7.3 Hz, 1H), 7.29 (td, J=7.7, 1.8 Hz, 1H), 5.88 (d, J=3.7 Hz, 1H), 5.51 (m, 1H), 4.45 (m, 2H), 4.12 (m, 1H), 1.38 (s, 3H), 1.24 (s, 3H) ppm. MS (m/z): calculated 420.01 (M+H$^+$), 443.00 (M+Na$^+$), found 420.9 (M+H$^+$), 443.0 (M+Na$^+$).

Example 529

Synthesis of Exemplary Compounds of the Invention

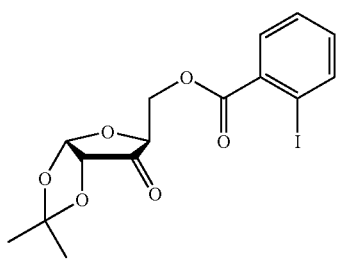

529-3

Synthesis of Compound 529-3: The product obtained in the previous step (7.6 g, 18.1 mmol, 1.0 eq.) was dissolved in 35 mL of anhydrous dichloromethane. Dess-Martin periodinane (9.6 g, 22.6 mmol, 1.25 eq.) was added. The mixture was stirred at room temperature for 14 h. A 1 M solution of sodium sulfite (7.5 mL) was added. The resulting mixture was stirred for another 2 h at room temperature. A saturated solution of NaHCO$_3$ was added in portions to adjust the pH of the aqueous phase to 6. The two layers were separated. The aqueous phase was extracted twice with 15 mL of dichloromethane. The combined organic extract was washed with brine, dried over anhydrous $Na_2SO_4$ for 4 h with good stirring. It was then filtered, and dried over excess amount of anhydrous $MgSO_4$ overnight with good stirring. The mixture was filtered and concentrated in vacuo to give a clear oil as product, which was used without further purification in the subsequent step. Yield: 6.7 g (89%). $^1H$ NMR (DMSO-$d_6$, 300 MHz): δ 8.02 (d, J=7.9 Hz, 1H), 7.71 (dd, J=7.8, 1.7 Hz, 1H), 7.52 (t, J=7.4 Hz, 1H), 7.29 (td, J=7.6, 1.5 Hz, 1H), 6.16 (d, J=4.6 Hz, 1H), 4.85 (m, 1H), 4.63 (d, J=4.6 Hz, 1H), 4.54 (dd, J=12.2, 2.7 Hz, 1H), 4.42 (dd, J=12.2, 4.3 Hz, 1H), 1.41 (s, 3H), 1.34 (s, 3H) ppm. MS (m/z): calculated 458.99 (M+H$_2$O$^+$Na$^+$), found 459.03 (M+H$_2$O$^+$Na$^+$).

Example 530

Synthesis of Exemplary Compounds of the Invention

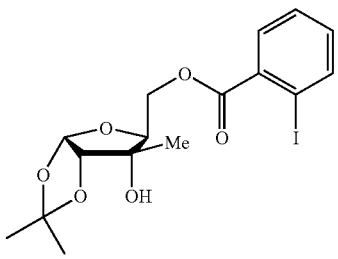

530-4

Synthesis of Compound 530-4: The product obtained in the previous step (6.15 g, 14.7 mmol, 1.0 eq.) was dissolved in 29 mL of anhydrous THF. The solution was cooled in an ice-water bath. A 3.0 M solution of methyl magnesium bromide in diethyl ether (5.39 mL, 16.2 mmol, 1.1 eq.) was added dropwise via syringe. The mixture was stirred at 0° C. for 2 h. Aqueous citric acid solution (1 M, 10 mL) was added to the reaction mixture. The resulting mixture was evaporated in vacuo to remove most of THF. The aqueous residue was extracted twice with 10 mL of EtOAc. The organic extract was washed with saturated NaHCO$_3$ and brine. The organic phase was dried over anyhydrous sodium sulfate, filtered, and evaporated in vacuo to give a white solid as product. Yield: 6.11 g (96%). $^1H$ NMR (DMSO-$d_6$, 300 MHz): δ 8.01 (dd, J=8.0, 1.0 Hz, 1H), 7.71 (dd, J=7.8, 1.7 Hz, 1H), 7.52 (td, J=7.5, 1.0 Hz, 1H), 7.29 (td, J=7.7, 1.8 Hz, 1H), 5.72 (d, J=3.7 Hz, 1H), 5.13 (s, 1H), 4.46 (dd, J=11.6, 2.3 Hz, 1H), 4.20 (dd, J=11.7, 8.5 Hz, 1H), 4.12 (d, J=3.6 Hz, 1H), 4.08 (dd, J=8.5, 2.1 Hz, 1H), 1.45 (s, 3H), 1.26 (s, 3H), 1.06 (s, 3H) ppm. MS (m/z): calculated 457.01 (M+Na$^+$), found 457.27 (M+Na$^+$).

Example 531

Synthesis of Exemplary Compounds of the Invention

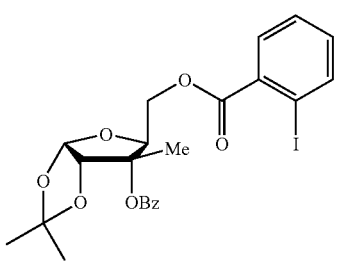

531-5

Synthesis of Compound 531-5: To a solution of 530-4 (6.1 g, 14.1 mmol) in 20 mL of anhydrous pyridine, was added triethylamine (3.13 mL, 22.5 mmol), DMAP (0.343 g, 2.8 mmol), followed by benzoyl chloride (2.61 mL, 22.5 mmol). The mixture was stirred at 70 C for 36 h, and then cooled to room temperature. The mixture was evaporated in vacuo to remove most of the pyridine. The residue was acidified with 1 M aqueous citric acid. The resulting mixture was extracted twice with ethyl acetate. The combined organic layer was washed with saturated NaHCO₃, and brine, dried over anhydrous Na₂SO₄, and evaporated in vacuo to give a crude product. This crude product was purified by silica gel chromatography (0-35% ethyl acetate in hexane) to give 7.0 g (92%) of 5. ¹H NMR (DMSO-d₆, 300 MHz): δ 8.03 (d, J=8.2 Hz, 1H), 7.90 (d, J=7.5 Hz, 2H), 7.79 (d, J=7.7 Hz, 1H), 7.64 (t, J=7.9 Hz, 1H), 7.5 (m, 3H), 7.30 (t, J=7.6 Hz, 1H), 5.92 (d, J=3.7 Hz, 1H), 4.92 (d, J=3.5 Hz, 1H), 4.63 (m, 1H), 4.46 (m, 2H), 1.50 (s, 3H), 1.39 (s, 3H), 1.25 (s, 3H) ppm. MS (m/z) 589.2 (M+H⁺), 611.3 (M+Na⁺). MS (m/z): calculated 561.04 (M+Na⁺), found 561.06 (M+Na⁺).

Example 532

Synthesis of Exemplary Compounds of the Invention

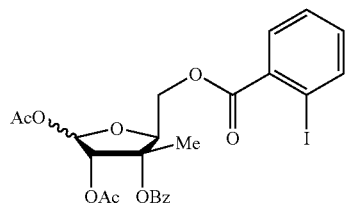

532-6

Synthesis of Compound 532-6: To a solution of 531-5 (7.0 g, 13 mmol) in 26 mL of glacial acetic acid, was added acetic anhydride (7.7 mL). The solution was cooled in an ice-water bath. Concentrated sulfuric acid (1.9 mL) was added dropwise via syringe over 10 min. The cooling bath was removed and the solution was allowed to warm to room temperature and stirred at that temperature for another 20 h. The reaction mixture was poured into a mixture of 75 mL of diethyl ether and 75 g of ice. The layers were separated and the aqueous layer was extracted with 75 mL of diethyl ether. The combined ether extract was stirred with 250 mL of water. Solid NaHCO3 was added in portions until gas evolution had stopped. The layers were separated. The aqueous layer was extracted with 75 mL of ether. The combined ether extract was washed with brine, dried over anhydrous MgSO₄, and concentrated in vacuo to give 6 as a yellow foam. Two diastereomers of the same molucular weight were present in the product mixture, presumably the two anomers. Yield: 6.76 g (89%). This crude product was used without further purification. MS (m/z): calculated 605.03 (M+Na⁺), found 604.93 (M+Na⁺).

Example 533

Synthesis of Exemplary Compounds of the Invention

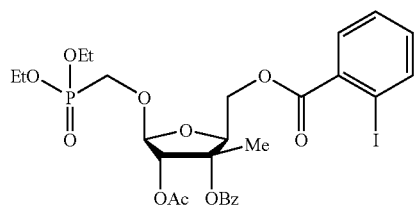

533-7

Synthesis of Compound 533-7: 532-6 (6.76 g, 11.6 mmol) was dissolved in 22 mL of dichloromethane. The solution was cooled in an ice-water bath. A solution of SnCl₄ in dichloromethane (1.0 M, 29 mL, 29 mmol) was added via syringe. The cooling bath was removed and the mixture was warmed to room temperature and stirred for another hour. The mixture was again cooled to 0° C. Triethylamine (15 mL) was added via syringe. The resulting solution was poured onto a mixture of 75 g of ice and 75 mL of EtOAc. The mixture was filtered through a pad of Celite. The solids were washed thoroughly with EtOAc. The combined filtrate was washed with saturated NaHCO₃, brine, dried over Na₂SO₄, and concentrated in vacuo to give a crude product, which was purified by silica gel chromatography (25-75% EtOAc in hexane) to give 7 as a light yellow foam. Yield: 6.0 g (75%). ¹H NMR (DMSO-d₆, 300 MHz): δ 8.00 (d, J=7.9 Hz, 1H), 7.86 (d, J=8.0 Hz, 2H), 7.79 (d, J=7.9 Hz, 1H), 7.61 (t, J=7.2 Hz, 1H), 7.45 (m, 3H), 7.25 (t, J=7.3 Hz, 1H), 5.28 (s, 1H), 5.07 (s, 1H), 4.65 (m, 2H), 4.49 (m, 1H), 4.10-3.90 (m, 5H), 3.83 (dd, J=13.9, 9.0 Hz, 1H), 1.88 (s, 3H), 1.69 (s, 3H), 1.18 (t, J=6.9 Hz, 6H) ppm. MS (m/z): calculated 713.06 (M+Na⁺), found 713.08 (M+Na⁺).

Example 534

Synthesis of Exemplary Compounds of the Invention

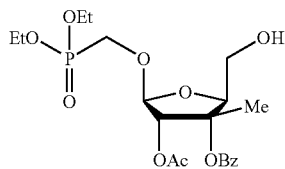

534-8

Synthesis of Compound 534-8: To a solution of 533-7 (4.7 g, 6.8 mmol) in 30 mL of dichloromethane was added 27.2 mL of a 1.0 M aqueous solution of KH₂PO₄. A 0.8 M solution of NaOCl in water was added. The mixture was stirred at room temperature for 1 h. Methanol (10 mL) was added. Solid K2CO3 was added in portions until the pH of the aqueous phase reached 9-10. The mixture was stirred for another hour at room temperature. An 1 M aqueous solution of Na₂SO₃ (10 mL) was added and the mixture was stirred for another 30 min at room temperature. The two layers were separated. The aqueous layer was further extracted with dichloromethane. The combined organic layer was washed with brine, dried over anhydrous Na2SO4, and evaporated in vacuo to give 534-8 as a yellow foam, which was used directly in the next step without further purification. ¹H NMR (DMSO-d₆, 300 MHz): δ 7.94 (d, J=7.8 Hz, 2H), 7.68 (t, J=7.5 Hz, 1H), 7.54 (t, J=7.6 Hz, 2H), 5.28 (d, J=1.0 Hz, 1H), 5.05 (d, J=1.2 Hz, 1H), 4.98 (t, J=5.6 Hz, 1H), 4.34 (dd, J=6.5, 4.6 Hz, 1H), 4.11-3.95 (m, 5H), 3.86 (dd, J=13.7, 8.8 Hz, 1H), 3.76 (m, 1H); 3.63 (m, 1H), 1.93 (s, 3H), 1.64 (s, 3H), 1.25 (t, J=7.0 Hz, 6H) ppm. ³¹P NMR (DMSO-d₆): δ 20.63 (s, 1P) ppm. MS (m/z): calculated 483.14 (M+Na⁺), found 483.30 (M+Na⁺).

Example 535

Synthesis of Exemplary Compounds of the Invention

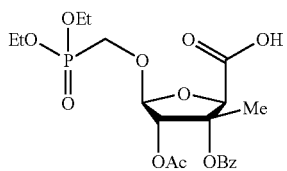

535-9

Synthesis of Compound 535-9: To a mixture of 533-8 obtained above and 6.8 mL of acetonitrile and 6.8 mL of water, was added iodobenzene diacetate (4.97 g, 15 mmol), and TEMPO (0.213 g, 1.36 mmol). The mixture was stirred vigorously for 6 h at room temperature. It was then frozen and lyophilized to give a orange colored solid, which was dissolved in dichloromethane and purified by silica gel chromatography (0-10% MeOH in $CH_2Cl_2$) to give 534-9 as a light yellow solid. Yield: 2.8 g (87% for two steps). $^1$H NMR (DMSO-$d_6$, 300 MHz): δ 13.39 (br s, 1H), 7.97 (d, J=7.8 Hz, 2H), 7.70 (t, J=7.3 Hz, 1H), 7.56 (t, J=7.5 Hz, 2H), 5.35 (s, 1H), 5.16 (s, 1H), 4.89 (s, 1H), 4.18 (dd, J=13.7, 8.8 Hz, 1H), 4.06 (m, 4H), 3.88 (dd, J=13.4, 9.7 Hz, 1H), 1.86 (s, 3H), 1.69 (s, 3H), 1.24 (dt, J=7.0, 2.7 Hz, 6H) ppm. $^{31}$P NMR (DMSO-$d_6$): δ 20.79 (s, 1P) ppm. MS (m/z): calculated 473.12 (M–H), found 472.95 (M–H$^-$).

Example 536

Synthesis of Exemplary Compounds of the Invention

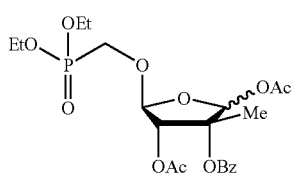

536-10

Synthesis of Compound 536-10: To a solution of 535-9 (474 mg, 1.0 mmol) in 2.0 mL of anhydrous DMF, was added pyridine (238 mg, 3.0 mmol), and lead tetraacetate (1.33 g, 3.0 mmol). The mixture was stirred while shielded from light for 7 h at room temperature. It was then poured into a mixture of 10 g of ice and 10 mL of diethyl ether. The mixture was filtered to remove precipitates. The two layers of the filtrate were separated. The aqueous phase was extracted twice with ether. The combined ether extract was washed with 1 M citric acid, saturated $NaHCO_3$, and brine. After drying with anhydrous $MgSO_4$, the ether solution was concentrated in vacuo to give crude 536-10 as a colorless oil, which was used without further purification. Yield: 255 mg (52%). MS (m/z): calculated 511.13 (M+Na$^+$), found 511.11 (M+Na$^+$).

Example 537

Synthesis of Exemplary Compounds of the Invention

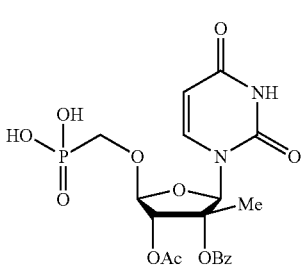

537-11

Synthesis of Compound 537-11: To a solution of 536-10 (211 mg, 0.43 mmol) in 2.0 mL of anhydrous acetonitrile, was added O,O-bis(trimethylsilyl)uracil (443 mg, 1.73 mmol), and TMS-OTf (384 mg, 1.73 mmol). The mixture was stirred at room temperature for 3 h. An additional 443 mg of O,O-bis(trimethylsilyl)uracil was added, and the mixture was stirred for another 4 h at room temperature. 2,6-Lutidine (371 mg, 3.46 mmol) was added dropwise via syringe, followed by TMS-I (259 mg, 1.3 mmol). The mixture was stirred for another hour at room temperature and then poured onto 10 g of ice. The mixture frozen and filtered through a pad of Celite. The filtrate was frozen and lyophilized to give a yellow solid, which was dissolved in water and purified by reversed phase HPLC to give 537-11 as a white solid. Yield: 20 mg (10%). MS (m/z): calculated 483.08 (M–H), found 483.34 (M–H$^-$).

Example 538

Synthesis of Exemplary Compounds of the Invention

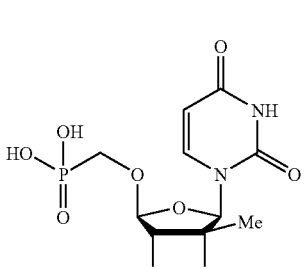

538-12

Synthesis of Compound 538-12: To a solution of 537-11 (17 mg, 0.035 mmol) in 0.3 mL water, was added NaOH (4.3 mg, 0.11 mmol). After stirring at room temperature for 2 h, the mixture acidified with trifluoroacetic acid and purified by HPLC to give 538-12 as a white powder. Yiled: 5 mg (42%). $^1$H NMR (D$_2$O, 300 MHz): δ 7.74 (d, J=8.2 Hz, 1H), 5.97 (s, 1H), 5.78 (d, J=8.2 Hz, 1H), 5.10 (d, J=4.9 Hz, 1H), 3.86 (dd, J=12.9, 10.0 Hz, 1H), 3.78 (d, J=4.7 Hz, 1H), 3.65 (dd, J=12.7, 9.3 Hz, 1H), 1.10 (s, 3H) ppm. $^{31}$P NMR (D$_2$O): δ 14.60 (s, 1P) ppm. MS (m/z): calculated 337.04 (M–H), found 337.38 (M–H$^-$).

Example 539

Synthesis of Exemplary Compounds of the Invention

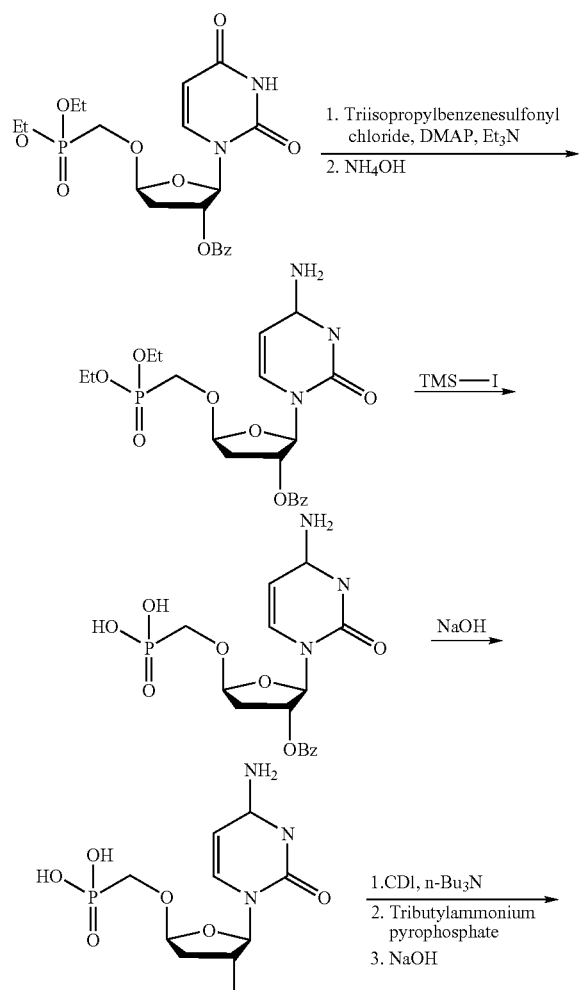

Example 540

Synthesis of Exemplary Compounds of the Invention

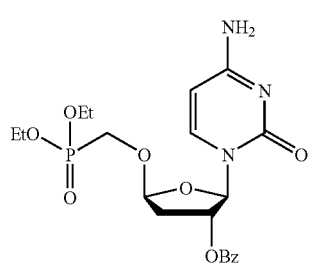

Synthesis of Compound 540-2 To a stirred solution of 527-1 (50 mg, 0.11 mmol) in 1 mL of acetonitrile under nitrogen was added 2,4,6-triisopropylbenzenesulfonyl chloride (65 mg, 0.21 mmol), DMAP (26 mg, 0.21 mmol), and triethylamine (22 mg, 0.21 mmol). The mixture was stirred at room temperature for 4 h. Aqueous ammonia (29%, 1 mL) was added. The mixture was stirred at room temperature for 2 h. Extraction with EtOAc, followed by purification by silica gel chromatography gave 540-2 as a white solid. MS (m/z): calculated 468.15 (M+H$^+$), found 468.0 (M+H$^+$).

Example 541

Synthesis of Exemplary Compounds of the Invention

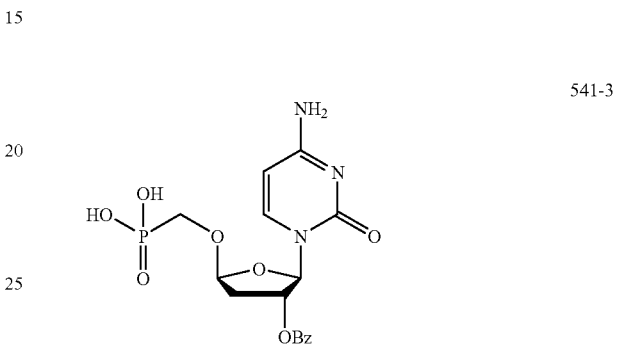

Synthesis of Compound 541-3: To a solution of 540-2 obtained above in acetonitrile was added 2,6-lutidine (118 mg, 1.10 mmol) and TMS-1 (165 mg, 0.84 mmol). The mixture was stirred at room temperature for 2 h. Triethylamine was added, followed by water. The mixture was then frozen and lyophilized to give a solid residue. This crude product was purified by reversed phase HPLC to give 541-3 as a white solid. Yiled 44 mg (97% for two steps). MS (m/z): calculated 410.1 (M−H), found 410.2 (M−H$^−$).

Example 542

Synthesis of Exemplary Compounds of the Invention

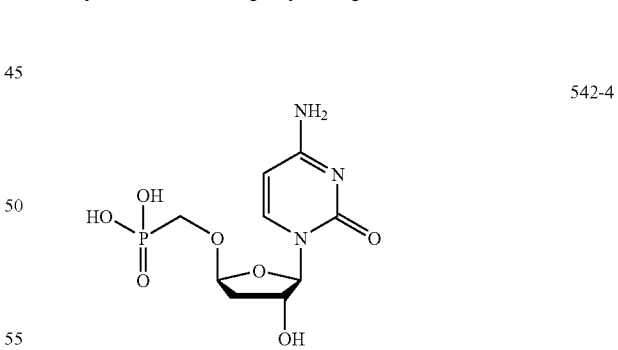

Synthesis of Compound 542-4: To solution of 541-3 (40 mg, 0.097 mmol) in 0.5 mL of water was added NaOH (20 mg, 0.5 mmol). The solution was stirred at room temperature for 30 min. Reversed phase HPLC purification gave 542-4 as a white solid. Yield: 28 mg (94%). $^1$H NMR (D$_2$O, 300 MHz) δ 7.79 (d, J=7.6 Hz, 1H), 5.95 (d, J=7.6 Hz, 1H), 5.88 (d, J=2.8 Hz, 1H), 5.40 (m, 1H), 4.42 (m, 1H), 3.78 (dd, J=12.8, 9.8 Hz, 1H), 3.55 (dd, J=13.1, 9.7 Hz, 1H), 2.20-2.05 (m, 2H) ppm. $^{31}$P NMR (D$_2$O, 300 MHz) δ 14.66 ppm. MS (m/z): calculated 306.05 (M−H), found 305.8 (M−H$^−$).

Example 543

Synthesis of Exemplary Compounds of the Invention

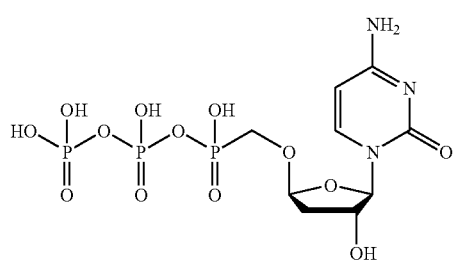

543-5

Synthesis of Compound 543-5: To phosphonic diacid 542-4 (9 mg, 0.029 mmol) in 0.25 mL of DMF was added tributylamine (5.4 mg, 0.03 mmol) followed by carbonyldiimidazole (48 mg, 0.3 mmol). Reaction mixture was stirred at room temperature for 4 h at which point MeOH (0.010 mL) was added and stirred for an additional 30 min. Tributyl ammonium pyrophosphate (161 mg, 0.3 mmol) in DMF (0.64 mL) was added the reaction mixture stirred for 14 h. After the solvents were evaporated in vacuo, the crude product was purified by ion exchange HPLC (0-40% TEAB) to give the triethylammonium salt of 543-5 as a white solid. Yield: 3 mg. $^1$H NMR (D$_2$O, 300 MHz) δ 7.78 (d, J=7.6 Hz, 1H), 6.02 (d, J=7.6 Hz, 1H), 5.88 (d, J=2.9 Hz, 1H), 5.42 (m, 1H), 4.41 (m, 1H), 4.05-3.62 (m, 2H), 3.05 (q, J=7.4 Hz, triethylammonium), 2.23-1.95 (m, 2H), 1.13 (t, J=7.4 Hz, triethylammonium) ppm. $^{31}$P NMR (D$_2$O, 300 MHz) δ 7.58 (d), −8.34 (d), −22.71 (t) ppm. MS (m/z): calculated 465.98 (M−H$^-$), found 466.16 (M−H$^-$).

Example 544

Synthesis of Exemplary Compounds of the Invention

Synthesis of 3'-Deoxy-CP

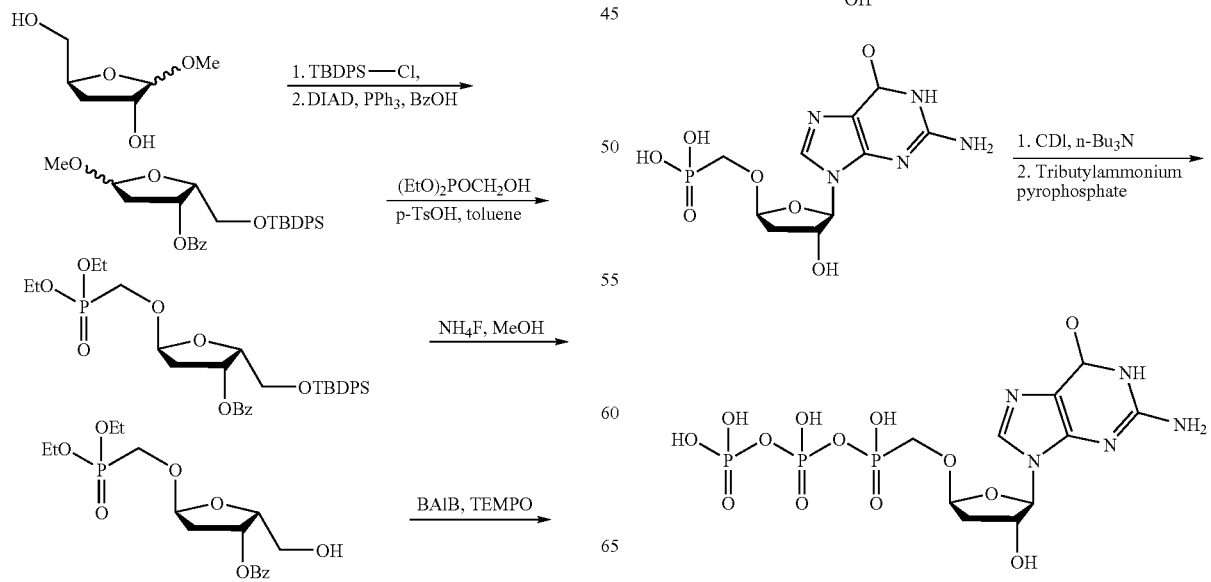

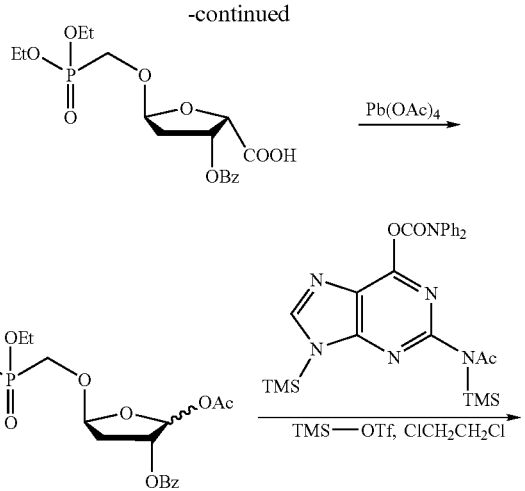

Example 545

Synthesis of Exemplary Compounds of the Invention

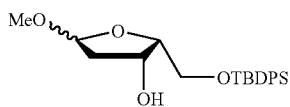

545-2

Synthesis of Compound 545-2 To a stirred solution of 1-O-methyl-2'-deoxy-D-ribose (23.9 g, 161.41 mmol) in pyridine under nitrogen was added t-butyldiphenylsilyl chloride (48 mL, 186 mmol) dropwise. When the addition was complete N,N-dimethyl-4-aminopyridine was added as a solid. The reaction was stirred at room temperature for 12 hr. and monitored by TLC. When the reaction was complete by TLC the pyridine was removed under vacuum. The oily residue was suspended in ethyl acetate (150 mL) and a white solid formed. The mixture was filtered and the solid was washed with 50 mL additional ethyl acetate. The solid was then discarded. The organic filtrates were combined and washed with water (2×100 mL), 1N HCl(aq) (2×100 mL) and sodium bicarbonate (sat'd) (2×100 mL). The organic phase was collected and dried over MgSO$_4$(anh). Evaporation and purification by column chromatography provides the desired mixture of diastereomers 545-2: yield 31.15 g (50 0%). $^1$H NMR (CD$_3$CN, 300 MHz): δ 1.08 m, 9H); 1.85 m 1H; 2.27 m 2H, 3.3 s 3H, 3.7 m 2H; 3.90 m 1H; 4.27 m 1H; 5.06 m 1H, 7.45 m 6H, 7.76 m 4H. ppm.

Example 546

Synthesis of Exemplary Compounds of the Invention

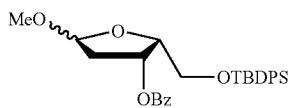

546-3

Synthesis of Compound 546-3: The alcohol 545-2 (5.00 g, 12.95 mmol) and triphenylphosphine (6.79 g. 25.9 mmol) were dissolved in anhydrous THF (50 mL) under nitrogen at room temperature. To this stirring solution was added dropwise, a mixture of benzoic acid (3.162 g, 25.9 mmol) and disopropylazodicarboxylate dissolved in anhydrous THF (30 mL). After the addition was complete the reaction was stirred for 12 hr. at room temperature. After the reaction was complete by TLC, the solvent was removed under vacuum. The residue was suspended in diethyl ether (60 mL). Hexane (120 mL) was added and the solid formed was filtered and discarded. The solvents were removed by rotary evaporation and the products 546-3 were purified by column chromatography (2% to 15% EtOAc in hexane): yield 3.074 g (48.4%). $^1$H NMR (CD$_3$CN, 300 MHz): δ 0.98 m 9H, 2.07 m 1H; 2.42 m 2H, 3.35 s 3H, 3.85 m 1H; 3.99 m 1H; 4.4 m 1H; 5.10 m 1H; 5.69 m 1H; 7.30 m 1H; 7.47 m 5H, 7.65 m 6H, 7.80 m 1H; 7.95 m 1H; 8.22 m 1H ppm.

Example 547

Synthesis of Exemplary Compounds of the Invention

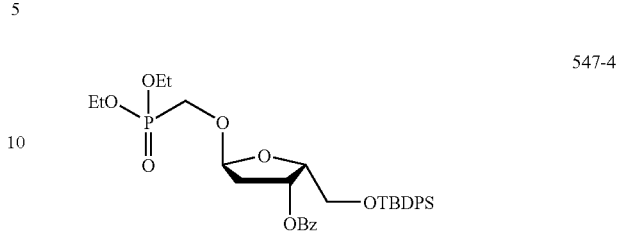

547-4

Synthesis of Compound 547-4: The acetal 546-3 (6.88 g, 12.95 mmol) and hydroxymethylphosphonate diethyl ester (7.76 mL, 52.65 mmol) were dissolved in 200 mL of toluene. The toluene was removed by rotary evaporation at 70° C. under vacuum to reduce the reaction volume to appoximately 25 mL. The reaction was cooled to room temperature and p-toluene sulfonic acid monohydrate (0.490 g, 2.58 mmol) was added as a solid along with toluene (200 mL). The toluene was removed by rotary evaporation at 70° C. under vacuum to reduce the reaction volume once again to appoximately 25 mL. Two additional aliquots of toluene were added and removal by evaporation is repeated each time. The reaction was monitored by TLC and when completed the residue was suspended in ethyl acetate (100 mL) The organic layer was washed with sodium bicarbonate (sat'd), brine and then dried over MgSO$_4$ (anh). The desired phosphonate 547-4 was purified by column chromatography (10% to 90% EtOAc in hexane): yield 2.89 g (33%). $^1$H NMR (DMSO-d$_6$, 300 MHz): δ 0.92 s 9H, 1.25 t 6H, 2.35 t 2H, 3.84 m 4H, 4.05 m 4H, 4.32 q 1H; 5.37 t 1H, 5.62 q 1H; 7.26 t 2H, 7.30-7.55 m 8H, 7.60 d 2H, 7.65 t 1H; 7.82 d 2H ppm.

Example 548

Synthesis of Exemplary Compounds of the Invention

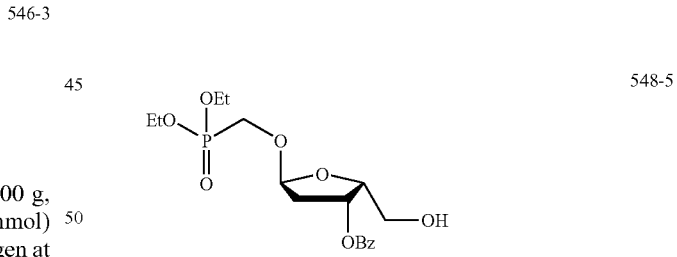

548-5

Synthesis of Compound 548-5: The silyl ether 547-4 (2.86 g, 4.57 mmol) was dissolved in a minimal amount of methanol (15 mL) and stirred a room temperature under nitrogen. Ammonium fluoride (1.69 g, 45.7 mmol) was added as a solid and the reaction was stirred at room temperature for 12 hr. The reaction was monitored by TLC and, when complete the methanol was removed under a stream of nitrogen. Add 6 mL of 1N Acetic acid (aq) and extract the aqueous phase with ethyl acetate (2×125 mL). Combine the organic extracts and dried over Na$_2$SO$_4$(anh). The final product 548-5 was purified by column chromatography (50% to 100% EtOAc in hexane): yield 1.59 g (90%). $^1$H NMR (DMSO-d$_6$, 300 MHz): δ 1.21 t 6H, 2.35 t 2H, 3.62-3.82 m 4H, 4.05 m 4H, 4.12 q 1H; 5.30 t 1H; 5.49 q 1H, 7.47 t 2H, 7.65 t 1H; 7.90 d 2H.

Example 549

Synthesis of Exemplary Compounds of the Invention

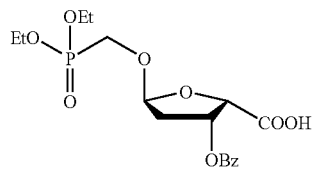

549-6

Synthesis of Compound 549-6: The primary alcohol 548-5 (1.43 g, 3.69 mmol) was dissolved in a 1:1 mixture of acetonitrile and water (10 mL) under nitrogen. Bisacetyliodobenzene (2.61 g, 8.12 mmol) was added as a solid along with a catalytic amount of TEMPO (0.15 g, 0.74 mmol). The reaction was stirred at room temperature for 12 hr. and monitored by TLC. When the reaction was complete, it was frozen and lyphilized. The carboxylic acid 549-6 was purified by column chromatography (0% to 10% methanol in dichloromethane): yield 0.750 g (51%). $^1$H NMR (CD$_3$CN, 300 MHz): δ 1.30 t 6H, 2.45 t 2H, 3.84 m 1H; 4.00-4.20 m 5H, 4.82 d 1H; 5.50 t 1H; 5.82 q 1H; 7.54 t 2H, 7.65 t 1H; 7.96 d 2H.

Example 550

Synthesis of Exemplary Compounds of the Invention

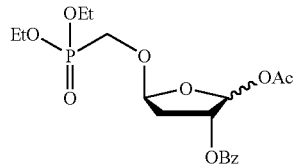

550-7

Synthesis of Compound 550-7 To acid 549-6 (88 mg, 0.22 mmol) in DMF (3.1 mL, 0.07 M) was added anhydrous pyridine (0.027 mL, 0.33 mmol) followed by lead tetraacetate (146 mg, 0.33 mmol). After 14 h at room temperature, Et$_2$O/H$_2$O (1:1, 3 mL) was added. The organics were separated, washed with 1M aqueous citric acid, saturated aqueous NaHCO$_3$, saturated aqueous NaCl and dried over sodium sulfate. After removal of solvent, the crude product 7 (50 mg, 54%) was used directly in the next reaction.

Example 551

Synthesis of Exemplary Compounds of the Invention

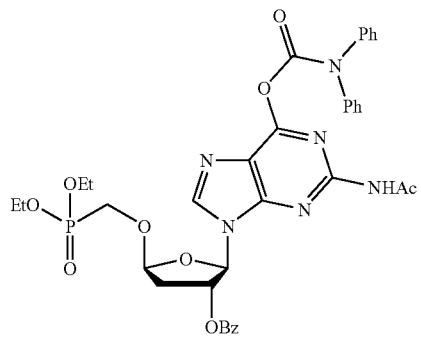

551-8

Synthesis of Compound 551-8: N-Acetoxy-diphenylcarbamoyl gaunine (43 mg, 0.11 mmol), synthesized as described in Can. J. Chem. 65: 1436 (1987), in dichloroethane (1.1 mL, 0.1 M) was treated with N,O-bis(trimethylsilyl)acetamide (0.054 mL, 0.22 mmol). The reaction mixture was heated to 80° C. for 20 min after which the solvents were removed in vacuo. The crude silylated protected guanine was combined with phosphonate 550-7 (50 mg, 0.12 mmol) in dichloroethane (1.1 mL, 0.1 M) to which TMSOTf (28 µL, 0.153 mmol) was added. The reaction mixture heated to 60° C. for 5 h after with the reaction was quenched with saturated aqueous NaHCO$_3$. The solution was extracted with CH$_2$Cl$_2$, washed with saturated aqueous NaHCO$_3$, and dried over sodium sulfate. After removal of solvent, the crude product was purified by column chromatography on silica (2% MeOH/CH$_2$Cl$_2$) to provide the phosphonate diester 551-8 (18 mg, 22%). $^1$H NMR (CDCl$_3$, 300 MHz) δ 8.30 (s, 1H), 8.15 (s, 1H), 8.02 (s, 1H) 8.00 (s, 1H), 7.35-7.62 (m, 12H), 6.43 (d, 1H), 6.02 (m, 1H), 5.65 (m, 1H), 4.18 (q, 4H), 3.78-4.01 (m, 2H), 2.86 (m, 1H), 2.63 (m, 1H), 2.53 (s, 3H), 1.37 (t, 6H) ppm. $^{31}$P NMR (CDCl$_3$, 300 MHz) δ 20.07 (s) ppm. MS (m/z): calculated 744.2 (M+H$^+$), found 744.9 (M+H$^+$).

Example 552

Synthesis of Exemplary Compounds of the Invention

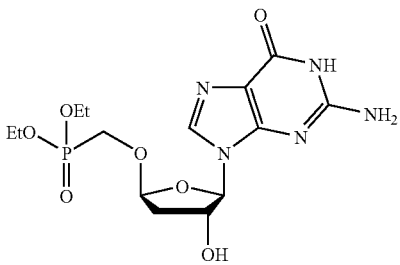

552-9

Synthesis of Compound 552-9 Phosphonate ester 551-8 (14 mg, 0.02 mmol) was treated with NH$_3$ in MeOH (2 mL, 2.0 N) at room temperature for 9 h. After solvents were removed in vacuo, the crude product was purified by column chromatography on silica (10% MeOH/CH$_2$Cl$_2$) to provide 552-9. $^1$H NMR (CD$_3$OD, 300 MHz) δ 7.89 (s, 1H), 5.96 (d, 1H), 5.45 (m, 1H), 4.10-4.21 (q, 4H), 3.8144.02 (m, 2H), 2.92-2.47 (m, 2H), 1.33 (t, 6H) ppm. $^{31}$P NMR (CD$_3$OD, 300 MHz) δ 21.75 ppm. MS (m/z): calculated 404.1 (M+H$^+$), found 404.2 (M+H$^+$).

Example 553

Synthesis of Exemplary Compounds of the Invention

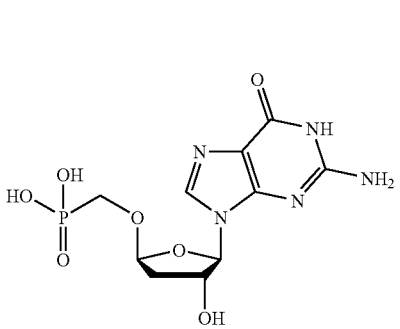

553-10

Synthesis of Compound 553-10: To phosphonate ester guanosine derivative 552-9 (5.8 mg, 0.02 mmol) in anhydrous acetonitrile (0.15 mL, 0.1 M) was added 2,6-lutidine (0.014 mL, 0.12 mmol) followed by iodotrimethylsilane (0.016 mL, 0.12 mmol). After stirring for 15 min, triethylamine (0.12 mmol) and methanol (0.020 mL) were added and solvents were removed in vacuo. The crude product was purified by reverse phase column chromatography on C18 (0-10% MeOH/H$_2$O-1% AcOH) to provide the phosphonic diacid 553-10. $^1$H NMR (D$_2$O, 300 MHz) δ 7.91 (s, 1H), 5.86 (d, 1H), 5.41 (m, 1H), 3.42-3.65 (m, 2H), 2.25-2.36 (m, 2H) ppm. $^{31}$P NMR (D$_2$O, 300 MHz) δ 15.16 ppm. MS (m/z): calculated 346.1 (M−H), found 346.3 (M−H$^-$).

Example 554

Synthesis of Exemplary Compounds of the Invention

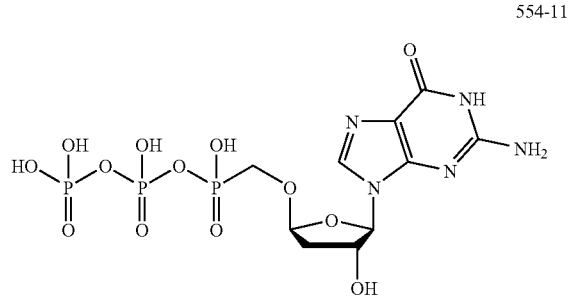

554-11

Synthesis of Compound 554-11: To phosphonic diacid 553-10 (2.5 mg, 7.2 μmol) in DMF (144 μL, 0.05 M) was added tributylamine (0.0086 mL, 0.036 mmol) followed by carbonyldiimidazole (12 mg, 0.072 mmol). Reaction was stirred at room temperature for 12 h at which point MeOH (0.005 mL) was added and stirred for an additional 30 min. Tributyl ammonium pyrophosphate (0.040 mg, 72 mmol) in DMF (0.16 mL) was added the reaction mixture stirred for 1 h. After the solvents were evaporated in vacuo, the crude product was purified by ion exchange HPLC (0-60% TEAB) to provide the diphosphophosphonate 554-11. $^1$H NMR (D$_2$O, 300 MHz) δ 7.94 (s, 1H), 5.85 (d, 1H), 4.47 (m, 1H), 3.71-3.78 (m, 2H), 2.27-2.39 (m, 2H) ppm. $^{31}$P NMR (D$_2$O, 300 MHz) δ 8.09 (d), 7.71 (s), −22.04 (t) ppm. MS (m/z): calculated 505.99 (M−H), found 506.2 (M−H$^-$).

Example 555

Synthesis of Exemplary Compounds of the Invention

The following Schemes 555-5 to 555-9 describes a general method of preparing the [3.1.0] bicyclo hexane scaffold of the Formula 555-1 and 555-11 compounds. Exemplary structures, intermediates, substituents, protecting groups, reagents, and synthetic routes chosen for description here are meant to merely illustrate general methods of preparation, and are not intended to any way limit or denote preference to the methods.

The [3.1.0] bicyclo hexane scaffold may be synthesized by intramolecular cyclopropanation of a carbene generated by decomposition of a diazo 1,3-ketoester (Moon etal (2000) *Organic Letters* 2(24):3793-3796). The requisite 1,3-ketoester 555-5.1 may be prepared from acetoacetate ester anion addition to ene-aldehydes, e.g. acrolein (Scheme 555-5a). For example, ethyl acetoacetate treated with 2 equivalents of lithium diisopropylamide at −78° C. and then one equivalent of acrolein gives the 1,3-ketoester 555-5.1 (Yoshimura etal (2002) *Jour. Org. Chem.* 67:5938-5945). Protection of the hydroxyl may be accomplished with phenyldimethylsilyl chloride to give 555-5.2 where PG is phenyldimethylsilyl (PhMe$_2$Si—). Other trialkylsilyl protecting groups may be useful. Diazotization with p-toluenesulfonyl azide gives 555-5.3. Treatment of 555-5.3 with a carbenoid insertion catalyst, e.g. CuSO$_4$ or Rh(OAc)$_2$, gives 555-5.4 as a mixture of diastereomers.

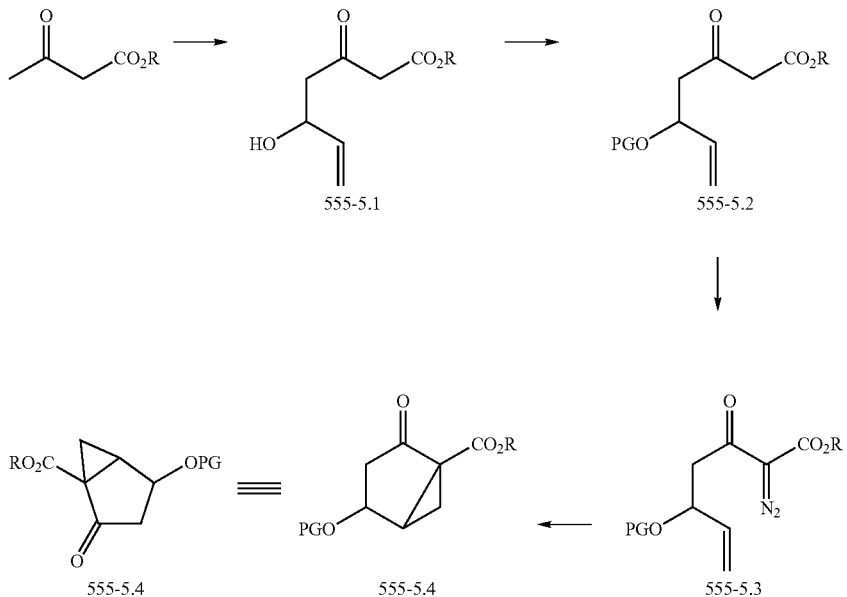

Scheme 555-5a

The ester of 555-5.4 may be hydrolyzed to the hydroxymethyl 555-5.5 or saponified directly to carboxylic acid 555-5.6 (Scheme 555-5b). Appropriate oxidant(s) can convert the primary alcohol 555-5.5 to carboxylic acid 555-5.6 or its corresponding ester. In the case of an ester, an additional deprotection step will give the carboxylic acid, 555-5.6. A variety of oxidation procedures exist in the literature and can be utilized here. These include but are not limited to the following methods: (i) pyridinium dichromate in Ac$_2$O, t-BuOH, and dichloromethane producing the t-butyl ester, followed by a deprotection using reagent such as trifluoroacetic acid to convert the ester to the corresponding carboxylic acid (see Classon, et al, *Acta Chem. Scand. Ser. B;* 39; 1985; 501-504. Cristalli, et al; *J. Med. Chem.;* 31; 1988; 1179-1183.); (ii) iodobenzene diacetate and 2,2,6,6-tetramethyl-1-piperidinyloxy, free radical (TEMPO) in acetonitrile, producing the carboxylic acid (See Epp, et al; *J. Org. Chem.* 64; 1999; 293-295. Jung et al; *J. Org. Chem.;* 66; 2001; 2624-2635.); (iii) sodium periodate, ruthenium(III) chloride in chloroform producing the carboxylic acid (see Kim, et al, *J. Med. Chem.* 37; 1994; 4020-4030. Homma, et al; *J. Med. Chem.;* 35; 1992; 2881-2890); (iv) chromium trioxide in acetic acid producing the carboxylic acid (see Olsson et al; *J. Med. Chem.;* 29; 1986; 1683-1689. Gallo-Rodriguez et al; *J. Med. Chem.;* 37; 1994; 636-646); (v) potassium permanganate in aqueous potassium hydroxide producing the carboxylic acid (see Ha, et al; *J. Med. Chem.;* 29; 1986; 1683-1689. Franchetti, et al; *J. Med. Chem.;* 41; 1998; 1.708-1715.) (vi) nucleoside oxidase from *S. maltophilia* to give the carboxylic acid (see Mahmoudian, et al; *Tetrahedron;* 54; 1998; 8171-8182.)

Carboxylic acid 555-5.6 may be converted by decarboxylation to acetate 555-5.7 using lead(IV) tetraacetate (Teng et al; (1994) *J. Org. Chem.;* 59:278-280; Schultz, et al; *J. Org. Chem.;* 48; 1983; 3408-3412. When lead(IV) tetraacetate is used together with lithium chloride (see Kochi, et al; *J. Am. Chem. Soc.;* 87; 1965; 2052), the corresponding chloride is obtained 555-5.8. Lead(IV) tetraacetate in combination with N-chlorosuccinimide can also produce 555-5.8 (Wang, et al; *Tet. Asym.;* 1; 1990; 527 and Wilson et al; *Tet. Asym.;* 1; 1990; 525). Alternatively, the acetate can also be converted to other leaving groups such as bromide by treatment of trimethylsilyl bromide (Spencer, et al; *J. Org. Chem.;* 64; 1999; 3987-3995).

Scheme 555-5b

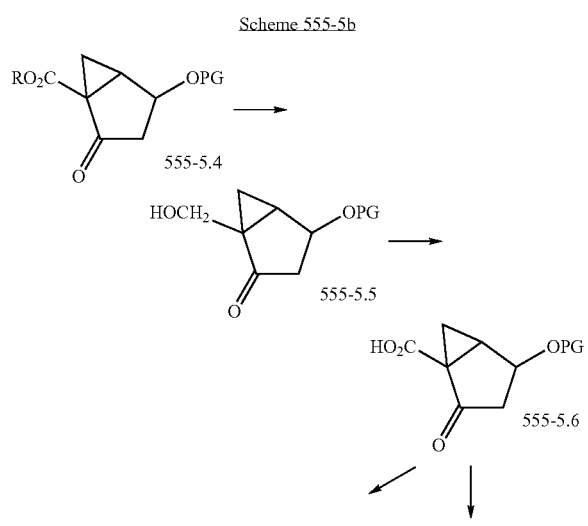

-continued

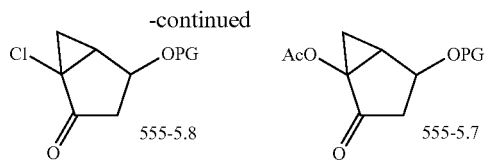

Intermediates 555-5.7 and 555-5.8 may react with a variety of nucleophiles as described by Teng et al; *Synlett;* 1996; 346-348 and U.S. Pat. No. 6,087,482; Column 54 line 64 to Column 55 line 20. Specifically, 555-5.7 may be reacted with diethyl hydroxymethylphosphonate in the presence of trimethylsilyl trifluoromethanesulfonate (TMS-OTf) to give 555-5.9 (Scheme 555-5c). It can be envisioned that other compounds with the general structure of HO-linker-POR$^{P1}$R$^{P2}$ can also be used so long as the functional groups in these compounds are compatible with the coupling reaction conditions. There are many examples in the published literature describing the coupling of 1' acetyl furanosyl compounds with a variety of alcohols. The reactions can be facilitated with a number of reagents, such as silver(I) salts (see Kim et al (1991) *J. Org. Chem.* 56:2642-2647, Toikka et al (1999) *J. Chem. Soc. Perkins Trans.* 1; 13:1877-1884); mercury(II) salts (see Veeneman et al (1987) *Rec. Trav. Chim. Pays-*Bas; 106:129-131); boron trifluoride diethyl etherate (see Kunz et al (1985) *Hel. Chim Acta;* 68:283-287); tin(II) chloride (see O'Leary et al (1994) *J. Org. Chem.* 59:6629-6636); alkoxide (see Shortnacy-Fowler et al (2001) *Nucleosides & Nucleotides;* 20:1583-1598); and iodine (see Kartha et al (2001) *J. Chem. Soc. Perkins Trans.* 1 770-772). These methods can be selectively used in conjunction with different methods in forming intermediates from 555-5.6 with various leaving groups (LG).

Scheme 555-5c

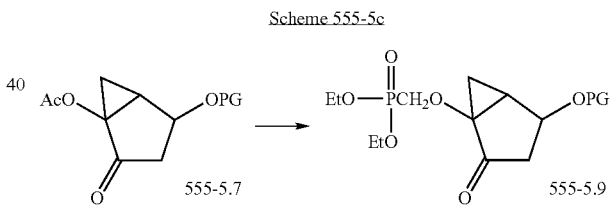

The introduction and removal of protecting groups (represented in the structures herein as PG) from a compound is common practice art in organic synthesis. Many sources of information of the art are available in the published literature, e.g. Greene and Wuts, *Protecting Groups in Organic Synthesis,* 3$^{rd}$ Ed., John Wiley & Sons, Inc., 1999. The main purpose is to temporarily transform a functional group and mask its reactivity so that it will survive a set of subsequent reaction procedures. Afterwards, the original functional group can be restored by a preconceived deprotection procedure. Therefore, the transformations in Schemes 555-(5a-c) are intended to build the [3.1.0] scaffold with the appropriate latent functionality or reactivity components.

The keto group of certain intermediates, e.g. 555-5.4 may be elaborated to ribofuranose-type analogs 555-6.1 where Z$^1$ are for example, each hydroxyl or protected hydroxyl (Scheme 555-6). The hydroxyl groups can be protected as benzoyl (Bz) esters to give 555-6.2. The bridgehead carboxylate ester can then be orthogonally hydrolyzed to give 555-6.3 or reduced to hydroxymethyl 555-6.4. Oxidation of 555-6.4, e.g. using iodobenzene diacetate and 2,2,6,6-tetramethyl-1- piperidinyloxy, free radical (TEMPO), converts the primary alcohol to the corresponding acid 555-6.3. Further oxidation of 555-6.3 using lead tetraacetate can produce acetate 555-6.5. Coupling between 555-6.5 and hydroxyalkyl dialkylphosponate compounds, e.g. diethyl hydroxymethylphosphonate (available from Sigma-Aldrich, Cat. No. 39,262-6) and TMS-OTf can afford 555-6.6. Treating 555-6.6 with TMS-Br converts the phosphodiester to the corresponding phosphonic acid 555-6.7. Deprotection, e.g. $NH_3$ in methanol, of the 2'- and 3'-hydroxyl gives 555-6.8.

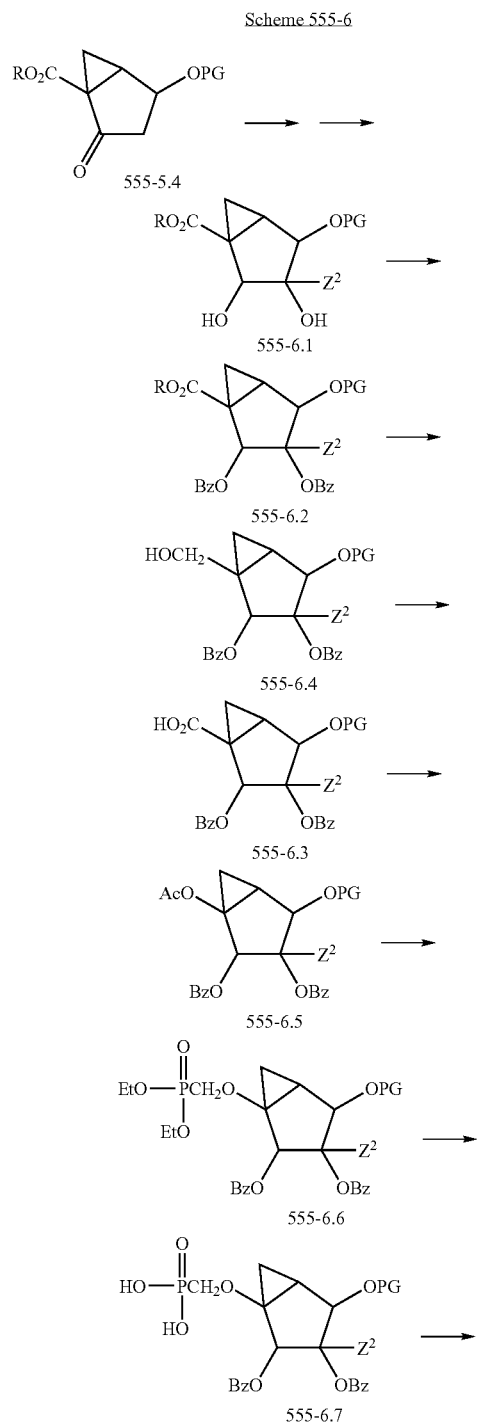

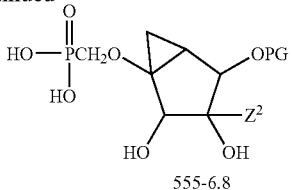

The phosphonic acids in 555-(6.6-6.8) are used as examples for illustration purpose. Other forms of phosphonates can be accessed via the phosphonic acid, or other forms, such as the corresponding diesters. See Schemes 555-A and 555-(1-4) for exemplary interconversions of phosphonate moieties.

Compounds such as 555-6.6 can be further elaborated by selective deprotection of PG and introduction of the nucleobase moiety (B). For example, where PG is trialkylsilyl, e.g. triethylsilyl, t-butyldimethylsilyl, or phenyldimethylsilyl, treatment of 555-6.6 with a fluoride reagent, e.g. tetrabutylammonium fluoride in THF, may selectively remove PG. The resulting hydroxyl may be converted to a leaving group (LG) such as chloro or acetate 555-7.1 under Vorbruggen-type reaction conditions, or the hydroxyl 555-7.2 reacted in situ, e.g. Mitsunobu conditions, to establish the carbon-nitrogen bond with a nucleobase or protected nucleobase reagent to give 555-7.3 (Scheme 555-7). Suitable nucleobase or protected nucleobase reagents (B) include thymidine, cytosine, adenine, guanine, and silylated forms thereof. The resulting covalent attachment may be 9-purinyl or 1-pyrimidinyl. Other positional isomers may result and conventional means of separation may be employed to generate pure 555-7.3 compounds. The 2' and 3' protecting groups (Bz=benzoyl) may be removed from intermediate 555-7.3 with aqueous base to give 555-7.4. The ethyl groups of 555-7.4 may be removed with a dealkylation reagent such as trimethylsilyl bromide to give phosphonic acid 555-7.5 which may be further elaborated according to the reactions shown in Schemes 555-A and 1-4 to other phosphonate moieties, including diphosphophosphonate and phosphophosphonate compounds.

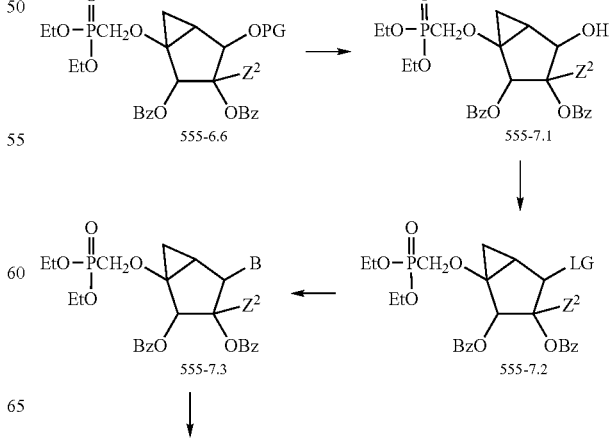

-continued

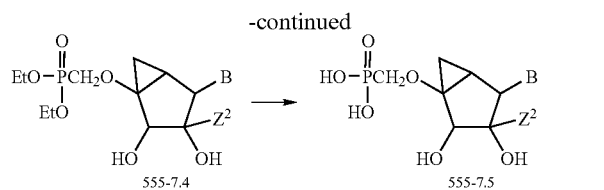

Scheme 555-8 shows an exemplary route to 2'-β-methyl, 2'-3' hydroxyl bicylco adenine compounds. The 3' and 5' hydroxyl groups of [3.1.0] bicyclo analog of adenosine 555-8.1 (Kim, et al (2002) J. Med. Chem. 45:208-218) may be selectively silylated to give 555-8.2. The 2' hydroxyl group may be oxidized under Dess-Martin periodinane conditions to give 555-83. The 2' keto of 555-8.3 may be methylenated with a Wittig reagent and desilylated to give 555-8.4. Epoxidation of 555-8.4 gives 555-8.5. Hydride attack on the methylene carbon of the epoxide 555-8.5 gives 555-8.6 with the 2',3'-α-dihydroxy, 2'-β-methyl motif. This synthetic route may be versatile in the preparation of a variety of 2',3'-α-dihydroxy, 2'-β-methyl[3.1.0] bicyclo compounds where B=any protected or unprotected nucleobase.

Scheme 555-8

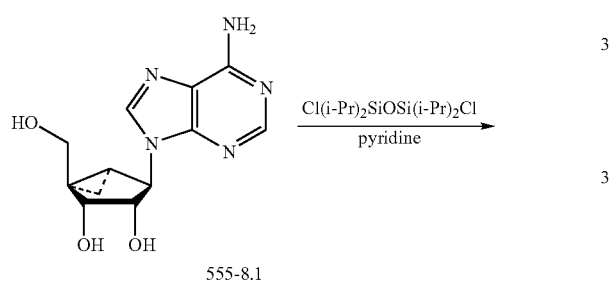

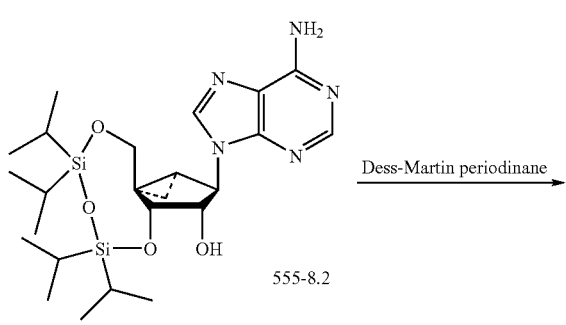

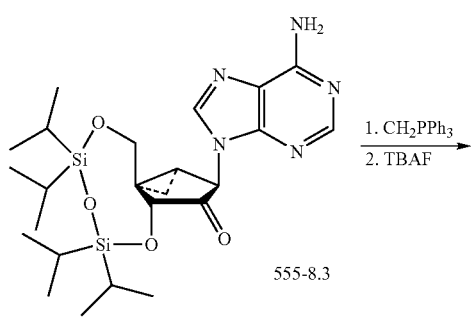

-continued

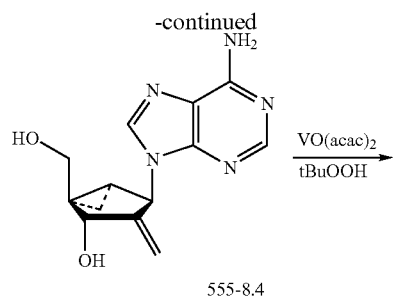

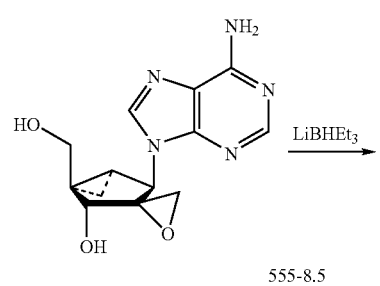

The 5' hydroxymethyl group of 2',3'-α-dihydroxy, 2'-β-methyl [3.1.0] bicyclo compounds, e.g. 555-8.6, may be elaborated by selective reactions such as those shown in Scheme 555-9. The 5' carbon may be removed by an oxidative decarboxylation to allow attachment of a phosphonate moiety through an oxygen atom bound directly to the [3.1.0] scaffold. The 5' hydroxyl group of 555-8.6 may be selectively protected as the 5' tert-butyldiphenylsilyl ether (TBDPS) and then the 2' and 3' hydroxyls may be protected as methoxymethyl ethers to give 555-9.1. The 5' TBDPSi group may be removed with tetra-butyl ammonium fluoride (TBAF) and the resulting hydroxymethyll oxidized with the periodinane reagent, PhI(OAc)$_2$ and TEMPO to the carboxylic acid 555-9.2. Oxidative decarboxylation of 555-9.2 with lead tetracetate and treatment with lithium hydroxide gives 555-9.3. Alkylation of the hydroxyl of 555-9.3 with bromomethyldiethyl phosphonate gives 555-9.4. The phosphonate ethyl groups and the 2',3' methoxymethyl (MOM) protecting groups may be removed with iodotrimethylsilane to give 555-9.5. The phosphonic acid group of 555-9.5 may be activated, for example with carbonyldiimidazole (CDI) and reacted with pyrophosphate anion to give diphosphophosphonate 555-9.6. Other phosphonic acid conversions may be conducted, as described in Schemes 555-A and 555 (1-4).

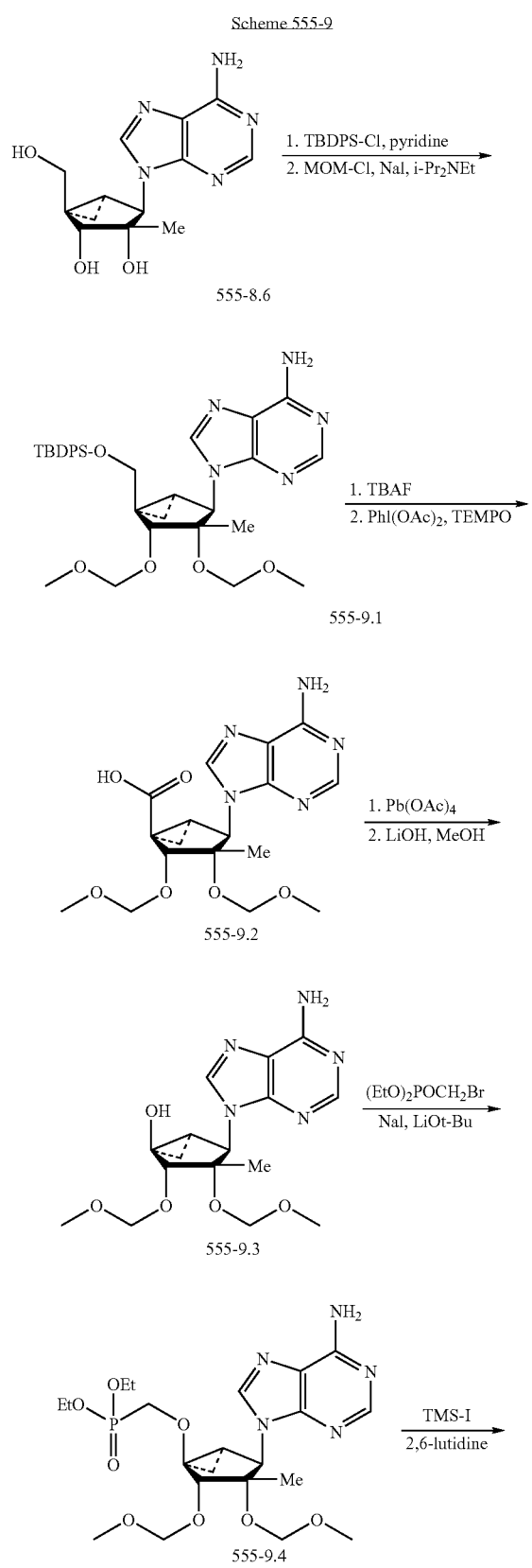

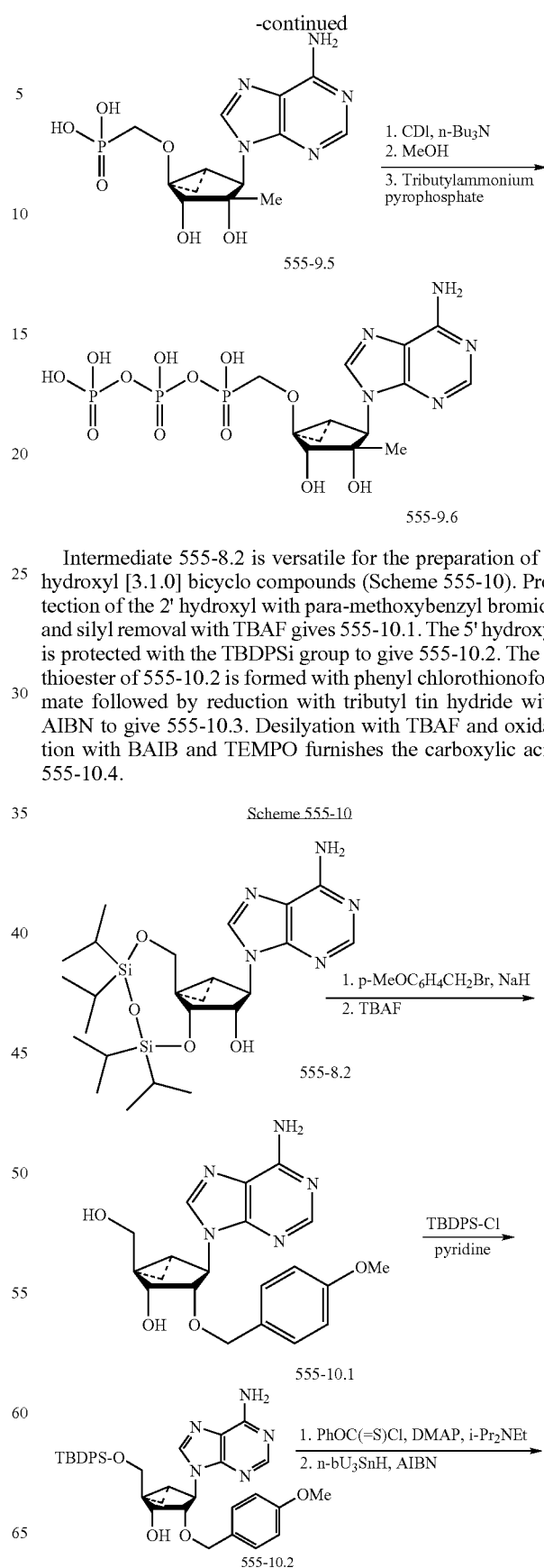

Intermediate 555-8.2 is versatile for the preparation of 2' hydroxyl [3.1.0] bicyclo compounds (Scheme 555-10). Protection of the 2' hydroxyl with para-methoxybenzyl bromide and silyl removal with TBAF gives 555-10.1. The 5' hydroxyl is protected with the TBDPSi group to give 555-10.2. The 3' thioester of 555-10.2 is formed with phenyl chlorothionoformate followed by reduction with tributyl tin hydride with AIBN to give 555-10.3. Desilation with TBAF and oxidation with BAIB and TEMPO furnishes the carboxylic acid 555-10.4.

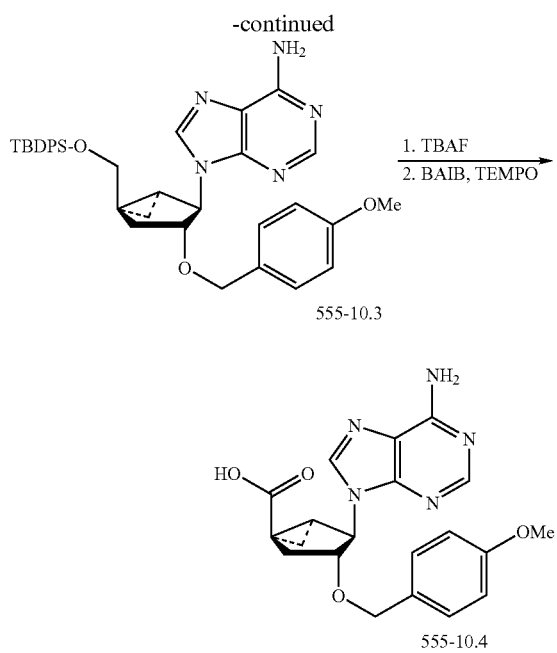

Oxidative decarboxylation of 555-10.4 with lead tetracetate followed by lithium hydroxide treatment gives the hydroxyl 555-11.1 (Scheme 555-11). Alkylation of hydroxyl 555-11.1 with bromomethyl diethyl phosphonate gives 555-11.2. Iodotrimethylsilane cleaves the ethyl groups from the diethylphosphonate and ceric ammonium nitrate deprotects the para-methoxy benzyl group of 555-11.2 to give 555-11.3. Phosphonate activation with CDI and addition of pyrophosphate gives the 2'-hydroxy diphosphophosphonate [3.1.0] compound 555-11.4.

Schedule 555-11

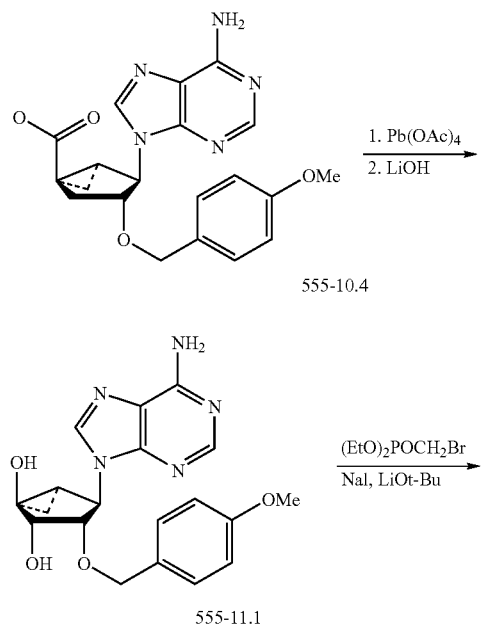

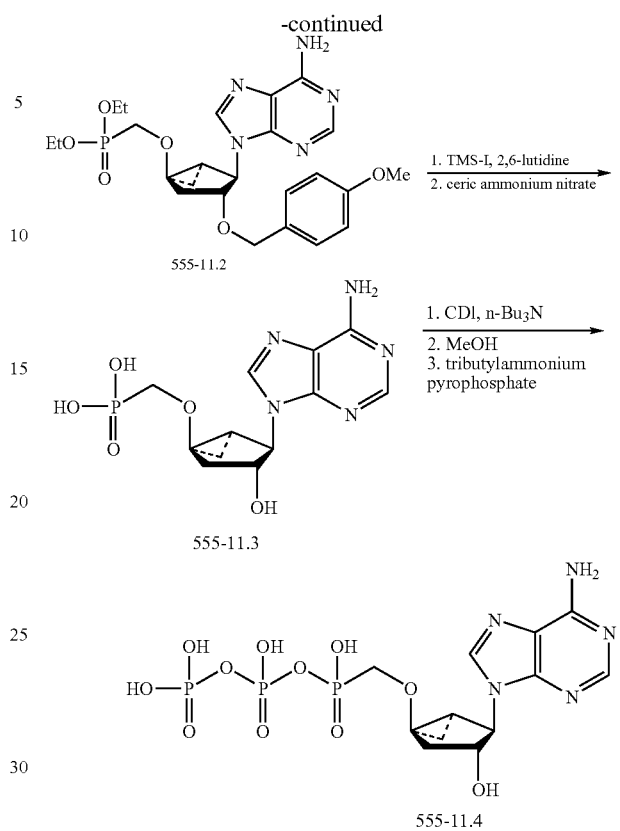

Example 556

Synthesis of Exemplary Compounds of the Invention

The following Schemes describe the general method of preparing the 2' fluoro, 2'-3' didehydro nucleosidescaffold of compounds of the present invention.

Methods of introduction of fluorine at the 2' position of ribonucleosides and nucleoside analogs are described in U.S. Pat. No. 5,824,793; U.S. Pat. No. 5,859,233; Choo, H. etal *Journal of Medicinal Chemistry* (2003), 46(3), 389-398; Moon, H. etal *Journal of the Chemical Society, Perkin Transactions* 1 (2002), (15), 1800-1804; Lee, Kyeong; Choi, Y. etal *Journal of Medicinal Chemistry* (2002), 45(6), 1313-1320; Lee, Kyeong; Choi, Yongseok; Hong, J. etal *Nucleosides & Nucleotides* (1999), 18(4 & 5), 537-540; Lee, K. etal *Journal of Medicinal Chemistry* (1999), 42(7), 1320-1328; Choi, Y. etal *Tetrahedron Letters* (1998), 39(25), 4437-4440; Chen, Shu-Hui etal *Bioorganic & Medicinal Chemistry Letters* (1998), 8(13), 1589-1594; Siddiqui, Maqbool etal *Tetrahedron Letters* (1998), 39(13), 1657-1660; Nakayama, Toshiaki etal *Nucleic Acids Symposium Series* (1991), 25(Symp. Nucleic Acids Chem., 18th, 1991), 191-2; Huang, Jai Tung etal *Journal of Medicinal Chemistry* (1991), 34(5), 1640-6; Sterzycki, Roman Z etal *Journal of Medicinal Chemistry* (1990), 33(8), 2150-7; Martin, Joseph A etal *Journal of Medicinal Chemistry* (1990), 33(8), 2137-45; Watanabe, Kyoichi etal *Journal of Medicinal Chemistry* (1990), 33(8), 2145-50; Zemlicka etal *Journal of the American Chemical Society* (1972) 94(9):3213-3218.

Schemes 556 (A-F) show the synthetic routes which have been utilized to prepare the exemplary embodiments shown therein.

Scheme 556-A

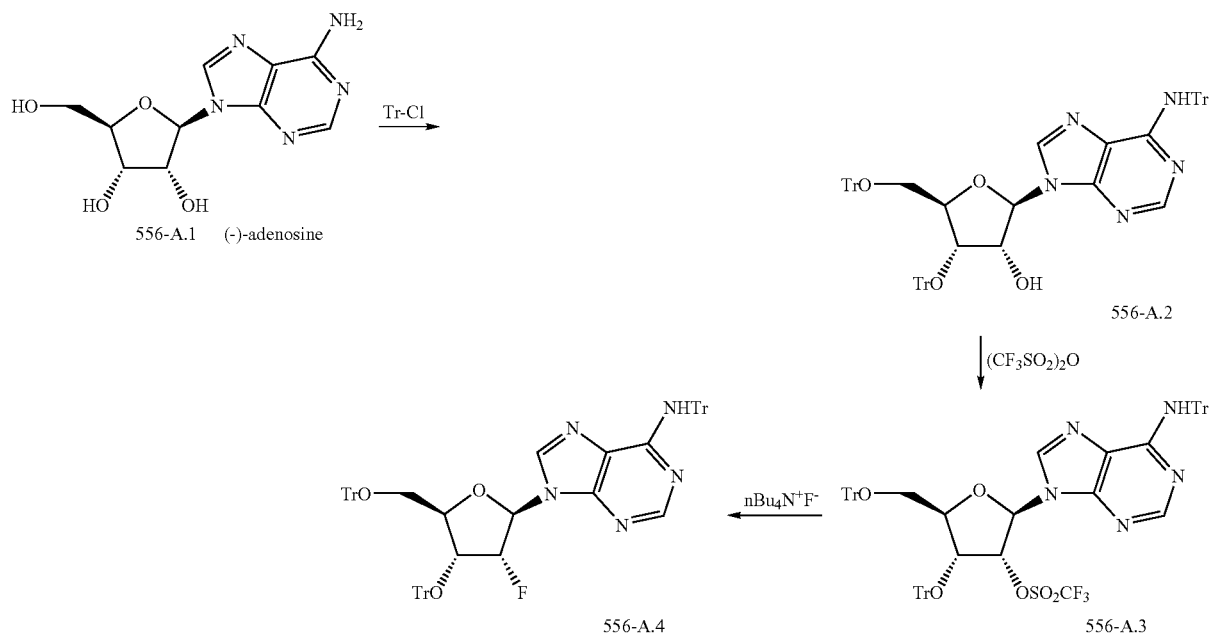

The (−) enantiomer of adenosine 556-A.1 was tritylated at the N-6 of the adenine exocyclic amine and the 5′ hydroxyl with an excess of trityl (Tr, triphenylmethyl, Ph$_3$C—) chloride with dimethylaminopyridine in pyridine to give bis-trityl 556-A.2 which was treated with triflic anhydride in dichloromethane and DMAP to give 556-A.3 (Scheme 556-A). The 2′ triflate group was displaced by fluoride with tetra-butylammonium fluoride in THF at room temperature to give 556-A.4.

-continued

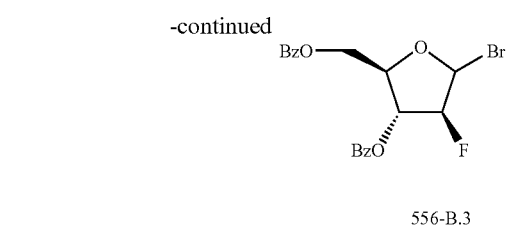

Scheme 556-B

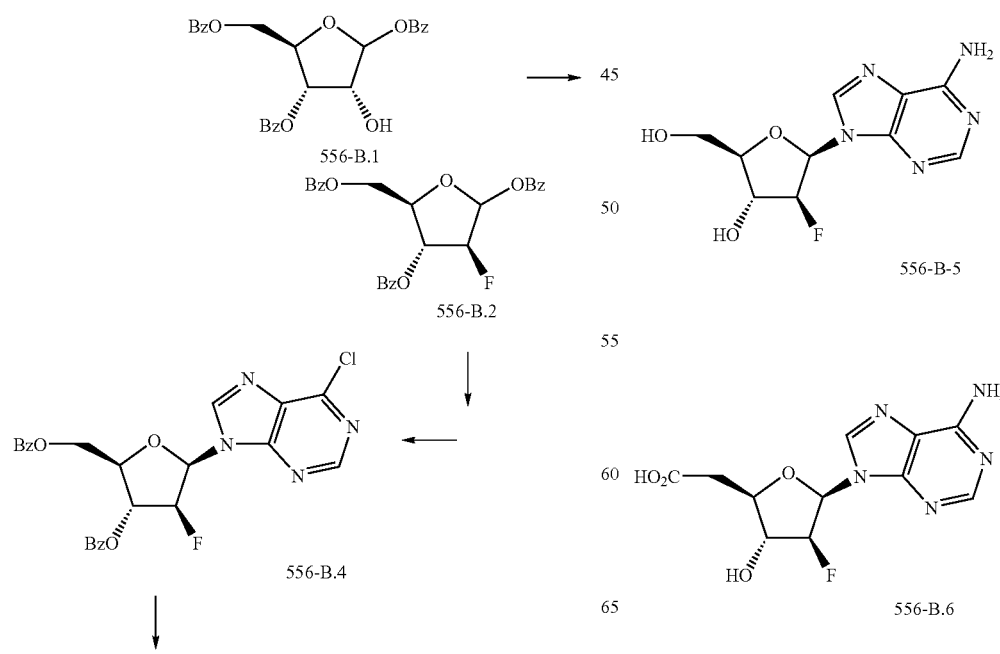

Scheme 556-C
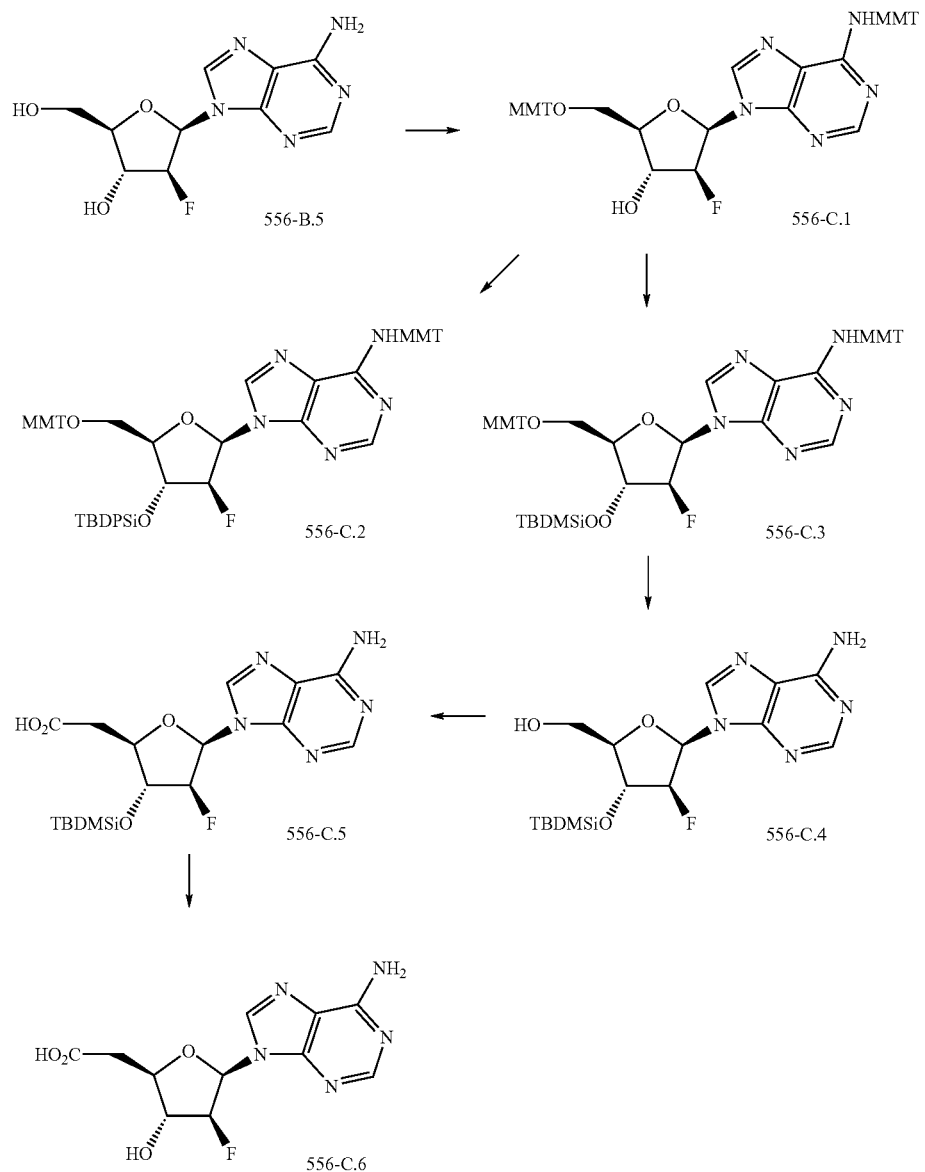
Scheme 556-D
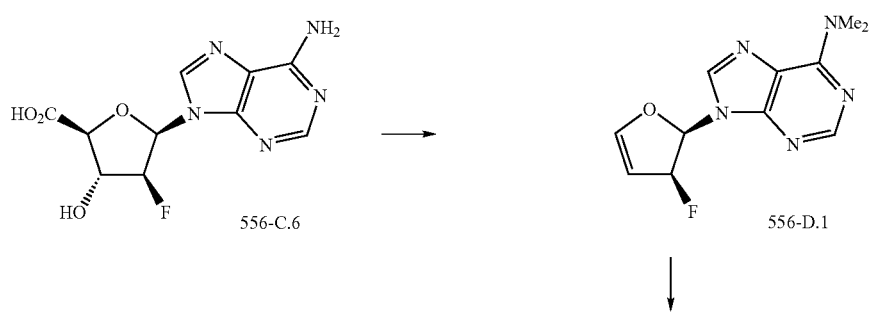

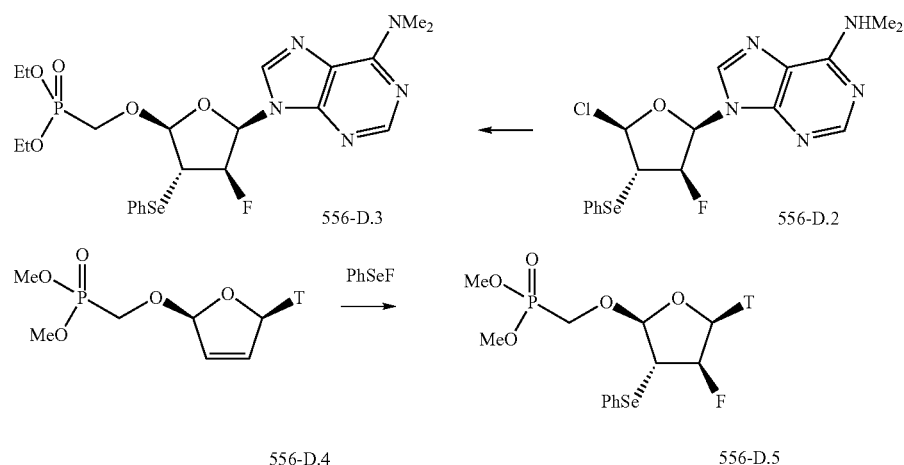
Scheme 556-E
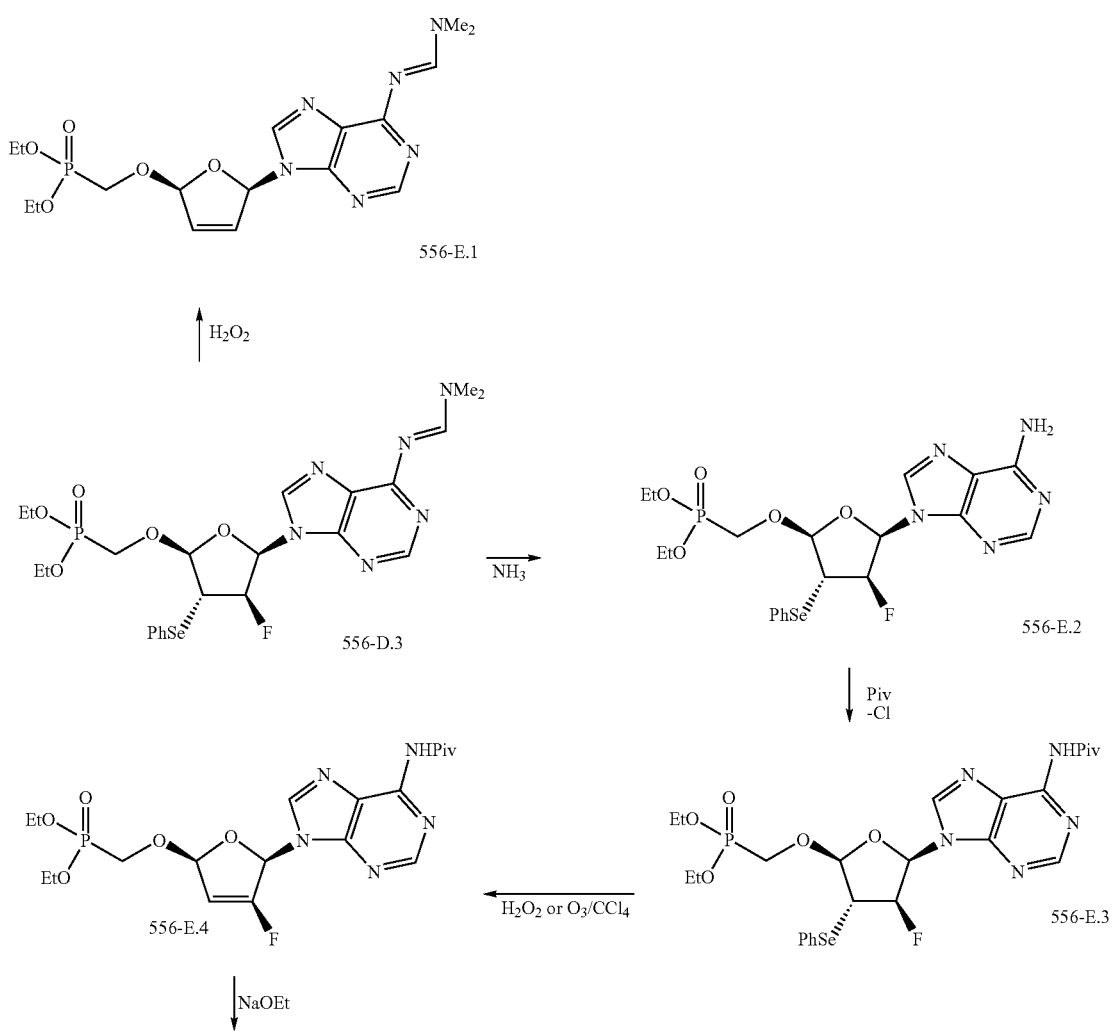

-continued

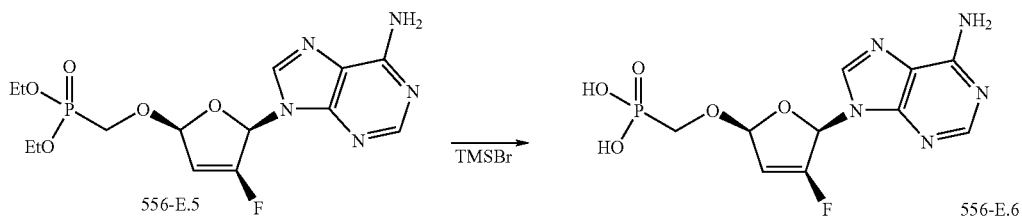

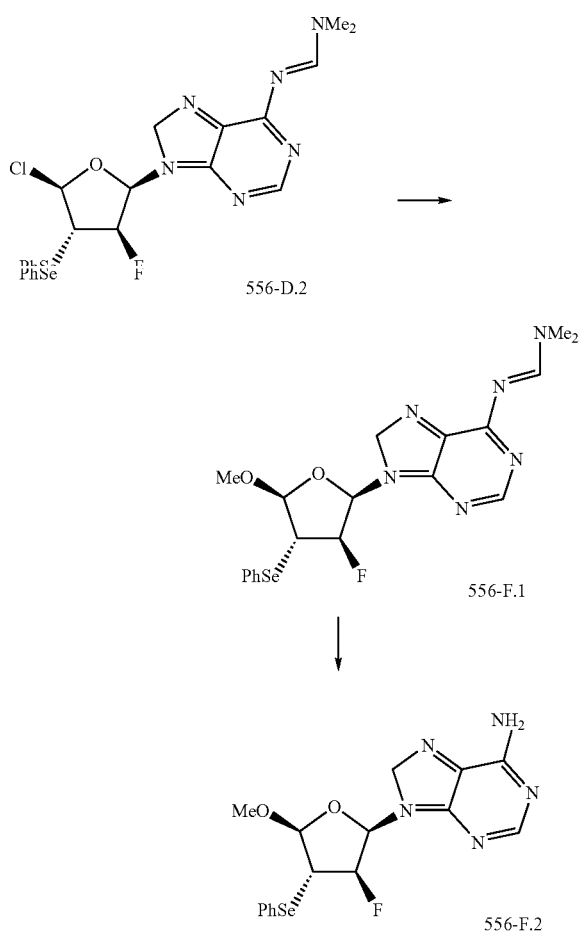

Example 600

By way of example and not limitation, embodiments of the invention are named below in tabular format (Table 100). These embodiments are of the general formula "MBF":

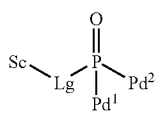

MBF

Ele;2qach embodiment of MBF is depicted as a substituted nucleus (Sc). Sc is described in formula 1-336 herein, wherein $A^0$ is the point of covalent attachment of Sc to Lg, as well as in Tables 1.1 to 1.5 below. For those embodiments described in Table 100, Sc is a nucleus designated by a number and each substituent is designated in order by letter or number. Tables 1.1 to 1.5 are a schedule of nuclei used in forming the embodiments of Table 100. Each nucleus (Sc) is given a number designation from Tables 1.1 to 1.5, and this designation appears first in each embodiment name. Similarly, Tables 10.1 to 10.19 and 20.1 to 20.36 list the selected linking groups (Lg) and prodrug ($Pd^1$ and $Pd^2$) substituents, again by letter or number designation, respectively. Accordingly, a compound of the formula MBF includes compounds having Sc groups based on formula 1-336 herein as well as compounds according to Table 100 below. In all cases, compounds of the formula MBF have groups Lg, $Pd^1$ and $Pd^2$ setforth in the Tables below.

Accordingly, each named embodiment of Table 100 is depicted by a number designating the nucleus from Table 1.1-1.5, followed by a letter designating the linking group (Lg) from Table 10.1-10.19, and two numbers designating the two prodrug groups ($Pd^1$ and $Pd^2$) from Table 20.1-20.36. In graphical tabular form, each embodiment of Table 100 appears as a name having the syntax:

Sc.Lg.$Pd^1$.$Pd^2$

Each Sc group is shown having a tilda ("~"). The tilda is the point of covalent attachment of Sc to Lg. $Q^1$ and $Q^2$ of the linking groups (Lg), it should be understood, do not represent groups or atoms but are simply connectivity designations. $Q^1$ is the site of the covalent bond to the nucleus (Sc) and $Q^2$ is the site of the covalent bond to the phosphorous atom of formula MBF. Each prodrug group ($Pd^1$ and $Pd^2$) are covalently bonded to the phosphorous atom of MBF at the tilda symbol ("~"). Some embodiments of Tables 10.1-10.19 and 20.1-20.36 may be designated as a combination of letters and numbers (Table 10.1-10.19) or number and letter (Table 20.1-20.36). For example there are Table 10 entries for BJ1 and BJ2. In any event, entries of Table 10.1-10.19 always begin with a letter and those of Table 20.1-20.36 always begin with a number. When a nucleus (Sc) is shown enclosed within square brackets ("[ ]") and a covalent bond extends outside the brackets, the point of covalent attachment of Sc to Lg may be at any substitutable site on SC. Selection of the point of attachment is described herein. By way of example and not limitation, the point of attachment is selected from those depicted in the schemes and examples.

TABLE 1.1
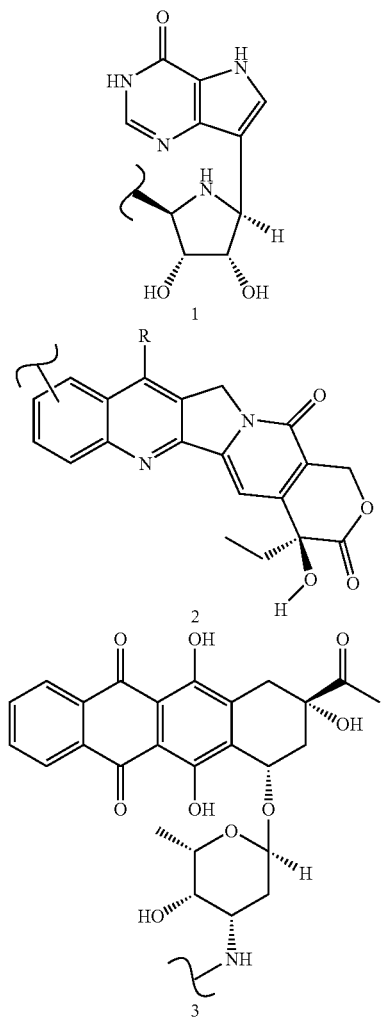
TABLE 1.1-continued
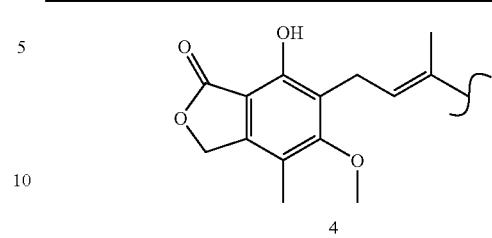
TABLE 1.2
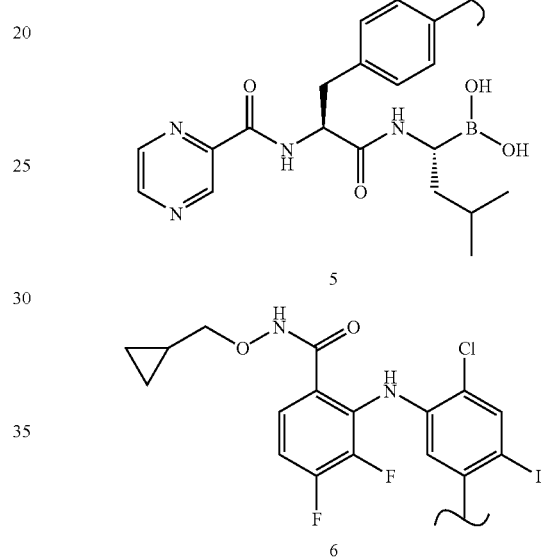
TABLE 1.3
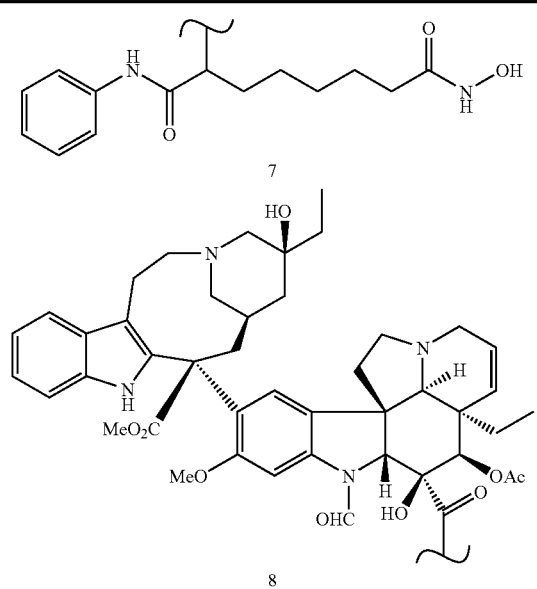

TABLE 1.3-continued
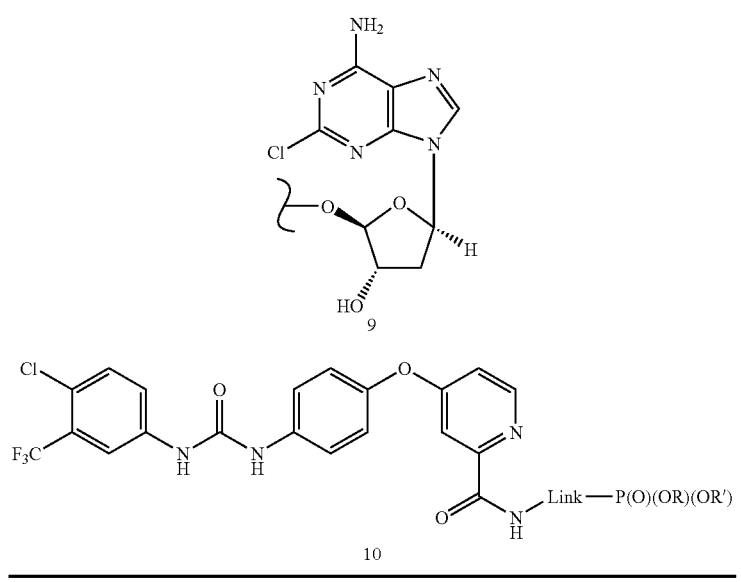
TABLE 1.4
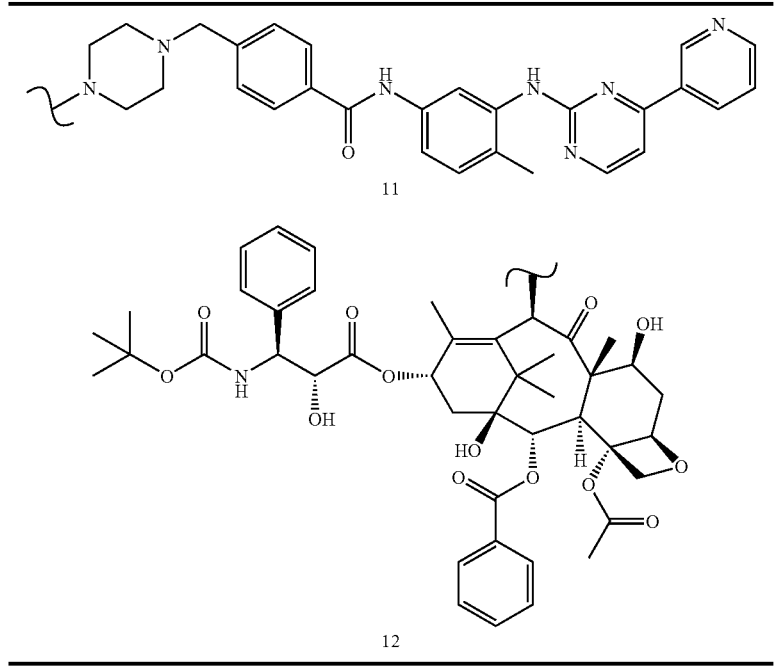
TABLE 1.5
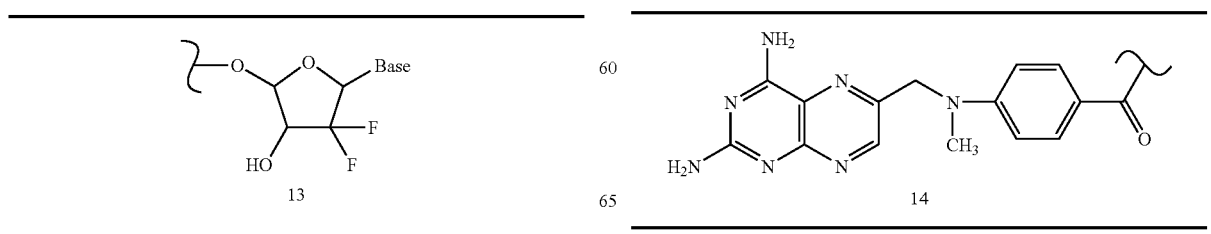

TABLE 10.1

| | |
|---|---|
| $Q^1\text{-}R^{5a}\text{-}Q^2$ A | |
| $Q^1\text{—}Q^2$ B | |
| $Q^1\text{-}Y^2\text{-}Q^2$ C | |
| $Q^1\text{-}W^{5a}\text{-}Q^2$ D | |
| $Q^1\text{-}Y^2\text{-}R^{5a}\text{-}Q^2$ E | |
| $Q^1\text{-}R^{5a}\text{-}Y^2\text{-}Q^2$ F | |
| $Q^1\text{-}Y^2\text{-}W^{5a}\text{-}Q^2$ G | |
| $Q^1\text{-}W^{5a}\text{-}Y^2\text{-}Q^2$ H | |
| $Q^1\text{-}W^{5a}\text{-}R^{5a}\text{-}Q^2$ I | |
| $Q^1\text{-}R^{5a}\text{-}W^{5a}\text{-}Q^2$ J | |
| $Q^1\text{-}W^{5a}\text{-}W^{5a}\text{-}Q^2$ K | |
| $Q^1\text{-}R^{5a}\text{-}W^{5a}\text{-}R^{5a}\text{-}Q^2$ L | |
| $Q^1\text{-}R^{5a}\text{-}W^{5a}\text{-}W^{5a}\text{-}Q^2$ M | |
| $Q^1\text{-}R^{5a}\text{-}W^{5a}\text{-}Y^2\text{-}Q^2$ N | |
| $Q^1\text{-}R^{5a}\text{-}Y^2\text{-}R^{5a}\text{-}Q^2$ O | |

TABLE 10.2

| | |
|---|---|
| $Q^1\text{-}R^{5a}\text{-}Y^2\text{-}W^{5a}\text{-}Q^2$ P | |
| $Q^1\text{-}W^{5a}\text{-}R^{5a}\text{-}W^{5a}\text{-}Q^2$ Q | |

TABLE 10.2-continued

| | |
|---|---|
| $Q^1\text{-}W^{5a}\text{-}R^{5a}\text{-}Y^2\text{-}Q^2$ R | |
| $Q^1\text{-}W^{5a}\text{-}W^{5a}\text{-}R^{5a}\text{-}Q^2$ S | |
| $Q^1\text{-}W^{5a}\text{-}W^{5a}\text{-}Y^2\text{-}Q^2$ T | |
| $Q^1\text{-}W^{5a}\text{-}Y^2\text{-}R^{5a}\text{-}Q^2$ U | |
| $Q^1\text{-}W^{5a}\text{-}Y^2\text{-}W^{5a}\text{-}Q^2$ V | |
| $Q^1\text{-}Y^2\text{-}R^{5a}\text{-}W^{5a}\text{-}Q^2$ W | |
| $Q^1\text{-}Y^2\text{-}R^{5a}\text{-}Y^2\text{-}Q^2$ X | |
| $Q^1\text{-}Y^2\text{-}W^{5a}\text{-}R^{5a}\text{-}Q^2$ Y | |
| $Q^1\text{-}Y^2\text{-}W^{5a}\text{-}W^{5a}\text{-}Q^2$ Z | |
| $Q^1\text{-}Y^2\text{-}W^{5a}\text{-}Y^2\text{-}Q^2$ AA | |

TABLE 10.3

| | |
|---|---|
| $Q^1\text{-}CH_2\text{-}Q^2$ AB | |
| $Q^1\text{-}CH(CH_3)\text{-}Q^2$ AC | |
| $Q^1\text{-}CH_2CH_2\text{-}Q^2$ AD | |
| $Q^1\text{-}CH_2CH_2CH_2\text{-}Q^2$ AE | |
| $Q^1\text{-}CH_2CH(CH_3)\text{-}Q^2$ AF | |

TABLE 10.3-continued
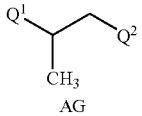
AG
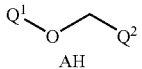
AH
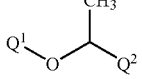
AI
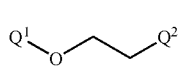
AJ
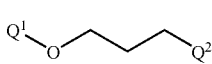
AK
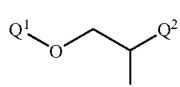
AL
AM
TABLE 10.4
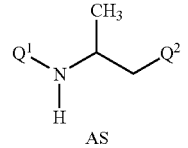
AN
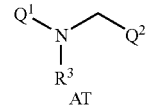
AO
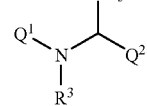
AP
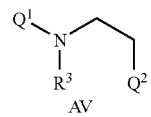
AQ
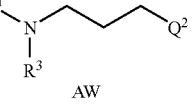
AR
TABLE 10.4-continued
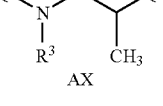
AS
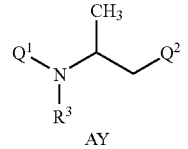
AT
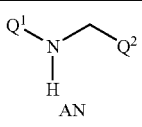
AU
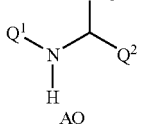
AV
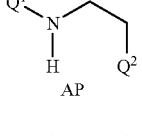
AW
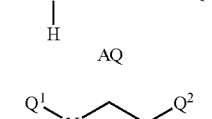
AX
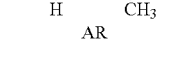
AY
TABLE 10.5
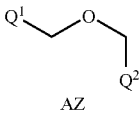
AZ
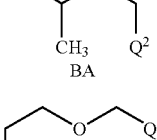
BA
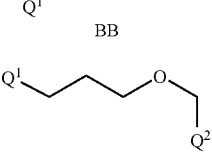
BB
BC

TABLE 10.5-continued
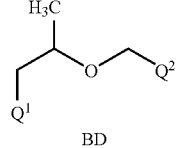
BD
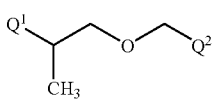
BE
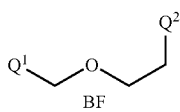
BF
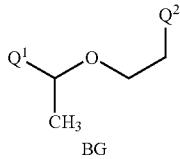
BG
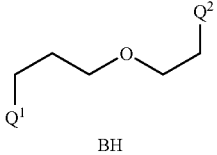
BH
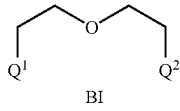
BI
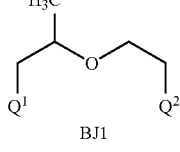
BJ1
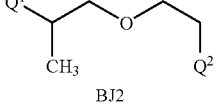
BJ2
TABLE 10.6
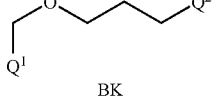
BK
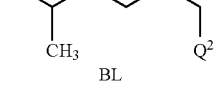
BL
TABLE 10.6-continued
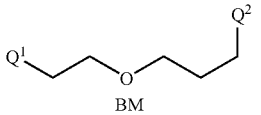
BM
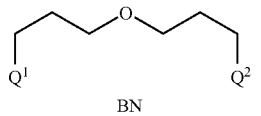
BN
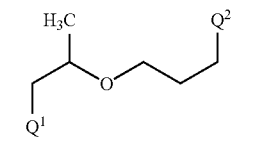
BO
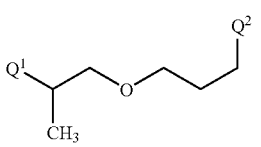
BP
TABLE 10.7
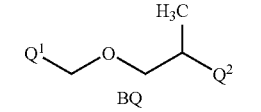
BQ
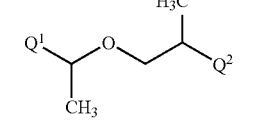
BR
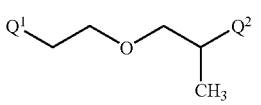
BS
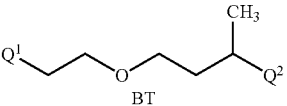
BT
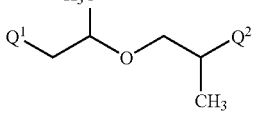
BU
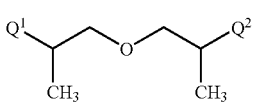
BV

TABLE 10.8
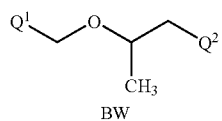
BW
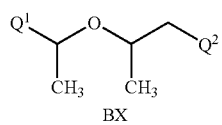
BX
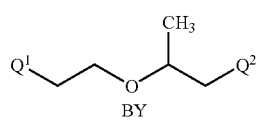
BY
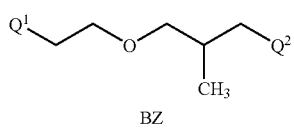
BZ
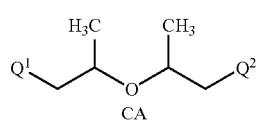
CA
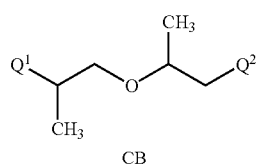
CB
TABLE 10.9
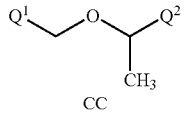
CC
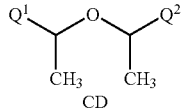
CD
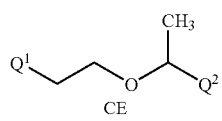
CE
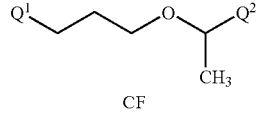
CF
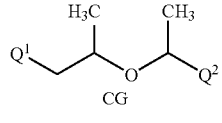
CG
TABLE 10.9-continued
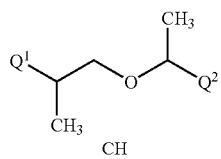
CH
TABLE 10.10
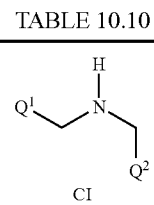
CI
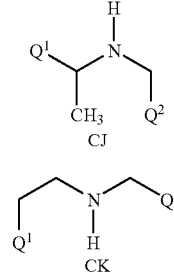
CJ
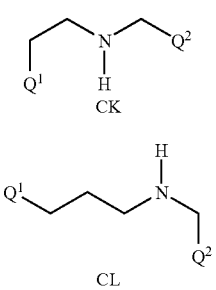
CK
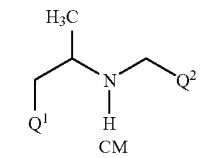
CL
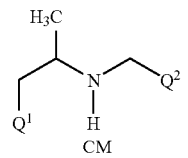
CM
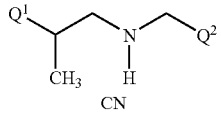
CN
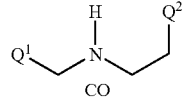
CO
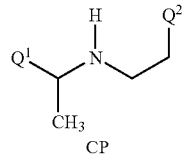
CP
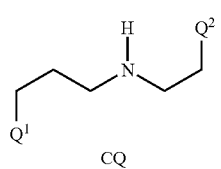
CQ TABLE 10.10-continued
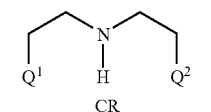
CR
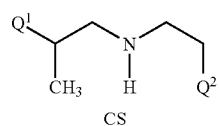
CS
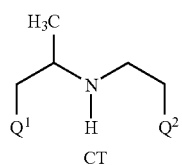
CT
TABLE 10.11
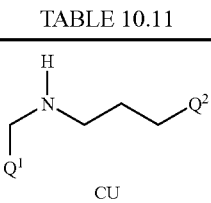
CU
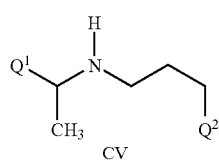
CV
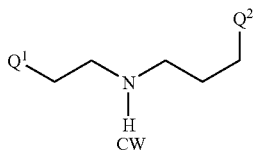
CW
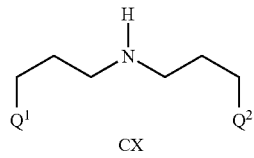
CX
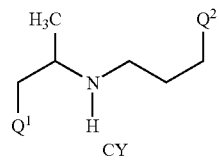
CY
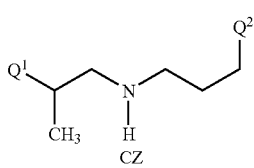
CZ
TABLE 10.12
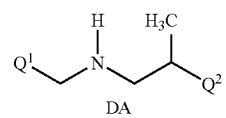
DA
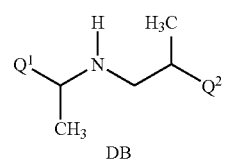
DB
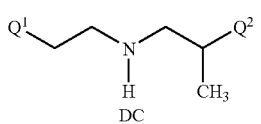
DC
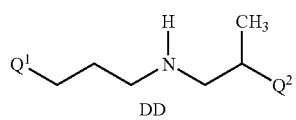
DD
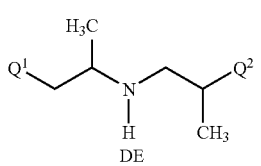
DE
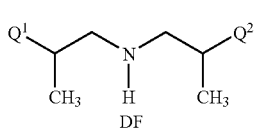
DF
TABLE 10.13
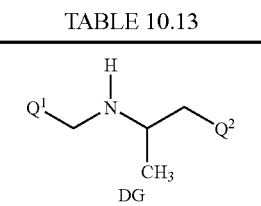
DG
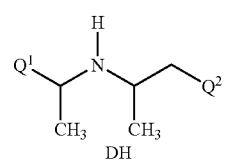
DH
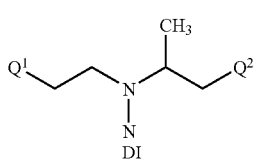
DI
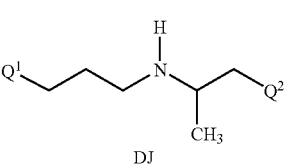
DJ

TABLE 10.13-continued
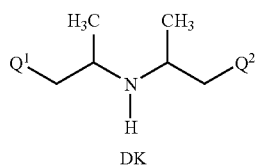
DK
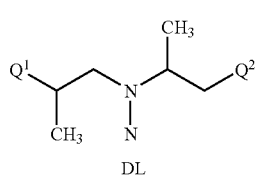
DL
TABLE 10.14
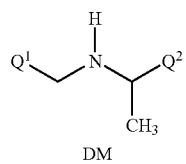
DM
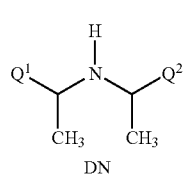
DN
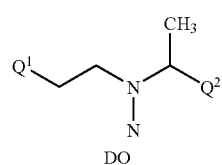
DO
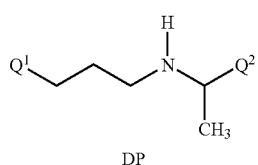
DP
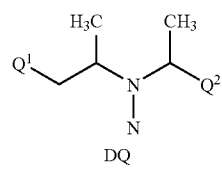
DQ
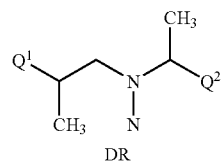
DR
TABLE 10.15
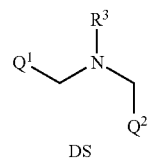
DS
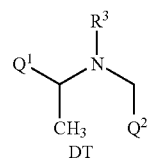
DT
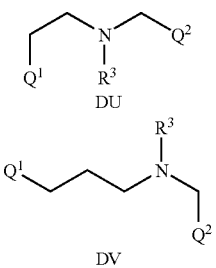
DU
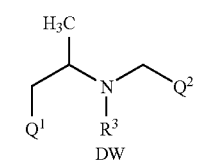
DV
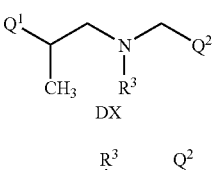
DW
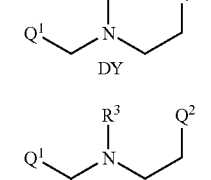
DX
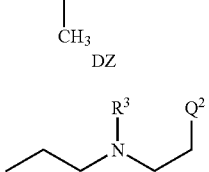
DY
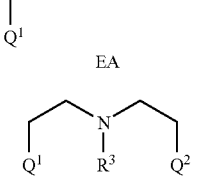
DZ
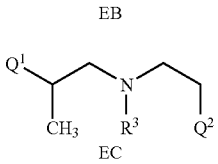
EA
EB
EC TABLE 10.15-continued
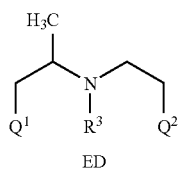
ED
TABLE 10.16
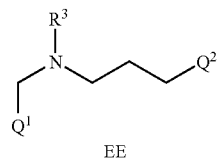
EE
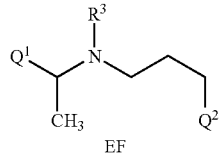
EF
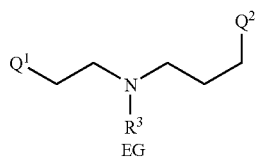
EG
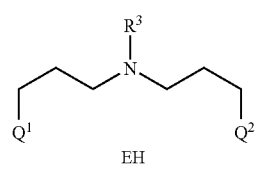
EH
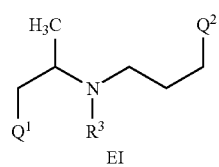
EI
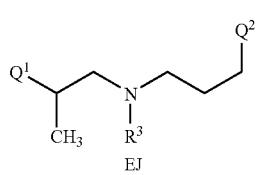
EJ
TABLE 10.17
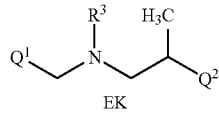
EK
TABLE 10.17-continued
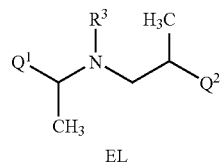
EL
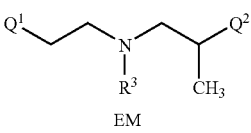
EM
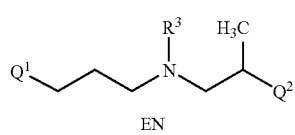
EN
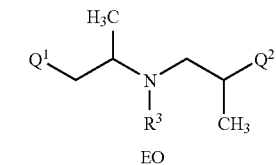
EO
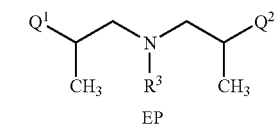
EP
TABLE 10.18
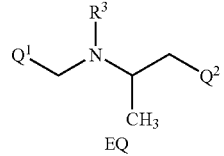
EQ
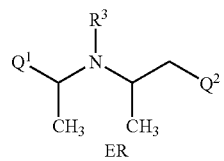
ER
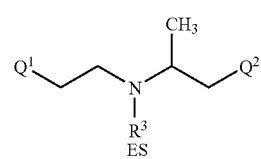
ES
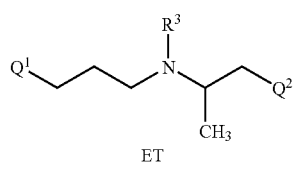
ET TABLE 10.18-continued
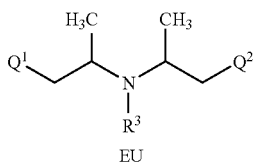
EU
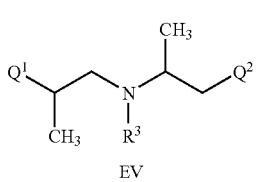
EV
TABLE 10.19
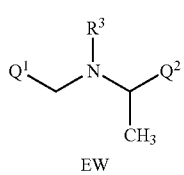
EW
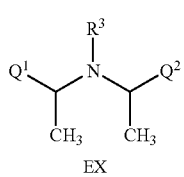
EX
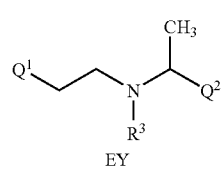
EY
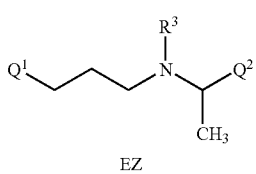
EZ
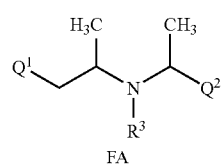
FA
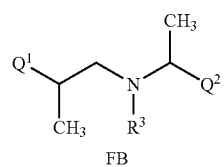
FB
TABLE 20.1
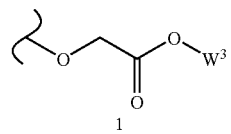
1
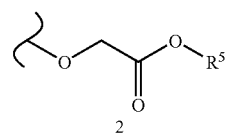
2
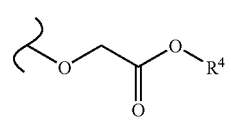
3
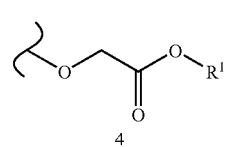
4
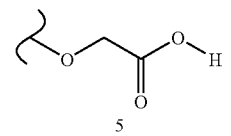
5
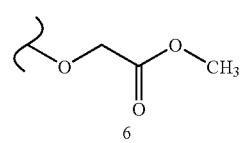
6
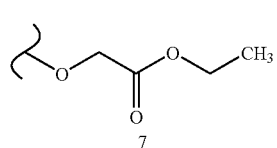
7
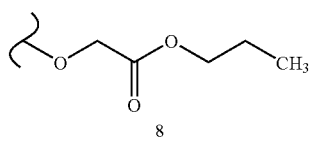
8
TABLE 20.2
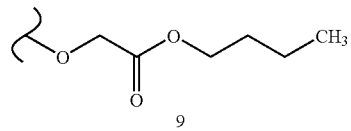
9
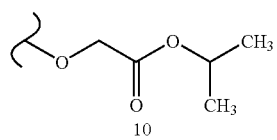
10

TABLE 20.2-continued
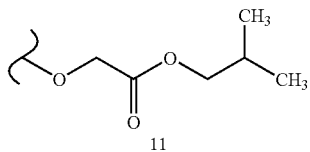
11
TAABLE 20.3
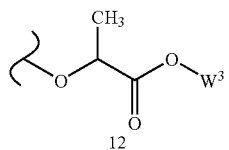
12
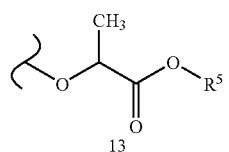
13
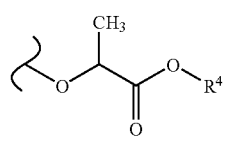
14
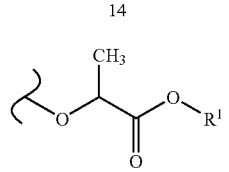
15
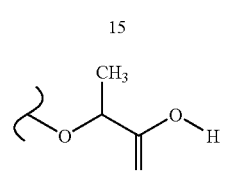
16
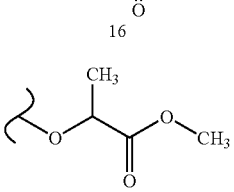
17
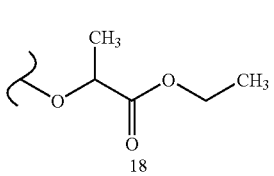
18
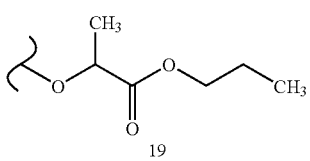
19
TABLE 20.4
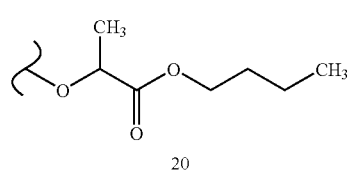
20
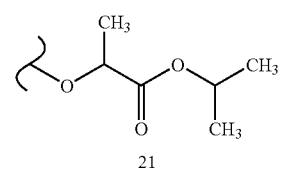
21
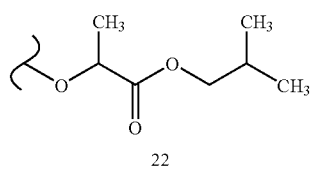
22
TABLE 20.5
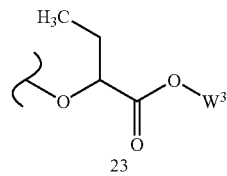
23
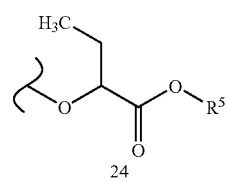
24
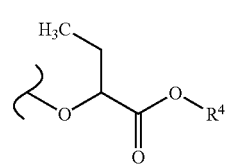
25
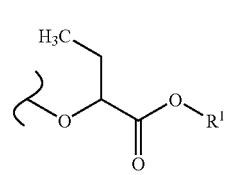
26
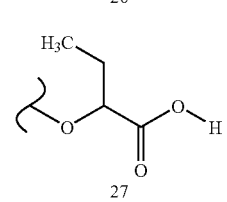
27

TABLE 20.5-continued
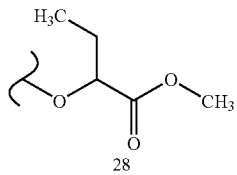
28
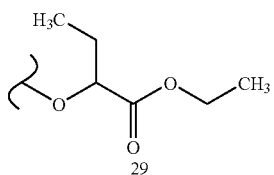
29
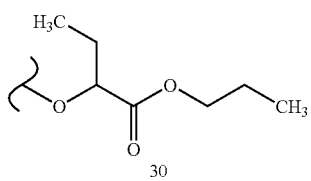
30
TABLE 20.6
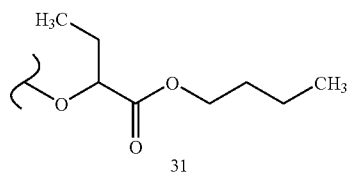
31
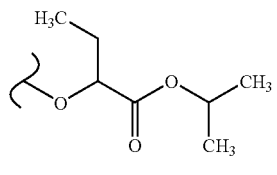
32
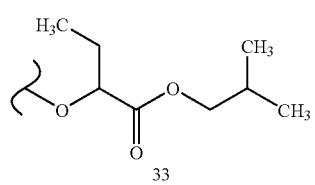
33
TAABLE 20.7
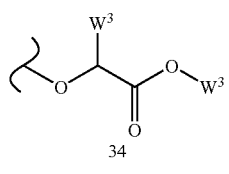
34
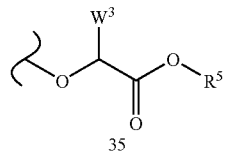
35
TAABLE 20.7-continued
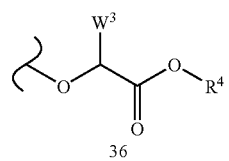
36
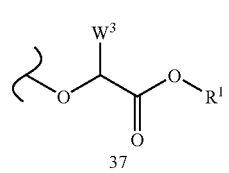
37
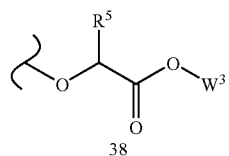
38
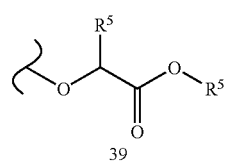
39
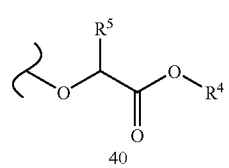
40
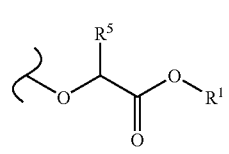
41
TABLE 20.8
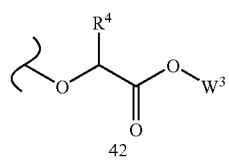
42
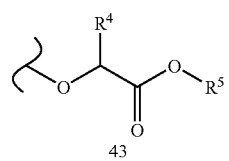
43
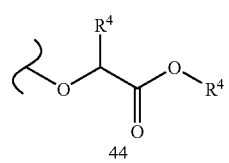
44

TABLE 20.8-continued
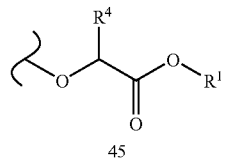
45
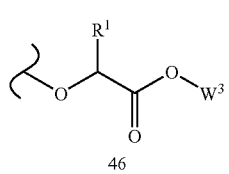
46
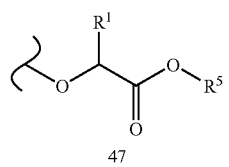
47
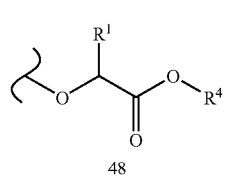
48
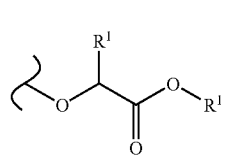
49
TABLE 20.9
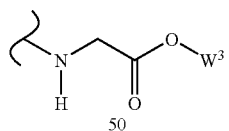
50
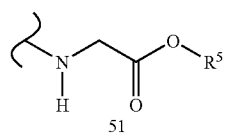
51
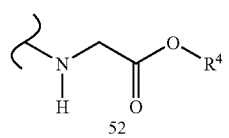
52
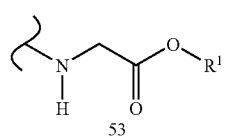
53
TABLE 20.9-continued
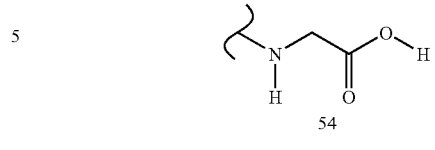
54
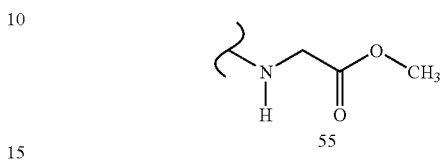
55
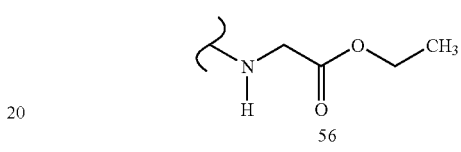
56
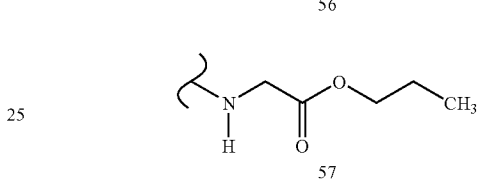
57
TABLE 20.10
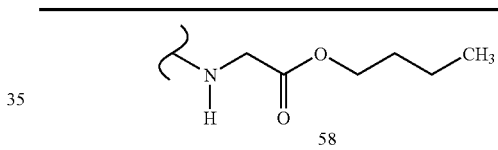
58
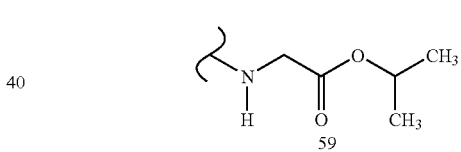
59
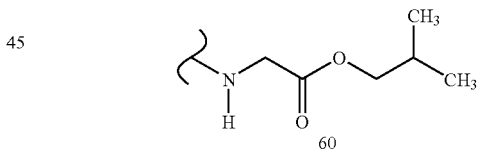
60
TABLE 20.11
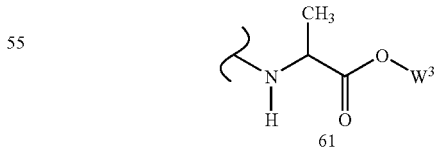
61
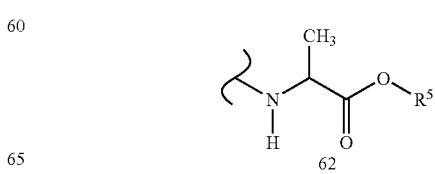
62

TABLE 20.11-continued 63, 64, 65, 66, 67, 68: alanine ester/acid structures with OR⁴, OR¹, OH, OCH₃, OEt, O-propyl

TABLE 20.12

69, 70, 71: alanine butyl, isopropyl, isobutyl esters

TABLE 20.13

72, 73, 74, 75, 76, 77, 78, 79: 2-aminobutyric acid derivatives with OW³, OR⁵, OR⁴, OR¹, OH, OCH₃, OEt, O-propyl TABLE 20.14
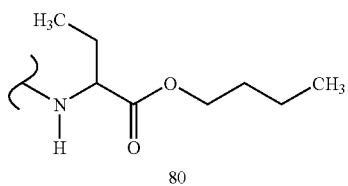
80
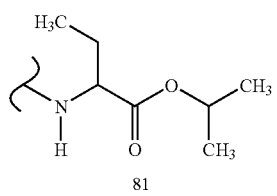
81
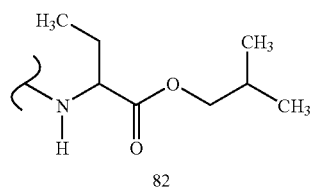
82
TABLE 20.15
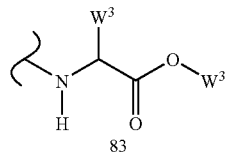
83
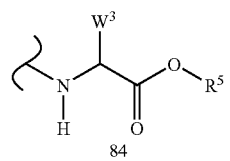
84
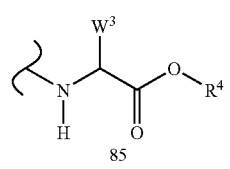
85
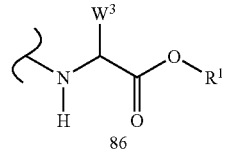
86
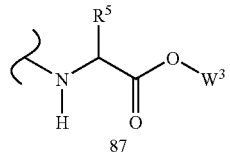
87
TABLE 20.15-continued
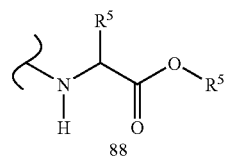
88
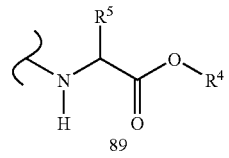
89
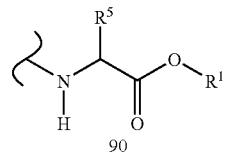
90
TABLE 20.16
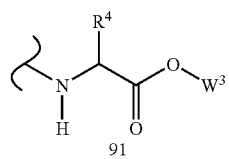
91
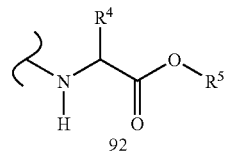
92
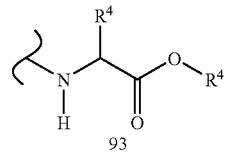
93
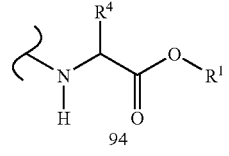
94
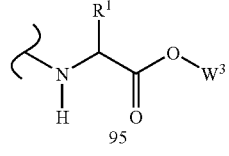
95
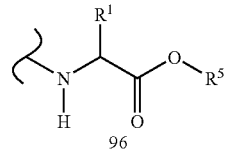
96

TABLE 20.16-continued
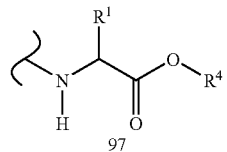
97
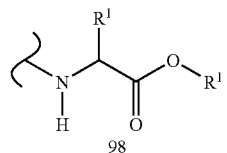
98
TABLE 20.17
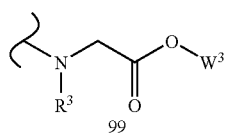
99
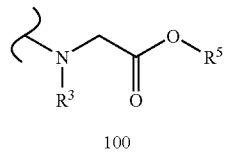
100
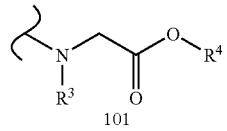
101
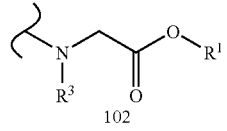
102
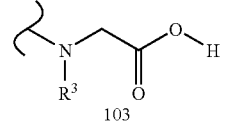
103
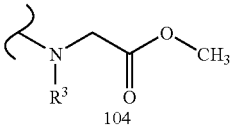
104
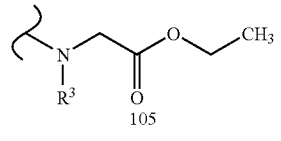
105
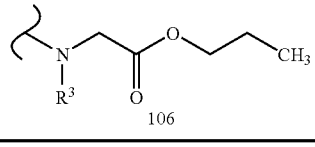
106
TABLE 20.18
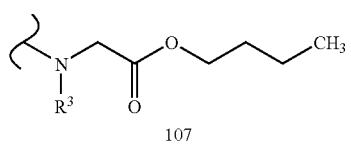
107
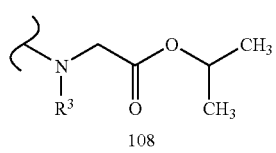
108
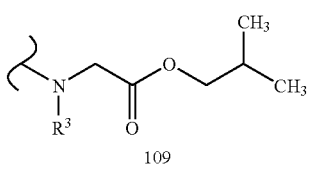
109
TABLE 20.19
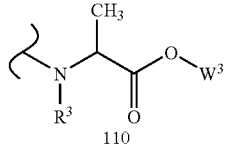
110
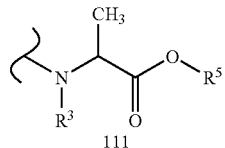
111
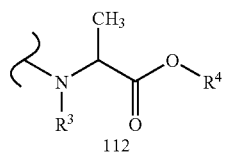
112
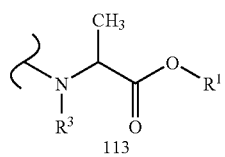
113
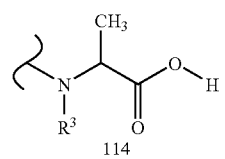
114
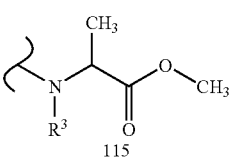
115

TABLE 20.19-continued
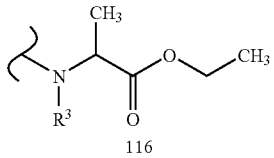
116
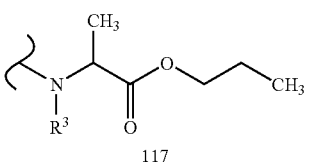
117
TABLE 20.20
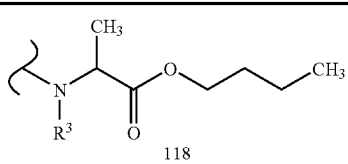
118
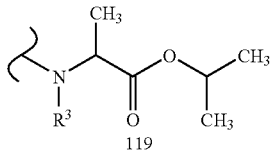
119
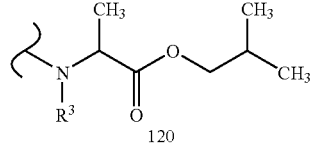
120
TABLE 20.21
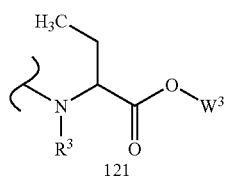
121
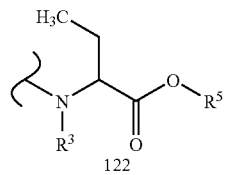
122
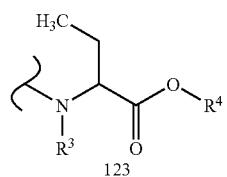
123
TABLE 20.21-continued
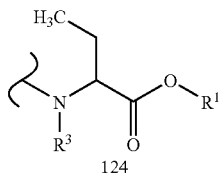
124
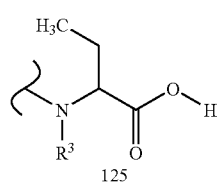
125
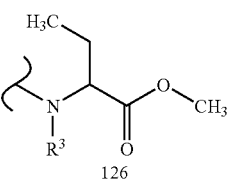
126
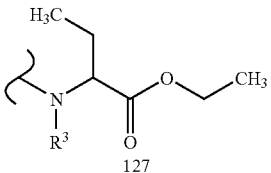
127
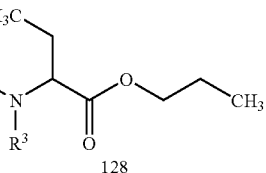
128
TABLE 20.22
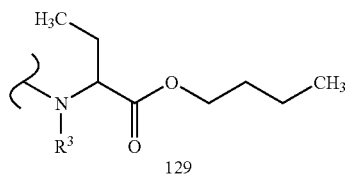
129
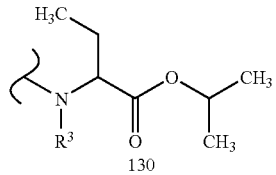
130
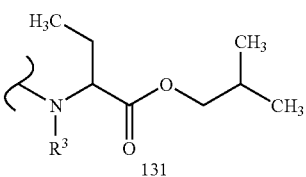
131

TABLE 20.23
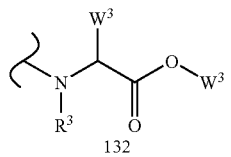
132
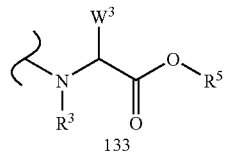
133
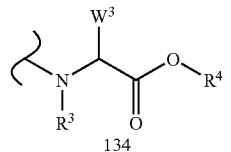
134
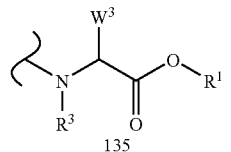
135
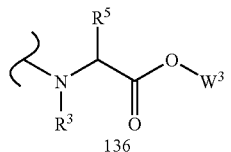
136
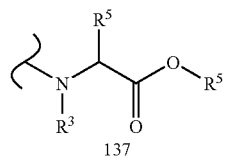
137
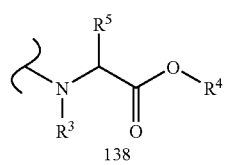
138
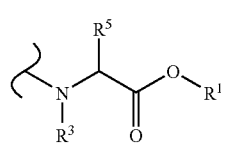
139
TABLE 20.24
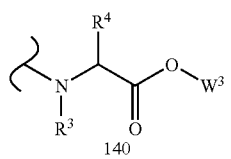
140
TABLE 20.24-continued
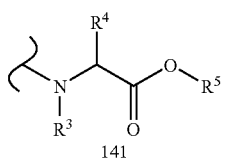
141
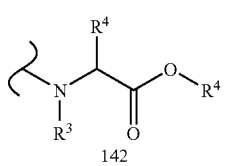
142
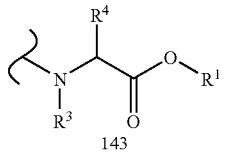
143
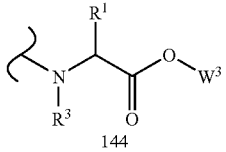
144
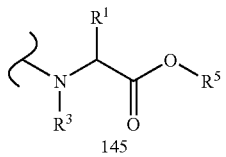
145
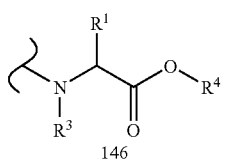
146
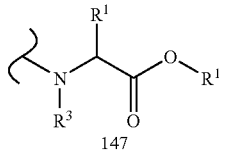
147
TABLE 20.25
148
149
150

| TABLE 20.25-continued | TABLE 20.26-continued |
|---|---|
|  151 | 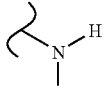 164 |
|  152 | 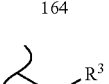 165 |
|  153 | 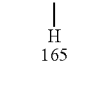 166 |
|  154 | 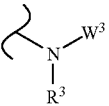 167 |
|  155 | 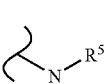 168 |
|  156 | 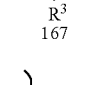 169 |
|  157 | 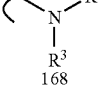 170 |
|  158 | 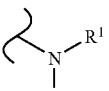 171 |
|  159 | |
| TABLE 20.26 | TABLE 20.27 |
|---|---|
|  160 | 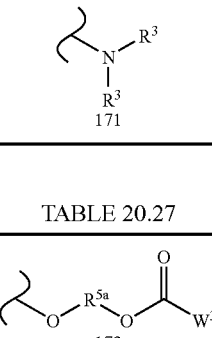 172 |
|  161 | 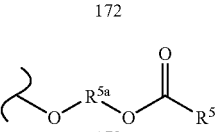 173 |
|  162 | 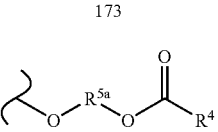 174 |
|  163 | |

TABLE 20.27-continued
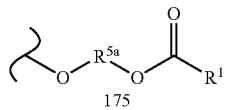
175
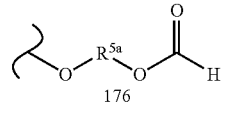
176
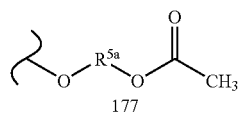
177
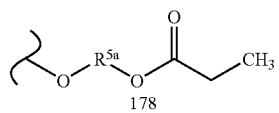
178
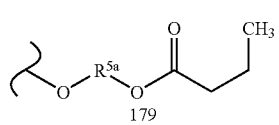
179
TABLE 20.28
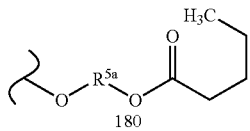
180
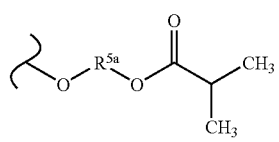
181
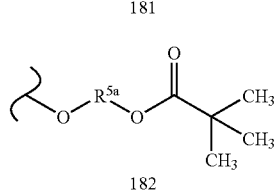
182
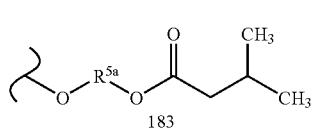
183
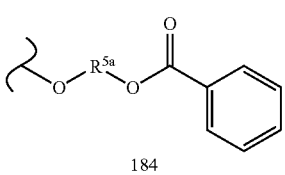
184
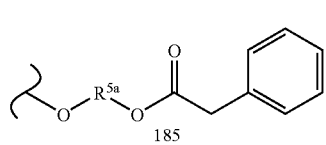
185
TABLE 20.29
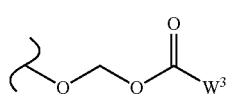
186
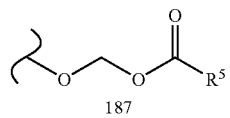
187
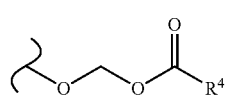
188
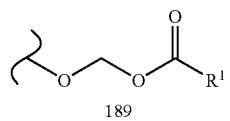
189
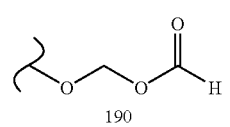
190
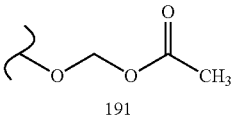
191
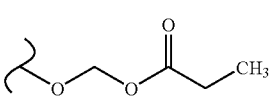
192
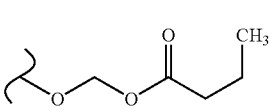
193
TABLE 20.30
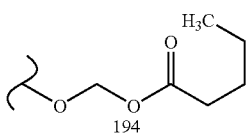
194
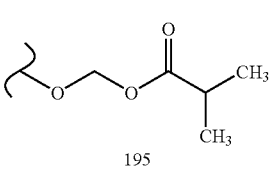
195

TABLE 20.30-continued
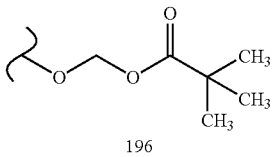
196
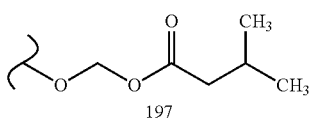
197
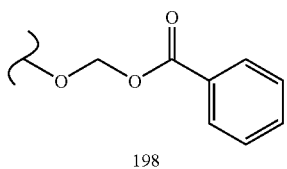
198
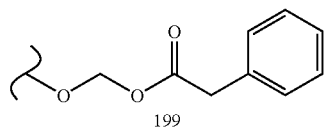
199
TABLE 20.31
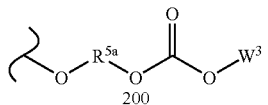
200
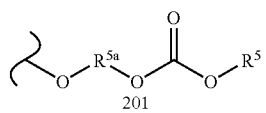
201
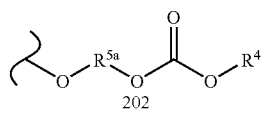
202
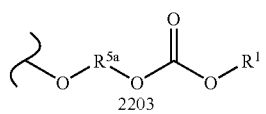
2203
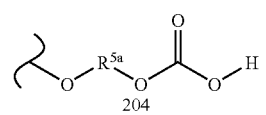
204
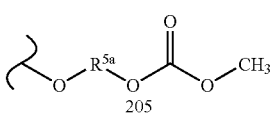
205
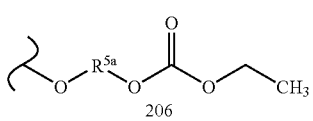
206
TABLE 20.31-continued
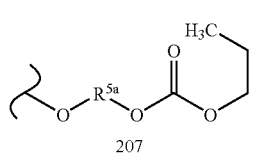
207
TABLE 20.32
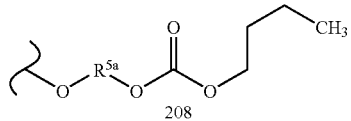
208
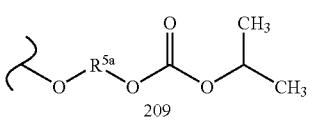
209
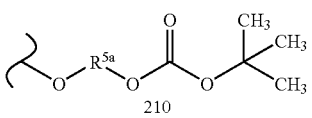
210
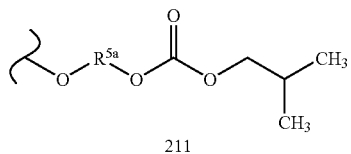
211
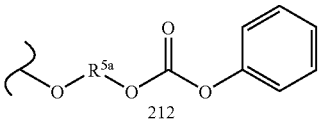
212
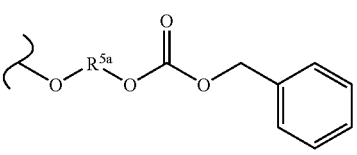
213
TABLE 20.33
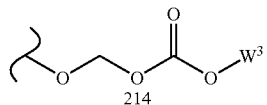
214
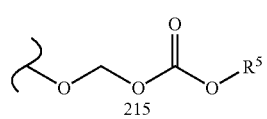
215
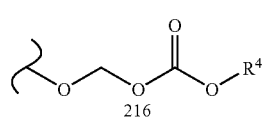
216

TABLE 20.33-continued
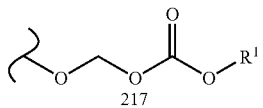
217
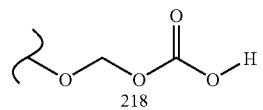
218
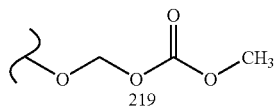
219
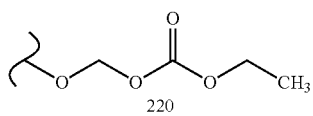
220
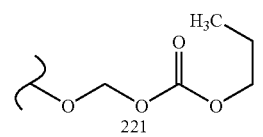
221
TABLE 20.34
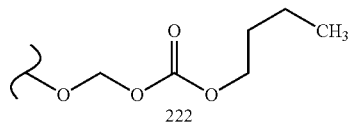
222
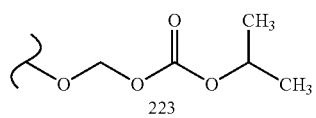
223
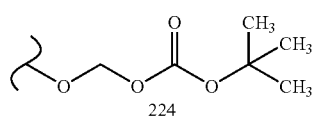
224
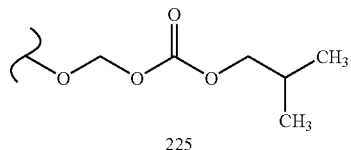
225
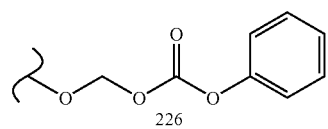
226
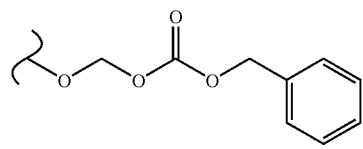
227
TABLE 20.35
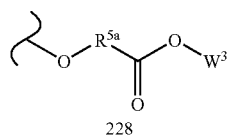
228
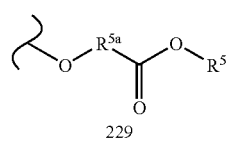
229
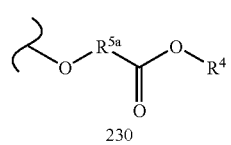
230
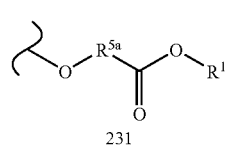
231
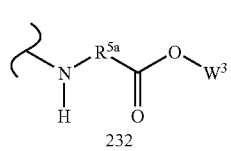
232
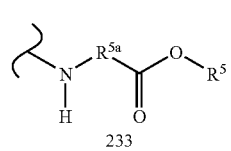
233
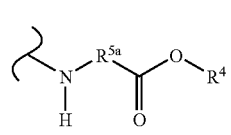
234
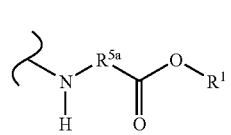
235
TABLE 20.36
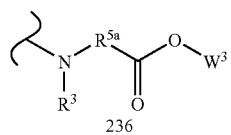
236
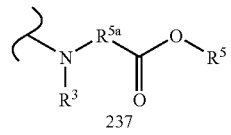
237

TABLE 20.36-continued
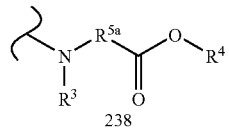
238
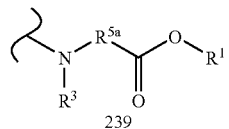
239
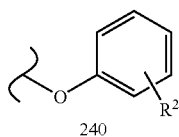
240
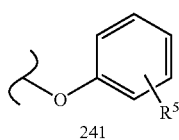
241
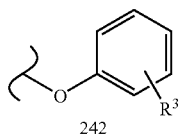
242
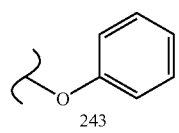
243
TABLE 20.37
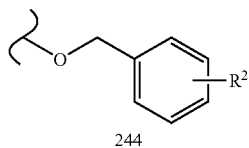
244
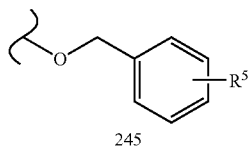
245
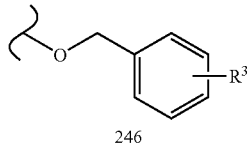
246
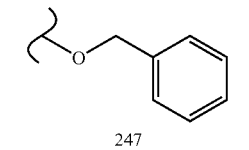
247
TABLE 100
Prodrugs of 1.B
1.B.228.228; 1.B.228.229; 1.B.228.230; 1.B.228.231; 1.B.228.236;
1.B.228.237; 1.B.228.238; 1.B.228.239; 1.B.228.154; 1.B.228.157; 1.B.228.166;
1.B.228.169; 1.B.228.172; 1.B.228.175; 1.B.228.240; 1.B.228.244; 1.B.229.228;
1.B.229.229; 1.B.229.230; 1.B.229.231; 1.B.229.236; 1.B.229.237; 1.B.229.238;
1.B.229.239; 1.B.229.154; 1.B.229.157; 1.B.229.166; 1.B.229.169; 1.B.229.172;
1.B.229.175; 1.B.229.240; 1.B.229.244; 1.B.230.228; 1.B.230.229; 1.B.230.230;
1.B.230.231; 1.B.230.236; 1.B.230.237; 1.B.230.238; 1.B.230.239; 1.B.230.154;
1.B.230.157; 1.B.230.166; 1.B.230.169; 1.B.230.172; 1.B.230.175; 1.B.230.240;
1.B.230.244; 1.B.231.228; 1.B.231.229; 1.B.231.230; 1.B.231.231; 1.B.231.236;
1.B.231.237; 1.B.231.238; 1.B.231.239; 1.B.231.154; 1.B.231.157; 1.B.231.166;
1.B.231.169; 1.B.231.172; 1.B.231.175; 1.B.231.240; 1.B.231.244; 1.B.236.228;
1.B.236.229; 1.B.236.230; 1.B.236.231; 1.B.236.236; 1.B.236.237; 1.B.236.238;
1.B.236.239; 1.B.236.154; 1.B.236.157; 1.B.236.166; 1.B.236.169; 1.B.236.172;
1.B.236.175; 1.B.236.240; 1.B.236.244; 1.B.237.228; 1.B.237.229; 1.B.237.230;
1.B.237.231; 1.B.237.236; 1.B.237.237; 1.B.237.238; 1.B.237.239; 1.B.237.154;
1.B.237.157; 1.B.237.166; 1.B.237.169; 1.B.237.172; 1.B.237.175; 1.B.237.240;
1.B.237.244; 1.B.238.228; 1.B.238.229; 1.B.238.230; 1.B.238.231; 1.B.238.236;
1.B.238.237; 1.B.238.238; 1.B.238.239; 1.B.238.154; 1.B.238.157; 1.B.238.166;
1.B.238.169; 1.B.238.172; 1.B.238.175; 1.B.238.240; 1.B.238.244; 1.B.239.228;
1.B.239.229; 1.B.239.230; 1.B.239.231; 1.B.239.236; 1.B.239.237; 1.B.239.238;
1.B.239.239; 1.B.239.154; 1.B.239.157; 1.B.239.166; 1.B.239.169; 1.B.239.172;
1.B.239.175; 1.B.239.240; 1.B.239.244; 1.B.154.228; 1.B.154.229; 1.B.154.230;
1.B.154.231; 1.B.154.236; 1.B.154.237; 1.B.154.238; 1.B.154.239; 1.B.154.154;
1.B.154.157; 1.B.154.166; 1.B.154.169; 1.B.154.172; 1.B.154.175; 1.B.154.240;
1.B.154.244; 1.B.157.228; 1.B.157.229; 1.B.157.230; 1.B.157.231; 1.B.157.236;
1.B.157.237; 1.B.157.238; 1.B.157.239; 1.B.157.154; 1.B.157.157; 1.B.157.166;
1.B.157.169; 1.B.157.172; 1.B.157.175; 1.B.157.240; 1.B.157.244; 1.B.166.228;
1.B.166.229; 1.B.166.230; 1.B.166.231; 1.B.166.236; 1.B.166.237; 1.B.166.238;

TABLE 100-continued

1.B.166.239; 1.B.166.154; 1.B.166.157; 1.B.166.166; 1.B.166.169; 1.B.166.172;
1.B.166.175; 1.B.166.240; 1.B.166.244; 1.B.169.228; 1.B.169.229; 1.B.169.230;
1.B.169.231; 1.B.169.236; 1.B.169.237; 1.B.169.238; 1.B.169.239; 1.B.169.154;
1.B.169.157; 1.B.169.166; 1.B.169.169; 1.B.169.172; 1.B.169.175; 1.B.169.240;
1.B.169.244; 1.B.172.228; 1.B.172.229; 1.B.172.230; 1.B.172.231; 1.B.172.236;
1.B.172.237; 1.B.172.238; 1.B.172.239; 1.B.172.154; 1.B.172.157; 1.B.172.166;
1.B.172.169; 1.B.172.172; 1.B.172.175; 1.B.172.240; 1.B.172.244; 1.B.175.228;
1.B.175.229; 1.B.175.230; 1.B.175.231; 1.B.175.236; 1.B.175.237; 1.B.175.238;
1.B.175.239; 1.B.175.154; 1.B.175.157; 1.B.175.166; 1.B.175.169; 1.B.175.172;
1.B.175.175; 1.B.175.240; 1.B.175.244; 1.B.240.228; 1.B.240.229; 1.B.240.230;
1.B.240.231; 1.B.240.236; 1.B.240.237; 1.B.240.238; 1.B.240.239; 1.B.240.154;
1.B.240.157; 1.B.240.166; 1.B.240.169; 1.B.240.172; 1.B.240.175; 1.B.240.240;
1.B.240.244; 1.B.244.228; 1.B.244.229; 1.B.244.230; 1.B.244.231; 1.B.244.236;
1.B.244.237; 1.B.244.238; 1.B.244.239; 1.B.244.154; 1.B.244.157; 1.B.244.166;
1.B.244.169; 1.B.244.172; 1.B.244.175; 1.B.244.240; 1.B.244.244;

Prodrugs of 1.D

1.D.228.228; 1.D.228.229; 1.D.228.230; 1.D.228.231; 1.D.228.236;
1.D.228.237; 1.D.228.238; 1.D.228.239; 1.D.228.154; 1.D.228.157;
1.D.228.166; 1.D.228.169; 1.D.228.172; 1.D.228.175; 1.D.228.240;
1.D.228.244; 1.D.229.228; 1.D.229.229; 1.D.229.230; 1.D.229.231;
1.D.229.236; 1.D.229.237; 1.D.229.238; 1.D.229.239; 1.D.229.154;
1.D.229.157; 1.D.229.166; 1.D.229.169; 1.D.229.172; 1.D.229.175;
1.D.229.240; 1.D.229.244; 1.D.230.228; 1.D.230.229; 1.D.230.230;
1.D.230.231; 1.D.230.236; 1.D.230.237; 1.D.230.238; 1.D.230.239;
1.D.230.154; 1.D.230.157; 1.D.230.166; 1.D.230.169; 1.D.230.172;
1.D.230.175; 1.D.230.240; 1.D.230.244; 1.D.231.228; 1.D.231.229;
1.D.231.230; 1.D.231.231; 1.D.231.236; 1.D.231.237; 1.D.231.238;
1.D.231.239; 1.D.231.154; 1.D.231.157; 1.D.231.166; 1.D.231.169;
1.D.231.172; 1.D.231.175; 1.D.231.240; 1.D.231.244; 1.D.236.228;
1.D.236.229; 1.D.236.230; 1.D.236.231; 1.D.236.236; 1.D.236.237;
1.D.236.238; 1.D.236.239; 1.D.236.154; 1.D.236.157; 1.D.236.166;
1.D.236.169; 1.D.236.172; 1.D.236.175; 1.D.236.240; 1.D.236.244;
1.D.237.228; 1.D.237.229; 1.D.237.230; 1.D.237.231; 1.D.237.236;
1.D.237.237; 1.D.237.238; 1.D.237.239; 1.D.237.154; 1.D.237.157;
1.D.237.166; 1.D.237.169; 1.D.237.172; 1.D.237.175; 1.D.237.240;
1.D.237.244; 1.D.238.228; 1.D.238.229; 1.D.238.230; 1.D.238.231;
1.D.238.236; 1.D.238.237; 1.D.238.238; 1.D.238.239; 1.D.238.154;
1.D.238.157; 1.D.238.166; 1.D.238.169; 1.D.238.172; 1.D.238.175;
1.D.238.240; 1.D.238.244; 1.D.239.228; 1.D.239.229; 1.D.239.230;
1.D.239.231; 1.D.239.236; 1.D.239.237; 1.D.239.238; 1.D.239.239;
1.D.239.154; 1.D.239.157; 1.D.239.166; 1.D.239.169; 1.D.239.172;
1.D.239.175; 1.D.239.240; 1.D.239.244; 1.D.154.228; 1.D.154.229;
1.D.154.230; 1.D.154.231; 1.D.154.236; 1.D.154.237; 1.D.154.238;
1.D.154.239; 1.D.154.154; 1.D.154.157; 1.D.154.166; 1.D.154.169;
1.D.154.172; 1.D.154.175; 1.D.154.240; 1.D.154.244; 1.D.157.228;
1.D.157.229; 1.D.157.230; 1.D.157.231; 1.D.157.236; 1.D.157.237;
1.D.157.238; 1.D.157.239; 1.D.157.154; 1.D.157.157; 1.D.157.166;
1.D.157.169; 1.D.157.172; 1.D.157.175; 1.D.157.240; 1.D.157.244;
1.D.166.228; 1.D.166.229; 1.D.166.230; 1.D.166.231; 1.D.166.236;
1.D.166.237; 1.D.166.238; 1.D.166.239; 1.D.166.154; 1.D.166.157;
1.D.166.166; 1.D.166.169; 1.D.166.172; 1.D.166.175; 1.D.166.240;
1.D.166.244; 1.D.169.228; 1.D.169.229; 1.D.169.230; 1.D.169.231;
1.D.169.236; 1.D.169.237; 1.D.169.238; 1.D.169.239; 1.D.169.154;
1.D.169.157; 1.D.169.166; 1.D.169.169; 1.D.169.172; 1.D.169.175;
1.D.169.240; 1.D.169.244; 1.D.172.228; 1.D.172.229; 1.D.172.230;
1.D.172.231; 1.D.172.236; 1.D.172.237; 1.D.172.238; 1.D.172.239;
1.D.172.154; 1.D.172.157; 1.D.172.166; 1.D.172.169; 1.D.172.172;
1.D.172.175; 1.D.172.240; 1.D.172.244; 1.D.175.228; 1.D.175.229;
1.D.175.230; 1.D.175.231; 1.D.175.236; 1.D.175.237; 1.D.175.238;
1.D.175.239; 1.D.175.154; 1.D.175.157; 1.D.175.166; 1.D.175.169;
1.D.175.172; 1.D.175.175; 1.D.175.240; 1.D.175.244; 1.D.240.228;
1.D.240.229; 1.D.240.230; 1.D.240.231; 1.D.240.236; 1.D.240.237;
1.D.240.238; 1.D.240.239; 1.D.240.154; 1.D.240.157; 1.D.240.166;
1.D.240.169; 1.D.240.172; 1.D.240.175; 1.D.240.240; 1.D.240.244;
1.D.244.228; 1.D.244.229; 1.D.244.230; 1.D.244.231; 1.D.244.236;
1.D.244.237; 1.D.244.238; 1.D.244.239; 1.D.244.154; 1.D.244.157;
1.D.244.166; 1.D.244.169; 1.D.244.172; 1.D.244.175; 1.D.244.240; 1.D.244.244;

Prodrugs of 1.E

1.E.228.228; 1.E.228.229; 1.E.228.230; 1.E.228.231; 1.E.228.236;
1.E.228.237; 1.E.228.238; 1.E.228.239; 1.E.228.154; 1.E.228.157; 1.E.228.166;
1.E.228.169; 1.E.228.172; 1.E.228.175; 1.E.228.240; 1.E.228.244; 1.E.229.228;
1.E.229.229; 1.E.229.230; 1.E.229.231; 1.E.229.236; 1.E.229.237; 1.E.229.238;
1.E.229.239; 1.E.229.154; 1.E.229.157; 1.E.229.166; 1.E.229.169; 1.E.229.172;
1.E.229.175; 1.E.229.240; 1.E.229.244; 1.E.230.228; 1.E.230.229; 1.E.230.230;
1.E.230.231; 1.E.230.236; 1.E.230.237; 1.E.230.238; 1.E.230.239; 1.E.230.154;
1.E.230.157; 1.E.230.166; 1.E.230.169; 1.E.230.172; 1.E.230.175; 1.E.230.240;
1.E.230.244; 1.E.231.228; 1.E.231.229; 1.E.231.230; 1.E.231.231; 1.E.231.236;

TABLE 100-continued

1.E.231.237; 1.E.231.238; 1.E.231.239; 1.E.231.154; 1.E.231.157; 1.E.231.166;
1.E.231.169; 1.E.231.172; 1.E.231.175; 1.E.231.240; 1.E.231.244; 1.E.236.228;
1.E.236.229; 1.E.236.230; 1.E.236.231; 1.E.236.236; 1.E.236.237; 1.E.236.238;
1.E.236.239; 1.E.236.154; 1.E.236.157; 1.E.236.166; 1.E.236.169; 1.E.236.172;
1.E.236.175; 1.E.236.240; 1.E.236.244; 1.E.237.228; 1.E.237.229; 1.E.237.230;
1.E.237.231; 1.E.237.236; 1.E.237.237; 1.E.237.238; 1.E.237.239; 1.E.237.154;
1.E.237.157; 1.E.237.166; 1.E.237.169; 1.E.237.172; 1.E.237.175; 1.E.237.240;
1.E.237.244; 1.E.238.228; 1.E.238.229; 1.E.238.230; 1.E.238.231; 1.E.238.236;
1.E.238.237; 1.E.238.238; 1.E.238.239; 1.E.238.154; 1.E.238.157; 1.E.238.166;
1.E.238.169; 1.E.238.172; 1.E.238.175; 1.E.238.240; 1.E.238.244; 1.E.239.228;
1.E.239.229; 1.E.239.230; 1.E.239.231; 1.E.239.236; 1.E.239.237; 1.E.239.238;
1.E.239.239; 1.E.239.154; 1.E.239.157; 1.E.239.166; 1.E.239.169; 1.E.239.172;
1.E.239.175; 1.E.239.240; 1.E.239.244; 1.E.154.228; 1.E.154.229; 1.E.154.230;
1.E.154.231; 1.E.154.236; 1.E.154.237; 1.E.154.238; 1.E.154.239; 1.E.154.154;
1.E.154.157; 1.E.154.166; 1.E.154.169; 1.E.154.172; 1.E.154.175; 1.E.154.240;
1.E.154.244; 1.E.157.228; 1.E.157.229; 1.E.157.230; 1.E.157.231; 1.E.157.236;
1.E.157.237; 1.E.157.238; 1.E.157.239; 1.E.157.154; 1.E.157.157; 1.E.157.166;
1.E.157.169; 1.E.157.172; 1.E.157.175; 1.E.157.240; 1.E.157.244; 1.E.166.228;
1.E.166.229; 1.E.166.230; 1.E.166.231; 1.E.166.236; 1.E.166.237; 1.E.166.238;
1.E.166.239; 1.E.166.154; 1.E.166.157; 1.E.166.166; 1.E.166.169; 1.E.166.172;
1.E.166.175; 1.E.166.240; 1.E.166.244; 1.E.169.228; 1.E.169.229; 1.E.169.230;
1.E.169.231; 1.E.169.236; 1.E.169.237; 1.E.169.238; 1.E.169.239; 1.E.169.154;
1.E.169.157; 1.E.169.166; 1.E.169.169; 1.E.169.172; 1.E.169.175; 1.E.169.240;
1.E.169.244; 1.E.172.228; 1.E.172.229; 1.E.172.230; 1.E.172.231; 1.E.172.236;
1.E.172.237; 1.E.172.238; 1.E.172.239; 1.E.172.154; 1.E.172.157; 1.E.172.166;
1.E.172.169; 1.E.172.172; 1.E.172.175; 1.E.172.240; 1.E.172.244; 1.E.175.228;
1.E.175.229; 1.E.175.230; 1.E.175.231; 1.E.175.236; 1.E.175.237; 1.E.175.238;
1.E.175.239; 1.E.175.154; 1.E.175.157; 1.E.175.166; 1.E.175.169; 1.E.175.172;
1.E.175.175; 1.E.175.240; 1.E.175.244; 1.E.240.228; 1.E.240.229; 1.E.240.230;
1.E.240.231; 1.E.240.236; 1.E.240.237; 1.E.240.238; 1.E.240.239; 1.E.240.154;
1.E.240.157; 1.E.240.166; 1.E.240.169; 1.E.240.172; 1.E.240.175; 1.E.240.240;
1.E.240.244; 1.E.244.228; 1.E.244.229; 1.E.244.230; 1.E.244.231; 1.E.244.236;
1.E.244.237; 1.E.244.238; 1.E.244.239; 1.E.244.154; 1.E.244.157; 1.E.244.166;
1.E.244.169; 1.E.244.172; 1.E.244.175; 1.E.244.240; 1.E.244.244;
Prodrugs of 1.G 1.G.228.228; 1.G.228.229; 1.G.228.230; 1.G.228.231; 1.G.228.236;
1.G.228.237; 1.G.228.238; 1.G.228.239; 1.G.228.154; 1.G.228.157;
1.G.228.166; 1.G.228.169; 1.G.228.172; 1.G.228.175; 1.G.228.240;
1.G.228.244; 1.G.229.228; 1.G.229.229; 1.G.229.230; 1.G.229.231;
1.G.229.236; 1.G.229.237; 1.G.229.238; 1.G.229.239; 1.G.229.154;
1.G.229.157; 1.G.229.166; 1.G.229.169; 1.G.229.172; 1.G.229.175;
1.G.229.240; 1.G.229.244; 1.G.230.228; 1.G.230.229; 1.G.230.230;
1.G.230.231; 1.G.230.236; 1.G.230.237; 1.G.230.238; 1.G.230.239;
1.G.230.154; 1.G.230.157; 1.G.230.166; 1.G.230.169; 1.G.230.172;
1.G.230.175; 1.G.230.240; 1.G.230.244; 1.G.231.228; 1.G.231.229;
1.G.231.230; 1.G.231.231; 1.G.231.236; 1.G.231.237; 1.G.231.238;
1.G.231.239; 1.G.231.154; 1.G.231.157; 1.G.231.166; 1.G.231.169;
1.G.231.172; 1.G.231.175; 1.G.231.240; 1.G.231.244; 1.G.236.228;
1.G.236.229; 1.G.236.230; 1.G.236.231; 1.G.236.236; 1.G.236.237;
1.G.236.238; 1.G.236.239; 1.G.236.154; 1.G.236.157; 1.G.236.166;
1.G.236.169; 1.G.236.172; 1.G.236.175; 1.G.236.240; 1.G.236.244;
1.G.237.228; 1.G.237.229; 1.G.237.230; 1.G.237.231; 1.G.237.236;
1.G.237.237; 1.G.237.238; 1.G.237.239; 1.G.237.154; 1.G.237.157;
1.G.237.166; 1.G.237.169; 1.G.237.172; 1.G.237.175; 1.G.237.240;
1.G.237.244; 1.G.238.228; 1.G.238.229; 1.G.238.230; 1.G.238.231;
1.G.238.236; 1.G.238.237; 1.G.238.238; 1.G.238.239; 1.G.238.154;
1.G.238.157; 1.G.238.166; 1.G.238.169; 1.G.238.172; 1.G.238.175;
1.G.238.240; 1.G.238.244; 1.G.239.228; 1.G.239.229; 1.G.239.230;
1.G.239.231; 1.G.239.236; 1.G.239.237; 1.G.239.238; 1.G.239.239;
1.G.239.154; 1.G.239.157; 1.G.239.166; 1.G.239.169; 1.G.239.172;
1.G.239.175; 1.G.239.240; 1.G.239.244; 1.G.154.228; 1.G.154.229;
1.G.154.230; 1.G.154.231; 1.G.154.236; 1.G.154.237; 1.G.154.238;
1.G.154.239; 1.G.154.154; 1.G.154.157; 1.G.154.166; 1.G.154.169;
1.G.154.172; 1.G.154.175; 1.G.154.240; 1.G.154.244; 1.G.157.228;
1.G.157.229; 1.G.157.230; 1.G.157.231; 1.G.157.236; 1.G.157.237;
1.G.157.238; 1.G.157.239; 1.G.157.154; 1.G.157.157; 1.G.157.166;
1.G.157.169; 1.G.157.172; 1.G.157.175; 1.G.157.240; 1.G.157.244;
1.G.166.228; 1.G.166.229; 1.G.166.230; 1.G.166.231; 1.G.166.236;
1.G.166.237; 1.G.166.238; 1.G.166.239; 1.G.166.154; 1.G.166.157;
1.G.166.166; 1.G.166.169; 1.G.166.172; 1.G.166.175; 1.G.166.240;
1.G.166.244; 1.G.169.228; 1.G.169.229; 1.G.169.230; 1.G.169.231;
1.G.169.236; 1.G.169.237; 1.G.169.238; 1.G.169.239; 1.G.169.154;
1.G.169.157; 1.G.169.166; 1.G.169.169; 1.G.169.172; 1.G.169.175;
1.G.169.240; 1.G.169.244; 1.G.172.228; 1.G.172.229; 1.G.172.230;
1.G.172.231; 1.G.172.236; 1.G.172.237; 1.G.172.238; 1.G.172.239;
1.G.172.154; 1.G.172.157; 1.G.172.166; 1.G.172.169; 1.G.172.172;
1.G.172.175; 1.G.172.240; 1.G.172.244; 1.G.175.228; 1.G.175.229;
1.G.175.230; 1.G.175.231; 1.G.175.236; 1.G.175.237; 1.G.175.238;

TABLE 100-continued

1.G.175.239; 1.G.175.154; 1.G.175.157; 1.G.175.166; 1.G.175.169;
1.G.175.172; 1.G.175.175; 1.G.175.240; 1.G.175.244; 1.G.240.228;
1.G.240.229; 1.G.240.230; 1.G.240.231; 1.G.240.236; 1.G.240.237;
1.G.240.238; 1.G.240.239; 1.G.240.154; 1.G.240.157; 1.G.240.166;
1.G.240.169; 1.G.240.172; 1.G.240.175; 1.G.240.240; 1.G.240.244;
1.G.244.228; 1.G.244.229; 1.G.244.230; 1.G.244.231; 1.G.244.236;
1.G.244.237; 1.G.244.238; 1.G.244.239; 1.G.244.154; 1.G.244.157;
1.G.244.166; 1.G.244.169; 1.G.244.172; 1.G.244.175; 1.G.244.240; 1.G.244.244;

Prodrugs of 1.I

1.I.228.228; 1.I.228.229; 1.I.228.230; 1.I.228.231; 1.I.228.236; 1.I.228.237;
1.I.228.238; 1.I.228.239; 1.I.228.154; 1.I.228.157; 1.I.228.166; 1.I.228.169;
1.I.228.172; 1.I.228.175; 1.I.228.240; 1.I.228.244; 1.I.229.228; 1.I.229.229;
1.I.229.230; 1.I.229.231; 1.I.229.236; 1.I.229.237; 1.I.229.238; 1.I.229.239;
1.I.229.154; 1.I.229.157; 1.I.229.166; 1.I.229.169; 1.I.229.172; 1.I.229.175;
1.I.229.240; 1.I.229.244; 1.I.230.228; 1.I.230.229; 1.I.230.230; 1.I.230.231;
1.I.230.236; 1.I.230.237; 1.I.230.238; 1.I.230.239; 1.I.230.154; 1.I.230.157;
1.I.230.166; 1.I.230.169; 1.I.230.172; 1.I.230.175; 1.I.230.240; 1.I.230.244;
1.I.231.228; 1.I.231.229; 1.I.231.230; 1.I.231.231; 1.I.231.236; 1.I.231.237;
1.I.231.238; 1.I.231.239; 1.I.231.154; 1.I.231.157; 1.I.231.166; 1.I.231.169;
1.I.231.172; 1.I.231.175; 1.I.231.240; 1.I.231.244; 1.I.236.228; 1.I.236.229;
1.I.236.230; 1.I.236.231; 1.I.236.236; 1.I.236.237; 1.I.236.238; 1.I.236.239;
1.I.236.154; 1.I.236.157; 1.I.236.166; 1.I.236.169; 1.I.236.172; 1.I.236.175;
1.I.236.240; 1.I.236.244; 1.I.237.228; 1.I.237.229; 1.I.237.230; 1.I.237.231;
1.I.237.236; 1.I.237.237; 1.I.237.238; 1.I.237.239; 1.I.237.154; 1.I.237.157;
1.I.237.166; 1.I.237.169; 1.I.237.172; 1.I.237.175; 1.I.237.240; 1.I.237.244;
1.I.238.228; 1.I.238.229; 1.I.238.230; 1.I.238.231; 1.I.238.236; 1.I.238.237;
1.I.238.238; 1.I.238.239; 1.I.238.154; 1.I.238.157; 1.I.238.166; 1.I.238.169;
1.I.238.172; 1.I.238.175; 1.I.238.240; 1.I.238.244; 1.I.239.228; 1.I.239.229;
1.I.239.230; 1.I.239.231; 1.I.239.236; 1.I.239.237; 1.I.239.238; 1.I.239.239;
1.I.239.154; 1.I.239.157; 1.I.239.166; 1.I.239.169; 1.I.239.172; 1.I.239.175;
1.I.239.240; 1.I.239.244; 1.I.154.228; 1.I.154.229; 1.I.154.230; 1.I.154.231;
1.I.154.236; 1.I.154.237; 1.I.154.238; 1.I.154.239; 1.I.154.154; 1.I.154.157;
1.I.154.166; 1.I.154.169; 1.I.154.172; 1.I.154.175; 1.I.154.240; 1.I.154.244;
1.I.157.228; 1.I.157.229; 1.I.157.230; 1.I.157.231; 1.I.157.236; 1.I.157.237;
1.I.157.238; 1.I.157.239; 1.I.157.154; 1.I.157.157; 1.I.157.166; 1.I.157.169;
1.I.157.172; 1.I.157.175; 1.I.157.240; 1.I.157.244; 1.I.166.228; 1.I.166.229;
1.I.166.230; 1.I.166.231; 1.I.166.236; 1.I.166.237; 1.I.166.238; 1.I.166.239;
1.I.166.154; 1.I.166.157; 1.I.166.166; 1.I.166.169; 1.I.166.172; 1.I.166.175;
1.I.166.240; 1.I.166.244; 1.I.169.228; 1.I.169.229; 1.I.169.230; 1.I.169.231;
1.I.169.236; 1.I.169.237; 1.I.169.238; 1.I.169.239; 1.I.169.154; 1.I.169.157;
1.I.169.166; 1.I.169.169; 1.I.169.172; 1.I.169.175; 1.I.169.240; 1.I.169.244;
1.I.172.228; 1.I.172.229; 1.I.172.230; 1.I.172.231; 1.I.172.236; 1.I.172.237;
1.I.172.238; 1.I.172.239; 1.I.172.154; 1.I.172.157; 1.I.172.166; 1.I.172.169;
1.I.172.172; 1.I.172.175; 1.I.172.240; 1.I.172.244; 1.I.175.228; 1.I.175.229;
1.I.175.230; 1.I.175.231; 1.I.175.236; 1.I.175.237; 1.I.175.238; 1.I.175.239;
1.I.175.154; 1.I.175.157; 1.I.175.166; 1.I.175.169; 1.I.175.172; 1.I.175.175;
1.I.175.240; 1.I.175.244; 1.I.240.228; 1.I.240.229; 1.I.240.230; 1.I.240.231;
1.I.240.236; 1.I.240.237; 1.I.240.238; 1.I.240.239; 1.I.240.154; 1.I.240.157;
1.I.240.166; 1.I.240.169; 1.I.240.172; 1.I.240.175; 1.I.240.240; 1.I.240.244;
1.I.244.228; 1.I.244.229; 1.I.244.230; 1.I.244.231; 1.I.244.236; 1.I.244.237;
1.I.244.238; 1.I.244.239; 1.I.244.154; 1.I.244.157; 1.I.244.166; 1.I.244.169;
1.I.244.172; 1.I.244.175; 1.I.244.240; 1.I.244.244;

Prodrugs of 1.J

1.J.228.228; 1.J.228.229; 1.J.228.230; 1.J.228.231; 1.J.228.236; 1.J.228.237;
1.J.228.238; 1.J.228.239; 1.J.228.154; 1.J.228.157; 1.J.228.166; 1.J.228.169;
1.J.228.172; 1.J.228.175; 1.J.228.240; 1.J.228.244; 1.J.229.228; 1.J.229.229;
1.J.229.230; 1.J.229.231; 1.J.229.236; 1.J.229.237; 1.J.229.238; 1.J.229.239;
1.J.229.154; 1.J.229.157; 1.J.229.166; 1.J.229.169; 1.J.229.172; 1.J.229.175;
1.J.229.240; 1.J.229.244; 1.J.230.228; 1.J.230.229; 1.J.230.230; 1.J.230.231;
1.J.230.236; 1.J.230.237; 1.J.230.238; 1.J.230.239; 1.J.230.154; 1.J.230.157;
1.J.230.166; 1.J.230.169; 1.J.230.172; 1.J.230.175; 1.J.230.240; 1.J.230.244;
1.J.231.228; 1.J.231.229; 1.J.231.230; 1.J.231.231; 1.J.231.236; 1.J.231.237;
1.J.231.238; 1.J.231.239; 1.J.231.154; 1.J.231.157; 1.J.231.166; 1.J.231.169;
1.J.231.172; 1.J.231.175; 1.J.231.240; 1.J.231.244; 1.J.236.228; 1.J.236.229;
1.J.236.230; 1.J.236.231; 1.J.236.236; 1.J.236.237; 1.J.236.238; 1.J.236.239;
1.J.236.154; 1.J.236.157; 1.J.236.166; 1.J.236.169; 1.J.236.172; 1.J.236.175;
1.J.236.240; 1.J.236.244; 1.J.237.228; 1.J.237.229; 1.J.237.230; 1.J.237.231;
1.J.237.236; 1.J.237.237; 1.J.237.238; 1.J.237.239; 1.J.237.154; 1.J.237.157;
1.J.237.166; 1.J.237.169; 1.J.237.172; 1.J.237.175; 1.J.237.240; 1.J.237.244;
1.J.238.228; 1.J.238.229; 1.J.238.230; 1.J.238.231; 1.J.238.236; 1.J.238.237;
1.J.238.238; 1.J.238.239; 1.J.238.154; 1.J.238.157; 1.J.238.166; 1.J.238.169;
1.J.238.172; 1.J.238.175; 1.J.238.240; 1.J.238.244; 1.J.239.228; 1.J.239.229;
1.J.239.230; 1.J.239.231; 1.J.239.236; 1.J.239.237; 1.J.239.238; 1.J.239.239;
1.J.239.154; 1.J.239.157; 1.J.239.166; 1.J.239.169; 1.J.239.172; 1.J.239.175;
1.J.239.240; 1.J.239.244; 1.J.154.228; 1.J.154.229; 1.J.154.230; 1.J.154.231;
1.J.154.236; 1.J.154.237; 1.J.154.238; 1.J.154.239; 1.J.154.154; 1.J.154.157;
1.J.154.166; 1.J.154.169; 1.J.154.172; 1.J.154.175; 1.J.154.240; 1.J.154.244;

TABLE 100-continued

1.J.157.228; 1.J.157.229; 1.J.157.230; 1.J.157.231; 1.J.157.236; 1.J.157.237;
1.J.157.238; 1.J.157.239; 1.J.157.154; 1.J.157.157; 1.J.157.166; 1.J.157.169;
1.J.157.172; 1.J.157.175; 1.J.157.240; 1.J.157.244; 1.J.166.228; 1.J.166.229;
1.J.166.230; 1.J.166.231; 1.J.166.236; 1.J.166.237; 1.J.166.238; 1.J.166.239;
1.J.166.154; 1.J.166.157; 1.J.166.166; 1.J.166.169; 1.J.166.172; 1.J.166.175;
1.J.166.240; 1.J.166.244; 1.J.169.228; 1.J.169.229; 1.J.169.230; 1.J.169.231;
1.J.169.236; 1.J.169.237; 1.J.169.238; 1.J.169.239; 1.J.169.154; 1.J.169.157;
1.J.169.166; 1.J.169.169; 1.J.169.172; 1.J.169.175; 1.J.169.240; 1.J.169.244;
1.J.172.228; 1.J.172.229; 1.J.172.230; 1.J.172.231; 1.J.172.236; 1.J.172.237;
1.J.172.238; 1.J.172.239; 1.J.172.154; 1.J.172.157; 1.J.172.166; 1.J.172.169;
1.J.172.172; 1.J.172.175; 1.J.172.240; 1.J.172.244; 1.J.175.228; 1.J.175.229;
1.J.175.230; 1.J.175.231; 1.J.175.236; 1.J.175.237; 1.J.175.238; 1.J.175.239;
1.J.175.154; 1.J.175.157; 1.J.175.166; 1.J.175.169; 1.J.175.172; 1.J.175.175;
1.J.175.240; 1.J.175.244; 1.J.240.228; 1.J.240.229; 1.J.240.230; 1.J.240.231;
1.J.240.236; 1.J.240.237; 1.J.240.238; 1.J.240.239; 1.J.240.154; 1.J.240.157;
1.J.240.166; 1.J.240.169; 1.J.240.172; 1.J.240.175; 1.J.240.240; 1.J.240.244;
1.J.244.228; 1.J.244.229; 1.J.244.230; 1.J.244.231; 1.J.244.236; 1.J.244.237;
1.J.244.238; 1.J.244.239; 1.J.244.154; 1.J.244.157; 1.J.244.166; 1.J.244.169;
1.J.244.172; 1.J.244.175; 1.J.244.240; 1.J.244.244;
Prodrugs of 1.L 1.L.228.228; 1.L.228.229; 1.L.228.230; 1.L.228.231; 1.L.228.236;
1.L.228.237; 1.L.228.238; 1.L.228.239; 1.L.228.154; 1.L.228.157; 1.L.228.166;
1.L.228.169; 1.L.228.172; 1.L.228.175; 1.L.228.240; 1.L.228.244; 1.L.229.228;
1.L.229.229; 1.L.229.230; 1.L.229.231; 1.L.229.236; 1.L.229.237; 1.L.229.238;
1.L.229.239; 1.L.229.154; 1.L.229.157; 1.L.229.166; 1.L.229.169; 1.L.229.172;
1.L.229.175; 1.L.229.240; 1.L.229.244; 1.L.230.228; 1.L.230.229; 1.L.230.230;
1.L.230.231; 1.L.230.236; 1.L.230.237; 1.L.230.238; 1.L.230.239; 1.L.230.154;
1.L.230.157; 1.L.230.166; 1.L.230.169; 1.L.230.172; 1.L.230.175; 1.L.230.240;
1.L.230.244; 1.L.231.228; 1.L.231.229; 1.L.231.230; 1.L.231.231; 1.L.231.236;
1.L.231.237; 1.L.231.238; 1.L.231.239; 1.L.231.154; 1.L.231.157; 1.L.231.166;
1.L.231.169; 1.L.231.172; 1.L.231.175; 1.L.231.240; 1.L.231.244; 1.L.236.228;
1.L.236.229; 1.L.236.230; 1.L.236.231; 1.L.236.236; 1.L.236.237; 1.L.236.238;
1.L.236.239; 1.L.236.154; 1.L.236.157; 1.L.236.166; 1.L.236.169; 1.L.236.172;
1.L.236.175; 1.L.236.240; 1.L.236.244; 1.L.237.228; 1.L.237.229; 1.L.237.230;
1.L.237.231; 1.L.237.236; 1.L.237.237; 1.L.237.238; 1.L.237.239; 1.L.237.154;
1.L.237.157; 1.L.237.166; 1.L.237.169; 1.L.237.172; 1.L.237.175; 1.L.237.240;
1.L.237.244; 1.L.238.228; 1.L.238.229; 1.L.238.230; 1.L.238.231; 1.L.238.236;
1.L.238.237; 1.L.238.238; 1.L.238.239; 1.L.238.154; 1.L.238.157; 1.L.238.166;
1.L.238.169; 1.L.238.172; 1.L.238.175; 1.L.238.240; 1.L.238.244; 1.L.239.228;
1.L.239.229; 1.L.239.230; 1.L.239.231; 1.L.239.236; 1.L.239.237; 1.L.239.238;
1.L.239.239; 1.L.239.154; 1.L.239.157; 1.L.239.166; 1.L.239.169; 1.L.239.172;
1.L.239.175; 1.L.239.240; 1.L.239.244; 1.L.154.228; 1.L.154.229; 1.L.154.230;
1.L.154.231; 1.L.154.236; 1.L.154.237; 1.L.154.238; 1.L.154.239; 1.L.154.154;
1.L.154.157; 1.L.154.166; 1.L.154.169; 1.L.154.172; 1.L.154.175; 1.L.154.240;
1.L.154.244; 1.L.157.228; 1.L.157.229; 1.L.157.230; 1.L.157.231; 1.L.157.236;
1.L.157.237; 1.L.157.238; 1.L.157.239; 1.L.157.154; 1.L.157.157; 1.L.157.166;
1.L.157.169; 1.L.157.172; 1.L.157.175; 1.L.157.240; 1.L.157.244; 1.L.166.228;
1.L.166.229; 1.L.166.230; 1.L.166.231; 1.L.166.236; 1.L.166.237; 1.L.166.238;
1.L.166.239; 1.L.166.154; 1.L.166.157; 1.L.166.166; 1.L.166.169; 1.L.166.172;
1.L.166.175; 1.L.166.240; 1.L.166.244; 1.L.169.228; 1.L.169.229; 1.L.169.230;
1.L.169.231; 1.L.169.236; 1.L.169.237; 1.L.169.238; 1.L.169.239; 1.L.169.154;
1.L.169.157; 1.L.169.166; 1.L.169.169; 1.L.169.172; 1.L.169.175; 1.L.169.240;
1.L.169.244; 1.L.172.228; 1.L.172.229; 1.L.172.230; 1.L.172.231; 1.L.172.236;
1.L.172.237; 1.L.172.238; 1.L.172.239; 1.L.172.154; 1.L.172.157; 1.L.172.166;
1.L.172.169; 1.L.172.172; 1.L.172.175; 1.L.172.240; 1.L.172.244; 1.L.175.228;
1.L.175.229; 1.L.175.230; 1.L.175.231; 1.L.175.236; 1.L.175.237; 1.L.175.238;
1.L.175.239; 1.L.175.154; 1.L.175.157; 1.L.175.166; 1.L.175.169; 1.L.175.172;
1.L.175.175; 1.L.175.240; 1.L.175.244; 1.L.240.228; 1.L.240.229; 1.L.240.230;
1.L.240.231; 1.L.240.236; 1.L.240.237; 1.L.240.238; 1.L.240.239; 1.L.240.154;
1.L.240.157; 1.L.240.166; 1.L.240.169; 1.L.240.172; 1.L.240.175; 1.L.240.240;
1.L.240.244; 1.L.244.228; 1.L.244.229; 1.L.244.230; 1.L.244.231; 1.L.244.236;
1.L.244.237; 1.L.244.238; 1.L.244.239; 1.L.244.154; 1.L.244.157; 1.L.244.166;
1.L.244.169; 1.L.244.172; 1.L.244.175; 1.L.244.240; 1.L.244.244;
Prodrugs of 1.O 1.O.228.228; 1.O.228.229; 1.O.228.230; 1.O.228.231; 1.O.228.236;
1.O.228.237; 1.O.228.238; 1.O.228.239; 1.O.228.154; 1.O.228.157;
1.O.228.166; 1.O.228.169; 1.O.228.172; 1.O.228.175; 1.O.228.240;
1.O.228.244; 1.O.229.228; 1.O.229.229; 1.O.229.230; 1.O.229.231;
1.O.229.236; 1.O.229.237; 1.O.229.238; 1.O.229.239; 1.O.229.154;
1.O.229.157; 1.O.229.166; 1.O.229.169; 1.O.229.172; 1.O.229.175;
1.O.229.240; 1.O.229.244; 1.O.230.228; 1.O.230.229; 1.O.230.230;
1.O.230.231; 1.O.230.236; 1.O.230.237; 1.O.230.238; 1.O.230.239;
1.O.230.154; 1.O.230.157; 1.O.230.166; 1.O.230.169; 1.O.230.172;
1.O.230.175; 1.O.230.240; 1.O.230.244; 1.O.231.228; 1.O.231.229;
1.O.231.230; 1.O.231.231; 1.O.231.236; 1.O.231.237; 1.O.231.238;
1.O.231.239; 1.O.231.154; 1.O.231.157; 1.O.231.166; 1.O.231.169;
1.O.231.172; 1.O.231.175; 1.O.231.240; 1.O.231.244; 1.O.236.228;

TABLE 100-continued

1.O.236.229; 1.O.236.230; 1.O.236.231; 1.O.236.236; 1.O.236.237;
1.O.236.238; 1.O.236.239; 1.O.236.154; 1.O.236.157; 1.O.236.166;
1.O.236.169; 1.O.236.172; 1.O.236.175; 1.O.236.240; 1.O.236.244;
1.O.237.228; 1.O.237.229; 1.O.237.230; 1.O.237.231; 1.O.237.236;
1.O.237.237; 1.O.237.238; 1.O.237.239; 1.O.237.154; 1.O.237.157;
1.O.237.166; 1.O.237.169; 1.O.237.172; 1.O.237.175; 1.O.237.240;
1.O.237.244; 1.O.238.228; 1.O.238.229; 1.O.238.230; 1.O.238.231;
1.O.238.236; 1.O.238.237; 1.O.238.238; 1.O.238.239; 1.O.238.154;
1.O.238.157; 1.O.238.166; 1.O.238.169; 1.O.238.172; 1.O.238.175;
1.O.238.240; 1.O.238.244; 1.O.239.228; 1.O.239.229; 1.O.239.230;
1.O.239.231; 1.O.239.236; 1.O.239.237; 1.O.239.238; 1.O.239.239;
1.O.239.154; 1.O.239.157; 1.O.239.166; 1.O.239.169; 1.O.239.172;
1.O.239.175; 1.O.239.240; 1.O.239.244; 1.O.154.228; 1.O.154.229;
1.O.154.230; 1.O.154.231; 1.O.154.236; 1.O.154.237; 1.O.154.238;
1.O.154.239; 1.O.154.154; 1.O.154.157; 1.O.154.166; 1.O.154.169;
1.O.154.172; 1.O.154.175; 1.O.154.240; 1.O.154.244; 1.O.157.228;
1.O.157.229; 1.O.157.230; 1.O.157.231; 1.O.157.236; 1.O.157.237;
1.O.157.238; 1.O.157.239; 1.O.157.154; 1.O.157.157; 1.O.157.166;
1.O.157.169; 1.O.157.172; 1.O.157.175; 1.O.157.240; 1.O.157.244;
1.O.166.228; 1.O.166.229; 1.O.166.230; 1.O.166.231; 1.O.166.236;
1.O.166.237; 1.O.166.238; 1.O.166.239; 1.O.166.154; 1.O.166.157;
1.O.166.166; 1.O.166.169; 1.O.166.172; 1.O.166.175; 1.O.166.240;
1.O.166.244; 1.O.169.228; 1.O.169.229; 1.O.169.230; 1.O.169.231;
1.O.169.236; 1.O.169.237; 1.O.169.238; 1.O.169.239; 1.O.169.154;
1.O.169.157; 1.O.169.166; 1.O.169.169; 1.O.169.172; 1.O.169.175;
1.O.169.240; 1.O.169.244; 1.O.172.228; 1.O.172.229; 1.O.172.230;
1.O.172.231; 1.O.172.236; 1.O.172.237; 1.O.172.238; 1.O.172.239;
1.O.172.154; 1.O.172.157; 1.O.172.166; 1.O.172.169; 1.O.172.172;
1.O.172.175; 1.O.172.240; 1.O.172.244; 1.O.175.228; 1.O.175.229;
1.O.175.230; 1.O.175.231; 1.O.175.236; 1.O.175.237; 1.O.175.238;
1.O.175.239; 1.O.175.154; 1.O.175.157; 1.O.175.166; 1.O.175.169;
1.O.175.172; 1.O.175.175; 1.O.175.240; 1.O.175.244; 1.O.240.228;
1.O.240.229; 1.O.240.230; 1.O.240.231; 1.O.240.236; 1.O.240.237;
1.O.240.238; 1.O.240.239; 1.O.240.154; 1.O.240.157; 1.O.240.166;
1.O.240.169; 1.O.240.172; 1.O.240.175; 1.O.240.240; 1.O.240.244;
1.O.244.228; 1.O.244.229; 1.O.244.230; 1.O.244.231; 1.O.244.236;
1.O.244.237; 1.O.244.238; 1.O.244.239; 1.O.244.154; 1.O.244.157;
1.O.244.166; 1.O.244.169; 1.O.244.172; 1.O.244.175; 1.O.244.240; 1.O.244.244;
Prodrugs of 1.P 1.P.228.228; 1.P.228.229; 1.P.228.230; 1.P.228.231; 1.P.228.236;
1.P.228.237; 1.P.228.238; 1.P.228.239; 1.P.228.154; 1.P.228.157; 1.P.228.166;
1.P.228.169; 1.P.228.172; 1.P.228.175; 1.P.228.240; 1.P.228.244; 1.P.229.228;
1.P.229.229; 1.P.229.230; 1.P.229.231; 1.P.229.236; 1.P.229.237; 1.P.229.238;
1.P.229.239; 1.P.229.154; 1.P.229.157; 1.P.229.166; 1.P.229.169; 1.P.229.172;
1.P.229.175; 1.P.229.240; 1.P.229.244; 1.P.230.228; 1.P.230.229; 1.P.230.230;
1.P.230.231; 1.P.230.236; 1.P.230.237; 1.P.230.238; 1.P.230.239; 1.P.230.154;
1.P.230.157; 1.P.230.166; 1.P.230.169; 1.P.230.172; 1.P.230.175; 1.P.230.240;
1.P.230.244; 1.P.231.228; 1.P.231.229; 1.P.231.230; 1.P.231.231; 1.P.231.236;
1.P.231.237; 1.P.231.238; 1.P.231.239; 1.P.231.154; 1.P.231.157; 1.P.231.166;
1.P.231.169; 1.P.231.172; 1.P.231.175; 1.P.231.240; 1.P.231.244; 1.P.236.228;
1.P.236.229; 1.P.236.230; 1.P.236.231; 1.P.236.236; 1.P.236.237; 1.P.236.238;
1.P.236.239; 1.P.236.154; 1.P.236.157; 1.P.236.166; 1.P.236.169; 1.P.236.172;
1.P.236.175; 1.P.236.240; 1.P.236.244; 1.P.237.228; 1.P.237.229; 1.P.237.230;
1.P.237.231; 1.P.237.236; 1.P.237.237; 1.P.237.238; 1.P.237.239; 1.P.237.154;
1.P.237.157; 1.P.237.166; 1.P.237.169; 1.P.237.172; 1.P.237.175; 1.P.237.240;
1.P.237.244; 1.P.238.228; 1.P.238.229; 1.P.238.230; 1.P.238.231; 1.P.238.236;
1.P.238.237; 1.P.238.238; 1.P.238.239; 1.P.238.154; 1.P.238.157; 1.P.238.166;
1.P.238.169; 1.P.238.172; 1.P.238.175; 1.P.238.240; 1.P.238.244; 1.P.239.228;
1.P.239.229; 1.P.239.230; 1.P.239.231; 1.P.239.236; 1.P.239.237; 1.P.239.238;
1.P.239.239; 1.P.239.154; 1.P.239.157; 1.P.239.166; 1.P.239.169; 1.P.239.172;
1.P.239.175; 1.P.239.240; 1.P.239.244; 1.P.154.228; 1.P.154.229; 1.P.154.230;
1.P.154.231; 1.P.154.236; 1.P.154.237; 1.P.154.238; 1.P.154.239; 1.P.154.154;
1.P.154.157; 1.P.154.166; 1.P.154.169; 1.P.154.172; 1.P.154.175; 1.P.154.240;
1.P.154.244; 1.P.157.228; 1.P.157.229; 1.P.157.230; 1.P.157.231; 1.P.157.236;
1.P.157.237; 1.P.157.238; 1.P.157.239; 1.P.157.154; 1.P.157.157; 1.P.157.166;
1.P.157.169; 1.P.157.172; 1.P.157.175; 1.P.157.240; 1.P.157.244; 1.P.166.228;
1.P.166.229; 1.P.166.230; 1.P.166.231; 1.P.166.236; 1.P.166.237; 1.P.166.238;
1.P.166.239; 1.P.166.154; 1.P.166.157; 1.P.166.166; 1.P.166.169; 1.P.166.172;
1.P.166.175; 1.P.166.240; 1.P.166.244; 1.P.169.228; 1.P.169.229; 1.P.169.230;
1.P.169.231; 1.P.169.236; 1.P.169.237; 1.P.169.238; 1.P.169.239; 1.P.169.154;
1.P.169.157; 1.P.169.166; 1.P.169.169; 1.P.169.172; 1.P.169.175; 1.P.169.240;
1.P.169.244; 1.P.172.228; 1.P.172.229; 1.P.172.230; 1.P.172.231; 1.P.172.236;
1.P.172.237; 1.P.172.238; 1.P.172.239; 1.P.172.154; 1.P.172.157; 1.P.172.166;
1.P.172.169; 1.P.172.172; 1.P.172.175; 1.P.172.240; 1.P.172.244; 1.P.175.228;
1.P.175.229; 1.P.175.230; 1.P.175.231; 1.P.175.236; 1.P.175.237; 1.P.175.238;
1.P.175.239; 1.P.175.154; 1.P.175.157; 1.P.175.166; 1.P.175.169; 1.P.175.172;
1.P.175.175; 1.P.175.240; 1.P.175.244; 1.P.240.228; 1.P.240.229; 1.P.240.230;
1.P.240.231; 1.P.240.236; 1.P.240.237; 1.P.240.238; 1.P.240.239; 1.P.240.154;

TABLE 100-continued

1.P.240.157; 1.P.240.166; 1.P.240.169; 1.P.240.172; 1.P.240.175; 1.P.240.240;
1.P.240.244; 1.P.244.228; 1.P.244.229; 1.P.244.230; 1.P.244.231; 1.P.244.236;
1.P.244.237; 1.P.244.238; 1.P.244.239; 1.P.244.154; 1.P.244.157; 1.P.244.166;
1.P.244.169; 1.P.244.172; 1.P.244.175; 1.P.244.240; 1.P.244.244;
Prodrugs of 1.U 1.U.228.228; 1.U.228.229; 1.U.228.230; 1.U.228.231; 1.U.228.236;
1.U.228.237; 1.U.228.238; 1.U.228.239; 1.U.228.154; 1.U.228.157;
1.U.228.166; 1.U.228.169; 1.U.228.172; 1.U.228.175; 1.U.228.240;
1.U.228.244; 1.U.229.228; 1.U.229.229; 1.U.229.230; 1.U.229.231;
1.U.229.236; 1.U.229.237; 1.U.229.238; 1.U.229.239; 1.U.229.154;
1.U.229.157; 1.U.229.166; 1.U.229.169; 1.U.229.172; 1.U.229.175;
1.U.229.240; 1.U.229.244; 1.U.230.228; 1.U.230.229; 1.U.230.230;
1.U.230.231; 1.U.230.236; 1.U.230.237; 1.U.230.238; 1.U.230.239;
1.U.230.154; 1.U.230.157; 1.U.230.166; 1.U.230.169; 1.U.230.172;
1.U.230.175; 1.U.230.240; 1.U.230.244; 1.U.231.228; 1.U.231.229;
1.U.231.230; 1.U.231.231; 1.U.231.236; 1.U.231.237; 1.U.231.238;
1.U.231.239; 1.U.231.154; 1.U.231.157; 1.U.231.166; 1.U.231.169;
1.U.231.172; 1.U.231.175; 1.U.231.240; 1.U.231.244; 1.U.236.228;
1.U.236.229; 1.U.236.230; 1.U.236.231; 1.U.236.236; 1.U.236.237;
1.U.236.238; 1.U.236.239; 1.U.236.154; 1.U.236.157; 1.U.236.166;
1.U.236.169; 1.U.236.172; 1.U.236.175; 1.U.236.240; 1.U.236.244;
1.U.237.228; 1.U.237.229; 1.U.237.230; 1.U.237.231; 1.U.237.236;
1.U.237.237; 1.U.237.238; 1.U.237.239; 1.U.237.154; 1.U.237.157;
1.U.237.166; 1.U.237.169; 1.U.237.172; 1.U.237.175; 1.U.237.240;
1.U.237.244; 1.U.238.228; 1.U.238.229; 1.U.238.230; 1.U.238.231;
1.U.238.236; 1.U.238.237; 1.U.238.238; 1.U.238.239; 1.U.238.154;
1.U.238.157; 1.U.238.166; 1.U.238.169; 1.U.238.172; 1.U.238.175;
1.U.238.240; 1.U.238.244; 1.U.239.228; 1.U.239.229; 1.U.239.230;
1.U.239.231; 1.U.239.236; 1.U.239.237; 1.U.239.238; 1.U.239.239;
1.U.239.154; 1.U.239.157; 1.U.239.166; 1.U.239.169; 1.U.239.172;
1.U.239.175; 1.U.239.240; 1.U.239.244; 1.U.154.228; 1.U.154.229;
1.U.154.230; 1.U.154.231; 1.U.154.236; 1.U.154.237; 1.U.154.238;
1.U.154.239; 1.U.154.154; 1.U.154.157; 1.U.154.166; 1.U.154.169;
1.U.154.172; 1.U.154.175; 1.U.154.240; 1.U.154.244; 1.U.157.228;
1.U.157.229; 1.U.157.230; 1.U.157.231; 1.U.157.236; 1.U.157.237;
1.U.157.238; 1.U.157.239; 1.U.157.154; 1.U.157.157; 1.U.157.166;
1.U.157.169; 1.U.157.172; 1.U.157.175; 1.U.157.240; 1.U.157.244;
1.U.166.228; 1.U.166.229; 1.U.166.230; 1.U.166.231; 1.U.166.236;
1.U.166.237; 1.U.166.238; 1.U.166.239; 1.U.166.154; 1.U.166.157;
1.U.166.166; 1.U.166.169; 1.U.166.172; 1.U.166.175; 1.U.166.240;
1.U.166.244; 1.U.169.228; 1.U.169.229; 1.U.169.230; 1.U.169.231;
1.U.169.236; 1.U.169.237; 1.U.169.238; 1.U.169.239; 1.U.169.154;
1.U.169.157; 1.U.169.166; 1.U.169.169; 1.U.169.172; 1.U.169.175;
1.U.169.240; 1.U.169.244; 1.U.172.228; 1.U.172.229; 1.U.172.230;
1.U.172.231; 1.U.172.236; 1.U.172.237; 1.U.172.238; 1.U.172.239;
1.U.172.154; 1.U.172.157; 1.U.172.166; 1.U.172.169; 1.U.172.172;
1.U.172.175; 1.U.172.240; 1.U.172.244; 1.U.175.228; 1.U.175.229;
1.U.175.230; 1.U.175.231; 1.U.175.236; 1.U.175.237; 1.U.175.238;
1.U.175.239; 1.U.175.154; 1.U.175.157; 1.U.175.166; 1.U.175.169;
1.U.175.172; 1.U.175.175; 1.U.175.240; 1.U.175.244; 1.U.240.228;
1.U.240.229; 1.U.240.230; 1.U.240.231; 1.U.240.236; 1.U.240.237;
1.U.240.238; 1.U.240.239; 1.U.240.154; 1.U.240.157; 1.U.240.166;
1.U.240.169; 1.U.240.172; 1.U.240.175; 1.U.240.240; 1.U.240.244;
1.U.244.228; 1.U.244.229; 1.U.244.230; 1.U.244.231; 1.U.244.236;
1.U.244.237; 1.U.244.238; 1.U.244.239; 1.U.244.154; 1.U.244.157;
1.U.244.166; 1.U.244.169; 1.U.244.172; 1.U.244.175; 1.U.244.240; 1.U.244.244;
Prodrugs of 1.W 1.W.228.228; 1.W.228.229; 1.W.228.230; 1.W.228.231; 1.W.228.236;
1.W.228.237; 1.W.228.238; 1.W.228.239; 1.W.228.154; 1.W.228.157;
1.W.228.166; 1.W.228.169; 1.W.228.172; 1.W.228.175; 1.W.228.240;
1.W.228.244; 1.W.229.228; 1.W.229.229; 1.W.229.230; 1.W.229.231;
1.W.229.236; 1.W.229.237; 1.W.229.238; 1.W.229.239; 1.W.229.154;
1.W.229.157; 1.W.229.166; 1.W.229.169; 1.W.229.172; 1.W.229.175;
1.W.229.240; 1.W.229.244; 1.W.230.228; 1.W.230.229; 1.W.230.230;
1.W.230.231; 1.W.230.236; 1.W.230.237; 1.W.230.238; 1.W.230.239;
1.W.230.154; 1.W.230.157; 1.W.230.166; 1.W.230.169; 1.W.230.172;
1.W.230.175; 1.W.230.240; 1.W.230.244; 1.W.231.228; 1.W.231.229;
1.W.231.230; 1.W.231.231; 1.W.231.236; 1.W.231.237; 1.W.231.238;
1.W.231.239; 1.W.231.154; 1.W.231.157; 1.W.231.166; 1.W.231.169;
1.W.231.172; 1.W.231.175; 1.W.231.240; 1.W.231.244; 1.W.236.228;
1.W.236.229; 1.W.236.230; 1.W.236.231; 1.W.236.236; 1.W.236.237;
1.W.236.238; 1.W.236.239; 1.W.236.154; 1.W.236.157; 1.W.236.166;
1.W.236.169; 1.W.236.172; 1.W.236.175; 1.W.236.240; 1.W.236.244;
1.W.237.228; 1.W.237.229; 1.W.237.230; 1.W.237.231; 1.W.237.236;
1.W.237.237; 1.W.237.238; 1.W.237.239; 1.W.237.154; 1.W.237.157;
1.W.237.166; 1.W.237.169; 1.W.237.172; 1.W.237.175; 1.W.237.240;
1.W.237.244; 1.W.238.228; 1.W.238.229; 1.W.238.230; 1.W.238.231;

TABLE 100-continued

1.W.238.236; 1.W.238.237; 1.W.238.238; 1.W.238.239; 1.W.238.154;
1.W.238.157; 1.W.238.166; 1.W.238.169; 1.W.238.172; 1.W.238.175;
1.W.238.240; 1.W.238.244; 1.W.239.228; 1.W.239.229; 1.W.239.230;
1.W.239.231; 1.W.239.236; 1.W.239.237; 1.W.239.238; 1.W.239.239;
1.W.239.154; 1.W.239.157; 1.W.239.166; 1.W.239.169; 1.W.239.172;
1.W.239.175; 1.W.239.240; 1.W.239.244; 1.W.154.228; 1.W.154.229;
1.W.154.230; 1.W.154.231; 1.W.154.236; 1.W.154.237; 1.W.154.238;
1.W.154.239; 1.W.154.154; 1.W.154.157; 1.W.154.166; 1.W.154.169;
1.W.154.172; 1.W.154.175; 1.W.154.240; 1.W.154.244; 1.W.157.228;
1.W.157.229; 1.W.157.230; 1.W.157.231; 1.W.157.236; 1.W.157.237;
1.W.157.238; 1.W.157.239; 1.W.157.154; 1.W.157.157; 1.W.157.166;
1.W.157.169; 1.W.157.172; 1.W.157.175; 1.W.157.240; 1.W.157.244;
1.W.166.228; 1.W.166.229; 1.W.166.230; 1.W.166.231; 1.W.166.236;
1.W.166.237; 1.W.166.238; 1.W.166.239; 1.W.166.154; 1.W.166.157;
1.W.166.166; 1.W.166.169; 1.W.166.172; 1.W.166.175; 1.W.166.240;
1.W.166.244; 1.W.169.228; 1.W.169.229; 1.W.169.230; 1.W.169.231;
1.W.169.236; 1.W.169.237; 1.W.169.238; 1.W.169.239; 1.W.169.154;
1.W.169.157; 1.W.169.166; 1.W.169.169; 1.W.169.172; 1.W.169.175;
1.W.169.240; 1.W.169.244; 1.W.172.228; 1.W.172.229; 1.W.172.230;
1.W.172.231; 1.W.172.236; 1.W.172.237; 1.W.172.238; 1.W.172.239;
1.W.172.154; 1.W.172.157; 1.W.172.166; 1.W.172.169; 1.W.172.172;
1.W.172.175; 1.W.172.240; 1.W.172.244; 1.W.175.228; 1.W.175.229;
1.W.175.230; 1.W.175.231; 1.W.175.236; 1.W.175.237; 1.W.175.238;
1.W.175.239; 1.W.175.154; 1.W.175.157; 1.W.175.166; 1.W.175.169;
1.W.175.172; 1.W.175.175; 1.W.175.240; 1.W.175.244; 1.W.240.228;
1.W.240.229; 1.W.240.230; 1.W.240.231; 1.W.240.236; 1.W.240.237;
1.W.240.238; 1.W.240.239; 1.W.240.154; 1.W.240.157; 1.W.240.166;
1.W.240.169; 1.W.240.172; 1.W.240.175; 1.W.240.240; 1.W.240.244;
1.W.244.228; 1.W.244.229; 1.W.244.230; 1.W.244.231; 1.W.244.236;
1.W.244.237; 1.W.244.238; 1.W.244.239; 1.W.244.154; 1.W.244.157;
1.W.244.166; 1.W.244.169; 1.W.244.172; 1.W.244.175; 1.W.244.240;
1.W.244.244;
Prodrugs of 1.Y 1.Y.228.228; 1.Y.228.229; 1.Y.228.230; 1.Y.228.231; 1.Y.228.236;
1.Y.228.237; 1.Y.228.238; 1.Y.228.239; 1.Y.228.154; 1.Y.228.157; 1.Y.228.166;
1.Y.228.169; 1.Y.228.172; 1.Y.228.175; 1.Y.228.240; 1.Y.228.244; 1.Y.229.228;
1.Y.229.229; 1.Y.229.230; 1.Y.229.231; 1.Y.229.236; 1.Y.229.237; 1.Y.229.238;
1.Y.229.239; 1.Y.229.154; 1.Y.229.157; 1.Y.229.166; 1.Y.229.169; 1.Y.229.172;
1.Y.229.175; 1.Y.229.240; 1.Y.229.244; 1.Y.230.228; 1.Y.230.229; 1.Y.230.230;
1.Y.230.231; 1.Y.230.236; 1.Y.230.237; 1.Y.230.238; 1.Y.230.239; 1.Y.230.154;
1.Y.230.157; 1.Y.230.166; 1.Y.230.169; 1.Y.230.172; 1.Y.230.175; 1.Y.230.240;
1.Y.230.244; 1.Y.231.228; 1.Y.231.229; 1.Y.231.230; 1.Y.231.231; 1.Y.231.236;
1.Y.231.237; 1.Y.231.238; 1.Y.231.239; 1.Y.231.154; 1.Y.231.157; 1.Y.231.166;
1.Y.231.169; 1.Y.231.172; 1.Y.231.175; 1.Y.231.240; 1.Y.231.244; 1.Y.236.228;
1.Y.236.229; 1.Y.236.230; 1.Y.236.231; 1.Y.236.236; 1.Y.236.237; 1.Y.236.238;
1.Y.236.239; 1.Y.236.154; 1.Y.236.157; 1.Y.236.166; 1.Y.236.169; 1.Y.236.172;
1.Y.236.175; 1.Y.236.240; 1.Y.236.244; 1.Y.237.228; 1.Y.237.229; 1.Y.237.230;
1.Y.237.231; 1.Y.237.236; 1.Y.237.237; 1.Y.237.238; 1.Y.237.239; 1.Y.237.154;
1.Y.237.157; 1.Y.237.166; 1.Y.237.169; 1.Y.237.172; 1.Y.237.175; 1.Y.237.240;
1.Y.237.244; 1.Y.238.228; 1.Y.238.229; 1.Y.238.230; 1.Y.238.231; 1.Y.238.236;
1.Y.238.237; 1.Y.238.238; 1.Y.238.239; 1.Y.238.154; 1.Y.238.157; 1.Y.238.166;
1.Y.238.169; 1.Y.238.172; 1.Y.238.175; 1.Y.238.240; 1.Y.238.244; 1.Y.239.228;
1.Y.239.229; 1.Y.239.230; 1.Y.239.231; 1.Y.239.236; 1.Y.239.237; 1.Y.239.238;
1.Y.239.239; 1.Y.239.154; 1.Y.239.157; 1.Y.239.166; 1.Y.239.169; 1.Y.239.172;
1.Y.239.175; 1.Y.239.240; 1.Y.239.244; 1.Y.154.228; 1.Y.154.229; 1.Y.154.230;
1.Y.154.231; 1.Y.154.236; 1.Y.154.237; 1.Y.154.238; 1.Y.154.239; 1.Y.154.154;
1.Y.154.157; 1.Y.154.166; 1.Y.154.169; 1.Y.154.172; 1.Y.154.175; 1.Y.154.240;
1.Y.154.244; 1.Y.157.228; 1.Y.157.229; 1.Y.157.230; 1.Y.157.231; 1.Y.157.236;
1.Y.157.237; 1.Y.157.238; 1.Y.157.239; 1.Y.157.154; 1.Y.157.157; 1.Y.157.166;
1.Y.157.169; 1.Y.157.172; 1.Y.157.175; 1.Y.157.240; 1.Y.157.244; 1.Y.166.228;
1.Y.166.229; 1.Y.166.230; 1.Y.166.231; 1.Y.166.236; 1.Y.166.237; 1.Y.166.238;
1.Y.166.239; 1.Y.166.154; 1.Y.166.157; 1.Y.166.166; 1.Y.166.169; 1.Y.166.172;
1.Y.166.175; 1.Y.166.240; 1.Y.166.244; 1.Y.169.228; 1.Y.169.229; 1.Y.169.230;
1.Y.169.231; 1.Y.169.236; 1.Y.169.237; 1.Y.169.238; 1.Y.169.239; 1.Y.169.154;
1.Y.169.157; 1.Y.169.166; 1.Y.169.169; 1.Y.169.172; 1.Y.169.175; 1.Y.169.240;
1.Y.169.244; 1.Y.172.228; 1.Y.172.229; 1.Y.172.230; 1.Y.172.231; 1.Y.172.236;
1.Y.172.237; 1.Y.172.238; 1.Y.172.239; 1.Y.172.154; 1.Y.172.157; 1.Y.172.166;
1.Y.172.169; 1.Y.172.172; 1.Y.172.175; 1.Y.172.240; 1.Y.172.244; 1.Y.175.228;
1.Y.175.229; 1.Y.175.230; 1.Y.175.231; 1.Y.175.236; 1.Y.175.237; 1.Y.175.238;
1.Y.175.239; 1.Y.175.154; 1.Y.175.157; 1.Y.175.166; 1.Y.175.169; 1.Y.175.172;
1.Y.175.175; 1.Y.175.240; 1.Y.175.244; 1.Y.240.228; 1.Y.240.229; 1.Y.240.230;
1.Y.240.231; 1.Y.240.236; 1.Y.240.237; 1.Y.240.238; 1.Y.240.239; 1.Y.240.154;
1.Y.240.157; 1.Y.240.166; 1.Y.240.169; 1.Y.240.172; 1.Y.240.175; 1.Y.240.240;
1.Y.240.244; 1.Y.244.228; 1.Y.244.229; 1.Y.244.230; 1.Y.244.231; 1.Y.244.236;
1.Y.244.237; 1.Y.244.238; 1.Y.244.239; 1.Y.244.154; 1.Y.244.157; 1.Y.244.166;
1.Y.244.169; 1.Y.244.172; 1.Y.244.175; 1.Y.244.240; 1.Y.244.244;

TABLE 100-continued

Prodrugs of 2.B

2.B.228.228; 2.B.228.229; 2.B.228.230; 2.B.228.231; 2.B.228.236;
2.B.228.237; 2.B.228.238; 2.B.228.239; 2.B.228.154; 2.B.228.157; 2.B.228.166;
2.B.228.169; 2.B.228.172; 2.B.228.175; 2.B.228.240; 2.B.228.244; 2.B.229.228;
2.B.229.229; 2.B.229.230; 2.B.229.231; 2.B.229.236; 2.B.229.237; 2.B.229.238;
2.B.229.239; 2.B.229.154; 2.B.229.157; 2.B.229.166; 2.B.229.169; 2.B.229.172;
2.B.229.175; 2.B.229.240; 2.B.229.244; 2.B.230.228; 2.B.230.229; 2.B.230.230;
2.B.230.231; 2.B.230.236; 2.B.230.237; 2.B.230.238; 2.B.230.239; 2.B.230.154;
2.B.230.157; 2.B.230.166; 2.B.230.169; 2.B.230.172; 2.B.230.175; 2.B.230.240;
2.B.230.244; 2.B.231.228; 2.B.231.229; 2.B.231.230; 2.B.231.231; 2.B.231.236;
2.B.231.237; 2.B.231.238; 2.B.231.239; 2.B.231.154; 2.B.231.157; 2.B.231.166;
2.B.231.169; 2.B.231.172; 2.B.231.175; 2.B.231.240; 2.B.231.244; 2.B.236.228;
2.B.236.229; 2.B.236.230; 2.B.236.231; 2.B.236.236; 2.B.236.237; 2.B.236.238;
2.B.236.239; 2.B.236.154; 2.B.236.157; 2.B.236.166; 2.B.236.169; 2.B.236.172;
2.B.236.175; 2.B.236.240; 2.B.236.244; 2.B.237.228; 2.B.237.229; 2.B.237.230;
2.B.237.231; 2.B.237.236; 2.B.237.237; 2.B.237.238; 2.B.237.239; 2.B.237.154;
2.B.237.157; 2.B.237.166; 2.B.237.169; 2.B.237.172; 2.B.237.175; 2.B.237.240;
2.B.237.244; 2.B.238.228; 2.B.238.229; 2.B.238.230; 2.B.238.231; 2.B.238.236;
2.B.238.237; 2.B.238.238; 2.B.238.239; 2.B.238.154; 2.B.238.157; 2.B.238.166;
2.B.238.169; 2.B.238.172; 2.B.238.175; 2.B.238.240; 2.B.238.244; 2.B.239.228;
2.B.239.229; 2.B.239.230; 2.B.239.231; 2.B.239.236; 2.B.239.237; 2.B.239.238;
2.B.239.239; 2.B.239.154; 2.B.239.157; 2.B.239.166; 2.B.239.169; 2.B.239.172;
2.B.239.175; 2.B.239.240; 2.B.239.244; 2.B.154.228; 2.B.154.229; 2.B.154.230;
2.B.154.231; 2.B.154.236; 2.B.154.237; 2.B.154.238; 2.B.154.239; 2.B.154.154;
2.B.154.157; 2.B.154.166; 2.B.154.169; 2.B.154.172; 2.B.154.175; 2.B.154.240;
2.B.154.244; 2.B.157.228; 2.B.157.229; 2.B.157.230; 2.B.157.231; 2.B.157.236;
2.B.157.237; 2.B.157.238; 2.B.157.239; 2.B.157.154; 2.B.157.157; 2.B.157.166;
2.B.157.169; 2.B.157.172; 2.B.157.175; 2.B.157.240; 2.B.157.244; 2.B.166.228;
2.B.166.229; 2.B.166.230; 2.B.166.231; 2.B.166.236; 2.B.166.237; 2.B.166.238;
2.B.166.239; 2.B.166.154; 2.B.166.157; 2.B.166.166; 2.B.166.169; 2.B.166.172;
2.B.166.175; 2.B.166.240; 2.B.166.244; 2.B.169.228; 2.B.169.229; 2.B.169.230;
2.B.169.231; 2.B.169.236; 2.B.169.237; 2.B.169.238; 2.B.169.239; 2.B.169.154;
2.B.169.157; 2.B.169.166; 2.B.169.169; 2.B.169.172; 2.B.169.175; 2.B.169.240;
2.B.169.244; 2.B.172.228; 2.B.172.229; 2.B.172.230; 2.B.172.231; 2.B.172.236;
2.B.172.237; 2.B.172.238; 2.B.172.239; 2.B.172.154; 2.B.172.157; 2.B.172.166;
2.B.172.169; 2.B.172.172; 2.B.172.175; 2.B.172.240; 2.B.172.244; 2.B.175.228;
2.B.175.229; 2.B.175.230; 2.B.175.231; 2.B.175.236; 2.B.175.237; 2.B.175.238;
2.B.175.239; 2.B.175.154; 2.B.175.157; 2.B.175.166; 2.B.175.169; 2.B.175.172;
2.B.175.175; 2.B.175.240; 2.B.175.244; 2.B.240.228; 2.B.240.229; 2.B.240.230;
2.B.240.231; 2.B.240.236; 2.B.240.237; 2.B.240.238; 2.B.240.239; 2.B.240.154;
2.B.240.157; 2.B.240.166; 2.B.240.169; 2.B.240.172; 2.B.240.175; 2.B.240.240;
2.B.240.244; 2.B.244.228; 2.B.244.229; 2.B.244.230; 2.B.244.231; 2.B.244.236;
2.B.244.237; 2.B.244.238; 2.B.244.239; 2.B.244.154; 2.B.244.157; 2.B.244.166;
2.B.244.169; 2.B.244.172; 2.B.244.175; 2.B.244.240; 2.B.244.244;

Prodrugs of 2.D

2.D.228.228; 2.D.228.229; 2.D.228.230; 2.D.228.231; 2.D.228.236;
2.D.228.237; 2.D.228.238; 2.D.228.239; 2.D.228.154; 2.D.228.157;
2.D.228.166; 2.D.228.169; 2.D.228.172; 2.D.228.175; 2.D.228.240;
2.D.228.244; 2.D.229.228; 2.D.229.229; 2.D.229.230; 2.D.229.231;
2.D.229.236; 2.D.229.237; 2.D.229.238; 2.D.229.239; 2.D.229.154;
2.D.229.157; 2.D.229.166; 2.D.229.169; 2.D.229.172; 2.D.229.175;
2.D.229.240; 2.D.229.244; 2.D.230.228; 2.D.230.229; 2.D.230.230;
2.D.230.231; 2.D.230.236; 2.D.230.237; 2.D.230.238; 2.D.230.239;
2.D.230.154; 2.D.230.157; 2.D.230.166; 2.D.230.169; 2.D.230.172;
2.D.230.175; 2.D.230.240; 2.D.230.244; 2.D.231.228; 2.D.231.229;
2.D.231.230; 2.D.231.231; 2.D.231.236; 2.D.231.237; 2.D.231.238;
2.D.231.239; 2.D.231.154; 2.D.231.157; 2.D.231.166; 2.D.231.169;
2.D.231.172; 2.D.231.175; 2.D.231.240; 2.D.231.244; 2.D.236.228;
2.D.236.229; 2.D.236.230; 2.D.236.231; 2.D.236.236; 2.D.236.237;
2.D.236.238; 2.D.236.239; 2.D.236.154; 2.D.236.157; 2.D.236.166;
2.D.236.169; 2.D.236.172; 2.D.236.175; 2.D.236.240; 2.D.236.244;
2.D.237.228; 2.D.237.229; 2.D.237.230; 2.D.237.231; 2.D.237.236;
2.D.237.237; 2.D.237.238; 2.D.237.239; 2.D.237.154; 2.D.237.157;
2.D.237.166; 2.D.237.169; 2.D.237.172; 2.D.237.175; 2.D.237.240;
2.D.237.244; 2.D.238.228; 2.D.238.229; 2.D.238.230; 2.D.238.231;
2.D.238.236; 2.D.238.237; 2.D.238.238; 2.D.238.239; 2.D.238.154;
2.D.238.157; 2.D.238.166; 2.D.238.169; 2.D.238.172; 2.D.238.175;
2.D.238.240; 2.D.238.244; 2.D.239.228; 2.D.239.229; 2.D.239.230;
2.D.239.231; 2.D.239.236; 2.D.239.237; 2.D.239.238; 2.D.239.239;
2.D.239.154; 2.D.239.157; 2.D.239.166; 2.D.239.169; 2.D.239.172;
2.D.239.175; 2.D.239.240; 2.D.239.244; 2.D.154.228; 2.D.154.229;
2.D.154.230; 2.D.154.231; 2.D.154.236; 2.D.154.237; 2.D.154.238;
2.D.154.239; 2.D.154.154; 2.D.154.157; 2.D.154.166; 2.D.154.169;
2.D.154.172; 2.D.154.175; 2.D.154.240; 2.D.154.244; 2.D.157.228;
2.D.157.229; 2.D.157.230; 2.D.157.231; 2.D.157.236; 2.D.157.237;
2.D.157.238; 2.D.157.239; 2.D.157.154; 2.D.157.157; 2.D.157.166;
2.D.157.169; 2.D.157.172; 2.D.157.175; 2.D.157.240; 2.D.157.244;

TABLE 100-continued

2.D.166.228; 2.D.166.229; 2.D.166.230; 2.D.166.231; 2.D.166.236;
2.D.166.237; 2.D.166.238; 2.D.166.239; 2.D.166.154; 2.D.166.157;
2.D.166.166; 2.D.166.169; 2.D.166.172; 2.D.166.175; 2.D.166.240;
2.D.166.244; 2.D.169.228; 2.D.169.229; 2.D.169.230; 2.D.169.231;
2.D.169.236; 2.D.169.237; 2.D.169.238; 2.D.169.239; 2.D.169.154;
2.D.169.157; 2.D.169.166; 2.D.169.169; 2.D.169.172; 2.D.169.175;
2.D.169.240; 2.D.169.244; 2.D.172.228; 2.D.172.229; 2.D.172.230;
2.D.172.231; 2.D.172.236; 2.D.172.237; 2.D.172.238; 2.D.172.239;
2.D.172.154; 2.D.172.157; 2.D.172.166; 2.D.172.169; 2.D.172.172;
2.D.172.175; 2.D.172.240; 2.D.172.244; 2.D.175.228; 2.D.175.229;
2.D.175.230; 2.D.175.231; 2.D.175.236; 2.D.175.237; 2.D.175.238;
2.D.175.239; 2.D.175.154; 2.D.175.157; 2.D.175.166; 2.D.175.169;
2.D.175.172; 2.D.175.175; 2.D.175.240; 2.D.175.244; 2.D.240.228;
2.D.240.229; 2.D.240.230; 2.D.240.231; 2.D.240.236; 2.D.240.237;
2.D.240.238; 2.D.240.239; 2.D.240.154; 2.D.240.157; 2.D.240.166;
2.D.240.169; 2.D.240.172; 2.D.240.175; 2.D.240.240; 2.D.240.244;
2.D.244.228; 2.D.244.229; 2.D.244.230; 2.D.244.231; 2.D.244.236;
2.D.244.237; 2.D.244.238; 2.D.244.239; 2.D.244.154; 2.D.244.157;
2.D.244.166; 2.D.244.169; 2.D.244.172; 2.D.244.175; 2.D.244.240; 2.D.244.244;
Prodrugs of 2.E 2.E.228.228; 2.E.228.229; 2.E.228.230; 2.E.228.231; 2.E.228.236;
2.E.228.237; 2.E.228.238; 2.E.228.239; 2.E.228.154; 2.E.228.157; 2.E.228.166;
2.E.228.169; 2.E.228.172; 2.E.228.175; 2.E.228.240; 2.E.228.244; 2.E.229.228;
2.E.229.229; 2.E.229.230; 2.E.229.231; 2.E.229.236; 2.E.229.237; 2.E.229.238;
2.E.229.239; 2.E.229.154; 2.E.229.157; 2.E.229.166; 2.E.229.169; 2.E.229.172;
2.E.229.175; 2.E.229.240; 2.E.229.244; 2.E.230.228; 2.E.230.229; 2.E.230.230;
2.E.230.231; 2.E.230.236; 2.E.230.237; 2.E.230.238; 2.E.230.239; 2.E.230.154;
2.E.230.157; 2.E.230.166; 2.E.230.169; 2.E.230.172; 2.E.230.175; 2.E.230.240;
2.E.230.244; 2.E.231.228; 2.E.231.229; 2.E.231.230; 2.E.231.231; 2.E.231.236;
2.E.231.237; 2.E.231.238; 2.E.231.239; 2.E.231.154; 2.E.231.157; 2.E.231.166;
2.E.231.169; 2.E.231.172; 2.E.231.175; 2.E.231.240; 2.E.231.244; 2.E.236.228;
2.E.236.229; 2.E.236.230; 2.E.236.231; 2.E.236.236; 2.E.236.237; 2.E.236.238;
2.E.236.239; 2.E.236.154; 2.E.236.157; 2.E.236.166; 2.E.236.169; 2.E.236.172;
2.E.236.175; 2.E.236.240; 2.E.236.244; 2.E.237.228; 2.E.237.229; 2.E.237.230;
2.E.237.231; 2.E.237.236; 2.E.237.237; 2.E.237.238; 2.E.237.239; 2.E.237.154;
2.E.237.157; 2.E.237.166; 2.E.237.169; 2.E.237.172; 2.E.237.175; 2.E.237.240;
2.E.237.244; 2.E.238.228; 2.E.238.229; 2.E.238.230; 2.E.238.231; 2.E.238.236;
2.E.238.237; 2.E.238.238; 2.E.238.239; 2.E.238.154; 2.E.238.157; 2.E.238.166;
2.E.238.169; 2.E.238.172; 2.E.238.175; 2.E.238.240; 2.E.238.244; 2.E.239.228;
2.E.239.229; 2.E.239.230; 2.E.239.231; 2.E.239.236; 2.E.239.237; 2.E.239.238;
2.E.239.239; 2.E.239.154; 2.E.239.157; 2.E.239.166; 2.E.239.169; 2.E.239.172;
2.E.239.175; 2.E.239.240; 2.E.239.244; 2.E.154.228; 2.E.154.229; 2.E.154.230;
2.E.154.231; 2.E.154.236; 2.E.154.237; 2.E.154.238; 2.E.154.239; 2.E.154.154;
2.E.154.157; 2.E.154.166; 2.E.154.169; 2.E.154.172; 2.E.154.175; 2.E.154.240;
2.E.154.244; 2.E.157.228; 2.E.157.229; 2.E.157.230; 2.E.157.231; 2.E.157.236;
2.E.157.237; 2.E.157.238; 2.E.157.239; 2.E.157.154; 2.E.157.157; 2.E.157.166;
2.E.157.169; 2.E.157.172; 2.E.157.175; 2.E.157.240; 2.E.157.244; 2.E.166.228;
2.E.166.229; 2.E.166.230; 2.E.166.231; 2.E.166.236; 2.E.166.237; 2.E.166.238;
2.E.166.239; 2.E.166.154; 2.E.166.157; 2.E.166.166; 2.E.166.169; 2.E.166.172;
2.E.166.175; 2.E.166.240; 2.E.166.244; 2.E.169.228; 2.E.169.229; 2.E.169.230;
2.E.169.231; 2.E.169.236; 2.E.169.237; 2.E.169.238; 2.E.169.239; 2.E.169.154;
2.E.169.157; 2.E.169.166; 2.E.169.169; 2.E.169.172; 2.E.169.175; 2.E.169.240;
2.E.169.244; 2.E.172.228; 2.E.172.229; 2.E.172.230; 2.E.172.231; 2.E.172.236;
2.E.172.237; 2.E.172.238; 2.E.172.239; 2.E.172.154; 2.E.172.157; 2.E.172.166;
2.E.172.169; 2.E.172.172; 2.E.172.175; 2.E.172.240; 2.E.172.244; 2.E.175.228;
2.E.175.229; 2.E.175.230; 2.E.175.231; 2.E.175.236; 2.E.175.237; 2.E.175.238;
2.E.175.239; 2.E.175.154; 2.E.175.157; 2.E.175.166; 2.E.175.169; 2.E.175.172;
2.E.175.175; 2.E.175.240; 2.E.175.244; 2.E.240.228; 2.E.240.229; 2.E.240.230;
2.E.240.231; 2.E.240.236; 2.E.240.237; 2.E.240.238; 2.E.240.239; 2.E.240.154;
2.E.240.157; 2.E.240.166; 2.E.240.169; 2.E.240.172; 2.E.240.175; 2.E.240.240;
2.E.240.244; 2.E.244.228; 2.E.244.229; 2.E.244.230; 2.E.244.231; 2.E.244.236;
2.E.244.237; 2.E.244.238; 2.E.244.239; 2.E.244.154; 2.E.244.157; 2.E.244.166;
2.E.244.169; 2.E.244.172; 2.E.244.175; 2.E.244.240; 2.E.244.244;
Prodrugs of 2.G 2.G.228.228; 2.G.228.229; 2.G.228.230; 2.G.228.231; 2.G.228.236;
2.G.228.237; 2.G.228.238; 2.G.228.239; 2.G.228.154; 2.G.228.157;
2.G.228.166; 2.G.228.169; 2.G.228.172; 2.G.228.175; 2.G.228.240;
2.G.228.244; 2.G.229.228; 2.G.229.229; 2.G.229.230; 2.G.229.231;
2.G.229.236; 2.G.229.237; 2.G.229.238; 2.G.229.239; 2.G.229.154;
2.G.229.157; 2.G.229.166; 2.G.229.169; 2.G.229.172; 2.G.229.175;
2.G.229.240; 2.G.229.244; 2.G.230.228; 2.G.230.229; 2.G.230.230;
2.G.230.231; 2.G.230.236; 2.G.230.237; 2.G.230.238; 2.G.230.239;
2.G.230.154; 2.G.230.157; 2.G.230.166; 2.G.230.169; 2.G.230.172;
2.G.230.175; 2.G.230.240; 2.G.230.244; 2.G.231.228; 2.G.231.229;
2.G.231.230; 2.G.231.231; 2.G.231.236; 2.G.231.237; 2.G.231.238;
2.G.231.239; 2.G.231.154; 2.G.231.157; 2.G.231.166; 2.G.231.169;
2.G.231.172; 2.G.231.175; 2.G.231.240; 2.G.231.244; 2.G.236.228;

TABLE 100-continued

2.G.236.229; 2.G.236.230; 2.G.236.231; 2.G.236.236; 2.G.236.237;
2.G.236.238; 2.G.236.239; 2.G.236.154; 2.G.236.157; 2.G.236.166;
2.G.236.169; 2.G.236.172; 2.G.236.175; 2.G.236.240; 2.G.236.244;
2.G.237.228; 2.G.237.229; 2.G.237.230; 2.G.237.231; 2.G.237.236;
2.G.237.237; 2.G.237.238; 2.G.237.239; 2.G.237.154; 2.G.237.157;
2.G.237.166; 2.G.237.169; 2.G.237.172; 2.G.237.175; 2.G.237.240;
2.G.237.244; 2.G.238.228; 2.G.238.229; 2.G.238.230; 2.G.238.231;
2.G.238.236; 2.G.238.237; 2.G.238.238; 2.G.238.239; 2.G.238.154;
2.G.238.157; 2.G.238.166; 2.G.238.169; 2.G.238.172; 2.G.238.175;
2.G.238.240; 2.G.238.244; 2.G.239.228; 2.G.239.229; 2.G.239.230;
2.G.239.231; 2.G.239.236; 2.G.239.237; 2.G.239.238; 2.G.239.239;
2.G.239.154; 2.G.239.157; 2.G.239.166; 2.G.239.169; 2.G.239.172;
2.G.239.175; 2.G.239.240; 2.G.239.244; 2.G.154.228; 2.G.154.229;
2.G.154.230; 2.G.154.231; 2.G.154.236; 2.G.154.237; 2.G.154.238;
2.G.154.239; 2.G.154.154; 2.G.154.157; 2.G.154.166; 2.G.154.169;
2.G.154.172; 2.G.154.175; 2.G.154.240; 2.G.154.244; 2.G.157.228;
2.G.157.229; 2.G.157.230; 2.G.157.231; 2.G.157.236; 2.G.157.237;
2.G.157.238; 2.G.157.239; 2.G.157.154; 2.G.157.157; 2.G.157.166;
2.G.157.169; 2.G.157.172; 2.G.157.175; 2.G.157.240; 2.G.157.244;
2.G.166.228; 2.G.166.229; 2.G.166.230; 2.G.166.231; 2.G.166.236;
2.G.166.237; 2.G.166.238; 2.G.166.239; 2.G.166.154; 2.G.166.157;
2.G.166.166; 2.G.166.169; 2.G.166.172; 2.G.166.175; 2.G.166.240;
2.G.166.244; 2.G.169.228; 2.G.169.229; 2.G.169.230; 2.G.169.231;
2.G.169.236; 2.G.169.237; 2.G.169.238; 2.G.169.239; 2.G.169.154;
2.G.169.157; 2.G.169.166; 2.G.169.169; 2.G.169.172; 2.G.169.175;
2.G.169.240; 2.G.169.244; 2.G.172.228; 2.G.172.229; 2.G.172.230;
2.G.172.231; 2.G.172.236; 2.G.172.237; 2.G.172.238; 2.G.172.239;
2.G.172.154; 2.G.172.157; 2.G.172.166; 2.G.172.169; 2.G.172.172;
2.G.172.175; 2.G.172.240; 2.G.172.244; 2.G.175.228; 2.G.175.229;
2.G.175.230; 2.G.175.231; 2.G.175.236; 2.G.175.237; 2.G.175.238;
2.G.175.239; 2.G.175.154; 2.G.175.157; 2.G.175.166; 2.G.175.169;
2.G.175.172; 2.G.175.175; 2.G.175.240; 2.G.175.244; 2.G.240.228;
2.G.240.229; 2.G.240.230; 2.G.240.231; 2.G.240.236; 2.G.240.237;
2.G.240.238; 2.G.240.239; 2.G.240.154; 2.G.240.157; 2.G.240.166;
2.G.240.169; 2.G.240.172; 2.G.240.175; 2.G.240.240; 2.G.240.244;
2.G.244.228; 2.G.244.229; 2.G.244.230; 2.G.244.231; 2.G.244.236;
2.G.244.237; 2.G.244.238; 2.G.244.239; 2.G.244.154; 2.G.244.157;
2.G.244.166; 2.G.244.169; 2.G.244.172; 2.G.244.175; 2.G.244.240; 2.G.244.244;
Prodrugs of 2.I 2.I.228.228; 2.I.228.229; 2.I.228.230; 2.I.228.231; 2.I.228.236; 2.I.228.237;
2.I.228.238; 2.I.228.239; 2.I.228.154; 2.I.228.157; 2.I.228.166; 2.I.228.169;
2.I.228.172; 2.I.228.175; 2.I.228.240; 2.I.228.244; 2.I.229.228; 2.I.229.229;
2.I.229.230; 2.I.229.231; 2.I.229.236; 2.I.229.237; 2.I.229.238; 2.I.229.239;
2.I.229.154; 2.I.229.157; 2.I.229.166; 2.I.229.169; 2.I.229.172; 2.I.229.175;
2.I.229.240; 2.I.229.244; 2.I.230.228; 2.I.230.229; 2.I.230.230; 2.I.230.231;
2.I.230.236; 2.I.230.237; 2.I.230.238; 2.I.230.239; 2.I.230.154; 2.I.230.157;
2.I.230.166; 2.I.230.169; 2.I.230.172; 2.I.230.175; 2.I.230.240; 2.I.230.244;
2.I.231.228; 2.I.231.229; 2.I.231.230; 2.I.231.231; 2.I.231.236; 2.I.231.237;
2.I.231.238; 2.I.231.239; 2.I.231.154; 2.I.231.157; 2.I.231.166; 2.I.231.169;
2.I.231.172; 2.I.231.175; 2.I.231.240; 2.I.231.244; 2.I.236.228; 2.I.236.229;
2.I.236.230; 2.I.236.231; 2.I.236.236; 2.I.236.237; 2.I.236.238; 2.I.236.239;
2.I.236.154; 2.I.236.157; 2.I.236.166; 2.I.236.169; 2.I.236.172; 2.I.236.175;
2.I.236.240; 2.I.236.244; 2.I.237.228; 2.I.237.229; 2.I.237.230; 2.I.237.231;
2.I.237.236; 2.I.237.237; 2.I.237.238; 2.I.237.239; 2.I.237.154; 2.I.237.157;
2.I.237.166; 2.I.237.169; 2.I.237.172; 2.I.237.175; 2.I.237.240; 2.I.237.244;
2.I.238.228; 2.I.238.229; 2.I.238.230; 2.I.238.231; 2.I.238.236; 2.I.238.237;
2.I.238.238; 2.I.238.239; 2.I.238.154; 2.I.238.157; 2.I.238.166; 2.I.238.169;
2.I.238.172; 2.I.238.175; 2.I.238.240; 2.I.238.244; 2.I.239.228; 2.I.239.229;
2.I.239.230; 2.I.239.231; 2.I.239.236; 2.I.239.237; 2.I.239.238; 2.I.239.239;
2.I.239.154; 2.I.239.157; 2.I.239.166; 2.I.239.169; 2.I.239.172; 2.I.239.175;
2.I.239.240; 2.I.239.244; 2.I.154.228; 2.I.154.229; 2.I.154.230; 2.I.154.231;
2.I.154.236; 2.I.154.237; 2.I.154.238; 2.I.154.239; 2.I.154.154; 2.I.154.157;
2.I.154.166; 2.I.154.169; 2.I.154.172; 2.I.154.175; 2.I.154.240; 2.I.154.244;
2.I.157.228; 2.I.157.229; 2.I.157.230; 2.I.157.231; 2.I.157.236; 2.I.157.237;
2.I.157.238; 2.I.157.239; 2.I.157.154; 2.I.157.157; 2.I.157.166; 2.I.157.169;
2.I.157.172; 2.I.157.175; 2.I.157.240; 2.I.157.244; 2.I.166.228; 2.I.166.229;
2.I.166.230; 2.I.166.231; 2.I.166.236; 2.I.166.237; 2.I.166.238; 2.I.166.239;
2.I.166.154; 2.I.166.157; 2.I.166.166; 2.I.166.169; 2.I.166.172; 2.I.166.175;
2.I.166.240; 2.I.166.244; 2.I.169.228; 2.I.169.229; 2.I.169.230; 2.I.169.231;
2.I.169.236; 2.I.169.237; 2.I.169.238; 2.I.169.239; 2.I.169.154; 2.I.169.157;
2.I.169.166; 2.I.169.169; 2.I.169.172; 2.I.169.175; 2.I.169.240; 2.I.169.244;
2.I.172.228; 2.I.172.229; 2.I.172.230; 2.I.172.231; 2.I.172.236; 2.I.172.237;
2.I.172.238; 2.I.172.239; 2.I.172.154; 2.I.172.157; 2.I.172.166; 2.I.172.169;
2.I.172.172; 2.I.172.175; 2.I.172.240; 2.I.172.244; 2.I.175.228; 2.I.175.229;
2.I.175.230; 2.I.175.231; 2.I.175.236; 2.I.175.237; 2.I.175.238; 2.I.175.239;
2.I.175.154; 2.I.175.157; 2.I.175.166; 2.I.175.169; 2.I.175.172; 2.I.175.175;
2.I.175.240; 2.I.175.244; 2.I.240.228; 2.I.240.229; 2.I.240.230; 2.I.240.231;
2.I.240.236; 2.I.240.237; 2.I.240.238; 2.I.240.239; 2.I.240.154; 2.I.240.157;

TABLE 100-continued

2.I.240.166; 2.I.240.169; 2.I.240.172; 2.I.240.175; 2.I.240.240; 2.I.240.244;
2.I.244.228; 2.I.244.229; 2.I.244.230; 2.I.244.231; 2.I.244.236; 2.I.244.237;
2.I.244.238; 2.I.244.239; 2.I.244.154; 2.I.244.157; 2.I.244.166; 2.I.244.169;
2.I.244.172; 2.I.244.175; 2.I.244.240; 2.I.244.244;
Prodrugs of 2.J 2.J.228.228; 2.J.228.229; 2.J.228.230; 2.J.228.231; 2.J.228.236; 2.J.228.237;
2.J.228.238; 2.J.228.239; 2.J.228.154; 2.J.228.157; 2.J.228.166; 2.J.228.169;
2.J.228.172; 2.J.228.175; 2.J.228.240; 2.J.228.244; 2.J.229.228; 2.J.229.229;
2.J.229.230; 2.J.229.231; 2.J.229.236; 2.J.229.237; 2.J.229.238; 2.J.229.239;
2.J.229.154; 2.J.229.157; 2.J.229.166; 2.J.229.169; 2.J.229.172; 2.J.229.175;
2.J.229.240; 2.J.229.244; 2.J.230.228; 2.J.230.229; 2.J.230.230; 2.J.230.231;
2.J.230.236; 2.J.230.237; 2.J.230.238; 2.J.230.239; 2.J.230.154; 2.J.230.157;
2.J.230.166; 2.J.230.169; 2.J.230.172; 2.J.230.175; 2.J.230.240; 2.J.230.244;
2.J.231.228; 2.J.231.229; 2.J.231.230; 2.J.231.231; 2.J.231.236; 2.J.231.237;
2.J.231.238; 2.J.231.239; 2.J.231.154; 2.J.231.157; 2.J.231.166; 2.J.231.169;
2.J.231.172; 2.J.231.175; 2.J.231.240; 2.J.231.244; 2.J.236.228; 2.J.236.229;
2.J.236.230; 2.J.236.231; 2.J.236.236; 2.J.236.237; 2.J.236.238; 2.J.236.239;
2.J.236.154; 2.J.236.157; 2.J.236.166; 2.J.236.169; 2.J.236.172; 2.J.236.175;
2.J.236.240; 2.J.236.244; 2.J.237.228; 2.J.237.229; 2.J.237.230; 2.J.237.231;
2.J.237.236; 2.J.237.237; 2.J.237.238; 2.J.237.239; 2.J.237.154; 2.J.237.157;
2.J.237.166; 2.J.237.169; 2.J.237.172; 2.J.237.175; 2.J.237.240; 2.J.237.244;
2.J.238.228; 2.J.238.229; 2.J.238.230; 2.J.238.231; 2.J.238.236; 2.J.238.237;
2.J.238.238; 2.J.238.239; 2.J.238.154; 2.J.238.157; 2.J.238.166; 2.J.238.169;
2.J.238.172; 2.J.238.175; 2.J.238.240; 2.J.238.244; 2.J.239.228; 2.J.239.229;
2.J.239.230; 2.J.239.231; 2.J.239.236; 2.J.239.237; 2.J.239.238; 2.J.239.239;
2.J.239.154; 2.J.239.157; 2.J.239.166; 2.J.239.169; 2.J.239.172; 2.J.239.175;
2.J.239.240; 2.J.239.244; 2.J.154.228; 2.J.154.229; 2.J.154.230; 2.J.154.231;
2.J.154.236; 2.J.154.237; 2.J.154.238; 2.J.154.239; 2.J.154.154; 2.J.154.157;
2.J.154.166; 2.J.154.169; 2.J.154.172; 2.J.154.175; 2.J.154.240; 2.J.154.244;
2.J.157.228; 2.J.157.229; 2.J.157.230; 2.J.157.231; 2.J.157.236; 2.J.157.237;
2.J.157.238; 2.J.157.239; 2.J.157.154; 2.J.157.157; 2.J.157.166; 2.J.157.169;
2.J.157.172; 2.J.157.175; 2.J.157.240; 2.J.157.244; 2.J.166.228; 2.J.166.229;
2.J.166.230; 2.J.166.231; 2.J.166.236; 2.J.166.237; 2.J.166.238; 2.J.166.239;
2.J.166.154; 2.J.166.157; 2.J.166.166; 2.J.166.169; 2.J.166.172; 2.J.166.175;
2.J.166.240; 2.J.166.244; 2.J.169.228; 2.J.169.229; 2.J.169.230; 2.J.169.231;
2.J.169.236; 2.J.169.237; 2.J.169.238; 2.J.169.239; 2.J.169.154; 2.J.169.157;
2.J.169.166; 2.J.169.169; 2.J.169.172; 2.J.169.175; 2.J.169.240; 2.J.169.244;
2.J.172.228; 2.J.172.229; 2.J.172.230; 2.J.172.231; 2.J.172.236; 2.J.172.237;
2.J.172.238; 2.J.172.239; 2.J.172.154; 2.J.172.157; 2.J.172.166; 2.J.172.169;
2.J.172.172; 2.J.172.175; 2.J.172.240; 2.J.172.244; 2.J.175.228; 2.J.175.229;
2.J.175.230; 2.J.175.231; 2.J.175.236; 2.J.175.237; 2.J.175.238; 2.J.175.239;
2.J.175.154; 2.J.175.157; 2.J.175.166; 2.J.175.169; 2.J.175.172; 2.J.175.175;
2.J.175.240; 2.J.175.244; 2.J.240.228; 2.J.240.229; 2.J.240.230; 2.J.240.231;
2.J.240.236; 2.J.240.237; 2.J.240.238; 2.J.240.239; 2.J.240.154; 2.J.240.157;
2.J.240.166; 2.J.240.169; 2.J.240.172; 2.J.240.175; 2.J.240.240; 2.J.240.244;
2.J.244.228; 2.J.244.229; 2.J.244.230; 2.J.244.231; 2.J.244.236; 2.J.244.237;
2.J.244.238; 2.J.244.239; 2.J.244.154; 2.J.244.157; 2.J.244.166; 2.J.244.169;
2.J.244.172; 2.J.244.175; 2.J.244.240; 2.J.244.244;
Prodrugs of 2.L 2.L.228.228; 2.L.228.229; 2.L.228.230; 2.L.228.231; 2.L.228.236;
2.L.228.237; 2.L.228.238; 2.L.228.239; 2.L.228.154; 2.L.228.157; 2.L.228.166;
2.L.228.169; 2.L.228.172; 2.L.228.175; 2.L.228.240; 2.L.228.244; 2.L.229.228;
2.L.229.229; 2.L.229.230; 2.L.229.231; 2.L.229.236; 2.L.229.237; 2.L.229.238;
2.L.229.239; 2.L.229.154; 2.L.229.157; 2.L.229.166; 2.L.229.169; 2.L.229.172;
2.L.229.175; 2.L.229.240; 2.L.229.244; 2.L.230.228; 2.L.230.229; 2.L.230.230;
2.L.230.231; 2.L.230.236; 2.L.230.237; 2.L.230.238; 2.L.230.239; 2.L.230.154;
2.L.230.157; 2.L.230.166; 2.L.230.169; 2.L.230.172; 2.L.230.175; 2.L.230.240;
2.L.230.244; 2.L.231.228; 2.L.231.229; 2.L.231.230; 2.L.231.231; 2.L.231.236;
2.L.231.237; 2.L.231.238; 2.L.231.239; 2.L.231.154; 2.L.231.157; 2.L.231.166;
2.L.231.169; 2.L.231.172; 2.L.231.175; 2.L.231.240; 2.L.231.244; 2.L.236.228;
2.L.236.229; 2.L.236.230; 2.L.236.231; 2.L.236.236; 2.L.236.237; 2.L.236.238;
2.L.236.239; 2.L.236.154; 2.L.236.157; 2.L.236.166; 2.L.236.169; 2.L.236.172;
2.L.236.175; 2.L.236.240; 2.L.236.244; 2.L.237.228; 2.L.237.229; 2.L.237.230;
2.L.237.231; 2.L.237.236; 2.L.237.237; 2.L.237.238; 2.L.237.239; 2.L.237.154;
2.L.237.157; 2.L.237.166; 2.L.237.169; 2.L.237.172; 2.L.237.175; 2.L.237.240;
2.L.237.244; 2.L.238.228; 2.L.238.229; 2.L.238.230; 2.L.238.231; 2.L.238.236;
2.L.238.237; 2.L.238.238; 2.L.238.239; 2.L.238.154; 2.L.238.157; 2.L.238.166;
2.L.238.169; 2.L.238.172; 2.L.238.175; 2.L.238.240; 2.L.238.244; 2.L.239.228;
2.L.239.229; 2.L.239.230; 2.L.239.231; 2.L.239.236; 2.L.239.237; 2.L.239.238;
2.L.239.239; 2.L.239.154; 2.L.239.157; 2.L.239.166; 2.L.239.169; 2.L.239.172;
2.L.239.175; 2.L.239.240; 2.L.239.244; 2.L.154.228; 2.L.154.229; 2.L.154.230;
2.L.154.231; 2.L.154.236; 2.L.154.237; 2.L.154.238; 2.L.154.239; 2.L.154.154;
2.L.154.157; 2.L.154.166; 2.L.154.169; 2.L.154.172; 2.L.154.175; 2.L.154.240;
2.L.154.244; 2.L.157.228; 2.L.157.229; 2.L.157.230; 2.L.157.231; 2.L.157.236;
2.L.157.237; 2.L.157.238; 2.L.157.239; 2.L.157.154; 2.L.157.157; 2.L.157.166;
2.L.157.169; 2.L.157.172; 2.L.157.175; 2.L.157.240; 2.L.157.244; 2.L.166.228;
2.L.166.229; 2.L.166.230; 2.L.166.231; 2.L.166.236; 2.L.166.237; 2.L.166.238;

TABLE 100-continued

2.L.166.239; 2.L.166.154; 2.L.166.157; 2.L.166.166; 2.L.166.169; 2.L.166.172; 2.L.166.175; 2.L.166.240; 2.L.166.244; 2.L.169.228; 2.L.169.229; 2.L.169.230; 2.L.169.231; 2.L.169.236; 2.L.169.237; 2.L.169.238; 2.L.169.239; 2.L.169.154; 2.L.169.157; 2.L.169.166; 2.L.169.169; 2.L.169.172; 2.L.169.175; 2.L.169.240; 2.L.169.244; 2.L.172.228; 2.L.172.229; 2.L.172.230; 2.L.172.231; 2.L.172.236; 2.L.172.237; 2.L.172.238; 2.L.172.239; 2.L.172.154; 2.L.172.157; 2.L.172.166; 2.L.172.169; 2.L.172.172; 2.L.172.175; 2.L.172.240; 2.L.172.244; 2.L.175.228; 2.L.175.229; 2.L.175.230; 2.L.175.231; 2.L.175.236; 2.L.175.237; 2.L.175.238; 2.L.175.239; 2.L.175.154; 2.L.175.157; 2.L.175.166; 2.L.175.169; 2.L.175.172; 2.L.175.175; 2.L.175.240; 2.L.175.244; 2.L.240.228; 2.L.240.229; 2.L.240.230; 2.L.240.231; 2.L.240.236; 2.L.240.237; 2.L.240.238; 2.L.240.239; 2.L.240.154; 2.L.240.157; 2.L.240.166; 2.L.240.169; 2.L.240.172; 2.L.240.175; 2.L.240.240; 2.L.240.244; 2.L.244.228; 2.L.244.229; 2.L.244.230; 2.L.244.231; 2.L.244.236; 2.L.244.237; 2.L.244.238; 2.L.244.239; 2.L.244.154; 2.L.244.157; 2.L.244.166; 2.L.244.169; 2.L.244.172; 2.L.244.175; 2.L.244.240; 2.L.244.244;
Prodrugs of 2.O 2.O.228.228; 2.O.228.229; 2.O.228.230; 2.O.228.231; 2.O.228.236; 2.O.228.237; 2.O.228.238; 2.O.228.239; 2.O.228.154; 2.O.228.157; 2.O.228.166; 2.O.228.169; 2.O.228.172; 2.O.228.175; 2.O.228.240; 2.O.228.244; 2.O.229.228; 2.O.229.229; 2.O.229.230; 2.O.229.231; 2.O.229.236; 2.O.229.237; 2.O.229.238; 2.O.229.239; 2.O.229.154; 2.O.229.157; 2.O.229.166; 2.O.229.169; 2.O.229.172; 2.O.229.175; 2.O.229.240; 2.O.229.244; 2.O.230.228; 2.O.230.229; 2.O.230.230; 2.O.230.231; 2.O.230.236; 2.O.230.237; 2.O.230.238; 2.O.230.239; 2.O.230.154; 2.O.230.157; 2.O.230.166; 2.O.230.169; 2.O.230.172; 2.O.230.175; 2.O.230.240; 2.O.230.244; 2.O.231.228; 2.O.231.229; 2.O.231.230; 2.O.231.231; 2.O.231.236; 2.O.231.237; 2.O.231.238; 2.O.231.239; 2.O.231.154; 2.O.231.157; 2.O.231.166; 2.O.231.169; 2.O.231.172; 2.O.231.175; 2.O.231.240; 2.O.231.244; 2.O.236.228; 2.O.236.229; 2.O.236.230; 2.O.236.231; 2.O.236.236; 2.O.236.237; 2.O.236.238; 2.O.236.239; 2.O.236.154; 2.O.236.157; 2.O.236.166; 2.O.236.169; 2.O.236.172; 2.O.236.175; 2.O.236.240; 2.O.236.244; 2.O.237.228; 2.O.237.229; 2.O.237.230; 2.O.237.231; 2.O.237.236; 2.O.237.237; 2.O.237.238; 2.O.237.239; 2.O.237.154; 2.O.237.157; 2.O.237.166; 2.O.237.169; 2.O.237.172; 2.O.237.175; 2.O.237.240; 2.O.237.244; 2.O.238.228; 2.O.238.229; 2.O.238.230; 2.O.238.231; 2.O.238.236; 2.O.238.237; 2.O.238.238; 2.O.238.239; 2.O.238.154; 2.O.238.157; 2.O.238.166; 2.O.238.169; 2.O.238.172; 2.O.238.175; 2.O.238.240; 2.O.238.244; 2.O.239.228; 2.O.239.229; 2.O.239.230; 2.O.239.231; 2.O.239.236; 2.O.239.237; 2.O.239.238; 2.O.239.239; 2.O.239.154; 2.O.239.157; 2.O.239.166; 2.O.239.169; 2.O.239.172; 2.O.239.175; 2.O.239.240; 2.O.239.244; 2.O.154.228; 2.O.154.229; 2.O.154.230; 2.O.154.231; 2.O.154.236; 2.O.154.237; 2.O.154.238; 2.O.154.239; 2.O.154.154; 2.O.154.157; 2.O.154.166; 2.O.154.169; 2.O.154.172; 2.O.154.175; 2.O.154.240; 2.O.154.244; 2.O.157.228; 2.O.157.229; 2.O.157.230; 2.O.157.231; 2.O.157.236; 2.O.157.237; 2.O.157.238; 2.O.157.239; 2.O.157.154; 2.O.157.157; 2.O.157.166; 2.O.157.169; 2.O.157.172; 2.O.157.175; 2.O.157.240; 2.O.157.244; 2.O.166.228; 2.O.166.229; 2.O.166.230; 2.O.166.231; 2.O.166.236; 2.O.166.237; 2.O.166.238; 2.O.166.239; 2.O.166.154; 2.O.166.157; 2.O.166.166; 2.O.166.169; 2.O.166.172; 2.O.166.175; 2.O.166.240; 2.O.166.244; 2.O.169.228; 2.O.169.229; 2.O.169.230; 2.O.169.231; 2.O.169.236; 2.O.169.237; 2.O.169.238; 2.O.169.239; 2.O.169.154; 2.O.169.157; 2.O.169.166; 2.O.169.169; 2.O.169.172; 2.O.169.175; 2.O.169.240; 2.O.169.244; 2.O.172.228; 2.O.172.229; 2.O.172.230; 2.O.172.231; 2.O.172.236; 2.O.172.237; 2.O.172.238; 2.O.172.239; 2.O.172.154; 2.O.172.157; 2.O.172.166; 2.O.172.169; 2.O.172.172; 2.O.172.175; 2.O.172.240; 2.O.172.244; 2.O.175.228; 2.O.175.229; 2.O.175.230; 2.O.175.231; 2.O.175.236; 2.O.175.237; 2.O.175.238; 2.O.175.239; 2.O.175.154; 2.O.175.157; 2.O.175.166; 2.O.175.169; 2.O.175.172; 2.O.175.175; 2.O.175.240; 2.O.175.244; 2.O.240.228; 2.O.240.229; 2.O.240.230; 2.O.240.231; 2.O.240.236; 2.O.240.237; 2.O.240.238; 2.O.240.239; 2.O.240.154; 2.O.240.157; 2.O.240.166; 2.O.240.169; 2.O.240.172; 2.O.240.175; 2.O.240.240; 2.O.240.244; 2.O.244.228; 2.O.244.229; 2.O.244.230; 2.O.244.231; 2.O.244.236; 2.O.244.237; 2.O.244.238; 2.O.244.239; 2.O.244.154; 2.O.244.157; 2.O.244.166; 2.O.244.169; 2.O.244.172; 2.O.244.175; 2.O.244.240; 2.O.244.244;
Prodrugs of 2.P 2.P.228.228; 2.P.228.229; 2.P.228.230; 2.P.228.231; 2.P.228.236; 2.P.228.237; 2.P.228.238; 2.P.228.239; 2.P.228.154; 2.P.228.157; 2.P.228.166; 2.P.228.169; 2.P.228.172; 2.P.228.175; 2.P.228.240; 2.P.228.244; 2.P.229.228; 2.P.229.229; 2.P.229.230; 2.P.229.231; 2.P.229.236; 2.P.229.237; 2.P.229.238; 2.P.229.239; 2.P.229.154; 2.P.229.157; 2.P.229.166; 2.P.229.169; 2.P.229.172; 2.P.229.175; 2.P.229.240; 2.P.229.244; 2.P.230.228; 2.P.230.229; 2.P.230.230; 2.P.230.231; 2.P.230.236; 2.P.230.237; 2.P.230.238; 2.P.230.239; 2.P.230.154; 2.P.230.157; 2.P.230.166; 2.P.230.169; 2.P.230.172; 2.P.230.175; 2.P.230.240; 2.P.230.244; 2.P.231.228; 2.P.231.229; 2.P.231.230; 2.P.231.231; 2.P.231.236;

TABLE 100-continued

2.P.231.237; 2.P.231.238; 2.P.231.239; 2.P.231.154; 2.P.231.157; 2.P.231.166;
2.P.231.169; 2.P.231.172; 2.P.231.175; 2.P.231.240; 2.P.231.244; 2.P.236.228;
2.P.236.229; 2.P.236.230; 2.P.236.231; 2.P.236.236; 2.P.236.237; 2.P.236.238;
2.P.236.239; 2.P.236.154; 2.P.236.157; 2.P.236.166; 2.P.236.169; 2.P.236.172;
2.P.236.175; 2.P.236.240; 2.P.236.244; 2.P.237.228; 2.P.237.229; 2.P.237.230;
2.P.237.231; 2.P.237.236; 2.P.237.237; 2.P.237.238; 2.P.237.239; 2.P.237.154;
2.P.237.157; 2.P.237.166; 2.P.237.169; 2.P.237.172; 2.P.237.175; 2.P.237.240;
2.P.237.244; 2.P.238.228; 2.P.238.229; 2.P.238.230; 2.P.238.231; 2.P.238.236;
2.P.238.237; 2.P.238.238; 2.P.238.239; 2.P.238.154; 2.P.238.157; 2.P.238.166;
2.P.238.169; 2.P.238.172; 2.P.238.175; 2.P.238.240; 2.P.238.244; 2.P.239.228;
2.P.239.229; 2.P.239.230; 2.P.239.231; 2.P.239.236; 2.P.239.237; 2.P.239.238;
2.P.239.239; 2.P.239.154; 2.P.239.157; 2.P.239.166; 2.P.239.169; 2.P.239.172;
2.P.239.175; 2.P.239.240; 2.P.239.244; 2.P.154.228; 2.P.154.229; 2.P.154.230;
2.P.154.231; 2.P.154.236; 2.P.154.237; 2.P.154.238; 2.P.154.239; 2.P.154.154;
2.P.154.157; 2.P.154.166; 2.P.154.169; 2.P.154.172; 2.P.154.175; 2.P.154.240;
2.P.154.244; 2.P.157.228; 2.P.157.229; 2.P.157.230; 2.P.157.231; 2.P.157.236;
2.P.157.237; 2.P.157.238; 2.P.157.239; 2.P.157.154; 2.P.157.157; 2.P.157.166;
2.P.157.169; 2.P.157.172; 2.P.157.175; 2.P.157.240; 2.P.157.244; 2.P.166.228;
2.P.166.229; 2.P.166.230; 2.P.166.231; 2.P.166.236; 2.P.166.237; 2.P.166.238;
2.P.166.239; 2.P.166.154; 2.P.166.157; 2.P.166.166; 2.P.166.169; 2.P.166.172;
2.P.166.175; 2.P.166.240; 2.P.166.244; 2.P.169.228; 2.P.169.229; 2.P.169.230;
2.P.169.231; 2.P.169.236; 2.P.169.237; 2.P.169.238; 2.P.169.239; 2.P.169.154;
2.P.169.157; 2.P.169.166; 2.P.169.169; 2.P.169.172; 2.P.169.175; 2.P.169.240;
2.P.169.244; 2.P.172.228; 2.P.172.229; 2.P.172.230; 2.P.172.231; 2.P.172.236;
2.P.172.237; 2.P.172.238; 2.P.172.239; 2.P.172.154; 2.P.172.157; 2.P.172.166;
2.P.172.169; 2.P.172.172; 2.P.172.175; 2.P.172.240; 2.P.172.244; 2.P.175.228;
2.P.175.229; 2.P.175.230; 2.P.175.231; 2.P.175.236; 2.P.175.237; 2.P.175.238;
2.P.175.239; 2.P.175.154; 2.P.175.157; 2.P.175.166; 2.P.175.169; 2.P.175.172;
2.P.175.175; 2.P.175.240; 2.P.175.244; 2.P.240.228; 2.P.240.229; 2.P.240.230;
2.P.240.231; 2.P.240.236; 2.P.240.237; 2.P.240.238; 2.P.240.239; 2.P.240.154;
2.P.240.157; 2.P.240.166; 2.P.240.169; 2.P.240.172; 2.P.240.175; 2.P.240.240;
2.P.240.244; 2.P.244.228; 2.P.244.229; 2.P.244.230; 2.P.244.231; 2.P.244.236;
2.P.244.237; 2.P.244.238; 2.P.244.239; 2.P.244.154; 2.P.244.157; 2.P.244.166;
2.P.244.169; 2.P.244.172; 2.P.244.175; 2.P.244.240; 2.P.244.244;
Prodrugs of 2.U 2.U.228.228; 2.U.228.229; 2.U.228.230; 2.U.228.231; 2.U.228.236;
2.U.228.237; 2.U.228.238; 2.U.228.239; 2.U.228.154; 2.U.228.157;
2.U.228.166; 2.U.228.169; 2.U.228.172; 2.U.228.175; 2.U.228.240;
2.U.228.244; 2.U.229.228; 2.U.229.229; 2.U.229.230; 2.U.229.231;
2.U.229.236; 2.U.229.237; 2.U.229.238; 2.U.229.239; 2.U.229.154;
2.U.229.157; 2.U.229.166; 2.U.229.169; 2.U.229.172; 2.U.229.175;
2.U.229.240; 2.U.229.244; 2.U.230.228; 2.U.230.229; 2.U.230.230;
2.U.230.231; 2.U.230.236; 2.U.230.237; 2.U.230.238; 2.U.230.239;
2.U.230.154; 2.U.230.157; 2.U.230.166; 2.U.230.169; 2.U.230.172;
2.U.230.175; 2.U.230.240; 2.U.230.244; 2.U.231.228; 2.U.231.229;
2.U.231.230; 2.U.231.231; 2.U.231.236; 2.U.231.237; 2.U.231.238;
2.U.231.239; 2.U.231.154; 2.U.231.157; 2.U.231.166; 2.U.231.169;
2.U.231.172; 2.U.231.175; 2.U.231.240; 2.U.231.244; 2.U.236.228;
2.U.236.229; 2.U.236.230; 2.U.236.231; 2.U.236.236; 2.U.236.237;
2.U.236.238; 2.U.236.239; 2.U.236.154; 2.U.236.157; 2.U.236.166;
2.U.236.169; 2.U.236.172; 2.U.236.175; 2.U.236.240; 2.U.236.244;
2.U.237.228; 2.U.237.229; 2.U.237.230; 2.U.237.231; 2.U.237.236;
2.U.237.237; 2.U.237.238; 2.U.237.239; 2.U.237.154; 2.U.237.157;
2.U.237.166; 2.U.237.169; 2.U.237.172; 2.U.237.175; 2.U.237.240;
2.U.237.244; 2.U.238.228; 2.U.238.229; 2.U.238.230; 2.U.238.231;
2.U.238.236; 2.U.238.237; 2.U.238.238; 2.U.238.239; 2.U.238.154;
2.U.238.157; 2.U.238.166; 2.U.238.169; 2.U.238.172; 2.U.238.175;
2.U.238.240; 2.U.238.244; 2.U.239.228; 2.U.239.229; 2.U.239.230;
2.U.239.231; 2.U.239.236; 2.U.239.237; 2.U.239.238; 2.U.239.239;
2.U.239.154; 2.U.239.157; 2.U.239.166; 2.U.239.169; 2.U.239.172;
2.U.239.175; 2.U.239.240; 2.U.239.244; 2.U.154.228; 2.U.154.229;
2.U.154.230; 2.U.154.231; 2.U.154.236; 2.U.154.237; 2.U.154.238;
2.U.154.239; 2.U.154.154; 2.U.154.157; 2.U.154.166; 2.U.154.169;
2.U.154.172; 2.U.154.175; 2.U.154.240; 2.U.154.244; 2.U.157.228;
2.U.157.229; 2.U.157.230; 2.U.157.231; 2.U.157.236; 2.U.157.237;
2.U.157.238; 2.U.157.239; 2.U.157.154; 2.U.157.157; 2.U.157.166;
2.U.157.169; 2.U.157.172; 2.U.157.175; 2.U.157.240; 2.U.157.244;
2.U.166.228; 2.U.166.229; 2.U.166.230; 2.U.166.231; 2.U.166.236;
2.U.166.237; 2.U.166.238; 2.U.166.239; 2.U.166.154; 2.U.166.157;
2.U.166.166; 2.U.166.169; 2.U.166.172; 2.U.166.175; 2.U.166.240;
2.U.166.244; 2.U.169.228; 2.U.169.229; 2.U.169.230; 2.U.169.231;
2.U.169.236; 2.U.169.237; 2.U.169.238; 2.U.169.239; 2.U.169.154;
2.U.169.157; 2.U.169.166; 2.U.169.169; 2.U.169.172; 2.U.169.175;
2.U.169.240; 2.U.169.244; 2.U.172.228; 2.U.172.229; 2.U.172.230;
2.U.172.231; 2.U.172.236; 2.U.172.237; 2.U.172.238; 2.U.172.239;
2.U.172.154; 2.U.172.157; 2.U.172.166; 2.U.172.169; 2.U.172.172;
2.U.172.175; 2.U.172.240; 2.U.172.244; 2.U.175.228; 2.U.175.229;
2.U.175.230; 2.U.175.231; 2.U.175.236; 2.U.175.237; 2.U.175.238;

TABLE 100-continued

2.U.175.239; 2.U.175.154; 2.U.175.157; 2.U.175.166; 2.U.175.169;
2.U.175.172; 2.U.175.175; 2.U.175.240; 2.U.175.244; 2.U.240.228;
2.U.240.229; 2.U.240.230; 2.U.240.231; 2.U.240.236; 2.U.240.237;
2.U.240.238; 2.U.240.239; 2.U.240.154; 2.U.240.157; 2.U.240.166;
2.U.240.169; 2.U.240.172; 2.U.240.175; 2.U.240.240; 2.U.240.244;
2.U.244.228; 2.U.244.229; 2.U.244.230; 2.U.244.231; 2.U.244.236;
2.U.244.237; 2.U.244.238; 2.U.244.239; 2.U.244.154; 2.U.244.157;
2.U.244.166; 2.U.244.169; 2.U.244.172; 2.U.244.175; 2.U.244.240; 2.U.244.244;
Prodrugs of 2.W 2.W.228.228; 2.W.228.229; 2.W.228.230; 2.W.228.231; 2.W.228.236;
2.W.228.237; 2.W.228.238; 2.W.228.239; 2.W.228.154; 2.W.228.157;
2.W.228.166; 2.W.228.169; 2.W.228.172; 2.W.228.175; 2.W.228.240;
2.W.228.244; 2.W.229.228; 2.W.229.229; 2.W.229.230; 2.W.229.231;
2.W.229.236; 2.W.229.237; 2.W.229.238; 2.W.229.239; 2.W.229.154;
2.W.229.157; 2.W.229.166; 2.W.229.169; 2.W.229.172; 2.W.229.175;
2.W.229.240; 2.W.229.244; 2.W.230.228; 2.W.230.229; 2.W.230.230;
2.W.230.231; 2.W.230.236; 2.W.230.237; 2.W.230.238; 2.W.230.239;
2.W.230.154; 2.W.230.157; 2.W.230.166; 2.W.230.169; 2.W.230.172;
2.W.230.175; 2.W.230.240; 2.W.230.244; 2.W.231.228; 2.W.231.229;
2.W.231.230; 2.W.231.231; 2.W.231.236; 2.W.231.237; 2.W.231.238;
2.W.231.239; 2.W.231.154; 2.W.231.157; 2.W.231.166; 2.W.231.169;
2.W.231.172; 2.W.231.175; 2.W.231.240; 2.W.231.244; 2.W.236.228;
2.W.236.229; 2.W.236.230; 2.W.236.231; 2.W.236.236; 2.W.236.237;
2.W.236.238; 2.W.236.239; 2.W.236.154; 2.W.236.157; 2.W.236.166;
2.W.236.169; 2.W.236.172; 2.W.236.175; 2.W.236.240; 2.W.236.244;
2.W.237.228; 2.W.237.229; 2.W.237.230; 2.W.237.231; 2.W.237.236;
2.W.237.237; 2.W.237.238; 2.W.237.239; 2.W.237.154; 2.W.237.157;
2.W.237.166; 2.W.237.169; 2.W.237.172; 2.W.237.175; 2.W.237.240;
2.W.237.244; 2.W.238.228; 2.W.238.229; 2.W.238.230; 2.W.238.231;
2.W.238.236; 2.W.238.237; 2.W.238.238; 2.W.238.239; 2.W.238.154;
2.W.238.157; 2.W.238.166; 2.W.238.169; 2.W.238.172; 2.W.238.175;
2.W.238.240; 2.W.238.244; 2.W.239.228; 2.W.239.229; 2.W.239.230;
2.W.239.231; 2.W.239.236; 2.W.239.237; 2.W.239.238; 2.W.239.239;
2.W.239.154; 2.W.239.157; 2.W.239.166; 2.W.239.169; 2.W.239.172;
2.W.239.175; 2.W.239.240; 2.W.239.244; 2.W.154.228; 2.W.154.229;
2.W.154.230; 2.W.154.231; 2.W.154.236; 2.W.154.237; 2.W.154.238;
2.W.154.239; 2.W.154.154; 2.W.154.157; 2.W.154.166; 2.W.154.169;
2.W.154.172; 2.W.154.175; 2.W.154.240; 2.W.154.244; 2.W.157.228;
2.W.157.229; 2.W.157.230; 2.W.157.231; 2.W.157.236; 2.W.157.237;
2.W.157.238; 2.W.157.239; 2.W.157.154; 2.W.157.157; 2.W.157.166;
2.W.157.169; 2.W.157.172; 2.W.157.175; 2.W.157.240; 2.W.157.244;
2.W.166.228; 2.W.166.229; 2.W.166.230; 2.W.166.231; 2.W.166.236;
2.W.166.237; 2.W.166.238; 2.W.166.239; 2.W.166.154; 2.W.166.157;
2.W.166.166; 2.W.166.169; 2.W.166.172; 2.W.166.175; 2.W.166.240;
2.W.166.244; 2.W.169.228; 2.W.169.229; 2.W.169.230; 2.W.169.231;
2.W.169.236; 2.W.169.237; 2.W.169.238; 2.W.169.239; 2.W.169.154;
2.W.169.157; 2.W.169.166; 2.W.169.169; 2.W.169.172; 2.W.169.175;
2.W.169.240; 2.W.169.244; 2.W.172.228; 2.W.172.229; 2.W.172.230;
2.W.172.231; 2.W.172.236; 2.W.172.237; 2.W.172.238; 2.W.172.239;
2.W.172.154; 2.W.172.157; 2.W.172.166; 2.W.172.169; 2.W.172.172;
2.W.172.175; 2.W.172.240; 2.W.172.244; 2.W.175.228; 2.W.175.229;
2.W.175.230; 2.W.175.231; 2.W.175.236; 2.W.175.237; 2.W.175.238;
2.W.175.239; 2.W.175.154; 2.W.175.157; 2.W.175.166; 2.W.175.169;
2.W.175.172; 2.W.175.175; 2.W.175.240; 2.W.175.244; 2.W.240.228;
2.W.240.229; 2.W.240.230; 2.W.240.231; 2.W.240.236; 2.W.240.237;
2.W.240.238; 2.W.240.239; 2.W.240.154; 2.W.240.157; 2.W.240.166;
2.W.240.169; 2.W.240.172; 2.W.240.175; 2.W.240.240; 2.W.240.244;
2.W.244.228; 2.W.244.229; 2.W.244.230; 2.W.244.231; 2.W.244.236;
2.W.244.237; 2.W.244.238; 2.W.244.239; 2.W.244.154; 2.W.244.157;
2.W.244.166; 2.W.244.169; 2.W.244.172; 2.W.244.175; 2.W.244.240; 2.W.244.244;
Prodrugs of 2.Y 2.Y.228.228; 2.Y.228.229; 2.Y.228.230; 2.Y.228.231; 2.Y.228.236;
2.Y.228.237; 2.Y.228.238; 2.Y.228.239; 2.Y.228.154; 2.Y.228.157; 2.Y.228.166;
2.Y.228.169; 2.Y.228.172; 2.Y.228.175; 2.Y.228.240; 2.Y.228.244; 2.Y.229.228;
2.Y.229.229; 2.Y.229.230; 2.Y.229.231; 2.Y.229.236; 2.Y.229.237; 2.Y.229.238;
2.Y.229.239; 2.Y.229.154; 2.Y.229.157; 2.Y.229.166; 2.Y.229.169; 2.Y.229.172;
2.Y.229.175; 2.Y.229.240; 2.Y.229.244; 2.Y.230.228; 2.Y.230.229; 2.Y.230.230;
2.Y.230.231; 2.Y.230.236; 2.Y.230.237; 2.Y.230.238; 2.Y.230.239; 2.Y.230.154;
2.Y.230.157; 2.Y.230.166; 2.Y.230.169; 2.Y.230.172; 2.Y.230.175; 2.Y.230.240;
2.Y.230.244; 2.Y.231.228; 2.Y.231.229; 2.Y.231.230; 2.Y.231.231; 2.Y.231.236;
2.Y.231.237; 2.Y.231.238; 2.Y.231.239; 2.Y.231.154; 2.Y.231.157; 2.Y.231.166;
2.Y.231.169; 2.Y.231.172; 2.Y.231.175; 2.Y.231.240; 2.Y.231.244; 2.Y.236.228;
2.Y.236.229; 2.Y.236.230; 2.Y.236.231; 2.Y.236.236; 2.Y.236.237; 2.Y.236.238;
2.Y.236.239; 2.Y.236.154; 2.Y.236.157; 2.Y.236.166; 2.Y.236.169; 2.Y.236.172;
2.Y.236.175; 2.Y.236.240; 2.Y.236.244; 2.Y.237.228; 2.Y.237.229; 2.Y.237.230;
2.Y.237.231; 2.Y.237.236; 2.Y.237.237; 2.Y.237.238; 2.Y.237.239; 2.Y.237.154;
2.Y.237.157; 2.Y.237.166; 2.Y.237.169; 2.Y.237.172; 2.Y.237.175; 2.Y.237.240;

TABLE 100-continued

2.Y.237.244; 2.Y.238.228; 2.Y.238.229; 2.Y.238.230; 2.Y.238.231; 2.Y.238.236;
2.Y.238.237; 2.Y.238.238; 2.Y.238.239; 2.Y.238.154; 2.Y.238.157; 2.Y.238.166;
2.Y.238.169; 2.Y.238.172; 2.Y.238.175; 2.Y.238.240; 2.Y.238.244; 2.Y.239.228;
2.Y.239.229; 2.Y.239.230; 2.Y.239.231; 2.Y.239.236; 2.Y.239.237; 2.Y.239.238;
2.Y.239.239; 2.Y.239.154; 2.Y.239.157; 2.Y.239.166; 2.Y.239.169; 2.Y.239.172;
2.Y.239.175; 2.Y.239.240; 2.Y.239.244; 2.Y.154.228; 2.Y.154.229; 2.Y.154.230;
2.Y.154.231; 2.Y.154.236; 2.Y.154.237; 2.Y.154.238; 2.Y.154.239; 2.Y.154.154;
2.Y.154.157; 2.Y.154.166; 2.Y.154.169; 2.Y.154.172; 2.Y.154.175; 2.Y.154.240;
2.Y.154.244; 2.Y.157.228; 2.Y.157.229; 2.Y.157.230; 2.Y.157.231; 2.Y.157.236;
2.Y.157.237; 2.Y.157.238; 2.Y.157.239; 2.Y.157.154; 2.Y.157.157; 2.Y.157.166;
2.Y.157.169; 2.Y.157.172; 2.Y.157.175; 2.Y.157.240; 2.Y.157.244; 2.Y.166.228;
2.Y.166.229; 2.Y.166.230; 2.Y.166.231; 2.Y.166.236; 2.Y.166.237; 2.Y.166.238;
2.Y.166.239; 2.Y.166.154; 2.Y.166.157; 2.Y.166.166; 2.Y.166.169; 2.Y.166.172;
2.Y.166.175; 2.Y.166.240; 2.Y.166.244; 2.Y.169.228; 2.Y.169.229; 2.Y.169.230;
2.Y.169.231; 2.Y.169.236; 2.Y.169.237; 2.Y.169.238; 2.Y.169.239; 2.Y.169.154;
2.Y.169.157; 2.Y.169.166; 2.Y.169.169; 2.Y.169.172; 2.Y.169.175; 2.Y.169.240;
2.Y.169.244; 2.Y.172.228; 2.Y.172.229; 2.Y.172.230; 2.Y.172.231; 2.Y.172.236;
2.Y.172.237; 2.Y.172.238; 2.Y.172.239; 2.Y.172.154; 2.Y.172.157; 2.Y.172.166;
2.Y.172.169; 2.Y.172.172; 2.Y.172.175; 2.Y.172.240; 2.Y.172.244; 2.Y.175.228;
2.Y.175.229; 2.Y.175.230; 2.Y.175.231; 2.Y.175.236; 2.Y.175.237; 2.Y.175.238;
2.Y.175.239; 2.Y.175.154; 2.Y.175.157; 2.Y.175.166; 2.Y.175.169; 2.Y.175.172;
2.Y.175.175; 2.Y.175.240; 2.Y.175.244; 2.Y.240.228; 2.Y.240.229; 2.Y.240.230;
2.Y.240.231; 2.Y.240.236; 2.Y.240.237; 2.Y.240.238; 2.Y.240.239; 2.Y.240.154;
2.Y.240.157; 2.Y.240.166; 2.Y.240.169; 2.Y.240.172; 2.Y.240.175; 2.Y.240.240;
2.Y.240.244; 2.Y.244.228; 2.Y.244.229; 2.Y.244.230; 2.Y.244.231; 2.Y.244.236;
2.Y.244.237; 2.Y.244.238; 2.Y.244.239; 2.Y.244.154; 2.Y.244.157; 2.Y.244.166;
2.Y.244.169; 2.Y.244.172; 2.Y.244.175; 2.Y.244.240; 2.Y.244.244;
Prodrugs of 3.B 3.B.228.228; 3.B.228.229; 3.B.228.230; 3.B.228.231; 3.B.228.236;
3.B.228.237; 3.B.228.238; 3.B.228.239; 3.B.228.154; 3.B.228.157; 3.B.228.166;
3.B.228.169; 3.B.228.172; 3.B.228.175; 3.B.228.240; 3.B.228.244; 3.B.229.228;
3.B.229.229; 3.B.229.230; 3.B.229.231; 3.B.229.236; 3.B.229.237; 3.B.229.238;
3.B.229.239; 3.B.229.154; 3.B.229.157; 3.B.229.166; 3.B.229.169; 3.B.229.172;
3.B.229.175; 3.B.229.240; 3.B.229.244; 3.B.230.228; 3.B.230.229; 3.B.230.230;
3.B.230.231; 3.B.230.236; 3.B.230.237; 3.B.230.238; 3.B.230.239; 3.B.230.154;
3.B.230.157; 3.B.230.166; 3.B.230.169; 3.B.230.172; 3.B.230.175; 3.B.230.240;
3.B.230.244; 3.B.231.228; 3.B.231.229; 3.B.231.230; 3.B.231.231; 3.B.231.236;
3.B.231.237; 3.B.231.238; 3.B.231.239; 3.B.231.154; 3.B.231.157; 3.B.231.166;
3.B.231.169; 3.B.231.172; 3.B.231.175; 3.B.231.240; 3.B.231.244; 3.B.236.228;
3.B.236.229; 3.B.236.230; 3.B.236.231; 3.B.236.236; 3.B.236.237; 3.B.236.238;
3.B.236.239; 3.B.236.154; 3.B.236.157; 3.B.236.166; 3.B.236.169; 3.B.236.172;
3.B.236.175; 3.B.236.240; 3.B.236.244; 3.B.237.228; 3.B.237.229; 3.B.237.230;
3.B.237.231; 3.B.237.236; 3.B.237.237; 3.B.237.238; 3.B.237.239; 3.B.237.154;
3.B.237.157; 3.B.237.166; 3.B.237.169; 3.B.237.172; 3.B.237.175; 3.B.237.240;
3.B.237.244; 3.B.238.228; 3.B.238.229; 3.B.238.230; 3.B.238.231; 3.B.238.236;
3.B.238.237; 3.B.238.238; 3.B.238.239; 3.B.238.154; 3.B.238.157; 3.B.238.166;
3.B.238.169; 3.B.238.172; 3.B.238.175; 3.B.238.240; 3.B.238.244; 3.B.239.228;
3.B.239.229; 3.B.239.230; 3.B.239.231; 3.B.239.236; 3.B.239.237; 3.B.239.238;
3.B.239.239; 3.B.239.154; 3.B.239.157; 3.B.239.166; 3.B.239.169; 3.B.239.172;
3.B.239.175; 3.B.239.240; 3.B.239.244; 3.B.154.228; 3.B.154.229; 3.B.154.230;
3.B.154.231; 3.B.154.236; 3.B.154.237; 3.B.154.238; 3.B.154.239; 3.B.154.154;
3.B.154.157; 3.B.154.166; 3.B.154.169; 3.B.154.172; 3.B.154.175; 3.B.154.240;
3.B.154.244; 3.B.157.228; 3.B.157.229; 3.B.157.230; 3.B.157.231; 3.B.157.236;
3.B.157.237; 3.B.157.238; 3.B.157.239; 3.B.157.154; 3.B.157.157; 3.B.157.166;
3.B.157.169; 3.B.157.172; 3.B.157.175; 3.B.157.240; 3.B.157.244; 3.B.166.228;
3.B.166.229; 3.B.166.230; 3.B.166.231; 3.B.166.236; 3.B.166.237; 3.B.166.238;
3.B.166.239; 3.B.166.154; 3.B.166.157; 3.B.166.166; 3.B.166.169; 3.B.166.172;
3.B.166.175; 3.B.166.240; 3.B.166.244; 3.B.169.228; 3.B.169.229; 3.B.169.230;
3.B.169.231; 3.B.169.236; 3.B.169.237; 3.B.169.238; 3.B.169.239; 3.B.169.154;
3.B.169.157; 3.B.169.166; 3.B.169.169; 3.B.169.172; 3.B.169.175; 3.B.169.240;
3.B.169.244; 3.B.172.228; 3.B.172.229; 3.B.172.230; 3.B.172.231; 3.B.172.236;
3.B.172.237; 3.B.172.238; 3.B.172.239; 3.B.172.154; 3.B.172.157; 3.B.172.166;
3.B.172.169; 3.B.172.172; 3.B.172.175; 3.B.172.240; 3.B.172.244; 3.B.175.228;
3.B.175.229; 3.B.175.230; 3.B.175.231; 3.B.175.236; 3.B.175.237; 3.B.175.238;
3.B.175.239; 3.B.175.154; 3.B.175.157; 3.B.175.166; 3.B.175.169; 3.B.175.172;
3.B.175.175; 3.B.175.240; 3.B.175.244; 3.B.240.228; 3.B.240.229; 3.B.240.230;
3.B.240.231; 3.B.240.236; 3.B.240.237; 3.B.240.238; 3.B.240.239; 3.B.240.154;
3.B.240.157; 3.B.240.166; 3.B.240.169; 3.B.240.172; 3.B.240.175; 3.B.240.240;
3.B.240.244; 3.B.244.228; 3.B.244.229; 3.B.244.230; 3.B.244.231; 3.B.244.236;
3.B.244.237; 3.B.244.238; 3.B.244.239; 3.B.244.154; 3.B.244.157; 3.B.244.166;
3.B.244.169; 3.B.244.172; 3.B.244.175; 3.B.244.240; 3.B.244.244;
Prodrugs of 3.D 3.D.228.228; 3.D.228.229; 3.D.228.230; 3.D.228.231; 3.D.228.236;
3.D.228.237; 3.D.228.238; 3.D.228.239; 3.D.228.154; 3.D.228.157;
3.D.228.166; 3.D.228.169; 3.D.228.172; 3.D.228.175; 3.D.228.240;
3.D.228.244; 3.D.229.228; 3.D.229.229; 3.D.229.230; 3.D.229.231;
3.D.229.236; 3.D.229.237; 3.D.229.238; 3.D.229.239; 3.D.229.154;

TABLE 100-continued

3.D.229.157; 3.D.229.166; 3.D.229.169; 3.D.229.172; 3.D.229.175;
3.D.229.240; 3.D.229.244; 3.D.230.228; 3.D.230.229; 3.D.230.230;
3.D.230.231; 3.D.230.236; 3.D.230.237; 3.D.230.238; 3.D.230.239;
3.D.230.154; 3.D.230.157; 3.D.230.166; 3.D.230.169; 3.D.230.172;
3.D.230.175; 3.D.230.240; 3.D.230.244; 3.D.231.228; 3.D.231.229;
3.D.231.230; 3.D.231.231; 3.D.231.236; 3.D.231.237; 3.D.231.238;
3.D.231.239; 3.D.231.154; 3.D.231.157; 3.D.231.166; 3.D.231.169;
3.D.231.172; 3.D.231.175; 3.D.231.240; 3.D.231.244; 3.D.236.228;
3.D.236.229; 3.D.236.230; 3.D.236.231; 3.D.236.236; 3.D.236.237;
3.D.236.238; 3.D.236.239; 3.D.236.154; 3.D.236.157; 3.D.236.166;
3.D.236.169; 3.D.236.172; 3.D.236.175; 3.D.236.240; 3.D.236.244;
3.D.237.228; 3.D.237.229; 3.D.237.230; 3.D.237.231; 3.D.237.236;
3.D.237.237; 3.D.237.238; 3.D.237.239; 3.D.237.154; 3.D.237.157;
3.D.237.166; 3.D.237.169; 3.D.237.172; 3.D.237.175; 3.D.237.240;
3.D.237.244; 3.D.238.228; 3.D.238.229; 3.D.238.230; 3.D.238.231;
3.D.238.236; 3.D.238.237; 3.D.238.238; 3.D.238.239; 3.D.238.154;
3.D.238.157; 3.D.238.166; 3.D.238.169; 3.D.238.172; 3.D.238.175;
3.D.238.240; 3.D.238.244; 3.D.239.228; 3.D.239.229; 3.D.239.230;
3.D.239.231; 3.D.239.236; 3.D.239.237; 3.D.239.238; 3.D.239.239;
3.D.239.154; 3.D.239.157; 3.D.239.166; 3.D.239.169; 3.D.239.172;
3.D.239.175; 3.D.239.240; 3.D.239.244; 3.D.154.228; 3.D.154.229;
3.D.154.230; 3.D.154.231; 3.D.154.236; 3.D.154.237; 3.D.154.238;
3.D.154.239; 3.D.154.154; 3.D.154.157; 3.D.154.166; 3.D.154.169;
3.D.154.172; 3.D.154.175; 3.D.154.240; 3.D.154.244; 3.D.157.228;
3.D.157.229; 3.D.157.230; 3.D.157.231; 3.D.157.236; 3.D.157.237;
3.D.157.238; 3.D.157.239; 3.D.157.154; 3.D.157.157; 3.D.157.166;
3.D.157.169; 3.D.157.172; 3.D.157.175; 3.D.157.240; 3.D.157.244;
3.D.166.228; 3.D.166.229; 3.D.166.230; 3.D.166.231; 3.D.166.236;
3.D.166.237; 3.D.166.238; 3.D.166.239; 3.D.166.154; 3.D.166.157;
3.D.166.166; 3.D.166.169; 3.D.166.172; 3.D.166.175; 3.D.166.240;
3.D.166.244; 3.D.169.228; 3.D.169.229; 3.D.169.230; 3.D.169.231;
3.D.169.236; 3.D.169.237; 3.D.169.238; 3.D.169.239; 3.D.169.154;
3.D.169.157; 3.D.169.166; 3.D.169.169; 3.D.169.172; 3.D.169.175;
3.D.169.240; 3.D.169.244; 3.D.172.228; 3.D.172.229; 3.D.172.230;
3.D.172.231; 3.D.172.236; 3.D.172.237; 3.D.172.238; 3.D.172.239;
3.D.172.154; 3.D.172.157; 3.D.172.166; 3.D.172.169; 3.D.172.172;
3.D.172.175; 3.D.172.240; 3.D.172.244; 3.D.175.228; 3.D.175.229;
3.D.175.230; 3.D.175.231; 3.D.175.236; 3.D.175.237; 3.D.175.238;
3.D.175.239; 3.D.175.154; 3.D.175.157; 3.D.175.166; 3.D.175.169;
3.D.175.172; 3.D.175.175; 3.D.175.240; 3.D.175.244; 3.D.240.228;
3.D.240.229; 3.D.240.230; 3.D.240.231; 3.D.240.236; 3.D.240.237;
3.D.240.238; 3.D.240.239; 3.D.240.154; 3.D.240.157; 3.D.240.166;
3.D.240.169; 3.D.240.172; 3.D.240.175; 3.D.240.240; 3.D.240.244;
3.D.244.228; 3.D.244.229; 3.D.244.230; 3.D.244.231; 3.D.244.236;
3.D.244.237; 3.D.244.238; 3.D.244.239; 3.D.244.154; 3.D.244.157;
3.D.244.166; 3.D.244.169; 3.D.244.172; 3.D.244.175; 3.D.244.240; 3.D.244.244;
Prodrugs of 3.E 3.E.228.228; 3.E.228.229; 3.E.228.230; 3.E.228.231; 3.E.228.236;
3.E.228.237; 3.E.228.238; 3.E.228.239; 3.E.228.154; 3.E.228.157; 3.E.228.166;
3.E.228.169; 3.E.228.172; 3.E.228.175; 3.E.228.240; 3.E.228.244; 3.E.229.228;
3.E.229.229; 3.E.229.230; 3.E.229.231; 3.E.229.236; 3.E.229.237; 3.E.229.238;
3.E.229.239; 3.E.229.154; 3.E.229.157; 3.E.229.166; 3.E.229.169; 3.E.229.172;
3.E.229.175; 3.E.229.240; 3.E.229.244; 3.E.230.228; 3.E.230.229; 3.E.230.230;
3.E.230.231; 3.E.230.236; 3.E.230.237; 3.E.230.238; 3.E.230.239; 3.E.230.154;
3.E.230.157; 3.E.230.166; 3.E.230.169; 3.E.230.172; 3.E.230.175; 3.E.230.240;
3.E.230.244; 3.E.231.228; 3.E.231.229; 3.E.231.230; 3.E.231.231; 3.E.231.236;
3.E.231.237; 3.E.231.238; 3.E.231.239; 3.E.231.154; 3.E.231.157; 3.E.231.166;
3.E.231.169; 3.E.231.172; 3.E.231.175; 3.E.231.240; 3.E.231.244; 3.E.236.228;
3.E.236.229; 3.E.236.230; 3.E.236.231; 3.E.236.236; 3.E.236.237; 3.E.236.238;
3.E.236.239; 3.E.236.154; 3.E.236.157; 3.E.236.166; 3.E.236.169; 3.E.236.172;
3.E.236.175; 3.E.236.240; 3.E.236.244; 3.E.237.228; 3.E.237.229; 3.E.237.230;
3.E.237.231; 3.E.237.236; 3.E.237.237; 3.E.237.238; 3.E.237.239; 3.E.237.154;
3.E.237.157; 3.E.237.166; 3.E.237.169; 3.E.237.172; 3.E.237.175; 3.E.237.240;
3.E.237.244; 3.E.238.228; 3.E.238.229; 3.E.238.230; 3.E.238.231; 3.E.238.236;
3.E.238.237; 3.E.238.238; 3.E.238.239; 3.E.238.154; 3.E.238.157; 3.E.238.166;
3.E.238.169; 3.E.238.172; 3.E.238.175; 3.E.238.240; 3.E.238.244; 3.E.239.228;
3.E.239.229; 3.E.239.230; 3.E.239.231; 3.E.239.236; 3.E.239.237; 3.E.239.238;
3.E.239.239; 3.E.239.154; 3.E.239.157; 3.E.239.166; 3.E.239.169; 3.E.239.172;
3.E.239.175; 3.E.239.240; 3.E.239.244; 3.E.154.228; 3.E.154.229; 3.E.154.230;
3.E.154.231; 3.E.154.236; 3.E.154.237; 3.E.154.238; 3.E.154.239; 3.E.154.154;
3.E.154.157; 3.E.154.166; 3.E.154.169; 3.E.154.172; 3.E.154.175; 3.E.154.240;
3.E.154.244; 3.E.157.228; 3.E.157.229; 3.E.157.230; 3.E.157.231; 3.E.157.236;
3.E.157.237; 3.E.157.238; 3.E.157.239; 3.E.157.154; 3.E.157.157; 3.E.157.166;
3.E.157.169; 3.E.157.172; 3.E.157.175; 3.E.157.240; 3.E.157.244; 3.E.166.228;
3.E.166.229; 3.E.166.230; 3.E.166.231; 3.E.166.236; 3.E.166.237; 3.E.166.238;
3.E.166.239; 3.E.166.154; 3.E.166.157; 3.E.166.166; 3.E.166.169; 3.E.166.172;
3.E.166.175; 3.E.166.240; 3.E.166.244; 3.E.169.228; 3.E.169.229; 3.E.169.230;
3.E.169.231; 3.E.169.236; 3.E.169.237; 3.E.169.238; 3.E.169.239; 3.E.169.154;

TABLE 100-continued

3.E.169.157; 3.E.169.166; 3.E.169.169; 3.E.169.172; 3.E.169.175; 3.E.169.240;
3.E.169.244; 3.E.172.228; 3.E.172.229; 3.E.172.230; 3.E.172.231; 3.E.172.236;
3.E.172.237; 3.E.172.238; 3.E.172.239; 3.E.172.154; 3.E.172.157; 3.E.172.166;
3.E.172.169; 3.E.172.172; 3.E.172.175; 3.E.172.240; 3.E.172.244; 3.E.175.228;
3.E.175.229; 3.E.175.230; 3.E.175.231; 3.E.175.236; 3.E.175.237; 3.E.175.238;
3.E.175.239; 3.E.175.154; 3.E.175.157; 3.E.175.166; 3.E.175.169; 3.E.175.172;
3.E.175.175; 3.E.175.240; 3.E.175.244; 3.E.240.228; 3.E.240.229; 3.E.240.230;
3.E.240.231; 3.E.240.236; 3.E.240.237; 3.E.240.238; 3.E.240.239; 3.E.240.154;
3.E.240.157; 3.E.240.166; 3.E.240.169; 3.E.240.172; 3.E.240.175; 3.E.240.240;
3.E.240.244; 3.E.244.228; 3.E.244.229; 3.E.244.230; 3.E.244.231; 3.E.244.236;
3.E.244.237; 3.E.244.238; 3.E.244.239; 3.E.244.154; 3.E.244.157; 3.E.244.166;
3.E.244.169; 3.E.244.172; 3.E.244.175; 3.E.244.240; 3.E.244.244;
Prodrugs of 3.G 3.G.228.228; 3.G.228.229; 3.G.228.230; 3.G.228.231; 3.G.228.236;
3.G.228.237; 3.G.228.238; 3.G.228.239; 3.G.228.154; 3.G.228.157;
3.G.228.166; 3.G.228.169; 3.G.228.172; 3.G.228.175; 3.G.228.240;
3.G.228.244; 3.G.229.228; 3.G.229.229; 3.G.229.230; 3.G.229.231;
3.G.229.236; 3.G.229.237; 3.G.229.238; 3.G.229.239; 3.G.229.154;
3.G.229.157; 3.G.229.166; 3.G.229.169; 3.G.229.172; 3.G.229.175;
3.G.229.240; 3.G.229.244; 3.G.230.228; 3.G.230.229; 3.G.230.230;
3.G.230.231; 3.G.230.236; 3.G.230.237; 3.G.230.238; 3.G.230.239;
3.G.230.154; 3.G.230.157; 3.G.230.166; 3.G.230.169; 3.G.230.172;
3.G.230.175; 3.G.230.240; 3.G.230.244; 3.G.231.228; 3.G.231.229;
3.G.231.230; 3.G.231.231; 3.G.231.236; 3.G.231.237; 3.G.231.238;
3.G.231.239; 3.G.231.154; 3.G.231.157; 3.G.231.166; 3.G.231.169;
3.G.231.172; 3.G.231.175; 3.G.231.240; 3.G.231.244; 3.G.236.228;
3.G.236.229; 3.G.236.230; 3.G.236.231; 3.G.236.236; 3.G.236.237;
3.G.236.238; 3.G.236.239; 3.G.236.154; 3.G.236.157; 3.G.236.166;
3.G.236.169; 3.G.236.172; 3.G.236.175; 3.G.236.240; 3.G.236.244;
3.G.237.228; 3.G.237.229; 3.G.237.230; 3.G.237.231; 3.G.237.236;
3.G.237.237; 3.G.237.238; 3.G.237.239; 3.G.237.154; 3.G.237.157;
3.G.237.166; 3.G.237.169; 3.G.237.172; 3.G.237.175; 3.G.237.240;
3.G.237.244; 3.G.238.228; 3.G.238.229; 3.G.238.230; 3.G.238.231;
3.G.238.236; 3.G.238.237; 3.G.238.238; 3.G.238.239; 3.G.238.154;
3.G.238.157; 3.G.238.166; 3.G.238.169; 3.G.238.172; 3.G.238.175;
3.G.238.240; 3.G.238.244; 3.G.239.228; 3.G.239.229; 3.G.239.230;
3.G.239.231; 3.G.239.236; 3.G.239.237; 3.G.239.238; 3.G.239.239;
3.G.239.154; 3.G.239.157; 3.G.239.166; 3.G.239.169; 3.G.239.172;
3.G.239.175; 3.G.239.240; 3.G.239.244; 3.G.154.228; 3.G.154.229;
3.G.154.230; 3.G.154.231; 3.G.154.236; 3.G.154.237; 3.G.154.238;
3.G.154.239; 3.G.154.154; 3.G.154.157; 3.G.154.166; 3.G.154.169;
3.G.154.172; 3.G.154.175; 3.G.154.240; 3.G.154.244; 3.G.157.228;
3.G.157.229; 3.G.157.230; 3.G.157.231; 3.G.157.236; 3.G.157.237;
3.G.157.238; 3.G.157.239; 3.G.157.154; 3.G.157.157; 3.G.157.166;
3.G.157.169; 3.G.157.172; 3.G.157.175; 3.G.157.240; 3.G.157.244;
3.G.166.228; 3.G.166.229; 3.G.166.230; 3.G.166.231; 3.G.166.236;
3.G.166.237; 3.G.166.238; 3.G.166.239; 3.G.166.154; 3.G.166.157;
3.G.166.166; 3.G.166.169; 3.G.166.172; 3.G.166.175; 3.G.166.240;
3.G.166.244; 3.G.169.228; 3.G.169.229; 3.G.169.230; 3.G.169.231;
3.G.169.236; 3.G.169.237; 3.G.169.238; 3.G.169.239; 3.G.169.154;
3.G.169.157; 3.G.169.166; 3.G.169.169; 3.G.169.172; 3.G.169.175;
3.G.169.240; 3.G.169.244; 3.G.172.228; 3.G.172.229; 3.G.172.230;
3.G.172.231; 3.G.172.236; 3.G.172.237; 3.G.172.238; 3.G.172.239;
3.G.172.154; 3.G.172.157; 3.G.172.166; 3.G.172.169; 3.G.172.172;
3.G.172.175; 3.G.172.240; 3.G.172.244; 3.G.175.228; 3.G.175.229;
3.G.175.230; 3.G.175.231; 3.G.175.236; 3.G.175.237; 3.G.175.238;
3.G.175.239; 3.G.175.154; 3.G.175.157; 3.G.175.166; 3.G.175.169;
3.G.175.172; 3.G.175.175; 3.G.175.240; 3.G.175.244; 3.G.240.228;
3.G.240.229; 3.G.240.230; 3.G.240.231; 3.G.240.236; 3.G.240.237;
3.G.240.238; 3.G.240.239; 3.G.240.154; 3.G.240.157; 3.G.240.166;
3.G.240.169; 3.G.240.172; 3.G.240.175; 3.G.240.240; 3.G.240.244;
3.G.244.228; 3.G.244.229; 3.G.244.230; 3.G.244.231; 3.G.244.236;
3.G.244.237; 3.G.244.238; 3.G.244.239; 3.G.244.154; 3.G.244.157;
3.G.244.166; 3.G.244.169; 3.G.244.172; 3.G.244.175; 3.G.244.240; 3.G.244.244;
Prodrugs of 3.I 3.I.228.228; 3.I.228.229; 3.I.228.230; 3.I.228.231; 3.I.228.236; 3.I.228.237;
3.I.228.238; 3.I.228.239; 3.I.228.154; 3.I.228.157; 3.I.228.166; 3.I.228.169;
3.I.228.172; 3.I.228.175; 3.I.228.240; 3.I.228.244; 3.I.229.228; 3.I.229.229;
3.I.229.230; 3.I.229.231; 3.I.229.236; 3.I.229.237; 3.I.229.238; 3.I.229.239;
3.I.229.154; 3.I.229.157; 3.I.229.166; 3.I.229.169; 3.I.229.172; 3.I.229.175;
3.I.229.240; 3.I.229.244; 3.I.230.228; 3.I.230.229; 3.I.230.230; 3.I.230.231;
3.I.230.236; 3.I.230.237; 3.I.230.238; 3.I.230.239; 3.I.230.154; 3.I.230.157;
3.I.230.166; 3.I.230.169; 3.I.230.172; 3.I.230.175; 3.I.230.240; 3.I.230.244;
3.I.231.228; 3.I.231.229; 3.I.231.230; 3.I.231.231; 3.I.231.236; 3.I.231.237;
3.I.231.238; 3.I.231.239; 3.I.231.154; 3.I.231.157; 3.I.231.166; 3.I.231.169;
3.I.231.172; 3.I.231.175; 3.I.231.240; 3.I.231.244; 3.I.236.228; 3.I.236.229;
3.I.236.230; 3.I.236.231; 3.I.236.236; 3.I.236.237; 3.I.236.238; 3.I.236.239;

TABLE 100-continued

3.I.236.154; 3.I.236.157; 3.I.236.166; 3.I.236.169; 3.I.236.172; 3.I.236.175;
3.I.236.240; 3.I.236.244; 3.I.237.228; 3.I.237.229; 3.I.237.230; 3.I.237.231;
3.I.237.236; 3.I.237.237; 3.I.237.238; 3.I.237.239; 3.I.237.154; 3.I.237.157;
3.I.237.166; 3.I.237.169; 3.I.237.172; 3.I.237.175; 3.I.237.240; 3.I.237.244;
3.I.238.228; 3.I.238.229; 3.I.238.230; 3.I.238.231; 3.I.238.236; 3.I.238.237;
3.I.238.238; 3.I.238.239; 3.I.238.154; 3.I.238.157; 3.I.238.166; 3.I.238.169;
3.I.238.172; 3.I.238.175; 3.I.238.240; 3.I.238.244; 3.I.239.228; 3.I.239.229;
3.I.239.230; 3.I.239.231; 3.I.239.236; 3.I.239.237; 3.I.239.238; 3.I.239.239;
3.I.239.154; 3.I.239.157; 3.I.239.166; 3.I.239.169; 3.I.239.172; 3.I.239.175;
3.I.239.240; 3.I.239.244; 3.I.154.228; 3.I.154.229; 3.I.154.230; 3.I.154.231;
3.I.154.236; 3.I.154.237; 3.I.154.238; 3.I.154.239; 3.I.154.154; 3.I.154.157;
3.I.154.166; 3.I.154.169; 3.I.154.172; 3.I.154.175; 3.I.154.240; 3.I.154.244;
3.I.157.228; 3.I.157.229; 3.I.157.230; 3.I.157.231; 3.I.157.236; 3.I.157.237;
3.I.157.238; 3.I.157.239; 3.I.157.154; 3.I.157.157; 3.I.157.166; 3.I.157.169;
3.I.157.172; 3.I.157.175; 3.I.157.240; 3.I.157.244; 3.I.166.228; 3.I.166.229;
3.I.166.230; 3.I.166.231; 3.I.166.236; 3.I.166.237; 3.I.166.238; 3.I.166.239;
3.I.166.154; 3.I.166.157; 3.I.166.166; 3.I.166.169; 3.I.166.172; 3.I.166.175;
3.I.166.240; 3.I.166.244; 3.I.169.228; 3.I.169.229; 3.I.169.230; 3.I.169.231;
3.I.169.236; 3.I.169.237; 3.I.169.238; 3.I.169.239; 3.I.169.154; 3.I.169.157;
3.I.169.166; 3.I.169.169; 3.I.169.172; 3.I.169.175; 3.I.169.240; 3.I.169.244;
3.I.172.228; 3.I.172.229; 3.I.172.230; 3.I.172.231; 3.I.172.236; 3.I.172.237;
3.I.172.238; 3.I.172.239; 3.I.172.154; 3.I.172.157; 3.I.172.166; 3.I.172.169;
3.I.172.172; 3.I.172.175; 3.I.172.240; 3.I.172.244; 3.I.175.228; 3.I.175.229;
3.I.175.230; 3.I.175.231; 3.I.175.236; 3.I.175.237; 3.I.175.238; 3.I.175.239;
3.I.175.154; 3.I.175.157; 3.I.175.166; 3.I.175.169; 3.I.175.172; 3.I.175.175;
3.I.175.240; 3.I.175.244; 3.I.240.228; 3.I.240.229; 3.I.240.230; 3.I.240.231;
3.I.240.236; 3.I.240.237; 3.I.240.238; 3.I.240.239; 3.I.240.154; 3.I.240.157;
3.I.240.166; 3.I.240.169; 3.I.240.172; 3.I.240.175; 3.I.240.240; 3.I.240.244;
3.I.244.228; 3.I.244.229; 3.I.244.230; 3.I.244.231; 3.I.244.236; 3.I.244.237;
3.I.244.238; 3.I.244.239; 3.I.244.154; 3.I.244.157; 3.I.244.166; 3.I.244.169;
3.I.244.172; 3.I.244.175; 3.I.244.240; 3.I.244.244;
Prodrugs of 3.J 3.J.228.228; 3.J.228.229; 3.J.228.230; 3.J.228.231; 3.J.228.236; 3.J.228.237;
3.J.228.238; 3.J.228.239; 3.J.228.154; 3.J.228.157; 3.J.228.166; 3.J.228.169;
3.J.228.172; 3.J.228.175; 3.J.228.240; 3.J.228.244; 3.J.229.228; 3.J.229.229;
3.J.229.230; 3.J.229.231; 3.J.229.236; 3.J.229.237; 3.J.229.238; 3.J.229.239;
3.J.229.154; 3.J.229.157; 3.J.229.166; 3.J.229.169; 3.J.229.172; 3.J.229.175;
3.J.229.240; 3.J.229.244; 3.J.230.228; 3.J.230.229; 3.J.230.230; 3.J.230.231;
3.J.230.236; 3.J.230.237; 3.J.230.238; 3.J.230.239; 3.J.230.154; 3.J.230.157;
3.J.230.166; 3.J.230.169; 3.J.230.172; 3.J.230.175; 3.J.230.240; 3.J.230.244;
3.J.231.228; 3.J.231.229; 3.J.231.230; 3.J.231.231; 3.J.231.236; 3.J.231.237;
3.J.231.238; 3.J.231.239; 3.J.231.154; 3.J.231.157; 3.J.231.166; 3.J.231.169;
3.J.231.172; 3.J.231.175; 3.J.231.240; 3.J.231.244; 3.J.236.228; 3.J.236.229;
3.J.236.230; 3.J.236.231; 3.J.236.236; 3.J.236.237; 3.J.236.238; 3.J.236.239;
3.J.236.154; 3.J.236.157; 3.J.236.166; 3.J.236.169; 3.J.236.172; 3.J.236.175;
3.J.236.240; 3.J.236.244; 3.J.237.228; 3.J.237.229; 3.J.237.230; 3.J.237.231;
3.J.237.236; 3.J.237.237; 3.J.237.238; 3.J.237.239; 3.J.237.154; 3.J.237.157;
3.J.237.166; 3.J.237.169; 3.J.237.172; 3.J.237.175; 3.J.237.240; 3.J.237.244;
3.J.238.228; 3.J.238.229; 3.J.238.230; 3.J.238.231; 3.J.238.236; 3.J.238.237;
3.J.238.238; 3.J.238.239; 3.J.238.154; 3.J.238.157; 3.J.238.166; 3.J.238.169;
3.J.238.172; 3.J.238.175; 3.J.238.240; 3.J.238.244; 3.J.239.228; 3.J.239.229;
3.J.239.230; 3.J.239.231; 3.J.239.236; 3.J.239.237; 3.J.239.238; 3.J.239.239;
3.J.239.154; 3.J.239.157; 3.J.239.166; 3.J.239.169; 3.J.239.172; 3.J.239.175;
3.J.239.240; 3.J.239.244; 3.J.154.228; 3.J.154.229; 3.J.154.230; 3.J.154.231;
3.J.154.236; 3.J.154.237; 3.J.154.238; 3.J.154.239; 3.J.154.154; 3.J.154.157;
3.J.154.166; 3.J.154.169; 3.J.154.172; 3.J.154.175; 3.J.154.240; 3.J.154.244;
3.J.157.228; 3.J.157.229; 3.J.157.230; 3.J.157.231; 3.J.157.236; 3.J.157.237;
3.J.157.238; 3.J.157.239; 3.J.157.154; 3.J.157.157; 3.J.157.166; 3.J.157.169;
3.J.157.172; 3.J.157.175; 3.J.157.240; 3.J.157.244; 3.J.166.228; 3.J.166.229;
3.J.166.230; 3.J.166.231; 3.J.166.236; 3.J.166.237; 3.J.166.238; 3.J.166.239;
3.J.166.154; 3.J.166.157; 3.J.166.166; 3.J.166.169; 3.J.166.172; 3.J.166.175;
3.J.166.240; 3.J.166.244; 3.J.169.228; 3.J.169.229; 3.J.169.230; 3.J.169.231;
3.J.169.236; 3.J.169.237; 3.J.169.238; 3.J.169.239; 3.J.169.154; 3.J.169.157;
3.J.169.166; 3.J.169.169; 3.J.169.172; 3.J.169.175; 3.J.169.240; 3.J.169.244;
3.J.172.228; 3.J.172.229; 3.J.172.230; 3.J.172.231; 3.J.172.236; 3.J.172.237;
3.J.172.238; 3.J.172.239; 3.J.172.154; 3.J.172.157; 3.J.172.166; 3.J.172.169;
3.J.172.172; 3.J.172.175; 3.J.172.240; 3.J.172.244; 3.J.175.228; 3.J.175.229;
3.J.175.230; 3.J.175.231; 3.J.175.236; 3.J.175.237; 3.J.175.238; 3.J.175.239;
3.J.175.154; 3.J.175.157; 3.J.175.166; 3.J.175.169; 3.J.175.172; 3.J.175.175;
3.J.175.240; 3.J.175.244; 3.J.240.228; 3.J.240.229; 3.J.240.230; 3.J.240.231;
3.J.240.236; 3.J.240.237; 3.J.240.238; 3.J.240.239; 3.J.240.154; 3.J.240.157;
3.J.240.166; 3.J.240.169; 3.J.240.172; 3.J.240.175; 3.J.240.240; 3.J.240.244;
3.J.244.228; 3.J.244.229; 3.J.244.230; 3.J.244.231; 3.J.244.236; 3.J.244.237;
3.J.244.238; 3.J.244.239; 3.J.244.154; 3.J.244.157; 3.J.244.166; 3.J.244.169;
3.J.244.172; 3.J.244.175; 3.J.244.240; 3.J.244.244;

TABLE 100-continued

Prodrugs of 3.L

3.L.228.228; 3.L.228.229; 3.L.228.230; 3.L.228.231; 3.L.228.236;
3.L.228.237; 3.L.228.238; 3.L.228.239; 3.L.228.154; 3.L.228.157; 3.L.228.166;
3.L.228.169; 3.L.228.172; 3.L.228.175; 3.L.228.240; 3.L.228.244; 3.L.229.228;
3.L.229.229; 3.L.229.230; 3.L.229.231; 3.L.229.236; 3.L.229.237; 3.L.229.238;
3.L.229.239; 3.L.229.154; 3.L.229.157; 3.L.229.166; 3.L.229.169; 3.L.229.172;
3.L.229.175; 3.L.229.240; 3.L.229.244; 3.L.230.228; 3.L.230.229; 3.L.230.230;
3.L.230.231; 3.L.230.236; 3.L.230.237; 3.L.230.238; 3.L.230.239; 3.L.230.154;
3.L.230.157; 3.L.230.166; 3.L.230.169; 3.L.230.172; 3.L.230.175; 3.L.230.240;
3.L.230.244; 3.L.231.228; 3.L.231.229; 3.L.231.230; 3.L.231.231; 3.L.231.236;
3.L.231.237; 3.L.231.238; 3.L.231.239; 3.L.231.154; 3.L.231.157; 3.L.231.166;
3.L.231.169; 3.L.231.172; 3.L.231.175; 3.L.231.240; 3.L.231.244; 3.L.236.228;
3.L.236.229; 3.L.236.230; 3.L.236.231; 3.L.236.236; 3.L.236.237; 3.L.236.238;
3.L.236.239; 3.L.236.154; 3.L.236.157; 3.L.236.166; 3.L.236.169; 3.L.236.172;
3.L.236.175; 3.L.236.240; 3.L.236.244; 3.L.237.228; 3.L.237.229; 3.L.237.230;
3.L.237.231; 3.L.237.236; 3.L.237.237; 3.L.237.238; 3.L.237.239; 3.L.237.154;
3.L.237.157; 3.L.237.166; 3.L.237.169; 3.L.237.172; 3.L.237.175; 3.L.237.240;
3.L.237.244; 3.L.238.228; 3.L.238.229; 3.L.238.230; 3.L.238.231; 3.L.238.236;
3.L.238.237; 3.L.238.238; 3.L.238.239; 3.L.238.154; 3.L.238.157; 3.L.238.166;
3.L.238.169; 3.L.238.172; 3.L.238.175; 3.L.238.240; 3.L.238.244; 3.L.239.228;
3.L.239.229; 3.L.239.230; 3.L.239.231; 3.L.239.236; 3.L.239.237; 3.L.239.238;
3.L.239.239; 3.L.239.154; 3.L.239.157; 3.L.239.166; 3.L.239.169; 3.L.239.172;
3.L.239.175; 3.L.239.240; 3.L.239.244; 3.L.154.228; 3.L.154.229; 3.L.154.230;
3.L.154.231; 3.L.154.236; 3.L.154.237; 3.L.154.238; 3.L.154.239; 3.L.154.154;
3.L.154.157; 3.L.154.166; 3.L.154.169; 3.L.154.172; 3.L.154.175; 3.L.154.240;
3.L.154.244; 3.L.157.228; 3.L.157.229; 3.L.157.230; 3.L.157.231; 3.L.157.236;
3.L.157.237; 3.L.157.238; 3.L.157.239; 3.L.157.154; 3.L.157.157; 3.L.157.166;
3.L.157.169; 3.L.157.172; 3.L.157.175; 3.L.157.240; 3.L.157.244; 3.L.166.228;
3.L.166.229; 3.L.166.230; 3.L.166.231; 3.L.166.236; 3.L.166.237; 3.L.166.238;
3.L.166.239; 3.L.166.154; 3.L.166.157; 3.L.166.166; 3.L.166.169; 3.L.166.172;
3.L.166.175; 3.L.166.240; 3.L.166.244; 3.L.169.228; 3.L.169.229; 3.L.169.230;
3.L.169.231; 3.L.169.236; 3.L.169.237; 3.L.169.238; 3.L.169.239; 3.L.169.154;
3.L.169.157; 3.L.169.166; 3.L.169.169; 3.L.169.172; 3.L.169.175; 3.L.169.240;
3.L.169.244; 3.L.172.228; 3.L.172.229; 3.L.172.230; 3.L.172.231; 3.L.172.236;
3.L.172.237; 3.L.172.238; 3.L.172.239; 3.L.172.154; 3.L.172.157; 3.L.172.166;
3.L.172.169; 3.L.172.172; 3.L.172.175; 3.L.172.240; 3.L.172.244; 3.L.175.228;
3.L.175.229; 3.L.175.230; 3.L.175.231; 3.L.175.236; 3.L.175.237; 3.L.175.238;
3.L.175.239; 3.L.175.154; 3.L.175.157; 3.L.175.166; 3.L.175.169; 3.L.175.172;
3.L.175.175; 3.L.175.240; 3.L.175.244; 3.L.240.228; 3.L.240.229; 3.L.240.230;
3.L.240.231; 3.L.240.236; 3.L.240.237; 3.L.240.238; 3.L.240.239; 3.L.240.154;
3.L.240.157; 3.L.240.166; 3.L.240.169; 3.L.240.172; 3.L.240.175; 3.L.240.240;
3.L.240.244; 3.L.244.228; 3.L.244.229; 3.L.244.230; 3.L.244.231; 3.L.244.236;
3.L.244.237; 3.L.244.238; 3.L.244.239; 3.L.244.154; 3.L.244.157; 3.L.244.166;
3.L.244.169; 3.L.244.172; 3.L.244.175; 3.L.244.240; 3.L.244.244;

Prodrugs of 3.O

3.O.228.228; 3.O.228.229; 3.O.228.230; 3.O.228.231; 3.O.228.236;
3.O.228.237; 3.O.228.238; 3.O.228.239; 3.O.228.154; 3.O.228.157;
3.O.228.166; 3.O.228.169; 3.O.228.172; 3.O.228.175; 3.O.228.240;
3.O.228.244; 3.O.229.228; 3.O.229.229; 3.O.229.230; 3.O.229.231;
3.O.229.236; 3.O.229.237; 3.O.229.238; 3.O.229.239; 3.O.229.154;
3.O.229.157; 3.O.229.166; 3.O.229.169; 3.O.229.172; 3.O.229.175;
3.O.229.240; 3.O.229.244; 3.O.230.228; 3.O.230.229; 3.O.230.230;
3.O.230.231; 3.O.230.236; 3.O.230.237; 3.O.230.238; 3.O.230.239;
3.O.230.154; 3.O.230.157; 3.O.230.166; 3.O.230.169; 3.O.230.172;
3.O.230.175; 3.O.230.240; 3.O.230.244; 3.O.231.228; 3.O.231.229;
3.O.231.230; 3.O.231.231; 3.O.231.236; 3.O.231.237; 3.O.231.238;
3.O.231.239; 3.O.231.154; 3.O.231.157; 3.O.231.166; 3.O.231.169;
3.O.231.172; 3.O.231.175; 3.O.231.240; 3.O.231.244; 3.O.236.228;
3.O.236.229; 3.O.236.230; 3.O.236.231; 3.O.236.236; 3.O.236.237;
3.O.236.238; 3.O.236.239; 3.O.236.154; 3.O.236.157; 3.O.236.166;
3.O.236.169; 3.O.236.172; 3.O.236.175; 3.O.236.240; 3.O.236.244;
3.O.237.228; 3.O.237.229; 3.O.237.230; 3.O.237.231; 3.O.237.236;
3.O.237.237; 3.O.237.238; 3.O.237.239; 3.O.237.154; 3.O.237.157;
3.O.237.166; 3.O.237.169; 3.O.237.172; 3.O.237.175; 3.O.237.240;
3.O.237.244; 3.O.238.228; 3.O.238.229; 3.O.238.230; 3.O.238.231;
3.O.238.236; 3.O.238.237; 3.O.238.238; 3.O.238.239; 3.O.238.154;
3.O.238.157; 3.O.238.166; 3.O.238.169; 3.O.238.172; 3.O.238.175;
3.O.238.240; 3.O.238.244; 3.O.239.228; 3.O.239.229; 3.O.239.230;
3.O.239.231; 3.O.239.236; 3.O.239.237; 3.O.239.238; 3.O.239.239;
3.O.239.154; 3.O.239.157; 3.O.239.166; 3.O.239.169; 3.O.239.172;
3.O.239.175; 3.O.239.240; 3.O.239.244; 3.O.154.228; 3.O.154.229;
3.O.154.230; 3.O.154.231; 3.O.154.236; 3.O.154.237; 3.O.154.238;
3.O.154.239; 3.O.154.154; 3.O.154.157; 3.O.154.166; 3.O.154.169;
3.O.154.172; 3.O.154.175; 3.O.154.240; 3.O.154.244; 3.O.157.228;
3.O.157.229; 3.O.157.230; 3.O.157.231; 3.O.157.236; 3.O.157.237;
3.O.157.238; 3.O.157.239; 3.O.157.154; 3.O.157.157; 3.O.157.166;
3.O.157.169; 3.O.157.172; 3.O.157.175; 3.O.157.240; 3.O.157.244;

TABLE 100-continued

3.O.166.228; 3.O.166.229; 3.O.166.230; 3.O.166.231; 3.O.166.236;
3.O.166.237; 3.O.166.238; 3.O.166.239; 3.O.166.154; 3.O.166.157;
3.O.166.166; 3.O.166.169; 3.O.166.172; 3.O.166.175; 3.O.166.240;
3.O.166.244; 3.O.169.228; 3.O.169.229; 3.O.169.230; 3.O.169.231;
3.O.169.236; 3.O.169.237; 3.O.169.238; 3.O.169.239; 3.O.169.154;
3.O.169.157; 3.O.169.166; 3.O.169.169; 3.O.169.172; 3.O.169.175;
3.O.169.240; 3.O.169.244; 3.O.172.228; 3.O.172.229; 3.O.172.230;
3.O.172.231; 3.O.172.236; 3.O.172.237; 3.O.172.238; 3.O.172.239;
3.O.172.154; 3.O.172.157; 3.O.172.166; 3.O.172.169; 3.O.172.172;
3.O.172.175; 3.O.172.240; 3.O.172.244; 3.O.175.228; 3.O.175.229;
3.O.175.230; 3.O.175.231; 3.O.175.236; 3.O.175.237; 3.O.175.238;
3.O.175.239; 3.O.175.154; 3.O.175.157; 3.O.175.166; 3.O.175.169;
3.O.175.172; 3.O.175.175; 3.O.175.240; 3.O.175.244; 3.O.240.228;
3.O.240.229; 3.O.240.230; 3.O.240.231; 3.O.240.236; 3.O.240.237;
3.O.240.238; 3.O.240.239; 3.O.240.154; 3.O.240.157; 3.O.240.166;
3.O.240.169; 3.O.240.172; 3.O.240.175; 3.O.240.240; 3.O.240.244;
3.O.244.228; 3.O.244.229; 3.O.244.230; 3.O.244.231; 3.O.244.236;
3.O.244.237; 3.O.244.238; 3.O.244.239; 3.O.244.154; 3.O.244.157;
3.O.244.166; 3.O.244.169; 3.O.244.172; 3.O.244.175; 3.O.244.240; 3.O.244.244;
Prodrugs of 3.P 3.P.228.228; 3.P.228.229; 3.P.228.230; 3.P.228.231; 3.P.228.236;
3.P.228.237; 3.P.228.238; 3.P.228.239; 3.P.228.154; 3.P.228.157; 3.P.228.166;
3.P.228.169; 3.P.228.172; 3.P.228.175; 3.P.228.240; 3.P.228.244; 3.P.229.228;
3.P.229.229; 3.P.229.230; 3.P.229.231; 3.P.229.236; 3.P.229.237; 3.P.229.238;
3.P.229.239; 3.P.229.154; 3.P.229.157; 3.P.229.166; 3.P.229.169; 3.P.229.172;
3.P.229.175; 3.P.229.240; 3.P.229.244; 3.P.230.228; 3.P.230.229; 3.P.230.230;
3.P.230.231; 3.P.230.236; 3.P.230.237; 3.P.230.238; 3.P.230.239; 3.P.230.154;
3.P.230.157; 3.P.230.166; 3.P.230.169; 3.P.230.172; 3.P.230.175; 3.P.230.240;
3.P.230.244; 3.P.231.228; 3.P.231.229; 3.P.231.230; 3.P.231.231; 3.P.231.236;
3.P.231.237; 3.P.231.238; 3.P.231.239; 3.P.231.154; 3.P.231.157; 3.P.231.166;
3.P.231.169; 3.P.231.172; 3.P.231.175; 3.P.231.240; 3.P.231.244; 3.P.236.228;
3.P.236.229; 3.P.236.230; 3.P.236.231; 3.P.236.236; 3.P.236.237; 3.P.236.238;
3.P.236.239; 3.P.236.154; 3.P.236.157; 3.P.236.166; 3.P.236.169; 3.P.236.172;
3.P.236.175; 3.P.236.240; 3.P.236.244; 3.P.237.228; 3.P.237.229; 3.P.237.230;
3.P.237.231; 3.P.237.236; 3.P.237.237; 3.P.237.238; 3.P.237.239; 3.P.237.154;
3.P.237.157; 3.P.237.166; 3.P.237.169; 3.P.237.172; 3.P.237.175; 3.P.237.240;
3.P.237.244; 3.P.238.228; 3.P.238.229; 3.P.238.230; 3.P.238.231; 3.P.238.236;
3.P.238.237; 3.P.238.238; 3.P.238.239; 3.P.238.154; 3.P.238.157; 3.P.238.166;
3.P.238.169; 3.P.238.172; 3.P.238.175; 3.P.238.240; 3.P.238.244; 3.P.239.228;
3.P.239.229; 3.P.239.230; 3.P.239.231; 3.P.239.236; 3.P.239.237; 3.P.239.238;
3.P.239.239; 3.P.239.154; 3.P.239.157; 3.P.239.166; 3.P.239.169; 3.P.239.172;
3.P.239.175; 3.P.239.240; 3.P.239.244; 3.P.154.228; 3.P.154.229; 3.P.154.230;
3.P.154.231; 3.P.154.236; 3.P.154.237; 3.P.154.238; 3.P.154.239; 3.P.154.154;
3.P.154.157; 3.P.154.166; 3.P.154.169; 3.P.154.172; 3.P.154.175; 3.P.154.240;
3.P.154.244; 3.P.157.228; 3.P.157.229; 3.P.157.230; 3.P.157.231; 3.P.157.236;
3.P.157.237; 3.P.157.238; 3.P.157.239; 3.P.157.154; 3.P.157.157; 3.P.157.166;
3.P.157.169; 3.P.157.172; 3.P.157.175; 3.P.157.240; 3.P.157.244; 3.P.166.228;
3.P.166.229; 3.P.166.230; 3.P.166.231; 3.P.166.236; 3.P.166.237; 3.P.166.238;
3.P.166.239; 3.P.166.154; 3.P.166.157; 3.P.166.166; 3.P.166.169; 3.P.166.172;
3.P.166.175; 3.P.166.240; 3.P.166.244; 3.P.169.228; 3.P.169.229; 3.P.169.230;
3.P.169.231; 3.P.169.236; 3.P.169.237; 3.P.169.238; 3.P.169.239; 3.P.169.154;
3.P.169.157; 3.P.169.166; 3.P.169.169; 3.P.169.172; 3.P.169.175; 3.P.169.240;
3.P.169.244; 3.P.172.228; 3.P.172.229; 3.P.172.230; 3.P.172.231; 3.P.172.236;
3.P.172.237; 3.P.172.238; 3.P.172.239; 3.P.172.154; 3.P.172.157; 3.P.172.166;
3.P.172.169; 3.P.172.172; 3.P.172.175; 3.P.172.240; 3.P.172.244; 3.P.175.228;
3.P.175.229; 3.P.175.230; 3.P.175.231; 3.P.175.236; 3.P.175.237; 3.P.175.238;
3.P.175.239; 3.P.175.154; 3.P.175.157; 3.P.175.166; 3.P.175.169; 3.P.175.172;
3.P.175.175; 3.P.175.240; 3.P.175.244; 3.P.240.228; 3.P.240.229; 3.P.240.230;
3.P.240.231; 3.P.240.236; 3.P.240.237; 3.P.240.238; 3.P.240.239; 3.P.240.154;
3.P.240.157; 3.P.240.166; 3.P.240.169; 3.P.240.172; 3.P.240.175; 3.P.240.240;
3.P.240.244; 3.P.244.228; 3.P.244.229; 3.P.244.230; 3.P.244.231; 3.P.244.236;
3.P.244.237; 3.P.244.238; 3.P.244.239; 3.P.244.154; 3.P.244.157; 3.P.244.166;
3.P.244.169; 3.P.244.172; 3.P.244.175; 3.P.244.240; 3.P.244.244;
Prodrugs of 3.U 3.U.228.228; 3.U.228.229; 3.U.228.230; 3.U.228.231; 3.U.228.236;
3.U.228.237; 3.U.228.238; 3.U.228.239; 3.U.228.154; 3.U.228.157;
3.U.228.166; 3.U.228.169; 3.U.228.172; 3.U.228.175; 3.U.228.240;
3.U.228.244; 3.U.229.228; 3.U.229.229; 3.U.229.230; 3.U.229.231;
3.U.229.236; 3.U.229.237; 3.U.229.238; 3.U.229.239; 3.U.229.154;
3.U.229.157; 3.U.229.166; 3.U.229.169; 3.U.229.172; 3.U.229.175;
3.U.229.240; 3.U.229.244; 3.U.230.228; 3.U.230.229; 3.U.230.230;
3.U.230.231; 3.U.230.236; 3.U.230.237; 3.U.230.238; 3.U.230.239;
3.U.230.154; 3.U.230.157; 3.U.230.166; 3.U.230.169; 3.U.230.172;
3.U.230.175; 3.U.230.240; 3.U.230.244; 3.U.231.228; 3.U.231.229;
3.U.231.230; 3.U.231.231; 3.U.231.236; 3.U.231.237; 3.U.231.238;
3.U.231.239; 3.U.231.154; 3.U.231.157; 3.U.231.166; 3.U.231.169;
3.U.231.172; 3.U.231.175; 3.U.231.240; 3.U.231.244; 3.U.236.228;

TABLE 100-continued

3.U.236.229; 3.U.236.230; 3.U.236.231; 3.U.236.236; 3.U.236.237;
3.U.236.238; 3.U.236.239; 3.U.236.154; 3.U.236.157; 3.U.236.166;
3.U.236.169; 3.U.236.172; 3.U.236.175; 3.U.236.240; 3.U.236.244;
3.U.237.228; 3.U.237.229; 3.U.237.230; 3.U.237.231; 3.U.237.236;
3.U.237.237; 3.U.237.238; 3.U.237.239; 3.U.237.154; 3.U.237.157;
3.U.237.166; 3.U.237.169; 3.U.237.172; 3.U.237.175; 3.U.237.240;
3.U.237.244; 3.U.238.228; 3.U.238.229; 3.U.238.230; 3.U.238.231;
3.U.238.236; 3.U.238.237; 3.U.238.238; 3.U.238.239; 3.U.238.154;
3.U.238.157; 3.U.238.166; 3.U.238.169; 3.U.238.172; 3.U.238.175;
3.U.238.240; 3.U.238.244; 3.U.239.228; 3.U.239.229; 3.U.239.230;
3.U.239.231; 3.U.239.236; 3.U.239.237; 3.U.239.238; 3.U.239.239;
3.U.239.154; 3.U.239.157; 3.U.239.166; 3.U.239.169; 3.U.239.172;
3.U.239.175; 3.U.239.240; 3.U.239.244; 3.U.154.228; 3.U.154.229;
3.U.154.230; 3.U.154.231; 3.U.154.236; 3.U.154.237; 3.U.154.238;
3.U.154.239; 3.U.154.154; 3.U.154.157; 3.U.154.166; 3.U.154.169;
3.U.154.172; 3.U.154.175; 3.U.154.240; 3.U.154.244; 3.U.157.228;
3.U.157.229; 3.U.157.230; 3.U.157.231; 3.U.157.236; 3.U.157.237;
3.U.157.238; 3.U.157.239; 3.U.157.154; 3.U.157.157; 3.U.157.166;
3.U.157.169; 3.U.157.172; 3.U.157.175; 3.U.157.240; 3.U.157.244;
3.U.166.228; 3.U.166.229; 3.U.166.230; 3.U.166.231; 3.U.166.236;
3.U.166.237; 3.U.166.238; 3.U.166.239; 3.U.166.154; 3.U.166.157;
3.U.166.166; 3.U.166.169; 3.U.166.172; 3.U.166.175; 3.U.166.240;
3.U.166.244; 3.U.169.228; 3.U.169.229; 3.U.169.230; 3.U.169.231;
3.U.169.236; 3.U.169.237; 3.U.169.238; 3.U.169.239; 3.U.169.154;
3.U.169.157; 3.U.169.166; 3.U.169.169; 3.U.169.172; 3.U.169.175;
3.U.169.240; 3.U.169.244; 3.U.172.228; 3.U.172.229; 3.U.172.230;
3.U.172.231; 3.U.172.236; 3.U.172.237; 3.U.172.238; 3.U.172.239;
3.U.172.154; 3.U.172.157; 3.U.172.166; 3.U.172.169; 3.U.172.172;
3.U.172.175; 3.U.172.240; 3.U.172.244; 3.U.175.228; 3.U.175.229;
3.U.175.230; 3.U.175.231; 3.U.175.236; 3.U.175.237; 3.U.175.238;
3.U.175.239; 3.U.175.154; 3.U.175.157; 3.U.175.166; 3.U.175.169;
3.U.175.172; 3.U.175.175; 3.U.175.240; 3.U.175.244; 3.U.240.228;
3.U.240.229; 3.U.240.230; 3.U.240.231; 3.U.240.236; 3.U.240.237;
3.U.240.238; 3.U.240.239; 3.U.240.154; 3.U.240.157; 3.U.240.166;
3.U.240.169; 3.U.240.172; 3.U.240.175; 3.U.240.240; 3.U.240.244;
3.U.244.228; 3.U.244.229; 3.U.244.230; 3.U.244.231; 3.U.244.236;
3.U.244.237; 3.U.244.238; 3.U.244.239; 3.U.244.154; 3.U.244.157;
3.U.244.166; 3.U.244.169; 3.U.244.172; 3.U.244.175; 3.U.244.240; 3.U.244.244;
Prodrugs of 3.W 3.W.228.228; 3.W.228.229; 3.W.228.230; 3.W.228.231; 3.W.228.236;
3.W.228.237; 3.W.228.238; 3.W.228.239; 3.W.228.154; 3.W.228.157;
3.W.228.166; 3.W.228.169; 3.W.228.172; 3.W.228.175; 3.W.228.240;
3.W.228.244; 3.W.229.228; 3.W.229.229; 3.W.229.230; 3.W.229.231;
3.W.229.236; 3.W.229.237; 3.W.229.238; 3.W.229.239; 3.W.229.154;
3.W.229.157; 3.W.229.166; 3.W.229.169; 3.W.229.172; 3.W.229.175;
3.W.229.240; 3.W.229.244; 3.W.230.228; 3.W.230.229; 3.W.230.230;
3.W.230.231; 3.W.230.236; 3.W.230.237; 3.W.230.238; 3.W.230.239;
3.W.230.154; 3.W.230.157; 3.W.230.166; 3.W.230.169; 3.W.230.172;
3.W.230.175; 3.W.230.240; 3.W.230.244; 3.W.231.228; 3.W.231.229;
3.W.231.230; 3.W.231.231; 3.W.231.236; 3.W.231.237; 3.W.231.238;
3.W.231.239; 3.W.231.154; 3.W.231.157; 3.W.231.166; 3.W.231.169;
3.W.231.172; 3.W.231.175; 3.W.231.240; 3.W.231.244; 3.W.236.228;
3.W.236.229; 3.W.236.230; 3.W.236.231; 3.W.236.236; 3.W.236.237;
3.W.236.238; 3.W.236.239; 3.W.236.154; 3.W.236.157; 3.W.236.166;
3.W.236.169; 3.W.236.172; 3.W.236.175; 3.W.236.240; 3.W.236.244;
3.W.237.228; 3.W.237.229; 3.W.237.230; 3.W.237.231; 3.W.237.236;
3.W.237.237; 3.W.237.238; 3.W.237.239; 3.W.237.154; 3.W.237.157;
3.W.237.166; 3.W.237.169; 3.W.237.172; 3.W.237.175; 3.W.237.240;
3.W.237.244; 3.W.238.228; 3.W.238.229; 3.W.238.230; 3.W.238.231;
3.W.238.236; 3.W.238.237; 3.W.238.238; 3.W.238.239; 3.W.238.154;
3.W.238.157; 3.W.238.166; 3.W.238.169; 3.W.238.172; 3.W.238.175;
3.W.238.240; 3.W.238.244; 3.W.239.228; 3.W.239.229; 3.W.239.230;
3.W.239.231; 3.W.239.236; 3.W.239.237; 3.W.239.238; 3.W.239.239;
3.W.239.154; 3.W.239.157; 3.W.239.166; 3.W.239.169; 3.W.239.172;
3.W.239.175; 3.W.239.240; 3.W.239.244; 3.W.154.228; 3.W.154.229;
3.W.154.230; 3.W.154.231; 3.W.154.236; 3.W.154.237; 3.W.154.238;
3.W.154.239; 3.W.154.154; 3.W.154.157; 3.W.154.166; 3.W.154.169;
3.W.154.172; 3.W.154.175; 3.W.154.240; 3.W.154.244; 3.W.157.228;
3.W.157.229; 3.W.157.230; 3.W.157.231; 3.W.157.236; 3.W.157.237;
3.W.157.238; 3.W.157.239; 3.W.157.154; 3.W.157.157; 3.W.157.166;
3.W.157.169; 3.W.157.172; 3.W.157.175; 3.W.157.240; 3.W.157.244;
3.W.166.228; 3.W.166.229; 3.W.166.230; 3.W.166.231; 3.W.166.236;
3.W.166.237; 3.W.166.238; 3.W.166.239; 3.W.166.154; 3.W.166.157;
3.W.166.166; 3.W.166.169; 3.W.166.172; 3.W.166.175; 3.W.166.240;
3.W.166.244; 3.W.169.228; 3.W.169.229; 3.W.169.230; 3.W.169.231;
3.W.169.236; 3.W.169.237; 3.W.169.238; 3.W.169.239; 3.W.169.154;
3.W.169.157; 3.W.169.166; 3.W.169.169; 3.W.169.172; 3.W.169.175;
3.W.169.240; 3.W.169.244; 3.W.172.228; 3.W.172.229; 3.W.172.230;

TABLE 100-continued

3.W.172.231; 3.W.172.236; 3.W.172.237; 3.W.172.238; 3.W.172.239;
3.W.172.154; 3.W.172.157; 3.W.172.166; 3.W.172.169; 3.W.172.172;
3.W.172.175; 3.W.172.240; 3.W.172.244; 3.W.175.228; 3.W.175.229;
3.W.175.230; 3.W.175.231; 3.W.175.236; 3.W.175.237; 3.W.175.238;
3.W.175.239; 3.W.175.154; 3.W.175.157; 3.W.175.166; 3.W.175.169;
3.W.175.172; 3.W.175.175; 3.W.175.240; 3.W.175.244; 3.W.240.228;
3.W.240.229; 3.W.240.230; 3.W.240.231; 3.W.240.236; 3.W.240.237;
3.W.240.238; 3.W.240.239; 3.W.240.154; 3.W.240.157; 3.W.240.166;
3.W.240.169; 3.W.240.172; 3.W.240.175; 3.W.240.240; 3.W.240.244;
3.W.244.228; 3.W.244.229; 3.W.244.230; 3.W.244.231; 3.W.244.236;
3.W.244.237; 3.W.244.238; 3.W.244.239; 3.W.244.154; 3.W.244.157;
3.W.244.166; 3.W.244.169; 3.W.244.172; 3.W.244.175; 3.W.244.240; 3.W.244.244;
Prodrugs of 3.Y 3.Y.228.228; 3.Y.228.229; 3.Y.228.230; 3.Y.228.231; 3.Y.228.236;
3.Y.228.237; 3.Y.228.238; 3.Y.228.239; 3.Y.228.154; 3.Y.228.157; 3.Y.228.166;
3.Y.228.169; 3.Y.228.172; 3.Y.228.175; 3.Y.228.240; 3.Y.228.244; 3.Y.229.228;
3.Y.229.229; 3.Y.229.230; 3.Y.229.231; 3.Y.229.236; 3.Y.229.237; 3.Y.229.238;
3.Y.229.239; 3.Y.229.154; 3.Y.229.157; 3.Y.229.166; 3.Y.229.169; 3.Y.229.172;
3.Y.229.175; 3.Y.229.240; 3.Y.229.244; 3.Y.230.228; 3.Y.230.229; 3.Y.230.230;
3.Y.230.231; 3.Y.230.236; 3.Y.230.237; 3.Y.230.238; 3.Y.230.239; 3.Y.230.154;
3.Y.230.157; 3.Y.230.166; 3.Y.230.169; 3.Y.230.172; 3.Y.230.175; 3.Y.230.240;
3.Y.230.244; 3.Y.231.228; 3.Y.231.229; 3.Y.231.230; 3.Y.231.231; 3.Y.231.236;
3.Y.231.237; 3.Y.231.238; 3.Y.231.239; 3.Y.231.154; 3.Y.231.157; 3.Y.231.166;
3.Y.231.169; 3.Y.231.172; 3.Y.231.175; 3.Y.231.240; 3.Y.231.244; 3.Y.236.228;
3.Y.236.229; 3.Y.236.230; 3.Y.236.231; 3.Y.236.236; 3.Y.236.237; 3.Y.236.238;
3.Y.236.239; 3.Y.236.154; 3.Y.236.157; 3.Y.236.166; 3.Y.236.169; 3.Y.236.172;
3.Y.236.175; 3.Y.236.240; 3.Y.236.244; 3.Y.237.228; 3.Y.237.229; 3.Y.237.230;
3.Y.237.231; 3.Y.237.236; 3.Y.237.237; 3.Y.237.238; 3.Y.237.239; 3.Y.237.154;
3.Y.237.157; 3.Y.237.166; 3.Y.237.169; 3.Y.237.172; 3.Y.237.175; 3.Y.237.240;
3.Y.237.244; 3.Y.238.228; 3.Y.238.229; 3.Y.238.230; 3.Y.238.231; 3.Y.238.236;
3.Y.238.237; 3.Y.238.238; 3.Y.238.239; 3.Y.238.154; 3.Y.238.157; 3.Y.238.166;
3.Y.238.169; 3.Y.238.172; 3.Y.238.175; 3.Y.238.240; 3.Y.238.244; 3.Y.239.228;
3.Y.239.229; 3.Y.239.230; 3.Y.239.231; 3.Y.239.236; 3.Y.239.237; 3.Y.239.238;
3.Y.239.239; 3.Y.239.154; 3.Y.239.157; 3.Y.239.166; 3.Y.239.169; 3.Y.239.172;
3.Y.239.175; 3.Y.239.240; 3.Y.239.244; 3.Y.154.228; 3.Y.154.229; 3.Y.154.230;
3.Y.154.231; 3.Y.154.236; 3.Y.154.237; 3.Y.154.238; 3.Y.154.239; 3.Y.154.154;
3.Y.154.157; 3.Y.154.166; 3.Y.154.169; 3.Y.154.172; 3.Y.154.175; 3.Y.154.240;
3.Y.154.244; 3.Y.157.228; 3.Y.157.229; 3.Y.157.230; 3.Y.157.231; 3.Y.157.236;
3.Y.157.237; 3.Y.157.238; 3.Y.157.239; 3.Y.157.154; 3.Y.157.157; 3.Y.157.166;
3.Y.157.169; 3.Y.157.172; 3.Y.157.175; 3.Y.157.240; 3.Y.157.244; 3.Y.166.228;
3.Y.166.229; 3.Y.166.230; 3.Y.166.231; 3.Y.166.236; 3.Y.166.237; 3.Y.166.238;
3.Y.166.239; 3.Y.166.154; 3.Y.166.157; 3.Y.166.166; 3.Y.166.169; 3.Y.166.172;
3.Y.166.175; 3.Y.166.240; 3.Y.166.244; 3.Y.169.228; 3.Y.169.229; 3.Y.169.230;
3.Y.169.231; 3.Y.169.236; 3.Y.169.237; 3.Y.169.238; 3.Y.169.239; 3.Y.169.154;
3.Y.169.157; 3.Y.169.166; 3.Y.169.169; 3.Y.169.172; 3.Y.169.175; 3.Y.169.240;
3.Y.169.244; 3.Y.172.228; 3.Y.172.229; 3.Y.172.230; 3.Y.172.231; 3.Y.172.236;
3.Y.172.237; 3.Y.172.238; 3.Y.172.239; 3.Y.172.154; 3.Y.172.157; 3.Y.172.166;
3.Y.172.169; 3.Y.172.172; 3.Y.172.175; 3.Y.172.240; 3.Y.172.244; 3.Y.175.228;
3.Y.175.229; 3.Y.175.230; 3.Y.175.231; 3.Y.175.236; 3.Y.175.237; 3.Y.175.238;
3.Y.175.239; 3.Y.175.154; 3.Y.175.157; 3.Y.175.166; 3.Y.175.169; 3.Y.175.172;
3.Y.175.175; 3.Y.175.240; 3.Y.175.244; 3.Y.240.228; 3.Y.240.229; 3.Y.240.230;
3.Y.240.231; 3.Y.240.236; 3.Y.240.237; 3.Y.240.238; 3.Y.240.239; 3.Y.240.154;
3.Y.240.157; 3.Y.240.166; 3.Y.240.169; 3.Y.240.172; 3.Y.240.175; 3.Y.240.240;
3.Y.240.244; 3.Y.244.228; 3.Y.244.229; 3.Y.244.230; 3.Y.244.231; 3.Y.244.236;
3.Y.244.237; 3.Y.244.238; 3.Y.244.239; 3.Y.244.154; 3.Y.244.157; 3.Y.244.166;
3.Y.244.169; 3.Y.244.172; 3.Y.244.175; 3.Y.244.240; 3.Y.244.244;
Prodrugs of 4.B 4.B.228.228; 4.B.228.229; 4.B.228.230; 4.B.228.231; 4.B.228.236;
4.B.228.237; 4.B.228.238; 4.B.228.239; 4.B.228.154; 4.B.228.157; 4.B.228.166;
4.B.228.169; 4.B.228.172; 4.B.228.175; 4.B.228.240; 4.B.228.244; 4.B.229.228;
4.B.229.229; 4.B.229.230; 4.B.229.231; 4.B.229.236; 4.B.229.237; 4.B.229.238;
4.B.229.239; 4.B.229.154; 4.B.229.157; 4.B.229.166; 4.B.229.169; 4.B.229.172;
4.B.229.175; 4.B.229.240; 4.B.229.244; 4.B.230.228; 4.B.230.229; 4.B.230.230;
4.B.230.231; 4.B.230.236; 4.B.230.237; 4.B.230.238; 4.B.230.239; 4.B.230.154;
4.B.230.157; 4.B.230.166; 4.B.230.169; 4.B.230.172; 4.B.230.175; 4.B.230.240;
4.B.230.244; 4.B.231.228; 4.B.231.229; 4.B.231.230; 4.B.231.231; 4.B.231.236;
4.B.231.237; 4.B.231.238; 4.B.231.239; 4.B.231.154; 4.B.231.157; 4.B.231.166;
4.B.231.169; 4.B.231.172; 4.B.231.175; 4.B.231.240; 4.B.231.244; 4.B.236.228;
4.B.236.229; 4.B.236.230; 4.B.236.231; 4.B.236.236; 4.B.236.237; 4.B.236.238;
4.B.236.239; 4.B.236.154; 4.B.236.157; 4.B.236.166; 4.B.236.169; 4.B.236.172;
4.B.236.175; 4.B.236.240; 4.B.236.244; 4.B.237.228; 4.B.237.229; 4.B.237.230;
4.B.237.231; 4.B.237.236; 4.B.237.237; 4.B.237.238; 4.B.237.239; 4.B.237.154;
4.B.237.157; 4.B.237.166; 4.B.237.169; 4.B.237.172; 4.B.237.175; 4.B.237.240;
4.B.237.244; 4.B.238.228; 4.B.238.229; 4.B.238.230; 4.B.238.231; 4.B.238.236;
4.B.238.237; 4.B.238.238; 4.B.238.239; 4.B.238.154; 4.B.238.157; 4.B.238.166;
4.B.238.169; 4.B.238.172; 4.B.238.175; 4.B.238.240; 4.B.238.244; 4.B.239.228;
4.B.239.229; 4.B.239.230; 4.B.239.231; 4.B.239.236; 4.B.239.237; 4.B.239.238;

TABLE 100-continued

4.B.239.239; 4.B.239.154; 4.B.239.157; 4.B.239.166; 4.B.239.169; 4.B.239.172;
4.B.239.175; 4.B.239.240; 4.B.239.244; 4.B.154.228; 4.B.154.229; 4.B.154.230;
4.B.154.231; 4.B.154.236; 4.B.154.237; 4.B.154.238; 4.B.154.239; 4.B.154.154;
4.B.154.157; 4.B.154.166; 4.B.154.169; 4.B.154.172; 4.B.154.175; 4.B.154.240;
4.B.154.244; 4.B.157.228; 4.B.157.229; 4.B.157.230; 4.B.157.231; 4.B.157.236;
4.B.157.237; 4.B.157.238; 4.B.157.239; 4.B.157.154; 4.B.157.157; 4.B.157.166;
4.B.157.169; 4.B.157.172; 4.B.157.175; 4.B.157.240; 4.B.157.244; 4.B.166.228;
4.B.166.229; 4.B.166.230; 4.B.166.231; 4.B.166.236; 4.B.166.237; 4.B.166.238;
4.B.166.239; 4.B.166.154; 4.B.166.157; 4.B.166.166; 4.B.166.169; 4.B.166.172;
4.B.166.175; 4.B.166.240; 4.B.166.244; 4.B.169.228; 4.B.169.229; 4.B.169.230;
4.B.169.231; 4.B.169.236; 4.B.169.237; 4.B.169.238; 4.B.169.239; 4.B.169.154;
4.B.169.157; 4.B.169.166; 4.B.169.169; 4.B.169.172; 4.B.169.175; 4.B.169.240;
4.B.169.244; 4.B.172.228; 4.B.172.229; 4.B.172.230; 4.B.172.231; 4.B.172.236;
4.B.172.237; 4.B.172.238; 4.B.172.239; 4.B.172.154; 4.B.172.157; 4.B.172.166;
4.B.172.169; 4.B.172.172; 4.B.172.175; 4.B.172.240; 4.B.172.244; 4.B.175.228;
4.B.175.229; 4.B.175.230; 4.B.175.231; 4.B.175.236; 4.B.175.237; 4.B.175.238;
4.B.175.239; 4.B.175.154; 4.B.175.157; 4.B.175.166; 4.B.175.169; 4.B.175.172;
4.B.175.175; 4.B.175.240; 4.B.175.244; 4.B.240.228; 4.B.240.229; 4.B.240.230;
4.B.240.231; 4.B.240.236; 4.B.240.237; 4.B.240.238; 4.B.240.239; 4.B.240.154;
4.B.240.157; 4.B.240.166; 4.B.240.169; 4.B.240.172; 4.B.240.175; 4.B.240.240;
4.B.240.244; 4.B.244.228; 4.B.244.229; 4.B.244.230; 4.B.244.231; 4.B.244.236;
4.B.244.237; 4.B.244.238; 4.B.244.239; 4.B.244.154; 4.B.244.157; 4.B.244.166;
4.B.244.169; 4.B.244.172; 4.B.244.175; 4.B.244.240; 4.B.244.244;
Prodrugs of 4.D 4.D.228.228; 4.D.228.229; 4.D.228.230; 4.D.228.231; 4.D.228.236;
4.D.228.237; 4.D.228.238; 4.D.228.239; 4.D.228.154; 4.D.228.157;
4.D.228.166; 4.D.228.169; 4.D.228.172; 4.D.228.175; 4.D.228.240;
4.D.228.244; 4.D.229.228; 4.D.229.229; 4.D.229.230; 4.D.229.231;
4.D.229.236; 4.D.229.237; 4.D.229.238; 4.D.229.239; 4.D.229.154;
4.D.229.157; 4.D.229.166; 4.D.229.169; 4.D.229.172; 4.D.229.175;
4.D.229.240; 4.D.229.244; 4.D.230.228; 4.D.230.229; 4.D.230.230;
4.D.230.231; 4.D.230.236; 4.D.230.237; 4.D.230.238; 4.D.230.239;
4.D.230.154; 4.D.230.157; 4.D.230.166; 4.D.230.169; 4.D.230.172;
4.D.230.175; 4.D.230.240; 4.D.230.244; 4.D.231.228; 4.D.231.229;
4.D.231.230; 4.D.231.231; 4.D.231.236; 4.D.231.237; 4.D.231.238;
4.D.231.239; 4.D.231.154; 4.D.231.157; 4.D.231.166; 4.D.231.169;
4.D.231.172; 4.D.231.175; 4.D.231.240; 4.D.231.244; 4.D.236.228;
4.D.236.229; 4.D.236.230; 4.D.236.231; 4.D.236.236; 4.D.236.237;
4.D.236.238; 4.D.236.239; 4.D.236.154; 4.D.236.157; 4.D.236.166;
4.D.236.169; 4.D.236.172; 4.D.236.175; 4.D.236.240; 4.D.236.244;
4.D.237.228; 4.D.237.229; 4.D.237.230; 4.D.237.231; 4.D.237.236;
4.D.237.237; 4.D.237.238; 4.D.237.239; 4.D.237.154; 4.D.237.157;
4.D.237.166; 4.D.237.169; 4.D.237.172; 4.D.237.175; 4.D.237.240;
4.D.237.244; 4.D.238.228; 4.D.238.229; 4.D.238.230; 4.D.238.231;
4.D.238.236; 4.D.238.237; 4.D.238.238; 4.D.238.239; 4.D.238.154;
4.D.238.157; 4.D.238.166; 4.D.238.169; 4.D.238.172; 4.D.238.175;
4.D.238.240; 4.D.238.244; 4.D.239.228; 4.D.239.229; 4.D.239.230;
4.D.239.231; 4.D.239.236; 4.D.239.237; 4.D.239.238; 4.D.239.239;
4.D.239.154; 4.D.239.157; 4.D.239.166; 4.D.239.169; 4.D.239.172;
4.D.239.175; 4.D.239.240; 4.D.239.244; 4.D.154.228; 4.D.154.229;
4.D.154.230; 4.D.154.231; 4.D.154.236; 4.D.154.237; 4.D.154.238;
4.D.154.239; 4.D.154.154; 4.D.154.157; 4.D.154.166; 4.D.154.169;
4.D.154.172; 4.D.154.175; 4.D.154.240; 4.D.154.244; 4.D.157.228;
4.D.157.229; 4.D.157.230; 4.D.157.231; 4.D.157.236; 4.D.157.237;
4.D.157.238; 4.D.157.239; 4.D.157.154; 4.D.157.157; 4.D.157.166;
4.D.157.169; 4.D.157.172; 4.D.157.175; 4.D.157.240; 4.D.157.244;
4.D.166.228; 4.D.166.229; 4.D.166.230; 4.D.166.231; 4.D.166.236;
4.D.166.237; 4.D.166.238; 4.D.166.239; 4.D.166.154; 4.D.166.157;
4.D.166.166; 4.D.166.169; 4.D.166.172; 4.D.166.175; 4.D.166.240;
4.D.166.244; 4.D.169.228; 4.D.169.229; 4.D.169.230; 4.D.169.231;
4.D.169.236; 4.D.169.237; 4.D.169.238; 4.D.169.239; 4.D.169.154;
4.D.169.157; 4.D.169.166; 4.D.169.169; 4.D.169.172; 4.D.169.175;
4.D.169.240; 4.D.169.244; 4.D.172.228; 4.D.172.229; 4.D.172.230;
4.D.172.231; 4.D.172.236; 4.D.172.237; 4.D.172.238; 4.D.172.239;
4.D.172.154; 4.D.172.157; 4.D.172.166; 4.D.172.169; 4.D.172.172;
4.D.172.175; 4.D.172.240; 4.D.172.244; 4.D.175.228; 4.D.175.229;
4.D.175.230; 4.D.175.231; 4.D.175.236; 4.D.175.237; 4.D.175.238;
4.D.175.239; 4.D.175.154; 4.D.175.157; 4.D.175.166; 4.D.175.169;
4.D.175.172; 4.D.175.175; 4.D.175.240; 4.D.175.244; 4.D.240.228;
4.D.240.229; 4.D.240.230; 4.D.240.231; 4.D.240.236; 4.D.240.237;
4.D.240.238; 4.D.240.239; 4.D.240.154; 4.D.240.157; 4.D.240.166;
4.D.240.169; 4.D.240.172; 4.D.240.175; 4.D.240.240; 4.D.240.244;
4.D.244.228; 4.D.244.229; 4.D.244.230; 4.D.244.231; 4.D.244.236;
4.D.244.237; 4.D.244.238; 4.D.244.239; 4.D.244.154; 4.D.244.157;
4.D.244.166; 4.D.244.169; 4.D.244.172; 4.D.244.175; 4.D.244.240; 4.D.244.244;

TABLE 100-continued

Prodrugs of 4.E

4.E.228.228; 4.E.228.229; 4.E.228.230; 4.E.228.231; 4.E.228.236; 4.E.228.237; 4.E.228.238; 4.E.228.239; 4.E.228.154; 4.E.228.157; 4.E.228.166; 4.E.228.169; 4.E.228.172; 4.E.228.175; 4.E.228.240; 4.E.228.244; 4.E.229.228; 4.E.229.229; 4.E.229.230; 4.E.229.231; 4.E.229.236; 4.E.229.237; 4.E.229.238; 4.E.229.239; 4.E.229.154; 4.E.229.157; 4.E.229.166; 4.E.229.169; 4.E.229.172; 4.E.229.175; 4.E.229.240; 4.E.229.244; 4.E.230.228; 4.E.230.229; 4.E.230.230; 4.E.230.231; 4.E.230.236; 4.E.230.237; 4.E.230.238; 4.E.230.239; 4.E.230.154; 4.E.230.157; 4.E.230.166; 4.E.230.169; 4.E.230.172; 4.E.230.175; 4.E.230.240; 4.E.230.244; 4.E.231.228; 4.E.231.229; 4.E.231.230; 4.E.231.231; 4.E.231.236; 4.E.231.237; 4.E.231.238; 4.E.231.239; 4.E.231.154; 4.E.231.157; 4.E.231.166; 4.E.231.169; 4.E.231.172; 4.E.231.175; 4.E.231.240; 4.E.231.244; 4.E.236.228; 4.E.236.229; 4.E.236.230; 4.E.236.231; 4.E.236.236; 4.E.236.237; 4.E.236.238; 4.E.236.239; 4.E.236.154; 4.E.236.157; 4.E.236.166; 4.E.236.169; 4.E.236.172; 4.E.236.175; 4.E.236.240; 4.E.236.244; 4.E.237.228; 4.E.237.229; 4.E.237.230; 4.E.237.231; 4.E.237.236; 4.E.237.237; 4.E.237.238; 4.E.237.239; 4.E.237.154; 4.E.237.157; 4.E.237.166; 4.E.237.169; 4.E.237.172; 4.E.237.175; 4.E.237.240; 4.E.237.244; 4.E.238.228; 4.E.238.229; 4.E.238.230; 4.E.238.231; 4.E.238.236; 4.E.238.237; 4.E.238.238; 4.E.238.239; 4.E.238.154; 4.E.238.157; 4.E.238.166; 4.E.238.169; 4.E.238.172; 4.E.238.175; 4.E.238.240; 4.E.238.244; 4.E.239.228; 4.E.239.229; 4.E.239.230; 4.E.239.231; 4.E.239.236; 4.E.239.237; 4.E.239.238; 4.E.239.239; 4.E.239.154; 4.E.239.157; 4.E.239.166; 4.E.239.169; 4.E.239.172; 4.E.239.175; 4.E.239.240; 4.E.239.244; 4.E.154.228; 4.E.154.229; 4.E.154.230; 4.E.154.231; 4.E.154.236; 4.E.154.237; 4.E.154.238; 4.E.154.239; 4.E.154.154; 4.E.154.157; 4.E.154.166; 4.E.154.169; 4.E.154.172; 4.E.154.175; 4.E.154.240; 4.E.154.244; 4.E.157.228; 4.E.157.229; 4.E.157.230; 4.E.157.231; 4.E.157.236; 4.E.157.237; 4.E.157.238; 4.E.157.239; 4.E.157.154; 4.E.157.157; 4.E.157.166; 4.E.157.169; 4.E.157.172; 4.E.157.175; 4.E.157.240; 4.E.157.244; 4.E.166.228; 4.E.166.229; 4.E.166.230; 4.E.166.231; 4.E.166.236; 4.E.166.237; 4.E.166.238; 4.E.166.239; 4.E.166.154; 4.E.166.157; 4.E.166.166; 4.E.166.169; 4.E.166.172; 4.E.166.175; 4.E.166.240; 4.E.166.244; 4.E.169.228; 4.E.169.229; 4.E.169.230; 4.E.169.231; 4.E.169.236; 4.E.169.237; 4.E.169.238; 4.E.169.239; 4.E.169.154; 4.E.169.157; 4.E.169.166; 4.E.169.169; 4.E.169.172; 4.E.169.175; 4.E.169.240; 4.E.169.244; 4.E.172.228; 4.E.172.229; 4.E.172.230; 4.E.172.231; 4.E.172.236; 4.E.172.237; 4.E.172.238; 4.E.172.239; 4.E.172.154; 4.E.172.157; 4.E.172.166; 4.E.172.169; 4.E.172.172; 4.E.172.175; 4.E.172.240; 4.E.172.244; 4.E.175.228; 4.E.175.229; 4.E.175.230; 4.E.175.231; 4.E.175.236; 4.E.175.237; 4.E.175.238; 4.E.175.239; 4.E.175.154; 4.E.175.157; 4.E.175.166; 4.E.175.169; 4.E.175.172; 4.E.175.175; 4.E.175.240; 4.E.175.244; 4.E.240.228; 4.E.240.229; 4.E.240.230; 4.E.240.231; 4.E.240.236; 4.E.240.237; 4.E.240.238; 4.E.240.239; 4.E.240.154; 4.E.240.157; 4.E.240.166; 4.E.240.169; 4.E.240.172; 4.E.240.175; 4.E.240.240; 4.E.240.244; 4.E.244.228; 4.E.244.229; 4.E.244.230; 4.E.244.231; 4.E.244.236; 4.E.244.237; 4.E.244.238; 4.E.244.239; 4.E.244.154; 4.E.244.157; 4.E.244.166; 4.E.244.169; 4.E.244.172; 4.E.244.175; 4.E.244.240; 4.E.244.244;

Prodrugs of 4.G

4.G.228.228; 4.G.228.229; 4.G.228.230; 4.G.228.231; 4.G.228.236; 4.G.228.237; 4.G.228.238; 4.G.228.239; 4.G.228.154; 4.G.228.157; 4.G.228.166; 4.G.228.169; 4.G.228.172; 4.G.228.175; 4.G.228.240; 4.G.228.244; 4.G.229.228; 4.G.229.229; 4.G.229.230; 4.G.229.231; 4.G.229.236; 4.G.229.237; 4.G.229.238; 4.G.229.239; 4.G.229.154; 4.G.229.157; 4.G.229.166; 4.G.229.169; 4.G.229.172; 4.G.229.175; 4.G.229.240; 4.G.229.244; 4.G.230.228; 4.G.230.229; 4.G.230.230; 4.G.230.231; 4.G.230.236; 4.G.230.237; 4.G.230.238; 4.G.230.239; 4.G.230.154; 4.G.230.157; 4.G.230.166; 4.G.230.169; 4.G.230.172; 4.G.230.175; 4.G.230.240; 4.G.230.244; 4.G.231.228; 4.G.231.229; 4.G.231.230; 4.G.231.231; 4.G.231.236; 4.G.231.237; 4.G.231.238; 4.G.231.239; 4.G.231.154; 4.G.231.157; 4.G.231.166; 4.G.231.169; 4.G.231.172; 4.G.231.175; 4.G.231.240; 4.G.231.244; 4.G.236.228; 4.G.236.229; 4.G.236.230; 4.G.236.231; 4.G.236.236; 4.G.236.237; 4.G.236.238; 4.G.236.239; 4.G.236.154; 4.G.236.157; 4.G.236.166; 4.G.236.169; 4.G.236.172; 4.G.236.175; 4.G.236.240; 4.G.236.244; 4.G.237.228; 4.G.237.229; 4.G.237.230; 4.G.237.231; 4.G.237.236; 4.G.237.237; 4.G.237.238; 4.G.237.239; 4.G.237.154; 4.G.237.157; 4.G.237.166; 4.G.237.169; 4.G.237.172; 4.G.237.175; 4.G.237.240; 4.G.237.244; 4.G.238.228; 4.G.238.229; 4.G.238.230; 4.G.238.231; 4.G.238.236; 4.G.238.237; 4.G.238.238; 4.G.238.239; 4.G.238.154; 4.G.238.157; 4.G.238.166; 4.G.238.169; 4.G.238.172; 4.G.238.175; 4.G.238.240; 4.G.238.244; 4.G.239.228; 4.G.239.229; 4.G.239.230; 4.G.239.231; 4.G.239.236; 4.G.239.237; 4.G.239.238; 4.G.239.239; 4.G.239.154; 4.G.239.157; 4.G.239.166; 4.G.239.169; 4.G.239.172; 4.G.239.175; 4.G.239.240; 4.G.239.244; 4.G.154.228; 4.G.154.229; 4.G.154.230; 4.G.154.231; 4.G.154.236; 4.G.154.237; 4.G.154.238; 4.G.154.239; 4.G.154.154; 4.G.154.157; 4.G.154.166; 4.G.154.169; 4.G.154.172; 4.G.154.175; 4.G.154.240; 4.G.154.244; 4.G.157.228; 4.G.157.229; 4.G.157.230; 4.G.157.231; 4.G.157.236; 4.G.157.237; 4.G.157.238; 4.G.157.239; 4.G.157.154; 4.G.157.157; 4.G.157.166; 4.G.157.169; 4.G.157.172; 4.G.157.175; 4.G.157.240; 4.G.157.244;

TABLE 100-continued

4.G.166.228; 4.G.166.229; 4.G.166.230; 4.G.166.231; 4.G.166.236;
4.G.166.237; 4.G.166.238; 4.G.166.239; 4.G.166.154; 4.G.166.157;
4.G.166.166; 4.G.166.169; 4.G.166.172; 4.G.166.175; 4.G.166.240;
4.G.166.244; 4.G.169.228; 4.G.169.229; 4.G.169.230; 4.G.169.231;
4.G.169.236; 4.G.169.237; 4.G.169.238; 4.G.169.239; 4.G.169.154;
4.G.169.157; 4.G.169.166; 4.G.169.169; 4.G.169.172; 4.G.169.175;
4.G.169.240; 4.G.169.244; 4.G.172.228; 4.G.172.229; 4.G.172.230;
4.G.172.231; 4.G.172.236; 4.G.172.237; 4.G.172.238; 4.G.172.239;
4.G.172.154; 4.G.172.157; 4.G.172.166; 4.G.172.169; 4.G.172.172;
4.G.172.175; 4.G.172.240; 4.G.172.244; 4.G.175.228; 4.G.175.229;
4.G.175.230; 4.G.175.231; 4.G.175.236; 4.G.175.237; 4.G.175.238;
4.G.175.239; 4.G.175.154; 4.G.175.157; 4.G.175.166; 4.G.175.169;
4.G.175.172; 4.G.175.175; 4.G.175.240; 4.G.175.244; 4.G.240.228;
4.G.240.229; 4.G.240.230; 4.G.240.231; 4.G.240.236; 4.G.240.237;
4.G.240.238; 4.G.240.239; 4.G.240.154; 4.G.240.157; 4.G.240.166;
4.G.240.169; 4.G.240.172; 4.G.240.175; 4.G.240.240; 4.G.240.244;
4.G.244.228; 4.G.244.229; 4.G.244.230; 4.G.244.231; 4.G.244.236;
4.G.244.237; 4.G.244.238; 4.G.244.239; 4.G.244.154; 4.G.244.157;
4.G.244.166; 4.G.244.169; 4.G.244.172; 4.G.244.175; 4.G.244.240; 4.G.244.244;
Prodrugs of 4.I 4.I.228.228; 4.I.228.229; 4.I.228.230; 4.I.228.231; 4.I.228.236; 4.I.228.237;
4.I.228.238; 4.I.228.239; 4.I.228.154; 4.I.228.157; 4.I.228.166; 4.I.228.169;
4.I.228.172; 4.I.228.175; 4.I.228.240; 4.I.228.244; 4.I.229.228; 4.I.229.229;
4.I.229.230; 4.I.229.231; 4.I.229.236; 4.I.229.237; 4.I.229.238; 4.I.229.239;
4.I.229.154; 4.I.229.157; 4.I.229.166; 4.I.229.169; 4.I.229.172; 4.I.229.175;
4.I.229.240; 4.I.229.244; 4.I.230.228; 4.I.230.229; 4.I.230.230; 4.I.230.231;
4.I.230.236; 4.I.230.237; 4.I.230.238; 4.I.230.239; 4.I.230.154; 4.I.230.157;
4.I.230.166; 4.I.230.169; 4.I.230.172; 4.I.230.175; 4.I.230.240; 4.I.230.244;
4.I.231.228; 4.I.231.229; 4.I.231.230; 4.I.231.231; 4.I.231.236; 4.I.231.237;
4.I.231.238; 4.I.231.239; 4.I.231.154; 4.I.231.157; 4.I.231.166; 4.I.231.169;
4.I.231.172; 4.I.231.175; 4.I.231.240; 4.I.231.244; 4.I.236.228; 4.I.236.229;
4.I.236.230; 4.I.236.231; 4.I.236.236; 4.I.236.237; 4.I.236.238; 4.I.236.239;
4.I.236.154; 4.I.236.157; 4.I.236.166; 4.I.236.169; 4.I.236.172; 4.I.236.175;
4.I.236.240; 4.I.236.244; 4.I.237.228; 4.I.237.229; 4.I.237.230; 4.I.237.231;
4.I.237.236; 4.I.237.237; 4.I.237.238; 4.I.237.239; 4.I.237.154; 4.I.237.157;
4.I.237.166; 4.I.237.169; 4.I.237.172; 4.I.237.175; 4.I.237.240; 4.I.237.244;
4.I.238.228; 4.I.238.229; 4.I.238.230; 4.I.238.231; 4.I.238.236; 4.I.238.237;
4.I.238.238; 4.I.238.239; 4.I.238.154; 4.I.238.157; 4.I.238.166; 4.I.238.169;
4.I.238.172; 4.I.238.175; 4.I.238.240; 4.I.238.244; 4.I.239.228; 4.I.239.229;
4.I.239.230; 4.I.239.231; 4.I.239.236; 4.I.239.237; 4.I.239.238; 4.I.239.239;
4.I.239.154; 4.I.239.157; 4.I.239.166; 4.I.239.169; 4.I.239.172; 4.I.239.175;
4.I.239.240; 4.I.239.244; 4.I.154.228; 4.I.154.229; 4.I.154.230; 4.I.154.231;
4.I.154.236; 4.I.154.237; 4.I.154.238; 4.I.154.239; 4.I.154.154; 4.I.154.157;
4.I.154.166; 4.I.154.169; 4.I.154.172; 4.I.154.175; 4.I.154.240; 4.I.154.244;
4.I.157.228; 4.I.157.229; 4.I.157.230; 4.I.157.231; 4.I.157.236; 4.I.157.237;
4.I.157.238; 4.I.157.239; 4.I.157.154; 4.I.157.157; 4.I.157.166; 4.I.157.169;
4.I.157.172; 4.I.157.175; 4.I.157.240; 4.I.157.244; 4.I.166.228; 4.I.166.229;
4.I.166.230; 4.I.166.231; 4.I.166.236; 4.I.166.237; 4.I.166.238; 4.I.166.239;
4.I.166.154; 4.I.166.157; 4.I.166.166; 4.I.166.169; 4.I.166.172; 4.I.166.175;
4.I.166.240; 4.I.166.244; 4.I.169.228; 4.I.169.229; 4.I.169.230; 4.I.169.231;
4.I.169.236; 4.I.169.237; 4.I.169.238; 4.I.169.239; 4.I.169.154; 4.I.169.157;
4.I.169.166; 4.I.169.169; 4.I.169.172; 4.I.169.175; 4.I.169.240; 4.I.169.244;
4.I.172.228; 4.I.172.229; 4.I.172.230; 4.I.172.231; 4.I.172.236; 4.I.172.237;
4.I.172.238; 4.I.172.239; 4.I.172.154; 4.I.172.157; 4.I.172.166; 4.I.172.169;
4.I.172.172; 4.I.172.175; 4.I.172.240; 4.I.172.244; 4.I.175.228; 4.I.175.229;
4.I.175.230; 4.I.175.231; 4.I.175.236; 4.I.175.237; 4.I.175.238; 4.I.175.239;
4.I.175.154; 4.I.175.157; 4.I.175.166; 4.I.175.169; 4.I.175.172; 4.I.175.175;
4.I.175.240; 4.I.175.244; 4.I.240.228; 4.I.240.229; 4.I.240.230; 4.I.240.231;
4.I.240.236; 4.I.240.237; 4.I.240.238; 4.I.240.239; 4.I.240.154; 4.I.240.157;
4.I.240.166; 4.I.240.169; 4.I.240.172; 4.I.240.175; 4.I.240.240; 4.I.240.244;
4.I.244.228; 4.I.244.229; 4.I.244.230; 4.I.244.231; 4.I.244.236; 4.I.244.237;
4.I.244.238; 4.I.244.239; 4.I.244.154; 4.I.244.157; 4.I.244.166; 4.I.244.169;
4.I.244.172; 4.I.244.175; 4.I.244.240; 4.I.244.244;
Prodrugs of 4.J 4.J.228.228; 4.J.228.229; 4.J.228.230; 4.J.228.231; 4.J.228.236; 4.J.228.237;
4.J.228.238; 4.J.228.239; 4.J.228.154; 4.J.228.157; 4.J.228.166; 4.J.228.169;
4.J.228.172; 4.J.228.175; 4.J.228.240; 4.J.228.244; 4.J.229.228; 4.J.229.229;
4.J.229.230; 4.J.229.231; 4.J.229.236; 4.J.229.237; 4.J.229.238; 4.J.229.239;
4.J.229.154; 4.J.229.157; 4.J.229.166; 4.J.229.169; 4.J.229.172; 4.J.229.175;
4.J.229.240; 4.J.229.244; 4.J.230.228; 4.J.230.229; 4.J.230.230; 4.J.230.231;
4.J.230.236; 4.J.230.237; 4.J.230.238; 4.J.230.239; 4.J.230.154; 4.J.230.157;
4.J.230.166; 4.J.230.169; 4.J.230.172; 4.J.230.175; 4.J.230.240; 4.J.230.244;
4.J.231.228; 4.J.231.229; 4.J.231.230; 4.J.231.231; 4.J.231.236; 4.J.231.237;
4.J.231.238; 4.J.231.239; 4.J.231.154; 4.J.231.157; 4.J.231.166; 4.J.231.169;
4.J.231.172; 4.J.231.175; 4.J.231.240; 4.J.231.244; 4.J.236.228; 4.J.236.229;
4.J.236.230; 4.J.236.231; 4.J.236.236; 4.J.236.237; 4.J.236.238; 4.J.236.239;
4.J.236.154; 4.J.236.157; 4.J.236.166; 4.J.236.169; 4.J.236.172; 4.J.236.175;

TABLE 100-continued

4.J.236.240; 4.J.236.244; 4.J.237.228; 4.J.237.229; 4.J.237.230; 4.J.237.231;
4.J.237.236; 4.J.237.237; 4.J.237.238; 4.J.237.239; 4.J.237.154; 4.J.237.157;
4.J.237.166; 4.J.237.169; 4.J.237.172; 4.J.237.175; 4.J.237.240; 4.J.237.244;
4.J.238.228; 4.J.238.229; 4.J.238.230; 4.J.238.231; 4.J.238.236; 4.J.238.237;
4.J.238.238; 4.J.238.239; 4.J.238.154; 4.J.238.157; 4.J.238.166; 4.J.238.169;
4.J.238.172; 4.J.238.175; 4.J.238.240; 4.J.238.244; 4.J.239.228; 4.J.239.229;
4.J.239.230; 4.J.239.231; 4.J.239.236; 4.J.239.237; 4.J.239.238; 4.J.239.239;
4.J.239.154; 4.J.239.157; 4.J.239.166; 4.J.239.169; 4.J.239.172; 4.J.239.175;
4.J.239.240; 4.J.239.244; 4.J.154.228; 4.J.154.229; 4.J.154.230; 4.J.154.231;
4.J.154.236; 4.J.154.237; 4.J.154.238; 4.J.154.239; 4.J.154.154; 4.J.154.157;
4.J.154.166; 4.J.154.169; 4.J.154.172; 4.J.154.175; 4.J.154.240; 4.J.154.244;
4.J.157.228; 4.J.157.229; 4.J.157.230; 4.J.157.231; 4.J.157.236; 4.J.157.237;
4.J.157.238; 4.J.157.239; 4.J.157.154; 4.J.157.157; 4.J.157.166; 4.J.157.169;
4.J.157.172; 4.J.157.175; 4.J.157.240; 4.J.157.244; 4.J.166.228; 4.J.166.229;
4.J.166.230; 4.J.166.231; 4.J.166.236; 4.J.166.237; 4.J.166.238; 4.J.166.239;
4.J.166.154; 4.J.166.157; 4.J.166.166; 4.J.166.169; 4.J.166.172; 4.J.166.175;
4.J.166.240; 4.J.166.244; 4.J.169.228; 4.J.169.229; 4.J.169.230; 4.J.169.231;
4.J.169.236; 4.J.169.237; 4.J.169.238; 4.J.169.239; 4.J.169.154; 4.J.169.157;
4.J.169.166; 4.J.169.169; 4.J.169.172; 4.J.169.175; 4.J.169.240; 4.J.169.244;
4.J.172.228; 4.J.172.229; 4.J.172.230; 4.J.172.231; 4.J.172.236; 4.J.172.237;
4.J.172.238; 4.J.172.239; 4.J.172.154; 4.J.172.157; 4.J.172.166; 4.J.172.169;
4.J.172.172; 4.J.172.175; 4.J.172.240; 4.J.172.244; 4.J.175.228; 4.J.175.229;
4.J.175.230; 4.J.175.231; 4.J.175.236; 4.J.175.237; 4.J.175.238; 4.J.175.239;
4.J.175.154; 4.J.175.157; 4.J.175.166; 4.J.175.169; 4.J.175.172; 4.J.175.175;
4.J.175.240; 4.J.175.244; 4.J.240.228; 4.J.240.229; 4.J.240.230; 4.J.240.231;
4.J.240.236; 4.J.240.237; 4.J.240.238; 4.J.240.239; 4.J.240.154; 4.J.240.157;
4.J.240.166; 4.J.240.169; 4.J.240.172; 4.J.240.175; 4.J.240.240; 4.J.240.244;
4.J.244.228; 4.J.244.229; 4.J.244.230; 4.J.244.231; 4.J.244.236; 4.J.244.237;
4.J.244.238; 4.J.244.239; 4.J.244.154; 4.J.244.157; 4.J.244.166; 4.J.244.169;
4.J.244.172; 4.J.244.175; 4.J.244.240; 4.J.244.244;

Prodrugs of 4.L

4.L.228.228; 4.L.228.229; 4.L.228.230; 4.L.228.231; 4.L.228.236;
4.L.228.237; 4.L.228.238; 4.L.228.239; 4.L.228.154; 4.L.228.157; 4.L.228.166;
4.L.228.169; 4.L.228.172; 4.L.228.175; 4.L.228.240; 4.L.228.244; 4.L.229.228;
4.L.229.229; 4.L.229.230; 4.L.229.231; 4.L.229.236; 4.L.229.237; 4.L.229.238;
4.L.229.239; 4.L.229.154; 4.L.229.157; 4.L.229.166; 4.L.229.169; 4.L.229.172;
4.L.229.175; 4.L.229.240; 4.L.229.244; 4.L.230.228; 4.L.230.229; 4.L.230.230;
4.L.230.231; 4.L.230.236; 4.L.230.237; 4.L.230.238; 4.L.230.239; 4.L.230.154;
4.L.230.157; 4.L.230.166; 4.L.230.169; 4.L.230.172; 4.L.230.175; 4.L.230.240;
4.L.230.244; 4.L.231.228; 4.L.231.229; 4.L.231.230; 4.L.231.231; 4.L.231.236;
4.L.231.237; 4.L.231.238; 4.L.231.239; 4.L.231.154; 4.L.231.157; 4.L.231.166;
4.L.231.169; 4.L.231.172; 4.L.231.175; 4.L.231.240; 4.L.231.244; 4.L.236.228;
4.L.236.229; 4.L.236.230; 4.L.236.231; 4.L.236.236; 4.L.236.237; 4.L.236.238;
4.L.236.239; 4.L.236.154; 4.L.236.157; 4.L.236.166; 4.L.236.169; 4.L.236.172;
4.L.236.175; 4.L.236.240; 4.L.236.244; 4.L.237.228; 4.L.237.229; 4.L.237.230;
4.L.237.231; 4.L.237.236; 4.L.237.237; 4.L.237.238; 4.L.237.239; 4.L.237.154;
4.L.237.157; 4.L.237.166; 4.L.237.169; 4.L.237.172; 4.L.237.175; 4.L.237.240;
4.L.237.244; 4.L.238.228; 4.L.238.229; 4.L.238.230; 4.L.238.231; 4.L.238.236;
4.L.238.237; 4.L.238.238; 4.L.238.239; 4.L.238.154; 4.L.238.157; 4.L.238.166;
4.L.238.169; 4.L.238.172; 4.L.238.175; 4.L.238.240; 4.L.238.244; 4.L.239.228;
4.L.239.229; 4.L.239.230; 4.L.239.231; 4.L.239.236; 4.L.239.237; 4.L.239.238;
4.L.239.239; 4.L.239.154; 4.L.239.157; 4.L.239.166; 4.L.239.169; 4.L.239.172;
4.L.239.175; 4.L.239.240; 4.L.239.244; 4.L.154.228; 4.L.154.229; 4.L.154.230;
4.L.154.231; 4.L.154.236; 4.L.154.237; 4.L.154.238; 4.L.154.239; 4.L.154.154;
4.L.154.157; 4.L.154.166; 4.L.154.169; 4.L.154.172; 4.L.154.175; 4.L.154.240;
4.L.154.244; 4.L.157.228; 4.L.157.229; 4.L.157.230; 4.L.157.231; 4.L.157.236;
4.L.157.237; 4.L.157.238; 4.L.157.239; 4.L.157.154; 4.L.157.157; 4.L.157.166;
4.L.157.169; 4.L.157.172; 4.L.157.175; 4.L.157.240; 4.L.157.244; 4.L.166.228;
4.L.166.229; 4.L.166.230; 4.L.166.231; 4.L.166.236; 4.L.166.237; 4.L.166.238;
4.L.166.239; 4.L.166.154; 4.L.166.157; 4.L.166.166; 4.L.166.169; 4.L.166.172;
4.L.166.175; 4.L.166.240; 4.L.166.244; 4.L.169.228; 4.L.169.229; 4.L.169.230;
4.L.169.231; 4.L.169.236; 4.L.169.237; 4.L.169.238; 4.L.169.239; 4.L.169.154;
4.L.169.157; 4.L.169.166; 4.L.169.169; 4.L.169.172; 4.L.169.175; 4.L.169.240;
4.L.169.244; 4.L.172.228; 4.L.172.229; 4.L.172.230; 4.L.172.231; 4.L.172.236;
4.L.172.237; 4.L.172.238; 4.L.172.239; 4.L.172.154; 4.L.172.157; 4.L.172.166;
4.L.172.169; 4.L.172.172; 4.L.172.175; 4.L.172.240; 4.L.172.244; 4.L.175.228;
4.L.175.229; 4.L.175.230; 4.L.175.231; 4.L.175.236; 4.L.175.237; 4.L.175.238;
4.L.175.239; 4.L.175.154; 4.L.175.157; 4.L.175.166; 4.L.175.169; 4.L.175.172;
4.L.175.175; 4.L.175.240; 4.L.175.244; 4.L.240.228; 4.L.240.229; 4.L.240.230;
4.L.240.231; 4.L.240.236; 4.L.240.237; 4.L.240.238; 4.L.240.239; 4.L.240.154;
4.L.240.157; 4.L.240.166; 4.L.240.169; 4.L.240.172; 4.L.240.175; 4.L.240.240;
4.L.240.244; 4.L.244.228; 4.L.244.229; 4.L.244.230; 4.L.244.231; 4.L.244.236;
4.L.244.237; 4.L.244.238; 4.L.244.239; 4.L.244.154; 4.L.244.157; 4.L.244.166;
4.L.244.169; 4.L.244.172; 4.L.244.175; 4.L.244.240; 4.L.244.244;

Prodrugs of 4.O

4.O.228.228; 4.O.228.229; 4.O.228.230; 4.O.228.231; 4.O.228.236;
4.O.228.237; 4.O.228.238; 4.O.228.239; 4.O.228.154; 4.O.228.157;

TABLE 100-continued

4.O.228.166; 4.O.228.169; 4.O.228.172; 4.O.228.175; 4.O.228.240;
4.O.228.244; 4.O.229.228; 4.O.229.229; 4.O.229.230; 4.O.229.231;
4.O.229.236; 4.O.229.237; 4.O.229.238; 4.O.229.239; 4.O.229.154;
4.O.229.157; 4.O.229.166; 4.O.229.169; 4.O.229.172; 4.O.229.175;
4.O.229.240; 4.O.229.244; 4.O.230.228; 4.O.230.229; 4.O.230.230;
4.O.230.231; 4.O.230.236; 4.O.230.237; 4.O.230.238; 4.O.230.239;
4.O.230.154; 4.O.230.157; 4.O.230.166; 4.O.230.169; 4.O.230.172;
4.O.230.175; 4.O.230.240; 4.O.230.244; 4.O.231.228; 4.O.231.229;
4.O.231.230; 4.O.231.231; 4.O.231.236; 4.O.231.237; 4.O.231.238;
4.O.231.239; 4.O.231.154; 4.O.231.157; 4.O.231.166; 4.O.231.169;
4.O.231.172; 4.O.231.175; 4.O.231.240; 4.O.231.244; 4.O.236.228;
4.O.236.229; 4.O.236.230; 4.O.236.231; 4.O.236.236; 4.O.236.237;
4.O.236.238; 4.O.236.239; 4.O.236.154; 4.O.236.157; 4.O.236.166;
4.O.236.169; 4.O.236.172; 4.O.236.175; 4.O.236.240; 4.O.236.244;
4.O.237.228; 4.O.237.229; 4.O.237.230; 4.O.237.231; 4.O.237.236;
4.O.237.237; 4.O.237.238; 4.O.237.239; 4.O.237.154; 4.O.237.157;
4.O.237.166; 4.O.237.169; 4.O.237.172; 4.O.237.175; 4.O.237.240;
4.O.237.244; 4.O.238.228; 4.O.238.229; 4.O.238.230; 4.O.238.231;
4.O.238.236; 4.O.238.237; 4.O.238.238; 4.O.238.239; 4.O.238.154;
4.O.238.157; 4.O.238.166; 4.O.238.169; 4.O.238.172; 4.O.238.175;
4.O.238.240; 4.O.238.244; 4.O.239.228; 4.O.239.229; 4.O.239.230;
4.O.239.231; 4.O.239.236; 4.O.239.237; 4.O.239.238; 4.O.239.239;
4.O.239.154; 4.O.239.157; 4.O.239.166; 4.O.239.169; 4.O.239.172;
4.O.239.175; 4.O.239.240; 4.O.239.244; 4.O.154.228; 4.O.154.229;
4.O.154.230; 4.O.154.231; 4.O.154.236; 4.O.154.237; 4.O.154.238;
4.O.154.239; 4.O.154.154; 4.O.154.157; 4.O.154.166; 4.O.154.169;
4.O.154.172; 4.O.154.175; 4.O.154.240; 4.O.154.244; 4.O.157.228;
4.O.157.229; 4.O.157.230; 4.O.157.231; 4.O.157.236; 4.O.157.237;
4.O.157.238; 4.O.157.239; 4.O.157.154; 4.O.157.157; 4.O.157.166;
4.O.157.169; 4.O.157.172; 4.O.157.175; 4.O.157.240; 4.O.157.244;
4.O.166.228; 4.O.166.229; 4.O.166.230; 4.O.166.231; 4.O.166.236;
4.O.166.237; 4.O.166.238; 4.O.166.239; 4.O.166.154; 4.O.166.157;
4.O.166.166; 4.O.166.169; 4.O.166.172; 4.O.166.175; 4.O.166.240;
4.O.166.244; 4.O.169.228; 4.O.169.229; 4.O.169.230; 4.O.169.231;
4.O.169.236; 4.O.169.237; 4.O.169.238; 4.O.169.239; 4.O.169.154;
4.O.169.157; 4.O.169.166; 4.O.169.169; 4.O.169.172; 4.O.169.175;
4.O.169.240; 4.O.169.244; 4.O.172.228; 4.O.172.229; 4.O.172.230;
4.O.172.231; 4.O.172.236; 4.O.172.237; 4.O.172.238; 4.O.172.239;
4.O.172.154; 4.O.172.157; 4.O.172.166; 4.O.172.169; 4.O.172.172;
4.O.172.175; 4.O.172.240; 4.O.172.244; 4.O.175.228; 4.O.175.229;
4.O.175.230; 4.O.175.231; 4.O.175.236; 4.O.175.237; 4.O.175.238;
4.O.175.239; 4.O.175.154; 4.O.175.157; 4.O.175.166; 4.O.175.169;
4.O.175.172; 4.O.175.175; 4.O.175.240; 4.O.175.244; 4.O.240.228;
4.O.240.229; 4.O.240.230; 4.O.240.231; 4.O.240.236; 4.O.240.237;
4.O.240.238; 4.O.240.239; 4.O.240.154; 4.O.240.157; 4.O.240.166;
4.O.240.169; 4.O.240.172; 4.O.240.175; 4.O.240.240; 4.O.240.244;
4.O.244.228; 4.O.244.229; 4.O.244.230; 4.O.244.231; 4.O.244.236;
4.O.244.237; 4.O.244.238; 4.O.244.239; 4.O.244.154; 4.O.244.157;
4.O.244.166; 4.O.244.169; 4.O.244.172; 4.O.244.175; 4.O.244.240; 4.O.244.244;

Prodrugs of 4.P

4.P.228.228; 4.P.228.229; 4.P.228.230; 4.P.228.231; 4.P.228.236;
4.P.228.237; 4.P.228.238; 4.P.228.239; 4.P.228.154; 4.P.228.157; 4.P.228.166;
4.P.228.169; 4.P.228.172; 4.P.228.175; 4.P.228.240; 4.P.228.244; 4.P.229.228;
4.P.229.229; 4.P.229.230; 4.P.229.231; 4.P.229.236; 4.P.229.237; 4.P.229.238;
4.P.229.239; 4.P.229.154; 4.P.229.157; 4.P.229.166; 4.P.229.169; 4.P.229.172;
4.P.229.175; 4.P.229.240; 4.P.229.244; 4.P.230.228; 4.P.230.229; 4.P.230.230;
4.P.230.231; 4.P.230.236; 4.P.230.237; 4.P.230.238; 4.P.230.239; 4.P.230.154;
4.P.230.157; 4.P.230.166; 4.P.230.169; 4.P.230.172; 4.P.230.175; 4.P.230.240;
4.P.230.244; 4.P.231.228; 4.P.231.229; 4.P.231.230; 4.P.231.231; 4.P.231.236;
4.P.231.237; 4.P.231.238; 4.P.231.239; 4.P.231.154; 4.P.231.157; 4.P.231.166;
4.P.231.169; 4.P.231.172; 4.P.231.175; 4.P.231.240; 4.P.231.244; 4.P.236.228;
4.P.236.229; 4.P.236.230; 4.P.236.231; 4.P.236.236; 4.P.236.237; 4.P.236.238;
4.P.236.239; 4.P.236.154; 4.P.236.157; 4.P.236.166; 4.P.236.169; 4.P.236.172;
4.P.236.175; 4.P.236.240; 4.P.236.244; 4.P.237.228; 4.P.237.229; 4.P.237.230;
4.P.237.231; 4.P.237.236; 4.P.237.237; 4.P.237.238; 4.P.237.239; 4.P.237.154;
4.P.237.157; 4.P.237.166; 4.P.237.169; 4.P.237.172; 4.P.237.175; 4.P.237.240;
4.P.237.244; 4.P.238.228; 4.P.238.229; 4.P.238.230; 4.P.238.231; 4.P.238.236;
4.P.238.237; 4.P.238.238; 4.P.238.239; 4.P.238.154; 4.P.238.157; 4.P.238.166;
4.P.238.169; 4.P.238.172; 4.P.238.175; 4.P.238.240; 4.P.238.244; 4.P.239.228;
4.P.239.229; 4.P.239.230; 4.P.239.231; 4.P.239.236; 4.P.239.237; 4.P.239.238;
4.P.239.239; 4.P.239.154; 4.P.239.157; 4.P.239.166; 4.P.239.169; 4.P.239.172;
4.P.239.175; 4.P.239.240; 4.P.239.244; 4.P.154.228; 4.P.154.229; 4.P.154.230;
4.P.154.231; 4.P.154.236; 4.P.154.237; 4.P.154.238; 4.P.154.239; 4.P.154.154;
4.P.154.157; 4.P.154.166; 4.P.154.169; 4.P.154.172; 4.P.154.175; 4.P.154.240;
4.P.154.244; 4.P.157.228; 4.P.157.229; 4.P.157.230; 4.P.157.231; 4.P.157.236;
4.P.157.237; 4.P.157.238; 4.P.157.239; 4.P.157.154; 4.P.157.157; 4.P.157.166;
4.P.157.169; 4.P.157.172; 4.P.157.175; 4.P.157.240; 4.P.157.244; 4.P.166.228;
4.P.166.229; 4.P.166.230; 4.P.166.231; 4.P.166.236; 4.P.166.237; 4.P.166.238;

TABLE 100-continued

4.P.166.239; 4.P.166.154; 4.P.166.157; 4.P.166.166; 4.P.166.169; 4.P.166.172;
4.P.166.175; 4.P.166.240; 4.P.166.244; 4.P.169.228; 4.P.169.229; 4.P.169.230;
4.P.169.231; 4.P.169.236; 4.P.169.237; 4.P.169.238; 4.P.169.239; 4.P.169.154;
4.P.169.157; 4.P.169.166; 4.P.169.169; 4.P.169.172; 4.P.169.175; 4.P.169.240;
4.P.169.244; 4.P.172.228; 4.P.172.229; 4.P.172.230; 4.P.172.231; 4.P.172.236;
4.P.172.237; 4.P.172.238; 4.P.172.239; 4.P.172.154; 4.P.172.157; 4.P.172.166;
4.P.172.169; 4.P.172.172; 4.P.172.175; 4.P.172.240; 4.P.172.244; 4.P.175.228;
4.P.175.229; 4.P.175.230; 4.P.175.231; 4.P.175.236; 4.P.175.237; 4.P.175.238;
4.P.175.239; 4.P.175.154; 4.P.175.157; 4.P.175.166; 4.P.175.169; 4.P.175.172;
4.P.175.175; 4.P.175.240; 4.P.175.244; 4.P.240.228; 4.P.240.229; 4.P.240.230;
4.P.240.231; 4.P.240.236; 4.P.240.237; 4.P.240.238; 4.P.240.239; 4.P.240.154;
4.P.240.157; 4.P.240.166; 4.P.240.169; 4.P.240.172; 4.P.240.175; 4.P.240.240;
4.P.240.244; 4.P.244.228; 4.P.244.229; 4.P.244.230; 4.P.244.231; 4.P.244.236;
4.P.244.237; 4.P.244.238; 4.P.244.239; 4.P.244.154; 4.P.244.157; 4.P.244.166;
4.P.244.169; 4.P.244.172; 4.P.244.175; 4.P.244.240; 4.P.244.244;
Prodrugs of 4.U 4.U.228.228; 4.U.228.229; 4.U.228.230; 4.U.228.231; 4.U.228.236;
4.U.228.237; 4.U.228.238; 4.U.228.239; 4.U.228.154; 4.U.228.157;
4.U.228.166; 4.U.228.169; 4.U.228.172; 4.U.228.175; 4.U.228.240;
4.U.228.244; 4.U.229.228; 4.U.229.229; 4.U.229.230; 4.U.229.231;
4.U.229.236; 4.U.229.237; 4.U.229.238; 4.U.229.239; 4.U.229.154;
4.U.229.157; 4.U.229.166; 4.U.229.169; 4.U.229.172; 4.U.229.175;
4.U.229.240; 4.U.229.244; 4.U.230.228; 4.U.230.229; 4.U.230.230;
4.U.230.231; 4.U.230.236; 4.U.230.237; 4.U.230.238; 4.U.230.239;
4.U.230.154; 4.U.230.157; 4.U.230.166; 4.U.230.169; 4.U.230.172;
4.U.230.175; 4.U.230.240; 4.U.230.244; 4.U.231.228; 4.U.231.229;
4.U.231.230; 4.U.231.231; 4.U.231.236; 4.U.231.237; 4.U.231.238;
4.U.231.239; 4.U.231.154; 4.U.231.157; 4.U.231.166; 4.U.231.169;
4.U.231.172; 4.U.231.175; 4.U.231.240; 4.U.231.244; 4.U.236.228;
4.U.236.229; 4.U.236.230; 4.U.236.231; 4.U.236.236; 4.U.236.237;
4.U.236.238; 4.U.236.239; 4.U.236.154; 4.U.236.157; 4.U.236.166;
4.U.236.169; 4.U.236.172; 4.U.236.175; 4.U.236.240; 4.U.236.244;
4.U.237.228; 4.U.237.229; 4.U.237.230; 4.U.237.231; 4.U.237.236;
4.U.237.237; 4.U.237.238; 4.U.237.239; 4.U.237.154; 4.U.237.157;
4.U.237.166; 4.U.237.169; 4.U.237.172; 4.U.237.175; 4.U.237.240;
4.U.237.244; 4.U.238.228; 4.U.238.229; 4.U.238.230; 4.U.238.231;
4.U.238.236; 4.U.238.237; 4.U.238.238; 4.U.238.239; 4.U.238.154;
4.U.238.157; 4.U.238.166; 4.U.238.169; 4.U.238.172; 4.U.238.175;
4.U.238.240; 4.U.238.244; 4.U.239.228; 4.U.239.229; 4.U.239.230;
4.U.239.231; 4.U.239.236; 4.U.239.237; 4.U.239.238; 4.U.239.239;
4.U.239.154; 4.U.239.157; 4.U.239.166; 4.U.239.169; 4.U.239.172;
4.U.239.175; 4.U.239.240; 4.U.239.244; 4.U.154.228; 4.U.154.229;
4.U.154.230; 4.U.154.231; 4.U.154.236; 4.U.154.237; 4.U.154.238;
4.U.154.239; 4.U.154.154; 4.U.154.157; 4.U.154.166; 4.U.154.169;
4.U.154.172; 4.U.154.175; 4.U.154.240; 4.U.154.244; 4.U.157.228;
4.U.157.229; 4.U.157.230; 4.U.157.231; 4.U.157.236; 4.U.157.237;
4.U.157.238; 4.U.157.239; 4.U.157.154; 4.U.157.157; 4.U.157.166;
4.U.157.169; 4.U.157.172; 4.U.157.175; 4.U.157.240; 4.U.157.244;
4.U.166.228; 4.U.166.229; 4.U.166.230; 4.U.166.231; 4.U.166.236;
4.U.166.237; 4.U.166.238; 4.U.166.239; 4.U.166.154; 4.U.166.157;
4.U.166.166; 4.U.166.169; 4.U.166.172; 4.U.166.175; 4.U.166.240;
4.U.166.244; 4.U.169.228; 4.U.169.229; 4.U.169.230; 4.U.169.231;
4.U.169.236; 4.U.169.237; 4.U.169.238; 4.U.169.239; 4.U.169.154;
4.U.169.157; 4.U.169.166; 4.U.169.169; 4.U.169.172; 4.U.169.175;
4.U.169.240; 4.U.169.244; 4.U.172.228; 4.U.172.229; 4.U.172.230;
4.U.172.231; 4.U.172.236; 4.U.172.237; 4.U.172.238; 4.U.172.239;
4.U.172.154; 4.U.172.157; 4.U.172.166; 4.U.172.169; 4.U.172.172;
4.U.172.175; 4.U.172.240; 4.U.172.244; 4.U.175.228; 4.U.175.229;
4.U.175.230; 4.U.175.231; 4.U.175.236; 4.U.175.237; 4.U.175.238;
4.U.175.239; 4.U.175.154; 4.U.175.157; 4.U.175.166; 4.U.175.169;
4.U.175.172; 4.U.175.175; 4.U.175.240; 4.U.175.244; 4.U.240.228;
4.U.240.229; 4.U.240.230; 4.U.240.231; 4.U.240.236; 4.U.240.237;
4.U.240.238; 4.U.240.239; 4.U.240.154; 4.U.240.157; 4.U.240.166;
4.U.240.169; 4.U.240.172; 4.U.240.175; 4.U.240.240; 4.U.240.244;
4.U.244.228; 4.U.244.229; 4.U.244.230; 4.U.244.231; 4.U.244.236;
4.U.244.237; 4.U.244.238; 4.U.244.239; 4.U.244.154; 4.U.244.157;
4.U.244.166; 4.U.244.169; 4.U.244.172; 4.U.244.175; 4.U.244.240; 4.U.244.244;
Prodrugs of 4.W 4.W.228.228; 4.W.228.229; 4.W.228.230; 4.W.228.231; 4.W.228.236;
4.W.228.237; 4.W.228.238; 4.W.228.239; 4.W.228.154; 4.W.228.157;
4.W.228.166; 4.W.228.169; 4.W.228.172; 4.W.228.175; 4.W.228.240;
4.W.228.244; 4.W.229.228; 4.W.229.229; 4.W.229.230; 4.W.229.231;
4.W.229.236; 4.W.229.237; 4.W.229.238; 4.W.229.239; 4.W.229.154;
4.W.229.157; 4.W.229.166; 4.W.229.169; 4.W.229.172; 4.W.229.175;
4.W.229.240; 4.W.229.244; 4.W.230.228; 4.W.230.229; 4.W.230.230;
4.W.230.231; 4.W.230.236; 4.W.230.237; 4.W.230.238; 4.W.230.239;
4.W.230.154; 4.W.230.157; 4.W.230.166; 4.W.230.169; 4.W.230.172;

TABLE 100-continued

4.W.230.175; 4.W.230.240; 4.W.230.244; 4.W.231.228; 4.W.231.229;
4.W.231.230; 4.W.231.231; 4.W.231.236; 4.W.231.237; 4.W.231.238;
4.W.231.239; 4.W.231.154; 4.W.231.157; 4.W.231.166; 4.W.231.169;
4.W.231.172; 4.W.231.175; 4.W.231.240; 4.W.231.244; 4.W.236.228;
4.W.236.229; 4.W.236.230; 4.W.236.231; 4.W.236.236; 4.W.236.237;
4.W.236.238; 4.W.236.239; 4.W.236.154; 4.W.236.157; 4.W.236.166;
4.W.236.169; 4.W.236.172; 4.W.236.175; 4.W.236.240; 4.W.236.244;
4.W.237.228; 4.W.237.229; 4.W.237.230; 4.W.237.231; 4.W.237.236;
4.W.237.237; 4.W.237.238; 4.W.237.239; 4.W.237.154; 4.W.237.157;
4.W.237.166; 4.W.237.169; 4.W.237.172; 4.W.237.175; 4.W.237.240;
4.W.237.244; 4.W.238.228; 4.W.238.229; 4.W.238.230; 4.W.238.231;
4.W.238.236; 4.W.238.237; 4.W.238.238; 4.W.238.239; 4.W.238.154;
4.W.238.157; 4.W.238.166; 4.W.238.169; 4.W.238.172; 4.W.238.175;
4.W.238.240; 4.W.238.244; 4.W.239.228; 4.W.239.229; 4.W.239.230;
4.W.239.231; 4.W.239.236; 4.W.239.237; 4.W.239.238; 4.W.239.239;
4.W.239.154; 4.W.239.157; 4.W.239.166; 4.W.239.169; 4.W.239.172;
4.W.239.175; 4.W.239.240; 4.W.239.244; 4.W.154.228; 4.W.154.229;
4.W.154.230; 4.W.154.231; 4.W.154.236; 4.W.154.237; 4.W.154.238;
4.W.154.239; 4.W.154.154; 4.W.154.157; 4.W.154.166; 4.W.154.169;
4.W.154.172; 4.W.154.175; 4.W.154.240; 4.W.154.244; 4.W.157.228;
4.W.157.229; 4.W.157.230; 4.W.157.231; 4.W.157.236; 4.W.157.237;
4.W.157.238; 4.W.157.239; 4.W.157.154; 4.W.157.157; 4.W.157.166;
4.W.157.169; 4.W.157.172; 4.W.157.175; 4.W.157.240; 4.W.157.244;
4.W.166.228; 4.W.166.229; 4.W.166.230; 4.W.166.231; 4.W.166.236;
4.W.166.237; 4.W.166.238; 4.W.166.239; 4.W.166.154; 4.W.166.157;
4.W.166.166; 4.W.166.169; 4.W.166.172; 4.W.166.175; 4.W.166.240;
4.W.166.244; 4.W.169.228; 4.W.169.229; 4.W.169.230; 4.W.169.231;
4.W.169.236; 4.W.169.237; 4.W.169.238; 4.W.169.239; 4.W.169.154;
4.W.169.157; 4.W.169.166; 4.W.169.169; 4.W.169.172; 4.W.169.175;
4.W.169.240; 4.W.169.244; 4.W.172.228; 4.W.172.229; 4.W.172.230;
4.W.172.231; 4.W.172.236; 4.W.172.237; 4.W.172.238; 4.W.172.239;
4.W.172.154; 4.W.172.157; 4.W.172.166; 4.W.172.169; 4.W.172.172;
4.W.172.175; 4.W.172.240; 4.W.172.244; 4.W.175.228; 4.W.175.229;
4.W.175.230; 4.W.175.231; 4.W.175.236; 4.W.175.237; 4.W.175.238;
4.W.175.239; 4.W.175.154; 4.W.175.157; 4.W.175.166; 4.W.175.169;
4.W.175.172; 4.W.175.175; 4.W.175.240; 4.W.175.244; 4.W.240.228;
4.W.240.229; 4.W.240.230; 4.W.240.231; 4.W.240.236; 4.W.240.237;
4.W.240.238; 4.W.240.239; 4.W.240.154; 4.W.240.157; 4.W.240.166;
4.W.240.169; 4.W.240.172; 4.W.240.175; 4.W.240.240; 4.W.240.244;
4.W.244.228; 4.W.244.229; 4.W.244.230; 4.W.244.231; 4.W.244.236;
4.W.244.237; 4.W.244.238; 4.W.244.239; 4.W.244.154; 4.W.244.157;
4.W.244.166; 4.W.244.169; 4.W.244.172; 4.W.244.175; 4.W.244.240; 4.W.244.244;
Prodrugs of 4.Y 4.Y.228.228; 4.Y.228.229; 4.Y.228.230; 4.Y.228.231; 4.Y.228.236;
4.Y.228.237; 4.Y.228.238; 4.Y.228.239; 4.Y.228.154; 4.Y.228.157; 4.Y.228.166;
4.Y.228.169; 4.Y.228.172; 4.Y.228.175; 4.Y.228.240; 4.Y.228.244; 4.Y.229.228;
4.Y.229.229; 4.Y.229.230; 4.Y.229.231; 4.Y.229.236; 4.Y.229.237; 4.Y.229.238;
4.Y.229.239; 4.Y.229.154; 4.Y.229.157; 4.Y.229.166; 4.Y.229.169; 4.Y.229.172;
4.Y.229.175; 4.Y.229.240; 4.Y.229.244; 4.Y.230.228; 4.Y.230.229; 4.Y.230.230;
4.Y.230.231; 4.Y.230.236; 4.Y.230.237; 4.Y.230.238; 4.Y.230.239; 4.Y.230.154;
4.Y.230.157; 4.Y.230.166; 4.Y.230.169; 4.Y.230.172; 4.Y.230.175; 4.Y.230.240;
4.Y.230.244; 4.Y.231.228; 4.Y.231.229; 4.Y.231.230; 4.Y.231.231; 4.Y.231.236;
4.Y.231.237; 4.Y.231.238; 4.Y.231.239; 4.Y.231.154; 4.Y.231.157; 4.Y.231.166;
4.Y.231.169; 4.Y.231.172; 4.Y.231.175; 4.Y.231.240; 4.Y.231.244; 4.Y.236.228;
4.Y.236.229; 4.Y.236.230; 4.Y.236.231; 4.Y.236.236; 4.Y.236.237; 4.Y.236.238;
4.Y.236.239; 4.Y.236.154; 4.Y.236.157; 4.Y.236.166; 4.Y.236.169; 4.Y.236.172;
4.Y.236.175; 4.Y.236.240; 4.Y.236.244; 4.Y.237.228; 4.Y.237.229; 4.Y.237.230;
4.Y.237.231; 4.Y.237.236; 4.Y.237.237; 4.Y.237.238; 4.Y.237.239; 4.Y.237.154;
4.Y.237.157; 4.Y.237.166; 4.Y.237.169; 4.Y.237.172; 4.Y.237.175; 4.Y.237.240;
4.Y.237.244; 4.Y.238.228; 4.Y.238.229; 4.Y.238.230; 4.Y.238.231; 4.Y.238.236;
4.Y.238.237; 4.Y.238.238; 4.Y.238.239; 4.Y.238.154; 4.Y.238.157; 4.Y.238.166;
4.Y.238.169; 4.Y.238.172; 4.Y.238.175; 4.Y.238.240; 4.Y.238.244; 4.Y.239.228;
4.Y.239.229; 4.Y.239.230; 4.Y.239.231; 4.Y.239.236; 4.Y.239.237; 4.Y.239.238;
4.Y.239.239; 4.Y.239.154; 4.Y.239.157; 4.Y.239.166; 4.Y.239.169; 4.Y.239.172;
4.Y.239.175; 4.Y.239.240; 4.Y.239.244; 4.Y.154.228; 4.Y.154.229; 4.Y.154.230;
4.Y.154.231; 4.Y.154.236; 4.Y.154.237; 4.Y.154.238; 4.Y.154.239; 4.Y.154.154;
4.Y.154.157; 4.Y.154.166; 4.Y.154.169; 4.Y.154.172; 4.Y.154.175; 4.Y.154.240;
4.Y.154.244; 4.Y.157.228; 4.Y.157.229; 4.Y.157.230; 4.Y.157.231; 4.Y.157.236;
4.Y.157.237; 4.Y.157.238; 4.Y.157.239; 4.Y.157.154; 4.Y.157.157; 4.Y.157.166;
4.Y.157.169; 4.Y.157.172; 4.Y.157.175; 4.Y.157.240; 4.Y.157.244; 4.Y.166.228;
4.Y.166.229; 4.Y.166.230; 4.Y.166.231; 4.Y.166.236; 4.Y.166.237; 4.Y.166.238;
4.Y.166.239; 4.Y.166.154; 4.Y.166.157; 4.Y.166.166; 4.Y.166.169; 4.Y.166.172;
4.Y.166.175; 4.Y.166.240; 4.Y.166.244; 4.Y.169.228; 4.Y.169.229; 4.Y.169.230;
4.Y.169.231; 4.Y.169.236; 4.Y.169.237; 4.Y.169.238; 4.Y.169.239; 4.Y.169.154;
4.Y.169.157; 4.Y.169.166; 4.Y.169.169; 4.Y.169.172; 4.Y.169.175; 4.Y.169.240;
4.Y.169.244; 4.Y.172.228; 4.Y.172.229; 4.Y.172.230; 4.Y.172.231; 4.Y.172.236;
4.Y.172.237; 4.Y.172.238; 4.Y.172.239; 4.Y.172.154; 4.Y.172.157; 4.Y.172.166;
4.Y.172.169; 4.Y.172.172; 4.Y.172.175; 4.Y.172.240; 4.Y.172.244; 4.Y.175.228;

TABLE 100-continued

4.Y.175.229; 4.Y.175.230; 4.Y.175.231; 4.Y.175.236; 4.Y.175.237; 4.Y.175.238;
4.Y.175.239; 4.Y.175.154; 4.Y.175.157; 4.Y.175.166; 4.Y.175.169; 4.Y.175.172;
4.Y.175.175; 4.Y.175.240; 4.Y.175.244; 4.Y.240.228; 4.Y.240.229; 4.Y.240.230;
4.Y.240.231; 4.Y.240.236; 4.Y.240.237; 4.Y.240.238; 4.Y.240.239; 4.Y.240.154;
4.Y.240.157; 4.Y.240.166; 4.Y.240.169; 4.Y.240.172; 4.Y.240.175; 4.Y.240.240;
4.Y.240.244; 4.Y.244.228; 4.Y.244.229; 4.Y.244.230; 4.Y.244.231; 4.Y.244.236;
4.Y.244.237; 4.Y.244.238; 4.Y.244.239; 4.Y.244.154; 4.Y.244.157; 4.Y.244.166;
4.Y.244.169; 4.Y.244.172; 4.Y.244.175; 4.Y.244.240; 4.Y.244.244;
Prodrugs of 5.B 5.B.228.228; 5.B.228.229; 5.B.228.230; 5.B.228.231; 5.B.228.236;
5.B.228.237; 5.B.228.238; 5.B.228.239; 5.B.228.154; 5.B.228.157; 5.B.228.166;
5.B.228.169; 5.B.228.172; 5.B.228.175; 5.B.228.240; 5.B.228.244; 5.B.229.228;
5.B.229.229; 5.B.229.230; 5.B.229.231; 5.B.229.236; 5.B.229.237; 5.B.229.238;
5.B.229.239; 5.B.229.154; 5.B.229.157; 5.B.229.166; 5.B.229.169; 5.B.229.172;
5.B.229.175; 5.B.229.240; 5.B.229.244; 5.B.230.228; 5.B.230.229; 5.B.230.230;
5.B.230.231; 5.B.230.236; 5.B.230.237; 5.B.230.238; 5.B.230.239; 5.B.230.154;
5.B.230.157; 5.B.230.166; 5.B.230.169; 5.B.230.172; 5.B.230.175; 5.B.230.240;
5.B.230.244; 5.B.231.228; 5.B.231.229; 5.B.231.230; 5.B.231.231; 5.B.231.236;
5.B.231.237; 5.B.231.238; 5.B.231.239; 5.B.231.154; 5.B.231.157; 5.B.231.166;
5.B.231.169; 5.B.231.172; 5.B.231.175; 5.B.231.240; 5.B.231.244; 5.B.236.228;
5.B.236.229; 5.B.236.230; 5.B.236.231; 5.B.236.236; 5.B.236.237; 5.B.236.238;
5.B.236.239; 5.B.236.154; 5.B.236.157; 5.B.236.166; 5.B.236.169; 5.B.236.172;
5.B.236.175; 5.B.236.240; 5.B.236.244; 5.B.237.228; 5.B.237.229; 5.B.237.230;
5.B.237.231; 5.B.237.236; 5.B.237.237; 5.B.237.238; 5.B.237.239; 5.B.237.154;
5.B.237.157; 5.B.237.166; 5.B.237.169; 5.B.237.172; 5.B.237.175; 5.B.237.240;
5.B.237.244; 5.B.238.228; 5.B.238.229; 5.B.238.230; 5.B.238.231; 5.B.238.236;
5.B.238.237; 5.B.238.238; 5.B.238.239; 5.B.238.154; 5.B.238.157; 5.B.238.166;
5.B.238.169; 5.B.238.172; 5.B.238.175; 5.B.238.240; 5.B.238.244; 5.B.239.228;
5.B.239.229; 5.B.239.230; 5.B.239.231; 5.B.239.236; 5.B.239.237; 5.B.239.238;
5.B.239.239; 5.B.239.154; 5.B.239.157; 5.B.239.166; 5.B.239.169; 5.B.239.172;
5.B.239.175; 5.B.239.240; 5.B.239.244; 5.B.154.228; 5.B.154.229; 5.B.154.230;
5.B.154.231; 5.B.154.236; 5.B.154.237; 5.B.154.238; 5.B.154.239; 5.B.154.154;
5.B.154.157; 5.B.154.166; 5.B.154.169; 5.B.154.172; 5.B.154.175; 5.B.154.240;
5.B.154.244; 5.B.157.228; 5.B.157.229; 5.B.157.230; 5.B.157.231; 5.B.157.236;
5.B.157.237; 5.B.157.238; 5.B.157.239; 5.B.157.154; 5.B.157.157; 5.B.157.166;
5.B.157.169; 5.B.157.172; 5.B.157.175; 5.B.157.240; 5.B.157.244; 5.B.166.228;
5.B.166.229; 5.B.166.230; 5.B.166.231; 5.B.166.236; 5.B.166.237; 5.B.166.238;
5.B.166.239; 5.B.166.154; 5.B.166.157; 5.B.166.166; 5.B.166.169; 5.B.166.172;
5.B.166.175; 5.B.166.240; 5.B.166.244; 5.B.169.228; 5.B.169.229; 5.B.169.230;
5.B.169.231; 5.B.169.236; 5.B.169.237; 5.B.169.238; 5.B.169.239; 5.B.169.154;
5.B.169.157; 5.B.169.166; 5.B.169.169; 5.B.169.172; 5.B.169.175; 5.B.169.240;
5.B.169.244; 5.B.172.228; 5.B.172.229; 5.B.172.230; 5.B.172.231; 5.B.172.236;
5.B.172.237; 5.B.172.238; 5.B.172.239; 5.B.172.154; 5.B.172.157; 5.B.172.166;
5.B.172.169; 5.B.172.172; 5.B.172.175; 5.B.172.240; 5.B.172.244; 5.B.175.228;
5.B.175.229; 5.B.175.230; 5.B.175.231; 5.B.175.236; 5.B.175.237; 5.B.175.238;
5.B.175.239; 5.B.175.154; 5.B.175.157; 5.B.175.166; 5.B.175.169; 5.B.175.172;
5.B.175.175; 5.B.175.240; 5.B.175.244; 5.B.240.228; 5.B.240.229; 5.B.240.230;
5.B.240.231; 5.B.240.236; 5.B.240.237; 5.B.240.238; 5.B.240.239; 5.B.240.154;
5.B.240.157; 5.B.240.166; 5.B.240.169; 5.B.240.172; 5.B.240.175; 5.B.240.240;
5.B.240.244; 5.B.244.228; 5.B.244.229; 5.B.244.230; 5.B.244.231; 5.B.244.236;
5.B.244.237; 5.B.244.238; 5.B.244.239; 5.B.244.154; 5.B.244.157; 5.B.244.166;
5.B.244.169; 5.B.244.172; 5.B.244.175; 5.B.244.240; 5.B.244.244;
Prodrugs of 5.D 5.D.228.228; 5.D.228.229; 5.D.228.230; 5.D.228.231; 5.D.228.236;
5.D.228.237; 5.D.228.238; 5.D.228.239; 5.D.228.154; 5.D.228.157;
5.D.228.166; 5.D.228.169; 5.D.228.172; 5.D.228.175; 5.D.228.240;
5.D.228.244; 5.D.229.228; 5.D.229.229; 5.D.229.230; 5.D.229.231;
5.D.229.236; 5.D.229.237; 5.D.229.238; 5.D.229.239; 5.D.229.154;
5.D.229.157; 5.D.229.166; 5.D.229.169; 5.D.229.172; 5.D.229.175;
5.D.229.240; 5.D.229.244; 5.D.230.228; 5.D.230.229; 5.D.230.230;
5.D.230.231; 5.D.230.236; 5.D.230.237; 5.D.230.238; 5.D.230.239;
5.D.230.154; 5.D.230.157; 5.D.230.166; 5.D.230.169; 5.D.230.172;
5.D.230.175; 5.D.230.240; 5.D.230.244; 5.D.231.228; 5.D.231.229;
5.D.231.230; 5.D.231.231; 5.D.231.236; 5.D.231.237; 5.D.231.238;
5.D.231.239; 5.D.231.154; 5.D.231.157; 5.D.231.166; 5.D.231.169;
5.D.231.172; 5.D.231.175; 5.D.231.240; 5.D.231.244; 5.D.236.228;
5.D.236.229; 5.D.236.230; 5.D.236.231; 5.D.236.236; 5.D.236.237;
5.D.236.238; 5.D.236.239; 5.D.236.154; 5.D.236.157; 5.D.236.166;
5.D.236.169; 5.D.236.172; 5.D.236.175; 5.D.236.240; 5.D.236.244;
5.D.237.228; 5.D.237.229; 5.D.237.230; 5.D.237.231; 5.D.237.236;
5.D.237.237; 5.D.237.238; 5.D.237.239; 5.D.237.154; 5.D.237.157;
5.D.237.166; 5.D.237.169; 5.D.237.172; 5.D.237.175; 5.D.237.240;
5.D.237.244; 5.D.238.228; 5.D.238.229; 5.D.238.230; 5.D.238.231;
5.D.238.236; 5.D.238.237; 5.D.238.238; 5.D.238.239; 5.D.238.154;
5.D.238.157; 5.D.238.166; 5.D.238.169; 5.D.238.172; 5.D.238.175;
5.D.238.240; 5.D.238.244; 5.D.239.228; 5.D.239.229; 5.D.239.230;
5.D.239.231; 5.D.239.236; 5.D.239.237; 5.D.239.238; 5.D.239.239;

TABLE 100-continued

5.D.239.154; 5.D.239.157; 5.D.239.166; 5.D.239.169; 5.D.239.172;
5.D.239.175; 5.D.239.240; 5.D.239.244; 5.D.154.228; 5.D.154.229;
5.D.154.230; 5.D.154.231; 5.D.154.236; 5.D.154.237; 5.D.154.238;
5.D.154.239; 5.D.154.154; 5.D.154.157; 5.D.154.166; 5.D.154.169;
5.D.154.172; 5.D.154.175; 5.D.154.240; 5.D.154.244; 5.D.157.228;
5.D.157.229; 5.D.157.230; 5.D.157.231; 5.D.157.236; 5.D.157.237;
5.D.157.238; 5.D.157.239; 5.D.157.154; 5.D.157.157; 5.D.157.166;
5.D.157.169; 5.D.157.172; 5.D.157.175; 5.D.157.240; 5.D.157.244;
5.D.166.228; 5.D.166.229; 5.D.166.230; 5.D.166.231; 5.D.166.236;
5.D.166.237; 5.D.166.238; 5.D.166.239; 5.D.166.154; 5.D.166.157;
5.D.166.166; 5.D.166.169; 5.D.166.172; 5.D.166.175; 5.D.166.240;
5.D.166.244; 5.D.169.228; 5.D.169.229; 5.D.169.230; 5.D.169.231;
5.D.169.236; 5.D.169.237; 5.D.169.238; 5.D.169.239; 5.D.169.154;
5.D.169.157; 5.D.169.166; 5.D.169.169; 5.D.169.172; 5.D.169.175;
5.D.169.240; 5.D.169.244; 5.D.172.228; 5.D.172.229; 5.D.172.230;
5.D.172.231; 5.D.172.236; 5.D.172.237; 5.D.172.238; 5.D.172.239;
5.D.172.154; 5.D.172.157; 5.D.172.166; 5.D.172.169; 5.D.172.172;
5.D.172.175; 5.D.172.240; 5.D.172.244; 5.D.175.228; 5.D.175.229;
5.D.175.230; 5.D.175.231; 5.D.175.236; 5.D.175.237; 5.D.175.238;
5.D.175.239; 5.D.175.154; 5.D.175.157; 5.D.175.166; 5.D.175.169;
5.D.175.172; 5.D.175.175; 5.D.175.240; 5.D.175.244; 5.D.240.228;
5.D.240.229; 5.D.240.230; 5.D.240.231; 5.D.240.236; 5.D.240.237;
5.D.240.238; 5.D.240.239; 5.D.240.154; 5.D.240.157; 5.D.240.166;
5.D.240.169; 5.D.240.172; 5.D.240.175; 5.D.240.240; 5.D.240.244;
5.D.244.228; 5.D.244.229; 5.D.244.230; 5.D.244.231; 5.D.244.236;
5.D.244.237; 5.D.244.238; 5.D.244.239; 5.D.244.154; 5.D.244.157;
5.D.244.166; 5.D.244.169; 5.D.244.172; 5.D.244.175; 5.D.244.240; 5.D.244.244;
Prodrugs of 5.E 5.E.228.228; 5.E.228.229; 5.E.228.230; 5.E.228.231; 5.E.228.236;
5.E.228.237; 5.E.228.238; 5.E.228.239; 5.E.228.154; 5.E.228.157; 5.E.228.166;
5.E.228.169; 5.E.228.172; 5.E.228.175; 5.E.228.240; 5.E.228.244; 5.E.229.228;
5.E.229.229; 5.E.229.230; 5.E.229.231; 5.E.229.236; 5.E.229.237; 5.E.229.238;
5.E.229.239; 5.E.229.154; 5.E.229.157; 5.E.229.166; 5.E.229.169; 5.E.229.172;
5.E.229.175; 5.E.229.240; 5.E.229.244; 5.E.230.228; 5.E.230.229; 5.E.230.230;
5.E.230.231; 5.E.230.236; 5.E.230.237; 5.E.230.238; 5.E.230.239; 5.E.230.154;
5.E.230.157; 5.E.230.166; 5.E.230.169; 5.E.230.172; 5.E.230.175; 5.E.230.240;
5.E.230.244; 5.E.231.228; 5.E.231.229; 5.E.231.230; 5.E.231.231; 5.E.231.236;
5.E.231.237; 5.E.231.238; 5.E.231.239; 5.E.231.154; 5.E.231.157; 5.E.231.166;
5.E.231.169; 5.E.231.172; 5.E.231.175; 5.E.231.240; 5.E.231.244; 5.E.236.228;
5.E.236.229; 5.E.236.230; 5.E.236.231; 5.E.236.236; 5.E.236.237; 5.E.236.238;
5.E.236.239; 5.E.236.154; 5.E.236.157; 5.E.236.166; 5.E.236.169; 5.E.236.172;
5.E.236.175; 5.E.236.240; 5.E.236.244; 5.E.237.228; 5.E.237.229; 5.E.237.230;
5.E.237.231; 5.E.237.236; 5.E.237.237; 5.E.237.238; 5.E.237.239; 5.E.237.154;
5.E.237.157; 5.E.237.166; 5.E.237.169; 5.E.237.172; 5.E.237.175; 5.E.237.240;
5.E.237.244; 5.E.238.228; 5.E.238.229; 5.E.238.230; 5.E.238.231; 5.E.238.236;
5.E.238.237; 5.E.238.238; 5.E.238.239; 5.E.238.154; 5.E.238.157; 5.E.238.166;
5.E.238.169; 5.E.238.172; 5.E.238.175; 5.E.238.240; 5.E.238.244; 5.E.239.228;
5.E.239.229; 5.E.239.230; 5.E.239.231; 5.E.239.236; 5.E.239.237; 5.E.239.238;
5.E.239.239; 5.E.239.154; 5.E.239.157; 5.E.239.166; 5.E.239.169; 5.E.239.172;
5.E.239.175; 5.E.239.240; 5.E.239.244; 5.E.154.228; 5.E.154.229; 5.E.154.230;
5.E.154.231; 5.E.154.236; 5.E.154.237; 5.E.154.238; 5.E.154.239; 5.E.154.154;
5.E.154.157; 5.E.154.166; 5.E.154.169; 5.E.154.172; 5.E.154.175; 5.E.154.240;
5.E.154.244; 5.E.157.228; 5.E.157.229; 5.E.157.230; 5.E.157.231; 5.E.157.236;
5.E.157.237; 5.E.157.238; 5.E.157.239; 5.E.157.154; 5.E.157.157; 5.E.157.166;
5.E.157.169; 5.E.157.172; 5.E.157.175; 5.E.157.240; 5.E.157.244; 5.E.166.228;
5.E.166.229; 5.E.166.230; 5.E.166.231; 5.E.166.236; 5.E.166.237; 5.E.166.238;
5.E.166.239; 5.E.166.154; 5.E.166.157; 5.E.166.166; 5.E.166.169; 5.E.166.172;
5.E.166.175; 5.E.166.240; 5.E.166.244; 5.E.169.228; 5.E.169.229; 5.E.169.230;
5.E.169.231; 5.E.169.236; 5.E.169.237; 5.E.169.238; 5.E.169.239; 5.E.169.154;
5.E.169.157; 5.E.169.166; 5.E.169.169; 5.E.169.172; 5.E.169.175; 5.E.169.240;
5.E.169.244; 5.E.172.228; 5.E.172.229; 5.E.172.230; 5.E.172.231; 5.E.172.236;
5.E.172.237; 5.E.172.238; 5.E.172.239; 5.E.172.154; 5.E.172.157; 5.E.172.166;
5.E.172.169; 5.E.172.172; 5.E.172.175; 5.E.172.240; 5.E.172.244; 5.E.175.228;
5.E.175.229; 5.E.175.230; 5.E.175.231; 5.E.175.236; 5.E.175.237; 5.E.175.238;
5.E.175.239; 5.E.175.154; 5.E.175.157; 5.E.175.166; 5.E.175.169; 5.E.175.172;
5.E.175.175; 5.E.175.240; 5.E.175.244; 5.E.240.228; 5.E.240.229; 5.E.240.230;
5.E.240.231; 5.E.240.236; 5.E.240.237; 5.E.240.238; 5.E.240.239; 5.E.240.154;
5.E.240.157; 5.E.240.166; 5.E.240.169; 5.E.240.172; 5.E.240.175; 5.E.240.240;
5.E.240.244; 5.E.244.228; 5.E.244.229; 5.E.244.230; 5.E.244.231; 5.E.244.236;
5.E.244.237; 5.E.244.238; 5.E.244.239; 5.E.244.154; 5.E.244.157; 5.E.244.166;
5.E.244.169; 5.E.244.172; 5.E.244.175; 5.E.244.240; 5.E.244.244;
Prodrugs of 5.G 5.G.228.228; 5.G.228.229; 5.G.228.230; 5.G.228.231; 5.G.228.236;
5.G.228.237; 5.G.228.238; 5.G.228.239; 5.G.228.154; 5.G.228.157;
5.G.228.166; 5.G.228.169; 5.G.228.172; 5.G.228.175; 5.G.228.240;
5.G.228.244; 5.G.229.228; 5.G.229.229; 5.G.229.230; 5.G.229.231;
5.G.229.236; 5.G.229.237; 5.G.229.238; 5.G.229.239; 5.G.229.154;

TABLE 100-continued

5.G.229.157; 5.G.229.166; 5.G.229.169; 5.G.229.172; 5.G.229.175;
5.G.229.240; 5.G.229.244; 5.G.230.228; 5.G.230.229; 5.G.230.230;
5.G.230.231; 5.G.230.236; 5.G.230.237; 5.G.230.238; 5.G.230.239;
5.G.230.154; 5.G.230.157; 5.G.230.166; 5.G.230.169; 5.G.230.172;
5.G.230.175; 5.G.230.240; 5.G.230.244; 5.G.231.228; 5.G.231.229;
5.G.231.230; 5.G.231.231; 5.G.231.236; 5.G.231.237; 5.G.231.238;
5.G.231.239; 5.G.231.154; 5.G.231.157; 5.G.231.166; 5.G.231.169;
5.G.231.172; 5.G.231.175; 5.G.231.240; 5.G.231.244; 5.G.236.228;
5.G.236.229; 5.G.236.230; 5.G.236.231; 5.G.236.236; 5.G.236.237;
5.G.236.238; 5.G.236.239; 5.G.236.154; 5.G.236.157; 5.G.236.166;
5.G.236.169; 5.G.236.172; 5.G.236.175; 5.G.236.240; 5.G.236.244;
5.G.237.228; 5.G.237.229; 5.G.237.230; 5.G.237.231; 5.G.237.236;
5.G.237.237; 5.G.237.238; 5.G.237.239; 5.G.237.154; 5.G.237.157;
5.G.237.166; 5.G.237.169; 5.G.237.172; 5.G.237.175; 5.G.237.240;
5.G.237.244; 5.G.238.228; 5.G.238.229; 5.G.238.230; 5.G.238.231;
5.G.238.236; 5.G.238.237; 5.G.238.238; 5.G.238.239; 5.G.238.154;
5.G.238.157; 5.G.238.166; 5.G.238.169; 5.G.238.172; 5.G.238.175;
5.G.238.240; 5.G.238.244; 5.G.239.228; 5.G.239.229; 5.G.239.230;
5.G.239.231; 5.G.239.236; 5.G.239.237; 5.G.239.238; 5.G.239.239;
5.G.239.154; 5.G.239.157; 5.G.239.166; 5.G.239.169; 5.G.239.172;
5.G.239.175; 5.G.239.240; 5.G.239.244; 5.G.154.228; 5.G.154.229;
5.G.154.230; 5.G.154.231; 5.G.154.236; 5.G.154.237; 5.G.154.238;
5.G.154.239; 5.G.154.154; 5.G.154.157; 5.G.154.166; 5.G.154.169;
5.G.154.172; 5.G.154.175; 5.G.154.240; 5.G.154.244; 5.G.157.228;
5.G.157.229; 5.G.157.230; 5.G.157.231; 5.G.157.236; 5.G.157.237;
5.G.157.238; 5.G.157.239; 5.G.157.154; 5.G.157.157; 5.G.157.166;
5.G.157.169; 5.G.157.172; 5.G.157.175; 5.G.157.240; 5.G.157.244;
5.G.166.228; 5.G.166.229; 5.G.166.230; 5.G.166.231; 5.G.166.236;
5.G.166.237; 5.G.166.238; 5.G.166.239; 5.G.166.154; 5.G.166.157;
5.G.166.166; 5.G.166.169; 5.G.166.172; 5.G.166.175; 5.G.166.240;
5.G.166.244; 5.G.169.228; 5.G.169.229; 5.G.169.230; 5.G.169.231;
5.G.169.236; 5.G.169.237; 5.G.169.238; 5.G.169.239; 5.G.169.154;
5.G.169.157; 5.G.169.166; 5.G.169.169; 5.G.169.172; 5.G.169.175;
5.G.169.240; 5.G.169.244; 5.G.172.228; 5.G.172.229; 5.G.172.230;
5.G.172.231; 5.G.172.236; 5.G.172.237; 5.G.172.238; 5.G.172.239;
5.G.172.154; 5.G.172.157; 5.G.172.166; 5.G.172.169; 5.G.172.172;
5.G.172.175; 5.G.172.240; 5.G.172.244; 5.G.175.228; 5.G.175.229;
5.G.175.230; 5.G.175.231; 5.G.175.236; 5.G.175.237; 5.G.175.238;
5.G.175.239; 5.G.175.154; 5.G.175.157; 5.G.175.166; 5.G.175.169;
5.G.175.172; 5.G.175.175; 5.G.175.240; 5.G.175.244; 5.G.240.228;
5.G.240.229; 5.G.240.230; 5.G.240.231; 5.G.240.236; 5.G.240.237;
5.G.240.238; 5.G.240.239; 5.G.240.154; 5.G.240.157; 5.G.240.166;
5.G.240.169; 5.G.240.172; 5.G.240.175; 5.G.240.240; 5.G.240.244;
5.G.244.228; 5.G.244.229; 5.G.244.230; 5.G.244.231; 5.G.244.236;
5.G.244.237; 5.G.244.238; 5.G.244.239; 5.G.244.154; 5.G.244.157;
5.G.244.166; 5.G.244.169; 5.G.244.172; 5.G.244.175; 5.G.244.240; 5.G.244.244;
Prodrugs of 5.I 5.I.228.228; 5.I.228.229; 5.I.228.230; 5.I.228.231; 5.I.228.236; 5.I.228.237;
5.I.228.238; 5.I.228.239; 5.I.228.154; 5.I.228.157; 5.I.228.166; 5.I.228.169;
5.I.228.172; 5.I.228.175; 5.I.228.240; 5.I.228.244; 5.I.229.228; 5.I.229.229;
5.I.229.230; 5.I.229.231; 5.I.229.236; 5.I.229.237; 5.I.229.238; 5.I.229.239;
5.I.229.154; 5.I.229.157; 5.I.229.166; 5.I.229.169; 5.I.229.172; 5.I.229.175;
5.I.229.240; 5.I.229.244; 5.I.230.228; 5.I.230.229; 5.I.230.230; 5.I.230.231;
5.I.230.236; 5.I.230.237; 5.I.230.238; 5.I.230.239; 5.I.230.154; 5.I.230.157;
5.I.230.166; 5.I.230.169; 5.I.230.172; 5.I.230.175; 5.I.230.240; 5.I.230.244;
5.I.231.228; 5.I.231.229; 5.I.231.230; 5.I.231.231; 5.I.231.236; 5.I.231.237;
5.I.231.238; 5.I.231.239; 5.I.231.154; 5.I.231.157; 5.I.231.166; 5.I.231.169;
5.I.231.172; 5.I.231.175; 5.I.231.240; 5.I.231.244; 5.I.236.228; 5.I.236.229;
5.I.236.230; 5.I.236.231; 5.I.236.236; 5.I.236.237; 5.I.236.238; 5.I.236.239;
5.I.236.154; 5.I.236.157; 5.I.236.166; 5.I.236.169; 5.I.236.172; 5.I.236.175;
5.I.236.240; 5.I.236.244; 5.I.237.228; 5.I.237.229; 5.I.237.230; 5.I.237.231;
5.I.237.236; 5.I.237.237; 5.I.237.238; 5.I.237.239; 5.I.237.154; 5.I.237.157;
5.I.237.166; 5.I.237.169; 5.I.237.172; 5.I.237.175; 5.I.237.240; 5.I.237.244;
5.I.238.228; 5.I.238.229; 5.I.238.230; 5.I.238.231; 5.I.238.236; 5.I.238.237;
5.I.238.238; 5.I.238.239; 5.I.238.154; 5.I.238.157; 5.I.238.166; 5.I.238.169;
5.I.238.172; 5.I.238.175; 5.I.238.240; 5.I.238.244; 5.I.239.228; 5.I.239.229;
5.I.239.230; 5.I.239.231; 5.I.239.236; 5.I.239.237; 5.I.239.238; 5.I.239.239;
5.I.239.154; 5.I.239.157; 5.I.239.166; 5.I.239.169; 5.I.239.172; 5.I.239.175;
5.I.239.240; 5.I.239.244; 5.I.154.228; 5.I.154.229; 5.I.154.230; 5.I.154.231;
5.I.154.236; 5.I.154.237; 5.I.154.238; 5.I.154.239; 5.I.154.154; 5.I.154.157;
5.I.154.166; 5.I.154.169; 5.I.154.172; 5.I.154.175; 5.I.154.240; 5.I.154.244;
5.I.157.228; 5.I.157.229; 5.I.157.230; 5.I.157.231; 5.I.157.236; 5.I.157.237;
5.I.157.238; 5.I.157.239; 5.I.157.154; 5.I.157.157; 5.I.157.166; 5.I.157.169;
5.I.157.172; 5.I.157.175; 5.I.157.240; 5.I.157.244; 5.I.166.228; 5.I.166.229;
5.I.166.230; 5.I.166.231; 5.I.166.236; 5.I.166.237; 5.I.166.238; 5.I.166.239;
5.I.166.154; 5.I.166.157; 5.I.166.166; 5.I.166.169; 5.I.166.172; 5.I.166.175;
5.I.166.240; 5.I.166.244; 5.I.169.228; 5.I.169.229; 5.I.169.230; 5.I.169.231;
5.I.169.236; 5.I.169.237; 5.I.169.238; 5.I.169.239; 5.I.169.154; 5.I.169.157;

TABLE 100-continued

5.I.169.166; 5.I.169.169; 5.I.169.172; 5.I.169.175; 5.I.169.240; 5.I.169.244;
5.I.172.228; 5.I.172.229; 5.I.172.230; 5.I.172.231; 5.I.172.236; 5.I.172.237;
5.I.172.238; 5.I.172.239; 5.I.172.154; 5.I.172.157; 5.I.172.166; 5.I.172.169;
5.I.172.172; 5.I.172.175; 5.I.172.240; 5.I.172.244; 5.I.175.228; 5.I.175.229;
5.I.175.230; 5.I.175.231; 5.I.175.236; 5.I.175.237; 5.I.175.238; 5.I.175.239;
5.I.175.154; 5.I.175.157; 5.I.175.166; 5.I.175.169; 5.I.175.172; 5.I.175.175;
5.I.175.240; 5.I.175.244; 5.I.240.228; 5.I.240.229; 5.I.240.230; 5.I.240.231;
5.I.240.236; 5.I.240.237; 5.I.240.238; 5.I.240.239; 5.I.240.154; 5.I.240.157;
5.I.240.166; 5.I.240.169; 5.I.240.172; 5.I.240.175; 5.I.240.240; 5.I.240.244;
5.I.244.228; 5.I.244.229; 5.I.244.230; 5.I.244.231; 5.I.244.236; 5.I.244.237;
5.I.244.238; 5.I.244.239; 5.I.244.154; 5.I.244.157; 5.I.244.166; 5.I.244.169; 5.I.244.172;
5.I.244.175; 5.I.244.240; 5.I.244.244;

Prodrugs of 5.J

5.J.228.228; 5.J.228.229; 5.J.228.230; 5.J.228.231; 5.J.228.236; 5.J.228.237;
5.J.228.238; 5.J.228.239; 5.J.228.154; 5.J.228.157; 5.J.228.166; 5.J.228.169;
5.J.228.172; 5.J.228.175; 5.J.228.240; 5.J.228.244; 5.J.229.228; 5.J.229.229;
5.J.229.230; 5.J.229.231; 5.J.229.236; 5.J.229.237; 5.J.229.238; 5.J.229.239;
5.J.229.154; 5.J.229.157; 5.J.229.166; 5.J.229.169; 5.J.229.172; 5.J.229.175;
5.J.229.240; 5.J.229.244; 5.J.230.228; 5.J.230.229; 5.J.230.230; 5.J.230.231;
5.J.230.236; 5.J.230.237; 5.J.230.238; 5.J.230.239; 5.J.230.154; 5.J.230.157;
5.J.230.166; 5.J.230.169; 5.J.230.172; 5.J.230.175; 5.J.230.240; 5.J.230.244;
5.J.231.228; 5.J.231.229; 5.J.231.230; 5.J.231.231; 5.J.231.236; 5.J.231.237;
5.J.231.238; 5.J.231.239; 5.J.231.154; 5.J.231.157; 5.J.231.166; 5.J.231.169;
5.J.231.172; 5.J.231.175; 5.J.231.240; 5.J.231.244; 5.J.236.228; 5.J.236.229;
5.J.236.230; 5.J.236.231; 5.J.236.236; 5.J.236.237; 5.J.236.238; 5.J.236.239;
5.J.236.154; 5.J.236.157; 5.J.236.166; 5.J.236.169; 5.J.236.172; 5.J.236.175;
5.J.236.240; 5.J.236.244; 5.J.237.228; 5.J.237.229; 5.J.237.230; 5.J.237.231;
5.J.237.236; 5.J.237.237; 5.J.237.238; 5.J.237.239; 5.J.237.154; 5.J.237.157;
5.J.237.166; 5.J.237.169; 5.J.237.172; 5.J.237.175; 5.J.237.240; 5.J.237.244;
5.J.238.228; 5.J.238.229; 5.J.238.230; 5.J.238.231; 5.J.238.236; 5.J.238.237;
5.J.238.238; 5.J.238.239; 5.J.238.154; 5.J.238.157; 5.J.238.166; 5.J.238.169;
5.J.238.172; 5.J.238.175; 5.J.238.240; 5.J.238.244; 5.J.239.228; 5.J.239.229;
5.J.239.230; 5.J.239.231; 5.J.239.236; 5.J.239.237; 5.J.239.238; 5.J.239.239;
5.J.239.154; 5.J.239.157; 5.J.239.166; 5.J.239.169; 5.J.239.172; 5.J.239.175;
5.J.239.240; 5.J.239.244; 5.J.154.228; 5.J.154.229; 5.J.154.230; 5.J.154.231;
5.J.154.236; 5.J.154.237; 5.J.154.238; 5.J.154.239; 5.J.154.154; 5.J.154.157;
5.J.154.166; 5.J.154.169; 5.J.154.172; 5.J.154.175; 5.J.154.240; 5.J.154.244;
5.J.157.228; 5.J.157.229; 5.J.157.230; 5.J.157.231; 5.J.157.236; 5.J.157.237;
5.J.157.238; 5.J.157.239; 5.J.157.154; 5.J.157.157; 5.J.157.166; 5.J.157.169;
5.J.157.172; 5.J.157.175; 5.J.157.240; 5.J.157.244; 5.J.166.228; 5.J.166.229;
5.J.166.230; 5.J.166.231; 5.J.166.236; 5.J.166.237; 5.J.166.238; 5.J.166.239;
5.J.166.154; 5.J.166.157; 5.J.166.166; 5.J.166.169; 5.J.166.172; 5.J.166.175;
5.J.166.240; 5.J.166.244; 5.J.169.228; 5.J.169.229; 5.J.169.230; 5.J.169.231;
5.J.169.236; 5.J.169.237; 5.J.169.238; 5.J.169.239; 5.J.169.154; 5.J.169.157;
5.J.169.166; 5.J.169.169; 5.J.169.172; 5.J.169.175; 5.J.169.240; 5.J.169.244;
5.J.172.228; 5.J.172.229; 5.J.172.230; 5.J.172.231; 5.J.172.236; 5.J.172.237;
5.J.172.238; 5.J.172.239; 5.J.172.154; 5.J.172.157; 5.J.172.166; 5.J.172.169;
5.J.172.172; 5.J.172.175; 5.J.172.240; 5.J.172.244; 5.J.175.228; 5.J.175.229;
5.J.175.230; 5.J.175.231; 5.J.175.236; 5.J.175.237; 5.J.175.238; 5.J.175.239;
5.J.175.154; 5.J.175.157; 5.J.175.166; 5.J.175.169; 5.J.175.172; 5.J.175.175;
5.J.175.240; 5.J.175.244; 5.J.240.228; 5.J.240.229; 5.J.240.230; 5.J.240.231;
5.J.240.236; 5.J.240.237; 5.J.240.238; 5.J.240.239; 5.J.240.154; 5.J.240.157;
5.J.240.166; 5.J.240.169; 5.J.240.172; 5.J.240.175; 5.J.240.240; 5.J.240.244;
5.J.244.228; 5.J.244.229; 5.J.244.230; 5.J.244.231; 5.J.244.236; 5.J.244.237;
5.J.244.238; 5.J.244.239; 5.J.244.154; 5.J.244.157; 5.J.244.166; 5.J.244.169;
5.J.244.172; 5.J.244.175; 5.J.244.240; 5.J.244.244;

Prodrugs of 5.L

5.L.228.228; 5.L.228.229; 5.L.228.230; 5.L.228.231; 5.L.228.236;
5.L.228.237; 5.L.228.238; 5.L.228.239; 5.L.228.154; 5.L.228.157; 5.L.228.166;
5.L.228.169; 5.L.228.172; 5.L.228.175; 5.L.228.240; 5.L.228.244; 5.L.229.228;
5.L.229.229; 5.L.229.230; 5.L.229.231; 5.L.229.236; 5.L.229.237; 5.L.229.238;
5.L.229.239; 5.L.229.154; 5.L.229.157; 5.L.229.166; 5.L.229.169; 5.L.229.172;
5.L.229.175; 5.L.229.240; 5.L.229.244; 5.L.230.228; 5.L.230.229; 5.L.230.230;
5.L.230.231; 5.L.230.236; 5.L.230.237; 5.L.230.238; 5.L.230.239; 5.L.230.154;
5.L.230.157; 5.L.230.166; 5.L.230.169; 5.L.230.172; 5.L.230.175; 5.L.230.240;
5.L.230.244; 5.L.231.228; 5.L.231.229; 5.L.231.230; 5.L.231.231; 5.L.231.236;
5.L.231.237; 5.L.231.238; 5.L.231.239; 5.L.231.154; 5.L.231.157; 5.L.231.166;
5.L.231.169; 5.L.231.172; 5.L.231.175; 5.L.231.240; 5.L.231.244; 5.L.236.228;
5.L.236.229; 5.L.236.230; 5.L.236.231; 5.L.236.236; 5.L.236.237; 5.L.236.238;
5.L.236.239; 5.L.236.154; 5.L.236.157; 5.L.236.166; 5.L.236.169; 5.L.236.172;
5.L.236.175; 5.L.236.240; 5.L.236.244; 5.L.237.228; 5.L.237.229; 5.L.237.230;
5.L.237.231; 5.L.237.236; 5.L.237.237; 5.L.237.238; 5.L.237.239; 5.L.237.154;
5.L.237.157; 5.L.237.166; 5.L.237.169; 5.L.237.172; 5.L.237.175; 5.L.237.240;
5.L.237.244; 5.L.238.228; 5.L.238.229; 5.L.238.230; 5.L.238.231; 5.L.238.236;
5.L.238.237; 5.L.238.238; 5.L.238.239; 5.L.238.154; 5.L.238.157; 5.L.238.166;
5.L.238.169; 5.L.238.172; 5.L.238.175; 5.L.238.240; 5.L.238.244; 5.L.239.228;
5.L.239.229; 5.L.239.230; 5.L.239.231; 5.L.239.236; 5.L.239.237; 5.L.239.238;

TABLE 100-continued

5.L.239.239; 5.L.239.154; 5.L.239.157; 5.L.239.166; 5.L.239.169; 5.L.239.172;
5.L.239.175; 5.L.239.240; 5.L.239.244; 5.L.154.228; 5.L.154.229; 5.L.154.230;
5.L.154.231; 5.L.154.236; 5.L.154.237; 5.L.154.238; 5.L.154.239; 5.L.154.154;
5.L.154.157; 5.L.154.166; 5.L.154.169; 5.L.154.172; 5.L.154.175; 5.L.154.240;
5.L.154.244; 5.L.157.228; 5.L.157.229; 5.L.157.230; 5.L.157.231; 5.L.157.236;
5.L.157.237; 5.L.157.238; 5.L.157.239; 5.L.157.154; 5.L.157.157; 5.L.157.166;
5.L.157.169; 5.L.157.172; 5.L.157.175; 5.L.157.240; 5.L.157.244; 5.L.166.228;
5.L.166.229; 5.L.166.230; 5.L.166.231; 5.L.166.236; 5.L.166.237; 5.L.166.238;
5.L.166.239; 5.L.166.154; 5.L.166.157; 5.L.166.166; 5.L.166.169; 5.L.166.172;
5.L.166.175; 5.L.166.240; 5.L.166.244; 5.L.169.228; 5.L.169.229; 5.L.169.230;
5.L.169.231; 5.L.169.236; 5.L.169.237; 5.L.169.238; 5.L.169.239; 5.L.169.154;
5.L.169.157; 5.L.169.166; 5.L.169.169; 5.L.169.172; 5.L.169.175; 5.L.169.240;
5.L.169.244; 5.L.172.228; 5.L.172.229; 5.L.172.230; 5.L.172.231; 5.L.172.236;
5.L.172.237; 5.L.172.238; 5.L.172.239; 5.L.172.154; 5.L.172.157; 5.L.172.166;
5.L.172.169; 5.L.172.172; 5.L.172.175; 5.L.172.240; 5.L.172.244; 5.L.175.228;
5.L.175.229; 5.L.175.230; 5.L.175.231; 5.L.175.236; 5.L.175.237; 5.L.175.238;
5.L.175.239; 5.L.175.154; 5.L.175.157; 5.L.175.166; 5.L.175.169; 5.L.175.172;
5.L.175.175; 5.L.175.240; 5.L.175.244; 5.L.240.228; 5.L.240.229; 5.L.240.230;
5.L.240.231; 5.L.240.236; 5.L.240.237; 5.L.240.238; 5.L.240.239; 5.L.240.154;
5.L.240.157; 5.L.240.166; 5.L.240.169; 5.L.240.172; 5.L.240.175; 5.L.240.240;
5.L.240.244; 5.L.244.228; 5.L.244.229; 5.L.244.230; 5.L.244.231; 5.L.244.236;
5.L.244.237; 5.L.244.238; 5.L.244.239; 5.L.244.154; 5.L.244.157; 5.L.244.166;
5.L.244.169; 5.L.244.172; 5.L.244.175; 5.L.244.240; 5.L.244.244;
Prodrugs of 5.O 5.O.228.228; 5.O.228.229; 5.O.228.230; 5.O.228.231; 5.O.228.236;
5.O.228.237; 5.O.228.238; 5.O.228.239; 5.O.228.154; 5.O.228.157;
5.O.228.166; 5.O.228.169; 5.O.228.172; 5.O.228.175; 5.O.228.240;
5.O.228.244; 5.O.229.228; 5.O.229.229; 5.O.229.230; 5.O.229.231;
5.O.229.236; 5.O.229.237; 5.O.229.238; 5.O.229.239; 5.O.229.154;
5.O.229.157; 5.O.229.166; 5.O.229.169; 5.O.229.172; 5.O.229.175;
5.O.229.240; 5.O.229.244; 5.O.230.228; 5.O.230.229; 5.O.230.230;
5.O.230.231; 5.O.230.236; 5.O.230.237; 5.O.230.238; 5.O.230.239;
5.O.230.154; 5.O.230.157; 5.O.230.166; 5.O.230.169; 5.O.230.172;
5.O.230.175; 5.O.230.240; 5.O.230.244; 5.O.231.228; 5.O.231.229;
5.O.231.230; 5.O.231.231; 5.O.231.236; 5.O.231.237; 5.O.231.238;
5.O.231.239; 5.O.231.154; 5.O.231.157; 5.O.231.166; 5.O.231.169;
5.O.231.172; 5.O.231.175; 5.O.231.240; 5.O.231.244; 5.O.236.228;
5.O.236.229; 5.O.236.230; 5.O.236.231; 5.O.236.236; 5.O.236.237;
5.O.236.238; 5.O.236.239; 5.O.236.154; 5.O.236.157; 5.O.236.166;
5.O.236.169; 5.O.236.172; 5.O.236.175; 5.O.236.240; 5.O.236.244;
5.O.237.228; 5.O.237.229; 5.O.237.230; 5.O.237.231; 5.O.237.236;
5.O.237.237; 5.O.237.238; 5.O.237.239; 5.O.237.154; 5.O.237.157;
5.O.237.166; 5.O.237.169; 5.O.237.172; 5.O.237.175; 5.O.237.240;
5.O.237.244; 5.O.238.228; 5.O.238.229; 5.O.238.230; 5.O.238.231;
5.O.238.236; 5.O.238.237; 5.O.238.238; 5.O.238.239; 5.O.238.154;
5.O.238.157; 5.O.238.166; 5.O.238.169; 5.O.238.172; 5.O.238.175;
5.O.238.240; 5.O.238.244; 5.O.239.228; 5.O.239.229; 5.O.239.230;
5.O.239.231; 5.O.239.236; 5.O.239.237; 5.O.239.238; 5.O.239.239;
5.O.239.154; 5.O.239.157; 5.O.239.166; 5.O.239.169; 5.O.239.172;
5.O.239.175; 5.O.239.240; 5.O.239.244; 5.O.154.228; 5.O.154.229;
5.O.154.230; 5.O.154.231; 5.O.154.236; 5.O.154.237; 5.O.154.238;
5.O.154.239; 5.O.154.154; 5.O.154.157; 5.O.154.166; 5.O.154.169;
5.O.154.172; 5.O.154.175; 5.O.154.240; 5.O.154.244; 5.O.157.228;
5.O.157.229; 5.O.157.230; 5.O.157.231; 5.O.157.236; 5.O.157.237;
5.O.157.238; 5.O.157.239; 5.O.157.154; 5.O.157.157; 5.O.157.166;
5.O.157.169; 5.O.157.172; 5.O.157.175; 5.O.157.240; 5.O.157.244;
5.O.166.228; 5.O.166.229; 5.O.166.230; 5.O.166.231; 5.O.166.236;
5.O.166.237; 5.O.166.238; 5.O.166.239; 5.O.166.154; 5.O.166.157;
5.O.166.166; 5.O.166.169; 5.O.166.172; 5.O.166.175; 5.O.166.240;
5.O.166.244; 5.O.169.228; 5.O.169.229; 5.O.169.230; 5.O.169.231;
5.O.169.236; 5.O.169.237; 5.O.169.238; 5.O.169.239; 5.O.169.154;
5.O.169.157; 5.O.169.166; 5.O.169.169; 5.O.169.172; 5.O.169.175;
5.O.169.240; 5.O.169.244; 5.O.172.228; 5.O.172.229; 5.O.172.230;
5.O.172.231; 5.O.172.236; 5.O.172.237; 5.O.172.238; 5.O.172.239;
5.O.172.154; 5.O.172.157; 5.O.172.166; 5.O.172.169; 5.O.172.172;
5.O.172.175; 5.O.172.240; 5.O.172.244; 5.O.175.228; 5.O.175.229;
5.O.175.230; 5.O.175.231; 5.O.175.236; 5.O.175.237; 5.O.175.238;
5.O.175.239; 5.O.175.154; 5.O.175.157; 5.O.175.166; 5.O.175.169;
5.O.175.172; 5.O.175.175; 5.O.175.240; 5.O.175.244; 5.O.240.228;
5.O.240.229; 5.O.240.230; 5.O.240.231; 5.O.240.236; 5.O.240.237;
5.O.240.238; 5.O.240.239; 5.O.240.154; 5.O.240.157; 5.O.240.166;
5.O.240.169; 5.O.240.172; 5.O.240.175; 5.O.240.240; 5.O.240.244;
5.O.244.228; 5.O.244.229; 5.O.244.230; 5.O.244.231; 5.O.244.236;
5.O.244.237; 5.O.244.238; 5.O.244.239; 5.O.244.154; 5.O.244.157;
5.O.244.166; 5.O.244.169; 5.O.244.172; 5.O.244.175; 5.O.244.240;
5.O.244.244;

TABLE 100-continued

Prodrugs of 5.P

5.P.228.228; 5.P.228.229; 5.P.228.230; 5.P.228.231; 5.P.228.236;
5.P.228.237; 5.P.228.238; 5.P.228.239; 5.P.228.154; 5.P.228.157; 5.P.228.166;
5.P.228.169; 5.P.228.172; 5.P.228.175; 5.P.228.240; 5.P.228.244; 5.P.229.228;
5.P.229.229; 5.P.229.230; 5.P.229.231; 5.P.229.236; 5.P.229.237; 5.P.229.238;
5.P.229.239; 5.P.229.154; 5.P.229.157; 5.P.229.166; 5.P.229.169; 5.P.229.172;
5.P.229.175; 5.P.229.240; 5.P.229.244; 5.P.230.228; 5.P.230.229; 5.P.230.230;
5.P.230.231; 5.P.230.236; 5.P.230.237; 5.P.230.238; 5.P.230.239; 5.P.230.154;
5.P.230.157; 5.P.230.166; 5.P.230.169; 5.P.230.172; 5.P.230.175; 5.P.230.240;
5.P.230.244; 5.P.231.228; 5.P.231.229; 5.P.231.230; 5.P.231.231; 5.P.231.236;
5.P.231.237; 5.P.231.238; 5.P.231.239; 5.P.231.154; 5.P.231.157; 5.P.231.166;
5.P.231.169; 5.P.231.172; 5.P.231.175; 5.P.231.240; 5.P.231.244; 5.P.236.228;
5.P.236.229; 5.P.236.230; 5.P.236.231; 5.P.236.236; 5.P.236.237; 5.P.236.238;
5.P.236.239; 5.P.236.154; 5.P.236.157; 5.P.236.166; 5.P.236.169; 5.P.236.172;
5.P.236.175; 5.P.236.240; 5.P.236.244; 5.P.237.228; 5.P.237.229; 5.P.237.230;
5.P.237.231; 5.P.237.236; 5.P.237.237; 5.P.237.238; 5.P.237.239; 5.P.237.154;
5.P.237.157; 5.P.237.166; 5.P.237.169; 5.P.237.172; 5.P.237.175; 5.P.237.240;
5.P.237.244; 5.P.238.228; 5.P.238.229; 5.P.238.230; 5.P.238.231; 5.P.238.236;
5.P.238.237; 5.P.238.238; 5.P.238.239; 5.P.238.154; 5.P.238.157; 5.P.238.166;
5.P.238.169; 5.P.238.172; 5.P.238.175; 5.P.238.240; 5.P.238.244; 5.P.239.228;
5.P.239.229; 5.P.239.230; 5.P.239.231; 5.P.239.236; 5.P.239.237; 5.P.239.238;
5.P.239.239; 5.P.239.154; 5.P.239.157; 5.P.239.166; 5.P.239.169; 5.P.239.172;
5.P.239.175; 5.P.239.240; 5.P.239.244; 5.P.154.228; 5.P.154.229; 5.P.154.230;
5.P.154.231; 5.P.154.236; 5.P.154.237; 5.P.154.238; 5.P.154.239; 5.P.154.154;
5.P.154.157; 5.P.154.166; 5.P.154.169; 5.P.154.172; 5.P.154.175; 5.P.154.240;
5.P.154.244; 5.P.157.228; 5.P.157.229; 5.P.157.230; 5.P.157.231; 5.P.157.236;
5.P.157.237; 5.P.157.238; 5.P.157.239; 5.P.157.154; 5.P.157.157; 5.P.157.166;
5.P.157.169; 5.P.157.172; 5.P.157.175; 5.P.157.240; 5.P.157.244; 5.P.166.228;
5.P.166.229; 5.P.166.230; 5.P.166.231; 5.P.166.236; 5.P.166.237; 5.P.166.238;
5.P.166.239; 5.P.166.154; 5.P.166.157; 5.P.166.166; 5.P.166.169; 5.P.166.172;
5.P.166.175; 5.P.166.240; 5.P.166.244; 5.P.169.228; 5.P.169.229; 5.P.169.230;
5.P.169.231; 5.P.169.236; 5.P.169.237; 5.P.169.238; 5.P.169.239; 5.P.169.154;
5.P.169.157; 5.P.169.166; 5.P.169.169; 5.P.169.172; 5.P.169.175; 5.P.169.240;
5.P.169.244; 5.P.172.228; 5.P.172.229; 5.P.172.230; 5.P.172.231; 5.P.172.236;
5.P.172.237; 5.P.172.238; 5.P.172.239; 5.P.172.154; 5.P.172.157; 5.P.172.166;
5.P.172.169; 5.P.172.172; 5.P.172.175; 5.P.172.240; 5.P.172.244; 5.P.175.228;
5.P.175.229; 5.P.175.230; 5.P.175.231; 5.P.175.236; 5.P.175.237; 5.P.175.238;
5.P.175.239; 5.P.175.154; 5.P.175.157; 5.P.175.166; 5.P.175.169; 5.P.175.172;
5.P.175.175; 5.P.175.240; 5.P.175.244; 5.P.240.228; 5.P.240.229; 5.P.240.230;
5.P.240.231; 5.P.240.236; 5.P.240.237; 5.P.240.238; 5.P.240.239; 5.P.240.154;
5.P.240.157; 5.P.240.166; 5.P.240.169; 5.P.240.172; 5.P.240.175; 5.P.240.240;
5.P.240.244; 5.P.244.228; 5.P.244.229; 5.P.244.230; 5.P.244.231; 5.P.244.236;
5.P.244.237; 5.P.244.238; 5.P.244.239; 5.P.244.154; 5.P.244.157; 5.P.244.166;
5.P.244.169; 5.P.244.172; 5.P.244.175; 5.P.244.240; 5.P.244.244;

Prodrugs of 5.U

5.U.228.228; 5.U.228.229; 5.U.228.230; 5.U.228.231; 5.U.228.236;
5.U.228.237; 5.U.228.238; 5.U.228.239; 5.U.228.154; 5.U.228.157;
5.U.228.166; 5.U.228.169; 5.U.228.172; 5.U.228.175; 5.U.228.240;
5.U.228.244; 5.U.229.228; 5.U.229.229; 5.U.229.230; 5.U.229.231;
5.U.229.236; 5.U.229.237; 5.U.229.238; 5.U.229.239; 5.U.229.154;
5.U.229.157; 5.U.229.166; 5.U.229.169; 5.U.229.172; 5.U.229.175;
5.U.229.240; 5.U.229.244; 5.U.230.228; 5.U.230.229; 5.U.230.230;
5.U.230.231; 5.U.230.236; 5.U.230.237; 5.U.230.238; 5.U.230.239;
5.U.230.154; 5.U.230.157; 5.U.230.166; 5.U.230.169; 5.U.230.172;
5.U.230.175; 5.U.230.240; 5.U.230.244; 5.U.231.228; 5.U.231.229;
5.U.231.230; 5.U.231.231; 5.U.231.236; 5.U.231.237; 5.U.231.238;
5.U.231.239; 5.U.231.154; 5.U.231.157; 5.U.231.166; 5.U.231.169;
5.U.231.172; 5.U.231.175; 5.U.231.240; 5.U.231.244; 5.U.236.228;
5.U.236.229; 5.U.236.230; 5.U.236.231; 5.U.236.236; 5.U.236.237;
5.U.236.238; 5.U.236.239; 5.U.236.154; 5.U.236.157; 5.U.236.166;
5.U.236.169; 5.U.236.172; 5.U.236.175; 5.U.236.240; 5.U.236.244;
5.U.237.228; 5.U.237.229; 5.U.237.230; 5.U.237.231; 5.U.237.236;
5.U.237.237; 5.U.237.238; 5.U.237.239; 5.U.237.154; 5.U.237.157;
5.U.237.166; 5.U.237.169; 5.U.237.172; 5.U.237.175; 5.U.237.240;
5.U.237.244; 5.U.238.228; 5.U.238.229; 5.U.238.230; 5.U.238.231;
5.U.238.236; 5.U.238.237; 5.U.238.238; 5.U.238.239; 5.U.238.154;
5.U.238.157; 5.U.238.166; 5.U.238.169; 5.U.238.172; 5.U.238.175;
5.U.238.240; 5.U.238.244; 5.U.239.228; 5.U.239.229; 5.U.239.230;
5.U.239.231; 5.U.239.236; 5.U.239.237; 5.U.239.238; 5.U.239.239;
5.U.239.154; 5.U.239.157; 5.U.239.166; 5.U.239.169; 5.U.239.172;
5.U.239.175; 5.U.239.240; 5.U.239.244; 5.U.154.228; 5.U.154.229;
5.U.154.230; 5.U.154.231; 5.U.154.236; 5.U.154.237; 5.U.154.238;
5.U.154.239; 5.U.154.154; 5.U.154.157; 5.U.154.166; 5.U.154.169;
5.U.154.172; 5.U.154.175; 5.U.154.240; 5.U.154.244; 5.U.157.228;
5.U.157.229; 5.U.157.230; 5.U.157.231; 5.U.157.236; 5.U.157.237;
5.U.157.238; 5.U.157.239; 5.U.157.154; 5.U.157.157; 5.U.157.166;
5.U.157.169; 5.U.157.172; 5.U.157.175; 5.U.157.240; 5.U.157.244;

TABLE 100-continued

5.U.166.228; 5.U.166.229; 5.U.166.230; 5.U.166.231; 5.U.166.236;
5.U.166.237; 5.U.166.238; 5.U.166.239; 5.U.166.154; 5.U.166.157;
5.U.166.166; 5.U.166.169; 5.U.166.172; 5.U.166.175; 5.U.166.240;
5.U.166.244; 5.U.169.228; 5.U.169.229; 5.U.169.230; 5.U.169.231;
5.U.169.236; 5.U.169.237; 5.U.169.238; 5.U.169.239; 5.U.169.154;
5.U.169.157; 5.U.169.166; 5.U.169.169; 5.U.169.172; 5.U.169.175;
5.U.169.240; 5.U.169.244; 5.U.172.228; 5.U.172.229; 5.U.172.230;
5.U.172.231; 5.U.172.236; 5.U.172.237; 5.U.172.238; 5.U.172.239;
5.U.172.154; 5.U.172.157; 5.U.172.166; 5.U.172.169; 5.U.172.172;
5.U.172.175; 5.U.172.240; 5.U.172.244; 5.U.175.228; 5.U.175.229;
5.U.175.230; 5.U.175.231; 5.U.175.236; 5.U.175.237; 5.U.175.238;
5.U.175.239; 5.U.175.154; 5.U.175.157; 5.U.175.166; 5.U.175.169;
5.U.175.172; 5.U.175.175; 5.U.175.240; 5.U.175.244; 5.U.240.228;
5.U.240.229; 5.U.240.230; 5.U.240.231; 5.U.240.236; 5.U.240.237;
5.U.240.238; 5.U.240.239; 5.U.240.154; 5.U.240.157; 5.U.240.166;
5.U.240.169; 5.U.240.172; 5.U.240.175; 5.U.240.240; 5.U.240.244;
5.U.244.228; 5.U.244.229; 5.U.244.230; 5.U.244.231; 5.U.244.236;
5.U.244.237; 5.U.244.238; 5.U.244.239; 5.U.244.154; 5.U.244.157;
5.U.244.166; 5.U.244.169; 5.U.244.172; 5.U.244.175; 5.U.244.240;
5.U.244.244;
Prodrugs of 5.W 5.W.228.228; 5.W.228.229; 5.W.228.230; 5.W.228.231; 5.W.228.236;
5.W.228.237; 5.W.228.238; 5.W.228.239; 5.W.228.154; 5.W.228.157;
5.W.228.166; 5.W.228.169; 5.W.228.172; 5.W.228.175; 5.W.228.240;
5.W.228.244; 5.W.229.228; 5.W.229.229; 5.W.229.230; 5.W.229.231;
5.W.229.236; 5.W.229.237; 5.W.229.238; 5.W.229.239; 5.W.229.154;
5.W.229.157; 5.W.229.166; 5.W.229.169; 5.W.229.172; 5.W.229.175;
5.W.229.240; 5.W.229.244; 5.W.230.228; 5.W.230.229; 5.W.230.230;
5.W.230.231; 5.W.230.236; 5.W.230.237; 5.W.230.238; 5.W.230.239;
5.W.230.154; 5.W.230.157; 5.W.230.166; 5.W.230.169; 5.W.230.172;
5.W.230.175; 5.W.230.240; 5.W.230.244; 5.W.231.228; 5.W.231.229;
5.W.231.230; 5.W.231.231; 5.W.231.236; 5.W.231.237; 5.W.231.238;
5.W.231.239; 5.W.231.154; 5.W.231.157; 5.W.231.166; 5.W.231.169;
5.W.231.172; 5.W.231.175; 5.W.231.240; 5.W.231.244; 5.W.236.228;
5.W.236.229; 5.W.236.230; 5.W.236.231; 5.W.236.236; 5.W.236.237;
5.W.236.238; 5.W.236.239; 5.W.236.154; 5.W.236.157; 5.W.236.166;
5.W.236.169; 5.W.236.172; 5.W.236.175; 5.W.236.240; 5.W.236.244;
5.W.237.228; 5.W.237.229; 5.W.237.230; 5.W.237.231; 5.W.237.236;
5.W.237.237; 5.W.237.238; 5.W.237.239; 5.W.237.154; 5.W.237.157;
5.W.237.166; 5.W.237.169; 5.W.237.172; 5.W.237.175; 5.W.237.240;
5.W.237.244; 5.W.238.228; 5.W.238.229; 5.W.238.230; 5.W.238.231;
5.W.238.236; 5.W.238.237; 5.W.238.238; 5.W.238.239; 5.W.238.154;
5.W.238.157; 5.W.238.166; 5.W.238.169; 5.W.238.172; 5.W.238.175;
5.W.238.240; 5.W.238.244; 5.W.239.228; 5.W.239.229; 5.W.239.230;
5.W.239.231; 5.W.239.236; 5.W.239.237; 5.W.239.238; 5.W.239.239;
5.W.239.154; 5.W.239.157; 5.W.239.166; 5.W.239.169; 5.W.239.172;
5.W.239.175; 5.W.239.240; 5.W.239.244; 5.W.154.228; 5.W.154.229;
5.W.154.230; 5.W.154.231; 5.W.154.236; 5.W.154.237; 5.W.154.238;
5.W.154.239; 5.W.154.154; 5.W.154.157; 5.W.154.166; 5.W.154.169;
5.W.154.172; 5.W.154.175; 5.W.154.240; 5.W.154.244; 5.W.157.228;
5.W.157.229; 5.W.157.230; 5.W.157.231; 5.W.157.236; 5.W.157.237;
5.W.157.238; 5.W.157.239; 5.W.157.154; 5.W.157.157; 5.W.157.166;
5.W.157.169; 5.W.157.172; 5.W.157.175; 5.W.157.240; 5.W.157.244;
5.W.166.228; 5.W.166.229; 5.W.166.230; 5.W.166.231; 5.W.166.236;
5.W.166.237; 5.W.166.238; 5.W.166.239; 5.W.166.154; 5.W.166.157;
5.W.166.166; 5.W.166.169; 5.W.166.172; 5.W.166.175; 5.W.166.240;
5.W.166.244; 5.W.169.228; 5.W.169.229; 5.W.169.230; 5.W.169.231;
5.W.169.236; 5.W.169.237; 5.W.169.238; 5.W.169.239; 5.W.169.154;
5.W.169.157; 5.W.169.166; 5.W.169.169; 5.W.169.172; 5.W.169.175;
5.W.169.240; 5.W.169.244; 5.W.172.228; 5.W.172.229; 5.W.172.230;
5.W.172.231; 5.W.172.236; 5.W.172.237; 5.W.172.238; 5.W.172.239;
5.W.172.154; 5.W.172.157; 5.W.172.166; 5.W.172.169; 5.W.172.172;
5.W.172.175; 5.W.172.240; 5.W.172.244; 5.W.175.228; 5.W.175.229;
5.W.175.230; 5.W.175.231; 5.W.175.236; 5.W.175.237; 5.W.175.238;
5.W.175.239; 5.W.175.154; 5.W.175.157; 5.W.175.166; 5.W.175.169;
5.W.175.172; 5.W.175.175; 5.W.175.240; 5.W.175.244; 5.W.240.228;
5.W.240.229; 5.W.240.230; 5.W.240.231; 5.W.240.236; 5.W.240.237;
5.W.240.238; 5.W.240.239; 5.W.240.154; 5.W.240.157; 5.W.240.166;
5.W.240.169; 5.W.240.172; 5.W.240.175; 5.W.240.240; 5.W.240.244;
5.W.244.228; 5.W.244.229; 5.W.244.230; 5.W.244.231; 5.W.244.236;
5.W.244.237; 5.W.244.238; 5.W.244.239; 5.W.244.154; 5.W.244.157;
5.W.244.166; 5.W.244.169; 5.W.244.172; 5.W.244.175; 5.W.244.240;
5.W.244.244;
Prodrugs of 5.Y 5.Y.228.228; 5.Y.228.229; 5.Y.228.230; 5.Y.228.231; 5.Y.228.236;
5.Y.228.237; 5.Y.228.238; 5.Y.228.239; 5.Y.228.154; 5.Y.228.157; 5.Y.228.166;
5.Y.228.169; 5.Y.228.172; 5.Y.228.175; 5.Y.228.240; 5.Y.228.244; 5.Y.229.228;

TABLE 100-continued

5.Y.229.229; 5.Y.229.230; 5.Y.229.231; 5.Y.229.236; 5.Y.229.237; 5.Y.229.238;
5.Y.229.239; 5.Y.229.154; 5.Y.229.157; 5.Y.229.166; 5.Y.229.169; 5.Y.229.172;
5.Y.229.175; 5.Y.229.240; 5.Y.229.244; 5.Y.230.228; 5.Y.230.229; 5.Y.230.230;
5.Y.230.231; 5.Y.230.236; 5.Y.230.237; 5.Y.230.238; 5.Y.230.239; 5.Y.230.154;
5.Y.230.157; 5.Y.230.166; 5.Y.230.169; 5.Y.230.172; 5.Y.230.175; 5.Y.230.240;
5.Y.230.244; 5.Y.231.228; 5.Y.231.229; 5.Y.231.230; 5.Y.231.231; 5.Y.231.236;
5.Y.231.237; 5.Y.231.238; 5.Y.231.239; 5.Y.231.154; 5.Y.231.157; 5.Y.231.166;
5.Y.231.169; 5.Y.231.172; 5.Y.231.175; 5.Y.231.240; 5.Y.231.244; 5.Y.236.228;
5.Y.236.229; 5.Y.236.230; 5.Y.236.231; 5.Y.236.236; 5.Y.236.237; 5.Y.236.238;
5.Y.236.239; 5.Y.236.154; 5.Y.236.157; 5.Y.236.166; 5.Y.236.169; 5.Y.236.172;
5.Y.236.175; 5.Y.236.240; 5.Y.236.244; 5.Y.237.228; 5.Y.237.229; 5.Y.237.230;
5.Y.237.231; 5.Y.237.236; 5.Y.237.237; 5.Y.237.238; 5.Y.237.239; 5.Y.237.154;
5.Y.237.157; 5.Y.237.166; 5.Y.237.169; 5.Y.237.172; 5.Y.237.175; 5.Y.237.240;
5.Y.237.244; 5.Y.238.228; 5.Y.238.229; 5.Y.238.230; 5.Y.238.231; 5.Y.238.236;
5.Y.238.237; 5.Y.238.238; 5.Y.238.239; 5.Y.238.154; 5.Y.238.157; 5.Y.238.166;
5.Y.238.169; 5.Y.238.172; 5.Y.238.175; 5.Y.238.240; 5.Y.238.244; 5.Y.239.228;
5.Y.239.229; 5.Y.239.230; 5.Y.239.231; 5.Y.239.236; 5.Y.239.237; 5.Y.239.238;
5.Y.239.239; 5.Y.239.154; 5.Y.239.157; 5.Y.239.166; 5.Y.239.169; 5.Y.239.172;
5.Y.239.175; 5.Y.239.240; 5.Y.239.244; 5.Y.154.228; 5.Y.154.229; 5.Y.154.230;
5.Y.154.231; 5.Y.154.236; 5.Y.154.237; 5.Y.154.238; 5.Y.154.239; 5.Y.154.154;
5.Y.154.157; 5.Y.154.166; 5.Y.154.169; 5.Y.154.172; 5.Y.154.175; 5.Y.154.240;
5.Y.154.244; 5.Y.157.228; 5.Y.157.229; 5.Y.157.230; 5.Y.157.231; 5.Y.157.236;
5.Y.157.237; 5.Y.157.238; 5.Y.157.239; 5.Y.157.154; 5.Y.157.157; 5.Y.157.166;
5.Y.157.169; 5.Y.157.172; 5.Y.157.175; 5.Y.157.240; 5.Y.157.244; 5.Y.166.228;
5.Y.166.229; 5.Y.166.230; 5.Y.166.231; 5.Y.166.236; 5.Y.166.237; 5.Y.166.238;
5.Y.166.239; 5.Y.166.154; 5.Y.166.157; 5.Y.166.166; 5.Y.166.169; 5.Y.166.172;
5.Y.166.175; 5.Y.166.240; 5.Y.166.244; 5.Y.169.228; 5.Y.169.229; 5.Y.169.230;
5.Y.169.231; 5.Y.169.236; 5.Y.169.237; 5.Y.169.238; 5.Y.169.239; 5.Y.169.154;
5.Y.169.157; 5.Y.169.166; 5.Y.169.169; 5.Y.169.172; 5.Y.169.175; 5.Y.169.240;
5.Y.169.244; 5.Y.172.228; 5.Y.172.229; 5.Y.172.230; 5.Y.172.231; 5.Y.172.236;
5.Y.172.237; 5.Y.172.238; 5.Y.172.239; 5.Y.172.154; 5.Y.172.157; 5.Y.172.166;
5.Y.172.169; 5.Y.172.172; 5.Y.172.175; 5.Y.172.240; 5.Y.172.244; 5.Y.175.228;
5.Y.175.229; 5.Y.175.230; 5.Y.175.231; 5.Y.175.236; 5.Y.175.237; 5.Y.175.238;
5.Y.175.239; 5.Y.175.154; 5.Y.175.157; 5.Y.175.166; 5.Y.175.169; 5.Y.175.172;
5.Y.175.175; 5.Y.175.240; 5.Y.175.244; 5.Y.240.228; 5.Y.240.229; 5.Y.240.230;
5.Y.240.231; 5.Y.240.236; 5.Y.240.237; 5.Y.240.238; 5.Y.240.239; 5.Y.240.154;
5.Y.240.157; 5.Y.240.166; 5.Y.240.169; 5.Y.240.172; 5.Y.240.175; 5.Y.240.240;
5.Y.240.244; 5.Y.244.228; 5.Y.244.229; 5.Y.244.230; 5.Y.244.231; 5.Y.244.236;
5.Y.244.237; 5.Y.244.238; 5.Y.244.239; 5.Y.244.154; 5.Y.244.157; 5.Y.244.166;
5.Y.244.169; 5.Y.244.172; 5.Y.244.175; 5.Y.244.240; 5.Y.244.244;
Prodrugs of 6.B 6.B.228.228; 6.B.228.229; 6.B.228.230; 6.B.228.231; 6.B.228.236;
6.B.228.237; 6.B.228.238; 6.B.228.239; 6.B.228.154; 6.B.228.157; 6.B.228.166;
6.B.228.169; 6.B.228.172; 6.B.228.175; 6.B.228.240; 6.B.228.244; 6.B.229.228;
6.B.229.229; 6.B.229.230; 6.B.229.231; 6.B.229.236; 6.B.229.237; 6.B.229.238;
6.B.229.239; 6.B.229.154; 6.B.229.157; 6.B.229.166; 6.B.229.169; 6.B.229.172;
6.B.229.175; 6.B.229.240; 6.B.229.244; 6.B.230.228; 6.B.230.229; 6.B.230.230;
6.B.230.231; 6.B.230.236; 6.B.230.237; 6.B.230.238; 6.B.230.239; 6.B.230.154;
6.B.230.157; 6.B.230.166; 6.B.230.169; 6.B.230.172; 6.B.230.175; 6.B.230.240;
6.B.230.244; 6.B.231.228; 6.B.231.229; 6.B.231.230; 6.B.231.231; 6.B.231.236;
6.B.231.237; 6.B.231.238; 6.B.231.239; 6.B.231.154; 6.B.231.157; 6.B.231.166;
6.B.231.169; 6.B.231.172; 6.B.231.175; 6.B.231.240; 6.B.231.244; 6.B.236.228;
6.B.236.229; 6.B.236.230; 6.B.236.231; 6.B.236.236; 6.B.236.237; 6.B.236.238;
6.B.236.239; 6.B.236.154; 6.B.236.157; 6.B.236.166; 6.B.236.169; 6.B.236.172;
6.B.236.175; 6.B.236.240; 6.B.236.244; 6.B.237.228; 6.B.237.229; 6.B.237.230;
6.B.237.231; 6.B.237.236; 6.B.237.237; 6.B.237.238; 6.B.237.239; 6.B.237.154;
6.B.237.157; 6.B.237.166; 6.B.237.169; 6.B.237.172; 6.B.237.175; 6.B.237.240;
6.B.237.244; 6.B.238.228; 6.B.238.229; 6.B.238.230; 6.B.238.231; 6.B.238.236;
6.B.238.237; 6.B.238.238; 6.B.238.239; 6.B.238.154; 6.B.238.157; 6.B.238.166;
6.B.238.169; 6.B.238.172; 6.B.238.175; 6.B.238.240; 6.B.238.244; 6.B.239.228;
6.B.239.229; 6.B.239.230; 6.B.239.231; 6.B.239.236; 6.B.239.237; 6.B.239.238;
6.B.239.239; 6.B.239.154; 6.B.239.157; 6.B.239.166; 6.B.239.169; 6.B.239.172;
6.B.239.175; 6.B.239.240; 6.B.239.244; 6.B.154.228; 6.B.154.229; 6.B.154.230;
6.B.154.231; 6.B.154.236; 6.B.154.237; 6.B.154.238; 6.B.154.239; 6.B.154.154;
6.B.154.157; 6.B.154.166; 6.B.154.169; 6.B.154.172; 6.B.154.175; 6.B.154.240;
6.B.154.244; 6.B.157.228; 6.B.157.229; 6.B.157.230; 6.B.157.231; 6.B.157.236;
6.B.157.237; 6.B.157.238; 6.B.157.239; 6.B.157.154; 6.B.157.157; 6.B.157.166;
6.B.157.169; 6.B.157.172; 6.B.157.175; 6.B.157.240; 6.B.157.244; 6.B.166.228;
6.B.166.229; 6.B.166.230; 6.B.166.231; 6.B.166.236; 6.B.166.237; 6.B.166.238;
6.B.166.239; 6.B.166.154; 6.B.166.157; 6.B.166.166; 6.B.166.169; 6.B.166.172;
6.B.166.175; 6.B.166.240; 6.B.166.244; 6.B.169.228; 6.B.169.229; 6.B.169.230;
6.B.169.231; 6.B.169.236; 6.B.169.237; 6.B.169.238; 6.B.169.239; 6.B.169.154;
6.B.169.157; 6.B.169.166; 6.B.169.169; 6.B.169.172; 6.B.169.175; 6.B.169.240;
6.B.169.244; 6.B.172.228; 6.B.172.229; 6.B.172.230; 6.B.172.231; 6.B.172.236;
6.B.172.237; 6.B.172.238; 6.B.172.239; 6.B.172.154; 6.B.172.157; 6.B.172.166;
6.B.172.169; 6.B.172.172; 6.B.172.175; 6.B.172.240; 6.B.172.244; 6.B.175.228;
6.B.175.229; 6.B.175.230; 6.B.175.231; 6.B.175.236; 6.B.175.237; 6.B.175.238;
6.B.175.239; 6.B.175.154; 6.B.175.157; 6.B.175.166; 6.B.175.169; 6.B.175.172;

TABLE 100-continued

6.B.175.175; 6.B.175.240; 6.B.175.244; 6.B.240.228; 6.B.240.229; 6.B.240.230;
6.B.240.231; 6.B.240.236; 6.B.240.237; 6.B.240.238; 6.B.240.239; 6.B.240.154;
6.B.240.157; 6.B.240.166; 6.B.240.169; 6.B.240.172; 6.B.240.175; 6.B.240.240;
6.B.240.244; 6.B.244.228; 6.B.244.229; 6.B.244.230; 6.B.244.231; 6.B.244.236;
6.B.244.237; 6.B.244.238; 6.B.244.239; 6.B.244.154; 6.B.244.157; 6.B.244.166;
6.B.244.169; 6.B.244.172; 6.B.244.175; 6.B.244.240; 6.B.244.244;
Prodrugs of 6.D 6.D.228.228; 6.D.228.229; 6.D.228.230; 6.D.228.231; 6.D.228.236;
6.D.228.237; 6.D.228.238; 6.D.228.239; 6.D.228.154; 6.D.228.157;
6.D.228.166; 6.D.228.169; 6.D.228.172; 6.D.228.175; 6.D.228.240;
6.D.228.244; 6.D.229.228; 6.D.229.229; 6.D.229.230; 6.D.229.231;
6.D.229.236; 6.D.229.237; 6.D.229.238; 6.D.229.239; 6.D.229.154;
6.D.229.157; 6.D.229.166; 6.D.229.169; 6.D.229.172; 6.D.229.175;
6.D.229.240; 6.D.229.244; 6.D.230.228; 6.D.230.229; 6.D.230.230;
6.D.230.231; 6.D.230.236; 6.D.230.237; 6.D.230.238; 6.D.230.239;
6.D.230.154; 6.D.230.157; 6.D.230.166; 6.D.230.169; 6.D.230.172;
6.D.230.175; 6.D.230.240; 6.D.230.244; 6.D.231.228; 6.D.231.229;
6.D.231.230; 6.D.231.231; 6.D.231.236; 6.D.231.237; 6.D.231.238;
6.D.231.239; 6.D.231.154; 6.D.231.157; 6.D.231.166; 6.D.231.169;
6.D.231.172; 6.D.231.175; 6.D.231.240; 6.D.231.244; 6.D.236.228;
6.D.236.229; 6.D.236.230; 6.D.236.231; 6.D.236.236; 6.D.236.237;
6.D.236.238; 6.D.236.239; 6.D.236.154; 6.D.236.157; 6.D.236.166;
6.D.236.169; 6.D.236.172; 6.D.236.175; 6.D.236.240; 6.D.236.244;
6.D.237.228; 6.D.237.229; 6.D.237.230; 6.D.237.231; 6.D.237.236;
6.D.237.237; 6.D.237.238; 6.D.237.239; 6.D.237.154; 6.D.237.157;
6.D.237.166; 6.D.237.169; 6.D.237.172; 6.D.237.175; 6.D.237.240;
6.D.237.244; 6.D.238.228; 6.D.238.229; 6.D.238.230; 6.D.238.231;
6.D.238.236; 6.D.238.237; 6.D.238.238; 6.D.238.239; 6.D.238.154;
6.D.238.157; 6.D.238.166; 6.D.238.169; 6.D.238.172; 6.D.238.175;
6.D.238.240; 6.D.238.244; 6.D.239.228; 6.D.239.229; 6.D.239.230;
6.D.239.231; 6.D.239.236; 6.D.239.237; 6.D.239.238; 6.D.239.239;
6.D.239.154; 6.D.239.157; 6.D.239.166; 6.D.239.169; 6.D.239.172;
6.D.239.175; 6.D.239.240; 6.D.239.244; 6.D.154.228; 6.D.154.229;
6.D.154.230; 6.D.154.231; 6.D.154.236; 6.D.154.237; 6.D.154.238;
6.D.154.239; 6.D.154.154; 6.D.154.157; 6.D.154.166; 6.D.154.169;
6.D.154.172; 6.D.154.175; 6.D.154.240; 6.D.154.244; 6.D.157.228;
6.D.157.229; 6.D.157.230; 6.D.157.231; 6.D.157.236; 6.D.157.237;
6.D.157.238; 6.D.157.239; 6.D.157.154; 6.D.157.157; 6.D.157.166;
6.D.157.169; 6.D.157.172; 6.D.157.175; 6.D.157.240; 6.D.157.244;
6.D.166.228; 6.D.166.229; 6.D.166.230; 6.D.166.231; 6.D.166.236;
6.D.166.237; 6.D.166.238; 6.D.166.239; 6.D.166.154; 6.D.166.157;
6.D.166.166; 6.D.166.169; 6.D.166.172; 6.D.166.175; 6.D.166.240;
6.D.166.244; 6.D.169.228; 6.D.169.229; 6.D.169.230; 6.D.169.231;
6.D.169.236; 6.D.169.237; 6.D.169.238; 6.D.169.239; 6.D.169.154;
6.D.169.157; 6.D.169.166; 6.D.169.169; 6.D.169.172; 6.D.169.175;
6.D.169.240; 6.D.169.244; 6.D.172.228; 6.D.172.229; 6.D.172.230;
6.D.172.231; 6.D.172.236; 6.D.172.237; 6.D.172.238; 6.D.172.239;
6.D.172.154; 6.D.172.157; 6.D.172.166; 6.D.172.169; 6.D.172.172;
6.D.172.175; 6.D.172.240; 6.D.172.244; 6.D.175.228; 6.D.175.229;
6.D.175.230; 6.D.175.231; 6.D.175.236; 6.D.175.237; 6.D.175.238;
6.D.175.239; 6.D.175.154; 6.D.175.157; 6.D.175.166; 6.D.175.169;
6.D.175.172; 6.D.175.175; 6.D.175.240; 6.D.175.244; 6.D.240.228;
6.D.240.229; 6.D.240.230; 6.D.240.231; 6.D.240.236; 6.D.240.237;
6.D.240.238; 6.D.240.239; 6.D.240.154; 6.D.240.157; 6.D.240.166;
6.D.240.169; 6.D.240.172; 6.D.240.175; 6.D.240.240; 6.D.240.244;
6.D.244.228; 6.D.244.229; 6.D.244.230; 6.D.244.231; 6.D.244.236;
6.D.244.237; 6.D.244.238; 6.D.244.239; 6.D.244.154; 6.D.244.157;
6.D.244.166; 6.D.244.169; 6.D.244.172; 6.D.244.175; 6.D.244.240;
6.D.244.244;
Prodrugs of 6.E 6.E.228.228; 6.E.228.229; 6.E.228.230; 6.E.228.231; 6.E.228.236;
6.E.228.237; 6.E.228.238; 6.E.228.239; 6.E.228.154; 6.E.228.157; 6.E.228.166;
6.E.228.169; 6.E.228.172; 6.E.228.175; 6.E.228.240; 6.E.228.244; 6.E.229.228;
6.E.229.229; 6.E.229.230; 6.E.229.231; 6.E.229.236; 6.E.229.237; 6.E.229.238;
6.E.229.239; 6.E.229.154; 6.E.229.157; 6.E.229.166; 6.E.229.169; 6.E.229.172;
6.E.229.175; 6.E.229.240; 6.E.229.244; 6.E.230.228; 6.E.230.229; 6.E.230.230;
6.E.230.231; 6.E.230.236; 6.E.230.237; 6.E.230.238; 6.E.230.239; 6.E.230.154;
6.E.230.157; 6.E.230.166; 6.E.230.169; 6.E.230.172; 6.E.230.175; 6.E.230.240;
6.E.230.244; 6.E.231.228; 6.E.231.229; 6.E.231.230; 6.E.231.231; 6.E.231.236;
6.E.231.237; 6.E.231.238; 6.E.231.239; 6.E.231.154; 6.E.231.157; 6.E.231.166;
6.E.231.169; 6.E.231.172; 6.E.231.175; 6.E.231.240; 6.E.231.244; 6.E.236.228;
6.E.236.229; 6.E.236.230; 6.E.236.231; 6.E.236.236; 6.E.236.237; 6.E.236.238;
6.E.236.239; 6.E.236.154; 6.E.236.157; 6.E.236.166; 6.E.236.169; 6.E.236.172;
6.E.236.175; 6.E.236.240; 6.E.236.244; 6.E.237.228; 6.E.237.229; 6.E.237.230;
6.E.237.231; 6.E.237.236; 6.E.237.237; 6.E.237.238; 6.E.237.239; 6.E.237.154;
6.E.237.157; 6.E.237.166; 6.E.237.169; 6.E.237.172; 6.E.237.175; 6.E.237.240;
6.E.237.244; 6.E.238.228; 6.E.238.229; 6.E.238.230; 6.E.238.231; 6.E.238.236;

TABLE 100-continued

6.E.238.237; 6.E.238.238; 6.E.238.239; 6.E.238.154; 6.E.238.157; 6.E.238.166;
6.E.238.169; 6.E.238.172; 6.E.238.175; 6.E.238.240; 6.E.238.244; 6.E.239.228;
6.E.239.229; 6.E.239.230; 6.E.239.231; 6.E.239.236; 6.E.239.237; 6.E.239.238;
6.E.239.239; 6.E.239.154; 6.E.239.157; 6.E.239.166; 6.E.239.169; 6.E.239.172;
6.E.239.175; 6.E.239.240; 6.E.239.244; 6.E.154.228; 6.E.154.229; 6.E.154.230;
6.E.154.231; 6.E.154.236; 6.E.154.237; 6.E.154.238; 6.E.154.239; 6.E.154.154;
6.E.154.157; 6.E.154.166; 6.E.154.169; 6.E.154.172; 6.E.154.175; 6.E.154.240;
6.E.154.244; 6.E.157.228; 6.E.157.229; 6.E.157.230; 6.E.157.231; 6.E.157.236;
6.E.157.237; 6.E.157.238; 6.E.157.239; 6.E.157.154; 6.E.157.157; 6.E.157.166;
6.E.157.169; 6.E.157.172; 6.E.157.175; 6.E.157.240; 6.E.157.244; 6.E.166.228;
6.E.166.229; 6.E.166.230; 6.E.166.231; 6.E.166.236; 6.E.166.237; 6.E.166.238;
6.E.166.239; 6.E.166.154; 6.E.166.157; 6.E.166.166; 6.E.166.169; 6.E.166.172;
6.E.166.175; 6.E.166.240; 6.E.166.244; 6.E.169.228; 6.E.169.229; 6.E.169.230;
6.E.169.231; 6.E.169.236; 6.E.169.237; 6.E.169.238; 6.E.169.239; 6.E.169.154;
6.E.169.157; 6.E.169.166; 6.E.169.169; 6.E.169.172; 6.E.169.175; 6.E.169.240;
6.E.169.244; 6.E.172.228; 6.E.172.229; 6.E.172.230; 6.E.172.231; 6.E.172.236;
6.E.172.237; 6.E.172.238; 6.E.172.239; 6.E.172.154; 6.E.172.157; 6.E.172.166;
6.E.172.169; 6.E.172.172; 6.E.172.175; 6.E.172.240; 6.E.172.244; 6.E.175.228;
6.E.175.229; 6.E.175.230; 6.E.175.231; 6.E.175.236; 6.E.175.237; 6.E.175.238;
6.E.175.239; 6.E.175.154; 6.E.175.157; 6.E.175.166; 6.E.175.169; 6.E.175.172;
6.E.175.175; 6.E.175.240; 6.E.175.244; 6.E.240.228; 6.E.240.229; 6.E.240.230;
6.E.240.231; 6.E.240.236; 6.E.240.237; 6.E.240.238; 6.E.240.239; 6.E.240.154;
6.E.240.157; 6.E.240.166; 6.E.240.169; 6.E.240.172; 6.E.240.175; 6.E.240.240;
6.E.240.244; 6.E.244.228; 6.E.244.229; 6.E.244.230; 6.E.244.231; 6.E.244.236;
6.E.244.237; 6.E.244.238; 6.E.244.239; 6.E.244.154; 6.E.244.157; 6.E.244.166;
6.E.244.169; 6.E.244.172; 6.E.244.175; 6.E.244.240; 6.E.244.244;

Prodrugs of 6.G

6.G.228.228; 6.G.228.229; 6.G.228.230; 6.G.228.231; 6.G.228.236;
6.G.228.237; 6.G.228.238; 6.G.228.239; 6.G.228.154; 6.G.228.157;
6.G.228.166; 6.G.228.169; 6.G.228.172; 6.G.228.175; 6.G.228.240;
6.G.228.244; 6.G.229.228; 6.G.229.229; 6.G.229.230; 6.G.229.231;
6.G.229.236; 6.G.229.237; 6.G.229.238; 6.G.229.239; 6.G.229.154;
6.G.229.157; 6.G.229.166; 6.G.229.169; 6.G.229.172; 6.G.229.175;
6.G.229.240; 6.G.229.244; 6.G.230.228; 6.G.230.229; 6.G.230.230;
6.G.230.231; 6.G.230.236; 6.G.230.237; 6.G.230.238; 6.G.230.239;
6.G.230.154; 6.G.230.157; 6.G.230.166; 6.G.230.169; 6.G.230.172;
6.G.230.175; 6.G.230.240; 6.G.230.244; 6.G.231.228; 6.G.231.229;
6.G.231.230; 6.G.231.231; 6.G.231.236; 6.G.231.237; 6.G.231.238;
6.G.231.239; 6.G.231.154; 6.G.231.157; 6.G.231.166; 6.G.231.169;
6.G.231.172; 6.G.231.175; 6.G.231.240; 6.G.231.244; 6.G.236.228;
6.G.236.229; 6.G.236.230; 6.G.236.231; 6.G.236.236; 6.G.236.237;
6.G.236.238; 6.G.236.239; 6.G.236.154; 6.G.236.157; 6.G.236.166;
6.G.236.169; 6.G.236.172; 6.G.236.175; 6.G.236.240; 6.G.236.244;
6.G.237.228; 6.G.237.229; 6.G.237.230; 6.G.237.231; 6.G.237.236;
6.G.237.237; 6.G.237.238; 6.G.237.239; 6.G.237.154; 6.G.237.157;
6.G.237.166; 6.G.237.169; 6.G.237.172; 6.G.237.175; 6.G.237.240;
6.G.237.244; 6.G.238.228; 6.G.238.229; 6.G.238.230; 6.G.238.231;
6.G.238.236; 6.G.238.237; 6.G.238.238; 6.G.238.239; 6.G.238.154;
6.G.238.157; 6.G.238.166; 6.G.238.169; 6.G.238.172; 6.G.238.175;
6.G.238.240; 6.G.238.244; 6.G.239.228; 6.G.239.229; 6.G.239.230;
6.G.239.231; 6.G.239.236; 6.G.239.237; 6.G.239.238; 6.G.239.239;
6.G.239.154; 6.G.239.157; 6.G.239.166; 6.G.239.169; 6.G.239.172;
6.G.239.175; 6.G.239.240; 6.G.239.244; 6.G.154.228; 6.G.154.229;
6.G.154.230; 6.G.154.231; 6.G.154.236; 6.G.154.237; 6.G.154.238;
6.G.154.239; 6.G.154.154; 6.G.154.157; 6.G.154.166; 6.G.154.169;
6.G.154.172; 6.G.154.175; 6.G.154.240; 6.G.154.244; 6.G.157.228;
6.G.157.229; 6.G.157.230; 6.G.157.231; 6.G.157.236; 6.G.157.237;
6.G.157.238; 6.G.157.239; 6.G.157.154; 6.G.157.157; 6.G.157.166;
6.G.157.169; 6.G.157.172; 6.G.157.175; 6.G.157.240; 6.G.157.244;
6.G.166.228; 6.G.166.229; 6.G.166.230; 6.G.166.231; 6.G.166.236;
6.G.166.237; 6.G.166.238; 6.G.166.239; 6.G.166.154; 6.G.166.157;
6.G.166.166; 6.G.166.169; 6.G.166.172; 6.G.166.175; 6.G.166.240;
6.G.166.244; 6.G.169.228; 6.G.169.229; 6.G.169.230; 6.G.169.231;
6.G.169.236; 6.G.169.237; 6.G.169.238; 6.G.169.239; 6.G.169.154;
6.G.169.157; 6.G.169.166; 6.G.169.169; 6.G.169.172; 6.G.169.175;
6.G.169.240; 6.G.169.244; 6.G.172.228; 6.G.172.229; 6.G.172.230;
6.G.172.231; 6.G.172.236; 6.G.172.237; 6.G.172.238; 6.G.172.239;
6.G.172.154; 6.G.172.157; 6.G.172.166; 6.G.172.169; 6.G.172.172;
6.G.172.175; 6.G.172.240; 6.G.172.244; 6.G.175.228; 6.G.175.229;
6.G.175.230; 6.G.175.231; 6.G.175.236; 6.G.175.237; 6.G.175.238;
6.G.175.239; 6.G.175.154; 6.G.175.157; 6.G.175.166; 6.G.175.169;
6.G.175.172; 6.G.175.175; 6.G.175.240; 6.G.175.244; 6.G.240.228;
6.G.240.229; 6.G.240.230; 6.G.240.231; 6.G.240.236; 6.G.240.237;
6.G.240.238; 6.G.240.239; 6.G.240.154; 6.G.240.157; 6.G.240.166;
6.G.240.169; 6.G.240.172; 6.G.240.175; 6.G.240.240; 6.G.240.244;
6.G.244.228; 6.G.244.229; 6.G.244.230; 6.G.244.231; 6.G.244.236;

TABLE 100-continued

6.G.244.237; 6.G.244.238; 6.G.244.239; 6.G.244.154; 6.G.244.157;
6.G.244.166; 6.G.244.169; 6.G.244.172; 6.G.244.175; 6.G.244.240;
6.G.244.244;

Prodrugs of 6.I

6.I.228.228; 6.I.228.229; 6.I.228.230; 6.I.228.231; 6.I.228.236; 6.I.228.237;
6.I.228.238; 6.I.228.239; 6.I.228.154; 6.I.228.157; 6.I.228.166; 6.I.228.169;
6.I.228.172; 6.I.228.175; 6.I.228.240; 6.I.228.244; 6.I.229.228; 6.I.229.229;
6.I.229.230; 6.I.229.231; 6.I.229.236; 6.I.229.237; 6.I.229.238; 6.I.229.239;
6.I.229.154; 6.I.229.157; 6.I.229.166; 6.I.229.169; 6.I.229.172; 6.I.229.175;
6.I.229.240; 6.I.229.244; 6.I.230.228; 6.I.230.229; 6.I.230.230; 6.I.230.231;
6.I.230.236; 6.I.230.237; 6.I.230.238; 6.I.230.239; 6.I.230.154; 6.I.230.157;
6.I.230.166; 6.I.230.169; 6.I.230.172; 6.I.230.175; 6.I.230.240; 6.I.230.244;
6.I.231.228; 6.I.231.229; 6.I.231.230; 6.I.231.231; 6.I.231.236; 6.I.231.237;
6.I.231.238; 6.I.231.239; 6.I.231.154; 6.I.231.157; 6.I.231.166; 6.I.231.169;
6.I.231.172; 6.I.231.175; 6.I.231.240; 6.I.231.244; 6.I.236.228; 6.I.236.229;
6.I.236.230; 6.I.236.231; 6.I.236.236; 6.I.236.237; 6.I.236.238; 6.I.236.239;
6.I.236.154; 6.I.236.157; 6.I.236.166; 6.I.236.169; 6.I.236.172; 6.I.236.175;
6.I.236.240; 6.I.236.244; 6.I.237.228; 6.I.237.229; 6.I.237.230; 6.I.237.231;
6.I.237.236; 6.I.237.237; 6.I.237.238; 6.I.237.239; 6.I.237.154; 6.I.237.157;
6.I.237.166; 6.I.237.169; 6.I.237.172; 6.I.237.175; 6.I.237.240; 6.I.237.244;
6.I.238.228; 6.I.238.229; 6.I.238.230; 6.I.238.231; 6.I.238.236; 6.I.238.237;
6.I.238.238; 6.I.238.239; 6.I.238.154; 6.I.238.157; 6.I.238.166; 6.I.238.169;
6.I.238.172; 6.I.238.175; 6.I.238.240; 6.I.238.244; 6.I.239.228; 6.I.239.229;
6.I.239.230; 6.I.239.231; 6.I.239.236; 6.I.239.237; 6.I.239.238; 6.I.239.239;
6.I.239.154; 6.I.239.157; 6.I.239.166; 6.I.239.169; 6.I.239.172; 6.I.239.175;
6.I.239.240; 6.I.239.244; 6.I.154.228; 6.I.154.229; 6.I.154.230; 6.I.154.231;
6.I.154.236; 6.I.154.237; 6.I.154.238; 6.I.154.239; 6.I.154.154; 6.I.154.157;
6.I.154.166; 6.I.154.169; 6.I.154.172; 6.I.154.175; 6.I.154.240; 6.I.154.244;
6.I.157.228; 6.I.157.229; 6.I.157.230; 6.I.157.231; 6.I.157.236; 6.I.157.237;
6.I.157.238; 6.I.157.239; 6.I.157.154; 6.I.157.157; 6.I.157.166; 6.I.157.169;
6.I.157.172; 6.I.157.175; 6.I.157.240; 6.I.157.244; 6.I.166.228; 6.I.166.229;
6.I.166.230; 6.I.166.231; 6.I.166.236; 6.I.166.237; 6.I.166.238; 6.I.166.239;
6.I.166.154; 6.I.166.157; 6.I.166.166; 6.I.166.169; 6.I.166.172; 6.I.166.175;
6.I.166.240; 6.I.166.244; 6.I.169.228; 6.I.169.229; 6.I.169.230; 6.I.169.231;
6.I.169.236; 6.I.169.237; 6.I.169.238; 6.I.169.239; 6.I.169.154; 6.I.169.157;
6.I.169.166; 6.I.169.169; 6.I.169.172; 6.I.169.175; 6.I.169.240; 6.I.169.244;
6.I.172.228; 6.I.172.229; 6.I.172.230; 6.I.172.231; 6.I.172.236; 6.I.172.237;
6.I.172.238; 6.I.172.239; 6.I.172.154; 6.I.172.157; 6.I.172.166; 6.I.172.169;
6.I.172.172; 6.I.172.175; 6.I.172.240; 6.I.172.244; 6.I.175.228; 6.I.175.229;
6.I.175.230; 6.I.175.231; 6.I.175.236; 6.I.175.237; 6.I.175.238; 6.I.175.239;
6.I.175.154; 6.I.175.157; 6.I.175.166; 6.I.175.169; 6.I.175.172; 6.I.175.175;
6.I.175.240; 6.I.175.244; 6.I.240.228; 6.I.240.229; 6.I.240.230; 6.I.240.231;
6.I.240.236; 6.I.240.237; 6.I.240.238; 6.I.240.239; 6.I.240.154; 6.I.240.157;
6.I.240.166; 6.I.240.169; 6.I.240.172; 6.I.240.175; 6.I.240.240; 6.I.240.244;
6.I.244.228; 6.I.244.229; 6.I.244.230; 6.I.244.231; 6.I.244.236; 6.I.244.237;
6.I.244.238; 6.I.244.239; 6.I.244.154; 6.I.244.157; 6.I.244.166; 6.I.244.169;
6.I.244.172; 6.I.244.175; 6.I.244.240; 6.I.244.244;

Prodrugs of 6.J

6.J.228.228; 6.J.228.229; 6.J.228.230; 6.J.228.231; 6.J.228.236; 6.J.228.237;
6.J.228.238; 6.J.228.239; 6.J.228.154; 6.J.228.157; 6.J.228.166; 6.J.228.169;
6.J.228.172; 6.J.228.175; 6.J.228.240; 6.J.228.244; 6.J.229.228; 6.J.229.229;
6.J.229.230; 6.J.229.231; 6.J.229.236; 6.J.229.237; 6.J.229.238; 6.J.229.239;
6.J.229.154; 6.J.229.157; 6.J.229.166; 6.J.229.169; 6.J.229.172; 6.J.229.175;
6.J.229.240; 6.J.229.244; 6.J.230.228; 6.J.230.229; 6.J.230.230; 6.J.230.231;
6.J.230.236; 6.J.230.237; 6.J.230.238; 6.J.230.239; 6.J.230.154; 6.J.230.157;
6.J.230.166; 6.J.230.169; 6.J.230.172; 6.J.230.175; 6.J.230.240; 6.J.230.244;
6.J.231.228; 6.J.231.229; 6.J.231.230; 6.J.231.231; 6.J.231.236; 6.J.231.237;
6.J.231.238; 6.J.231.239; 6.J.231.154; 6.J.231.157; 6.J.231.166; 6.J.231.169;
6.J.231.172; 6.J.231.175; 6.J.231.240; 6.J.231.244; 6.J.236.228; 6.J.236.229;
6.J.236.230; 6.J.236.231; 6.J.236.236; 6.J.236.237; 6.J.236.238; 6.J.236.239;
6.J.236.154; 6.J.236.157; 6.J.236.166; 6.J.236.169; 6.J.236.172; 6.J.236.175;
6.J.236.240; 6.J.236.244; 6.J.237.228; 6.J.237.229; 6.J.237.230; 6.J.237.231;
6.J.237.236; 6.J.237.237; 6.J.237.238; 6.J.237.239; 6.J.237.154; 6.J.237.157;
6.J.237.166; 6.J.237.169; 6.J.237.172; 6.J.237.175; 6.J.237.240; 6.J.237.244;
6.J.238.228; 6.J.238.229; 6.J.238.230; 6.J.238.231; 6.J.238.236; 6.J.238.237;
6.J.238.238; 6.J.238.239; 6.J.238.154; 6.J.238.157; 6.J.238.166; 6.J.238.169;
6.J.238.172; 6.J.238.175; 6.J.238.240; 6.J.238.244; 6.J.239.228; 6.J.239.229;
6.J.239.230; 6.J.239.231; 6.J.239.236; 6.J.239.237; 6.J.239.238; 6.J.239.239;
6.J.239.154; 6.J.239.157; 6.J.239.166; 6.J.239.169; 6.J.239.172; 6.J.239.175;
6.J.239.240; 6.J.239.244; 6.J.154.228; 6.J.154.229; 6.J.154.230; 6.J.154.231;
6.J.154.236; 6.J.154.237; 6.J.154.238; 6.J.154.239; 6.J.154.154; 6.J.154.157;
6.J.154.166; 6.J.154.169; 6.J.154.172; 6.J.154.175; 6.J.154.240; 6.J.154.244;
6.J.157.228; 6.J.157.229; 6.J.157.230; 6.J.157.231; 6.J.157.236; 6.J.157.237;
6.J.157.238; 6.J.157.239; 6.J.157.154; 6.J.157.157; 6.J.157.166; 6.J.157.169;
6.J.157.172; 6.J.157.175; 6.J.157.240; 6.J.157.244; 6.J.166.228; 6.J.166.229;
6.J.166.230; 6.J.166.231; 6.J.166.236; 6.J.166.237; 6.J.166.238; 6.J.166.239;
6.J.166.154; 6.J.166.157; 6.J.166.166; 6.J.166.169; 6.J.166.172; 6.J.166.175;

TABLE 100-continued

6.J.166.240; 6.J.166.244; 6.J.169.228; 6.J.169.229; 6.J.169.230; 6.J.169.231;
6.J.169.236; 6.J.169.237; 6.J.169.238; 6.J.169.239; 6.J.169.154; 6.J.169.157;
6.J.169.166; 6.J.169.169; 6.J.169.172; 6.J.169.175; 6.J.169.240; 6.J.169.244;
6.J.172.228; 6.J.172.229; 6.J.172.230; 6.J.172.231; 6.J.172.236; 6.J.172.237;
6.J.172.238; 6.J.172.239; 6.J.172.154; 6.J.172.157; 6.J.172.166; 6.J.172.169;
6.J.172.172; 6.J.172.175; 6.J.172.240; 6.J.172.244; 6.J.175.228; 6.J.175.229;
6.J.175.230; 6.J.175.231; 6.J.175.236; 6.J.175.237; 6.J.175.238; 6.J.175.239;
6.J.175.154; 6.J.175.157; 6.J.175.166; 6.J.175.169; 6.J.175.172; 6.J.175.175;
6.J.175.240; 6.J.175.244; 6.J.240.228; 6.J.240.229; 6.J.240.230; 6.J.240.231;
6.J.240.236; 6.J.240.237; 6.J.240.238; 6.J.240.239; 6.J.240.154; 6.J.240.157;
6.J.240.166; 6.J.240.169; 6.J.240.172; 6.J.240.175; 6.J.240.240; 6.J.240.244;
6.J.244.228; 6.J.244.229; 6.J.244.230; 6.J.244.231; 6.J.244.236; 6.J.244.237;
6.J.244.238; 6.J.244.239; 6.J.244.154; 6.J.244.157; 6.J.244.166; 6.J.244.169;
6.J.244.172; 6.J.244.175; 6.J.244.240; 6.J.244.244;
Prodrugs of 6.L 6.L.228.228; 6.L.228.229; 6.L.228.230; 6.L.228.231; 6.L.228.236;
6.L.228.237; 6.L.228.238; 6.L.228.239; 6.L.228.154; 6.L.228.157; 6.L.228.166;
6.L.228.169; 6.L.228.172; 6.L.228.175; 6.L.228.240; 6.L.228.244; 6.L.229.228;
6.L.229.229; 6.L.229.230; 6.L.229.231; 6.L.229.236; 6.L.229.237; 6.L.229.238;
6.L.229.239; 6.L.229.154; 6.L.229.157; 6.L.229.166; 6.L.229.169; 6.L.229.172;
6.L.229.175; 6.L.229.240; 6.L.229.244; 6.L.230.228; 6.L.230.229; 6.L.230.230;
6.L.230.231; 6.L.230.236; 6.L.230.237; 6.L.230.238; 6.L.230.239; 6.L.230.154;
6.L.230.157; 6.L.230.166; 6.L.230.169; 6.L.230.172; 6.L.230.175; 6.L.230.240;
6.L.230.244; 6.L.231.228; 6.L.231.229; 6.L.231.230; 6.L.231.231; 6.L.231.236;
6.L.231.237; 6.L.231.238; 6.L.231.239; 6.L.231.154; 6.L.231.157; 6.L.231.166;
6.L.231.169; 6.L.231.172; 6.L.231.175; 6.L.231.240; 6.L.231.244; 6.L.236.228;
6.L.236.229; 6.L.236.230; 6.L.236.231; 6.L.236.236; 6.L.236.237; 6.L.236.238;
6.L.236.239; 6.L.236.154; 6.L.236.157; 6.L.236.166; 6.L.236.169; 6.L.236.172;
6.L.236.175; 6.L.236.240; 6.L.236.244; 6.L.237.228; 6.L.237.229; 6.L.237.230;
6.L.237.231; 6.L.237.236; 6.L.237.237; 6.L.237.238; 6.L.237.239; 6.L.237.154;
6.L.237.157; 6.L.237.166; 6.L.237.169; 6.L.237.172; 6.L.237.175; 6.L.237.240;
6.L.237.244; 6.L.238.228; 6.L.238.229; 6.L.238.230; 6.L.238.231; 6.L.238.236;
6.L.238.237; 6.L.238.238; 6.L.238.239; 6.L.238.154; 6.L.238.157; 6.L.238.166;
6.L.238.169; 6.L.238.172; 6.L.238.175; 6.L.238.240; 6.L.238.244; 6.L.239.228;
6.L.239.229; 6.L.239.230; 6.L.239.231; 6.L.239.236; 6.L.239.237; 6.L.239.238;
6.L.239.239; 6.L.239.154; 6.L.239.157; 6.L.239.166; 6.L.239.169; 6.L.239.172;
6.L.239.175; 6.L.239.240; 6.L.239.244; 6.L.154.228; 6.L.154.229; 6.L.154.230;
6.L.154.231; 6.L.154.236; 6.L.154.237; 6.L.154.238; 6.L.154.239; 6.L.154.154;
6.L.154.157; 6.L.154.166; 6.L.154.169; 6.L.154.172; 6.L.154.175; 6.L.154.240;
6.L.154.244; 6.L.157.228; 6.L.157.229; 6.L.157.230; 6.L.157.231; 6.L.157.236;
6.L.157.237; 6.L.157.238; 6.L.157.239; 6.L.157.154; 6.L.157.157; 6.L.157.166;
6.L.157.169; 6.L.157.172; 6.L.157.175; 6.L.157.240; 6.L.157.244; 6.L.166.228;
6.L.166.229; 6.L.166.230; 6.L.166.231; 6.L.166.236; 6.L.166.237; 6.L.166.238;
6.L.166.239; 6.L.166.154; 6.L.166.157; 6.L.166.166; 6.L.166.169; 6.L.166.172;
6.L.166.175; 6.L.166.240; 6.L.166.244; 6.L.169.228; 6.L.169.229; 6.L.169.230;
6.L.169.231; 6.L.169.236; 6.L.169.237; 6.L.169.238; 6.L.169.239; 6.L.169.154;
6.L.169.157; 6.L.169.166; 6.L.169.169; 6.L.169.172; 6.L.169.175; 6.L.169.240;
6.L.169.244; 6.L.172.228; 6.L.172.229; 6.L.172.230; 6.L.172.231; 6.L.172.236;
6.L.172.237; 6.L.172.238; 6.L.172.239; 6.L.172.154; 6.L.172.157; 6.L.172.166;
6.L.172.169; 6.L.172.172; 6.L.172.175; 6.L.172.240; 6.L.172.244; 6.L.175.228;
6.L.175.229; 6.L.175.230; 6.L.175.231; 6.L.175.236; 6.L.175.237; 6.L.175.238;
6.L.175.239; 6.L.175.154; 6.L.175.157; 6.L.175.166; 6.L.175.169; 6.L.175.172;
6.L.175.175; 6.L.175.240; 6.L.175.244; 6.L.240.228; 6.L.240.229; 6.L.240.230;
6.L.240.231; 6.L.240.236; 6.L.240.237; 6.L.240.238; 6.L.240.239; 6.L.240.154;
6.L.240.157; 6.L.240.166; 6.L.240.169; 6.L.240.172; 6.L.240.175; 6.L.240.240;
6.L.240.244; 6.L.244.228; 6.L.244.229; 6.L.244.230; 6.L.244.231; 6.L.244.236;
6.L.244.237; 6.L.244.238; 6.L.244.239; 6.L.244.154; 6.L.244.157; 6.L.244.166;
6.L.244.169; 6.L.244.172; 6.L.244.175; 6.L.244.240; 6.L.244.244;
Prodrugs of 6.O 6.O.228.228; 6.O.228.229; 6.O.228.230; 6.O.228.231; 6.O.228.236;
6.O.228.237; 6.O.228.238; 6.O.228.239; 6.O.228.154; 6.O.228.157;
6.O.228.166; 6.O.228.169; 6.O.228.172; 6.O.228.175; 6.O.228.240;
6.O.228.244; 6.O.229.228; 6.O.229.229; 6.O.229.230; 6.O.229.231;
6.O.229.236; 6.O.229.237; 6.O.229.238; 6.O.229.239; 6.O.229.154;
6.O.229.157; 6.O.229.166; 6.O.229.169; 6.O.229.172; 6.O.229.175;
6.O.229.240; 6.O.229.244; 6.O.230.228; 6.O.230.229; 6.O.230.230;
6.O.230.231; 6.O.230.236; 6.O.230.237; 6.O.230.238; 6.O.230.239;
6.O.230.154; 6.O.230.157; 6.O.230.166; 6.O.230.169; 6.O.230.172;
6.O.230.175; 6.O.230.240; 6.O.230.244; 6.O.231.228; 6.O.231.229;
6.O.231.230; 6.O.231.231; 6.O.231.236; 6.O.231.237; 6.O.231.238;
6.O.231.239; 6.O.231.154; 6.O.231.157; 6.O.231.166; 6.O.231.169;
6.O.231.172; 6.O.231.175; 6.O.231.240; 6.O.231.244; 6.O.236.228;
6.O.236.229; 6.O.236.230; 6.O.236.231; 6.O.236.236; 6.O.236.237;
6.O.236.238; 6.O.236.239; 6.O.236.154; 6.O.236.157; 6.O.236.166;
6.O.236.169; 6.O.236.172; 6.O.236.175; 6.O.236.240; 6.O.236.244;
6.O.237.228; 6.O.237.229; 6.O.237.230; 6.O.237.231; 6.O.237.236;
6.O.237.237; 6.O.237.238; 6.O.237.239; 6.O.237.154; 6.O.237.157;

TABLE 100-continued

6.O.237.166; 6.O.237.169; 6.O.237.172; 6.O.237.175; 6.O.237.240;
6.O.237.244; 6.O.238.228; 6.O.238.229; 6.O.238.230; 6.O.238.231;
6.O.238.236; 6.O.238.237; 6.O.238.238; 6.O.238.239; 6.O.238.154;
6.O.238.157; 6.O.238.166; 6.O.238.169; 6.O.238.172; 6.O.238.175;
6.O.238.240; 6.O.238.244; 6.O.239.228; 6.O.239.229; 6.O.239.230;
6.O.239.231; 6.O.239.236; 6.O.239.237; 6.O.239.238; 6.O.239.239;
6.O.239.154; 6.O.239.157; 6.O.239.166; 6.O.239.169; 6.O.239.172;
6.O.239.175; 6.O.239.240; 6.O.239.244; 6.O.154.228; 6.O.154.229;
6.O.154.230; 6.O.154.231; 6.O.154.236; 6.O.154.237; 6.O.154.238;
6.O.154.239; 6.O.154.154; 6.O.154.157; 6.O.154.166; 6.O.154.169;
6.O.154.172; 6.O.154.175; 6.O.154.240; 6.O.154.244; 6.O.157.228;
6.O.157.229; 6.O.157.230; 6.O.157.231; 6.O.157.236; 6.O.157.237;
6.O.157.238; 6.O.157.239; 6.O.157.154; 6.O.157.157; 6.O.157.166;
6.O.157.169; 6.O.157.172; 6.O.157.175; 6.O.157.240; 6.O.157.244;
6.O.166.228; 6.O.166.229; 6.O.166.230; 6.O.166.231; 6.O.166.236;
6.O.166.237; 6.O.166.238; 6.O.166.239; 6.O.166.154; 6.O.166.157;
6.O.166.166; 6.O.166.169; 6.O.166.172; 6.O.166.175; 6.O.166.240;
6.O.166.244; 6.O.169.228; 6.O.169.229; 6.O.169.230; 6.O.169.231;
6.O.169.236; 6.O.169.237; 6.O.169.238; 6.O.169.239; 6.O.169.154;
6.O.169.157; 6.O.169.166; 6.O.169.169; 6.O.169.172; 6.O.169.175;
6.O.169.240; 6.O.169.244; 6.O.172.228; 6.O.172.229; 6.O.172.230;
6.O.172.231; 6.O.172.236; 6.O.172.237; 6.O.172.238; 6.O.172.239;
6.O.172.154; 6.O.172.157; 6.O.172.166; 6.O.172.169; 6.O.172.172;
6.O.172.175; 6.O.172.240; 6.O.172.244; 6.O.175.228; 6.O.175.229;
6.O.175.230; 6.O.175.231; 6.O.175.236; 6.O.175.237; 6.O.175.238;
6.O.175.239; 6.O.175.154; 6.O.175.157; 6.O.175.166; 6.O.175.169;
6.O.175.172; 6.O.175.175; 6.O.175.240; 6.O.175.244; 6.O.240.228;
6.O.240.229; 6.O.240.230; 6.O.240.231; 6.O.240.236; 6.O.240.237;
6.O.240.238; 6.O.240.239; 6.O.240.154; 6.O.240.157; 6.O.240.166;
6.O.240.169; 6.O.240.172; 6.O.240.175; 6.O.240.240; 6.O.240.244;
6.O.244.228; 6.O.244.229; 6.O.244.230; 6.O.244.231; 6.O.244.236;
6.O.244.237; 6.O.244.238; 6.O.244.239; 6.O.244.154; 6.O.244.157;
6.O.244.166; 6.O.244.169; 6.O.244.172; 6.O.244.175; 6.O.244.240;
6.O.244.244;

Prodrugs of 6.P

6.P.228.228; 6.P.228.229; 6.P.228.230; 6.P.228.231; 6.P.228.236;
6.P.228.237; 6.P.228.238; 6.P.228.239; 6.P.228.154; 6.P.228.157; 6.P.228.166;
6.P.228.169; 6.P.228.172; 6.P.228.175; 6.P.228.240; 6.P.228.244; 6.P.229.228;
6.P.229.229; 6.P.229.230; 6.P.229.231; 6.P.229.236; 6.P.229.237; 6.P.229.238;
6.P.229.239; 6.P.229.154; 6.P.229.157; 6.P.229.166; 6.P.229.169; 6.P.229.172;
6.P.229.175; 6.P.229.240; 6.P.229.244; 6.P.230.228; 6.P.230.229; 6.P.230.230;
6.P.230.231; 6.P.230.236; 6.P.230.237; 6.P.230.238; 6.P.230.239; 6.P.230.154;
6.P.230.157; 6.P.230.166; 6.P.230.169; 6.P.230.172; 6.P.230.175; 6.P.230.240;
6.P.230.244; 6.P.231.228; 6.P.231.229; 6.P.231.230; 6.P.231.231; 6.P.231.236;
6.P.231.237; 6.P.231.238; 6.P.231.239; 6.P.231.154; 6.P.231.157; 6.P.231.166;
6.P.231.169; 6.P.231.172; 6.P.231.175; 6.P.231.240; 6.P.231.244; 6.P.236.228;
6.P.236.229; 6.P.236.230; 6.P.236.231; 6.P.236.236; 6.P.236.237; 6.P.236.238;
6.P.236.239; 6.P.236.154; 6.P.236.157; 6.P.236.166; 6.P.236.169; 6.P.236.172;
6.P.236.175; 6.P.236.240; 6.P.236.244; 6.P.237.228; 6.P.237.229; 6.P.237.230;
6.P.237.231; 6.P.237.236; 6.P.237.237; 6.P.237.238; 6.P.237.239; 6.P.237.154;
6.P.237.157; 6.P.237.166; 6.P.237.169; 6.P.237.172; 6.P.237.175; 6.P.237.240;
6.P.237.244; 6.P.238.228; 6.P.238.229; 6.P.238.230; 6.P.238.231; 6.P.238.236;
6.P.238.237; 6.P.238.238; 6.P.238.239; 6.P.238.154; 6.P.238.157; 6.P.238.166;
6.P.238.169; 6.P.238.172; 6.P.238.175; 6.P.238.240; 6.P.238.244; 6.P.239.228;
6.P.239.229; 6.P.239.230; 6.P.239.231; 6.P.239.236; 6.P.239.237; 6.P.239.238;
6.P.239.239; 6.P.239.154; 6.P.239.157; 6.P.239.166; 6.P.239.169; 6.P.239.172;
6.P.239.175; 6.P.239.240; 6.P.239.244; 6.P.154.228; 6.P.154.229; 6.P.154.230;
6.P.154.231; 6.P.154.236; 6.P.154.237; 6.P.154.238; 6.P.154.239; 6.P.154.154;
6.P.154.157; 6.P.154.166; 6.P.154.169; 6.P.154.172; 6.P.154.175; 6.P.154.240;
6.P.154.244; 6.P.157.228; 6.P.157.229; 6.P.157.230; 6.P.157.231; 6.P.157.236;
6.P.157.237; 6.P.157.238; 6.P.157.239; 6.P.157.154; 6.P.157.157; 6.P.157.166;
6.P.157.169; 6.P.157.172; 6.P.157.175; 6.P.157.240; 6.P.157.244; 6.P.166.228;
6.P.166.229; 6.P.166.230; 6.P.166.231; 6.P.166.236; 6.P.166.237; 6.P.166.238;
6.P.166.239; 6.P.166.154; 6.P.166.157; 6.P.166.166; 6.P.166.169; 6.P.166.172;
6.P.166.175; 6.P.166.240; 6.P.166.244; 6.P.169.228; 6.P.169.229; 6.P.169.230;
6.P.169.231; 6.P.169.236; 6.P.169.237; 6.P.169.238; 6.P.169.239; 6.P.169.154;
6.P.169.157; 6.P.169.166; 6.P.169.169; 6.P.169.172; 6.P.169.175; 6.P.169.240;
6.P.169.244; 6.P.172.228; 6.P.172.229; 6.P.172.230; 6.P.172.231; 6.P.172.236;
6.P.172.237; 6.P.172.238; 6.P.172.239; 6.P.172.154; 6.P.172.157; 6.P.172.166;
6.P.172.169; 6.P.172.172; 6.P.172.175; 6.P.172.240; 6.P.172.244; 6.P.175.228;
6.P.175.229; 6.P.175.230; 6.P.175.231; 6.P.175.236; 6.P.175.237; 6.P.175.238;
6.P.175.239; 6.P.175.154; 6.P.175.157; 6.P.175.166; 6.P.175.169; 6.P.175.172;
6.P.175.175; 6.P.175.240; 6.P.175.244; 6.P.240.228; 6.P.240.229; 6.P.240.230;
6.P.240.231; 6.P.240.236; 6.P.240.237; 6.P.240.238; 6.P.240.239; 6.P.240.154;
6.P.240.157; 6.P.240.166; 6.P.240.169; 6.P.240.172; 6.P.240.175; 6.P.240.240;
6.P.240.244; 6.P.244.228; 6.P.244.229; 6.P.244.230; 6.P.244.231; 6.P.244.236;
6.P.244.237; 6.P.244.238; 6.P.244.239; 6.P.244.154; 6.P.244.157; 6.P.244.166;
6.P.244.169; 6.P.244.172; 6.P.244.175; 6.P.244.240; 6.P.244.244;

TABLE 100-continued

Prodrugs of 6.U

6.U.228.228; 6.U.228.229; 6.U.228.230; 6.U.228.231; 6.U.228.236;
6.U.228.237; 6.U.228.238; 6.U.228.239; 6.U.228.154; 6.U.228.157;
6.U.228.166; 6.U.228.169; 6.U.228.172; 6.U.228.175; 6.U.228.240;
6.U.228.244; 6.U.229.228; 6.U.229.229; 6.U.229.230; 6.U.229.231;
6.U.229.236; 6.U.229.237; 6.U.229.238; 6.U.229.239; 6.U.229.154;
6.U.229.157; 6.U.229.166; 6.U.229.169; 6.U.229.172; 6.U.229.175;
6.U.229.240; 6.U.229.244; 6.U.230.228; 6.U.230.229; 6.U.230.230;
6.U.230.231; 6.U.230.236; 6.U.230.237; 6.U.230.238; 6.U.230.239;
6.U.230.154; 6.U.230.157; 6.U.230.166; 6.U.230.169; 6.U.230.172;
6.U.230.175; 6.U.230.240; 6.U.230.244; 6.U.231.228; 6.U.231.229;
6.U.231.230; 6.U.231.231; 6.U.231.236; 6.U.231.237; 6.U.231.238;
6.U.231.239; 6.U.231.154; 6.U.231.157; 6.U.231.166; 6.U.231.169;
6.U.231.172; 6.U.231.175; 6.U.231.240; 6.U.231.244; 6.U.236.228;
6.U.236.229; 6.U.236.230; 6.U.236.231; 6.U.236.236; 6.U.236.237;
6.U.236.238; 6.U.236.239; 6.U.236.154; 6.U.236.157; 6.U.236.166;
6.U.236.169; 6.U.236.172; 6.U.236.175; 6.U.236.240; 6.U.236.244;
6.U.237.228; 6.U.237.229; 6.U.237.230; 6.U.237.231; 6.U.237.236;
6.U.237.237; 6.U.237.238; 6.U.237.239; 6.U.237.154; 6.U.237.157;
6.U.237.166; 6.U.237.169; 6.U.237.172; 6.U.237.175; 6.U.237.240;
6.U.237.244; 6.U.238.228; 6.U.238.229; 6.U.238.230; 6.U.238.231;
6.U.238.236; 6.U.238.237; 6.U.238.238; 6.U.238.239; 6.U.238.154;
6.U.238.157; 6.U.238.166; 6.U.238.169; 6.U.238.172; 6.U.238.175;
6.U.238.240; 6.U.238.244; 6.U.239.228; 6.U.239.229; 6.U.239.230;
6.U.239.231; 6.U.239.236; 6.U.239.237; 6.U.239.238; 6.U.239.239;
6.U.239.154; 6.U.239.157; 6.U.239.166; 6.U.239.169; 6.U.239.172;
6.U.239.175; 6.U.239.240; 6.U.239.244; 6.U.154.228; 6.U.154.229;
6.U.154.230; 6.U.154.231; 6.U.154.236; 6.U.154.237; 6.U.154.238;
6.U.154.239; 6.U.154.154; 6.U.154.157; 6.U.154.166; 6.U.154.169;
6.U.154.172; 6.U.154.175; 6.U.154.240; 6.U.154.244; 6.U.157.228;
6.U.157.229; 6.U.157.230; 6.U.157.231; 6.U.157.236; 6.U.157.237;
6.U.157.238; 6.U.157.239; 6.U.157.154; 6.U.157.157; 6.U.157.166;
6.U.157.169; 6.U.157.172; 6.U.157.175; 6.U.157.240; 6.U.157.244;
6.U.166.228; 6.U.166.229; 6.U.166.230; 6.U.166.231; 6.U.166.236;
6.U.166.237; 6.U.166.238; 6.U.166.239; 6.U.166.154; 6.U.166.157;
6.U.166.166; 6.U.166.169; 6.U.166.172; 6.U.166.175; 6.U.166.240;
6.U.166.244; 6.U.169.228; 6.U.169.229; 6.U.169.230; 6.U.169.231;
6.U.169.236; 6.U.169.237; 6.U.169.238; 6.U.169.239; 6.U.169.154;
6.U.169.157; 6.U.169.166; 6.U.169.169; 6.U.169.172; 6.U.169.175;
6.U.169.240; 6.U.169.244; 6.U.172.228; 6.U.172.229; 6.U.172.230;
6.U.172.231; 6.U.172.236; 6.U.172.237; 6.U.172.238; 6.U.172.239;
6.U.172.154; 6.U.172.157; 6.U.172.166; 6.U.172.169; 6.U.172.172;
6.U.172.175; 6.U.172.240; 6.U.172.244; 6.U.175.228; 6.U.175.229;
6.U.175.230; 6.U.175.231; 6.U.175.236; 6.U.175.237; 6.U.175.238;
6.U.175.239; 6.U.175.154; 6.U.175.157; 6.U.175.166; 6.U.175.169;
6.U.175.172; 6.U.175.175; 6.U.175.240; 6.U.175.244; 6.U.240.228;
6.U.240.229; 6.U.240.230; 6.U.240.231; 6.U.240.236; 6.U.240.237;
6.U.240.238; 6.U.240.239; 6.U.240.154; 6.U.240.157; 6.U.240.166;
6.U.240.169; 6.U.240.172; 6.U.240.175; 6.U.240.240; 6.U.240.244;
6.U.244.228; 6.U.244.229; 6.U.244.230; 6.U.244.231; 6.U.244.236;
6.U.244.237; 6.U.244.238; 6.U.244.239; 6.U.244.154; 6.U.244.157;
6.U.244.166; 6.U.244.169; 6.U.244.172; 6.U.244.175; 6.U.244.240;
6.U.244.244;

Prodrugs of 6.W

6.W.228.228; 6.W.228.229; 6.W.228.230; 6.W.228.231; 6.W.228.236;
6.W.228.237; 6.W.228.238; 6.W.228.239; 6.W.228.154; 6.W.228.157;
6.W.228.166; 6.W.228.169; 6.W.228.172; 6.W.228.175; 6.W.228.240;
6.W.228.244; 6.W.229.228; 6.W.229.229; 6.W.229.230; 6.W.229.231;
6.W.229.236; 6.W.229.237; 6.W.229.238; 6.W.229.239; 6.W.229.154;
6.W.229.157; 6.W.229.166; 6.W.229.169; 6.W.229.172; 6.W.229.175;
6.W.229.240; 6.W.229.244; 6.W.230.228; 6.W.230.229; 6.W.230.230;
6.W.230.231; 6.W.230.236; 6.W.230.237; 6.W.230.238; 6.W.230.239;
6.W.230.154; 6.W.230.157; 6.W.230.166; 6.W.230.169; 6.W.230.172;
6.W.230.175; 6.W.230.240; 6.W.230.244; 6.W.231.228; 6.W.231.229;
6.W.231.230; 6.W.231.231; 6.W.231.236; 6.W.231.237; 6.W.231.238;
6.W.231.239; 6.W.231.154; 6.W.231.157; 6.W.231.166; 6.W.231.169;
6.W.231.172; 6.W.231.175; 6.W.231.240; 6.W.231.244; 6.W.236.228;
6.W.236.229; 6.W.236.230; 6.W.236.231; 6.W.236.236; 6.W.236.237;
6.W.236.238; 6.W.236.239; 6.W.236.154; 6.W.236.157; 6.W.236.166;
6.W.236.169; 6.W.236.172; 6.W.236.175; 6.W.236.240; 6.W.236.244;
6.W.237.228; 6.W.237.229; 6.W.237.230; 6.W.237.231; 6.W.237.236;
6.W.237.237; 6.W.237.238; 6.W.237.239; 6.W.237.154; 6.W.237.157;
6.W.237.166; 6.W.237.169; 6.W.237.172; 6.W.237.175; 6.W.237.240;
6.W.237.244; 6.W.238.228; 6.W.238.229; 6.W.238.230; 6.W.238.231;
6.W.238.236; 6.W.238.237; 6.W.238.238; 6.W.238.239; 6.W.238.154;
6.W.238.157; 6.W.238.166; 6.W.238.169; 6.W.238.172; 6.W.238.175;
6.W.238.240; 6.W.238.244; 6.W.239.228; 6.W.239.229; 6.W.239.230;

TABLE 100-continued

6.W.239.231; 6.W.239.236; 6.W.239.237; 6.W.239.238; 6.W.239.239;
6.W.239.154; 6.W.239.157; 6.W.239.166; 6.W.239.169; 6.W.239.172;
6.W.239.175; 6.W.239.240; 6.W.239.244; 6.W.154.228; 6.W.154.229;
6.W.154.230; 6.W.154.231; 6.W.154.236; 6.W.154.237; 6.W.154.238;
6.W.154.239; 6.W.154.154; 6.W.154.157; 6.W.154.166; 6.W.154.169;
6.W.154.172; 6.W.154.175; 6.W.154.240; 6.W.154.244; 6.W.157.228;
6.W.157.229; 6.W.157.230; 6.W.157.231; 6.W.157.236; 6.W.157.237;
6.W.157.238; 6.W.157.239; 6.W.157.154; 6.W.157.157; 6.W.157.166;
6.W.157.169; 6.W.157.172; 6.W.157.175; 6.W.157.240; 6.W.157.244;
6.W.166.228; 6.W.166.229; 6.W.166.230; 6.W.166.231; 6.W.166.236;
6.W.166.237; 6.W.166.238; 6.W.166.239; 6.W.166.154; 6.W.166.157;
6.W.166.166; 6.W.166.169; 6.W.166.172; 6.W.166.175; 6.W.166.240;
6.W.166.244; 6.W.169.228; 6.W.169.229; 6.W.169.230; 6.W.169.231;
6.W.169.236; 6.W.169.237; 6.W.169.238; 6.W.169.239; 6.W.169.154;
6.W.169.157; 6.W.169.166; 6.W.169.169; 6.W.169.172; 6.W.169.175;
6.W.169.240; 6.W.169.244; 6.W.172.228; 6.W.172.229; 6.W.172.230;
6.W.172.231; 6.W.172.236; 6.W.172.237; 6.W.172.238; 6.W.172.239;
6.W.172.154; 6.W.172.157; 6.W.172.166; 6.W.172.169; 6.W.172.172;
6.W.172.175; 6.W.172.240; 6.W.172.244; 6.W.175.228; 6.W.175.229;
6.W.175.230; 6.W.175.231; 6.W.175.236; 6.W.175.237; 6.W.175.238;
6.W.175.239; 6.W.175.154; 6.W.175.157; 6.W.175.166; 6.W.175.169;
6.W.175.172; 6.W.175.175; 6.W.175.240; 6.W.175.244; 6.W.240.228;
6.W.240.229; 6.W.240.230; 6.W.240.231; 6.W.240.236; 6.W.240.237;
6.W.240.238; 6.W.240.239; 6.W.240.154; 6.W.240.157; 6.W.240.166;
6.W.240.169; 6.W.240.172; 6.W.240.175; 6.W.240.240; 6.W.240.244;
6.W.244.228; 6.W.244.229; 6.W.244.230; 6.W.244.231; 6.W.244.236;
6.W.244.237; 6.W.244.238; 6.W.244.239; 6.W.244.154; 6.W.244.157;
6.W.244.166; 6.W.244.169; 6.W.244.172; 6.W.244.175; 6.W.244.240;
6.W.244.244;
Prodrugs of 6.Y 6.Y.228.228; 6.Y.228.229; 6.Y.228.230; 6.Y.228.231; 6.Y.228.236;
6.Y.228.237; 6.Y.228.238; 6.Y.228.239; 6.Y.228.154; 6.Y.228.157;
6.Y.228.166; 6.Y.228.169; 6.Y.228.172; 6.Y.228.175; 6.Y.228.240;
6.Y.228.244; 6.Y.229.228; 6.Y.229.229; 6.Y.229.230; 6.Y.229.231;
6.Y.229.236; 6.Y.229.237; 6.Y.229.238; 6.Y.229.239; 6.Y.229.154;
6.Y.229.157; 6.Y.229.166; 6.Y.229.169; 6.Y.229.172; 6.Y.229.175;
6.Y.229.240; 6.Y.229.244; 6.Y.230.228; 6.Y.230.229; 6.Y.230.230;
6.Y.230.231; 6.Y.230.236; 6.Y.230.237; 6.Y.230.238; 6.Y.230.239;
6.Y.230.154; 6.Y.230.157; 6.Y.230.166; 6.Y.230.169; 6.Y.230.172;
6.Y.230.175; 6.Y.230.240; 6.Y.230.244; 6.Y.231.228; 6.Y.231.229;
6.Y.231.230; 6.Y.231.231; 6.Y.231.236; 6.Y.231.237; 6.Y.231.238;
6.Y.231.239; 6.Y.231.154; 6.Y.231.157; 6.Y.231.166; 6.Y.231.169;
6.Y.231.172; 6.Y.231.175; 6.Y.231.240; 6.Y.231.244; 6.Y.236.228;
6.Y.236.229; 6.Y.236.230; 6.Y.236.231; 6.Y.236.236; 6.Y.236.237;
6.Y.236.238; 6.Y.236.239; 6.Y.236.154; 6.Y.236.157; 6.Y.236.166;
6.Y.236.169; 6.Y.236.172; 6.Y.236.175; 6.Y.236.240; 6.Y.236.244;
6.Y.237.228; 6.Y.237.229; 6.Y.237.230; 6.Y.237.231; 6.Y.237.236;
6.Y.237.237; 6.Y.237.238; 6.Y.237.239; 6.Y.237.154; 6.Y.237.157;
6.Y.237.166; 6.Y.237.169; 6.Y.237.172; 6.Y.237.175; 6.Y.237.240;
6.Y.237.244; 6.Y.238.228; 6.Y.238.229; 6.Y.238.230; 6.Y.238.231;
6.Y.238.236; 6.Y.238.237; 6.Y.238.238; 6.Y.238.239; 6.Y.238.154;
6.Y.238.157; 6.Y.238.166; 6.Y.238.169; 6.Y.238.172; 6.Y.238.175;
6.Y.238.240; 6.Y.238.244; 6.Y.239.228; 6.Y.239.229; 6.Y.239.230;
6.Y.239.231; 6.Y.239.236; 6.Y.239.237; 6.Y.239.238; 6.Y.239.239;
6.Y.239.154; 6.Y.239.157; 6.Y.239.166; 6.Y.239.169; 6.Y.239.172;
6.Y.239.175; 6.Y.239.240; 6.Y.239.244; 6.Y.154.228; 6.Y.154.229;
6.Y.154.230; 6.Y.154.231; 6.Y.154.236; 6.Y.154.237; 6.Y.154.238;
6.Y.154.239; 6.Y.154.154; 6.Y.154.157; 6.Y.154.166; 6.Y.154.169;
6.Y.154.172; 6.Y.154.175; 6.Y.154.240; 6.Y.154.244; 6.Y.157.228;
6.Y.157.229; 6.Y.157.230; 6.Y.157.231; 6.Y.157.236; 6.Y.157.237;
6.Y.157.238; 6.Y.157.239; 6.Y.157.154; 6.Y.157.157; 6.Y.157.166;
6.Y.157.169; 6.Y.157.172; 6.Y.157.175; 6.Y.157.240; 6.Y.157.244;
6.Y.166.228; 6.Y.166.229; 6.Y.166.230; 6.Y.166.231; 6.Y.166.236;
6.Y.166.237; 6.Y.166.238; 6.Y.166.239; 6.Y.166.154; 6.Y.166.157;
6.Y.166.166; 6.Y.166.169; 6.Y.166.172; 6.Y.166.175; 6.Y.166.240;
6.Y.166.244; 6.Y.169.228; 6.Y.169.229; 6.Y.169.230; 6.Y.169.231;
6.Y.169.236; 6.Y.169.237; 6.Y.169.238; 6.Y.169.239; 6.Y.169.154;
6.Y.169.157; 6.Y.169.166; 6.Y.169.169; 6.Y.169.172; 6.Y.169.175;
6.Y.169.240; 6.Y.169.244; 6.Y.172.228; 6.Y.172.229; 6.Y.172.230;
6.Y.172.231; 6.Y.172.236; 6.Y.172.237; 6.Y.172.238; 6.Y.172.239;
6.Y.172.154; 6.Y.172.157; 6.Y.172.166; 6.Y.172.169; 6.Y.172.172;
6.Y.172.175; 6.Y.172.240; 6.Y.172.244; 6.Y.175.228; 6.Y.175.229;
6.Y.175.230; 6.Y.175.231; 6.Y.175.236; 6.Y.175.237; 6.Y.175.238;
6.Y.175.239; 6.Y.175.154; 6.Y.175.157; 6.Y.175.166; 6.Y.175.169;
6.Y.175.172; 6.Y.175.175; 6.Y.175.240; 6.Y.175.244; 6.Y.240.228;
6.Y.240.229; 6.Y.240.230; 6.Y.240.231; 6.Y.240.236; 6.Y.240.237;
6.Y.240.238; 6.Y.240.239; 6.Y.240.154; 6.Y.240.157; 6.Y.240.166;
6.Y.240.169; 6.Y.240.172; 6.Y.240.175; 6.Y.240.240; 6.Y.240.244;

TABLE 100-continued

6.Y.244.228; 6.Y.244.229; 6.Y.244.230; 6.Y.244.231; 6.Y.244.236;
6.Y.244.237; 6.Y.244.238; 6.Y.244.239; 6.Y.244.154; 6.Y.244.157;
6.Y.244.166; 6.Y.244.169; 6.Y.244.172; 6.Y.244.175; 6.Y.244.240;
6.Y.244.244;
Prodrugs of 7.AH 7.AH.4.157; 7.AH.4.158; 7.AH.4.196; 7.AH.4.223; 7.AH.4.240; 7.AH.4.244;
7.AH.4.243; 7.AH.4.247; 7.AH.5.157; 7.AH.5.158; 7.AH.5.196; 7.AH.5.223;
7.AH.5.240; 7.AH.5.244; 7.AH.5.243; 7.AH.5.247; 7.AH.7.157; 7.AH.7.158;
7.AH.7.196; 7.AH.7.223; 7.AH.7.240; 7.AH.7.244; 7.AH.7.243; 7.AH.7.247;
7.AH.15.157; 7.AH.15.158; 7.AH.15.196; 7.AH.15.223; 7.AH.15.240;
7.AH.15.244; 7.AH.15.243; 7.AH.15.247; 7.AH.16.157; 7.AH.16.158;
7.AH.16.196; 7.AH.16.223; 7.AH.16.240; 7.AH.16.244; 7.AH.16.243;
7.AH.16.247; 7.AH.18.157; 7.AH.18.158; 7.AH.18.196; 7.AH.18.223;
7.AH.18.240; 7.AH.18.244; 7.AH.18.243; 7.AH.18.247; 7.AH.26.157;
7.AH.26.158; 7.AH.26.196; 7.AH.26.223; 7.AH.26.240; 7.AH.26.244;
7.AH.26.243; 7.AH.26.247; 7.AH.27.157; 7.AH.27.158; 7.AH.27.196;
7.AH.27.223; 7.AH.27.240; 7.AH.27.244; 7.AH.27.243; 7.AH.27.247;
7.AH.29.157; 7.AH.29.158; 7.AH.29.196; 7.AH.29.223; 7.AH.29.240;
7.AH.29.244; 7.AH.29.243; 7.AH.29.247; 7.AH.54.157; 7.AH.54.158;
7.AH.54.196; 7.AH.54.223; 7.AH.54.240; 7.AH.54.244; 7.AH.54.243;
7.AH.54.247; 7.AH.55.157; 7.AH.55.158; 7.AH.55.196; 7.AH.55.223;
7.AH.55.240; 7.AH.55.244; 7.AH.55.243; 7.AH.55.247; 7.AH.56.157;
7.AH.56.158; 7.AH.56.196; 7.AH.56.223; 7.AH.56.240; 7.AH.56.244;
7.AH.56.243; 7.AH.56.247; 7.AH.157.157; 7.AH.157.158; 7.AH.157.196;
7.AH.157.223; 7.AH.157.240; 7.AH.157.244; 7.AH.157.243; 7.AH.157.247;
7.AH.196.157; 7.AH.196.158; 7.AH.196.196; 7.AH.196.223; 7.AH.196.240;
7.AH.196.244; 7.AH.196.243; 7.AH.196.247; 7.AH.223.157; 7.AH.223.158;
7.AH.223.196; 7.AH.223.223; 7.AH.223.240; 7.AH.223.244; 7.AH.223.243;
7.AH.223.247; 7.AH.240.157; 7.AH.240.158; 7.AH.240.196; 7.AH.240.223;
7.AH.240.240; 7.AH.240.244; 7.AH.240.243; 7.AH.240.247; 7.AH.244.157;
7.AH.244.158; 7.AH.244.196; 7.AH.244.223; 7.AH.244.240; 7.AH.244.244;
7.AH.244.243; 7.AH.244.247; 7.AH.247.157; 7.AH.247.158; 7.AH.247.196;
7.AH.247.223; 7.AH.247.240; 7.AH.247.244; 7.AH.247.243; 7.AH.247.247;
Prodrugs of 7.AJ 7.AJ.4.157; 7.AJ.4.158; 7.AJ.4.196; 7.AJ.4.223; 7.AJ.4.240; 7.AJ.4.244;
7.AJ.4.243; 7.AJ.4.247; 7.AJ.5.157; 7.AJ.5.158; 7.AJ.5.196; 7.AJ.5.223;
7.AJ.5.240; 7.AJ.5.244; 7.AJ.5.243; 7.AJ.5.247; 7.AJ.7.157; 7.AJ.7.158;
7.AJ.7.196; 7.AJ.7.223; 7.AJ.7.240; 7.AJ.7.244; 7.AJ.7.243; 7.AJ.7.247;
7.AJ.15.157; 7.AJ.15.158; 7.AJ.15.196; 7.AJ.15.223; 7.AJ.15.240; 7.AJ.15.244;
7.AJ.15.243; 7.AJ.15.247; 7.AJ.16.157; 7.AJ.16.158; 7.AJ.16.196; 7.AJ.16.223;
7.AJ.16.240; 7.AJ.16.244; 7.AJ.16.243; 7.AJ.16.247; 7.AJ.18.157; 7.AJ.18.158;
7.AJ.18.196; 7.AJ.18.223; 7.AJ.18.240; 7.AJ.18.244; 7.AJ.18.243; 7.AJ.18.247;
7.AJ.26.157; 7.AJ.26.158; 7.AJ.26.196; 7.AJ.26.223; 7.AJ.26.240; 7.AJ.26.244;
7.AJ.26.243; 7.AJ.26.247; 7.AJ.27.157; 7.AJ.27.158; 7.AJ.27.196; 7.AJ.27.223;
7.AJ.27.240; 7.AJ.27.244; 7.AJ.27.243; 7.AJ.27.247; 7.AJ.29.157; 7.AJ.29.158;
7.AJ.29.196; 7.AJ.29.223; 7.AJ.29.240; 7.AJ.29.244; 7.AJ.29.243; 7.AJ.29.247;
7.AJ.54.157; 7.AJ.54.158; 7.AJ.54.196; 7.AJ.54.223; 7.AJ.54.240; 7.AJ.54.244;
7.AJ.54.243; 7.AJ.54.247; 7.AJ.55.157; 7.AJ.55.158; 7.AJ.55.196; 7.AJ.55.223;
7.AJ.55.240; 7.AJ.55.244; 7.AJ.55.243; 7.AJ.55.247; 7.AJ.56.157; 7.AJ.56.158;
7.AJ.56.196; 7.AJ.56.223; 7.AJ.56.240; 7.AJ.56.244; 7.AJ.56.243; 7.AJ.56.247;
7.AJ.157.157; 7.AJ.157.158; 7.AJ.157.196; 7.AJ.157.223; 7.AJ.157.240;
7.AJ.157.244; 7.AJ.157.243; 7.AJ.157.247; 7.AJ.196.157; 7.AJ.196.158;
7.AJ.196.196; 7.AJ.196.223; 7.AJ.196.240; 7.AJ.196.244; 7.AJ.196.243;
7.AJ.196.247; 7.AJ.223.157; 7.AJ.223.158; 7.AJ.223.196; 7.AJ.223.223;
7.AJ.223.240; 7.AJ.223.244; 7.AJ.223.243; 7.AJ.223.247; 7.AJ.240.157;
7.AJ.240.158; 7.AJ.240.196; 7.AJ.240.223; 7.AJ.240.240; 7.AJ.240.244;
7.AJ.240.243; 7.AJ.240.247; 7.AJ.244.157; 7.AJ.244.158; 7.AJ.244.196;
7.AJ.244.223; 7.AJ.244.240; 7.AJ.244.244; 7.AJ.244.243; 7.AJ.244.247;
7.AJ.247.157; 7.AJ.247.158; 7.AJ.247.196; 7.AJ.247.223; 7.AJ.247.240;
7.AJ.247.244; 7.AJ.247.243; 7.AJ.247.247;
Prodrugs of 7.AN 7.AN.4.157; 7.AN.4.158; 7.AN.4.196; 7.AN.4.223; 7.AN.4.240; 7.AN.4.244;
7.AN.4.243; 7.AN.4.247; 7.AN.5.157; 7.AN.5.158; 7.AN.5.196; 7.AN.5.223;
7.AN.5.240; 7.AN.5.244; 7.AN.5.243; 7.AN.5.247; 7.AN.7.157; 7.AN.7.158;
7.AN.7.196; 7.AN.7.223; 7.AN.7.240; 7.AN.7.244; 7.AN.7.243; 7.AN.7.247;
7.AN.15.157; 7.AN.15.158; 7.AN.15.196; 7.AN.15.223; 7.AN.15.240;
7.AN.15.244; 7.AN.15.243; 7.AN.15.247; 7.AN.16.157; 7.AN.16.158;
7.AN.16.196; 7.AN.16.223; 7.AN.16.240; 7.AN.16.244; 7.AN.16.243;
7.AN.16.247; 7.AN.18.157; 7.AN.18.158; 7.AN.18.196; 7.AN.18.223;
7.AN.18.240; 7.AN.18.244; 7.AN.18.243; 7.AN.18.247; 7.AN.26.157;
7.AN.26.158; 7.AN.26.196; 7.AN.26.223; 7.AN.26.240; 7.AN.26.244;
7.AN.26.243; 7.AN.26.247; 7.AN.27.157; 7.AN.27.158; 7.AN.27.196;
7.AN.27.223; 7.AN.27.240; 7.AN.27.244; 7.AN.27.243; 7.AN.27.247;
7.AN.29.157; 7.AN.29.158; 7.AN.29.196; 7.AN.29.223; 7.AN.29.240;
7.AN.29.244; 7.AN.29.243; 7.AN.29.247; 7.AN.54.157; 7.AN.54.158;
7.AN.54.196; 7.AN.54.223; 7.AN.54.240; 7.AN.54.244; 7.AN.54.243;

TABLE 100-continued

7.AN.54.247; 7.AN.55.157; 7.AN.55.158; 7.AN.55.196; 7.AN.55.223;
7.AN.55.240; 7.AN.55.244; 7.AN.55.243; 7.AN.55.247; 7.AN.56.157;
7.AN.56.158; 7.AN.56.196; 7.AN.56.223; 7.AN.56.240; 7.AN.56.244;
7.AN.56.243; 7.AN.56.247; 7.AN.157.157; 7.AN.157.158; 7.AN.157.196;
7.AN.157.223; 7.AN.157.240; 7.AN.157.244; 7.AN.157.243; 7.AN.157.247;
7.AN.196.157; 7.AN.196.158; 7.AN.196.196; 7.AN.196.223; 7.AN.196.240;
7.AN.196.244; 7.AN.196.243; 7.AN.196.247; 7.AN.223.157; 7.AN.223.158;
7.AN.223.196; 7.AN.223.223; 7.AN.223.240; 7.AN.223.244; 7.AN.223.243;
7.AN.223.247; 7.AN.240.157; 7.AN.240.158; 7.AN.240.196; 7.AN.240.223;
7.AN.240.240; 7.AN.240.244; 7.AN.240.243; 7.AN.240.247; 7.AN.244.157;
7.AN.244.158; 7.AN.244.196; 7.AN.244.223; 7.AN.244.240; 7.AN.244.244;
7.AN.244.243; 7.AN.244.247; 7.AN.247.157; 7.AN.247.158; 7.AN.247.196;
7.AN.247.223; 7.AN.247.240; 7.AN.247.244; 7.AN.247.243; 7.AN.247.247;
Prodrugs of 7.AP 7.AP.4.157; 7.AP.4.158; 7.AP.4.196; 7.AP.4.223; 7.AP.4.240; 7.AP.4.244;
7.AP.4.243; 7.AP.4.247; 7.AP.5.157; 7.AP.5.158; 7.AP.5.196; 7.AP.5.223;
7.AP.5.240; 7.AP.5.244; 7.AP.5.243; 7.AP.5.247; 7.AP.7.157; 7.AP.7.158;
7.AP.7.196; 7.AP.7.223; 7.AP.7.240; 7.AP.7.244; 7.AP.7.243; 7.AP.7.247;
7.AP.15.157; 7.AP.15.158; 7.AP.15.196; 7.AP.15.223; 7.AP.15.240;
7.AP.15.244; 7.AP.15.243; 7.AP.15.247; 7.AP.16.157; 7.AP.16.158;
7.AP.16.196; 7.AP.16.223; 7.AP.16.240; 7.AP.16.244; 7.AP.16.243;
7.AP.16.247; 7.AP.18.157; 7.AP.18.158; 7.AP.18.196; 7.AP.18.223;
7.AP.18.240; 7.AP.18.244; 7.AP.18.243; 7.AP.18.247; 7.AP.26.157;
7.AP.26.158; 7.AP.26.196; 7.AP.26.223; 7.AP.26.240; 7.AP.26.244;
7.AP.26.243; 7.AP.26.247; 7.AP.27.157; 7.AP.27.158; 7.AP.27.196;
7.AP.27.223; 7.AP.27.240; 7.AP.27.244; 7.AP.27.243; 7.AP.27.247;
7.AP.29.157; 7.AP.29.158; 7.AP.29.196; 7.AP.29.223; 7.AP.29.240;
7.AP.29.244; 7.AP.29.243; 7.AP.29.247; 7.AP.54.157; 7.AP.54.158;
7.AP.54.196; 7.AP.54.223; 7.AP.54.240; 7.AP.54.244; 7.AP.54.243;
7.AP.54.247; 7.AP.55.157; 7.AP.55.158; 7.AP.55.196; 7.AP.55.223;
7.AP.55.240; 7.AP.55.244; 7.AP.55.243; 7.AP.55.247; 7.AP.56.157;
7.AP.56.158; 7.AP.56.196; 7.AP.56.223; 7.AP.56.240; 7.AP.56.244;
7.AP.56.243; 7.AP.56.247; 7.AP.157.157; 7.AP.157.158; 7.AP.157.196;
7.AP.157.223; 7.AP.157.240; 7.AP.157.244; 7.AP.157.243; 7.AP.157.247;
7.AP.196.157; 7.AP.196.158; 7.AP.196.196; 7.AP.196.223; 7.AP.196.240;
7.AP.196.244; 7.AP.196.243; 7.AP.196.247; 7.AP.223.157; 7.AP.223.158;
7.AP.223.196; 7.AP.223.223; 7.AP.223.240; 7.AP.223.244; 7.AP.223.243;
7.AP.223.247; 7.AP.240.157; 7.AP.240.158; 7.AP.240.196; 7.AP.240.223;
7.AP.240.240; 7.AP.240.244; 7.AP.240.243; 7.AP.240.247; 7.AP.244.157;
7.AP.244.158; 7.AP.244.196; 7.AP.244.223; 7.AP.244.240; 7.AP.244.244;
7.AP.244.243; 7.AP.244.247; 7.AP.247.157; 7.AP.247.158; 7.AP.247.196;
7.AP.247.223; 7.AP.247.240; 7.AP.247.244; 7.AP.247.243; 7.AP.247.247;
Prodrugs of 7.AZ 7.AZ.4.157; 7.AZ.4.158; 7.AZ.4.196; 7.AZ.4.223; 7.AZ.4.240; 7.AZ.4.244;
7.AZ.4.243; 7.AZ.4.247; 7.AZ.5.157; 7.AZ.5.158; 7.AZ.5.196; 7.AZ.5.223;
7.AZ.5.240; 7.AZ.5.244; 7.AZ.5.243; 7.AZ.5.247; 7.AZ.7.157; 7.AZ.7.158;
7.AZ.7.196; 7.AZ.7.223; 7.AZ.7.240; 7.AZ.7.244; 7.AZ.7.243; 7.AZ.7.247;
7.AZ.15.157; 7.AZ.15.158; 7.AZ.15.196; 7.AZ.15.223; 7.AZ.15.240;
7.AZ.15.244; 7.AZ.15.243; 7.AZ.15.247; 7.AZ.16.157; 7.AZ.16.158;
7.AZ.16.196; 7.AZ.16.223; 7.AZ.16.240; 7.AZ.16.244; 7.AZ.16.243;
7.AZ.16.247; 7.AZ.18.157; 7.AZ.18.158; 7.AZ.18.196; 7.AZ.18.223;
7.AZ.18.240; 7.AZ.18.244; 7.AZ.18.243; 7.AZ.18.247; 7.AZ.26.157;
7.AZ.26.158; 7.AZ.26.196; 7.AZ.26.223; 7.AZ.26.240; 7.AZ.26.244;
7.AZ.26.243; 7.AZ.26.247; 7.AZ.27.157; 7.AZ.27.158; 7.AZ.27.196;
7.AZ.27.223; 7.AZ.27.240; 7.AZ.27.244; 7.AZ.27.243; 7.AZ.27.247;
7.AZ.29.157; 7.AZ.29.158; 7.AZ.29.196; 7.AZ.29.223; 7.AZ.29.240;
7.AZ.29.244; 7.AZ.29.243; 7.AZ.29.247; 7.AZ.54.157; 7.AZ.54.158;
7.AZ.54.196; 7.AZ.54.223; 7.AZ.54.240; 7.AZ.54.244; 7.AZ.54.243;
7.AZ.54.247; 7.AZ.55.157; 7.AZ.55.158; 7.AZ.55.196; 7.AZ.55.223;
7.AZ.55.240; 7.AZ.55.244; 7.AZ.55.243; 7.AZ.55.247; 7.AZ.56.157;
7.AZ.56.158; 7.AZ.56.196; 7.AZ.56.223; 7.AZ.56.240; 7.AZ.56.244;
7.AZ.56.243; 7.AZ.56.247; 7.AZ.157.157; 7.AZ.157.158; 7.AZ.157.196;
7.AZ.157.223; 7.AZ.157.240; 7.AZ.157.244; 7.AZ.157.243; 7.AZ.157.247;
7.AZ.196.157; 7.AZ.196.158; 7.AZ.196.196; 7.AZ.196.223; 7.AZ.196.240;
7.AZ.196.244; 7.AZ.196.243; 7.AZ.196.247; 7.AZ.223.157; 7.AZ.223.158;
7.AZ.223.196; 7.AZ.223.223; 7.AZ.223.240; 7.AZ.223.244; 7.AZ.223.243;
7.AZ.223.247; 7.AZ.240.157; 7.AZ.240.158; 7.AZ.240.196; 7.AZ.240.223;
7.AZ.240.240; 7.AZ.240.244; 7.AZ.240.243; 7.AZ.240.247; 7.AZ.244.157;
7.AZ.244.158; 7.AZ.244.196; 7.AZ.244.223; 7.AZ.244.240; 7.AZ.244.244;
7.AZ.244.243; 7.AZ.244.247; 7.AZ.247.157; 7.AZ.247.158; 7.AZ.247.196;
7.AZ.247.223; 7.AZ.247.240; 7.AZ.247.244; 7.AZ.247.243; 7.AZ.247.247;
Prodrugs of 7.BF 7.BF.4.157; 7.BF.4.158; 7.BF.4.196; 7.BF.4.223; 7.BF.4.240; 7.BF.4.244;
7.BF.4.243; 7.BF.4.247; 7.BF.5.157; 7.BF.5.158; 7.BF.5.196; 7.BF.5.223;
7.BF.5.240; 7.BF.5.244; 7.BF.5.243; 7.BF.5.247; 7.BF.7.157; 7.BF.7.158;
7.BF.7.196; 7.BF.7.223; 7.BF.7.240; 7.BF.7.244; 7.BF.7.243; 7.BF.7.247;

TABLE 100-continued

7.BF.15.157; 7.BF.15.158; 7.BF.15.196; 7.BF.15.223; 7.BF.15.240;
7.BF.15.244; 7.BF.15.243; 7.BF.15.247; 7.BF.16.157; 7.BF.16.158;
7.BF.16.196; 7.BF.16.223; 7.BF.16.240; 7.BF.16.244; 7.BF.16.243;
7.BF.16.247; 7.BF.18.157; 7.BF.18.158; 7.BF.18.196; 7.BF.18.223;
7.BF.18.240; 7.BF.18.244; 7.BF.18.243; 7.BF.18.247; 7.BF.26.157;
7.BF.26.158; 7.BF.26.196; 7.BF.26.223; 7.BF.26.240; 7.BF.26.244;
7.BF.26.243; 7.BF.26.247; 7.BF.27.157; 7.BF.27.158; 7.BF.27.196;
7.BF.27.223; 7.BF.27.240; 7.BF.27.244; 7.BF.27.243; 7.BF.27.247;
7.BF.29.157; 7.BF.29.158; 7.BF.29.196; 7.BF.29.223; 7.BF.29.240;
7.BF.29.244; 7.BF.29.243; 7.BF.29.247; 7.BF.54.157; 7.BF.54.158;
7.BF.54.196; 7.BF.54.223; 7.BF.54.240; 7.BF.54.244; 7.BF.54.243;
7.BF.54.247; 7.BF.55.157; 7.BF.55.158; 7.BF.55.196; 7.BF.55.223;
7.BF.55.240; 7.BF.55.244; 7.BF.55.243; 7.BF.55.247; 7.BF.56.157;
7.BF.56.158; 7.BF.56.196; 7.BF.56.223; 7.BF.56.240; 7.BF.56.244;
7.BF.56.243; 7.BF.56.247; 7.BF.157.157; 7.BF.157.158; 7.BF.157.196;
7.BF.157.223; 7.BF.157.240; 7.BF.157.244; 7.BF.157.243; 7.BF.157.247;
7.BF.196.157; 7.BF.196.158; 7.BF.196.196; 7.BF.196.223; 7.BF.196.240;
7.BF.196.244; 7.BF.196.243; 7.BF.196.247; 7.BF.223.157; 7.BF.223.158;
7.BF.223.196; 7.BF.223.223; 7.BF.223.240; 7.BF.223.244; 7.BF.223.243;
7.BF.223.247; 7.BF.240.157; 7.BF.240.158; 7.BF.240.196; 7.BF.240.223;
7.BF.240.240; 7.BF.240.244; 7.BF.240.243; 7.BF.240.247; 7.BF.244.157;
7.BF.244.158; 7.BF.244.196; 7.BF.244.223; 7.BF.244.240; 7.BF.244.244;
7.BF.244.243; 7.BF.244.247; 7.BF.247.157; 7.BF.247.158; 7.BF.247.196;
7.BF.247.223; 7.BF.247.240; 7.BF.247.244; 7.BF.247.243; 7.BF.247.247;
Prodrugs of 7.CI 7.CI.4.157; 7.CI.4.158; 7.CI.4.196; 7.CI.4.223; 7.CI.4.240; 7.CI.4.244;
7.CI.4.243; 7.CI.4.247; 7.CI.5.157; 7.CI.5.158; 7.CI.5.196; 7.CI.5.223;
7.CI.5.240; 7.CI.5.244; 7.CI.5.243; 7.CI.5.247; 7.CI.7.157; 7.CI.7.158;
7.CI.7.196; 7.CI.7.223; 7.CI.7.240; 7.CI.7.244; 7.CI.7.243; 7.CI.7.247;
7.CI.15.157; 7.CI.15.158; 7.CI.15.196; 7.CI.15.223; 7.CI.15.240; 7.CI.15.244;
7.CI.15.243; 7.CI.15.247; 7.CI.16.157; 7.CI.16.158; 7.CI.16.196; 7.CI.16.223;
7.CI.16.240; 7.CI.16.244; 7.CI.16.243; 7.CI.16.247; 7.CI.18.157; 7.CI.18.158;
7.CI.18.196; 7.CI.18.223; 7.CI.18.240; 7.CI.18.244; 7.CI.18.243; 7.CI.18.247;
7.CI.26.157; 7.CI.26.158; 7.CI.26.196; 7.CI.26.223; 7.CI.26.240; 7.CI.26.244;
7.CI.26.243; 7.CI.26.247; 7.CI.27.157; 7.CI.27.158; 7.CI.27.196; 7.CI.27.223;
7.CI.27.240; 7.CI.27.244; 7.CI.27.243; 7.CI.27.247; 7.CI.29.157; 7.CI.29.158;
7.CI.29.196; 7.CI.29.223; 7.CI.29.240; 7.CI.29.244; 7.CI.29.243; 7.CI.29.247;
7.CI.54.157; 7.CI.54.158; 7.CI.54.196; 7.CI.54.223; 7.CI.54.240; 7.CI.54.244;
7.CI.54.243; 7.CI.54.247; 7.CI.55.157; 7.CI.55.158; 7.CI.55.196; 7.CI.55.223;
7.CI.55.240; 7.CI.55.244; 7.CI.55.243; 7.CI.55.247; 7.CI.56.157; 7.CI.56.158;
7.CI.56.196; 7.CI.56.223; 7.CI.56.240; 7.CI.56.244; 7.CI.56.243; 7.CI.56.247;
7.CI.157.157; 7.CI.157.158; 7.CI.157.196; 7.CI.157.223; 7.CI.157.240;
7.CI.157.244; 7.CI.157.243; 7.CI.157.247; 7.CI.196.157; 7.CI.196.158;
7.CI.196.196; 7.CI.196.223; 7.CI.196.240; 7.CI.196.244; 7.CI.196.243;
7.CI.196.247; 7.CI.223.157; 7.CI.223.158; 7.CI.223.196; 7.CI.223.223;
7.CI.223.240; 7.CI.223.244; 7.CI.223.243; 7.CI.223.247; 7.CI.240.157;
7.CI.240.158; 7.CI.240.196; 7.CI.240.223; 7.CI.240.240; 7.CI.240.244;
7.CI.240.243; 7.CI.240.247; 7.CI.244.157; 7.CI.244.158; 7.CI.244.196;
7.CI.244.223; 7.CI.244.240; 7.CI.244.244; 7.CI.244.243; 7.CI.244.247;
7.CI.247.157; 7.CI.247.158; 7.CI.247.196; 7.CI.247.223; 7.CI.247.240;
7.CI.247.244; 7.CI.247.243; 7.CI.247.247;
Prodrugs of 7.CO 7.CO.4.157; 7.CO.4.158; 7.CO.4.196; 7.CO.4.223; 7.CO.4.240; 7.CO.4.244;
7.CO.4.243; 7.CO.4.247; 7.CO.5.157; 7.CO.5.158; 7.CO.5.196; 7.CO.5.223;
7.CO.5.240; 7.CO.5.244; 7.CO.5.243; 7.CO.5.247; 7.CO.7.157; 7.CO.7.158;
7.CO.7.196; 7.CO.7.223; 7.CO.7.240; 7.CO.7.244; 7.CO.7.243; 7.CO.7.247;
7.CO.15.157; 7.CO.15.158; 7.CO.15.196; 7.CO.15.223; 7.CO.15.240;
7.CO.15.244; 7.CO.15.243; 7.CO.15.247; 7.CO.16.157; 7.CO.16.158;
7.CO.16.196; 7.CO.16.223; 7.CO.16.240; 7.CO.16.244; 7.CO.16.243;
7.CO.16.247; 7.CO.18.157; 7.CO.18.158; 7.CO.18.196; 7.CO.18.223;
7.CO.18.240; 7.CO.18.244; 7.CO.18.243; 7.CO.18.247; 7.CO.26.157;
7.CO.26.158; 7.CO.26.196; 7.CO.26.223; 7.CO.26.240; 7.CO.26.244;
7.CO.26.243; 7.CO.26.247; 7.CO.27.157; 7.CO.27.158; 7.CO.27.196;
7.CO.27.223; 7.CO.27.240; 7.CO.27.244; 7.CO.27.243; 7.CO.27.247;
7.CO.29.157; 7.CO.29.158; 7.CO.29.196; 7.CO.29.223; 7.CO.29.240;
7.CO.29.244; 7.CO.29.243; 7.CO.29.247; 7.CO.54.157; 7.CO.54.158;
7.CO.54.196; 7.CO.54.223; 7.CO.54.240; 7.CO.54.244; 7.CO.54.243;
7.CO.54.247; 7.CO.55.157; 7.CO.55.158; 7.CO.55.196; 7.CO.55.223;
7.CO.55.240; 7.CO.55.244; 7.CO.55.243; 7.CO.55.247; 7.CO.56.157;
7.CO.56.158; 7.CO.56.196; 7.CO.56.223; 7.CO.56.240; 7.CO.56.244;
7.CO.56.243; 7.CO.56.247; 7.CO.157.157; 7.CO.157.158; 7.CO.157.196;
7.CO.157.223; 7.CO.157.240; 7.CO.157.244; 7.CO.157.243; 7.CO.157.247;
7.CO.196.157; 7.CO.196.158; 7.CO.196.196; 7.CO.196.223; 7.CO.196.240;
7.CO.196.244; 7.CO.196.243; 7.CO.196.247; 7.CO.223.157; 7.CO.223.158;
7.CO.223.196; 7.CO.223.223; 7.CO.223.240; 7.CO.223.244; 7.CO.223.243;
7.CO.223.247; 7.CO.240.157; 7.CO.240.158; 7.CO.240.196; 7.CO.240.223;
7.CO.240.240; 7.CO.240.244; 7.CO.240.243; 7.CO.240.247; 7.CO.244.157;

TABLE 100-continued

7.CO.244.158; 7.CO.244.196; 7.CO.244.223; 7.CO.244.240; 7.CO.244.244;
7.CO.244.243; 7.CO.244.247; 7.CO.4.157; 7.CO.4.158; 7.CO.4.196;
7.CO.4.223; 7.CO.4.240; 7.CO.4.244; 7.CO.4.243; 7.CO.4.247;

Prodrugs of 8.AH

8.AH.4.157; 8.AH.4.158; 8.AH.4.196; 8.AH.4.223; 8.AH.4.240; 8.AH.4.244;
8.AH.4.243; 8.AH.4.247; 8.AH.5.157; 8.AH.5.158; 8.AH.5.196; 8.AH.5.223;
8.AH.5.240; 8.AH.5.244; 8.AH.5.243; 8.AH.5.247; 8.AH.7.157; 8.AH.7.158;
8.AH.7.196; 8.AH.7.223; 8.AH.7.240; 8.AH.7.244; 8.AH.7.243; 8.AH.7.247;
8.AH.15.157; 8.AH.15.158; 8.AH.15.196; 8.AH.15.223; 8.AH.15.240;
8.AH.15.244; 8.AH.15.243; 8.AH.15.247; 8.AH.16.157; 8.AH.16.158;
8.AH.16.196; 8.AH.16.223; 8.AH.16.240; 8.AH.16.244; 8.AH.16.243;
8.AH.16.247; 8.AH.18.157; 8.AH.18.158; 8.AH.18.196; 8.AH.18.223;
8.AH.18.240; 8.AH.18.244; 8.AH.18.243; 8.AH.18.247; 8.AH.26.157;
8.AH.26.158; 8.AH.26.196; 8.AH.26.223; 8.AH.26.240; 8.AH.26.244;
8.AH.26.243; 8.AH.26.247; 8.AH.27.157; 8.AH.27.158; 8.AH.27.196;
8.AH.27.223; 8.AH.27.240; 8.AH.27.244; 8.AH.27.243; 8.AH.27.247;
8.AH.29.157; 8.AH.29.158; 8.AH.29.196; 8.AH.29.223; 8.AH.29.240;
8.AH.29.244; 8.AH.29.243; 8.AH.29.247; 8.AH.54.157; 8.AH.54.158;
8.AH.54.196; 8.AH.54.223; 8.AH.54.240; 8.AH.54.244; 8.AH.54.243;
8.AH.54.247; 8.AH.55.157; 8.AH.55.158; 8.AH.55.196; 8.AH.55.223;
8.AH.55.240; 8.AH.55.244; 8.AH.55.243; 8.AH.55.247; 8.AH.56.157;
8.AH.56.158; 8.AH.56.196; 8.AH.56.223; 8.AH.56.240; 8.AH.56.244;
8.AH.56.243; 8.AH.56.247; 8.AH.157.157; 8.AH.157.158; 8.AH.157.196;
8.AH.157.223; 8.AH.157.240; 8.AH.157.244; 8.AH.157.243; 8.AH.157.247;
8.AH.196.157; 8.AH.196.158; 8.AH.196.196; 8.AH.196.223; 8.AH.196.240;
8.AH.196.244; 8.AH.196.243; 8.AH.196.247; 8.AH.223.157; 8.AH.223.158;
8.AH.223.196; 8.AH.223.223; 8.AH.223.240; 8.AH.223.244; 8.AH.223.243;
8.AH.223.247; 8.AH.240.157; 8.AH.240.158; 8.AH.240.196; 8.AH.240.223;
8.AH.240.240; 8.AH.240.244; 8.AH.240.243; 8.AH.240.247; 8.AH.244.157;
8.AH.244.158; 8.AH.244.196; 8.AH.244.223; 8.AH.244.240; 8.AH.244.244;
8.AH.244.243; 8.AH.244.247; 8.AH.247.157; 8.AH.247.158; 8.AH.247.196;
8.AH.247.223; 8.AH.247.240; 8.AH.247.244; 8.AH.247.243; 8.AH.247.247;

Prodrugs of 8.AJ

8.AJ.4.157; 8.AJ.4.158; 8.AJ.4.196; 8.AJ.4.223; 8.AJ.4.240; 8.AJ.4.244;
8.AJ.4.243; 8.AJ.4.247; 8.AJ.5.157; 8.AJ.5.158; 8.AJ.5.196; 8.AJ.5.223;
8.AJ.5.240; 8.AJ.5.244; 8.AJ.5.243; 8.AJ.5.247; 8.AJ.7.157; 8.AJ.7.158;
8.AJ.7.196; 8.AJ.7.223; 8.AJ.7.240; 8.AJ.7.244; 8.AJ.7.243; 8.AJ.7.247;
8.AJ.15.157; 8.AJ.15.158; 8.AJ.15.196; 8.AJ.15.223; 8.AJ.15.240; 8.AJ.15.244;
8.AJ.15.243; 8.AJ.15.247; 8.AJ.16.157; 8.AJ.16.158; 8.AJ.16.196; 8.AJ.16.223;
8.AJ.16.240; 8.AJ.16.244; 8.AJ.16.243; 8.AJ.16.247; 8.AJ.18.157; 8.AJ.18.158;
8.AJ.18.196; 8.AJ.18.223; 8.AJ.18.240; 8.AJ.18.244; 8.AJ.18.243; 8.AJ.18.247;
8.AJ.26.157; 8.AJ.26.158; 8.AJ.26.196; 8.AJ.26.223; 8.AJ.26.240; 8.AJ.26.244;
8.AJ.26.243; 8.AJ.26.247; 8.AJ.27.157; 8.AJ.27.158; 8.AJ.27.196; 8.AJ.27.223;
8.AJ.27.240; 8.AJ.27.244; 8.AJ.27.243; 8.AJ.27.247; 8.AJ.29.157; 8.AJ.29.158;
8.AJ.29.196; 8.AJ.29.223; 8.AJ.29.240; 8.AJ.29.244; 8.AJ.29.243; 8.AJ.29.247;
8.AJ.54.157; 8.AJ.54.158; 8.AJ.54.196; 8.AJ.54.223; 8.AJ.54.240; 8.AJ.54.244;
8.AJ.54.243; 8.AJ.54.247; 8.AJ.55.157; 8.AJ.55.158; 8.AJ.55.196; 8.AJ.55.223;
8.AJ.55.240; 8.AJ.55.244; 8.AJ.55.243; 8.AJ.55.247; 8.AJ.56.157; 8.AJ.56.158;
8.AJ.56.196; 8.AJ.56.223; 8.AJ.56.240; 8.AJ.56.244; 8.AJ.56.243; 8.AJ.56.247;
8.AJ.157.157; 8.AJ.157.158; 8.AJ.157.196; 8.AJ.157.223; 8.AJ.157.240;
8.AJ.157.244; 8.AJ.157.243; 8.AJ.157.247; 8.AJ.196.157; 8.AJ.196.158;
8.AJ.196.196; 8.AJ.196.223; 8.AJ.196.240; 8.AJ.196.244; 8.AJ.196.243;
8.AJ.196.247; 8.AJ.223.157; 8.AJ.223.158; 8.AJ.223.196; 8.AJ.223.223;
8.AJ.223.240; 8.AJ.223.244; 8.AJ.223.243; 8.AJ.223.247; 8.AJ.240.157;
8.AJ.240.158; 8.AJ.240.196; 8.AJ.240.223; 8.AJ.240.240; 8.AJ.240.244;
8.AJ.240.243; 8.AJ.240.247; 8.AJ.244.157; 8.AJ.244.158; 8.AJ.244.196;
8.AJ.244.223; 8.AJ.244.240; 8.AJ.244.244; 8.AJ.244.243; 8.AJ.244.247;
8.AJ.247.157; 8.AJ.247.158; 8.AJ.247.196; 8.AJ.247.223; 8.AJ.247.240;
8.AJ.247.244; 8.AJ.247.243; 8.AJ.247.247;

Prodrugs of 8.AN

8.AN.4.157; 8.AN.4.158; 8.AN.4.196; 8.AN.4.223; 8.AN.4.240; 8.AN.4.244;
8.AN.4.243; 8.AN.4.247; 8.AN.5.157; 8.AN.5.158; 8.AN.5.196; 8.AN.5.223;
8.AN.5.240; 8.AN.5.244; 8.AN.5.243; 8.AN.5.247; 8.AN.7.157; 8.AN.7.158;
8.AN.7.196; 8.AN.7.223; 8.AN.7.240; 8.AN.7.244; 8.AN.7.243; 8.AN.7.247;
8.AN.15.157; 8.AN.15.158; 8.AN.15.196; 8.AN.15.223; 8.AN.15.240;
8.AN.15.244; 8.AN.15.243; 8.AN.15.247; 8.AN.16.157; 8.AN.16.158;
8.AN.16.196; 8.AN.16.223; 8.AN.16.240; 8.AN.16.244; 8.AN.16.243;
8.AN.16.247; 8.AN.18.157; 8.AN.18.158; 8.AN.18.196; 8.AN.18.223;
8.AN.18.240; 8.AN.18.244; 8.AN.18.243; 8.AN.18.247; 8.AN.26.157;
8.AN.26.158; 8.AN.26.196; 8.AN.26.223; 8.AN.26.240; 8.AN.26.244;
8.AN.26.243; 8.AN.26.247; 8.AN.27.157; 8.AN.27.158; 8.AN.27.196;
8.AN.27.223; 8.AN.27.240; 8.AN.27.244; 8.AN.27.243; 8.AN.27.247;
8.AN.29.157; 8.AN.29.158; 8.AN.29.196; 8.AN.29.223; 8.AN.29.240;
8.AN.29.244; 8.AN.29.243; 8.AN.29.247; 8.AN.54.157; 8.AN.54.158;
8.AN.54.196; 8.AN.54.223; 8.AN.54.240; 8.AN.54.244; 8.AN.54.243;
8.AN.54.247; 8.AN.55.157; 8.AN.55.158; 8.AN.55.196; 8.AN.55.223;

TABLE 100-continued

8.AN.55.240; 8.AN.55.244; 8.AN.55.243; 8.AN.55.247; 8.AN.56.157;
8.AN.56.158; 8.AN.56.196; 8.AN.56.223; 8.AN.56.240; 8.AN.56.244;
8.AN.56.243; 8.AN.56.247; 8.AN.157.157; 8.AN.157.158; 8.AN.157.196;
8.AN.157.223; 8.AN.157.240; 8.AN.157.244; 8.AN.157.243; 8.AN.157.247;
8.AN.196.157; 8.AN.196.158; 8.AN.196.196; 8.AN.196.223; 8.AN.196.240;
8.AN.196.244; 8.AN.196.243; 8.AN.196.247; 8.AN.223.157; 8.AN.223.158;
8.AN.223.196; 8.AN.223.223; 8.AN.223.240; 8.AN.223.244; 8.AN.223.243;
8.AN.223.247; 8.AN.240.157; 8.AN.240.158; 8.AN.240.196; 8.AN.240.223;
8.AN.240.240; 8.AN.240.244; 8.AN.240.243; 8.AN.240.247; 8.AN.244.157;
8.AN.244.158; 8.AN.244.196; 8.AN.244.223; 8.AN.244.240; 8.AN.244.244;
8.AN.244.243; 8.AN.244.247; 8.AN.247.157; 8.AN.247.158; 8.AN.247.196;
8.AN.247.223; 8.AN.247.240; 8.AN.247.244; 8.AN.247.243; 8.AN.247.247;
Prodrugs of 8.AP 8.AP.4.157; 8.AP.4.158; 8.AP.4.196; 8.AP.4.223; 8.AP.4.240; 8.AP.4.244;
8.AP.4.243; 8.AP.4.247; 8.AP.5.157; 8.AP.5.158; 8.AP.5.196; 8.AP.5.223;
8.AP.5.240; 8.AP.5.244; 8.AP.5.243; 8.AP.5.247; 8.AP.7.157; 8.AP.7.158;
8.AP.7.196; 8.AP.7.223; 8.AP.7.240; 8.AP.7.244; 8.AP.7.243; 8.AP.7.247;
8.AP.15.157; 8.AP.15.158; 8.AP.15.196; 8.AP.15.223; 8.AP.15.240;
8.AP.15.244; 8.AP.15.243; 8.AP.15.247; 8.AP.16.157; 8.AP.16.158;
8.AP.16.196; 8.AP.16.223; 8.AP.16.240; 8.AP.16.244; 8.AP.16.243;
8.AP.16.247; 8.AP.18.157; 8.AP.18.158; 8.AP.18.196; 8.AP.18.223;
8.AP.18.240; 8.AP.18.244; 8.AP.18.243; 8.AP.18.247; 8.AP.26.157;
8.AP.26.158; 8.AP.26.196; 8.AP.26.223; 8.AP.26.240; 8.AP.26.244;
8.AP.26.243; 8.AP.26.247; 8.AP.27.157; 8.AP.27.158; 8.AP.27.196;
8.AP.27.223; 8.AP.27.240; 8.AP.27.244; 8.AP.27.243; 8.AP.27.247;
8.AP.29.157; 8.AP.29.158; 8.AP.29.196; 8.AP.29.223; 8.AP.29.240;
8.AP.29.244; 8.AP.29.243; 8.AP.29.247; 8.AP.54.157; 8.AP.54.158;
8.AP.54.196; 8.AP.54.223; 8.AP.54.240; 8.AP.54.244; 8.AP.54.243;
8.AP.54.247; 8.AP.55.157; 8.AP.55.158; 8.AP.55.196; 8.AP.55.223;
8.AP.55.240; 8.AP.55.244; 8.AP.55.243; 8.AP.55.247; 8.AP.56.157;
8.AP.56.158; 8.AP.56.196; 8.AP.56.223; 8.AP.56.240; 8.AP.56.244;
8.AP.56.243; 8.AP.56.247; 8.AP.157.157; 8.AP.157.158; 8.AP.157.196;
8.AP.157.223; 8.AP.157.240; 8.AP.157.244; 8.AP.157.243; 8.AP.157.247;
8.AP.196.157; 8.AP.196.158; 8.AP.196.196; 8.AP.196.223; 8.AP.196.240;
8.AP.196.244; 8.AP.196.243; 8.AP.196.247; 8.AP.223.157; 8.AP.223.158;
8.AP.223.196; 8.AP.223.223; 8.AP.223.240; 8.AP.223.244; 8.AP.223.243;
8.AP.223.247; 8.AP.240.157; 8.AP.240.158; 8.AP.240.196; 8.AP.240.223;
8.AP.240.240; 8.AP.240.244; 8.AP.240.243; 8.AP.240.247; 8.AP.244.157;
8.AP.244.158; 8.AP.244.196; 8.AP.244.223; 8.AP.244.240; 8.AP.244.244;
8.AP.244.243; 8.AP.244.247; 8.AP.247.157; 8.AP.247.158; 8.AP.247.196;
8.AP.247.223; 8.AP.247.240; 8.AP.247.244; 8.AP.247.243; 8.AP.247.247;
Prodrugs of 8.AZ 8.AZ.4.157; 8.AZ.4.158; 8.AZ.4.196; 8.AZ.4.223; 8.AZ.4.240; 8.AZ.4.244;
8.AZ.4.243; 8.AZ.4.247; 8.AZ.5.157; 8.AZ.5.158; 8.AZ.5.196; 8.AZ.5.223;
8.AZ.5.240; 8.AZ.5.244; 8.AZ.5.243; 8.AZ.5.247; 8.AZ.7.157; 8.AZ.7.158;
8.AZ.7.196; 8.AZ.7.223; 8.AZ.7.240; 8.AZ.7.244; 8.AZ.7.243; 8.AZ.7.247;
8.AZ.15.157; 8.AZ.15.158; 8.AZ.15.196; 8.AZ.15.223; 8.AZ.15.240;
8.AZ.15.244; 8.AZ.15.243; 8.AZ.15.247; 8.AZ.16.157; 8.AZ.16.158;
8.AZ.16.196; 8.AZ.16.223; 8.AZ.16.240; 8.AZ.16.244; 8.AZ.16.243;
8.AZ.16.247; 8.AZ.18.157; 8.AZ.18.158; 8.AZ.18.196; 8.AZ.18.223;
8.AZ.18.240; 8.AZ.18.244; 8.AZ.18.243; 8.AZ.18.247; 8.AZ.26.157;
8.AZ.26.158; 8.AZ.26.196; 8.AZ.26.223; 8.AZ.26.240; 8.AZ.26.244;
8.AZ.26.243; 8.AZ.26.247; 8.AZ.27.157; 8.AZ.27.158; 8.AZ.27.196;
8.AZ.27.223; 8.AZ.27.240; 8.AZ.27.244; 8.AZ.27.243; 8.AZ.27.247;
8.AZ.29.157; 8.AZ.29.158; 8.AZ.29.196; 8.AZ.29.223; 8.AZ.29.240;
8.AZ.29.244; 8.AZ.29.243; 8.AZ.29.247; 8.AZ.54.157; 8.AZ.54.158;
8.AZ.54.196; 8.AZ.54.223; 8.AZ.54.240; 8.AZ.54.244; 8.AZ.54.243;
8.AZ.54.247; 8.AZ.55.157; 8.AZ.55.158; 8.AZ.55.196; 8.AZ.55.223;
8.AZ.55.240; 8.AZ.55.244; 8.AZ.55.243; 8.AZ.55.247; 8.AZ.56.157;
8.AZ.56.158; 8.AZ.56.196; 8.AZ.56.223; 8.AZ.56.240; 8.AZ.56.244;
8.AZ.56.243; 8.AZ.56.247; 8.AZ.157.157; 8.AZ.157.158; 8.AZ.157.196;
8.AZ.157.223; 8.AZ.157.240; 8.AZ.157.244; 8.AZ.157.243; 8.AZ.157.247;
8.AZ.196.157; 8.AZ.196.158; 8.AZ.196.196; 8.AZ.196.223; 8.AZ.196.240;
8.AZ.196.244; 8.AZ.196.243; 8.AZ.196.247; 8.AZ.223.157; 8.AZ.223.158;
8.AZ.223.196; 8.AZ.223.223; 8.AZ.223.240; 8.AZ.223.244; 8.AZ.223.243;
8.AZ.223.247; 8.AZ.240.157; 8.AZ.240.158; 8.AZ.240.196; 8.AZ.240.223;
8.AZ.240.240; 8.AZ.240.244; 8.AZ.240.243; 8.AZ.240.247; 8.AZ.244.157;
8.AZ.244.158; 8.AZ.244.196; 8.AZ.244.223; 8.AZ.244.240; 8.AZ.244.244;
8.AZ.244.243; 8.AZ.244.247; 8.AZ.247.157; 8.AZ.247.158; 8.AZ.247.196;
8.AZ.247.223; 8.AZ.247.240; 8.AZ.247.244; 8.AZ.247.243; 8.AZ.247.247;
Prodrugs of 8.BF 8.BF.4.157; 8.BF.4.158; 8.BF.4.196; 8.BF.4.223; 8.BF.4.240; 8.BF.4.244;
8.BF.4.243; 8.BF.4.247; 8.BF.5.157; 8.BF.5.158; 8.BF.5.196; 8.BF.5.223;
8.BF.5.240; 8.BF.5.244; 8.BF.5.243; 8.BF.5.247; 8.BF.7.157; 8.BF.7.158;
8.BF.7.196; 8.BF.7.223; 8.BF.7.240; 8.BF.7.244; 8.BF.7.243; 8.BF.7.247;
8.BF.15.157; 8.BF.15.158; 8.BF.15.196; 8.BF.15.223; 8.BF.15.240;

TABLE 100-continued

8.BF.15.244; 8.BF.15.243; 8.BF.15.247; 8.BF.16.157; 8.BF.16.158;
8.BF.16.196; 8.BF.16.223; 8.BF.16.240; 8.BF.16.244; 8.BF.16.243;
8.BF.16.247; 8.BF.18.157; 8.BF.18.158; 8.BF.18.196; 8.BF.18.223;
8.BF.18.240; 8.BF.18.244; 8.BF.18.243; 8.BF.18.247; 8.BF.26.157;
8.BF.26.158; 8.BF.26.196; 8.BF.26.223; 8.BF.26.240; 8.BF.26.244;
8.BF.26.243; 8.BF.26.247; 8.BF.27.157; 8.BF.27.158; 8.BF.27.196;
8.BF.27.223; 8.BF.27.240; 8.BF.27.244; 8.BF.27.243; 8.BF.27.247;
8.BF.29.157; 8.BF.29.158; 8.BF.29.196; 8.BF.29.223; 8.BF.29.240;
8.BF.29.244; 8.BF.29.243; 8.BF.29.247; 8.BF.54.157; 8.BF.54.158;
8.BF.54.196; 8.BF.54.223; 8.BF.54.240; 8.BF.54.244; 8.BF.54.243;
8.BF.54.247; 8.BF.55.157; 8.BF.55.158; 8.BF.55.196; 8.BF.55.223;
8.BF.55.240; 8.BF.55.244; 8.BF.55.243; 8.BF.55.247; 8.BF.56.157;
8.BF.56.158; 8.BF.56.196; 8.BF.56.223; 8.BF.56.240; 8.BF.56.244;
8.BF.56.243; 8.BF.56.247; 8.BF.157.157; 8.BF.157.158; 8.BF.157.196;
8.BF.157.223; 8.BF.157.240; 8.BF.157.244; 8.BF.157.243; 8.BF.157.247;
8.BF.196.157; 8.BF.196.158; 8.BF.196.196; 8.BF.196.223; 8.BF.196.240;
8.BF.196.244; 8.BF.196.243; 8.BF.196.247; 8.BF.223.157; 8.BF.223.158;
8.BF.223.196; 8.BF.223.223; 8.BF.223.240; 8.BF.223.244; 8.BF.223.243;
8.BF.223.247; 8.BF.240.157; 8.BF.240.158; 8.BF.240.196; 8.BF.240.223;
8.BF.240.240; 8.BF.240.244; 8.BF.240.243; 8.BF.240.247; 8.BF.244.157;
8.BF.244.158; 8.BF.244.196; 8.BF.244.223; 8.BF.244.240; 8.BF.244.244;
8.BF.244.243; 8.BF.244.247; 8.BF.247.157; 8.BF.247.158; 8.BF.247.196;
8.BF.247.223; 8.BF.247.240; 8.BF.247.244; 8.BF.247.243; 8.BF.247.247;
Prodrugs of 8.CI 8.CI.4.157; 8.CI.4.158; 8.CI.4.196; 8.CI.4.223; 8.CI.4.240; 8.CI.4.244;
8.CI.4.243; 8.CI.4.247; 8.CI.5.157; 8.CI.5.158; 8.CI.5.196; 8.CI.5.223;
8.CI.5.240; 8.CI.5.244; 8.CI.5.243; 8.CI.5.247; 8.CI.7.157; 8.CI.7.158;
8.CI.7.196; 8.CI.7.223; 8.CI.7.240; 8.CI.7.244; 8.CI.7.243; 8.CI.7.247;
8.CI.15.157; 8.CI.15.158; 8.CI.15.196; 8.CI.15.223; 8.CI.15.240; 8.CI.15.244;
8.CI.15.243; 8.CI.15.247; 8.CI.16.157; 8.CI.16.158; 8.CI.16.196; 8.CI.16.223;
8.CI.16.240; 8.CI.16.244; 8.CI.16.243; 8.CI.16.247; 8.CI.18.157; 8.CI.18.158;
8.CI.18.196; 8.CI.18.223; 8.CI.18.240; 8.CI.18.244; 8.CI.18.243; 8.CI.18.247;
8.CI.26.157; 8.CI.26.158; 8.CI.26.196; 8.CI.26.223; 8.CI.26.240; 8.CI.26.244;
8.CI.26.243; 8.CI.26.247; 8.CI.27.157; 8.CI.27.158; 8.CI.27.196; 8.CI.27.223;
8.CI.27.240; 8.CI.27.244; 8.CI.27.243; 8.CI.27.247; 8.CI.29.157; 8.CI.29.158;
8.CI.29.196; 8.CI.29.223; 8.CI.29.240; 8.CI.29.244; 8.CI.29.243; 8.CI.29.247;
8.CI.54.157; 8.CI.54.158; 8.CI.54.196; 8.CI.54.223; 8.CI.54.240; 8.CI.54.244;
8.CI.54.243; 8.CI.54.247; 8.CI.55.157; 8.CI.55.158; 8.CI.55.196; 8.CI.55.223;
8.CI.55.240; 8.CI.55.244; 8.CI.55.243; 8.CI.55.247; 8.CI.56.157; 8.CI.56.158;
8.CI.56.196; 8.CI.56.223; 8.CI.56.240; 8.CI.56.244; 8.CI.56.243; 8.CI.56.247;
8.CI.157.157; 8.CI.157.158; 8.CI.157.196; 8.CI.157.223; 8.CI.157.240;
8.CI.157.244; 8.CI.157.243; 8.CI.157.247; 8.CI.196.157; 8.CI.196.158;
8.CI.196.196; 8.CI.196.223; 8.CI.196.240; 8.CI.196.244; 8.CI.196.243;
8.CI.196.247; 8.CI.223.157; 8.CI.223.158; 8.CI.223.196; 8.CI.223.223;
8.CI.223.240; 8.CI.223.244; 8.CI.223.243; 8.CI.223.247; 8.CI.240.157;
8.CI.240.158; 8.CI.240.196; 8.CI.240.223; 8.CI.240.240; 8.CI.240.244;
8.CI.240.243; 8.CI.240.247; 8.CI.244.157; 8.CI.244.158; 8.CI.244.196;
8.CI.244.223; 8.CI.244.240; 8.CI.244.244; 8.CI.244.243; 8.CI.244.247;
8.CI.247.157; 8.CI.247.158; 8.CI.247.196; 8.CI.247.223; 8.CI.247.240;
8.CI.247.244; 8.CI.247.243; 8.CI.247.247;
Prodrugs of 8.CO 8.CO.4.157; 8.CO.4.158; 8.CO.4.196; 8.CO.4.223; 8.CO.4.240; 8.CO.4.244;
8.CO.4.243; 8.CO.4.247; 8.CO.5.157; 8.CO.5.158; 8.CO.5.196; 8.CO.5.223;
8.CO.5.240; 8.CO.5.244; 8.CO.5.243; 8.CO.5.247; 8.CO.7.157; 8.CO.7.158;
8.CO.7.196; 8.CO.7.223; 8.CO.7.240; 8.CO.7.244; 8.CO.7.243; 8.CO.7.247;
8.CO.15.157; 8.CO.15.158; 8.CO.15.196; 8.CO.15.223; 8.CO.15.240;
8.CO.15.244; 8.CO.15.243; 8.CO.15.247; 8.CO.16.157; 8.CO.16.158;
8.CO.16.196; 8.CO.16.223; 8.CO.16.240; 8.CO.16.244; 8.CO.16.243;
8.CO.16.247; 8.CO.18.157; 8.CO.18.158; 8.CO.18.196; 8.CO.18.223;
8.CO.18.240; 8.CO.18.244; 8.CO.18.243; 8.CO.18.247; 8.CO.26.157;
8.CO.26.158; 8.CO.26.196; 8.CO.26.223; 8.CO.26.240; 8.CO.26.244;
8.CO.26.243; 8.CO.26.247; 8.CO.27.157; 8.CO.27.158; 8.CO.27.196;
8.CO.27.223; 8.CO.27.240; 8.CO.27.244; 8.CO.27.243; 8.CO.27.247;
8.CO.29.157; 8.CO.29.158; 8.CO.29.196; 8.CO.29.223; 8.CO.29.240;
8.CO.29.244; 8.CO.29.243; 8.CO.29.247; 8.CO.54.157; 8.CO.54.158;
8.CO.54.196; 8.CO.54.223; 8.CO.54.240; 8.CO.54.244; 8.CO.54.243;
8.CO.54.247; 8.CO.55.157; 8.CO.55.158; 8.CO.55.196; 8.CO.55.223;
8.CO.55.240; 8.CO.55.244; 8.CO.55.243; 8.CO.55.247; 8.CO.56.157;
8.CO.56.158; 8.CO.56.196; 8.CO.56.223; 8.CO.56.240; 8.CO.56.244;
8.CO.56.243; 8.CO.56.247; 8.CO.157.157; 8.CO.157.158; 8.CO.157.196;
8.CO.157.223; 8.CO.157.240; 8.CO.157.244; 8.CO.157.243; 8.CO.157.247;
8.CO.196.157; 8.CO.196.158; 8.CO.196.196; 8.CO.196.223; 8.CO.196.240;
8.CO.196.244; 8.CO.196.243; 8.CO.196.247; 8.CO.223.157; 8.CO.223.158;
8.CO.223.196; 8.CO.223.223; 8.CO.223.240; 8.CO.223.244; 8.CO.223.243;
8.CO.223.247; 8.CO.240.157; 8.CO.240.158; 8.CO.240.196; 8.CO.240.223;
8.CO.240.240; 8.CO.240.244; 8.CO.240.243; 8.CO.240.247; 8.CO.244.157;
8.CO.244.158; 8.CO.244.196; 8.CO.244.223; 8.CO.244.240; 8.CO.244.244;

TABLE 100-continued

8.CO.244.243; 8.CO.244.247; 8.CO.247.157; 8.CO.247.158; 8.CO.247.196;
8.CO.247.223; 8.CO.247.240; 8.CO.247.244; 8.CO.247.243; 8.CO.247.247;
Prodrugs of 9.AH 9.AH.4.157; 9.AH.4.158; 9.AH.4.196; 9.AH.4.223; 9.AH.4.240; 9.AH.4.244;
9.AH.4.243; 9.AH.4.247; 9.AH.5.157; 9.AH.5.158; 9.AH.5.196; 9.AH.5.223;
9.AH.5.240; 9.AH.5.244; 9.AH.5.243; 9.AH.5.247; 9.AH.7.157; 9.AH.7.158;
9.AH.7.196; 9.AH.7.223; 9.AH.7.240; 9.AH.7.244; 9.AH.7.243; 9.AH.7.247;
9.AH.15.157; 9.AH.15.158; 9.AH.15.196; 9.AH.15.223; 9.AH.15.240;
9.AH.15.244; 9.AH.15.243; 9.AH.15.247; 9.AH.16.157; 9.AH.16.158;
9.AH.16.196; 9.AH.16.223; 9.AH.16.240; 9.AH.16.244; 9.AH.16.243;
9.AH.16.247; 9.AH.18.157; 9.AH.18.158; 9.AH.18.196; 9.AH.18.223;
9.AH.18.240; 9.AH.18.244; 9.AH.18.243; 9.AH.18.247; 9.AH.26.157;
9.AH.26.158; 9.AH.26.196; 9.AH.26.223; 9.AH.26.240; 9.AH.26.244;
9.AH.26.243; 9.AH.26.247; 9.AH.27.157; 9.AH.27.158; 9.AH.27.196;
9.AH.27.223; 9.AH.27.240; 9.AH.27.244; 9.AH.27.243; 9.AH.27.247;
9.AH.29.157; 9.AH.29.158; 9.AH.29.196; 9.AH.29.223; 9.AH.29.240;
9.AH.29.244; 9.AH.29.243; 9.AH.29.247; 9.AH.54.157; 9.AH.54.158;
9.AH.54.196; 9.AH.54.223; 9.AH.54.240; 9.AH.54.244; 9.AH.54.243;
9.AH.54.247; 9.AH.55.157; 9.AH.55.158; 9.AH.55.196; 9.AH.55.223;
9.AH.55.240; 9.AH.55.244; 9.AH.55.243; 9.AH.55.247; 9.AH.56.157;
9.AH.56.158; 9.AH.56.196; 9.AH.56.223; 9.AH.56.240; 9.AH.56.244;
9.AH.56.243; 9.AH.56.247; 9.AH.157.157; 9.AH.157.158; 9.AH.157.196;
9.AH.157.223; 9.AH.157.240; 9.AH.157.244; 9.AH.157.243; 9.AH.157.247;
9.AH.196.157; 9.AH.196.158; 9.AH.196.196; 9.AH.196.223; 9.AH.196.240;
9.AH.196.244; 9.AH.196.243; 9.AH.196.247; 9.AH.223.157; 9.AH.223.158;
9.AH.223.196; 9.AH.223.223; 9.AH.223.240; 9.AH.223.244; 9.AH.223.243;
9.AH.223.247; 9.AH.240.157; 9.AH.240.158; 9.AH.240.196; 9.AH.240.223;
9.AH.240.240; 9.AH.240.244; 9.AH.240.243; 9.AH.240.247; 9.AH.244.157;
9.AH.244.158; 9.AH.244.196; 9.AH.244.223; 9.AH.244.240; 9.AH.244.244;
9.AH.244.243; 9.AH.244.247; 9.AH.247.157; 9.AH.247.158; 9.AH.247.196;
9.AH.247.223; 9.AH.247.240; 9.AH.247.244; 9.AH.247.243; 9.AH.247.247;
Prodrugs of 9.AJ 9.AJ.4.157; 9.AJ.4.158; 9.AJ.4.196; 9.AJ.4.223; 9.AJ.4.240; 9.AJ.4.244;
9.AJ.4.243; 9.AJ.4.247; 9.AJ.5.157; 9.AJ.5.158; 9.AJ.5.196; 9.AJ.5.223;
9.AJ.5.240; 9.AJ.5.244; 9.AJ.5.243; 9.AJ.5.247; 9.AJ.7.157; 9.AJ.7.158;
9.AJ.7.196; 9.AJ.7.223; 9.AJ.7.240; 9.AJ.7.244; 9.AJ.7.243; 9.AJ.7.247;
9.AJ.15.157; 9.AJ.15.158; 9.AJ.15.196; 9.AJ.15.223; 9.AJ.15.240; 9.AJ.15.244;
9.AJ.15.243; 9.AJ.15.247; 9.AJ.16.157; 9.AJ.16.158; 9.AJ.16.196; 9.AJ.16.223;
9.AJ.16.240; 9.AJ.16.244; 9.AJ.16.243; 9.AJ.16.247; 9.AJ.18.157; 9.AJ.18.158;
9.AJ.18.196; 9.AJ.18.223; 9.AJ.18.240; 9.AJ.18.244; 9.AJ.18.243; 9.AJ.18.247;
9.AJ.26.157; 9.AJ.26.158; 9.AJ.26.196; 9.AJ.26.223; 9.AJ.26.240; 9.AJ.26.244;
9.AJ.26.243; 9.AJ.26.247; 9.AJ.27.157; 9.AJ.27.158; 9.AJ.27.196; 9.AJ.27.223;
9.AJ.27.240; 9.AJ.27.244; 9.AJ.27.243; 9.AJ.27.247; 9.AJ.29.157; 9.AJ.29.158;
9.AJ.29.196; 9.AJ.29.223; 9.AJ.29.240; 9.AJ.29.244; 9.AJ.29.243; 9.AJ.29.247;
9.AJ.54.157; 9.AJ.54.158; 9.AJ.54.196; 9.AJ.54.223; 9.AJ.54.240; 9.AJ.54.244;
9.AJ.54.243; 9.AJ.54.247; 9.AJ.55.157; 9.AJ.55.158; 9.AJ.55.196; 9.AJ.55.223;
9.AJ.55.240; 9.AJ.55.244; 9.AJ.55.243; 9.AJ.55.247; 9.AJ.56.157; 9.AJ.56.158;
9.AJ.56.196; 9.AJ.56.223; 9.AJ.56.240; 9.AJ.56.244; 9.AJ.56.243; 9.AJ.56.247;
9.AJ.157.157; 9.AJ.157.158; 9.AJ.157.196; 9.AJ.157.223; 9.AJ.157.240;
9.AJ.157.244; 9.AJ.157.243; 9.AJ.157.247; 9.AJ.196.157; 9.AJ.196.158;
9.AJ.196.196; 9.AJ.196.223; 9.AJ.196.240; 9.AJ.196.244; 9.AJ.196.243;
9.AJ.196.247; 9.AJ.223.157; 9.AJ.223.158; 9.AJ.223.196; 9.AJ.223.223;
9.AJ.223.240; 9.AJ.223.244; 9.AJ.223.243; 9.AJ.223.247; 9.AJ.240.157;
9.AJ.240.158; 9.AJ.240.196; 9.AJ.240.223; 9.AJ.240.240; 9.AJ.240.244;
9.AJ.240.243; 9.AJ.240.247; 9.AJ.244.157; 9.AJ.244.158; 9.AJ.244.196;
9.AJ.244.223; 9.AJ.244.240; 9.AJ.244.244; 9.AJ.244.243; 9.AJ.244.247;
9.AJ.247.157; 9.AJ.247.158; 9.AJ.247.196; 9.AJ.247.223; 9.AJ.247.240;
9.AJ.247.244; 9.AJ.247.243; 9.AJ.247.247;
Prodrugs of 9.AN 9.AN.4.157; 9.AN.4.158; 9.AN.4.196; 9.AN.4.223; 9.AN.4.240; 9.AN.4.244;
9.AN.4.243; 9.AN.4.247; 9.AN.5.157; 9.AN.5.158; 9.AN.5.196; 9.AN.5.223;
9.AN.5.240; 9.AN.5.244; 9.AN.5.243; 9.AN.5.247; 9.AN.7.157; 9.AN.7.158;
9.AN.7.196; 9.AN.7.223; 9.AN.7.240; 9.AN.7.244; 9.AN.7.243; 9.AN.7.247;
9.AN.15.157; 9.AN.15.158; 9.AN.15.196; 9.AN.15.223; 9.AN.15.240;
9.AN.15.244; 9.AN.15.243; 9.AN.15.247; 9.AN.16.157; 9.AN.16.158;
9.AN.16.196; 9.AN.16.223; 9.AN.16.240; 9.AN.16.244; 9.AN.16.243;
9.AN.16.247; 9.AN.18.157; 9.AN.18.158; 9.AN.18.196; 9.AN.18.223;
9.AN.18.240; 9.AN.18.244; 9.AN.18.243; 9.AN.18.247; 9.AN.26.157;
9.AN.26.158; 9.AN.26.196; 9.AN.26.223; 9.AN.26.240; 9.AN.26.244;
9.AN.26.243; 9.AN.26.247; 9.AN.27.157; 9.AN.27.158; 9.AN.27.196;
9.AN.27.223; 9.AN.27.240; 9.AN.27.244; 9.AN.27.243; 9.AN.27.247;
9.AN.29.157; 9.AN.29.158; 9.AN.29.196; 9.AN.29.223; 9.AN.29.240;
9.AN.29.244; 9.AN.29.243; 9.AN.29.247; 9.AN.54.157; 9.AN.54.158;
9.AN.54.196; 9.AN.54.223; 9.AN.54.240; 9.AN.54.244; 9.AN.54.243;
9.AN.54.247; 9.AN.55.157; 9.AN.55.158; 9.AN.55.196; 9.AN.55.223;
9.AN.55.240; 9.AN.55.244; 9.AN.55.243; 9.AN.55.247; 9.AN.56.157;

TABLE 100-continued

9.AN.56.158; 9.AN.56.196; 9.AN.56.223; 9.AN.56.240; 9.AN.56.244;
9.AN.56.243; 9.AN.56.247; 9.AN.157.157; 9.AN.157.158; 9.AN.157.196;
9.AN.157.223; 9.AN.157.240; 9.AN.157.244; 9.AN.157.243; 9.AN.157.247;
9.AN.196.157; 9.AN.196.158; 9.AN.196.196; 9.AN.196.223; 9.AN.196.240;
9.AN.196.244; 9.AN.196.243; 9.AN.196.247; 9.AN.223.157; 9.AN.223.158;
9.AN.223.196; 9.AN.223.223; 9.AN.223.240; 9.AN.223.244; 9.AN.223.243;
9.AN.223.247; 9.AN.240.157; 9.AN.240.158; 9.AN.240.196; 9.AN.240.223;
9.AN.240.240; 9.AN.240.244; 9.AN.240.243; 9.AN.240.247; 9.AN.244.157;
9.AN.244.158; 9.AN.244.196; 9.AN.244.223; 9.AN.244.240; 9.AN.244.244;
9.AN.244.243; 9.AN.244.247; 9.AN.247.157; 9.AN.247.158; 9.AN.247.196;
9.AN.247.223; 9.AN.247.240; 9.AN.247.244; 9.AN.247.243; 9.AN.247.247;

Prodrugs of 9.AP

9.AP.4.157; 9.AP.4.158; 9.AP.4.196; 9.AP.4.223; 9.AP.4.240; 9.AP.4.244;
9.AP.4.243; 9.AP.4.247; 9.AP.5.157; 9.AP.5.158; 9.AP.5.196; 9.AP.5.223;
9.AP.5.240; 9.AP.5.244; 9.AP.5.243; 9.AP.5.247; 9.AP.7.157; 9.AP.7.158;
9.AP.7.196; 9.AP.7.223; 9.AP.7.240; 9.AP.7.244; 9.AP.7.243; 9.AP.7.247;
9.AP.15.157; 9.AP.15.158; 9.AP.15.196; 9.AP.15.223; 9.AP.15.240;
9.AP.15.244; 9.AP.15.243; 9.AP.15.247; 9.AP.16.157; 9.AP.16.158;
9.AP.16.196; 9.AP.16.223; 9.AP.16.240; 9.AP.16.244; 9.AP.16.243;
9.AP.16.247; 9.AP.18.157; 9.AP.18.158; 9.AP.18.196; 9.AP.18.223;
9.AP.18.240; 9.AP.18.244; 9.AP.18.243; 9.AP.18.247; 9.AP.26.157;
9.AP.26.158; 9.AP.26.196; 9.AP.26.223; 9.AP.26.240; 9.AP.26.244;
9.AP.26.243; 9.AP.26.247; 9.AP.27.157; 9.AP.27.158; 9.AP.27.196;
9.AP.27.223; 9.AP.27.240; 9.AP.27.244; 9.AP.27.243; 9.AP.27.247;
9.AP.29.157; 9.AP.29.158; 9.AP.29.196; 9.AP.29.223; 9.AP.29.240;
9.AP.29.244; 9.AP.29.243; 9.AP.29.247; 9.AP.54.157; 9.AP.54.158;
9.AP.54.196; 9.AP.54.223; 9.AP.54.240; 9.AP.54.244; 9.AP.54.243;
9.AP.54.247; 9.AP.55.157; 9.AP.55.158; 9.AP.55.196; 9.AP.55.223;
9.AP.55.240; 9.AP.55.244; 9.AP.55.243; 9.AP.55.247; 9.AP.56.157;
9.AP.56.158; 9.AP.56.196; 9.AP.56.223; 9.AP.56.240; 9.AP.56.244;
9.AP.56.243; 9.AP.56.247; 9.AP.157.157; 9.AP.157.158; 9.AP.157.196;
9.AP.157.223; 9.AP.157.240; 9.AP.157.244; 9.AP.157.243; 9.AP.157.247;
9.AP.196.157; 9.AP.196.158; 9.AP.196.196; 9.AP.196.223; 9.AP.196.240;
9.AP.196.244; 9.AP.196.243; 9.AP.196.247; 9.AP.223.157; 9.AP.223.158;
9.AP.223.196; 9.AP.223.223; 9.AP.223.240; 9.AP.223.244; 9.AP.223.243;
9.AP.223.247; 9.AP.240.157; 9.AP.240.158; 9.AP.240.196; 9.AP.240.223;
9.AP.240.240; 9.AP.240.244; 9.AP.240.243; 9.AP.240.247; 9.AP.244.157;
9.AP.244.158; 9.AP.244.196; 9.AP.244.223; 9.AP.244.240; 9.AP.244.244;
9.AP.244.243; 9.AP.244.247; 9.AP.247.157; 9.AP.247.158; 9.AP.247.196;
9.AP.247.223; 9.AP.247.240; 9.AP.247.244; 9.AP.247.243; 9.AP.247.247;

Prodrugs of 9.AZ

9.AZ.4.157; 9.AZ.4.158; 9.AZ.4.196; 9.AZ.4.223; 9.AZ.4.240; 9.AZ.4.244;
9.AZ.4.243; 9.AZ.4.247; 9.AZ.5.157; 9.AZ.5.158; 9.AZ.5.196; 9.AZ.5.223;
9.AZ.5.240; 9.AZ.5.244; 9.AZ.5.243; 9.AZ.5.247; 9.AZ.7.157; 9.AZ.7.158;
9.AZ.7.196; 9.AZ.7.223; 9.AZ.7.240; 9.AZ.7.244; 9.AZ.7.243; 9.AZ.7.247;
9.AZ.15.157; 9.AZ.15.158; 9.AZ.15.196; 9.AZ.15.223; 9.AZ.15.240;
9.AZ.15.244; 9.AZ.15.243; 9.AZ.15.247; 9.AZ.16.157; 9.AZ.16.158;
9.AZ.16.196; 9.AZ.16.223; 9.AZ.16.240; 9.AZ.16.244; 9.AZ.16.243;
9.AZ.16.247; 9.AZ.18.157; 9.AZ.18.158; 9.AZ.18.196; 9.AZ.18.223;
9.AZ.18.240; 9.AZ.18.244; 9.AZ.18.243; 9.AZ.18.247; 9.AZ.26.157;
9.AZ.26.158; 9.AZ.26.196; 9.AZ.26.223; 9.AZ.26.240; 9.AZ.26.244;
9.AZ.26.243; 9.AZ.26.247; 9.AZ.27.157; 9.AZ.27.158; 9.AZ.27.196;
9.AZ.27.223; 9.AZ.27.240; 9.AZ.27.244; 9.AZ.27.243; 9.AZ.27.247;
9.AZ.29.157; 9.AZ.29.158; 9.AZ.29.196; 9.AZ.29.223; 9.AZ.29.240;
9.AZ.29.244; 9.AZ.29.243; 9.AZ.29.247; 9.AZ.54.157; 9.AZ.54.158;
9.AZ.54.196; 9.AZ.54.223; 9.AZ.54.240; 9.AZ.54.244; 9.AZ.54.243;
9.AZ.54.247; 9.AZ.55.157; 9.AZ.55.158; 9.AZ.55.196; 9.AZ.55.223;
9.AZ.55.240; 9.AZ.55.244; 9.AZ.55.243; 9.AZ.55.247; 9.AZ.56.157;
9.AZ.56.158; 9.AZ.56.196; 9.AZ.56.223; 9.AZ.56.240; 9.AZ.56.244;
9.AZ.56.243; 9.AZ.56.247; 9.AZ.157.157; 9.AZ.157.158; 9.AZ.157.196;
9.AZ.157.223; 9.AZ.157.240; 9.AZ.157.244; 9.AZ.157.243; 9.AZ.157.247;
9.AZ.196.157; 9.AZ.196.158; 9.AZ.196.196; 9.AZ.196.223; 9.AZ.196.240;
9.AZ.196.244; 9.AZ.196.243; 9.AZ.196.247; 9.AZ.223.157; 9.AZ.223.158;
9.AZ.223.196; 9.AZ.223.223; 9.AZ.223.240; 9.AZ.223.244; 9.AZ.223.243;
9.AZ.223.247; 9.AZ.240.157; 9.AZ.240.158; 9.AZ.240.196; 9.AZ.240.223;
9.AZ.240.240; 9.AZ.240.244; 9.AZ.240.243; 9.AZ.240.247; 9.AZ.244.157;
9.AZ.244.158; 9.AZ.244.196; 9.AZ.244.223; 9.AZ.244.240; 9.AZ.244.244;
9.AZ.244.243; 9.AZ.244.247; 9.AZ.247.157; 9.AZ.247.158; 9.AZ.247.196;
9.AZ.247.223; 9.AZ.247.240; 9.AZ.247.244; 9.AZ.247.243; 9.AZ.247.247;

Prodrugs of 9.BF

9.BF.4.157; 9.BF.4.158; 9.BF.4.196; 9.BF.4.223; 9.BF.4.240; 9.BF.4.244;
9.BF.4.243; 9.BF.4.247; 9.BF.5.157; 9.BF.5.158; 9.BF.5.196; 9.BF.5.223;
9.BF.5.240; 9.BF.5.244; 9.BF.5.243; 9.BF.5.247; 9.BF.7.157; 9.BF.7.158;
9.BF.7.196; 9.BF.7.223; 9.BF.7.240; 9.BF.7.244; 9.BF.7.243; 9.BF.7.247;
9.BF.15.157; 9.BF.15.158; 9.BF.15.196; 9.BF.15.223; 9.BF.15.240;
9.BF.15.244; 9.BF.15.243; 9.BF.15.247; 9.BF.16.157; 9.BF.16.158;

TABLE 100-continued

9.BF.16.196; 9.BF.16.223; 9.BF.16.240; 9.BF.16.244; 9.BF.16.243;
9.BF.16.247; 9.BF.18.157; 9.BF.18.158; 9.BF.18.196; 9.BF.18.223;
9.BF.18.240; 9.BF.18.244; 9.BF.18.243; 9.BF.18.247; 9.BF.26.157;
9.BF.26.158; 9.BF.26.196; 9.BF.26.223; 9.BF.26.240; 9.BF.26.244;
9.BF.26.243; 9.BF.26.247; 9.BF.27.157; 9.BF.27.158; 9.BF.27.196;
9.BF.27.223; 9.BF.27.240; 9.BF.27.244; 9.BF.27.243; 9.BF.27.247;
9.BF.29.157; 9.BF.29.158; 9.BF.29.196; 9.BF.29.223; 9.BF.29.240;
9.BF.29.244; 9.BF.29.243; 9.BF.29.247; 9.BF.54.157; 9.BF.54.158;
9.BF.54.196; 9.BF.54.223; 9.BF.54.240; 9.BF.54.244; 9.BF.54.243;
9.BF.54.247; 9.BF.55.157; 9.BF.55.158; 9.BF.55.196; 9.BF.55.223;
9.BF.55.240; 9.BF.55.244; 9.BF.55.243; 9.BF.55.247; 9.BF.56.157;
9.BF.56.158; 9.BF.56.196; 9.BF.56.223; 9.BF.56.240; 9.BF.56.244;
9.BF.56.243; 9.BF.56.247; 9.BF.157.157; 9.BF.157.158; 9.BF.157.196;
9.BF.157.223; 9.BF.157.240; 9.BF.157.244; 9.BF.157.243; 9.BF.157.247;
9.BF.196.157; 9.BF.196.158; 9.BF.196.196; 9.BF.196.223; 9.BF.196.240;
9.BF.196.244; 9.BF.196.243; 9.BF.196.247; 9.BF.223.157; 9.BF.223.158;
9.BF.223.196; 9.BF.223.223; 9.BF.223.240; 9.BF.223.244; 9.BF.223.243;
9.BF.223.247; 9.BF.240.157; 9.BF.240.158; 9.BF.240.196; 9.BF.240.223;
9.BF.240.240; 9.BF.240.244; 9.BF.240.243; 9.BF.240.247; 9.BF.244.157;
9.BF.244.158; 9.BF.244.196; 9.BF.244.223; 9.BF.244.240; 9.BF.244.244;
9.BF.244.243; 9.BF.244.247; 9.BF.247.157; 9.BF.247.158; 9.BF.247.196;
9.BF.247.223; 9.BF.247.240; 9.BF.247.244; 9.BF.247.243; 9.BF.247.247;

Prodrugs of 9.CI

9.CI.4.157; 9.CI.4.158; 9.CI.4.196; 9.CI.4.223; 9.CI.4.240; 9.CI.4.244;
9.CI.4.243; 9.CI.4.247; 9.CI.5.157; 9.CI.5.158; 9.CI.5.196; 9.CI.5.223;
9.CI.5.240; 9.CI.5.244; 9.CI.5.243; 9.CI.5.247; 9.CI.7.157; 9.CI.7.158;
9.CI.7.196; 9.CI.7.223; 9.CI.7.240; 9.CI.7.244; 9.CI.7.243; 9.CI.7.247;
9.CI.15.157; 9.CI.15.158; 9.CI.15.196; 9.CI.15.223; 9.CI.15.240; 9.CI.15.244;
9.CI.15.243; 9.CI.15.247; 9.CI.16.157; 9.CI.16.158; 9.CI.16.196; 9.CI.16.223;
9.CI.16.240; 9.CI.16.244; 9.CI.16.243; 9.CI.16.247; 9.CI.18.157; 9.CI.18.158;
9.CI.18.196; 9.CI.18.223; 9.CI.18.240; 9.CI.18.244; 9.CI.18.243; 9.CI.18.247;
9.CI.26.157; 9.CI.26.158; 9.CI.26.196; 9.CI.26.223; 9.CI.26.240; 9.CI.26.244;
9.CI.26.243; 9.CI.26.247; 9.CI.27.157; 9.CI.27.158; 9.CI.27.196; 9.CI.27.223;
9.CI.27.240; 9.CI.27.244; 9.CI.27.243; 9.CI.27.247; 9.CI.29.157; 9.CI.29.158;
9.CI.29.196; 9.CI.29.223; 9.CI.29.240; 9.CI.29.244; 9.CI.29.243; 9.CI.29.247;
9.CI.54.157; 9.CI.54.158; 9.CI.54.196; 9.CI.54.223; 9.CI.54.240; 9.CI.54.244;
9.CI.54.243; 9.CI.54.247; 9.CI.55.157; 9.CI.55.158; 9.CI.55.196; 9.CI.55.223;
9.CI.55.240; 9.CI.55.244; 9.CI.55.243; 9.CI.55.247; 9.CI.56.157; 9.CI.56.158;
9.CI.56.196; 9.CI.56.223; 9.CI.56.240; 9.CI.56.244; 9.CI.56.243; 9.CI.56.247;
9.CI.157.157; 9.CI.157.158; 9.CI.157.196; 9.CI.157.223; 9.CI.157.240;
9.CI.157.244; 9.CI.157.243; 9.CI.157.247; 9.CI.196.157; 9.CI.196.158;
9.CI.196.196; 9.CI.196.223; 9.CI.196.240; 9.CI.196.244; 9.CI.196.243;
9.CI.196.247; 9.CI.223.157; 9.CI.223.158; 9.CI.223.196; 9.CI.223.223;
9.CI.223.240; 9.CI.223.244; 9.CI.223.243; 9.CI.223.247; 9.CI.240.157;
9.CI.240.158; 9.CI.240.196; 9.CI.240.223; 9.CI.240.240; 9.CI.240.244;
9.CI.240.243; 9.CI.240.247; 9.CI.244.157; 9.CI.244.158; 9.CI.244.196;
9.CI.244.223; 9.CI.244.240; 9.CI.244.244; 9.CI.244.243; 9.CI.244.247;
9.CI.247.157; 9.CI.247.158; 9.CI.247.196; 9.CI.247.223; 9.CI.247.240;
9.CI.247.244; 9.CI.247.243; 9.CI.247.247;

Prodrugs of 9.CO

9.CO.4.157; 9.CO.4.158; 9.CO.4.196; 9.CO.4.223; 9.CO.4.240; 9.CO.4.244; 9.CO.4.243;
9.CO.4.247; 9.CO.5.157; 9.CO.5.158; 9.CO.5.196; 9.CO.5.223;
9.CO.5.240; 9.CO.5.244; 9.CO.5.243; 9.CO.5.247; 9.CO.7.157; 9.CO.7.158;
9.CO.7.196; 9.CO.7.223; 9.CO.7.240; 9.CO.7.244; 9.CO.7.243; 9.CO.7.247;
9.CO.15.157; 9.CO.15.158; 9.CO.15.196; 9.CO.15.223; 9.CO.15.240;
9.CO.15.244; 9.CO.15.243; 9.CO.15.247; 9.CO.16.157; 9.CO.16.158;
9.CO.16.196; 9.CO.16.223; 9.CO.16.240; 9.CO.16.244; 9.CO.16.243;
9.CO.16.247; 9.CO.18.157; 9.CO.18.158; 9.CO.18.196; 9.CO.18.223;
9.CO.18.240; 9.CO.18.244; 9.CO.18.243; 9.CO.18.247; 9.CO.26.157;
9.CO.26.158; 9.CO.26.196; 9.CO.26.223; 9.CO.26.240; 9.CO.26.244;
9.CO.26.243; 9.CO.26.247; 9.CO.27.157; 9.CO.27.158; 9.CO.27.196;
9.CO.27.223; 9.CO.27.240; 9.CO.27.244; 9.CO.27.243; 9.CO.27.247;
9.CO.29.157; 9.CO.29.158; 9.CO.29.196; 9.CO.29.223; 9.CO.29.240;
9.CO.29.244; 9.CO.29.243; 9.CO.29.247; 9.CO.54.157; 9.CO.54.158;
9.CO.54.196; 9.CO.54.223; 9.CO.54.240; 9.CO.54.244; 9.CO.54.243;
9.CO.54.247; 9.CO.55.157; 9.CO.55.158; 9.CO.55.196; 9.CO.55.223;
9.CO.55.240; 9.CO.55.244; 9.CO.55.243; 9.CO.55.247; 9.CO.56.157;
9.CO.56.158; 9.CO.56.196; 9.CO.56.223; 9.CO.56.240; 9.CO.56.244;
9.CO.56.243; 9.CO.56.247; 9.CO.157.157; 9.CO.157.158; 9.CO.157.196;
9.CO.157.223; 9.CO.157.240; 9.CO.157.244; 9.CO.157.243; 9.CO.157.247;
9.CO.196.157; 9.CO.196.158; 9.CO.196.196; 9.CO.196.223; 9.CO.196.240;
9.CO.196.244; 9.CO.196.243; 9.CO.196.247; 9.CO.223.157; 9.CO.223.158;
9.CO.223.196; 9.CO.223.223; 9.CO.223.240; 9.CO.223.244; 9.CO.223.243;
9.CO.223.247; 9.CO.240.157; 9.CO.240.158; 9.CO.240.196; 9.CO.240.223;
9.CO.240.240; 9.CO.240.244; 9.CO.240.243; 9.CO.240.247; 9.CO.244.157;

TABLE 100-continued

9.CO.244.158; 9.CO.244.196; 9.CO.244.223; 9.CO.244.240; 9.CO.244.244;
9.CO.244.243; 9.CO.244.247; 9.CO.247.157; 9.CO.247.158; 9.CO.247.196;
9.CO.247.223; 9.CO.247.240; 9.CO.247.244; 9.CO.247.243; 9.CO.247.247;
Prodrugs of 10.AH 10.AH.4.157; 10.AH.4.158; 10.AH.4.196; 10.AH.4.223; 10.AH.4.240;
10.AH.4.244; 10.AH.4.243; 10.AH.4.247; 10.AH.5.157; 10.AH.5.158;
10.AH.5.196; 10.AH.5.223; 10.AH.5.240; 10.AH.5.244; 10.AH.5.243;
10.AH.5.247; 10.AH.7.157; 10.AH.7.158; 10.AH.7.196; 10.AH.7.223;
10.AH.7.240; 10.AH.7.244; 10.AH.7.243; 10.AH.7.247; 10.AH.15.157;
10.AH.15.158; 10.AH.15.196; 10.AH.15.223; 10.AH.15.240; 10.AH.15.244;
10.AH.15.243; 10.AH.15.247; 10.AH.16.157; 10.AH.16.158; 10.AH.16.196;
10.AH.16.223; 10.AH.16.240; 10.AH.16.244; 10.AH.16.243; 10.AH.16.247;
10.AH.18.157; 10.AH.18.158; 10.AH.18.196; 10.AH.18.223; 10.AH.18.240;
10.AH.18.244; 10.AH.18.243; 10.AH.18.247; 10.AH.26.157; 10.AH.26.158;
10.AH.26.196; 10.AH.26.223; 10.AH.26.240; 10.AH.26.244; 10.AH.26.243;
10.AH.26.247; 10.AH.27.157; 10.AH.27.158; 10.AH.27.196; 10.AH.27.223;
10.AH.27.240; 10.AH.27.244; 10.AH.27.243; 10.AH.27.247; 10.AH.29.157;
10.AH.29.158; 10.AH.29.196; 10.AH.29.223; 10.AH.29.240; 10.AH.29.244;
10.AH.29.243; 10.AH.29.247; 10.AH.54.157; 10.AH.54.158; 10.AH.54.196;
10.AH.54.223; 10.AH.54.240; 10.AH.54.244; 10.AH.54.243; 10.AH.54.247;
10.AH.55.157; 10.AH.55.158; 10.AH.55.196; 10.AH.55.223; 10.AH.55.240;
10.AH.55.244; 10.AH.55.243; 10.AH.55.247; 10.AH.56.157; 10.AH.56.158;
10.AH.56.196; 10.AH.56.223; 10.AH.56.240; 10.AH.56.244; 10.AH.56.243;
10.AH.56.247; 10.AH.157.157; 10.AH.157.158; 10.AH.157.196;
10.AH.157.223; 10.AH.157.240; 10.AH.157.244; 10.AH.157.243;
10.AH.157.247; 10.AH.196.157; 10.AH.196.158; 10.AH.196.196;
10.AH.196.223; 10.AH.196.240; 10.AH.196.244; 10.AH.196.243;
10.AH.196.247; 10.AH.223.157; 10.AH.223.158; 10.AH.223.196;
10.AH.223.223; 10.AH.223.240; 10.AH.223.244; 10.AH.223.243;
10.AH.223.247; 10.AH.240.157; 10.AH.240.158; 10.AH.240.196;
10.AH.240.223; 10.AH.240.240; 10.AH.240.244; 10.AH.240.243;
10.AH.240.247; 10.AH.244.157; 10.AH.244.158; 10.AH.244.196;
10.AH.244.223; 10.AH.244.240; 10.AH.244.244; 10.AH.244.243;
10.AH.244.247; 10.AH.247.157; 10.AH.247.158; 10.AH.247.196;
10.AH.247.223; 10.AH.247.240; 10.AH.247.244; 10.AH.247.243;
10.AH.247.247;
Prodrugs of 10.AJ 10.AJ.4.157; 10.AJ.4.158; 10.AJ.4.196; 10.AJ.4.223; 10.AJ.4.240;
10.AJ.4.244; 10.AJ.4.243; 10.AJ.4.247; 10.AJ.5.157; 10.AJ.5.158; 10.AJ.5.196;
10.AJ.5.223; 10.AJ.5.240; 10.AJ.5.244; 10.AJ.5.243; 10.AJ.5.247; 10.AJ.7.157;
10.AJ.7.158; 10.AJ.7.196; 10.AJ.7.223; 10.AJ.7.240; 10.AJ.7.244; 10.AJ.7.243;
10.AJ.7.247; 10.AJ.15.157; 10.AJ.15.158; 10.AJ.15.196; 10.AJ.15.223;
10.AJ.15.240; 10.AJ.15.244; 10.AJ.15.243; 10.AJ.15.247; 10.AJ.16.157;
10.AJ.16.158; 10.AJ.16.196; 10.AJ.16.223; 10.AJ.16.240; 10.AJ.16.244;
10.AJ.16.243; 10.AJ.16.247; 10.AJ.18.157; 10.AJ.18.158; 10.AJ.18.196;
10.AJ.18.223; 10.AJ.18.240; 10.AJ.18.244; 10.AJ.18.243; 10.AJ.18.247;
10.AJ.26.157; 10.AJ.26.158; 10.AJ.26.196; 10.AJ.26.223; 10.AJ.26.240;
10.AJ.26.244; 10.AJ.26.243; 10.AJ.26.247; 10.AJ.27.157; 10.AJ.27.158;
10.AJ.27.196; 10.AJ.27.223; 10.AJ.27.240; 10.AJ.27.244; 10.AJ.27.243;
10.AJ.27.247; 10.AJ.29.157; 10.AJ.29.158; 10.AJ.29.196; 10.AJ.29.223;
10.AJ.29.240; 10.AJ.29.244; 10.AJ.29.243; 10.AJ.29.247; 10.AJ.54.157;
10.AJ.54.158; 10.AJ.54.196; 10.AJ.54.223; 10.AJ.54.240; 10.AJ.54.244;
10.AJ.54.243; 10.AJ.54.247; 10.AJ.55.157; 10.AJ.55.158; 10.AJ.55.196;
10.AJ.55.223; 10.AJ.55.240; 10.AJ.55.244; 10.AJ.55.243; 10.AJ.55.247;
10.AJ.56.157; 10.AJ.56.158; 10.AJ.56.196; 10.AJ.56.223; 10.AJ.56.240;
10.AJ.56.244; 10.AJ.56.243; 10.AJ.56.247; 10.AJ.157.157; 10.AJ.157.158;
10.AJ.157.196; 10.AJ.157.223; 10.AJ.157.240; 10.AJ.157.244; 10.AJ.157.243;
10.AJ.157.247; 10.AJ.196.157; 10.AJ.196.158; 10.AJ.196.196; 10.AJ.196.223;
10.AJ.196.240; 10.AJ.196.244; 10.AJ.196.243; 10.AJ.196.247; 10.AJ.223.157;
10.AJ.223.158; 10.AJ.223.196; 10.AJ.223.223; 10.AJ.223.240; 10.AJ.223.244;
10.AJ.223.243; 10.AJ.223.247; 10.AJ.240.157; 10.AJ.240.158; 10.AJ.240.196;
10.AJ.240.223; 10.AJ.240.240; 10.AJ.240.244; 10.AJ.240.243; 10.AJ.240.247;
10.AJ.244.157; 10.AJ.244.158; 10.AJ.244.196; 10.AJ.244.223; 10.AJ.244.240;
10.AJ.244.244; 10.AJ.244.243; 10.AJ.244.247; 10.AJ.247.157; 10.AJ.247.158;
10.AJ.247.196; 10.AJ.247.223; 10.AJ.247.240; 10.AJ.247.244; 10.AJ.247.243;
10.AJ.247.247;
Prodrugs of 10.AN 10.AN.4.157; 10.AN.4.158; 10.AN.4.196; 10.AN.4.223; 10.AN.4.240;
10.AN.4.244; 10.AN.4.243; 10.AN.4.247; 10.AN.5.157; 10.AN.5.158;
10.AN.5.196; 10.AN.5.223; 10.AN.5.240; 10.AN.5.244; 10.AN.5.243;
10.AN.5.247; 10.AN.7.157; 10.AN.7.158; 10.AN.7.196; 10.AN.7.223;
10.AN.7.240; 10.AN.7.244; 10.AN.7.243; 10.AN.7.247; 10.AN.15.157;
10.AN.15.158; 10.AN.15.196; 10.AN.15.223; 10.AN.15.240; 10.AN.15.244;
10.AN.15.243; 10.AN.15.247; 10.AN.16.157; 10.AN.16.158; 10.AN.16.196;
10.AN.16.223; 10.AN.16.240; 10.AN.16.244; 10.AN.16.243; 10.AN.16.247;
10.AN.18.157; 10.AN.18.158; 10.AN.18.196; 10.AN.18.223; 10.AN.18.240;

TABLE 100-continued

10.AN.18.244; 10.AN.18.243; 10.AN.18.247; 10.AN.26.157; 10.AN.26.158;
10.AN.26.196; 10.AN.26.223; 10.AN.26.240; 10.AN.26.244; 10.AN.26.243;
10.AN.26.247; 10.AN.27.157; 10.AN.27.158; 10.AN.27.196; 10.AN.27.223;
10.AN.27.240; 10.AN.27.244; 10.AN.27.243; 10.AN.27.247; 10.AN.29.157;
10.AN.29.158; 10.AN.29.196; 10.AN.29.223; 10.AN.29.240; 10.AN.29.244;
10.AN.29.243; 10.AN.29.247; 10.AN.54.157; 10.AN.54.158; 10.AN.54.196;
10.AN.54.223; 10.AN.54.240; 10.AN.54.244; 10.AN.54.243; 10.AN.54.247;
10.AN.55.157; 10.AN.55.158; 10.AN.55.196; 10.AN.55.223; 10.AN.55.240;
10.AN.55.244; 10.AN.55.243; 10.AN.55.247; 10.AN.56.157; 10.AN.56.158;
10.AN.56.196; 10.AN.56.223; 10.AN.56.240; 10.AN.56.244; 10.AN.56.243;
10.AN.56.247; 10.AN.157.157; 10.AN.157.158; 10.AN.157.196;
10.AN.157.223; 10.AN.157.240; 10.AN.157.244; 10.AN.157.243;
10.AN.157.247; 10.AN.196.157; 10.AN.196.158; 10.AN.196.196;
10.AN.196.223; 10.AN.196.240; 10.AN.196.244; 10.AN.196.243;
10.AN.196.247; 10.AN.223.157; 10.AN.223.158; 10.AN.223.196;
10.AN.223.223; 10.AN.223.240; 10.AN.223.244; 10.AN.223.243;
10.AN.223.247; 10.AN.240.157; 10.AN.240.158; 10.AN.240.196;
10.AN.240.223; 10.AN.240.240; 10.AN.240.244; 10.AN.240.243;
10.AN.240.247; 10.AN.244.157; 10.AN.244.158; 10.AN.244.196;
10.AN.244.223; 10.AN.244.240; 10.AN.244.244; 10.AN.244.243;
10.AN.244.247; 10.AN.247.157; 10.AN.247.158; 10.AN.247.196;
10.AN.247.223; 10.AN.247.240; 10.AN.247.244; 10.AN.247.243;
10.AN.247.247;
Prodrugs of 10.AP 10.AP.4.157; 10.AP.4.158; 10.AP.4.196; 10.AP.4.223; 10.AP.4.240;
10.AP.4.244; 10.AP.4.243; 10.AP.4.247; 10.AP.5.157; 10.AP.5.158;
10.AP.5.196; 10.AP.5.223; 10.AP.5.240; 10.AP.5.244; 10.AP.5.243;
10.AP.5.247; 10.AP.7.157; 10.AP.7.158; 10.AP.7.196; 10.AP.7.223;
10.AP.7.240; 10.AP.7.244; 10.AP.7.243; 10.AP.7.247; 10.AP.15.157;
10.AP.15.158; 10.AP.15.196; 10.AP.15.223; 10.AP.15.240; 10.AP.15.244;
10.AP.15.243; 10.AP.15.247; 10.AP.16.157; 10.AP.16.158; 10.AP.16.196;
10.AP.16.223; 10.AP.16.240; 10.AP.16.244; 10.AP.16.243; 10.AP.16.247;
10.AP.18.157; 10.AP.18.158; 10.AP.18.196; 10.AP.18.223; 10.AP.18.240;
10.AP.18.244; 10.AP.18.243; 10.AP.18.247; 10.AP.26.157; 10.AP.26.158;
10.AP.26.196; 10.AP.26.223; 10.AP.26.240; 10.AP.26.244; 10.AP.26.243;
10.AP.26.247; 10.AP.27.157; 10.AP.27.158; 10.AP.27.196; 10.AP.27.223;
10.AP.27.240; 10.AP.27.244; 10.AP.27.243; 10.AP.27.247; 10.AP.29.157;
10.AP.29.158; 10.AP.29.196; 10.AP.29.223; 10.AP.29.240; 10.AP.29.244;
10.AP.29.243; 10.AP.29.247; 10.AP.54.157; 10.AP.54.158; 10.AP.54.196;
10.AP.54.223; 10.AP.54.240; 10.AP.54.244; 10.AP.54.243; 10.AP.54.247;
10.AP.55.157; 10.AP.55.158; 10.AP.55.196; 10.AP.55.223; 10.AP.55.240;
10.AP.55.244; 10.AP.55.243; 10.AP.55.247; 10.AP.56.157; 10.AP.56.158;
10.AP.56.196; 10.AP.56.223; 10.AP.56.240; 10.AP.56.244; 10.AP.56.243;
10.AP.56.247; 10.AP.157.157; 10.AP.157.158; 10.AP.157.196; 10.AP.157.223;
10.AP.157.240; 10.AP.157.244; 10.AP.157.243; 10.AP.157.247;
10.AP.196.157; 10.AP.196.158; 10.AP.196.196; 10.AP.196.223;
10.AP.196.240; 10.AP.196.244; 10.AP.196.243; 10.AP.196.247;
10.AP.223.157; 10.AP.223.158; 10.AP.223.196; 10.AP.223.223;
10.AP.223.240; 10.AP.223.244; 10.AP.223.243; 10.AP.223.247;
10.AP.240.157; 10.AP.240.158; 10.AP.240.196; 10.AP.240.223;
10.AP.240.240; 10.AP.240.244; 10.AP.240.243; 10.AP.240.247;
10.AP.244.157; 10.AP.244.158; 10.AP.244.196; 10.AP.244.223;
10.AP.244.240; 10.AP.244.244; 10.AP.244.243; 10.AP.244.247;
10.AP.247.157; 10.AP.247.158; 10.AP.247.196; 10.AP.247.223;
10.AP.247.240; 10.AP.247.244; 10.AP.247.243; 10.AP.247.247;
Prodrugs of 10.AZ 10.AZ.4.157; 10.AZ.4.158; 10.AZ.4.196; 10.AZ.4.223; 10.AZ.4.240;
10.AZ.4.244; 10.AZ.4.243; 10.AZ.4.247; 10.AZ.5.157; 10.AZ.5.158;
10.AZ.5.196; 10.AZ.5.223; 10.AZ.5.240; 10.AZ.5.244; 10.AZ.5.243;
10.AZ.5.247; 10.AZ.7.157; 10.AZ.7.158; 10.AZ.7.196; 10.AZ.7.223;
10.AZ.7.240; 10.AZ.7.244; 10.AZ.7.243; 10.AZ.7.247; 10.AZ.15.157;
10.AZ.15.158; 10.AZ.15.196; 10.AZ.15.223; 10.AZ.15.240; 10.AZ.15.244;
10.AZ.15.243; 10.AZ.15.247; 10.AZ.16.157; 10.AZ.16.158; 10.AZ.16.196;
10.AZ.16.223; 10.AZ.16.240; 10.AZ.16.244; 10.AZ.16.243; 10.AZ.16.247;
10.AZ.18.157; 10.AZ.18.158; 10.AZ.18.196; 10.AZ.18.223; 10.AZ.18.240;
10.AZ.18.244; 10.AZ.18.243; 10.AZ.18.247; 10.AZ.26.157; 10.AZ.26.158;
10.AZ.26.196; 10.AZ.26.223; 10.AZ.26.240; 10.AZ.26.244; 10.AZ.26.243;
10.AZ.26.247; 10.AZ.27.157; 10.AZ.27.158; 10.AZ.27.196; 10.AZ.27.223;
10.AZ.27.240; 10.AZ.27.244; 10.AZ.27.243; 10.AZ.27.247; 10.AZ.29.157;
10.AZ.29.158; 10.AZ.29.196; 10.AZ.29.223; 10.AZ.29.240; 10.AZ.29.244;
10.AZ.29.243; 10.AZ.29.247; 10.AZ.54.157; 10.AZ.54.158; 10.AZ.54.196;
10.AZ.54.223; 10.AZ.54.240; 10.AZ.54.244; 10.AZ.54.243; 10.AZ.54.247;
10.AZ.55.157; 10.AZ.55.158; 10.AZ.55.196; 10.AZ.55.223; 10.AZ.55.240;
10.AZ.55.244; 10.AZ.55.243; 10.AZ.55.247; 10.AZ.56.157; 10.AZ.56.158;
10.AZ.56.196; 10.AZ.56.223; 10.AZ.56.240; 10.AZ.56.244; 10.AZ.56.243;
10.AZ.56.247; 10.AZ.157.157; 10.AZ.157.158; 10.AZ.157.196; 10.AZ.157.223;
10.AZ.157.240; 10.AZ.157.244; 10.AZ.157.243; 10.AZ.157.247;

TABLE 100-continued

10.AZ.196.157; 10.AZ.196.158; 10.AZ.196.196; 10.AZ.196.223;
10.AZ.196.240; 10.AZ.196.244; 10.AZ.196.243; 10.AZ.196.247;
10.AZ.223.157; 10.AZ.223.158; 10.AZ.223.196; 10.AZ.223.223;
10.AZ.223.240; 10.AZ.223.244; 10.AZ.223.243; 10.AZ.223.247;
10.AZ.240.157; 10.AZ.240.158; 10.AZ.240.196; 10.AZ.240.223;
10.AZ.240.240; 10.AZ.240.244; 10.AZ.240.243; 10.AZ.240.247;
10.AZ.244.157; 10.AZ.244.158; 10.AZ.244.196; 10.AZ.244.223;
10.AZ.244.240; 10.AZ.244.244; 10.AZ.244.243; 10.AZ.244.247;
10.AZ.247.157; 10.AZ.247.158; 10.AZ.247.196; 10.AZ.247.223;
10.AZ.247.240; 10.AZ.247.244; 10.AZ.247.243; 10.AZ.247.247;
Prodrugs of 10.BF 10.BF.4.157; 10.BF.4.158; 10.BF.4.196; 10.BF.4.223; 10.BF.4.240;
10.BF.4.244; 10.BF.4.243; 10.BF.4.247; 10.BF.5.157; 10.BF.5.158;
10.BF.5.196; 10.BF.5.223; 10.BF.5.240; 10.BF.5.244; 10.BF.5.243;
10.BF.5.247; 10.BF.7.157; 10.BF.7.158; 10.BF.7.196; 10.BF.7.223;
10.BF.7.240; 10.BF.7.244; 10.BF.7.243; 10.BF.7.247; 10.BF.15.157;
10.BF.15.158; 10.BF.15.196; 10.BF.15.223; 10.BF.15.240; 10.BF.15.244;
10.BF.15.243; 10.BF.15.247; 10.BF.16.157; 10.BF.16.158; 10.BF.16.196;
10.BF.16.223; 10.BF.16.240; 10.BF.16.244; 10.BF.16.243; 10.BF.16.247;
10.BF.18.157; 10.BF.18.158; 10.BF.18.196; 10.BF.18.223; 10.BF.18.240;
10.BF.18.244; 10.BF.18.243; 10.BF.18.247; 10.BF.26.157; 10.BF.26.158;
10.BF.26.196; 10.BF.26.223; 10.BF.26.240; 10.BF.26.244; 10.BF.26.243;
10.BF.26.247; 10.BF.27.157; 10.BF.27.158; 10.BF.27.196; 10.BF.27.223;
10.BF.27.240; 10.BF.27.244; 10.BF.27.243; 10.BF.27.247; 10.BF.29.157;
10.BF.29.158; 10.BF.29.196; 10.BF.29.223; 10.BF.29.240; 10.BF.29.244;
10.BF.29.243; 10.BF.29.247; 10.BF.54.157; 10.BF.54.158; 10.BF.54.196;
10.BF.54.223; 10.BF.54.240; 10.BF.54.244; 10.BF.54.243; 10.BF.54.247;
10.BF.55.157; 10.BF.55.158; 10.BF.55.196; 10.BF.55.223; 10.BF.55.240;
10.BF.55.244; 10.BF.55.243; 10.BF.55.247; 10.BF.56.157; 10.BF.56.158;
10.BF.56.196; 10.BF.56.223; 10.BF.56.240; 10.BF.56.244; 10.BF.56.243;
10.BF.56.247; 10.BF.157.157; 10.BF.157.158; 10.BF.157.196; 10.BF.157.223;
10.BF.157.240; 10.BF.157.244; 10.BF.157.243; 10.BF.157.247; 10.BF.196.157;
10.BF.196.158; 10.BF.196.196; 10.BF.196.223; 10.BF.196.240; 10.BF.196.244;
10.BF.196.243; 10.BF.196.247; 10.BF.223.157; 10.BF.223.158; 10.BF.223.196;
10.BF.223.223; 10.BF.223.240; 10.BF.223.244; 10.BF.223.243; 10.BF.223.247;
10.BF.240.157; 10.BF.240.158; 10.BF.240.196; 10.BF.240.223; 10.BF.240.240;
10.BF.240.244; 10.BF.240.243; 10.BF.240.247; 10.BF.244.157; 10.BF.244.158;
10.BF.244.196; 10.BF.244.223; 10.BF.244.240; 10.BF.244.244; 10.BF.244.243;
10.BF.244.247; 10.BF.247.157; 10.BF.247.158; 10.BF.247.196; 10.BF.247.223;
10.BF.247.240; 10.BF.247.244; 10.BF.247.243; 10.BF.247.247;
Prodrugs of 10.CI 10.CI.4.157; 10.CI.4.158; 10.CI.4.196; 10.CI.4.223; 10.CI.4.240;
10.CI.4.244; 10.CI.4.243; 10.CI.4.247; 10.CI.5.157; 10.CI.5.158; 10.CI.5.196;
10.CI.5.223; 10.CI.5.240; 10.CI.5.244; 10.CI.5.243; 10.CI.5.247; 10.CI.7.157;
10.CI.7.158; 10.CI.7.196; 10.CI.7.223; 10.CI.7.240; 10.CI.7.244; 10.CI.7.243;
10.CI.7.247; 10.CI.15.157; 10.CI.15.158; 10.CI.15.196; 10.CI.15.223;
10.CI.15.240; 10.CI.15.244; 10.CI.15.243; 10.CI.15.247; 10.CI.16.157;
10.CI.16.158; 10.CI.16.196; 10.CI.16.223; 10.CI.16.240; 10.CI.16.244;
10.CI.16.243; 10.CI.16.247; 10.CI.18.157; 10.CI.18.158; 10.CI.18.196;
10.CI.18.223; 10.CI.18.240; 10.CI.18.244; 10.CI.18.243; 10.CI.18.247;
10.CI.26.157; 10.CI.26.158; 10.CI.26.196; 10.CI.26.223; 10.CI.26.240;
10.CI.26.244; 10.CI.26.243; 10.CI.26.247; 10.CI.27.157; 10.CI.27.158;
10.CI.27.196; 10.CI.27.223; 10.CI.27.240; 10.CI.27.244; 10.CI.27.243;
10.CI.27.247; 10.CI.29.157; 10.CI.29.158; 10.CI.29.196; 10.CI.29.223;
10.CI.29.240; 10.CI.29.244; 10.CI.29.243; 10.CI.29.247; 10.CI.54.157;
10.CI.54.158; 10.CI.54.196; 10.CI.54.223; 10.CI.54.240; 10.CI.54.244;
10.CI.54.243; 10.CI.54.247; 10.CI.55.157; 10.CI.55.158; 10.CI.55.196;
10.CI.55.223; 10.CI.55.240; 10.CI.55.244; 10.CI.55.243; 10.CI.55.247;
10.CI.56.157; 10.CI.56.158; 10.CI.56.196; 10.CI.56.223; 10.CI.56.240;
10.CI.56.244; 10.CI.56.243; 10.CI.56.247; 10.CI.157.157; 10.CI.157.158;
10.CI.157.196; 10.CI.157.223; 10.CI.157.240; 10.CI.157.244; 10.CI.157.243;
10.CI.157.247; 10.CI.196.157; 10.CI.196.158; 10.CI.196.196; 10.CI.196.223;
10.CI.196.240; 10.CI.196.244; 10.CI.196.243; 10.CI.196.247; 10.CI.223.157;
10.CI.223.158; 10.CI.223.196; 10.CI.223.223; 10.CI.223.240; 10.CI.223.244;
10.CI.223.243; 10.CI.223.247; 10.CI.240.157; 10.CI.240.158; 10.CI.240.196;
10.CI.240.223; 10.CI.240.240; 10.CI.240.244; 10.CI.240.243; 10.CI.240.247;
10.CI.244.157; 10.CI.244.158; 10.CI.244.196; 10.CI.244.223; 10.CI.244.240;
10.CI.244.244; 10.CI.244.243; 10.CI.244.247; 10.CI.247.157; 10.CI.247.158;
10.CI.247.196; 10.CI.247.223; 10.CI.247.240; 10.CI.247.244; 10.CI.247.243;
10.CI.247.247;
Prodrugs of 10.CO 10.CO.4.157; 10.CO.4.158; 10.CO.4.196; 10.CO.4.223; 10.CO.4.240;
10.CO.4.244; 10.CO.4.243; 10.CO.4.247; 10.CO.5.157; 10.CO.5.158;
10.CO.5.196; 10.CO.5.223; 10.CO.5.240; 10.CO.5.244; 10.CO.5.243;
10.CO.5.247; 10.CO.7.157; 10.CO.7.158; 10.CO.7.196; 10.CO.7.223;
10.CO.7.240; 10.CO.7.244; 10.CO.7.243; 10.CO.7.247; 10.CO.15.157;

TABLE 100-continued

10.CO.15.158; 10.CO.15.196; 10.CO.15.223; 10.CO.15.240; 10.CO.15.244;
10.CO.15.243; 10.CO.15.247; 10.CO.16.157; 10.CO.16.158; 10.CO.16.196;
10.CO.16.223; 10.CO.16.240; 10.CO.16.244; 10.CO.16.243; 10.CO.16.247;
10.CO.18.157; 10.CO.18.158; 10.CO.18.196; 10.CO.18.223; 10.CO.18.240;
10.CO.18.244; 10.CO.18.243; 10.CO.18.247; 10.CO.26.157; 10.CO.26.158;
10.CO.26.196; 10.CO.26.223; 10.CO.26.240; 10.CO.26.244; 10.CO.26.243;
10.CO.26.247; 10.CO.27.157; 10.CO.27.158; 10.CO.27.196; 10.CO.27.223;
10.CO.27.240; 10.CO.27.244; 10.CO.27.243; 10.CO.27.247; 10.CO.29.157;
10.CO.29.158; 10.CO.29.196; 10.CO.29.223; 10.CO.29.240; 10.CO.29.244;
10.CO.29.243; 10.CO.29.247; 10.CO.54.157; 10.CO.54.158; 10.CO.54.196;
10.CO.54.223; 10.CO.54.240; 10.CO.54.244; 10.CO.54.243; 10.CO.54.247;
10.CO.55.157; 10.CO.55.158; 10.CO.55.196; 10.CO.55.223; 10.CO.55.240;
10.CO.55.244; 10.CO.55.243; 10.CO.55.247; 10.CO.56.157; 10.CO.56.158;
10.CO.56.196; 10.CO.56.223; 10.CO.56.240; 10.CO.56.244; 10.CO.56.243;
10.CO.56.247; 10.CO.157.157; 10.CO.157.158; 10.CO.157.196;
10.CO.157.223; 10.CO.157.240; 10.CO.157.244; 10.CO.157.243;
10.CO.157.247; 10.CO.196.157; 10.CO.196.158; 10.CO.196.196;
10.CO.196.223; 10.CO.196.240; 10.CO.196.244; 10.CO.196.243;
10.CO.196.247; 10.CO.223.157; 10.CO.223.158; 10.CO.223.196;
10.CO.223.223; 10.CO.223.240; 10.CO.223.244; 10.CO.223.243;
10.CO.223.247; 10.CO.240.157; 10.CO.240.158; 10.CO.240.196;
10.CO.240.223; 10.CO.240.240; 10.CO.240.244; 10.CO.240.243;
10.CO.240.247; 10.CO.244.157; 10.CO.244.158; 10.CO.244.196;
10.CO.244.223; 10.CO.244.240; 10.CO.244.244; 10.CO.244.243;
10.CO.244.247; 10.CO.247.157; 10.CO.247.158; 10.CO.247.196;
10.CO.247.223; 10.CO.247.240; 10.CO.247.244; 10.CO.247.243;
10.CO.247.247;
Prodrugs of 11.AH 11.AH.4.157; 11.AH.4.158; 11.AH.4.196; 11.AH.4.223; 11.AH.4.240;
11.AH.4.244; 11.AH.4.243; 11.AH.4.247; 11.AH.5.157; 11.AH.5.158;
11.AH.5.196; 11.AH.5.223; 11.AH.5.240; 11.AH.5.244; 11.AH.5.243;
11.AH.5.247; 11.AH.7.157; 11.AH.7.158; 11.AH.7.196; 11.AH.7.223;
11.AH.7.240; 11.AH.7.244; 11.AH.7.243; 11.AH.7.247; 11.AH.15.157;
11.AH.15.158; 11.AH.15.196; 11.AH.15.223; 11.AH.15.240; 11.AH.15.244;
11.AH.15.243; 11.AH.15.247; 11.AH.16.157; 11.AH.16.158; 11.AH.16.196;
11.AH.16.223; 11.AH.16.240; 11.AH.16.244; 11.AH.16.243; 11.AH.16.247;
11.AH.18.157; 11.AH.18.158; 11.AH.18.196; 11.AH.18.223; 11.AH.18.240;
11.AH.18.244; 11.AH.18.243; 11.AH.18.247; 11.AH.26.157; 11.AH.26.158;
11.AH.26.196; 11.AH.26.223; 11.AH.26.240; 11.AH.26.244; 11.AH.26.243;
11.AH.26.247; 11.AH.27.157; 11.AH.27.158; 11.AH.27.196; 11.AH.27.223;
11.AH.27.240; 11.AH.27.244; 11.AH.27.243; 11.AH.27.247; 11.AH.29.157;
11.AH.29.158; 11.AH.29.196; 11.AH.29.223; 11.AH.29.240; 11.AH.29.244;
11.AH.29.243; 11.AH.29.247; 11.AH.54.157; 11.AH.54.158; 11.AH.54.196;
11.AH.54.223; 11.AH.54.240; 11.AH.54.244; 11.AH.54.243; 11.AH.54.247;
11.AH.55.157; 11.AH.55.158; 11.AH.55.196; 11.AH.55.223; 11.AH.55.240;
11.AH.55.244; 11.AH.55.243; 11.AH.55.247; 11.AH.56.157; 11.AH.56.158;
11.AH.56.196; 11.AH.56.223; 11.AH.56.240; 11.AH.56.244; 11.AH.56.243;
11.AH.56.247; 11.AH.157.157; 11.AH.157.158; 11.AH.157.196;
11.AH.157.223; 11.AH.157.240; 11.AH.157.244; 11.AH.157.243;
11.AH.157.247; 11.AH.196.157; 11.AH.196.158; 11.AH.196.196;
11.AH.196.223; 11.AH.196.240; 11.AH.196.244; 11.AH.196.243;
11.AH.196.247; 11.AH.223.157; 11.AH.223.158; 11.AH.223.196;
11.AH.223.223; 11.AH.223.240; 11.AH.223.244; 11.AH.223.243;
11.AH.223.247; 11.AH.240.157; 11.AH.240.158; 11.AH.240.196;
11.AH.240.223; 11.AH.240.240; 11.AH.240.244; 11.AH.240.243;
11.AH.240.247; 11.AH.244.157; 11.AH.244.158; 11.AH.244.196;
11.AH.244.223; 11.AH.244.240; 11.AH.244.244; 11.AH.244.243;
11.AH.244.247; 11.AH.247.157; 11.AH.247.158; 11.AH.247.196;
11.AH.247.223; 11.AH.247.240; 11.AH.247.244; 11.AH.247.243;
11.AH.247.247;
Prodrugs of 11.AJ 11.AJ.4.157; 11.AJ.4.158; 11.AJ.4.196; 11.AJ.4.223; 11.AJ.4.240;
11.AJ.4.244; 11.AJ.4.243; 11.AJ.4.247; 11.AJ.5.157; 11.AJ.5.158; 11.AJ.5.196;
11.AJ.5.223; 11.AJ.5.240; 11.AJ.5.244; 11.AJ.5.243; 11.AJ.5.247; 11.AJ.7.157;
11.AJ.7.158; 11.AJ.7.196; 11.AJ.7.223; 11.AJ.7.240; 11.AJ.7.244; 11.AJ.7.243;
11.AJ.7.247; 11.AJ.15.157; 11.AJ.15.158; 11.AJ.15.196; 11.AJ.15.223;
11.AJ.15.240; 11.AJ.15.244; 11.AJ.15.243; 11.AJ.15.247; 11.AJ.16.157;
11.AJ.16.158; 11.AJ.16.196; 11.AJ.16.223; 11.AJ.16.240; 11.AJ.16.244;
11.AJ.16.243; 11.AJ.16.247; 11.AJ.18.157; 11.AJ.18.158; 11.AJ.18.196;
11.AJ.18.223; 11.AJ.18.240; 11.AJ.18.244; 11.AJ.18.243; 11.AJ.18.247;
11.AJ.26.157; 11.AJ.26.158; 11.AJ.26.196; 11.AJ.26.223; 11.AJ.26.240;
11.AJ.26.244; 11.AJ.26.243; 11.AJ.26.247; 11.AJ.27.157; 11.AJ.27.158;
11.AJ.27.196; 11.AJ.27.223; 11.AJ.27.240; 11.AJ.27.244; 11.AJ.27.243;
11.AJ.27.247; 11.AJ.29.157; 11.AJ.29.158; 11.AJ.29.196; 11.AJ.29.223;
11.AJ.29.240; 11.AJ.29.244; 11.AJ.29.243; 11.AJ.29.247; 11.AJ.54.157;
11.AJ.54.158; 11.AJ.54.196; 11.AJ.54.223; 11.AJ.54.240; 11.AJ.54.244;
11.AJ.54.243; 11.AJ.54.247; 11.AJ.55.157; 11.AJ.55.158; 11.AJ.55.196;

TABLE 100-continued

11.AJ.55.223; 11.AJ.55.240; 11.AJ.55.244; 11.AJ.55.243; 11.AJ.55.247;
11.AJ.56.157; 11.AJ.56.158; 11.AJ.56.196; 11.AJ.56.223; 11.AJ.56.240;
11.AJ.56.244; 11.AJ.56.243; 11.AJ.56.247; 11.AJ.157.157; 11.AJ.157.158;
11.AJ.157.196; 11.AJ.157.223; 11.AJ.157.240; 11.AJ.157.244; 11.AJ.157.243;
11.AJ.157.247; 11.AJ.196.157; 11.AJ.196.158; 11.AJ.196.196; 11.AJ.196.223;
11.AJ.196.240; 11.AJ.196.244; 11.AJ.196.243; 11.AJ.196.247; 11.AJ.223.157;
11.AJ.223.158; 11.AJ.223.196; 11.AJ.223.223; 11.AJ.223.240; 11.AJ.223.244;
11.AJ.223.243; 11.AJ.223.247; 11.AJ.240.157; 11.AJ.240.158; 11.AJ.240.196;
11.AJ.240.223; 11.AJ.240.240; 11.AJ.240.244; 11.AJ.240.243; 11.AJ.240.247;
11.AJ.244.157; 11.AJ.244.158; 11.AJ.244.196; 11.AJ.244.223; 11.AJ.244.240;
11.AJ.244.244; 11.AJ.244.243; 11.AJ.244.247; 11.AJ.247.157; 11.AJ.247.158;
11.AJ.247.196; 11.AJ.247.223; 11.AJ.247.240; 11.AJ.247.244; 11.AJ.247.243;
11.AJ.247.247;
Prodrugs of 11.AN 11.AN.4.157; 11.AN.4.158; 11.AN.4.196; 11.AN.4.223; 11.AN.4.240;
11.AN.4.244; 11.AN.4.243; 11.AN.4.247; 11.AN.5.157; 11.AN.5.158;
11.AN.5.196; 11.AN.5.223; 11.AN.5.240; 11.AN.5.244; 11.AN.5.243;
11.AN.5.247; 11.AN.7.157; 11.AN.7.158; 11.AN.7.196; 11.AN.7.223;
11.AN.7.240; 11.AN.7.244; 11.AN.7.243; 11.AN.7.247; 11.AN.15.157;
11.AN.15.158; 11.AN.15.196; 11.AN.15.223; 11.AN.15.240; 11.AN.15.244;
11.AN.15.243; 11.AN.15.247; 11.AN.16.157; 11.AN.16.158; 11.AN.16.196;
11.AN.16.223; 11.AN.16.240; 11.AN.16.244; 11.AN.16.243; 11.AN.16.247;
11.AN.18.157; 11.AN.18.158; 11.AN.18.196; 11.AN.18.223; 11.AN.18.240;
11.AN.18.244; 11.AN.18.243; 11.AN.18.247; 11.AN.26.157; 11.AN.26.158;
11.AN.26.196; 11.AN.26.223; 11.AN.26.240; 11.AN.26.244; 11.AN.26.243;
11.AN.26.247; 11.AN.27.157; 11.AN.27.158; 11.AN.27.196; 11.AN.27.223;
11.AN.27.240; 11.AN.27.244; 11.AN.27.243; 11.AN.27.247; 11.AN.29.157;
11.AN.29.158; 11.AN.29.196; 11.AN.29.223; 11.AN.29.240; 11.AN.29.244;
11.AN.29.243; 11.AN.29.247; 11.AN.54.157; 11.AN.54.158; 11.AN.54.196;
11.AN.54.223; 11.AN.54.240; 11.AN.54.244; 11.AN.54.243; 11.AN.54.247;
11.AN.55.157; 11.AN.55.158; 11.AN.55.196; 11.AN.55.223; 11.AN.55.240;
11.AN.55.244; 11.AN.55.243; 11.AN.55.247; 11.AN.56.157; 11.AN.56.158;
11.AN.56.196; 11.AN.56.223; 11.AN.56.240; 11.AN.56.244; 11.AN.56.243;
11.AN.56.247; 11.AN.157.157; 11.AN.157.158; 11.AN.157.196;
11.AN.157.223; 11.AN.157.240; 11.AN.157.244; 11.AN.157.243;
11.AN.157.247; 11.AN.196.157; 11.AN.196.158; 11.AN.196.196;
11.AN.196.223; 11.AN.196.240; 11.AN.196.244; 11.AN.196.243;
11.AN.196.247; 11.AN.223.157; 11.AN.223.158; 11.AN.223.196;
11.AN.223.223; 11.AN.223.240; 11.AN.223.244; 11.AN.223.243;
11.AN.223.247; 11.AN.240.157; 11.AN.240.158; 11.AN.240.196;
11.AN.240.223; 11.AN.240.240; 11.AN.240.244; 11.AN.240.243;
11.AN.240.247; 11.AN.244.157; 11.AN.244.158; 11.AN.244.196;
11.AN.244.223; 11.AN.244.240; 11.AN.244.244; 11.AN.244.243;
11.AN.244.247; 11.AN.247.157; 11.AN.247.158; 11.AN.247.196;
11.AN.247.223; 11.AN.247.240; 11.AN.247.244; 11.AN.247.243;
11.AN.247.247;
Prodrugs of 11.AP 11.AP.4.157; 11.AP.4.158; 11.AP.4.196; 11.AP.4.223; 11.AP.4.240;
11.AP.4.244; 11.AP.4.243; 11.AP.4.247; 11.AP.5.157; 11.AP.5.158;
11.AP.5.196; 11.AP.5.223; 11.AP.5.240; 11.AP.5.244; 11.AP.5.243;
11.AP.5.247; 11.AP.7.157; 11.AP.7.158; 11.AP.7.196; 11.AP.7.223;
11.AP.7.240; 11.AP.7.244; 11.AP.7.243; 11.AP.7.247; 11.AP.15.157;
11.AP.15.158; 11.AP.15.196; 11.AP.15.223; 11.AP.15.240; 11.AP.15.244;
11.AP.15.243; 11.AP.15.247; 11.AP.16.157; 11.AP.16.158; 11.AP.16.196;
11.AP.16.223; 11.AP.16.240; 11.AP.16.244; 11.AP.16.243; 11.AP.16.247;
11.AP.18.157; 11.AP.18.158; 11.AP.18.196; 11.AP.18.223; 11.AP.18.240;
11.AP.18.244; 11.AP.18.243; 11.AP.18.247; 11.AP.26.157; 11.AP.26.158;
11.AP.26.196; 11.AP.26.223; 11.AP.26.240; 11.AP.26.244; 11.AP.26.243;
11.AP.26.247; 11.AP.27.157; 11.AP.27.158; 11.AP.27.196; 11.AP.27.223;
11.AP.27.240; 11.AP.27.244; 11.AP.27.243; 11.AP.27.247; 11.AP.29.157;
11.AP.29.158; 11.AP.29.196; 11.AP.29.223; 11.AP.29.240; 11.AP.29.244;
11.AP.29.243; 11.AP.29.247; 11.AP.54.157; 11.AP.54.158; 11.AP.54.196;
11.AP.54.223; 11.AP.54.240; 11.AP.54.244; 11.AP.54.243; 11.AP.54.247;
11.AP.55.157; 11.AP.55.158; 11.AP.55.196; 11.AP.55.223; 11.AP.55.240;
11.AP.55.244; 11.AP.55.243; 11.AP.55.247; 11.AP.56.157; 11.AP.56.158;
11.AP.56.196; 11.AP.56.223; 11.AP.56.240; 11.AP.56.244; 11.AP.56.243;
11.AP.56.247; 11.AP.157.157; 11.AP.157.158; 11.AP.157.196; 11.AP.157.223;
11.AP.157.240; 11.AP.157.244; 11.AP.157.243; 11.AP.157.247;
11.AP.196.157; 11.AP.196.158; 11.AP.196.196; 11.AP.196.223;
11.AP.196.240; 11.AP.196.244; 11.AP.196.243; 11.AP.196.247;
11.AP.223.157; 11.AP.223.158; 11.AP.223.196; 11.AP.223.223;
11.AP.223.240; 11.AP.223.244; 11.AP.223.243; 11.AP.223.247;
11.AP.240.157; 11.AP.240.158; 11.AP.240.196; 11.AP.240.223;
11.AP.240.240; 11.AP.240.244; 11.AP.240.243; 11.AP.240.247;
11.AP.244.157; 11.AP.244.158; 11.AP.244.196; 11.AP.244.223;

TABLE 100-continued

11.AP.244.240; 11.AP.244.244; 11.AP.244.243; 11.AP.244.247;
11.AP.247.157; 11.AP.247.158; 11.AP.247.196; 11.AP.247.223;
11.AP.247.240; 11.AP.247.244; 11.AP.247.243; 11.AP.247.247;

Prodrugs of 11.AZ

11.AZ.4.157; 11.AZ.4.158; 11.AZ.4.196; 11.AZ.4.223; 11.AZ.4.240;
11.AZ.4.244; 11.AZ.4.243; 11.AZ.4.247; 11.AZ.5.157; 11.AZ.5.158;
11.AZ.5.196; 11.AZ.5.223; 11.AZ.5.240; 11.AZ.5.244; 11.AZ.5.243;
11.AZ.5.247; 11.AZ.7.157; 11.AZ.7.158; 11.AZ.7.196; 11.AZ.7.223;
11.AZ.7.240; 11.AZ.7.244; 11.AZ.7.243; 11.AZ.7.247; 11.AZ.15.157;
11.AZ.15.158; 11.AZ.15.196; 11.AZ.15.223; 11.AZ.15.240; 11.AZ.15.244;
11.AZ.15.243; 11.AZ.15.247; 11.AZ.16.157; 11.AZ.16.158; 11.AZ.16.196;
11.AZ.16.223; 11.AZ.16.240; 11.AZ.16.244; 11.AZ.16.243; 11.AZ.16.247;
11.AZ.18.157; 11.AZ.18.158; 11.AZ.18.196; 11.AZ.18.223; 11.AZ.18.240;
11.AZ.18.244; 11.AZ.18.243; 11.AZ.18.247; 11.AZ.26.157; 11.AZ.26.158;
11.AZ.26.196; 11.AZ.26.223; 11.AZ.26.240; 11.AZ.26.244; 11.AZ.26.243;
11.AZ.26.247; 11.AZ.27.157; 11.AZ.27.158; 11.AZ.27.196; 11.AZ.27.223;
11.AZ.27.240; 11.AZ.27.244; 11.AZ.27.243; 11.AZ.27.247; 11.AZ.29.157;
11.AZ.29.158; 11.AZ.29.196; 11.AZ.29.223; 11.AZ.29.240; 11.AZ.29.244;
11.AZ.29.243; 11.AZ.29.247; 11.AZ.54.157; 11.AZ.54.158; 11.AZ.54.196;
11.AZ.54.223; 11.AZ.54.240; 11.AZ.54.244; 11.AZ.54.243; 11.AZ.54.247;
11.AZ.55.157; 11.AZ.55.158; 11.AZ.55.196; 11.AZ.55.223; 11.AZ.55.240;
11.AZ.55.244; 11.AZ.55.243; 11.AZ.55.247; 11.AZ.56.157; 11.AZ.56.158;
11.AZ.56.196; 11.AZ.56.223; 11.AZ.56.240; 11.AZ.56.244; 11.AZ.56.243;
11.AZ.56.247; 11.AZ.157.157; 11.AZ.157.158; 11.AZ.157.196; 11.AZ.157.223;
11.AZ.157.240; 11.AZ.157.244; 11.AZ.157.243; 11.AZ.157.247;
11.AZ.196.157; 11.AZ.196.158; 11.AZ.196.196; 11.AZ.196.223;
11.AZ.196.240; 11.AZ.196.244; 11.AZ.196.243; 11.AZ.196.247;
11.AZ.223.157; 11.AZ.223.158; 11.AZ.223.196; 11.AZ.223.223;
11.AZ.223.240; 11.AZ.223.244; 11.AZ.223.243; 11.AZ.223.247;
11.AZ.240.157; 11.AZ.240.158; 11.AZ.240.196; 11.AZ.240.223;
11.AZ.240.240; 11.AZ.240.244; 11.AZ.240.243; 11.AZ.240.247;
11.AZ.244.157; 11.AZ.244.158; 11.AZ.244.196; 11.AZ.244.223;
11.AZ.244.240; 11.AZ.244.244; 11.AZ.244.243; 11.AZ.244.247;
11.AZ.247.157; 11.AZ.247.158; 11.AZ.247.196; 11.AZ.247.223;
11.AZ.247.240; 11.AZ.247.244; 11.AZ.247.243; 11.AZ.247.247;

Prodrugs of 11.BF

11.BF.4.157; 11.BF.4.158; 11.BF.4.196; 11.BF.4.223; 11.BF.4.240;
11.BF.4.244; 11.BF.4.243; 11.BF.4.247; 11.BF.5.157; 11.BF.5.158;
11.BF.5.196; 11.BF.5.223; 11.BF.5.240; 11.BF.5.244; 11.BF.5.243;
11.BF.5.247; 11.BF.7.157; 11.BF.7.158; 11.BF.7.196; 11.BF.7.223;
11.BF.7.240; 11.BF.7.244; 11.BF.7.243; 11.BF.7.247; 11.BF.15.157;
11.BF.15.158; 11.BF.15.196; 11.BF.15.223; 11.BF.15.240; 11.BF.15.244;
11.BF.15.243; 11.BF.15.247; 11.BF.16.157; 11.BF.16.158; 11.BF.16.196;
11.BF.16.223; 11.BF.16.240; 11.BF.16.244; 11.BF.16.243; 11.BF.16.247;
11.BF.18.157; 11.BF.18.158; 11.BF.18.196; 11.BF.18.223; 11.BF.18.240;
11.BF.18.244; 11.BF.18.243; 11.BF.18.247; 11.BF.26.157; 11.BF.26.158;
11.BF.26.196; 11.BF.26.223; 11.BF.26.240; 11.BF.26.244; 11.BF.26.243;
11.BF.26.247; 11.BF.27.157; 11.BF.27.158; 11.BF.27.196; 11.BF.27.223;
11.BF.27.240; 11.BF.27.244; 11.BF.27.243; 11.BF.27.247; 11.BF.29.157;
11.BF.29.158; 11.BF.29.196; 11.BF.29.223; 11.BF.29.240; 11.BF.29.244;
11.BF.29.243; 11.BF.29.247; 11.BF.54.157; 11.BF.54.158; 11.BF.54.196;
11.BF.54.223; 11.BF.54.240; 11.BF.54.244; 11.BF.54.243; 11.BF.54.247;
11.BF.55.157; 11.BF.55.158; 11.BF.55.196; 11.BF.55.223; 11.BF.55.240;
11.BF.55.244; 11.BF.55.243; 11.BF.55.247; 11.BF.56.157; 11.BF.56.158;
11.BF.56.196; 11.BF.56.223; 11.BF.56.240; 11.BF.56.244; 11.BF.56.243;
11.BF.56.247; 11.BF.157.157; 11.BF.157.158; 11.BF.157.196; 11.BF.157.223;
11.BF.157.240; 11.BF.157.244; 11.BF.157.243; 11.BF.157.247; 11.BF.196.157;
11.BF.196.158; 11.BF.196.196; 11.BF.196.223; 11.BF.196.240; 11.BF.196.244;
11.BF.196.243; 11.BF.196.247; 11.BF.223.157; 11.BF.223.158; 11.BF.223.196;
11.BF.223.223; 11.BF.223.240; 11.BF.223.244; 11.BF.223.243; 11.BF.223.247;
11.BF.240.157; 11.BF.240.158; 11.BF.240.196; 11.BF.240.223; 11.BF.240.240;
11.BF.240.244; 11.BF.240.243; 11.BF.240.247; 11.BF.244.157; 11.BF.244.158;
11.BF.244.196; 11.BF.244.223; 11.BF.244.240; 11.BF.244.244; 11.BF.244.243;
11.BF.244.247; 11.BF.247.157; 11.BF.247.158; 11.BF.247.196; 11.BF.247.223;
11.BF.247.240; 11.BF.247.244; 11.BF.247.243; 11.BF.247.247;

Prodrugs of 11.CI

11.CI.4.157; 11.CI.4.158; 11.CI.4.196; 11.CI.4.223; 11.CI.4.240;
11.CI.4.244; 11.CI.4.243; 11.CI.4.247; 11.CI.5.157; 11.CI.5.158; 11.CI.5.196;
11.CI.5.223; 11.CI.5.240; 11.CI.5.244; 11.CI.5.243; 11.CI.5.247; 11.CI.7.157;
11.CI.7.158; 11.CI.7.196; 11.CI.7.223; 11.CI.7.240; 11.CI.7.244; 11.CI.7.243;
11.CI.7.247; 11.CI.15.157; 11.CI.15.158; 11.CI.15.196; 11.CI.15.223;
11.CI.15.240; 11.CI.15.244; 11.CI.15.243; 11.CI.15.247; 11.CI.16.157;
11.CI.16.158; 11.CI.16.196; 11.CI.16.223; 11.CI.16.240; 11.CI.16.244;
11.CI.16.243; 11.CI.16.247; 11.CI.18.157; 11.CI.18.158; 11.CI.18.196;
11.CI.18.223; 11.CI.18.240; 11.CI.18.244; 11.CI.18.243; 11.CI.18.247;
11.CI.26.157; 11.CI.26.158; 11.CI.26.196; 11.CI.26.223; 11.CI.26.240;

TABLE 100-continued

11.CI.26.244; 11.CI.26.243; 11.CI.26.247; 11.CI.27.157; 11.CI.27.158;
11.CI.27.196; 11.CI.27.223; 11.CI.27.240; 11.CI.27.244; 11.CI.27.243;
11.CI.27.247; 11.CI.29.157; 11.CI.29.158; 11.CI.29.196; 11.CI.29.223;
11.CI.29.240; 11.CI.29.244; 11.CI.29.243; 11.CI.29.247; 11.CI.54.157;
11.CI.54.158; 11.CI.54.196; 11.CI.54.223; 11.CI.54.240; 11.CI.54.244;
11.CI.54.243; 11.CI.54.247; 11.CI.55.157; 11.CI.55.158; 11.CI.55.196;
11.CI.55.223; 11.CI.55.240; 11.CI.55.244; 11.CI.55.243; 11.CI.55.247;
11.CI.56.157; 11.CI.56.158; 11.CI.56.196; 11.CI.56.223; 11.CI.56.240;
11.CI.56.244; 11.CI.56.243; 11.CI.56.247; 11.CI.157.157; 11.CI.157.158;
11.CI.157.196; 11.CI.157.223; 11.CI.157.240; 11.CI.157.244; 11.CI.157.243;
11.CI.157.247; 11.CI.196.157; 11.CI.196.158; 11.CI.196.196; 11.CI.196.223;
11.CI.196.240; 11.CI.196.244; 11.CI.196.243; 11.CI.196.247; 11.CI.223.157;
11.CI.223.158; 11.CI.223.196; 11.CI.223.223; 11.CI.223.240; 11.CI.223.244;
11.CI.223.243; 11.CI.223.247; 11.CI.240.157; 11.CI.240.158; 11.CI.240.196;
11.CI.240.223; 11.CI.240.240; 11.CI.240.244; 11.CI.240.243; 11.CI.240.247;
11.CI.244.157; 11.CI.244.158; 11.CI.244.196; 11.CI.244.223; 11.CI.244.240;
11.CI.244.244; 11.CI.244.243; 11.CI.244.247; 11.CI.247.157; 11.CI.247.158;
11.CI.247.196; 11.CI.247.223; 11.CI.247.240; 11.CI.247.244; 11.CI.247.243;
11.CI.247.247;
Prodrugs of 11.CO 11.CO.4.157; 11.CO.4.158; 11.CO.4.196; 11.CO.4.223; 11.CO.4.240;
11.CO.4.244; 11.CO.4.243; 11.CO.4.247; 11.CO.5.157; 11.CO.5.158;
11.CO.5.196; 11.CO.5.223; 11.CO.5.240; 11.CO.5.244; 11.CO.5.243;
11.CO.5.247; 11.CO.7.157; 11.CO.7.158; 11.CO.7.196; 11.CO.7.223;
11.CO.7.240; 11.CO.7.244; 11.CO.7.243; 11.CO.7.247; 11.CO.15.157;
11.CO.15.158; 11.CO.15.196; 11.CO.15.223; 11.CO.15.240; 11.CO.15.244;
11.CO.15.243; 11.CO.15.247; 11.CO.16.157; 11.CO.16.158; 11.CO.16.196;
11.CO.16.223; 11.CO.16.240; 11.CO.16.244; 11.CO.16.243; 11.CO.16.247;
11.CO.18.157; 11.CO.18.158; 11.CO.18.196; 11.CO.18.223; 11.CO.18.240;
11.CO.18.244; 11.CO.18.243; 11.CO.18.247; 11.CO.26.157; 11.CO.26.158;
11.CO.26.196; 11.CO.26.223; 11.CO.26.240; 11.CO.26.244; 11.CO.26.243;
11.CO.26.247; 11.CO.27.157; 11.CO.27.158; 11.CO.27.196; 11.CO.27.223;
11.CO.27.240; 11.CO.27.244; 11.CO.27.243; 11.CO.27.247; 11.CO.29.157;
11.CO.29.158; 11.CO.29.196; 11.CO.29.223; 11.CO.29.240; 11.CO.29.244;
11.CO.29.243; 11.CO.29.247; 11.CO.54.157; 11.CO.54.158; 11.CO.54.196;
11.CO.54.223; 11.CO.54.240; 11.CO.54.244; 11.CO.54.243; 11.CO.54.247;
11.CO.55.157; 11.CO.55.158; 11.CO.55.196; 11.CO.55.223; 11.CO.55.240;
11.CO.55.244; 11.CO.55.243; 11.CO.55.247; 11.CO.56.157; 11.CO.56.158;
11.CO.56.196; 11.CO.56.223; 11.CO.56.240; 11.CO.56.244; 11.CO.56.243;
11.CO.56.247; 11.CO.157.157; 11.CO.157.158; 11.CO.157.196;
11.CO.157.223; 11.CO.157.240; 11.CO.157.244; 11.CO.157.243;
11.CO.157.247; 11.CO.196.157; 11.CO.196.158; 11.CO.196.196;
11.CO.196.223; 11.CO.196.240; 11.CO.196.244; 11.CO.196.243;
11.CO.196.247; 11.CO.223.157; 11.CO.223.158; 11.CO.223.196;
11.CO.223.223; 11.CO.223.240; 11.CO.223.244; 11.CO.223.243;
11.CO.223.247; 11.CO.240.157; 11.CO.240.158; 11.CO.240.196;
11.CO.240.223; 11.CO.240.240; 11.CO.240.244; 11.CO.240.243;
11.CO.240.247; 11.CO.244.157; 11.CO.244.158; 11.CO.244.196;
11.CO.244.223; 11.CO.244.240; 11.CO.244.244; 11.CO.244.243;
11.CO.244.247; 11.CO.247.157; 11.CO.247.158; 11.CO.247.196;
11.CO.247.223; 11.CO.247.240; 11.CO.247.244; 11.CO.247.243;
11.CO.247.247;
Prodrugs of 12.AH 12.AH.4.157; 12.AH.4.158; 12.AH.4.196; 12.AH.4.223; 12.AH.4.240;
12.AH.4.244; 12.AH.4.243; 12.AH.4.247; 12.AH.5.157; 12.AH.5.158;
12.AH.5.196; 12.AH.5.223; 12.AH.5.240; 12.AH.5.244; 12.AH.5.243;
12.AH.5.247; 12.AH.7.157; 12.AH.7.158; 12.AH.7.196; 12.AH.7.223;
12.AH.7.240; 12.AH.7.244; 12.AH.7.243; 12.AH.7.247; 12.AH.15.157;
12.AH.15.158; 12.AH.15.196; 12.AH.15.223; 12.AH.15.240; 12.AH.15.244;
12.AH.15.243; 12.AH.15.247; 12.AH.16.157; 12.AH.16.158; 12.AH.16.196;
12.AH.16.223; 12.AH.16.240; 12.AH.16.244; 12.AH.16.243; 12.AH.16.247;
12.AH.18.157; 12.AH.18.158; 12.AH.18.196; 12.AH.18.223; 12.AH.18.240;
12.AH.18.244; 12.AH.18.243; 12.AH.18.247; 12.AH.26.157; 12.AH.26.158;
12.AH.26.196; 12.AH.26.223; 12.AH.26.240; 12.AH.26.244; 12.AH.26.243;
12.AH.26.247; 12.AH.27.157; 12.AH.27.158; 12.AH.27.196; 12.AH.27.223;
12.AH.27.240; 12.AH.27.244; 12.AH.27.243; 12.AH.27.247; 12.AH.29.157;
12.AH.29.158; 12.AH.29.196; 12.AH.29.223; 12.AH.29.240; 12.AH.29.244;
12.AH.29.243; 12.AH.29.247; 12.AH.54.157; 12.AH.54.158; 12.AH.54.196;
12.AH.54.223; 12.AH.54.240; 12.AH.54.244; 12.AH.54.243; 12.AH.54.247;
12.AH.55.157; 12.AH.55.158; 12.AH.55.196; 12.AH.55.223; 12.AH.55.240;
12.AH.55.244; 12.AH.55.243; 12.AH.55.247; 12.AH.56.157; 12.AH.56.158;
12.AH.56.196; 12.AH.56.223; 12.AH.56.240; 12.AH.56.244; 12.AH.56.243;
12.AH.56.247; 12.AH.157.157; 12.AH.157.158; 12.AH.157.196;
12.AH.157.223; 12.AH.157.240; 12.AH.157.244; 12.AH.157.243;
12.AH.157.247; 12.AH.196.157; 12.AH.196.158; 12.AH.196.196;
12.AH.196.223; 12.AH.196.240; 12.AH.196.244; 12.AH.196.243;
12.AH.196.247; 12.AH.223.157; 12.AH.223.158; 12.AH.223.196;

TABLE 100-continued

12.AH.223.223; 12.AH.223.240; 12.AH.223.244; 12.AH.223.243;
12.AH.223.247; 12.AH.240.157; 12.AH.240.158; 12.AH.240.196;
12.AH.240.223; 12.AH.240.240; 12.AH.240.244; 12.AH.240.243;
12.AH.240.247; 12.AH.244.157; 12.AH.244.158; 12.AH.244.196;
12.AH.244.223; 12.AH.244.240; 12.AH.244.244; 12.AH.244.243;
12.AH.244.247; 12.AH.247.157; 12.AH.247.158; 12.AH.247.196;
12.AH.247.223; 12.AH.247.240; 12.AH.247.244; 12.AH.247.243;
12.AH.247.247;
Prodrugs of 12.AJ 12.AJ.4.157; 12.AJ.4.158; 12.AJ.4.196; 12.AJ.4.223; 12.AJ.4.240;
12.AJ.4.244; 12.AJ.4.243; 12.AJ.4.247; 12.AJ.5.157; 12.AJ.5.158; 12.AJ.5.196;
12.AJ.5.223; 12.AJ.5.240; 12.AJ.5.244; 12.AJ.5.243; 12.AJ.5.247; 12.AJ.7.157;
12.AJ.7.158; 12.AJ.7.196; 12.AJ.7.223; 12.AJ.7.240; 12.AJ.7.244; 12.AJ.7.243;
12.AJ.7.247; 12.AJ.15.157; 12.AJ.15.158; 12.AJ.15.196; 12.AJ.15.223;
12.AJ.15.240; 12.AJ.15.244; 12.AJ.15.243; 12.AJ.15.247; 12.AJ.16.157;
12.AJ.16.158; 12.AJ.16.196; 12.AJ.16.223; 12.AJ.16.240; 12.AJ.16.244;
12.AJ.16.243; 12.AJ.16.247; 12.AJ.18.157; 12.AJ.18.158; 12.AJ.18.196;
12.AJ.18.223; 12.AJ.18.240; 12.AJ.18.244; 12.AJ.18.243; 12.AJ.18.247;
12.AJ.26.157; 12.AJ.26.158; 12.AJ.26.196; 12.AJ.26.223; 12.AJ.26.240;
12.AJ.26.244; 12.AJ.26.243; 12.AJ.26.247; 12.AJ.27.157; 12.AJ.27.158;
12.AJ.27.196; 12.AJ.27.223; 12.AJ.27.240; 12.AJ.27.244; 12.AJ.27.243;
12.AJ.27.247; 12.AJ.29.157; 12.AJ.29.158; 12.AJ.29.196; 12.AJ.29.223;
12.AJ.29.240; 12.AJ.29.244; 12.AJ.29.243; 12.AJ.29.247; 12.AJ.54.157;
12.AJ.54.158; 12.AJ.54.196; 12.AJ.54.223; 12.AJ.54.240; 12.AJ.54.244;
12.AJ.54.243; 12.AJ.54.247; 12.AJ.55.157; 12.AJ.55.158; 12.AJ.55.196;
12.AJ.55.223; 12.AJ.55.240; 12.AJ.55.244; 12.AJ.55.243; 12.AJ.55.247;
12.AJ.56.157; 12.AJ.56.158; 12.AJ.56.196; 12.AJ.56.223; 12.AJ.56.240;
12.AJ.56.244; 12.AJ.56.243; 12.AJ.56.247; 12.AJ.157.157; 12.AJ.157.158;
12.AJ.157.196; 12.AJ.157.223; 12.AJ.157.240; 12.AJ.157.244; 12.AJ.157.243;
12.AJ.157.247; 12.AJ.196.157; 12.AJ.196.158; 12.AJ.196.196; 12.AJ.196.223;
12.AJ.196.240; 12.AJ.196.244; 12.AJ.196.243; 12.AJ.196.247; 12.AJ.223.157;
12.AJ.223.158; 12.AJ.223.196; 12.AJ.223.223; 12.AJ.223.240; 12.AJ.223.244;
12.AJ.223.243; 12.AJ.223.247; 12.AJ.240.157; 12.AJ.240.158; 12.AJ.240.196;
12.AJ.240.223; 12.AJ.240.240; 12.AJ.240.244; 12.AJ.240.243; 12.AJ.240.247;
12.AJ.244.157; 12.AJ.244.158; 12.AJ.244.196; 12.AJ.244.223; 12.AJ.244.240;
12.AJ.244.244; 12.AJ.244.243; 12.AJ.244.247; 12.AJ.247.157; 12.AJ.247.158;
12.AJ.247.196; 12.AJ.247.223; 12.AJ.247.240; 12.AJ.247.244; 12.AJ.247.243;
12.AJ.247.247;
Prodrugs of 12.AN 12.AN.4.157; 12.AN.4.158; 12.AN.4.196; 12.AN.4.223; 12.AN.4.240;
12.AN.4.244; 12.AN.4.243; 12.AN.4.247; 12.AN.5.157; 12.AN.5.158;
12.AN.5.196; 12.AN.5.223; 12.AN.5.240; 12.AN.5.244; 12.AN.5.243;
12.AN.5.247; 12.AN.7.157; 12.AN.7.158; 12.AN.7.196; 12.AN.7.223;
12.AN.7.240; 12.AN.7.244; 12.AN.7.243; 12.AN.7.247; 12.AN.15.157;
12.AN.15.158; 12.AN.15.196; 12.AN.15.223; 12.AN.15.240; 12.AN.15.244;
12.AN.15.243; 12.AN.15.247; 12.AN.16.157; 12.AN.16.158; 12.AN.16.196;
12.AN.16.223; 12.AN.16.240; 12.AN.16.244; 12.AN.16.243; 12.AN.16.247;
12.AN.18.157; 12.AN.18.158; 12.AN.18.196; 12.AN.18.223; 12.AN.18.240;
12.AN.18.244; 12.AN.18.243; 12.AN.18.247; 12.AN.26.157; 12.AN.26.158;
12.AN.26.196; 12.AN.26.223; 12.AN.26.240; 12.AN.26.244; 12.AN.26.243;
12.AN.26.247; 12.AN.27.157; 12.AN.27.158; 12.AN.27.196; 12.AN.27.223;
12.AN.27.240; 12.AN.27.244; 12.AN.27.243; 12.AN.27.247; 12.AN.29.157;
12.AN.29.158; 12.AN.29.196; 12.AN.29.223; 12.AN.29.240; 12.AN.29.244;
12.AN.29.243; 12.AN.29.247; 12.AN.54.157; 12.AN.54.158; 12.AN.54.196;
12.AN.54.223; 12.AN.54.240; 12.AN.54.244; 12.AN.54.243; 12.AN.54.247;
12.AN.55.157; 12.AN.55.158; 12.AN.55.196; 12.AN.55.223; 12.AN.55.240;
12.AN.55.244; 12.AN.55.243; 12.AN.55.247; 12.AN.56.157; 12.AN.56.158;
12.AN.56.196; 12.AN.56.223; 12.AN.56.240; 12.AN.56.244; 12.AN.56.243;
12.AN.56.247; 12.AN.157.157; 12.AN.157.158; 12.AN.157.196;
12.AN.157.223; 12.AN.157.240; 12.AN.157.244; 12.AN.157.243;
12.AN.157.247; 12.AN.196.157; 12.AN.196.158; 12.AN.196.196;
12.AN.196.223; 12.AN.196.240; 12.AN.196.244; 12.AN.196.243;
12.AN.196.247; 12.AN.223.157; 12.AN.223.158; 12.AN.223.196;
12.AN.223.223; 12.AN.223.240; 12.AN.223.244; 12.AN.223.243;
12.AN.223.247; 12.AN.240.157; 12.AN.240.158; 12.AN.240.196;
12.AN.240.223; 12.AN.240.240; 12.AN.240.244; 12.AN.240.243;
12.AN.240.247; 12.AN.244.157; 12.AN.244.158; 12.AN.244.196;
12.AN.244.223; 12.AN.244.240; 12.AN.244.244; 12.AN.244.243;
12.AN.244.247; 12.AN.247.157; 12.AN.247.158; 12.AN.247.196;
12.AN.247.223; 12.AN.247.240; 12.AN.247.244; 12.AN.247.243;
12.AN.247.247;
Prodrugs of 12.AP 12.AP.4.157; 12.AP.4.158; 12.AP.4.196; 12.AP.4.223; 12.AP.4.240;
12.AP.4.244; 12.AP.4.243; 12.AP.4.247; 12.AP.5.157; 12.AP.5.158;
12.AP.5.196; 12.AP.5.223; 12.AP.5.240; 12.AP.5.244; 12.AP.5.243;
12.AP.5.247; 12.AP.7.157; 12.AP.7.158; 12.AP.7.196; 12.AP.7.223;

TABLE 100-continued

12.AP.7.240; 12.AP.7.244; 12.AP.7.243; 12.AP.7.247; 12.AP.15.157;
12.AP.15.158; 12.AP.15.196; 12.AP.15.223; 12.AP.15.240; 12.AP.15.244;
12.AP.15.243; 12.AP.15.247; 12.AP.16.157; 12.AP.16.158; 12.AP.16.196;
12.AP.16.223; 12.AP.16.240; 12.AP.16.244; 12.AP.16.243; 12.AP.16.247;
12.AP.18.157; 12.AP.18.158; 12.AP.18.196; 12.AP.18.223; 12.AP.18.240;
12.AP.18.244; 12.AP.18.243; 12.AP.18.247; 12.AP.26.157; 12.AP.26.158;
12.AP.26.196; 12.AP.26.223; 12.AP.26.240; 12.AP.26.244; 12.AP.26.243;
12.AP.26.247; 12.AP.27.157; 12.AP.27.158; 12.AP.27.196; 12.AP.27.223;
12.AP.27.240; 12.AP.27.244; 12.AP.27.243; 12.AP.27.247; 12.AP.29.157;
12.AP.29.158; 12.AP.29.196; 12.AP.29.223; 12.AP.29.240; 12.AP.29.244;
12.AP.29.243; 12.AP.29.247; 12.AP.54.157; 12.AP.54.158; 12.AP.54.196;
12.AP.54.223; 12.AP.54.240; 12.AP.54.244; 12.AP.54.243; 12.AP.54.247;
12.AP.55.157; 12.AP.55.158; 12.AP.55.196; 12.AP.55.223; 12.AP.55.240;
12.AP.55.244; 12.AP.55.243; 12.AP.55.247; 12.AP.56.157; 12.AP.56.158;
12.AP.56.196; 12.AP.56.223; 12.AP.56.240; 12.AP.56.244; 12.AP.56.243;
12.AP.56.247; 12.AP.157.157; 12.AP.157.158; 12.AP.157.196; 12.AP.157.223;
12.AP.157.240; 12.AP.157.244; 12.AP.157.243; 12.AP.157.247;
12.AP.196.157; 12.AP.196.158; 12.AP.196.196; 12.AP.196.223;
12.AP.196.240; 12.AP.196.244; 12.AP.196.243; 12.AP.196.247;
12.AP.223.157; 12.AP.223.158; 12.AP.223.196; 12.AP.223.223;
12.AP.223.240; 12.AP.223.244; 12.AP.223.243; 12.AP.223.247;
12.AP.240.157; 12.AP.240.158; 12.AP.240.196; 12.AP.240.223;
12.AP.240.240; 12.AP.240.244; 12.AP.240.243; 12.AP.240.247;
12.AP.244.157; 12.AP.244.158; 12.AP.244.196; 12.AP.244.223;
12.AP.244.240; 12.AP.244.244; 12.AP.244.243; 12.AP.244.247;
12.AP.247.157; 12.AP.247.158; 12.AP.247.196; 12.AP.247.223;
12.AP.247.240; 12.AP.247.244; 12.AP.247.243; 12.AP.247.247;
Prodrugs of 12.AZ 12.AZ.4.157; 12.AZ.4.158; 12.AZ.4.196; 12.AZ.4.223; 12.AZ.4.240;
12.AZ.4.244; 12.AZ.4.243; 12.AZ.4.247; 12.AZ.5.157; 12.AZ.5.158;
12.AZ.5.196; 12.AZ.5.223; 12.AZ.5.240; 12.AZ.5.244; 12.AZ.5.243;
12.AZ.5.247; 12.AZ.7.157; 12.AZ.7.158; 12.AZ.7.196; 12.AZ.7.223;
12.AZ.7.240; 12.AZ.7.244; 12.AZ.7.243; 12.AZ.7.247; 12.AZ.15.157;
12.AZ.15.158; 12.AZ.15.196; 12.AZ.15.223; 12.AZ.15.240; 12.AZ.15.244;
12.AZ.15.243; 12.AZ.15.247; 12.AZ.16.157; 12.AZ.16.158; 12.AZ.16.196;
12.AZ.16.223; 12.AZ.16.240; 12.AZ.16.244; 12.AZ.16.243; 12.AZ.16.247;
12.AZ.18.157; 12.AZ.18.158; 12.AZ.18.196; 12.AZ.18.223; 12.AZ.18.240;
12.AZ.18.244; 12.AZ.18.243; 12.AZ.18.247; 12.AZ.26.157; 12.AZ.26.158;
12.AZ.26.196; 12.AZ.26.223; 12.AZ.26.240; 12.AZ.26.244; 12.AZ.26.243;
12.AZ.26.247; 12.AZ.27.157; 12.AZ.27.158; 12.AZ.27.196; 12.AZ.27.223;
12.AZ.27.240; 12.AZ.27.244; 12.AZ.27.243; 12.AZ.27.247; 12.AZ.29.157;
12.AZ.29.158; 12.AZ.29.196; 12.AZ.29.223; 12.AZ.29.240; 12.AZ.29.244;
12.AZ.29.243; 12.AZ.29.247; 12.AZ.54.157; 12.AZ.54.158; 12.AZ.54.196;
12.AZ.54.223; 12.AZ.54.240; 12.AZ.54.244; 12.AZ.54.243; 12.AZ.54.247;
12.AZ.55.157; 12.AZ.55.158; 12.AZ.55.196; 12.AZ.55.223; 12.AZ.55.240;
12.AZ.55.244; 12.AZ.55.243; 12.AZ.55.247; 12.AZ.56.157; 12.AZ.56.158;
12.AZ.56.196; 12.AZ.56.223; 12.AZ.56.240; 12.AZ.56.244; 12.AZ.56.243;
12.AZ.56.247; 12.AZ.157.157; 12.AZ.157.158; 12.AZ.157.196; 12.AZ.157.223;
12.AZ.157.240; 12.AZ.157.244; 12.AZ.157.243; 12.AZ.157.247;
12.AZ.196.157; 12.AZ.196.158; 12.AZ.196.196; 12.AZ.196.223;
12.AZ.196.240; 12.AZ.196.244; 12.AZ.196.243; 12.AZ.196.247;
12.AZ.223.157; 12.AZ.223.158; 12.AZ.223.196; 12.AZ.223.223;
12.AZ.223.240; 12.AZ.223.244; 12.AZ.223.243; 12.AZ.223.247;
12.AZ.240.157; 12.AZ.240.158; 12.AZ.240.196; 12.AZ.240.223;
12.AZ.240.240; 12.AZ.240.244; 12.AZ.240.243; 12.AZ.240.247;
12.AZ.244.157; 12.AZ.244.158; 12.AZ.244.196; 12.AZ.244.223;
12.AZ.244.240; 12.AZ.244.244; 12.AZ.244.243; 12.AZ.244.247;
12.AZ.247.157; 12.AZ.247.158; 12.AZ.247.196; 12.AZ.247.223;
12.AZ.247.240; 12.AZ.247.244; 12.AZ.247.243; 12.AZ.247.247;
Prodrugs of 12.BF 12.BF.4.157; 12.BF.4.158; 12.BF.4.196; 12.BF.4.223; 12.BF.4.240;
12.BF.4.244; 12.BF.4.243; 12.BF.4.247; 12.BF.5.157; 12.BF.5.158;
12.BF.5.196; 12.BF.5.223; 12.BF.5.240; 12.BF.5.244; 12.BF.5.243;
12.BF.5.247; 12.BF.7.157; 12.BF.7.158; 12.BF.7.196; 12.BF.7.223;
12.BF.7.240; 12.BF.7.244; 12.BF.7.243; 12.BF.7.247; 12.BF.15.157;
12.BF.15.158; 12.BF.15.196; 12.BF.15.223; 12.BF.15.240; 12.BF.15.244;
12.BF.15.243; 12.BF.15.247; 12.BF.16.157; 12.BF.16.158; 12.BF.16.196;
12.BF.16.223; 12.BF.16.240; 12.BF.16.244; 12.BF.16.243; 12.BF.16.247;
12.BF.18.157; 12.BF.18.158; 12.BF.18.196; 12.BF.18.223; 12.BF.18.240;
12.BF.18.244; 12.BF.18.243; 12.BF.18.247; 12.BF.26.157; 12.BF.26.158;
12.BF.26.196; 12.BF.26.223; 12.BF.26.240; 12.BF.26.244; 12.BF.26.243;
12.BF.26.247; 12.BF.27.157; 12.BF.27.158; 12.BF.27.196; 12.BF.27.223;
12.BF.27.240; 12.BF.27.244; 12.BF.27.243; 12.BF.27.247; 12.BF.29.157;
12.BF.29.158; 12.BF.29.196; 12.BF.29.223; 12.BF.29.240; 12.BF.29.244;
12.BF.29.243; 12.BF.29.247; 12.BF.54.157; 12.BF.54.158; 12.BF.54.196;
12.BF.54.223; 12.BF.54.240; 12.BF.54.244; 12.BF.54.243; 12.BF.54.247;
12.BF.55.157; 12.BF.55.158; 12.BF.55.196; 12.BF.55.223; 12.BF.55.240;

TABLE 100-continued

12.BF.55.244; 12.BF.55.243; 12.BF.55.247; 12.BF.56.157; 12.BF.56.158;
12.BF.56.196; 12.BF.56.223; 12.BF.56.240; 12.BF.56.244; 12.BF.56.243;
12.BF.56.247; 12.BF.157.157; 12.BF.157.158; 12.BF.157.196; 12.BF.157.223;
12.BF.157.240; 12.BF.157.244; 12.BF.157.243; 12.BF.157.247; 12.BF.196.157;
12.BF.196.158; 12.BF.196.196; 12.BF.196.223; 12.BF.196.240; 12.BF.196.244;
12.BF.196.243; 12.BF.196.247; 12.BF.223.157; 12.BF.223.158; 12.BF.223.196;
12.BF.223.223; 12.BF.223.240; 12.BF.223.244; 12.BF.223.243; 12.BF.223.247;
12.BF.240.157; 12.BF.240.158; 12.BF.240.196; 12.BF.240.223; 12.BF.240.240;
12.BF.240.244; 12.BF.240.243; 12.BF.240.247; 12.BF.244.157; 12.BF.244.158;
12.BF.244.196; 12.BF.244.223; 12.BF.244.240; 12.BF.244.244; 12.BF.244.243;
12.BF.244.247; 12.BF.247.157; 12.BF.247.158; 12.BF.247.196; 12.BF.247.223;
12.BF.247.240; 12.BF.247.244; 12.BF.247.243; 12.BF.247.247;
Prodrugs of 12.CI 12.CI.4.157; 12.CI.4.158; 12.CI.4.196; 12.CI.4.223; 12.CI.4.240;
12.CI.4.244; 12.CI.4.243; 12.CI.4.247; 12.CI.5.157; 12.CI.5.158; 12.CI.5.196;
12.CI.5.223; 12.CI.5.240; 12.CI.5.244; 12.CI.5.243; 12.CI.5.247; 12.CI.7.157;
12.CI.7.158; 12.CI.7.196; 12.CI.7.223; 12.CI.7.240; 12.CI.7.244; 12.CI.7.243;
12.CI.7.247; 12.CI.15.157; 12.CI.15.158; 12.CI.15.196; 12.CI.15.223;
12.CI.15.240; 12.CI.15.244; 12.CI.15.243; 12.CI.15.247; 12.CI.16.157;
12.CI.16.158; 12.CI.16.196; 12.CI.16.223; 12.CI.16.240; 12.CI.16.244;
12.CI.16.243; 12.CI.16.247; 12.CI.18.157; 12.CI.18.158; 12.CI.18.196;
12.CI.18.223; 12.CI.18.240; 12.CI.18.244; 12.CI.18.243; 12.CI.18.247;
12.CI.26.157; 12.CI.26.158; 12.CI.26.196; 12.CI.26.223; 12.CI.26.240;
12.CI.26.244; 12.CI.26.243; 12.CI.26.247; 12.CI.27.157; 12.CI.27.158;
12.CI.27.196; 12.CI.27.223; 12.CI.27.240; 12.CI.27.244; 12.CI.27.243;
12.CI.27.247; 12.CI.29.157; 12.CI.29.158; 12.CI.29.196; 12.CI.29.223;
12.CI.29.240; 12.CI.29.244; 12.CI.29.243; 12.CI.29.247; 12.CI.54.157;
12.CI.54.158; 12.CI.54.196; 12.CI.54.223; 12.CI.54.240; 12.CI.54.244;
12.CI.54.243; 12.CI.54.247; 12.CI.55.157; 12.CI.55.158; 12.CI.55.196;
12.CI.55.223; 12.CI.55.240; 12.CI.55.244; 12.CI.55.243; 12.CI.55.247;
12.CI.56.157; 12.CI.56.158; 12.CI.56.196; 12.CI.56.223; 12.CI.56.240;
12.CI.56.244; 12.CI.56.243; 12.CI.56.247; 12.CI.157.157; 12.CI.157.158;
12.CI.157.196; 12.CI.157.223; 12.CI.157.240; 12.CI.157.244; 12.CI.157.243;
12.CI.157.247; 12.CI.196.157; 12.CI.196.158; 12.CI.196.196; 12.CI.196.223;
12.CI.196.240; 12.CI.196.244; 12.CI.196.243; 12.CI.196.247; 12.CI.223.157;
12.CI.223.158; 12.CI.223.196; 12.CI.223.223; 12.CI.223.240; 12.CI.223.244;
12.CI.223.243; 12.CI.223.247; 12.CI.240.157; 12.CI.240.158; 12.CI.240.196;
12.CI.240.223; 12.CI.240.240; 12.CI.240.244; 12.CI.240.243; 12.CI.240.247;
12.CI.244.157; 12.CI.244.158; 12.CI.244.196; 12.CI.244.223; 12.CI.244.240;
12.CI.244.244; 12.CI.244.243; 12.CI.244.247; 12.CI.247.157; 12.CI.247.158;
12.CI.247.196; 12.CI.247.223; 12.CI.247.240; 12.CI.247.244; 12.CI.247.243;
12.CI.247.247;
Prodrugs of 12.CO 12.CO.4.157; 12.CO.4.158; 12.CO.4.196; 12.CO.4.223; 12.CO.4.240;
12.CO.4.244; 12.CO.4.243; 12.CO.4.247; 12.CO.5.157; 12.CO.5.158;
12.CO.5.196; 12.CO.5.223; 12.CO.5.240; 12.CO.5.244; 12.CO.5.243;
12.CO.5.247; 12.CO.7.157; 12.CO.7.158; 12.CO.7.196; 12.CO.7.223;
12.CO.7.240; 12.CO.7.244; 12.CO.7.243; 12.CO.7.247; 12.CO.15.157;
12.CO.15.158; 12.CO.15.196; 12.CO.15.223; 12.CO.15.240; 12.CO.15.244;
12.CO.15.243; 12.CO.15.247; 12.CO.16.157; 12.CO.16.158; 12.CO.16.196;
12.CO.16.223; 12.CO.16.240; 12.CO.16.244; 12.CO.16.243; 12.CO.16.247;
12.CO.18.157; 12.CO.18.158; 12.CO.18.196; 12.CO.18.223; 12.CO.18.240;
12.CO.18.244; 12.CO.18.243; 12.CO.18.247; 12.CO.26.157; 12.CO.26.158;
12.CO.26.196; 12.CO.26.223; 12.CO.26.240; 12.CO.26.244; 12.CO.26.243;
12.CO.26.247; 12.CO.27.157; 12.CO.27.158; 12.CO.27.196; 12.CO.27.223;
12.CO.27.240; 12.CO.27.244; 12.CO.27.243; 12.CO.27.247; 12.CO.29.157;
12.CO.29.158; 12.CO.29.196; 12.CO.29.223; 12.CO.29.240; 12.CO.29.244;
12.CO.29.243; 12.CO.29.247; 12.CO.54.157; 12.CO.54.158; 12.CO.54.196;
12.CO.54.223; 12.CO.54.240; 12.CO.54.244; 12.CO.54.243; 12.CO.54.247;
12.CO.55.157; 12.CO.55.158; 12.CO.55.196; 12.CO.55.223; 12.CO.55.240;
12.CO.55.244; 12.CO.55.243; 12.CO.55.247; 12.CO.56.157; 12.CO.56.158;
12.CO.56.196; 12.CO.56.223; 12.CO.56.240; 12.CO.56.244; 12.CO.56.243;
12.CO.56.247; 12.CO.157.157; 12.CO.157.158; 12.CO.157.196;
12.CO.157.223; 12.CO.157.240; 12.CO.157.244; 12.CO.157.243;
12.CO.157.247; 12.CO.196.157; 12.CO.196.158; 12.CO.196.196;
12.CO.196.223; 12.CO.196.240; 12.CO.196.244; 12.CO.196.243;
12.CO.196.247; 12.CO.223.157; 12.CO.223.158; 12.CO.223.196;
12.CO.223.223; 12.CO.223.240; 12.CO.223.244; 12.CO.223.243;
12.CO.223.247; 12.CO.240.157; 12.CO.240.158; 12.CO.240.196;
12.CO.240.223; 12.CO.240.240; 12.CO.240.244; 12.CO.240.243;
12.CO.240.247; 12.CO.244.157; 12.CO.244.158; 12.CO.244.196;
12.CO.244.223; 12.CO.244.240; 12.CO.244.244; 12.CO.244.243;
12.CO.244.247; 12.CO.247.157; 12.CO.247.158; 12.CO.247.196;
12.CO.247.223; 12.CO.247.240; 12.CO.247.244; 12.CO.247.243;
12.CO.247.247.

TABLE 100-continued

Prodrugs of 13.B

13.B.228.228; 13.B.228.229; 13.B.228.230; 13.B.228.231; 13.B.228.236;
13.B.228.237; 13.B.228.238; 13.B.228.239; 13.B.228.154; 13.B.228.157;
13.B.228.166; 13.B.228.169; 13.B.228.172; 13.B.228.175; 13.B.228.240;
13.B.228.244; 13.B.229.228; 13.B.229.229; 13.B.229.230; 13.B.229.231;
13.B.229.236; 13.B.229.237; 13.B.229.238; 13.B.229.239; 13.B.229.154;
13.B.229.157; 13.B.229.166; 13.B.229.169; 13.B.229.172; 13.B.229.175;
13.B.229.240; 13.B.229.244; 13.B.230.228; 13.B.230.229; 13.B.230.230;
13.B.230.231; 13.B.230.236; 13.B.230.237; 13.B.230.238; 13.B.230.239;
13.B.230.154; 13.B.230.157; 13.B.230.166; 13.B.230.169; 13.B.230.172;
13.B.230.175; 13.B.230.240; 13.B.230.244; 13.B.231.228; 13.B.231.229;
13.B.231.230; 13.B.231.231; 13.B.231.236; 13.B.231.237; 13.B.231.238;
13.B.231.239; 13.B.231.154; 13.B.231.157; 13.B.231.166; 13.B.231.169;
13.B.231.172; 13.B.231.175; 13.B.231.240; 13.B.231.244; 13.B.236.228;
13.B.236.229; 13.B.236.230; 13.B.236.231; 13.B.236.236; 13.B.236.237;
13.B.236.238; 13.B.236.239; 13.B.236.154; 13.B.236.157; 13.B.236.166;
13.B.236.169; 13.B.236.172; 13.B.236.175; 13.B.236.240; 13.B.236.244;
13.B.237.228; 13.B.237.229; 13.B.237.230; 13.B.237.231; 13.B.237.236;
13.B.237.237; 13.B.237.238; 13.B.237.239; 13.B.237.154; 13.B.237.157;
13.B.237.166; 13.B.237.169; 13.B.237.172; 13.B.237.175; 13.B.237.240;
13.B.237.244; 13.B.238.228; 13.B.238.229; 13.B.238.230; 13.B.238.231;
13.B.238.236; 13.B.238.237; 13.B.238.238; 13.B.238.239; 13.B.238.154;
13.B.238.157; 13.B.238.166; 13.B.238.169; 13.B.238.172; 13.B.238.175;
13.B.238.240; 13.B.238.244; 13.B.239.228; 13.B.239.229; 13.B.239.230;
13.B.239.231; 13.B.239.236; 13.B.239.237; 13.B.239.238; 13.B.239.239;
13.B.239.154; 13.B.239.157; 13.B.239.166; 13.B.239.169; 13.B.239.172;
13.B.239.175; 13.B.239.240; 13.B.239.244; 13.B.154.228; 13.B.154.229;
13.B.154.230; 13.B.154.231; 13.B.154.236; 13.B.154.237; 13.B.154.238;
13.B.154.239; 13.B.154.154; 13.B.154.157; 13.B.154.166; 13.B.154.169;
13.B.154.172; 13.B.154.175; 13.B.154.240; 13.B.154.244; 13.B.157.228;
13.B.157.229; 13.B.157.230; 13.B.157.231; 13.B.157.236; 13.B.157.237;
13.B.157.238; 13.B.157.239; 13.B.157.154; 13.B.157.157; 13.B.157.166;
13.B.157.169; 13.B.157.172; 13.B.157.175; 13.B.157.240; 13.B.157.244;
13.B.166.228; 13.B.166.229; 13.B.166.230; 13.B.166.231; 13.B.166.236;
13.B.166.237; 13.B.166.238; 13.B.166.239; 13.B.166.154; 13.B.166.157;
13.B.166.166; 13.B.166.169; 13.B.166.172; 13.B.166.175; 13.B.166.240;
13.B.166.244; 13.B.169.228; 13.B.169.229; 13.B.169.230; 13.B.169.231;
13.B.169.236; 13.B.169.237; 13.B.169.238; 13.B.169.239; 13.B.169.154;
13.B.169.157; 13.B.169.166; 13.B.169.169; 13.B.169.172; 13.B.169.175;
13.B.169.240; 13.B.169.244; 13.B.172.228; 13.B.172.229; 13.B.172.230;
13.B.172.231; 13.B.172.236; 13.B.172.237; 13.B.172.238; 13.B.172.239;
13.B.172.154; 13.B.172.157; 13.B.172.166; 13.B.172.169; 13.B.172.172;
13.B.172.175; 13.B.172.240; 13.B.172.244; 13.B.175.228; 13.B.175.229;
13.B.175.230; 13.B.175.231; 13.B.175.236; 13.B.175.237; 13.B.175.238;
13.B.175.239; 13.B.175.154; 13.B.175.157; 13.B.175.166; 13.B.175.169;
13.B.175.172; 13.B.175.175; 13.B.175.240; 13.B.175.244; 13.B.240.228;
13.B.240.229; 13.B.240.230; 13.B.240.231; 13.B.240.236; 13.B.240.237;
13.B.240.238; 13.B.240.239; 13.B.240.154; 13.B.240.157; 13.B.240.166;
13.B.240.169; 13.B.240.172; 13.B.240.175; 13.B.240.240; 13.B.240.244;
13.B.244.228; 13.B.244.229; 13.B.244.230; 13.B.244.231; 13.B.244.236;
13.B.244.237; 13.B.244.238; 13.B.244.239; 13.B.244.154; 13.B.244.157;
13.B.244.166; 13.B.244.169; 13.B.244.172; 13.B.244.175; 13.B.244.240;
13.B.244.244;

Prodrugs of 13.D

13.D.228.228; 13.D.228.229; 13.D.228.230; 13.D.228.231; 13.D.228.236;
13.D.228.237; 13.D.228.238; 13.D.228.239; 13.D.228.154; 13.D.228.157;
13.D.228.166; 13.D.228.169; 13.D.228.172; 13.D.228.175; 13.D.228.240;
13.D.228.244; 13.D.229.228; 13.D.229.229; 13.D.229.230; 13.D.229.231;
13.D.229.236; 13.D.229.237; 13.D.229.238; 13.D.229.239; 13.D.229.154;
13.D.229.157; 13.D.229.166; 13.D.229.169; 13.D.229.172; 13.D.229.175;
13.D.229.240; 13.D.229.244; 13.D.230.228; 13.D.230.229; 13.D.230.230;
13.D.230.231; 13.D.230.236; 13.D.230.237; 13.D.230.238; 13.D.230.239;
13.D.230.154; 13.D.230.157; 13.D.230.166; 13.D.230.169; 13.D.230.172;
13.D.230.175; 13.D.230.240; 13.D.230.244; 13.D.231.228; 13.D.231.229;
13.D.231.230; 13.D.231.231; 13.D.231.236; 13.D.231.237; 13.D.231.238;
13.D.231.239; 13.D.231.154; 13.D.231.157; 13.D.231.166; 13.D.231.169;
13.D.231.172; 13.D.231.175; 13.D.231.240; 13.D.231.244; 13.D.236.228;
13.D.236.229; 13.D.236.230; 13.D.236.231; 13.D.236.236; 13.D.236.237;
13.D.236.238; 13.D.236.239; 13.D.236.154; 13.D.236.157; 13.D.236.166;
13.D.236.169; 13.D.236.172; 13.D.236.175; 13.D.236.240; 13.D.236.244;
13.D.237.228; 13.D.237.229; 13.D.237.230; 13.D.237.231; 13.D.237.236;
13.D.237.237; 13.D.237.238; 13.D.237.239; 13.D.237.154; 13.D.237.157;
13.D.237.166; 13.D.237.169; 13.D.237.172; 13.D.237.175; 13.D.237.240;
13.D.237.244; 13.D.238.228; 13.D.238.229; 13.D.238.230; 13.D.238.231;
13.D.238.236; 13.D.238.237; 13.D.238.238; 13.D.238.239; 13.D.238.154;

TABLE 100-continued

13.D.238.157; 13.D.238.166; 13.D.238.169; 13.D.238.172; 13.D.238.175;
13.D.238.240; 13.D.238.244; 13.D.239.228; 13.D.239.229; 13.D.239.230;
13.D.239.231; 13.D.239.236; 13.D.239.237; 13.D.239.238; 13.D.239.239;
13.D.239.154; 13.D.239.157; 13.D.239.166; 13.D.239.169; 13.D.239.172;
13.D.239.175; 13.D.239.240; 13.D.239.244; 13.D.154.228; 13.D.154.229;
13.D.154.230; 13.D.154.231; 13.D.154.236; 13.D.154.237; 13.D.154.238;
13.D.154.239; 13.D.154.154; 13.D.154.157; 13.D.154.166; 13.D.154.169;
13.D.154.172; 13.D.154.175; 13.D.154.240; 13.D.154.244; 13.D.157.228;
13.D.157.229; 13.D.157.230; 13.D.157.231; 13.D.157.236; 13.D.157.237;
13.D.157.238; 13.D.157.239; 13.D.157.154; 13.D.157.157; 13.D.157.166;
13.D.157.169; 13.D.157.172; 13.D.157.175; 13.D.157.240; 13.D.157.244;
13.D.166.228; 13.D.166.229; 13.D.166.230; 13.D.166.231; 13.D.166.236;
13.D.166.237; 13.D.166.238; 13.D.166.239; 13.D.166.154; 13.D.166.157;
13.D.166.166; 13.D.166.169; 13.D.166.172; 13.D.166.175; 13.D.166.240;
13.D.166.244; 13.D.169.228; 13.D.169.229; 13.D.169.230; 13.D.169.231;
13.D.169.236; 13.D.169.237; 13.D.169.238; 13.D.169.239; 13.D.169.154;
13.D.169.157; 13.D.169.166; 13.D.169.169; 13.D.169.172; 13.D.169.175;
13.D.169.240; 13.D.169.244; 13.D.172.228; 13.D.172.229; 13.D.172.230;
13.D.172.231; 13.D.172.236; 13.D.172.237; 13.D.172.238; 13.D.172.239;
13.D.172.154; 13.D.172.157; 13.D.172.166; 13.D.172.169; 13.D.172.172;
13.D.172.175; 13.D.172.240; 13.D.172.244; 13.D.175.228; 13.D.175.229;
13.D.175.230; 13.D.175.231; 13.D.175.236; 13.D.175.237; 13.D.175.238;
13.D.175.239; 13.D.175.154; 13.D.175.157; 13.D.175.166; 13.D.175.169;
13.D.175.172; 13.D.175.175; 13.D.175.240; 13.D.175.244; 13.D.240.228;
13.D.240.229; 13.D.240.230; 13.D.240.231; 13.D.240.236; 13.D.240.237;
13.D.240.238; 13.D.240.239; 13.D.240.154; 13.D.240.157; 13.D.240.166;
13.D.240.169; 13.D.240.172; 13.D.240.175; 13.D.240.240; 13.D.240.244;
13.D.244.228; 13.D.244.229; 13.D.244.230; 13.D.244.231; 13.D.244.236;
13.D.244.237; 13.D.244.238; 13.D.244.239; 13.D.244.154; 13.D.244.157;
13.D.244.166; 13.D.244.169; 13.D.244.172; 13.D.244.175; 13.D.244.240;
13.D.244.244;
Prodrugs of 13.E 13.E.228.228; 13.E.228.229; 13.E.228.230; 13.E.228.231; 13.E.228.236;
13.E.228.237; 13.E.228.238; 13.E.228.239; 13.E.228.154; 13.E.228.157;
13.E.228.166; 13.E.228.169; 13.E.228.172; 13.E.228.175; 13.E.228.240;
13.E.228.244; 13.E.229.228; 13.E.229.229; 13.E.229.230; 13.E.229.231;
13.E.229.236; 13.E.229.237; 13.E.229.238; 13.E.229.239; 13.E.229.154;
13.E.229.157; 13.E.229.166; 13.E.229.169; 13.E.229.172; 13.E.229.175;
13.E.229.240; 13.E.229.244; 13.E.230.228; 13.E.230.229; 13.E.230.230;
13.E.230.231; 13.E.230.236; 13.E.230.237; 13.E.230.238; 13.E.230.239;
13.E.230.154; 13.E.230.157; 13.E.230.166; 13.E.230.169; 13.E.230.172;
13.E.230.175; 13.E.230.240; 13.E.230.244; 13.E.231.228; 13.E.231.229;
13.E.231.230; 13.E.231.231; 13.E.231.236; 13.E.231.237; 13.E.231.238;
13.E.231.239; 13.E.231.154; 13.E.231.157; 13.E.231.166; 13.E.231.169;
13.E.231.172; 13.E.231.175; 13.E.231.240; 13.E.231.244; 13.E.236.228;
13.E.236.229; 13.E.236.230; 13.E.236.231; 13.E.236.236; 13.E.236.237;
13.E.236.238; 13.E.236.239; 13.E.236.154; 13.E.236.157; 13.E.236.166;
13.E.236.169; 13.E.236.172; 13.E.236.175; 13.E.236.240; 13.E.236.244;
13.E.237.228; 13.E.237.229; 13.E.237.230; 13.E.237.231; 13.E.237.236;
13.E.237.237; 13.E.237.238; 13.E.237.239; 13.E.237.154; 13.E.237.157;
13.E.237.166; 13.E.237.169; 13.E.237.172; 13.E.237.175; 13.E.237.240;
13.E.237.244; 13.E.238.228; 13.E.238.229; 13.E.238.230; 13.E.238.231;
13.E.238.236; 13.E.238.237; 13.E.238.238; 13.E.238.239; 13.E.238.154;
13.E.238.157; 13.E.238.166; 13.E.238.169; 13.E.238.172; 13.E.238.175;
13.E.238.240; 13.E.238.244; 13.E.239.228; 13.E.239.229; 13.E.239.230;
13.E.239.231; 13.E.239.236; 13.E.239.237; 13.E.239.238; 13.E.239.239;
13.E.239.154; 13.E.239.157; 13.E.239.166; 13.E.239.169; 13.E.239.172;
13.E.239.175; 13.E.239.240; 13.E.239.244; 13.E.154.228; 13.E.154.229;
13.E.154.230; 13.E.154.231; 13.E.154.236; 13.E.154.237; 13.E.154.238;
13.E.154.239; 13.E.154.154; 13.E.154.157; 13.E.154.166; 13.E.154.169;
13.E.154.172; 13.E.154.175; 13.E.154.240; 13.E.154.244; 13.E.157.228;
13.E.157.229; 13.E.157.230; 13.E.157.231; 13.E.157.236; 13.E.157.237;
13.E.157.238; 13.E.157.239; 13.E.157.154; 13.E.157.157; 13.E.157.166;
13.E.157.169; 13.E.157.172; 13.E.157.175; 13.E.157.240; 13.E.157.244;
13.E.166.228; 13.E.166.229; 13.E.166.230; 13.E.166.231; 13.E.166.236;
13.E.166.237; 13.E.166.238; 13.E.166.239; 13.E.166.154; 13.E.166.157;
13.E.166.166; 13.E.166.169; 13.E.166.172; 13.E.166.175; 13.E.166.240;
13.E.166.244; 13.E.169.228; 13.E.169.229; 13.E.169.230; 13.E.169.231;
13.E.169.236; 13.E.169.237; 13.E.169.238; 13.E.169.239; 13.E.169.154;
13.E.169.157; 13.E.169.166; 13.E.169.169; 13.E.169.172; 13.E.169.175;
13.E.169.240; 13.E.169.244; 13.E.172.228; 13.E.172.229; 13.E.172.230;
13.E.172.231; 13.E.172.236; 13.E.172.237; 13.E.172.238; 13.E.172.239;
13.E.172.154; 13.E.172.157; 13.E.172.166; 13.E.172.169; 13.E.172.172;
13.E.172.175; 13.E.172.240; 13.E.172.244; 13.E.175.228; 13.E.175.229;
13.E.175.230; 13.E.175.231; 13.E.175.236; 13.E.175.237; 13.E.175.238;
13.E.175.239; 13.E.175.154; 13.E.175.157; 13.E.175.166; 13.E.175.169;

TABLE 100-continued

13.E.175.172; 13.E.175.175; 13.E.175.240; 13.E.175.244; 13.E.240.228;
13.E.240.229; 13.E.240.230; 13.E.240.231; 13.E.240.236; 13.E.240.237;
13.E.240.238; 13.E.240.239; 13.E.240.154; 13.E.240.157; 13.E.240.166;
13.E.240.169; 13.E.240.172; 13.E.240.175; 13.E.240.240; 13.E.240.244;
13.E.244.228; 13.E.244.229; 13.E.244.230; 13.E.244.231; 13.E.244.236;
13.E.244.237; 13.E.244.238; 13.E.244.239; 13.E.244.154; 13.E.244.157;
13.E.244.166; 13.E.244.169; 13.E.244.172; 13.E.244.175; 13.E.244.240;
13.E.244.244;

Prodrugs of 13.G

13.G.228.228; 13.G.228.229; 13.G.228.230; 13.G.228.231; 13.G.228.236;
13.G.228.237; 13.G.228.238; 13.G.228.239; 13.G.228.154; 13.G.228.157;
13.G.228.166; 13.G.228.169; 13.G.228.172; 13.G.228.175; 13.G.228.240;
13.G.228.244; 13.G.229.228; 13.G.229.229; 13.G.229.230; 13.G.229.231;
13.G.229.236; 13.G.229.237; 13.G.229.238; 13.G.229.239; 13.G.229.154;
13.G.229.157; 13.G.229.166; 13.G.229.169; 13.G.229.172; 13.G.229.175;
13.G.229.240; 13.G.229.244; 13.G.230.228; 13.G.230.229; 13.G.230.230;
13.G.230.231; 13.G.230.236; 13.G.230.237; 13.G.230.238; 13.G.230.239;
13.G.230.154; 13.G.230.157; 13.G.230.166; 13.G.230.169; 13.G.230.172;
13.G.230.175; 13.G.230.240; 13.G.230.244; 13.G.231.228; 13.G.231.229;
13.G.231.230; 13.G.231.231; 13.G.231.236; 13.G.231.237; 13.G.231.238;
13.G.231.239; 13.G.231.154; 13.G.231.157; 13.G.231.166; 13.G.231.169;
13.G.231.172; 13.G.231.175; 13.G.231.240; 13.G.231.244; 13.G.236.228;
13.G.236.229; 13.G.236.230; 13.G.236.231; 13.G.236.236; 13.G.236.237;
13.G.236.238; 13.G.236.239; 13.G.236.154; 13.G.236.157; 13.G.236.166;
13.G.236.169; 13.G.236.172; 13.G.236.175; 13.G.236.240; 13.G.236.244;
13.G.237.228; 13.G.237.229; 13.G.237.230; 13.G.237.231; 13.G.237.236;
13.G.237.237; 13.G.237.238; 13.G.237.239; 13.G.237.154; 13.G.237.157;
13.G.237.166; 13.G.237.169; 13.G.237.172; 13.G.237.175; 13.G.237.240;
13.G.237.244; 13.G.238.228; 13.G.238.229; 13.G.238.230; 13.G.238.231;
13.G.238.236; 13.G.238.237; 13.G.238.238; 13.G.238.239; 13.G.238.154;
13.G.238.157; 13.G.238.166; 13.G.238.169; 13.G.238.172; 13.G.238.175;
13.G.238.240; 13.G.238.244; 13.G.239.228; 13.G.239.229; 13.G.239.230;
13.G.239.231; 13.G.239.236; 13.G.239.237; 13.G.239.238; 13.G.239.239;
13.G.239.154; 13.G.239.157; 13.G.239.166; 13.G.239.169; 13.G.239.172;
13.G.239.175; 13.G.239.240; 13.G.239.244; 13.G.154.228; 13.G.154.229;
13.G.154.230; 13.G.154.231; 13.G.154.236; 13.G.154.237; 13.G.154.238;
13.G.154.239; 13.G.154.154; 13.G.154.157; 13.G.154.166; 13.G.154.169;
13.G.154.172; 13.G.154.175; 13.G.154.240; 13.G.154.244; 13.G.157.228;
13.G.157.229; 13.G.157.230; 13.G.157.231; 13.G.157.236; 13.G.157.237;
13.G.157.238; 13.G.157.239; 13.G.157.154; 13.G.157.157; 13.G.157.166;
13.G.157.169; 13.G.157.172; 13.G.157.175; 13.G.157.240; 13.G.157.244;
13.G.166.228; 13.G.166.229; 13.G.166.230; 13.G.166.231; 13.G.166.236;
13.G.166.237; 13.G.166.238; 13.G.166.239; 13.G.166.154; 13.G.166.157;
13.G.166.166; 13.G.166.169; 13.G.166.172; 13.G.166.175; 13.G.166.240;
13.G.166.244; 13.G.169.228; 13.G.169.229; 13.G.169.230; 13.G.169.231;
13.G.169.236; 13.G.169.237; 13.G.169.238; 13.G.169.239; 13.G.169.154;
13.G.169.157; 13.G.169.166; 13.G.169.169; 13.G.169.172; 13.G.169.175;
13.G.169.240; 13.G.169.244; 13.G.172.228; 13.G.172.229; 13.G.172.230;
13.G.172.231; 13.G.172.236; 13.G.172.237; 13.G.172.238; 13.G.172.239;
13.G.172.154; 13.G.172.157; 13.G.172.166; 13.G.172.169; 13.G.172.172;
13.G.172.175; 13.G.172.240; 13.G.172.244; 13.G.175.228; 13.G.175.229;
13.G.175.230; 13.G.175.231; 13.G.175.236; 13.G.175.237; 13.G.175.238;
13.G.175.239; 13.G.175.154; 13.G.175.157; 13.G.175.166; 13.G.175.169;
13.G.175.172; 13.G.175.175; 13.G.175.240; 13.G.175.244; 13.G.240.228;
13.G.240.229; 13.G.240.230; 13.G.240.231; 13.G.240.236; 13.G.240.237;
13.G.240.238; 13.G.240.239; 13.G.240.154; 13.G.240.157; 13.G.240.166;
13.G.240.169; 13.G.240.172; 13.G.240.175; 13.G.240.240; 13.G.240.244;
13.G.244.228; 13.G.244.229; 13.G.244.230; 13.G.244.231; 13.G.244.236;
13.G.244.237; 13.G.244.238; 13.G.244.239; 13.G.244.154; 13.G.244.157;
13.G.244.166; 13.G.244.169; 13.G.244.172; 13.G.244.175; 13.G.244.240;
13.G.244.244;

Prodrugs of 13.I

13.I.228.228; 13.I.228.229; 13.I.228.230; 13.I.228.231; 13.I.228.236;
13.I.228.237; 13.I.228.238; 13.I.228.239; 13.I.228.154; 13.I.228.157;
13.I.228.166; 13.I.228.169; 13.I.228.172; 13.I.228.175; 13.I.228.240;
13.I.228.244; 13.I.229.228; 13.I.229.229; 13.I.229.230; 13.I.229.231;
13.I.229.236; 13.I.229.237; 13.I.229.238; 13.I.229.239; 13.I.229.154;
13.I.229.157; 13.I.229.166; 13.I.229.169; 13.I.229.172; 13.I.229.175;
13.I.229.240; 13.I.229.244; 13.I.230.228; 13.I.230.229; 13.I.230.230;
13.I.230.231; 13.I.230.236; 13.I.230.237; 13.I.230.238; 13.I.230.239;
13.I.230.154; 13.I.230.157; 13.I.230.166; 13.I.230.169; 13.I.230.172;
13.I.230.175; 13.I.230.240; 13.I.230.244; 13.I.231.228; 13.I.231.229;
13.I.231.230; 13.I.231.231; 13.I.231.236; 13.I.231.237; 13.I.231.238;
13.I.231.239; 13.I.231.154; 13.I.231.157; 13.I.231.166; 13.I.231.169;
13.I.231.172; 13.I.231.175; 13.I.231.240; 13.I.231.244; 13.I.236.228;

TABLE 100-continued

13.I.236.229; 13.I.236.230; 13.I.236.231; 13.I.236.236; 13.I.236.237;
13.I.236.238; 13.I.236.239; 13.I.236.154; 13.I.236.157; 13.I.236.166;
13.I.236.169; 13.I.236.172; 13.I.236.175; 13.I.236.240; 13.I.236.244;
13.I.237.228; 13.I.237.229; 13.I.237.230; 13.I.237.231; 13.I.237.236;
13.I.237.237; 13.I.237.238; 13.I.237.239; 13.I.237.154; 13.I.237.157;
13.I.237.166; 13.I.237.169; 13.I.237.172; 13.I.237.175; 13.I.237.240;
13.I.237.244; 13.I.238.228; 13.I.238.229; 13.I.238.230; 13.I.238.231;
13.I.238.236; 13.I.238.237; 13.I.238.238; 13.I.238.239; 13.I.238.154;
13.I.238.157; 13.I.238.166; 13.I.238.169; 13.I.238.172; 13.I.238.175;
13.I.238.240; 13.I.238.244; 13.I.239.228; 13.I.239.229; 13.I.239.230;
13.I.239.231; 13.I.239.236; 13.I.239.237; 13.I.239.238; 13.I.239.239;
13.I.239.154; 13.I.239.157; 13.I.239.166; 13.I.239.169; 13.I.239.172;
13.I.239.175; 13.I.239.240; 13.I.239.244; 13.I.154.228; 13.I.154.229;
13.I.154.230; 13.I.154.231; 13.I.154.236; 13.I.154.237; 13.I.154.238;
13.I.154.239; 13.I.154.154; 13.I.154.157; 13.I.154.166; 13.I.154.169;
13.I.154.172; 13.I.154.175; 13.I.154.240; 13.I.154.244; 13.I.157.228;
13.I.157.229; 13.I.157.230; 13.I.157.231; 13.I.157.236; 13.I.157.237;
13.I.157.238; 13.I.157.239; 13.I.157.154; 13.I.157.157; 13.I.157.166;
13.I.157.169; 13.I.157.172; 13.I.157.175; 13.I.157.240; 13.I.157.244;
13.I.166.228; 13.I.166.229; 13.I.166.230; 13.I.166.231; 13.I.166.236;
13.I.166.237; 13.I.166.238; 13.I.166.239; 13.I.166.154; 13.I.166.157;
13.I.166.166; 13.I.166.169; 13.I.166.172; 13.I.166.175; 13.I.166.240;
13.I.166.244; 13.I.169.228; 13.I.169.229; 13.I.169.230; 13.I.169.231;
13.I.169.236; 13.I.169.237; 13.I.169.238; 13.I.169.239; 13.I.169.154;
13.I.169.157; 13.I.169.166; 13.I.169.169; 13.I.169.172; 13.I.169.175;
13.I.169.240; 13.I.169.244; 13.I.172.228; 13.I.172.229; 13.I.172.230;
13.I.172.231; 13.I.172.236; 13.I.172.237; 13.I.172.238; 13.I.172.239;
13.I.172.154; 13.I.172.157; 13.I.172.166; 13.I.172.169; 13.I.172.172;
13.I.172.175; 13.I.172.240; 13.I.172.244; 13.I.175.228; 13.I.175.229;
13.I.175.230; 13.I.175.231; 13.I.175.236; 13.I.175.237; 13.I.175.238;
13.I.175.239; 13.I.175.154; 13.I.175.157; 13.I.175.166; 13.I.175.169;
13.I.175.172; 13.I.175.175; 13.I.175.240; 13.I.175.244; 13.I.240.228;
13.I.240.229; 13.I.240.230; 13.I.240.231; 13.I.240.236; 13.I.240.237;
13.I.240.238; 13.I.240.239; 13.I.240.154; 13.I.240.157; 13.I.240.166;
13.I.240.169; 13.I.240.172; 13.I.240.175; 13.I.240.240; 13.I.240.244;
13.I.244.228; 13.I.244.229; 13.I.244.230; 13.I.244.231; 13.I.244.236;
13.I.244.237; 13.I.244.238; 13.I.244.239; 13.I.244.154; 13.I.244.157;
13.I.244.166; 13.I.244.169; 13.I.244.172; 13.I.244.175; 13.I.244.240;
13.I.244.244;
Prodrugs of 13.J 13.J.228.228; 13.J.228.229; 13.J.228.230; 13.J.228.231; 13.J.228.236;
13.J.228.237; 13.J.228.238; 13.J.228.239; 13.J.228.154; 13.J.228.157;
13.J.228.166; 13.J.228.169; 13.J.228.172; 13.J.228.175; 13.J.228.240;
13.J.228.244; 13.J.229.228; 13.J.229.229; 13.J.229.230; 13.J.229.231;
13.J.229.236; 13.J.229.237; 13.J.229.238; 13.J.229.239; 13.J.229.154;
13.J.229.157; 13.J.229.166; 13.J.229.169; 13.J.229.172; 13.J.229.175;
13.J.229.240; 13.J.229.244; 13.J.230.228; 13.J.230.229; 13.J.230.230;
13.J.230.231; 13.J.230.236; 13.J.230.237; 13.J.230.238; 13.J.230.239;
13.J.230.154; 13.J.230.157; 13.J.230.166; 13.J.230.169; 13.J.230.172;
13.J.230.175; 13.J.230.240; 13.J.230.244; 13.J.231.228; 13.J.231.229;
13.J.231.230; 13.J.231.231; 13.J.231.236; 13.J.231.237; 13.J.231.238;
13.J.231.239; 13.J.231.154; 13.J.231.157; 13.J.231.166; 13.J.231.169;
13.J.231.172; 13.J.231.175; 13.J.231.240; 13.J.231.244; 13.J.236.228;
13.J.236.229; 13.J.236.230; 13.J.236.231; 13.J.236.236; 13.J.236.237;
13.J.236.238; 13.J.236.239; 13.J.236.154; 13.J.236.157; 13.J.236.166;
13.J.236.169; 13.J.236.172; 13.J.236.175; 13.J.236.240; 13.J.236.244;
13.J.237.228; 13.J.237.229; 13.J.237.230; 13.J.237.231; 13.J.237.236;
13.J.237.237; 13.J.237.238; 13.J.237.239; 13.J.237.154; 13.J.237.157;
13.J.237.166; 13.J.237.169; 13.J.237.172; 13.J.237.175; 13.J.237.240;
13.J.237.244; 13.J.238.228; 13.J.238.229; 13.J.238.230; 13.J.238.231;
13.J.238.236; 13.J.238.237; 13.J.238.238; 13.J.238.239; 13.J.238.154;
13.J.238.157; 13.J.238.166; 13.J.238.169; 13.J.238.172; 13.J.238.175;
13.J.238.240; 13.J.238.244; 13.J.239.228; 13.J.239.229; 13.J.239.230;
13.J.239.231; 13.J.239.236; 13.J.239.237; 13.J.239.238; 13.J.239.239;
13.J.239.154; 13.J.239.157; 13.J.239.166; 13.J.239.169; 13.J.239.172;
13.J.239.175; 13.J.239.240; 13.J.239.244; 13.J.154.228; 13.J.154.229;
13.J.154.230; 13.J.154.231; 13.J.154.236; 13.J.154.237; 13.J.154.238;
13.J.154.239; 13.J.154.154; 13.J.154.157; 13.J.154.166; 13.J.154.169;
13.J.154.172; 13.J.154.175; 13.J.154.240; 13.J.154.244; 13.J.157.228;
13.J.157.229; 13.J.157.230; 13.J.157.231; 13.J.157.236; 13.J.157.237;
13.J.157.238; 13.J.157.239; 13.J.157.154; 13.J.157.157; 13.J.157.166;
13.J.157.169; 13.J.157.172; 13.J.157.175; 13.J.157.240; 13.J.157.244;
13.J.166.228; 13.J.166.229; 13.J.166.230; 13.J.166.231; 13.J.166.236;
13.J.166.237; 13.J.166.238; 13.J.166.239; 13.J.166.154; 13.J.166.157;
13.J.166.166; 13.J.166.169; 13.J.166.172; 13.J.166.175; 13.J.166.240;
13.J.166.244; 13.J.169.228; 13.J.169.229; 13.J.169.230; 13.J.169.231;

TABLE 100-continued

13.J.169.236; 13.J.169.237; 13.J.169.238; 13.J.169.239; 13.J.169.154;
13.J.169.157; 13.J.169.166; 13.J.169.169; 13.J.169.172; 13.J.169.175;
13.J.169.240; 13.J.169.244; 13.J.172.228; 13.J.172.229; 13.J.172.230;
13.J.172.231; 13.J.172.236; 13.J.172.237; 13.J.172.238; 13.J.172.239;
13.J.172.154; 13.J.172.157; 13.J.172.166; 13.J.172.169; 13.J.172.172;
13.J.172.175; 13.J.172.240; 13.J.172.244; 13.J.175.228; 13.J.175.229;
13.J.175.230; 13.J.175.231; 13.J.175.236; 13.J.175.237; 13.J.175.238;
13.J.175.239; 13.J.175.154; 13.J.175.157; 13.J.175.166; 13.J.175.169;
13.J.175.172; 13.J.175.175; 13.J.175.240; 13.J.175.244; 13.J.240.228;
13.J.240.229; 13.J.240.230; 13.J.240.231; 13.J.240.236; 13.J.240.237;
13.J.240.238; 13.J.240.239; 13.J.240.154; 13.J.240.157; 13.J.240.166;
13.J.240.169; 13.J.240.172; 13.J.240.175; 13.J.240.240; 13.J.240.244;
13.J.244.228; 13.J.244.229; 13.J.244.230; 13.J.244.231; 13.J.244.236;
13.J.244.237; 13.J.244.238; 13.J.244.239; 13.J.244.154; 13.J.244.157;
13.J.244.166; 13.J.244.169; 13.J.244.172; 13.J.244.175; 13.J.244.240;
13.J.244.244;
Prodrugs of 13.L 13.L.228.228; 13.L.228.229; 13.L.228.230; 13.L.228.231; 13.L.228.236;
13.L.228.237; 13.L.228.238; 13.L.228.239; 13.L.228.154; 13.L.228.157;
13.L.228.166; 13.L.228.169; 13.L.228.172; 13.L.228.175; 13.L.228.240;
13.L.228.244; 13.L.229.228; 13.L.229.229; 13.L.229.230; 13.L.229.231;
13.L.229.236; 13.L.229.237; 13.L.229.238; 13.L.229.239; 13.L.229.154;
13.L.229.157; 13.L.229.166; 13.L.229.169; 13.L.229.172; 13.L.229.175;
13.L.229.240; 13.L.229.244; 13.L.230.228; 13.L.230.229; 13.L.230.230;
13.L.230.231; 13.L.230.236; 13.L.230.237; 13.L.230.238; 13.L.230.239;
13.L.230.154; 13.L.230.157; 13.L.230.166; 13.L.230.169; 13.L.230.172;
13.L.230.175; 13.L.230.240; 13.L.230.244; 13.L.231.228; 13.L.231.229;
13.L.231.230; 13.L.231.231; 13.L.231.236; 13.L.231.237; 13.L.231.238;
13.L.231.239; 13.L.231.154; 13.L.231.157; 13.L.231.166; 13.L.231.169;
13.L.231.172; 13.L.231.175; 13.L.231.240; 13.L.231.244; 13.L.236.228;
13.L.236.229; 13.L.236.230; 13.L.236.231; 13.L.236.236; 13.L.236.237;
13.L.236.238; 13.L.236.239; 13.L.236.154; 13.L.236.157; 13.L.236.166;
13.L.236.169; 13.L.236.172; 13.L.236.175; 13.L.236.240; 13.L.236.244;
13.L.237.228; 13.L.237.229; 13.L.237.230; 13.L.237.231; 13.L.237.236;
13.L.237.237; 13.L.237.238; 13.L.237.239; 13.L.237.154; 13.L.237.157;
13.L.237.166; 13.L.237.169; 13.L.237.172; 13.L.237.175; 13.L.237.240;
13.L.237.244; 13.L.238.228; 13.L.238.229; 13.L.238.230; 13.L.238.231;
13.L.238.236; 13.L.238.237; 13.L.238.238; 13.L.238.239; 13.L.238.154;
13.L.238.157; 13.L.238.166; 13.L.238.169; 13.L.238.172; 13.L.238.175;
13.L.238.240; 13.L.238.244; 13.L.239.228; 13.L.239.229; 13.L.239.230;
13.L.239.231; 13.L.239.236; 13.L.239.237; 13.L.239.238; 13.L.239.239;
13.L.239.154; 13.L.239.157; 13.L.239.166; 13.L.239.169; 13.L.239.172;
13.L.239.175; 13.L.239.240; 13.L.239.244; 13.L.154.228; 13.L.154.229;
13.L.154.230; 13.L.154.231; 13.L.154.236; 13.L.154.237; 13.L.154.238;
13.L.154.239; 13.L.154.154; 13.L.154.157; 13.L.154.166; 13.L.154.169;
13.L.154.172; 13.L.154.175; 13.L.154.240; 13.L.154.244; 13.L.157.228;
13.L.157.229; 13.L.157.230; 13.L.157.231; 13.L.157.236; 13.L.157.237;
13.L.157.238; 13.L.157.239; 13.L.157.154; 13.L.157.157; 13.L.157.166;
13.L.157.169; 13.L.157.172; 13.L.157.175; 13.L.157.240; 13.L.157.244;
13.L.166.228; 13.L.166.229; 13.L.166.230; 13.L.166.231; 13.L.166.236;
13.L.166.237; 13.L.166.238; 13.L.166.239; 13.L.166.154; 13.L.166.157;
13.L.166.166; 13.L.166.169; 13.L.166.172; 13.L.166.175; 13.L.166.240;
13.L.166.244; 13.L.169.228; 13.L.169.229; 13.L.169.230; 13.L.169.231;
13.L.169.236; 13.L.169.237; 13.L.169.238; 13.L.169.239; 13.L.169.154;
13.L.169.157; 13.L.169.166; 13.L.169.169; 13.L.169.172; 13.L.169.175;
13.L.169.240; 13.L.169.244; 13.L.172.228; 13.L.172.229; 13.L.172.230;
13.L.172.231; 13.L.172.236; 13.L.172.237; 13.L.172.238; 13.L.172.239;
13.L.172.154; 13.L.172.157; 13.L.172.166; 13.L.172.169; 13.L.172.172;
13.L.172.175; 13.L.172.240; 13.L.172.244; 13.L.175.228; 13.L.175.229;
13.L.175.230; 13.L.175.231; 13.L.175.236; 13.L.175.237; 13.L.175.238;
13.L.175.239; 13.L.175.154; 13.L.175.157; 13.L.175.166; 13.L.175.169;
13.L.175.172; 13.L.175.175; 13.L.175.240; 13.L.175.244; 13.L.240.228;
13.L.240.229; 13.L.240.230; 13.L.240.231; 13.L.240.236; 13.L.240.237;
13.L.240.238; 13.L.240.239; 13.L.240.154; 13.L.240.157; 13.L.240.166;
13.L.240.169; 13.L.240.172; 13.L.240.175; 13.L.240.240; 13.L.240.244;
13.L.244.228; 13.L.244.229; 13.L.244.230; 13.L.244.231; 13.L.244.236;
13.L.244.237; 13.L.244.238; 13.L.244.239; 13.L.244.154; 13.L.244.157;
13.L.244.166; 13.L.244.169; 13.L.244.172; 13.L.244.175; 13.L.244.240;
13.L.244.244;
Prodrugs of 13.O 13.O.228.228; 13.O.228.229; 13.O.228.230; 13.O.228.231; 13.O.228.236;
13.O.228.237; 13.O.228.238; 13.O.228.239; 13.O.228.154; 13.O.228.157;
13.O.228.166; 13.O.228.169; 13.O.228.172; 13.O.228.175; 13.O.228.240;
13.O.228.244; 13.O.229.228; 13.O.229.229; 13.O.229.230; 13.O.229.231;
13.O.229.236; 13.O.229.237; 13.O.229.238; 13.O.229.239; 13.O.229.154;

TABLE 100-continued

13.O.229.157; 13.O.229.166; 13.O.229.169; 13.O.229.172; 13.O.229.175;
13.O.229.240; 13.O.229.244; 13.O.230.228; 13.O.230.229; 13.O.230.230;
13.O.230.231; 13.O.230.236; 13.O.230.237; 13.O.230.238; 13.O.230.239;
13.O.230.154; 13.O.230.157; 13.O.230.166; 13.O.230.169; 13.O.230.172;
13.O.230.175; 13.O.230.240; 13.O.230.244; 13.O.231.228; 13.O.231.229;
13.O.231.230; 13.O.231.231; 13.O.231.236; 13.O.231.237; 13.O.231.238;
13.O.231.239; 13.O.231.154; 13.O.231.157; 13.O.231.166; 13.O.231.169;
13.O.231.172; 13.O.231.175; 13.O.231.240; 13.O.231.244; 13.O.236.228;
13.O.236.229; 13.O.236.230; 13.O.236.231; 13.O.236.236; 13.O.236.237;
13.O.236.238; 13.O.236.239; 13.O.236.154; 13.O.236.157; 13.O.236.166;
13.O.236.169; 13.O.236.172; 13.O.236.175; 13.O.236.240; 13.O.236.244;
13.O.237.228; 13.O.237.229; 13.O.237.230; 13.O.237.231; 13.O.237.236;
13.O.237.237; 13.O.237.238; 13.O.237.239; 13.O.237.154; 13.O.237.157;
13.O.237.166; 13.O.237.169; 13.O.237.172; 13.O.237.175; 13.O.237.240;
13.O.237.244; 13.O.238.228; 13.O.238.229; 13.O.238.230; 13.O.238.231;
13.O.238.236; 13.O.238.237; 13.O.238.238; 13.O.238.239; 13.O.238.154;
13.O.238.157; 13.O.238.166; 13.O.238.169; 13.O.238.172; 13.O.238.175;
13.O.238.240; 13.O.238.244; 13.O.239.228; 13.O.239.229; 13.O.239.230;
13.O.239.231; 13.O.239.236; 13.O.239.237; 13.O.239.238; 13.O.239.239;
13.O.239.154; 13.O.239.157; 13.O.239.166; 13.O.239.169; 13.O.239.172;
13.O.239.175; 13.O.239.240; 13.O.239.244; 13.O.154.228; 13.O.154.229;
13.O.154.230; 13.O.154.231; 13.O.154.236; 13.O.154.237; 13.O.154.238;
13.O.154.239; 13.O.154.154; 13.O.154.157; 13.O.154.166; 13.O.154.169;
13.O.154.172; 13.O.154.175; 13.O.154.240; 13.O.154.244; 13.O.157.228;
13.O.157.229; 13.O.157.230; 13.O.157.231; 13.O.157.236; 13.O.157.237;
13.O.157.238; 13.O.157.239; 13.O.157.154; 13.O.157.157; 13.O.157.166;
13.O.157.169; 13.O.157.172; 13.O.157.175; 13.O.157.240; 13.O.157.244;
13.O.166.228; 13.O.166.229; 13.O.166.230; 13.O.166.231; 13.O.166.236;
13.O.166.237; 13.O.166.238; 13.O.166.239; 13.O.166.154; 13.O.166.157;
13.O.166.166; 13.O.166.169; 13.O.166.172; 13.O.166.175; 13.O.166.240;
13.O.166.244; 13.O.169.228; 13.O.169.229; 13.O.169.230; 13.O.169.231;
13.O.169.236; 13.O.169.237; 13.O.169.238; 13.O.169.239; 13.O.169.154;
13.O.169.157; 13.O.169.166; 13.O.169.169; 13.O.169.172; 13.O.169.175;
13.O.169.240; 13.O.169.244; 13.O.172.228; 13.O.172.229; 13.O.172.230;
13.O.172.231; 13.O.172.236; 13.O.172.237; 13.O.172.238; 13.O.172.239;
13.O.172.154; 13.O.172.157; 13.O.172.166; 13.O.172.169; 13.O.172.172;
13.O.172.175; 13.O.172.240; 13.O.172.244; 13.O.175.228; 13.O.175.229;
13.O.175.230; 13.O.175.231; 13.O.175.236; 13.O.175.237; 13.O.175.238;
13.O.175.239; 13.O.175.154; 13.O.175.157; 13.O.175.166; 13.O.175.169;
13.O.175.172; 13.O.175.175; 13.O.175.240; 13.O.175.244; 13.O.240.228;
13.O.240.229; 13.O.240.230; 13.O.240.231; 13.O.240.236; 13.O.240.237;
13.O.240.238; 13.O.240.239; 13.O.240.154; 13.O.240.157; 13.O.240.166;
13.O.240.169; 13.O.240.172; 13.O.240.175; 13.O.240.240; 13.O.240.244;
13.O.244.228; 13.O.244.229; 13.O.244.230; 13.O.244.231; 13.O.244.236;
13.O.244.237; 13.O.244.238; 13.O.244.239; 13.O.244.154; 13.O.244.157;
13.O.244.166; 13.O.244.169; 13.O.244.172; 13.O.244.175; 13.O.244.240;
13.O.244.244;
Prodrugs of 13.P 13.P.228.228; 13.P.228.229; 13.P.228.230; 13.P.228.231; 13.P.228.236;
13.P.228.237; 13.P.228.238; 13.P.228.239; 13.P.228.154; 13.P.228.157;
13.P.228.166; 13.P.228.169; 13.P.228.172; 13.P.228.175; 13.P.228.240;
13.P.228.244; 13.P.229.228; 13.P.229.229; 13.P.229.230; 13.P.229.231;
13.P.229.236; 13.P.229.237; 13.P.229.238; 13.P.229.239; 13.P.229.154;
13.P.229.157; 13.P.229.166; 13.P.229.169; 13.P.229.172; 13.P.229.175;
13.P.229.240; 13.P.229.244; 13.P.230.228; 13.P.230.229; 13.P.230.230;
13.P.230.231; 13.P.230.236; 13.P.230.237; 13.P.230.238; 13.P.230.239;
13.P.230.154; 13.P.230.157; 13.P.230.166; 13.P.230.169; 13.P.230.172;
13.P.230.175; 13.P.230.240; 13.P.230.244; 13.P.231.228; 13.P.231.229;
13.P.231.230; 13.P.231.231; 13.P.231.236; 13.P.231.237; 13.P.231.238;
13.P.231.239; 13.P.231.154; 13.P.231.157; 13.P.231.166; 13.P.231.169;
13.P.231.172; 13.P.231.175; 13.P.231.240; 13.P.231.244; 13.P.236.228;
13.P.236.229; 13.P.236.230; 13.P.236.231; 13.P.236.236; 13.P.236.237;
13.P.236.238; 13.P.236.239; 13.P.236.154; 13.P.236.157; 13.P.236.166;
13.P.236.169; 13.P.236.172; 13.P.236.175; 13.P.236.240; 13.P.236.244;
13.P.237.228; 13.P.237.229; 13.P.237.230; 13.P.237.231; 13.P.237.236;
13.P.237.237; 13.P.237.238; 13.P.237.239; 13.P.237.154; 13.P.237.157;
13.P.237.166; 13.P.237.169; 13.P.237.172; 13.P.237.175; 13.P.237.240;
13.P.237.244; 13.P.238.228; 13.P.238.229; 13.P.238.230; 13.P.238.231;
13.P.238.236; 13.P.238.237; 13.P.238.238; 13.P.238.239; 13.P.238.154;
13.P.238.157; 13.P.238.166; 13.P.238.169; 13.P.238.172; 13.P.238.175;
13.P.238.240; 13.P.238.244; 13.P.239.228; 13.P.239.229; 13.P.239.230;
13.P.239.231; 13.P.239.236; 13.P.239.237; 13.P.239.238; 13.P.239.239;
13.P.239.154; 13.P.239.157; 13.P.239.166; 13.P.239.169; 13.P.239.172;
13.P.239.175; 13.P.239.240; 13.P.239.244; 13.P.154.228; 13.P.154.229;
13.P.154.230; 13.P.154.231; 13.P.154.236; 13.P.154.237; 13.P.154.238;
13.P.154.239; 13.P.154.154; 13.P.154.157; 13.P.154.166; 13.P.154.169;
13.P.154.172; 13.P.154.175; 13.P.154.240; 13.P.154.244; 13.P.157.228;
13.P.157.229; 13.P.157.230; 13.P.157.231; 13.P.157.236; 13.P.157.237;

TABLE 100-continued

13.P.157.238; 13.P.157.239; 13.P.157.154; 13.P.157.157; 13.P.157.166;
13.P.157.169; 13.P.157.172; 13.P.157.175; 13.P.157.240; 13.P.157.244;
13.P.166.228; 13.P.166.229; 13.P.166.230; 13.P.166.231; 13.P.166.236;
13.P.166.237; 13.P.166.238; 13.P.166.239; 13.P.166.154; 13.P.166.157;
13.P.166.166; 13.P.166.169; 13.P.166.172; 13.P.166.175; 13.P.166.240;
13.P.166.244; 13.P.169.228; 13.P.169.229; 13.P.169.230; 13.P.169.231;
13.P.169.236; 13.P.169.237; 13.P.169.238; 13.P.169.239; 13.P.169.154;
13.P.169.157; 13.P.169.166; 13.P.169.169; 13.P.169.172; 13.P.169.175;
13.P.169.240; 13.P.169.244; 13.P.172.228; 13.P.172.229; 13.P.172.230;
13.P.172.231; 13.P.172.236; 13.P.172.237; 13.P.172.238; 13.P.172.239;
13.P.172.154; 13.P.172.157; 13.P.172.166; 13.P.172.169; 13.P.172.172;
13.P.172.175; 13.P.172.240; 13.P.172.244; 13.P.175.228; 13.P.175.229;
13.P.175.230; 13.P.175.231; 13.P.175.236; 13.P.175.237; 13.P.175.238;
13.P.175.239; 13.P.175.154; 13.P.175.157; 13.P.175.166; 13.P.175.169;
13.P.175.172; 13.P.175.175; 13.P.175.240; 13.P.175.244; 13.P.240.228;
13.P.240.229; 13.P.240.230; 13.P.240.231; 13.P.240.236; 13.P.240.237;
13.P.240.238; 13.P.240.239; 13.P.240.154; 13.P.240.157; 13.P.240.166;
13.P.240.169; 13.P.240.172; 13.P.240.175; 13.P.240.240; 13.P.240.244;
13.P.244.228; 13.P.244.229; 13.P.244.230; 13.P.244.231; 13.P.244.236;
13.P.244.237; 13.P.244.238; 13.P.244.239; 13.P.244.154; 13.P.244.157;
13.P.244.166; 13.P.244.169; 13.P.244.172; 13.P.244.175; 13.P.244.240;
13.P.244.244;

Prodrugs of 13.U

13.U.228.228; 13.U.228.229; 13.U.228.230; 13.U.228.231; 13.U.228.236;
13.U.228.237; 13.U.228.238; 13.U.228.239; 13.U.228.154; 13.U.228.157;
13.U.228.166; 13.U.228.169; 13.U.228.172; 13.U.228.175; 13.U.228.240;
13.U.228.244; 13.U.229.228; 13.U.229.229; 13.U.229.230; 13.U.229.231;
13.U.229.236; 13.U.229.237; 13.U.229.238; 13.U.229.239; 13.U.229.154;
13.U.229.157; 13.U.229.166; 13.U.229.169; 13.U.229.172; 13.U.229.175;
13.U.229.240; 13.U.229.244; 13.U.230.228; 13.U.230.229; 13.U.230.230;
13.U.230.231; 13.U.230.236; 13.U.230.237; 13.U.230.238; 13.U.230.239;
13.U.230.154; 13.U.230.157; 13.U.230.166; 13.U.230.169; 13.U.230.172;
13.U.230.175; 13.U.230.240; 13.U.230.244; 13.U.231.228; 13.U.231.229;
13.U.231.230; 13.U.231.231; 13.U.231.236; 13.U.231.237; 13.U.231.238;
13.U.231.239; 13.U.231.154; 13.U.231.157; 13.U.231.166; 13.U.231.169;
13.U.231.172; 13.U.231.175; 13.U.231.240; 13.U.231.244; 13.U.236.228;
13.U.236.229; 13.U.236.230; 13.U.236.231; 13.U.236.236; 13.U.236.237;
13.U.236.238; 13.U.236.239; 13.U.236.154; 13.U.236.157; 13.U.236.166;
13.U.236.169; 13.U.236.172; 13.U.236.175; 13.U.236.240; 13.U.236.244;
13.U.237.228; 13.U.237.229; 13.U.237.230; 13.U.237.231; 13.U.237.236;
13.U.237.237; 13.U.237.238; 13.U.237.239; 13.U.237.154; 13.U.237.157;
13.U.237.166; 13.U.237.169; 13.U.237.172; 13.U.237.175; 13.U.237.240;
13.U.237.244; 13.U.238.228; 13.U.238.229; 13.U.238.230; 13.U.238.231;
13.U.238.236; 13.U.238.237; 13.U.238.238; 13.U.238.239; 13.U.238.154;
13.U.238.157; 13.U.238.166; 13.U.238.169; 13.U.238.172; 13.U.238.175;
13.U.238.240; 13.U.238.244; 13.U.239.228; 13.U.239.229; 13.U.239.230;
13.U.239.231; 13.U.239.236; 13.U.239.237; 13.U.239.238; 13.U.239.239;
13.U.239.154; 13.U.239.157; 13.U.239.166; 13.U.239.169; 13.U.239.172;
13.U.239.175; 13.U.239.240; 13.U.239.244; 13.U.154.228; 13.U.154.229;
13.U.154.230; 13.U.154.231; 13.U.154.236; 13.U.154.237; 13.U.154.238;
13.U.154.239; 13.U.154.154; 13.U.154.157; 13.U.154.166; 13.U.154.169;
13.U.154.172; 13.U.154.175; 13.U.154.240; 13.U.154.244; 13.U.157.228;
13.U.157.229; 13.U.157.230; 13.U.157.231; 13.U.157.236; 13.U.157.237;
13.U.157.238; 13.U.157.239; 13.U.157.154; 13.U.157.157; 13.U.157.166;
13.U.157.169; 13.U.157.172; 13.U.157.175; 13.U.157.240; 13.U.157.244;
13.U.166.228; 13.U.166.229; 13.U.166.230; 13.U.166.231; 13.U.166.236;
13.U.166.237; 13.U.166.238; 13.U.166.239; 13.U.166.154; 13.U.166.157;
13.U.166.166; 13.U.166.169; 13.U.166.172; 13.U.166.175; 13.U.166.240;
13.U.166.244; 13.U.169.228; 13.U.169.229; 13.U.169.230; 13.U.169.231;
13.U.169.236; 13.U.169.237; 13.U.169.238; 13.U.169.239; 13.U.169.154;
13.U.169.157; 13.U.169.166; 13.U.169.169; 13.U.169.172; 13.U.169.175;
13.U.169.240; 13.U.169.244; 13.U.172.228; 13.U.172.229; 13.U.172.230;
13.U.172.231; 13.U.172.236; 13.U.172.237; 13.U.172.238; 13.U.172.239;
13.U.172.154; 13.U.172.157; 13.U.172.166; 13.U.172.169; 13.U.172.172;
13.U.172.175; 13.U.172.240; 13.U.172.244; 13.U.175.228; 13.U.175.229;
13.U.175.230; 13.U.175.231; 13.U.175.236; 13.U.175.237; 13.U.175.238;
13.U.175.239; 13.U.175.154; 13.U.175.157; 13.U.175.166; 13.U.175.169;
13.U.175.172; 13.U.175.175; 13.U.175.240; 13.U.175.244; 13.U.240.228;
13.U.240.229; 13.U.240.230; 13.U.240.231; 13.U.240.236; 13.U.240.237;
13.U.240.238; 13.U.240.239; 13.U.240.154; 13.U.240.157; 13.U.240.166;
13.U.240.169; 13.U.240.172; 13.U.240.175; 13.U.240.240; 13.U.240.244;
13.U.244.228; 13.U.244.229; 13.U.244.230; 13.U.244.231; 13.U.244.236;
13.U.244.237; 13.U.244.238; 13.U.244.239; 13.U.244.154; 13.U.244.157;
13.U.244.166; 13.U.244.169; 13.U.244.172; 13.U.244.175; 13.U.244.240;
13.U.244.244;

Prodrugs of 13.W

13.W.228.228; 13.W.228.229; 13.W.228.230; 13.W.228.231; 13.W.228.236;

TABLE 100-continued

13.W.228.237; 13.W.228.238; 13.W.228.239; 13.W.228.154; 13.W.228.157;
13.W.228.166; 13.W.228.169; 13.W.228.172; 13.W.228.175; 13.W.228.240;
13.W.228.244; 13.W.229.228; 13.W.229.229; 13.W.229.230; 13.W.229.231;
13.W.229.236; 13.W.229.237; 13.W.229.238; 13.W.229.239; 13.W.229.154;
13.W.229.157; 13.W.229.166; 13.W.229.169; 13.W.229.172; 13.W.229.175;
13.W.229.240; 13.W.229.244; 13.W.230.228; 13.W.230.229; 13.W.230.230;
13.W.230.231; 13.W.230.236; 13.W.230.237; 13.W.230.238; 13.W.230.239;
13.W.230.154; 13.W.230.157; 13.W.230.166; 13.W.230.169; 13.W.230.172;
13.W.230.175; 13.W.230.240; 13.W.230.244; 13.W.231.228; 13.W.231.229;
13.W.231.230; 13.W.231.231; 13.W.231.236; 13.W.231.237; 13.W.231.238;
13.W.231.239; 13.W.231.154; 13.W.231.157; 13.W.231.166; 13.W.231.169;
13.W.231.172; 13.W.231.175; 13.W.231.240; 13.W.231.244; 13.W.236.228;
13.W.236.229; 13.W.236.230; 13.W.236.231; 13.W.236.236; 13.W.236.237;
13.W.236.238; 13.W.236.239; 13.W.236.154; 13.W.236.157; 13.W.236.166;
13.W.236.169; 13.W.236.172; 13.W.236.175; 13.W.236.240; 13.W.236.244;
13.W.237.228; 13.W.237.229; 13.W.237.230; 13.W.237.231; 13.W.237.236;
13.W.237.237; 13.W.237.238; 13.W.237.239; 13.W.237.154; 13.W.237.157;
13.W.237.166; 13.W.237.169; 13.W.237.172; 13.W.237.175; 13.W.237.240;
13.W.237.244; 13.W.238.228; 13.W.238.229; 13.W.238.230; 13.W.238.231;
13.W.238.236; 13.W.238.237; 13.W.238.238; 13.W.238.239; 13.W.238.154;
13.W.238.157; 13.W.238.166; 13.W.238.169; 13.W.238.172; 13.W.238.175;
13.W.238.240; 13.W.238.244; 13.W.239.228; 13.W.239.229; 13.W.239.230;
13.W.239.231; 13.W.239.236; 13.W.239.237; 13.W.239.238; 13.W.239.239;
13.W.239.154; 13.W.239.157; 13.W.239.166; 13.W.239.169; 13.W.239.172;
13.W.239.175; 13.W.239.240; 13.W.239.244; 13.W.154.228; 13.W.154.229;
13.W.154.230; 13.W.154.231; 13.W.154.236; 13.W.154.237; 13.W.154.238;
13.W.154.239; 13.W.154.154; 13.W.154.157; 13.W.154.166; 13.W.154.169;
13.W.154.172; 13.W.154.175; 13.W.154.240; 13.W.154.244; 13.W.157.228;
13.W.157.229; 13.W.157.230; 13.W.157.231; 13.W.157.236; 13.W.157.237;
13.W.157.238; 13.W.157.239; 13.W.157.154; 13.W.157.157; 13.W.157.166;
13.W.157.169; 13.W.157.172; 13.W.157.175; 13.W.157.240; 13.W.157.244;
13.W.166.228; 13.W.166.229; 13.W.166.230; 13.W.166.231; 13.W.166.236;
13.W.166.237; 13.W.166.238; 13.W.166.239; 13.W.166.154; 13.W.166.157;
13.W.166.166; 13.W.166.169; 13.W.166.172; 13.W.166.175; 13.W.166.240;
13.W.166.244; 13.W.169.228; 13.W.169.229; 13.W.169.230; 13.W.169.231;
13.W.169.236; 13.W.169.237; 13.W.169.238; 13.W.169.239; 13.W.169.154;
13.W.169.157; 13.W.169.166; 13.W.169.169; 13.W.169.172; 13.W.169.175;
13.W.169.240; 13.W.169.244; 13.W.172.228; 13.W.172.229; 13.W.172.230;
13.W.172.231; 13.W.172.236; 13.W.172.237; 13.W.172.238; 13.W.172.239;
13.W.172.154; 13.W.172.157; 13.W.172.166; 13.W.172.169; 13.W.172.172;
13.W.172.175; 13.W.172.240; 13.W.172.244; 13.W.175.228; 13.W.175.229;
13.W.175.230; 13.W.175.231; 13.W.175.236; 13.W.175.237; 13.W.175.238;
13.W.175.239; 13.W.175.154; 13.W.175.157; 13.W.175.166; 13.W.175.169;
13.W.175.172; 13.W.175.175; 13.W.175.240; 13.W.175.244; 13.W.240.228;
13.W.240.229; 13.W.240.230; 13.W.240.231; 13.W.240.236; 13.W.240.237;
13.W.240.238; 13.W.240.239; 13.W.240.154; 13.W.240.157; 13.W.240.166;
13.W.240.169; 13.W.240.172; 13.W.240.175; 13.W.240.240; 13.W.240.244;
13.W.244.228; 13.W.244.229; 13.W.244.230; 13.W.244.231; 13.W.244.236;
13.W.244.237; 13.W.244.238; 13.W.244.239; 13.W.244.154; 13.W.244.157;
13.W.244.166; 13.W.244.169; 13.W.244.172; 13.W.244.175; 13.W.244.240;
13.W.244.244;

Prodrugs of 13.Y

13.Y.228.228; 13.Y.228.229; 13.Y.228.230; 13.Y.228.231; 13.Y.228.236;
13.Y.228.237; 13.Y.228.238; 13.Y.228.239; 13.Y.228.154; 13.Y.228.157;
13.Y.228.166; 13.Y.228.169; 13.Y.228.172; 13.Y.228.175; 13.Y.228.240;
13.Y.228.244; 13.Y.229.228; 13.Y.229.229; 13.Y.229.230; 13.Y.229.231;
13.Y.229.236; 13.Y.229.237; 13.Y.229.238; 13.Y.229.239; 13.Y.229.154;
13.Y.229.157; 13.Y.229.166; 13.Y.229.169; 13.Y.229.172; 13.Y.229.175;
13.Y.229.240; 13.Y.229.244; 13.Y.230.228; 13.Y.230.229; 13.Y.230.230;
13.Y.230.231; 13.Y.230.236; 13.Y.230.237; 13.Y.230.238; 13.Y.230.239;
13.Y.230.154; 13.Y.230.157; 13.Y.230.166; 13.Y.230.169; 13.Y.230.172;
13.Y.230.175; 13.Y.230.240; 13.Y.230.244; 13.Y.231.228; 13.Y.231.229;
13.Y.231.230; 13.Y.231.231; 13.Y.231.236; 13.Y.231.237; 13.Y.231.238;
13.Y.231.239; 13.Y.231.154; 13.Y.231.157; 13.Y.231.166; 13.Y.231.169;
13.Y.231.172; 13.Y.231.175; 13.Y.231.240; 13.Y.231.244; 13.Y.236.228;
13.Y.236.229; 13.Y.236.230; 13.Y.236.231; 13.Y.236.236; 13.Y.236.237;
13.Y.236.238; 13.Y.236.239; 13.Y.236.154; 13.Y.236.157; 13.Y.236.166;
13.Y.236.169; 13.Y.236.172; 13.Y.236.175; 13.Y.236.240; 13.Y.236.244;
13.Y.237.228; 13.Y.237.229; 13.Y.237.230; 13.Y.237.231; 13.Y.237.236;
13.Y.237.237; 13.Y.237.238; 13.Y.237.239; 13.Y.237.154; 13.Y.237.157;
13.Y.237.166; 13.Y.237.169; 13.Y.237.172; 13.Y.237.175; 13.Y.237.240;
13.Y.237.244; 13.Y.238.228; 13.Y.238.229; 13.Y.238.230; 13.Y.238.231;
13.Y.238.236; 13.Y.238.237; 13.Y.238.238; 13.Y.238.239; 13.Y.238.154;
13.Y.238.157; 13.Y.238.166; 13.Y.238.169; 13.Y.238.172; 13.Y.238.175;
13.Y.238.240; 13.Y.238.244; 13.Y.239.228; 13.Y.239.229; 13.Y.239.230;
13.Y.239.231; 13.Y.239.236; 13.Y.239.237; 13.Y.239.238; 13.Y.239.239;
13.Y.239.154; 13.Y.239.157; 13.Y.239.166; 13.Y.239.169; 13.Y.239.172;
13.Y.239.175; 13.Y.239.240; 13.Y.239.244; 13.Y.154.228; 13.Y.154.229;

TABLE 100-continued

13.Y.154.230; 13.Y.154.231; 13.Y.154.236; 13.Y.154.237; 13.Y.154.238;
13.Y.154.239; 13.Y.154.154; 13.Y.154.157; 13.Y.154.166; 13.Y.154.169;
13.Y.154.172; 13.Y.154.175; 13.Y.154.240; 13.Y.154.244; 13.Y.157.228;
13.Y.157.229; 13.Y.157.230; 13.Y.157.231; 13.Y.157.236; 13.Y.157.237;
13.Y.157.238; 13.Y.157.239; 13.Y.157.154; 13.Y.157.157; 13.Y.157.166;
13.Y.157.169; 13.Y.157.172; 13.Y.157.175; 13.Y.157.240; 13.Y.157.244;
13.Y.166.228; 13.Y.166.229; 13.Y.166.230; 13.Y.166.231; 13.Y.166.236;
13.Y.166.237; 13.Y.166.238; 13.Y.166.239; 13.Y.166.154; 13.Y.166.157;
13.Y.166.166; 13.Y.166.169; 13.Y.166.172; 13.Y.166.175; 13.Y.166.240;
13.Y.166.244; 13.Y.169.228; 13.Y.169.229; 13.Y.169.230; 13.Y.169.231;
13.Y.169.236; 13.Y.169.237; 13.Y.169.238; 13.Y.169.239; 13.Y.169.154;
13.Y.169.157; 13.Y.169.166; 13.Y.169.169; 13.Y.169.172; 13.Y.169.175;
13.Y.169.240; 13.Y.169.244; 13.Y.172.228; 13.Y.172.229; 13.Y.172.230;
13.Y.172.231; 13.Y.172.236; 13.Y.172.237; 13.Y.172.238; 13.Y.172.239;
13.Y.172.154; 13.Y.172.157; 13.Y.172.166; 13.Y.172.169; 13.Y.172.172;
13.Y.172.175; 13.Y.172.240; 13.Y.172.244; 13.Y.175.228; 13.Y.175.229;
13.Y.175.230; 13.Y.175.231; 13.Y.175.236; 13.Y.175.237; 13.Y.175.238;
13.Y.175.239; 13.Y.175.154; 13.Y.175.157; 13.Y.175.166; 13.Y.175.169;
13.Y.175.172; 13.Y.175.175; 13.Y.175.240; 13.Y.175.244; 13.Y.240.228;
13.Y.240.229; 13.Y.240.230; 13.Y.240.231; 13.Y.240.236; 13.Y.240.237;
13.Y.240.238; 13.Y.240.239; 13.Y.240.154; 13.Y.240.157; 13.Y.240.166;
13.Y.240.169; 13.Y.240.172; 13.Y.240.175; 13.Y.240.240; 13.Y.240.244;
13.Y.244.228; 13.Y.244.229; 13.Y.244.230; 13.Y.244.231; 13.Y.244.236;
13.Y.244.237; 13.Y.244.238; 13.Y.244.239; 13.Y.244.154; 13.Y.244.157;
13.Y.244.166; 13.Y.244.169; 13.Y.244.172; 13.Y.244.175; 13.Y.244.240;
13.Y.244.244;
Prodrugs of 14.AH 14.AH.4.157; 14.AH.4.158; 14.AH.4.196; 14.AH.4.223; 14.AH.4.240;
14.AH.4.244; 14.AH.4.243; 14.AH.4.247; 14.AH.5.157; 14.AH.5.158;
14.AH.5.196; 14.AH.5.223; 14.AH.5.240; 14.AH.5.244; 14.AH.5.243;
14.AH.5.247; 14.AH.7.157; 14.AH.7.158; 14.AH.7.196; 14.AH.7.223;
14.AH.7.240; 14.AH.7.244; 14.AH.7.243; 14.AH.7.247; 14.AH.15.157;
14.AH.15.158; 14.AH.15.196; 14.AH.15.223; 14.AH.15.240; 14.AH.15.244;
14.AH.15.243; 14.AH.15.247; 14.AH.16.157; 14.AH.16.158; 14.AH.16.196;
14.AH.16.223; 14.AH.16.240; 14.AH.16.244; 14.AH.16.243; 14.AH.16.247;
14.AH.18.157; 14.AH.18.158; 14.AH.18.196; 14.AH.18.223; 14.AH.18.240;
14.AH.18.244; 14.AH.18.243; 14.AH.18.247; 14.AH.26.157; 14.AH.26.158;
14.AH.26.196; 14.AH.26.223; 14.AH.26.240; 14.AH.26.244; 14.AH.26.243;
14.AH.26.247; 14.AH.27.157; 14.AH.27.158; 14.AH.27.196; 14.AH.27.223;
14.AH.27.240; 14.AH.27.244; 14.AH.27.243; 14.AH.27.247; 14.AH.29.157;
14.AH.29.158; 14.AH.29.196; 14.AH.29.223; 14.AH.29.240; 14.AH.29.244;
14.AH.29.243; 14.AH.29.247; 14.AH.54.157; 14.AH.54.158; 14.AH.54.196;
14.AH.54.223; 14.AH.54.240; 14.AH.54.244; 14.AH.54.243; 14.AH.54.247;
14.AH.55.157; 14.AH.55.158; 14.AH.55.196; 14.AH.55.223; 14.AH.55.240;
14.AH.55.244; 14.AH.55.243; 14.AH.55.247; 14.AH.56.157; 14.AH.56.158;
14.AH.56.196; 14.AH.56.223; 14.AH.56.240; 14.AH.56.244; 14.AH.56.243;
14.AH.56.247; 14.AH.157.157; 14.AH.157.158; 14.AH.157.196;
14.AH.157.223; 14.AH.157.240; 14.AH.157.244; 14.AH.157.243;
14.AH.157.247; 14.AH.196.157; 14.AH.196.158; 14.AH.196.196;
14.AH.196.223; 14.AH.196.240; 14.AH.196.244; 14.AH.196.243;
14.AH.196.247; 14.AH.223.157; 14.AH.223.158; 14.AH.223.196;
14.AH.223.223; 14.AH.223.240; 14.AH.223.244; 14.AH.223.243;
14.AH.223.247; 14.AH.240.157; 14.AH.240.158; 14.AH.240.196;
14.AH.240.223; 14.AH.240.240; 14.AH.240.244; 14.AH.240.243;
14.AH.240.247; 14.AH.244.157; 14.AH.244.158; 14.AH.244.196;
14.AH.244.223; 14.AH.244.240; 14.AH.244.244; 14.AH.244.243;
14.AH.244.247; 14.AH.247.157; 14.AH.247.158; 14.AH.247.196;
14.AH.247.223; 14.AH.247.240; 14.AH.247.244; 14.AH.247.243;
14.AH.247.247;
Prodrugs of 14.AJ 14.AJ.4.157; 14.AJ.4.158; 14.AJ.4.196; 14.AJ.4.223; 14.AJ.4.240;
14.AJ.4.244; 14.AJ.4.243; 14.AJ.4.247; 14.AJ.5.157; 14.AJ.5.158; 14.AJ.5.196;
14.AJ.5.223; 14.AJ.5.240; 14.AJ.5.244; 14.AJ.5.243; 14.AJ.5.247; 14.AJ.7.157;
14.AJ.7.158; 14.AJ.7.196; 14.AJ.7.223; 14.AJ.7.240; 14.AJ.7.244; 14.AJ.7.243;
14.AJ.7.247; 14.AJ.15.157; 14.AJ.15.158; 14.AJ.15.196; 14.AJ.15.223;
14.AJ.15.240; 14.AJ.15.244; 14.AJ.15.243; 14.AJ.15.247; 14.AJ.16.157;
14.AJ.16.158; 14.AJ.16.196; 14.AJ.16.223; 14.AJ.16.240; 14.AJ.16.244;
14.AJ.16.243; 14.AJ.16.247; 14.AJ.18.157; 14.AJ.18.158; 14.AJ.18.196;
14.AJ.18.223; 14.AJ.18.240; 14.AJ.18.244; 14.AJ.18.243; 14.AJ.18.247;
14.AJ.26.157; 14.AJ.26.158; 14.AJ.26.196; 14.AJ.26.223; 14.AJ.26.240;
14.AJ.26.244; 14.AJ.26.243; 14.AJ.26.247; 14.AJ.27.157; 14.AJ.27.158;
14.AJ.27.196; 14.AJ.27.223; 14.AJ.27.240; 14.AJ.27.244; 14.AJ.27.243;
14.AJ.27.247; 14.AJ.29.157; 14.AJ.29.158; 14.AJ.29.196; 14.AJ.29.223;
14.AJ.29.240; 14.AJ.29.244; 14.AJ.29.243; 14.AJ.29.247; 14.AJ.54.157;
14.AJ.54.158; 14.AJ.54.196; 14.AJ.54.223; 14.AJ.54.240; 14.AJ.54.244;
14.AJ.54.243; 14.AJ.54.247; 14.AJ.55.157; 14.AJ.55.158; 14.AJ.55.196;
14.AJ.55.223; 14.AJ.55.240; 14.AJ.55.244; 14.AJ.55.243; 14.AJ.55.247;

TABLE 100-continued

14.AJ.56.157; 14.AJ.56.158; 14.AJ.56.196; 14.AJ.56.223; 14.AJ.56.240;
14.AJ.56.244; 14.AJ.56.243; 14.AJ.56.247; 14.AJ.157.157; 14.AJ.157.158;
14.AJ.157.196; 14.AJ.157.223; 14.AJ.157.240; 14.AJ.157.244; 14.AJ.157.243;
14.AJ.157.247; 14.AJ.196.157; 14.AJ.196.158; 14.AJ.196.196; 14.AJ.196.223;
14.AJ.196.240; 14.AJ.196.244; 14.AJ.196.243; 14.AJ.196.247; 14.AJ.223.157;
14.AJ.223.158; 14.AJ.223.196; 14.AJ.223.223; 14.AJ.223.240; 14.AJ.223.244;
14.AJ.223.243; 14.AJ.223.247; 14.AJ.240.157; 14.AJ.240.158; 14.AJ.240.196;
14.AJ.240.223; 14.AJ.240.240; 14.AJ.240.244; 14.AJ.240.243; 14.AJ.240.247;
14.AJ.244.157; 14.AJ.244.158; 14.AJ.244.196; 14.AJ.244.223; 14.AJ.244.240;
14.AJ.244.244; 14.AJ.244.243; 14.AJ.244.247; 14.AJ.247.157; 14.AJ.247.158;
14.AJ.247.196; 14.AJ.247.223; 14.AJ.247.240; 14.AJ.247.244; 14.AJ.247.243;
14.AJ.247.247;
Prodrugs of 14.AN 14.AN.4.157; 14.AN.4.158; 14.AN.4.196; 14.AN.4.223; 14.AN.4.240;
14.AN.4.244; 14.AN.4.243; 14.AN.4.247; 14.AN.5.157; 14.AN.5.158;
14.AN.5.196; 14.AN.5.223; 14.AN.5.240; 14.AN.5.244; 14.AN.5.243;
14.AN.5.247; 14.AN.7.157; 14.AN.7.158; 14.AN.7.196; 14.AN.7.223;
14.AN.7.240; 14.AN.7.244; 14.AN.7.243; 14.AN.7.247; 14.AN.15.157;
14.AN.15.158; 14.AN.15.196; 14.AN.15.223; 14.AN.15.240; 14.AN.15.244;
14.AN.15.243; 14.AN.15.247; 14.AN.16.157; 14.AN.16.158; 14.AN.16.196;
14.AN.16.223; 14.AN.16.240; 14.AN.16.244; 14.AN.16.243; 14.AN.16.247;
14.AN.18.157; 14.AN.18.158; 14.AN.18.196; 14.AN.18.223; 14.AN.18.240;
14.AN.18.244; 14.AN.18.243; 14.AN.18.247; 14.AN.26.157; 14.AN.26.158;
14.AN.26.196; 14.AN.26.223; 14.AN.26.240; 14.AN.26.244; 14.AN.26.243;
14.AN.26.247; 14.AN.27.157; 14.AN.27.158; 14.AN.27.196; 14.AN.27.223;
14.AN.27.240; 14.AN.27.244; 14.AN.27.243; 14.AN.27.247; 14.AN.29.157;
14.AN.29.158; 14.AN.29.196; 14.AN.29.223; 14.AN.29.240; 14.AN.29.244;
14.AN.29.243; 14.AN.29.247; 14.AN.54.157; 14.AN.54.158; 14.AN.54.196;
14.AN.54.223; 14.AN.54.240; 14.AN.54.244; 14.AN.54.243; 14.AN.54.247;
14.AN.55.157; 14.AN.55.158; 14.AN.55.196; 14.AN.55.223; 14.AN.55.240;
14.AN.55.244; 14.AN.55.243; 14.AN.55.247; 14.AN.56.157; 14.AN.56.158;
14.AN.56.196; 14.AN.56.223; 14.AN.56.240; 14.AN.56.244; 14.AN.56.243;
14.AN.56.247; 14.AN.157.157; 14.AN.157.158; 14.AN.157.196;
14.AN.157.223; 14.AN.157.240; 14.AN.157.244; 14.AN.157.243;
14.AN.157.247; 14.AN.196.157; 14.AN.196.158; 14.AN.196.196;
14.AN.196.223; 14.AN.196.240; 14.AN.196.244; 14.AN.196.243;
14.AN.196.247; 14.AN.223.157; 14.AN.223.158; 14.AN.223.196;
14.AN.223.223; 14.AN.223.240; 14.AN.223.244; 14.AN.223.243;
14.AN.223.247; 14.AN.240.157; 14.AN.240.158; 14.AN.240.196;
14.AN.240.223; 14.AN.240.240; 14.AN.240.244; 14.AN.240.243;
14.AN.240.247; 14.AN.244.157; 14.AN.244.158; 14.AN.244.196;
14.AN.244.223; 14.AN.244.240; 14.AN.244.244; 14.AN.244.243;
14.AN.244.247; 14.AN.247.157; 14.AN.247.158; 14.AN.247.196;
14.AN.247.223; 14.AN.247.240; 14.AN.247.244; 14.AN.247.243;
14.AN.247.247;
Prodrugs of 14.AP 14.AP.4.157; 14.AP.4.158; 14.AP.4.196; 14.AP.4.223; 14.AP.4.240;
14.AP.4.244; 14.AP.4.243; 14.AP.4.247; 14.AP.5.157; 14.AP.5.158;
14.AP.5.196; 14.AP.5.223; 14.AP.5.240; 14.AP.5.244; 14.AP.5.243;
14.AP.5.247; 14.AP.7.157; 14.AP.7.158; 14.AP.7.196; 14.AP.7.223;
14.AP.7.240; 14.AP.7.244; 14.AP.7.243; 14.AP.7.247; 14.AP.15.157;
14.AP.15.158; 14.AP.15.196; 14.AP.15.223; 14.AP.15.240; 14.AP.15.244;
14.AP.15.243; 14.AP.15.247; 14.AP.16.157; 14.AP.16.158; 14.AP.16.196;
14.AP.16.223; 14.AP.16.240; 14.AP.16.244; 14.AP.16.243; 14.AP.16.247;
14.AP.18.157; 14.AP.18.158; 14.AP.18.196; 14.AP.18.223; 14.AP.18.240;
14.AP.18.244; 14.AP.18.243; 14.AP.18.247; 14.AP.26.157; 14.AP.26.158;
14.AP.26.196; 14.AP.26.223; 14.AP.26.240; 14.AP.26.244; 14.AP.26.243;
14.AP.26.247; 14.AP.27.157; 14.AP.27.158; 14.AP.27.196; 14.AP.27.223;
14.AP.27.240; 14.AP.27.244; 14.AP.27.243; 14.AP.27.247; 14.AP.29.157;
14.AP.29.158; 14.AP.29.196; 14.AP.29.223; 14.AP.29.240; 14.AP.29.244;
14.AP.29.243; 14.AP.29.247; 14.AP.54.157; 14.AP.54.158; 14.AP.54.196;
14.AP.54.223; 14.AP.54.240; 14.AP.54.244; 14.AP.54.243; 14.AP.54.247;
14.AP.55.157; 14.AP.55.158; 14.AP.55.196; 14.AP.55.223; 14.AP.55.240;
14.AP.55.244; 14.AP.55.243; 14.AP.55.247; 14.AP.56.157; 14.AP.56.158;
14.AP.56.196; 14.AP.56.223; 14.AP.56.240; 14.AP.56.244; 14.AP.56.243;
14.AP.56.247; 14.AP.157.157; 14.AP.157.158; 14.AP.157.196; 14.AP.157.223;
14.AP.157.240; 14.AP.157.244; 14.AP.157.243; 14.AP.157.247;
14.AP.196.157; 14.AP.196.158; 14.AP.196.196; 14.AP.196.223;
14.AP.196.240; 14.AP.196.244; 14.AP.196.243; 14.AP.196.247;
14.AP.223.157; 14.AP.223.158; 14.AP.223.196; 14.AP.223.223;
14.AP.223.240; 14.AP.223.244; 14.AP.223.243; 14.AP.223.247;
14.AP.240.157; 14.AP.240.158; 14.AP.240.196; 14.AP.240.223;
14.AP.240.240; 14.AP.240.244; 14.AP.240.243; 14.AP.240.247;
14.AP.244.157; 14.AP.244.158; 14.AP.244.196; 14.AP.244.223;
14.AP.244.240; 14.AP.244.244; 14.AP.244.243; 14.AP.244.247;
14.AP.247.157; 14.AP.247.158; 14.AP.247.196; 14.AP.247.223;
14.AP.247.240; 14.AP.247.244; 14.AP.247.243; 14.AP.247.247;

TABLE 100-continued

Prodrugs of 14.AZ

14.AZ.4.157; 14.AZ.4.158; 14.AZ.4.196; 14.AZ.4.223; 14.AZ.4.240;
14.AZ.4.244; 14.AZ.4.243; 14.AZ.4.247; 14.AZ.5.157; 14.AZ.5.158;
14.AZ.5.196; 14.AZ.5.223; 14.AZ.5.240; 14.AZ.5.244; 14.AZ.5.243;
14.AZ.5.247; 14.AZ.7.157; 14.AZ.7.158; 14.AZ.7.196; 14.AZ.7.223;
14.AZ.7.240; 14.AZ.7.244; 14.AZ.7.243; 14.AZ.7.247; 14.AZ.15.157;
14.AZ.15.158; 14.AZ.15.196; 14.AZ.15.223; 14.AZ.15.240; 14.AZ.15.244;
14.AZ.15.243; 14.AZ.15.247; 14.AZ.16.157; 14.AZ.16.158; 14.AZ.16.196;
14.AZ.16.223; 14.AZ.16.240; 14.AZ.16.244; 14.AZ.16.243; 14.AZ.16.247;
14.AZ.18.157; 14.AZ.18.158; 14.AZ.18.196; 14.AZ.18.223; 14.AZ.18.240;
14.AZ.18.244; 14.AZ.18.243; 14.AZ.18.247; 14.AZ.26.157; 14.AZ.26.158;
14.AZ.26.196; 14.AZ.26.223; 14.AZ.26.240; 14.AZ.26.244; 14.AZ.26.243;
14.AZ.26.247; 14.AZ.27.157; 14.AZ.27.158; 14.AZ.27.196; 14.AZ.27.223;
14.AZ.27.240; 14.AZ.27.244; 14.AZ.27.243; 14.AZ.27.247; 14.AZ.29.157;
14.AZ.29.158; 14.AZ.29.196; 14.AZ.29.223; 14.AZ.29.240; 14.AZ.29.244;
14.AZ.29.243; 14.AZ.29.247; 14.AZ.54.157; 14.AZ.54.158; 14.AZ.54.196;
14.AZ.54.223; 14.AZ.54.240; 14.AZ.54.244; 14.AZ.54.243; 14.AZ.54.247;
14.AZ.55.157; 14.AZ.55.158; 14.AZ.55.196; 14.AZ.55.223; 14.AZ.55.240;
14.AZ.55.244; 14.AZ.55.243; 14.AZ.55.247; 14.AZ.56.157; 14.AZ.56.158;
14.AZ.56.196; 14.AZ.56.223; 14.AZ.56.240; 14.AZ.56.244; 14.AZ.56.243;
14.AZ.56.247; 14.AZ.157.157; 14.AZ.157.158; 14.AZ.157.196; 14.AZ.157.223;
14.AZ.157.240; 14.AZ.157.244; 14.AZ.157.243; 14.AZ.157.247;
14.AZ.196.157; 14.AZ.196.158; 14.AZ.196.196; 14.AZ.196.223;
14.AZ.196.240; 14.AZ.196.244; 14.AZ.196.243; 14.AZ.196.247;
14.AZ.223.157; 14.AZ.223.158; 14.AZ.223.196; 14.AZ.223.223;
14.AZ.223.240; 14.AZ.223.244; 14.AZ.223.243; 14.AZ.223.247;
14.AZ.240.157; 14.AZ.240.158; 14.AZ.240.196; 14.AZ.240.223;
14.AZ.240.240; 14.AZ.240.244; 14.AZ.240.243; 14.AZ.240.247;
14.AZ.244.157; 14.AZ.244.158; 14.AZ.244.196; 14.AZ.244.223;
14.AZ.244.240; 14.AZ.244.244; 14.AZ.244.243; 14.AZ.244.247;
14.AZ.247.157; 14.AZ.247.158; 14.AZ.247.196; 14.AZ.247.223;
14.AZ.247.240; 14.AZ.247.244; 14.AZ.247.243; 14.AZ.247.247;

Prodrugs of 14.BF

14.BF.4.157; 14.BF.4.158; 14.BF.4.196; 14.BF.4.223; 14.BF.4.240;
14.BF.4.244; 14.BF.4.243; 14.BF.4.247; 14.BF.5.157; 14.BF.5.158;
14.BF.5.196; 14.BF.5.223; 14.BF.5.240; 14.BF.5.244; 14.BF.5.243;
14.BF.5.247; 14.BF.7.157; 14.BF.7.158; 14.BF.7.196; 14.BF.7.223;
14.BF.7.240; 14.BF.7.244; 14.BF.7.243; 14.BF.7.247; 14.BF.15.157;
14.BF.15.158; 14.BF.15.196; 14.BF.15.223; 14.BF.15.240; 14.BF.15.244;
14.BF.15.243; 14.BF.15.247; 14.BF.16.157; 14.BF.16.158; 14.BF.16.196;
14.BF.16.223; 14.BF.16.240; 14.BF.16.244; 14.BF.16.243; 14.BF.16.247;
14.BF.18.157; 14.BF.18.158; 14.BF.18.196; 14.BF.18.223; 14.BF.18.240;
14.BF.18.244; 14.BF.18.243; 14.BF.18.247; 14.BF.26.157; 14.BF.26.158;
14.BF.26.196; 14.BF.26.223; 14.BF.26.240; 14.BF.26.244; 14.BF.26.243;
14.BF.26.247; 14.BF.27.157; 14.BF.27.158; 14.BF.27.196; 14.BF.27.223;
14.BF.27.240; 14.BF.27.244; 14.BF.27.243; 14.BF.27.247; 14.BF.29.157;
14.BF.29.158; 14.BF.29.196; 14.BF.29.223; 14.BF.29.240; 14.BF.29.244;
14.BF.29.243; 14.BF.29.247; 14.BF.54.157; 14.BF.54.158; 14.BF.54.196;
14.BF.54.223; 14.BF.54.240; 14.BF.54.244; 14.BF.54.243; 14.BF.54.247;
14.BF.55.157; 14.BF.55.158; 14.BF.55.196; 14.BF.55.223; 14.BF.55.240;
14.BF.55.244; 14.BF.55.243; 14.BF.55.247; 14.BF.56.157; 14.BF.56.158;
14.BF.56.196; 14.BF.56.223; 14.BF.56.240; 14.BF.56.244; 14.BF.56.243;
14.BF.56.247; 14.BF.157.157; 14.BF.157.158; 14.BF.157.196; 14.BF.157.223;
14.BF.157.240; 14.BF.157.244; 14.BF.157.243; 14.BF.157.247; 14.BF.196.157;
14.BF.196.158; 14.BF.196.196; 14.BF.196.223; 14.BF.196.240; 14.BF.196.244;
14.BF.196.243; 14.BF.196.247; 14.BF.223.157; 14.BF.223.158; 14.BF.223.196;
14.BF.223.223; 14.BF.223.240; 14.BF.223.244; 14.BF.223.243; 14.BF.223.247;
14.BF.240.157; 14.BF.240.158; 14.BF.240.196; 14.BF.240.223; 14.BF.240.240;
14.BF.240.244; 14.BF.240.243; 14.BF.240.247; 14.BF.244.157; 14.BF.244.158;
14.BF.244.196; 14.BF.244.223; 14.BF.244.240; 14.BF.244.244; 14.BF.244.243;
14.BF.244.247; 14.BF.247.157; 14.BF.247.158; 14.BF.247.196; 14.BF.247.223;
14.BF.247.240; 14.BF.247.244; 14.BF.247.243; 14.BF.247.247;

Prodrugs of 14.CI

14.CI.4.157; 14.CI.4.158; 14.CI.4.196; 14.CI.4.223; 14.CI.4.240;
14.CI.4.244; 14.CI.4.243; 14.CI.4.247; 14.CI.5.157; 14.CI.5.158; 14.CI.5.196;
14.CI.5.223; 14.CI.5.240; 14.CI.5.244; 14.CI.5.243; 14.CI.5.247; 14.CI.7.157;
14.CI.7.158; 14.CI.7.196; 14.CI.7.223; 14.CI.7.240; 14.CI.7.244; 14.CI.7.243;
14.CI.7.247; 14.CI.15.157; 14.CI.15.158; 14.CI.15.196; 14.CI.15.223;
14.CI.15.240; 14.CI.15.244; 14.CI.15.243; 14.CI.15.247; 14.CI.16.157;
14.CI.16.158; 14.CI.16.196; 14.CI.16.223; 14.CI.16.240; 14.CI.16.244;
14.CI.16.243; 14.CI.16.247; 14.CI.18.157; 14.CI.18.158; 14.CI.18.196;
14.CI.18.223; 14.CI.18.240; 14.CI.18.244; 14.CI.18.243; 14.CI.18.247;
14.CI.26.157; 14.CI.26.158; 14.CI.26.196; 14.CI.26.223; 14.CI.26.240;
14.CI.26.244; 14.CI.26.243; 14.CI.26.247; 14.CI.27.157; 14.CI.27.158;
14.CI.27.196; 14.CI.27.223; 14.CI.27.240; 14.CI.27.244; 14.CI.27.243;
14.CI.27.247; 14.CI.29.157; 14.CI.29.158; 14.CI.29.196; 14.CI.29.223;

TABLE 100-continued

14.CI.29.240; 14.CI.29.244; 14.CI.29.243; 14.CI.29.247; 14.CI.54.157;
14.CI.54.158; 14.CI.54.196; 14.CI.54.223; 14.CI.54.240; 14.CI.54.244;
14.CI.54.243; 14.CI.54.247; 14.CI.55.157; 14.CI.55.158; 14.CI.55.196;
14.CI.55.223; 14.CI.55.240; 14.CI.55.244; 14.CI.55.243; 14.CI.55.247;
14.CI.56.157; 14.CI.56.158; 14.CI.56.196; 14.CI.56.223; 14.CI.56.240;
14.CI.56.244; 14.CI.56.243; 14.CI.56.247; 14.CI.157.157; 14.CI.157.158;
14.CI.157.196; 14.CI.157.223; 14.CI.157.240; 14.CI.157.244; 14.CI.157.243;
14.CI.157.247; 14.CI.196.157; 14.CI.196.158; 14.CI.196.196; 14.CI.196.223;
14.CI.196.240; 14.CI.196.244; 14.CI.196.243; 14.CI.196.247; 14.CI.223.157;
14.CI.223.158; 14.CI.223.196; 14.CI.223.223; 14.CI.223.240; 14.CI.223.244;
14.CI.223.243; 14.CI.223.247; 14.CI.240.157; 14.CI.240.158; 14.CI.240.196;
14.CI.240.223; 14.CI.240.240; 14.CI.240.244; 14.CI.240.243; 14.CI.240.247;
14.CI.244.157; 14.CI.244.158; 14.CI.244.196; 14.CI.244.223; 14.CI.244.240;
14.CI.244.244; 14.CI.244.243; 14.CI.244.247; 14.CI.247.157; 14.CI.247.158;
14.CI.247.196; 14.CI.247.223; 14.CI.247.240; 14.CI.247.244; 14.CI.247.243;
14.CI.247.247;
Prodrugs of 14.CO 14.CO.4.157; 14.CO.4.158; 14.CO.4.196; 14.CO.4.223; 14.CO.4.240;
14.CO.4.244; 14.CO.4.243; 14.CO.4.247; 14.CO.5.157; 14.CO.5.158;
14.CO.5.196; 14.CO.5.223; 14.CO.5.240; 14.CO.5.244; 14.CO.5.243;
14.CO.5.247; 14.CO.7.157; 14.CO.7.158; 14.CO.7.196; 14.CO.7.223;
14.CO.7.240; 14.CO.7.244; 14.CO.7.243; 14.CO.7.247; 14.CO.15.157;
14.CO.15.158; 14.CO.15.196; 14.CO.15.223; 14.CO.15.240; 14.CO.15.244;
14.CO.15.243; 14.CO.15.247; 14.CO.16.157; 14.CO.16.158; 14.CO.16.196;
14.CO.16.223; 14.CO.16.240; 14.CO.16.244; 14.CO.16.243; 14.CO.16.247;
14.CO.18.157; 14.CO.18.158; 14.CO.18.196; 14.CO.18.223; 14.CO.18.240;
14.CO.18.244; 14.CO.18.243; 14.CO.18.247; 14.CO.26.157; 14.CO.26.158;
14.CO.26.196; 14.CO.26.223; 14.CO.26.240; 14.CO.26.244; 14.CO.26.243;
14.CO.26.247; 14.CO.27.157; 14.CO.27.158; 14.CO.27.196; 14.CO.27.223;
14.CO.27.240; 14.CO.27.244; 14.CO.27.243; 14.CO.27.247; 14.CO.29.157;
14.CO.29.158; 14.CO.29.196; 14.CO.29.223; 14.CO.29.240; 14.CO.29.244;
14.CO.29.243; 14.CO.29.247; 14.CO.54.157; 14.CO.54.158; 14.CO.54.196;
14.CO.54.223; 14.CO.54.240; 14.CO.54.244; 14.CO.54.243; 14.CO.54.247;
14.CO.55.157; 14.CO.55.158; 14.CO.55.196; 14.CO.55.223; 14.CO.55.240;
14.CO.55.244; 14.CO.55.243; 14.CO.55.247; 14.CO.56.157; 14.CO.56.158;
14.CO.56.196; 14.CO.56.223; 14.CO.56.240; 14.CO.56.244; 14.CO.56.243;
14.CO.56.247; 14.CO.157.157; 14.CO.157.158; 14.CO.157.196;
14.CO.157.223; 14.CO.157.240; 14.CO.157.244; 14.CO.157.243;
14.CO.157.247; 14.CO.196.157; 14.CO.196.158; 14.CO.196.196;
14.CO.196.223; 14.CO.196.240; 14.CO.196.244; 14.CO.196.243;
14.CO.196.247; 14.CO.223.157; 14.CO.223.158; 14.CO.223.196;
14.CO.223.223; 14.CO.223.240; 14.CO.223.244; 14.CO.223.243;
14.CO.223.247; 14.CO.240.157; 14.CO.240.158; 14.CO.240.196;
14.CO.240.223; 14.CO.240.240; 14.CO.240.244; 14.CO.240.243;
14.CO.240.247; 14.CO.244.157; 14.CO.244.158; 14.CO.244.196;
14.CO.244.223; 14.CO.244.240; 14.CO.244.244; 14.CO.244.243;
14.CO.244.247; 14.CO.4.157; 14.CO.4.158; 14.CO.4.196; 14.CO.4.223;
14.CO.4.240; 14.CO.4.244; 14.CO.4.243; 14.CO.4.247;

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention.

In the claims hereinbelow, the subscript and superscripts of a given variable are distinct. For example, $R_1$ is distinct from $R^1$.

We claim:

1. A method of inhibiting leukemia cells in vitro comprising the step of contacting a sample in need of such treatment with a conjugate or a pharmaceutically acceptable salt or solvate thereof wherein the conjugate is a compound of the formula:

[DRUG]–(A⁰)$_{nn}$;

wherein:
DRUG is a compound of formula 557:

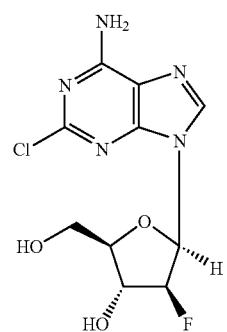

557 wherein:
nn is 1, 2 or 3;
A⁰ is A¹, A² or W³ with the proviso that the conjugate includes at least one A¹;

$A^1$ is:

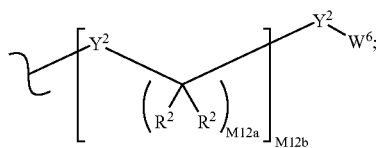

$A^2$ is:

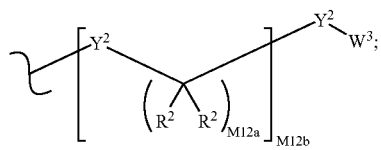

$A^3$ is:

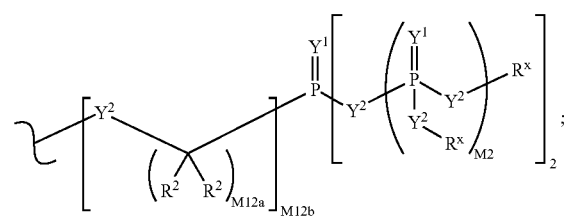

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, —S(O)$_{M2}$—, or —S(O)$_{M2}$—S(O)$_{M2}$—; and when $Y^2$ joins two phosphorous atoms $Y^2$ can also be $C(R^2)(R^2)$;

$R^x$ is independently H, $R^1$, $R^2$, $W^3$, a protecting group, or the formula:

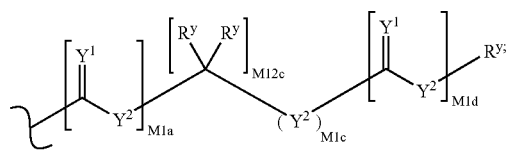

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, —CN, $N_3$ or —NO$_2$;
$R^{3b}$ is $Y^1$;
$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)$ $OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;
$R^{3d}$ is —$C(Y^1)R^x$, —$C(Y^1)OR^x$ or —$C(Y^1)(N(R^x)(R^x))$;
$R^4$ is an alkyl of 1 to 18 carbon atoms, alkenyl of 2 to 18 carbon atoms, or alkynyl of 2 to 18 carbon atoms;
$R^5$ is $R^4$ wherein each $R^4$ is substituted with 0 to 3 $R^3$ groups;
$W^3$ is $W^4$ or $W^5$;
$W^4$ is $R^5$, —$C(Y^1)R^5$, —$C(Y^1)W^5$, —$SO_{M2}R^5$, or —$SO_{M2}W^5$;
$W^5$ is carbocycle wherein $W^5$ is independently substituted with 0 to 3 $R^2$ groups;
$W^6$ is $W^3$ independently substituted with 1, 2, or 3 $A^3$ groups;
M2 is 0, 1 or 2;
M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1; and
M12c is 0, 1, 2, 3, 4, 5, 6, 7, 8, 9, 10, 11 or 12.

2. A method of treating leukemia in a mammal, comprising administering a conjugate or a pharmaceutically acceptable salt or solvate thereof, to the mammal wherein the conjugate is a compound of formula:

[DRUG]–(A$^0$)$_{nn}$;

wherein:
DRUG is a compound of formula 557:

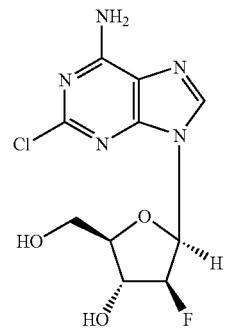

557 wherein:
nn is 1, 2 or 3;
$A^0$ is $A^1$, $A^2$ or $W^3$ with the proviso that the conjugate includes at least one $A^1$;

$A^1$ is:

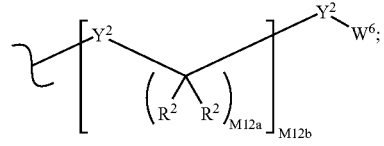

$A^2$ is:

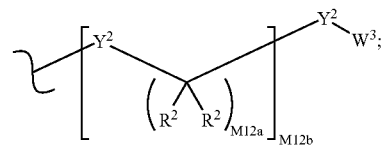

-continued $A^3$ is:

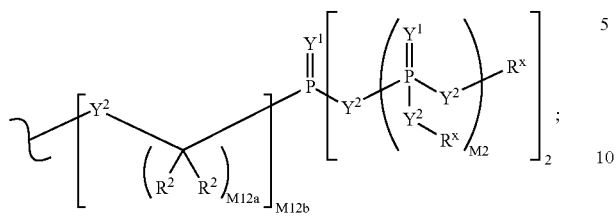

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, —$S(O)_{M2}$—, or —$S(O)_{M2}$—$S(O)_{M2}$—; and when $Y^2$ joins two phosphorous atoms $Y^2$ can also be $C(R^2)(R^2)$;

$R^x$ is independently H, $R^1$, $R^2$, $W^3$, a protecting group, or the formula:

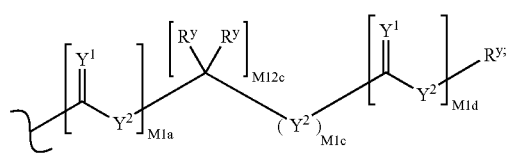

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;

$R^{3d}$ is —$C(Y^1)R^x$, —$C(Y^1)OR^x$ or —$C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —$C(Y^1)R^5$, —$C(Y^1)W^5$, —$SO_{M2}R^5$, or —$SO_{M2}W^5$;

$W^5$ is carbocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

3. The method of claim 1 where the conjugate has formula 211 or 212:

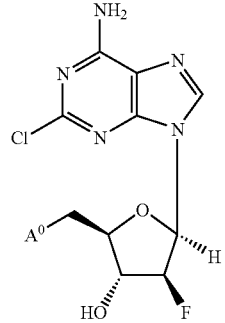

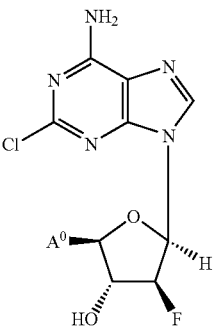

wherein:

one $A^0$ is $A^1$.

4. The method of claim 1 wherein each $A^3$ is of the formula:

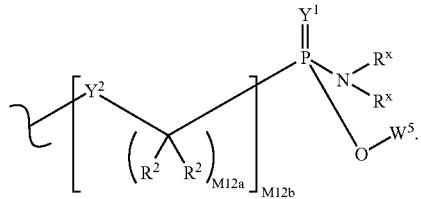

5. The method of claim 1 wherein each $A^3$ is of the formula:

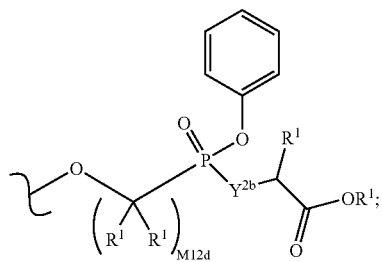

wherein the phenyl carbocycle is substituted with 0, 1, 2, or 3 $R^2$ groups.

6. The method of claim 1 wherein each $A^3$ is of the formula:

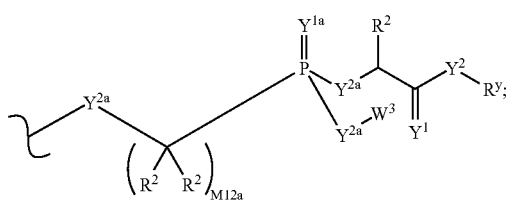

wherein:

$Y^{1a}$ is O or S; and $Y^{2a}$ is O, $N(R^2)$ or S.

7. The method of claim 1 wherein $A^0$ is of the formula:

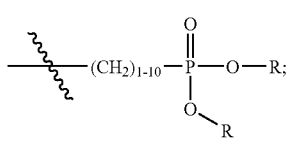

wherein each R is independently alkyl.

8. The method of claim 2 where the conjugate has formula 211 or 212:

211

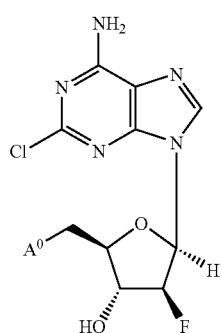

212

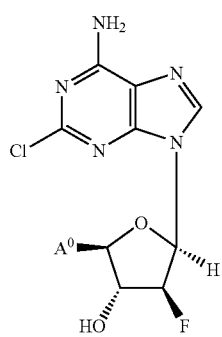

wherein:

one $A^0$ is $A^1$.

9. The method of claim 2 wherein $A^0$ is of the formula:

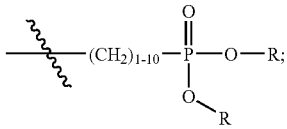

wherein each R is independently alkyl.

10. The method of claim 2 wherein each $A^3$ is of the formula:

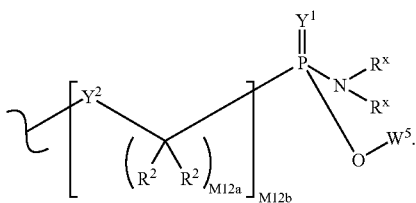

11. The method of claim 2 wherein each $A^3$ is of the formula:

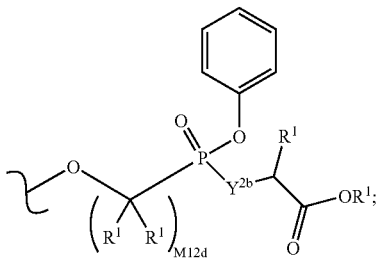

wherein the phenyl carbocycle is substituted with 0, 1, 2, or 3 $R^2$ groups.

12. The method of claim 2 wherein each $A^3$ is of the formula:

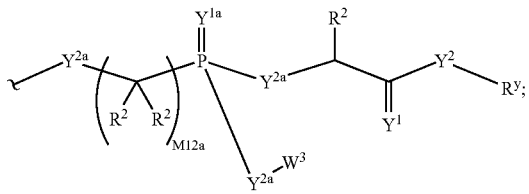

wherein:

$Y^{1a}$ is O or S; and $Y^{2a}$ is O, $N(R^2)$ or S.

13. The method of claim 2 wherein the leukemia is acute myelogenous leukemia, chronic lymphocytic leukemia, chronic myelogenous leukemia, or hairy-cell leukemia.

\* \* \* \* \*